US010446765B2

(12) United States Patent
Lee et al.

(10) Patent No.: US 10,446,765 B2
(45) Date of Patent: Oct. 15, 2019

(54) HETEROCYCLIC COMPOUND AND ORGANIC LIGHT EMITTING ELEMENT USING SAME

(71) Applicant: HEESUNG MATERIAL LTD., Yongin, Gyeonggi-do (KR)

(72) Inventors: Jung-Hyun Lee, Osan (KR); Su-Jin Jung, Yongin (KR); Sang-Kyu Kang, Seongnam (KR); Kee-Yong Kim, Suwon (KR); Dong-Jun Kim, Yongin (KR); Jin-Seok Choi, Suwon (KR); Dae-Hyuk Choi, Yongin (KR); Sung-Jin Eum, Yongin (KR); Joo-Dong Lee, Seongnam (KR)

(73) Assignee: HEESUNG MATERIAL LTD., Yongin (KR)

( * ) Notice: Subject to any disclaimer, the term of this patent is extended or adjusted under 35 U.S.C. 154(b) by 15 days.

(21) Appl. No.: 15/318,901

(22) PCT Filed: Jun. 30, 2015

(86) PCT No.: PCT/KR2015/006723

§ 371 (c)(1),
(2) Date: Dec. 14, 2016

(87) PCT Pub. No.: WO2016/003171

PCT Pub. Date: Jan. 7, 2016

(65) Prior Publication Data

US 2017/0133602 A1 May 11, 2017

(30) Foreign Application Priority Data

Jun. 30, 2014 (KR) ........................ 10-2014-0081206
Sep. 23, 2014 (KR) ........................ 10-2014-0127222

(51) Int. Cl.
*H01L 51/00* (2006.01)
*C09K 11/06* (2006.01)
(Continued)

(52) U.S. Cl.
CPC ........ *H01L 51/0072* (2013.01); *C07D 221/18* (2013.01); *C07D 401/10* (2013.01);
(Continued)

(58) Field of Classification Search
None
See application file for complete search history.

(56) References Cited

U.S. PATENT DOCUMENTS

| | | | |
|---|---|---|---|
| 4,356,429 | A | 10/1982 | Tang |
| 5,728,709 | A | 3/1998 | Ikuina et al. |
| 2014/0145169 | A1 | 5/2014 | Lee et al. |

FOREIGN PATENT DOCUMENTS

| | | | |
|---|---|---|---|
| KR | 10-2010-0108924 A | 10/2010 |
| WO | WO 96-28447 A1 | 9/1996 |

(Continued)

OTHER PUBLICATIONS

Zhang et al. (Angew. Chem. Int. 2013, 52, p. 10792).*

(Continued)

*Primary Examiner* — Jay Yang
(74) *Attorney, Agent, or Firm* — Birch, Stewart, Kolasch & Birch, LLP

(57) ABSTRACT

The present specification relates to a novel hetero-cyclic compound, and an organic light emitting device using the same.

14 Claims, 23 Drawing Sheets

(51) Int. Cl.

| | |
|---|---|
| ***C09K 11/02*** | (2006.01) |
| ***C07F 9/576*** | (2006.01) |
| ***C07D 405/12*** | (2006.01) |
| ***C07D 491/048*** | (2006.01) |
| ***C07D 221/18*** | (2006.01) |
| ***C07D 401/14*** | (2006.01) |
| ***C07D 401/10*** | (2006.01) |
| ***C07D 471/04*** | (2006.01) |
| ***C07D 495/04*** | (2006.01) |
| ***C07F 9/6561*** | (2006.01) |
| *H01L 51/50* | (2006.01) |

(52) U.S. Cl.

CPC ......... *C07D 401/14* (2013.01); *C07D 405/12* (2013.01); *C07D 471/04* (2013.01); *C07D 491/048* (2013.01); *C07D 495/04* (2013.01); *C07F 9/5765* (2013.01); *C07F 9/6561* (2013.01); *C09K 11/02* (2013.01); *C09K 11/06* (2013.01); *H01L 51/0054* (2013.01); *H01L 51/0061* (2013.01); *H01L 51/0067* (2013.01); *H01L 51/0071* (2013.01); *H01L 51/0074* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01); *H01L 51/0052* (2013.01); *H01L 51/0073* (2013.01); *H01L 51/5016* (2013.01); *H01L 51/5056* (2013.01); *H01L 51/5072* (2013.01)

(56) References Cited

FOREIGN PATENT DOCUMENTS

| | | | |
|---|---|---|---|
| WO | WO 2010/114264 A2 | | 10/2010 |
| WO | WO 2013-191355 A1 | | 12/2013 |
| WO | WO-2016/064088 A2 | * | 4/2016 |

OTHER PUBLICATIONS

Machine English translation of Jang et al. (WO 2016/064088 A2). Oct. 18, 2017.*

Zhu et al. (Org. Lett. 2014, 16, p. 1260).*

International Search Report for PCT/KR2015/006723 (PCT/ISA/210) dated Oct. 5, 2015.

Klemm et al. "Synthesis of 1H Indolo[2,3-i]phenanthridine(I)", Journal of Heterocyclic Chemistry, vol. 9. No. 4, 1972, p. 927.

Laronze-Cochard et al., "Synthesis and biological evaluation of new penta- and heptacyclic indolo-and quinolinocarbazole ring systems obtained via $Pd^0$ catalysed reductive N-heteroannulation", Organic & Biolomolecular Chemistry, vol. 8, 2010, pp. 4625-4636.

Office Action of Taiwanese Patent Office for TW 104121145 dated Jun. 13, 2016.

Zhu et al., "Synthesis of Quinolinyl/Isoquinolinyl[a]pyrrolo [3,4-c] Carbazoles as Cyclin DI/CDK4 Inhibitors", Bioorganic & Medicinal Chemistry Letters, vol. 13, 2003, pp. 1231-1235.

Zhang, B., et al, "6-Trifluoromethyl-Phenanthridines through Radical Trifluoromethylation of Isonitriles," Angew. Chem. Int. Ed., 2013, vol. 52, pp. 10792-10795.

Lyakhova et al., "Bromine-containing alkaloids from the marine sponge Penares sp.", Tetrahedron Letters, vol. 53, Issue 45, 2012 (published online Sep. 7, 2012), pp. 6119-6122.

Mohanakrishnan et al., "A Versatile Construction of the 8H-Quino[4,3-b]carbazole Ring System as a Potential DNA Binder", J. Org. Chem., 1995, vol. 60, No. 7, pp. 1939-1946.

Ramkumar et al., "Total Synthesis of Calothrixin A and B via C-H Activation", J. Org. Chem. 2013, vol. 78, No. 6, pp. 2802-2807.

* cited by examiner

[Figure 1]
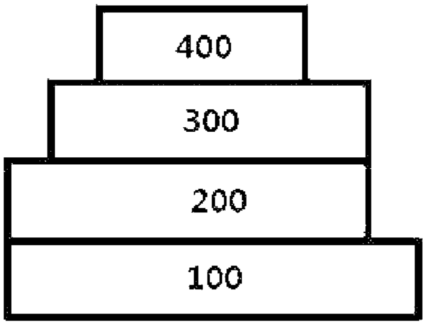
[Figure 2]
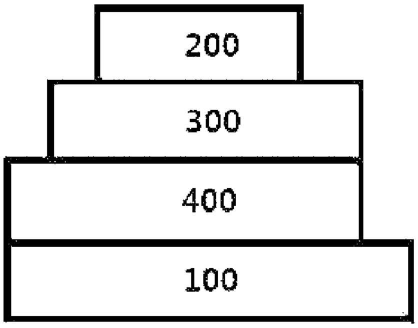

[Figure 3]
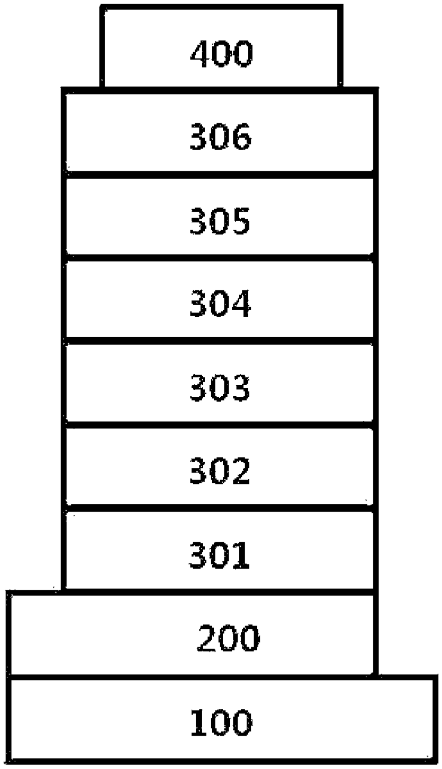

[Figure 4]
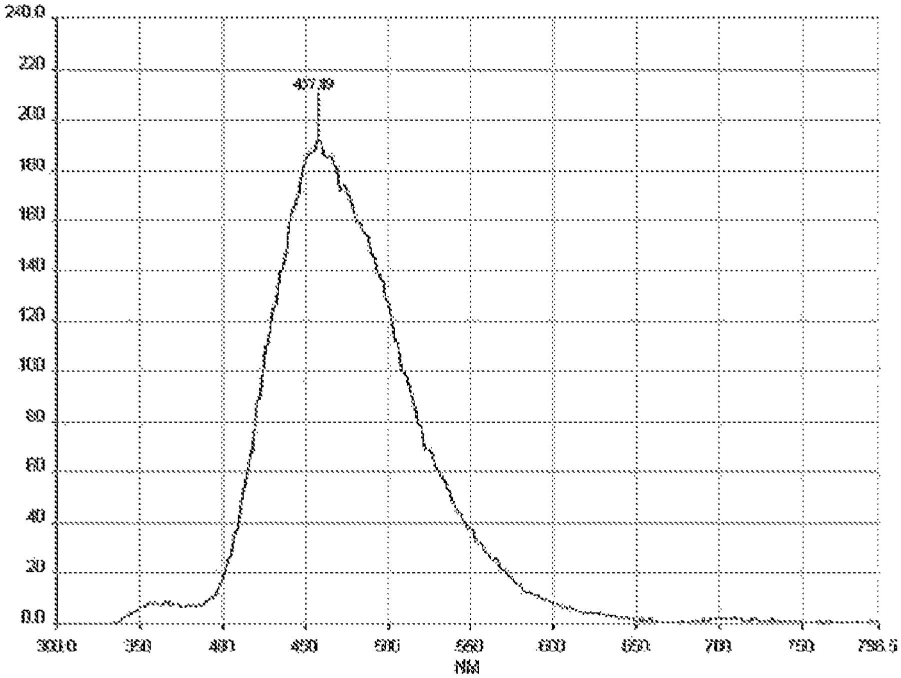

[Figure 5]
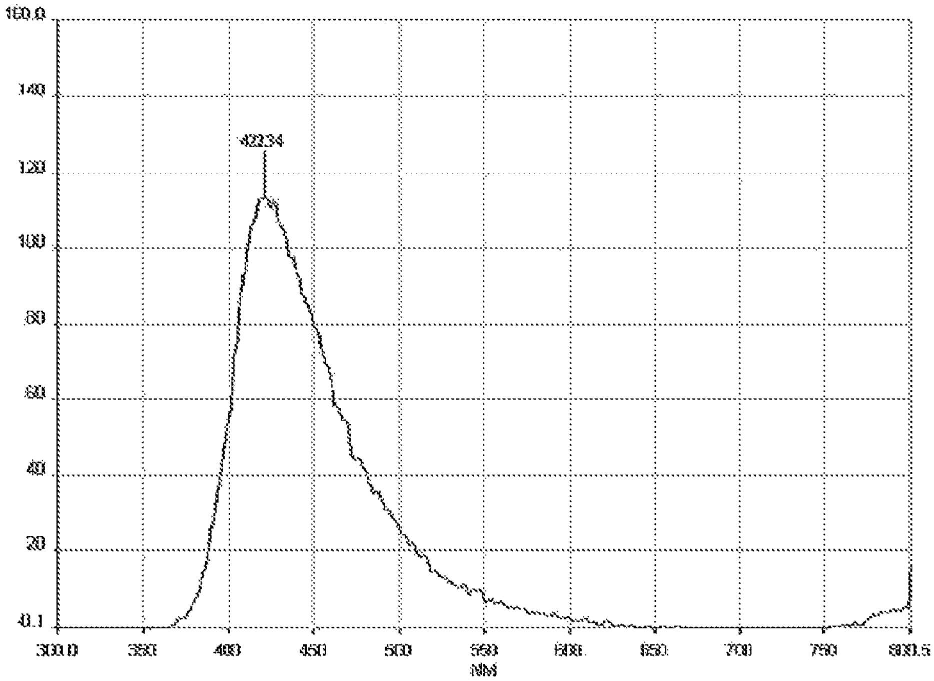

[Figure 6]
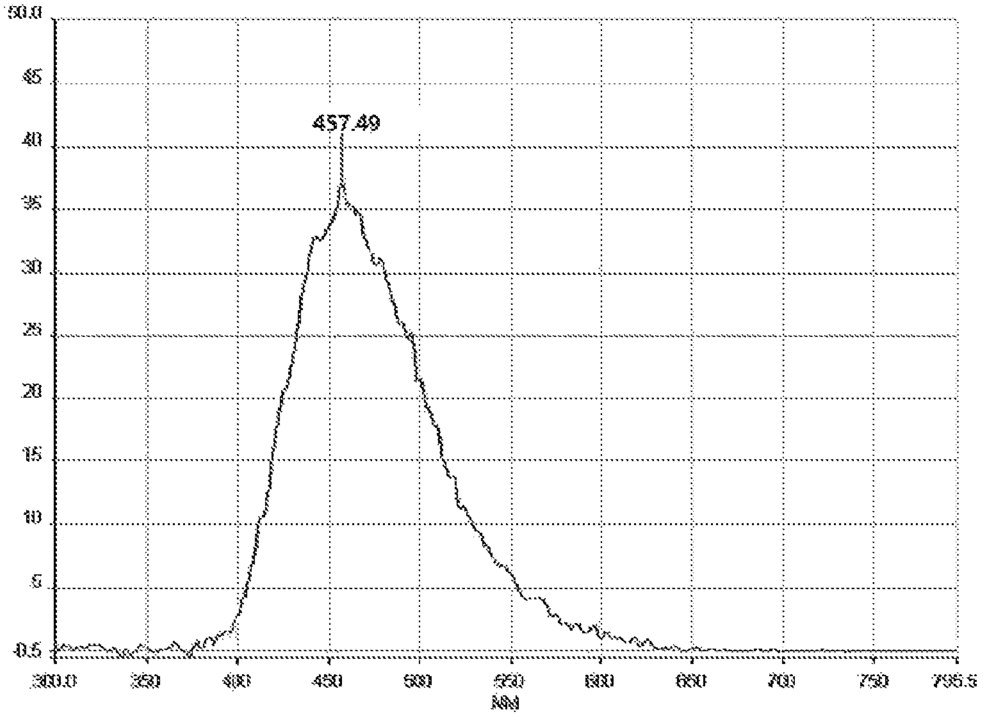

[Figure 7]
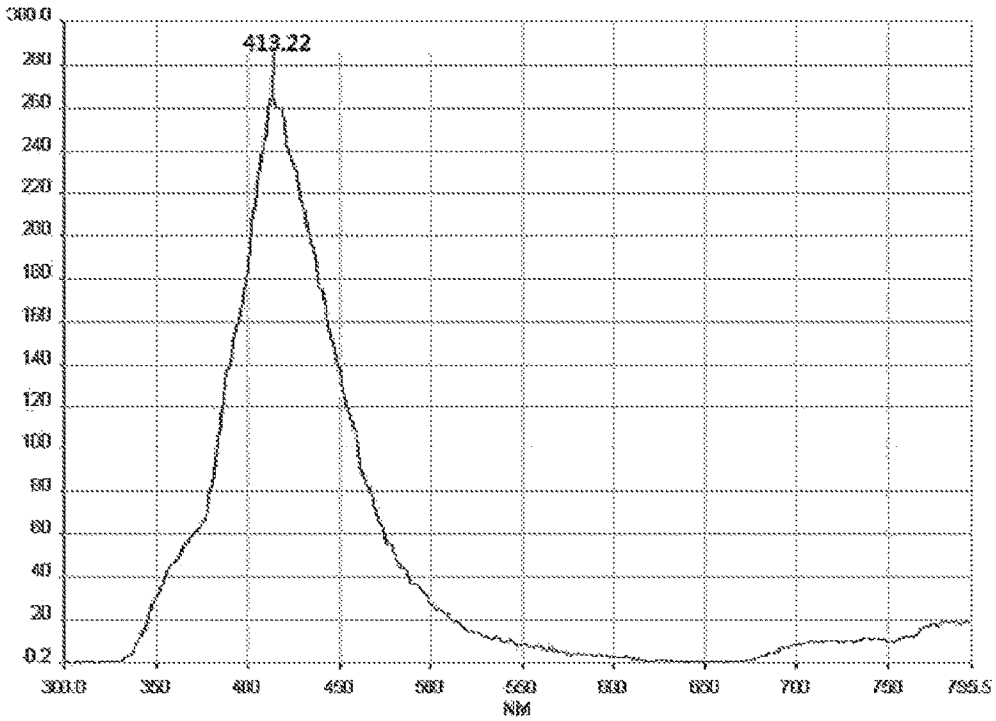

[Figure 8]
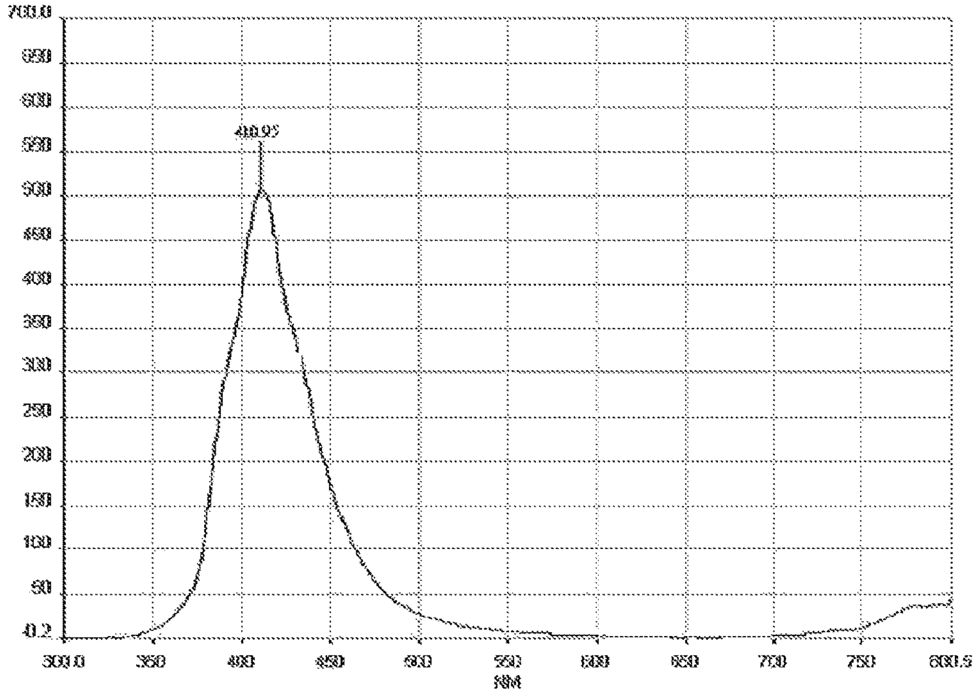

[Figure 9]
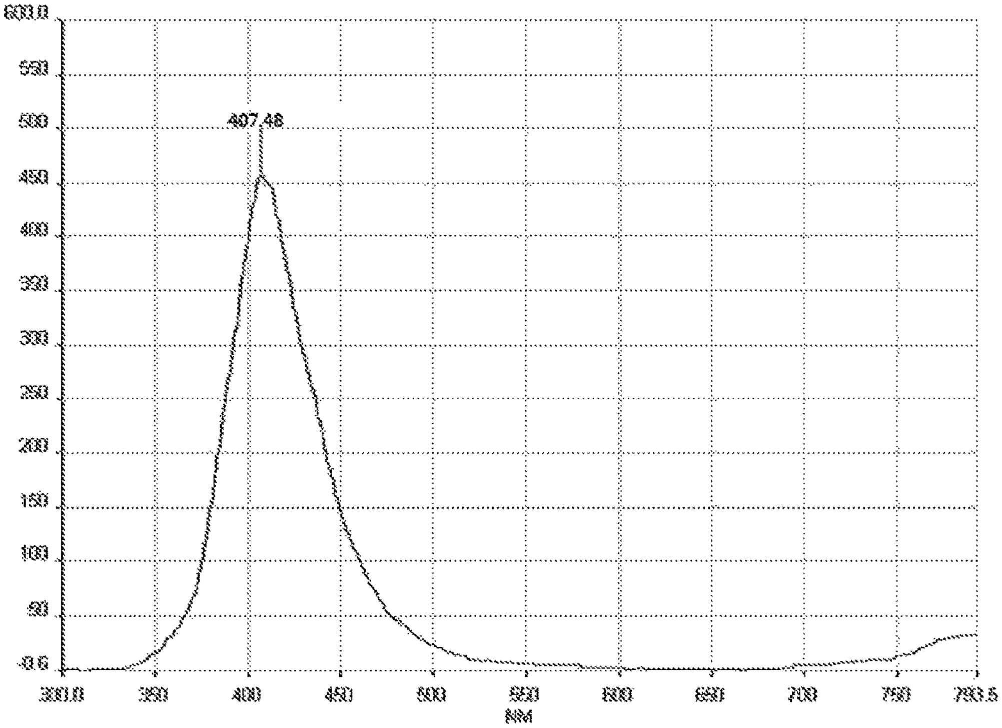

[Figure 10]
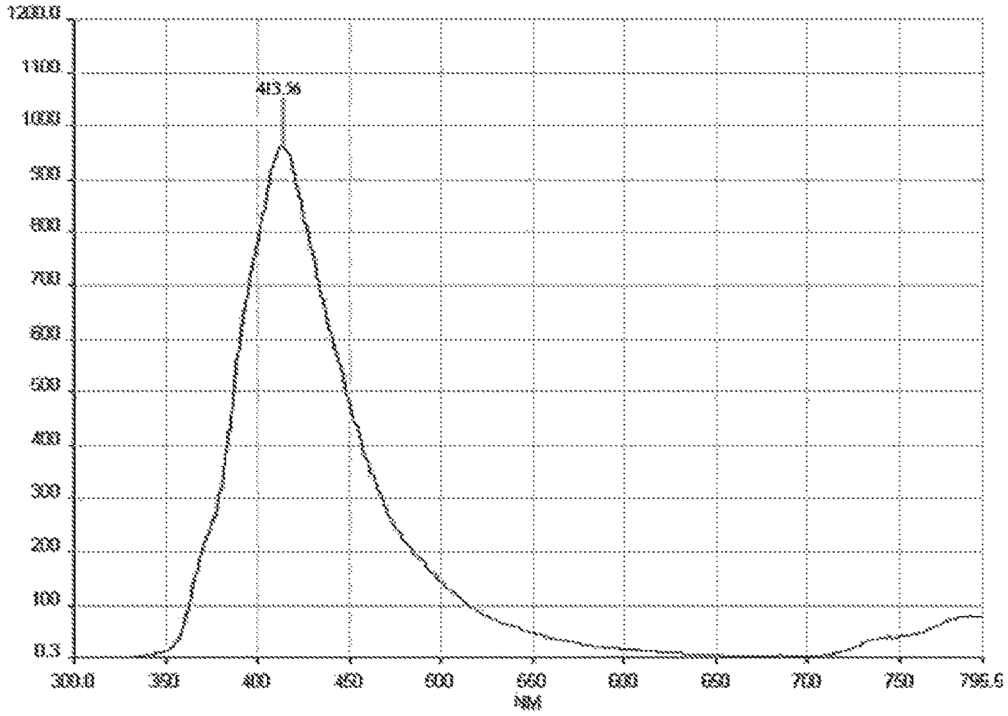

[Figure 11]
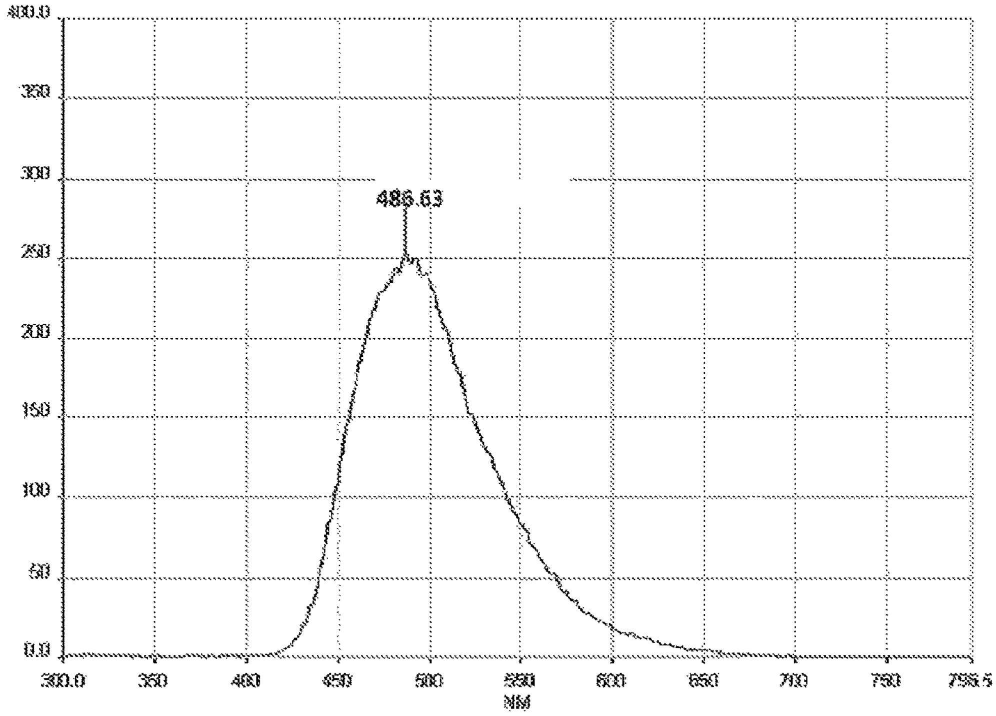

[Figure 12]
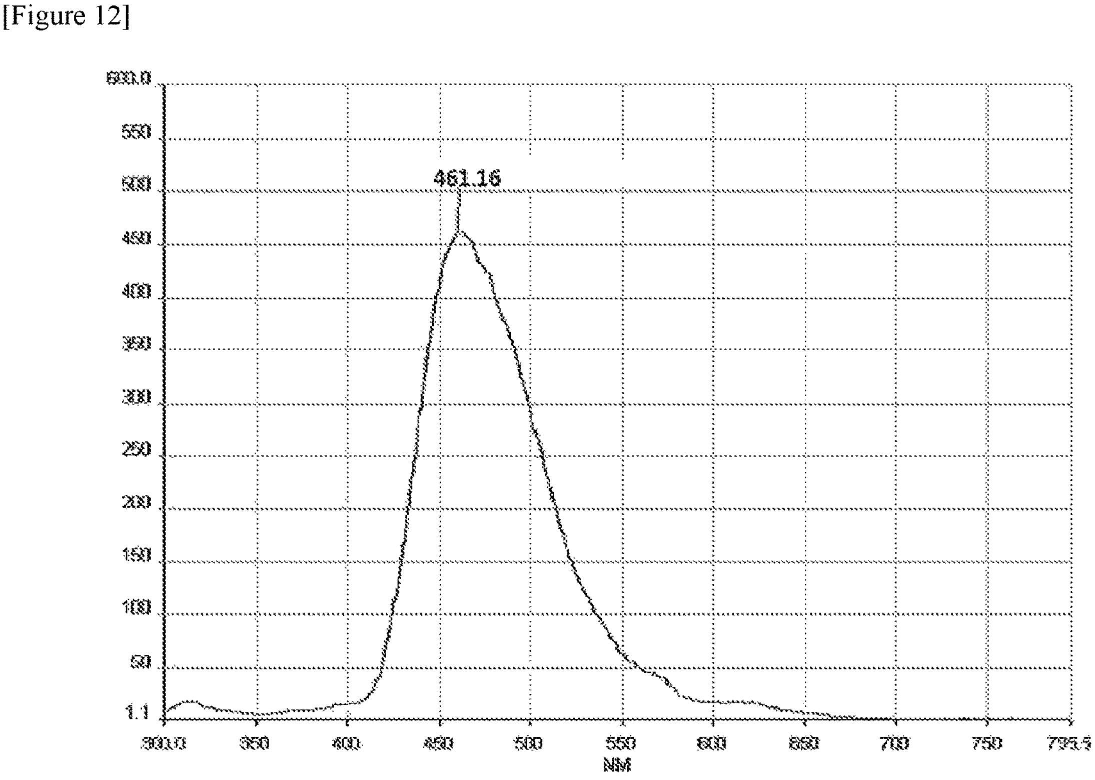

[Figure 13]
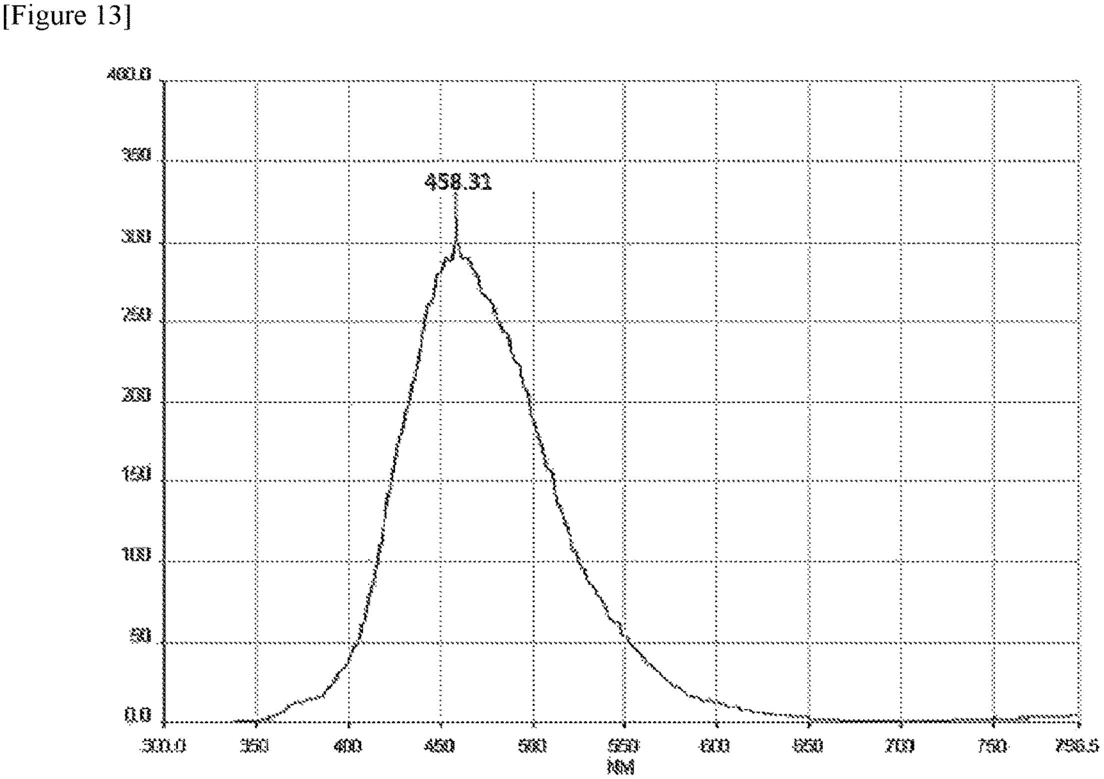

[Figure 14]
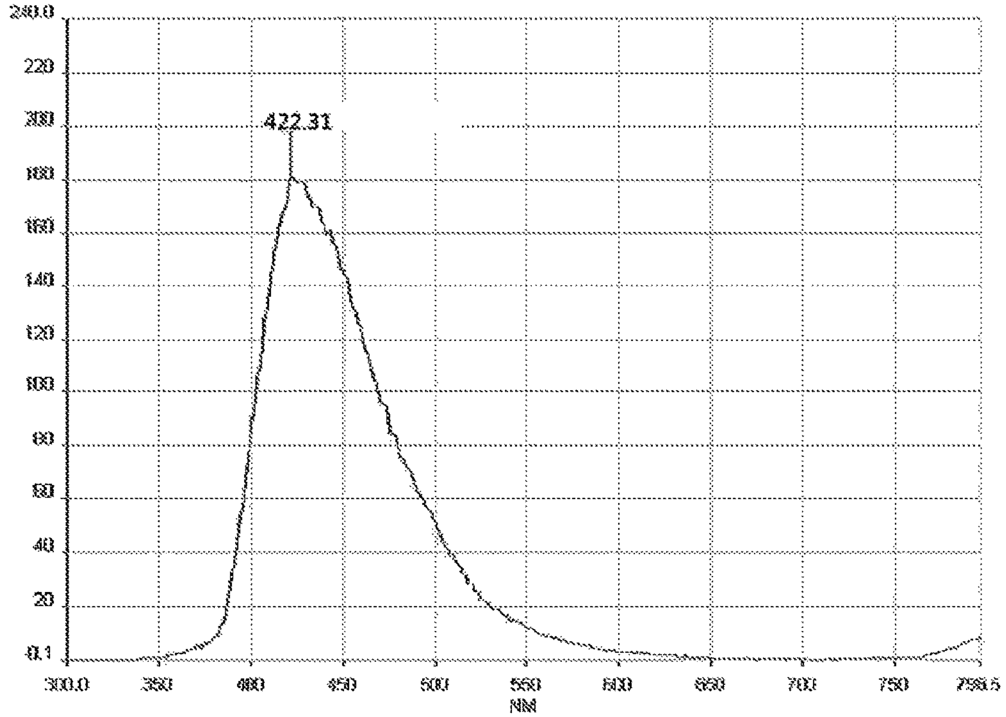

[Figure 15]
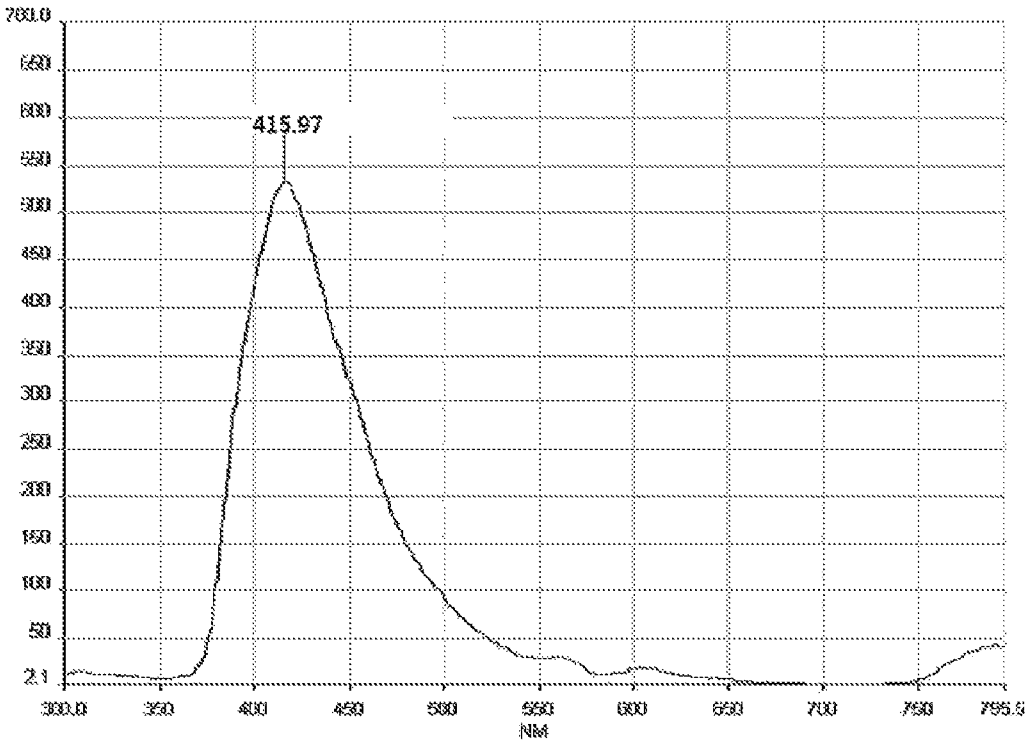

[Figure 16]
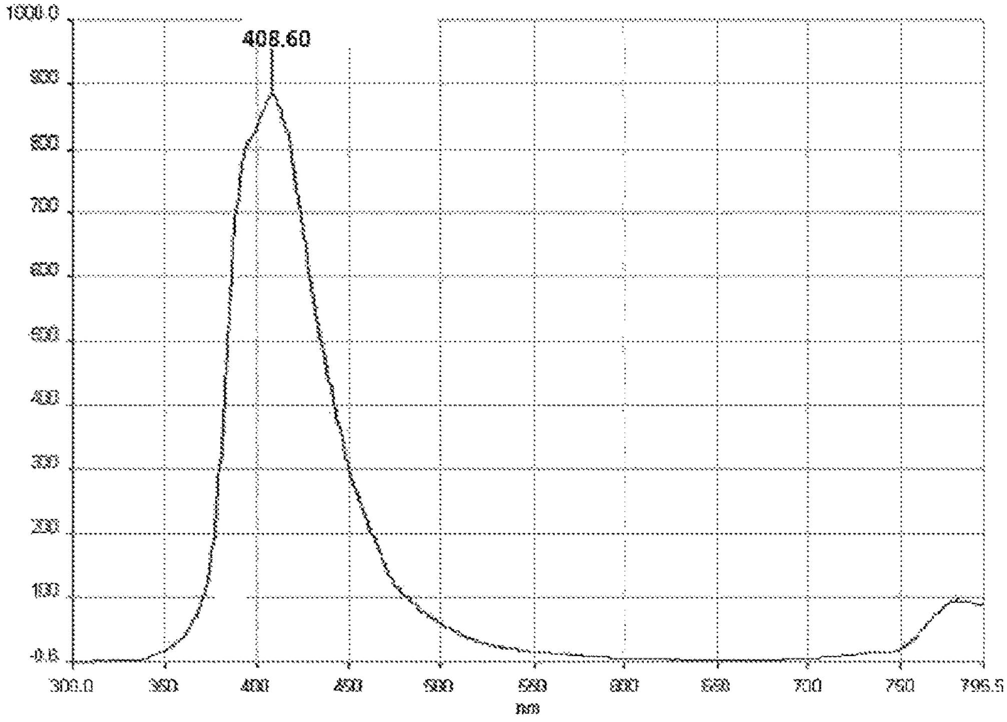

[Figure 17]
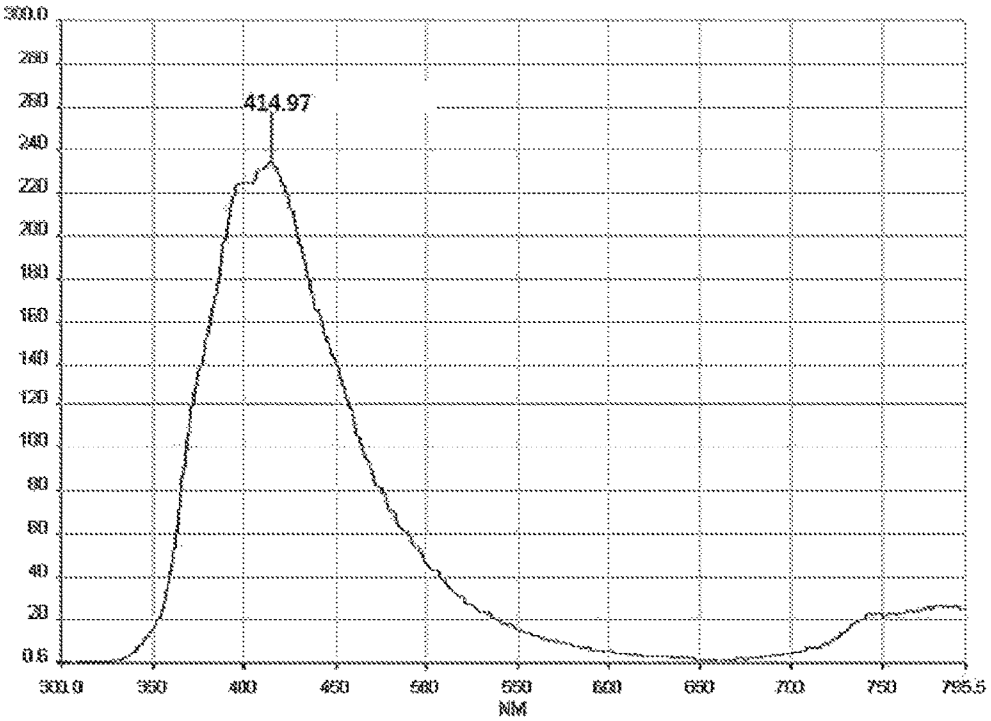

[Figure 18]
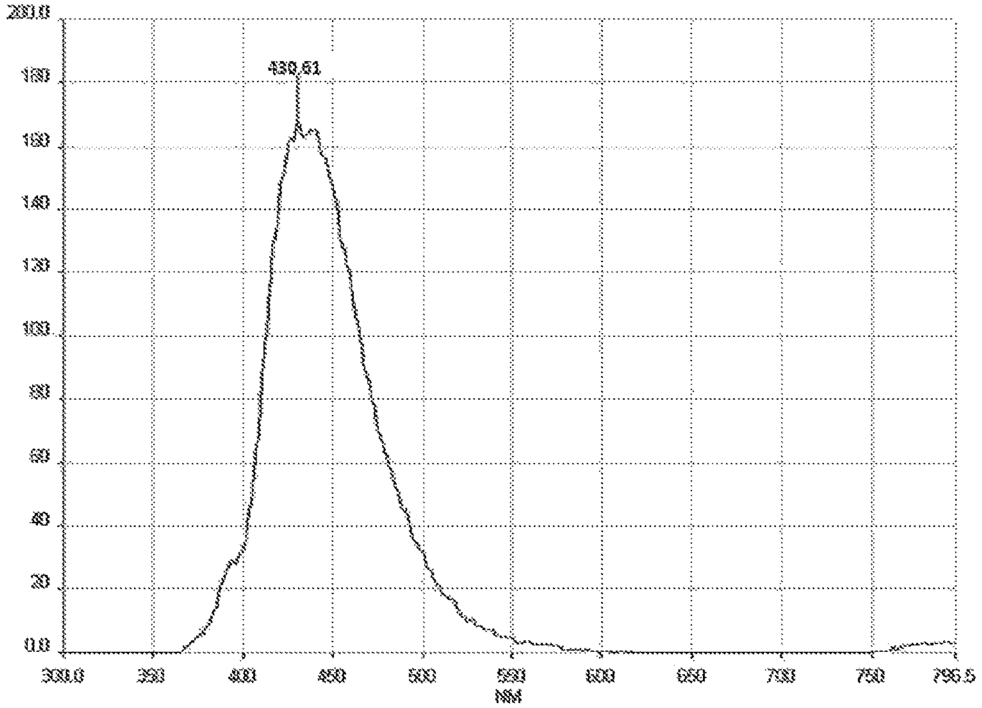
[Figure 19]
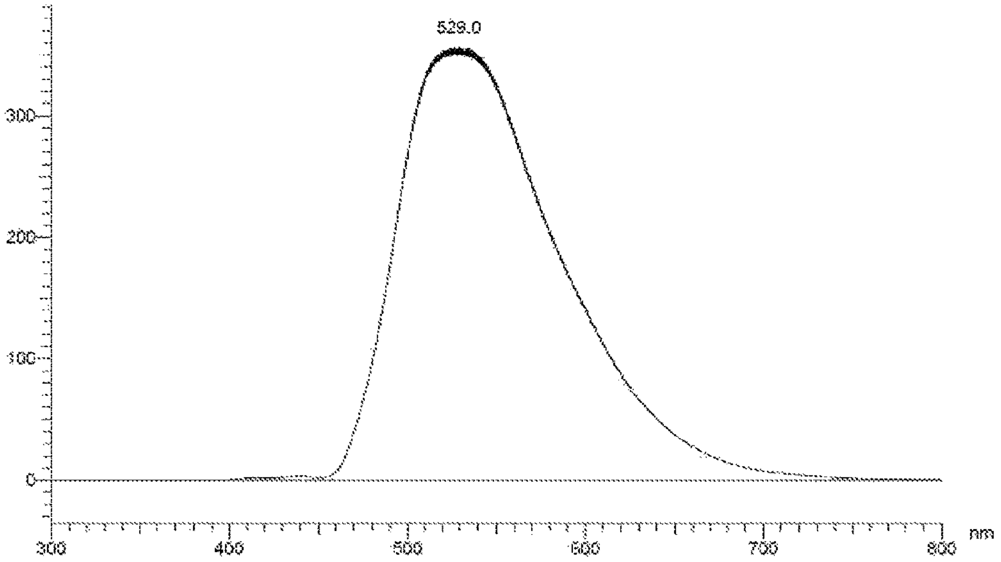

[Figure 20]
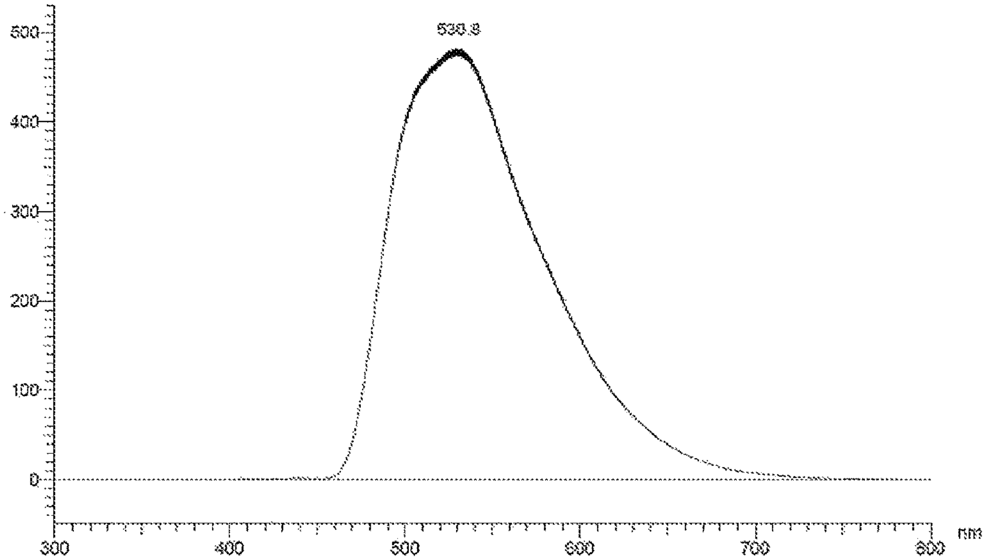
[Figure 21]
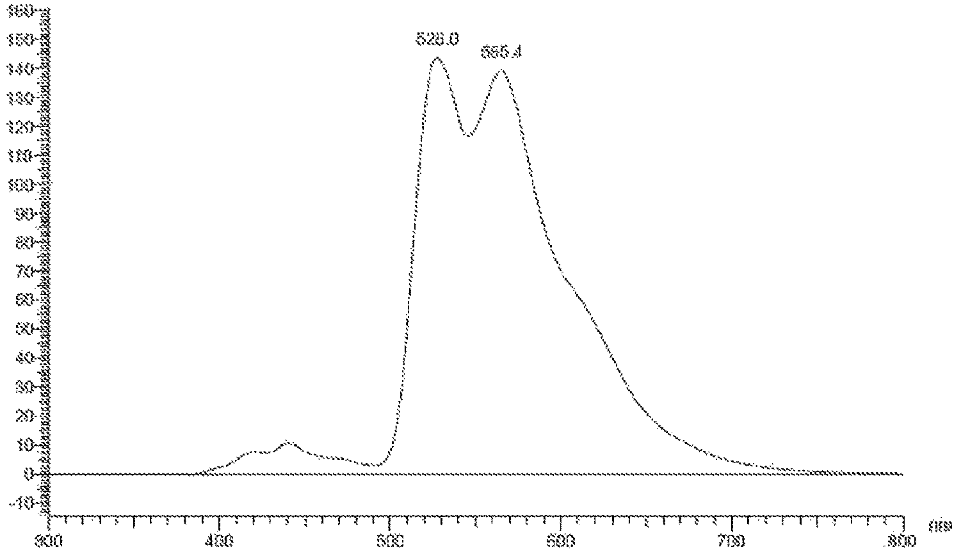

[Figure 22]
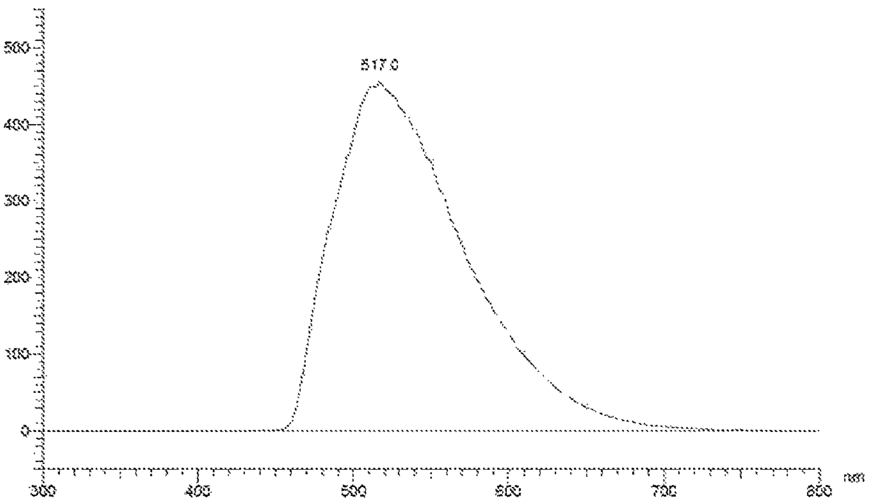
[Figure 23]
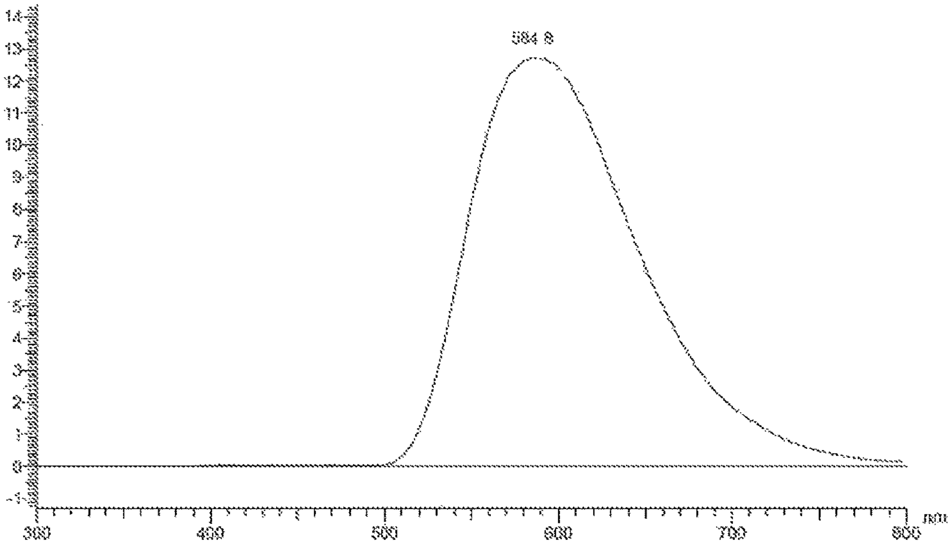

[Figure 24]
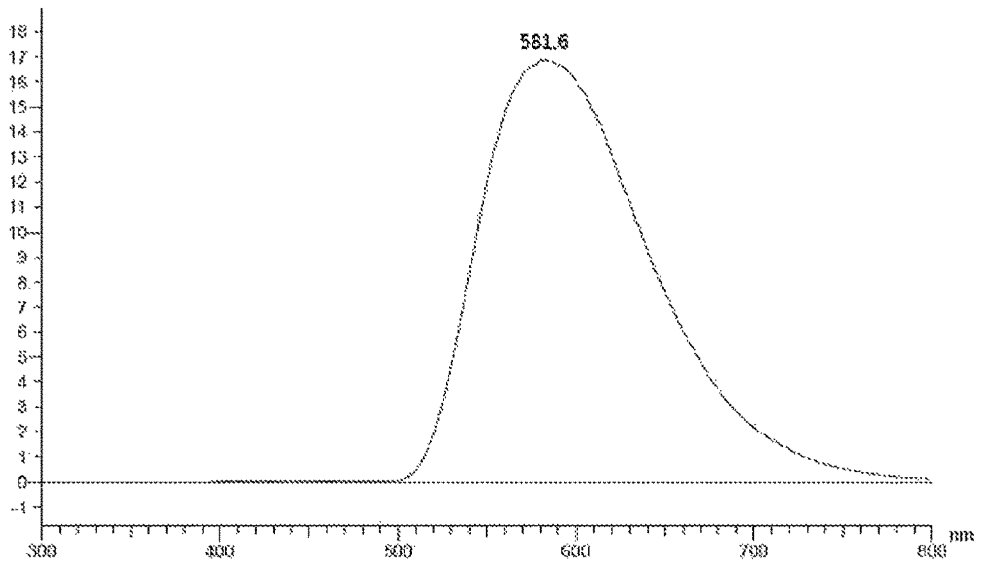
[Figure 25]
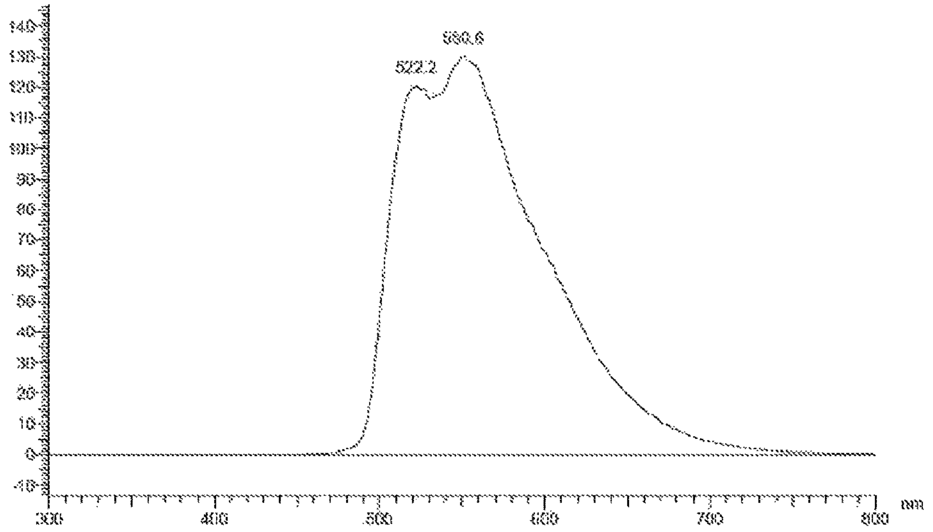

[Figure 26]
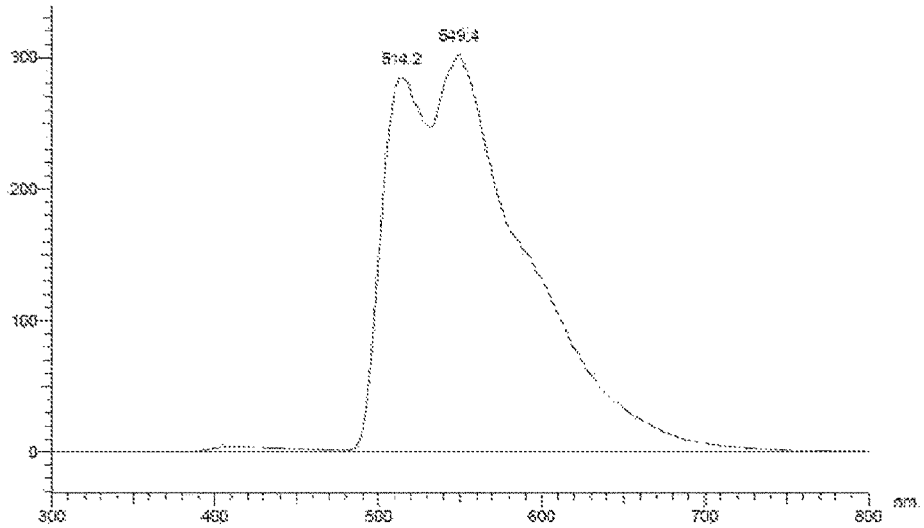
[Figure 27]
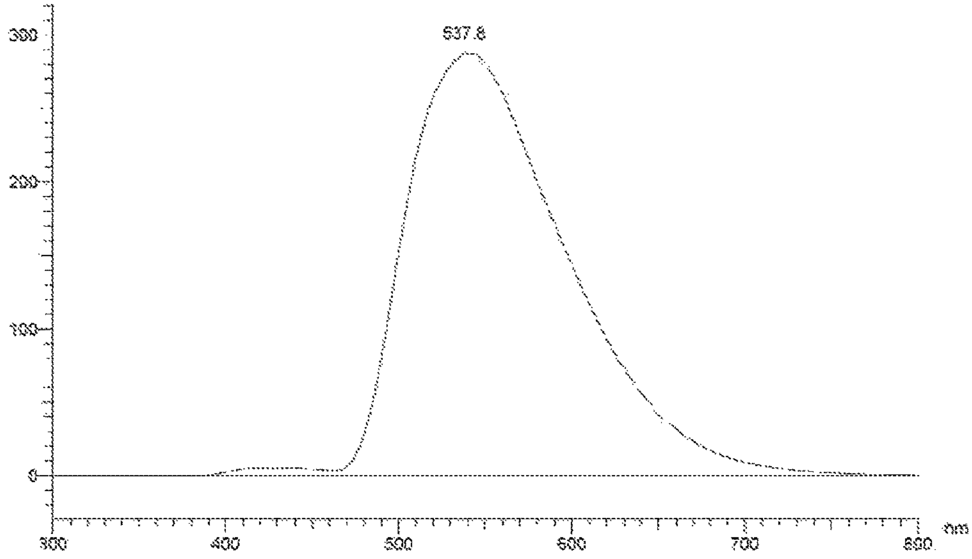

[Figure 28]
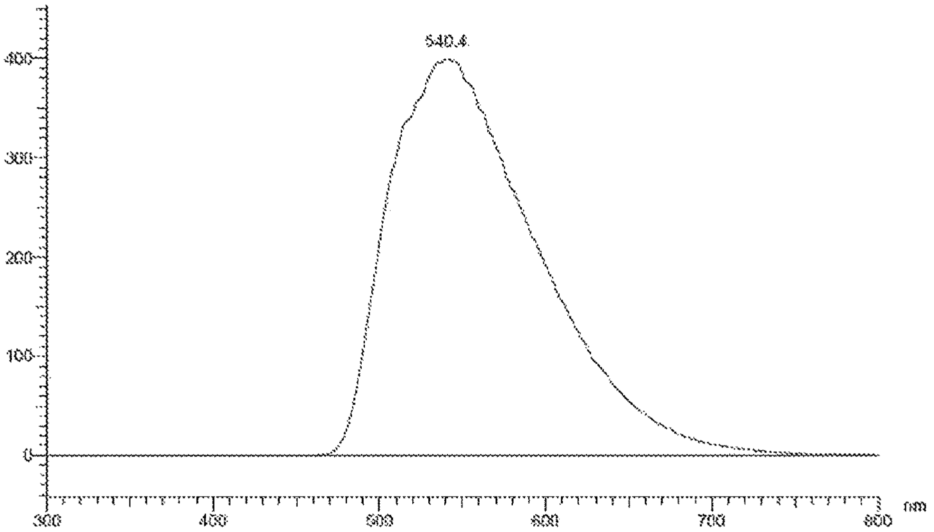
[Figure 29]
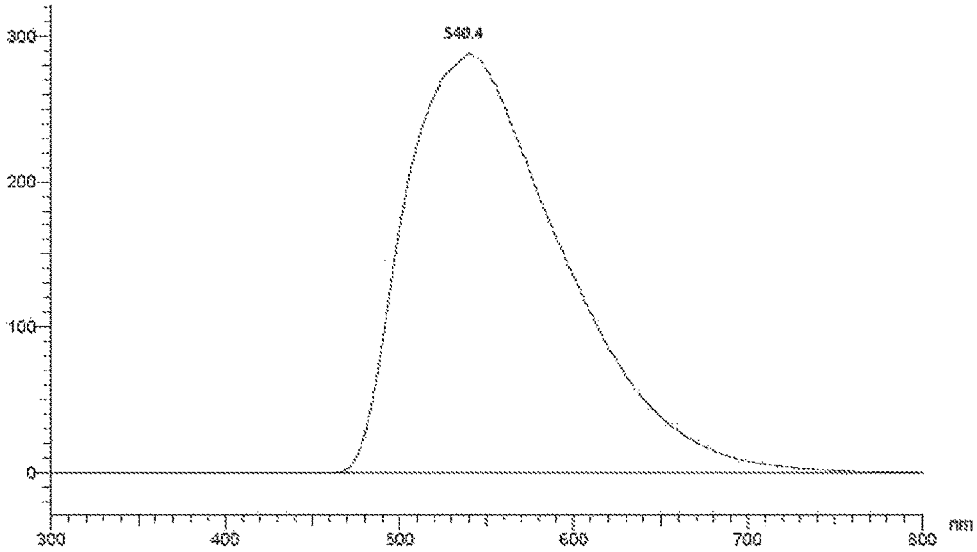

[Figure 30]
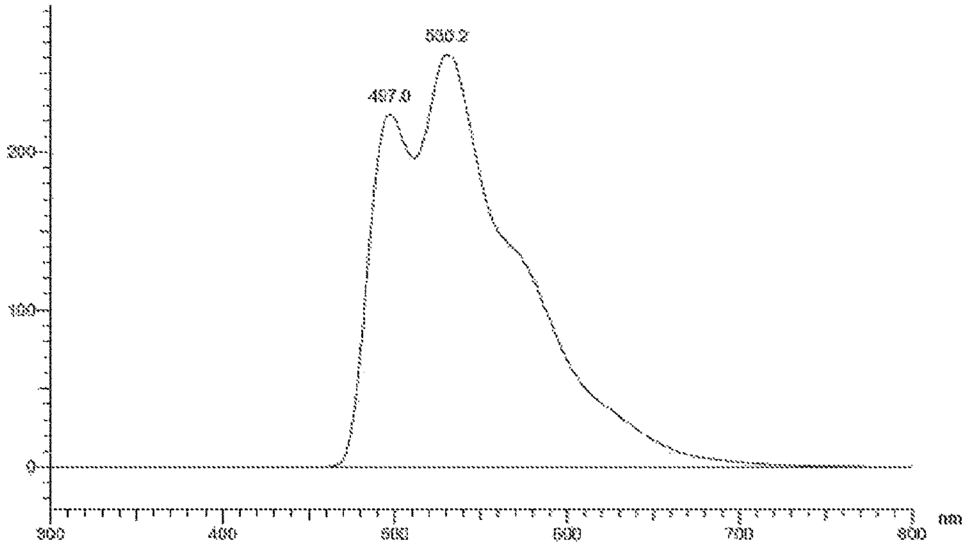

HETEROCYCLIC COMPOUND AND ORGANIC LIGHT EMITTING ELEMENT USING SAME

CROSS-REFERENCE TO RELATED APPLICATIONS

This application claims priority to and the benefit of Korean Patent Application No. 10-2014-0081206 and 10-2011-0127222 filed in the Korean Intellectual Property Office on Jun. 30, 2014 and Sep. 23, 2014, respectively, the entire contents of which are incorporated herein by reference.

TECHNICAL FIELD

The present specification relates to a novel hetero-cyclic compound, and an organic light emitting device using the same.

BACKGROUND ART

An electroluminescence device is a kind of self-light emitting type display device, and has merits in that a viewing angle is wide, a contrast is excellent, and a response rate is rapid.

An organic light emitting device has a structure where an organic thin film is disposed between two electrodes. If a voltage is applied to the organic light emitting device having the structure, electrons and holes injected from the two electrodes are bonded in the organic thin film to form a pair and then dissipate to emit light. The organic thin film may be constituted by a single layer or multilayers if necessary.

A material of the organic thin film may have a light emitting function if necessary. For example, a compound that may constitute a light emitting layer by itself alone or a compound that may act as a host or a dopant of a host-dopant-based light emitting layer may be used as the material of the organic thin film. In addition, a compound that may serve to inject or transport the holes, block the electrons or the holes, or transport or inject the electrons may be used as the material of the organic thin film.

There is a continuous demand for development of the material of the organic thin film in order to improve performance, a life-span, or efficiency of the organic light emitting device.

SUMMARY OF THE INVENTION

The present specification has been made in an effort to provide a novel hetero-cyclic compound, and an organic light emitting device using the same.

An exemplary embodiment of the present specification provides a compound of the following Chemical Formula 1.

[Chemical Formula 1]

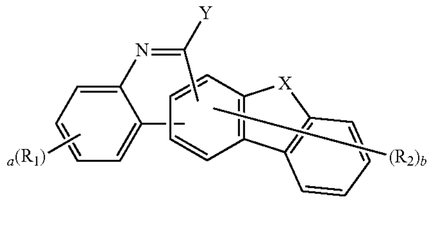

In Chemical Formula 1,

X is $NR_3$, $CR_4R_5$, S, O, or Se,

Y is selected from the group consisting of hydrogen; deuterium; halogen; —P(=O)$R_6R_7$; substituted or unsubstituted $C_6$ to $C_{60}$ monocyclic or polycyclic aryl; substituted or unsubstituted $C_2$ to $C_{60}$ monocyclic or polycyclic heteroaryl; substituted or unsubstituted $C_1$ to $C_{60}$ straight-chain or branch-chain alkyl; and amine substituted or unsubstituted by substituted or unsubstituted $C_1$ to $C_{20}$ alkyl, substituted or unsubstituted $C_6$ to $C_{60}$ monocyclic or polycyclic aryl, or substituted or unsubstituted $C_2$ to $C_{60}$ monocyclic or polycyclic heteroaryl, $R_1$ and $R_2$ are the same as or different from each other, and are each independently selected from the group consisting of hydrogen; deuterium; halogen; —P(=O)$R_8R_9$; substituted or unsubstituted $C_1$ to $C_{60}$ straight-chain or branch-chain alkyl; substituted or unsubstituted $C_2$ to $C_{60}$ straight-chain or branch-chain alkenyl; substituted or unsubstituted $C_2$ to $C_{60}$ straight-chain or branch-chain alkynyl; substituted or unsubstituted $C_1$ to $C_{60}$ straight-chain or branch-chain alkoxy; substituted or unsubstituted $C_3$ to $C_{60}$ monocyclic or polycyclic cycloalkyl; substituted or unsubstituted $C_2$ to $C_{60}$ monocyclic or polycyclic heterocycloalkyl; substituted or unsubstituted $C_6$ to $C_{60}$ monocyclic or polycyclic aryl; substituted or unsubstituted $C_2$ to $C_{60}$ monocyclic or polycyclic heteroaryl; and amine substituted or unsubstituted by substituted or unsubstituted $C_1$ to $C_{20}$ alkyl, substituted or unsubstituted $C_6$ to $C_{60}$ monocyclic or polycyclic aryl, or substituted or unsubstituted $C_2$ to $C_{60}$ monocyclic or polycyclic heteroaryl, a is an integer of 0 to 4, in which when a is 2 or more, $R_1$s are the same as or different from each other, b is an integer of 0 to 6, in which when b is 2 or more, $R_2$s are the same as or different from each other, $R_3$ is selected from the group consisting of hydrogen; deuterium; halogen; —P(=O)$R_6R_7$; substituted or unsubstituted $C_6$ to $C_{60}$ monocyclic or polycyclic aryl; substituted or unsubstituted $C_2$ to $C_{60}$ monocyclic or polycyclic heteroaryl; and amine substituted or unsubstituted by substituted or unsubstituted $C_1$ to $C_{20}$ alkyl, substituted or unsubstituted $C_6$ to $C_{60}$ monocyclic or polycyclic aryl, or substituted or unsubstituted $C_2$ to $C_{60}$ monocyclic or polycyclic heteroaryl, and $R_4$ to $R_9$ are the same as or different from each other, and are each independently hydrogen; substituted or unsubstituted $C_1$ to $C_{60}$ straight-chain or branch-chain alkyl; substituted or unsubstituted $C_3$ to $C_{60}$ monocyclic or polycyclic cycloalkyl; substituted or unsubstituted $C_6$ to $C_{60}$ monocyclic or polycyclic aryl; or substituted or unsubstituted $C_2$ to $C_{60}$ monocyclic or polycyclic heteroaryl.

Another exemplary embodiment of the present specification provides an organic light emitting device including: an anode, a cathode, and one or more layers of organic material layers provided between the anode and the cathode, in which one or more layers of the organic material layers include the compound of Chemical Formula 1.

A compound described in the present specification may be used as a material of an organic material layer of an organic light emitting device. The compound may be used as a material of an electron transport layer, a hole blocking layer, a light emitting layer, or the like in the organic light emitting device. Particularly, the compound of Chemical Formula 1 may be used as the material of the electron transport layer, the hole blocking layer, or the light emitting layer of the organic light emitting device. Further, the compound of Chemical Formula 1 may be used as the material of the electron transport layer or the light emitting layer.

BRIEF DESCRIPTION OF THE DRAWINGS

FIGS. 1 to 3 illustrate examples of a lamination order of electrodes and organic material layers of an organic light emitting device according to exemplary embodiments of the present specification.

FIG. 4 illustrates a PL measurement graph of compound 1-1 at a wavelength of 274 nm.

FIG. 5 illustrates a PL measurement graph of compound 1-12 at a wavelength of 233 nm.

FIG. 6 illustrates a PL measurement graph of compound 1-36 at a wavelength of 276 nm.

FIG. 7 illustrates a PL measurement graph of compound 1-113 at a wavelength of 240 nm.

FIG. 8 illustrates a PL measurement graph of compound 1-119 at a wavelength of 270 nm.

FIG. 9 illustrates a PL measurement graph of compound 1-124 at a wavelength of 240 nm.

FIG. 10 illustrates a PL measurement graph of compound 1-318 at a wavelength of 309 nm.

FIG. 11 illustrates a PL measurement graph of compound 2-36 at a wavelength of 282 nm.

FIG. 12 illustrates a PL measurement graph of compound 2-38 at a wavelength of 284 nm.

FIG. 13 illustrates a PL measurement graph of compound 3-39 at a wavelength of 307 nm.

FIG. 14 illustrates a PL measurement graph of compound 3-46 at a wavelength of 310 nm.

FIG. 15 illustrates a PL measurement graph of compound 4-56 at a wavelength of 278 nm.

FIG. 16 illustrates a PL measurement graph of compound 4-58 at a wavelength of 290 nm.

FIG. 17 illustrates a PL measurement graph of compound 4-76 at a wavelength of 267 nm.

FIG. 18 illustrates a PL measurement graph of compound 4-169 at a wavelength of 264 nm.

FIG. 19 illustrates a LTPL measurement graph of compound 1-1 at a wavelength of 309 nm.

FIG. 20 illustrates a LTPL measurement graph of compound 1-12 at a wavelength of 338 nm.

FIG. 21 illustrates a LTPL measurement graph of compound 1-36 at a wavelength of 310 nm.

FIG. 22 illustrates a LTPL measurement graph of compound 1-318 at a wavelength of 309 nm.

FIG. 23 illustrates a LTPL measurement graph of compound 2-36 at a wavelength of 409 nm.

FIG. 24 illustrates a LTPL measurement graph of compound 2-38 at a wavelength of 408 nm.

FIG. 25 illustrates a LTPL measurement graph of compound 3-39 at a wavelength of 307 nm.

FIG. 26 illustrates a LTPL measurement graph of compound 3-46 at a wavelength of 268 nm.

FIG. 27 illustrates a LTPL measurement graph of compound 4-56 at a wavelength of 278 nm.

FIG. 28 illustrates a LTPL measurement graph of compound 4-58 at a wavelength of 329 nm.

FIG. 29 illustrates a LTPL measurement graph of compound 4-76 at a wavelength of 365 nm.

FIG. 30 illustrates a LTPL measurement graph of compound 4-169 at a wavelength of 365 nm.

EXPLANATION OF REFERENCE NUMERALS AND SYMBOLS

100: Substrate
200: Positive electrode
300: Organic material layer

301: Hole injection layer
302: Hole transport layer
303: Light emitting layer
304: Hole blocking layer
305: Electron transport layer
306: Electron injection layer
400: Negative electrode

DETAILED DESCRIPTION

Hereinafter, the present invention will be described in detail.

A compound described in the present specification may be represented by Chemical Formula 1. Specifically, the compound of Chemical Formula 1 may be used as a material of an organic material layer of an organic light emitting device due to a structural characteristic of a core structure and a substituent group as described above.

In the present specification, the term "substituted or unsubstituted" means that there is substitution or no substitution is performed by one or more substituent groups selected from the group consisting of deuterium; halogen; $C_1$ to $C_{60}$ straight-chain or branch-chain alkyl; $C_2$ to $C_{60}$ straight-chain or branch-chain alkenyl; $C_2$ to $C_{60}$ straight-chain or branch-chain alkynyl; $C_1$ to $C_{60}$ straight-chain or branch-chain alkoxy; $C_3$ to $C_{60}$ monocyclic or polycyclic cycloalkyl; $C_2$ to $C_{60}$ monocyclic or polycyclic heterocycloalkyl; $C_6$ to $C_{60}$ monocyclic or polycyclic aryl; $C_2$ to $C_{60}$ monocyclic or polycyclic heteroaryl; —SiRR'R"; —P(═O)RR'; $C_1$ to $C_{20}$ alkylamine; $C_6$ to $C_{60}$ monocyclic or polycyclic arylamine; and $C_2$ to $C_{60}$ monocyclic or polycyclic heteroarylamine, by a substituent group where two or more of the aforementioned substituent groups are bonded, or by a substituent group where two or more substituent groups selected from the exemplified substituent groups are connected. For example, the "substituent group where two or more substituent groups are connected" may be a biphenyl group. That is, the biphenyl group may be an aryl group, or may be interpreted as a substituent group where two phenyl groups are connected. The additional substituent groups may be further substituted.

R, R', and R" are the same as or different from each other, and are each independently hydrogen; substituted or unsubstituted $C_1$ to $C_{60}$ straight-chain or branch-chain alkyl; substituted or unsubstituted $C_3$ to $C_{60}$ monocyclic or polycyclic cycloalkyl; substituted or unsubstituted $C_6$ to $C_{60}$ monocyclic or polycyclic aryl; or substituted or unsubstituted $C_2$ to $C_{60}$ monocyclic or polycyclic heteroaryl.

According to an exemplary embodiment of the present invention, the term "substituted or unsubstituted" means that there is substitution or no substitution is performed by one or more substituent groups selected from deuterium, halogen, —SiRR'R", —P(═O)RR', $C_6$ to $C_{60}$ aryl, and $C_2$ to $C_{60}$ heteroaryl, or a substituent group where two or more substituent groups selected from the aforementioned substituent groups are connected.

According to another exemplary embodiment of the present specification, R, R', and R" are the same as or different from each other, and are each independently hydrogen; $C_1$ to $C_{60}$ straight-chain or branch-chain alkyl substituted or unsubstituted by one or more substituent groups selected from deuterium, halogen, $C_6$ to $C_{60}$ aryl, and $C_2$ to $C_{60}$ heteroaryl; $C_3$ to $C_{60}$ monocyclic or polycyclic cycloalkyl substituted or unsubstituted by one or more substituent groups selected from deuterium, halogen, $C_6$ to $C_{60}$ aryl, and $C_2$ to $C_{60}$ heteroaryl; $C_6$ to $C_{60}$ monocyclic or polycyclic aryl substituted or unsubstituted by one or more substituent groups selected from deuterium, halogen, $C_6$ to $C_{60}$ aryl, and $C_2$ to $C_{60}$ heteroaryl; or $C_2$ to $C_{60}$ monocyclic or polycyclic heteroaryl substituted or unsubstituted by one or more substituent groups selected from deuterium, halogen, $C_6$ to $C_{60}$ aryl, and $C_2$ to $C_{60}$ heteroaryl.

In the present specification, halogen may be fluorine, chlorine, bromine, or iodine.

In the present specification, alkyl includes a straight-chain or a branch-chain having 1 to 60 carbon atoms, and may be further substituted by another substituent group. The number of carbon atoms of alkyl may be 1 to 60, specifically 1 to 40, and more specifically 1 to 20.

In the present specification, alkenyl includes a straight-chain or a branch-chain having 2 to 60 carbon atoms, and may be further substituted by another substituent group. The number of carbon atoms of alkenyl may be 2 to 60, specifically 2 to 40, and more specifically 2 to 20.

In the present specification, alkynyl includes a straight-chain or a branch-chain having 2 to 60 carbon atoms, and may be further substituted by another substituent group. The number of carbon atoms of alkynyl may be 2 to 60, specifically 2 to 40, and more specifically 2 to 20.

In the present specification, cycloalkyl includes a monocycle or a polycycle having 3 to 60 carbon atoms, and may be further substituted by another substituent group. Herein, the polycycle means a group where cycloalkyl is directly connected to another cycle group or condensed. Herein, another cycle group may be cycloalkyl or another kind of cycle group, for example, heterocycloalkyl, aryl, heteroaryl, or the like. The number of carbon atoms of cycloalkyl may be 3 to 60, specifically 3 to 40, and more specifically 5 to 20.

In the present specification, heterocycloalkyl includes O, S, Se, N, or Si as heteroatoms, includes a monocycle or a polycycle having 2 to 60 carbon atoms, and may be further substituted by another substituent group. Herein, the polycycle means a group where heterocycloalkyl is directly connected to another cycle group or condensed. Herein, another cycle group may be heterocycloalkyl or another kind of cycle group, for example, cycloalkyl, aryl, heteroaryl, or the like. The number of carbon atoms of heterocycloalkyl may be 2 to 60, specifically 2 to 40, and more specifically 3 to 20.

In the present specification, aryl includes a monocycle or a polycycle having 6 to 60 carbon atoms, and may be further substituted by another substituent group. Herein, the polycycle means a group where aryl is directly connected to another cycle group or condensed. Herein, another cycle group may be aryl or another kind of cycle group, for example, cycloalkyl, heterocycloalkyl, heteroaryl, or the like. Aryl includes a Spiro group. The number of carbon atoms of aryl may be 6 to 60, specifically 6 to 40, and more specifically 6 to 25. Specific examples of aryl include phenyl, biphenyl, triphenyl, naphthyl, anthryl, chrysenyl, phenanthrenyl, perylenyl, fluoranthenyl, triphenylenyl, phenalenyl, pyrenyl, tetracenyl, pentacenyl, fluorenyl, indenyl, acenaphthylenyl, benzofluorenyl, spirobifluorenyl, 2,3-dihydro-1H-indenyl, or a condensation cycle thereof, but are not limited thereto.

In the present specification, the spiro group is a group including a spiro structure, and may have 15 to 60 carbon atoms. For example, the spiro group may include a structure where a 2,3-dihydro-1H-indene group or a cyclohexane group is spiro-bonded to a fluorene group. Specifically, the Spiro group includes groups of the following Structural Formulas.

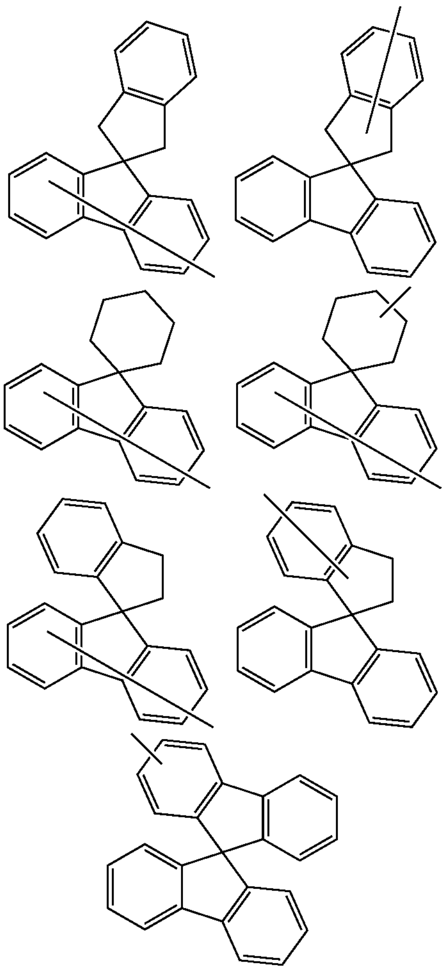

In the present specification, heteroaryl includes S, O, Se, N, or Si as heteroatoms, includes a monocycle or a polycycle having 2 to 60 carbon atoms, and may be further substituted by another substituent group. Herein, the polycycle means a group where heteroaryl is directly connected to another cycle group or condensed. Herein, another cycle group may be heteroaryl or another kind of cycle group, for example, cycloalkyl, heterocycloalkyl, aryl, or the like. The number of carbon atoms of heteroaryl may be 2 to 60, specifically 2 to 40, and more specifically 3 to 25. Specific examples of heteroaryl include pyridyl, pyrrolyl, pyrimidyl, pyridazinyl, furanyl, a thiophene group, imidazolyl, pyrazolyl, oxazolyl, isooxazolyl, thiazolyl, isothiazolyl, triazolyl, furazanyl, oxadiazolyl, thiadiazolyl, dithiazolyl, tetrazolyl, pyranyl, thiopyranyl, diazynyl, oxazinyl, thiazynyl, dioxinyl, triazinyl, tetrazinyl, quinolyl, isoquinolyl, quinazolinyl, isoquinazolinyl, quinoxalinyl, naphthyridyl, acridyl, phenanthridynyl, imidazopyridyl, diazanaphthyl, triazaindene, indolyl, indolizinyl, benzothiazolyl, benzoxazolyl, benzimidazolyl, a benzothiophene group, a benzofuran group, a dibenzothiophene group, a dibenzofuran group, carbazolyl, benzocarbazolyl, dibenzocarbazolyl, phenazinyl, dibenzosilol, spirobi(dibenzosilol), dihydrophenazinyl, phenoxazinyl, phenanthridyl, imidazopyridyl, thienyl, indolo[2,3-a]carbazolyl, indolo[2,3-b]carbazolyl, 10, 11-dihydro-dibenzo[b,f]azepine group, 9,10-dihydroacridyl, phenanthrazinyl, phenothiazynyl, phthalazinyl, naphthylidyl, phenanthrolinyl, benzo[c][1,2,5]thiadiazolyl, 5,10-dihydrodibenzo[b,e][1,4]

azasilynyl, pyrazolo[1,5-c]quinazolinyl, pyrido[1,2-b]indazollyl, pyrido[1,2-a]imidazo[1,2-e]indolyl, 5,11-dihydroindeno[1,2-b]carbazolyl, dibenzo[c, h]acridyl, or a condensation cycle thereof, but are not limited thereto.

In the present specification, amine may be selected from the group consisting of —$NH_2$; dialkylamine; diarylamine; diheteroarylamine; alkylarylamine; alkylheteroarylamine; and arylheteroarylamine, and the number of carbon atoms thereof is not particularly limited, but is preferably 1 to 30. Specific examples of amine include methylamine, dimethylamine, ethylamine, diethylamine, phenylamine, naphthylamine, biphenylamine, dibiphenylamine, anthracenylamine, 9-methyl-anthracenylamine, diphenylamine, phenylnaphthylamine, ditolylamine, phenyltolylamine, triphenylamine, and the like, but are not limited thereto.

According to the exemplary embodiment of the present specification,

X of Chemical Formula 1 is $NR_3$, at least one of Y and $R_3$ is $-(L)_m(Z)_n$, X of Chemical Formula 1 is $CR_4R_5$, S, O, or Se, Y is $-(L)_m-(Z)_n$, L is selected from the group consisting of a direct bond; —P(═O)$R_{10}$—; substituted or unsubstituted $C_6$ to $C_{60}$ monocyclic or polycyclic arylene; substituted or unsubstituted $C_2$ to $C_{60}$ monocyclic or polycyclic heteroarylene; and amine substituted or unsubstituted by substituted or unsubstituted $C_1$ to $C_{20}$ alkyl, substituted or unsubstituted $C_6$ to $C_{60}$ monocyclic or polycyclic aryl, or substituted or unsubstituted $C_2$ to $C_{60}$ monocyclic or polycyclic heteroaryl, m is an integer of 1 to 6, n is an integer of 1 to 5, Z is selected from the group consisting of hydrogen; deuterium; halogen; —P(═O)$R_{11}R_{12}$; substituted or unsubstituted $C_1$ to $C_{60}$ straight-chain or branch-chain alkyl; substituted or unsubstituted $C_6$ to $C_{60}$ monocyclic or polycyclic aryl; substituted or unsubstituted $C_2$ to $C_{60}$ monocyclic or polycyclic heteroaryl; and amine substituted or unsubstituted by substituted or unsubstituted $C_1$ to $C_{20}$ alkyl, substituted or unsubstituted $C_6$ to $C_{60}$ monocyclic or polycyclic aryl, or substituted or unsubstituted $C_2$ to $C_{60}$ monocyclic or polycyclic heteroaryl, and $R_4$, $R_5$, and $R_{10}$ to $R_{12}$ are each independently hydrogen; substituted or unsubstituted $C_1$ to $C_{60}$ straight-chain or branch-chain alkyl; substituted or unsubstituted $C_3$ to $C_{60}$ monocyclic or polycyclic cycloalkyl; substituted or unsubstituted $C_6$ to $C_{60}$ monocyclic or polycyclic aryl; or substituted or unsubstituted $C_2$ to $C_{60}$ monocyclic or polycyclic heteroaryl.

According to the exemplary embodiment of the present specification,

X of Chemical Formula 1 is $NR_3$, at least one of Y and $R_3$ is $-(L)_m-(Z)_n$, X of Chemical Formula 1 is $CR_4R_5$, S, O, or Se, Y is $-(L)_m-(Z)_n$, L is selected from the group consisting of a direct bond; —P(═O)$R_{10}$—; $C_6$ to $C_{60}$ monocyclic or polycyclic arylene substituted or unsubstituted by one or more substituent groups selected from deuterium, halogen, —SiRR'R", —P(═O)RR', $C_6$ to $C_{60}$ monocyclic or polycyclic aryl, and $C_2$ to $C_{60}$ monocyclic or polycyclic heteroaryl; $C_2$ to $C_{60}$ monocyclic or polycyclic heteroarylene substituted or unsubstituted by one or more substituent groups selected from deuterium, halogen, —SiRR'R", —P(═O)RR', $C_6$ to $C_{60}$ monocyclic or polycyclic aryl, and $C_2$ to $C_{60}$ monocyclic or polycyclic heteroaryl; and amine substituted or unsubstituted by $C_1$ to $C_{20}$ alkyl, $C_6$ to $C_{60}$ monocyclic or polycyclic aryl, or $C_2$ to $C_{60}$ monocyclic or polycyclic heteroaryl, m is an integer of 1 to 6, n is an integer of 1 to 5, Z is selected from the group consisting of hydrogen; deuterium; halogen; —P(═O)$R_{11}R_{12}$; $C_1$ to $C_{60}$ straight-chain or branch-chain alkyl substituted or unsubstituted by one or more substituent groups selected from deuterium, halogen, —SiRR'R", —P(═O)RR', $C_6$ to $C_{60}$ monocyclic or polycyclic aryl, and $C_2$ to $C_{60}$ monocyclic or polycyclic heteroaryl; $C_6$ to $C_{60}$ monocyclic or polycyclic aryl substituted or unsubstituted by one or more substituent groups selected from deuterium, halogen, —SiRR'R", —P(═O)RR', $C_6$ to $C_{60}$ monocyclic or polycyclic aryl, and $C_2$ to $C_{60}$ monocyclic or polycyclic heteroaryl; $C_2$ to $C_{60}$ monocyclic or polycyclic heteroaryl substituted or unsubstituted by one or more substituent groups selected from deuterium, halogen, —SiRR'R", —P(═O)RR', $C_6$ to $C_{60}$ monocyclic or polycyclic aryl, and $C_2$ to $C_{60}$ monocyclic or polycyclic heteroaryl; and amine substituted or unsubstituted by $C_1$ to $C_{20}$ alkyl, $C_6$ to $C_{60}$ monocyclic or polycyclic aryl, or $C_2$ to $C_{60}$ monocyclic or polycyclic heteroaryl, and R, R", $R_4$, $R_5$, and $R_{10}$ to $R_{12}$ are the same as or different from each other, and are each independently hydrogen; $C_1$ to $C_{60}$ straight-chain or branch-chain alkyl substituted or unsubstituted by one or more substituent groups selected from deuterium, halogen, $C_6$ to $C_{60}$ monocyclic or polycyclic aryl, and $C_2$ to $C_{60}$ monocyclic or polycyclic heteroaryl; substituted or unsubstituted $C_3$ to $C_{60}$ monocyclic or polycyclic cycloalkyl substituted or unsubstituted by one or more substituent groups selected from deuterium, halogen, $C_6$ to $C_{60}$ monocyclic or polycyclic aryl, and $C_2$ to $C_{60}$ monocyclic or polycyclic heteroaryl; $C_6$ to $C_{60}$ monocyclic or polycyclic aryl substituted or unsubstituted by one or more substituent groups selected from deuterium, halogen, $C_6$ to $C_{60}$ monocyclic or polycyclic aryl, and $C_2$ to $C_{60}$ monocyclic or polycyclic heteroaryl; or $C_2$ to $C_{60}$ monocyclic or polycyclic heteroaryl substituted or unsubstituted by one or more substituent groups selected from deuterium, halogen, $C_6$ to $C_{60}$ monocyclic or polycyclic aryl, and $C_2$ to $C_{60}$ monocyclic or polycyclic heteroaryl.

According to another exemplary embodiment of the present specification,

L is selected from the group consisting of a direct bond; $C_6$ to $C_{60}$ monocyclic or polycyclic arylene substituted or unsubstituted by one or more substituent groups selected from deuterium, halogen, —SiRR'R", —P(═O)RR', substituted or unsubstituted $C_6$ to $C_{60}$ aryl, and substituted or unsubstituted $C_2$ to $C_{60}$ heteroaryl; $C_2$ to $C_{60}$ monocyclic or polycyclic heteroarylene substituted or unsubstituted by one or more substituent groups selected from deuterium, halogen, —SiRR'R", —P(═O)RR', substituted or unsubstituted $C_6$ to $C_{60}$ aryl, and substituted or unsubstituted $C_2$ to $C_{60}$ heteroaryl; —P(═O)$R_{10}$—; substituted or unsubstituted $C_1$ to $C_{20}$ alkylamine; substituted or unsubstituted $C_0$ to $C_{60}$ monocyclic or polycyclic arylamine; and substituted or unsubstituted $C_2$ to $C_{60}$ monocyclic or polycyclic heteroarylamine, and R, R', R", and $R_{10}$ are the same as those described in the above.

According to another exemplary embodiment of the present specification,

L is selected from the group consisting of a direct bond; $C_6$ to $C_{60}$ monocyclic or polycyclic arylene substituted or unsubstituted by one or more substituent groups selected from deuterium, halogen, —SiRR'R", —P(═O)RR', $C_6$ to $C_{60}$ aryl, and $C_2$ to $C_{60}$ heteroaryl; $C_2$ to $C_{60}$ monocyclic or polycyclic heteroarylene substituted or unsubstituted by one or more substituent groups selected from deuterium, halogen, —SiRR'R", —P(═O)RR', $C_6$ to $C_{60}$ aryl, and $C_2$ to $C_{60}$ heteroaryl; —P(═O)$R_{10}$—; substituted or unsubstituted $C_1$ to $C_{20}$ alkylamine; substituted or unsubstituted $C_6$ to $C_{60}$ monocyclic or polycyclic arylamine; and substituted or unsubstituted $C_2$ to $C_{60}$ monocyclic or polycyclic heteroarylamine, and R, R', R", and $R_{10}$ are the same as those described in the above.

According to another exemplary embodiment of the present specification,

L is selected from the group consisting of a direct bond; —P(═O)$R_{10}$—; substituted or unsubstituted phenylene; substituted or unsubstituted biphenylene; substituted or unsubstituted naphthylene; substituted or unsubstituted anthrylene; substituted or unsubstituted phenanthrenylene; substituted or unsubstituted triphenylenylene; substituted or unsubstituted 9,9-diphenyl-9H-fluorenylene; substituted or unsubstituted pyridylene; substituted or unsubstituted pyrimidylene; substituted or unsubstituted triazinylene; substituted or unsubstituted quinolylene; substituted or unsubstituted quinazolinylene; substituted or unsubstituted benzothiazolylene; substituted or unsubstituted benzoxazolylene; substituted or unsubstituted benzimidazolylene; a substituted or unsubstituted divalent dibenzothiophene group; substituted or unsubstituted dibenzofuranylene; substituted or unsubstituted carbazolylene; substituted or unsubstituted indolo[2, 3-a]carbazolylene; substituted or unsubstituted naphthylidinylene; substituted or unsubstituted oxadiazolylene; substituted or unsubstituted pyrazolo[1, 5-c]quinazolinylene; substituted or unsubstituted pyrido[1,2-a]indazolylene; substituted or unsubstituted dibenzo[c, h]acridylene; substituted or unsubstituted dialkylamine; substituted or unsubstituted diarylamine; substituted or unsubstituted diheteroarylamine; substituted or unsubstituted alkylarylamine; substituted or unsubstituted alkylheteroarylamine; and substituted or unsubstituted arylheteroarylamine, and in the case where L is substituted, the substituent group is selected from deuterium, halogen, —SiRR'R", —P(═O)RR', substituted or unsubstituted $C_6$ to $C_{60}$ aryl, and substituted or unsubstituted $C_2$ to $C_{60}$ heteroaryl, and R, R', R", and $R_{10}$ are the same as those described in the above.

According to another exemplary embodiment of the present specification,

L is selected from the group consisting of a direct bond; —P(═O)$R_{10}$—; phenylene; biphenylene; naphthylene; anthrylene; phenanthrenylene; triphenylenylene; 9,9-diphenyl-9H-fluorenylene; pyridylene; pyrimidylene; triazinylene; quinolylene; quinazolinylene; benzothiazolylene; benzoxazolylene; benzimidazolylene; divalent dibenzothiophene group; dibenzofuranylene; carbazolylene; indolo[2, 3-a]carbazolylene; naphthylidinylene; oxadiazolylene; pyrazolo[1, 5-c]quinazolinylene; pyrido[1,2-a]indazolylene; dibenzo[c, h]acridylene; dialkylamine; diarylamine; diheteroarylamine; alkylarylamine; alkylheteroarylamine; and arylheteroarylamine, and $R_{10}$ is the same as that described in the above.

According to another exemplary embodiment of the present specification,

L is selected from the group consisting of a direct bond; —P(═O)$R_{10}$—; phenylene; biphenylene; naphthylene; anthrylene; phenanthrenylene; triphenylenylene; 9,9-diphenyl-9H-fluorenylene; pyridylene; pyrimidylene; triazinylene; quinolylene; quinazolinylene; benzothiazolylene; benzooxazolylene; benzoimidazolylene; a divalent dibenzothiophene group; dibenzofuranylene; carbazolylene; indolo [2, 3-a]carbazolylene; naphthylidinylene; oxadiazolylene; pyrazolo[1, 5-c]quinazolinylene; pyrido[1,2-a]indazolylene; dibenzo[c, h]acridylene; diphenylamine; dibiphenylamine; and phenylnaphthylamine, and $R_{10}$ is the same as that described in the above.

According to another exemplary embodiment of the present specification,

Z is selected from the group consisting of hydrogen; deuterium; halogen; —P(═O)$R_{11}R_{12}$; $C_1$ to $C_{60}$ straight-chain or branch-chain alkyl substituted or unsubstituted by one or more substituent groups selected from deuterium, halogen, —SiRR'R", —P(═O)RR', substituted or unsubstituted $C_6$ to $C_{60}$ aryl, and substituted or unsubstituted $C_2$ to $C_{60}$ heteroaryl; $C_6$ to $C_{60}$ monocyclic or polycyclic aryl substituted or unsubstituted by one or more substituent groups selected from deuterium, halogen, —SiRR'R", —P(═O)RR', substituted or unsubstituted $C_6$ to $C_{60}$ aryl, and substituted or unsubstituted $C_2$ to $C_{60}$ heteroaryl; $C_2$ to $C_{60}$ monocyclic or polycyclic heteroaryl substituted or unsubstituted by one or more substituent groups selected from deuterium, halogen, —SiRR'R", —P(═O)RR', substituted or unsubstituted $C_6$ to $C_{60}$ aryl, and substituted or unsubstituted $C_2$ to $C_{60}$ heteroaryl; substituted or unsubstituted $C_1$ to $C_{20}$ alkylamine; substituted or unsubstituted $C_6$ to $C_{60}$ monocyclic or polycyclic arylamine; and substituted or unsubstituted $C_2$ to $C_{60}$ monocyclic or polycyclic heteroarylamine, and R, R', R", $R_{11}$, and $R_{12}$ are the same as those described in the above.

Z is selected from the group consisting of hydrogen; deuterium; halogen; —P(═O)$R_{11}R_{12}$; $C_1$ to $C_{60}$ straight-chain or branch-chain alkyl substituted or unsubstituted by one or more substituent groups selected from deuterium, halogen, —SiRR'R", —P(═O)RR', $C_6$ to $C_{60}$ aryl, and $C_2$ to $C_{60}$ heteroaryl; $C_6$ to $C_{60}$ monocyclic or polycyclic aryl substituted or unsubstituted by one or more substituent groups selected from deuterium, halogen, —SiRR'R", —P(═O)RR', $C_6$ to $C_{60}$ aryl, and $C_2$ to $C_{60}$ heteroaryl; $C_2$ to $C_{60}$ monocyclic or polycyclic heteroaryl substituted or unsubstituted by one or more substituent groups selected from deuterium, halogen, —SiRR'R", —P(═O)RR', $C_6$ to $C_{60}$ aryl, and $C_2$ to $C_{60}$ heteroaryl; substituted or unsubstituted $C_1$ to $C_{20}$ alkylamine; substituted or unsubstituted $C_6$ to $C_{60}$ monocyclic or polycyclic arylamine; and substituted or unsubstituted $C_2$ to $C_{60}$ monocyclic or polycyclic heteroarylamine, and R, R', R", $R_{11}$, and $R_{12}$ are the same as those described in the above.

According to another exemplary embodiment of the present specification,

Z is selected from the group consisting of hydrogen; deuterium; halogen; —P(═O)$R_{11}R_{12}$; substituted or unsubstituted ethyl; substituted or unsubstituted phenyl; substituted or unsubstituted biphenyl; substituted or unsubstituted naphthyl; substituted or unsubstituted anthryl; substituted or unsubstituted phenanthrenyl; substituted or unsubstituted triphenylenyl; substituted or unsubstituted 9,9-diphenyl-9H-fluorenyl; substituted or unsubstituted pyridyl; substituted or unsubstituted pyrimidyl; substituted or unsubstituted triazinyl; substituted or unsubstituted quinolyl; substituted or unsubstituted quinazolinyl; substituted or unsubstituted benzothiazolyl; substituted or unsubstituted benzoxazolyl; substituted or unsubstituted benzimidazolyl; substituted or unsubstituted dibenzothiophenyl; substituted or unsubstituted dibenzofuranyl; substituted or unsubstituted carbazolyl; substituted or unsubstituted indolo[2, 3-a]carbazolyl, substituted or unsubstituted naphthylidinyl; substituted or unsubstituted oxadiazolyl; substituted or unsubstituted pyrazolo[1, 5-c]quinazolinyl; substituted or unsubstituted pyrido [1,2-a]indazolyl; substituted or unsubstituted dibenzo[c, h]acridyl; substituted or unsubstituted benzo[b]naphtho[2, 3-d]thiophene group; substituted or unsubstituted benzo[h]naphtho[2,3-c]acridyl; substituted or unsubstituted benzo[f]quinolyl; substituted or unsubstituted dialkylamine; substituted or unsubstituted diarylamine; substituted or unsubstituted diheteroarylamine; substituted or unsubstituted alkylarylamine; substituted or unsubstituted alkylheteroarylamine; and substituted or unsubstituted arylheteroarylamine, and in the case where Z is substituted, the substituent group is selected from deuterium, halogen, —SiRR'R", —P(═O)RR', substituted or unsubstituted $C_6$ to $C_{60}$ aryl, and substituted or unsubstituted $C_2$ to $C_{60}$ heteroaryl, and R, R', R", $R_{11}$, and $R_{12}$ are the same as those described in the above.

According to another exemplary embodiment of the present specification,

Z is selected from the group consisting of hydrogen; deuterium; halogen; —P(═O)$R_{11}R_{12}$; ethyl; phenyl; biphenyl; naphthyl; anthryl; phenanthrenyl; triphenylenyl; 9,9-diphenyl-9H-fluorenyl; pyridyl; pyrimidyl; triazinyl; quinolyl; quinazolinyl; benzothiazolyl; benzoxazolyl; benzimidazolyl; dibenzothiophenyl; dibenzofuranyl; carbazolyl; indolo[2, 3-a]carbazolyl, naphthylidinyl; oxadiazolyl; pyrazolo[1, 5-c]quinazolinyl; pyrido[1,2-a]indazolyl; dibenzo[c, h]acridyl; benzo[b]naphtho[2,3-d]thiophene group; benzo[h]naphtho[2,3-c]acridyl; benzo[f]quinolyl; dialkylamine; diarylamine; diheteroarylamine; alkylarylamine; alkylheteroarylamine; and arylheteroarylamine, and $R_{11}$ and $R_{12}$ are the same as those described in the above.

According to another exemplary embodiment of the present specification,

Z is selected from the group consisting of hydrogen; deuterium; halogen; —P(═O)$R_{11}R_{12}$; ethyl; phenyl; biphenyl; naphthyl; anthryl; phenanthrenyl; triphenylenyl; 9,9-diphenyl-9H-fluorenyl; pyridyl; pyrimidyl; triazinyl; quinolyl; quinazolinyl; benzothiazolyl; benzooxazolyl; benzoimidazolyl; dibenzothiophenyl; dibenzofuranyl; carbazolyl; indolo[2, 3-a]carbazolyl, naphthylidinyl; oxadiazolyl; pyrazolo[1, 5-c]quinazolinyl; pyrido[1,2-a]indazolyl; dibenzo[c, h]acridyl; benzo[b]naphtho[2,3-d]thiophene group; benzo[h]naphtho[2,3-c]acridyl; benzo[f]quinolyl; diphenylamine; dibiphenylamine; and phenylnaphthylamine, and $R_{11}$ and $R_{12}$ are the same as those described in the above.

According to another exemplary embodiment of the present specification,

Z is substituted or unsubstituted $C_2$ to $C_{60}$ monocyclic or polycyclic heteroaryl, and heteroaryl includes at least one selected from N, O, and S as heteroatoms.

According to another exemplary embodiment of the present specification,

Z is

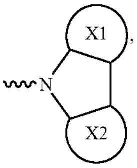, and X1 and X2 are a substituted or unsubstituted $C_6$ to $C_{60}$ monocyclic or polycyclic aromatic hydrocarbon cycle; or a substituted or unsubstituted $C_2$ to $C_{60}$ monocyclic or polycyclic aromatic hetero cycle.

According to another exemplary embodiment of the present specification,

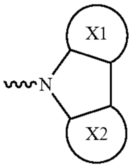

is represented by the following Structural Formulas.

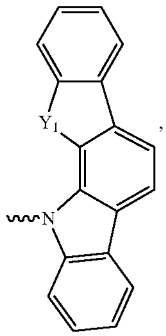,

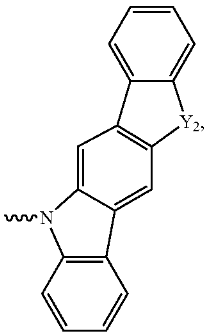

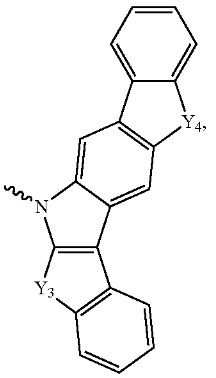

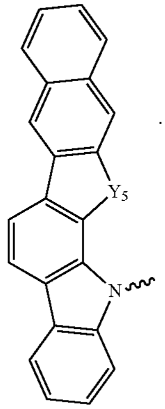.

In the Structural Formulas, $Y_1$ to $Y_5$ are the same as or different from each other, and are each independently S, NY', or CY'Y", and Y' and Y" are the same as or different from each other, and are each independently hydrogen; substituted or unsubstituted $C_1$ to $C_{60}$ straight-chain or branch-chain alkyl; or substituted or unsubstituted $C_6$ to $C_{60}$ monocyclic or polycyclic aryl.

According to a first exemplary embodiment of the present specification, in Chemical Formula 1 of the aforementioned exemplary embodiment, X is $NR_3$, at least one of Y and $R_3$ is $-(L)_m-(Z)_n$, L is substituted or unsubstituted phenylene; or substituted or unsubstituted $C_5$ heteroarylene, Z, m, and n are the same as those of the aforementioned exemplary embodiment, and Z is bonded to an atom bonded to a core of L at a para or meta position thereof.

According to another exemplary embodiment of the present specification,

X of the aforementioned first exemplary embodiment is $NR_3$, Y is $-(L)_m-(Z)_n$, $R_3$ is the same as that of the aforementioned exemplary embodiment, L, Z, m, and n are the same as those of the aforementioned first exemplary embodiment, and Z is bonded to an atom bonded to a core of L at a para position thereof.

According to another exemplary embodiment of the present specification,

X of the aforementioned first exemplary embodiment is $NR_3$, Y is $-(L)_m-(Z)_n$, $R_3$ is the same as that of the aforementioned exemplary embodiment, L, Z, m, and n are the same as those of the aforementioned first exemplary embodiment, and Z is bonded to an atom bonded to a core of L at a meta position thereof.

According to another exemplary embodiment of the present specification,

X of the aforementioned first exemplary embodiment is $NR_3$, $R_3$ is $-(L)_m-(Z)_n$, L, Z, m, and n are the same as those of the aforementioned first exemplary embodiment, and Z is bonded to an atom bonded to a core of L at a para position thereof.

According to another exemplary embodiment of the present specification,

X of the aforementioned first exemplary embodiment is $NR_3$, $R_3$ is $-(L)_m-(Z)_n$, L, Z, m, and n are the same as those of the aforementioned first exemplary embodiment, and Z is bonded to an atom bonded to a core of L at a meta position thereof.

According to a second exemplary embodiment of the present specification, in Chemical Formula 1 of the aforementioned exemplary embodiment, X is $CR_4R_5$, S, O, or Se, Y is $-(L)_m-(Z)_n$, L is the same as that of the aforementioned first exemplary embodiment, $R_4$, $R_5$, Z, m, and n are the same as those of the aforementioned exemplary embodiment, and Z is bonded to an atom bonded to a core of L at a para or meta position thereof.

According to another exemplary embodiment of the present specification,

X of the aforementioned second exemplary embodiment is $CR_4R_5$, S, O, or Se, Y is $-(L)_m-(Z)_n$, $R_4$, $R_5$, L, Z, m, and n are the same as those of the aforementioned second exemplary embodiment, and Z is bonded to an atom bonded to a core of L at a para position thereof.

According to another exemplary embodiment of the present specification,

X of the aforementioned second exemplary embodiment is $CR_4R_5$, S, O, or Se, Y is $-(L)_m-(Z)_n$, $R_4$, $R_5$, L, Z, m, and n are the same as those of the aforementioned second exemplary embodiment, and Z is bonded to an atom bonded to a core of L at a meta position thereof.

According to the first and second exemplary embodiments of the present specification, L is substituted or unsubstituted phenylene; or substituted or unsubstituted pyridylene.

According to the first and second exemplary embodiments of the present specification, L is phenylene; or pyridylene.

According to the exemplary embodiment of the present specification,

Chemical Formula 1 according to the aforementioned exemplary embodiment is represented by any one of the following Chemical Formulas 2 to 7.

[Chemical Formula 2]

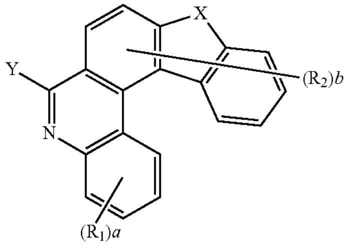

[Chemical Formula 3]

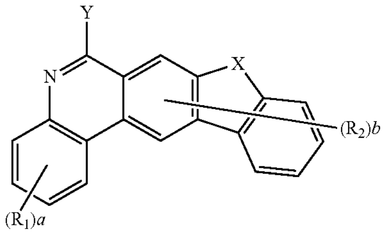

[Chemical Formula 4]

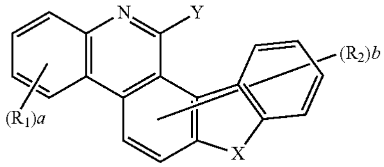

[Chemical Formula 5]

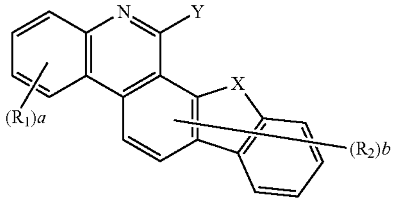

[Chemical Formula 6]

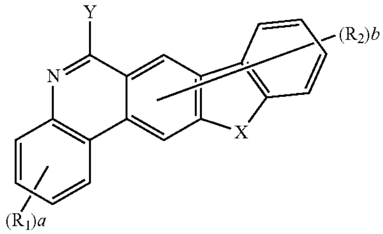

[Chemical Formula 7]

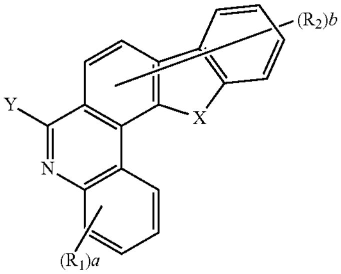

In Chemical Formulas 2 to 7, X, Y, $R_1$, $R_2$, a, and b are the same as those of Chemical Formula 1 according to the aforementioned exemplary embodiment.

According to another exemplary embodiment of the present specification,

Chemical Formula 1 according to the aforementioned exemplary embodiment is represented by any one of the following Chemical Formulas 8 to 12.

[Chemical Formula 8]

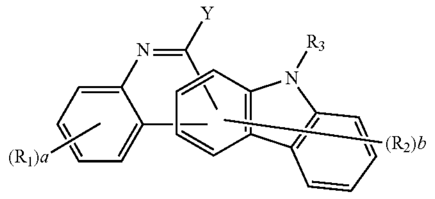

[Chemical Formula 9]

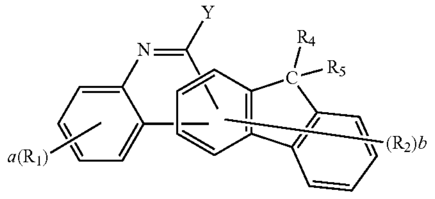

[Chemical Formula 10]

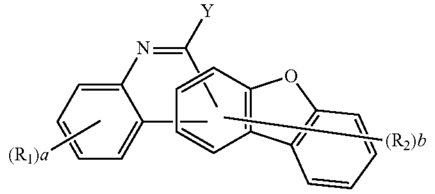

[Chemical Formula 11]

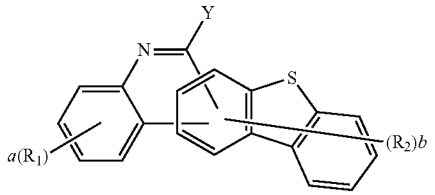

[Chemical Formula 12]

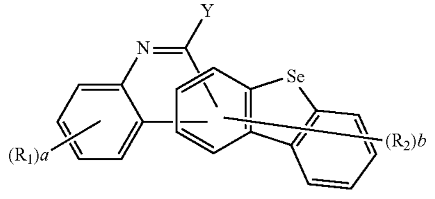

In Chemical Formulas 8 to 12, Y, a, b, and $R_1$ to $R_5$ are the same as those of Chemical Formula 1 according to the aforementioned exemplary embodiment.

According to another exemplary embodiment of the present specification,

Chemical Formula 8 according to the aforementioned exemplary embodiment is represented by any one of the following Chemical Formulas 13 to 24.

[Chemical Formula 13]

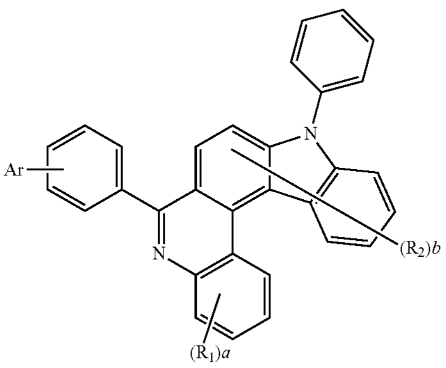

[Chemical Formula 14]

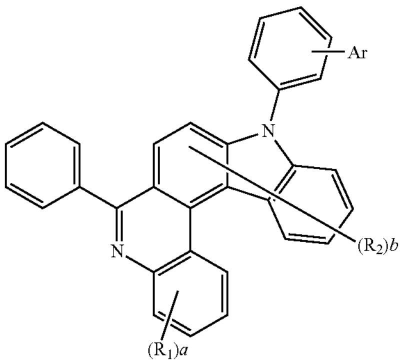

[Chemical Formula 15]

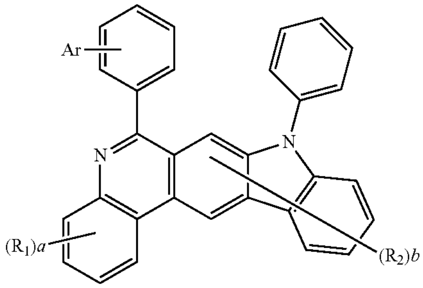

[Chemical Formula 16]

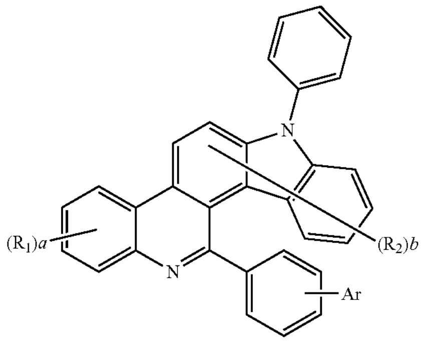

-continued

[Chemical Formula 17]

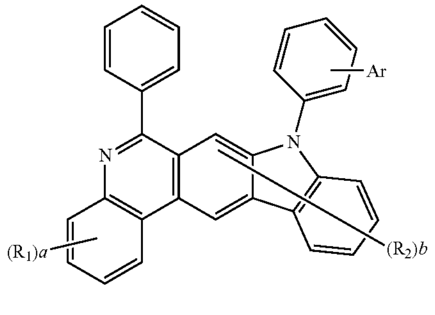

[Chemical Formula 18]

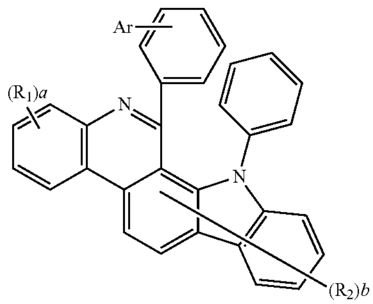

[Chemical Formula 19]

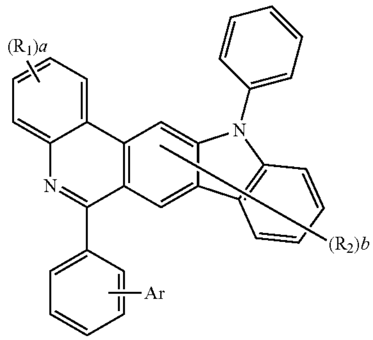

[Chemical Formula 20]

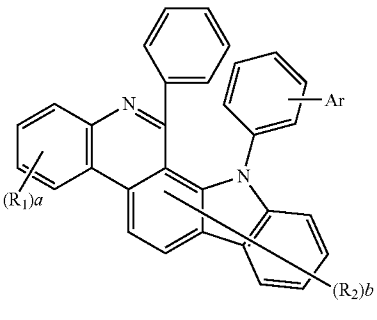

-continued

[Chemical Formula 21]

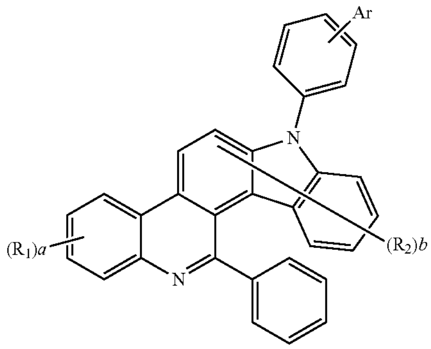

[Chemical Formual 22]

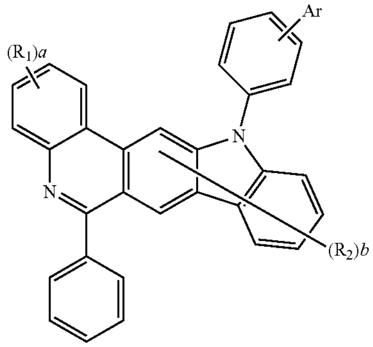

[Chemical Formula 23]

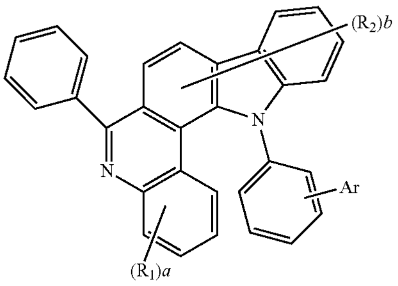

[Chemical Formula 24]

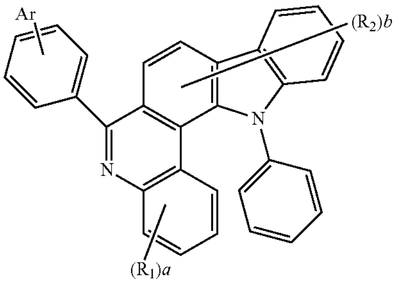

In Chemical Formulas 13 to 24,

Ar is selected from the group consisting of hydrogen; deuterium; halogen; $—P(═O)R_{11}R_{12}$; substituted or unsubstituted $C_6$ to $C_{60}$ monocyclic or polycyclic aryl; substituted or unsubstituted $C_2$ to $C_{60}$ monocyclic or polycyclic heteroaryl; substituted or unsubstituted $C_1$ to $C_{60}$ straight-chain or branch-chain alkyl; and amine substituted or unsubstituted by substituted or unsubstituted $C_1$ to $C_{20}$ alkyl, substituted or unsubstituted $C_6$ to $C_{60}$ monocyclic or polycyclic aryl, or substituted or unsubstituted $C_2$ to $C_{60}$ monocyclic or polycyclic heteroaryl, $R_{11}$ and $R_{12}$ are the same as or different from each other, and are each independently hydrogen; substituted or unsubstituted $C_1$ to $C_{60}$ straight-chain or branch-chain alkyl; substituted or unsubstituted $C_3$ to $C_{60}$ monocyclic or polycyclic cycloalkyl; substituted or unsubstituted $C_6$ to $C_{60}$ monocyclic or polycyclic aryl; or substituted or unsubstituted $C_2$ to $C_{60}$ monocyclic or polycyclic heteroaryl, and $R_1$, $R_2$, a, and b are the same as those of Chemical Formula 1 according to the aforementioned exemplary embodiment.

According to another exemplary embodiment of the present specification,

Chemical Formulas 2 to 7 according to the aforementioned exemplary embodiment are represented by the following Chemical Formulas 25 to 30, respectively.

[Chemical Formula 25]

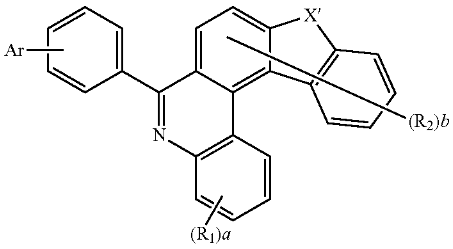

[Chemical Formula 26]

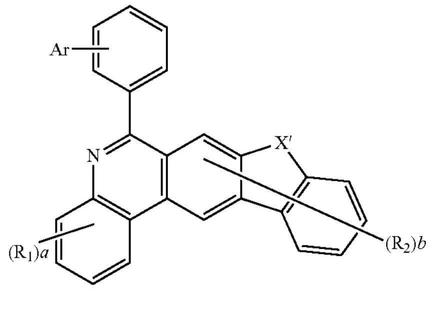

[Chemical Formula 27]

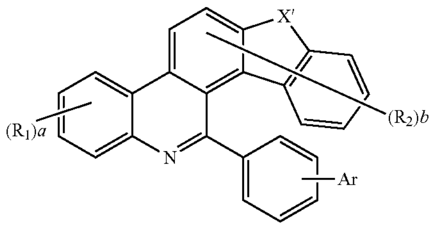

[Chemical Formula 28]

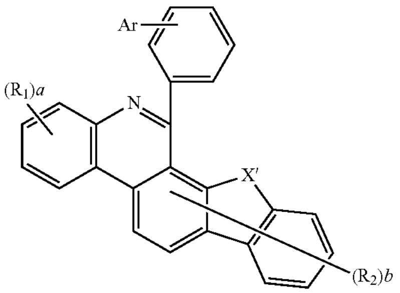

-continued

[Chemical Formula 29]

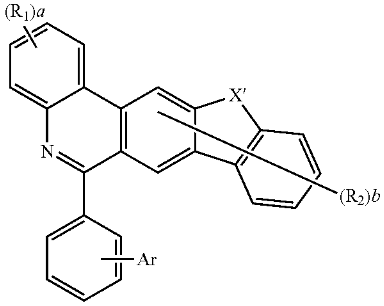

[Chemical Formula 30]

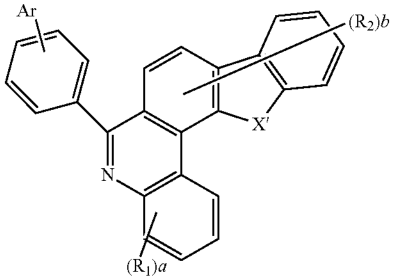

In Chemical Formulas 25 to 30, X' is $CR_4R_5$, O, S, or Se,

Ar is selected from the group consisting of hydrogen; deuterium; halogen; —P(=O)$R_{11}R_{12}$; substituted or unsubstituted $C_6$ to $C_{60}$ monocyclic or polycyclic aryl; substituted or unsubstituted $C_2$ to $C_{60}$ monocyclic or polycyclic heteroaryl; substituted or unsubstituted $C_1$ to $C_{60}$ straight-chain or branch-chain alkyl; and amine substituted or unsubstituted by substituted or unsubstituted $C_1$ to $C_{20}$ alkyl, substituted or unsubstituted $C_6$ to $C_{60}$ monocyclic or polycyclic aryl, or substituted or unsubstituted $C_2$ to $C_{60}$ monocyclic or polycyclic heteroaryl, $R_4$, $R_5$, $R_{11}$, and $R_{12}$ are the same as or different from each other, and are each independently hydrogen; substituted or unsubstituted $C_1$ to $C_{60}$ straight-chain or branch-chain alkyl; substituted or unsubstituted $C_3$ to $C_{60}$ monocyclic or polycyclic cycloalkyl; substituted or unsubstituted $C_6$ to $C_{60}$ monocyclic or polycyclic aryl; or substituted or unsubstituted $C_2$ to $C_{60}$ monocyclic or polycyclic heteroaryl, and $R_1$, $R_2$, a, and b are the same as those of Chemical Formula 1 according to the aforementioned exemplary embodiment.

According to the exemplary embodiment of the present specification,

Chemical Formula 1 may be selected from the following compounds.

According to another exemplary embodiment of the present specification, in Chemical Formulas 13 and 25, Ar may be bonded to an atom bonded to a core of phenyl at a para position thereof, and Chemical Formulas 13 and 25 may be selected from the following compounds.

1-1
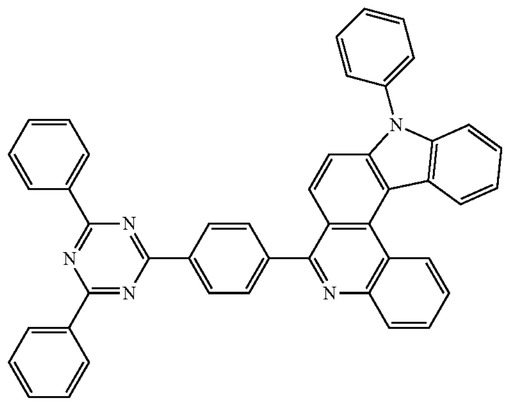
1-2
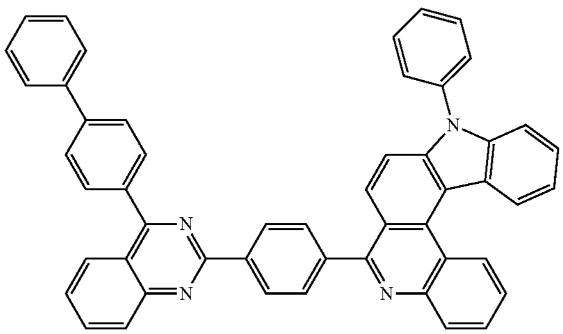
1-3
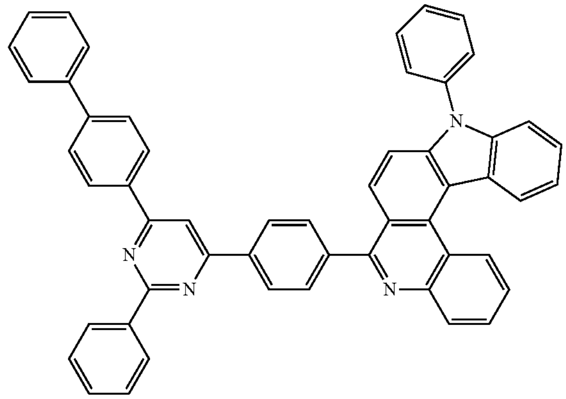
1-4
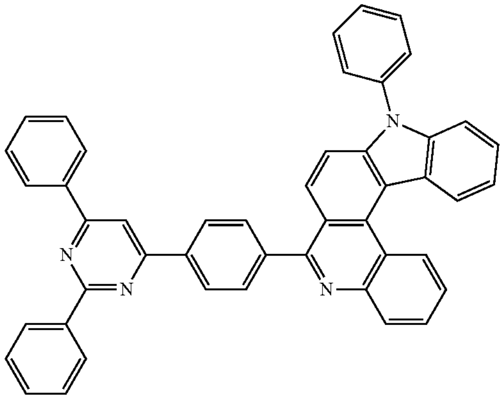
1-5
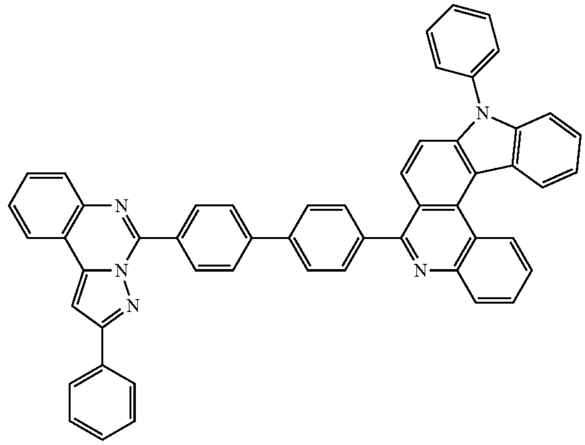
1-6
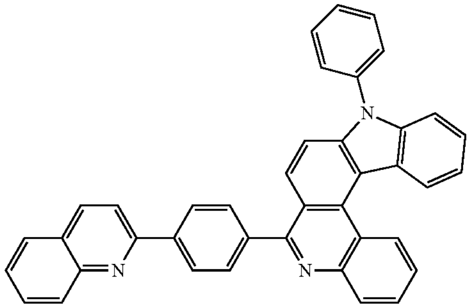
1-7
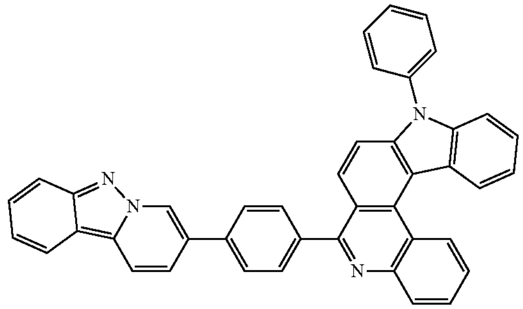
1-8
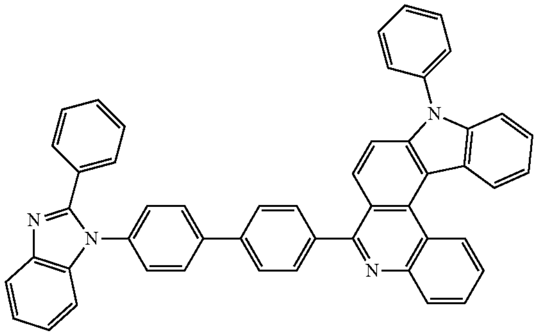

-continued
1-9
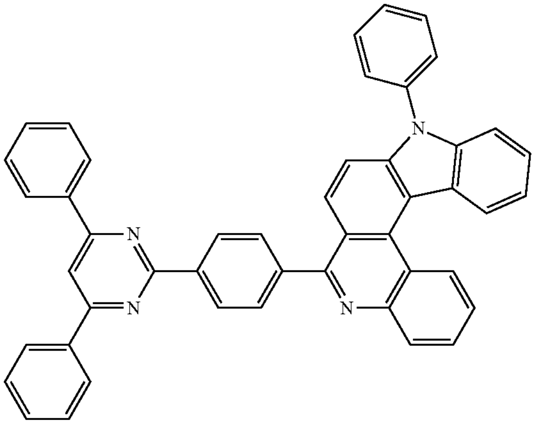
1-10
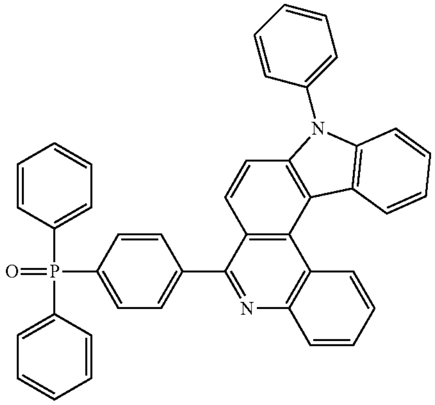
1-11
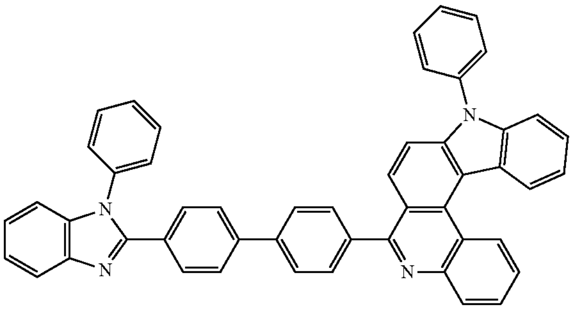
1-12
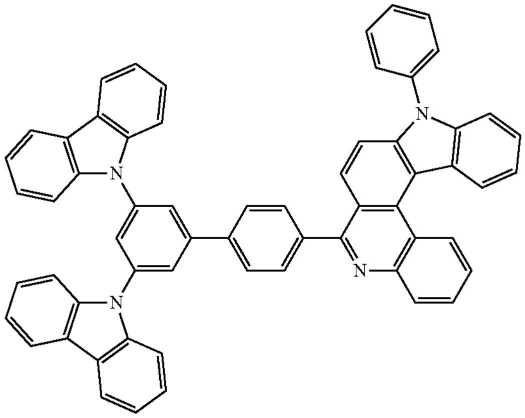
1-13
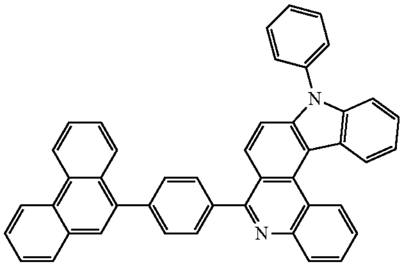
1-14
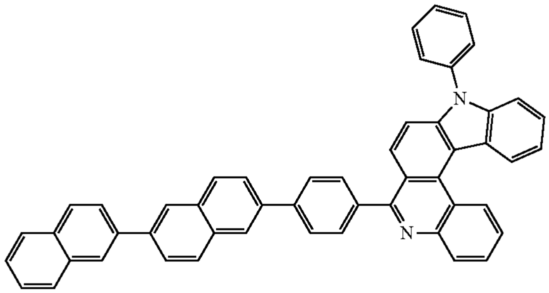
1-15
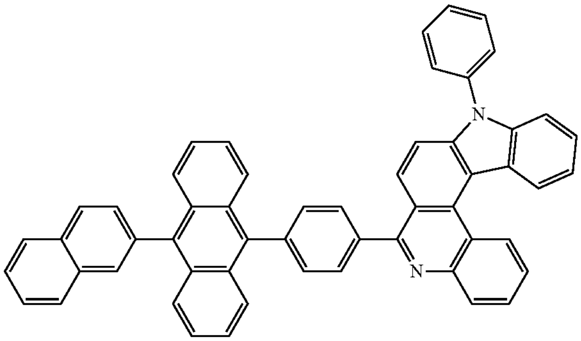
1-16
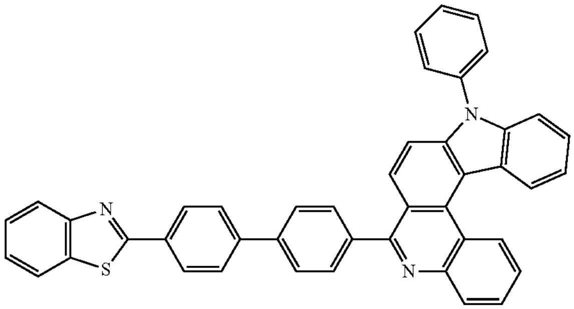

-continued
1-17
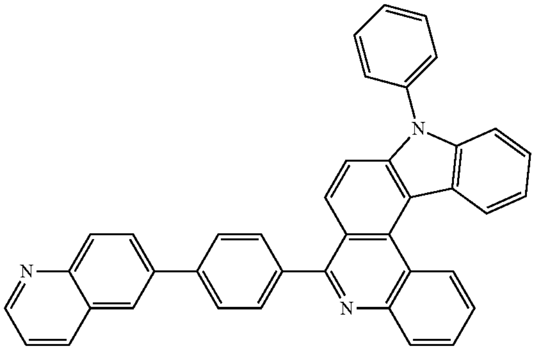
1-18
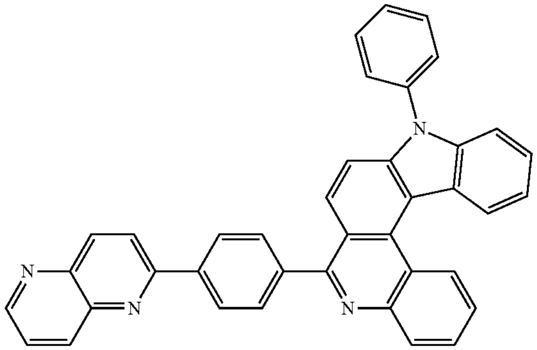
1-19
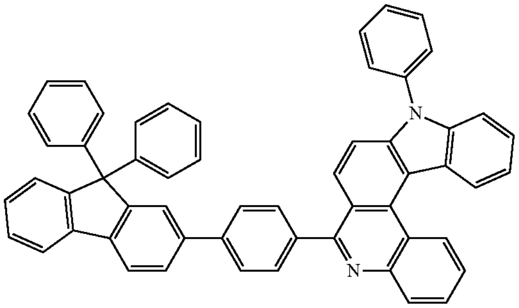
1-20
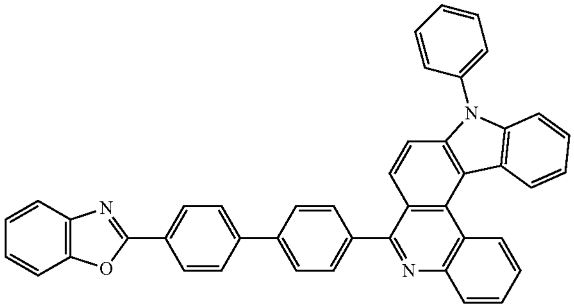
1-21
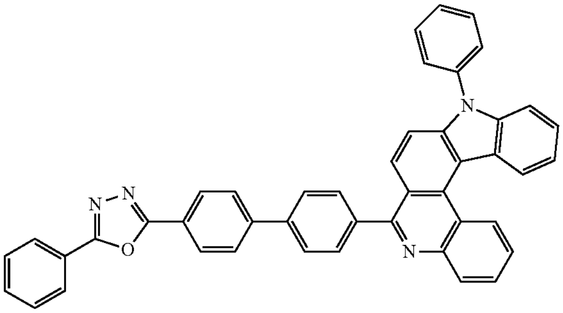
1-22
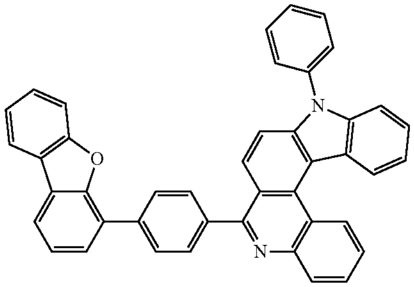
1-23
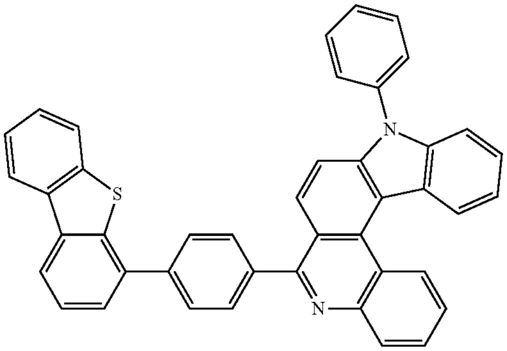
1-24
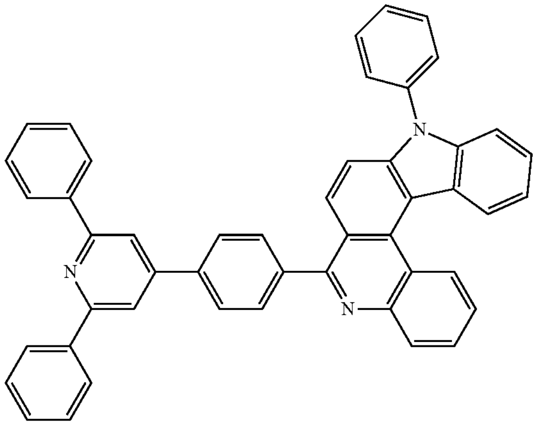

-continued
1-25
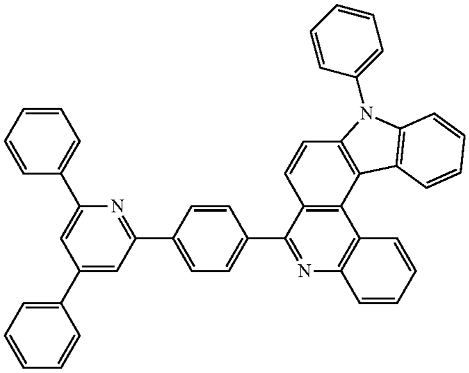
1-26
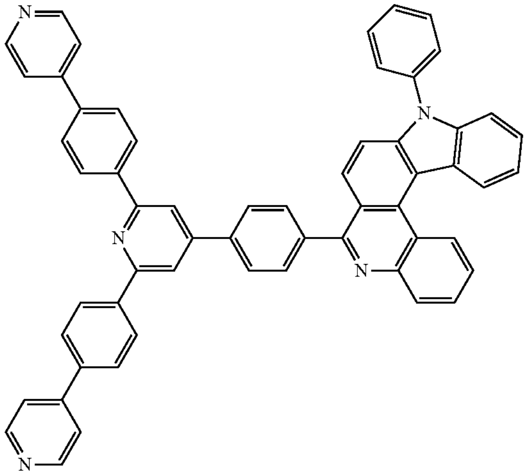
1-27
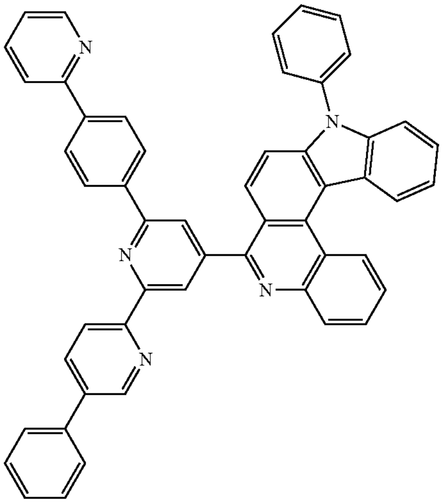
1-28
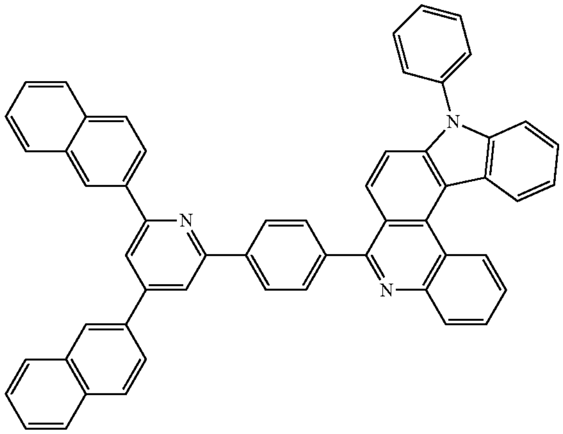
1-29
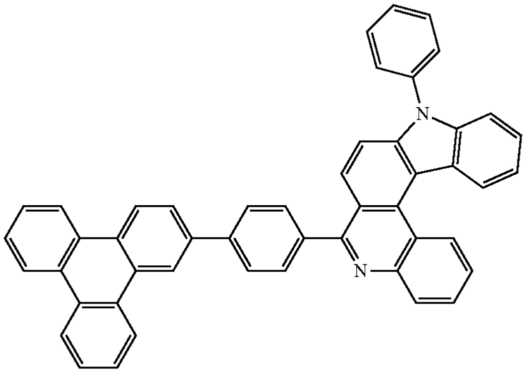
1-30
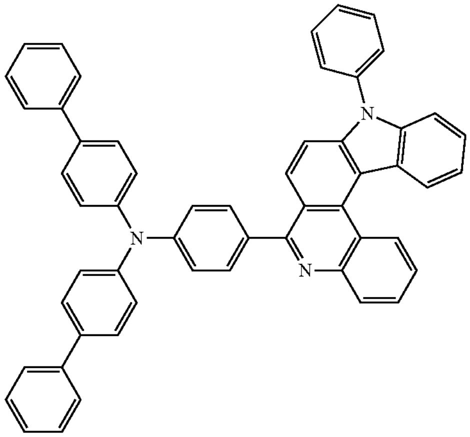

-continued
1-31
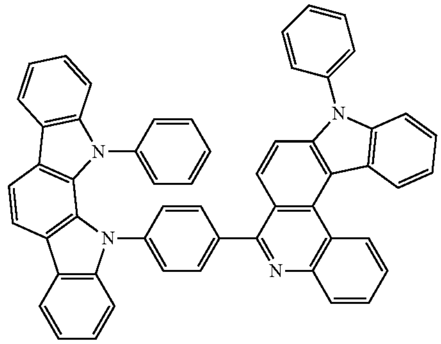
1-32
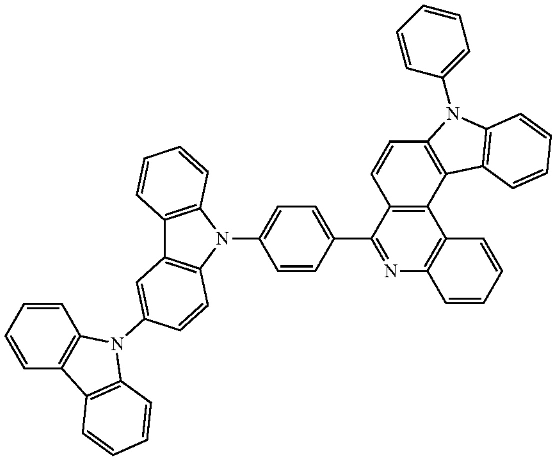
1-33
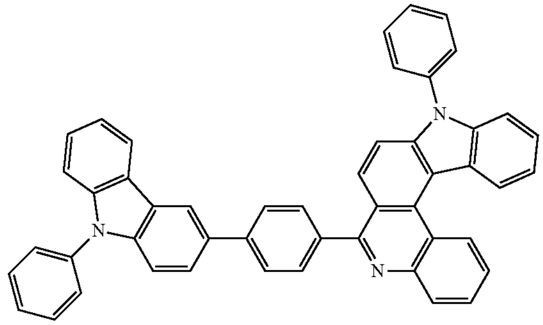
1-34
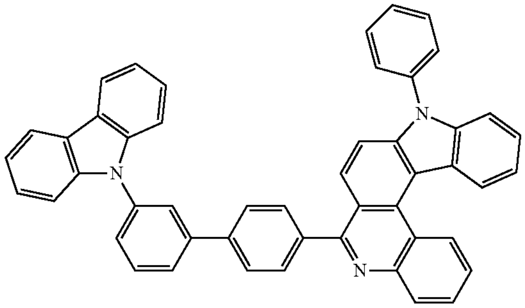
1-35
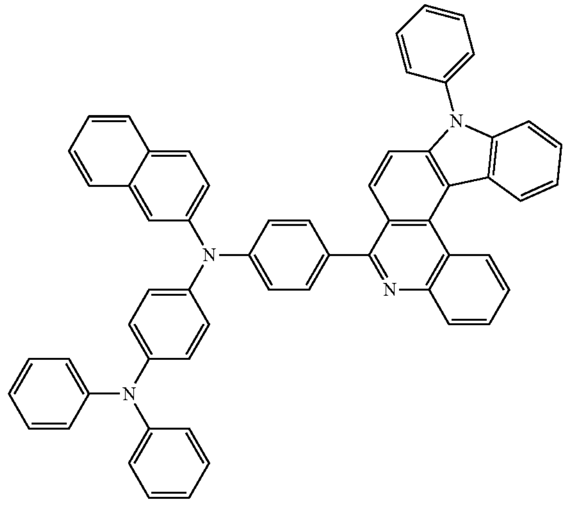
1-36
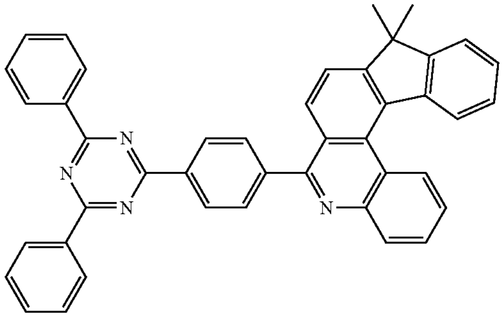

-continued
1-37
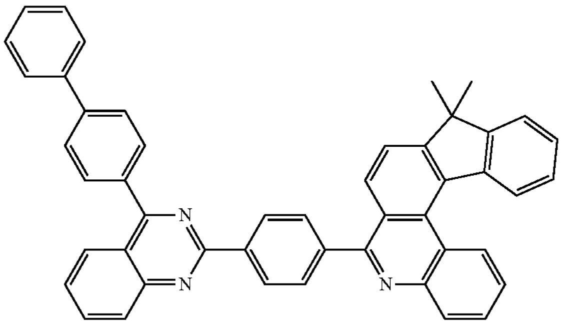
1-38
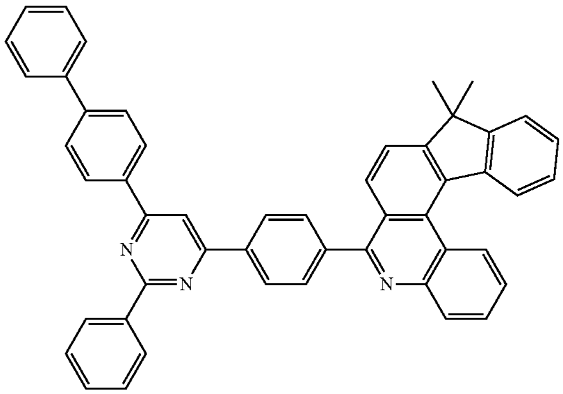
1-39
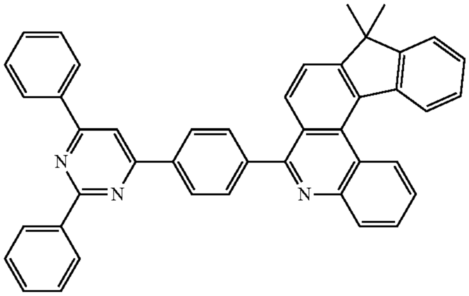
1-40
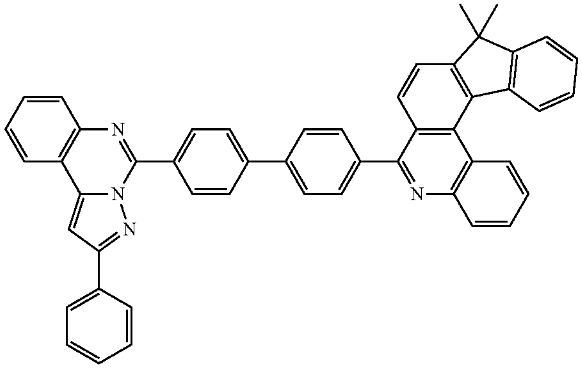
1-41
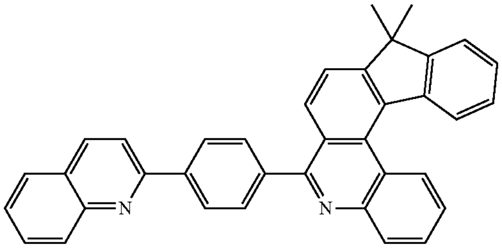
1-42
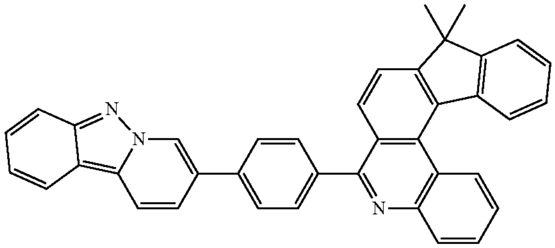
1-43
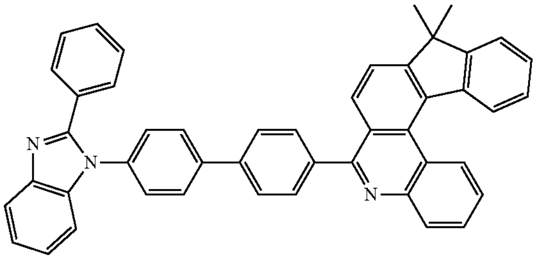
1-44
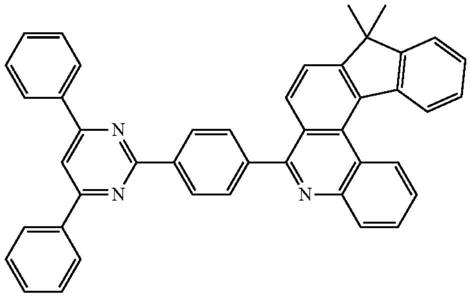

-continued
1-45
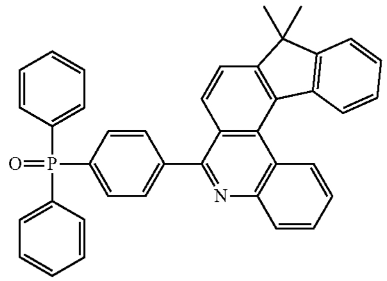
1-46
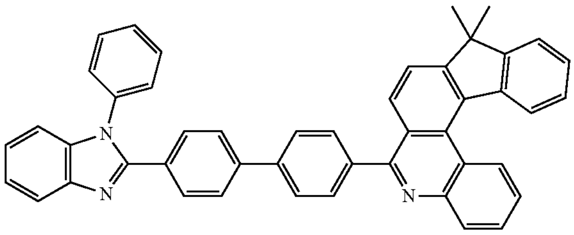
1-47
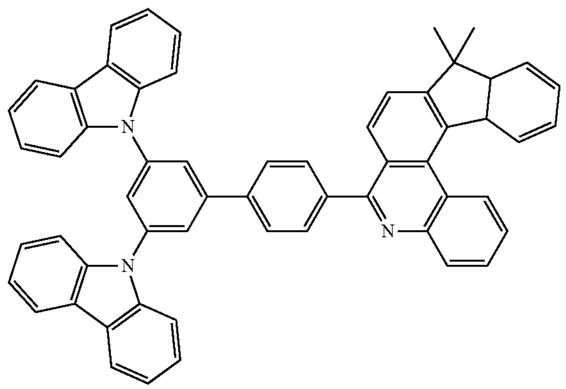
1-48
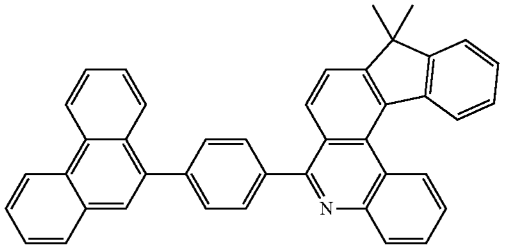
1-49
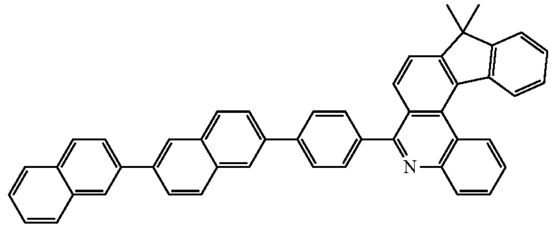
1-50
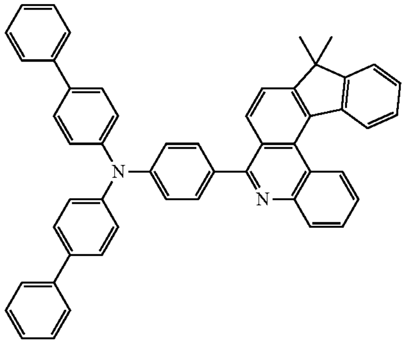
1-51
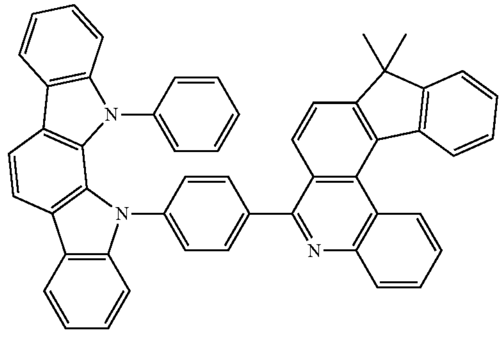
1-52
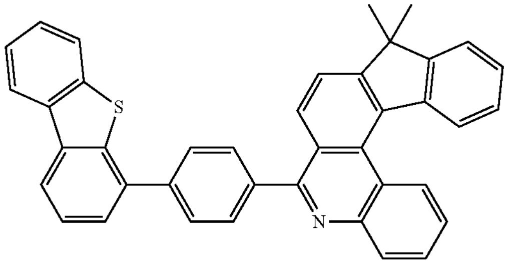

-continued
1-53
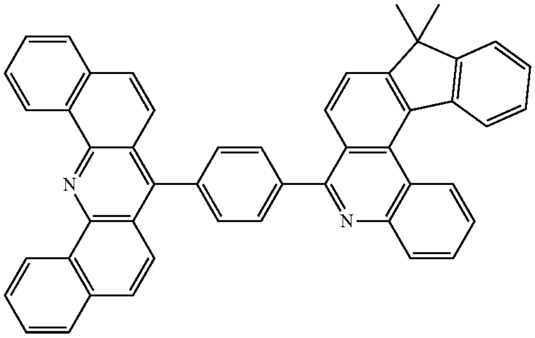
1-54
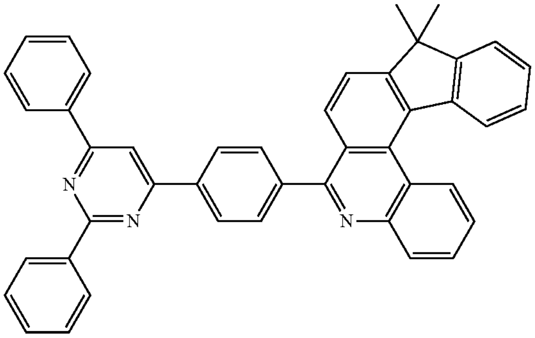
1-55
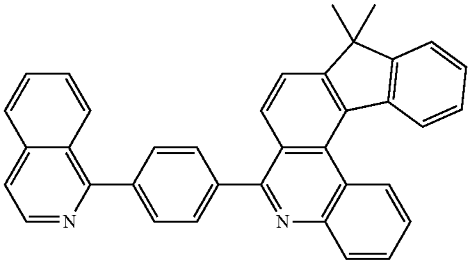
1-56
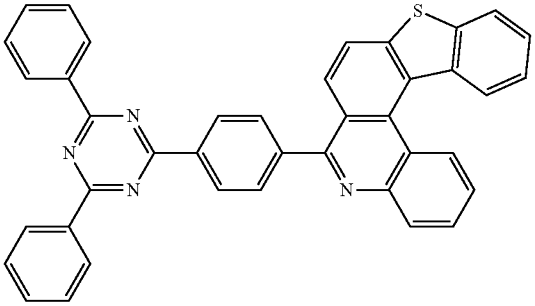
1-57
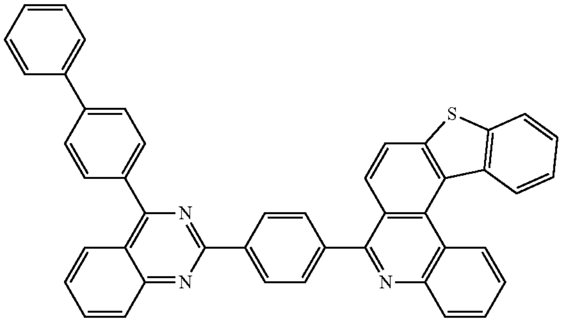
1-58
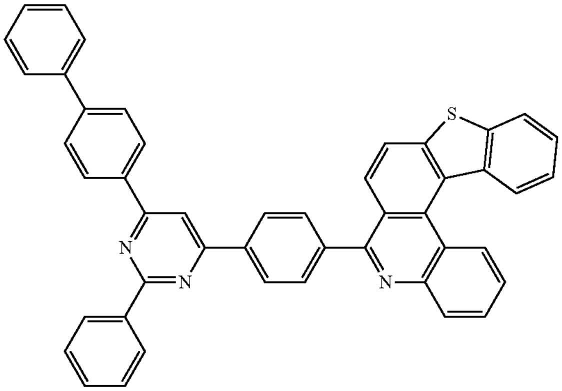
1-59
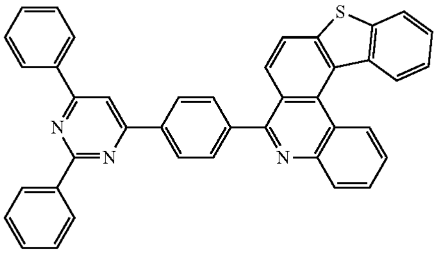
1-60
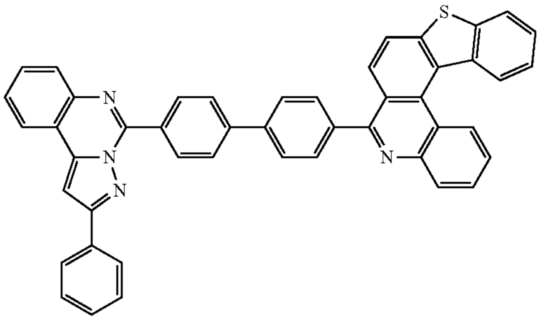
1-61
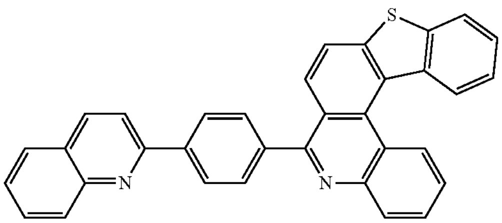
1-62
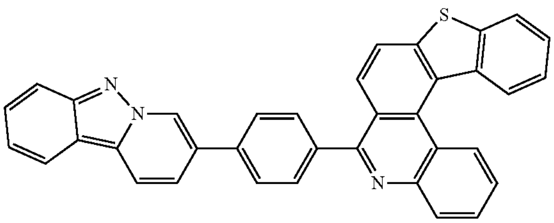

-continued
1-63
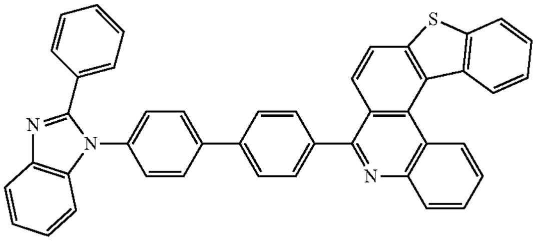
1-64
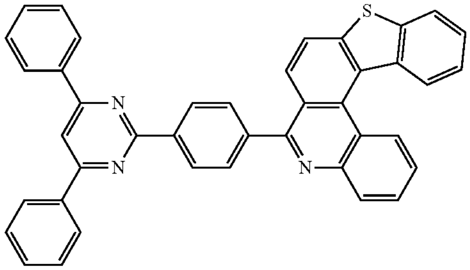
1-65
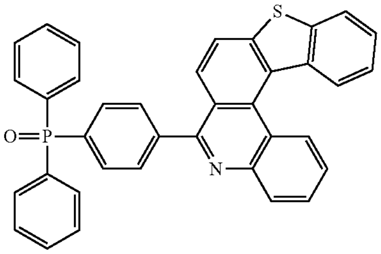
1-66
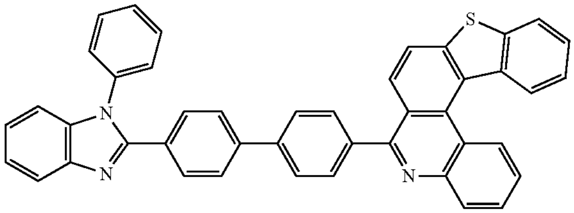
1-67
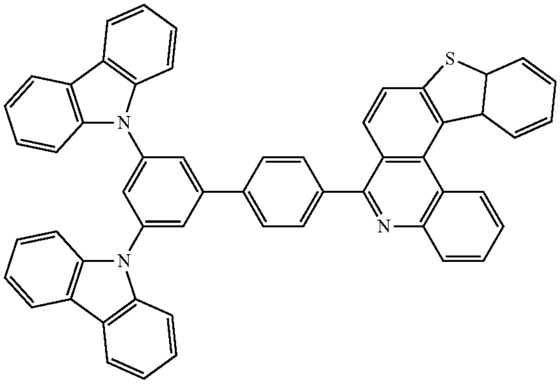
1-68
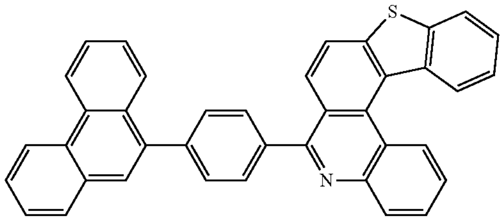
1-69
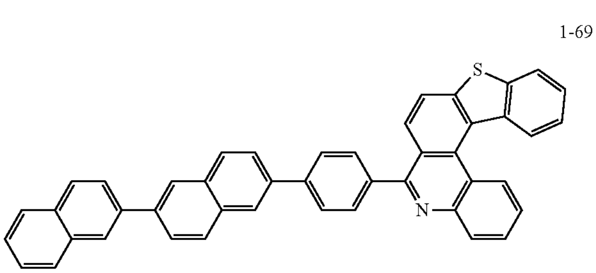
1-70
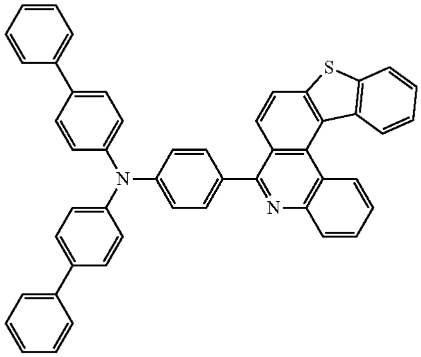

-continued
1-71
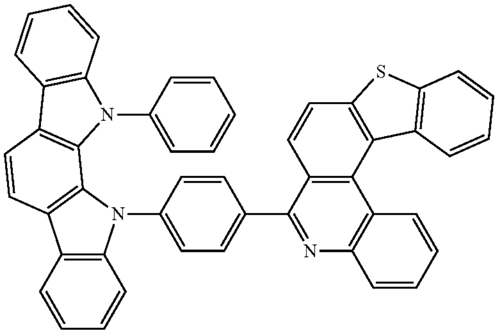
1-72
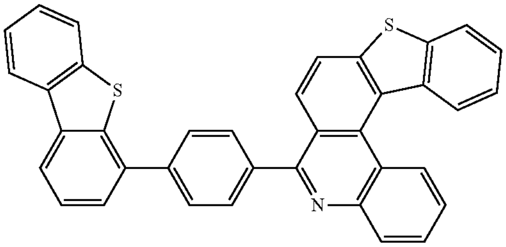
1-73
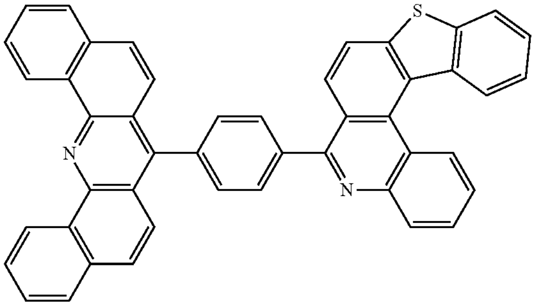
1-74
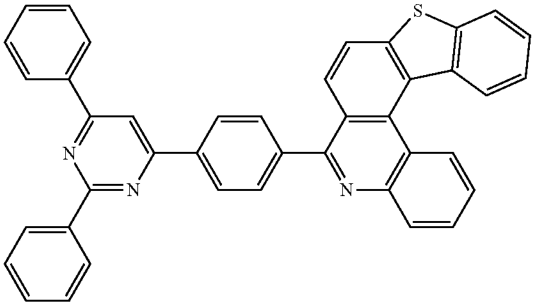
1-75
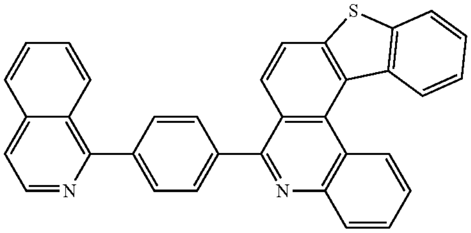
1-76
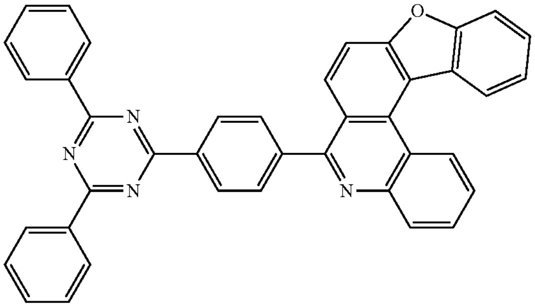
1-77
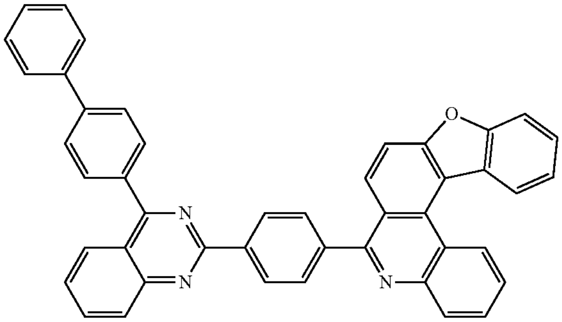
1-78
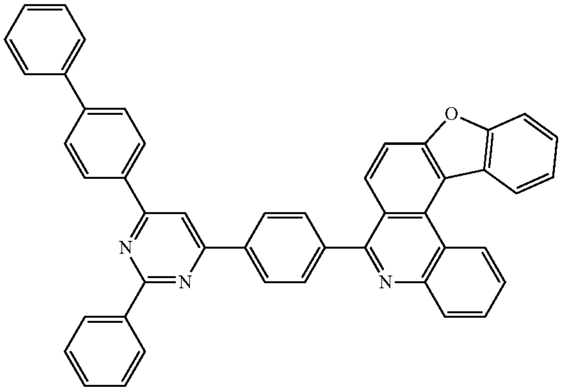

-continued
1-79
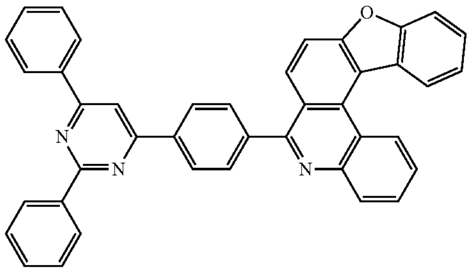
1-80
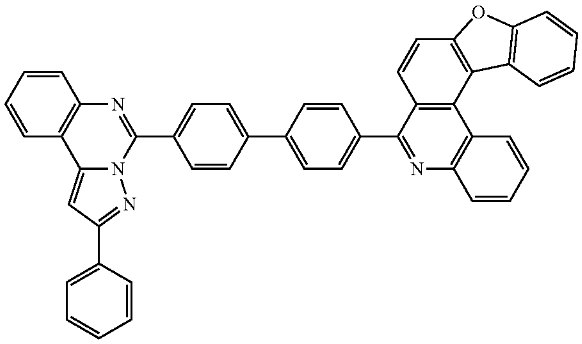
1-81
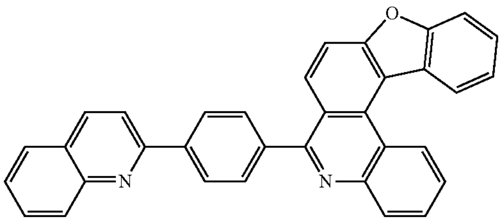
1-82
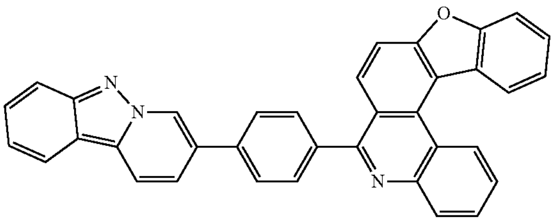
1-83
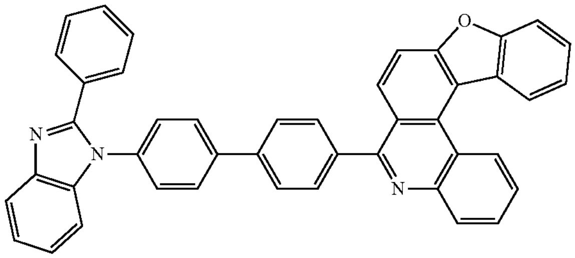
1-84
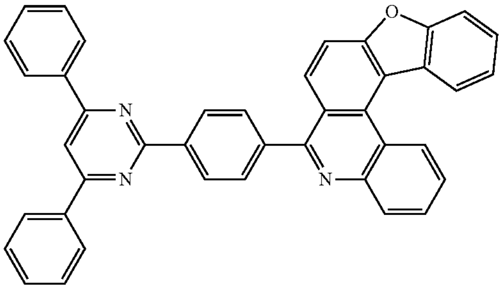
1-85
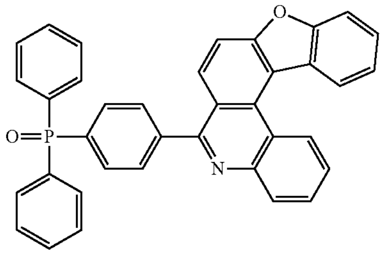
1-86
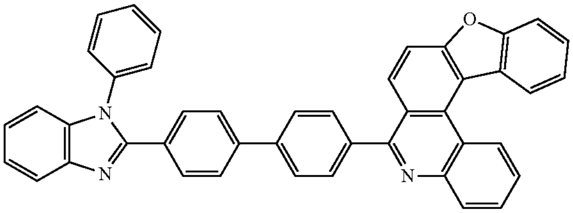
1-87
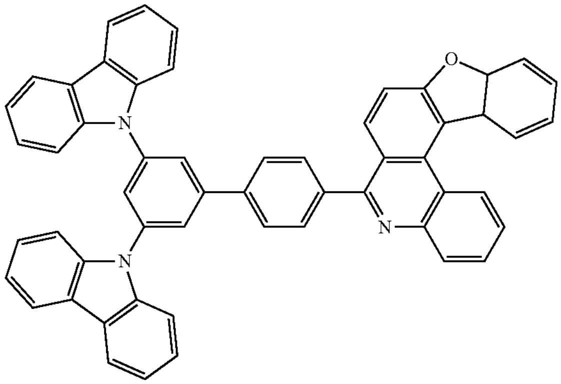
1-88
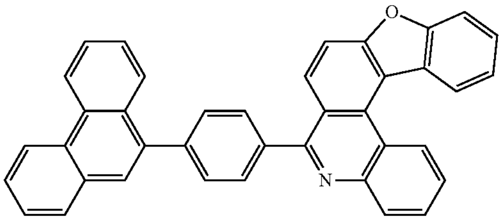

-continued
1-89
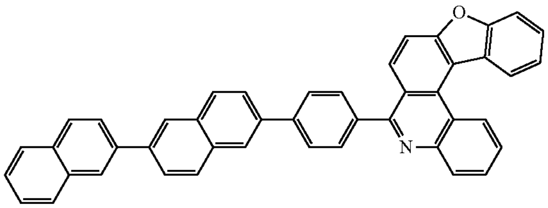
1-90
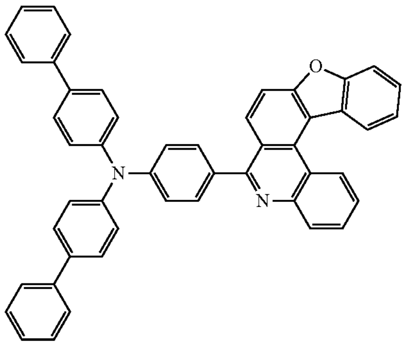
1-251
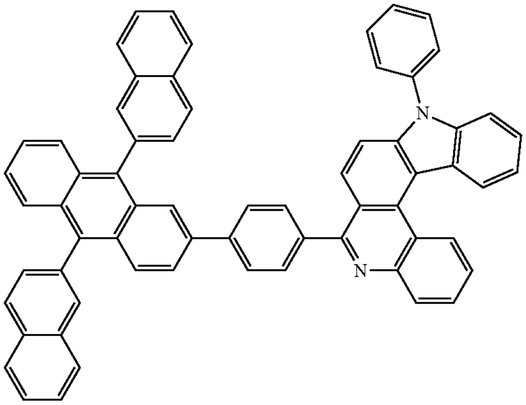
1-252
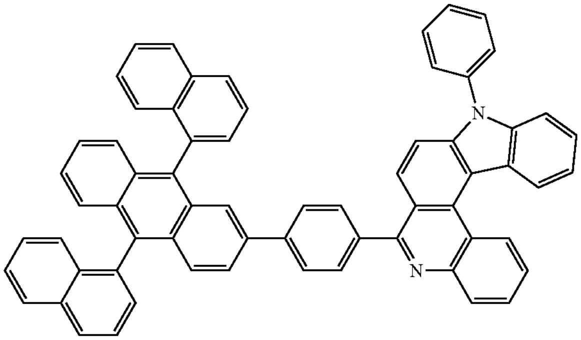
1-253
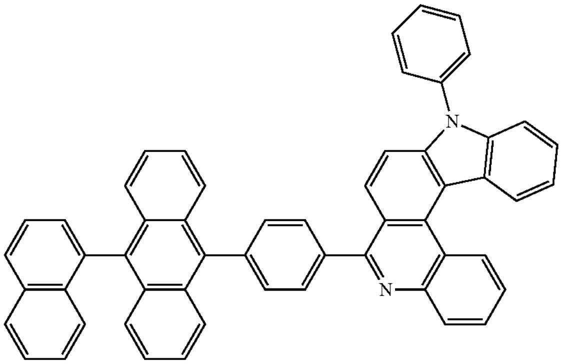
1-254
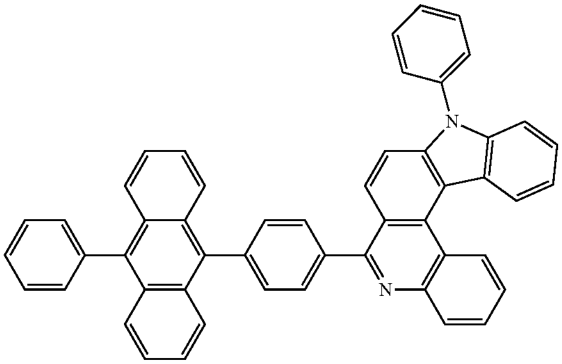
1-255
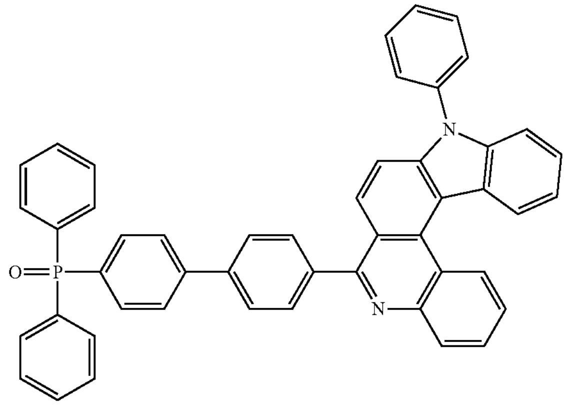
1-256
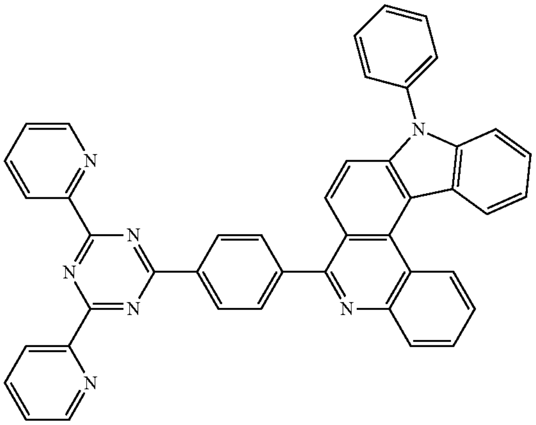

-continued
1-257
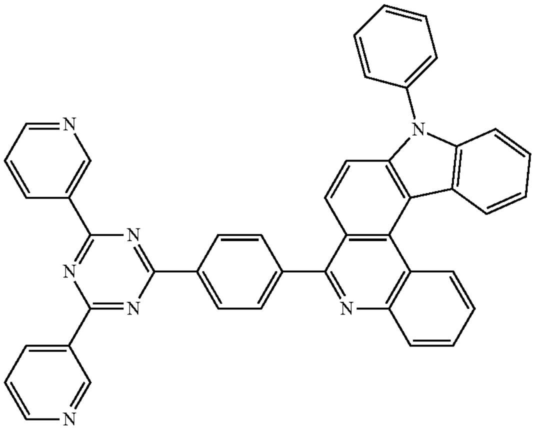
1-258
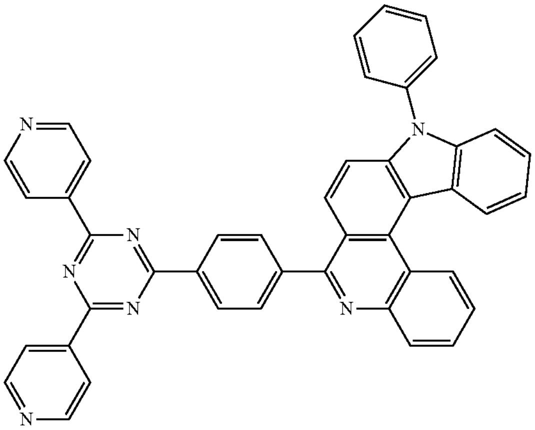
1-259
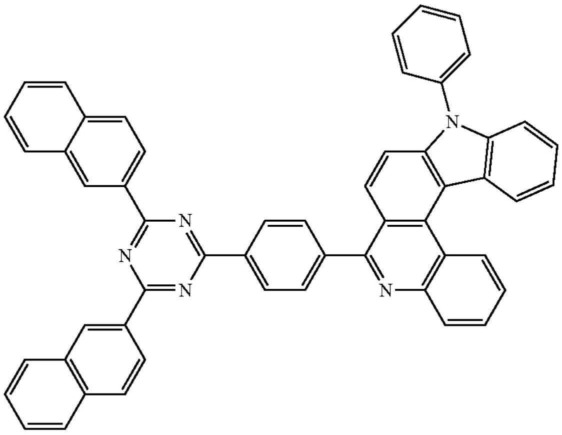
1-260
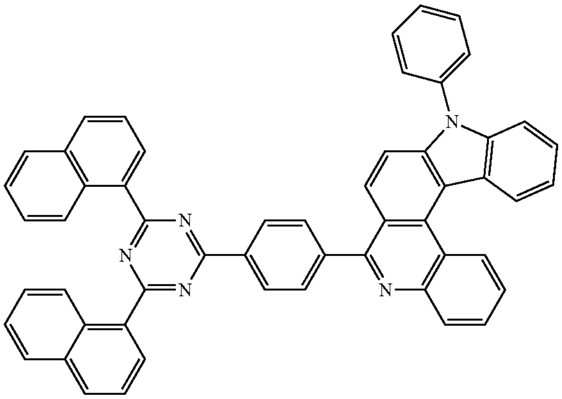
1-261
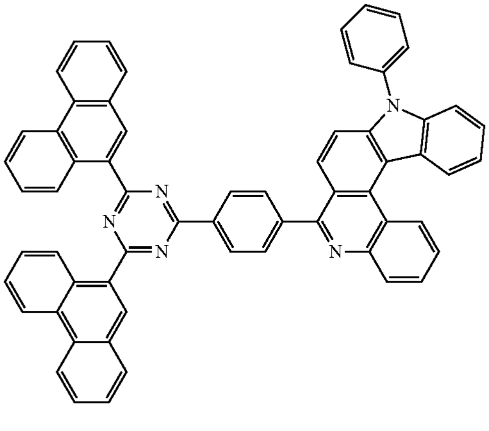
1-262
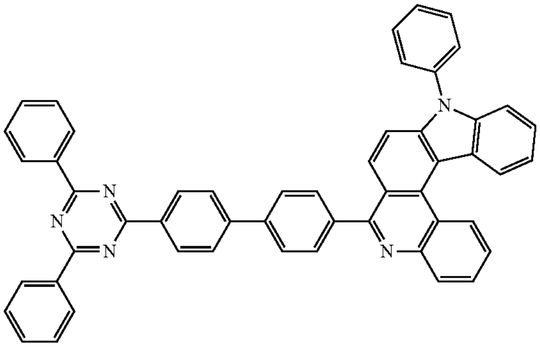

-continued
1-263
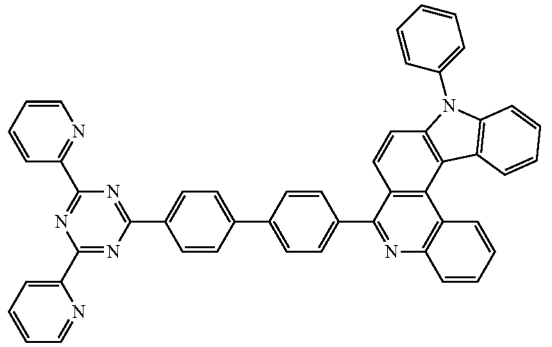
1-264
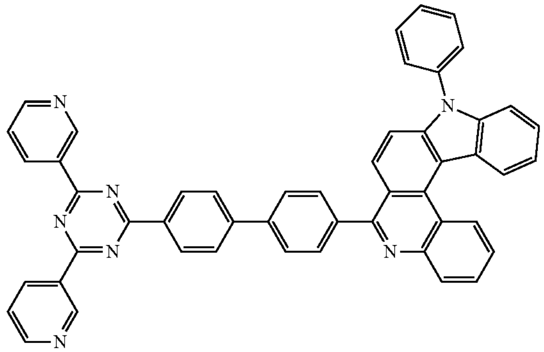
1-265
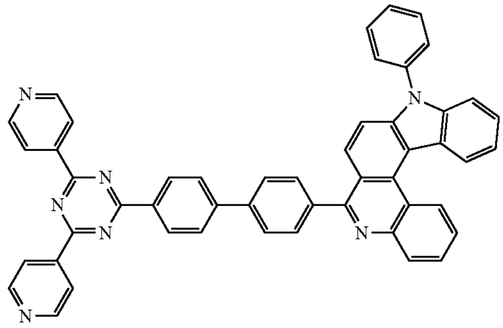
1-266
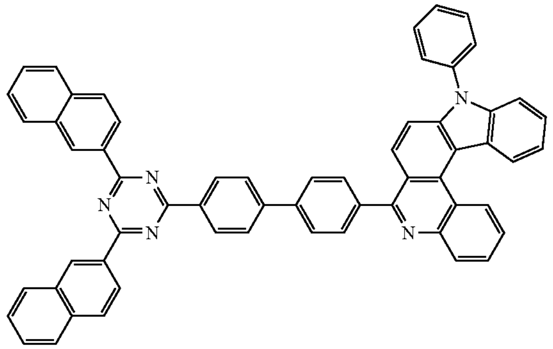
1-267
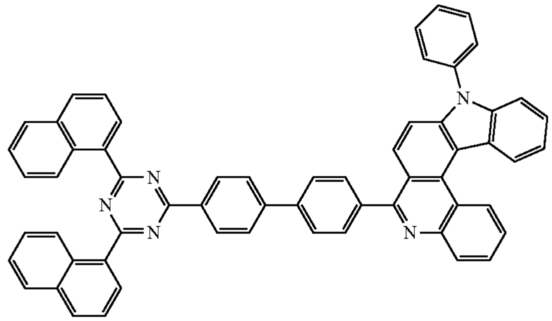
1-268
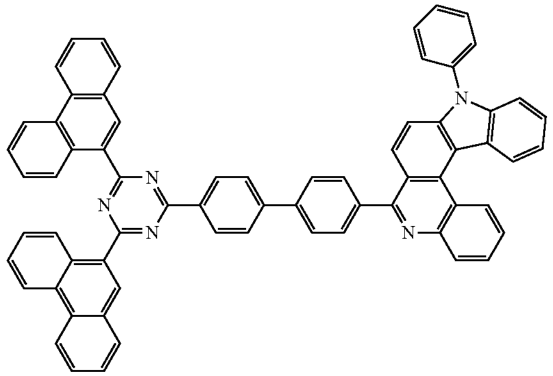
1-269
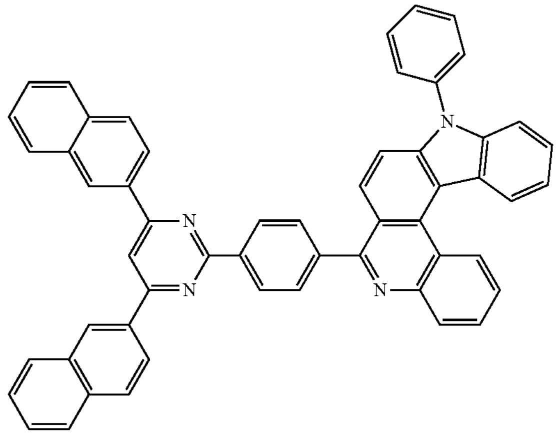
1-270
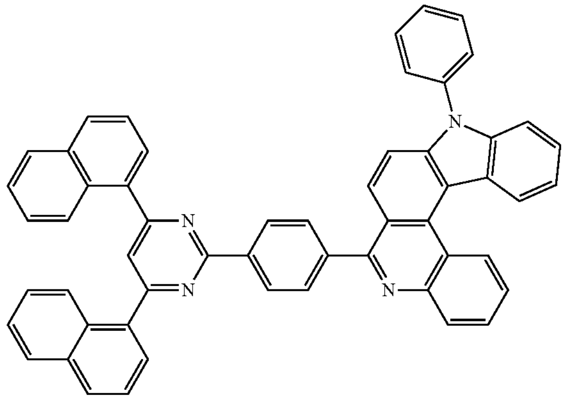

-continued
1-271
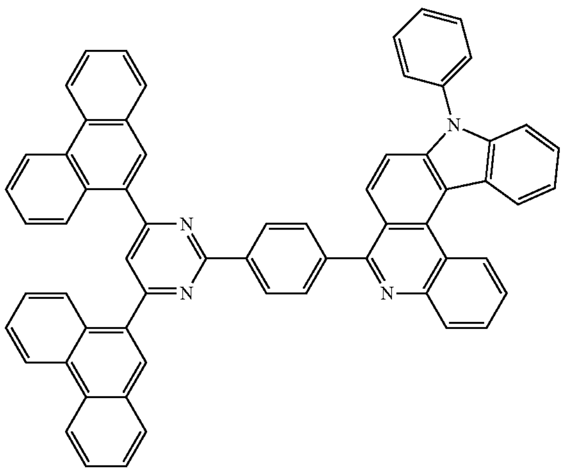
1-272
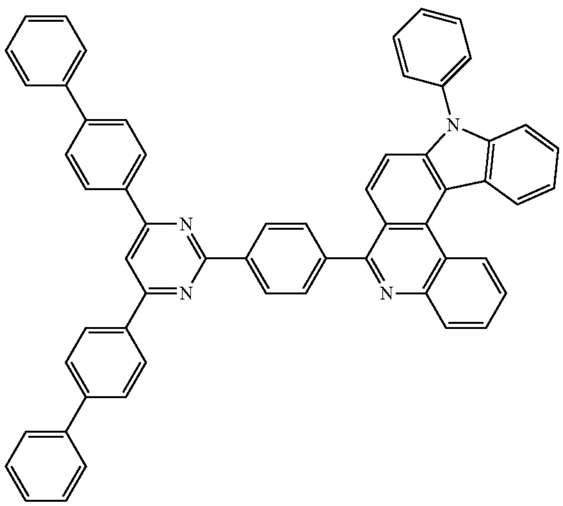
1-273
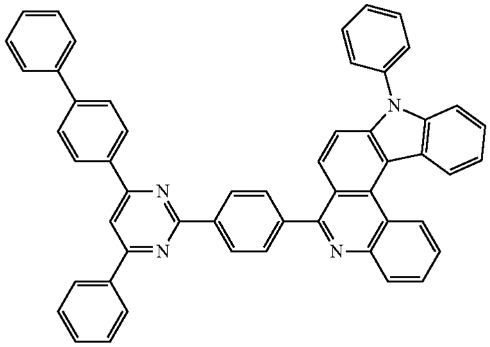
1-274
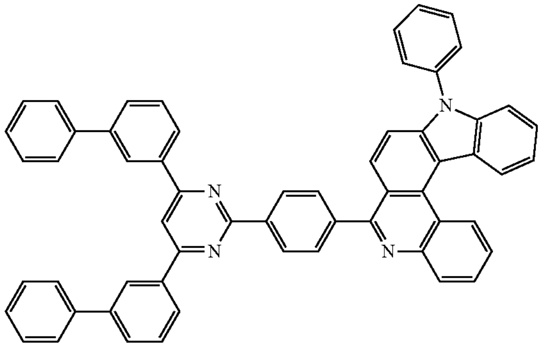
1-275
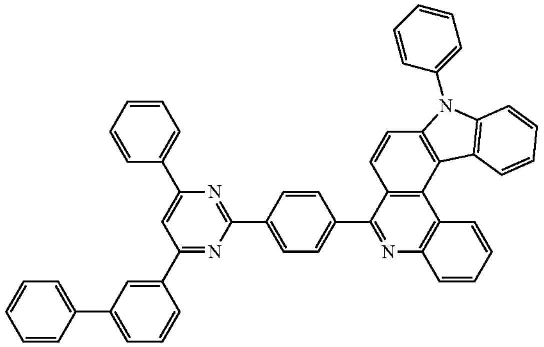
1-276
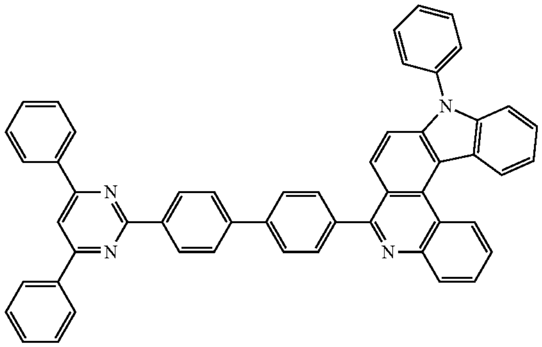
1-277
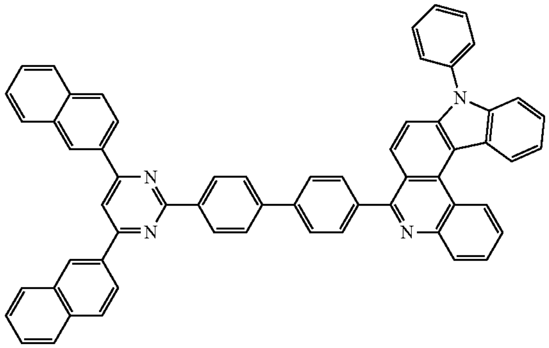
1-278
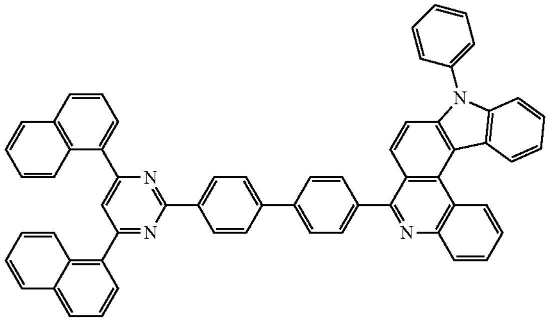

-continued
1-279
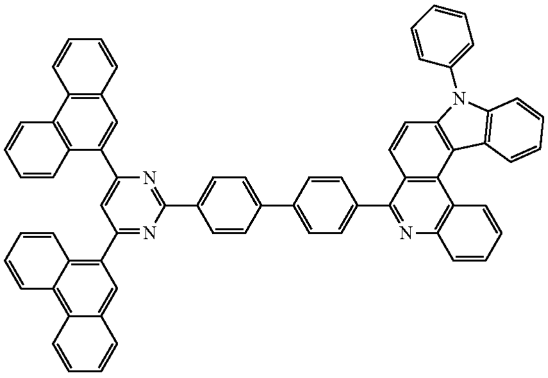
1-280
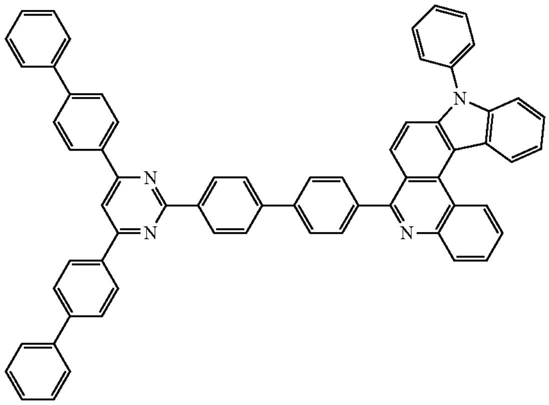
1-281
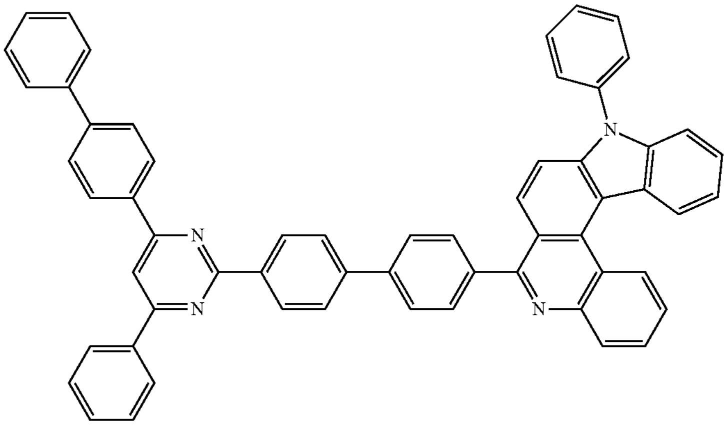
1-282
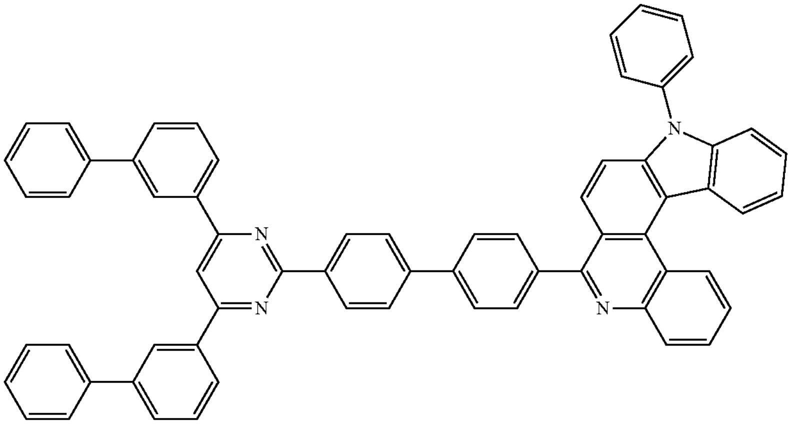

-continued
1-283
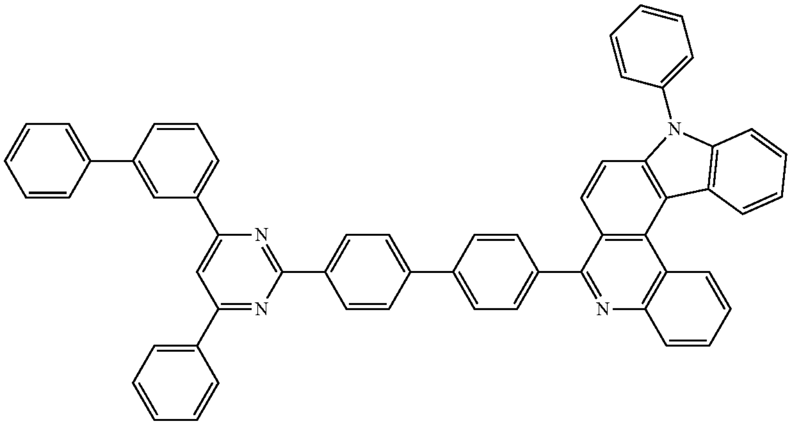
1-284
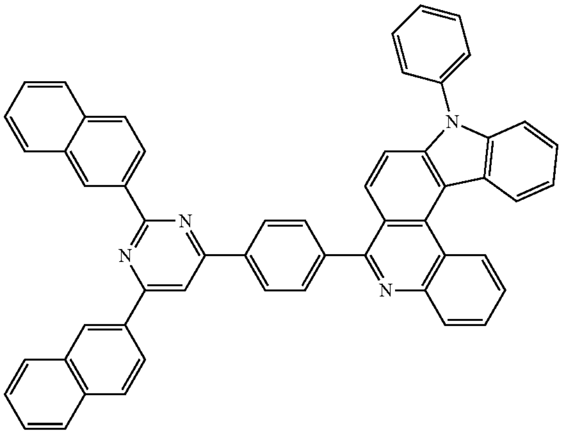
1-285
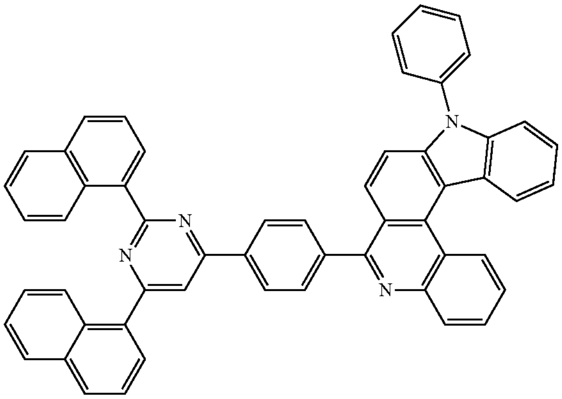
1-286
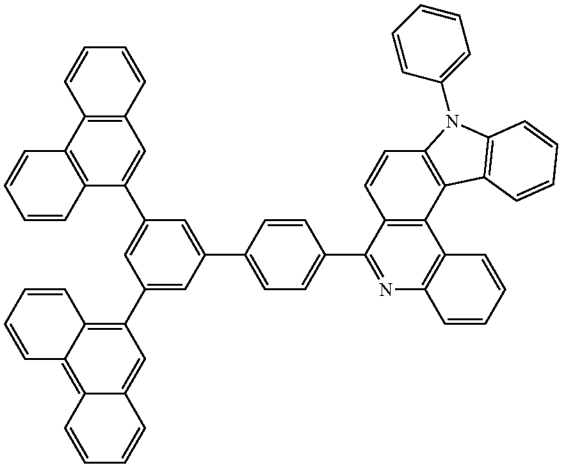
1-287
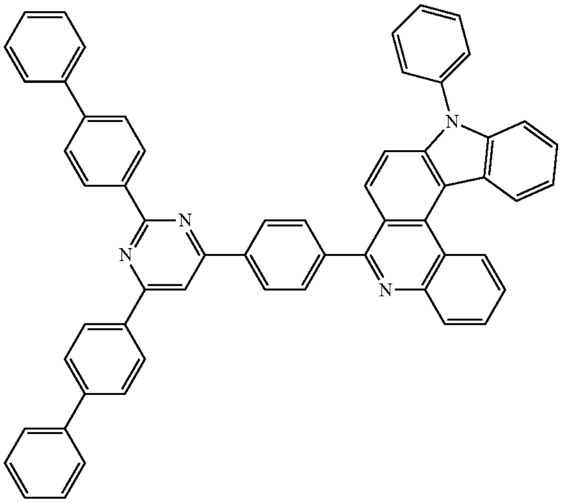

-continued
1-288
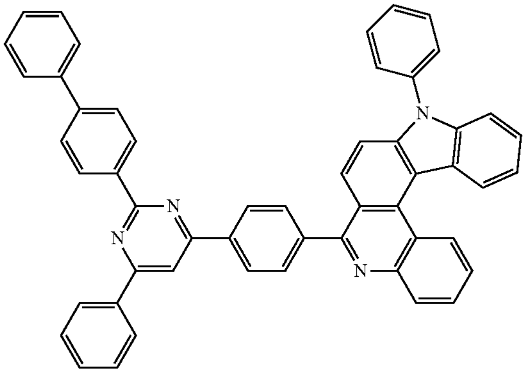
1-289
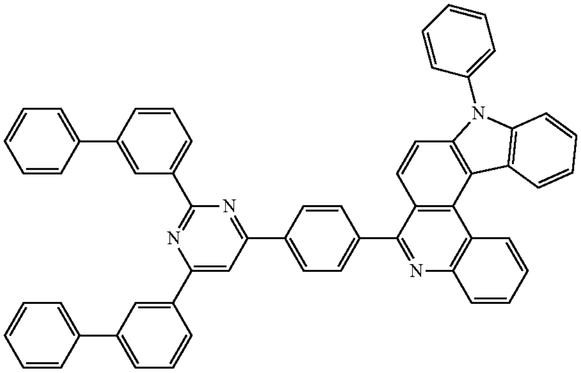
1-290
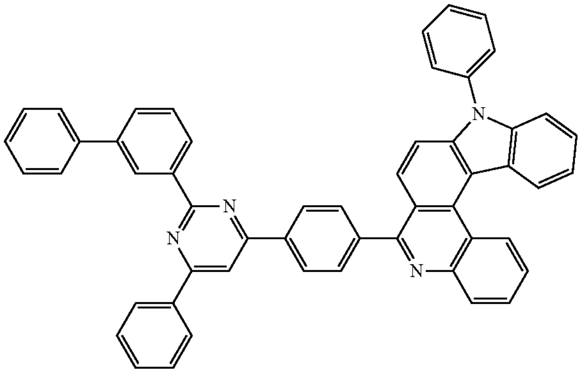
1-291
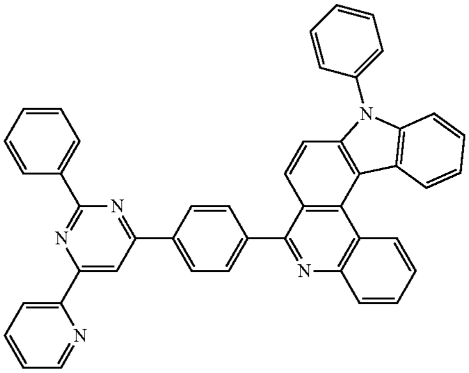
1-292
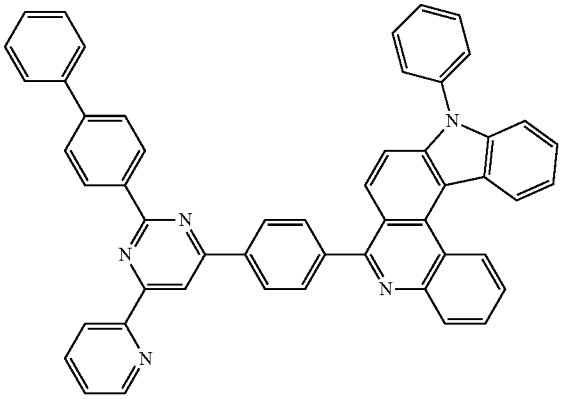
1-293
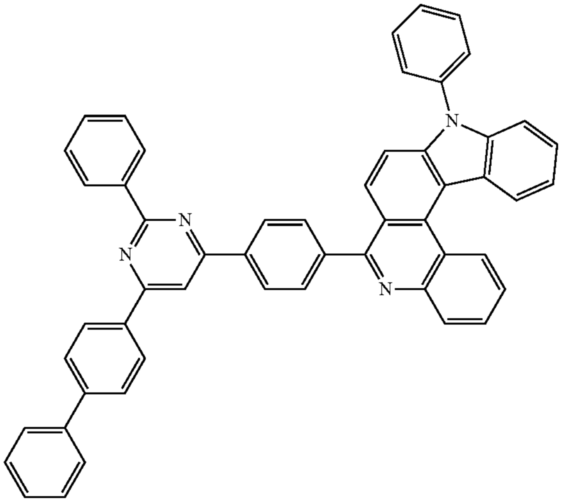

-continued
1-294
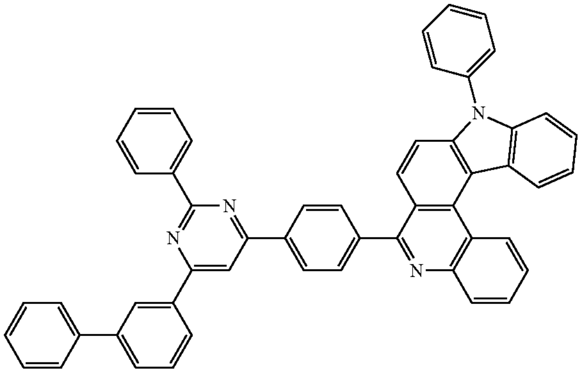
1-295
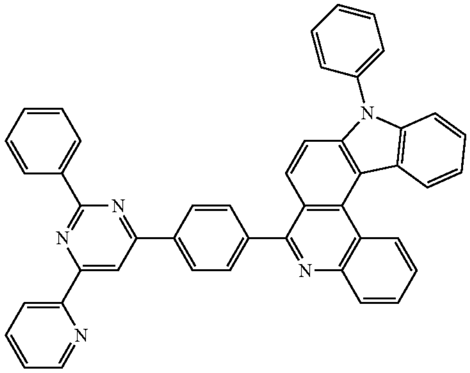
1-296
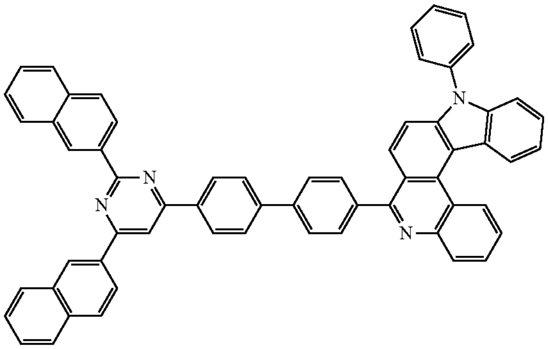
1-297
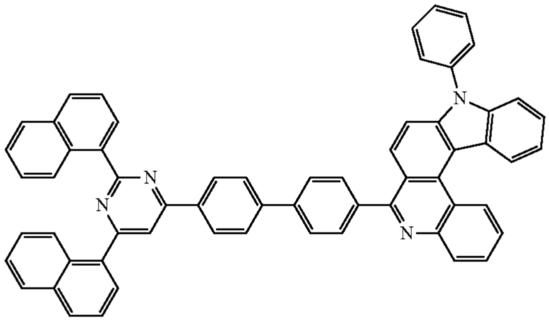
1-298
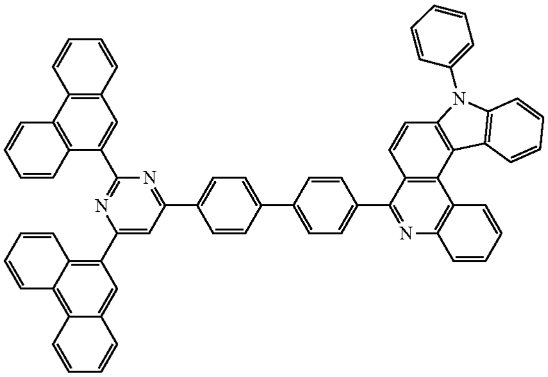
1-299
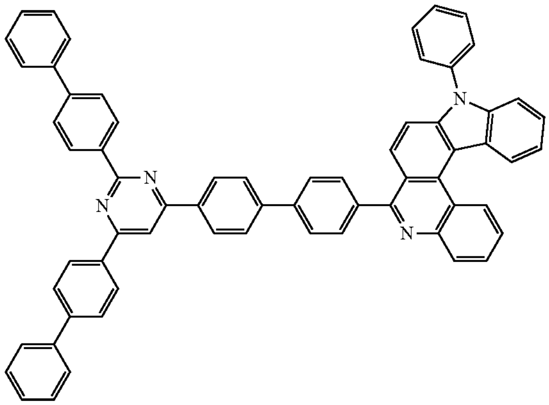
1-300
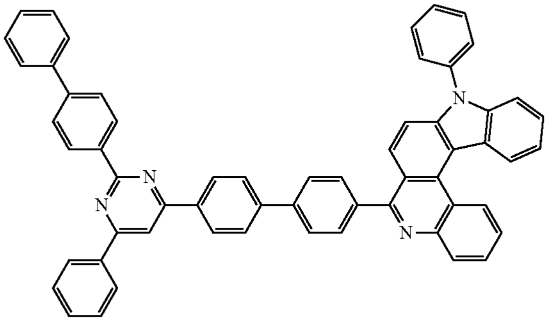
1-301
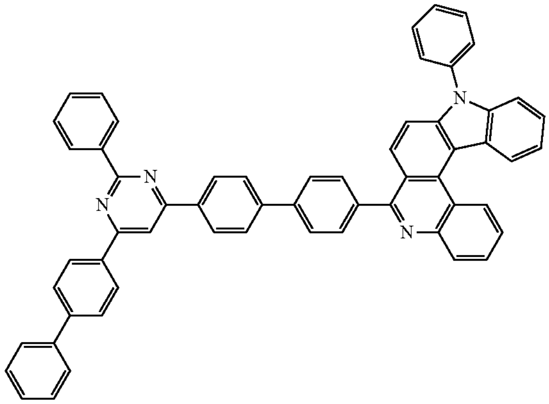

-continued
1-302
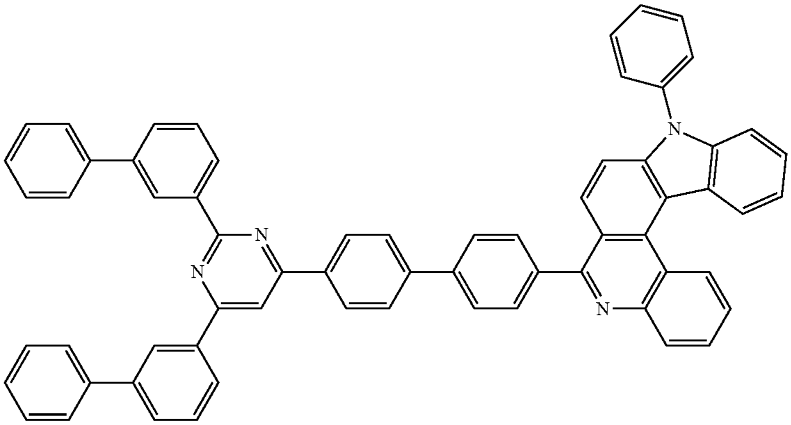
1-303
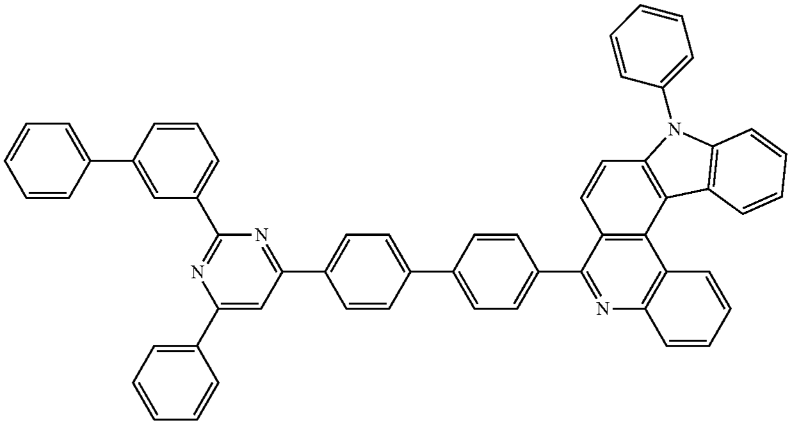
1-304
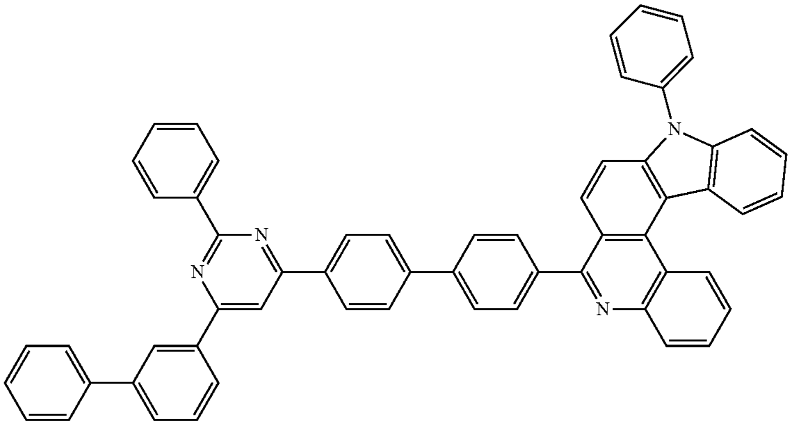
1-305
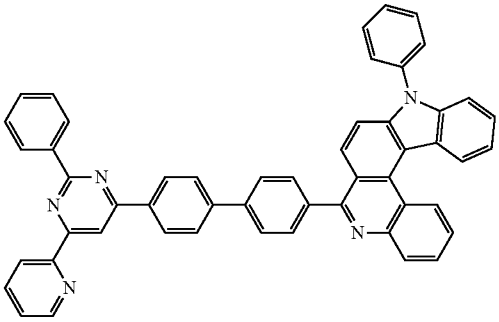
1-306
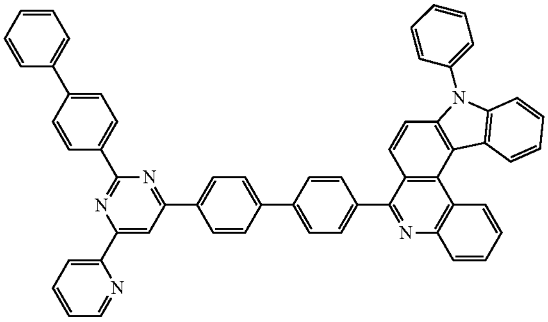

-continued
1-307
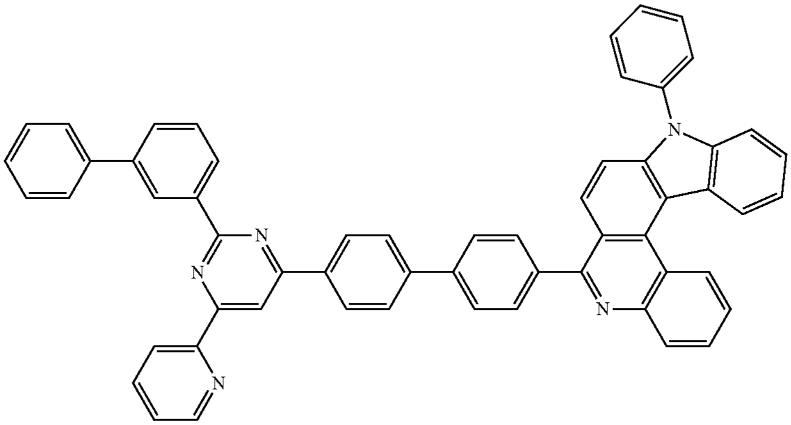
1-308
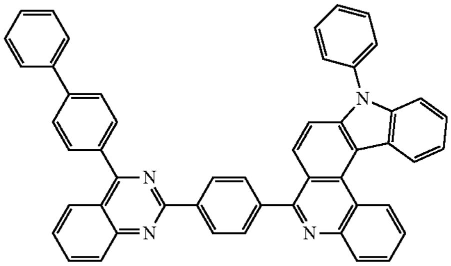
1-309
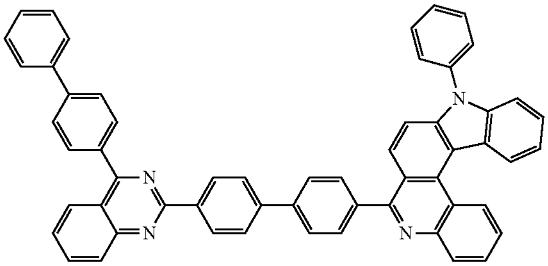
1-310
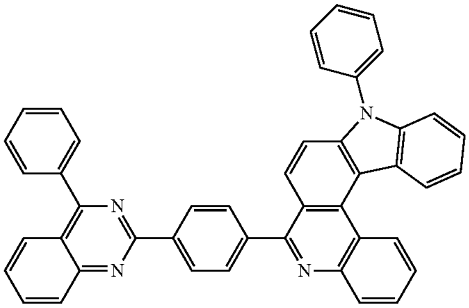
1-311
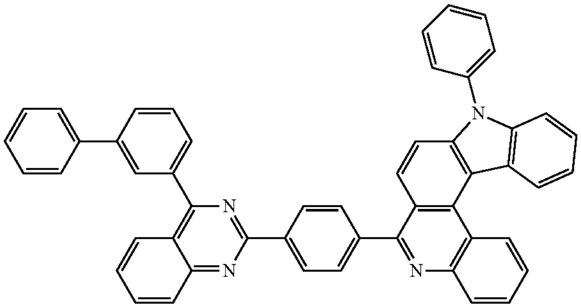
1-312
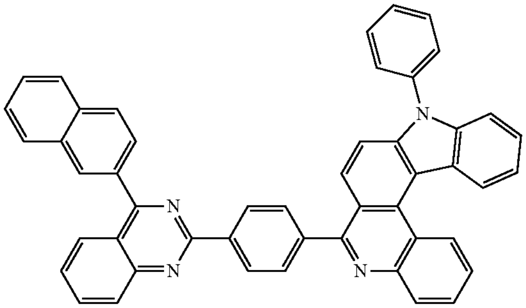
1-313
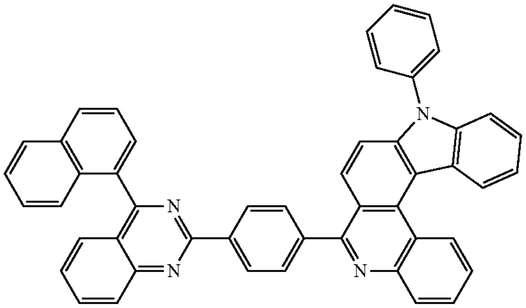

-continued
1-314
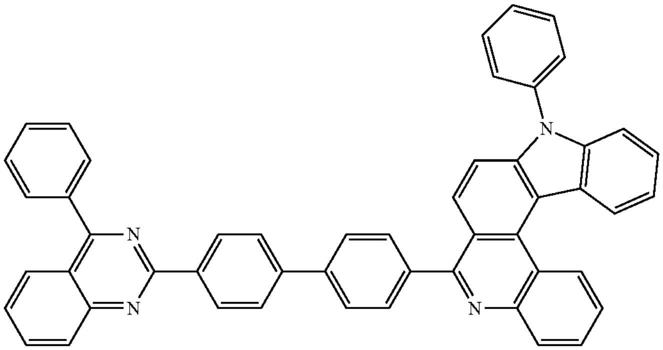
1-315
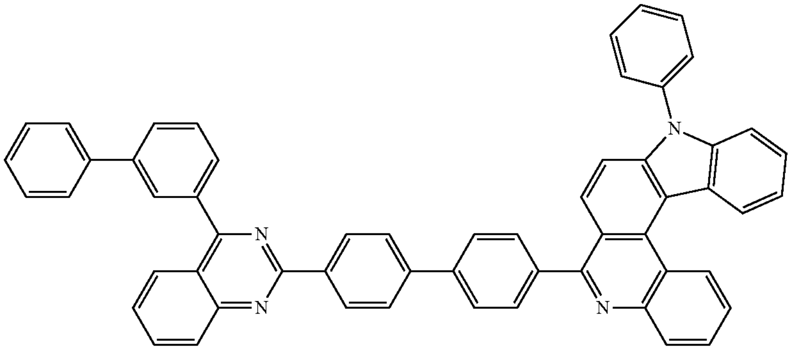
1-316
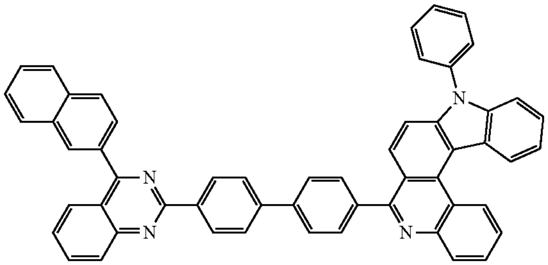
1-317
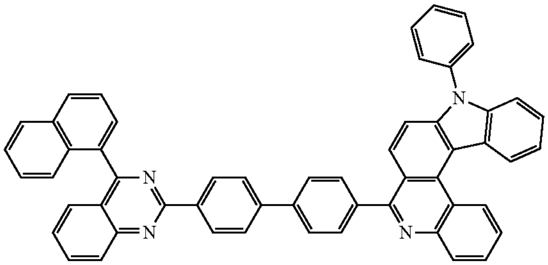
1-318
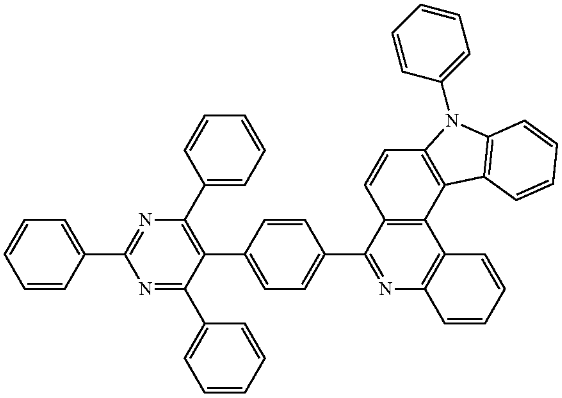
1-319
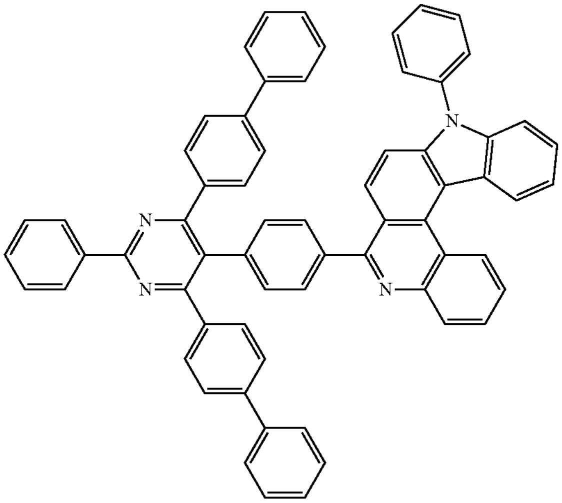

-continued
1-320
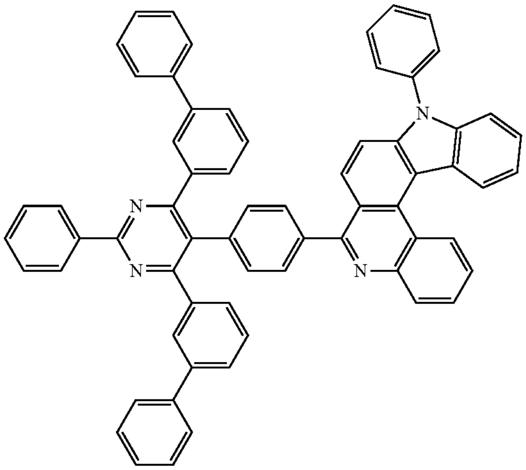
1-321
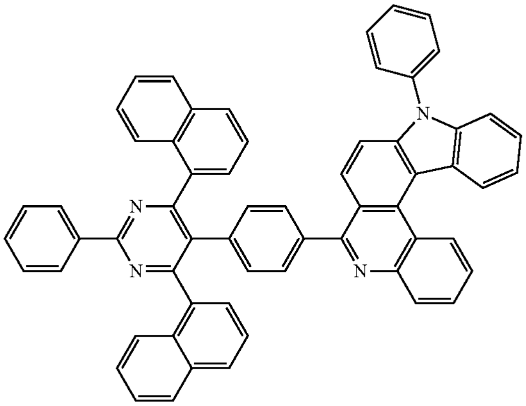
1-322
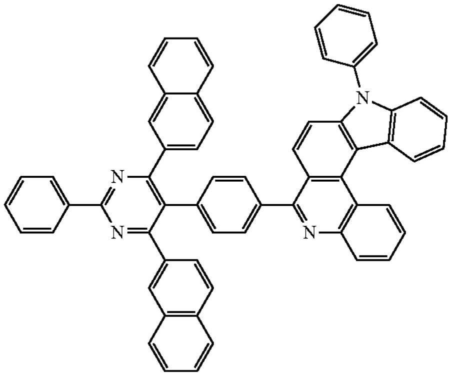
1-323
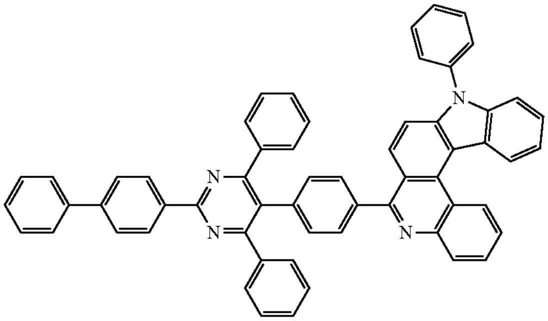
1-324
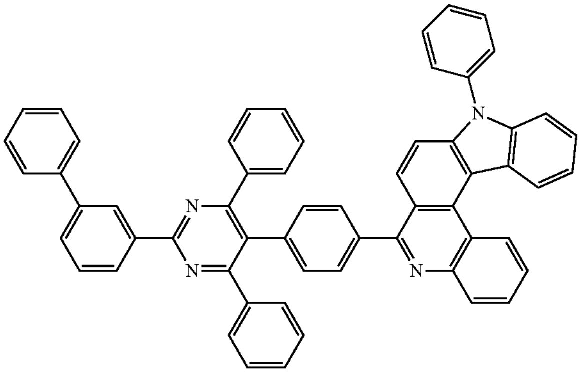
1-326
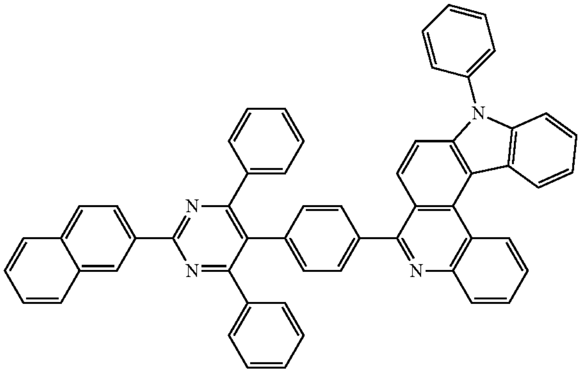

-continued
1-326
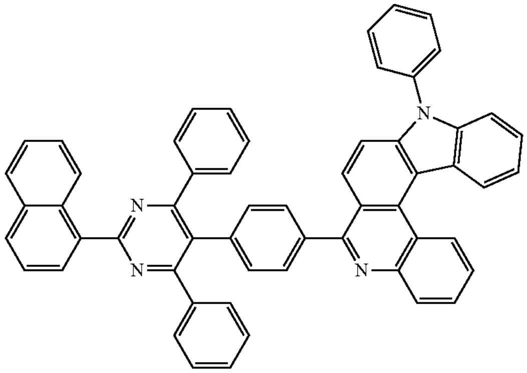
1-327
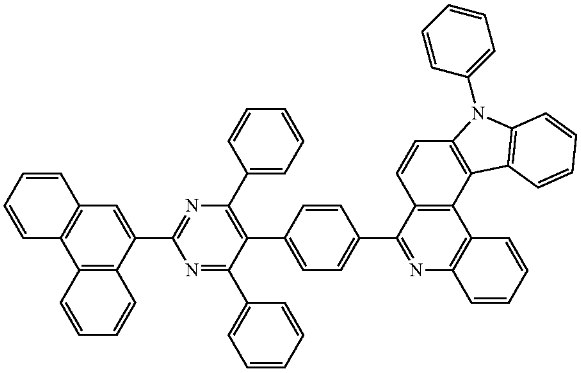
1-328
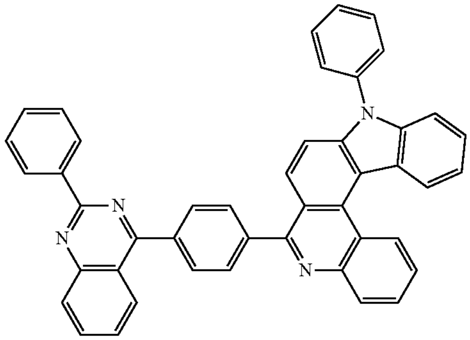
1-329
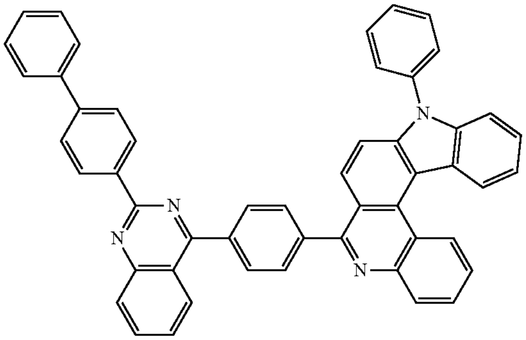
1-330
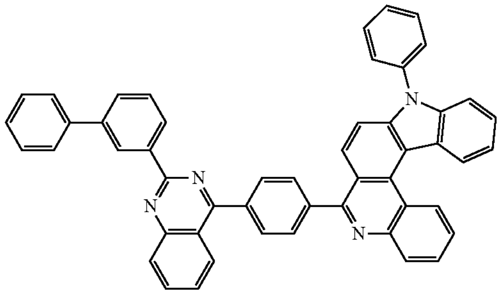
1-331
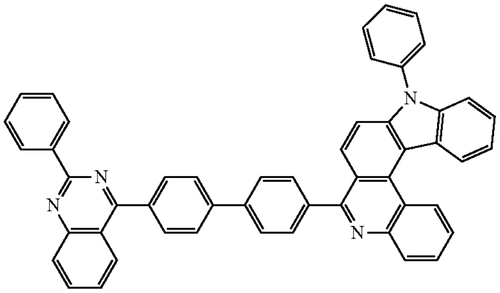
1-332
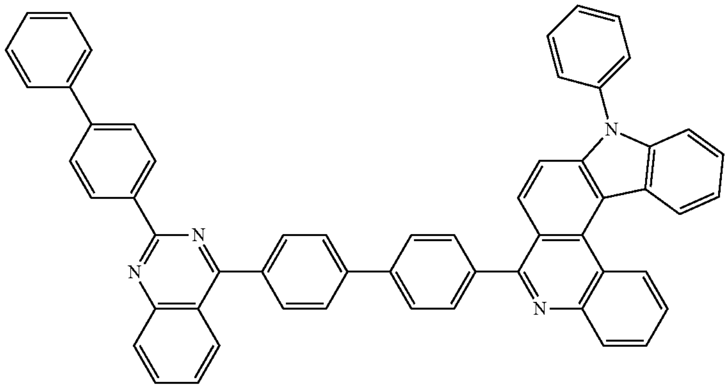

-continued
1-333
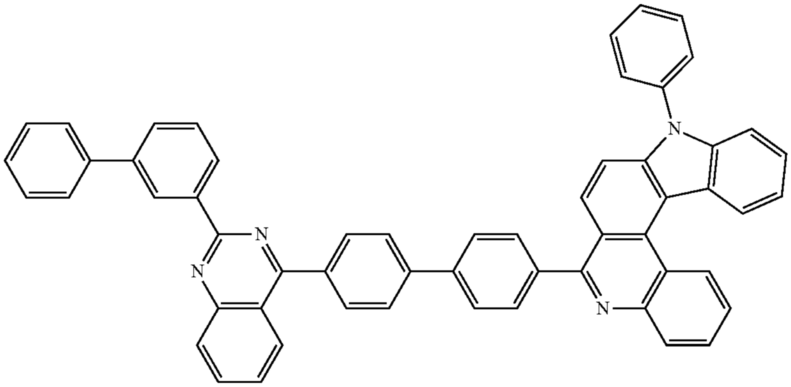
1-334
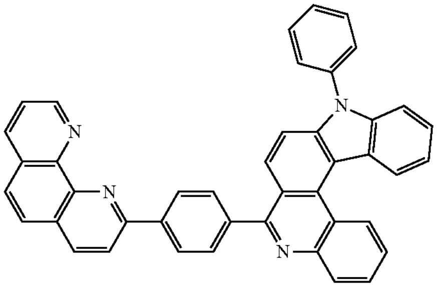
1-335
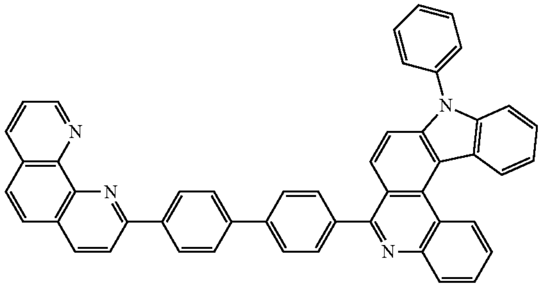
1-336
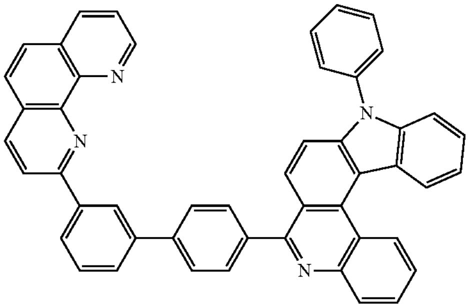
1-337
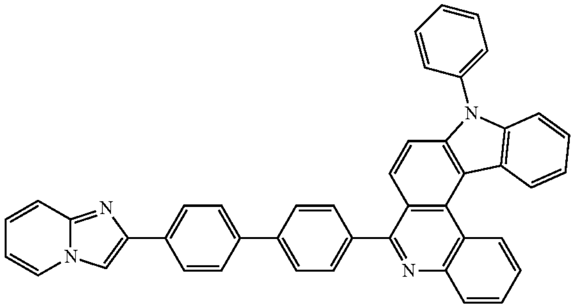
1-338
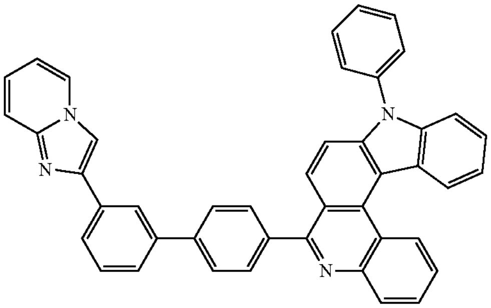
1-339
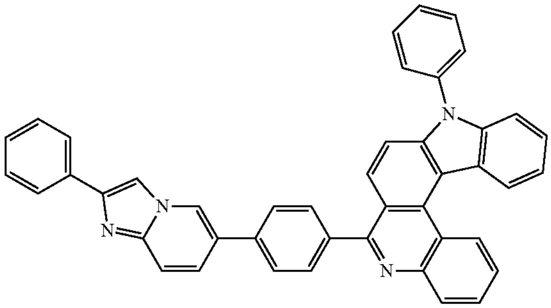

-continued
1-340
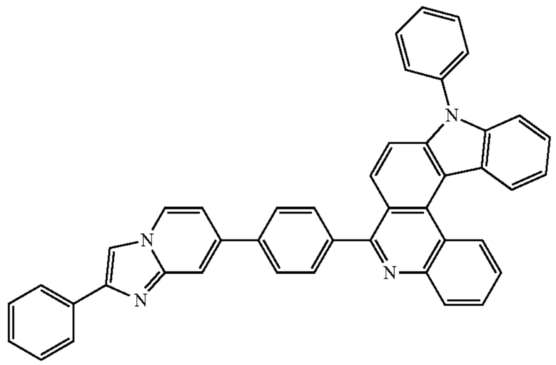
1-341
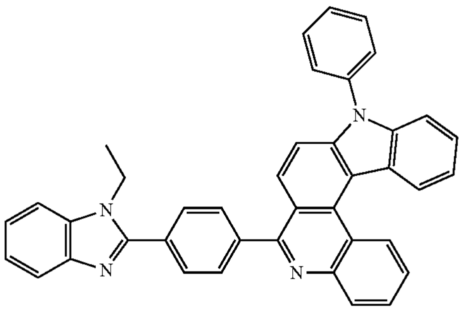
1-342
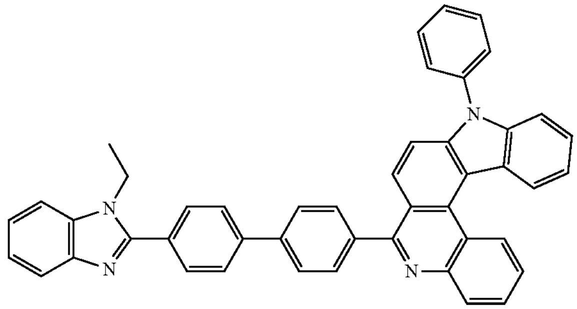
1-343
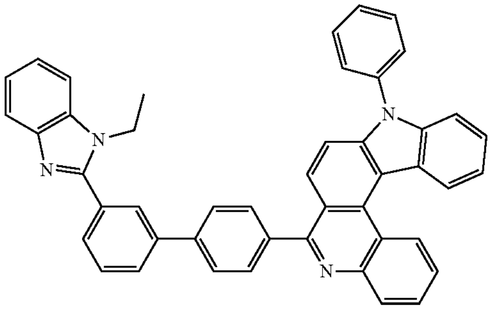
1-344
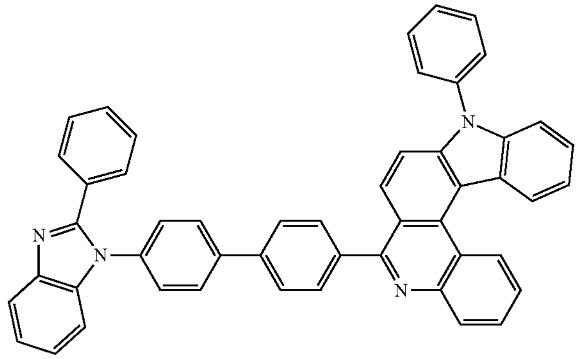
1-345
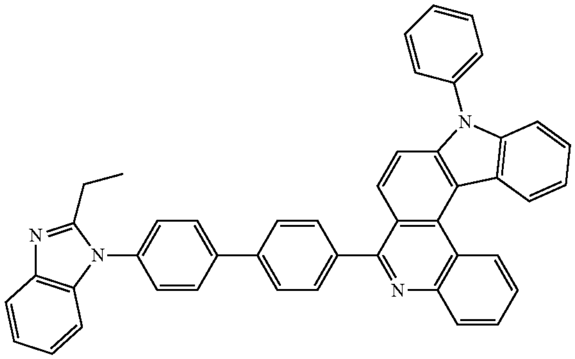
1-346
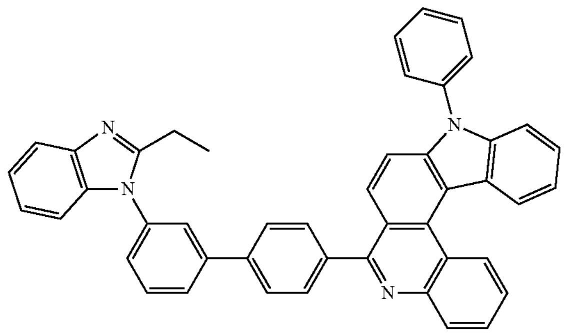
1-347
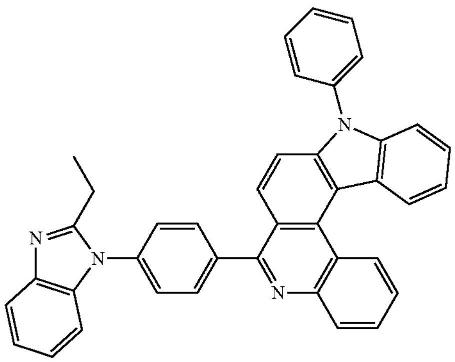

-continued
1-348
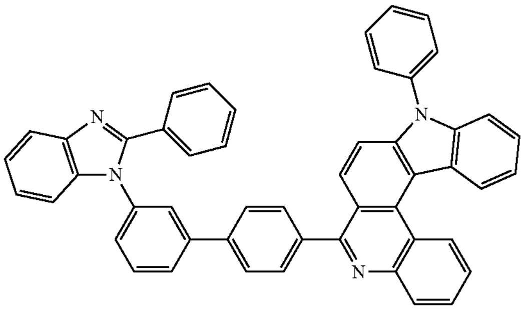
1-349
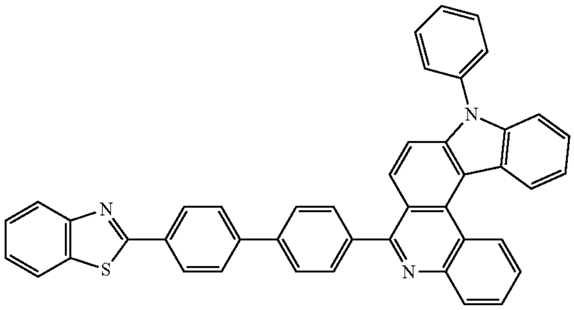
1-350
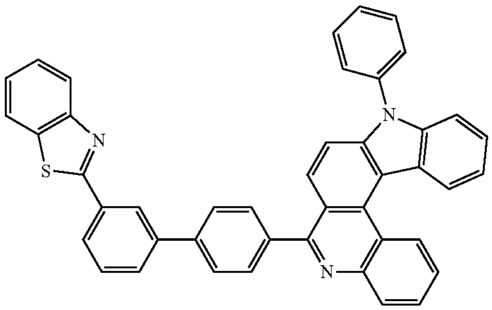
1-351
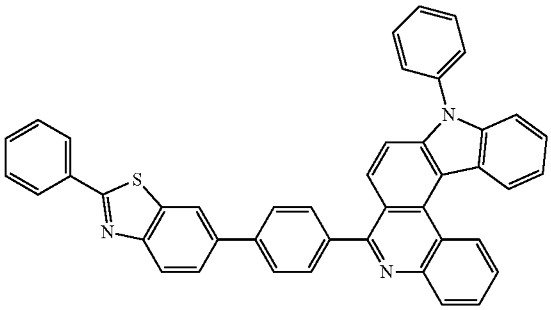
1-352
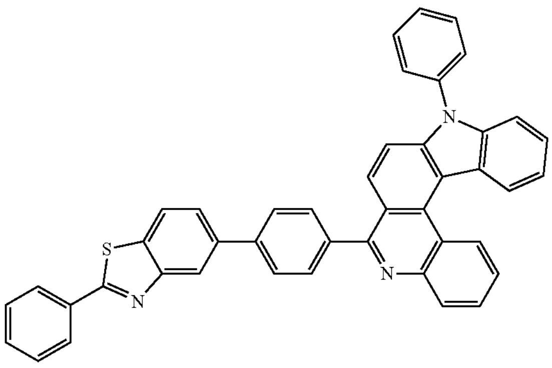
1-353
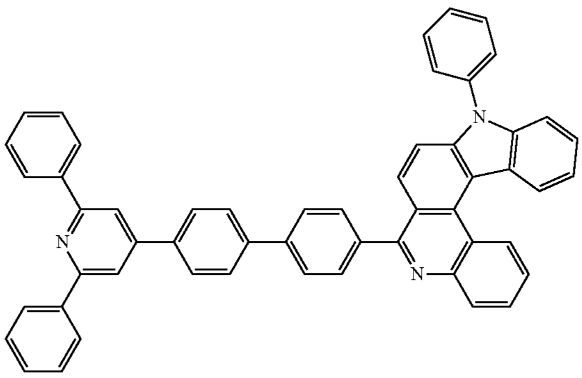
1-354
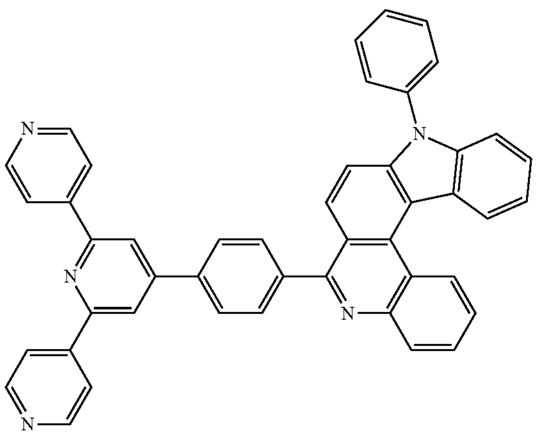
1-355
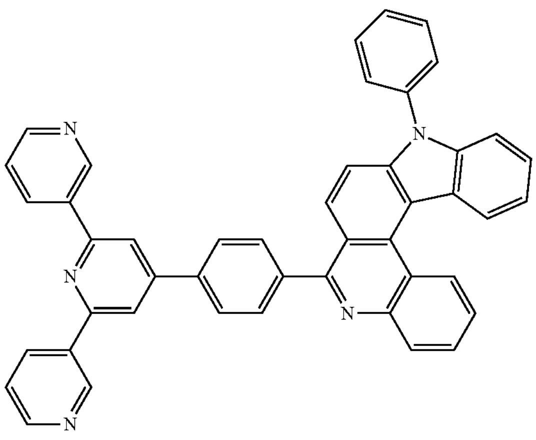

-continued
1-356
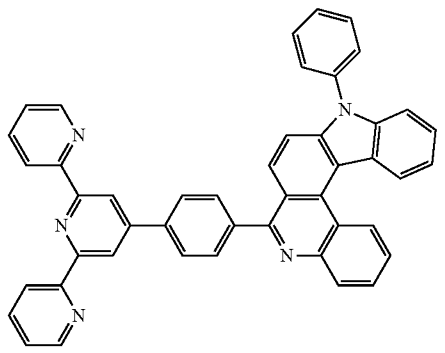
1-357
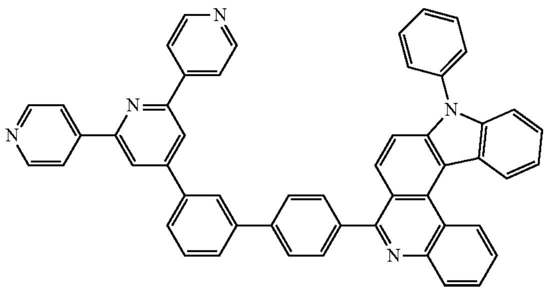
1-358
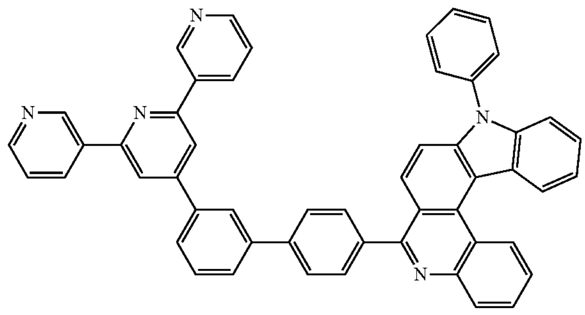
1-359
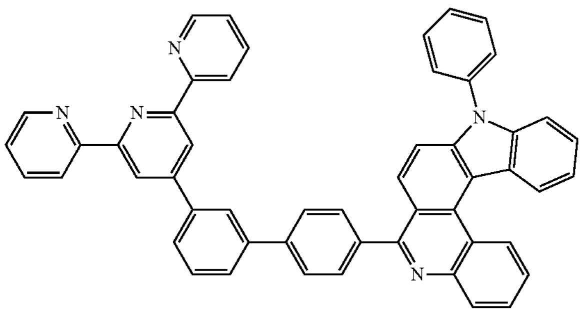
1-360
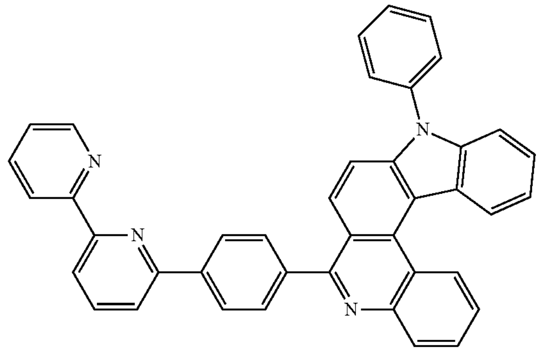
1-361
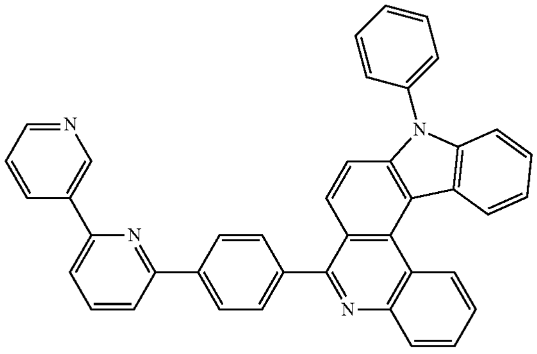
1-362
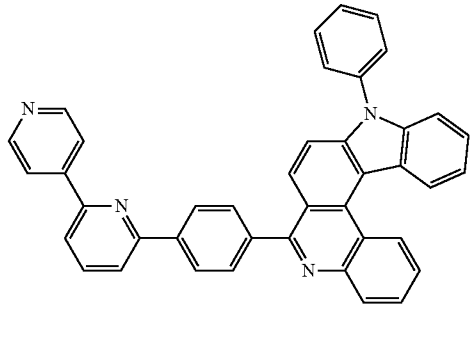
1-363
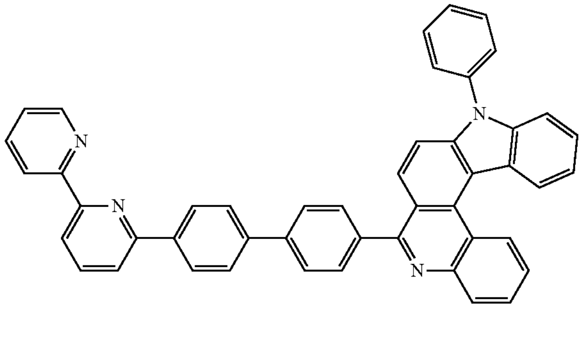

-continued
1-364
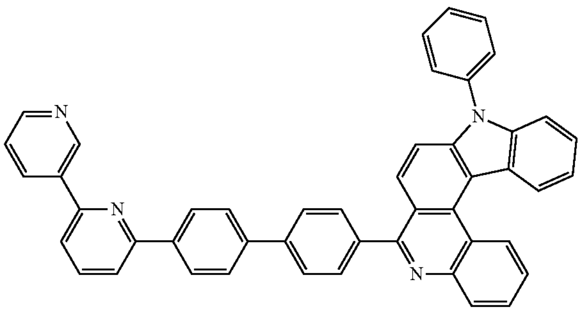
1-365
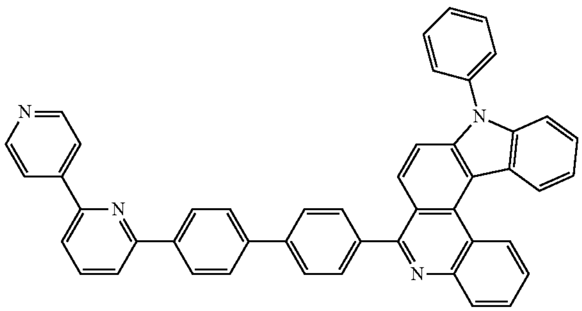
1-495
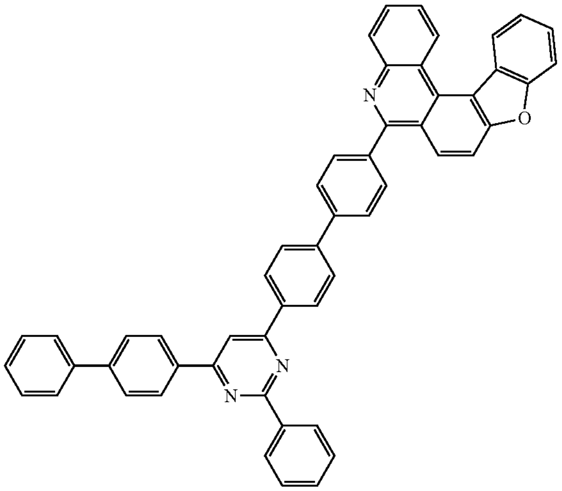
1-496
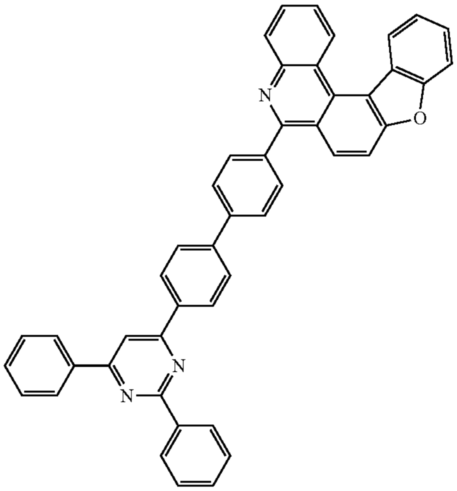
1-497
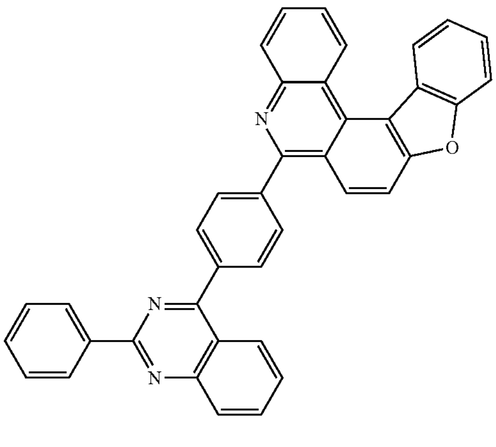
1-498
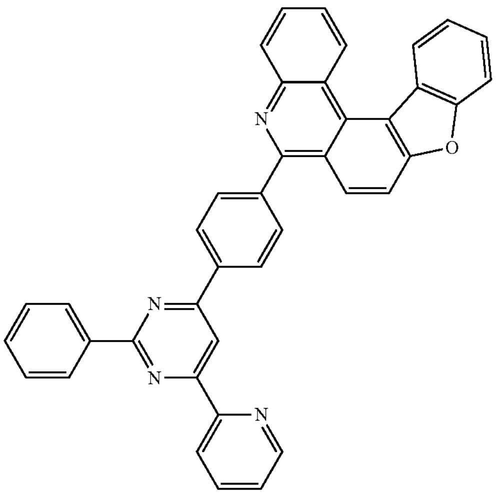

-continued
1-499
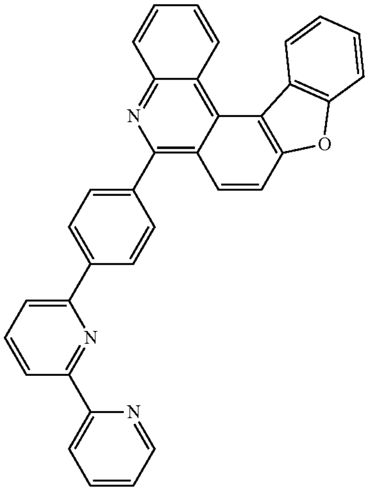
1-500
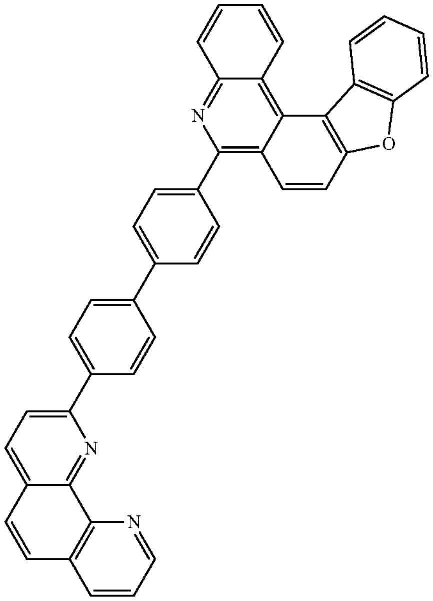
1-501
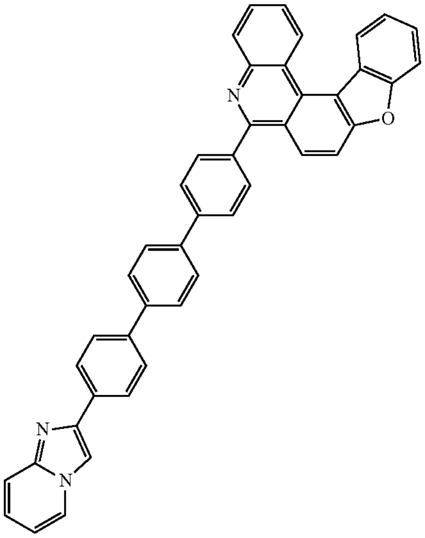
1-502
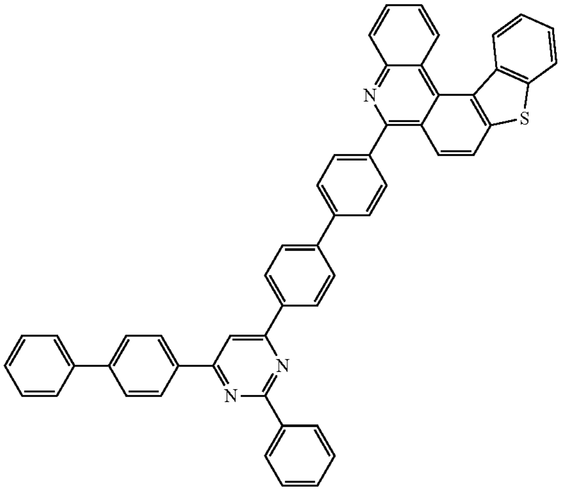

-continued
1-503
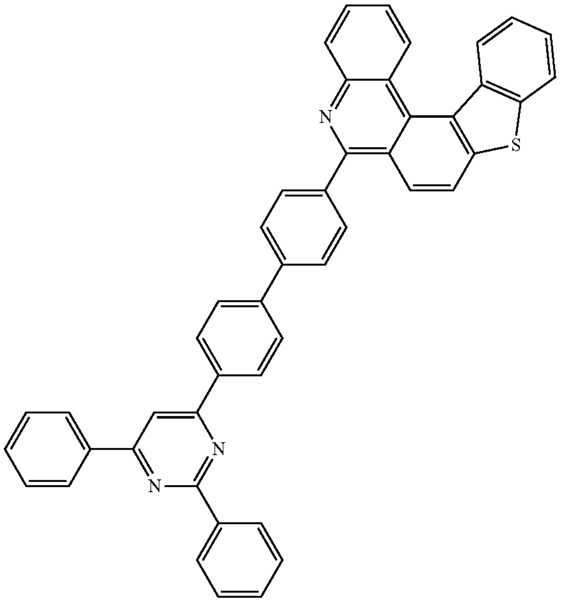
1-504
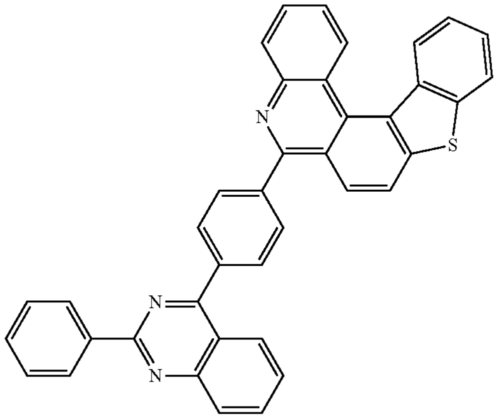
1-505
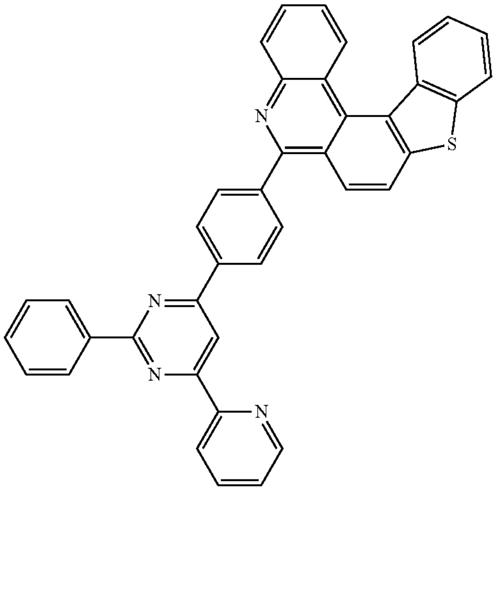
1-506
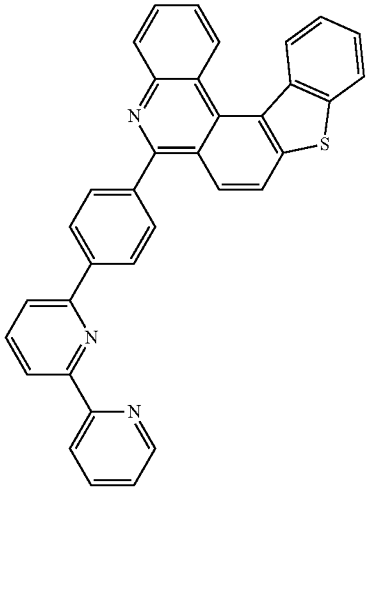

-continued
1-507
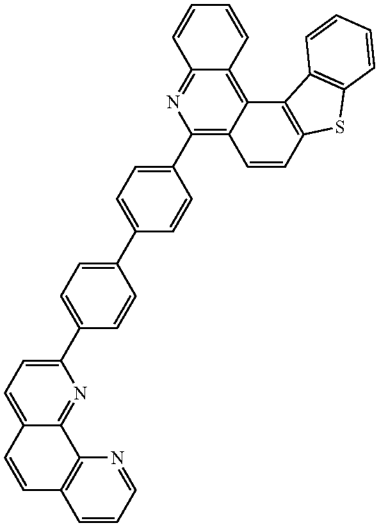
1-508
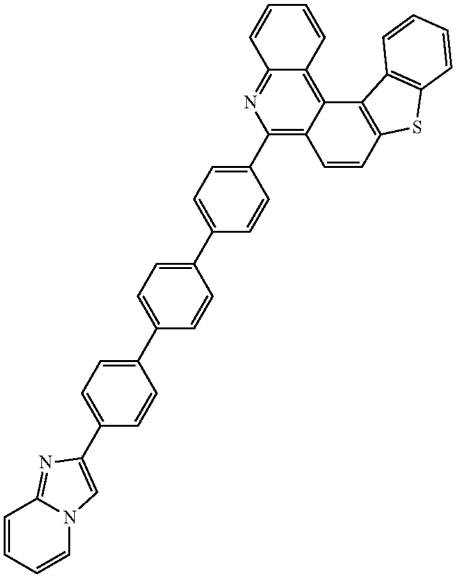
1-509
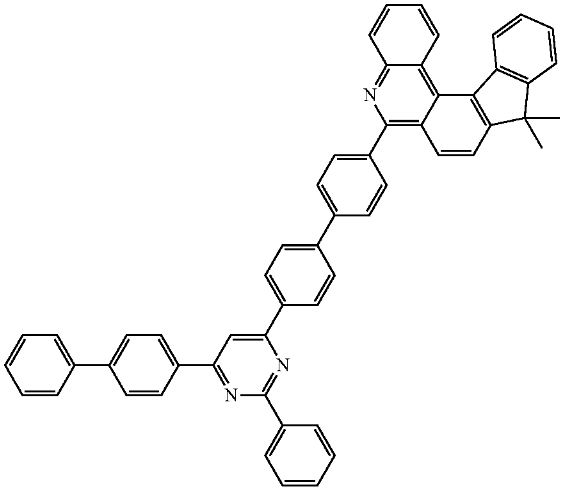
1-510
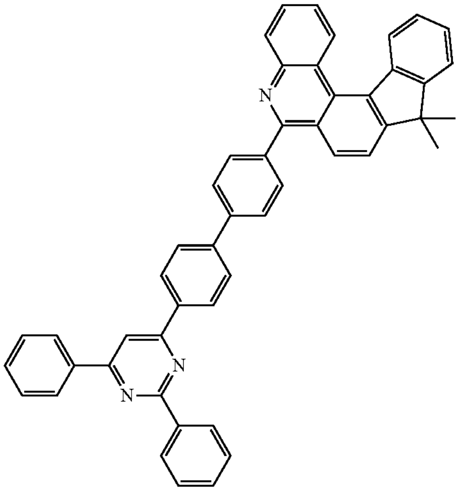
1-511
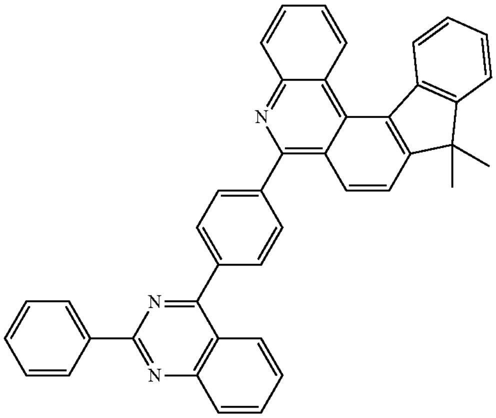
1-512
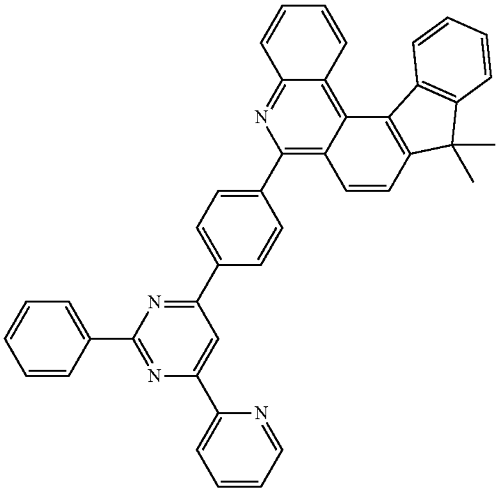

-continued
1-513
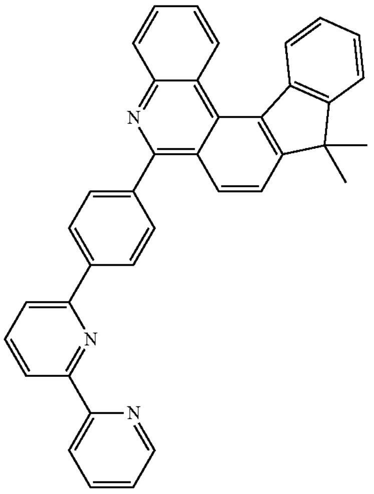
1-514
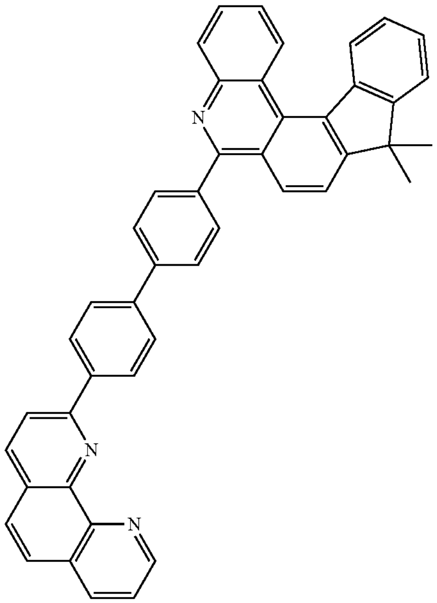
1-515
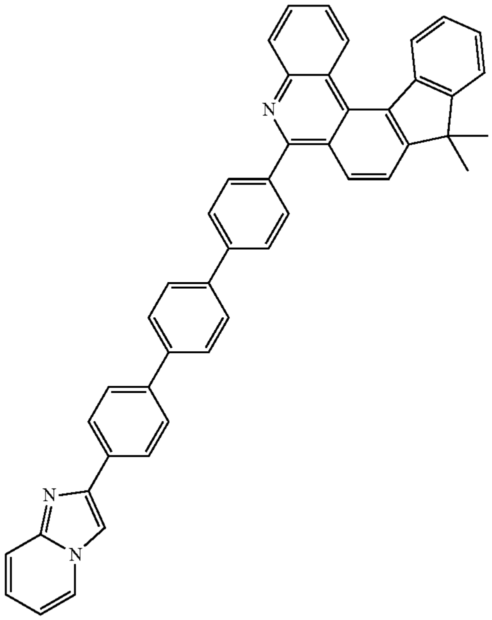
According to another exemplary embodiment of the present specification,
in Chemical Formulas 13 and 25, Ar may be bonded to an atom bonded to a core of phenyl at a meta position thereof, and Chemical Formulas 13 and 25 may be selected from the following compounds.

-continued
1-91
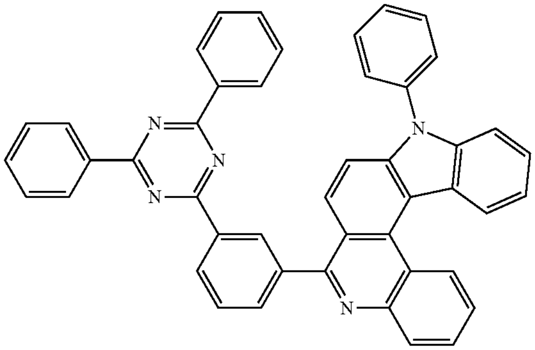
1-92
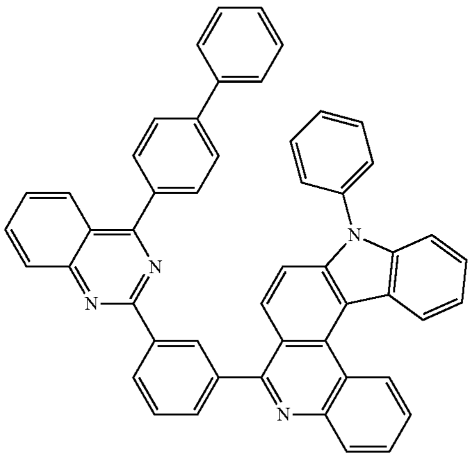
1-93
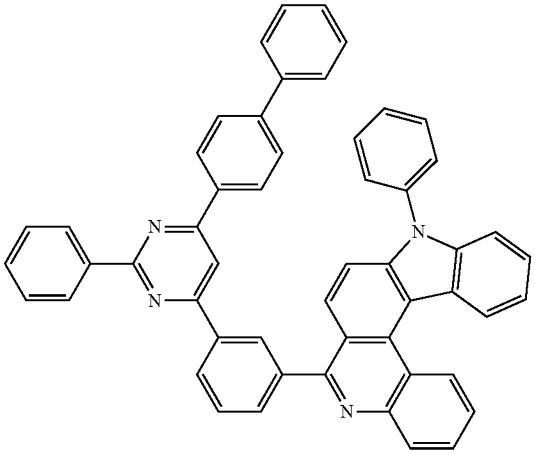
1-94
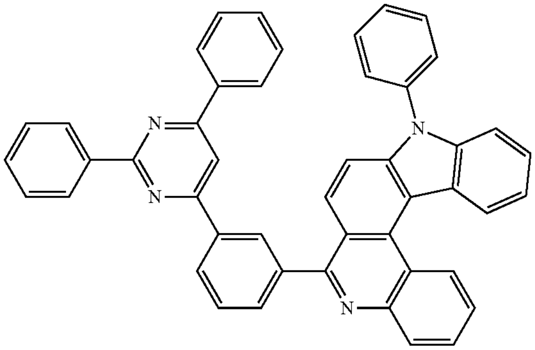
1-95
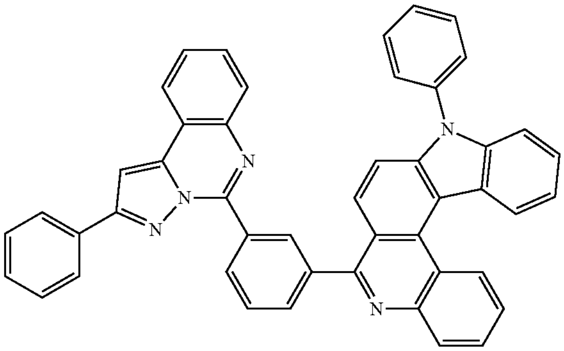
1-96
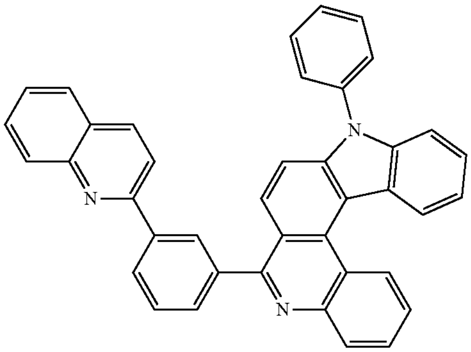
1-97
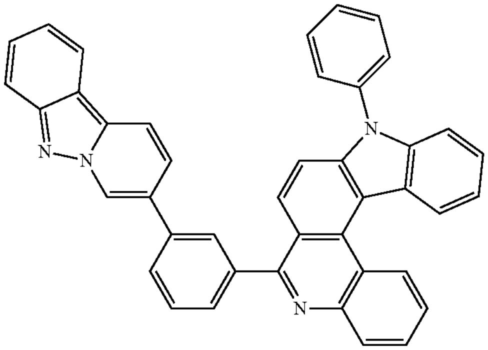

-continued
1-98
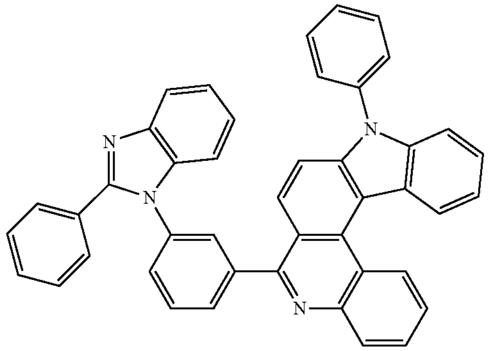
1-99
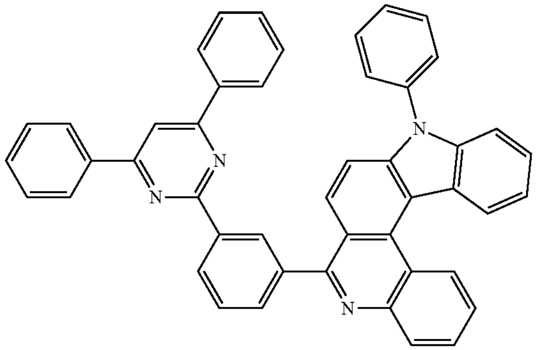
1-100
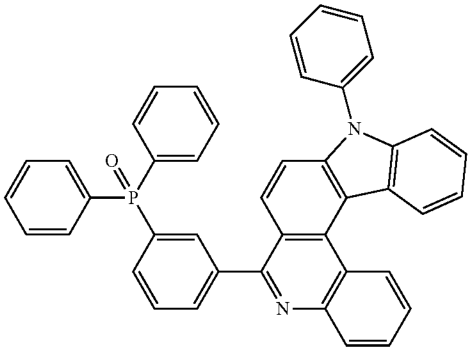
1-101
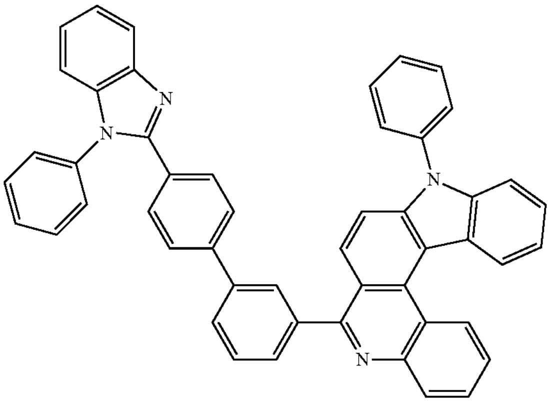
-continued
1-102
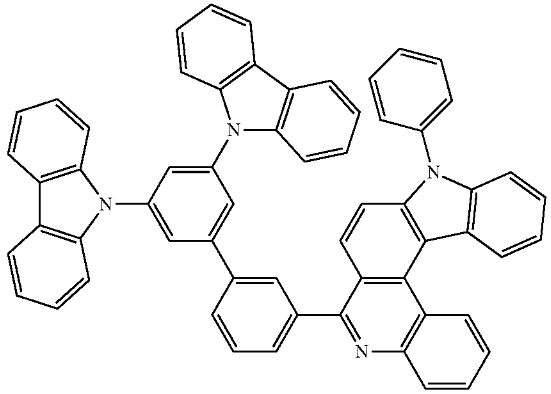
1-103
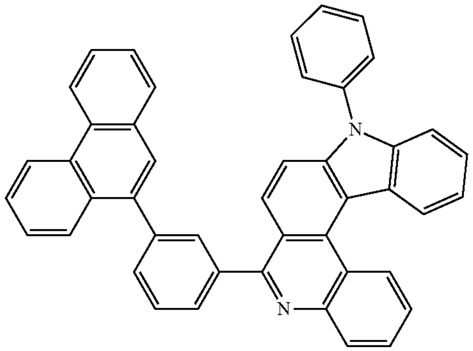
1-104
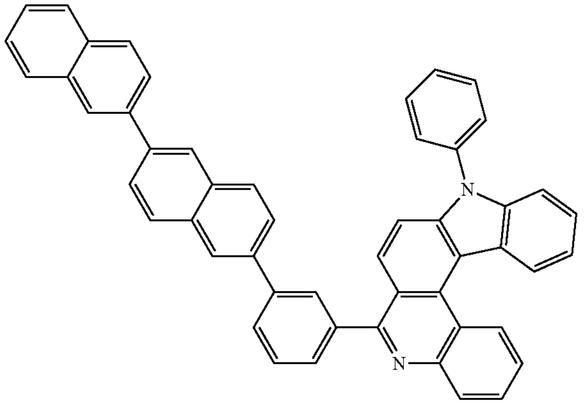
1-105
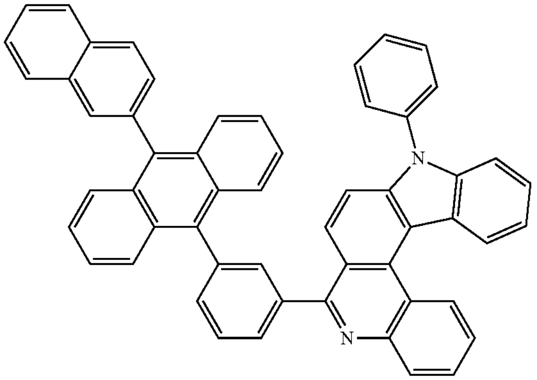

-continued
1-106
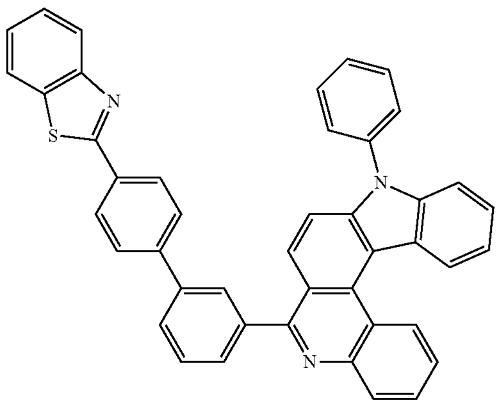
1-107
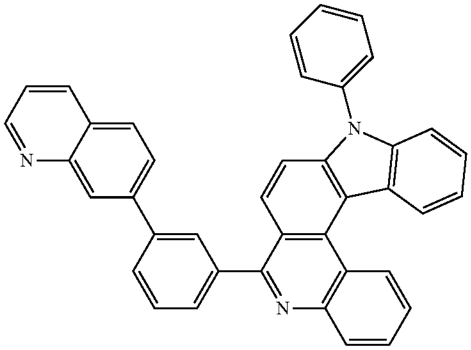
1-108
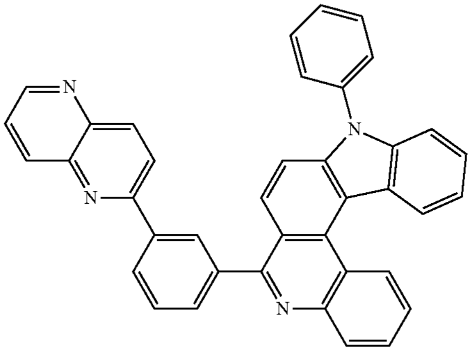
1-109
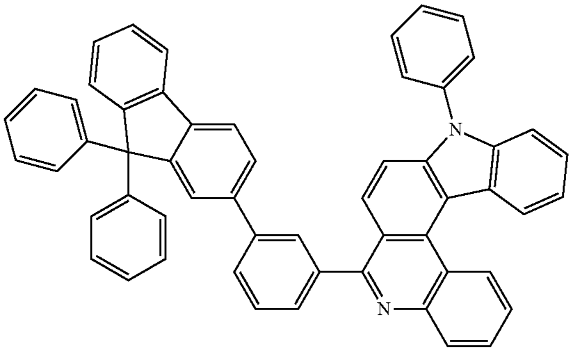
-continued
1-110
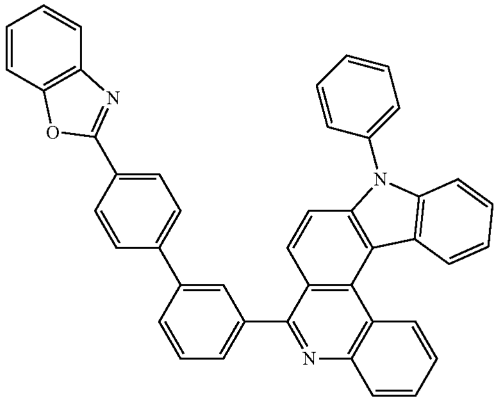
1-111
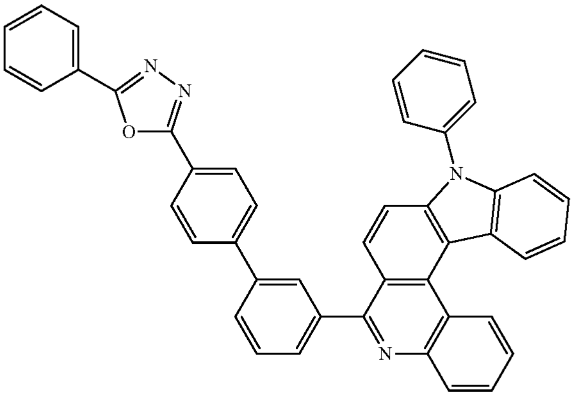
1-112
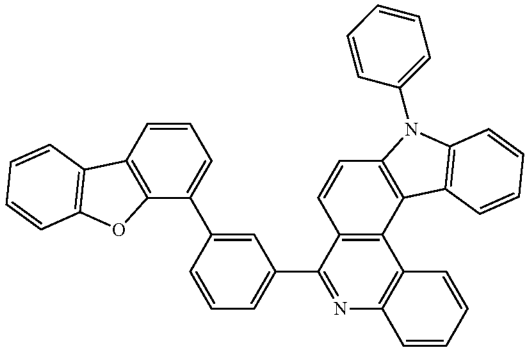
1-113
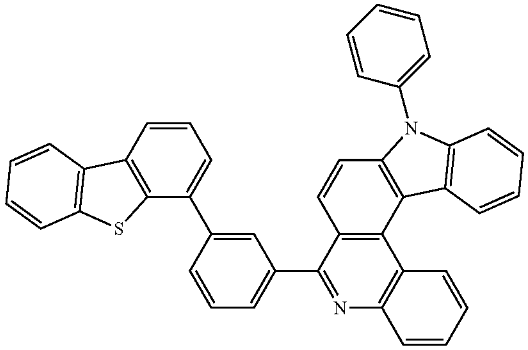

-continued
1-114
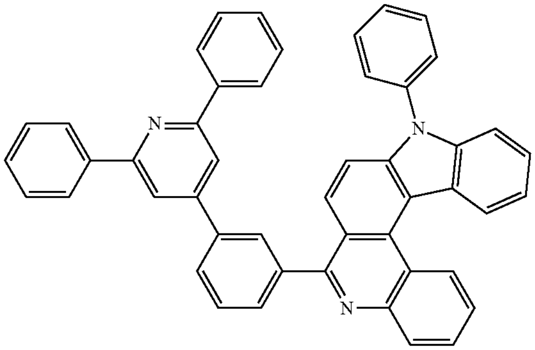
1-115
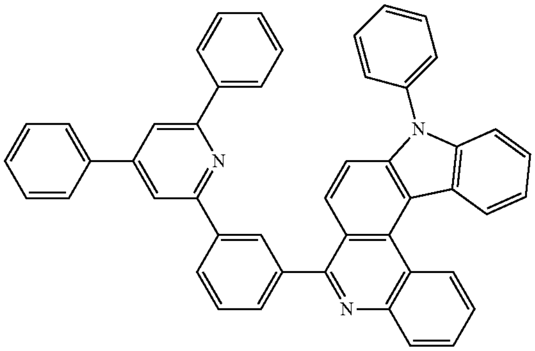
1-116
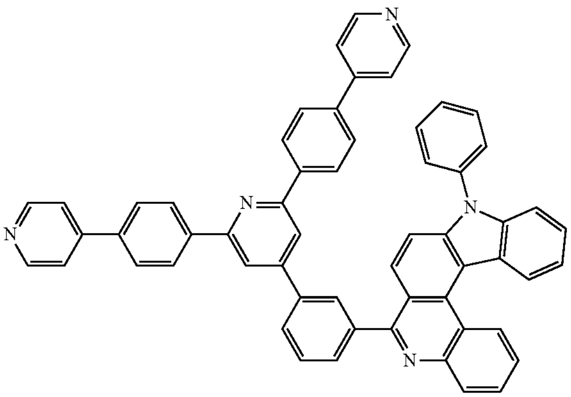
1-117
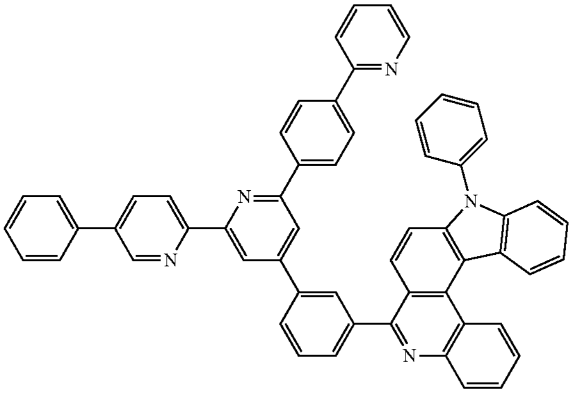
-continued
1-118
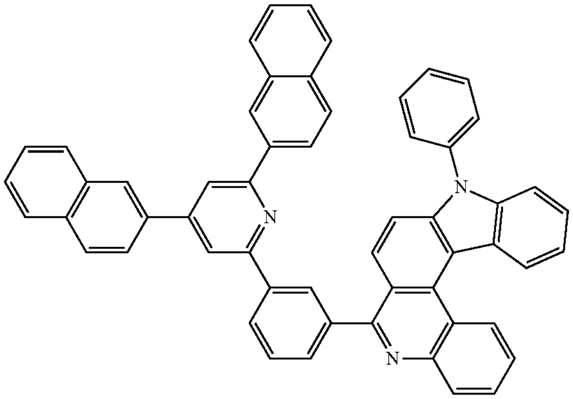
1-119
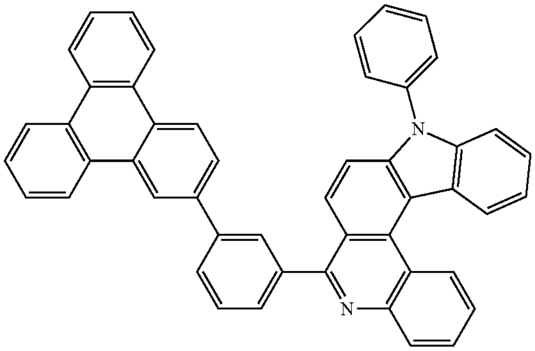
1-120
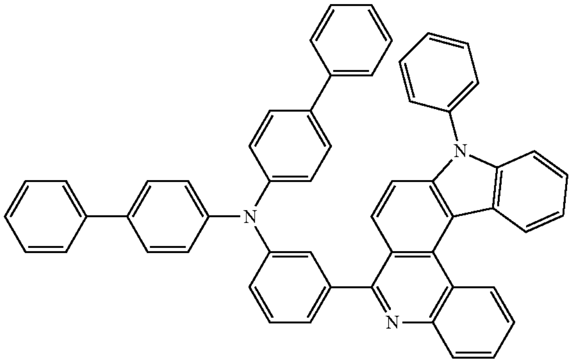
1-121
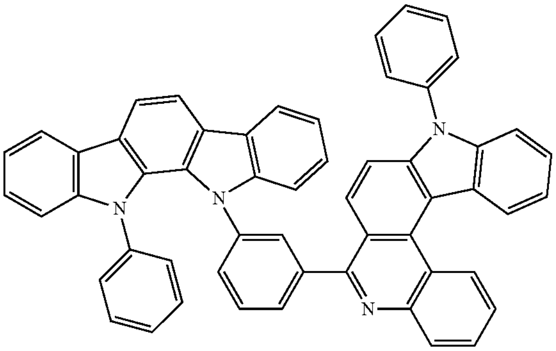

-continued
1-122
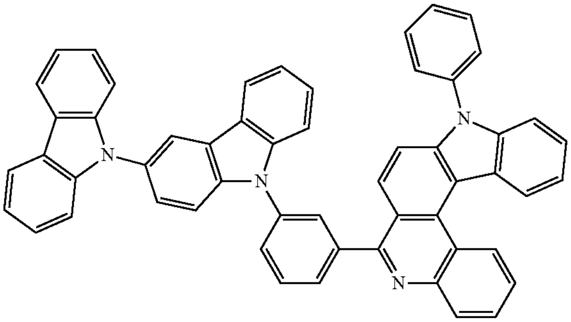
1-123
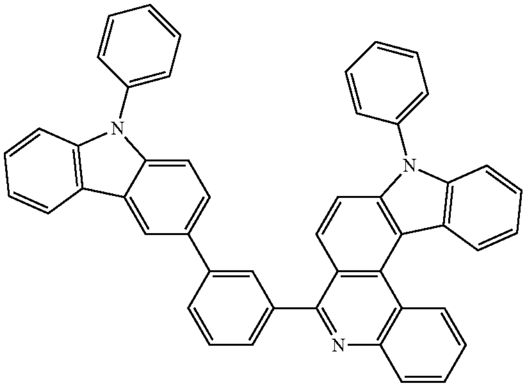
1-124
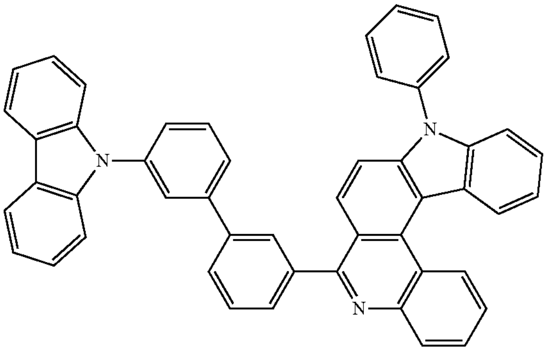
1-125
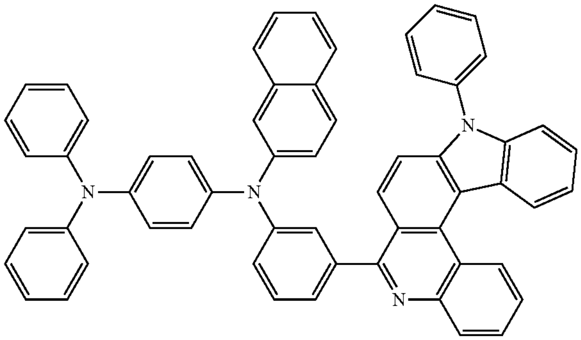
-continued
1-126
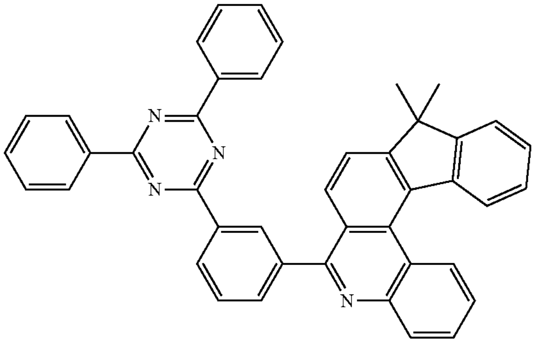
1-127
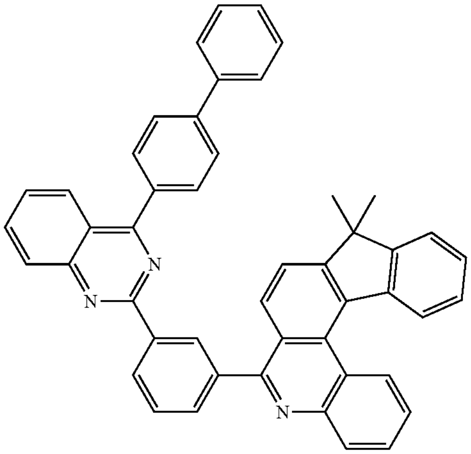
1-128
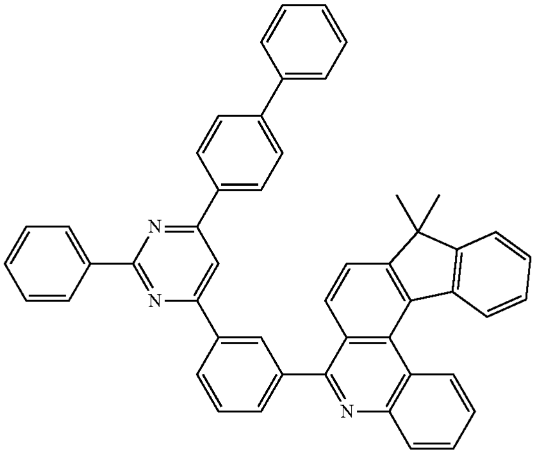

-continued
1-129
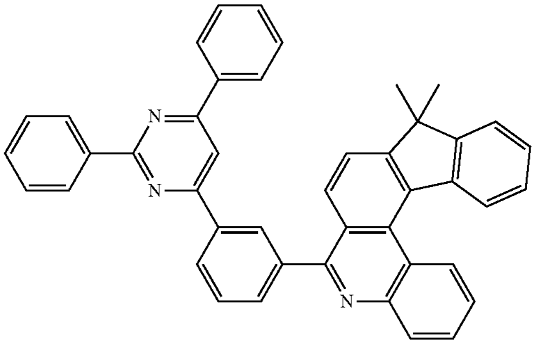
1-130
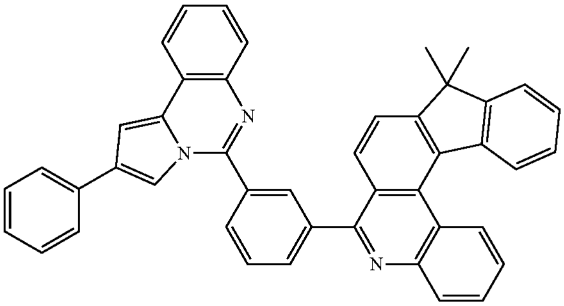
1-131
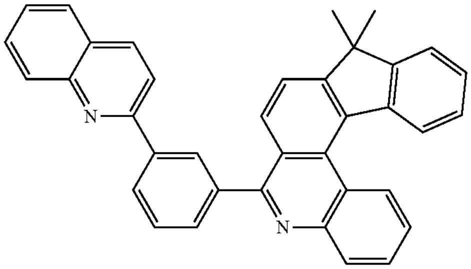
1-132
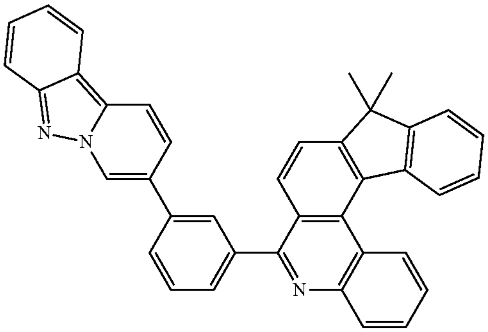
1-133
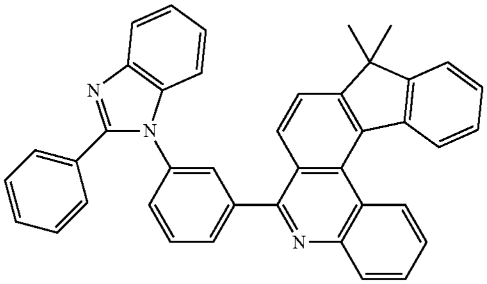
-continued
1-134
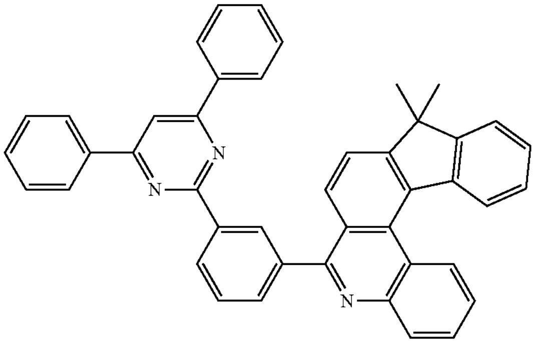
1-135
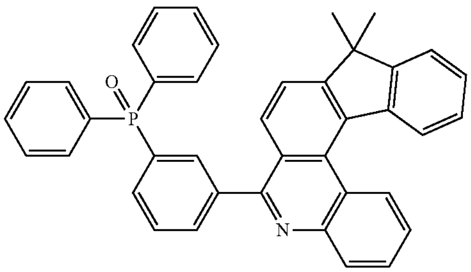
1-136
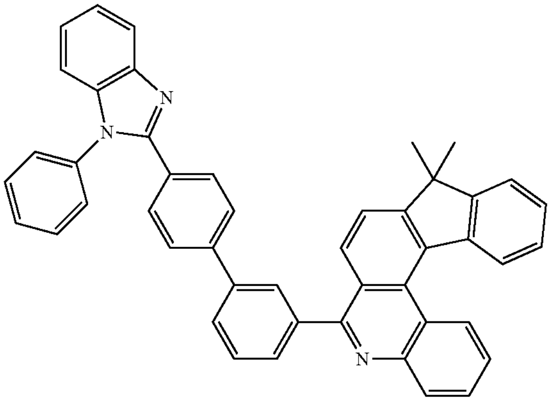
1-137
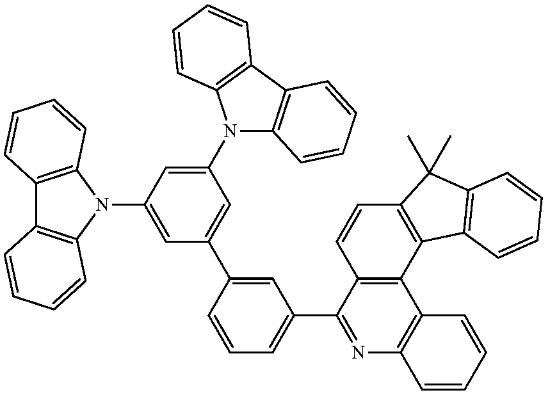

-continued
1-138
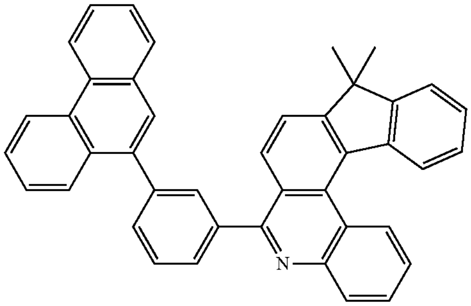
1-139
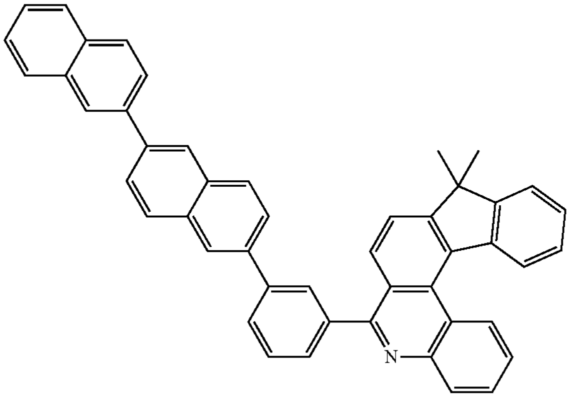
1-140
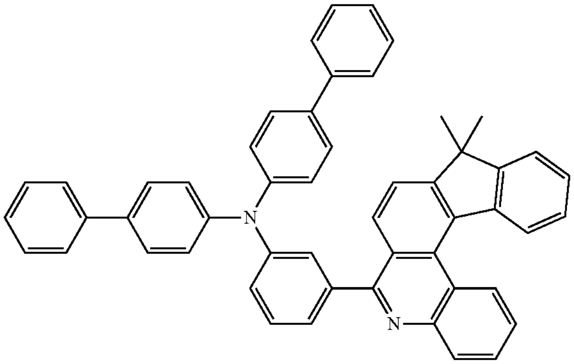
1-141
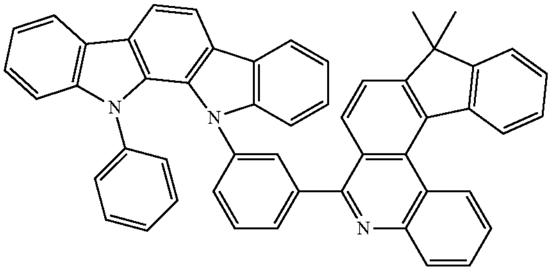
-continued
1-142
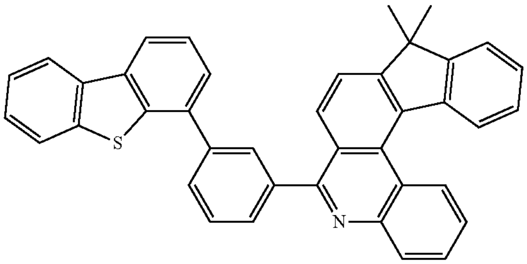
1-143
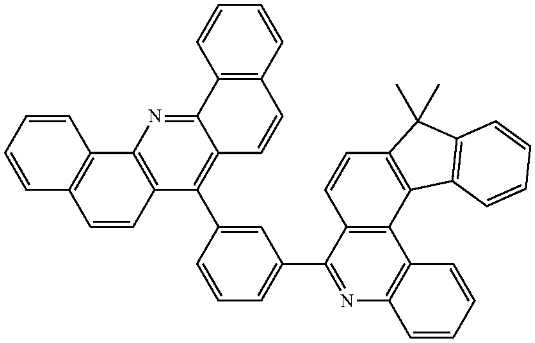
1-144
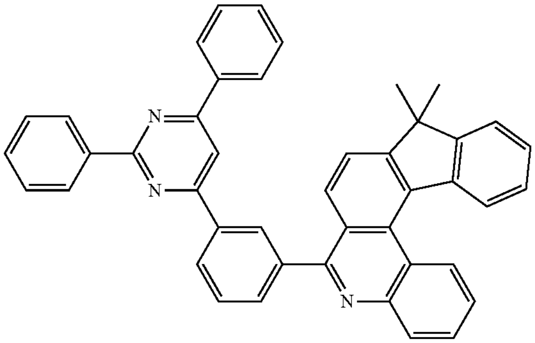
1-145
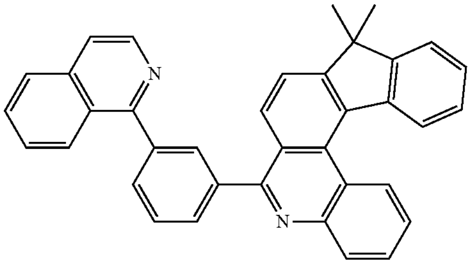

-continued
1-146
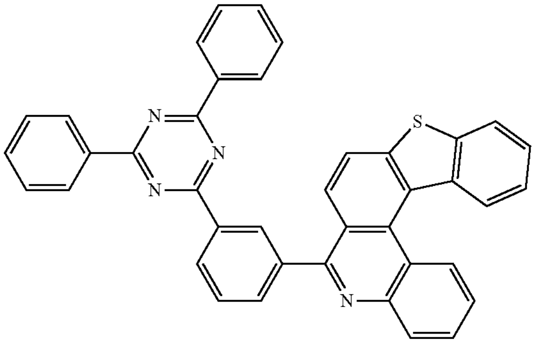
1-147
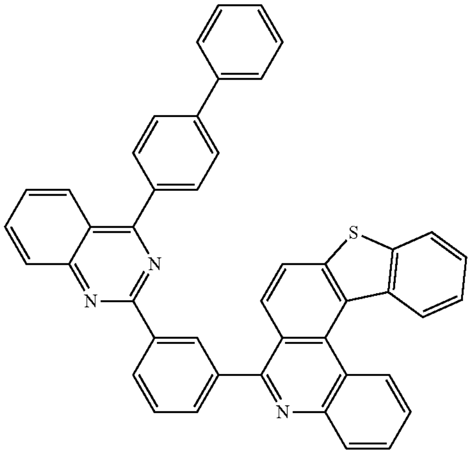
1-148
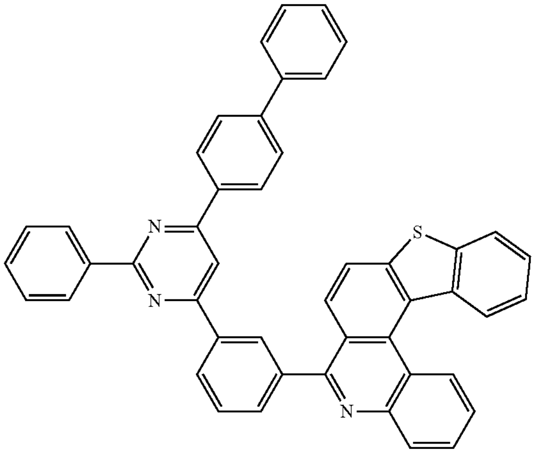
-continued
1-149
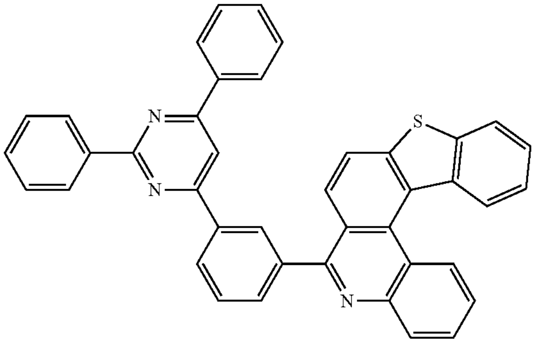
1-150
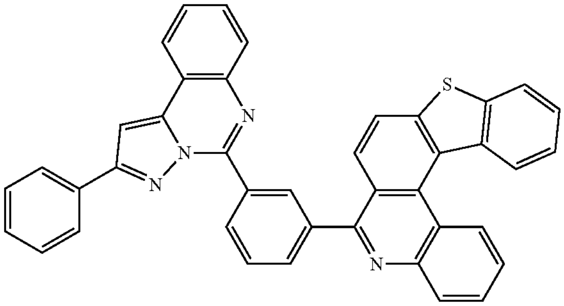
1-151
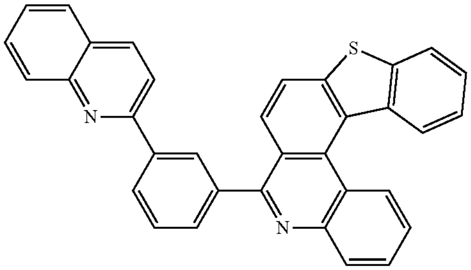
1-152
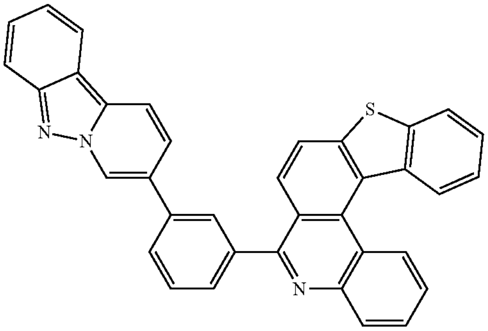
1-153
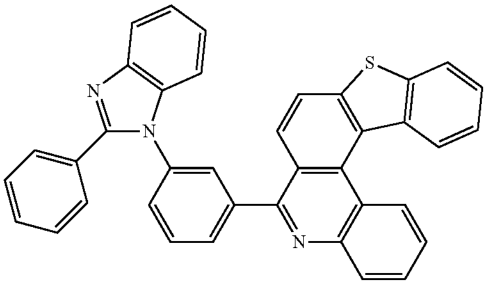

-continued
1-154
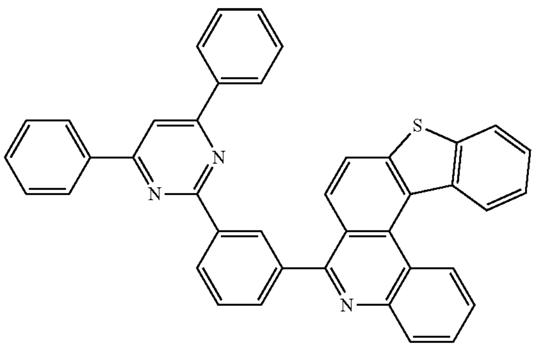
1-155
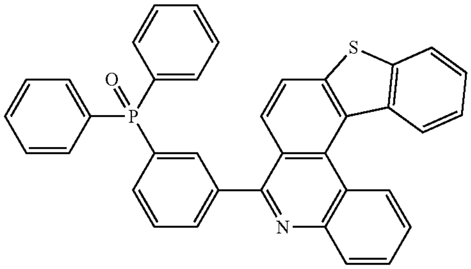
1-156
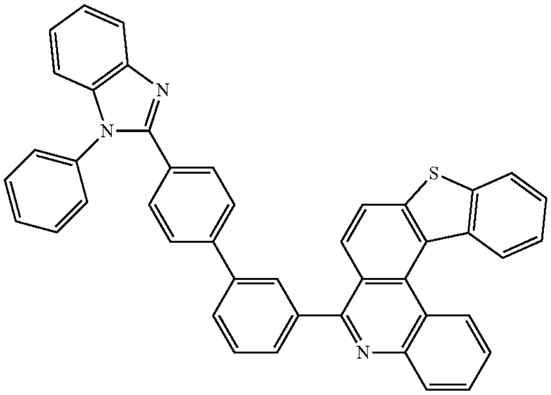
1-157
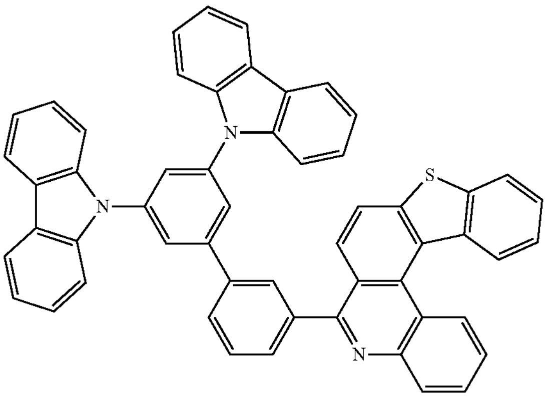
-continued
1-158
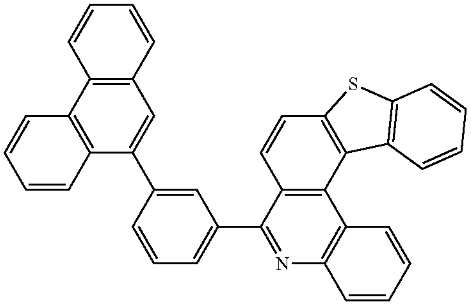
1-159
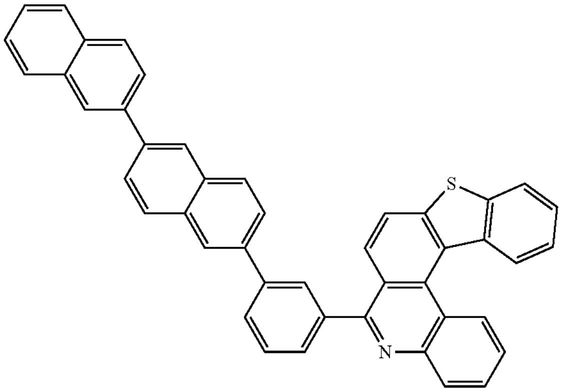
1-160
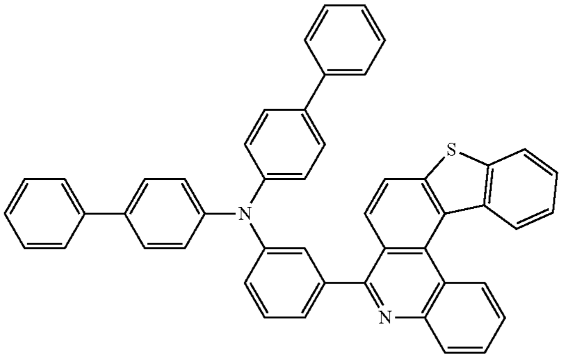
1-161
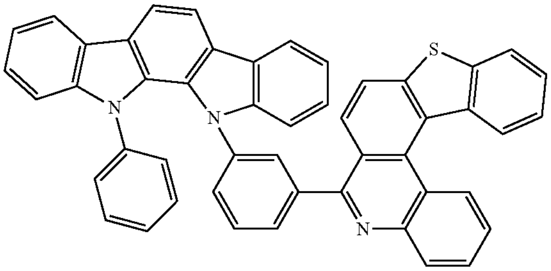

-continued
1-162
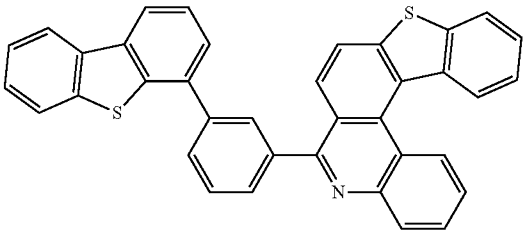
1-163
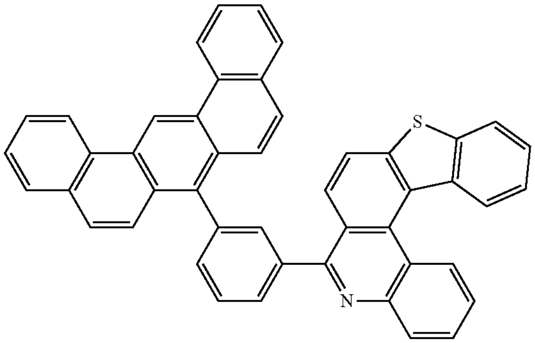
1-164
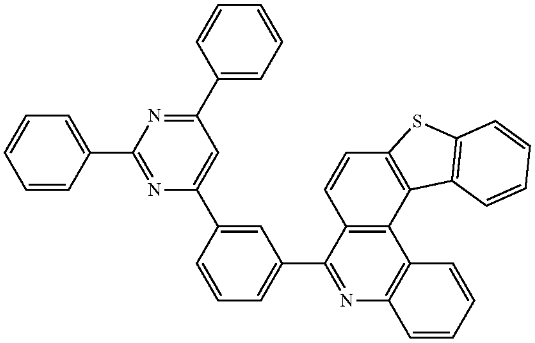
1-165
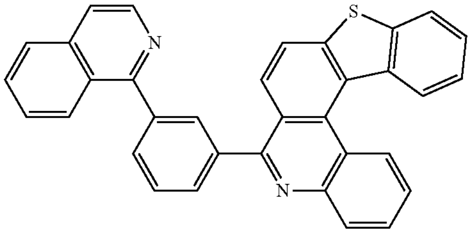
1-166
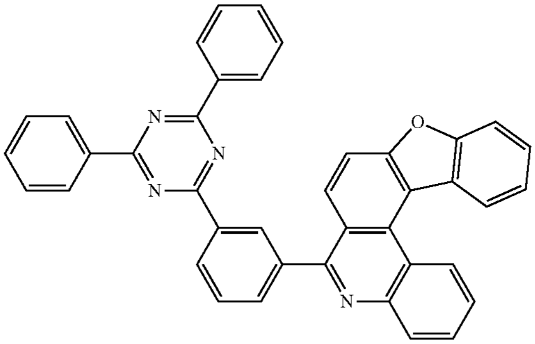
-continued
1-167
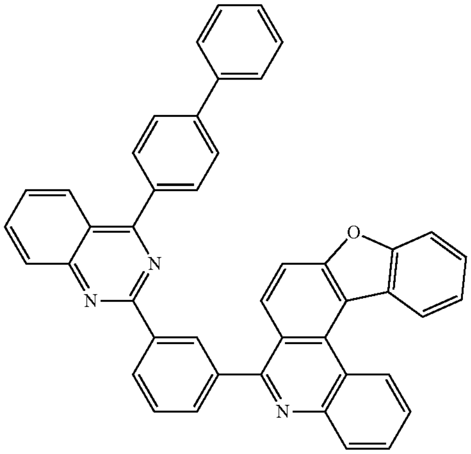
1-168
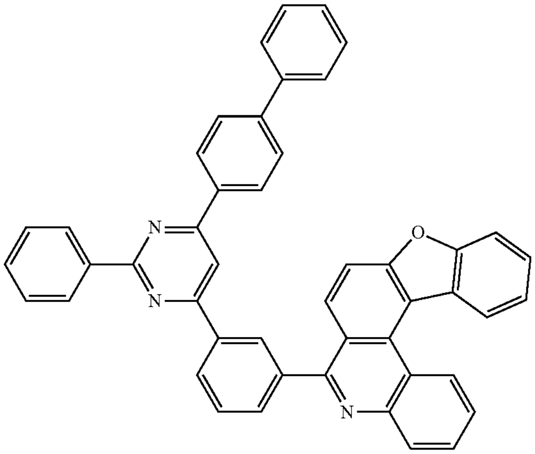
1-169
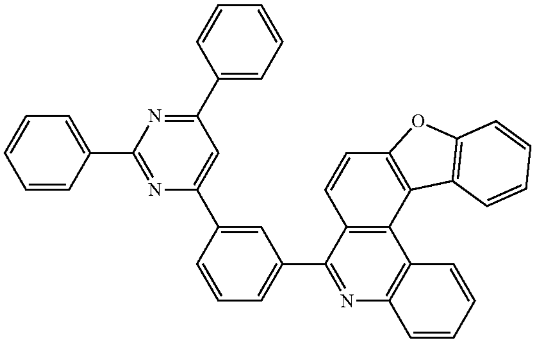
1-170
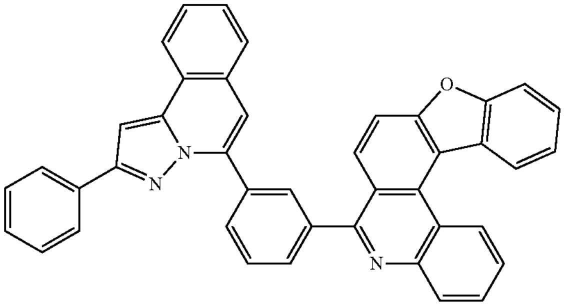

-continued
1-171
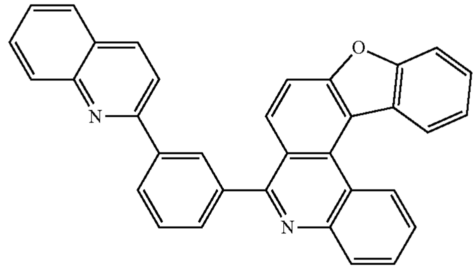
1-172
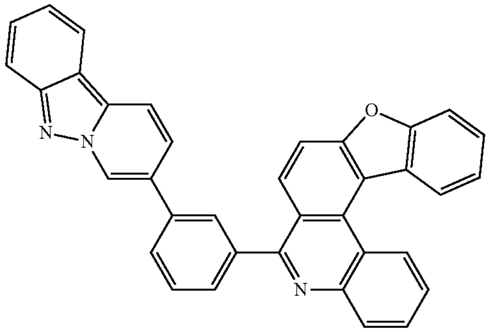
1-173
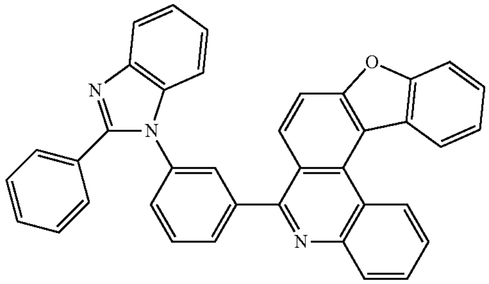
1-174
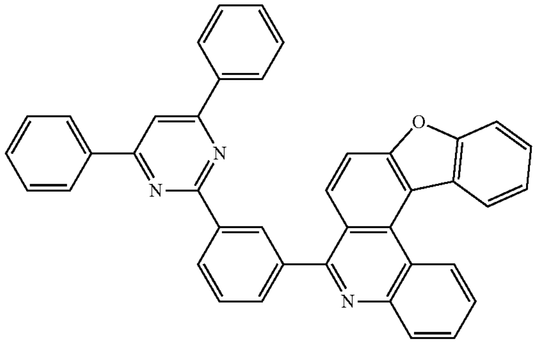
1-175
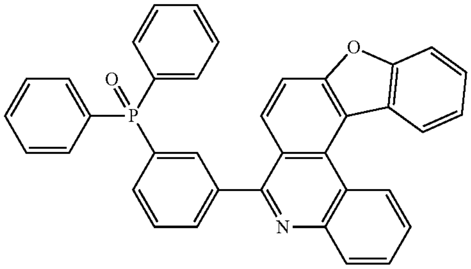
-continued
1-176
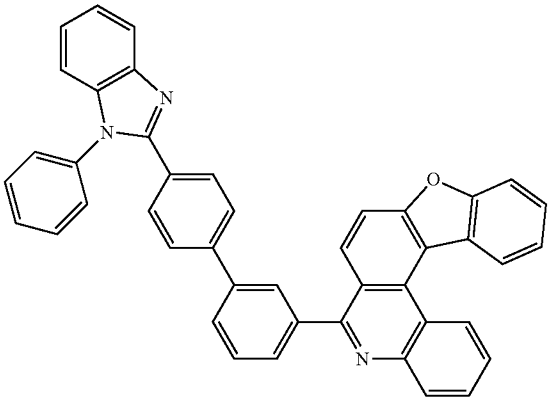
1-177
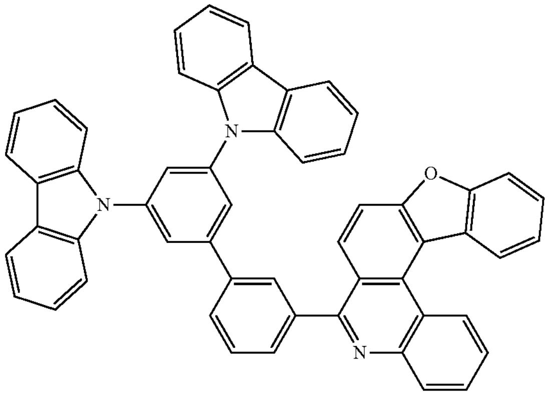
1-178
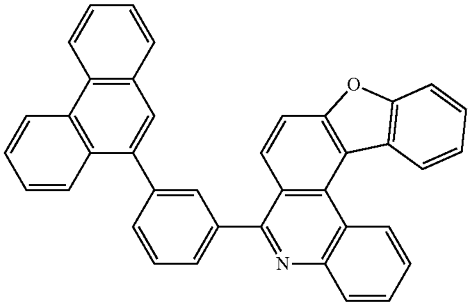
1-179
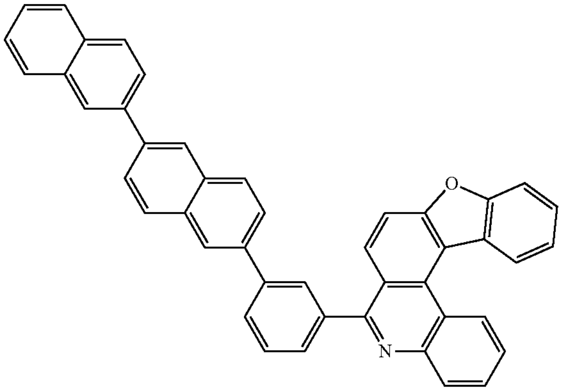

-continued
1-180
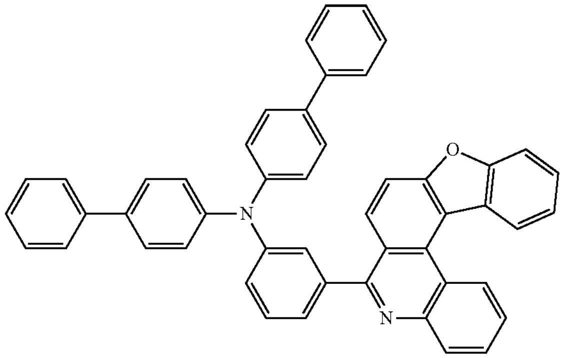
1-366
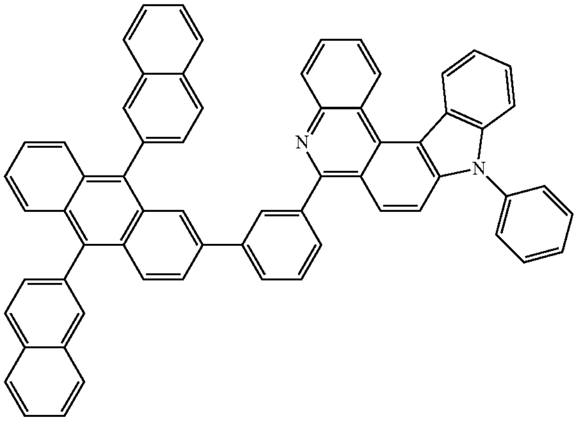
1-367
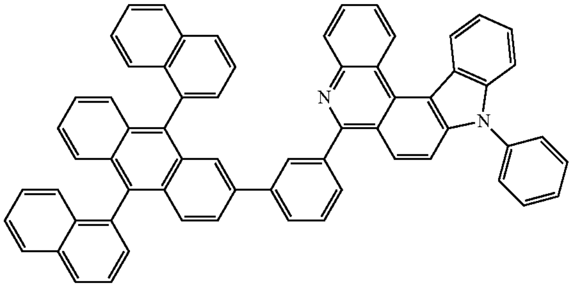
1-368
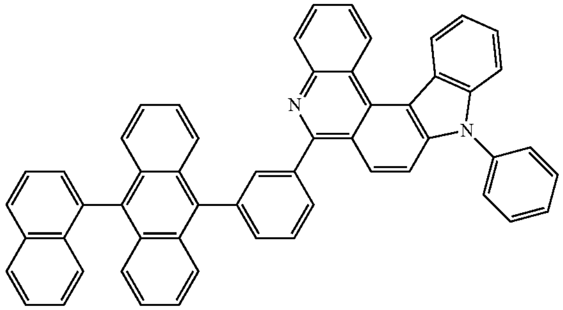
-continued
1-369
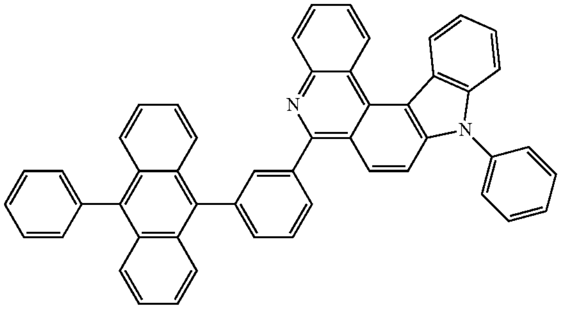
1-370
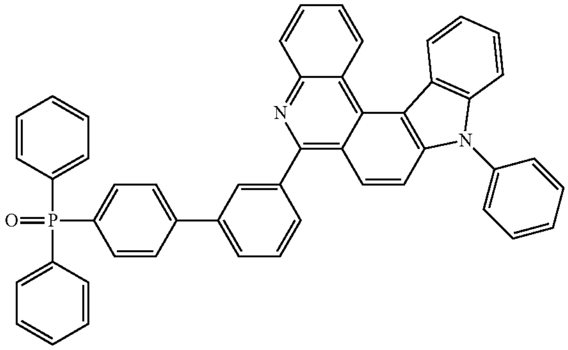
1-371
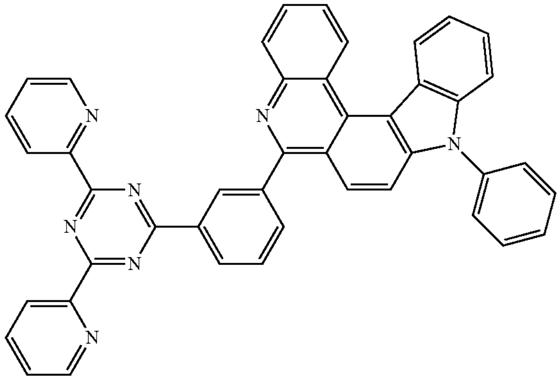
1-372
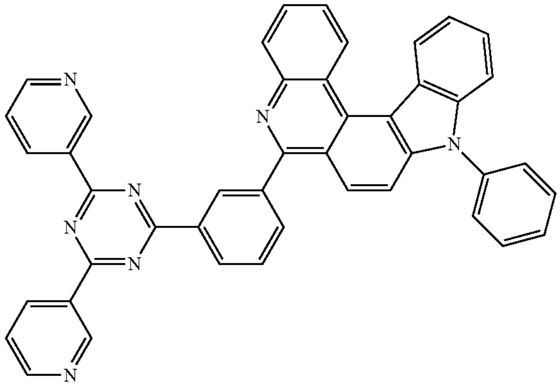

-continued
1-373
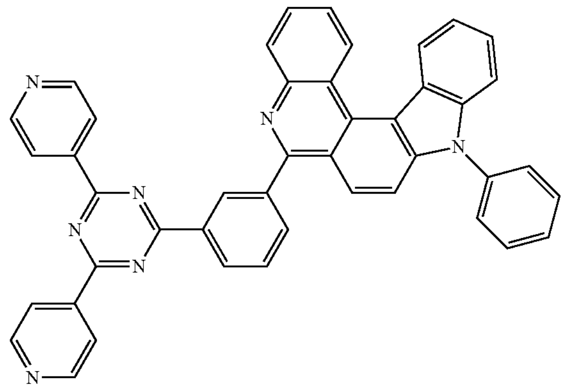
1-374
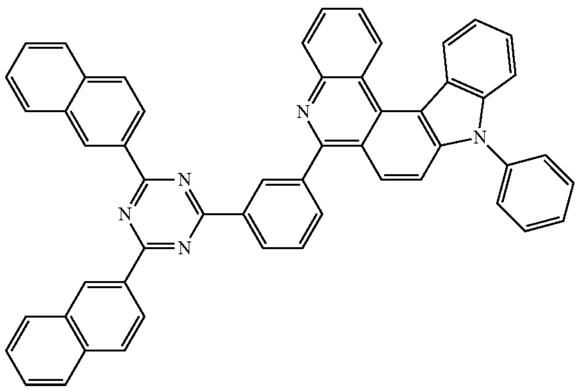
1-375
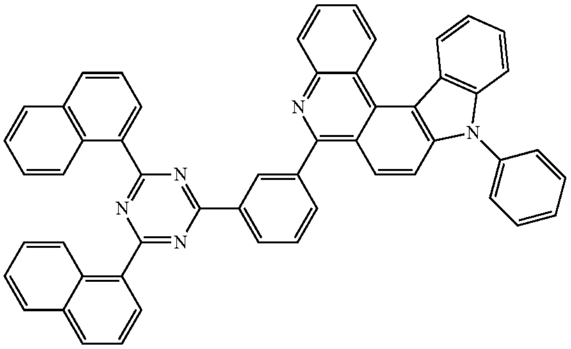
1-376
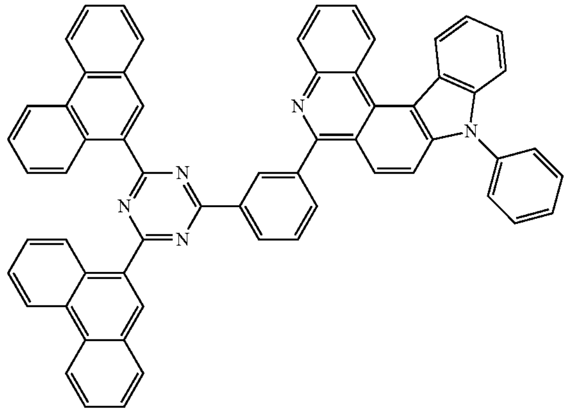
-continued
1-377
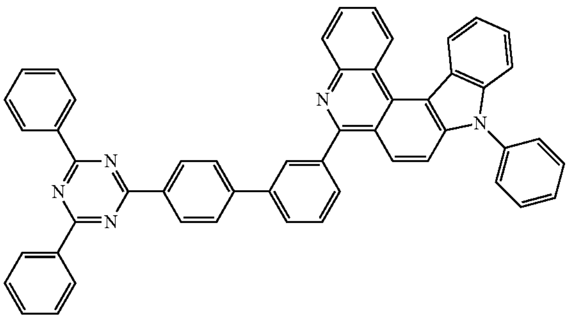
1-378
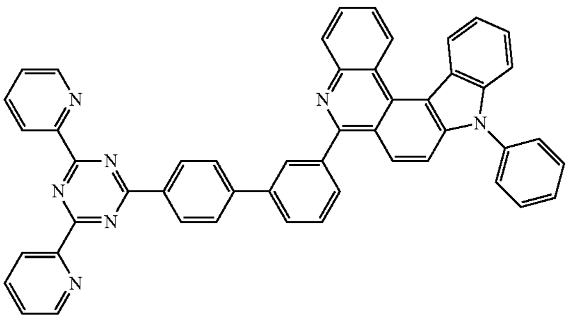
1-379
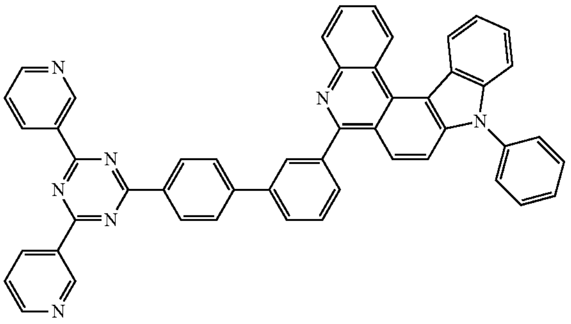
1-380
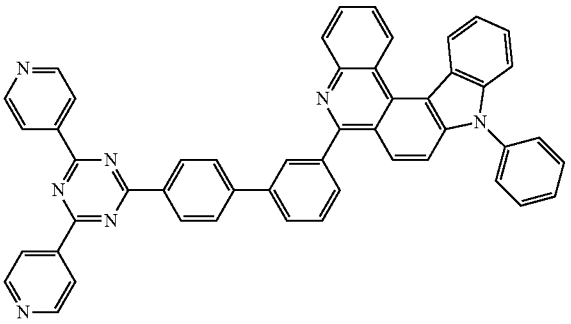

-continued
1-381
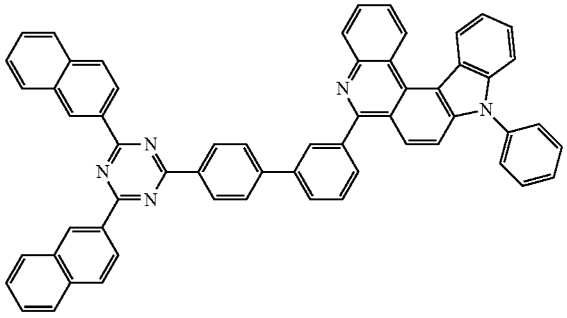
1-382
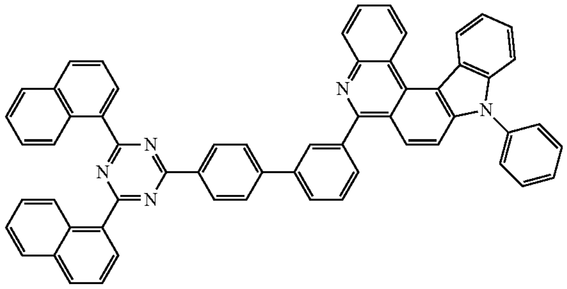
1-383
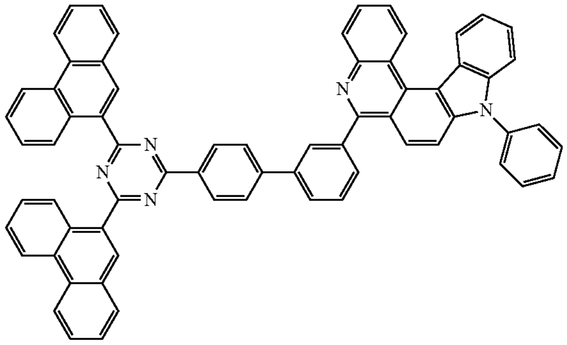
1-384
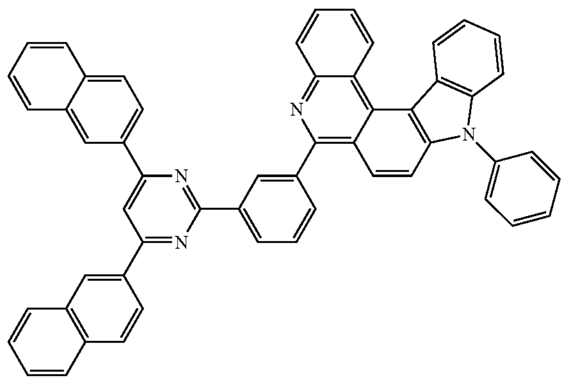
-continued
1-385
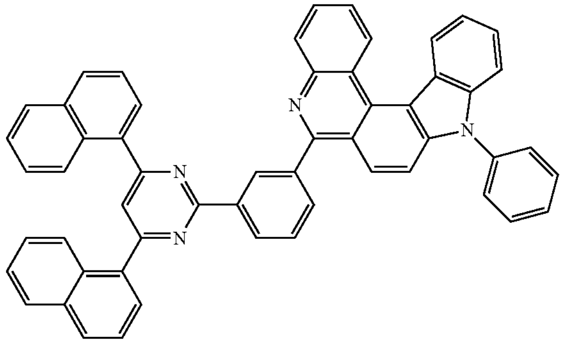
1-386
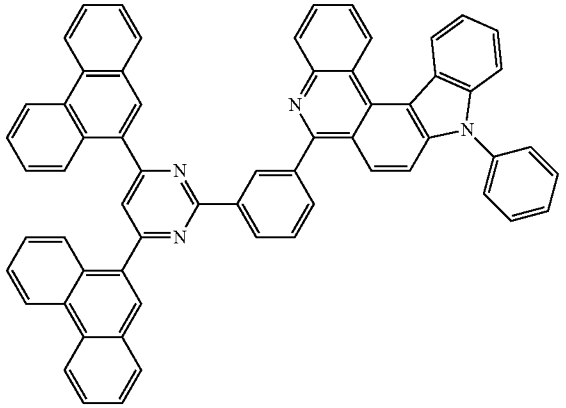
1-387
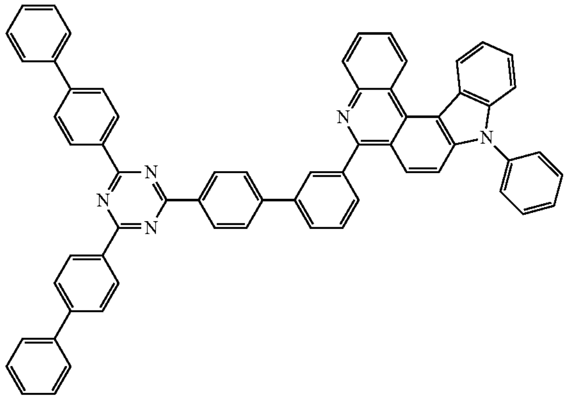
1-388
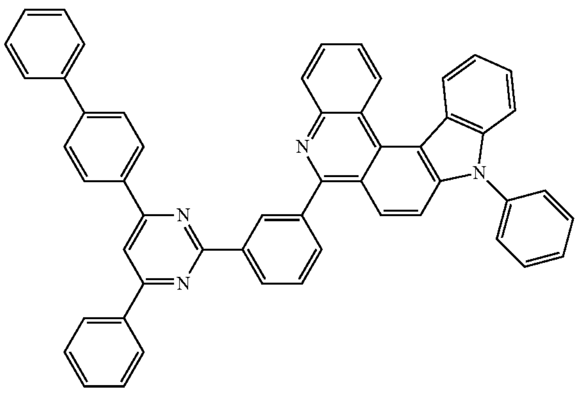

-continued
1-389
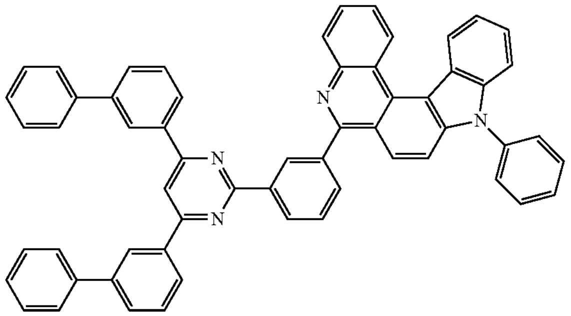
1-390
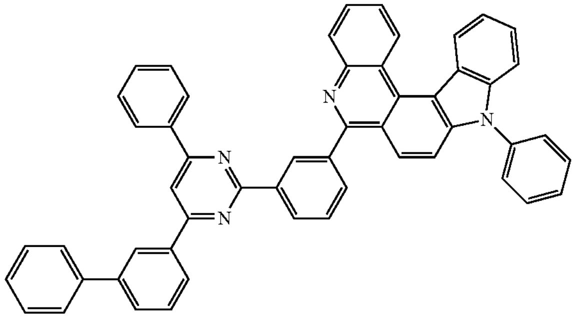
1-391
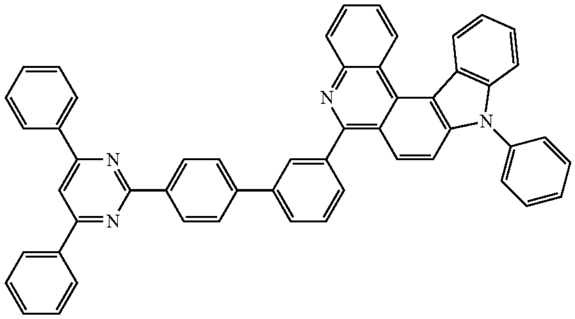
1-392
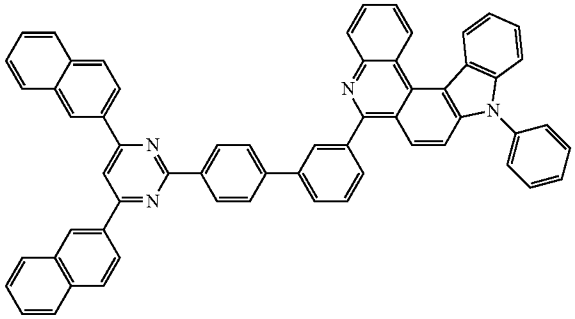
-continued
1-393
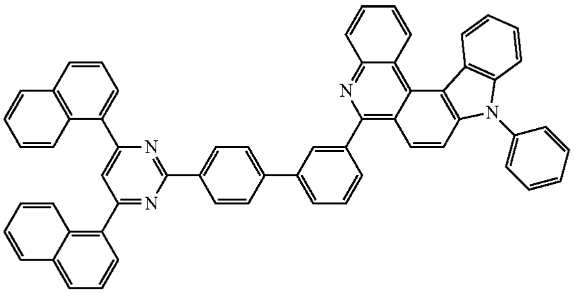
1-394
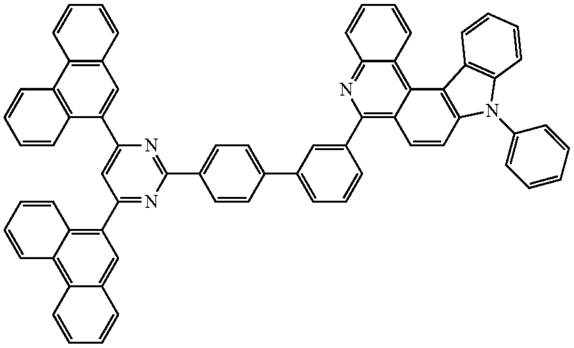
1-395
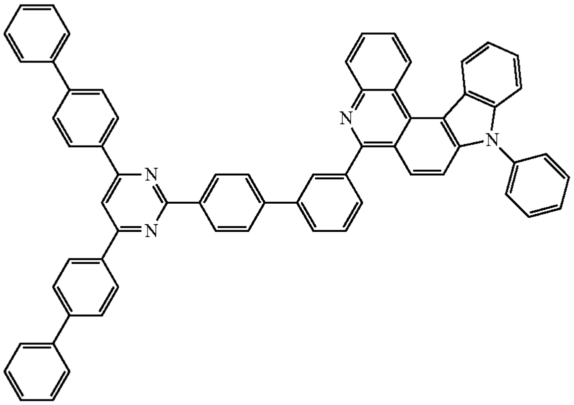
1-396
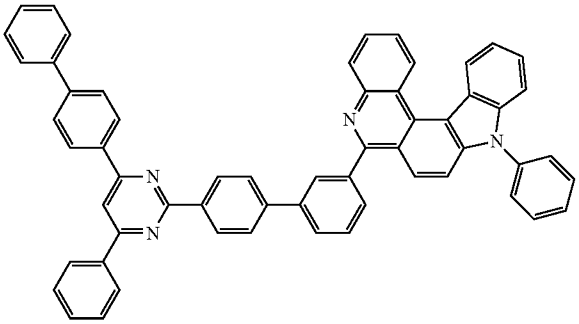

-continued
1-397
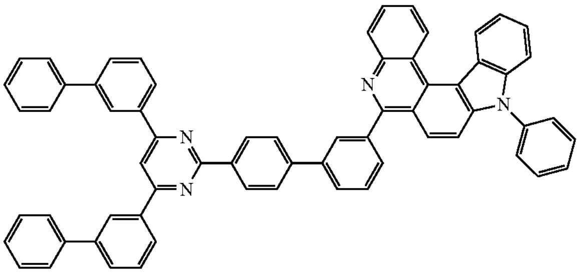
1-398
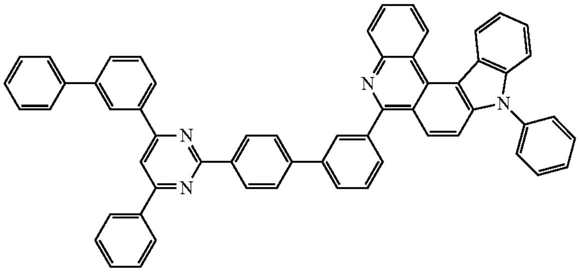
1-399
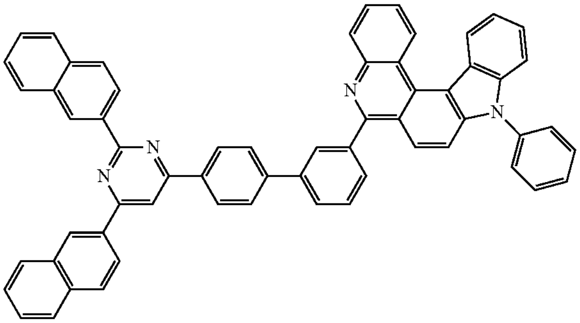
1-400
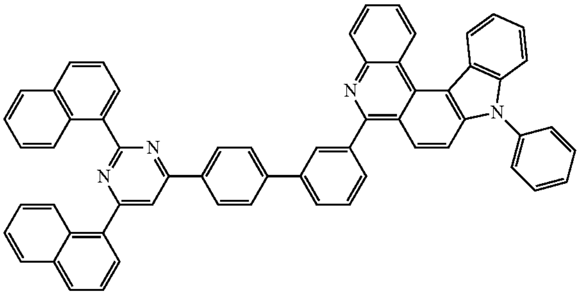
1-401
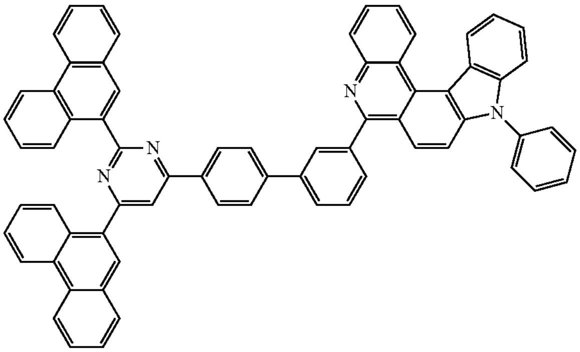
-continued
1-402
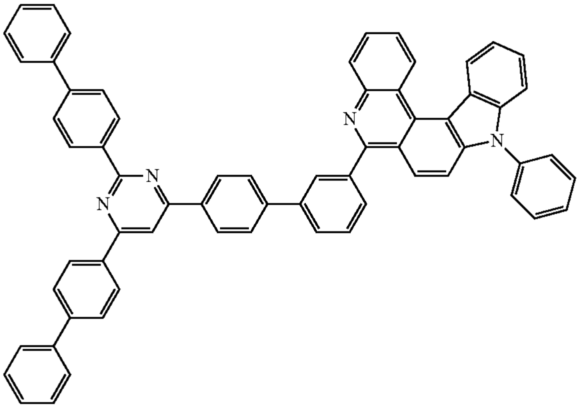
1-403
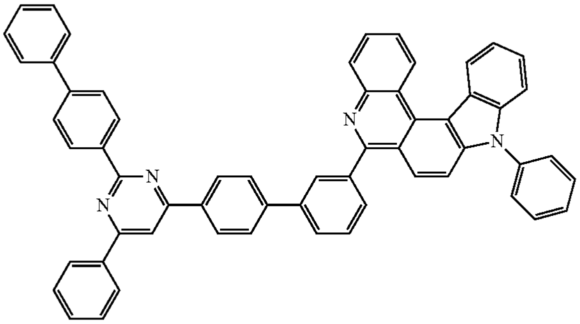
1-404
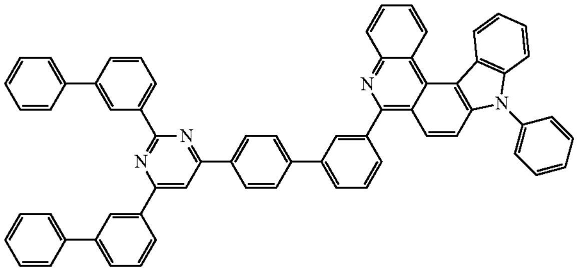
1-405
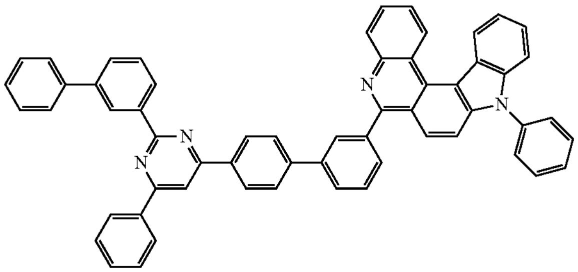

-continued
1-406
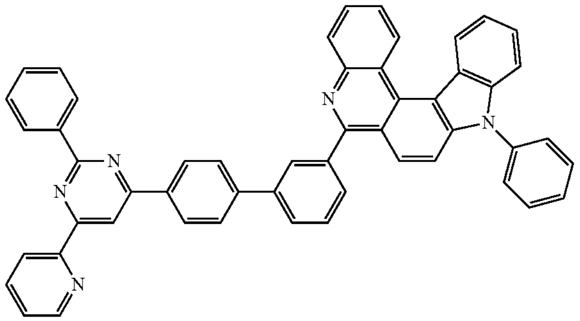
1-407
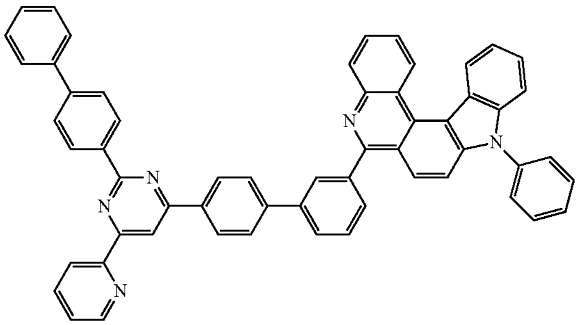
1-408
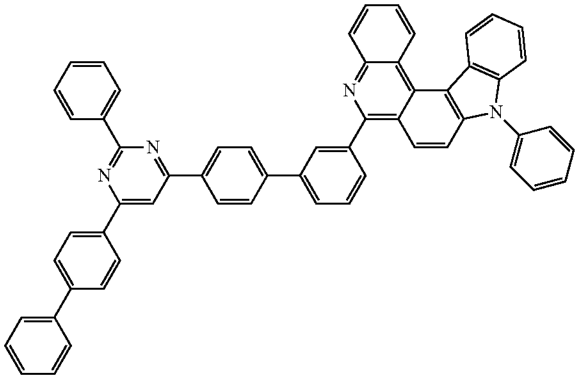
1-409
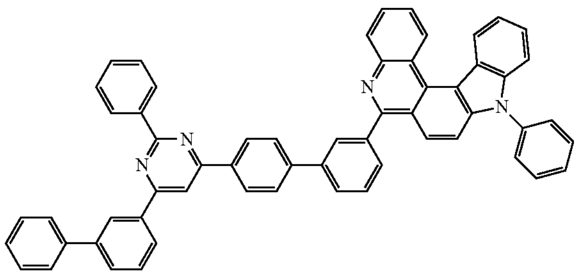
-continued
1-410
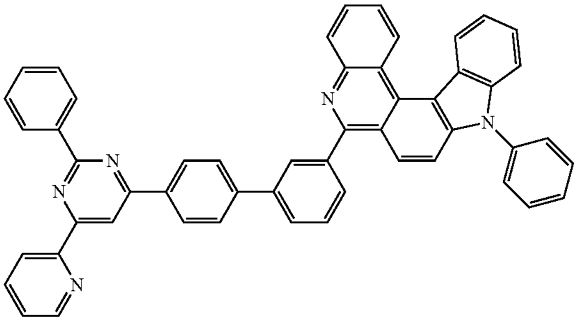
1-411
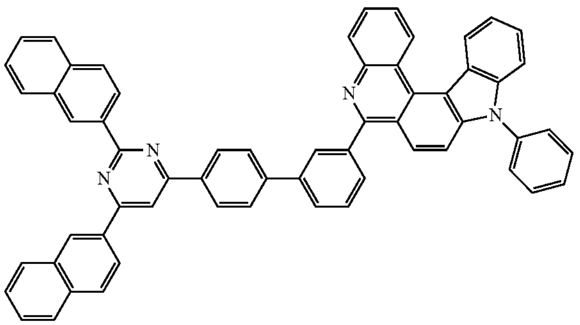
1-412
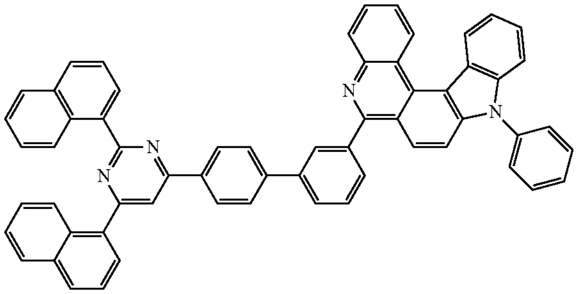
1-413
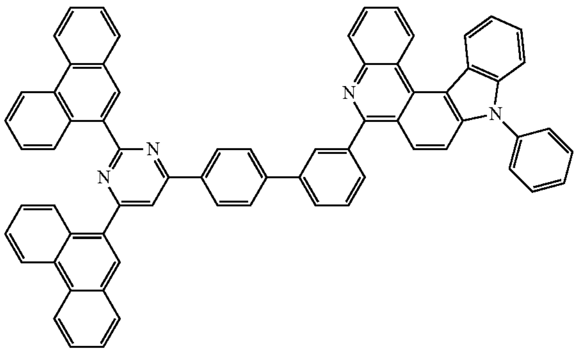

-continued
1-414
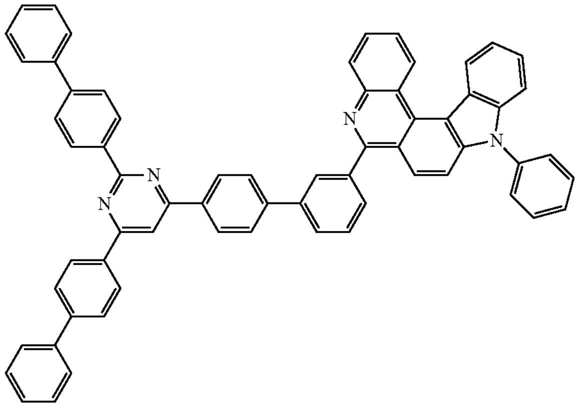
1-415
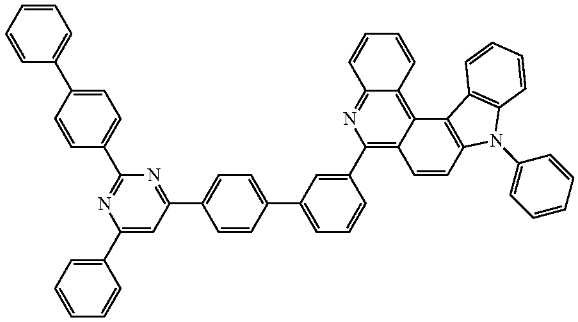
1-416
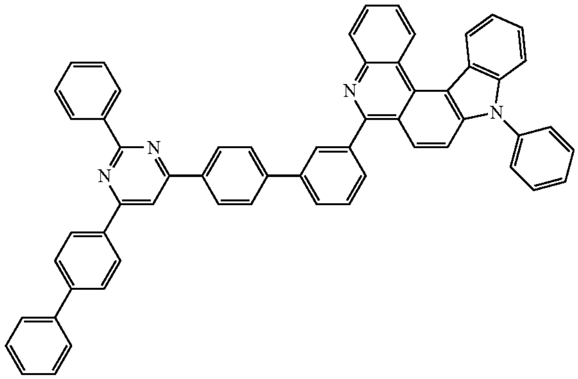
1-417
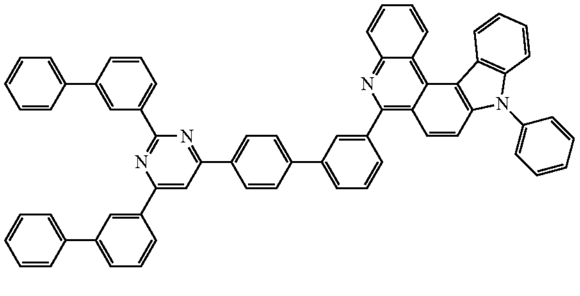
-continued
1-418
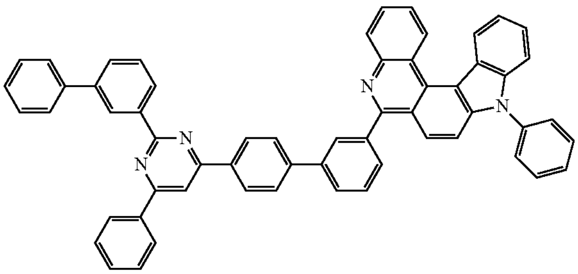
1-419
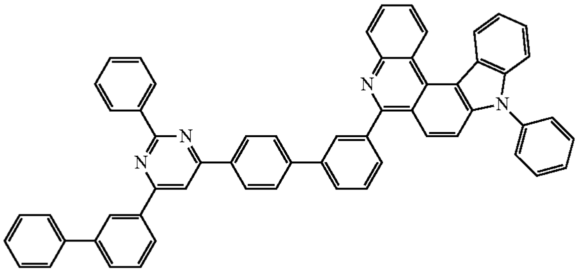
1-420
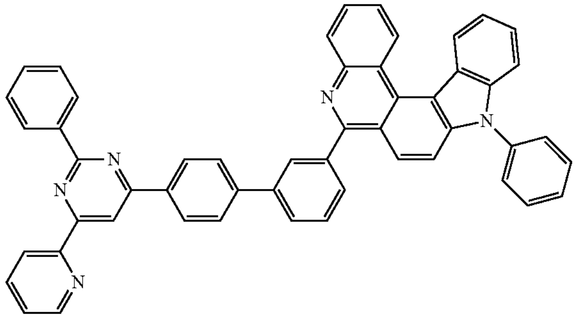
1-421
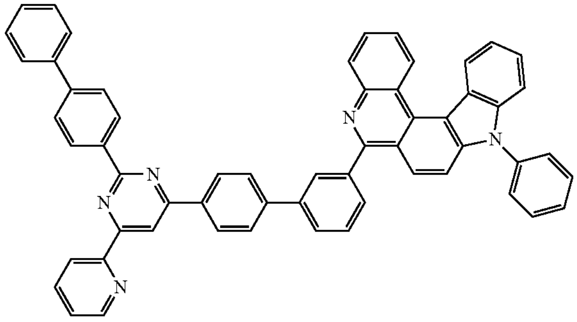
1-422
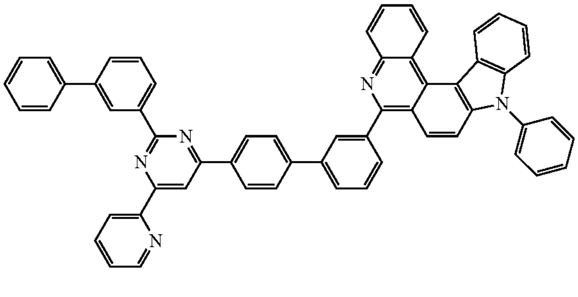

-continued
1-423
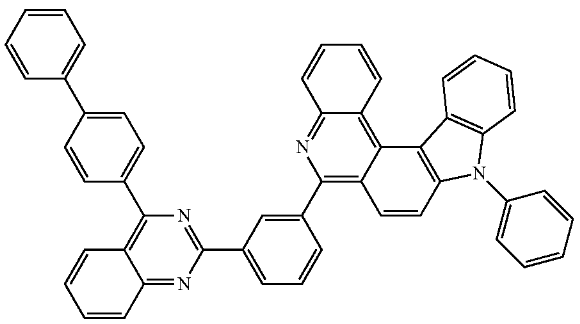
1-424
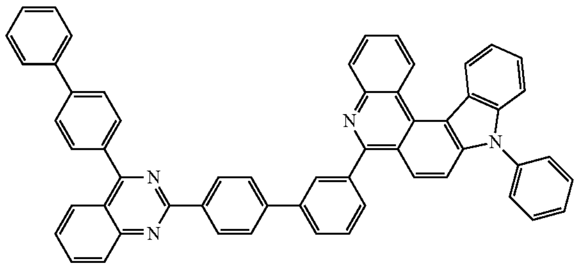
1-425
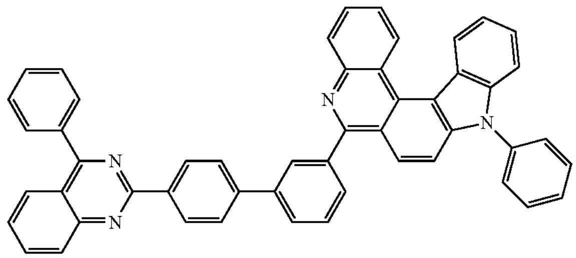
1-426
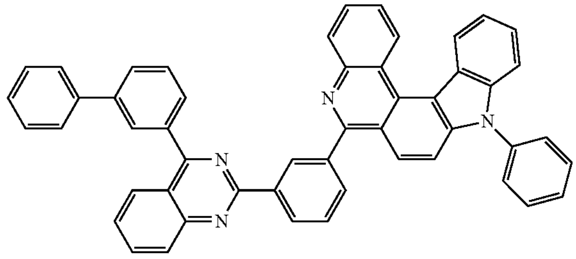
1-427
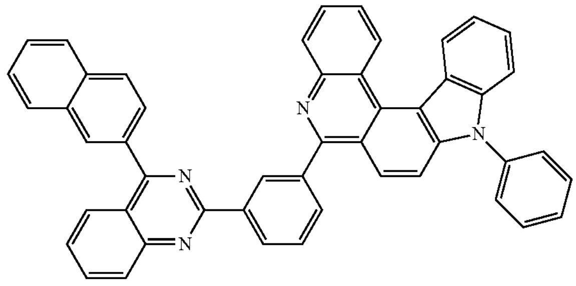
-continued
1-428
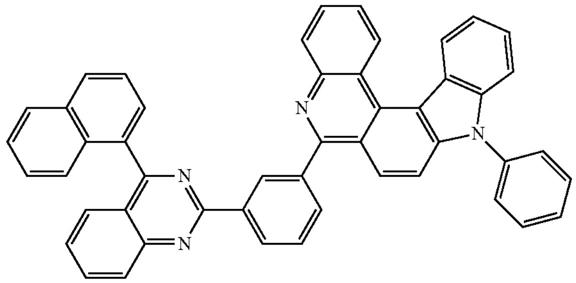
1-429
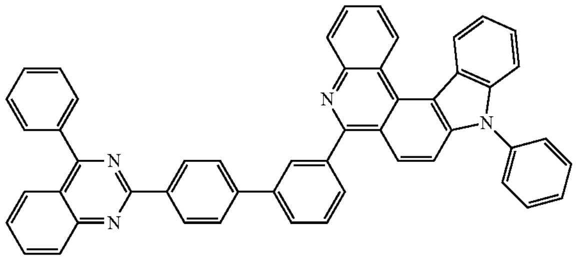
1-430
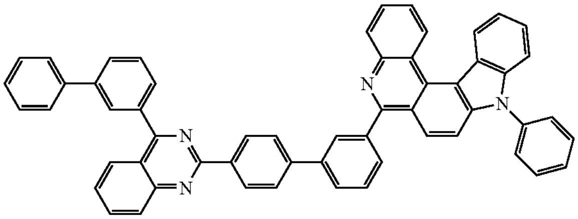
1-431
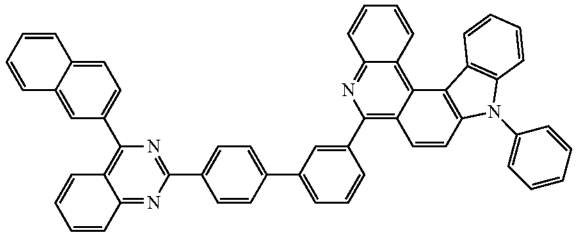
1-432
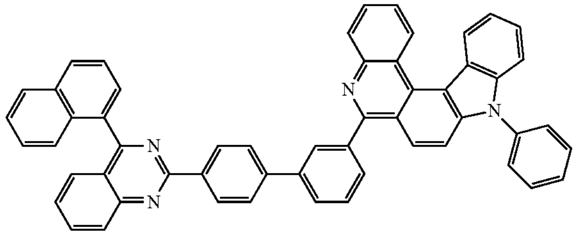

1-433
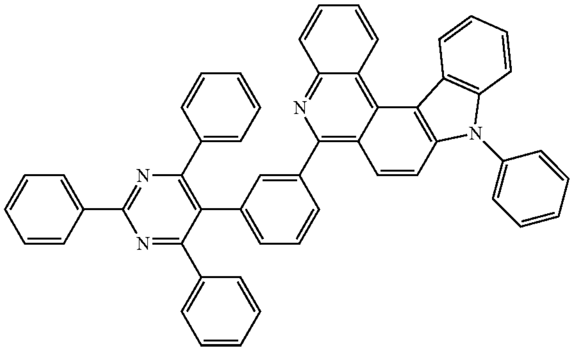
1-434
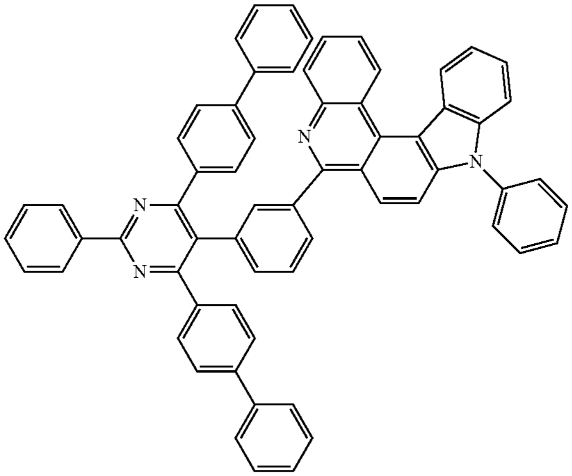
1-435
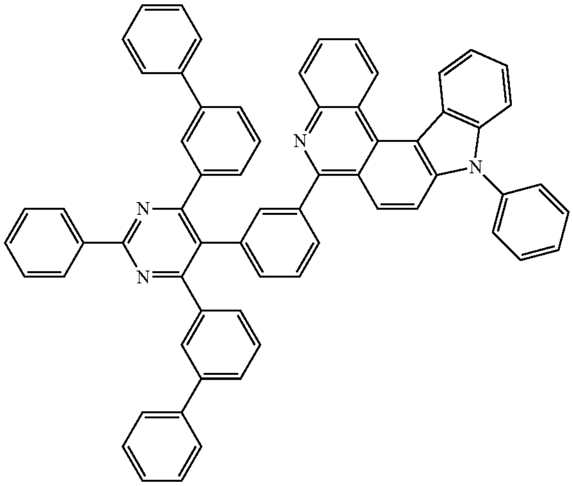
1-436
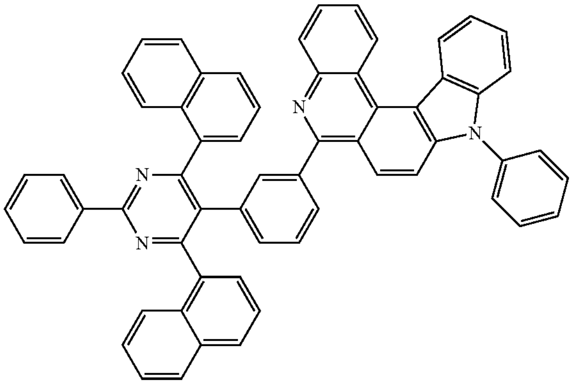
1-437
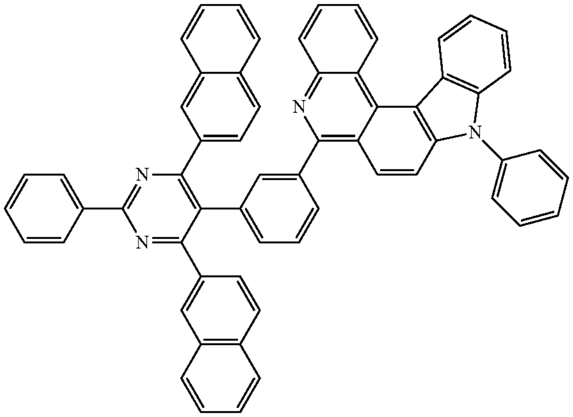
1-438
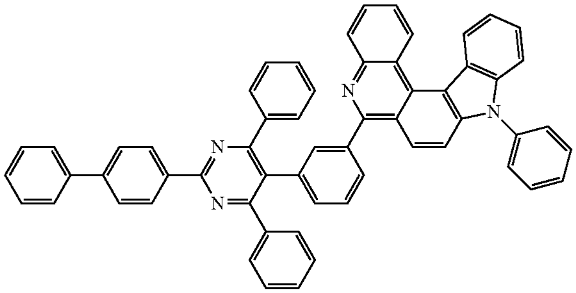
1-439
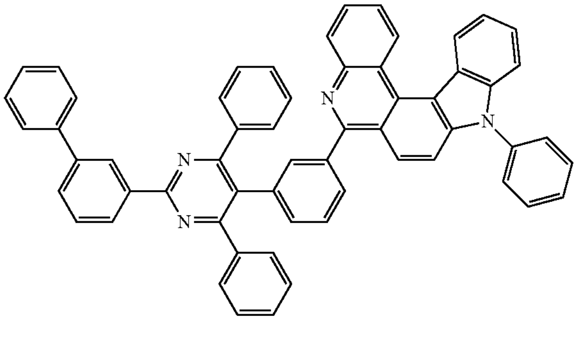

-continued
1-440
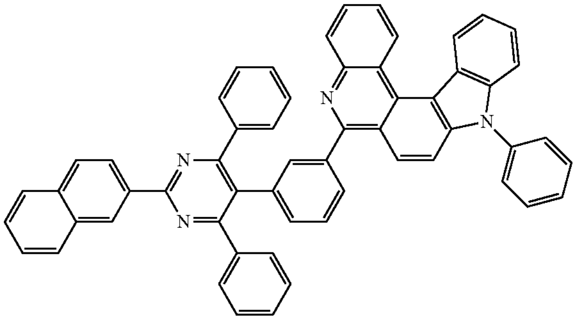
1-441
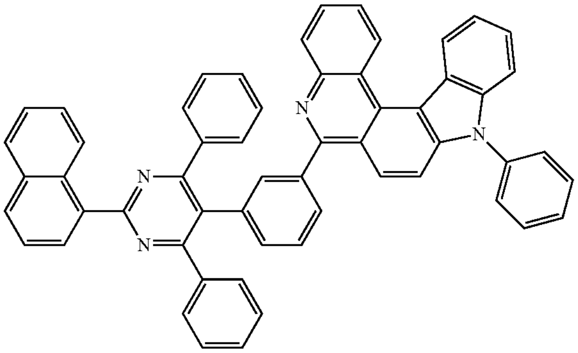
1-442
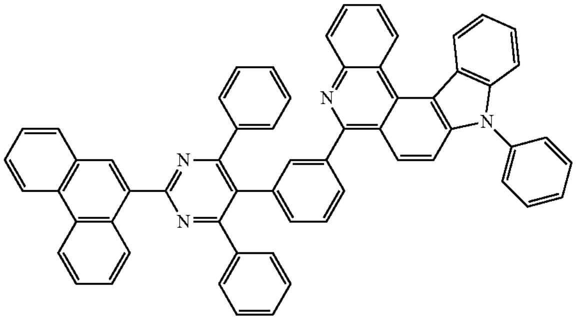
1-443
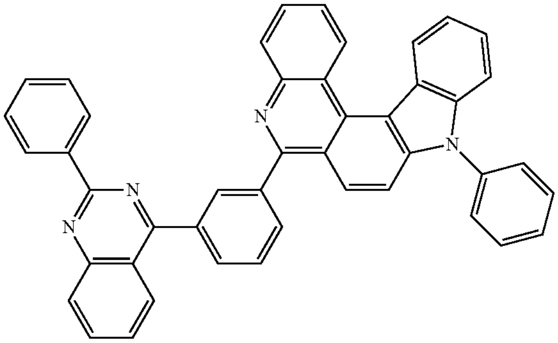
-continued
1-444
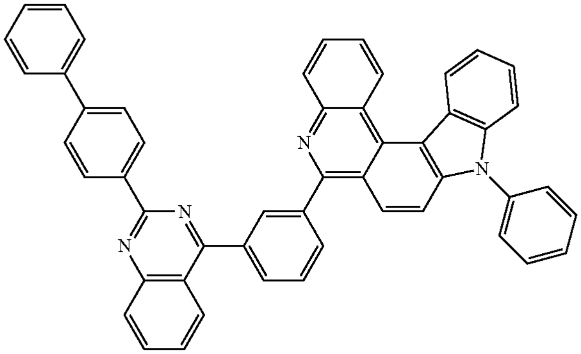
1-445
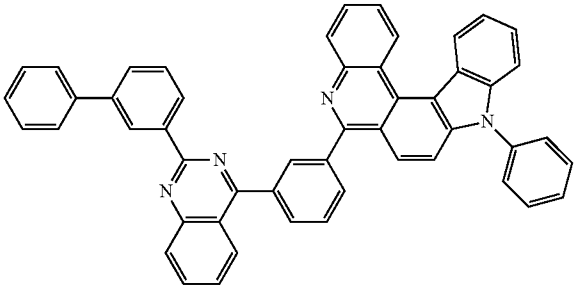
1-446
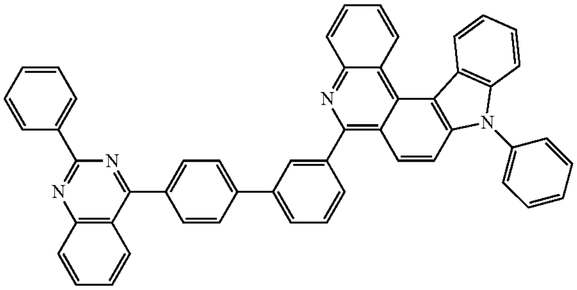
1-447
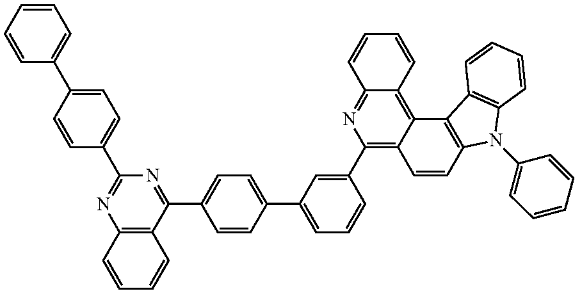
1-448
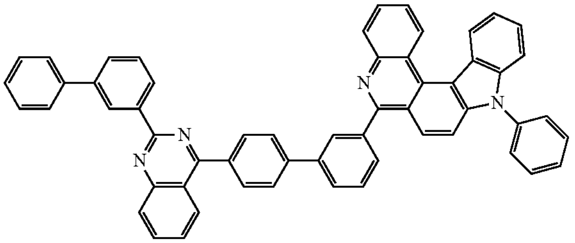

-continued
1-449
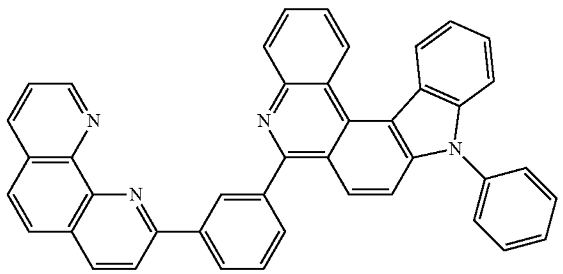
1-450
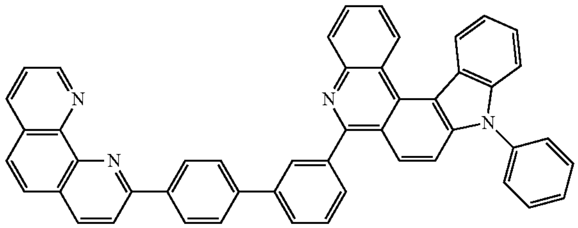
1-451
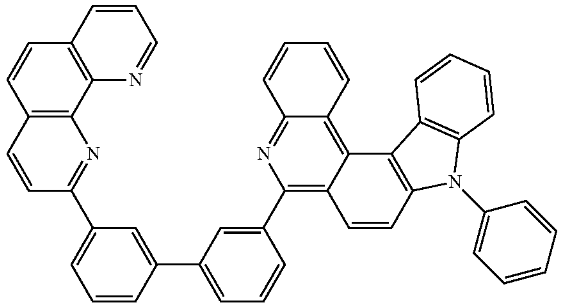
1-452
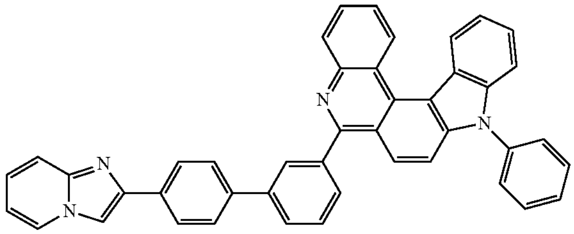
1-453
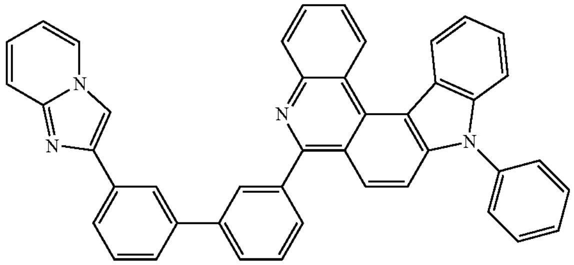
-continued
1-454
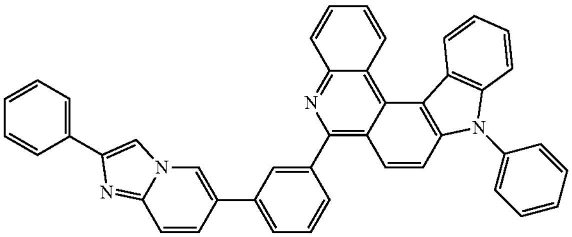
1-455
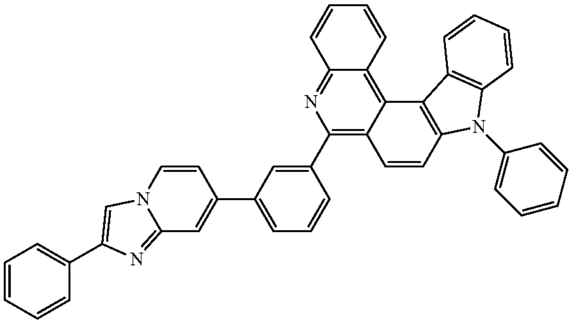
1-456
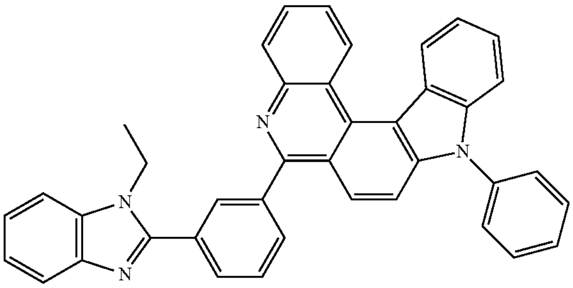
1-457
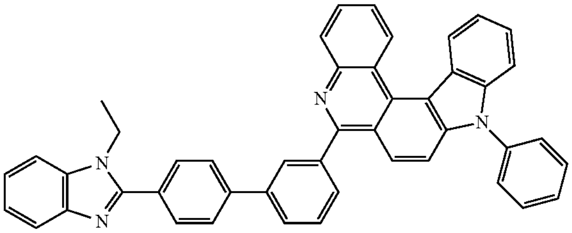
1-458
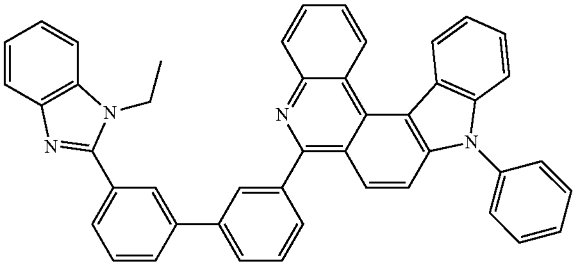

-continued
1-459
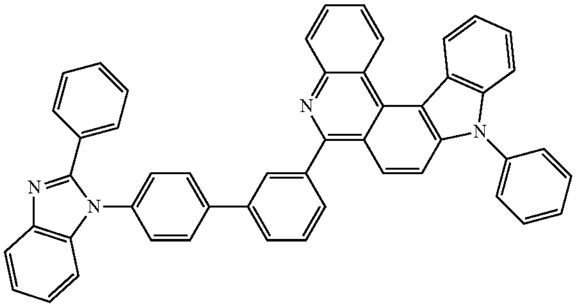
1-460
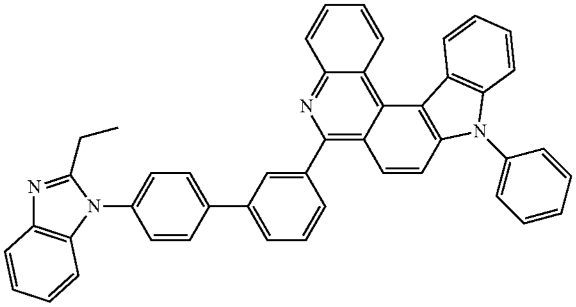
1-461
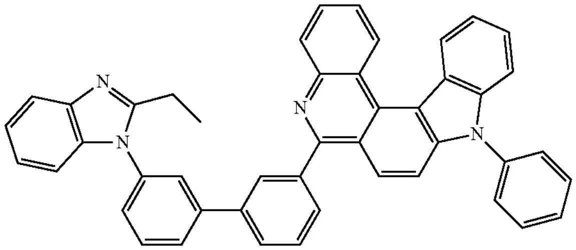
1-462
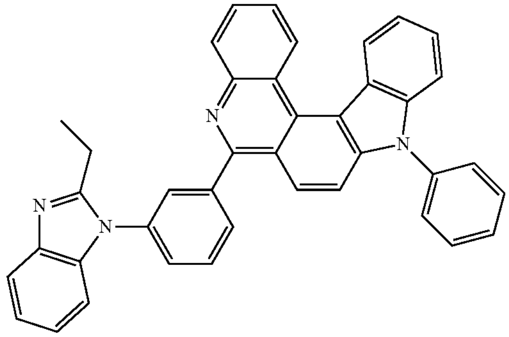
1-463
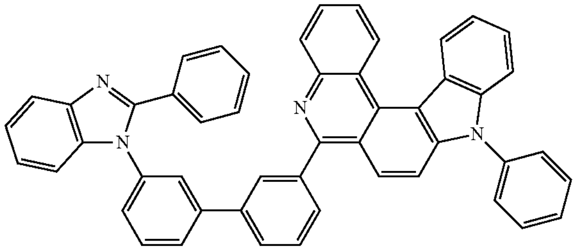
-continued
1-464
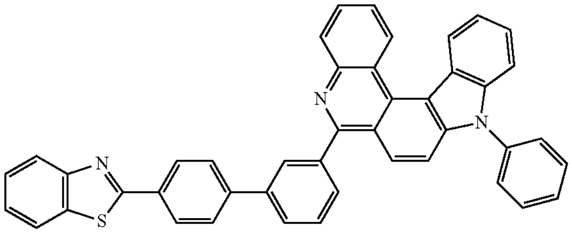
1-465
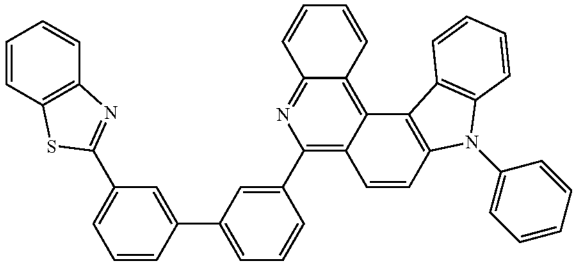
1-466
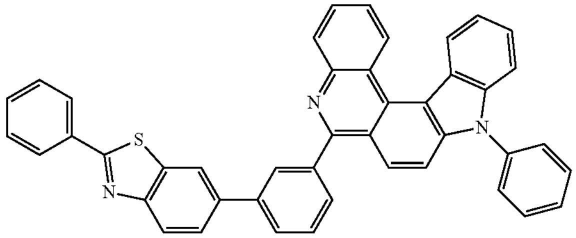
1-467
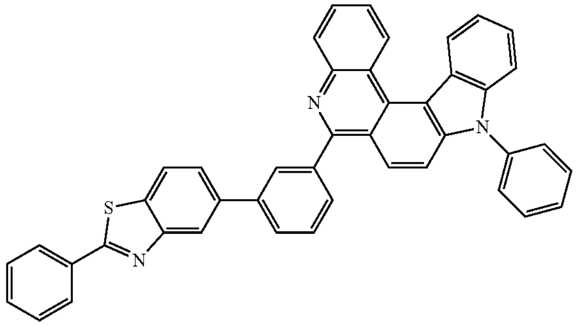
1-468
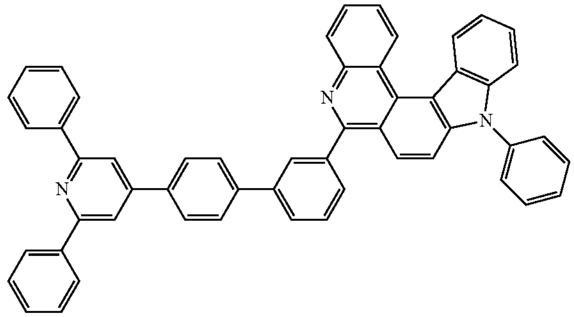

-continued
1-469
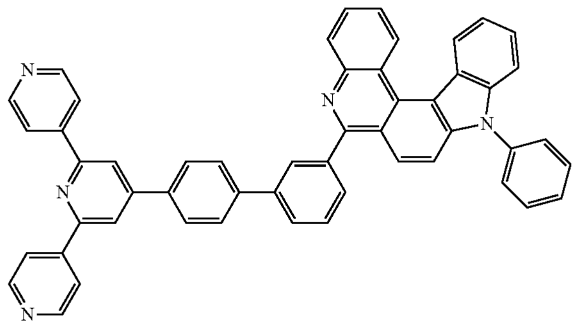
1-470
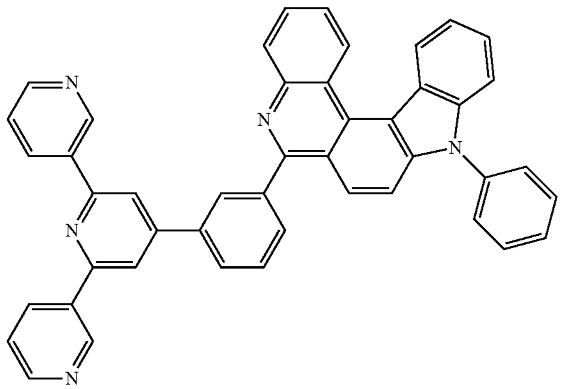
1-471
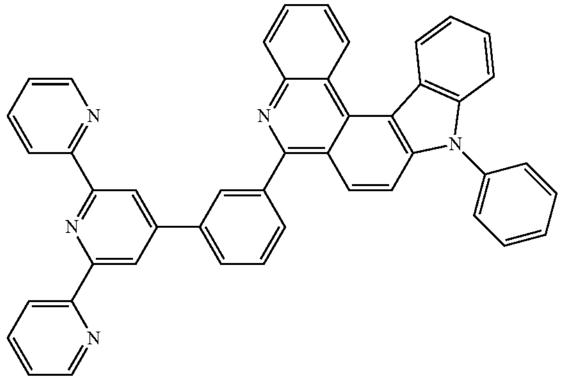
1-472
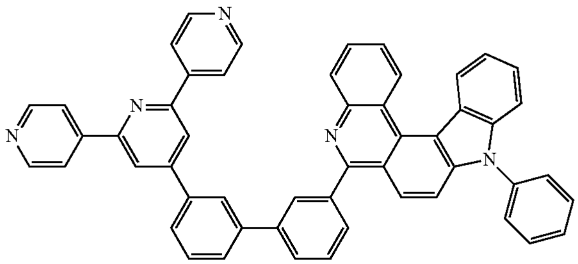
-continued
1-473
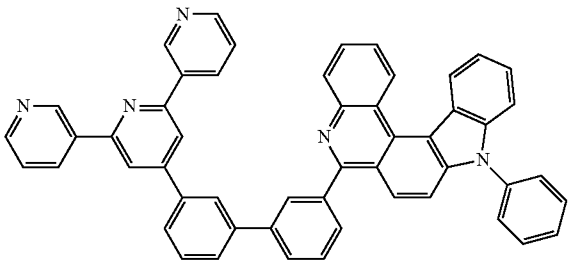
1-474
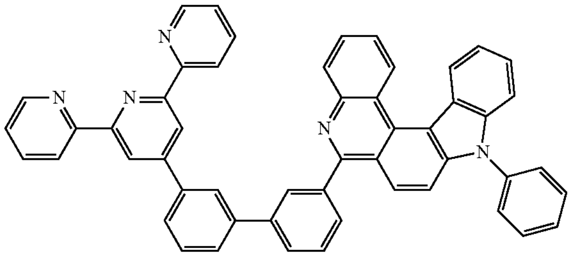
1-475
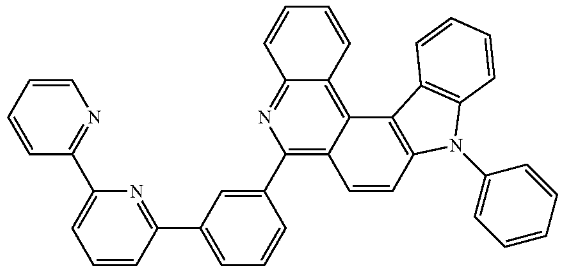
1-476
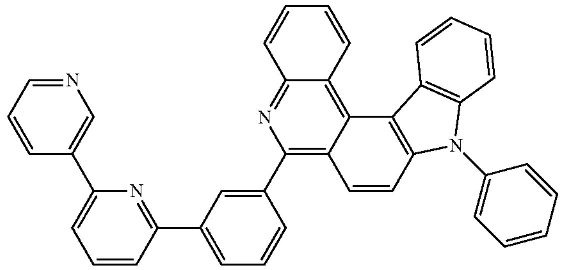
1-477
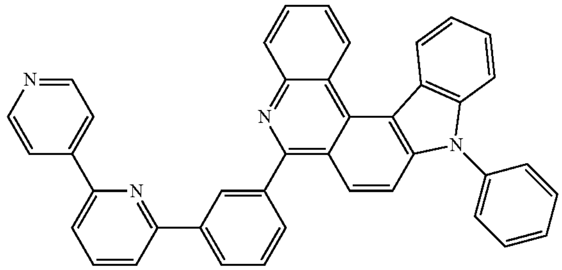

-continued
1-478
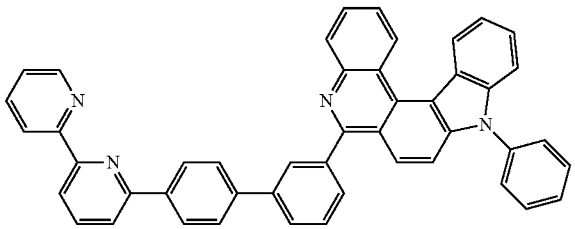
1-479
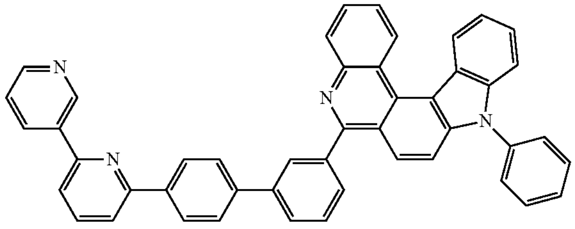
1-480
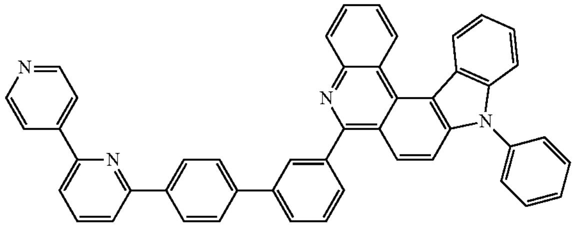
According to another exemplary embodiment of the present specification,
in Chemical Formula 14, Ar may be bonded to an atom bonded to a core of phenyl at a para position thereof, and Chemical Formula 14 may be selected from the following compounds.
1-181
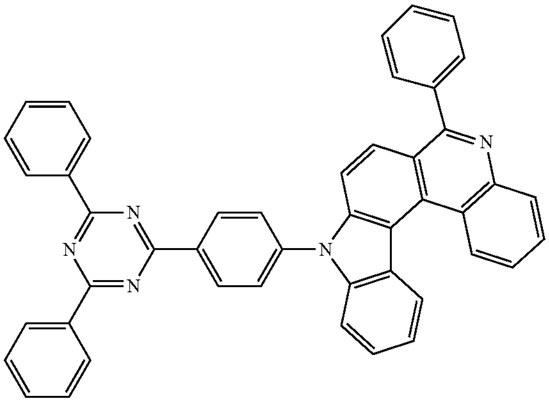
-continued
1-182
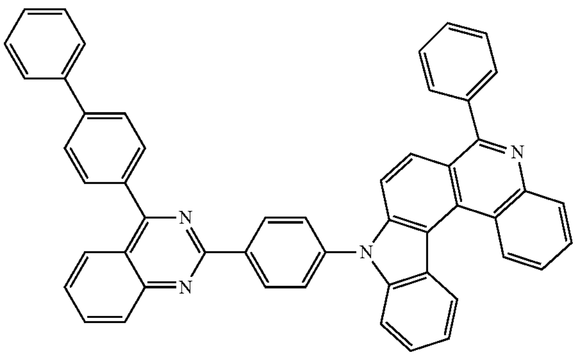
1-183
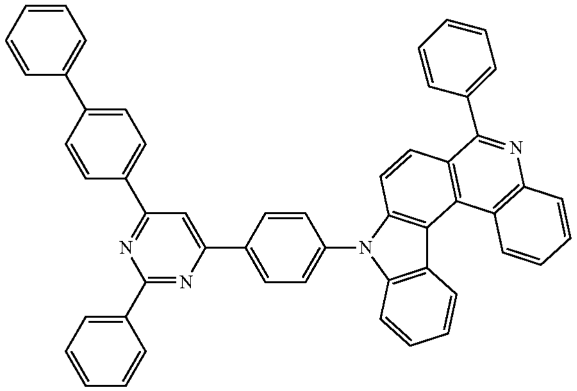
1-184
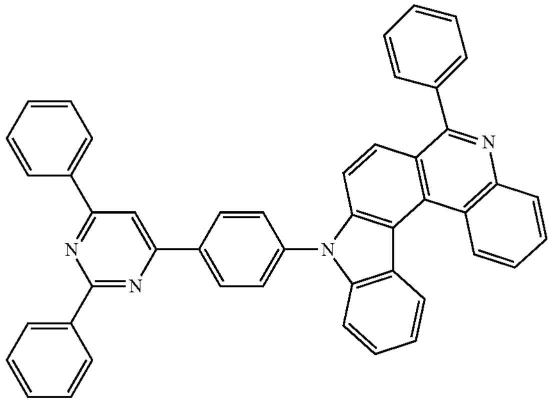
1-185
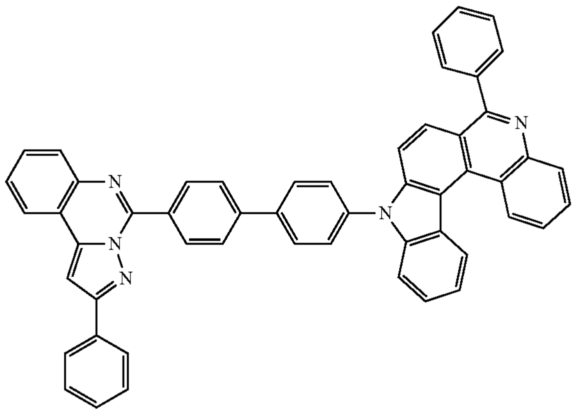

1-186
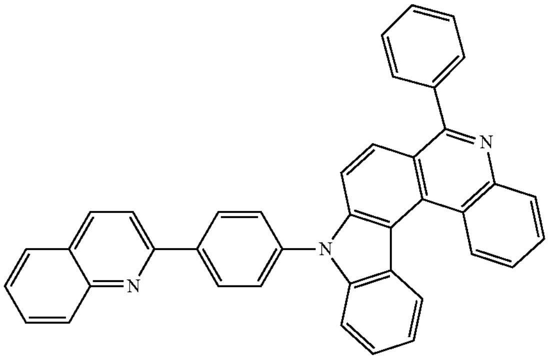
1-187
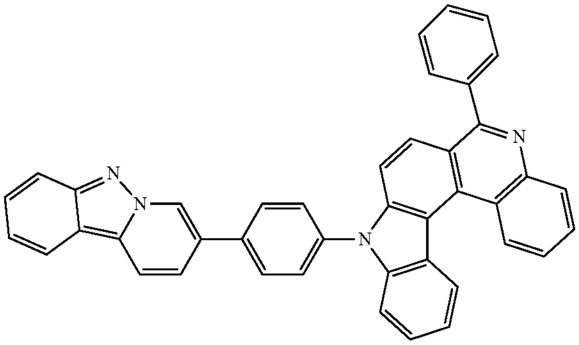
1-188
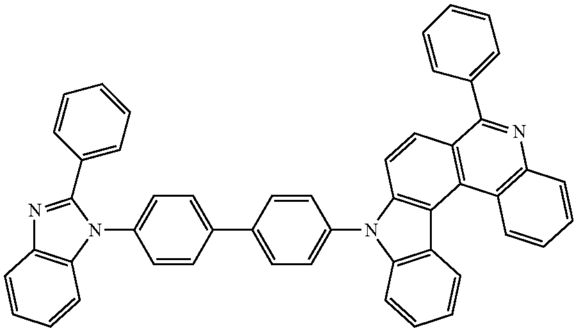
1-189
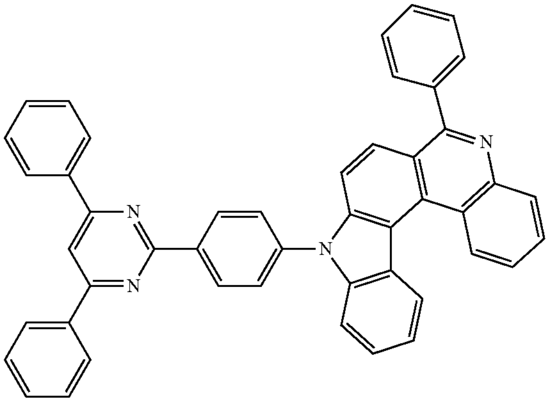
1-190
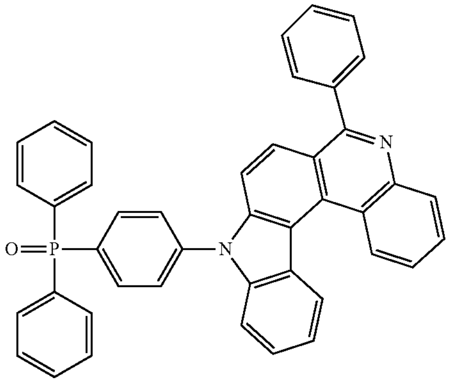
1-191
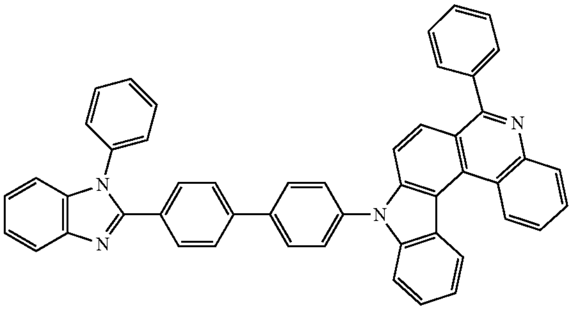
1-192
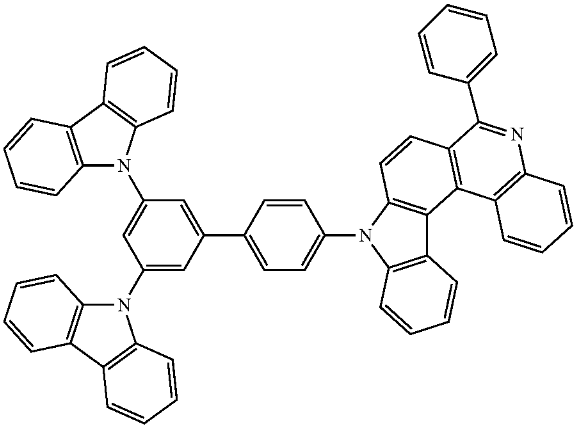
1-193
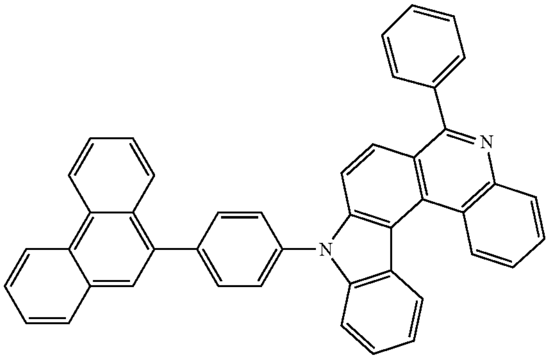

-continued
1-194
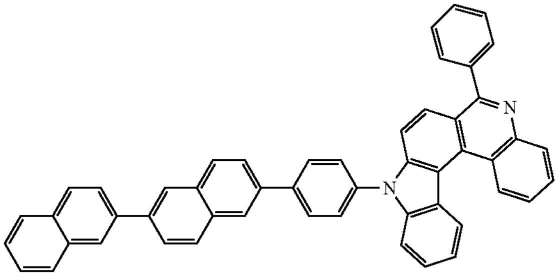
1-195
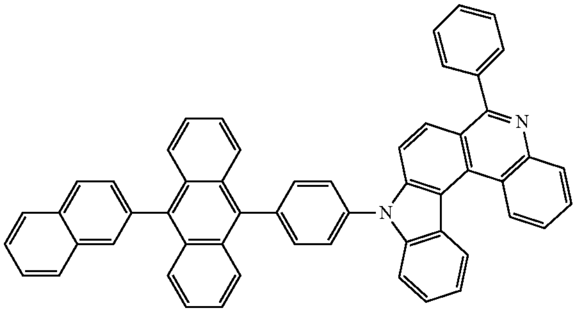
1-196
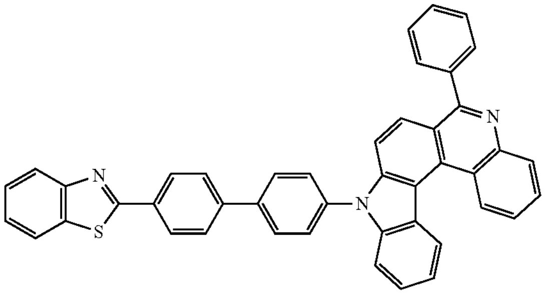
1-197
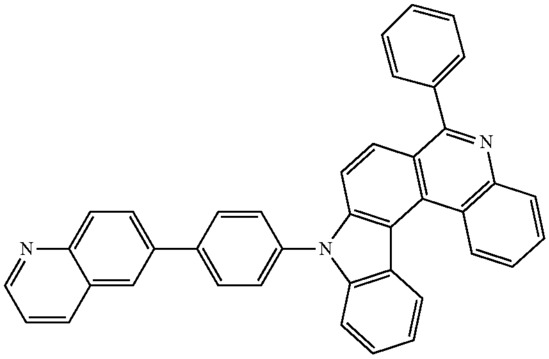
-continued
1-198
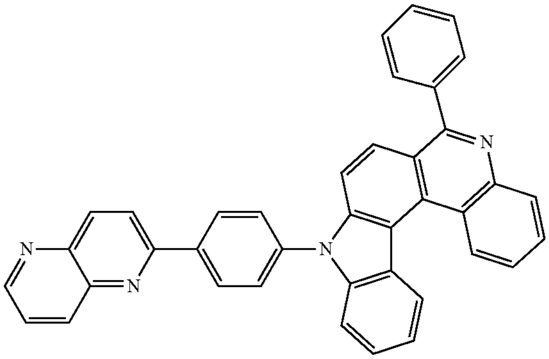
1-199
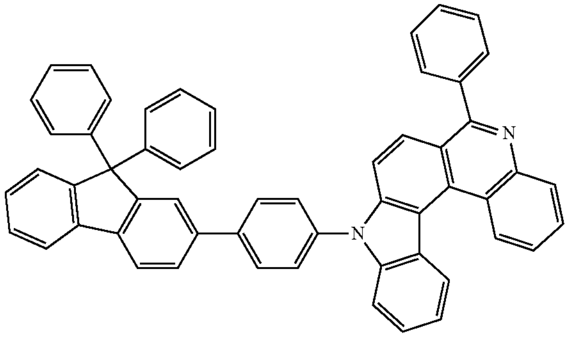
1-200
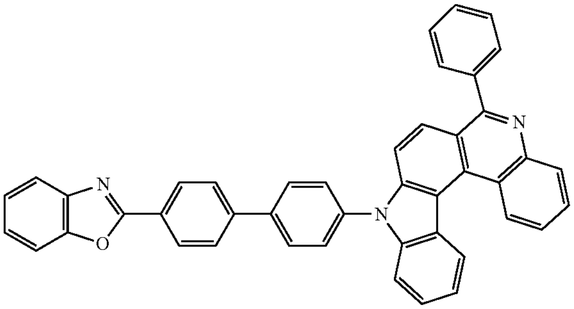
1-201
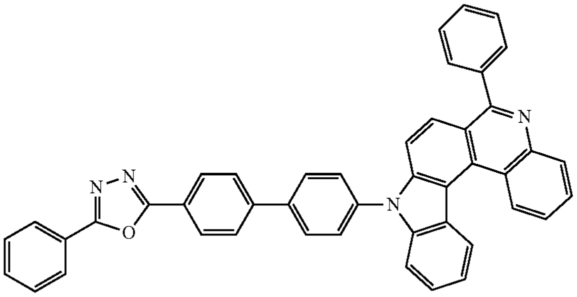

-continued
1-202
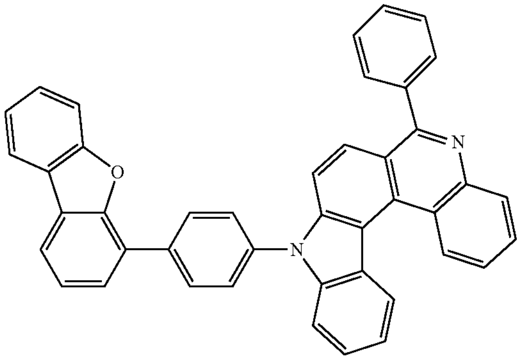
1-203
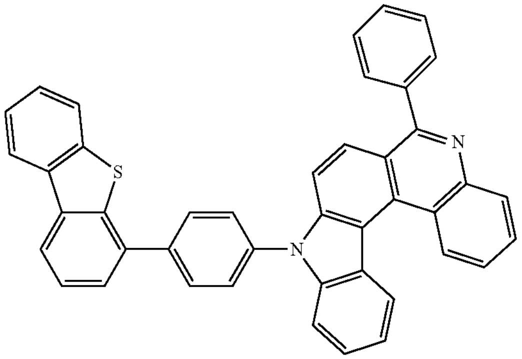
1-204
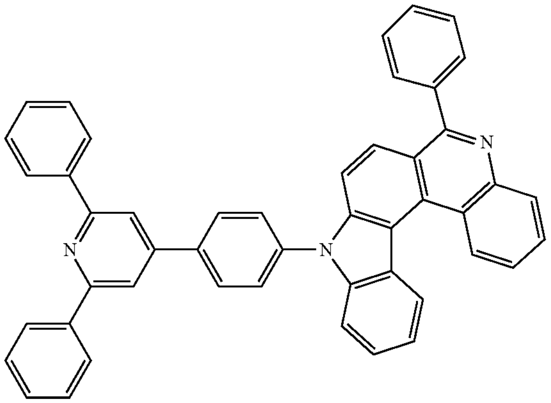
1-205
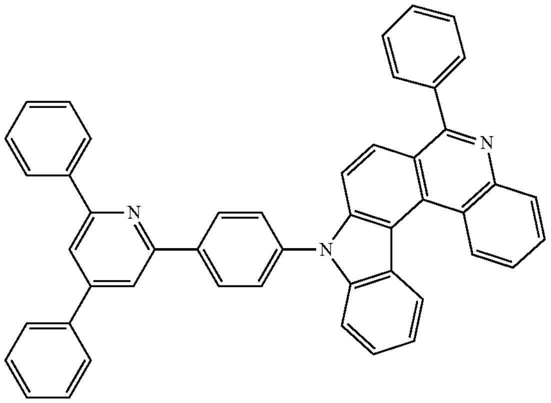
-continued
1-206
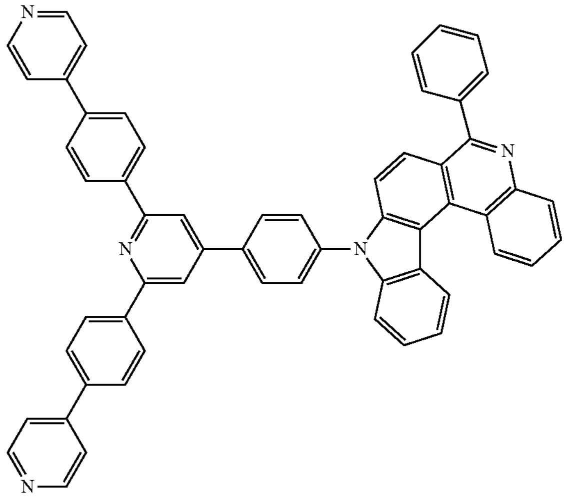
1-207
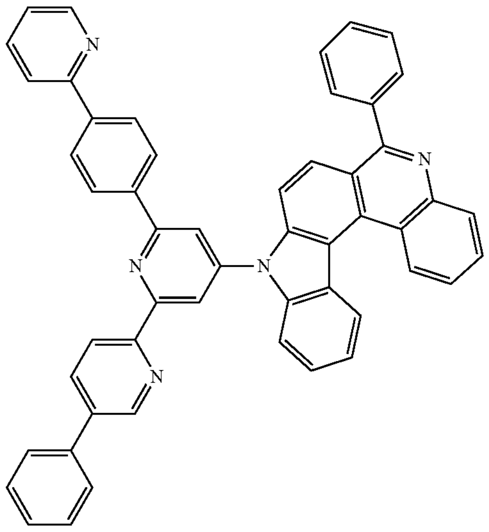
1-208
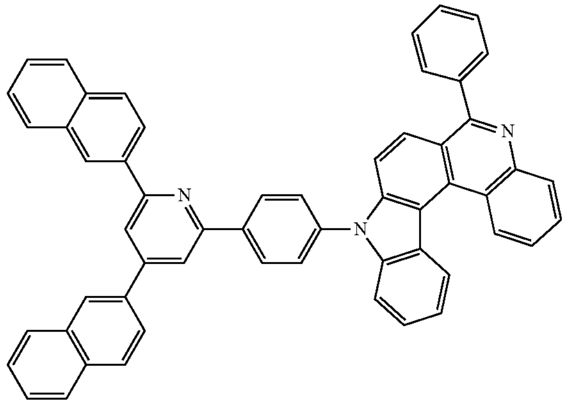

-continued
1-209
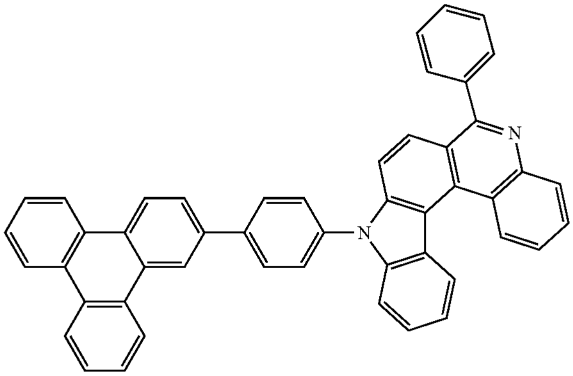
1-210
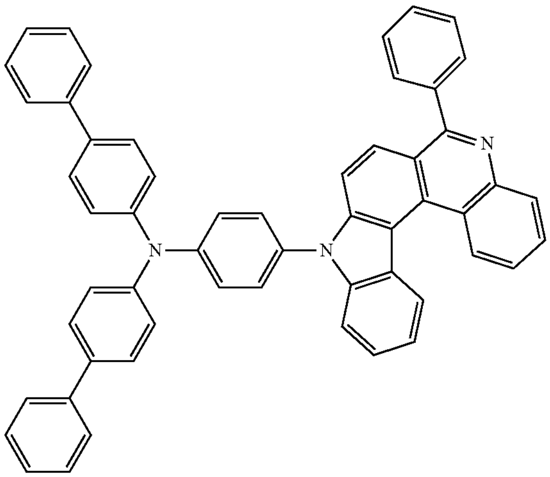
1-211
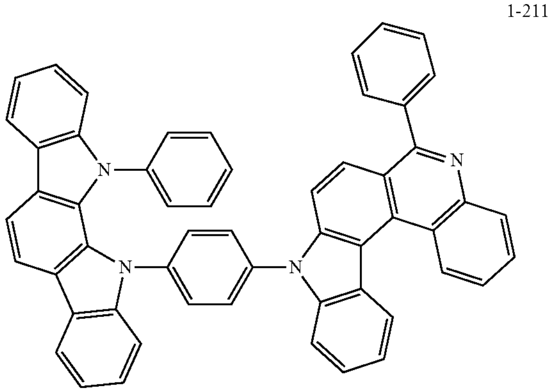
-continued
1-212
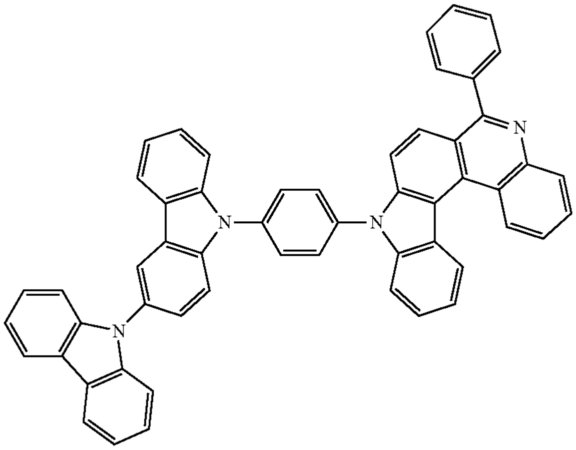
1-213
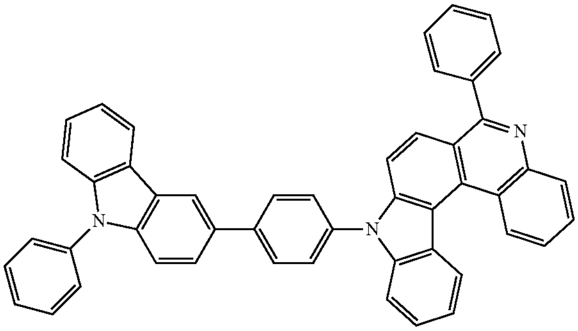
1-214
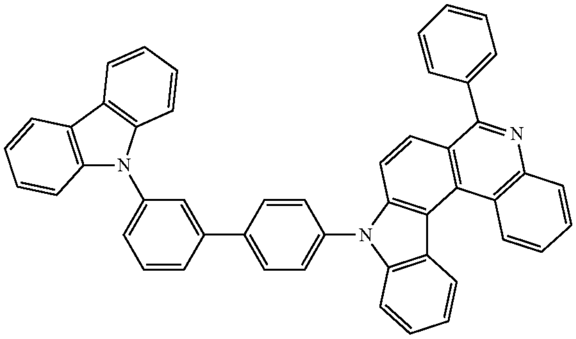

-continued
1-215
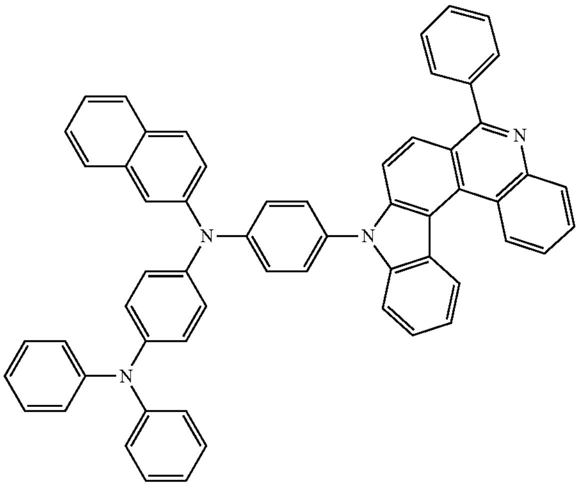
1-481
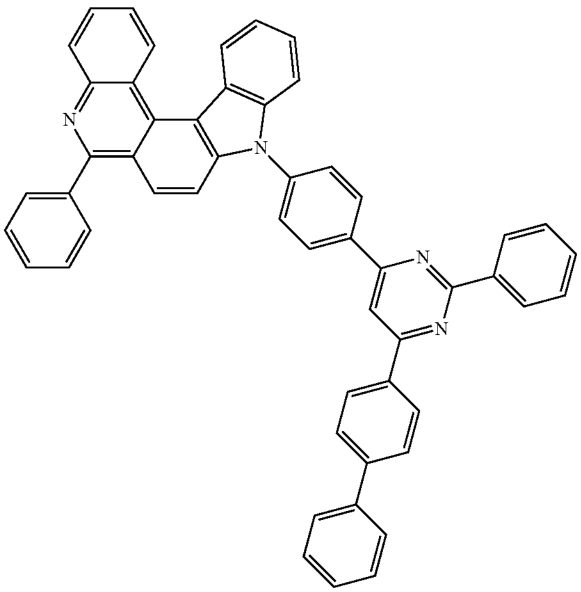
1-482
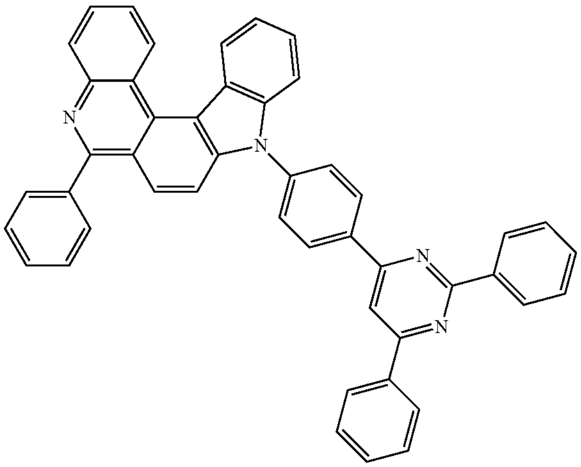
-continued
1-483
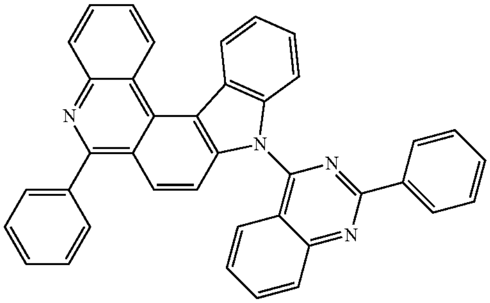
1-484
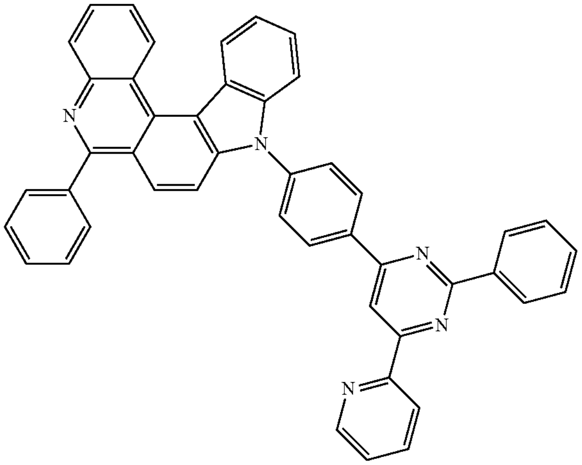
1-485
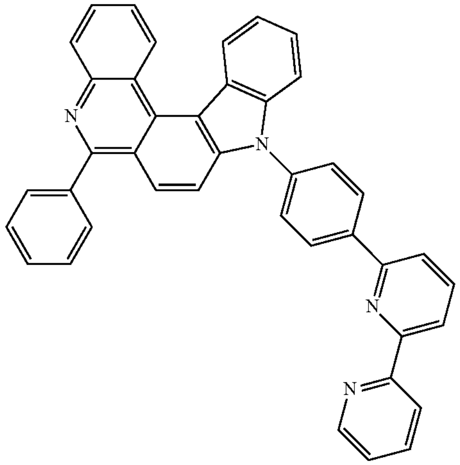
1-486
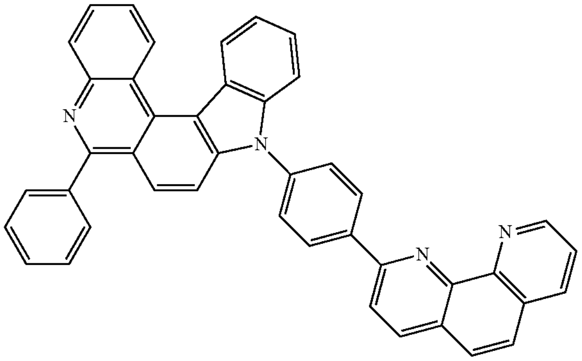

-continued
1-487
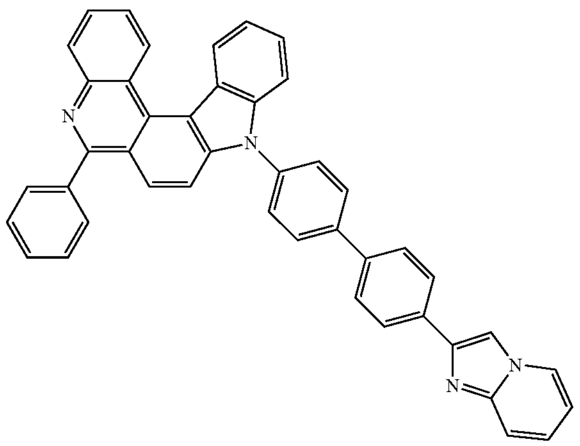
According to another exemplary embodiment of the present specification,
in Chemical Formula 14, Ar may be bonded to an atom bonded to a core of phenyl at a meta position thereof, and Chemical Formula 14 may be selected from the following compounds.
1-216
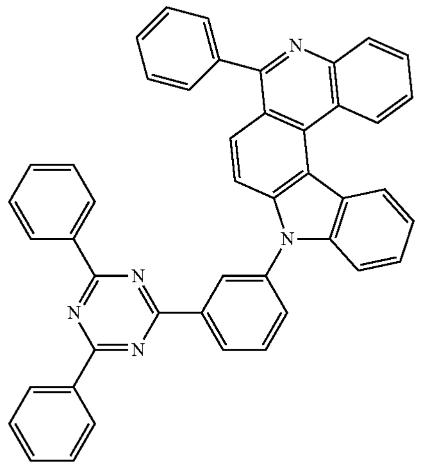
1-217
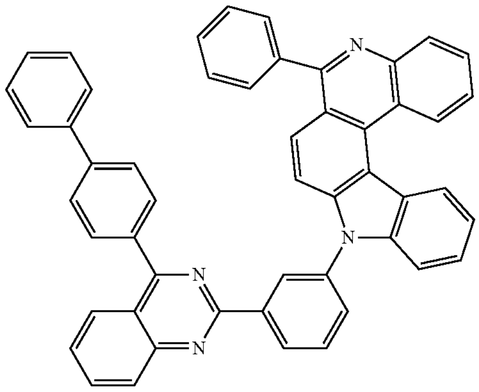
-continued
1-218
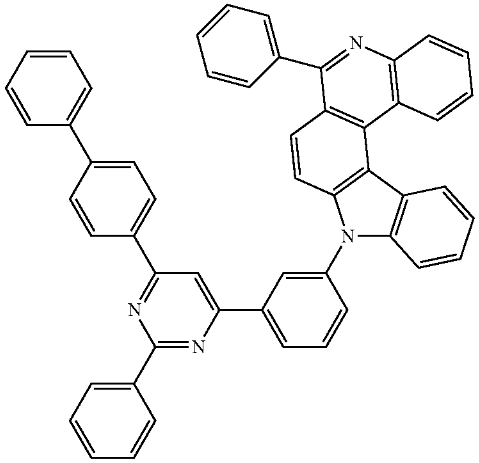
1-219
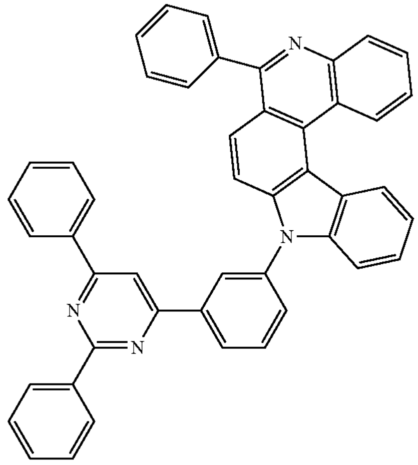
1-220
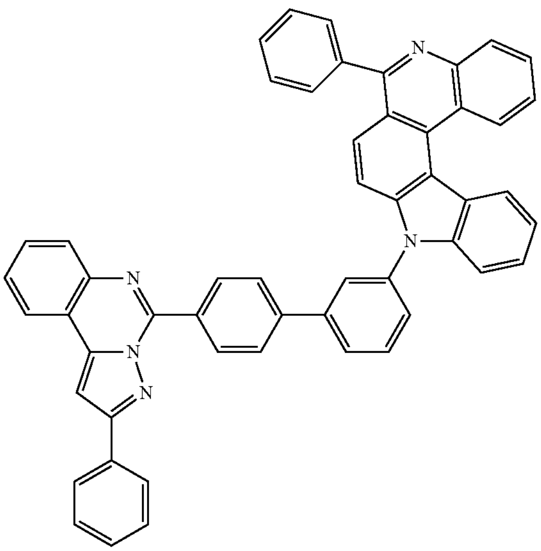

-continued
1-221
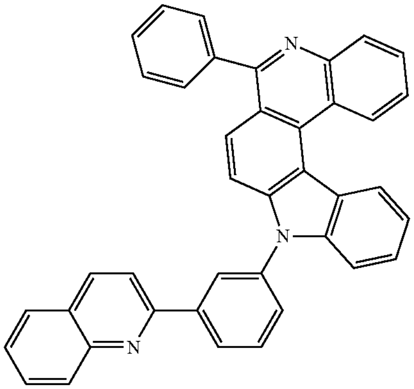
1-222
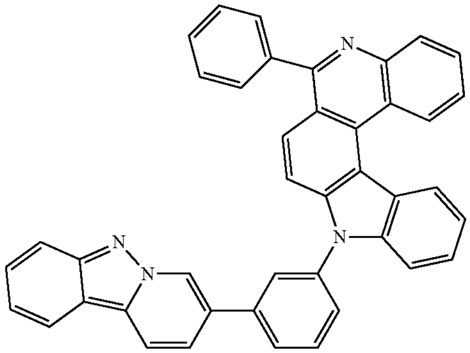
1-223
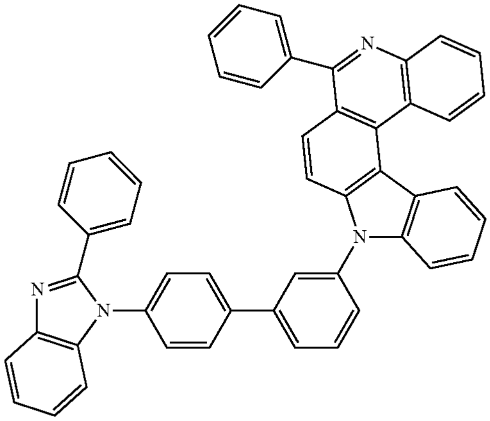
1-224
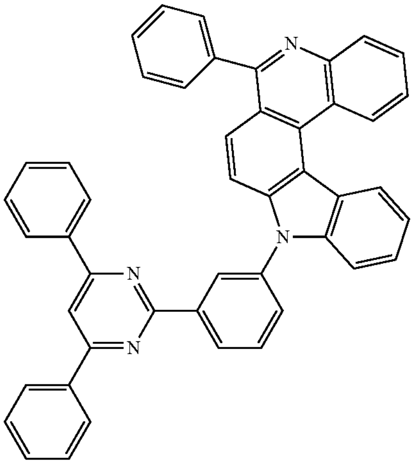
-continued
1-225
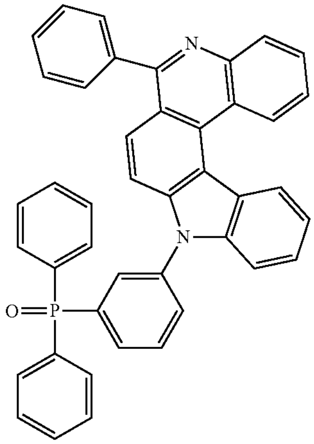
1-226
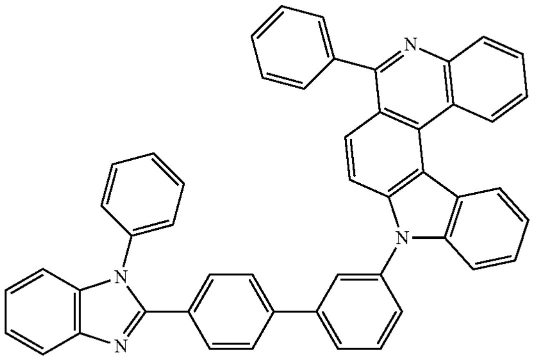
1-227
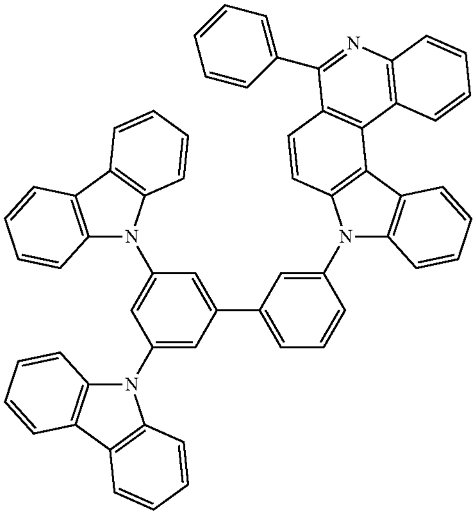

-continued
1-228
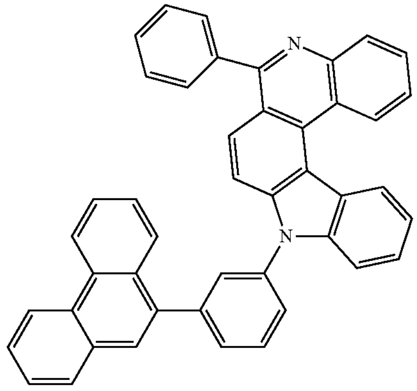
1-229
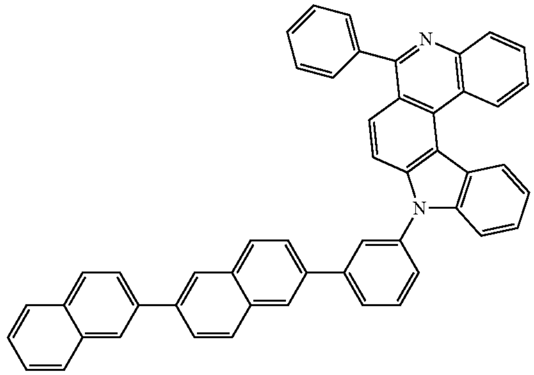
1-230
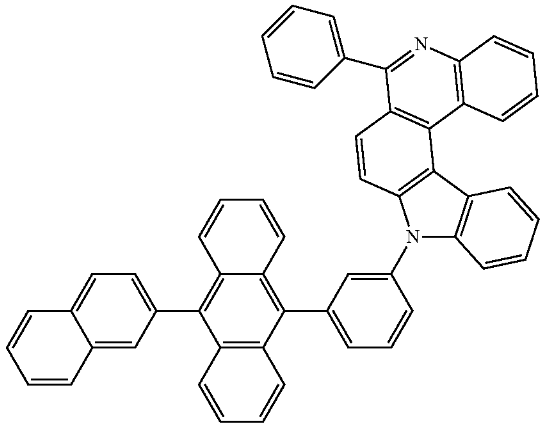
1-231
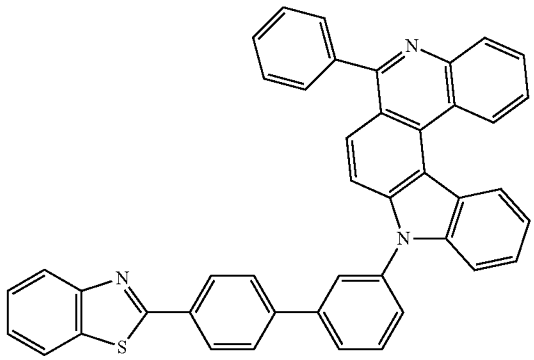
-continued
1-232
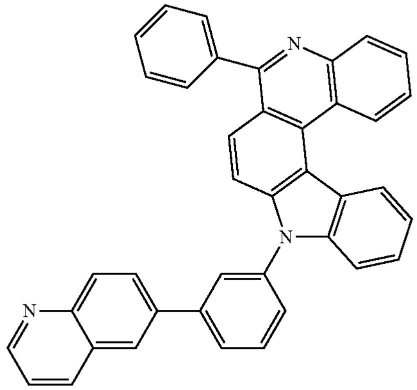
1-233
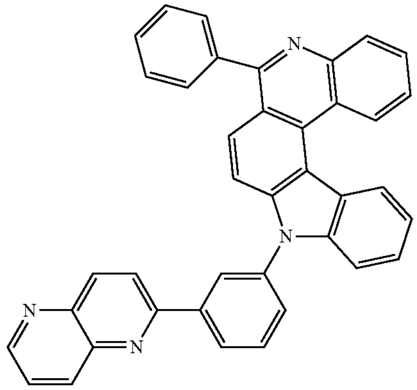
1-234
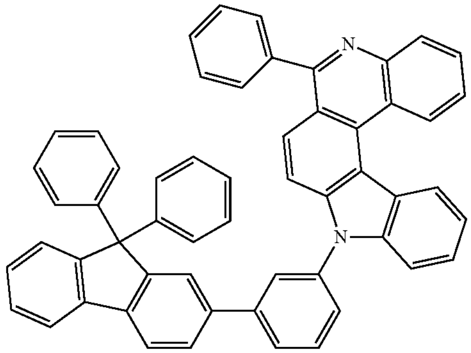
1-235
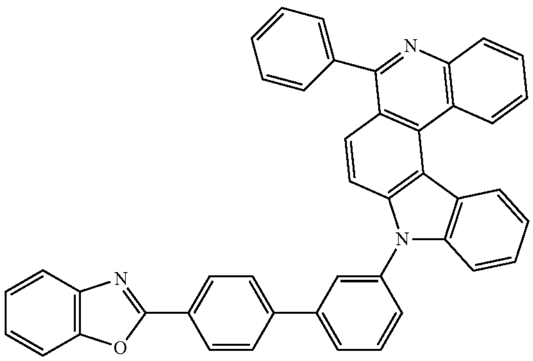

-continued
1-236
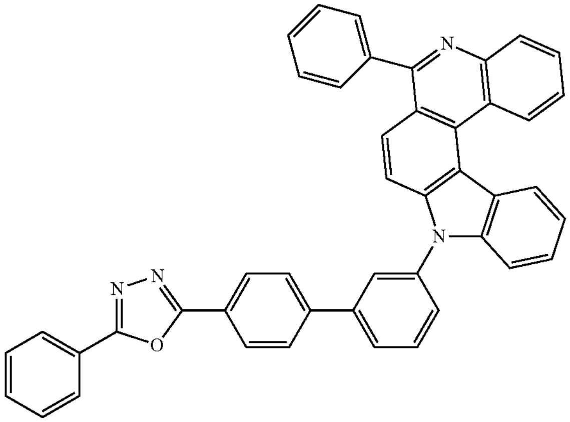
1-237
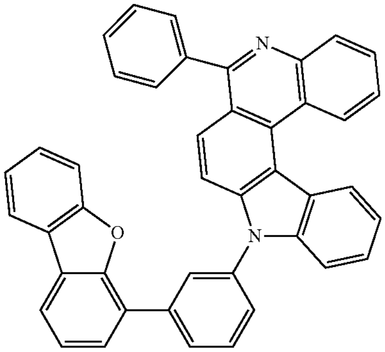
1-238
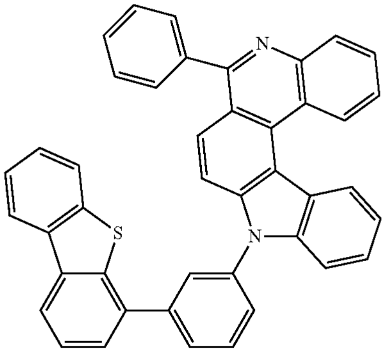
1-239
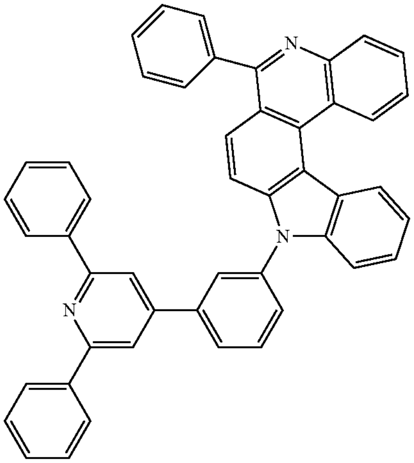
-continued
1-240
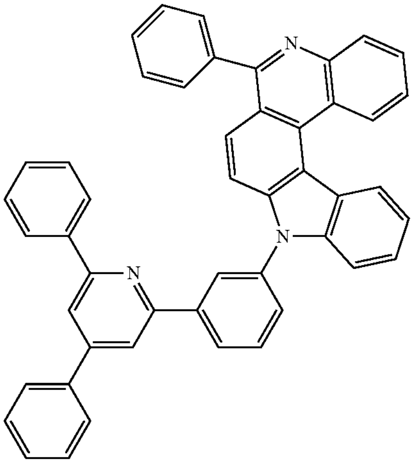
1-241
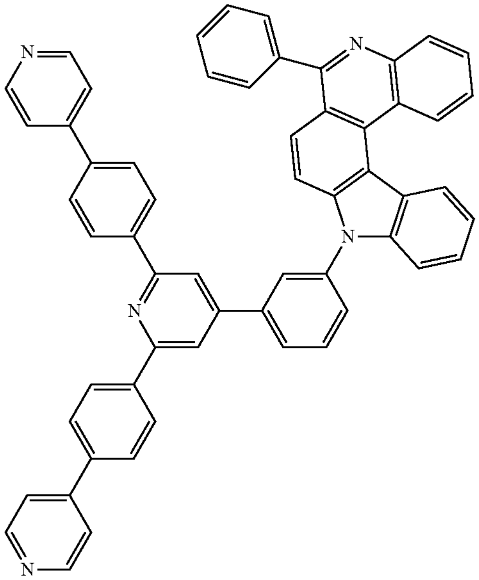
1-242
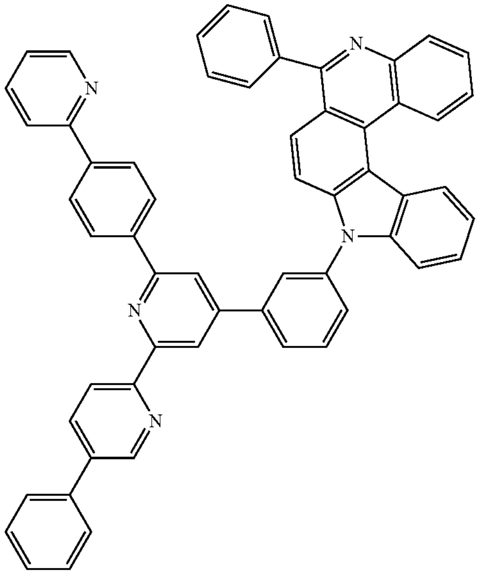

-continued
1-243
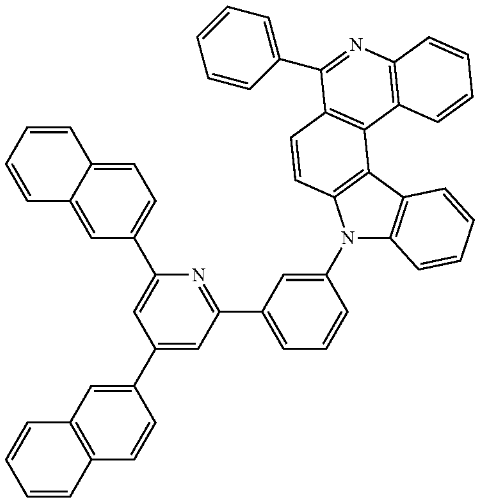
1-244
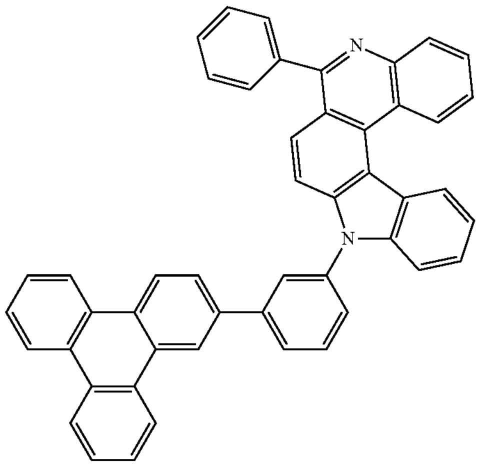
1-245
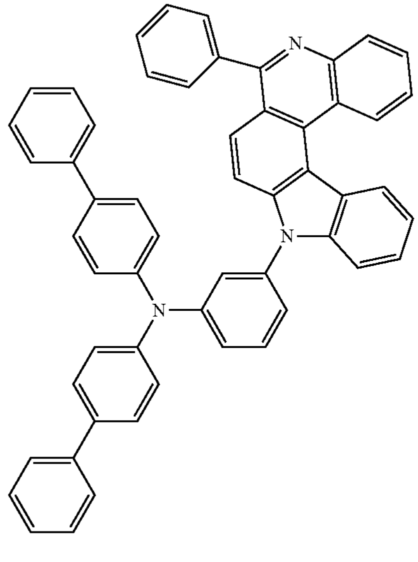
-continued
1-246
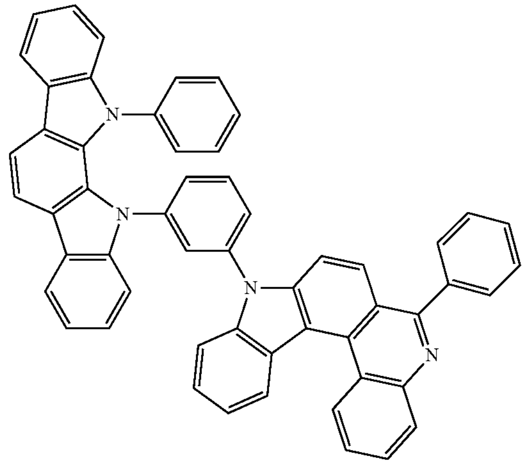
1-247
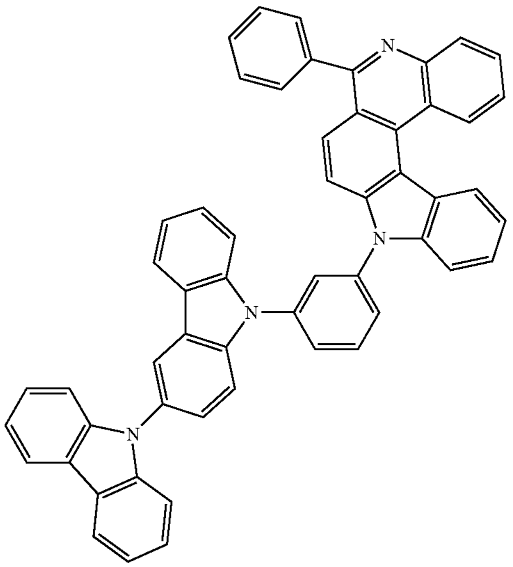
1-248
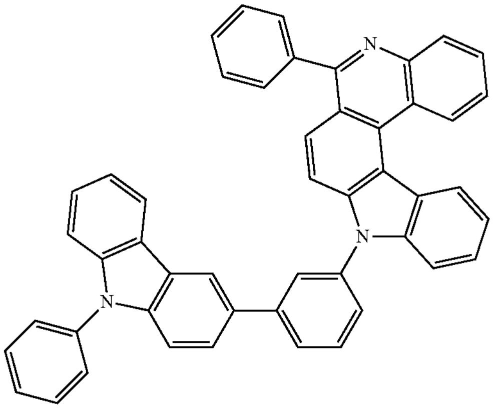

-continued
1-249
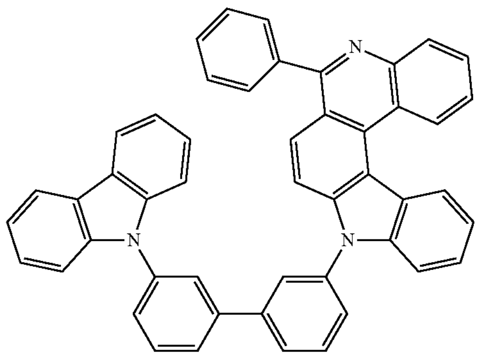
1-250
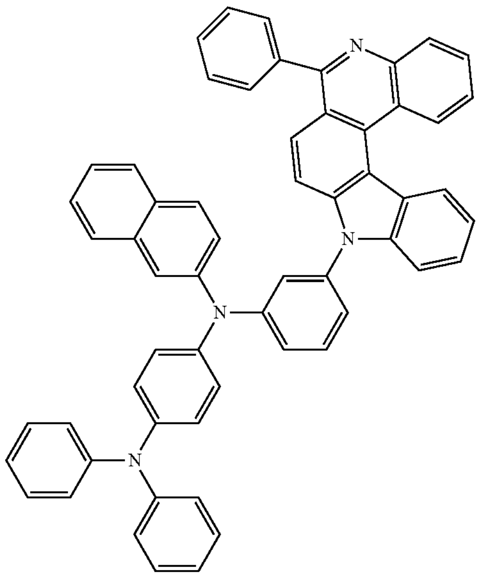
1-488
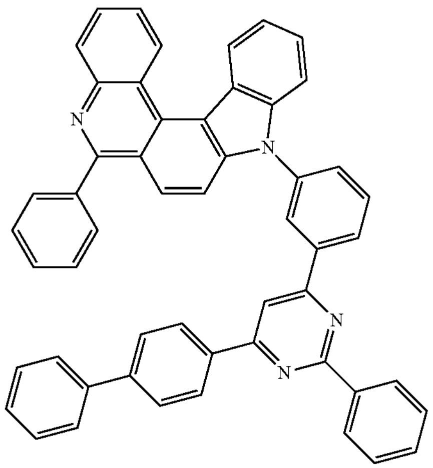
-continued
1-489
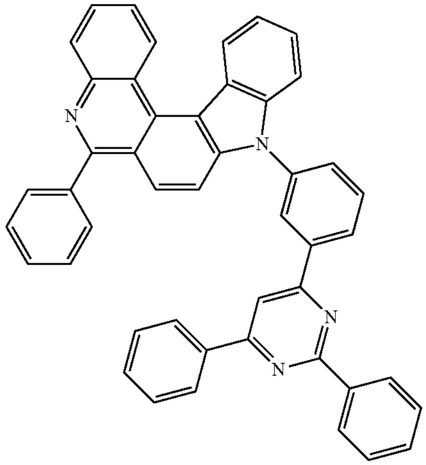
1-490
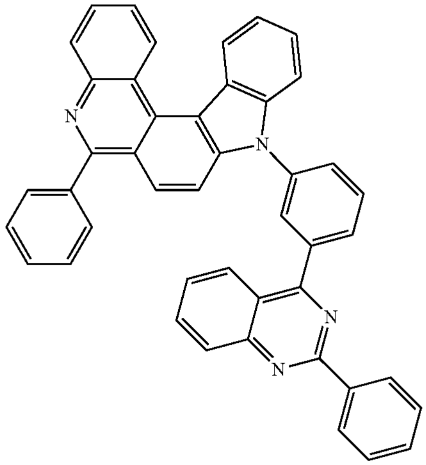
1-491
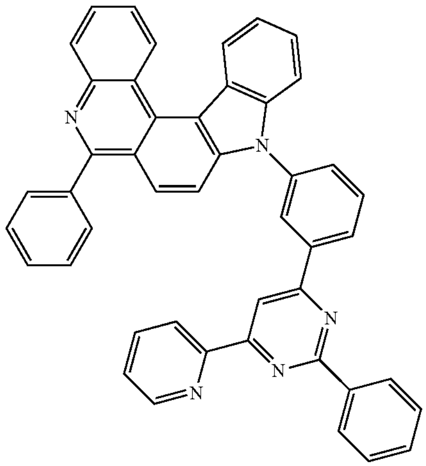

-continued
1-492
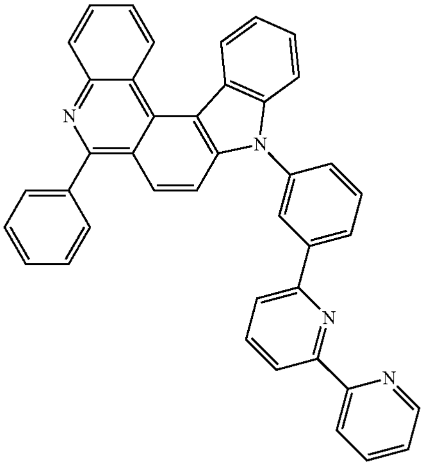
1-493
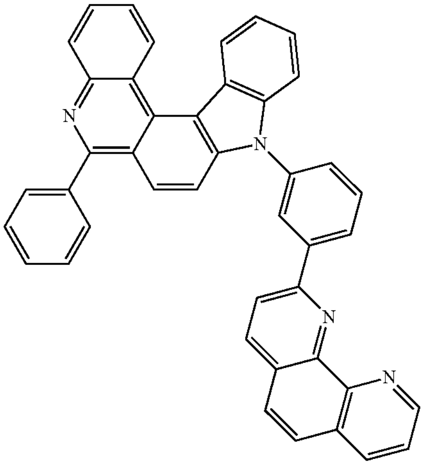
1-494
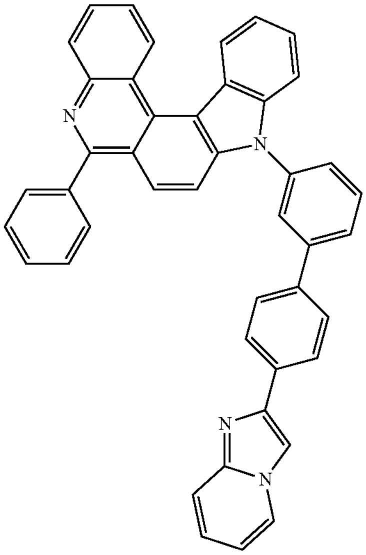
In Chemical Formulas 15, 16, and 26, Ar may be bonded to an atom bonded to a core of phenyl at a para position thereof, and Chemical Formulas 15, 16, and 26 may be selected from the following compounds.
2-1
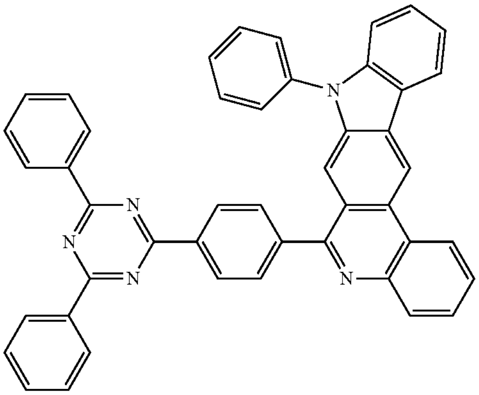
2-2
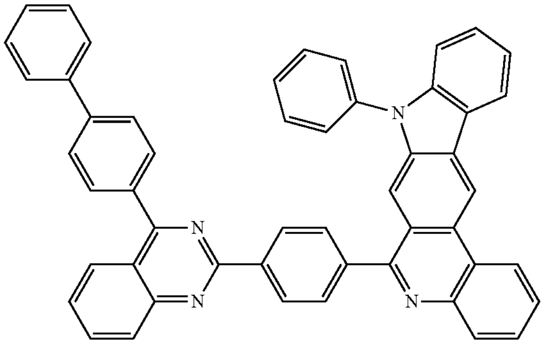
2-3
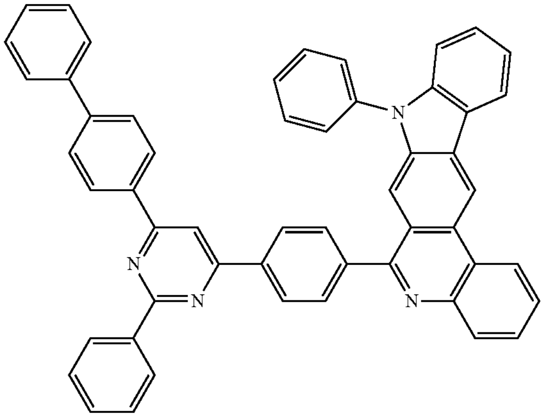
2-4
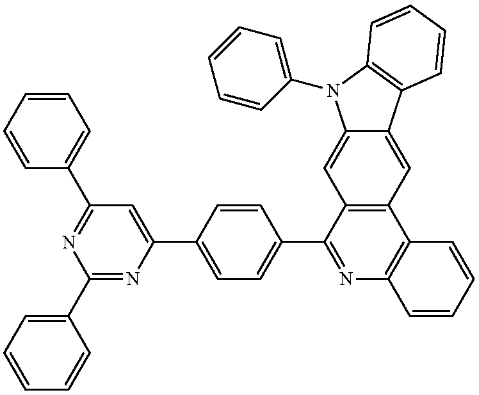

-continued
2-5
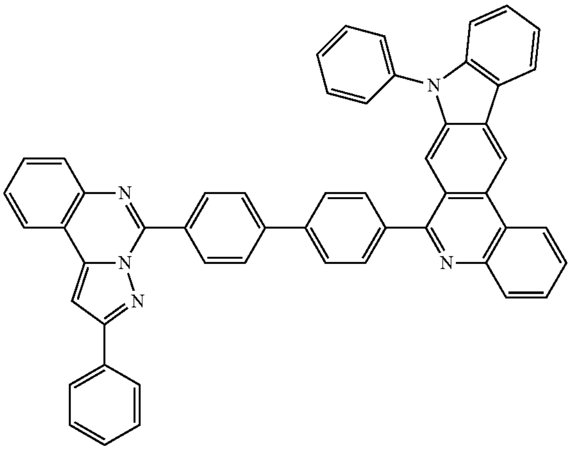
2-6
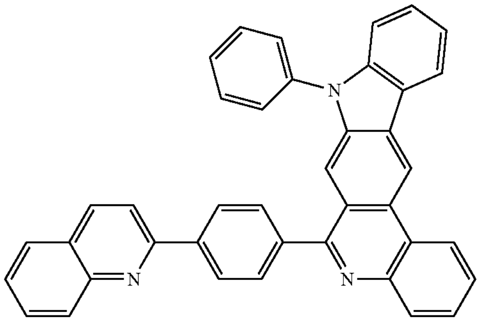
2-7
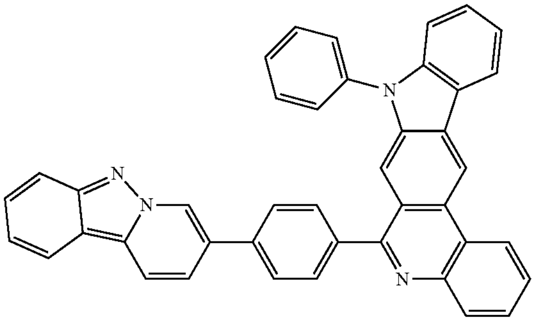
2-8
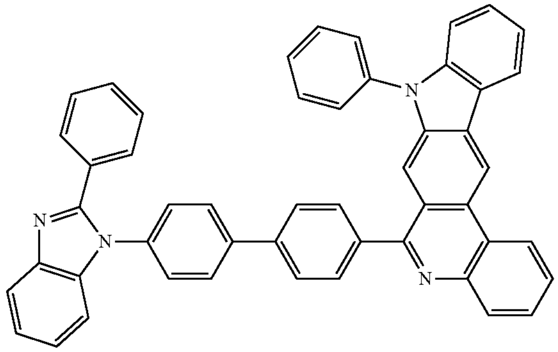
-continued
2-9
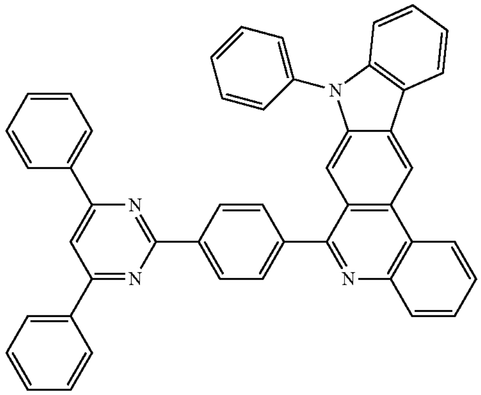
2-10
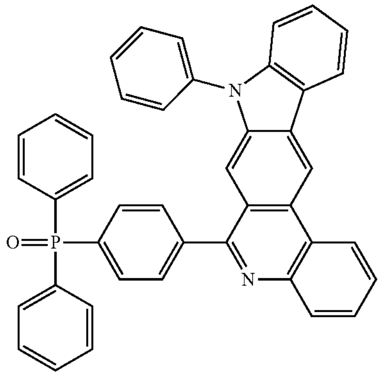
2-11
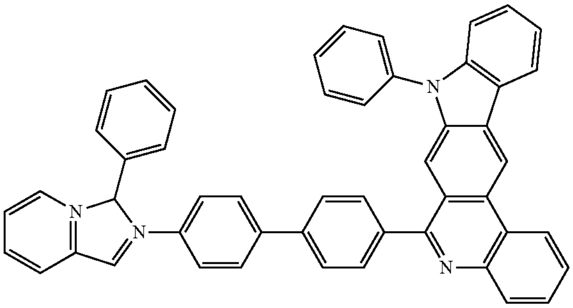
2-12
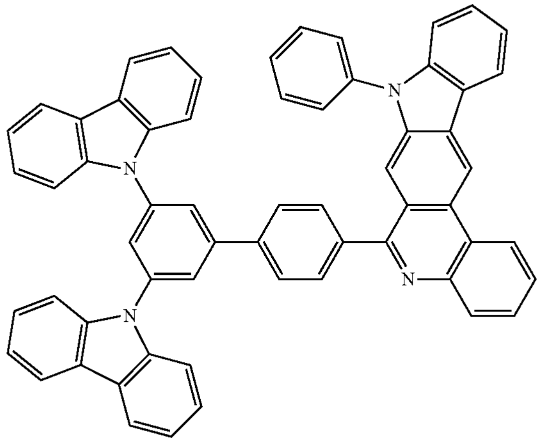

-continued
2-13
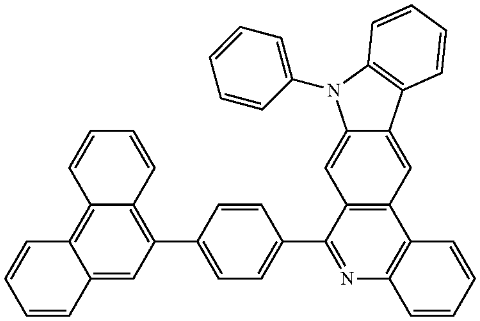
2-14
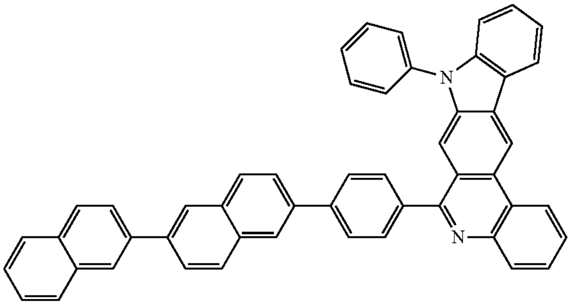
2-15
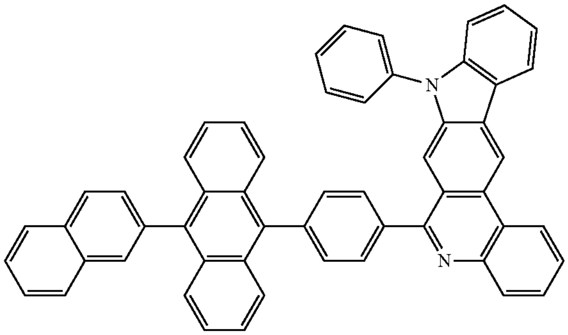
2-16
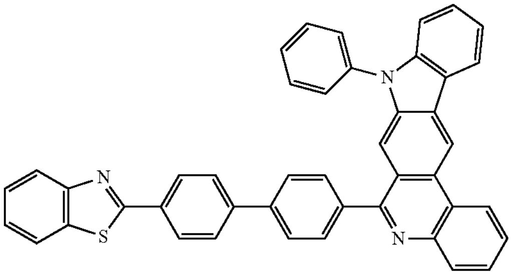
2-17
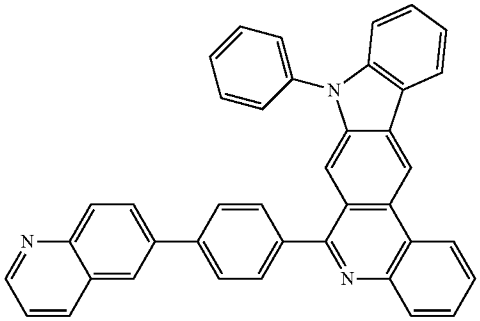
-continued
2-18
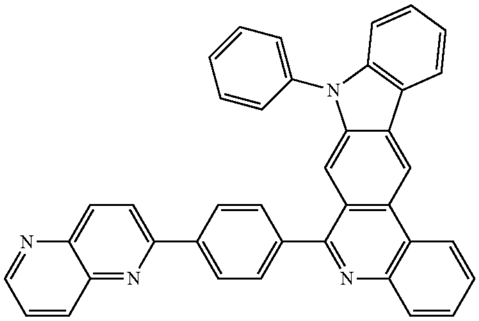
2-19
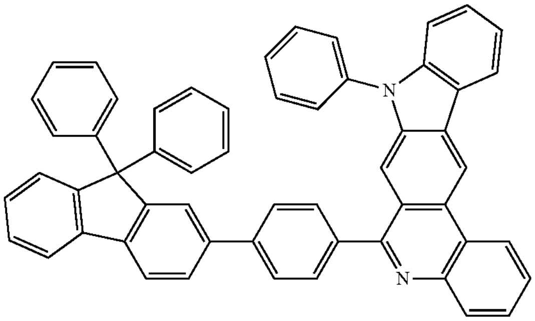
2-20
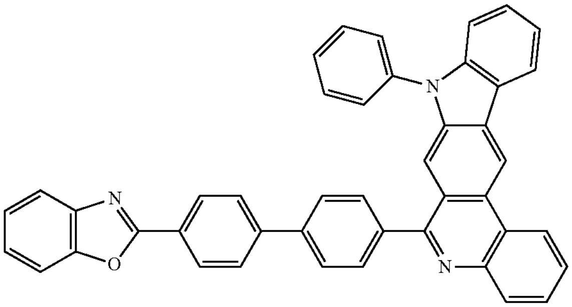
2-21
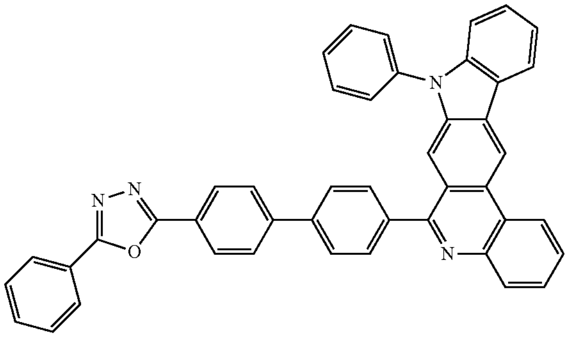

-continued
2-22
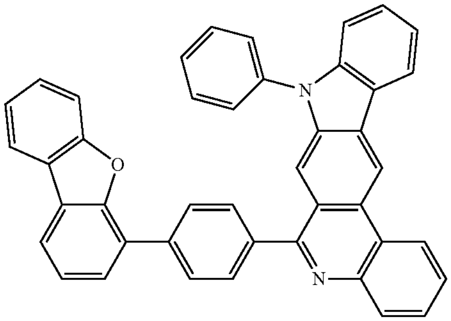
2-23
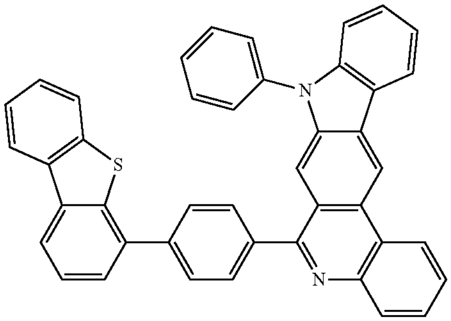
2-24
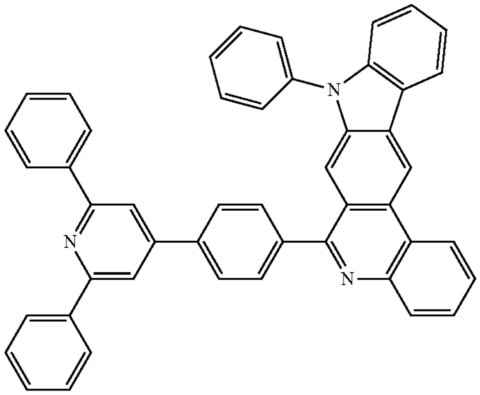
2-25
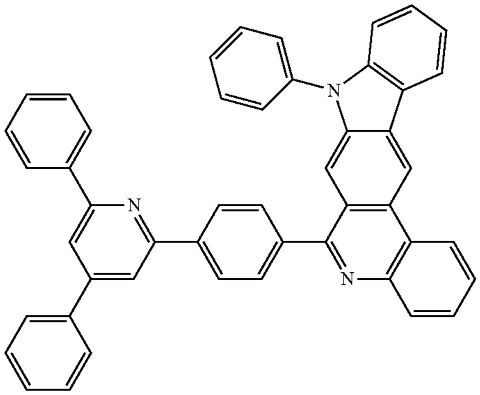
-continued
2-26
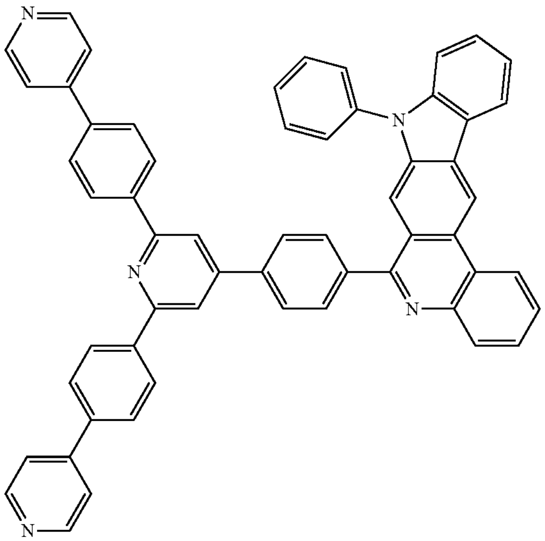
2-27
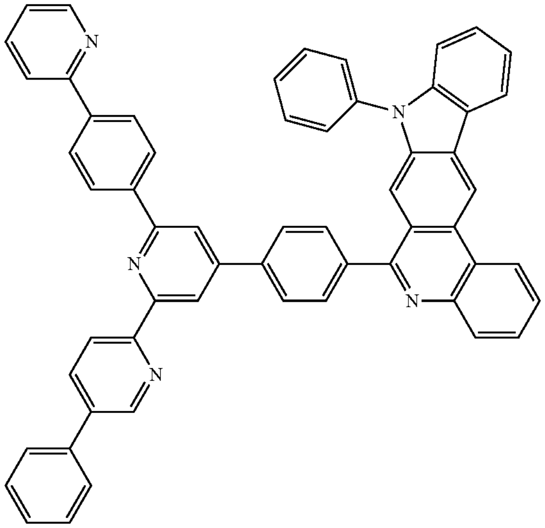
2-28
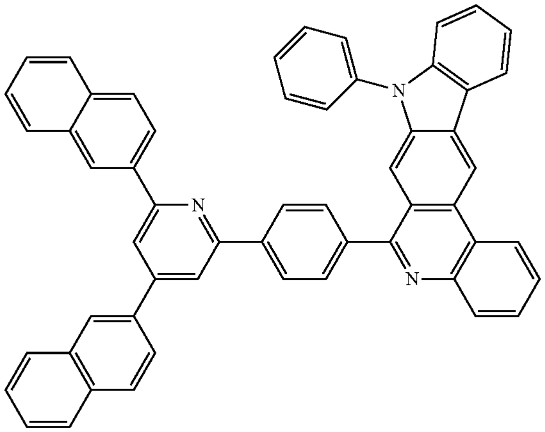

-continued
2-29
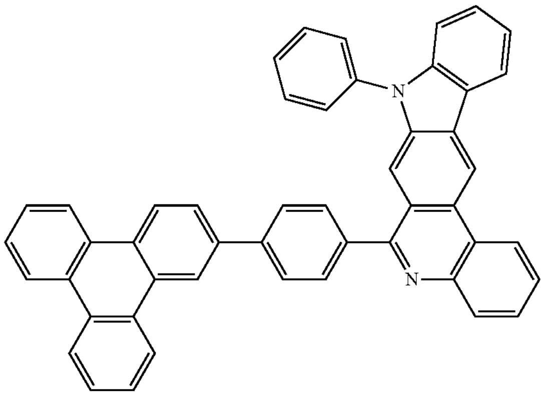
2-30
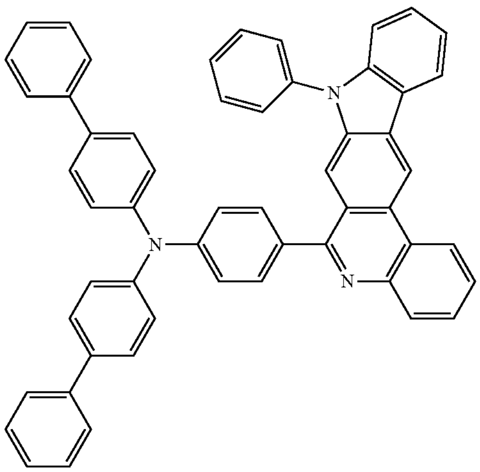
2-31
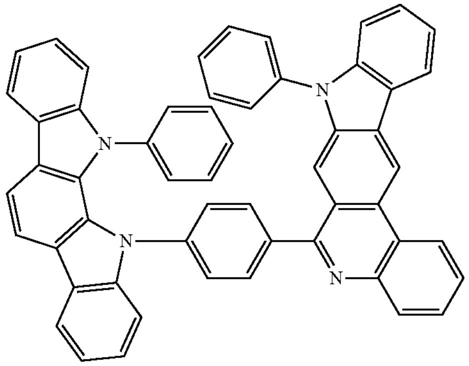
-continued
2-32
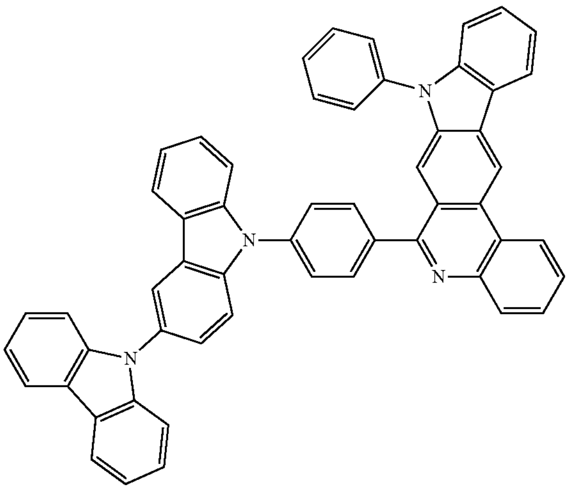
2-33
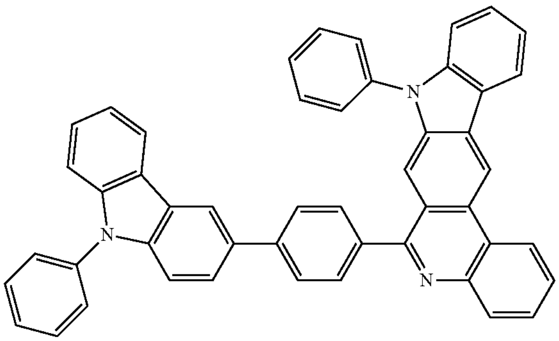
2-34
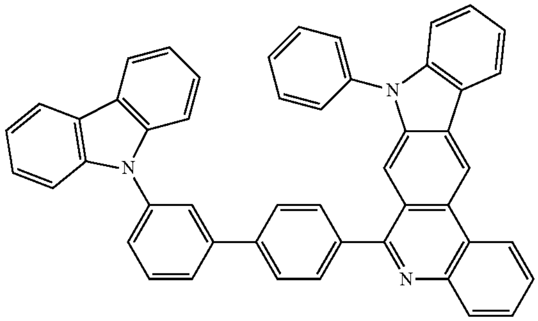

-continued
2-35
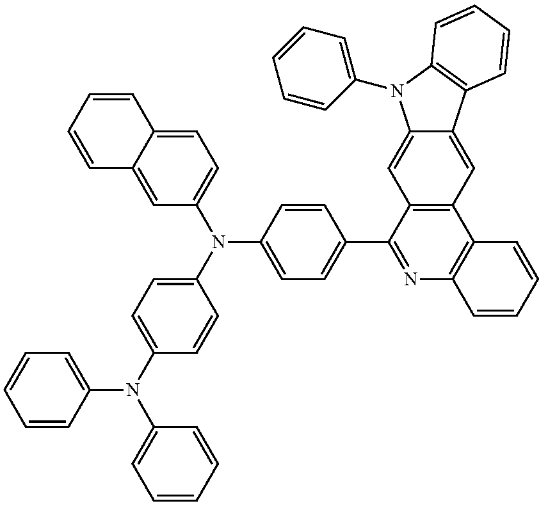
2-36
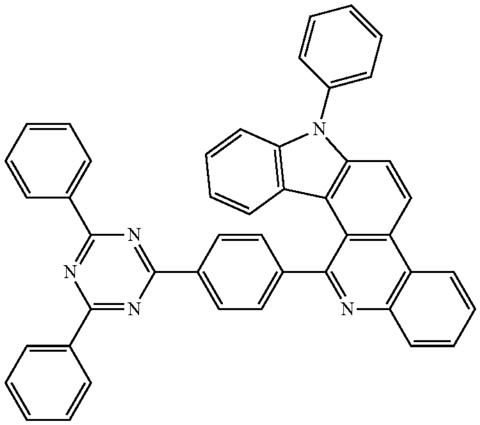
2-37
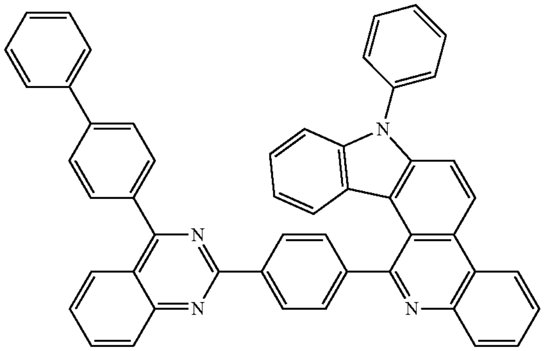
-continued
2-38
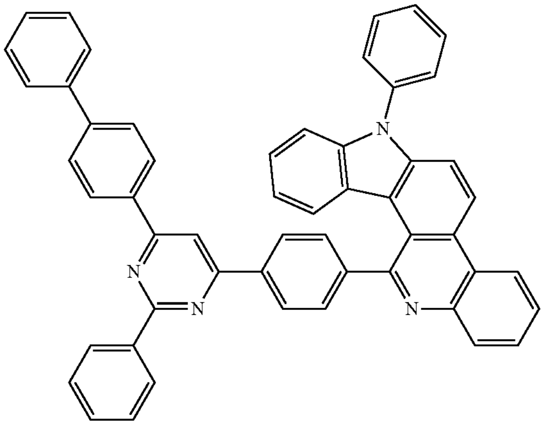
2-38
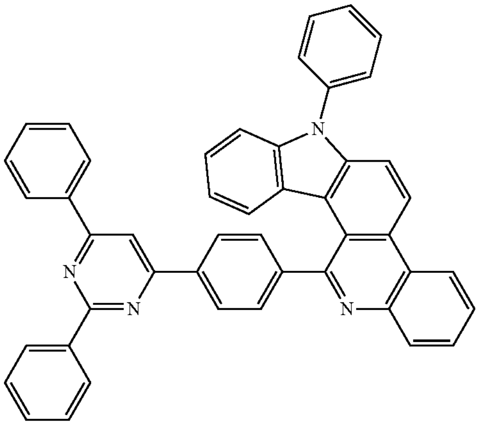
2-40
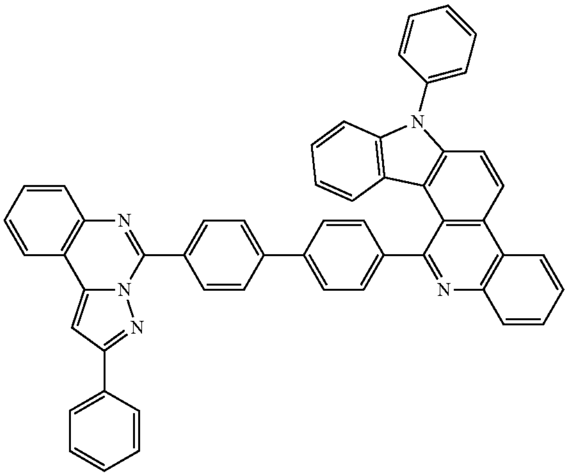

-continued
2-41
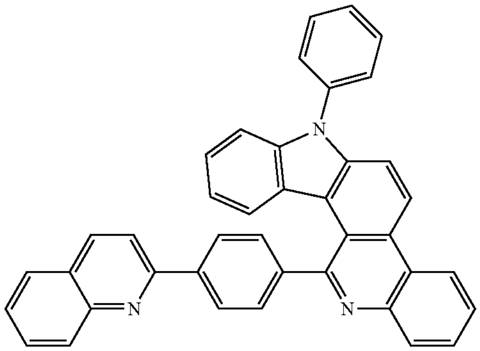
2-42
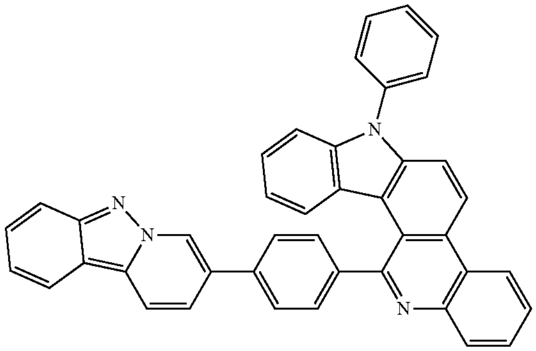
2-43
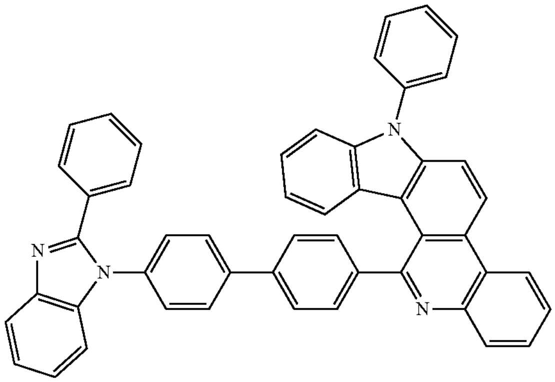
2-44
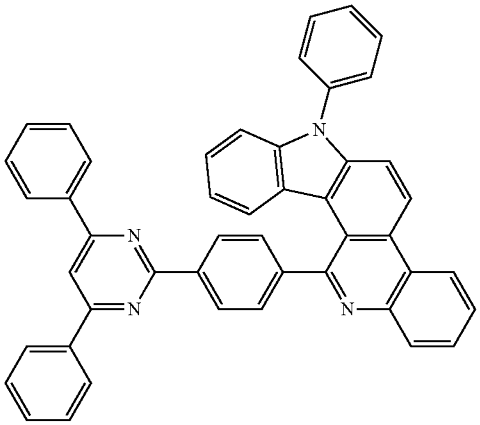
-continued
2-45
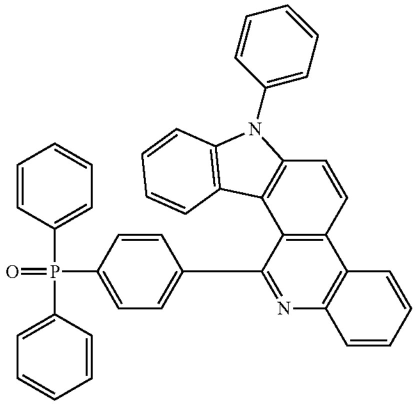
2-46
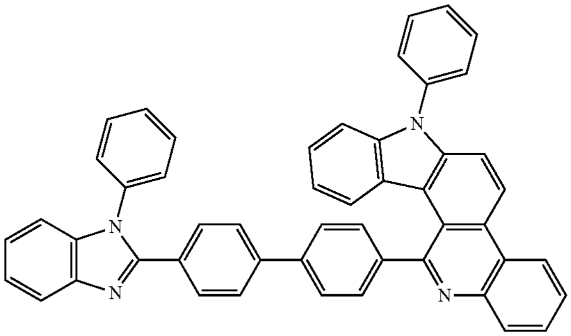
2-47
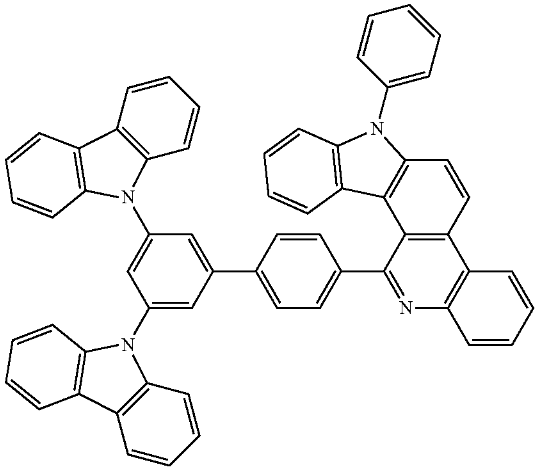
2-48
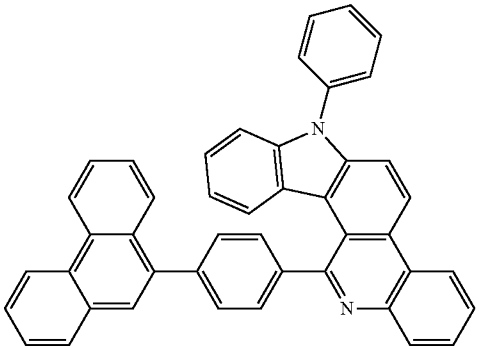

-continued
2-49
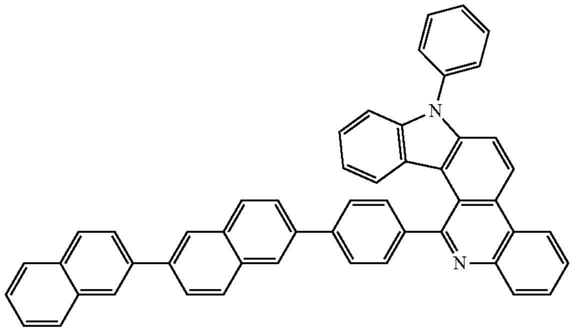
2-50
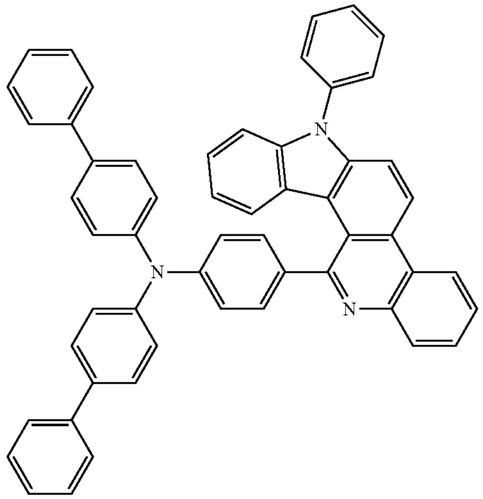
2-51
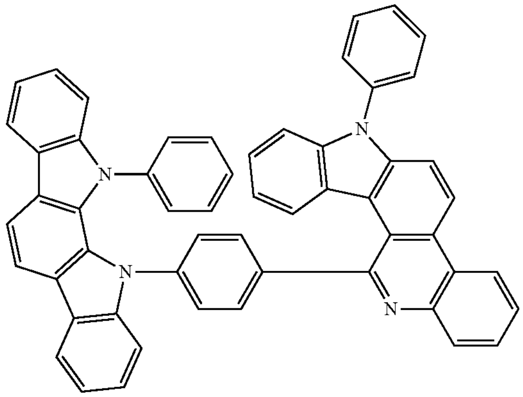
2-52
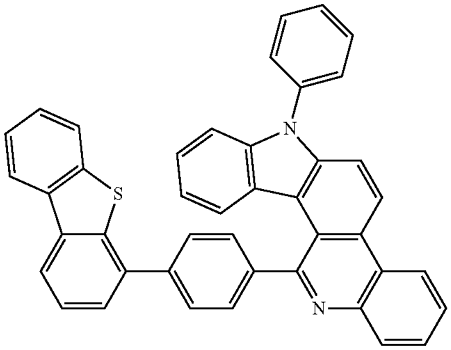
-continued
2-53
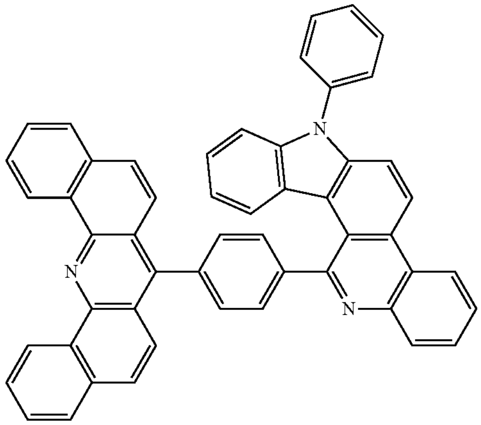
2-54
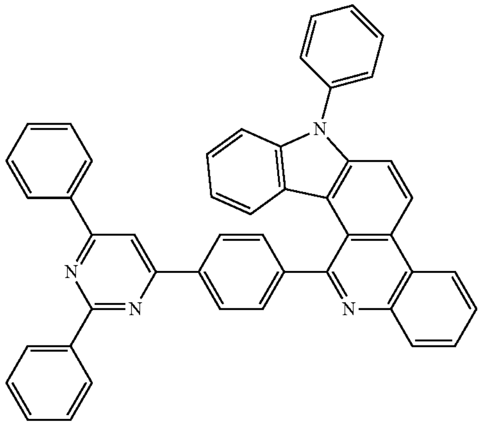
2-55
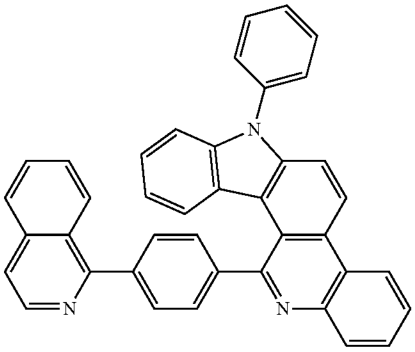
2-56
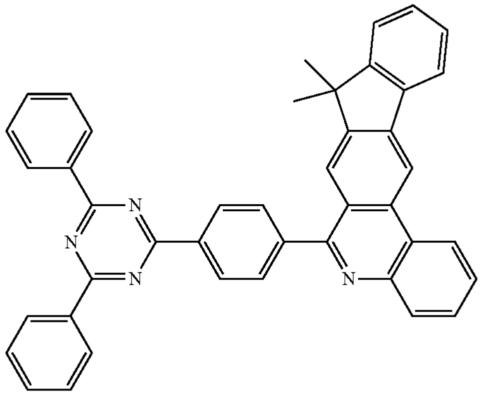

-continued
2-57
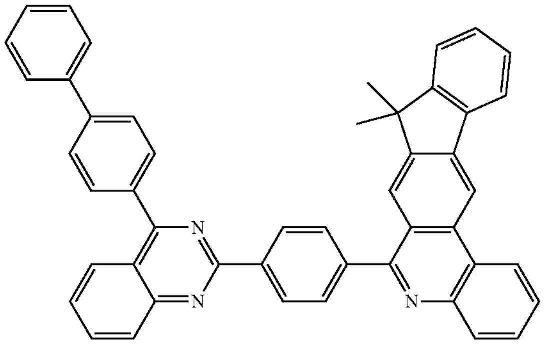
2-58
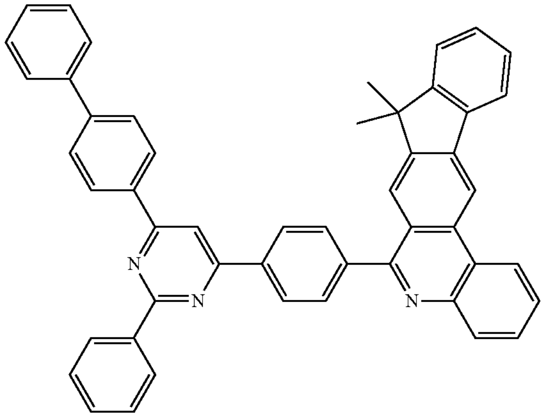
2-59
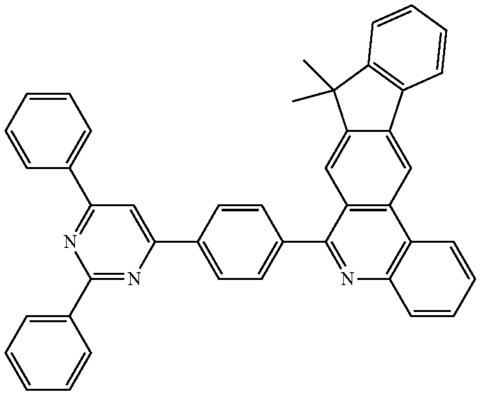
-continued
2-60
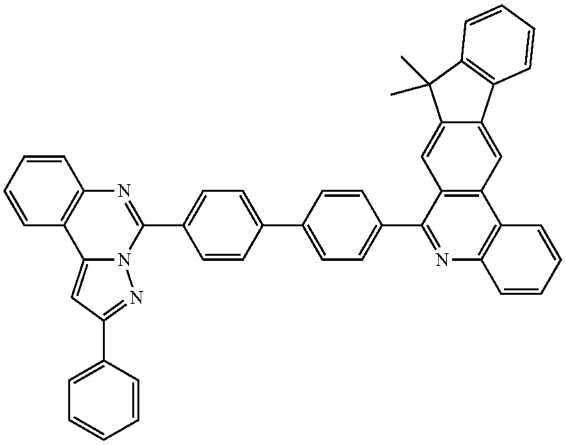
2-61
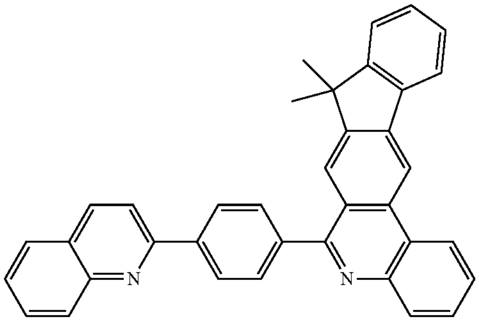
2-62
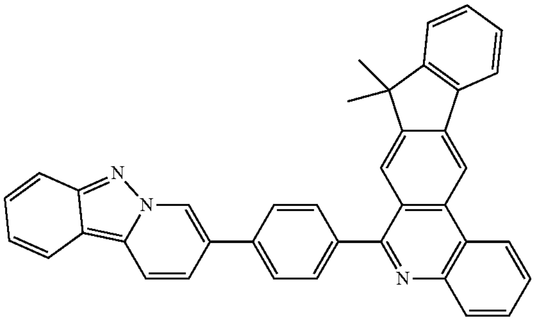
2-63
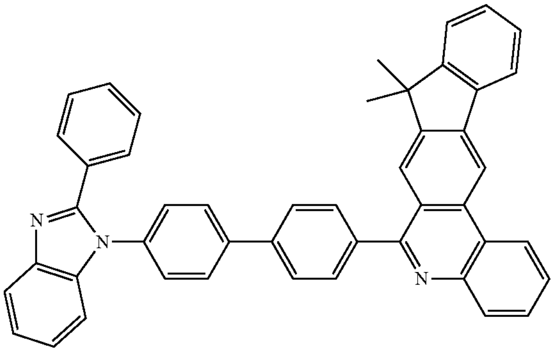

-continued
2-64
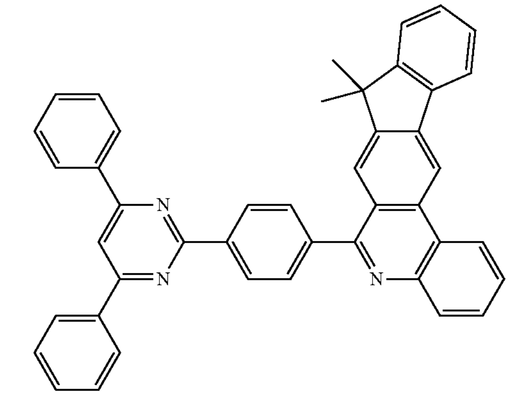
2-65
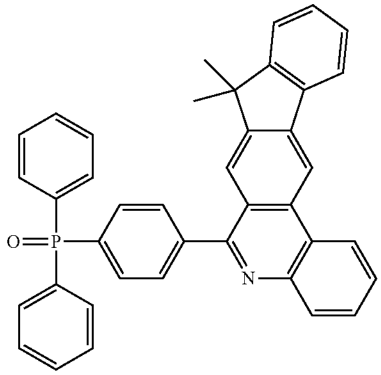
2-66
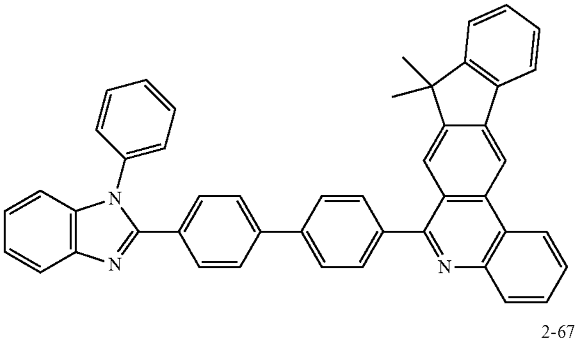
2-67
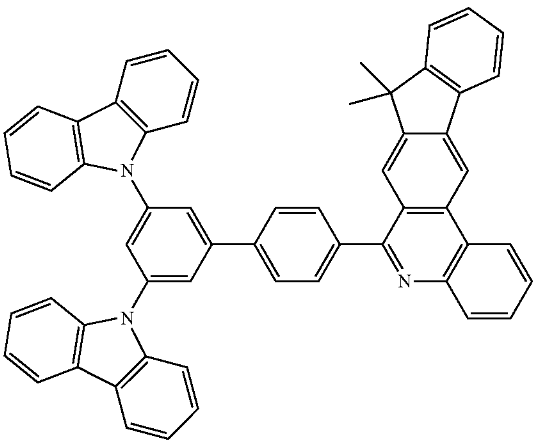
-continued
2-68
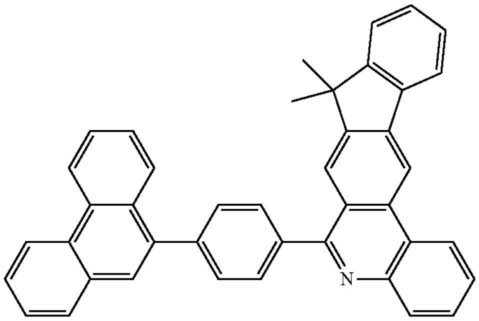
2-69
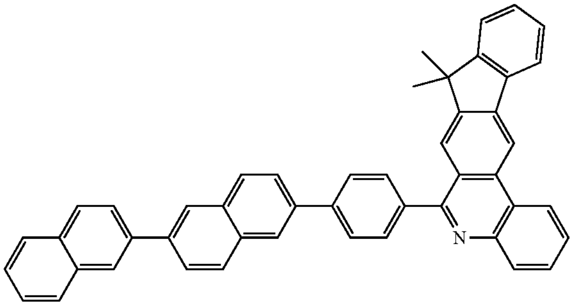
2-70
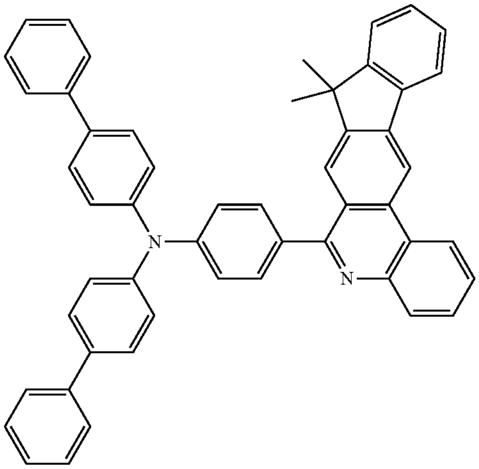
2-71
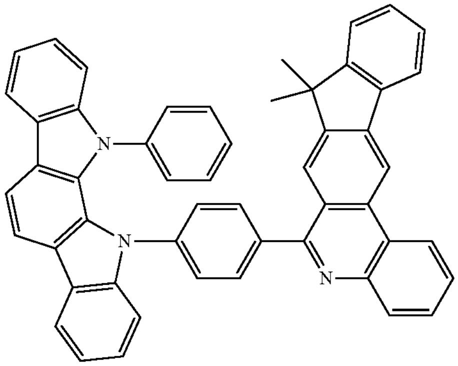

-continued
2-72
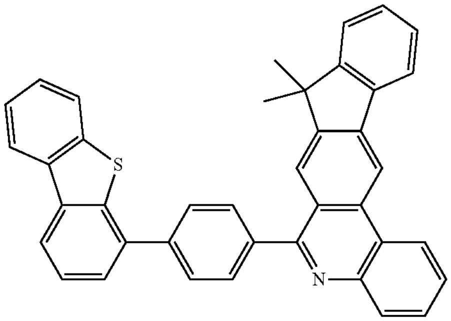
2-73
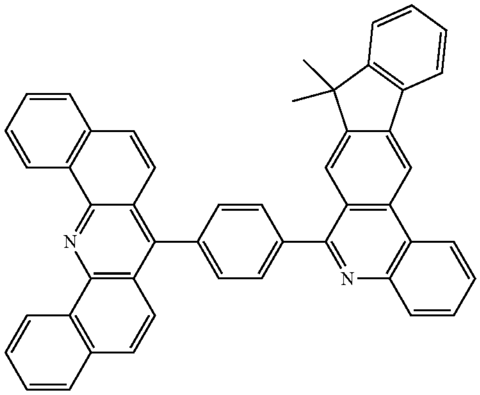
2-74
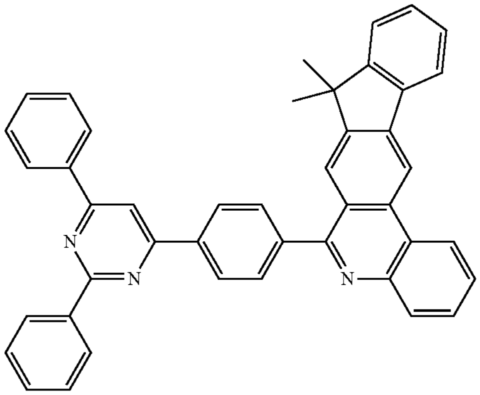
2-75
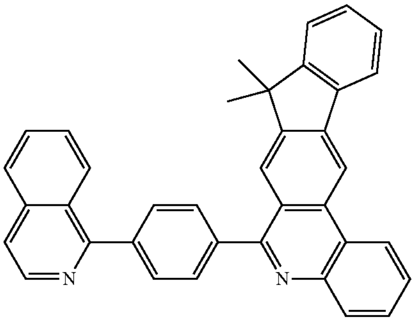
-continued
2-76
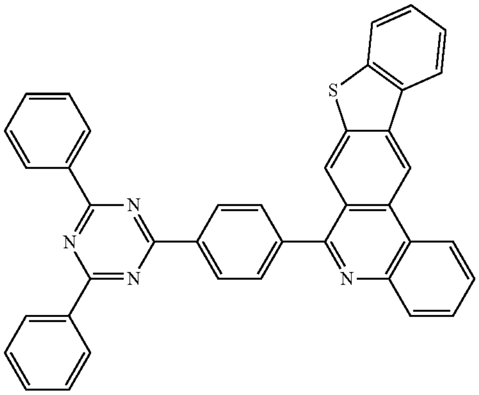
2-77
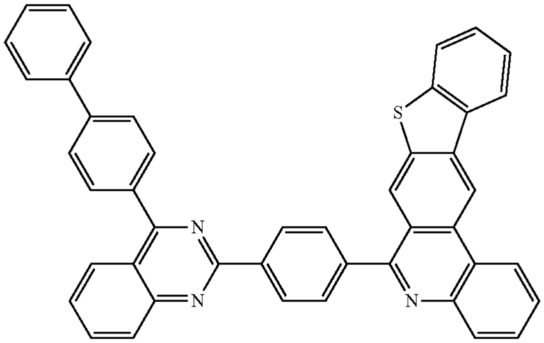
2-78
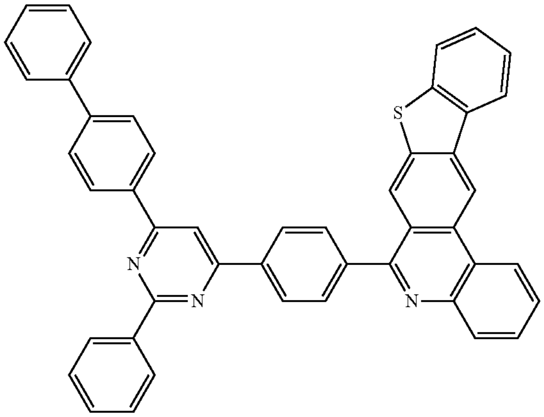
2-79
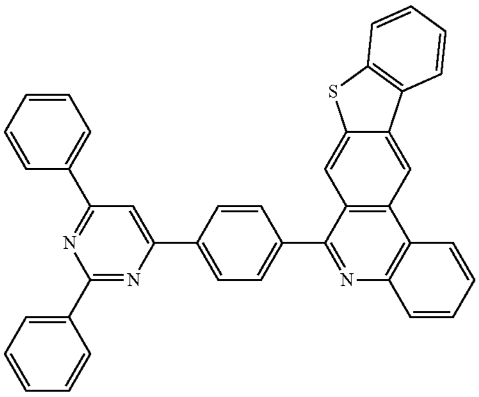

-continued
2-80
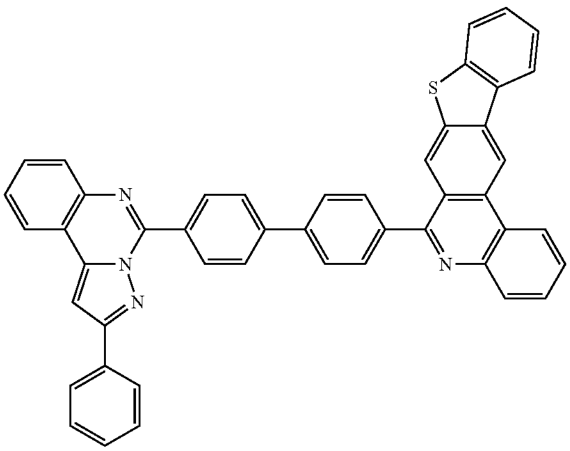
2-81
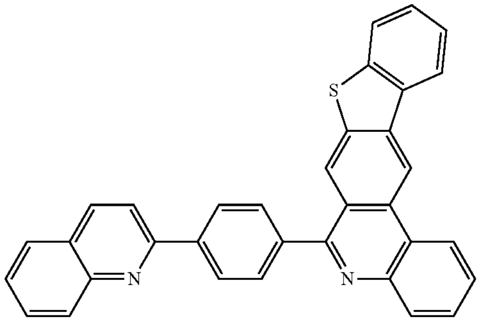
2-82
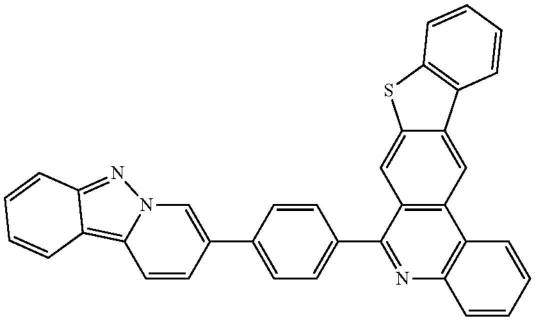
2-83
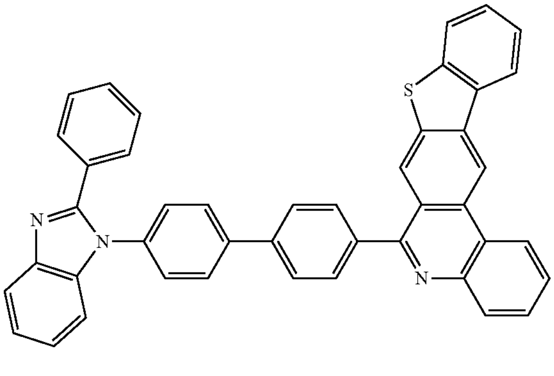
-continued
2-84
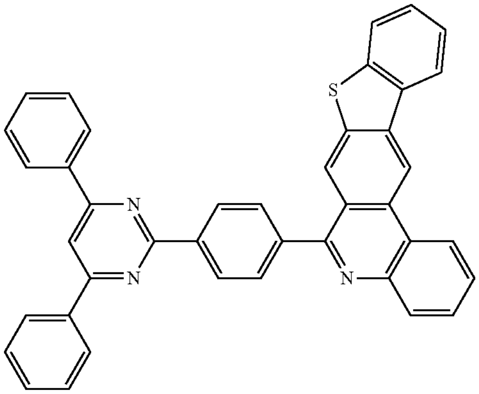
2-85
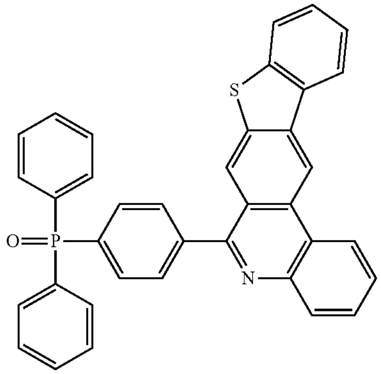
2-86
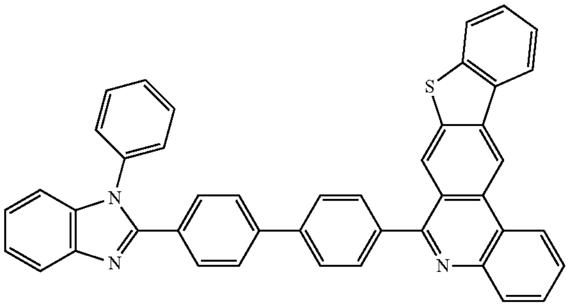
2-87
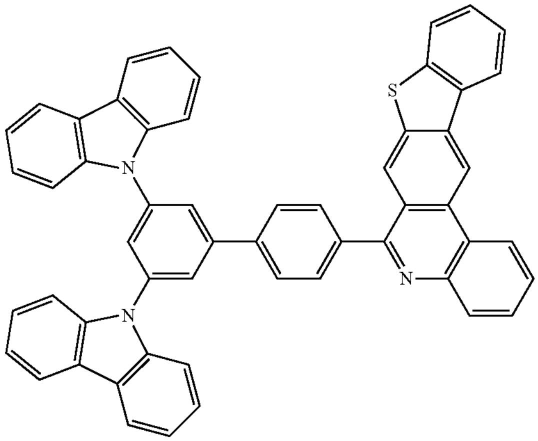

-continued
2-88
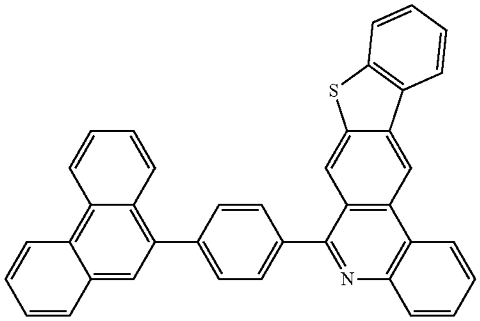
2-89
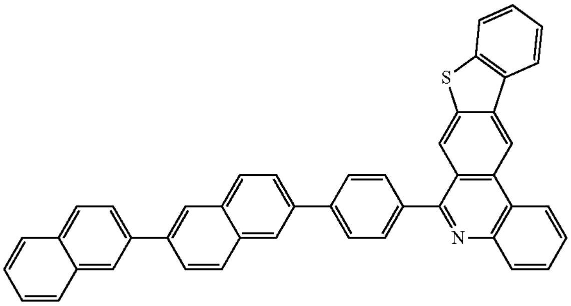
2-90
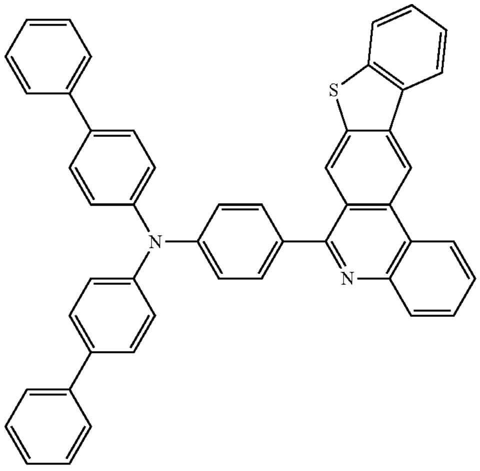
2-91
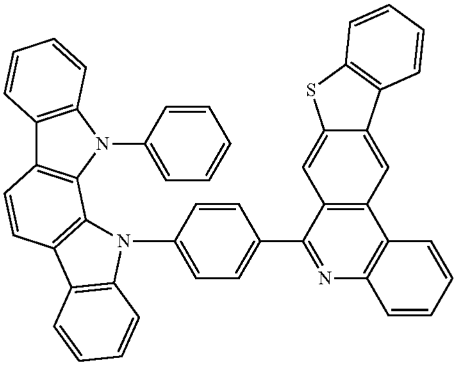
-continued
2-92
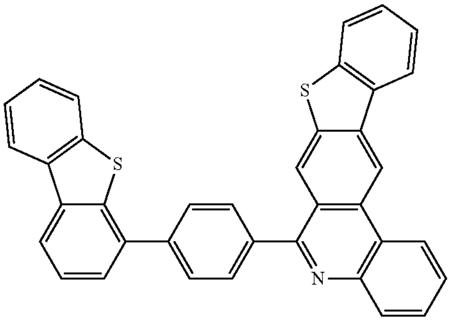
2-93
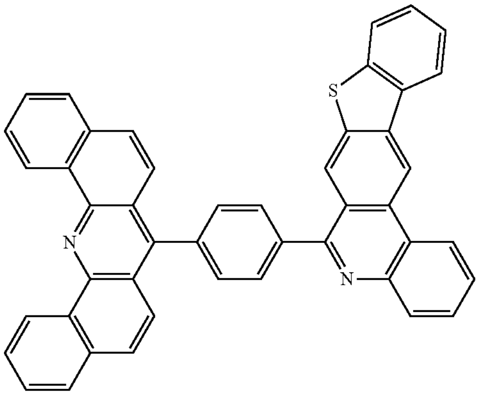
2-94
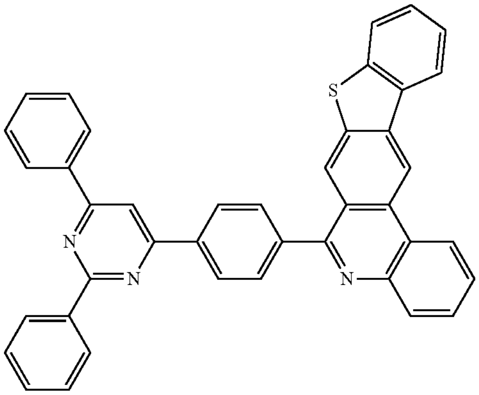
2-95
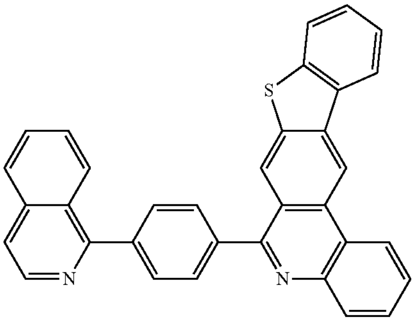

-continued
2-96
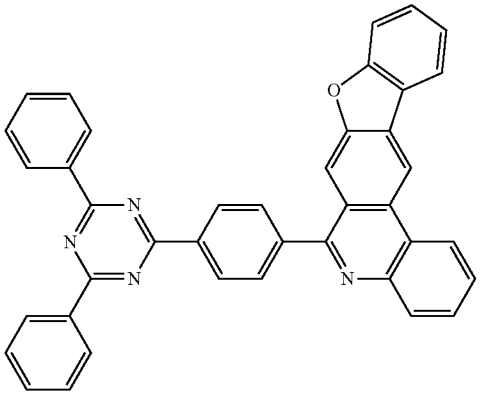
2-97
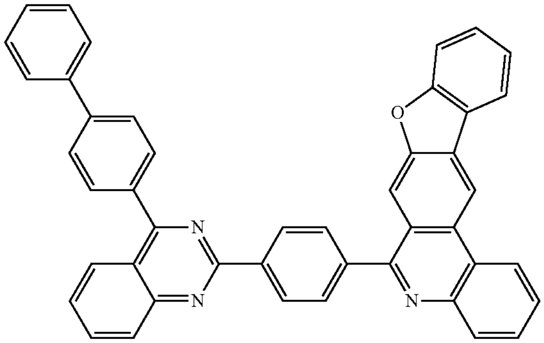
2-98
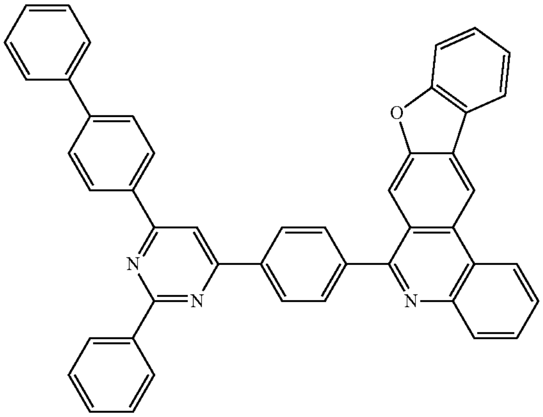
2-99
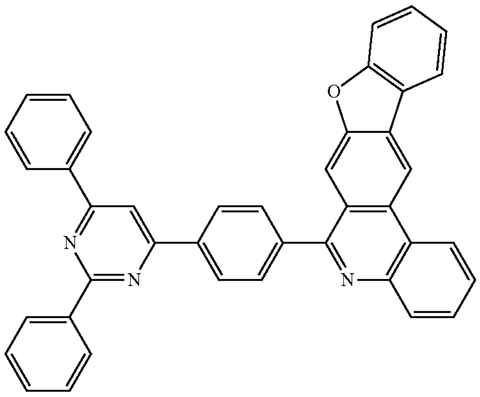
-continued
2-100
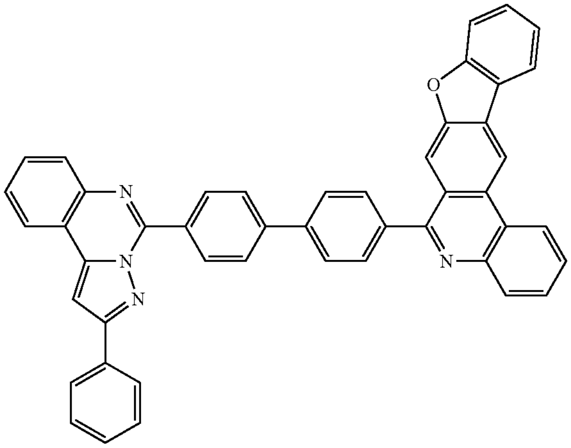
2-101
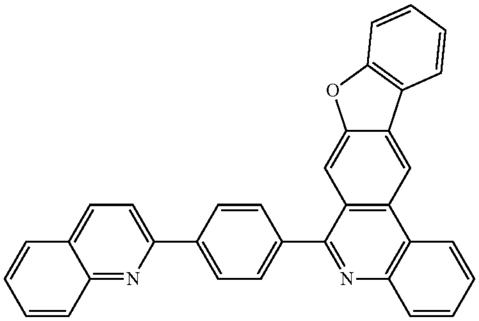
2-102
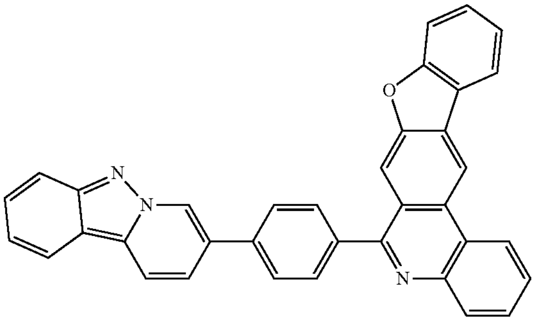
2-103
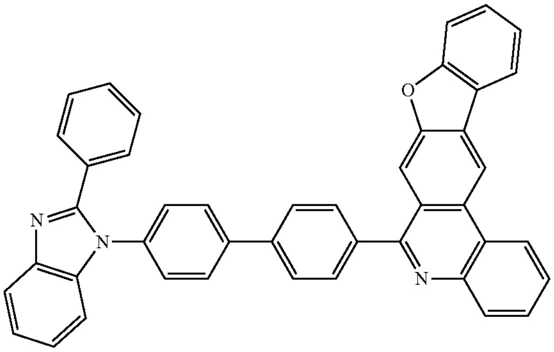

-continued
2-104
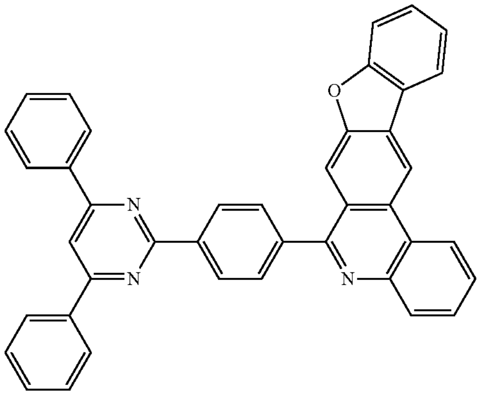
2-105
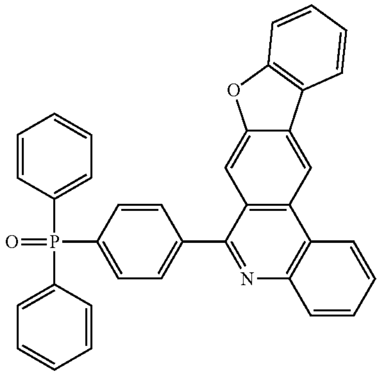
2-106
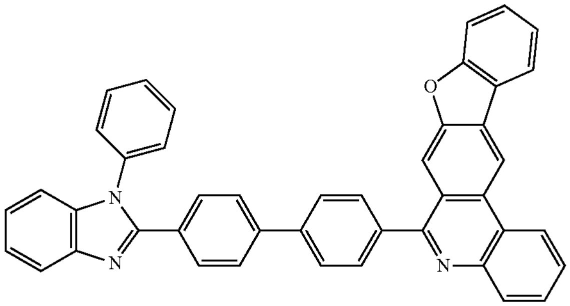
2-107
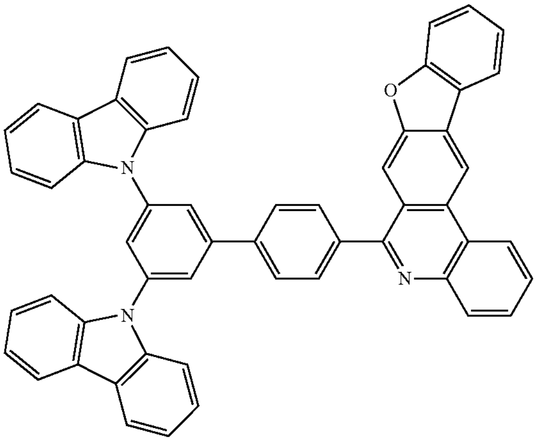
-continued
2-108
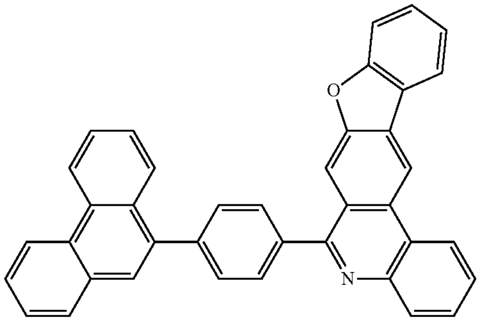
2-109
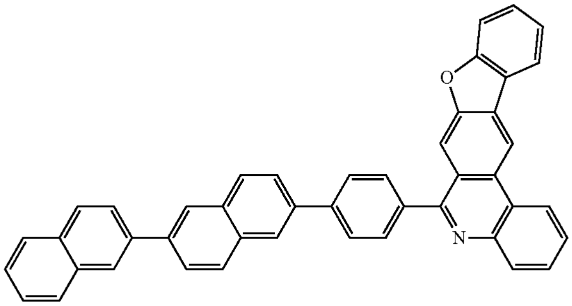
2-110
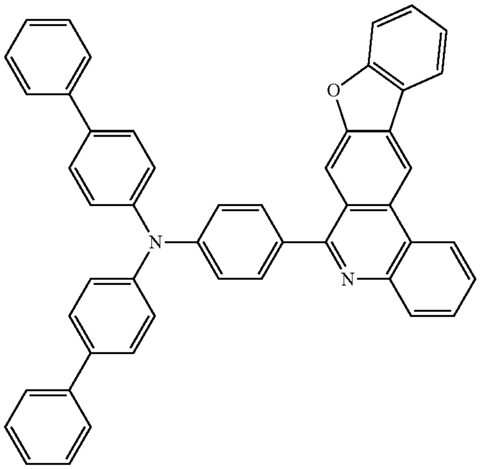
2-111
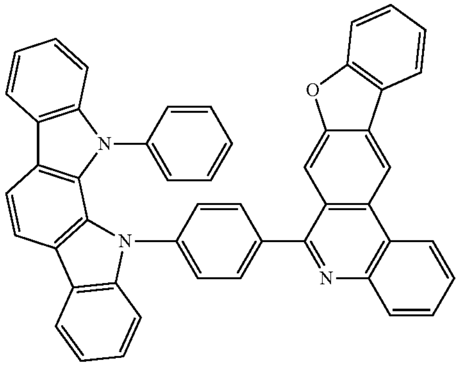

-continued
2-112
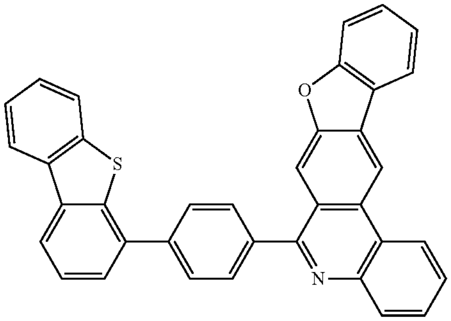
2-113
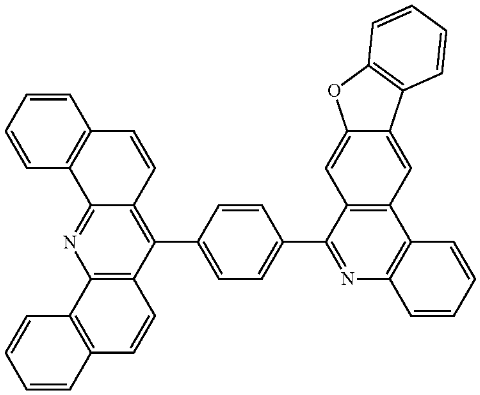
2-114
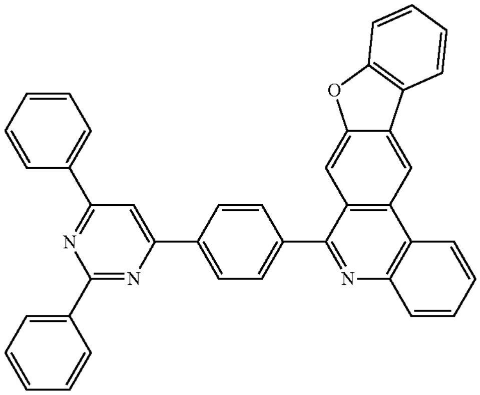
2-115
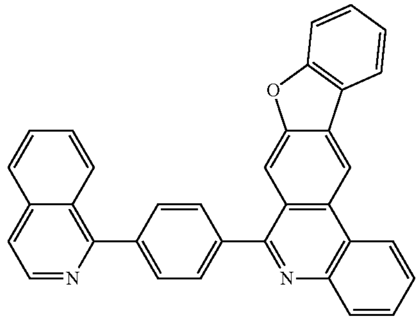
According to another exemplary embodiment of the present specification,
In Chemical Formulas 15, 16, and 26, Ar may be bonded to an atom bonded to a core of phenyl at a meta position thereof, and Chemical Formulas 15, 16, and 26 may be selected from the following compounds.
2-141
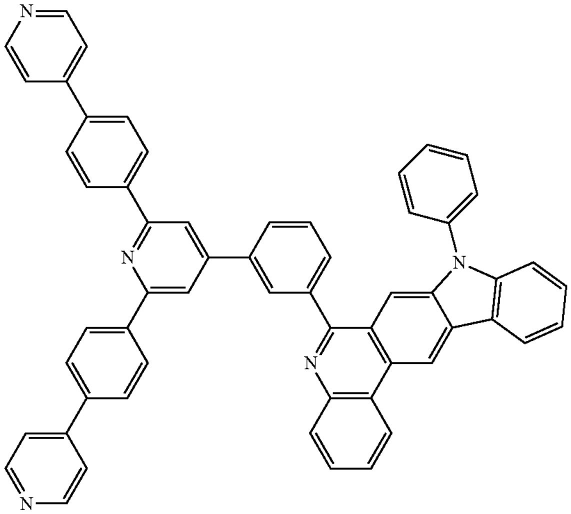
2-142
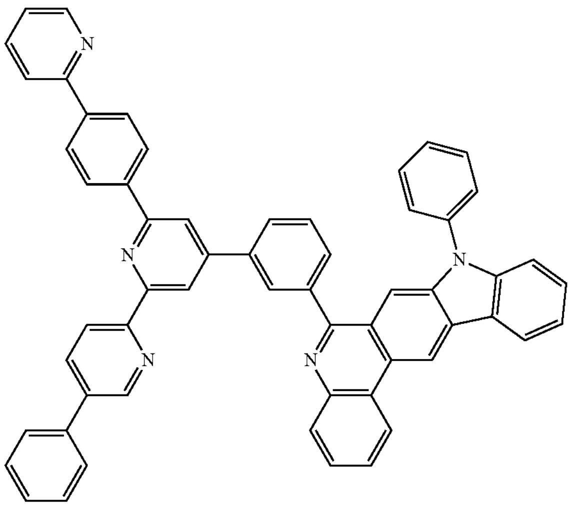
2-143
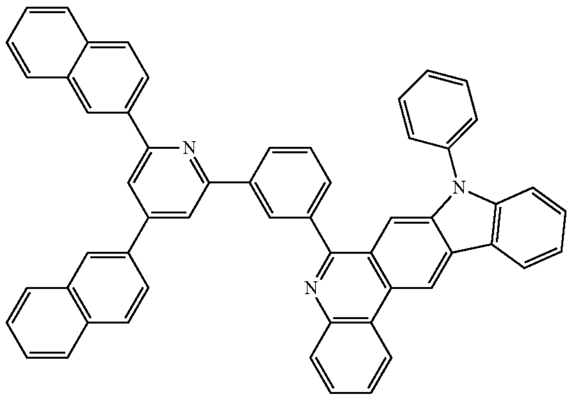

-continued
2-144
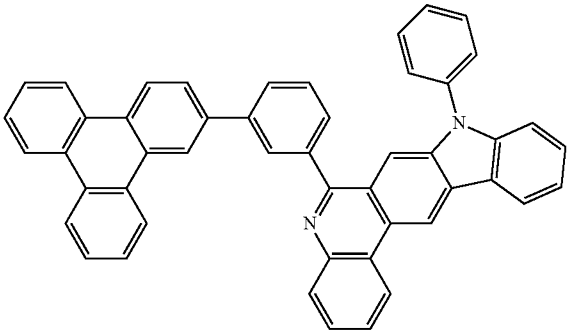
2-145
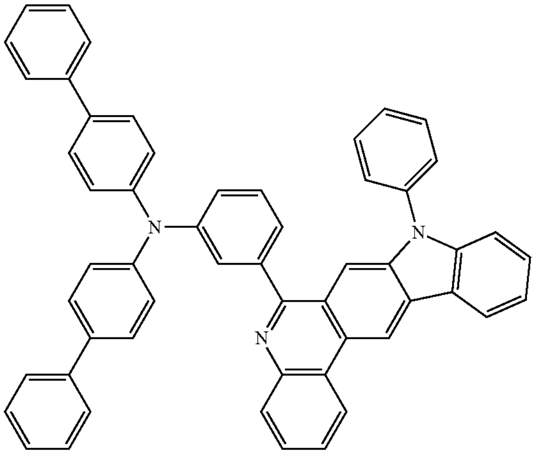
2-146
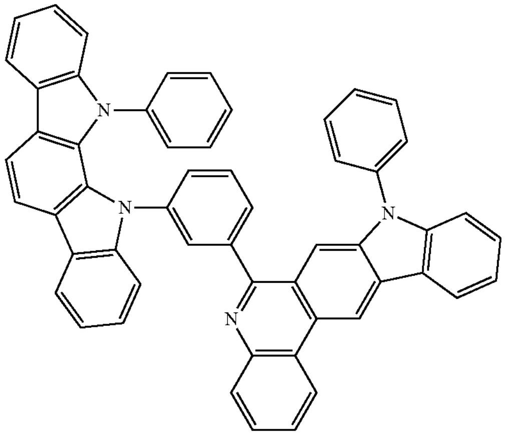
-continued
2-147
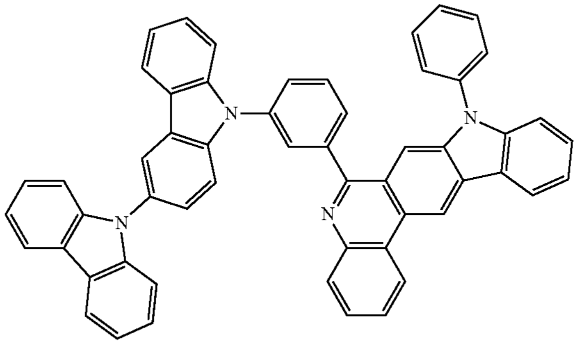
2-148
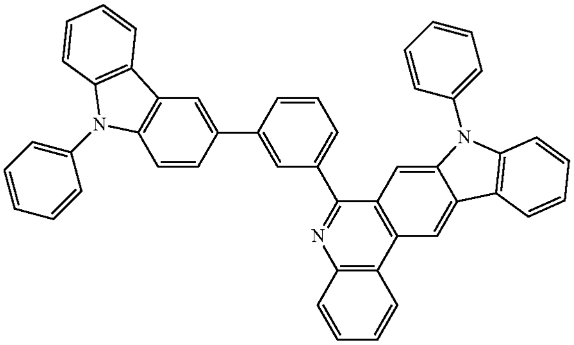
2-149
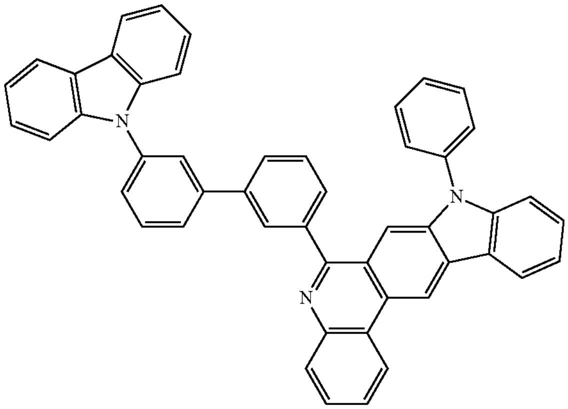
2-150
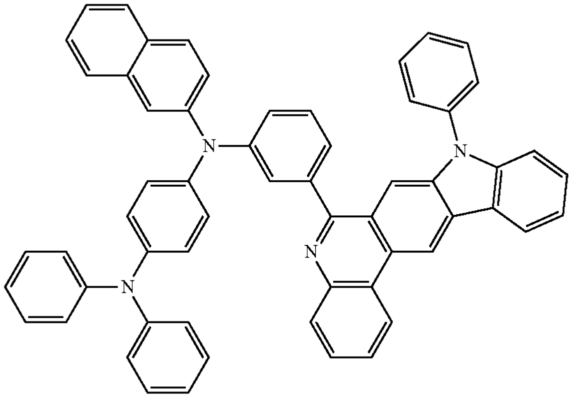

-continued
2-151
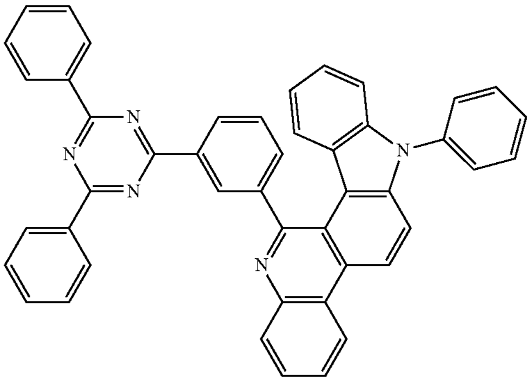
2-152
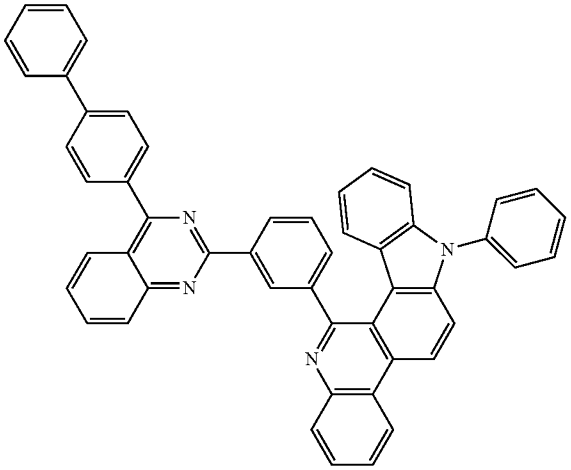
2-153
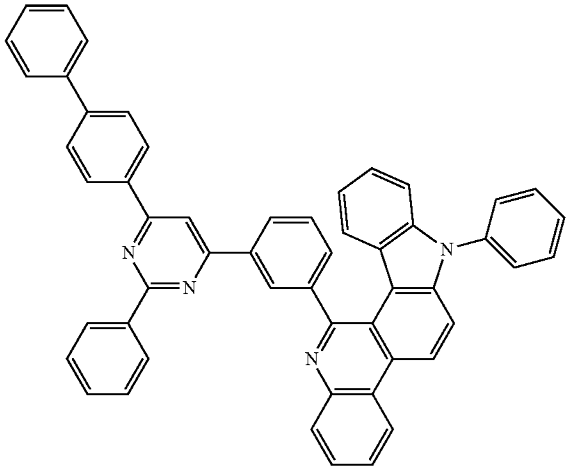
-continued
2-154
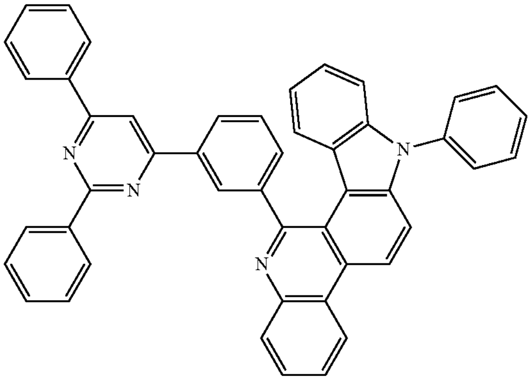
2-155
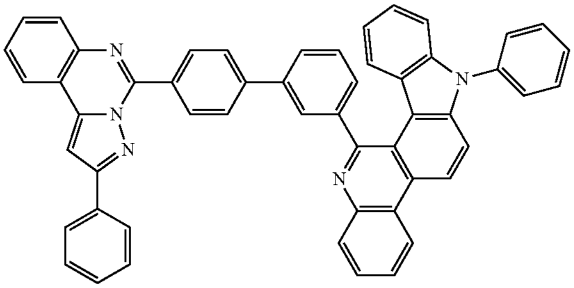
2-156
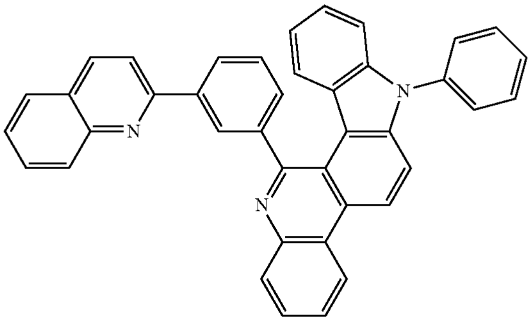
2-157
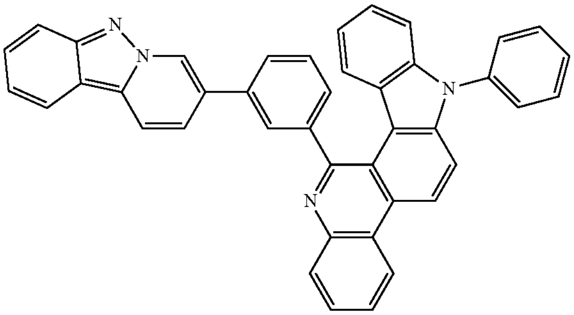

-continued
2-158
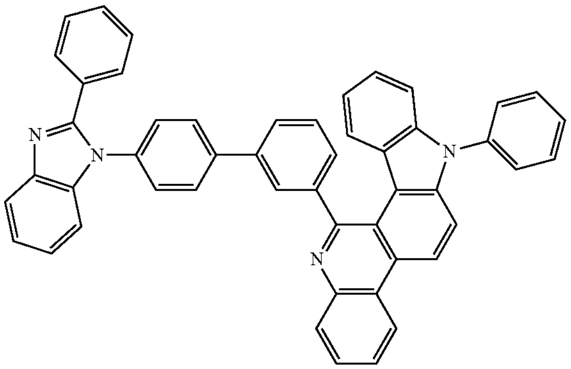
2-159
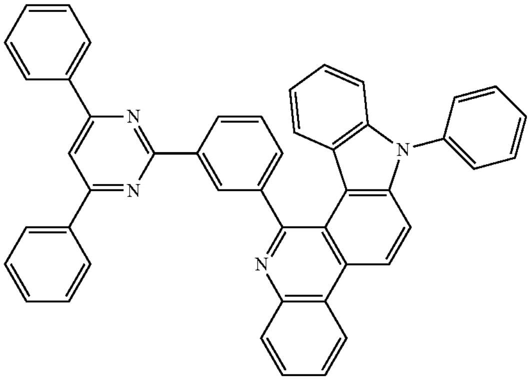
2-160
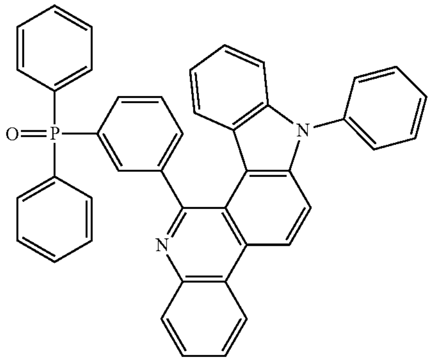
2-161
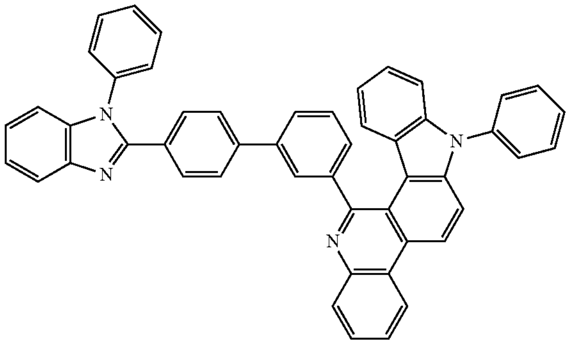
-continued
2-162
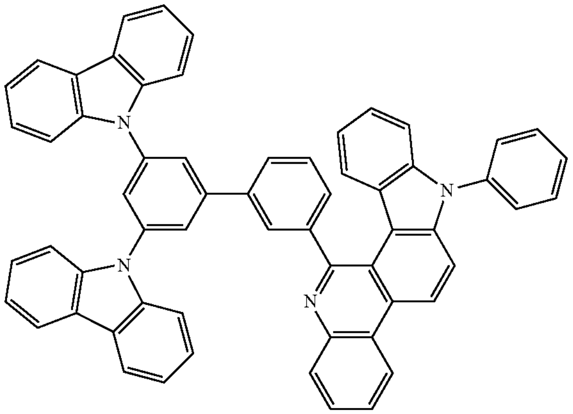
2-163
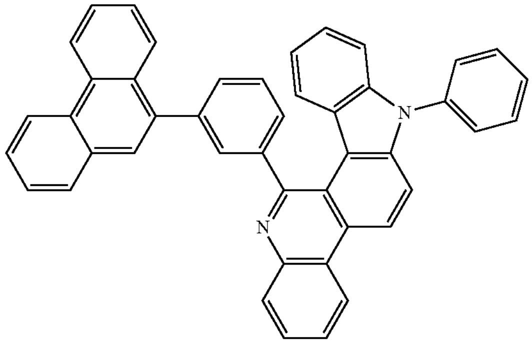
2-164
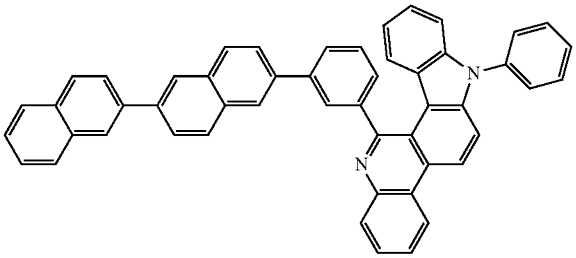
2-165
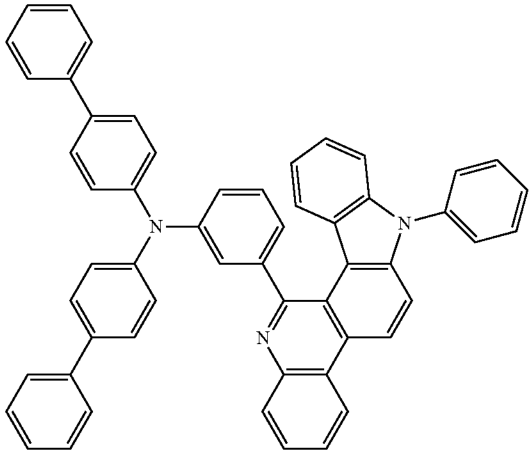

-continued
2-166
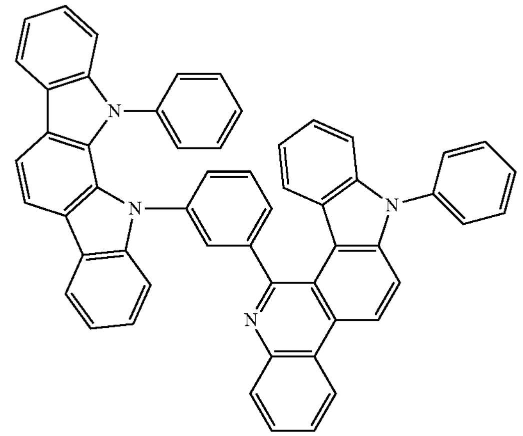
2-167
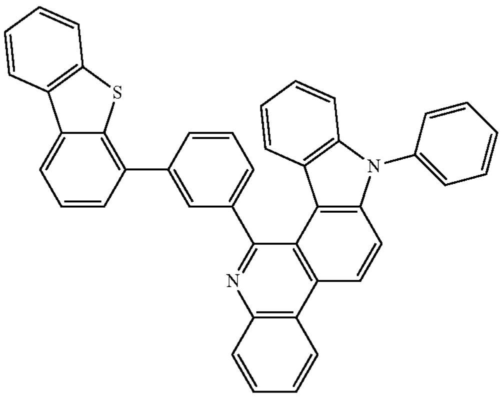
2-168
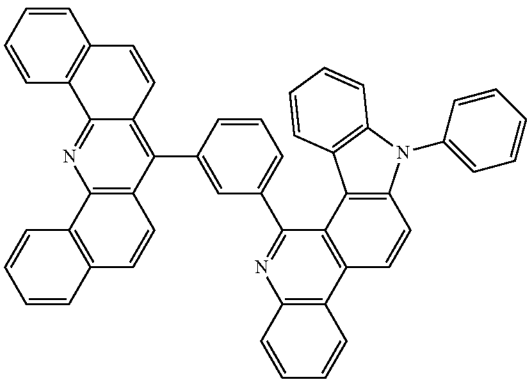
-continued
2-169
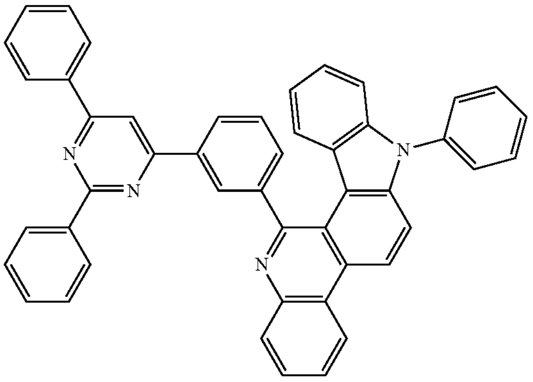
2-170
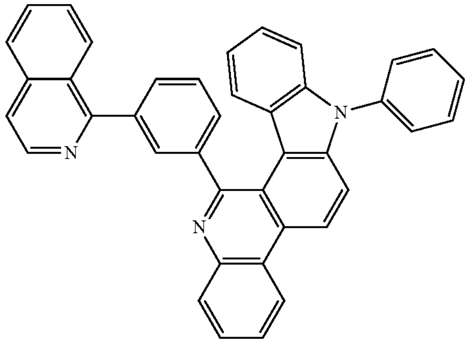
2-171
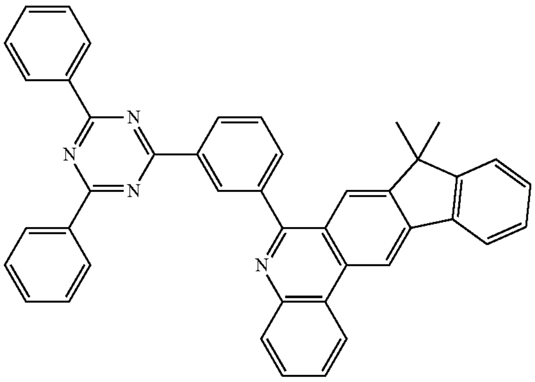
2-172
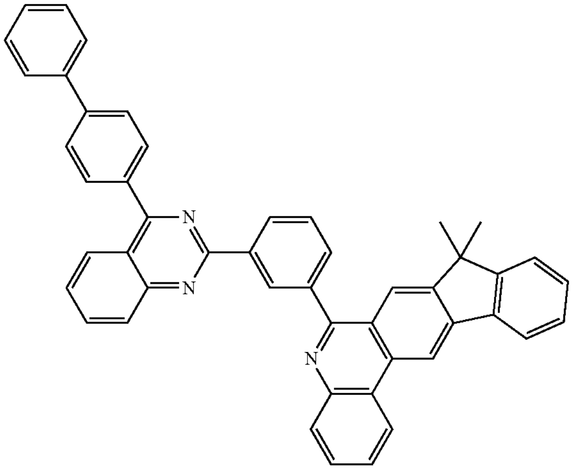

-continued
2-173
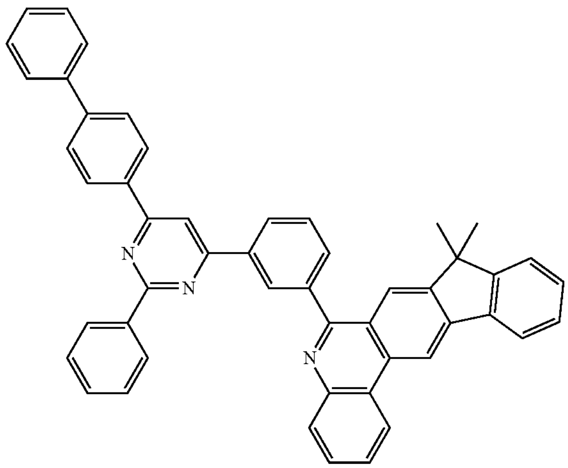
2-174
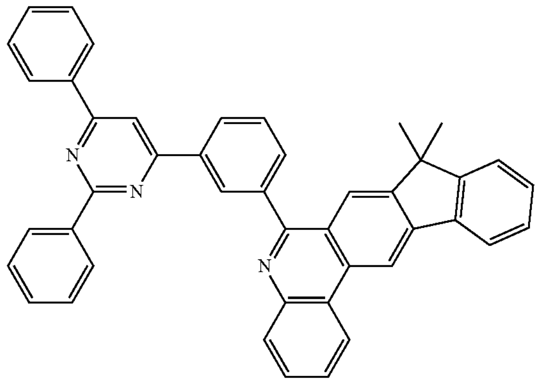
2-175
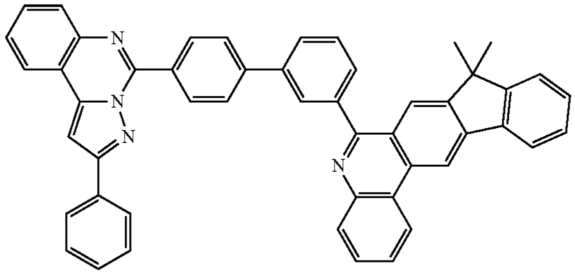
2-176
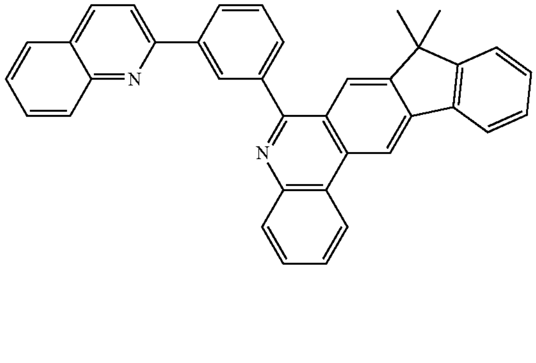
-continued
2-177
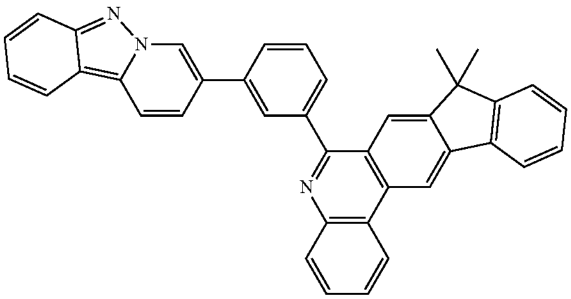
2-178
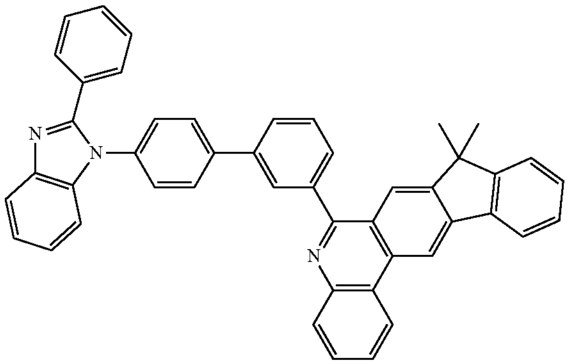
2-179
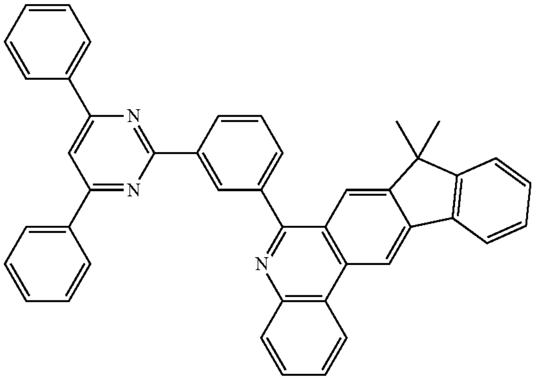
2-180
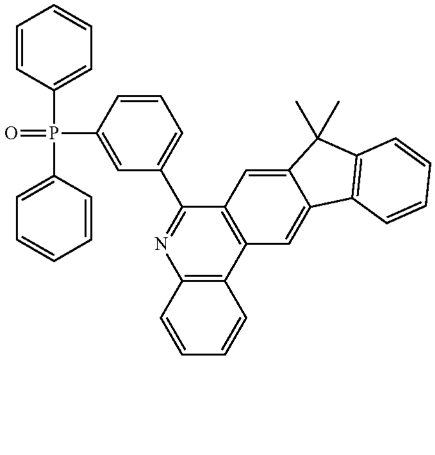

-continued
2-181
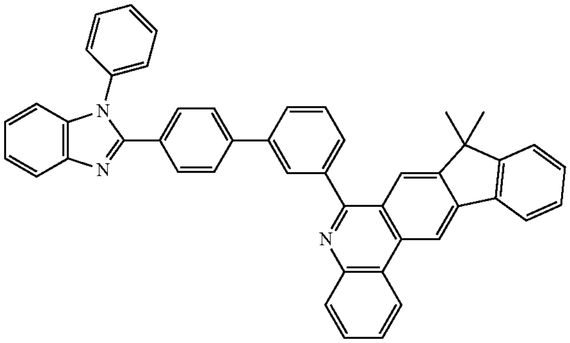
2-182
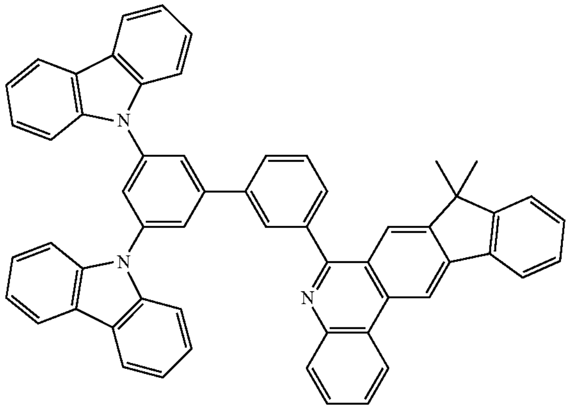
2-183
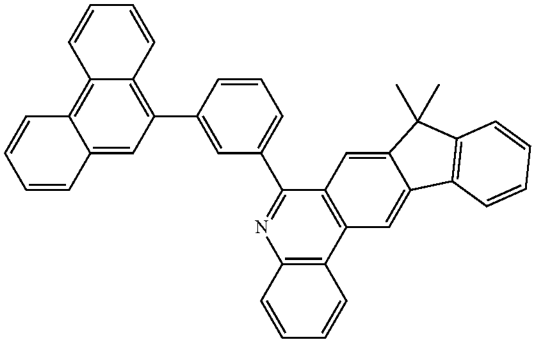
2-184
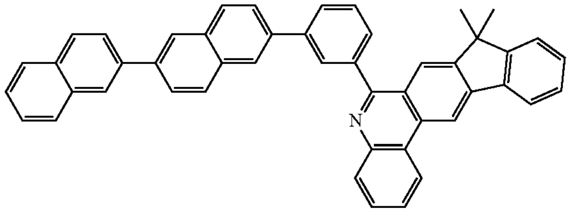
-continued
2-185
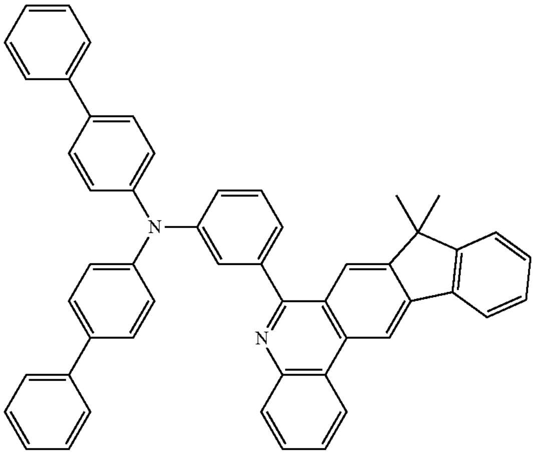
2-186
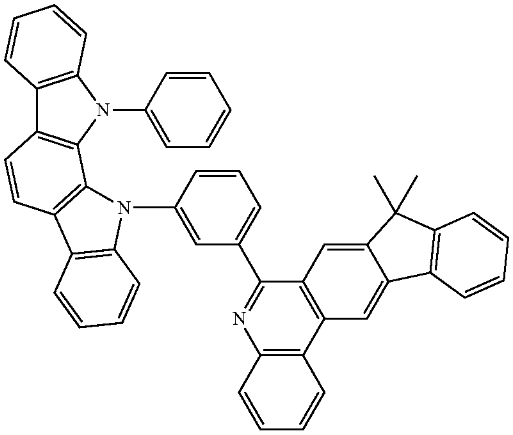
2-187
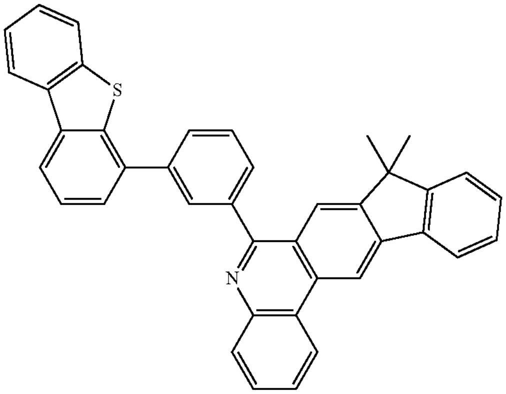

-continued
2-188
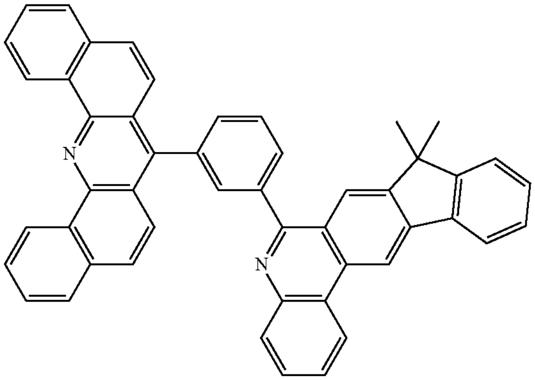
2-189
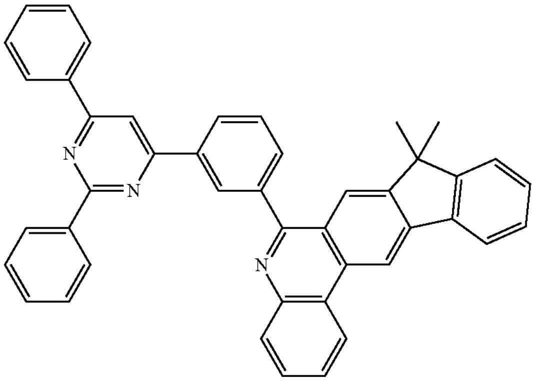
2-190
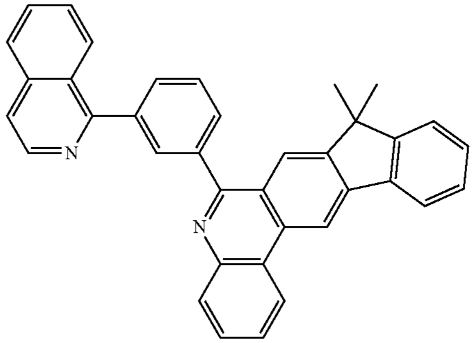
2-191
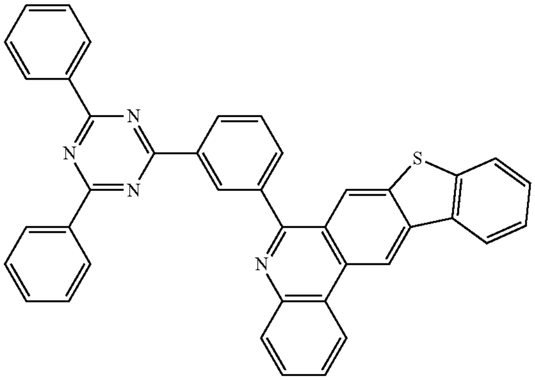
-continued
2-192
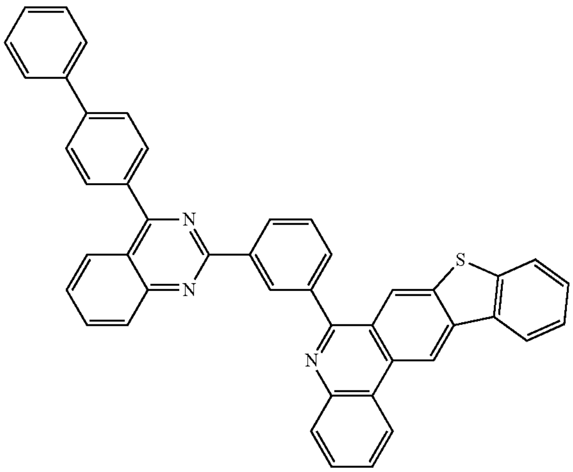
2-193
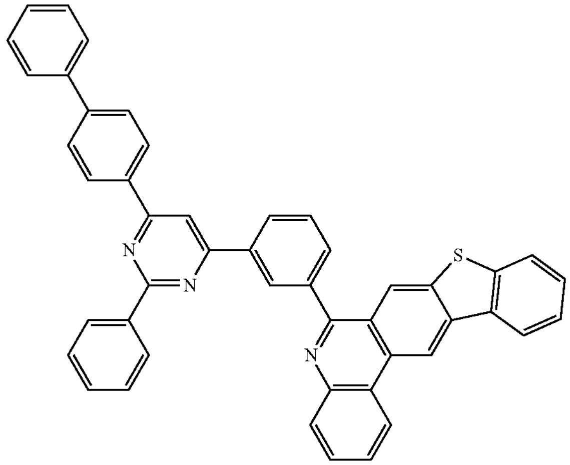
2-194
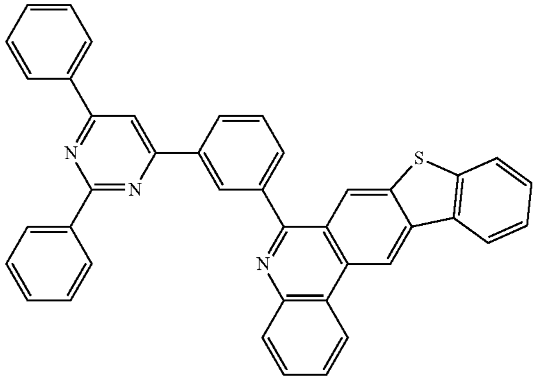

-continued
2-195
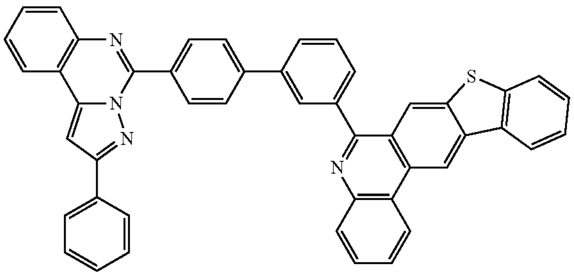
2-196
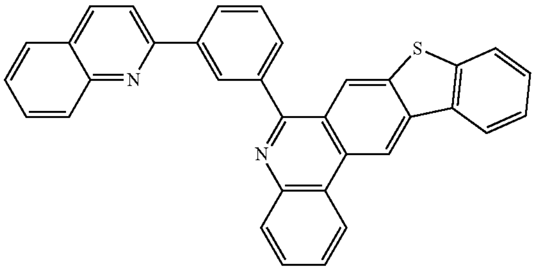
2-197
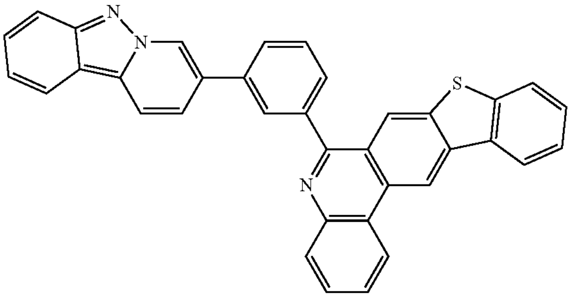
2-198
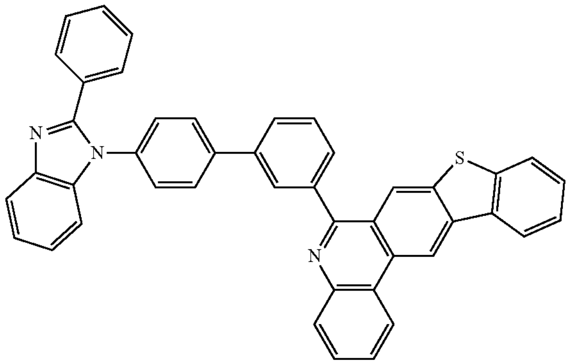
-continued
2-199
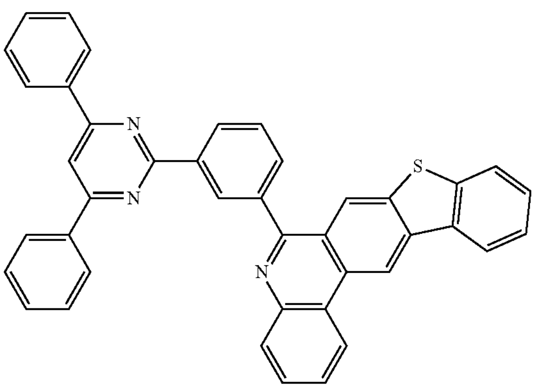
2-200
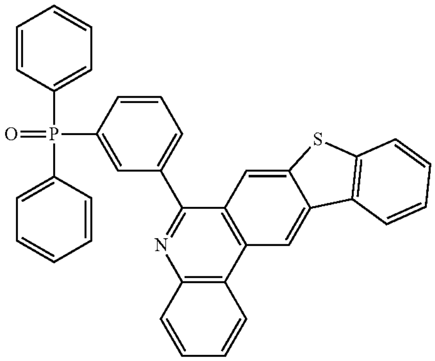
2-201
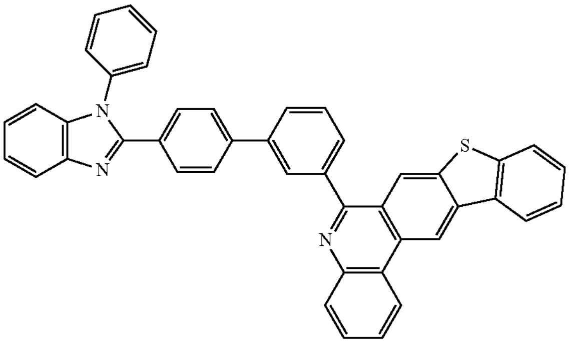
2-202
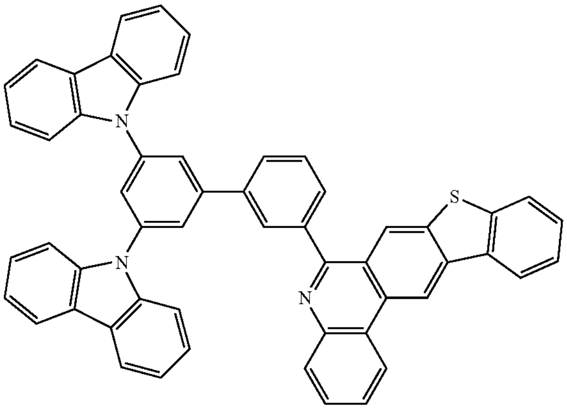

-continued
2-203
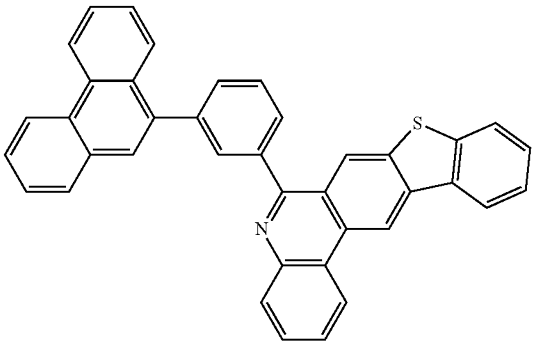
2-204
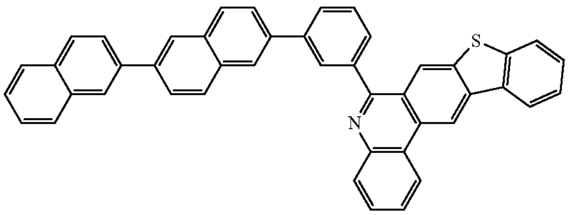
2-205
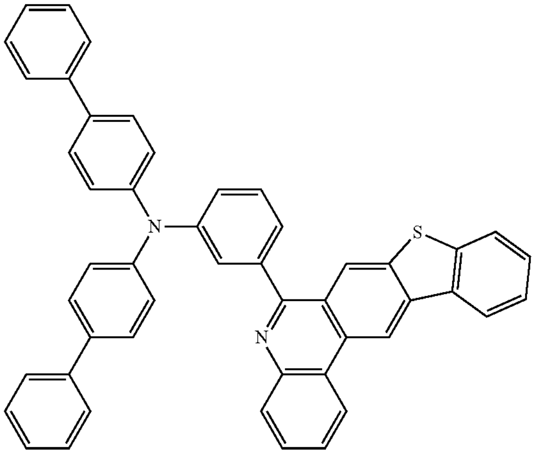
2-206
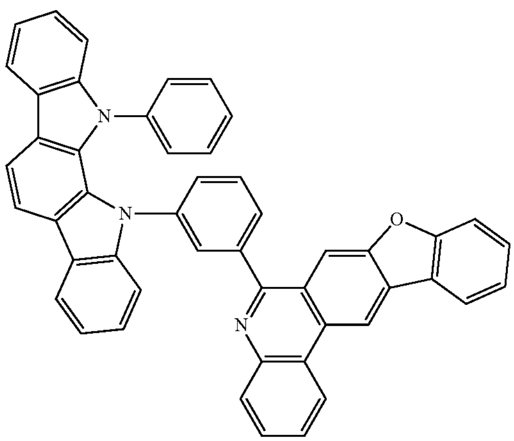
-continued
2-207
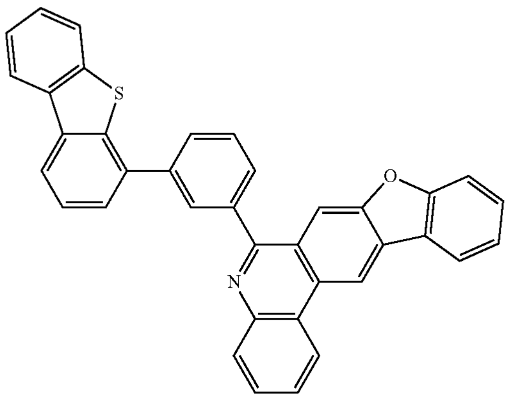
2-208
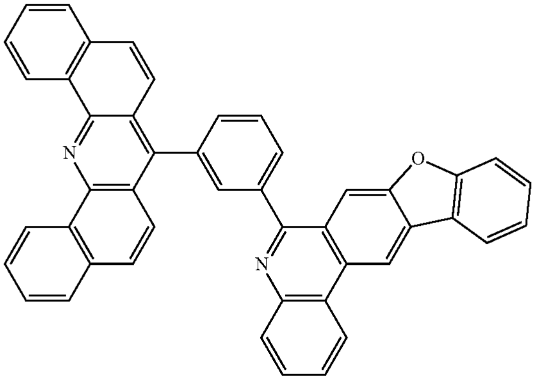
2-209
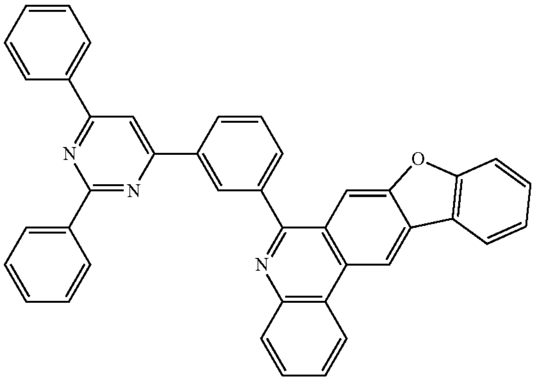
2-210
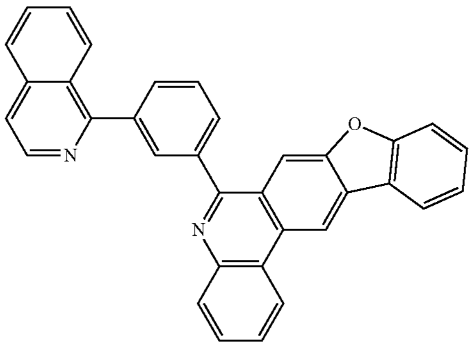

-continued
2-211
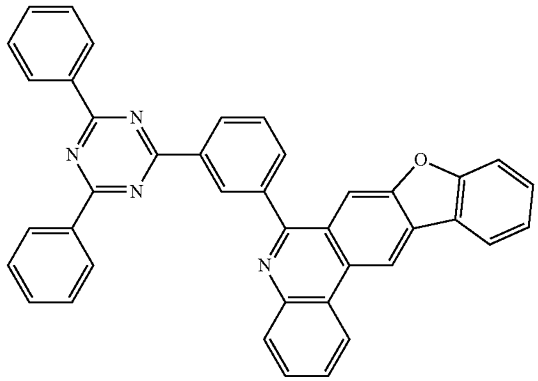
2-212
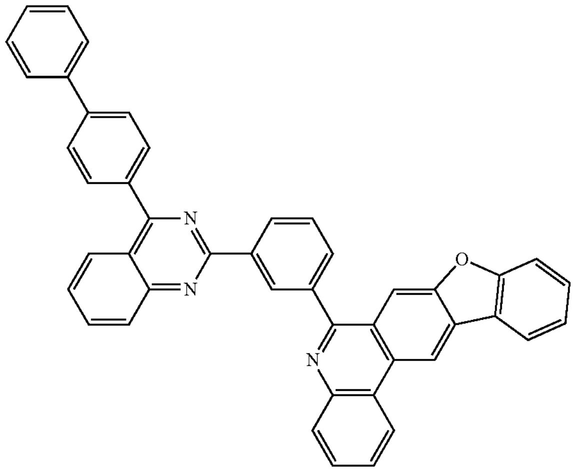
2-213
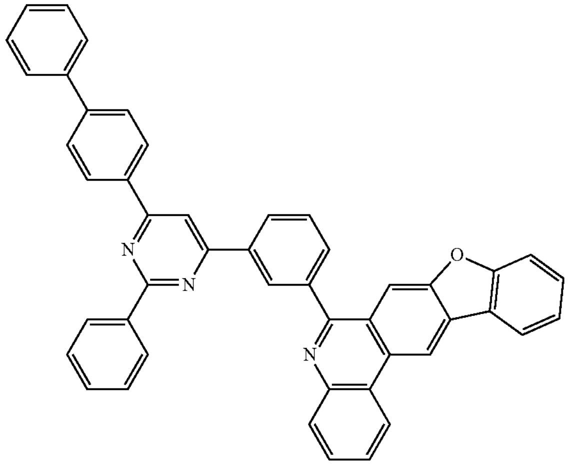
-continued
2-214
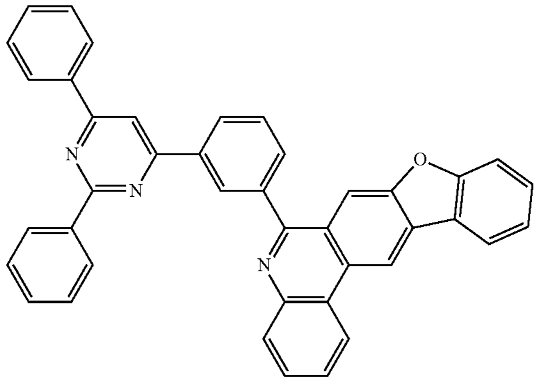
2-215
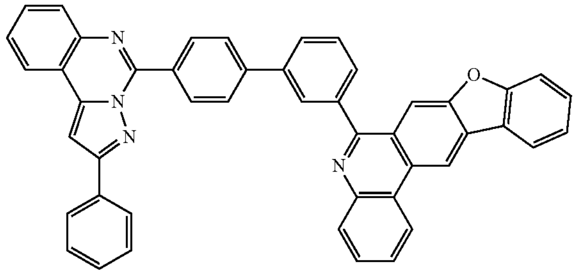
2-216
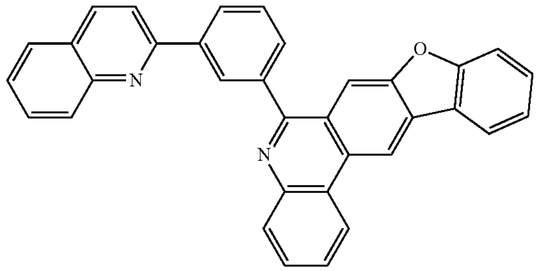
2-217
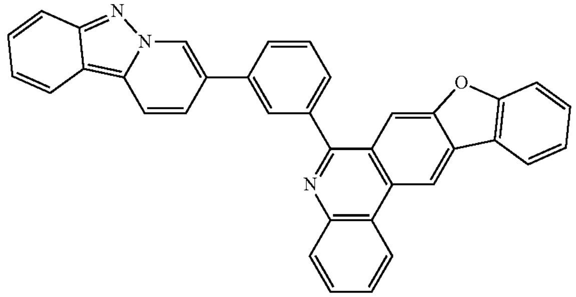

2-218
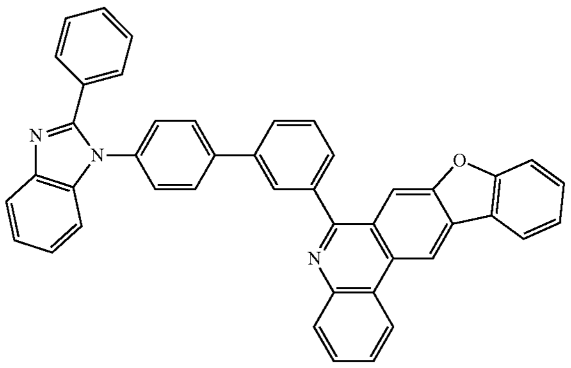
2-219
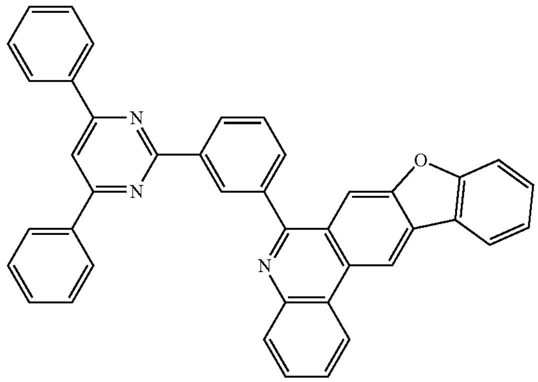
2-220
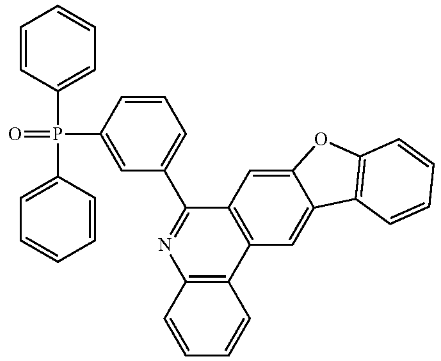
2-221
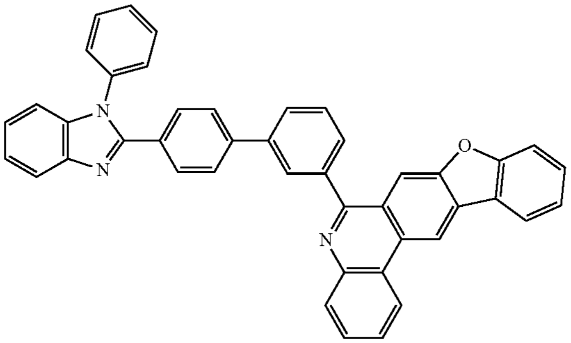
2-222
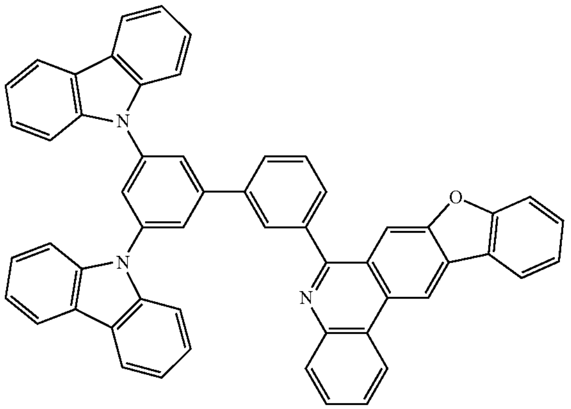
2-223
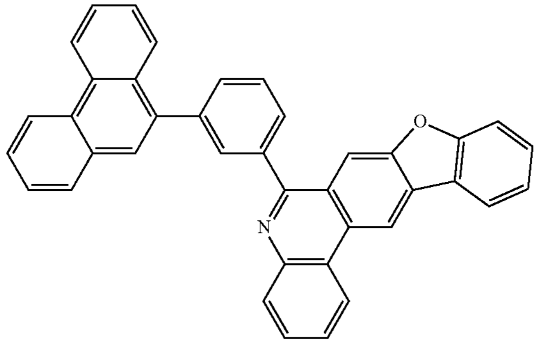
2-224
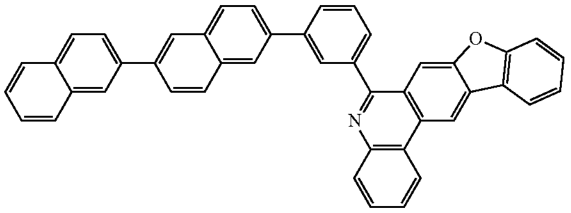
2-225
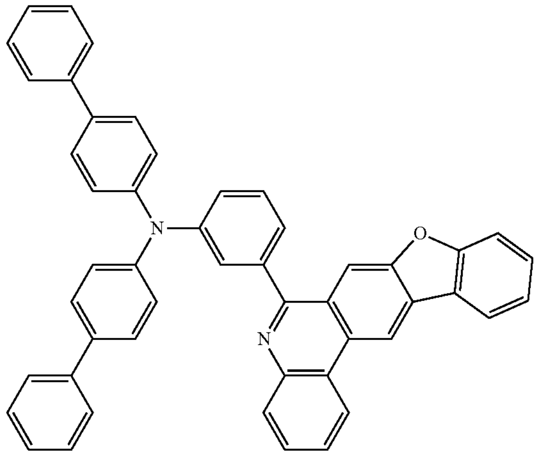

-continued
2-226
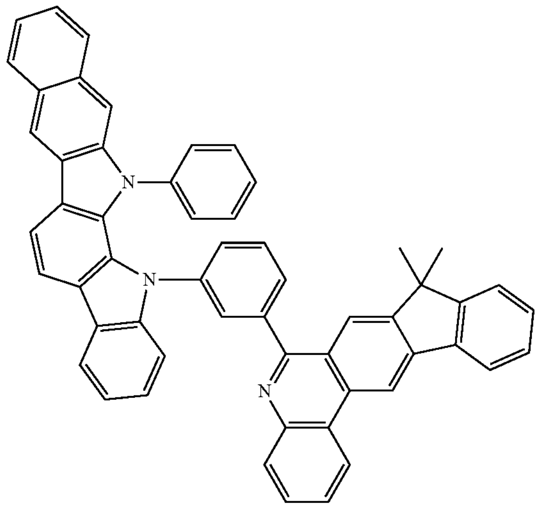
2-227
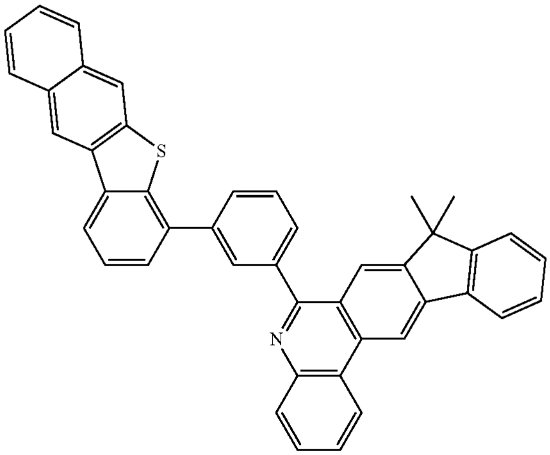
2-228
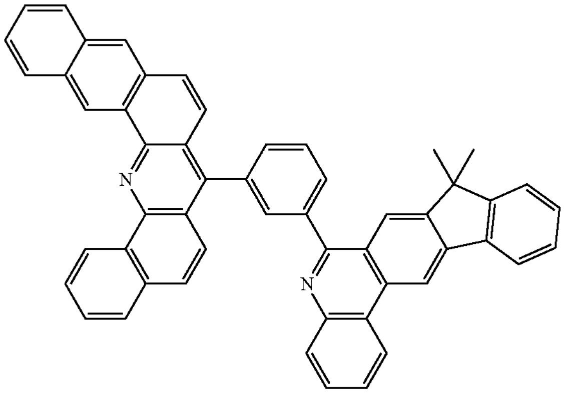
-continued
2-229
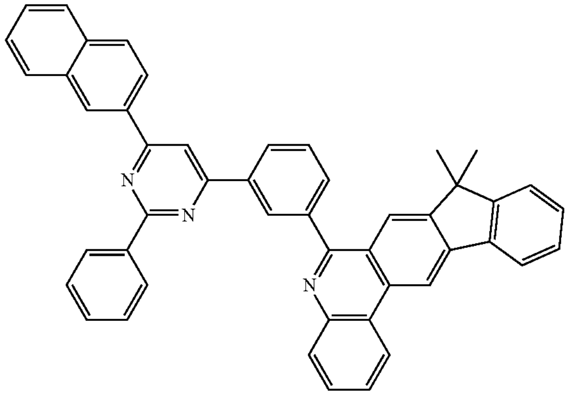
2-230
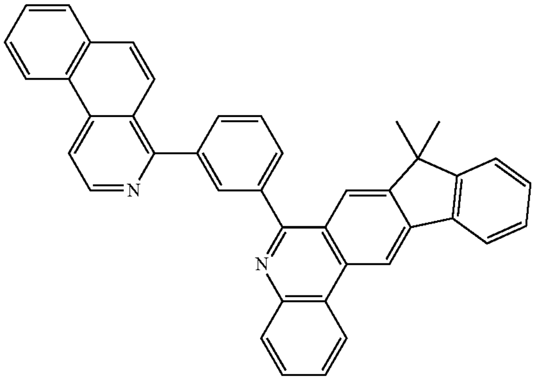
According to another exemplary embodiment of the present specification,
in Chemical Formula 17, Ar may be bonded to an atom bonded to a core of phenyl at a para position thereof, and Chemical Formula 17 may be selected from the following compounds.
2-231
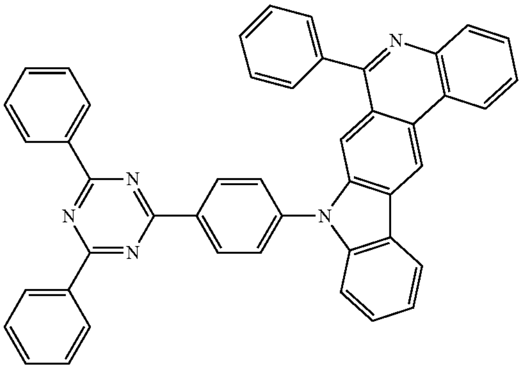

-continued
2-232
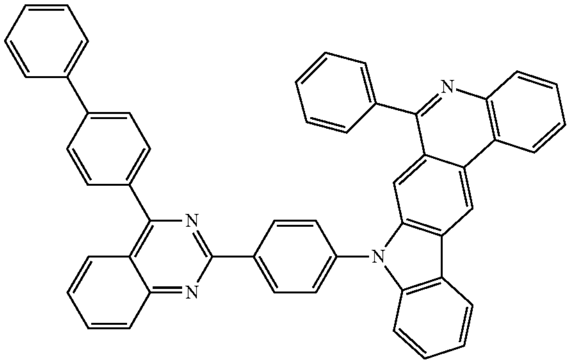
2-233
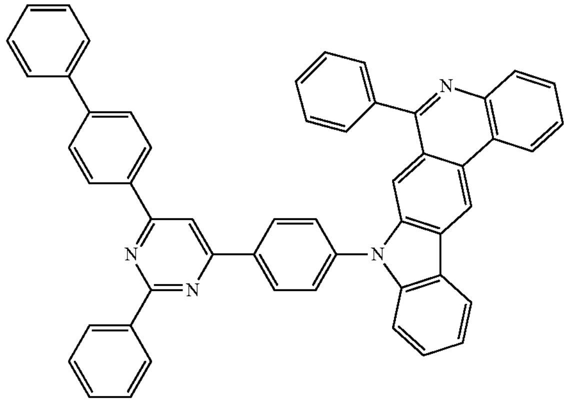
2-234
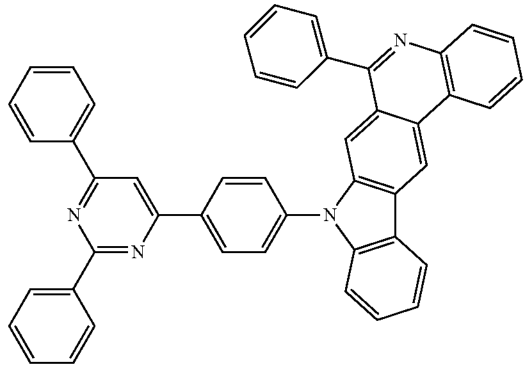
2-235
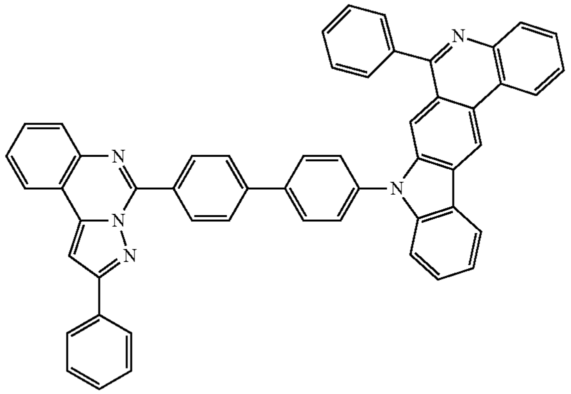
-continued
2-236
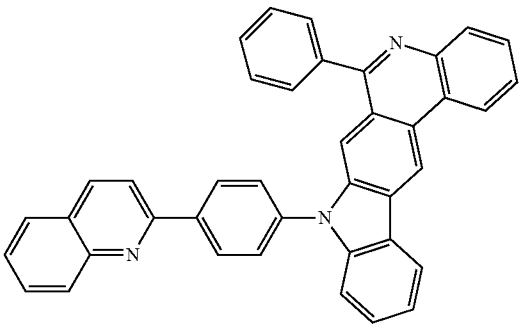
2-237
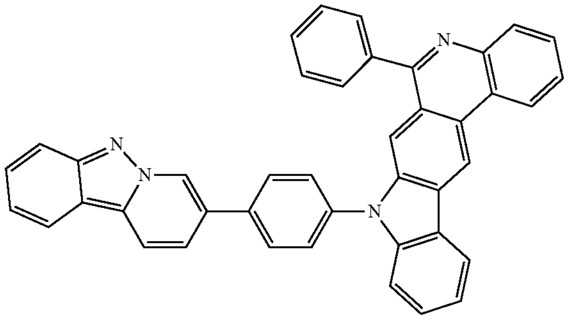
2-238
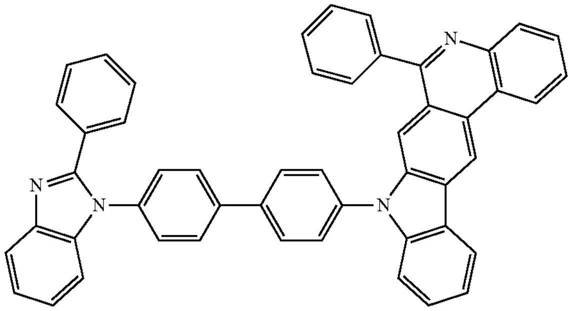
2-239
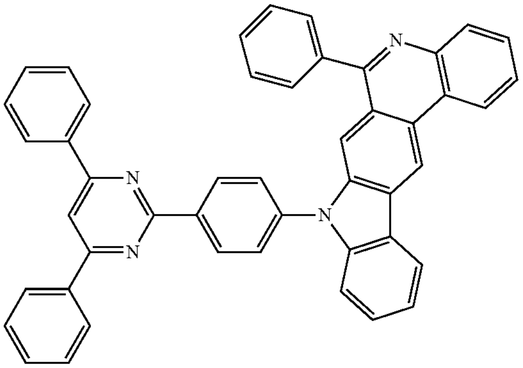

-continued
2-240
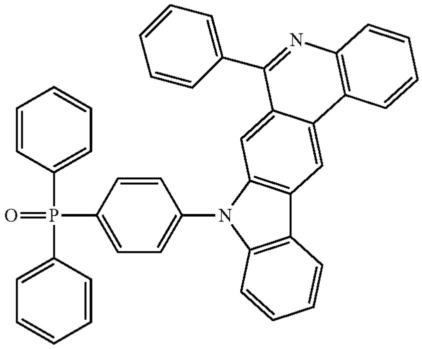
2-241
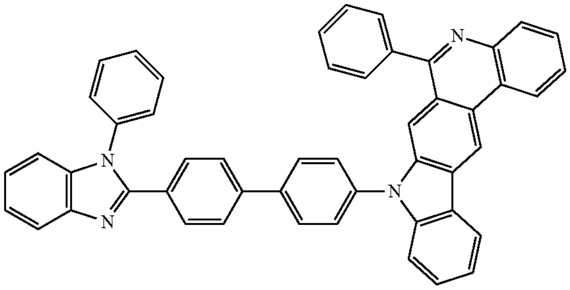
2-242
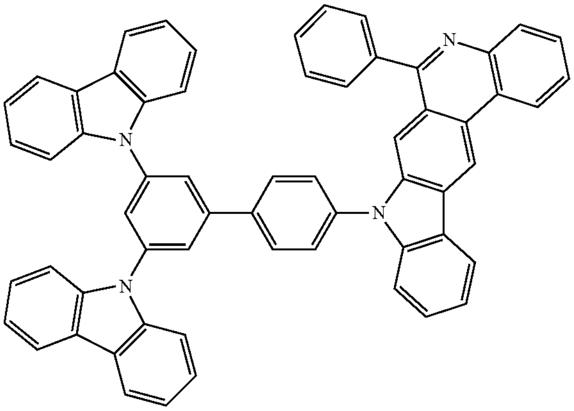
2-243
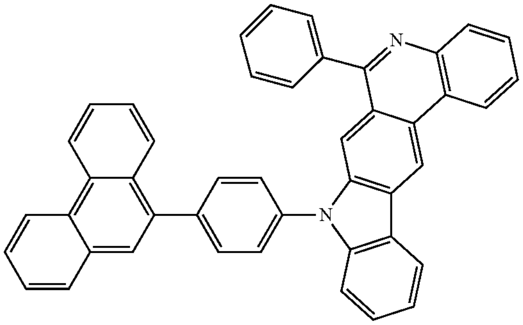
-continued
2-244
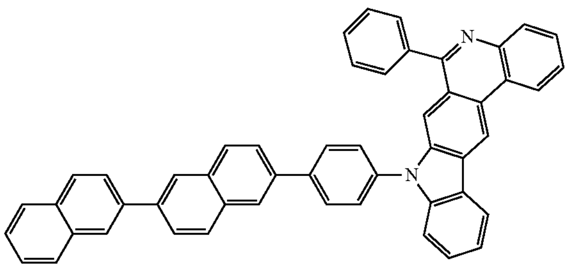
2-245
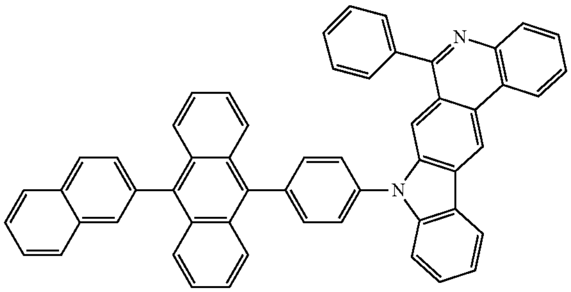
2-246
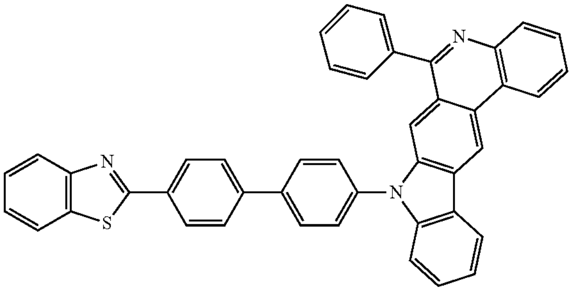
2-247
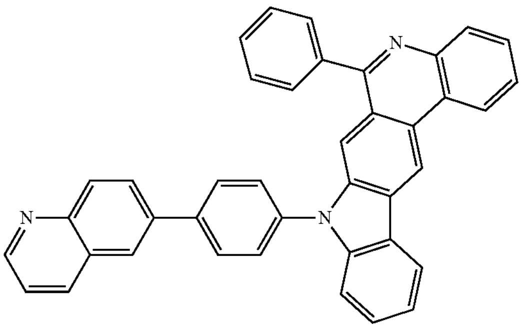
2-248
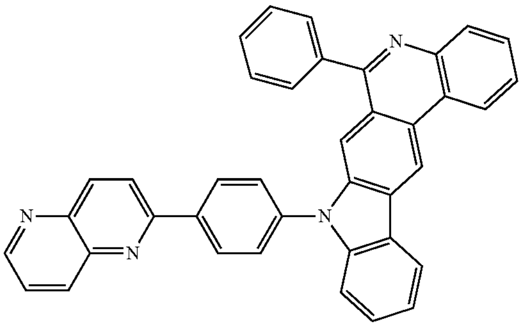

-continued
2-249
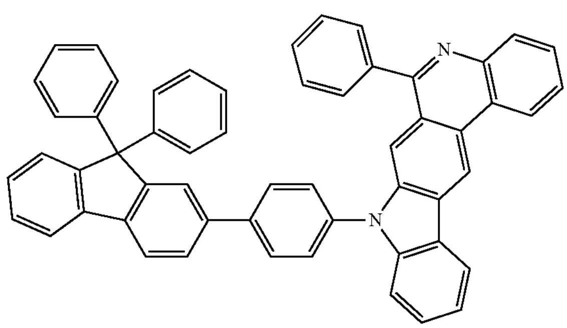
2-250
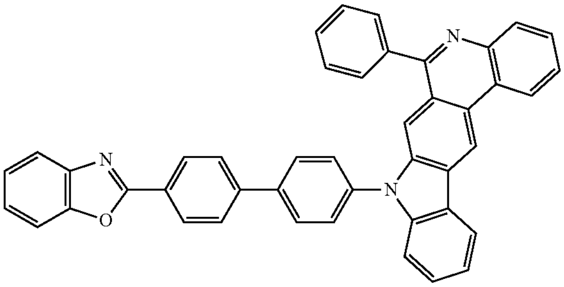
2-251
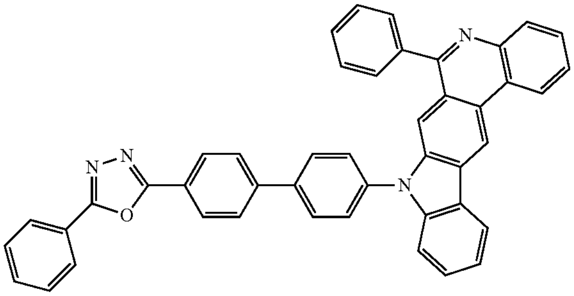
2-252
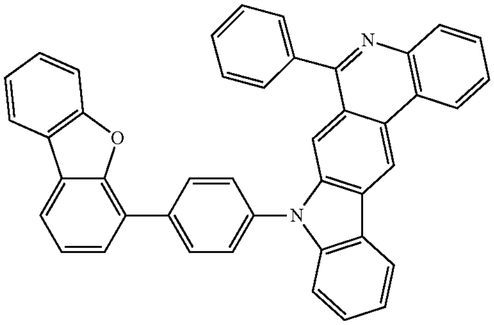
-continued
2-253
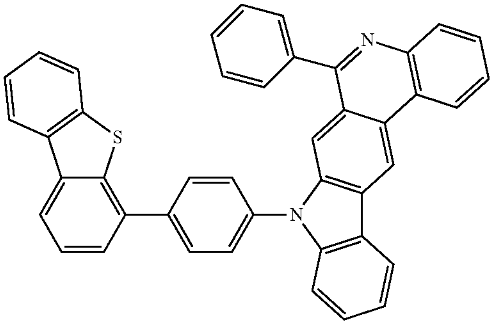
2-254
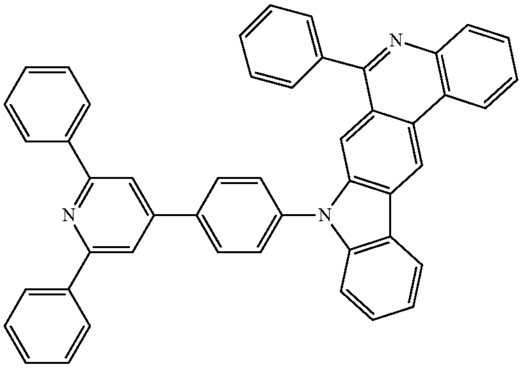
2-255
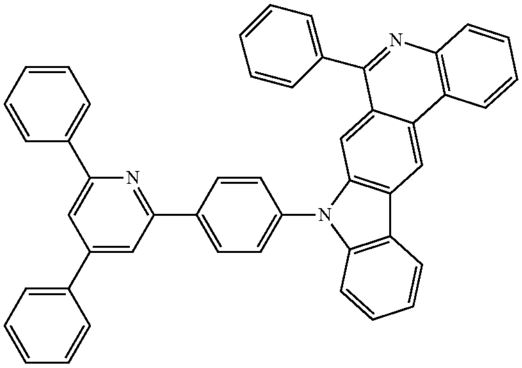

-continued
2-256
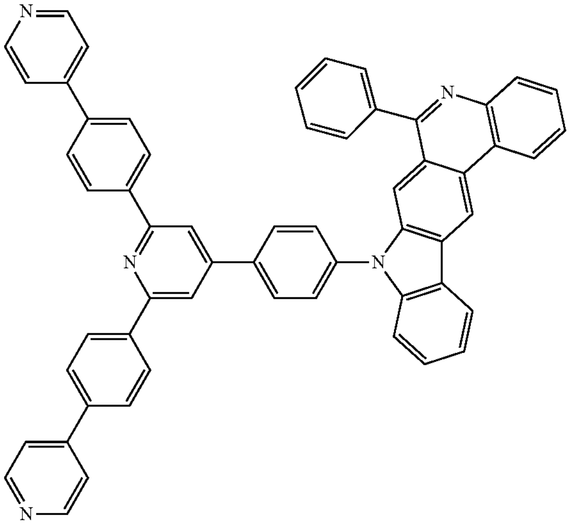
2-257
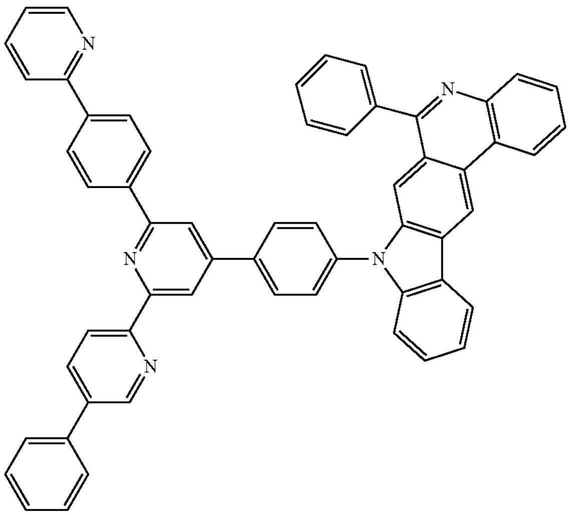
2-258
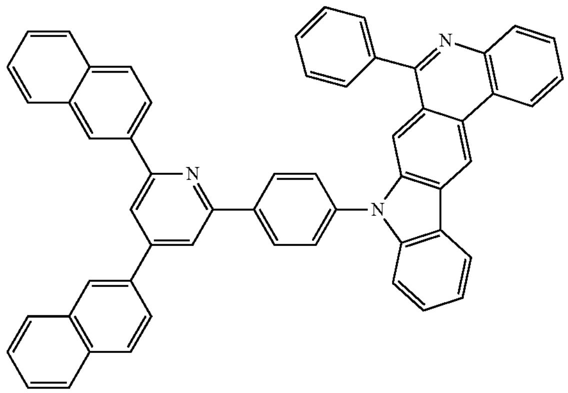
-continued
2-259
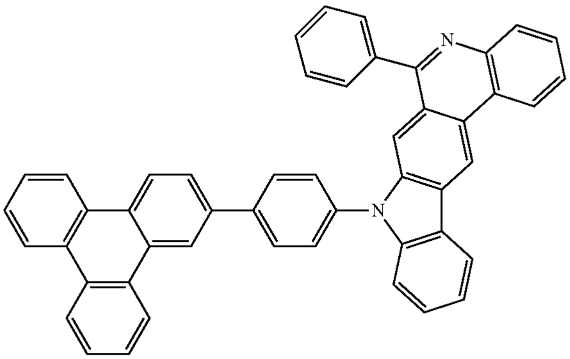
2-260
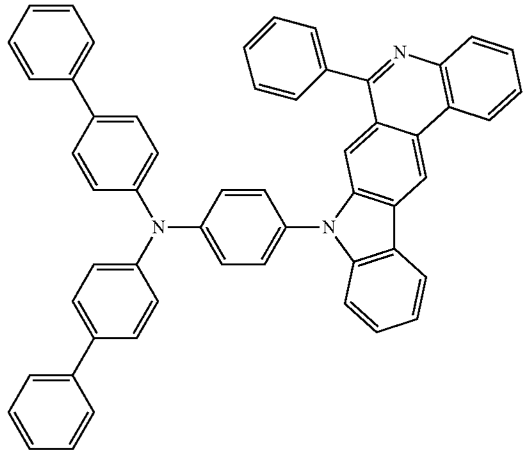
2-261
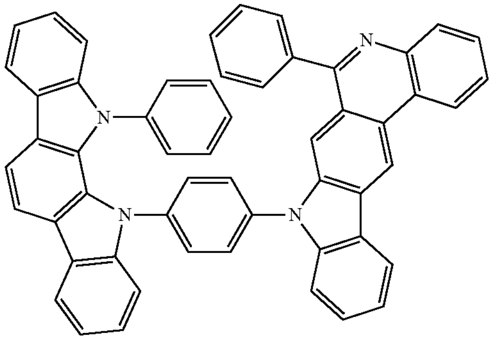
2-262
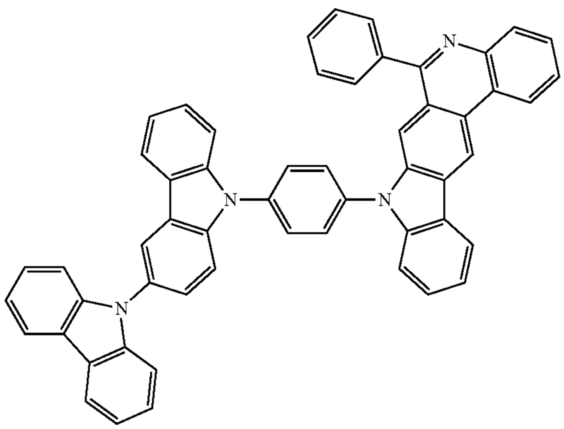

-continued
2-263
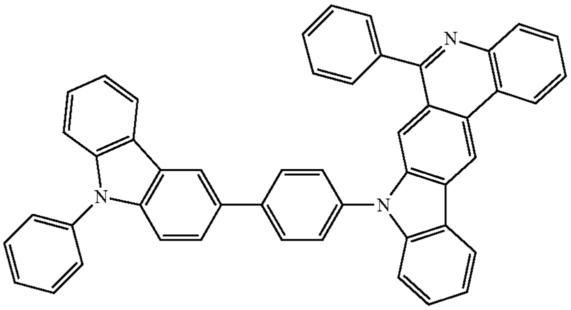
2-264
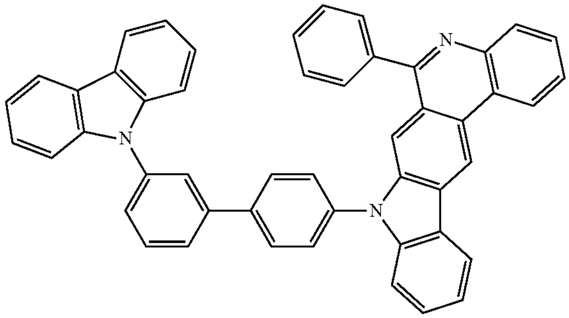
2-265
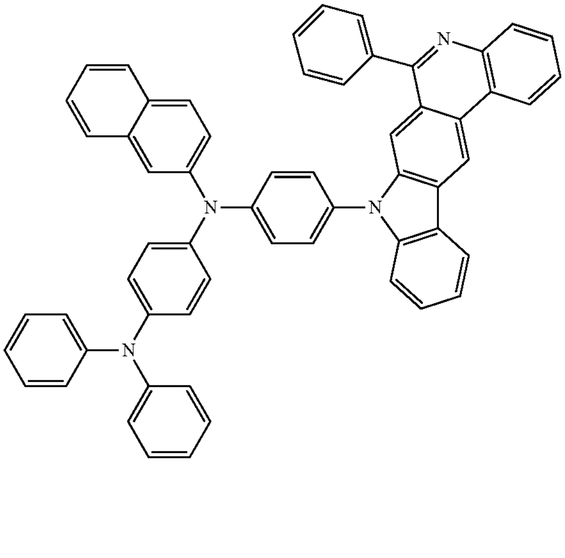
According to another exemplary embodiment of the present specification,
in Chemical Formula 17, Ar may be bonded to an atom bonded to a core of phenyl at a meta position thereof, and Chemical Formula 17 may be selected from the following compounds.
2-266
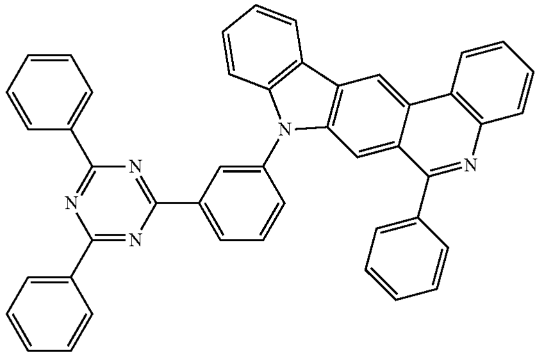
2-267
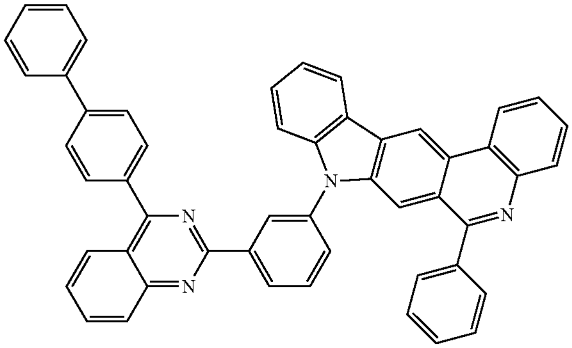
2-268
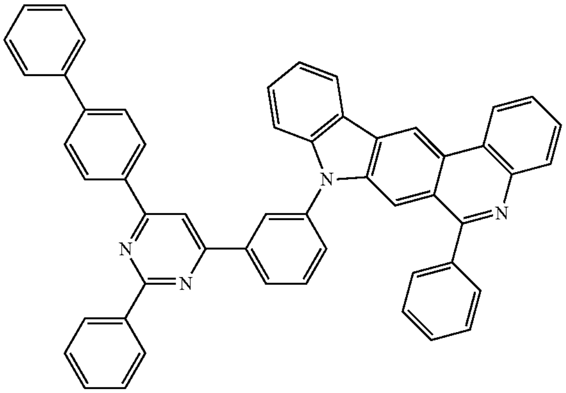
2-269
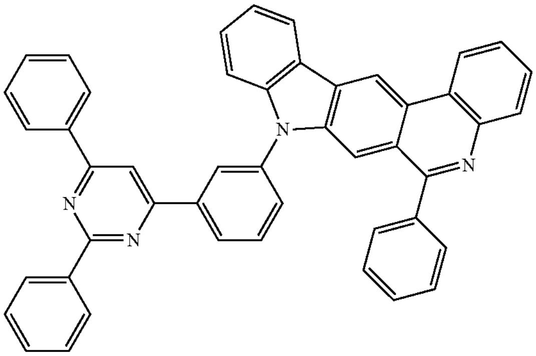

-continued
2-270
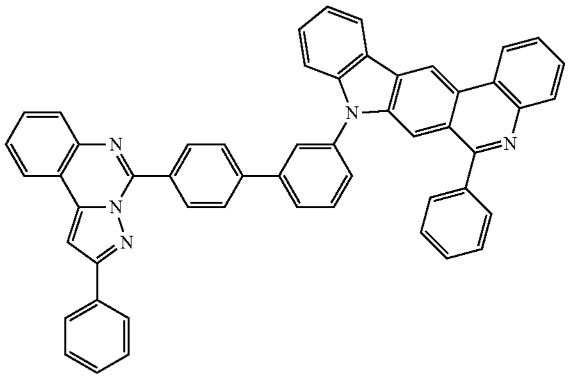
2-271
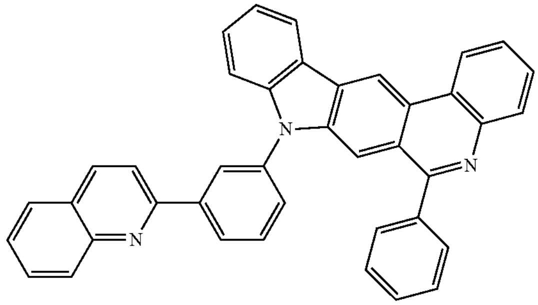
2-272
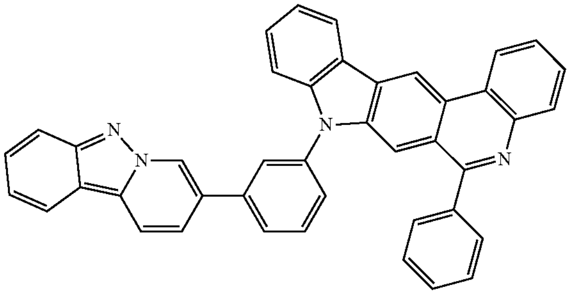
2-273
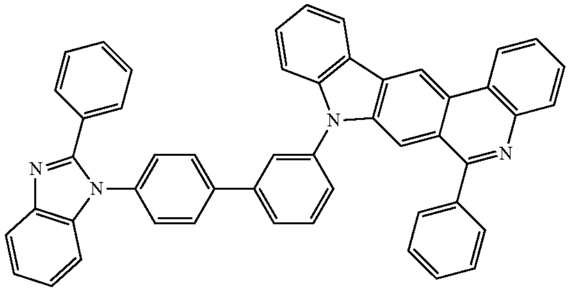
-continued
2-274
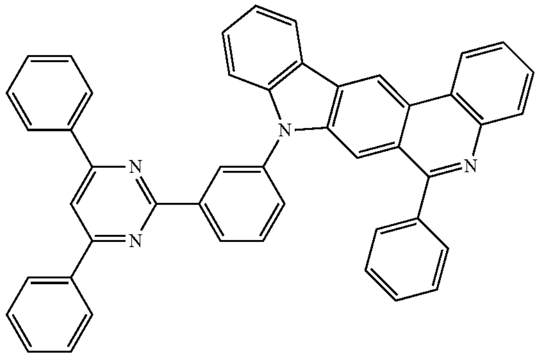
2-275
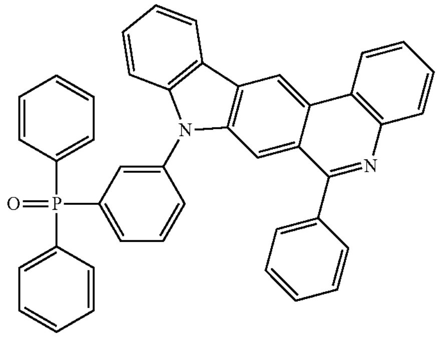
2-276
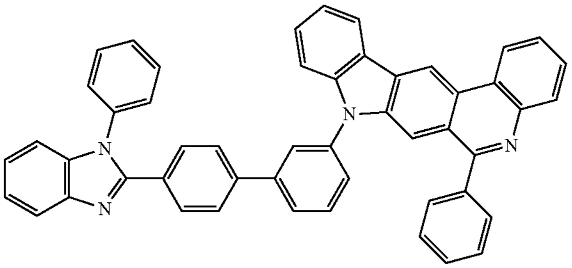
2-277
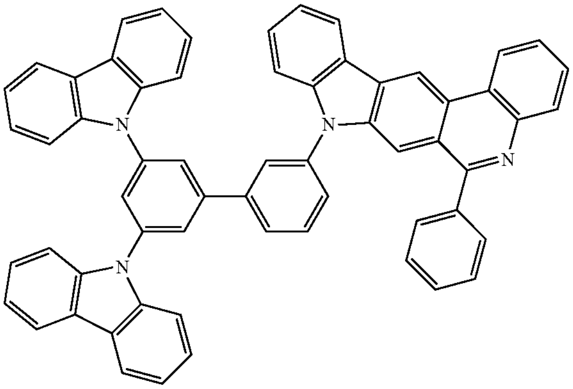

-continued
2-278
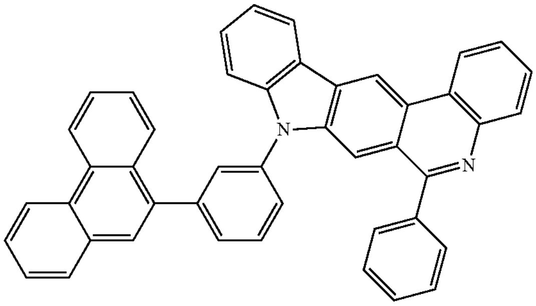
2-279
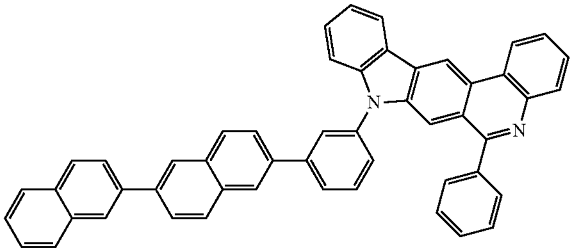
2-280
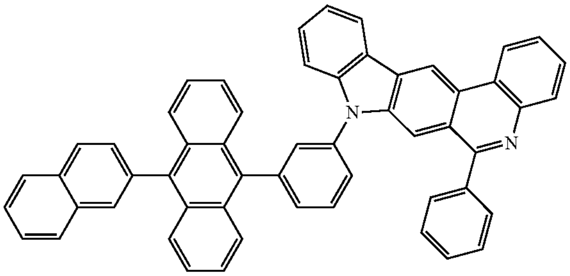
2-281
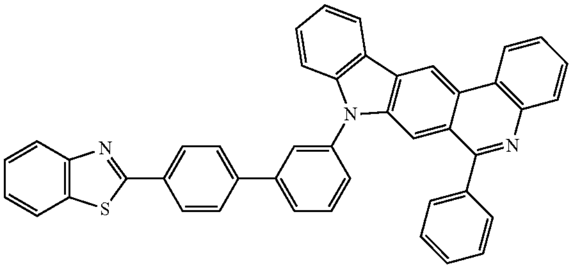
2-282
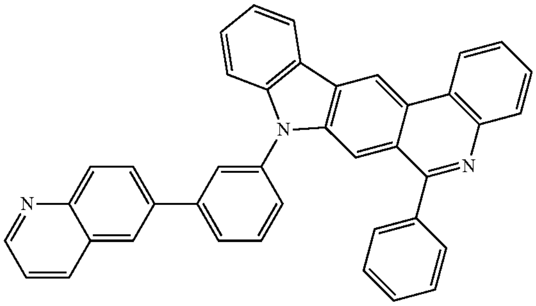
-continued
2-283
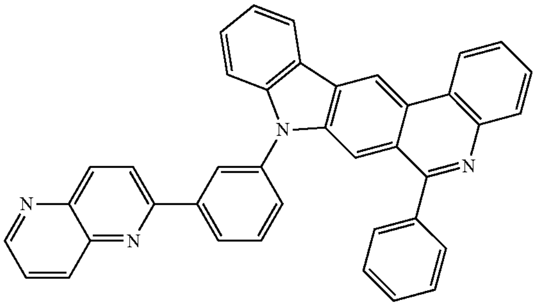
2-284
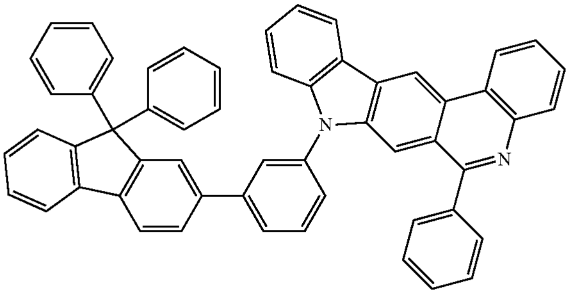
2-285
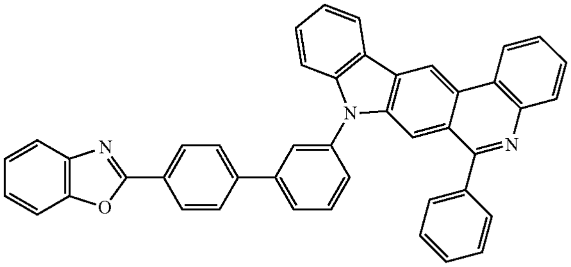
2-286
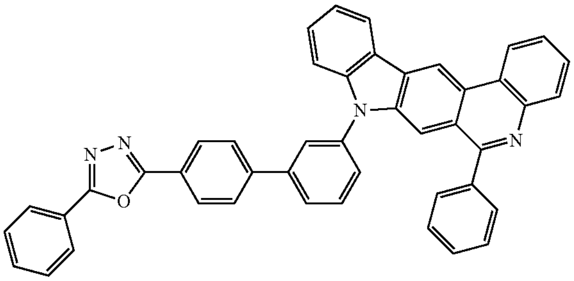
2-287
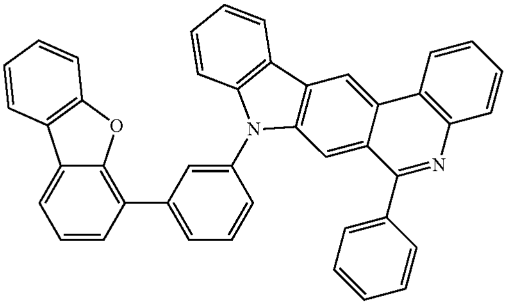

-continued
2-288
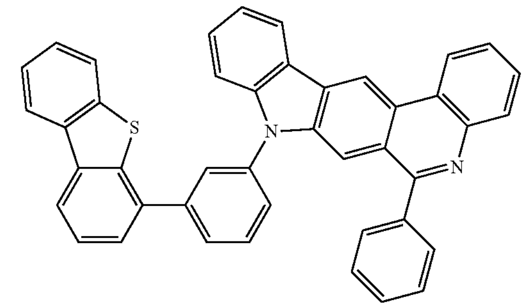
2-289
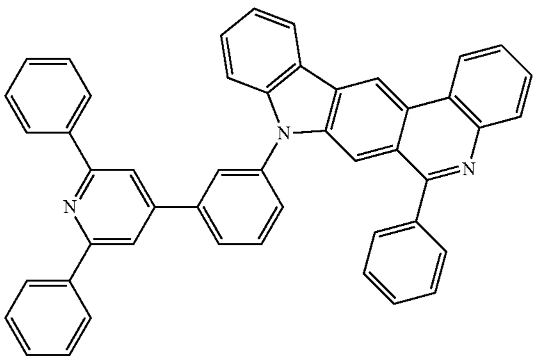
2-290
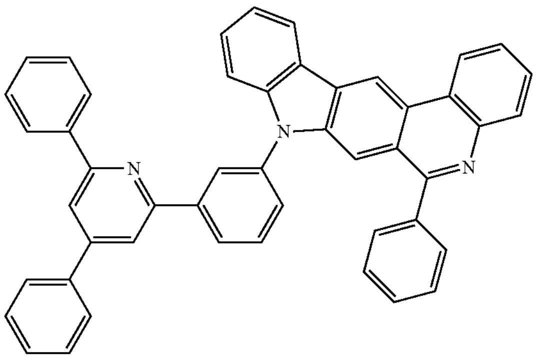
2-291
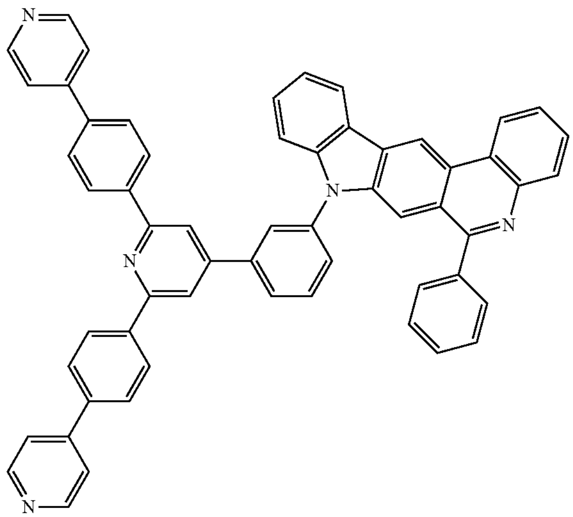
-continued
2-292
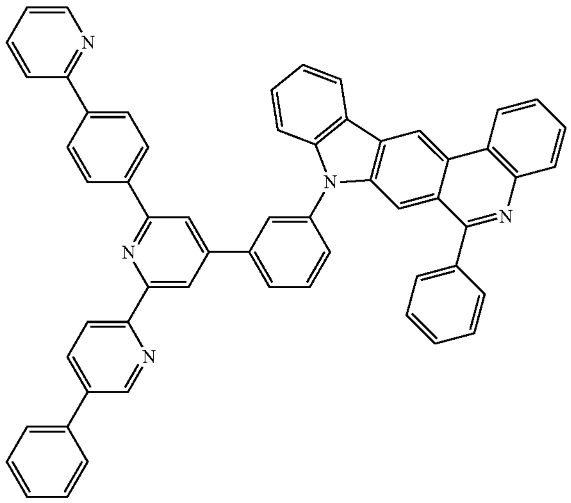
2-293
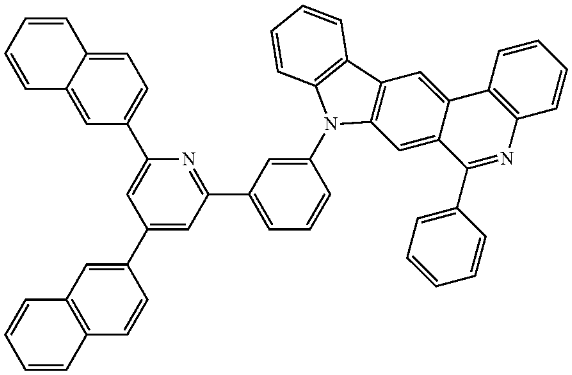
2-294
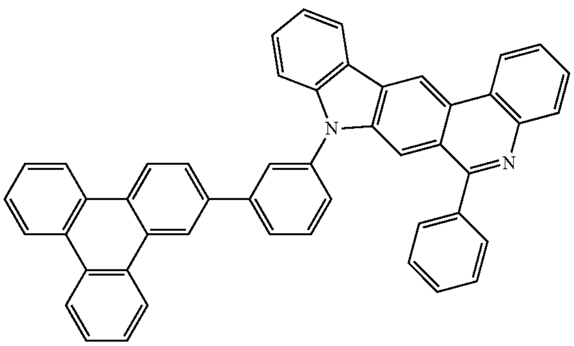

-continued
2-295
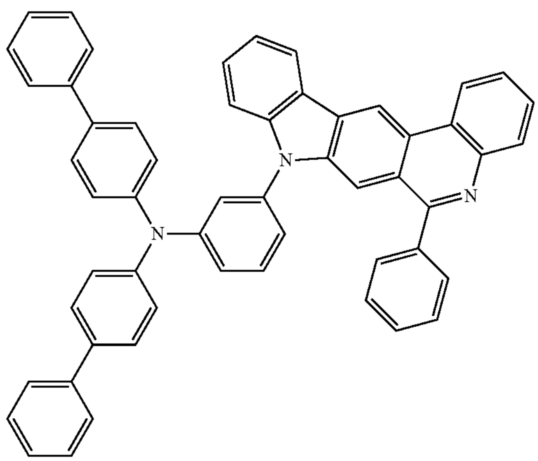
2-296
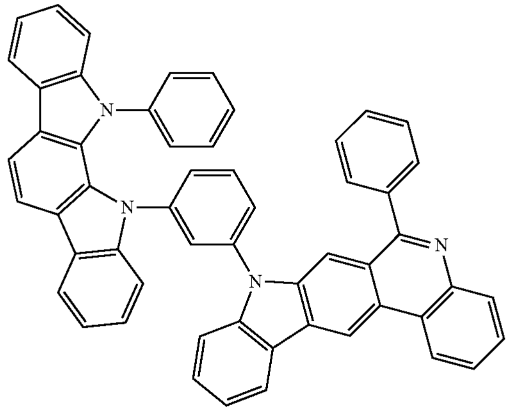
2-297
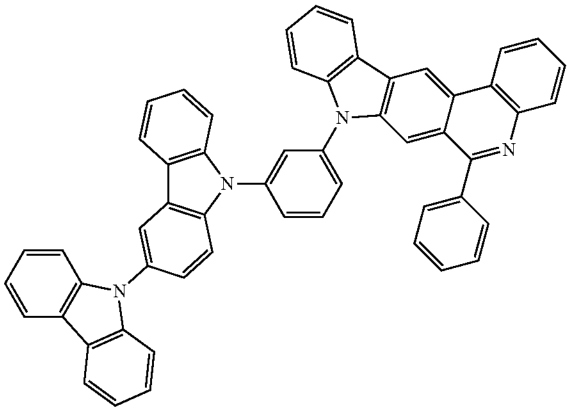
2-298
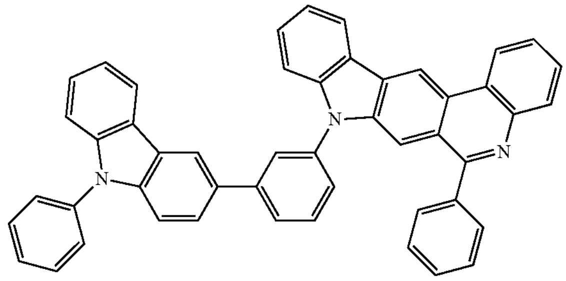
-continued
2-299
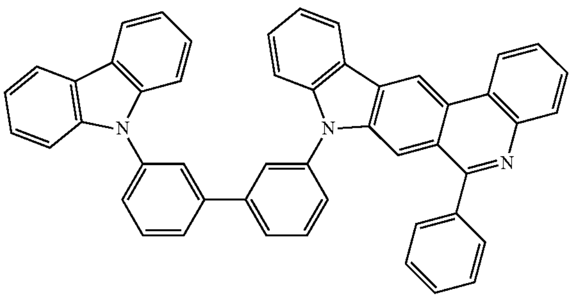
2-300
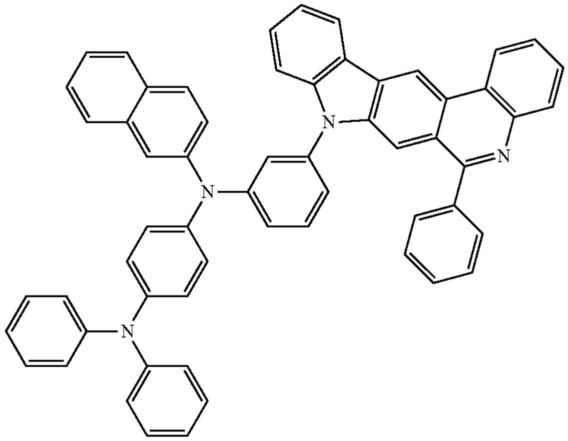
According to another exemplary embodiment of the present specification,
in Chemical Formulas 18, 19, 28, and 29, Ar may be bonded to an atom bonded to a core of phenyl at a para position thereof, and Chemical Formulas 18, 19, 28, and 29 may be selected from the following compounds.
3-1
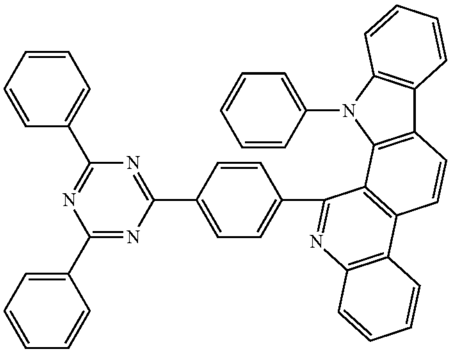

-continued
3-2
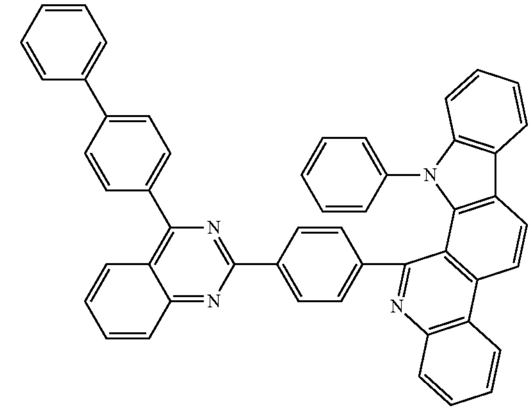
3-3
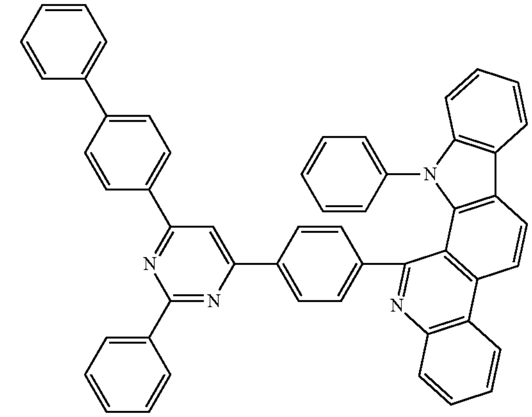
3-4
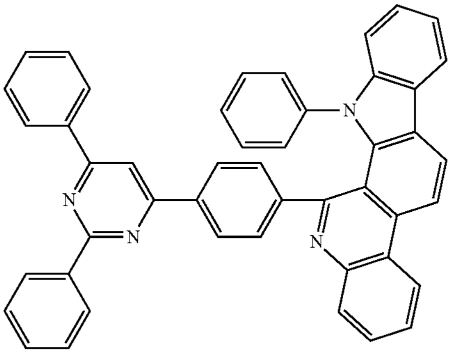
3-5
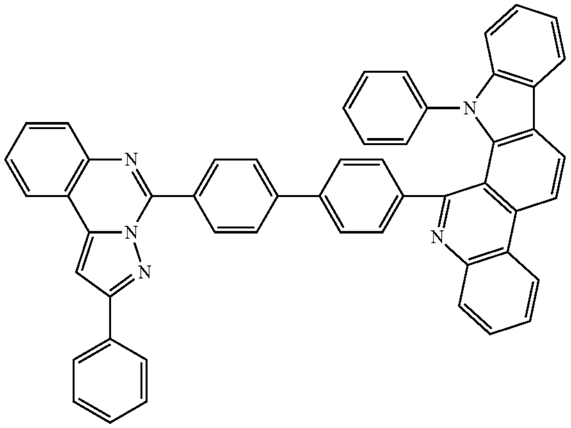
-continued
3-6
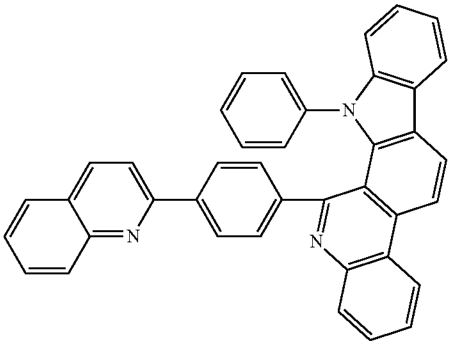
3-7
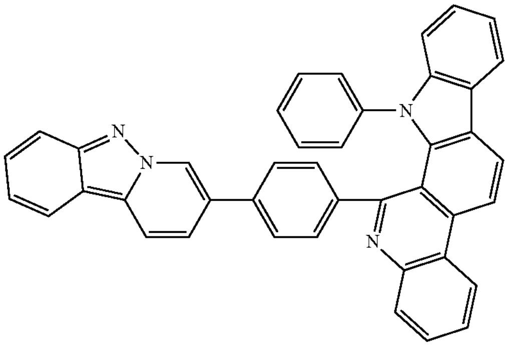
3-8
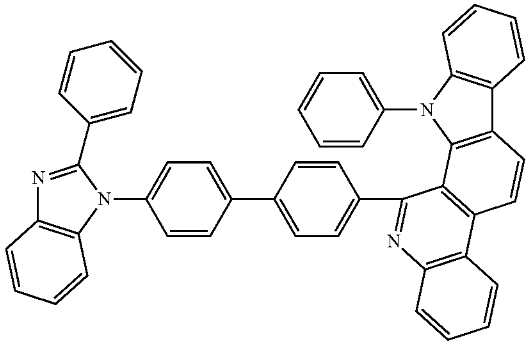
3-9
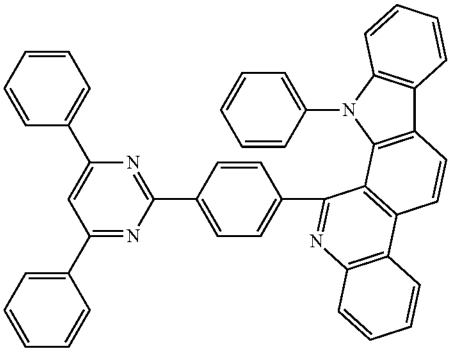

-continued
3-10
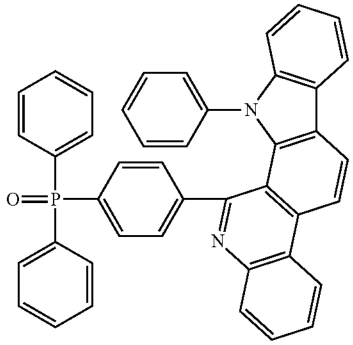
3-11
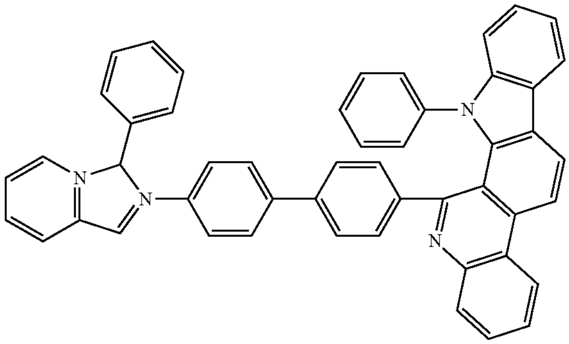
3-12
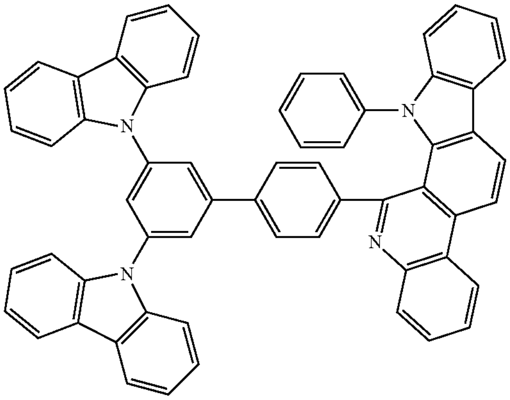
3-13
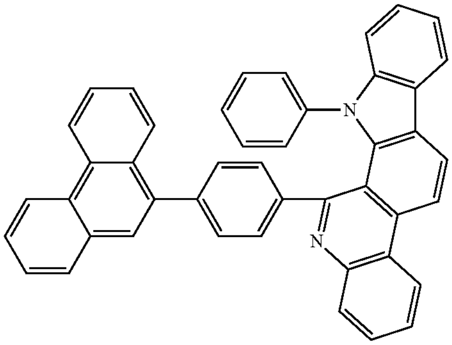
-continued
3-14
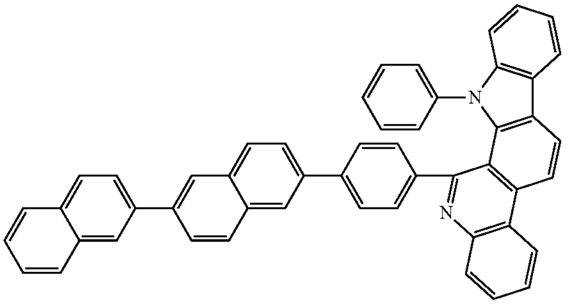
3-15
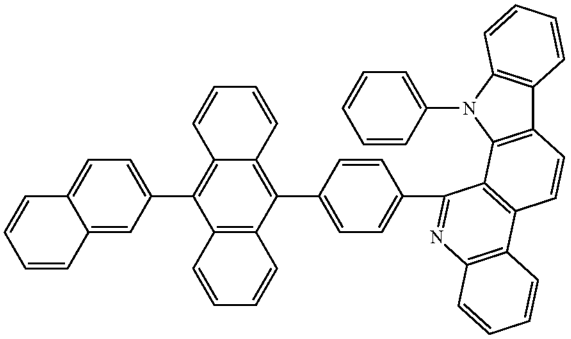
3-16
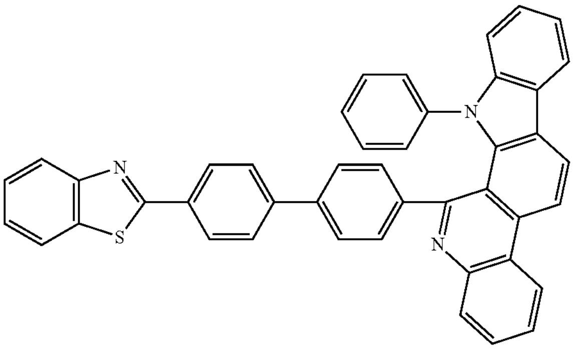
3-17
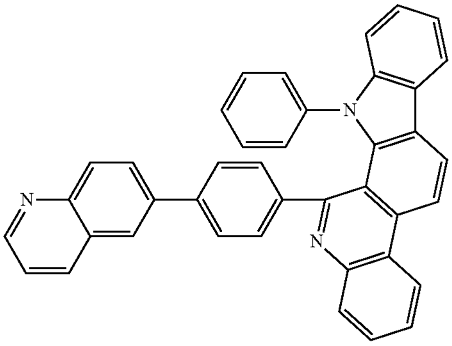

-continued
3-18
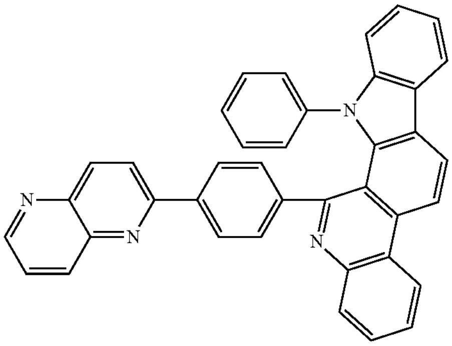
3-19
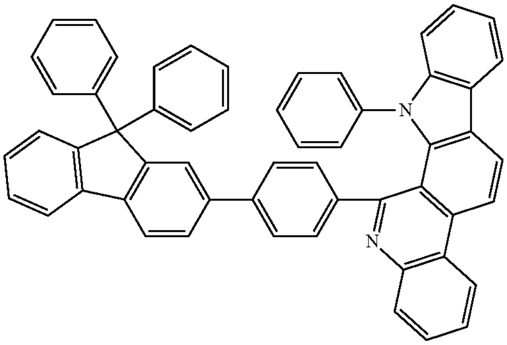
3-20
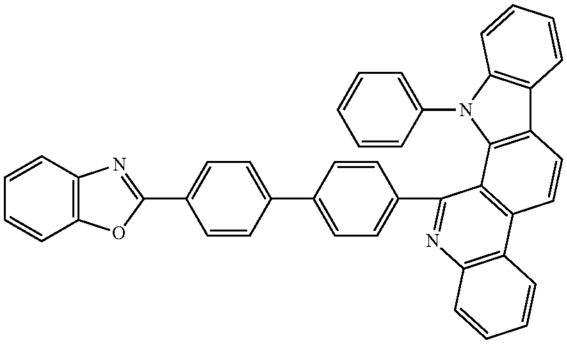
3-21
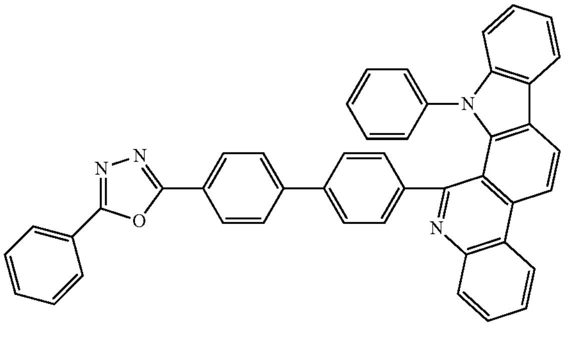
-continued
3-22
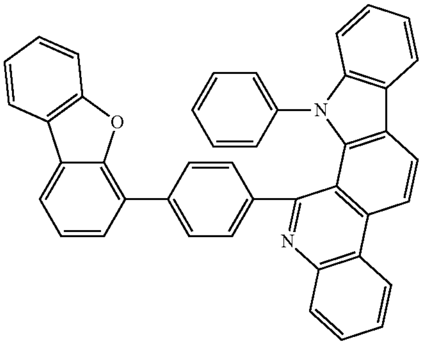
3-23
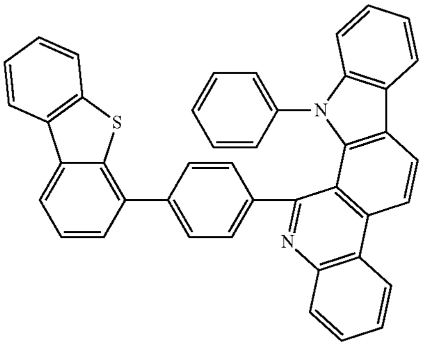
3-24
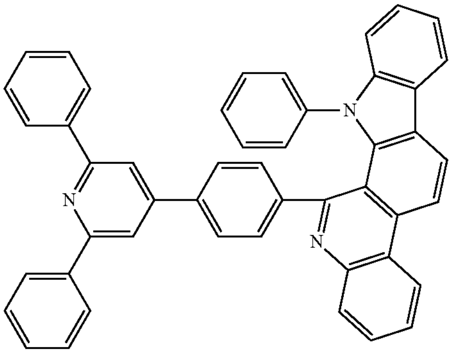
3-25
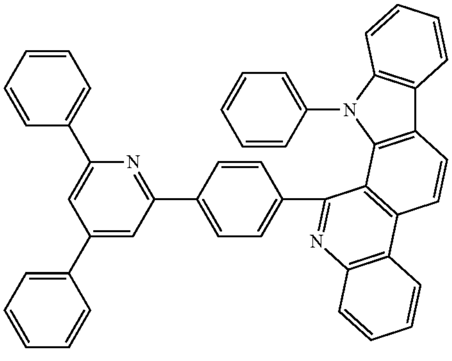

-continued
3-26
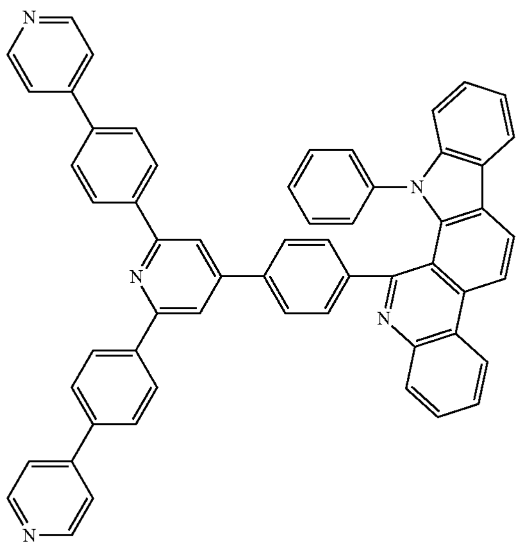
3-27
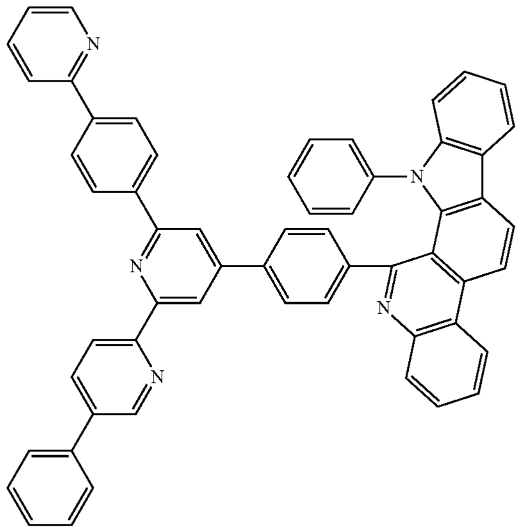
3-28
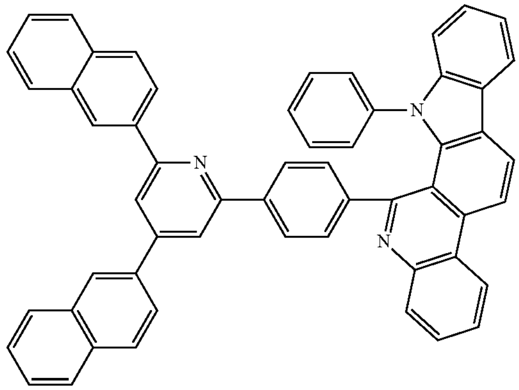
-continued
3-29
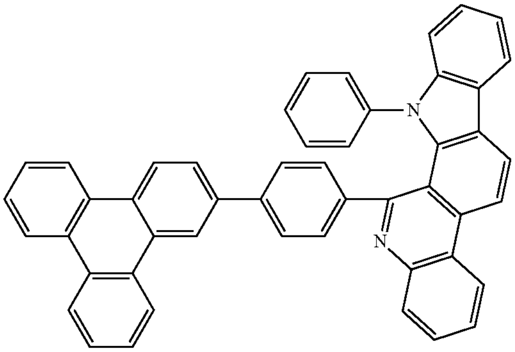
3-30
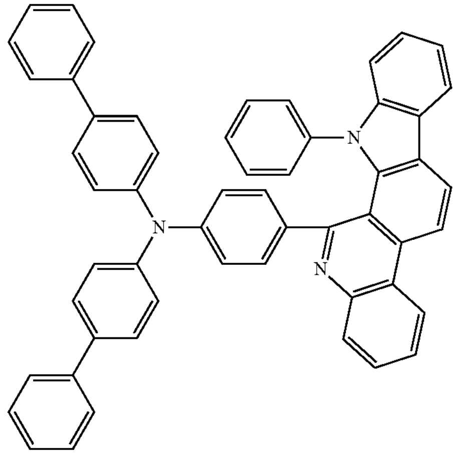
3-31
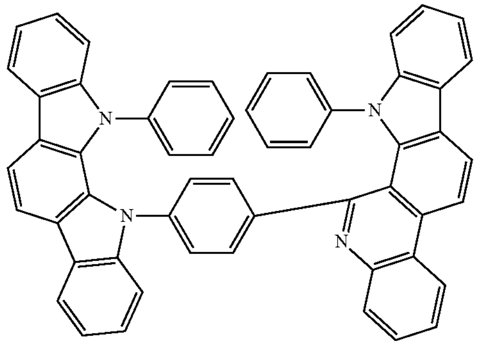
3-32
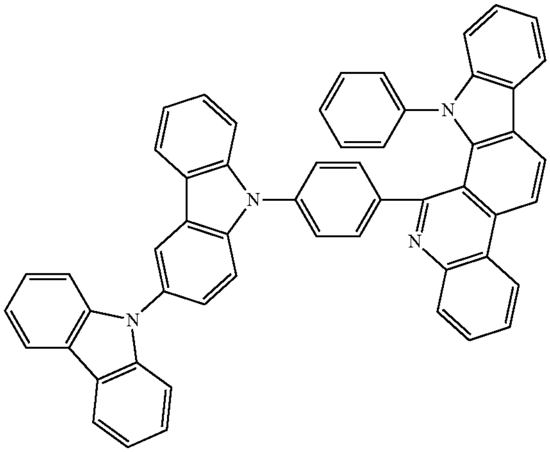

-continued
3-33
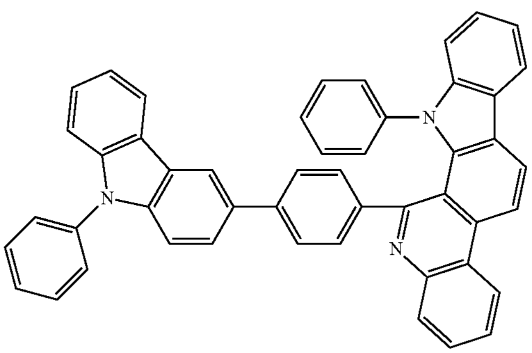
3-34
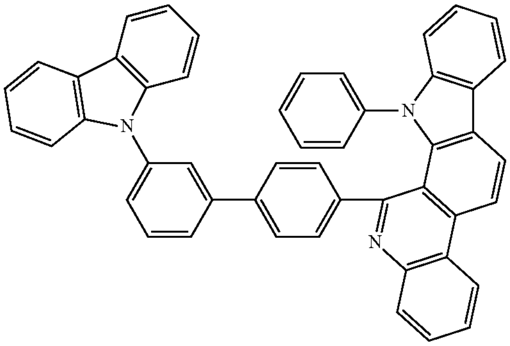
3-35
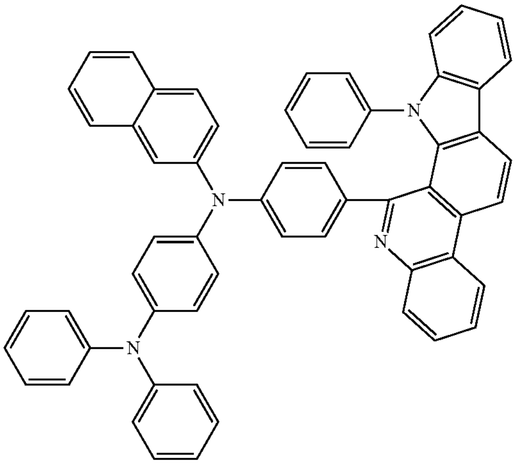
3-36
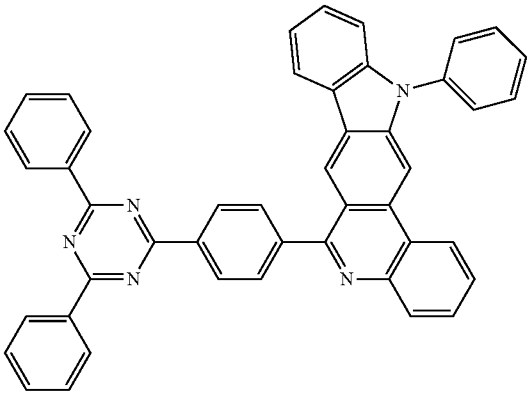
-continued
3-37
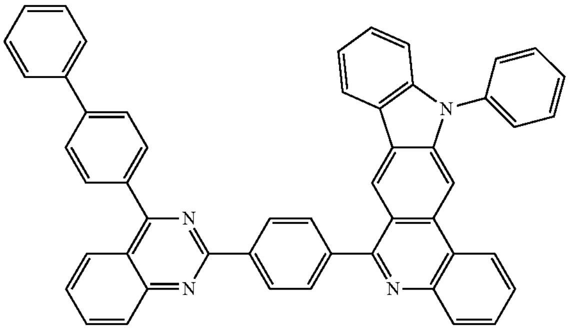
3-38
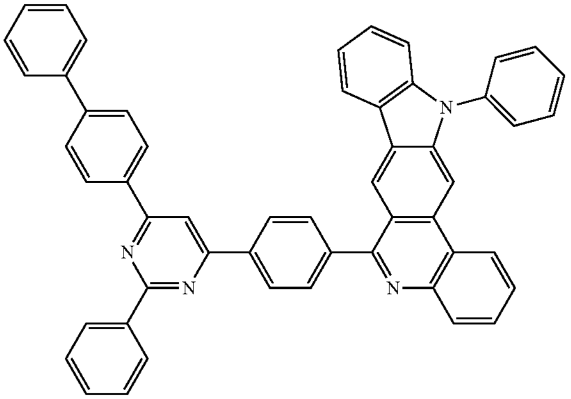
3-39
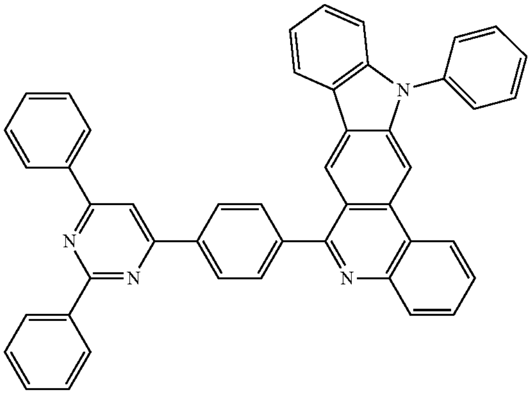
3-40
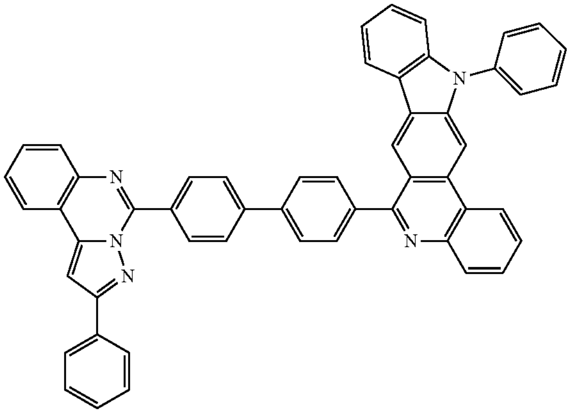

-continued
3-41
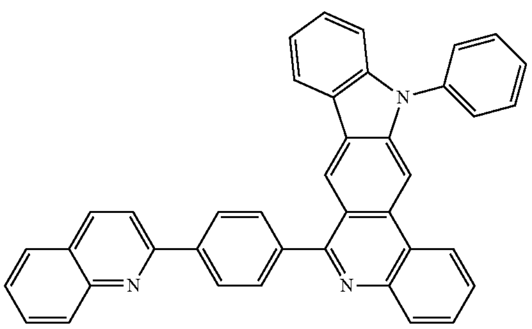
3-42
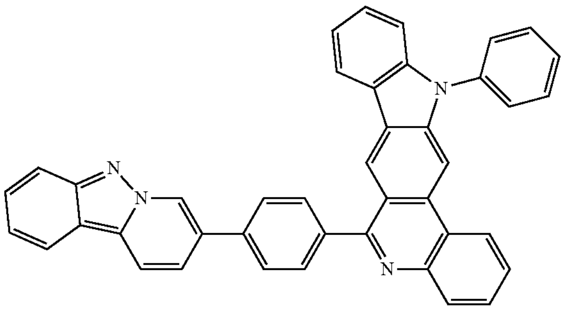
3-43
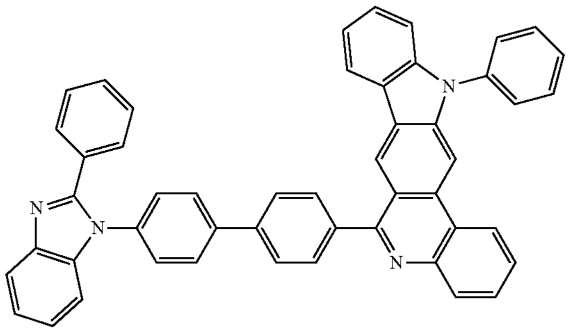
3-44
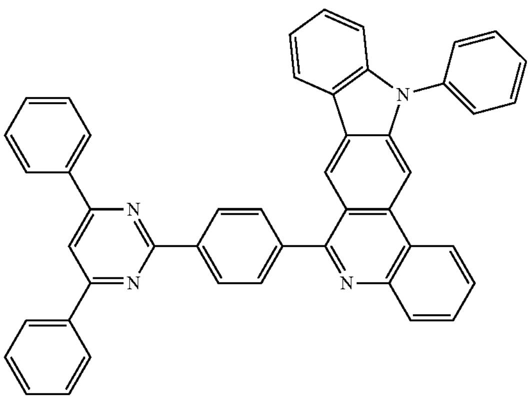
-continued
3-45
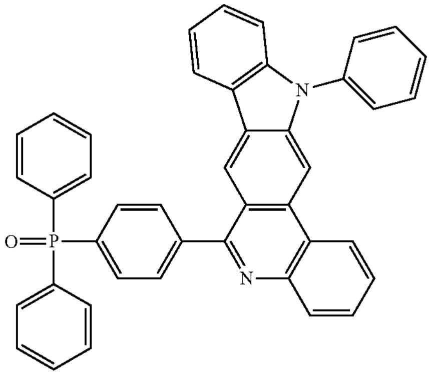
3-46
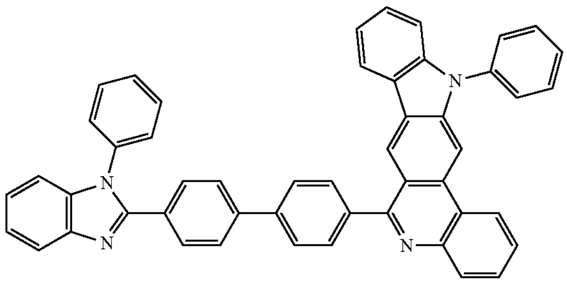
3-47
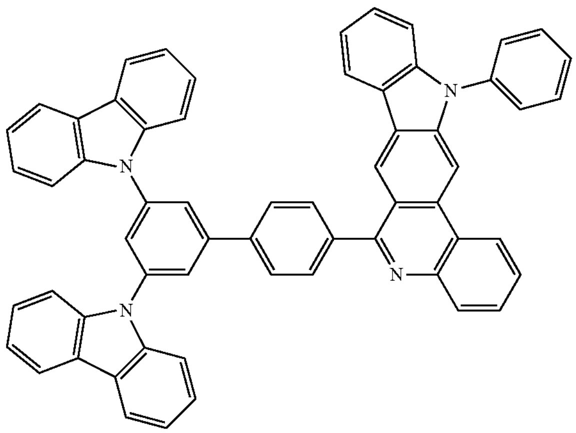
3-48
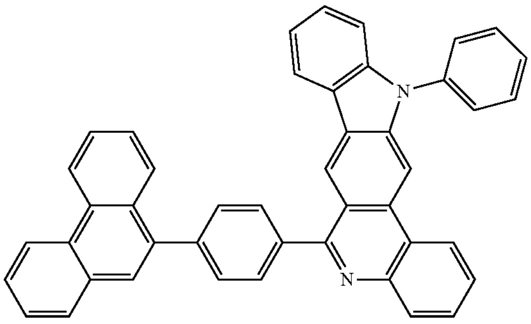

-continued
3-49
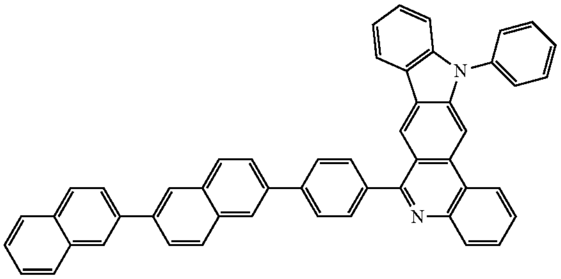
3-50
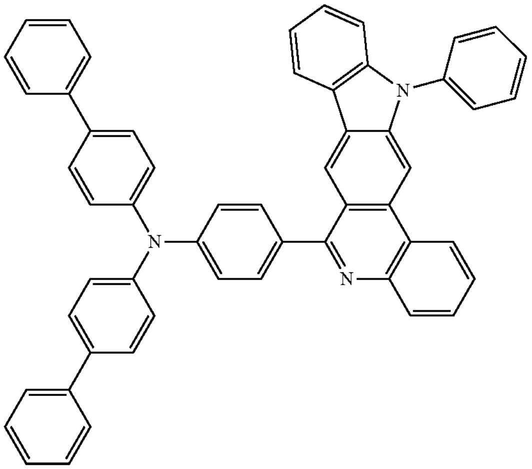
3-51
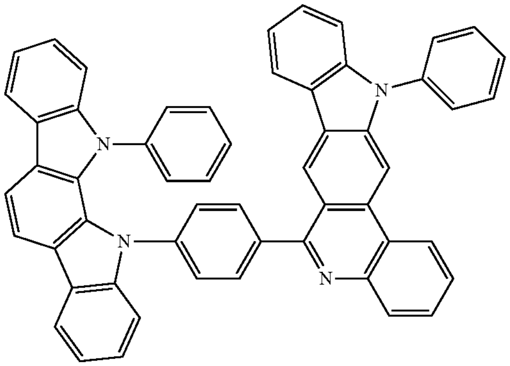
3-52
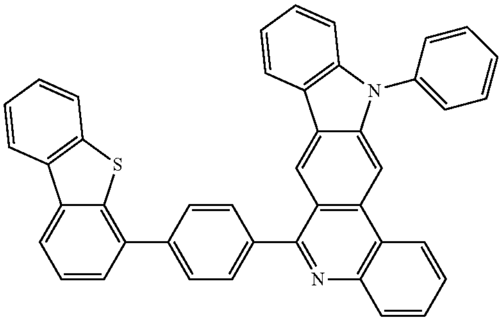
-continued
3-53
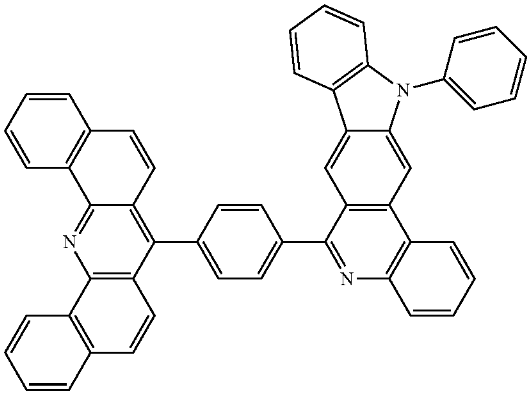
3-54
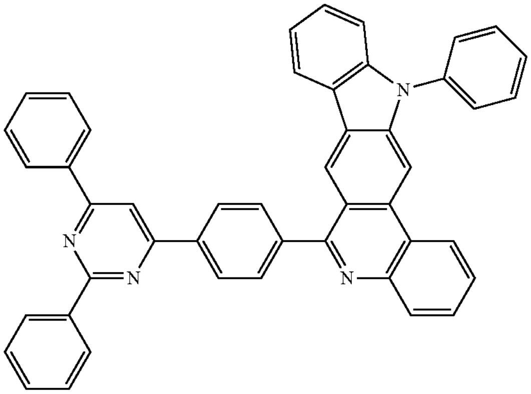
3-55
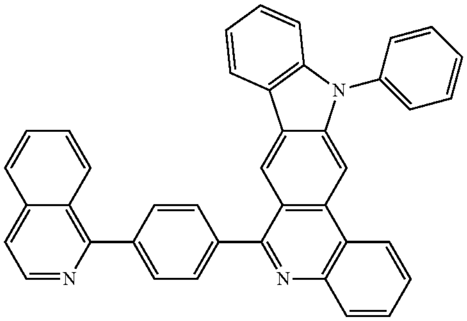
3-56
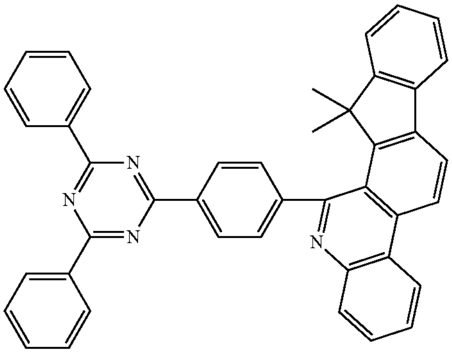

-continued
3-57
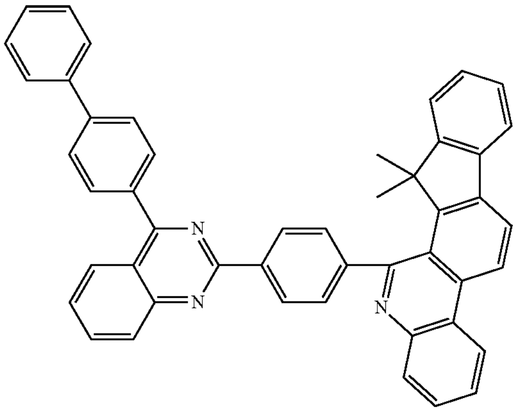
3-58
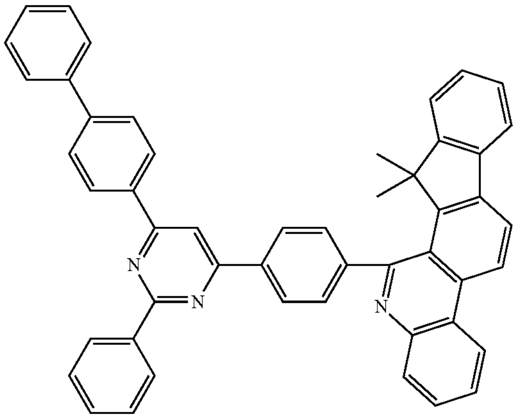
3-59
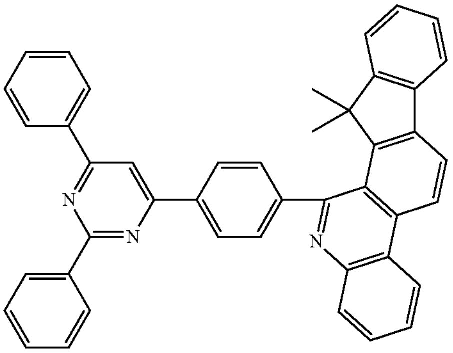
-continued
3-60
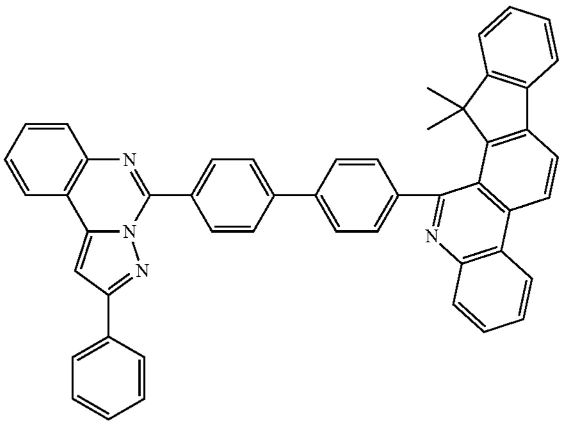
3-61
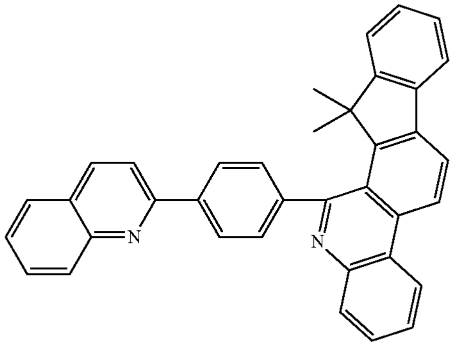
3-62
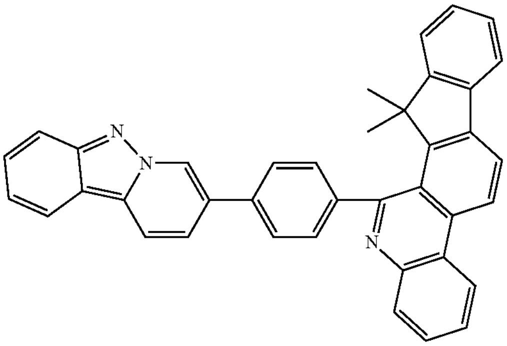
3-63
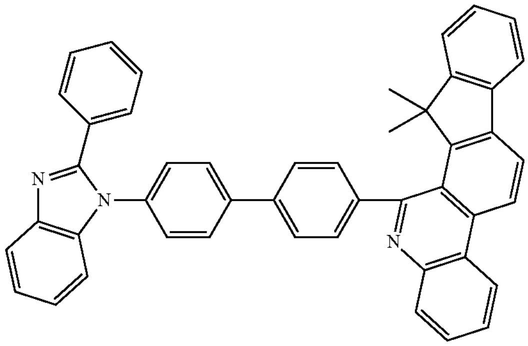

-continued
3-64
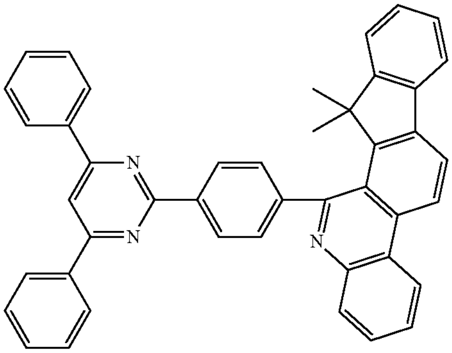
3-65
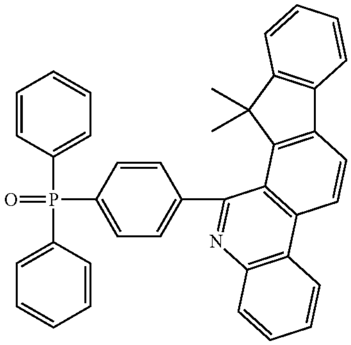
3-66
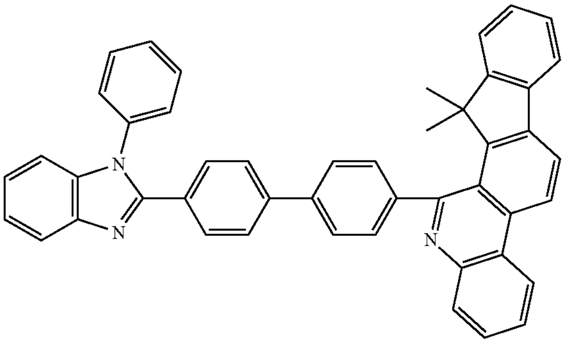
3-67
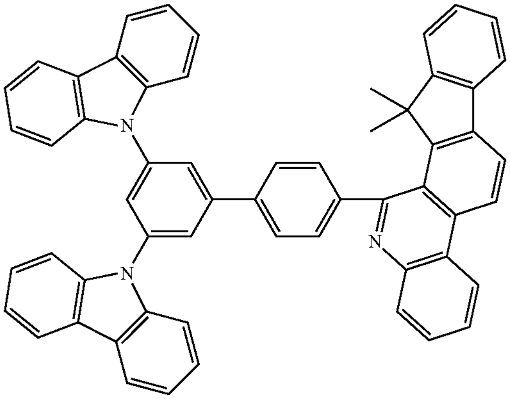
-continued
3-68
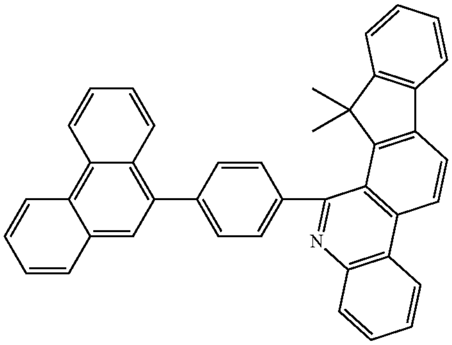
3-69
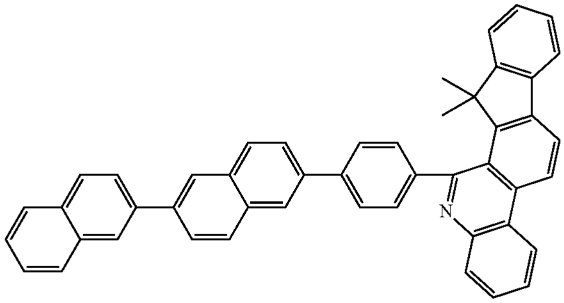
3-70
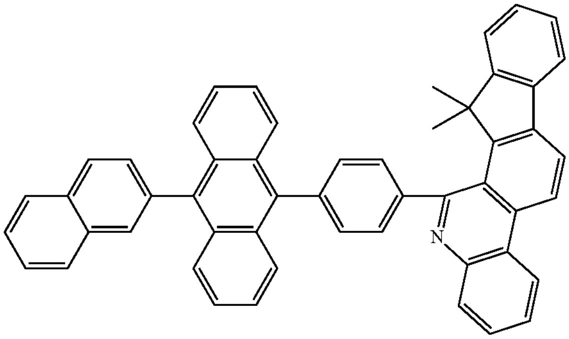
3-71
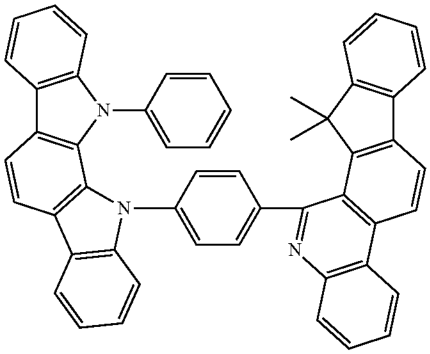

-continued
3-72
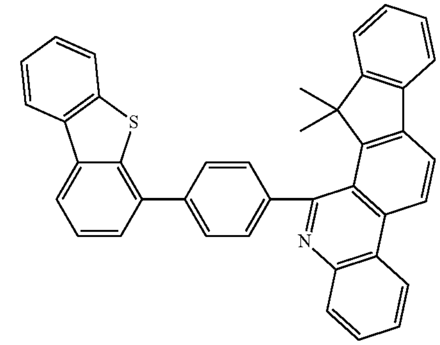
3-73
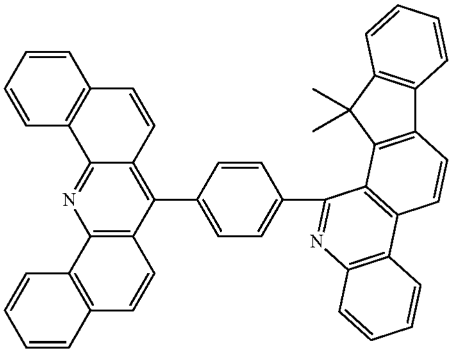
3-74
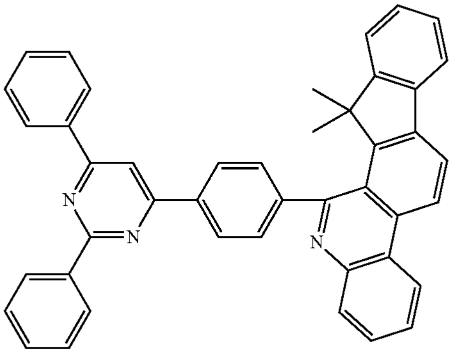
3-75
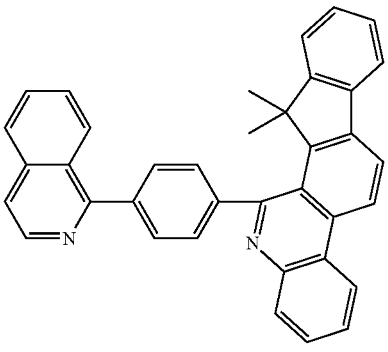
-continued
3-76
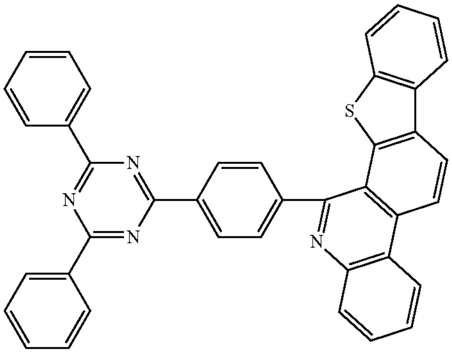
3-77
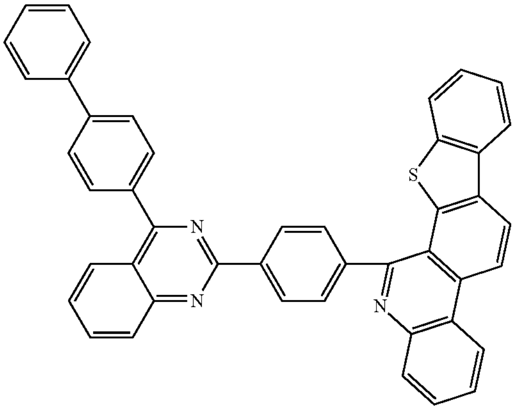
3-78
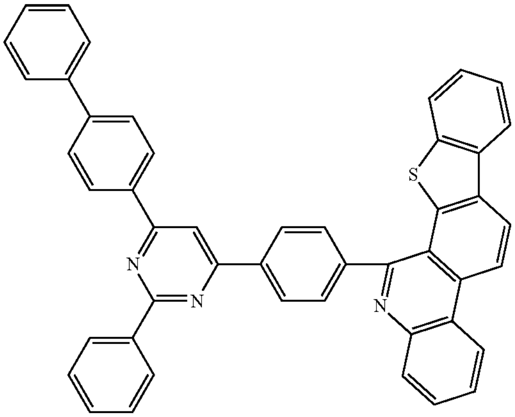
3-79
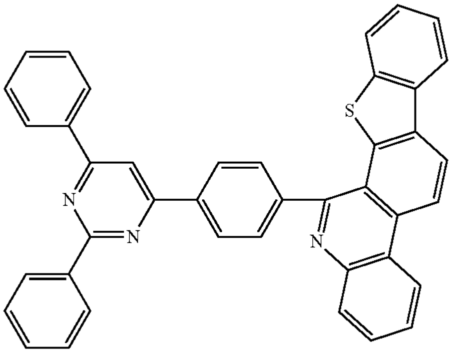

-continued
3-80
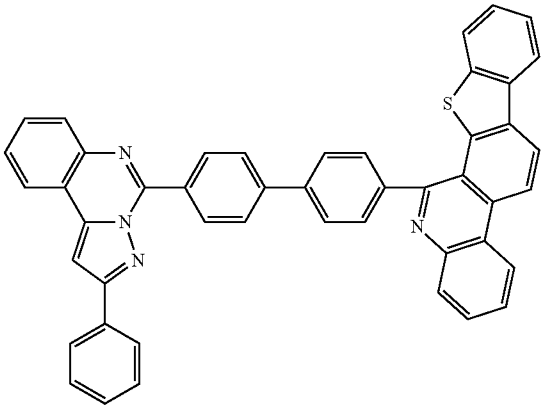
3-81
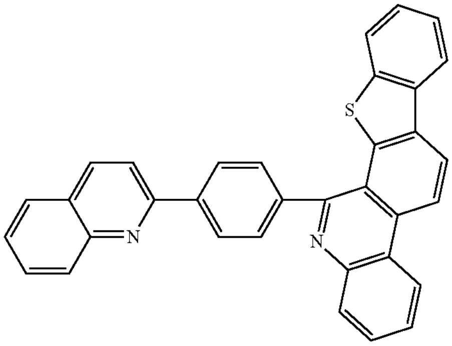
3-82
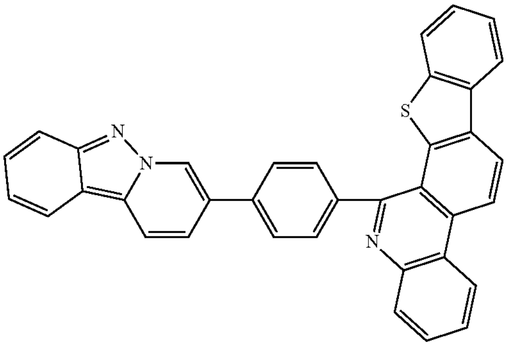
3-83
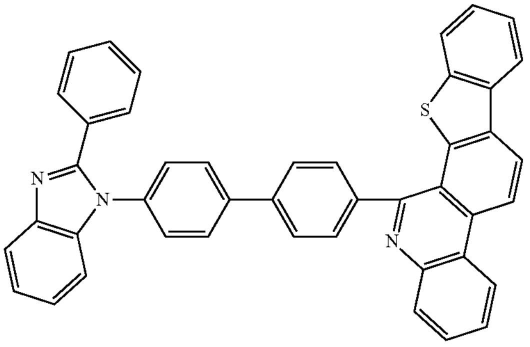
-continued
3-84
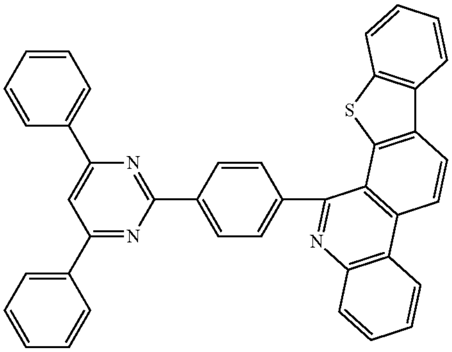
3-85
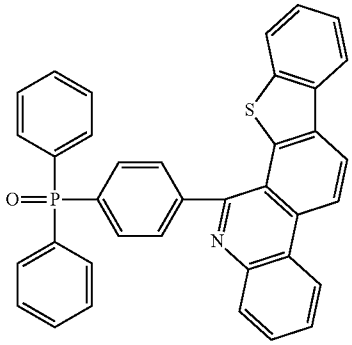
3-86
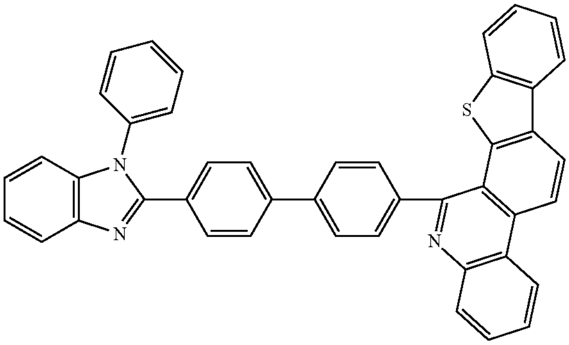
3-87
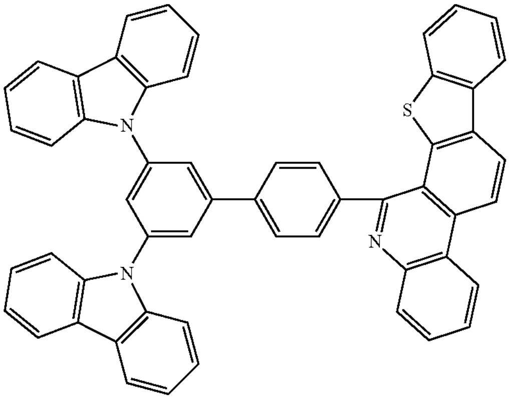

-continued
3-88
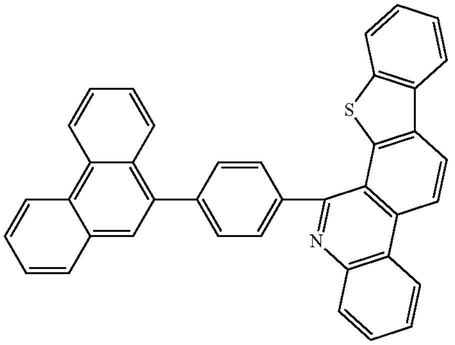
3-89
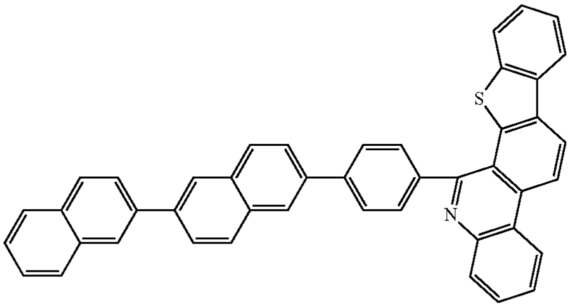
3-90
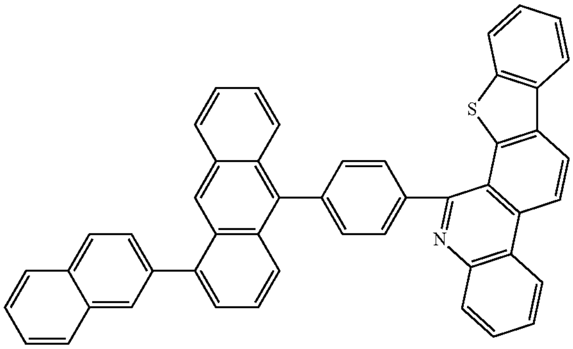
3-91
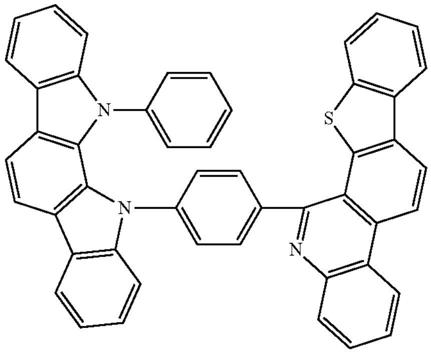
-continued
3-92
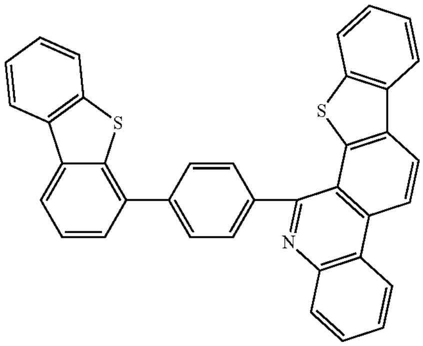
3-93
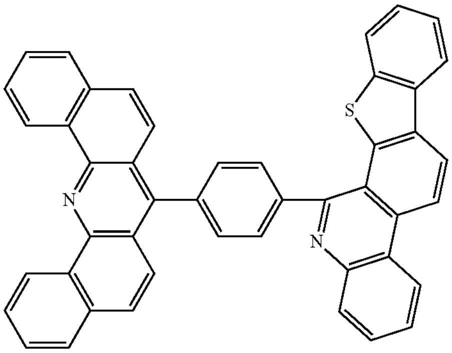
3-94
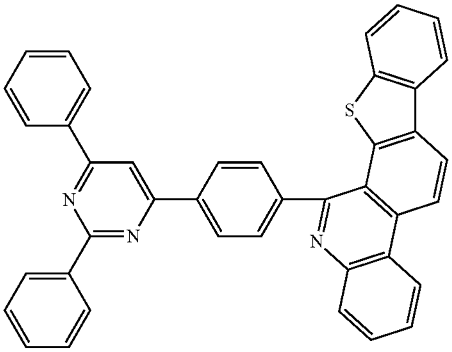
3-95
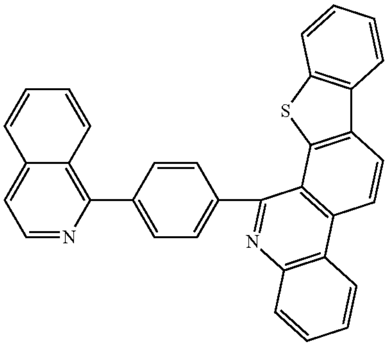

-continued
3-96
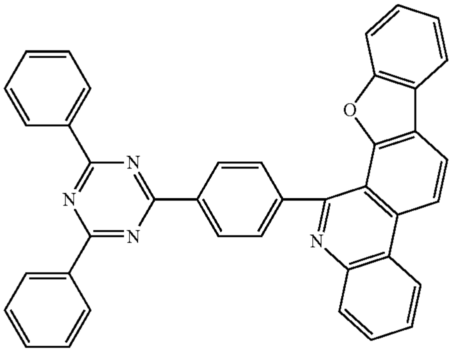
3-97
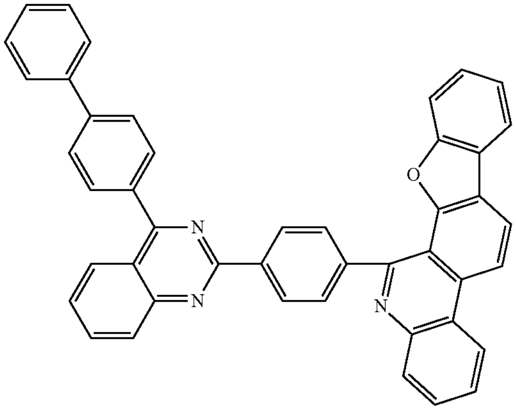
3-98
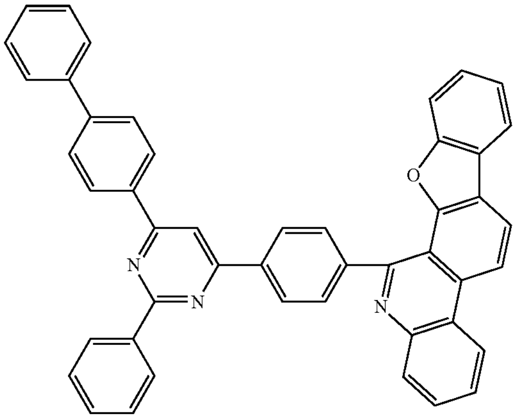
3-99
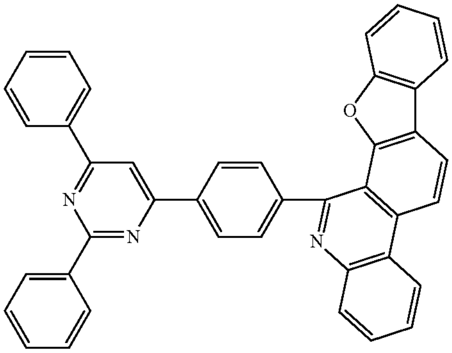
-continued
3-100
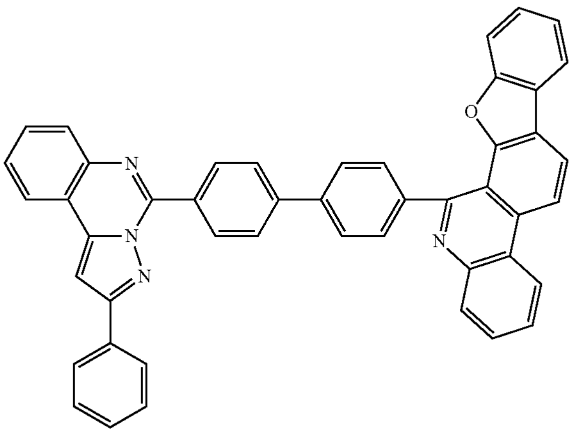
3-101
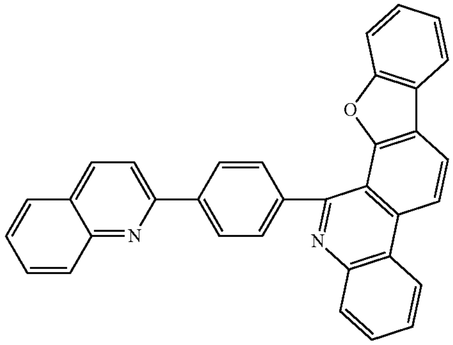
3-102
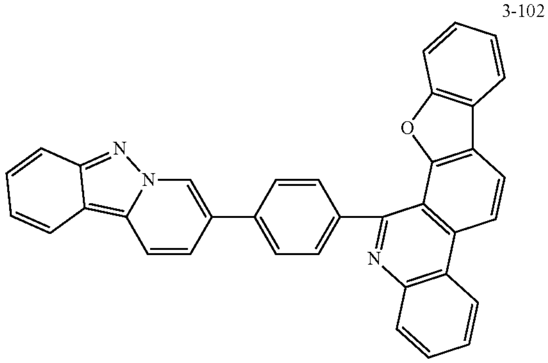
3-103
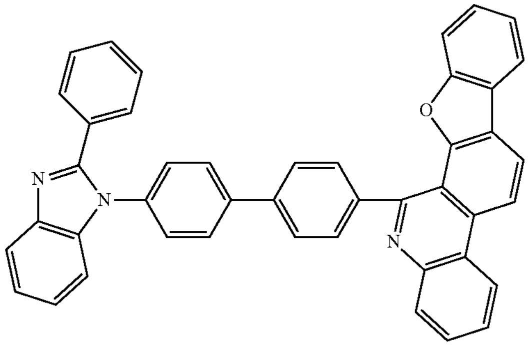

-continued
3-104
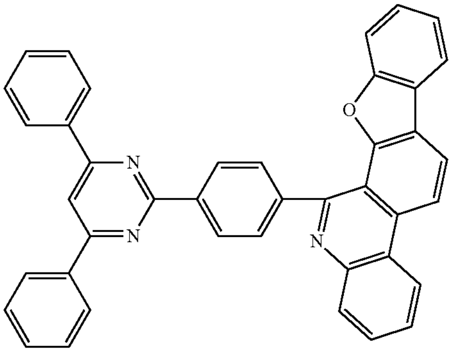
3-105
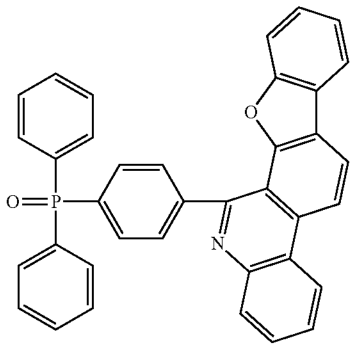
3-106
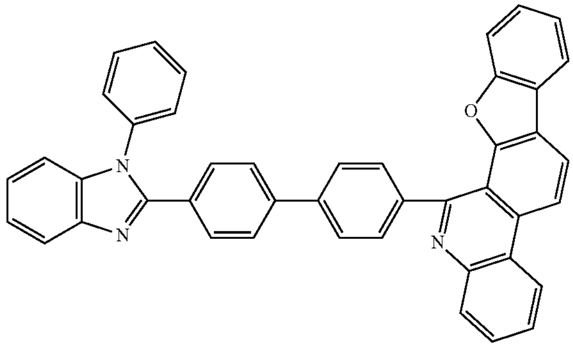
3-107
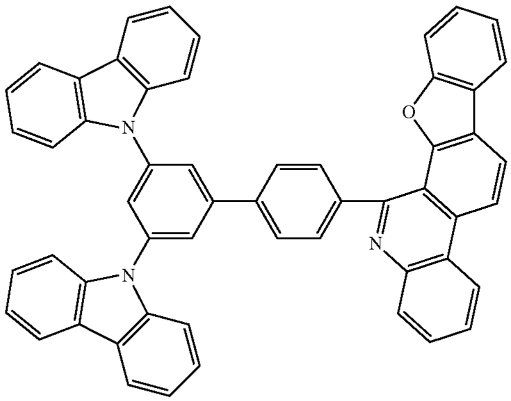
-continued
3-108
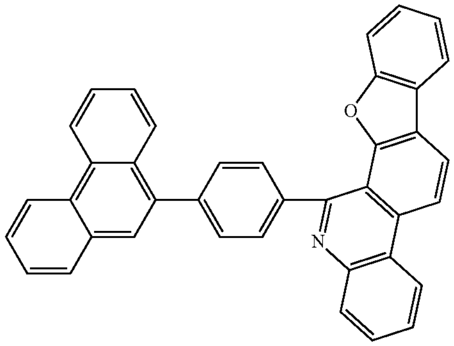
3-109
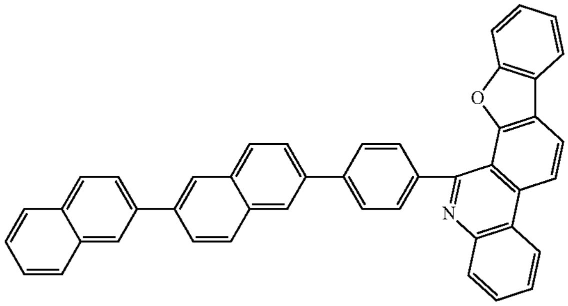
3-110
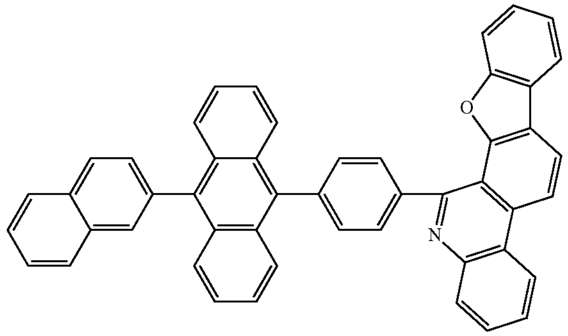
3-111
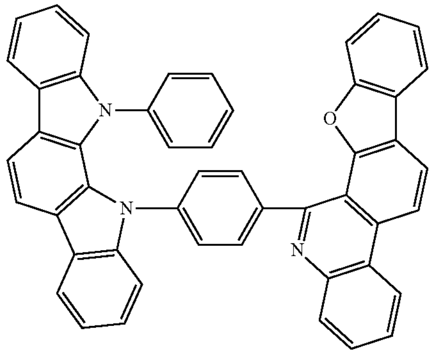

-continued
3-112
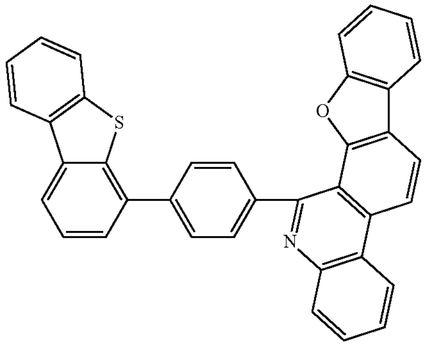
3-113
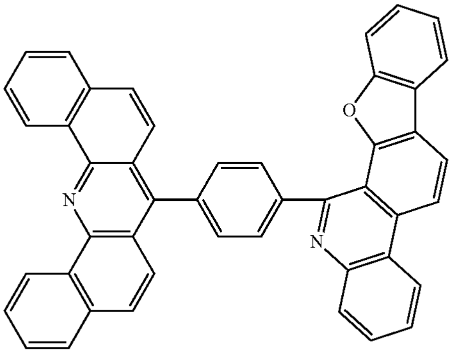
3-114
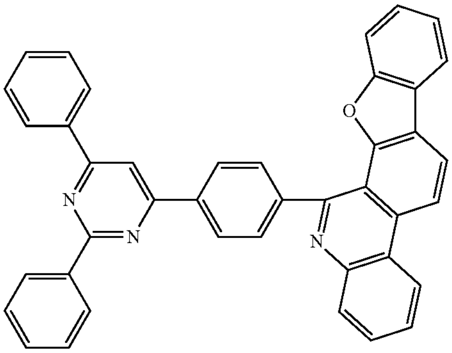
3-115
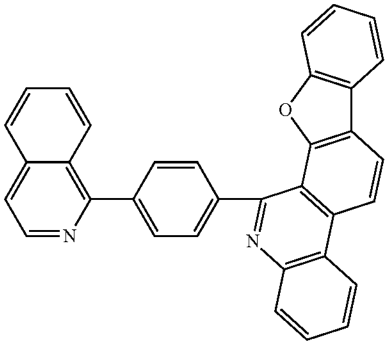
According to another exemplary embodiment of the present specification,
in Chemical Formulas 18, 19, 28, and 29, Ar may be bonded to an atom bonded to a core of phenyl at a meta position thereof, and Chemical Formulas 18, 19, 28, and 29 may be selected from the following compounds.
3-116
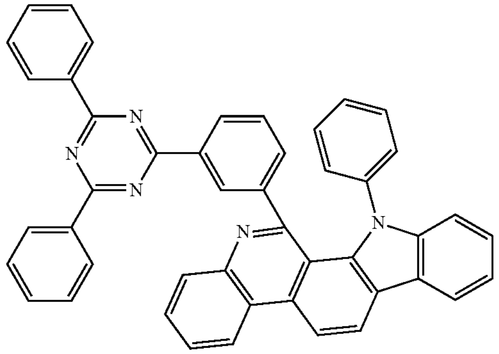
3-117
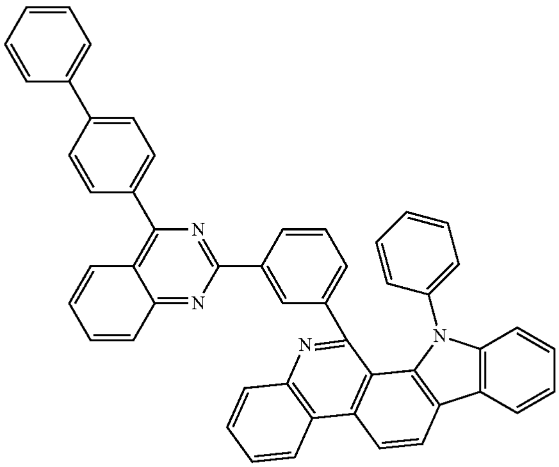
3-118
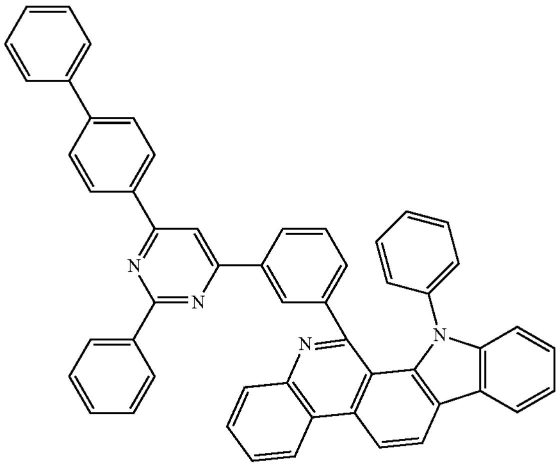

-continued
3-119
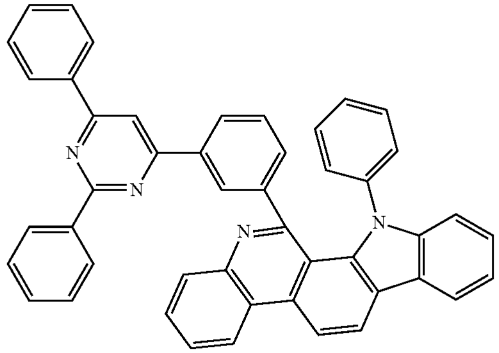
3-120
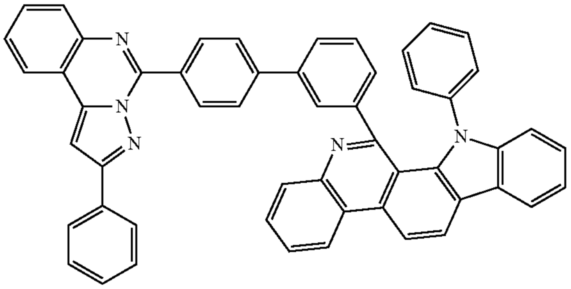
3-121
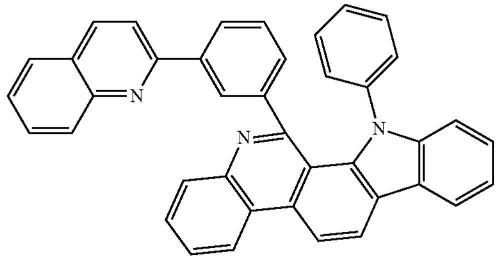
3-122
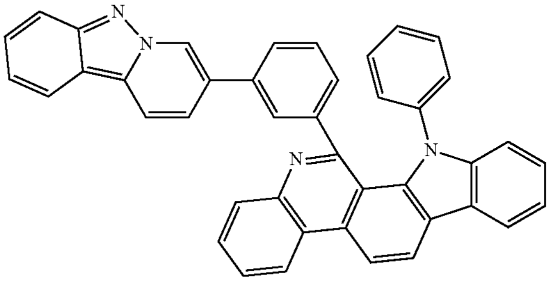
3-123
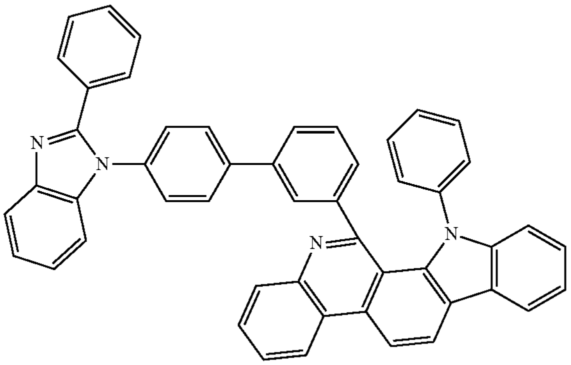
-continued
3-124
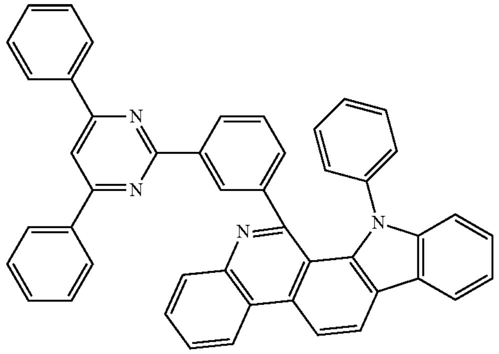
3-125
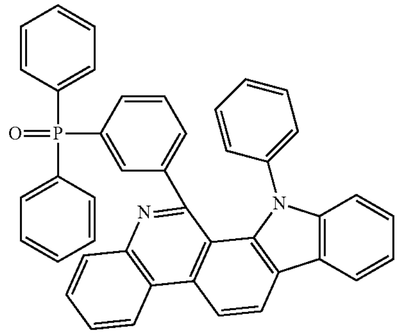
3-126
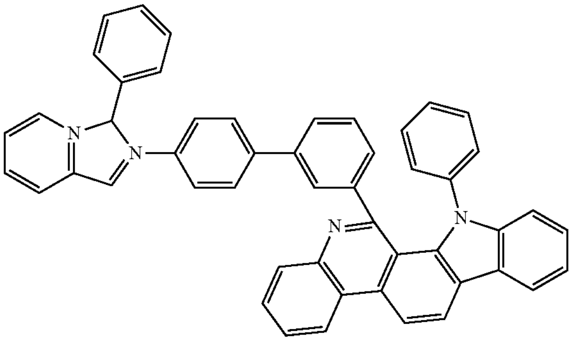
3-127
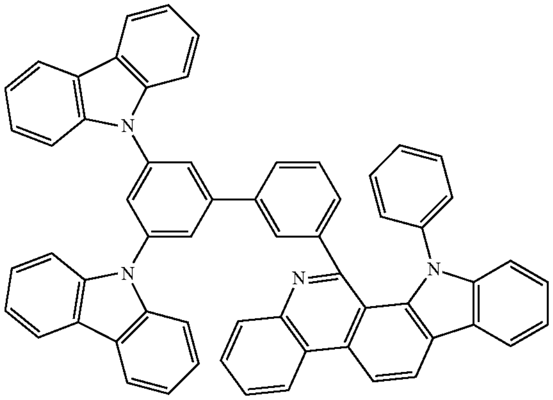

-continued
3-128
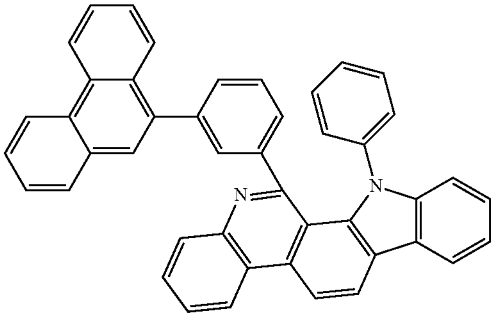
3-129
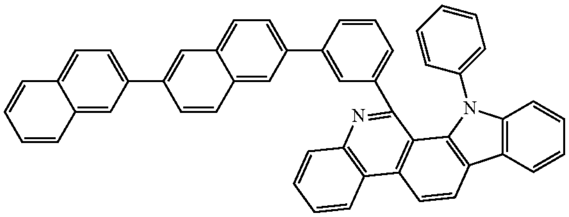
3-130
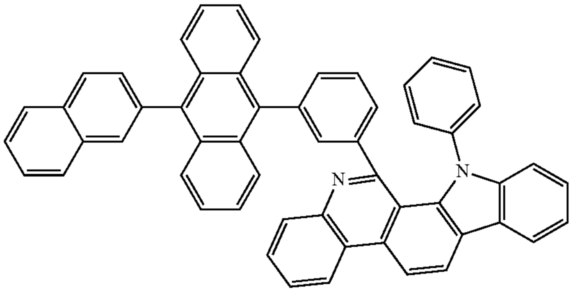
3-131
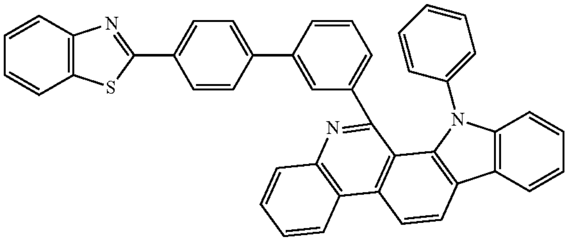
3-132
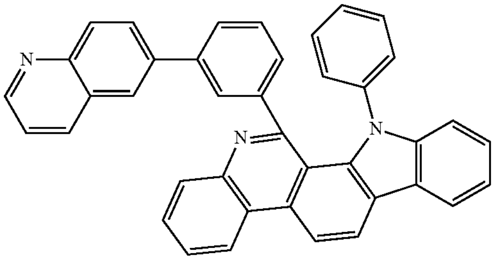
-continued
3-133
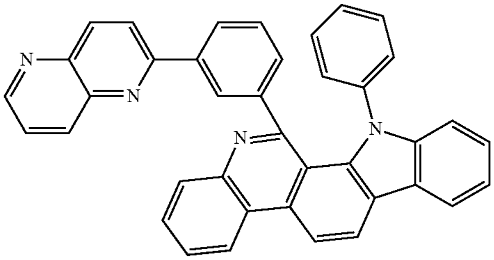
3-134
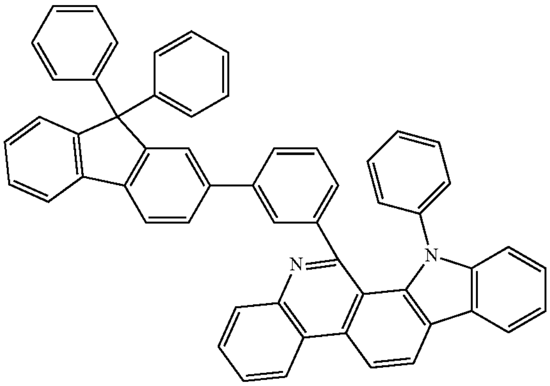
3-135
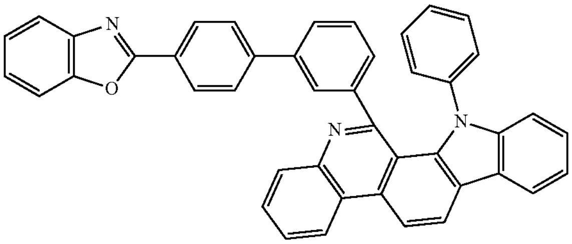
3-136
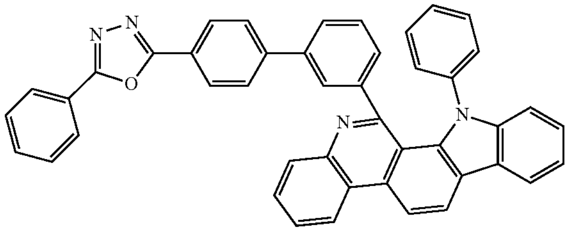
3-137
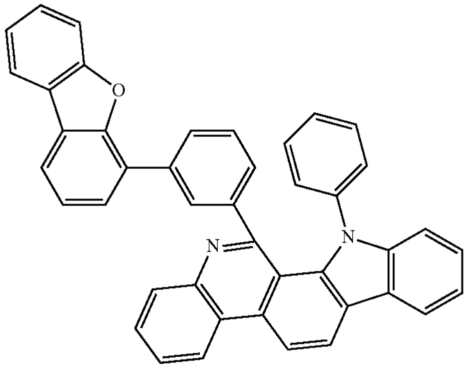

-continued
3-138
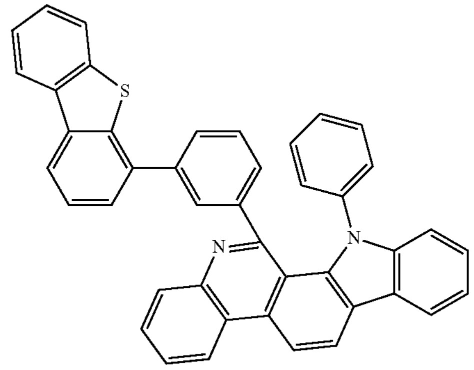
3-139
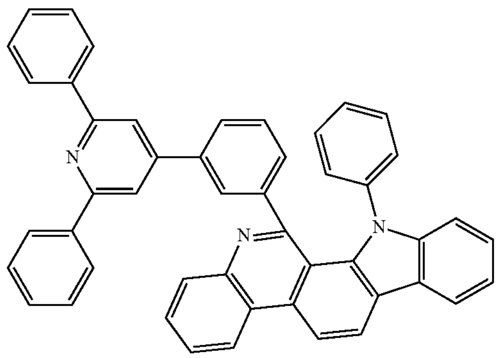
3-140
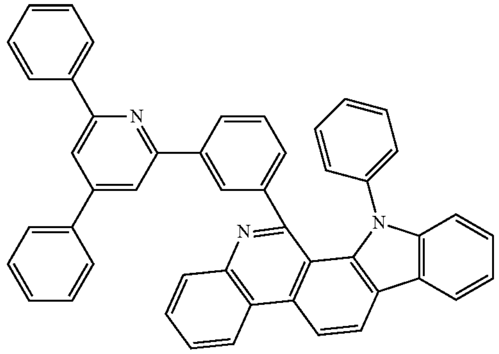
-continued
3-141
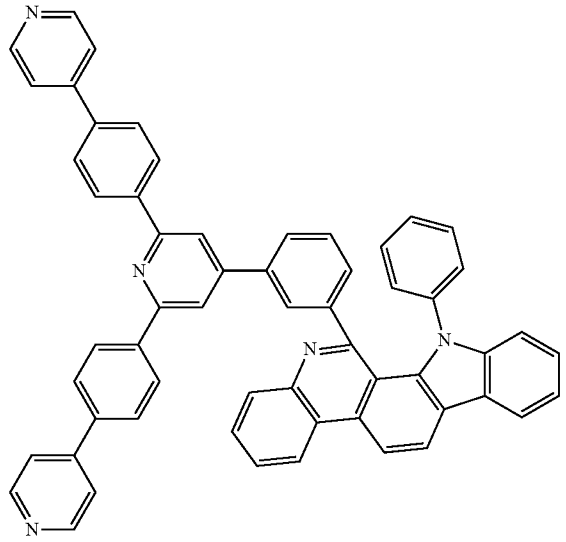
3-142
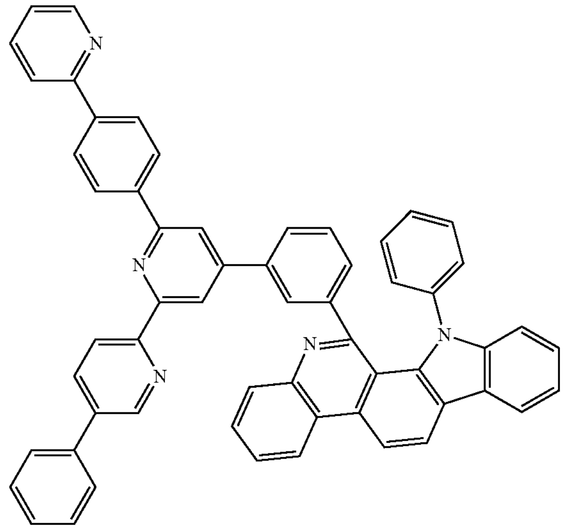
3-143
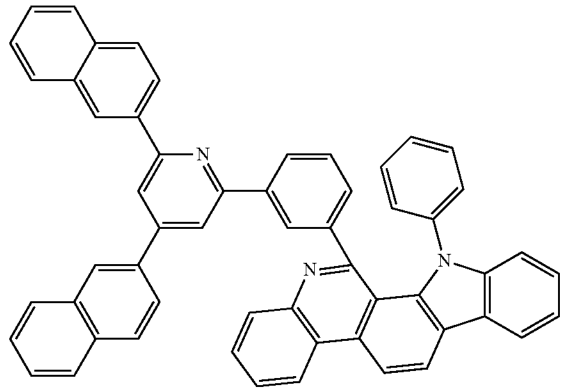

-continued
3-144
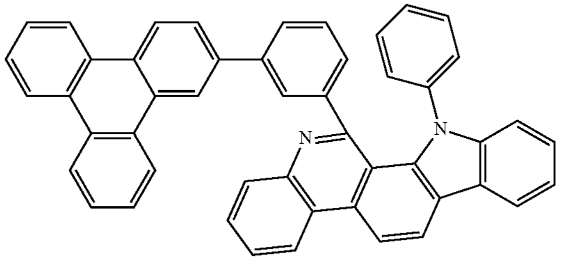
3-145
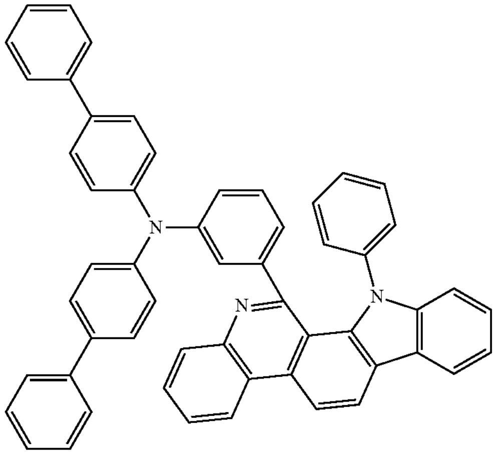
3-146
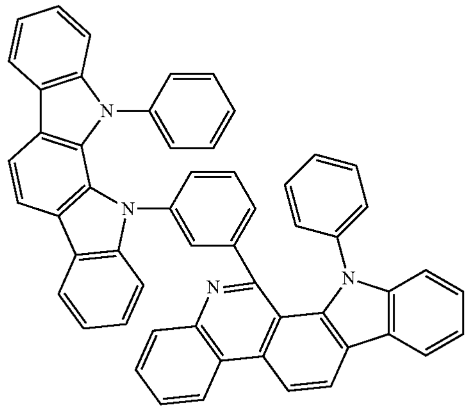
3-147
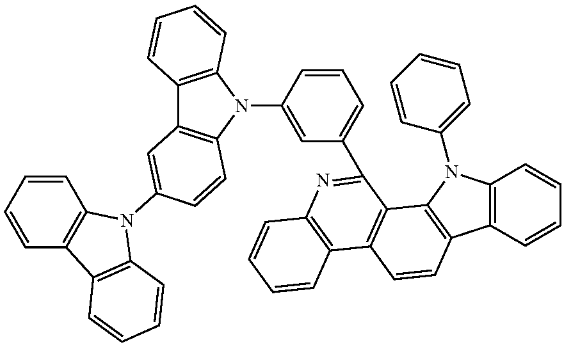
-continued
3-148
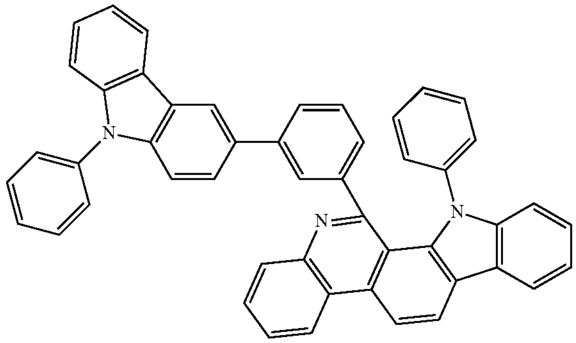
3-149
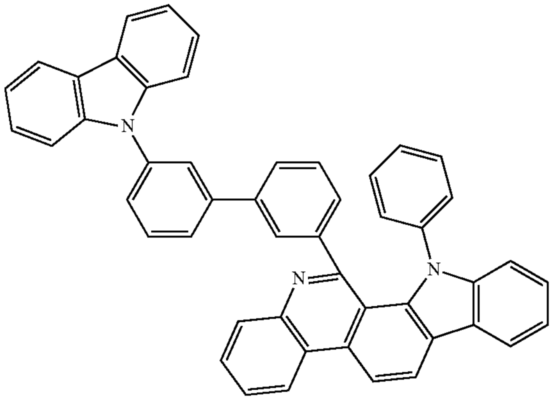
3-150
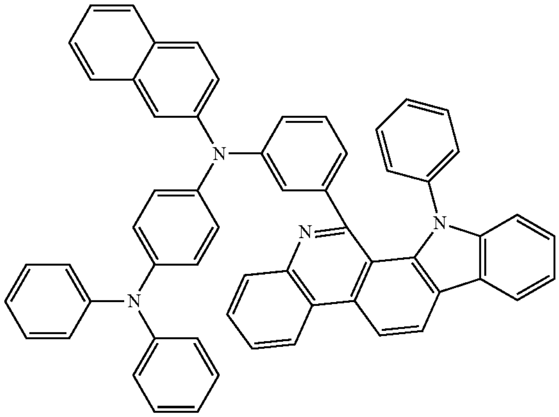
3-151
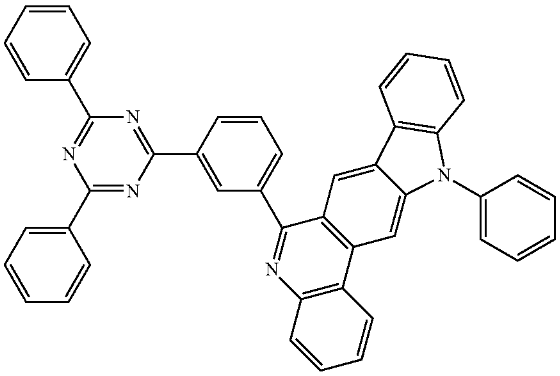

-continued
3-152
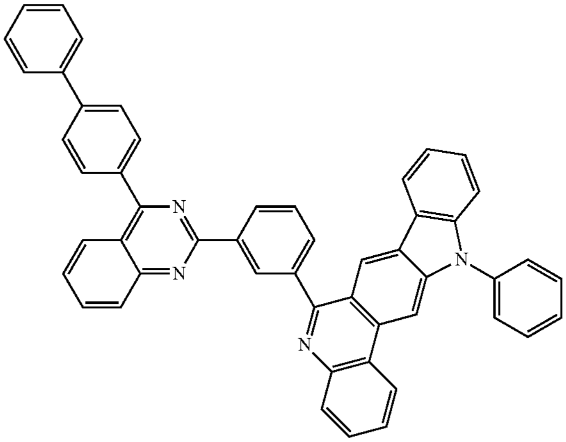
3-153
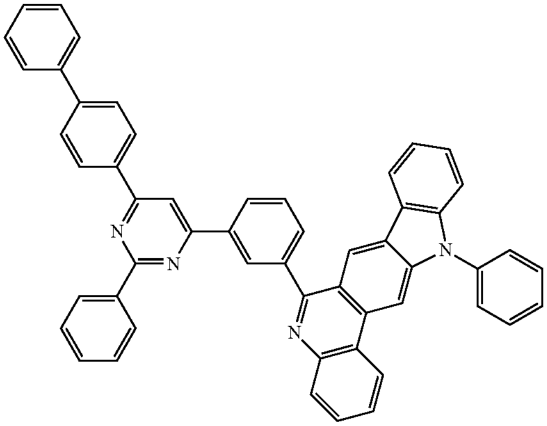
3-154
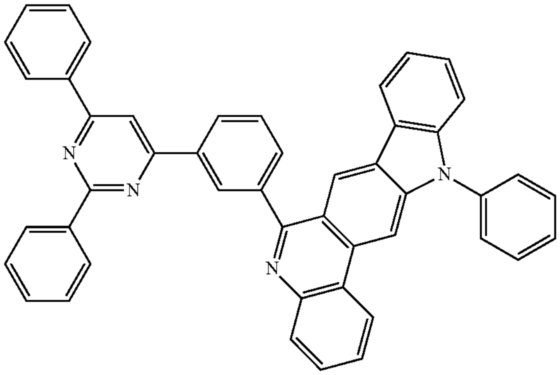
3-155
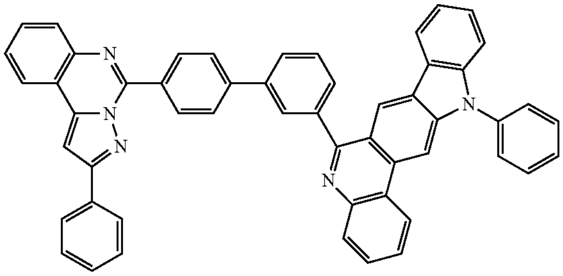
-continued
3-156
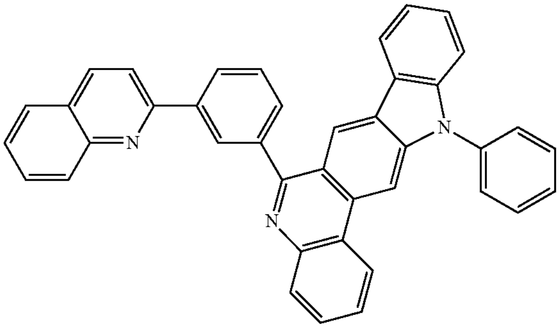
3-157
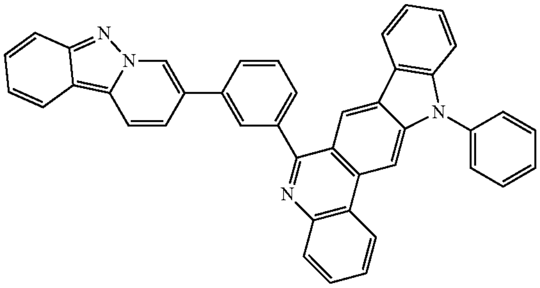
3-158
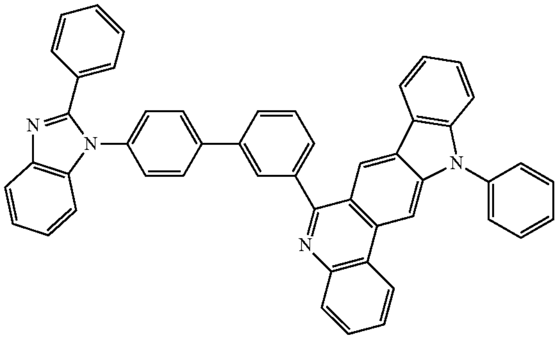
3-159
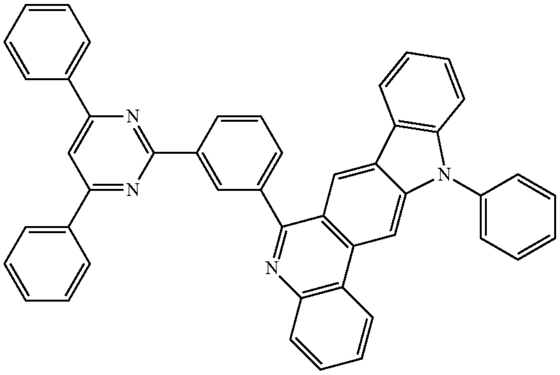

-continued
3-160
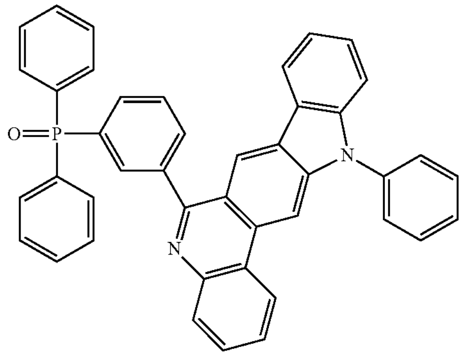
3-161
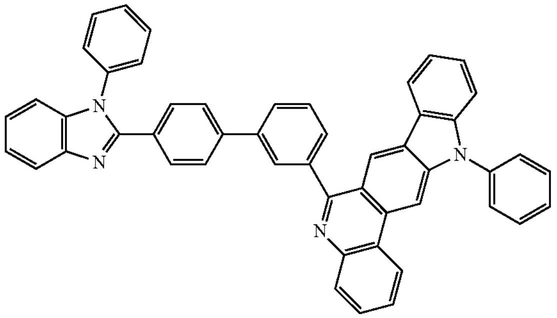
3-162
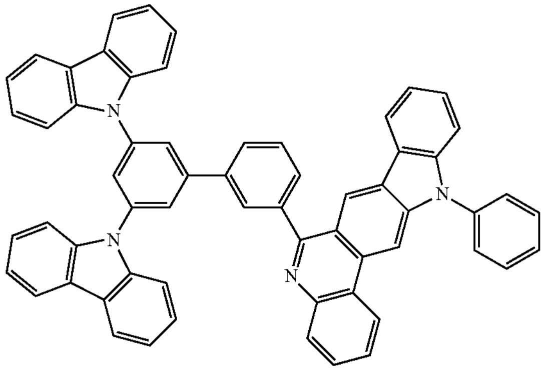
3-163
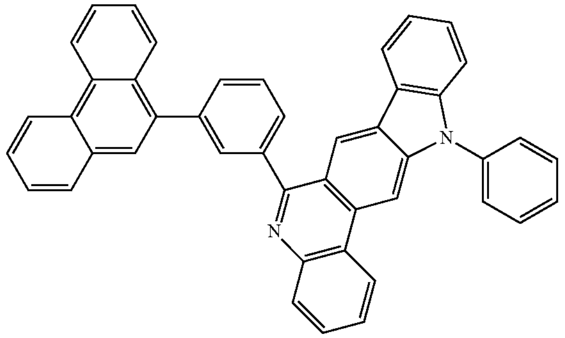
-continued
3-164
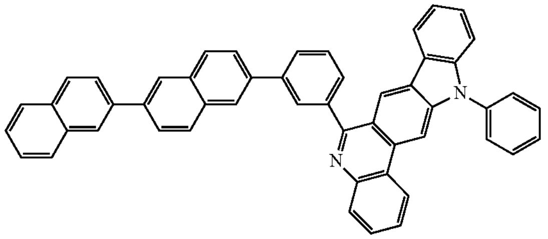
3-165
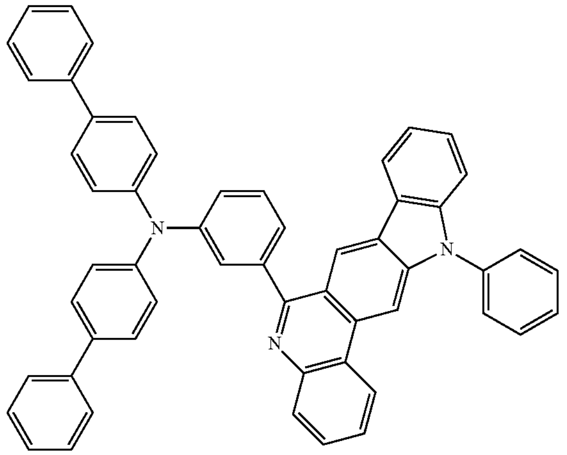
3-166
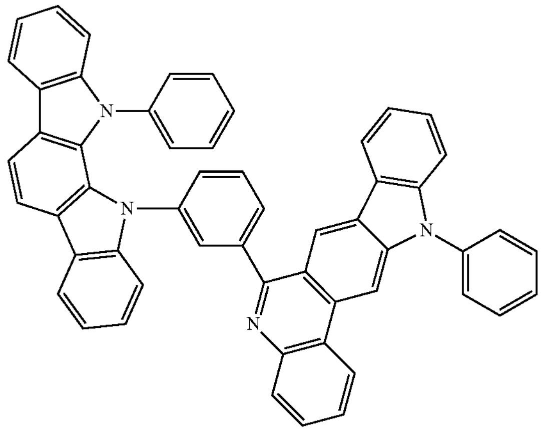
3-167
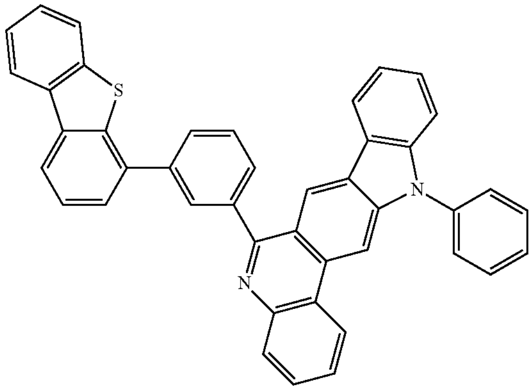

-continued
3-168
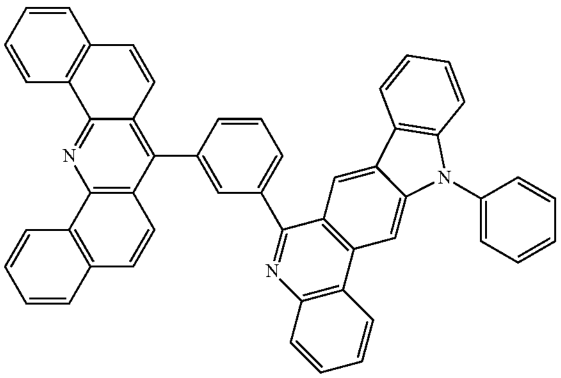
3-169
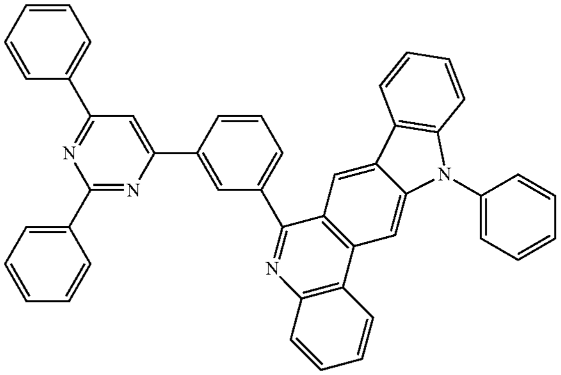
3-170
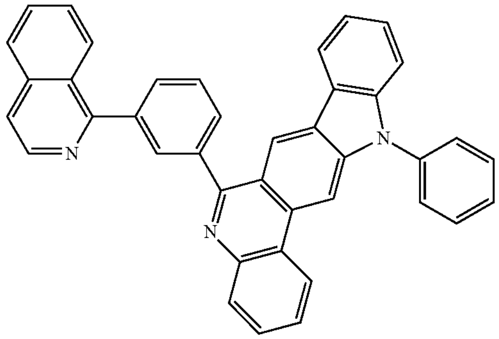
3-171
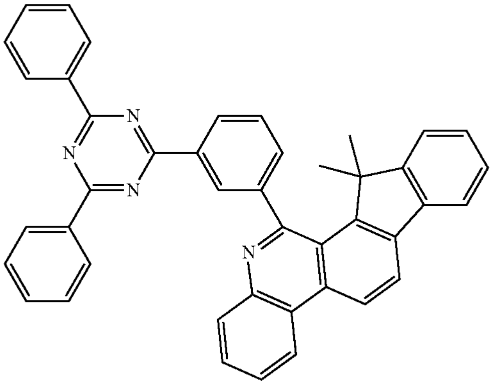
-continued
3-172
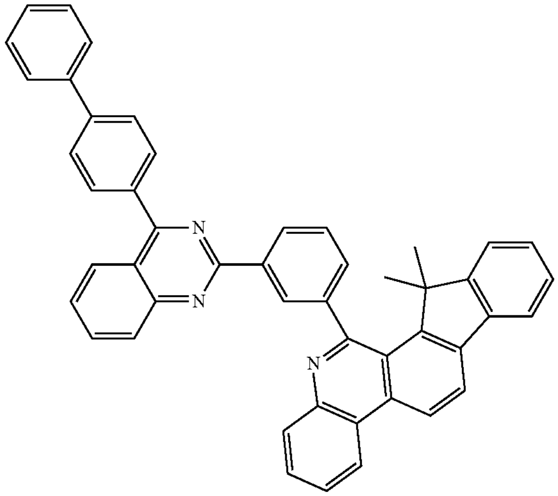
3-173
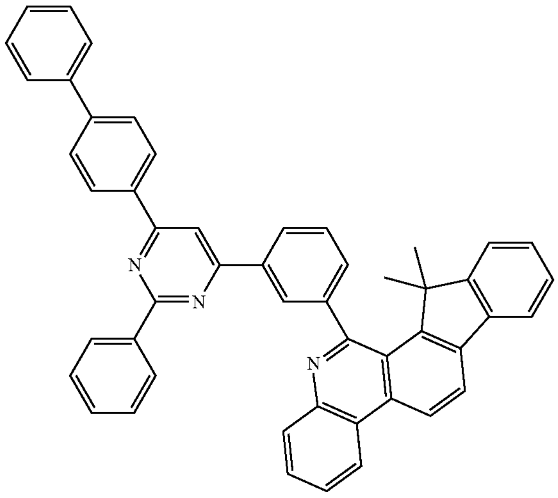
3-174
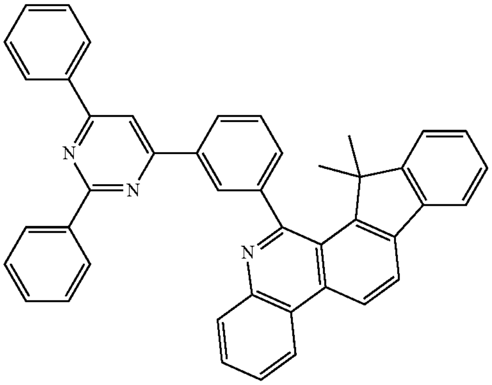

-continued
3-175
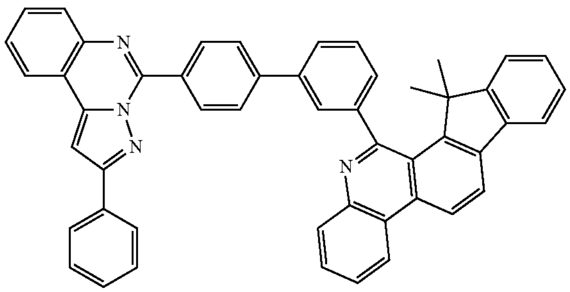
3-176
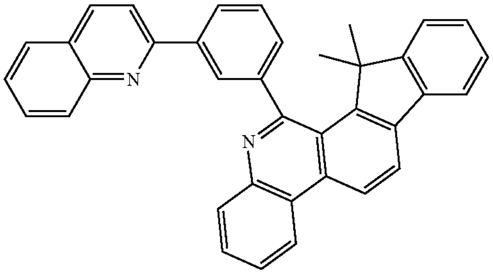
3-177
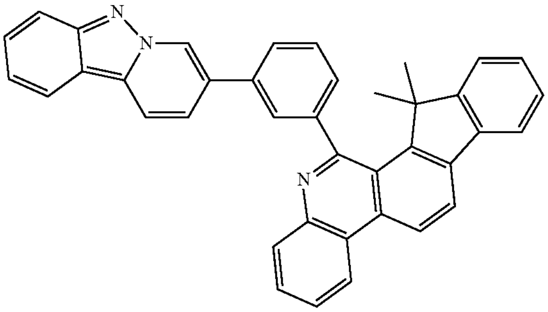
3-178
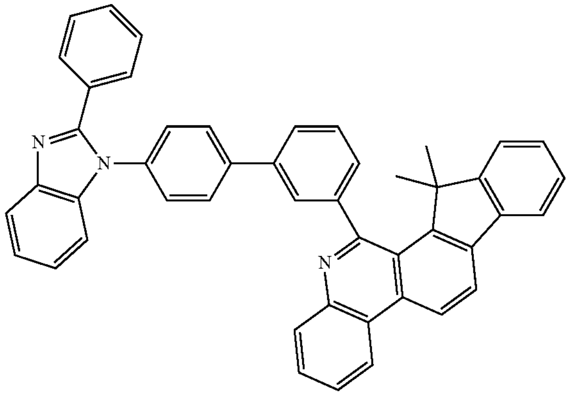
-continued
3-179
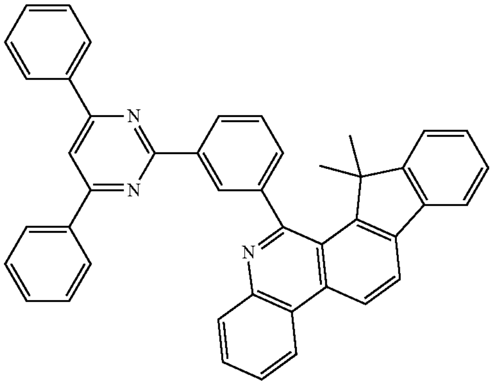
3-180
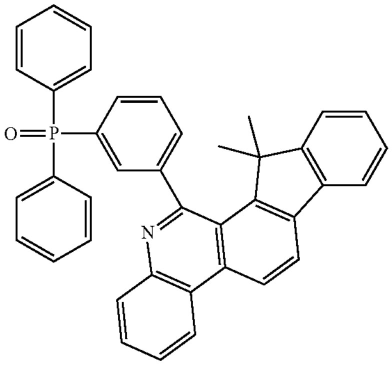
3-181
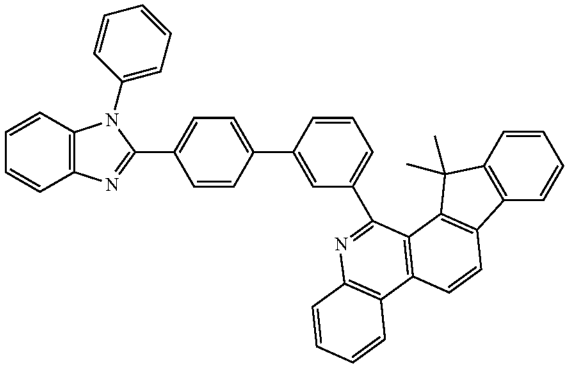
3-182
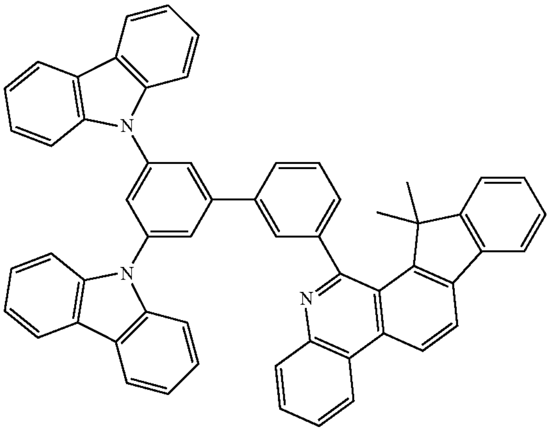

-continued
3-183
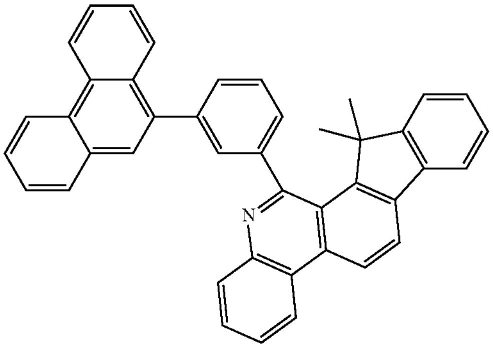
3-184
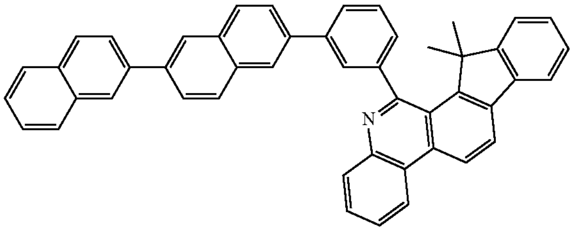
3-185
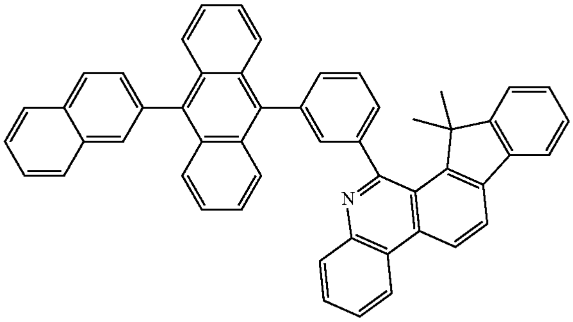
3-186
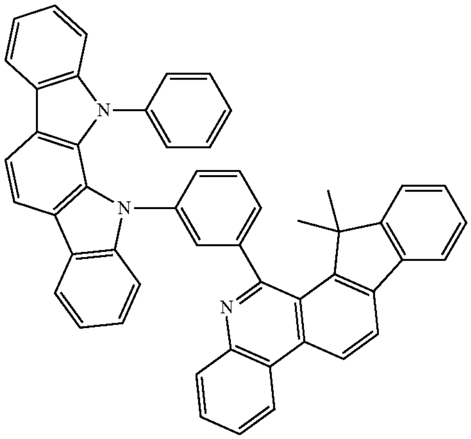
-continued
3-187
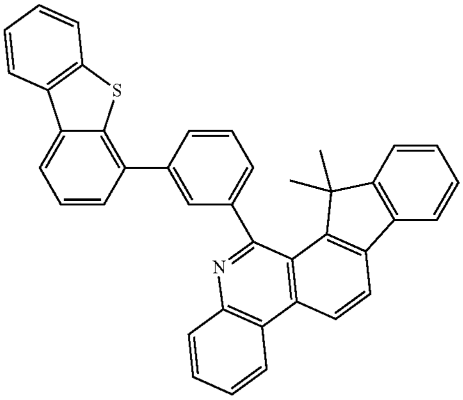
3-188
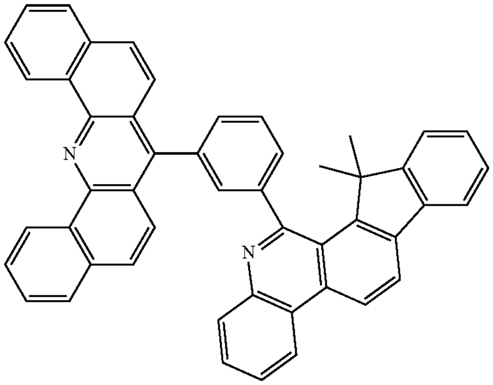
3-189
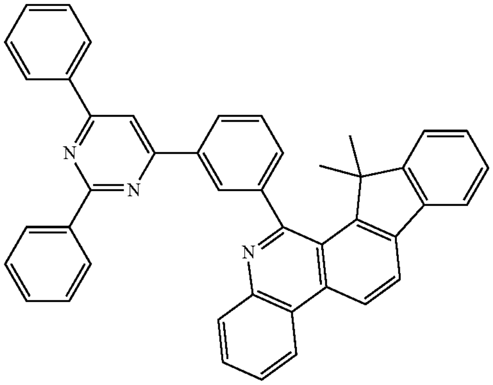
3-190
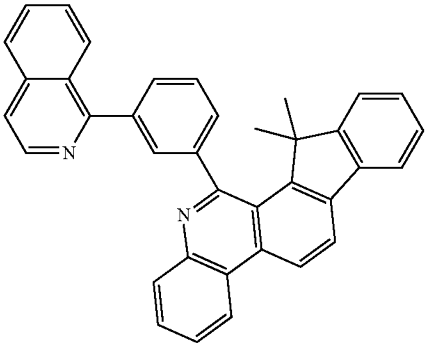

-continued
3-191
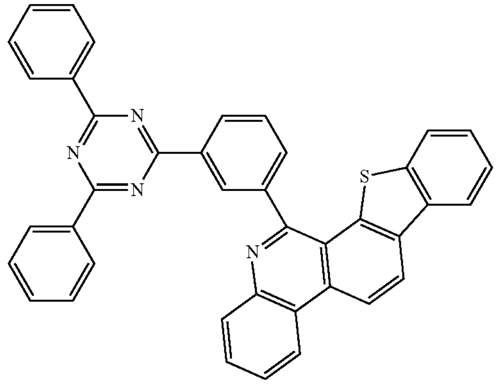
3-192
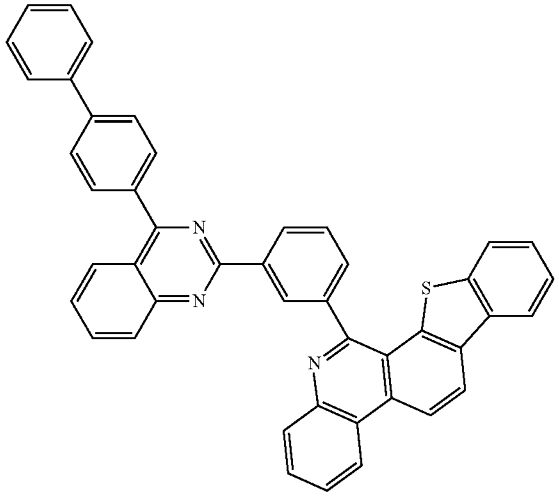
3-193
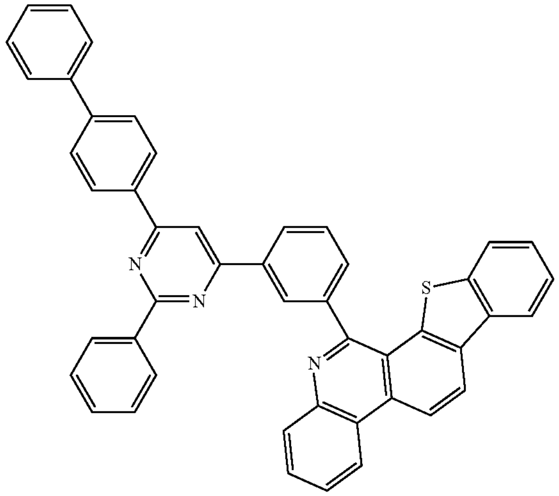
-continued
3-194
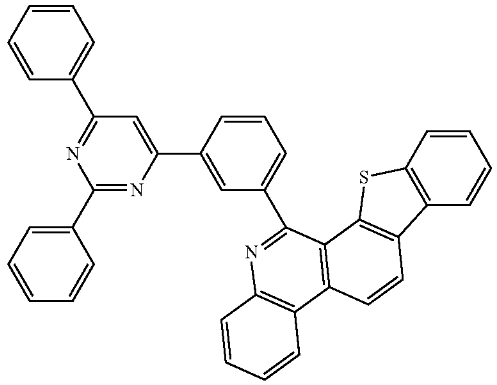
3-195
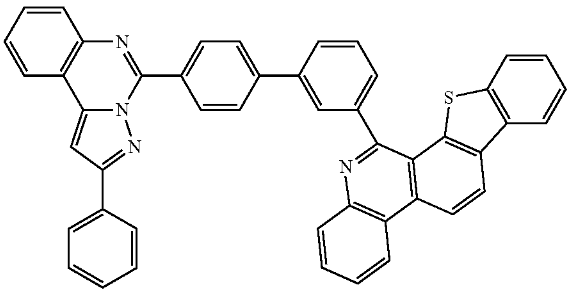
3-196
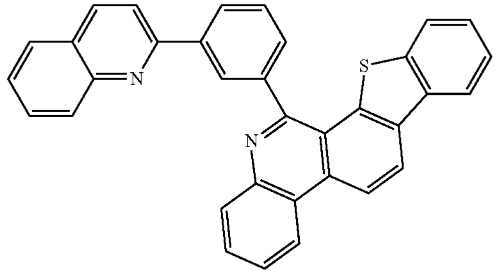
3-197
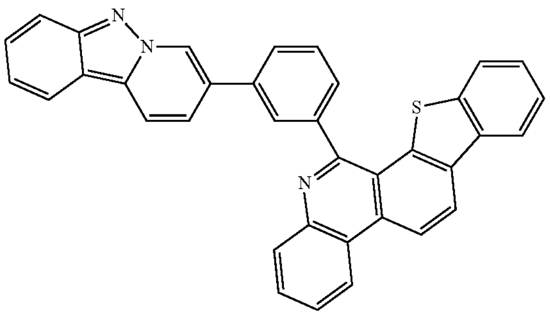

-continued
3-198
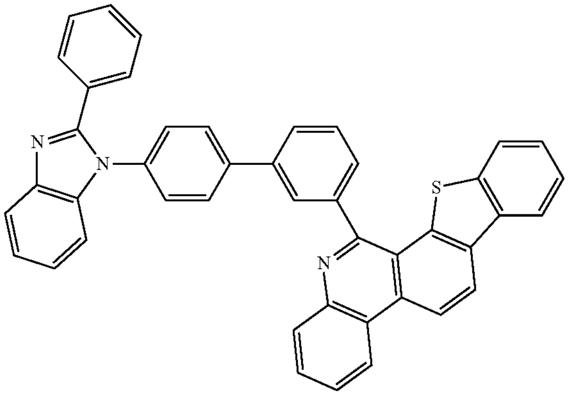
3-199
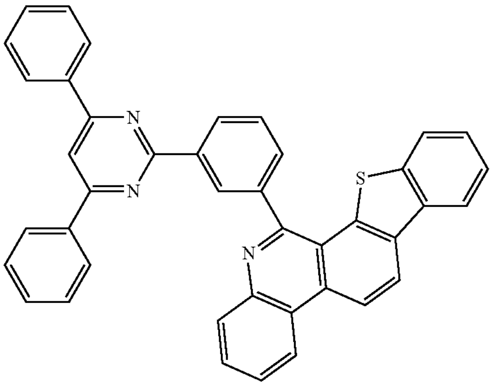
3-200
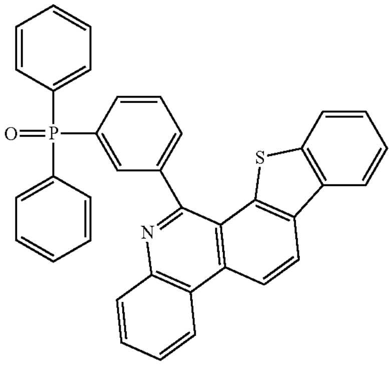
3-201
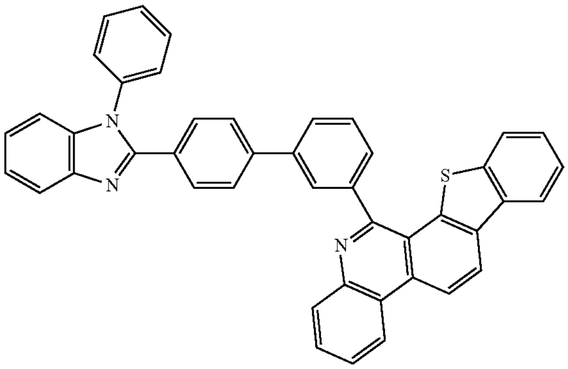
-continued
3-202
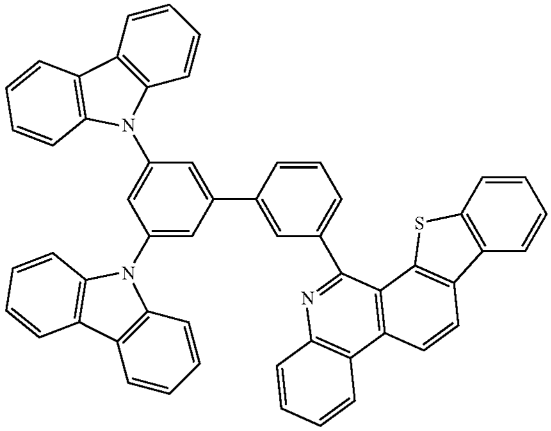
3-203
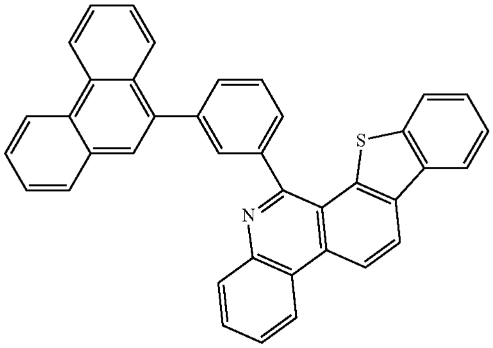
3-204
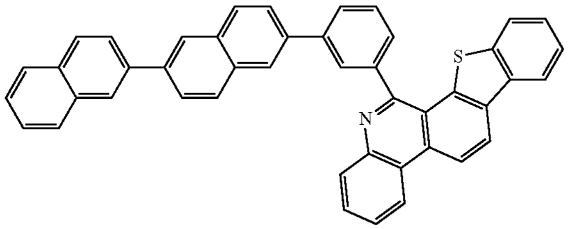
3-205
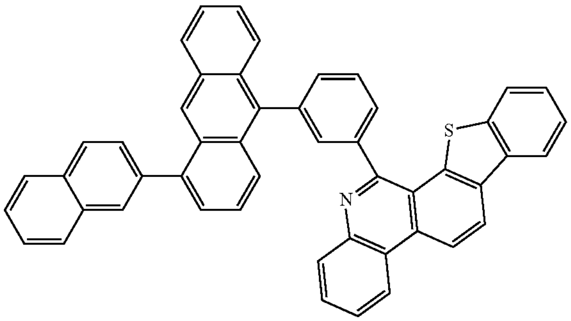

-continued
3-206
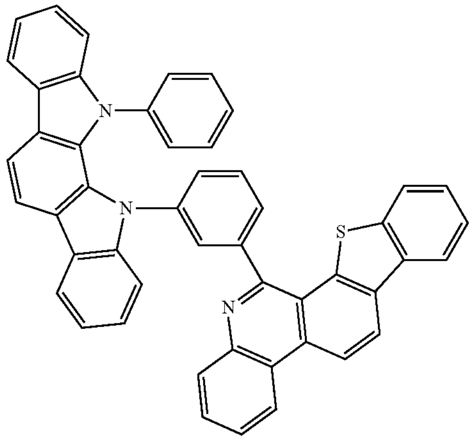
3-207
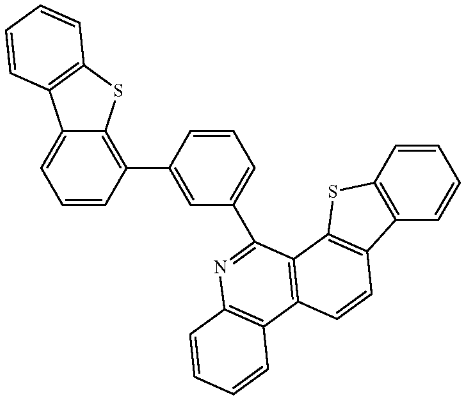
3-208
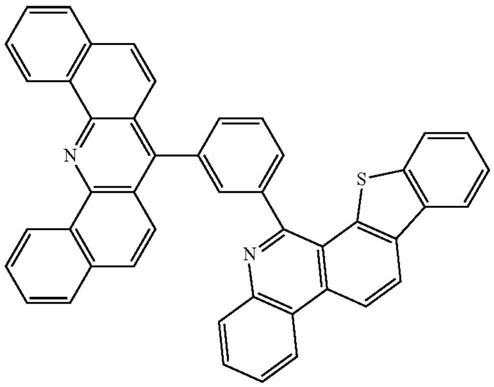
3-209
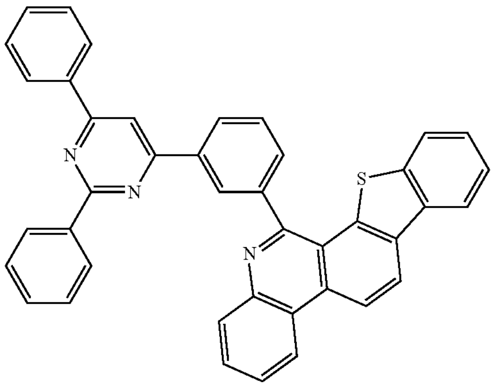
-continued
3-210
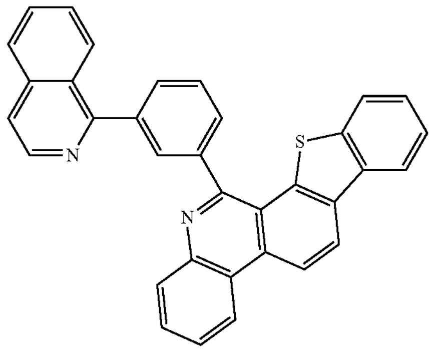
3-211
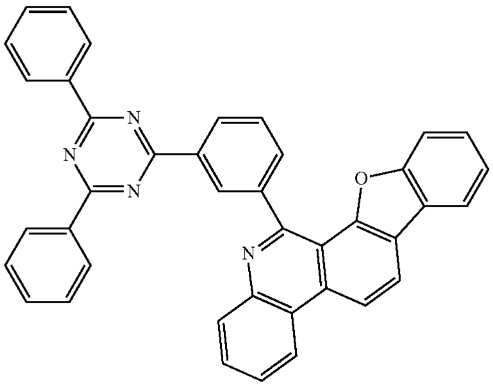
3-212
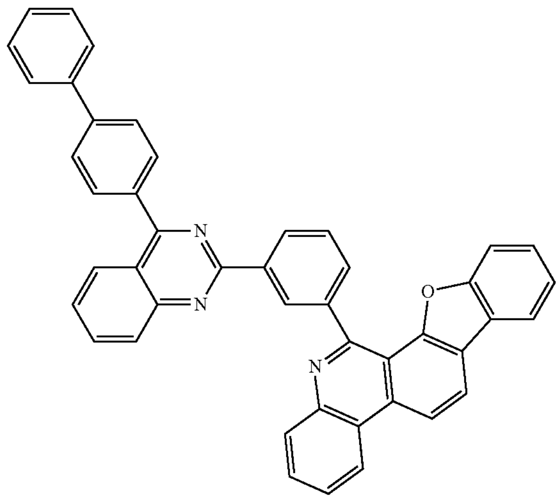

-continued
3-213
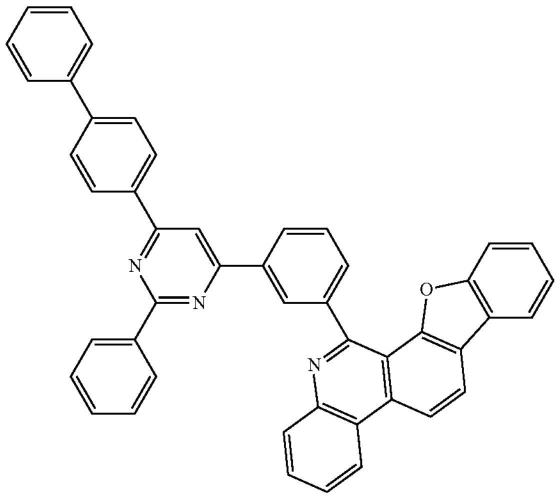
3-214
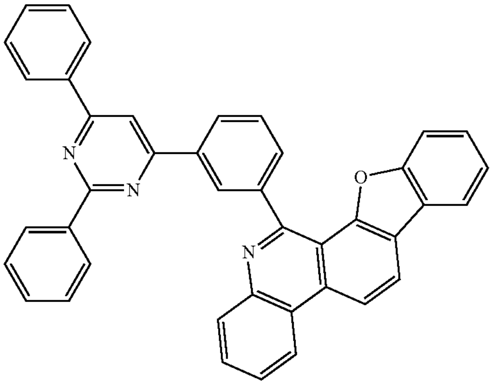
3-215
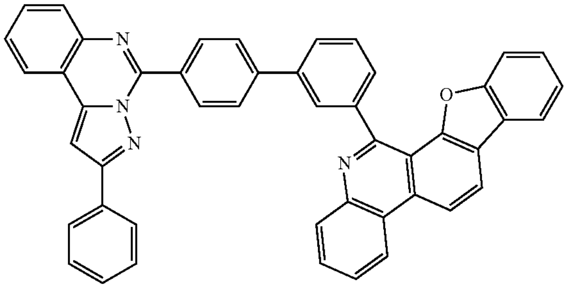
3-216
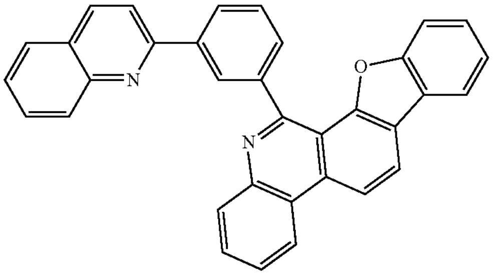
-continued
3-217
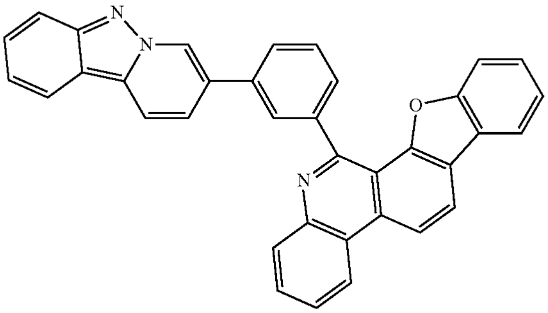
3-218
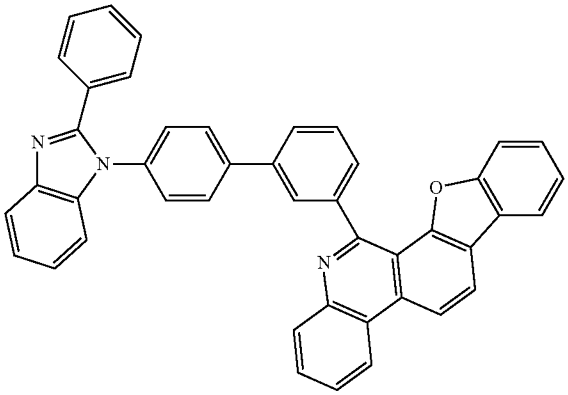
3-219
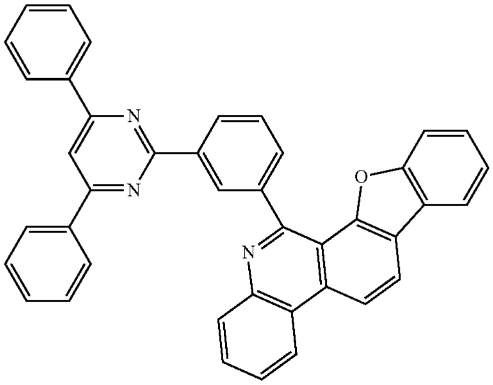
3-220
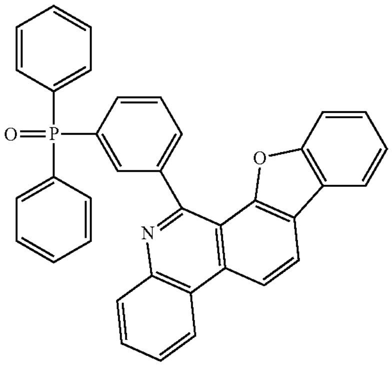

-continued
3-221
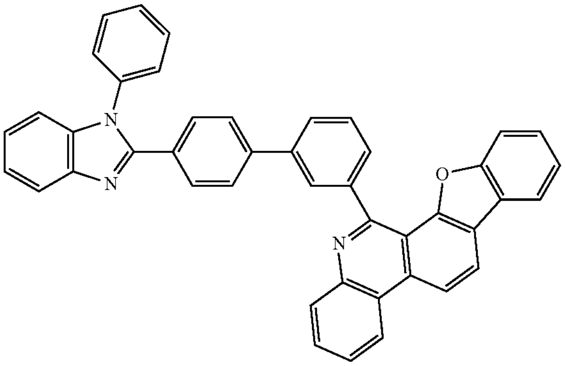
3-222
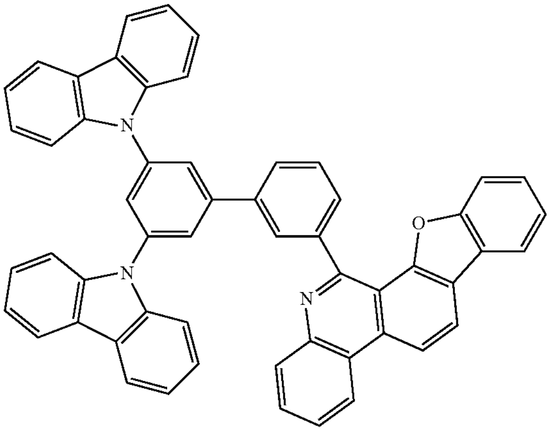
3-223
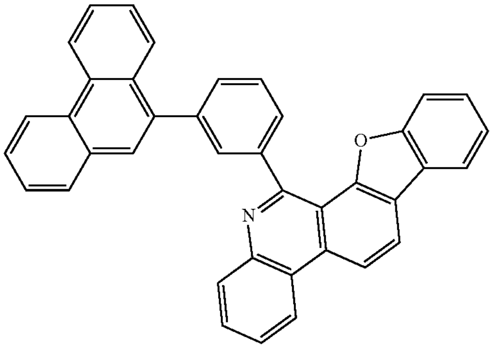
3-224
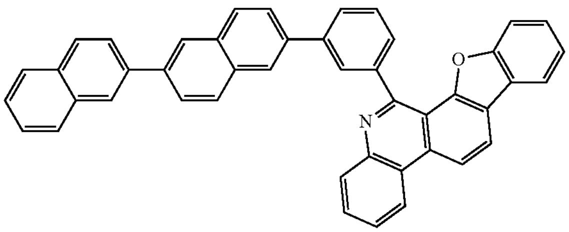
-continued
3-225
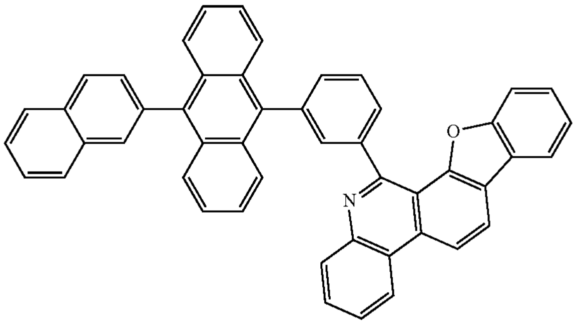
3-226
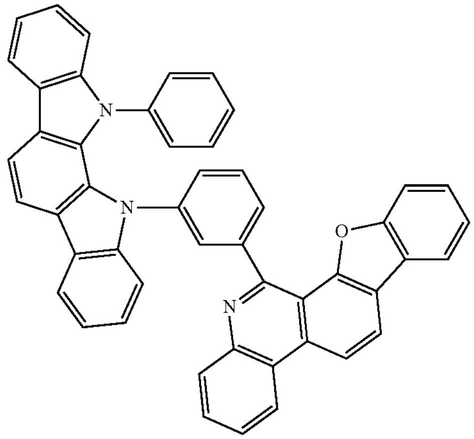
3-227
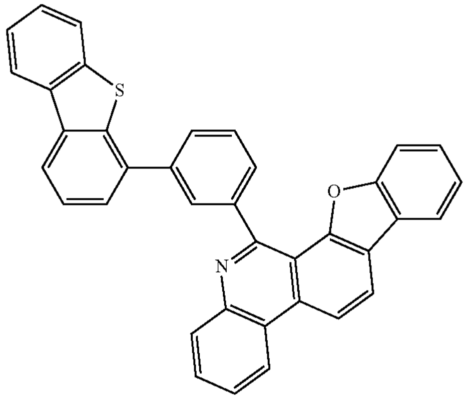
3-228
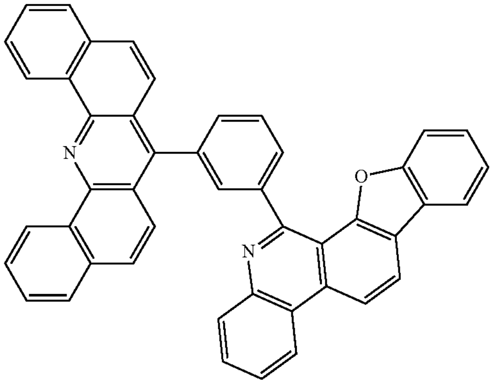

-continued
3-229
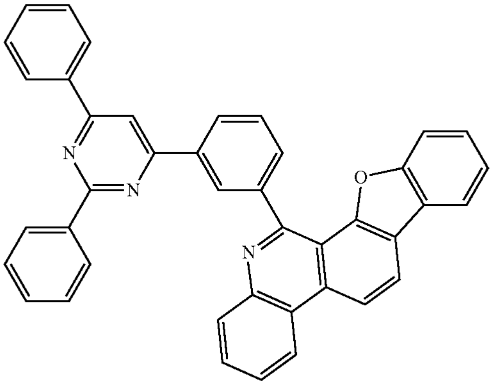
3-230
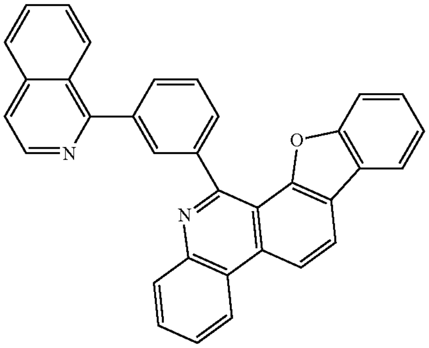
According to another exemplary embodiment of the present specification,
in Chemical Formula 20, Ar may be bonded to an atom bonded to a core of phenyl at a para position thereof, and Chemical Formula 20 may be selected from the following compounds.
3-231
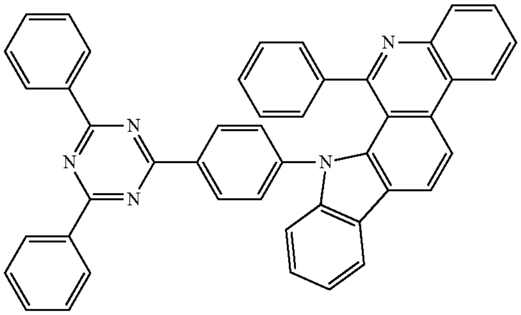
-continued
3-232
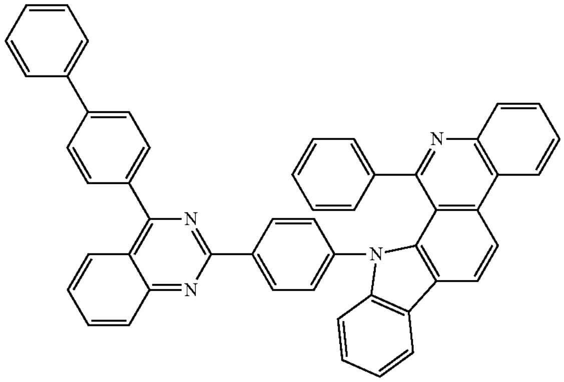
3-233
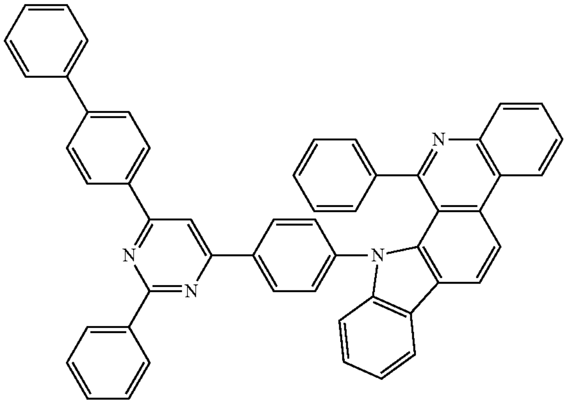
3-234
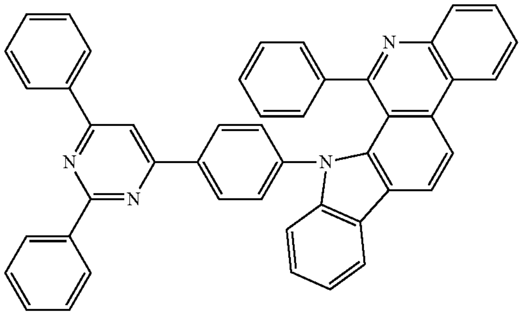
3-235
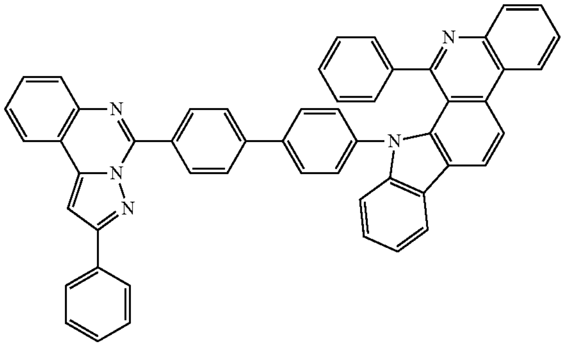

-continued
3-236
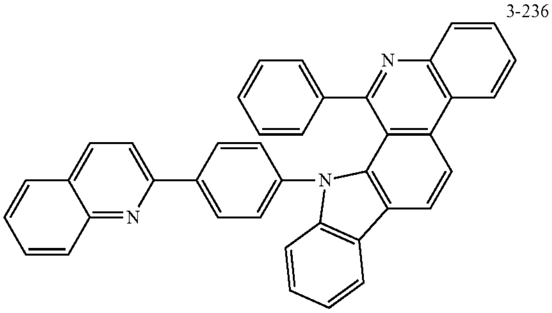
3-237
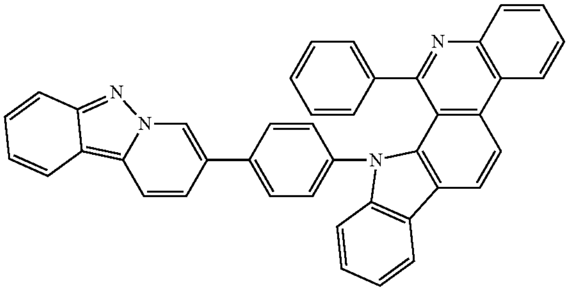
3-238
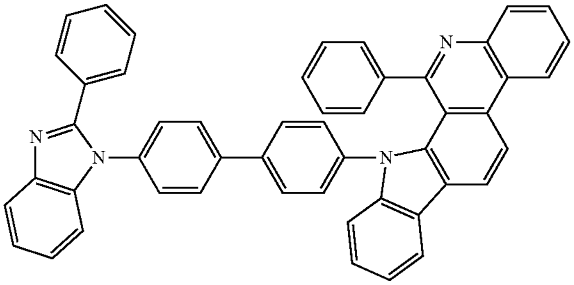
3-239
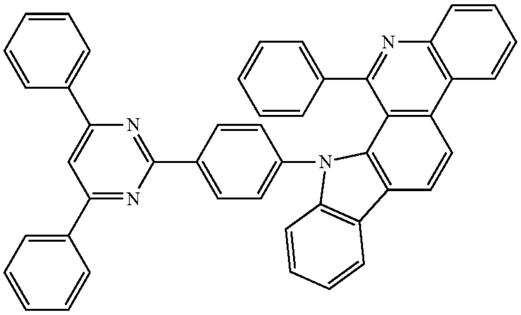
3-240
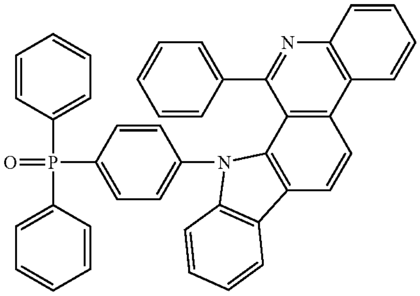
-continued
3-241
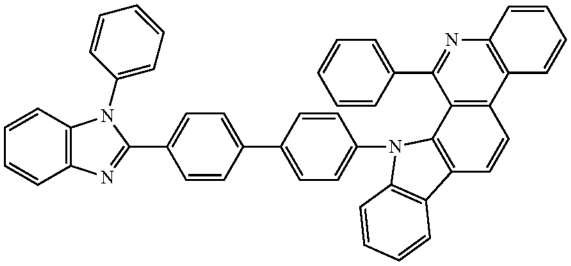
3-242
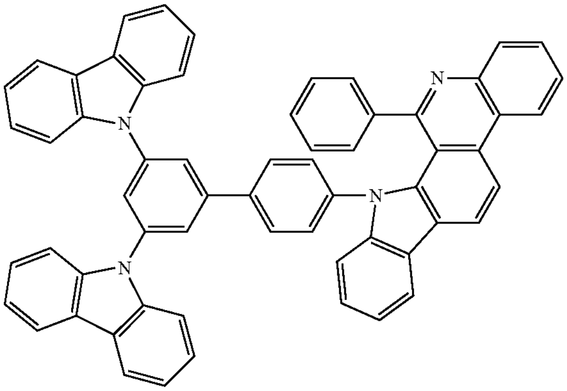
3-243
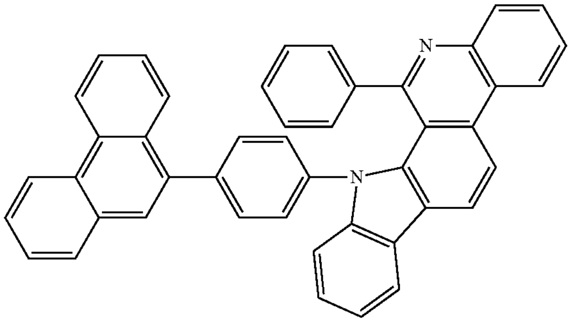
3-244
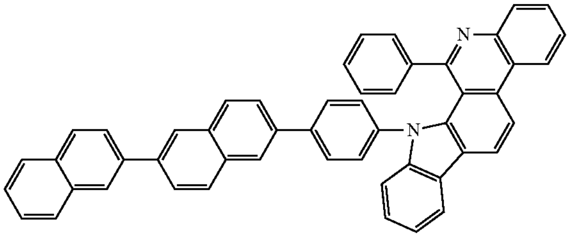
3-245
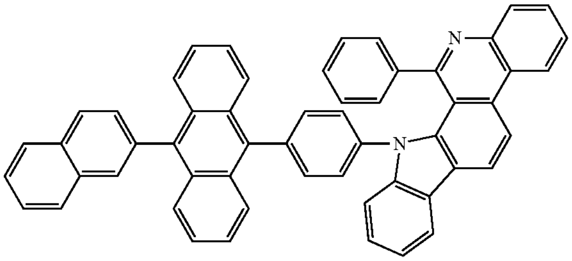

3-246
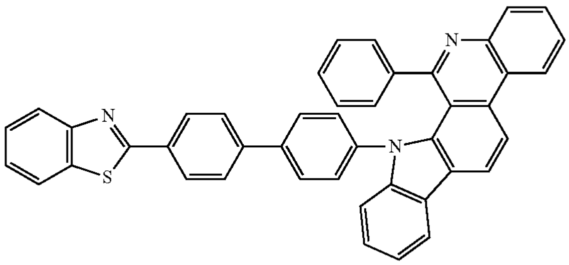
3-247
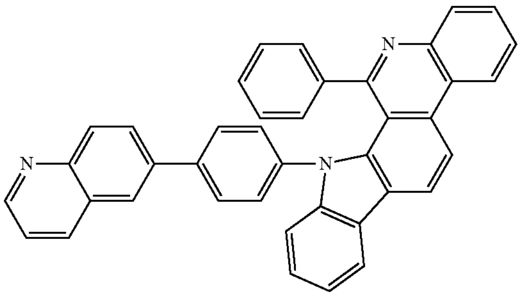
3-248
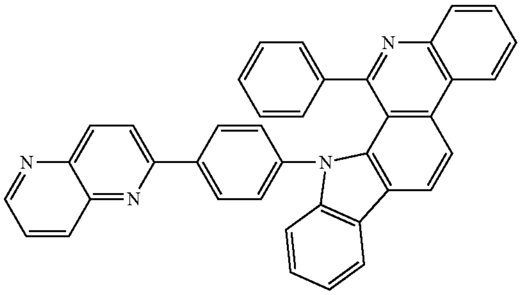
3-249
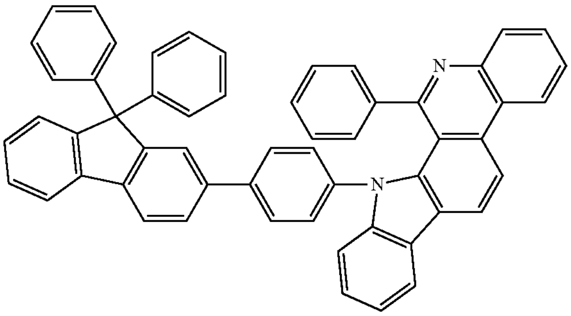
3-250
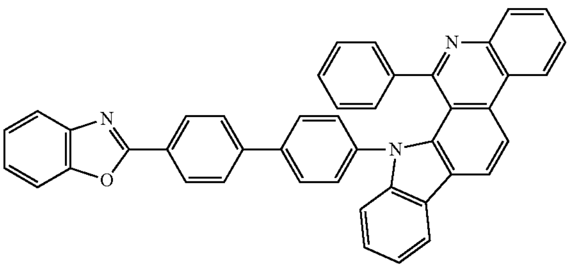
3-251
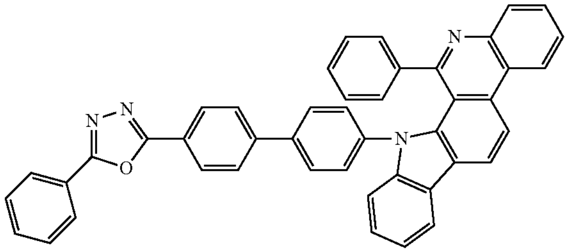
3-252
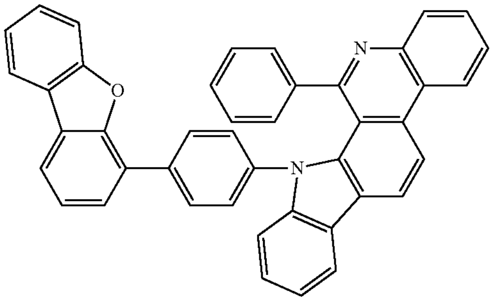
3-253
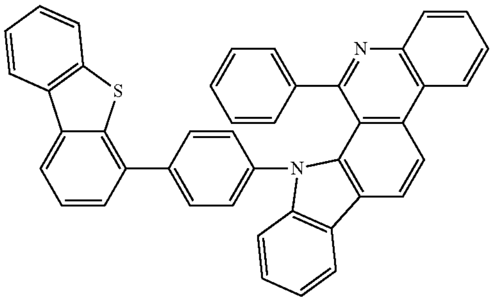
3-254
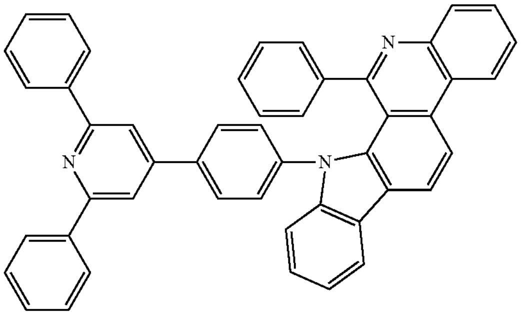
3-255
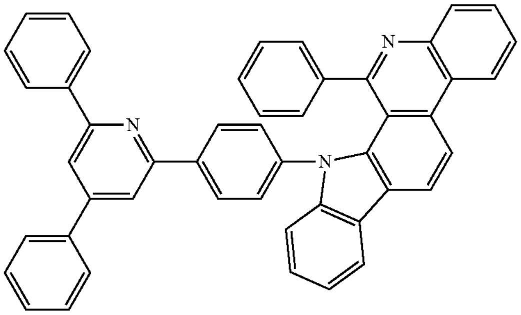

-continued
3-256
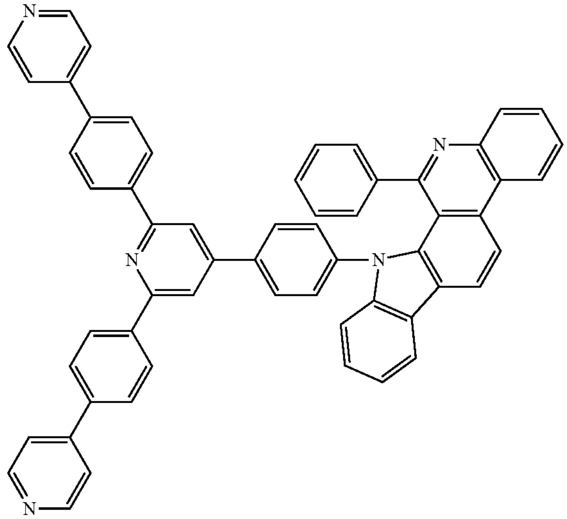
3-257
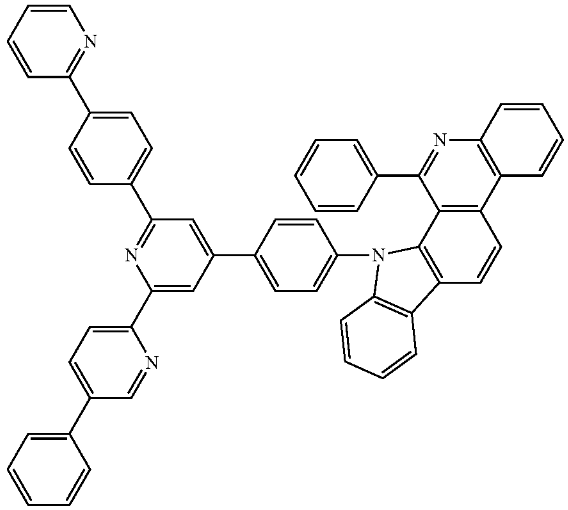
3-258
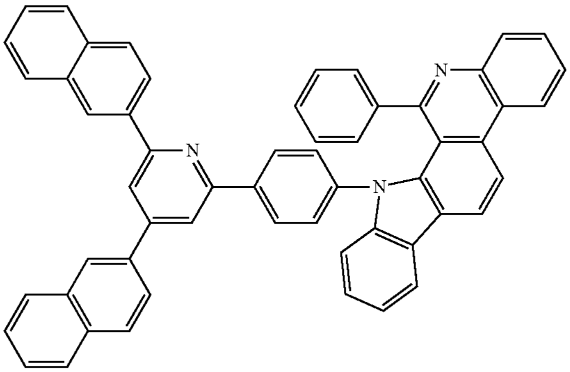
-continued
3-259
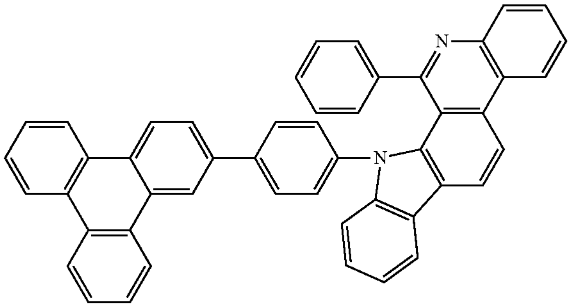
3-260
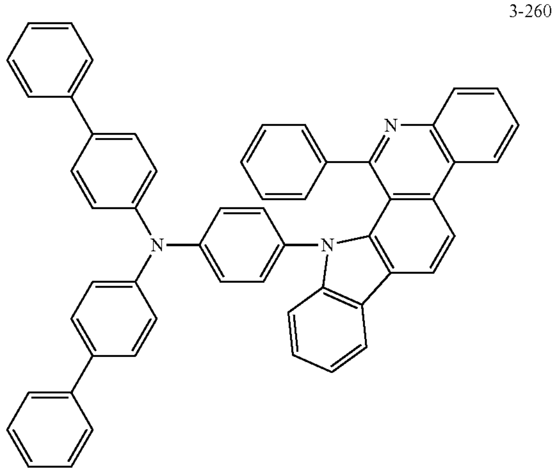
3-261
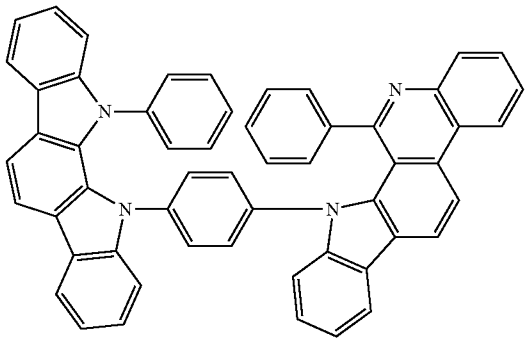
3-262
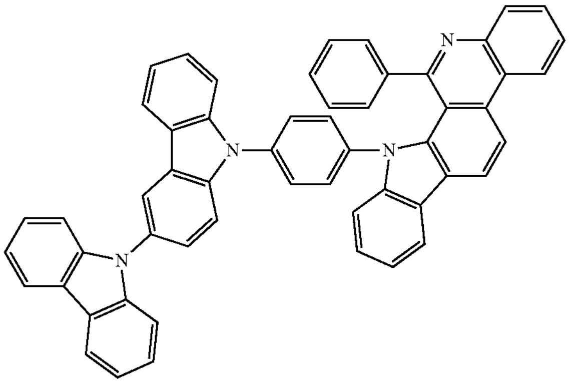

-continued
3-263
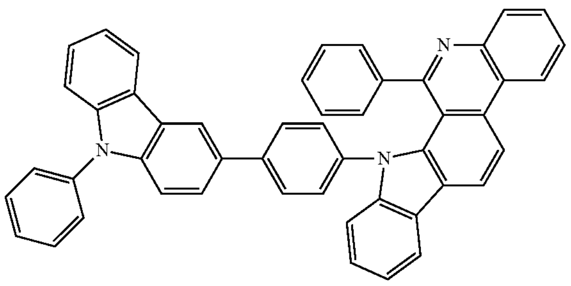
3-264
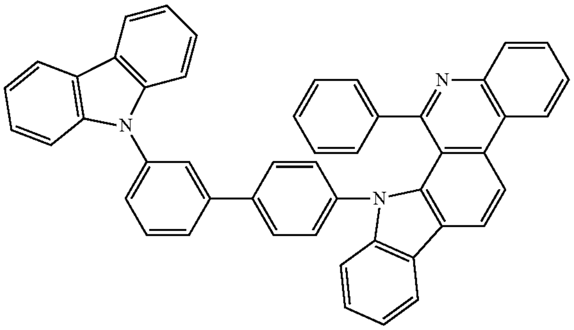
3-265
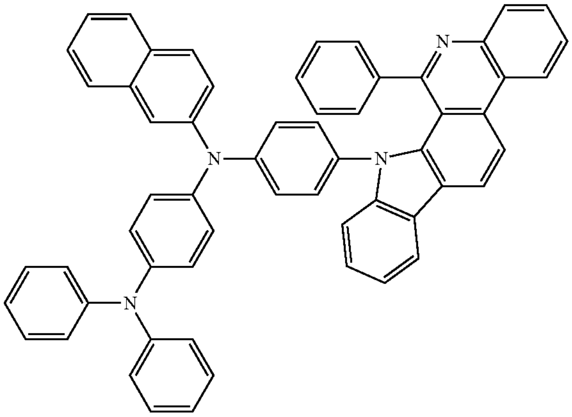
According to another exemplary embodiment of the present specification,
in Chemical Formula 20, Ar may be bonded to an atom bonded to a core of phenyl at a meta position thereof, and Chemical Formula 20 may be selected from the following compounds.
3-266
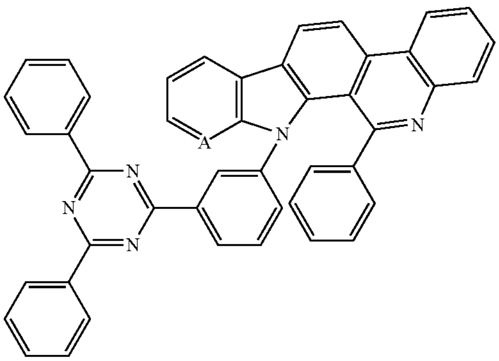
3-267
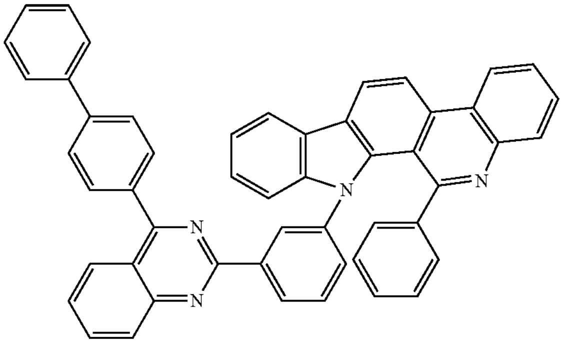
3-268
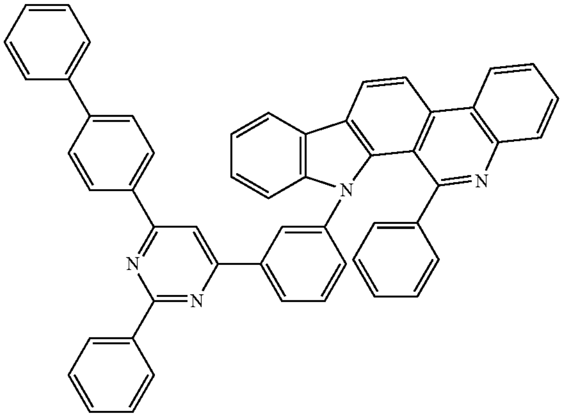
3-269
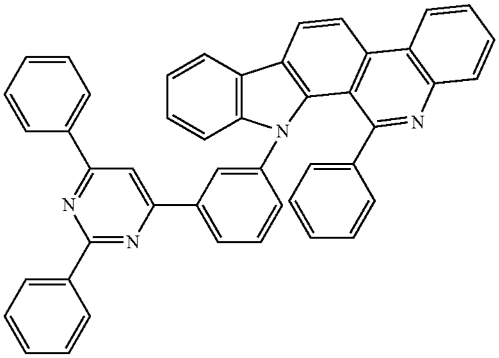

-continued
3-270
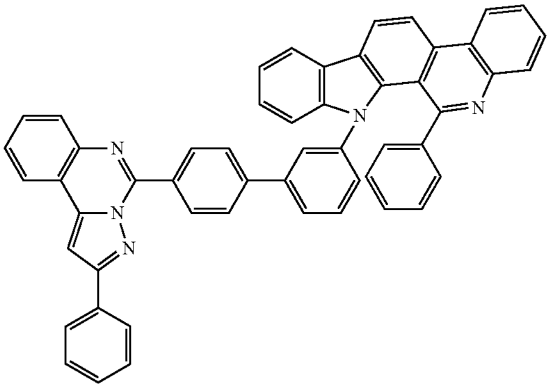
3-271
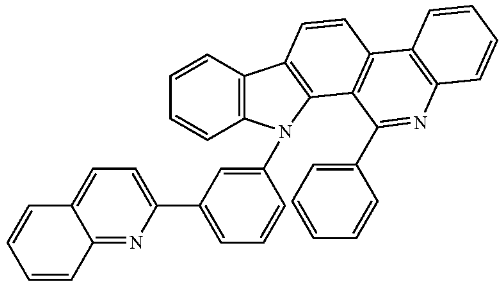
3-272
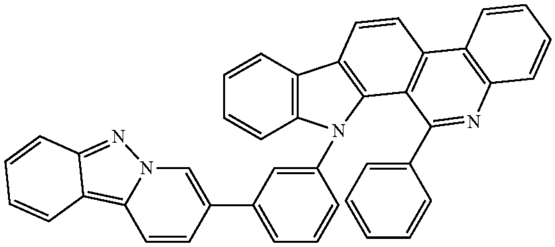
3-273
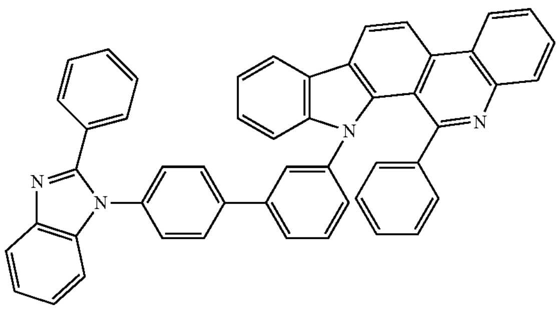
-continued
3-274
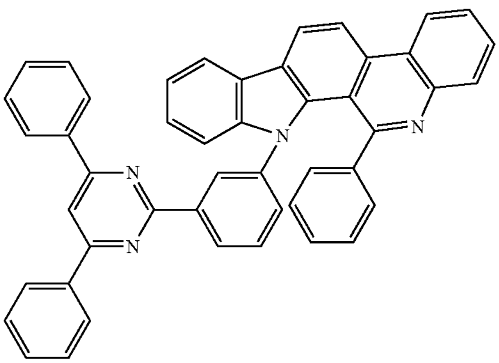
3-275
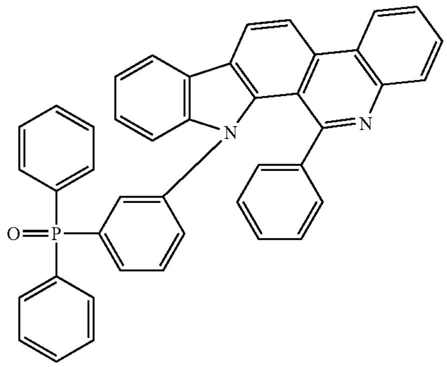
3-276
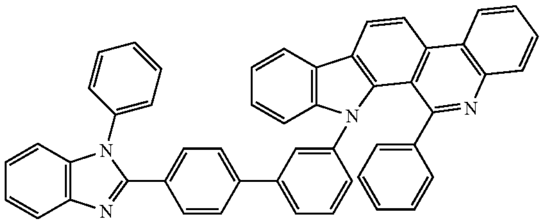
3-277
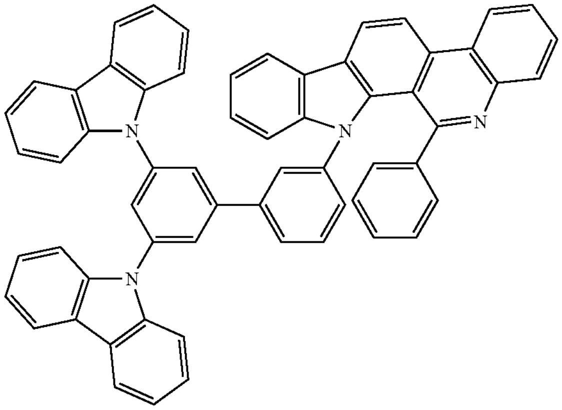

-continued
3-278
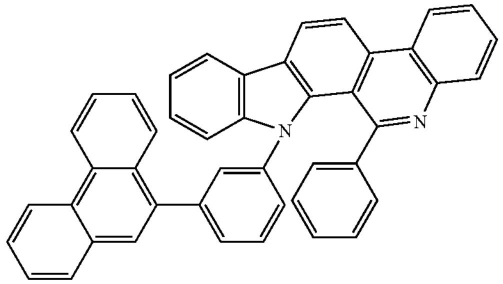
3-279
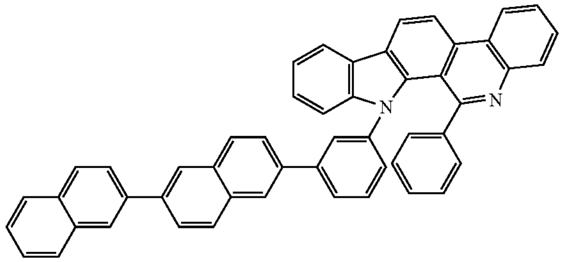
3-280
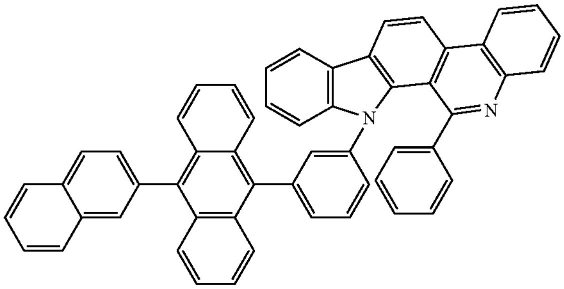
3-281
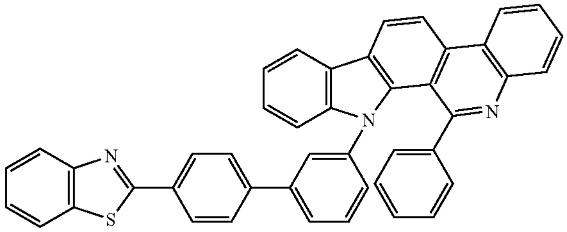
3-282
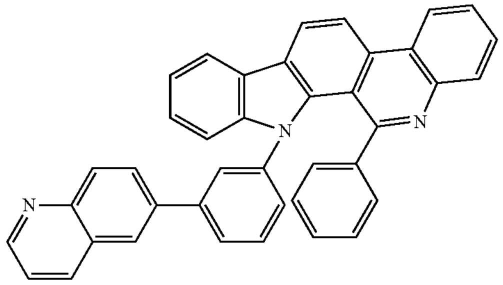
-continued
3-283
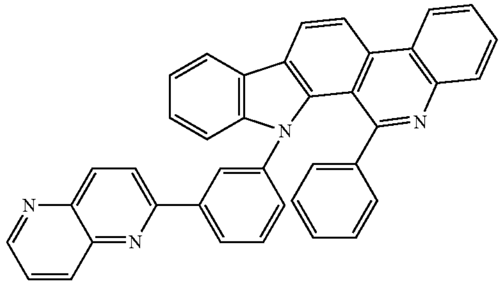
3-284
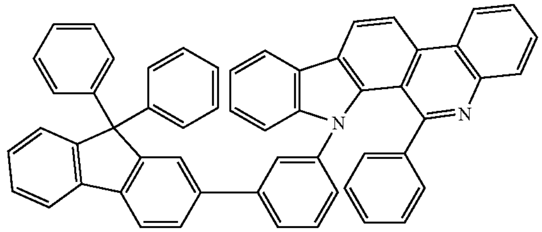
3-285
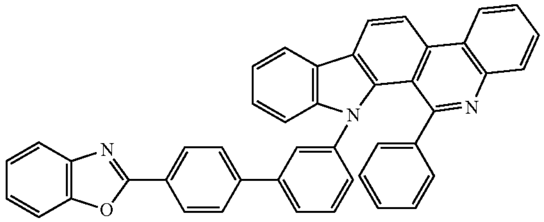
3-286
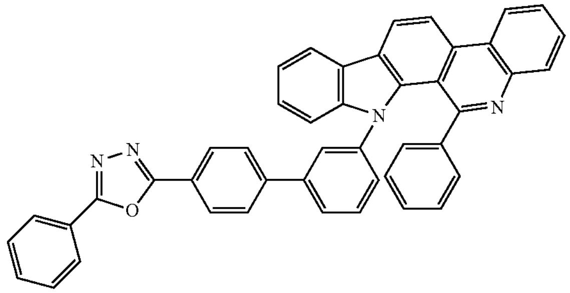
3-287
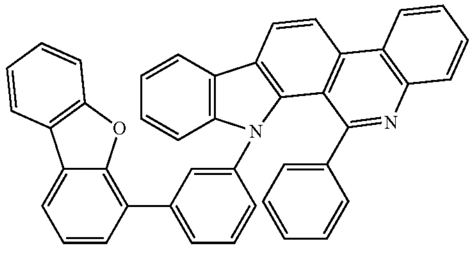
3-288
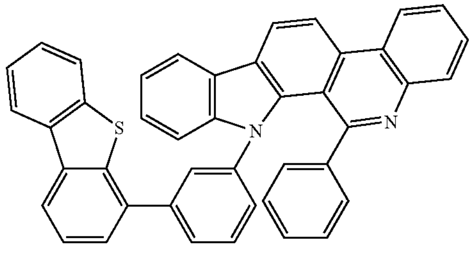

-continued
3-289
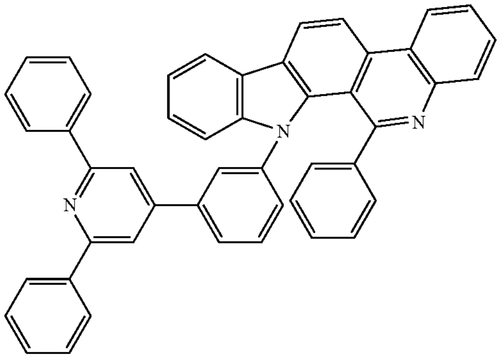
3-290
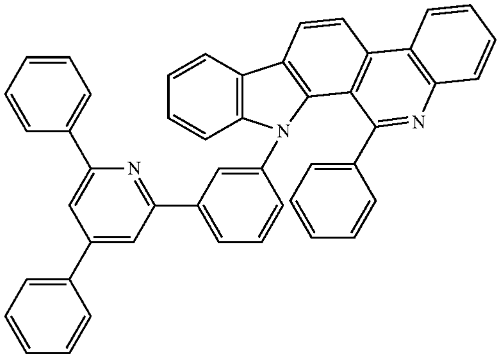
3-291
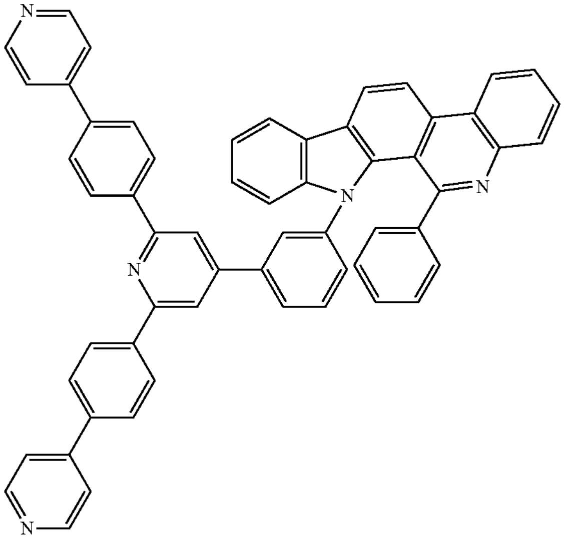
-continued
3-292
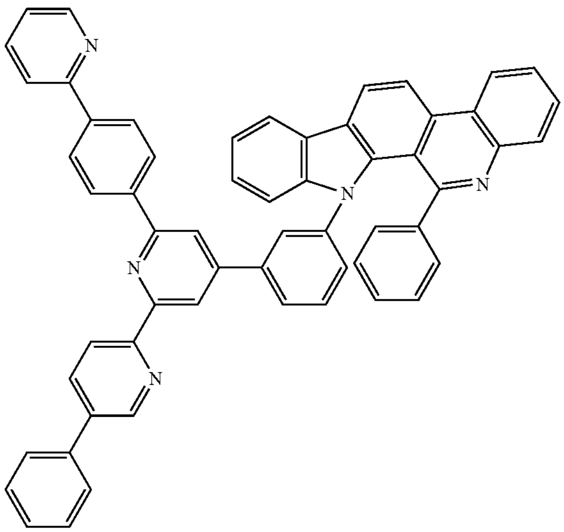
3-293
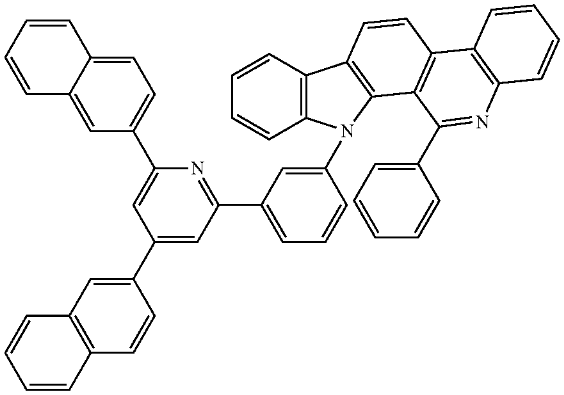
3-294
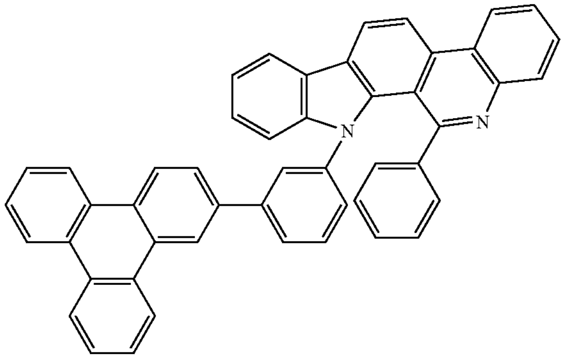

-continued
3-295
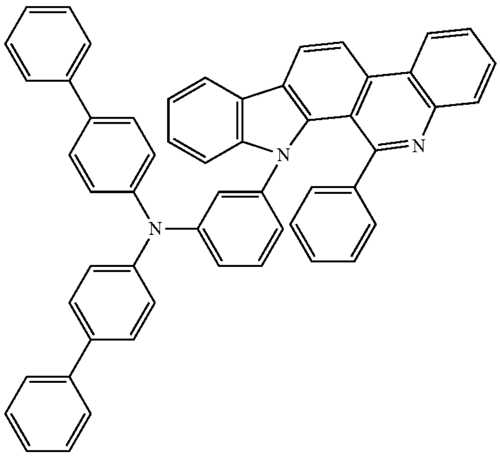
3-296
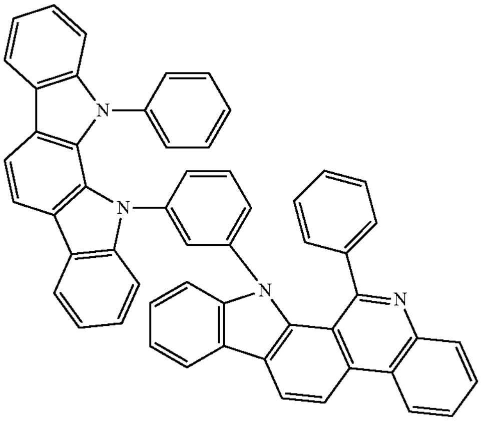
3-297
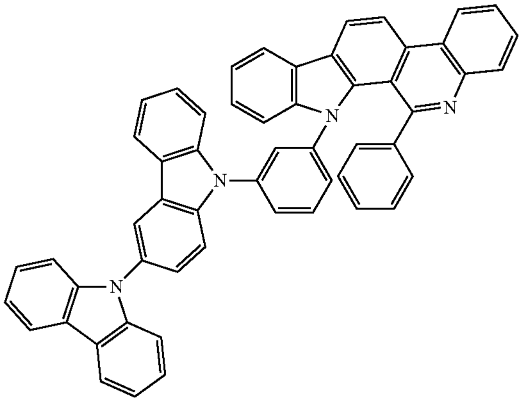
3-298
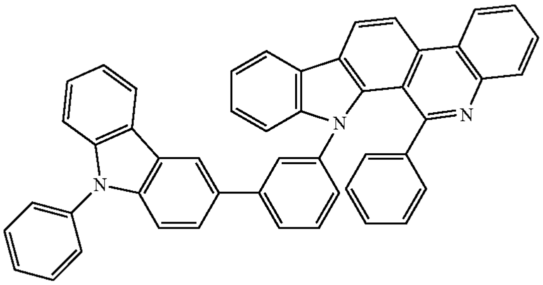
-continued
3-299
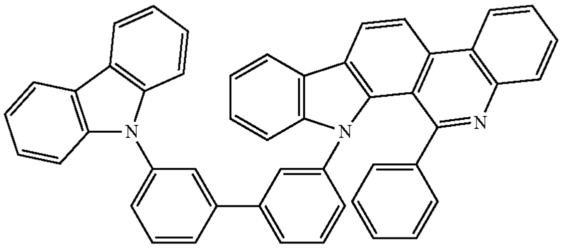
3-300
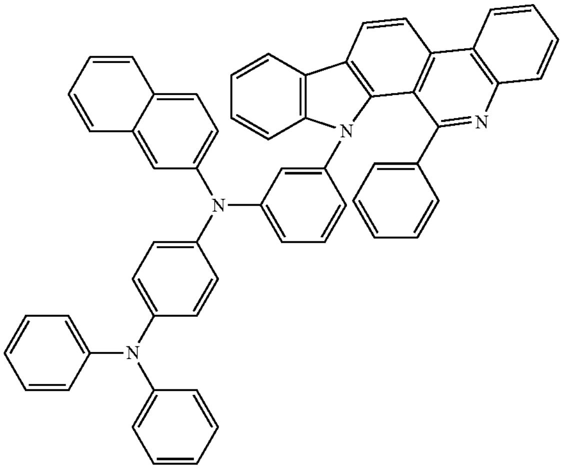
According to another exemplary embodiment of the present specification,
in Chemical Formulas 24 and 30, Ar may be bonded to an atom bonded to a core of phenyl at a para position thereof, and Chemical Formulas 24 and 30 may be selected from the following compounds.
4-1
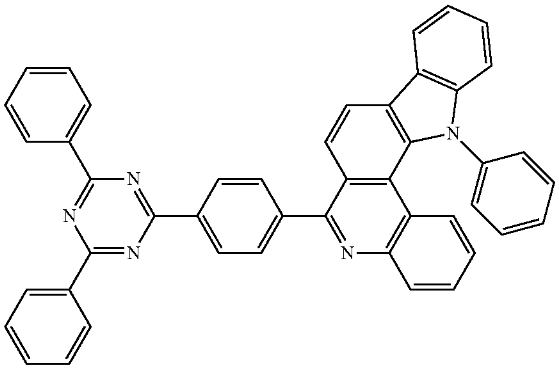

4-2
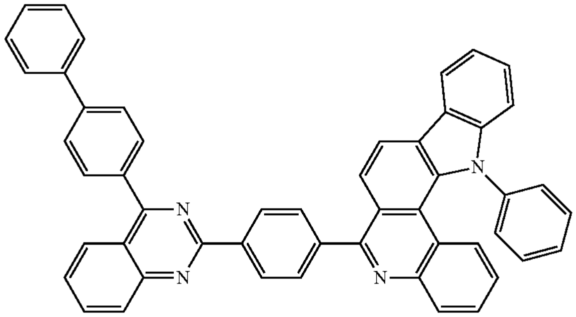
4-3
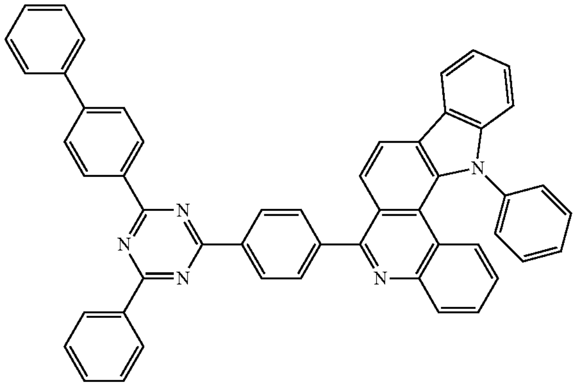
4-4
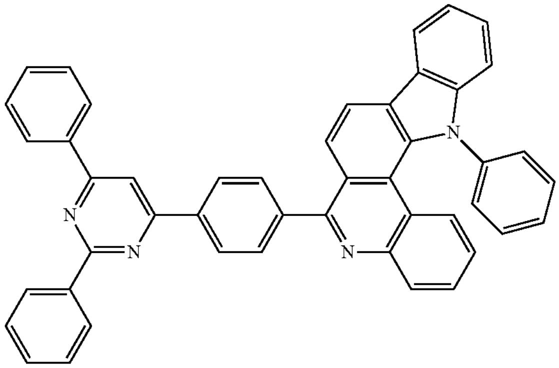
4-5
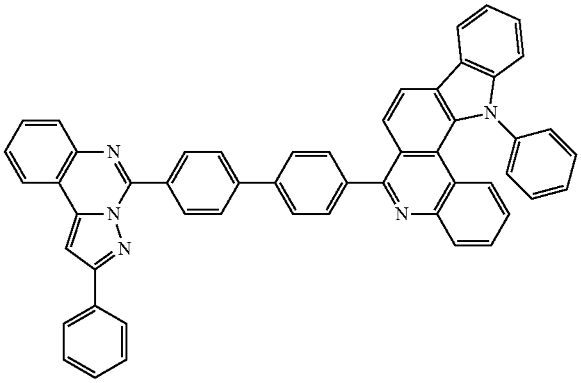
4-6
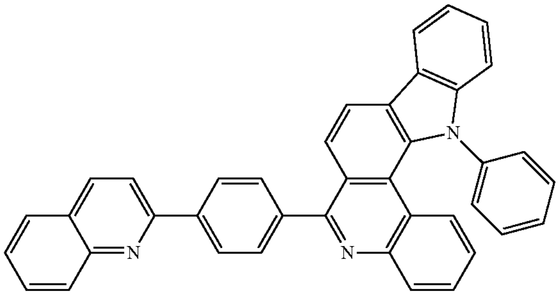
4-7
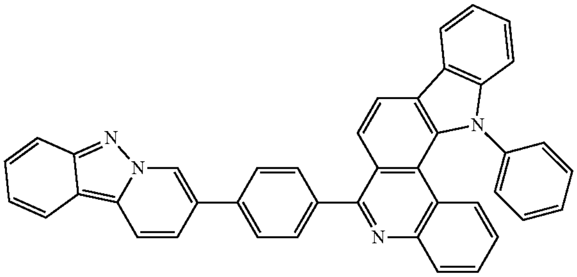
4-8
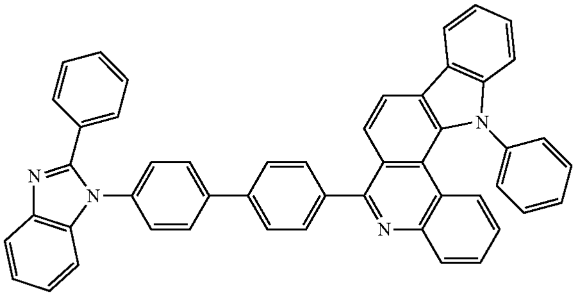
4-9
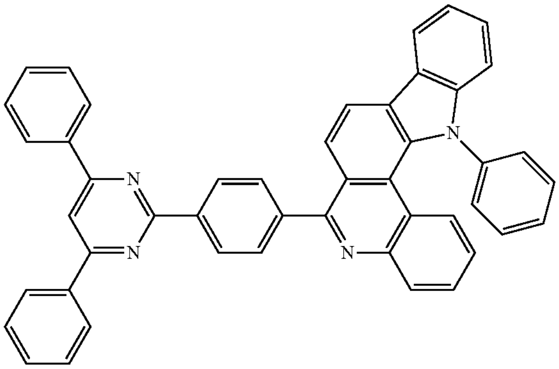

-continued
4-10
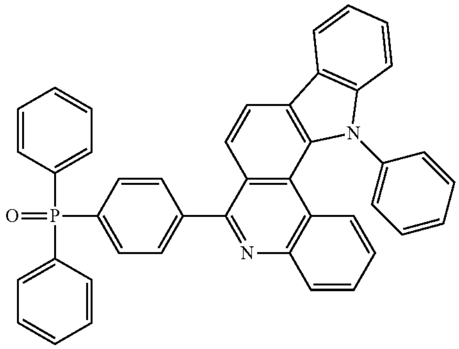
4-11
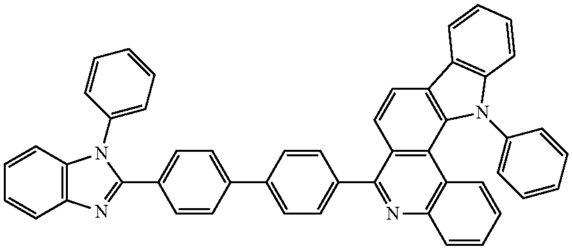
4-12
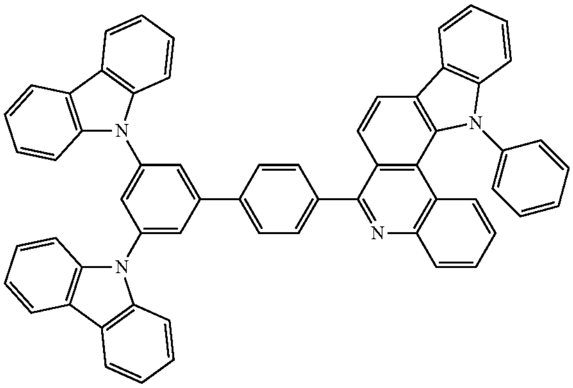
4-13
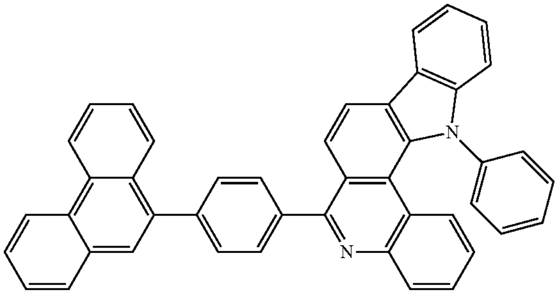
4-14
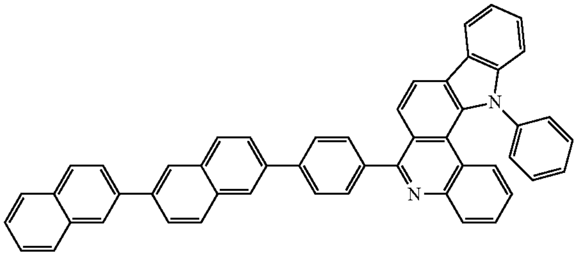
-continued
4-15
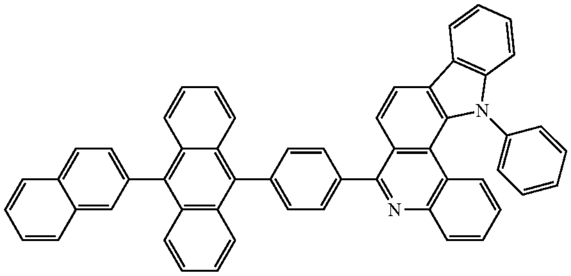
4-16
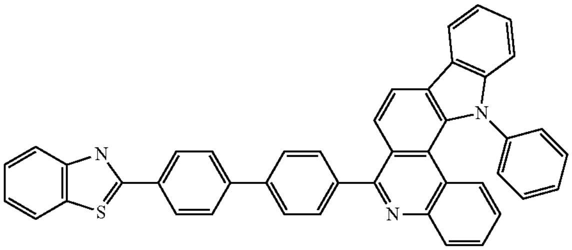
4-17
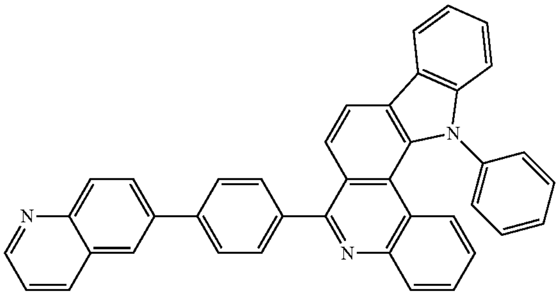
4-18
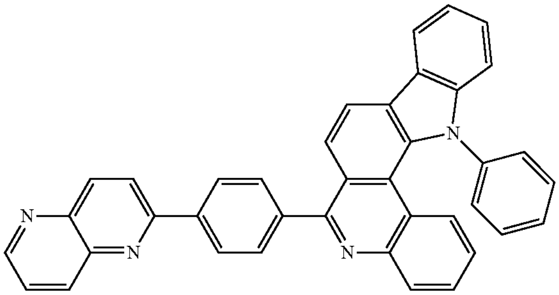
4-19
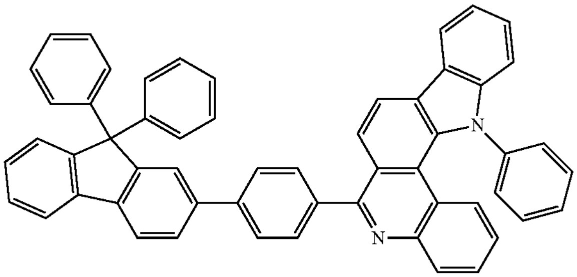

4-20
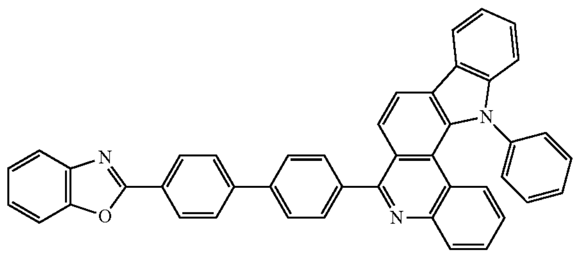
4-21
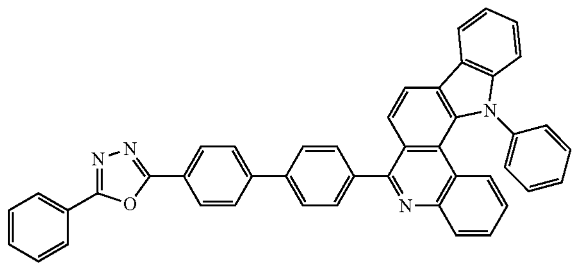
4-22
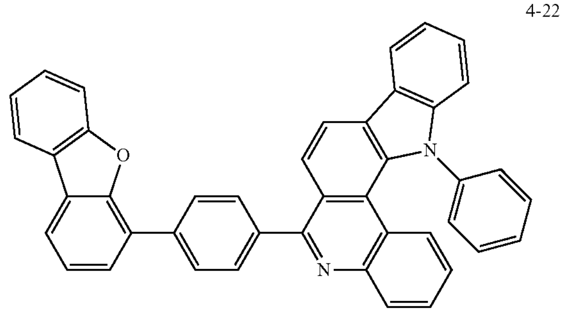
4-23
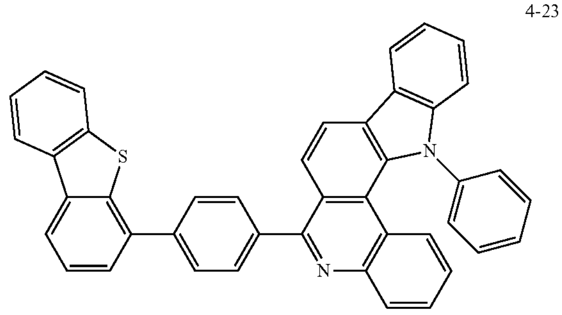
4-24
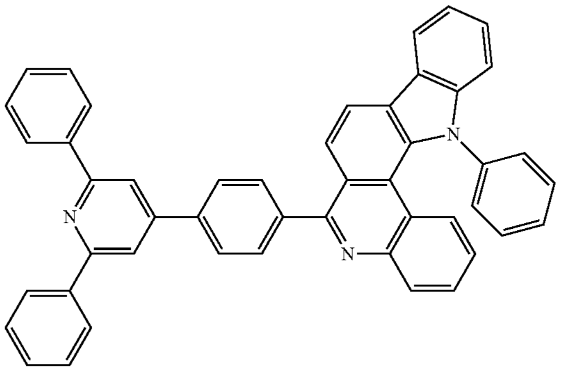
4-25
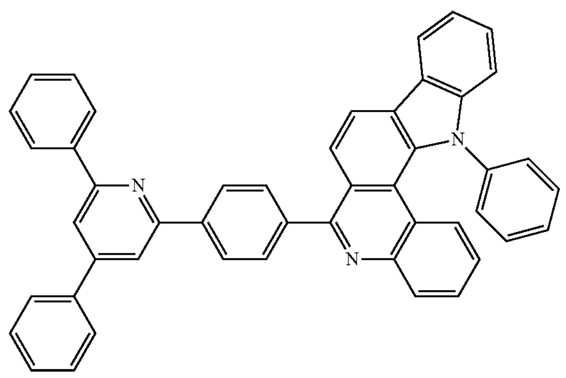
4-26
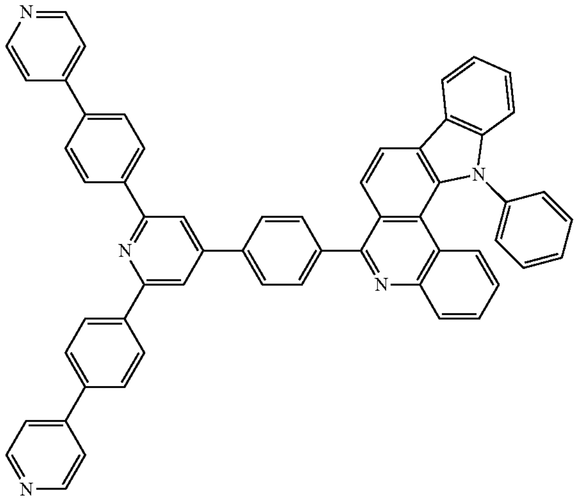
4-27
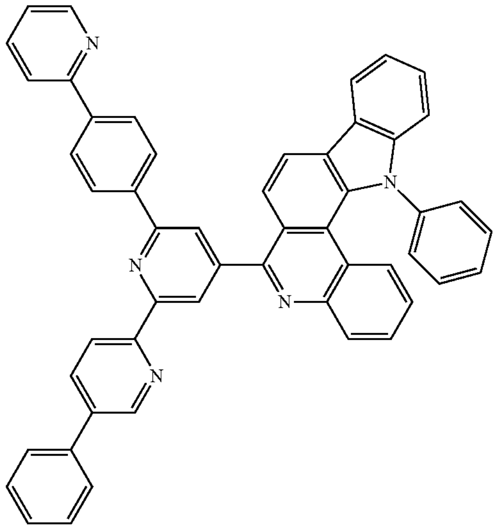

-continued
4-28
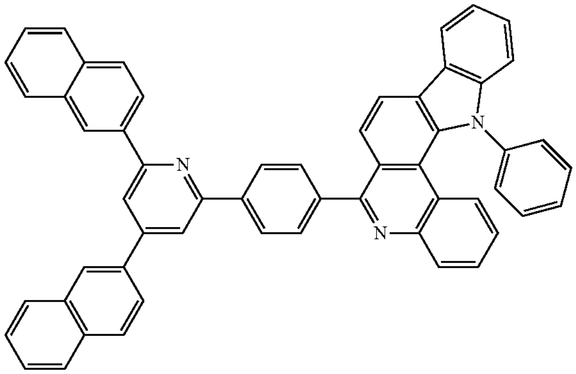
4-29
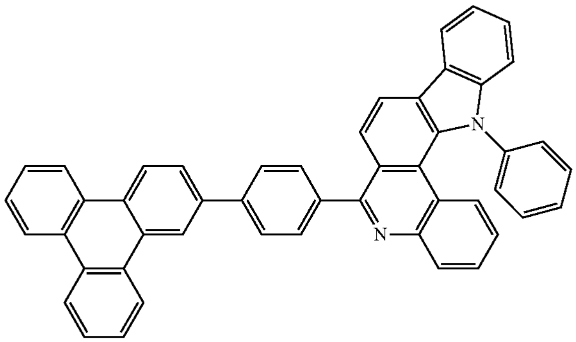
4-30
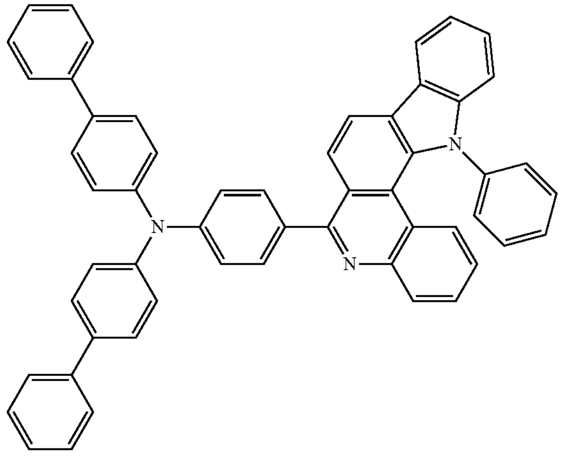
4-31
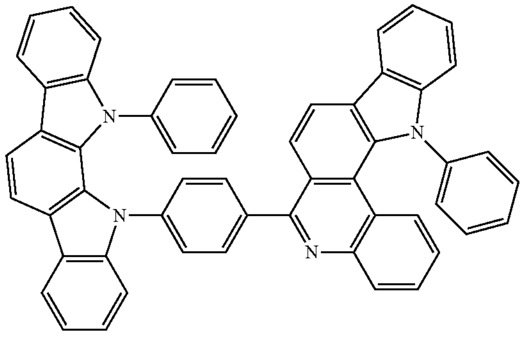
-continued
4-32
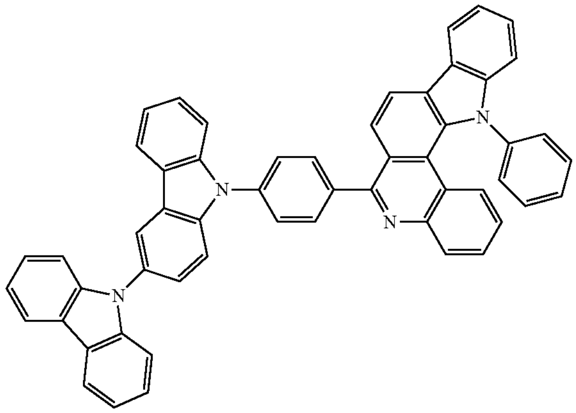
4-33
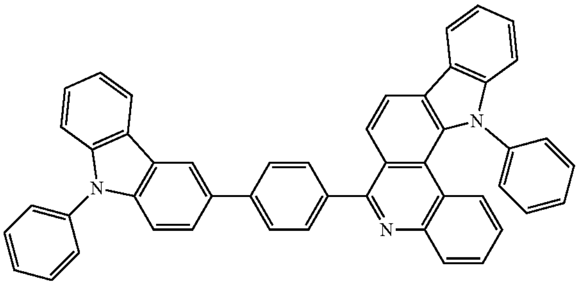
4-34
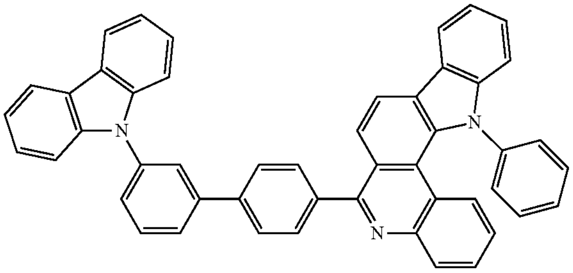
4-35
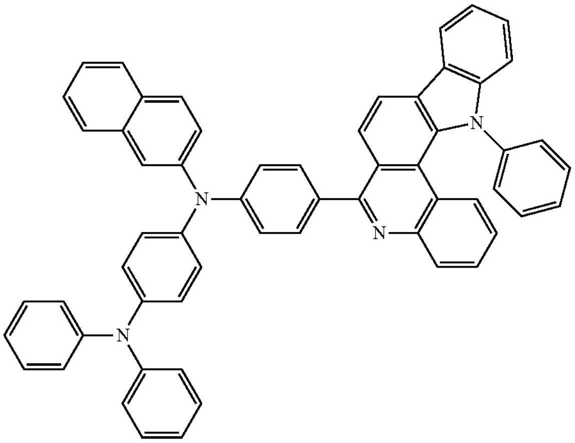

-continued
4-36
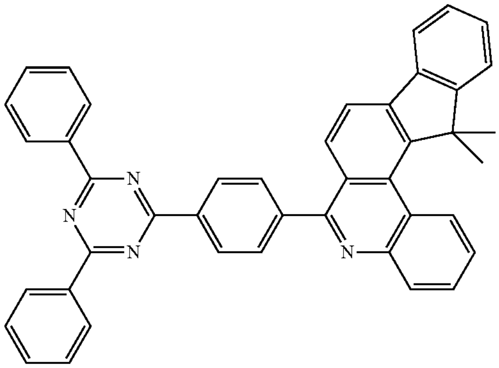
4-37
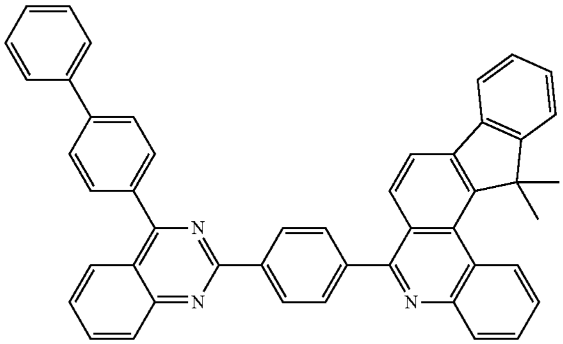
4-38
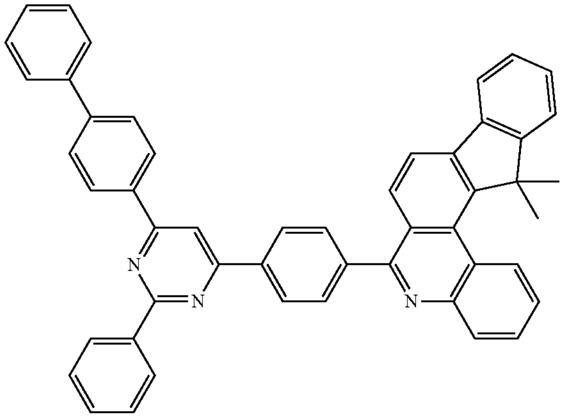
4-39
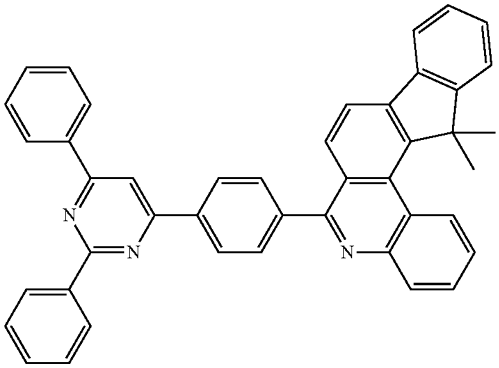
-continued
4-40
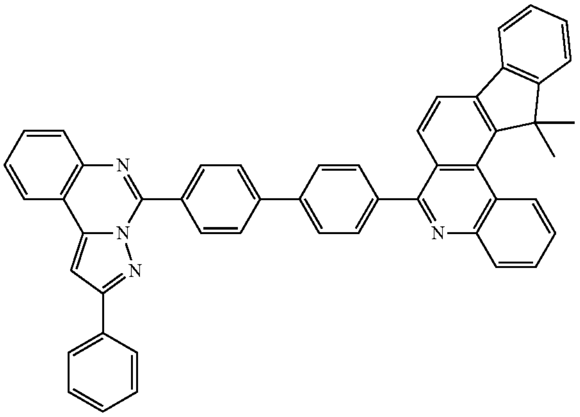
4-41
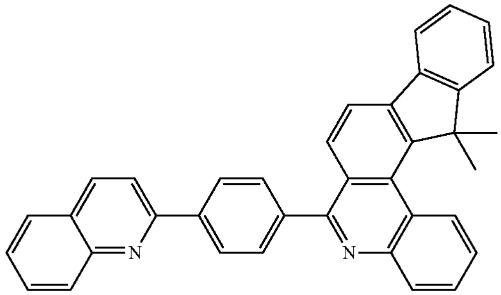
4-42
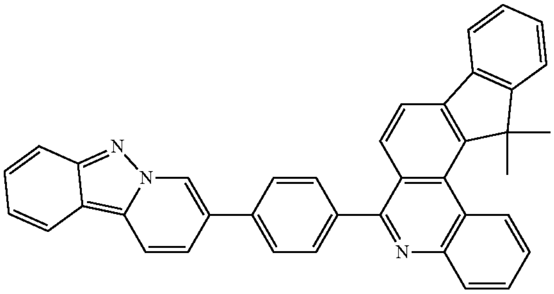
4-43
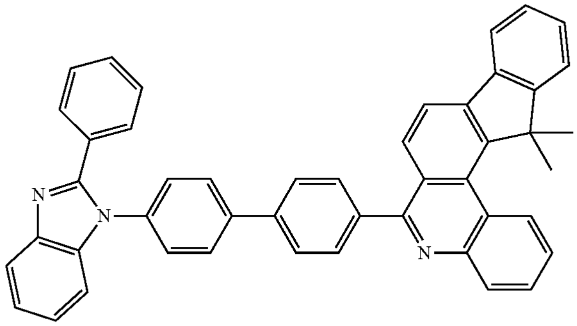

4-44
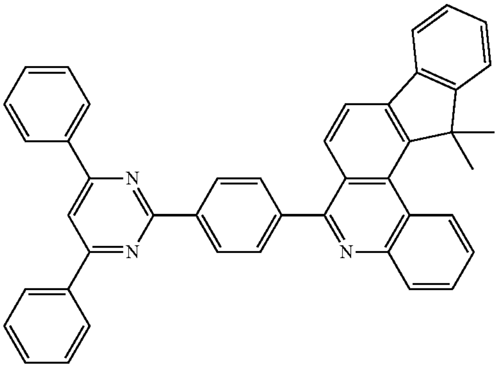
4-45
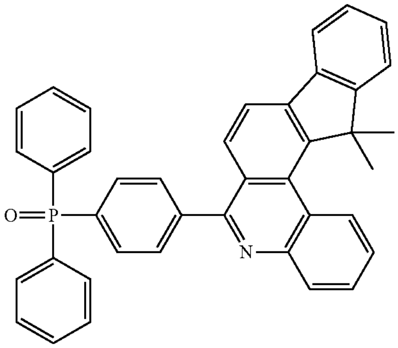
4-46
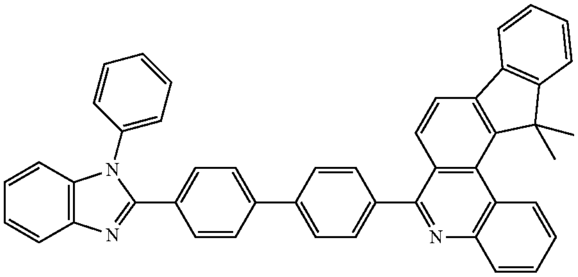
4-47
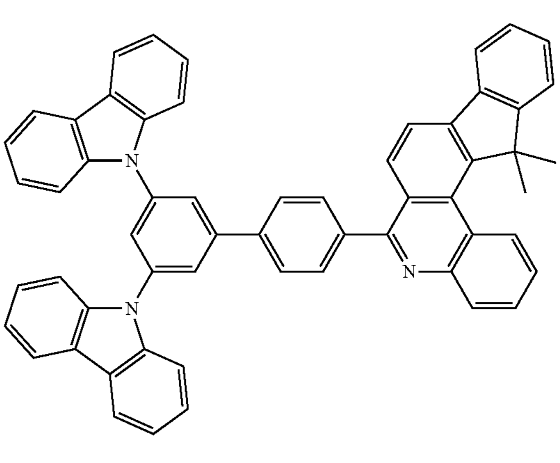
4-48
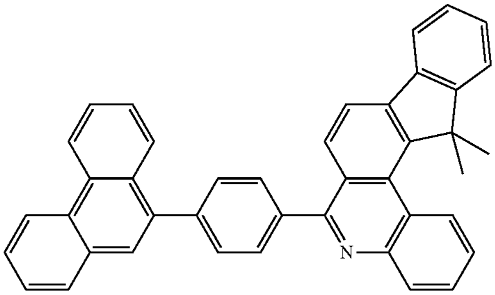
4-49
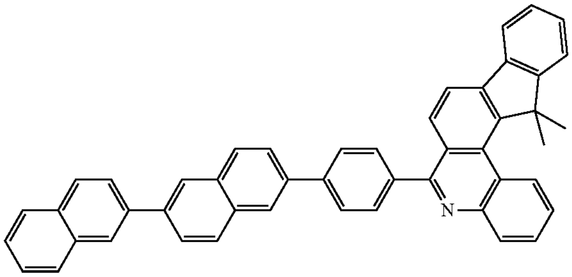
4-50
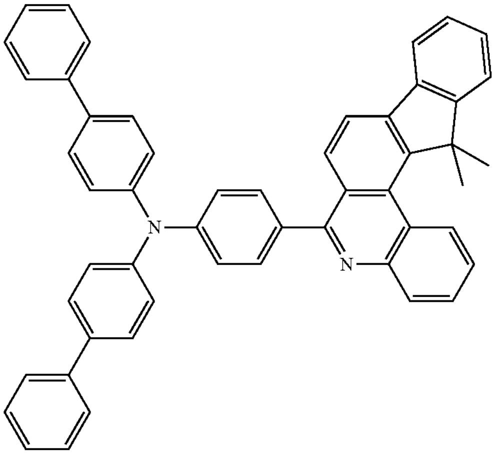
4-51
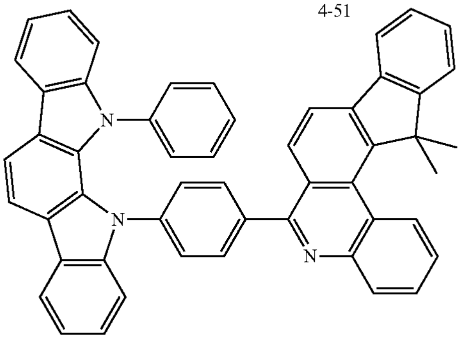

-continued
4-52
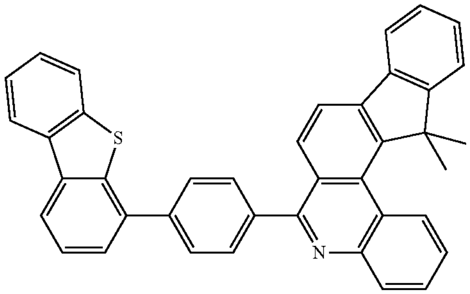
4-53
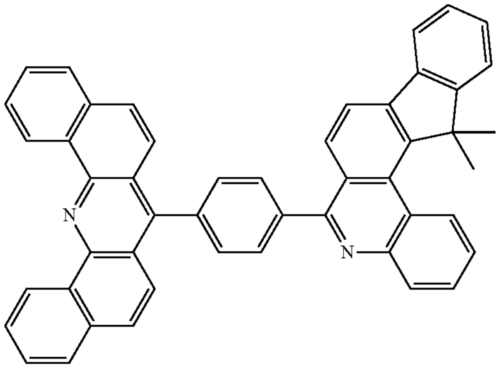
4-54
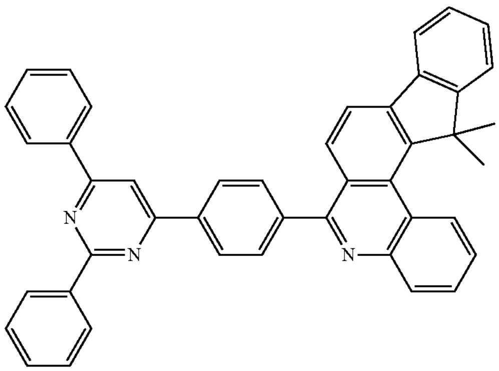
4-55
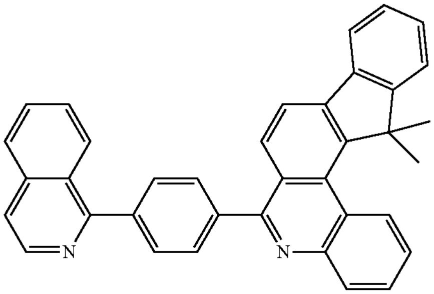
-continued
4-56
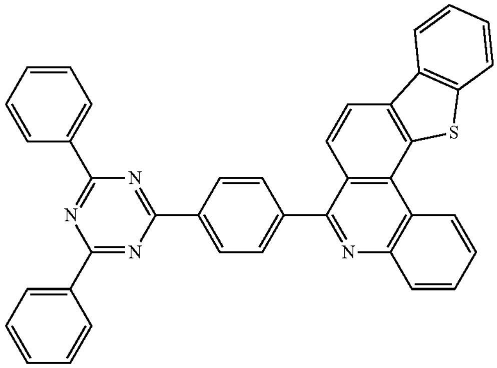
4-57
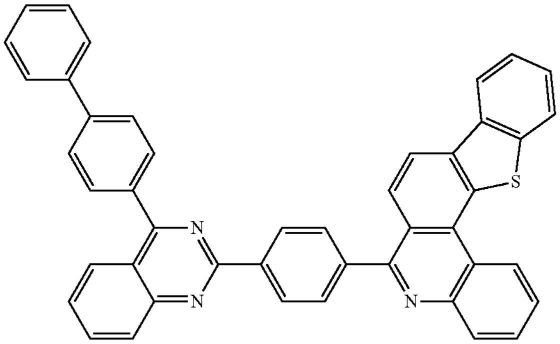
4-58
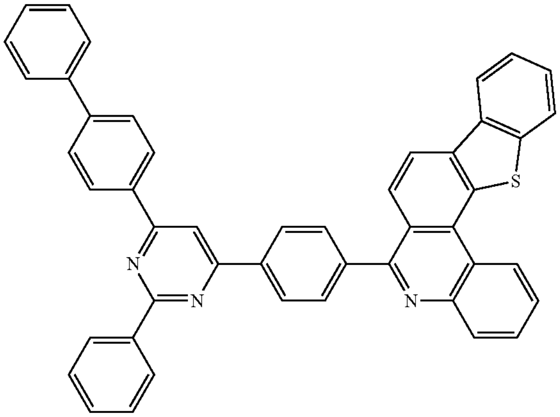
4-59
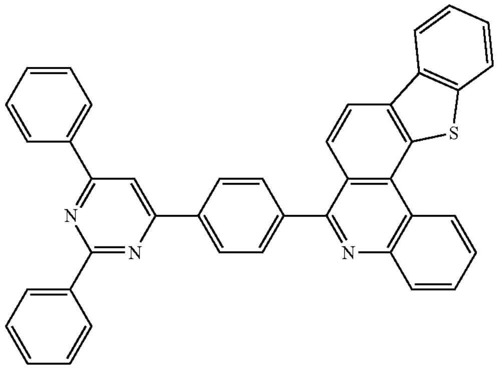

-continued
4-60
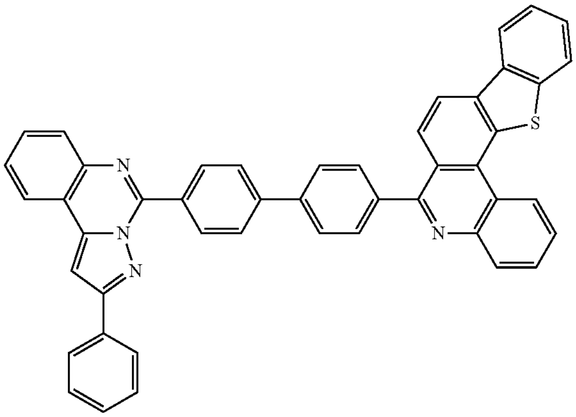
4-61
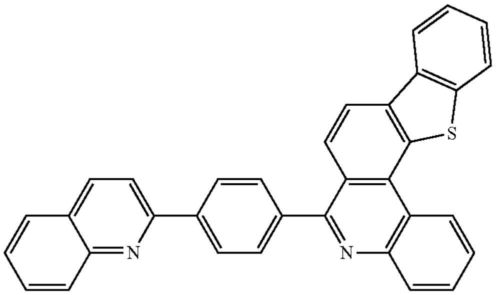
4-62
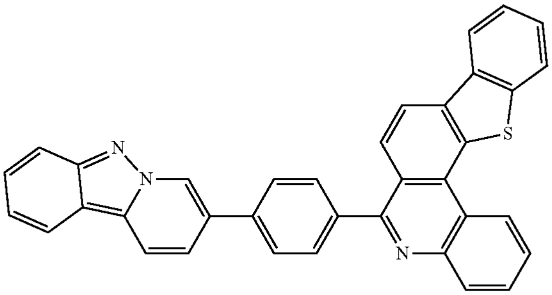
4-63
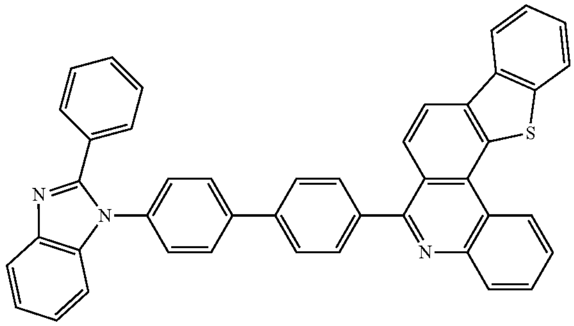
-continued
4-64
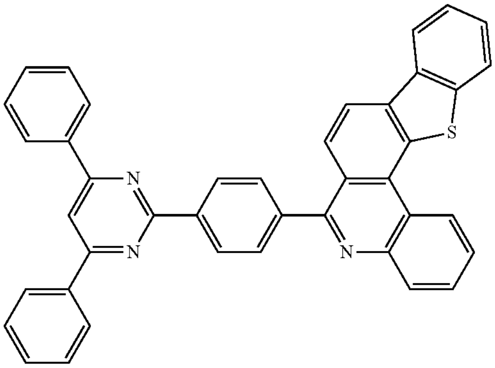
4-65
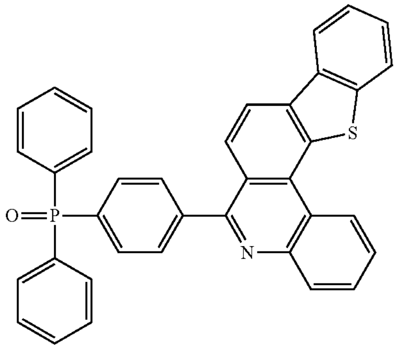
4-66
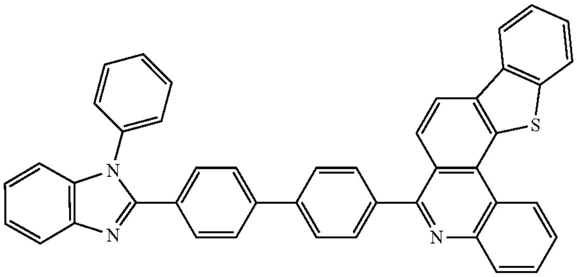
4-67
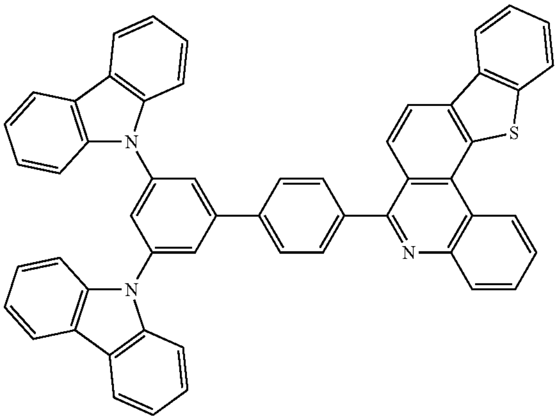

-continued
4-68
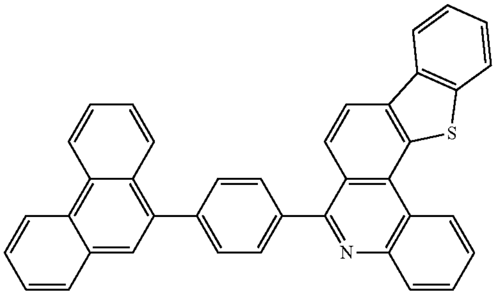
4-69
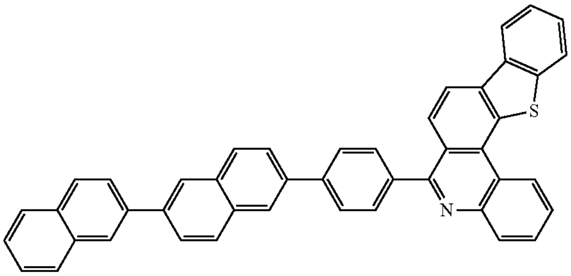
4-70
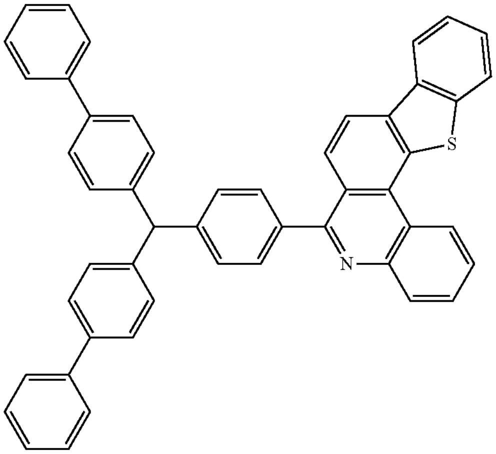
4-71
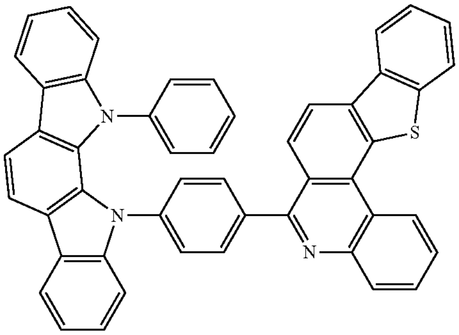
-continued
4-72
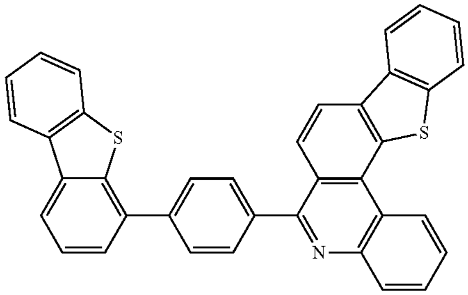
4-73
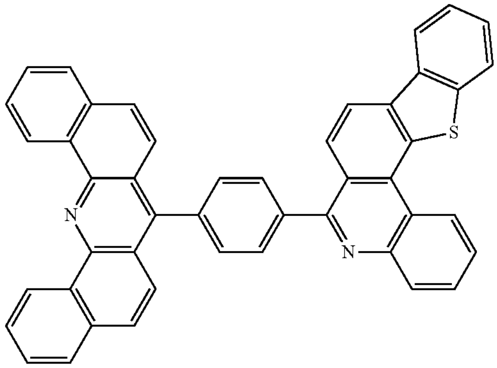
4-74
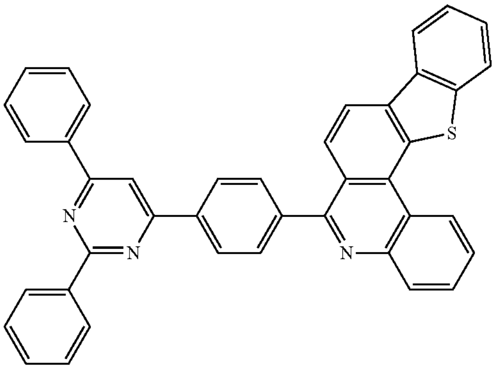
4-75
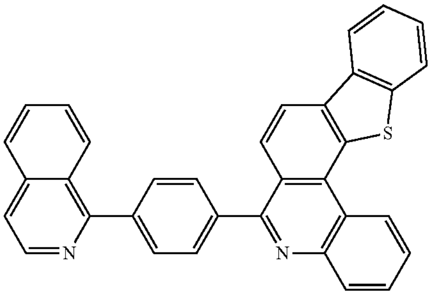

-continued
4-76
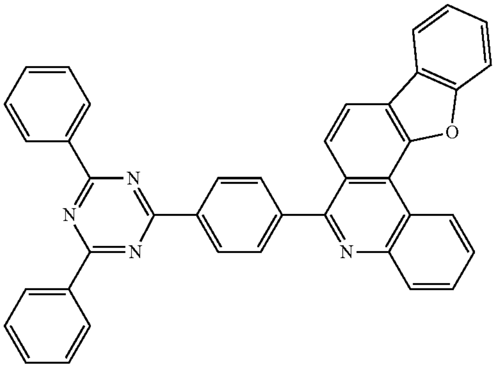
4-77
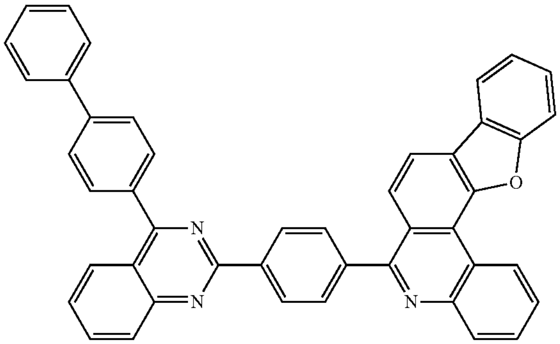
4-78
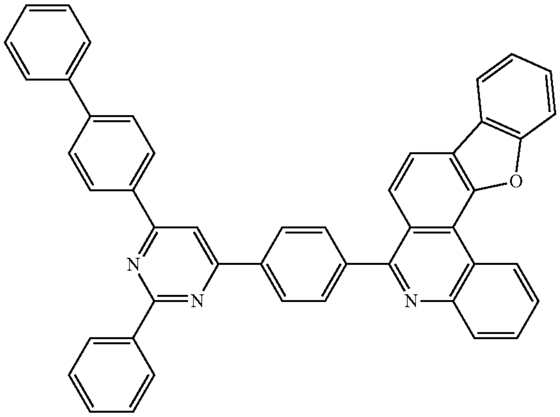
4-79
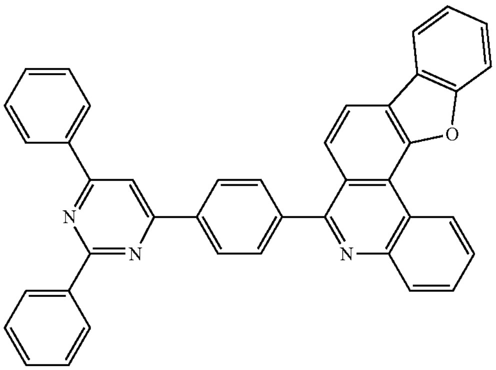
-continued
4-80
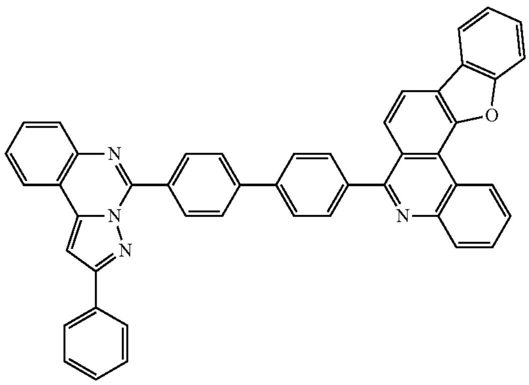
4-81
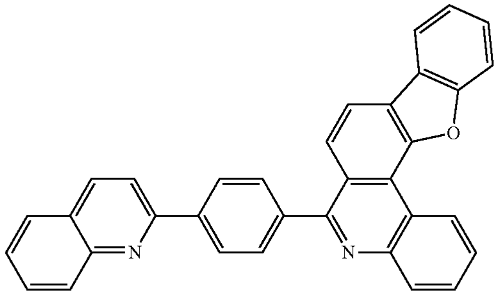
4-82
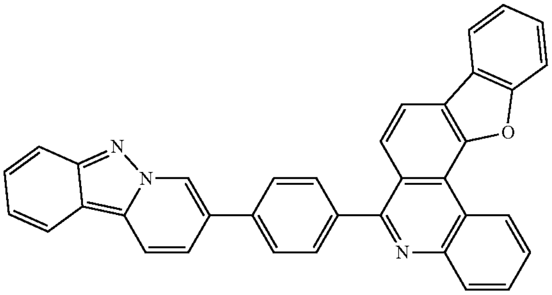
4-83
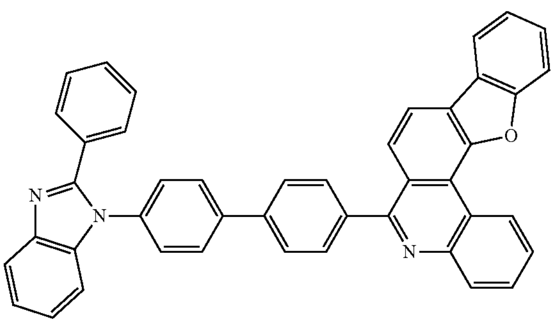

-continued
4-84
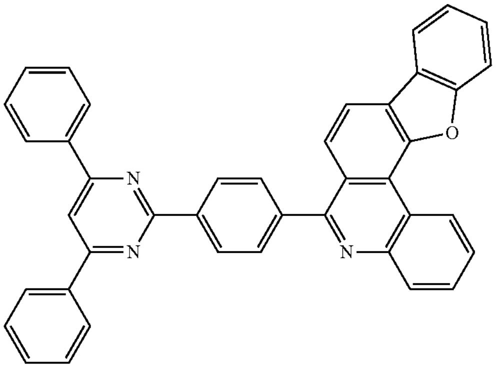
4-85
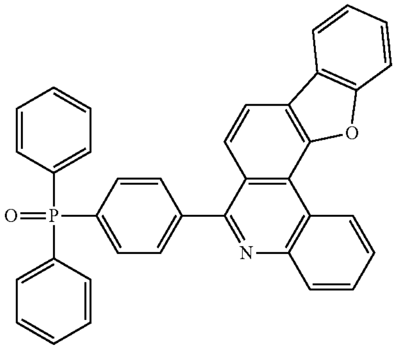
4-86
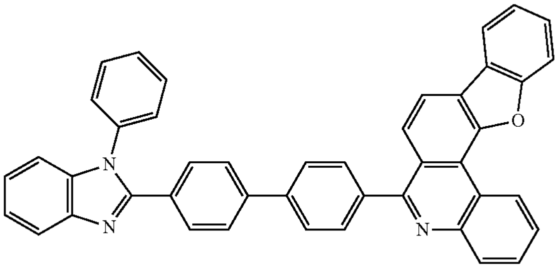
4-87
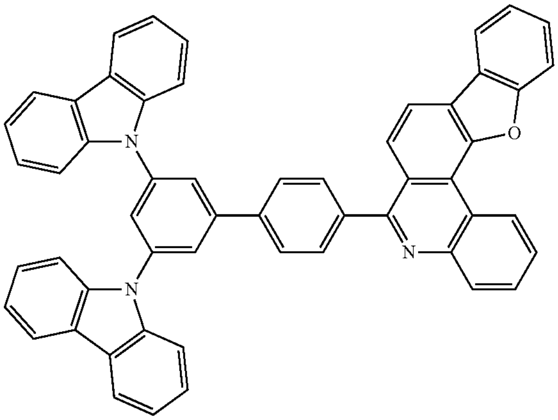
-continued
4-88
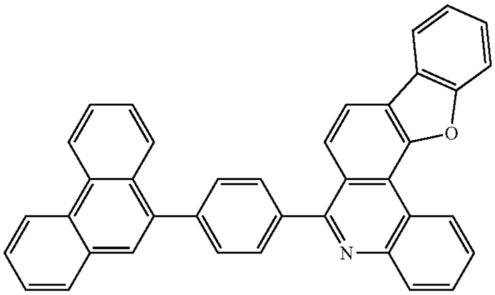
4-89
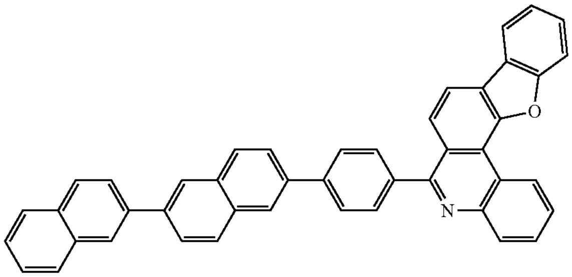
4-90
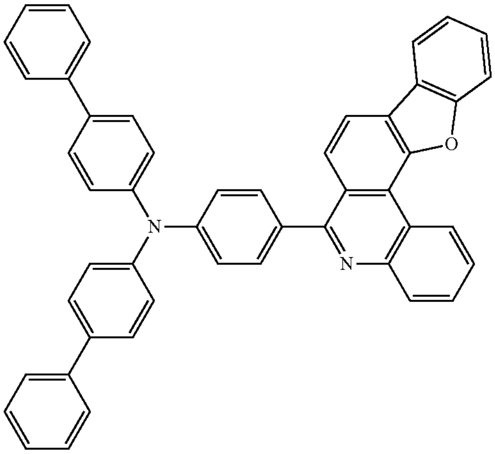
4-251
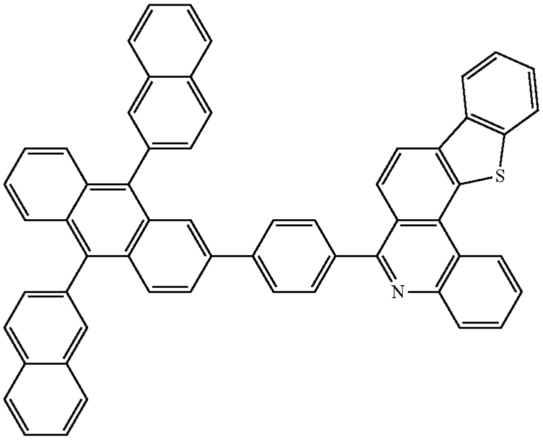

-continued
4-252
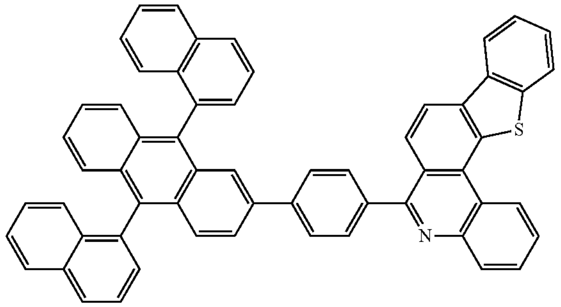
4-253
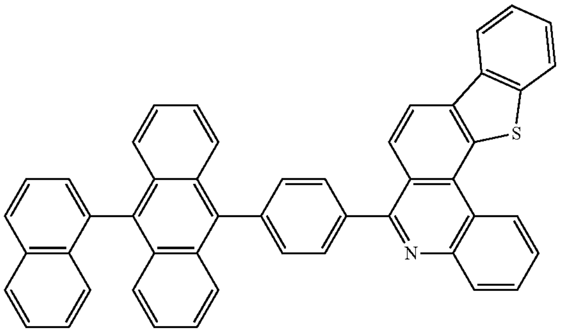
4-254
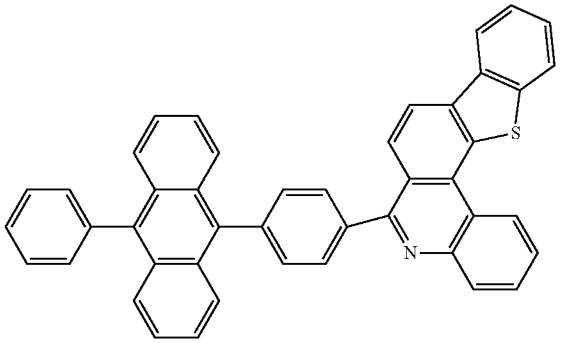
4-255
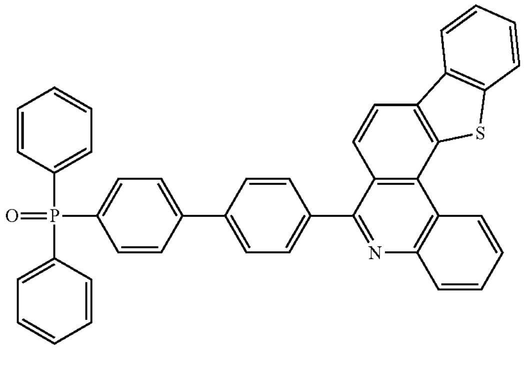
-continued
4-256
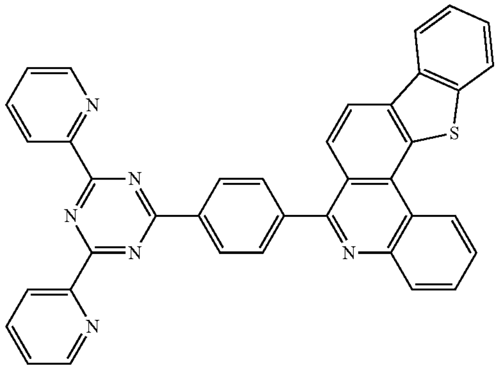
4-257
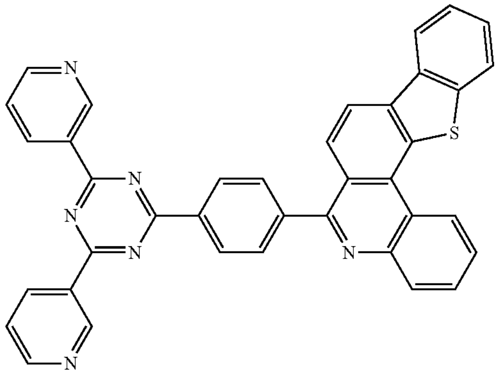
4-258
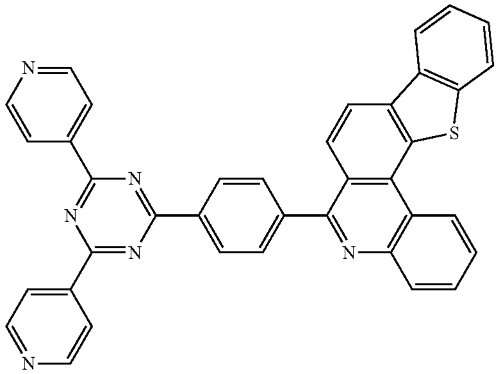
4-259
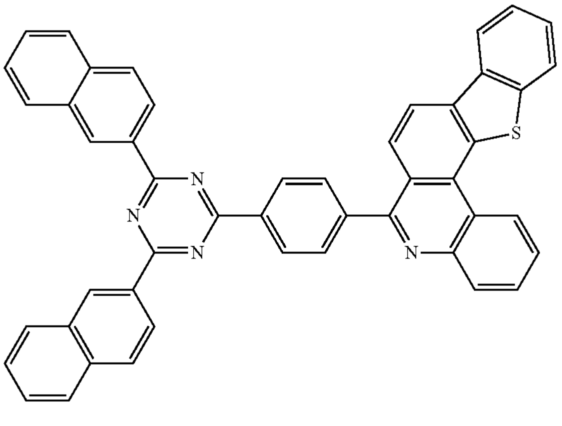

-continued
4-260
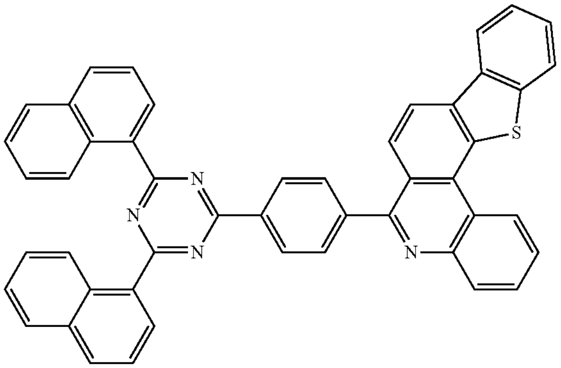
4-261
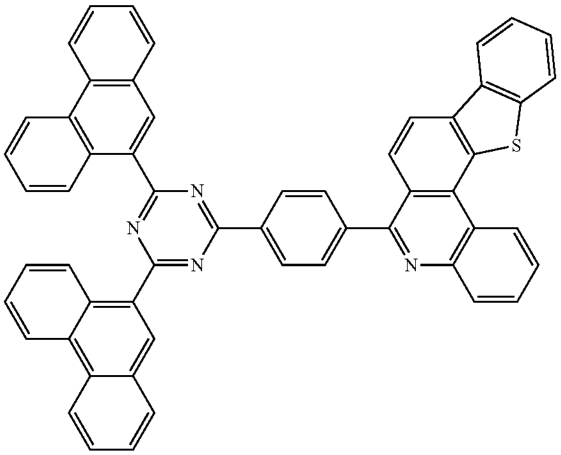
4-262
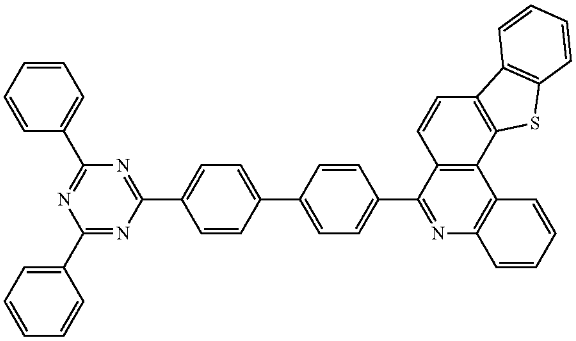
4-263
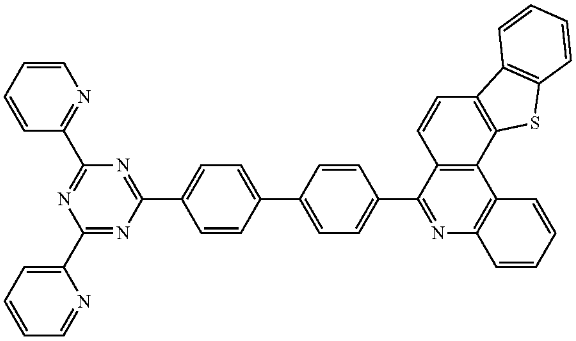
-continued
4-264
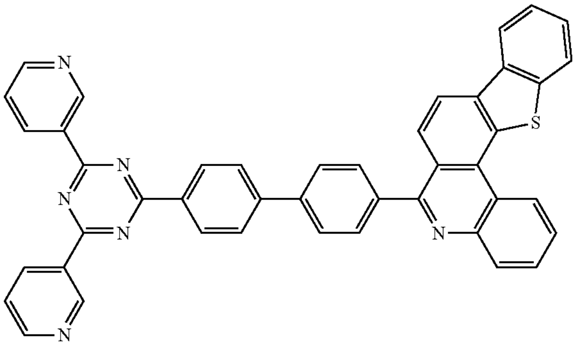
4-265
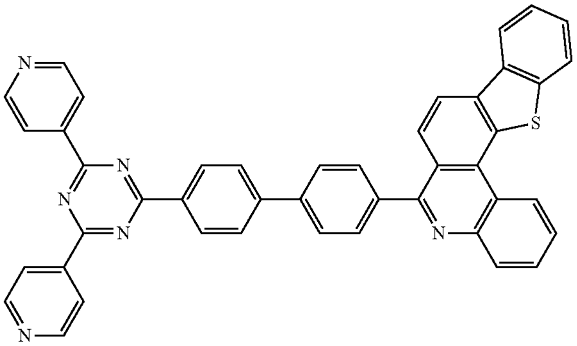
4-266
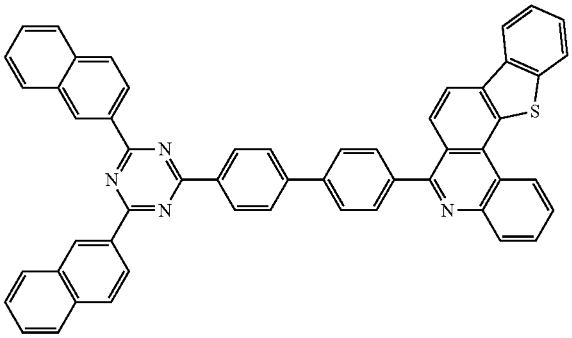
4-267
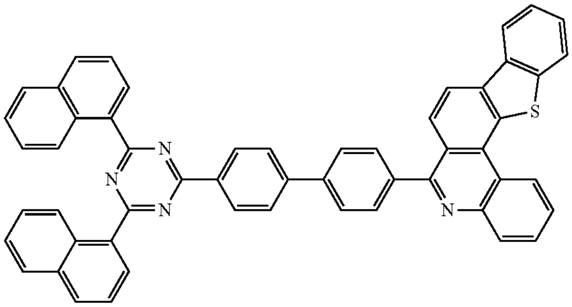

-continued
4-268
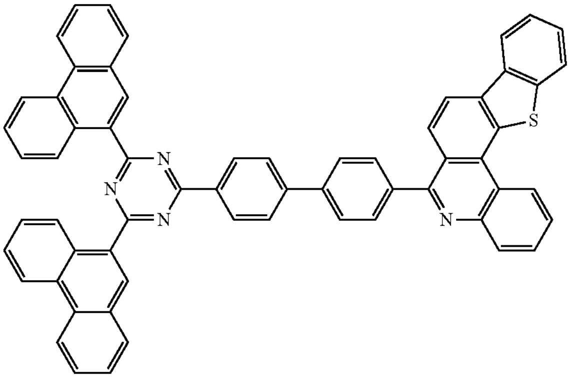
4-269
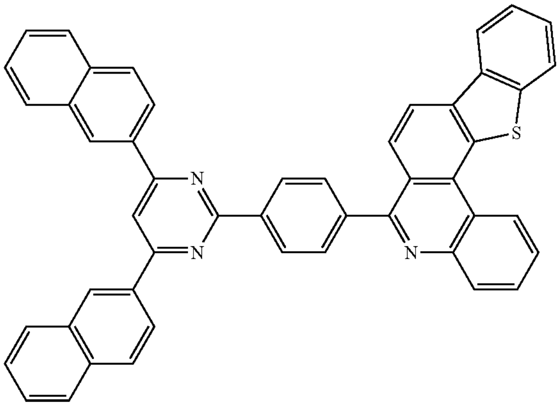
4-270
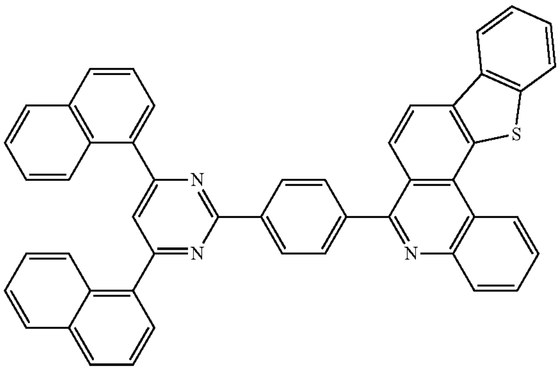
-continued
4-271
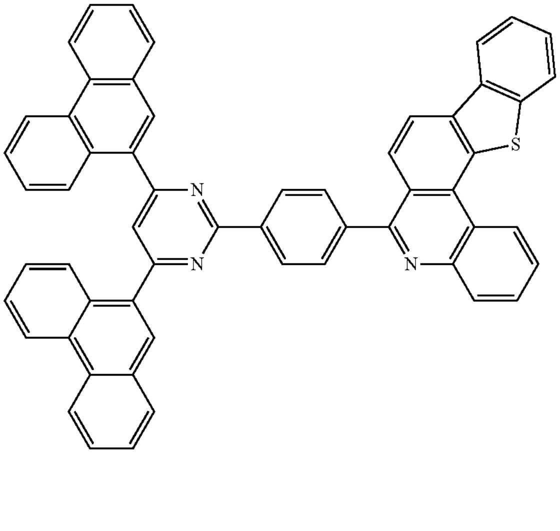
4-272
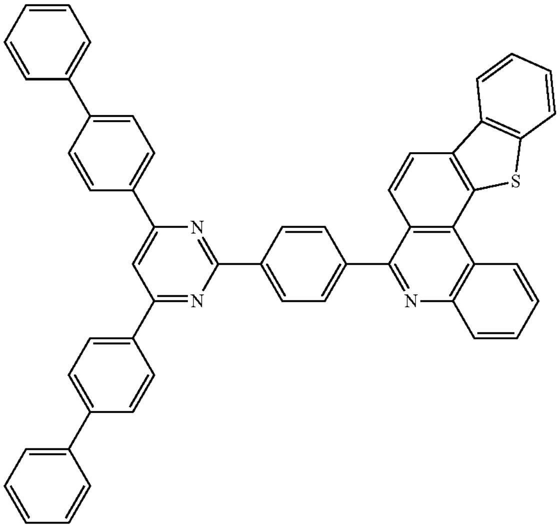
4-273
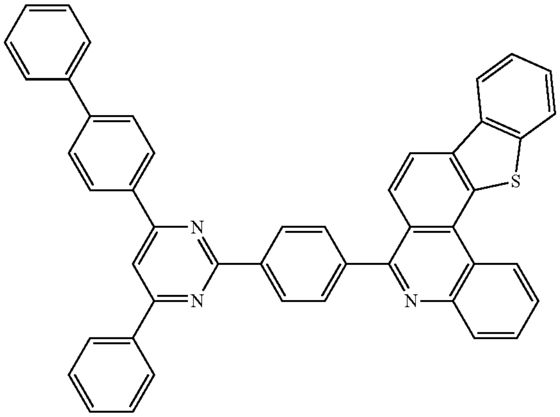

-continued
4-274
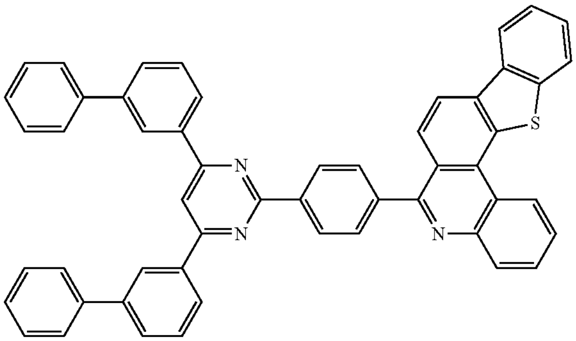
4-275
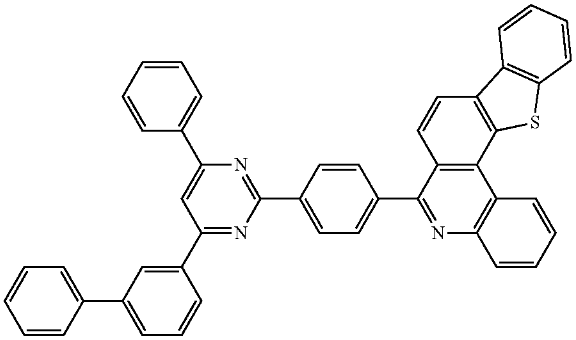
4-276
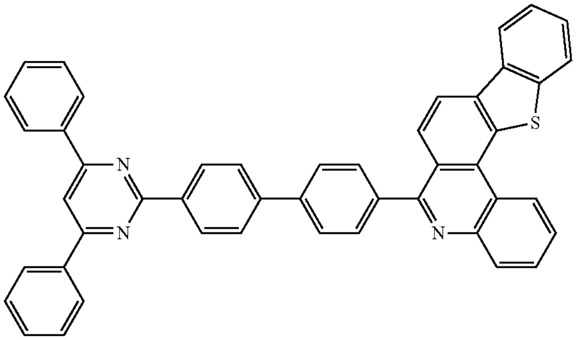
4-277
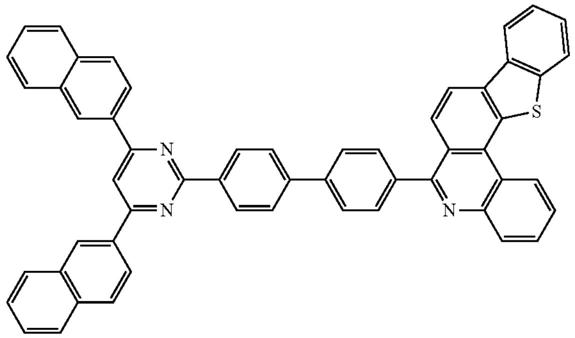
-continued
4-278
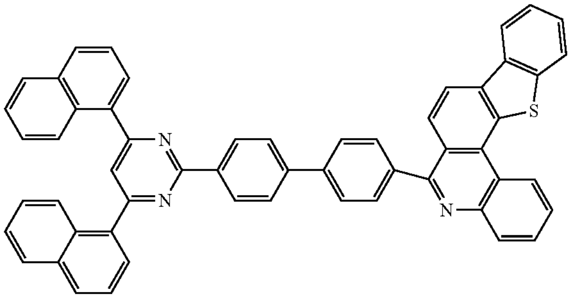
4-279
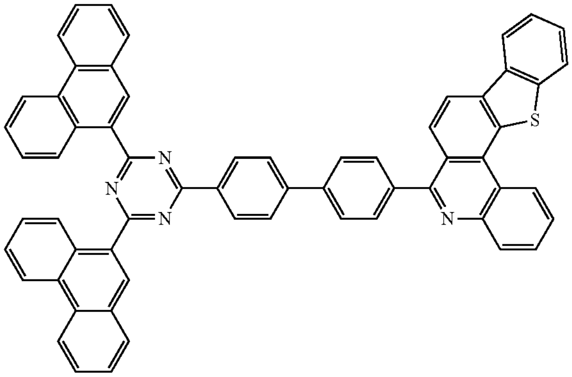
4-280
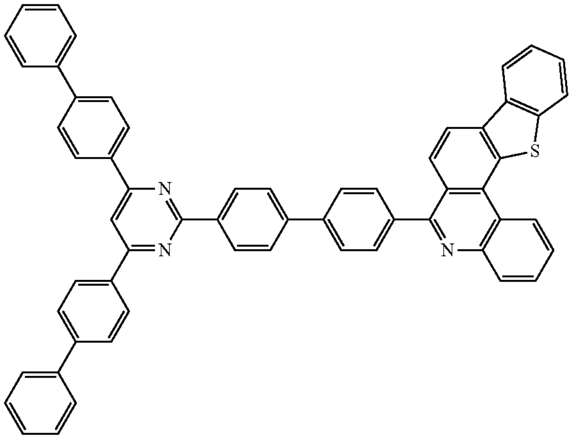
4-281
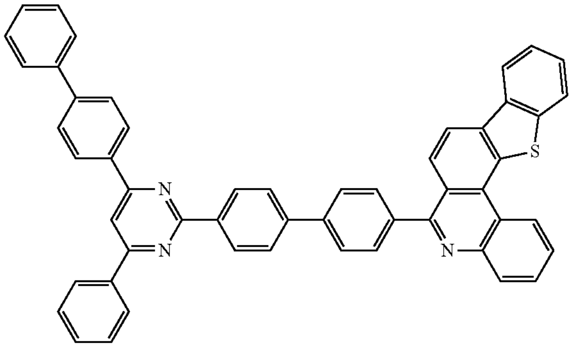

-continued
4-282
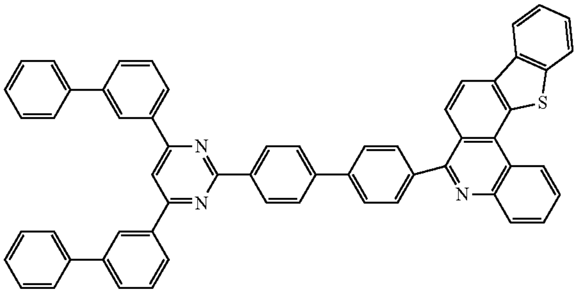
4-283
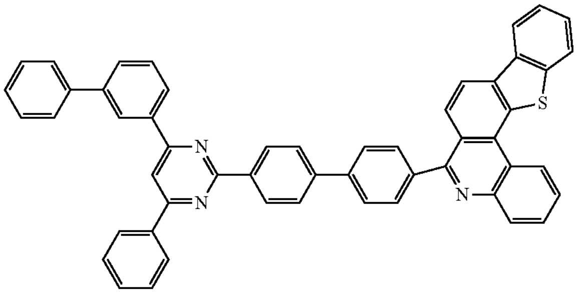
4-284
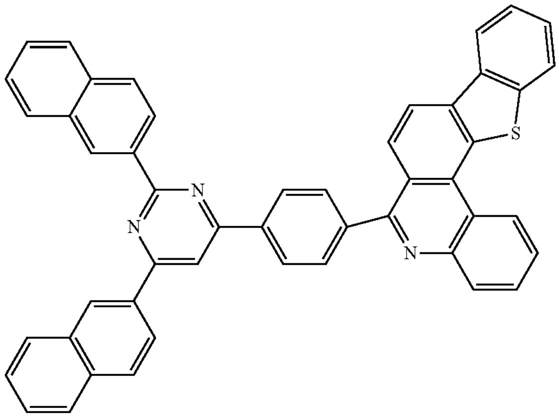
4-285
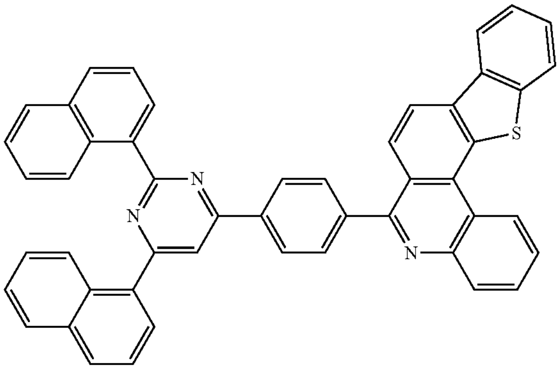
-continued
4-286
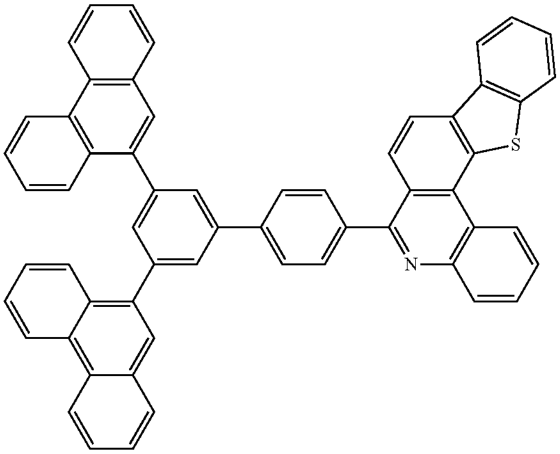
4-287
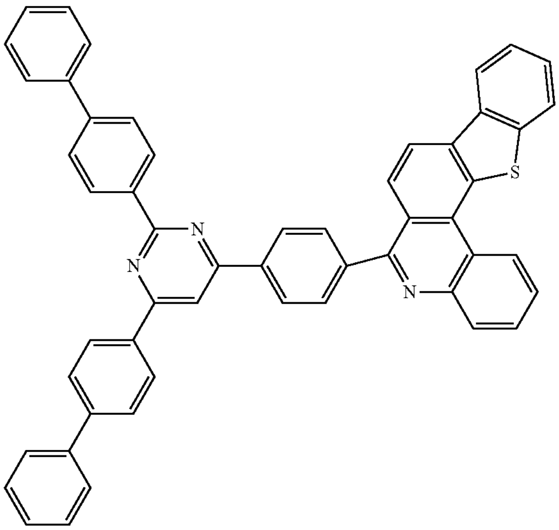
4-288
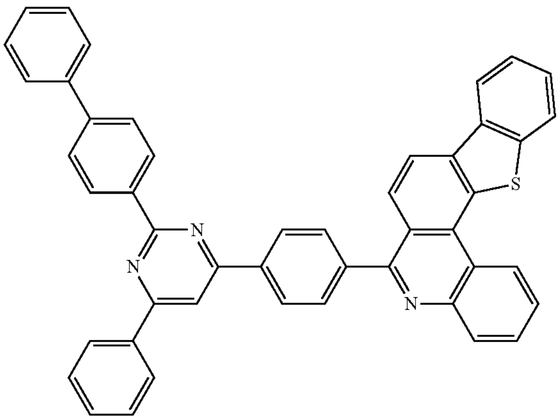

4-289
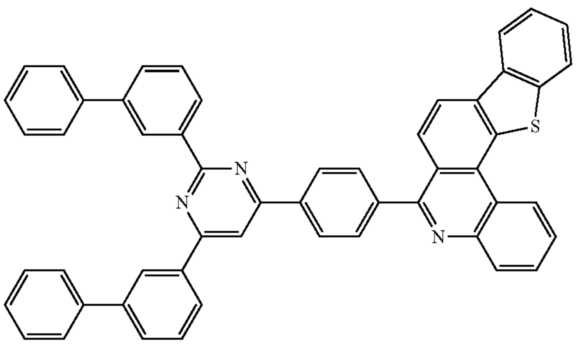
4-290
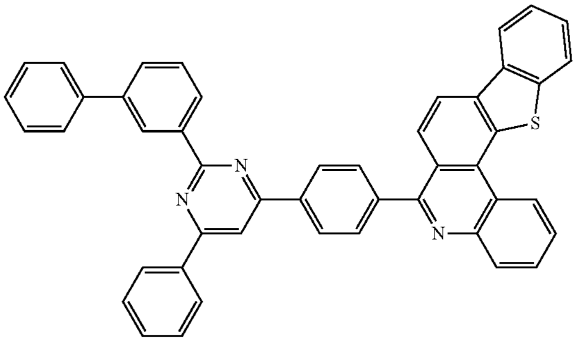
4-291
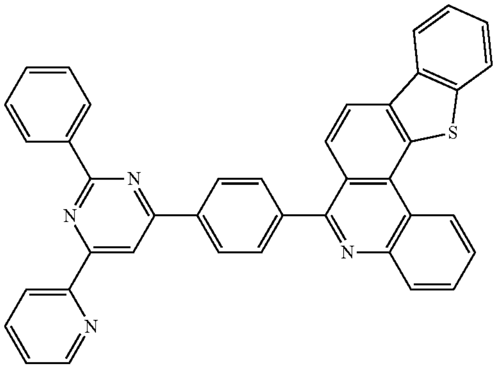
4-292
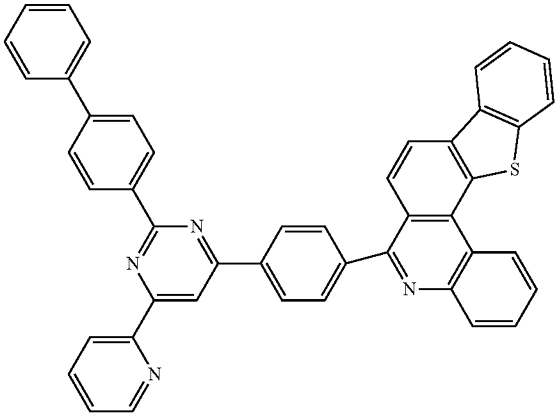
4-293
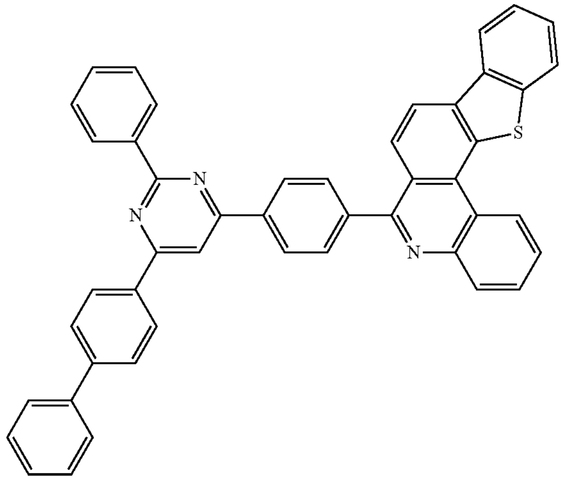
4-294
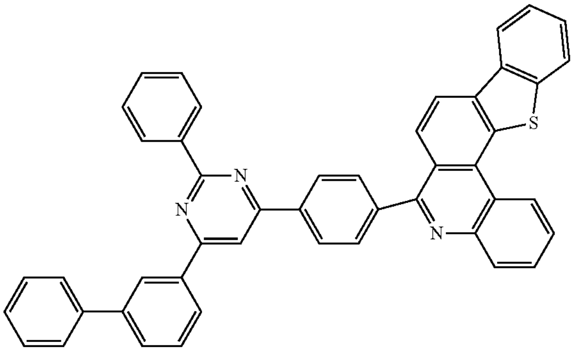
4-295
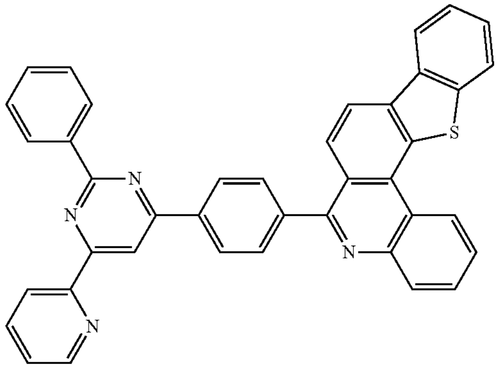
4-296
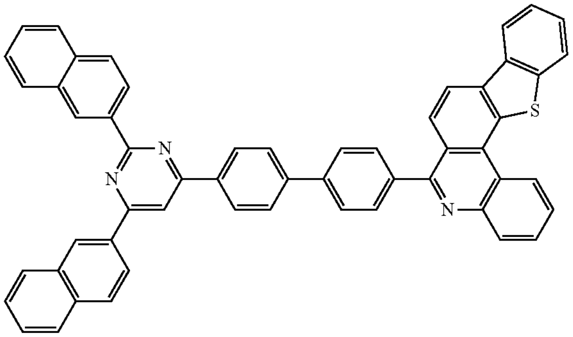

4-297
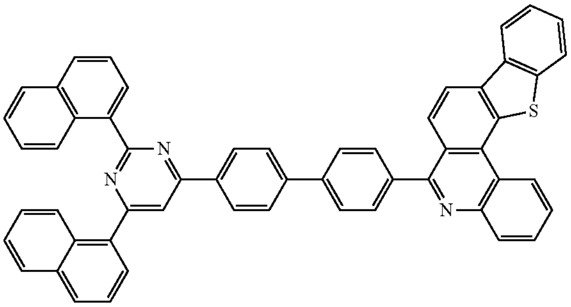
4-298
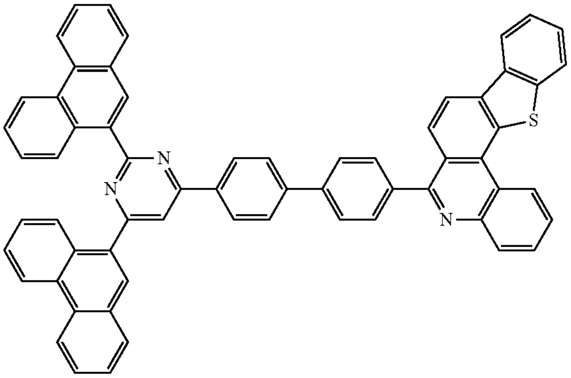
4-299
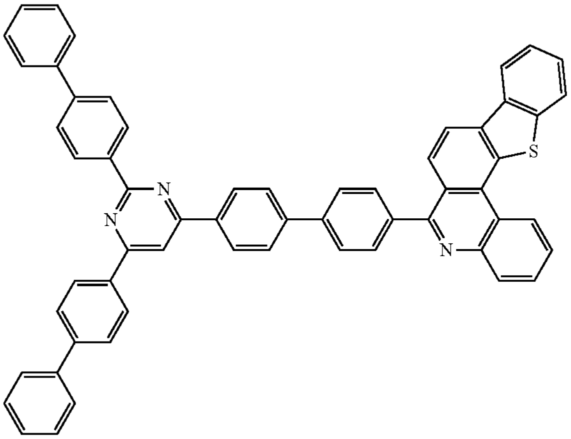
4-300
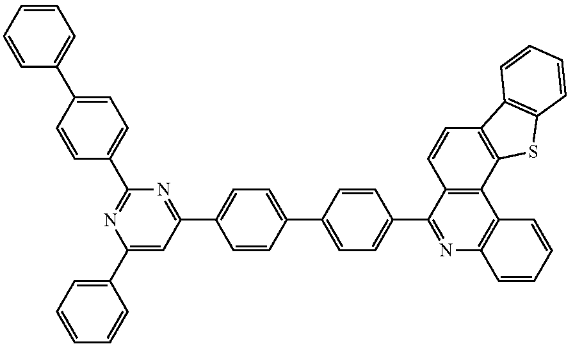
4-301
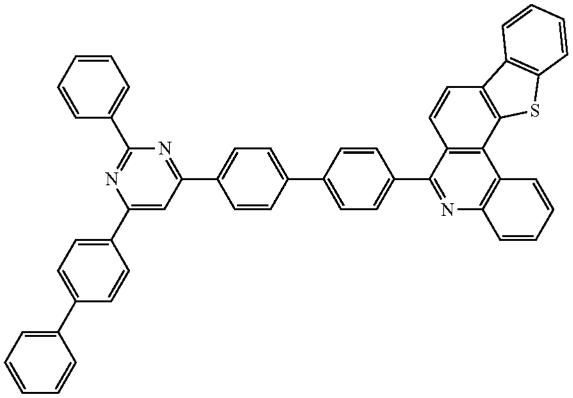
4-302
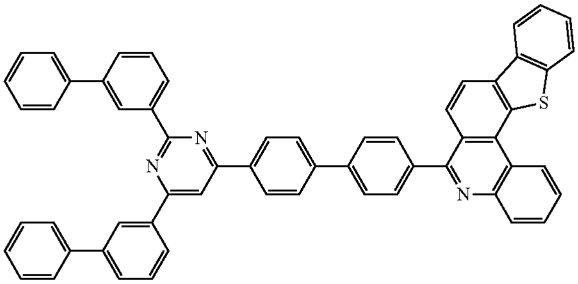
4-303
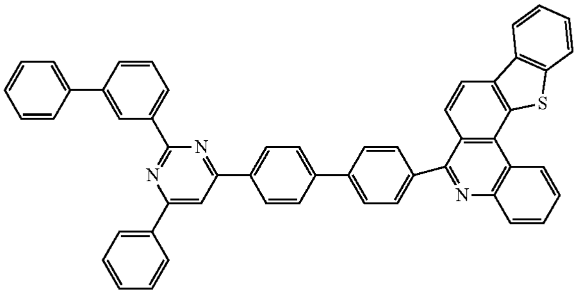
4-304
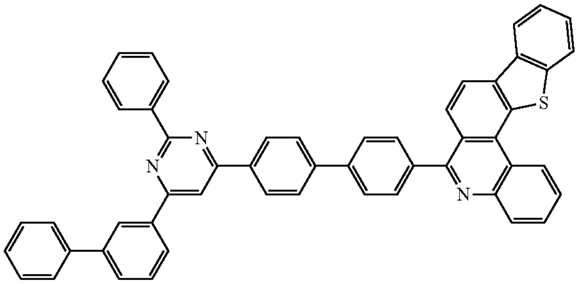

-continued
4-305
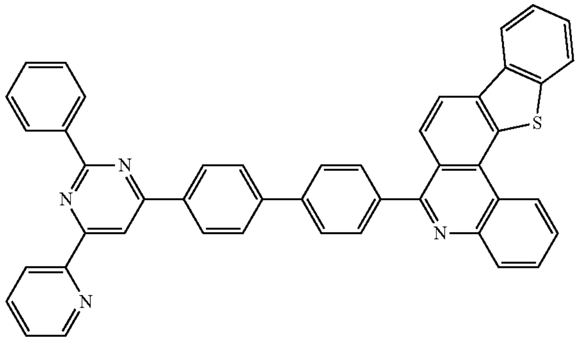
4-306
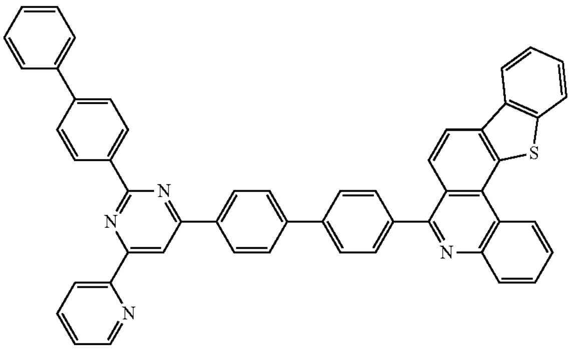
4-307
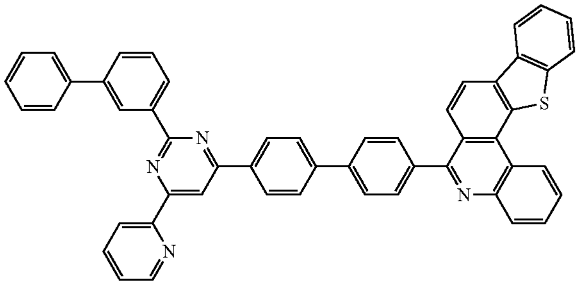
4-308
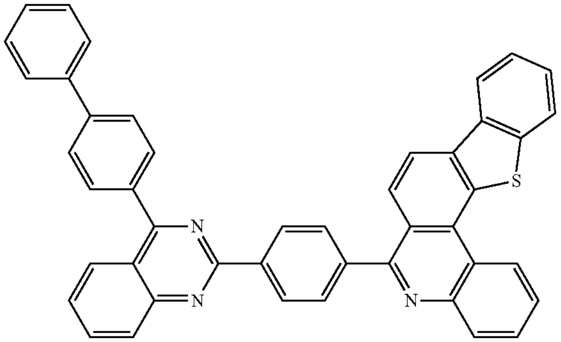
-continued
4-309
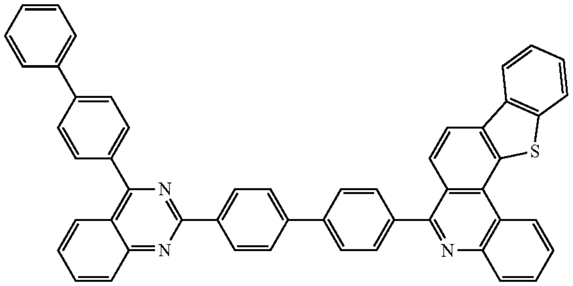
4-310
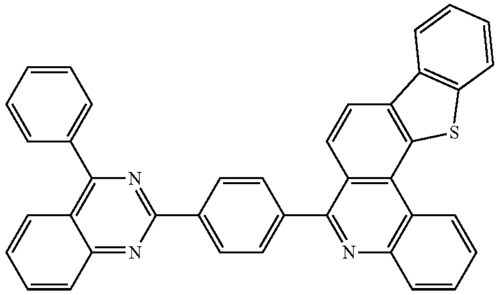
4-311
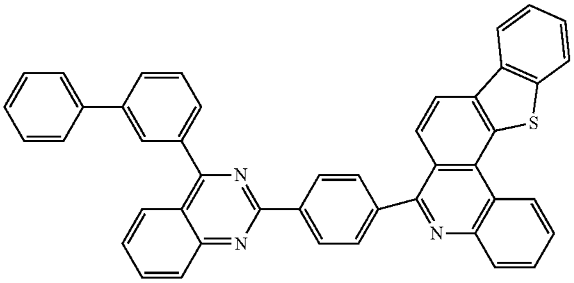
4-312
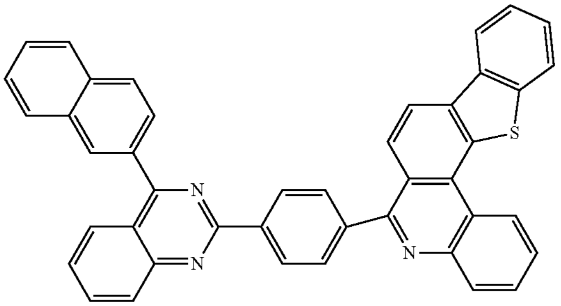
4-313
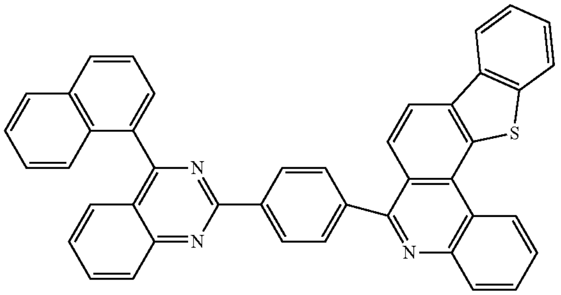

-continued
4-314
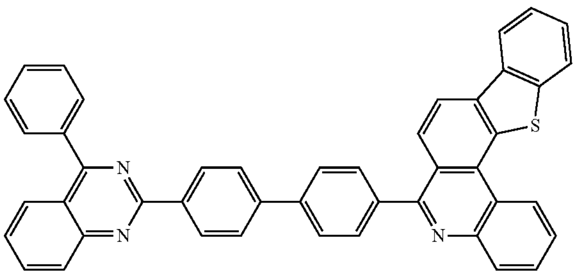
4-315
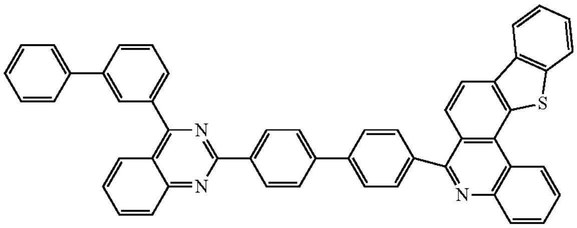
4-316
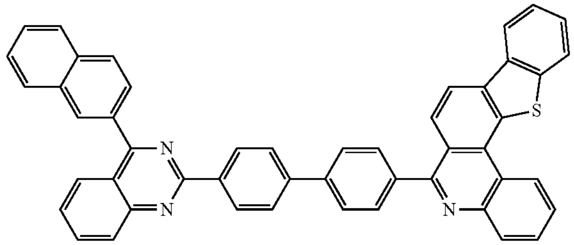
4-317
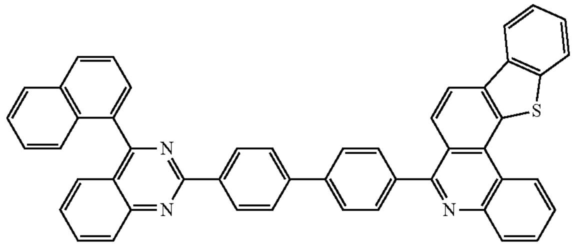
4-318
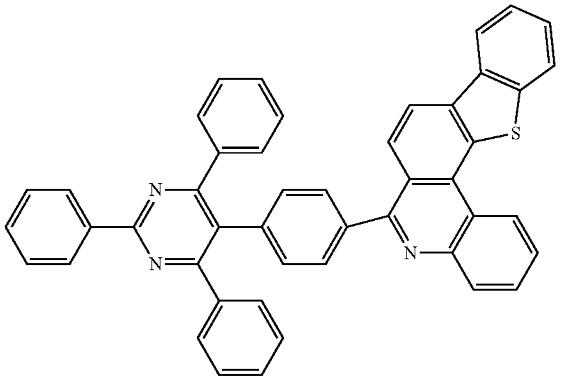
-continued
4-319
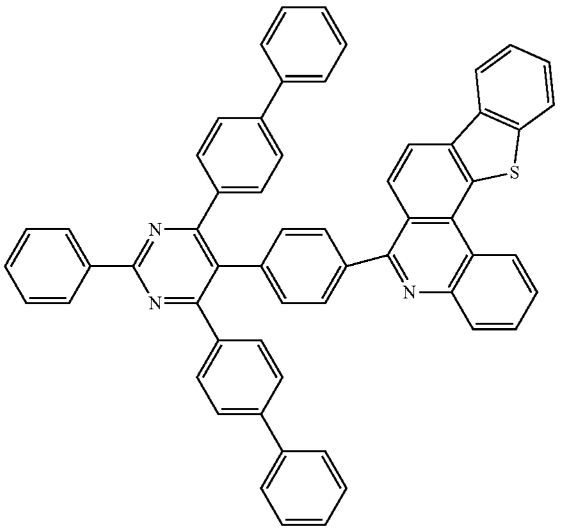
4-320
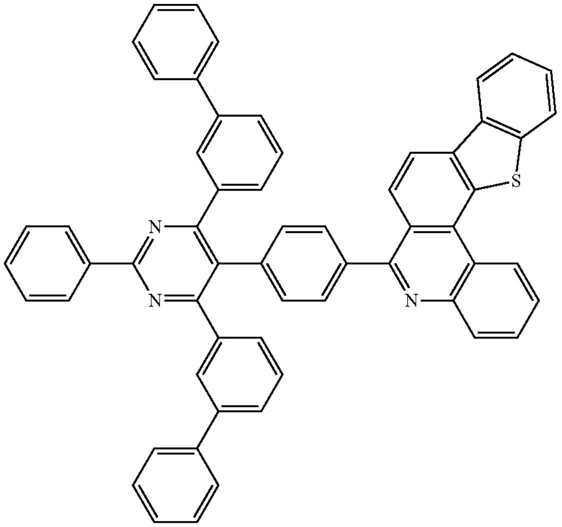
4-321
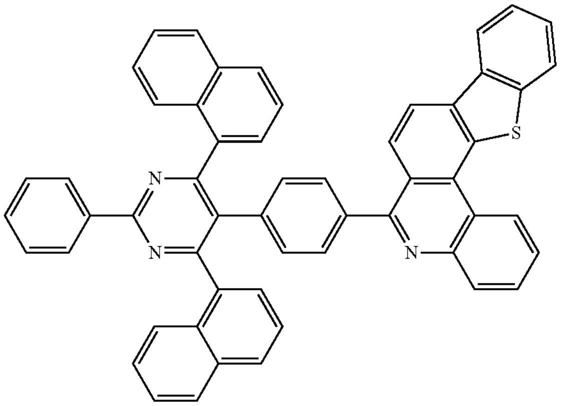

-continued
4-322
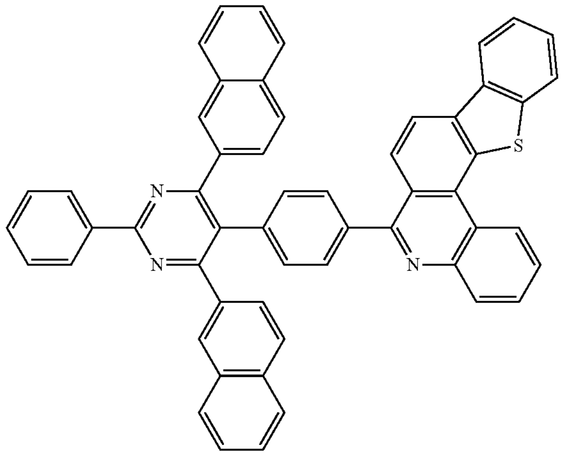
4-323
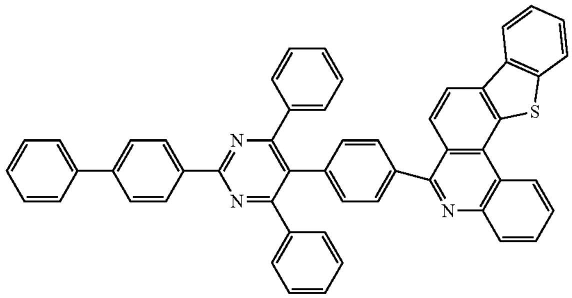
4-324
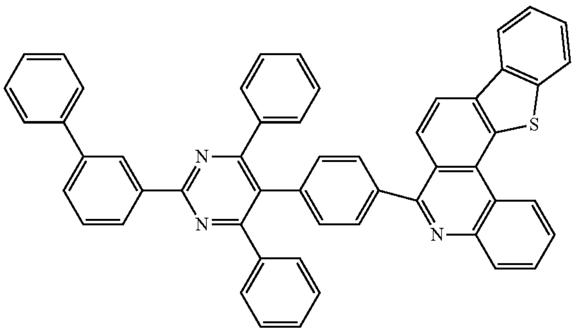
4-325
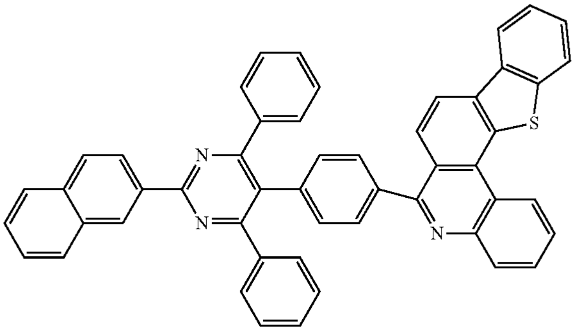
-continued
4-326
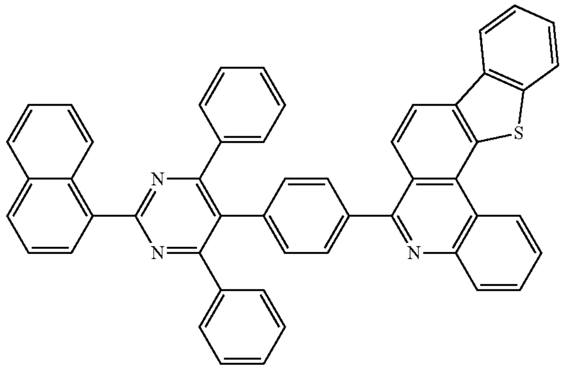
4-327
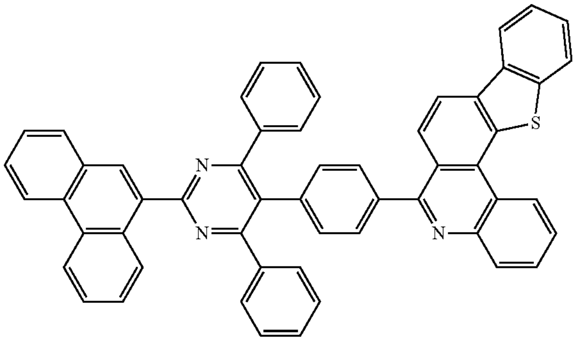
4-328
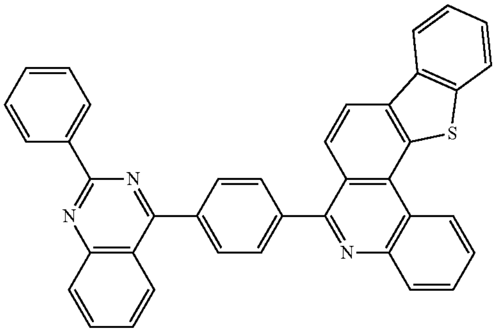
4-329
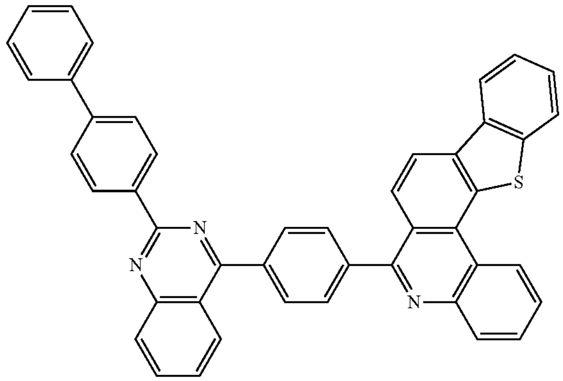

-continued
4-330
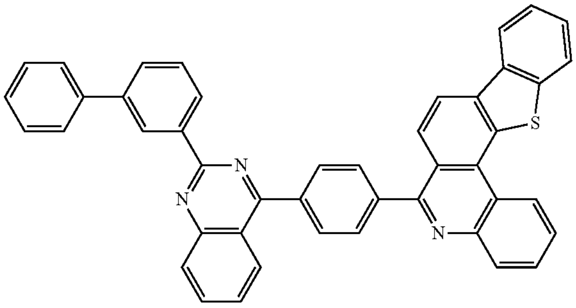
4-331
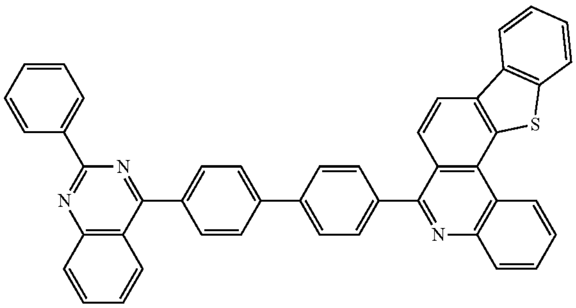
4-332
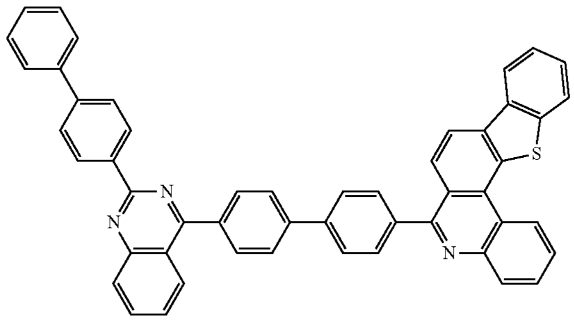
4-333
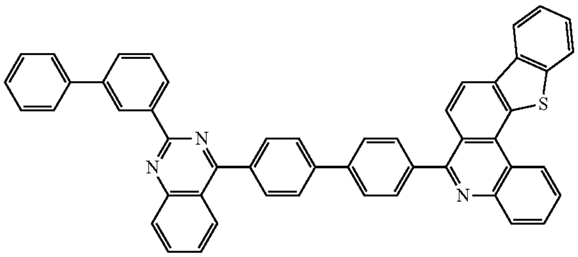
4-334
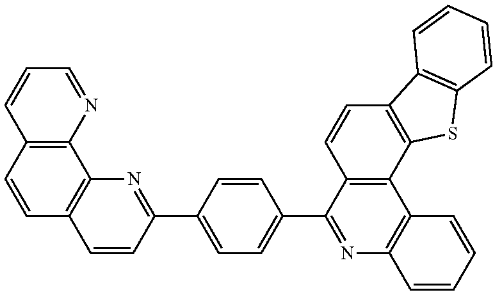
-continued
4-335
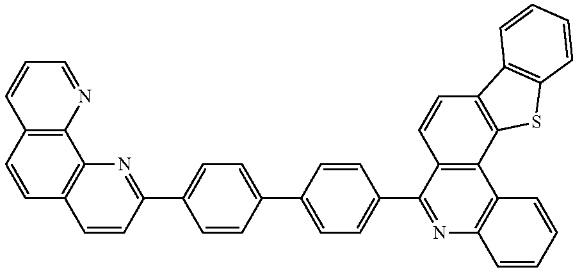
4-336
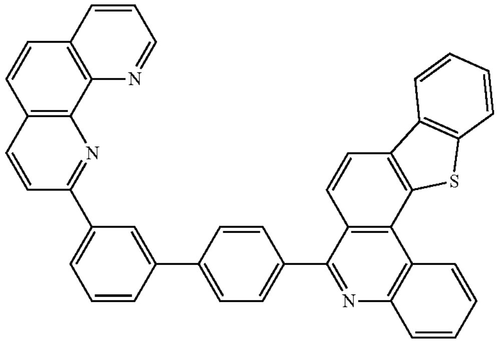
4-337
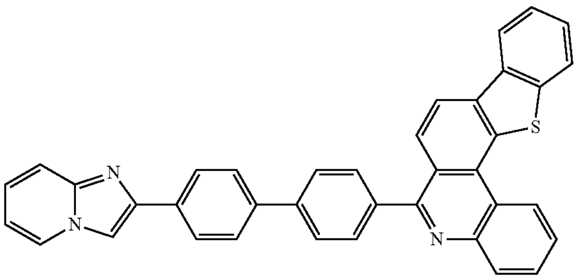
4-338
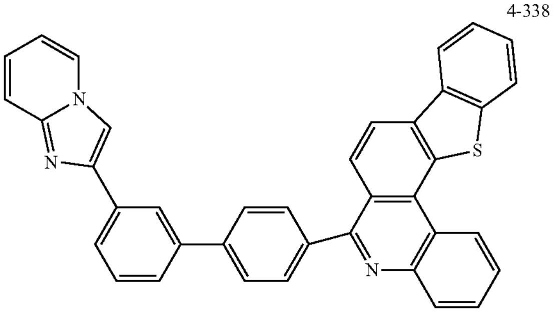
4-339
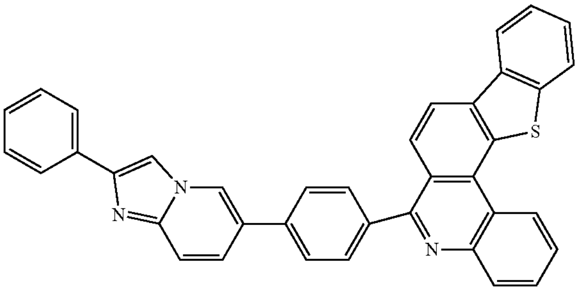

-continued
4-340
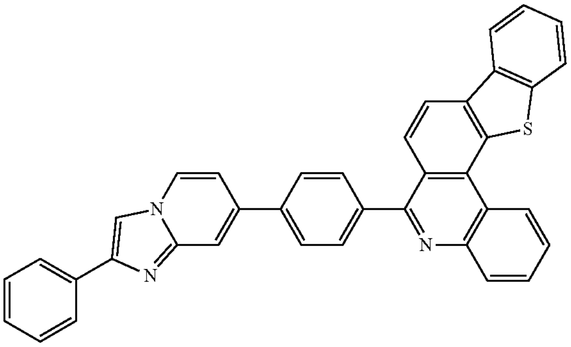
4-341
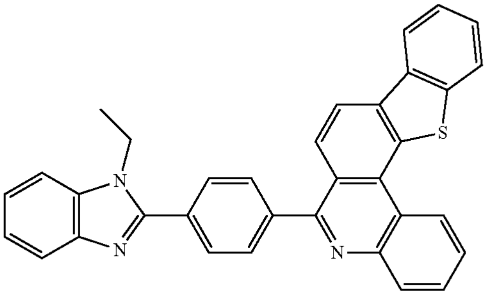
4-342
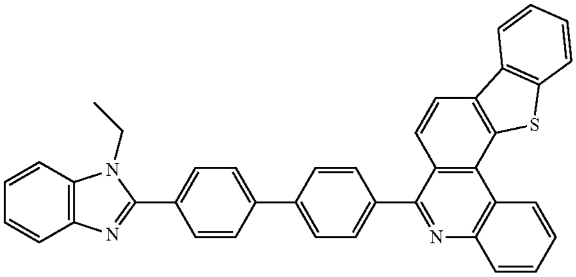
4-343
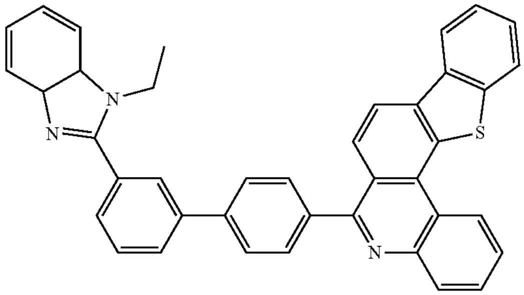
-continued
4-344
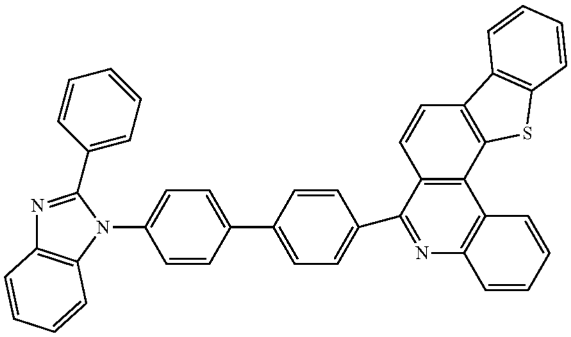
4-345
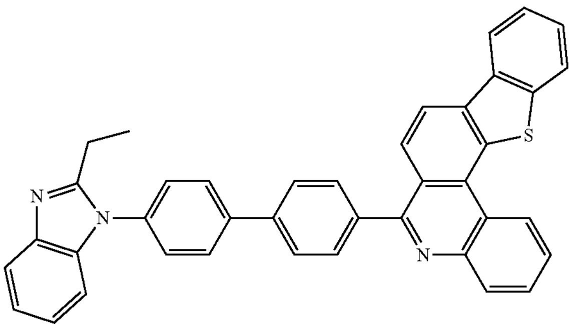
4-346
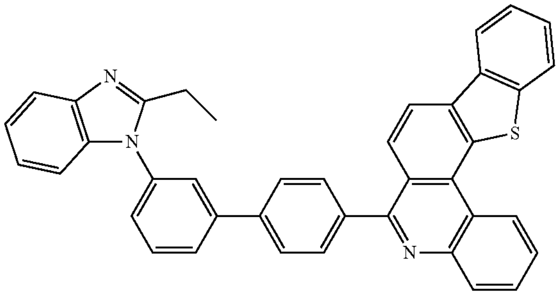
4-347
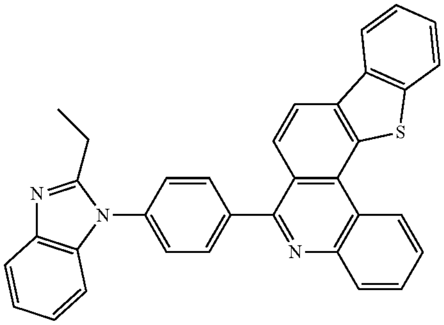

-continued
4-348
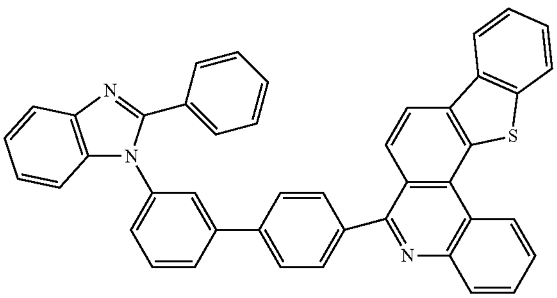
4-349
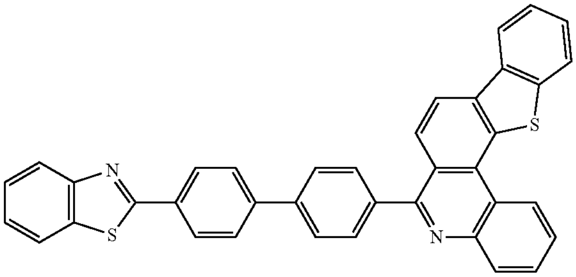
4-350
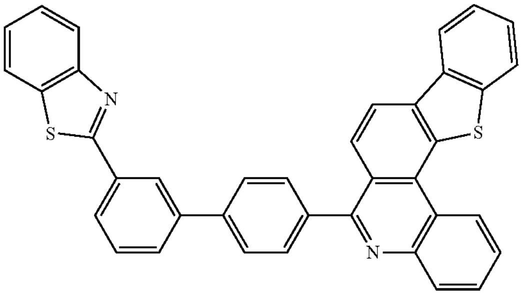
4-351
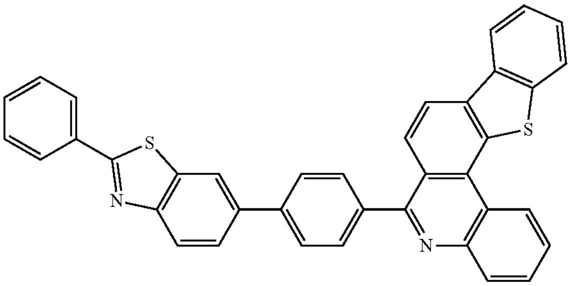
4-352
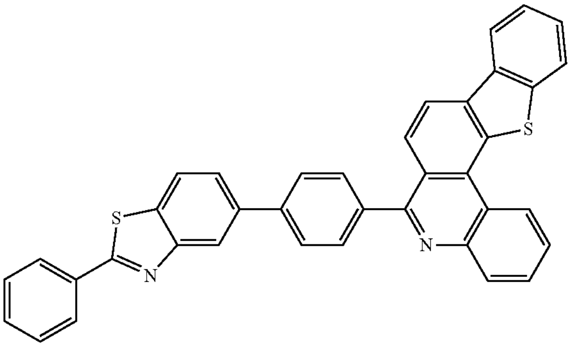
-continued
4-353
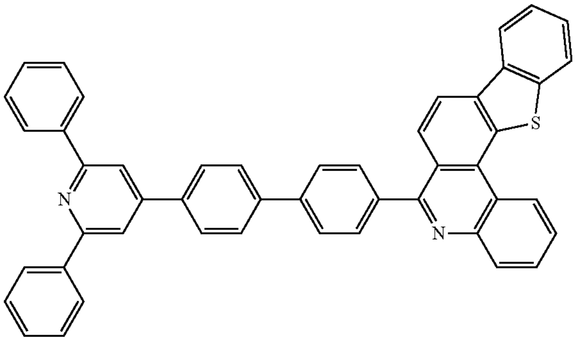
4-354
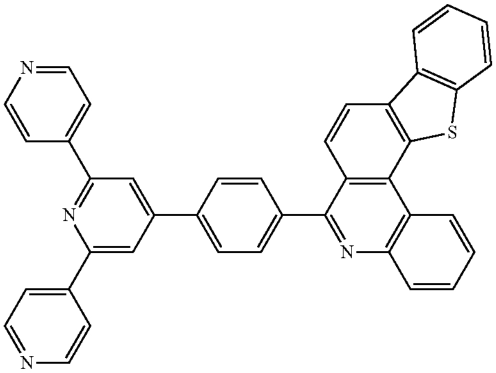
4-355
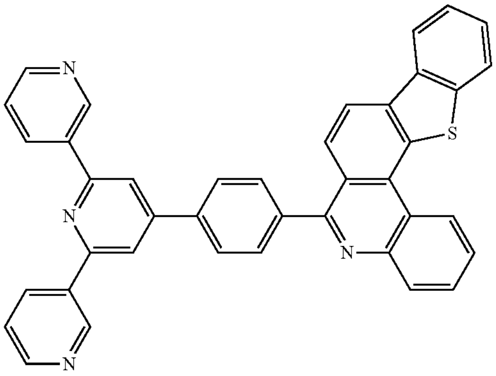
4-356
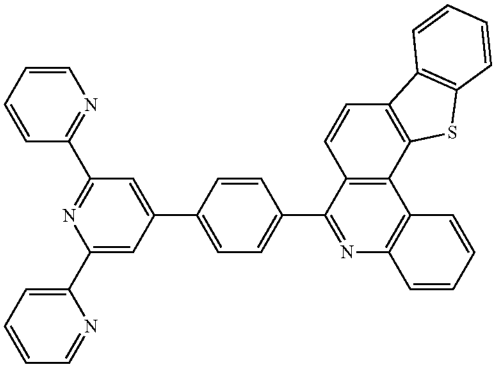

-continued
4-357
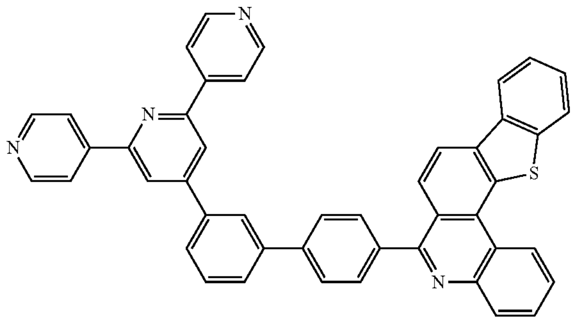
4-358
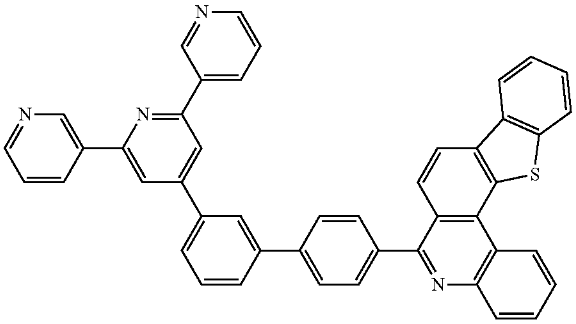
4-359
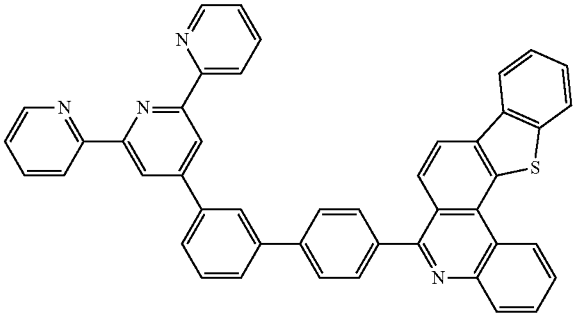
4-360
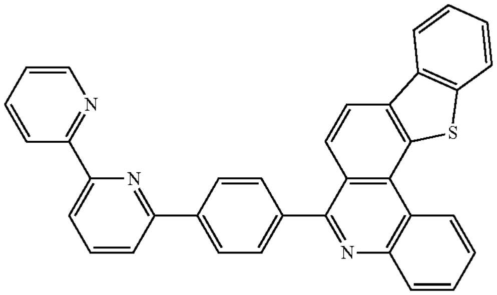
4-361
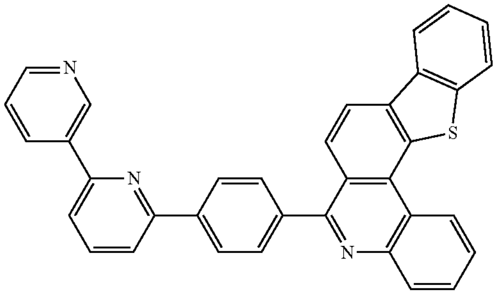
-continued
4-362
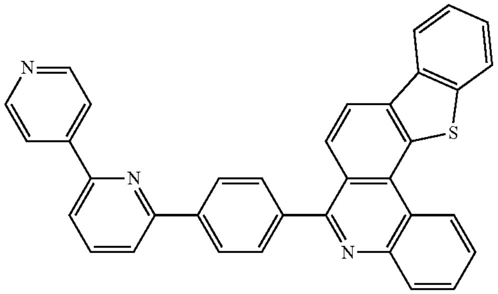
4-363
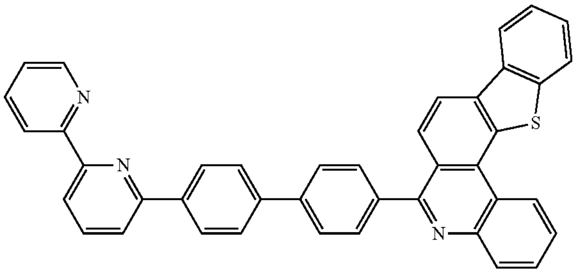
4-364
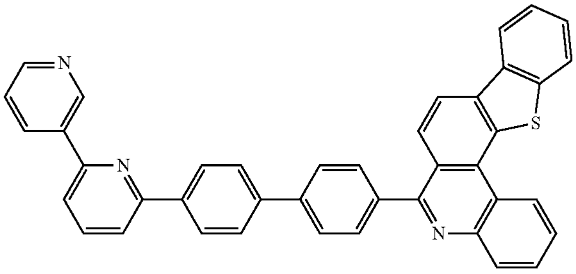
4-365
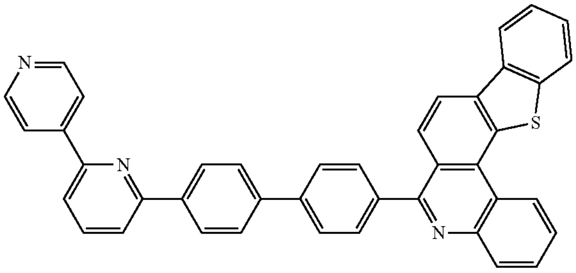

-continued
4-481
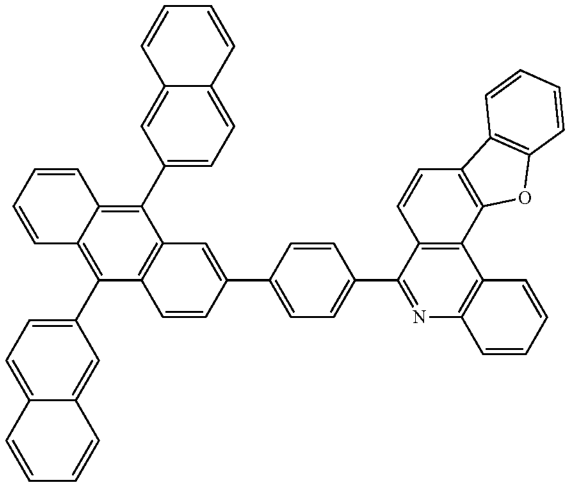
4-482
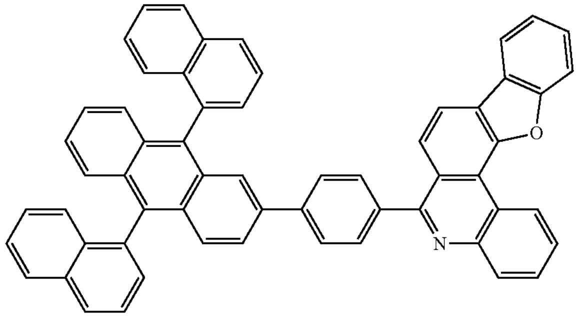
4-483
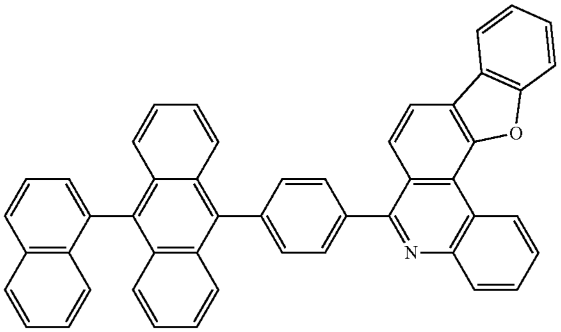
4-484
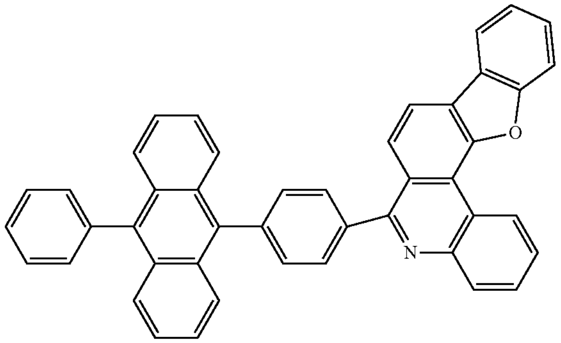
-continued
4-485
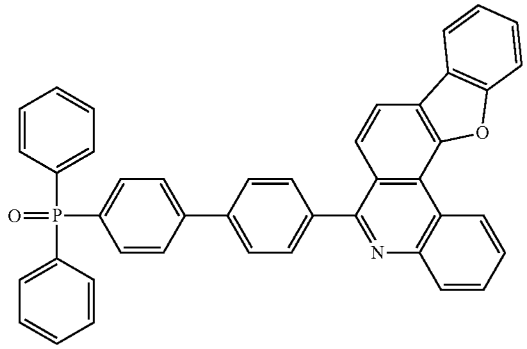
4-486
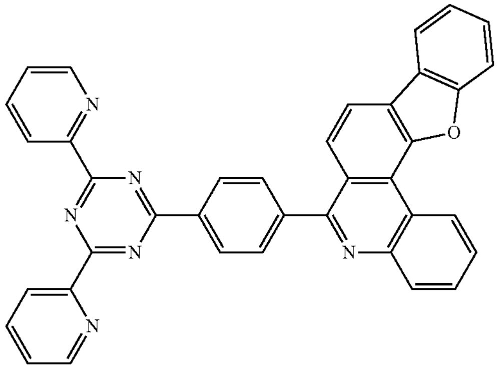
4-487
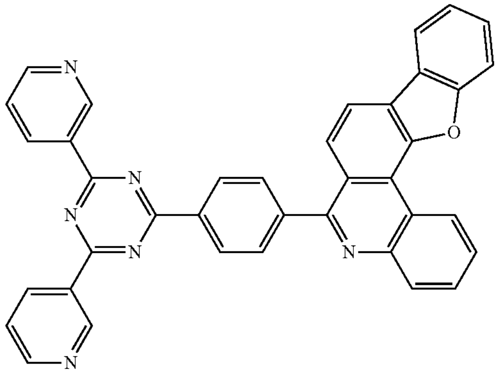
4-488
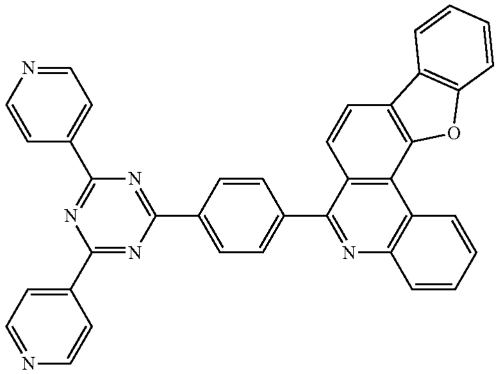

-continued
4-489
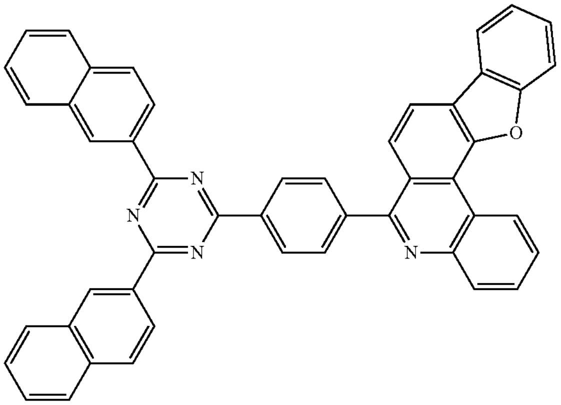
4-490
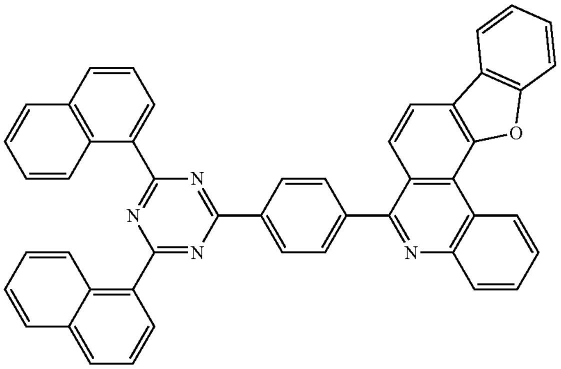
4-491
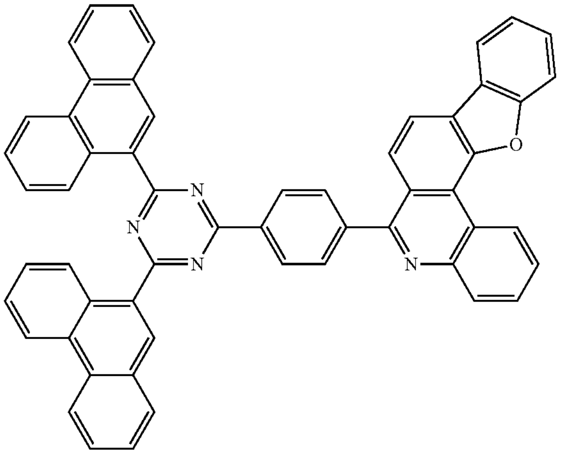
-continued
4-492
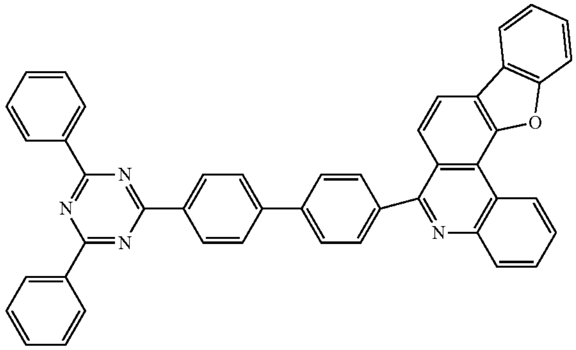
4-493
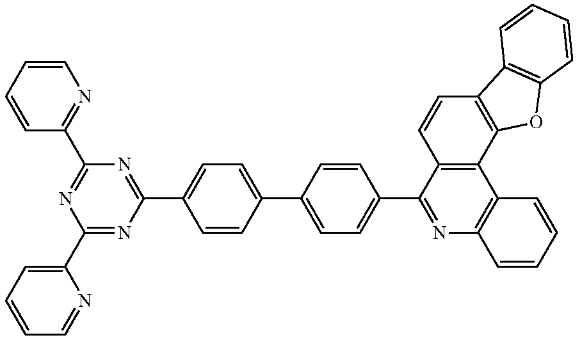
4-494
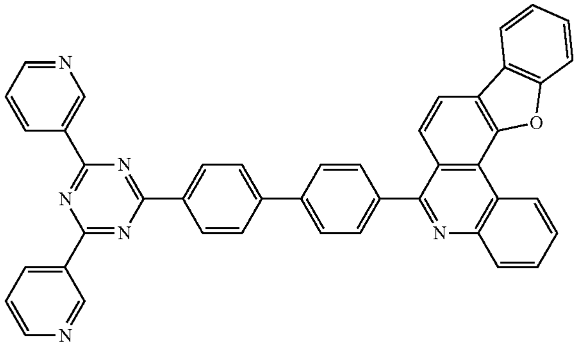
4-495
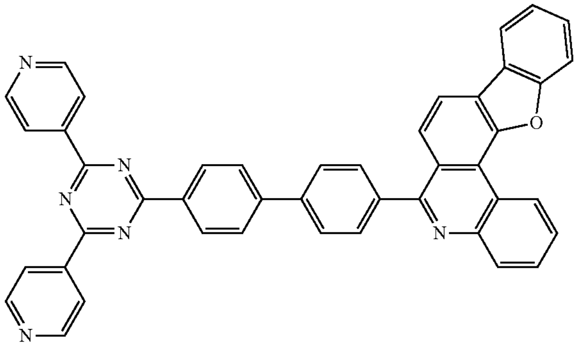

-continued
4-496
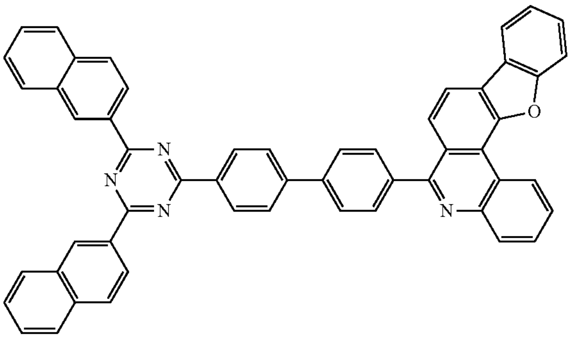
4-497
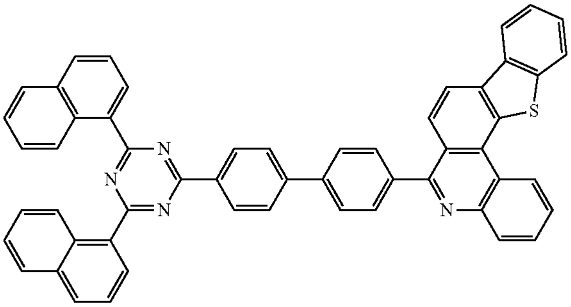
4-498
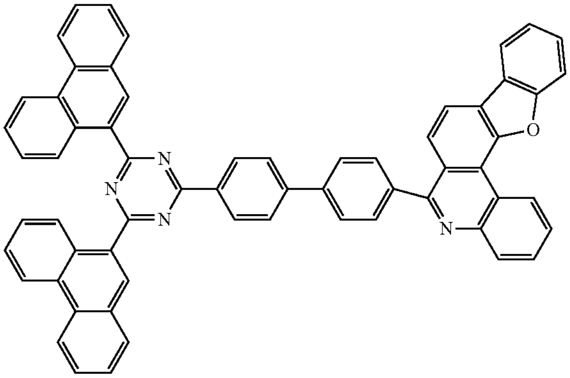
4-499
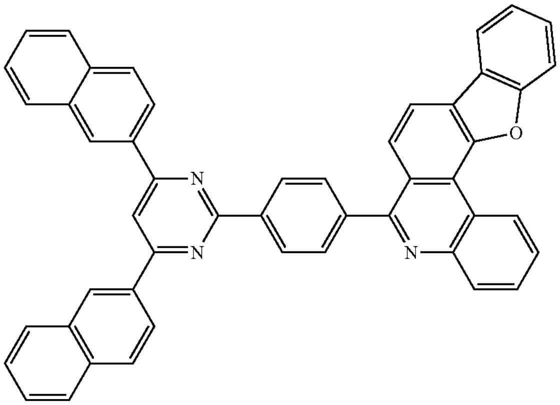
-continued
4-500
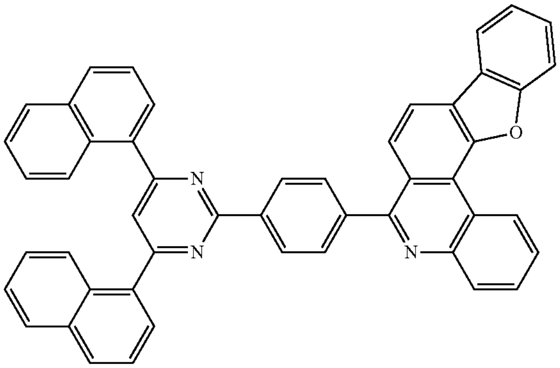
4-501
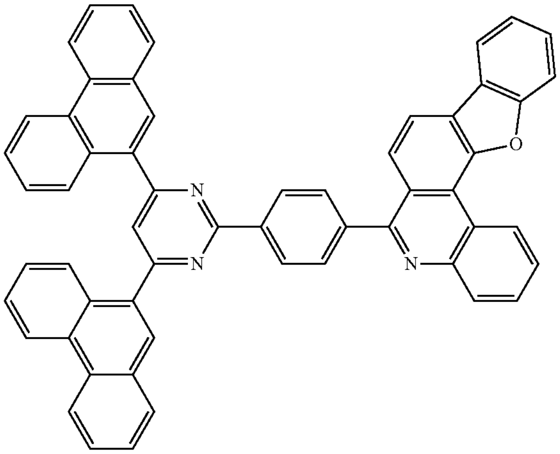
4-502
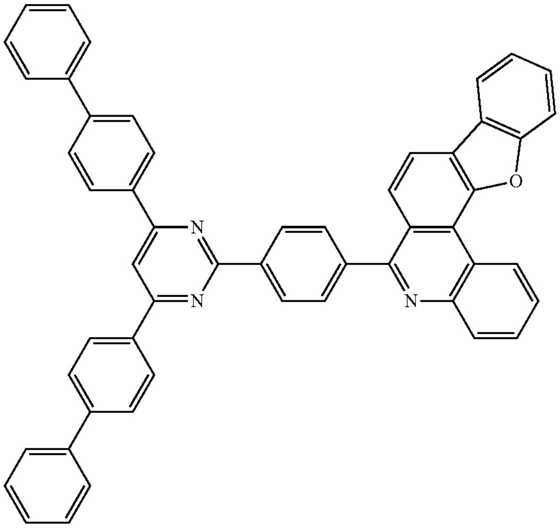

-continued
4-503
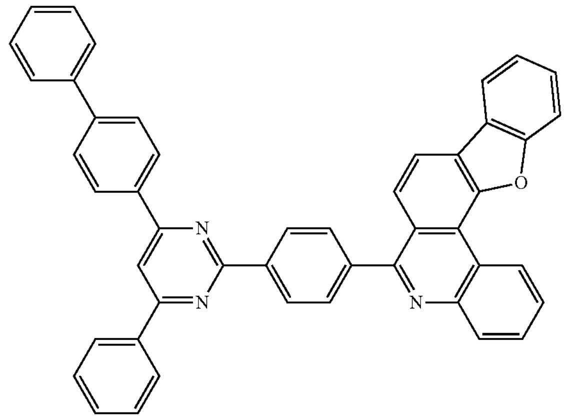
4-504
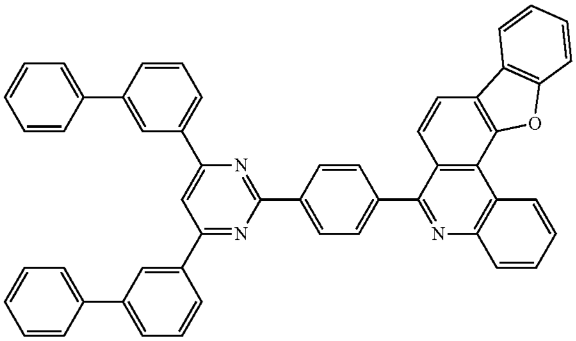
4-505
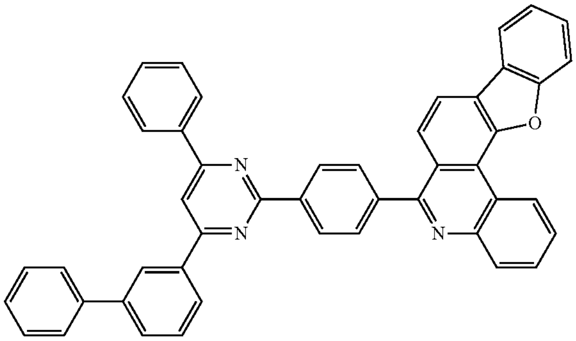
4-506
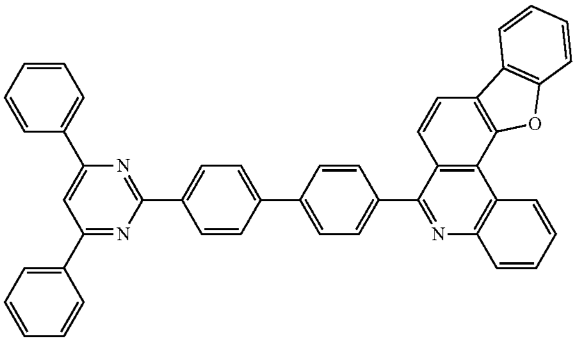
-continued
4-507
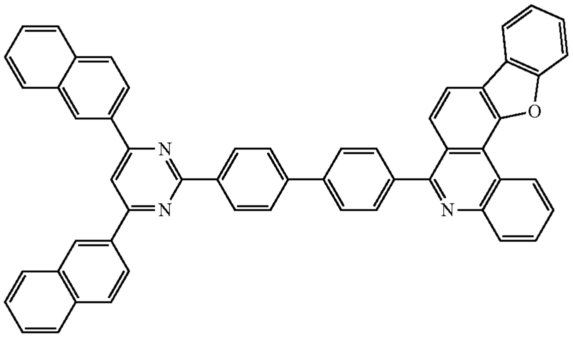
4-508
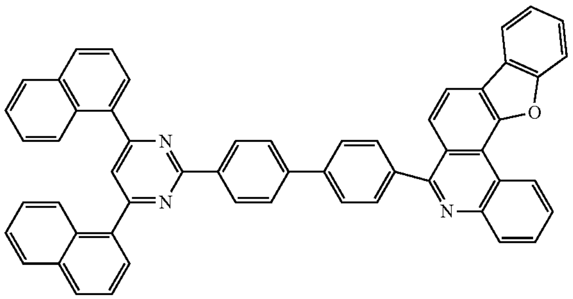
4-509
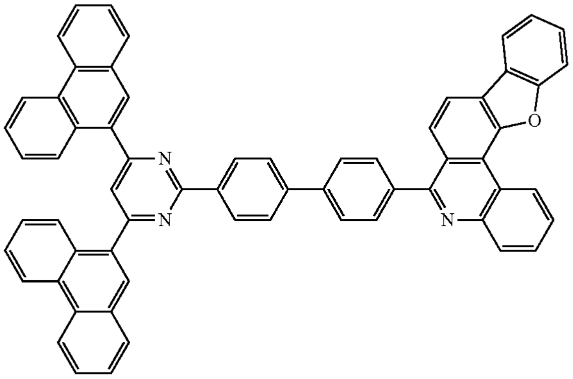
4-510
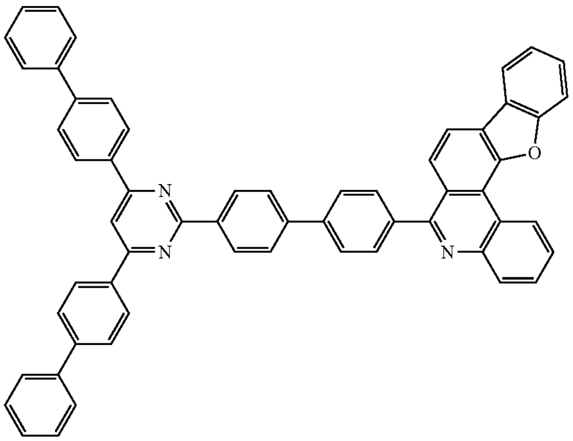

-continued
4-511
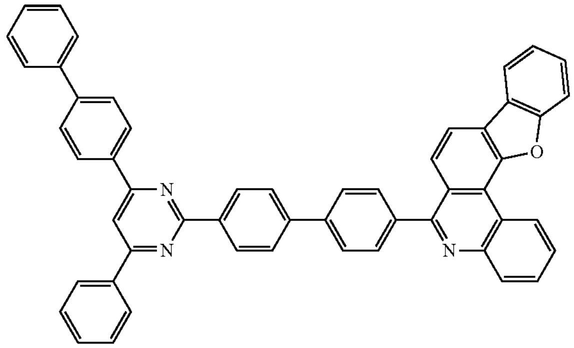
4-512
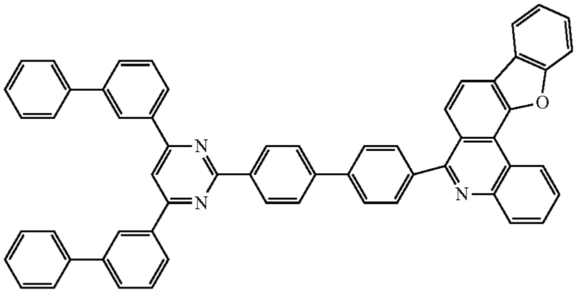
4-513
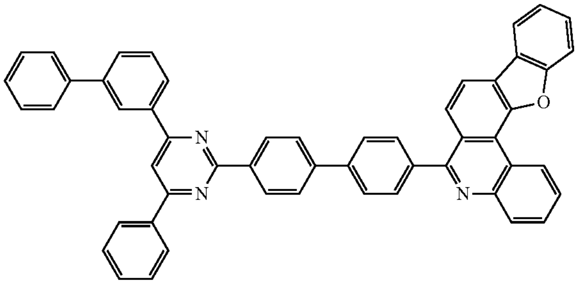
4-514
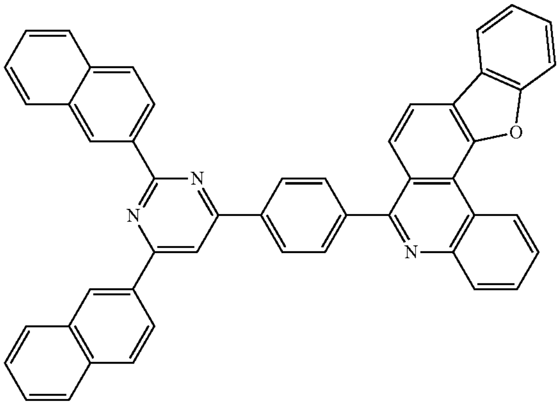
-continued
4-515
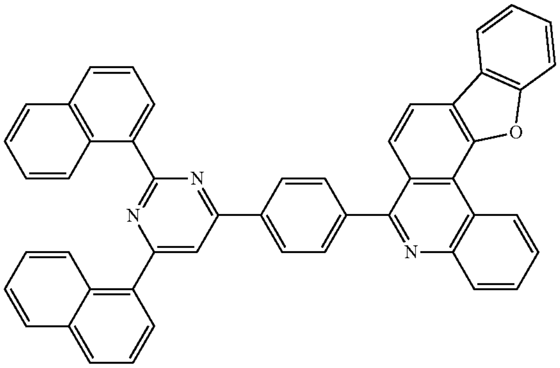
4-516
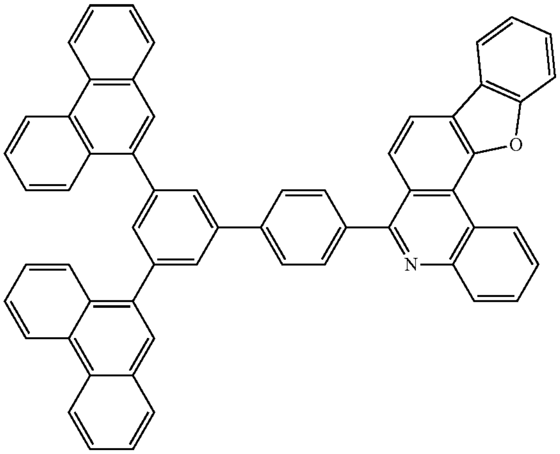
4-517
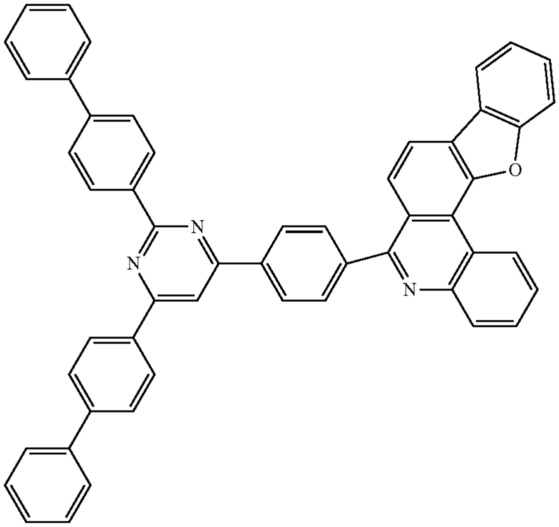

-continued
4-518
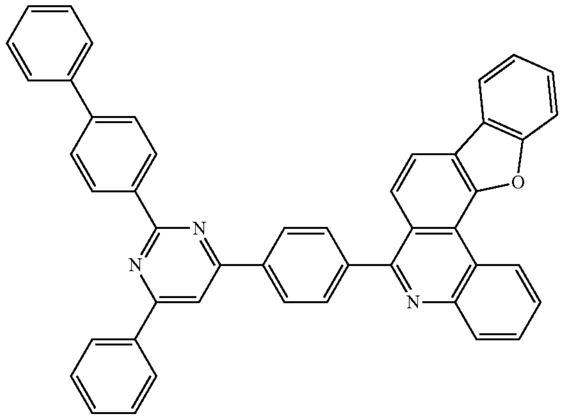
4-519
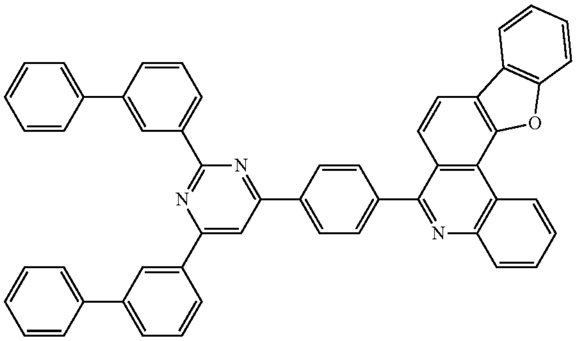
4-520
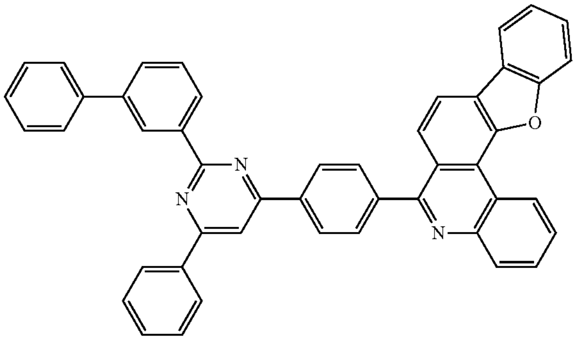
4-521
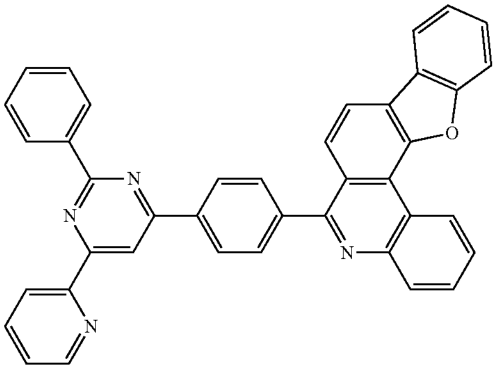
-continued
4-522
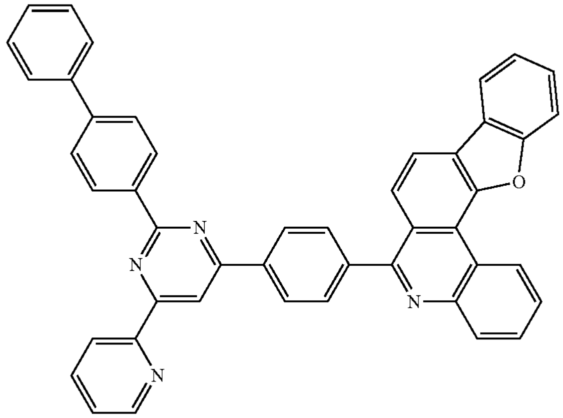
4-523
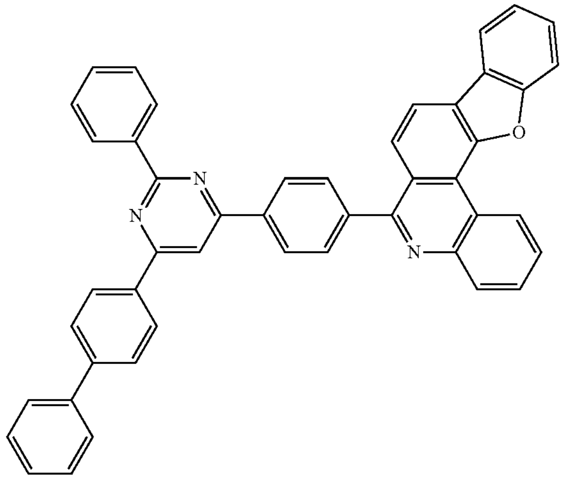
4-524
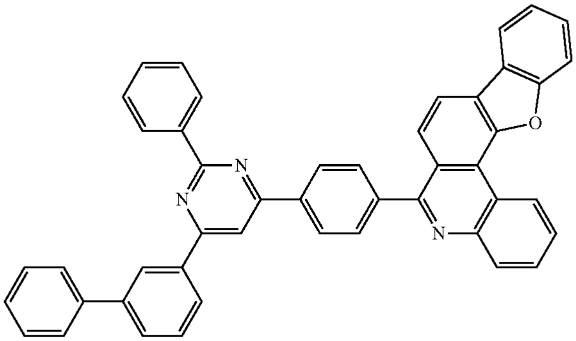

-continued
4-525
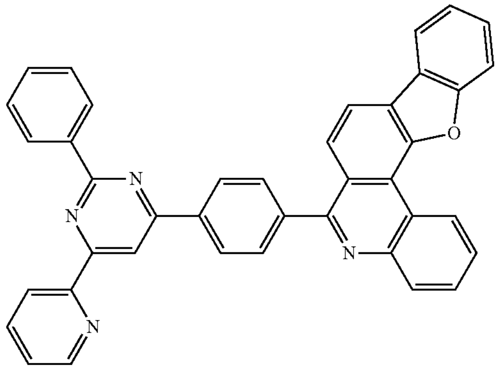
4-526
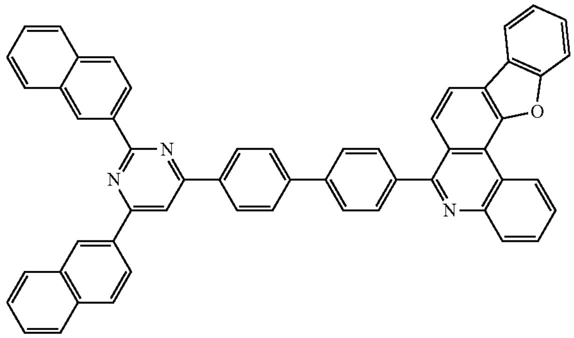
4-527
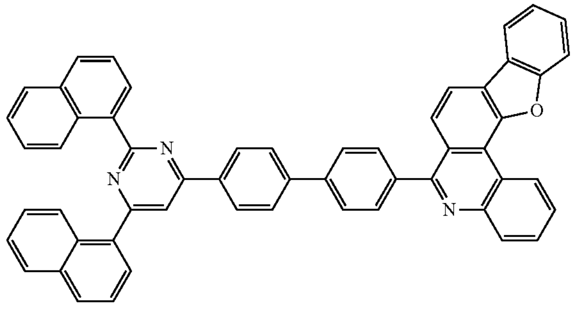
4-528
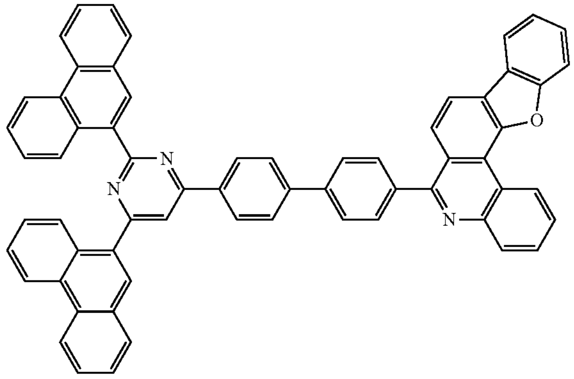
-continued
4-529
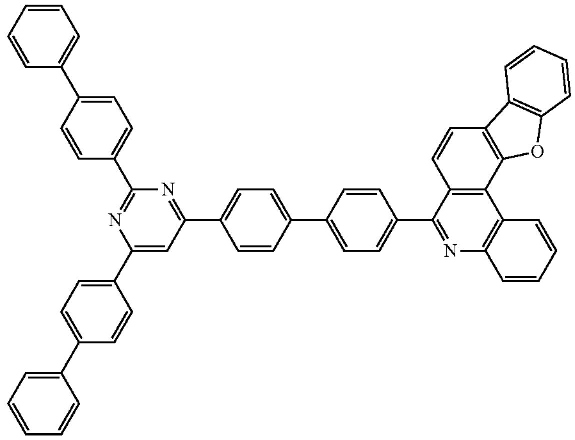
4-530
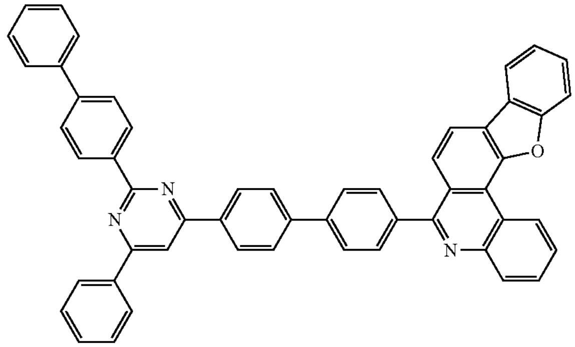
4-531
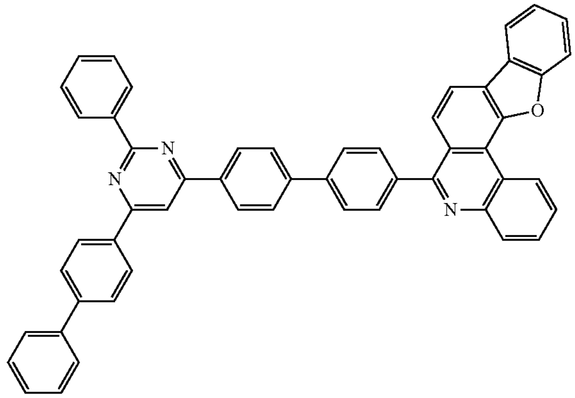
4-532
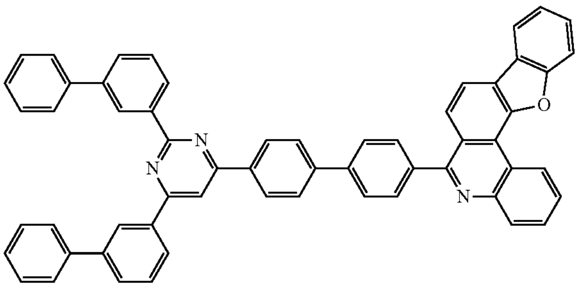

-continued
4-533
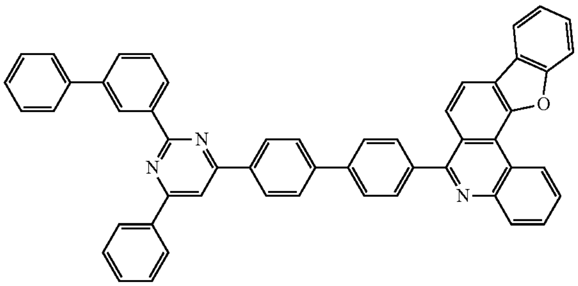
4-534
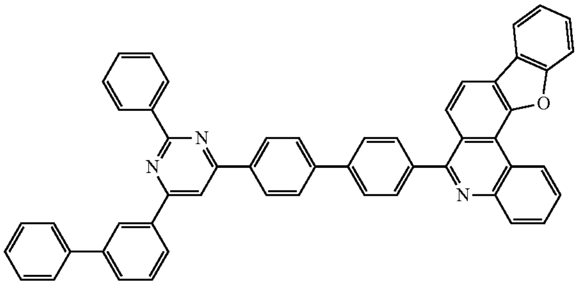
4-535
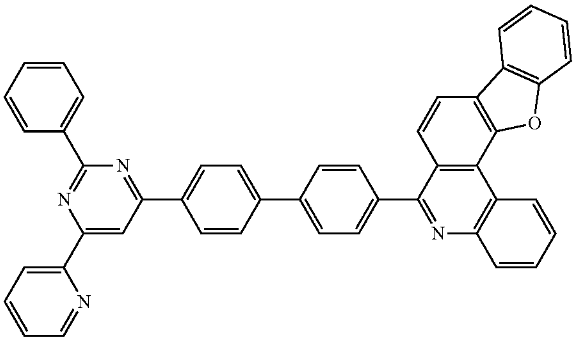
4-536
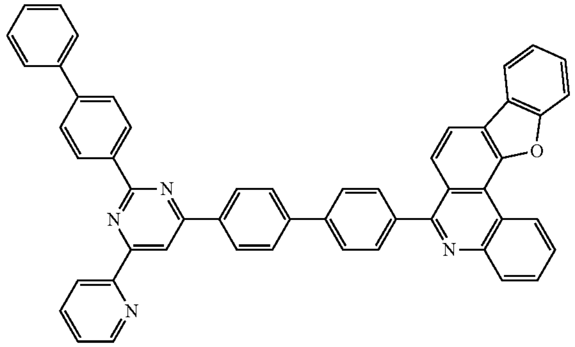
-continued
4-537
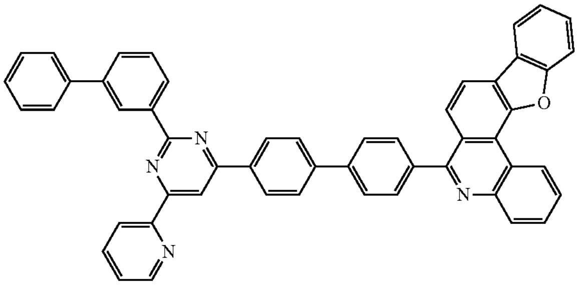
4-538
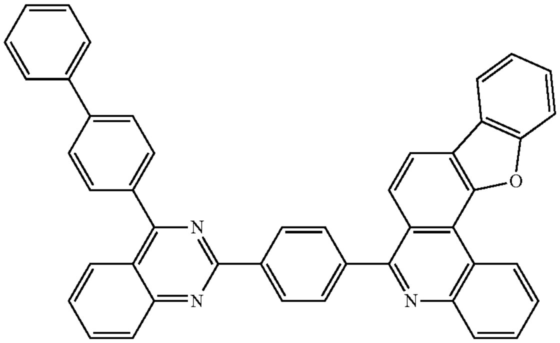
4-539
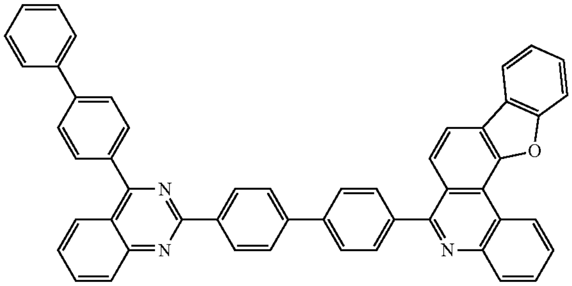
4-540
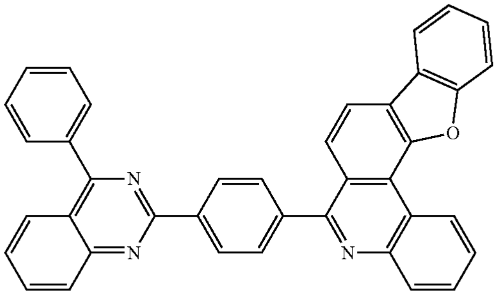
4-541
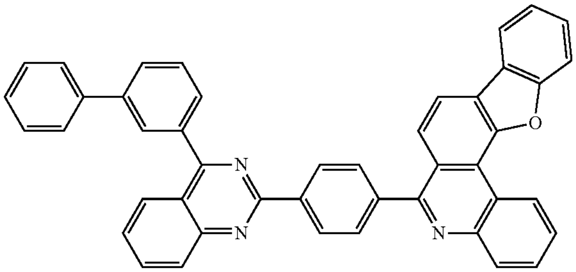

4-542
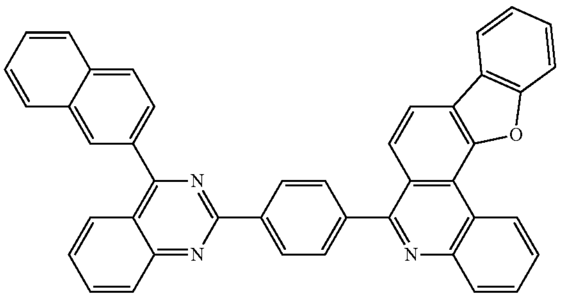
4-543
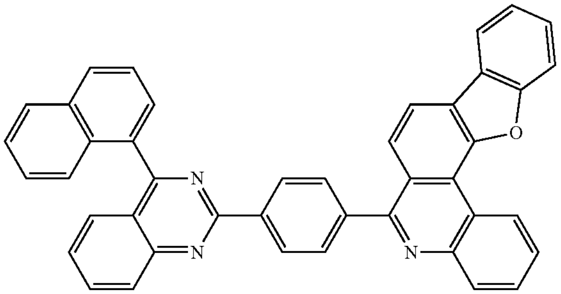
4-544
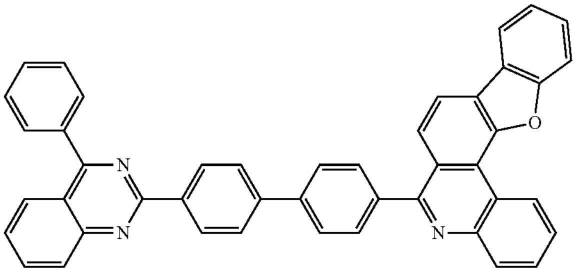
4-545
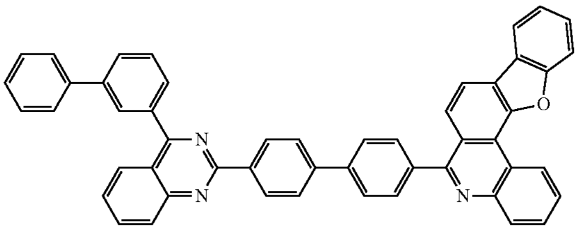
4-546
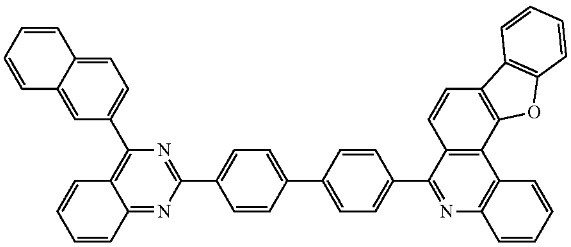
4-547
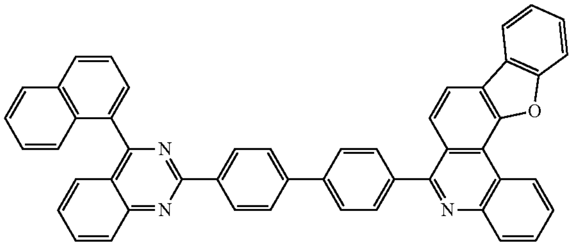
4-548
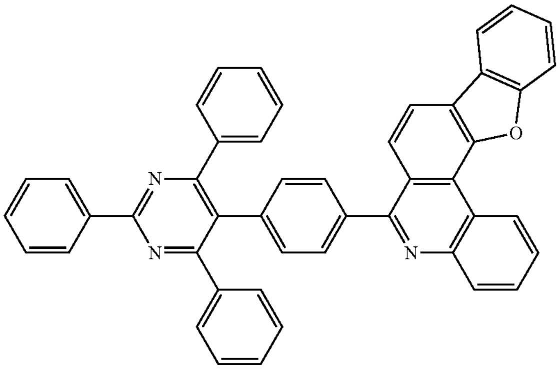
4-549
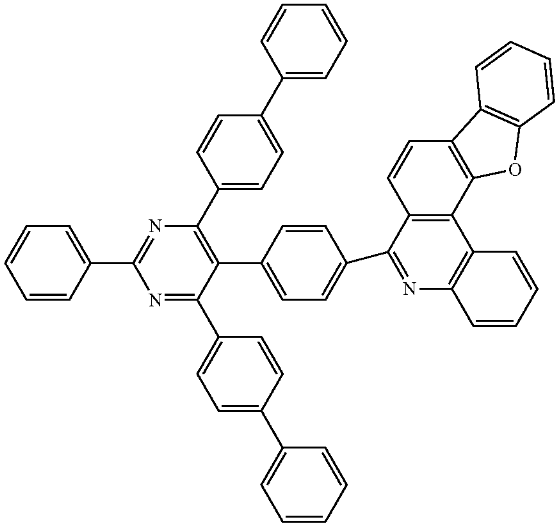

-continued
4-550
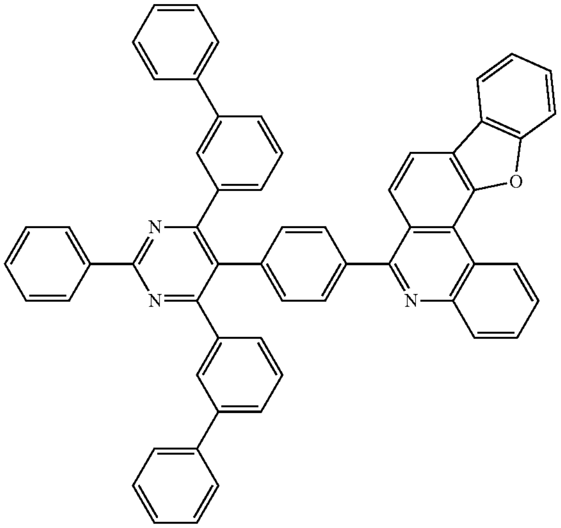
4-551
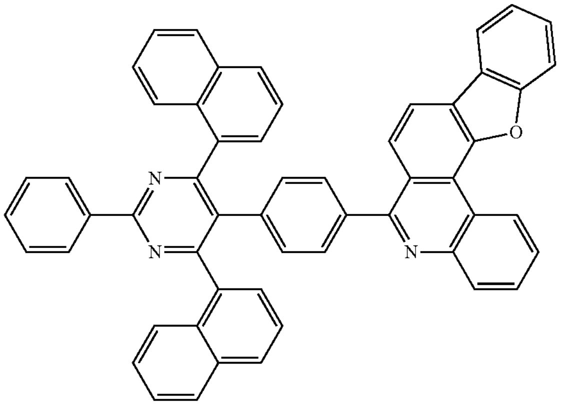
4-552
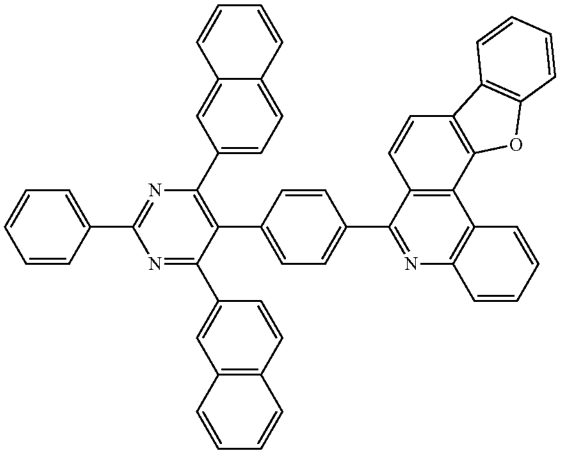
-continued
4-553
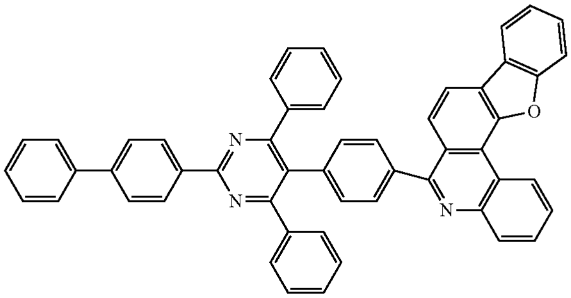
4-554
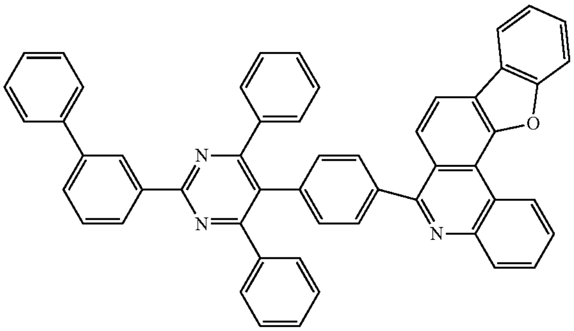
4-555
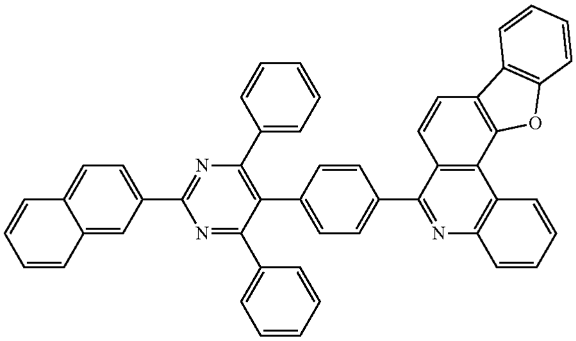
4-556
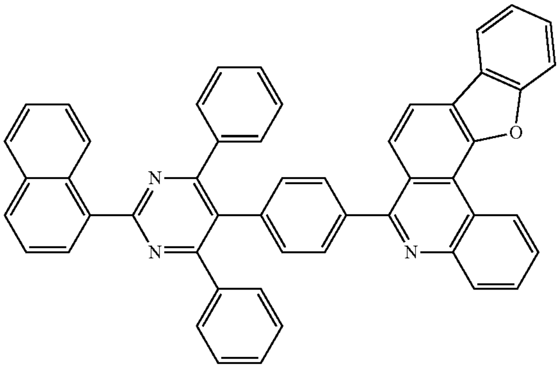

-continued
4-557
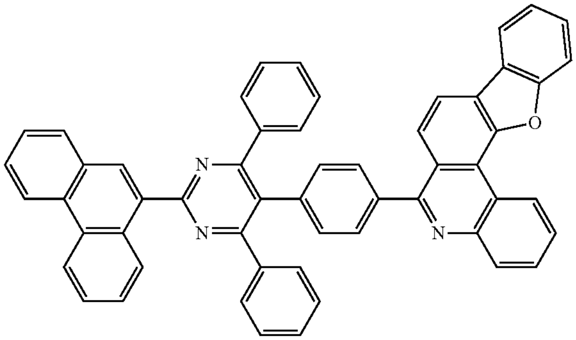
4-558
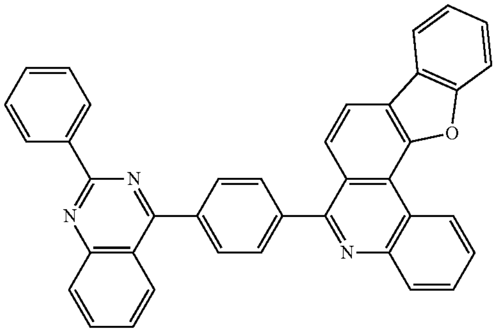
4-559
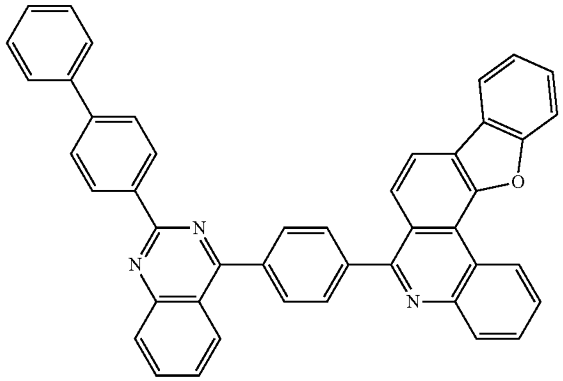
4-560
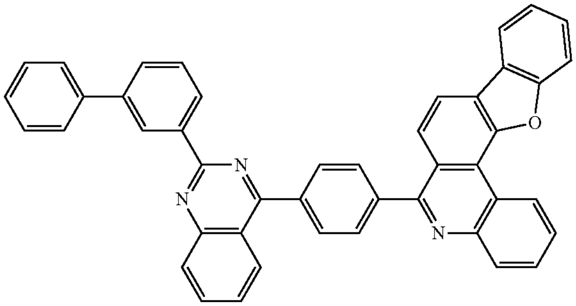
-continued
4-561
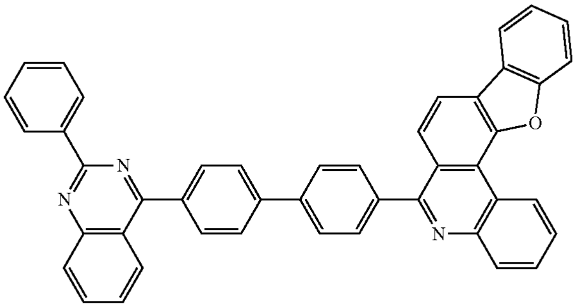
4-562
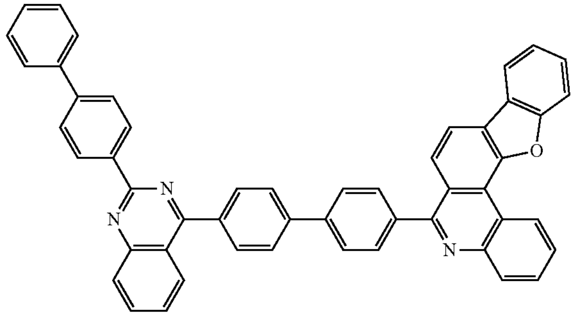
4-563
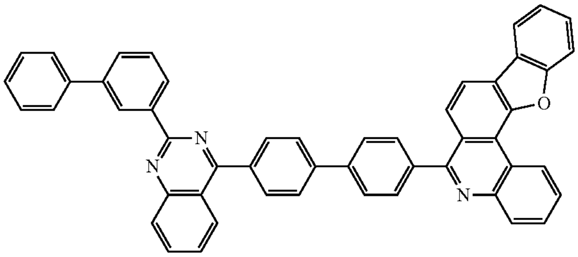
4-564
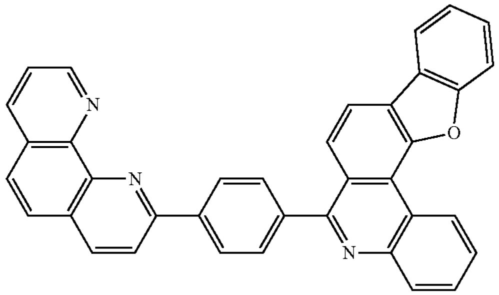
4-565
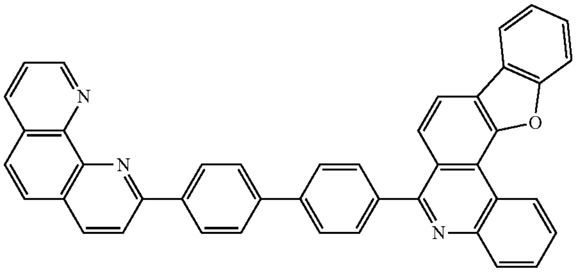

-continued
4-566
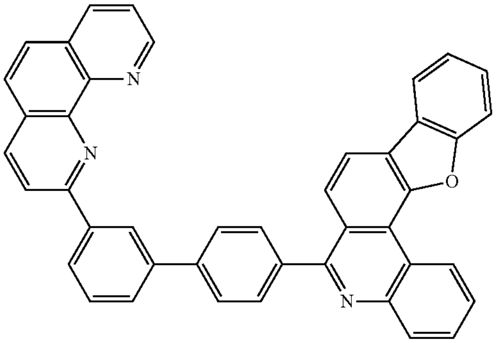
4-567
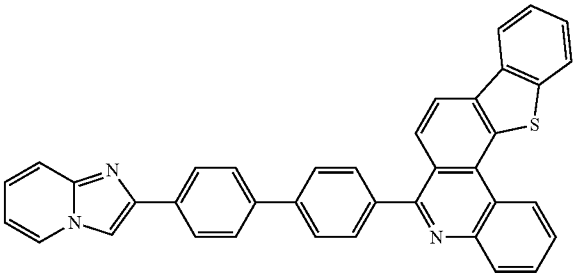
4-568
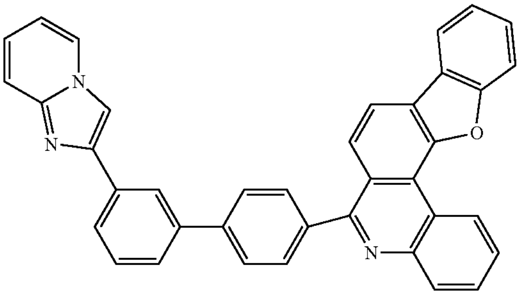
4-569
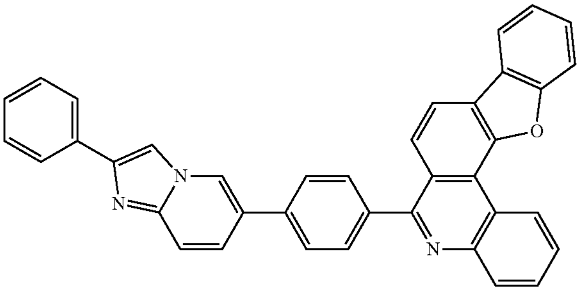
-continued
4-570
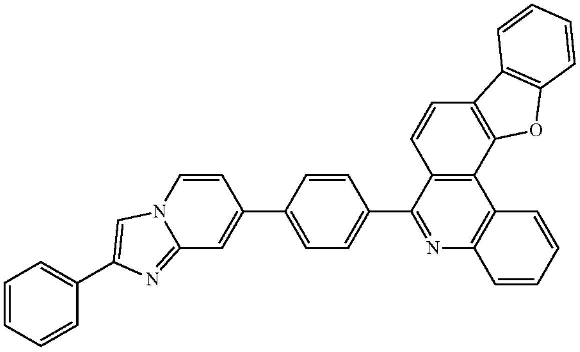
4-571
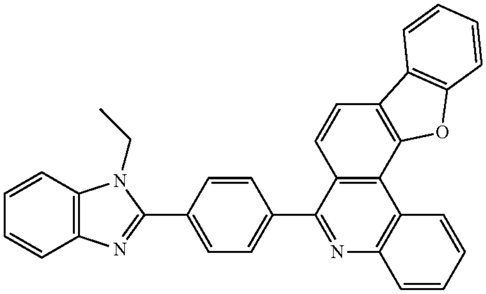
4-572
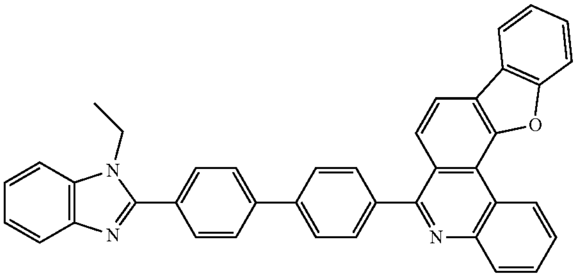
4-573
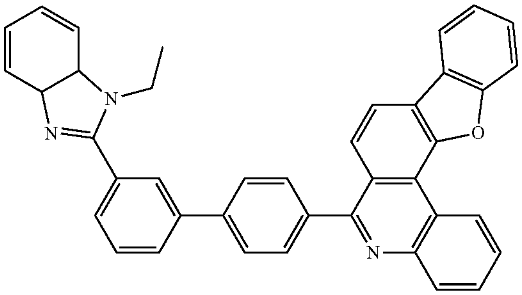
4-574
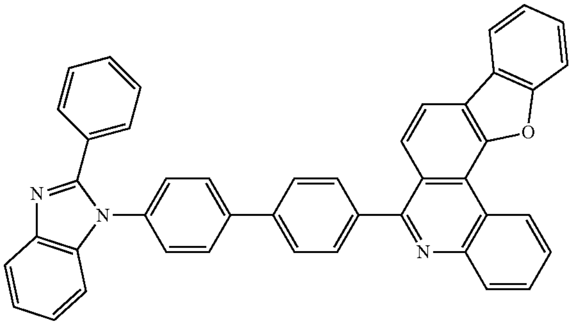

4-575
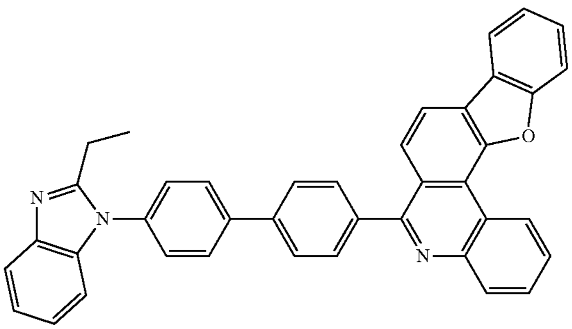
4-576
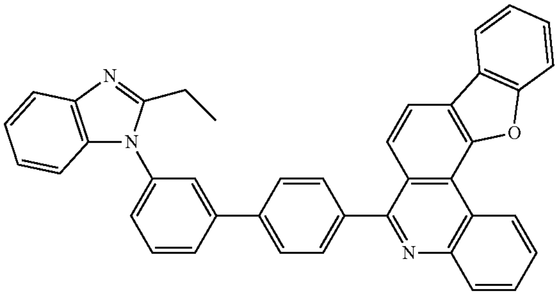
4-577
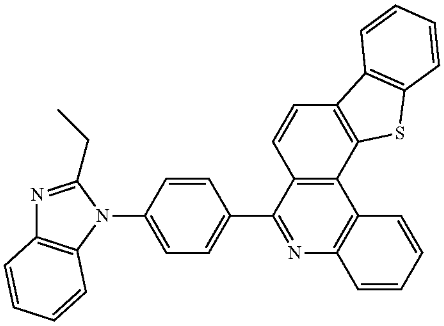
4-578
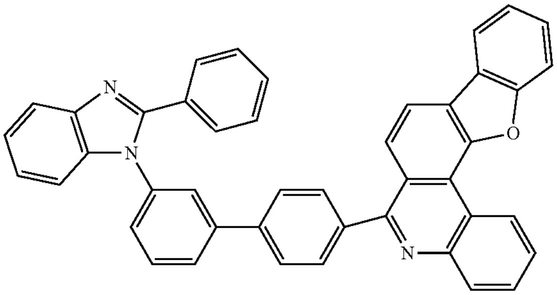
4-579
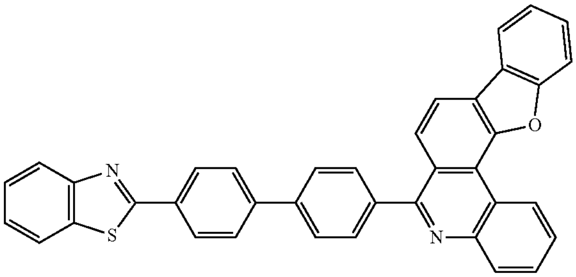
4-580
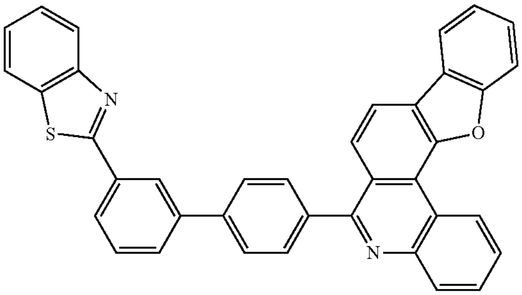
4-581
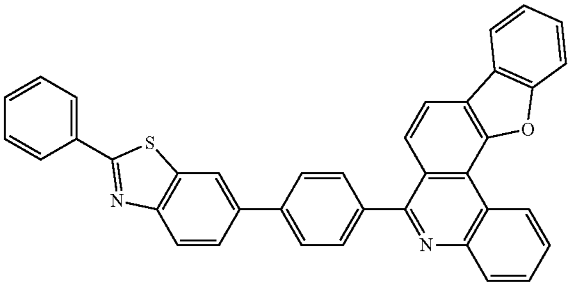
4-582
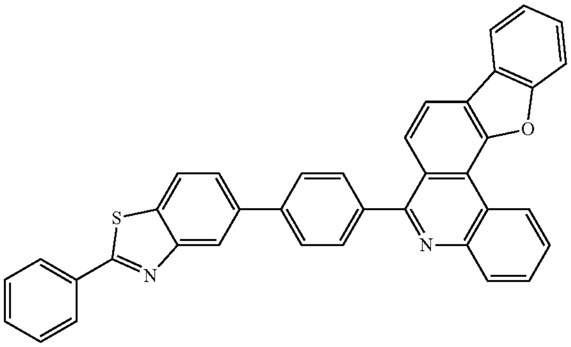
4-583
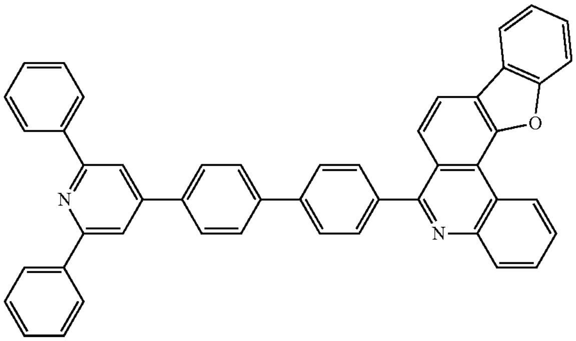

-continued
4-584
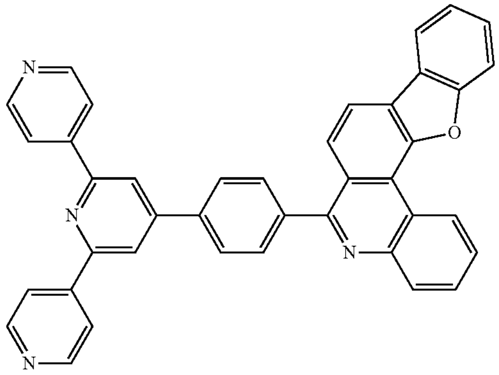
4-585
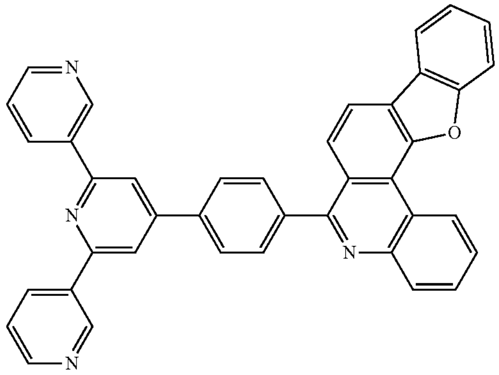
4-586
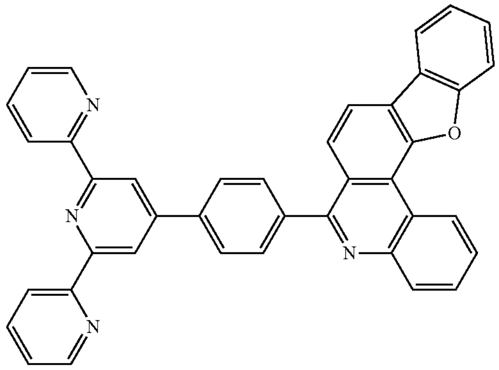
4-587
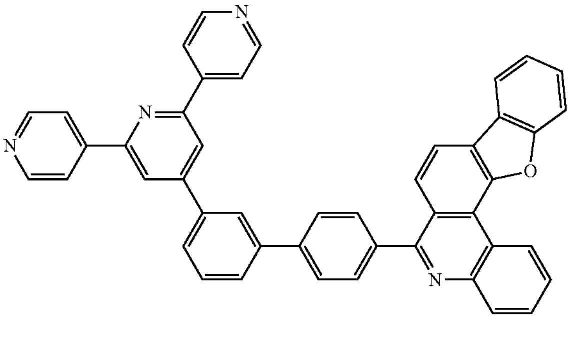
-continued
4-588
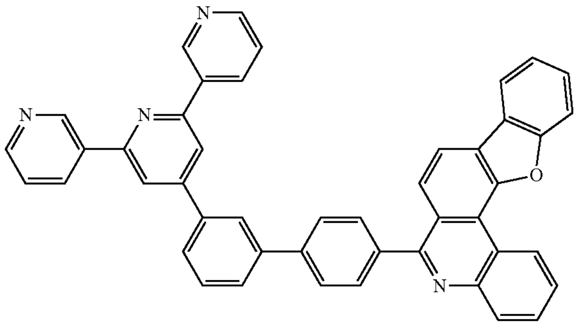
4-589
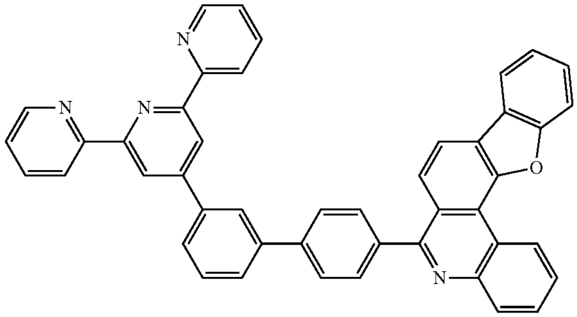
4-590
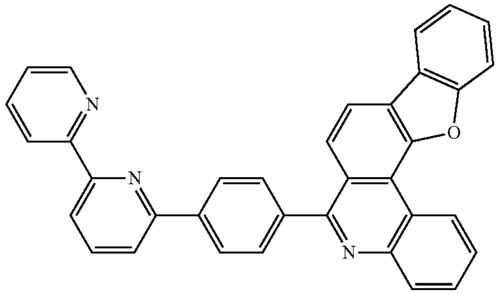
4-591
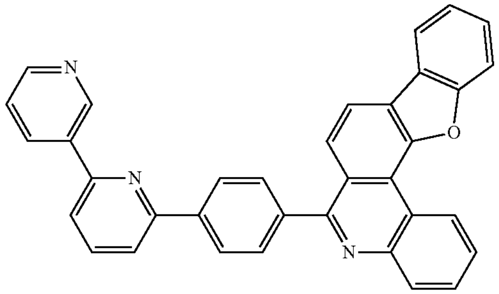
4-592
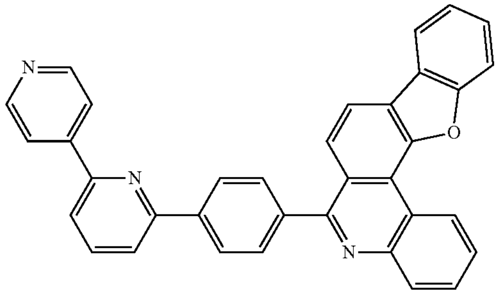

-continued
4-593
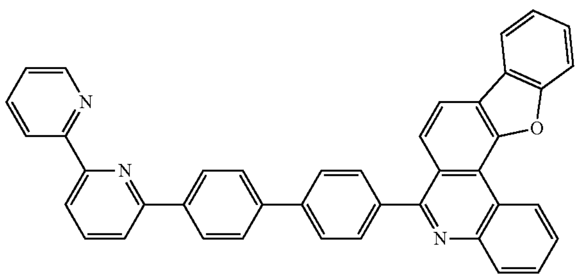
4-594
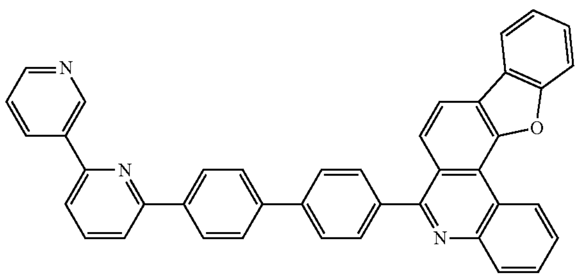
4-595
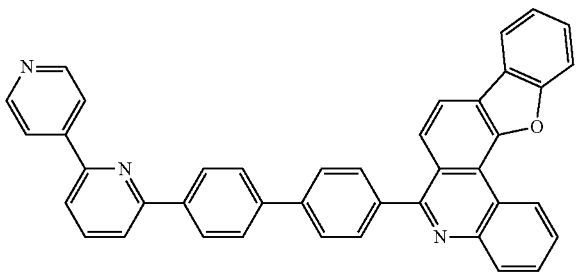
According to another exemplary embodiment of the present specification,
in Chemical Formulas 24 and 30, Ar may be bonded to an atom bonded to a core of phenyl at a meta position thereof, and Chemical Formulas 24 and 30 may be selected from the following compounds.
4-91
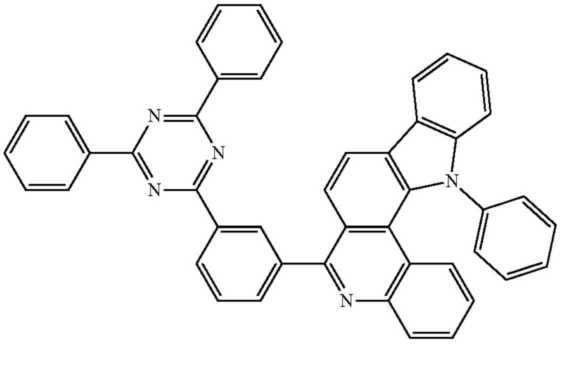
-continued
4-92
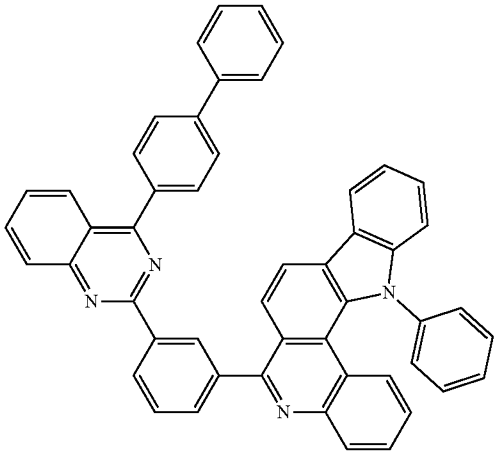
4-93
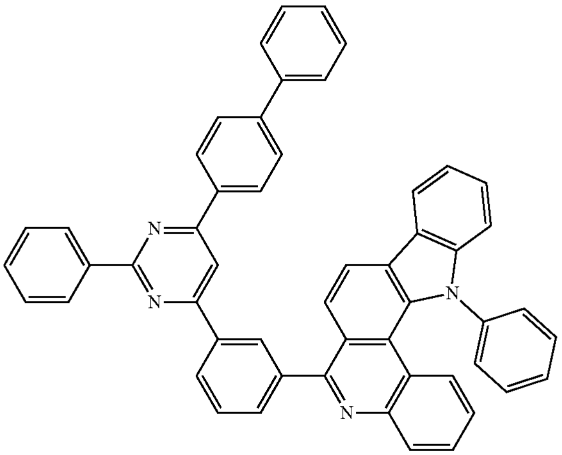
4-94
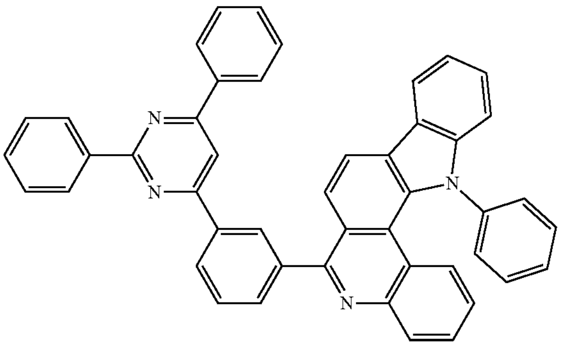
4-95
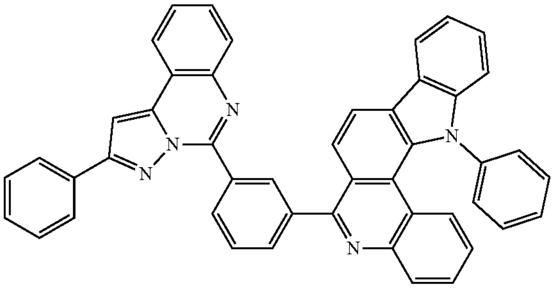

-continued
4-96
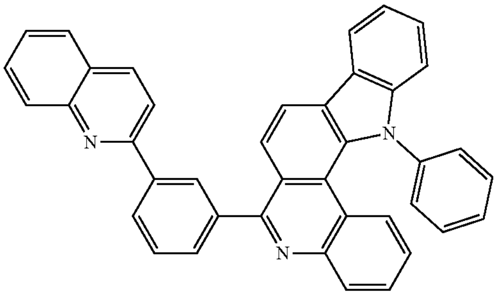
4-97
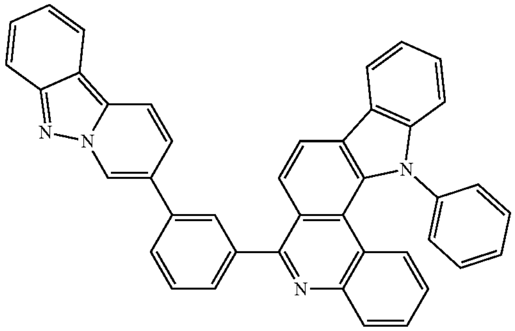
4-98
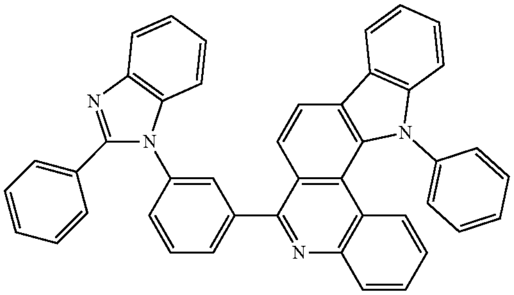
4-99
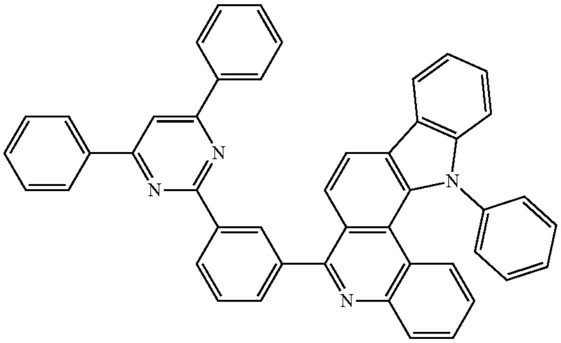
-continued
4-100
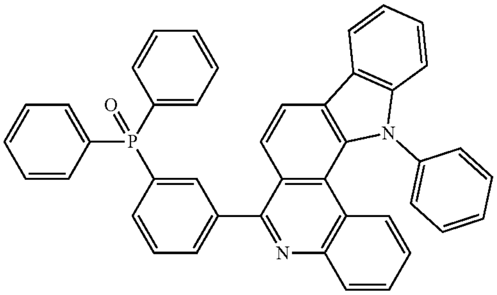
4-101
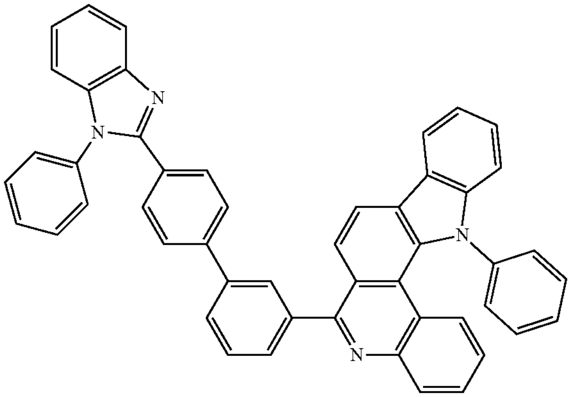
4-102
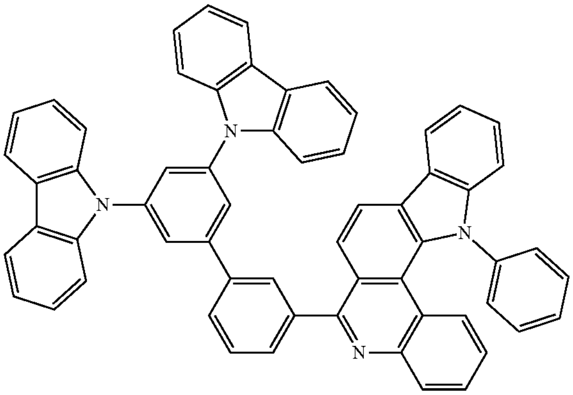
4-103
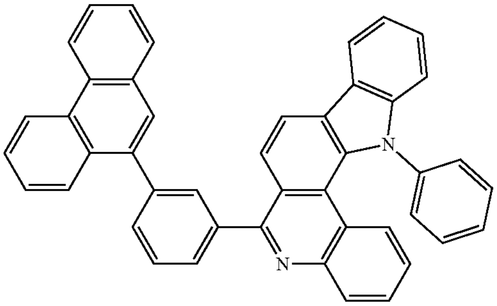

-continued
4-104
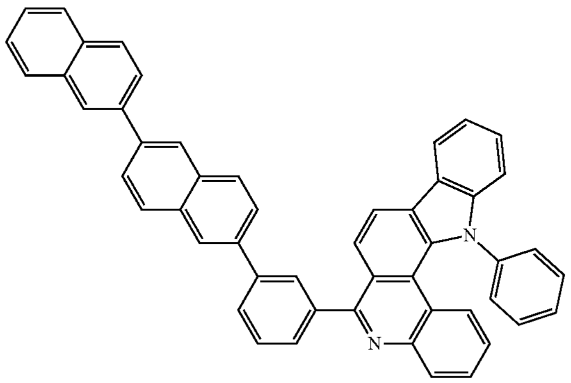
4-105
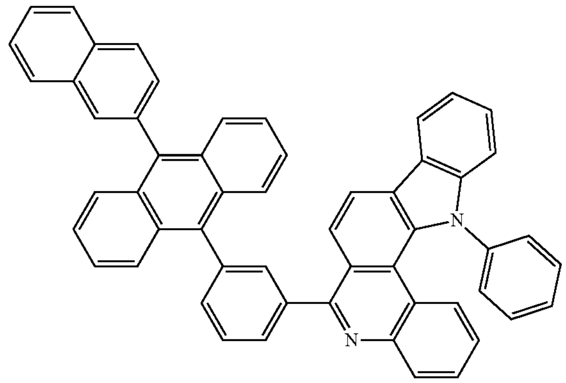
4-106
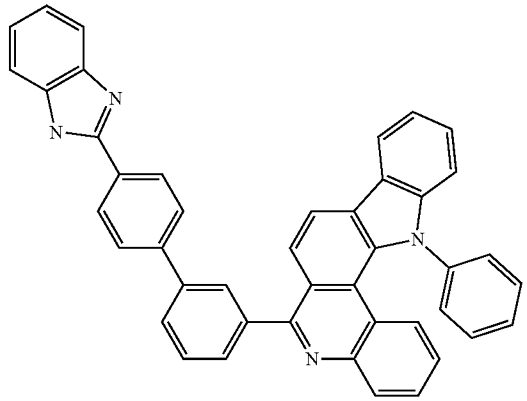
4-107
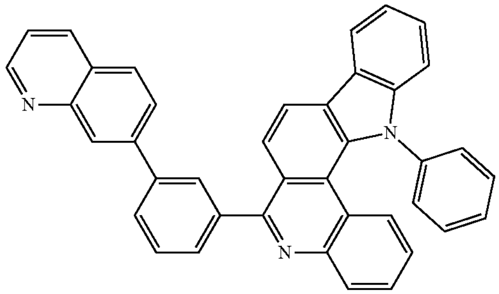
-continued
4-108
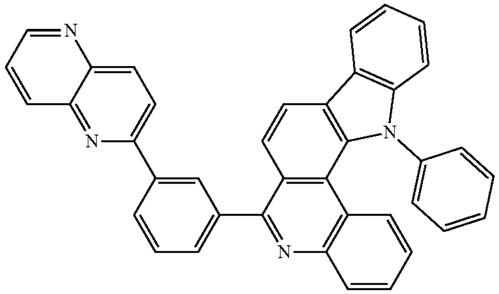
4-109
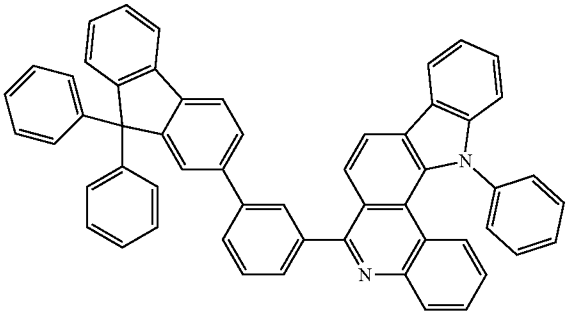
4-110
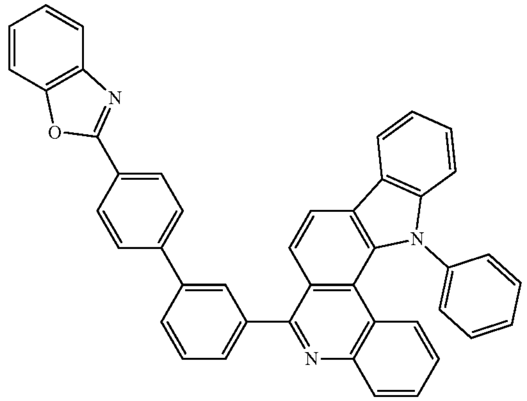
4-111
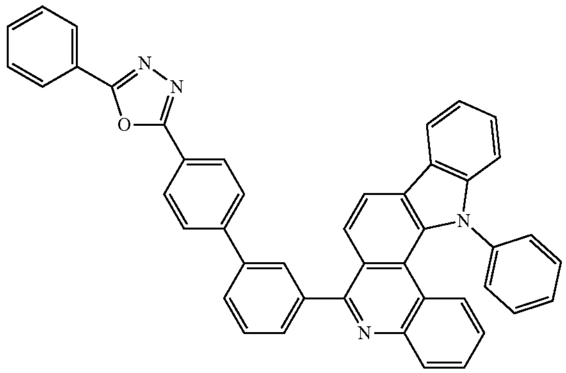

-continued
4-112
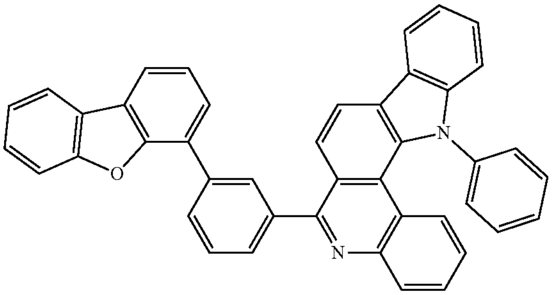
4-113
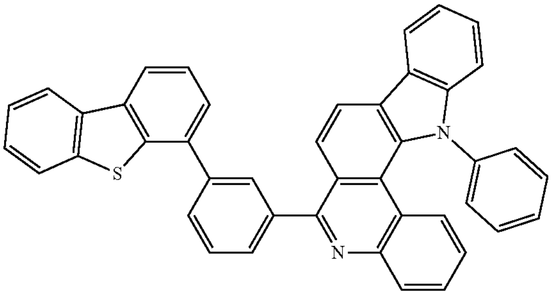
4-114
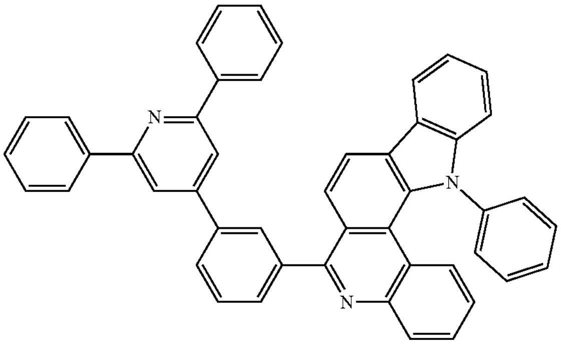
4-115
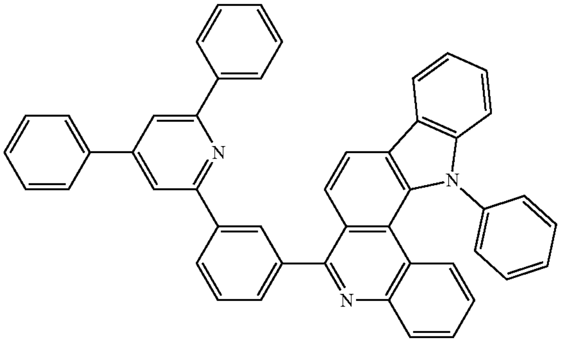
-continued
4-116
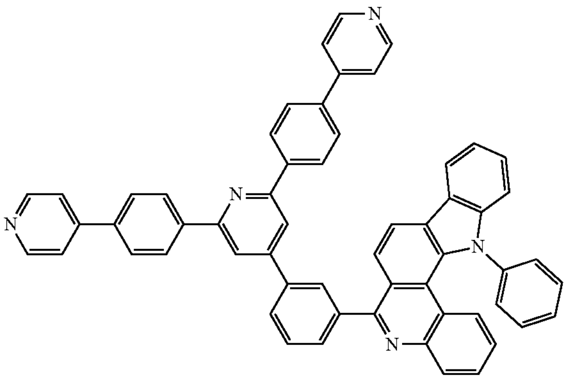
4-117
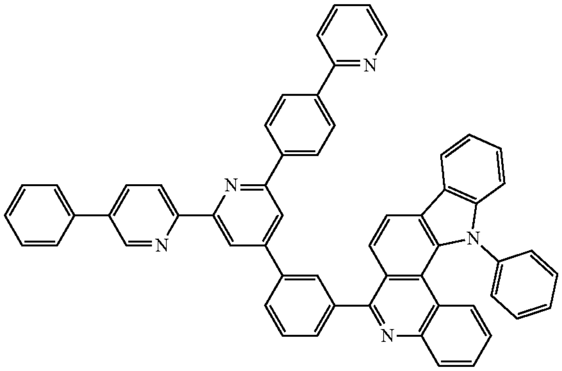
4-118
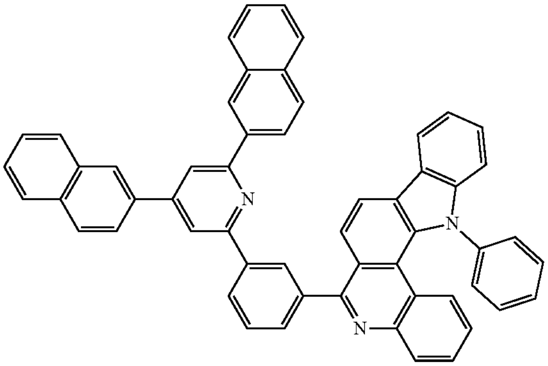
4-119
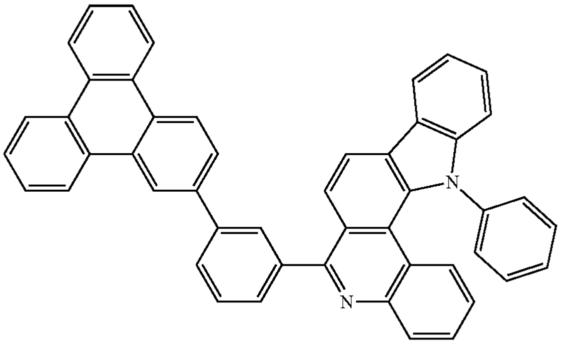

-continued
4-120
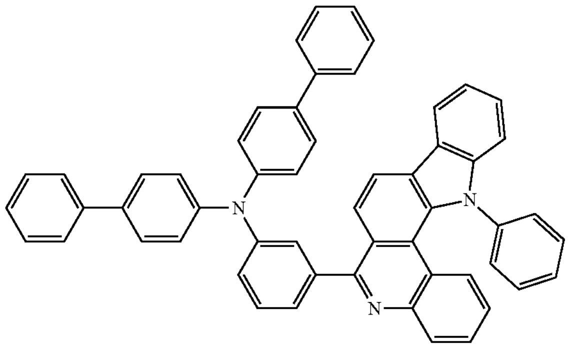
4-121
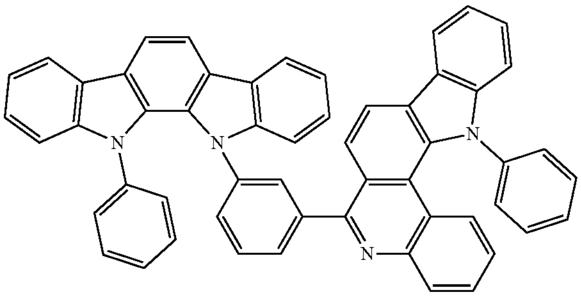
4-122
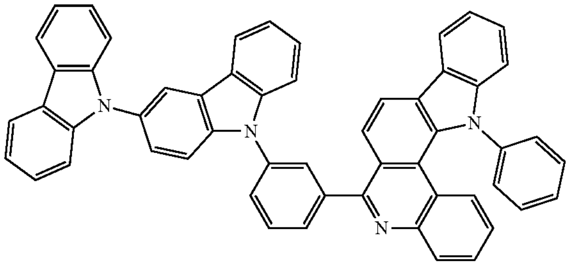
4-123
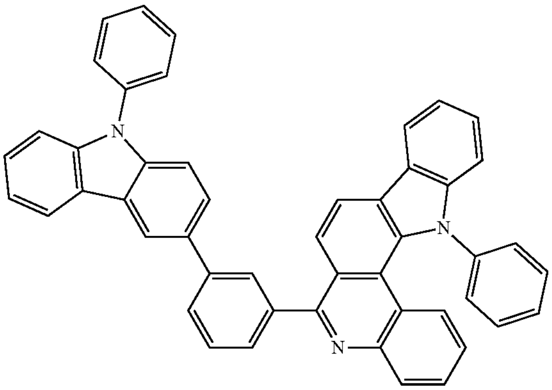
-continued
4-124
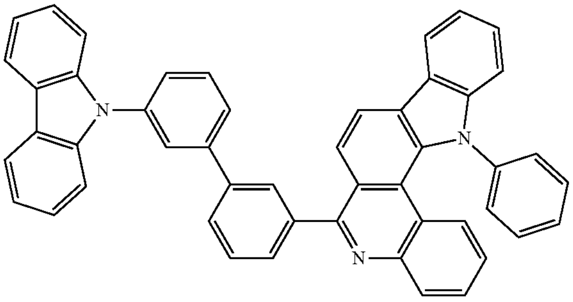
4-125
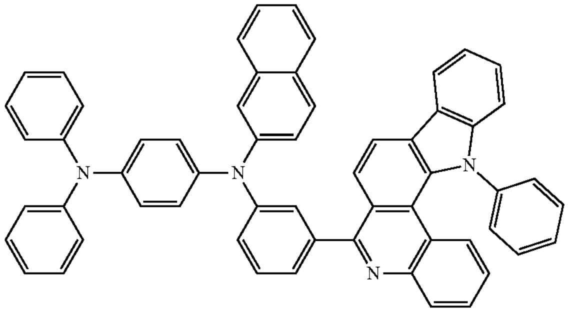
4-126
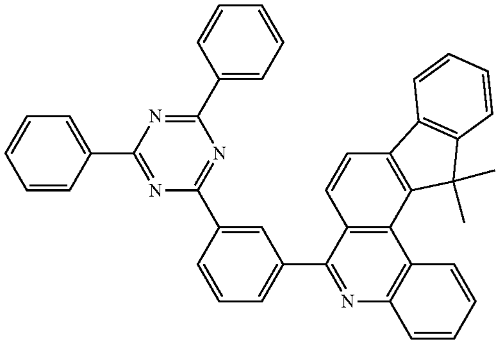
4-127
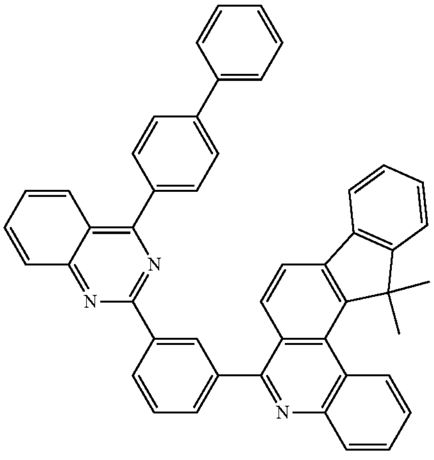

-continued
4-128
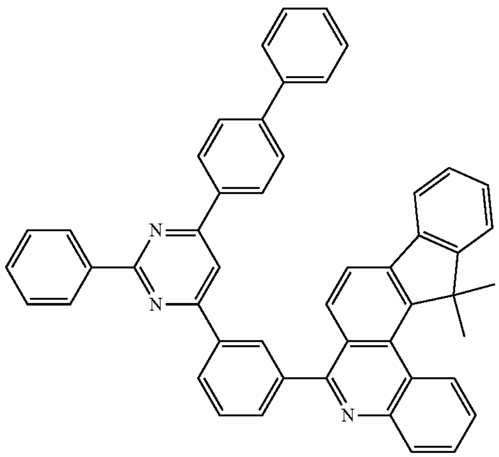
4-129
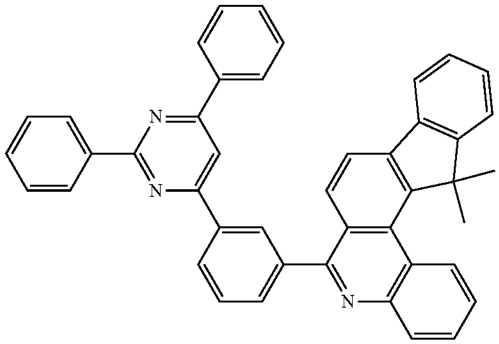
4-130
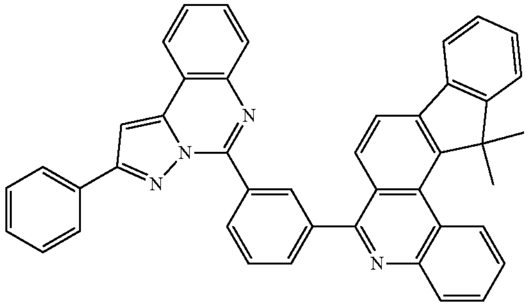
4-131
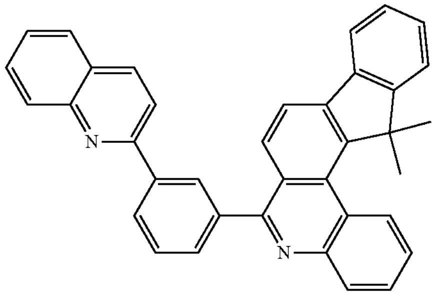
-continued
4-132
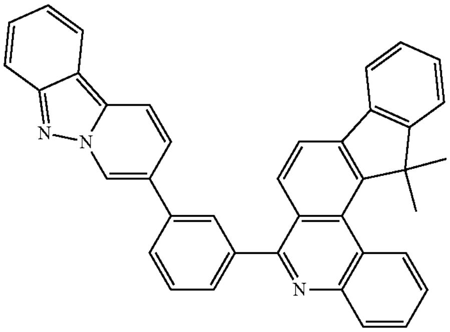
4-133
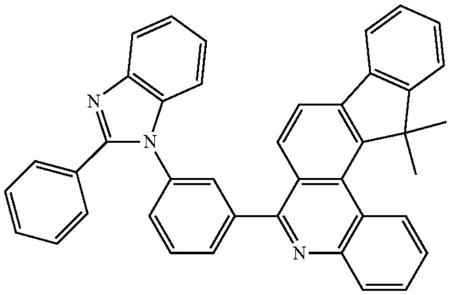
4-134
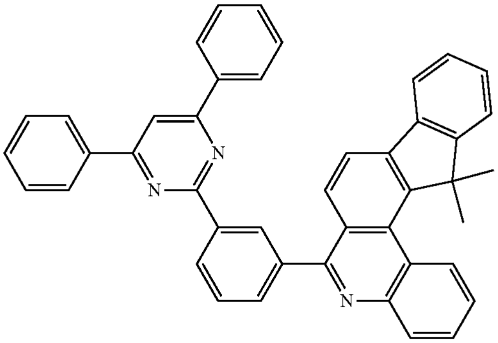
4-135
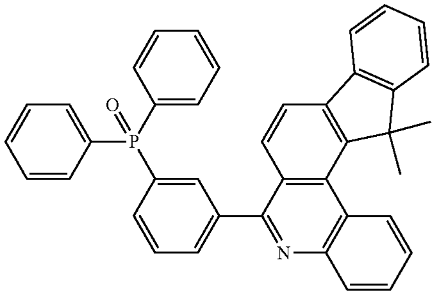

-continued
4-136
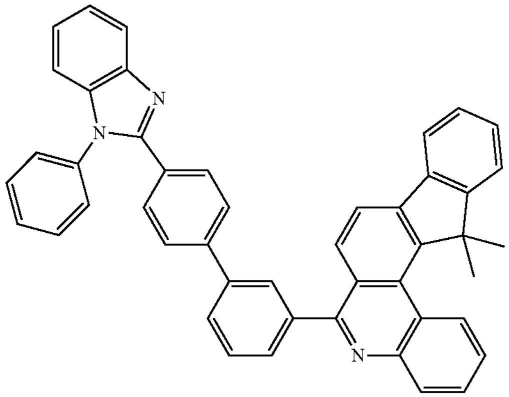
4-137
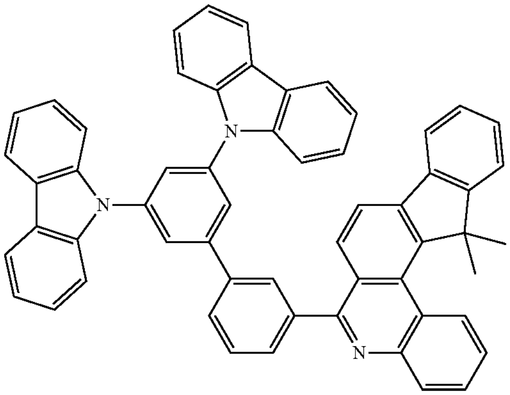
4-138
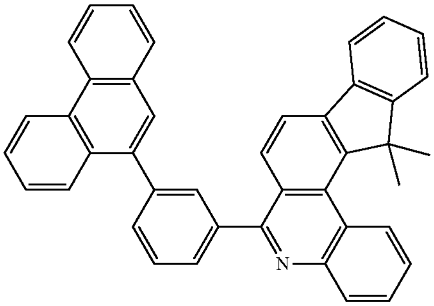
4-139
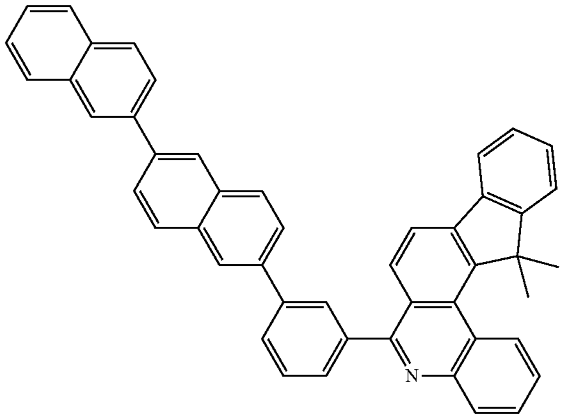
-continued
4-140
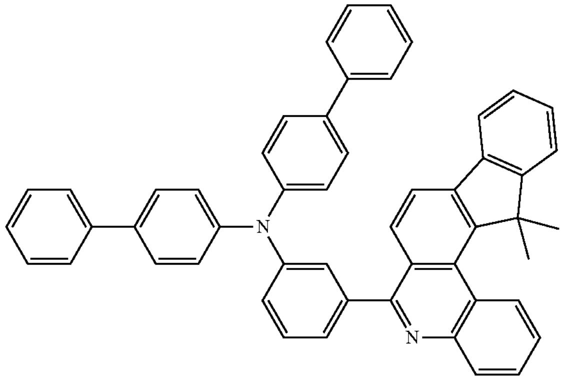
4-141
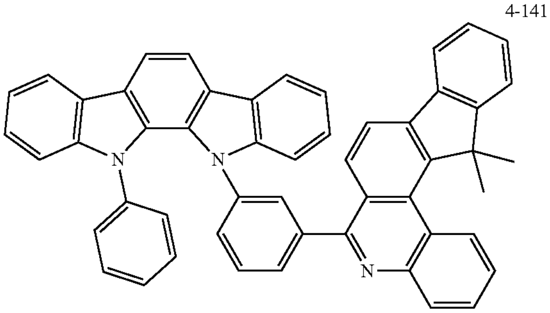
4-142
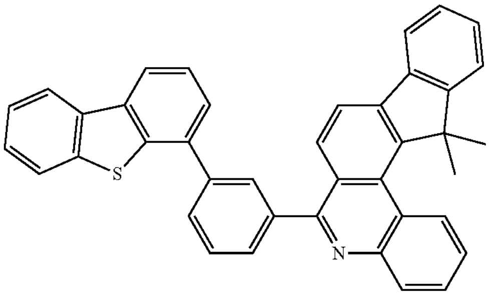
4-143
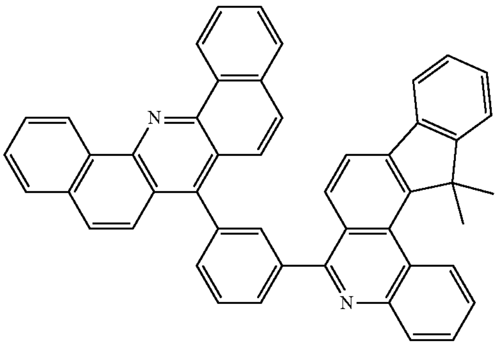

-continued
4-144
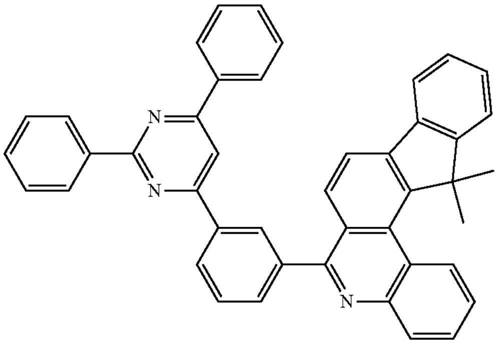
4-145
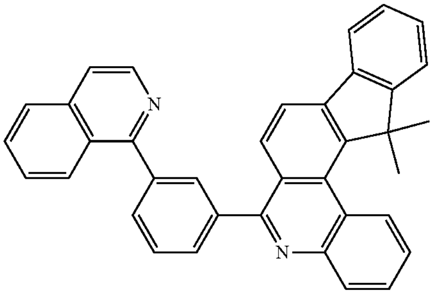
4-146
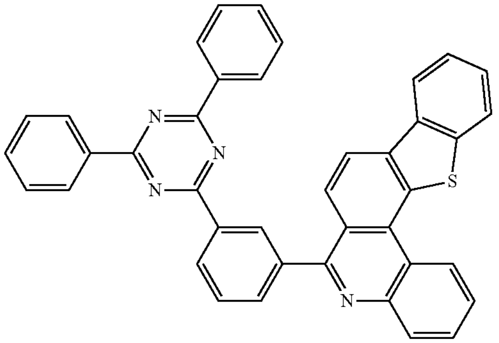
4-147
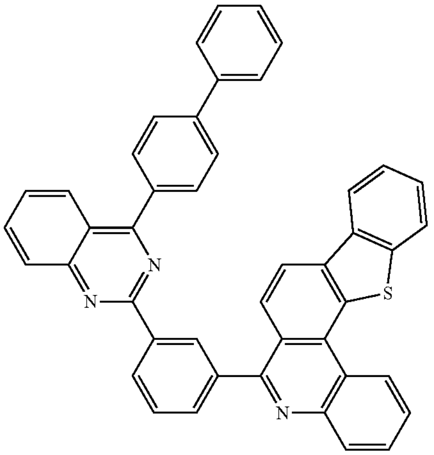
-continued
4-148
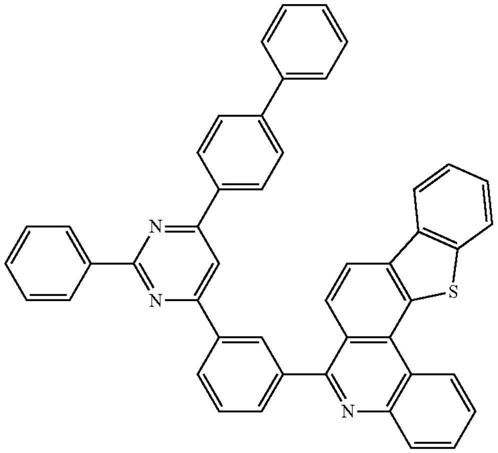
4-149
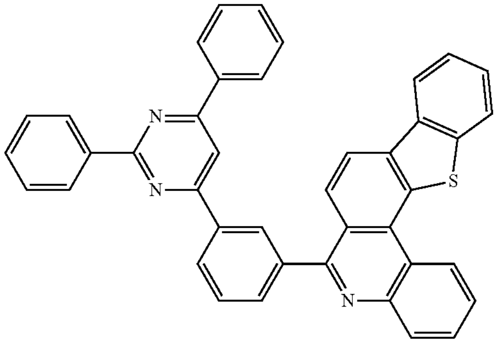
4-150
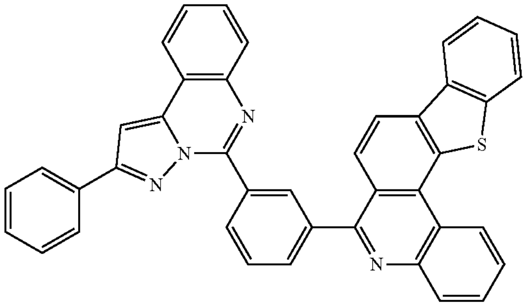
4-151
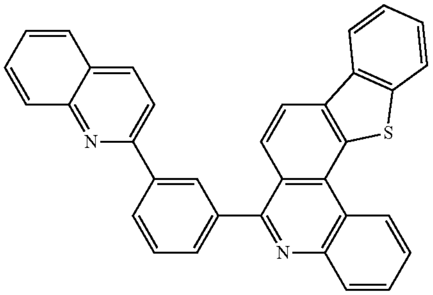

-continued
4-152
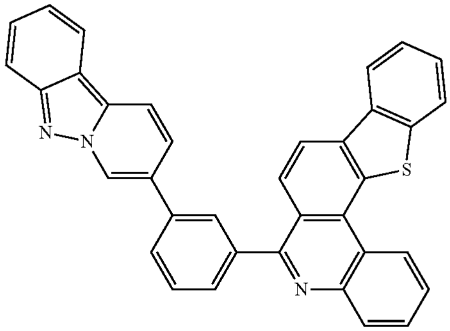
4-153
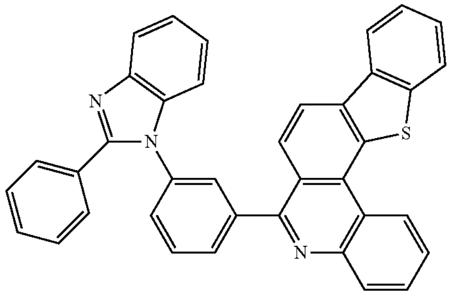
4-154
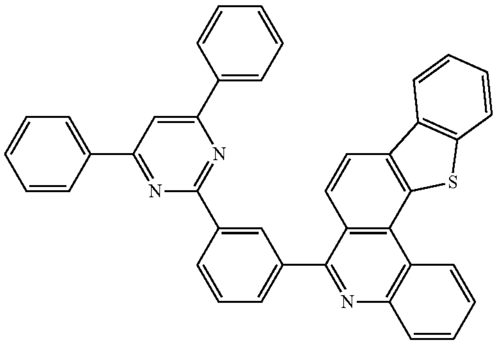
4-155
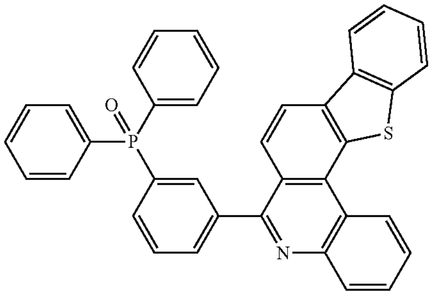
-continued
4-156
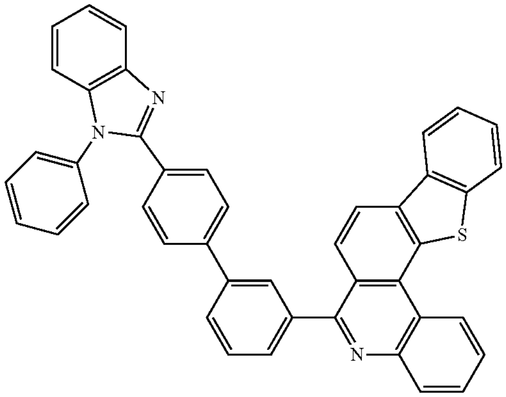
4-157
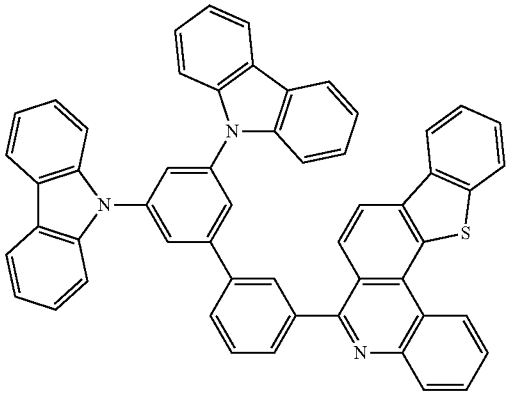
4-158
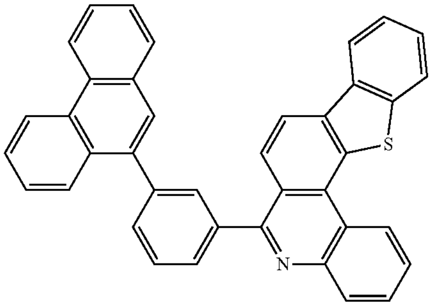
4-159
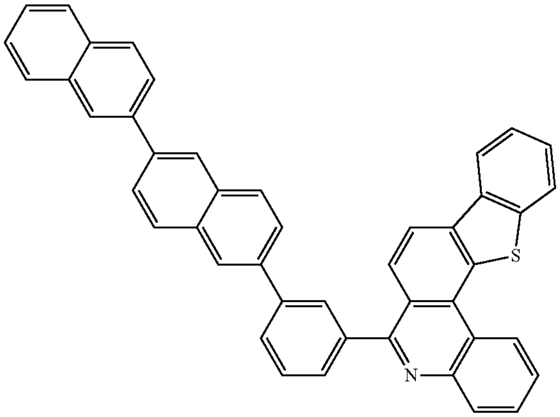

-continued
4-160
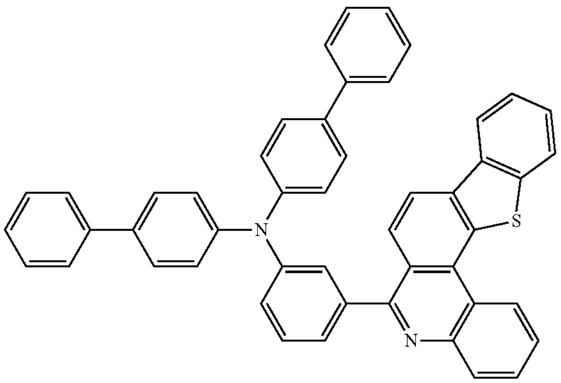
4-161
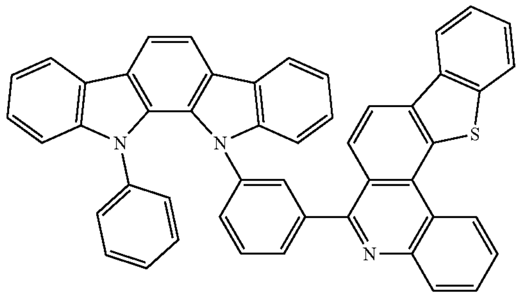
4-162
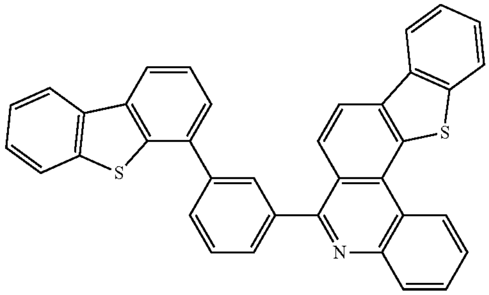
4-163
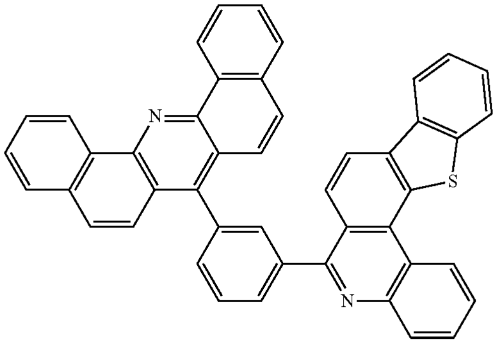
-continued
4-164
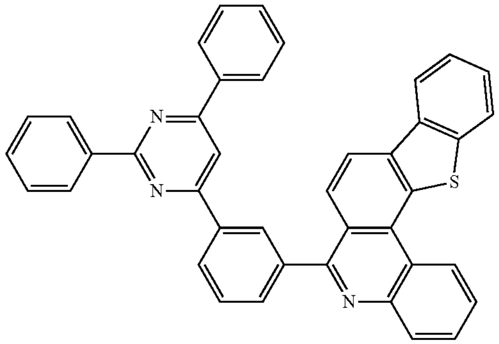
4-165
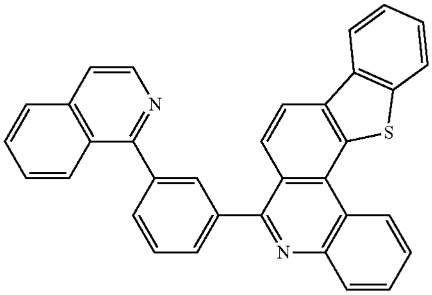
4-166
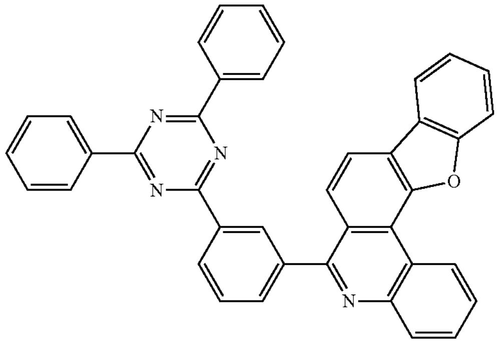
4-167
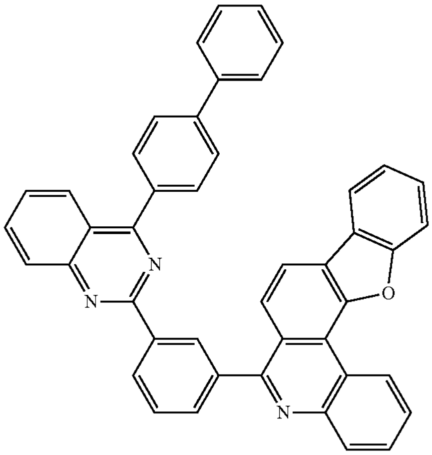

-continued
4-168
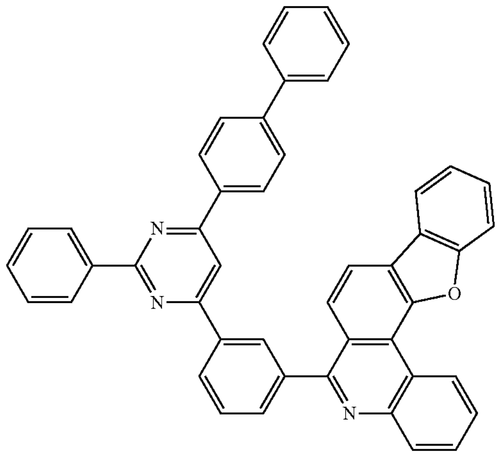
4-169
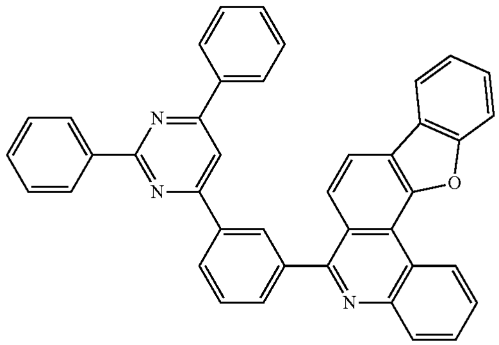
4-170
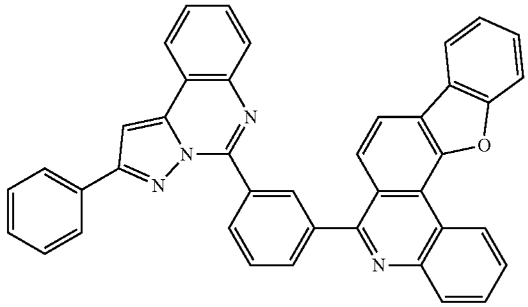
4-171
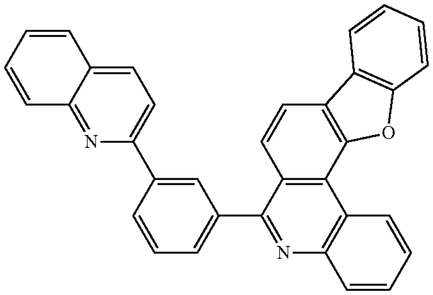
-continued
4-172
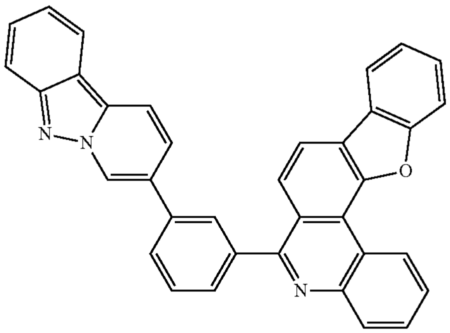
4-173
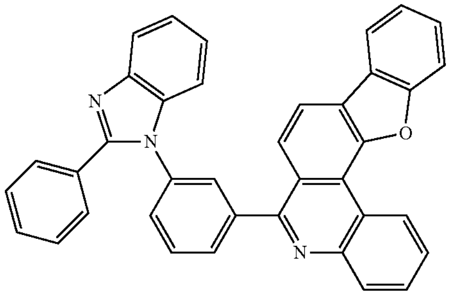
4-174
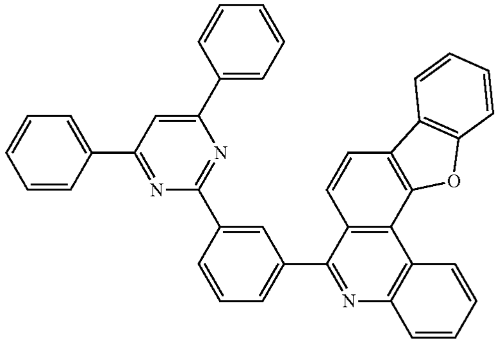
4-175
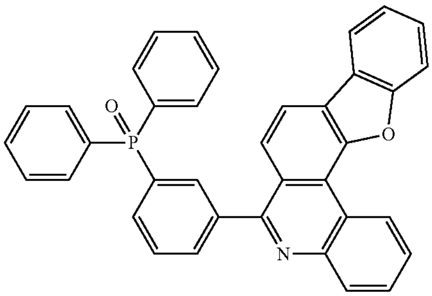

-continued
4-176
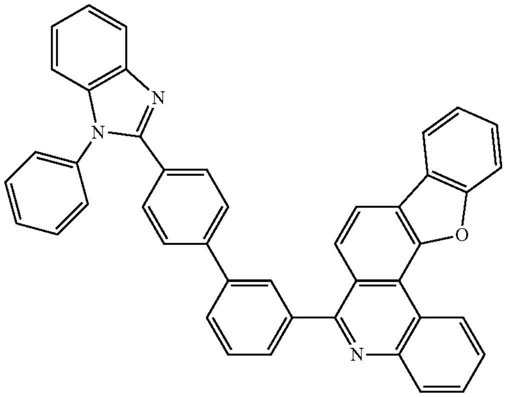
4-177
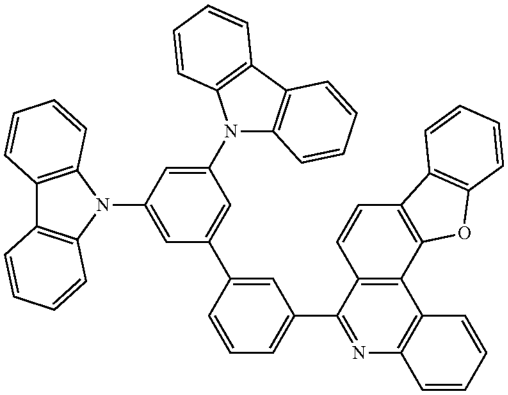
4-178
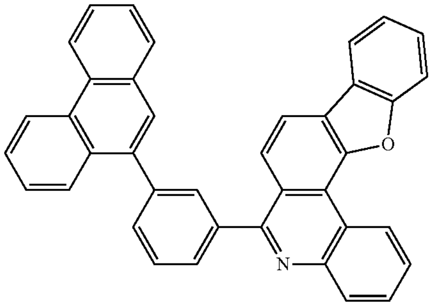
4-179
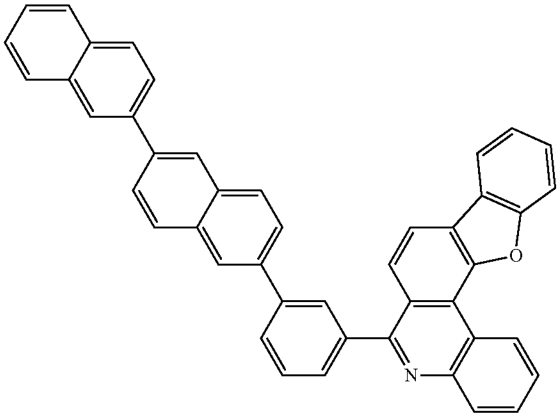
-continued
4-180
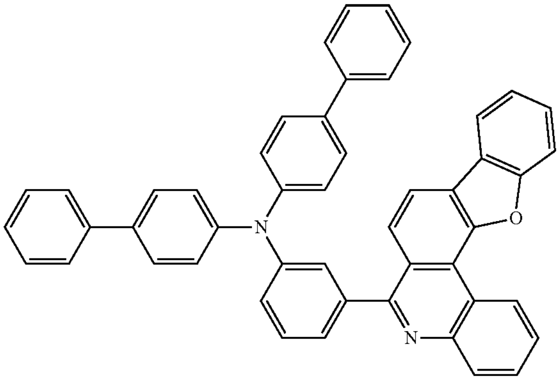
4-366
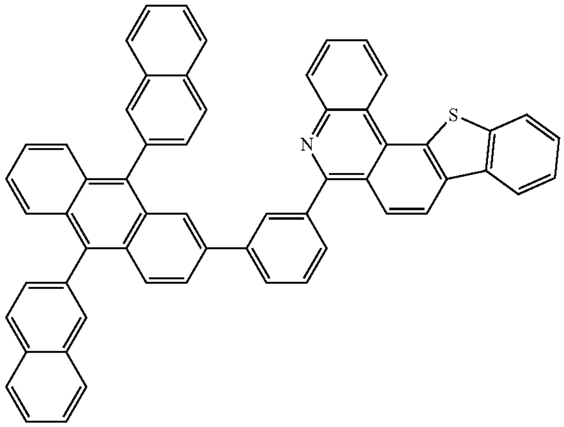
4-367
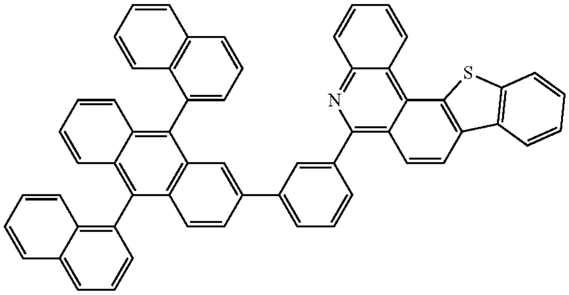
4-368
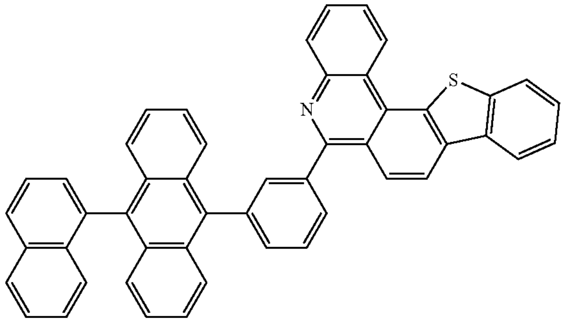

-continued
4-369
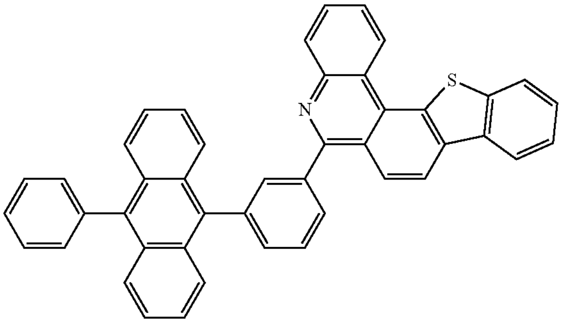
4-370
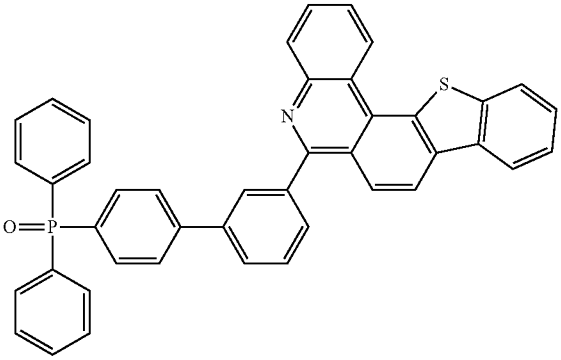
4-371
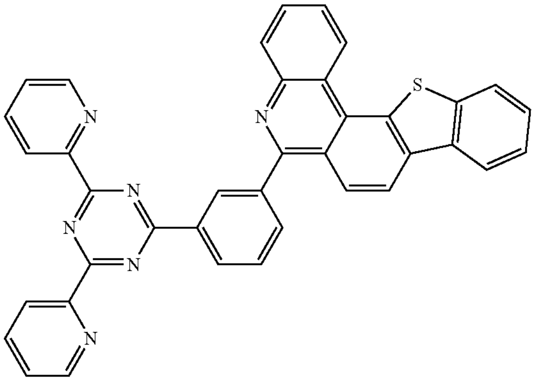
4-372
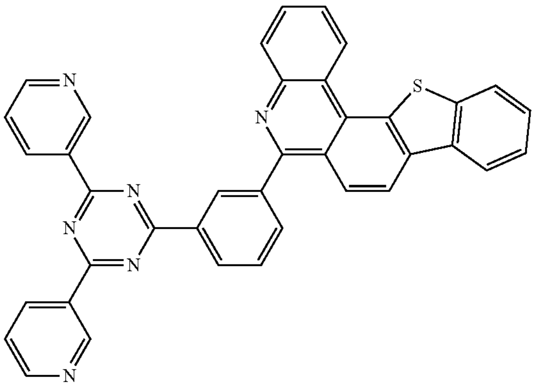
-continued
4-373
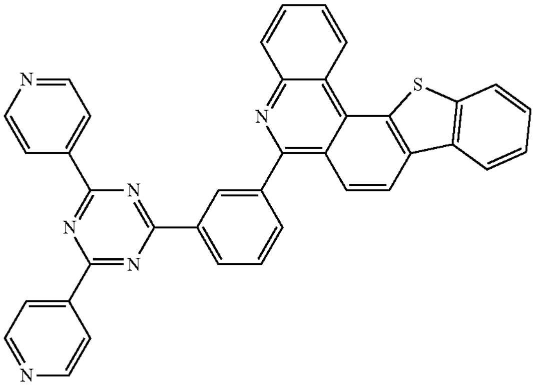
4-374
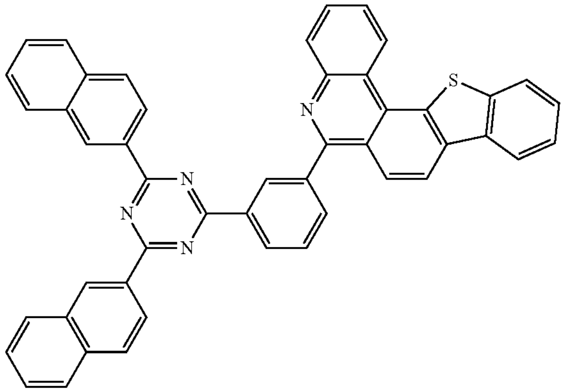
4-375
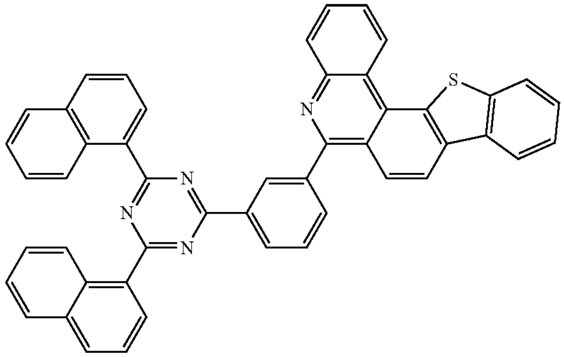
4-376
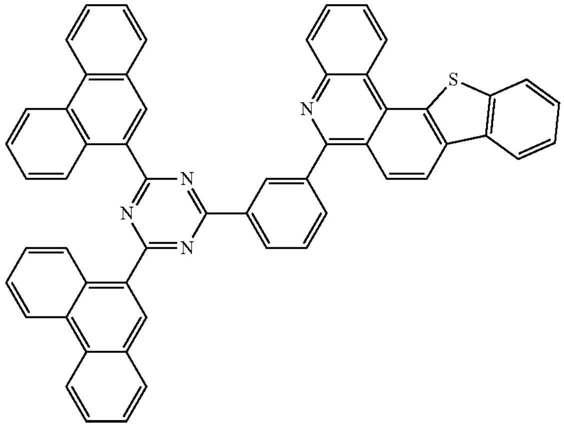

-continued
4-377
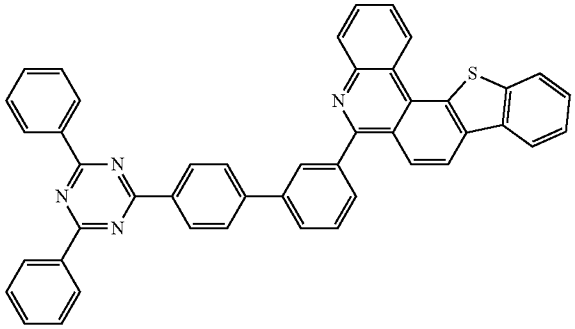
4-378
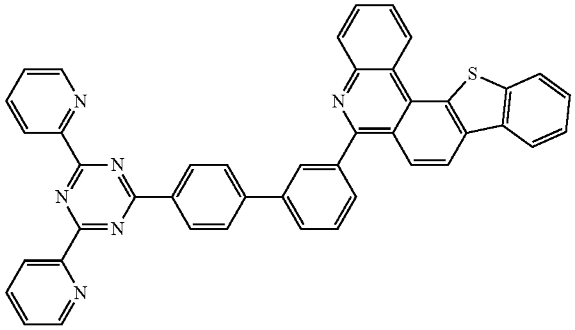
4-379
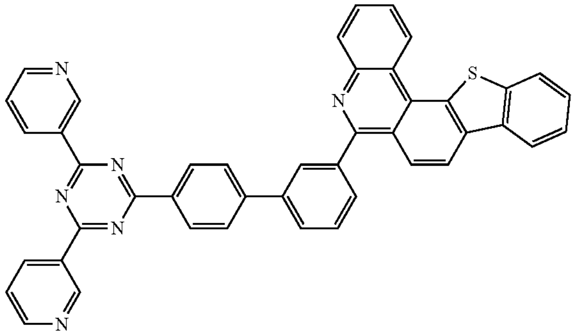
4-380
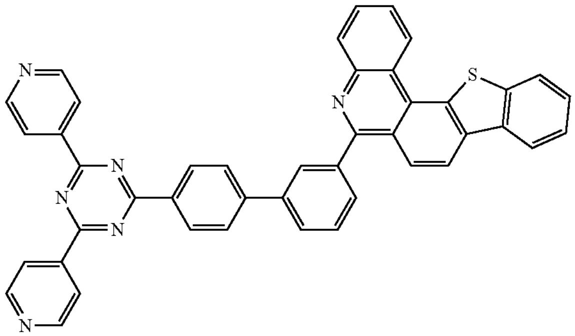
-continued
4-381
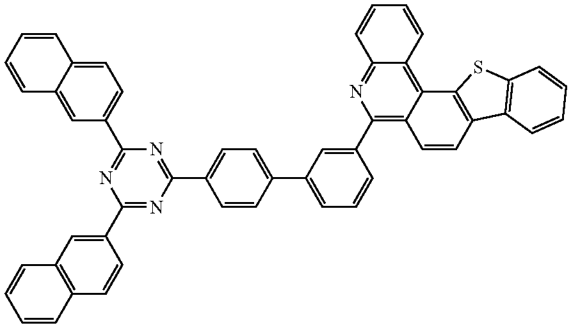
4-382
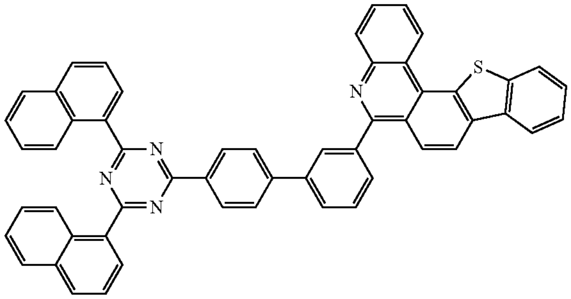
4-383
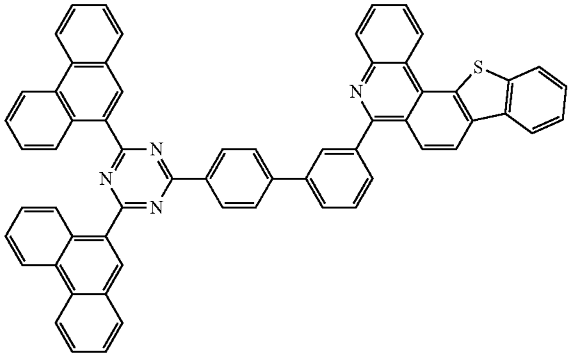
4-384
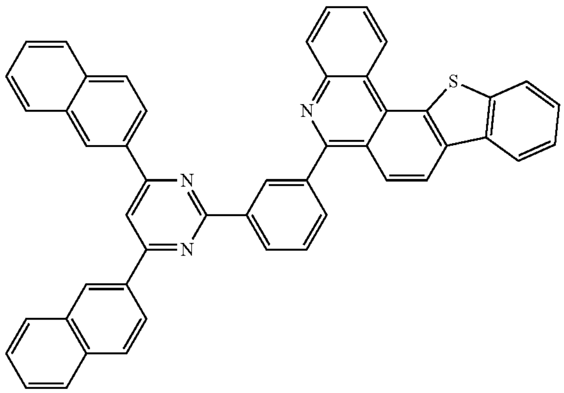

-continued
4-385
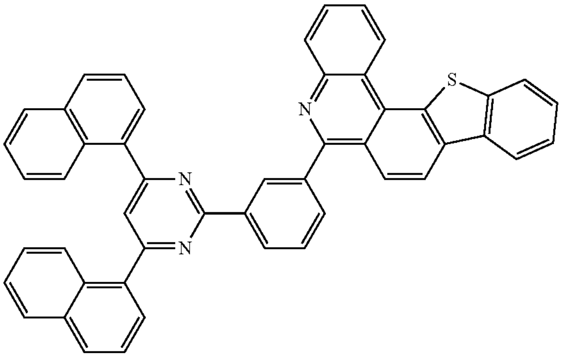
4-386
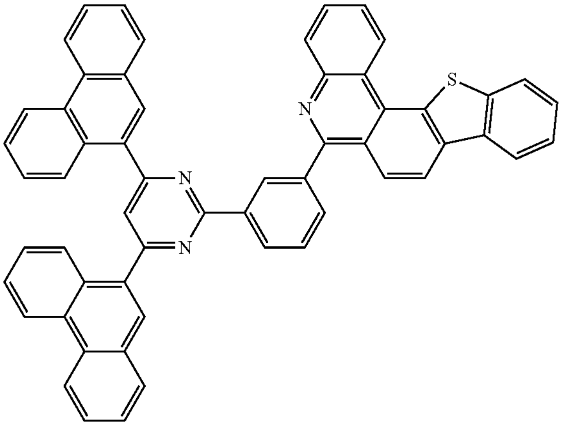
4-387
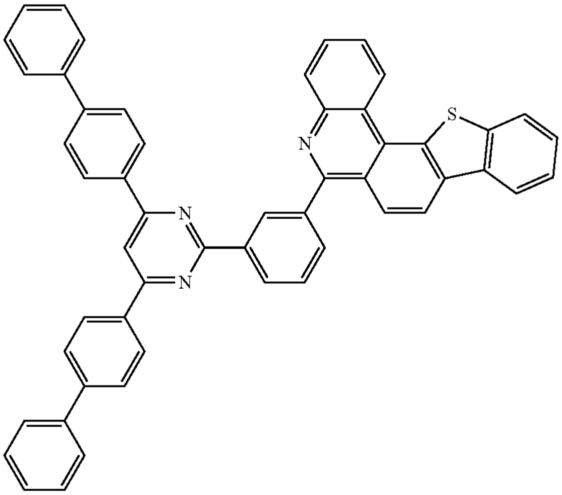
-continued
4-388
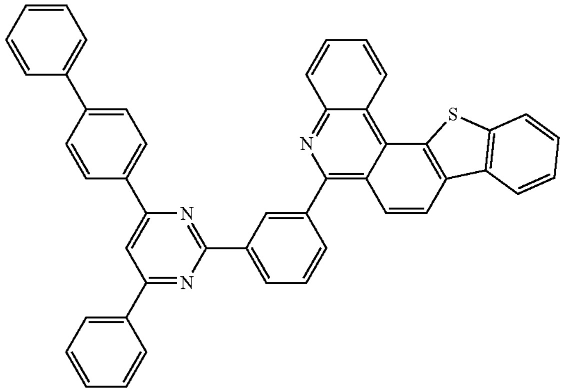
4-389
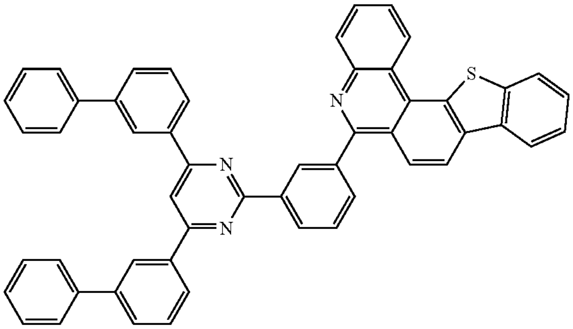
4-390
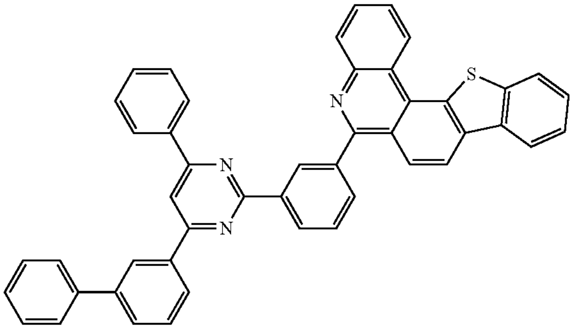
4-391
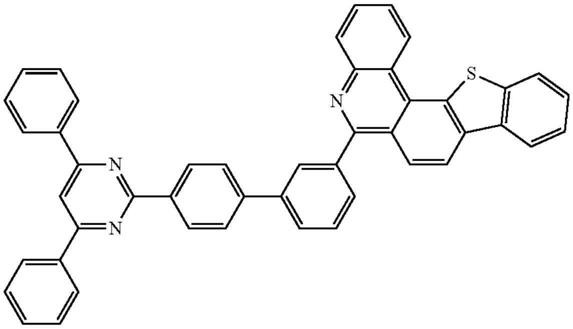

-continued
4-392
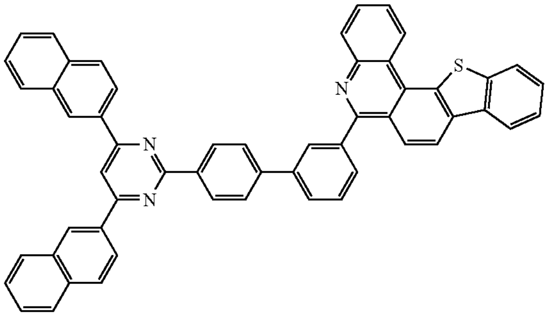
4-393
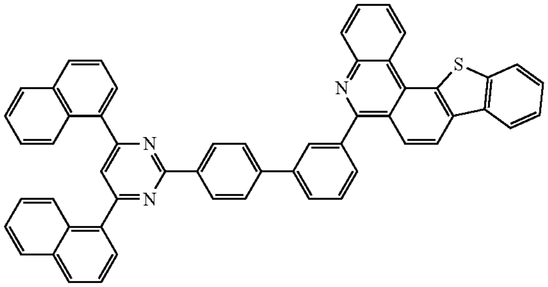
4-394
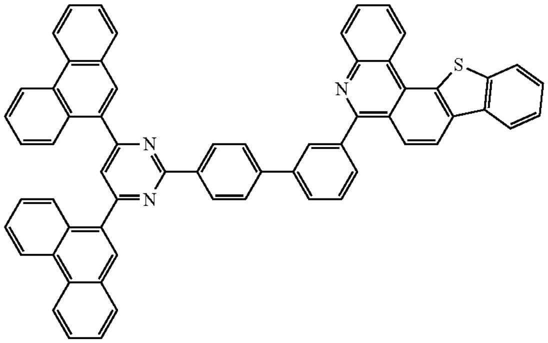
4-395
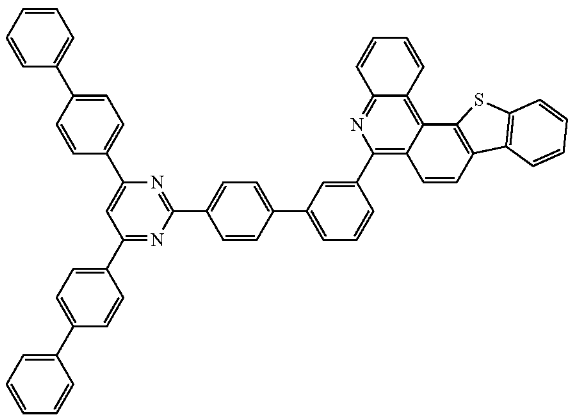
-continued
4-396
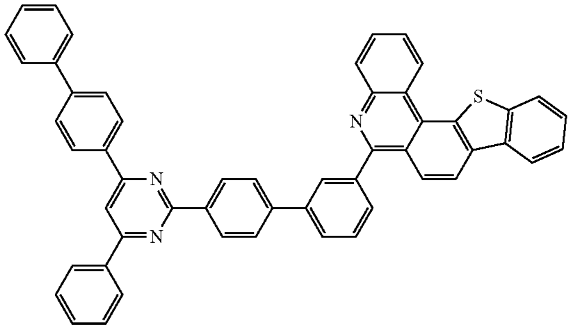
4-397
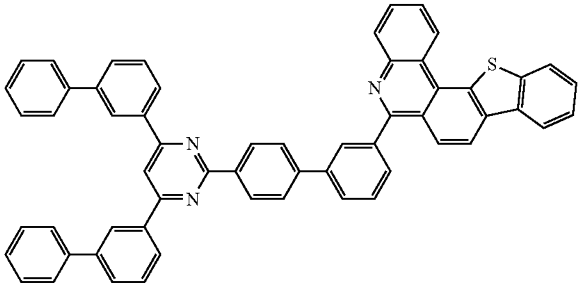
4-398
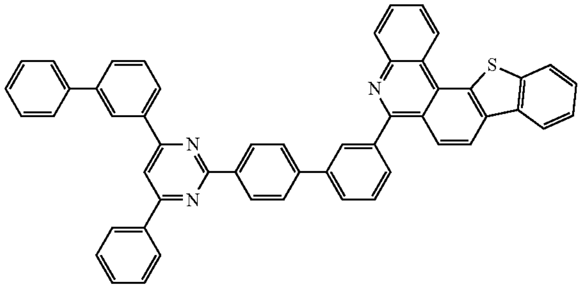
4-399
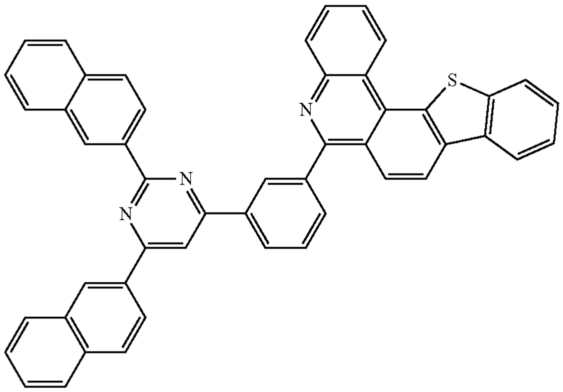

-continued
4-400
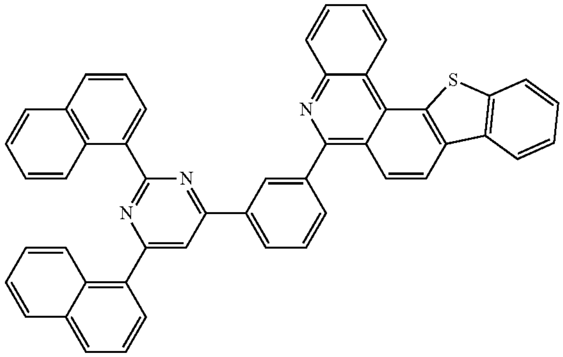
4-401
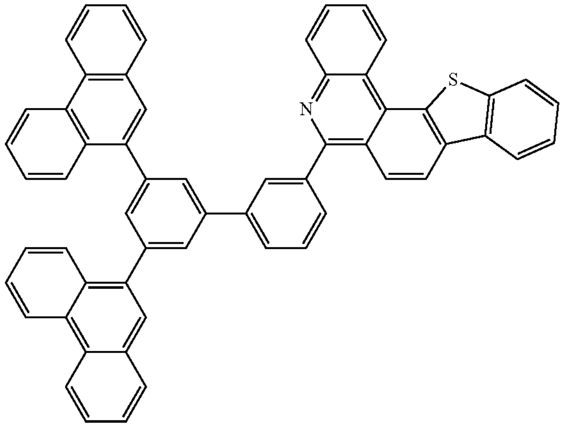
4-402
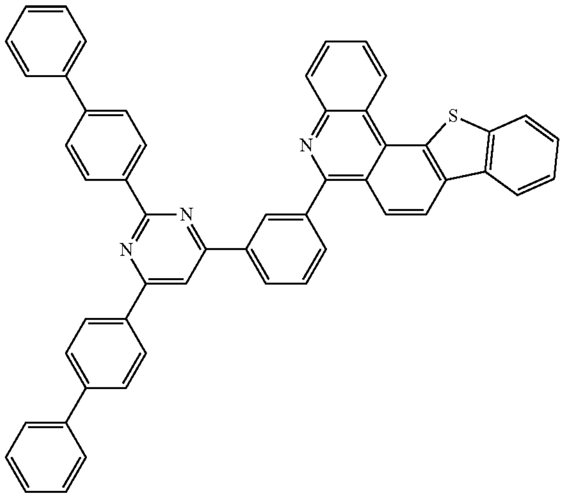
-continued
4-403
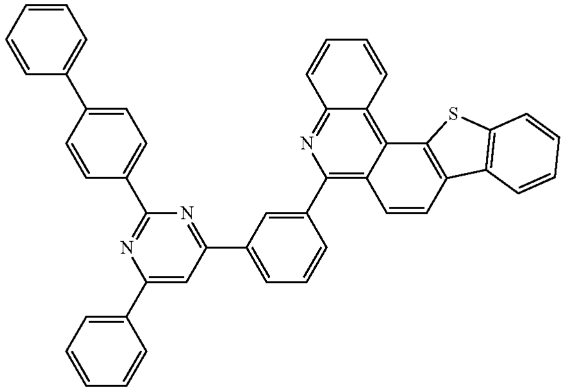
4-404
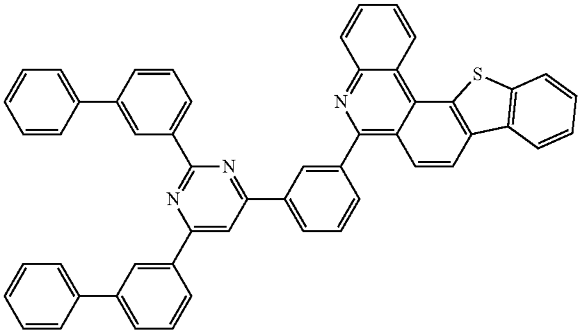
4-405
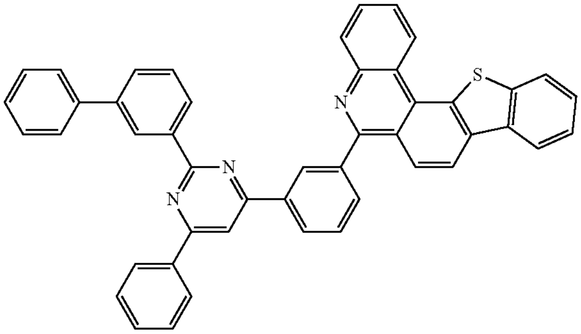
4-406
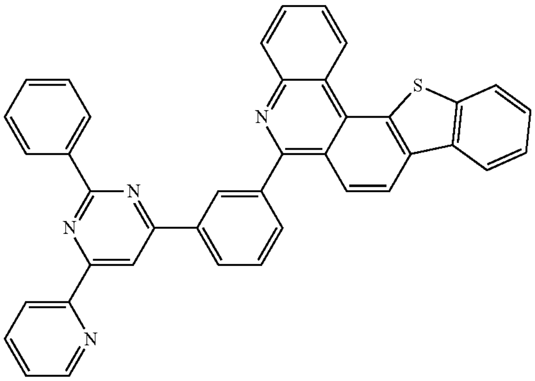

-continued
4-407
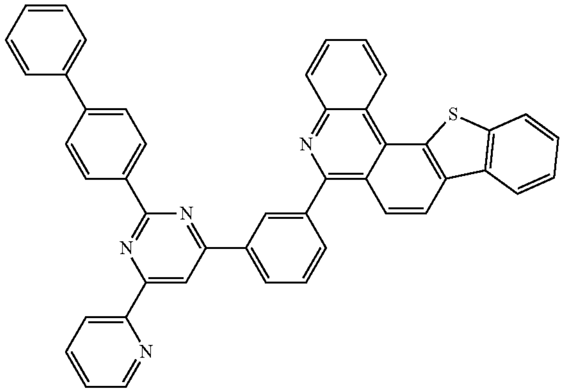
4-408
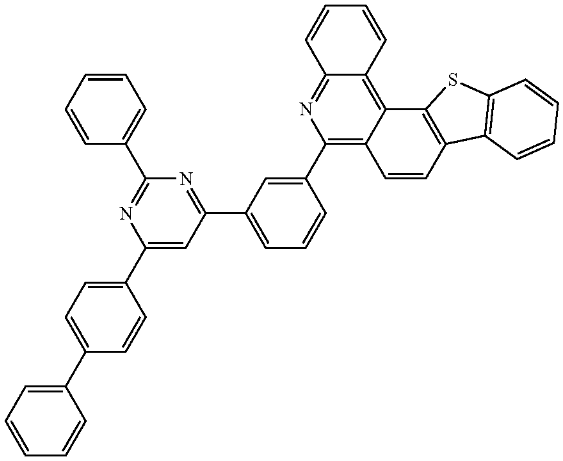
4-409
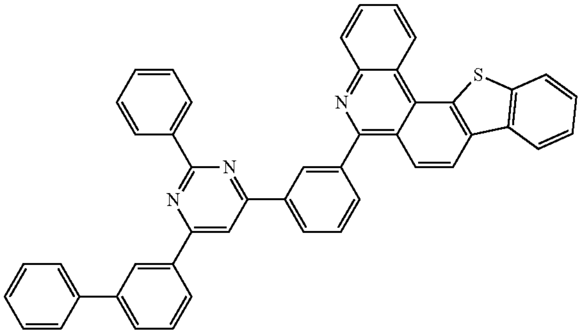
4-410
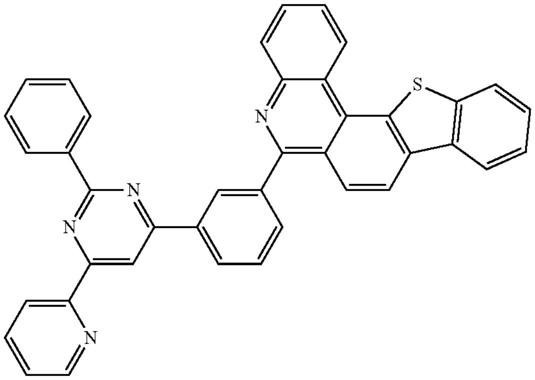
-continued
4-411
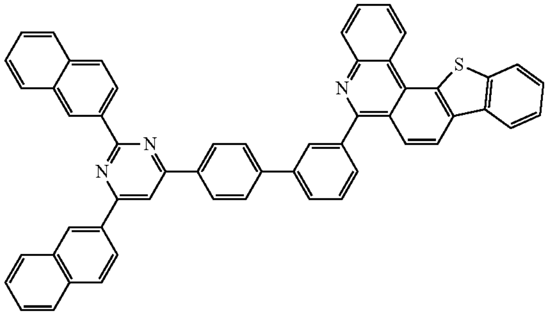
4-412
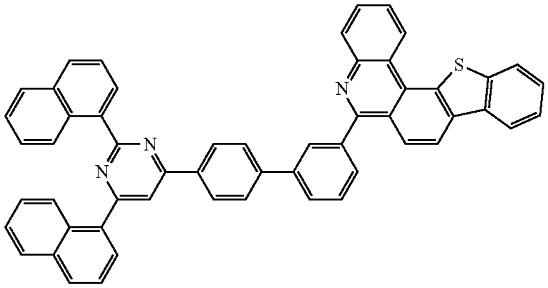
4-413
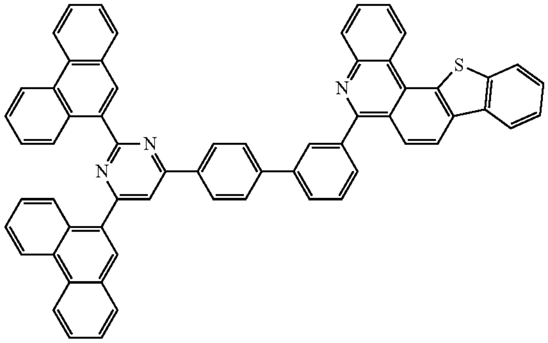
4-414
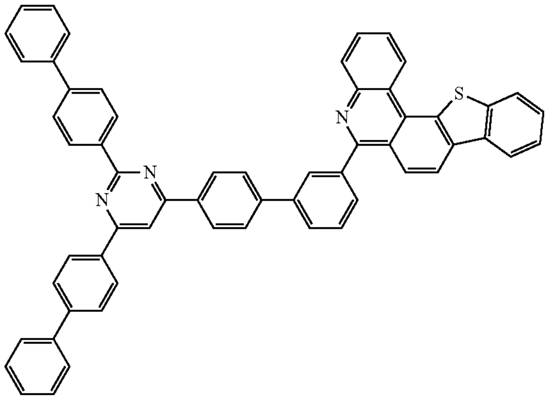

-continued
4-415
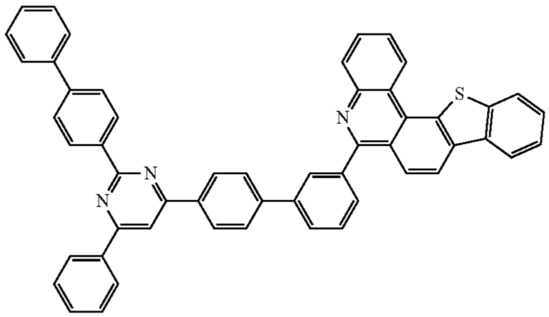
4-416
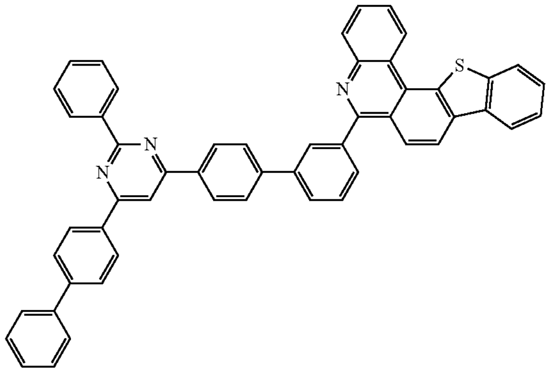
4-417
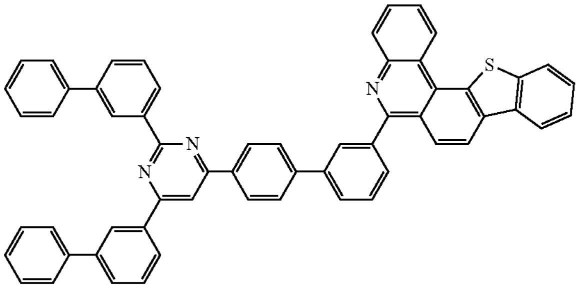
4-418
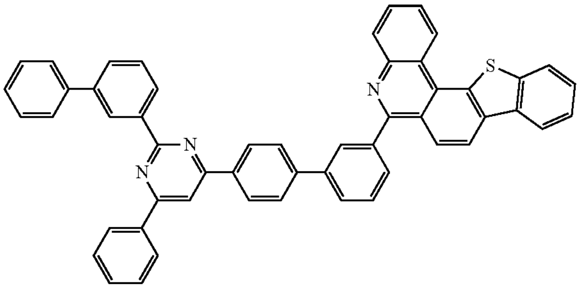
-continued
4-419
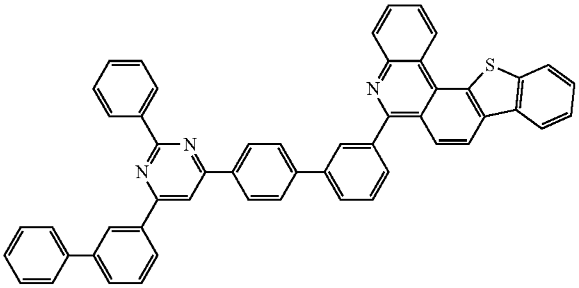
4-420
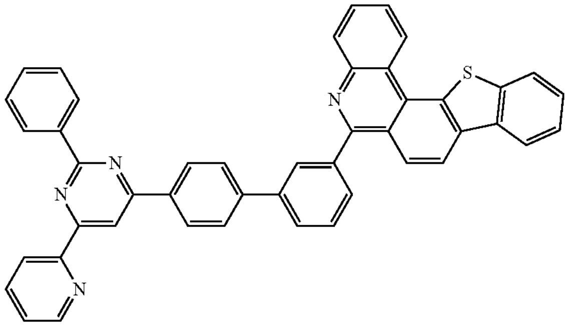
4-421
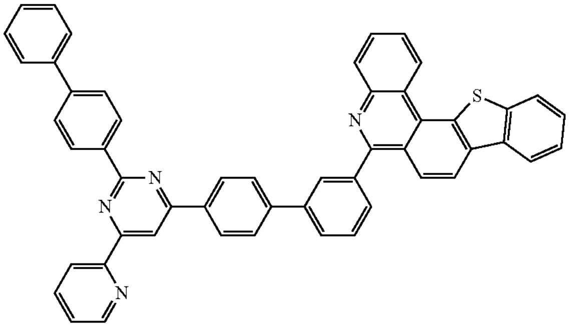
4-422
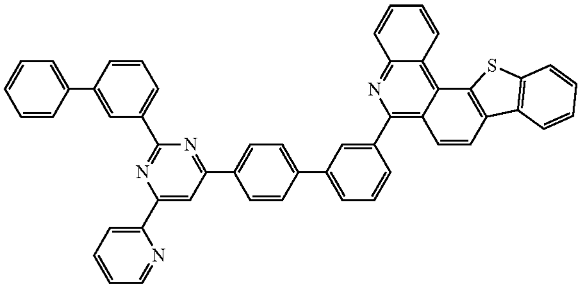

-continued
4-423
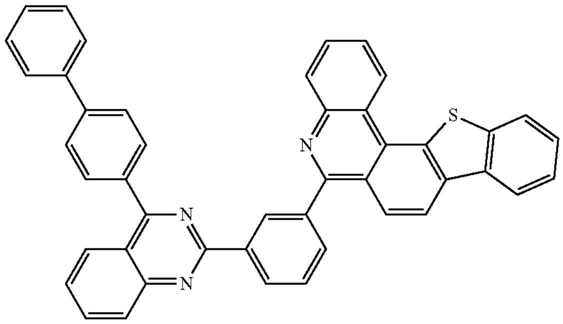
4-424
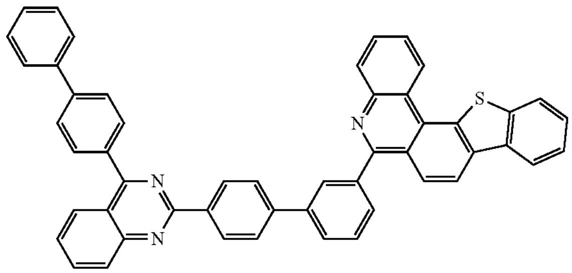
4-425
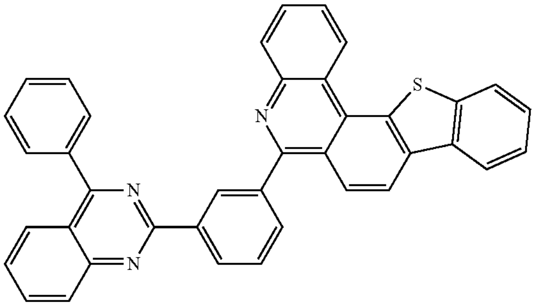
4-426
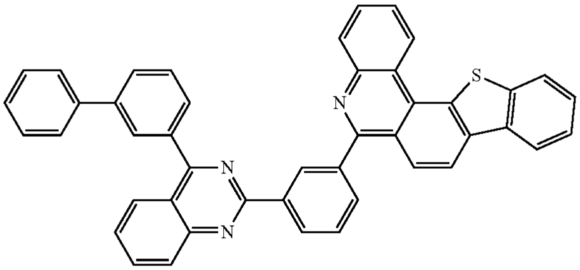
4-427
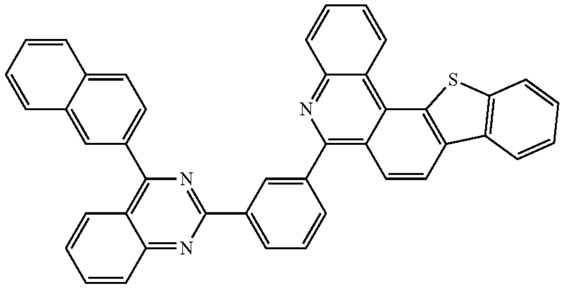
-continued
4-428
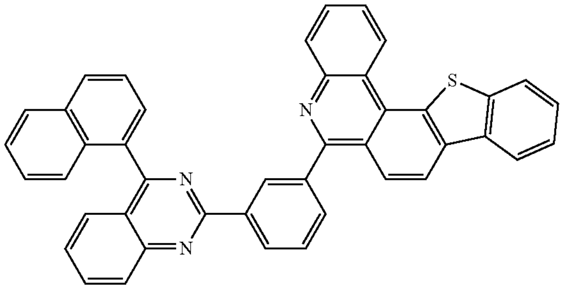
4-429
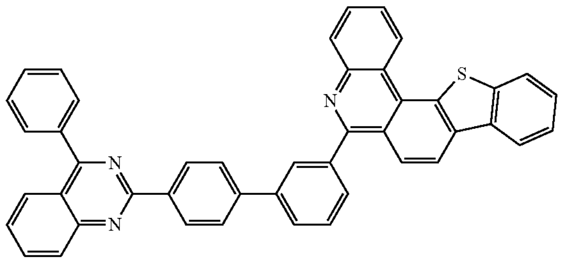
4-430
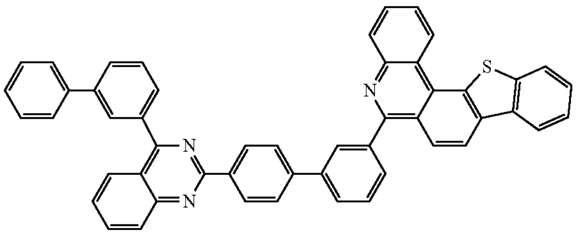
4-431
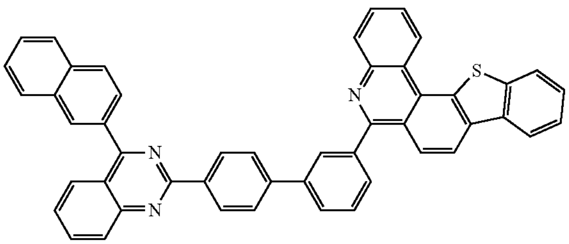
4-432
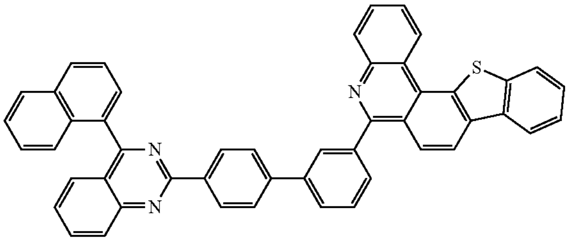

-continued
4-433
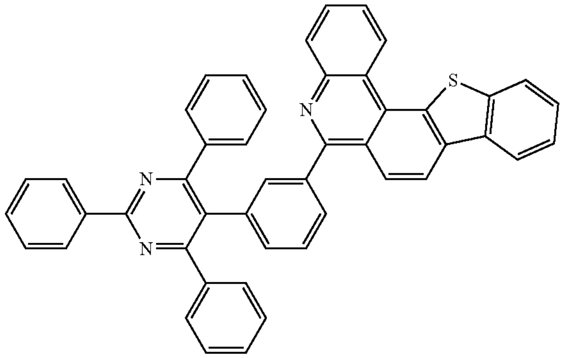
4-434
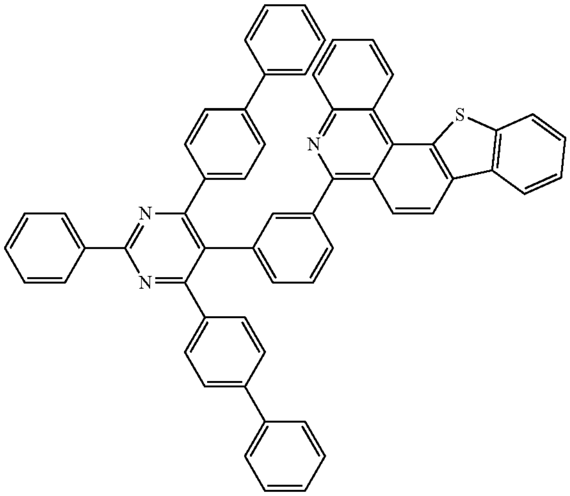
4-435
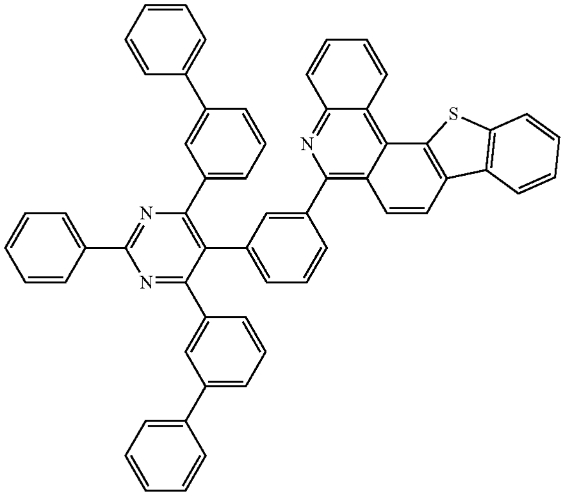
-continued
4-436
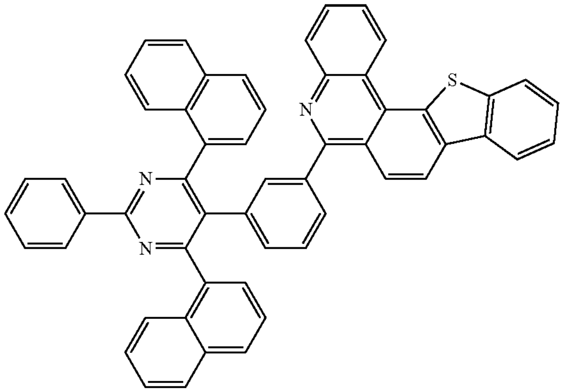
4-437
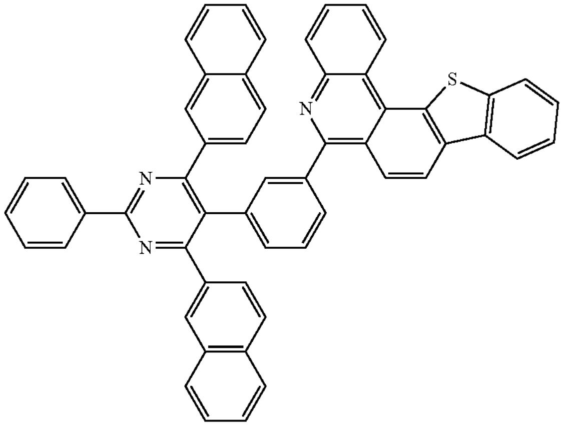
4-438
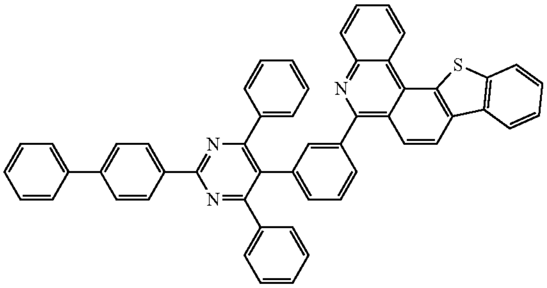
4-439
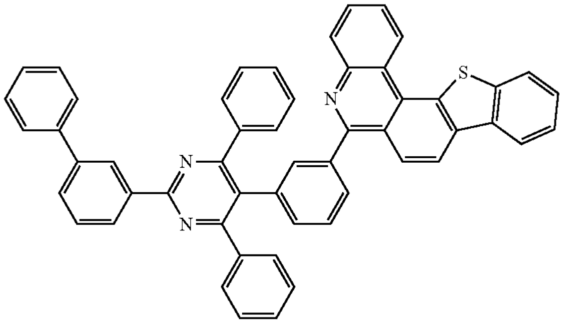

-continued
4-440
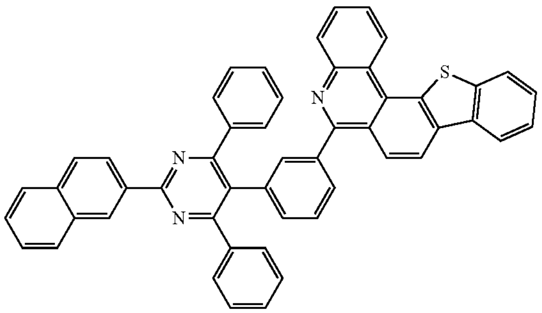
4-441
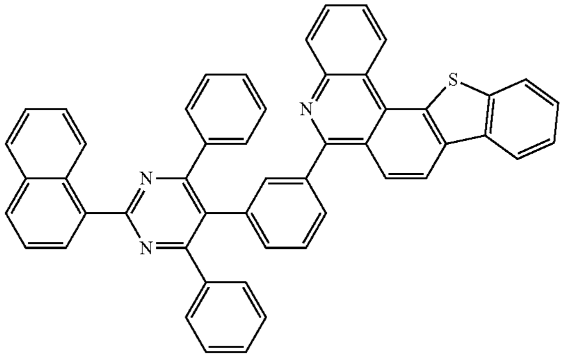
4-442
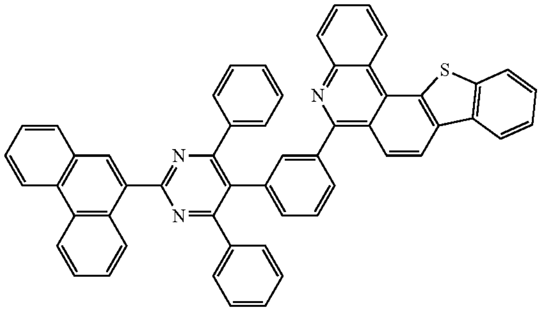
4-443
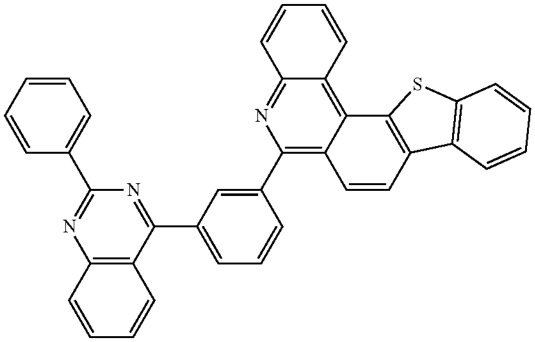
-continued
4-444
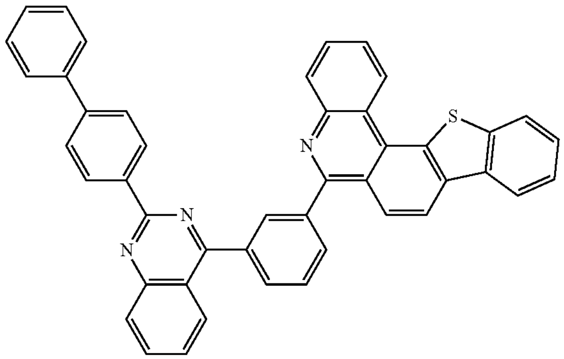
4-445
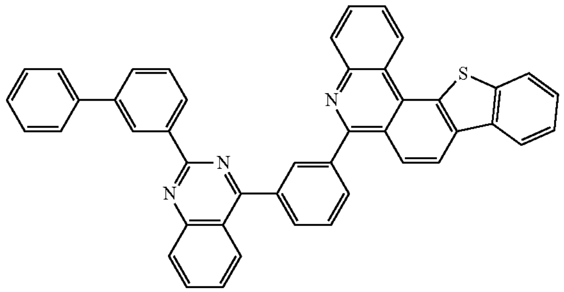
4-446
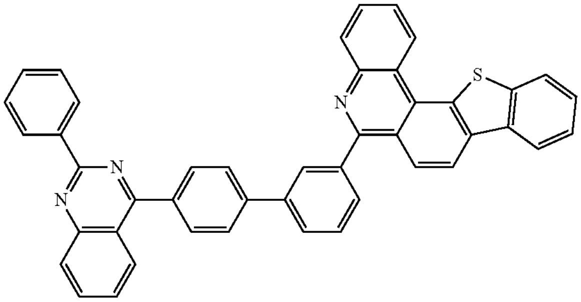
4-447
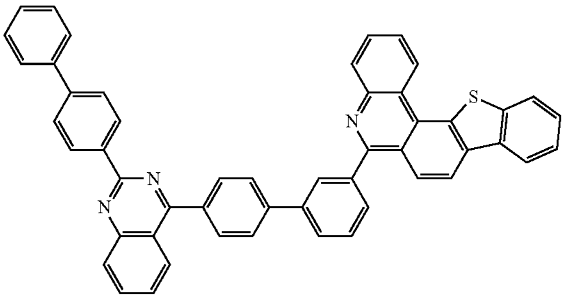
4-448
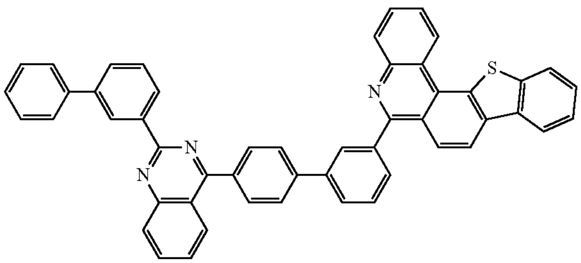

-continued
4-449
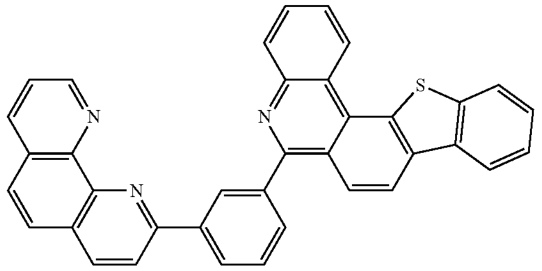
4-450
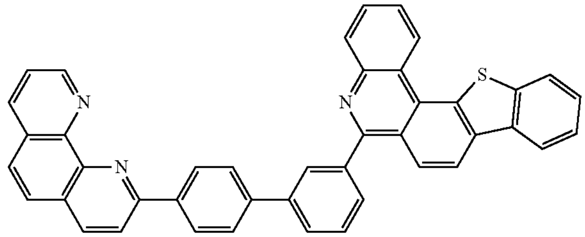
4-451
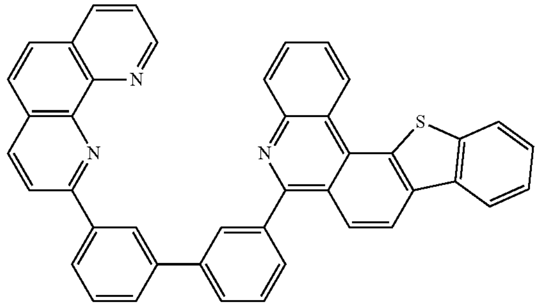
4-452
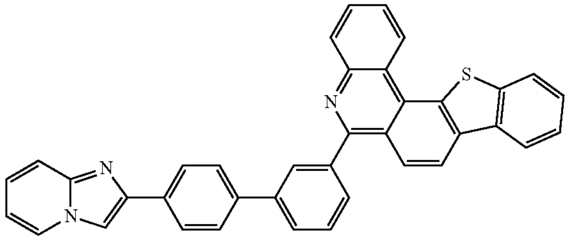
4-453
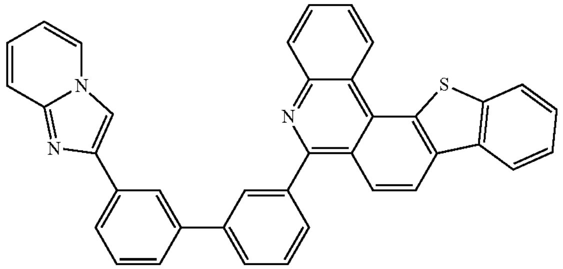
-continued
4-454
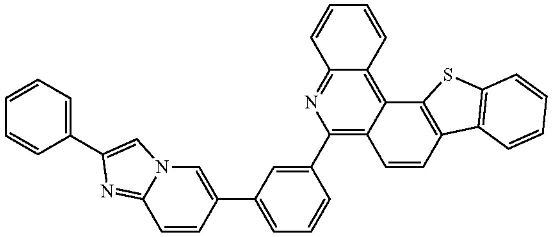
4-455
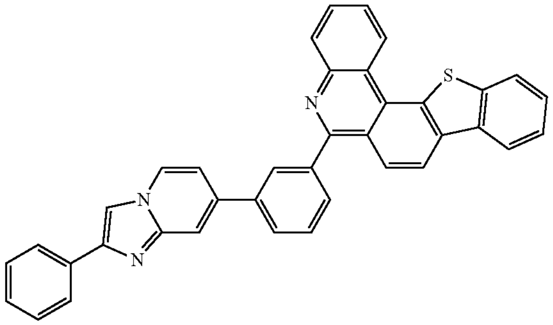
4-456
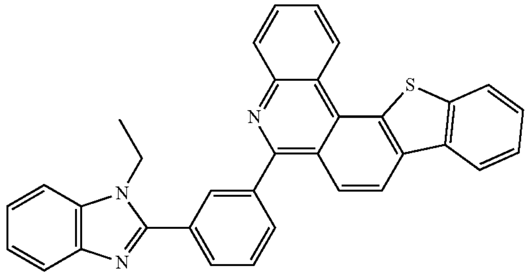
4-457
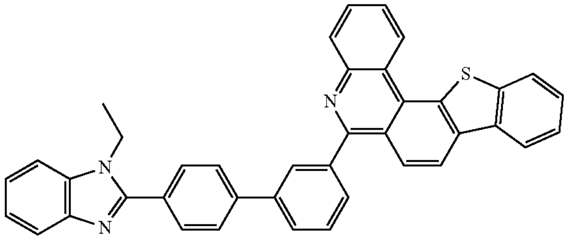
4-458
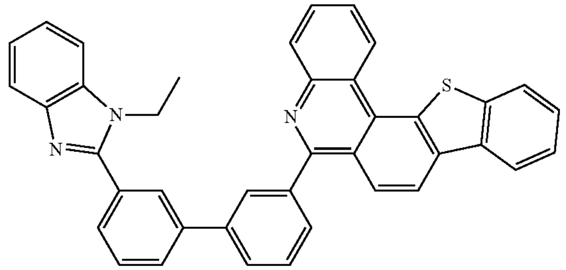

-continued
4-459
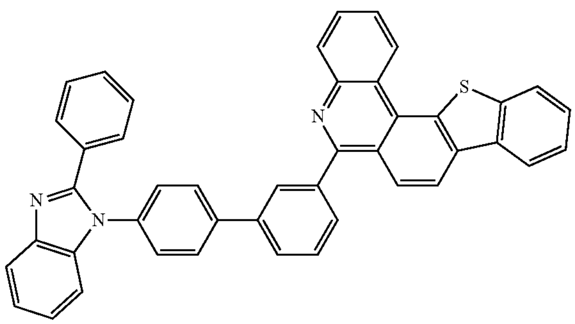
4-460
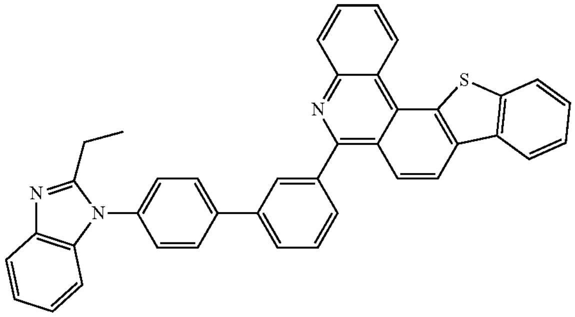
4-461
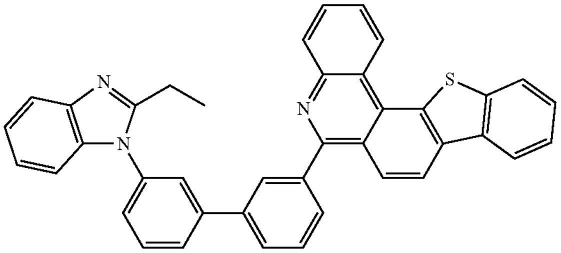
4-462
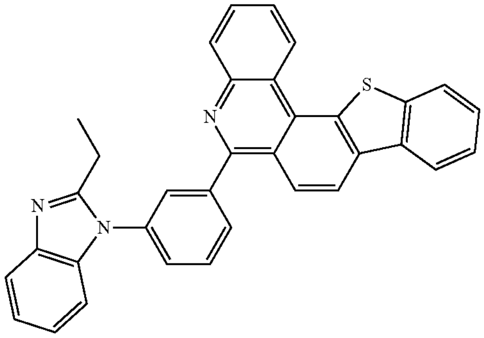
4-463
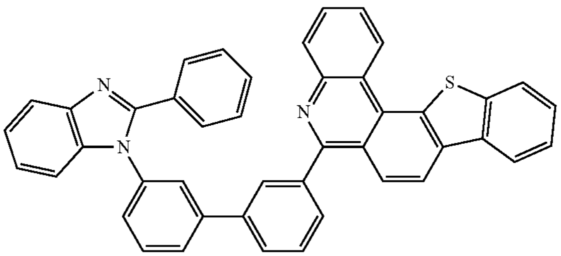
-continued
4-464
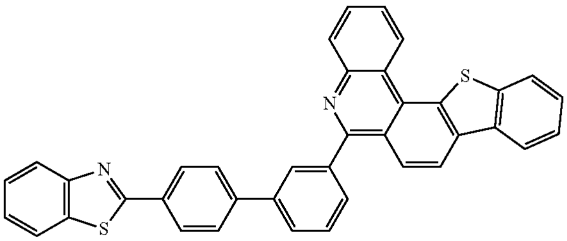
4-465
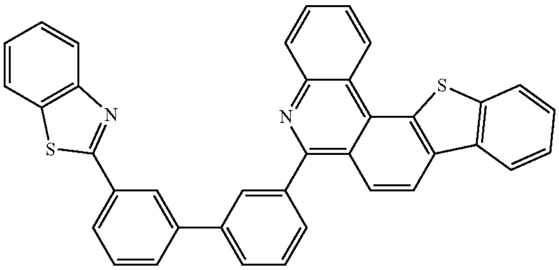
4-466
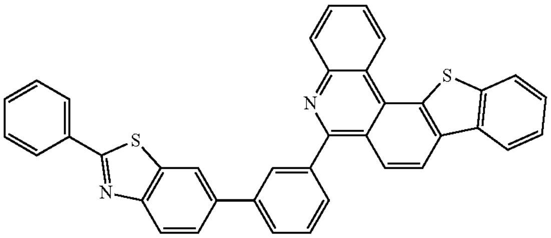
4-467
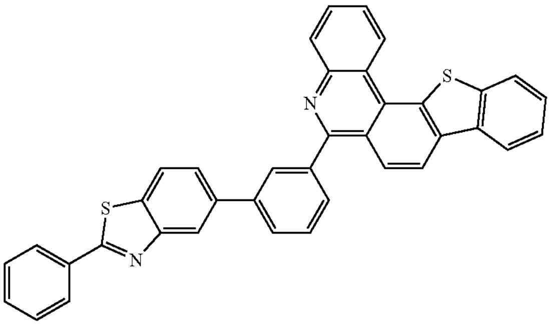
4-468
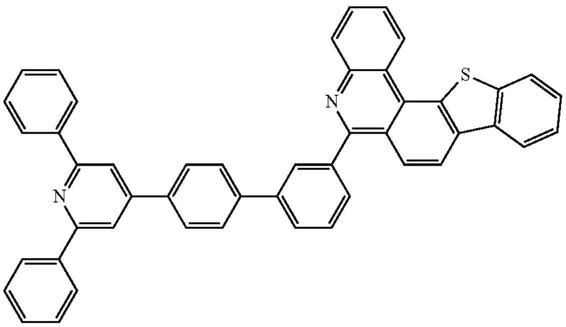

-continued
4-469
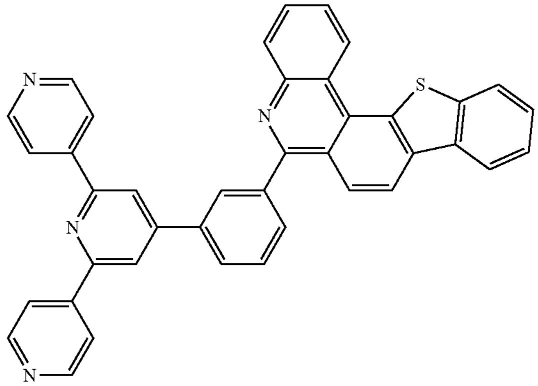
4-470
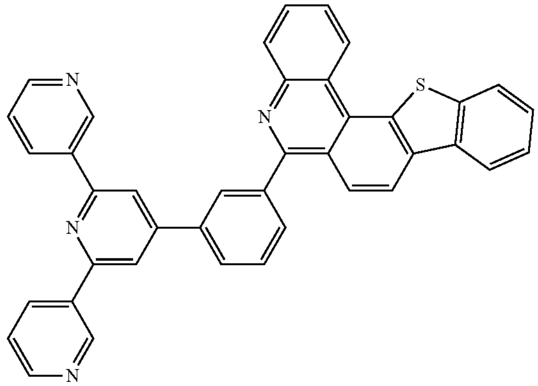
4-471
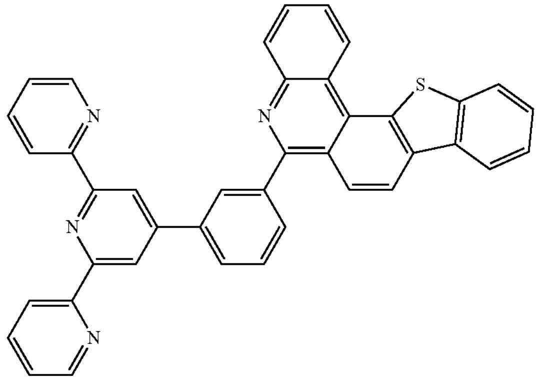
4-472
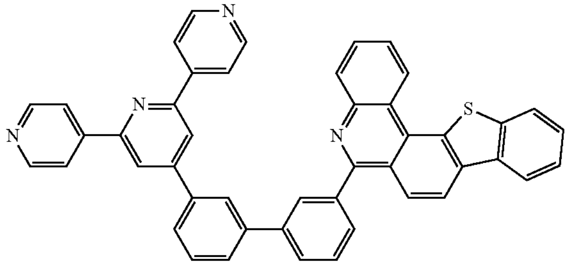
-continued
4-473
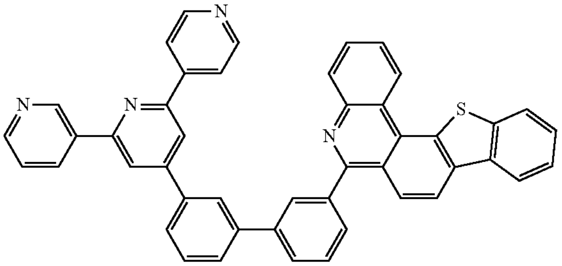
4-474
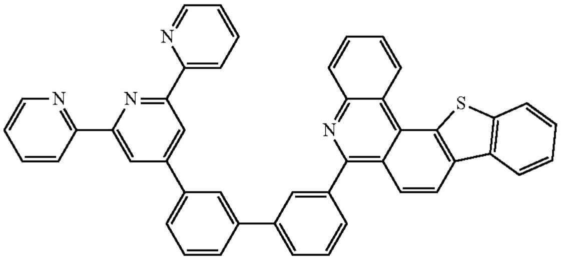
4-475
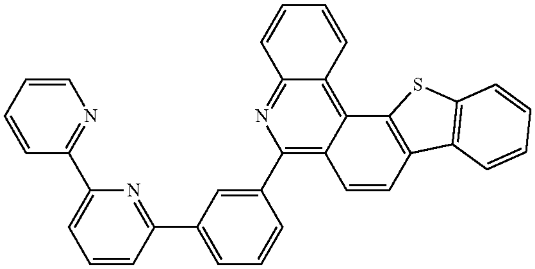
4-476
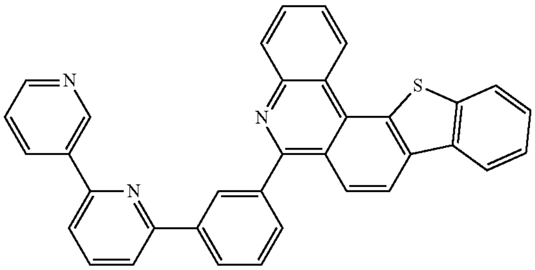
4-477
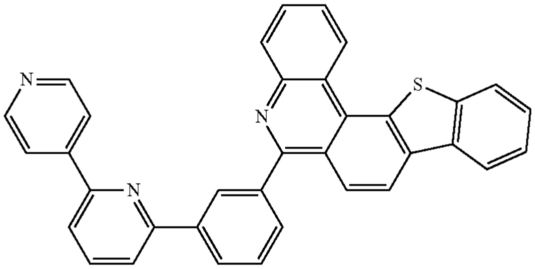

-continued
4-478
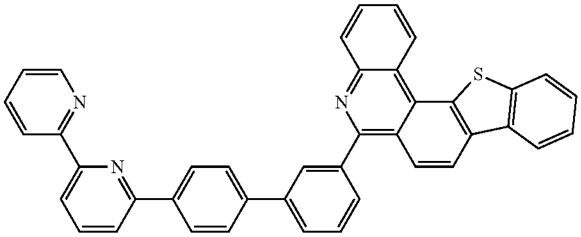
4-479
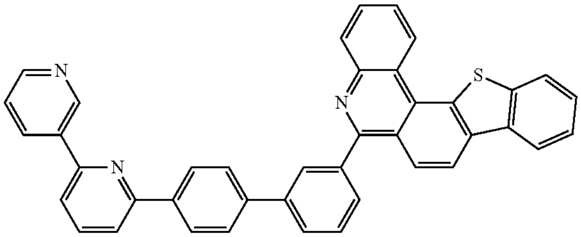
4-480
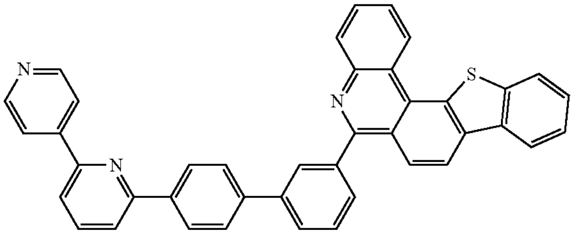
4-596
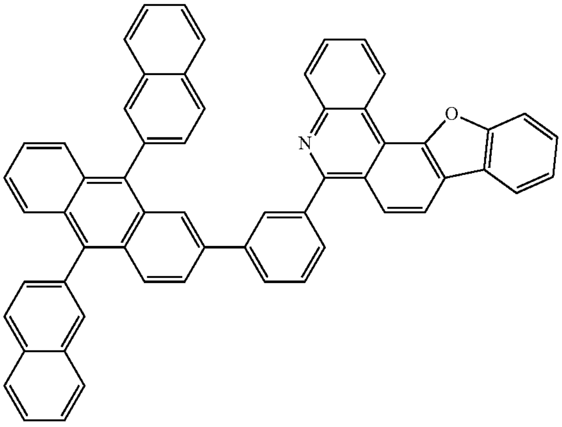
4-597
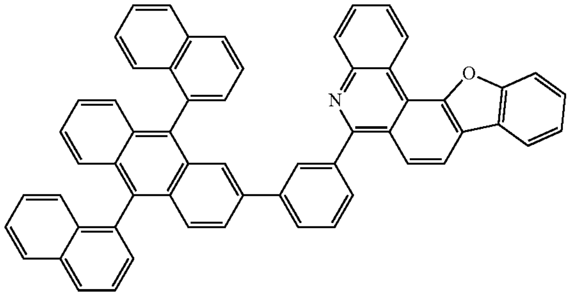
-continued
4-598
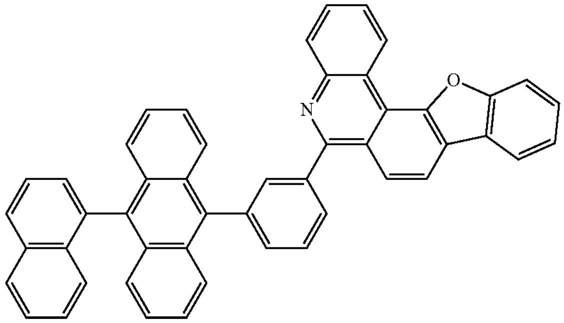
4-599
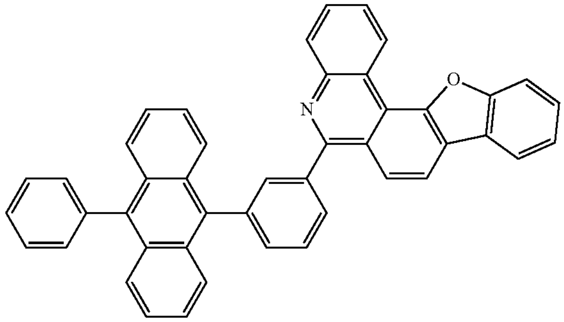
4-600
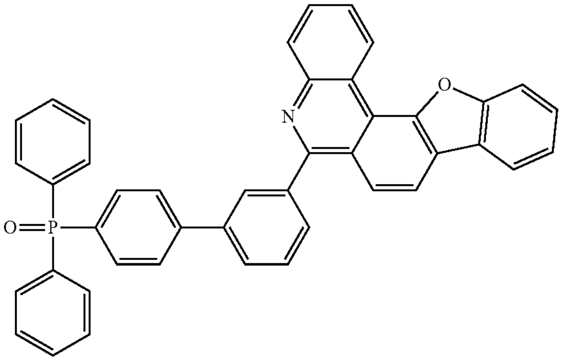
4-601
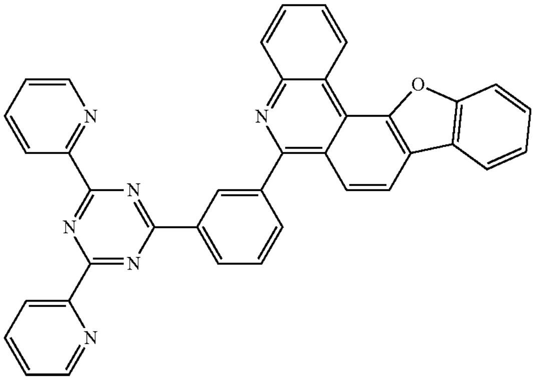

-continued
4-602
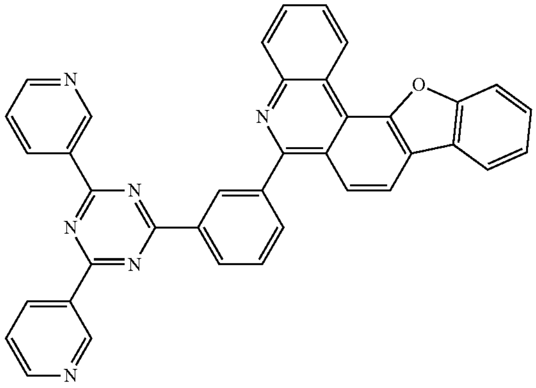
4-603
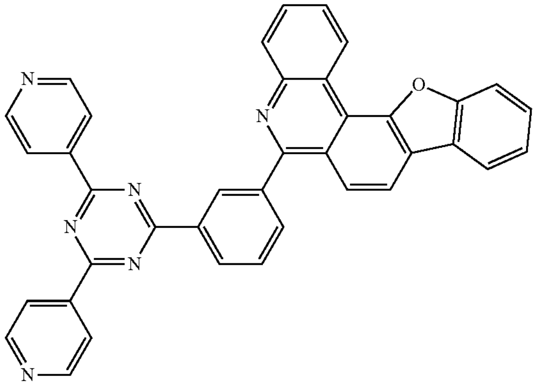
4-604
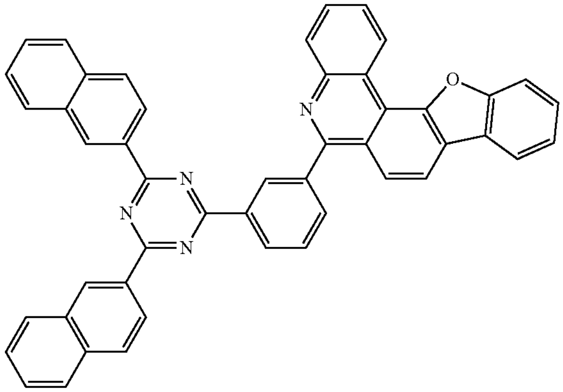
4-605
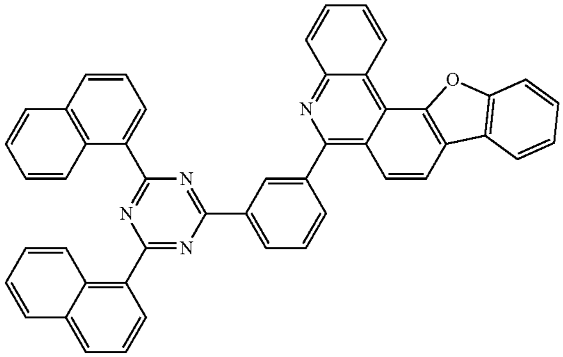
-continued
4-606
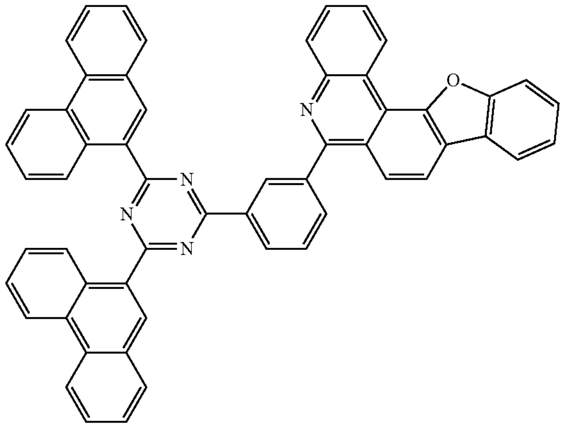
4-607
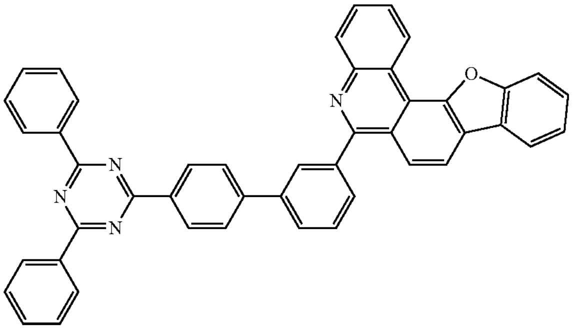
4-608
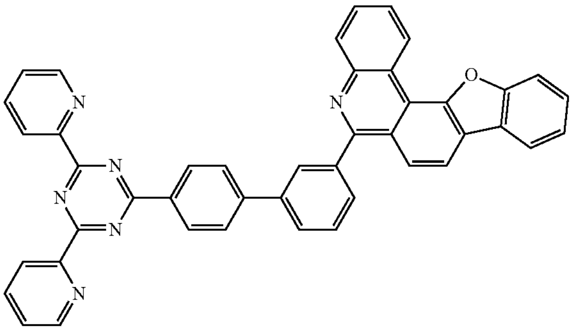
4-609
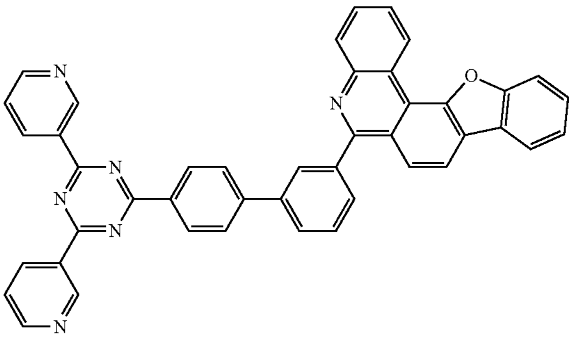

-continued
4-610
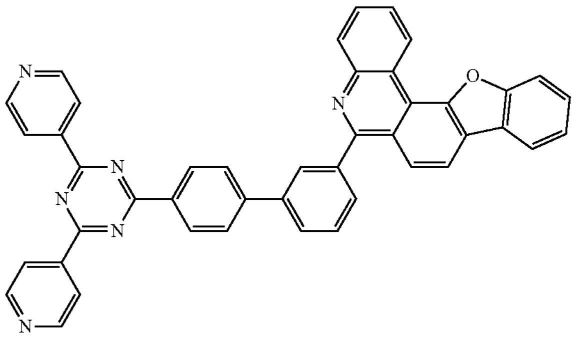
4-611
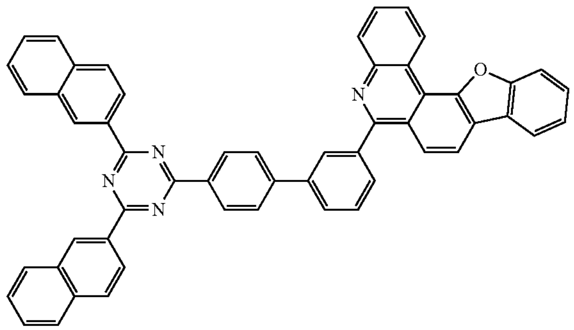
4-612
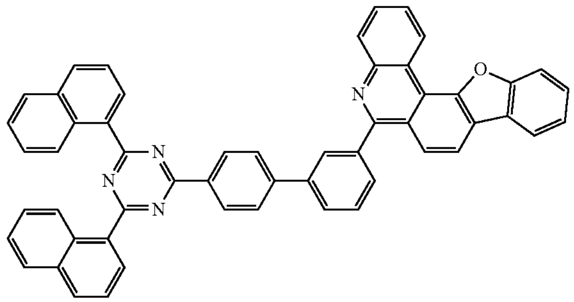
4-613
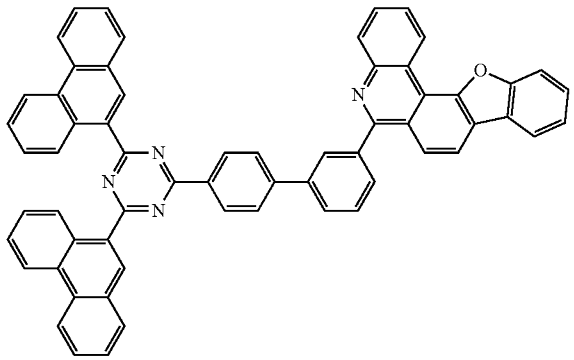
-continued
4-614
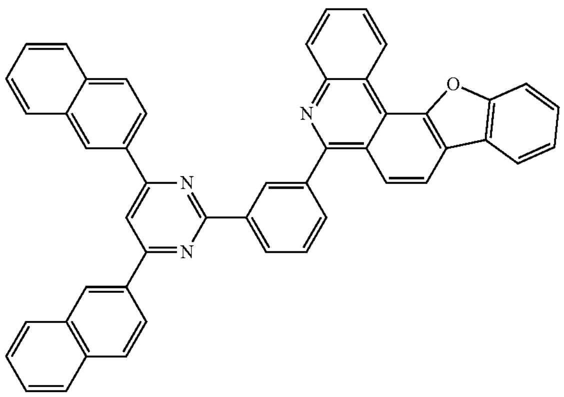
4-615
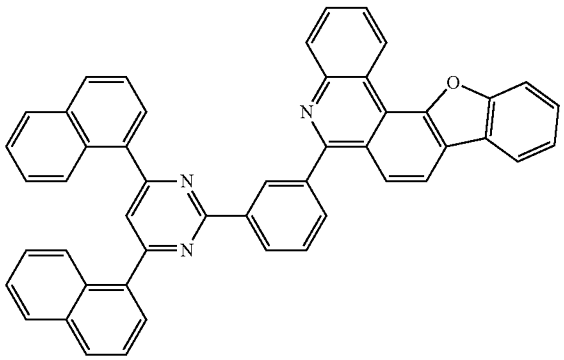
4-616
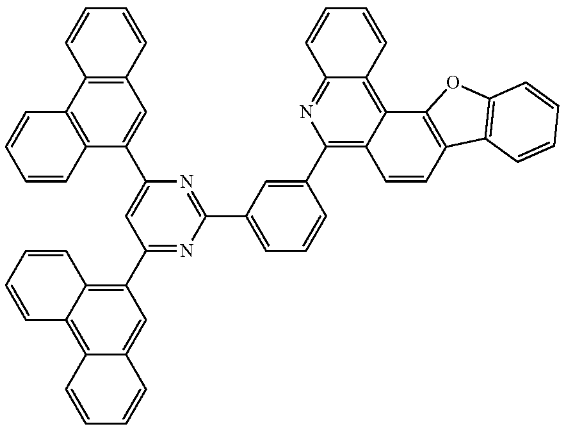

-continued
4-617
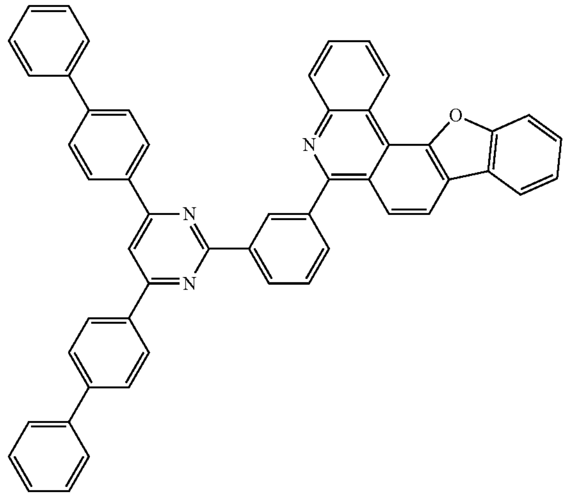
4-618
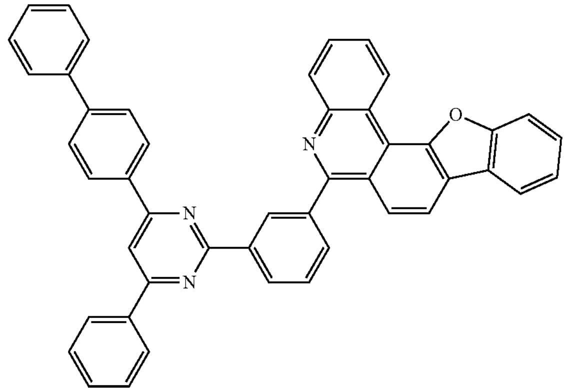
4-619
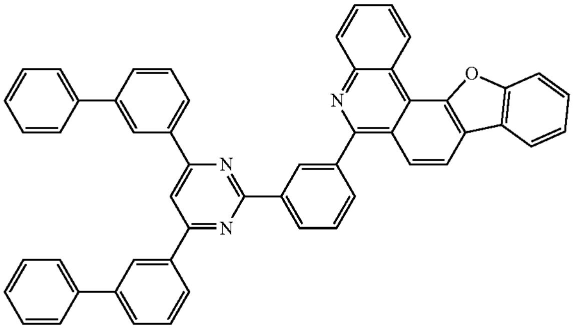
4-620
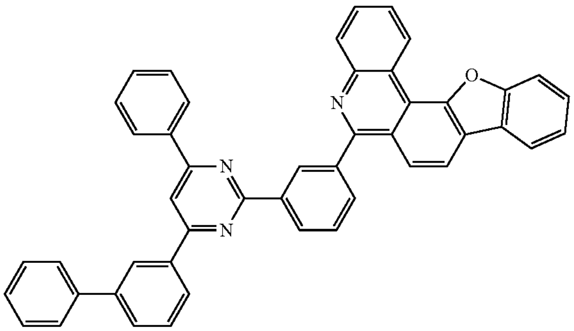
-continued
4-621
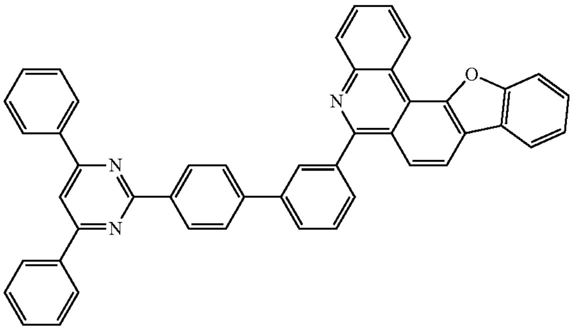
4-622
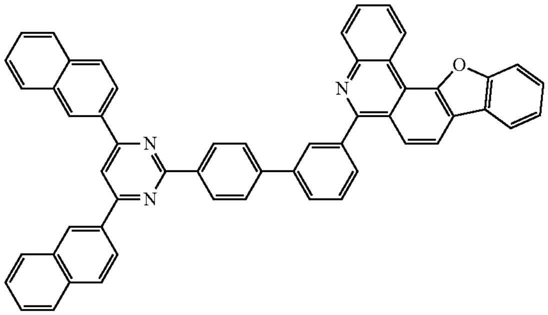
4-623
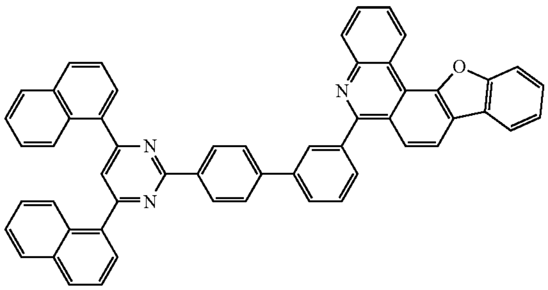
4-624
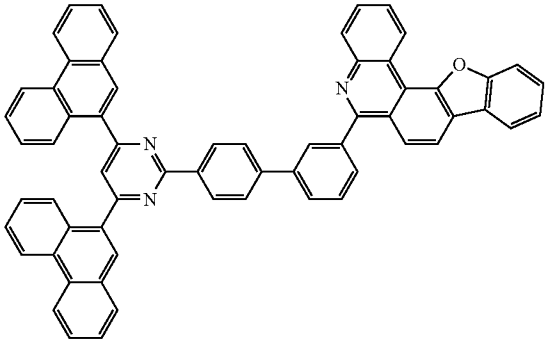

-continued
4-625
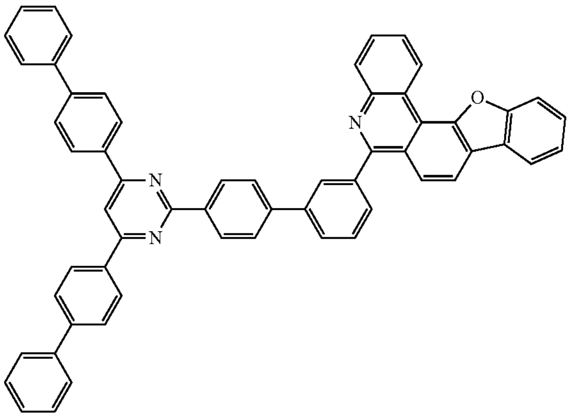
4-626
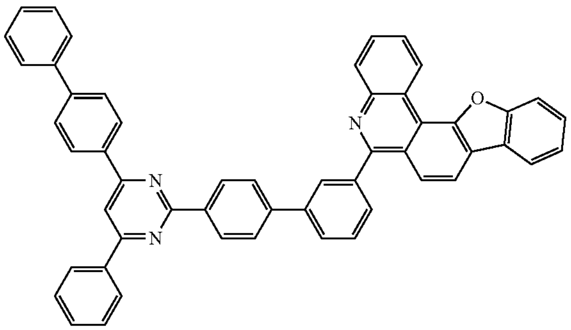
4-627
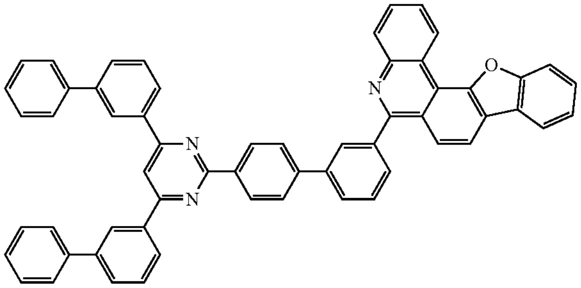
4-628
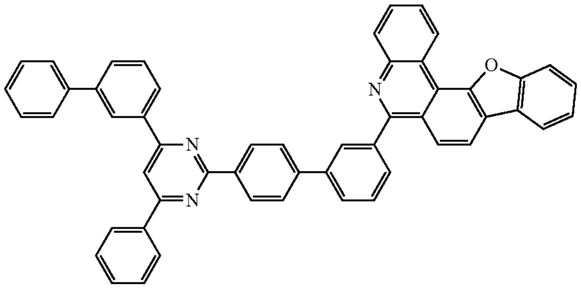
-continued
4-629
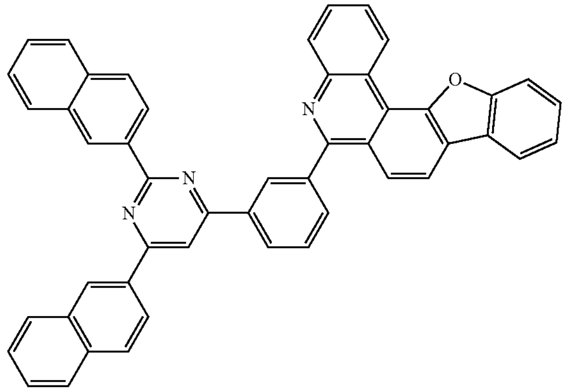
4-630
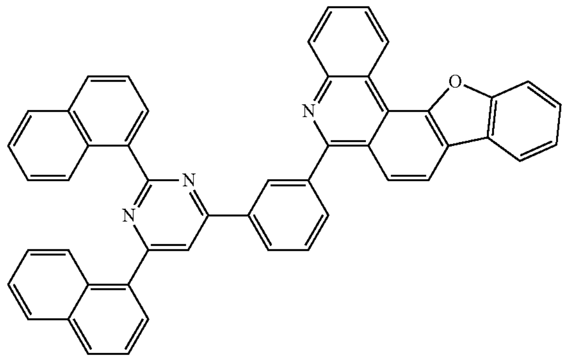
4-631
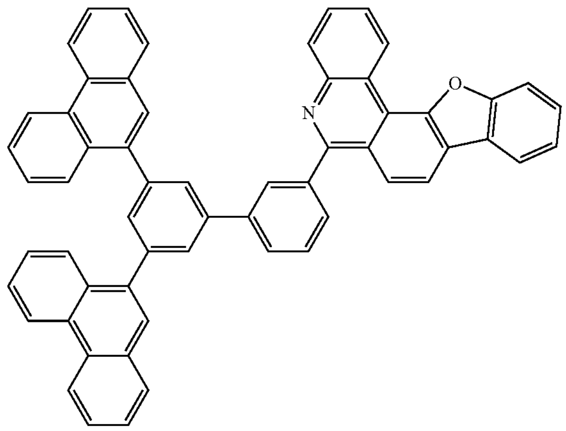

-continued
4-632
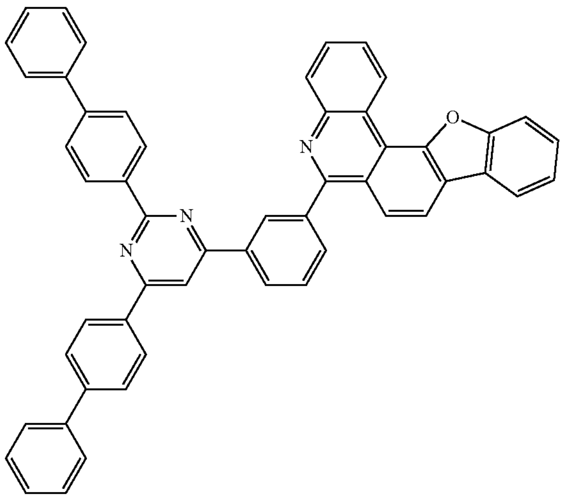
4-633
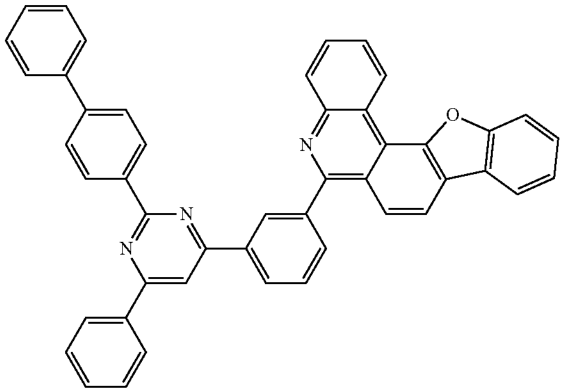
4-634
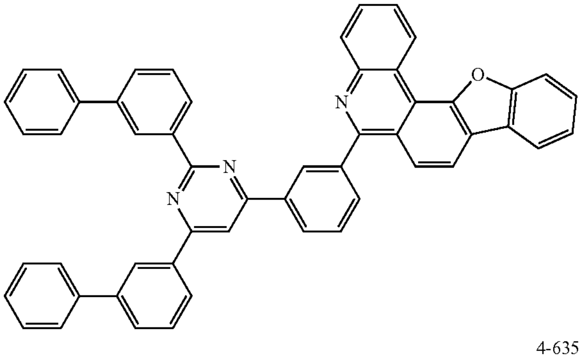
4-635
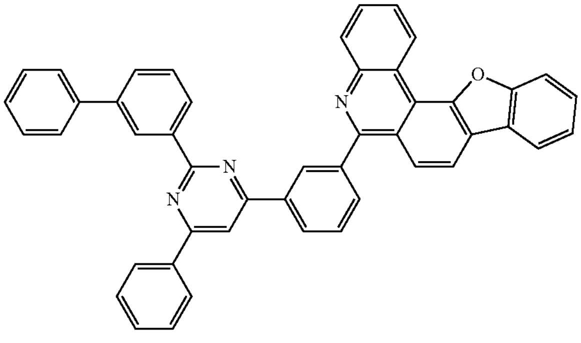
-continued
4-636
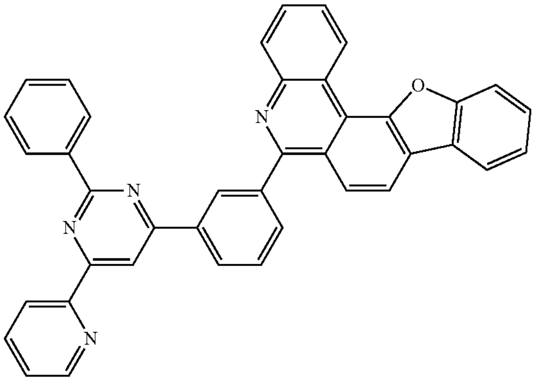
4-637
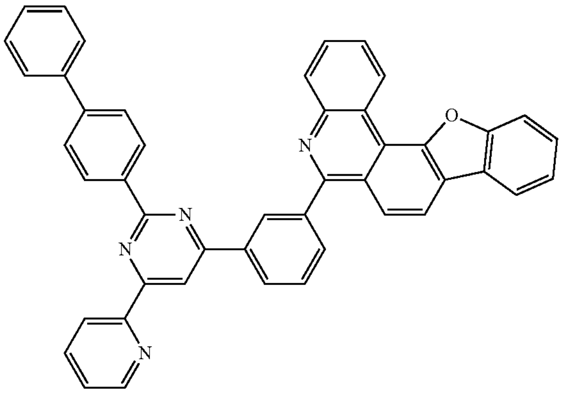
4-638
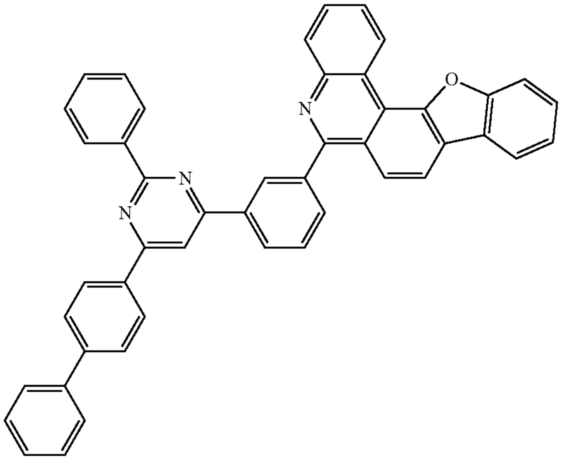
4-639
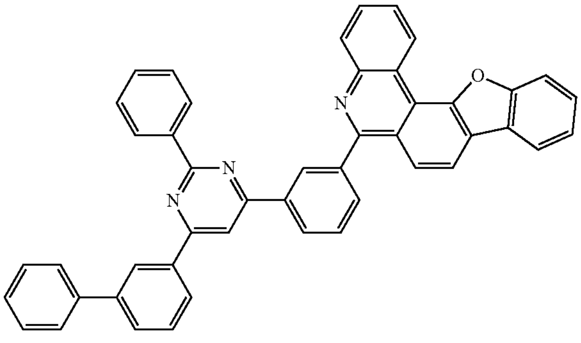

-continued
4-640
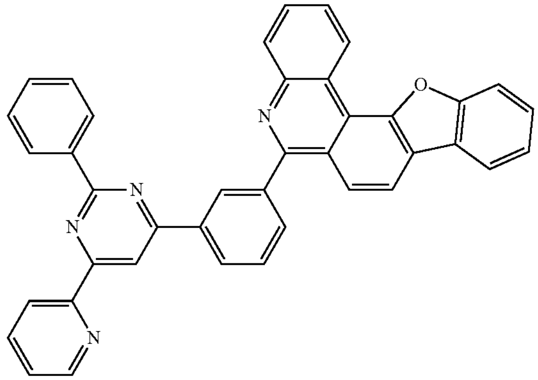
4-641
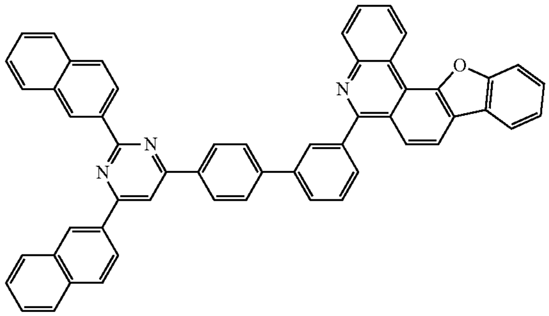
4-642
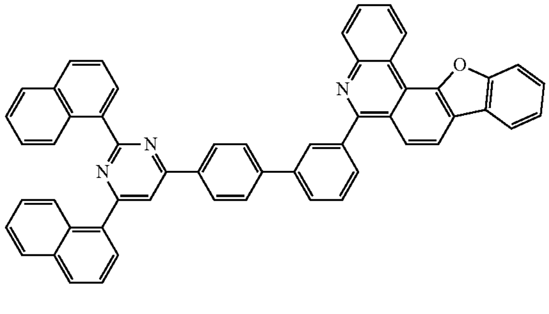
4-643
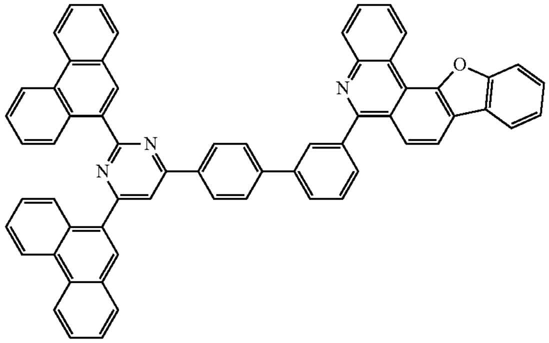
-continued
4-644
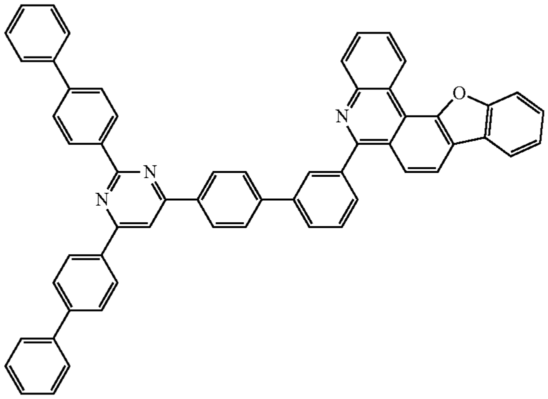
4-645
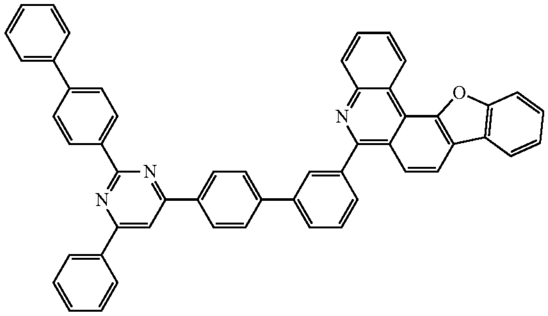
4-646
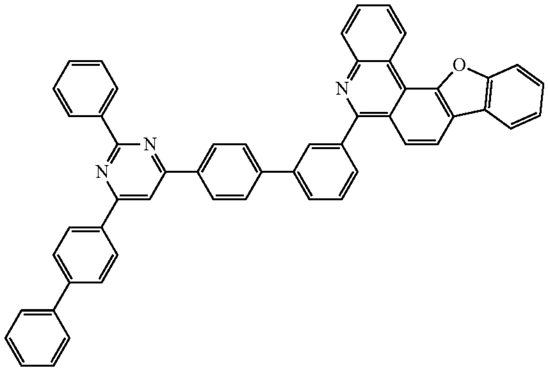
4-647
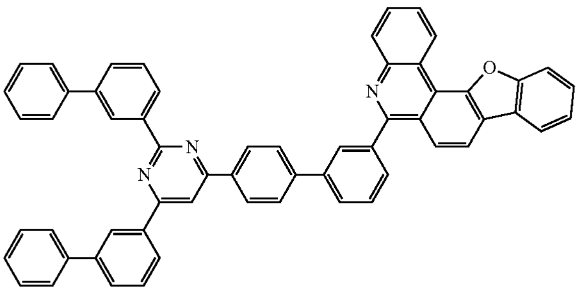

-continued
4-648
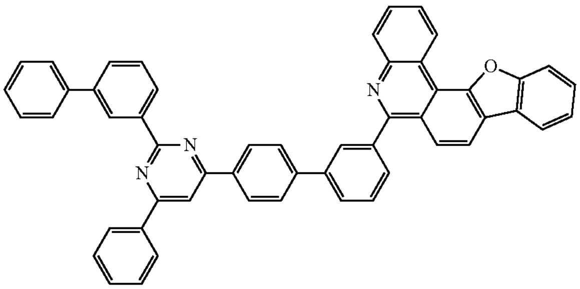
4-649
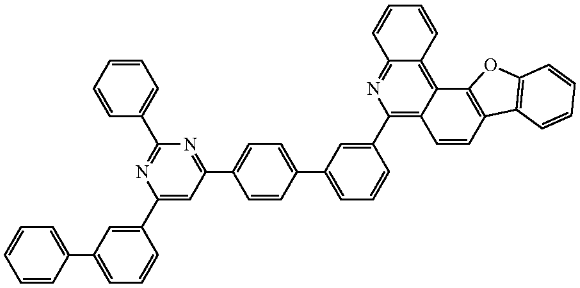
4-650
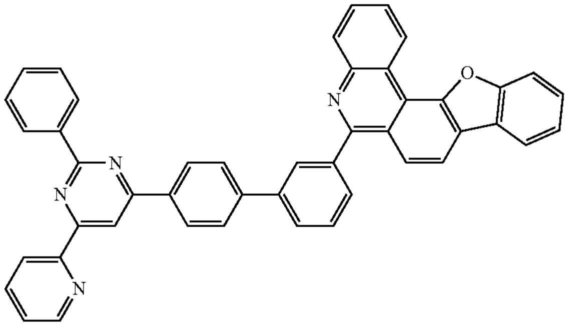
4-651
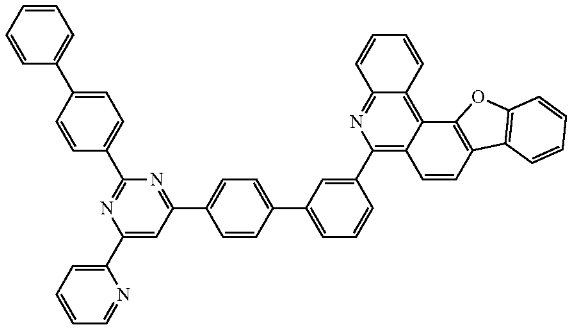
4-652
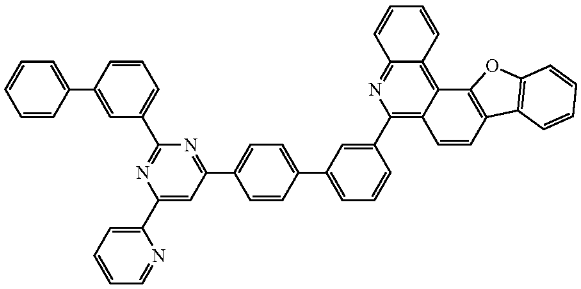
-continued
4-653
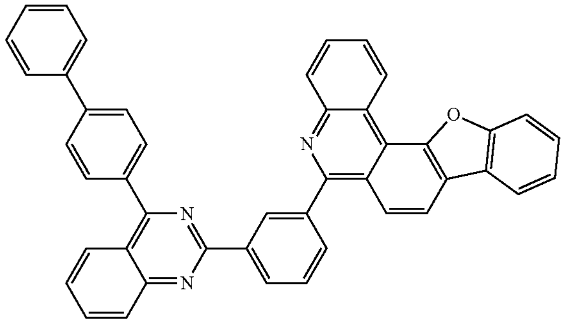
4-654
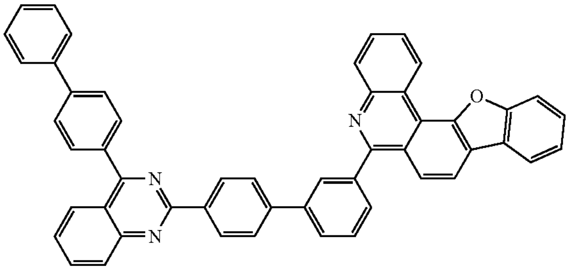
4-655
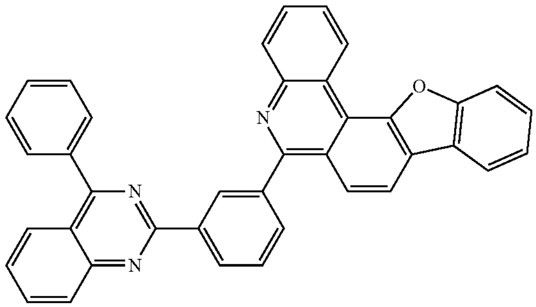
4-656
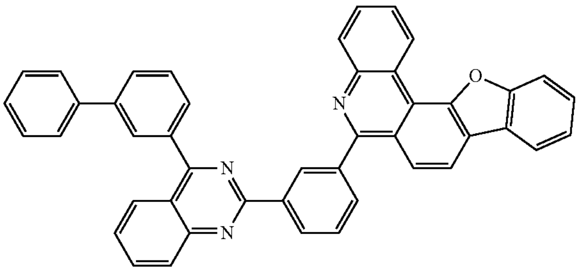
4-657
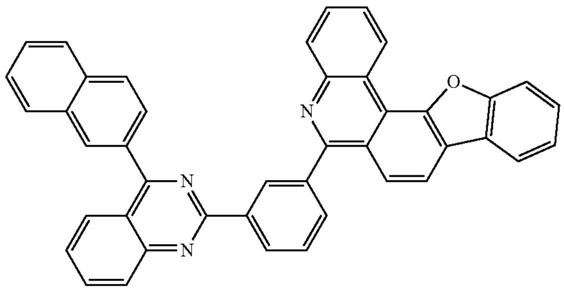

-continued
4-658
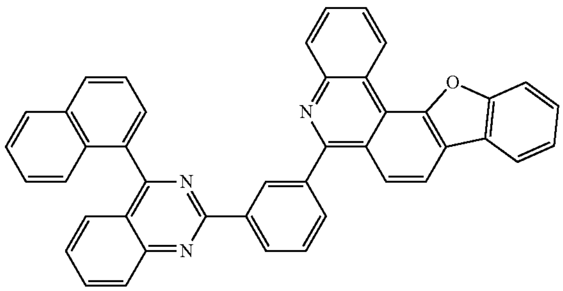
4-659
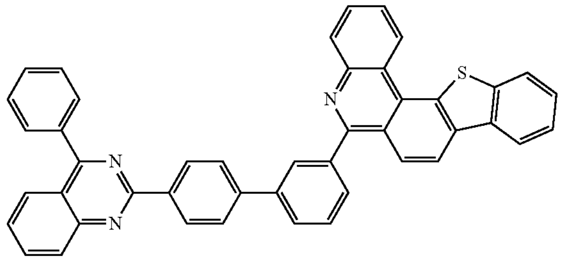
4-660
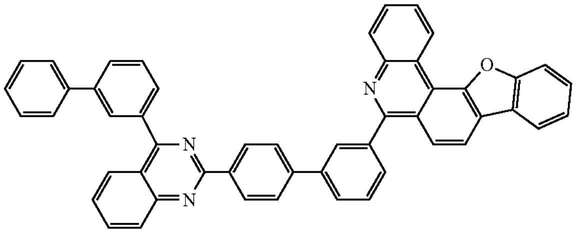
4-661
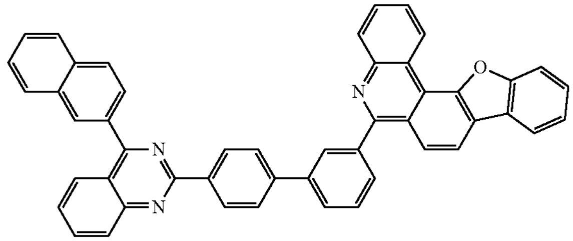
4-662
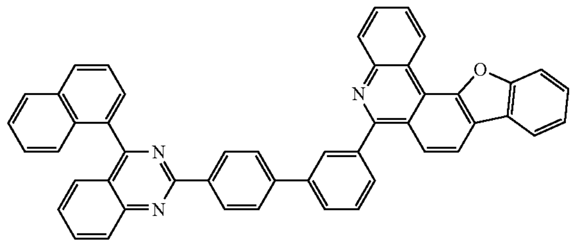
-continued
4-663
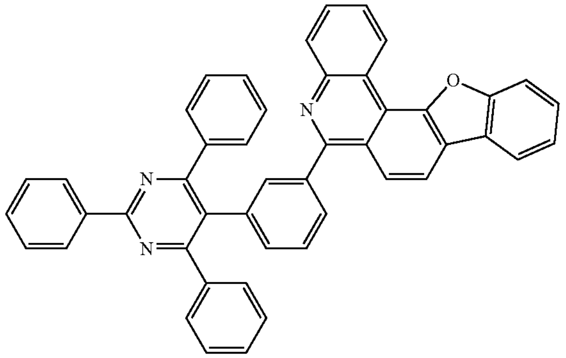
4-664
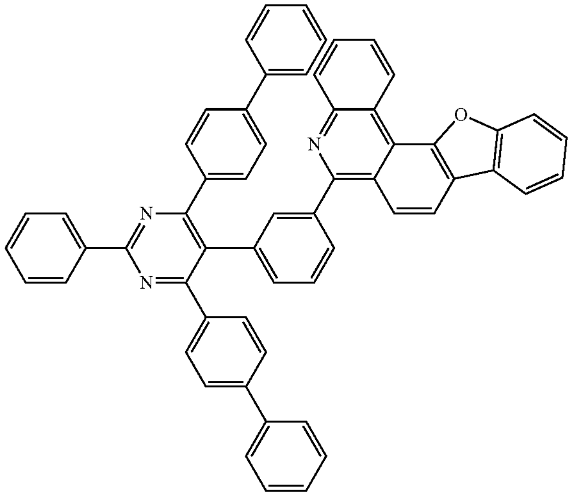
4-665
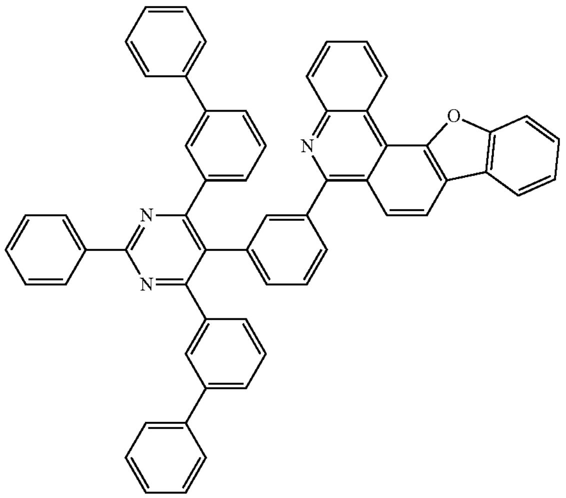

-continued
4-666
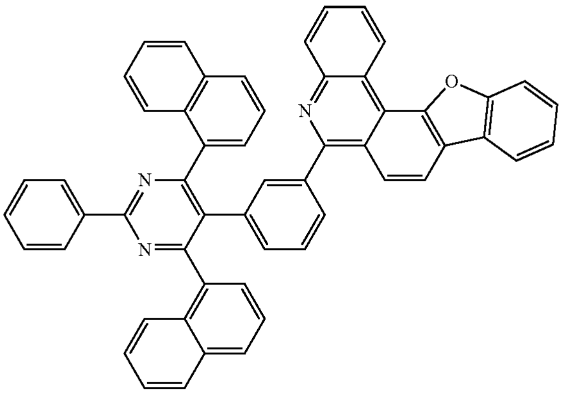
4-667
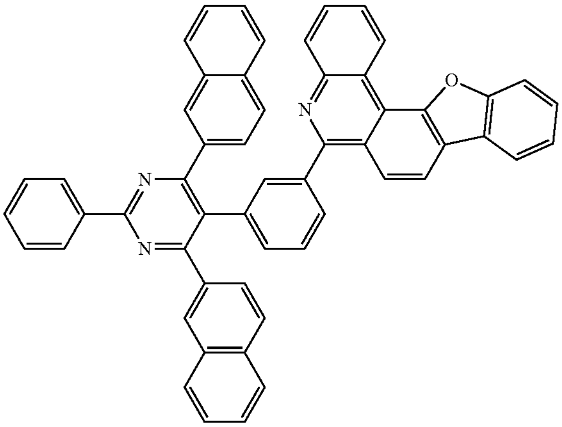
4-668
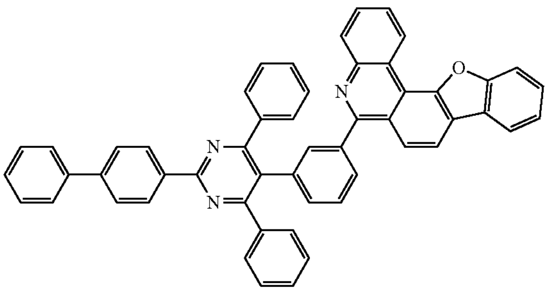
4-669
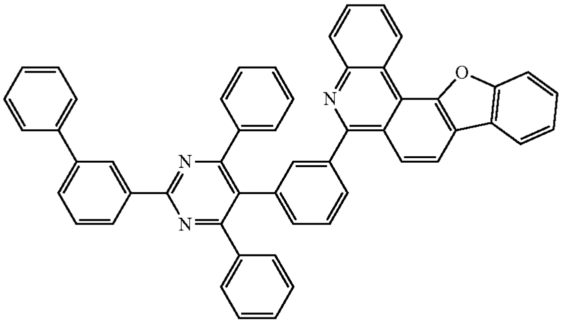
-continued
4-670
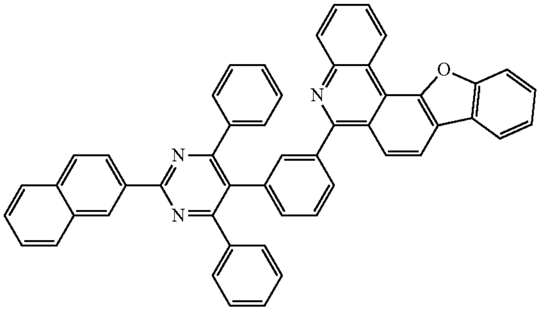
4-671
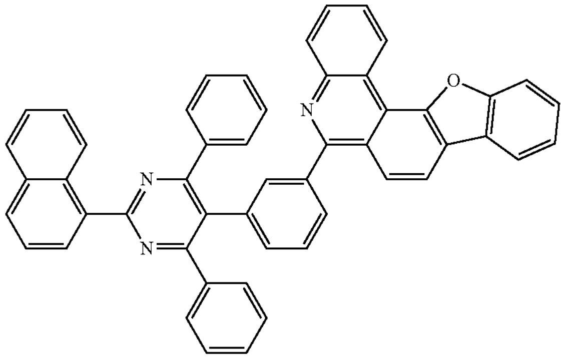
4-672
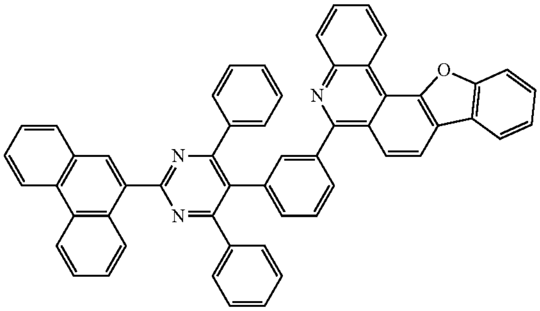
4-673
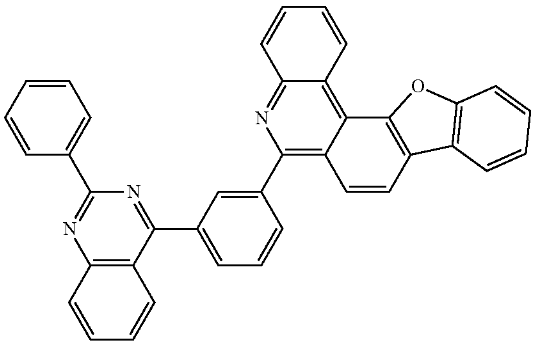

-continued
4-674
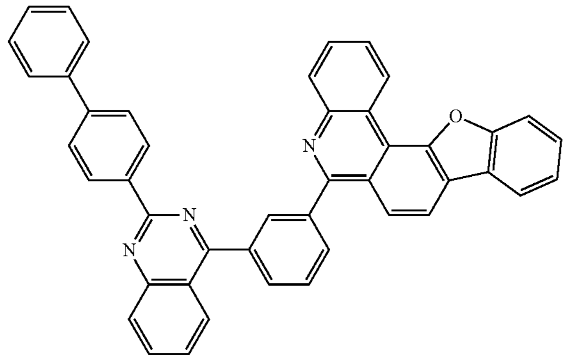
4-675
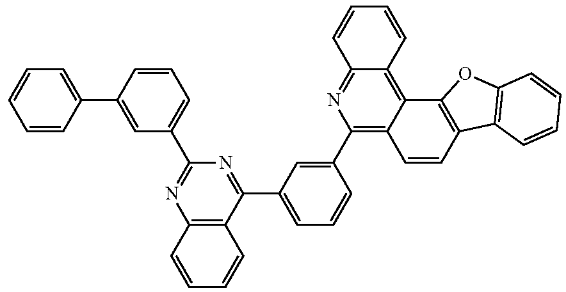
4-676
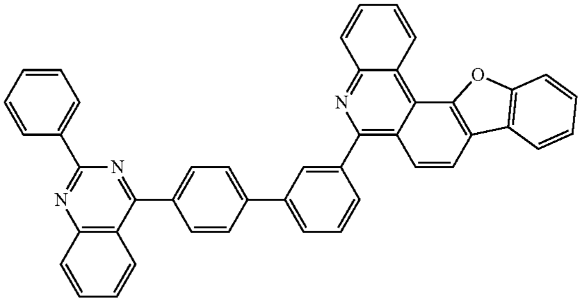
4-677
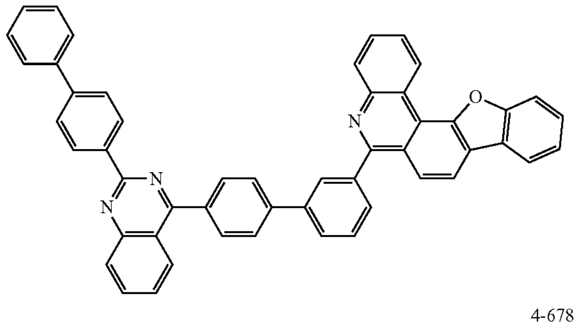
4-678
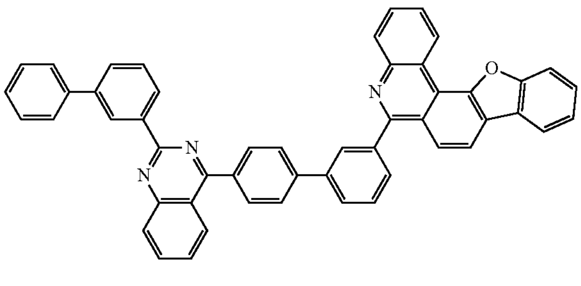
-continued
4-679
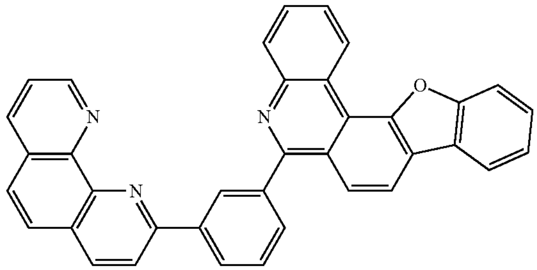
4-680
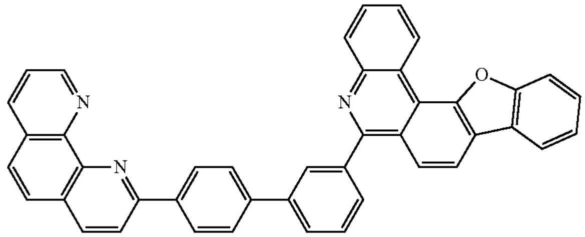
4-681
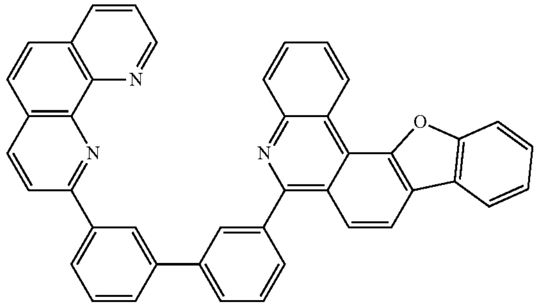
4-682
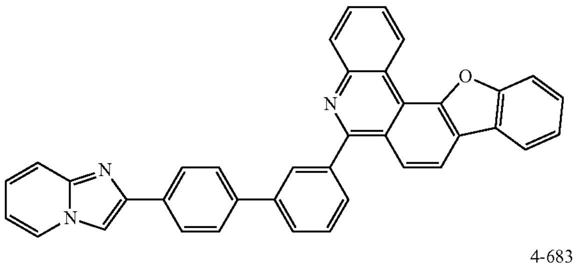
4-683
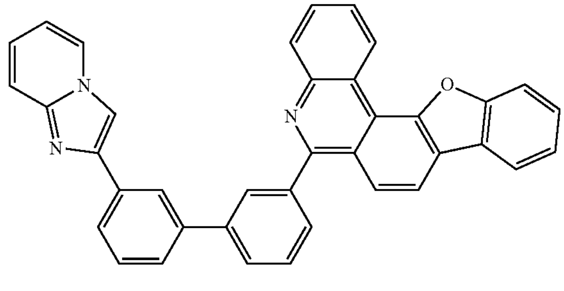

-continued
4-684
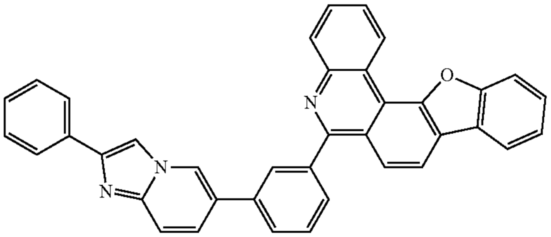
4-685
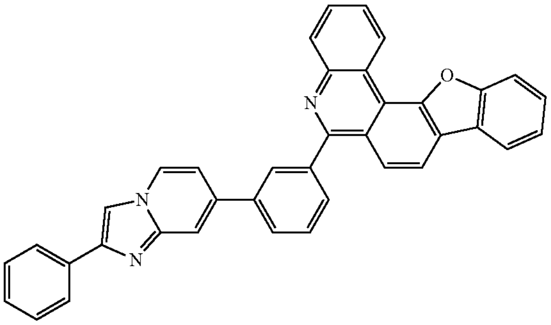
4-686
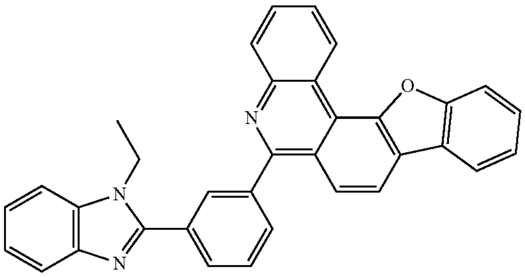
4-687
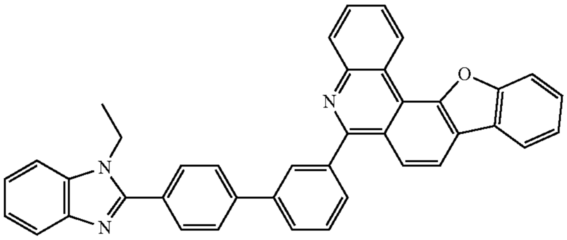
4-688
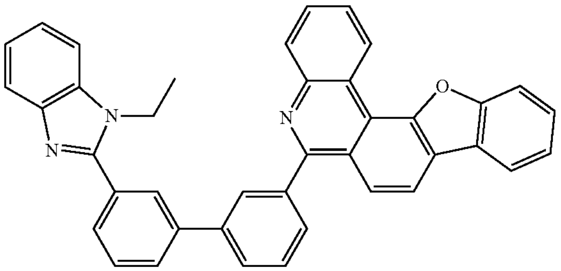
-continued
4-689
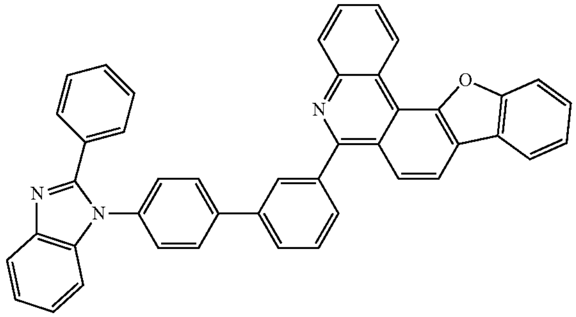
4-690
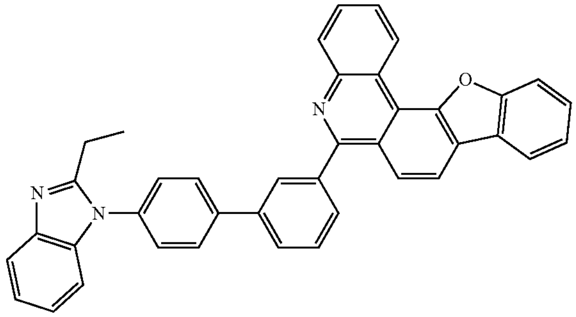
4-691
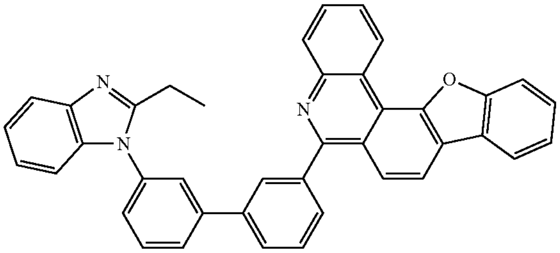
4-692
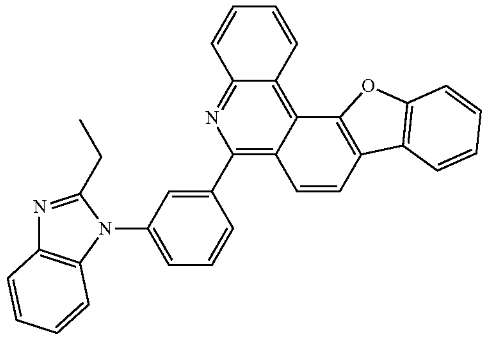
4-693
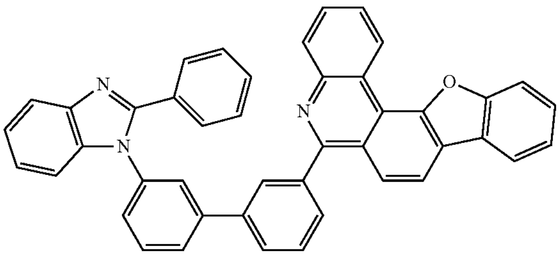

4-694
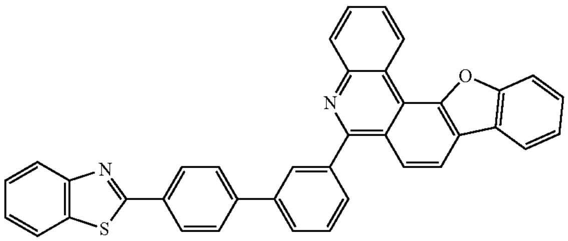
4-695
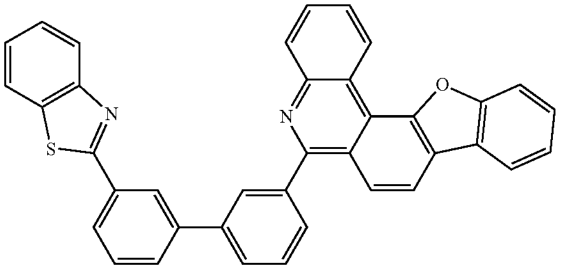
4-696
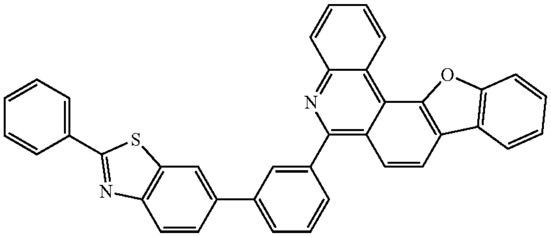
4-697
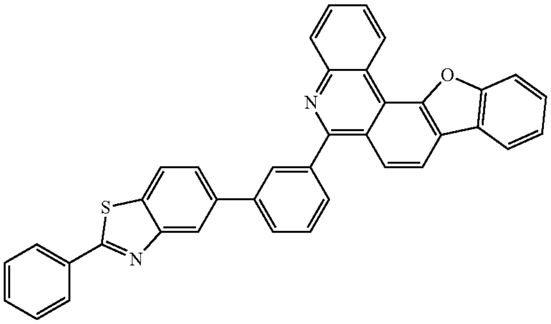
4-698
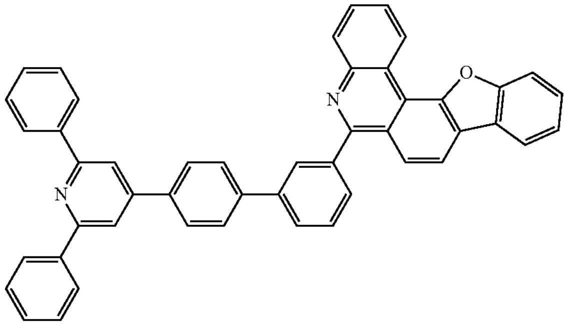
4-699
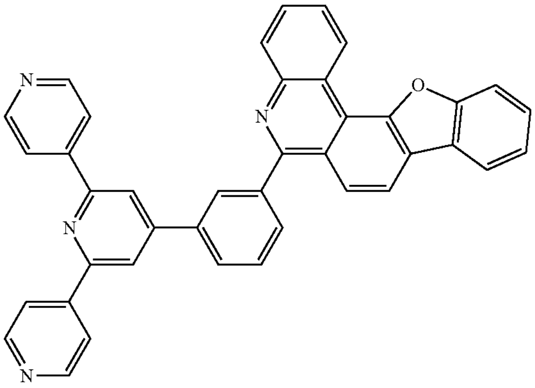
4-700
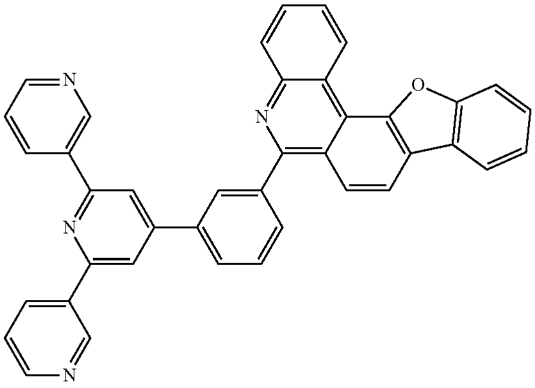
4-701
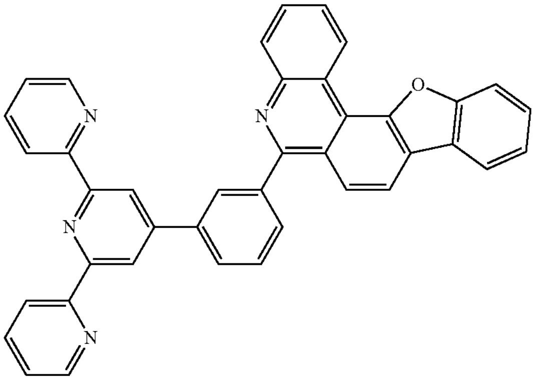
4-702
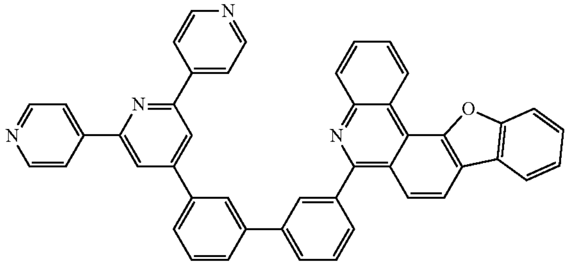

-continued
4-703
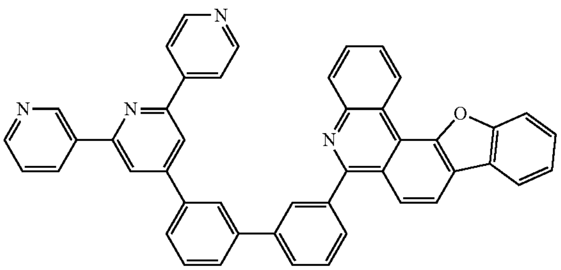
4-704
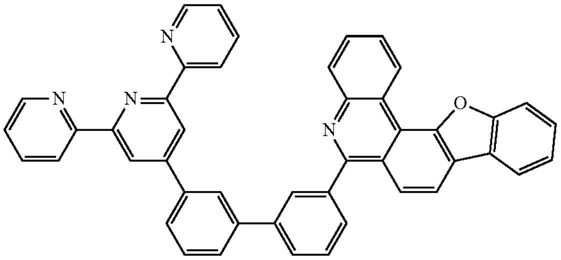
4-705
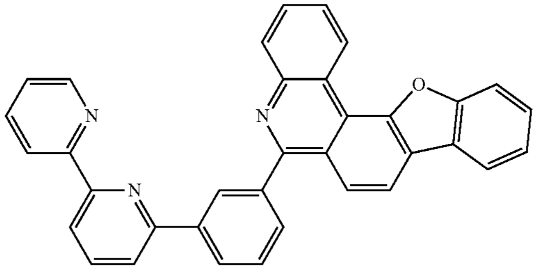
4-706
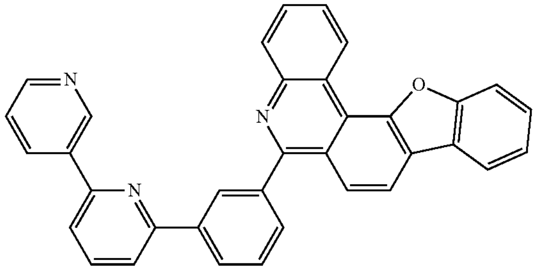
4-707
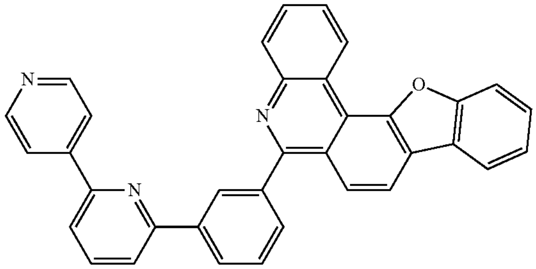
-continued
4-708
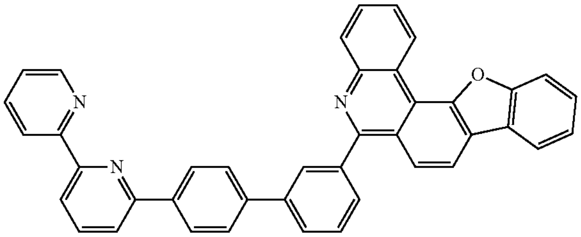
4-709
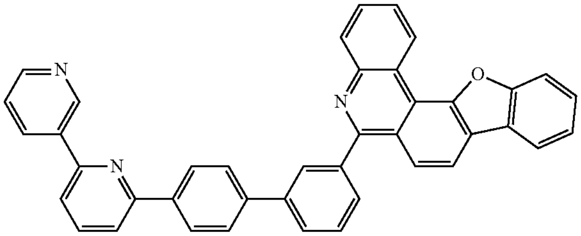
4-710
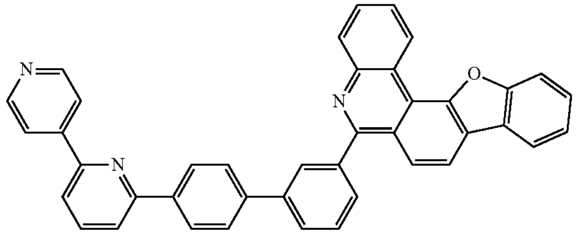
According to another exemplary embodiment of the present specification,
in Chemical Formula 23, Ar may be bonded to an atom bonded to a core of phenyl at a para position thereof, and Chemical Formula 23 may be selected from the following compounds.
4-181
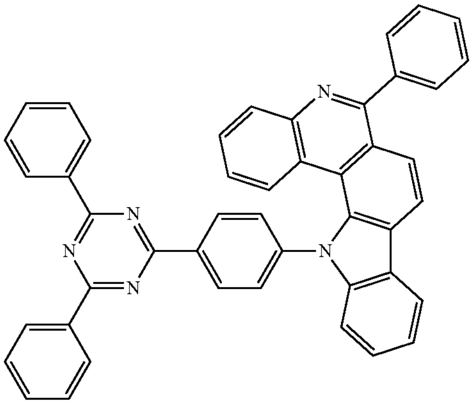

4-182
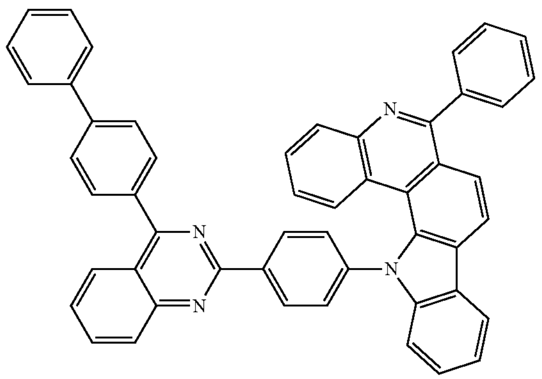
4-183
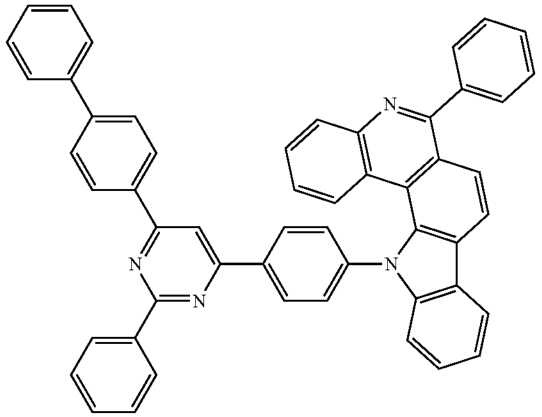
4-184
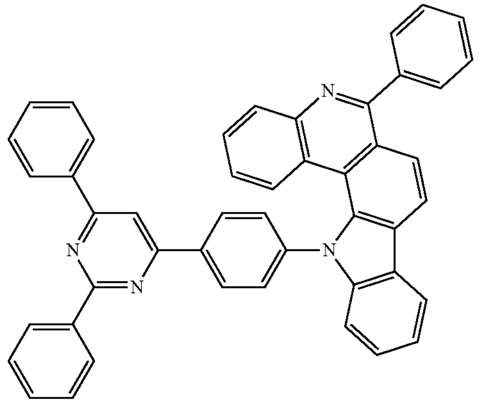
4-185
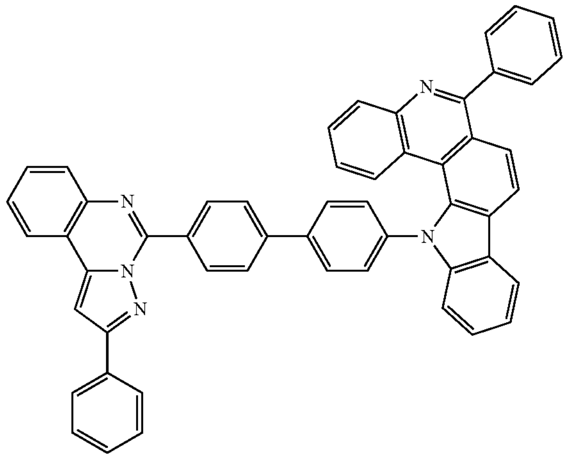
4-186
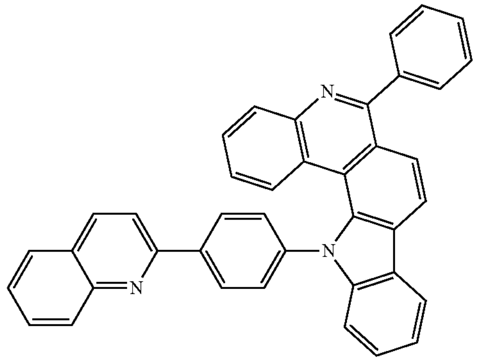
4-187
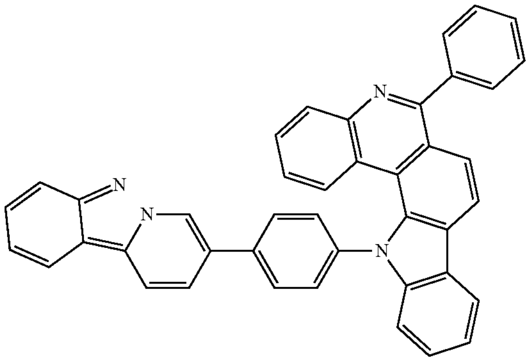
4-188
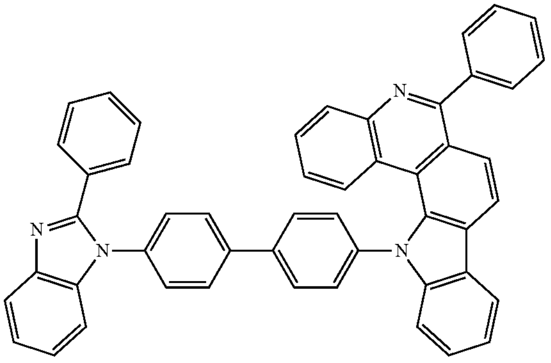

-continued
4-189
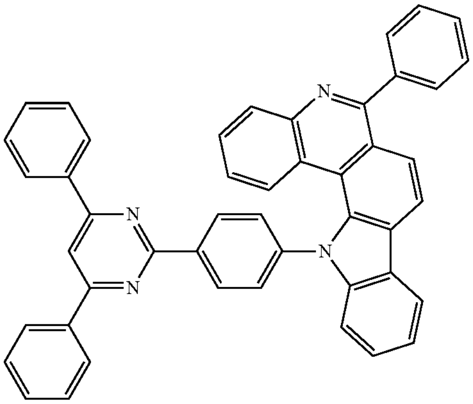
4-190
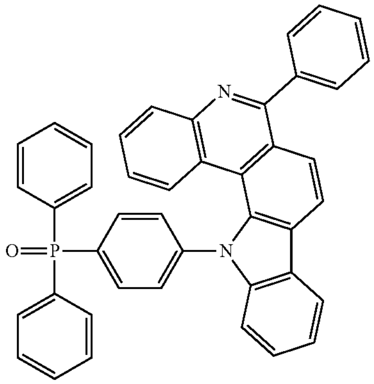
4-191
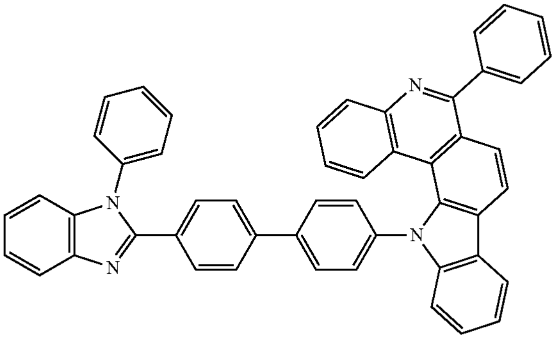
4-192
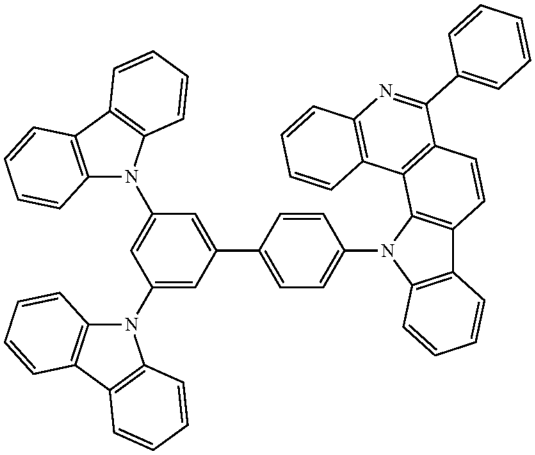
-continued
4-193
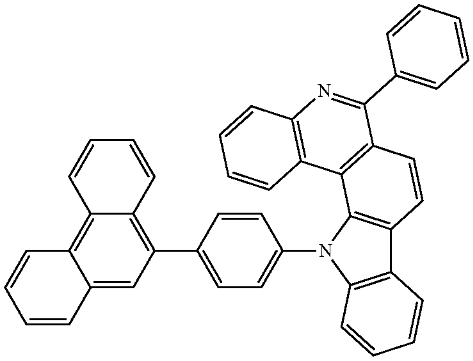
4-194
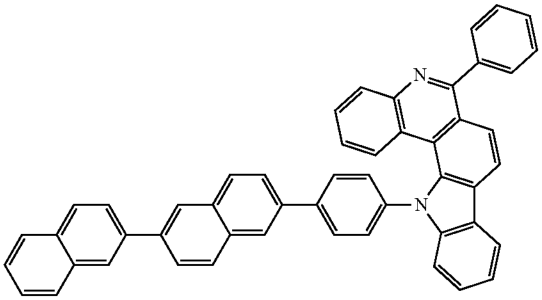
4-195
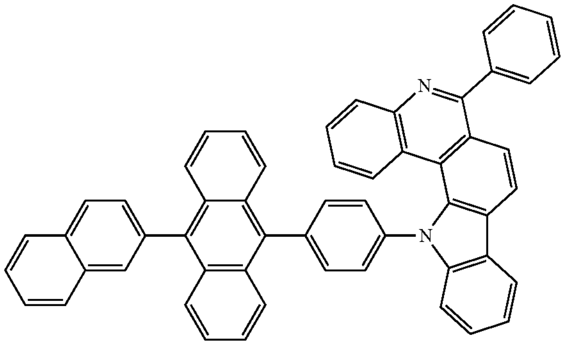
4-196
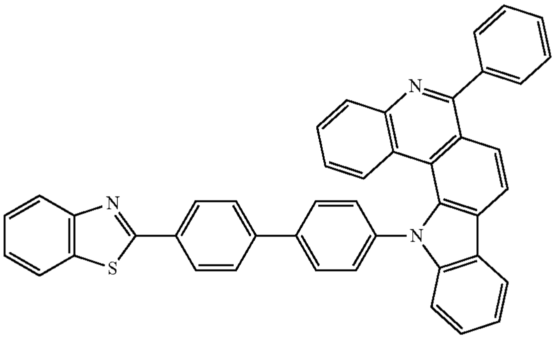

-continued
4-197
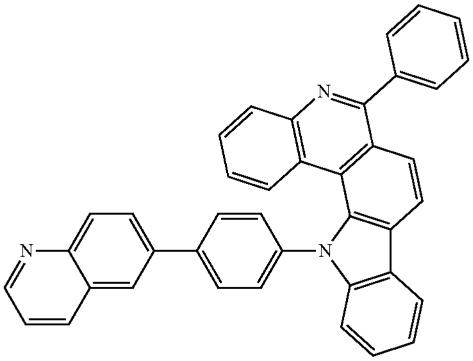
4-198
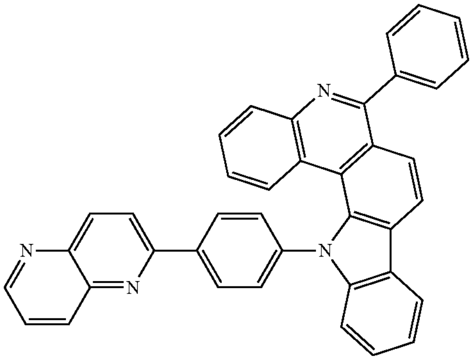
4-199
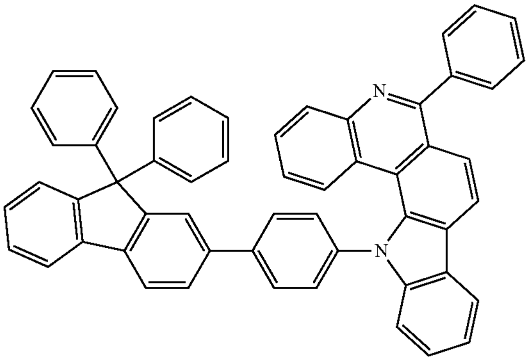
4-200
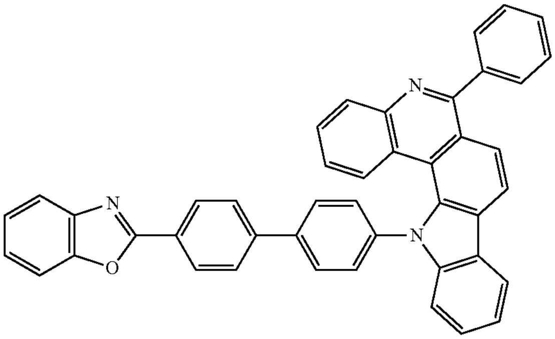
-continued
4-201
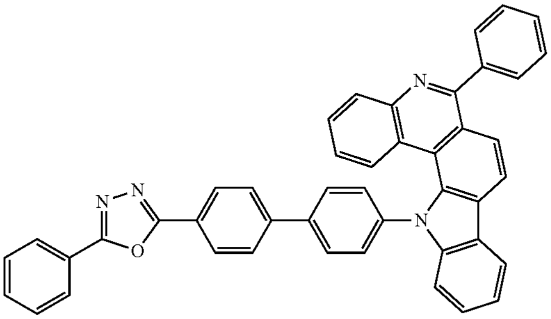
4-202
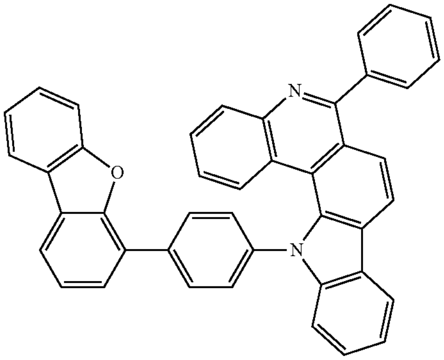
4-203
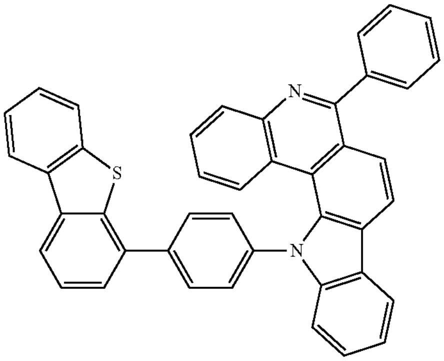
4-204
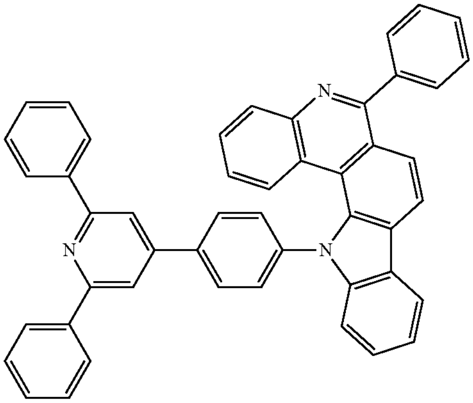

-continued
4-205
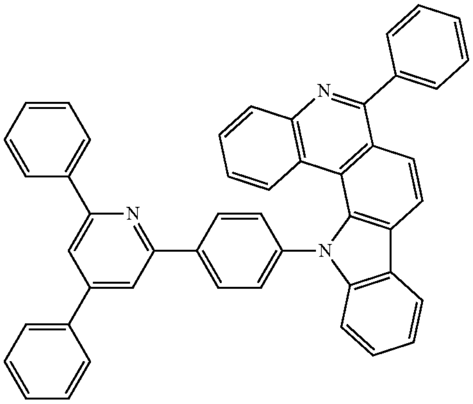
4-206
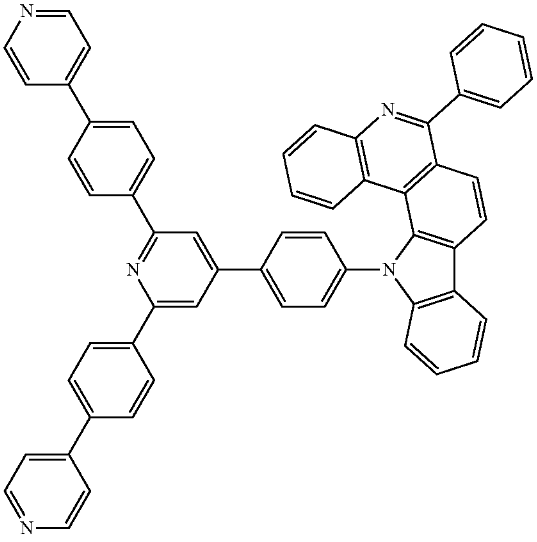
4-207
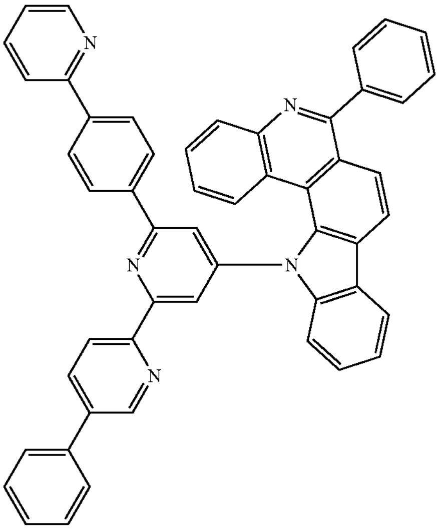
-continued
4-208
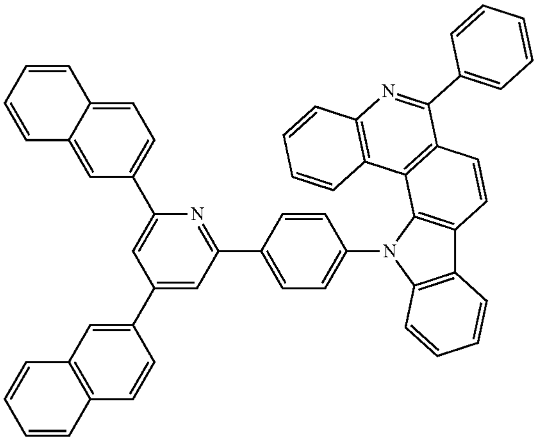
4-209
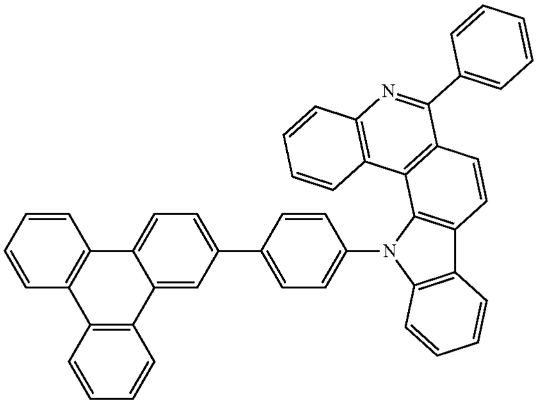
4-210
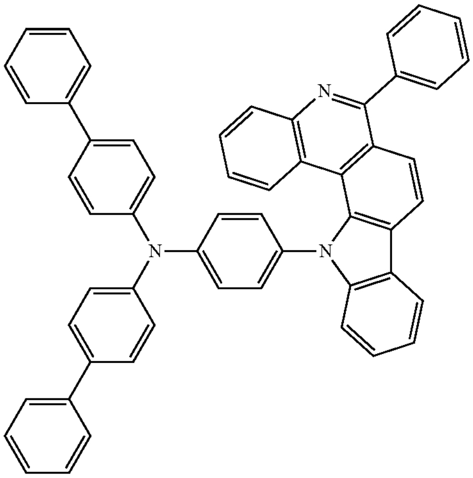

-continued
4-211
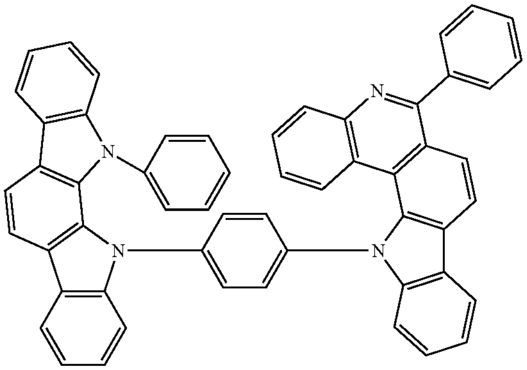
4-212
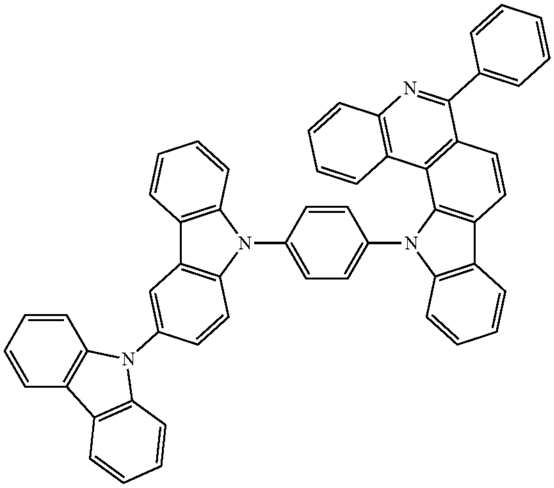
4-213
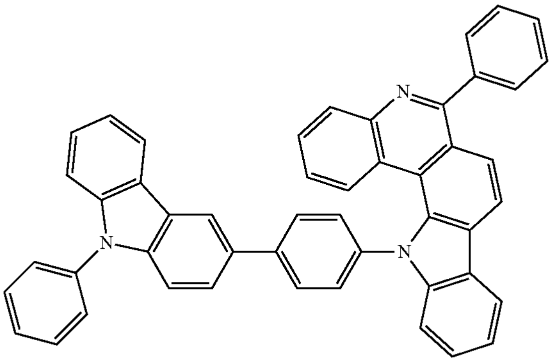
-continued
4-214
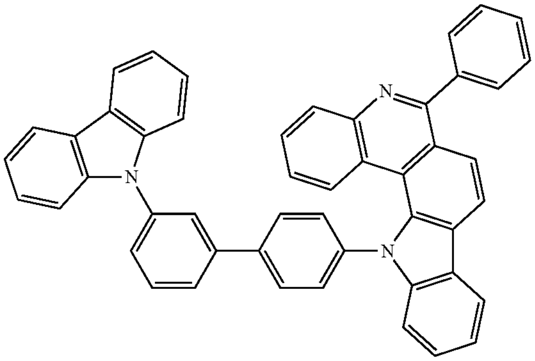
4-215
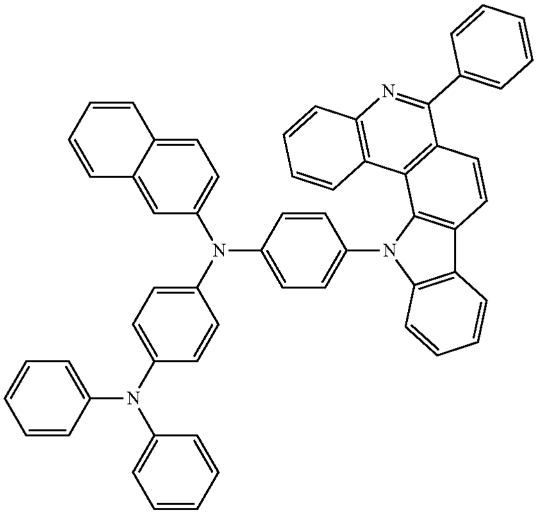
According to another exemplary embodiment of the present specification,
in Chemical Formula 23, Ar may be bonded to an atom bonded to a core of phenyl at a meta position thereof, and Chemical Formula 23 may be selected from the following compounds.
4-216
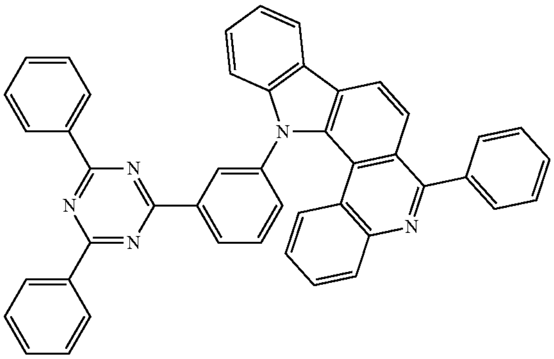

-continued
4217
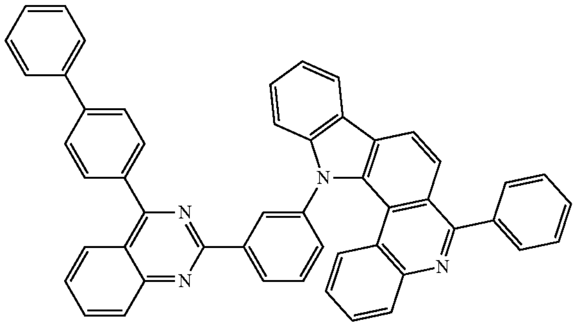
4-218
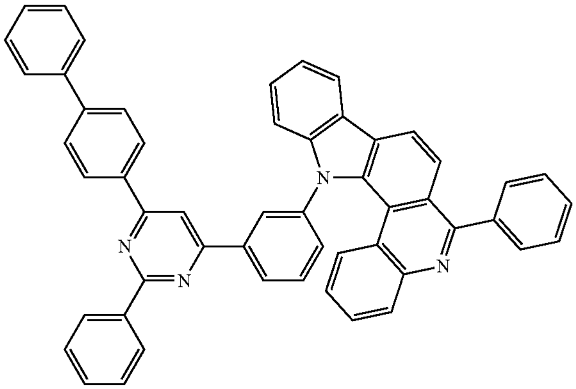
4-219
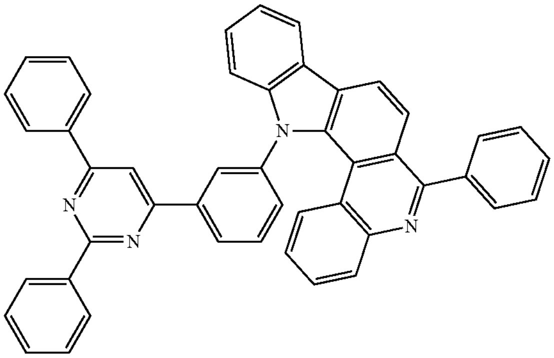
4-220
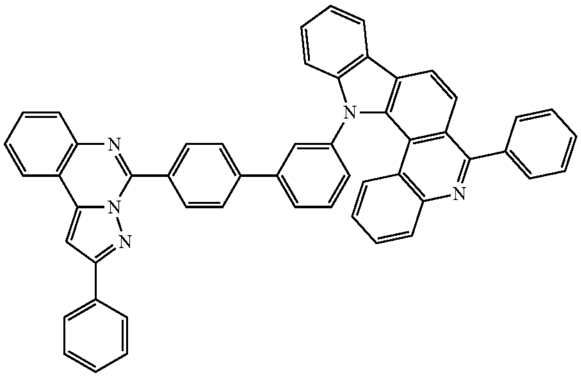
-continued
4-221
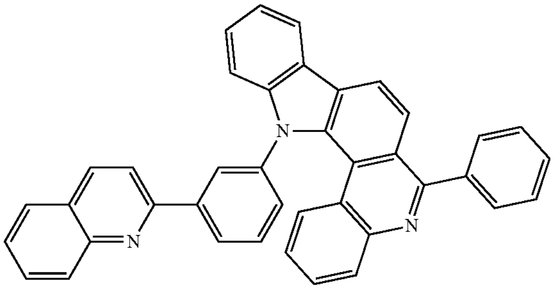
4-222
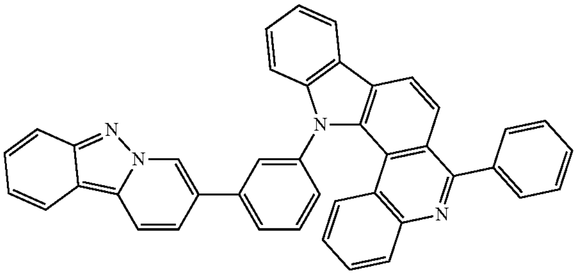
4-223
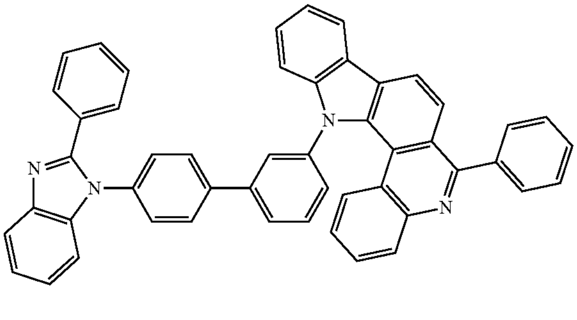
4-224
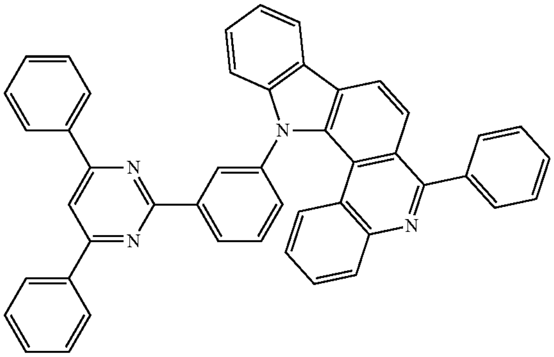

-continued
4-225
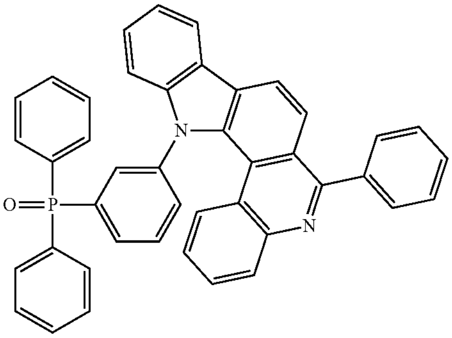
4-226
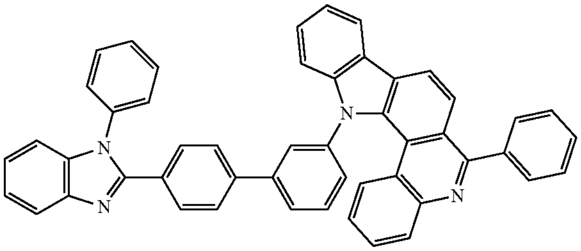
4-227
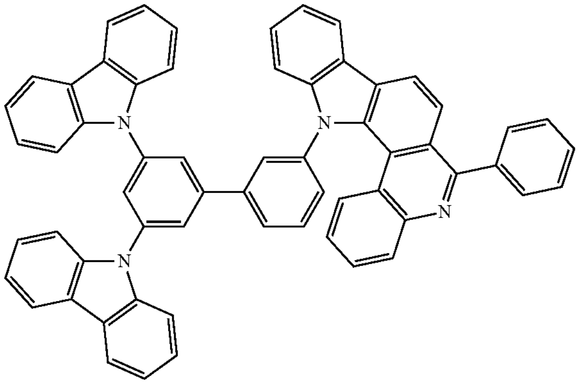
4-228
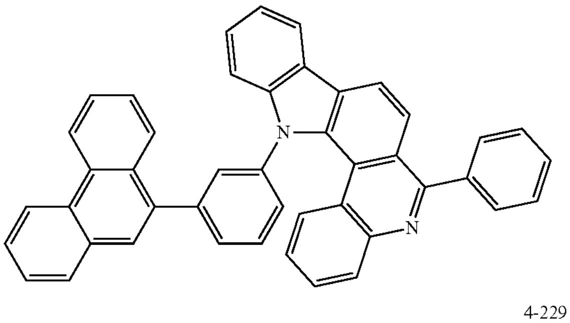
4-229
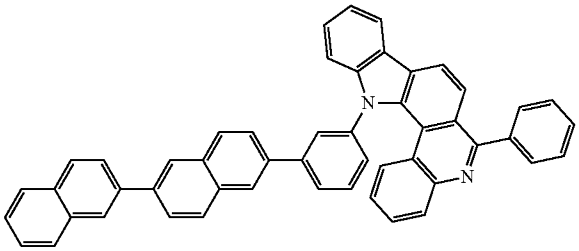
-continued
4-230
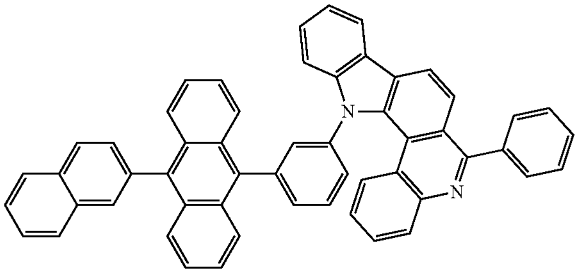
4-231
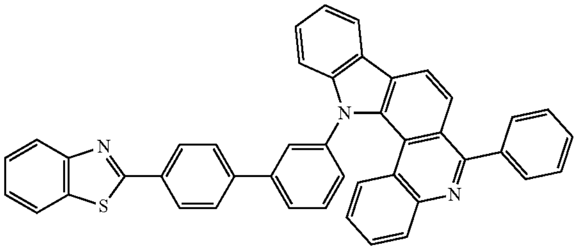
4-232
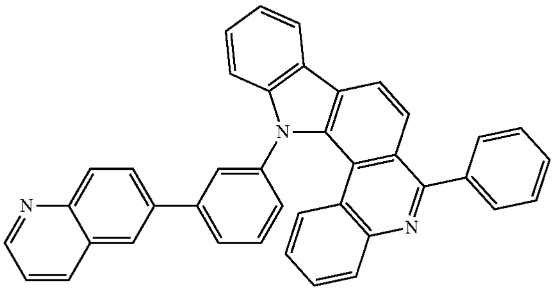
4-233
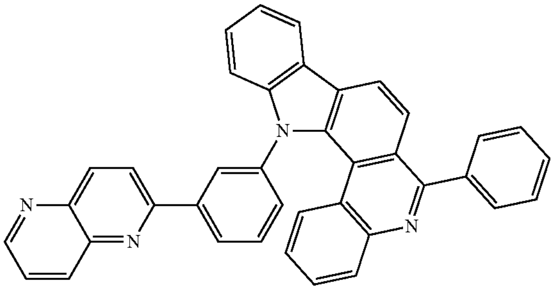
4-234
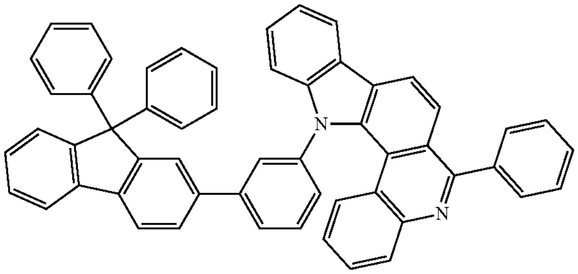

-continued
4-235
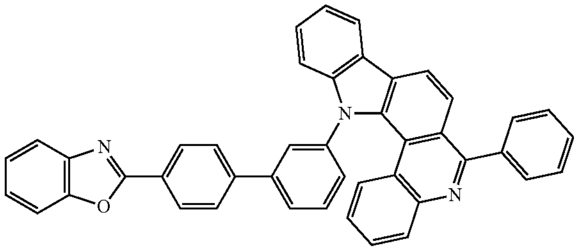
4-236
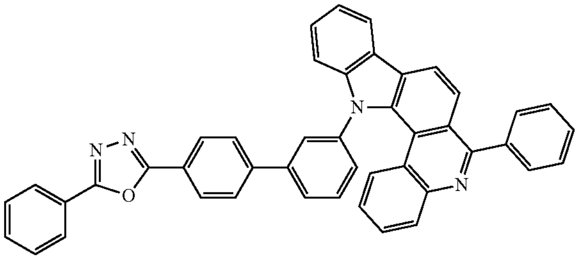
4-237
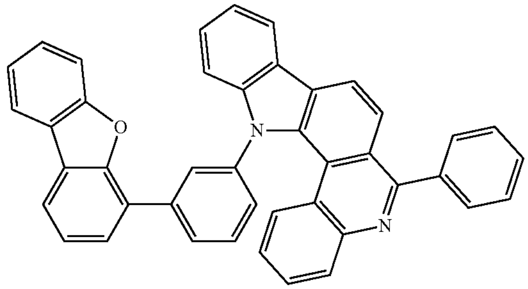
4-238
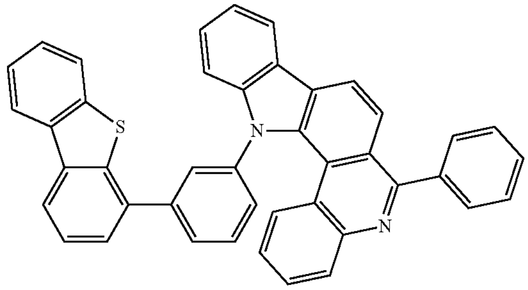
4-239
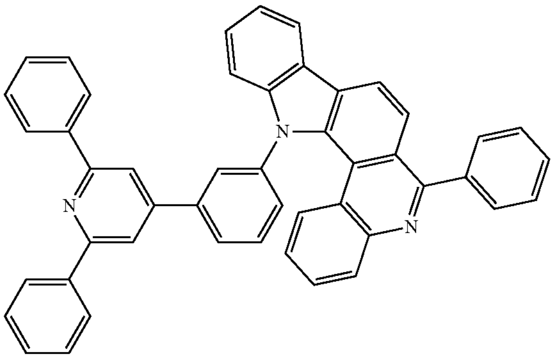
-continued
4-240
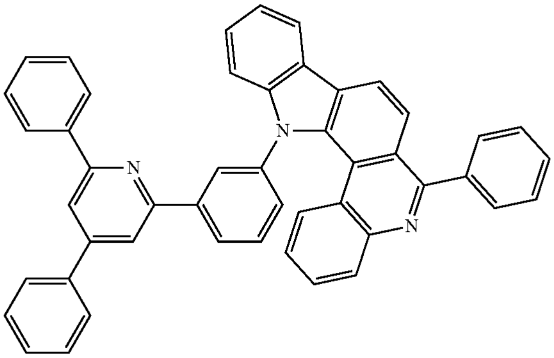
4-241
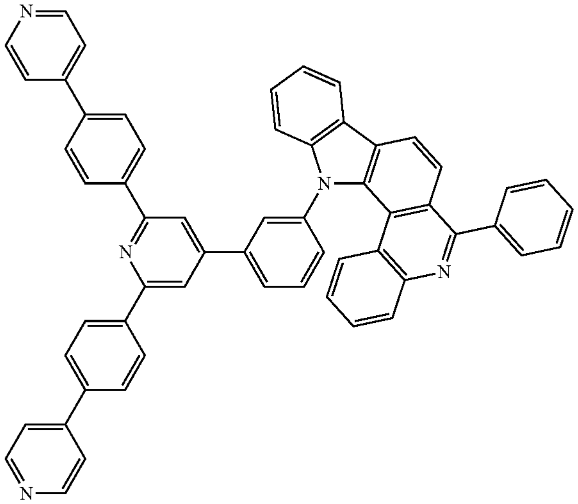
4-242
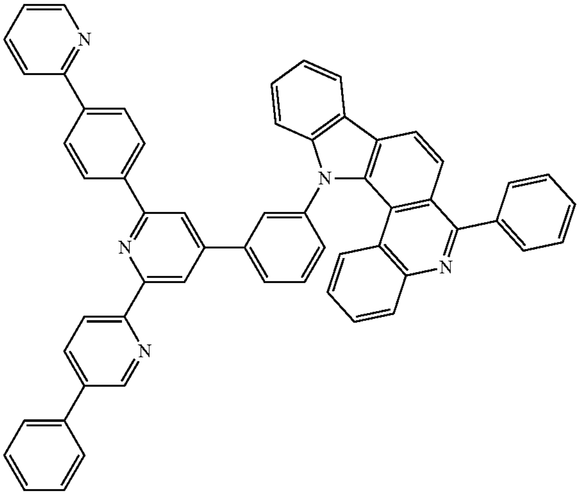

-continued
4-243
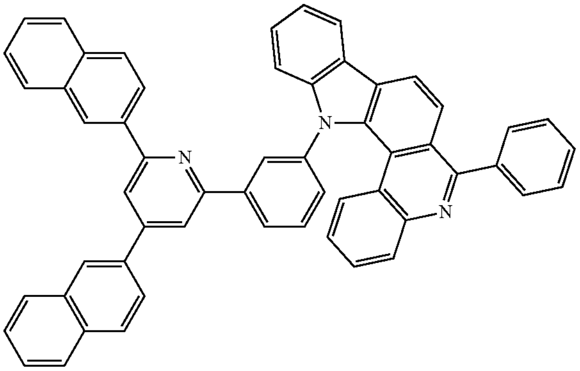
4-244
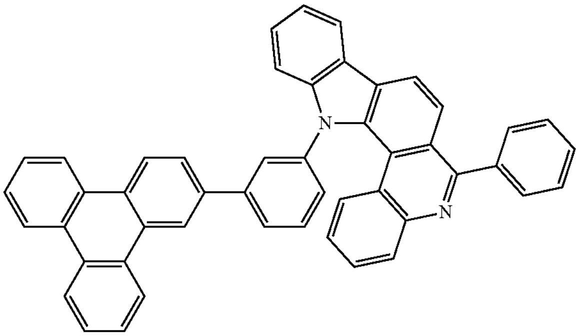
4-245
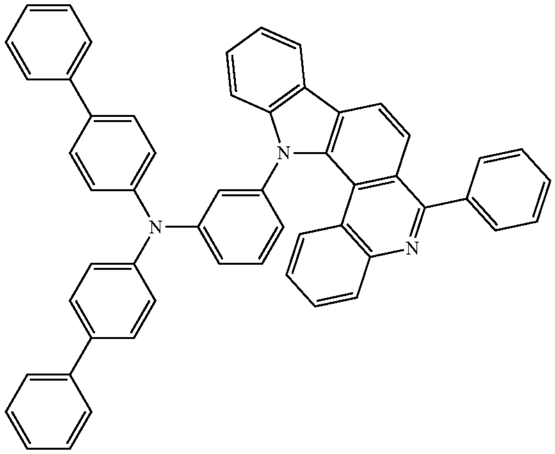
-continued
4-246
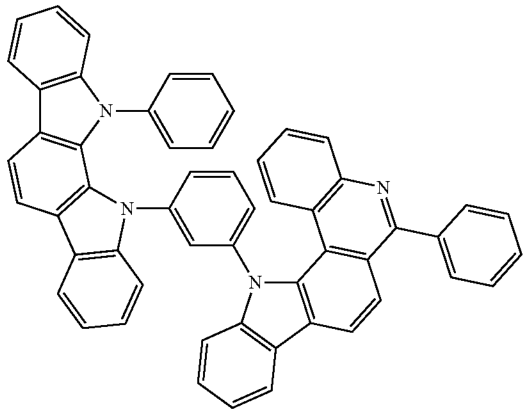
4-247
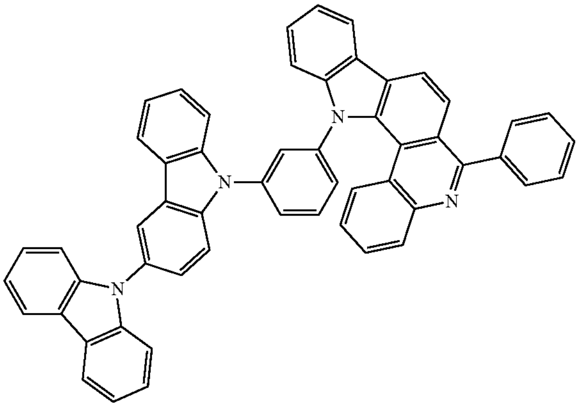
4-248
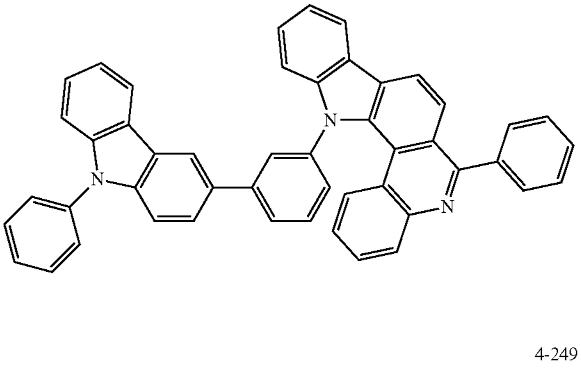
4-249
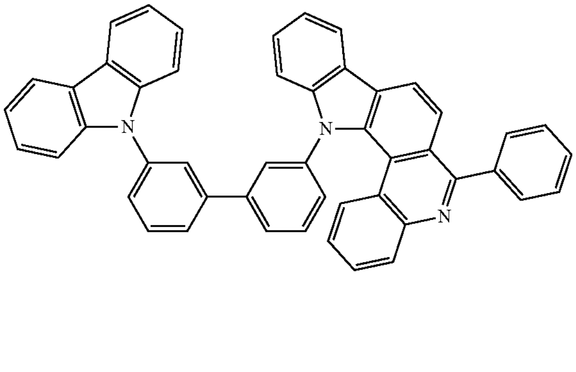

-continued
4-250
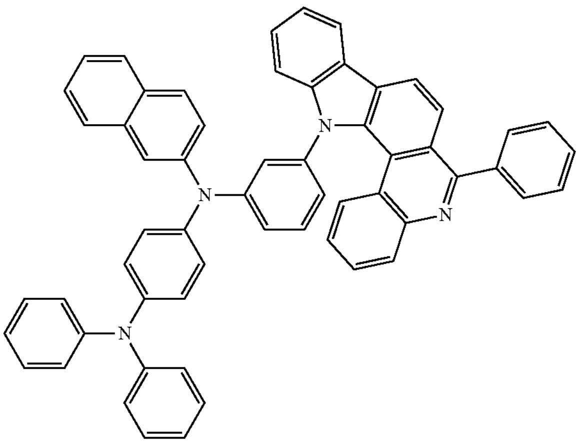
5-1
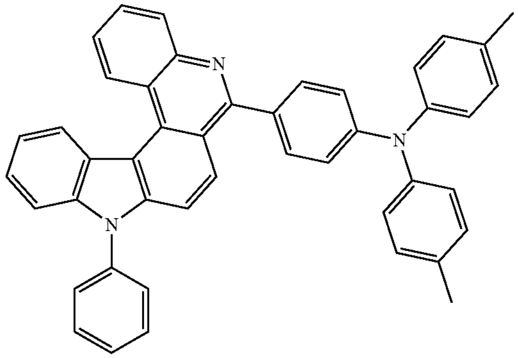
5-2
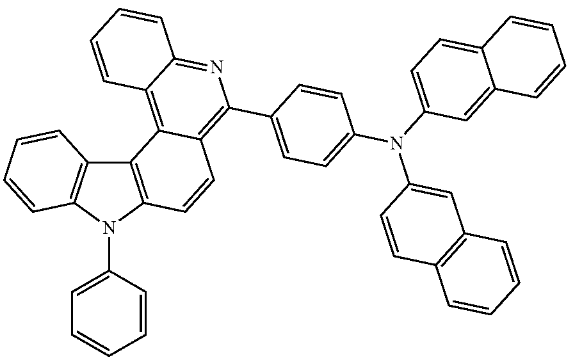
5-3
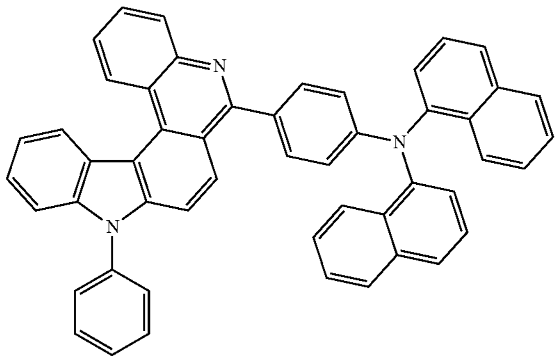
-continued
5-4
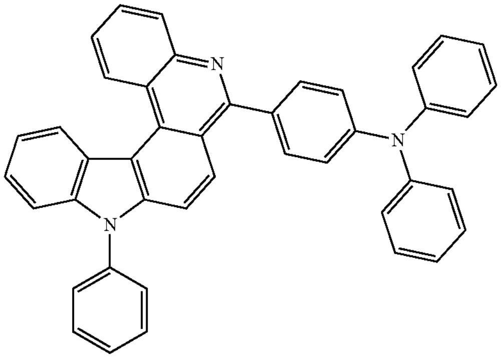
5-5
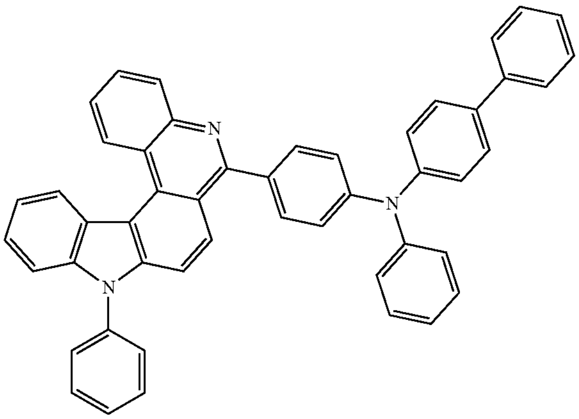
5-6
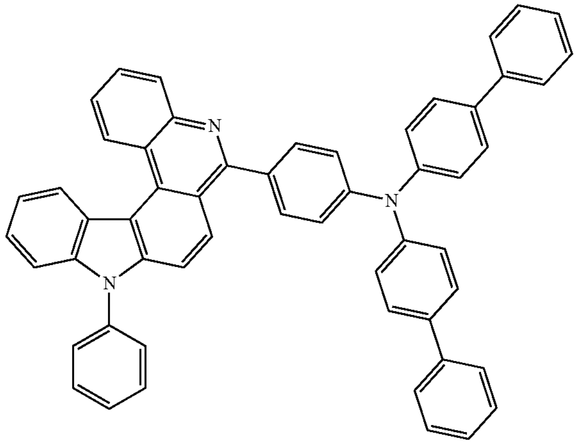
5-7
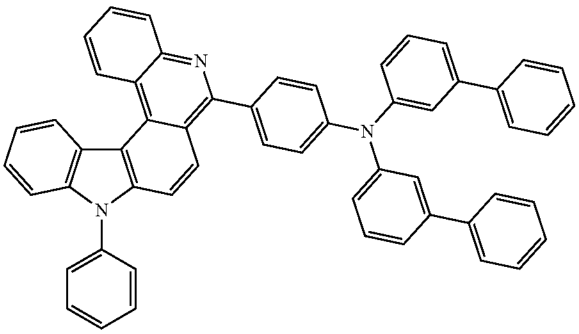

-continued
5-8
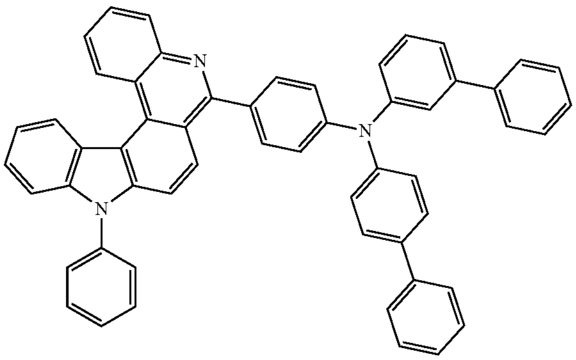
5-9
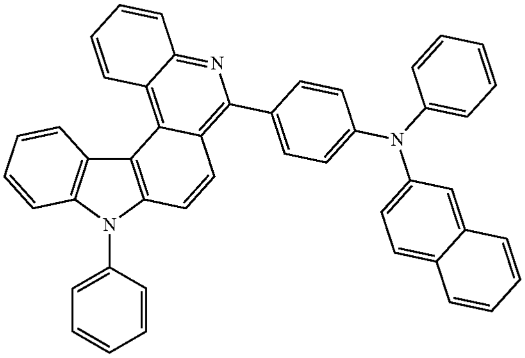
5-10
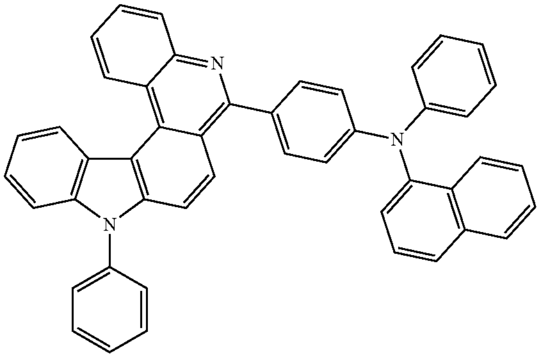
5-11
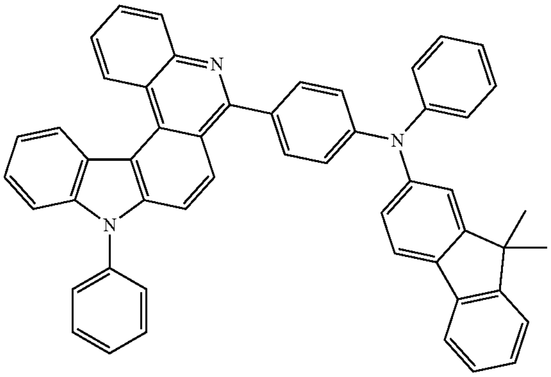
-continued
5-12
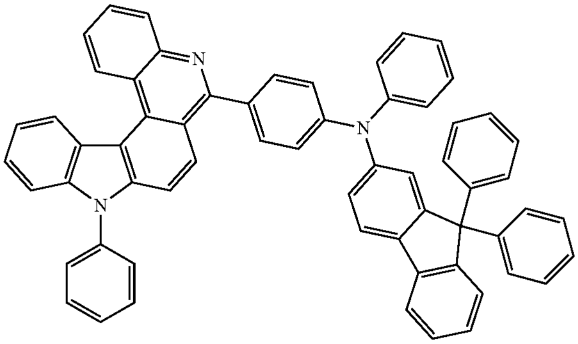
5-13
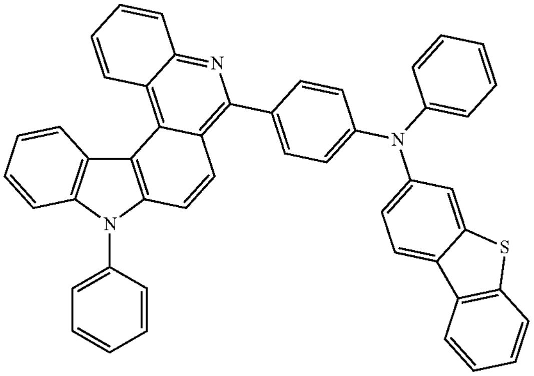
5-14
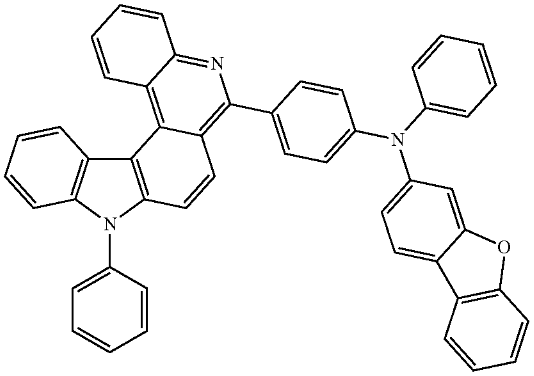
5-15
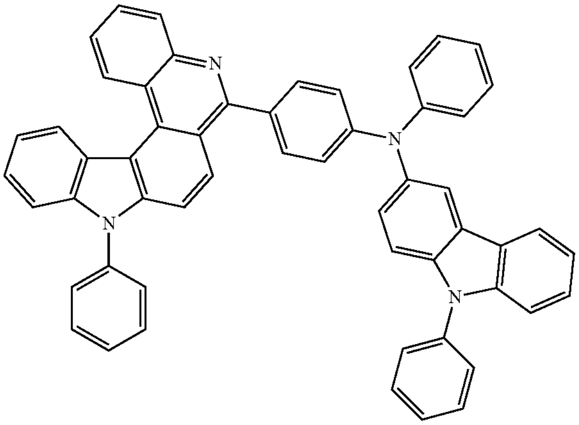

-continued
5-16
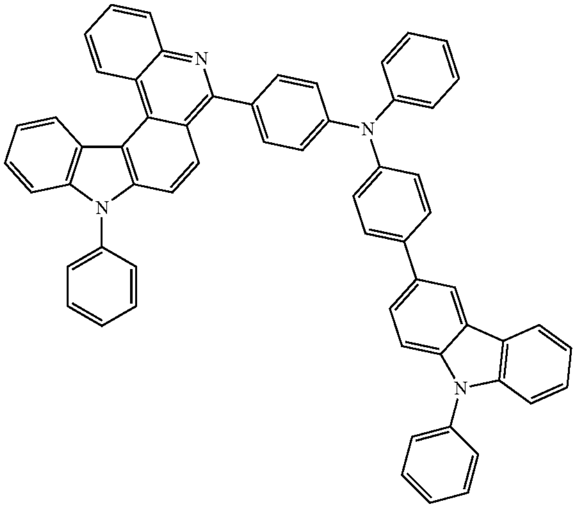
5-17
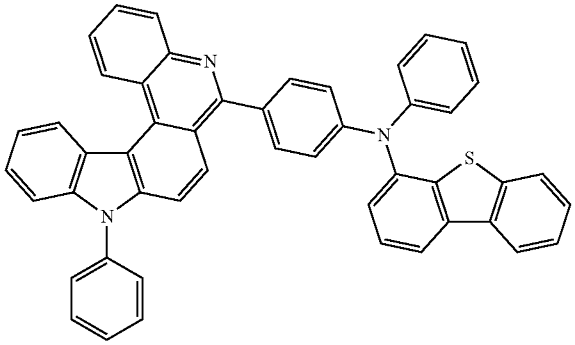
5-18
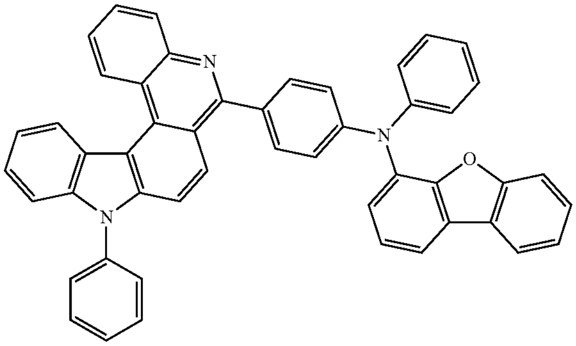
-continued
5-19
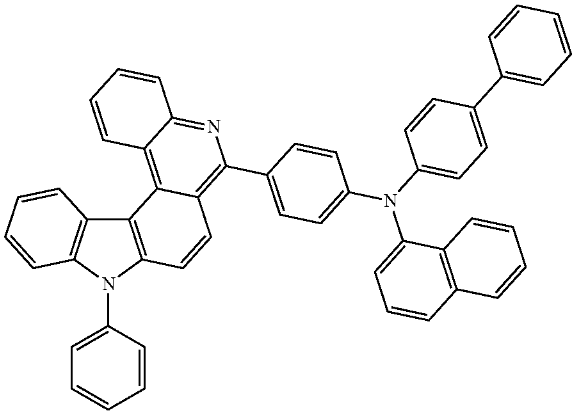
5-20
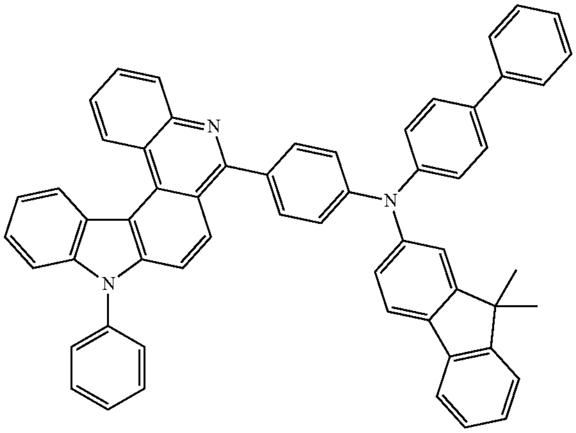
5-21
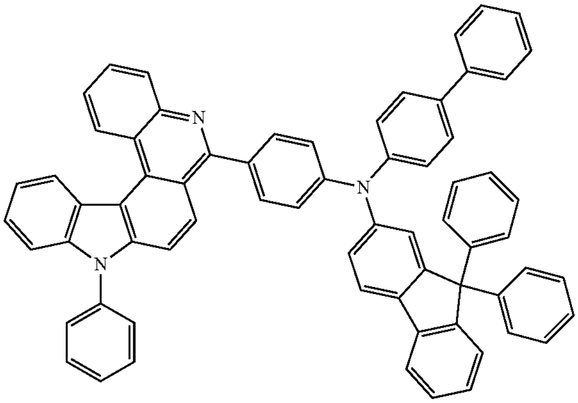

-continued
5-22
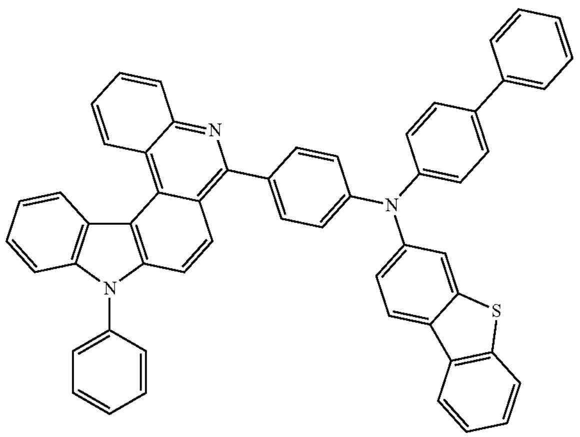
5-23
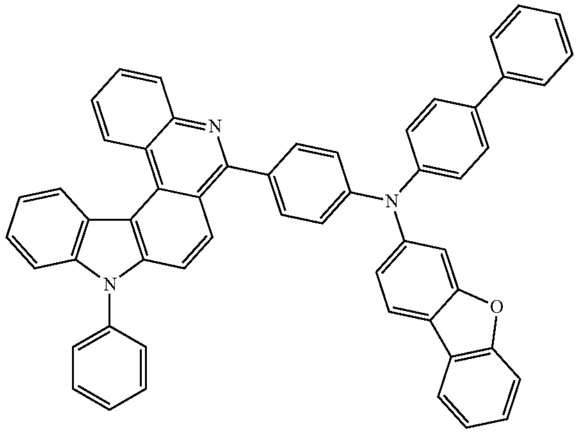
5-24
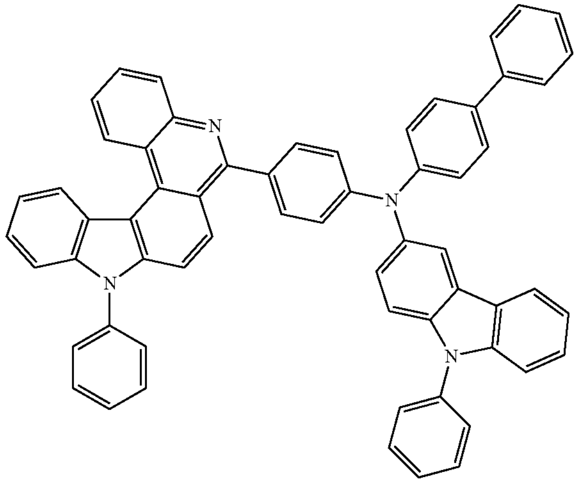
-continued
5-25
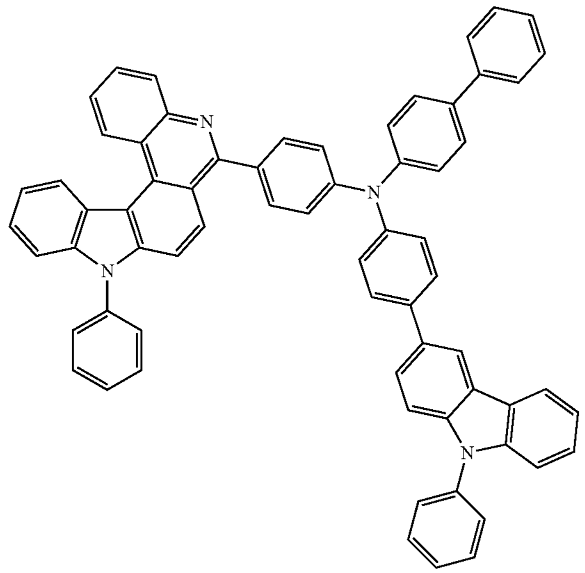
5-26
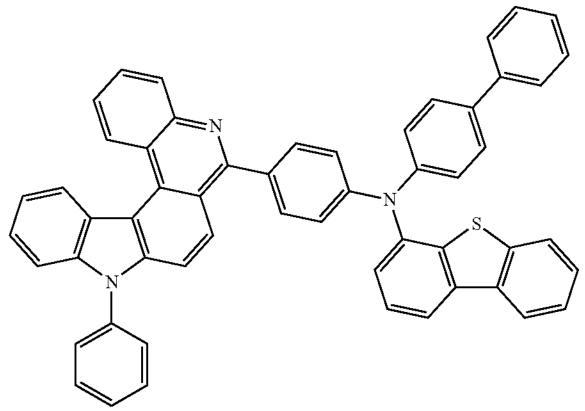
5-27
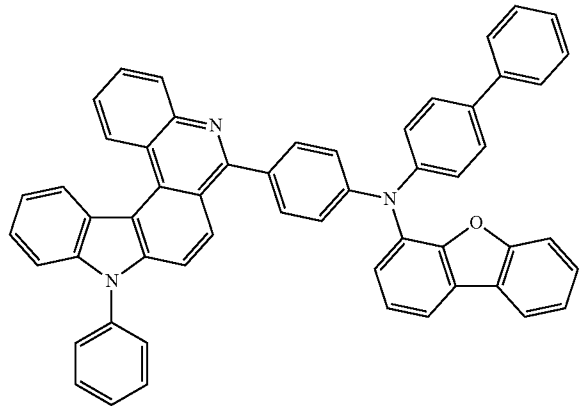

-continued
5-28
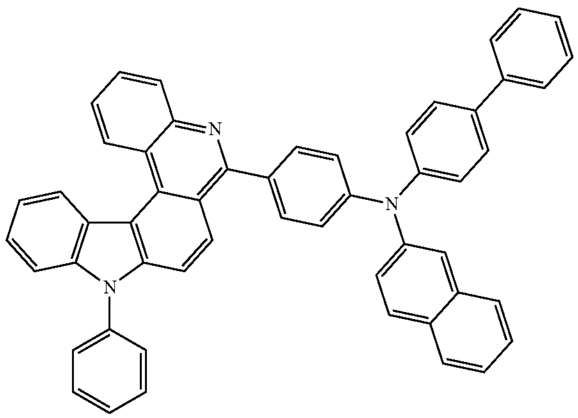
5-29
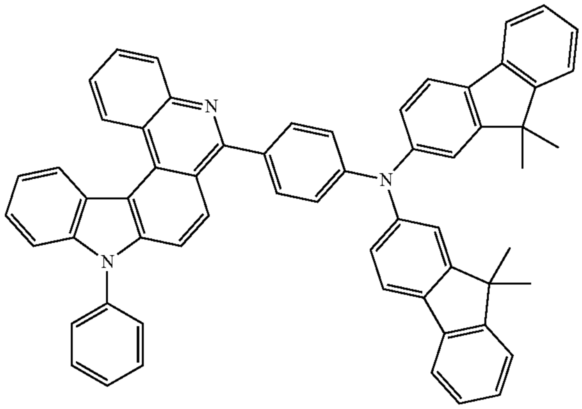
5-30
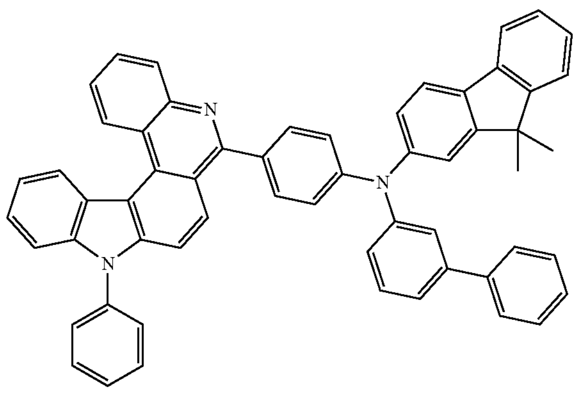
-continued
5-31
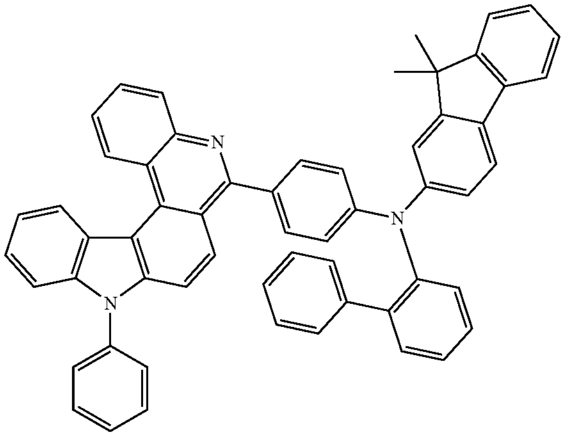
5-32
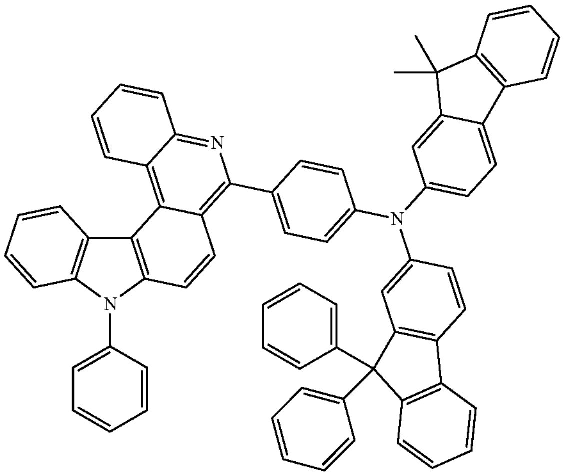
5-33
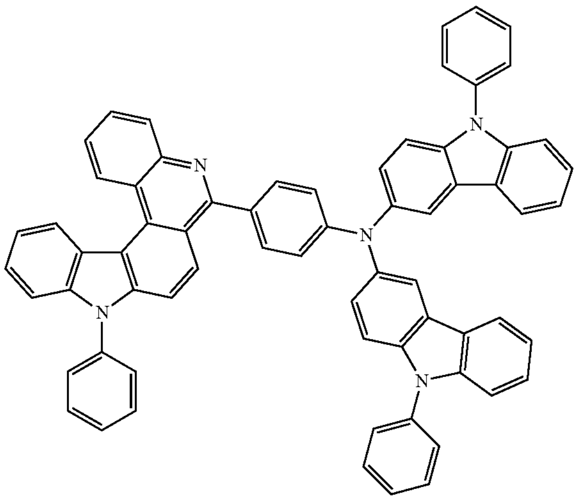

-continued
5-34
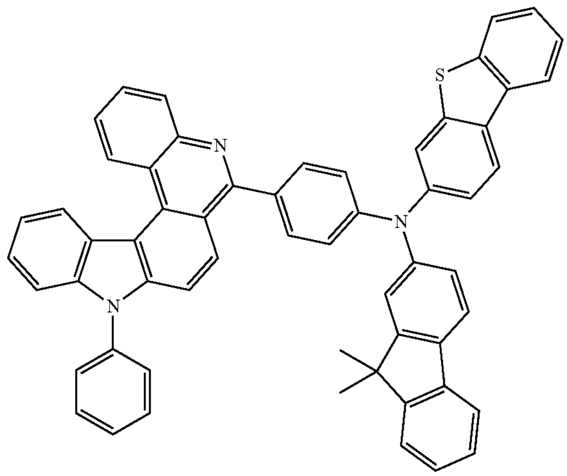
5-35
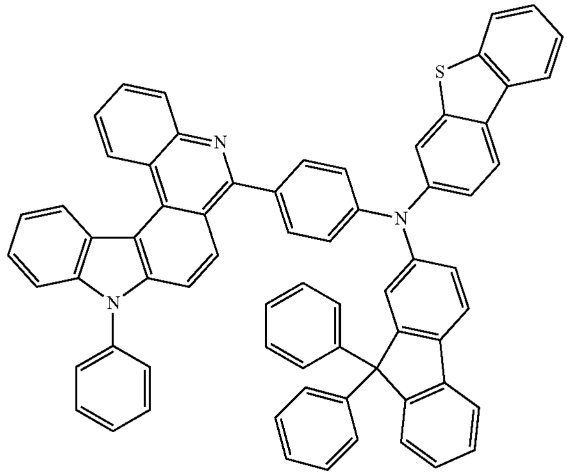
5-36
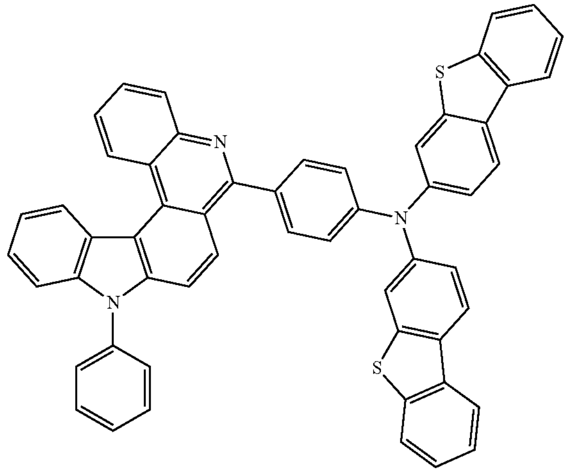
-continued
5-37
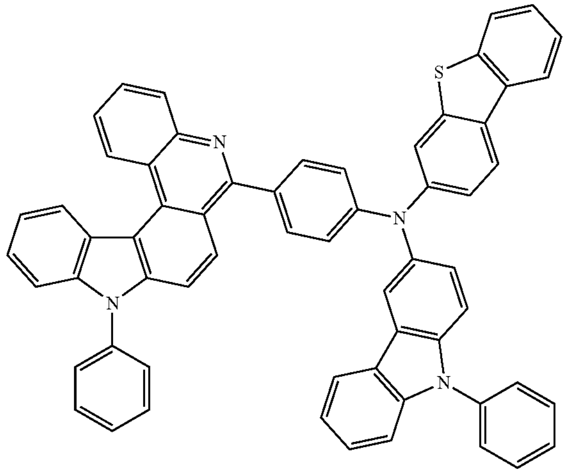
5-38
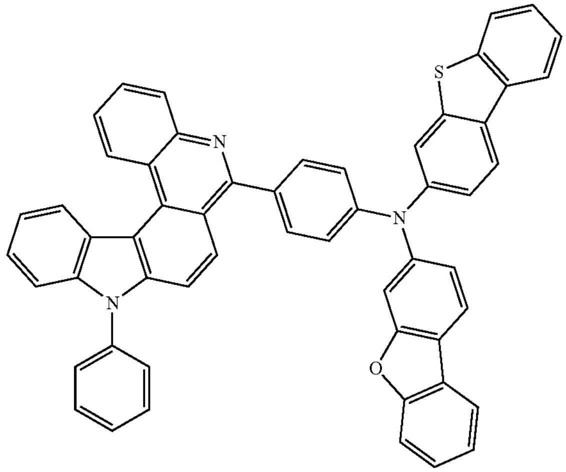
5-39
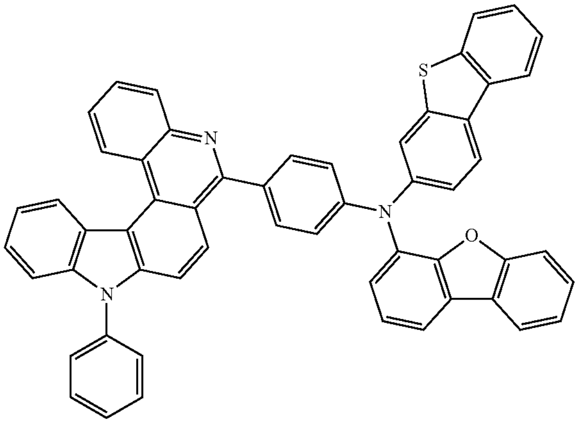

-continued
5-40
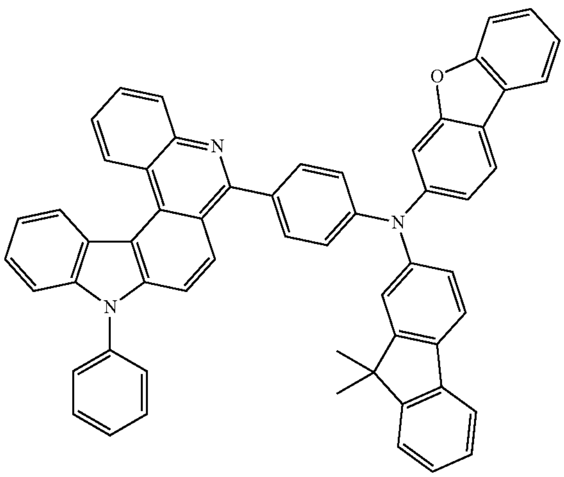
5-41
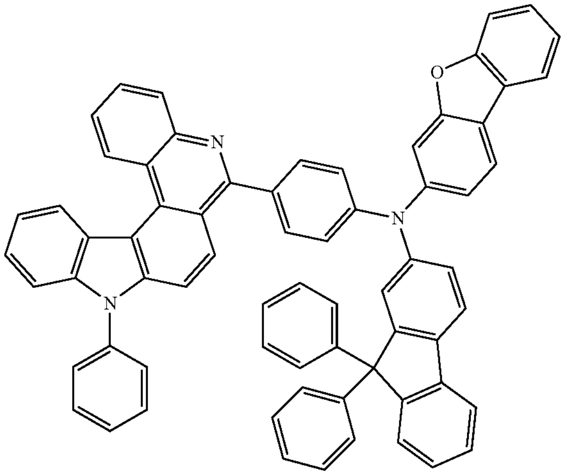
5-42
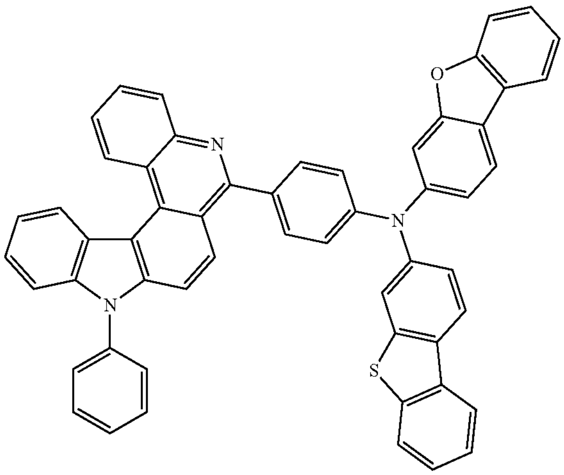
-continued
5-43
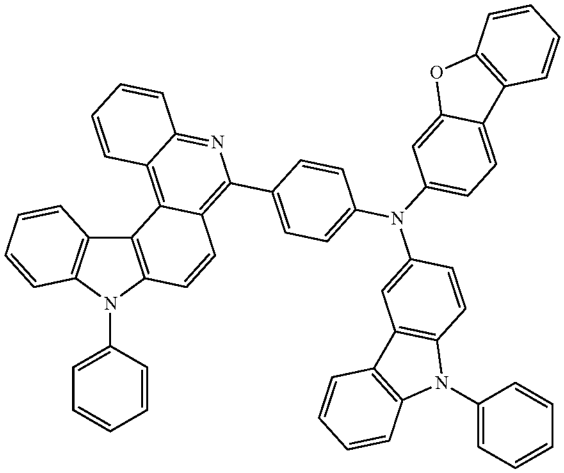
5-44
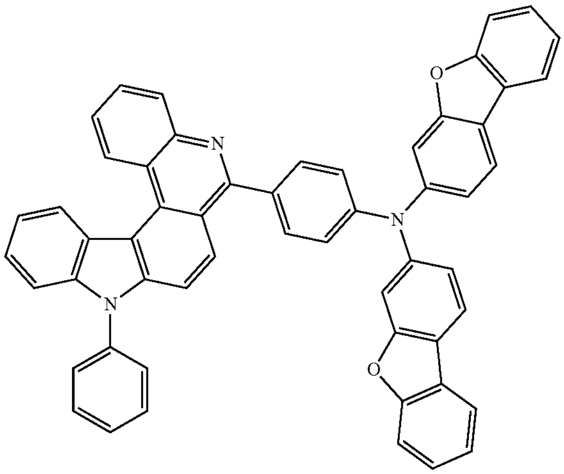
5-45
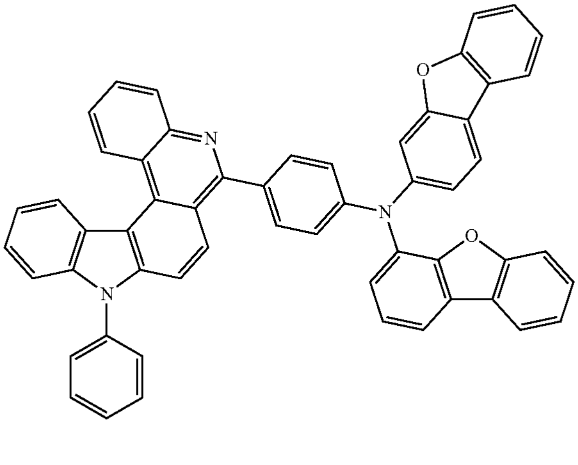

-continued
5-46
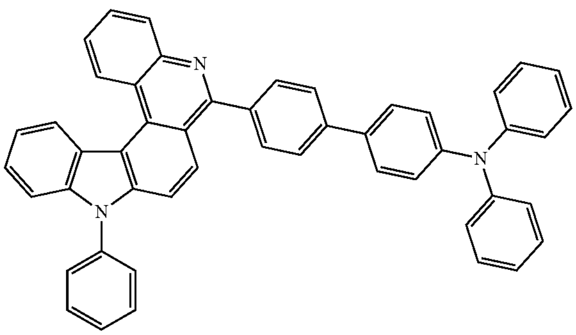
5-47
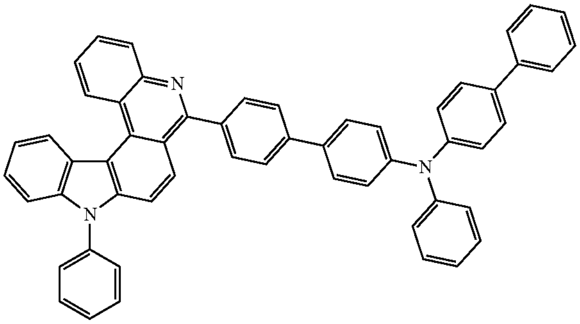
5-48
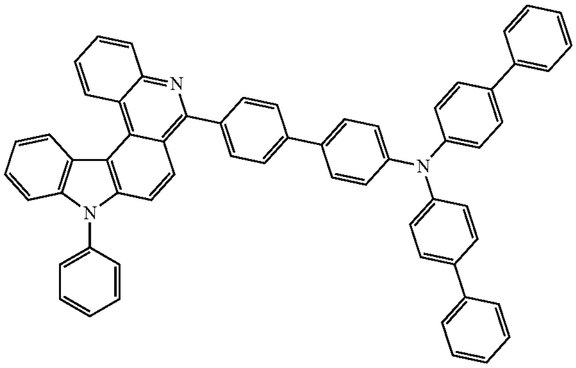
5-49
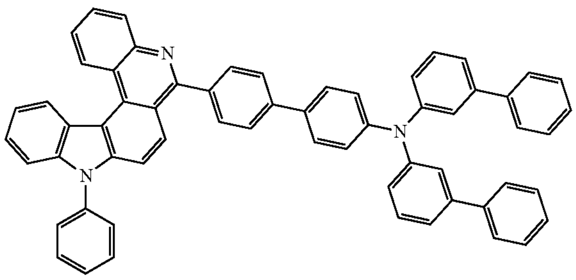
-continued
5-50
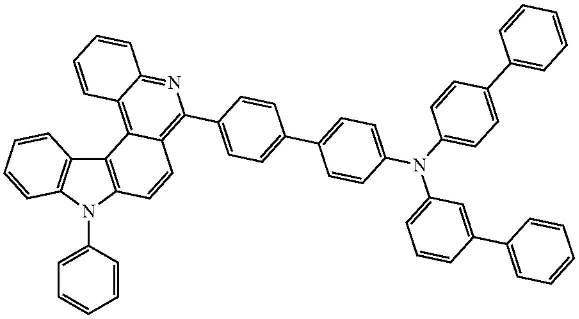
5-51
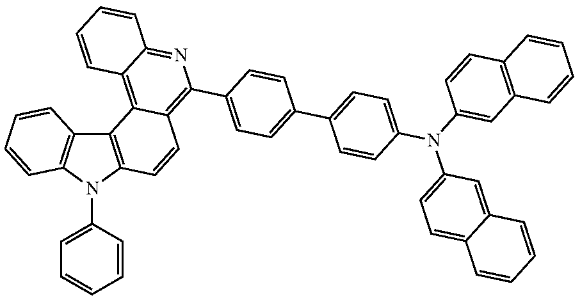
5-52
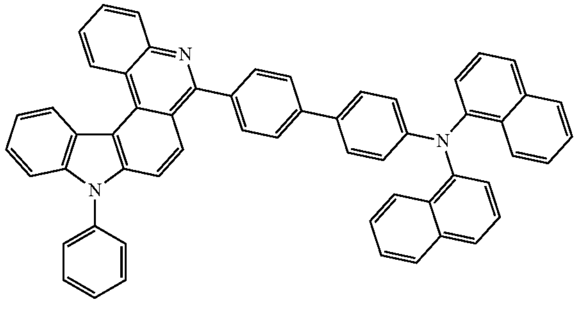
5-53
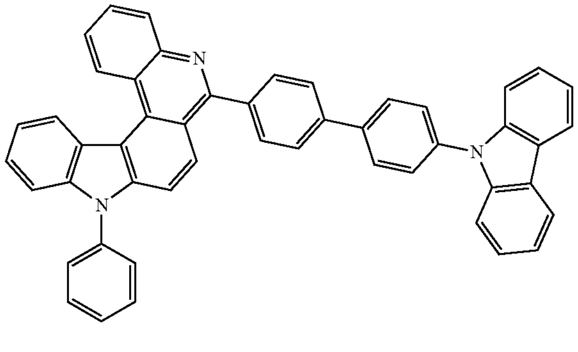

-continued
5-54
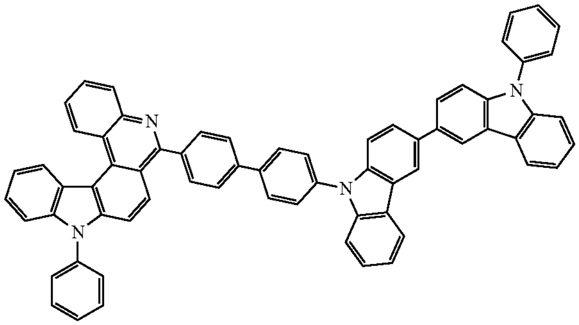
5-55
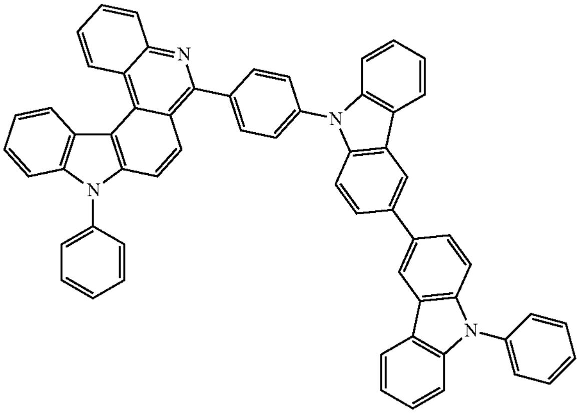
5-56
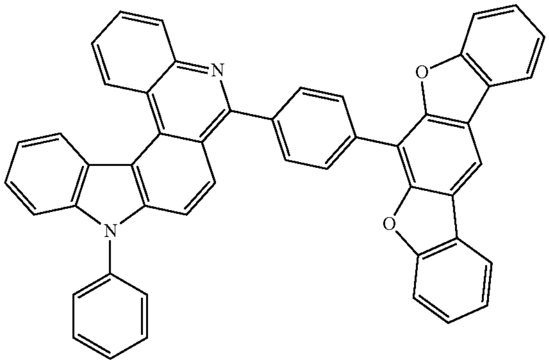
5-57
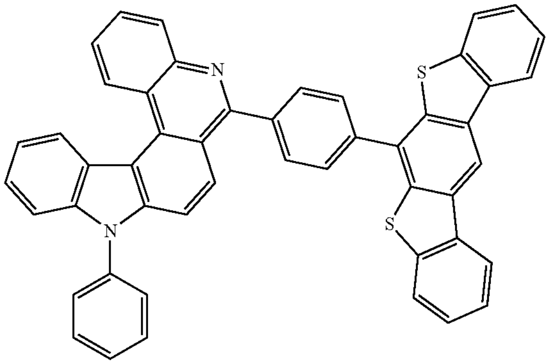
-continued
5-58
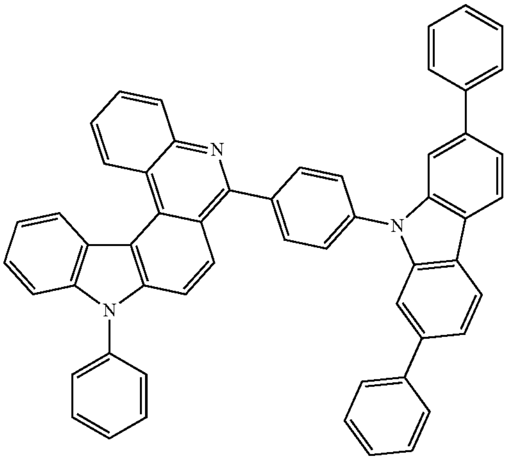
5-59
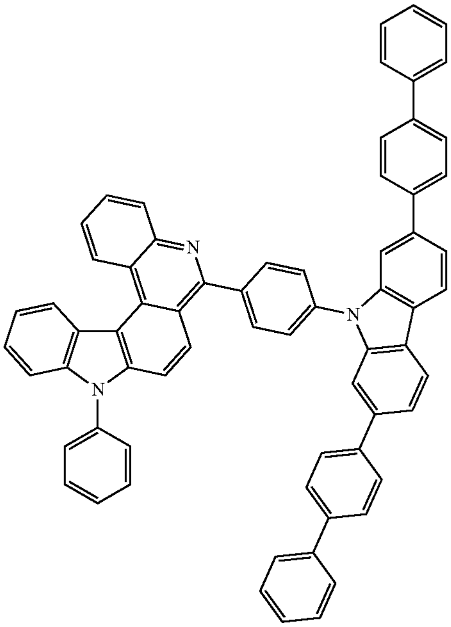

-continued
5-60
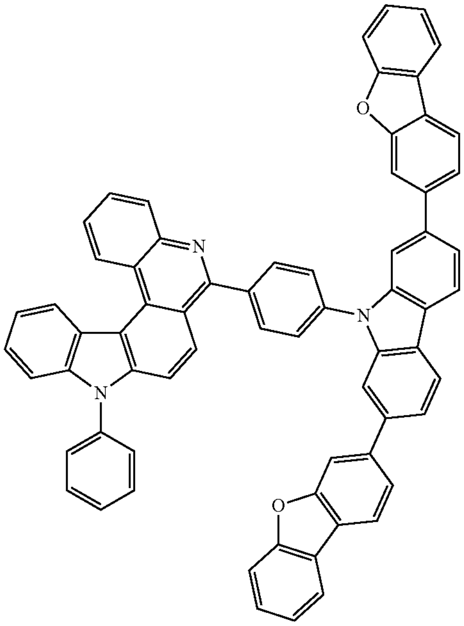
5-61
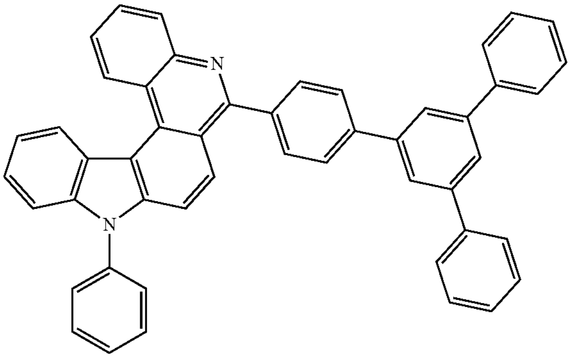
5-62
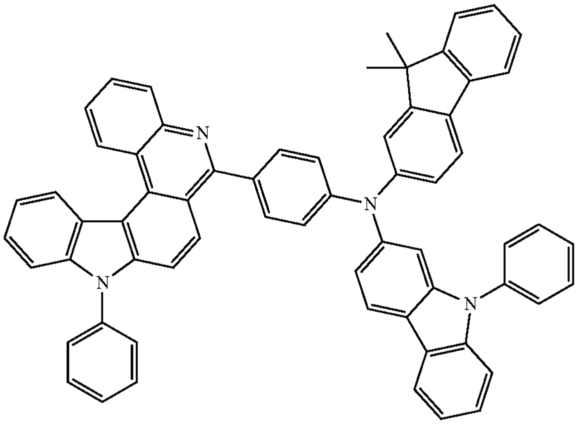
-continued
5-63
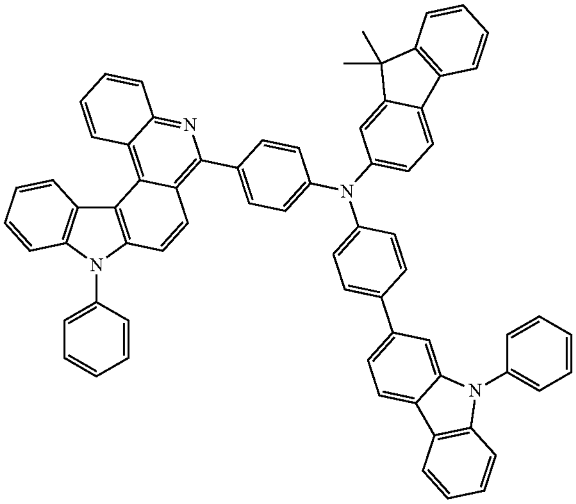
5-64
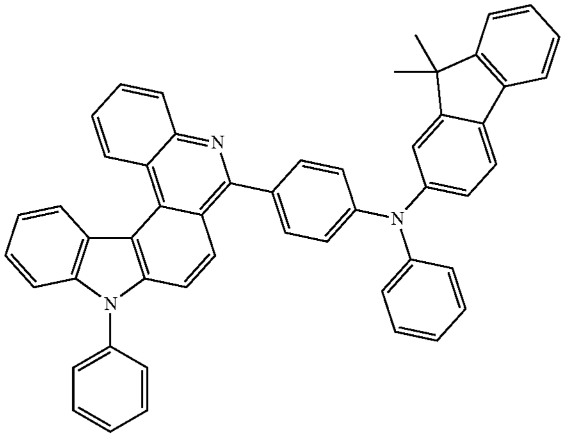
5-65
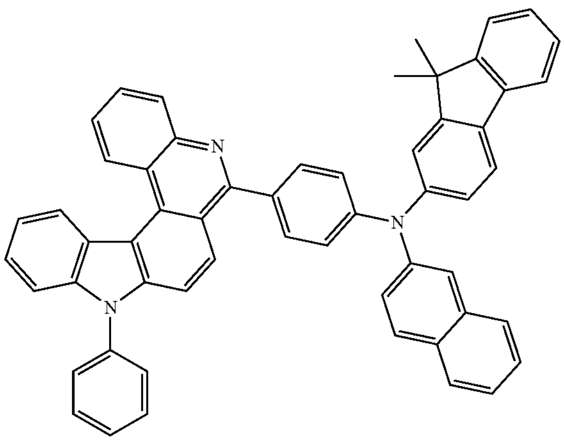

-continued
5-66
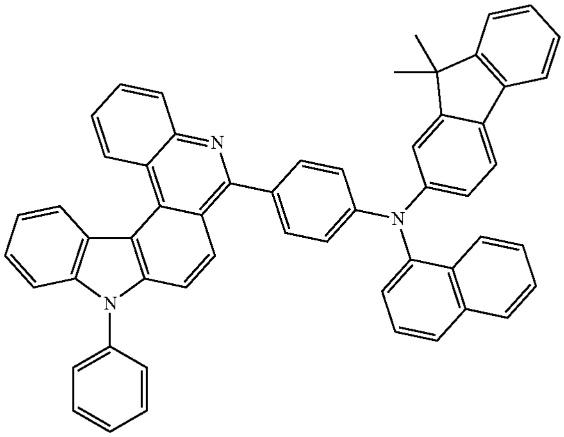
5-67
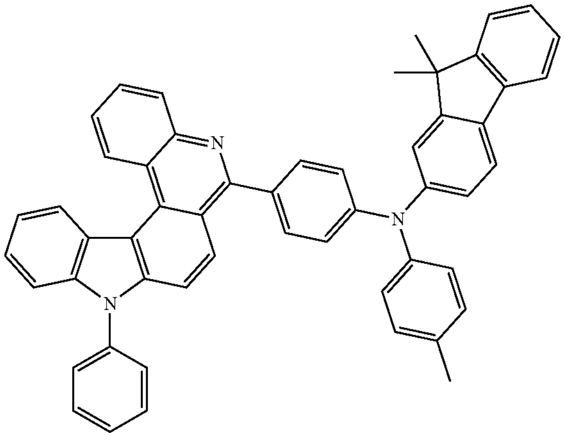
5-68
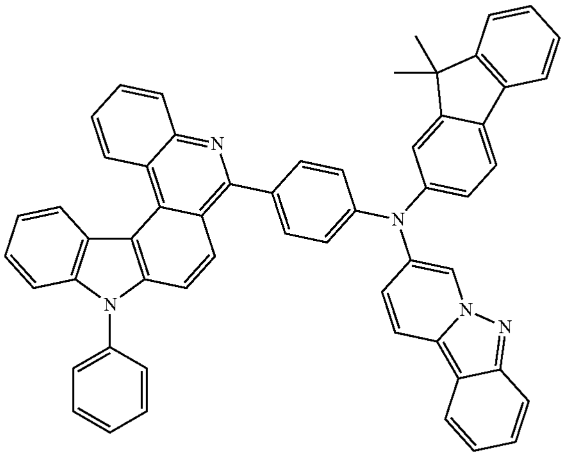
-continued
5-69
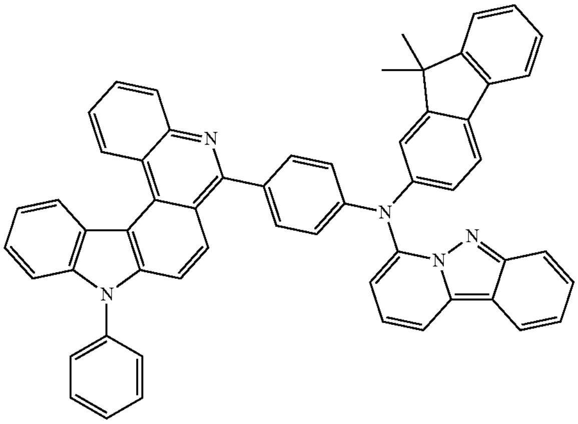
5-70
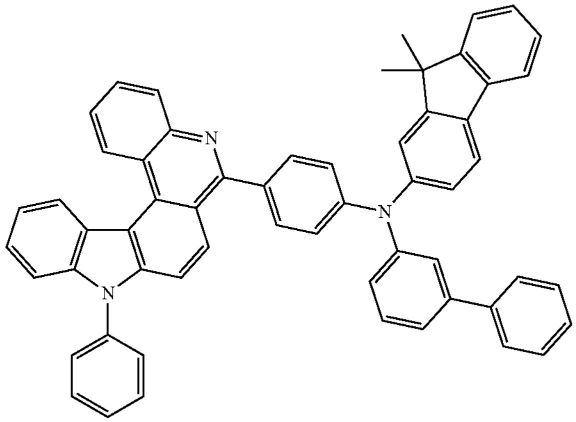
5-71
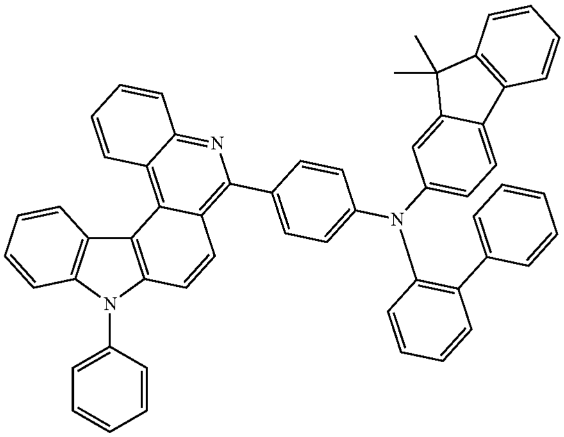

-continued
5-72
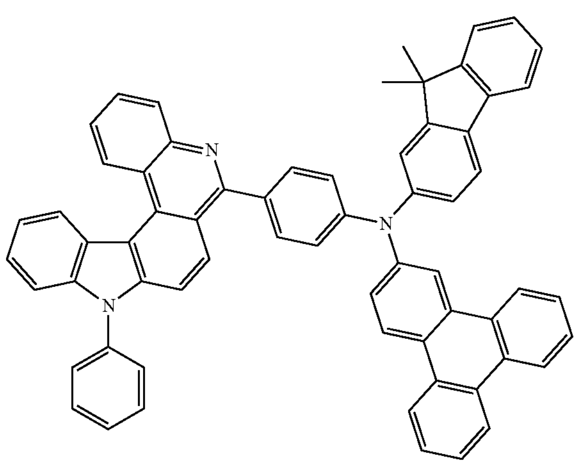
5-73
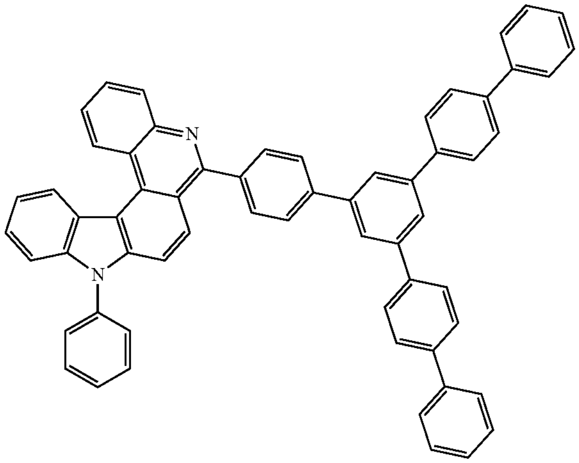
5-74
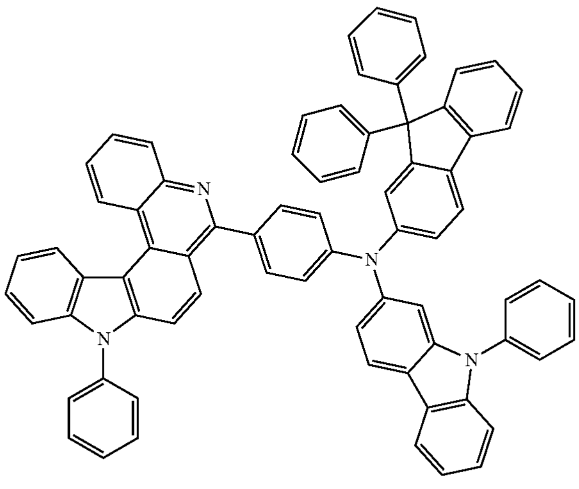
-continued
5-75
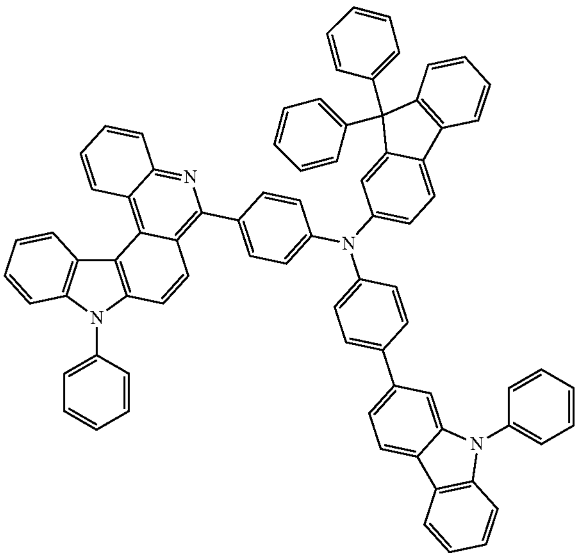
5-76
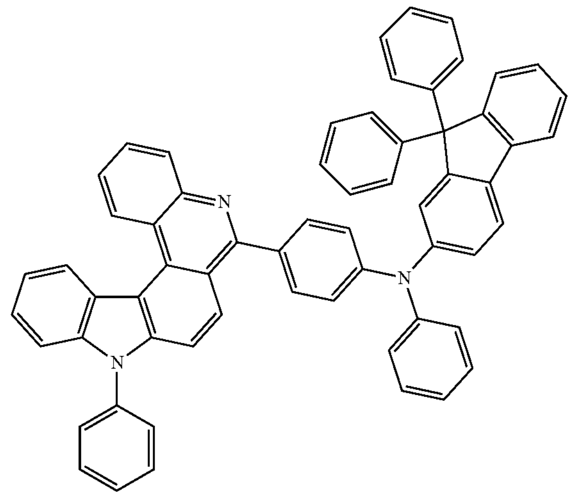
5-77
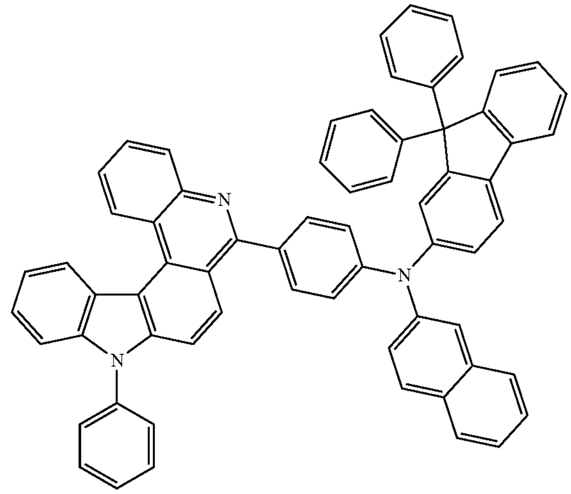

-continued
5-78
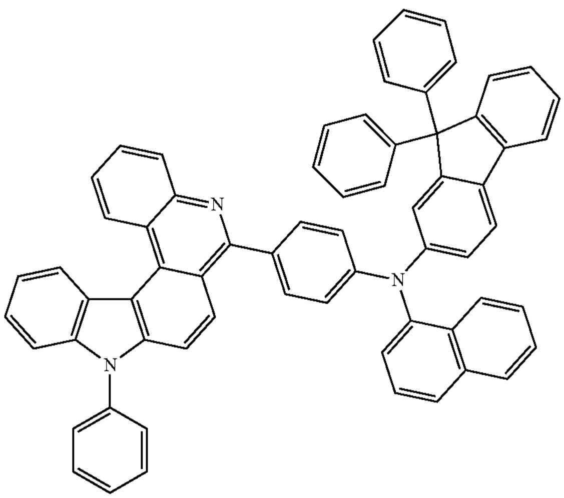
5-79
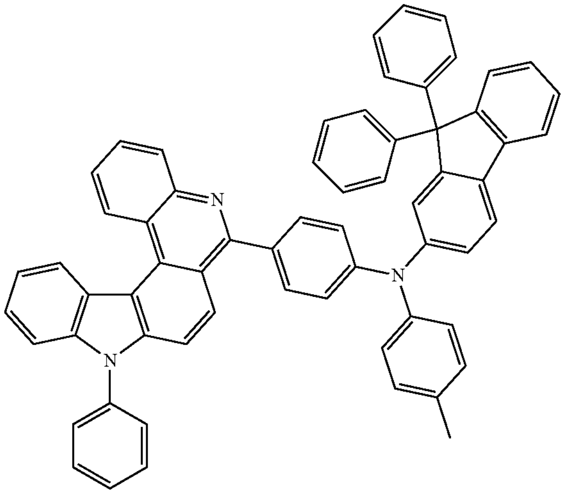
5-80
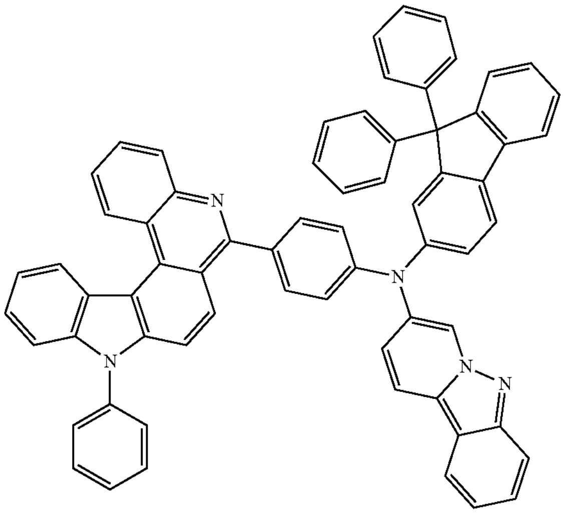
-continued
5-81
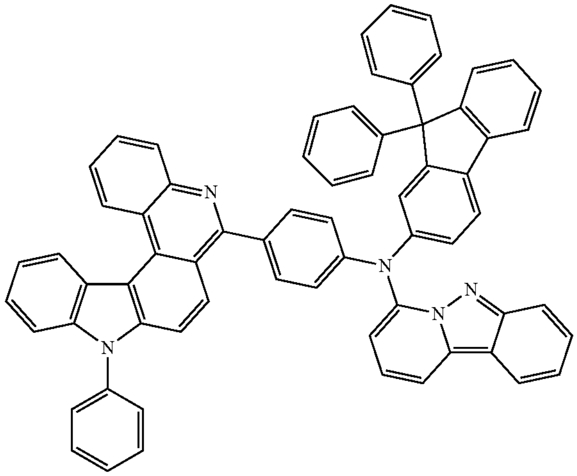
5-82
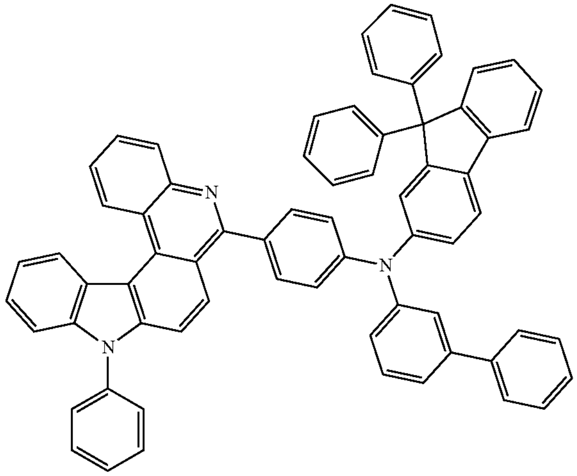
5-83
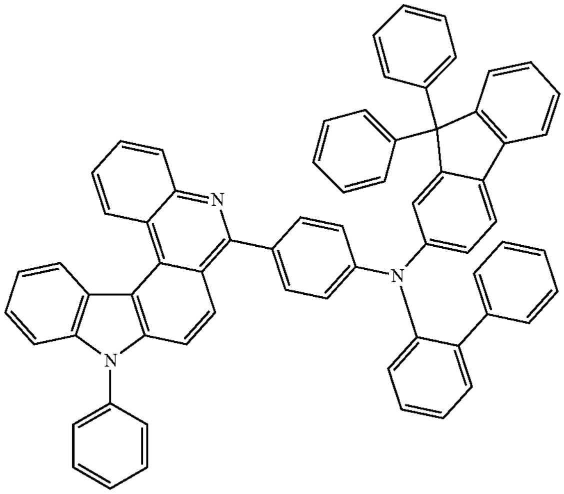

-continued
5-84
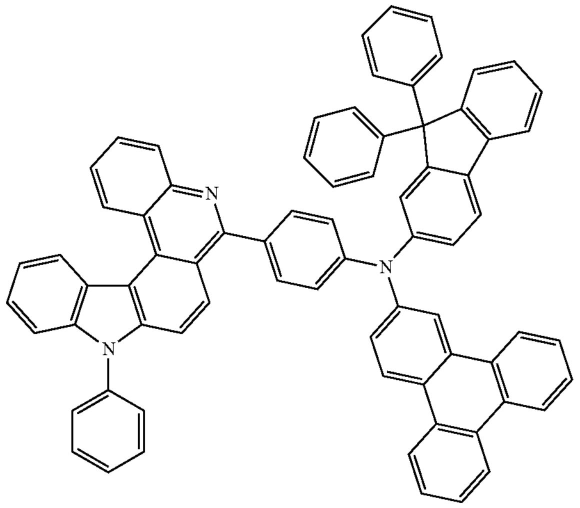
5-85
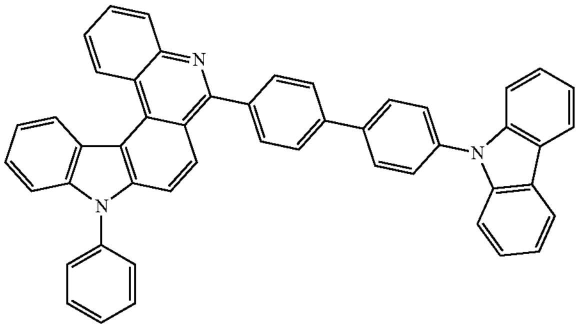
5-86
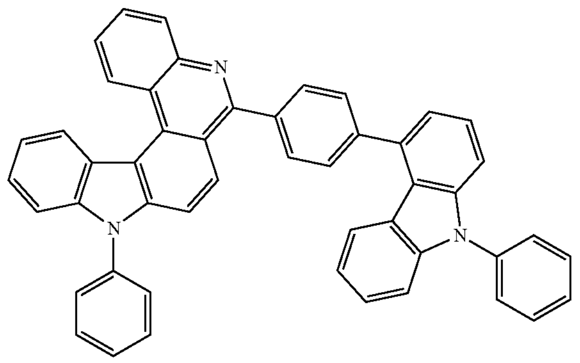
5-87
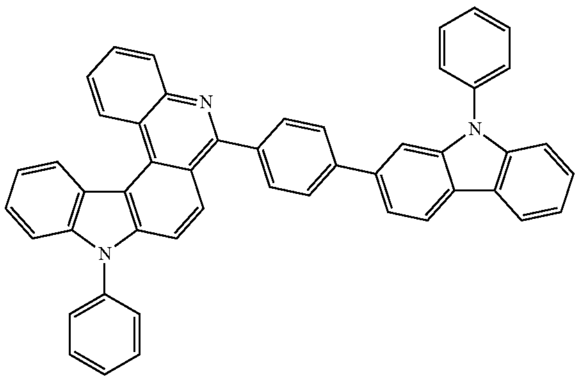
-continued
5-88
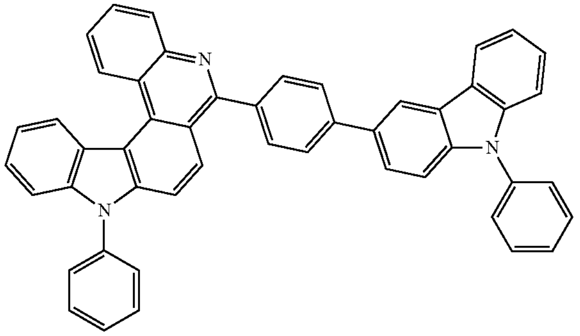
6-1
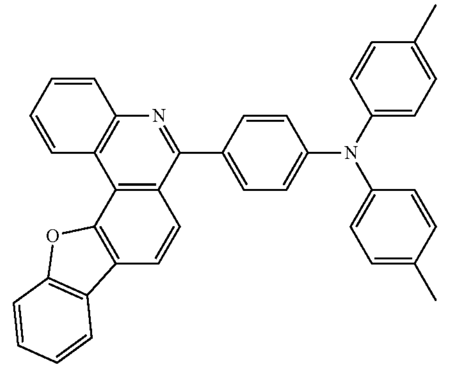
6-2
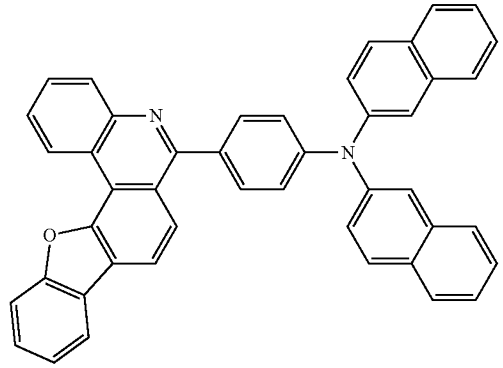
6-3
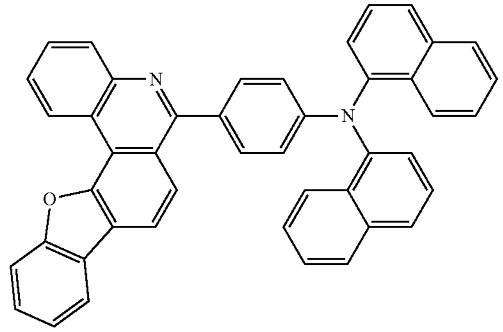

-continued
6-4
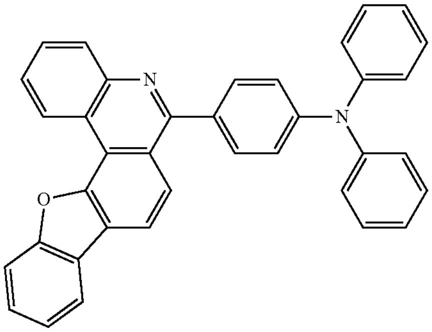
6-5
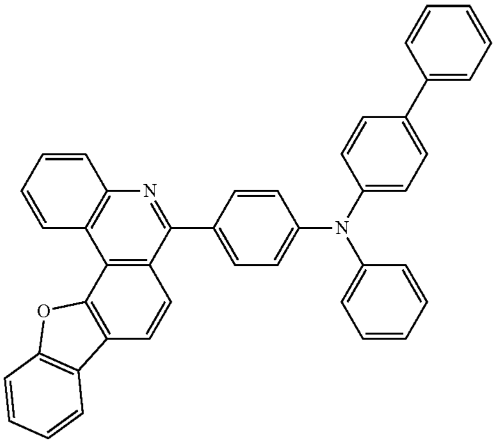
6-6
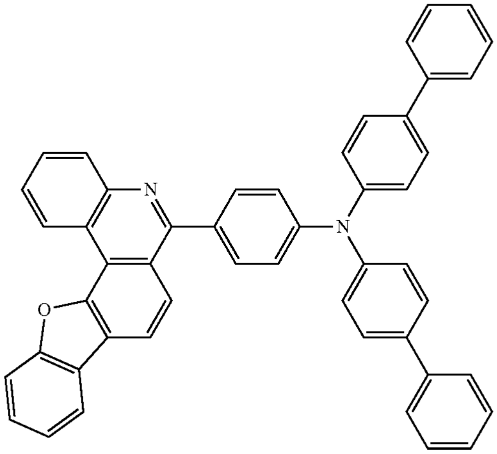
6-7
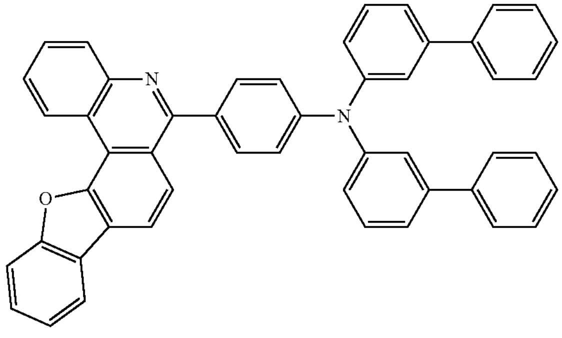
-continued
6-8
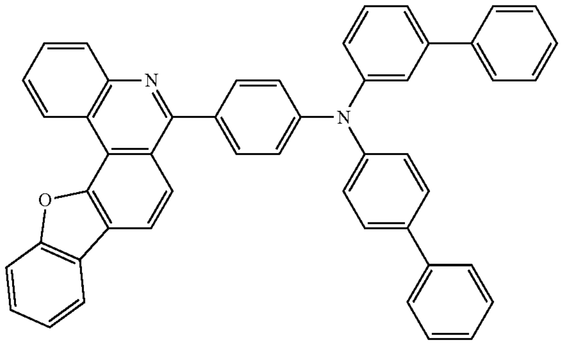
6-9
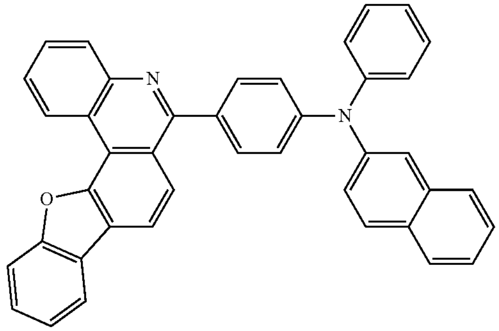
6-10
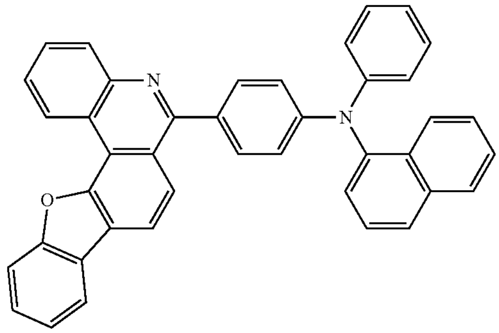
6-11
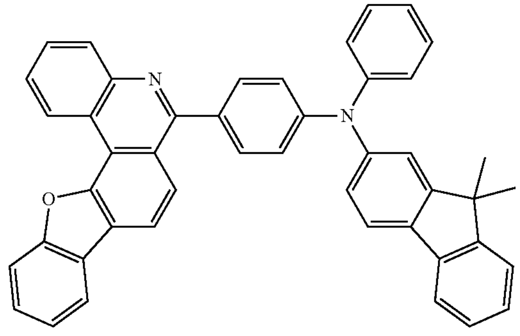

6-12
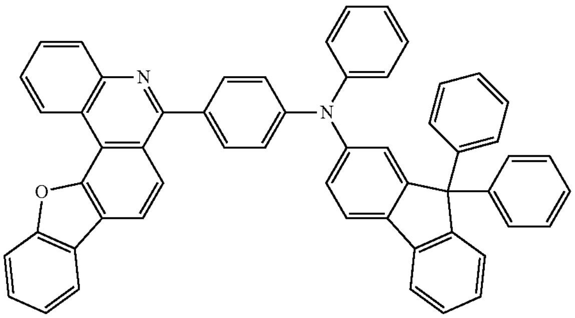
6-13
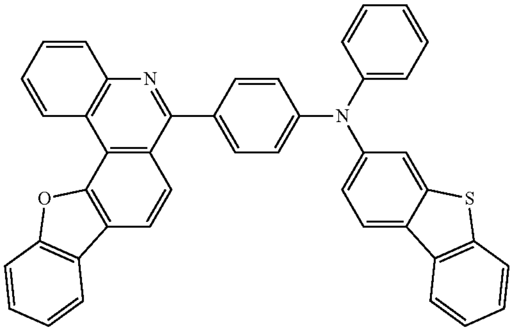
6-14
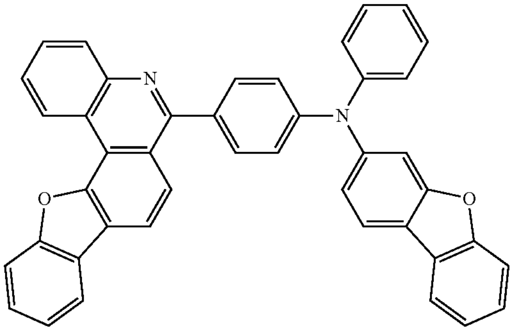
6-15
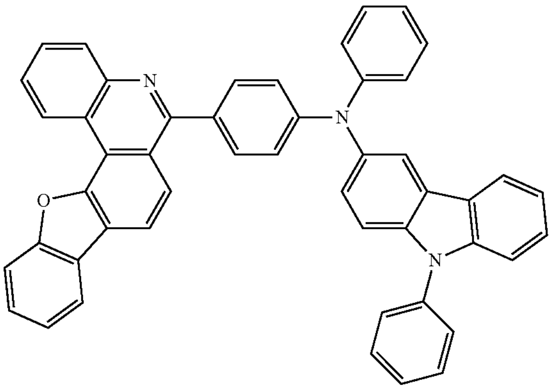
6-16
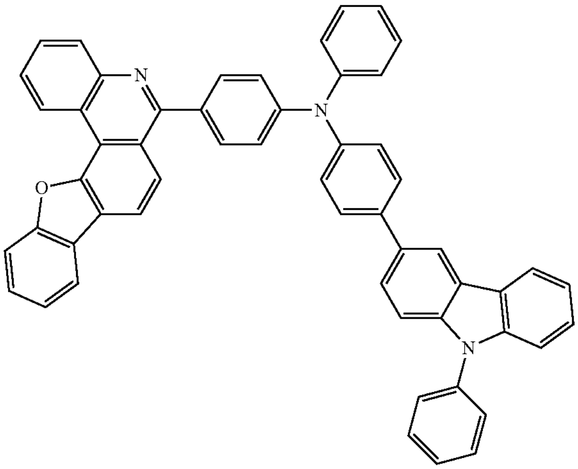
6-17
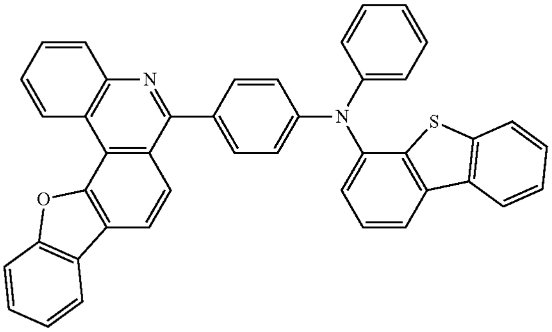
6-18
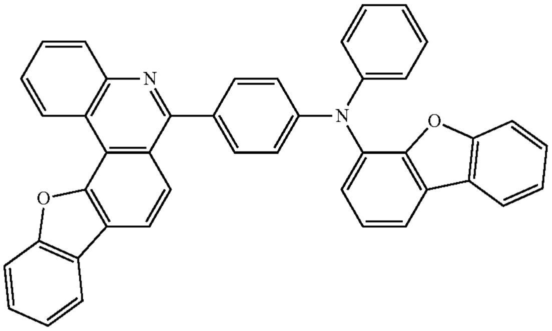
6-19
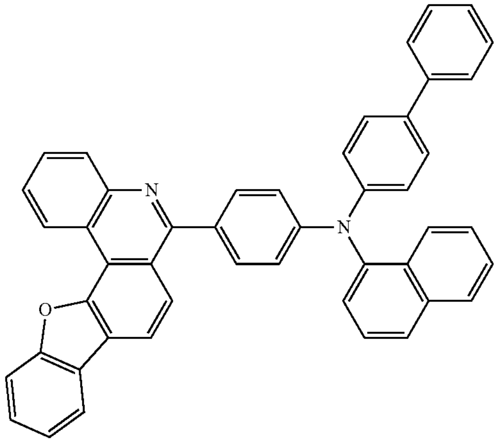

-continued
6-20
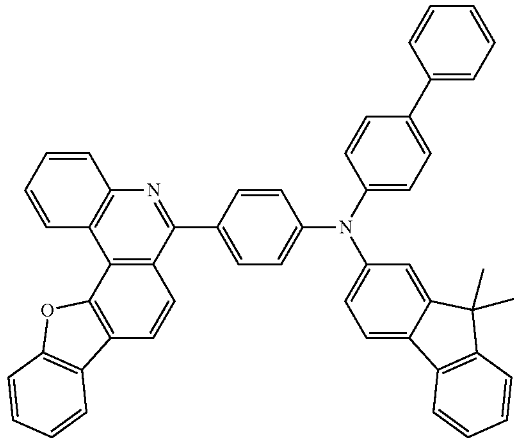
6-21
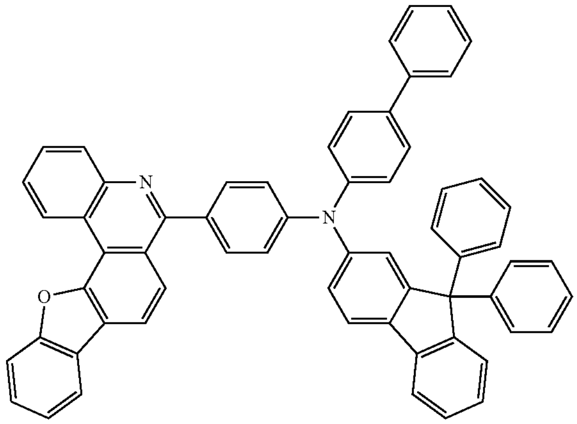
6-22
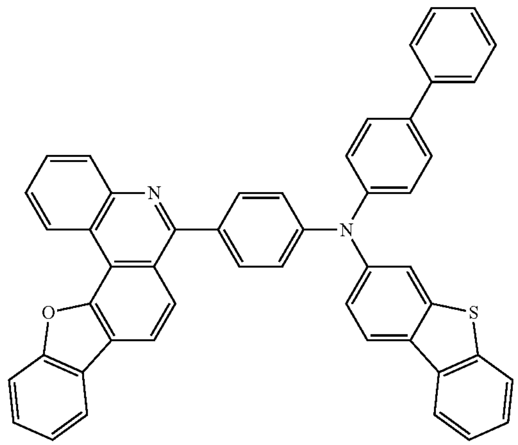
-continued
6-23
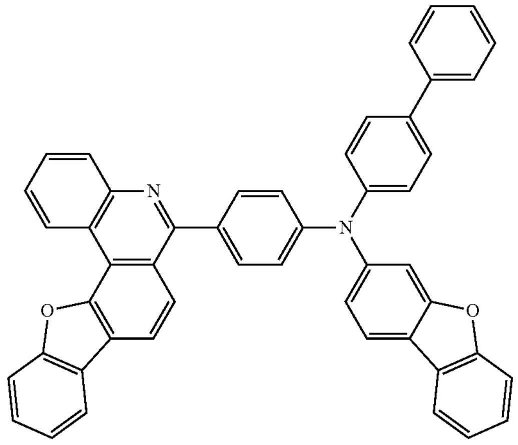
6-24
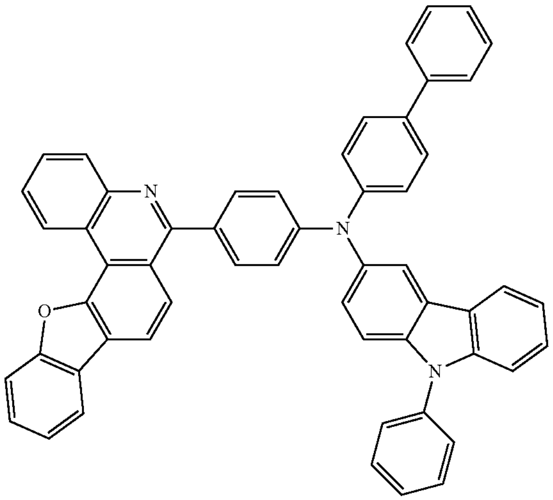
6-25
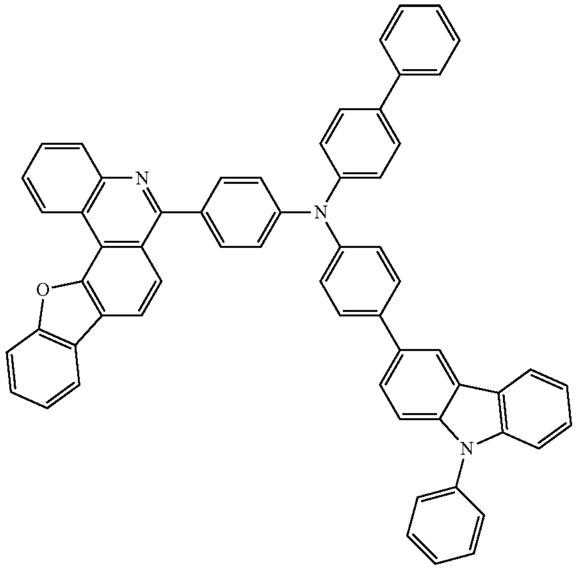

-continued
6-26
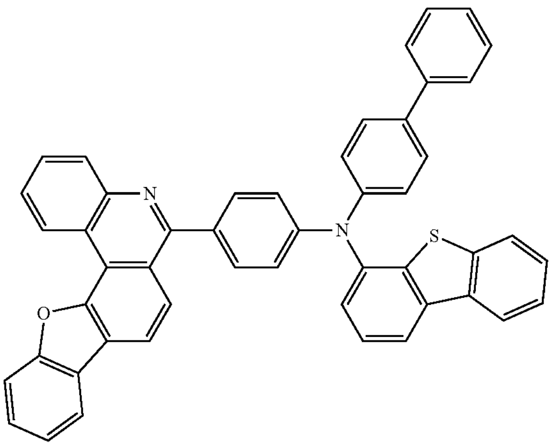
6-27
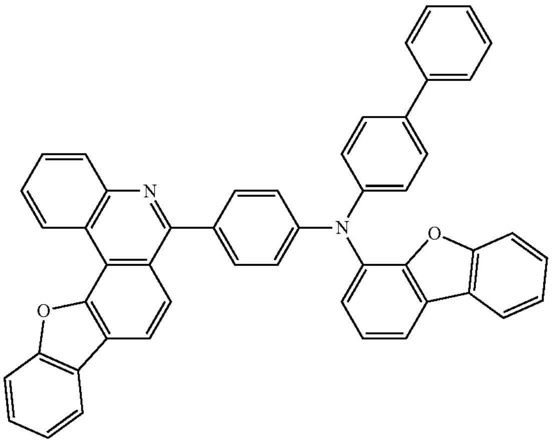
6-28
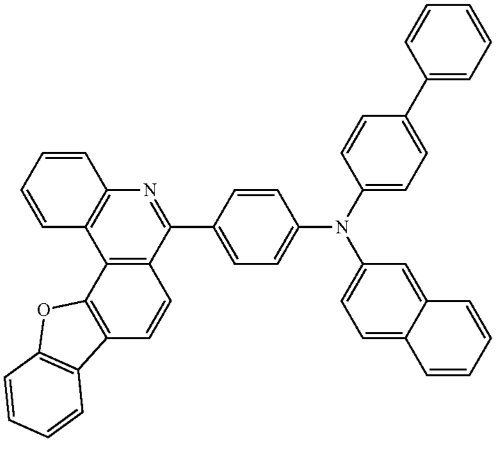
-continued
6-29
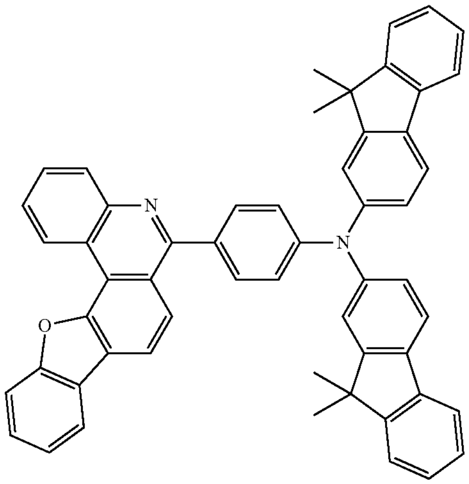
6-30
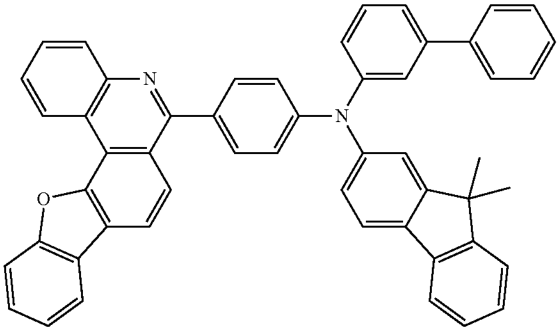
6-31
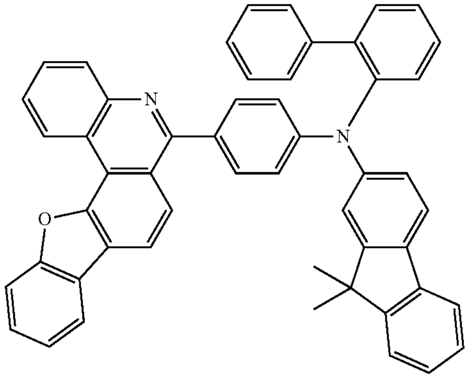

-continued
6-32
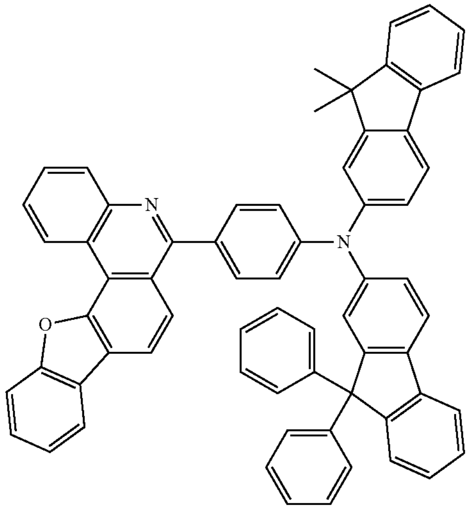
6-33
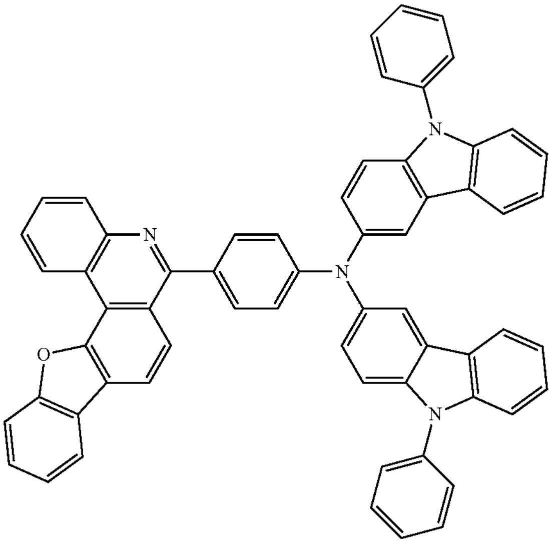
6-34
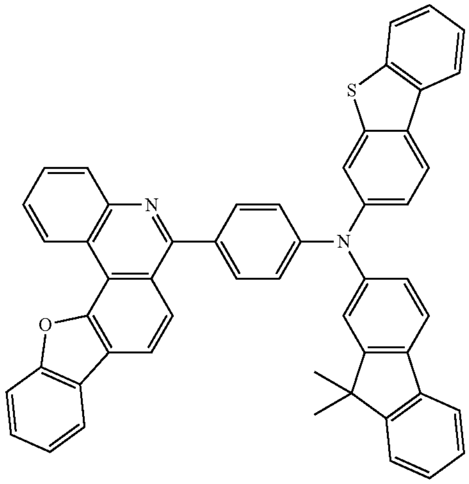
-continued
6-35
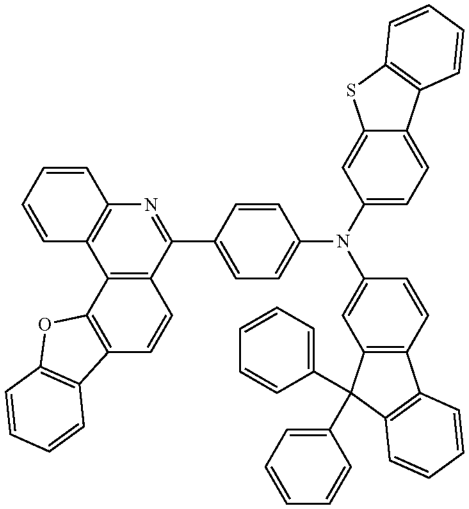
6-36
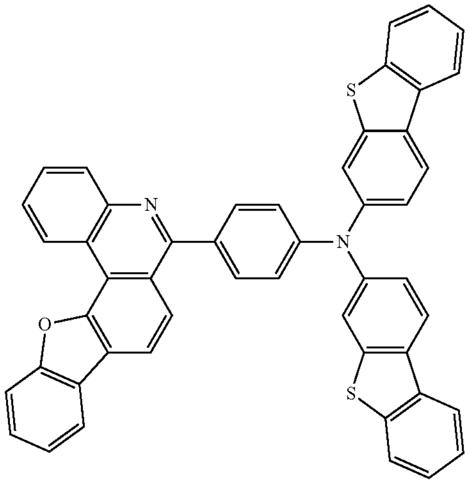
6-37
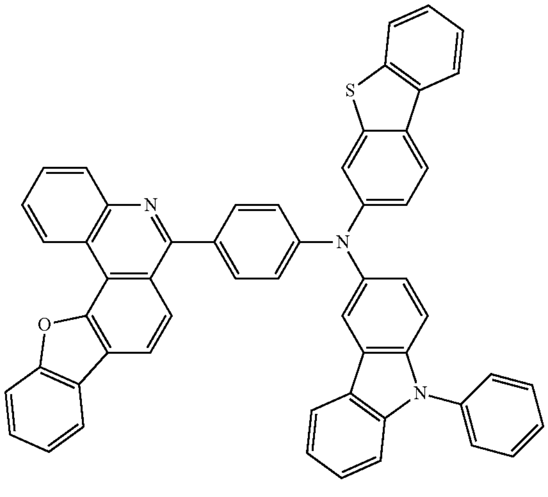

-continued
6-38
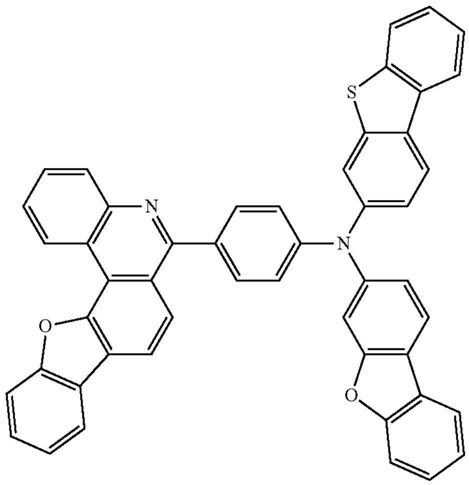
6-39
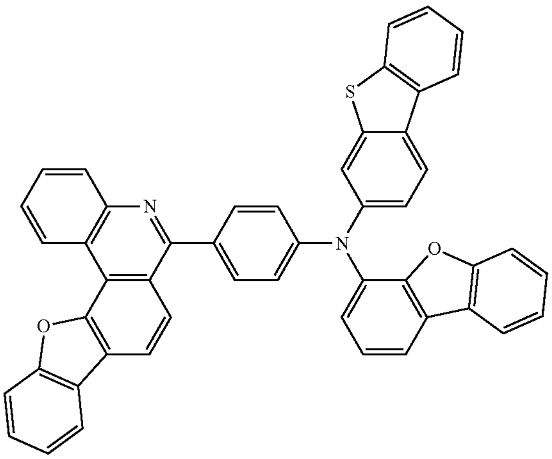
6-40
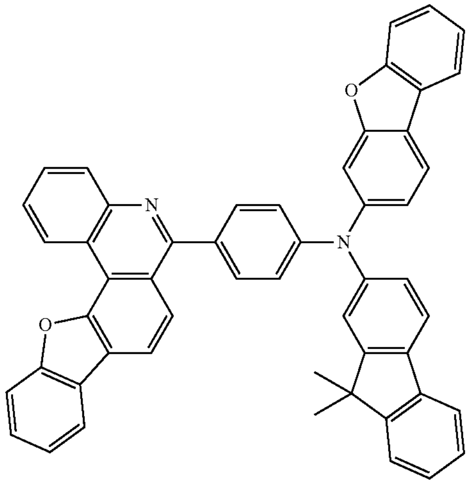
-continued
6-41
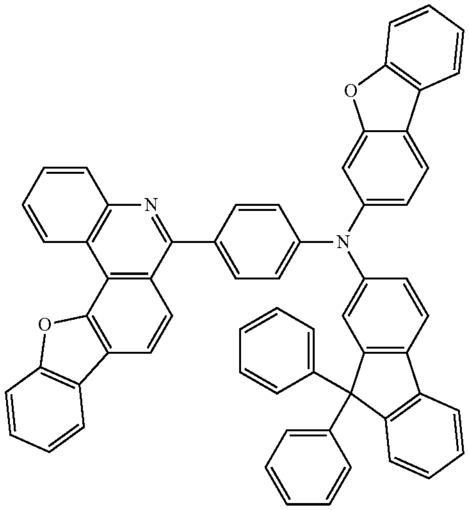
6-42
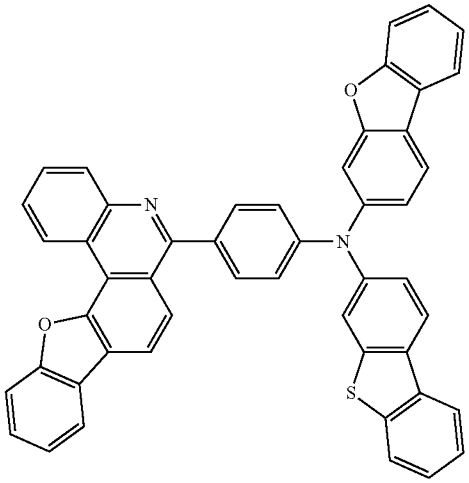
6-43
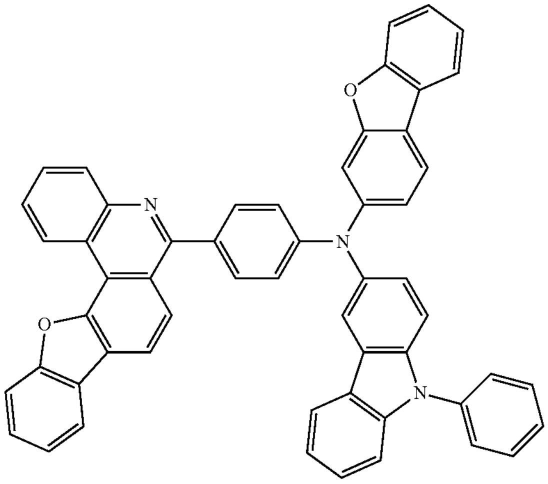

-continued
6-44
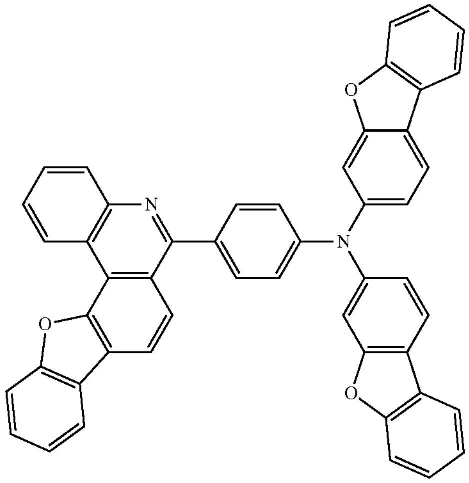
6-45
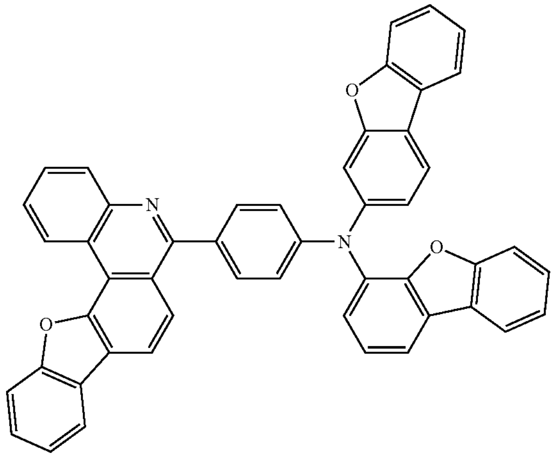
6-46
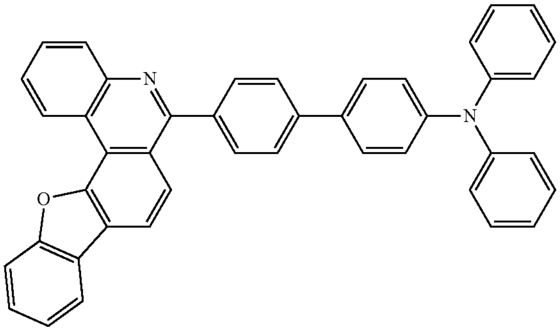
-continued
6-47
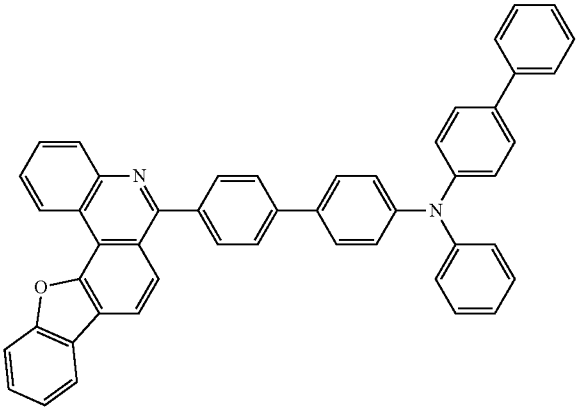
6-48
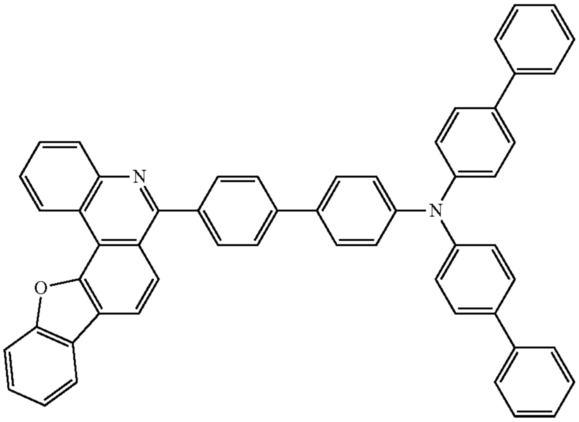
6-49
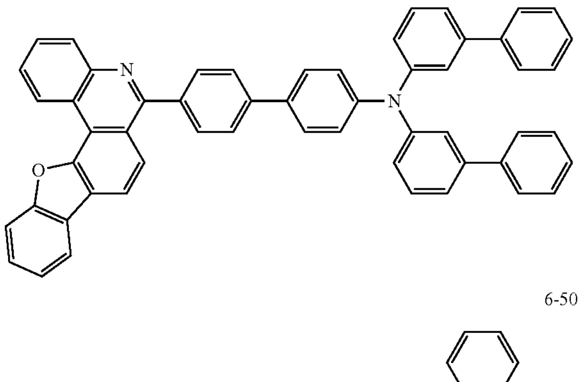
6-50
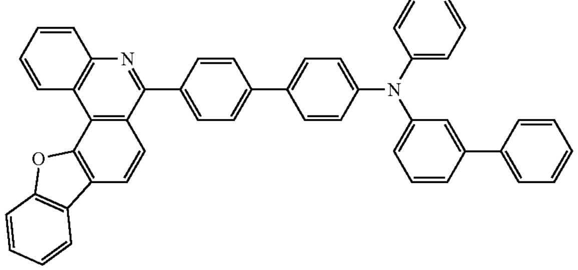

-continued
6-51
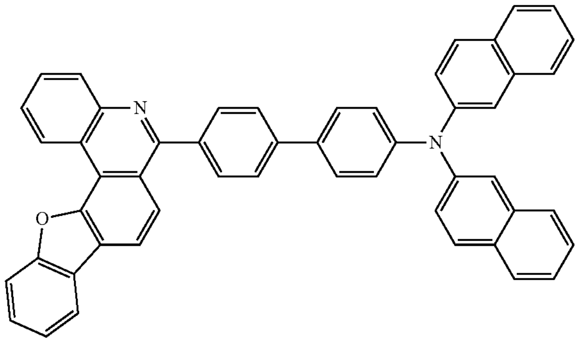
6-52
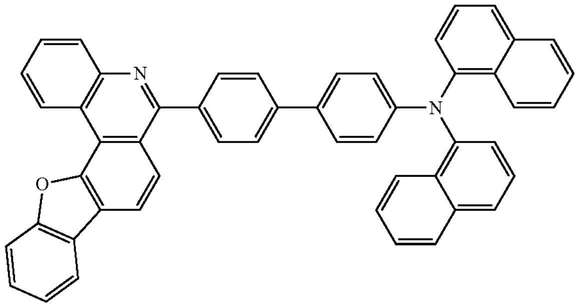
6-53
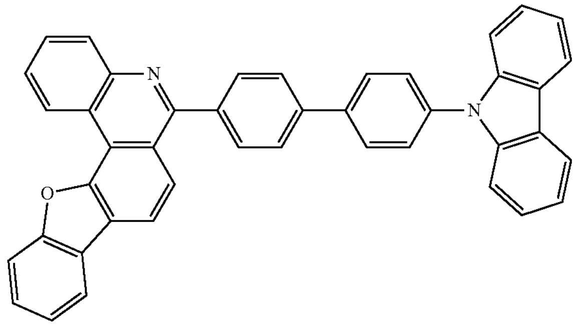
6-54
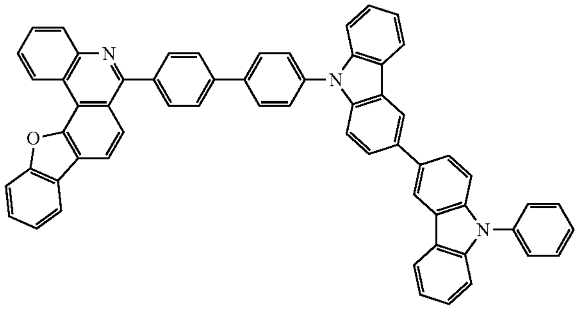
-continued
6-55
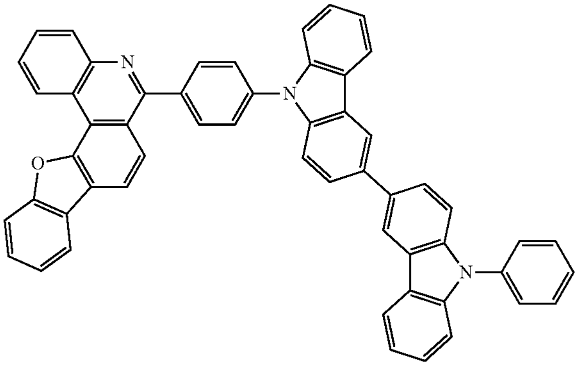
6-56
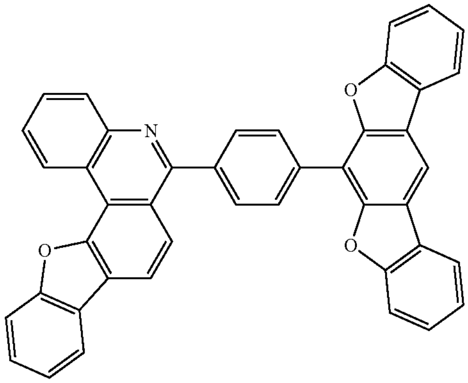
6-57
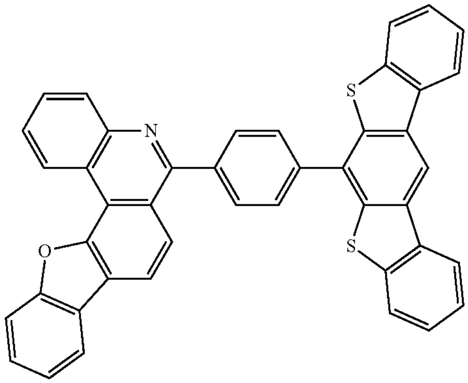
6-58
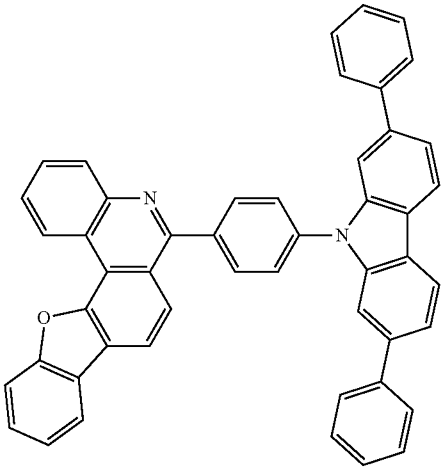

-continued
6-59
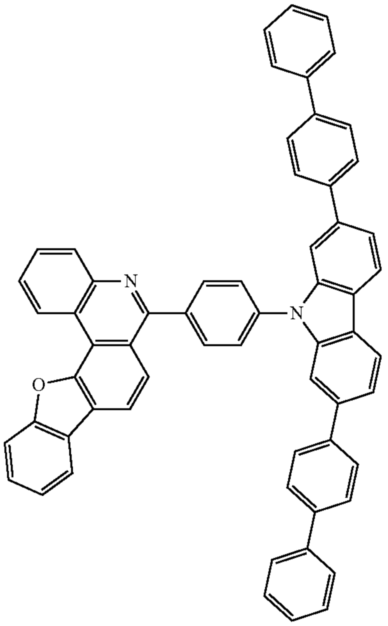
6-60
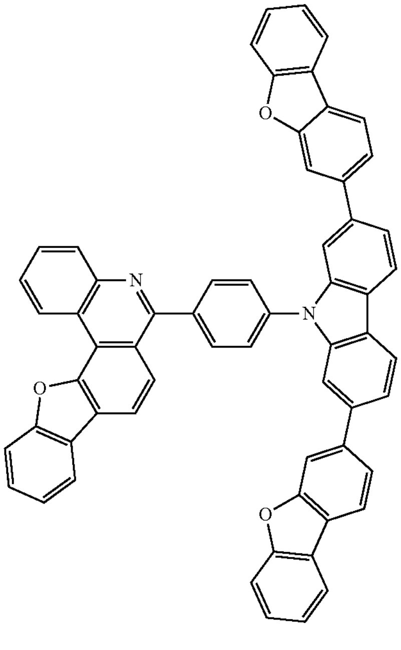
6-61
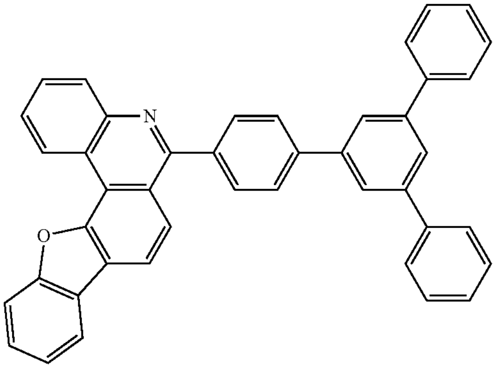
-continued
6-62
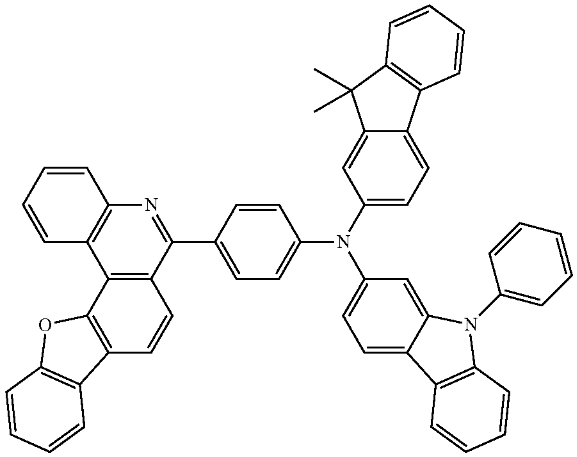
6-63
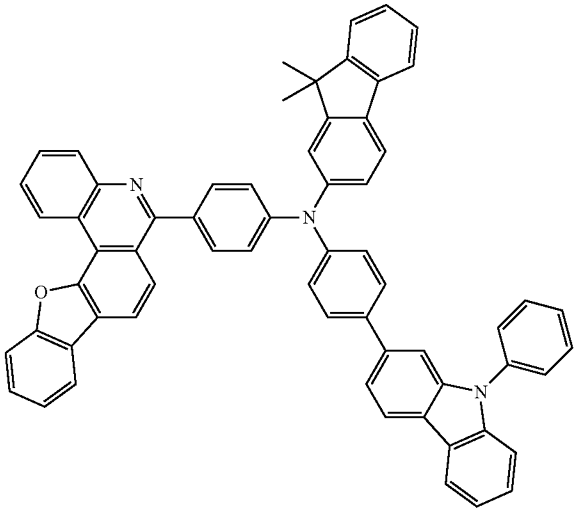
6-64
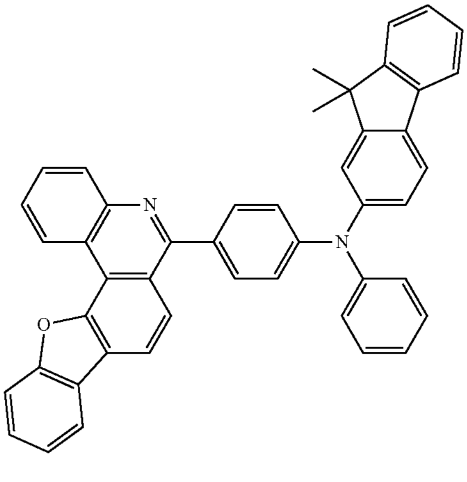

-continued
6-65
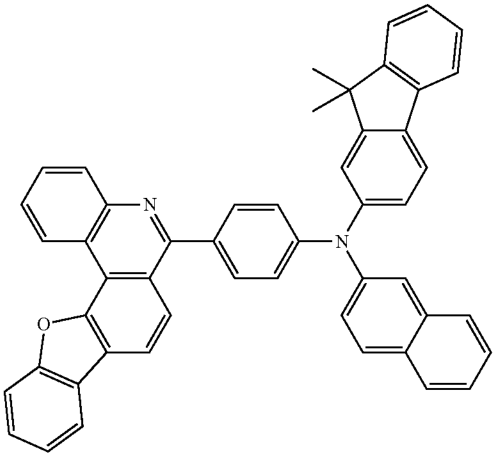
6-66
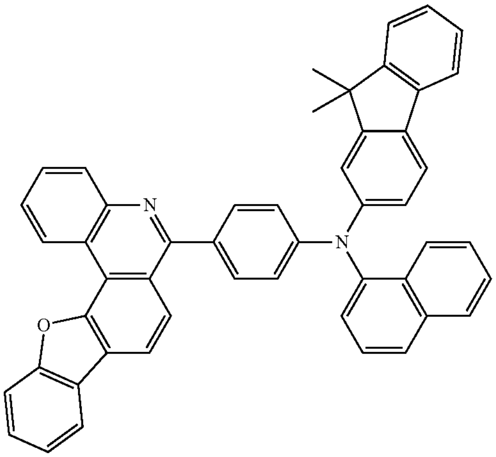
6-67
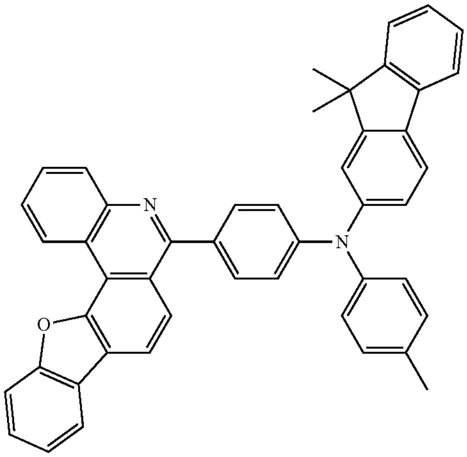
-continued
6-68
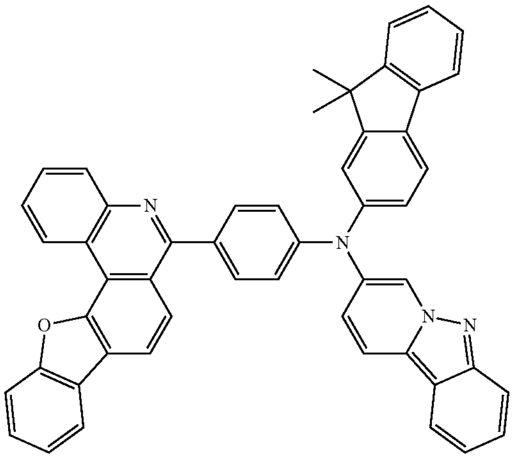
6-69
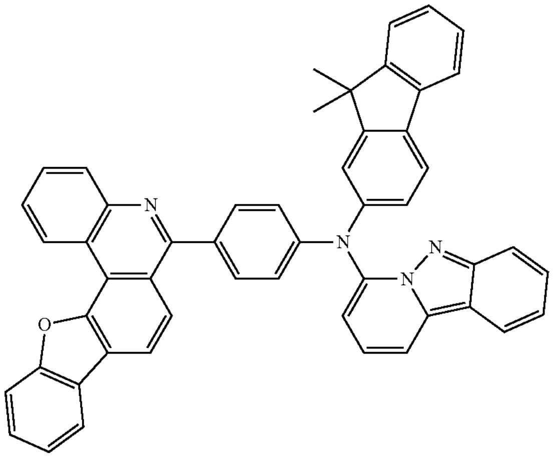
6-70
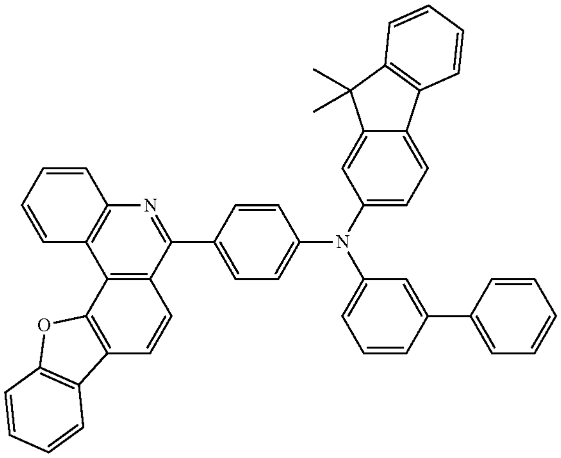

-continued
6-71
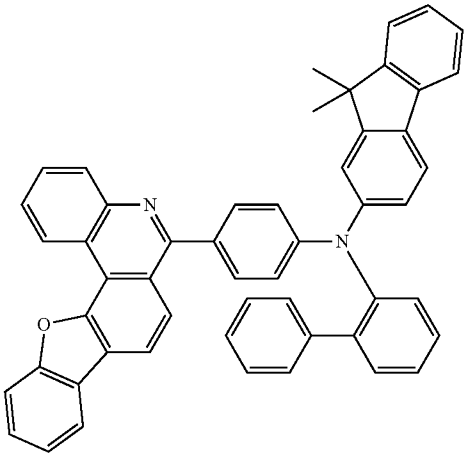
6-72
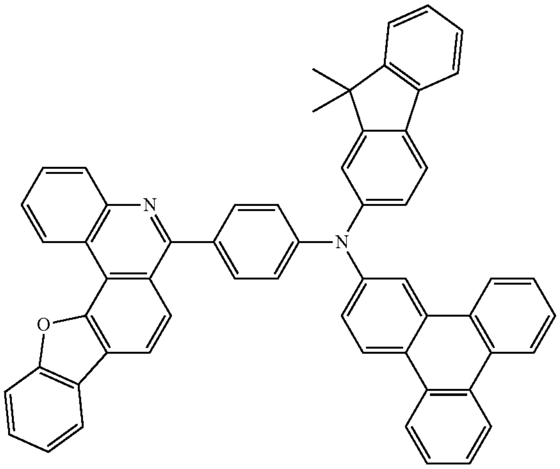
6-73
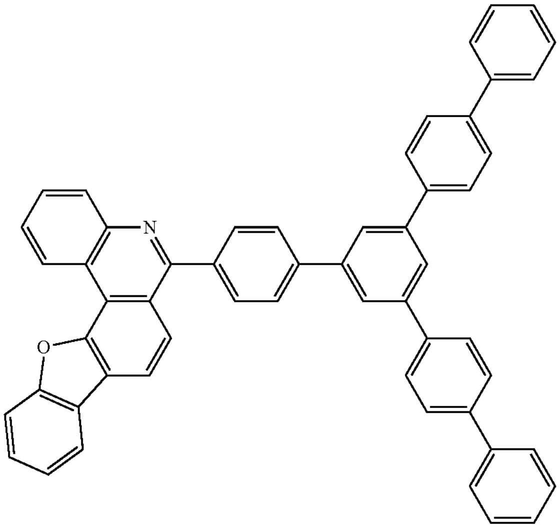
-continued
6-74
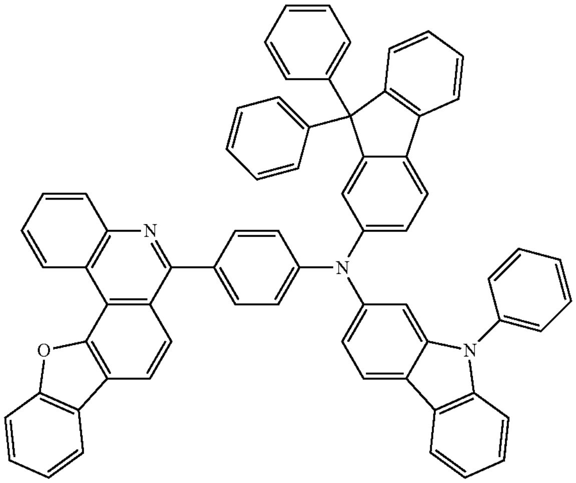
6-75
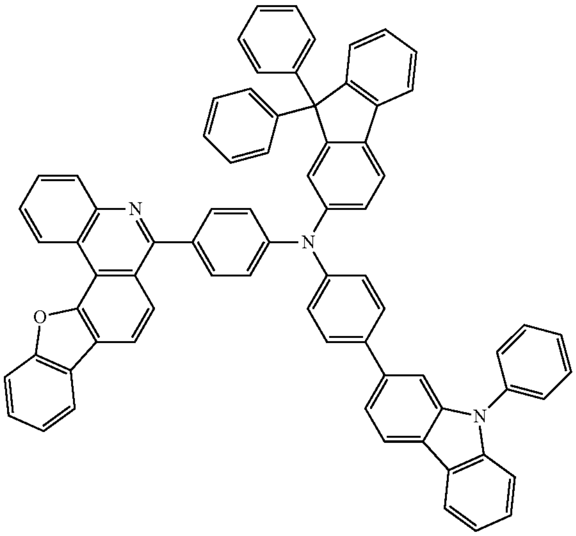
6-76
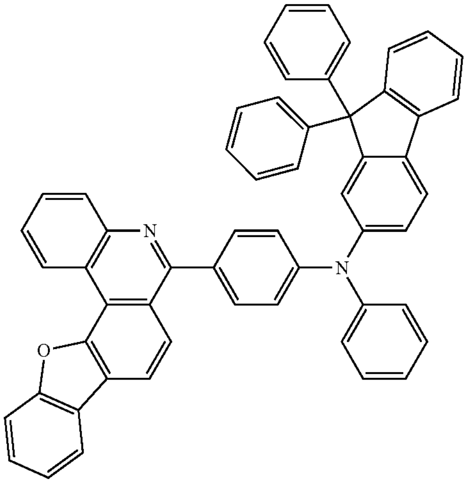

6-77
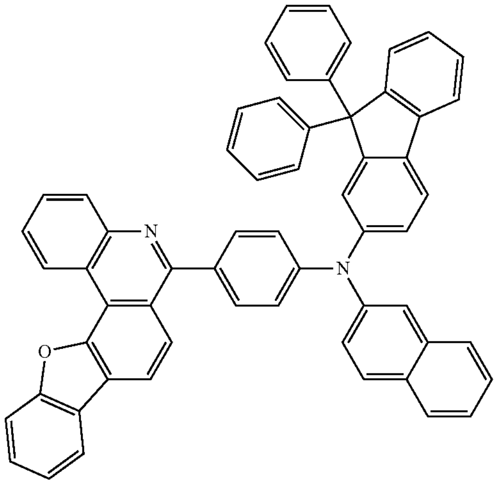
6-78
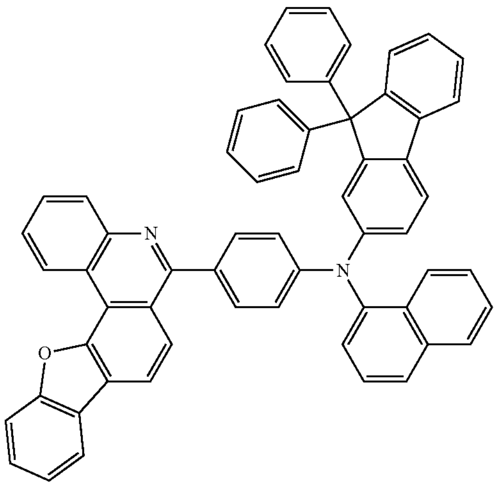
6-79
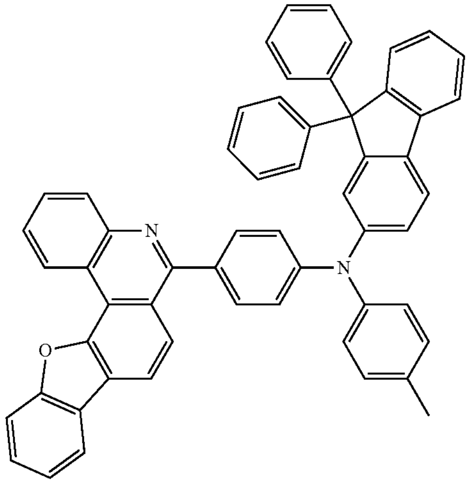
6-80
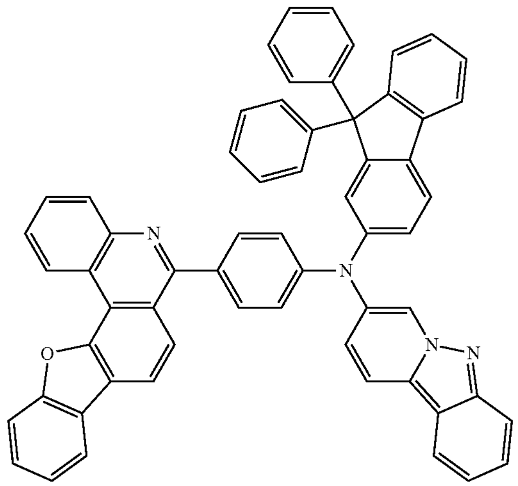
6-81
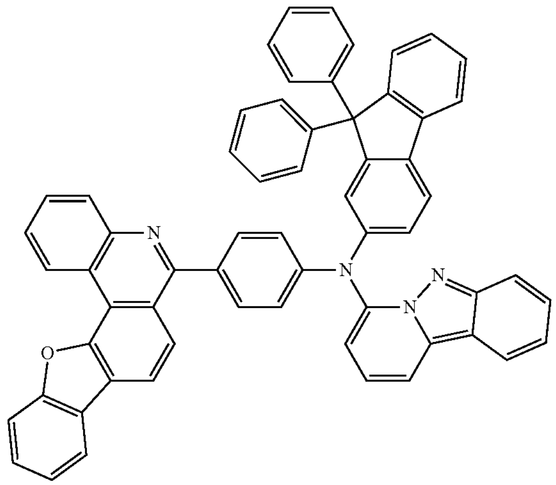
6-82
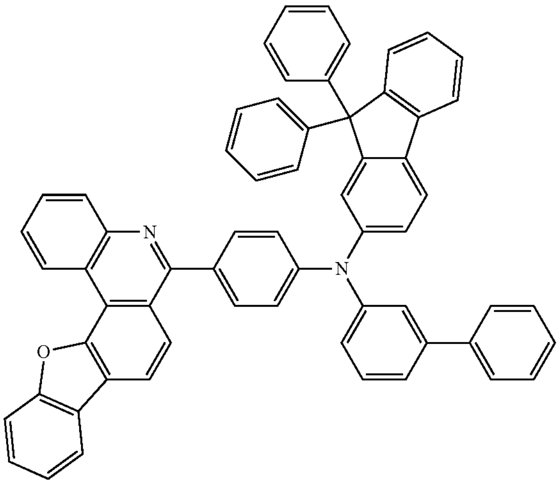

-continued
6-83
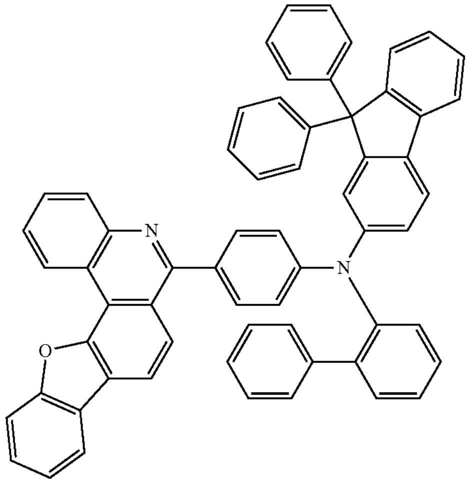
6-84
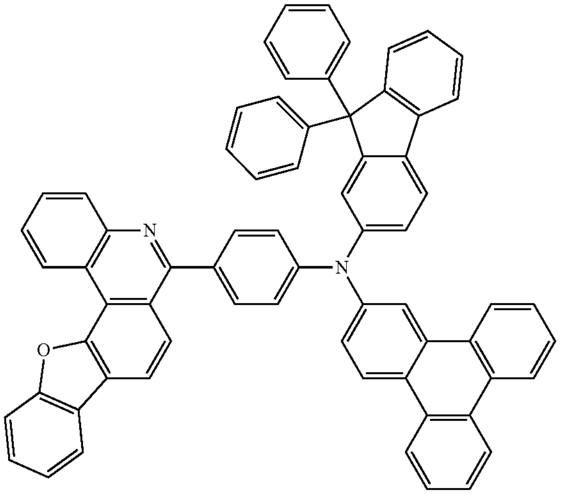
6-85
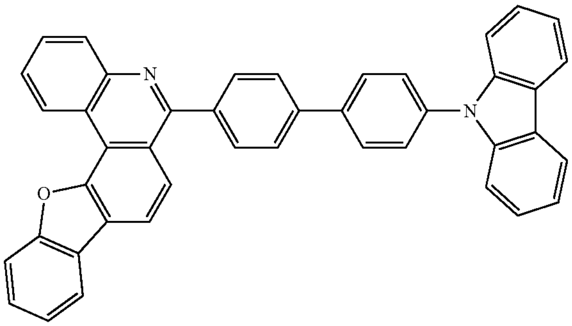
-continued
6-86
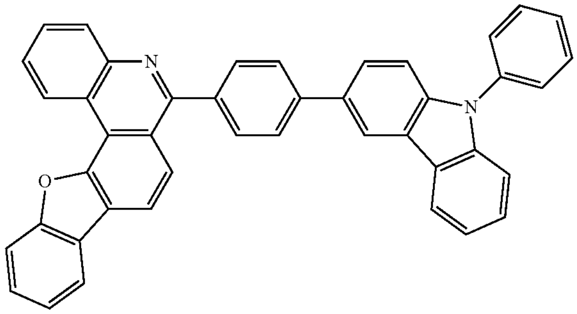
6-87
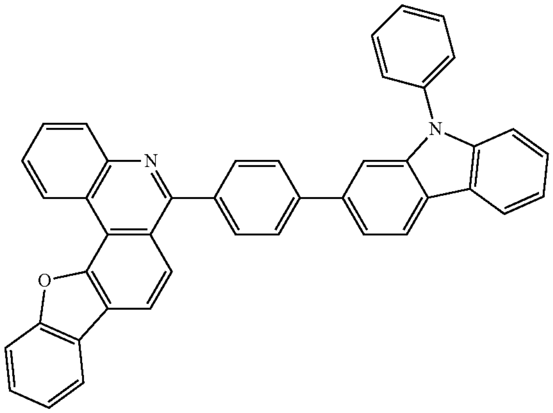
6-88
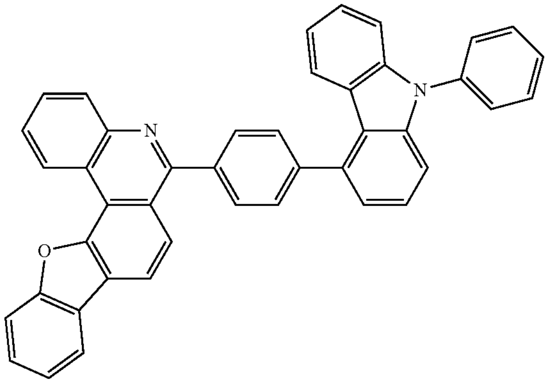
7-1
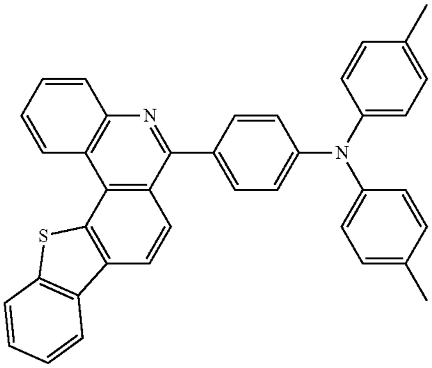

-continued
7-2
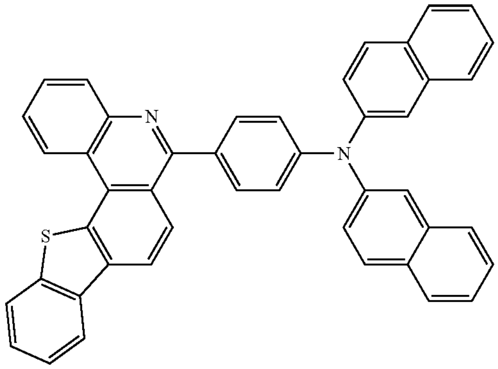
7-3
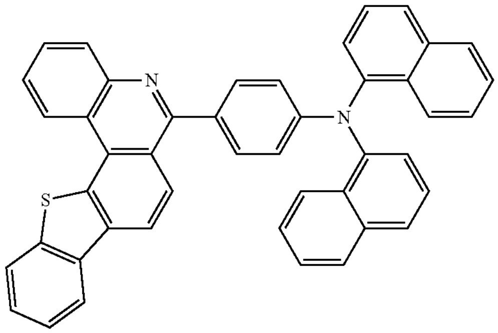
7-4
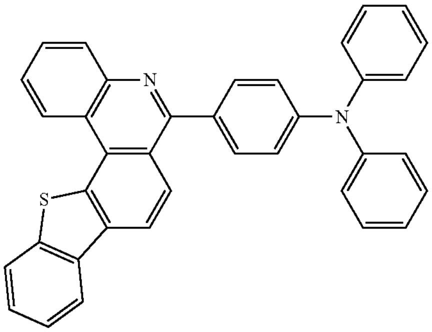
7-5
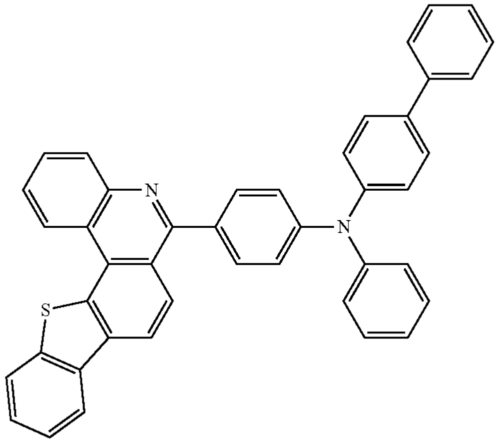
-continued
7-6
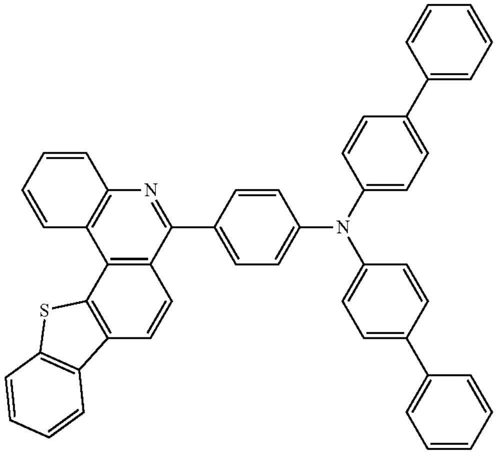
7-7
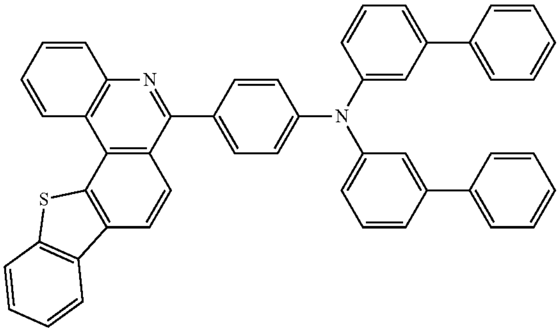
7-8
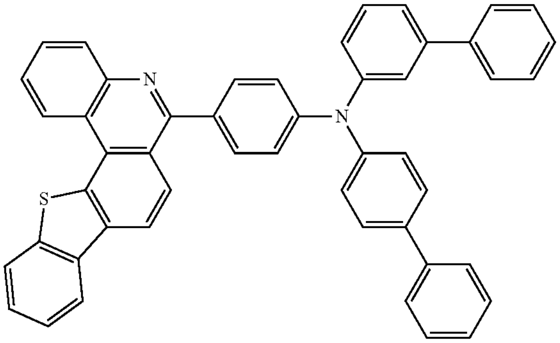
7-9
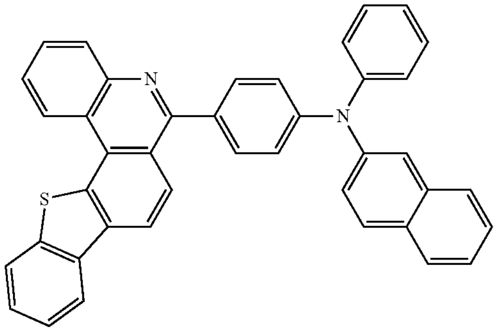

-continued
7-10
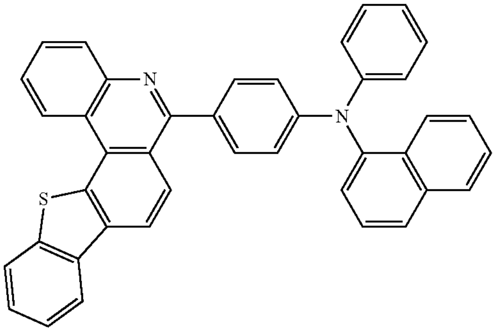
7-11
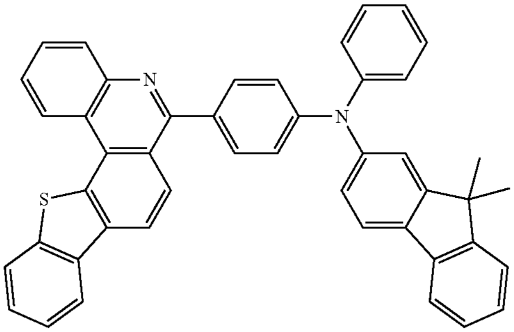
7-12
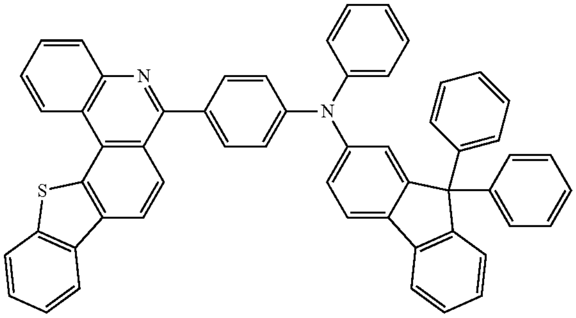
7-13
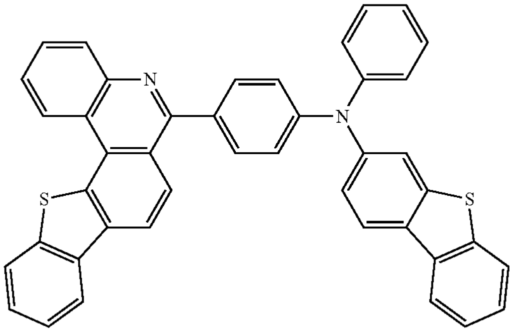
-continued
7-14
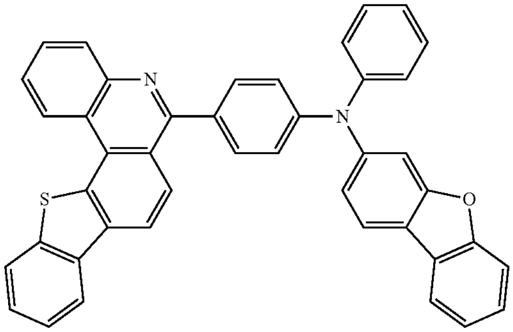
7-15
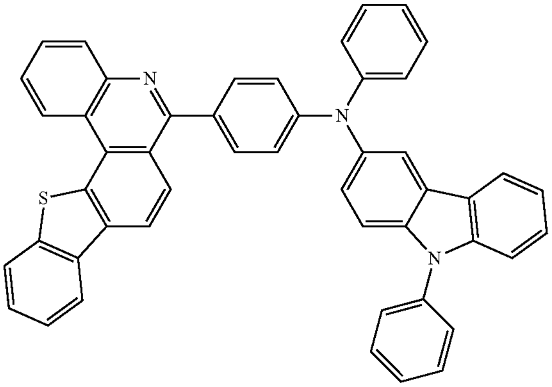
7-16
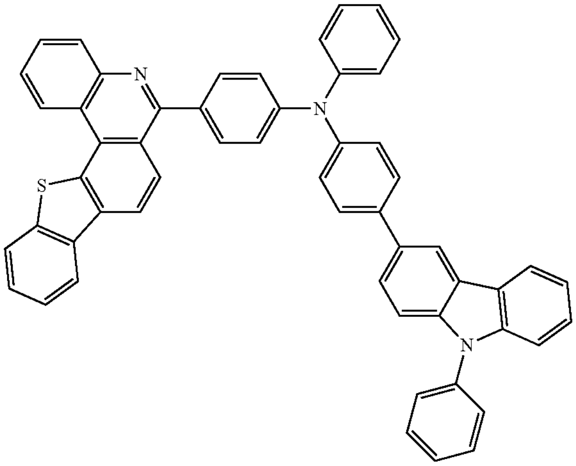
7-17
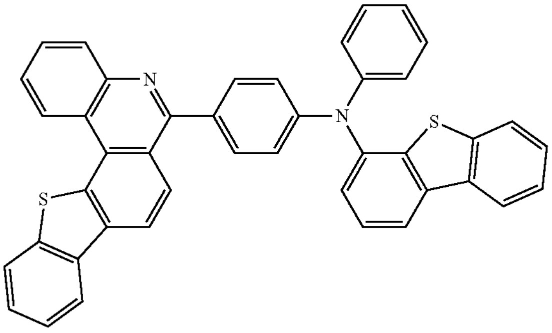

-continued
7-18
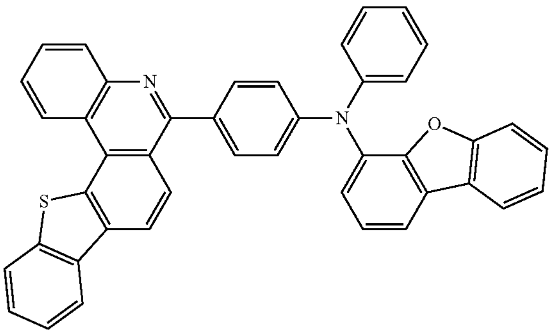
7-19
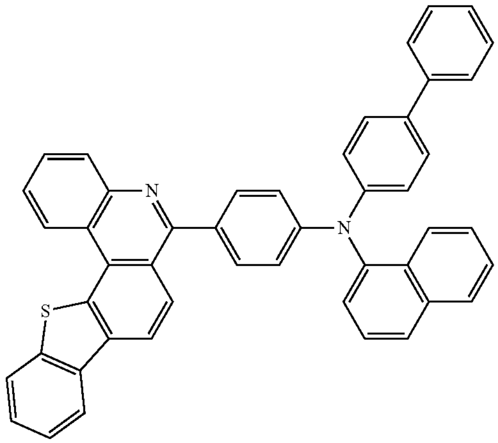
7-20
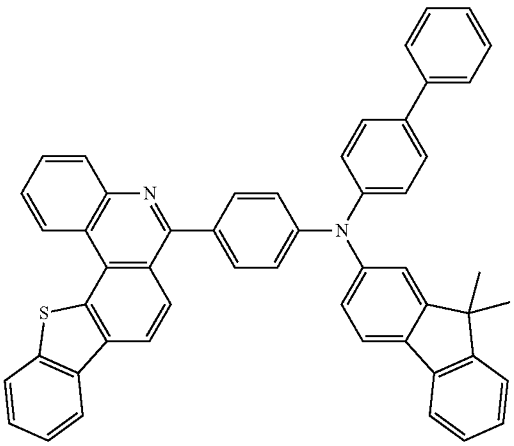
-continued
7-21
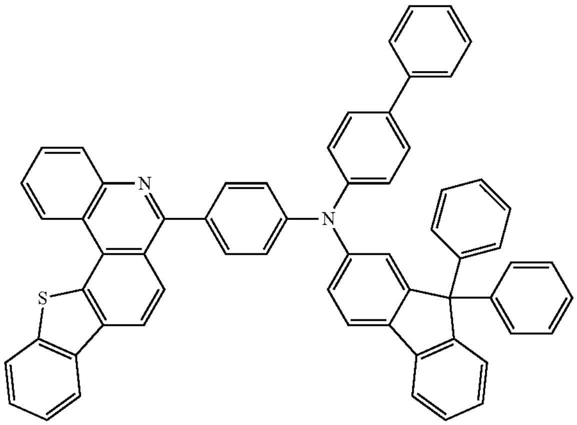
7-22
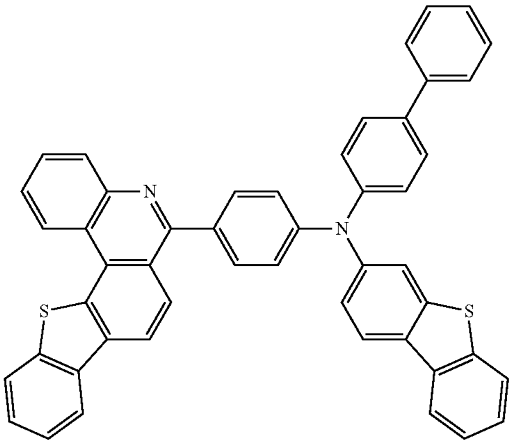
7-23
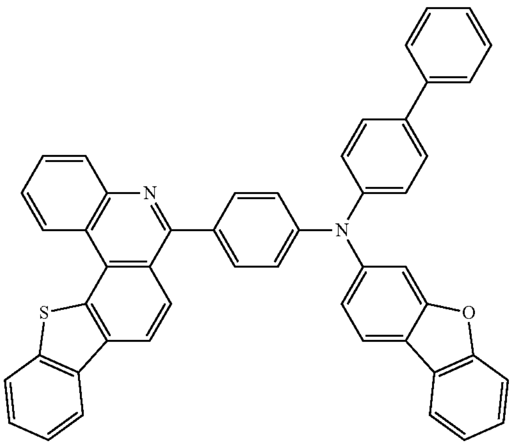

-continued
7-24
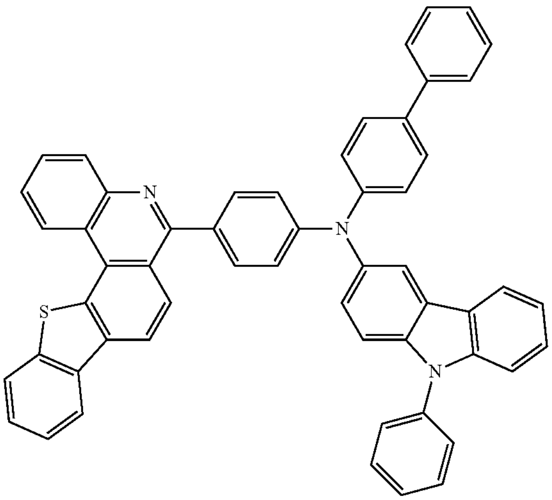
7-25
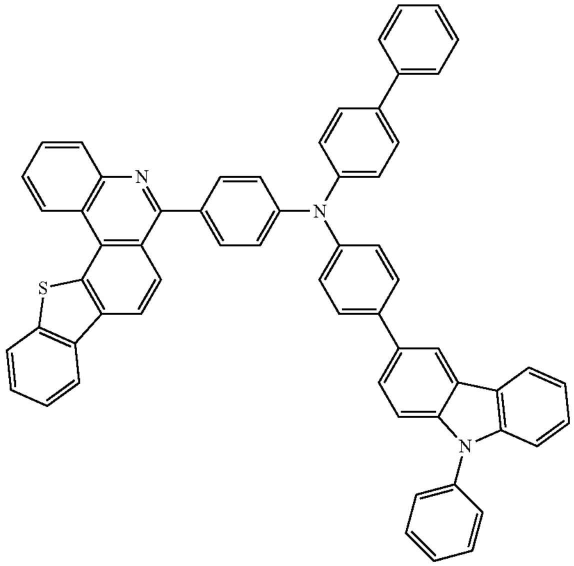
7-26
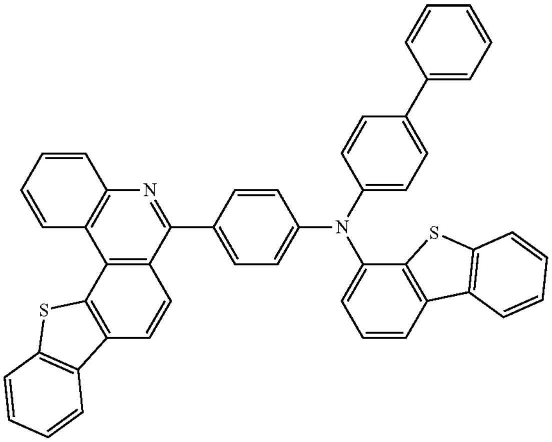
-continued
7-27
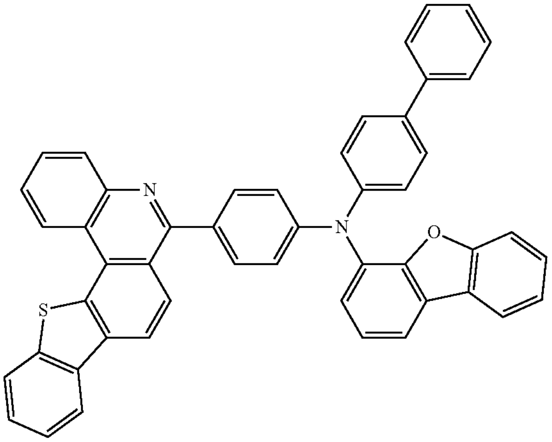
7-28
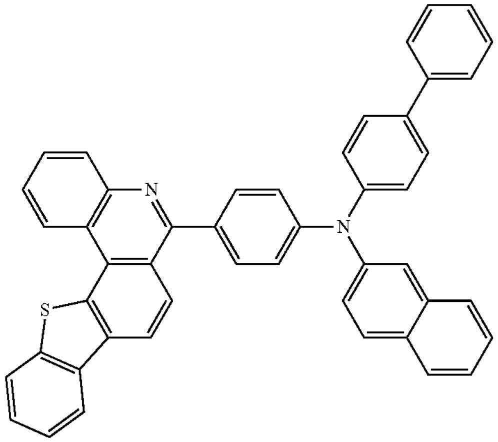
7-29
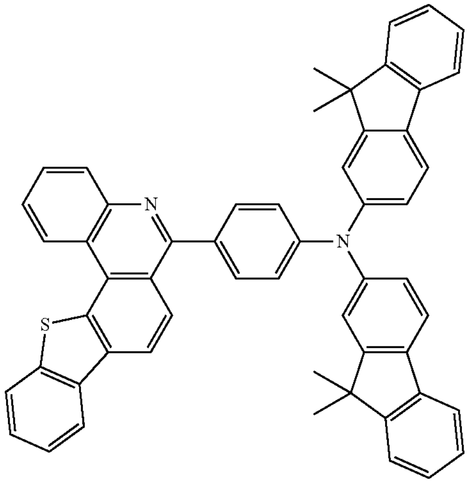

-continued
7-30
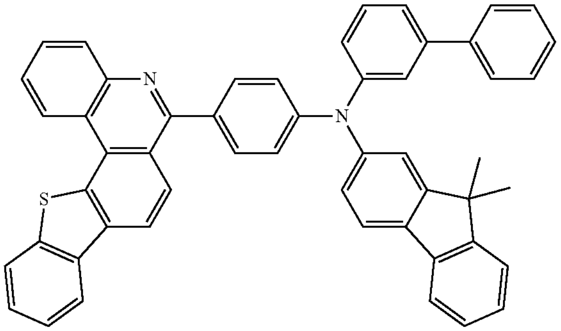
7-31
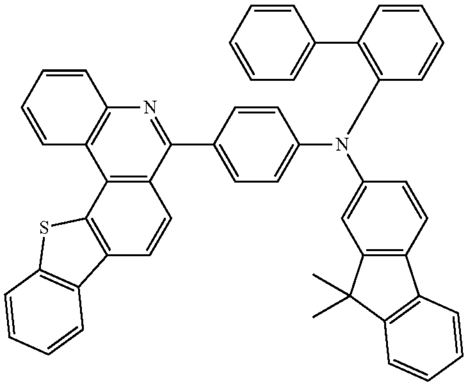
7-32
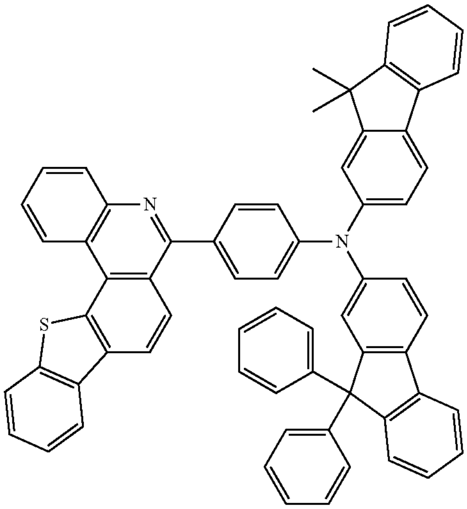
-continued
7-33
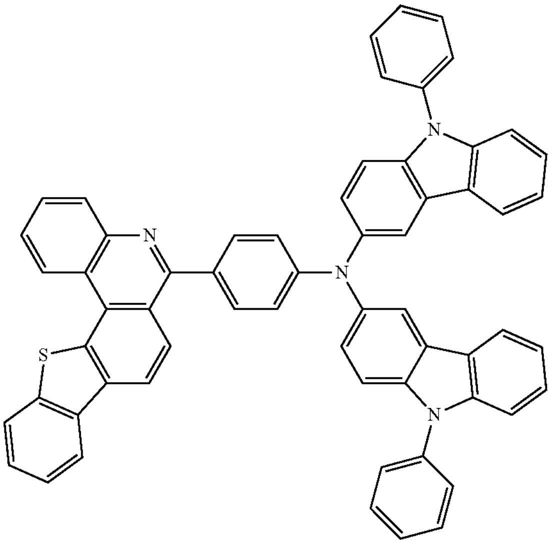
7-34
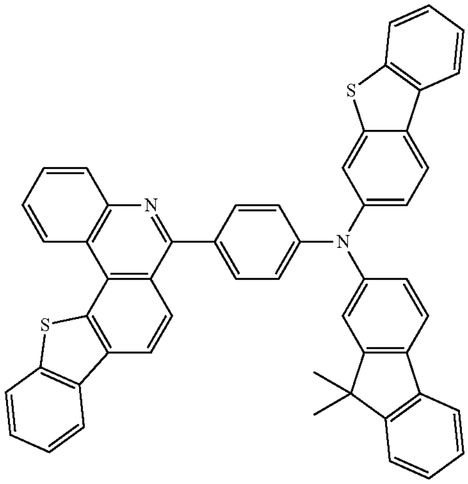
7-35
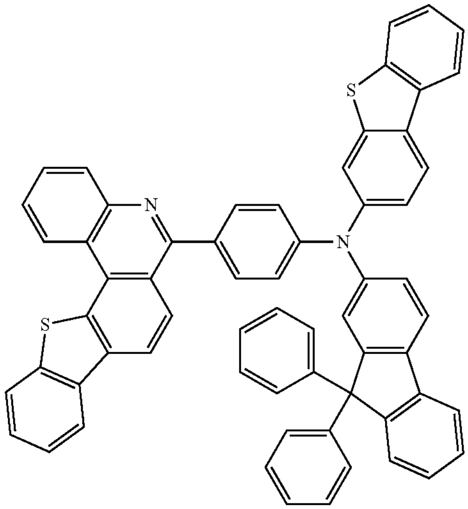

-continued
7-36
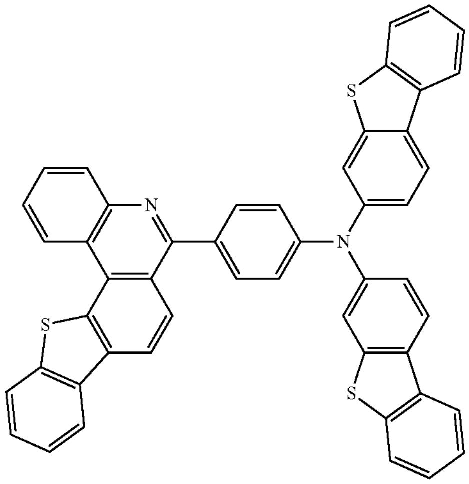
7-37
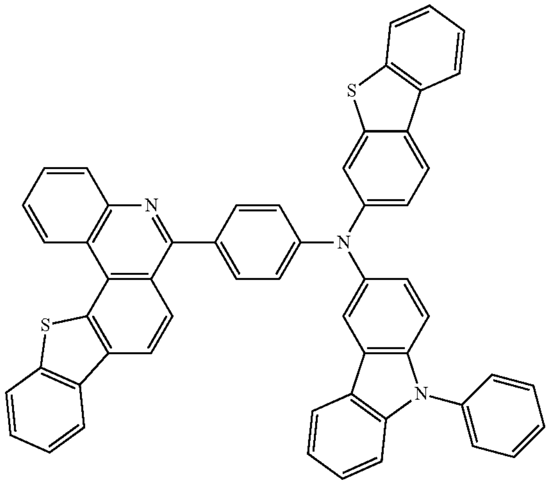
7-38
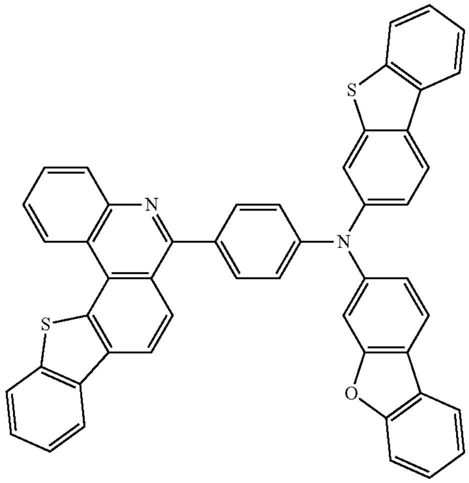
-continued
7-39
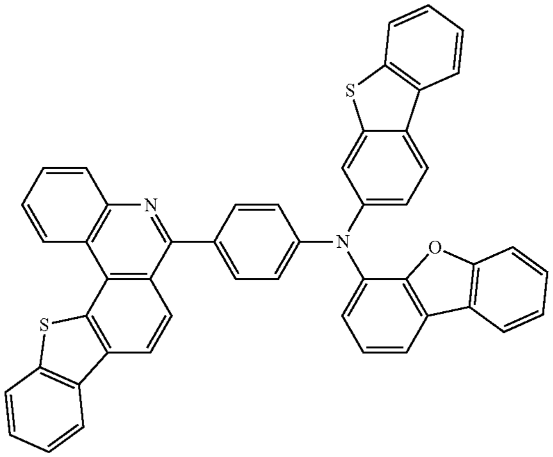
7-40
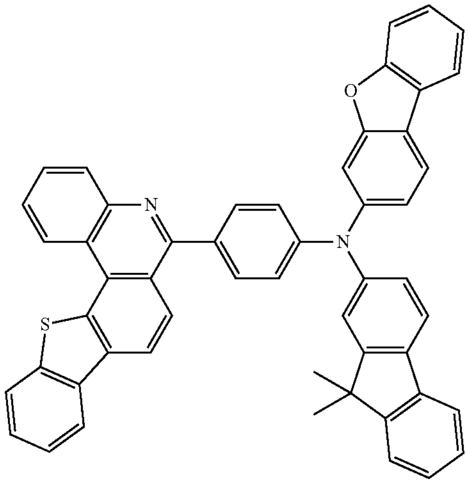
7-41
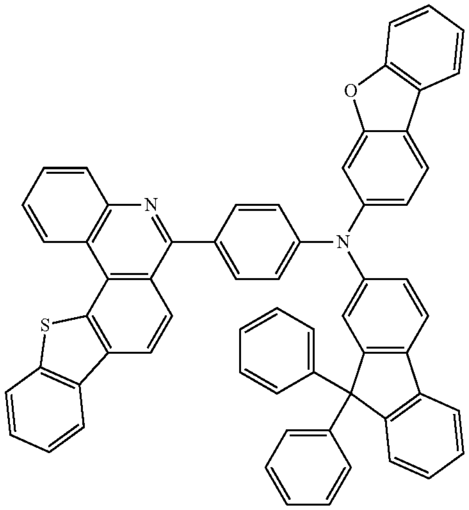

-continued
7-42
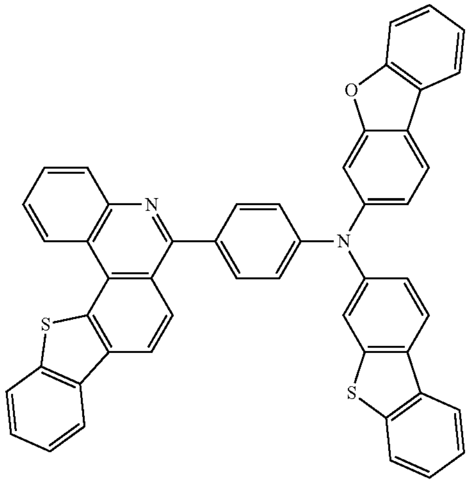
7-43
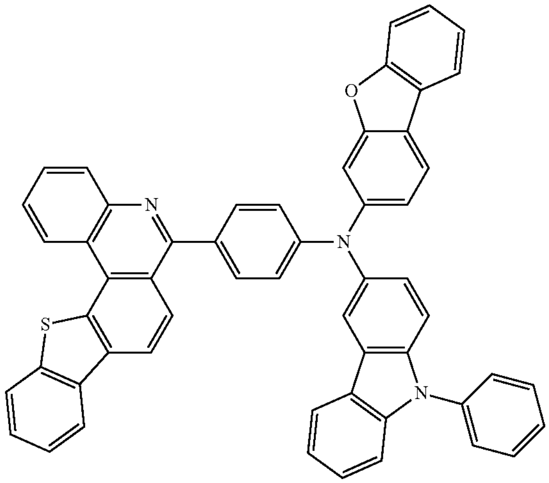
7-44
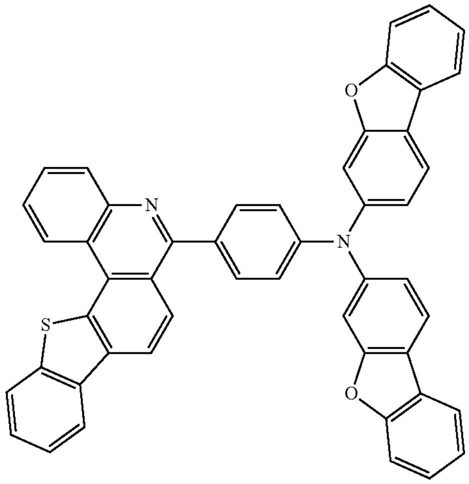
-continued
7-45
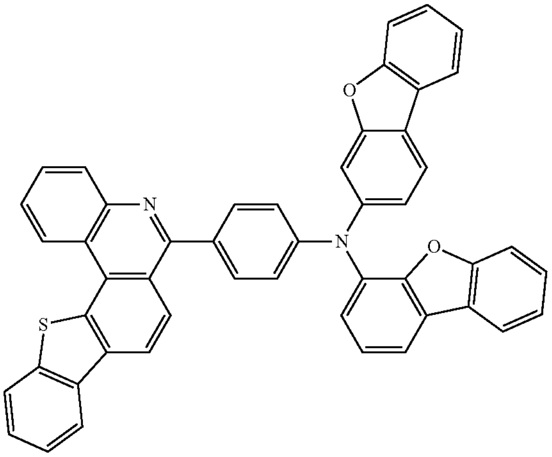
7-46
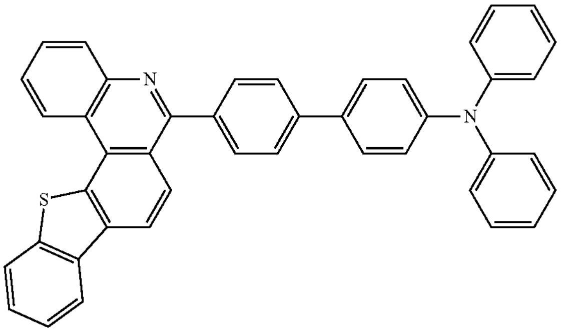
7-47
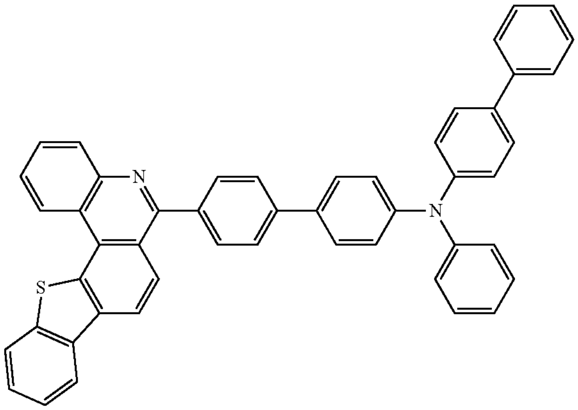

7-48
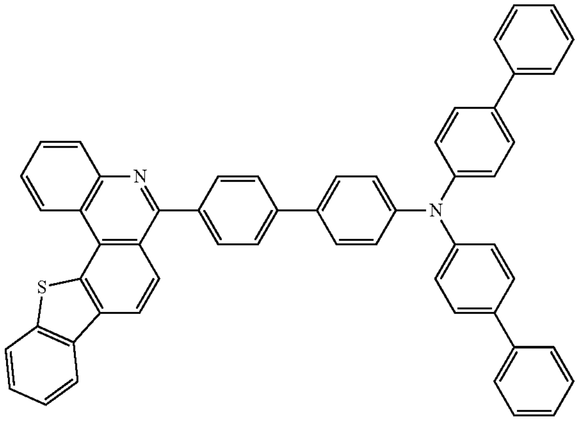
7-49
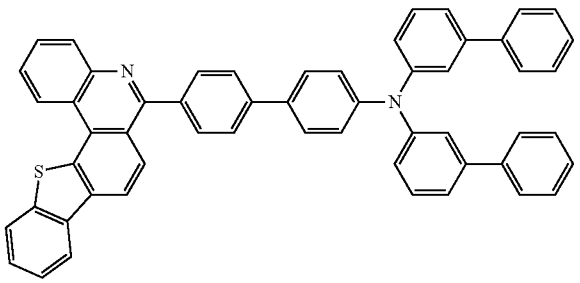
7-50
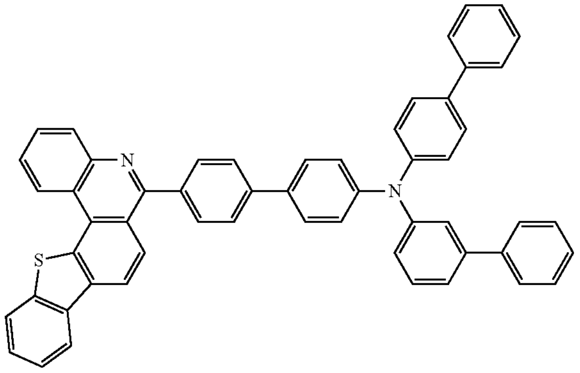
7-51
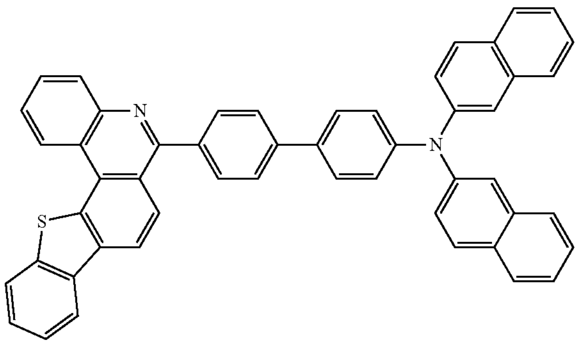
7-52
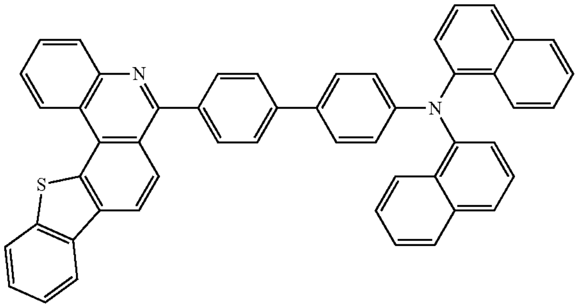
7-53
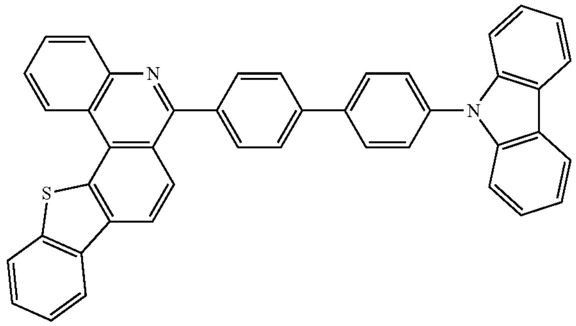
7-54
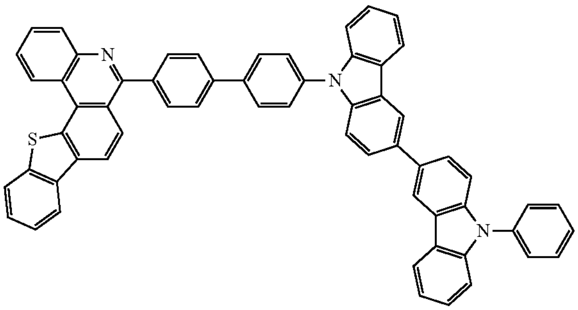
7-55
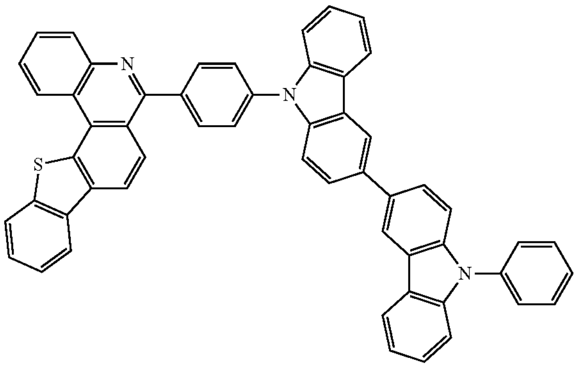

-continued
7-56
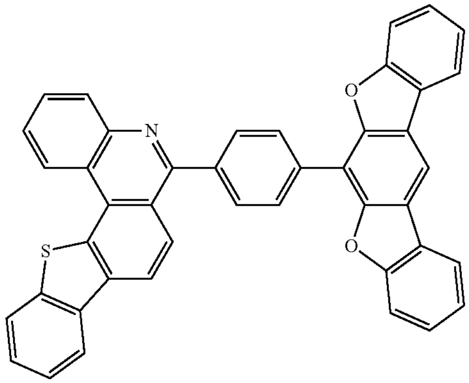
7-57
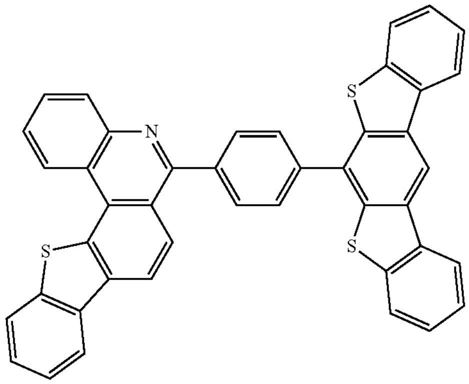
5-58
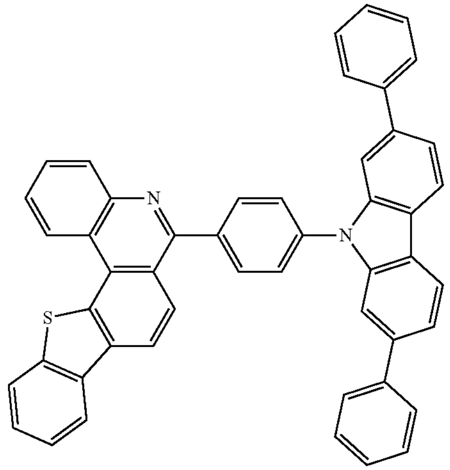
-continued
7-59
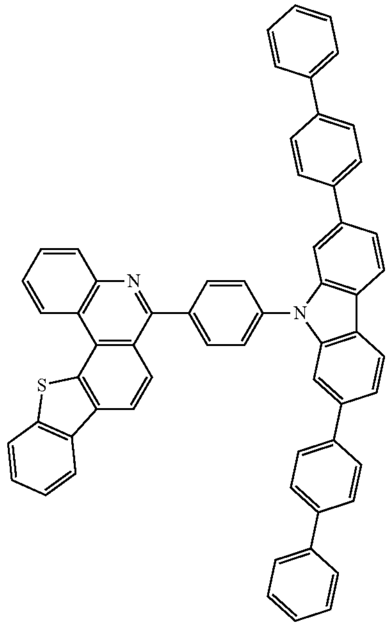
7-60
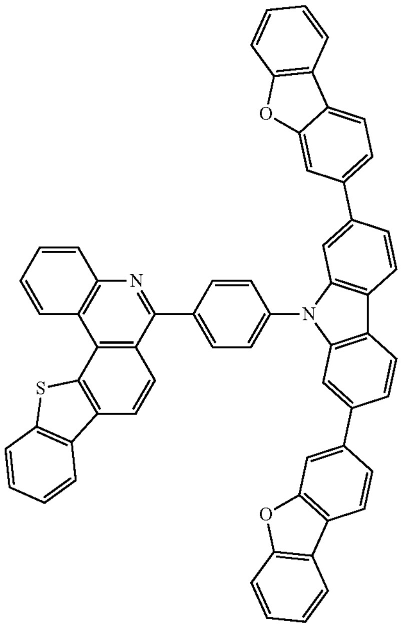
7-61
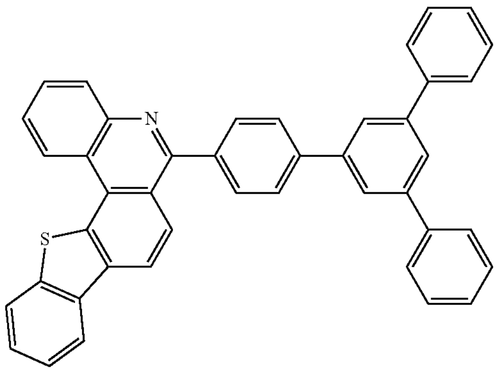

-continued
7-62
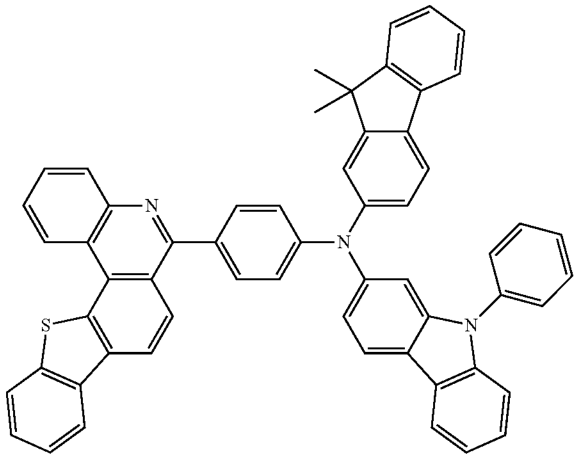
7-63
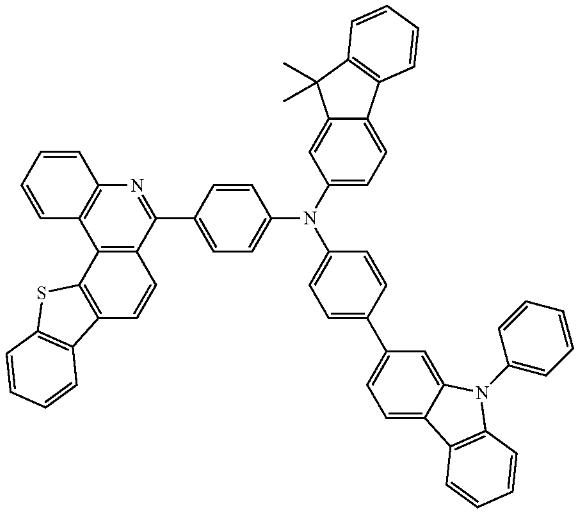
7-64
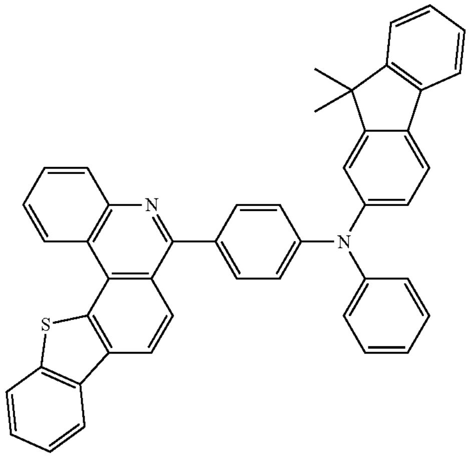
-continued
7-65
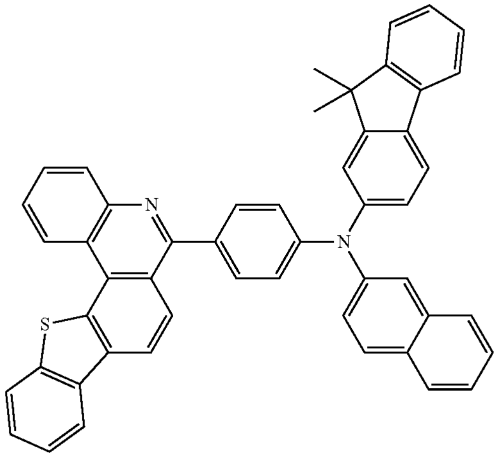
7-66
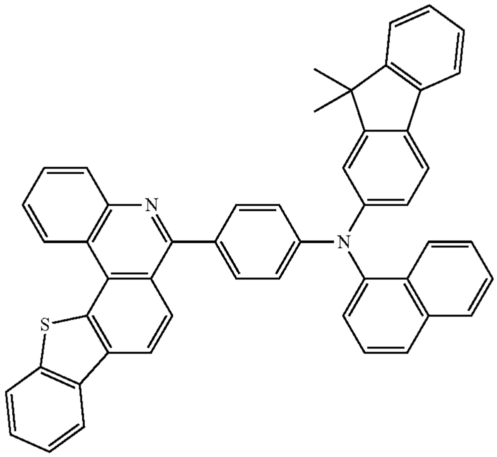
7-67
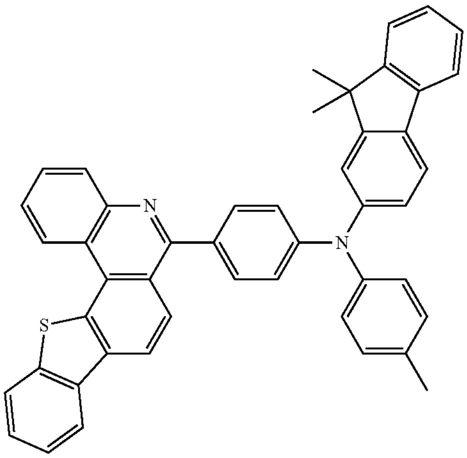

-continued
7-68
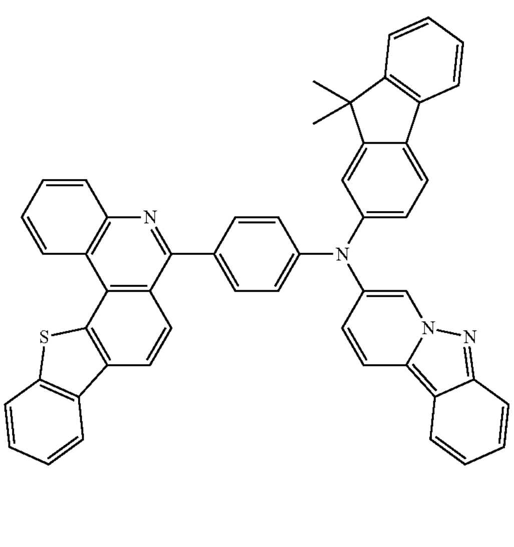
7-69
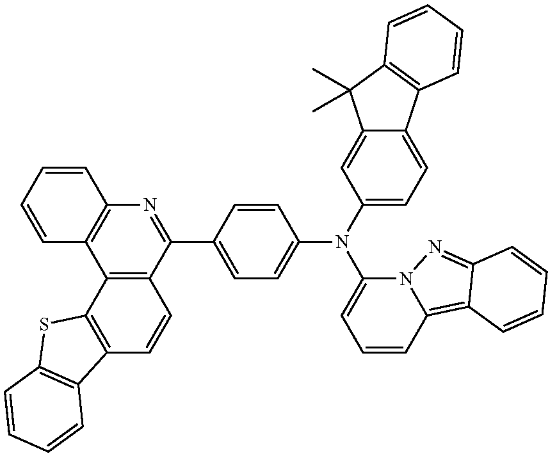
7-70
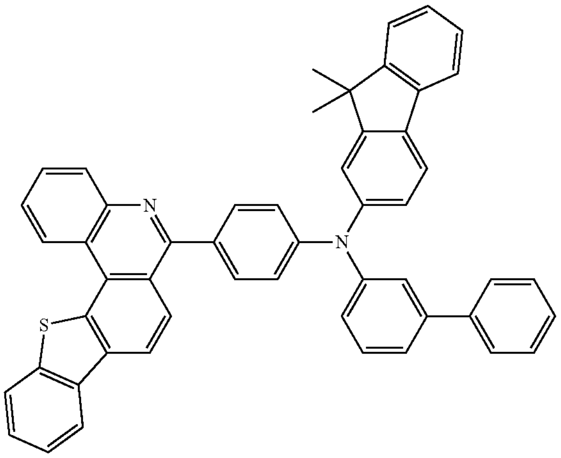
-continued
7-71
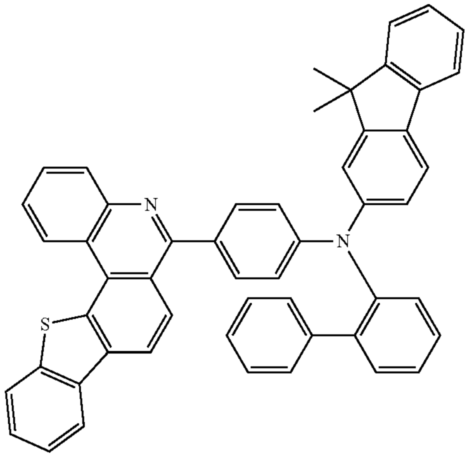
7-72
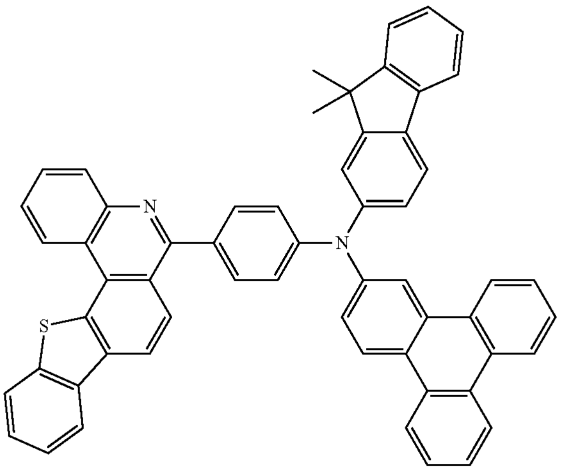
7-73
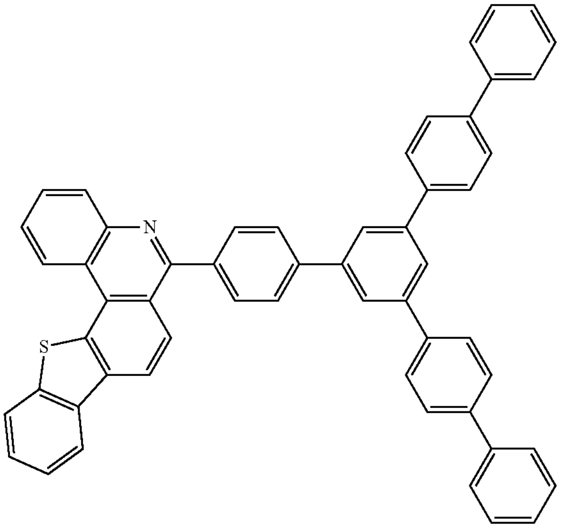

-continued
6-74
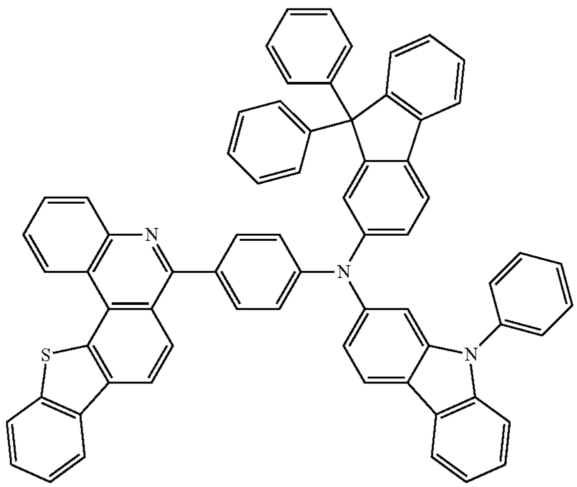
7-75
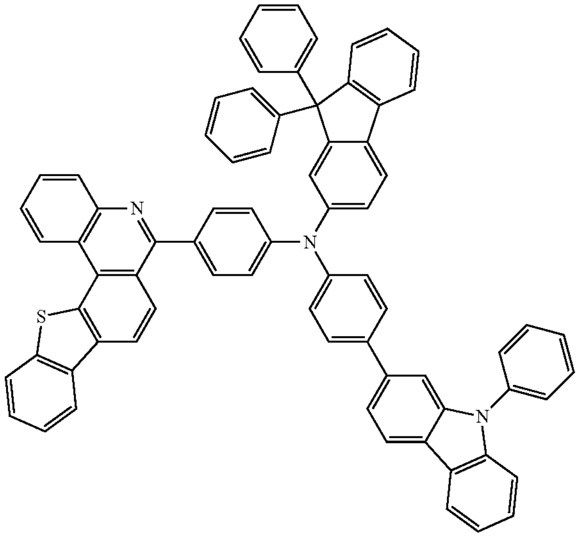
7-76
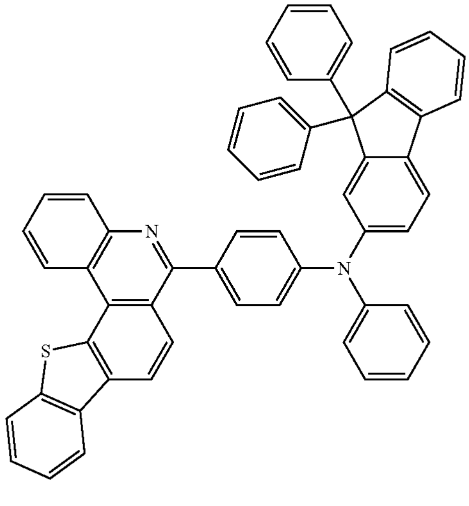
-continued
7-77
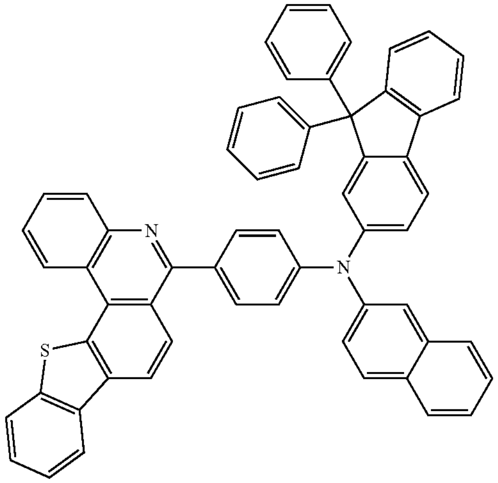
7-78
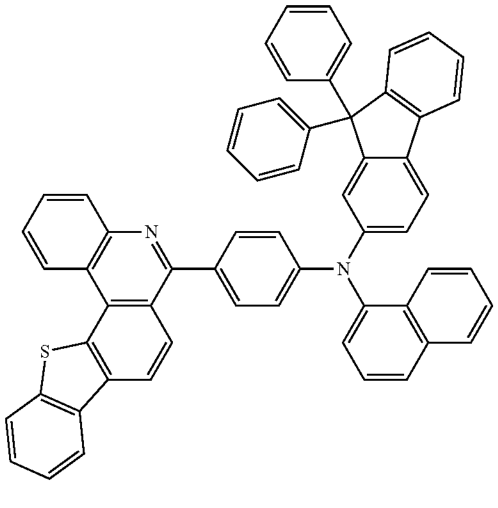
7-79
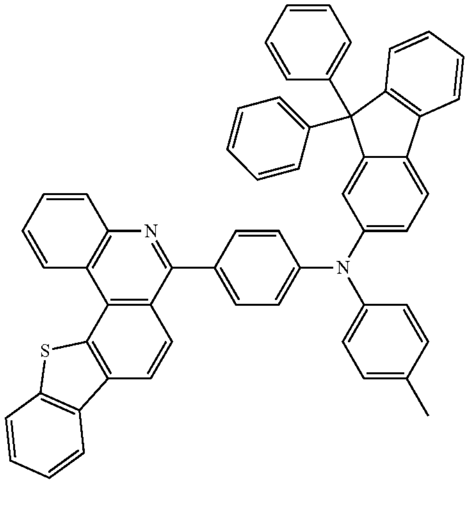

-continued
7-80
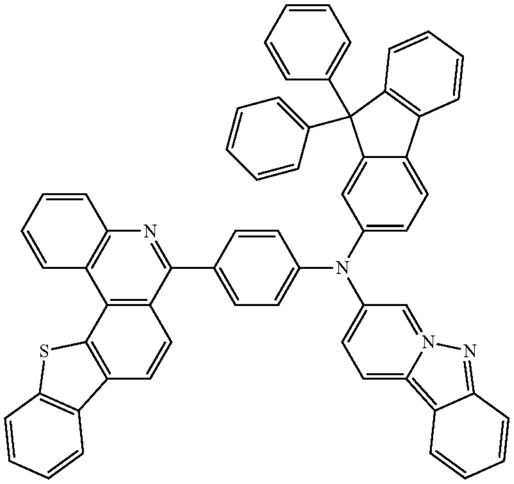
7-81
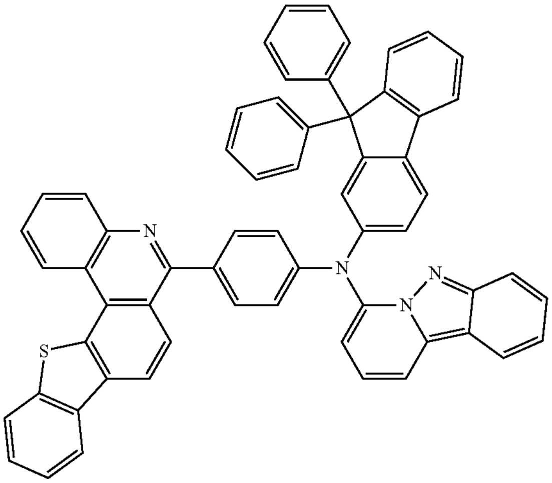
7-82
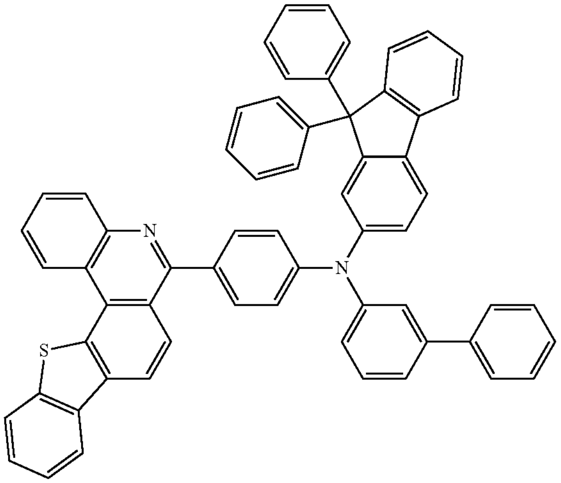
-continued
7-83
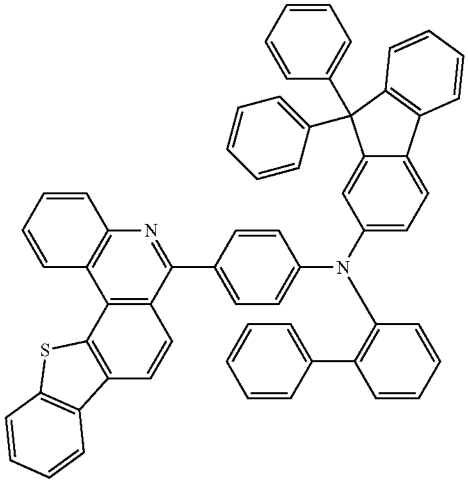
7-84
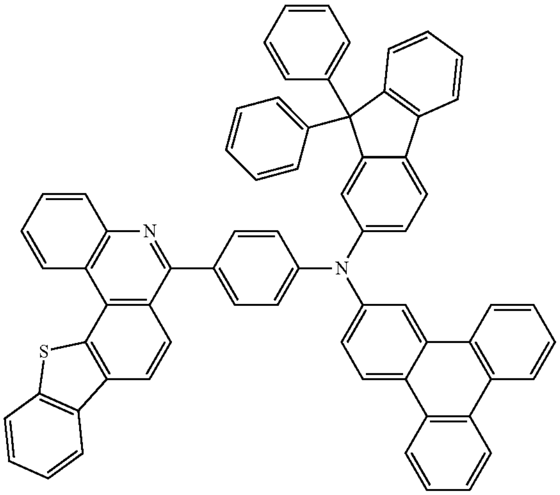
7-85
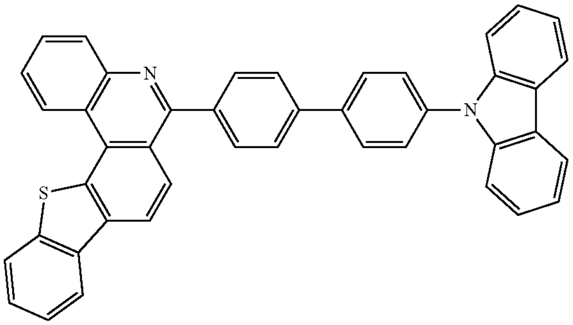

-continued
7-86
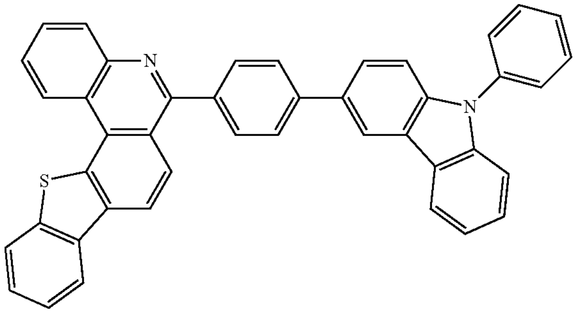
7-87
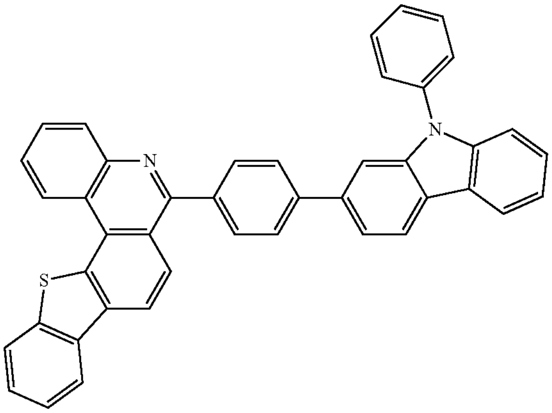
7-88
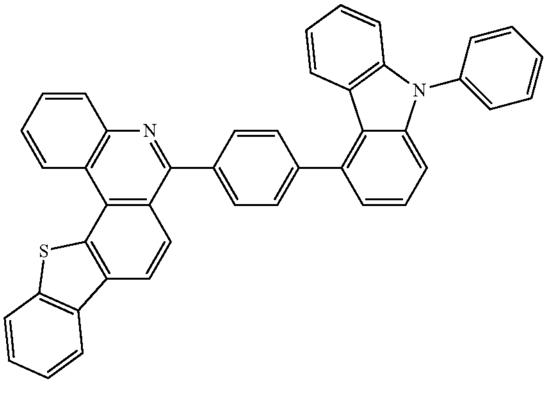
-continued
10-1
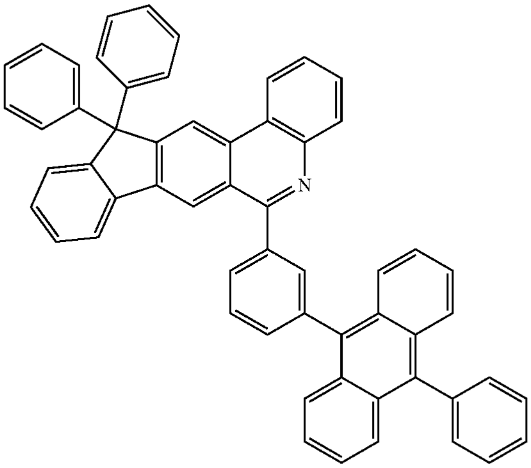
10-2
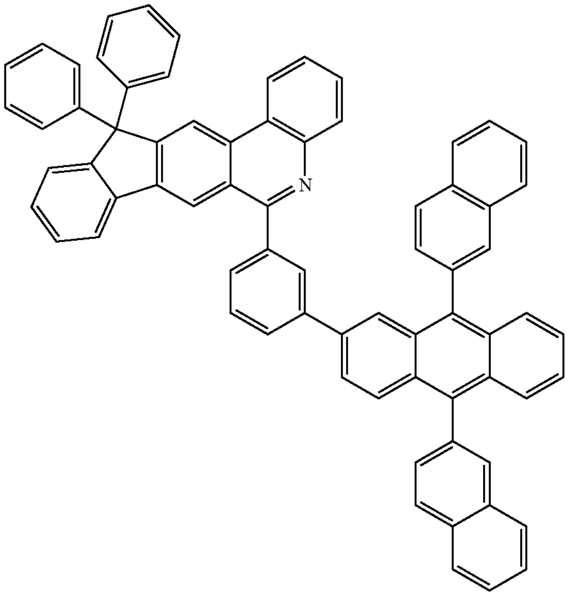
10-3
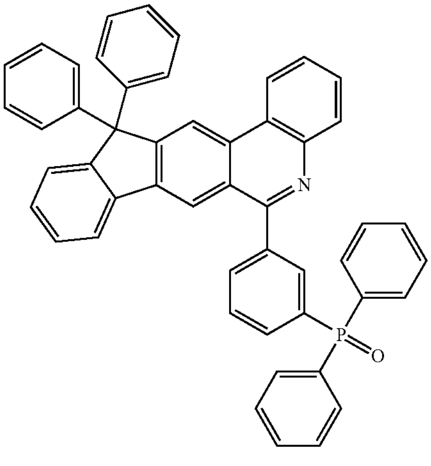

-continued
10-4
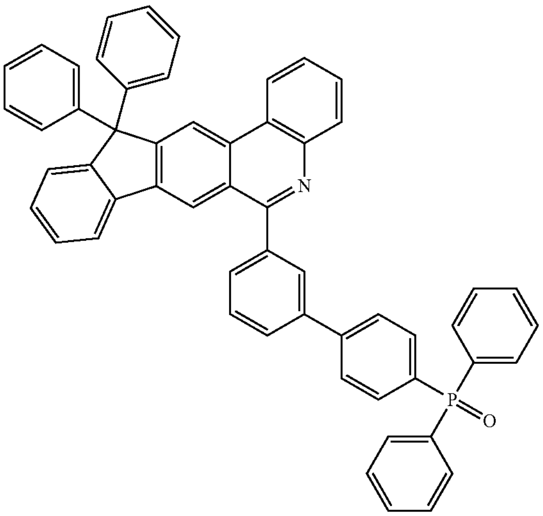
10-5
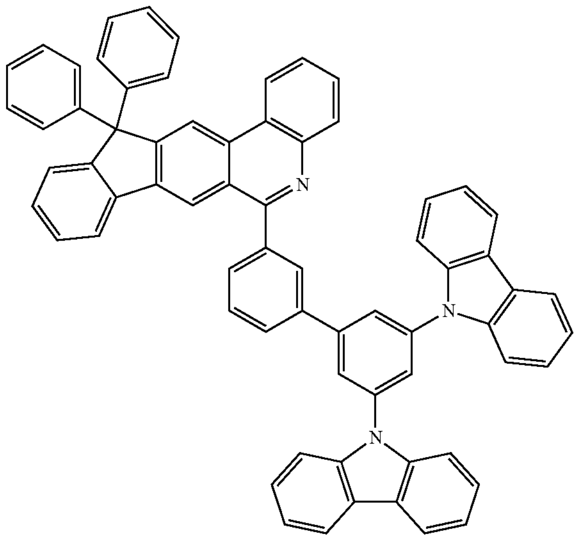
10-6
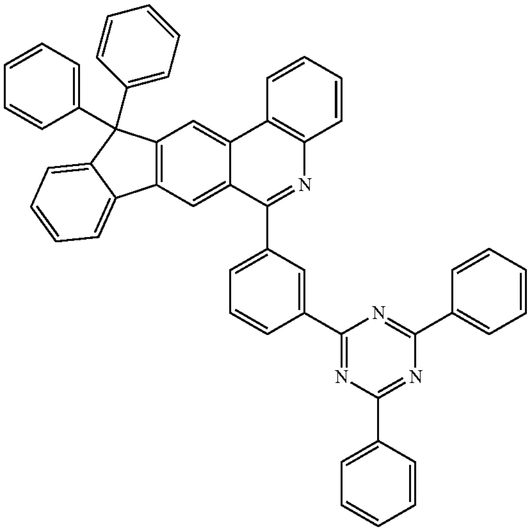
-continued
10-7
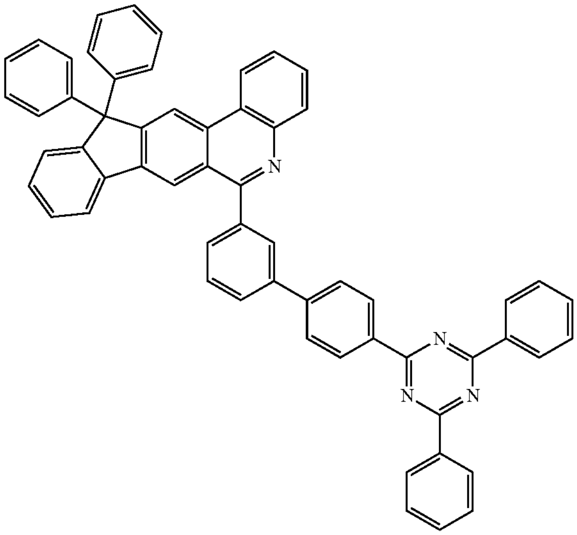
10-8
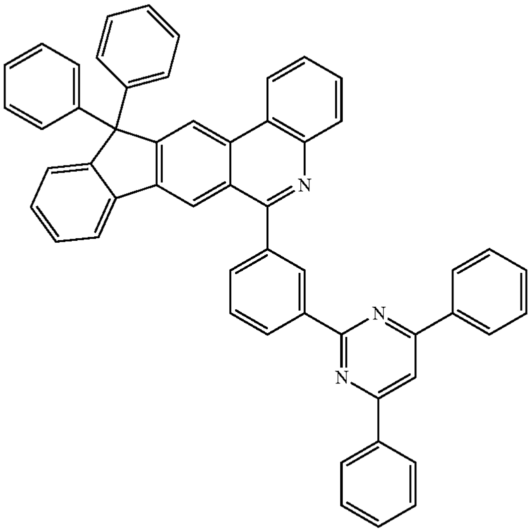
10-9
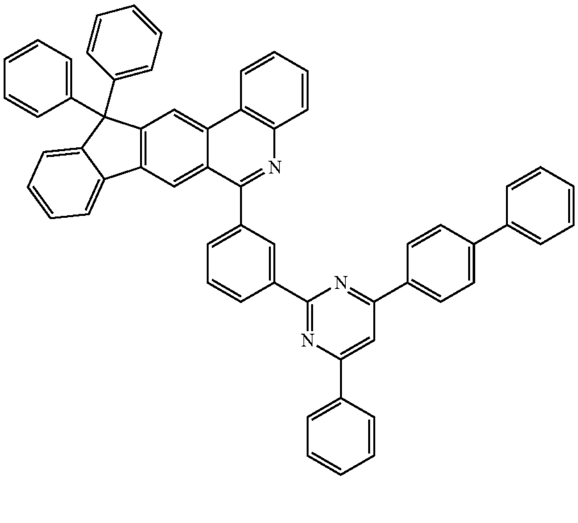

-continued
10-10
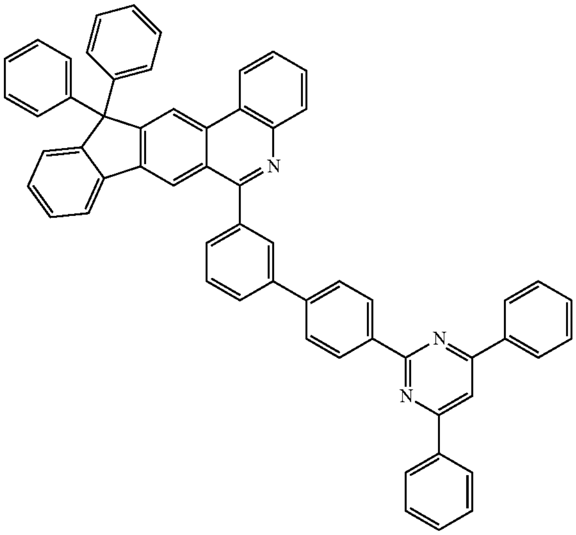
10-11
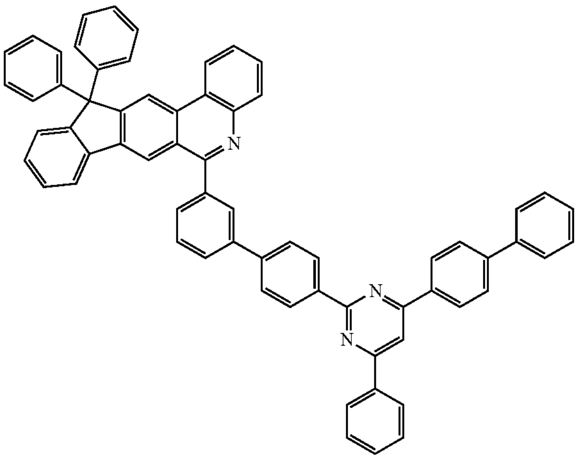
10-12
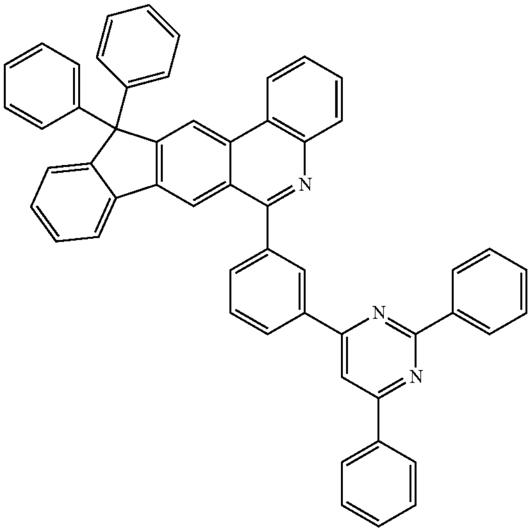
-continued
10-13
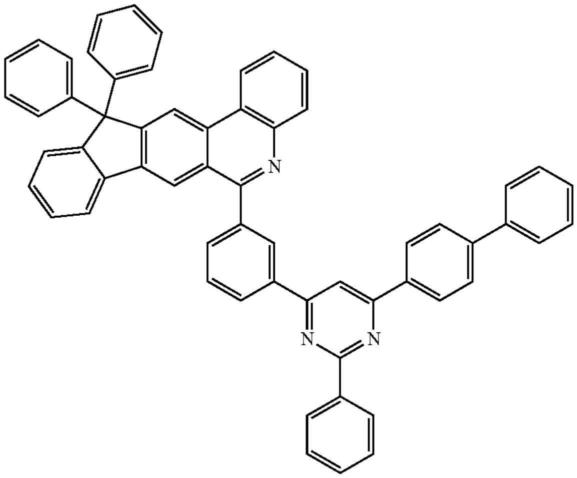
10-14
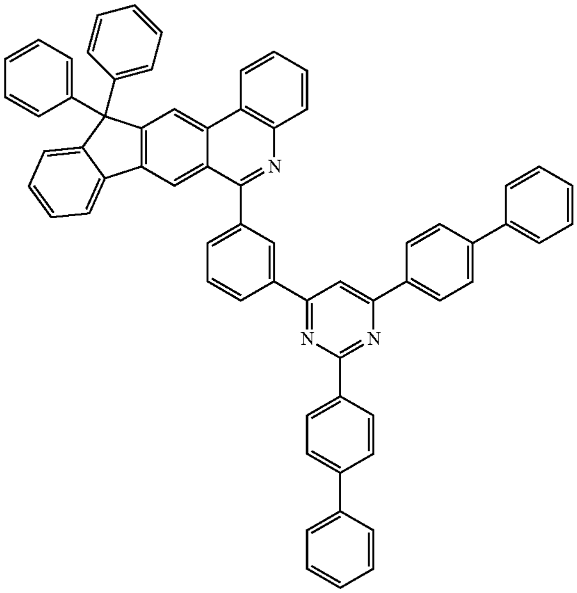
10-15
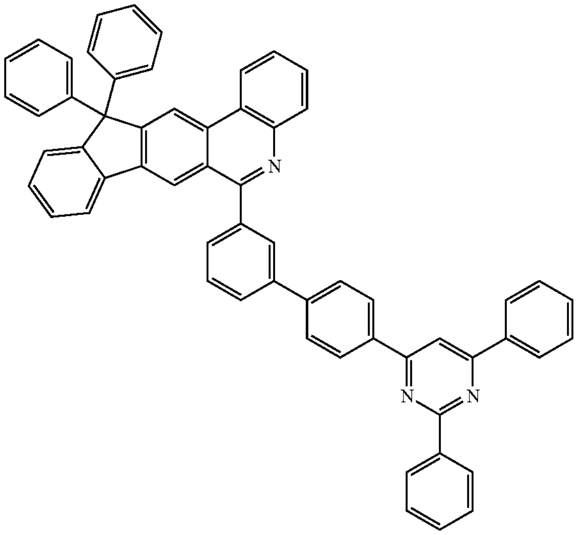

-continued
10-16
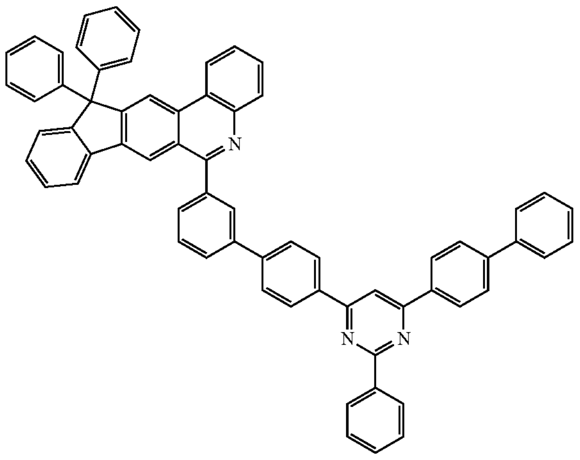
10-17
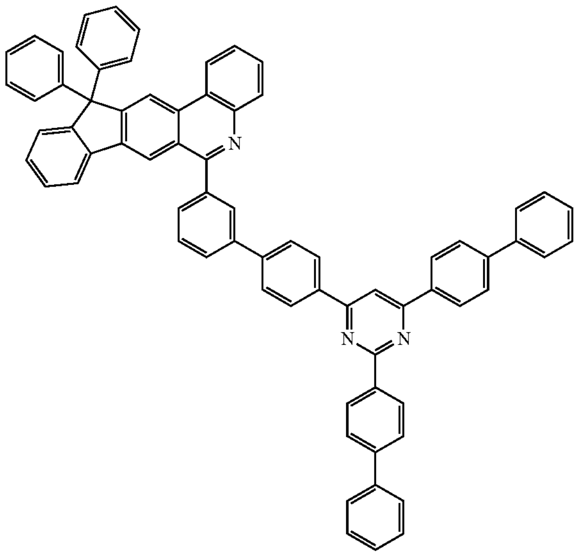
10-18
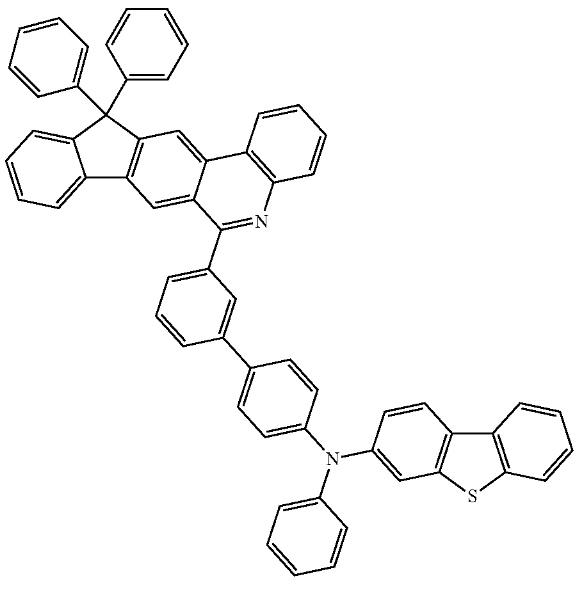
-continued
10-19
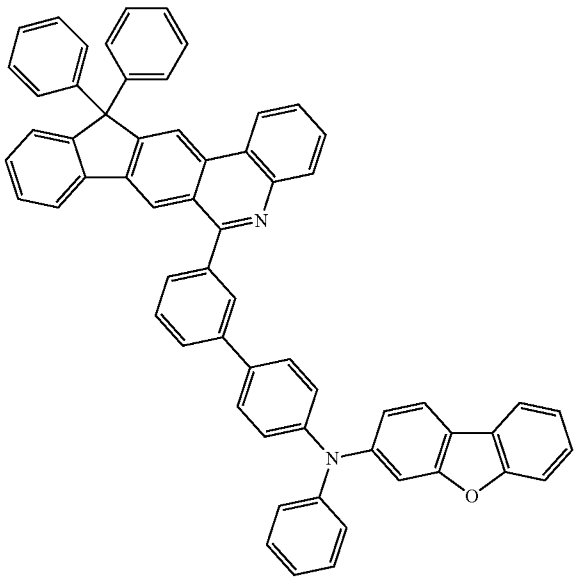
10-20
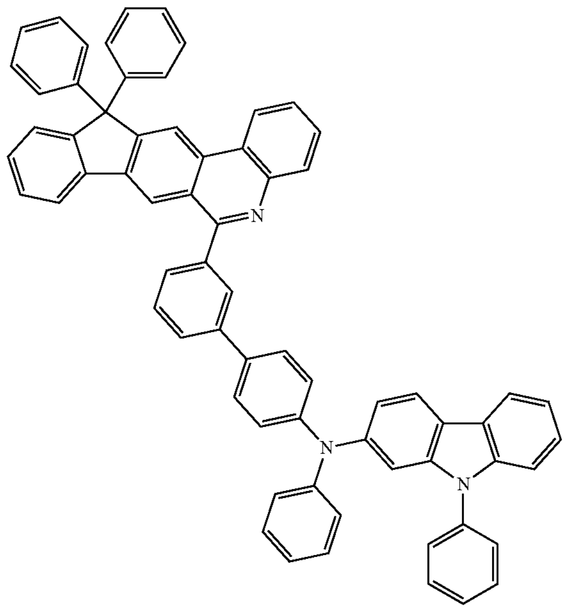

-continued
10-21
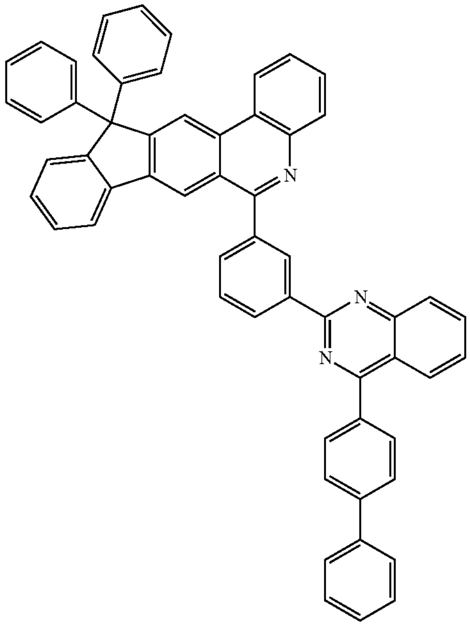
10-22
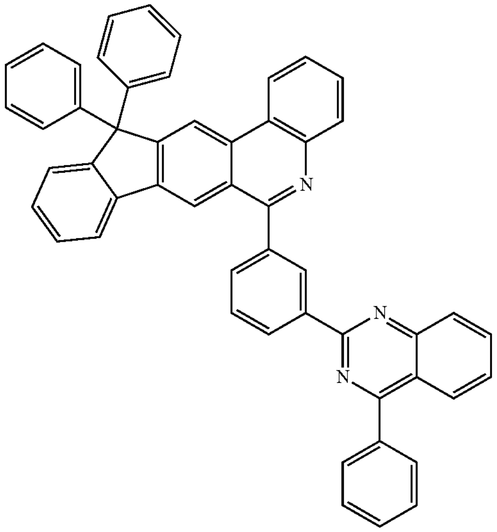
-continued
10-23
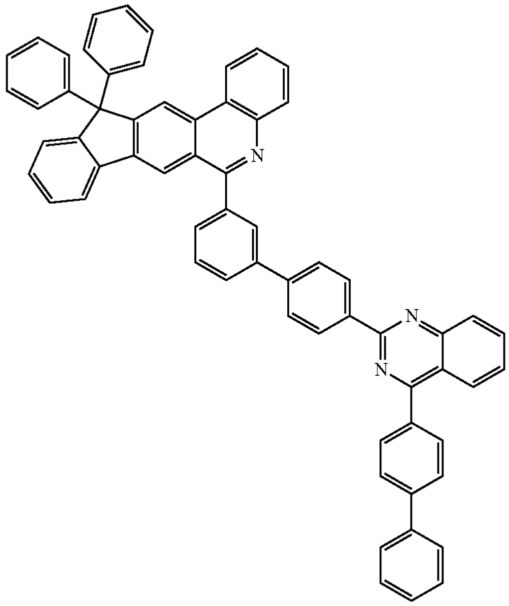
10-24
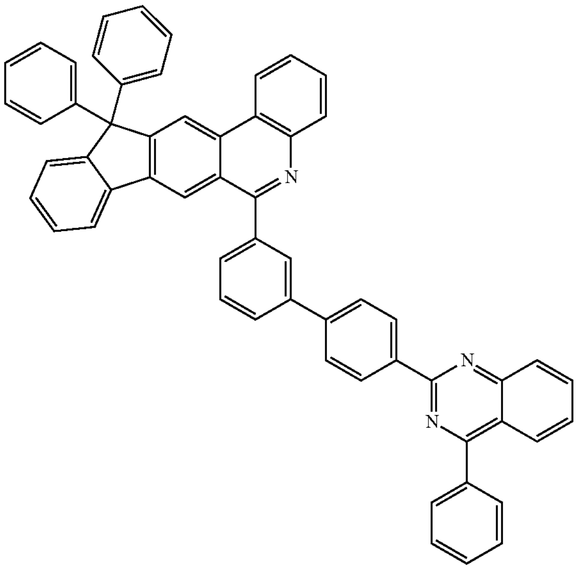

-continued
10-25
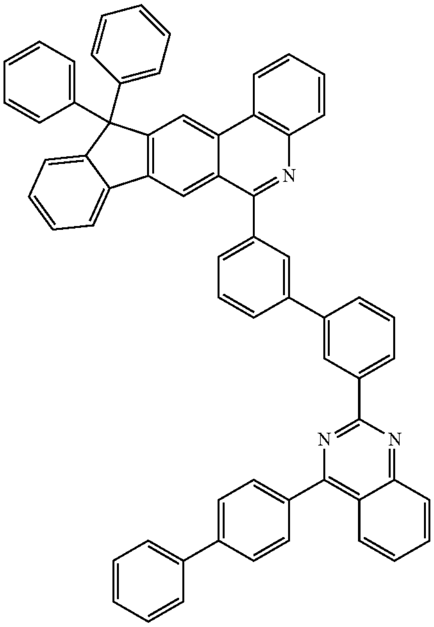
10-26
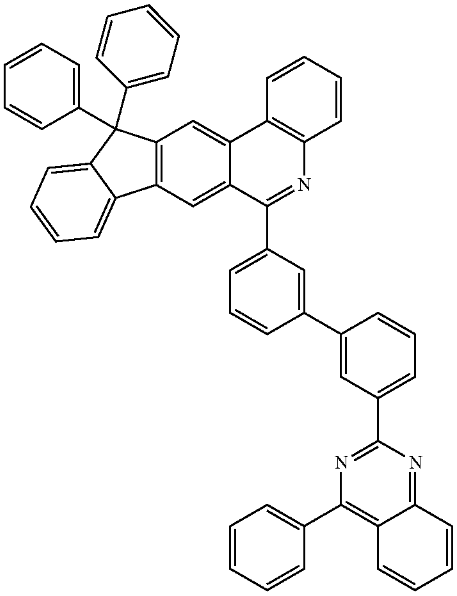
-continued
10-27
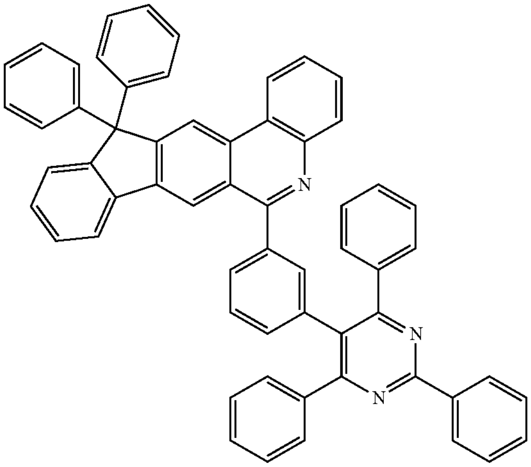
10-28
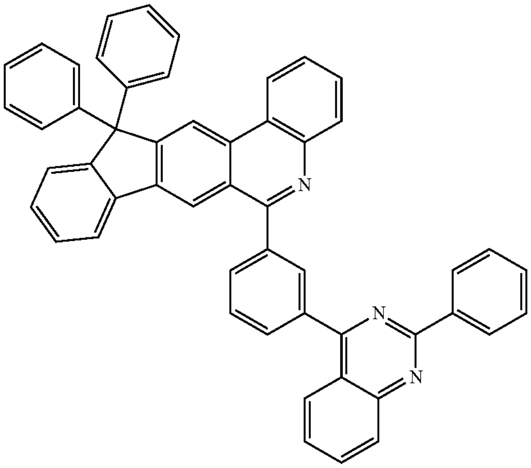
10-29
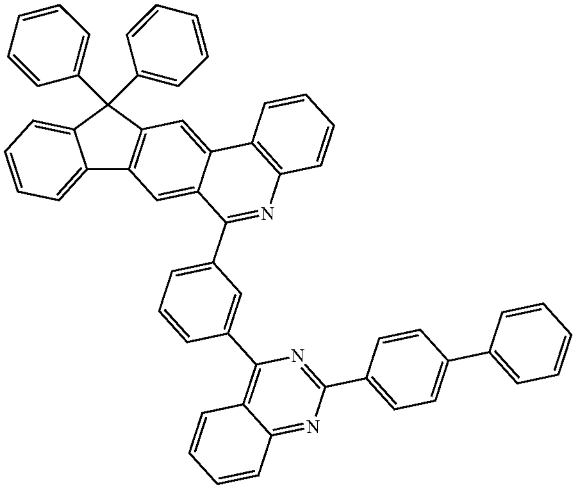

-continued
10-30
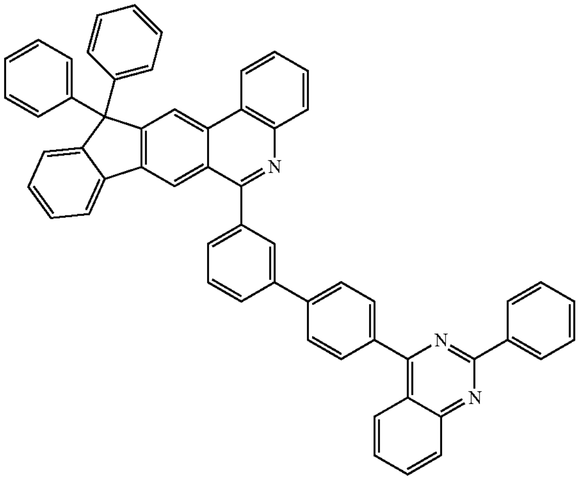
10-31
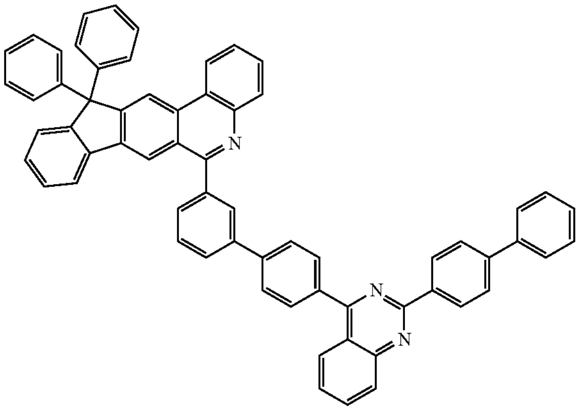
10-32
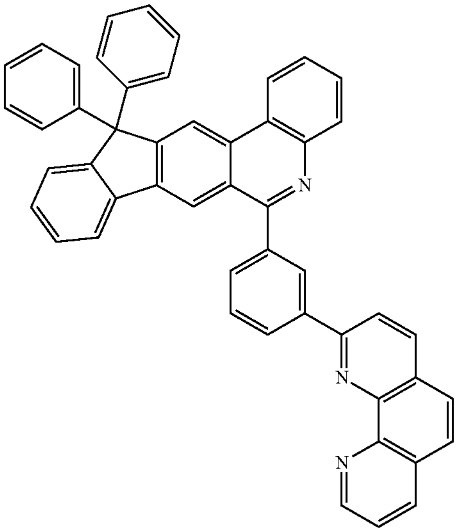
-continued
10-33
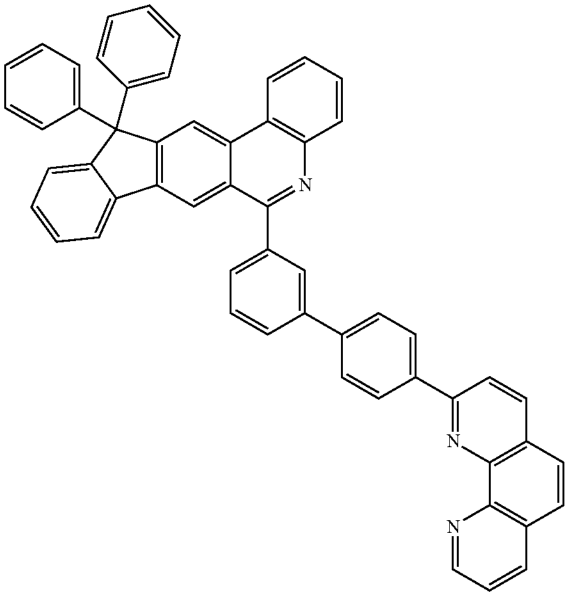
10-34
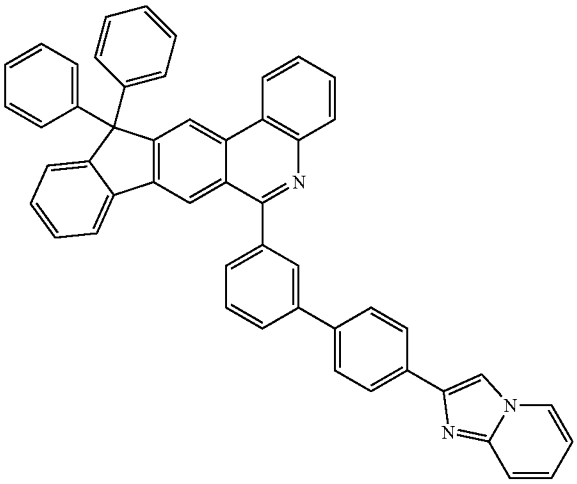

10-35
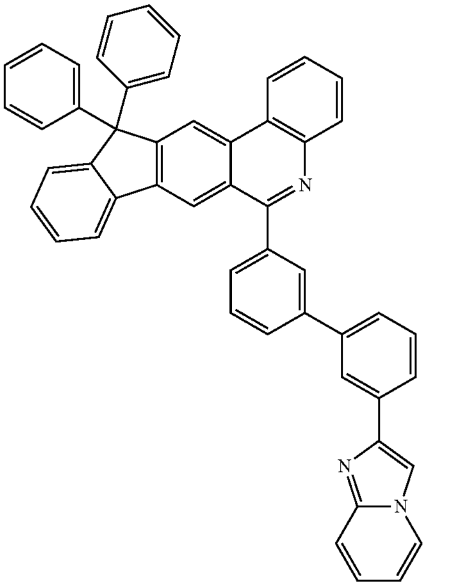
10-36
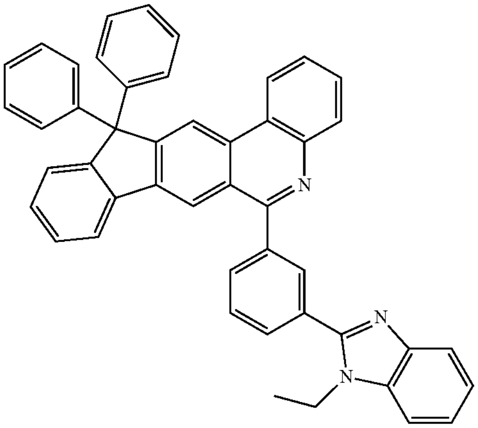
10-37
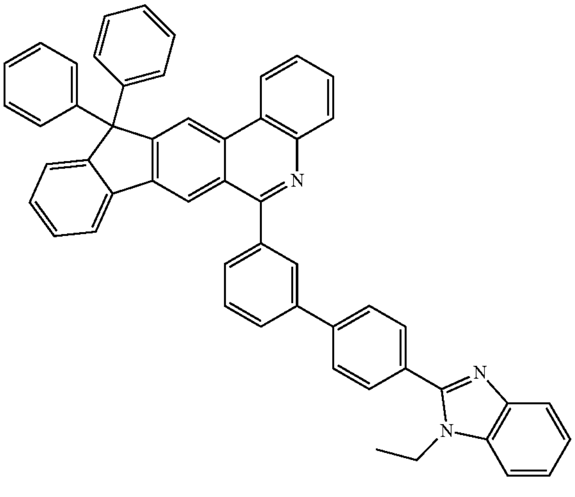
10-38
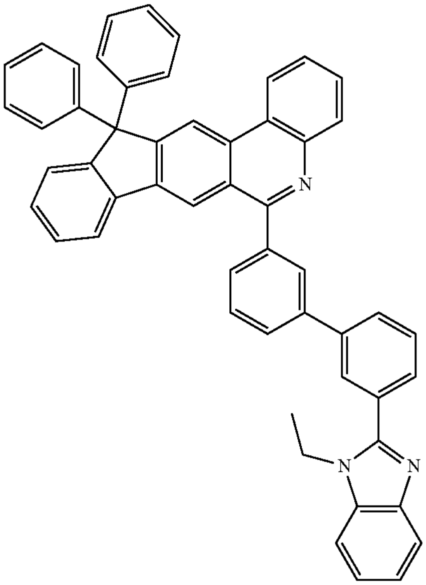
10-39
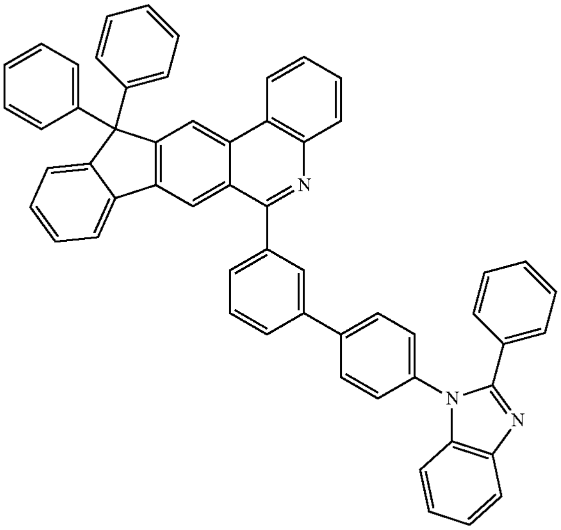

-continued
10-40
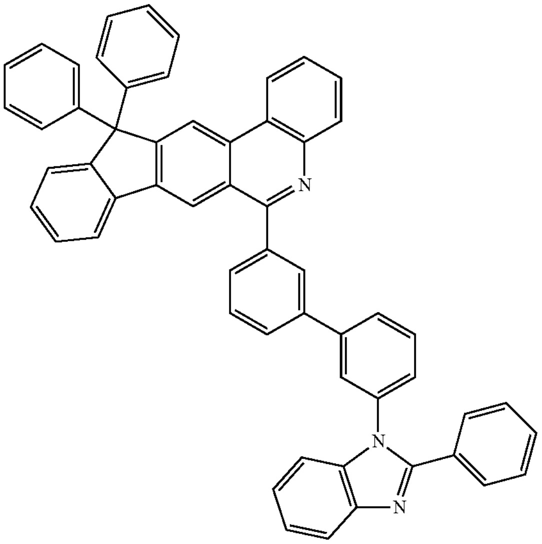
10-41
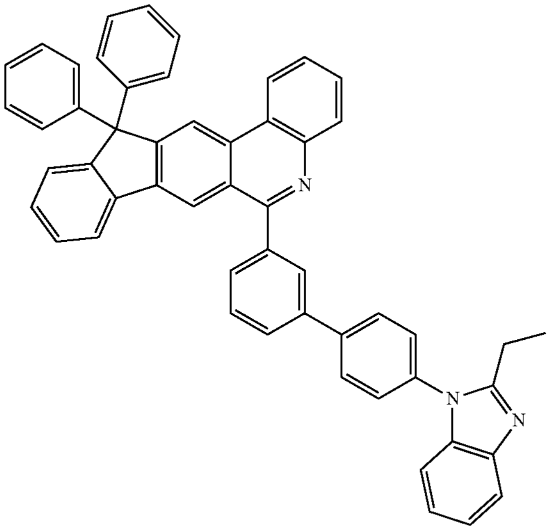
10-42
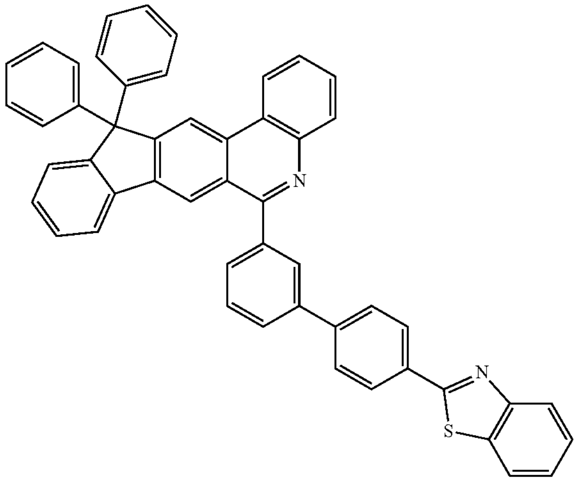
-continued
10-43
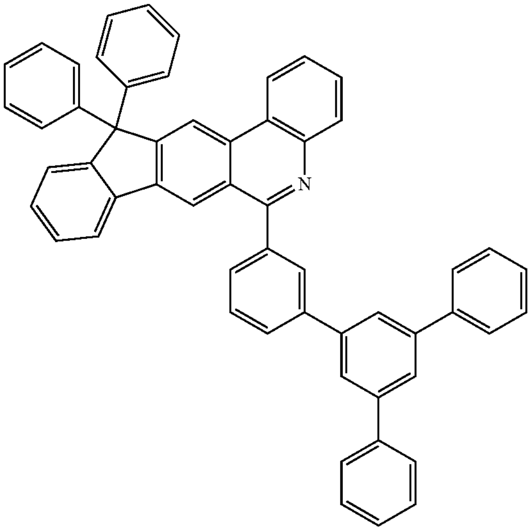
10-44
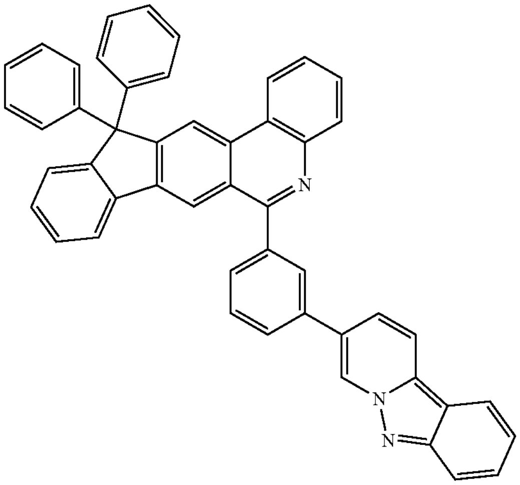
10-45
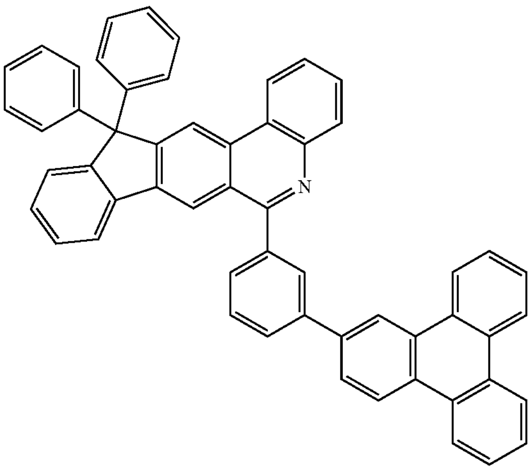

-continued
10-46
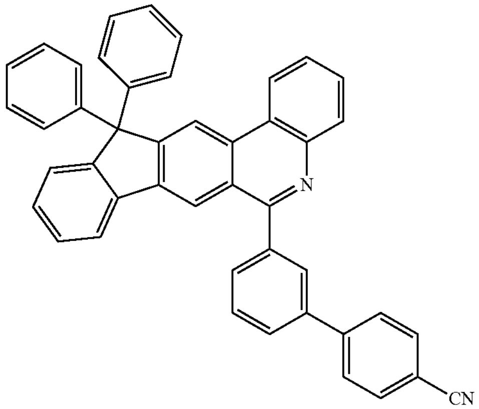
10-47
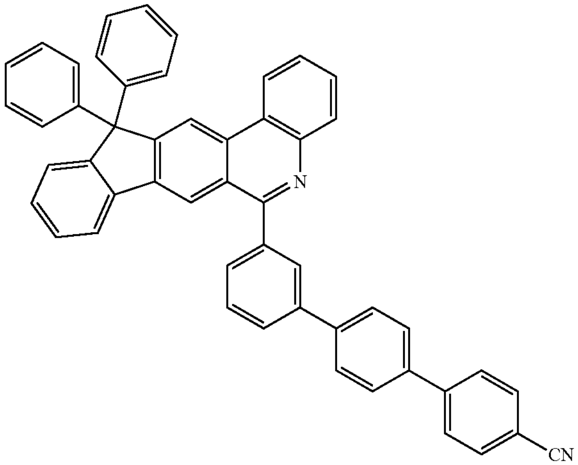
10-48
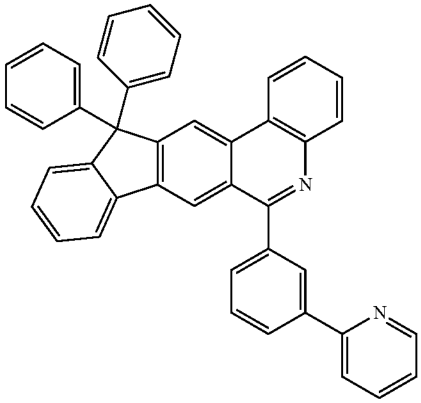
-continued
10-49
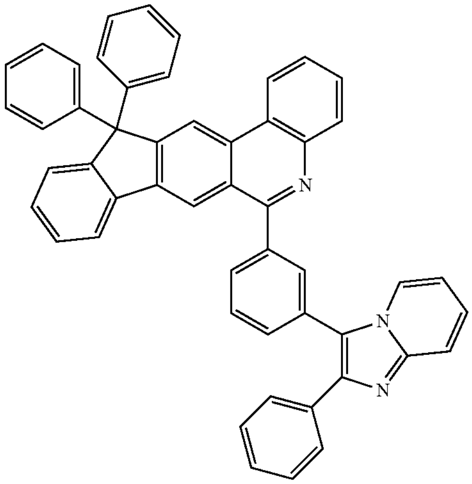
10-50
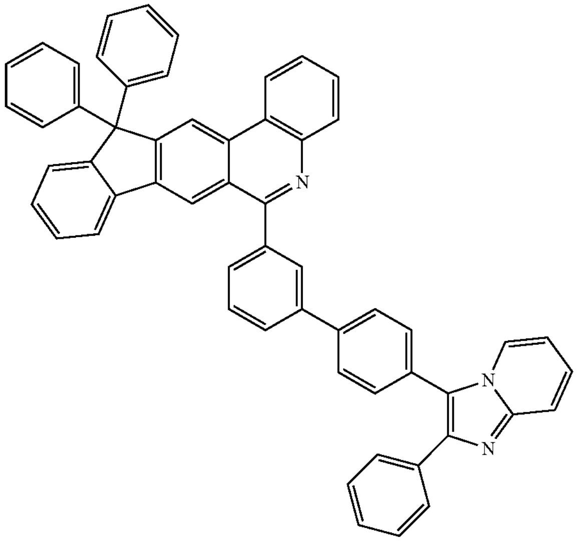
10-51
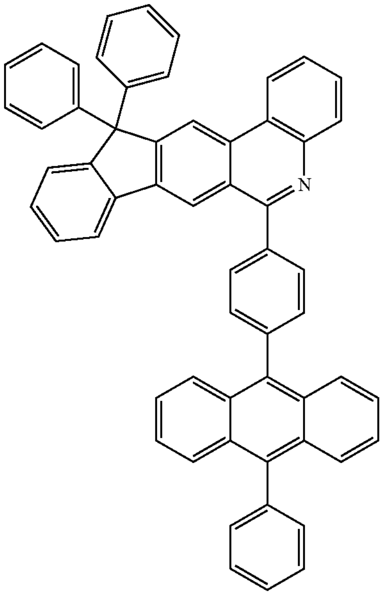

-continued
10-52
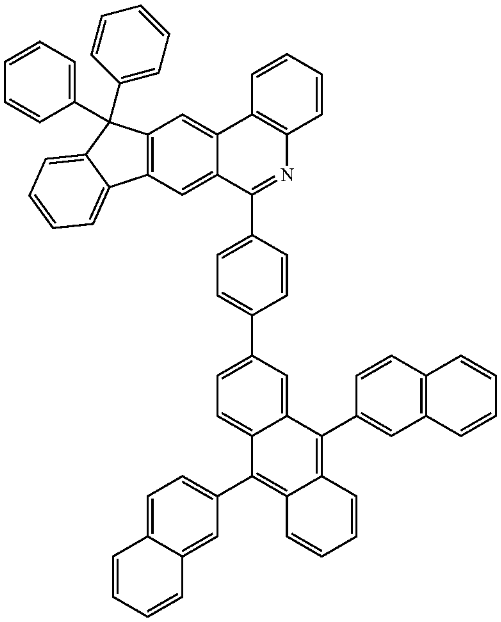
10-53
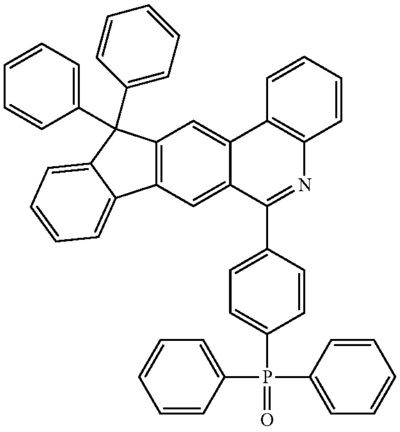
10-54
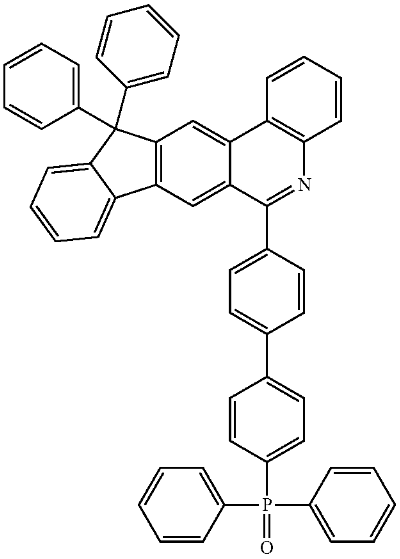
-continued
10-55
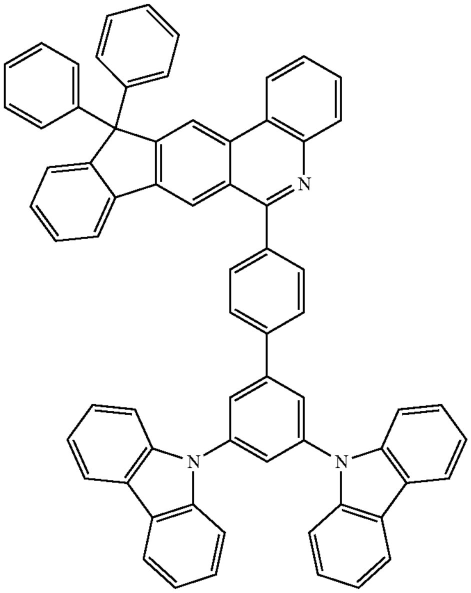
10-56
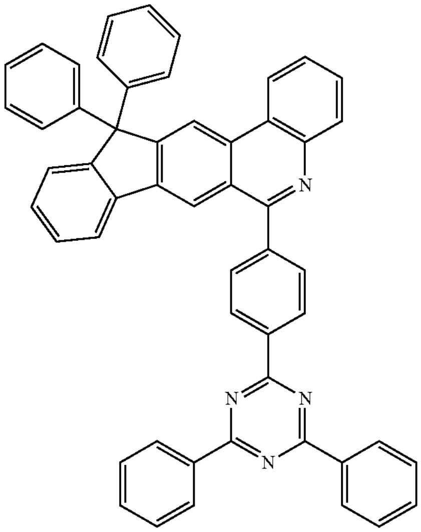

-continued
10-57
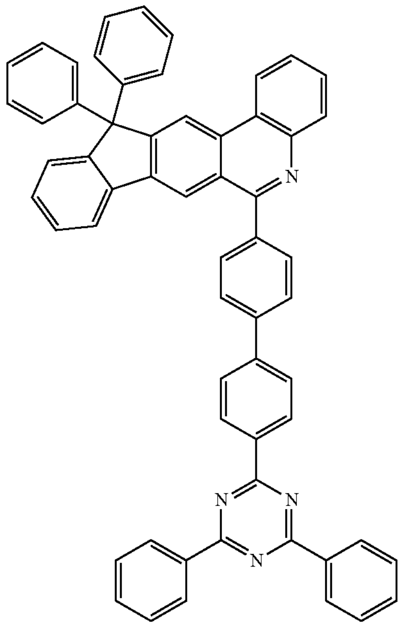
10-58
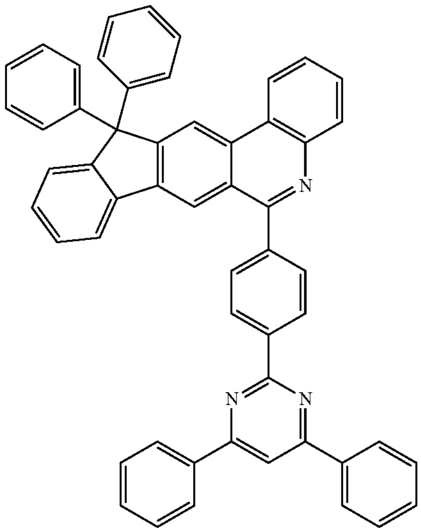
-continued
10-59
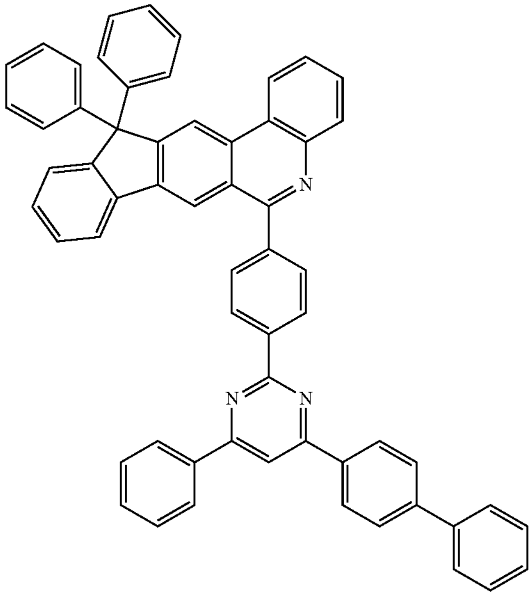
10-60
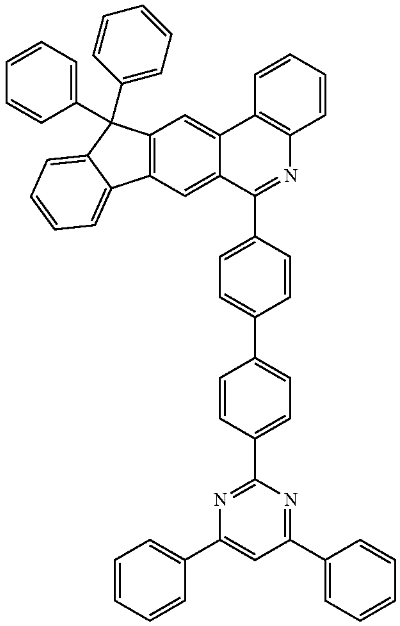

-continued
10-61
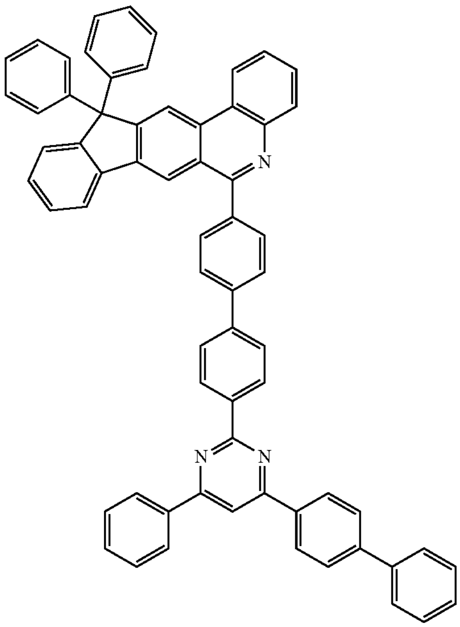
10-62
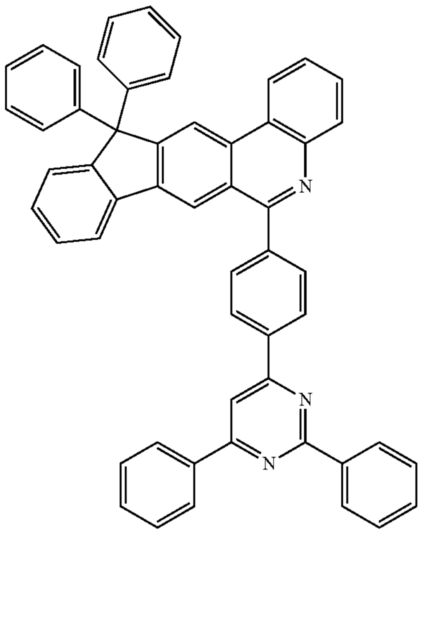
-continued
10-63
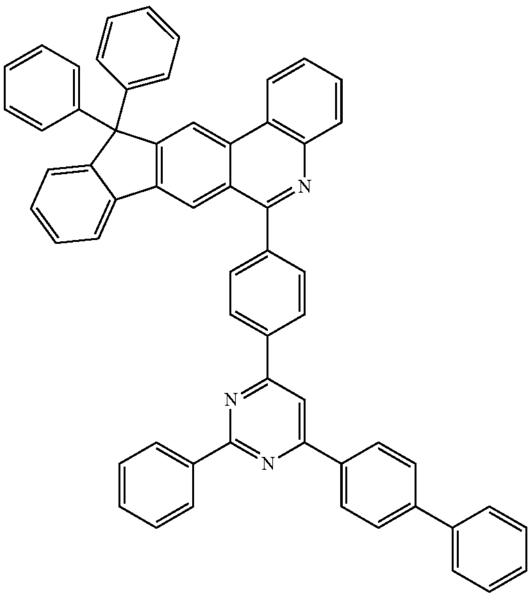
10-64
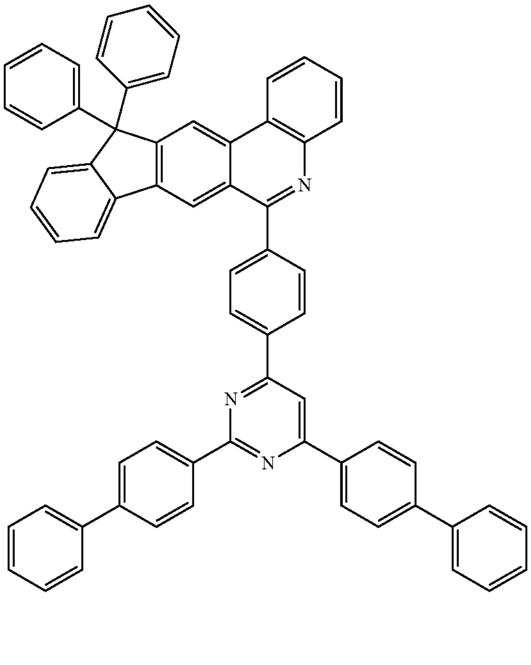

-continued
10-65
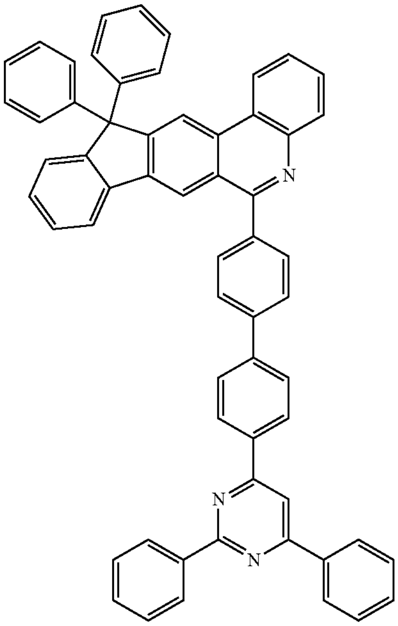
10-66
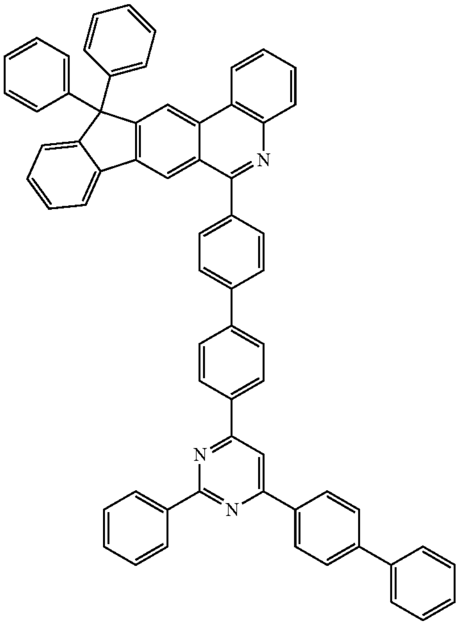
-continued
10-67
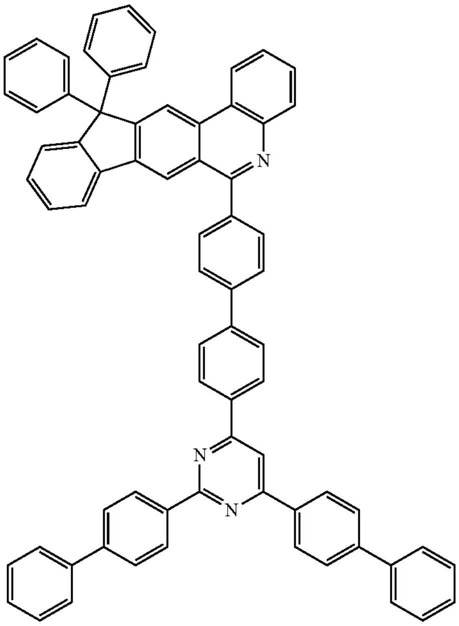
10-68
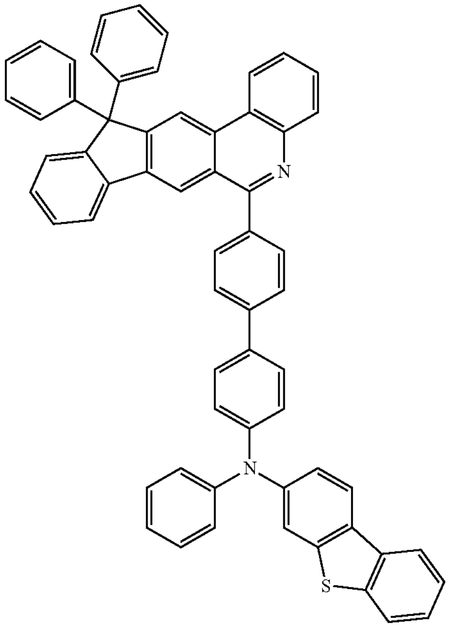

-continued
10-69
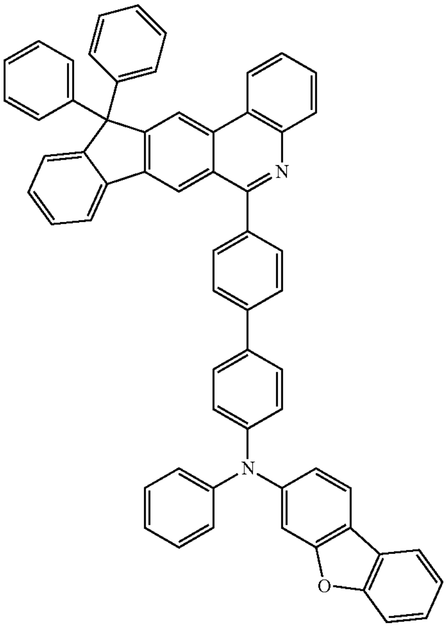
10-70
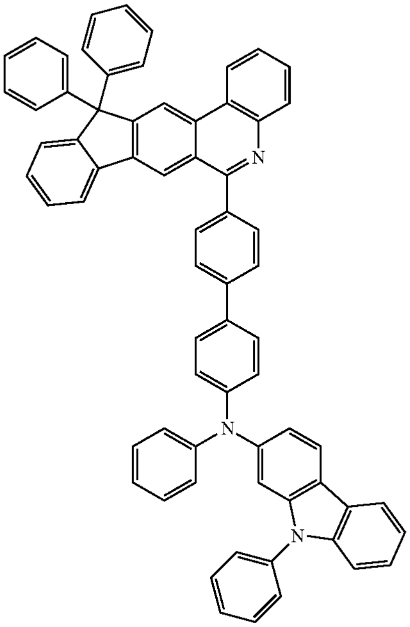
-continued
10-71
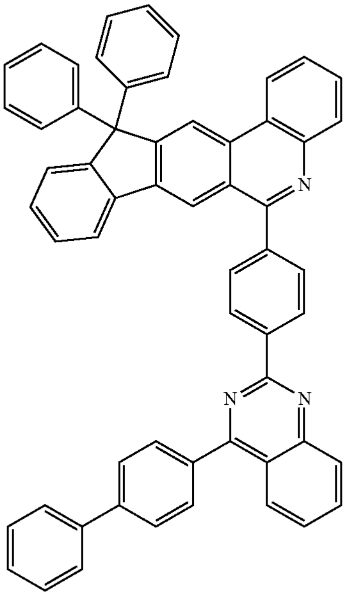
10-72
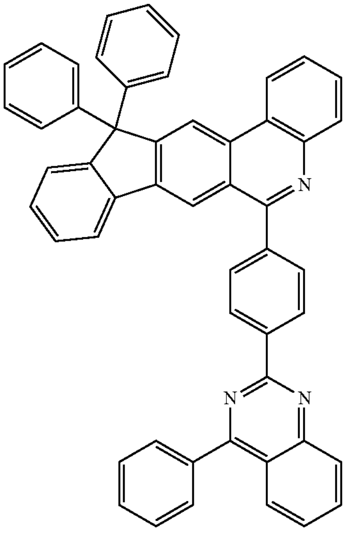

-continued
10-73
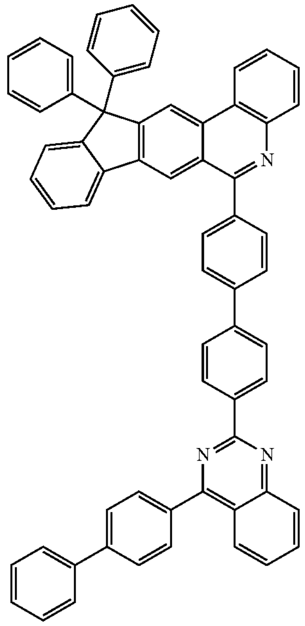
10-74
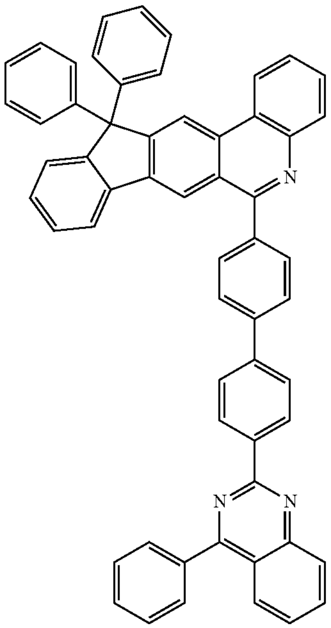
-continued
10-75
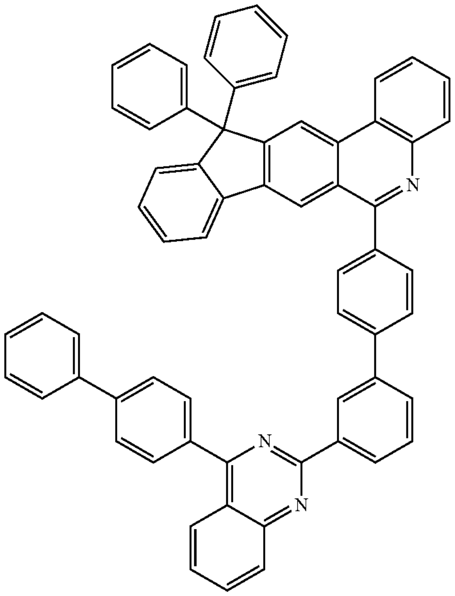
10-76
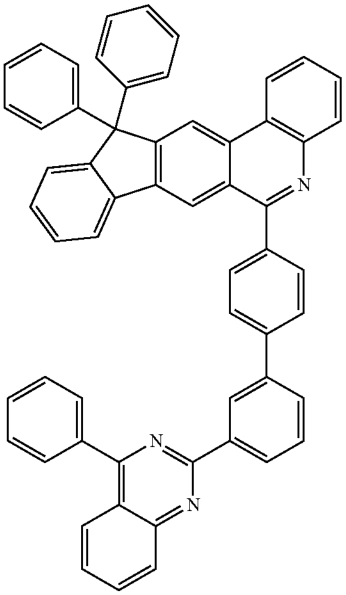

-continued
10-77
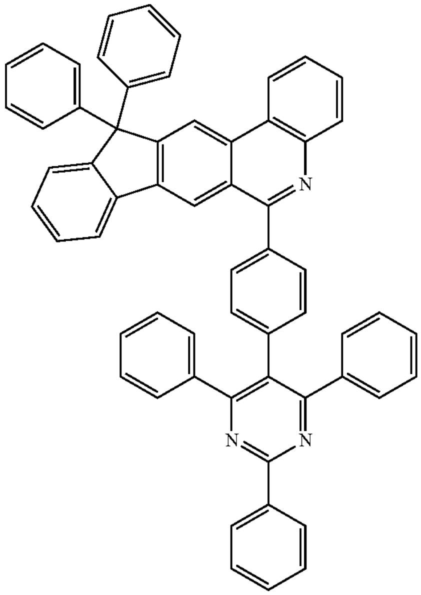
10-78
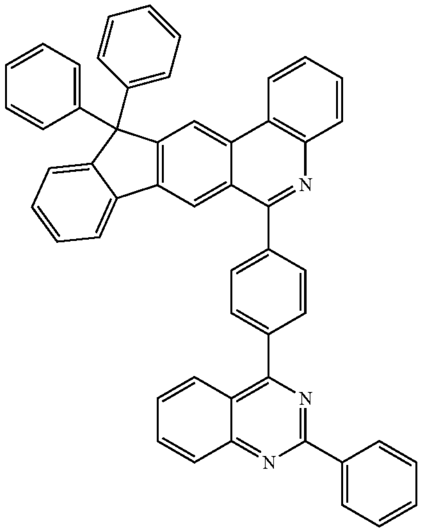
-continued
10-79
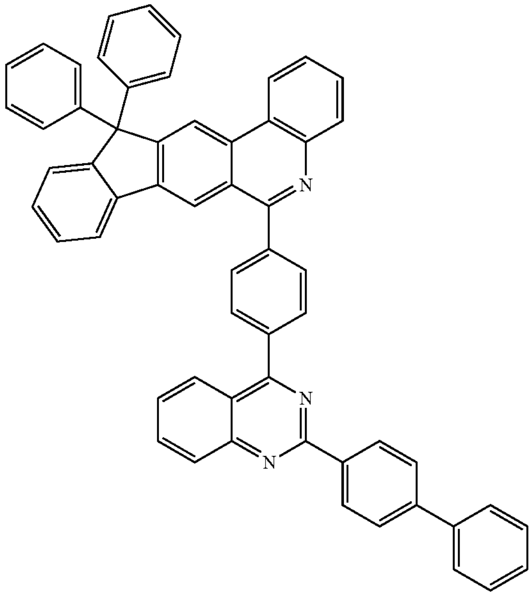
10-80
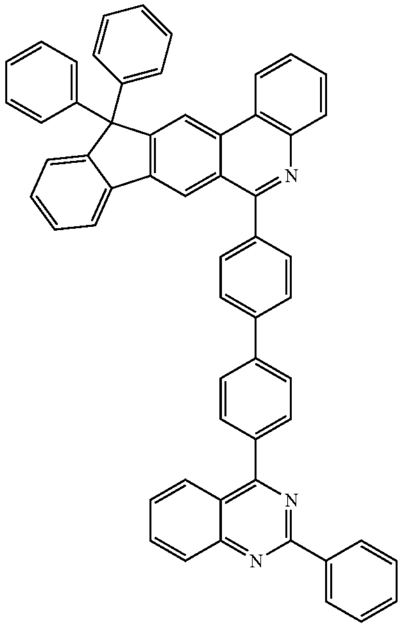

-continued
10-81
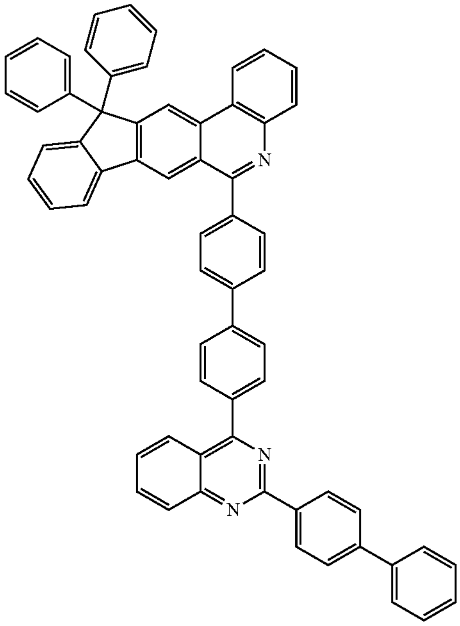
10-82
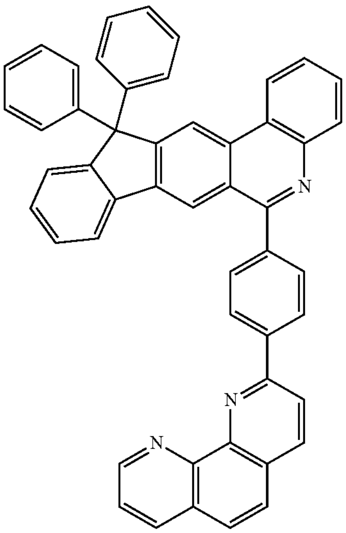
-continued
10-83
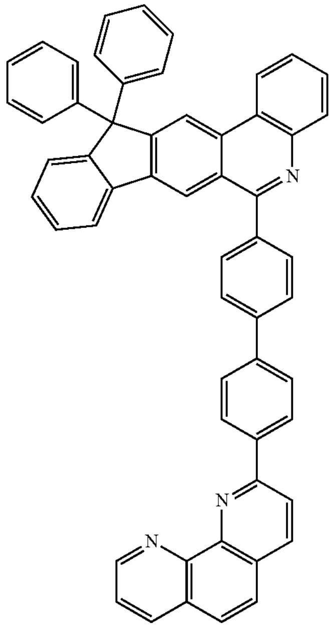
10-84
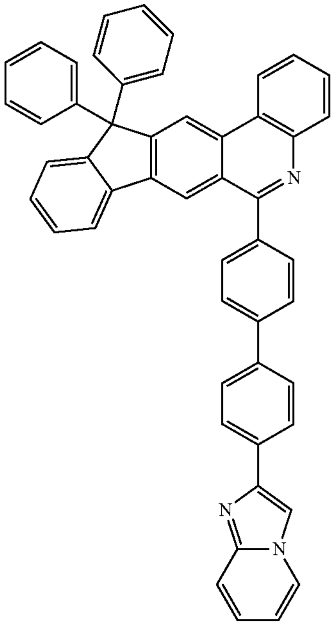

-continued
10-85
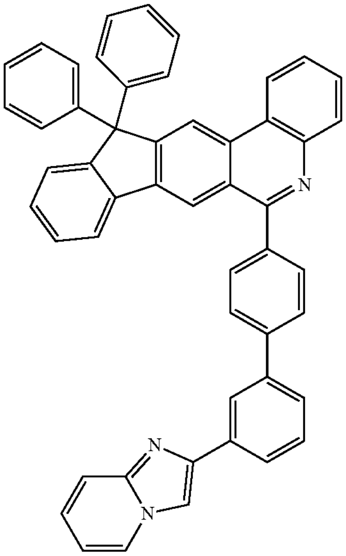
10-86
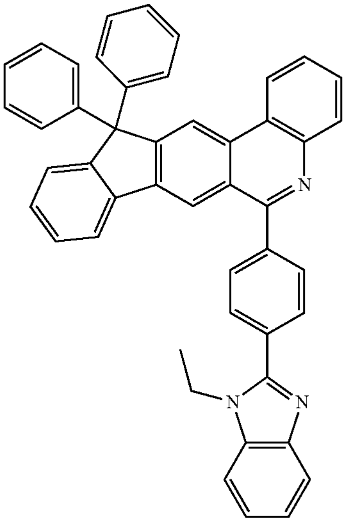
-continued
10-87
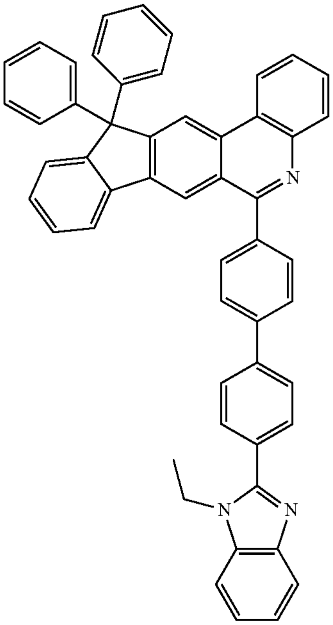
10-88
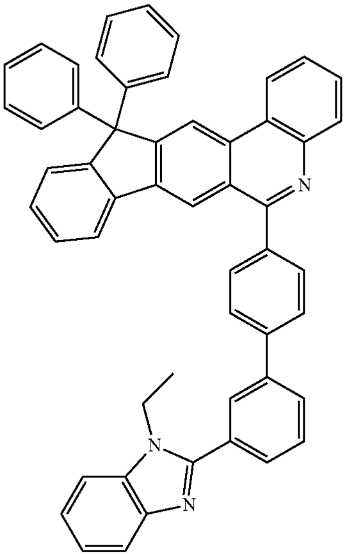

-continued
10-89
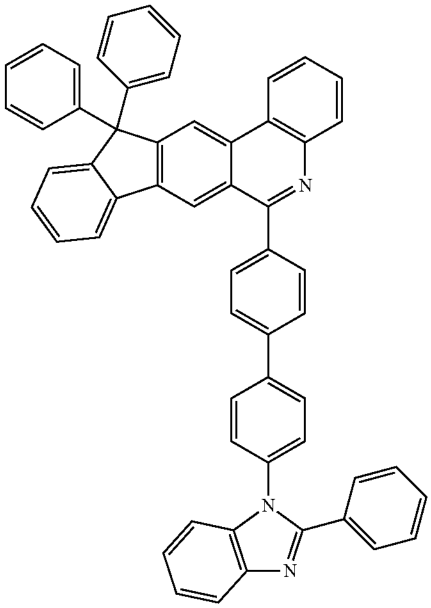
-continued
10-91
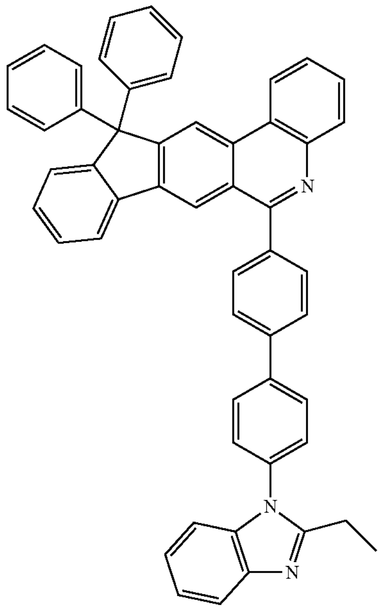
10-90
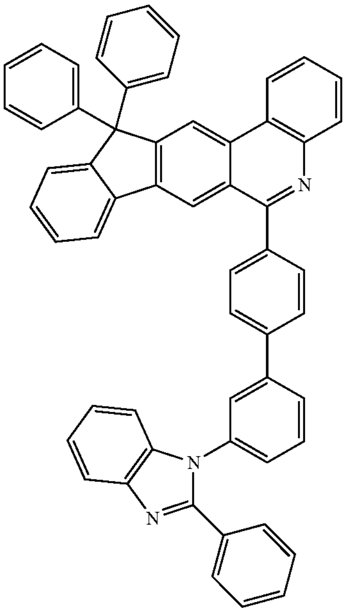
10-92
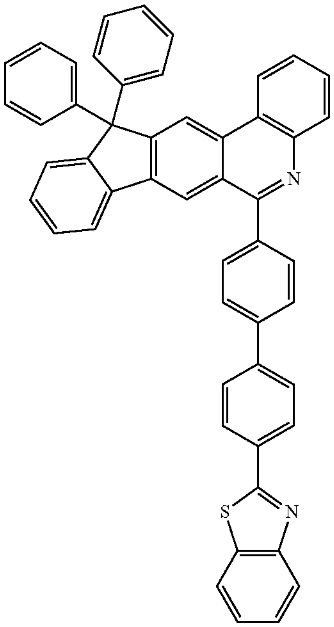

-continued
10-93
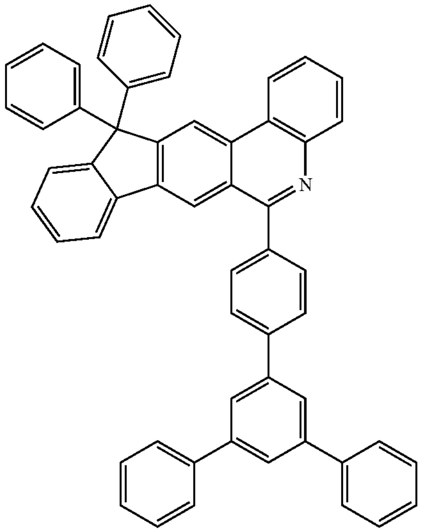
10-94
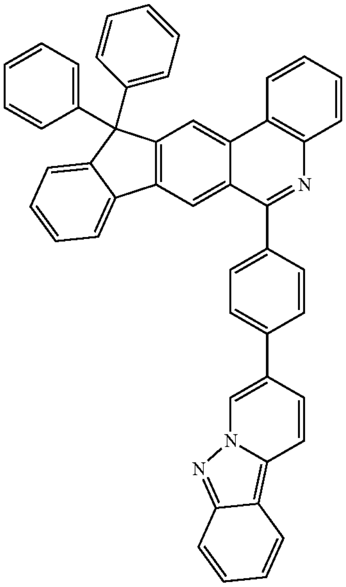
-continued
10-95
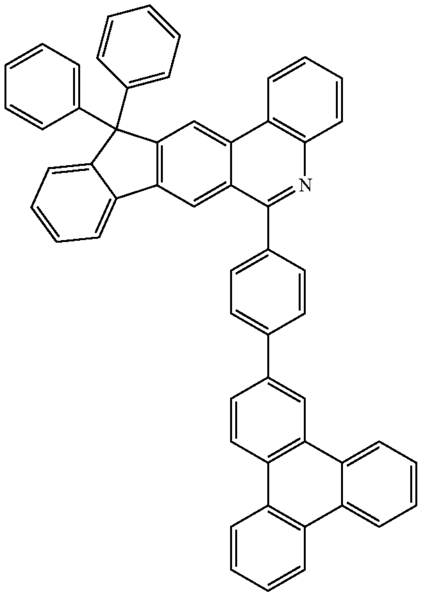
10-96
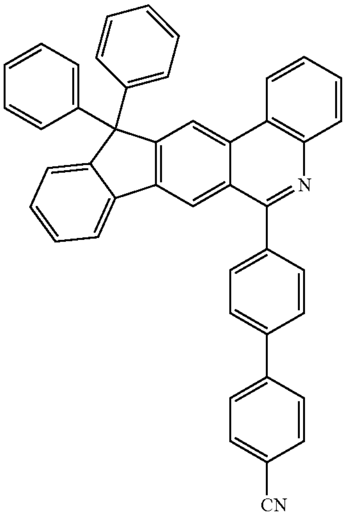

-continued
10-97
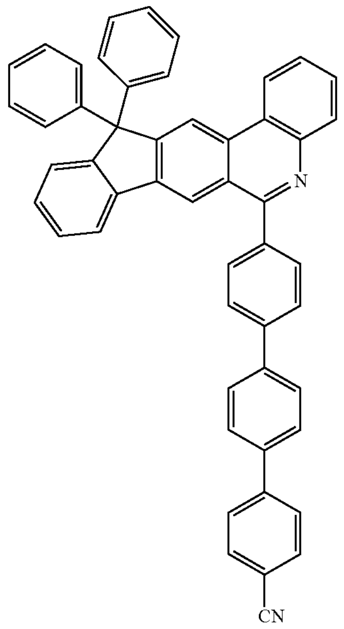
10-98
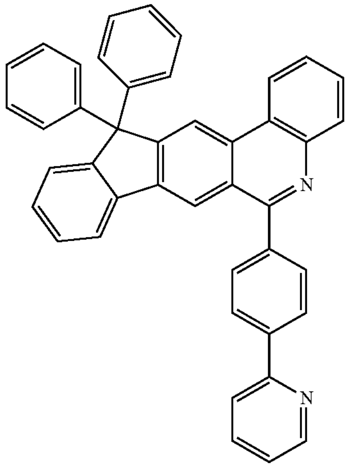
10-99
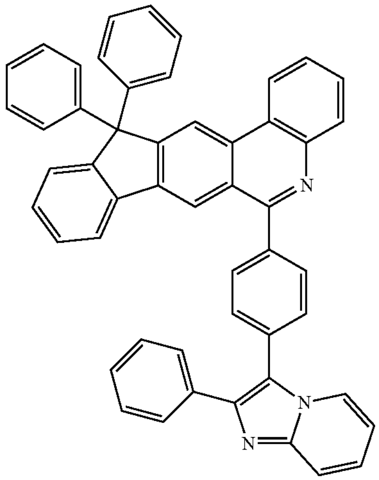
-continued
10-100
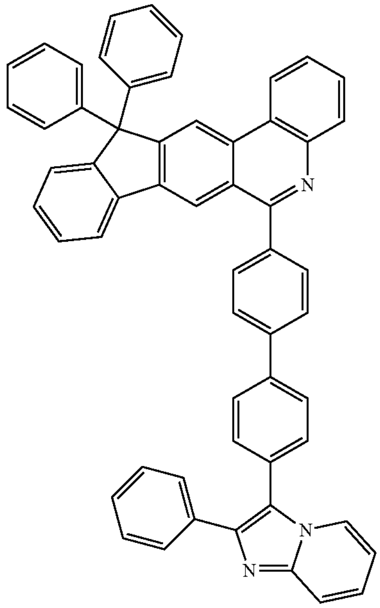
11-1
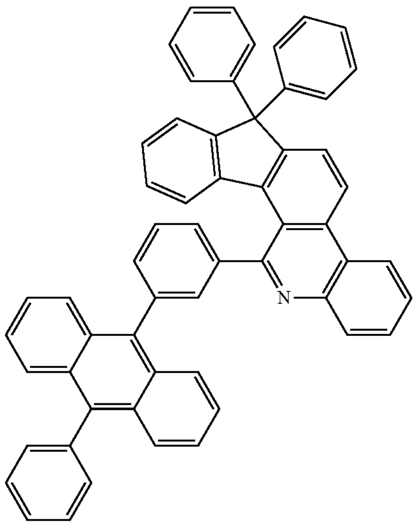

-continued
11-2
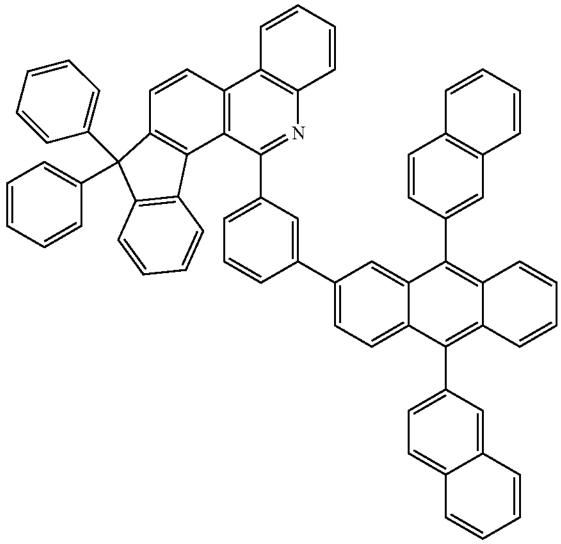
11-3
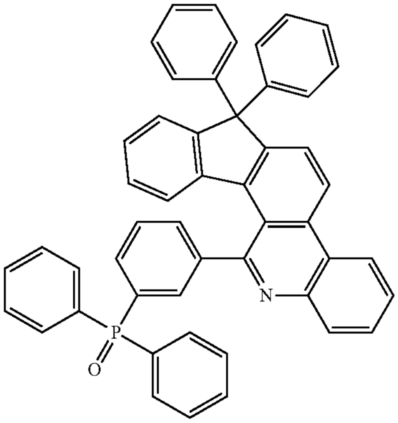
11-4
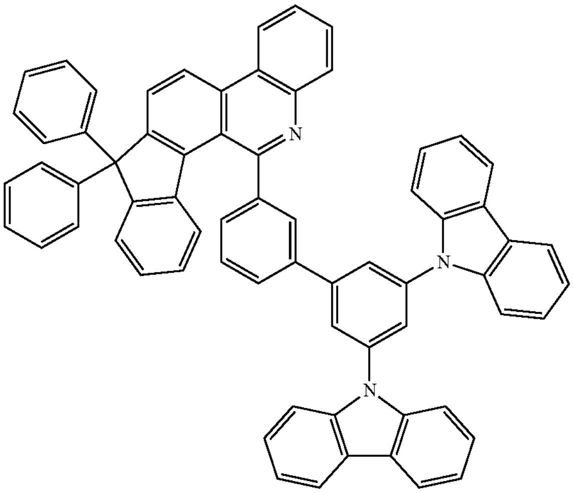
-continued
11-5
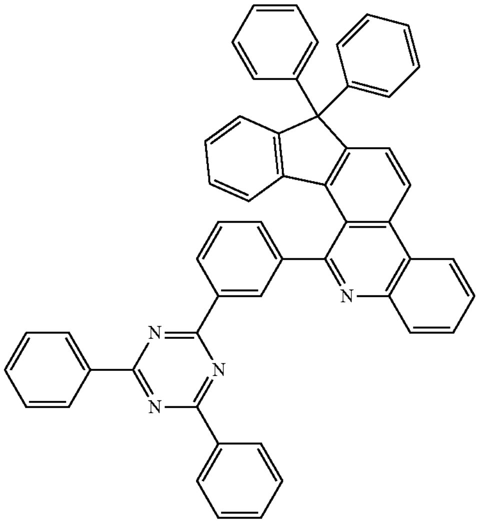
11-6
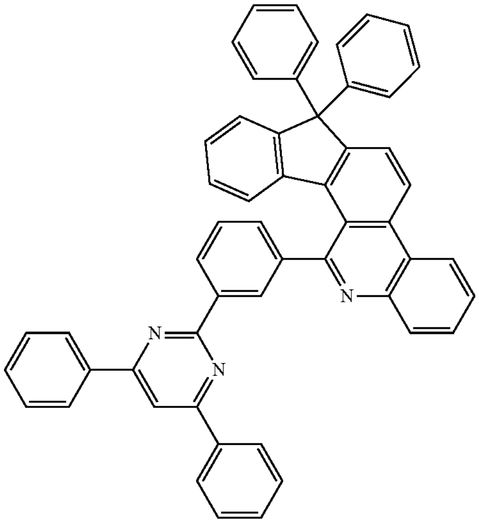

-continued
11-7
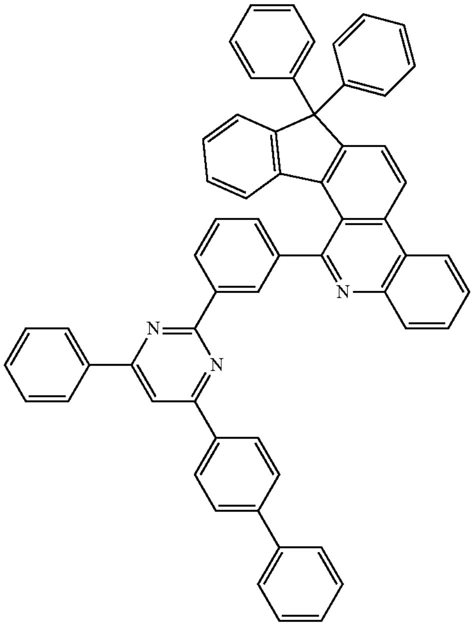
11-8
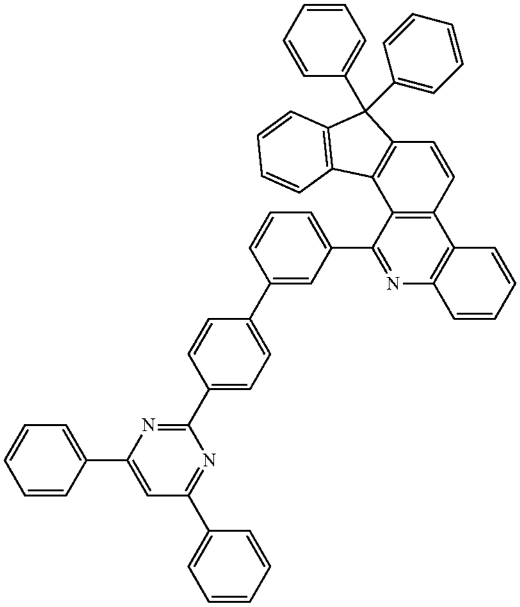
-continued
11-9
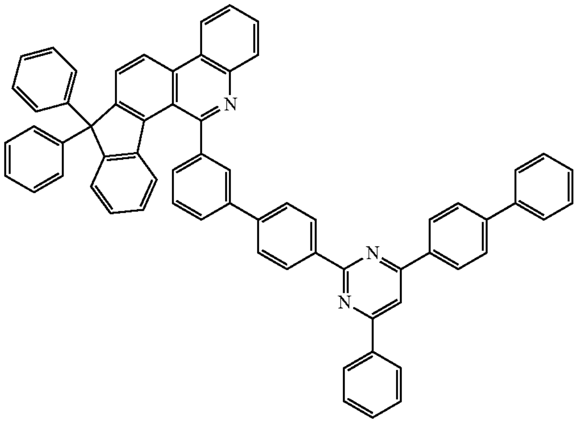
11-10
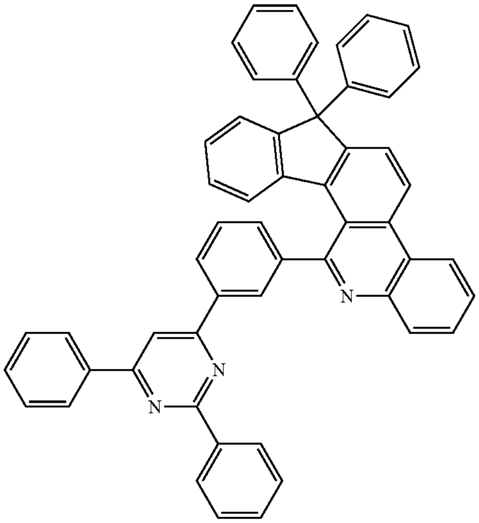
11-11
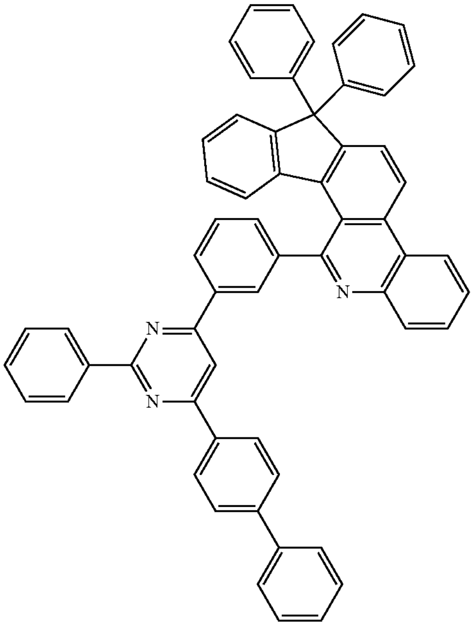

-continued
11-12
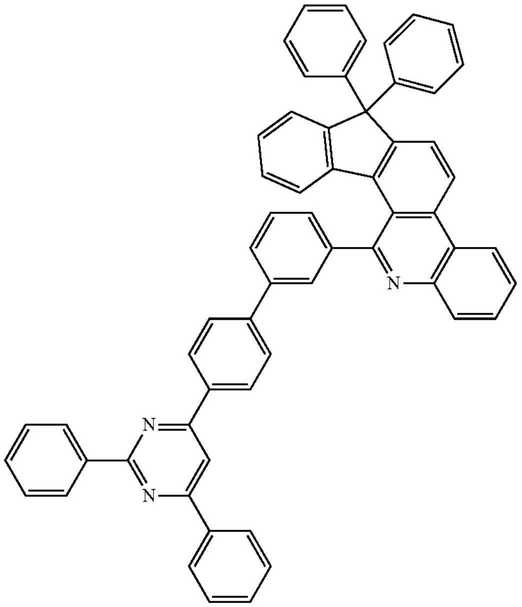
11-13
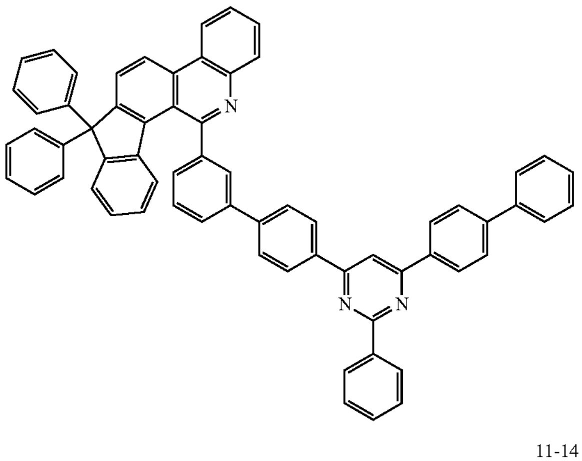
11-14
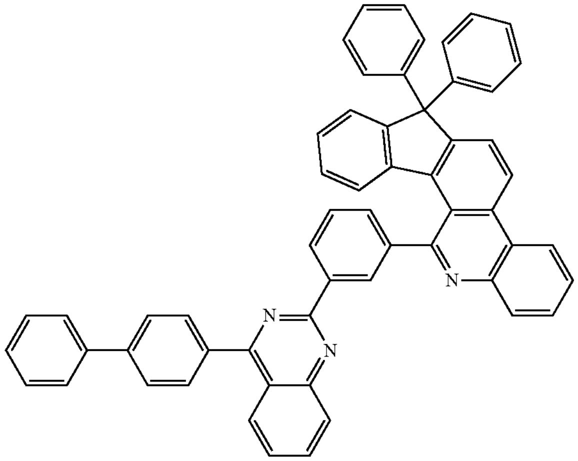
-continued
11-15
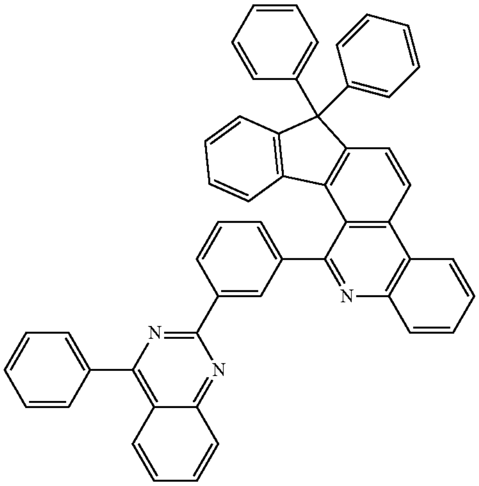
11-16
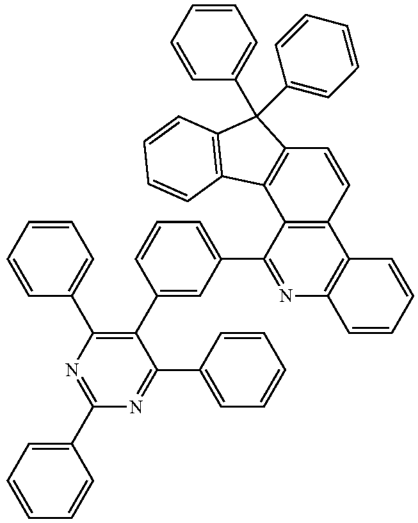
11-17
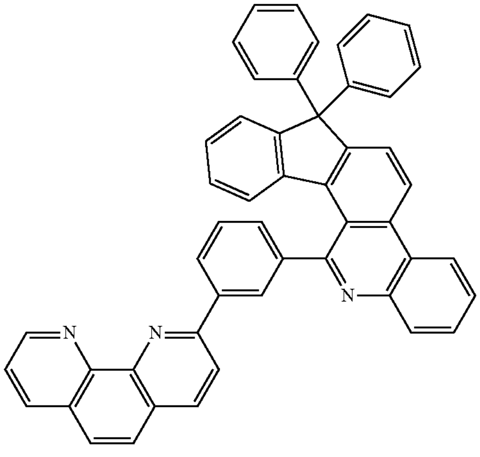

11-18
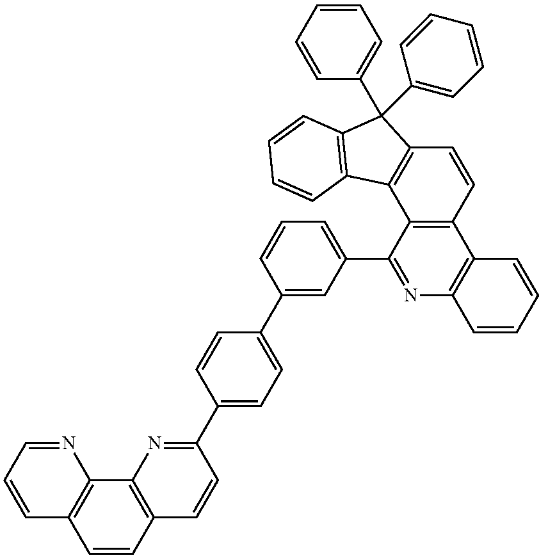
11-19
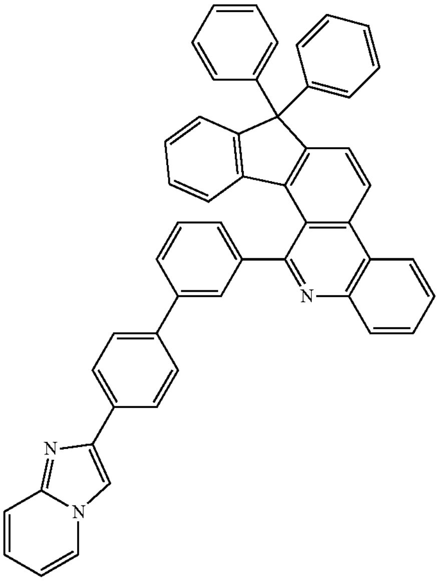
11-20
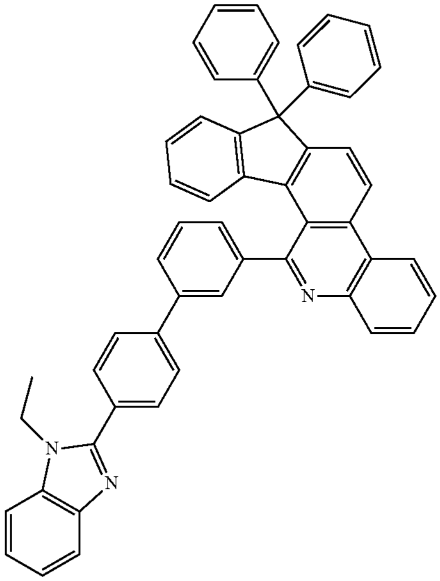
11-21
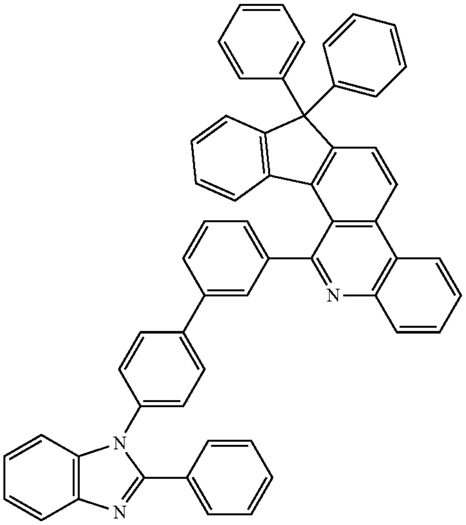
11-22
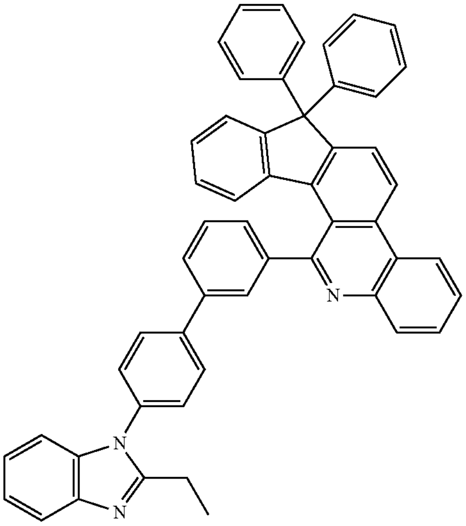

-continued
11-23
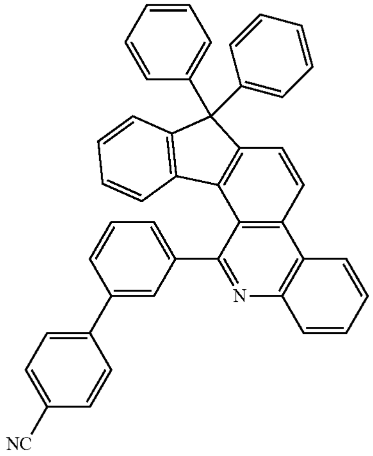
11-24
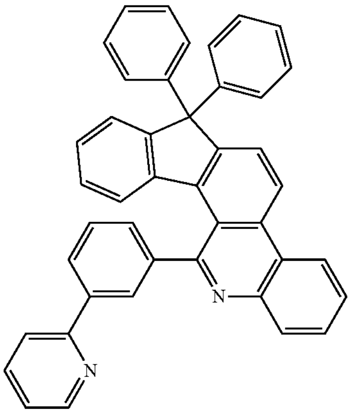
11-25
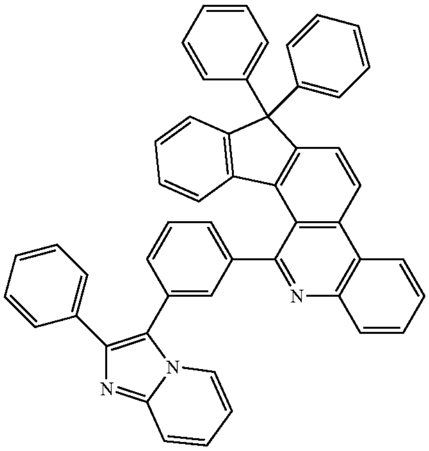
-continued
11-26
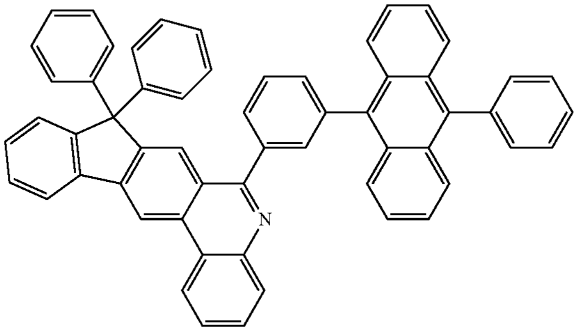
11-27
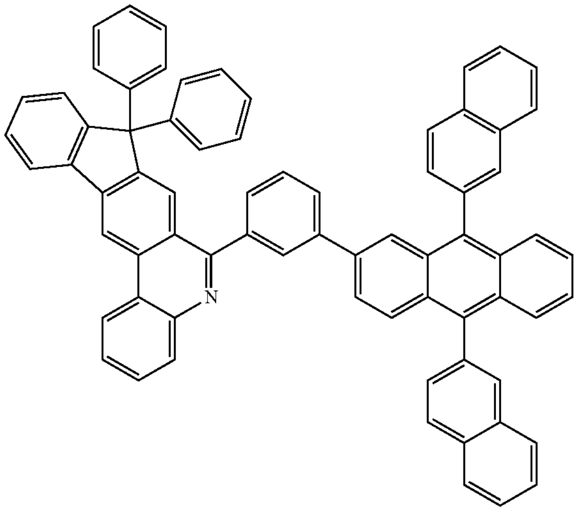
11-28
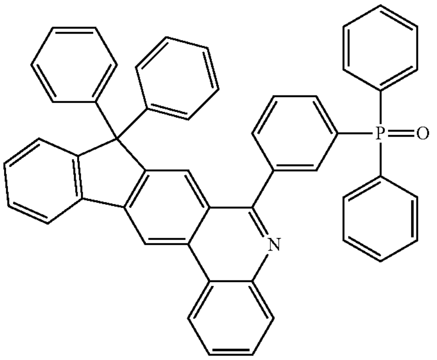

-continued
11-29
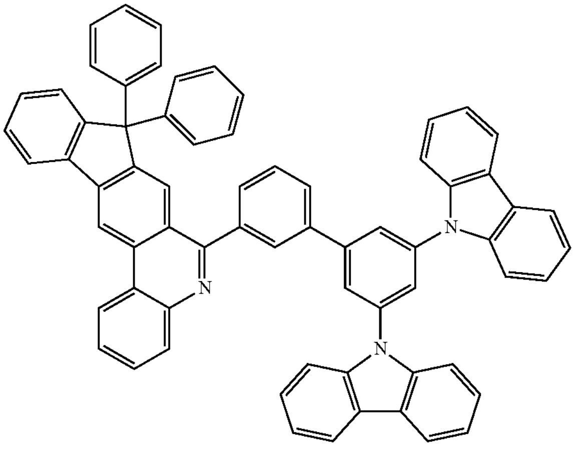
11-30
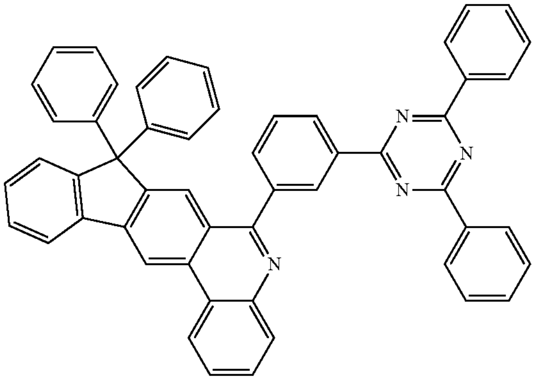
11-31
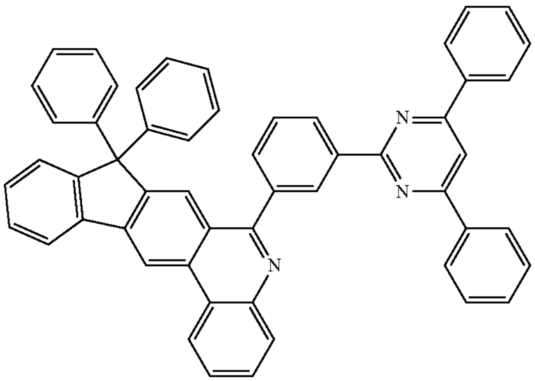
-continued
11-32
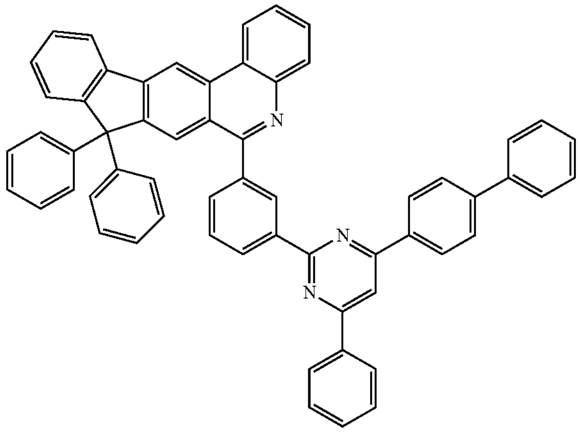
11-33
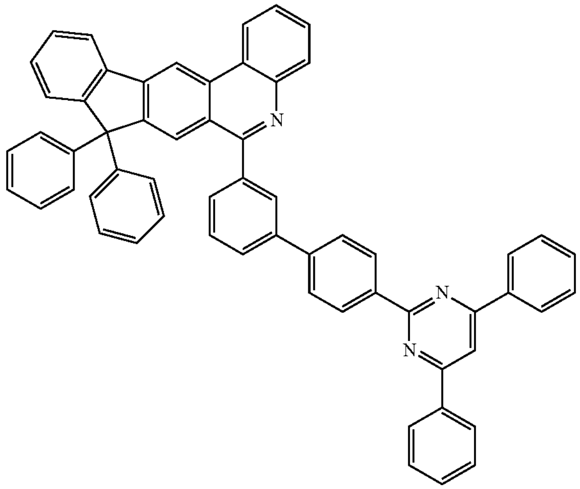
11-34
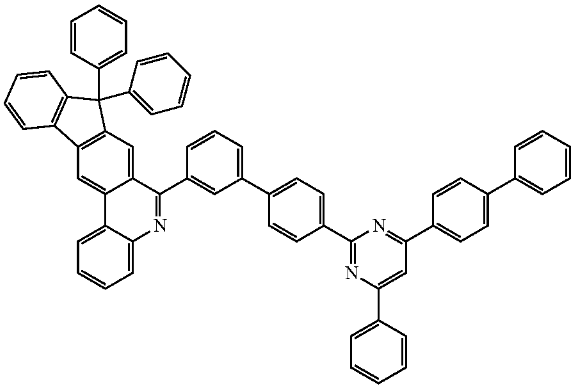

-continued
11-35
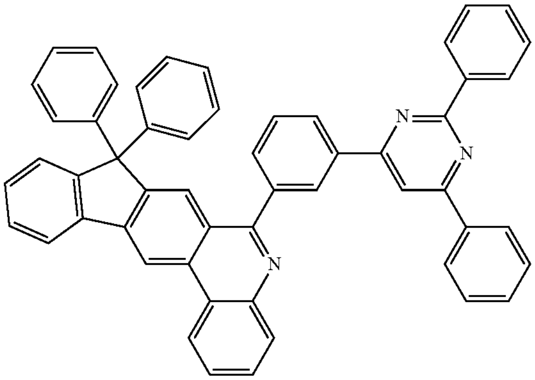
11-36
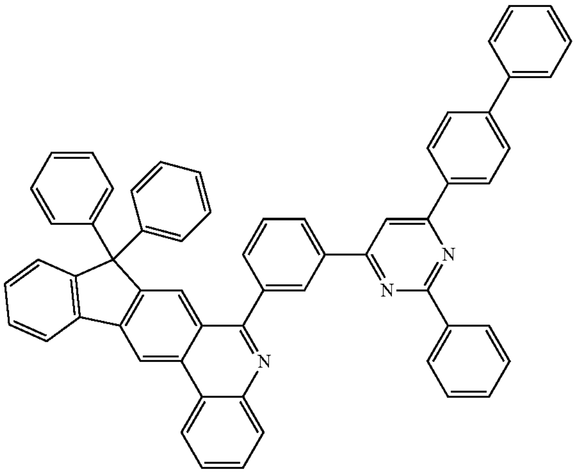
11-37
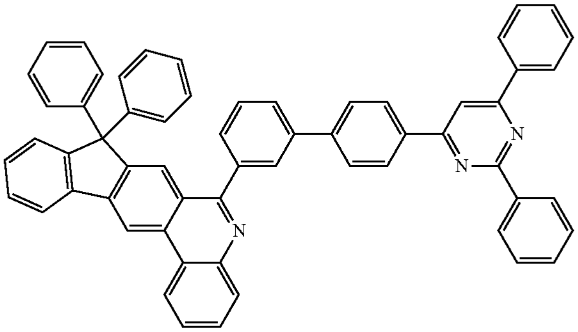
-continued
11-38
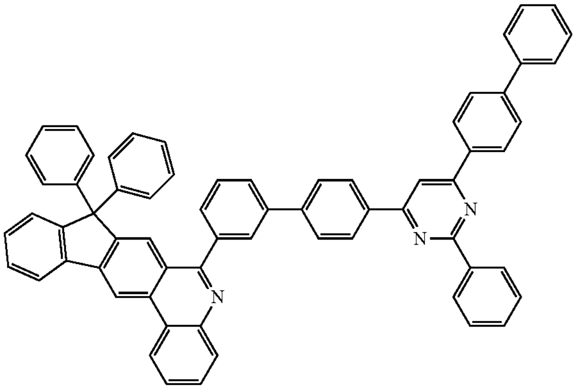
11-39
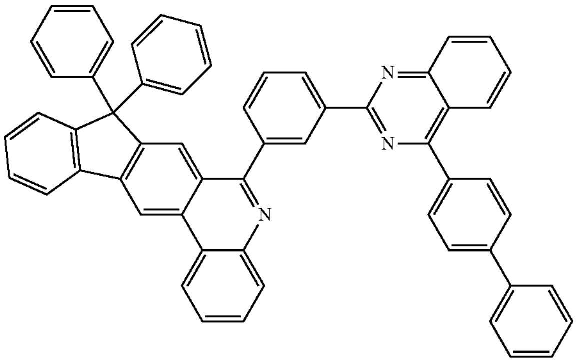
11-40
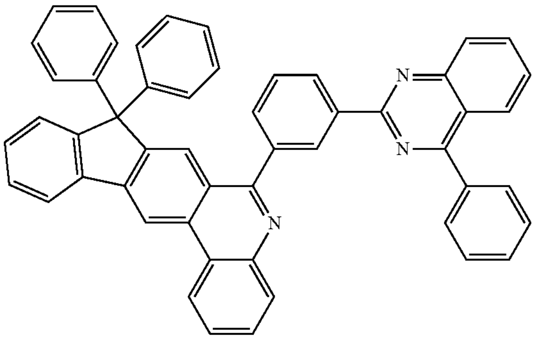
11-41
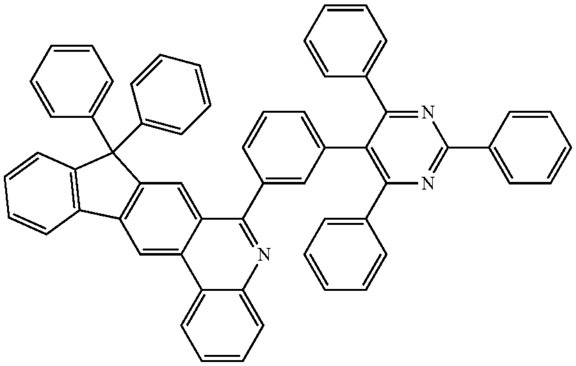

-continued
11-42
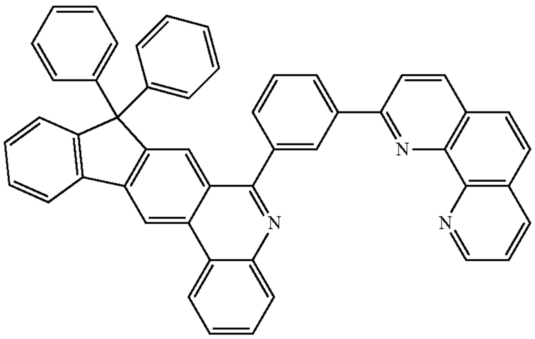
11-43
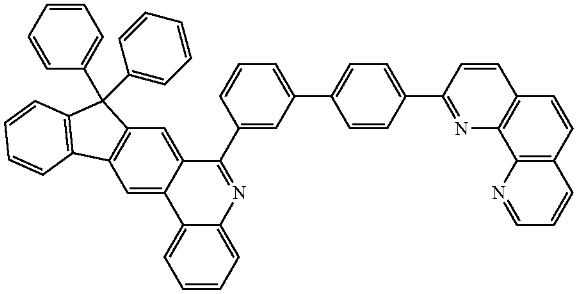
11-44
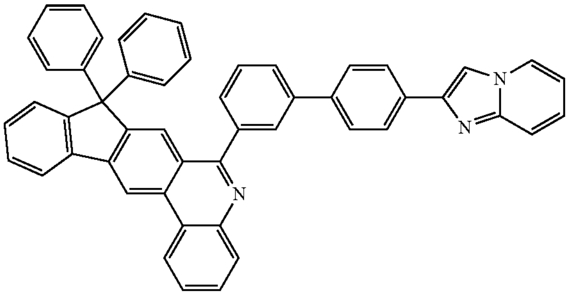
11-45
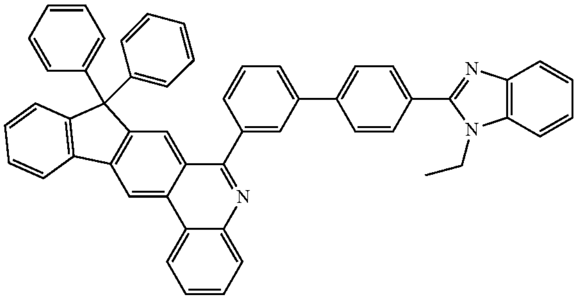
-continued
11-46
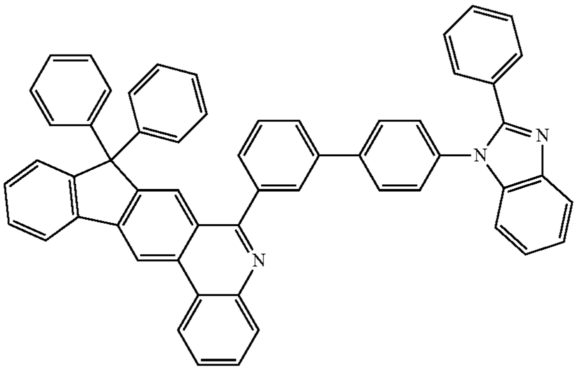
11-47
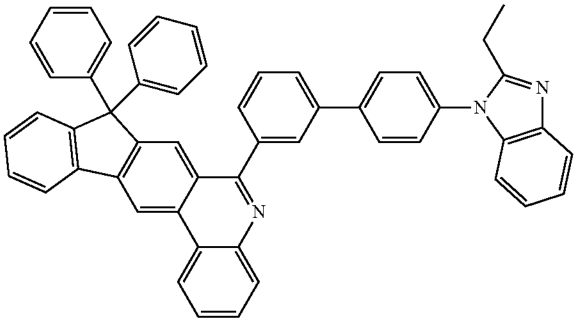
11-48
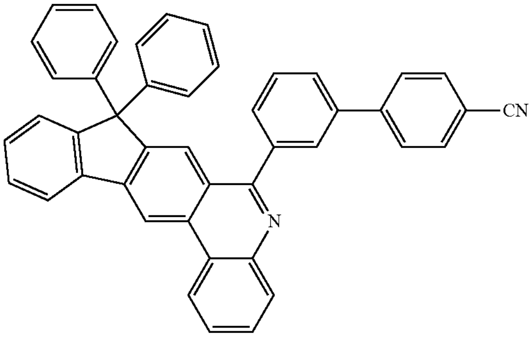
11-49
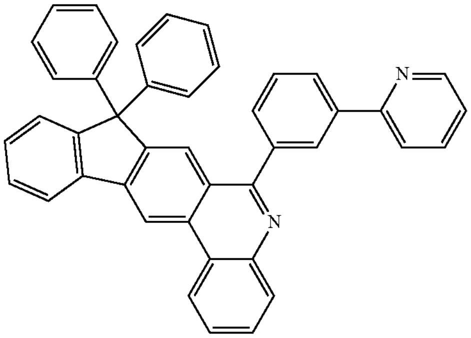

-continued
11-50
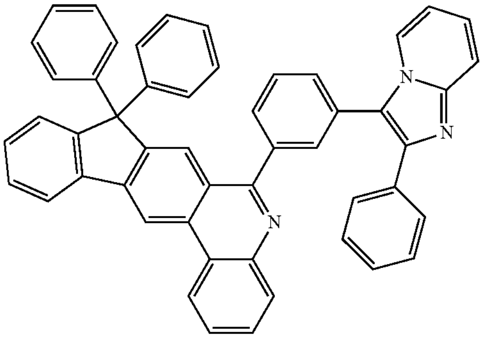
11-51
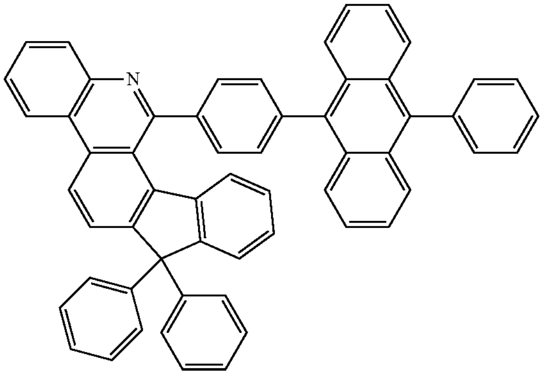
11-52
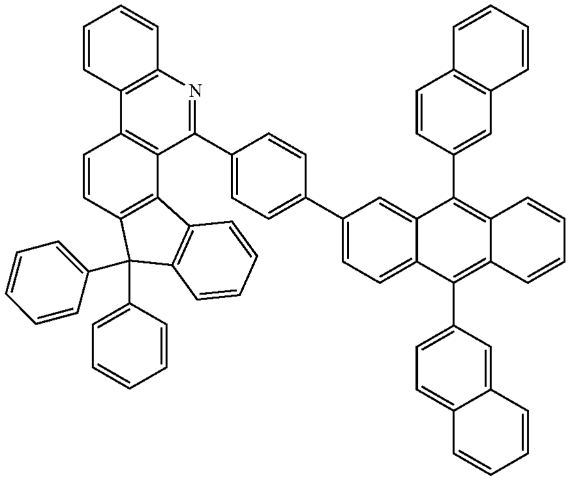
11-53
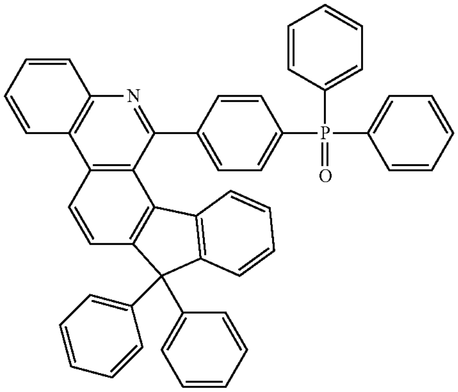
-continued
11-54
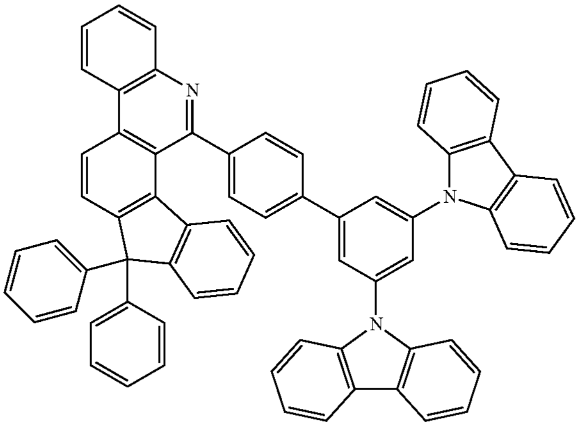
11-55
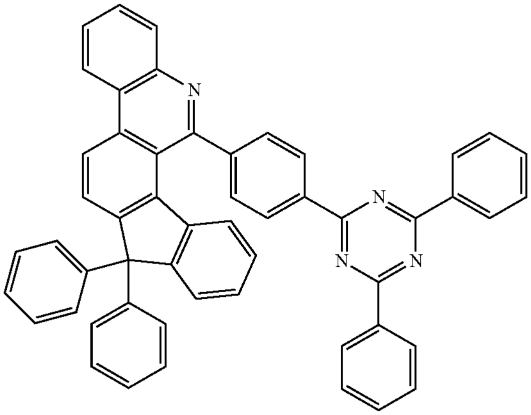
11-56
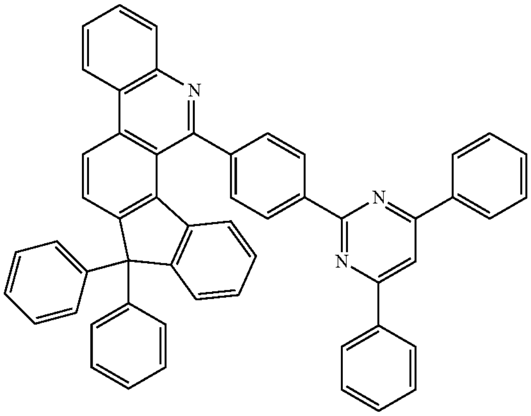

-continued
11-57
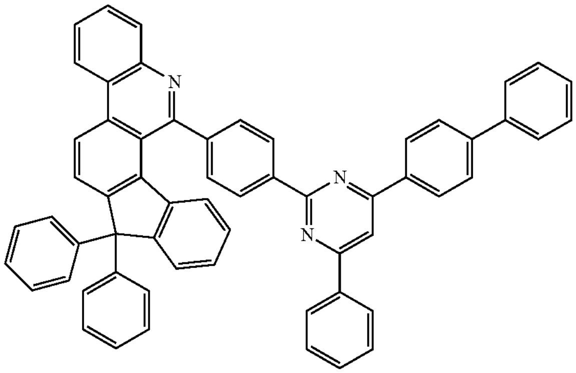
11-58
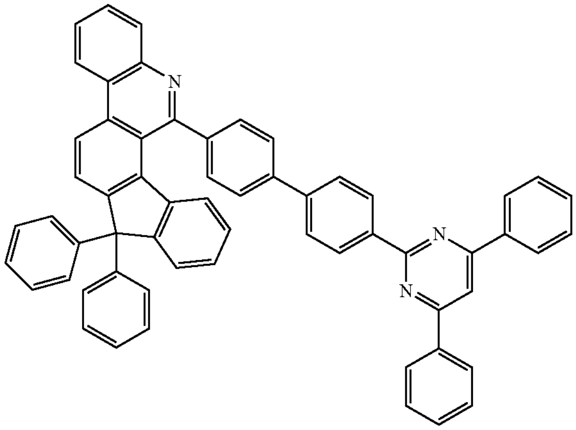
11-59
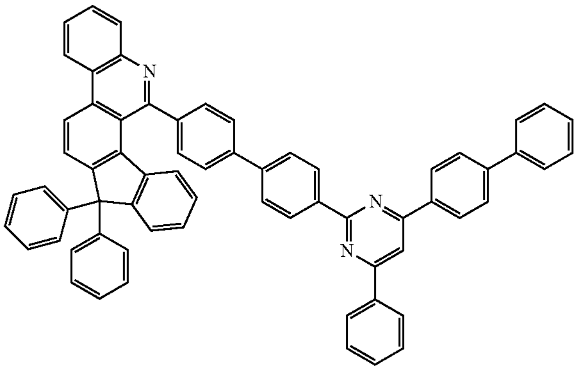
-continued
11-60
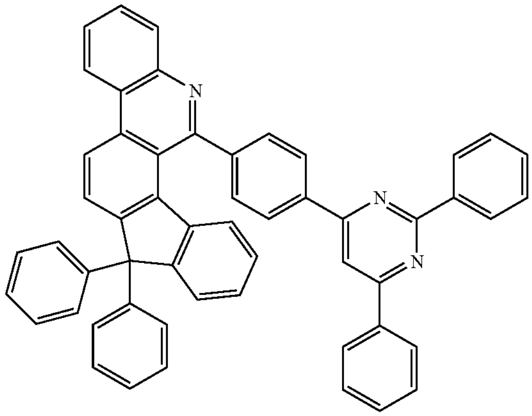
11-61
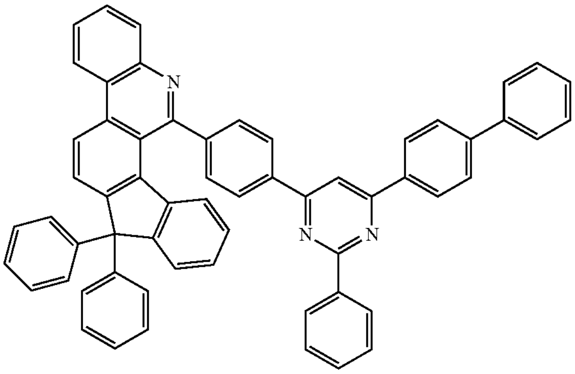
11-62
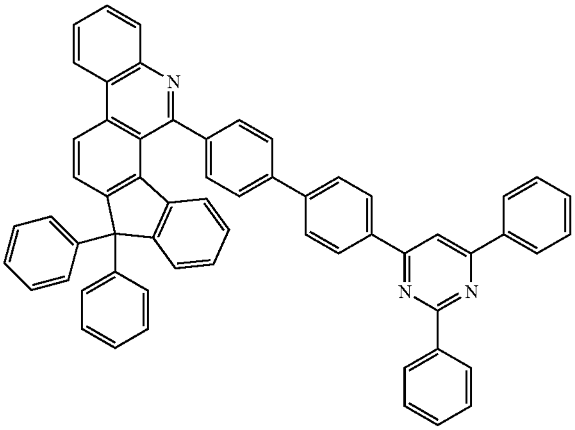

-continued
11-63
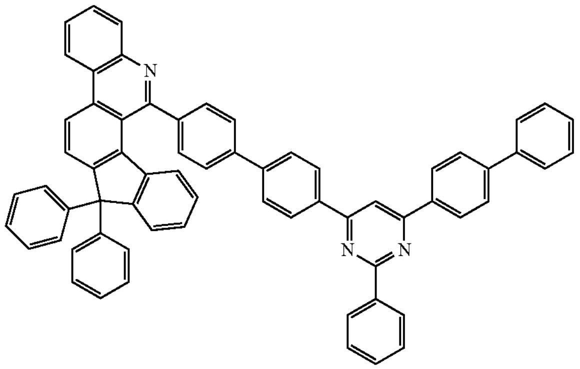
11-64
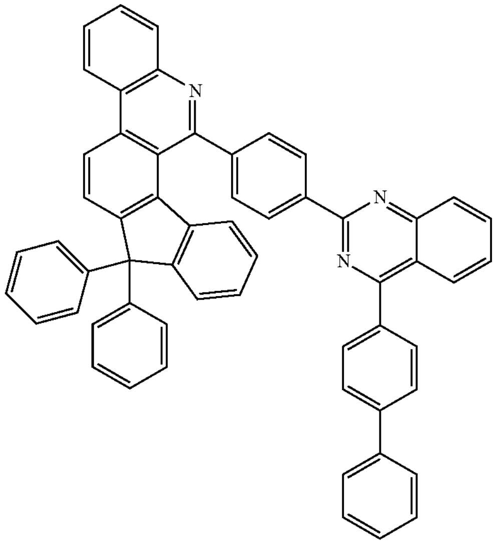
11-65
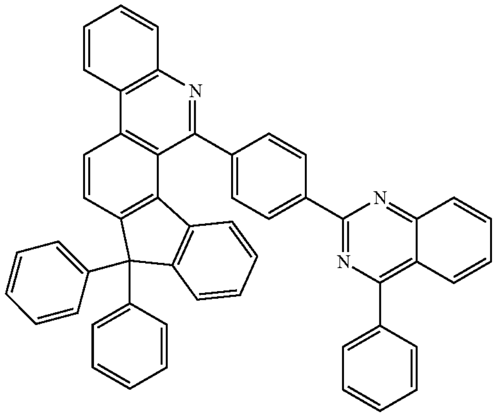
-continued
11-66
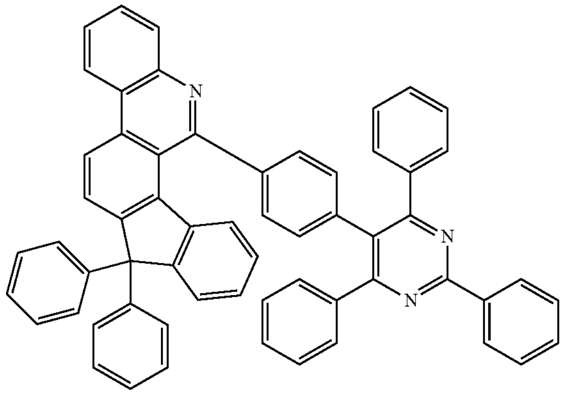
11-67
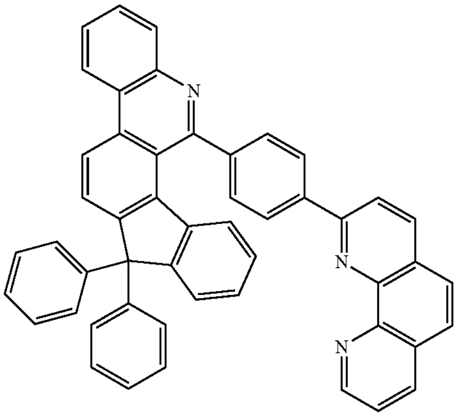
11-68
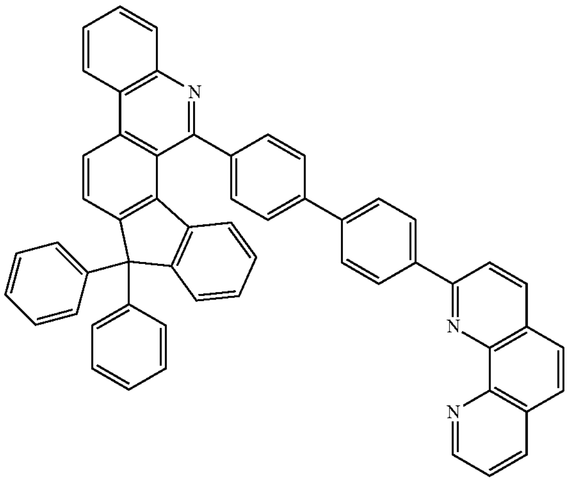

-continued
11-69
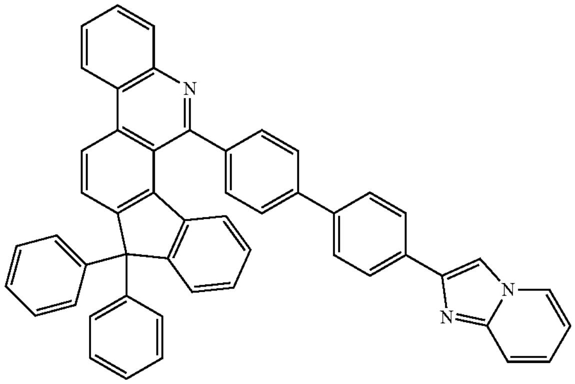
11-70
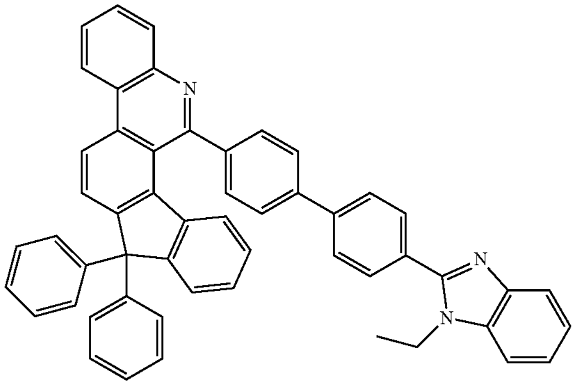
11-71
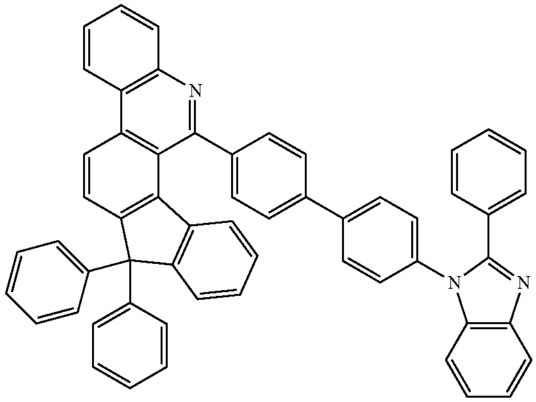
-continued
11-72
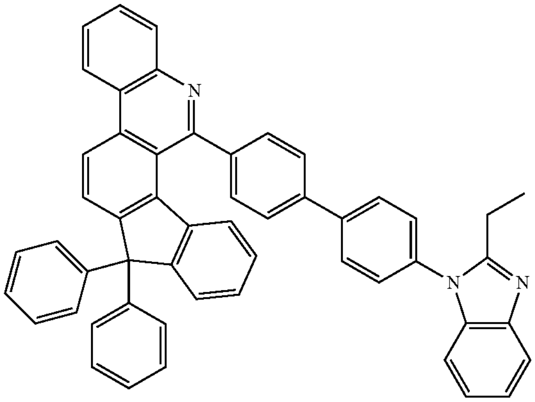
11-73
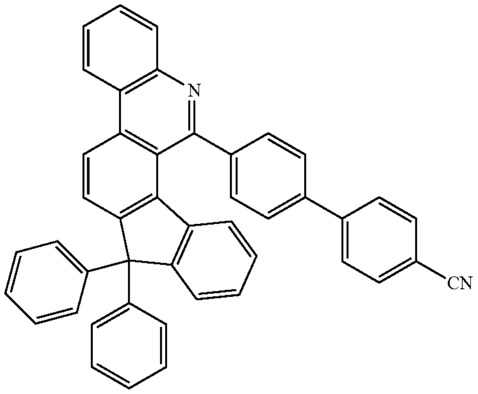
11-74
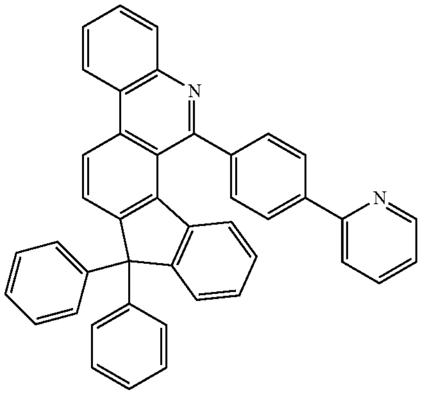
11-75
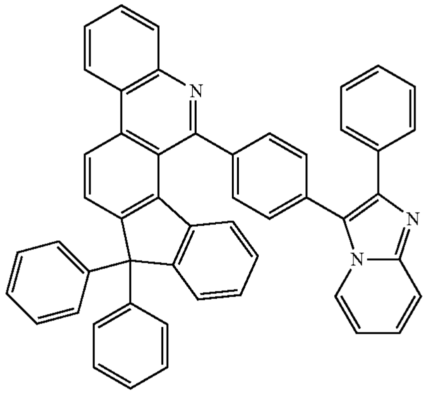

-continued
11-76
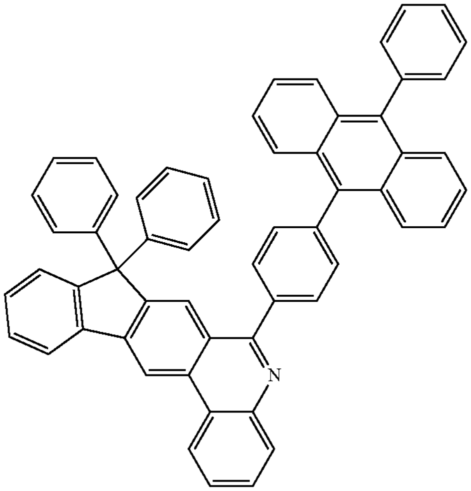
11-77
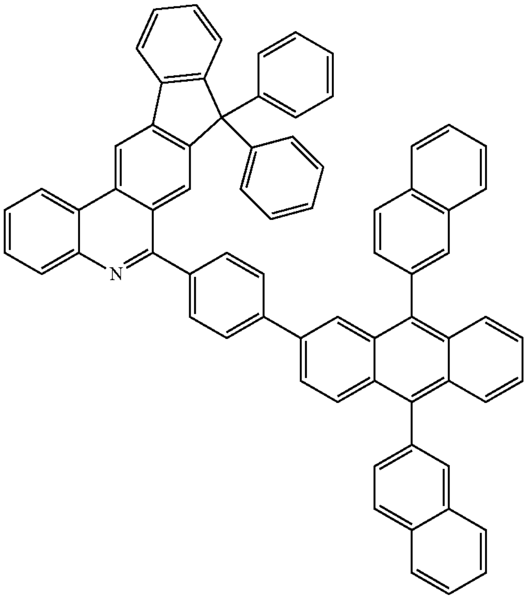
11-78
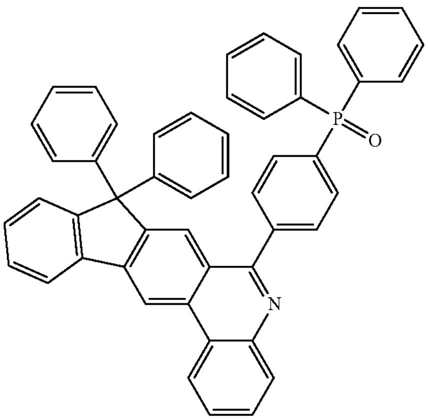
-continued
11-79
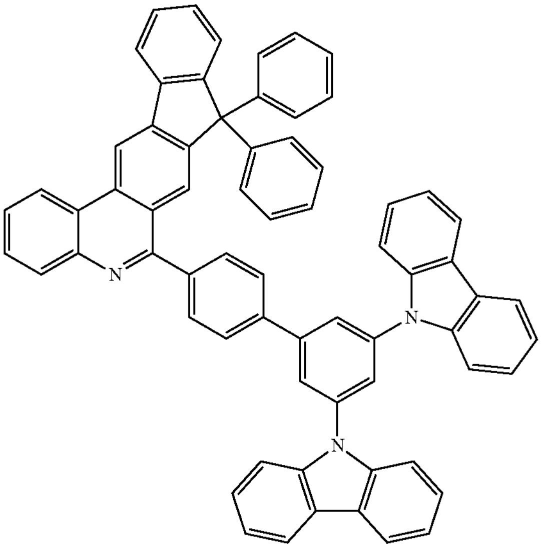
11-80
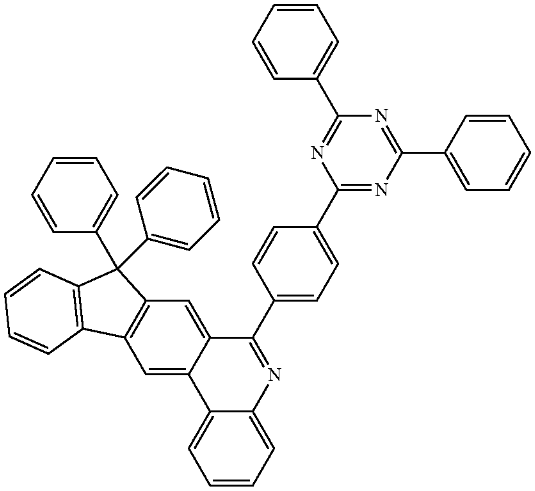
11-81
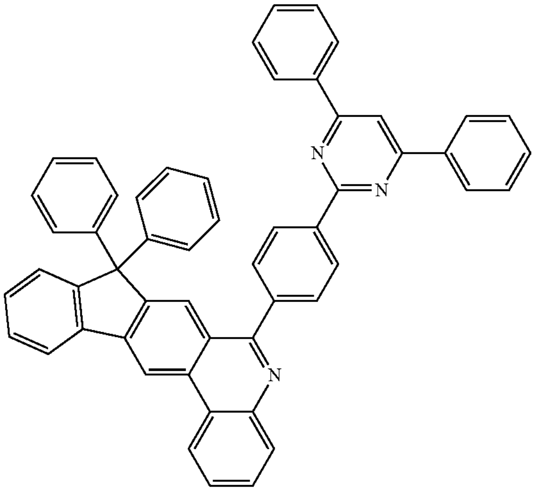

-continued
11-82
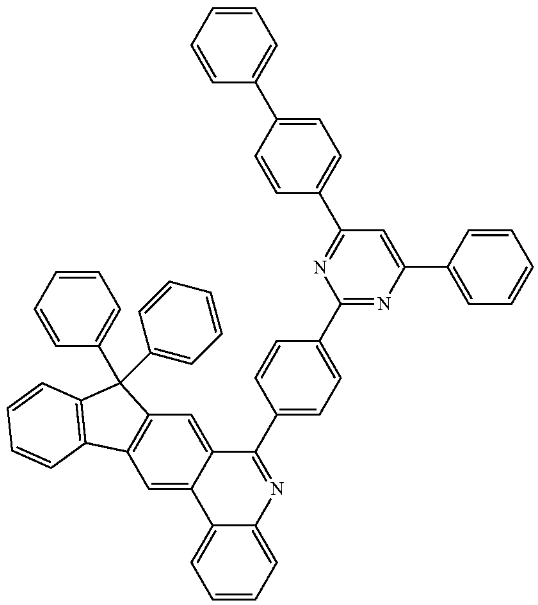
11-83
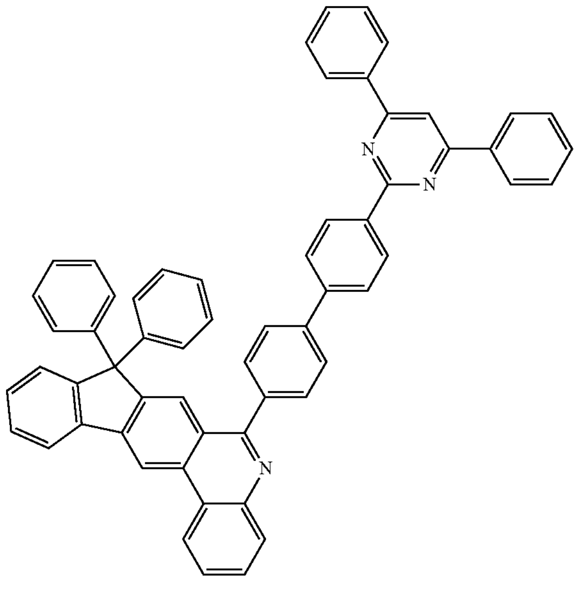
-continued
11-84
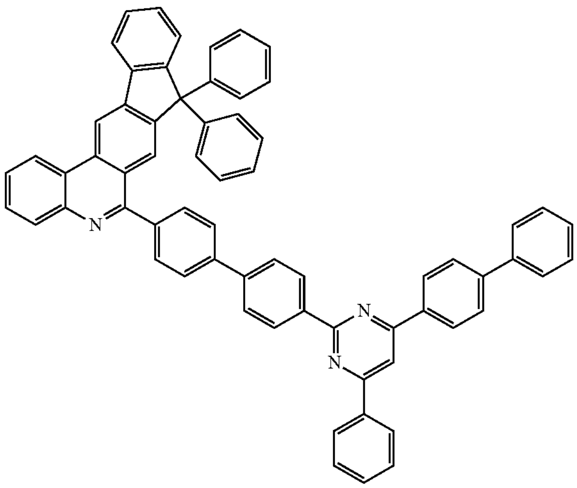
11-85
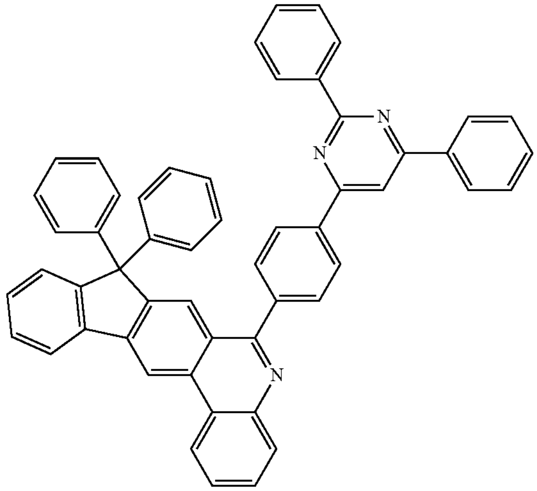
11-86
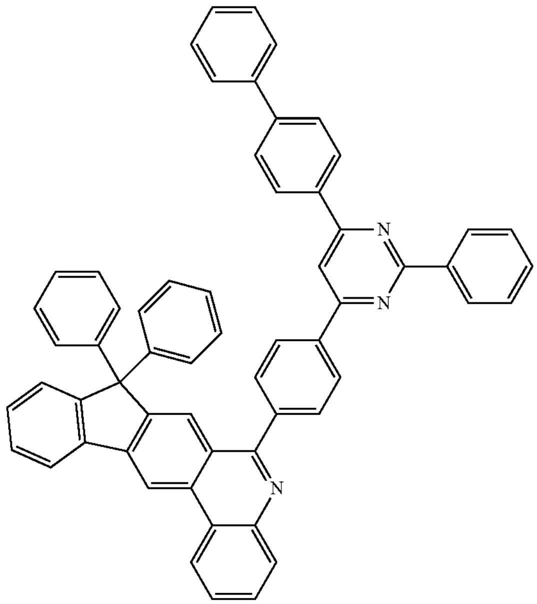

-continued
11-87
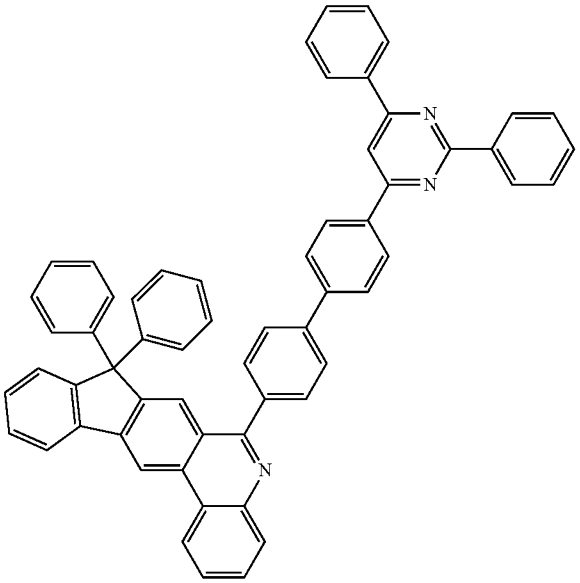
11-88
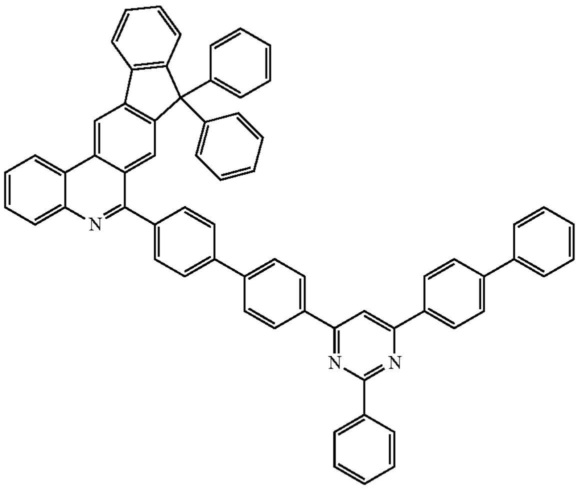
11-89
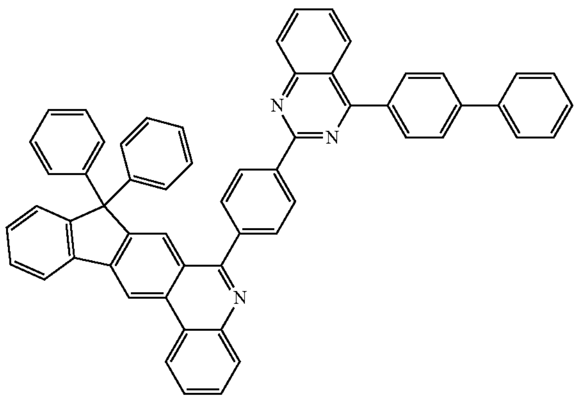
-continued
11-90
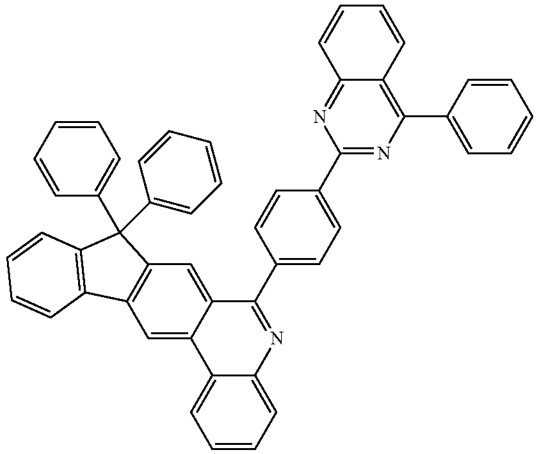
11-91
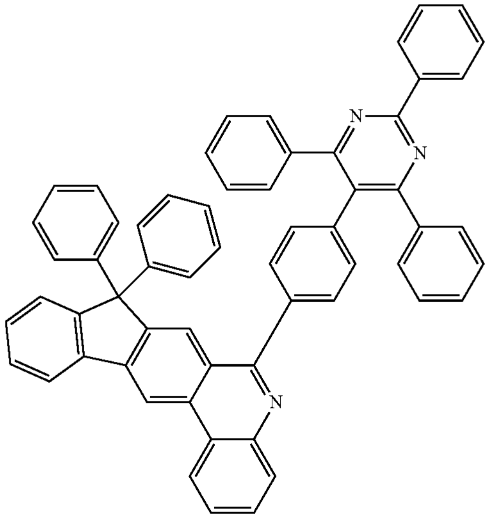
11-92
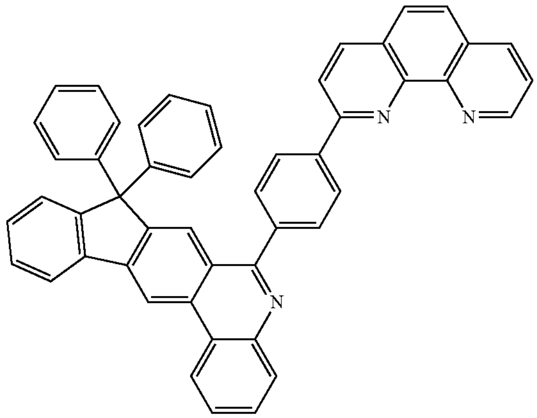

-continued
11-93
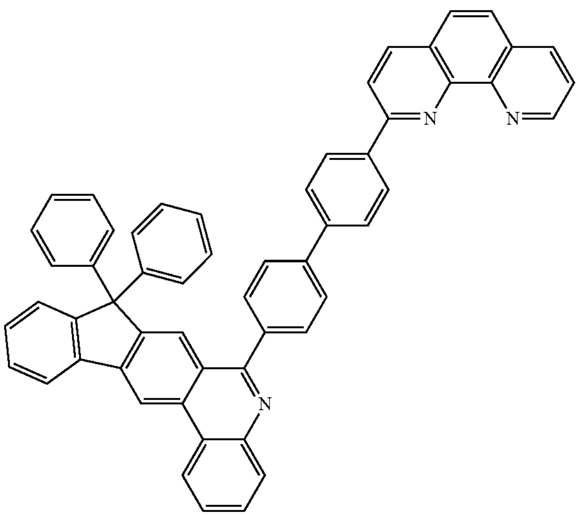
11-94
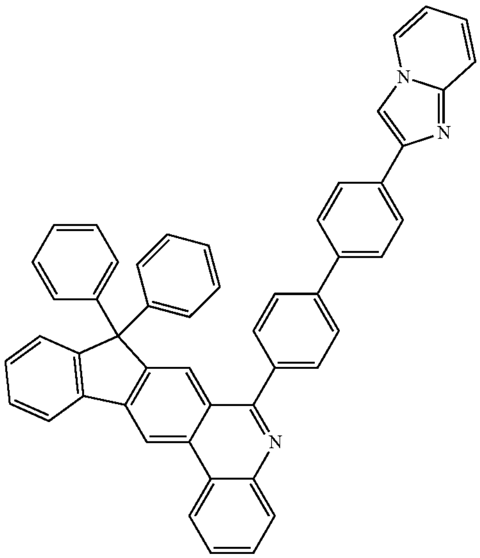
11-95
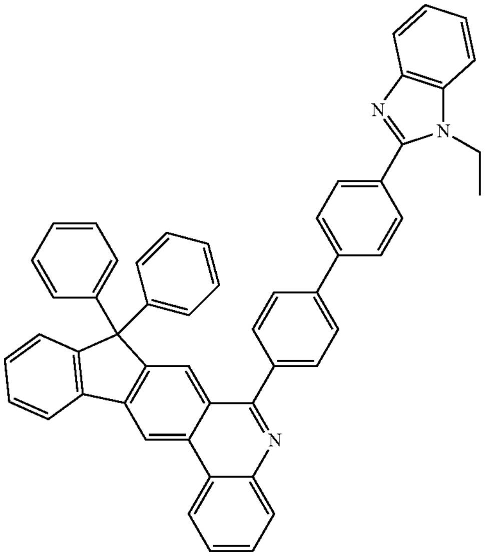
-continued
11-96
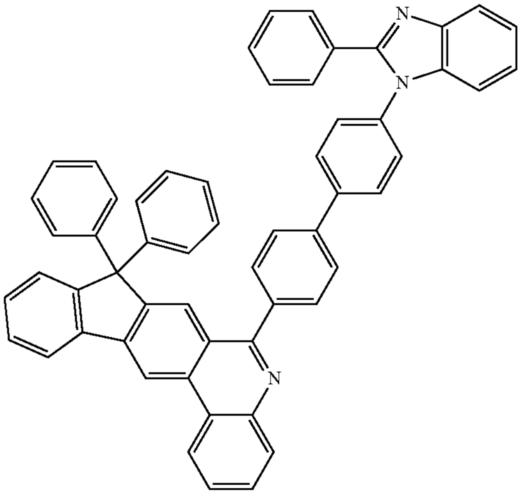
11-97
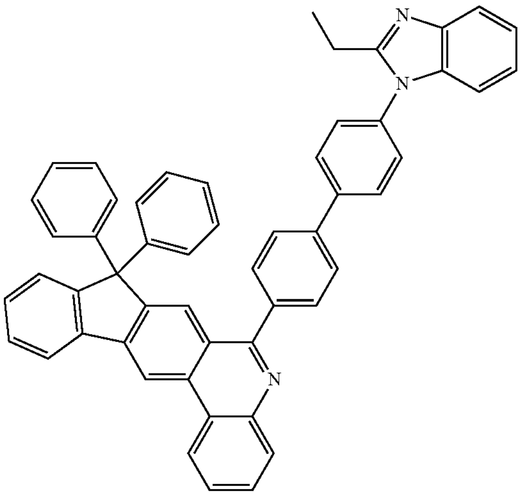
11-98
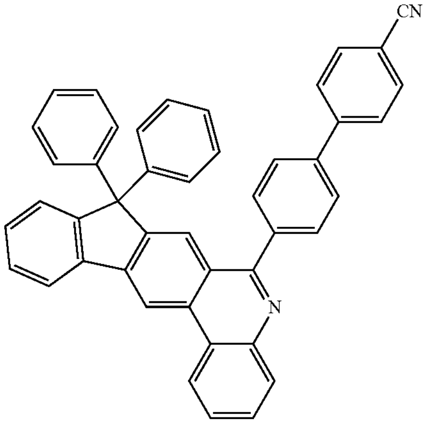

-continued
11-99
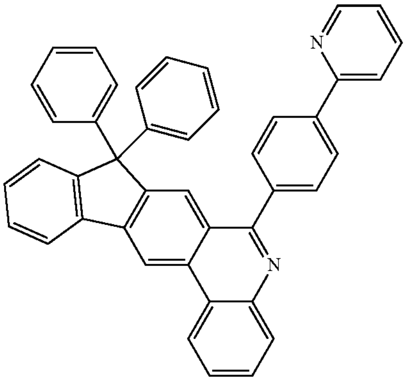
11-100
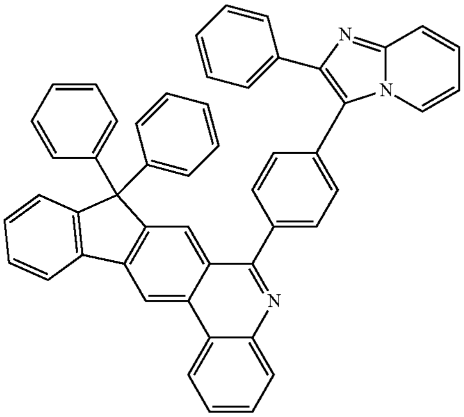
12-1
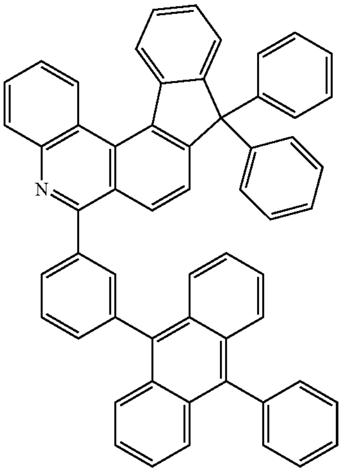
-continued
12-2
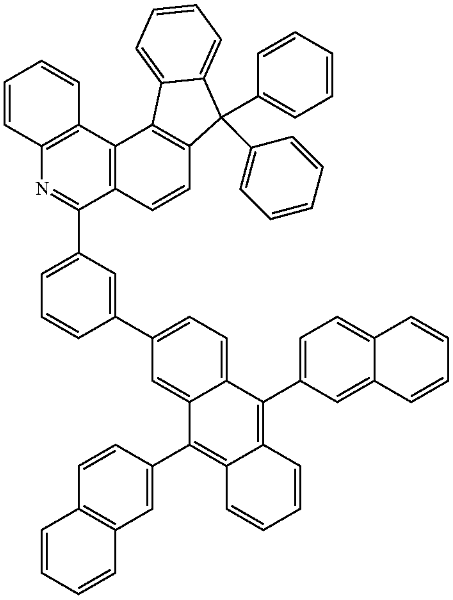
12-3
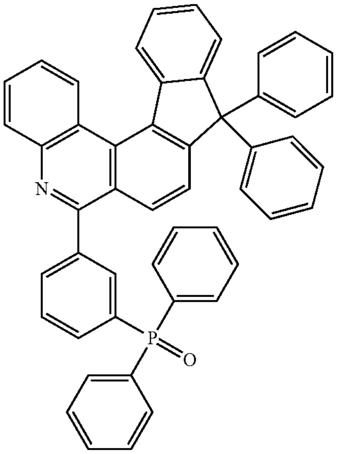
12-4
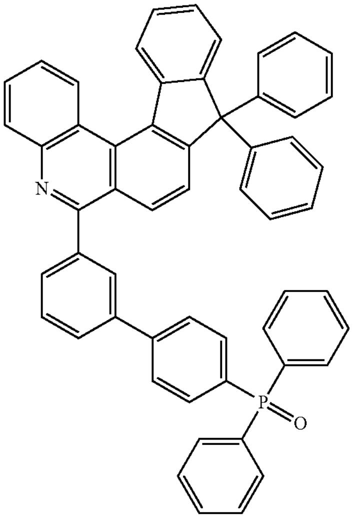

-continued
12-5
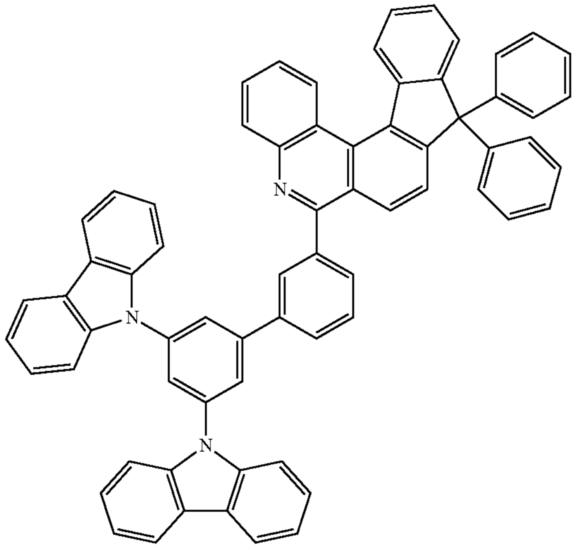
12-6
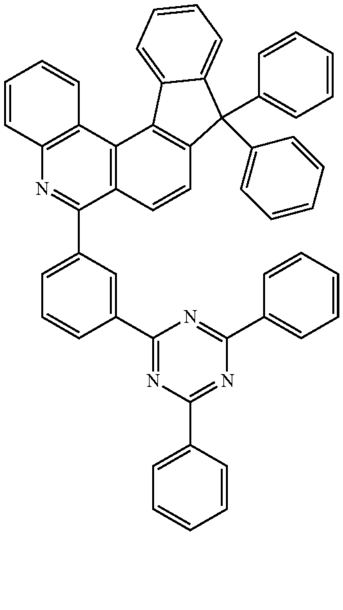
-continued
12-7
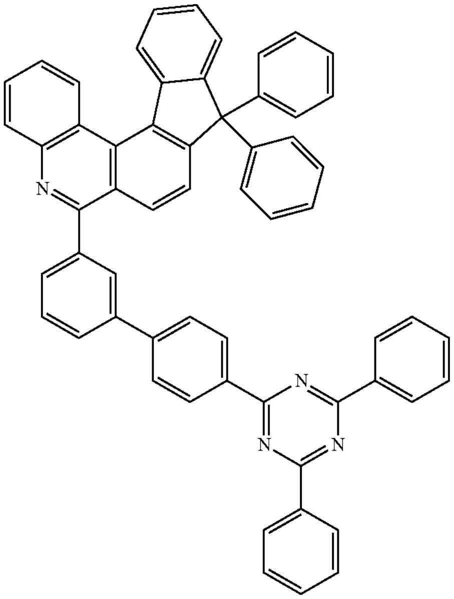
12-8
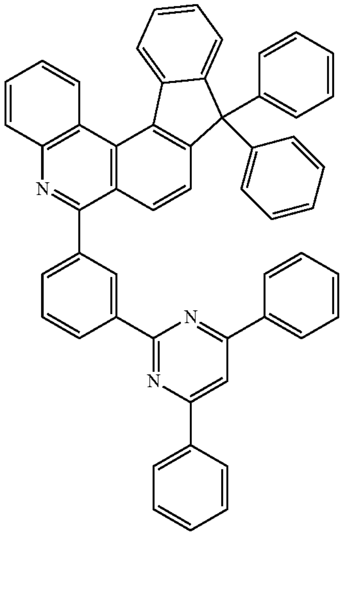

-continued
12-9
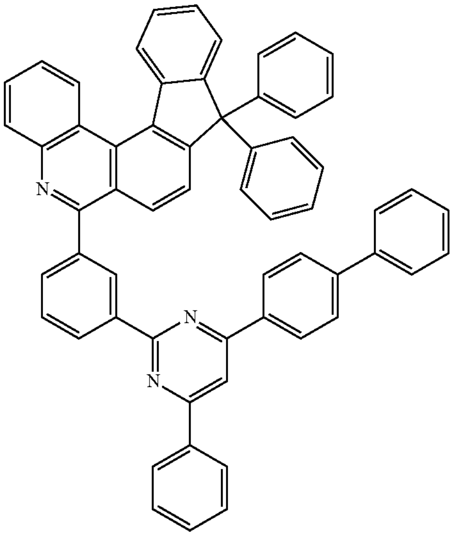
12-10
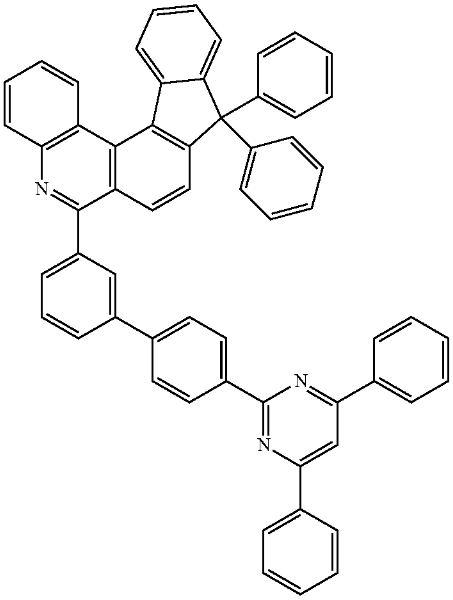
-continued
12-11
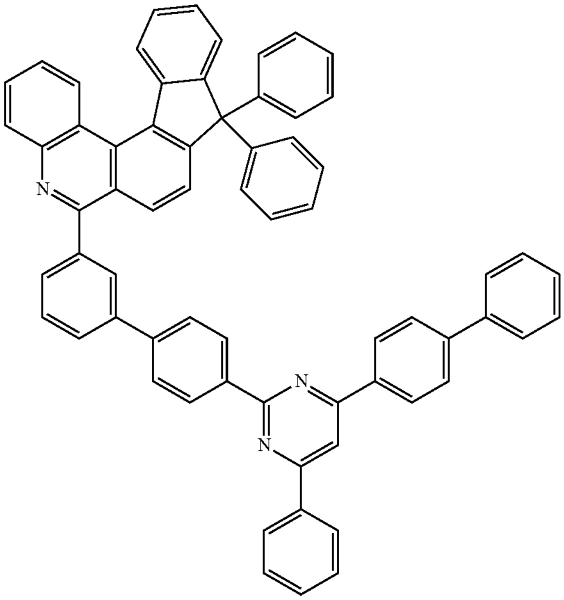
12-12
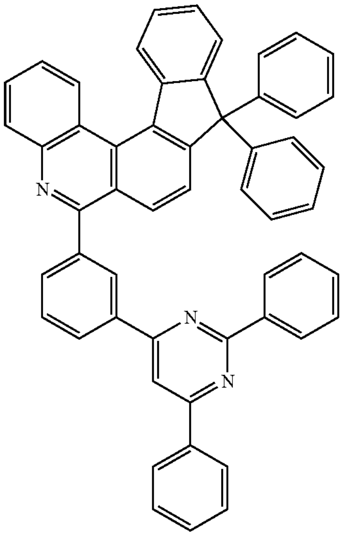

-continued
12-13
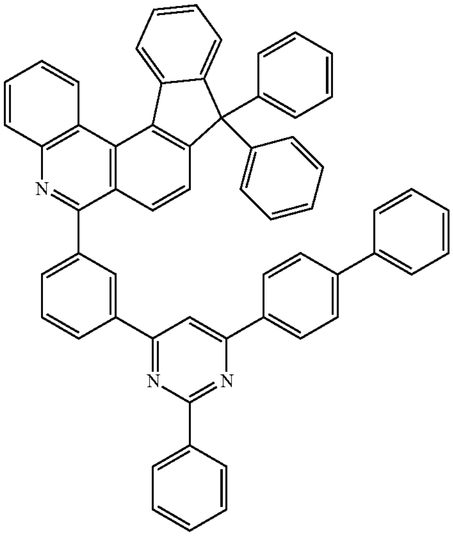
12-14
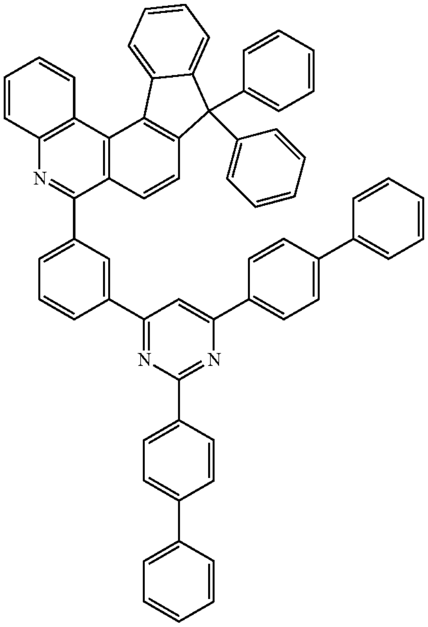
-continued
12-15
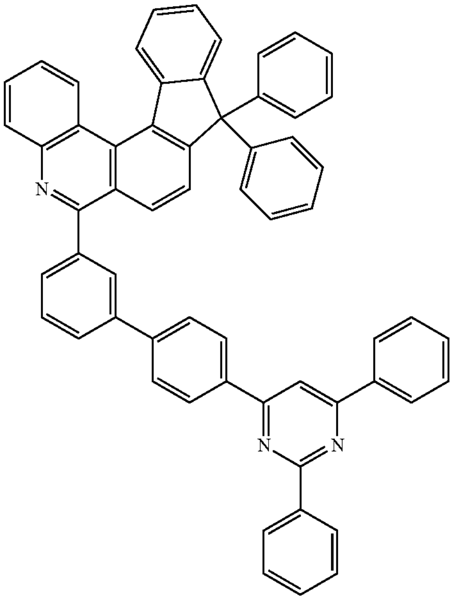
12-16
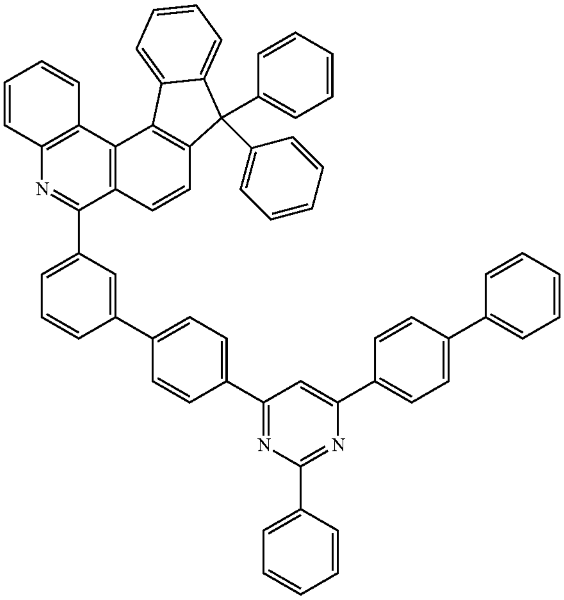

-continued
12-17
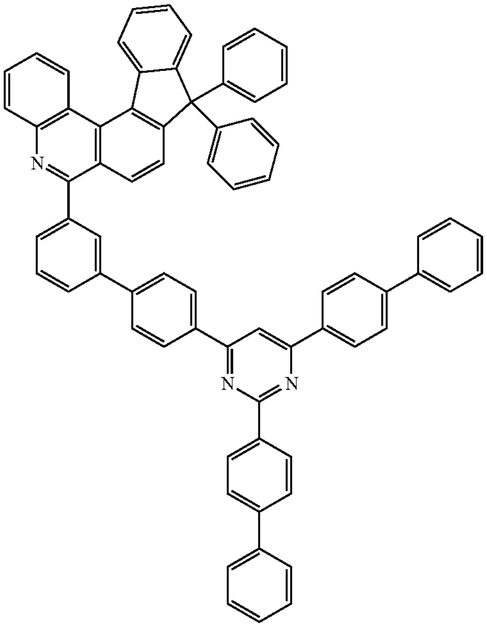
12-18
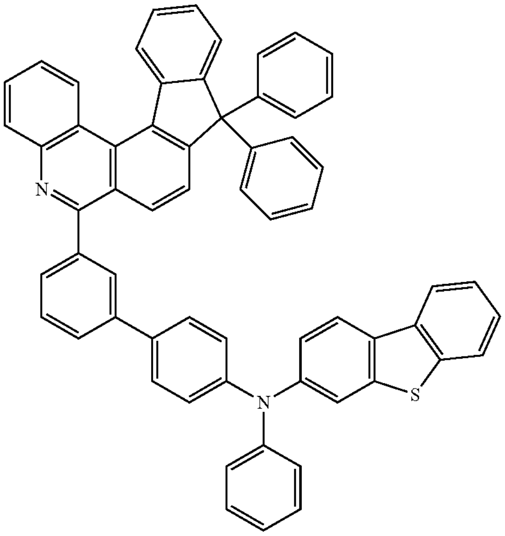
-continued
12-19
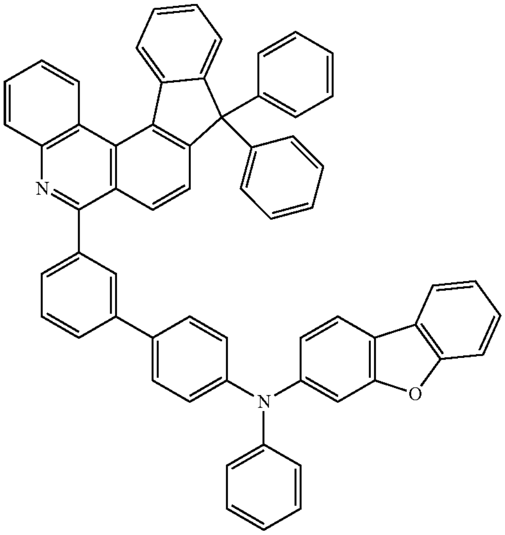
12-20
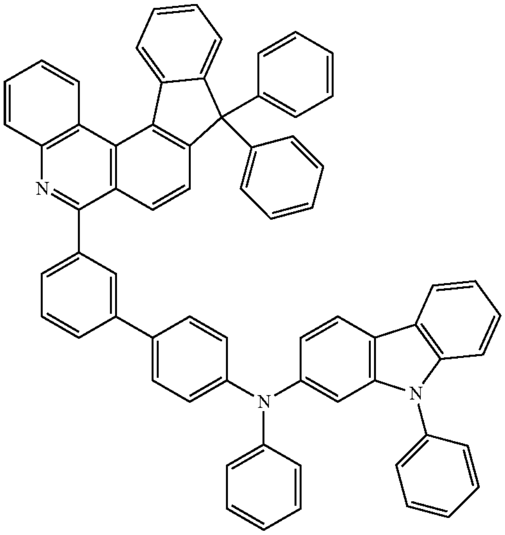

-continued
12-21
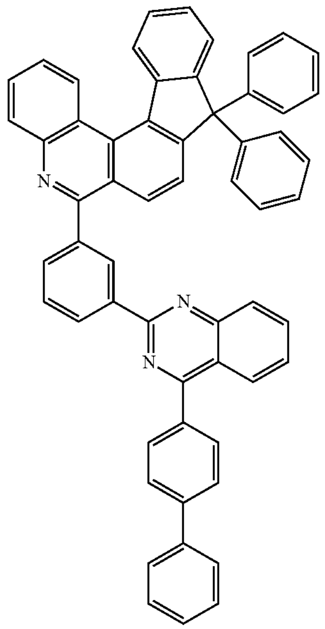
-continued
12-23
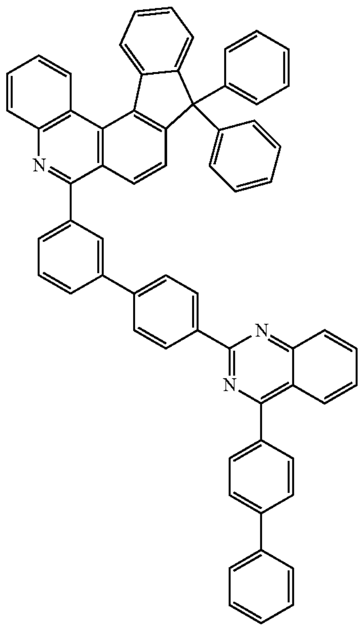
12-22
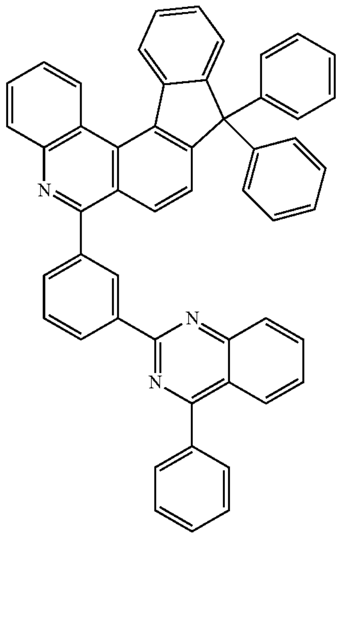
12-24
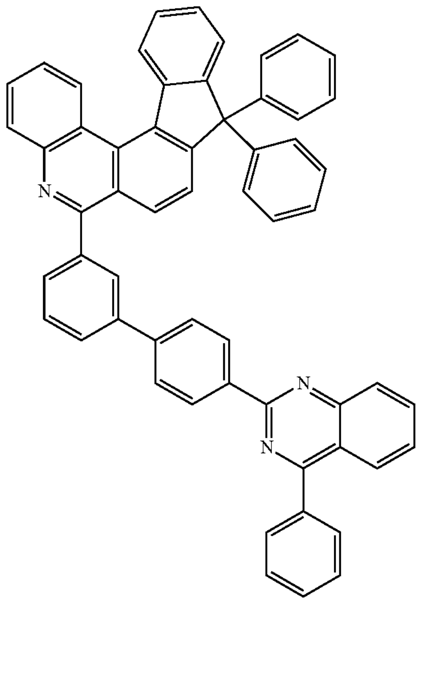

-continued
12-25
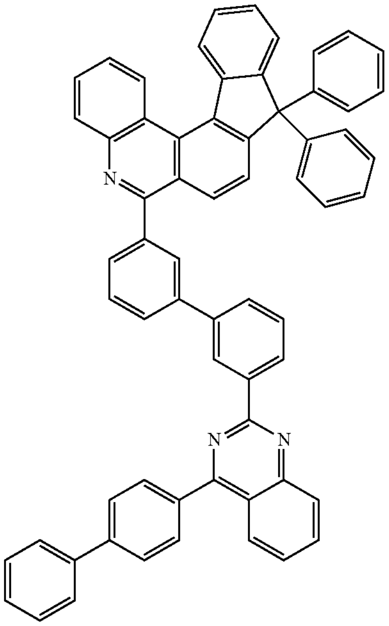
12-26
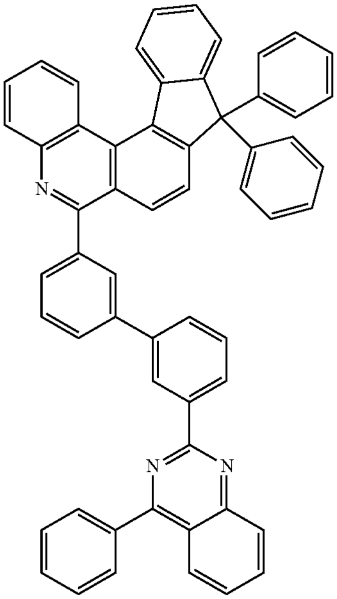
-continued
12-27
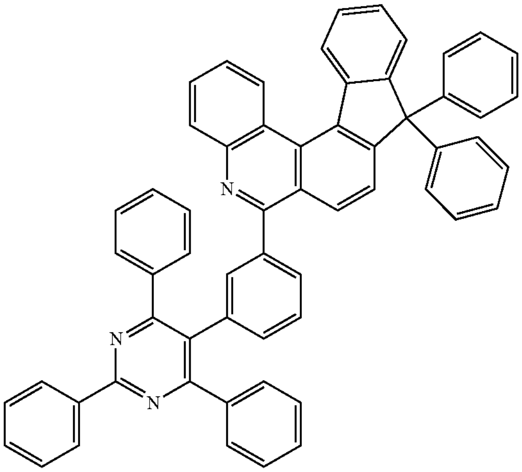
12-28
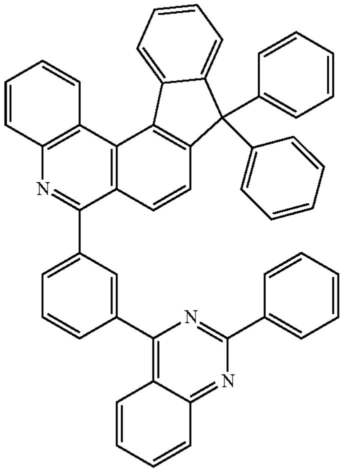
12-29
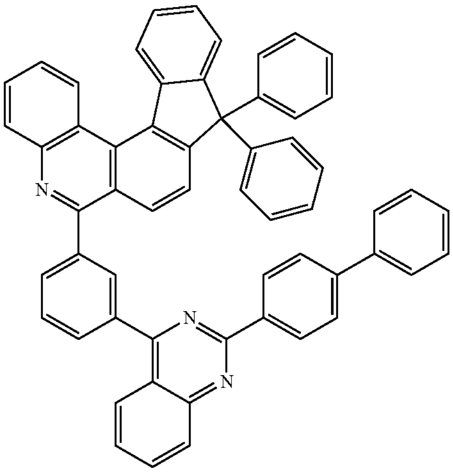

-continued
12-30
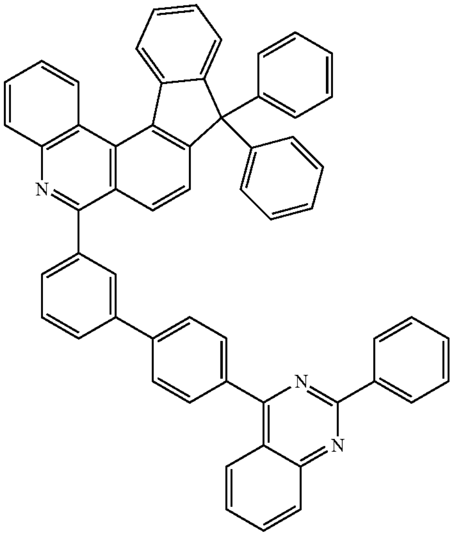
12-31
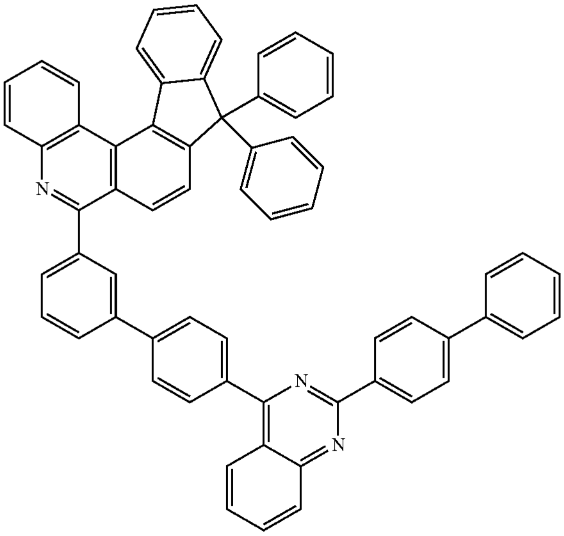
12-32
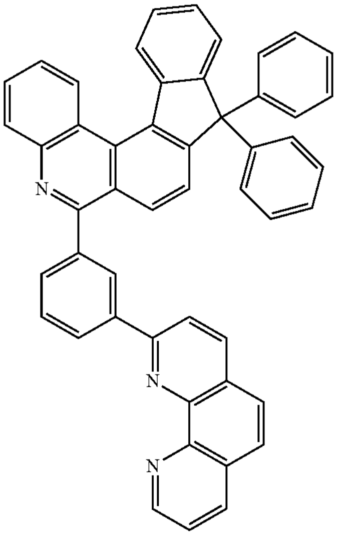
-continued
12-33
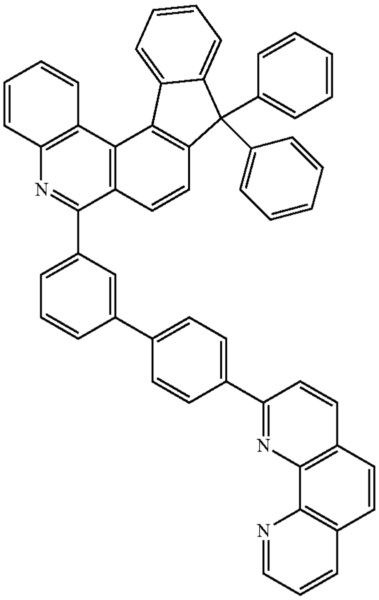
12-34
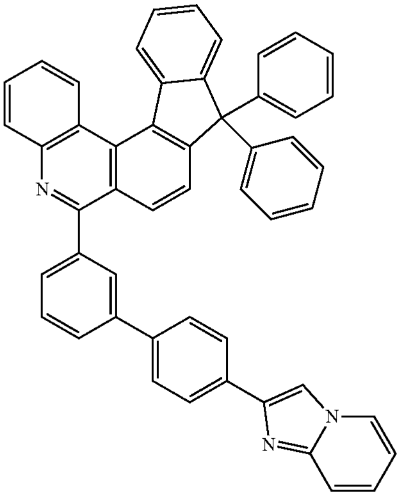

-continued
12-35
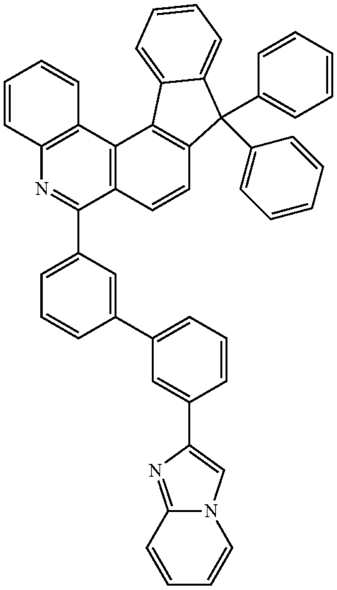
12-36
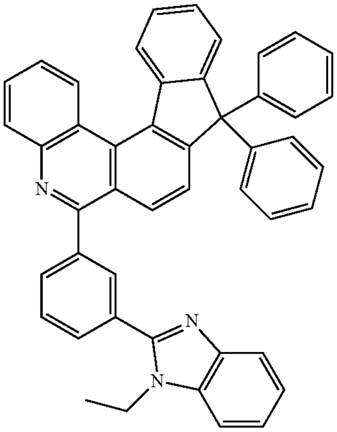
12-37
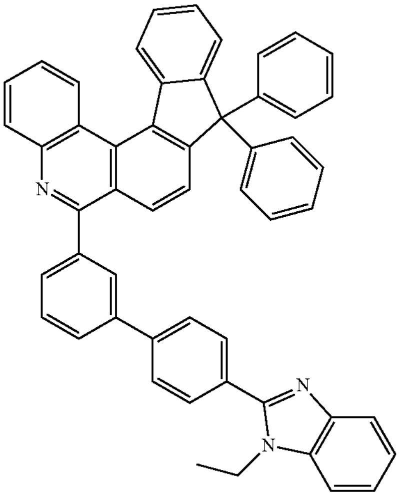
-continued
12-38
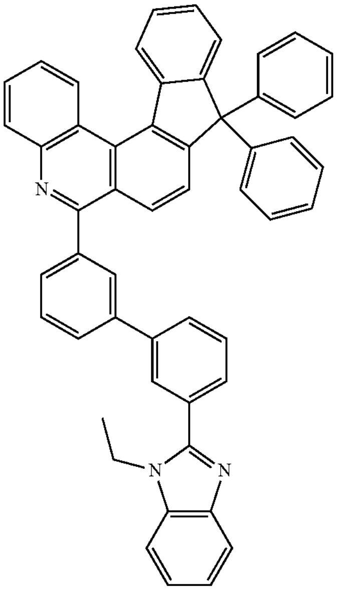
12-39
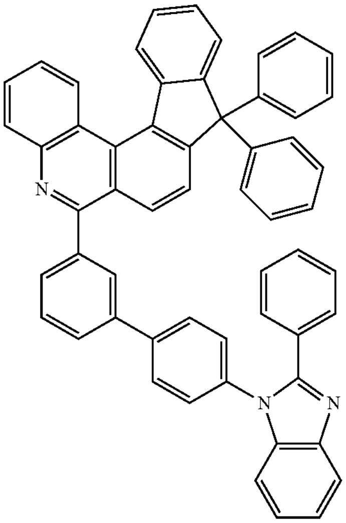
12-40
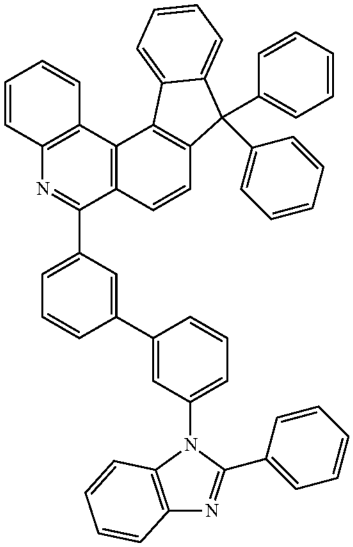

-continued
12-41
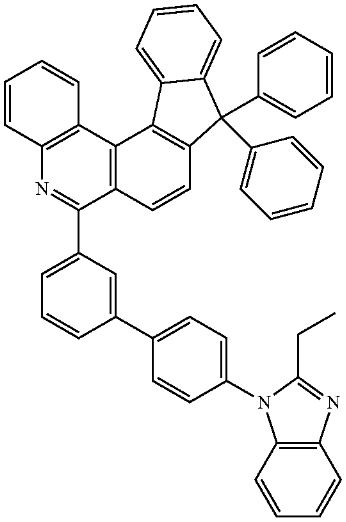
12-42
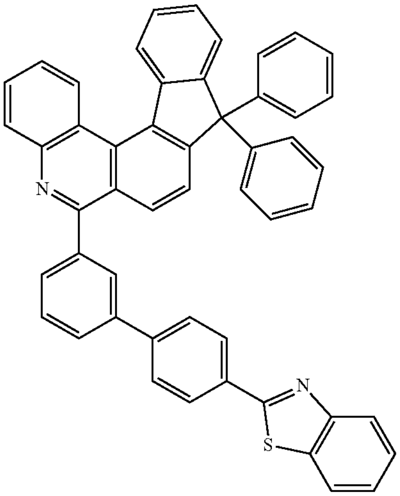
12-43
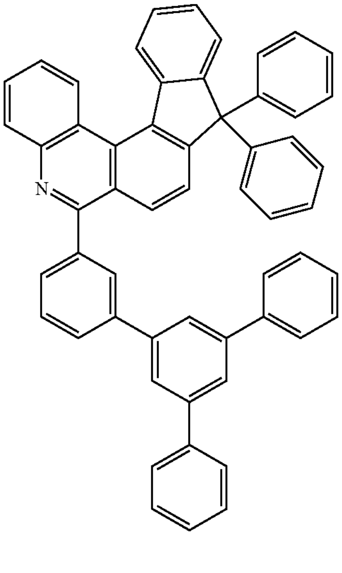
-continued
12-44
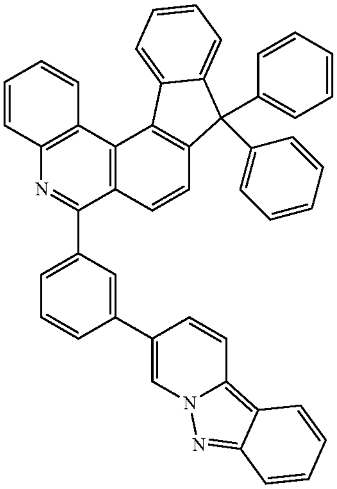
12-45
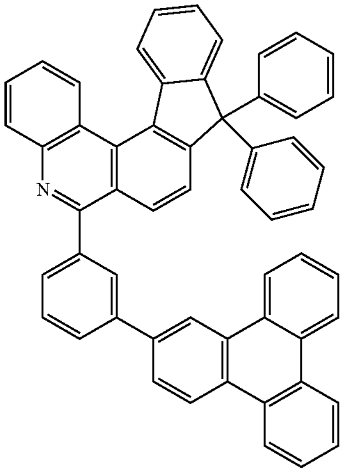
12-46
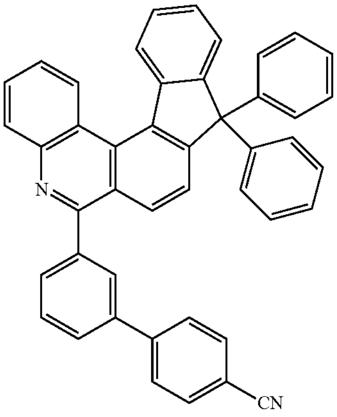

-continued
12-47
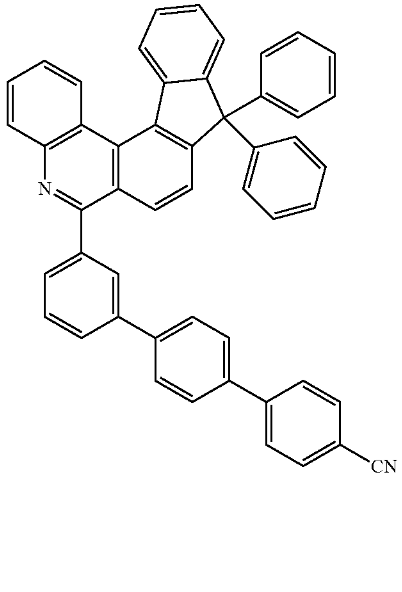
12-48
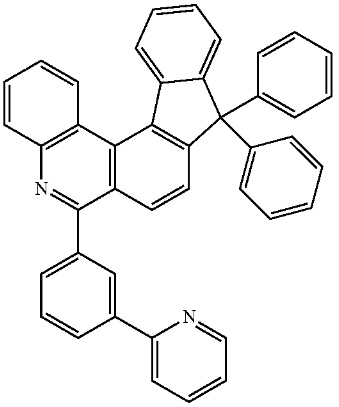
12-49
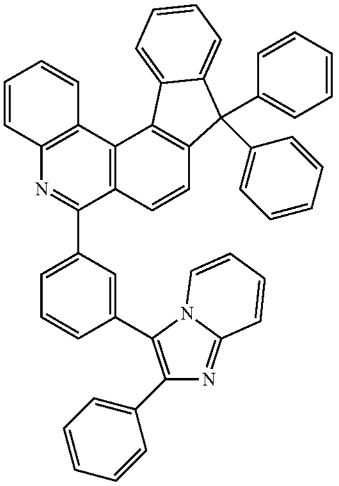
-continued
12-50
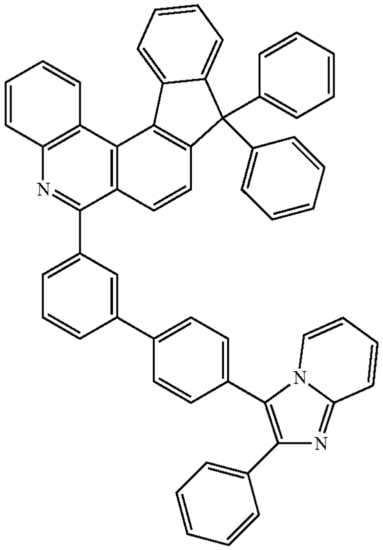
12-51
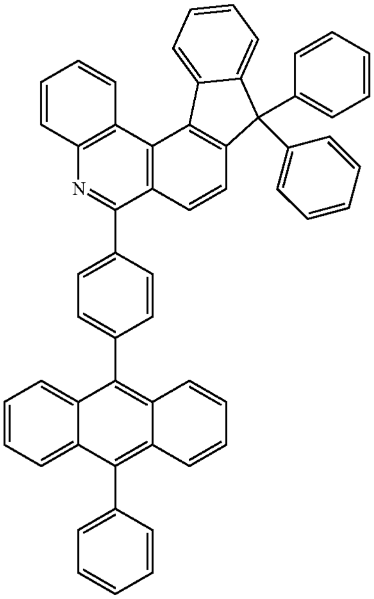

-continued
12-52
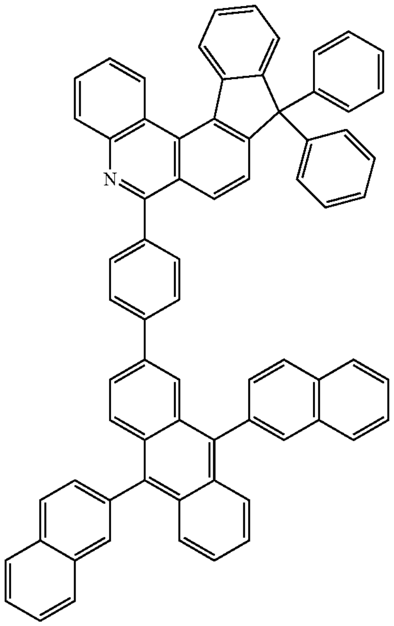
12-53
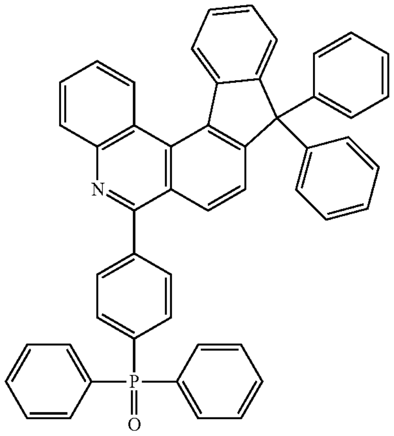
12-54
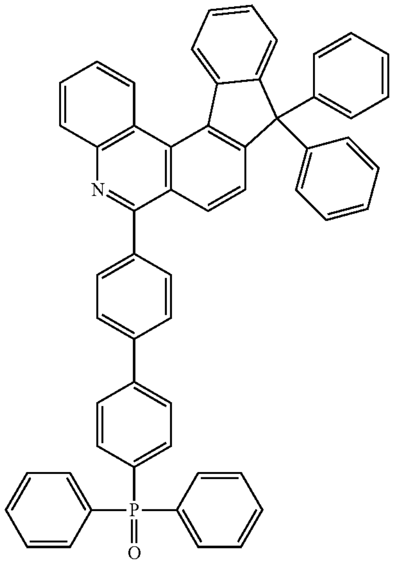
-continued
12-55
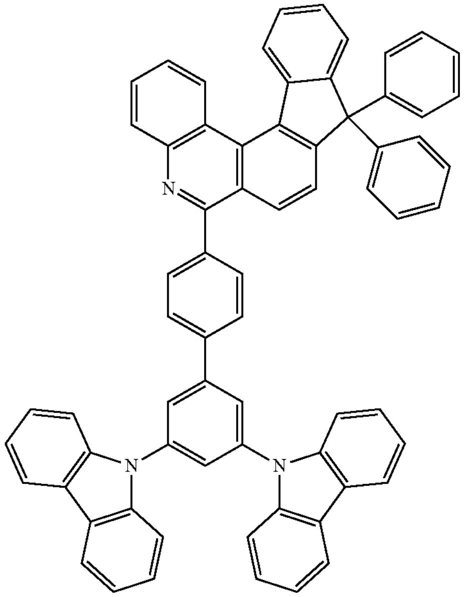
12-56
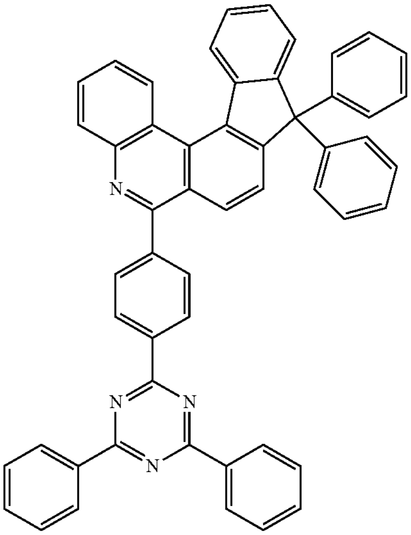

-continued
12-57
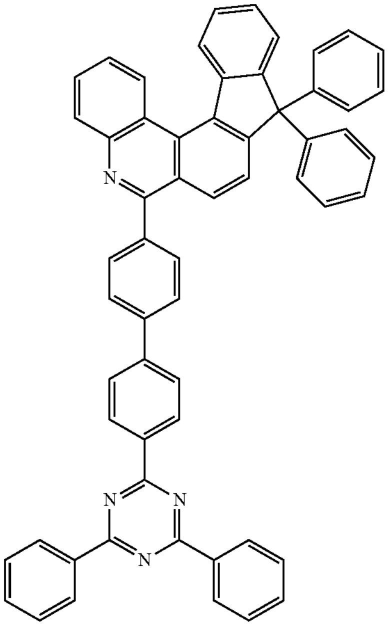
12-58
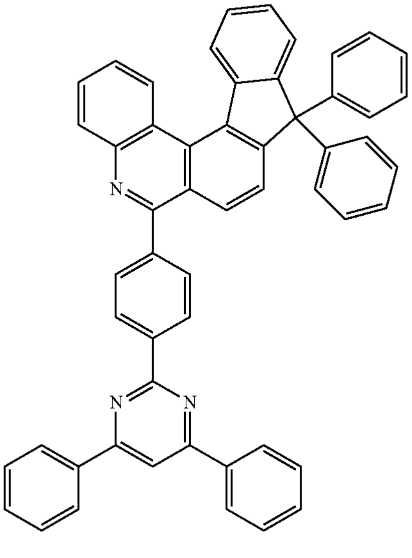
-continued
12-59
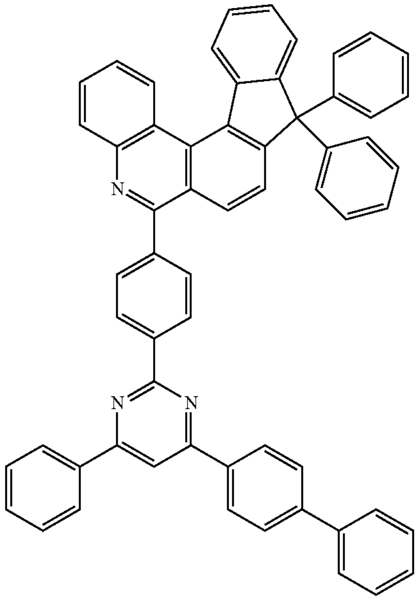
12-60
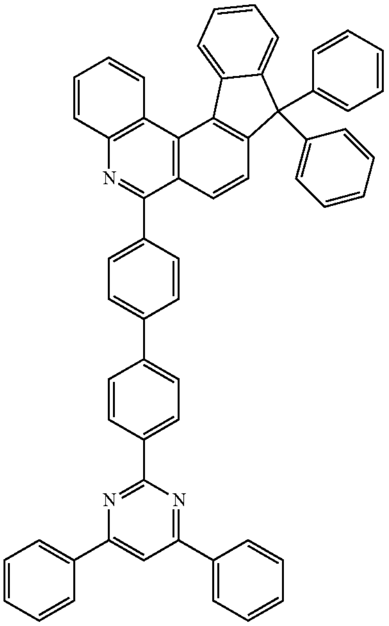

12-61
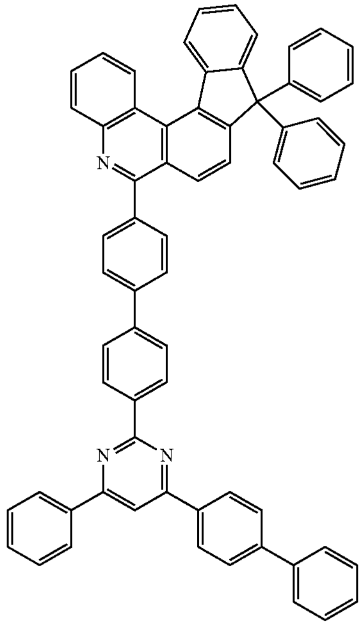
12-62
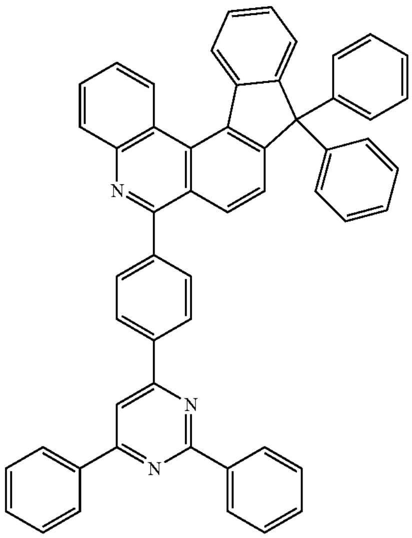
12-63
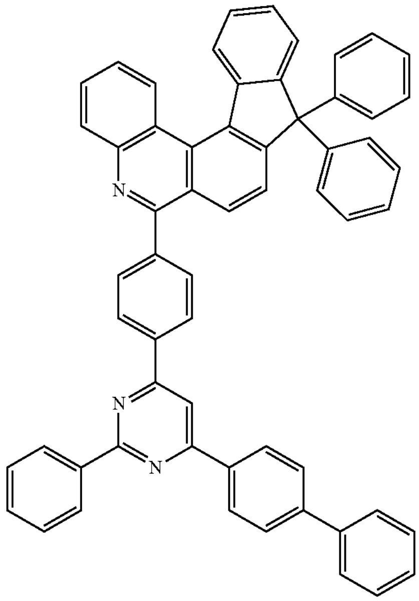
12-64
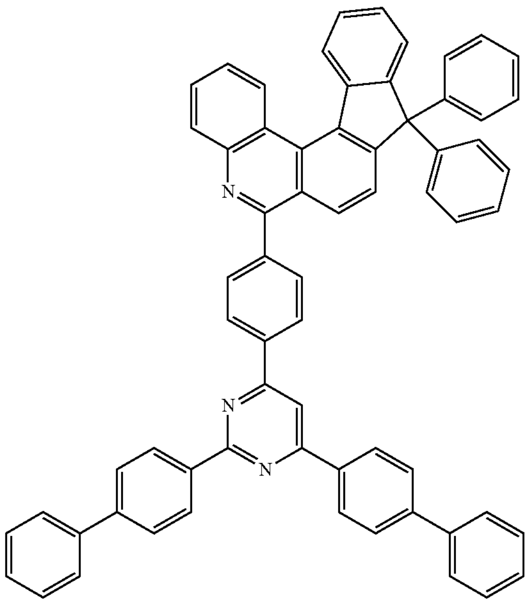

-continued
12-65
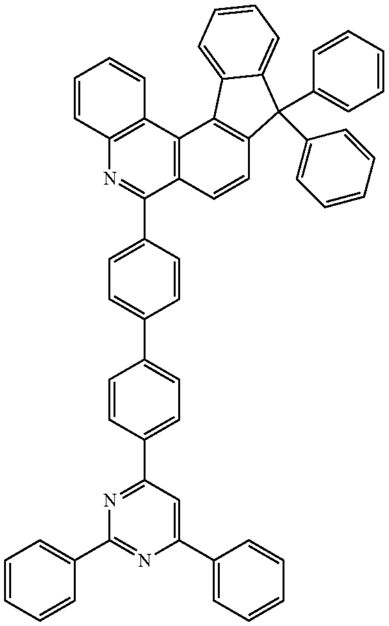
-continued
12-67
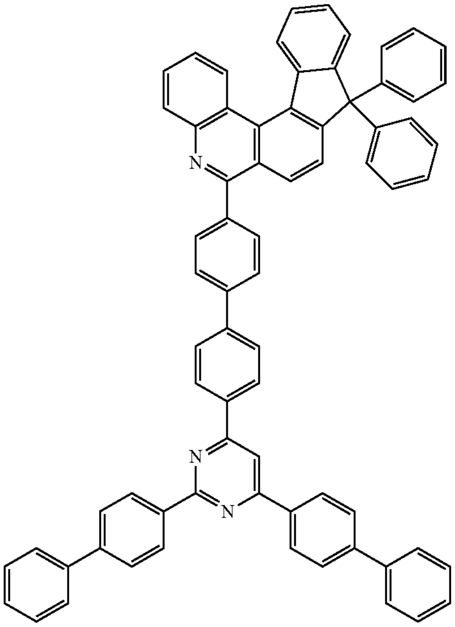
12-66
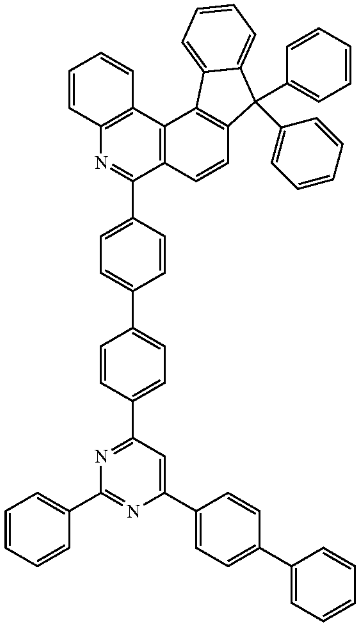
12-68
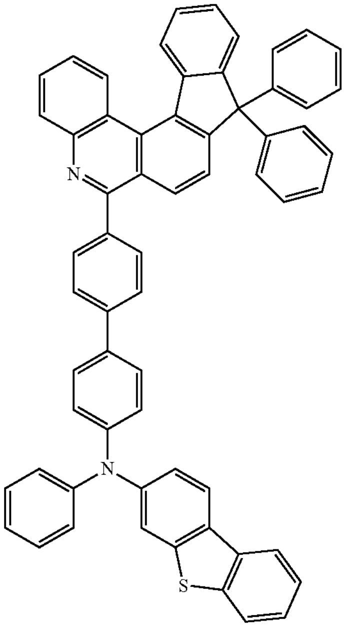

-continued
12-69
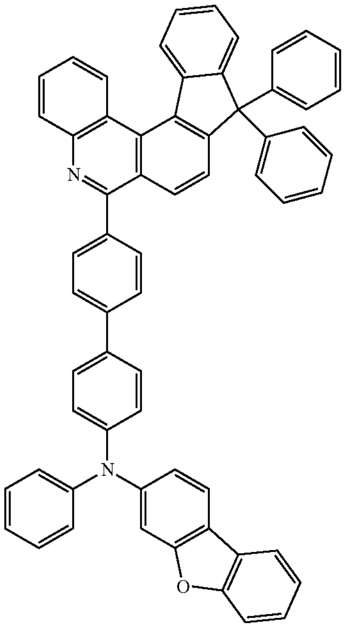
12-70
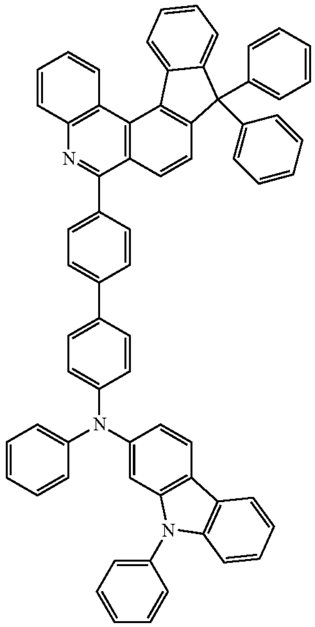
-continued
12-71
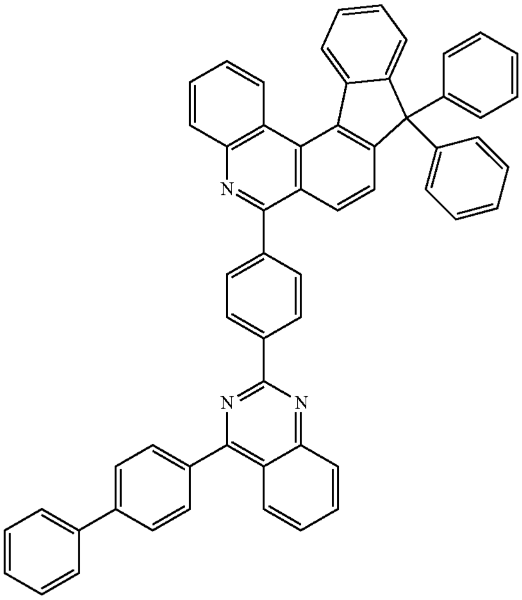
12-72
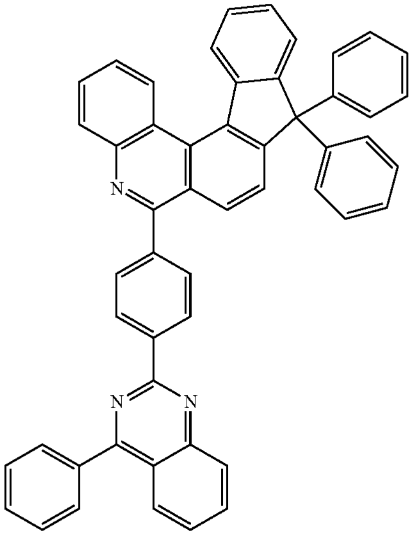

-continued
12-73
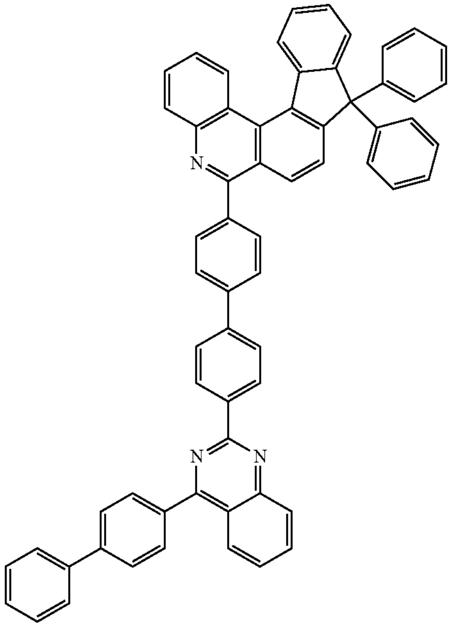
12-74
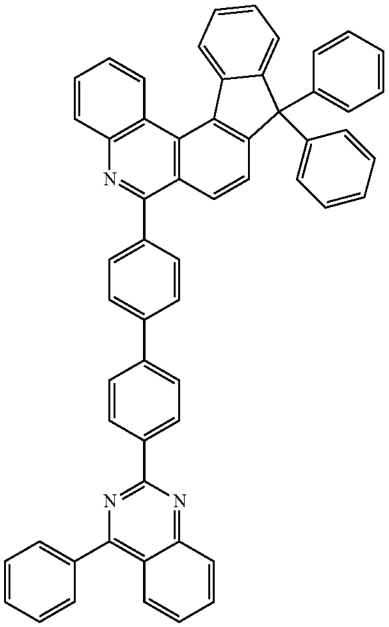
-continued
12-75
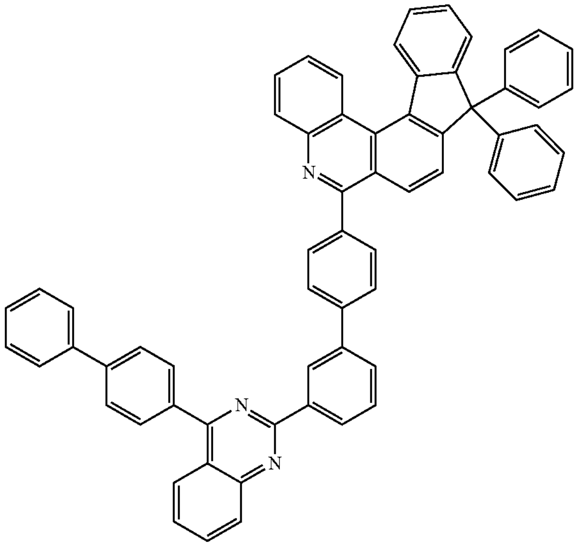
12-76
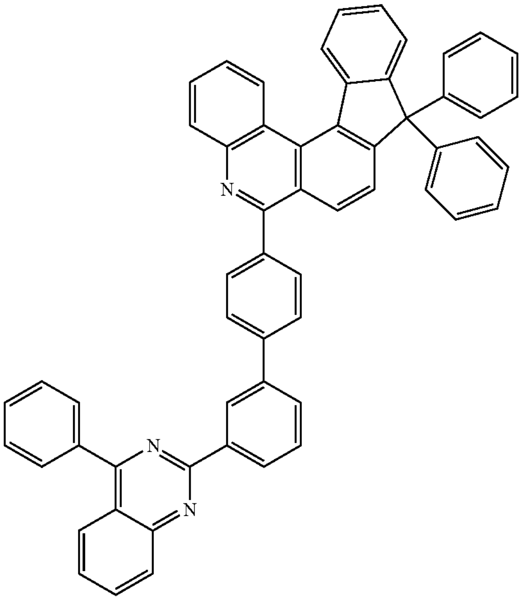

-continued
12-77
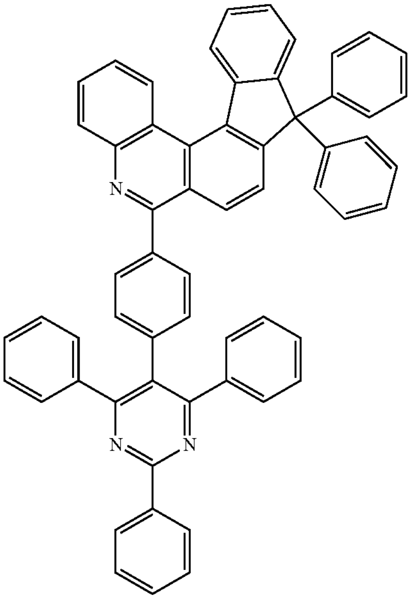
12-78
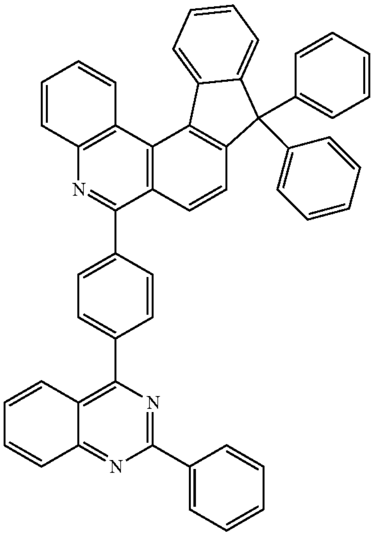
-continued
12-79
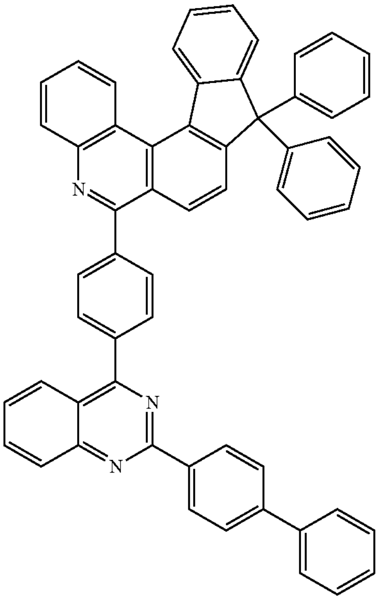
12-80
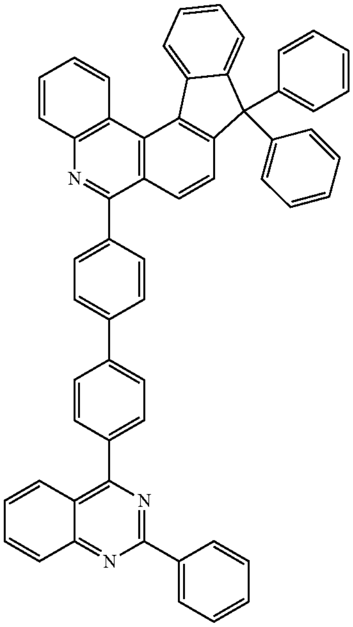

-continued
12-81
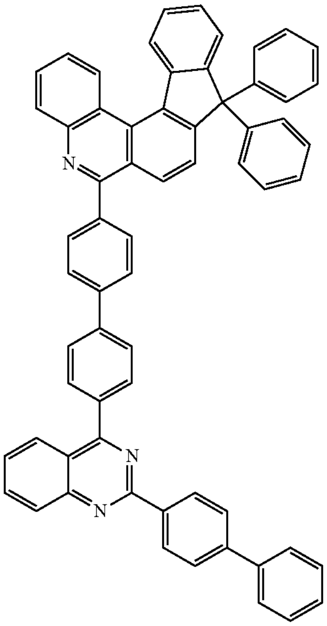
12-82
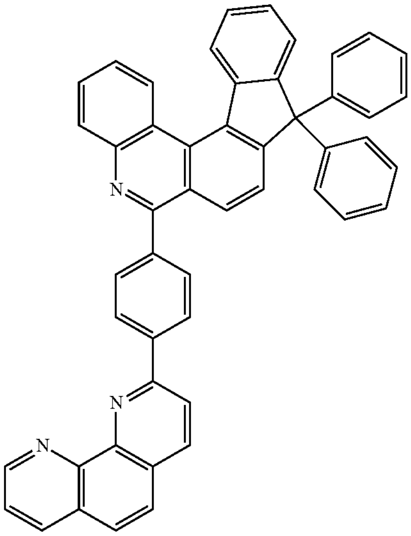
-continued
12-83
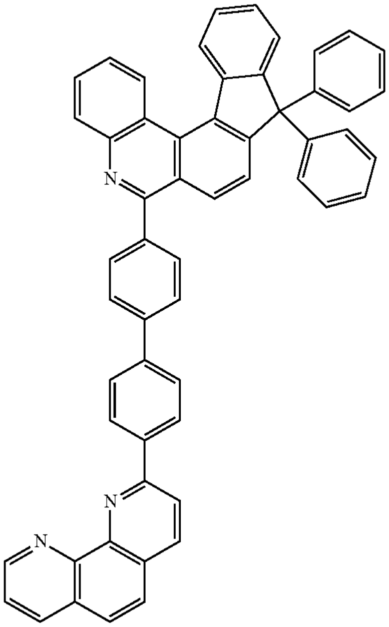
12-84
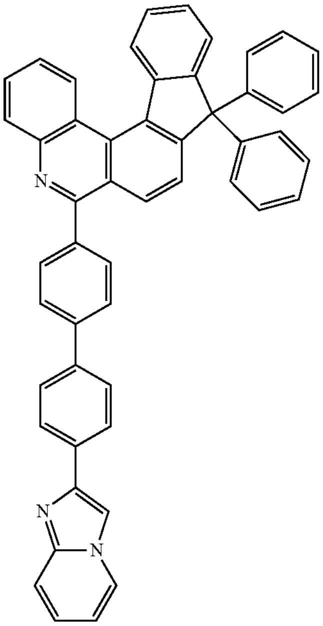

-continued
12-85
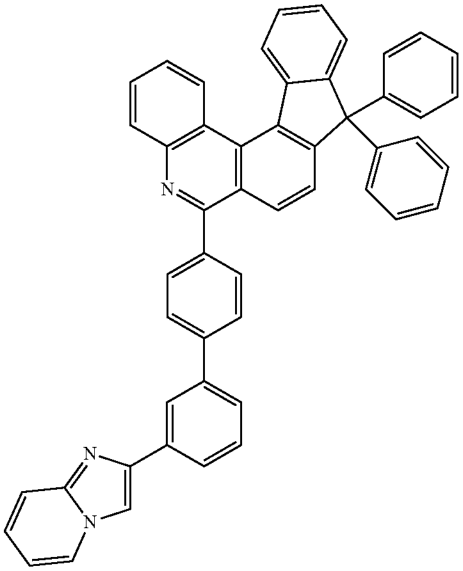
12-86
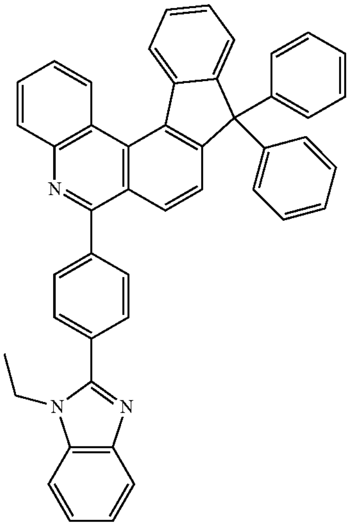
-continued
12-87
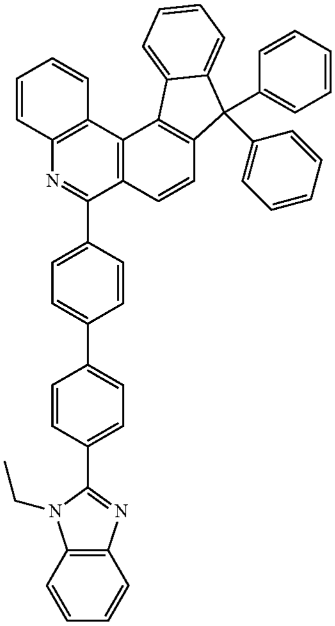
12-88
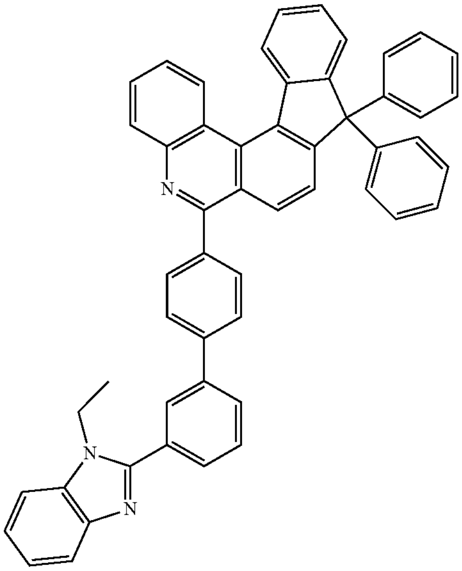

-continued
12-89
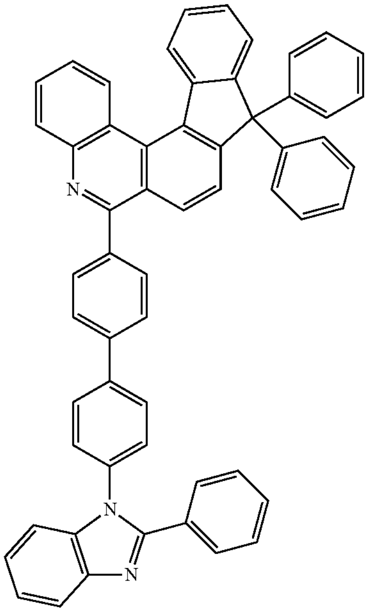
12-90
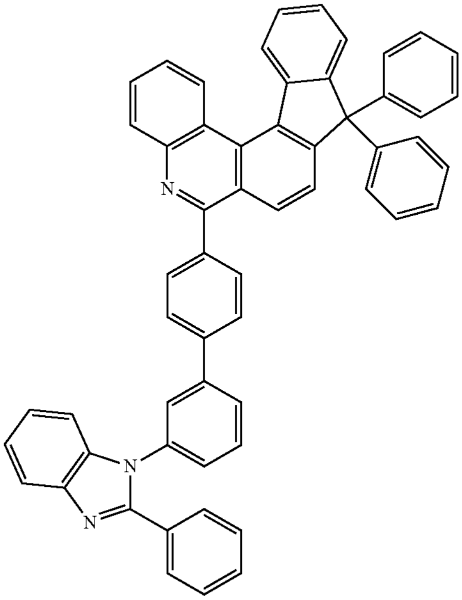
-continued
12-91
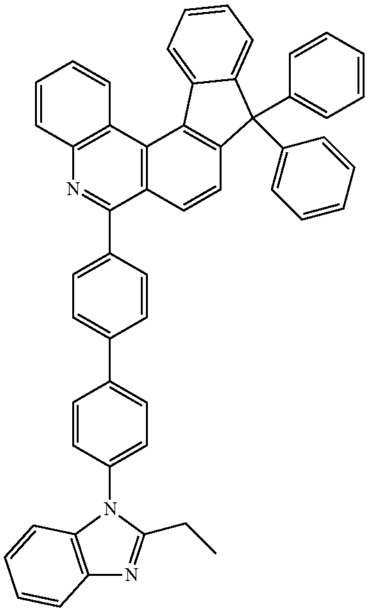
12-92
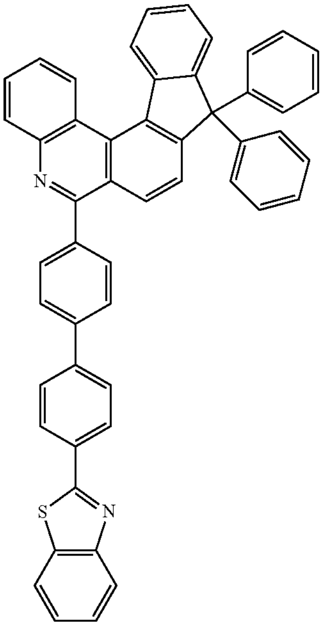

-continued
12-93
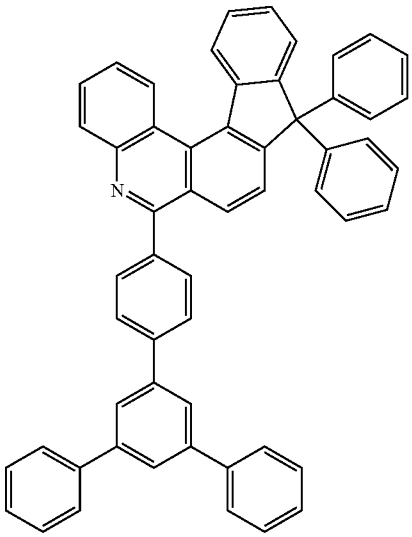
12-94
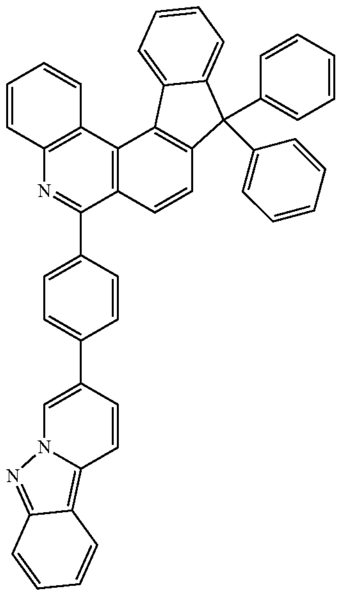
-continued
12-95
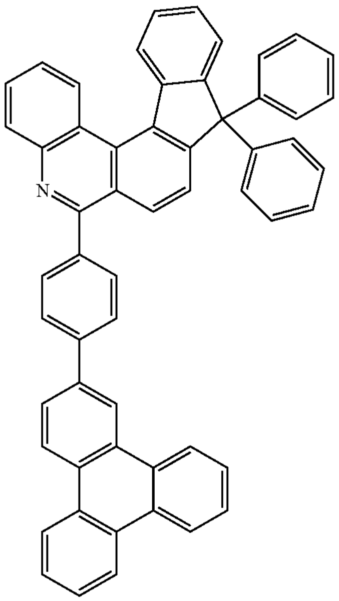
12-96
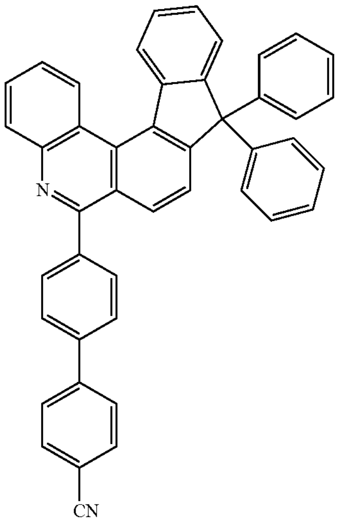

-continued 12-97

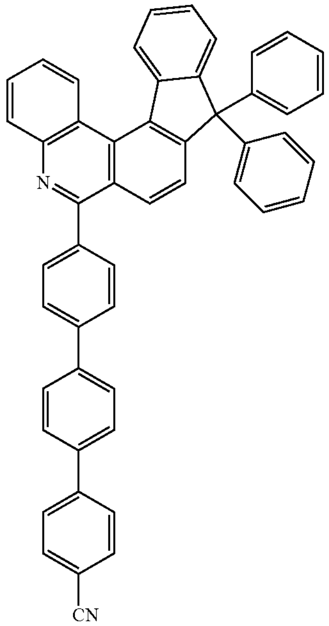

12-98

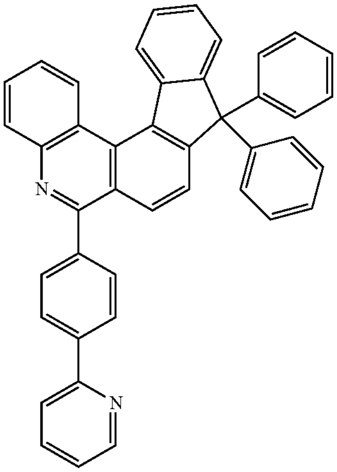

12-99

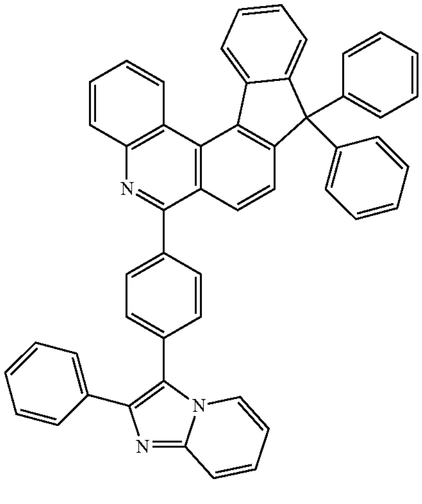

-continued 12-100

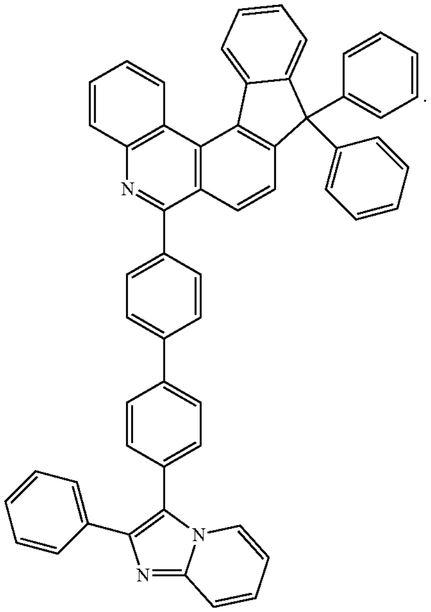

The aforementioned compounds may be prepared based on Preparation Examples as will be described later. Representative examples are described in the Preparation Examples as will be described later, but if necessary, the substituent group may be added or excluded, and a position of the substituent group may be changed. Further, a starting material, a reaction material, a reaction condition, and the like may be changed based on the technology known in the art. If necessary, a kind or a position of the substituent groups at remaining positions may be changed by a person with ordinary skill in the art using the technology known in the art.

Hereinafter, the present application will be described in more detail through Examples, which are set forth only to illustrate the present application, but are not to be construed to limit the scope of the present application.

For example, with regard to the compounds of Chemical Formulas 2, 13 to 20, 23, and 24, the core structures may be prepared like the following General Formulas 1 to 9.

The substituent groups may be bonded by the method known in the art, and a position or number of the substituent group may be changed according to the technology known in the art.

[General Formula 1]

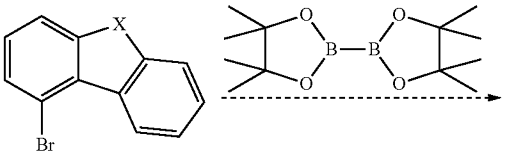

-continued
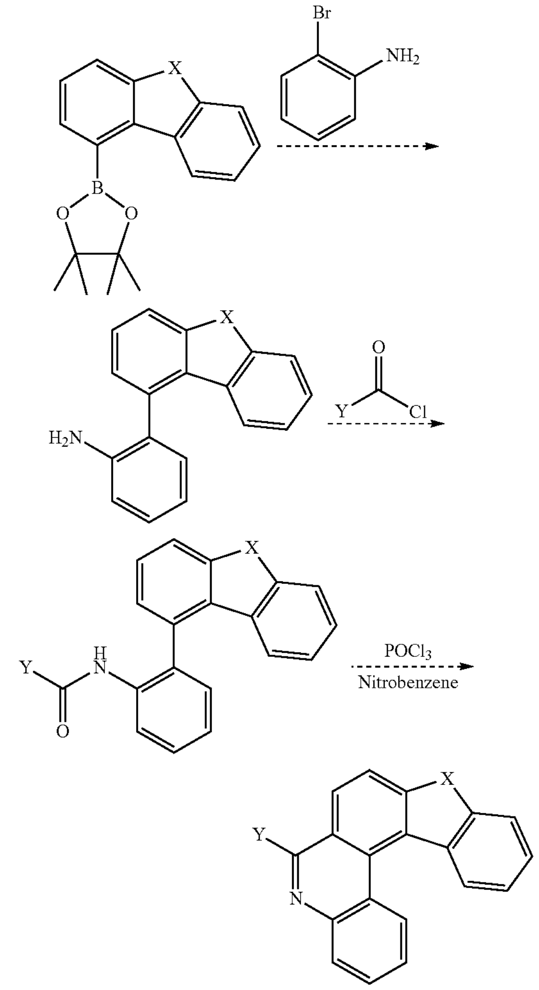
In General Formula 1, X and Y are the same as those of Chemical Formula 1 according to the aforementioned exemplary embodiment, and General Formula 1 is an example of the reaction preparing the core structure of Chemical Formula 2.
[General Formula 2]
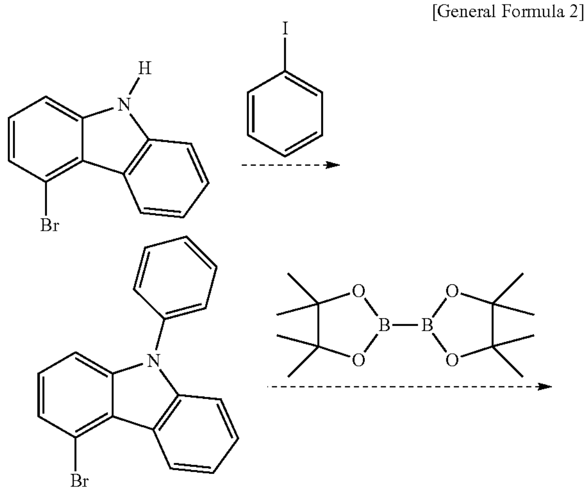
-continued
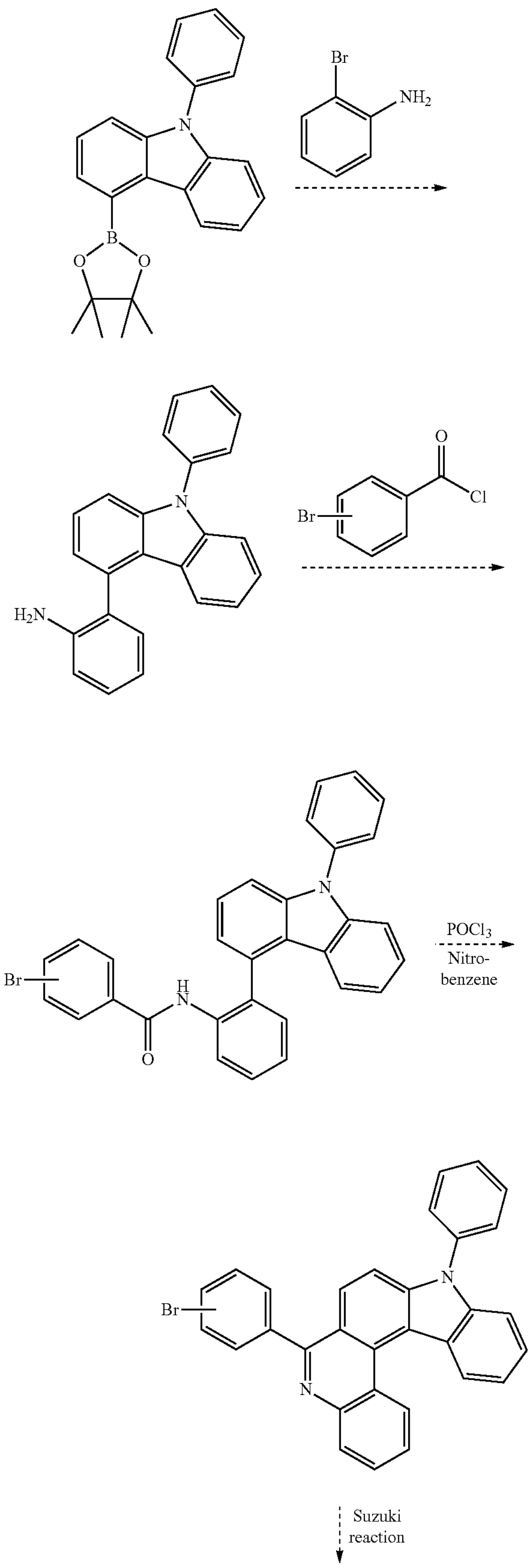

-continued

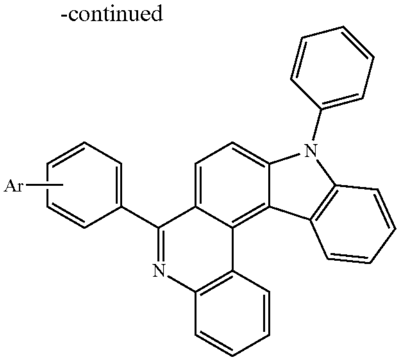

In General Formula 2, Ar is the same as that of the aforementioned exemplary embodiment, and General Formula 2 is an example of the reaction preparing the core structure of Chemical Formula 13.

[General Formula 3]

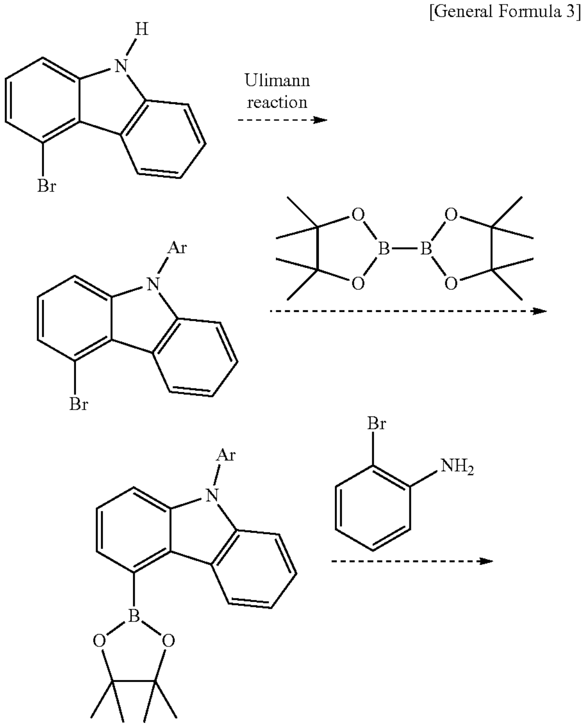

-continued

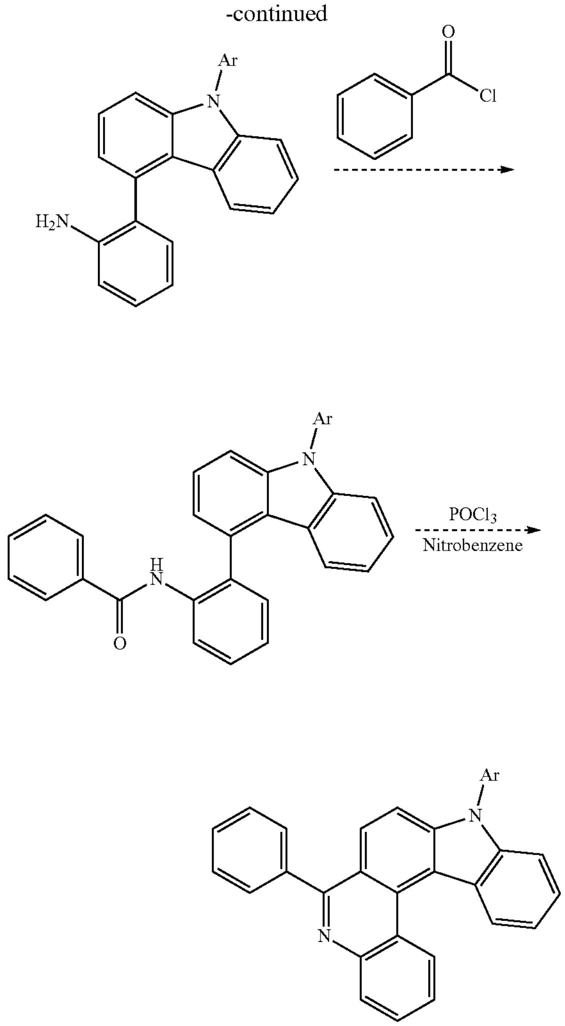

In General Formula 3, Ar is the same as $R_3$ defined in Chemical Formula 1 according to the aforementioned exemplary embodiment, and General Formula 3 is an example of the reaction preparing the core structure of Chemical Formula 14.

[General Formula 4]

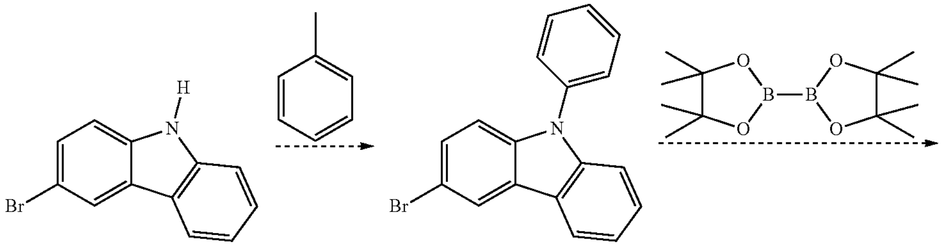

-continued
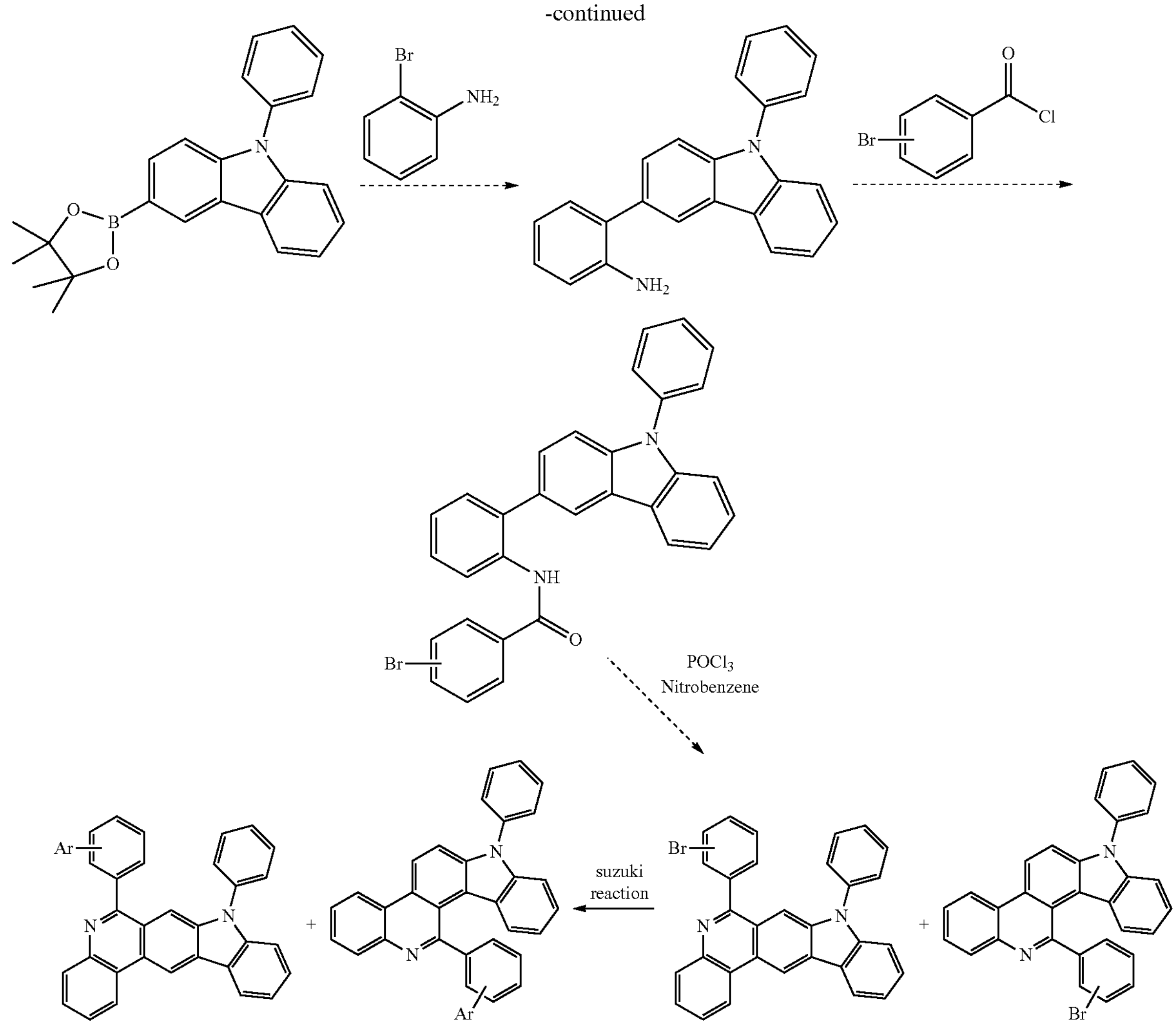
In General Formula 4, Ar is the same as that of the aforementioned exemplary embodiment, and General Formula 4 is an example of the reaction preparing the core structures of Chemical Formulas 15 to 16.
[General Formula 5]
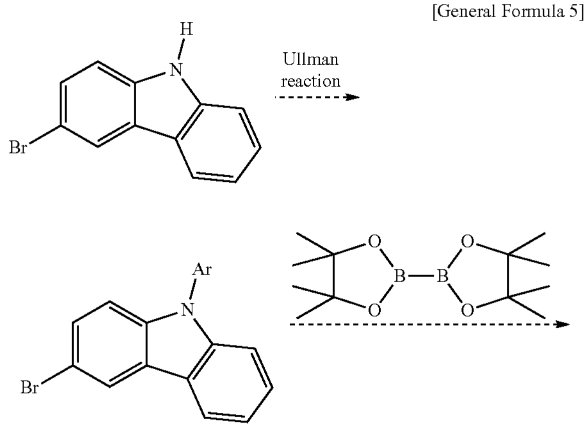
-continued
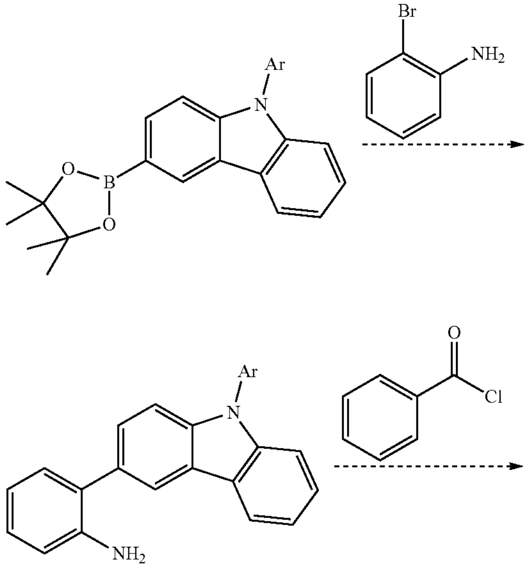

-continued
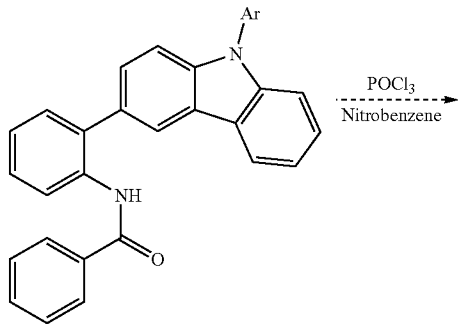
-continued
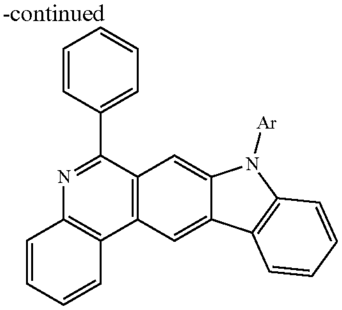
In General Formula 5, Ar is the same as that of the aforementioned exemplary embodiment, and General Formula 5 is an example of the reaction preparing the core structure of Chemical Formula 17.
[General Formula 6]
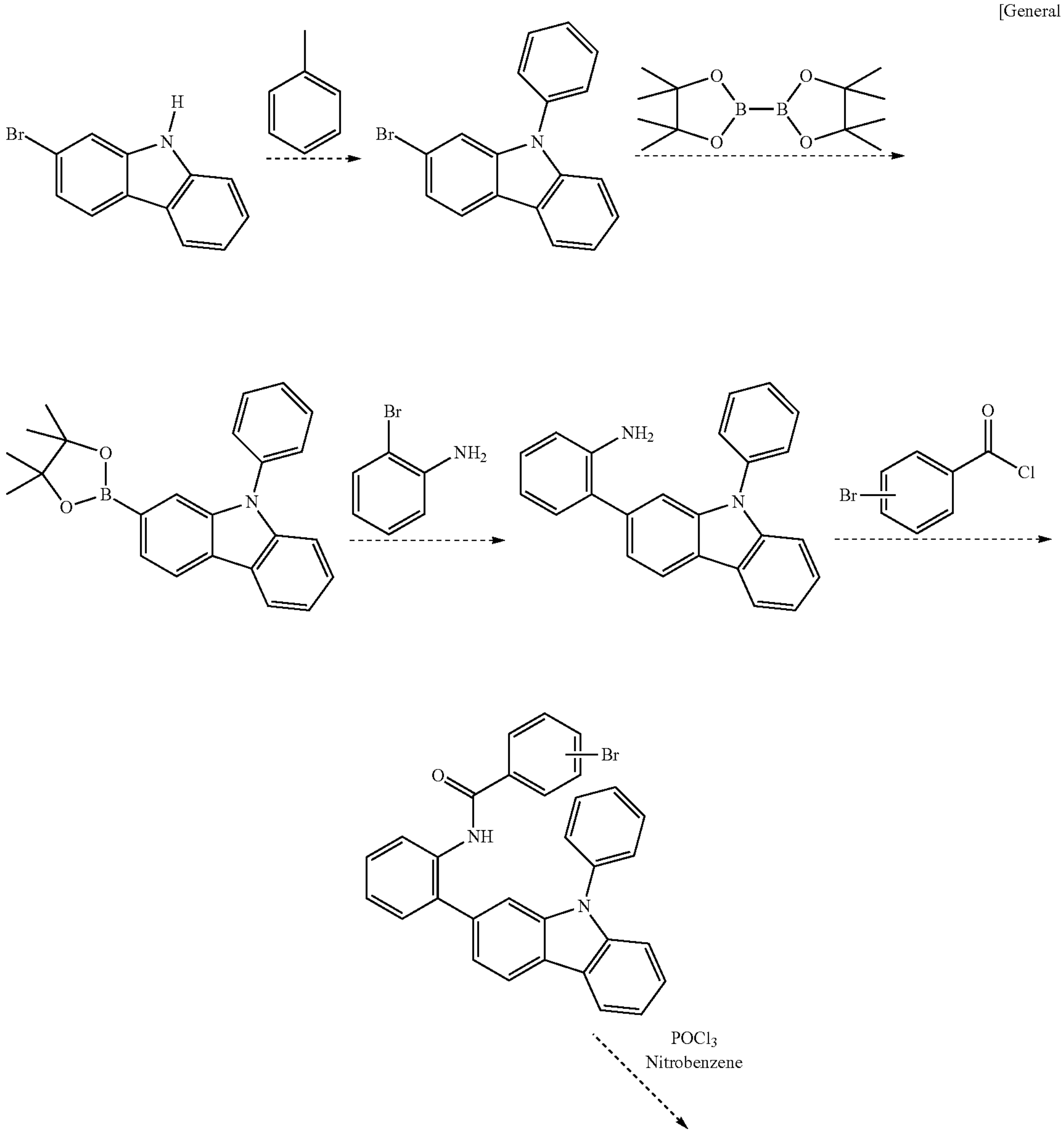

-continued

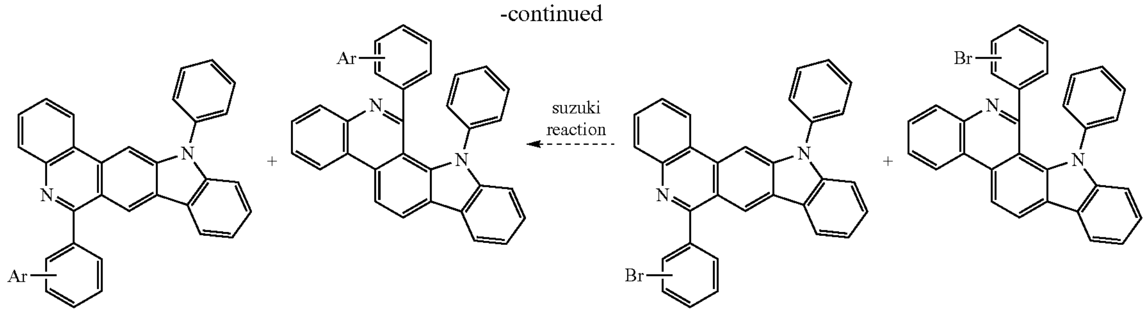

In General Formula 6, Ar is the same as that of the aforementioned exemplary embodiment, and General Formula 6 is an example of the reaction preparing the core structures of Chemical Formulas 18 to 19.

[General Formula 7]

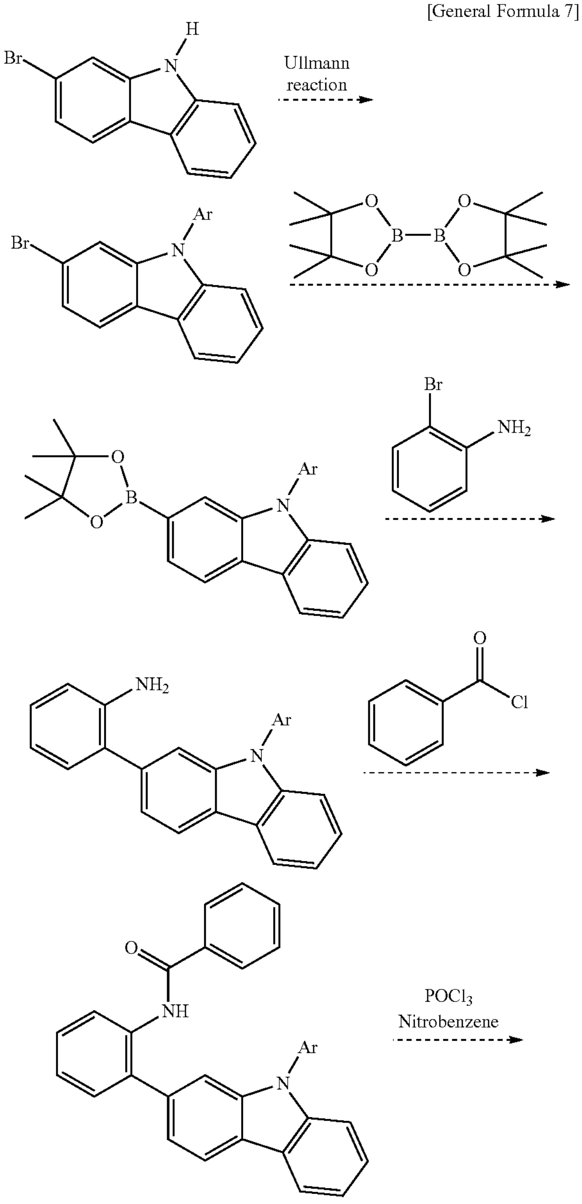

-continued

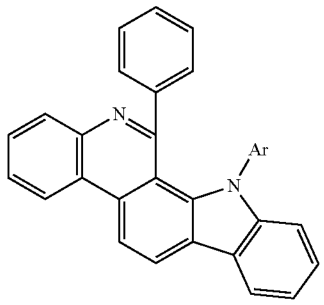

In General Formula 7, Ar is the same as $R_3$ defined in Chemical Formula 1 according to the aforementioned exemplary embodiment, and General Formula 7 is an example of the reaction preparing the core structure of Chemical Formula 20.

[General Formula 8]

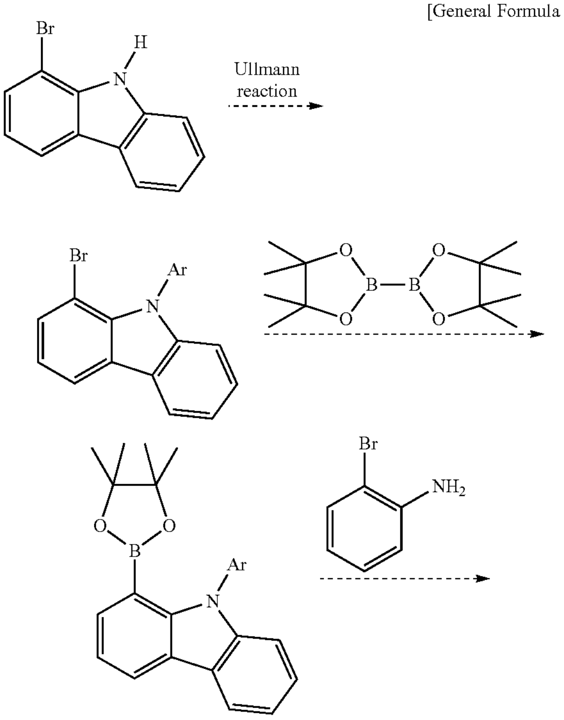

-continued

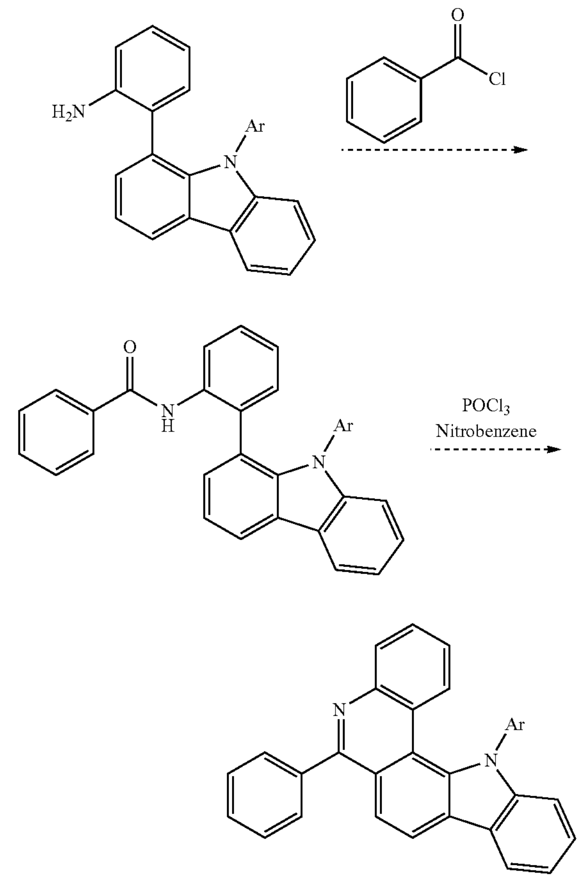

In General Formula 8, Ar is the same as $R_3$ defined in Chemical Formula 1 according to the aforementioned exemplary embodiment, and General Formula 8 is an example of the reaction preparing the core structure of Chemical Formula 23.

[General Formula 9]

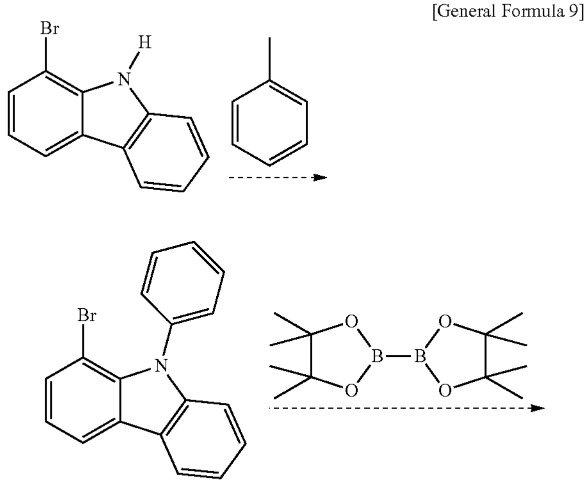

-continued

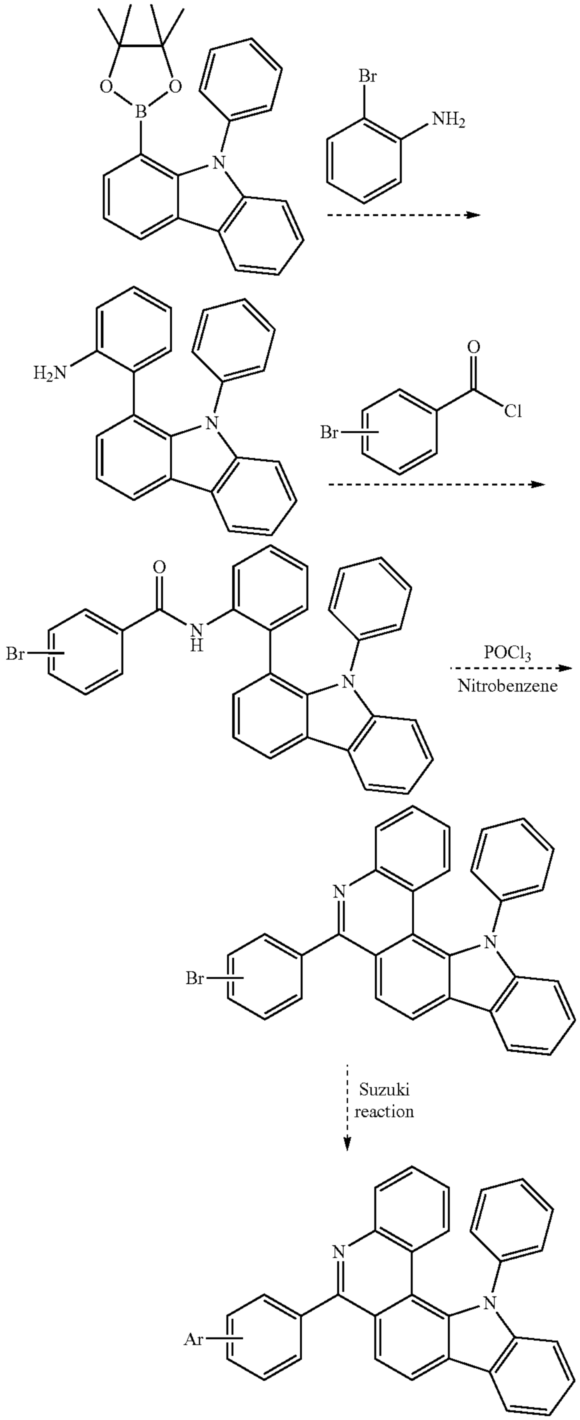

In General Formula 9, Ar is the same as that of the aforementioned exemplary embodiment, and General Formula 9 is an example of the reaction preparing the core structure of Chemical Formula 24.

Another exemplary embodiment of the present specification provides an organic light emitting device including the aforementioned compound of Chemical Formula 1. Specifically, the organic light emitting device according to the present application includes an anode, a cathode, and one or more layers of organic material layers provided between the anode and the cathode, and one or more layers of the organic material layers include the compound of Chemical Formula 1.

FIGS. 1 to 3 illustrate examples of a lamination order of the electrodes and the organic material layers of the organic light emitting device according to the exemplary embodiments of the present application. However, the scope of the present application is not intended to be limited by the drawings, but the structure of the organic light emitting device known in the art may be applied to the present application.

FIG. 1 illustrates an organic light emitting device where an anode 200, an organic material layer 300, and a cathode 400 are sequentially laminated on a substrate 100. However, the organic light emitting device is not limited to the aforementioned structure, but like FIG. 2, an organic light emitting device where the cathode, the organic material layer, and the anode are sequentially laminated on the substrate may be implemented.

FIG. 3 illustrates the case where the organic material layer has multilayers. The organic light emitting device according to FIG. 3 includes a hole injection layer 301, a hole transport layer 302, a light emitting layer 303, a hole blocking layer 304, an electron transport layer 305, and an electron injection layer 306. However, the scope of the present application is not limited by the lamination structure, but if necessary, the residual layers other than the light emitting layer may be omitted, and other required functional layers may be further added.

The organic light emitting device according to the present specification may be manufactured by materials and methods known in the art, except that one or more layers of the organic material layers include the compound of Chemical Formula 1.

The compound of Chemical Formula 1 may solely constitute one or more layers of the organic material layers of the organic light emitting device. However, if necessary, the compound of Chemical Formula 1 may be mixed with another material to constitute the organic material layer.

the compound of Chemical Formula 1 may be used as the material of the electron transport layer, the hole blocking layer, or the light emitting layer in the organic light emitting device. As an example, the compound of Chemical Formula 1 may be used as the material of the electron transport layer or the light emitting layer of the organic light emitting device. Further, the compound of Chemical Formula 1 may be used as the material of the electron transport layer or the phosphorescent host of the light emitting layer.

In the organic light emitting device according to the present specification, the material other than the compound of Chemical Formula 1 is exemplified below, but the materials are only examples but are not construed to limit the scope of the present application, and may be replaced by materials known in the art.

Materials having a relatively high work function may be used as an anode material, and transparent conductive oxide, metal, a conductive polymer, or the like may be used.

Materials having a relatively low work function may be used as a cathode material, and metal, metal oxide, a conductive polymer, or the like may be used.

A known hole injection material may be used as the hole injection material, and for example, phthalocyanine compounds such as copper phthalocyanine disclosed in U.S. Pat. No. 4,356,429, or starburst type amine derivatives described in a document [Advanced Material, 6, p. 677 (1994)], for example, tris(4-carbazoyl-9-ylphenyl)amine (TCTA), 4,4',4"-tri[phenyl(m-tolyl)amino]triphenylamine (m-MTDATA), 1,3,5-tris[4-(3-methylphenylphenylamino)phenyl]benzene (m-MTDAPB), Pani/DB SA (polyaniline/dodecylbenzenesulfonic acid) or PEDOT/PSS (poly(3,4-ethylenedioxythiophene)/poly(4-styrene sulfonate)) that is a conductive polymer having solubility, Pani/CSA (polyaniline/camphor sulfonic acid), PANI/PSS (polyaniline/poly(4-styrene-sulfonate), or the like may be used.

A pyrazoline derivative, an arylamine-based derivative, a stilbene derivative, a triphenyldiamine derivative, or the like may be used as the hole transport material, or a low molecular material or a polymer material may be used.

Metal complexes of an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, and 8-hydroxyquinoline and a derivative thereof may be used as the electron transport material, and a low molecular material and a polymer material may be used.

For example, LiF is representatively used in the art as the electron injection material, but the present application is not limited thereto.

A red, green, or blue light emitting material may be used as the light emitting material, and if necessary, two or more light emitting materials may be used while being mixed. Further, a fluorescent material may be used as the light emitting material, but a phosphorescent material may be used. A material bonding holes and electrons injected from the anode and the cathode, respectively, to emit light may be used alone as the light emitting material, but host materials and dopant materials may be used together as materials involved in light emission.

Hereinafter, the present application will be described in more detail through Examples, which are set forth only to illustrate the present application, but are not to be construed to limit the scope of the present application.

[Preparation Example 1] Preparation of Compound 1-1

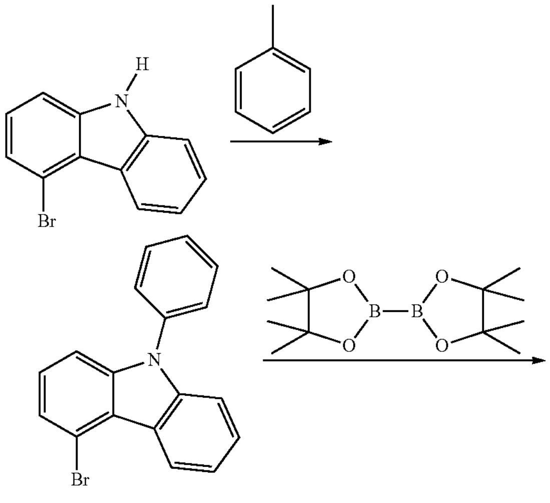

A-1

-continued

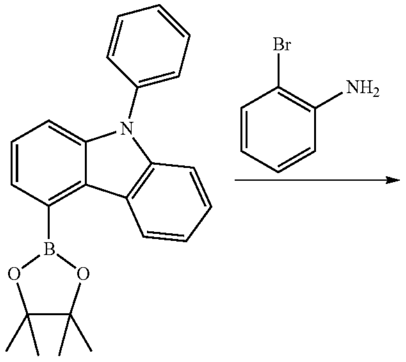

A-2

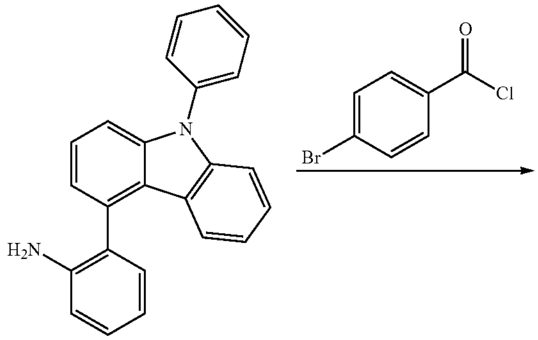

A-3

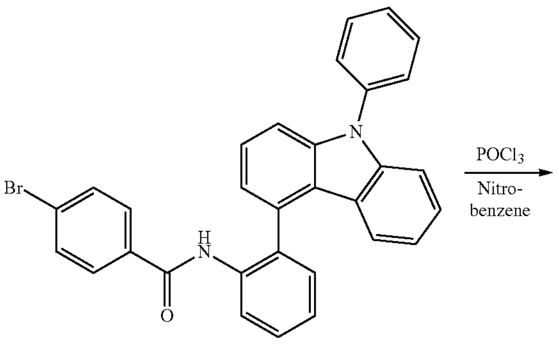

A-4

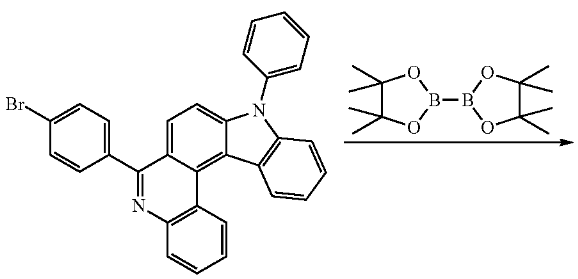

A-5

-continued

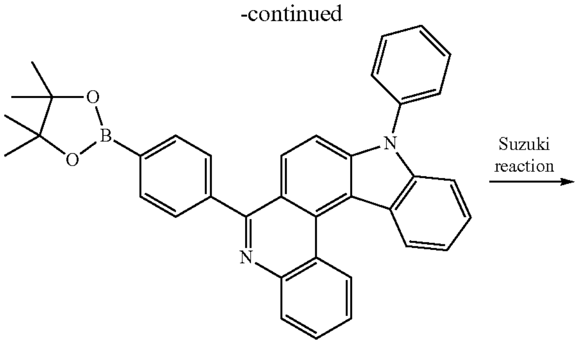

B-1

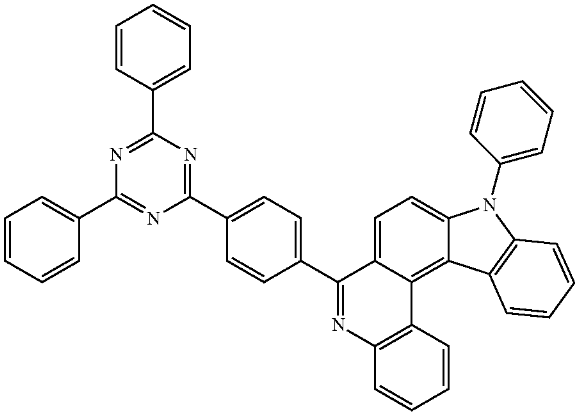

1-1

Synthesis of Compound A-1

50 g (203.16 mmol) of 4-bromo-9H-carbazole, 68 mL (609.48 mmol) of iodobenzene, 1.3 g (20.32 mmol) of Cu, 56 g (406.32 mmol) of $K_2CO_3$, and 6.6 g (20.32 mmol) of 18-crown-6-ether were reacted together with 1 L of 1,2-dichlorobenzene in the sealed tube at 140° C. for 16 hours. After the reaction was finished, cooling was performed to room temperature, and extraction was then performed with distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 60.0 g (92%) of target compound A-1.

Synthesis of Compound A-2

60 g (186.22 mmol) of A-1, 94.5 g (372.44 mmol) of bis(pinacolato)diboron, 54.8 g (558.66 mmol) of potassium acetate (KOAc), and 6.8 g (9.31 mmol) of [1,1'-bis(diphenylphosphino)ferrocene]dichloropalladium(II) were refluxed and stirred under 1,4-dioxane at 120° C. for 3 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane to obtain 42.0 g (61%) of target compound A-2.

Synthesis of Compound A-3

38.8 g (105.0 mmol) of A-2, 36.1 g (210.0 mmol) of 2-bromoaniline, 6.1 g (5.25 mmol) of tetrakis(triphenylphosphine)palladium(0), and 67.0 g (315.0 mmol) of $K_3PO_4$ were refluxed and stirred under 400 mL of 1,4-dioxane and 80 mL of $H_2O$ at 120° C. for 2 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane to obtain 17.5 g (50%) of target compound A-3.

Synthesis of Compound A-4

20 g (59.8 mmol) of A-3, and 8.4 mL (59.8 mmol) of triethylamine were totally dissolved by dichloromethane, and then maintained at 0° C. Thereafter, 13.1 g (59.8 mmol) of 4-bromobenzoyl chloride was slowly dripped to perform stirring while maintaining the temperature for 1 hour. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 23.5 g (76%) of target compound A-4.

Synthesis of Compound A-5

After 29.6 g (57.21 mmol) of A-4 was totally dissolved in 300 mL of nitrobenzene, 6.45 mL (57.21 mmol) of $POCl_3$ was slowly dripped. Thereafter, stirring was performed for 2 hours while the temperature was maintained at 150° C. After the reaction was finished, extraction was performed with distilled water and dichloromethane, the organic layer was dried with anhydrous $MgSO_4$, the solvent was removed by the rotary evaporator, and washing was performed by methanol (MeOH) to obtain 25.5 g (89%) of target compound A-5.

Synthesis of Compound B-1

15 g (30.04 mmol) of A-5, 15.3 g (60.07 mmol) of bis(pinacolato)diboron, 8.84 g (90.12 mmol) of potassium acetate (KOAc), and 1.1 g (1.5 mmol) of [1,1'-bis(diphenylphosphino)ferrocene]dichloropalladium(II) were stirred under 70 mL of dimethylformamide (DMF) at 120° C. for 3 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane and methanol (MeOH) to obtain 12.6 g (77%) of target compound B-1.

Synthesis of Compound 1-1

9.0 g (16.47 mmol) of B-1, 5.3 g (19.76 mmol) of 2-chloro-4,6-diphenyl-1,3,5-triazine, 1.9 g (1.65 mmol) of tetrakis(triphenylphosphine)palladium(0), and 6.8 g (49.41 mmol) of $K_2CO_3$ were stirred under 90 mL of toluene and 18 mL of each of ethanol (EtOH)/$H_2O$ at 120° C. for 3 hours. After the reaction was finished, cooling was performed to room temperature to generate the solid, and the solid was filtered, and then washed with dichloromethane, ethyl acetate (EA), and methanol (MeOH). Thereafter, the solid was totally dissolved by an excessive amount of dichloromethane, and filtered by the silica gel to obtain 5.7 g (53%) of target compound 1-1.

[Preparation Example 2] Preparation of Compound 1-12

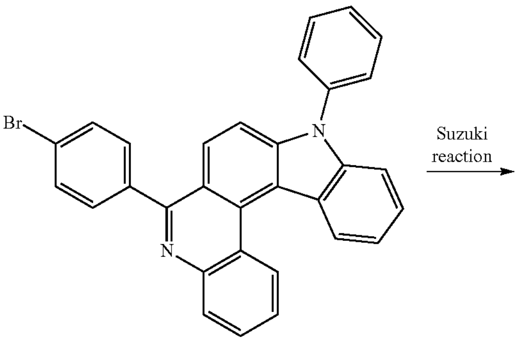

A-5

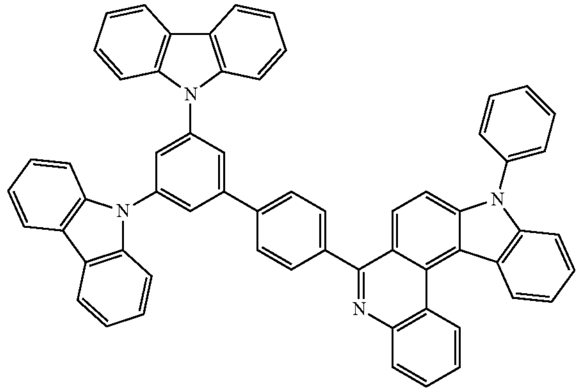

1-12

Synthesis of Compound 1-12

8.0 g (16.02 mmol) of A-5, 10.3 g (19.22 mmol) of 9,9'-(5-(4,4,5,5-tetramethyl-1,3,2-dioxaborolan-2-yl)-1,3-phenylene)bis(9H-carbazole), 0.93 g (0.8 mmol) of tetrakis(triphenylphosphine)palladium(0), and 10.2 g (48.06 mmol) of $K_3PO_4$ were refluxed and stirred under 160 mL of 1,4-dioxane and 32 mL of $H_2O$ at 120° C. for 2 hours. After the reaction was finished, cooling was performed to room temperature to generate the solid, and the solid was filtered, and then washed with dichloromethane, ethyl acetate (EA), and methanol (MeOH). Thereafter, the solid was totally dissolved by an excessive amount of dichloromethane, and then filtered by the silica gel to obtain 10.3 g (78%) of target compound 1-12.

[Preparation Example 3] Preparation of Compound 1-16

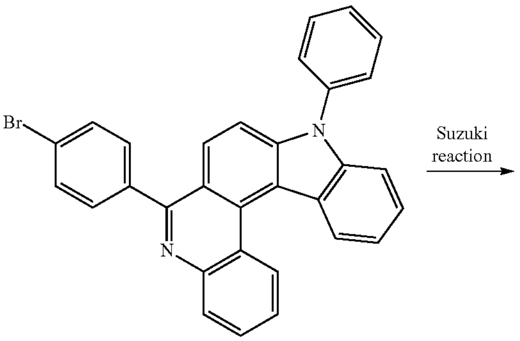

A-5

-continued

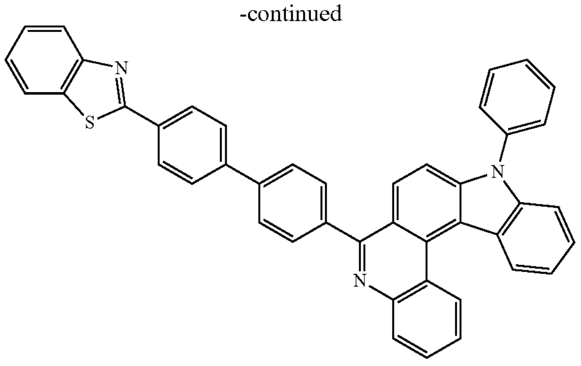

1-16

Synthesis of Compound 1-16

8.0 g (16.02 mmol) of A-5, 6.48 g (19.22 mmol) of 2-(4-(4,4,5,5-tetramethyl-1,3,2-dioxaborolan-2-yl)phenyl) benzo[d]thiazole, 0.93 g (0.8 mmol) of tetrakis(triphenyl-phosphine)palladium(0), and 10.2 g (48.06 mmol) of $K_3PO_4$ were refluxed and stirred under 160 mL of 1,4-dioxane and 32 mL of $H_2O$ at 120° C. for 4 hours. After the reaction was finished, cooling was performed to room temperature to generate the solid, and the solid was filtered, and then washed with dichloromethane, ethyl acetate (EA), and methanol (MeOH). Thereafter, the solid was totally dissolved by an excessive amount of dichloromethane, and then filtered by the silica gel to obtain 7.9 g (78%) of target compound 1-16.

[Preparation Example 4] Preparation of Compound 1-36

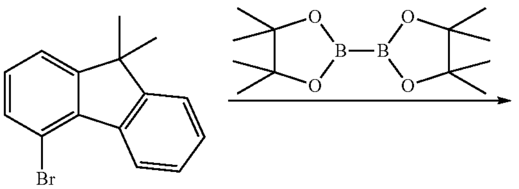

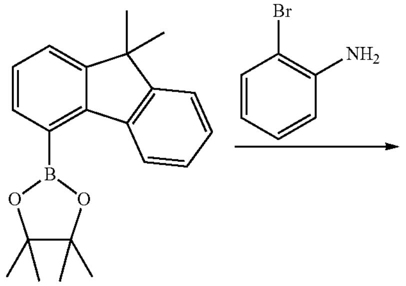

C-1

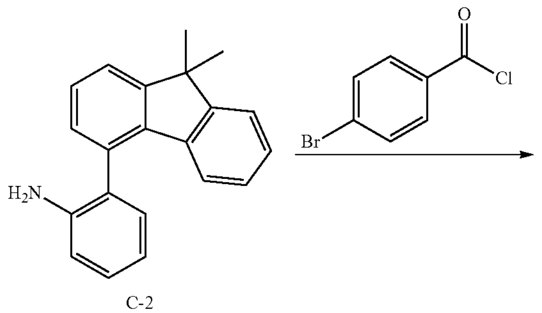

C-2

-continued

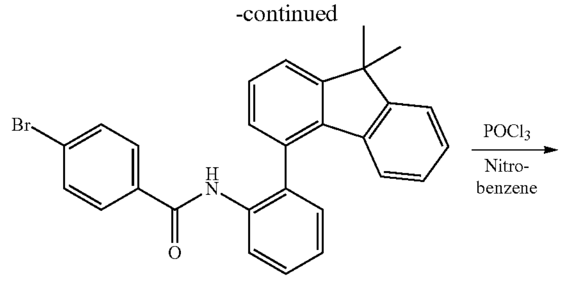

C-3

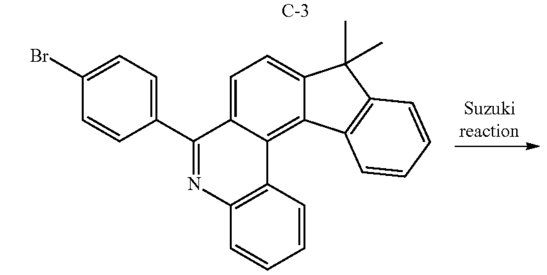

C-4

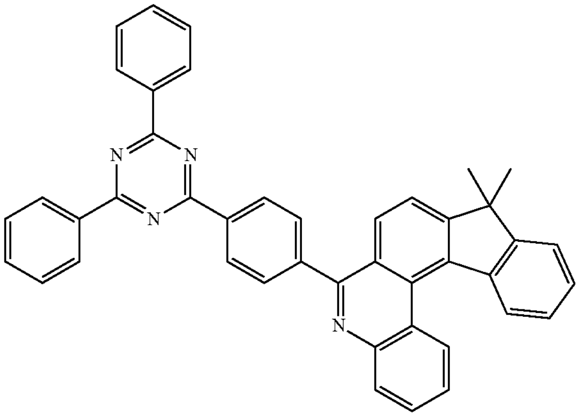

1-36

Synthesis of Compound C-1

20 g (73.21 mmol) of 4-bromo-9,9-dimethyl-9H-fluorene, 37.2 g (146.43 mmol) of bis(pinacolato)diboron, 21.5 g (219.63 mmol) of potassium acetate (KOAc), and 2.68 g (3.66 mmol) of [1,1'-bis(diphenylphosphino)ferrocene]dichloropalladium(II) were stirred under 200 mL of dimethylformamide (DMF) at 120° C. for 16 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane to obtain 19.0 g (81%) of target compound C-1.

Synthesis of Compound C-2

17.3 g (54.02 mmol) of C-1, 18.6 g (108.04 mmol) of 2-bromoaniline, 3.12 g (2.70 mmol) of tetrakis(triphenyl-phosphine)palladium(0), and 34.4 g (162.06 mmol) of $K_3PO_4$ were refluxed and stirred under 170 mL of 1,4-dioxane and 30 mL of $H_2O$ at 120° C. for 3 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane and methanol (MeOH) (small amount) to obtain 13.0 g (84%) of target compound C-2.

Synthesis of Compound C-3

13.0 g (45.55 mmol) of C-2, and 6.4 mL (45.55 mmol) of triethylamine were totally dissolved by dichloromethane, and then maintained at 0° C. Thereafter, 9.99 g (45.55 mmol) of 4-bromobenzoyl chloride was slowly dripped to perform stirring while maintaining the temperature for 1 hour. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 15.0 g (76%) of target compound C-3.

Synthesis of Compound C-4

After 15.0 g (32.02 mmol) of C-3 was totally dissolved in 150 mL of nitrobenzene, 3.6 mL (32.02 mmol) of $POCl_3$ was slowly dripped. Thereafter, stirring was performed for 2 hours while the temperature was maintained at 150° C. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 8.8 g (61%) of target compound C-4.

Synthesis of Compound 1-36

10.0 g (20.10 mmol) of C-4, 6.46 g (24.12 mmol) of 2-chloro-4,6-diphenyl-1,3,5-triazine, 2.3 g (2.01 mmol) of tetrakis(triphenylphosphine)palladium(0), and 12.8 g (60.3 mmol) of $K_3PO_4$ were refluxed and stirred under 120 mL of 1,4-dioxane and 20 mL of $H_2O$ at 120° C. for 2 hours. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 8.2 g (68%) of target compound 1-36.

[Preparation Example 5] Preparation of Compound 1-113

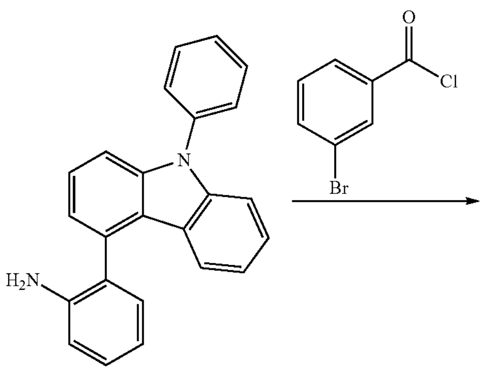

A-3

-continued

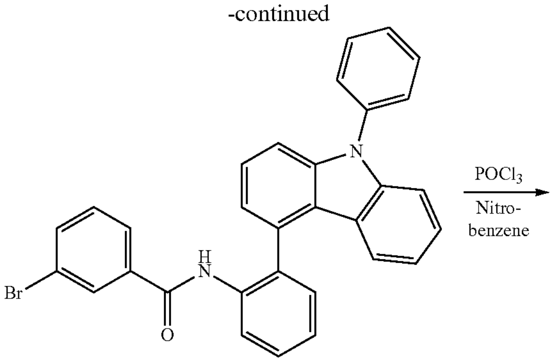

D-1

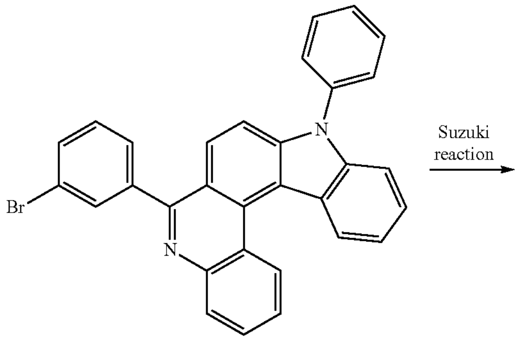

D-2

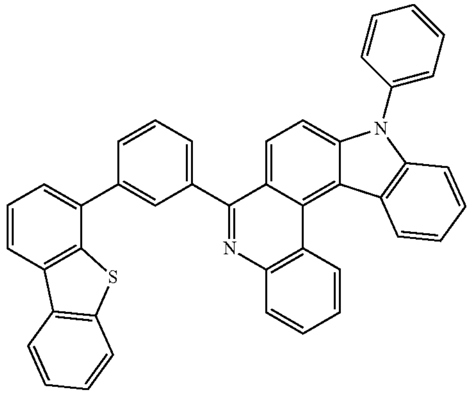

1-113

Synthesis of Compound D-1

20 g (59.8 mmol) of A-3, and 8.4 mL (59.8 mmol) of triethylamine were totally dissolved by dichloromethane, and then maintained at 0° C. Thereafter, 13.1 g (59.8 mmol) of 3-bromobenzoyl chloride was slowly dripped to perform stirring while maintaining the temperature for 1 hour. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 24.9 g (80%) of target compound D-1.

Synthesis of Compound D-2

After 27.0 g (52.18 mmol) of D-1 was totally dissolved in 300 mL of nitrobenzene, 5.9 mL (52.18 mmol) of $POCl_3$ was slowly dripped. Thereafter, stirring was performed for 2 hours while the temperature was maintained at 150° C. After the reaction was finished, extraction was performed with distilled water and dichloromethane, the organic layer was dried with anhydrous $MgSO_4$, the solvent was removed by the rotary evaporator, and washing was performed by methanol (MeOH) to obtain 26.7 g (93%) of target compound D-2.

Synthesis of Compound 1-113

10 g (20.02 mmol) of D-2, 5.5 g (24.03 mmol) of dibenzo[b,d]thiophen-4-yl boronic acid, 2.3 g (2.0 mmol) of tetrakis(triphenylphosphine)palladium(0), and 8.3 g (60.06 mmol) of $K_2CO_3$ were refluxed and stirred under 200 mL of toluene, 40 mL of ethanol (EtOH), and 40 mL of $H_2O$ at 120° C. for 6 hours. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 9.5 g (79%) of target compound 1-113.

[Preparation Example 6] Preparation of Compound 1-119

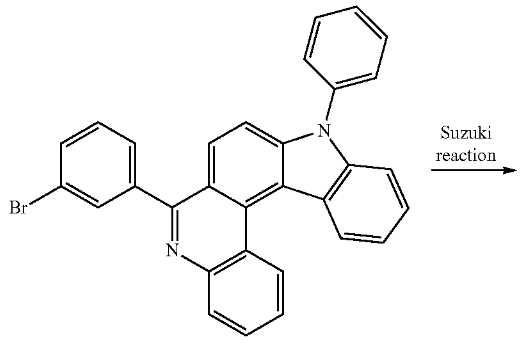

D-2

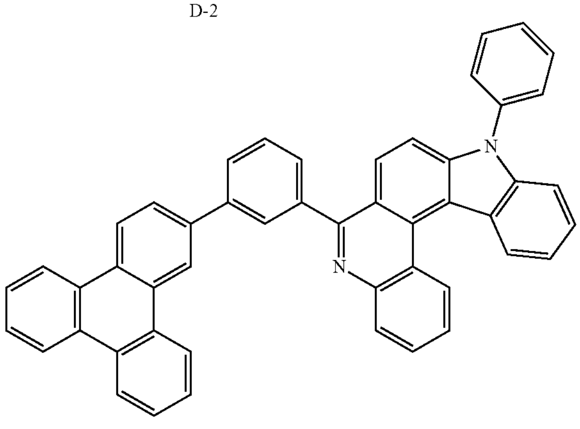

1-119

Synthesis of Compound 1-119

7 g (14.02 mmol) of D-2, 5.96 g (16.82 mmol) of 4,4,5,5-tetramethyl-2-(triphenylen-2-yl)-1,3,2-dioxaborolane, 1.62 g (1.4 mmol) of tetrakis(triphenylphosphine) palladium(0), and 5.81 g (42.06 mmol) of $K_2CO_3$ were refluxed and stirred under 140 mL of toluene, 28 mL of ethanol (EtOH), and 28 mL of $H_2O$ at 120° C. for 3 hours. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 4.92 g (54%) of target compound 1-119.

[Preparation Example 7] Preparation of Compound 1-124

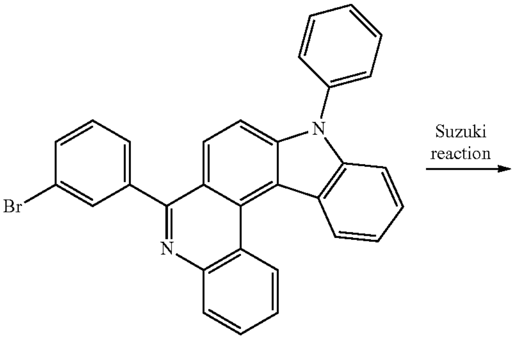

D-2

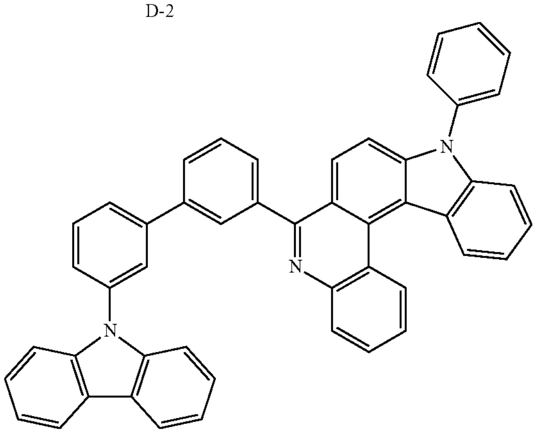

1-124

Synthesis of Compound 1-124

7 g (14.02 mmol) of D-2, 6.21 g (16.82 mmol) of 9-(3-(4,4,5,5-tetramethyl-1,3,2-dioxaborolan-2-yl)phenyl)-9H-carbazole, 1.62 g (1.4 mmol) of tetrakis(triphenylphosphine)palladium(0), and 5.81 g (42.06 mmol) of $K_2CO_3$ were refluxed and stirred under 140 mL of toluene, 28 mL of ethanol (EtOH), and 28 mL of $H_2O$ at 120° C. for 4 hours. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 6.39 g (69%) of target compound 1-124.

[Preparation Example 8] Preparation of Compound 1-157

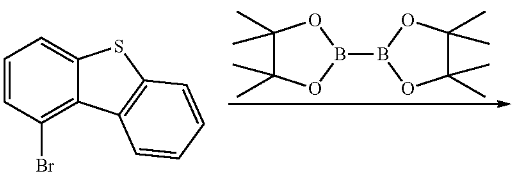

-continued

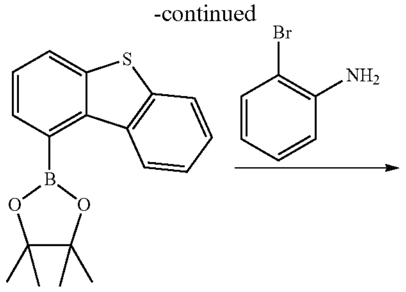

E-1

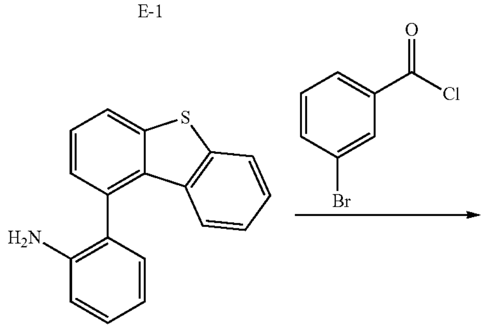

E-2

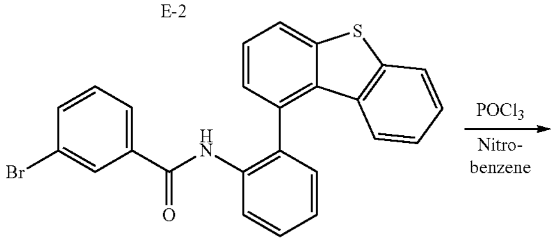

E-3

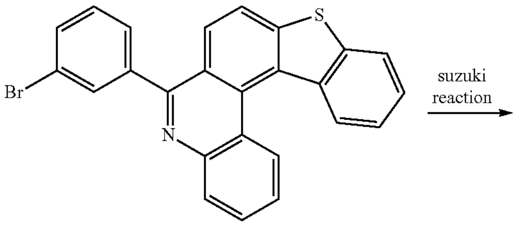

E-4

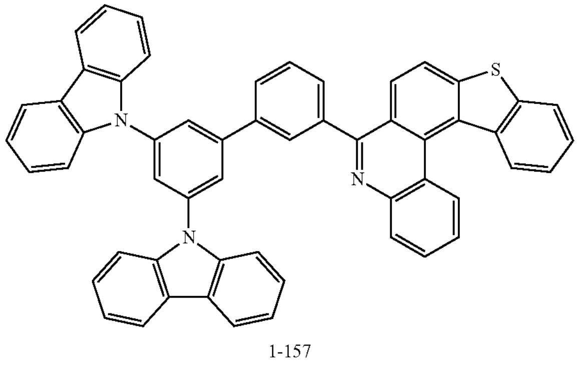 [SMILES: c1cc(-c2cc(-n3c4ccccc4c4ccccc43)cc(-n3c4ccccc4c4ccccc43)c2)cc(-c2nc3ccccc3c3c2ccc2sc4ccccc4c23)c1]

1-157

Synthesis of Compound E-1

50 g (190.0 mmol) of 1-bromodibenzothiophene, 96.5 g (380.0 mmol) of bis(pinacolato)diboron, 55.9 g (570.0 mmol) of potassium acetate (KOAc), and 6.95 g (9.50 mmol) of [1, F-bis(diphenylphosphino)ferrocene]dichloropalladium(II) were stirred under 500 mL of 1,4-dioxane at 120° C. for 16 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane to obtain 51.6 g (88%) of target compound E-1.

Synthesis of Compound E-2

50.0 g (161.17 mmol) of E-1, 55.5 g (322.35 mmol) of 2-bromoaniline, 9.3 g (8.06 mmol) of tetrakis(triphenylphosphine)palladium(0), and 102.63 g (483.51 mmol) of $K_3PO_4$ were refluxed and stirred under 500 mL of 1,4-dioxane and 100 mL of $H_2O$ at 120° C. for 6 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane to obtain 33.8 g (76%) of target compound E-2.

Synthesis of Compound E-3

30 g (108.94 mmol) of E-2, and 15.3 mL (108.94 mmol) of triethylamine were totally dissolved by dichloromethane, and then maintained at 0° C. Thereafter, 23.9 g (108.94 mmol) of 3-bromobenzoyl chloride was slowly dripped to perform stirring while maintaining the temperature for 2 hour. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 43.7 g (87%) of target compound E-3.

Synthesis of Compound E-4

After 43.0 g (93.8 mmol) of E-3 was totally dissolved in 430 mL of nitrobenzene, 10.6 mL (93.8 mmol) of $POCl_3$ was slowly dripped. Thereafter, stirring was performed for 1 hours while the temperature was maintained at 150° C. After the reaction was finished, extraction was performed with distilled water and dichloromethane, the organic layer was dried with anhydrous $MgSO_4$, the solvent was removed by the rotary evaporator, and washing was performed by methanol (MeOH) to obtain 37.5 g (91%) of target compound E-4.

Synthesis of Compound 1-157

8.0 g (18.17 mmol) of E-4, 11.85 g (21.8 mmol) of 9,9'-(5-(4,4,5,5-tetramethyl-1,3,2-dioxaborolan-2-yl)-1,3-phenylene)bis(9H-carbazole), 1.05 g (0.91 mmol) of tetrakis (triphenylphosphine)palladium(0), and 11.57 g (54.51 mmol) of $K_3PO_4$ were refluxed and stirred under 160 mL of 1,4-dioxane and 32 mL of $H_2O$ at 120° C. for 7 hours. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 9.5 g (68%) of target compound 1-157.

[Preparation Example 9] Preparation of Compound 1-190

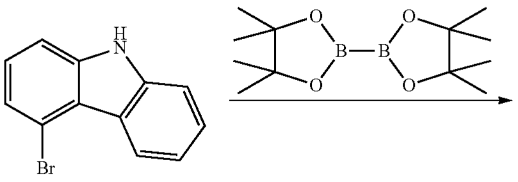

-continued

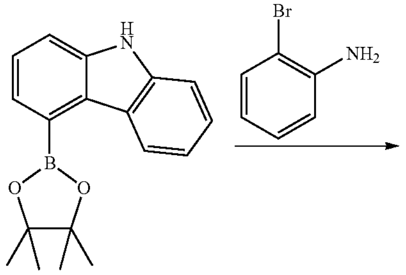

F-1

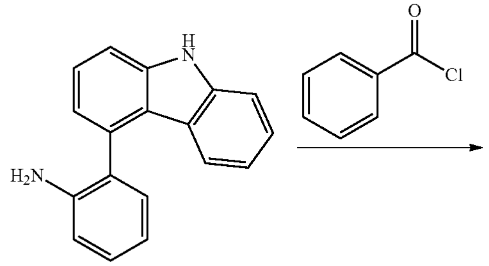

F-2

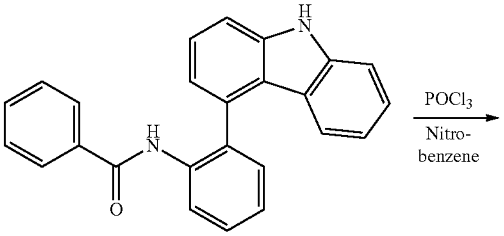

F-3

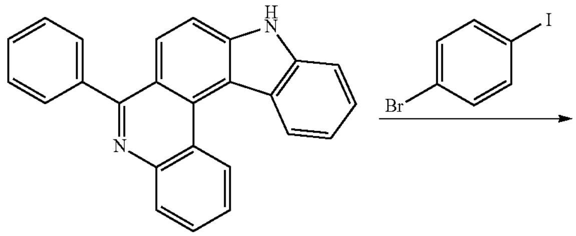

F-4

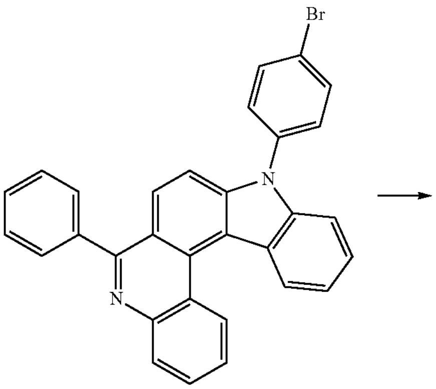

F-5

-continued

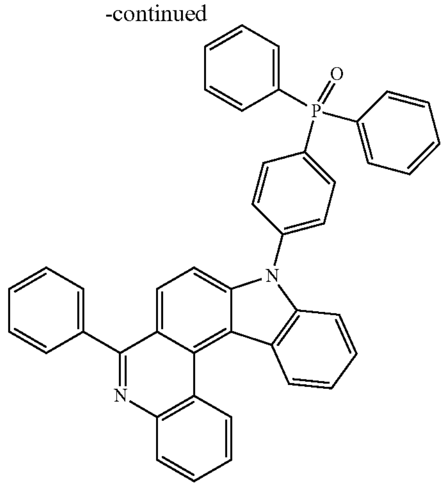

1-190

Synthesis of Compound F-1

20 g (81.26 mmol) of 4-bromo-9H-carbazole, 41.3 g (162.52 mmol) of bis(pinacolato)diboron, 23.9 g (243.78 mmol) of potassium acetate (KOAc), and 2.97 g (4.1 mmol) of [1,1'-bis(diphenylphosphino)ferrocene]dichloropalladium(II) were refluxed and stirred under 100 mL of 1,4-dioxane at 120° C. for 6 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane to obtain 21.2 g (89%) of target compound F-1.

Synthesis of Compound F-2

20.0 g (68.22 mmol) of F-1, 23.5 g (136.44 mmol) of 2-bromoaniline, 3.94 g (3.41 mmol) of tetrakis(triphenylphosphine)palladium(0), and 43.44 g (204.66 mmol) of $K_3PO_4$ were refluxed and stirred under 200 mL of 1,4-dioxane and 40 mL of $H_2O$ at 120° C. for 8 hours. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 11.7 g (66%) of target compound F-2.

Synthesis of Compound F-3

11.7 g (45.3 mmol) of F-2, and 6.37 mL (45.3 mmol) of triethylamine were totally dissolved by dichloromethane, and then maintained at 0° C. Thereafter, 6.37 g (45.3 mmol) of benzoyl chloride was slowly dripped to perform stirring while maintaining the temperature for 1 hour. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 14.5 g (88%) of target compound F-3.

Synthesis of Compound F-4

After 14.0 g (38.63 mmol) of F-3 was totally dissolved in 140 mL of nitrobenzene, 4.36 mL (38.63 mmol) of $POCl_3$ was slowly dripped. Thereafter, stirring was performed for 2 hours while the temperature was maintained at 150° C. After the reaction was finished, extraction was performed with distilled water and dichloromethane, the organic layer was dried with anhydrous $MgSO_4$, the solvent was removed by the rotary evaporator, and washing was performed by methanol (MeOH) to obtain 10.5 g (79%) of target compound F-4.

Synthesis of Compound F-5

10.0 g (29.03 mmol) of F-4, 9.84 g (34.84 mmol) of 1-iodo-4-bromobenzene, 1.68 g (1.45 mmol) of tetrakis (triphenylphosphine)palladium(0), and 18.49 g (87.09 mmol) of $K_3PO_4$ were refluxed and stirred under 100 mL of 1,4-dioxane and 20 mL of $H_2O$ at 120° C. for 3 hours. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 12.7 g (87%) of target compound F-5.

Synthesis of Compound 1-190

After 10 g (20.02 mmol) of F-5 was totally dissolved in 30 mL of tetrahydrofuran (THF), 10.4 mL (26.02 mmol) of n-butyllithium (n-BuLi) (2.5M in hexane) was slowly dripped while the temperature was maintained at −78° C., followed by stirring for 1 hour. 4.8 mL (26.02 mmol) of chlorodiphenylphosphine was dripped on the resultant solution, followed by stirring at room temperature for 12 hours. After the organic layer was dried with anhydrous $MgSO_4$, the solvent was removed by the rotary evaporator, the resulting organic layer was dissolved in 150 mL of dichloromethane, followed by stirring together with 10 mL of 30% $H_2O_2$ aqueous solution at room temperature for 16 hours. After the organic layer was dried with anhydrous $MgSO_4$, the solvent was removed by the rotary evaporator, and purification was performed by the column chromatography by using dichloromethane and hexane as the developing solvent to obtain 6.3 g (51%) of target compound 1-190.

[Preparation Example 10] Preparation of Compound 2-3

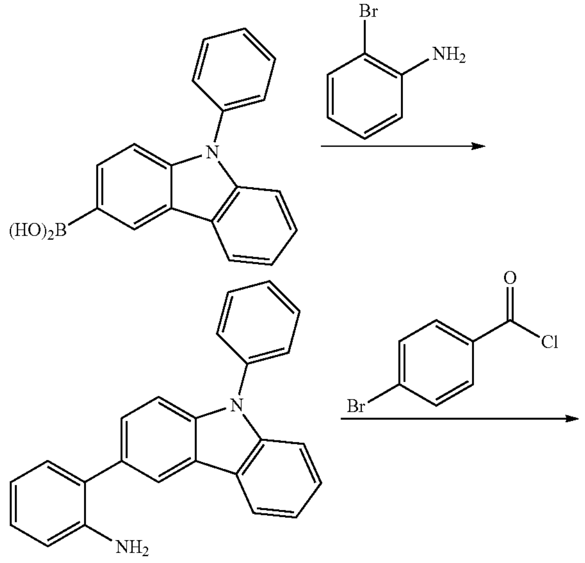

G-1

-continued

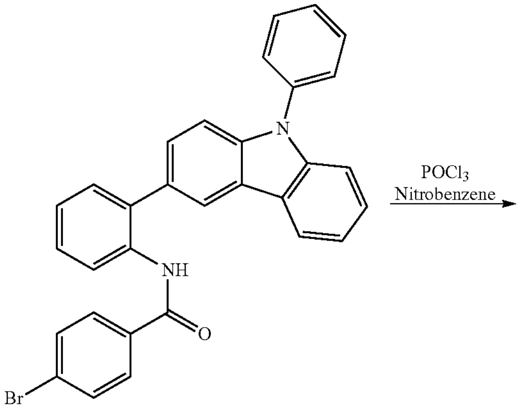

G-2

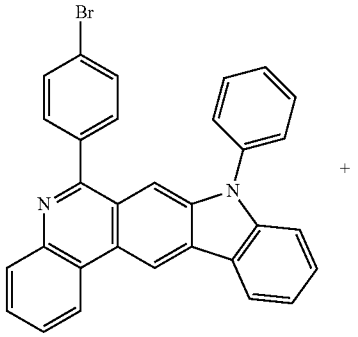

G-3

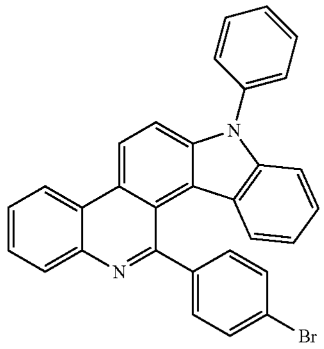

G-3'

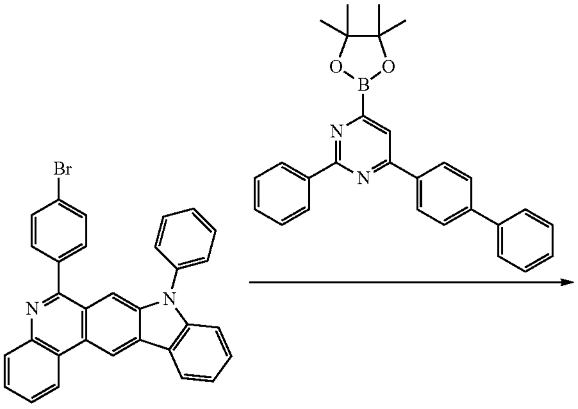

G-3

-continued

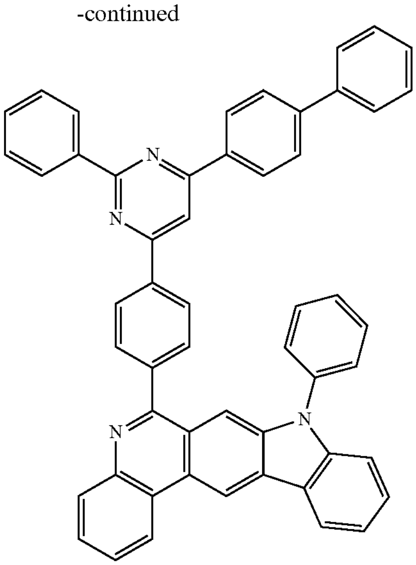

2-3

Synthesis of Compound G-1

38.8 g (105.0 mmol) of (9-phenyl-9H-carbazol-3-yl)boronic acid, 36.1 g (210.0 mmol) of 2-bromoaniline, 6.1 g (5.25 mmol) of tetrakis(triphenylphosphine)palladium(0), and 67.0 g (315.0 mmol) of $K_3PO_4$ were refluxed and stirred under 400 mL of 1,4-dioxane and 80 mL of $H_2O$ at 120° C. for 2 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane to obtain 22.3 g (63%) of target compound G-1.

Synthesis of Compound G-2

20 g (59.8 mmol) of G-1, and 8.4 mL (59.8 mmol) of triethylamine were totally dissolved by dichloromethane, and then maintained at 0° C. Thereafter, 13.1 g (59.8 mmol) of 4-bromobenzoyl chloride was slowly dripped to perform stirring while maintaining the temperature for 1 hour. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 28.0 g (91%) of target compound G-2.

Synthesis of Compounds G-3 and G-3'

After 29.6 g (57.21 mmol) of G-2 was totally dissolved in 300 mL of nitrobenzene, 6.45 mL (57.21 mmol) of $POCl_3$ was slowly dripped. Thereafter, stirring was performed for 2 hours while the temperature was maintained at 150° C. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 18.9 g (66%) of target compound G-3 and 6.24 g (22%) of target compound G-3'.

Synthesis of Compound 2-3

10.0 g (20.02 mmol) of G-3, 10.4 g (24.03 mmol) of 4-([1,1'-biphenyl]-4-yl)-2-phenyl-6-(4,4,5,5-tetramethyl-1,3,2-dioxaborolan-2-yl)pyrimidine, 2.3 g (2.0 mmol) of tetrakis(triphenylphosphine)palladium(0), and 12.75 g (60.06 mmol) of $K_3PO_4$ were refluxed and stirred under 200 mL of 1,4-dioxane and 40 mL of $H_2O$ at 120° C. for 8 hours. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 9.6 g (66%) of target compound 2-3.

[Preparation Example 11] Preparation of Compound 2-44

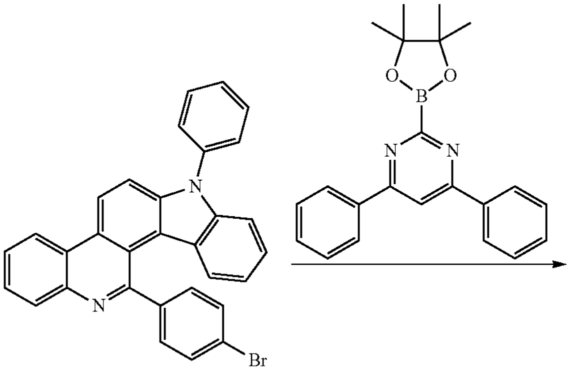

G-3'

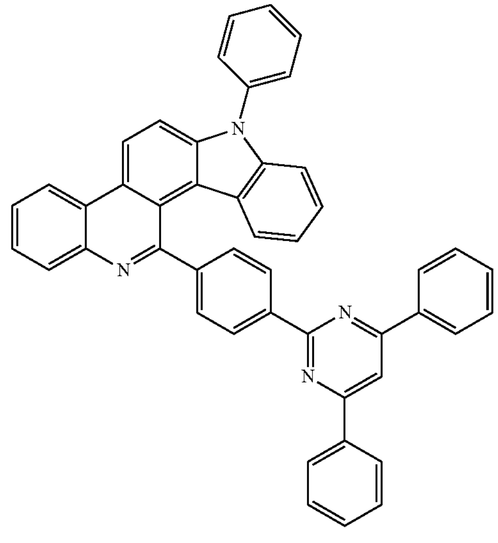

2-44

Synthesis of Compound 2-44

6.0 g (12.01 mmol) of G-3', 5.16 g (14.42 mmol) of 4,6-diphenyl-2-(4,4,5,5-tetramethyl-1,3,2-dioxaborolan-2-yl)pyrimidine, 1.39 g (1.2 mmol) of tetrakis(triphenylphosphine)palladium(0), and 7.65 g (36.03 mmol) of $K_3PO_4$ were refluxed and stirred under 120 mL of 1,4-dioxane and 24 mL of $H_2O$ at 120° C. for 2 hours. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 6.64 g (85%) of target compound 2-44.

[Preparation Example 12] Preparation of Compound 2-107

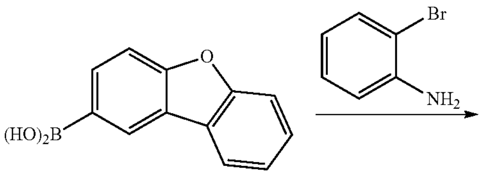

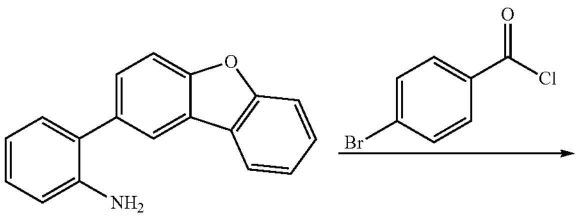

H-1

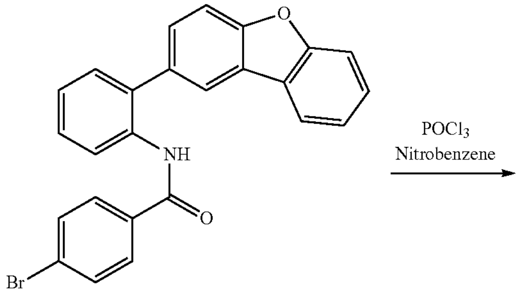

H-2

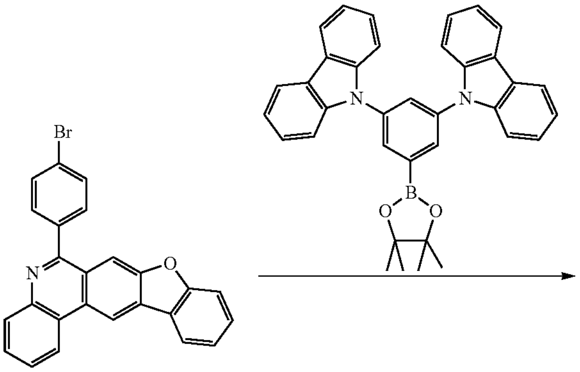

H-3

-continued

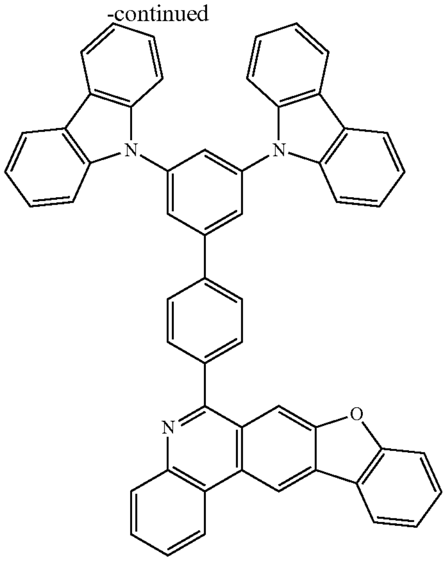

2-107

Synthesis of Compound H-1

20.0 g (94.33 mmol) of dibenzofuran-2-yl boronic acid, 32.45 g (188.66 mmol) of 2-bromoaniline, 5.45 g (4.72 mmol) of tetrakis(triphenylphosphine)palladium(0), and 60.07 g (282.99 mmol) of $K_3PO_4$ were refluxed and stirred under 400 mL of 1,4-dioxane and 80 mL of $H_2O$ at 120° C. for 3 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane to obtain 21.5 g (88%) of target compound H-1.

Synthesis of Compound H-2

20 g (77.13 mmol) of H-1, and 10.8 mL (77.13 mmol) of triethylamine were totally dissolved by dichloromethane, and then maintained at 0° C. Thereafter, 16.9 g (77.13 mmol) of 4-bromobenzoyl chloride was slowly dripped to perform stirring while maintaining the temperature for 1 hour. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 32.4 g (95%) of target compound H-2.

Synthesis of Compound H-3

After 32.0 g (72.35 mmol) of H-2 was totally dissolved in 600 mL of nitrobenzene, 8.16 mL (72.35 mmol) of $POCl_3$ was slowly dripped. Thereafter, stirring was performed for 2 hours while the temperature was maintained at 150° C. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 17.8 g (58%) of target compound H-3.

Synthesis of Compound 2-107

10.0 g (23.57 mmol) of H-3, 15.1 g (28.28 mmol) of 9,9'-(5-(4,4,5,5-tetramethyl-1,3,2-dioxaborolan-2-yl)-1,3-phenylene)bis(9H-carbazole), 1.36 g (1.18 mmol) of tetrakis (triphenylphosphine)palladium(0), and 15.0 g (70.71 mmol)

of $K_3PO_4$ were refluxed and stirred under 200 mL of 1,4-dioxane and 40 mL of $H_2O$ at 120° C. for 2 hours. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 12.1 g (68%) of target compound 2-107.

[Preparation Example 13] Preparation of Compound 2-123

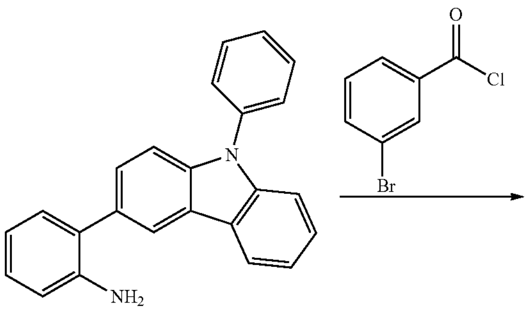

G-1

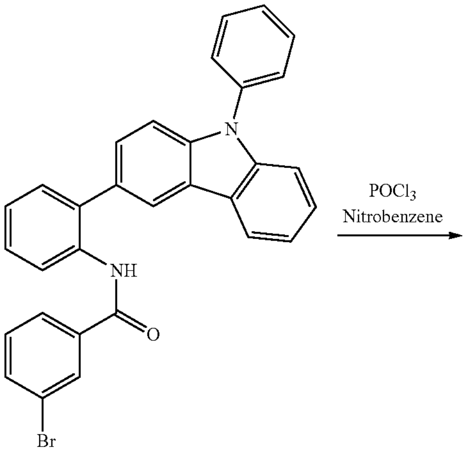

I-1

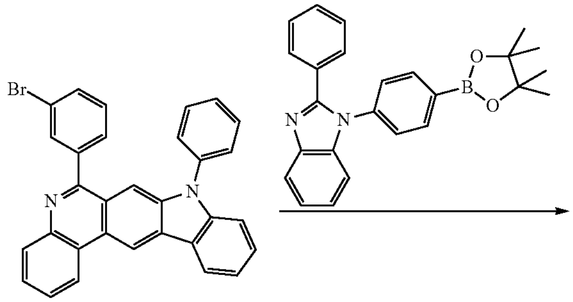

I-2

-continued

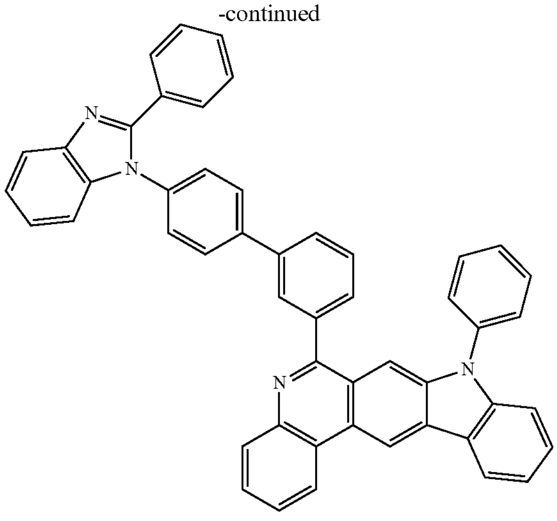

2-123

Synthesis of Compound I-1

20 g (59.8 mmol) of G-1, and 8.4 mL (59.8 mmol) of triethylamine were totally dissolved by dichloromethane, and then maintained at 0° C. Thereafter, 13.1 g (59.8 mmol) of 4-bromobenzoyl chloride was slowly dripped to perform stirring while maintaining the temperature for 1 hour. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 29.0 g (94%) of target compound I-1.

Synthesis of Compound 1-2

After 29.6 g (57.21 mmol) of I-1 was totally dissolved in 300 mL of nitrobenzene, 6.45 mL (57.21 mmol) of $POCl_3$ was slowly dripped. Thereafter, stirring was performed for 2 hours while the temperature was maintained at 150° C. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 21.2 g (74%) of target compound 1-2.

Synthesis of Compound 2-123

10.0 g (20.02 mmol) of I-2, 9.52 g (24.03 mmol) of 2-phenyl-1-(4-(4,4,5,5-tetramethyl-1,3,2-dioxaborolan-2-yl)phenyl)-1H-benzo[d]imidazole, 2.3 g (2.0 mmol) of tetrakis(triphenylphosphine)palladium(0), and 12.75 g (60.06 mmol) of $K_3PO_4$ were refluxed and stirred under 200 mL of 1,4-dioxane and 40 mL of $H_2O$ at 120° C. for 8 hours. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 9.79 g (71%) of target compound 2-123.

[Preparation Example 14] Preparation of Compound 2-243

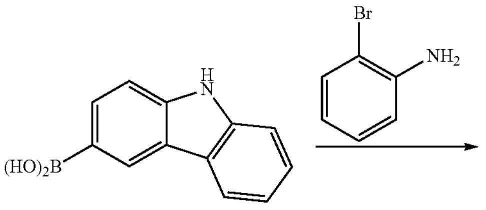

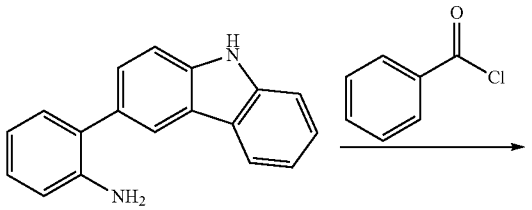

J-1

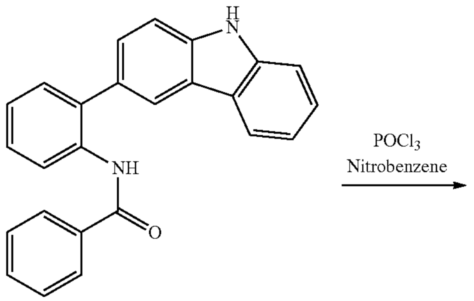

J-2

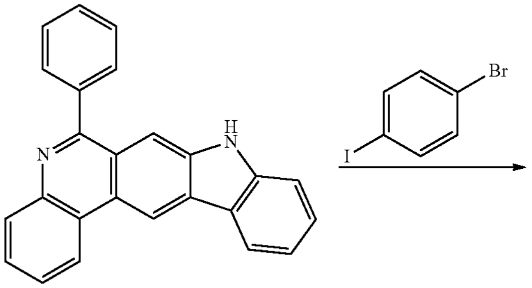

J-3

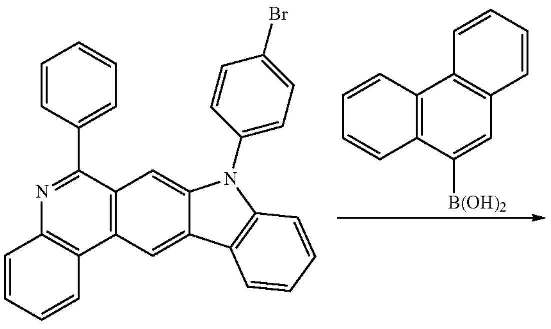

K-1

-continued

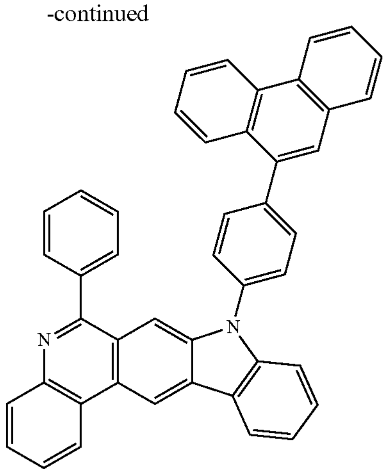

2-243

Synthesis of Compound J-1

20.0 g (94.77 mmol) of (9H-carbazol-3-yl)boronic acid, 32.6 g (189.55 mmol) of 2-bromoaniline, 5.48 g (4.74 mmol) of tetrakis(triphenylphosphine)palladium(0), and 60.35 g (284.31 mmol) of $K_3PO_4$ were refluxed and stirred under 400 mL of 1,4-dioxane and 80 mL of $H_2O$ at 120° C. for 3 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane to obtain 13.9 g (57%) of target compound J-1.

Synthesis of Compound J-2

13 g (50.32 mmol) of J-1, and 7.07 mL (50.32 mmol) of triethylamine were totally dissolved by dichloromethane, and then maintained at 0° C. Thereafter, 7.07 mL (50.32 mmol) of benzoyl chloride was slowly dripped to perform stirring while maintaining the temperature for 1 hour. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 16.6 g (91%) of target compound J-2.

Synthesis of Compound J-3

After 16.0 g (44.15 mmol) of J-2 was totally dissolved in 320 mL of nitrobenzene, 4.98 mL (44.15 mmol) of $POCl_3$ was slowly dripped. Thereafter, stirring was performed for 1 hours while the temperature was maintained at 150° C. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 13.4 g (88%) of target compound J-3.

Synthesis of Compound K-1

10.0 g (29.03 mmol) of J-3, 9.84 g (34.84 mmol) of 1-iodo-4-bromobenzene, 1.68 g (1.45 mmol) of tetrakis (triphenylphosphine)palladium(0), and 18.49 g (87.09 mmol) of $K_3PO_4$ were refluxed and stirred under 100 mL of 1,4-dioxane and 20 mL of $H_2O$ at 120° C. for 3 hours. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 10.2 g (70%) of target compound K-1.

Synthesis of Compound 2-243

10.0 g (20.02 mmol) of K-1, 5.34 g (24.03 mmol) of phenanthren-9-ylboronic acid, 1.16 g (1.0 mmol) of tetrakis (triphenylphosphine)palladium(0), and 12.75 g (60.06 mmol) of $K_3PO_4$ were refluxed and stirred under 200 mL of 1,4-dioxane and 40 mL of $H_2O$ at 120° C. for 8 hours. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 6.93 g (58%) of target compound 2-243.

[Preparation Example 15] Preparation of Compound 3-19

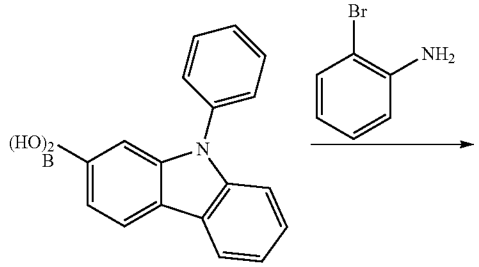

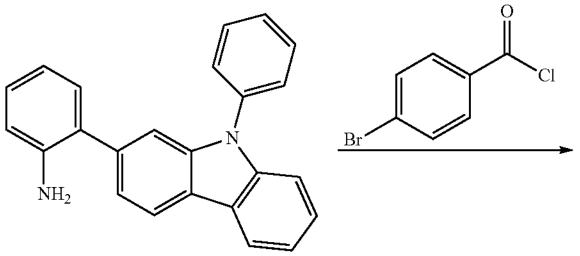

L-1

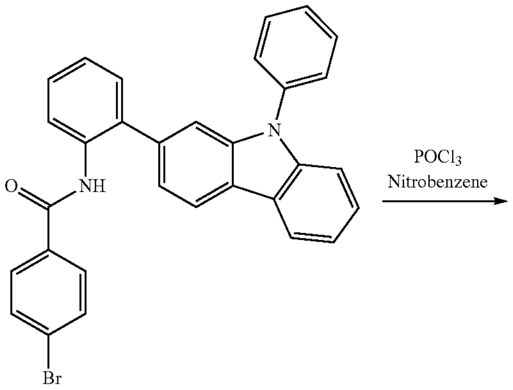

L-2

-continued

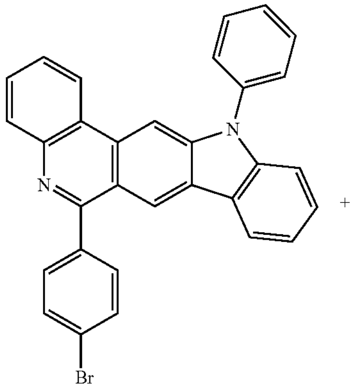

L-3

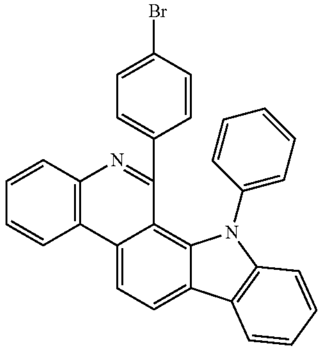

L-3'

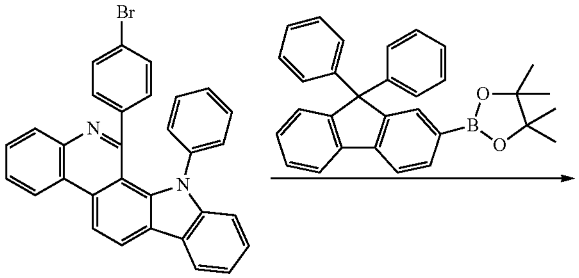

L-3'

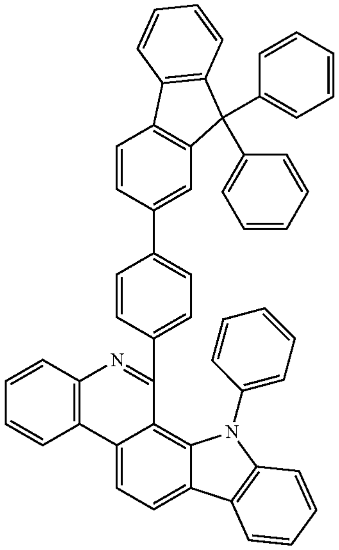

3-19

Synthesis of Compound L-1

40.0 g (139.3 mmol) of (9-Phenyl-9H-carbazol-2-yl)boronic acid, 35.9 g (208.9 mmol) of 2-bromoaniline, 8.05 g (6.96 mmol) of tetrakis(triphenylphosphine)palladium(0), and 88.7 g (417.9 mmol) of $K_3PO_4$ were refluxed and stirred under 800 mL of 1,4-dioxane and 160 mL of $H_2O$ at 120° C. for 1 hour. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane to obtain 36.3 g (78%) of target compound L-1.

Synthesis of Compound L-2

36 g (107.6 mmol) of L-1, and 15.1 mL (107.6 mmol) of triethylamine were totally dissolved by dichloromethane, and then maintained at 0° C. Thereafter, 23.6 g (107.6 mmol) of 4-bromobenzoyl chloride was slowly dripped to perform stirring while maintaining the temperature for 1 hour. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 50.1 g (90%) of target compound L-2.

Synthesis of Compounds L-3 and L-3'

After 30 g (57.97 mmol) of L-2 was totally dissolved in 600 mL of nitrobenzene, 6.54 mL (57.97 mmol) of $POCl_3$ was slowly dripped. Thereafter, stirring was performed for 2 hours while the temperature was maintained at 150° C. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 20.27 g (70%) of target compound L-3 and 5.21 g (18%) of target compound L-3'.

Synthesis of Compound 3-19

5.0 g (10.01 mmol) of L-3', 5.34 g (12.01 mmol) of 2-(9,9-diphenyl-9H-fluoren-2-yl)-4,4,5,5-tetramethyl-1,3,2-dioxaborolane, 0.58 g (0.5 mmol) of tetrakis(triphenylphosphine)palladium(0), and 6.37 g (30.0 mmol) of $K_3PO_4$ were refluxed and stirred under 100 mL of 1,4-dioxane and 20 mL of $H_2O$ at 120° C. for 8 hours. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 6.49 g (88%) of target compound 3-19.

[Preparation Example 16] Preparation of Compound 3-43

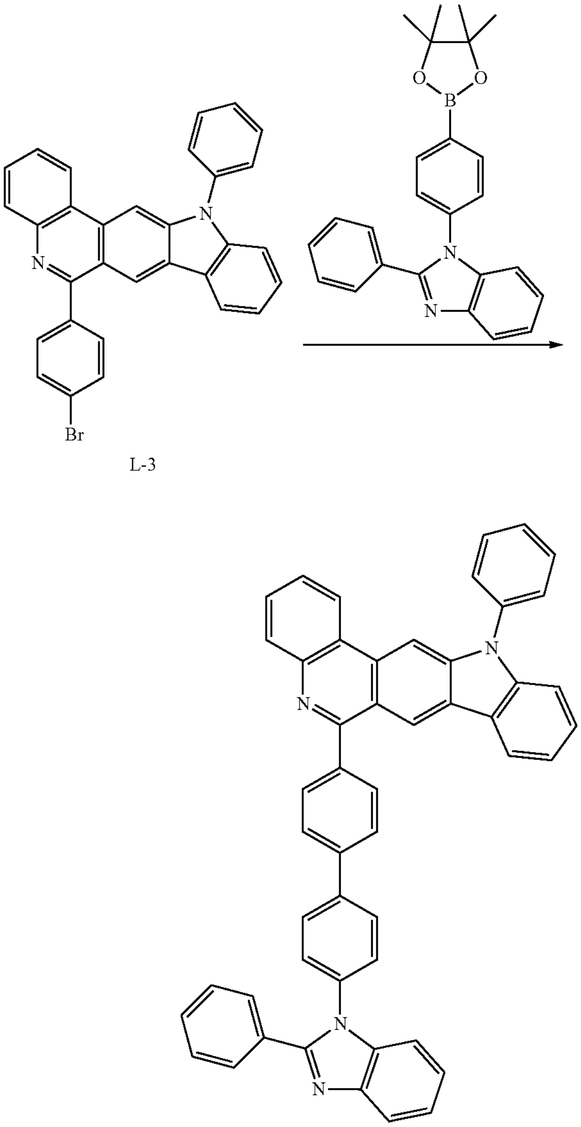

L-3

3-43

Synthesis of Compound 3-43

10.0 g (20.02 mmol) of L-3, 9.52 g (24.03 mmol) of 2-phenyl-1-(4-(4,4,5,5-tetramethyl-1,3,2-dioxaborolan-2-yl)phenyl)-1H-benzo[d]imidazole, 1.16 g (1.0 mmol) of tetrakis(triphenylphosphine)palladium(0), and 12.7 g (60.06 mmol) of $K_3PO_4$ were refluxed and stirred under 200 mL of 1,4-dioxane and 40 mL of $H_2O$ at 120° C. for 6 hours. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 10.6 g (77%) of target compound 3-43.

[Preparation Example 17] Preparation of Compound 4-1

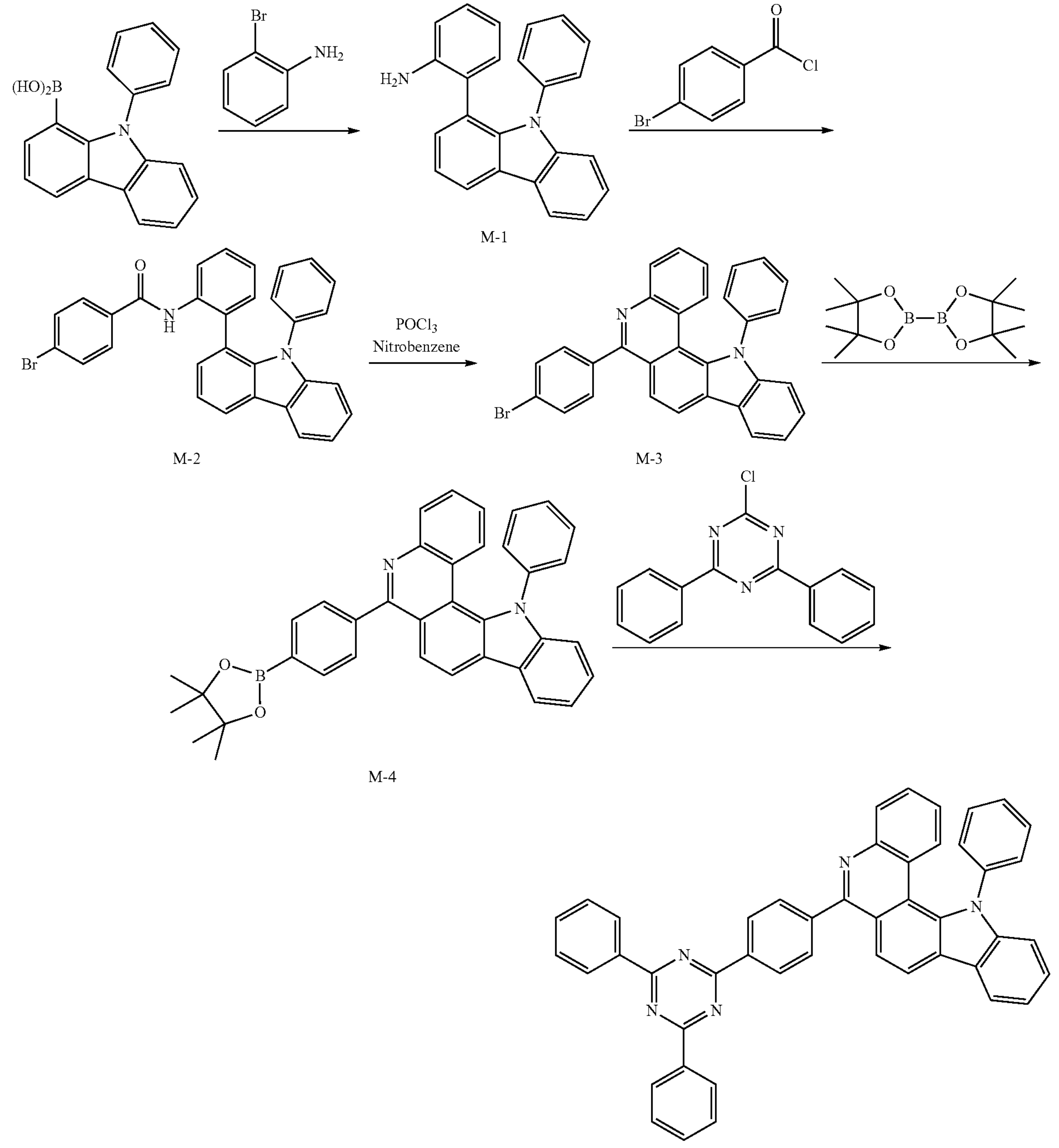

M-1, M-2, M-3, M-4, 4-1

Synthesis of Compound M-1

40.0 g (139.3 mmol) of (9-phenyl-9H-carbazol-1-yl)boronic acid, 35.9 g (208.9 mmol) of 2-bromoaniline, 8.05 g (6.96 mmol) of tetrakis(triphenylphosphine)palladium(0), and 88.7 g (417.9 mmol) of $K_3PO_4$ were refluxed and stirred under 800 mL of 1,4-dioxane and 160 mL of $H_2O$ at 120° C. for 1 hour. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane to obtain 37.7 g (81%) of target compound M-1.

Synthesis of Compound M-2

36 g (107.6 mmol) of M-1, and 15.1 mL (107.6 mmol) of triethylamine were totally dissolved by dichloromethane, and then maintained at 0° C. Thereafter, 23.6 g (107.6 mmol) of 4-bromobenzoyl chloride was slowly dripped to perform stirring while maintaining the temperature for 1 hour. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 42.2 g (76%) of target compound M-2.

Synthesis of Compound M-3

After 30 g (57.97 mmol) of M-2 was totally dissolved in 600 mL of nitrobenzene, 6.54 mL (57.97 mmol) of $POCl_3$ was slowly dripped. Thereafter, stirring was performed for 2 hours while the temperature was maintained at 150° C. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 22.2 g (77%) of target compound M-3.

Synthesis of Compound M-4

20 g (40.05 mmol) of M-3, 20.3 g (80.09 mmol) of bis(pinacolato)diboron, 11.8 g (120.15 mmol) of potassium acetate (KOAc), and 1.5 g (2.0 mmol) of [1,1'-bis(diphenylphosphino)ferrocene]dichloropalladium(H) were stirred under 100 mL of 1,4-dioxane at 120° C. for 6 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane and methanol (MeOH) to obtain 18.8 g (86%) of target compound M-4.

Synthesis of Compound 4-1

10.0 g (18.3 mmol) of M-4, 5.88 g (21.96 mmol) of 2-chloro-4,6-diphenyl-1,3,5-triazine, 1.06 g (0.92 mmol) of tetrakis(triphenylphosphine)palladium(0), and 7.59 g (54.9 mmol) of $K_2CO_3$ were stirred under 100 mL of toluene and 20 mL of each of ethanol (EtOH) and $H_2O$ at 120° C. for 3 hours. After the reaction was finished, cooling was performed to room temperature to generate the solid, and the solid was filtered, and then washed with dichloromethane, ethyl acetate (EA), and methanol (MeOH). Thereafter, the solid was totally dissolved by an excessive amount of dichloromethane, and then filtered by the silica gel to obtain 6.6 g (55%) of target compound 4-1.

[Preparation Example 18] Preparation of Compound 1-318

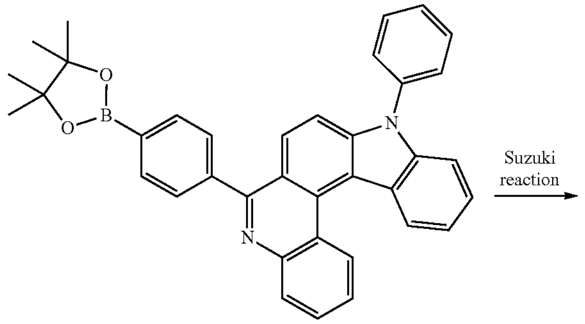

B-1

-continued

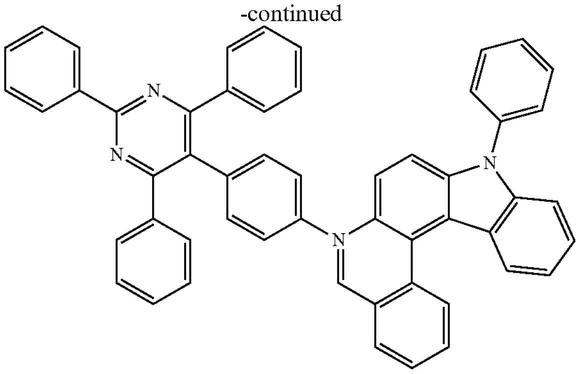

1-318

Preparation of Compound 1-318

6.0 g (10.98 mmol) of B-1, 5.1 g (13.18 mmol) of 5-bromo-2,4,6-triphenylpyrimidine, 1.3 g (1.1 mmol) of tetrakis(triphenylphosphine)palladium(0), and 6.99 g (32.94 mmol) of $K_3PO_4$ were refluxed and stirred under 60 mL of 1,4-dioxane and 12 mL of $H_2O$ at 120° C. for 2 hours. After the reaction was finished, cooling was performed to room temperature to generate the solid, and the solid was filtered, and then washed with ethyl acetate (EA) and methanol (MeOH). Thereafter, the solid was totally dissolved by an excessive amount of dichloromethane, and then filtered by the silica gel to obtain 5.0 g (63%) of target compound 1-318.

[Preparation Example 19] Preparation of Compound 2-36

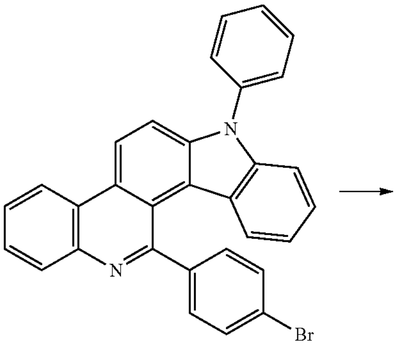

G-3'

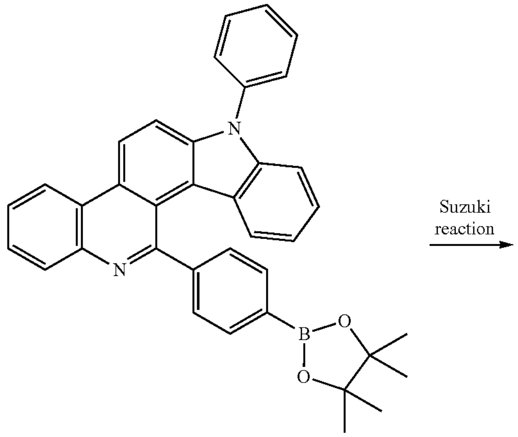

N-1

-continued

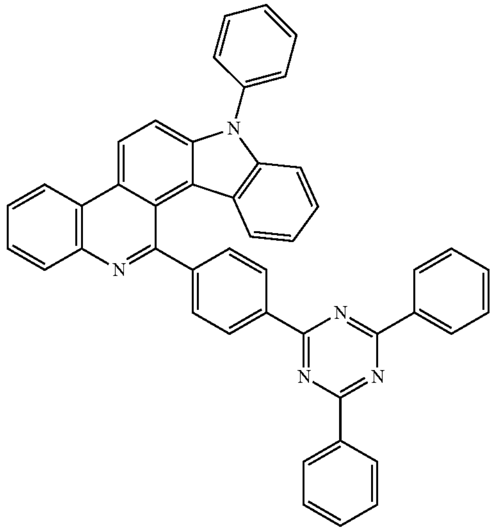

2-36

Preparation of Compound N-1

20 g (40.05 mmol) of G-3', 20.3 g (80.09 mmol) of bis(pinacolato)diboron, 11.8 g (120.15 mmol) of potassium acetate (KOAc), and 1.5 g (2.0 mmol) of [1,1'-bis(diphenylphosphino)ferrocene]dichloropalladium(II) were stirred under 100 mL of 1,4-dioxane at 120° C. for 3 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane and methanol (MeOH) to obtain 20.1 g (92%) of target compound N-1.

Preparation of Compound 2-36

6.0 g (10.98 mmol) of N-1, 3.5 g (13.18 mmol) of 2-chloro-4,6-diphenyl-1,3,5-triazine, 1.3 g (1.1 mmol) of tetrakis(triphenylphosphine)palladium(0), and 6.99 g (32.94 mmol) of $K_3PO_4$ were refluxed and stirred under 60 mL of 1,4-dioxane and 12 mL of $H_2O$ at 120° C. for 8 hours. After the reaction was finished, cooling was performed to room temperature to generate the solid, and the solid was filtered, and then washed with ethyl acetate (EA) and methanol (MeOH). Thereafter, the solid was totally dissolved by an excessive amount of dichloromethane, and then filtered by the silica gel to obtain 4.7 g (66%) of target compound 2-36.

[Preparation Example 20] Preparation of Compound 2-38

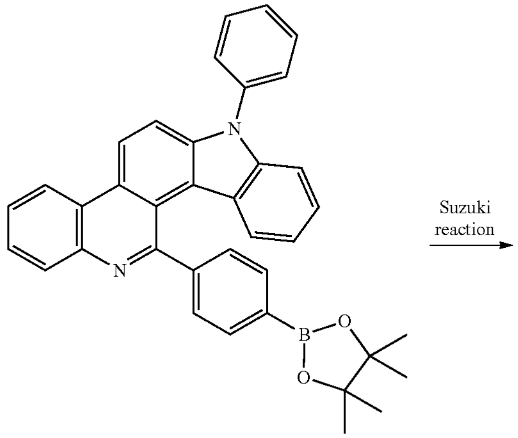

N-1

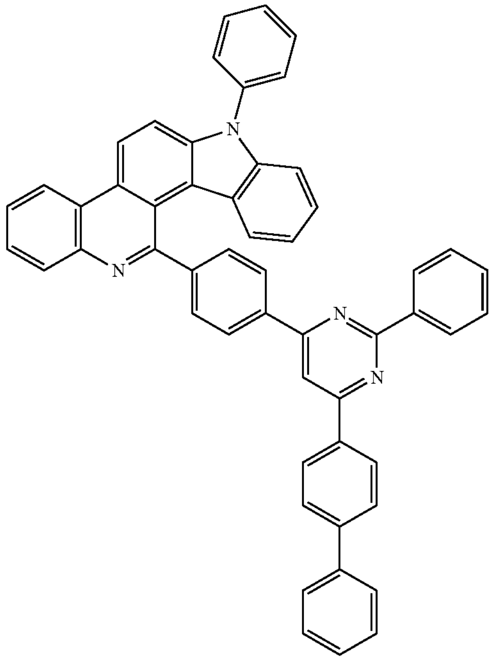

2-38

Preparation of Compound 2-38

6.0 g (10.98 mmol) of N-1, 5.1 g (13.18 mmol) of 4-([1,1'-biphenyl]-4-yl)-6-bromo-2-phenylpyrimidine, 1.3 g (1.1 mmol) of tetrakis(triphenylphosphine)palladium(0), and 6.99 g (32.94 mmol) of $K_3PO_4$ were refluxed and stirred under 60 mL of 1,4-dioxane and 12 mL of $H_2O$ at 120° C. for 8 hours. After the reaction was finished, cooling was performed to room temperature to generate the solid, and the solid was filtered, and then washed with ethyl acetate (EA) and methanol (MeOH). Thereafter, the solid was totally dissolved by an excessive amount of dichloromethane, and then filtered by the silica gel to obtain 4.4 g (55%) of target compound 2-38.

[Preparation Example 21] Preparation of Compound 3-39

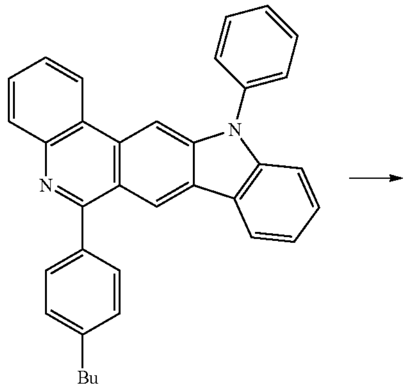

L-3

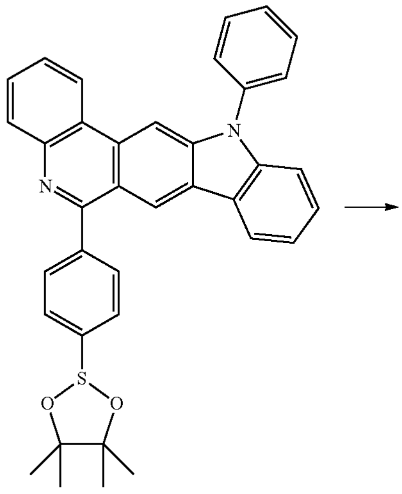

O-1

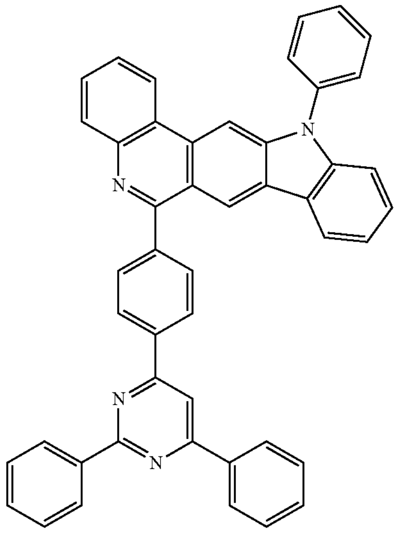

3-39

Preparation of Compound 0-1

20 g (40.05 mmol) of L-3, 20.3 g (80.09 mmol) of bis(pinacolato)diboron, 11.8 g (120.15 mmol) of potassium acetate (KOAc), and 1.5 g (2.0 mmol) of [1,1'-bis(diphenylphosphino)ferrocene]dichloropalladium(II) were stirred under 100 mL of 1,4-dioxane at 120° C. for 7 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane and methanol (MeOH) to obtain 18.8 g (86%) of target compound 0-1.

Preparation of Compound 3-39

6.0 g (10.98 mmol) of 0-1, 5.1 g (13.18 mmol) of 4-([1,1'-biphenyl]-4-yl)-6-bromo-2-phenylpyrimidine, 1.3 g (1.1 mmol) of tetrakis(triphenylphosphine)palladium(0), and 6.99 g (32.94 mmol) of $K_3PO_4$ were refluxed and stirred under 60 mL of 1,4-dioxane and 12 mL of $H_2O$ at 120° C. for 2 hours. After the reaction was finished, cooling was performed to room temperature to generate the solid, and the solid was filtered, and then washed with ethyl acetate (EA) and methanol (MeOH). Thereafter, the solid was totally dissolved by an excessive amount of dichloromethane, and then filtered by the silica gel to obtain 6.1 g (85%) of target compound 3-39.

[Preparation Example 22] Preparation of Compound 3-46

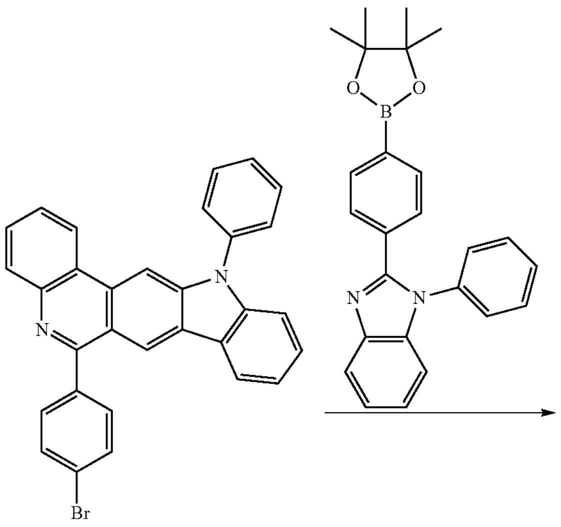

L-3

-continued

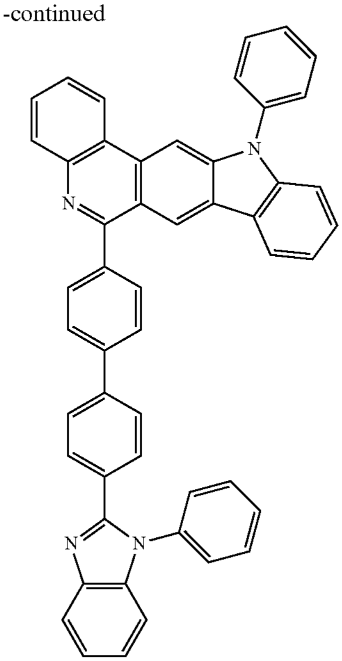

3-48

Preparation of Compound 3-46

10.0 g (20.02 mmol) of L-3, 9.52 g (24.03 mmol) of 1-phenyl-2-(4-(4,4,5,5-tetramethyl-1,3,2-dioxaborolan-2-yl)phenyl)-1H-benzo[d]imidazole, 1.16 g (1.0 mmol) of tetrakis(triphenylphosphine)palladium(0), and 12.7 g (60.06 mmol) of $K_3PO_4$ were refluxed and stirred under 200 mL of 1,4-dioxane and 40 mL of $H_2O$ at 120° C. for 4 hours. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 8.7 g (63%) of target compound 3-46.

[Preparation Example 23] Preparation of Compound 4-56

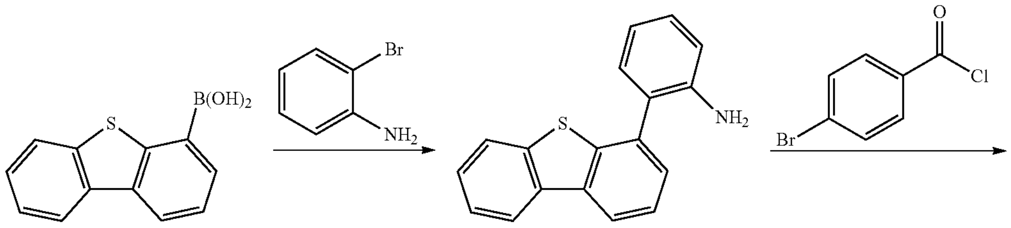

P-1

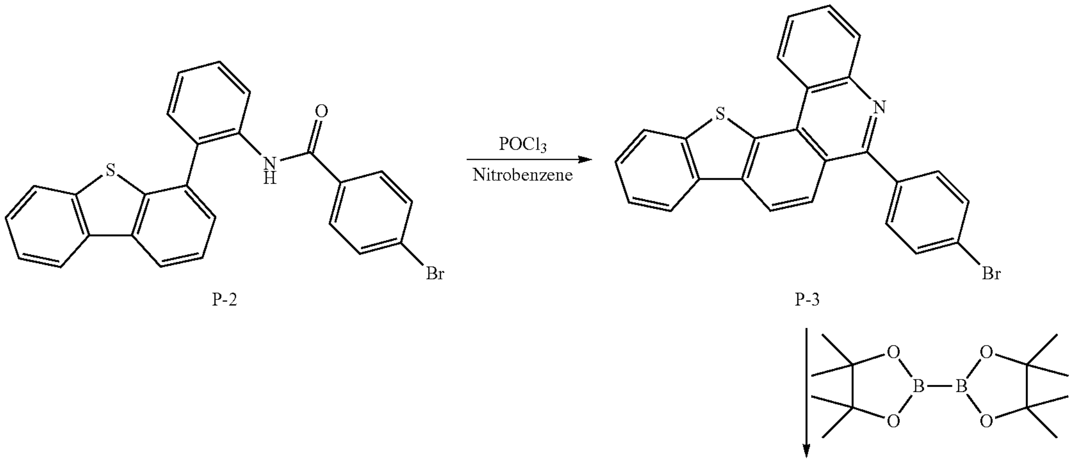

P-2

P-3

-continued

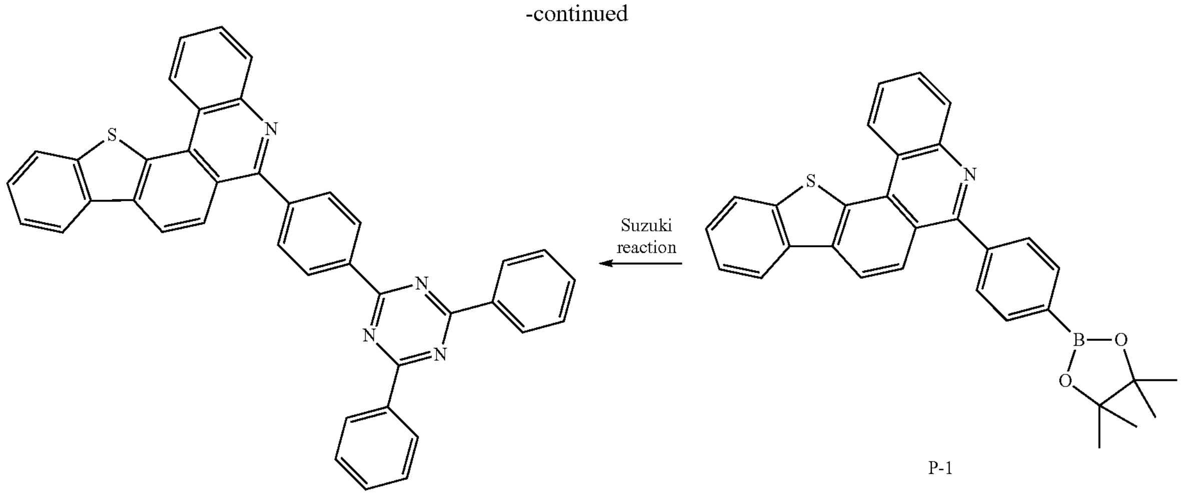

4-58 P-1

Preparation of Compound P-1

50.0 g (219.2 mmol) of dibenzo[b,d]thiophen-4-yl boronic acid, 56.5 g (328.8 mmol) of 2-bromoaniline, 25.0 g (10.96 mmol) of tetrakis(triphenylphosphine)palladium (0), and 140.0 g (657.6 mmol) of $K_3PO_4$ were refluxed and stirred under 500 mL of 1,4-dioxane and 100 mL of $H_2O$ at 120° C. for 3 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and column purification was performed at a ratio of dichloromethane and hexane of 1:4 to obtain 54.08 g (89%) of target compound P-1.

Preparation of Compound P-2

54 g (196.1 mmol) of P-1, and 27.5 mL (196.1 mmol) of triethylamine were totally dissolved by dichloromethane, and then maintained at 0° C. Thereafter, 43.0 g (196.1 mmol) of 4-bromobenzoyl chloride was slowly dripped to perform stirring while maintaining the temperature for 2 hour. After the reaction was finished, extraction was performed by distilled water and dichloromethane. After the organic layer was dried with anhydrous $MgSO_4$, the solvent was removed by the rotary evaporator to obtain 85.0 g (95%) of target compound P-2.

Preparation of Compound P-3

After 85.0 g (185.44 mmol) of P-2 was totally dissolved in 600 mL of nitrobenzene, 21.0 mL (185.44 mmol) of $POCl_3$ was slowly dripped. Thereafter, stirring was performed for 3 hours while the temperature was maintained at 150° C. After the reaction was finished, extraction was performed with distilled water and dichloromethane, the organic layer was dried with anhydrous $MgSO_4$, the solvent was removed by the rotary evaporator, and washing was performed by methanol (MeOH) to obtain 55.0 g (67%) of target compound P-3.

Preparation of Compound P-4

20 g (45.4 mmol) of P-3, 23.0 g (90.8 mmol) of bis (pinacolato)diboron, 13.3 g (136.2 mmol) of potassium acetate (KOAc), and 1.6 g (2.27 mmol) of [1,1'-bis(diphenylphosphino)ferrocene]dichloropalladium(II) were stirred under 200 mL of 1,4-dioxane at 120° C. for 3 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane and methanol (MeOH) to obtain 16.0 g (72%) of target compound P-4.

Preparation of Compound 4-56

7.0 g (14.36 mmol) of P-4, 3.8 g (14.36 mmol) of 2-chloro-4,6-diphenyl-1,3,5-triazine, 1.6 g (1.44 mmol) of tetrakis(triphenylphosphine)palladium(0), and 9.1 g (43.08 mmol) of $K_3PO_4$ were refluxed and stirred under 100 mL of 1,4-dioxane and 20 mL of $H_2O$ at 120° C. for 2 hours. After the reaction was finished, cooling was performed to room temperature to generate the solid, and the solid was filtered, and then washed with ethyl acetate (EA) and methanol (MeOH). Thereafter, the solid was boiled in an excessive amount of 1,2-dichloroethane and then filtered to obtain 6.6 g (78%) of target compound 4-56.

[Preparation Example 24] Preparation of Compound 4-58

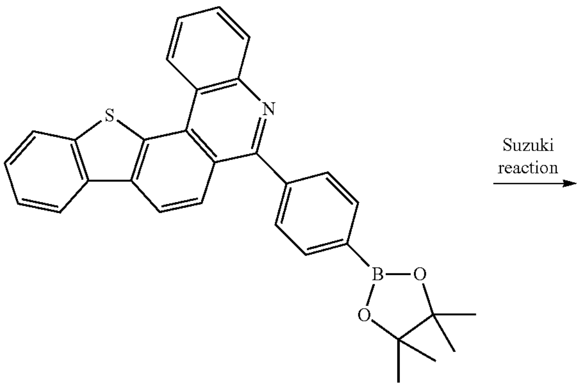

P-4

-continued

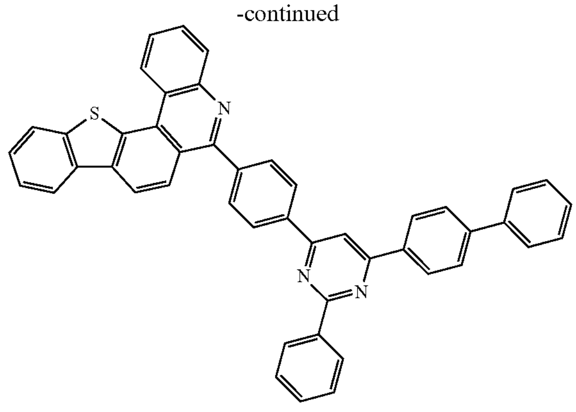

4-58

Preparation of Compound 4-58

6.3 g (12.91 mmol) of P-4, 5.0 g (12.91 mmol) of 4-([1,1'-biphenyl]-4-yl)-6-bromo-2-phenylpyrimidine, 1.5 g (1.29 mmol) of tetrakis(triphenylphosphine)palladium(0), and 8.2 g (38.73 mmol) of $K_3PO_4$ were refluxed and stirred under 100 mL of 1,4-dioxane and 20 mL of $H_2O$ at 120° C. for 2 hours. After the reaction was finished, cooling was performed to room temperature to generate the solid, and the solid was filtered, and then washed with ethyl acetate (EA) and methanol (MeOH). Thereafter, the solid was boiled in an excessive amount of 1,2-dichloroethane and then filtered to obtain 5.7 g (66%) of target compound 4-58.

[Preparation Example 25] Preparation of Compound 4-76

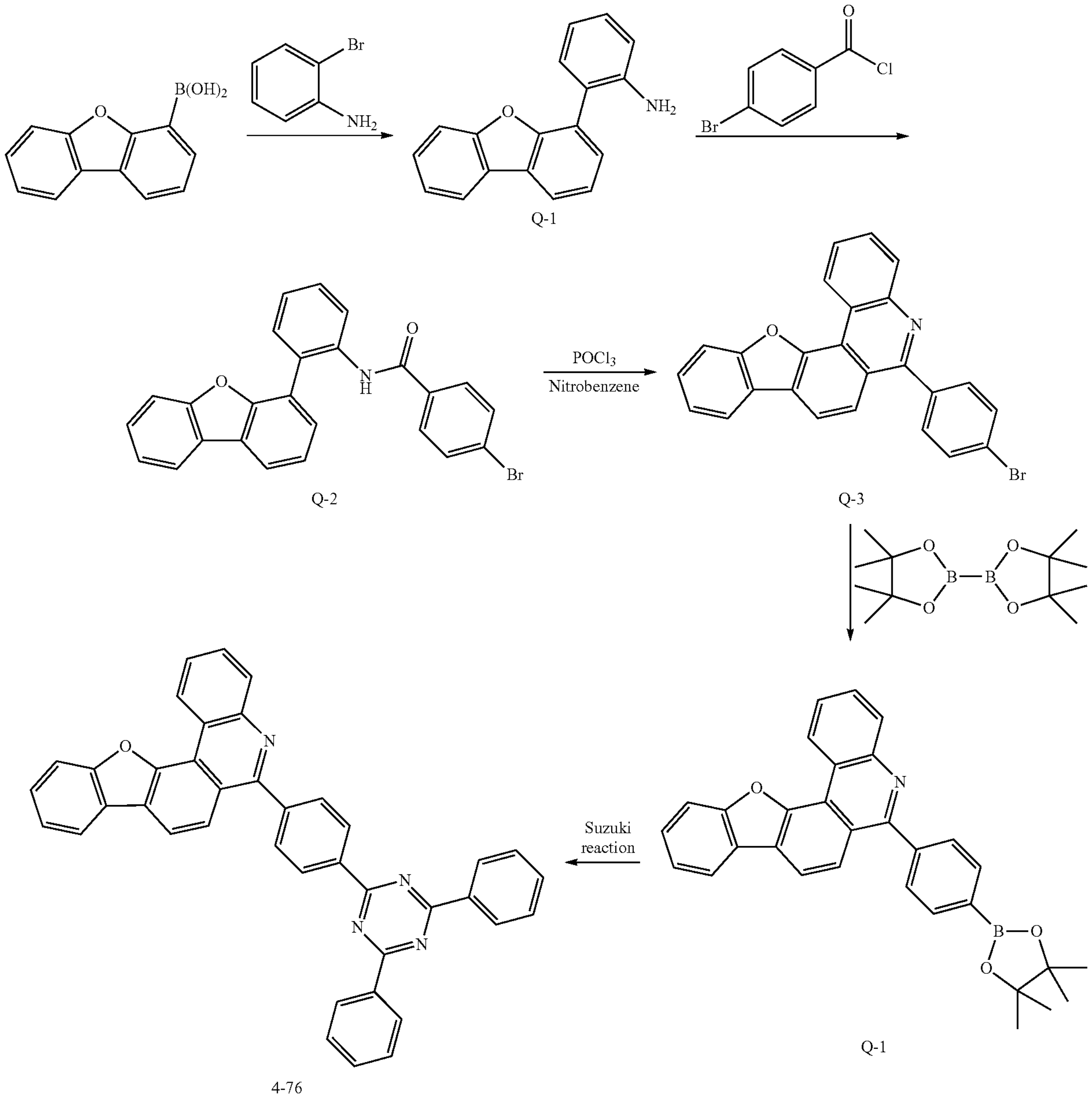

Preparation of Compound Q-1

20.0 g (94.33 mmol) of dibenzofuran-4-yl boronic acid, 32.45 g (188.66 mmol) of 2-bromoaniline, 5.45 g (4.72 mmol) of tetrakis(triphenylphosphine)palladium(0), and 60.07 g (282.99 mmol) of $K_3PO_4$ were refluxed and stirred under 400 mL of 1,4-dioxane and 80 mL of $H_2O$ at 120° C. for 3 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane to obtain 21.5 g (88%) of target compound Q-1.

Preparation of Compound Q-2

20 g (77.13 mmol) of Q-1, and 10.8 mL (77.13 mmol) of triethylamine were totally dissolved by dichloromethane, and then maintained at 0° C. Thereafter, 16.9 g (77.13 mmol) of 4-bromobenzoyl chloride was slowly dripped to perform stirring while maintaining the temperature for 1 hour. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 32.4 g (95%) of target compound Q-2.

Preparation of Compound Q-3

After 32.0 g (72.35 mmol) of Q-2 was totally dissolved in 600 mL of nitrobenzene, 8.16 mL (72.35 mmol) of $POCl_3$ was slowly dripped. Thereafter, stirring was performed for 2 hours while the temperature was maintained at 150° C. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 17.8 g (58%) of target compound Q-3.

Preparation of Compound Q-4

18.3 g (43.1 mmol) of Q-3, 21.9 g (86.3 mmol) of bis(pinacolato)diboron, 12.7 g (129.3 mmol) of potassium acetate (KOAc), and 1.6 g (2.16 mmol) of [1,1'-bis(diphenylphosphino)ferrocene]dichloropalladium(II) were stirred under 150 mL of 1,4-dioxane at 120° C. for 2 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane and methanol (MeOH) to obtain 20.0 g (84%) of target compound Q-4.

Preparation of Compound 4-76

8.0 g (16.9 mmol) of Q-4, 5.45 g (20.37 mmol) of 2-chloro-4,6-diphenyl-1,3,5-triazine, 1.96 g (1.7 mmol) of tetrakis(triphenylphosphine)palladium(0), and 10.8 g (50.91 mmol) of $K_3PO_4$ were refluxed and stirred under 160 mL of 1,4-dioxane and 30 mL of $H_2O$ at 120° C. for 3 hours. After the reaction was finished, cooling was performed to room temperature to generate the solid, and the solid was filtered, and then washed with ethyl acetate (EA) and methanol (MeOH). Thereafter, the solid was boiled in an excessive amount of toluene, and then filtered to obtain 3.3 g (34%) of target compound 4-76.

[Preparation Example 26] Preparation of Compound 4-169

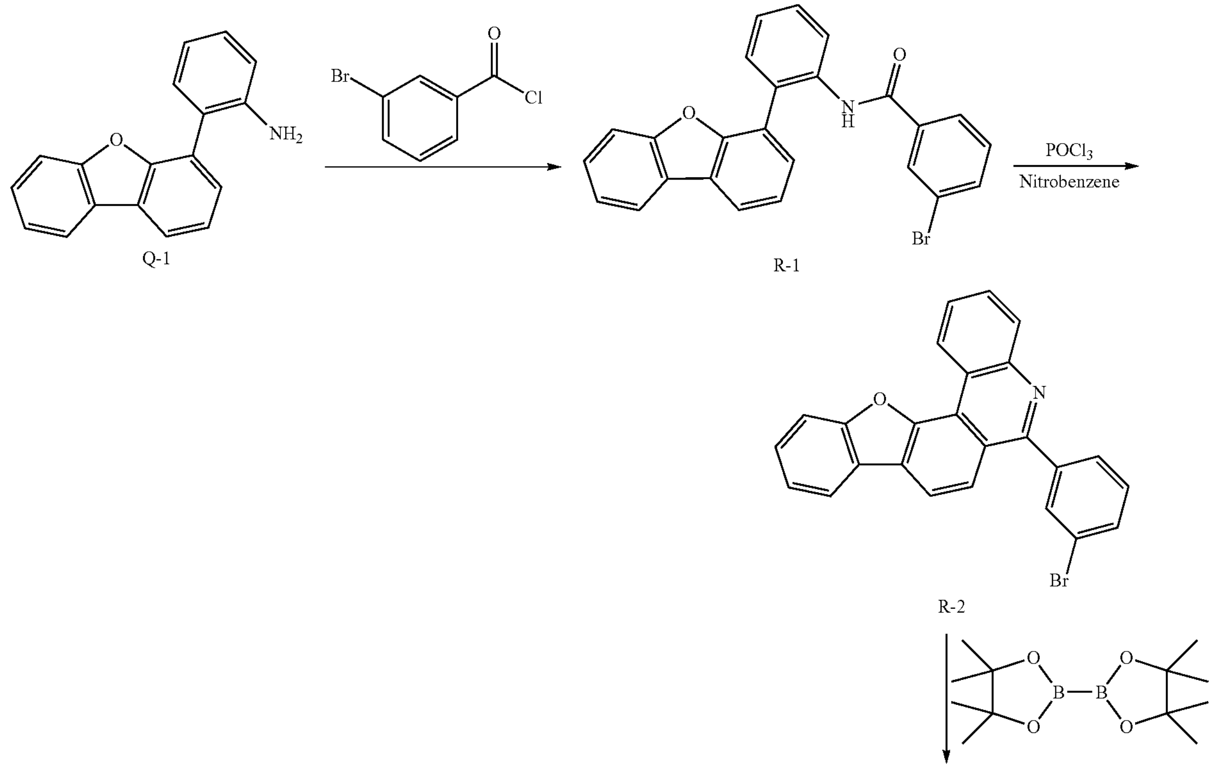

Q-1
R-1
R-2

-continued

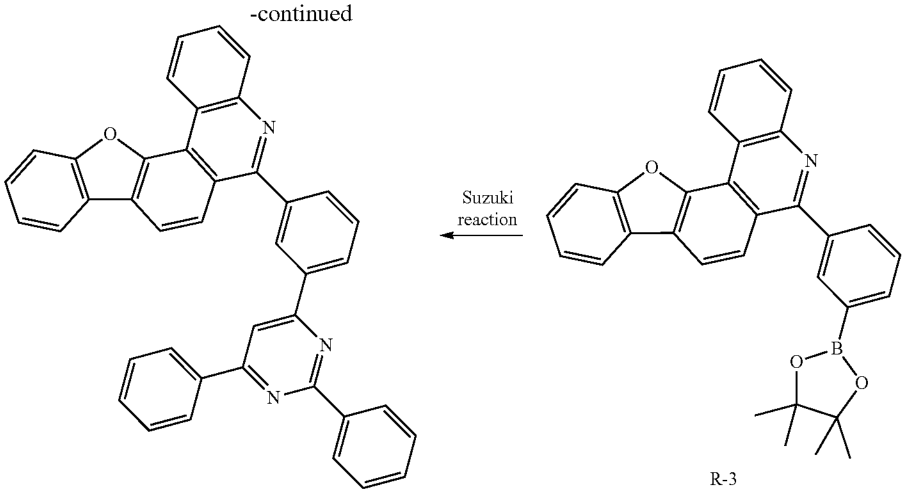

4-159 R-3

Preparation of Compound R-1

20 g (77.13 mmol) of Q-1, and 10.8 mL (77.13 mmol) of triethylamine were totally dissolved by dichloromethane, and then maintained at 0° C. Thereafter, 16.9 g (77.13 mmol) of 3-bromobenzoyl chloride was slowly dripped to perform stirring while maintaining the temperature for 1 hour. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 32.4 g (95%) of target compound R-1.

Preparation of Compound R-2

After 32.0 g (72.35 mmol) of R-1 was totally dissolved in 600 mL of nitrobenzene, 8.16 mL (72.35 mmol) of $POCl_3$ was slowly dripped. Thereafter, stirring was performed for 2 hours while the temperature was maintained at 150° C. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 17.8 g (58%) of target compound R-2.

Preparation of Compound R-3

18.3 g (43.1 mmol) of R-2, 21.9 g (86.3 mmol) of bis(pinacolato)diboron, 12.7 g (129.3 mmol) of potassium acetate (KOAc), and 1.6 g (2.16 mmol) of [1,1'-bis(diphenylphosphino)ferrocene]dichloropalladium(II) were stirred under 150 mL of 1,4-dioxane at 120° C. for 2 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane and methanol (MeOH) to obtain 20.0 g (84%) of target compound R-3.

Preparation of Compound 4-169

8.0 g (16.9 mmol) of R-3, 6.34 g (20.37 mmol) of 4-([1,1'-biphenyl]-4-yl)-6-bromo-2-phenylpyrimidine, 1.96 g (1.7 mmol) of tetrakis(triphenylphosphine)palladium(0), and 10.8 g (50.91 mmol) of $K_3PO_4$ were refluxed and stirred under 160 mL of 1,4-dioxane and 30 mL of $H_2O$ at 120° C. for 3 hours. After the reaction was finished, cooling was performed to room temperature to generate the solid, and the solid was filtered, and then washed with ethyl acetate (EA) and methanol (MeOH). Thereafter, the solid was boiled in an excessive amount of toluene, and then filtered to obtain 6.4 g (66%) of target compound 4-169.

[Preparation Example 27] Preparation of Compound 1-482

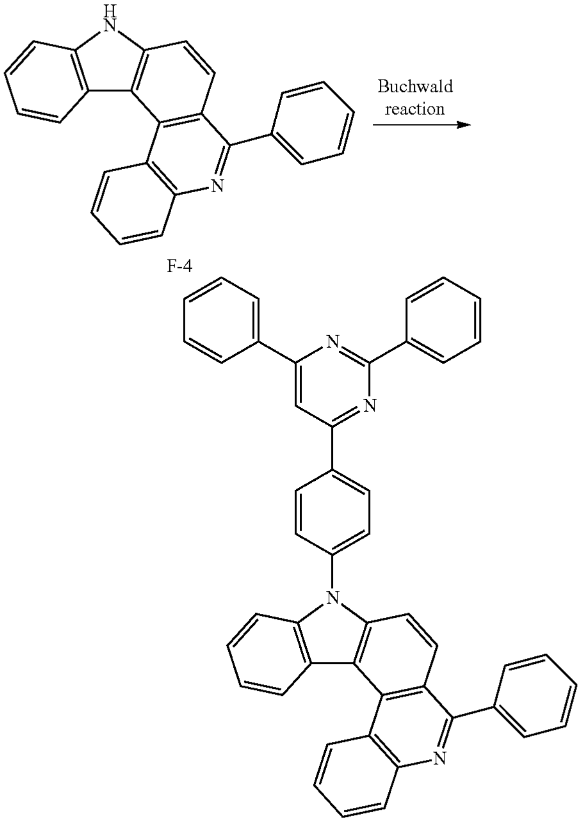

F-4

1-482

Preparation of Compound 1-482

8.0 g (23.23 mmol) of F-4, 9.9 g (25.55 mmol) of 4-(4-bromophenyl)-2,6-diphenylpyridine, 2.1 g (2.323 mmol) of $Pd_2(dba)_3$, 0.22 g (2.323 mmol) of $P(t\text{-}Bu)_3$, and 14.1 g (69.69 mmol) of sodium tert-butoxide were refluxed and stirred under 150 mL of toluene at 120° C. for 6 hours. After the reaction was finished, cooling was performed to room temperature to generate the solid, and the solid was filtered, and then washed with ethyl acetate (EA) and methanol (MeOH). Thereafter, the solid was boiled in an excessive amount of toluene, and then filtered to obtain 10.8 g (71%) of target compound 1-482.

[Preparation Example 28] Preparation of Compound 1-483

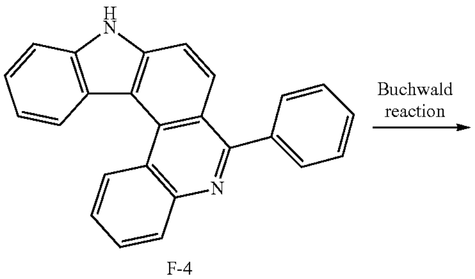

F-4

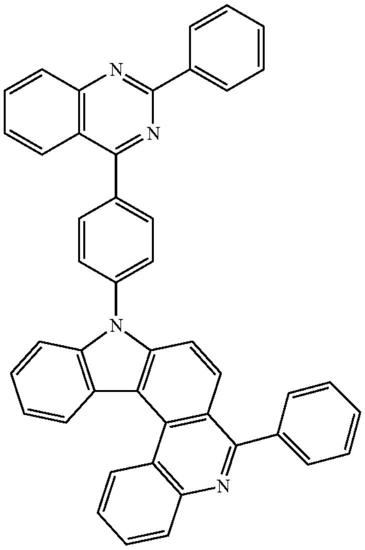

1-483

Preparation of Compound 1-483

8.0 g (23.23 mmol) of F-4, 7.28 g (25.55 mmol) of 4-bromo-2-phenylquinazoline, 2.1 g (2.323 mmol) of $Pd_2(dba)_3$, 0.22 g (2.323 mmol) of $P(t\text{-}Bu)_3$, and 14.1 g (69.69 mmol) of sodium tert-butoxide were refluxed and stirred under 150 mL of toluene at 120° C. for 3 hours. After the reaction was finished, cooling was performed to room temperature to generate the solid, and the solid was filtered, and then washed with ethyl acetate (EA) and methanol (MeOH). Thereafter, the solid was boiled in an excessive amount of toluene, and then filtered to obtain 9.1 g (71%) of target compound 1-483.

[Preparation Example 29] Preparation of Compound 2-127

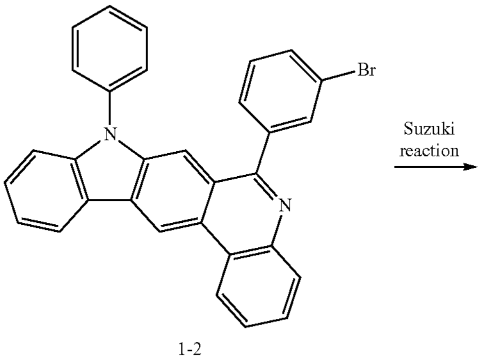

1-2

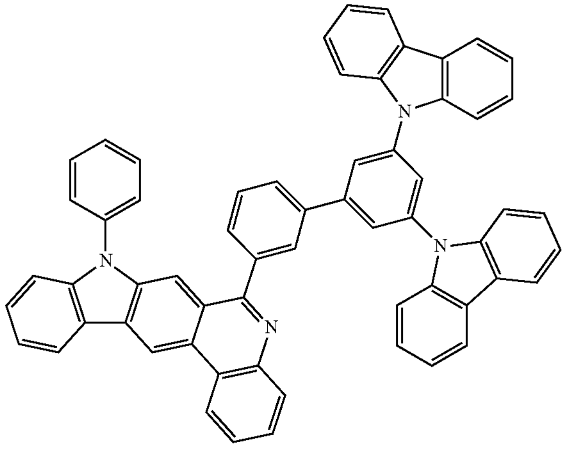

2-127

Preparation of Compound 2-127

10.0 g (20.02 mmol) of 1-2, 12.9 g (24.03 mmol) of 9,9'-(5-(4,4,5,5-tetramethyl-1,3,2-dioxaborolan-2-yl)-1,3-phenylene)bis(9H-carbazole), 2.3 g (2.0 mmol) of tetrakis (triphenylphosphine)palladium(0), and 12.75 g (60.06 mmol) of $K_3PO_4$ were refluxed and stirred under 200 mL of 1,4-dioxane and 40 mL of $H_2O$ at 120° C. for 8 hours. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 13.8 g (83%) of target compound 2-127.

[Preparation Example 30] Preparation of Compound 2-148

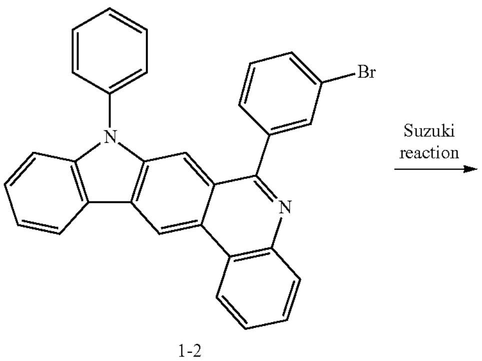

1-2

-continued

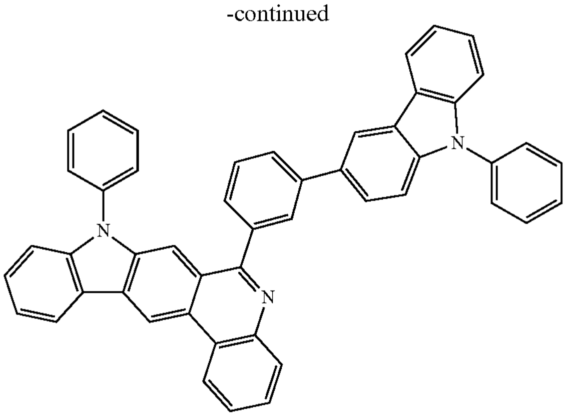

2-148

-continued

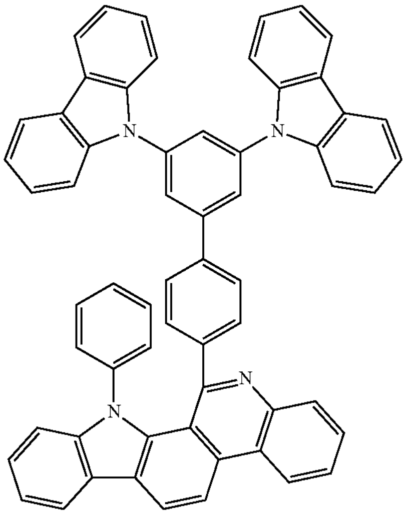

3-12

Preparation of Compound 2-148

10.0 g (20.02 mmol) of 1-2, 6.9 g (24.03 mmol) of (9-phenyl-9H-carbazol-3-yl)boronic acid, 2.3 g (2.0 mmol) of tetrakis(triphenylphosphine)palladium(0), and 12.75 g (60.06 mmol) of $K_3PO_4$ were refluxed and stirred under 200 mL of 1,4-dioxane and 40 mL of $H_2O$ at 120° C. for 8 hours. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 8.9 g (67%) of target compound 2-148.

[Preparation Example 31] Preparation of Compound 3-12

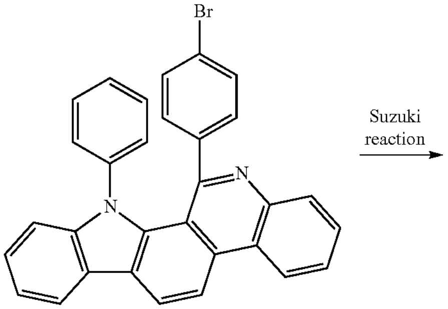

L-3'

Preparation of Compound 3-12

5.0 g (10.01 mmol) of L-3', 6.42 g (12.01 mmol) of 9,9'-(5-(4,4,5,5-tetramethyl-1,3,2-dioxaborolan-2-yl)-1,3-phenylene)bis(9H-carbazole), 0.58 g (0.5 mmol) of tetrakis (triphenylphosphine)palladium(0), and 6.37 g (30.0 mmol) of $K_3PO_4$ were refluxed and stirred under 100 mL of 1,4-dioxane and 20 mL of $H_2O$ at 120° C. for 8 hours. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 5.6 g (68%) of target compound 3-12.

[Preparation Example 32] Preparation of Compound 4-109

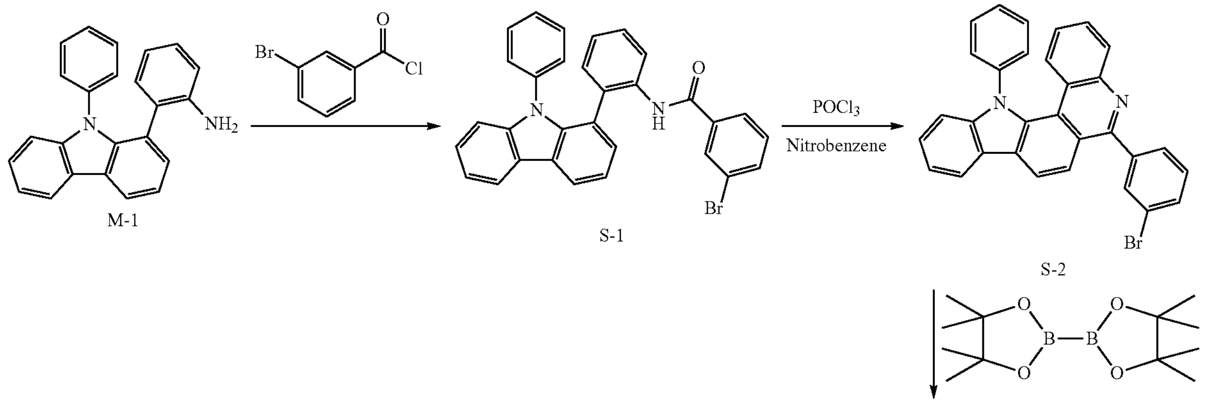

M-1 S-1 S-2

-continued

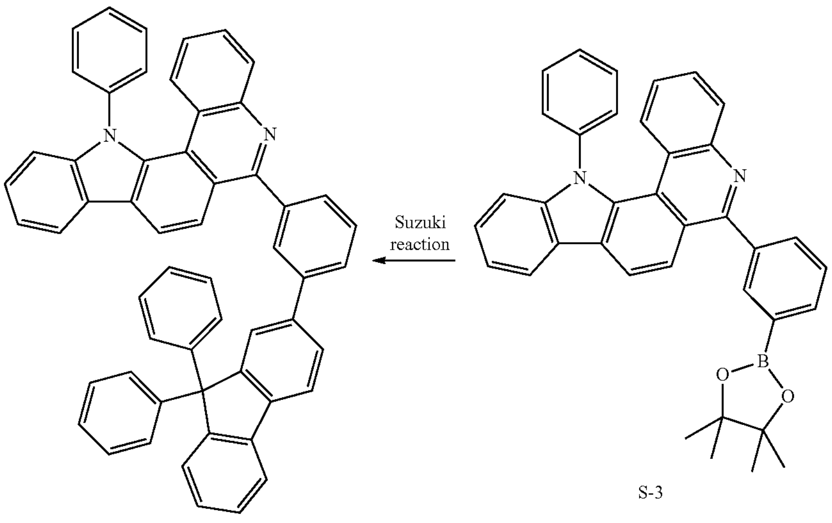

4-109

S-3

Preparation of Compound S-1

36 g (107.6 mmol) of M-1, and 15.1 mL (107.6 mmol) of triethylamine were totally dissolved by dichloromethane, and then maintained at 0° C. Thereafter, 23.6 g (107.6 mmol) of 3-bromobenzoyl chloride was slowly dripped to perform stirring while maintaining the temperature for 1 hour. After the reaction was finished, extraction was performed by distilled water and dichloromethane. After the organic layer was dried with anhydrous $MgSO_4$, the solvent was removed by the rotary evaporator, and purification was performed by the column chromatography by using dichloromethane and hexane as the developing solvent to obtain 42.2 g (76%) of target compound S-1.

Preparation of Compound S-2

After 30 g (57.97 mmol) of S-1 was totally dissolved in 600 mL of nitrobenzene, 6.54 mL (57.97 mmol) of $POCl_3$ was slowly dripped. Thereafter, stirring was performed for 2 hours while the temperature was maintained at 150° C. After the reaction was finished, extraction was performed with distilled water and dichloromethane, the organic layer was dried with anhydrous $MgSO_4$, the solvent was removed by the rotary evaporator, and purification was performed by the column chromatography by using dichloromethane and hexane as the developing solvent to obtain 22.2 g (77%) of target compound S-2.

Preparation of Compound S-3

20 g (40.05 mmol) of S-2, 20.3 g (80.09 mmol) of bis(pinacolato)diboron, 11.8 g (120.15 mmol) of potassium acetate (KOAc), and 1.5 g (2.0 mmol) of [1,1'-bis(diphenylphosphino)ferrocene]dichloropalladium(II) were stirred under 100 mL of 1,4-dioxane at 120° C. for 6 hours. After the reaction was finished, cooling was performed to room temperature, and extraction was then performed with distilled water and dichloromethane. After the organic layer was dried with anhydrous $MgSO_4$, the solvent was removed by the rotary evaporator, filtering was performed by the silica gel, and washing was performed by hexane and methanol (MeOH) to obtain 18.8 g (86%) of target compound S-3.

Preparation of Compound 4-109

6.0 g (10.98 mmol) of S-3, 5.2 g (13.18 mmol) of 2-bromo-9,9-diphenyl-9H-fluorene, 1.3 g (1.1 mmol) of tetrakis(triphenylphosphine)palladium(0), and 6.99 g (32.94 mmol) of $K_3PO_4$ were refluxed and stirred under 60 mL of 1,4-dioxane and 12 mL of $H_2O$ at 120° C. for 2 hours. After the reaction was finished, cooling was performed to room temperature to generate the solid, and the solid was filtered, and then washed with ethyl acetate (EA) and methanol (MeOH). Thereafter, the solid was totally dissolved in an excessive amount of dichloromethane, and then filtered by the silica gel to obtain 7.1 g (88%) of target compound 4-109.

[Preparation Example 33] Preparation of Compound 4-113

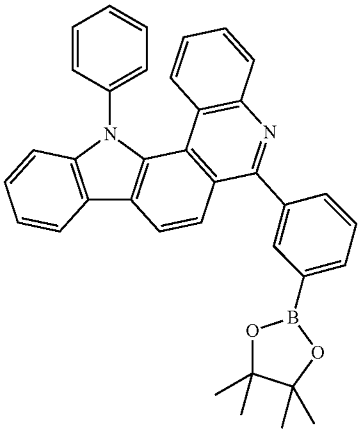

S-3

-continued

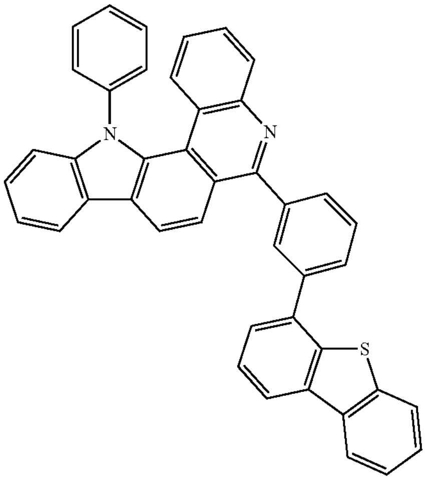

4-113

-continued

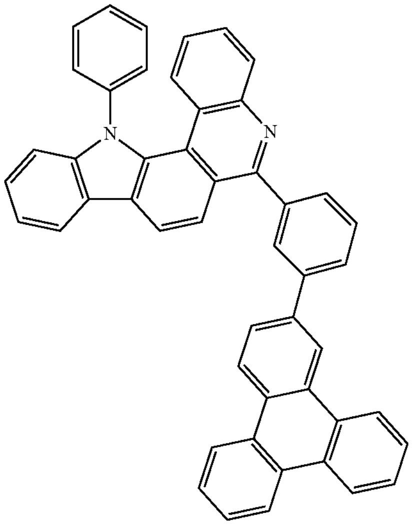

4-119

Preparation of Compound 4-113

6.0 g (10.98 mmol) of S-3, 3.5 g (13.18 mmol) of 4-bromodibenzo[b,d]thiophene, 1.3 g (1.1 mmol) of tetrakis (triphenylphosphine)palladium(0), and 6.99 g (32.94 mmol) of $K_3PO_4$ were refluxed and stirred under 60 mL of 1,4-dioxane and 12 mL of $H_2O$ at 120° C. for 2 hours. After the reaction was finished, cooling was performed to room temperature to generate the solid, and the solid was filtered, and then washed with ethyl acetate (EA) and methanol (MeOH). Thereafter, the solid was totally dissolved in an excessive amount of dichloromethane, and then filtered by the silica gel to obtain 4.3 g (65%) of target compound 4-113.

[Preparation Example 34] Preparation of Compound 4-119

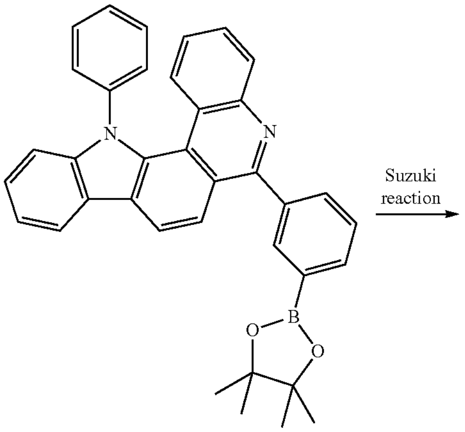

S-3

Preparation of Compound 4-119

6.0 g (10.98 mmol) of S-3, 4.05 g (13.18 mmol) of 2-bromotriphenylene, 1.3 g (1.1 mmol) of tetrakis(triphenylphosphine)palladium(0), and 6.99 g (32.94 mmol) of $K_3PO_4$ were refluxed and stirred under 60 mL of 1,4-dioxane and 12 mL of $H_2O$ at 120° C. for 2 hours. After the reaction was finished, cooling was performed to room temperature to generate the solid, and the solid was filtered, and then washed with ethyl acetate (EA) and methanol (MeOH). Thereafter, the solid was totally dissolved in an excessive amount of dichloromethane, and then filtered by the silica gel to obtain 4.8 g (68%) of target compound 4-119.

[Preparation Example 35] Preparation of Compound 5-15

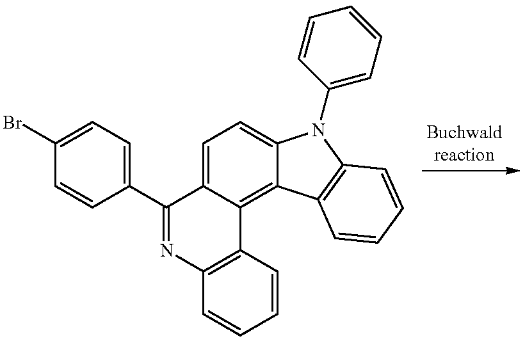

A-5

-continued

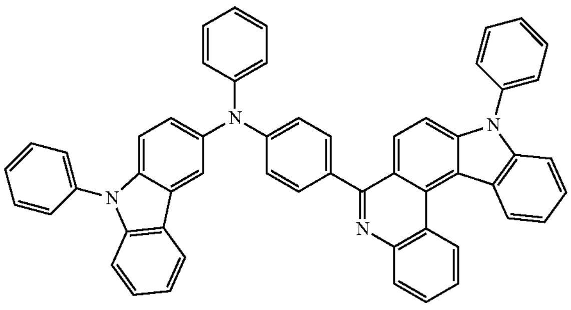

5-15

10.0 g (20.02 mmol) of A-5, 6.03 g (18.02 mmol) of N,9-diphenyl-9H-carbazol-3-amine, 1.83 g (2.0 mmol) of $Pd_2(dba)_3$, 1.9 g (4.0 mmol) of XPhos, and 8.1 g (40.04 mmol) of NaOtBu were stirred under 100 mL of toluene at 120° C. for 2 hours. After completion of the reaction, the reaction product was cooled to room temperature, and then extracted with MC and allowed to evaporate all the reaction products. The resulting oil was column purified to obtain 9.65 g (64%) of Target Compound 5-15.

[Preparation Example 36] Preparation of Compound 5-20

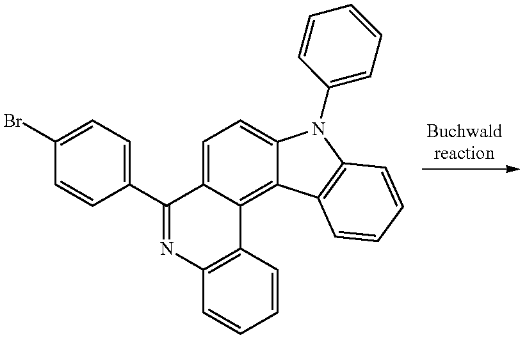

A-5

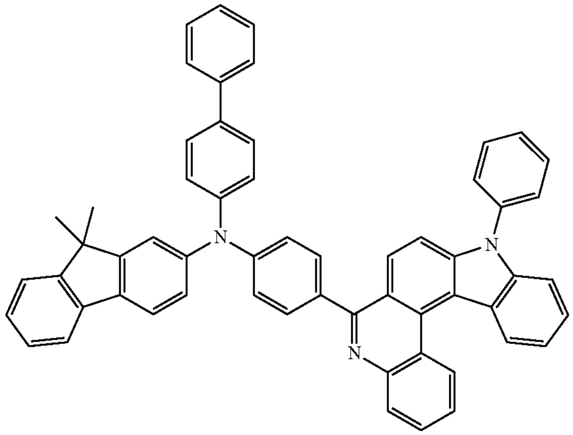

5-20

10.0 g (20.02 mmol) of A-5, 6.51 g (18.02 mmol) of N-([1,1'-biphenyl]-4-yl)-9,9-dimethyl-9H-fluoren-2-amine, 1.83 g (2.0 mmol) of $Pd_2(dba)_3$, 1.9 g (4.0 mmol) of XPhos, and 8.1 g (40.04 mmol) of NaOtBu were stirred under 100 mL of toluene at 120° C. for 2 hours. After completion of the reaction, the reaction product was cooled to room temperature, and then extracted with MC and allowed to evaporate all the reaction products. The resulting oil was column purified to obtain 8.53 g (55%) of Target Compound 5-20.

[Preparation Example 37] Preparation of Compound 5-33

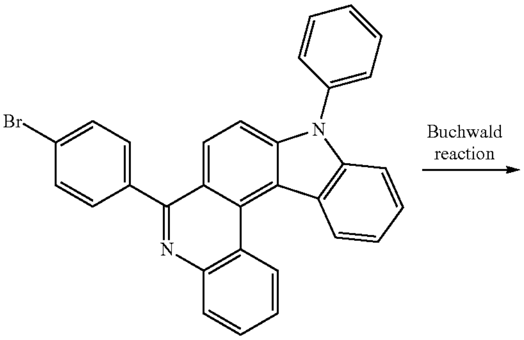

A-5

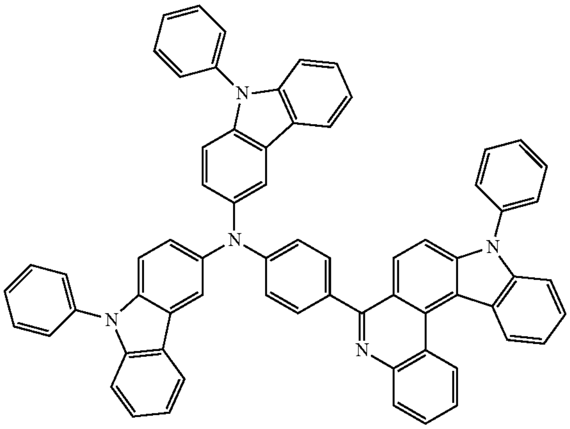

5-33

10.0 g (20.02 mmol) of A-5, 9.0 g (18.02 mmol) of bis(9-phenyl-9H-carbazol-3-yl)amine, 1.83 g (2.0 mmol) of $Pd_2(dba)_3$, 1.9 g (4.0 mmol) of XPhos, and 8.1 g (40.04 mmol) of NaOtBu were stirred under 100 mL of toluene at 120° C. for 6 hours. After completion of the reaction, the reaction product was cooled to room temperature, and then extracted with MC and allowed to evaporate all the reaction products. The resulting solid was column purified to obtain 14.1 g (77%) of Target Compound 5-33.

[Preparation Example 38] Preparation of Compound 5-55

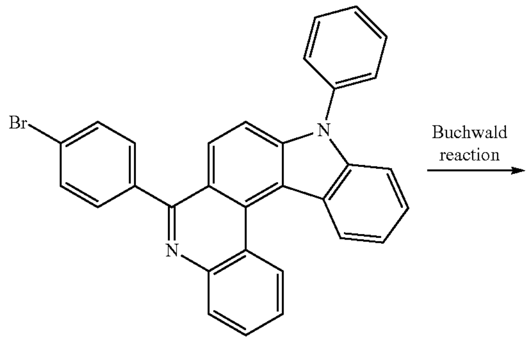

A-5

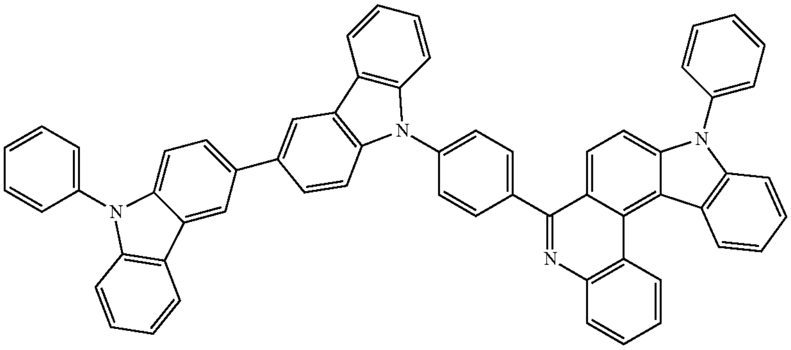

5-33

10.0 g (20.02 mmol) of A-5, 7.36 g (18.02 mmol) of 9-phenyl-9H,9'H-3,3'-bicarbazole, 1.83 g (2.0 mmol) of $Pd_2(dba)_3$, 1.9 g (4.0 mmol) of XPhos, and 8.1 g (40.04 mmol) of NaOtBu were stirred under 100 mL of toluene at 120° C. for 3 hours. After completion of the reaction, the reaction product was cooled to room temperature, and then extracted with MC and allowed to evaporate all the reaction products. The resulting solid was column purified to obtain 8.11 g (49%) of Target Compound 5-55.

[Preparation Example 39] Preparation of Compound 5-82

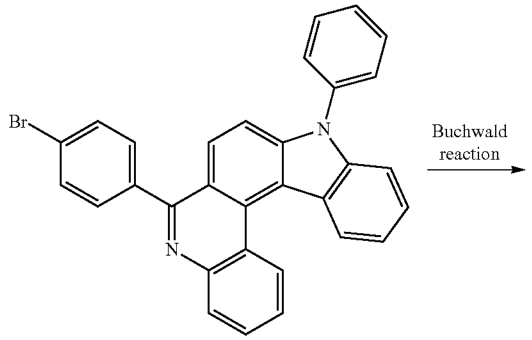

A-5

-continued

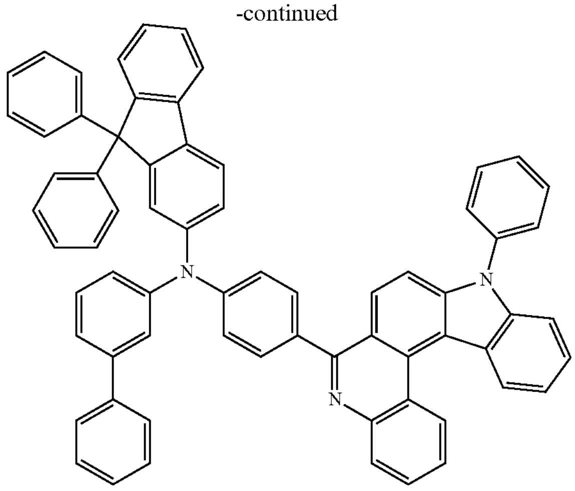

5-82

10.0 g (20.02 mmol) of A-5, 8.75 g (18.02 mmol) of N-([1,1'-biphenyl]-3-yl)-9,9-diphenyl-9H-fluoren-2-amine, 1.83 g (2.0 mmol) of $Pd_2(dba)_3$, 1.9 g (4.0 mmol) of XPhos, and 8.1 g (40.04 mmol) of NaOtBu were stirred under 100 mL of toluene at 120° C. for 7 hours. After completion of the reaction, the reaction product was cooled to room temperature, and then extracted with MC and allowed to evaporate all the reaction products. The resulting solid was column purified to obtain 7.60 g (42%) of Target Compound 5-82.

[Preparation Example 39] Preparation of Compound 6-14

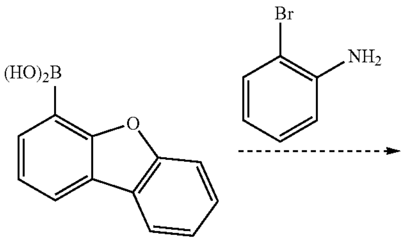

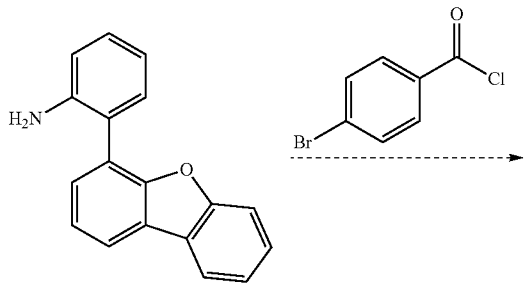

T-1

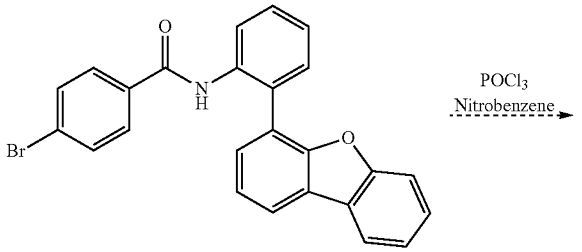

T-2

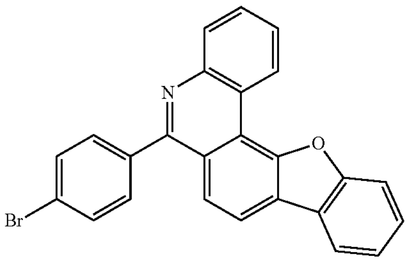

T-3

Synthesis of T-1

30.0 g (141.5 mmol) of SM, 29.2 g (169.8 mmol) of 2-bromoaniline, 8.2 g (7.07 mmol) of $Pd(PPh_3)_4$, and 90.1 g (424.5 mmol) of $K_3PO_4$ were stirred under reflux under 300 mL of 1,4-dioxane and 60 mL of $H_2O$ at 120° C. for 3 hours. After completion of the reaction, the reaction product was cooled to room temperature, and then extracted with distilled water and dichloromethane (MC). After the organic layer was dried over anhydrous $MgSO_4$, the solvent was removed by a rotary evaporator, and then the resulting product was filtered with silica gel and washed with hexane to obtain 29.0 g (79%) of Target Compound T-1.

Synthesis of T-2

29 g (111.84 mmol) of T-1 and 15.7 mL (111.84 mmol) of triethylamine were thoroughly dissolved in dichloromethane (MC), and then the temperature was maintained at 0° C. And then, 26.9 g (123.02 mmol) of 4-bromobenzoylchloride was slowly added dropwise thereto and the resulting mixture was stirred for 1 hour while maintaining the temperature. After completion of the reaction, an excessive amount of hexane was added thereto, and the resulting solid was filtered. 39.6 g (80%) of Target Compound T-2 was obtained.

Synthesis of T-3

39.6 g (89.53 mmol) of T2 was thoroughly dissolved in 300 mL of nitrobenzene, and then 10.0 mL (89.53 mmol) of $POCl_3$ was slowly added dropwise thereto. And then, the resulting mixture was stirred for 16 hours while maintaining the temperature at 150° C. After completion of the reaction, the reaction product was cooled to room temperature, and then an excessive amount of hexane was added thereto. 22.6 g (59%) of Target Compound 1-3 was obtained.

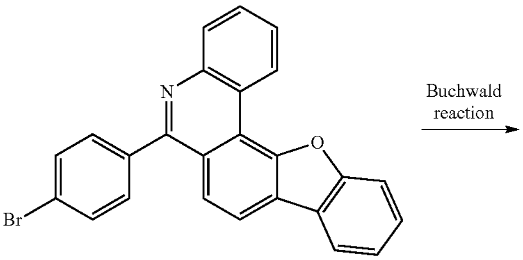

T-3

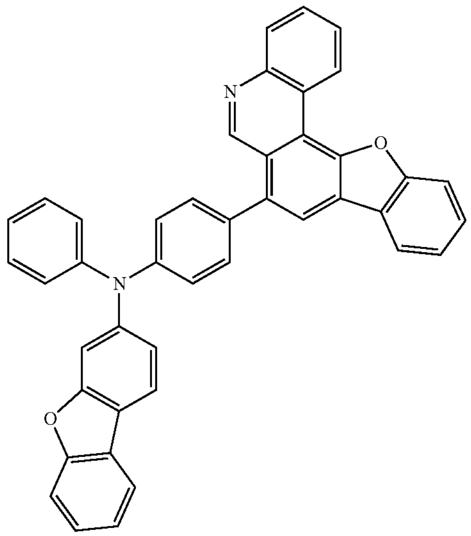

6-14

Synthesis of 6-14

10.0 g (23.57 mmol) of T-3, 5.5 g (21.21 mmol) of N-phenyldibenzo[b,d]furan-3-amine, 2.11 g (2.3 mmol) of $Pd_2(dba)_3$, 2.19 g (4.6 mmol) of XPhos, and 9.54 g (47.14 mmol) of NaOtBu were stirred under 100 mL of toluene at 120° C. for 3 hours. After completion of the reaction, the reaction product was cooled to room temperature, and then extracted with MC and allowed to evaporate all the reaction products. The resulting solid was column purified to obtain 9.38 g (66%) of Target Compound 6-14.

[Preparation Example 40] Preparation of Compound 6-37

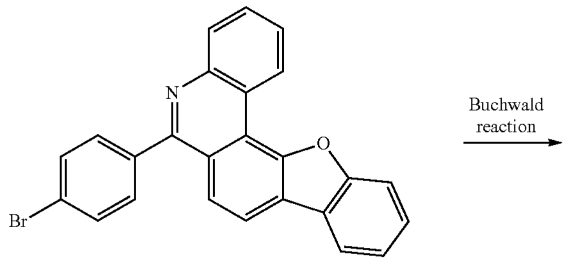

T-3

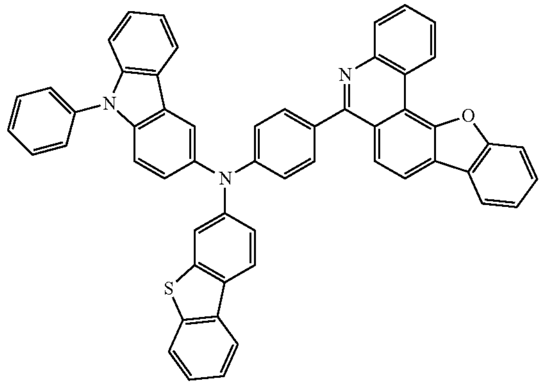

6-37

10.0 g (23.57 mmol) of T-3, 9.34 g (21.21 mmol) of N-phenyldibenzo[b,d]furan-3-amine, 2.11 g (2.3 mmol) of $Pd_2(dba)_3$, 2.19 g (4.6 mmol) of XPhos, and 9.54 g (47.14 mmol) of NaOtBu were stirred under 100 mL of toluene at 120° C. for 5 hours. After completion of the reaction, the reaction product was cooled to room temperature, and then extracted with MC and allowed to evaporate all the reaction products. The resulting solid was column purified to obtain 13.7 g (74%) of Target Compound 6-37.

[Preparation Example 41] Preparation of Compound 6-55

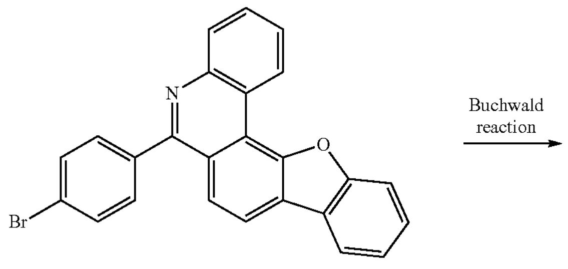

T-3

-continued

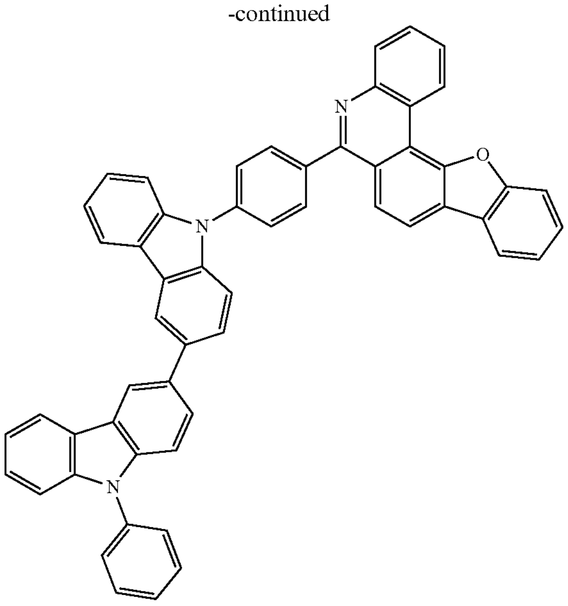

6-55

10.0 g (23.57 mmol) of T-3, 8.66 g (21.21 mmol) of 9-phenyl-9H,9'H-3,3'-bicarbazole, 2.11 g (2.3 mmol) of $Pd_2(dba)_3$, 2.19 g (4.6 mmol) of XPhos, and 9.54 g (47.14 mmol) of NaOtBu were stirred under 100 mL of toluene at 120° C. for 2 hours. After completion of the reaction, the reaction product was cooled to room temperature, and then extracted with MC and allowed to evaporate all the reaction products. The resulting solid was column purified to obtain 6.91 g (39%) of Target Compound 6-55.

[Preparation Example 41] Preparation of Compound 6-65

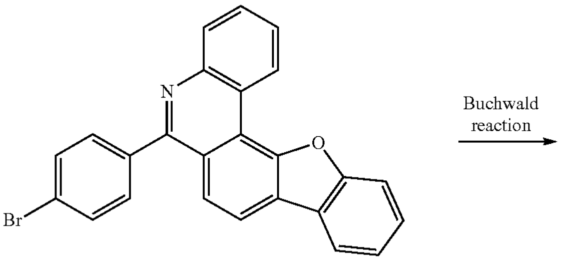

T-3

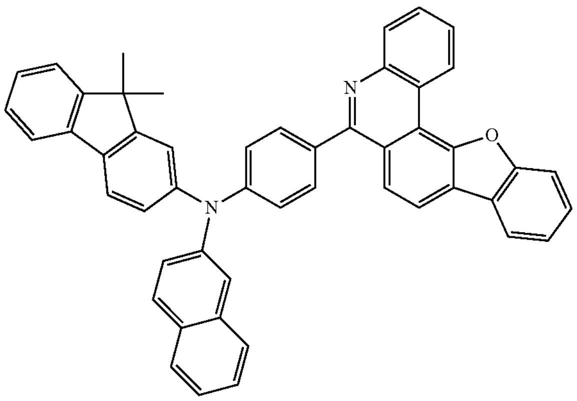

6-65

10.0 g (23.57 mmol) of T-3, 7.11 g (21.21 mmol) of 9,9-dimethyl-N-(naphthalen-2-yl)-9H-fluoren-2-amine, 2.11 g (2.3 mmol) of $Pd_2(dba)_3$, 2.19 g (4.6 mmol) of XPhos, and 9.54 g (47.14 mmol) of NaOtBu were stirred under 100 mL of toluene at 120° C. for 5 hours. After completion of the reaction, the reaction product was cooled to room temperature, and then extracted with MC and allowed to evaporate all the reaction products. The resulting solid was column purified to obtain 8.8 g (55%) of Target Compound 6-65.

[Preparation Example 42] Preparation of Compound 6-85

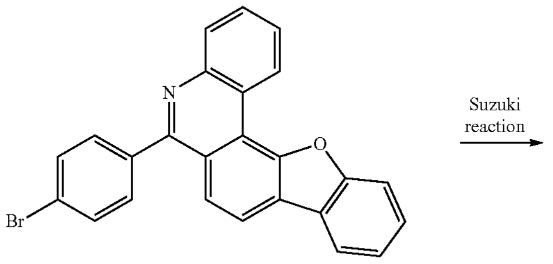

T-3

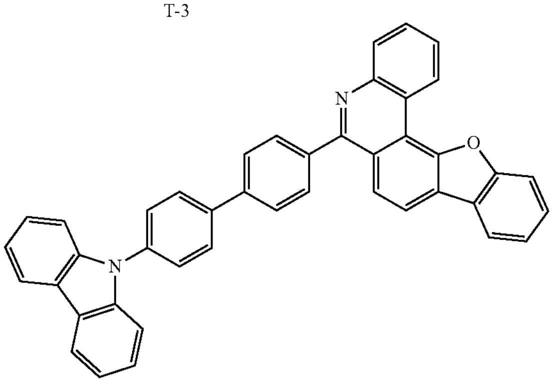

6-85

10.0 g (23.57 mmol) of T-3, 6.09 g (21.21 mmol) of (4-(9H-carbazol-9-yl)phenyl)boronic acid, 2.72 g (2.3 mmol) of $Pd(PPh_3)_4$, and 15.0 g (70.71 mmol) of $K_3PO_4$ were stirred under 100 mL of dioxane and 20 mL of $H_2O$ at 120° C. for 2 hours. After completion of the reaction, the reaction product was cooled to room temperature, and then extracted with MC and allowed to evaporate all the reaction products. The resulting solid was column purified to obtain 10.6 g (77%) of Target Compound 6-85.

[Preparation Example 43] Preparation of Compound 7-24

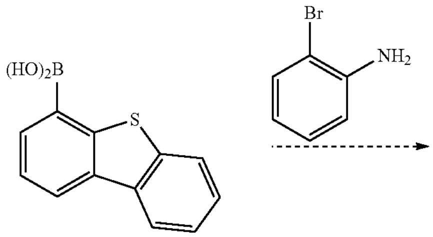

-continued

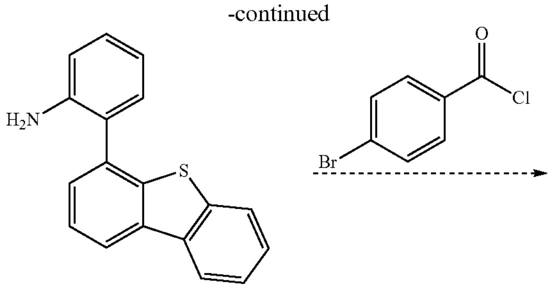

U-1

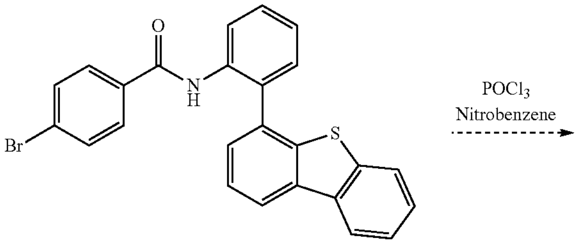

U-2

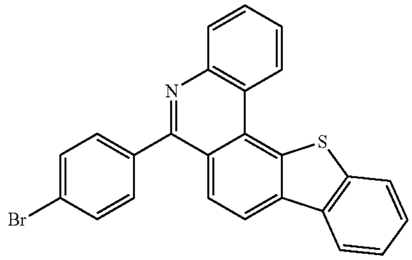

U-3

Synthesis of U-1

50.0 g (219.2 mmol) of SM, 56.5 g (328.8 mmol) of 2-bromoaniline, 25.0 g (10.96 mmol) of $Pd(PPh_3)_4$, and 140.0 g (657.6 mmol) of $K_3PO_4$ were stirred under reflux under 500 mL of 1,4-dioxane and 100 mL of $H_2O$ at 120° C. for 3 hours. After completion of the reaction, the reaction product was cooled to room temperature, and then extracted with distilled water and dichloromethane (MC). After the organic layer was dried over anhydrous $MgSO_4$, the solvent was removed by a rotary evaporator, and then the resulting product was filtered with silica gel and washed with hexane to obtain 54.0 g (89%) of Target Compound U-1.

Synthesis of U-2

54.0 g (196.1 mmol) of U-1 and 27.5 mL (196.1 mmol) of triethylamine were thoroughly dissolved in dichloromethane (MC), and then the temperature was maintained at 0° C. And then, 43.0 g (196.1 mmol) of 4-bromobenzoylchloride was slowly added dropwise thereto and the resulting mixture was stirred for 1 hour while maintaining the temperature. After completion of the reaction, an excessive amount of hexane was added thereto, and the resulting solid was filtered. 85.0 g (95%) of Target Compound U-2 was obtained.

Synthesis of U-3

85.0 g (185.44 mmol) of U-2 was thoroughly dissolved in 600 mL of nitrobenzene, and then 21.0 mL (185.44 mmol) of $POCl_3$ was slowly added dropwise thereto. And then, the resulting mixture was stirred for 3 hours while maintaining the temperature at 150° C. After completion of the reaction, the reaction product was cooled to room temperature, and then an excessive amount of EA was added thereto. 55.0 g (67%) of Target Compound U-3 was obtained.

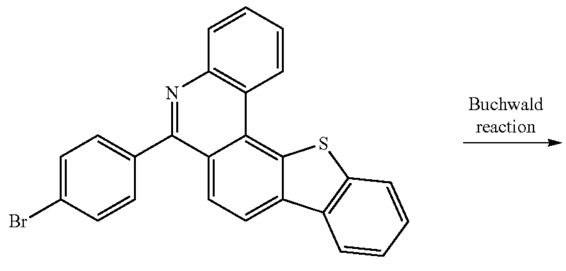

U-3

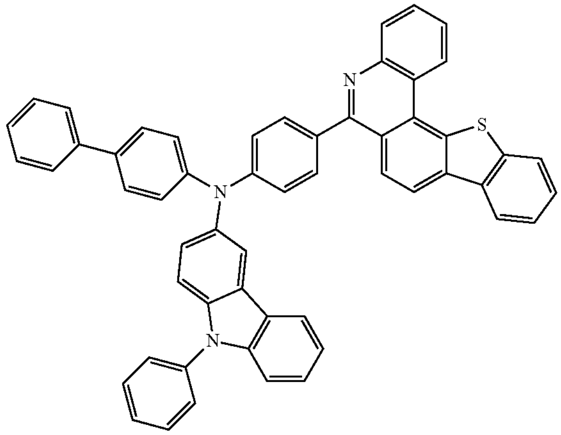

7-24

Synthesis of 7-24

10.0 g (22.57 mmol) of U-3, 8.71 g (20.3 mmol) of N-([1,1'-biphenyl]-4-yl)-9-phenyl-9H-carbazol-3-amine, 2.01 g (2.2 mmol) of $Pd_2(dba)_3$, 2.19 g (4.6 mmol) of XPhos, and 9.13 g (45.14 mmol) of NaOtBu were stirred under 100 mL of toluene at 120° C. for 1 hour. After completion of the reaction, the reaction product was cooled to room temperature, and then extracted with MC and allowed to evaporate all the reaction products. The resulting solid was column purified to obtain 15.6 g (86%) of Target Compound 7-24.

[Preparation Example 44] Preparation of Compound 7-48

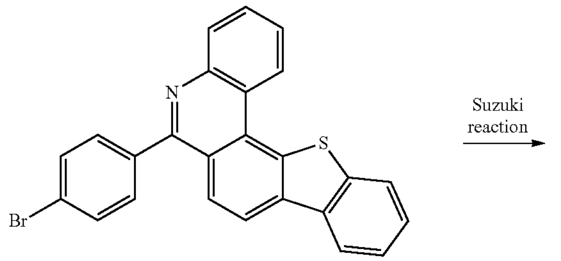

U-3

-continued

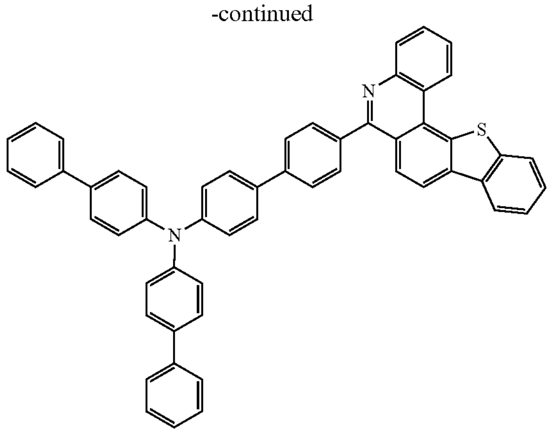

7-48

10.0 g (22.57 mmol) of U-3, 8.71 g (20.3 mmol) of N-([1,1'-biphenyl]-4-yl)-9-phenyl-9H-carbazol-3-amine, 2.72 g (2.3 mmol) of $Pd(PPh_3)_4$, and 14.4 g (67.71 mmol) of $K_3PO_4$ were stirred under 100 mL of 1,4-dioxane and 20 mL of $H_2O$ at 120° C. for 2 hours. After completion of the reaction, the reaction product was cooled to room temperature, and then extracted with MC and allowed to evaporate all the reaction products. The resulting solid was column purified to obtain 6.67 g (39%) of Target Compound 7-48.

[Preparation Example 45] Preparation of Compound 7-75

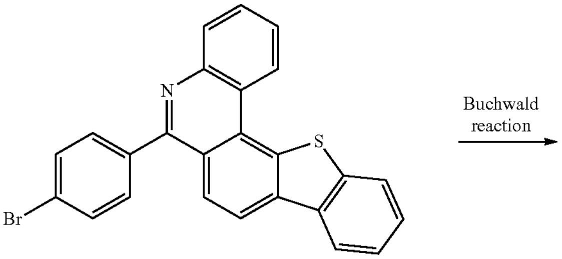

U-3

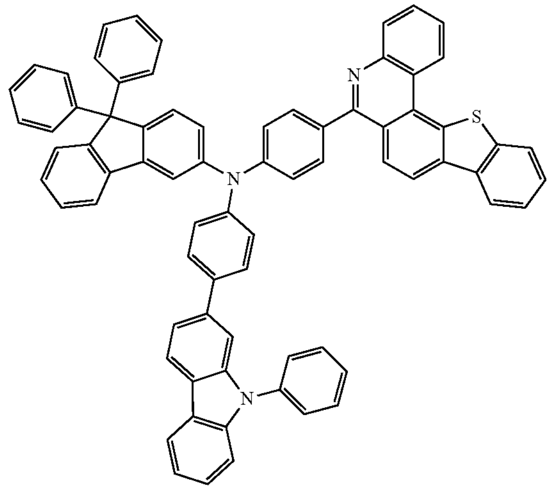

7-75

10.0 g (22.57 mmol) of U-3, 13.8 g (21.21 mmol) of 9,9-diphenyl-N-(4-(9-phenyl-9H-carbazol-2-yl)phenyl)-

9H-fluoren-3-amine, 2.01 g (2.3 mmol) of $Pd_2(dba)_3$, 2.19 g (4.6 mmol) of XPhos, and 9.13 g (45.14 mmol) of NaOtBu were stirred under 100 mL of toluene at 120° C. for 8 hours. After completion of the reaction, the reaction product was cooled to room temperature, and then extracted with MC and allowed to evaporate all the reaction products. The resulting solid was column purified to obtain 11.2 g (47%) of Target Compound 7-75.

[Preparation Example 46] Preparation of Compound 7-88

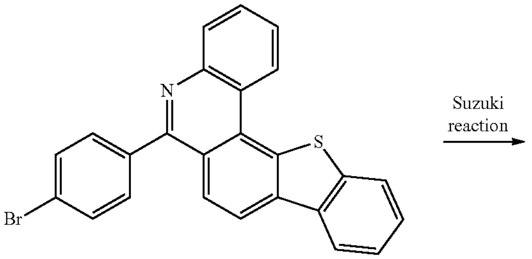

U-3

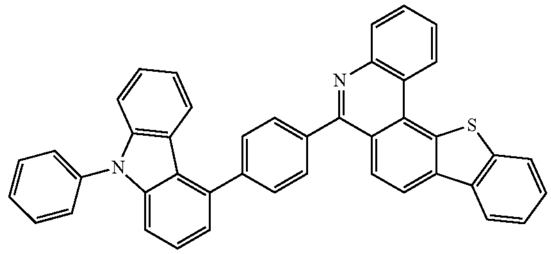

7-88

10.0 g (22.57 mmol) of U-3, 13.8 g (20.3 mmol) of 9,9-diphenyl-N-(4-(9-phenyl-9H-carbazol-2-yl)phenyl)-9H-fluoren-3-amine, 2.72 g (2.3 mmol) of $Pd(PPh_3)_4$, and 14.4 g (67.71 mmol) of $K_3PO_4$ were stirred under 100 mL of 1,4-dioxane and 20 mL of $H_2O$ at 120° C. for 2 hours. After completion of the reaction, the reaction product was cooled to room temperature, and then extracted with MC and allowed to evaporate all the reaction products. The resulting solid was column purified to obtain 12.0 g (88%) of Target Compound 7-88.

[Preparation Example 47] Preparation of Compound 1-3

The title compound was prepared in the same manner as in the preparation method of Compound 1-1, except that 4-([1,1'-biphenyl]-4-yl)-6-bromo-2-phenylpyrimidine was used instead of 2-chloro-4,6-diphenyl-1,3,5-triazine. (Yield: 54%)

[Preparation Example 48] Preparation of Compound 1-4

The title compound was prepared in the same manner as in the preparation method of Compound 1-1, except that 4-bromo-2,6-diphenylpyrimidine was used instead of 2-chloro-4,6-diphenyl-1,3,5-triazine. (Yield: 50%)

[Preparation Example 49] Preparation of Compound 1-8

The title compound was prepared in the same manner as in the preparation method of Compound 1-1, except that 1-(4-bromophenyl)-2-phenyl-1H-benzo[d]imidazole was used instead of 2-chloro-4,6-diphenyl-1,3,5-triazine. (Yield: 71%)

[Preparation Example 50] Preparation of Compound 1-10

The title compound was prepared in the same manner as in the preparation method of Compound 1-65, except that 6-(4-bromophenyl)-9-phenyl-9H-indolo[2,3-k]phenanthridine was used instead of 6-(4-bromophenyl)benzo[4,5]thieno[2,3-k]phenanthridine. (Yield: 38%)

[Preparation Example 51] Preparation of Compound 1-100

The title compound, was prepared in the same manner as in the preparation method of Compound 1-65, except that 6-(4-bromophenyl)-9-phenyl-9H-indolo[2,3-k]phenanthridine was used instead of 6-(3-bromophenyl)benzo[4,5]thieno[2,3-k]phenanthridine. (Yield: 44%)

[Preparation Example 52] Preparation of Compound 1-102

The title compound was prepared in the same manner as in the preparation method of Compound 1-113, except that (3,5-di(9H-carbazol-9-yl)phenyl)boronic acid was used instead of dibenzo[b,d]thiophen-4-ylboronic acid. (Yield: 88%)

[Preparation Example 53] Preparation of Compound 1-10

The title compound was prepared in the same manner as in the preparation method of Compound 1-113, except that (9,9-diphenyl-9H-fluoren-2-yl)boronic acid was used instead of dibenzo[b,d]thiophen-4-ylboronic acid. (Yield: 49%)

[Preparation Example 54] Preparation of Compound 1-123

The title compound was prepared in the same manner as in the preparation method of Compound 1-113, except that (9-phenyl-9H-carbazol-3-yl)boronic acid was used instead of dibenzo[b,d]thiophen-4-ylboronic acid. (Yield: 58%)

[Preparation Example 55] Preparation of Compound 1-175

The title compound was prepared in the same manner as in the preparation method of Compound 1-65, except that 6-(3-bromophenyl)benzofuro[2,3-k]phenanthridine was used instead of 6-(4-bromophenyl)benzo[4,5]thieno[2,3-k]phenanthridine. (Yield: 51%)

[Preparation Example 56] Preparation of Compound 1-251

The title compound was prepared in the same manner as in the preparation method of Compound 1-1, except that 2-bromo-9,10-di(naphthalen-2-yl)anthracene was used instead of 2-chloro-4,6-diphenyl-1,3,5-triazine. (Yield: 81%)

[Preparation Example 57] Preparation of Compound 1-366

The title compound was prepared in the same manner as in the preparation method of Compound 1-113, except that (9,10-di(naphthalen-2-yl)anthracen-2-yl)boronic acid was used instead of dibenzo[b,d]thiophen-4-ylboronic acid. (Yield: 71%)

[Preparation Example 58] Preparation of Compound 1-369

The title compound was prepared in the same manner as in the preparation method of Compound 1-113, except that (10-phenylanthracen-9-yl)boronic acid was used instead of dibenzo[b,d]thiophen-4-ylboronic acid. (Yield: 51%)

[Preparation Example 59] Preparation of Compound 1-391

The title compound was prepared in the same manner as in the preparation method of Compound 1-113, except that (4-(4,6-diphenylpyrimidin-2-yl)phenyl)boronic acid was used instead of dibenzo[b,d]thiophen-4-ylboronic acid. (Yield: 71%)

[Preparation Example 60] Preparation of Compound 1-401

The title compound was prepared in the same manner as in the preparation method of Compound 1-113, except that (3,5-di(phenanthren-9-yl)phenyl)boronic acid was used instead of dibenzo[b,d]thiophen-4-ylboronic acid. (Yield: 71%)

[Preparation Example 61] Preparation of Compound 1-416

The title compound was prepared in the same manner as in the preparation method of Compound 1-113, except that (4-(6-([1,1'-biphenyl]-4-yl)-2-phenylpyrimidin-4-yl)phenyl)boronic acid was used instead of dibenzo[b,d]thiophen-4-ylboronic acid. (Yield: 47%)

[Preparation Example 62] Preparation of Compound 1-451

The title compound was prepared in the same manner as in the preparation method of Compound 1-113, except that (4-(1,10-phenanthrolin-2-yl)phenyl)boronic acid was used instead of dibenzo[b,d]thiophen-4-ylboronic acid. (Yield: 63%)

[Preparation Example 63] Preparation of Compound 1-452

The title compound was prepared in the same manner as in the preparation method of Compound 1-113, except that (4-(imidazo[1,2-a]pyridin-2-yl)phenyl)boronic acid was used instead of dibenzo[b,d]thiophen-4-ylboronic acid. (Yield: 50%)

[Preparation Example 64] Preparation of Compound 1-459

The title compound was prepared in the same manner as in the preparation method of Compound 1-113, except that (4-(2-phenyl-1H-benzo[d]imidazol-1-yl)phenyl)boronic acid was used instead of dibenzo[b,d]thiophen-4-ylboronic acid. (Yield: 54%)

[Preparation Example 65] Preparation of Compound 1-460

The title compound was prepared in the same manner as in the preparation method of Compound 1-113, except that (4-(2-ethyl-1H-benzo[d]imidazol-1-yl)phenyl)boronic acid was used instead of dibenzo[b,d]thiophen-4-ylboronic acid. (Yield: 49%)

[Preparation Example 66] Preparation of Compound 1-471

The title compound was prepared in the same manner as in the preparation method of Compound 1-113, except that [2,2':6',2"-terpyridin]-4'-ylboronic acid was used instead of dibenzo[b,d]thiophen-4-ylboronic acid. (Yield: 55%)

[Preparation Example 67] Preparation of Compound 1-39

The title compound was prepared in the same manner as in the preparation method of Compound 1-36, except that (2,6-diphenylpyrimidin-4-yl)boronic acid was used instead of 2-chloro-4,6-diphenyl-1,3,5-triazine. (Yield: 47%)

[Preparation Example 68] Preparation of Compound 1-41

The title compound was prepared in the same manner as in the preparation method of Compound 1-36, except that quinolin-2-ylboronic acid was used instead of 2-chloro-4,6-diphenyl-1,3,5-triazine. (Yield: 55%)

[Preparation Example 69] Preparation of Compound 1-43

The title compound was prepared in the same manner as in the preparation method of Compound 1-36, except that (4-(2-phenyl-1H-benzo[d]imidazol-1-yl)phenyl)boronic acid was used instead of 2-chloro-4,6-diphenyl-1,3,5-triazine. (Yield: 74%)

[Preparation Example 70] Preparation of Compound 1-44

The title compound was prepared in the same manner as in the preparation method of Compound 1-36, except that (4,6-diphenylpyrimidin-2-yl)boronic acid was used instead of 2-chloro-4,6-diphenyl-1,3,5-triazine. (Yield: 69%)

[Preparation Example 71] Preparation of Compound 1-47

The title compound was prepared in the same manner as in the preparation method of Compound 1-36, except that (3,5-di(9H-carbazol-9-yl)phenyl)boronic acid was used instead of 2-chloro-4,6-diphenyl-1,3,5-triazine. (Yield: 84%)

[Preparation Example 72] Preparation of Compound 1-67

The title compound was prepared in the same manner as in the preparation method of Compound 1-56, except that (3,5-di(9H-carbazol-9-yl)phenyl)boronic acid was used instead of 2-chloro-4,6-diphenyl-1,3,5-triazine. (Yield: 77%)

[Preparation Example 73] Preparation of Compound 1-58

The title compound was prepared in the same manner as in the preparation method of Compound 1-56, except that (3,5-di(9H-carbazol-9-yl)phenyl)boronic acid was used instead of 2-chloro-4,6-diphenyl-1,3,5-triazine. (Yield: 77%)

[Preparation Example 74] Preparation of Compound 1-67

The title compound was prepared in the same manner as in the preparation method of Compound 1-56, except that (6-([1,1'-biphenyl]-4-yl)-2-phenylpyrimidin-4-yl)boronic acid was used instead of 2-chloro-4,6-diphenyl-1,3,5-triazine. (Yield: 70%)

[Preparation Example 75] Preparation of Compound 1-74

The title compound was prepared in the same manner as in the preparation method of Compound 1-56, except that (2,6-diphenylpyrimidin-4-yl)boronic acid was used instead of 2-chloro-4,6-diphenyl-1,3,5-triazine. (Yield: 49%)

[Preparation Example 76] Preparation of Compound 1-146

The title compound was prepared in the same manner as in the preparation method of Compound 1-157, except that 9,9'-(5-(4,4,5,5-tetramethyl-1,3,2-dioxaborolan-2-yl)-1,3-phenylene)bis(9H-carbazole) 2-chloro-4,6-diphenyl-1,3,5-triazine was used. (Yield: 77%)

[Preparation Example 77] Preparation of Compound 1-155

The title compound was prepared in the same manner as in the preparation method of Compound 1-65, except that 6-(3-bromophenyl)benzo[4,5]thieno[2,3-k]phenanthridine was used instead of 6-(4-bromophenyl)benzo[4,5]thieno[2,3-k]phenanthridine. (Yield: 47%)

[Preparation Example 78] Preparation of Compound 1-166

The title compound was prepared in the same manner as in the preparation method of Compound 1-177, except that 2-((14-oxidanylidene)boranyl)-4,6-diphenyl-1,3,5-triazine was used instead of 9,9'-(5-(4,4,5,5-tetramethyl-1,3,2-dioxaborolan-2-yl)-1,3-phenylene)bis(9H-carbazole). (Yield: 49%)

[Preparation Example 78] Preparation of Compound 1-168

The title compound was prepared in the same manner as in the preparation method of Compound 1-177, except that (6-([1,1'-biphenyl]-4-yl)-2-phenylpyrimidin-4-yl)boronic acid was used instead of 9,9'-(5-(4,4,5,5-tetramethyl-1,3,2-dioxaborolan-2-yl)-1,3-phenylene)bis(9H-carbazole). (Yield: 63%)

[Preparation Example 79] Preparation of Compound 1-169

The title compound was prepared in the same manner as in the preparation method of Compound 1-177, except that (2,6-diphenylpyrimidin-4-yl)boronic acid was used instead of 9,9'-(5-(4,4,5,5-tetramethyl-1,3,2-dioxaborolan-2-yl)-1,3-phenylene)bis(9H-carbazole). (Yield: 74%)

[Preparation Example 80] Preparation of Compound 1-178

The title compound was prepared in the same manner as in the preparation method of Compound 1-177, except that phenanthren-9-ylboronic acid was used instead of 9,9'-(5-(4,4,5,5-tetramethyl-1,3,2-dioxaborolan-2-yl)-1,3-phenylene)bis(9H-carbazole). (Yield: 41%)

[Preparation Example 81] Preparation of Compound 1-179

The title compound was prepared in the same manner as in the preparation method of Compound 1-177, except that [2,2'-binaphthalen]-6-ylboronic acid was used instead of 9,9'-(5-(4,4,5,5-tetramethyl-1,3,2-dioxaborolan-2-yl)-1,3-phenylene)bis(9H-carbazole). (Yield: 71%)

[Preparation Example 82] Preparation of Compound 4-3

The title compound was prepared in the same manner as in the preparation method of Compound 4-1, except that 4-([1,1'-biphenyl]-4-yl)-6-bromo-2-phenylpyrimidine was used instead of 2-chloro-4,6-diphenyl-1,3,5-triazine. (Yield: 55%)

[Preparation Example 83] Preparation of Compound 4-4

The title compound was prepared in the same manner as in the preparation method of Compound 4-1, except that 4-bromo-2,6-diphenylpyrimidine was used instead of 2-chloro-4,6-diphenyl-1,3,5-triazine. (Yield: 87%)

[Preparation Example 84] Preparation of Compound 4-8

The title compound was prepared in the same manner as in the preparation method of Compound 4-1, except that 1-(4-bromophenyl)-2-phenyl-1H-benzo[d]imidazole was used instead of 2-chloro-4,6-diphenyl-1,3,5-triazine. (Yield: 77%)

[Preparation Example 85] Preparation of Compound 4-9

The title compound was prepared in the same manner as in the preparation method of Compound 4-1, except that 2-bromo-4,6-diphenylpyrimidine was used instead of 2-chloro-4,6-diphenyl-1,3,5-triazine. (Yield: 64%)

[Preparation Example 86] Preparation of Compound 4-10

The title compound was prepared in the same manner as in the preparation method of Compound 1-65, except that 6-(4-bromophenyl)-13-phenyl-13H-indolo[3,2-k]phenanthridine was used instead of 6-(4-bromophenyl)benzo[4,5]thieno[2,3-k]phenanthridine. (Yield: 38%)

[Preparation Example 87] Preparation of Compound 4-12

The title compound was prepared in the same manner as in the preparation method of Compound 4-1, except that 9,9'-(5-bromo-1,3-phenylene)bis(9H-carbazole) was used instead of 2-chloro-4,6-diphenyl-1,3,5-triazine. (Yield: 55%)

[Preparation Example 88] Preparation of Compound 4-15

The title compound was prepared in the same manner as in the preparation method of Compound 4-1, except that 9-bromo-10-(naphthalen-2-yl)anthracene was used instead of 2-chloro-4,6-diphenyl-1,3,5-triazine. (Yield: 70%)

[Preparation Example 89] Preparation of Compound 4-19

The title compound was prepared in the same manner as in the preparation method of Compound 4-1, except that 2-bromo-9,9-diphenyl-9H-fluorene was used instead of 2-chloro-4,6-diphenyl-1,3,5-triazine. (Yield: 70%)

[Preparation Example 90] Preparation of Compound 4-22

The title compound was prepared in the same manner as in the preparation method of Compound 4-1, except that 4-bromodibenzo[b,d]furan was used instead of 2-chloro-4,6-diphenyl-1,3,5-triazine. (Yield: 70%)

[Preparation Example 91] Preparation of Compound 4-29

The title compound was prepared in the same manner as in the preparation method of Compound 4-1, except that 2-bromotriphenylene was used instead of 2-chloro-4,6-diphenyl-1,3,5-triazine. (Yield: 87%)

[Preparation Example 92] Preparation of Compound 4-33

The title compound was prepared in the same manner as in the preparation method of Compound 4-1, except that 3-bromo-9-phenyl-9H-carbazole was used instead of 2-chloro-4,6-diphenyl-1,3,5-triazine. (Yield: 74%)

[Preparation Example 93] Preparation of Compound 4-91

The title compound was prepared in the same manner as in the preparation method of Compound 4-119, except that 2-chloro-4,6-diphenyl-1,3,5-triazine was used instead of 2-bromotriphenylene. (Yield: 74%)

[Preparation Example 94] Preparation of Compound 4-93

The title compound was prepared in the same manner as in the preparation method of Compound 4-119, except that 4-([1,1'-biphenyl]-4-yl)-6-bromo-2-phenylpyrimidine was used instead of 2-bromotriphenylene. (Yield: 59%)

[Preparation Example 95] Preparation of Compound 4-94

The title compound was prepared in the same manner as in the preparation method of Compound 4-119, except that 4-bromo-2,6-diphenylpyrimidine was used instead of 2-bromotriphenylene. (Yield: 57%)

[Preparation Example 96] Preparation of Compound 4-99

The title compound was prepared in the same manner as in the preparation method of Compound 4-119, except that 2-bromo-4,6-diphenylpyrimidine was used instead of 2-bromotriphenylene. (Yield: 51%)

[Preparation Example 97] Preparation of Compound 4-100

The title compound was prepared in the same manner as in the preparation method of Compound 1-65, except that 6-(3-bromophenyl)-13-phenyl-13H-indolo[3,2-k]phenanthridine was used instead of 6-(4-bromophenyl)benzo[4,5]thieno[2,3-k]phenanthridine. (Yield: 38%)

[Preparation Example 98] Preparation of Compound 4-101

The title compound was prepared in the same manner as in the preparation method of Compound 4-119, except that 2-(4-bromophenyl)-1-phenyl-1H-benzo[d]imidazole was used instead of 2-bromotriphenylene. (Yield: 77%)

[Preparation Example 99] Preparation of Compound 4-102

The title compound was prepared in the same manner as in the preparation method of Compound 4-119, except that 9,9'-(5-bromo-1,3-phenylene)bis(9H-carbazole) was used instead of 2-bromotriphenylene. (Yield: (56%)

[Preparation Example 100] Preparation of Compound 4-106

The title compound was prepared in the same manner as in the preparation method of Compound 4-119, except that 7-bromoquinoline was used instead of 2-bromotriphenylene. (Yield: 40%)

[Preparation Example 101] Preparation of Compound 4-109

The title compound was prepared in the same manner as in the preparation method of Compound 4-119, except that 2-bromo-9,9-diphenyl-9H-fluorene was used instead of 2-bromotriphenylene. (Yield: 81%)

[Preparation Example 102] Preparation of Compound 4-113

The title compounds was prepared in the same manner as in the preparation method of Compound 4-119, except that 4-bromodibenzo[b,d]thiophene was used instead of 2-bromotriphenylene. (Yield: 91%)

[Preparation Example 103] Preparation of Compound 4-36

The title compound was prepared in the same manner as in the preparation method of Compound 4-46, except that (4,6-diphenyl-1,3,5-triazin-2-yl)boronic acid was used instead of 1-phenyl-2-(4-(4,4,5,5-tetramethyl-1,3,2-dioxaborolan-2-yl)phenyl)-1H-benzo[d]imidazole. (Yield: 49%)

[Preparation Example 104] Preparation of Compound 4-38

The title compound was prepared in the same manner as in the preparation method of Compound 4-46, except that (6-([1,1'-biphenyl]-4-yl)-2-phenylpyrimidin-4-yl)boronic acid was used instead of 1-phenyl-2-(4-(4,4,5,5-tetramethyl-1,3,2-dioxaborolan-2-yl)phenyl)-1H-benzo[d]imidazole. (Yield: 53%)

[Preparation Example 104] Preparation of Compound 4-39

The title compound was prepared in the same manner as in the preparation method of Compound 4-46, except that (2,6-diphenylpyrimidin-4-yl)boronic acid was used instead of 1-phenyl-2-(4-(4,4,5,5-tetramethyl-1,3,2-dioxaborolan-2-yl)phenyl)-1H-benzo[d]imidazole (Yield: 51%)

[Preparation Example 105] Preparation of Compound 4-43

The title compound was prepared in the same manner as in the preparation method of Compound 4-46, except that (4-(2-phenyl-1H-benzo[d]imidazol-1-yl)phenyl)boronic acid was used instead of 1-phenyl-2-(4-(4,4,5,5-tetramethyl-1,3,2-dioxaborolan-2-yl)phenyl)-1H-benzo[d]imidazole. (Yield: 49%)

[Preparation Example 106] Preparation of Compound 4-49

The title compound was prepared in the same manner as in the preparation method of Compound 4-46, except that [2,2'-binaphthalen]-6-ylboronic acid was used instead of 1-phenyl-244-(4,4,5,5-tetramethyl-1,3,2-dioxaborolan-2-yl) phenyl)-1H-benzo[d]imidazole. (Yield: 71%)

[Preparation Example 107] Preparation of Compound 4-59

The title compound was prepared in the same manner as in the preparation method of Compound 4-66, except that (2,6-diphenylpyrimidin-4-yl)boronic acid was used instead of 1-phenyl-2-(4-(4,4,5,5-tetramethyl-1,3,2-dioxaborolan-2-yl)phenyl)-1H-benzo[d]imidazole. (Yield: 59%)

[Preparation Example 108] Preparation of Compound 4-61

The title compound was prepared in the same manner as in the preparation method of Compound 4-66, except that 2-bromoquinoline was used instead of 1-phenyl-2-(4-(4,4,5,5-tetramethyl-1,3,2-dioxaborolan-2-yl)phenyl)-1H-benzo[d]imidazole. (Yield: 37%)

[Preparation Example 109] Preparation of Compound 4-63

The title compound was prepared in the same manner as in the preparation method of Compound 4-66, except that (4-(2-phenyl-1H-benzo[d]imidazol-1-yl)phenyl)boronic acid was used instead of 1-phenyl-2-(4-(4,4,5,5-tetramethyl-1,3,2-dioxaborolan-2-yl)phenyl)-1H-benzo[d]imidazole. (Yield: 69%)

[Preparation Example 110] Preparation of Compound 4-64

The title compound was prepared in the same manner as in the preparation method of Compound 4-66, except that (4,6-diphenylpyrimidin-2-yl)boronic acid was used instead of 1-phenyl-2-(4-(4,4,5,5-tetramethyl-1,3,2-dioxaborolan-2-yl)phenyl)-1H-benzo[d]imidazole. (Yield: 60%)

[Preparation Example 111] Preparation of Compound 4-65

The title compound was prepared in the same manner as in the preparation method of Compound 1-65, except that 6-(3-bromophenyl)benzo[4,5]thieno[3,2-k]phenanthridine was used instead of 6-(4-bromophenyl)benzo[4,5]thieno[2,3-k]phenanthridine. (Yield: 48%)

[Preparation Example 112] Preparation of Compound 4-72

The title compound was prepared in the same manner as in the preparation method of Compound 4-66, except that dibenzo[b,d]thiophen-4-ylboronic acid was used instead of 1-phenyl-2-(4-(4,4,5,5-tetramethyl-1,3,2-dioxaborolan-2-yl)phenyl)-1H-benzo[d]imidazole. (Yield: 60%)

[Preparation Example 113] Preparation of Compound 4-251

The title compound was prepared in the same manner as in the preparation method of Compound 4-66, except that (9,10-di(naphthalen-2-yl)anthracen-2-yl)boronic acid was used instead of 1-phenyl-2-(4-(4,4,5,5-tetramethyl-1,3,2-dioxaborolan-2-yl)phenyl)-1H-benzo[d]imidazole. (Yield: 55%)

[Preparation Example 114] Preparation of Compound 4-254

The title compound was prepared in the same manner as in the preparation method of Compound 4-66, except that (10-phenylanthracen-9-yl)boronic acid was used instead of 1-phenyl-2-(4-(4,4,5,5-tetramethyl-1,3,2-dioxaborolan-2-yl)phenyl)-1H-benzo[d]imidazole (Yield: 61%)

[Preparation Example 115] Preparation of Compound 4-336

The title compound was prepared in the same manner as in the preparation method of Compound 4-66, except that (3-(1,10-phenanthrolin-2-yl)phenyl)boronic acid was used instead of 1-phenyl-2-(4-(4,4,5,5-tetramethyl-1,3,2-dioxaborolan-2-yl)phenyl)-1H-benzo[d]imidazole. (Yield: 49%)

[Preparation Example 116] Preparation of Compound 4-362

The title compound was prepared in the same manner as in the preparation method of Compound 4-66, except that

[2,3'-bipyridin]-6-ylboronic acid was used instead of 1-phenyl-2-(4-(4,4,5,5-tetramethyl-1,3,2-dioxaborolan-2-yl)phenyl)-1H-benzo[d]imidazole. (Yield: 80%)

[Preparation Example 117] Preparation of Compound 4-79

The title compound was prepared in the same manner as in the preparation method of Compound 4-78, except that (2,6-diphenylpyrimidin-4-yl)boronic acid was used instead of (6-([1,1'-biphenyl]-4-yl)-2-phenylpyrimidin-4-yl)boronic acid. (Yield: 70%)

[Preparation Example 118] Preparation of Compound 4-84

The title compound was prepared in the same manner as in the preparation method of Compound 4-78, except that (4,6-diphenylpyrimidin-2-yl)boronic acid was used instead of (6-([1,1'-biphenyl]-4-yl)-2-phenylpyrimidin-4-yl)boronic acid. (Yield: 73%)

[Preparation Example 119] Preparation of Compound 4-85

The title compound was prepared in the same manner as in the preparation method of Compound 1-65, except that 6-(3-bromophenyl)benzofuro[3,2-k]phenanthridine was used instead of 6-(4-bromophenyl)benzo[4,5]thieno[2,3-k]phenanthridine. (Yield: 44%)

[Preparation Example 120] Preparation of Compound 4-89

The title compound was prepared in the same manner as in the preparation method of Compound 4-78, except that [2,2'-binaphthalen]-6-ylboronic acid was used instead of (6-([1,1'-biphenyl]-4-yl)-2-phenylpyrimidin-4-yl)boronic acid. (Yield: 47%)

[Preparation Example 121] Preparation of Compound 4-166

The title compound was prepared in the same manner as in the preparation method of Compound 4-168, except that 2-chloro-4,6-diphenyl-1,3,5-triazine was used instead of 4-([1,1'-biphenyl]-4-yl)-6-bromo-2-phenylpyrimidine. (Yield: 73%)

[Preparation Example 122] Preparation of Compound 4-174

The title compound was prepared in the same manner as in the preparation method of Compound 4-168, except that 2-bromo-4,6-diphenylpyrimidine was used instead of 4-([1,1'-biphenyl]-4-yl)-6-bromo-2-phenylpyrimidine. (Yield: 44%)

[Preparation Example 123] Preparation of Compound 4-177

The title compound was prepared in the same manner as in the preparation method of Compound 4-168, except that 9,9'-(5-bromo-1,3-phenylene)bis(9H-carbazole) was used instead of 4-([1,1'-biphenyl]-4-yl)-6-bromo-2-phenylpyrimidine. (Yield: 54%)

[Preparation Example 124] Preparation of Compound 4-179

The title compound was prepared in the same manner as in the preparation method of Compound 4-168, except that 6-bromo-2,2'-binaphthalene was used instead of 4-([1,1'-biphenyl]-4-yl)-6-bromo-2-phenylpyrimidine. (Yield: 54%)

[Preparation Example 125] Preparation of Compound 4-481

The title compound was prepared in the same manner as in the preparation method of Compound 4-78, except that (9,10-di(naphthalen-2-yl)anthracen-2-yl)boronic acid was used instead of (6-([1,1'-biphenyl]-4-yl)-2-phenylpyrimidin-4-yl)boronic acid. (Yield: 40%)

[Preparation Example 126] Preparation of Compound 4-484

The title compound was prepared in the same manner as in the preparation method of Compound 4-78, except that (10-phenylanthracen-9-yl)boronic acid was used instead of (6-([1,1'-biphenyl]-4-yl)-2-phenylpyrimidine-4-yl)boronic acid. (Yield: 49%)

[Preparation Example 126] Preparation of Compound 4-485

The title compound was prepared in the same manner as in the preparation method of Compound 4-78, except that (4-(diphenylphosphoryl)phenyl)boronic acid was used instead of (6-([1,1'-biphenyl]-4-yl)-2-phenylpyrimidine-4-yl)boronic acid. (Yield: 62%)

[Preparation Example 127] Preparation of Compound 4-564

The title compound was prepared in the same manner as in the preparation method of Compound 4-78, except that (1,10-phenanthrolin-2-yl)boronic acid was used instead of (6-([1,1'-biphenyl]-4-yl)-2-phenylpyrimidine-4-yl)boronic acid. (Yield: 49%)

[Preparation Example 128] Preparation of Compound 4-565

The title compound was prepared in the same manner as in the preparation method of Compound 4-78, except that (4-(1,10-phenanthrolin-2-yl)phenyl)boronic acid was used instead of (6-([1,1'-biphenyl]-4-yl)-2-phenylpyrimidine-4-yl)boronic acid. (Yield: 39%)

[Preparation Example 129] Preparation of Compound 4-574

The title compound was prepared in the same manner as in the preparation method of Compound 4-78, except that (4-(2-phenyl-1H-benzo[d]imidazol-1-yl)phenyl)boronic acid was used instead of (6-([1,1'-biphenyl]-4-yl)-2-phenylpyrimidine-4-yl)boronic acid. (Yield: 39%)

[Preparation Example 130] Preparation of Compound 4-576

The title compound was prepared in the same manner as in the preparation method of Compound 4-78, except that 1-(3-(borino-13-oxidanyl)phenyl)-2-ethyl-1H-benzo[d]imidazole was used instead of (6-([1,1'-biphenyl]-4-yl)-2-phenylpyrimidine-4-yl)boronic acid. (Yield: 66%)

[Preparation Example 131] Preparation of Compound 4-578

The title compound was prepared in the same manner as in the preparation method of Compound 4-78, except that 1-(3-(borino-13-oxidanyl)phenyl)-2-phenyl-1H-benzo[d] imidazole was used instead of (6-([1,1'-biphenyl]-4-yl)-2-phenylpyrimidine-4-yl)boronic acid. (Yield: 66%)

[Preparation Example 132] Preparation of Compound 4-590

The title compound was prepared in the same manner as in the preparation method of Compound 4-78, except that [2,2'-bipyridin]-6-ylboronic acid was used instead of (6-([1,1'-biphenyl]-4-yl)-2-phenylpyrimidine-4-yl)boronic acid. (Yield: 76%)

[Preparation Example 133] Preparation of Compound 4-591

The title compound was prepared in the same manner as in the preparation method of Compound 4-78, except that [2,3'-bipyridin]-6-ylboronic acid was used instead of (6-([1,1'-biphenyl]-4-yl)-2-phenylpyrimidine-4-yl)boronic acid. (Yield: 76%)

[Preparation Example 134] Preparation of Compound 4-599

The title compound was prepared in the same manner as in the preparation method of Compound 4-168, except that 9-bromo-10-phenylanthracene was used instead of 4-([1,1'-biphenyl]-4-yl)-6-bromo-2-phenylpyrimidine. (Yield: 81%)

[Preparation Example 135] Preparation of Compound 4-600

The title compound was prepared in the same manner as in the preparation method of Compound 4-168, except that (4-bromophenyl)diphenylphosphine oxide was used instead of 4-([1,1'-biphenyl]-4-yl)-6-bromo-2-phenylpyrimidine. (Yield: 88%)

[Preparation Example 136] Preparation of Compound 10-1

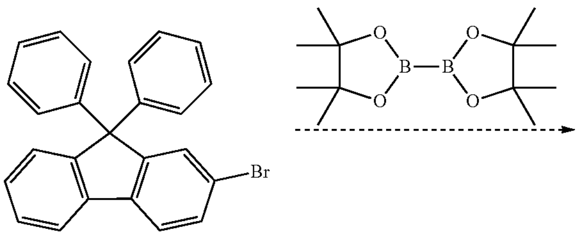

-continued

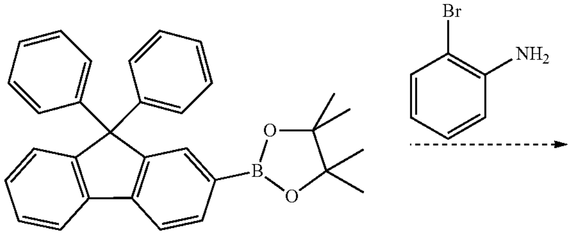

X-1

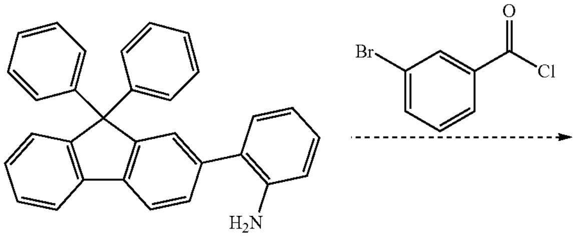

X-2

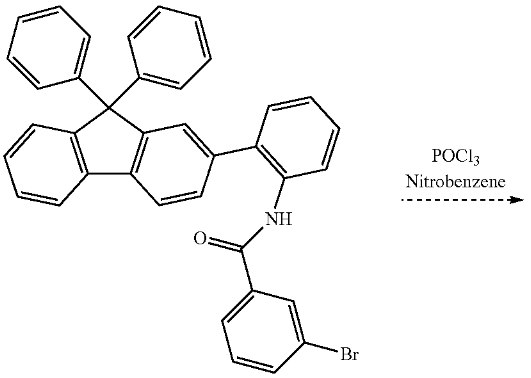

X-3

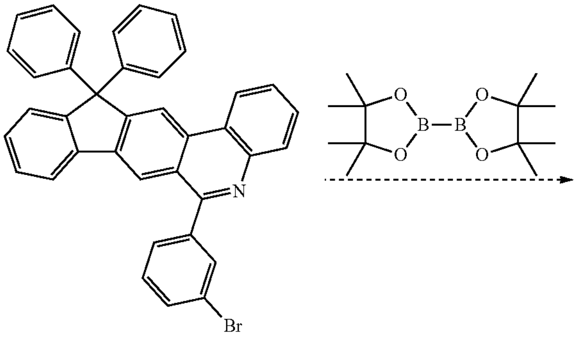

X-4

-continued

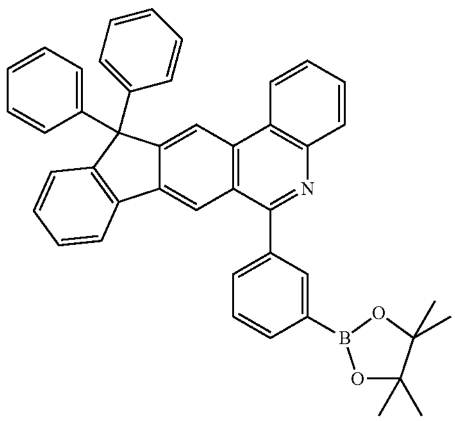

X-5

Synthesis of X-1

61 g (153.5 mmol) of 2-bromo-9,9-diphenyl-9H-fluorene, 58.5 g (230.3 mmol) of dioxaborolane, 5.6 g (7.7 mmol) of $PdCl_2$(dppf), and 45.2 g (460.6 mmol) of KOAc were stirred under reflux under 600 mL of 1,4-dioxane at 120° C. for 2 hours. After completion of the reaction, the reaction product was cooled to room temperature, and then extracted with distilled water and dichloromethane (MC). After the organic layer was dried over anhydrous $MgSO_4$, the solvent was removed by a rotary evaporator, and then the resulting product was filtered with silica gel and washed with hexane to obtain 63.6 g (93%) of Target Compound X-1.

Synthesis of X-2

63.6 g (143.1 mmol) of X-1, 27.1 g (157.4 mmol) of 2-bromoaniline, 8.3 g (7.2 mmol) of $Pd(PPh_3)_4$, and 91.1 g (429.4 mmol) of $K_3PO_4$ were stirred under reflux under 500 mL of 1,4-dioxane and 100 mL of $H_2O$ at 120° C. for 17 hours. After completion of the reaction, the reaction product was cooled to room temperature, and then extracted with distilled water and dichloromethane (MC). After the organic layer was dried over anhydrous $MgSO_4$, the solvent was removed by a rotary evaporator, and then the resulting product was filtered with silica gel and washed with hexane to obtain 42.3 g (75%) of Target Compound X-2.

Synthesis of X-3

42.3 g (103.3 mmol) of X-2 and 43.2 mL (309.9 mmol) of triethylamine were thoroughly dissolved in dichloromethane (MC), and then the temperature was maintained at 0° C. And then, 34.0 g (154.9 mmol) of 3-bromobenzoylchloride was slowly added dropwise thereto and the resulting mixture was stirred for 1 hour while maintaining the temperature. After completion of the reaction, an excessive amount of hexane was added thereto, and the resulting solid was filtered. 59.3 g (97%) of Target Compound X-3 was obtained.

Synthesis of X-4

59.3 g (100.0 mmol) of X-3 was thoroughly dissolved in 600 L of nitrobenzene, and then 10.3 mL (110.1 mmol) of $POCl_3$ was slowly added dropwise thereto. And then, the resulting mixture was stirred for 16 hours while maintaining the temperature at 150° C. After completion of the reaction, the reaction product was cooled to room temperature, and then an excessive amount of hexane was added thereto. 55.1 g (92%) of Target Compound X-4 was obtained.

Synthesis of X-5

The synthesis was performed in the same manner as in the synthesis method of X-1 by using 55.1 g (95.9 mmol) of X-4 instead of 2-bromo-9,9-diphenyl-9H-fluorene. 59.6 g (100%) of Target Compound X-5 was obtained.

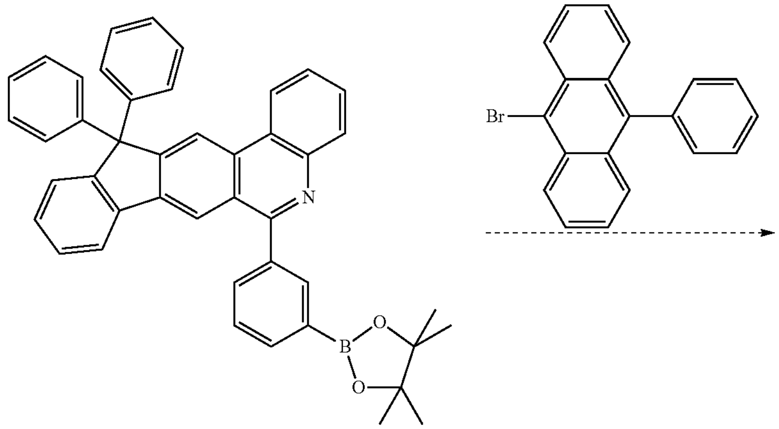

X-5

-continued

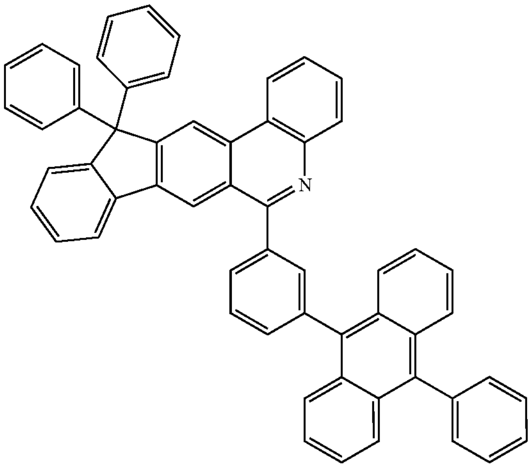

10-1

Synthesis of 10-1

10.0 g (16.1 mmol) of X-5, 5.9 g (17.7 mmol) of 9-bromo-10-phenylanthracene, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.97 g (82%) of Target Compound 10-1.

[Preparation Example 137] Preparation of Compound 10-3

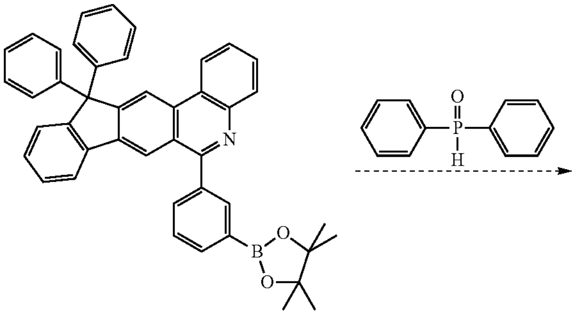

X-5

-continued

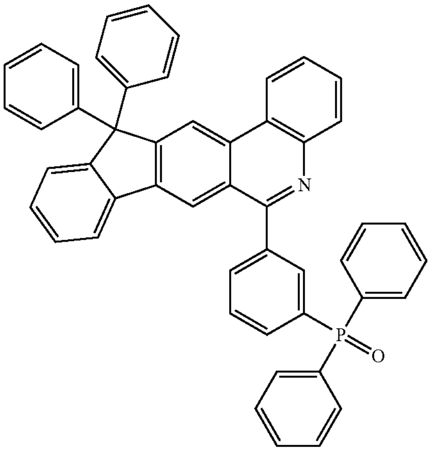

10-3

10.0 g (16.1 mmol) of X-5, 6.5 g (32.2 mmol) of diphenyl phosphineoxide, 1.9 g (1.6 mmol) of $Pd(PPh_3)_4$, and 3.1 mL (22.5 mmol) of TEA were stirred under reflux under 100 mL of toluene at 120° C. for 5 hours. After completion of the reaction, the reaction product was cooled to room temperature, and then a solid was produced and filtered, and then washed with MC, EA, and MeOH. And then, the resulting product was purified by column chromatography using dichloromethane and EA as an eluting solvent to obtain 4.7 g (42%) of Target Compound 10-3.

[Preparation Example 138] Preparation of Compound 10-5

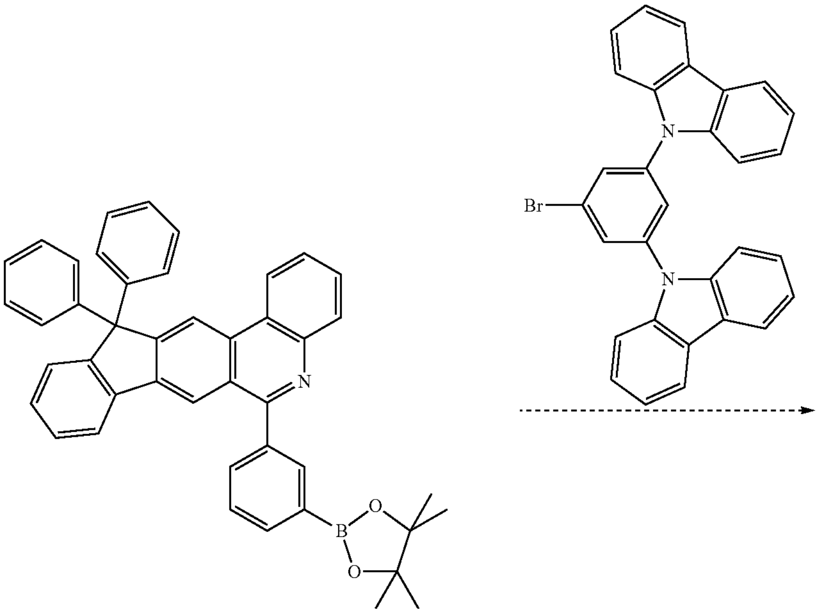

X-5

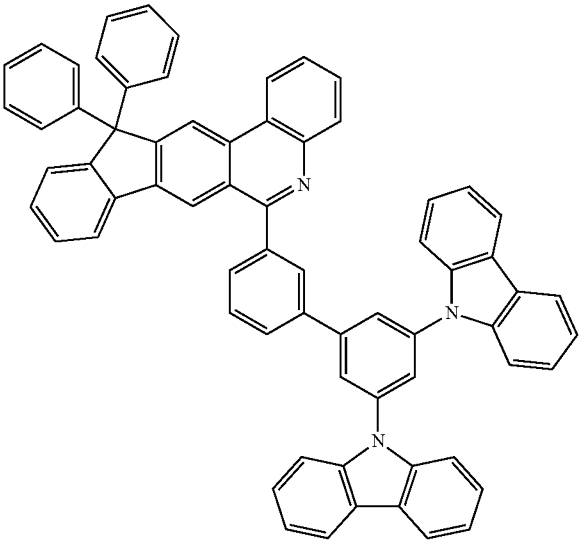

10-5

10.0 g (16.1 mmol) of X-5, 8.6 g (17.7 mmol) of 9,9'-(5-bromo-1,3-phenylene)bis(9H-carbazole), 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 11.5 g (79%) of Target Compound 10-5.

[Preparation Example 139] Preparation of Compound 10-6

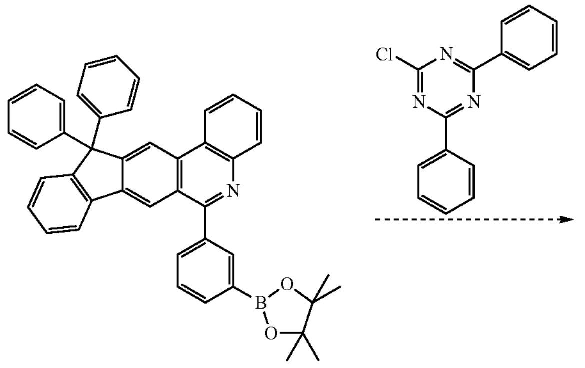

X-5

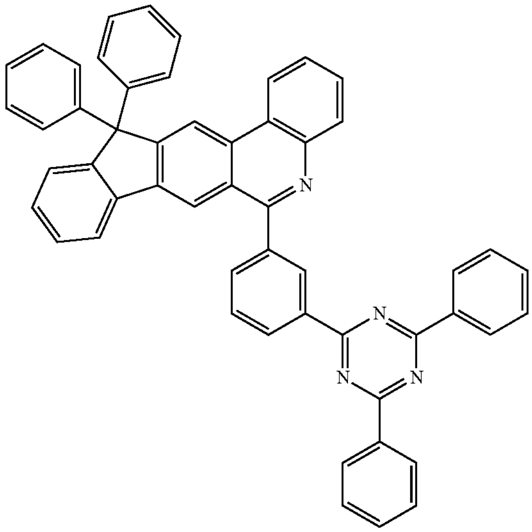

10-6

10.0 g (16.1 mmol) of X-5, 4.7 g (17.7 mmol) of 2-chloro-4,6-diphenyl-1,3,5-triazine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.8 g (84%) of Target Compound 10-6.

[Preparation Example 140] Preparation of Compound 10-12

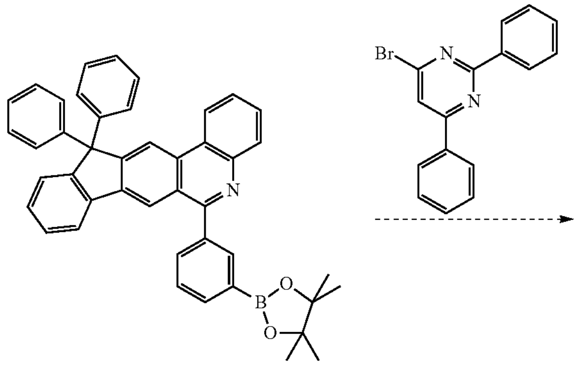

X-5

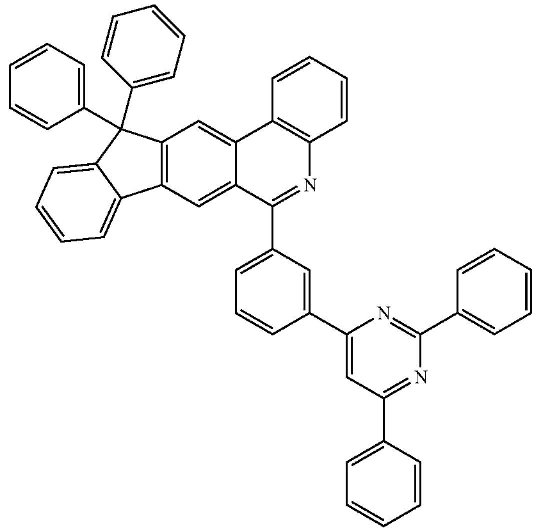

10-12

10.0 g (16.1 mmol) of X-5, 5.5 g (17.7 mmol) of 4-bromo-2,6-diphenylpyrimidine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 4 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 10.2 g (87%) of Target Compound 10-12.

[Preparation Example 141] Preparation of Compound 10-13

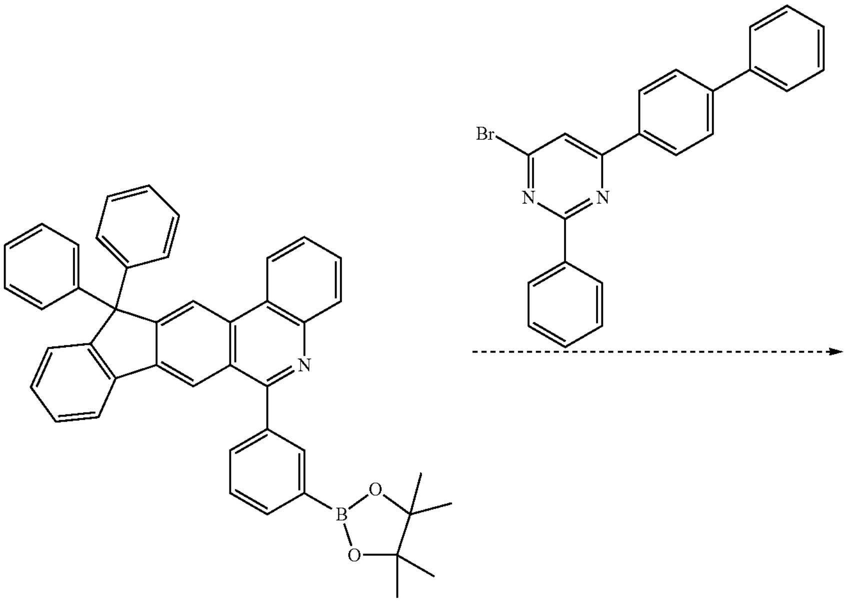

X-5

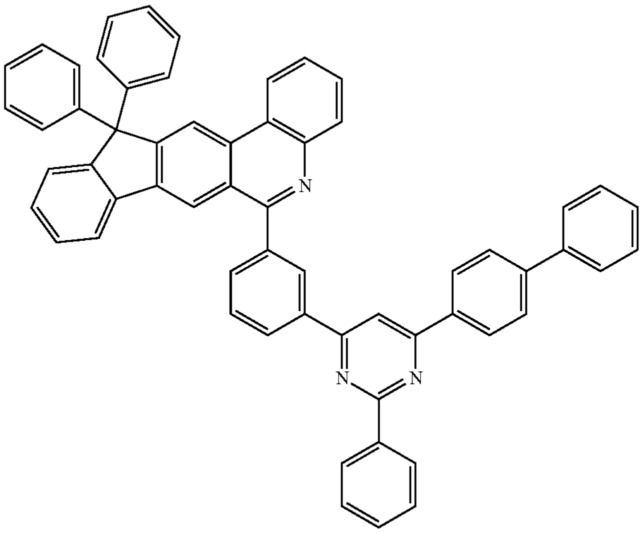

10-13

10.0 g (16.1 mmol) of X-5, 6.9 g (17.7 mmol) of 4-([1, 1'-biphenyl]-4-yl)-6-bromo-2-phenylpyrimidine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 11.1 g (86%) of Target Compound 10-13.

[Preparation Example 142] Preparation of Compound 10-37

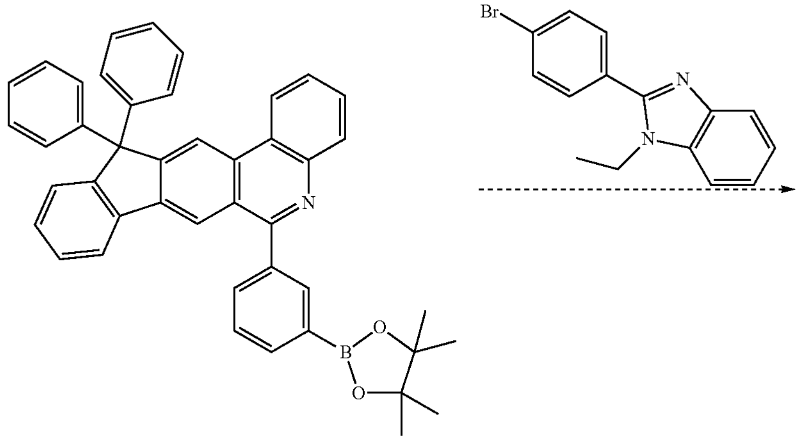

X-5

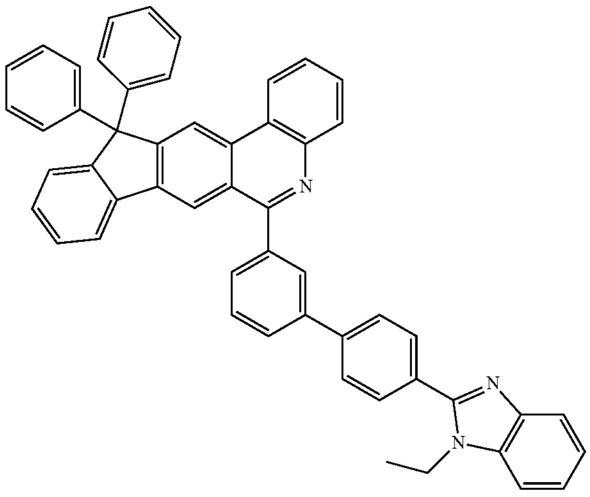

10-37

10.0 g (16.1 mmol) of X-5, 5.3 g (17.7 mmol) of 2-(4-bromophenyl)-1-ethyl-1H-benzo[d]imidazole, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 7 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.0 g (78%) of Target Compound 10-37.

[Preparation Example 143] Preparation of Compound 10-46

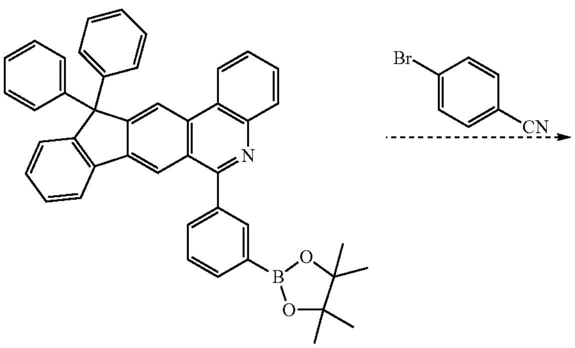

X-5

-continued

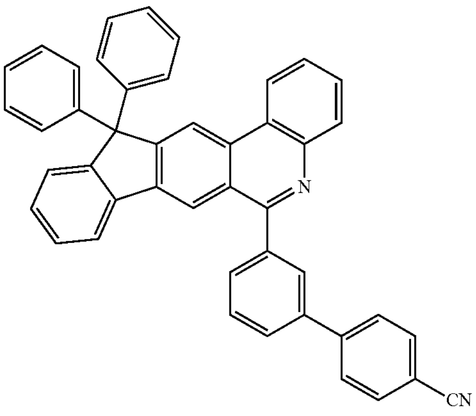

10-46

10.0 g (16.1 mmol) of X-5, 3.2 g (17.7 mmol) of 4-bromobenzonitrile, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 8 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 6.8 g (71%) of Target Compound 10-46.

[Preparation Example 144] Preparation of Compound 10-48

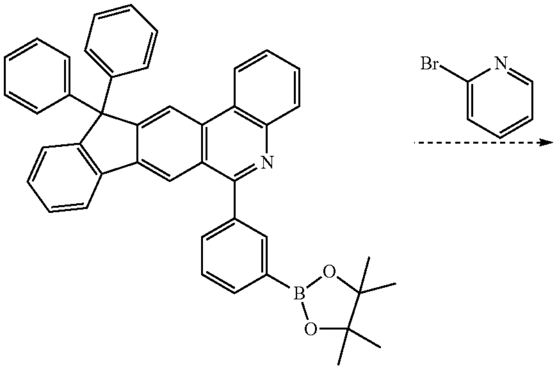

X-5

-continued

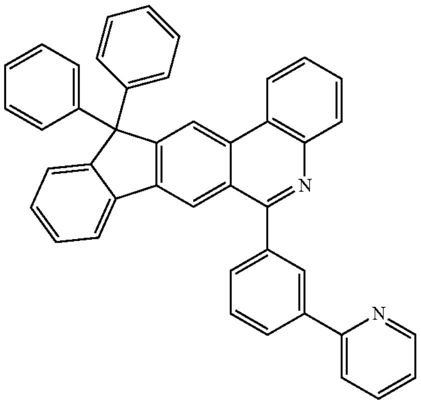

10-48

10.0 g (16.1 mmol) of X-5, 2.8 g (17.7 mmol) of 2-bromopyridine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 7.5 g (81%) of Target Compound 10-48.

[Preparation Example 145] Preparation of Compound 10-49

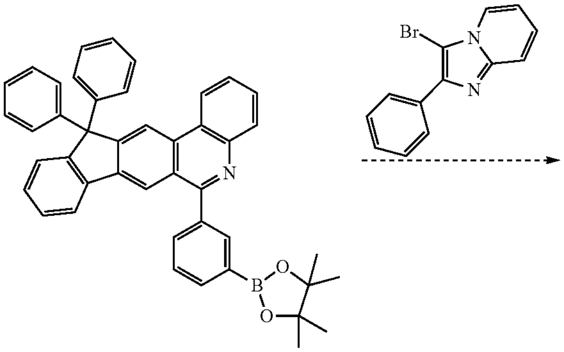

X-5

-continued

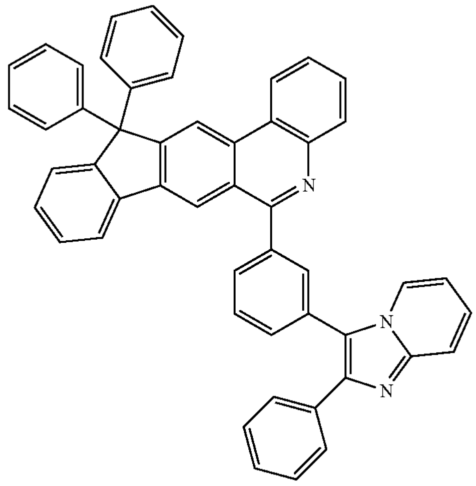

10-49

10.0 g (16.1 mmol) of X-5, 4.8 g (17.7 mmol) of 3-bromo-2-phenylimidazo[1,2-a]pyridine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.5 g (86%) of Target Compound 10-49.

[Preparation Example 146] Preparation of Compound 10-51

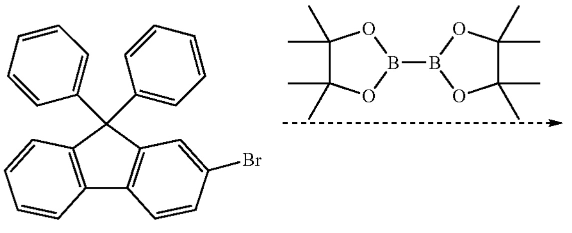

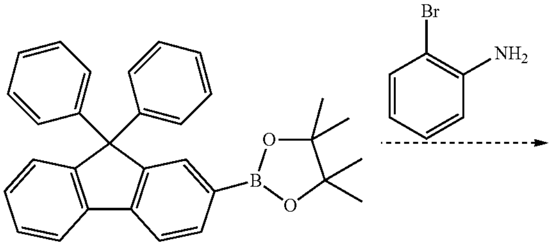

X-1

-continued

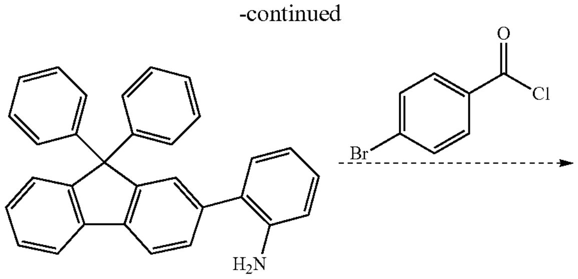

X-2

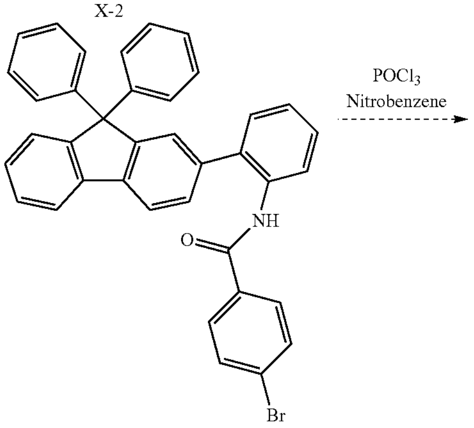

Y-3

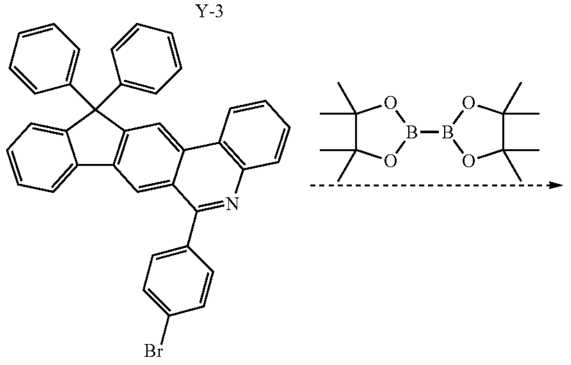

Y-4

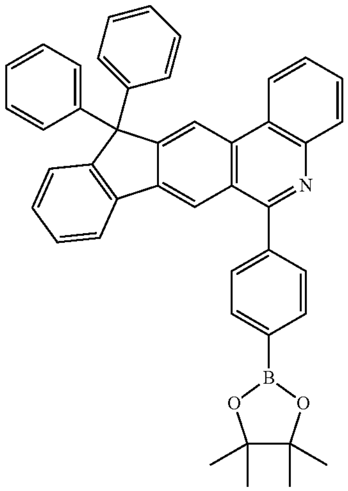

Y-5

Synthesis of Y-3

Synthesis was performed in the same manner as in the synthesis method of A-3 using 32.0 g (145.7 mmol) of 4-bromobenzoylchloride instead of 3-bromobenzoylchloride. 56.0 g (97%) of Target Compound Y-3 was obtained.

Synthesis of Y-4

Synthesis was performed in the same manner as in the synthesis method of X-4 using 56.0 g (94.5 mmol) of Y-3 instead of X-3. 50.0 g (92%) of Target Compound Y-4 was obtained.

Synthesis of Y-5

Synthesis was performed in the same manner as in the synthesis method of X-5 using 50.0 g (87.0 mmol) of Y-4 instead of X-4. 54.1 g (100%) of Target Compound Y-5 was obtained.

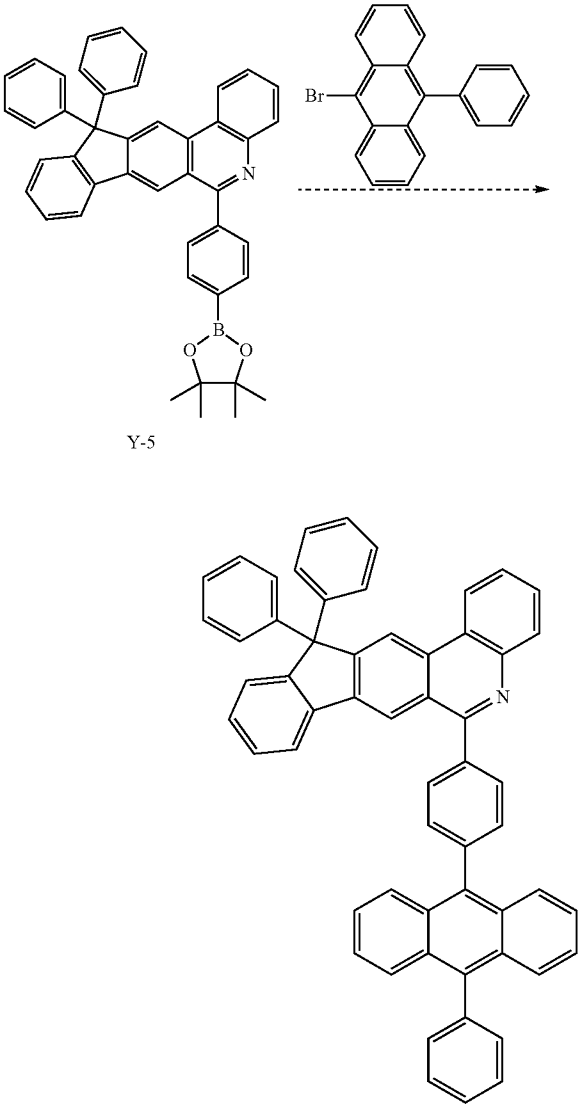

Y-5

10-51

Synthesis of 10-51

10.0 g (16.1 mmol) of Y-5, 5.9 g (17.7 mmol) of 9-bromo-10-phenylanthracene, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 10.1 g (83%) of Target Compound 10-51.

[Preparation Example 147] Preparation of Compound 10-53

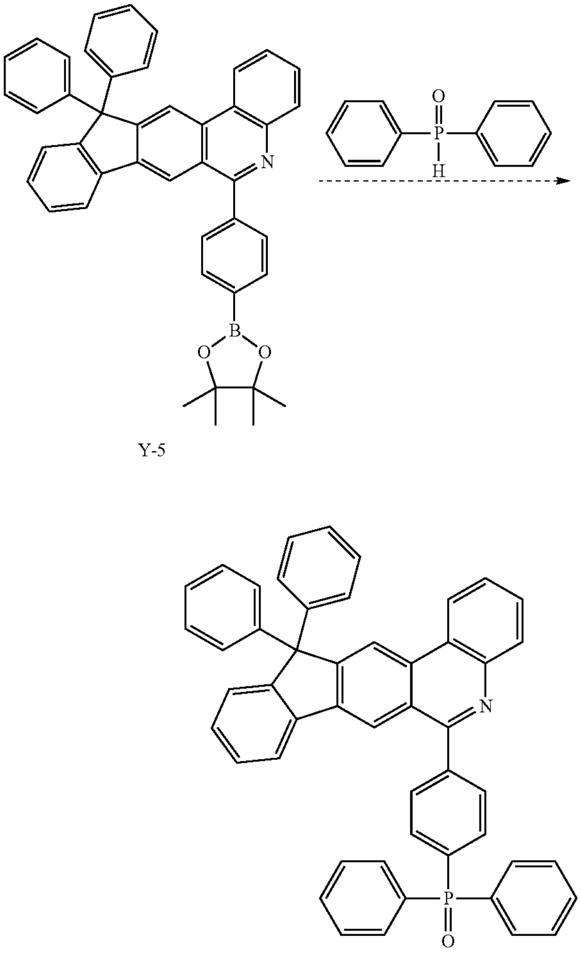

Y-5

10-53

10.0 g (16.1 mmol) of Y-5, 6.5 g (32.2 mmol) of diphenyl phosphineoxide, 1.9 g (1.6 mmol) of $Pd(PPh_3)_4$, and 3.1 mL (22.5 mmol) of TEA were stirred under reflux under 100 mL of toluene at 120° C. for 6 hours. After completion of the reaction, the reaction product was cooled to room temperature, and then a solid was produced and filtered, and then washed with MC, EA, and MeOH. And then, the resulting product was purified by column chromatography using dichloromethane and EA as an eluting solvent to obtain 5.0 g (45%) of Target Compound 10-53.

[Preparation Example 148] Preparation of Compound 10-55

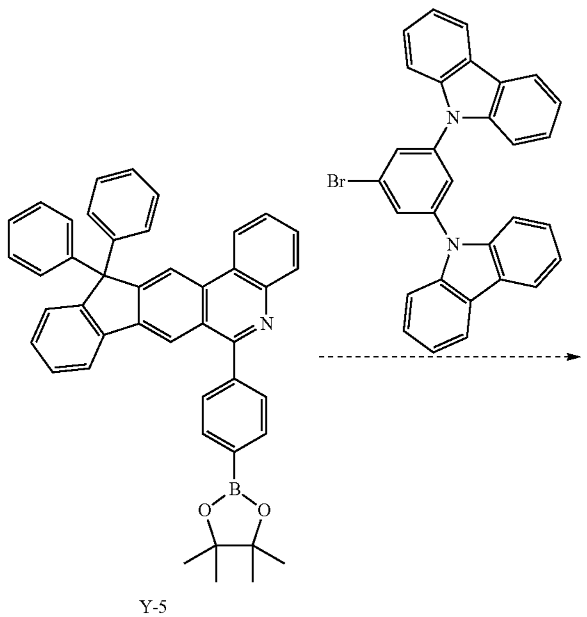

Y-5

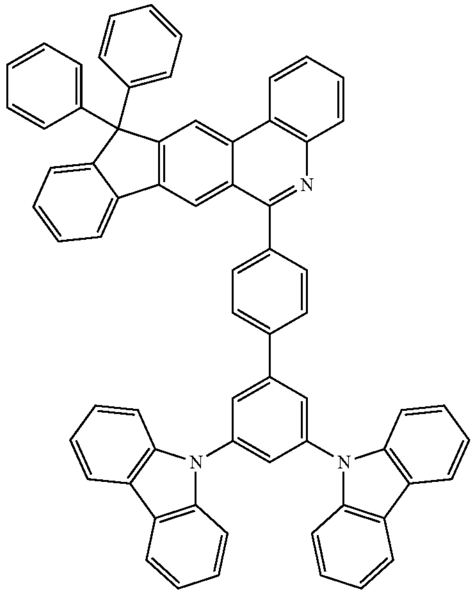

10-55

10.0 g (16.1 mmol) of Y-5, 8.6 g (17.7 mmol) of 9,9'-(5-bromo-1,3-phenylene)bis(9H-carbazole), 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 11.6 g (80%) of Target Compound 10-55.

[Preparation Example 149] Preparation of Compound 10-56

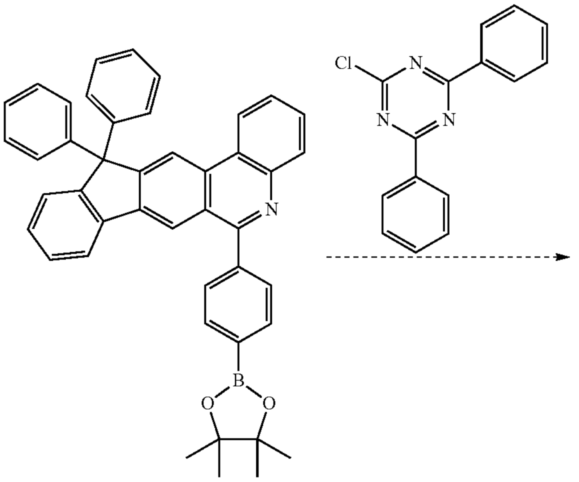

Y-5

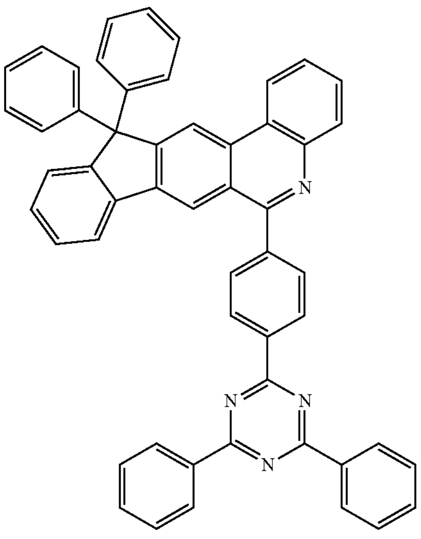

10-56

10.0 g (16.1 mmol) of Y-5, 4.7 g (17.7 mmol) of 2-chloro-4,6-diphenyl-1,3,5-triazine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.6 g (82%) of Target Compound 10-56.

[Preparation Example 150] Preparation of Compound 10-62

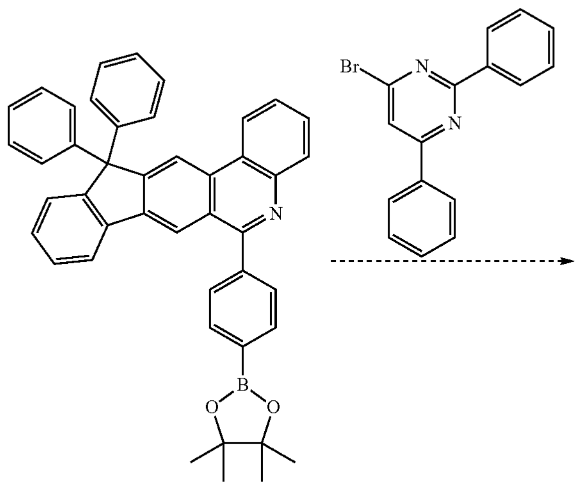

Y-5

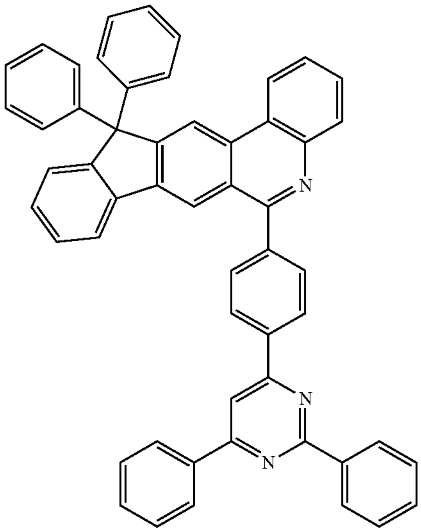

10-62

10.0 g (16.1 mmol) of Y-5, 5.5 g (17.7 mmol) of 4-bromo-2,6-diphenylpyrimidine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 10.3 g (88%) of Target Compound 10-62.

[Preparation Example 151] Preparation of Compound 10-63

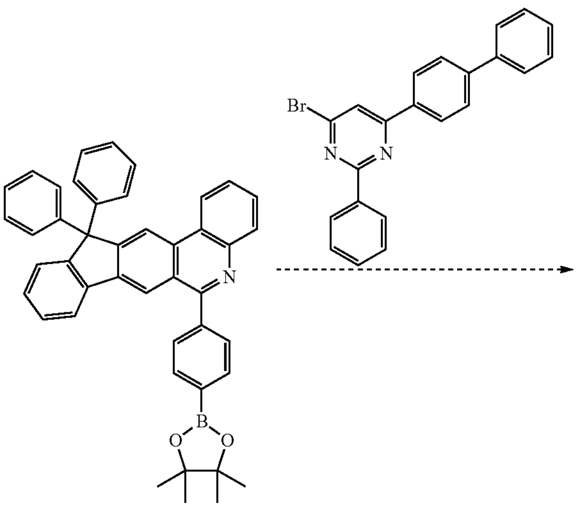

Y-5

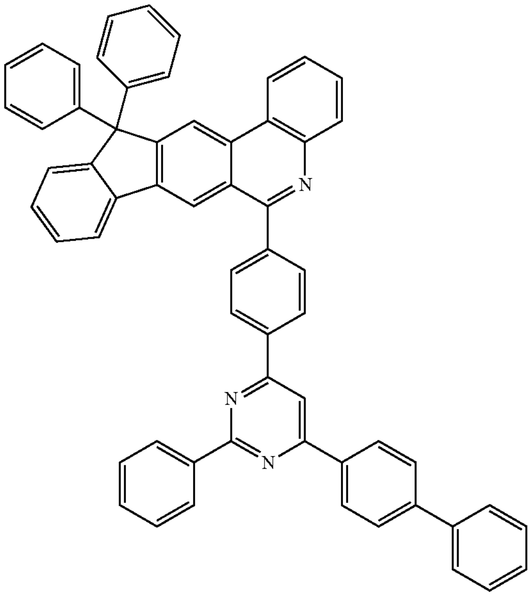

10-63

10.0 g (16.1 mmol) of Y-5, 6.9 g (17.7 mmol) of 4-([1, 1'-biphenyl]-4-yl)-6-bromo-2-phenylpyrimidine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 11.0 g (85%) of Target Compound 10-63.

[Preparation Example 152] Preparation of Compound 10-87

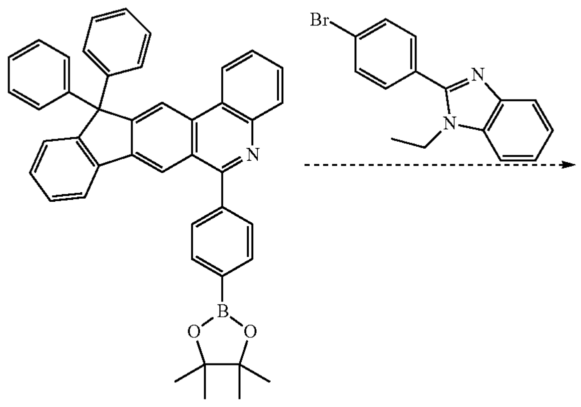

Y-5

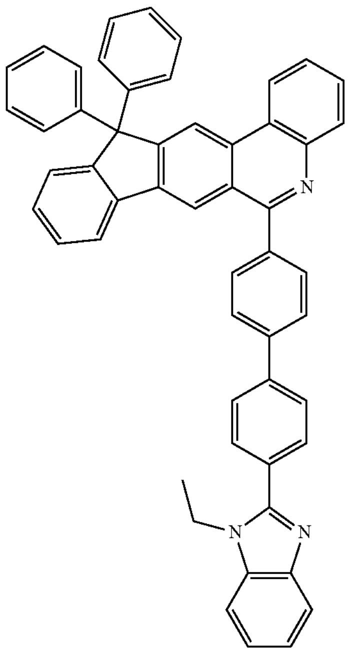

10-87

10.0 g (16.1 mmol) of Y-5, 5.3 g (17.7 mmol) of 2-(4-bromophenyl)-1-ethyl-1H-benzo[d]imidazole, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.2 g (80%) of Target Compound 10-87.

[Preparation Example 153] Preparation of Compound 10-96

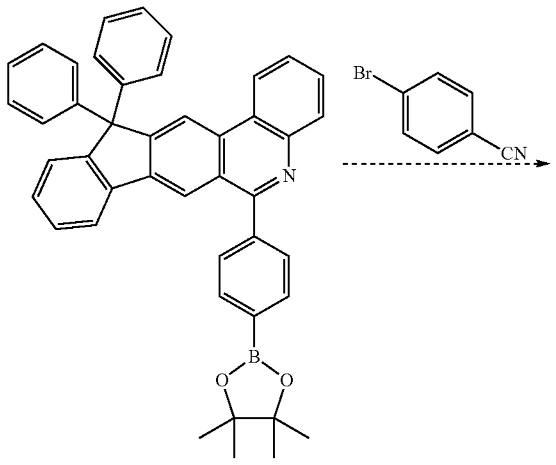

Y-5

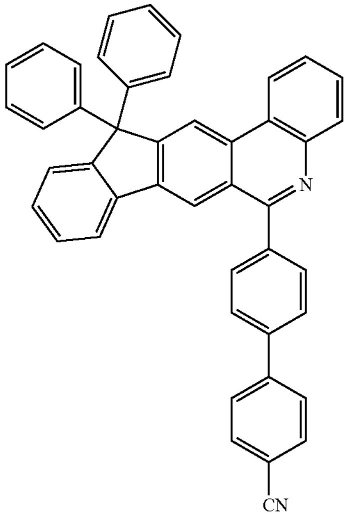

10-96

10.0 g (16.1 mmol) of Y-5, 3.2 g (17.7 mmol) of 4-bromobenzonitrile, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 6.3 g (74%) of Target Compound 10-96.

[Preparation Example 154] Preparation of Compound 10-98

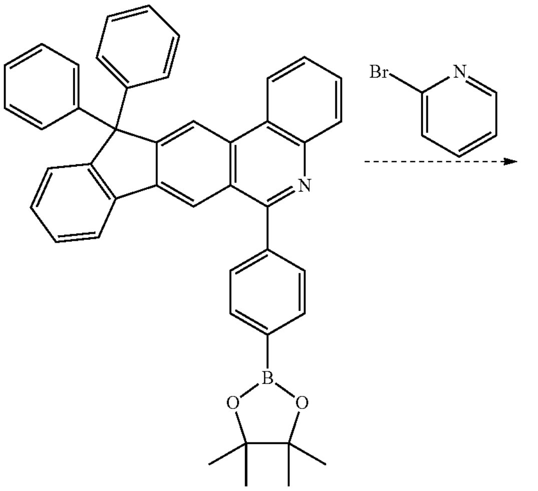

Y-5

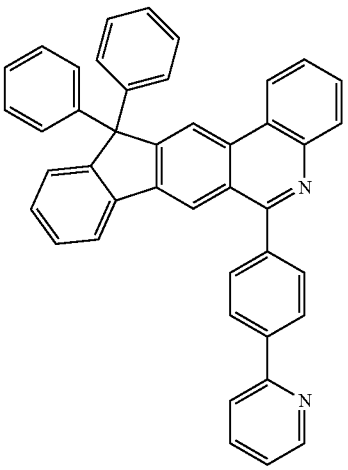

10-98

10.0 g (16.1 mmol) of Y-5, 2.8 g (17.7 mmol) of 2-bromopyridine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 7.7 g (83%) of Target Compound 10-98.

[Preparation Example 155] Preparation of Compound 10-99

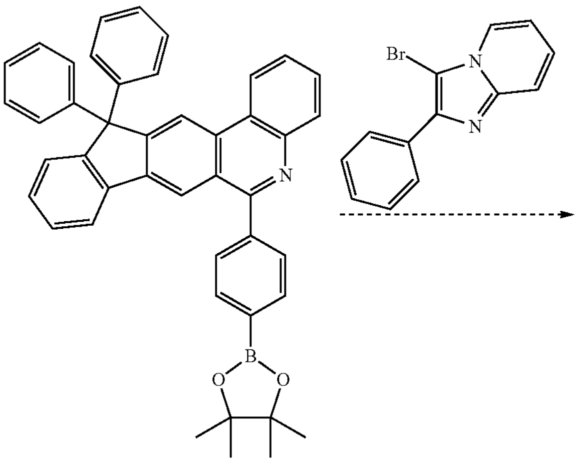

Y-5

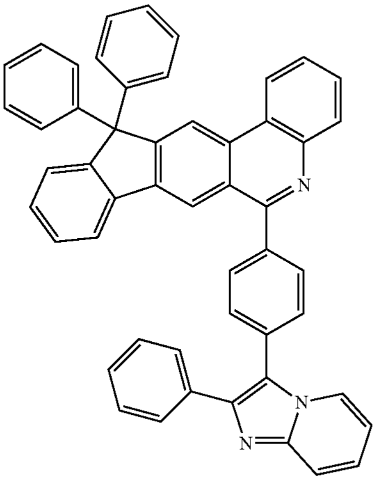

10-99

10.0 g (16.1 mmol) of Y-5, 4.8 g (17.7 mmol) of 3-bromo-2-phenylimidazo[1,2-a]pyridine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 7 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.4 g (85%) of Target Compound 10-99.

[Preparation Example 156] Preparation of Compound 11-26

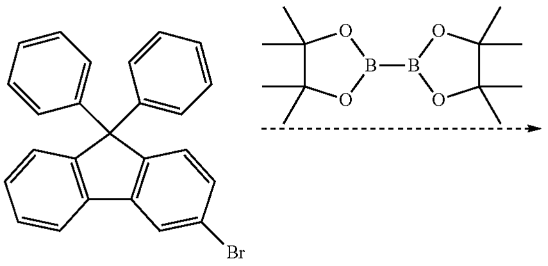

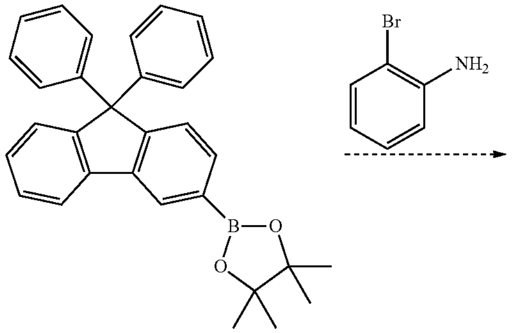

V-1

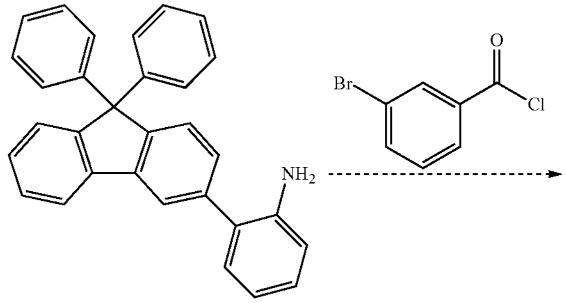

V-2

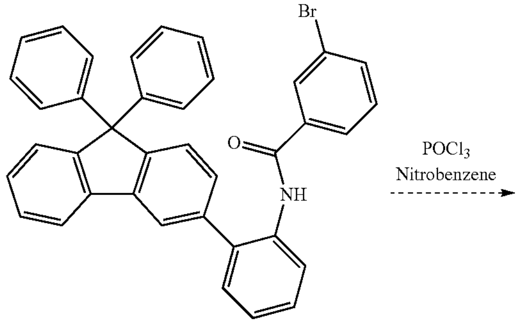

V-3

-continued

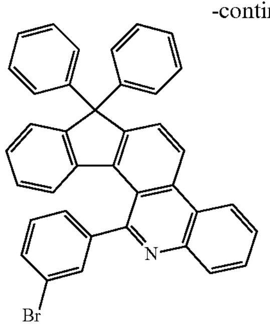

V-4

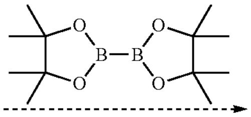

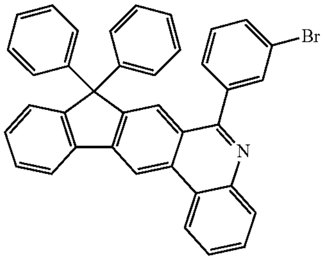

W-4

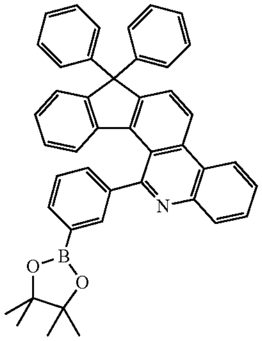

V-5

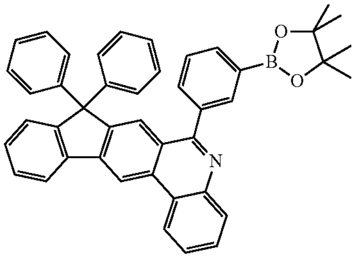

W-5

Synthesis of V-1

The synthesis was performed in the same manner as in the synthesis method of X-1 by using 120 g (302.0 mmol) of 3-bromo-9,9-diphenyl-9H-fluorene instead of 2-bromo-9,9-diphenyl-9H-fluorene. 134.2 g (100%) of Target Compound was obtained.

Synthesis of V-2

Synthesis was performed in the same manner as in the synthesis method of X-2 using 134.2 g (302.0 mmol) of V-1 instead of X-1. 91.5 g (74%) of Target Compound V-2 was obtained.

Synthesis of V-3

Synthesis was performed in the same manner as in the synthesis method of X-3 using 91.5 g (223.4 mmol) of V-2 instead of X-2. 119.2 g (90%) of Target Compound V-3 was obtained.

Synthesis of V-4 and W-4

119.2 g (201.2 mmol) of V-3 was thoroughly dissolved in 1200 L of nitrobenzene, and then 20.6 mL (221.3 mmol) of $POCl_3$ was slowly added dropwise thereto. And then, the resulting mixture was stirred for 16 hours while maintaining the temperature at 150° C. After completion of the reaction, the reaction product was cooled to room temperature, and then an excessive amount of hexane was added thereto. The resulting solid was purified by column chromatography using dichloromethane and hexane as an eluting solvent to obtain 42.8 g (37%) and 63.6 g (55%) of Target Compounds V-4 and W-4, respectively.

Synthesis of V-5

Synthesis was performed in the same manner as in the synthesis method of X-1 using 42.8 g (74.5 mmol) of V-4 instead of X-4. 46.3 g (100%) of Target Compound V-5 was obtained.

Synthesis of W-5

Synthesis was performed in the same manner as in the synthesis method of X-1 using 63.6 g (110.7 mmol) of W-4 instead of X-4. 68.8 g (100%) of Target Compound W-5 was obtained.

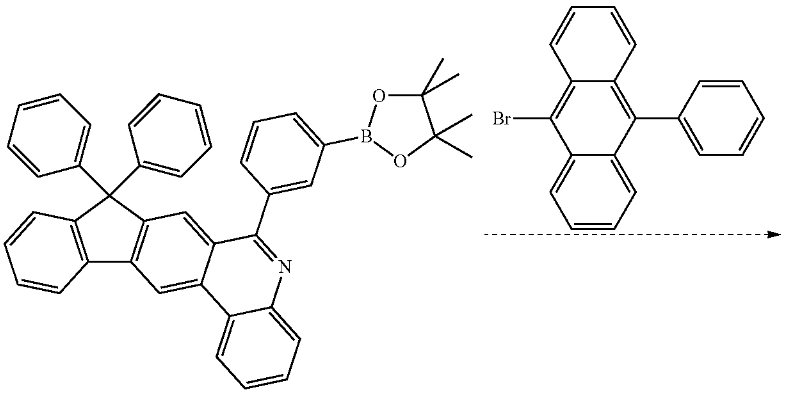

W-5

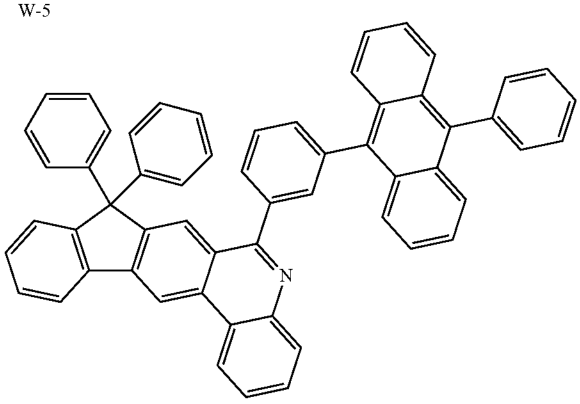

11-26

Synthesis of 11-26

10.0 g (16.1 mmol) of W-5, 5.9 g (17.7 mmol) of 9-bromo-10-phenylanthracene, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 10.0 g (82%) of Target Compound 11-26.

[Preparation Example 157] Preparation of Compound 11-28

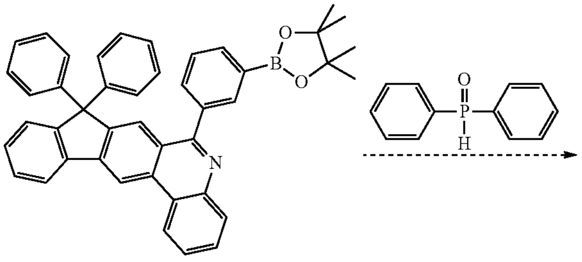

W-5

-continued

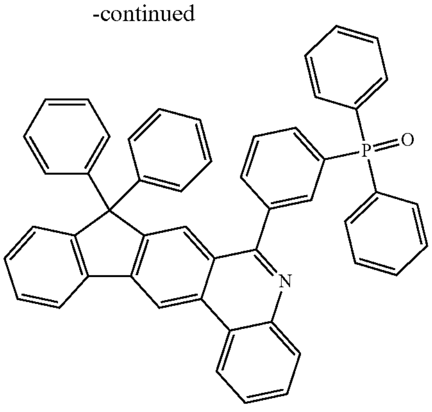

11-28

10.0 g (16.1 mmol) of W-5, 6.5 g (32.2 mmol) of diphenyl phosphineoxide, 1.9 g (1.6 mmol) of $Pd(PPh_3)_4$, and 3.1 mL (22.5 mmol) of TEA were stirred under reflux under 100 mL of toluene at 120° C. for 5 hours. After completion of the reaction, the reaction product was cooled to room temperature, and then a solid was produced and filtered, and then washed with MC, EA, and MeOH. And then, the resulting product was purified by column chromatography using dichloromethane and EA as an eluting solvent to obtain 4.7 g (42%) of Target Compound 11-28.

[Preparation Example 158] Preparation of Compound 11-29

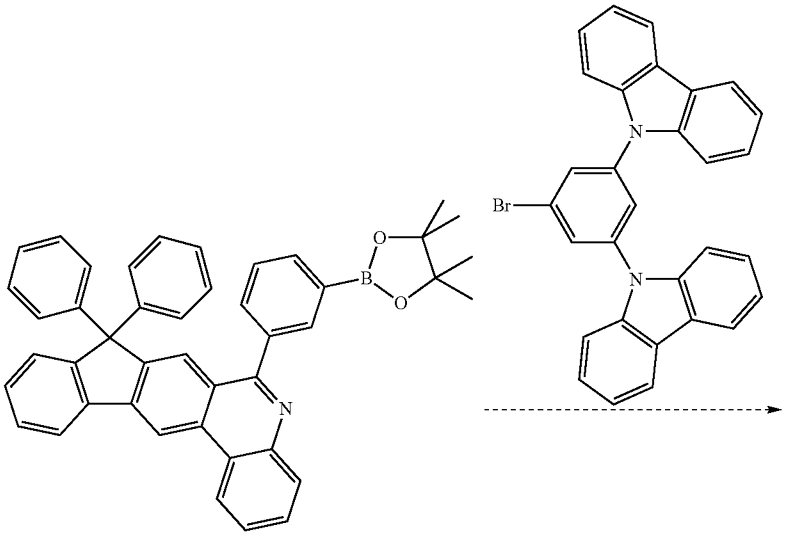

W-5

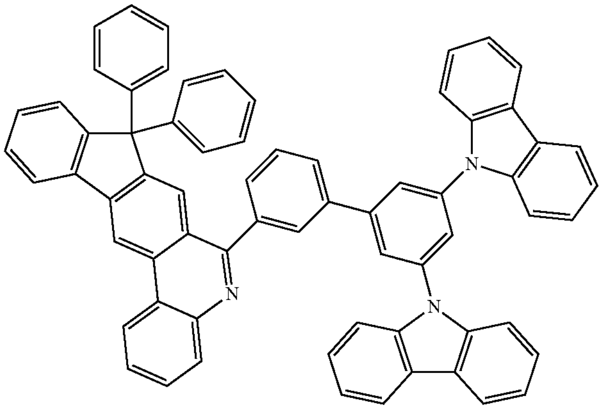

11-29

10.0 g (16.1 mmol) of W-5, 8.6 g (17.7 mmol) of 9,9'-(5-bromo-1,3-phenylene)bis(9H-carbazole), 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 12.0 g (83%) of Target Compound 11-29.

[Preparation Example 159] Preparation of Compound 11-30

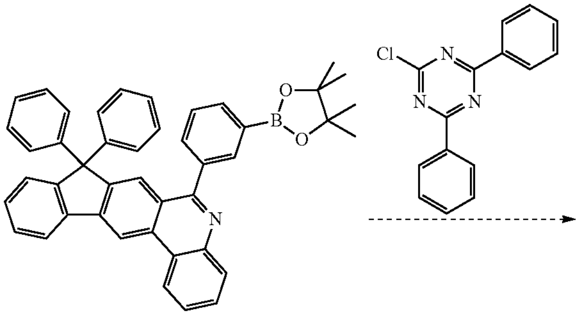

W-5

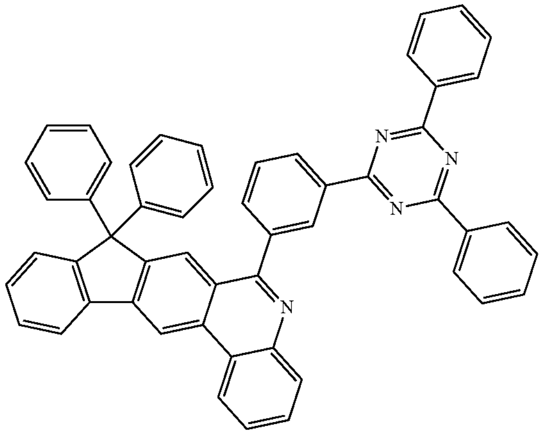

11-30

10.0 g (16.1 mmol) of W-5, 4.7 g (17.7 mmol) of 2-chloro-4,6-diphenyl-1,3,5-triazine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 4 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.2 g (79%) of Target Compound 11-30.

[Preparation Example 160] Preparation of Compound 11-35

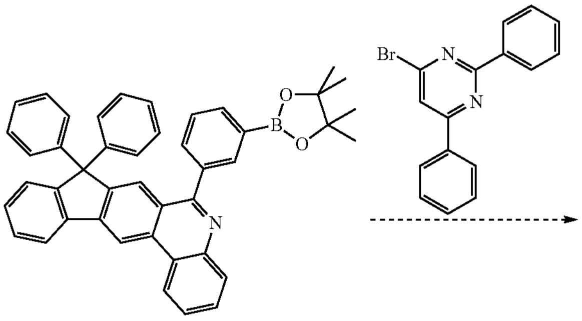

W-5

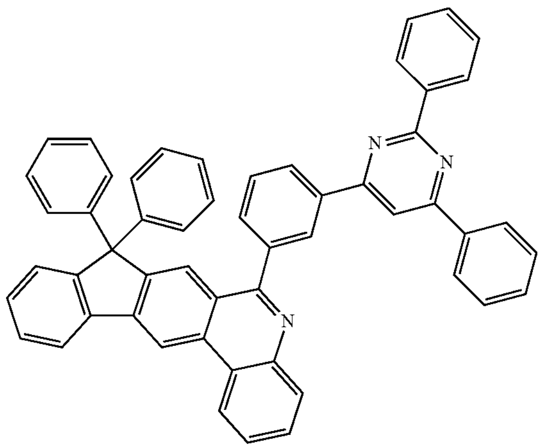

11-35

10.0 g (16.1 mmol) of W-5, 5.5 g (17.7 mmol) of 4-bromo-2,6-diphenylpyrimidine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.9 g (85%) of Target Compound 11-35.

[Preparation Example 161] Preparation of Compound 11-36

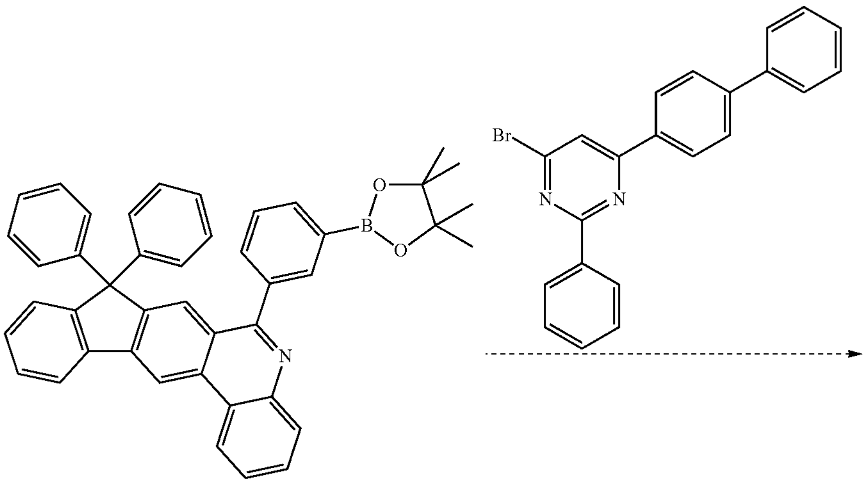

W-5

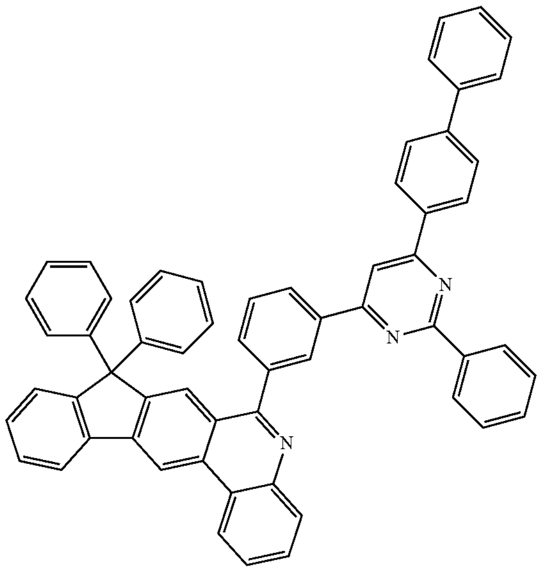

11-36

10.0 g (16.1 mmol) of W-5, 6.9 g (17.7 mmol) of 4-([1,1'-biphenyl]-4-yl)-6-bromo-2-phenylpyrimidine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 10.9 g (84%) of Target Compound 11-36.

[Preparation Example 162] Preparation of Compound 11-45

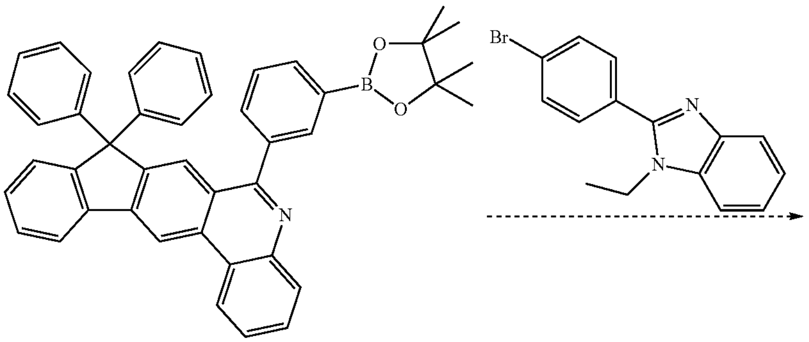

W-5

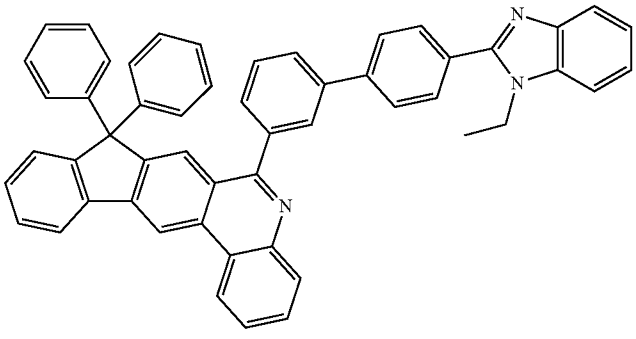

11-45

10.0 g (16.1 mmol) of W-5, 5.3 g (17.7 mmol) of 2-(4-bromophenyl)-1-ethyl-1H-benzo[d]imidazole, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.8 g (85%) of Target Compound 11-45.

[Preparation Example 163] Preparation of Compound 11-48

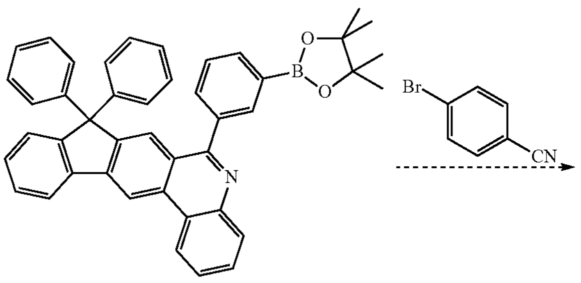

W-5

-continued

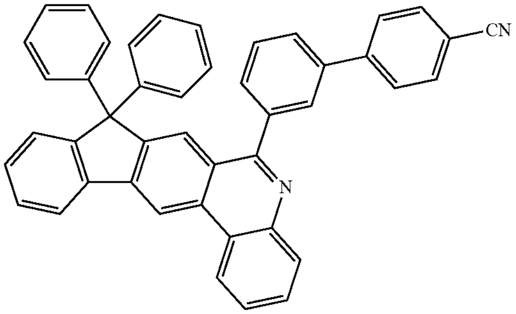

11-48

10.0 g (16.1 mmol) of W-5, 3.2 g (17.7 mmol) of 4-bromobenzonitrile, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 6.8 g (80%) of Target Compound 11-48.

[Preparation Example 164] Preparation of Compound 11-49

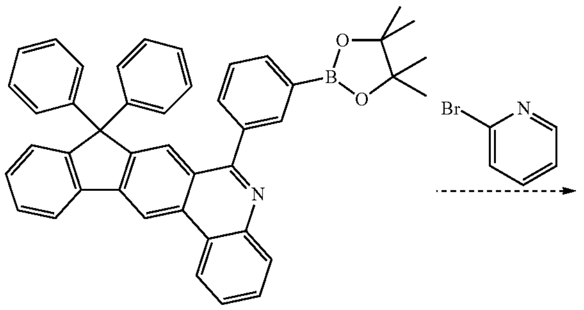

W-5

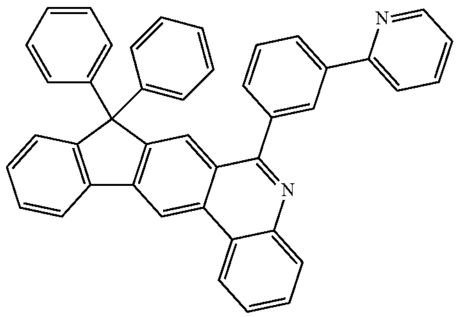

11-49

10.0 g (16.1 mmol) of W-5, 2.8 g (17.7 mmol) of 2-bromopyridine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 7 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 7.3 g (79%) of Target Compound 11-49.

[Preparation Example 165] Preparation of Compound 11-50

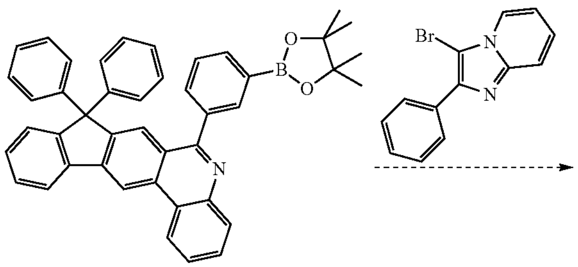

W-5

-continued

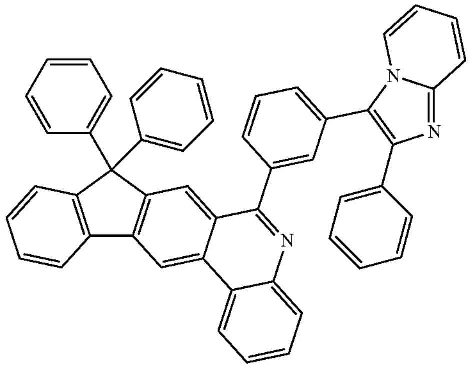

11-50

10.0 g (16.1 mmol) of W-5, 4.8 g (17.7 mmol) of 3-bromo-2-phenylimidazo[1,2-a]pyridine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.2 g (83%) of Target Compound 11-50.

[Preparation Example 166] Preparation of Compound 11-76

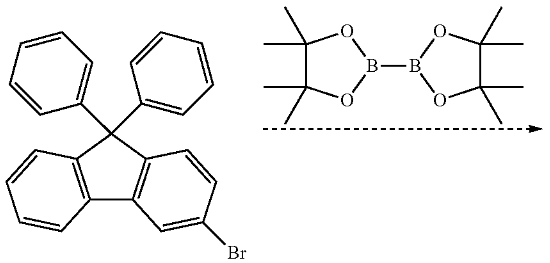

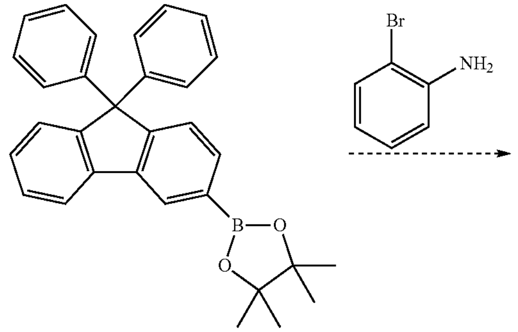

V-1

-continued

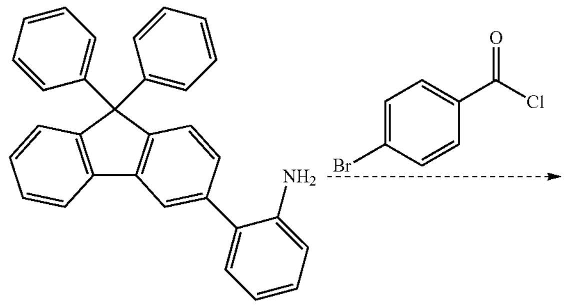

V-2

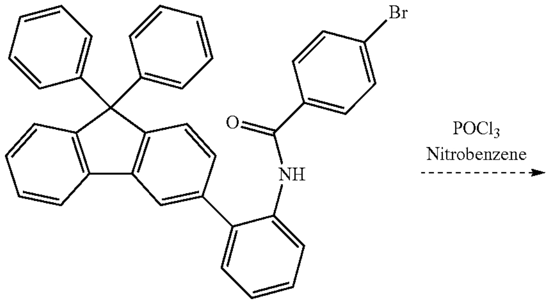

Z-3

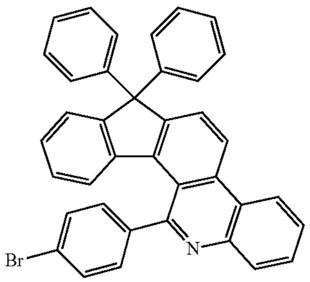

Z-4

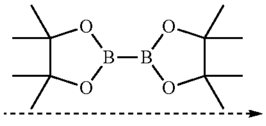

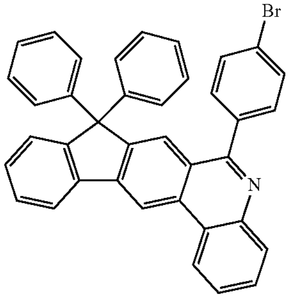

Z-1-4

-continued

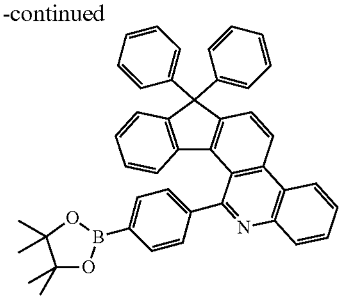

Z-5

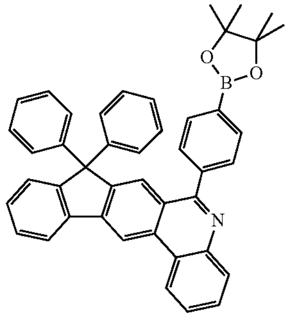

Z-1-5

Synthesis of Z-3

Synthesis was performed in the same manner as in the synthesis method of X-3 using 93.2 g (227.6 mmol) of V-2 instead of Y-2. 125.4 g (93%) of Target Compound Z-3 was obtained.

Synthesis of Z-4 and Z-1-4

Synthesis was performed in the same manner as in the synthesis method of V-4 using 125.4 g (211.6 mmol) of Z-3 instead of V-3. 48.6 g (40%) of Target Compound Z-4 and 64.4 g (53%) of Target Compound Z-1-4 were obtained.

Synthesis of Z-5

Synthesis was performed in the same manner as in the synthesis method of X-1 using 48.6 g (84.6 mmol) of Z-4 instead of Y-4. 52.6 g (100%) of Target Compound Z-5 was obtained.

Synthesis of Z-1-5

Synthesis was performed in the same manner as in the synthesis method of X-1 using 64.4 g (112.1 mmol) of Z-1-4 instead of Y-4. 69.7 g (100%) of Target Compound Z-1-5 was obtained.

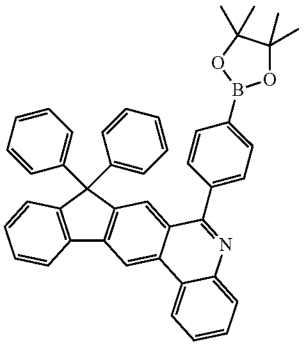

Z-1-5

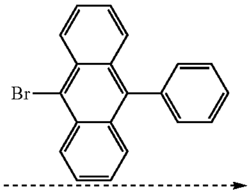

-continued

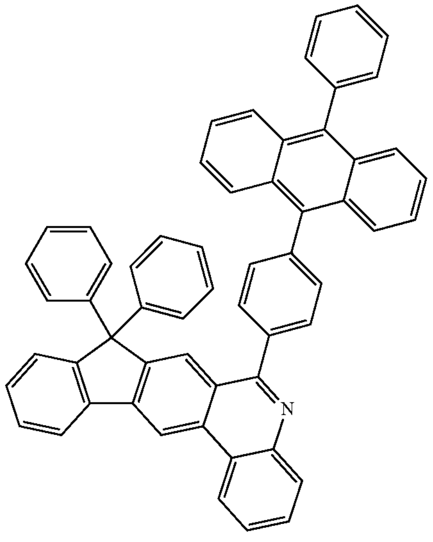

11-76

Synthesis of 11-76

10.0 g (16.1 mmol) of Z-1-5, 5.9 g (17.7 mmol) of 9-bromo-10-phenylanthracene, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.8 g (80%) of Target Compound 11-76.

[Preparation Example 167] Preparation of Compound 11-78

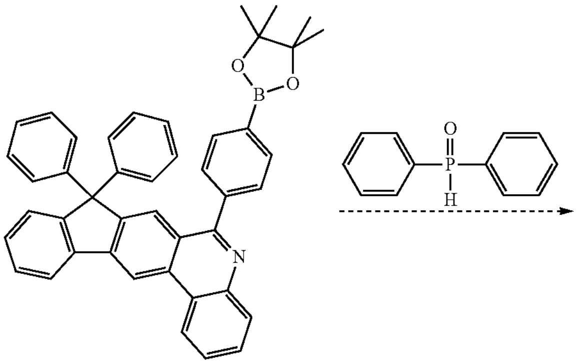

Z-1-5

-continued

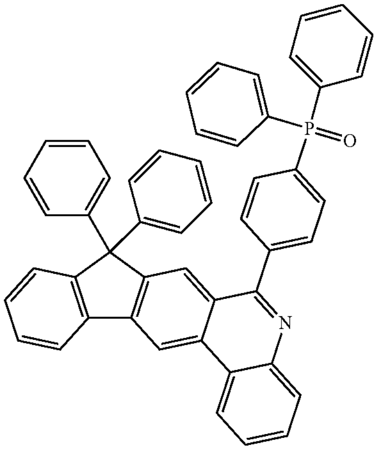

11-78

10.0 g (16.1 mmol) of Z-1-5, 6.5 g (32.2 mmol) of diphenyl phosphineoxide, 1.9 g (1.6 mmol) of $Pd(PPh_3)_4$, and 3.1 mL (22.5 mmol) of TEA were stirred under reflux under 100 mL of toluene at 120° C. for 4 hours. After completion of the reaction, the reaction product was cooled to room temperature, and then a solid was produced and filtered, and then washed with MC, EA, and MeOH. And then, the resulting product was purified by column chromatography using dichloromethane and EA as an eluting solvent to obtain 4.5 g (40%) of Target Compound 11-78.

[Preparation Example 168] Preparation of Compound 11-79

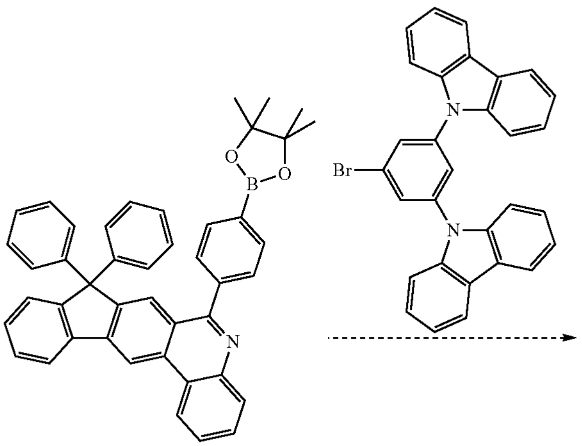

Z-1-5

-continued

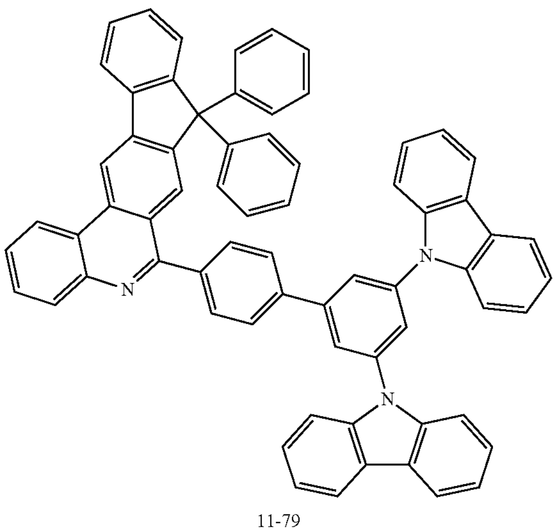

11-79

10.0 g (16.1 mmol) of Z-1-5, 8.6 g (17.7 mmol) of 9,9'-(5-bromo-1,3-phenylene)bis(9H-carbazole), 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 12.3 g (85%) of Target Compound 11-79.

[Preparation Example 169] Preparation of Compound 11-80

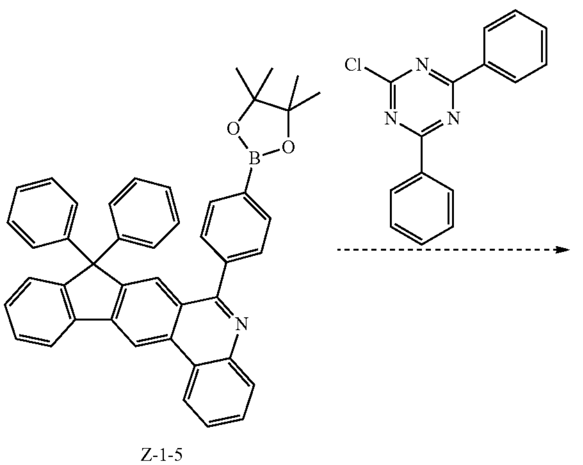

Z-1-5

-continued

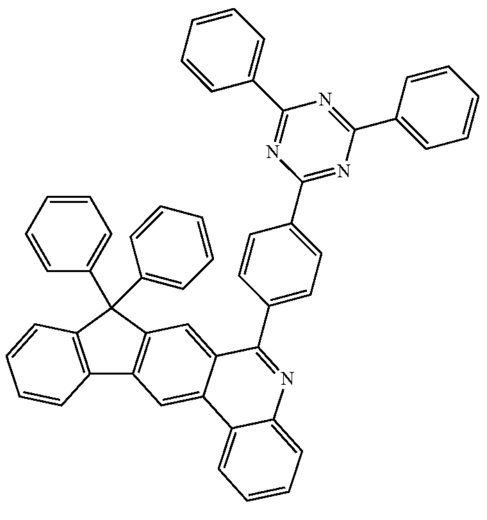

11-80

10.0 g (16.1 mmol) of Z-1-5, 4.7 g (17.7 mmol) of 2-chloro-4,6-diphenyl-1,3,5-triazine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 3 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.3 g (80%) of Target Compound 11-80.

[Preparation Example 170] Preparation of Compound 11-85

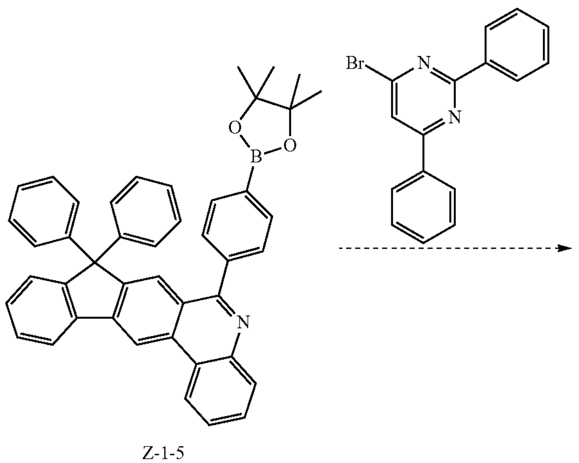

Z-1-5

-continued

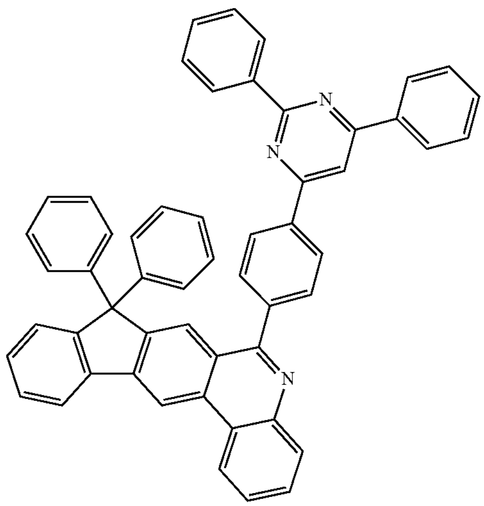

11-85

10.0 g (16.1 mmol) of Z-1-5, 5.5 g (17.7 mmol) of 4-bromo-2,6-diphenylpyrimidine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 10.2 g (88%) of Target Compound 11-85.

[Preparation Example 171] Preparation of Compound 11-86

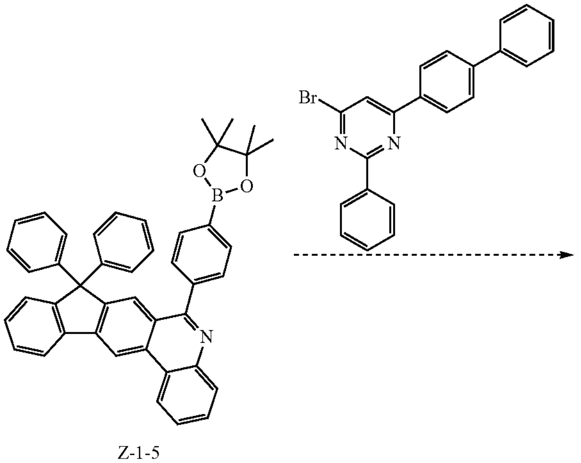

Z-1-5

-continued

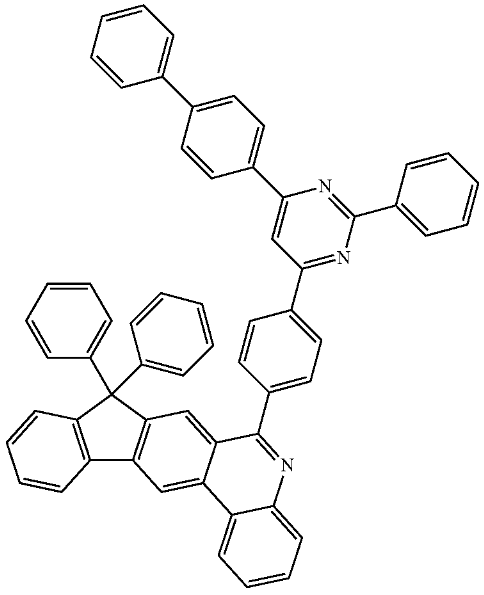

11-86

10.0 g (16.1 mmol) of Z-1-5, 6.9 g (17.7 mmol) of 4-([1,1'-biphenyl]-4-yl)-6-bromo-2-phenylpyrimidine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 10.6 g (82%) of Target Compound 11-86.

[Preparation Example 172] Preparation of Compound 11-95

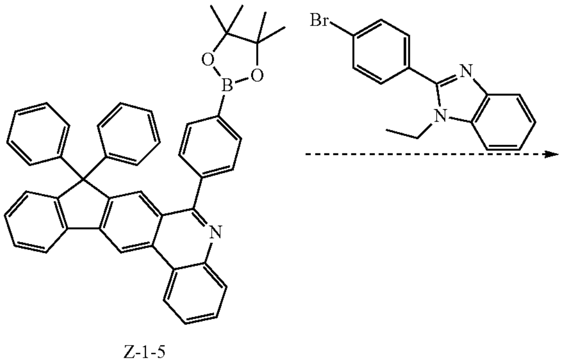

Z-1-5

-continued

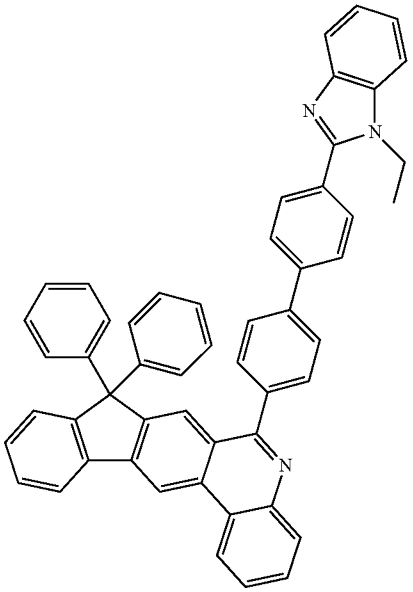

11-95

10.0 g (16.1 mmol) of Z-1-5, 5.3 g (17.7 mmol) of 2-(4-bromophenyl)-1-ethyl-1H-benzo[d]imidazole, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 10.0 g (87%) of Target Compound 11-95.

[Preparation Example 173] Preparation of Compound 11-98

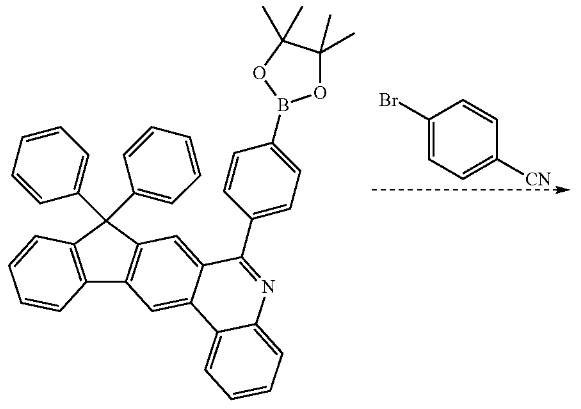

Z-1-5

-continued

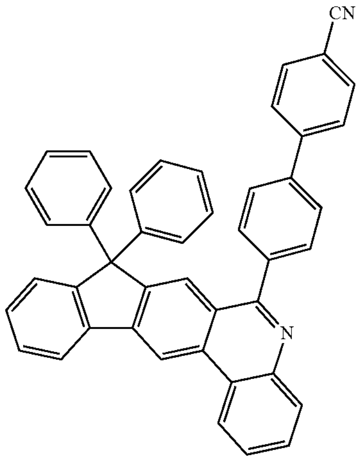

11-98

10.0 g (16.1 mmol) of Z-1-5, 3.2 g (17.7 mmol) of 4-bromobenzonitrile, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 7.2 g (85%) of Target Compound 11-98.

[Preparation Example 174] Preparation of Compound 11-99

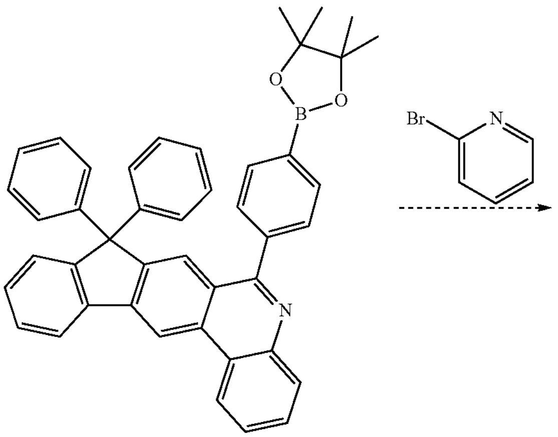

Z-1-5

-continued

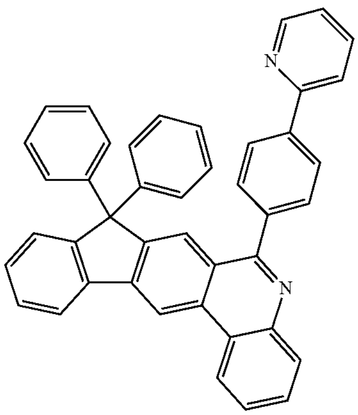

11-99

10.0 g (16.1 mmol) of Z-1-5, 2.8 g (17.7 mmol) of 2-bromopyridine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 7.6 g (82%) of Target Compound 11-99.

[Preparation Example 175] Preparation of Compound 11-100

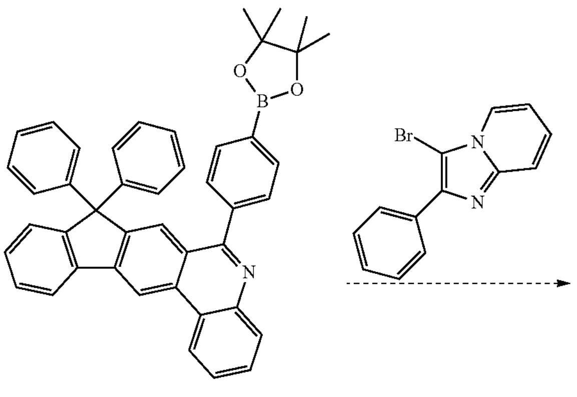

Z-1-5

-continued

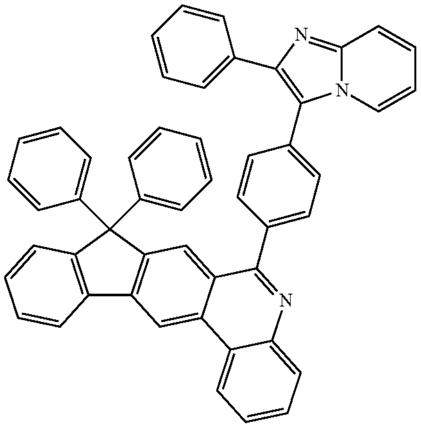

11-100

10.0 g (16.1 mmol) of Z-1-5, 4.8 g (17.7 mmol) of 3-bromo-2-phenylimidazo[1,2-a]pyridine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 7 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.4 g (85%) of Target Compound 11-100.

[Preparation Example 176] Preparation of Compound 12-1

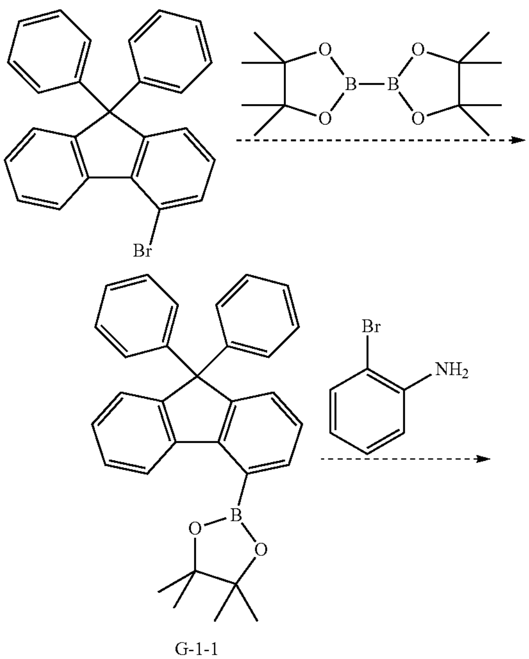

G-1-1

-continued

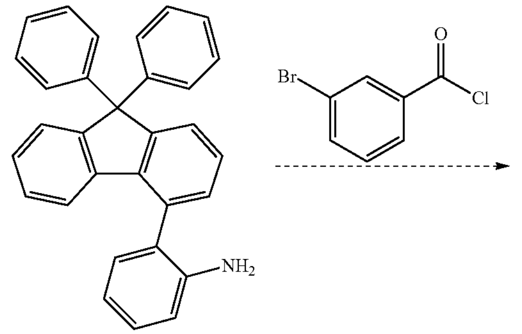

G-1-2

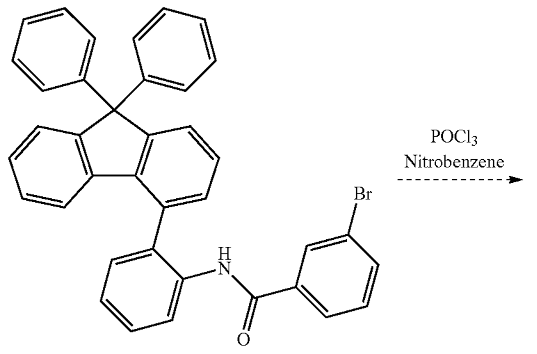

G-1-3

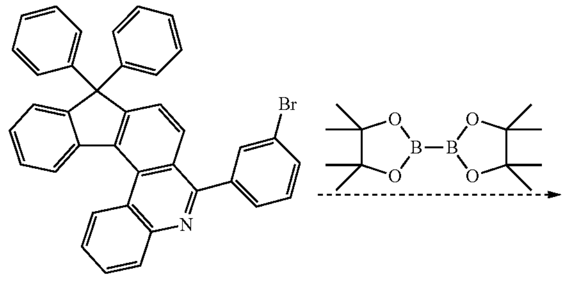

G-1-4

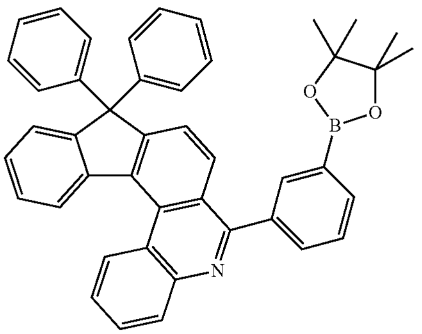

G-1-5

Synthesis of G-1-1

The synthesis was performed in the same manner as in the synthesis method of X-1 by using 60.0 g (151.0 mmol) of 4-bromo-9,9-diphenyl-9H-fluorene instead of 2-bromo-9,9-diphenyl-9H-fluorene. 65.1 g (97%) of Target Compound G-1-1 was obtained.

Synthesis of G-1-2

Synthesis was performed in the same manner as in the synthesis method of X-2 using 65.1 g (146.5 mmol) of G-1-1 instead of X-1. 51.0 g (85%) of Target Compound G-1-2 was obtained.

Synthesis of G-1-3

Synthesis was performed in the same manner as in the synthesis method of X-3 using 51.0 g (124.5 mmol) of G-1-2 instead of X-2. 70.1 g (95%) of Target Compound G-1-3 was obtained.

Synthesis of G-1-4

Synthesis was performed in the same manner as in the synthesis method of X-4 using 70.1 g (118.3 mmol) of G-1-3 instead of X-3. 61.9 g (91%) of Target Compound G-1-4 was obtained.

Synthesis of G-1-5

Synthesis was performed in the same manner as in the synthesis method of X-5 using 61.9 g (107.7 mmol) of G-1-4 instead of X-4. 67.0 g (100%) of Target Compound G-1-5 was obtained.

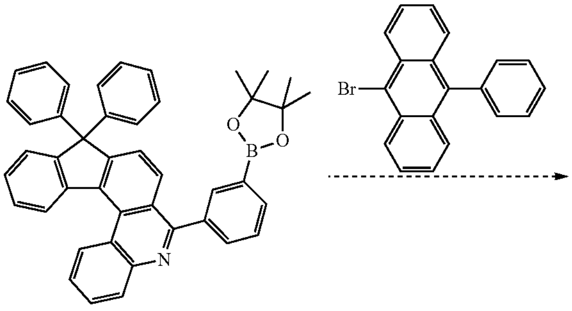

G-5

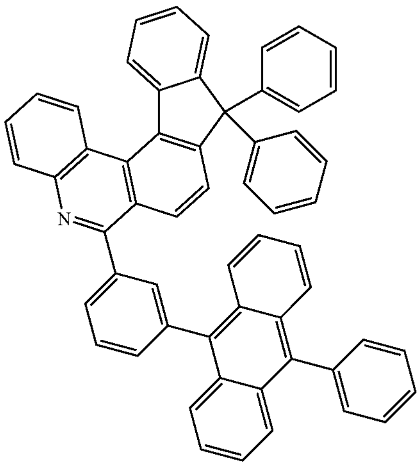

12-1

Synthesis of 12-1

10.0 g (16.1 mmol) of G-1-5, 5.9 g (17.7 mmol) of 9-bromo-10-phenylanthracene, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 10.2 g (83%) of Target Compound 12-1.

[Preparation Example 177] Preparation of Compound 12-3

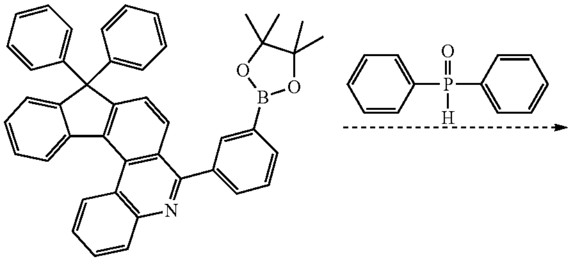

G-1-5

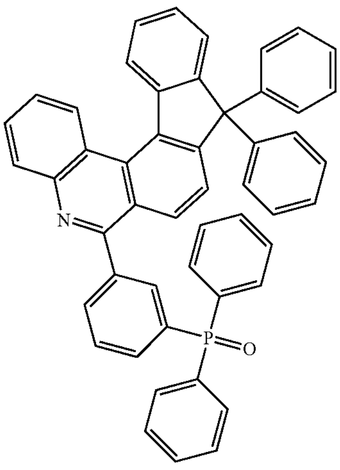

12-3

10.0 g (16.1 mmol) of G-1-5, 6.5 g (32.2 mmol) of diphenyl phosphineoxide, 1.9 g (1.6 mmol) of $Pd(PPh_3)_4$, and 3.1 mL (22.5 mmol) of TEA were stirred under reflux under 100 mL of toluene at 120° C. for 6 hours. After completion of the reaction, the reaction product was cooled to room temperature, and then a solid was produced and filtered, and then washed with MC, EA, and MeOH. And then, the resulting product was purified by column chromatography using dichloromethane and EA as an eluting solvent to obtain 4.8 g (43%) of Target Compound 12-3.

[Preparation Example 178] Preparation of Compound 12-5

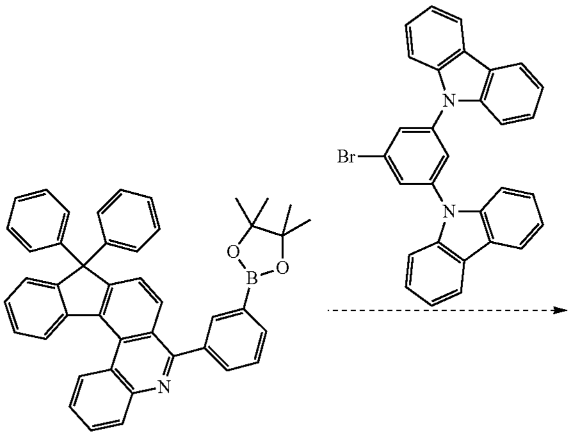

G-1-5

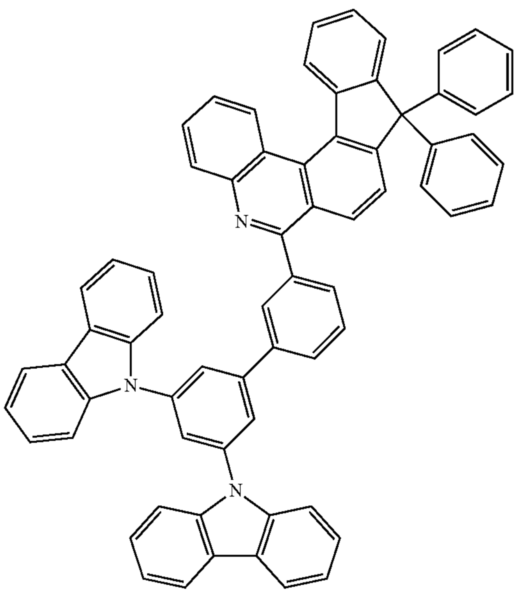

12-5

10.0 g (16.1 mmol) of G-1-5, 8.6 g (17.7 mmol) of 9,9'-(5-bromo-1,3-phenylene)bis(9H-carbazole), 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 12.7 g (88%) of Target Compound 12-5.

[Preparation Example 179] Preparation of Compound 12-6

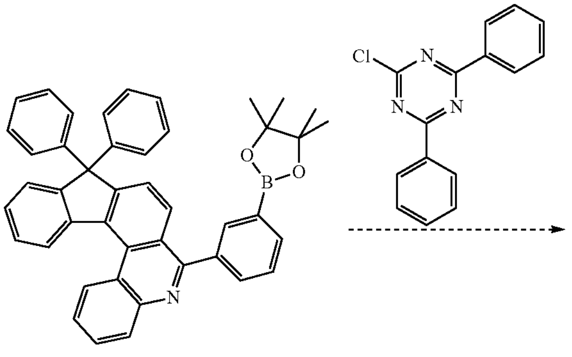

G-1-5

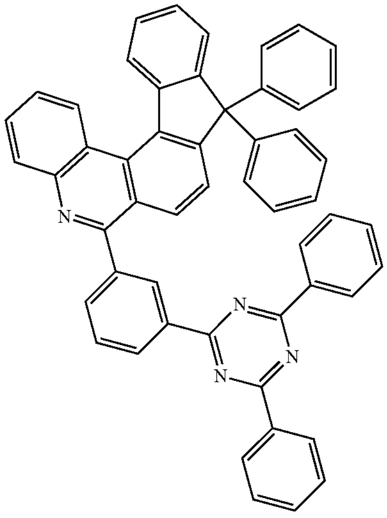

12-6

10.0 g (16.1 mmol) of G-1-5, 4.7 g (17.7 mmol) of 2-chloro-4,6-diphenyl-1,3,5-triazine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 4 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.9 g (85%) of Target Compound 12-6.

[Preparation Example 180] Preparation of Compound 12-12

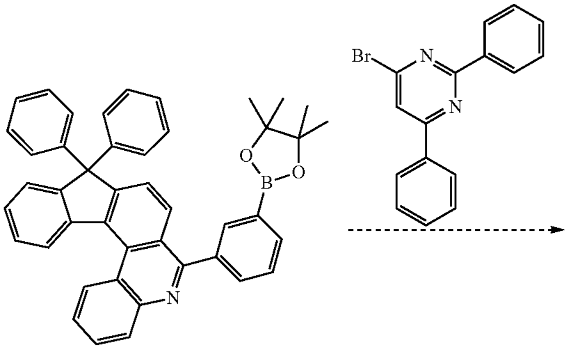

G-1-5

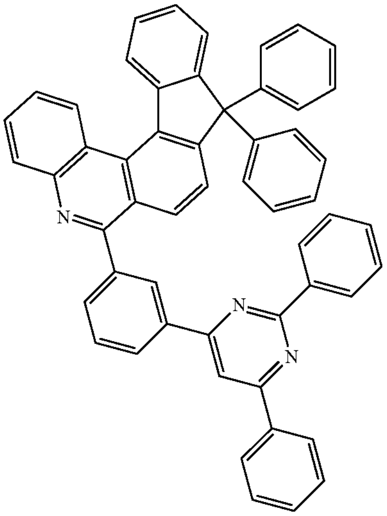

12-12

10.0 g (16.1 mmol) of G-1-5, 5.5 g (17.7 mmol) of 4-bromo-2,6-diphenylpyrimidine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 10.4 g (90%) of Target Compound 12-12.

[Preparation Example 181] Preparation of Compound 12-13

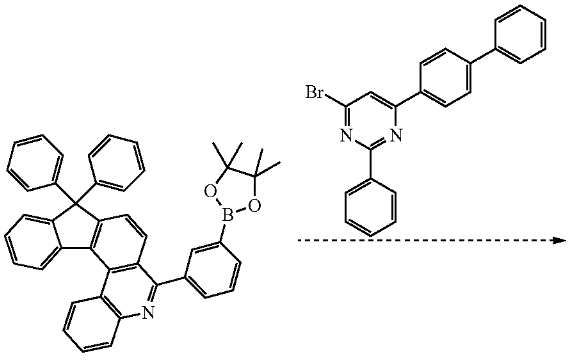

G-1-5

-continued

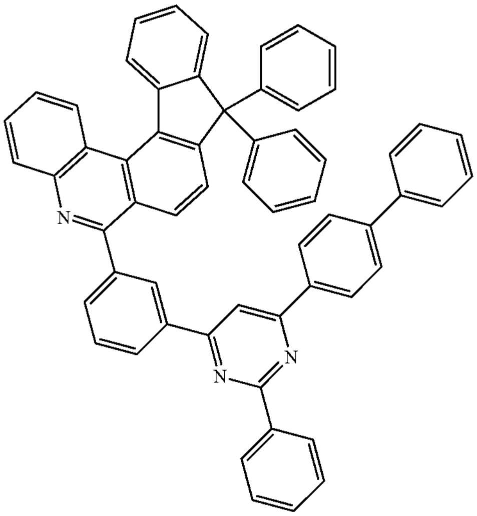

12-13

10.0 g (16.1 mmol) of G-1-5, 6.9 g (17.7 mmol) of 4-([1,1'-biphenyl]-4-yl)-6-bromo-2-phenylpyrimidine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 11.0 g (85%) of Target Compound 12-13.

[Preparation Example 182] Preparation of Compound 12-37

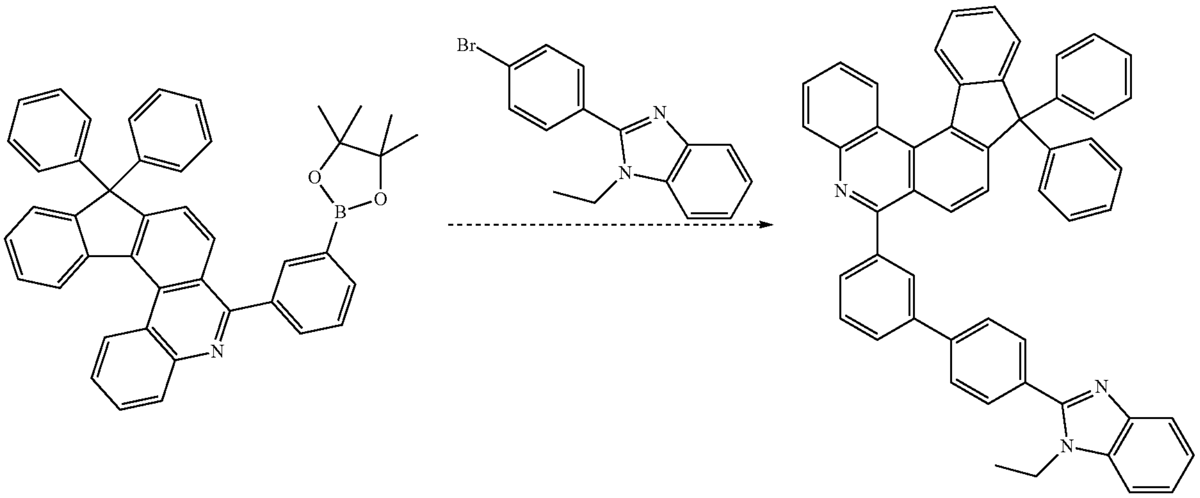

G-1-5

12-37

10.0 g (16.1 mmol) of G-1-5, 5.3 g (17.7 mmol) of 2-(4-bromophenyl)-1-ethyl-1H-benzo[d]imidazole, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.8 g (85%) of Target Compound 12-37.

[Preparation Example 183] Preparation of Compound 12-46

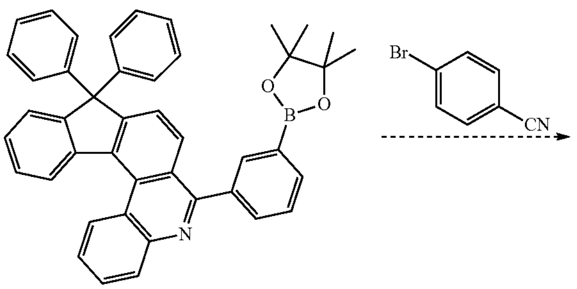

G-1-5

-continued

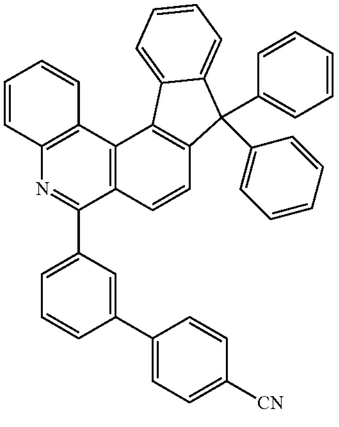

12-46

-continued

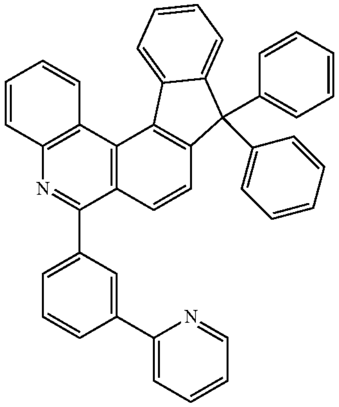

12-48

10.0 g (16.1 mmol) of G-1-5, 3.2 g (17.7 mmol) of 4-bromobenzonitrile, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 7.5 g (88%) of Target Compound 12-46.

[Preparation Example 184] Preparation of Compound 12-48

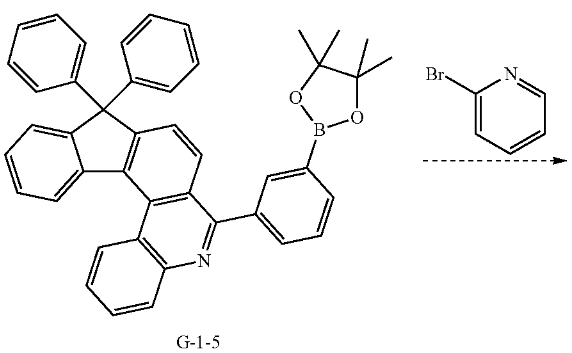

G-1-5

10.0 g (16.1 mmol) of G-1-5, 2.8 g (17.7 mmol) of 2-bromopyridine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 7.9 g (85%) of Target Compound 12-48.

[Preparation Example 185] Preparation of Compound 12-49

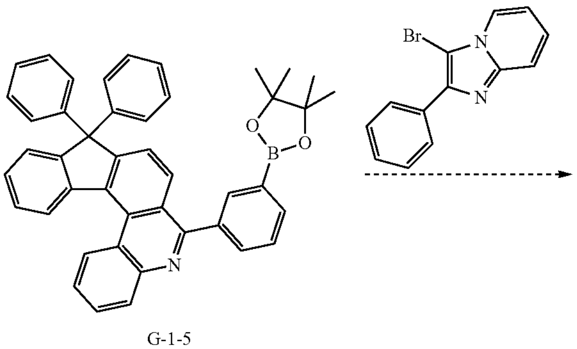

G-1-5

-continued

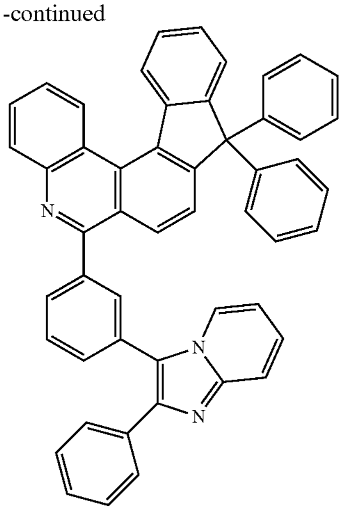

12-49

10.0 g (16.1 mmol) of G-1-5, 4.8 g (17.7 mmol) of 3-bromo-2-phenylimidazo[1,2-a]pyridine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.6 g (87%) of Target Compound 12-49.

[Preparation Example 185] Preparation of Compound 12-51

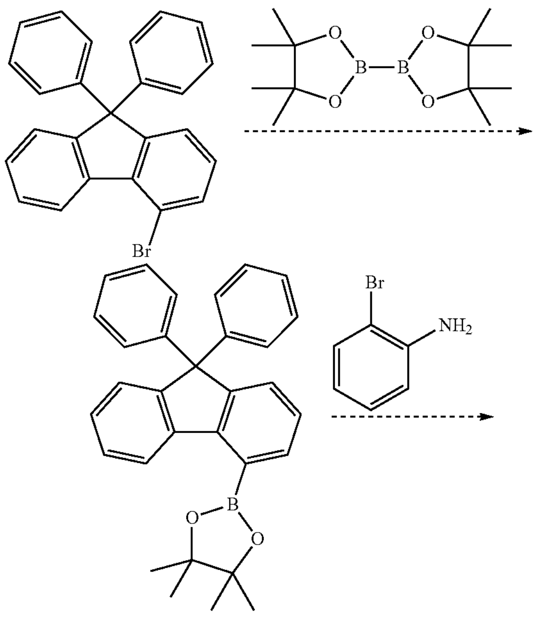

G-1-1

-continued

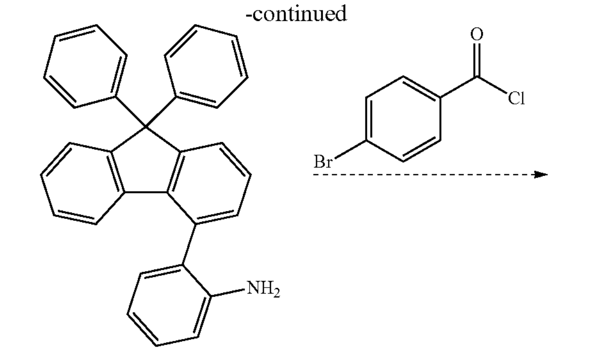

G-1-2

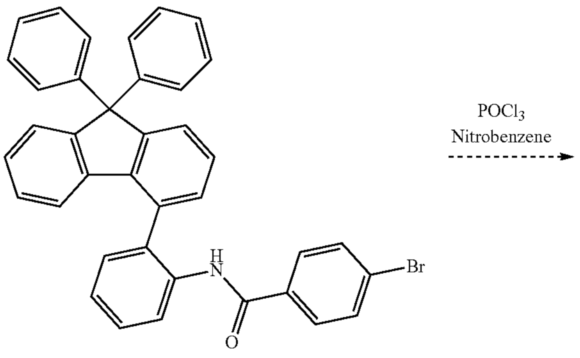

H-1-3

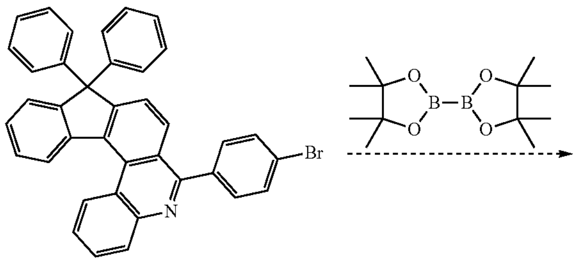

H-1-4

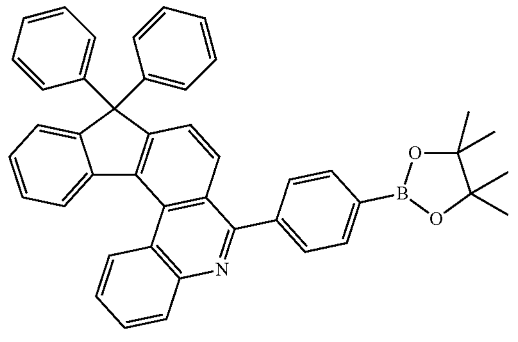

H-1-5

Synthesis of H-1-3

Synthesis was performed in the same manner as in the synthesis method of X-3 using 40.0 g (97.7 mmol) of G-1-2 instead of Y-2. 55.0 g (95%) of Target Compound H-1-3 was obtained.

Synthesis of H-1-4

Synthesis was performed in the same manner as in the synthesis method of X-4 using 55.0 g (92.8 mmol) of H-1-3 instead of Y-3. 50.1 g (94%) of Target Compound H-1-4 was obtained.

Synthesis of H-1-5

Synthesis was performed in the same manner as in the synthesis method of X-5 using 50.1 g (87.2 mmol) of H-1-4 instead of Y-4. 54.2 g (100%) of Target Compound H-1-5 was obtained.

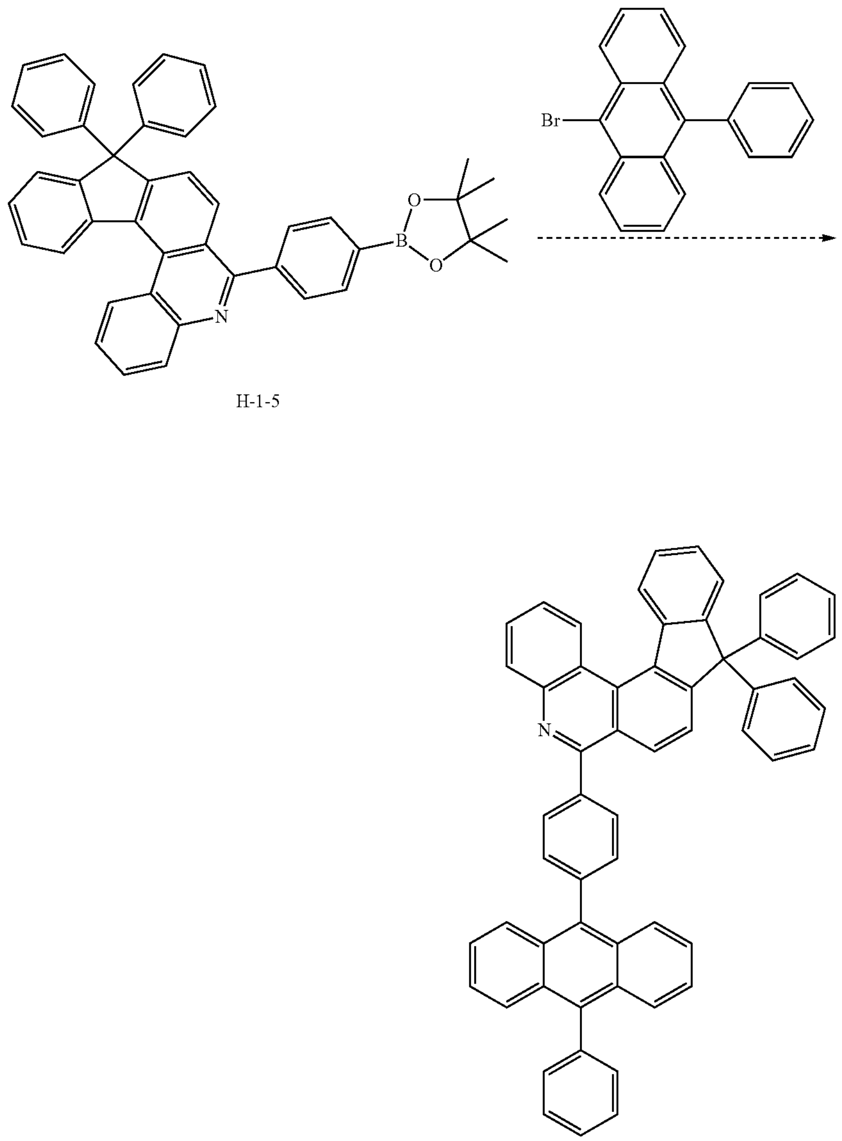

H-1-5

12-51

Synthesis of 12-51

10.0 g (16.1 mmol) of H-1-5, 5.9 g (17.7 mmol) of 9-bromo-10-phenylanthracene, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 10.2 g (83%) of Target Compound 12-51.

[Preparation Example 186] Preparation of Compound 12-53

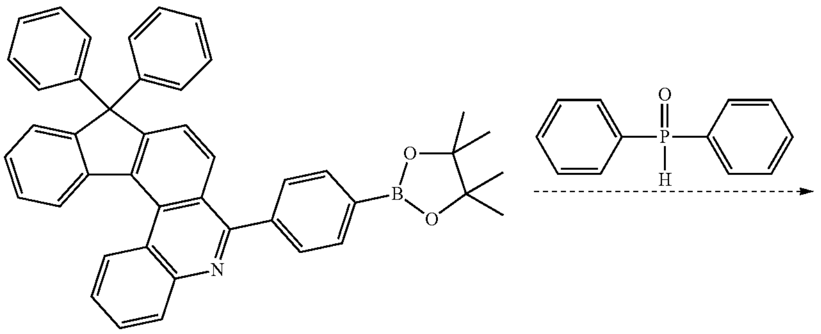

H-1-5

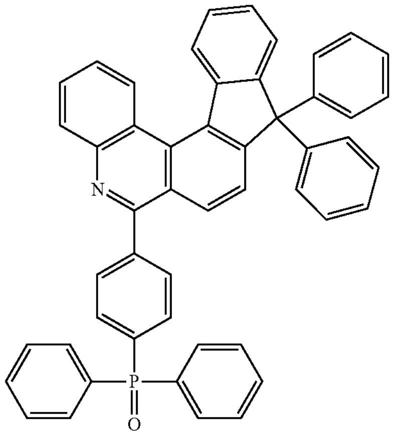

12-53

10.0 g (16.1 mmol) of H-1-5, 6.5 g (32.2 mmol) of diphenyl phosphineoxide, 1.9 g (1.6 mmol) of $Pd(PPh_3)_4$, and 3.1 mL (22.5 mmol) of TEA were stirred under reflux under 100 mL of toluene at 120° C. for 7 hours. After completion of the reaction, the reaction product was cooled to room temperature, and then a solid was produced and filtered, and then washed with MC, EA, and MeOH. And then, the resulting product was purified by column chromatography using dichloromethane and EA as an eluting solvent to obtain 5.4 g (48%) of Target Compound 12-53.

[Preparation Example 187] Preparation of Compound 12-55

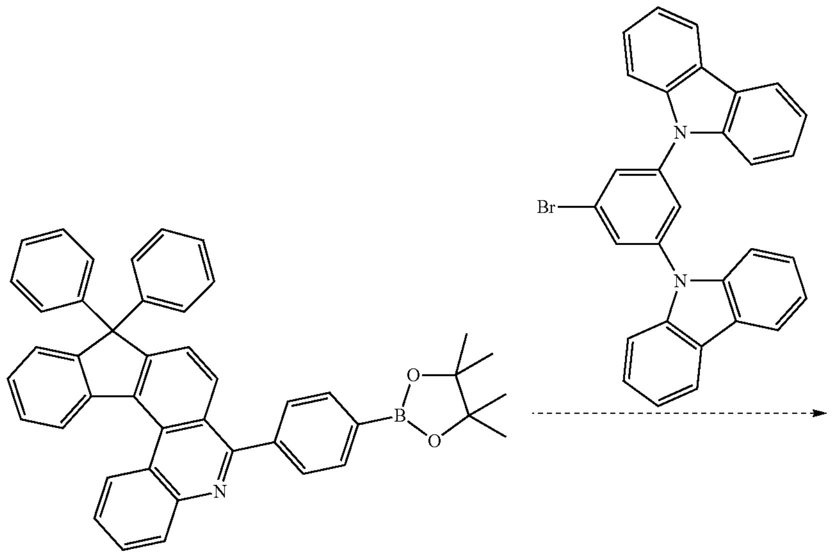

H-1-5

-continued

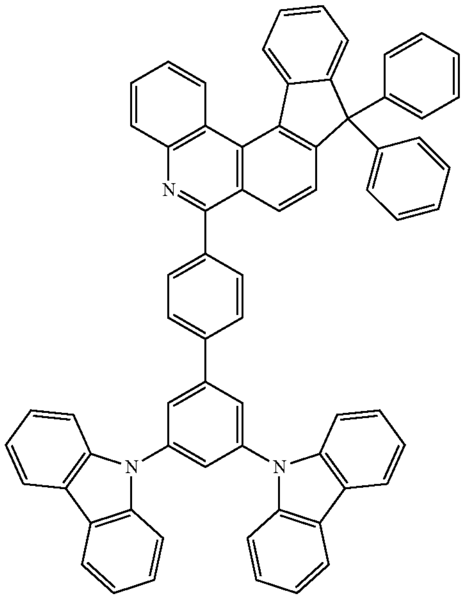

12-55

10.0 g (16.1 mmol) of H-1-5, 8.6 g (17.7 mmol) of 9,9'-(5-bromo-1,3-phenylene)bis(9H-carbazole), 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 12.3 g (85%) of Target Compound 12-55.

[Preparation Example 188] Preparation of Compound 12-56

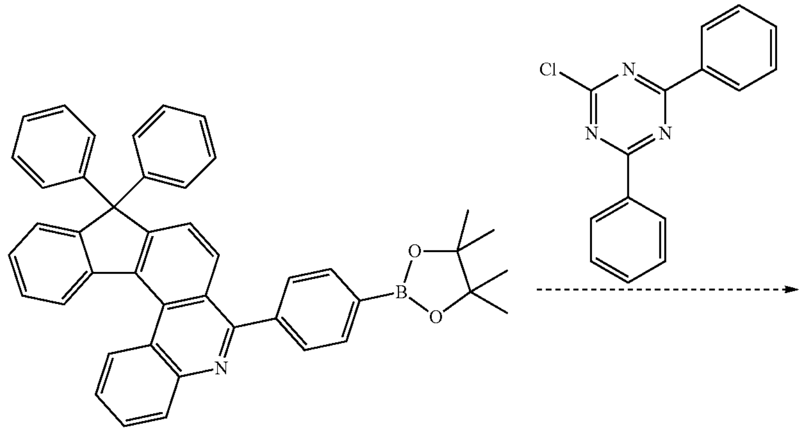

H-1-5

-continued

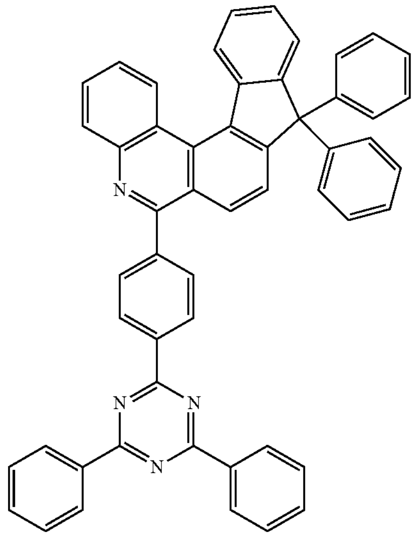

12-56

10.0 g (16.1 mmol) of H-1-5, 4.7 g (17.7 mmol) of 2-chloro-4,6-diphenyl-1,3,5-triazine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 3 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.7 g (83%) of Target Compound 12-56.

[Preparation Example 188] Preparation of Compound 12-62

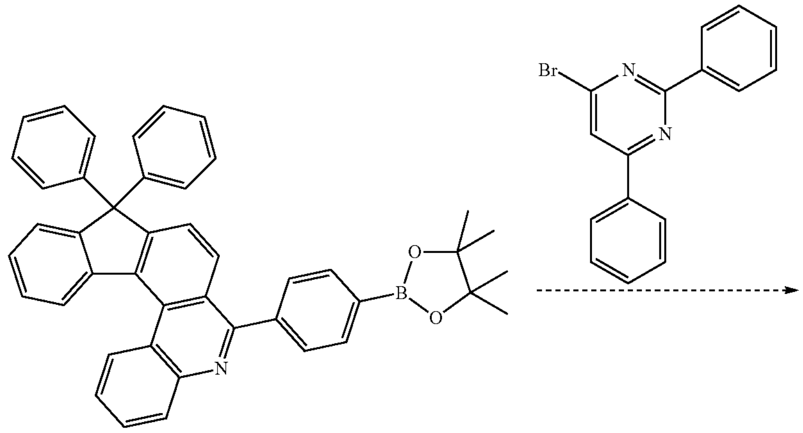

H-1-5

-continued

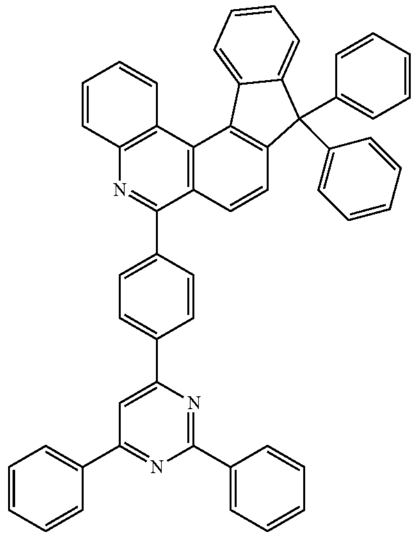

12-62

10.0 g (16.1 mmol) of H-1-5, 5.5 g (17.7 mmol) of 4-bromo-2,6-diphenylpyrimidine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 10.2 g (88%) of Target Compound 12-62.

[Preparation Example 189] Preparation of Compound 12-63

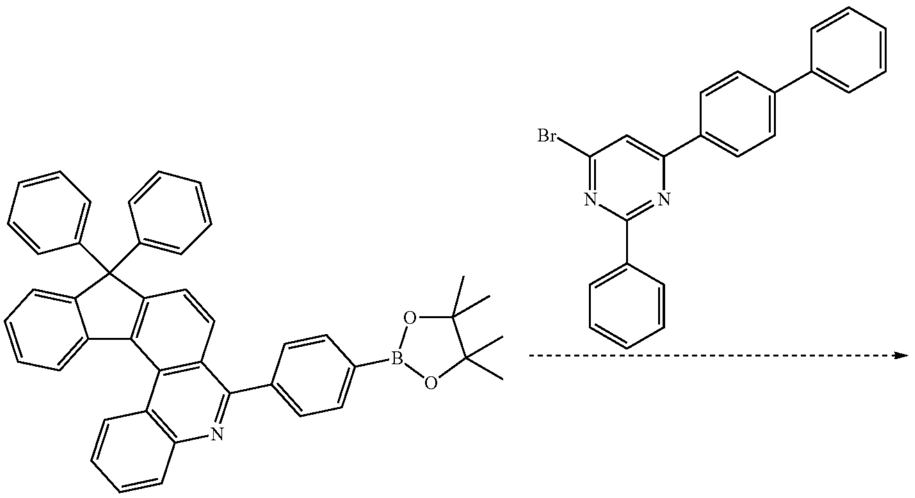

H-1-5

-continued

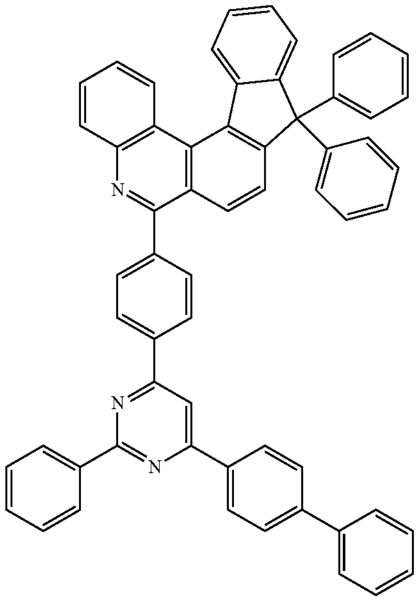

12-63

10.0 g (16.1 mmol) of H-1-5, 6.9 g (17.7 mmol) of 4-([1,1'-biphenyl]-4-yl)-6-bromo-2-phenylpyrimidine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 5 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 11.4 g (88%) of Target Compound 12-63.

[Preparation Example 190] Preparation of Compound 12-87

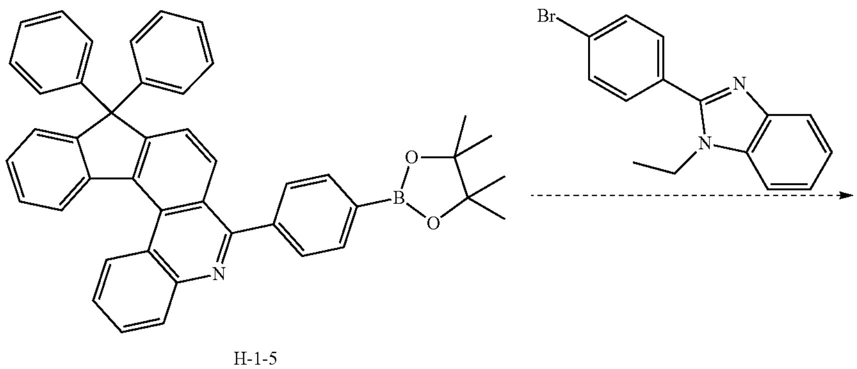

H-1-5

-continued

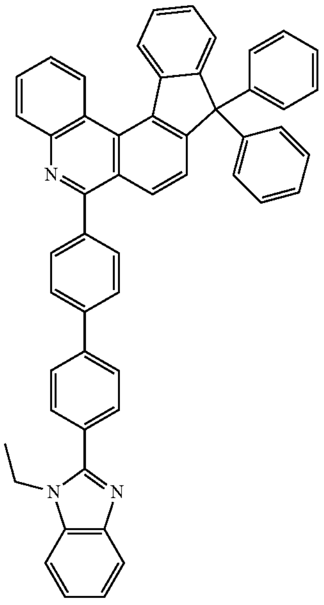

12-87

10.0 g (16.1 mmol) of H-1-5, 5.3 g (17.7 mmol) of 2-(4-bromophenyl)-1-ethyl-1H-benzo[d]imidazole, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.5 g (82%) of Target Compound 12-87.

[Preparation Example 191] Preparation of Compound 12-96

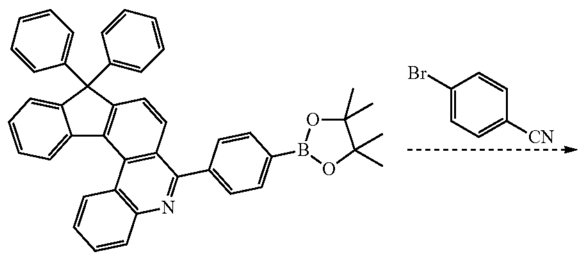

H-1-5

-continued

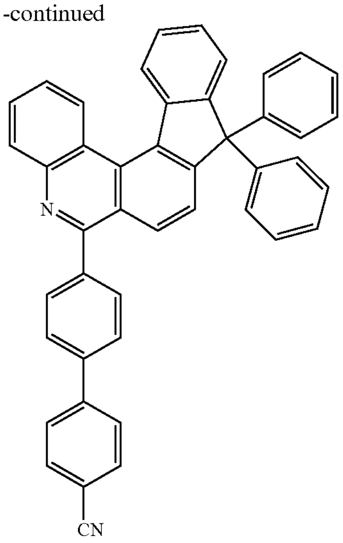

12-96

10.0 g (16.1 mmol) of H-1-5, 3.2 g (17.7 mmol) of 4-bromobenzonitrile, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 7.7 g (90%) of Target Compound 12-96.

1[Preparation Example 192] Preparation of Compound 12-98

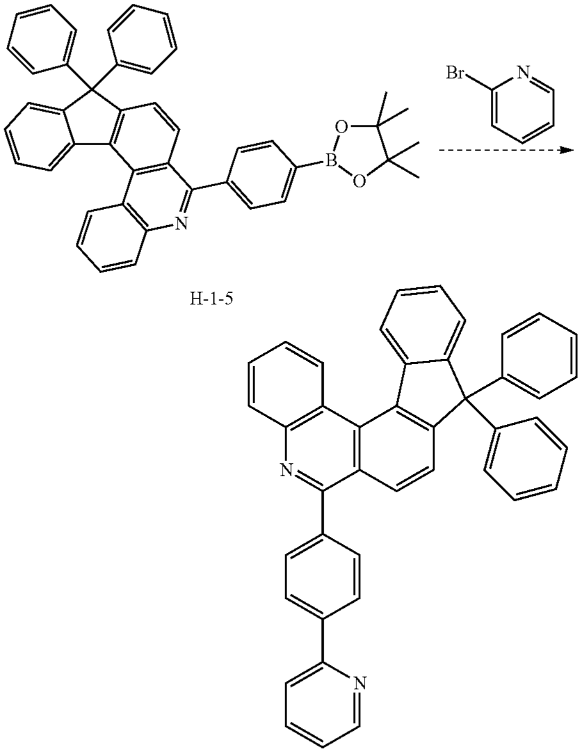

H-1-5

12-98

10.0 g (16.1 mmol) of H-1-5, 2.8 g (17.7 mmol) of 2-bromopyridine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 7 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 7.7 g (83%) of Target Compound 12-98.

[Preparation Example 193] Preparation of Compound 12-99

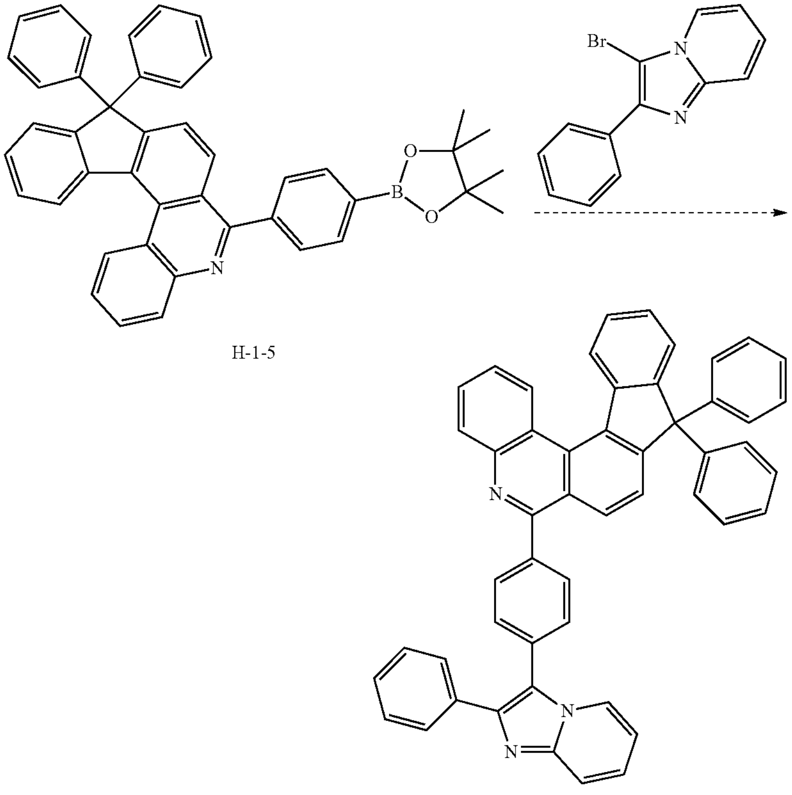

H-1-5

12-99

10.0 g (16.1 mmol) of H-1-5, 4.8 g (17.7 mmol) of 3-bromo-2-phenylimidazo[1,2-a]pyridine, 0.9 g (0.8 mmol) of $Pd(PPh_3)_4$, and 10.2 g (48.3 mmol) of $K_3PO_4$ were stirred under reflux under 170 mL of 1,4-dioxane and 30 mL of $H_2O$ at 120° C. for 6 hours. After completion of the reaction, the reaction product was extracted with distilled water and dichloromethane (MC). After the organic layer was dried over anhydrous $MgSO_4$, the solvent was removed by a rotary evaporator, and then the resulting product was purified by column chromatography using dichloromethane and hexane as an eluting solvent to obtain 9.8 g (89%) of Target Compound 12-99.

The compound was prepared by the same method as the Preparation Examples, and the synthesis confirmation results are described in Tables 1 and 2. Table 1 is a $^1H$ NMR ($CDCl_3$, 200 Mz) measurement value, and Table 2 is a FD-MS (field desorption mass spectrometry) measurement value.

TABLE 1

| Compound | $^1H$ NMR ($CDCl_3$, 200 Mz) |
|---|---|
| 1-1 | δ = 7.15~7.28 (m, 4H), 7.40~7.78 (m, 16H), 7.87~7.90 (t, 1H), 7.97~7.99 (d, 2H), 8.04~8.06 (d, 1H), 8.43~8.44 (s, 1H), 8.81~8.83 (dd, 4H), 8.91~8.99 (m, 3H), 9.40~9.42 (d, 1H) |
| 1-12 | δ = 7.17~7.19 (m, 1H), 7.24~7.70 (m, 22H), 7.78~7.94 (m, 7H), 8.05~8.20 (m, 7H), 8.8~8.90 (d, 1H), 9.40~9.41 (d, 1H) |
| 1-16 | δ = 7.16~7.25 (3H, m), 7.35 (1H, t), 7.50~7.70 (9H, m), 7.85~8.02 (8H, m), 8.18~8.20 (2H, m), 8.55 (1H, d), 8.69 (2H, m) |
| 1-36 | δ = 1.60 (s, 6H), 7.33~7.41 (m, 2H), 7.55~7.68 (m, 9H), 7.77~7.80 (t, 1H), 7.95~8.02 (m, 3H), 8.28~8.29 (d, 1H), 8.47~8.48 (d, 1H), 8.81~8.83 (m, 4H), 8.97~8.99 (d, 2H), 9.14~9.15 (d, 1H) |
| 1-113 | δ = 7.25~7.92 (19H, m), 8.09~8.18 (4H, m), 8.34~8.36 (1H, d), 8.90~8.92 (1H, d), 9.38~9.40 (1H, d) |
| 1-119 | δ = 7.39~8.00 (18H, m), 8.11~8.13 (1H, m), 8.19 (1H, s), 8.38~8.40 (1H, m), 8.65~8.73 (5H, m), 8.92~8.94 (2H, m), 9.40~9.42 (1H, d) |
| 1-124 | δ = 7.25~7.29 (3H, m), 7.39~7.88 (22H, m), 8.03~8.05 (2H, m), 8.12~8.14 (2H, m), 8.32~8.34 (1H, d), 8.89~8.91 (1H, d), 9.37~9.39 (1H, d) |
| 1-157 | δ = 7.16~7.20 (4H, m), 7.35 (2H, m), 7.49~7.70 (11H, m), 7.85~7.99 (6H, m), 8.17~8.20 (4H, m), 8.33 (2H, m), 8.45 (1H, d), 8.55 (2H, m) |
| 1-190 | δ = 7.16 (1H, t), 7.35 (1H, t), 7.49~7.51 (8H, m), 7.65~7.99 (15H, m), 8.19~8.20 (3H, m), 8.55 (1H, d) |
| 2-3 | δ = 7.20 (1H, t), 7.41~7.75 (17H, m), 7.85~7.87 (4H, m), 7.94 (1H, d), 8.19~8.35 (9H, m), 8.69 (2H, m) |
| 2-44 | δ = 7.16 (1H, t), 7.35 (1H, t), 7.49~7.70 (13H, m), 7.83~7.96 (9H, m), 8.20~8.23 (2H, m), 8.55 (1H, d), 8.69 (2H, m) |
| 2-123 | δ = 7.20~7.28 (2H, m), 7.50~7.85 (22H, m), 7.94 (1H, d), 8.19~8.33 (6H, m), 8.56 (1H, d) |
| 2-107 | δ = 7.16~7.20 (3H, m), 7.31~7.39 (4H, m), 7.50~7.73 (10H, m), 7.85~7.98 (6H, m), 8.17~8.20 (5H, m), 8.33 (2H, m), 8.55 (2H, m) |
| 2-243 | δ = 7.16 (1H, t), 7.35 (1H, t), 7.49 (1H, t), 7.64~7.70 (8H, m), 7.85~7.94 (9H, m), 8.05 (1H, s), 8.19~8.27 (4H, m), 8.55 (1H, d), 8.84 (1H, d), 9.08 (1H, d) |
| 3-19 | δ = 7.16~7.38 (14H, m), 7.55~7.94 (17H, m), 8.09 (1H, d), 8.20 (1H, d), 8.55 (1H, d), 8.69 (2H, m) |
| 3-43 | δ = 7.20~7.28 (2H, m), 7.50~7.85 (22H, m), 7.94 (1H, d), 8.19~8.28 (4H, m), 8.56 (1H, d), 8.69 (2H, m) |
| 4-1 | δ = 7.16 (1H, t), 7.35 (1H, t), 7.50~7.70 (13H, m), 7.85 (1H, t), 7.94~7.99 (5H, m), 8.20 (1H, d), 8.36 (4H, m), 8.55 (1H, d), 8.69 (2H, m) |
| 1-318 | 7.17-7.24 (m, 3H), 7.30~7.3 (m, 6H), 7.36~7.40 (m, 1H), 7.46~7.62 (m, 15H), 7.67~7.72 (3H, m), 7.80~7.84 (d, 2H), 8.30~8.32 (d, 1H), 8.66~8.69 (m, 2H), 8.87~8.89 (d, 1H), 9.35~9.37 (d, 1H) |
| 2-36 | 6.76~6.77 (d, 2H), 7.17~7.32 (m, 2H), 7.55~7.79 (m, 13H), 7.94~7.96 (d, 1H), 8.13~8.15 (d, 2H), 8.48~8.49 (d, 1H), 8.64~8.65 (d, 1H), 8.75~8.80 (m, 6H), 8.90~8.92 (d, 2H) |
| 2-38 | 6.76~6.77 (d, 2H), 7.17~7.80 (m, 19H), 7.91~7.94 (d, 1H), 8.11~8.13 (m, 3H), 8.34~8.39 (d, 2H), 8.44~8.46 (d, 2H), 8.64~8.66 (d, 2H), 8.74~8.77 (m, 3H) |
| 3-39 | 7.28~7.75 (m, 18H), 7.82~7.85 (d, 2H), 8.01~8.09 (d, 2H), 8.20~8.29 (m, 3H), 8.44~8.47 (d, 2H), 8.56~8.61 (m, 4H), 8.82~8.84 (d, 2H), 8.89 (s, 1H) |
| 3-46 | 7.26~7.63 (m, 13H), 7.69~7.76 (m, 9H), 7.85~7.88 (d, 2H), 7.93~7.95 (d, 2H), 8.52~8.54 (d, 2H), 8.88 (s, 1H) |
| 4-56 | 8.69 (d, 2H), 8.45 (d, 1H), 8.36 (d, 4H), 8.20 (d, 1H), 7.99-7.93 (m, 5H), 7.85 (t, 1H), 7.70 (t, 1H), 7.62 (d, 1H), 7.56 (t, 1H), 7.50-7.49 (m, 7H) |
| 4-58 | 8.69 (d, 2H), 8.45 (d, 1H), 8.35 (d, 2H), 8.30 (d, 4H), 8.23 (s, 1H), 8.20 (d, 1H), 7.99 (d, 1H), 7.94-7.93 (m, 2H), 7.85 (d, 3H), 7.75 (d, 2H), 7.70 (d, 1H), 7.62 (d, 1H), 7.56 (t, 1H), 7.50-7.49 (m, 6H), 7.41-7.40 (m, 1H) |
| 4-76 | 8.69 (d, 2H), 8.36 (d, 4H), 8.20 (d, 1H), 7.99-7.94 (m, 5H), 7.85 (t, 1H), 7.70 (t, 1H), 7.62 (d, 1H), 7.54-7.50 (m, 7H), 7.39 (t, 1H), 7.31 (t, 1H) |
| 4-169 | 8.35-8.33 (m, 4H), 8.23 (s, 1H), 8.20 (d, 1H), 7.99-7.98 (m, 2H), 7.94 (d, 4H), 7.85 (t, 1H), 7.73-7.70 (m, 2H), 7.62 (d, 1H), 7.55-7.49 (m, 7H), 7.39 (t, 1H), 7.31 (t, 1H) |
| 1-482 | 8.55 (d, 1H), 8.35 (d, 2H), 8.23 (s, 1H), 8.20-8.19 (m, 3H), 7.99 (d, 1H), 7.94-7.91 (m, 8H), 7.85 (t, 1H), 7.70 (t, 1H), 7.65 (t, 2H), 7.55-7.49 (m, 8H), 7.35 (t, 1H), 7.16 (t, 1H) |
| 1-483 | 8.55 (d, 1H), 8.20-8.19 (m, 5H), 8.13 (d, 1H), 7.99 (d, 1H), 7.94 (d, 2H), 7.85-7.83 (m, 3H), 7.70 (t, 1H), 7.65 (t, 2H), 7.58 (t, 1H), 7.50-7.49 (m, 5H), 7.35 (t, 1H), 7.16 (t, 1H) |

TABLE 1-continued

| Compound | $^1$H NMR ($CDCl_3$, 200 Mz) |
|---|---|
| 2-127 | 8.55 (d, 3H), 8.33 (d, 2H), 8.20-8.17 (m, 5H), 7.94 (d, 4H), 7.87 (s, 1H), 7.85 (t, 1H), 7.73-7.70 (m, 3H), 7.62-7.58 (m, 7H), 7.50-7.49 (m, 4H), 7.35 (t, 3H), 7.20-7.16 (m, 5H) |
| 2-148 | 8.55 (d, 1H), 8.33-8.30 (m, 3H), 8.20-8.19 (m, 2H), 8.13 (d, 1H), 7.94 (d, 2H), 7.89 (s, 1H), 7.87 (s, 1H), 7.85 (t, 1H), 7.73-7.70 (m, 3H), 7.62-7.58 (m, 8H), 7.50 (d, 5H), 7.35 (t, 1H), 7.20-7.16 (m, 2H) |
| 3-12 | 8.69 (d, 2H), 8.55 (d, 3H), 8.20-8.17 (m, 5H), 7.94 (d, 4H), 7.85-7.83 (m, 4H), 7.70-7.69 (m, 2H), 7.62-7.58 (m, 6H), 7.50 (t, 4H), 7.35 (t, 3H), 7.20-7.16 (m, 5H) |
| 4-109 | 8.55 (d, 1H), 8.33 (d, 2H), 8.20 (d, 1H), 8.09 (d, 1H), 7.99-7.85 (m, 6H), 7.78-7.70 (m, 3H), 7.62-7.50 (m, 8H), 7.38-7.35 (m, 2H), 7.28-7.26 (m, 5H), 7.18-7.16 (m, 3H), 7.10 (d, 4H) |
| 4-113 | 8.55 (d, 2H), 8.45 (d, 1H), 8.33-8.32 (m, 3H), 8.20 (d, 1H), 7.99-7.93 (m, 4H), 7.85 (t, 1H), 7.73-7.70 (m, 3H), 7.62-7.56 (m, 6H), 7.50-7.49 (m, 3H), 7.35 (t, 1H), 7.16 (t, 1H) |
| 4-119 | 9.27 (s, 1H), 8.79 (d, 1H), 8.55 (d, 1H), 8.37-8.30 (m, 6H), 8.20 (d, 1H), 7.99-7.94 (m, 3H), 7.85 (t, 1H), 7.73-7.58 (m, 11H), 7.52-7.50 (m, 3H), 7.35 (t, 1H), 7.16 (t, 1H) |
| 5-15 | δ = 6.48 (1H, d), 7.00~7.24 (7H, m), 7.35~7.37 (3H, m), 7.50~7.70 (14H, m), 7.85~8.01 (6H, m), 8.12~8.20 (4H, m), 8.55 (1H, d) |
| 5-20 | δ = 1.69 (6H, d), 7.16 (2H, m), 7.28~7.75 (23H, m), 7.85~7.94 (6H, m), 8.12 (2H, d), 8.20 (1H, d), 8.55 (1H, d) |
| 5-33 | δ = 6.48 (1H, s), 7.16~7.20 (3H, m), 7.33~7.37 (6H, m), 7.50~7.70 (20H, m), 7.85~8.01 (7H, m), 8.12~8.20 (4H, m), 8.55 (2H, d) |
| 5-55 | δ = 7.16~7.35 (6H, m), 7.50~7.94 (26H, m), 8.20 (1H, d), 8.30 (2H, m), 8.55 (3H, m) |
| 5-82 | δ = 7.10~7.62 (35H, m), 7.85~7.99 (6H, m), 8.12 (2H, m), 8.20 (1H, d), 8.55 (1H, d) |
| 6-14 | δ = 6.91 (1H, d), 7.00~7.08 (3H, m), 7.24~7.39 (8H, m), 7.54~7.70 (4H, m), 7.80~7.85 (2H, m), 7.94~8.03 (5H, m), 8.12~8.20 (3H, m) |
| 6-37 | δ = 7.16 (1H, t), 7.31~7.70 (20H, m), 7.94~8.01 (7H, m), 8.12~8.20 (3H, m), 8.45~8.55 (2H, m) |
| 6-55 | δ = 7.16 (2H, m), 7.31~7.39 (4H, m), 7.50~7.99 (22H, m), 8.20 (1H, d), 8.30 (2H, m), 8.55 (2H, m) |
| 6-65 | δ = 1.69 (6H, s), 7.11~7.16 (2H, m), 7.28~7.45 (10H, m), 7.55~7.90 (13H, m), 8.12 (2H, m), 8.20 (1H, d) |
| 6-85 | δ = 7.16~7.20 (2H, m), 7.31~7.39 (3H, m), 7.50~7.70 (5H, m), 7.85~7.99 (11H, m), 8.19~8.20 (2H, m), 8.55 (1H, d), 8.69 (2H, m) |
| 7-24 | δ = 6.48 (1H, d), 7.20 (1H, t), 7.37~7.70 (22H, m), 7.85~8.01 (6H, m), 8.12~8.20 (4H, m), 8.45 (1H, d) |
| 7-48 | δ = 7.37~7.70 (26H, m), 7.85~7.99 (6H, m), 8.20 (1H, d), 8.45 (1H, d), 8.69 (2H, d) |
| 7-55 | δ = 7.16 (2H, m), 7.35 (2H, m), 7.50~7.99 (23H, m), 8.20 (1H, d), 8.30 (2H, m), 8.45 (1H, d), 8.55~8.56 (2H, m) |
| 7-75 | δ = 7.20~7.38 (19H, m), 7.55~7.70 (15H, m), 7.85~7.99 (6H, m), 8.12~8.22 (5H, m), 8.45 (1H, d), 8.62 (1H, d) |
| 7-88 | δ = 7.20~7.25 (3H, m), 7.50~7.70 (12H, m), 7.85~8.04 (5H, m), 8.19~8.22 (3H, m), 8.45 (1H, d), 8.69 (2H, m) |
| 10-1 | δ = 7.10~7.26 (10H, m), 7.37~7.41 (6H, m), 7.40~7.70 (10H, m), 7.85~7.94 (3H, m), 8.20~8.24 (6H, m), 8.32~8.34 (2H, m) |
| 10-3 | δ = 7.10~7.26 (10H, m), 7.38 (1H, t), 7.51~7.57 (7H, m), 7.70~7.94 (12H, m), 8.20~8.24 (2H, m), 8.48 (1H, d), 8.52 (1H, s) |
| 10-5 | δ = 7.16~7.40 (17H, m), 7.50~7.73 (11H, m), 7.85~7.94 (5H, m), 8.17~8.24 (6H, m), 8.32~8.24 (2H, m), 8.55 (2H, d) |
| 10-6 | δ = 7.10~7.26 (10H, m), 7.38 (1H, t), 7.48~7.52 (6H, m), 7.57 (1H, t), 7.70~7.74 (4H, m), 7.85 (1H, t), 7.89 (1H, s), 7.94 (1H, d), 8.20 (1H, d), 8.24 (1H, d), 8.33~8.38 (7H, m) |
| 10-12 | δ = 7.10~7.26 (10H, m), 7.38 (1H, t), 7.49~7.57 (7H, m), 7.70~7.74 (4H, m), 7.85~7.94 (6H, m), 8.20~8.24 (3H, m), 8.33,~8.35 (4H, m) |
| 10-13 | δ = 7.10~7.26 (10H, m), 7.38~7.57 (8H, m), 7.70~7.75 (6H, m), 7.85~7.94 (6H, m), 8.20~8.24 (3H, m), 8.30~8.35 (6H, m) |
| 10-37 | δ = 1.31 (3H, t), 4.12 (2H, q), 7.10~7.27 (14H, m), 7.38 (1H, t), 7.40~7.73 (8H, m), 7.85~7.96 (5H, m), 8.20 (1H, d), 8.24 (1H, d), 8.32~8.34 (2H, m) |
| 10-46 | δ = 7.10~7.26 (14H, m), 7.38 (1H, t), 7.57 (1H, d), 7.61 (1H, d), 7.70~7.74 (4H, m), 7.84~7.94 (7H, m), 8.20 (1H, d), 8.24 (1H, d), 8.32~8.34 (2H, m) |
| 10-48 | δ = 6.90 (1H, dd), 7.10~7.26 (11H, m), 7.37~7.39 (2H, m), 7.57 (1H, t), 7.70~7.73 (4H, m), 7.85 (1H, t), 7.89 (1H, s), 7.94 (1H, d), 8.20 (1H, d), 8.24 (1H, d), 8.33~8.37 (3H, m), 8.72 (1H, s) |
| 10-49 | δ = 6.86 (1H, t), 7.10~7.28 (13H, m), 7.38 (1H, t), 7.47~7.50 (4H, m), 7.57 (1H, t), 7.70~7.73 (4H, m), 7.85~7.94 (4H, m), 8.20 (1H, d), 8.24 (1H, d), 8.32~8.34 (2H, m), 8.48 (1H, d) |
| 10-51 | δ = 7.10~7.41 (18H, m), 7.55~7.70 (8H, m), 7.85 (1H, t), 7.89 (1H, s), 7.94 (1H, d), 8.20~8.24 (6H, m), 8.68 (2H, d) |
| 10-53 | δ = 7.10~7.26 (10H, m), 7.38 (1H, t), 7.50~7.52 (6H, m), 7.57 (1H, t), 7.70~7.94 (12H, m), 8.20 (1H, d), 8.24 (1H, d), 8.36 (2H, d) |
| 10-55 | δ = 7.10~7.38 (16H, m), 7.50~7.60 (6H, m), 7.69~7.71 (3H, m), 7.85~7.94 (7H, m), 8.17~8.24 (6H, m), 8.55 (2H, d), 8.69 (2H, d) |
| 10-56 | δ = 7.10~7.26 (10H, m), 7.38 (1H, t), 7.48~7.52 (6H, m), 7.57 (1H, t), 7.70~7.74 (3H, m), 7.85 (1H, t), 7.89 (1H, s), 7.94 (1H, d), 7.96 (2H, d), 8.20 (1H, d), 8.24 (1H, d), 8.35~8.37 (4H, m), 8.69 (2H, d) |

TABLE 1-continued

| Compound | $^1H$ NMR ($CDCl_3$, 200 Mz) |
|---|---|
| 10-62 | δ = 7.10~7.26 (10H, m), 7.38 (1H, t), 7.49~7.57 (7H, m), 7.70~7.74 (3H, m), 7.85 (1H, t), 7.89 (1H, s), 7.93~7.95 (3H, m), 8.20~8.35 (7H, m), 8.69 (2H, d) |
| 10-63 | δ = 7.10~7.26 (10H, m), 7.38~7.57 (8H, m), 7.70~7.74 (5H, m), 7.85~7.94 (5H, m), 8.20~8.35 (9H, m), 8.69 (2H, d) |
| 10-87 | δ = 1.31 (3H, t), 4.12 (2H, q), 7.10~7.27 (14H, m), 7.38 (1H, t), 7.57~7.74 (6H, m), 7.85~7.96 (7H, m), 8.20 (1H, d), 8.24 (1H, d), 8.69 (2H, d) |
| 10-96 | δ = 7.10~7.27 (14H, m), 7.38 (1H, t), 7.57 (1H, t), 7.70~7.74 (3H, m), 7.85~7.94 (9H, m), 8.20 (1H, d), 8.24 (1H, d), 8.69 (2H, d) |
| 10-98 | δ = 6.90 (1H, t), 7.10~7.26 (11H, m), 7.37~7.39 (2H, m), 7.57 (1H, t), 7.70~7.74 (3H, m), 7.85 (1H, t), 7.89 (1H, s), 7.94 (1H, d), 8.20 (1H, d), 8.24 (1H, d), 8.68~8.70 (4H, m) |
| 10-99 | δ = 6.86 (1H, t), 7.10~7.28 (13H, m), 7.38 (1H, t), 7.47~7.50 (4H, m), 7.57 (1H, t), 7.70~7.74 (3H, m), 7.85 (1H, t), 7.89 (1H, s), 7.94 (1H, d), 8.20 (1H, d), 8.24 (1H, d), 8.30 (2H, d), 8.48 (1H, d), 8.69 (2H, d) |
| 11-26 | δ = 7.10~7.26 (10H, m), 7.37~7.41 (6H, m), 7.55~7.74 (10H, m), 7.85 (1H, dd), 7.88 (1H, s), 7.94 (1H, d), 8.20~8.24 (6H, m), 8.32~8.34 (2H, m) |
| 11-28 | δ = 7.10~7.26 (10H, m), 7.38 (1H, t), 7.48~7.54 (6H, m), 7.57 (1H, t), 7.70~7.94 (12H, m), 8.20 (1H, d), 8.24 (1H, d), 8.48 (1H, d), 8.52 (1H, s) |
| 11-29 | δ = 7.16~7.38 (17H, m), 7.50~7.74 (11H, m), 7.85 (1H, t), 7.88 (1H, s), 7.93~7.95 (3H, m), 8.17~8.24 (6H, m), 8.32~8.24 (2H, m), 8.55 (2H, d) |
| 11-30 | δ = 7.10~7.26 (10H, m), 7.38 (1H, t), 7.48~7.52 (6H, m), 7.57 (1H, t), 7.70~7.74 (4H, m), 7.85 (1H, t), 7.89 (1H, s), 7.94 (1H, d), 8.20 (1H, d), 8.24 (1H, d), 8.33~8.38 (7H, m) |
| 11-35 | δ = 7.10~7.26 (10H, m), 7.38 (1H, t), 7.49~7.57 (7H, m), 7.70~7.74 (4H, m), 7.85 (1H, t), 7.88 (1H, s), 7.92~7.96 (4H, m), 8.20~8.24 (3H, m), 8.33~8.35 (4H, m) |
| 11-36 | δ = 7.10~7.26 (10H, m), 7.38~7.57 (8H, m), 7.70~7.75 (6H, m), 7.85~7.94 (6H, m), 8.20~8.35 (9H, m) |
| 11-45 | δ = 1.31 (3H, t), 4.12 (2H, q), 7.10~7.27 (14H, m), 7.38 (1H, t), 7.57~7.73 (8H, m), 7.85 (1H, t), 7.88 (1H, s), 7.94~7.96 (3H, m), 8.20 (1H, d), 8.24 (1H, d), 8.32~8.34 (2H, m) |
| 11-48 | δ = 7.10~7.26 (10H, m), 7.38 (1H, t), 7.57 (1H, t), 7.61 (1H, d), 7.70~7.74 (4H, m), 7.84~7.94 (7H, m), 8.20 (1H, d), 8.24 (1H, d), 8.32~8.34 (2H, m) |
| 11-49 | δ = 6.90 (1H, t), 7.10~7.26 (11H, m), 7.37~7.39 (2H, m), 7.57 (1H, t), 7.70~7.74 (4H, m), 7.85 (1H, t), 7.88 (1H, s), 7.94 (1H, d), 8.20 (1H, d), 8.24 (1H, d), 8.33~8.37 (3H, m), 8.72 (1H, s) |
| 11-50 | δ = 6.86 (1H, t), 7.10~7.28 (13H, m), 7.38 (1H, t), 7.47~7.50 (4H, m), 7.57 (1H, t), 7.70~7.73 (4H, m), 7.85~7.94 (4H, m), 8.20 (1H, d), 8.24 (1H, d), 8.32~8.34 (2H, m), 8.48 (1H, d) |
| 11-76 | δ = 7.10~7.41 (18H, m), 7.55~7.74 (8H, m), 7.85 (1H, t), 7.89 (1H, s), 7.94 (1H, d), 8.20~8.24 (6H, m), 8.69 (2H, d) |
| 11-78 | δ = 7.10~7.26 (10H, m), 7.38 (1H, t), 7.50~7.52 (6H, m), 7.57 (1H, t), 7.70~7.96 (12H, m), 8.20 (1H, d), 8.24 (1H, d), 8.36 (2H, d) |
| 11-79 | δ = 7.10~7.35 (17H, m), 7.50~7.60 (6H, m), 7.70~7.73 (3H, m), 7.85~7.94 (7H, m), 8.17~8.24 (6H, m), 8.55 (2H, d), 8.69 (2H, d) |
| 11-80 | δ = 7.10~7.26 (10H, m), 7.38 (1H, t), 7.48~7.52 (6H, m), 7.57 (1H, t), 7.70~7.74 (3H, m), 7.85 (1H, t), 7.89 (1H, s), 7.94~7.96 (3H, m), 8.20 (1H, d), 8.24 (1H, d), 8.35~8.37 (4H, m), 8.69 (2H, d) |
| 11-85 | δ = 7.10~7.26 (10H, m), 7.38 (1H, t), 7.49~7.57 (7H, m), 7.70~7.74 (3H, m), 7.85 (1H, t), 7.89 (1H, s), 7.93~7.95 (3H, m), 8.20~8.35 (7H, m), 8.69 (2H, d) |
| 11-86 | δ = 7.10~7.26 (10H, m), 7.38~7.57 (8H, m), 7.70~7.74 (5H, m), 7.85~7.94 (5H, m), 8.20~8.35 (9H, m), 8.69 (2H, d) |
| 11-95 | δ = 1.31 (3H, t), 4.12 (2H, q), 7.10~7.27 (14H, m), 7.38 (1H, t), 7.57 (1H, t), 7.64~7.74 (5H, m), 7.85~7.96 (7H, m), 8.20 (1H, d), 8.24 (1H, d), 8.69 (2H, d) |
| 11-98 | δ = 7.10~7.26 (10H, m), 7.38 (1H, t), 7.57 (1H, t), 7.70~7.74 (3H, m), 7.84~7.94 (9H, m), 8.20 (1H, d), 8.24 (1H, d), 8.69 (2H, d) |
| 11-99 | δ = 6.90 (1H, t), 7.10~7.26 (11H, m), 7.37~7.39 (2H, m), 7.57 (1H, t), 7.70~7.74 (3H, m), 7.85 (1H, t), 7.88 (1H, s), 7.94 (1H, d), 8.20 (1H, d), 8.24 (1H, d), 8.37 (1H, d), 8.68~8.70 (4H, m) |
| 11-100 | δ = 6.86 (1H, t), 7.10~7.28 (13H, m), 7.38 (1H, t), 7.47~7.50 (4H, m), 7.57 (1H, t), 7.70~7.74 (3H, m), 7.85 (1H, t), 7.88 (1H, s), 7.94 (1H, d), 8.20 (1H, d), 8.24 (1H, d), 8.30 (2H, d), 8.48 (1H, d), 8.69 (2H, d) |
| 12-1 | δ = 7.10~7.26 (10H, m), 7.37~7.41 (6H, m), 7.55~7.75 (10H, m), 7.85 (1H, t), 7.94 (1H, d), 8.20~8.24 (6H, m), 8.32~8.34 (2H, m) |
| 12-3 | δ = 7.10~7.26 (10H, m), 7.38 (1H, t), 7.48~7.54 (7H, m), 7.57 (1H, t), 7.70~7.94 (11H, m), 8.20 (1H, d), 8.24 (1H, d), 8.48 (1H, d), 8.52 (1H, s) |
| 12-5 | δ = 7.16~7.73 (29H, m), 7.85 (1H, t), 7.93~7.95 (3H, m), 8.17~8.24 (6H, m), 8.32~8.24 (2H, m), 8.55 (2H, d) |
| 12-6 | δ = 7.10~7.26 (10H, m), 7.38 (1H, t), 7.46~7.50 (7H, m), 7.57 (1H, t), 7.70~7.75 (4H, m), 7.85 (1H, t), 7.94 (1H, d), 8.20 (1H, d), 8.24 (1H, d), 8.33~8.38 (7H, m) |
| 12-12 | δ = 7.10~7.26 (10H, m), 7.38 (1H, t), 7.49~7.57 (8H, m), 7.70~7.75 (4H, m), 7.85 (1H, t), 7.92~7.96 (4H, m), 8.20~8.24 (3H, m), 8.33~8.35 (4H, m) |
| 12-13 | δ = 7.10~7.26 (10H, m), 7.38~7.50 (8H, m), 7.57 (1H, t), 7.70~7.75 (6H, m), 7.85~7.94 (5H, m), 8.20~8.35 (9H, m) |
| 12-37 | δ = 1.31 (3H, t), 4.12 (2H, q), 7.10~7.27 (14H, m), 7.38 (1H, t), 7.46 (1H, d), 7.57~7.73 (8H, m), 7.85 (1H, t), 7.94~7.96 (3H, m), 8.20 (1H, d), 8.24 (1H, d), 8.32~8.34 (2H, m) |

TABLE 1-continued

| Compound | $^1H$ NMR ($CDCl_3$, 200 Mz) |
|---|---|
| 12-46 | δ = 7.10~7.26 (10H, m), 7.38 (1H, t), 7.46 (1H, d), 7.57 (1H, t), 7.61 (1H, d), 7.70~7.75 (4H, m), 7.84~7.85 (5H, m), 7.94 (1H, d), 8.20 (1H, d), 8.24 (1H, d), 8.32~8.34 (2H, m) |
| 12-48 | δ = 6.90 (1H, t), 7.10~7.26 (11H, m), 7.37~7.39 (2H, m), 7.46 (1H, d), 7.57 (1H, t), 7.70~7.75 (4H, m), 7.85 (1H, t), 7.94 (1H, d), 8.20 (1H, d), 8.24 (1H, d), 8.33~8.37 (3H, m), 8.72 (1H, s) |
| 12-49 | δ = 6.86 (1H, t), 7.10~7.28 (13H, m), 7.38 (1H, t), 7.46~7.50 (5H, m), 7.57 (1H, t), 7.70~7.75 (4H, m), 7.85 (1H, t), 7.73~7.95 (2H, m), 8.20 (1H, d), 8.24 (1H, d), 8.32~8.34 (2H, m), 8.48 (1H, d) |
| 12-51 | δ = 7.10~7.46 (19H, m), 7.55~7.75 (8H, m), 7.85 (1H, t), 7.94 (1H, d), 8.20~8.24 (6H, m), 8.69 (2H, d) |
| 12-53 | δ 7.10~7.26 (10H, m), 7.38 (1H, t), 7.46~7.51 (7H, m), 7.57 (1H, t), 7.70~7.77 (7H, m), 7.85 (1H, t), 7.94~7.96 (3H, m), 8.20 (1H, d), 8.24 (1H, d), 8.36 (2H, d) |
| 12-55 | δ = 7.10~7.38 (17H, m), 7.46~7.60 (7H, m), 7.70~7.75 (3H, m), 7.85~7.94 (6H, m), 8.17~8.24 (6H, m), 8.55 (2H, d), 8.69 (2H, d) |
| 12-56 | δ = 7.10~7.26 (10H, m), 7.38 (1H, t), 7.46~7.50 (7H, m), 7.57 (1H, t), 7.70~7.75 (3H, m), 7.85 (1H, t), 7.94~7.96 (3H, m), 8.20 (1H, d), 8.24 (1H, d), 8.35~8.37 (4H, m), 8.69 (2H, d) |
| 12-62 | δ = 7.10~7.26 (10H, m), 7.38 (1H, t), 7.46~7.57 (8H, m), 7.70~7.75 (3H, m), 7.85 (1H, t), 7.93~7.95 (3H, m), 8.20~8.35 (7H, m), 8.69 (2H, d) |
| 12-63 | δ = 7.10~7.26 (10H, m), 7.38~7.57 (9H, m), 7.70~7.75 (5H, m), 7.84~7.86 (3H, m), 7.94 (1H, d), 8.20~8.35 (9H, m), 8.69 (2H, d) |
| 12-87 | δ = 1.31 (3H, t), 4.12 (2H, q), 7.10~7.27 (14H, m), 7.38 (1H, t), 7.46 (1H, d), 7.57 (1H, t), 7.64~7.75 (5H, m), 7.84~7.86 (3H, m), 7.94~7.96 (3H, m), 8.20 (1H, d), 8.24 (1H, d), 8.69 (2H, d) |
| 12-96 | δ = 7.10~7.26 (10H, m), 7.38 (1H, t), 7.46 (1H, d), 7.57 (1H, t), 7.70~7.75 (3H, m), 7.84~7.85 (7H, m), 7.94 (1H, d), 8.20 (1H, d), 8.24 (1H, d), 8.69 (2H, d) |
| 12-98 | δ = 6.90 (1H, t), 7.10~7.26 (11H, m), 7.37~7.39 (2H, m), 7.46 (1H, d), 7.57 (1H, t), 7.70~7.75 (3H, m), 7.85 (1H, t), 7.94 (1H, d), 8.20 (1H, d), 8.24 (1H, d), 8.37 (1H, d), 8.68~8.70 (4H, m) |
| 12-99 | δ = 6.86 (1H, t), 7.10~7.28 (13H, m), 7.38 (1H, t), 7.46~7.50 (5H, m), 7.57 (1H, t), 7.70~7.75 (3H, m), 7.85 (1H, t), 7.94 (1H, d), 8.20 (1H, d), 8.24 (1H, d), 8.30 (2H, d), 8.48 (1H, d), 8.69 (2H, d) |

TABLE 2

| Compound | FD-MS | Compound | FD-MS |
|---|---|---|---|
| 1-1 | m/z = 651.24 (C46H29N5 = 651.77) | 1-2 | m/z = 700.26 (C51H32N4 = 700.84) |
| 1-3 | m/z = 726.28 (C53H34N4 = 726.88) | 1-4 | m/z = 650.25 (C47H30N4 = 650.78) |
| 1-5 | m/z = 739.27 (C53H33N5 = 739.88) | 1-6 | m/z = 547.20 (C40H25N3 = 547.66) |
| 1-7 | m/z = 586.22 (C42H26N4 = 586.70) | 1-8 | m/z = 688.26 (C50H32N4 = 688.83) |
| 1-9 | m/z = 650.25 (C47H30N4 = 650.78) | 1-10 | m/z = 620.20 (C43H29N2OP = 620.69) |
| 1-11 | m/z = 688.26 (C50H32N4 = 688.83) | 1-12 | m/z = 826.31 (C61H38N4 = 870.00) |
| 1-13 | m/z = 596.23 (C45H28N2 = 596.73) | 1-14 | m/z = 672.26 (C51H32N2 = 672.83) |
| 1-15 | m/z = 722.27 (C55H34N2 = 722.89) | 1-16 | m/z = 629.19 (C44H27N3S = 629.78) |
| 1-17 | m/z = 547.20 (C40H25N3 = 547.66) | 1-18 | m/z = 548.20 (C39H24N4 = 548.65) |
| 1-19 | m/z = 736.29 (C56H36N2 = 736.92) | 1-20 | m/z = 613.22 (C44H27N3O = 613.72) |
| 1-21 | m/z = 640.23 (C45H28N4O = 640.75) | 1-22 | m/z = 586.20 (C43H26N2O = 586.69) |
| 1-23 | m/z = 602.18 (C43H26N2S = 602.75) | 1-24 | m/z = 649.25 (C48H31N3 = 649.80) |
| 1-25 | m/z = 649.25 (C48H31N3 = 649.80) | 1-26 | m/z = 803.30 (C58H37N5 = 803.97) |
| 1-27 | m/z = 803.30 (C58H37N5 = 803.97) | 1-28 | m/z = 749.28 (C56H35N3 = 749.92) |
| 1-29 | m/z = 646.24 (C49H30N2 = 646.79) | 1-30 | m/z = 739.30 (C55H37N3 = 739.92) |
| 1-31 | m/z = 750.28 (C55H34N4 = 750.90) | 1-32 | m/z = 750.28 (C55H34N4 = 750.90) |
| 1-33 | m/z = 661.25 (C49H31N3 = 661.82) | 1-34 | m/z = 661.25 (C49H31N3 = 661.82) |
| 1-35 | m/z = 804.33 (C59H40N4 = 805.00) | 1-36 | m/z = 602.25 (C43H30N4 = 602.74) |
| 1-37 | m/z = 651.27 (C48H33N3 = 651.82) | 1-38 | m/z = 677.28 (C50H35N3 = 677.85) |
| 1-39 | m/z = 601.25 (C44H31N3 = 601.75) | 1-40 | m/z = 690.28 (C50H34N4 = 690.85) |
| 1-41 | m/z = 498.21 (C37H26N2 = 498.63) | 1-42 | m/z = 537.22 (C39H27N3 = 537.67) |
| 1-43 | m/z = 639.27 (C47H33N3 = 639.80) | 1-44 | m/z = 601.25 (C44H31N3 = 601.75) |
| 1-45 | m/z = 571.22 (C40H30NPO = 571.66) | 1-46 | m/z = 639.27 (C47H33N3 = 639.80) |
| 1-47 | m/z = 779.33 (C58H41N3 = 779.99) | 1-48 | m/z = 547.23 (C42H29N = 547.70) |
| 1-49 | m/z = 623.26 (C48H33N = 623.80) | 1-50 | m/z = 690.30 (C52H38N2 = 690.89) |
| 1-51 | m/z = 701.28 (C52H35N3 = 701.87) | 1-52 | m/z = 553.19 (C40H27NS = 553.72) |
| 1-53 | m/z = 648.26 (C49H32N2 = 648.81) | 1-54 | m/z = 601.25 (C44H31N3 = 601.75) |
| 1-55 | m/z = 498.21 (C37H26N2 = 498.63) | 1-56 | m/z = 592.17 (C40H24N4S = 592.72) |
| 1-57 | m/z = 641.19 (C45H27N3S = 641.79) | 1-58 | m/z = 667.21 (C47H29N3S = 667.83) |
| 1-59 | m/z = 591.18 (C41H25N3S = 591.73) | 1-60 | m/z = 680.20 (C47H28N4S = 680.83) |
| 1-61 | m/z = 488.13 (C34H20N2S = 488.61) | 1-62 | m/z = 527.15 (C36H21N3S = 527.64) |
| 1-63 | m/z = 629.19 (C44H27N3S = 629.78) | 1-64 | m/z = 519.18 (C41H25N3S = 519.73) |
| 1-65 | m/z = 561.13 (C37H24NOPS = 561.64) | 1-66 | m/z = 629.19 (C44H27N3S = 692.78) |
| 1-67 | m/z = 769.26 (C55H35N3S = 769.97) | 1-68 | m/z = 537.16 (C39H23NS = 537.68) |
| 1-69 | m/z = 613.19 (C45H27NS = 613.78) | 1-70 | m/z = 680.23 (C49H32N2S = 680.87) |
| 1-71 | m/z = 691.21 (C49H29N3S = 691.85) | 1-72 | m/z = 543.11 (C37H21NS2 = 543.70) |

TABLE 2-continued

| Compound | FD-MS | Compound | FD-MS |
|---|---|---|---|
| 1-73 | m/z = 638.18 (C46H26N2S = 638.79) | 1-74 | m/z = 591.18 (C41H25N3S = 591.73) |
| 1-75 | m/z = 488.13 (C34H20N2S = 488.61) | 1-76 | m/z = 576.20 (C40H24N4 = 576.66) |
| 1-77 | m/z = 625.22 (C45H27N3O = 625.73) | 1-78 | m/z = 651.23 (C47H29N3O = 651.77) |
| 1-79 | m/z = 575.20 (C41H25N3O = 575.67) | 1-80 | m/z = 664.23 (C47H28N4O = 664.77) |
| 1-81 | m/z = 472.16 (C34H20N2O = 472.55) | 1-82 | m/z = 511.17 (C36H21N3O = 511.58) |
| 1-83 | m/z = 613.22 (C44H27N3O = 613.72) | 1-84 | m/z = 575.20 (C41H25N3O = 575.67) |
| 1-85 | m/z = 545.15 (C37H24NO2P = 545.58) | 1-86 | m/z = 613.22 (C44H27N3O = 613.72) |
| 1-87 | m/z = 753.28 (C55H35N3O = 735.90) | 1-88 | m/z = 521.18 (C39H23NO = 521.62) |
| 1-89 | m/z = 597.21 (C45H27NO = 597.72) | 1-90 | m/z = 664.25 (C49H32N2O = 664.81) |
| 1-91 | m/z = 651.24 (C46H29N5 = 651.77) | 1-92 | m/z = 700.26 (C51H32N4 = 700.84) |
| 1-93 | m/z = 726.28 (C53H34N4 = 726.88) | 1-94 | m/z = 650.25 (C47H30N4 = 650.78) |
| 1-95 | m/z = 739.27 (C53H33N5 = 739.88) | 1-96 | m/z = 547.20 (C40H25N3 = 547.66) |
| 1-97 | m/z = 586.22 (C42H26N4 = 586.70) | 1-98 | m/z = 688.26 (C50H32N4 = 688.83) |
| 1-99 | m/z = 650.25 (C47H30N4 = 650.78) | 1-100 | m/z = 620.20 (C43H29N2OP = 620.69) |
| 1-101 | m/z = 688.26 (C50H32N4 = 688.83) | 1-102 | m/z = 826.31 (C61H38N4 = 870.00) |
| 1-103 | m/z = 596.23 (C45H28N2 = 596.73) | 1-104 | m/z = 672.26 (C51H32N2 = 672.83) |
| 1-105 | m/z = 722.27 (C55H34N2 = 722.89) | 1-106 | m/z = 629.19 (C44H27N3S = 629.78) |
| 1-107 | m/z = 547.20 (C40H25N3 = 547.66) | 1-108 | m/z = 548.20 (C39H24N4 = 548.65) |
| 1-109 | m/z = 736.29 (C56H36N2 = 736.92) | 1-110 | m/z = 613.22 (C44H27N3O = 613.72) |
| 1-111 | m/z = 640.23 (C45H28N4O = 640.75) | 1-112 | m/z = 586.20 (C43H26N2O = 586.69) |
| 1-113 | m/z = 602.18 (C43H26N2S = 602.75) | 1-114 | m/z = 649.25 (C48H31N3 = 649.80) |
| 1-115 | m/z = 649.25 (C48H31N3 = 649.80) | 1-116 | m/z = 803.30 (C58H37N5 = 803.97) |
| 1-117 | m/z = 803.30 (C58H37N5 = 803.97) | 1-118 | m/z = 749.28 (C56H35N3 = 749.92) |
| 1-119 | m/z = 646.24 (C49H30N2 = 646.79) | 1-120 | m/z = 739.30 (C55H37N3 = 739.92) |
| 1-121 | m/z = 750.28 (C55H34N4 = 750.90) | 1-122 | m/z = 750.28 (C55H34N4 = 750.90) |
| 1-123 | m/z = 661.25 (C49H31N3 = 661.82) | 1-124 | m/z = 661.25 (C49H31N3 = 661.82) |
| 1-125 | m/z = 804.33 (C59H40N4 = 805.00) | 1-126 | m/z = 602.25 (C43H30N4 = 602.74) |
| 1-127 | m/z = 651.27 (C48H33N3 = 651.82) | 1-128 | m/z = 677.28 (C50H35N3 = 677.85) |
| 1-129 | m/z = 601.25 (C44H31N3 = 601.75) | 1-130 | m/z = 690.28 (C50H34N4 = 690.85) |
| 1-131 | m/z = 498.21 (C37H26N2 = 498.63) | 1-132 | m/z = 537.22 (C39H27N3 = 537.67) |
| 1-133 | m/z = 639.27 (C47H33N3 = 639.80) | 1-134 | m/z = 601.25 (C44H31N3 = 601.75) |
| 1-135 | m/z = 571.22 (C40H30NPO = 571.66) | 1-136 | m/z = 639.27 (C47H33N3 = 639.80) |
| 1-137 | m/z = 779.33 (C58H41N3 = 779.99) | 1-138 | m/z = 547.23 (C42H29N = 547.70) |
| 1-139 | m/z = 623.26 (C48H33N = 623.80) | 1-140 | m/z = 690.30 (C52H38N2 = 690.89) |
| 1-141 | m/z = 701.28 (C52H35N3 = 701.87) | 1-142 | m/z = 553.19 (C40H27NS = 553.72) |
| 1-143 | m/z = 648.26 (C49H32N2 = 648.81) | 1-144 | m/z = 601.25 (C44H31N3 = 601.75) |
| 1-145 | m/z = 498.21 (C37H26N2 = 498.63) | 1-146 | m/z = 592.17 (C40H24N4S = 592.72) |
| 1-147 | m/z = 641.19 (C45H27N3S = 641.79) | 1-148 | m/z = 667.21 (C47H29N3S = 667.83) |
| 1-149 | m/z = 591.18 (C41H25N3S = 591.73) | 1-150 | m/z = 680.20 (C47H28N4S = 680.83) |
| 1-151 | m/z = 488.13 (C34H20N2S = 488.61) | 1-152 | m/z = 527.15 (C36H21N3S = 527.64) |
| 1-153 | m/z = 629.19 (C44H27N3S = 629.78) | 1-154 | m/z = 519.18 (C41H25N3S = 519.73) |
| 1-155 | m/z = 561.13 (C37H24NOPS = 561.64) | 1-156 | m/z = 629.19 (C44H27N3S = 692.78) |
| 1-157 | m/z = 769.26 (C55H35N3S = 769.97) | 1-158 | m/z = 537.16 (C39H23NS = 537.68) |
| 1-159 | m/z = 613.19 (C45H27NS = 613.78) | 1-160 | m/z = 680.23 (C49H32N2S = 680.87) |
| 1-161 | m/z = 691.21 (C49H29N3S = 691.85) | 1-162 | m/z = 543.11 (C37H21NS2 = 543.70) |
| 1-163 | m/z = 638.18 (C46H26N2S = 638.79) | 1-164 | m/z = 591.18 (C41H25N3S = 591.73) |
| 1-165 | m/z = 488.13 (C34H20N2S = 488.61) | 1-166 | m/z = 576.20 (C40H24N4 = 576.66) |
| 1-167 | m/z = 625.22 (C45H27N3O = 625.73) | 1-168 | m/z = 651.23 (C47H29N3O = 651.77) |
| 1-169 | m/z = 575.20 (C41H25N3O = 575.67) | 1-170 | m/z = 664.23 (C47H28N4O = 664.77) |
| 1-171 | m/z = 472.16 (C34H20N2O = 472.55) | 1-172 | m/z = 511.17 (C36H21N3O = 511.58) |
| 1-173 | m/z = 613.22 (C44H27N3O = 613.72) | 1-174 | m/z = 575.20 (C41H25N3O = 575.67) |
| 1-175 | m/z = 545.15 (C37H24NO2P = 545.58) | 1-176 | m/z = 613.22 (C44H27N3O = 613.72) |
| 1-177 | m/z = 753.28 (C55H35N3O = 735.90) | 1-178 | m/z = 521.18 (C39H23NO = 521.62) |
| 1-179 | m/z = 597.21 (C45H27NO = 597.72) | 1-180 | m/z = 664.25 (C49H32N2O = 664.81) |
| 1-181 | m/z = 651.24 (C46H29N5 = 651.77) | 1-182 | m/z = 700.26 (C51H32N4 = 700.84) |
| 1-183 | m/z = 726.28 (C53H34N4 = 726.88) | 1-184 | m/z = 650.25 (C47H30N4 = 650.78) |
| 1-185 | m/z = 739.27 (C53H33N5 = 739.88) | 1-186 | m/z = 547.20 (C40H25N3 = 547.66) |
| 1-187 | m/z = 586.22 (C42H26N4 = 586.70) | 1-188 | m/z = 688.26 (C50H32N4 = 688.83) |
| 1-189 | m/z = 650.25 (C47H30N4 = 650.78) | 1-190 | m/z = 620.20 (C43H29N2OP = 620.69) |
| 1-191 | m/z = 688.26 (C50H32N4 = 688.83) | 1-192 | m/z = 826.31 (C61H38N4 = 827.00) |
| 1-193 | m/z = 596.23 (C45H28N2 = 596.73) | 1-194 | m/z = 672.26 (C51H32N2 = 672.83) |
| 1-195 | m/z = 722.27 (C55H34N2 = 722.89) | 1-196 | m/z = 629.19 (C44H27N3S = 629.78) |
| 1-197 | m/z = 547.20 (C40H25N3 = 547.66) | 1-198 | m/z = 548.20 (C39H24N4 = 548.65) |
| 1-199 | m/z = 736.29 (C56H36N2 = 736.92) | 1-200 | m/z = 613.22 (C44H27N3O = 613.72) |
| 1-201 | m/z = 640.23 (C45H28N4O = 640.75) | 1-202 | m/z = 586.20 (C43H26N2O = 586.69) |
| 1-203 | m/z = 602.18 (C43H26N2S = 602.75) | 1-204 | m/z = 649.25 (C48H31N3 = 649.80) |
| 1-205 | m/z = 649.25 (C48H31N3 = 649.80) | 1-206 | m/z = 803.30 (C58H37N5 = 803.97) |
| 1-207 | m/z = 803.30 (C58H37N5 = 803.97) | 1-208 | m/z = 749.28 (C56H35N3 = 749.92) |
| 1-209 | m/z = 646.24 (C49H30N2 = 646.79) | 1-210 | m/z = 739.30 (C55H37N3 = 739.92) |
| 1-211 | m/z = 750.28 (C55H34N4 = 750.90) | 1-212 | m/z = 750.28 (C55H34N4 = 750.90) |
| 1-213 | m/z = 661.25 (C49H31N3 = 661.81) | 1-214 | m/z = 661.25 (C49H31N3 = 661.81) |
| 1-215 | m/z = 804.33 (C59H40N4 = 805.00) | 1-216 | m/z = 651.24 (C46H29N5 = 651.77) |
| 1-217 | m/z = 700.26 (C51H32N4 = 700.84) | 1-218 | m/z = 726.28 (C53H34N4 = 726.88) |
| 1-219 | m/z = 650.25 (C47H30N4 = 650.78) | 1-220 | m/z = 739.27 (C53H33N5 = 739.88) |
| 1-221 | m/z = 547.20 (C40H25N3 = 547.66) | 1-222 | m/z = 586.22 (C42H26N4 = 586.70) |
| 1-223 | m/z = 688.26 (C50H32N4 = 688.83) | 1-224 | m/z = 650.25 (C47H30N4 = 650.78) |
| 1-225 | m/z = 620.20 (C43H29N2OP = 620.69) | 1-226 | m/z = 688.26 (C50H32N4 = 688.83) |
| 1-227 | m/z = 826.31 (C61H38N4 = 827.00) | 1-228 | m/z = 596.23 (C45H28N2 = 596.73) |

TABLE 2-continued

| Compound | FD-MS | Compound | FD-MS |
|---|---|---|---|
| 1-229 | m/z = 672.26 ($C_{51}H_{32}N_2$ = 672.83) | 1-230 | m/z = 722.27 ($C_{55}H_{34}N_2$ = 722.89) |
| 1-231 | m/z = 629.19 ($C_{44}H_{27}N_3S$ = 629.78) | 1-232 | m/z = 547.20 ($C_{40}H_{25}N_3$ = 547.66) |
| 1-233 | m/z = 548.20 ($C_{39}H_{24}N_4$ = 548.65) | 1-234 | m/z = 736.29 ($C_{56}H_{36}N_2$ = 736.92) |
| 1-235 | m/z = 613.22 ($C_{44}H_{27}N_3O$ = 613.72) | 1-236 | m/z = 640.23 ($C_{45}H_{28}N_4O$ = 640.75) |
| 1-237 | m/z = 586.20 ($C_{43}H_{26}N_2O$ = 586.69) | 1-238 | m/z = 602.18 ($C_{43}H_{26}N_2S$ = 602.75) |
| 1-239 | m/z = 649.25 ($C_{48}H_{31}N_3$ = 649.80) | 1-240 | m/z = 649.25 ($C_{48}H_{31}N_3$ = 649.80) |
| 1-241 | m/z = 803.30 ($C_{58}H_{37}N_5$ = 803.97) | 1-242 | m/z = 803.30 ($C_{58}H_{37}N_5$ = 803.97) |
| 1-243 | m/z = 749.28 ($C_{56}H_{35}N_3$ = 749.92) | 1-244 | m/z = 646.24 ($C_{49}H_{30}N_2$ = 646.79) |
| 1-245 | m/z = 739.30 ($C_{55}H_{37}N_3$ = 739.92) | 1-246 | m/z = 750.28 ($C_{55}H_{34}N_4$ = 750.90) |
| 1-247 | m/z = 750.28 ($C_{55}H_{34}N_4$ = 750.90) | 1-248 | m/z = 661.25 ($C_{49}H_{31}N_3$ = 661.81) |
| 1-249 | m/z = 661.25 ($C_{49}H_{31}N_3$ = 661.81) | 1-250 | m/z = 804.33 ($C_{59}H_{40}N_4$ = 805.00) |
| 1-251 | m/z = 848.32 ($C_{65}H_{40}N_2$ = 849.05) | 1-252 | m/z = 848.32 ($C_{65}H_{40}N_2$ = 849.05) |
| 1-253 | m/z = 722.27 ($C_{55}H_{34}N_2$ = 722.89) | 1-254 | m/z = 672.26 ($C_{51}H_{32}N_2$ = 672.83) |
| 1-255 | m/z = 696.23 ($C_{49}H_{33}N_2OP$ = 696.79) | 1-256 | m/z = 653.23 ($C_{44}H_{27}N_7$ = 653.75) |
| 1-257 | m/z = 653.23 ($C_{44}H_{27}N_7$ = 653.75) | 1-258 | m/z = 653.23 ($C_{44}H_{27}N_7$ = 653.75) |
| 1-259 | m/z = 751.27 ($C_{54}H_{33}N_5$ = 751.89) | 1-260 | m/z = 751.27 ($C_{54}H_{33}N_5$ = 751.89) |
| 1-261 | m/z = 851.30 ($C_{62}H_{37}N_5$ = 852.01) | 1-262 | m/z = 727.27 ($C_{52}H_{33}N_5$ = 727.87) |
| 1-263 | m/z = 729.26 ($C_{50}H_{31}N_7$ = 729.85) | 1-264 | m/z = 729.26 ($C_{50}H_{31}N_7$ = 729.85) |
| 1-265 | m/z = 729.26 ($C_{50}H_{31}N_7$ = 729.85) | 1-266 | m/z = 827.30 ($C_{60}H_{37}N_5$ = 827.99) |
| 1-267 | m/z = 827.30 ($C_{60}H_{37}N_5$ = 827.99) | 1-268 | m/z = 927.34 ($C_{68}H_{41}N_5$ = 928.11) |
| 1-269 | m/z = 750.28 ($C_{55}H_{34}N_4$ = 750.90) | 1-270 | m/z = 750.28 ($C_{55}H_{34}N_4$ = 750.90) |
| 1-271 | m/z = 850.31 ($C_{63}H_{38}N_4$ = 851.02) | 1-272 | m/z = 802.31 ($C_{59}H_{38}N_4$ = 802.98) |
| 1-273 | m/z = 726.28 ($C_{53}H_{34}N_4$ = 726.88) | 1-274 | m/z = 802.31 ($C_{59}H_{38}N_4$ = 802.98) |
| 1-275 | m/z = 726.28 ($C_{53}H_{34}N_4$ = 726.88) | 1-276 | m/z = 726.28 ($C_{53}H_{34}N_4$ = 726.88) |
| 1-277 | m/z = 826.31 ($C_{61}H_{38}N_4$ = 827.00) | 1-278 | m/z = 826.31 ($C_{61}H_{38}N_4$ = 827.00) |
| 1-279 | m/z = 926.34 ($C_{69}H_{42}N_4$ = 927.12) | 1-280 | m/z = 878.34 ($C_{65}H_{42}N_4$ = 879.08) |
| 1-281 | m/z = 802.31 ($C_{59}H_{38}N_4$ = 802.98) | 1-282 | m/z = 878.34 ($C_{65}H_{42}N_4$ = 879.08) |
| 1-283 | m/z = 802.31 ($C_{59}H_{38}N_4$ = 802.98) | 1-284 | m/z = 750.28 ($C_{55}H_{34}N_4$ = 750.90) |
| 1-285 | m/z = 750.28 ($C_{55}H_{34}N_4$ = 750.90) | 1-286 | m/z = 848.32 ($C_{65}H_{40}N_2$ = 849.05) |
| 1-287 | m/z = 802.31 ($C_{59}H_{38}N_4$ = 802.98) | 1-288 | m/z = 726.28 ($C_{53}H_{34}N_4$ = 726.88) |
| 1-289 | m/z = 802.31 ($C_{59}H_{38}N_4$ = 802.98) | 1-290 | m/z = 726.28 ($C_{53}H_{34}N_4$ = 726.88) |
| 1-291 | m/z = 651.24 ($C_{46}H_{29}N_5$ = 651.77) | 1-292 | m/z = 727.27 ($C_{52}H_{33}N_5$ = 727.87) |
| 1-293 | m/z = 726.28 ($C_{53}H_{34}N_4$ = 726.88) | 1-294 | m/z = 726.28 ($C_{53}H_{34}N_4$ = 726.88) |
| 1-295 | m/z = 651.24 ($C_{46}H_{29}N_5$ = 651.77) | 1-296 | m/z = 826.31 ($C_{61}H_{38}N_4$ = 827.00) |
| 1-297 | m/z = 826.31 ($C_{61}H_{38}N_4$ = 827.00) | 1-298 | m/z = 926.34 ($C_{69}H_{42}N_4$ = 927.12) |
| 1-299 | m/z = 878.34 ($C_{65}H_{42}N_4$ = 879.08) | 1-300 | m/z = 802.31 ($C_{59}H_{38}N_4$ = 802.98) |
| 1-301 | m/z = 802.31 ($C_{59}H_{38}N_4$ = 802.98) | 1-302 | m/z = 878.34 ($C_{65}H_{42}N_4$ = 879.08) |
| 1-303 | m/z = 802.31 ($C_{59}H_{38}N_4$ = 802.98) | 1-304 | m/z = 802.31 ($C_{59}H_{38}N_4$ = 802.98) |
| 1-305 | m/z = 727.27 ($C_{52}H_{33}N_5$ = 727.87) | 1-306 | m/z = 803.30 ($C_{58}H_{37}N_5$ = 803.97) |
| 1-307 | m/z = 803.30 ($C_{58}H_{37}N_5$ = 803.97) | 1-308 | m/z = 700.26 ($C_{51}H_{32}N_4$ = 700.84) |
| 1-309 | m/z = 776.29 ($C_{57}H_{36}N_4$ = 776.94) | 1-310 | m/z = 624.23 ($C_{45}H_{28}N_4$ = 624.75) |
| 1-311 | m/z = 700.26 ($C_{51}H_{32}N_4$ = 700.84) | 1-312 | m/z = 674.25 ($C_{49}H_{30}N_4$ = 674.81) |
| 1-313 | m/z = 674.25 ($C_{49}H_{30}N_4$ = 674.81) | 1-314 | m/z = 700.26 ($C_{51}H_{32}N_4$ = 700.84) |
| 1-315 | m/z = 776.29 ($C_{57}H_{36}N_4$ = 776.94) | 1-316 | m/z = 750.28 ($C_{55}H_{34}N_4$ = 750.90) |
| 1-317 | m/z = 750.28 ($C_{55}H_{34}N_4$ = 750.90) | 1-318 | m/z = 726.28 ($C_{53}H_{34}N_4$ = 726.88) |
| 1-319 | m/z = 878.34 ($C_{65}H_{42}N_4$ = 879.08) | 1-320 | m/z = 878.34 ($C_{65}H_{42}N_4$ = 879.08) |
| 1-321 | m/z = 826.31 ($C_{61}H_{38}N_4$ = 827.00) | 1-322 | m/z = 826.31 ($C_{61}H_{38}N_4$ = 827.00) |
| 1-323 | m/z = 802.31 ($C_{59}H_{38}N_4$ = 802.98) | 1-324 | m/z = 802.31 ($C_{59}H_{38}N_4$ = 802.98) |
| 1-325 | m/z = 776.29 ($C_{57}H_{36}N_4$ = 776.94) | 1-326 | m/z = 776.29 ($C_{57}H_{36}N_4$ = 776.94) |
| 1-327 | m/z = 826.31 ($C_{61}H_{38}N_4$ = 827.00) | 1-328 | m/z = 624.23 ($C_{45}H_{28}N_4$ = 624.75) |
| 1-329 | m/z = 700.26 ($C_{51}H_{32}N_4$ = 700.84) | 1-330 | m/z = 700.26 ($C_{51}H_{32}N_4$ = 700.84) |
| 1-331 | m/z = 700.26 ($C_{51}H_{32}N_4$ = 700.84) | 1-332 | m/z = 776.29 ($C_{57}H_{36}N_4$ = 776.94) |
| 1-333 | m/z = 776.29 ($C_{57}H_{36}N_4$ = 776.94) | 1-334 | m/z = 598.22 ($C_{43}H_{26}N_4$ = 598.71) |
| 1-335 | m/z = 674.25 ($C_{49}H_{30}N_4$ = 674.81) | 1-336 | m/z = 674.25 ($C_{49}H_{30}N_4$ = 674.81) |
| 1-337 | m/z = 612.23 ($C_{44}H_{28}N_4$ = 612.74) | 1-338 | m/z = 612.23 ($C_{44}H_{28}N_4$ = 612.74) |
| 1-339 | m/z = 612.23 ($C_{44}H_{28}N_4$ = 612.74) | 1-340 | m/z = 612.23 ($C_{44}H_{28}N_4$ = 612.74) |
| 1-341 | m/z = 564.23 ($C_{40}H_{28}N_4$ = 564.69) | 1-342 | m/z = 640.26 ($C_{46}H_{32}N_4$ = 640.79) |
| 1-343 | m/z = 640.26 ($C_{46}H_{32}N_4$ = 640.79) | 1-344 | m/z = 688.26 ($C_{50}H_{32}N_4$ = 688.83) |
| 1-345 | m/z = 640.26 ($C_{46}H_{32}N_4$ = 640.79) | 1-346 | m/z = 640.26 ($C_{46}H_{32}N_4$ = 640.79) |
| 1-347 | m/z = 564.23 ($C_{40}H_{28}N_4$ = 564.69) | 1-348 | m/z = 688.26 ($C_{50}H_{32}N_4$ = 688.83) |
| 1-349 | m/z = 629.19 ($C_{44}H_{27}N_3S$ = 629.78) | 1-350 | m/z = 629.19 ($C_{44}H_{27}N_3S$ = 629.78) |
| 1-351 | m/z = 629.19 ($C_{44}H_{27}N_3S$ = 629.78) | 1-352 | m/z = 629.19 ($C_{44}H_{27}N_3S$ = 629.78) |
| 1-353 | m/z = 725.28 ($C_{54}H_{35}N_3$ = 725.89) | 1-354 | m/z = 651.24 ($C_{46}H_{29}N_5$ = 651.77) |
| 1-355 | m/z = 651.24 ($C_{46}H_{29}N_5$ = 651.77) | 1-356 | m/z = 651.24 ($C_{46}H_{29}N_5$ = 651.77) |
| 1-357 | m/z = 727.27 ($C_{52}H_{33}N_5$ = 727.87) | 1-358 | m/z = 727.27 ($C_{52}H_{33}N_5$ = 727.87) |
| 1-359 | m/z = 727.27 ($C_{52}H_{33}N_5$ = 727.87) | 1-360 | m/z = 574.22 ($C_{41}H_{26}N_4$ = 574.69) |
| 1-361 | m/z = 574.22 ($C_{41}H_{26}N_4$ = 574.69) | 1-362 | m/z = 574.22 ($C_{41}H_{26}N_4$ = 574.69) |
| 1-363 | m/z = 650.25 ($C_{47}H_{30}N_4$ = 650.78) | 1-364 | m/z = 650.25 ($C_{47}H_{30}N_4$ = 650.78) |
| 1-365 | m/z = 650.25 ($C_{47}H_{30}N_4$ = 650.78) | 1-366 | m/z = 848.32 ($C_{65}H_{40}N_2$ = 849.05) |
| 1-367 | m/z = 848.32 ($C_{65}H_{40}N_2$ = 849.05) | 1-368 | m/z = 722.27 ($C_{55}H_{34}N_2$ = 722.89) |
| 1-369 | m/z = 672.26 ($C_{51}H_{32}N_2$ = 672.83) | 1-370 | m/z = 696.23 ($C_{49}H_{33}N_2OP$ = 696.79) |
| 1-371 | m/z = 653.23 ($C_{44}H_{27}N_7$ = 653.75) | 1-372 | m/z = 653.23 ($C_{44}H_{27}N_7$ = 653.75) |
| 1-373 | m/z = 653.23 ($C_{44}H_{27}N_7$ = 653.75) | 1-374 | m/z = 751.27 ($C_{54}H_{33}N_5$ = 751.89) |
| 1-375 | m/z = 751.27 ($C_{54}H_{33}N_5$ = 751.89) | 1-376 | m/z = 851.30 ($C_{62}H_{37}N_5$ = 852.01) |
| 1-377 | m/z = 727.27 ($C_{52}H_{33}N_5$ = 727.87) | 1-378 | m/z = 729.26 ($C_{50}H_{31}N_7$ = 729.85) |
| 1-379 | m/z = 729.26 ($C_{50}H_{31}N_7$ = 729.85) | 1-380 | m/z = 729.26 ($C_{50}H_{31}N_7$ = 729.85) |
| 1-381 | m/z = 827.30 ($C_{60}H_{37}N_5$ = 827.99) | 1-382 | m/z = 827.30 ($C_{60}H_{37}N_5$ = 827.99) |
| 1-383 | m/z = 927.34 ($C_{68}H_{41}N_5$ = 928.11) | 1-384 | m/z = 750.28 ($C_{55}H_{34}N_4$ = 750.90) |

TABLE 2-continued

| Compound | FD-MS | Compound | FD-MS |
|---|---|---|---|
| 1-385 | m/z = 750.28 (C55H34N4 = 750.90) | 1-386 | m/z = 850.31 (C63H38N4 = 851.02) |
| 1-387 | m/z = 802.31 (C59H38N4 = 802.98) | 1-388 | m/z = 726.28 (C53H34N4 = 726.88) |
| 1-389 | m/z = 802.31 (C59H38N4 = 802.98) | 1-390 | m/z = 726.28 (C53H34N4 = 726.88) |
| 1-391 | m/z = 726.28 (C53H34N4 = 726.88) | 1-392 | m/z = 826.31 (C61H38N4 = 827.00) |
| 1-393 | m/z = 826.31 (C61H38N4 = 827.00) | 1-394 | m/z = 926.34 (C69H42N4 = 927.12) |
| 1-395 | m/z = 878.34 (C65H42N4 = 879.08) | 1-396 | m/z = 802.31 (C59H38N4 = 802.98) |
| 1-397 | m/z = 878.34 (C65H42N4 = 879.08) | 1-398 | m/z = 802.31 (C59H38N4 = 802.98) |
| 1-399 | m/z = 750.28 (C55H34N4 = 750.90) | 1-400 | m/z = 750.28 (C55H34N4 = 750.90) |
| 1-401 | m/z = 848.32 (C65H40N2 = 849.05) | 1-402 | m/z = 802.31 (C59H38N4 = 802.98) |
| 1-403 | m/z = 726.28 (C53H34N4 = 726.88) | 1-404 | m/z = 802.31 (C59H38N4 = 802.98) |
| 1-405 | m/z = 726.28 (C53H34N4 = 726.88) | 1-406 | m/z = 651.24 (C46H29N5 = 651.77) |
| 1-407 | m/z = 727.27 (C52H33N5 = 727.87) | 1-408 | m/z = 726.28 (C53H34N4 = 726.88) |
| 1-409 | m/z = 726.28 (C53H34N4 = 726.88) | 1-410 | m/z = 651.24 (C46H29N5 = 651.77) |
| 1-411 | m/z = 826.31 (C61H38N4 = 827.00) | 1-412 | m/z = 826.31 (C61H38N4 = 827.00) |
| 1-413 | m/z = 926.34 (C69H42N4 = 927.12) | 1-414 | m/z = 878.34 (C65H42N4 = 879.08) |
| 1-415 | m/z = 802.31 (C59H38N4 = 802.98) | 1-416 | m/z = 802.31 (C59H38N4 = 802.98) |
| 1-417 | m/z = 878.34 (C65H42N4 = 879.08) | 1-418 | m/z = 802.31 (C59H38N4 = 802.98) |
| 1-419 | m/z = 802.31 (C59H38N4 = 802.98) | 1-420 | m/z = 727.27 (C52H33N5 = 727.87) |
| 1-421 | m/z = 803.30 (C58H37N5 = 803.97) | 1-422 | m/z = 803.30 (C58H37N5 = 803.97) |
| 1-423 | m/z = 700.26 (C51H32N4 = 700.84) | 1-424 | m/z = 776.29 (C57H36N4 = 776.94) |
| 1-425 | m/z = 624.23 (C45H28N4 = 624.75) | 1-426 | m/z = 700.26 (C51H32N4 = 700.84) |
| 1-427 | m/z = 674.25 (C49H30N4 = 674.81) | 1-428 | m/z = 674.25 (C49H30N4 = 674.81) |
| 1-429 | m/z = 700.26 (C51H32N4 = 700.84) | 1-430 | m/z = 776.29 (C57H36N4 = 776.94) |
| 1-431 | m/z = 750.28 (C55H34N4 = 750.90) | 1-432 | m/z = 750.28 (C55H34N4 = 750.90) |
| 1-433 | m/z = 726.28 (C53H34N4 = 726.88) | 1-434 | m/z = 878.34 (C65H42N4 = 879.08) |
| 1-435 | m/z = 878.34 (C65H42N4 = 879.08) | 1-436 | m/z = 826.31 (C61H38N4 = 827.00) |
| 1-437 | m/z = 826.31 (C61H38N4 = 827.00) | 1-438 | m/z = 802.31 (C59H38N4 = 802.98) |
| 1-439 | m/z = 802.31 (C59H38N4 = 802.98) | 1-440 | m/z = 776.29 (C57H36N4 = 776.94) |
| 1-441 | m/z = 776.29 (C57H36N4 = 776.94) | 1-442 | m/z = 826.31 (C61H38N4 = 827.00) |
| 1-443 | m/z = 624.23 (C45H28N4 = 624.75) | 1-444 | m/z = 700.26 (C51H32N4 = 700.84) |
| 1-445 | m/z = 700.26 (C51H32N4 = 700.84) | 1-446 | m/z = 700.26 (C51H32N4 = 700.84) |
| 1-447 | m/z = 776.29 (C57H36N4 = 776.94) | 1-448 | m/z = 776.29 (C57H36N4 = 776.94) |
| 1-449 | m/z = 598.22 (C43H26N4 = 598.71) | 1-450 | m/z = 674.25 (C49H30N4 = 674.81) |
| 1-451 | m/z = 674.25 (C49H30N4 = 674.81) | 1-452 | m/z = 612.23 (C44H28N4 = 612.74) |
| 1-453 | m/z = 612.23 (C44H28N4 = 612.74) | 1-454 | m/z = 612.23 (C44H28N4 = 612.74) |
| 1-455 | m/z = 612.23 (C44H28N4 = 612.74) | 1-456 | m/z = 564.23 (C40H28N4 = 564.69) |
| 1-457 | m/z = 640.26 (C46H32N4 = 640.79) | 1-458 | m/z = 640.26 (C46H32N4 = 640.79) |
| 1-459 | m/z = 688.26 (C50H32N4 = 688.83) | 1-460 | m/z = 640.26 (C46H32N4 = 640.79) |
| 1-461 | m/z = 640.26 (C46H32N4 = 640.79) | 1-462 | m/z = 564.23 (C40H28N4 = 564.69) |
| 1-463 | m/z = 688.26 (C50H32N4 = 688.83) | 1-464 | m/z = 629.19 (C44H27N3S = 629.78) |
| 1-465 | m/z = 629.19 (C44H27N3S = 629.78) | 1-466 | m/z = 629.19 (C44H27N3S = 629.78) |
| 1-467 | m/z = 629.19 (C44H27N3S = 629.78) | 1-468 | m/z = 725.28 (C54H35N3 = 725.89) |
| 1-469 | m/z = 651.24 (C46H29N5 = 651.77) | 1-470 | m/z = 651.24 (C46H29N5 = 651.77) |
| 1-471 | m/z = 651.24 (C46H29N5 = 651.77) | 1-472 | m/z = 727.27 (C52H33N5 = 727.87) |
| 1-473 | m/z = 727.27 (C52H33N5 = 727.87) | 1-474 | m/z = 727.27 (C52H33N5 = 727.87) |
| 1-475 | m/z = 574.22 (C41H26N4 = 574.69) | 1-476 | m/z = 574.22 (C41H26N4 = 574.69) |
| 1-477 | m/z = 574.22 (C41H26N4 = 574.69) | 1-478 | m/z = 650.25 (C47H30N4 = 650.78) |
| 1-479 | m/z = 650.25 (C47H30N4 = 650.78) | 1-480 | m/z = 650.25 (C47H30N4 = 650.78) |
| 1-481 | m/z = 726.28 (C53H34N4 = 726.88) | 1-482 | m/z = 650.25 (C47H30N4 = 650.78) |
| 1-483 | m/z = 548.20 (C39H24N4 = 548.65) | 1-484 | m/z = 651.24 (C46H29N5 = 651.77) |
| 1-485 | m/z = 574.22 (C41H26N4 = 574.69) | 1-486 | m/z = 598.22 (C43H26N4 = 598.71) |
| 1-487 | m/z = 612.23 (C44H28N4 = 612.74) | 1-488 | m/z = 726.28 (C53H34N4 = 726.88) |
| 1-489 | m/z = 650.25 (C47H30N4 = 650.78) | 1-490 | m/z = 624.23 (C45H28N4 = 624.75) |
| 1-491 | m/z = 651.24 (C46H29N5 = 651.77) | 1-492 | m/z = 574.22 (C41H26N4 = 574.69) |
| 1-493 | m/z = 598.22 (C43H26N4 = 598.71) | 1-494 | m/z = 612.23 (C44H28N4 = 612.74) |
| 1-495 | m/z = 727.26 (C53H33N3O = 727.87) | 1-496 | m/z = 651.23 (C47H29N3O = 651.77) |
| 1-497 | m/z = 549.18 (C39H23N3O = 549.63) | 1-498 | m/z = 576.20 (C40H24N4O = 576.66) |
| 1-499 | m/z = 499.17 (C35H21N3O = 499.57) | 1-500 | m/z = 599.20 (C43H25N3O = 599.69) |
| 1-501 | m/z = 613.22 (C44H27N3O = 613.72) | 1-502 | m/z = 743.24 (C53H33N3S = 743.93) |
| 1-503 | m/z = 667.21 (C47H29N3S = 667.83) | 1-504 | m/z = 565.16 (C39H23N3S = 565.69) |
| 1-505 | m/z = 592.17 (C40H24N4S = 592.72) | 1-506 | m/z = 515.15 (C35H21N3S = 515.63) |
| 1-507 | m/z = 615.18 (C43H25N3S = 615.75) | 1-508 | m/z = 629.19 (C44H27N3S = 629.78) |
| 1-509 | m/z = 753.31 (C56H39N3 = 753.95) | 1-510 | m/z = 677.28 (C50H35N3 = 677.85) |
| 1-511 | m/z = 575.24 (C42H29N3 = 575.71) | 1-512 | m/z = 602.25 (C43H30N4 = 602.74) |
| 1-513 | m/z = 525.22 (C38H27N3 = 525.65) | 1-514 | m/z = 625.25 (C46H31N3 = 625.77) |
| 1-515 | m/z = 639.27 (C47H33N3 = 639.80) | | |
| 2-1 | m/z = 651.24 (C46H29N5 = 651.77) | 2-2 | m/z = 700.26 (C51H32N4 = 700.84) |
| 2-3 | m/z = 726.28 (C53H34N4 = 726.88) | 2-4 | m/z = 650.25 (C47H30N4 = 650.78) |
| 2-5 | m/z = 739.27 (C53H33N5 = 739.88) | 2-6 | m/z = 547.20 (C40H25N3 = 547.66) |
| 2-7 | m/z = 586.22 (C42H26N4 = 586.70) | 2-8 | m/z = 688.26 (C50H32N4 = 688.83) |
| 2-9 | m/z = 650.25 (C47H30N4 = 650.78) | 2-10 | m/z = 620.20 (C43H29N2OP = 620.69) |
| 2-11 | m/z = 688.26 (C50H32N4 = 688.83) | 2-12 | m/z = 826.31 (C61H38N4 = 870.00) |
| 2-13 | m/z = 596.23 (C45H28N2 = 596.73) | 2-14 | m/z = 672.26 (C51H32N2 = 672.83) |
| 2-15 | m/z = 722.27 (C55H34N2 = 722.89) | 2-16 | m/z = 629.19 (C44H27N3S = 629.78) |
| 2-17 | m/z = 547.20 (C40H25N3 = 547.66) | 2-18 | m/z = 548.20 (C39H24N4 = 548.65) |
| 2-19 | m/z = 736.29 (C56H36N2 = 736.92) | 2-20 | m/z = 613.22 (C44H27N3O = 613.72) |
| 2-21 | m/z = 640.23 (C45H28N4O = 640.75) | 2-22 | m/z = 586.20 (C43H26N2O = 586.69) |
| 2-23 | m/z = 602.18 (C43H26N2S = 602.75) | 2-24 | m/z = 649.25 (C48H31N3 = 649.80) |

TABLE 2-continued

| Compound | FD-MS | Compound | FD-MS |
|---|---|---|---|
| 2-25 | m/z = 649.25 (C48H31N3 = 649.80) | 2-26 | m/z = 803.30 (C58H37N5 = 803.97) |
| 2-27 | m/z = 803.30 (C58H37N5 = 803.97) | 2-28 | m/z = 749.28 (C56H35N3 = 749.92) |
| 2-29 | m/z = 646.24 (C49H30N2 = 646.79) | 2-30 | m/z = 739.30 (C55H37N3 = 739.92) |
| 2-31 | m/z = 750.28 (C55H34N4 = 750.90) | 2-32 | m/z = 750.28 (C55H34N4 = 750.90) |
| 2-33 | m/z = 661.25 (C49H31N3 = 661.82) | 2-34 | m/z = 661.25 (C49H31N3 = 661.82) |
| 2-35 | m/z = 804.33 (C59H40N4 = 805.00) | 2-36 | m/z = 651.24 (C46H29N5 = 651.77) |
| 2-37 | m/z = 700.26 (C51H32N4 = 700.84) | 2-38 | m/z = 726.28 (C53H34N4 = 726.88) |
| 2-39 | m/z = 650.25 (C47H30N4 = 650.78) | 2-40 | m/z = 739.27 (C53H33N5 = 739.88) |
| 2-41 | m/z = 547.20 (C40H25N3 = 547.66) | 2-42 | m/z = 586.22 (C42H26N4 = 586.70) |
| 2-43 | m/z = 688.26 (C50H32N4 = 688.83) | 2-44 | m/z = 650.25 (C47H30N4 = 650.78) |
| 2-45 | m/z = 620.20 (C43H29N2OP = 620.69) | 2-46 | m/z = 688.26 (C50H32N4 = 688.83) |
| 2-47 | m/z = 826.31 (C61H38N4 = 827.00) | 2-48 | m/z = 596.23 (C45H28N2 = 596.73) |
| 2-49 | m/z = 672.26 (C51H32N2 = 672.83) | 2-50 | m/z = 739.30 (C55H37N3 = 739.92) |
| 2-51 | m/z = 750.28 (C55H34N4 = 750.90) | 2-52 | m/z = 602.18 (C43H26N2S = 602.75) |
| 2-53 | m/z = 697.25 (C52H31N3 = 697.84) | 2-54 | m/z = 650.25 (C47H30N4 = 650.78) |
| 2-55 | m/z = 547.20 (C40H25N3 = 547.66) | 2-56 | m/z = 602.25 (C43H30N4 = 602.74) |
| 2-57 | m/z = 651.27 (C48H33N3 = 651.82) | 2-58 | m/z = 677.28 (C50H35N3 = 677.85) |
| 2-59 | m/z = 601.25 (C44H31N3 = 601.75) | 2-60 | m/z = 690.28 (C50H34N4 = 690.85) |
| 2-61 | m/z = 498.21 (C37H26N2 = 498.63) | 2-62 | m/z = 537.22 (C39H27N3 = 537.67) |
| 2-63 | m/z = 639.27 (C47H33N3 = 639.80) | 2-64 | m/z = 601.25 (C44H31N3 = 601.75) |
| 2-65 | m/z = 571.22 (C40H30NPO = 571.66) | 2-66 | m/z = 639.27 (C47H33N3 = 639.80) |
| 2-67 | m/z = 779.33 (C58H41N3 = 779.99) | 2-68 | m/z = 547.23 (C42H29N = 547.70) |
| 2-69 | m/z = 623.26 (C48H33N = 623.80) | 2-70 | m/z = 690.30 (C52H38N2 = 690.89) |
| 2-71 | m/z = 701.28 (C52H35N3 = 701.87) | 2-72 | m/z = 553.19 (C40H27NS = 553.72) |
| 2-73 | m/z = 648.26 (C49H32N2 = 648.81) | 2-74 | m/z = 601.25 (C44H31N3 = 601.75) |
| 2-75 | m/z = 498.21 (C37H26N2 = 498.63) | 2-76 | m/z = 592.17 (C40H24N4S = 592.72) |
| 2-77 | m/z = 641.19 (C45H27N3S = 641.79) | 2-78 | m/z = 667.21 (C47H29N3S = 667.83) |
| 2-79 | m/z = 591.18 (C41H25N3S = 591.73) | 2-80 | m/z = 680.20 (C47H28N4S = 680.83) |
| 2-81 | m/z = 488.13 (C34H20N2S = 488.61) | 2-82 | m/z = 527.15 (C36H21N3S = 527.64) |
| 2-83 | m/z = 629.19 (C44H27N3S = 629.78) | 2-84 | m/z = 519.18 (C41H25N3S = 519.73) |
| 2-85 | m/z = 561.13 (C37H24NOPS = 561.64) | 2-86 | m/z = 629.19 (C44H27N3S = 692.78) |
| 2-87 | m/z = 769.26 (C55H35N3S = 769.97) | 2-88 | m/z = 537.16 (C39H23NS = 537.68) |
| 2-89 | m/z = 613.19 (C45H27NS = 613.78) | 2-90 | m/z = 680.23 (C49H32N2S = 680.87) |
| 2-91 | m/z = 691.21 (C49H29N3S = 691.85) | 2-92 | m/z = 543.11 (C37H21NS2 = 543.70) |
| 2-93 | m/z = 638.18 (C46H26N2S = 638.79) | 2-94 | m/z = 591.18 (C41H25N3S = 591.73) |
| 2-95 | m/z = 488.13 (C34H20N2S = 488.61) | 2-96 | m/z = 576.20 (C40H24N4 = 576.66) |
| 2-97 | m/z = 625.22 (C45H27N3O = 625.73) | 2-98 | m/z = 651.23 (C47H29N3O = 651.77) |
| 2-99 | m/z = 575.20 (C41H25N3O = 575.67) | 2-100 | m/z = 664.23 (C47H28N4O = 664.77) |
| 2-101 | m/z = 472.16 (C34H20N2O = 472.55) | 2-102 | m/z = 511.17 (C36H21N3O = 511.58) |
| 2-103 | m/z = 613.22 (C44H27N3O = 613.72) | 2-104 | m/z = 575.20 (C41H25N3O = 575.67) |
| 2-105 | m/z = 545.15 (C37H24NO2P = 545.58) | 2-106 | m/z = 613.22 (C44H27N3O = 613.72) |
| 2-107 | m/z = 753.28 (C55H35N3O = 735.90) | 2-108 | m/z = 521.18 (C39H23NO = 521.62) |
| 2-109 | m/z = 597.21 (C45H27NO = 597.72) | 2-110 | m/z = 664.25 (C49H32N2O = 664.81) |
| 2-111 | m/z = 675.23 (C49H29N3O = 675.79) | 2-112 | m/z = 527.13 (C37H21NOS = 527.64) |
| 2-113 | m/z = 622.20 (C46H26N2O = 622.73) | 2-114 | m/z = 575.20 (C41H25N3O = 575.67) |
| 2-115 | m/z = 472.16 (C34H20N2O = 472.55) | 2-116 | m/z = 651.24 (C46H29N5 = 651.77) |
| 2-117 | m/z = 700.26 (C51H32N4 = 700.84) | 2-118 | m/z = 726.28 (C53H34N4 = 726.88) |
| 2-119 | m/z = 650.25 (C47H30N4 = 650.78) | 2-120 | m/z = 739.27 (C53H33N5 = 739.88) |
| 2-121 | m/z = 547.20 (C40H25N3 = 547.66) | 2-122 | m/z = 586.22 (C42H26N4 = 586.70) |
| 2-123 | m/z = 688.26 (C50H32N4 = 688.83) | 2-124 | m/z = 650.25 (C47H30N4 = 650.78) |
| 2-125 | m/z = 620.20 (C43H29N2OP = 620.69) | 2-126 | m/z = 688.26 (C50H32N4 = 688.83) |
| 2-127 | m/z = 826.31 (C61H38N4 = 870.00) | 2-128 | m/z = 596.23 (C45H28N2 = 596.73) |
| 2-129 | m/z = 672.26 (C51H32N2 = 672.83) | 2-130 | m/z = 722.27 (C55H34N2 = 722.89) |
| 2-131 | m/z = 629.19 (C44H27N3S = 629.78) | 2-132 | m/z = 547.20 (C40H25N3 = 547.66) |
| 2-133 | m/z = 548.20 (C39H24N4 = 548.65) | 2-134 | m/z = 736.29 (C56H36N2 = 736.92) |
| 2-135 | m/z = 613.22 (C44H27N3O = 613.72) | 2-136 | m/z = 640.23 (C45H28N4O = 640.75) |
| 2-137 | m/z = 586.20 (C43H26N2O = 586.69) | 2-138 | m/z = 602.18 (C43H26N2S = 602.75) |
| 2-139 | m/z = 649.25 (C48H31N3 = 649.80) | 2-140 | m/z = 649.25 (C48H31N3 = 649.80) |
| 2-141 | m/z = 803.30 (C58H37N5 = 803.97) | 2-142 | m/z = 803.30 (C58H37N5 = 803.97) |
| 2-143 | m/z = 749.28 (C56H35N3 = 749.92) | 2-144 | m/z = 646.24 (C49H30N2 = 646.79) |
| 2-145 | m/z = 739.30 (C55H37N3 = 739.92) | 2-146 | m/z = 750.28 (C55H34N4 = 750.90) |
| 2-147 | m/z = 750.28 (C55H34N4 = 750.90) | 2-148 | m/z = 661.25 (C49H31N3 = 661.82) |
| 2-149 | m/z = 661.25 (C49H31N3 = 661.82) | 2-150 | m/z = 804.33 (C59H40N4 = 805.00) |
| 2-151 | m/z = 700.26 (C51H32N4 = 700.84) | 2-152 | m/z = 651.24 (C46H29N5 = 651.77) |
| 2-153 | m/z = 650.25 (C47H30N4 = 650.78) | 2-154 | m/z = 726.28 (C53H34N4 = 726.88) |
| 2-155 | m/z = 547.20 (C40H25N3 = 547.66) | 2-156 | m/z = 739.27 (C53H33N5 = 739.88) |
| 2-157 | m/z = 688.26 (C50H32N4 = 688.83) | 2-158 | m/z = 586.22 (C42H26N4 = 586.70) |
| 2-159 | m/z = 620.20 (C43H29N2OP = 620.69) | 2-160 | m/z = 650.25 (C47H30N4 = 650.78) |
| 2-161 | m/z = 826.31 (C61H38N4 = 827.00) | 2-162 | m/z = 688.26 (C50H32N4 = 688.83) |
| 2-163 | m/z = 672.26 (C51H32N2 = 672.83) | 2-164 | m/z = 596.23 (C45H28N2 = 596.73) |
| 2-165 | m/z = 750.28 (C55H34N4 = 750.90) | 2-166 | m/z = 739.30 (C55H37N3 = 739.92) |
| 2-167 | m/z = 697.25 (C52H31N3 = 697.84) | 2-168 | m/z = 602.18 (C43H26N2S = 602.75) |
| 2-169 | m/z = 547.20 (C40H25N3 = 547.66) | 2-170 | m/z = 650.25 (C47H30N4 = 650.78) |
| 2-171 | m/z = 602.25 (C43H30N4 = 602.74) | 2-172 | m/z = 651.27 (C48H33N3 = 651.82) |
| 2-173 | m/z = 677.28 (C50H35N3 = 677.85) | 2-174 | m/z = 601.25 (C44H31N3 = 601.75) |
| 2-175 | m/z = 690.28 (C50H34N4 = 690.85) | 2-176 | m/z = 498.21 (C37H26N2 = 498.63) |
| 2-177 | m/z = 537.22 (C39H27N3 = 537.67) | 2-178 | m/z = 639.27 (C47H33N3 = 639.80) |
| 2-179 | m/z = 601.25 (C44H31N3 = 601.75) | 2-180 | m/z = 571.22 (C40H30NPO = 571.66) |

TABLE 2-continued

| Compound | FD-MS | Compound | FD-MS |
|---|---|---|---|
| 2-181 | m/z = 639.27 (C47H33N3 = 639.80) | 2-182 | m/z = 779.33 (C58H41N3 = 779.99) |
| 2-183 | m/z = 547.23 (C42H29N = 547.70) | 2-184 | m/z = 623.26 (C48H33N = 623.80) |
| 2-185 | m/z = 690.30 (C52H38N2 = 690.89) | 2-186 | m/z = 701.28 (C52H35N3 = 701.87) |
| 2-187 | m/z = 553.19 (C40H27NS = 553.72) | 2-188 | m/z = 648.26 (C49H32N2 = 648.81) |
| 2-189 | m/z = 601.25 (C44H31N3 = 601.75) | 2-190 | m/z = 498.21 (C37H26N2 = 498.63) |
| 2-191 | m/z = 592.17 (C40H24N4S = 592.72) | 2-192 | m/z = 641.19 (C45H27N3S = 641.79) |
| 2-193 | m/z = 667.21 (C47H29N3S = 667.83) | 2-194 | m/z = 591.18 (C41H25N3S = 591.73) |
| 2-195 | m/z = 680.20 (C47H28N4S = 680.83) | 2-196 | m/z = 488.13 (C34H20N2S = 488.61) |
| 2-197 | m/z = 527.15 (C36H21N3S = 527.64) | 2-198 | m/z = 629.19 (C44H27N3S = 629.78) |
| 2-199 | m/z = 519.18 (C41H25N3S = 519.73) | 2-200 | m/z = 561.13 (C37H24NOPS = 561.64) |
| 2-201 | m/z = 629.19 (C44H27N3S = 692.78) | 2-202 | m/z = 769.26 (C55H35N3S = 769.97) |
| 2-203 | m/z = 537.16 (C39H23NS = 537.68) | 2-204 | m/z = 613.19 (C45H27NS = 613.78) |
| 2-205 | m/z = 680.23 (C49H32N2S = 680.87) | 2-206 | m/z = 675.23 (C49H29N3O = 675.77) |
| 2-207 | m/z = 527.13 (C37H21NSO = 527.63) | 2-208 | m/z = 622.20 (C46H26N2O = 622.71) |
| 2-209 | m/z = 575.20 (C41H25N3O = 575.20) | 2-210 | m/z = 472.16 (C34H20N2O = 472.54) |
| 2-211 | m/z = 576.20 (C40H24N4 = 576.66) | 2-212 | m/z = 625.22 (C45H27N3O = 625.73) |
| 2-213 | m/z = 651.23 (C47H29N3O = 651.77) | 2-214 | m/z = 575.20 (C41H25N3O = 575.67) |
| 2-215 | m/z = 664.23 (C47H28N4O = 664.77) | 2-216 | m/z = 472.16 (C34H20N2O = 472.55) |
| 2-217 | m/z = 511.17 (C36H21N3O = 511.58) | 2-218 | m/z = 613.22 (C44H27N3O = 613.72) |
| 2-219 | m/z = 575.20 (C41H25N3O = 575.67) | 2-220 | m/z = 545.15 (C37H24NO2P = 545.58) |
| 2-221 | m/z = 613.22 (C44H27N3O = 613.72) | 2-222 | m/z = 753.28 (C55H35N3O = 735.90) |
| 2-223 | m/z = 521.18 (C39H23NO = 521.62) | 2-224 | m/z = 597.21 (C45H27NO = 597.72) |
| 2-225 | m/z = 664.25 (C49H32N2O = 664.81) | 2-226 | m/z = 751.30 (C56H37N3 = 751.91) |
| 2-227 | m/z = 603.20 (C44H29NS = 603.77) | 2-228 | m/z = 698.27 (C53H34N2 = 698.85) |
| 2-229 | m/z = 651.27 (C48H33N3 = 651.80) | 2-230 | m/z = 548.23 (C41H28N2 = 548.67) |
| 2-231 | m/z = 651.24 (C46H29N5 = 651.77) | 2-232 | m/z = 700.26 (C51H32N4 = 700.84) |
| 2-233 | m/z = 726.28 (C53H34N4 = 726.88) | 2-234 | m/z = 650.25 (C47H30N4 = 650.78) |
| 2-235 | m/z = 739.27 (C53H33N5 = 739.88) | 2-236 | m/z = 547.20 (C40H25N3 = 547.66) |
| 2-237 | m/z = 586.22 (C42H26N4 = 586.70) | 2-238 | m/z = 688.26 (C50H32N4 = 688.83) |
| 2-239 | m/z = 650.25 (C47H30N4 = 650.78) | 2-240 | m/z = 620.20 (C43H29N2OP = 620.69) |
| 2-241 | m/z = 688.26 (C50H32N4 = 688.83) | 2-242 | m/z = 826.31 (C61H38N4 = 827.00) |
| 2-243 | m/z = 596.23 (C45H28N2 = 596.73) | 2-244 | m/z = 672.26 (C51H32N2 = 672.83) |
| 2-245 | m/z = 722.27 (C55H34N2 = 722.89) | 2-246 | m/z = 629.19 (C44H27N3S = 629.78) |
| 2-247 | m/z = 547.20 (C40H25N3 = 547.66) | 2-248 | m/z = 548.20 (C39H24N4 = 548.65) |
| 2-249 | m/z = 736.29 (C56H36N2 = 736.92) | 2-250 | m/z = 613.22 (C44H27N3O = 613.72) |
| 2-251 | m/z = 640.23 (C45H28N4O = 640.75) | 2-252 | m/z = 586.20 (C43H26N2O = 586.69) |
| 2-253 | m/z = 602.18 (C43H26N2S = 602.75) | 2-254 | m/z = 649.25 (C48H31N3 = 649.80) |
| 2-255 | m/z = 649.25 (C48H31N3 = 649.80) | 2-256 | m/z = 803.30 (C58H37N5 = 803.97) |
| 2-257 | m/z = 803.30 (C58H37N5 = 803.97) | 2-258 | m/z = 749.28 (C56H35N3 = 749.92) |
| 2-259 | m/z = 646.24 (C49H30N2 = 646.79) | 2-260 | m/z = 739.30 (C55H37N3 = 739.92) |
| 2-261 | m/z = 750.28 (C55H34N4 = 750.90) | 2-262 | m/z = 750.28 (C55H34N4 = 750.90) |
| 2-263 | m/z = 661.25 (C49H31N3 = 661.81) | 2-264 | m/z = 661.25 (C49H31N3 = 661.81) |
| 2-265 | m/z = 804.33 (C59H40N4 = 805.00) | 2-266 | m/z = 651.24 (C46H29N5 = 651.77) |
| 2-267 | m/z = 700.26 (C51H32N4 = 700.84) | 2-268 | m/z = 726.28 (C53H34N4 = 726.88) |
| 2-269 | m/z = 650.25 (C47H30N4 = 650.78) | 2-270 | m/z = 739.27 (C53H33N5 = 739.88) |
| 2-271 | m/z = 547.20 (C40H25N3 = 547.66) | 2-272 | m/z = 586.22 (C42H26N4 = 586.70) |
| 2-273 | m/z = 688.26 (C50H32N4 = 688.83) | 2-274 | m/z = 650.25 (C47H30N4 = 650.78) |
| 2-275 | m/z = 620.20 (C43H29N2OP = 620.69) | 2-276 | m/z = 688.26 (C50H32N4 = 688.83) |
| 2-277 | m/z = 826.31 (C61H38N4 = 827.00) | 2-278 | m/z = 596.23 (C45H28N2 = 596.73) |
| 2-279 | m/z = 672.26 (C51H32N2 = 672.83) | 2-280 | m/z = 722.27 (C55H34N2 = 722.89) |
| 2-281 | m/z = 629.19 (C44H27N3S = 629.78) | 2-282 | m/z = 547.20 (C40H25N3 = 547.66) |
| 2-283 | m/z = 548.20 (C39H24N4 = 548.65) | 2-284 | m/z = 736.29 (C56H36N2 = 736.92) |
| 2-285 | m/z = 613.22 (C44H27N3O = 613.72) | 2-286 | m/z = 640.23 (C45H28N4O = 640.75) |
| 2-287 | m/z = 586.20 (C43H26N2O = 586.69) | 2-288 | m/z = 602.18 (C43H26N2S = 602.75) |
| 2-289 | m/z = 649.25 (C48H31N3 = 649.80) | 2-290 | m/z = 649.25 (C48H31N3 = 649.80) |
| 2-291 | m/z = 803.30 (C58H37N5 = 803.97) | 2-292 | m/z = 803.30 (C58H37N5 = 803.97) |
| 2-293 | m/z = 749.28 (C56H35N3 = 749.92) | 2-294 | m/z = 646.24 (C49H30N2 = 646.79) |
| 2-295 | m/z = 739.30 (C55H37N3 = 739.92) | 2-296 | m/z = 750.28 (C55H34N4 = 750.90) |
| 2-297 | m/z = 750.28 (C55H34N4 = 750.90) | 2-298 | m/z = 661.25 (C49H31N3 = 661.81) |
| 2-299 | m/z = 661.25 (C49H31N3 = 661.81) | 2-300 | m/z = 804.33 (C59H40N4 = 805.00) |
| 3-1 | m/z = 651.24 (C46H29N5 = 651.77) | 3-2 | m/z = 700.26 (C51H32N4 = 700.84) |
| 3-3 | m/z = 726.28 (C53H34N4 = 726.88) | 3-4 | m/z = 650.25 (C47H30N4 = 650.78) |
| 3-5 | m/z = 739.27 (C53H33N5 = 739.88) | 3-6 | m/z = 547.20 (C40H25N3 = 547.66) |
| 3-7 | m/z = 586.22 (C42H26N4 = 586.70) | 3-8 | m/z = 688.26 (C50H32N4 = 688.83) |
| 3-9 | m/z = 650.25 (C47H30N4 = 650.78) | 3-10 | m/z = 620.20 (C43H29N2OP = 620.69) |
| 3-11 | m/z = 688.26 (C50H32N4 = 688.83) | 3-12 | m/z = 826.31 (C61H38N4 = 870.00) |
| 3-13 | m/z = 596.23 (C45H28N2 = 596.73) | 3-14 | m/z = 672.26 (C51H32N2 = 672.83) |
| 3-15 | m/z = 722.27 (C55H34N2 = 722.89) | 3-16 | m/z = 629.19 (C44H27N3S = 629.78) |
| 3-17 | m/z = 547.20 (C40H25N3 = 547.66) | 3-18 | m/z = 548.20 (C39H24N4 = 548.65) |
| 3-19 | m/z = 736.29 (C56H36N2 = 736.92) | 3-20 | m/z = 613.22 (C44H27N3O = 613.72) |
| 3-21 | m/z = 640.23 (C45H28N4O = 640.75) | 3-22 | m/z = 586.20 (C43H26N2O = 586.69) |
| 3-23 | m/z = 602.18 (C43H26N2S = 602.75) | 3-24 | m/z = 649.25 (C48H31N3 = 649.80) |
| 3-25 | m/z = 649.25 (C48H31N3 = 649.80) | 3-26 | m/z = 803.30 (C58H37N5 = 803.97) |
| 3-27 | m/z = 803.30 (C58H37N5 = 803.97) | 3-28 | m/z = 749.28 (C56H35N3 = 749.92) |
| 3-29 | m/z = 646.24 (C49H30N2 = 646.79) | 3-30 | m/z = 739.30 (C55H37N3 = 739.92) |
| 3-31 | m/z = 750.28 (C55H34N4 = 750.90) | 3-32 | m/z = 750.28 (C55H34N4 = 750.90) |
| 3-33 | m/z = 661.25 (C49H31N3 = 661.82) | 3-34 | m/z = 661.25 (C49H31N3 = 661.82) |
| 3-35 | m/z = 804.33 (C59H40N4 = 805.00) | 3-36 | m/z = 651.24 (C46H29N5 = 651.77) |

TABLE 2-continued

| Compound | FD-MS | Compound | FD-MS |
|---|---|---|---|
| 3-37 | m/z = 700.26 (C51H32N4 = 700.84) | 3-38 | m/z = 726.28 (C53H34N4 = 726.88) |
| 3-39 | m/z = 650.25 (C47H30N4 = 650.78) | 3-40 | m/z = 739.27 (C53H33N5 = 739.88) |
| 3-41 | m/z = 547.20 (C40H25N3 = 547.66) | 3-42 | m/z = 586.22 (C42H26N4 = 586.70) |
| 3-43 | m/z = 688.26 (C50H32N4 = 688.83) | 3-44 | m/z = 650.25 (C47H30N4 = 650.78) |
| 3 45 | m/z = 620.20 (C43H29N2OP = 620.69) | 3-46 | m/z = 688.26 (C50H32N4 = 688.83) |
| 3-47 | m/z = 826.31 (C61H38N4 = 827.00) | 3-48 | m/z = 596.23 (C45H28N2 = 596.73) |
| 3-49 | m/z = 672.26 (C51H32N2 = 672.83) | 3-50 | m/z = 739.30 (C55H37N3 = 739.92) |
| 3-51 | m/z = 750.28 (C55H34N4 = 750.90) | 3-52 | m/z = 602.18 (C43H26N2S = 602.75) |
| 3-53 | m/z = 697.25 (C52H31N3 = 697.84) | 3-54 | m/z = 650.25 (C47H30N4 = 650.78) |
| 3-55 | m/z = 547.20 (C40H25N3 = 547.66) | 3-56 | m/z = 602.25 (C43H30N4 = 602.74) |
| 3-57 | m/z = 651.27 (C48H33N3 = 651.82) | 3-58 | m/z = 677.28 (C50H35N3 = 677.85) |
| 3-59 | m/z = 601.25 (C44H31N3 = 601.75) | 3-60 | m/z = 690.28 (C50H34N4 = 690.85) |
| 3-61 | m/z = 498.21 (C37H26N2 = 498.63) | 3-62 | m/z = 537.22 (C39H27N3 = 537.67) |
| 3-63 | m/z = 639.27 (C47H33N3 = 639.80) | 3-64 | m/z = 601.25 (C44H31N3 = 601.75) |
| 3-65 | m/z = 571.22 (C40H30NPO = 571.66) | 3-66 | m/z = 639.27 (C47H33N3 = 639.80) |
| 3-67 | m/z = 779.33 (C58H41N3 = 779.99) | 3-68 | m/z = 547.23 (C42H29N = 547.70) |
| 3-69 | m/z = 623.26 (C48H33N = 623.80) | 3-70 | m/z = 690.30 (C52H38N2 = 690.89) |
| 3-71 | m/z = 701.28 (C52H35N3 = 701.87) | 3-72 | m/z = 553.19 (C40H27NS = 553.72) |
| 3-73 | m/z = 648.26 (C49H32N2 = 648.81) | 3-74 | m/z = 601.25 (C44H31N3 = 601.75) |
| 3-75 | m/z = 498.21 (C37H26N2 = 498.63) | 3-76 | m/z = 592.17 (C40H24N4S = 592.72) |
| 3-77 | m/z = 641.19 (C45H27N3S = 641.79) | 3-78 | m/z = 667.21 (C47H29N3S = 667.83) |
| 3-79 | m/z = 591.18 (C41H25N3S = 591.73) | 3-80 | m/z = 680.20 (C47H28N4S = 680.83) |
| 3-81 | m/z = 488.13 (C34H20N2S = 488.61) | 3-82 | m/z = 527.15 (C36H21N3S = 527.64) |
| 3-83 | m/z = 629.19 (C44H27N3S = 629.78) | 3-84 | m/z = 519.18 (C41H25N3S = 519.73) |
| 3-85 | m/z = 561.13 (C37H24NOPS = 561.64) | 3-86 | m/z = 629.19 (C44H27N3S = 692.78) |
| 3-87 | m/z = 769.26 (C55H35N3S = 769.97) | 3-88 | m/z = 537.16 (C39H23NS = 537.68) |
| 3-89 | m/z = 613.19 (C45H27NS = 613.78) | 3-90 | m/z = 680.23 (C49H32N2S = 680.87) |
| 3-91 | m/z = 691.21 (C49H29N3S = 691.85) | 3-92 | m/z = 543.11 (C37H21NS2 = 543.70) |
| 3-93 | m/z = 638.18 (C46H26N2S = 638.79) | 3-94 | m/z = 591.18 (C41H25N3S = 591.73) |
| 3-95 | m/z = 488.13 (C34H20N2S = 488.61) | 3-96 | m/z = 576.20 (C40H24N4 = 576.66) |
| 3-97 | m/z = 625.22 (C45H27N3O = 625.73) | 3-98 | m/z = 651.23 (C47H29N3O = 651.77) |
| 3-99 | m/z = 575.20 (C41H25N3O = 575.67) | 3-100 | m/z = 664.23 (C47H28N4O = 664.77) |
| 3-101 | m/z = 472.16 (C34H20N2O = 472.55) | 3-102 | m/z = 511.17 (C36H21N3O = 511.58) |
| 3-103 | m/z = 613.22 (C44H27N3O = 613.72) | 3-104 | m/z = 575.20 (C41H25N3O = 575.67) |
| 3-105 | m/z = 545.15 (C37H24NO2P = 545.58) | 3-106 | m/z = 613.22 (C44H27N3O = 613.72) |
| 3-107 | m/z = 753.28 (C55H35N3O = 735.90) | 3-108 | m/z = 521.18 (C39H23NO = 521.62) |
| 3-109 | m/z = 597.21 (C45H27NO = 597.72) | 3-110 | m/z = 664.25 (C49H32N2O = 664.81) |
| 3-111 | m/z = 675.23 (C49H29N3O = 675.79) | 3-112 | m/z = 527.13 (C37H21NOS = 527.64) |
| 3-113 | m/z = 622.20 (C46H26N2O = 622.73) | 3-114 | m/z = 575.20 (C41H25N3O = 575.67) |
| 3-115 | m/z = 472.16 (C34H20N2O = 472.55) | 3-116 | m/z = 651.24 (C46H29N5 = 651.77) |
| 3-117 | m/z = 700.26 (C51H32N4 = 700.84) | 3-118 | m/z = 726.28 (C53H34N4 = 726.88) |
| 3-119 | m/z = 650.25 (C47H30N4 = 650.78) | 3-120 | m/z = 739.27 (C53H33N5 = 739.88) |
| 3-121 | m/z = 547.20 (C40H25N3 = 547.66) | 3-122 | m/z = 586.22 (C42H26N4 = 586.70) |
| 3-123 | m/z = 688.26 (C50H32N4 = 688.83) | 3-124 | m/z = 650.25 (C47H30N4 = 650.78) |
| 3-125 | m/z = 620.20 (C43H29N2OP = 620.69) | 3-126 | m/z = 688.26 (C50H32N4 = 688.83) |
| 3-127 | m/z = 826.31 (C61H38N4 = 870.00) | 3-128 | m/z = 596.23 (C45H28N2 = 596.73) |
| 3-129 | m/z = 672.26 (C51H32N2 = 672.83) | 3-130 | m/z = 722.27 (C55H34N2 = 722.89) |
| 3-131 | m/z = 629.19 (C44H27N3S = 629.78) | 3-132 | m/z = 547.20 (C40H25N3 = 547.66) |
| 3-133 | m/z = 548.20 (C39H24N4 = 548.65) | 3-134 | m/z = 736.29 (C56H36N2 = 736.92) |
| 3-135 | m/z = 613.22 (C44H27N3O = 613.72) | 3-136 | m/z = 640.23 (C45H28N4O = 640.75) |
| 3-137 | m/z = 586.20 (C43H26N2O = 586.69) | 3-138 | m/z = 602.18 (C43H26N2S = 602.75) |
| 3-139 | m/z = 649.25 (C48H31N3 = 649.80) | 3-140 | m/z = 649.25 (C48H31N3 = 649.80) |
| 3-141 | m/z = 803.30 (C58H37N5 = 803.97) | 3-142 | m/z = 803.30 (C58H37N5 = 803.97) |
| 3-143 | m/z = 749.28 (C56H35N3 = 749.92) | 3-144 | m/z = 646.24 (C49H30N2 = 646.79) |
| 3-145 | m/z = 739.30 (C55H37N3 = 739.92) | 3-146 | m/z = 750.28 (C55H34N4 = 750.90) |
| 3-147 | m/z = 750.28 (C55H34N4 = 750.90) | 3-148 | m/z = 661.25 (C49H31N3 = 661.82) |
| 3-149 | m/z = 661.25 (C49H31N3 = 661.82) | 3-150 | m/z = 804.33 (C59H40N4 = 805.00) |
| 3-151 | m/z = 700.26 (C51H32N4 = 700.84) | 3-152 | m/z = 651.24 (C46H29N5 = 651.77) |
| 3-153 | m/z = 650.25 (C47H30N4 = 650.78) | 3-154 | m/z = 726.28 (C53H34N4 = 726.88) |
| 3-155 | m/z = 547.20 (C40H25N3 = 547.66) | 3-156 | m/z = 739.27 (C53H33N5 = 739.88) |
| 3-157 | m/z = 688.26 (C50H32N4 = 688.83) | 3-158 | m/z = 586.22 (C42H26N4 = 586.70) |
| 3-159 | m/z = 620.20 (C43H29N2OP = 620.69) | 3-160 | m/z = 650.25 (C47H30N4 = 650.78) |
| 3-161 | m/z = 826.31 (C61H38N4 = 827.00) | 3-162 | m/z = 688.26 (C50H32N4 = 688.83) |
| 3-163 | m/z = 672.26 (C51H32N2 = 672.83) | 3-164 | m/z = 596.23 (C45H28N2 = 596.73) |
| 3-165 | m/z = 750.28 (C55H34N4 = 750.90) | 3-166 | m/z = 739.30 (C55H37N3 = 739.92) |
| 3-167 | m/z = 697.25 (C52H31N3 = 697.84) | 3-168 | m/z = 602.18 (C43H26N2S = 602.75) |
| 3-169 | m/z = 547.20 (C40H25N3 = 547.66) | 3-170 | m/z = 650.25 (C47H30N4 = 650.78) |
| 3-171 | m/z = 602.25 (C43H30N4 = 602.74) | 3-172 | m/z = 651.27 (C48H33N3 = 651.82) |
| 3-173 | m/z = 677.28 (C50H35N3 = 677.85) | 3-174 | m/z = 601.25 (C44H31N3 = 601.75) |
| 3-175 | m/z = 690.28 (C50H34N4 = 690.85) | 3-176 | m/z = 498.21 (C37H26N2 = 498.63) |
| 3-177 | m/z = 537.22 (C39H27N3 = 537.67) | 3-178 | m/z = 639.27 (C47H33N3 = 639.80) |
| 3-179 | m/z = 601.25 (C44H31N3 = 601.75) | 3-180 | m/z = 571.22 (C40H30NPO = 571.66) |
| 3-181 | m/z = 639.27 (C47H33N3 = 639.80) | 3-182 | m/z = 779.33 (C58H41N3 = 779.99) |
| 3-183 | m/z = 547.23 (C42H29N = 547.70) | 3-184 | m/z = 623.26 (C48H33N = 623.80) |
| 3-185 | m/z = 690.30 (C52H38N2 = 690.89) | 3-186 | m/z = 701.28 (C52H35N3 = 701.87) |
| 3-187 | m/z = 553.19 (C40H27NS = 553.72) | 3-188 | m/z = 648.26 (C49H32N2 = 648.81) |
| 3-189 | m/z = 601.25 (C44H31N3 = 601.75) | 3-190 | m/z = 498.21 (C37H26N2 = 498.63) |
| 3-191 | m/z = 592.17 (C40H24N4S = 592.72) | 3-192 | m/z = 641.19 (C45H27N3S = 641.79) |

TABLE 2-continued

| Compound | FD-MS | Compound | FD-MS |
|---|---|---|---|
| 3-193 | m/z = 667.21 (C47H29N3S = 667.83) | 3-194 | m/z = 591.18 (C41H25N3S = 591.73) |
| 3-195 | m/z = 680.20 (C47H28N4S = 680.83) | 3-196 | m/z = 488.13 (C34H20N2S = 488.61) |
| 3-197 | m/z = 527.15 (C36H21N3S = 527.64) | 3-198 | m/z = 629.19 (C44H27N3S = 629.78) |
| 3-199 | m/z = 519.18 (C41H25N3S = 519.73) | 3-200 | m/z = 561.13 (C37H24NOPS = 561.64) |
| 3-201 | m/z = 629.19 (C44H27N3S = 692.78) | 3-202 | m/z = 769.26 (C55H35N3S = 769.97) |
| 3-203 | m/z = 537.16 (C39H23NS = 537.68) | 3-204 | m/z = 613.19 (C45H27NS = 613.78) |
| 3-205 | m/z = 680.23 (C49H32N2S = 680.87) | 3-206 | m/z = 691.21 (C49H29N3S = 691.85) |
| 3-207 | m/z = 543.11 (C37H21NS2 = 543.70) | 3-208 | m/z = 638.18 (C46H26N2S = 638.79) |
| 3-209 | m/z = 591.18 (C41H25N3S = 591.73) | 3-210 | m/z = 488.13 (C34H20N2S = 488.61) |
| 3-211 | m/z = 576.20 (C40H24N4 = 576.66) | 3-212 | m/z = 625.22 (C45H27N3O = 625.73) |
| 3-213 | m/z = 651.23 (C47H29N3O = 651.77) | 3-214 | m/z = 575.20 (C41H25N3O = 575.67) |
| 3-215 | m/z = 664.23 (C47H28N4O = 664.77) | 3-216 | m/z = 472.16 (C34H20N2O = 472.55) |
| 3-217 | m/z = 511.17 (C36H21N3O = 511.58) | 3-218 | m/z = 613.22 (C44H27N3O = 613.72) |
| 3-219 | m/z = 575.20 (C41H25N3O = 575.67) | 3-220 | m/z = 545.15 (C37H24NO2P = 545.58) |
| 3-221 | m/z = 613.22 (C44H27N3O = 613.72) | 3-222 | m/z = 753.28 (C55H35N3O = 735.90) |
| 3-223 | m/z = 521.18 (C39H23NO = 521.62) | 3-224 | m/z = 597.21 (C45H27NO = 597.72) |
| 3-225 | m/z = 664.25 (C49H32N2O = 664.81) | 3-226 | m/z = 675.23 (C49H29N3O = 675.79) |
| 3-227 | m/z = 527.13 (C37H21NOS = 527.64) | 3-228 | m/z = 622.20 (C46H26N2O = 622.73) |
| 3-229 | m/z = 575.20 (C41H25N3O = 575.67) | 3-230 | m/z = 472.16 (C34H20N2O = 472.55) |
| 3-231 | m/z = 651.24 (C46H29N5 = 651.77) | 3-232 | m/z = 700.26 (C51H32N4 = 700.84) |
| 3-233 | m/z = 726.28 (C53H34N4 = 726.88) | 3-234 | m/z = 650.25 (C47H30N4 = 650.78) |
| 3-235 | m/z = 739.27 (C53H33N5 = 739.88) | 3-236 | m/z = 547.20 (C40H25N3 = 547.66) |
| 3-237 | m/z = 586.22 (C42H26N4 = 586.70) | 3-238 | m/z = 688.26 (C50H32N4 = 688.83) |
| 3-239 | m/z = 650.25 (C47H30N4 = 650.78) | 3-240 | m/z = 620.20 (C43H29N2OP = 620.69) |
| 3-241 | m/z = 688.26 (C50H32N4 = 688.83) | 3-242 | m/z = 826.31 (C61H38N4 = 827.00) |
| 3-243 | m/z = 596.23 (C45H28N2 = 596.73) | 3-244 | m/z = 672.26 (C51H32N2 = 672.83) |
| 3-245 | m/z = 722.27 (C55H34N2 = 722.89) | 3-246 | m/z = 629.19 (C44H27N3S = 629.78) |
| 3-247 | m/z = 547.20 (C40H25N3 = 547.66) | 3-248 | m/z = 548.20 (C39H24N4 = 548.65) |
| 3-249 | m/z = 736.29 (C56H36N2 = 736.92) | 3-250 | m/z = 613.22 (C44H27N3O = 613.72) |
| 3-251 | m/z = 640.23 (C45H28N4O = 640.75) | 3-252 | m/z = 586.20 (C43H26N2O = 586.69) |
| 3-253 | m/z = 602.18 (C43H26N2S = 602.75) | 3-254 | m/z = 649.25 (C48H31N3 = 649.80) |
| 3-255 | m/z = 649.25 (C48H31N3 = 649.80) | 3-256 | m/z = 803.30 (C58H37N5 = 803.97) |
| 3-257 | m/z = 803.30 (C58H37N5 = 803.97) | 3-258 | m/z = 749.28 (C56H35N3 = 749.92) |
| 3-259 | m/z = 646.24 (C49H30N2 = 646.79) | 3-260 | m/z = 739.30 (C55H37N3 = 739.92) |
| 3-261 | m/z = 750.28 (C55H34N4 = 750.90) | 3-262 | m/z = 750.28 (C55H34N4 = 750.90) |
| 3-263 | m/z = 661.25 (C49H31N3 = 661.81) | 3-264 | m/z = 661.25 (C49H31N3 = 661.81) |
| 3-265 | m/z = 804.33 (C59H40N4 = 805.00) | 3-266 | m/z = 651.24 (C46H29N5 = 651.77) |
| 3-267 | m/z = 700.26 (C51H32N4 = 700.84) | 3-268 | m/z = 726.28 (C53H34N4 = 726.88) |
| 3-269 | m/z = 650.25 (C47H30N4 = 650.78) | 3-270 | m/z = 739.27 (C53H33N5 = 739.88) |
| 3-271 | m/z = 547.20 (C40H25N3 = 547.66) | 3-272 | m/z = 586.22 (C42H26N4 = 586.70) |
| 3-273 | m/z = 688.26 (C50H32N4 = 688.83) | 3-274 | m/z = 650.25 (C47H30N4 = 650.78) |
| 3-275 | m/z = 620.20 (C43H29N2OP = 620.69) | 3-276 | m/z = 688.26 (C50H32N4 = 688.83) |
| 3-277 | m/z = 826.31 (C61H38N4 = 827.00) | 3-278 | m/z = 596.23 (C45H28N2 = 596.73) |
| 3-279 | m/z = 672.26 (C51H32N2 = 672.83) | 3-280 | m/z = 722.27 (C55H34N2 = 722.89) |
| 3-281 | m/z = 629.19 (C44H27N3S = 629.78) | 3-282 | m/z = 547.20 (C40H25N3 = 547.66) |
| 3-283 | m/z = 548.20 (C39H24N4 = 548.65) | 3-284 | m/z = 736.29 (C56H36N2 = 736.92) |
| 3-285 | m/z = 613.22 (C44H27N3O = 613.72) | 3-286 | m/z = 640.23 (C45H28N4O = 640.75) |
| 3-287 | m/z = 586.20 (C43H26N2O = 586.69) | 3-288 | m/z = 602.18 (C43H26N2S = 602.75) |
| 3-289 | m/z = 649.25 (C48H31N3 = 649.80) | 3-290 | m/z = 649.25 (C48H31N3 = 649.80) |
| 3-291 | m/z = 803.30 (C58H37N5 = 803.97) | 3-292 | m/z = 803.30 (C58H37N5 = 803.97) |
| 3-293 | m/z = 749.28 (C56H35N3 = 749.92) | 3-294 | m/z = 646.24 (C49H30N2 = 646.79) |
| 3-295 | m/z = 739.30 (C55H37N3 = 739.92) | 3-296 | m/z = 750.28 (C55H34N4 = 750.90) |
| 3-297 | m/z = 750.28 (C55H34N4 = 750.90) | 3-298 | m/z = 661.25 (C49H31N3 = 661.81) |
| 3-299 | m/z = 661.25 (C49H31N3 = 661.81) | 3-300 | m/z = 804.33 (C59H40N4 = 805.00) |
| 4-1 | m/z = 651.24 (C46H29N5 = 651.77) | 4-2 | m/z = 700.26 (C51H32N4 = 700.84) |
| 4-3 | m/z = 726.28 (C53H34N4 = 726.88) | 4-4 | m/z = 650.25 (C47H30N4 = 650.78) |
| 4-5 | m/z = 739.27 (C53H33N5 = 739.88) | 4-6 | m/z = 547.20 (C40H25N3 = 547.66) |
| 4-7 | m/z = 586.22 (C42H26N4 = 586.70) | 4-8 | m/z = 688.26 (C50H32N4 = 688.83) |
| 4-9 | m/z = 650.25 (C47H30N4 = 650.78) | 4-10 | m/z = 620.20 (C43H29N2OP = 620.69) |
| 4-11 | m/z = 688.26 (C50H32N4 = 688.83) | 4-12 | m/z = 826.31 (C61H38N4 = 870.00) |
| 4-13 | m/z = 596.23 (C45H28N2 = 596.73) | 4-14 | m/z = 672.26 (C51H32N2 = 672.83) |
| 4-15 | m/z = 722.27 (C55H34N2 = 722.89) | 4-16 | m/z = 629.19 (C44H27N3S = 629.78) |
| 4-17 | m/z = 547.20 (C40H25N3 = 547.66) | 4-18 | m/z = 548.20 (C39H24N4 = 548.65) |
| 4-19 | m/z = 736.29 (C56H36N2 = 736.92) | 4-20 | m/z = 613.22 (C44H27N3O = 613.72) |
| 4-21 | m/z = 640.23 (C45H28N4O = 640.75) | 4-22 | m/z = 586.20 (C43H26N2O = 586.69) |
| 4-23 | m/z = 602.18 (C43H26N2S = 602.75) | 4-24 | m/z = 649.25 (C48H31N3 = 649.80) |
| 4-25 | m/z = 649.25 (C48H31N3 = 649.80) | 4-26 | m/z = 803.30 (C58H37N5 = 803.97) |
| 4-27 | m/z = 803.30 (C58H37N5 = 803.97) | 4-28 | m/z = 749.28 (C56H35N3 = 749.92) |
| 4-29 | m/z = 646.24 (C49H30N2 = 646.79) | 4-30 | m/z = 739.30 (C55H37N3 = 739.92) |
| 4-31 | m/z = 750.28 (C55H34N4 = 750.90) | 4-32 | m/z = 750.28 (C55H34N4 = 750.90) |
| 4-33 | m/z = 661.25 (C49H31N3 = 661.82) | 4-34 | m/z = 661.25 (C49H31N3 = 661.82) |
| 4-35 | m/z = 804.33 (C59H40N4 = 805.00) | 4-36 | m/z = 602.25 (C43H30N4 = 602.74) |
| 4-37 | m/z = 651.27 (C48H33N3 = 651.82) | 4-38 | m/z = 677.28 (C50H35N3 = 677.85) |
| 4-39 | m/z = 601.25 (C44H31N3 = 601.75) | 4-40 | m/z = 690.28 (C50H34N4 = 690.85) |
| 4-41 | m/z = 498.21 (C37H26N2 = 498.63) | 4-42 | m/z = 537.22 (C39H27N3 = 537.67) |
| 4-43 | m/z = 639.27 (C47H33N3 = 639.80) | 4-44 | m/z = 601.25 (C44H31N3 = 601.75) |
| 4-45 | m/z = 571.22 (C40H30NPO = 571.66) | 4-46 | m/z = 639.27 (C47H33N3 = 639.80) |
| 4-47 | m/z = 779.33 (C58H41N3 = 779.99) | 4-48 | m/z = 547.23 (C42H29N = 547.70) |

TABLE 2-continued

| Compound | FD-MS | Compound | FD-MS |
|---|---|---|---|
| 4-49 | m/z = 623.26 (C48H33N = 623.80) | 4-50 | m/z = 690.30 (C52H38N2 = 690.89) |
| 4-51 | m/z = 701.28 (C52H35N3 = 701.87) | 4-52 | m/z = 553.19 (C40H27NS = 553.72) |
| 4-53 | m/z = 648.26 (C49H32N2 = 648.81) | 4-54 | m/z = 601.25 (C44H31N3 = 601.75) |
| 4-55 | m/z = 498.21 (C37H26N2 = 498.63) | 4-56 | m/z = 592.17 (C40H24N4S = 592.72) |
| 4-57 | m/z = 641.19 (C45H27N3S = 641.79) | 4-58 | m/z = 667.21 (C47H29N3S = 667.83) |
| 4-59 | m/z = 591.18 (C41H25N3S = 591.73) | 4-60 | m/z = 680.20 (C47H28N4S = 680.83) |
| 4-61 | m/z = 488.13 (C34H20N2S = 488.61) | 4-62 | m/z = 527.15 (C36H21N3S = 527.64) |
| 4-63 | m/z = 629.19 (C44H27N3S = 629.78) | 4-64 | m/z = 519.18 (C41H25N3S = 519.73) |
| 4-65 | m/z = 561.13 (C37H24NOPS = 561.64) | 4-66 | m/z = 629.19 (C44H27N3S = 692.78) |
| 4-67 | m/z = 769.26 (C55H35N3S = 769.97) | 4-68 | m/z = 537.16 (C39H23NS = 537.68) |
| 4-69 | m/z = 613.19 (C45H27NS = 613.78) | 4-70 | m/z = 680.23 (C49H32N2S = 680.87) |
| 4-71 | m/z = 691.21 (C49H29N3S = 691.85) | 4-72 | m/z = 543.11 (C37H21NS2 = 543.70) |
| 4-73 | m/z = 638.18 (C46H26N2S = 638.79) | 4-74 | m/z = 591.18 (C41H25N3S = 591.73) |
| 4-75 | m/z = 488.13 (C34H20N2S = 488.61) | 4-76 | m/z = 576.20 (C40H24N4 = 576.66) |
| 4-77 | m/z = 625.22 (C45H27N3O = 625.73) | 4-78 | m/z = 651.23 (C47H29N3O = 651.77) |
| 4-79 | m/z = 575.20 (C41H25N3O = 575.67) | 4-80 | m/z = 664.23 (C47H28N4O = 664.77) |
| 4-81 | m/z = 472.16 (C34H20N2O = 472.55) | 4-82 | m/z = 511.17 (C36H21N3O = 511.58) |
| 4-83 | m/z = 613.22 (C44H27N3O = 613.72) | 4-84 | m/z = 575.20 (C41H25N3O = 575.67) |
| 4-85 | m/z = 545.15 (C37H24NO2P = 545.58) | 4-86 | m/z = 613.22 (C44H27N3O = 613.72) |
| 4-87 | m/z = 753.28 (C55H35N3O = 735.90) | 4-88 | m/z = 521.18 (C39H23NO = 521.62) |
| 4-89 | m/z = 597.21 (C45H27NO = 597.72) | 4-90 | m/z = 664.25 (C49H32N2O = 664.81) |
| 4-91 | m/z = 651.24 (C46H29N5 = 651.77) | 4-92 | m/z = 700.26 (C51H32N4 = 700.84) |
| 4-93 | m/z = 726.28 (C53H34N4 = 726.88) | 4-94 | m/z = 650.25 (C47H30N4 = 650.78) |
| 4-95 | m/z = 739.27 (C53H33N5 = 739.88) | 4-96 | m/z = 547.20 (C40H25N3 = 547.66) |
| 4-97 | m/z = 586.22 (C42H26N4 = 586.70) | 4-98 | m/z = 688.26 (C50H32N4 = 688.83) |
| 4-99 | m/z = 650.25 (C47H30N4 = 650.78) | 4-100 | m/z = 620.20 (C43H29N2OP = 620.69) |
| 4-101 | m/z = 688.26 (C50H32N4 = 688.83) | 4-102 | m/z = 826.31 (C61H38N4 = 870.00) |
| 4-103 | m/z = 596.23 (C45H28N2 = 596.73) | 4-104 | m/z = 672.26 (C51H32N2 = 672.83) |
| 4-105 | m/z = 722.27 (C55H34N2 = 722.89) | 4-106 | m/z = 629.19 (C44H27N3S = 629.78) |
| 4-107 | m/z = 547.20 (C40H25N3 = 547.66) | 4-108 | m/z = 548.20 (C39H24N4 = 548.65) |
| 4-109 | m/z = 736.29 (C56H36N2 = 736.92) | 4-110 | m/z = 613.22 (C44H27N3O = 613.72) |
| 4-111 | m/z = 640.23 (C45H28N4O = 640.75) | 4-112 | m/z = 586.20 (C43H26N2O = 586.69) |
| 4-113 | m/z = 602.18 (C43H26N2S = 602.75) | 4-114 | m/z = 649.25 (C48H31N3 = 649.80) |
| 4-115 | m/z = 649.25 (C48H31N3 = 649.80) | 4-116 | m/z = 803.30 (C58H37N5 = 803.97) |
| 4-117 | m/z = 803.30 (C58H37N5 = 803.97) | 4-118 | m/z = 749.28 (C56H35N3 = 749.92) |
| 4-119 | m/z = 646.24 (C49H30N2 = 646.79) | 4-120 | m/z = 739.30 (C55H37N3 = 739.92) |
| 4-121 | m/z = 750.28 (C55H34N4 = 750.90) | 4-122 | m/z = 750.28 (C55H34N4 = 750.90) |
| 4-123 | m/z = 661.25 (C49H31N3 = 661.82) | 4-124 | m/z = 661.25 (C49H31N3 = 661.82) |
| 4-125 | m/z = 804.33 (C59H40N4 = 805.00) | 4-126 | m/z = 602.25 (C43H30N4 = 602.74) |
| 4-127 | m/z = 651.27 (C48H33N3 = 651.82) | 4-128 | m/z = 677.28 (C50H35N3 = 677.85) |
| 4-129 | m/z = 601.25 (C44H31N3 = 601.75) | 4-130 | m/z = 690.28 (C50H34N4 = 690.85) |
| 4-131 | m/z = 498.21 (C37H26N2 = 498.63) | 4-132 | m/z = 537.22 (C39H27N3 = 537.67) |
| 4-133 | m/z = 639.27 (C47H33N3 = 639.80) | 4-134 | m/z = 601.25 (C44H31N3 = 601.75) |
| 4-135 | m/z = 571.22 (C40H30NPO = 571.66) | 4-136 | m/z = 639.27 (C47H33N3 = 639.80) |
| 4-137 | m/z = 779.33 (C58H41N3 = 779.99) | 4-138 | m/z = 547.23 (C42H29N = 547.70) |
| 4-139 | m/z = 623.26 (C48H33N = 623.80) | 4-140 | m/z = 690.30 (C52H38N2 = 690.89) |
| 4-141 | m/z = 701.28 (C52H35N3 = 701.87) | 4-142 | m/z = 553.19 (C40H27NS = 553.72) |
| 4-143 | m/z = 648.26 (C49H32N2 = 648.81) | 4-144 | m/z = 601.25 (C44H31N3 = 601.75) |
| 4-145 | m/z = 498.21 (C37H26N2 = 498.63) | 4-146 | m/z = 592.17 (C40H24N4S = 592.72) |
| 4-147 | m/z = 641.19 (C45H27N3S = 641.79) | 4-148 | m/z = 667.21 (C47H29N3S = 667.83) |
| 4-149 | m/z = 591.18 (C41H25N3S = 591.73) | 4-150 | m/z = 680.20 (C47H28N4S = 680.83) |
| 4-151 | m/z = 488.13 (C34H20N2S = 488.61) | 4-152 | m/z = 527.15 (C36H21N3S = 527.64) |
| 4-153 | m/z = 629.19 (C44H27N3S = 629.78) | 4-154 | m/z = 519.18 (C41H25N3S = 519.73) |
| 4-155 | m/z = 561.13 (C37H24NOPS = 561.64) | 4-156 | m/z = 629.19 (C44H27N3S = 692.78) |
| 4-157 | m/z = 769.26 (C55H35N3S = 769.97) | 4-158 | m/z = 537.16 (C39H23NS = 537.68) |
| 4-159 | m/z = 613.19 (C45H27NS = 613.78) | 4-160 | m/z = 680.23 (C49H32N2S = 680.87) |
| 4-161 | m/z = 691.21 (C49H29N3S = 691.85) | 4-162 | m/z = 543.11 (C37H21NS2 = 543.70) |
| 4-163 | m/z = 638.18 (C46H26N2S = 638.79) | 4-164 | m/z = 591.18 (C41H25N3S = 591.73) |
| 4-165 | m/z = 488.13 (C34H20N2S = 488.61) | 4-166 | m/z = 576.20 (C40H24N4 = 576.66) |
| 4-167 | m/z = 625.22 (C45H27N3O = 625.73) | 4-168 | m/z = 651.23 (C47H29N3O = 651.77) |
| 4-169 | m/z = 575.20 (C41H25N3O = 575.67) | 4-170 | m/z = 664.23 (C47H28N4O = 664.77) |
| 4-171 | m/z = 472.16 (C34H20N2O = 472.55) | 4-172 | m/z = 511.17 (C36H21N3O = 511.58) |
| 4-173 | m/z = 613.22 (C44H27N3O = 613.72) | 4-174 | m/z = 575.20 (C41H25N3O = 575.67) |
| 4-175 | m/z = 545.15 (C37H24NO2P = 545.58) | 4-176 | m/z = 613.22 (C44H27N3O = 613.72) |
| 4-177 | m/z = 753.28 (C55H35N3O = 735.90) | 4-178 | m/z = 521.18 (C39H23NO = 521.62) |
| 4-179 | m/z = 597.21 (C45H27NO = 597.72) | 4-180 | m/z = 664.25 (C49H32N2O = 664.81) |
| 4-181 | m/z = 651.24 (C46H29N5 = 651.77) | 4-182 | m/z = 700.26 (C51H32N4 = 700.84) |
| 4-183 | m/z = 726.28 (C53H34N4 = 726.88) | 4-184 | m/z = 650.25 (C47H30N4 = 650.78) |
| 4-185 | m/z = 739.27 (C53H33N5 = 739.88) | 4-186 | m/z = 547.20 (C40H25N3 = 547.66) |
| 4-187 | m/z = 586.22 (C42H26N4 = 586.70) | 4-188 | m/z = 688.26 (C50H32N4 = 688.83) |
| 4-189 | m/z = 650.25 (C47H30N4 = 650.78) | 4-190 | m/z = 620.20 (C43H29N2OP = 620.69) |
| 4-191 | m/z = 688.26 (C50H32N4 = 688.83) | 4-192 | m/z = 826.31 (C61H38N4 = 827.00) |
| 4-193 | m/z = 596.23 (C45H28N2 = 596.73) | 4-194 | m/z = 672.26 (C51H32N2 = 672.83) |
| 4-195 | m/z = 722.27 (C55H34N2 = 722.89) | 4-196 | m/z = 629.19 (C44H27N3S = 629.78) |
| 4-197 | m/z = 547.20 (C40H25N3 = 547.66) | 4-198 | m/z = 548.20 (C39H24N4 = 548.65) |
| 4-199 | m/z = 736.29 (C56H36N2 = 736.92) | 4-200 | m/z = 613.22 (C44H27N3O = 613.72) |
| 4-201 | m/z = 640.23 (C45H28N4O = 640.75) | 4-202 | m/z = 586.20 (C43H26N2O = 586.69) |
| 4-203 | m/z = 602.18 (C43H26N2S = 602.75) | 4-204 | m/z = 649.25 (C48H31N3 = 649.80) |

TABLE 2-continued

| Compound | FD-MS | Compound | FD-MS |
| --- | --- | --- | --- |
| 4-205 | m/z = 649.25 (C48H31N3 = 649.80) | 4-206 | m/z = 803.30 (C58H37N5 = 803.97) |
| 4-207 | m/z = 803.30 (C58H37N5 = 803.97) | 4-208 | m/z = 749.28 (C56H35N3 = 749.92) |
| 4-209 | m/z = 646.24 (C49H30N2 = 646.79) | 4-210 | m/z = 739.30 (C55H37N3 = 739.92) |
| 4-211 | m/z = 750.28 (C55H34N4 = 750.90) | 4-212 | m/z = 750.28 (C55H34N4 = 750.90) |
| 4-213 | m/z = 661.25 (C49H31N3 = 661.81) | 4-214 | m/z = 661.25 (C49H31N3 = 661.81) |
| 4-215 | m/z = 804.33 (C59H40N4 = 805.00) | 4-216 | m/z = 651.24 (C46H29N5 = 651.77) |
| 4-217 | m/z = 700.26 (C51H32N4 = 700.84) | 4-218 | m/z = 726.28 (C53H34N4 = 726.88) |
| 4-219 | m/z = 650.25 (C47H30N4 = 650.78) | 4-220 | m/z = 739.27 (C53H33N5 = 739.88) |
| 4-221 | m/z = 547.20 (C40H25N3 = 547.66) | 4-222 | m/z = 586.22 (C42H26N4 = 586.70) |
| 4-223 | m/z = 688.26 (C50H32N4 = 688.83) | 4-224 | m/z = 650.25 (C47H30N4 = 650.78) |
| 4-225 | m/z = 620.20 (C43H29N2OP = 620.69) | 4-226 | m/z = 688.26 (C50H32N4 = 688.83) |
| 4-227 | m/z = 826.31 (C61H38N4 = 827.00) | 4-228 | m/z = 596.23 (C45H28N2 = 596.73) |
| 4-229 | m/z = 672.26 (C51H32N2 = 672.83) | 4-230 | m/z = 722.27 (C55H34N2 = 722.89) |
| 4-231 | m/z = 629.19 (C44H27N3S = 629.78) | 4-232 | m/z = 547.20 (C40H25N3 = 547.66) |
| 4-233 | m/z = 548.20 (C39H24N4 = 548.65) | 4-234 | m/z = 736.29 (C56H36N2 = 736.92) |
| 4-235 | m/z = 613.22 (C44H27N3O = 613.72) | 4-236 | m/z = 640.23 (C45H28N4O = 640.75) |
| 4-237 | m/z = 586.20 (C43H26N2O = 586.69) | 4-238 | m/z = 602.18 (C43H26N2S = 602.75) |
| 4-239 | m/z = 649.25 (C48H31N3 = 649.80) | 4-240 | m/z = 649.25 (C48H31N3 = 649.80) |
| 4-241 | m/z = 803.30 (C58H37N5 = 803.97) | 4-242 | m/z = 803.30 (C58H37N5 = 803.97) |
| 4-243 | m/z = 749.28 (C56H35N3 = 749.92) | 4-244 | m/z = 646.24 (C49H30N2 = 646.79) |
| 4-245 | m/z = 739.30 (C55H37N3 = 739.92) | 4-246 | m/z = 750.28 (C55H34N4 = 750.90) |
| 4-247 | m/z = 750.28 (C55H34N4 = 750.90) | 4-248 | m/z = 661.25 (C49H31N3 = 661.81) |
| 4-249 | m/z = 661.25 (C49H31N3 = 661.81) | 4-250 | m/z = 804.33 (C59H40N4 = 805.00) |
| 4-251 | m/z = 789.25 (C59H35NS = 790.00) | 4-252 | m/z = 789.25 (C59H35NS = 790.00) |
| 4-253 | m/z = 663.20 (C49H29NS = 663.84) | 4-254 | m/z = 613.19 (C45H27NS = 613.78) |
| 4-255 | m/z = 637.16 (C43H28NOPS = 637.74) | 4-256 | m/z = 594.16 (C38H22N6S = 594.70) |
| 4-257 | m/z = 594.16 (C38H22N6S = 594.70) | 4-258 | m/z = 594.16 (C38H22N6S = 594.70) |
| 4-259 | m/z = 692.20 (C48H28N4S = 692.84) | 4-260 | m/z = 692.20 (C48H28N4S = 692.84) |
| 4-261 | m/z = 792.23 (C56H32N4S = 792.96) | 4-262 | m/z = 668.20 (C46H28N4S = 668.82) |
| 4-263 | m/z = 670.19 (C44H26N6S = 670.79) | 4-264 | m/z = 670.19 (C44H26N6S = 670.79) |
| 4-265 | m/z = 670.19 (C44H26N6S = 670.79) | 4-266 | m/z = 768.23 (C54H32N4S = 768.94) |
| 4-267 | m/z = 768.23 (C54H32N4S = 768.94) | 4-268 | m/z = 868.27 (C62H36N4S = 869.06) |
| 4-269 | m/z = 691.21 (C49H29N3S = 691.85) | 4-270 | m/z = 691.21 (C49H29N3S = 691.85) |
| 4-271 | m/z = 791.24 (C57H33N3S = 791.97) | 4-272 | m/z = 743.24 (C53H33N3S = 743.93) |
| 4-273 | m/z = 667.21 (C47H29N3S = 667.83) | 4-274 | m/z = 743.24 (C53H33N3S = 743.93) |
| 4-275 | m/z = 667.21 (C47H29N3S = 667.83) | 4-276 | m/z = 667.21 (C47H29N3S = 667.83) |
| 4-277 | m/z = 767.24 (C55H33N3S = 767.95) | 4-278 | m/z = 767.24 (C55H33N3S = 767.95) |
| 4-279 | m/z = 867.27 (C63H37N3S = 868.07) | 4-280 | m/z = 819.27 (C59H37N3S = 820.03) |
| 4-281 | m/z = 743.24 (C53H33N3S = 743.93) | 4-282 | m/z = 819.27 (C59H37N3S = 820.03) |
| 4-283 | m/z = 743.24 (C53H33N3S = 743.93) | 4-284 | m/z = 691.21 (C49H29N3S = 691.85) |
| 4-285 | m/z = 691.21 (C49H29N3S = 691.85) | 4-286 | m/z = 789.25 (C59H35NS = 790.00) |
| 4-287 | m/z = 743.24 (C53H33N3S = 743.93) | 4-288 | m/z = 667.21 (C47H29N3S = 667.83) |
| 4-289 | m/z = 743.24 (C53H33N3S = 743.93) | 4-290 | m/z = 667.21 (C47H29N3S = 667.83) |
| 4-291 | m/z = 592.17 (C40H24N4S = 592.72) | 4-292 | m/z = 668.20 (C46H28N4S = 668.82) |
| 4-293 | m/z = 667.21 (C47H29N3S = 667.83) | 4-294 | m/z = 667.21 (C47H29N3S = 667.83) |
| 4-295 | m/z = 592.17 (C40H24N4S = 592.72) | 4-296 | m/z = 767.24 (C55H33N3S = 767.95) |
| 4-297 | m/z = 767.24 (C55H33N3S = 767.95) | 4-298 | m/z = 867.27 (C63H37N3S = 868.07) |
| 4-299 | m/z = 819.27 (C59H37N3S = 820.03) | 4-300 | m/z = 743.24 (C53H33N3S = 743.93) |
| 4-301 | m/z = 743.24 (C53H33N3S = 743.93) | 4-302 | m/z = 819.27 (C59H37N3S = 820.03) |
| 4-303 | m/z = 743.24 (C53H33N3S = 743.93) | 4-304 | m/z = 743.24 (C53H33N3S = 743.93) |
| 4-305 | m/z = 668.20 (C46H28N4S = 668.82) | 4-306 | m/z = 744.23 (C52H32N4S = 744.92) |
| 4-307 | m/z = 744.23 (C52H32N4S = 744.92) | 4-308 | m/z = 641.19 (C45H27N3S = 641.79) |
| 4-309 | m/z = 717.22 (C51H31N3S = 717.89) | 4-310 | m/z = 565.16 (C39H23N3S = 565.69) |
| 4-311 | m/z = 641.19 (C45H27N3S = 641.79) | 4-312 | m/z = 615.18 (C43H25N3S = 615.75) |
| 4-313 | m/z = 615.18 (C43H25N3S = 615.75) | 4-314 | m/z = 641.19 (C45H27N3S = 641.79) |
| 4-315 | m/z = 717.22 (C51H31N3S = 717.89) | 4-316 | m/z = 691.21 (C49H29N3S = 691.85) |
| 4-317 | m/z = 691.21 (C49H29N3S = 691.85) | 4-318 | m/z = 667.21 (C47H29N3S = 667.83) |
| 4-319 | m/z = 819.27 (C59H37N3S = 820.03) | 4-320 | m/z = 819.27 (C59H37N3S = 820.03) |
| 4-321 | m/z = 767.24 (C55H33N3S = 767.95) | 4-322 | m/z = 767.24 (C55H33N3S = 767.95) |
| 4-323 | m/z = 743.24 (C53H33N3S = 743.93) | 4-324 | m/z = 743.24 (C53H33N3S = 743.93) |
| 4-325 | m/z = 717.22 (C51H31N3S = 717.89) | 4-326 | m/z = 717.22 (C51H31N3S = 717.89) |
| 4-327 | m/z = 767.24 (C55H33N3S = 767.95) | 4-328 | m/z = 565.16 (C39H23N3S = 565.69) |
| 4-329 | m/z = 641.19 (C45H27N3S = 641.79) | 4-330 | m/z = 641.19 (C45H27N3S = 641.79) |
| 4-331 | m/z = 641.19 (C45H27N3S = 641.79) | 4-332 | m/z = 717.22 (C51H31N3S = 717.89) |
| 4-333 | m/z = 717.22 (C51H31N3S = 717.89) | 4-334 | m/z = 539.15 (C37H21N3S = 539.66) |
| 4-335 | m/z = 615.18 (C43H25N3S = 615.75) | 4-336 | m/z = 615.18 (C43H25N3S = 615.75) |
| 4-337 | m/z = 553.16 (C38H23N3S = 553.68) | 4-338 | m/z = 553.16 (C38H23N3S = 553.68) |
| 4-339 | m/z = 553.16 (C38H23N3S = 553.68) | 4-340 | m/z = 553.16 (C38H23N3S = 553.68) |
| 4-341 | m/z = 505.16 (C34H23N3S = 505.64) | 4-342 | m/z = 581.19 (C40H27N3S = 581.74) |
| 4-343 | m/z = 581.19 (C40H27N3S = 581.74) | 4-344 | m/z = 629.19 (C44H27N3S = 629.78) |
| 4-345 | m/z = 581.19 (C40H27N3S = 581.74) | 4-346 | m/z = 581.19 (C40H27N3S = 581.74) |
| 4-347 | m/z = 505.16 (C34H23N3S = 505.64) | 4-348 | m/z = 629.19 (C44H27N3S = 629.78) |
| 4-349 | m/z = 570.12 (C38H22N2S2 = 570.73) | 4-350 | m/z = 570.12 (C38H22N2S2 = 570.73) |
| 4-351 | m/z = 570.12 (C38H22N2S2 = 570.73) | 4-352 | m/z = 570.12 (C38H22N2S2 = 570.73) |
| 4-353 | m/z = 666.21 (C48H30N2S = 666.84) | 4-354 | m/z = 592.17 (C40H24N4S = 592.72) |
| 4-355 | m/z = 592.17 (C40H24N4S = 592.72) | 4-356 | m/z = 592.17 (C40H24N4S = 592.72) |
| 4-357 | m/z = 668.20 (C46H28N4S = 668.82) | 4-358 | m/z = 668.20 (C46H28N4S = 668.82) |
| 4-359 | m/z = 668.20 (C46H28N4S = 668.82) | 4-360 | m/z = 515.15 (C35H21N3S = 515.63) |

TABLE 2-continued

| Compound | FD-MS | Compound | FD-MS |
|---|---|---|---|
| 4-361 | m/z = 515.15 (C35H21N3S = 515.63) | 4-362 | m/z = 515.15 (C35H21N3S = 515.63) |
| 4-363 | m/z = 591.18 (C41H25N3S = 591.73) | 4-364 | m/z = 591.18 (C41H25N3S = 591.73) |
| 4-365 | m/z = 591.18 (C41H25N3S = 591.73) | 4-366 | m/z = 789.25 (C59H35NS = 790.00) |
| 4-367 | m/z = 789.25 (C59H35NS = 790.00) | 4-368 | m/z = 663.20 (C49H29NS = 663.84) |
| 4-369 | m/z = 613.19 (C45H27NS = 613.78) | 4-370 | m/z = 637.16 (C43H28NOPS = 637.74) |
| 4-371 | m/z = 594.16 (C38H22N6S = 594.70) | 4-372 | m/z = 594.16 (C38H22N6S = 594.70) |
| 4-373 | m/z = 594.16 (C38H22N6S = 594.70) | 4-374 | m/z = 692.20 (C48H28N4S = 692.84) |
| 4-375 | m/z = 692.20 (C48H28N4S = 692.84) | 4-376 | m/z = 792.23 (C56H32N4S = 792.96) |
| 4-377 | m/z = 668.20 (C46H28N4S = 668.82) | 4-378 | m/z = 670.19 (C44H26N6S = 670.79) |
| 4-379 | m/z = 670.19 (C44H26N6S = 670.79) | 4-380 | m/z = 670.19 (C44H26N6S = 670.79) |
| 4-381 | m/z = 768.23 (C54H32N4S = 768.94) | 4-382 | m/z = 768.23 (C54H32N4S = 768.94) |
| 4-383 | m/z = 868.27 (C62H36N4S = 869.06) | 4-384 | m/z = 691.21 (C49H29N3S = 691.85) |
| 4-385 | m/z = 691.21 (C49H29N3S = 691.85) | 4-386 | m/z = 791.24 (C57H33N3S = 791.97) |
| 4-387 | m/z = 743.24 (C53H33N3S = 743.93) | 4-388 | m/z = 667.21 (C47H29N3S = 667.83) |
| 4-389 | m/z = 743.24 (C53H33N3S = 743.93) | 4-390 | m/z = 667.21 (C47H29N3S = 667.83) |
| 4-391 | m/z = 667.21 (C47H29N3S = 667.83) | 4-392 | m/z = 767.24 (C55H33N3S = 767.95) |
| 4-393 | m/z = 767.24 (C55H33N3S = 767.95) | 4-394 | m/z = 867.27 (C63H37N3S = 868.07) |
| 4-395 | m/z = 819.27 (C59H37N3S = 820.03) | 4-396 | m/z = 743.24 (C53H33N3S = 743.93) |
| 4-397 | m/z = 819.27 (C59H37N3S = 820.03) | 4-398 | m/z = 743.24 (C53H33N3S = 743.93) |
| 4-399 | m/z = 691.21 (C49H29N3S = 691.85) | 4-400 | m/z = 691.21 (C49H29N3S = 691.85) |
| 4-401 | m/z = 789.25 (C59H35NS = 790.00) | 4-402 | m/z = 743.24 (C53H33N3S = 743.93) |
| 4-403 | m/z = 667.21 (C47H29N3S = 667.83) | 4-404 | m/z = 743.24 (C53H33N3S = 743.93) |
| 4-405 | m/z = 667.21 (C47H29N3S = 667.83) | 4-406 | m/z = 592.17 (C40H24N4S = 592.72) |
| 4-407 | m/z = 668.20 (C46H28N4S = 668.82) | 4-408 | m/z = 667.21 (C47H29N3S = 667.83) |
| 4-409 | m/z = 667.21 (C47H29N3S = 667.83) | 4-410 | m/z = 592.17 (C40H24N4S = 592.72) |
| 4-411 | m/z = 767.24 (C55H33N3S = 767.95) | 4-412 | m/z = 767.24 (C55H33N3S = 767.95) |
| 4-413 | m/z = 867.27 (C63H37N3S = 868.07) | 4-414 | m/z = 819.27 (C59H37N3S = 820.03) |
| 4-415 | m/z = 743.24 (C53H33N3S = 743.93) | 4-416 | m/z = 743.24 (C53H33N3S = 743.93) |
| 4-417 | m/z = 819.27 (C59H37N3S = 820.03) | 4-418 | m/z = 743.24 (C53H33N3S = 743.93) |
| 4-419 | m/z = 743.24 (C53H33N3S = 743.93) | 4-420 | m/z = 668.20 (C46H28N4S = 668.82) |
| 4-421 | m/z = 744.23 (C52H32N4S = 744.92) | 4-422 | m/z = 744.23 (C52H32N4S = 744.92) |
| 4-423 | m/z = 641.19 (C45H27N3S = 641.79) | 4-424 | m/z = 717.22 (C51H31N3S = 717.89) |
| 4-425 | m/z = 565.16 (C39H23N3S = 565.69) | 4-426 | m/z = 641.19 (C45H27N3S = 641.79) |
| 4-427 | m/z = 615.18 (C43H25N3S = 615.75) | 4-428 | m/z = 615.18 (C43H25N3S = 615.75) |
| 4-429 | m/z = 641.19 (C45H27N3S = 641.79) | 4-430 | m/z = 717.22 (C51H31N3S = 717.89) |
| 4-431 | m/z = 691.21 (C49H29N3S = 691.85) | 4-432 | m/z = 691.21 (C49H29N3S = 691.85) |
| 4-433 | m/z = 667.21 (C47H29N3S = 667.83) | 4-434 | m/z = 819.27 (C59H37N3S = 820.03) |
| 4-435 | m/z = 819.27 (C59H37N3S = 820.03) | 4-436 | m/z = 767.24 (C55H33N3S = 767.95) |
| 4-437 | m/z = 767.24 (C55H33N3S = 767.95) | 4-438 | m/z = 743.24 (C53H33N3S = 743.93) |
| 4-439 | m/z = 743.24 (C53H33N3S = 743.93) | 4-440 | m/z = 717.22 (C51H31N3S = 717.89) |
| 4-441 | m/z = 717.22 (C51H31N3S = 717.89) | 4-442 | m/z = 767.24 (C55H33N3S = 767.95) |
| 4-443 | m/z = 565.16 (C39H23N3S = 565.69) | 4-444 | m/z = 641.19 (C45H27N3S = 641.79) |
| 4-445 | m/z = 641.19 (C45H27N3S = 641.79) | 4-446 | m/z = 641.19 (C45H27N3S = 641.79) |
| 4-447 | m/z = 717.22 (C51H31N3S = 717.89) | 4-448 | m/z = 717.22 (C51H31N3S = 717.89) |
| 4-449 | m/z = 539.15 (C37H21N3S = 539.66) | 4-450 | m/z = 615.18 (C43H25N3S = 615.75) |
| 4-451 | m/z = 615.18 (C43H25N3S = 615.75) | 4-452 | m/z = 553.16 (C38H23N3S = 553.68) |
| 4-453 | m/z = 553.16 (C38H23N3S = 553.68) | 4-454 | m/z = 553.16 (C38H23N3S = 553.68) |
| 4-455 | m/z = 553.16 (C38H23N3S = 553.68) | 4-456 | m/z = 505.16 (C34H23N3S = 505.64) |
| 4-457 | m/z = 581.19 (C40H27N3S = 581.74) | 4-458 | m/z = 581.19 (C40H27N3S = 581.74) |
| 4-459 | m/z = 629.19 (C44H27N3S = 629.78) | 4-460 | m/z = 581.19 (C40H27N3S = 581.74) |
| 4-461 | m/z = 581.19 (C40H27N3S = 581.74) | 4-462 | m/z = 505.16 (C34H23N3S = 505.64) |
| 4-463 | m/z = 629.19 (C44H27N3S = 629.78) | 4-464 | m/z = 570.12 (C38H22N2S2 = 570.73) |
| 4-465 | m/z = 570.12 (C38H22N2S2 = 570.73) | 4-466 | m/z = 570.12 (C38H22N2S2 = 570.73) |
| 4-467 | m/z = 570.12 (C38H22N2S2 = 570.73) | 4-468 | m/z = 666.21 (C48H30N2S = 666.84) |
| 4-469 | m/z = 592.17 (C40H24N4S = 592.72) | 4-470 | m/z = 592.17 (C40H24N4S = 592.72) |
| 4-471 | m/z = 592.17 (C40H24N4S = 592.72) | 4-472 | m/z = 668.20 (C46H28N4S = 668.82) |
| 4-473 | m/z = 668.20 (C46H28N4S = 668.82) | 4-474 | m/z = 668.20 (C46H28N4S = 668.82) |
| 4-475 | m/z = 515.15 (C35H21N3S = 515.63) | 4-476 | m/z = 515.15 (C35H21N3S = 515.63) |
| 4-477 | m/z = 515.15 (C35H21N3S = 515.63) | 4-478 | m/z = 591.18 (C41H25N3S = 591.73) |
| 4-479 | m/z = 591.18 (C41H25N3S = 591.73) | 4-480 | m/z = 591.18 (C41H25N3S = 591.73) |
| 4-481 | m/z = 773.27 (C59H35NO = 773.93) | 4-482 | m/z = 773.27 (C59H35NO = 773.93) |
| 4-483 | m/z = 647.22 (C49H29NO = 647.78) | 4-484 | m/z = 597.21 (C45H27NO = 597.72) |
| 4-485 | m/z = 621.19 (C43H28NO2P = 621.68) | 4-486 | m/z = 578.19 (C38H22N6O = 578.63) |
| 4-487 | m/z = 578.19 (C38H22N6O = 578.63) | 4-488 | m/z = 578.19 (C38H22N6O = 578.63) |
| 4-489 | m/z = 676.23 (C48H28N4O = 676.78) | 4-490 | m/z = 676.23 (C48H28N4O = 676.78) |
| 4-491 | m/z = 776.26 (C56H32N4O = 776.90) | 4-492 | m/z = 652.23 (C46H28N4O = 652.76) |
| 4-493 | m/z = 654.22 (C44H26N6O = 654.73) | 4-494 | m/z = 654.22 (C44H26N6O = 654.73) |
| 4-495 | m/z = 654.22 (C44H26N6O = 654.73) | 4-496 | m/z = 752.26 (C54H32N4O = 752.88) |
| 4-497 | m/z = 752.26 (C54H32N4O = 752.88) | 4-498 | m/z = 852.29 (C62H36N4O = 853.00) |
| 4-499 | m/z = 675.23 (C49H29N3O = 675.79) | 4-500 | m/z = 675.23 (C49H29N3O = 675.79) |
| 4-501 | m/z = 775.26 (C57H33N3O = 775.91) | 4-502 | m/z = 727.26 (C53H33N3O = 727.87) |
| 4-503 | m/z = 651.23 (C47H29N3O = 651.77) | 4-504 | m/z = 727.26 (C53H33N3O = 727.87) |
| 4-505 | m/z = 651.23 (C47H29N3O = 651.77) | 4-506 | m/z = 651.23 (C47H29N3O = 651.77) |
| 4-507 | m/z = 751.26 (C55H33N3O = 751.89) | 4-508 | m/z = 751.26 (C55H33N3O = 751.89) |
| 4-509 | m/z = 851.29 (C63H37N3O = 852.01) | 4-510 | m/z = 803.29 (C59H37N3O = 803.97) |
| 4-511 | m/z = 727.26 (C53H33N3O = 727.87) | 4-512 | m/z = 803.29 (C59H37N3O = 803.97) |
| 4-513 | m/z = 727.26 (C53H33N3O = 727.87) | 4-514 | m/z = 675.23 (C49H29N3O = 675.79) |
| 4-515 | m/z = 675.23 (C49H29N3O = 675.79) | 4-516 | m/z = 773.27 (C59H35NO = 773.93) |

TABLE 2-continued

| Compound | FD-MS | Compound | FD-MS |
|---|---|---|---|
| 4-517 | m/z = 727.26 (C53H33N3O = 727.87) | 4-518 | m/z = 651.23 (C47H29N3O = 651.77) |
| 4-519 | m/z = 727.26 (C53H33N3O = 727.87) | 4-520 | m/z = 651.23 (C47H29N3O = 651.77) |
| 4-521 | m/z = 576.20 (C40H24N4O = 576.66) | 4-522 | m/z = 652.23 (C46H28N4O = 652.76) |
| 4-523 | m/z = 651.23 (C47H29N3O = 651.77) | 4-524 | m/z = 651.23 (C47H29N3O = 651.77) |
| 4-525 | m/z = 576.20 (C40H24N4O = 576.66) | 4-526 | m/z = 751.26 (C55H33N3O = 751.89) |
| 4-527 | m/z = 751.26 (C55H33N3O = 751.89) | 4-528 | m/z = 851.29 (C63H37N3O = 852.01) |
| 4-529 | m/z = 803.29 (C59H37N3O = 803.97) | 4-530 | m/z = 727.26 (C53H33N3O = 727.87) |
| 4-531 | m/z = 727.26 (C53H33N3O = 727.87) | 4-532 | m/z = 803.29 (C59H37N3O = 803.97) |
| 4-533 | m/z = 727.26 (C53H33N3O = 727.87) | 4-534 | m/z = 727.26 (C53H33N3O = 727.87) |
| 4-535 | m/z = 652.23 (C46H28N4O = 652.76) | 4-536 | m/z = 728.26 (C52H32N4O = 728.86) |
| 4-537 | m/z = 728.26 (C52H32N4O = 728.86) | 4-538 | m/z = 625.22 (C45H27N3O = 625.73) |
| 4-539 | m/z = 701.25 (C51H31N3O = 701.83) | 4-540 | m/z = 549.18 (C52H32N4O = 549.63) |
| 4-541 | m/z = 625.22 (C45H27N3O = 625.73) | 4-542 | m/z = 599.20 (C43H25N3O = 599.69) |
| 4-543 | m/z = 599.20 (C43H25N3O = 599.69) | 4-544 | m/z = 625.22 (C45H27N3O = 625.73) |
| 4-545 | m/z = 701.25 (C51H31N3O = 701.83) | 4-546 | m/z = 675.23 (C49H29N3O = 675.79) |
| 4-547 | m/z = 675.23 (C49H29N3O = 675.79) | 4-548 | m/z = 651.23 (C47H29N3O = 651.77) |
| 4-549 | m/z = 803.29 (C59H37N3O = 803.97) | 4-550 | m/z = 803.29 (C59H37N3O = 803.97) |
| 4-551 | m/z = 751.26 (C55H33N3O = 751.89) | 4-552 | m/z = 751.26 (C55H33N3O = 751.89) |
| 4-553 | m/z = 727.26 (C53H33N3O = 727.87) | 4-554 | m/z = 727.26 (C53H33N3O = 727.87) |
| 4-555 | m/z = 701.25 (C51H31N3O = 701.83) | 4-556 | m/z = 701.25 (C51H31N3O = 701.83) |
| 4-557 | m/z = 751.26 (C55H33N3O = 751.89) | 4-558 | m/z = 549.18 (C52H32N4O = 549.63) |
| 4-559 | m/z = 625.22 (C45H27N3O = 625.73) | 4-560 | m/z = 625.22 (C45H27N3O = 625.73) |
| 4-561 | m/z = 625.22 (C45H27N3O = 625.73) | 4-562 | m/z = 701.25 (C51H31N3O = 701.83) |
| 4-563 | m/z = 701.25 (C51H31N3O = 701.83) | 4-564 | m/z = 523.17 (C37H21N3O = 523.60) |
| 4-565 | m/z = 599.20 (C43H25N3O = 599.69) | 4-566 | m/z = 599.20 (C43H25N3O = 599.69) |
| 4-567 | m/z = 537.18 (C38H23N3O = 537.62) | 4-568 | m/z = 537.18 (C38H23N3O = 537.62) |
| 4-569 | m/z = 537.18 (C38H23N3O = 537.62) | 4-570 | m/z = 537.18 (C38H23N3O = 537.62) |
| 4-571 | m/z = 489.18 (C34H23N3O = 489.58) | 4-572 | m/z = 565.22 (C40H27N3O = 565.68) |
| 4-573 | m/z = 565.22 (C40H27N3O = 565.68) | 4-574 | m/z = 613.22 (C44H27N3O = 613.72) |
| 4-575 | m/z = 565.22 (C40H27N3O = 565.68) | 4-576 | m/z = 565.22 (C40H27N3O = 565.68) |
| 4-577 | m/z = 489.18 (C34H23N3O = 489.58) | 4-578 | m/z = 613.22 (C44H27N3O = 613.72) |
| 4-579 | m/z = 554.15 (C38H22N2OS = 554.67) | 4-580 | m/z = 554.15 (C38H22N2OS = 554.67) |
| 4-581 | m/z = 554.15 (C38H22N2OS = 554.67) | 4-582 | m/z = 554.15 (C38H22N2OS = 554.67) |
| 4-583 | m/z = 650.24 (C48H30N2O = 650.78) | 4-584 | m/z = 576.20 (C40H24N4O = 576.66) |
| 4-585 | m/z = 576.20 (C40H24N4O = 576.66) | 4-586 | m/z = 576.20 (C40H24N4O = 576.66) |
| 4-587 | m/z = 652.23 (C46H28N4O = 652.76) | 4-588 | m/z = 652.23 (C46H28N4O = 652.76) |
| 4-589 | m/z = 652.23 (C46H28N4O = 652.76) | 4-590 | m/z = 499.17 (C35H21N3O = 499.57) |
| 4-591 | m/z = 499.17 (C35H21N3O = 499.57) | 4-592 | m/z = 499.17 (C35H21N3O = 499.57) |
| 4-593 | m/z = 575.20 (C41H25N3O = 575.67) | 4-594 | m/z = 575.20 (C41H25N3O = 575.67) |
| 4-595 | m/z = 575.20 (C41H25N3O = 575.67) | 4-596 | m/z = 773.27 (C59H35NO = 773.93) |
| 4-597 | m/z = 773.27 (C59H35NO = 773.93) | 4-598 | m/z = 647.22 (C49H29NO = 647.78) |
| 4-599 | m/z = 597.21 (C45H27NO = 597.72) | 4-600 | m/z = 621.19 (C43H28NO2P = 621.68) |
| 4-601 | m/z = 578.19 (C38H22N6O = 578.63) | 4-602 | m/z = 578.19 (C38H22N6O = 578.63) |
| 4-603 | m/z = 578.19 (C38H22N6O = 578.63) | 4-604 | m/z = 676.23 (C48H28N4O = 676.78) |
| 4-605 | m/z = 676.23 (C48H28N4O = 676.78) | 4-606 | m/z = 776.26 (C56H32N4O = 776.90) |
| 4-607 | m/z = 652.23 (C46H28N4O = 652.76) | 4-608 | m/z = 654.22 (C44H26N6O = 654.73) |
| 4-609 | m/z = 654.22 (C44H26N6O = 654.73) | 4-610 | m/z = 654.22 (C44H26N6O = 654.73) |
| 4-611 | m/z = 752.26 (C54H32N4O = 752.88) | 4-612 | m/z = 752.26 (C54H32N4O = 752.88) |
| 4-613 | m/z = 852.29 (C62H36N4O = 853.00) | 4-614 | m/z = 675.23 (C49H29N3O = 675.79) |
| 4-615 | m/z = 675.23 (C49H29N3O = 675.79) | 4-616 | m/z = 775.26 (C57H33N3O = 775.91) |
| 4-617 | m/z = 727.26 (C53H33N3O = 727.87) | 4-618 | m/z = 651.23 (C47H29N3O = 651.77) |
| 4-619 | m/z = 727.26 (C53H33N3O = 727.87) | 4-620 | m/z = 651.23 (C47H29N3O = 651.77) |
| 4-621 | m/z = 651.23 (C47H29N3O = 651.77) | 4-622 | m/z = 751.26 (C55H33N3O = 751.89) |
| 4-623 | m/z = 751.26 (C55H33N3O = 751.89) | 4-624 | m/z = 851.29 (C63H37N3O = 852.01) |
| 4-625 | m/z = 803.29 (C59H37N3O = 803.97) | 4-626 | m/z = 727.26 (C53H33N3O = 727.87) |
| 4-627 | m/z = 803.29 (C59H37N3O = 803.97) | 4-628 | m/z = 727.26 (C53H33N3O = 727.87) |
| 4-629 | m/z = 675.23 (C49H29N3O = 675.79) | 4-630 | m/z = 675.23 (C49H29N3O = 675.79) |
| 4-631 | m/z = 773.27 (C59H35NO = 773.93) | 4-632 | m/z = 727.26 (C53H33N3O = 727.87) |
| 4-633 | m/z = 651.23 (C47H29N3O = 651.77) | 4-634 | m/z = 727.26 (C53H33N3O = 727.87) |
| 4-635 | m/z = 651.23 (C47H29N3O = 651.77) | 4-636 | m/z = 576.20 (C40H24N4O = 576.66) |
| 4-637 | m/z = 652.23 (C46H28N4O = 652.76) | 4-638 | m/z = 651.23 (C47H29N3O = 651.77) |
| 4-639 | m/z = 651.23 (C47H29N3O = 651.77) | 4-640 | m/z = 576.20 (C40H24N4O = 576.66) |
| 4-641 | m/z = 751.26 (C55H33N3O = 751.89) | 4-642 | m/z = 751.26 (C55H33N3O = 751.89) |
| 4-643 | m/z = 851.29 (C63H37N3O = 852.01) | 4-644 | m/z = 803.29 (C59H37N3O = 803.97) |
| 4-645 | m/z = 727.26 (C53H33N3O = 727.87) | 4-646 | m/z = 727.26 (C53H33N3O = 727.87) |
| 4-647 | m/z = 803.29 (C59H37N3O = 803.97) | 4-648 | m/z = 727.26 (C53H33N3O = 727.87) |
| 4-649 | m/z = 727.26 (C53H33N3O = 727.87) | 4-650 | m/z = 652.23 (C46H28N4O = 652.76) |
| 4-651 | m/z = 728.26 (C52H32N4O = 728.86) | 4-652 | m/z = 728.26 (C52H32N4O = 728.86) |
| 4-653 | m/z = 625.22 (C45H27N3O = 625.73) | 4-654 | m/z = 701.25 (C51H31N3O = 701.83) |
| 4-655 | m/z = 549.18 (C52H32N4O = 549.63) | 4-656 | m/z = 625.22 (C45H27N3O = 625.73) |
| 4-657 | m/z = 599.20 (C43H25N3O = 599.69) | 4-658 | m/z = 599.20 (C43H25N3O = 599.69) |
| 4-659 | m/z = 625.22 (C45H27N3O = 625.73) | 4-660 | m/z = 701.25 (C51H31N3O = 701.83) |
| 4-661 | m/z = 675.23 (C49H29N3O = 675.79) | 4-662 | m/z = 675.23 (C49H29N3O = 675.79) |
| 4-663 | m/z = 651.23 (C47H29N3O = 651.77) | 4-664 | m/z = 803.29 (C59H37N3O = 803.97) |
| 4-665 | m/z = 803.29 (C59H37N3O = 803.97) | 4-666 | m/z = 751.26 (C55H33N3O = 751.89) |
| 4-667 | m/z = 751.26 (C55H33N3O = 751.89) | 4-668 | m/z = 727.26 (C53H33N3O = 727.87) |
| 4-669 | m/z = 727.26 (C53H33N3O = 727.87) | 4-670 | m/z = 701.25 (C51H31N3O = 701.83) |
| 4-671 | m/z = 701.25 (C51H31N3O = 701.83) | 4-672 | m/z = 751.26 (C55H33N3O = 751.89) |

TABLE 2-continued

| Compound | FD-MS | Compound | FD-MS |
|---|---|---|---|
| 4-673 | m/z = 549.18 (C52H32N4O = 549.63) | 4-674 | m/z = 625.22 (C45H27N3O = 625.73) |
| 4-675 | m/z = 625.22 (C45H27N3O = 625.73) | 4-676 | m/z = 625.22 (C45H27N3O = 625.73) |
| 4-677 | m/z = 701.25 (C51H31N3O = 701.83) | 4-678 | m/z = 701.25 (C51H31N3O = 701.83) |
| 4-679 | m/z = 523.17 (C37H21N3O = 523.60) | 4-680 | m/z = 599.20 (C43H25N3O = 599.69) |
| 4-681 | m/z = 599.20 (C43H25N3O = 599.69) | 4-682 | m/z = 537.18 (C38H23N3O = 537.62) |
| 4-683 | m/z = 537.18 (C38H23N3O = 537.62) | 4-684 | m/z = 537.18 (C38H23N3O = 537.62) |
| 4-685 | m/z = 537.18 (C38H23N3O = 537.62) | 4-686 | m/z = 489.18 (C34H23N3O = 489.58) |
| 4-687 | m/z = 565.22 (C40H27N3O = 565.68) | 4-688 | m/z = 565.22 (C40H27N3O = 565.68) |
| 4-689 | m/z = 613.22 (C44H27N3O = 613.72) | 4-690 | m/z = 565.22 (C40H27N3O = 565.68) |
| 4-691 | m/z = 565.22 (C40H27N3O = 565.68) | 4-692 | m/z = 489.18 (C34H23N3O = 489.58) |
| 4-693 | m/z = 613.22 (C44H27N3O = 613.72) | 4-694 | m/z = 554.15 (C38H22N2OS = 554.67) |
| 4-695 | m/z = 554.15 (C38H22N2OS = 554.67) | 4-696 | m/z = 554.15 (C38H22N2OS = 554.67) |
| 4-697 | m/z = 554.15 (C38H22N2OS = 554.67) | 4-698 | m/z = 650.24 (C48H30N2O = 650.78) |
| 4-699 | m/z = 576.20 (C40H24N4O = 576.66) | 4-700 | m/z = 576.20 (C40H24N4O = 576.66) |
| 4-701 | m/z = 576.20 (C40H24N4O = 576.66) | 4-702 | m/z = 652.23 (C46H28N4O = 652.76) |
| 4-703 | m/z = 652.23 (C46H28N4O = 652.76) | 4-704 | m/z = 652.23 (C46H28N4O = 652.76) |
| 4-705 | m/z = 499.17 (C35H21N3O = 499.57) | 4-706 | m/z = 499.17 (C35H21N3O = 499.57) |
| 4-707 | m/z = 499.17 (C35H21N3O = 499.57) | 4-708 | m/z = 575.20 (C41H25N3O = 575.67) |
| 4-709 | m/z = 575.20 (C41H25N3O = 575.67) | 4-710 | m/z = 575.20 (C41H25N3O = 575.67) |
| 5-1 | m/z = 615.27 (C45H33N3 = 615.78) | 5-2 | m/z = 687.27 (C51H33N3 = 687.85) |
| 5-3 | m/z = 687.27 (C51H33N3 = 687.85) | 5-4 | m/z = 587.24 (C43H29N3 = 587.73) |
| 5-5 | m/z = 663.27 (C49H33N3 = 663.82) | 5-6 | m/z = 739.30 (C55H37N3 = 739.92) |
| 5-7 | m/z = 739.30 (C55H37N3 = 739.92) | 5-8 | m/z = 739.30 (C55H37N3 = 739.92) |
| 5-9 | m/z = 637.25 (C47H31N3 = 637.79) | 5-10 | m/z = 637.25 (C47H31N3 = 637.79) |
| 5-11 | m/z = 703.30 (C52H37N3 = 703.89) | 5-12 | m/z = 827.33 (C62H41N3 = 828.03) |
| 5-13 | m/z = 693.22 (C49H31N3S = 693.87) | 5-14 | m/z = 677.25 (C49H31N3O = 677.82) |
| 5-15 | m/z = 752.29 (C55H36N4 = 752.92) | 5-16 | m/z = 828.33 (C61H40N4 = 829.02) |
| 5-17 | m/z = 693.22 (C49H31N3S = 693.87) | 5-18 | m/z = 677.25 (C49H31N3O = 677.82) |
| 5-19 | m/z = 713.28 (C53H35N3 = 713.88) | 5-20 | m/z = 779.33 (C58H41N3 = 779.99) |
| 5-21 | m/z = 903.36 (C68H45N3 = 904.13) | 5-22 | m/z = 769.26 (C55H35N3S = 769.97) |
| 5-23 | m/z = 753.28 (C55H35N3O = 753.90) | 5-24 | m/z = 828.33 (C61H40N4 = 829.02) |
| 5-25 | m/z = 904.36 (C67H44N4 = 905.12) | 5-26 | m/z = 769.26 (C55H35N3S = 769.97) |
| 5-27 | m/z = 753.28 (C55H35N3O = 753.90) | 5-28 | m/z = 713.28 (C53H35N3 = 713.88) |
| 5-29 | m/z = 819.36 (C61H45N3 = 820.05) | 5-30 | m/z = 779.33 (C58H41N3 = 779.99) |
| 5-31 | m/z = 779.33 (C58H41N3 = 779.99) | 5-32 | m/z = 943.39 (C71H49N3 = 944.19) |
| 5-33 | m/z = 917.35 (C67H43N5 = 918.12) | 5-34 | m/z = 809.29 (C58H39N3S = 810.03) |
| 5-35 | m/z = 933.32 (C68H43N3S = 934.17) | 5-36 | m/z = 799.21 (C55H33N3S2 = 800.01) |
| 5-37 | m/z = 858.28 (C61H38N4S = 859.06) | 5-38 | m/z = 783.23 (C55H33N3OS = 783.95) |
| 5-39 | m/z = 783.23 (C55H33N3OS = 783.95) | 5-40 | m/z = 793.31 (C58H39N3O = 793.97) |
| 5-41 | m/z = 917.34 (C68H43N3O = 918.11) | 5-42 | m/z = 783.23 (C55H33N3OS = 783.95) |
| 5-43 | m/z = 842.30 (C61H38N4O = 843.00) | 5-44 | m/z = 767.26 (C55H33N3O2 = 767.89) |
| 5-45 | m/z = 767.26 (C55H33N3O2 = 767.89) | 5-46 | m/z = 663.27 (C49H33N3 = 663.82) |
| 5-47 | m/z = 739.30 (C55H37N3 = 739.92) | 5-48 | m/z = 815.33 (C61H41N3 = 816.02) |
| 5-49 | m/z = 815.33 (C61H41N3 = 816.02) | 5-50 | m/z = 815.33 (C61H41N3 = 816.02) |
| 5-51 | m/z = 763.30 (C57H37N3 = 763.94) | 5-52 | m/z = 763.30 (C57H37N3 = 763.94) |
| 5-53 | m/z = 661.25 (C49H31N3 = 661.81) | 5-54 | m/z = 902.34 (C67H42N4 = 903.10) |
| 5-55 | m/z = 826.31 (C61H38N4 = 827.00) | 5-56 | m/z = 676.22 (C49H28N2O2 = 676.78) |
| 5-57 | m/z = 708.17 (C49H28N2S2 = 708.90) | 5-58 | m/z = 737.28 (C55H35N3 = 737.91) |
| 5-59 | m/z = 889.35 (C67H43N3 = 890.10) | 5-60 | m/z = 917.30 (C67H39N3O2 = 918.07) |
| 5-61 | m/z = 648.26 (C49H32N2 = 648.81) | 5-62 | m/z = 868.06 (C64H44N4 = 869.08) |
| 5-63 | m/z = 944.39 (C70H48N4 = 945.18) | 5-64 | m/z = 703.30 (C52H37N3 = 703.89) |
| 5-65 | m/z = 753.31 (C56H39N3 = 753.95) | 5-66 | m/z = 753.31 (C56H39N3 = 753.95) |
| 5-67 | m/z = 717.32 (C53H39N3 = 717.92) | 5-68 | m/z = 793.32 (C57H39N5 = 793.97) |
| 5-69 | m/z = 793.32 (C57H39N5 = 793.97) | 5-70 | m/z = 779.33 (C58H41N3 = 779.99) |
| 5-71 | m/z = 779.33 (C58H41N3 = 779.99) | 5-72 | m/z = 853.35 (C64H43N3 = 854.07) |
| 5-73 | m/z = 800.32 (C61H40N2 = 801.01) | 5-74 | m/z = 992.39 (C74H48N4 = 993.23) |
| 5-75 | m/z = 1068.42 (C80H52N4 = 1069.32) | 5-76 | m/z = 827.33 (C62H41N3 = 828.03) |
| 5-77 | m/z = 877.35 (C66H43N3 = 878.09) | 5-78 | m/z = 877.35 (C66H43N3 = 878.09) |
| 5-79 | m/z = 841.35 (C63H43N3 = 842.06) | 5-80 | m/z = 917.35 (C67H43N5 = 918.12) |
| 5-81 | m/z = 917.35 (C67H43N5 = 918.12) | 5-82 | m/z = 903.36 (C68H45N3 = 904.13) |
| 5-83 | m/z = 903.36 (C68H45N3 = 904.13) | 5-84 | m/z = 977.38 (C74H47N3 = 978.21) |
| 5-85 | m/z = 661.25 (C49H31N3 = 661.82) | 5-86 | m/z = 661.25 (C49H31N3 = 661.82) |
| 5-87 | m/z = 661.25 (C49H31N3 = 661.82) | 5-88 | m/z = 661.25 (C49H31N3 = 661.82) |
| 6-1 | m/z = 540.22 (C39H28N2O = 540.67) | 6-2 | m/z = 612.22 (C45H28N2O = 612.73) |
| 6-3 | m/z = 612.22 (C45H28N2O = 612.73) | 6-4 | m/z = 512.19 (C37H24N2O = 512.62) |
| 6-5 | m/z = 588.22 (C43H28N2O = 588.71) | 6-6 | m/z = 664.25 (C49H32N2O = 664.82) |
| 6-7 | m/z = 664.25 (C49H32N2O = 664.82) | 6-8 | m/z = 664.25 (C49H32N2O = 664.82) |
| 6-9 | m/z = 562.20 (C41H26N2O = 562.67) | 6-10 | m/z = 562.20 (C41H26N2O = 562.67) |
| 6-11 | m/z = 628.25 (C46H32N2O = 628.77) | 6-12 | m/z = 752.28 (C56H36N2O = 752.92) |
| 6-13 | m/z = 618.18 (C43H26N2OS = 618.75) | 6-14 | m/z = 602.20 (C43H26N2O2 = 602.69) |
| 6-15 | m/z = 677.25 (C49H31N3O = 677.82) | 6-16 | m/z = 753.28 (C55H35N3O = 753.90) |
| 6-17 | m/z = 618.18 (C43H26N2OS = 618.75) | 6-18 | m/z = 602.20 (C43H26N2O2 = 602.69) |
| 6-19 | m/z = 638.24 (C47H30N2O = 628.77) | 6-20 | m/z = 704.28 (C52H36N2O = 704.87) |
| 6-21 | m/z = 828.31 (C62H40N2O = 829.01) | 6-22 | m/z = 694.21 (C49H30N2OS = 694.85) |
| 6-23 | m/z = 678.23 (C49H30N2O2 = 678.79) | 6-24 | m/z = 753.28 (C55H35N3O = 753.90) |
| 6-25 | m/z = 829.31 (C61H39N3O = 830.00) | 6-26 | m/z = 694.21 (C49H30N2OS = 694.85) |
| 6-27 | m/z = 678.23 (C49H30N2O2 = 678.79) | 6-28 | m/z = 638.24 (C47H30N2O = 638.77) |
| 6-29 | m/z = 744.31 (C55H40N2O = 744.94) | 6-30 | m/z = 704.28 (C52H36N2O = 704.87) |

TABLE 2-continued

| Compound | FD-MS | Compound | FD-MS |
|---|---|---|---|
| 6-31 | m/z = 704.28 (C52H36N2O = 704.87) | 6-32 | m/z = 868.35 (C65H44N2O = 869.08) |
| 6-33 | m/z = 842.30 (C61H38N4O = 843.00) | 6-34 | m/z = 734.24 (C52H34N2OS = 734.92) |
| 6-35 | m/z = 858.27 (C62H38N2OS = 859.06) | 6-36 | m/z = 724.16 (C49H28N2OS2 = 724.90) |
| 6-37 | m/z = 783.24 (C55H33N3OS = 783.95) | 6-38 | m/z = 708.19 (C49H28N2O2S = 708.84) |
| 6-39 | m/z = 708.19 (C49H28N2O2S = 708.84) | 6-40 | m/z = 718.26 (C52H34N2O2 = 718.86) |
| 6-41 | m/z = 842.29 (C62H38N2O2 = 843.00) | 6-42 | m/z = 708.19 (C49H28N2O2S = 708.84) |
| 6-43 | m/z = 767.26 (C55H33N3O2 = 767.89) | 6-44 | m/z = 692.21 (C49H28N2O3 = 692.77) |
| 6-45 | m/z = 692.21 (C49H28N2O3 = 692.77) | 6-46 | m/z = 588.21 (C43H28N2O = 588.72) |
| 6-47 | m/z = 664.25 (C49H32N2O = 664.81) | 6-48 | m/z = 740.28 (C55H36N2O = 740.91) |
| 6-49 | m/z = 740.28 (C55H36N2O = 740.91) | 6-50 | m/z = 740.28 (C55H36N2O = 740.91) |
| 6-51 | m/z = 688.25 (C51H32N2O = 688.83) | 6-52 | m/z = 688.25 (C51H32N2O = 688.83) |
| 6-53 | m/z = 586.20 (C43H26N2O = 586.69) | 6-54 | m/z = 827.29 (C61H37N3O = 827.99) |
| 6-55 | m/z = 751.26 (C55H33N3O = 751.89) | 6-56 | m/z = 601.17 (C43H23NO3 = 601.66) |
| 6-57 | m/z = 633.12 (C43H23NOS2 = 633.78) | 6-58 | m/z = 662.24 (C49H30N2O = 662.79) |
| 6-59 | m/z = 814.30 (C61H38N2O = 814.99) | 6-60 | m/z = 842.26 (C61H34N2O3 = 842.95) |
| 6-61 | m/z = 573.21 (C43H27NO = 573.69) | 6-62 | m/z = 793.31 (C58H39N3O = 793.97) |
| 6-63 | m/z = 869.34 (C64H43N3O = 870.07) | 6-64 | m/z = 628.25 (C46H32N2O = 628.77) |
| 6-65 | m/z = 678.27 (C50H34N2O = 678.84) | 6-66 | m/z = 678.27 (C50H34N2O = 678.84) |
| 6-67 | m/z = 642.27 (C47H34N2O = 642.80) | 6-68 | m/z = 718.27 (C51H34N4O = 718.86) |
| 6-69 | m/z = 718.27 (C51H34N4O = 718.86) | 6-70 | m/z = 704.28 (C52H36N2O = 704.87) |
| 6-71 | m/z = 704.28 (C52H36N2O = 704.87) | 6-72 | m/z = 778.30 (C58H38N2O = 778.95) |
| 6-73 | m/z = 725.27 (C55H35NO = 725.89) | 6-74 | m/z = 917.34 (C68H43N3O = 918.11) |
| 6-75 | m/z = 993.37 (C74H47N3O = 994.21) | 6-76 | m/z = 752.28 (C56H36N2O = 752.92) |
| 6-77 | m/z = 802.30 (C60H38N2O = 802.98) | 6-78 | m/z = 802.30 (C60H38N2O = 802.98) |
| 6-79 | m/z = 766.30 (C5738N2O = 766.94) | 6-80 | m/z = 842.30 (C61H38N4O = 843.00) |
| 6-81 | m/z = 842.30 (C61H38N4O = 843.00) | 6-82 | m/z = 828.31 (C62H40N2O = 829.01) |
| 6-83 | m/z = 828.31 (C62H40N2O = 829.01) | 6-84 | m/z = 902.33 (C68H42N2O = 903.10) |
| 6-85 | m/z = 586.20 (C43H26N2O = 586.69) | 6-86 | m/z = 586.20 (C43H26N2O = 586.69) |
| 6-87 | m/z = 586.20 (C43H26N2O = 586.69) | 6-88 | m/z = 586.20 (C43H26N2O = 586.69) |
| 7-1 | m/z = 556.20 (C39H28N2S = 556.73) | 7-2 | m/z = 628.20 (C45H28N2S = 628.79) |
| 7-3 | m/z = 628.20 (C45H28N2S = 628.79) | 7-4 | m/z = 528.17 (C37H24N2S = 528.67) |
| 7-5 | m/z = 604.20 (C43H28N2S = 604.77) | 7-6 | m/z = 680.23 (C49H32N2S = 680.87) |
| 7-7 | m/z = 680.23 (C49H32N2S = 680.87) | 7-8 | m/z = 680.23 (C49H32N2S = 680.87) |
| 7-9 | m/z = 578.18 (C41H26N2S = 578.73) | 7-10 | m/z = 578.18 (C41H26N2S = 578.73) |
| 7-11 | m/z = 644.23 (C46H32N2S = 644.84) | 7-12 | m/z = 768.26 (C56H36N2S = 768.98) |
| 7-13 | m/z = 634.15 (C43H26N2S2 = 634.82) | 7-14 | m/z = 618.18 (C43H26N2OS = 618.75) |
| 7-15 | m/z = 693.22 (C49H31N3S = 693.87) | 7-16 | m/z = 769.26 (C55H35N3S = 769.97) |
| 7-17 | m/z = 634.15 (C43H26N2S2 = 634.82) | 7-18 | m/z = 618.18 (C43H26N2OS = 618.75) |
| 7-19 | m/z = 654.21 (C47H30N2S = 654.83) | 7-20 | m/z = 720.26 (C52H36N2S = 720.93) |
| 7-21 | m/z = 844.29 (C62H40N2S = 845.08) | 7-22 | m/z = 710.19 (C49H30N2S2 = 710.91) |
| 7-23 | m/z = 694.21 (C49H30N2OS = 694.85) | 7-24 | m/z = 769.26 (C55H35N3S = 769.97) |
| 7-25 | m/z = 845.29 (C61H39N3S = 846.06) | 7-26 | m/z = 710.19 (C49H30N2S2 = 710.91) |
| 7-27 | m/z = 694.21 (C49H30N2OS = 694.85) | 7-28 | m/z = 654.21 (C47H30N2S = 654.83) |
| 7-29 | m/z = 760.29 (C55H40N2S = 761.00) | 7-30 | m/z = 720.26 (C52H36N2S = 720.93) |
| 7-31 | m/z = 720.26 (C52H36N2S = 720.93) | 7-32 | m/z = 884.32 (C65H44N2S = 885.14) |
| 7-33 | m/z = 858.28 (C61H38N4S = 859.06) | 7-34 | m/z = 750.22 (C52H34N2S2 = 750.98) |
| 7-35 | m/z = 874.25 (C62H38N2S2 = 875.12) | 7-36 | m/z = 740.14 (C49H28N2S3 = 740.69) |
| 7-37 | m/z = 799.21 (C55H33N3S2 = 800.01) | 7-38 | m/z = 724.16 (C4649H28N2OS2 = 724.90) |
| 7-39 | m/z = 724.16 (C4649H28N2OS2 = 724.90) | 7-40 | m/z = 734.24 (C52H34N2OS = 734.92) |
| 7-41 | m/z = 858.27 (C62H38N2OS = 859.06) | 7-42 | m/z = 724.16 (C4649H28N2OS2 = 724.90) |
| 7-43 | m/z = 783.23 (C55H33N3OS = 783.95) | 7-44 | m/z = 708.19 (C49H28N2O2S = 708.84) |
| 7-45 | m/z = 708.19 (C49H28N2O2S = 708.84) | 7-46 | m/z = 604.20 (C43H28N2S = 604.77) |
| 7-47 | m/z = 680.23 (C4932N2S = 680.87) | 7-48 | m/z = 756.26 (C55H36N2S = 756.97) |
| 7-49 | m/z = 756.26 (C55H36N2S = 756.97) | 7-50 | m/z = 756.26 (C55H36N2S = 756.97) |
| 7-51 | m/z = 704.23 (C51H32N2S = 704.89) | 7-52 | m/z = 704.23 (C51H32N2S = 704.89) |
| 7-53 | m/z = 602.18 (C43H26N2S = 602.75) | 7-54 | m/z = 843.27 (C61H37N2S = 844.05) |
| 7-55 | m/z = 767.24 (C55H33N3S = 767.95) | 7-56 | m/z = 617.14 (C43H23N2S = 617.72) |
| 7-57 | m/z = 649.10 (C43H23NS3 = 649.84) | 7-58 | m/z = 678.21 (C49H30N2S = 678.85) |
| 7-59 | m/z = 830.28 (C61H38N2S = 831.05) | 7-60 | m/z = 858.23 (C61H34N2O2S = 859.02) |
| 7-61 | m/z = 589.19 (C43H27NS = 589.76) | 7-62 | m/z = 809.29 (C58H39N3S = 810.03) |
| 7-63 | m/z = 885.32 (C64H43N3S = 886.13) | 7-64 | m/z = 644.23 (C46H32N2S = 644.84) |
| 7-65 | m/z = 694.25 (C50H34N2S = 694.90) | 7-66 | m/z = 694.25 (C50H34N2S = 694.90) |
| 7-67 | m/z = 658.24 (C47H34N2S = 658.86) | 7-68 | m/z = 734.25 (C51H34N4S = 734.92) |
| 7-69 | m/z = 734.25 (C51H34N4S = 734.92) | 7-70 | m/z = 720.26 (C52H36N2S = 720.93) |
| 7-71 | m/z = 720.26 (C52H36N2S = 720.93) | 7-72 | m/z = 794.28 (C46H29N2S = 795.02) |
| 7-73 | m/z = 741.25 (C55H35NS = 741.95) | 7-74 | m/z = 933.32 (C68H43N3S = 934.17) |
| 7-75 | m/z = 1009.35 (C74H47N3S = 1010.27) | 7-76 | m/z = 768.26 (C56H36N2S = 768.98) |
| 7-77 | m/z = 818.28 (C60H38N2S = 819.04) | 7-78 | m/z = 818.28 (C60H38N2S = 819.04) |
| 7-79 | m/z = 782.28 (C57H38N2S = 783.00) | 7-80 | m/z = 858.28 (C61H38N4S = 859.06) |
| 7-81 | m/z = 858.28 (C61H38N4S = 859.06) | 7-82 | m/z = 844.29 (C62H40N2S = 845.08) |
| 7-83 | m/z = 844.29 (C62H40N2S = 845.08) | 7-84 | m/z = 918.31 (C68H42N2S = 919.16) |
| 7-85 | m/z = 602.18 (C43H26N2S = 602.75) | 7-86 | m/z = 602.18 (C43H26N2S = 602.75) |
| 7-87 | m/z = 602.18 (C43H26N2S = 602.75) | 7-88 | m/z = 602.18 (C43H26N2S = 602.75) |
| 10-1 | m/z = 747.29 (C58H37N = 747.94) | 10-2 | m/z = 923.36 (C72H45N = 924.16) |
| 10-3 | m/z = 695.24 (C50H34NOP = 695.80) | 10-4 | m/z = 771.27 (C56H38NOP = 771.90) |
| 10-5 | m/z = 901.35 (C68H43N3 = 902.11) | 10-6 | m/z = 726.28 (C53H34N4 = 726.88) |
| 10-7 | m/z = 802.31 (C59H38N4 = 802.98) | 10-8 | m/z = 725.28 (C54H35N3 = 725.89) |
| 10-9 | m/z = 801.31 (C60H39N3 = 801.99) | 10-10 | m/z = 801.31 (C60H39N3 = 801.99) |

TABLE 2-continued

| Compound | FD-MS | Compound | FD-MS |
|---|---|---|---|
| 10-11 | m/z = 877.35 (C66H43N3 = 878.09) | 10-12 | m/z = 725.28 (C54H35N3 = 725.89) |
| 10-13 | m/z = 801.31 (C60H39N3 = 801.99) | 10-14 | m/z = 877.35 (C66H43N3 = 878.09) |
| 10-15 | m/z = 801.31 (C60H39N3 = 801.99) | 10-16 | m/z = 877.35 (C66H43N3 = 878.09) |
| 10-17 | m/z = 953.38 (C72H47N3 = 954.19) | 10-18 | m/z = 844.29 (C62H40N2S = 845.08) |
| 10-19 | m/z = 828.31 (C62H40N2O = 829.01) | 10-20 | m/z = 903.36 (C68H45N3 = 904.13) |
| 10-21 | m/z = 775.30 (C58H37N3 = 775.95) | 10-22 | m/z = 699.27 (C52H33N3 = 699.86) |
| 10-23 | m/z = 851.33 (C64H41N3 = 852.05) | 10-24 | m/z = 775.30 (C58H37N3 = 775.95) |
| 10-25 | m/z = 851.33 (C64H41N3 = 852.05) | 10-26 | m/z = 775.30 (C58H37N3 = 775.95) |
| 10-27 | m/z = 801.31 (C60H39N3 = 801.99) | 10-28 | m/z = 699.27 (C52H33N3 = 699.86) |
| 10-29 | m/z = 775.30 (C58H37N3 = 775.95) | 10-30 | m/z = 775.30 (C58H37N3 = 775.95) |
| 10-31 | m/z = 851.33 (C64H41N3 = 852.05) | 10-32 | m/z = 673.25 (C50H31N3 = 673.82) |
| 10-33 | m/z = 749.28 (C56H35N3 = 749.92) | 10-34 | m/z = 687.27 (C51H33N3 = 687.85) |
| 10-35 | m/z = 687.27 (C51H33N3 = 687.85) | 10-36 | m/z = 639.27 (C47H33N3 = 639.80) |
| 10-37 | m/z = 715.30 (C53H37N3 = 715.90) | 10-38 | m/z = 715.30 (C53H37N3 = 715.90) |
| 10-39 | m/z = 763.30 (C57H37N3 = 763.94) | 10-40 | m/z = 763.30 (C57H37N3 = 763.94) |
| 10-41 | m/z = 715.30 (C53H37N3 = 715.90) | 10-42 | m/z = 704.23 (C51H32N2S = 704.89) |
| 10-43 | m/z = 723.29 (C56H37N = 723.92) | 10-44 | m/z = 661.25 (C49H31N3 = 661.81) |
| 10-45 | m/z = 721.28 (C56H35N = 721.90) | 10-46 | m/z = 596.23 (C45H28N2 = 596.73) |
| 10-47 | m/z = 672.26 (C51H32N2 = 672.83) | 10-48 | m/z = 572.23 (C43H28N2 = 572.71) |
| 10-49 | m/z = 687.27 (C51H33N3 = 687.85) | 10-50 | m/z = 763.30 (C57H37N3 = 763.94) |
| 10-51 | m/z = 747.29 (C58H37N = 747.94) | 10-52 | m/z = 923.36 (C72H45N = 924.16) |
| 10-53 | m/z = 695.24 (C50H34NOP = 695.80) | 10-54 | m/z = 771.27 (C56H38NOP = 771.90) |
| 10-55 | m/z = 901.35 (C68H43N3 = 902.11) | 10-56 | m/z = 726.28 (C53H34N4 = 726.88) |
| 10-57 | m/z = 802.31 (C59H38N4 = 802.98) | 10-58 | m/z = 725.28 (C54H35N3 = 725.89) |
| 10-59 | m/z = 801.31 (C60H39N3 = 801.99) | 10-60 | m/z = 801.31 (C60H39N3 = 801.99) |
| 10-61 | m/z = 877.35 (C66H43N3 = 878.09) | 10-62 | m/z = 725.28 (C54H35N3 = 725.89) |
| 10-63 | m/z = 801.31 (C60H39N3 = 801.99) | 10-64 | m/z = 877.35 (C66H43N3 = 878.09) |
| 10-65 | m/z = 801.31 (C60H39N3 = 801.99) | 10-66 | m/z = 877.35 (C66H43N3 = 878.09) |
| 10-67 | m/z = 953.38 (C72H47N3 = 954.19) | 10-68 | m/z = 844.29 (C62H40N2S = 845.08) |
| 10-69 | m/z = 828.31 (C62H40N2O = 829.01) | 10-70 | m/z = 903.36 (C68H45N3 = 904.13) |
| 10-71 | m/z = 775.30 (C58H37N3 = 775.95) | 10-72 | m/z = 699.27 (C52H33N3 = 699.86) |
| 10-73 | m/z = 851.33 (C64H41N3 = 852.05) | 10-74 | m/z = 775.30 (C58H37N3 = 775.95) |
| 10-75 | m/z = 851.33 (C64H41N3 = 852.05) | 10-76 | m/z = 775.30 (C58H37N3 = 775.95) |
| 10-77 | m/z = 801.31 (C60H39N3 = 801.99) | 10-78 | m/z = 699.27 (C52H33N3 = 699.86) |
| 10-79 | m/z = 775.30 (C58H37N3 = 775.95) | 10-80 | m/z = 775.30 (C58H37N3 = 775.95) |
| 10-81 | m/z = 851.33 (C64H41N3 = 852.05) | 10-82 | m/z = 673.25 (C50H31N3 = 673.82) |
| 10-83 | m/z = 749.28 (C56H35N3 = 749.92) | 10-84 | m/z = 687.27 (C51H33N3 = 687.85) |
| 10-85 | m/z = 687.27 (C51H33N3 = 687.85) | 10-86 | m/z = 639.27 (C47H33N3 = 639.80) |
| 10-87 | m/z = 715.30 (C53H37N3 = 715.90) | 10-88 | m/z = 715.30 (C53H37N3 = 715.90) |
| 10-89 | m/z = 763.30 (C57H37N3 = 763.94) | 10-90 | m/z = 763.30 (C57H37N3 = 763.94) |
| 10-91 | m/z = 715.30 (C53H37N3 = 715.90) | 10-92 | m/z = 704.23 (C51H32N2S = 704.89) |
| 10-93 | m/z = 723.29 (C56H37N = 723.92) | 10-94 | m/z = 661.25 (C49H31N3 = 661.81) |
| 10-95 | m/z = 721.28 (C56H35N = 721.90) | 10-96 | m/z = 596.23 (C45H28N2 = 596.73) |
| 10-97 | m/z = 672.26 (C51H32N2 = 672.83) | 10-98 | m/z = 572.23 (C43H28N2 = 572.71) |
| 10-99 | m/z = 687.27 (C51H33N3 = 687.85) | 10-100 | m/z = 763.30 (C57H37N3 = 763.94) |
| 11-1 | m/z = 747.29 (C58H37N = 747.94) | 11-2 | m/z = 923.36 (C72H45N = 924.16) |
| 11-3 | m/z = 695.24 (C50H34NOP = 695.80) | 11-4 | m/z = 771.27 (C56H38NOP = 771.90) |
| 11-5 | m/z = 901.35 (C68H43N3 = 902.11) | 11-6 | m/z = 726.28 (C53H34N4 = 726.88) |
| 11-7 | m/z = 802.31 (C59H38N4 = 802.98) | 11-8 | m/z = 725.28 (C54H35N3 = 725.89) |
| 11-9 | m/z = 801.31 (C60H39N3 = 801.99) | 11-10 | m/z = 801.31 (C60H39N3 = 801.99) |
| 11-11 | m/z = 877.35 (C66H43N3 = 878.09) | 11-12 | m/z = 725.28 (C54H35N3 = 725.89) |
| 11-13 | m/z = 801.31 (C60H39N3 = 801.99) | 11-14 | m/z = 877.35 (C66H43N3 = 878.09) |
| 11-15 | m/z = 801.31 (C60H39N3 = 801.99) | 11-16 | m/z = 877.35 (C66H43N3 = 878.09) |
| 11-17 | m/z = 953.38 (C72H47N3 = 954.19) | 11-18 | m/z = 844.29 (C62H40N2S = 845.08) |
| 11-19 | m/z = 828.31 (C62H40N2O = 829.01) | 11-20 | m/z = 903.36 (C68H45N3 = 904.13) |
| 11-21 | m/z = 775.30 (C58H37N3 = 775.95) | 11-22 | m/z = 699.27 (C52H33N3 = 699.86) |
| 11-23 | m/z = 851.33 (C64H41N3 = 852.05) | 11-24 | m/z = 775.30 (C58H37N3 = 775.95) |
| 11-25 | m/z = 851.33 (C64H41N3 = 852.05) | 11-26 | m/z = 775.30 (C58H37N3 = 775.95) |
| 11-27 | m/z = 801.31 (C60H39N3 = 801.99) | 11-28 | m/z = 699.27 (C52H33N3 = 699.86) |
| 11-29 | m/z = 775.30 (C58H37N3 = 775.95) | 11-30 | m/z = 775.30 (C58H37N3 = 775.95) |
| 11-31 | m/z = 851.33 (C64H41N3 = 852.05) | 11-32 | m/z = 673.25 (C50H31N3 = 673.82) |
| 11-33 | m/z = 749.28 (C56H35N3 = 749.92) | 11-34 | m/z = 687.27 (C51H33N3 = 687.85) |
| 11-35 | m/z = 687.27 (C51H33N3 = 687.85) | 11-36 | m/z = 639.27 (C47H33N3 = 639.80) |
| 11-37 | m/z = 715.30 (C53H37N3 = 715.90) | 11-38 | m/z = 715.30 (C53H37N3 = 715.90) |
| 11-39 | m/z = 763.30 (C57H37N3 = 763.94) | 11-40 | m/z = 763.30 (C57H37N3 = 763.94) |
| 11-41 | m/z = 715.30 (C53H37N3 = 715.90) | 11-42 | m/z = 704.23 (C51H32N2S = 704.89) |
| 11-43 | m/z = 723.29 (C56H37N = 723.92) | 11-44 | m/z = 661.25 (C49H31N3 = 661.81) |
| 11-45 | m/z = 721.28 (C56H35N = 721.90) | 11-46 | m/z = 596.23 (C45H28N2 = 596.73) |
| 11-47 | m/z = 672.26 (C51H32N2 = 672.83) | 11-48 | m/z = 572.23 (C43H28N2 = 572.71) |
| 11-49 | m/z = 687.27 (C51H33N3 = 687.85) | 11-50 | m/z = 763.30 (C57H37N3 = 763.94) |
| 11-51 | m/z = 747.29 (C58H37N = 747.94) | 11-52 | m/z = 923.36 (C72H45N = 924.16) |
| 11-53 | m/z = 695.24 (C50H34NOP = 695.80) | 11-54 | m/z = 771.27 (C56H38NOP = 771.90) |
| 11-55 | m/z = 901.35 (C68H43N3 = 902.11) | 11-56 | m/z = 726.28 (C53H34N4 = 726.88) |
| 11-57 | m/z = 802.31 (C59H38N4 = 802.98) | 11-58 | m/z = 725.28 (C54H35N3 = 725.89) |
| 11-59 | m/z = 801.31 (C60H39N3 = 801.99) | 11-60 | m/z = 801.31 (C60H39N3 = 801.99) |
| 11-61 | m/z = 877.35 (C66H43N3 = 878.09) | 11-62 | m/z = 725.28 (C54H35N3 = 725.89) |
| 11-63 | m/z = 801.31 (C60H39N3 = 801.99) | 11-64 | m/z = 877.35 (C66H43N3 = 878.09) |
| 11-65 | m/z = 801.31 (C60H39N3 = 801.99) | 11-66 | m/z = 877.35 (C66H43N3 = 878.09) |

TABLE 2-continued

| Compound | FD-MS | Compound | FD-MS |
|---|---|---|---|
| 11-67 | m/z = 953.38 ($C_{72}H_{47}N_3$ = 954.19) | 11-68 | m/z = 844.29 ($C_{62}H_{40}N_2S$ = 845.08) |
| 11-69 | m/z = 828.31 ($C_{62}H_{40}N_2O$ = 829.01) | 11-70 | m/z = 903.36 ($C_{68}H_{45}N_3$ = 904.13) |
| 11-71 | m/z = 775.30 ($C_{58}H_{37}N_3$ = 775.95) | 11-72 | m/z = 699.27 ($C_{52}H_{33}N_3$ = 699.86) |
| 11-73 | m/z = 851.33 ($C_{64}H_{41}N_3$ = 852.05) | 11-74 | m/z = 775.30 ($C_{58}H_{37}N_3$ = 775.95) |
| 11-75 | m/z = 851.33 ($C_{64}H_{41}N_3$ = 852.05) | 11-76 | m/z = 775.30 ($C_{58}H_{37}N_3$ = 775.95) |
| 11-77 | m/z = 801.31 ($C_{60}H_{39}N_3$ = 801.99) | 11-78 | m/z = 699.27 ($C_{52}H_{33}N_3$ = 699.86) |
| 11-79 | m/z = 775.30 ($C_{58}H_{37}N_3$ = 775.95) | 11-80 | m/z = 775.30 ($C_{58}H_{37}N_3$ = 775.95) |
| 11-81 | m/z = 851.33 ($C_{64}H_{41}N_3$ = 852.05) | 11-82 | m/z = 673.25 ($C_{50}H_{31}N_3$ = 673.82) |
| 11-83 | m/z = 749.28 ($C_{56}H_{35}N_3$ = 749.92) | 11-84 | m/z = 687.27 ($C_{51}H_{33}N_3$ = 687.85) |
| 11-85 | m/z = 687.27 ($C_{51}H_{33}N_3$ = 687.85) | 11-86 | m/z = 639.27 ($C_{47}H_{33}N_3$ = 639.80) |
| 11-87 | m/z = 715.30 ($C_{53}H_{37}N_3$ = 715.90) | 11-88 | m/z = 715.30 ($C_{53}H_{37}N_3$ = 715.90) |
| 11-89 | m/z = 763.30 ($C_{57}H_{37}N_3$ = 763.94) | 11-90 | m/z = 763.30 ($C_{57}H_{37}N_3$ = 763.94) |
| 11-91 | m/z = 715.30 ($C_{53}H_{37}N_3$ = 715.90) | 11-92 | m/z = 704.23 ($C_{51}H_{32}N_2S$ = 704.89) |
| 11-93 | m/z = 723.29 ($C_{56}H_{37}N$ = 723.92) | 11-94 | m/z = 661.25 ($C_{49}H_{31}N_3$ = 661.81) |
| 11-95 | m/z = 721.28 ($C_{56}H_{35}N$ = 721.90) | 11-96 | m/z = 596.23 ($C_{45}H_{28}N_2$ = 596.73) |
| 11-97 | m/z = 672.26 ($C_{51}H_{32}N_2$ = 672.83) | 11-98 | m/z = 572.23 ($C_{43}H_{28}N_2$ = 572.71) |
| 11-99 | m/z = 687.27 ($C_{51}H_{33}N_3$ = 687.85) | 11-100 | m/z = 763.30 ($C_{57}H_{37}N_3$ = 763.94) |
| 12-1 | m/z = 747.29 ($C_{58}H_{37}N$ = 747.94) | 12-2 | m/z = 923.36 ($C_{72}H_{45}N$ = 924.16) |
| 12-3 | m/z = 695.24 ($C_{50}H_{34}NOP$ = 695.80) | 12-4 | m/z = 771.27 ($C_{56}H_{38}NOP$ = 771.90) |
| 12-5 | m/z = 901.35 ($C_{68}H_{43}N_3$ = 902.11) | 12-6 | m/z = 726.28 ($C_{53}H_{34}N_4$ = 726.88) |
| 12-7 | m/z = 802.31 ($C_{59}H_{38}N_4$ = 802.98) | 12-8 | m/z = 725.28 ($C_{54}H_{35}N_3$ = 725.89) |
| 12-9 | m/z = 801.31 ($C_{60}H_{39}N_3$ = 801.99) | 12-10 | m/z = 801.31 ($C_{60}H_{39}N_3$ = 801.99) |
| 12-11 | m/z = 877.35 ($C_{66}H_{43}N_3$ = 878.09) | 12-12 | m/z = 725.28 ($C_{54}H_{35}N_3$ = 725.89) |
| 12-13 | m/z = 801.31 ($C_{60}H_{39}N_3$ = 801.99) | 12-14 | m/z = 877.35 ($C_{66}H_{43}N_3$ = 878.09) |
| 12-15 | m/z = 801.31 ($C_{60}H_{39}N_3$ = 801.99) | 12-16 | m/z = 877.35 ($C_{66}H_{43}N_3$ = 878.09) |
| 12-17 | m/z = 953.38 ($C_{72}H_{47}N_3$ = 954.19) | 12-18 | m/z = 844.29 ($C_{62}H_{40}N_2S$ = 845.08) |
| 12-19 | m/z = 828.31 ($C_{62}H_{40}N_2O$ = 829.01) | 12-20 | m/z = 903.36 ($C_{68}H_{45}N_3$ = 904.13) |
| 12-21 | m/z = 775.30 ($C_{58}H_{37}N_3$ = 775.95) | 12-22 | m/z = 699.27 ($C_{52}H_{33}N_3$ = 699.86) |
| 12-23 | m/z = 851.33 ($C_{64}H_{41}N_3$ = 852.05) | 12-24 | m/z = 775.30 ($C_{58}H_{37}N_3$ = 775.95) |
| 12-25 | m/z = 851.33 ($C_{64}H_{41}N_3$ = 852.05) | 12-26 | m/z = 775.30 ($C_{58}H_{37}N_3$ = 775.95) |
| 12-27 | m/z = 801.31 ($C_{60}H_{39}N_3$ = 801.99) | 12-28 | m/z = 699.27 ($C_{52}H_{33}N_3$ = 699.86) |
| 12-29 | m/z = 775.30 ($C_{58}H_{37}N_3$ = 775.95) | 12-30 | m/z = 775.30 ($C_{58}H_{37}N_3$ = 775.95) |
| 12-31 | m/z = 851.33 ($C_{64}H_{41}N_3$ = 852.05) | 12-32 | m/z = 673.25 ($C_{50}H_{31}N_3$ = 673.82) |
| 12-33 | m/z = 749.28 ($C_{56}H_{35}N_3$ = 749.92) | 12-34 | m/z = 687.27 ($C_{51}H_{33}N_3$ = 687.85) |
| 12-35 | m/z = 687.27 ($C_{51}H_{33}N_3$ = 687.85) | 12-36 | m/z = 639.27 ($C_{47}H_{33}N_3$ = 639.80) |
| 12-37 | m/z = 715.30 ($C_{53}H_{37}N_3$ = 715.90) | 12-38 | m/z = 715.30 ($C_{53}H_{37}N_3$ = 715.90) |
| 12-39 | m/z = 763.30 ($C_{57}H_{37}N_3$ = 763.94) | 12-40 | m/z = 763.30 ($C_{57}H_{37}N_3$ = 763.94) |
| 12-41 | m/z = 715.30 ($C_{53}H_{37}N_3$ = 715.90) | 12-42 | m/z = 704.23 ($C_{51}H_{32}N_2S$ = 704.89) |
| 12-43 | m/z = 723.29 ($C_{56}H_{37}N$ = 723.92) | 12-44 | m/z = 661.25 ($C_{49}H_{31}N_3$ = 661.81) |
| 12-45 | m/z = 721.28 ($C_{56}H_{35}N$ = 721.90) | 12-46 | m/z = 596.23 ($C_{45}H_{28}N_2$ = 596.73) |
| 12-47 | m/z = 672.26 ($C_{51}H_{32}N_2$ = 672.83) | 12-48 | m/z = 572.23 ($C_{43}H_{28}N_2$ = 572.71) |
| 12-49 | m/z = 687.27 ($C_{51}H_{33}N_3$ = 687.85) | 12-50 | m/z = 763.30 ($C_{57}H_{37}N_3$ = 763.94) |
| 12-51 | m/z = 747.29 ($C_{58}H_{37}N$ = 747.94) | 12-52 | m/z = 923.36 ($C_{72}H_{45}N$ = 924.16) |
| 12-53 | m/z = 695.24 ($C_{50}H_{34}NOP$ = 695.80) | 12-54 | m/z = 771.27 ($C_{56}H_{38}NOP$ = 771.90) |
| 12-55 | m/z = 901.35 ($C_{68}H_{43}N_3$ = 902.11) | 12-56 | m/z = 726.28 ($C_{53}H_{34}N_4$ = 726.88) |
| 12-57 | m/z = 802.31 ($C_{59}H_{38}N_4$ = 802.98) | 12-58 | m/z = 725.28 ($C_{54}H_{35}N_3$ = 725.89) |
| 12-59 | m/z = 801.31 ($C_{60}H_{39}N_3$ = 801.99) | 12-60 | m/z = 801.31 ($C_{60}H_{39}N_3$ = 801.99) |
| 12-61 | m/z = 877.35 ($C_{66}H_{43}N_3$ = 878.09) | 12-62 | m/z = 725.28 ($C_{54}H_{35}N_3$ = 725.89) |
| 12-63 | m/z = 801.31 ($C_{60}H_{39}N_3$ = 801.99) | 12-64 | m/z = 877.35 ($C_{66}H_{43}N_3$ = 878.09) |
| 12-65 | m/z = 801.31 ($C_{60}H_{39}N_3$ = 801.99) | 12-66 | m/z = 877.35 ($C_{66}H_{43}N_3$ = 878.09) |
| 12-67 | m/z = 953.38 ($C_{72}H_{47}N_3$ = 954.19) | 12-68 | m/z = 844.29 ($C_{62}H_{40}N_2S$ = 845.08) |
| 12-69 | m/z = 828.31 ($C_{62}H_{40}N_2O$ = 829.01) | 12-70 | m/z = 903.36 ($C_{68}H_{45}N_3$ = 904.13) |
| 12-71 | m/z = 775.30 ($C_{58}H_{37}N_3$ = 775.95) | 12-72 | m/z = 699.27 ($C_{52}H_{33}N_3$ = 699.86) |
| 12-73 | m/z = 851.33 ($C_{64}H_{41}N_3$ = 852.05) | 12-74 | m/z = 775.30 ($C_{58}H_{37}N_3$ = 775.95) |
| 12-75 | m/z = 851.33 ($C_{64}H_{41}N_3$ = 852.05) | 12-76 | m/z = 775.30 ($C_{58}H_{37}N_3$ = 775.95) |
| 12-77 | m/z = 801.31 ($C_{60}H_{39}N_3$ = 801.99) | 12-78 | m/z = 699.27 ($C_{52}H_{33}N_3$ = 699.86) |
| 12-79 | m/z = 775.30 ($C_{58}H_{37}N_3$ = 775.95) | 12-80 | m/z = 775.30 ($C_{58}H_{37}N_3$ = 775.95) |
| 12-81 | m/z = 851.33 ($C_{64}H_{41}N_3$ = 852.05) | 12-82 | m/z = 673.25 ($C_{50}H_{31}N_3$ = 673.82) |
| 12-83 | m/z = 749.28 ($C_{56}H_{35}N_3$ = 749.92) | 12-84 | m/z = 687.27 ($C_{51}H_{33}N_3$ = 687.85) |
| 12-85 | m/z = 687.27 ($C_{51}H_{33}N_3$ = 687.85) | 12-86 | m/z = 639.27 ($C_{47}H_{33}N_3$ = 639.80) |
| 12-87 | m/z = 715.30 ($C_{53}H_{37}N_3$ = 715.90) | 12-88 | m/z = 715.30 ($C_{53}H_{37}N_3$ = 715.90) |
| 12-89 | m/z = 763.30 ($C_{57}H_{37}N_3$ = 763.94) | 12-90 | m/z = 763.30 ($C_{57}H_{37}N_3$ = 763.94) |
| 12-91 | m/z = 715.30 ($C_{53}H_{37}N_3$ = 715.90) | 12-92 | m/z = 704.23 ($C_{51}H_{32}N_2S$ = 704.89) |
| 12-93 | m/z = 723.29 ($C_{56}H_{37}N$ = 723.92) | 12-94 | m/z = 661.25 ($C_{49}H_{31}N_3$ = 661.81) |
| 12-95 | m/z = 721.28 ($C_{56}H_{35}N$ = 721.90) | 12-96 | m/z = 596.23 ($C_{45}H_{28}N_2$ = 596.73) |
| 12-97 | m/z = 672.26 ($C_{51}H_{32}N_2$ = 672.83) | 12-98 | m/z = 572.23 ($C_{43}H_{28}N_2$ = 572.71) |
| 12-99 | m/z = 687.27 ($C_{51}H_{33}N_3$ = 687.85) | 12-100 | m/z = 763.30 ($C_{57}H_{37}N_3$ = 763.94) |

Meanwhile, FIGS. 4 to 30 are graphs illustrating a PL (photoluminescence) or LTPL (low temperature photoluminescence) measurement light emitting absorption spectrum in a region of a special UV wavelength. PL measurement was performed at room temperature by using the model name LS55 spectrometer manufactured by Perkin Elmer Inc., LTPL measurement was performed by using the model name F7000 apparatus manufactured by HITACHI, Ltd., and analysis was performed by using liquid nitrogen under the low temperature condition of −196° C. (77K).

FIG. 4 illustrates a PL measurement graph of compound 1-1 at a wavelength of 274 nm.

FIG. 5 illustrates a PL measurement graph of compound 1-12 at a wavelength of 233 nm.

FIG. 6 illustrates a PL measurement graph of compound 1-36 at a wavelength of 276 nm.

FIG. 7 illustrates a PL measurement graph of compound 1-113 at a wavelength of 240 nm.

FIG. 8 illustrates a PL measurement graph of compound 1-119 at a wavelength of 270 nm.

FIG. 9 illustrates a PL measurement graph of compound 1-124 at a wavelength of 240 nm.

FIG. 10 illustrates a PL measurement graph of compound 1-318 at a wavelength of 309 nm.

FIG. 11 illustrates a PL measurement graph of compound 2-36 at a wavelength of 282 nm.

FIG. 12 illustrates a PL measurement graph of compound 2-38 at a wavelength of 284 nm.

FIG. 13 illustrates a PL measurement graph of compound 3-39 at a wavelength of 307 nm.

FIG. 14 illustrates a PL measurement graph of compound 3-46 at a wavelength of 310 nm.

FIG. 15 illustrates a PL measurement graph of compound 4-56 at a wavelength of 278 nm.

FIG. 16 illustrates a PL measurement graph of compound 4-58 at a wavelength of 290 nm.

FIG. 17 illustrates a PL measurement graph of compound 4-76 at a wavelength of 267 nm.

FIG. 18 illustrates a PL measurement graph of compound 4-169 at a wavelength of 264 nm.

FIG. 19 illustrates a LTPL measurement graph of compound 1-1 at a wavelength of 309 nm.

FIG. 20 illustrates a LTPL measurement graph of compound 1-12 at a wavelength of 338 nm.

FIG. 21 illustrates a LTPL measurement graph of compound 1-36 at a wavelength of 310 nm.

FIG. 22 illustrates a LTPL measurement graph of compound 1-318 at a wavelength of 309 nm.

FIG. 23 illustrates a LTPL measurement graph of compound 2-36 at a wavelength of 409 nm.

FIG. 24 illustrates a LTPL measurement graph of compound 2-38 at a wavelength of 408 nm.

FIG. 25 illustrates a LTPL measurement graph of compound 3-39 at a wavelength of 307 nm.

FIG. 26 illustrates a LTPL measurement graph of compound 3-46 at a wavelength of 268 nm.

FIG. 27 illustrates a LTPL measurement graph of compound 4-56 at a wavelength of 278 nm.

FIG. 28 illustrates a LTPL measurement graph of compound 4-58 at a wavelength of 329 nm.

FIG. 29 illustrates a LTPL measurement graph of compound 4-76 at a wavelength of 365 nm.

FIG. 30 illustrates a LTPL measurement graph of compound 4-169 at a wavelength of 365 nm.

In the graphs of FIGS. 4 to 30, y axes are each intensity, and the x axes are each a wavelength (unit: nm).

Manufacturing of organic electroluminescence device

Comparative Example 1

The organic electroluminescence device was manufactured by the following method.

The glass substrate on which indium tin oxide (ITO) was applied in the thin film in a thickness of 1500 Å was washed by distilled water and the ultrasonic wave. If washing by distilled water was finished, washing by the ultrasonic wave was performed by the solvent such as acetone, methanol, and isopropyl alcohol, followed by drying, and UVO treatment was performed in the UV washing machine by using UV for 5 minutes. Thereafter, the substrate was transported to the plasma washing machine (PT), and plasma treatment was performed for the work function and removal of the residual film of indium tin oxide (ITO) in the vacuum state to transport the substrate to the heat deposition apparatus for organic deposition.

On the above prepared indium tin oxide (ITO) transparent electrode (anode), the hole injection layer of 4,4',4"-tris(N,N-(2-naphthyl)-phenylamino)triphenyl amine (2-TNATA) and the hole transport layer of N,N'-bis(α-naphthyl)-N,N'-diphenyl-4,4'-diamine (NPB) as the common layers were sequentially formed.

On the hole transport layer, the light emitting layer was thermally deposited under the vacuum as will be described below. On the hole transport layer, the light emitting layer was deposited in a thickness of 400 Å by using CBP (4,4'-N,N'-dicarbazole-biphenyl) as the host and $Ir(ppy)_3$ (tris(2-phenylpyridine)iridium) as the dopant at the ratio of 93:7. Thereafter, on the light emitting layer, BCP as the hole blocking layer was deposited in a thickness of 60 Å, and on the hole blocking layer, $Alq_3$ as the electron transport layer was deposited in a thickness of 200 Å. Finally, after on the electron transport layer, lithium fluoride (LiF) was deposited in a thickness of 10 Å to form the electron injection layer, on the electron injection layer, the aluminum (Al) cathode was deposited in a thickness of 1200 Å to form the cathode and thus manufacture the organic electroluminescence device.

Meanwhile, all organic compounds required to manufacture the OLED device were used in manufacturing of the OLED device by performing vacuum sublimation and purification under $10^{-6}$ to $10^{-8}$ torr for each material.

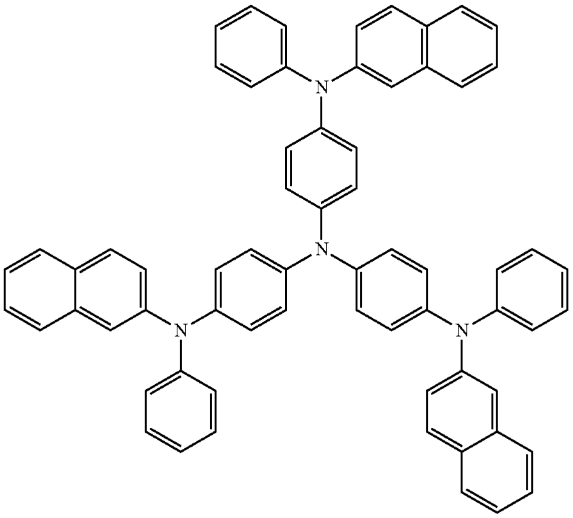

2-TNATA

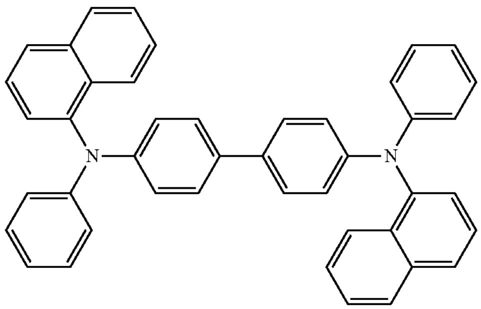

NPB

-continued

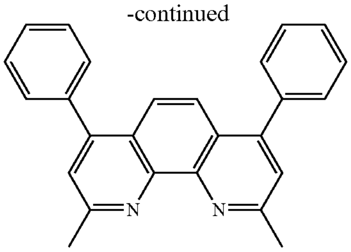

BCP

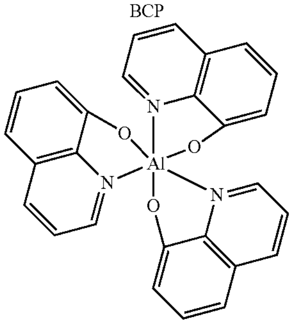

Alq3

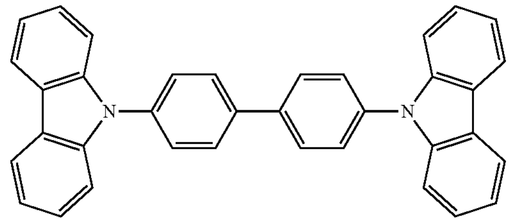

CBP

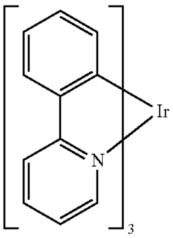

Ir(ppy)3

Comparative Example 2

The transparent electrode ITO thin film obtained from glass for the OLED (manufactured by Samsung Corning Co., Ltd.) was washed by the ultrasonic wave for 5 minutes for each of sequentially used trichloroethylene, acetone, ethanol, and distilled water, put into isopropanol to be stored, and then used.

Next, the ITO substrate was installed in the vacuum deposition apparatus. Thereafter, in the vacuum chamber, the hole injection layer was formed by depositing 4,4',4"-tris(N,N-(2-naphthyl)-phenylamino)triphenyl amine (2-TNATA) in a thickness of 600 Å under the vacuum on the ITO.

Thereafter, the hole transport layer was formed by depositing N,N'-bis(α-naphthyl)-N,N'-diphenyl-4,4'-diamine (NPB) in a thickness of 300 Å under the vacuum on the hole injection layer.

Then, the light emitting layer was deposited in a thickness 200 Å under the vacuum on the hole transport layer using the blue light emitting host material H1 and the blue light emitting dopant material D1 at the ratio of 95:5.

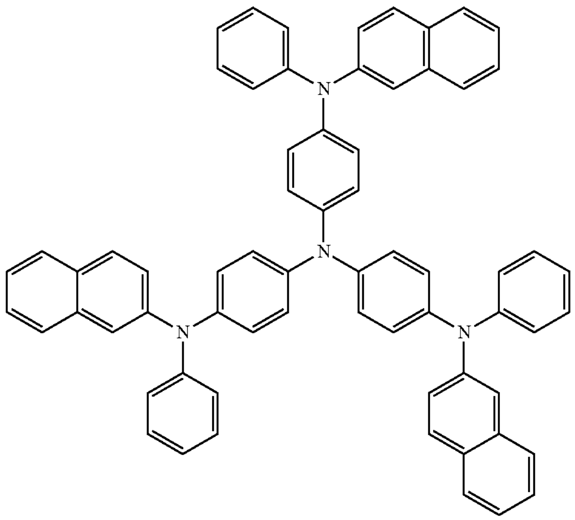

2-TNATA

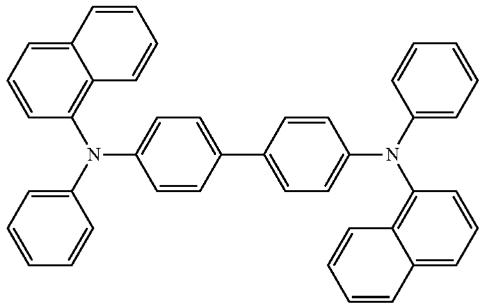

NPB

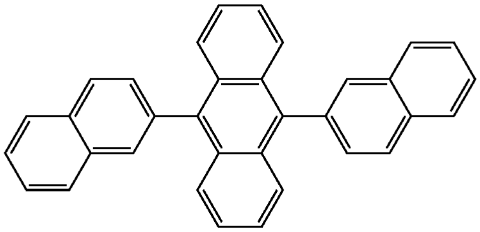

H1

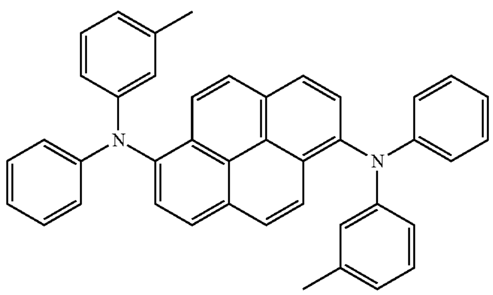

D1

Subsequently, the electron transport layer was formed by depositing the compound of the following Structural Formula E1 in a thickness of 300 Å on the light emitting layer.

E1

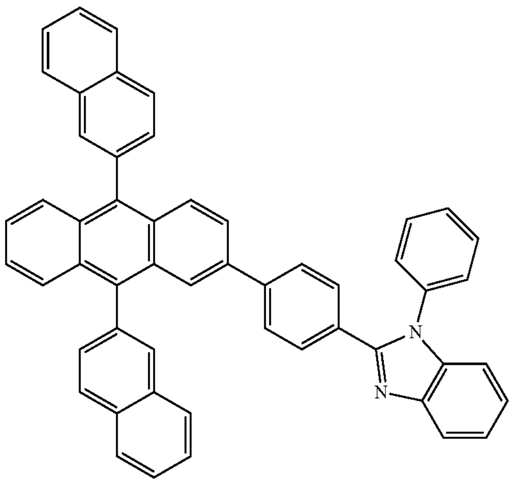

Thereafter, the OLED device was manufactured by depositing lithium fluoride (LiF) as the electron injection layer in a thickness 10 Å on the electron transport layer and depositing Al in a thickness of 1000 Å on the electron injection layer to form the cathode.

Meanwhile, all organic compounds required to manufacture the OLED device were used in manufacturing of the OLED by performing vacuum sublimation and purification under $10^{-6}$ to $10^{-8}$ torr for each material.

Examples 1-1 to 1-10

The same method as Comparative Example 1 was performed to manufacture the organic electroluminescence device, except that compounds 1-113, 1-119, 1-121, 1-122, 1-124, 1-141, 1-157, 1-211, 1-212, and 1-248 synthesized in the present invention were used instead of the host CPB used when the light emitting layer was formed in Comparative Example 1.

Examples 2-1 to 2-267

The same method as Comparative Example 2 was performed to manufacture the organic electroluminescence device, except that compounds prepared by the present invention were used instead of E1 used when the electron transport layer was formed in Comparative Example 2.

Driving voltage and light emitting efficiency of organic electroluminescence device Experimental Example 1

Electroluminescence (EL) properties of the organic electroluminescence devices manufactured in thusly manufactured Examples 1-1 to 1-10 and Comparative Example 1 were measured by M7000 manufactured by McScience Inc., and the life-span (T90) when reference luminance was 6000 cd/m$^2$ was measured by using the aforementioned measurement result through the life-span measurement apparatus (M6000) manufactured by McScience Inc. Properties of the organic electroluminescence device of the present invention are described in Table 3.

TABLE 3

| | Compound | Driving voltage (V) | Luminance (cd/m$^2$) | Efficiency (cd/A) | Color coordinate (x, y) | Life-span ($T_{90}$) |
|---|---|---|---|---|---|---|
| Example 1-1 | 1-113 | 4.73 | 6000 | 57.7 | (0.294, 0.654) | 59.3 |
| Example 1-2 | 1-119 | 4.71 | 6000 | 58.8 | (0.293, 0.653) | 60.9 |
| Example 1-3 | 1-124 | 4.92 | 6000 | 58.5 | (0.295, 0.654) | 58.2 |
| Example 1-4 | 1-157 | 4.78 | 6000 | 56.8 | (0.296, 0.655) | 58.7 |
| Example 1-5 | 2-127 | 4.92 | 6000 | 56.3 | (0.296, 0.654) | 57.4 |
| Example 1-6 | 2-148 | 4.69 | 6000 | 57.2 | (0.297, 0.653) | 56.1 |
| Example 1-7 | 3-12 | 4.68 | 6000 | 56.2 | (0.296, 0.652) | 55.4 |
| Example 1-8 | 4-109 | 4.87 | 6000 | 56.2 | (0.292, 0.653) | 61.4 |
| Example 1-9 | 4-113 | 4.87 | 6000 | 60.9 | (0.293, 0.654) | 55.7 |
| Example 1-10 | 4-119 | 4.82 | 6000 | 59.2 | (0.294, 0.652) | 58.2 |
| Comparative Example 1 | CBP | 5.24 | 6000 | 48.1 | (0.295, 0.651) | 50.0 |

As seen from the result of Table 3, in the organic electroluminescence device using the light emitting layer material of the organic electroluminescence device of the present invention, the driving voltage was low, light emitting efficiency was improved, and the life-span was significantly improved as compared to Comparative Example 1.

Experimental Example 2

The driving voltage, efficiency, the color coordinate, and the life-span of each of the organic electroluminescence devices manufactured in Comparative Example 2 and Examples 2-1 to 2-267 when light emitting luminance was 700 cd/m$^2$ were measured to be evaluated, and the result is described in the following Table 4. In this case, the life-span was measured by using M6000PMX manufactured by McScience Inc.

TABLE 4

| | Electron transport layer material | Light emitting luminance ($cd/m^2$) | Driving voltage (V) | Efficiency (cd/A) | Color coordinate (x, y) x | y | Life-span ($T_{50}$) |
|---|---|---|---|---|---|---|---|
| Comparative Example 1 | E1 | 700 | 4.70 | 4.50 | 0.150 | 0.180 | 330 |
| Example 2-1 | 1-1 | 700 | 5.55 | 3.59 | 0.150 | 0.172 | 595 |
| Example 2-2 | 1-12 | 700 | 6.14 | 3.37 | 0.149 | 0.179 | 317 |
| Example 2-3 | 1-16 | 700 | 4.37 | 4.52 | 0.150 | 0.178 | 586 |
| Example 2-4 | 1-36 | 700 | 6.29 | 2.15 | 0.149 | 0.170 | 72 |
| Example 2-5 | 1-190 | 700 | 4.25 | 4.47 | 0.150 | 0.150 | 355 |
| Example 2-6 | 1-318 | 700 | 5.43 | 4.48 | 0.150 | 0.180 | 15 |
| Example 2-7 | 1-482 | 700 | 4.60 | 4.49 | 0.147 | 0.153 | 557 |
| Example 2-8 | 1-483 | 700 | 4.58 | 4.94 | 0.150 | 0.157 | 595 |
| Example 2-9 | 2-3 | 700 | 4.37 | 5.09 | 0.150 | 0.189 | 595 |
| Example 2-10 | 2-36 | 700 | 5.59 | 2.96 | 0.151 | 0.150 | 432 |
| Example 2-11 | 2-38 | 700 | 5.23 | 3.87 | 0.150 | 0.150 | 298 |
| Example 2-12 | 2-44 | 700 | 4.25 | 5.17 | 0.149 | 0.182 | 605 |
| Example 2-13 | 2-107 | 700 | 4.60 | 4.47 | 0.152 | 0.175 | 586 |
| Example 2-14 | 2-123 | 700 | 4.71 | 4.64 | 0.150 | 0.150 | 317 |
| Example 2-15 | 2-243 | 700 | 4.72 | 4.49 | 0.153 | 0.150 | 595 |
| Example 2-16 | 3-19 | 700 | 4.37 | 3.88 | 0.145 | 0.153 | 365 |
| Example 2-17 | 3-39 | 700 | 5.26 | 4.55 | 0.147 | 0.150 | 166 |
| Example 2-18 | 3-43 | 700 | 4.60 | 5.09 | 0.150 | 0.152 | 653 |
| Example 2-19 | 3-46 | 700 | 5.31 | 3.82 | 0.150 | 0.150 | 414 |
| Example 2-20 | 4-1 | 700 | 4.72 | 4.71 | 0.150 | 0.140 | 576 |
| Example 2-21 | 4-56 | 700 | 4.60 | 4.64 | 0.148 | 0.161 | 499 |
| Example 2-22 | 4-58 | 700 | 4.87 | 4.25 | 0.151 | 0.168 | 566 |
| Example 2-23 | 4-76 | 700 | 4.48 | 4.64 | 0.149 | 0.169 | 509 |
| Example 2-24 | 4-169 | 700 | 4.61 | 4.55 | 0.148 | 0.151 | 518 |
| Example 2-25 | 1-3 | 700 | 4.69 | 4.72 | 0.150 | 0.169 | 481 |
| Example 2-26 | 1-4 | 700 | 4.55 | 4.92 | 0.150 | 0.168 | 360 |
| Example 2-27 | 1-8 | 700 | 4.89 | 4.68 | 0.153 | 0.150 | 522 |
| Example 2-28 | 1-10 | 700 | 5.01 | 4.78 | 0.151 | 0.150 | 489 |
| Example 2-29 | 1-251 | 700 | 4.69 | 4.72 | 0.150 | 0.169 | 481 |
| Example 2-30 | 1-255 | 700 | 4.47 | 4.93 | 0.150 | 0.157 | 592 |
| Example 2-31 | 1-100 | 700 | 4.88 | 5.22 | 0.149 | 0.167 | 397 |
| Example 2-32 | 1-109 | 700 | 4.61 | 5.09 | 0.150 | 0.168 | 420 |
| Example 2-33 | 1-102 | 700 | 4.92 | 5.18 | 0.150 | 0.177 | 500 |
| Example 2-34 | 1-123 | 700 | 4.82 | 5.18 | 0.151 | 0.170 | 502 |
| Example 2-35 | 1-366 | 700 | 4.97 | 5.22 | 0.150 | 0.177 | 411 |
| Example 2-36 | 1-369 | 700 | 4.92 | 4.95 | 0.150 | 0.173 | 330 |
| Example 2-37 | 1-416 | 700 | 4.89 | 4.68 | 0.153 | 0.150 | 522 |
| Example 2-38 | 1-451 | 700 | 5.01 | 4.78 | 0.151 | 0.150 | 489 |
| Example 2-39 | 1-452 | 700 | 4.69 | 4.72 | 0.150 | 0.169 | 481 |
| Example 2-40 | 1-459 | 700 | 5.00 | 5.07 | 0.150 | 0.166 | 487 |
| Example 2-41 | 1-460 | 700 | 4.92 | 5.18 | 0.150 | 0.177 | 500 |
| Example 2-42 | 1-471 | 700 | 4.72 | 5.03 | 0.150 | 0.150 | 392 |
| Example 2-43 | 1-401 | 700 | 4.79 | 4.97 | 0.150 | 0.159 | 351 |
| Example 2-44 | 1-391 | 700 | 4.73 | 4.88 | 0.149 | 0.155 | 401 |
| Example 2-45 | 1-370 | 700 | 5.00 | 5.07 | 0.150 | 0.166 | 487 |
| Example 2-46 | 1-175 | 700 | 4.92 | 5.18 | 0.150 | 0.177 | 500 |
| Example 2-47 | 1-39 | 700 | 4.82 | 5.18 | 0.151 | 0.170 | 502 |
| Example 2-48 | 1-41 | 700 | 4.97 | 5.22 | 0.150 | 0.177 | 411 |
| Example 2-49 | 1-43 | 700 | 4.92 | 4.95 | 0.150 | 0.173 | 330 |
| Example 2-50 | 1-44 | 700 | 5.07 | 4.99 | 0.150 | 0.177 | 359 |
| Example 2-51 | 1-47 | 700 | 5.19 | 4.41 | 0.150 | 0.188 | 366 |
| Example 2-52 | 1-146 | 700 | 4.69 | 5.32 | 0.151 | 0.170 | 379 |
| Example 2-53 | 1-155 | 700 | 4.88 | 5.22 | 0.149 | 0.167 | 397 |
| Example 2-54 | 1-58 | 700 | 4.61 | 5.09 | 0.150 | 0.168 | 420 |
| Example 2-55 | 1-67 | 700 | 4.82 | 5.00 | 0.148 | 0.151 | 433 |
| Example 2-56 | 1-74 | 700 | 4.82 | 5.18 | 0.151 | 0.170 | 502 |
| Example 2-57 | 1-166 | 700 | 4.97 | 5.22 | 0.150 | 0.177 | 411 |
| Example 2-58 | 1-178 | 700 | 4.92 | 4.95 | 0.150 | 0.173 | 330 |
| Example 2-59 | 1-179 | 700 | 5.07 | 4.99 | 0.150 | 0.177 | 359 |
| Example 2-60 | 1-168 | 700 | 5.19 | 4.41 | 0.150 | 0.188 | 366 |
| Example 2-61 | 1-169 | 700 | 4.92 | 5.18 | 0.150 | 0.177 | 500 |
| Example 2-62 | 4-3 | 700 | 4.47 | 4.93 | 0.150 | 0.157 | 592 |
| Example 2-63 | 4-4 | 700 | 5.21 | 5.20 | 0.œ | 0.150 | 548 |
| Example 2-64 | 4-8 | 700 | 4.88 | 4.55 | 0.150 | 0.153 | 528 |
| Example 2-65 | 4-9 | 700 | 4.89 | 4.68 | 0.153 | 0.150 | 522 |
| Example 2-66 | 4-10 | 700 | 5.01 | 4.78 | 0.151 | 0.150 | 489 |
| Example 2-67 | 4-12 | 700 | 4.69 | 4.72 | 0.150 | 0.169 | 481 |
| Example 2-68 | 4-15 | 700 | 4.55 | 4.92 | 0.150 | 0.168 | 360 |
| Example 2-69 | 4-19 | 700 | 4.92 | 5.02 | 0.152 | 0.151 | 331 |
| Example 2-70 | 4-22 | 700 | 5.22 | 4.50 | 0.149 | 0.161 | 390 |
| Example 2-71 | 4-29 | 700 | 4.99 | 4.71 | 0.148 | 0.177 | 399 |
| Example 2-72 | 4-33 | 700 | 5.09 | 5.09 | 0.150 | 0.182 | 429 |

TABLE 4-continued

| | Electron transport layer material | Light emitting luminance (cd/m$^2$) | Driving voltage (V) | Efficiency (cd/A) | Color coordinate (x, y) x | y | Life-span ($T_{50}$) |
|---|---|---|---|---|---|---|---|
| Example 2-73 | 4-91 | 700 | 4.79 | 5.16 | 0.150 | 0.180 | 522 |
| Example 2-74 | 4-93 | 700 | 4.79 | 4.47 | 0.150 | 0.180 | 429 |
| Example 2-75 | 4-94 | 700 | 5.11 | 4.54 | 0.151 | 0.177 | 422 |
| Example 2-76 | 4-99 | 700 | 4.62 | 4.55 | 0.149 | 0.176 | 449 |
| Example 2-77 | 4-100 | 700 | 5.33 | 4.53 | 0.150 | 0.188 | 330 |
| Example 2-78 | 4-101 | 700 | 5.27 | 4.54 | 0.152 | 0.182 | 337 |
| Example 2-79 | 4-102 | 700 | 4.72 | 5.03 | 0.150 | 0.150 | 392 |
| Example 2-80 | 4-107 | 700 | 4.79 | 4.97 | 0.150 | 0.159 | 351 |
| Example 2-81 | 4-109 | 700 | 4.73 | 4.88 | 0.149 | 0.155 | 401 |
| Example 2-82 | 4-113 | 700 | 5.00 | 5.07 | 0.150 | 0.166 | 487 |
| Example 2-83 | 4-43 | 700 | 4.92 | 5.18 | 0.150 | 0.177 | 500 |
| Example 2-84 | 4-36 | 700 | 4.82 | 5.18 | 0.151 | 0.170 | 502 |
| Example 2-85 | 4-38 | 700 | 4.97 | 5.22 | 0.150 | 0.177 | 411 |
| Example 2-86 | 4-39 | 700 | 4.92 | 4.95 | 0.150 | 0.173 | 330 |
| Example 2-87 | 4-49 | 700 | 5.07 | 4.99 | 0.150 | 0.177 | 359 |
| Example 2-88 | 4-59 | 700 | 5.19 | 4.41 | 0.150 | 0.188 | 366 |
| Example 2-89 | 4-61 | 700 | 4.69 | 5.32 | 0.151 | 0.170 | 379 |
| Example 2-90 | 4-63 | 700 | 4.88 | 5.22 | 0.149 | 0.167 | 397 |
| Example 2-91 | 4-64 | 700 | 4.61 | 5.09 | 0.150 | 0.168 | 420 |
| Example 2-92 | 4-65 | 700 | 4.82 | 5.00 | 0.148 | 0.151 | 433 |
| Example 2-93 | 4-72 | 700 | 4.82 | 5.18 | 0.151 | 0.170 | 502 |
| Example 2-94 | 4-254 | 700 | 4.97 | 5.22 | 0.150 | 0.177 | 411 |
| Example 2-95 | 4-251 | 700 | 4.92 | 4.95 | 0.150 | 0.173 | 330 |
| Example 2-96 | 4-336 | 700 | 5.07 | 4.99 | 0.150 | 0.177 | 359 |
| Example 2-97 | 4-362 | 700 | 5.19 | 4.41 | 0.150 | 0.188 | 366 |
| Example 2-98 | 4-79 | 700 | 4.92 | 5.18 | 0.150 | 0.177 | 500 |
| Example 2-99 | 4-84 | 700 | 5.33 | 4.53 | 0.150 | 0.188 | 330 |
| Example 2-100 | 4-85 | 700 | 5.00 | 5.07 | 0.150 | 0.166 | 487 |
| Example 2-101 | 4-89 | 700 | 4.92 | 5.18 | 0.150 | 0.177 | 500 |
| Example 2-102 | 4-166 | 700 | 4.69 | 4.72 | 0.150 | 0.169 | 481 |
| Example 2-103 | 4-174 | 700 | 4.89 | 4.68 | 0.153 | 0.150 | 522 |
| Example 2-104 | 4-177 | 700 | 5.01 | 4.78 | 0.151 | 0.150 | 489 |
| Example 2-105 | 4-179 | 700 | 4.69 | 4.72 | 0.150 | 0.169 | 481 |
| Example 2-106 | 4-481 | 700 | 4.55 | 4.92 | 0.150 | 0.168 | 360 |
| Example 2-107 | 4-484 | 700 | 4.92 | 5.02 | 0.152 | 0.151 | 331 |
| Example 2-108 | 4-485 | 700 | 5.22 | 4.50 | 0.149 | 0.161 | 390 |
| Example 2-109 | 4-564 | 700 | 4.47 | 4.93 | 0.150 | 0.157 | 592 |
| Example 2-110 | 4-565 | 700 | 4.88 | 5.22 | 0.149 | 0.167 | 397 |
| Example 2-111 | 4-574 | 700 | 4.61 | 5.09 | 0.150 | 0.168 | 420 |
| Example 2-112 | 4-576 | 700 | 4.82 | 5.00 | 0.148 | 0.151 | 433 |
| Example 2-113 | 4-578 | 700 | 4.82 | 5.18 | 0.151 | 0.170 | 502 |
| Example 2-114 | 4-590 | 700 | 4.79 | 5.16 | 0.150 | 0.180 | 522 |
| Example 2-115 | 4-591 | 700 | 4.79 | 4.47 | 0.150 | 0.180 | 429 |
| Example 2-116 | 4-599 | 700 | 5.11 | 4.54 | 0.151 | 0.177 | 422 |
| Example 2-117 | 4-600 | 700 | 4.62 | 4.55 | 0.149 | 0.176 | 449 |
| Example 2-118 | 10-1 | 700 | 4.79 | 4.97 | 0.150 | 0.159 | 351 |
| Example 2-119 | 10-3 | 700 | 4.73 | 4.88 | 0.149 | 0.155 | 401 |
| Example 2-120 | 10-5 | 700 | 5.07 | 4.99 | 0.150 | 0.177 | 359 |
| Example 2-121 | 10-6 | 700 | 5.19 | 4.41 | 0.150 | 0.188 | 366 |
| Example 2-122 | 10-10 | 700 | 4.69 | 5.32 | 0.151 | 0.170 | 379 |
| Example 2-123 | 10-12 | 700 | 5.01 | 4.78 | 0.151 | 0.150 | 489 |
| Example 2-124 | 10-13 | 700 | 4.88 | 5.22 | 0.149 | 0.167 | 397 |
| Example 2-125 | 10-15 | 700 | 4.73 | 4.88 | 0.149 | 0.155 | 401 |
| Example 2-126 | 10-19 | 700 | 4.82 | 5.00 | 0.148 | 0.151 | 433 |
| Example 2-127 | 10-21 | 700 | 4.82 | 5.18 | 0.151 | 0.170 | 502 |
| Example 2-128 | 10-23 | 700 | 4.82 | 5.18 | 0.151 | 0.170 | 502 |
| Example 2-129 | 10-25 | 700 | 4.97 | 5.22 | 0.150 | 0.177 | 411 |
| Example 2-130 | 10-27 | 700 | 4.92 | 4.95 | 0.150 | 0.173 | 330 |
| Example 2-131 | 10-29 | 700 | 4.92 | 5.18 | 0.150 | 0.177 | 500 |
| Example 2-132 | 10-31 | 700 | 4.72 | 5.03 | 0.150 | 0.150 | 392 |
| Example 2-133 | 10-33 | 700 | 4.79 | 4.97 | 0.150 | 0.159 | 351 |
| Example 2-134 | 10-35 | 700 | 4.73 | 4.88 | 0.149 | 0.155 | 401 |
| Example 2-135 | 10-37 | 700 | 4.92 | 5.02 | 0.152 | 0.151 | 331 |
| Example 2-136 | 10-39 | 700 | 4.82 | 5.18 | 0.151 | 0.170 | 502 |
| Example 2-137 | 10-41 | 700 | 4.73 | 4.88 | 0.149 | 0.155 | 401 |
| Example 2-138 | 10-43 | 700 | 5.00 | 5.07 | 0.150 | 0.166 | 487 |
| Example 2-139 | 10-45 | 700 | 4.62 | 4.55 | 0.149 | 0.176 | 449 |
| Example 2-140 | 10-46 | 700 | 4.97 | 5.22 | 0.150 | 0.177 | 411 |
| Example 2-141 | 10-48 | 700 | 4.92 | 4.95 | 0.150 | 0.173 | 330 |
| Example 2-142 | 10-49 | 700 | 5.00 | 5.07 | 0.150 | 0.166 | 487 |
| Example 2-143 | 10-51 | 700 | 4.92 | 5.18 | 0.150 | 0.177 | 500 |
| Example 2-144 | 10-53 | 700 | 4.72 | 5.03 | 0.150 | 0.150 | 392 |
| Example 2-145 | 10-55 | 700 | 4.79 | 4.97 | 0.150 | 0.159 | 351 |
| Example 2-146 | 10-56 | 700 | 4.73 | 4.88 | 0.149 | 0.155 | 401 |

TABLE 4-continued

| | Electron transport layer material | Light emitting luminance (cd/m$^2$) | Driving voltage (V) | Efficiency (cd/A) | Color coordinate (x, y) x | y | Life-span ($T_{50}$) |
|---|---|---|---|---|---|---|---|
| Example 2-147 | 10-60 | 700 | 4.61 | 5.09 | 0.150 | 0.168 | 420 |
| Example 2-148 | 10-62 | 700 | 4.82 | 5.00 | 0.148 | 0.151 | 433 |
| Example 2-149 | 10-63 | 700 | 4.82 | 5.18 | 0.151 | 0.170 | 502 |
| Example 2-150 | 10-65 | 700 | 4.97 | 5.22 | 0.150 | 0.177 | 411 |
| Example 2-151 | 10-69 | 700 | 4.92 | 4.95 | 0.150 | 0.173 | 330 |
| Example 2-152 | 10-71 | 700 | 4.73 | 4.88 | 0.149 | 0.155 | 401 |
| Example 2-153 | 10-73 | 700 | 5.00 | 5.07 | 0.150 | 0.166 | 487 |
| Example 2-154 | 10-75 | 700 | 4.62 | 4.55 | 0.149 | 0.176 | 449 |
| Example 2-155 | 10-77 | 700 | 5.33 | 4.53 | 0.150 | 0.188 | 330 |
| Example 2-156 | 10-79 | 700 | 5.27 | 4.54 | 0.152 | 0.182 | 337 |
| Example 2-157 | 10-81 | 700 | 4.72 | 5.03 | 0.150 | 0.150 | 392 |
| Example 2-158 | 10-83 | 700 | 4.79 | 4.97 | 0.150 | 0.159 | 351 |
| Example 2-159 | 10-85 | 700 | 4.73 | 4.88 | 0.149 | 0.155 | 401 |
| Example 2-160 | 10-87 | 700 | 5.07 | 4.99 | 0.150 | 0.177 | 359 |
| Example 2-161 | 10-89 | 700 | 5.19 | 4.41 | 0.150 | 0.188 | 366 |
| Example 2-162 | 10-91 | 700 | 4.69 | 5.32 | 0.151 | 0.170 | 379 |
| Example 2-163 | 10-93 | 700 | 5.01 | 4.78 | 0.151 | 0.150 | 489 |
| Example 2-164 | 10-95 | 700 | 4.69 | 4.72 | 0.150 | 0.169 | 481 |
| Example 2-165 | 10-96 | 700 | 4.55 | 4.92 | 0.150 | 0.168 | 360 |
| Example 2-166 | 10-98 | 700 | 4.92 | 5.02 | 0.152 | 0.151 | 331 |
| Example 2-167 | 10-99 | 700 | 5.22 | 4.50 | 0.149 | 0.161 | 390 |
| Example 2-168 | 11-1 | 700 | 4.73 | 4.88 | 0.149 | 0.155 | 401 |
| Example 2-169 | 11-3 | 700 | 5.00 | 5.07 | 0.150 | 0.166 | 487 |
| Example 2-170 | 11-5 | 700 | 4.92 | 5.18 | 0.150 | 0.177 | 500 |
| Example 2-171 | 11-6 | 700 | 4.82 | 5.18 | 0.151 | 0.170 | 502 |
| Example 2-172 | 11-10 | 700 | 4.97 | 5.22 | 0.150 | 0.177 | 411 |
| Example 2-173 | 11-12 | 700 | 4.89 | 4.68 | 0.153 | 0.150 | 522 |
| Example 2-174 | 11-13 | 700 | 5.01 | 4.78 | 0.151 | 0.150 | 489 |
| Example 2-175 | 11-15 | 700 | 4.69 | 4.72 | 0.150 | 0.169 | 481 |
| Example 2-176 | 11-19 | 700 | 5.00 | 5.07 | 0.150 | 0.166 | 487 |
| Example 2-177 | 11-21 | 700 | 4.69 | 4.72 | 0.150 | 0.169 | 481 |
| Example 2-178 | 11-23 | 700 | 4.55 | 4.92 | 0.150 | 0.168 | 360 |
| Example 2-179 | 11-26 | 700 | 4.92 | 5.02 | 0.152 | 0.151 | 331 |
| Example 2-180 | 11-28 | 700 | 4.73 | 4.88 | 0.149 | 0.155 | 401 |
| Example 2-181 | 11-29 | 700 | 5.00 | 5.07 | 0.150 | 0.166 | 487 |
| Example 2-182 | 11-30 | 700 | 4.62 | 4.55 | 0.149 | 0.176 | 449 |
| Example 2-183 | 11-33 | 700 | 5.33 | 4.53 | 0.150 | 0.188 | 330 |
| Example 2-184 | 11-35 | 700 | 5.27 | 4.54 | 0.152 | 0.182 | 337 |
| Example 2-185 | 11-36 | 700 | 4.72 | 5.03 | 0.150 | 0.150 | 392 |
| Example 2-186 | 11-39 | 700 | 4.69 | 5.32 | 0.151 | 0.170 | 379 |
| Example 2-187 | 11-41 | 700 | 4.88 | 5.22 | 0.149 | 0.167 | 397 |
| Example 2-188 | 11-43 | 700 | 4.61 | 5.09 | 0.150 | 0.168 | 420 |
| Example 2-189 | 11-45 | 700 | 4.82 | 5.00 | 0.148 | 0.151 | 433 |
| Example 2-190 | 11-46 | 700 | 4.82 | 5.18 | 0.151 | 0.170 | 502 |
| Example 2-191 | 11-48 | 700 | 4.82 | 5.18 | 0.151 | 0.170 | 502 |
| Example 2-192 | 11-49 | 700 | 4.97 | 5.22 | 0.150 | 0.177 | 411 |
| Example 2-193 | 11-50 | 700 | 4.92 | 4.95 | 0.150 | 0.173 | 330 |
| Example 2-194 | 11-53 | 700 | 4.92 | 5.18 | 0.150 | 0.177 | 500 |
| Example 2-195 | 11-55 | 700 | 4.72 | 5.03 | 0.150 | 0.150 | 392 |
| Example 2-196 | 11-56 | 700 | 4.79 | 4.97 | 0.150 | 0.159 | 351 |
| Example 2-197 | 11-60 | 700 | 4.73 | 4.88 | 0.149 | 0.155 | 401 |
| Example 2-198 | 11-62 | 700 | 4.92 | 5.02 | 0.152 | 0.151 | 331 |
| Example 2-199 | 11-63 | 700 | 4.82 | 5.18 | 0.151 | 0.170 | 502 |
| Example 2-200 | 11-65 | 700 | 4.97 | 5.22 | 0.150 | 0.177 | 411 |
| Example 2-201 | 11-69 | 700 | 4.92 | 4.95 | 0.150 | 0.173 | 330 |
| Example 2-202 | 11-71 | 700 | 5.07 | 4.99 | 0.150 | 0.177 | 359 |
| Example 2-203 | 11-73 | 700 | 5.19 | 4.41 | 0.150 | 0.188 | 366 |
| Example 2-204 | 11-76 | 700 | 4.92 | 5.18 | 0.150 | 0.177 | 500 |
| Example 2-205 | 11-78 | 700 | 5.33 | 4.53 | 0.150 | 0.188 | 330 |
| Example 2-206 | 11-79 | 700 | 5.00 | 5.07 | 0.150 | 0.166 | 487 |
| Example 2-207 | 11-80 | 700 | 4.92 | 5.18 | 0.150 | 0.177 | 500 |
| Example 2-208 | 11-83 | 700 | 4.69 | 4.72 | 0.150 | 0.169 | 481 |
| Example 2-209 | 11-85 | 700 | 4.89 | 4.68 | 0.153 | 0.150 | 522 |
| Example 2-210 | 11-86 | 700 | 5.01 | 4.78 | 0.151 | 0.150 | 489 |
| Example 2-211 | 11-89 | 700 | 4.69 | 4.72 | 0.150 | 0.169 | 481 |
| Example 2-212 | 11-91 | 700 | 4.55 | 4.92 | 0.150 | 0.168 | 360 |
| Example 2-213 | 11-95 | 700 | 4.92 | 5.02 | 0.152 | 0.151 | 331 |
| Example 2-214 | 11-97 | 700 | 5.22 | 4.50 | 0.149 | 0.161 | 390 |
| Example 2-215 | 11-98 | 700 | 4.47 | 4.93 | 0.150 | 0.157 | 592 |
| Example 2-216 | 11-99 | 700 | 4.88 | 5.22 | 0.149 | 0.167 | 397 |
| Example 2-217 | 11-100 | 700 | 4.61 | 5.09 | 0.150 | 0.168 | 420 |
| Example 2-218 | 12-1 | 700 | 5.22 | 4.50 | 0.149 | 0.161 | 390 |
| Example 2-219 | 12-3 | 700 | 4.99 | 4.71 | 0.148 | 0.177 | 399 |
| Example 2-220 | 12-5 | 700 | 5.09 | 5.09 | 0.150 | 0.182 | 429 |

TABLE 4-continued

| | Electron transport layer material | Light emitting luminance (cd/m$^2$) | Driving voltage (V) | Efficiency (cd/A) | Color coordinate (x, y) x | y | Life-span ($T_{50}$) |
|---|---|---|---|---|---|---|---|
| Example 2-221 | 12-6 | 700 | 4.89 | 4.68 | 0.153 | 0.150 | 522 |
| Example 2-222 | 12-10 | 700 | 5.01 | 4.78 | 0.151 | 0.150 | 489 |
| Example 2-223 | 12-12 | 700 | 4.69 | 4.72 | 0.150 | 0.169 | 481 |
| Example 2-224 | 12-13 | 700 | 4.55 | 4.92 | 0.150 | 0.168 | 360 |
| Example 2-225 | 12-15 | 700 | 4.92 | 5.02 | 0.152 | 0.151 | 331 |
| Example 2-226 | 12-19 | 700 | 5.22 | 4.50 | 0.149 | 0.161 | 390 |
| Example 2-227 | 12-21 | 700 | 4.99 | 4.71 | 0.148 | 0.177 | 399 |
| Example 2-228 | 12-23 | 700 | 5.09 | 5.09 | 0.150 | 0.182 | 429 |
| Example 2-229 | 12-25 | 700 | 4.79 | 5.16 | 0.150 | 0.180 | 522 |
| Example 2-230 | 12-27 | 700 | 4.79 | 4.47 | 0.150 | 0.180 | 429 |
| Example 2-231 | 12-29 | 700 | 5.11 | 4.54 | 0.151 | 0.177 | 422 |
| Example 2-232 | 12-31 | 700 | 4.62 | 4.55 | 0.149 | 0.176 | 449 |
| Example 2-233 | 12-33 | 700 | 5.33 | 4.53 | 0.150 | 0.188 | 330 |
| Example 2-234 | 12-35 | 700 | 5.27 | 4.54 | 0.152 | 0.182 | 337 |
| Example 2-235 | 12-37 | 700 | 4.72 | 5.03 | 0.150 | 0.150 | 392 |
| Example 2-236 | 12-39 | 700 | 4.79 | 4.97 | 0.150 | 0.159 | 351 |
| Example 2-237 | 12-41 | 700 | 4.73 | 4.88 | 0.149 | 0.155 | 401 |
| Example 2-238 | 12-43 | 700 | 4.69 | 4.72 | 0.150 | 0.169 | 481 |
| Example 2-239 | 12-45 | 700 | 4.55 | 4.92 | 0.150 | 0.168 | 360 |
| Example 2-240 | 12-46 | 700 | 4.92 | 5.02 | 0.152 | 0.151 | 331 |
| Example 2-241 | 12-48 | 700 | 4.97 | 5.22 | 0.150 | 0.177 | 411 |
| Example 2-242 | 12-49 | 700 | 4.92 | 4.95 | 0.150 | 0.173 | 330 |
| Example 2-243 | 12-51 | 700 | 5.07 | 4.99 | 0.150 | 0.177 | 359 |
| Example 2-244 | 12-53 | 700 | 5.19 | 4.41 | 0.150 | 0.188 | 366 |
| Example 2-245 | 12-55 | 700 | 4.69 | 5.32 | 0.151 | 0.170 | 379 |
| Example 2-246 | 12-56 | 700 | 4.88 | 5.22 | 0.149 | 0.167 | 397 |
| Example 2-247 | 12-60 | 700 | 4.61 | 5.09 | 0.150 | 0.168 | 420 |
| Example 2-248 | 12-62 | 700 | 4.82 | 5.00 | 0.148 | 0.151 | 433 |
| Example 2-249 | 12-63 | 700 | 4.82 | 5.18 | 0.151 | 0.170 | 502 |
| Example 2-250 | 12-65 | 700 | 4.82 | 5.18 | 0.151 | 0.170 | 502 |
| Example 2-251 | 12-69 | 700 | 4.97 | 5.22 | 0.150 | 0.177 | 411 |
| Example 2-252 | 12-71 | 700 | 4.92 | 4.95 | 0.150 | 0.173 | 330 |
| Example 2-253 | 12-73 | 700 | 5.07 | 4.99 | 0.150 | 0.177 | 359 |
| Example 2-254 | 12-75 | 700 | 5.19 | 4.41 | 0.150 | 0.188 | 366 |
| Example 2-255 | 12-77 | 700 | 4.69 | 5.32 | 0.151 | 0.170 | 379 |
| Example 2-256 | 12-79 | 700 | 5.00 | 5.07 | 0.150 | 0.166 | 487 |
| Example 2-257 | 12-81 | 700 | 4.92 | 5.18 | 0.150 | 0.177 | 500 |
| Example 2-258 | 12-83 | 700 | 4.69 | 4.72 | 0.150 | 0.169 | 481 |
| Example 2-259 | 12-85 | 700 | 4.89 | 4.68 | 0.153 | 0.150 | 522 |
| Example 2-260 | 12-87 | 700 | 5.01 | 4.78 | 0.151 | 0.150 | 489 |
| Example 2-261 | 12-89 | 700 | 4.69 | 4.72 | 0.150 | 0.169 | 481 |
| Example 2-262 | 12-91 | 700 | 4.55 | 4.92 | 0.150 | 0.168 | 360 |
| Example 2-263 | 12-93 | 700 | 4.92 | 5.02 | 0.152 | 0.151 | 331 |
| Example 2-264 | 12-95 | 700 | 5.22 | 4.50 | 0.149 | 0.161 | 390 |
| Example 2-265 | 12-96 | 700 | 4.47 | 4.93 | 0.150 | 0.157 | 592 |
| Example 2-266 | 12-98 | 700 | 4.88 | 5.22 | 0.149 | 0.167 | 397 |
| Example 2-267 | 12-99 | 700 | 4.61 | 5.09 | 0.150 | 0.168 | 420 |

Table 4 shows that in the organic electroluminescence devices of Examples 2-1 to 2-267 using compounds according to the present invention, the driving voltage is low and light emitting efficiency is high as compared to the organic electroluminescence device using the E1 electron transport layer material of the Comparative Example. Further, it is shown that device durability, that is, the life-span property is better than that of the Comparative Example.

What is claimed is:

1. A compound of the following Chemical Formula 1:

[Chemical Formula 1]

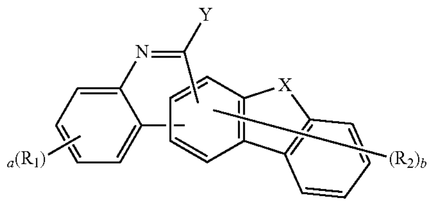

in Chemical Formula 1,

X is $NR_3$, $CR_4R_5$, S, O, or Se,

Y is -(L)m-(Z)n,

L is selected from the group consisting of —P(═O)$R_{10}$—; substituted or unsubstituted $C_6$ to $C_{60}$ monocyclic or polycyclic arylene; substituted or unsubstituted $C_2$ to $C_{60}$ monocyclic or polycyclic heteroarylene; and amine substituted or unsubstituted by substituted or unsubstituted $C_6$ to $C_{60}$ monocyclic or polycyclic aryl, or substituted or unsubstituted $C_2$ to $C_{60}$ monocyclic or polycyclic heteroaryl, m is an integer of 1 to 6, n is an integer of 1 to 5, Z is selected from the group consisting of deuterium; halogen; —P(═O)$R_{11}R_{12}$; substituted or unsubstituted $C_1$ to $C_{60}$ straight-chain or branch-chain alkyl; substituted or unsubstituted $C_6$ to $C_{60}$ monocyclic or polycyclic aryl; substituted or unsubstituted $C_2$ to $C_{60}$ monocyclic or polycyclic heteroaryl; and amine substituted or unsubstituted by substituted or unsubstituted $C_6$ to $C_{60}$ monocyclic or polycyclic aryl, or substituted or unsubstituted $C_2$ to $C_{60}$ monocyclic or polycyclic heteroaryl, and $R_{10}$ to $R_{12}$ are the same as or different from each other, and are each independently hydrogen; substituted or unsubstituted $C_1$ to $C_{60}$ straight-chain or branch-chain alkyl; substituted or unsubstituted $C_3$ to $C_{60}$ monocyclic or polycyclic cycloalkyl; substituted or unsubstituted $C_6$ to $C_{60}$ monocyclic or polycyclic aryl; or substituted or unsubstituted $C_2$ to $C_{60}$ monocyclic or polycyclic heteroaryl, $R_1$ is hydrogen, $R_2$ is selected from the group consisting of hydrogen; deuterium; halogen; —P(═O)$R_8R_9$; substituted or unsubstituted $C_1$ to $C_{60}$ straight-chain or branch-chain alkyl; substituted or unsubstituted $C_2$ to $C_{60}$ straight-chain or branch-chain alkenyl; substituted or unsubstituted $C_2$ to $C_{60}$ straight-chain or branch-chain alkynyl; substituted or unsubstituted $C_1$ to $C_{60}$ straight-chain or branch-chain alkoxy; substituted or unsubstituted $C_3$ to $C_{60}$ monocyclic or polycyclic cycloalkyl; substituted or unsubstituted $C_2$ to $C_{60}$ monocyclic or polycyclic heterocycloalkyl; substituted or unsubstituted $C_6$ to $C_{60}$ monocyclic or polycyclic aryl; substituted or unsubstituted $C_2$ to $C_{60}$ monocyclic or polycyclic heteroaryl; and amine substituted or unsubstituted by substituted or unsubstituted $C_1$ to $C_{20}$ alkyl, substituted or unsubstituted $C_6$ to $C_{60}$ monocyclic or polycyclic aryl, or substituted or unsubstituted $C_2$ to $C_{60}$ monocyclic or polycyclic heteroaryl, a is an integer of 0 to 4, in the case wherein when a is 2 or more, $R_1$s are the same as or different from each other, b is an integer of 0 to 6, in the case wherein when b is 2 or more, $R_2$s are the same as or different from each other, $R_3$ is selected from the group consisting of deuterium; halogen; —P(═O)$R_6R_7$; substituted or unsubstituted $C_6$ to $C_{60}$ monocyclic or polycyclic aryl; substituted or unsubstituted $C_2$ to $C_{60}$ monocyclic or polycyclic heteroaryl; and amine substituted or unsubstituted by substituted or unsubstituted $C_1$ to $C_{20}$ alkyl, substituted or unsubstituted $C_6$ to $C_{60}$ monocyclic or polycyclic aryl, or substituted or unsubstituted $C_2$ to $C_{60}$ monocyclic or polycyclic heteroaryl, and $R_4$ to $R_9$ are the same as or different from each other, and are each independently hydrogen; substituted or unsubstituted $C_1$ to $C_{60}$ straight-chain or branch-chain alkyl; substituted or unsubstituted $C_3$ to $C_{60}$ monocyclic or polycyclic cycloalkyl; substituted or unsubstituted $C_6$ to $C_{60}$ monocyclic or polycyclic aryl; or substituted or unsubstituted $C_2$ to $C_{60}$ monocyclic or polycyclic heteroaryl.

2. The compound of claim 1, wherein the term "substituted or unsubstituted" means that there is substitution or no substitution is performed by one or more substituent groups selected from deuterium, halogen, —SiRR'R", —P(═O)RR', $C_6$ to $C_{60}$ aryl, and $C_2$ to $C_{60}$ heteroaryl, or a substituent group where two or more substituent groups selected from the aforementioned substituent groups are connected, and R, R', and R" are the same as or different from each other, and are each independently hydrogen; $C_1$ to $C_{60}$ straight-chain or branch-chain alkyl substituted or unsubstituted by one or more substituent groups selected from deuterium, halogen, $C_6$ to $C_{60}$ monocyclic or polycyclic aryl, and $C_2$ to $C_{60}$ monocyclic or polycyclic heteroaryl; $C_3$ to $C_{60}$ monocyclic or polycyclic cycloalkyl substituted or unsubstituted by one or more substituent groups selected from deuterium, halogen, $C_6$ to $C_{60}$ monocyclic or polycyclic aryl, and $C_2$ to $C_{60}$ monocyclic or polycyclic heteroaryl; $C_6$ to $C_{60}$ monocyclic or polycyclic aryl substituted or unsubstituted by one or more substituent groups selected from deuterium, halogen, $C_6$ to $C_{60}$ monocyclic or polycyclic aryl, and $C_2$ to $C_{60}$ monocyclic or polycyclic heteroaryl; or $C_2$ to $C_{60}$ monocyclic or polycyclic heteroaryl substituted or unsubstituted by one or more substituent groups selected from deuterium, halogen, $C_6$ to $C_{60}$ monocyclic or polycyclic aryl, and $C_2$ to $C_{60}$ monocyclic or polycyclic heteroaryl.

3. The compound of claim 1, wherein L is selected from the group consisting of —P(═O)$R_{10}$—; substituted or unsubstituted phenylene; substituted or unsubstituted biphenylene; substituted or unsubstituted naphthylene; substituted or unsubstituted anthrylene; substituted or unsubstituted phenanthrenylene; substituted or unsubstituted triphenylenyl ene; substituted or unsubstituted 9,9-diphenyl-9H-fluorenylene; substituted or unsubstituted pyridylene; substituted or unsubstituted pyrimidylene; substituted or unsubstituted triazinylene; substituted or unsubstituted quinolylene; substituted or unsubstituted quinazolinylene; substituted or unsubstituted benzothiazolylene; substituted or unsubstituted benzoxazolylene; substituted or unsubstituted benzimidazolylene; substituted or unsubstituted divalent dibenzothiophene group; substituted or unsubstituted dibenzofuranylene; substituted or unsubstituted carbazolylene; substituted or unsubstituted indolo[2, 3-a]carbazolylene; substituted or unsubstituted naphthylidinylene; substituted or unsubstituted oxadiazolylene; substituted or unsubstituted pyrazolo[1, 5-c] quinazolinylene; substituted or unsubstituted pyrido[1,2-a]indazolylene; substituted or unsubstituted dibenzo[c, h]acridyl; substituted or unsubstituted diarylamine; substituted or unsubstituted diheteroarylamine; and substituted or unsubstituted arylheteroarylamine, in the case where L is substituted, a substituent group is selected from deuterium, halogen, —SiRR'R", —P(═O)RR', substituted or unsubstituted $C_6$ to $C_{60}$ monocyclic or polycyclic aryl, and substituted or unsubstituted $C_2$ to $C_{60}$ monocyclic or polycyclic heteroaryl, and R, R', R", and $R_{10}$ are the same as or different from each other, and are each independently hydrogen; substituted or unsubstituted $C_1$ to $C_{60}$ straight-chain or branch-chain alkyl; substituted or unsubstituted $C_3$ to $C_{60}$ monocyclic or polycyclic cycloalkyl; substituted or unsubstituted $C_6$ to $C_{60}$ monocyclic or polycyclic aryl; or substituted or unsubstituted $C_2$ to $C_{60}$ monocyclic or polycyclic heteroaryl.

4. The compound of claim 1, wherein Z is selected from the group consisting of deuterium; halogen; —P(═O)$R_{11}R_{12}$; substituted or unsubstituted ethyl; substituted or unsubstituted phenyl; substituted or unsubstituted biphenyl; substituted or unsubstituted naphthyl; substituted or unsubstituted anthryl; substituted or unsubstituted phenanthrenyl; substituted or unsubstituted triphenylenyl; substituted or unsubstituted 9,9-diphenyl-9H-fluorenyl; substituted or unsubstituted pyridyl; substituted or unsubstituted pyrimidyl; substituted or unsubstituted triazinyl; substituted or unsubstituted quinolyl; substituted or unsubstituted quinazolinyl; substituted or unsubstituted benzothiazolyl; substituted or unsubstituted benzoxazolyl; substituted or unsubstituted benzimidazolyl; substituted or unsubstituted dibenzothiophenyl; substituted or unsubstituted dibenzofuranyl; substituted or unsubstituted carbazolyl; substituted or unsubstituted indolo[2, 3-a]carbazolyl, substituted or unsubstituted naphthylidyl; substituted or unsubstituted oxadiazolyl; substituted or unsubstituted pyrazolo[1, 5-c] quinazolinyl; substituted or unsubstituted pyrido[1,2-a]indazolyl; substituted or unsubstituted dibenzo[c, h]acridyl; substituted or unsubstituted benzo[b]naphtho[2,3-d]thiophene group; substituted or unsubstituted benzo[h]naphtho [2,3-c]acridyl; substituted or unsubstituted benzo[f]quinolyl; substituted or unsubstituted diarylamine; substituted or unsubstituted diheteroarylamine; and substituted or unsubstituted arylheteroarylamine, in the case where Z is substituted, a substituent group is selected from deuterium, halogen, —SiRR'R", —P(═O)RR', substituted or unsubstituted $C_6$ to $C_{60}$ monocyclic or polycyclic aryl, and substituted or unsubstituted $C_2$ to $C_{60}$ monocyclic or polycyclic heteroaryl, and R, R', R", $R_{11}$, and $R_{12}$ are the same as or different from each other, and are each independently hydrogen; substituted or unsubstituted $C_1$ to $C_{60}$ straight-chain or branch-chain alkyl; substituted or unsubstituted $C_3$ to $C_{60}$ monocyclic or polycyclic cycloalkyl; substituted or unsubstituted $C_6$ to $C_{60}$ monocyclic or polycyclic aryl; or substituted or unsubstituted $C_2$ to $C_{60}$ monocyclic or polycyclic heteroaryl.

5. The compound of claim 1, wherein Z is substituted or unsubstituted $C_2$ to $C_{60}$ monocyclic or polycyclic heteroaryl, and wherein heteroaryl includes at least one selected from N, O, and S as a hetero atom.

6. The compound of claim 1, wherein in Chemical Formula 1, X is $CR_4R_5$, S, O, or Se, L is substituted or unsubstituted phenylene; or substituted or unsubstituted pyridylene, $R_4$ and $R_5$ are the same as $R_4$ and $R_5$ of Chemical Formula 1, m is an integer of 1 to 6, n is an integer of 1 to 5, Z is selected from the group consisting of deuterium; halogen; —P(═O)$R_{11}R_{12}$; substituted or unsubstituted $C_1$ to $C_{60}$ straight-chain or branch-chain alkyl; substituted or unsubstituted $C_6$ to $C_{60}$ monocyclic or polycyclic aryl; substituted or unsubstituted $C_2$ to $C_{60}$ monocyclic or polycyclic heteroaryl; and amine substituted or unsubstituted by substituted or unsubstituted $C_6$ to $C_{60}$ monocyclic or polycyclic aryl, or substituted or unsubstituted $C_2$ to $C_{60}$ monocyclic or polycyclic heteroaryl, $R_{11}$ and $R_{12}$ are the same as or different from each other, and are each independently hydrogen; substituted or unsubstituted $C_1$ to $C_{60}$ straight-chain or branch-chain alkyl; substituted or unsubstituted $C_3$ to $C_{60}$ monocyclic or polycyclic cycloalkyl; substituted or unsubstituted $C_6$ to $C_{60}$ monocyclic or polycyclic aryl; or substituted or unsubstituted $C_2$ to $C_{60}$ monocyclic or polycyclic heteroaryl, and Z is bonded to an atom bonded to a core of L at a para or meta position thereof.

7. The compound of claim 1, wherein Chemical Formula 1 is represented by any one of the following Chemical Formulas 2 to 7:

[Chemical Formula 2]

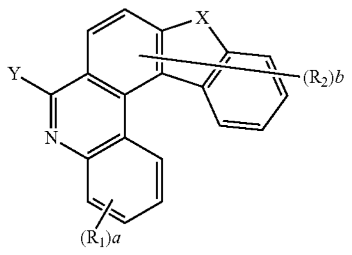

[Chemical Formula 3]

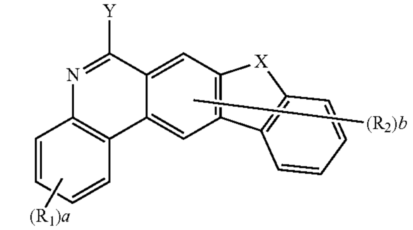

[Chemical Formula 4]

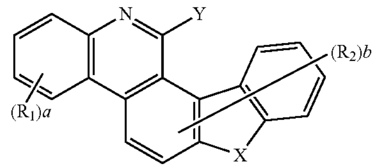

[Chemical Formula 5]

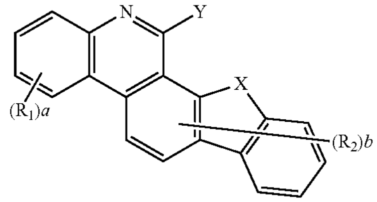

[Chemical Formula 6]

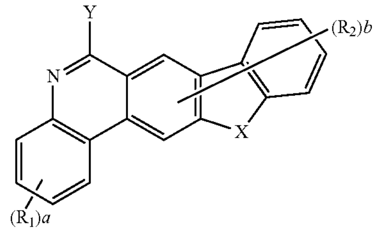

[Chemical Formula 7]

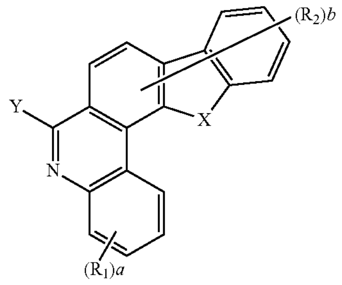

in Chemical Formulas 2 to 7, definitions of X, Y, $R_1$, $R_2$, a, and b are the same as definitions of X, Y, $R_1$, $R_2$, a, and b of Chemical Formula 1.

8. The compound of claim 1, wherein Chemical Formula 1 is represented by any one of the following Chemical Formulas 8 to 12:

[Chemical Formula 8]

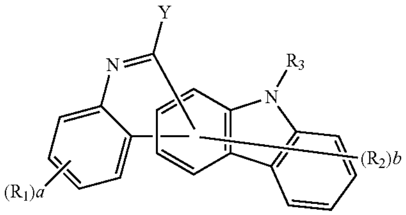

[Chemical Formula 9]

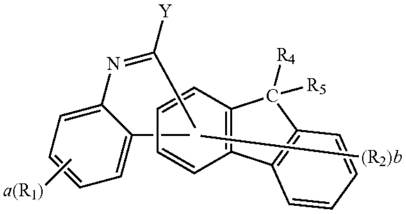

[Chemical Formula 10]

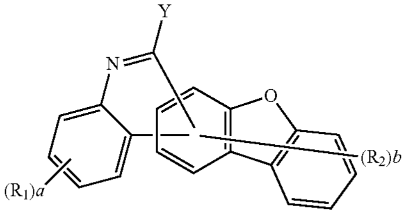

[Chemical Formula 11]

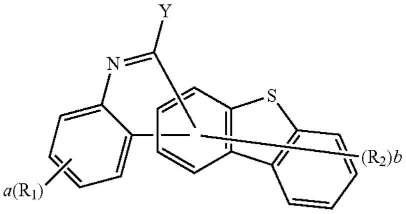

[Chemical Formula 12]

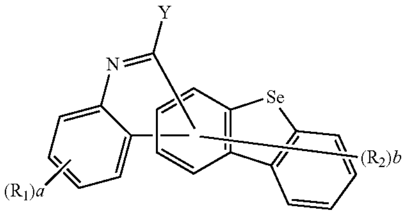

in Chemical Formulas 8 to 12, Y, a, b, and $R_1$ to $R_5$ are the same as Y, a, b, and $R_1$ to $R_5$ of Chemical Formula 1.

9. The compound of claim 8, wherein Chemical Formula 8 is represented by any one of the following Chemical Formulas 13 to 24:

[Chemical Formula 13]

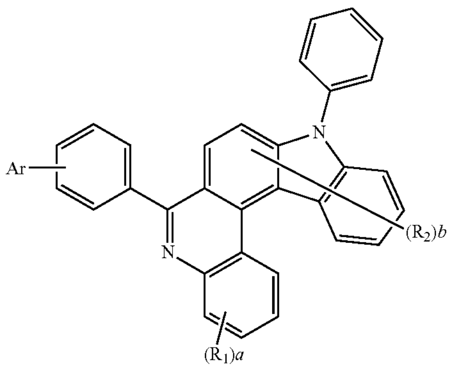

[Chemical Formula 14]

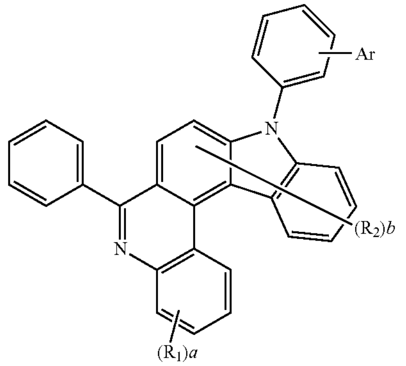

[Chemical Formula 15]

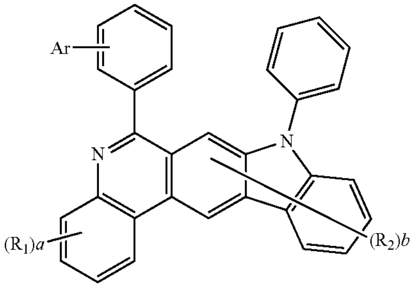

[Chemical Formula 16]

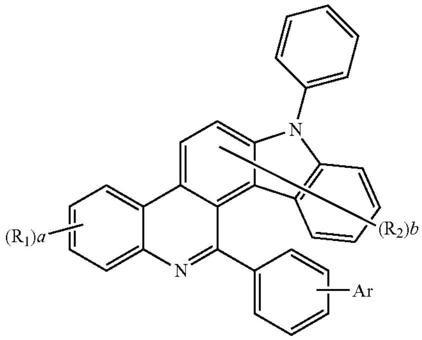

-continued

[Chemical Formula 17]

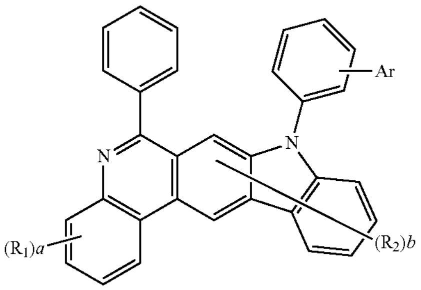

[Chemical Formula 18]

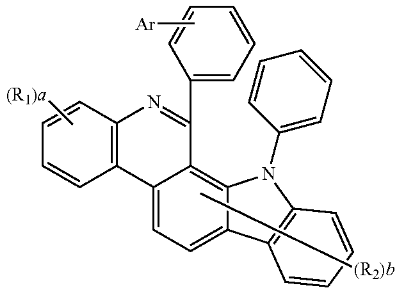

[Chemical Formula 19]

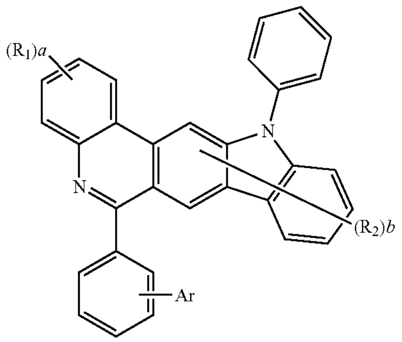

[Chemical Formula 20]

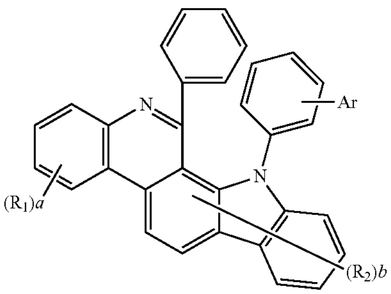

-continued

[Chemical Formula 21]

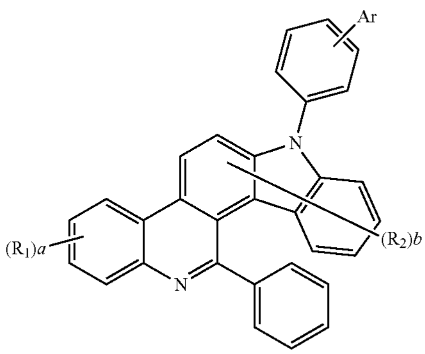

[Chemical Formula 22]

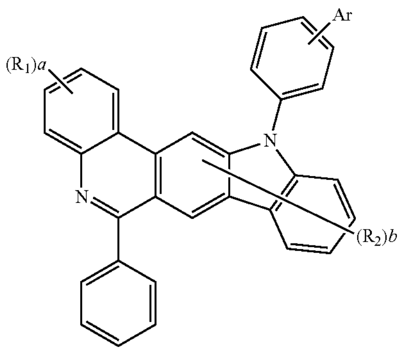

[Chemical Formula 23]

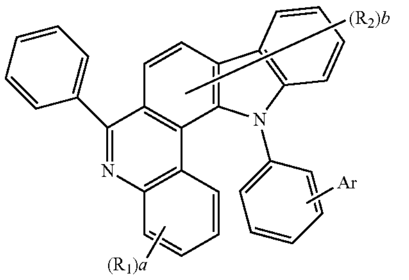

[Chemical Formula 24]

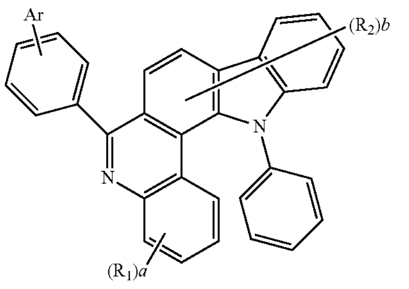

in Chemical Formulas 13 to 24, $R_1$ is hydrogen, $R_2$ is selected from the group consisting of hydrogen; deuterium; halogen; —P(=O)$R_8R_9$;

substituted or unsubstituted $C_1$ to $C_{60}$ straight-chain or branch-chain alkyl; substituted or unsubstituted $C_2$ to $C_{60}$ straight-chain or branch-chain alkenyl; substituted or unsubstituted $C_2$ to $C_{60}$ straight-chain or branch-chain alkynyl; substituted or unsubstituted $C_1$ to $C_{60}$ straight-chain or branch-chain alkoxy; substituted or unsubstituted $C_3$ to $C_{60}$ monocyclic or polycyclic cycloalkyl; substituted or unsubstituted $C_2$ to $C_{60}$ monocyclic or polycyclic heterocycloalkyl; substituted or unsubstituted $C_6$ to $C_{60}$ monocyclic or polycyclic aryl; substituted or unsubstituted $C_2$ to $C_{60}$ monocyclic or polycyclic heteroaryl; and amine substituted or unsubstituted by substituted or unsubstituted $C_1$ to $C_{20}$ alkyl, substituted or unsubstituted $C_6$ to $C_{60}$ monocyclic or polycyclic aryl, or substituted or unsubstituted $C_2$ to $C_{60}$ monocyclic or polycyclic heteroaryl, a is an integer of 0 to 4, in the case wherein when a is 2 or more, $R_1$s are the same as or different from each other, b is an integer of 0 to 6, in the case wherein when b is 2 or more, $R_2$s are the same as or different from each other, Ar is selected from the group consisting of hydrogen; deuterium; halogen; —P(═O)$R_{11}R_{12}$; substituted or unsubstituted $C_6$ to $C_{60}$ monocyclic or polycyclic aryl; substituted or unsubstituted $C_2$ to $C_{60}$ monocyclic or polycyclic heteroaryl; substituted or unsubstituted $C_1$ to $C_{60}$ straight-chain or branch-chain alkyl; and amine substituted or unsubstituted by substituted or unsubstituted $C_6$ to $C_{60}$ monocyclic or polycyclic aryl, or substituted or unsubstituted $C_2$ to $C_{60}$ monocyclic or polycyclic heteroaryl, and $R_8$, $R_9$, $R_{11}$, and $R_{12}$ are the same as or different from each other, and are each independently hydrogen; substituted or unsubstituted $C_1$ to $C_{60}$ straight-chain or branch-chain alkyl; substituted or unsubstituted $C_3$ to $C_{60}$ monocyclic or polycyclic cycloalkyl; substituted or unsubstituted $C_6$ to $C_{60}$ monocyclic or polycyclic aryl; or substituted or unsubstituted $C_2$ to $C_{60}$ monocyclic or polycyclic heteroaryl.

10. The compound of claim 7, wherein Chemical Formulas 2 to 7 are represented by the following Chemical Formulas 25 to 30, respectively:

[Chemical Formula 25]

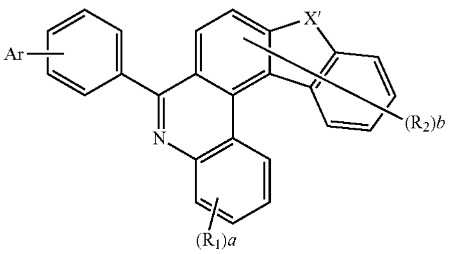

[Chemical Formula 26]

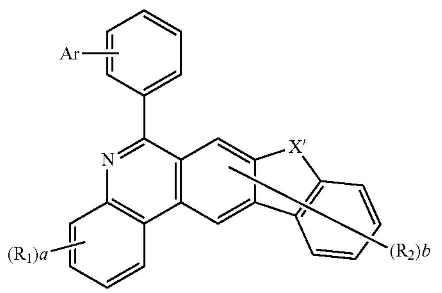

-continued

[Chemical Formula 27]

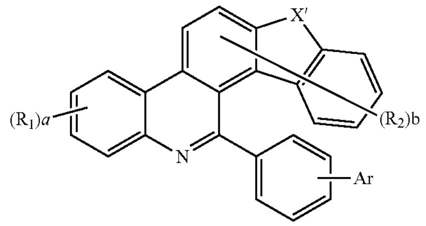

[Chemical Formula 28]

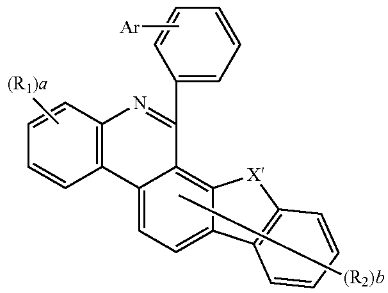

[Chemical Formula 29]

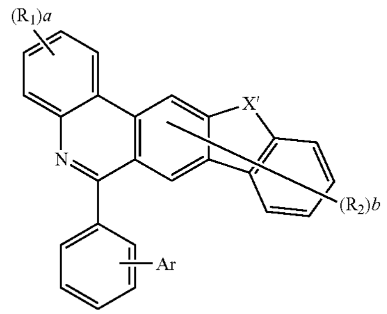

[Chemical Formula 30]

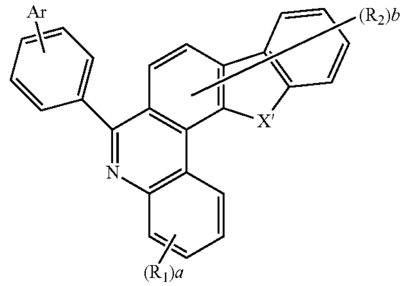

in Chemical Formulas 25 to 30, X' is $CR_4R_5$, O, S, or Se, $R_1$ is hydrogen, $R_2$ is selected from the group consisting of hydrogen; deuterium; halogen; —P(═O)$R_8R_9$;

substituted or unsubstituted $C_1$ to $C_{60}$ straight-chain or branch-chain alkyl; substituted or unsubstituted $C_2$ to $C_{60}$ straight-chain or branch-chain alkenyl; substituted or unsubstituted $C_2$ to $C_{60}$ straight-chain or branch-chain alkynyl; substituted or unsubstituted $C_1$ to $C_{60}$ straight-chain or branch-chain alkoxy; substituted or unsubstituted $C_3$ to $C_{60}$ monocyclic or polycyclic cycloalkyl; substituted or unsubstituted $C_2$ to $C_{60}$ monocyclic or polycyclic heterocycloalkyl; substituted or unsubstituted $C_6$ to $C_{60}$ monocyclic or polycyclic aryl; substituted or unsubstituted $C_2$ to $C_{60}$ monocyclic or polycyclic heteroaryl; and amine substituted or unsubstituted by substituted or unsubstituted $C_1$ to $C_{20}$ alkyl, substituted or unsubstituted $C_6$ to $C_{60}$ monocyclic or polycyclic aryl, or substituted or unsubstituted $C_2$ to $C_{60}$ monocyclic or polycyclic heteroaryl, a is an integer of 0 to 4, in the case wherein when a is 2 or more, $R_1$s are the same as or different from each other, b is an integer of 0 to 6, in the case wherein when b is 2 or more, $R_2$s are the same as or different from each other, Ar is selected from the group consisting of hydrogen; deuterium; halogen; —P(═O)$R_{11}R_{12}$; substituted or unsubstituted $C_1$ to $C_{60}$ straight-chain or branch-chain alkyl; substituted or unsubstituted $C_6$ to $C_{60}$ monocyclic or polycyclic aryl; substituted or unsubstituted $C_2$ to $C_{60}$ monocyclic or polycyclic heteroaryl; and amine substituted or unsubstituted by substituted or unsubstituted $C_6$ to $C_{60}$ monocyclic or polycyclic aryl, or substituted or unsubstituted $C_2$ to $C_{60}$ monocyclic or polycyclic heteroaryl, and $R_4$, $R_5$, $R_8$, $R_9$, $R_{11}$, and $R_{12}$ are the same as or different from each other, and are each independently hydrogen; substituted or unsubstituted $C_1$ to $C_{60}$ straight-chain or branch-chain alkyl; substituted or unsubstituted $C_3$ to $C_{60}$ monocyclic or polycyclic cycloalkyl; substituted or unsubstituted $C_6$ to $C_{60}$ monocyclic or polycyclic aryl; or substituted or unsubstituted $C_2$ to $C_{60}$ monocyclic or polycyclic heteroaryl.

11. The compound of claim 1, wherein the compound of Chemical Formula 1 is selected from the following compounds:

1-1

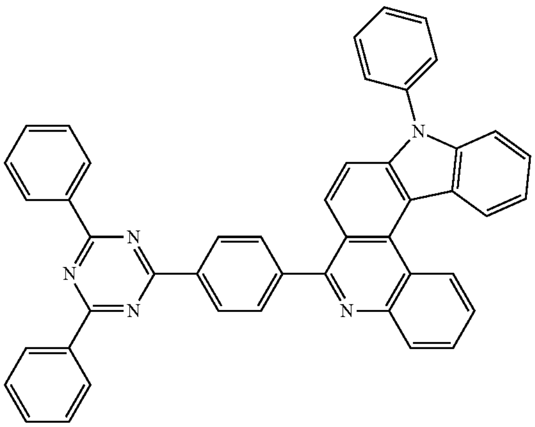

1-2

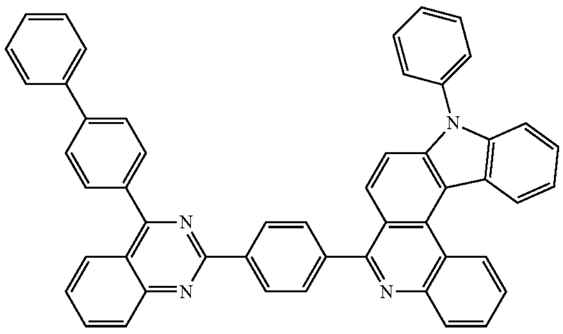

1-3

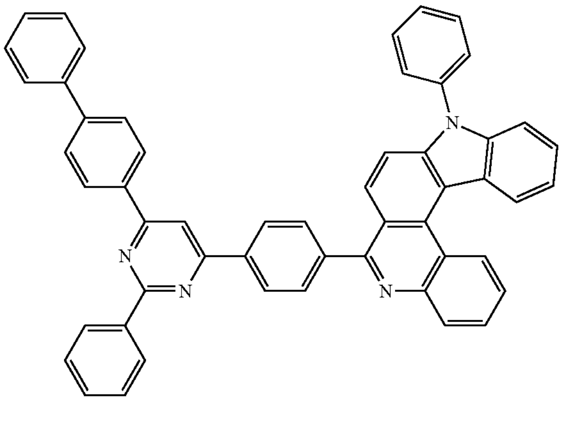

1-4

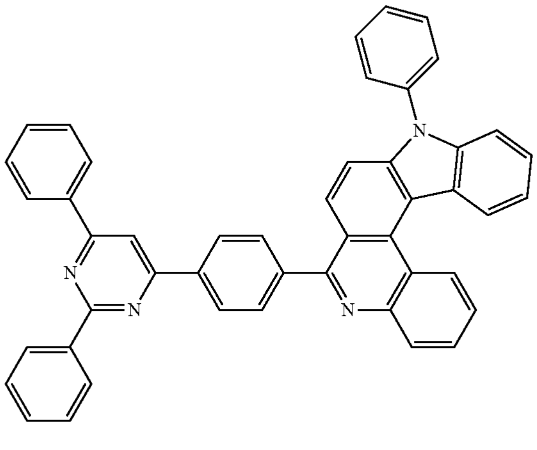

-continued
1-5
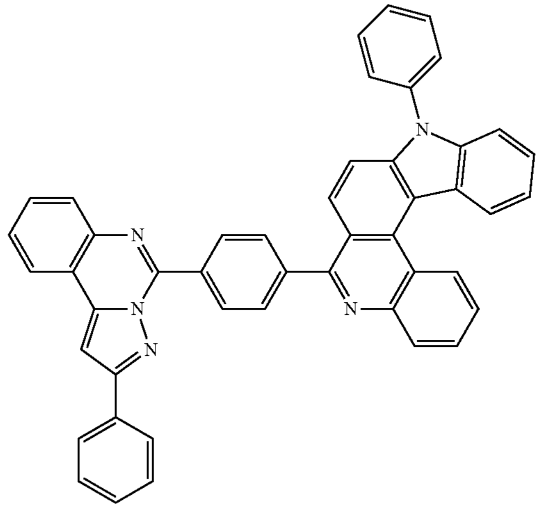
1-6
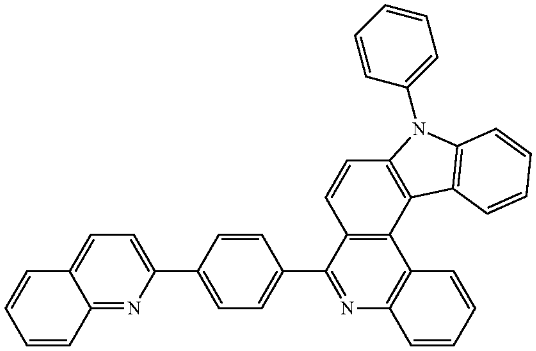
1-7
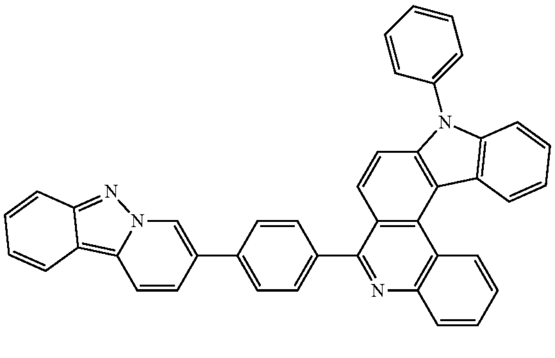
1-8
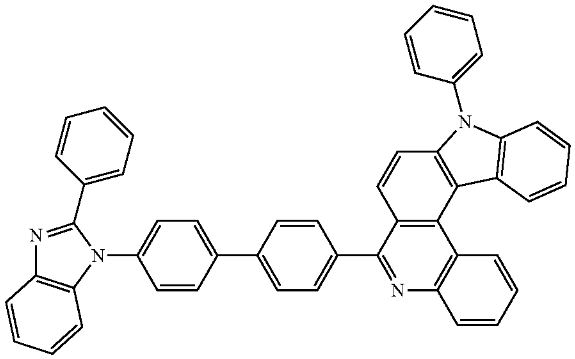
1-9
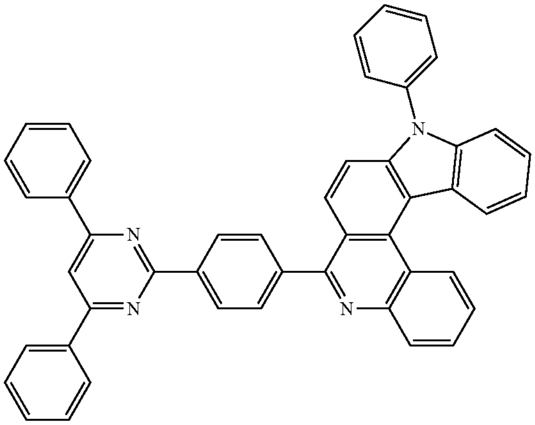
1-10
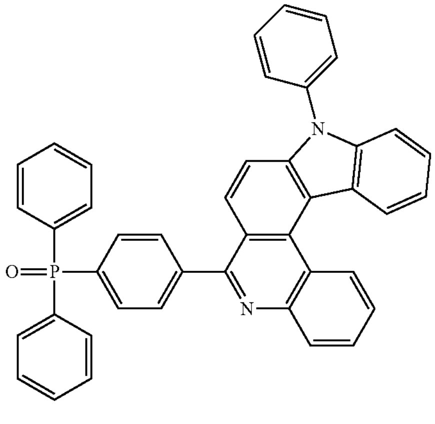

-continued
1-11
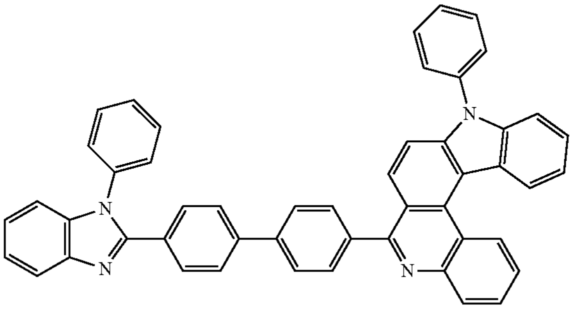
1-12
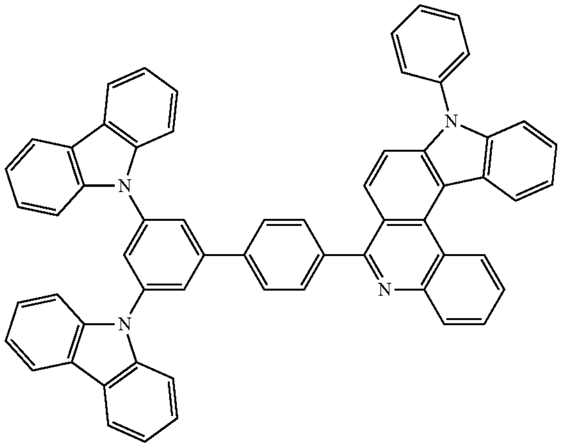
1-13
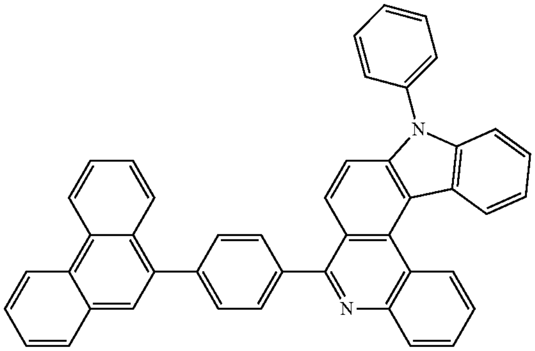
1-14
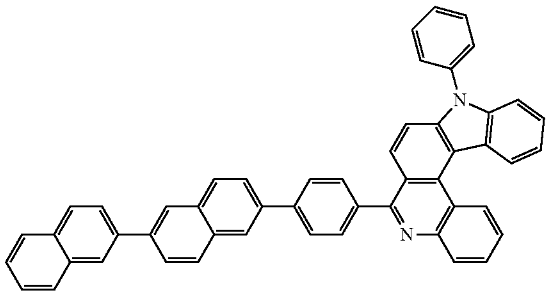
1-15
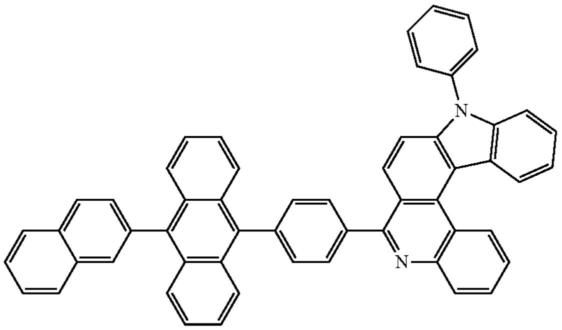
1-16
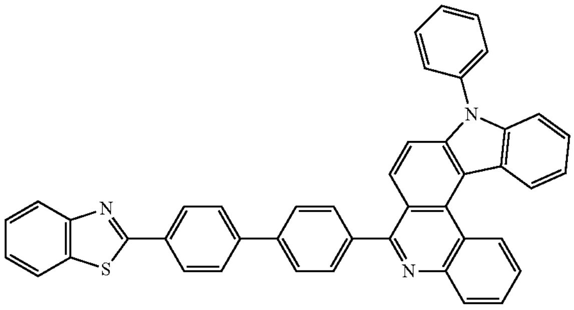
1-17
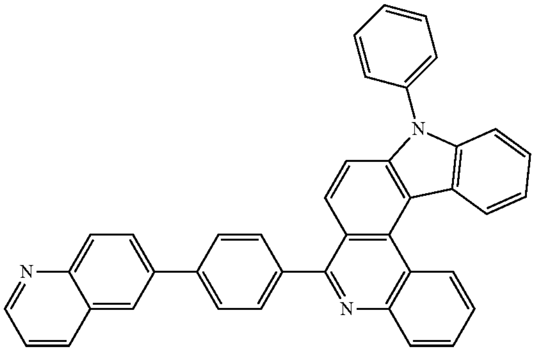
1-18
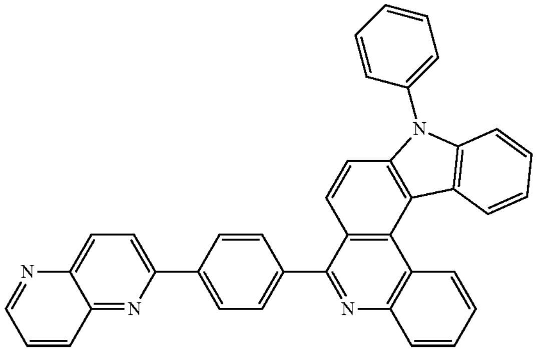

-continued
1-19
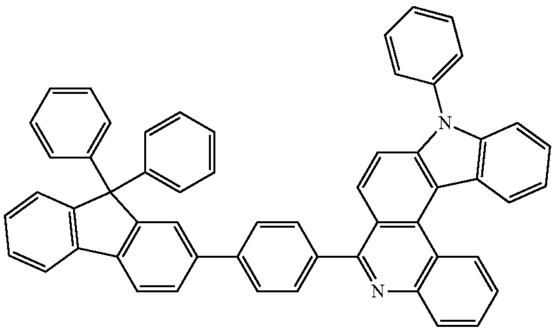
1-20
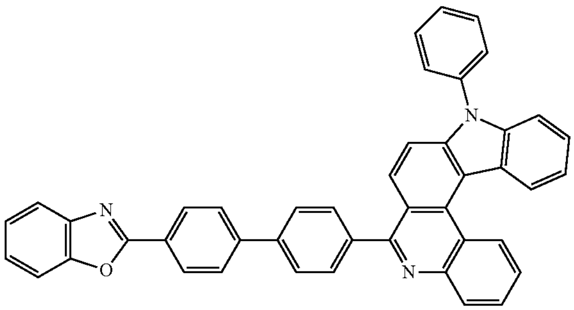
1-21
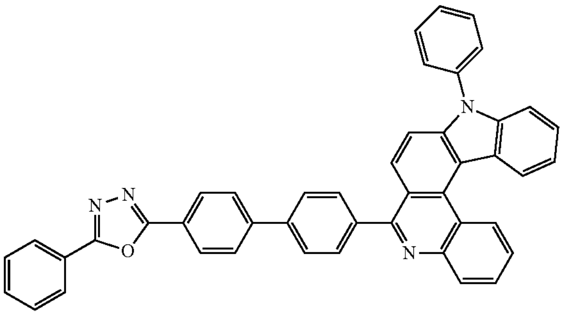
1-22
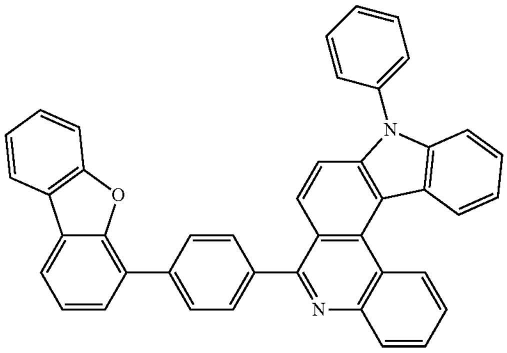
1-23
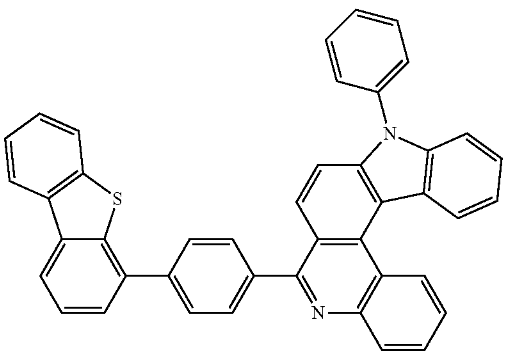
1-24
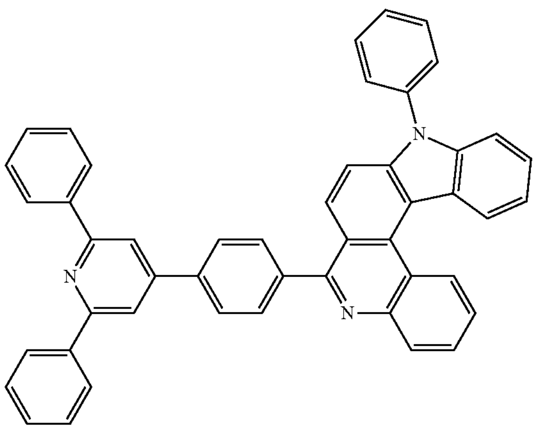

-continued
1-25
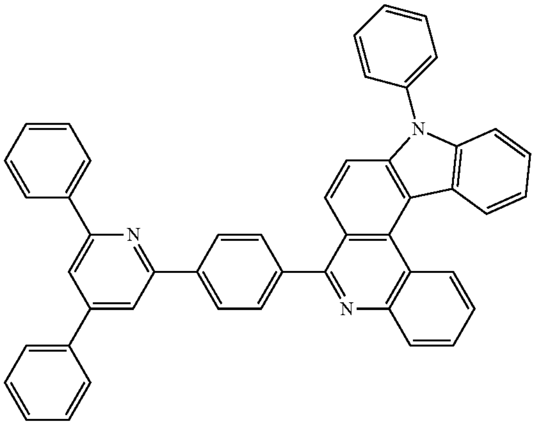
1-26
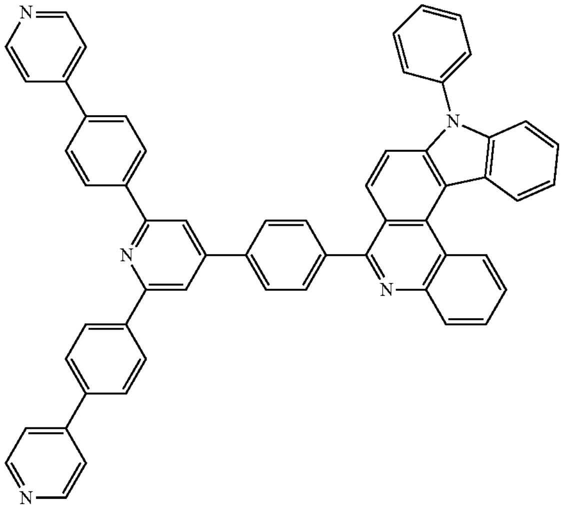
1-27
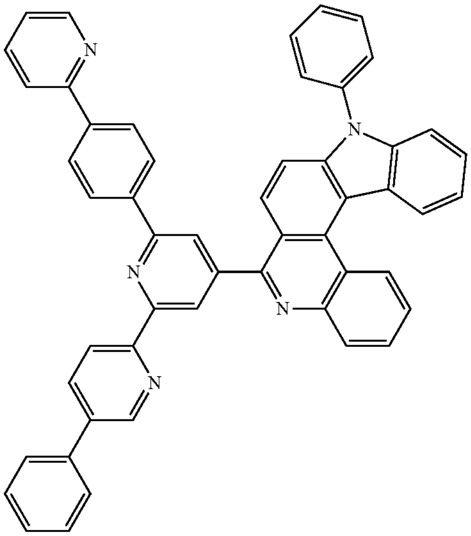
1-28
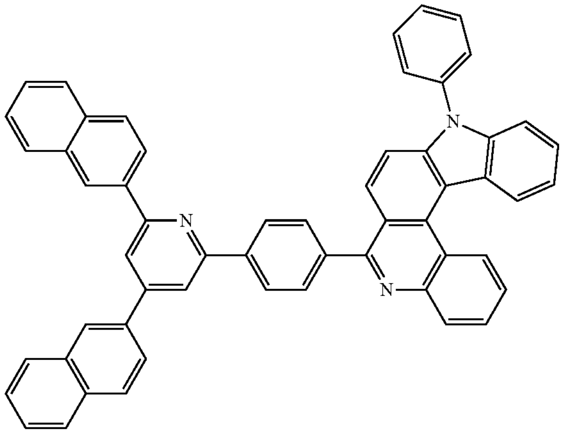
1-29
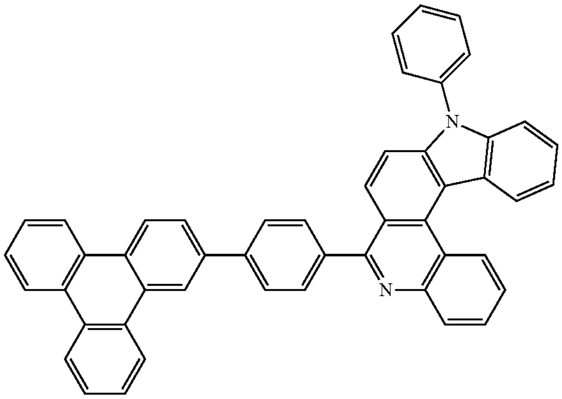
1-30
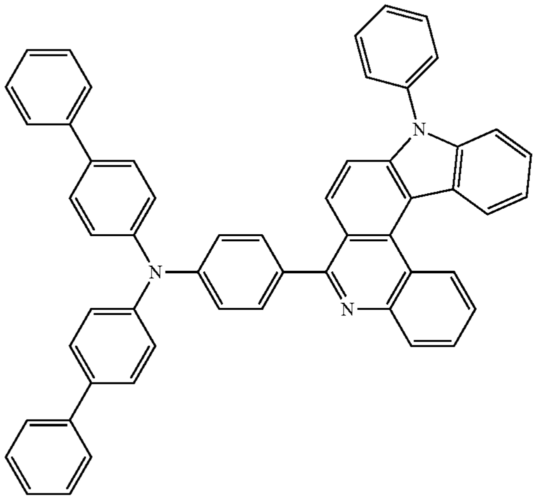

-continued
1-31
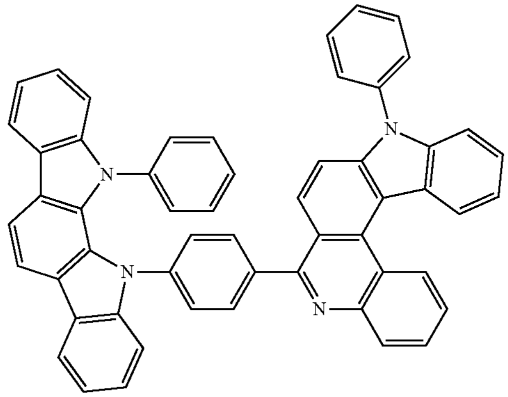
1-32
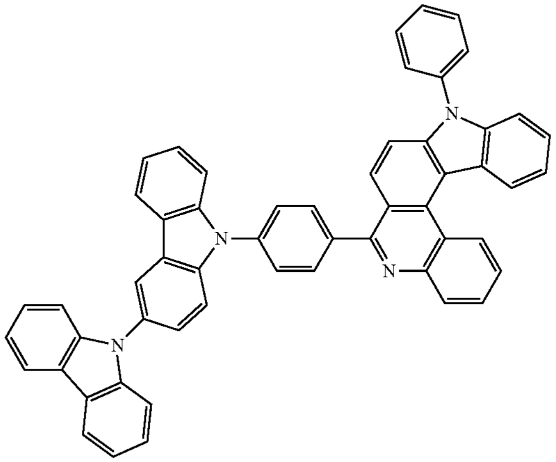
1-33
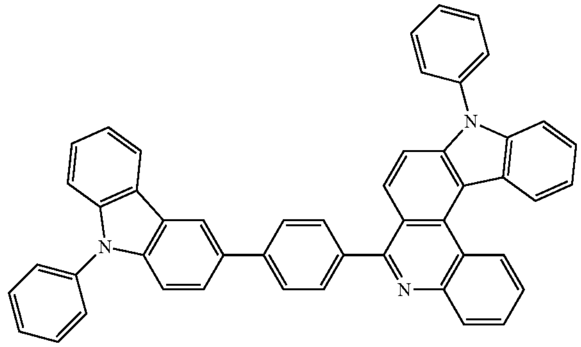
1-34
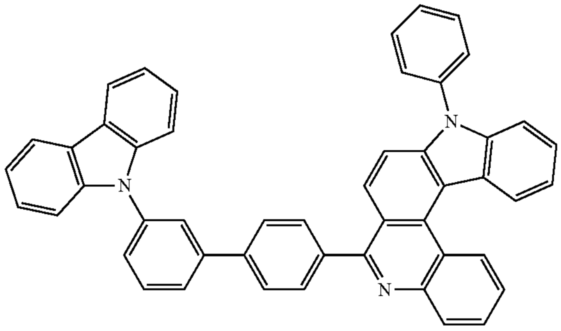
1-35
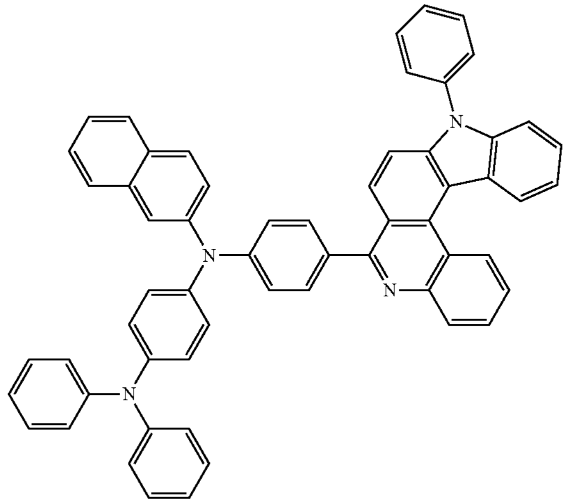
1-36
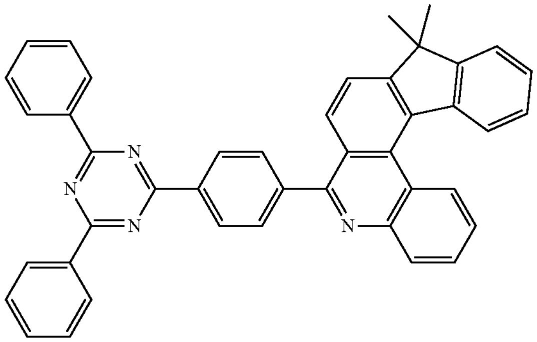

-continued
1-37
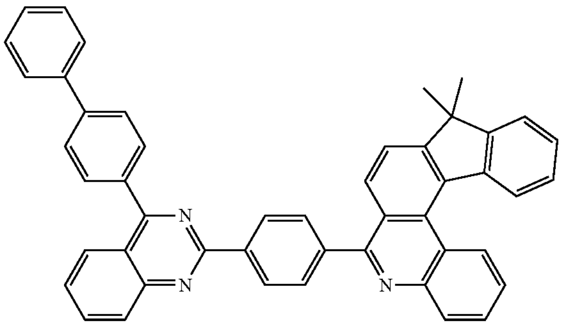
1-38
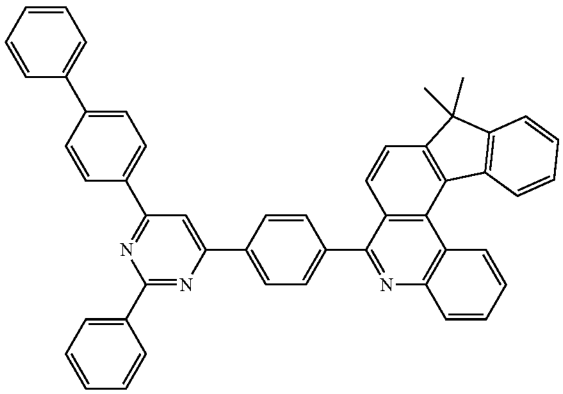
1-39
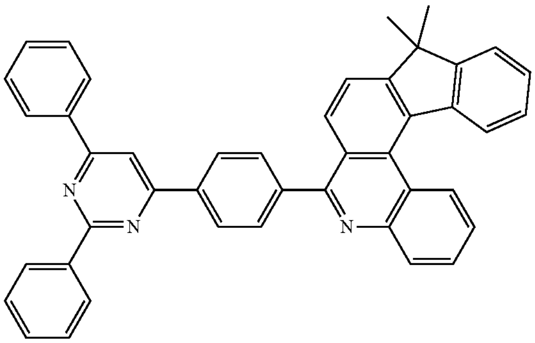
1-40
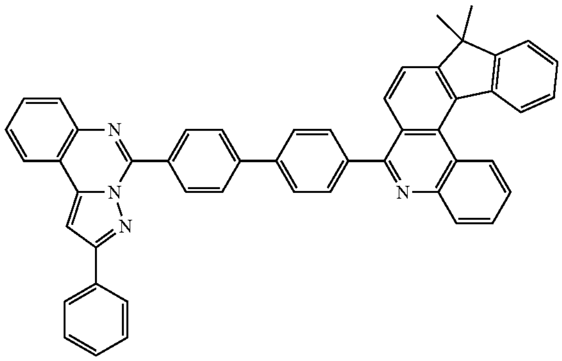
1-41
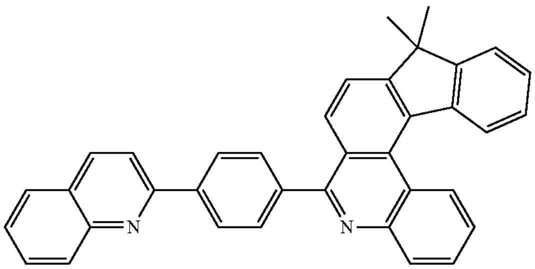
1-42
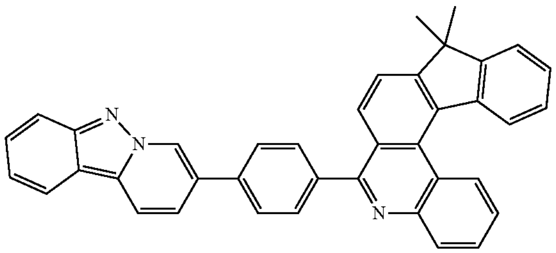
1-43
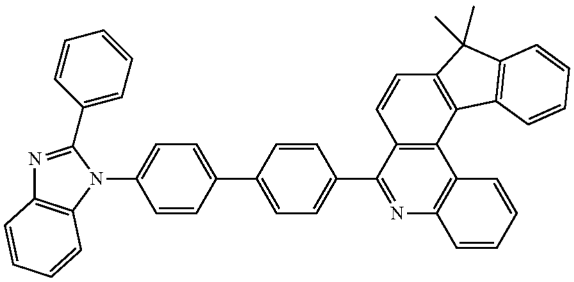
1-44
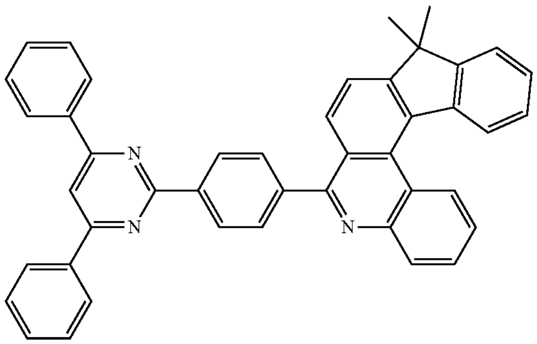

-continued
1-45
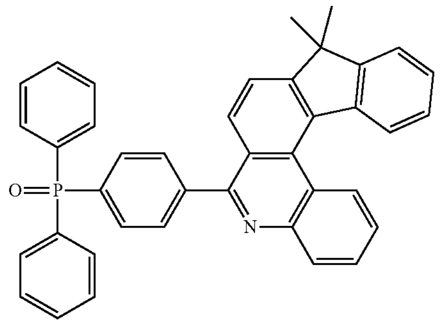
1-46
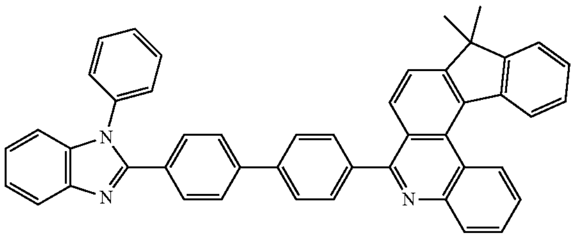
1-47
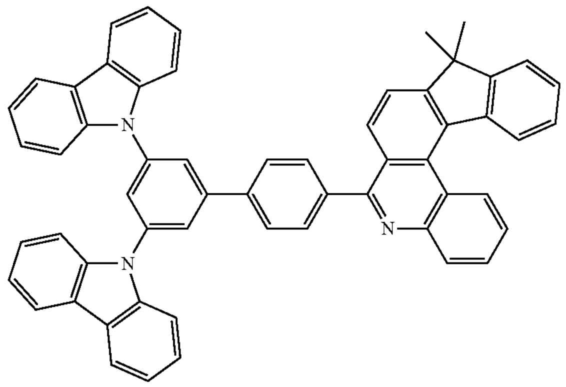
1-48
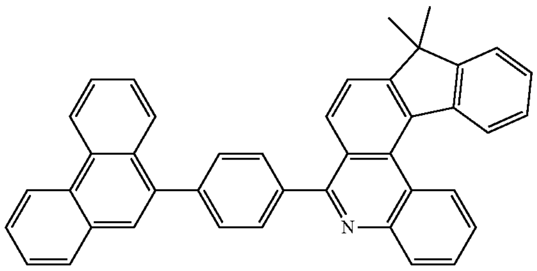
1-49
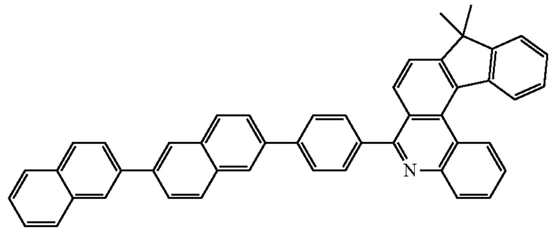
1-50
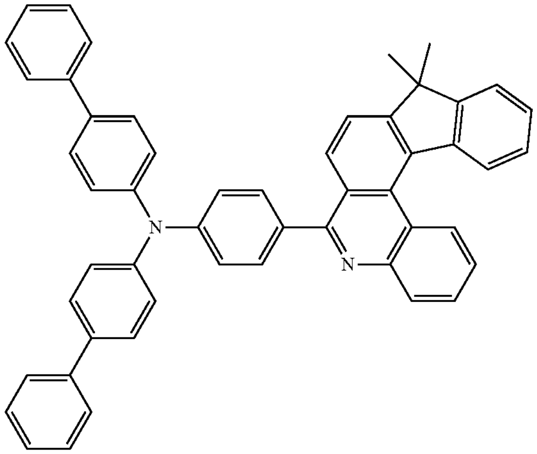
1-51
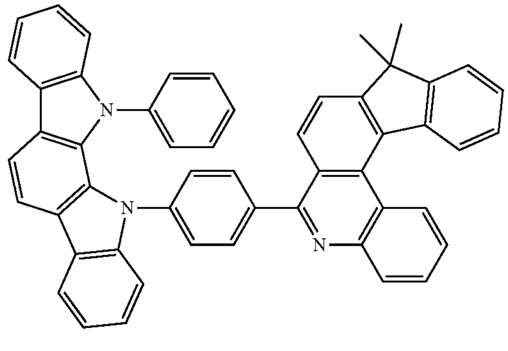
1-52
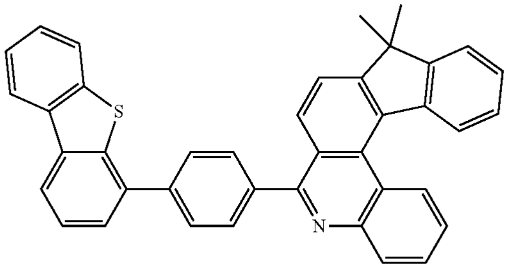

-continued
1-53
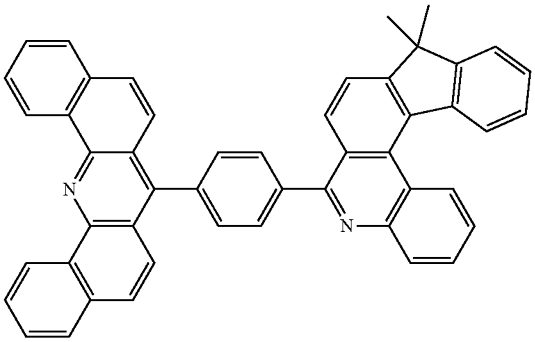
1-54
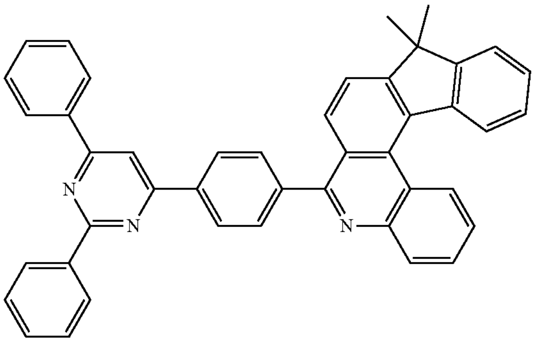
1-55
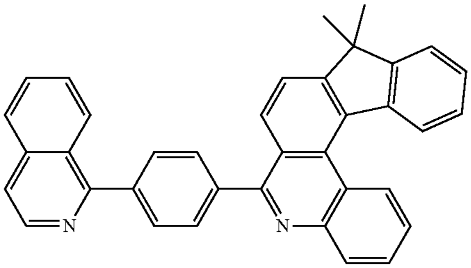
1-56
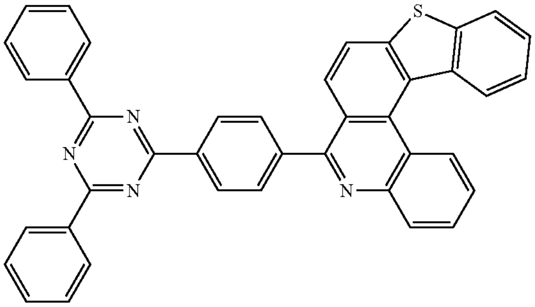
1-57
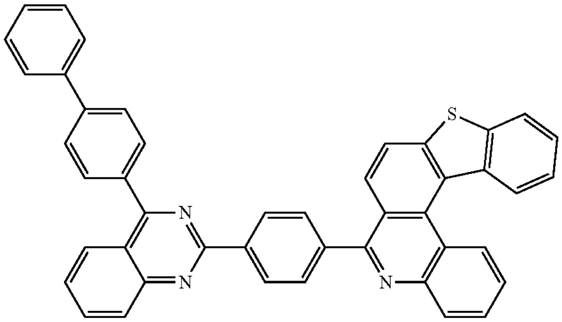
1-58
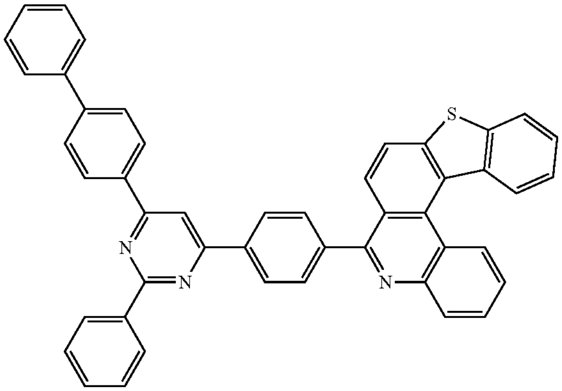
1-59
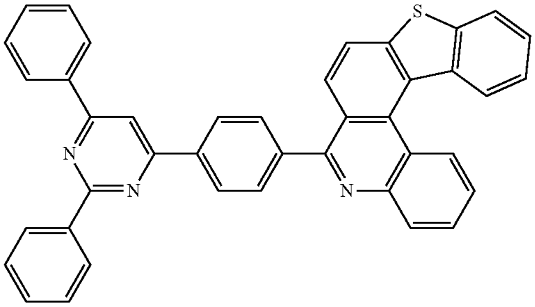
1-60
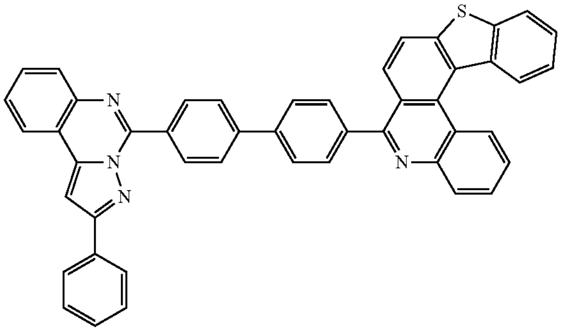

-continued
1-61
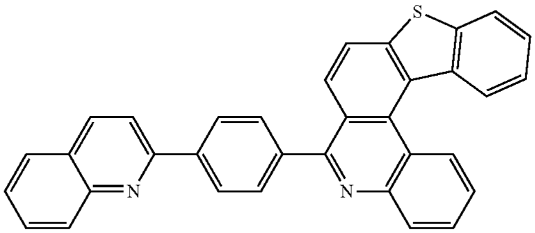
1-62
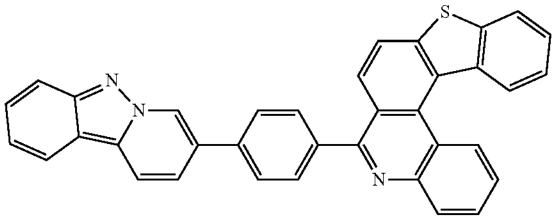
1-63
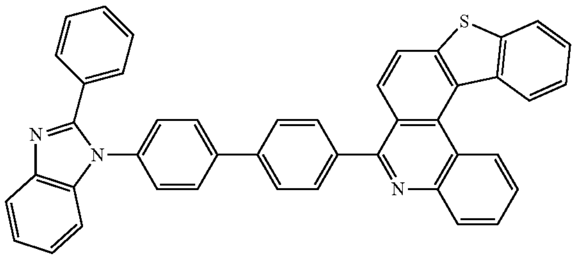
1-64
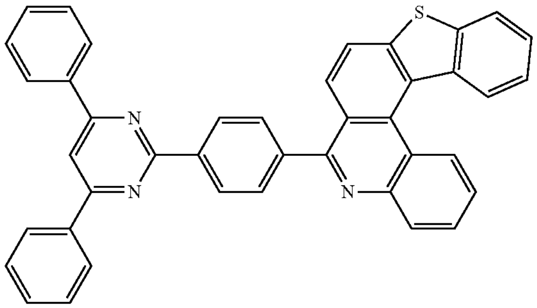
1-65
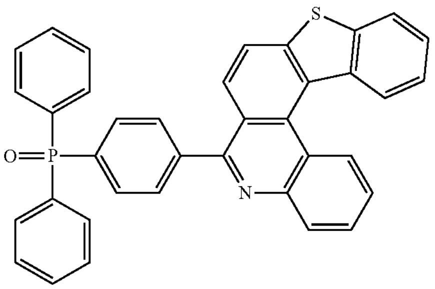
1-66
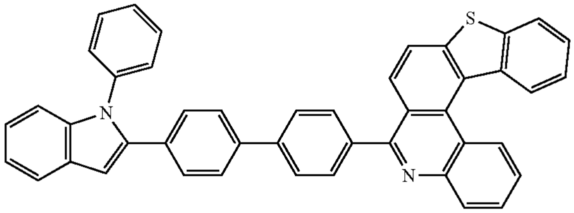
1-67
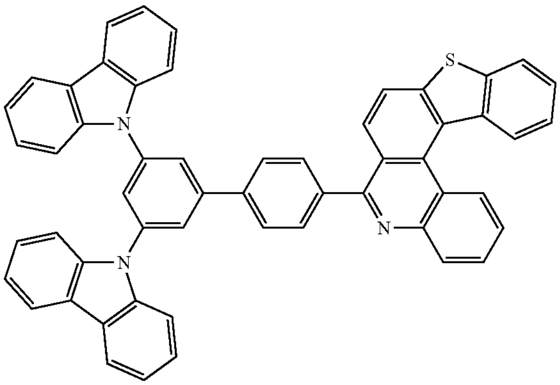
1-68
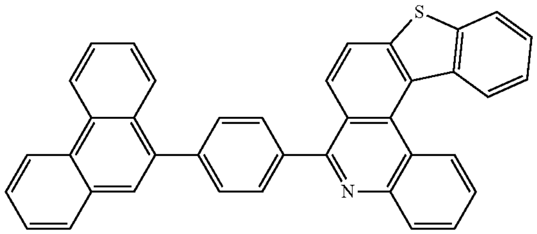

-continued
1-69
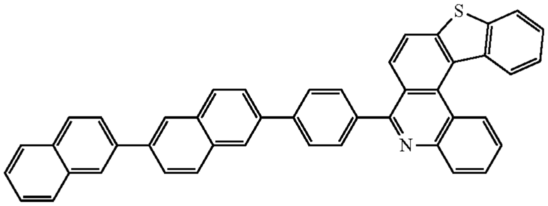
1-70
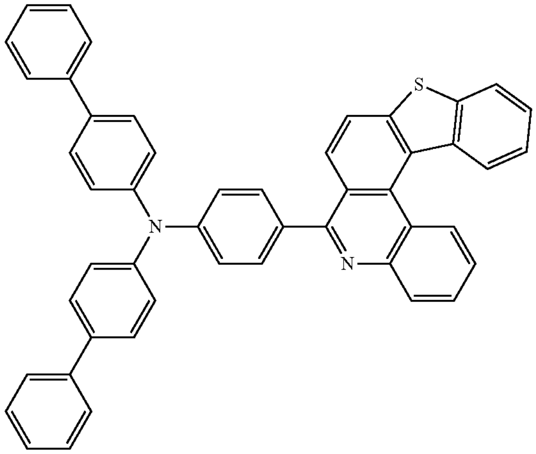
1-71
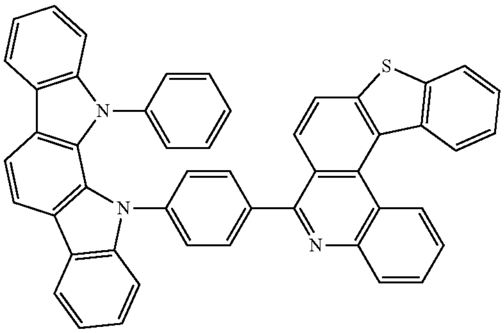
1-72
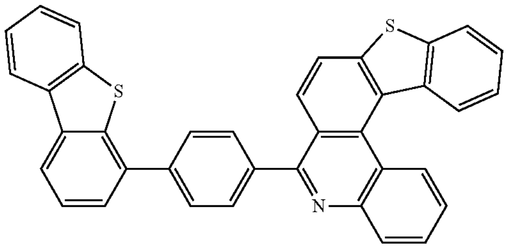
1-73
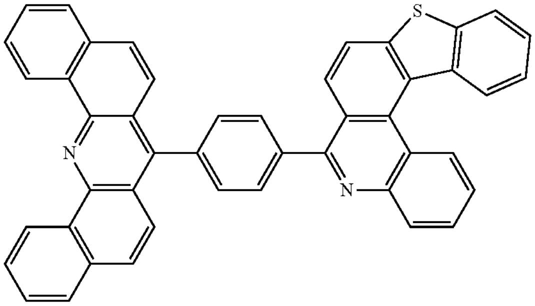
1-74
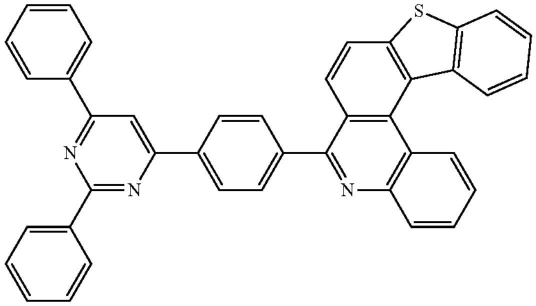
1-75
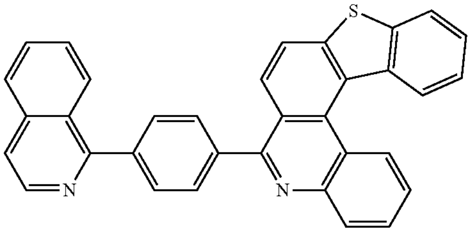
1-76
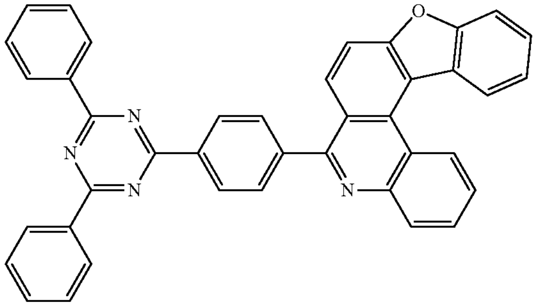

-continued
1-77
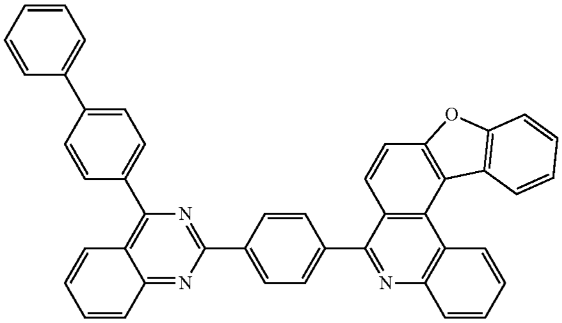
1-78
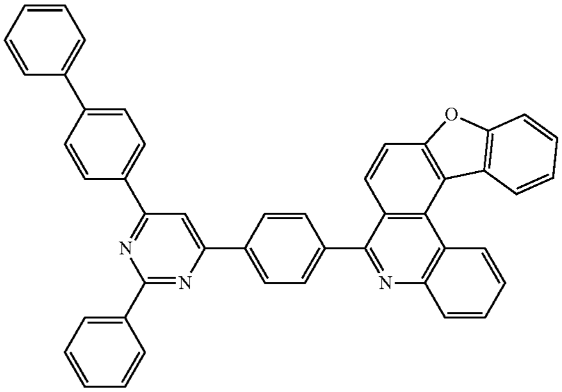
1-79
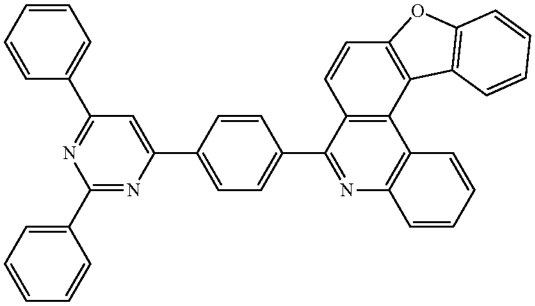
1-80
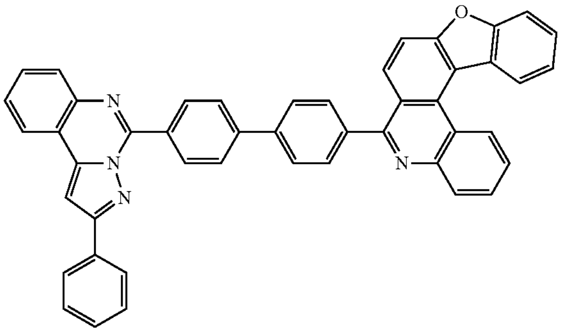
1-81
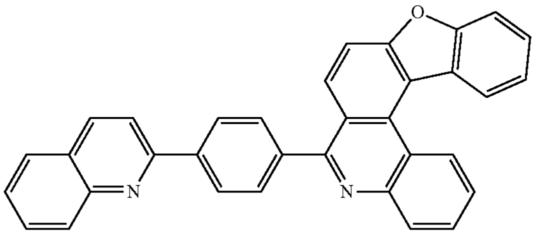
1-82
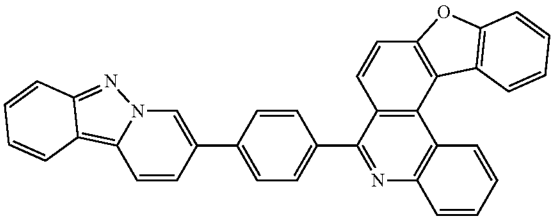
1-83
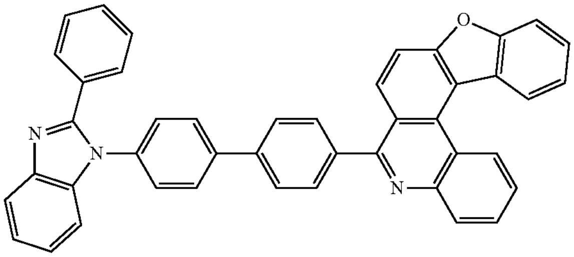
1-84
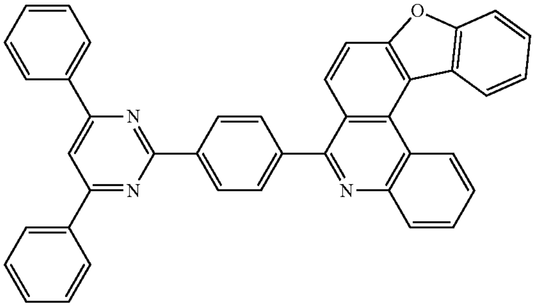

-continued
1-85
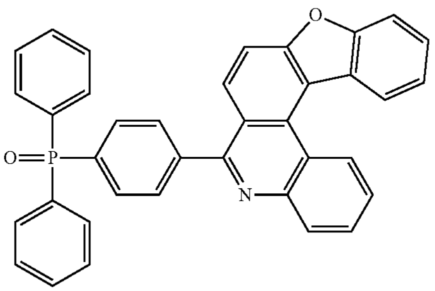
1-86
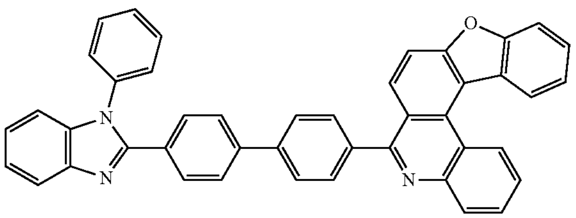
1-87
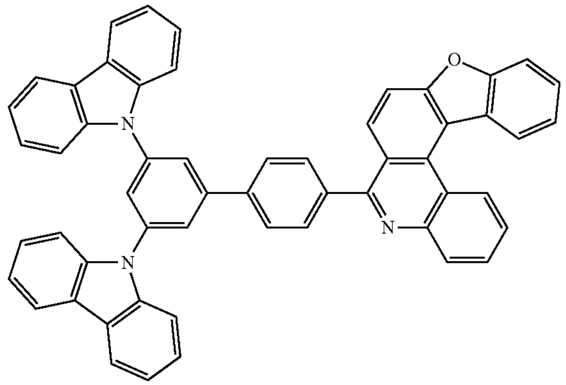
1-88
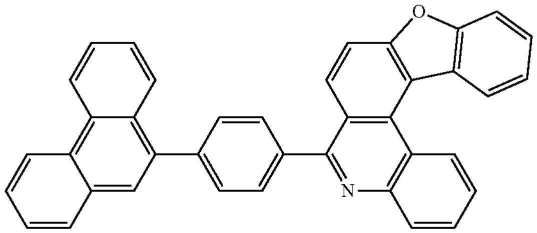
1-89
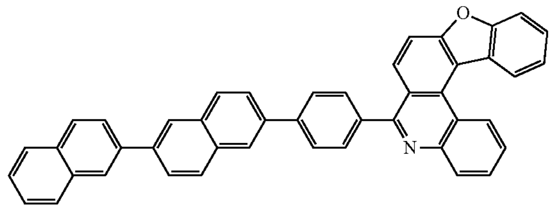
1-90
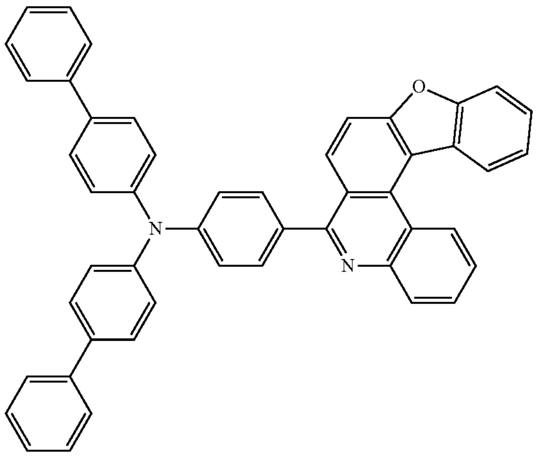
1-251
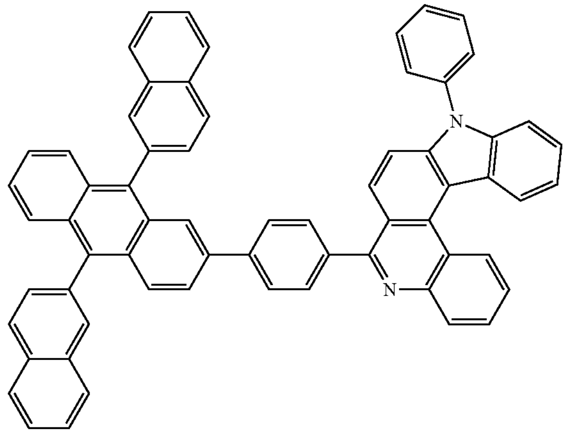
1-252
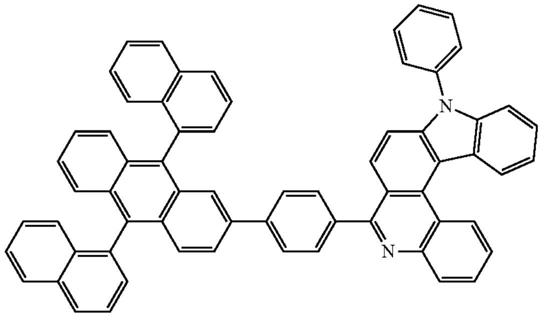

-continued
1-253
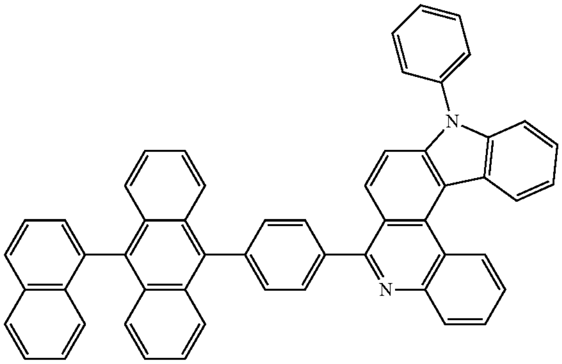
1-254
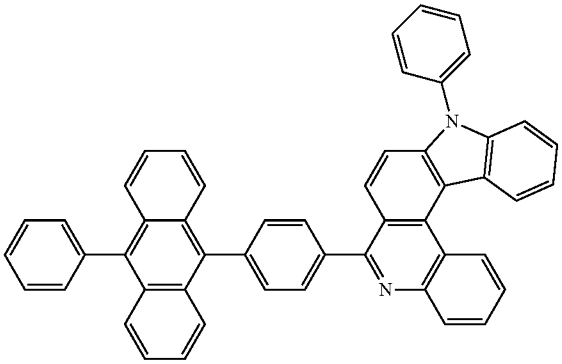
1-255
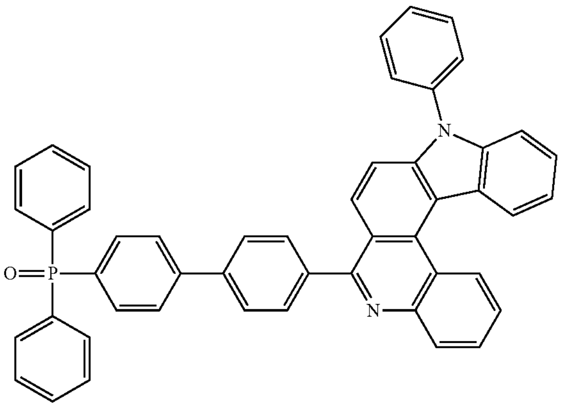
1-256
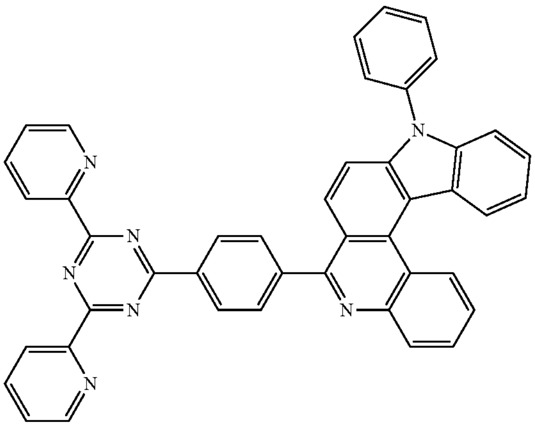
1-257
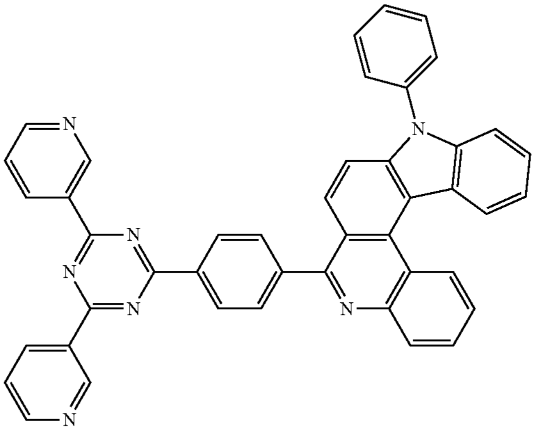
1-258
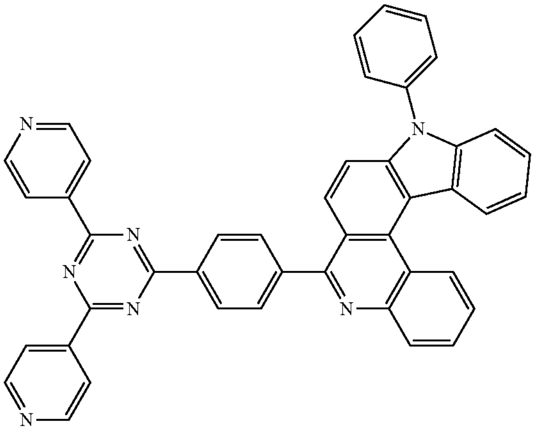

-continued
1-259
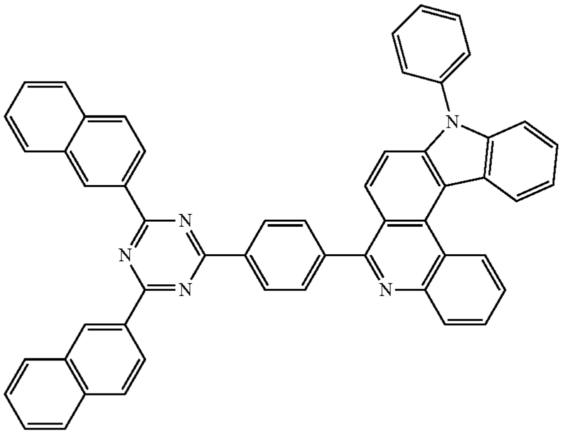
1-260
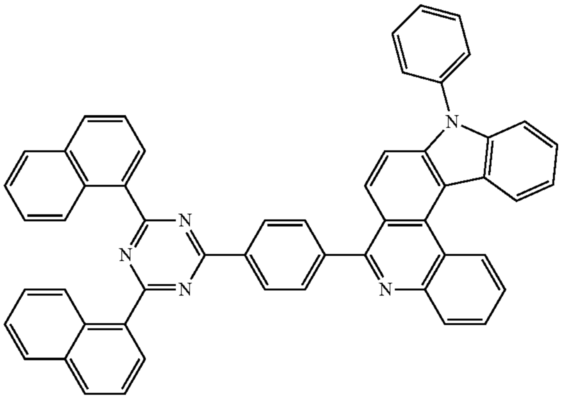
1-261
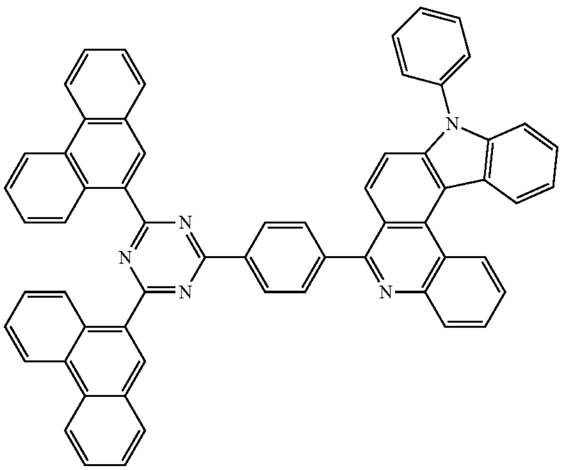
1-262
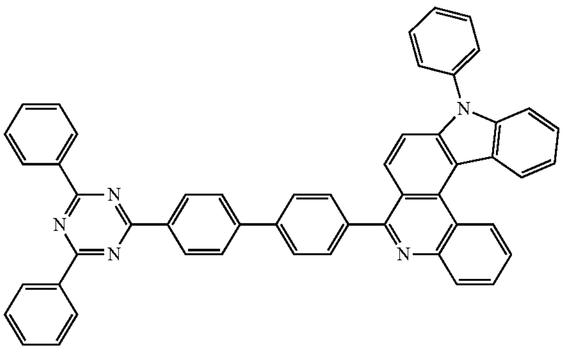
1-263
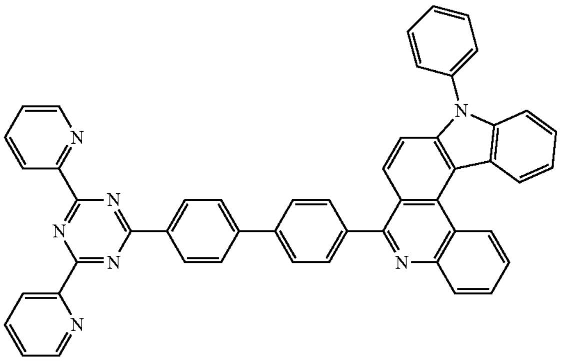
1-264
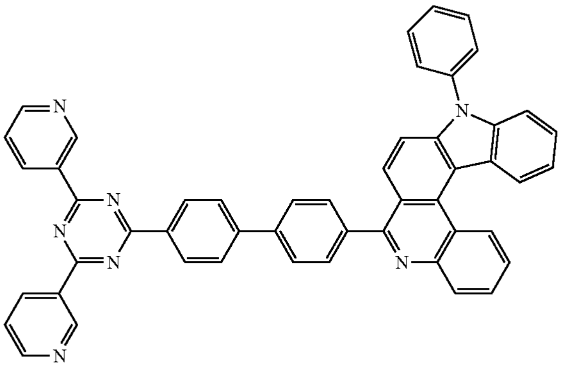

-continued
1-265
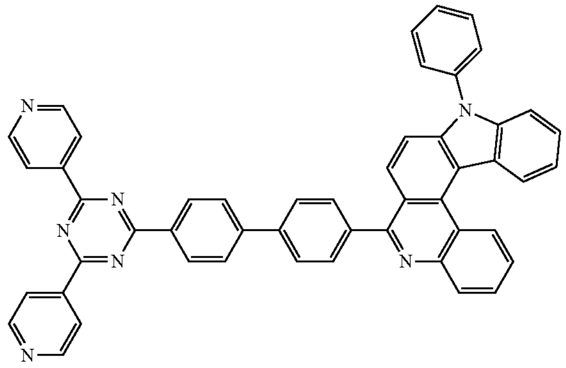
1-266
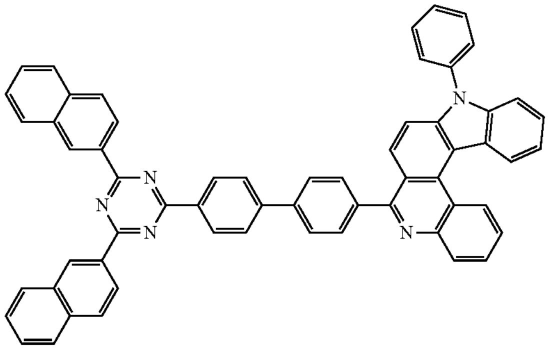
1-267
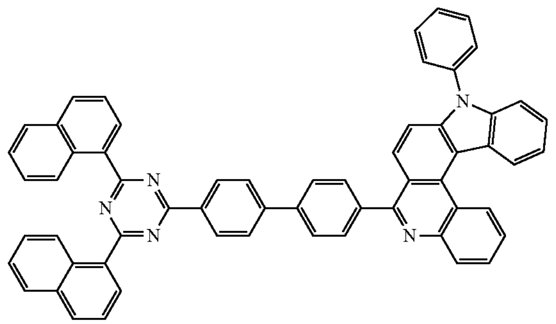
1-268
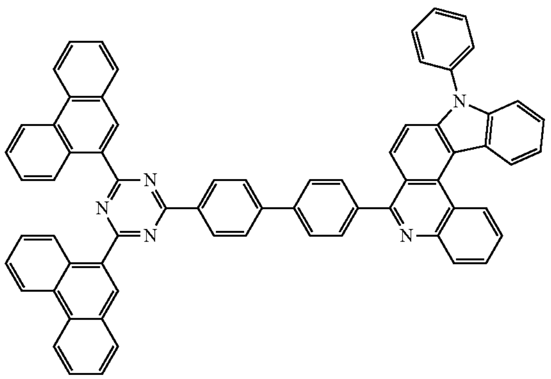
1-269
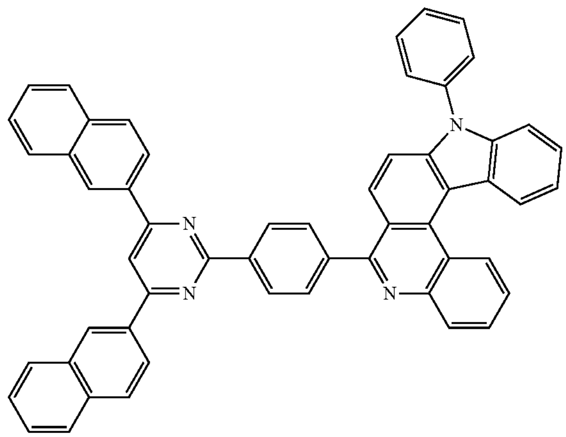
1-270
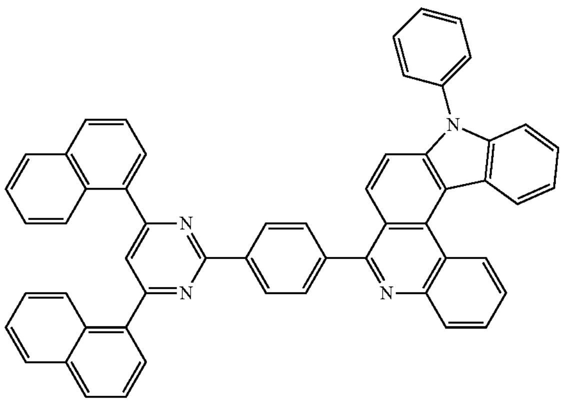

-continued
1-271
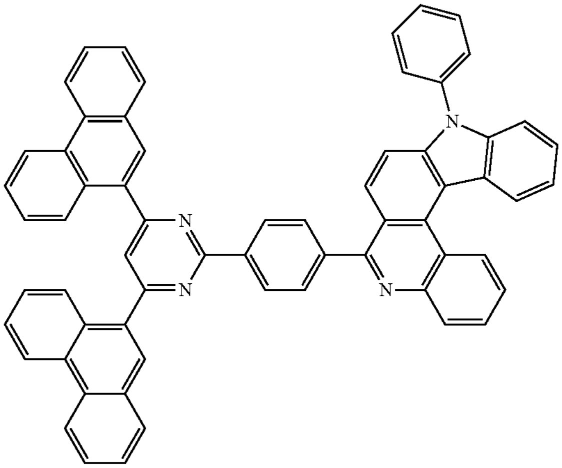
1-272
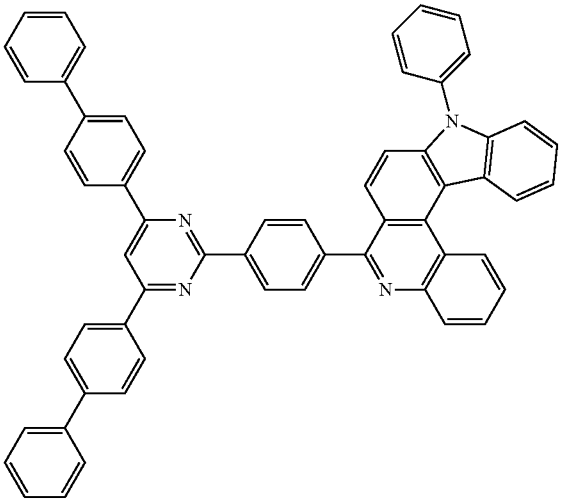
1-273
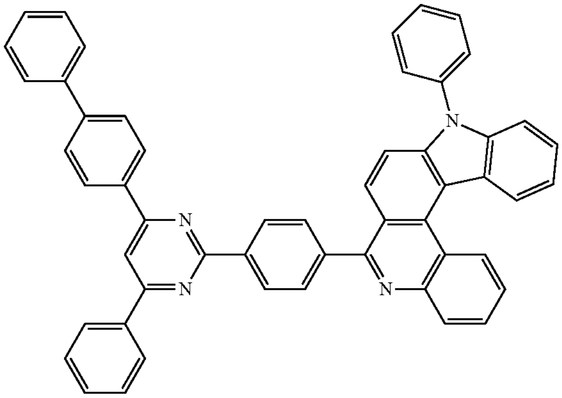
1-274
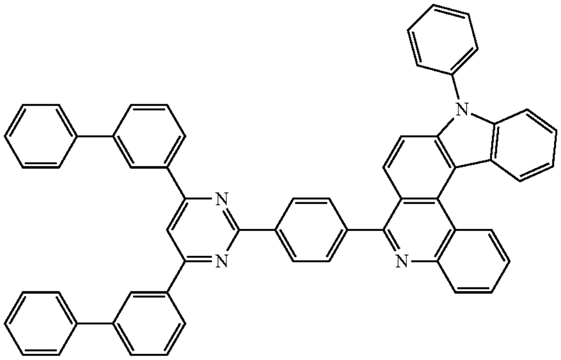
1-275
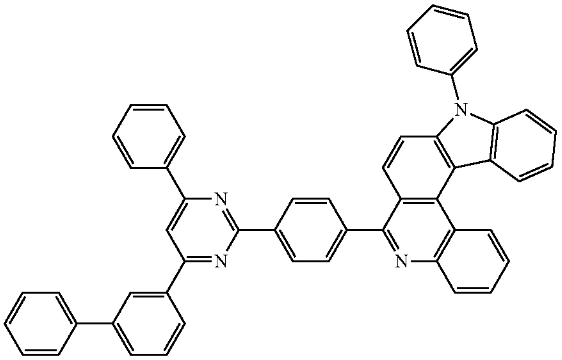
1-276
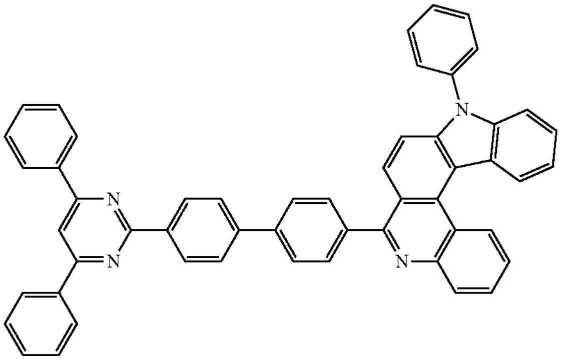

-continued
1-277
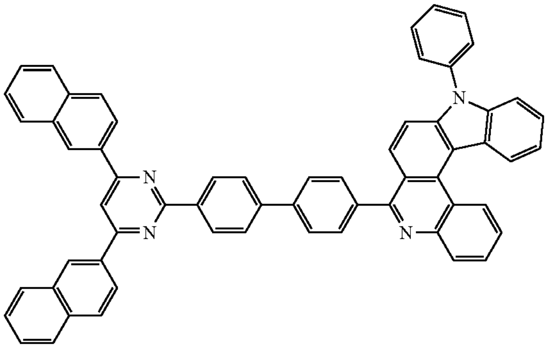
1-278
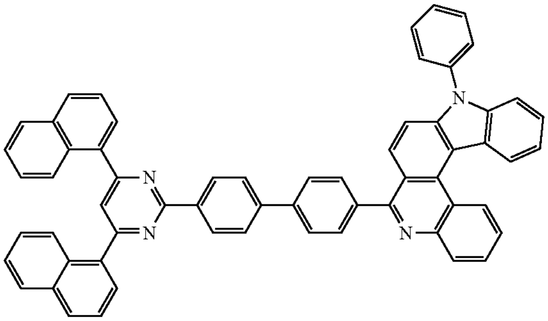
1-279
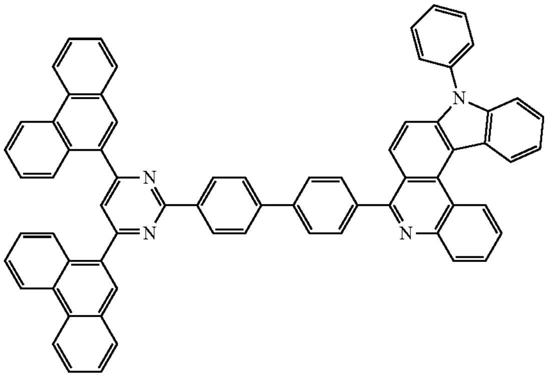
1-280
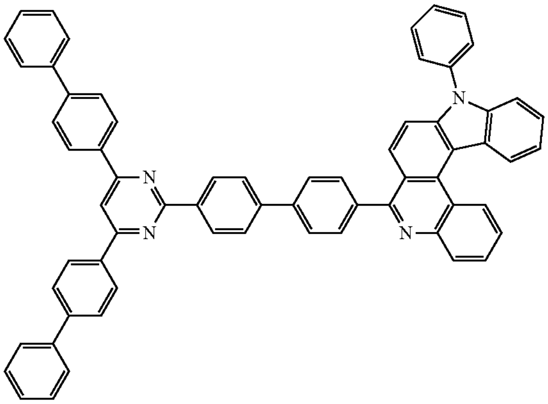
1-281
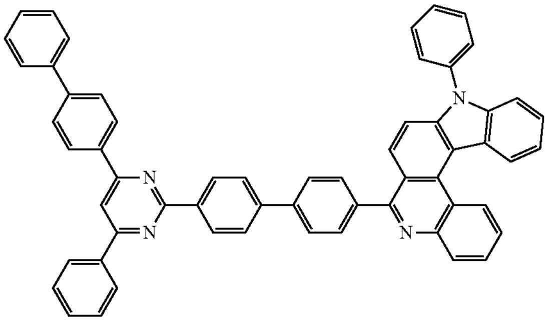
1-282
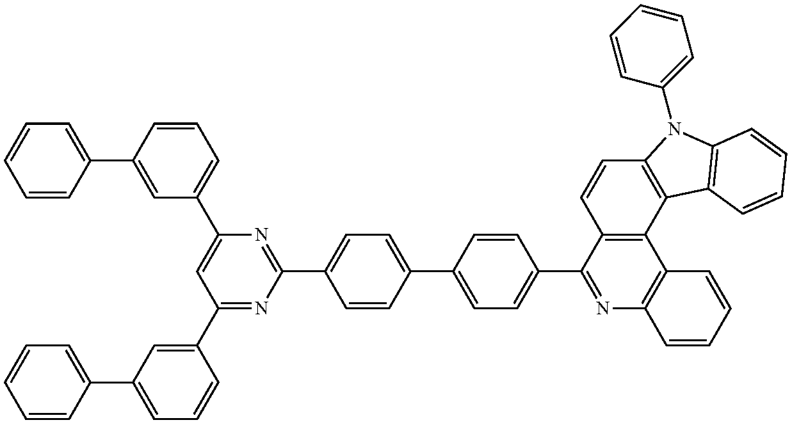

-continued
1-283
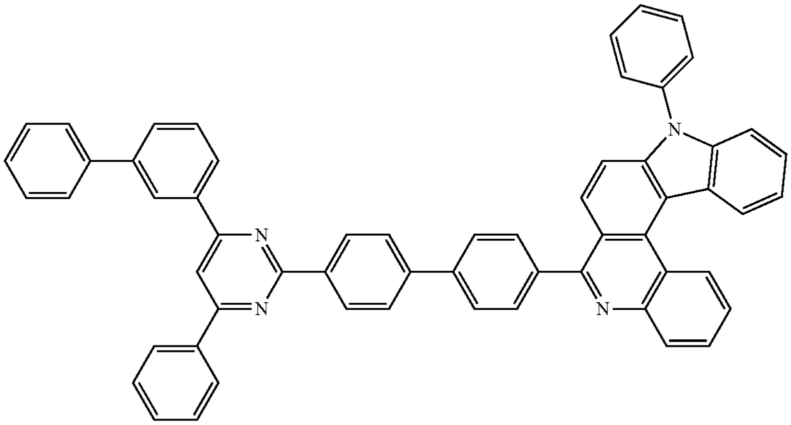
1-284
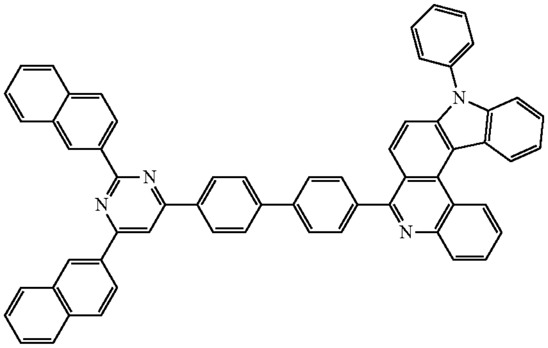
1-285
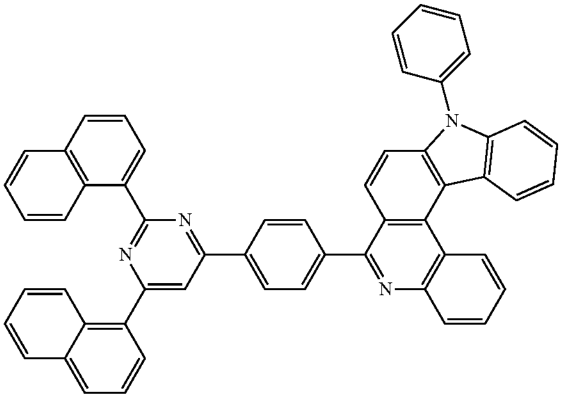
1-286
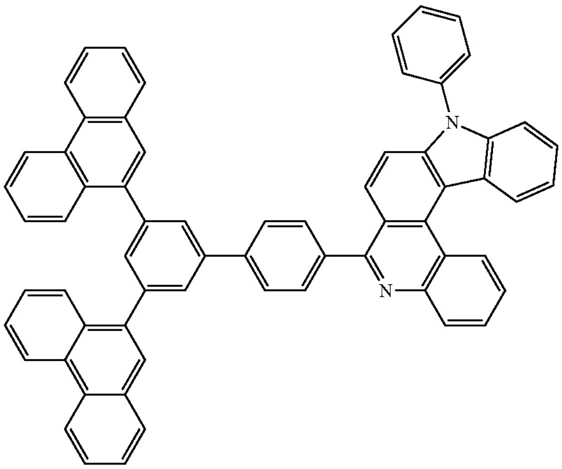
1-287
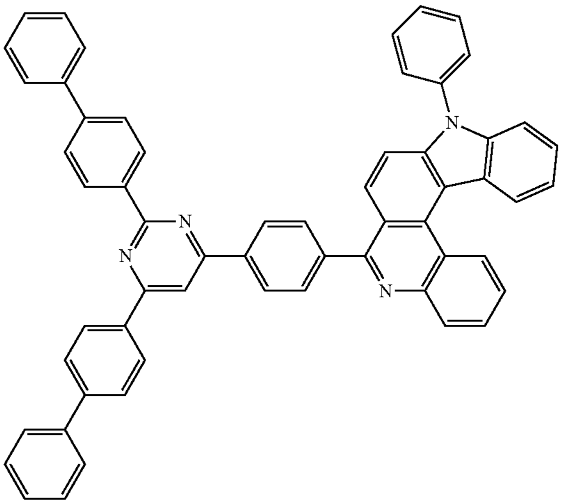

-continued
1-288
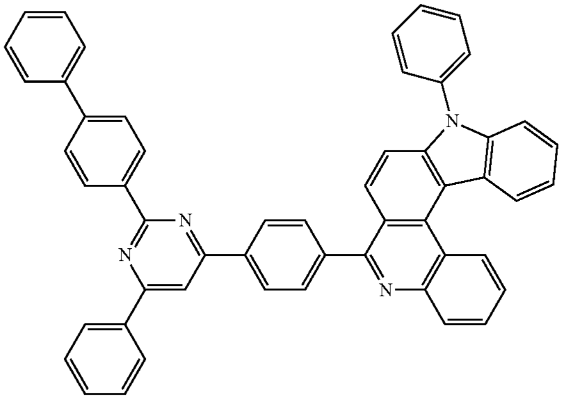
1-289
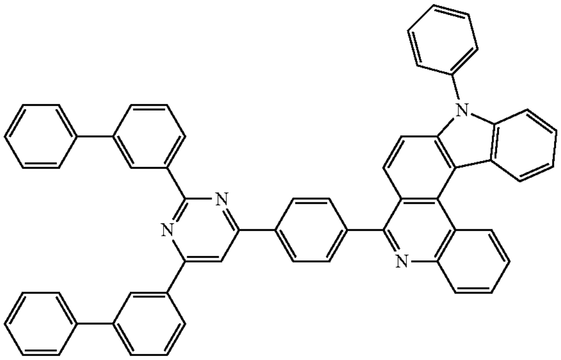
1-290
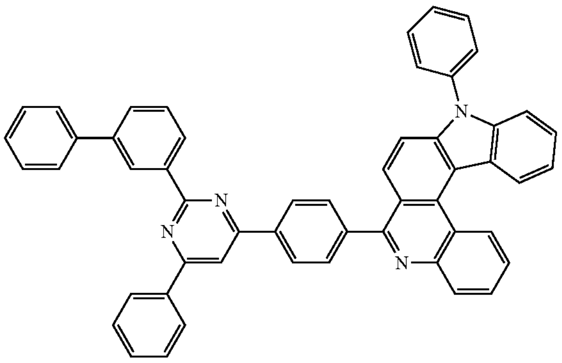
1-291
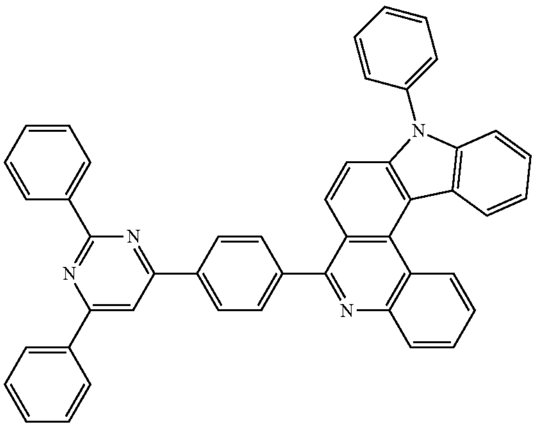
1-292
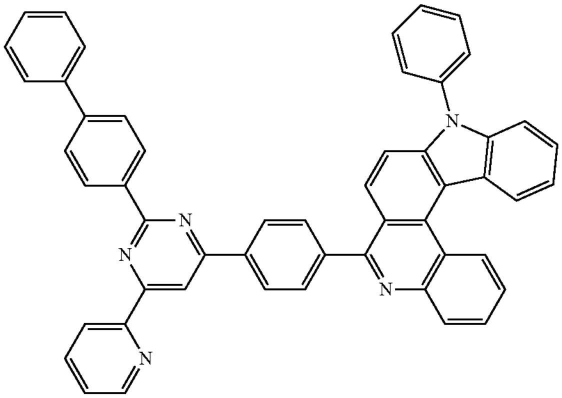
1-293
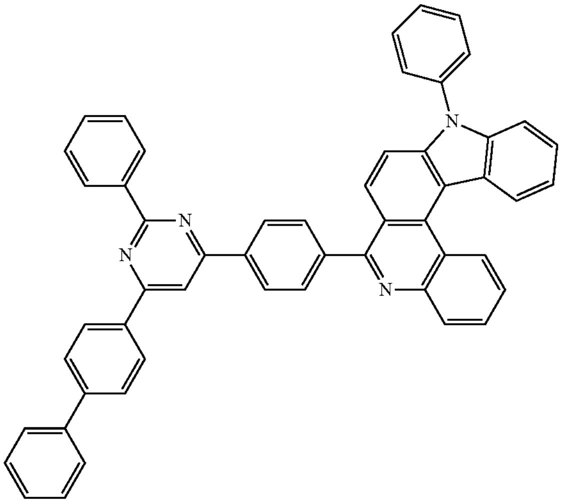

-continued
1-294
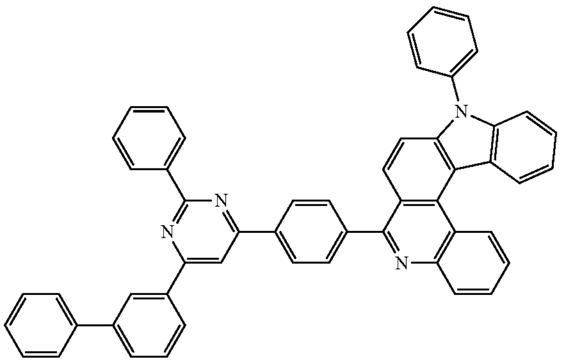
1-295
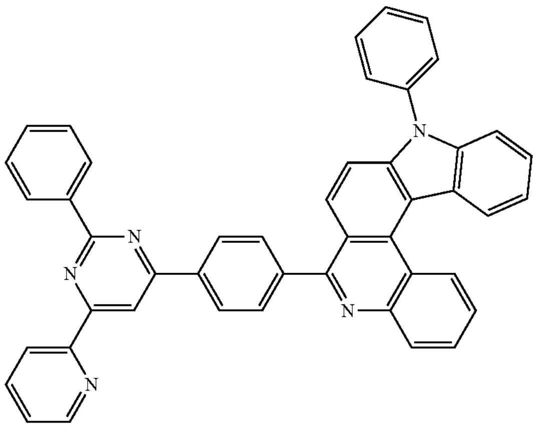
1-296
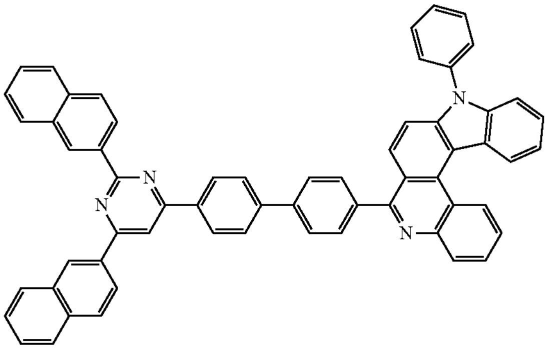
1-297
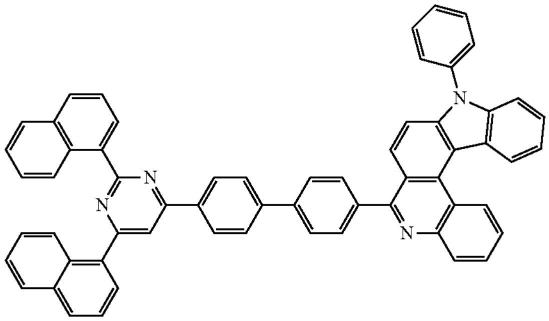
1-298
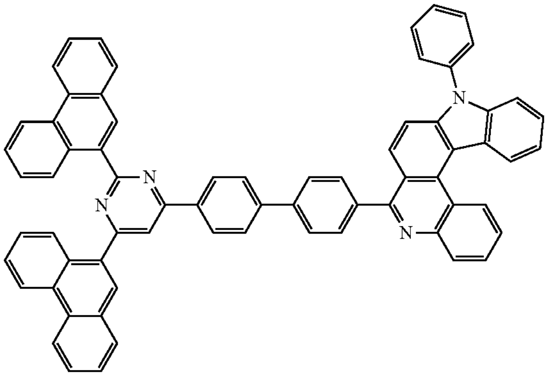
1-299
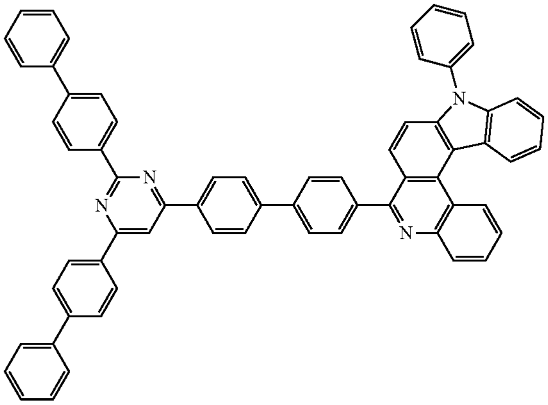
1-300
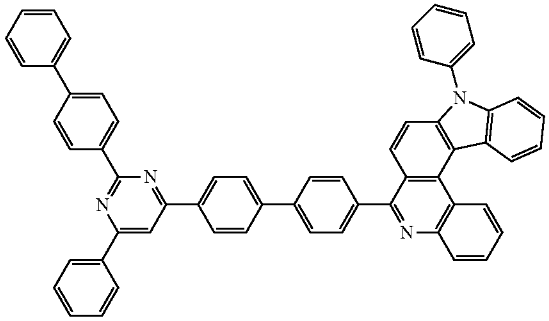

-continued
1-301
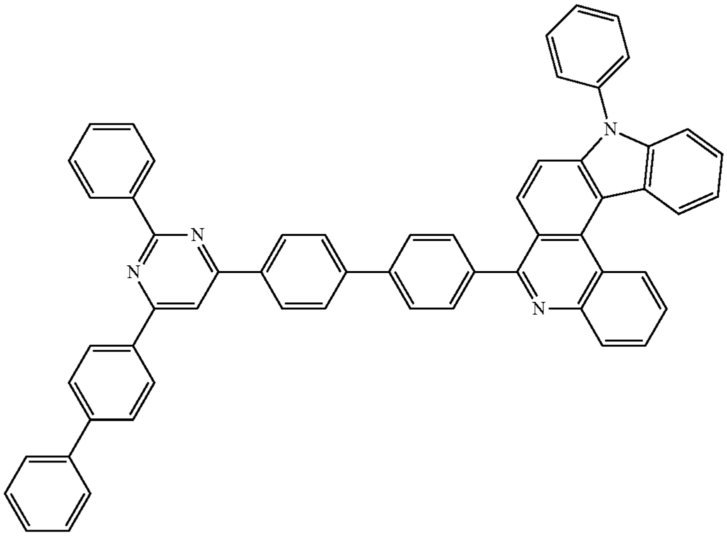
1-302
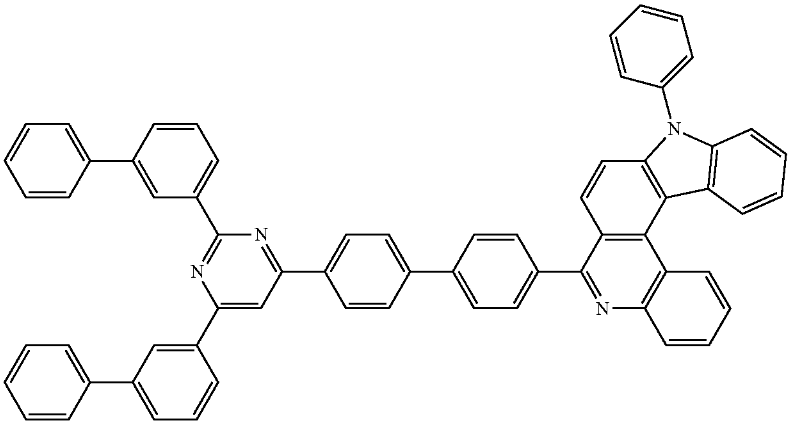
1-303
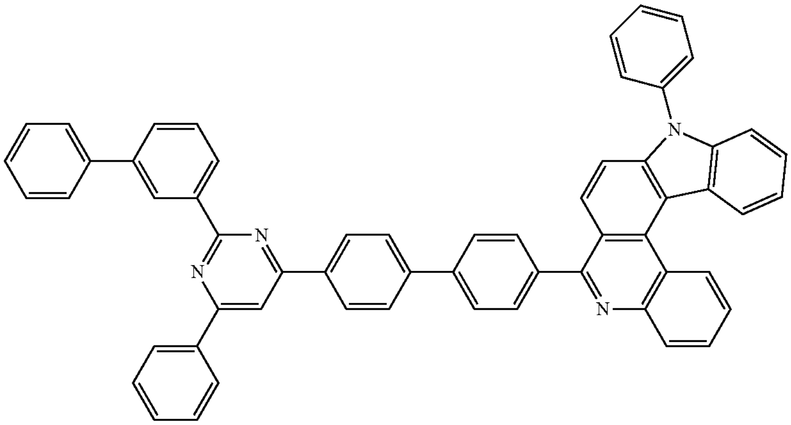

-continued
1-304
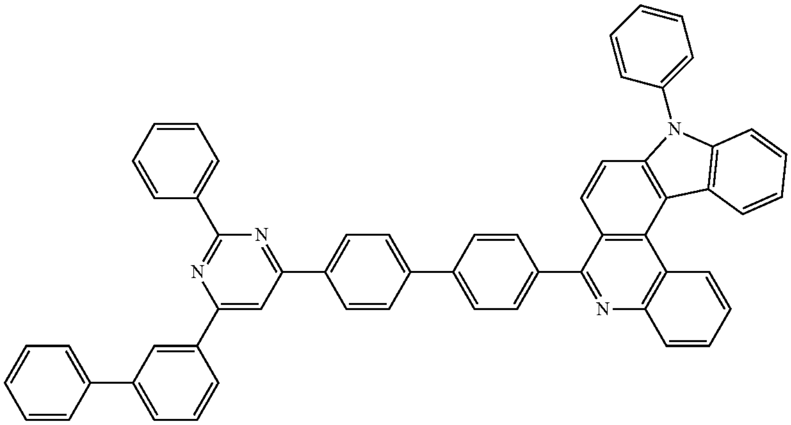
1-305
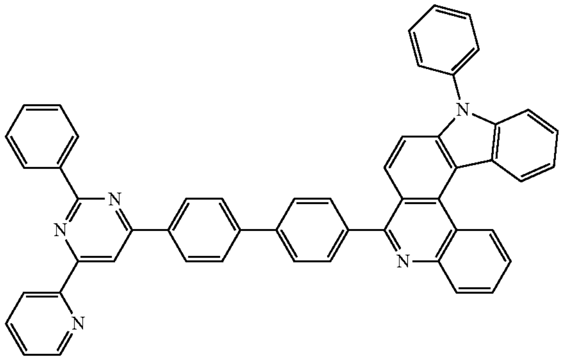
1-306
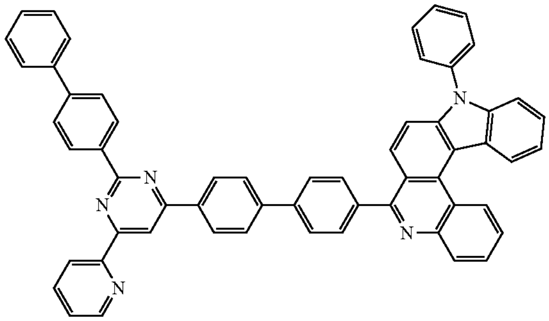
1-307
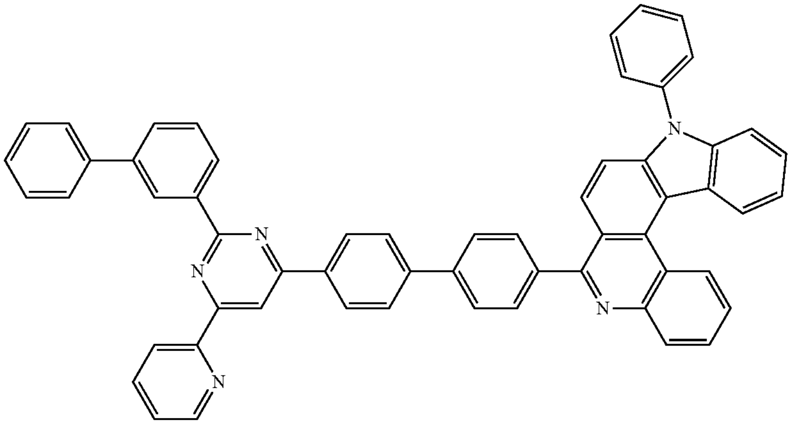
1-308
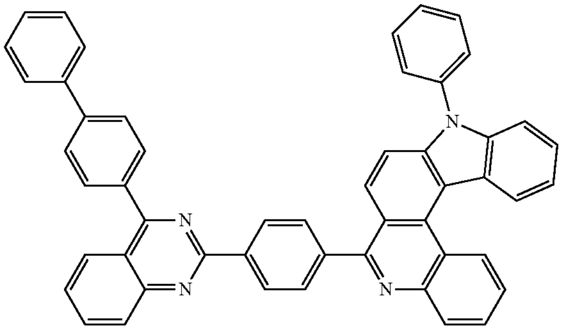
1-309
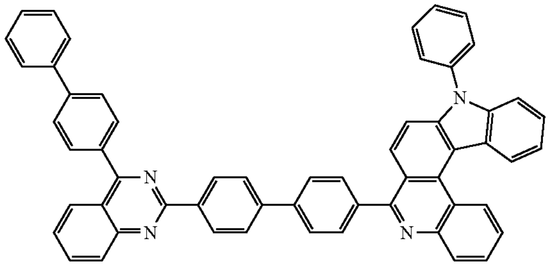

-continued
1-310
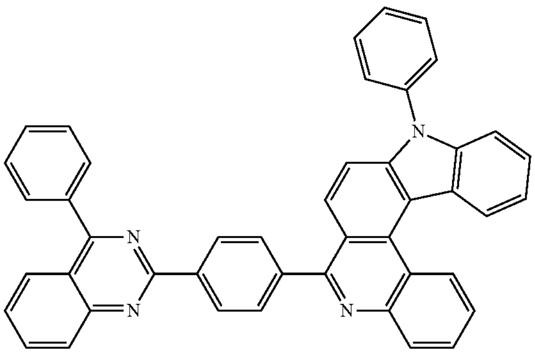
1-311
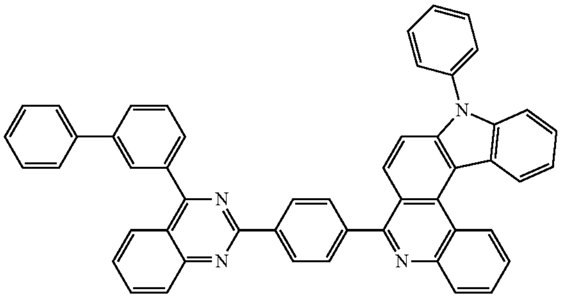
1-312
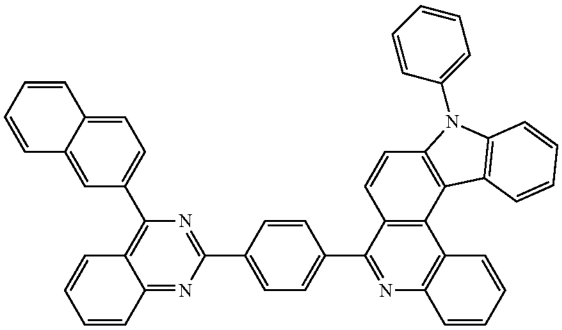
1-313
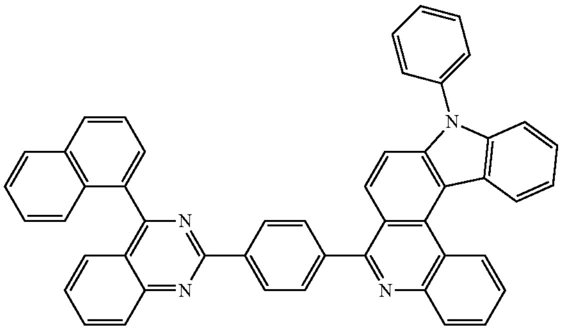
1-314
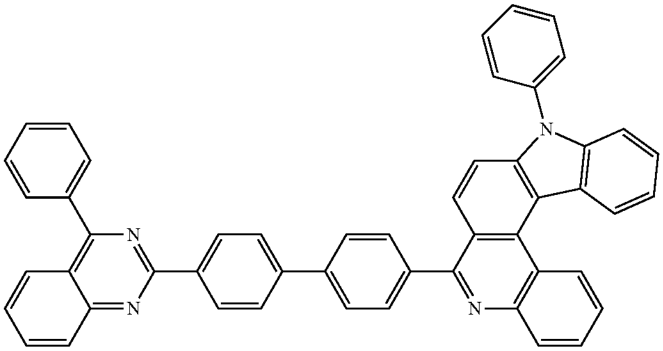
1-315
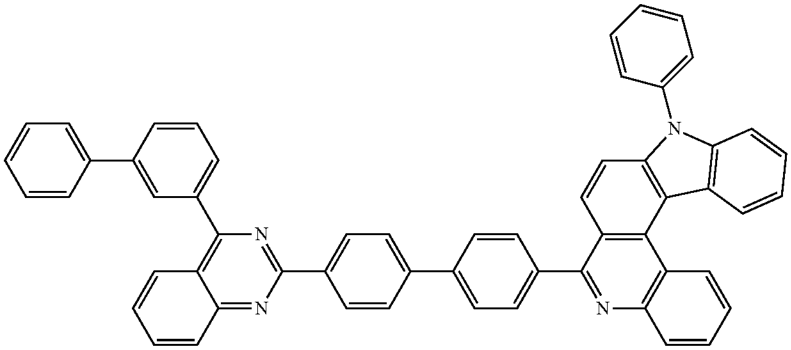

-continued
1-316
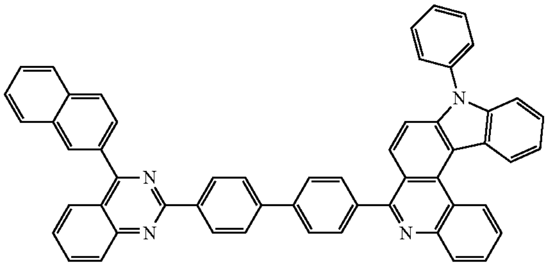
1-317
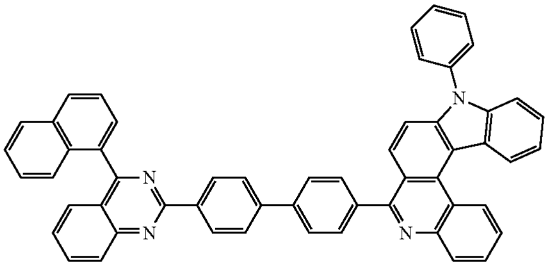
1-318
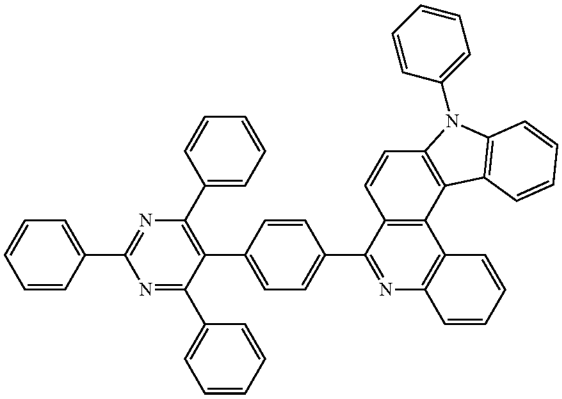
1-319
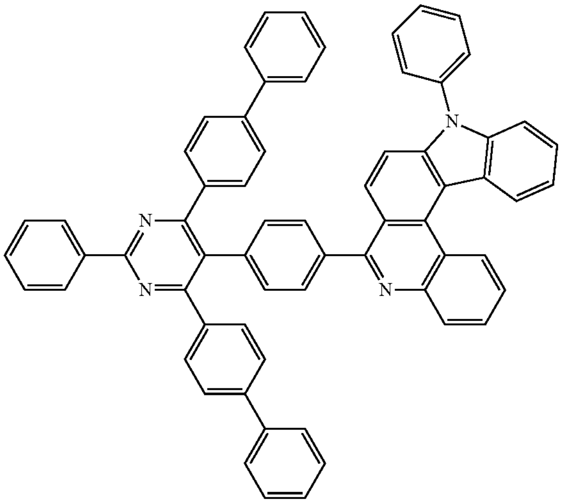
1-320
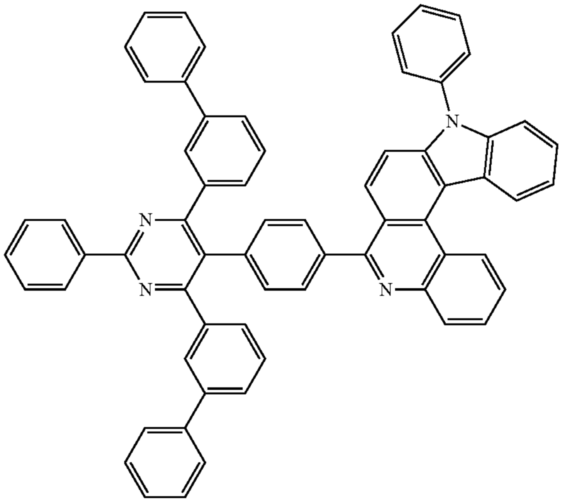
1-321
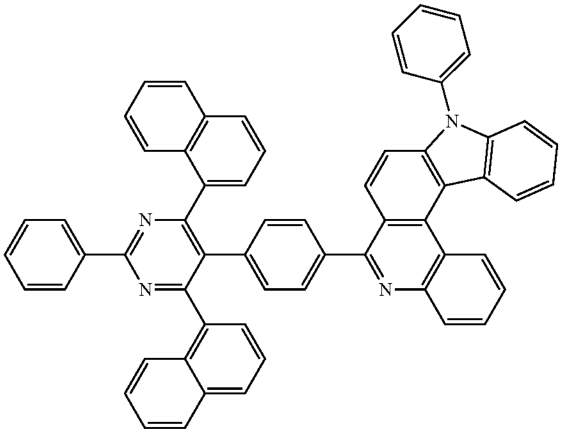

-continued
1-322
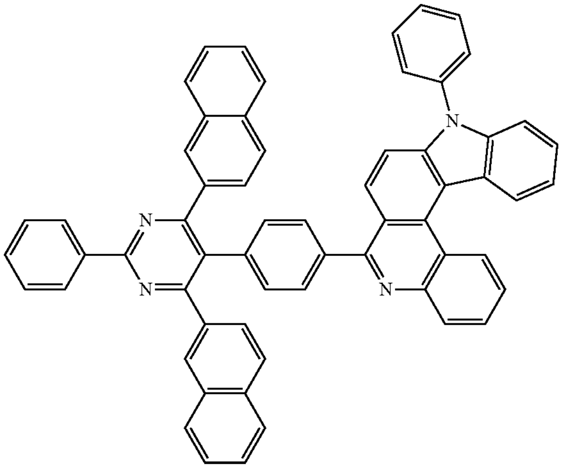
1-323
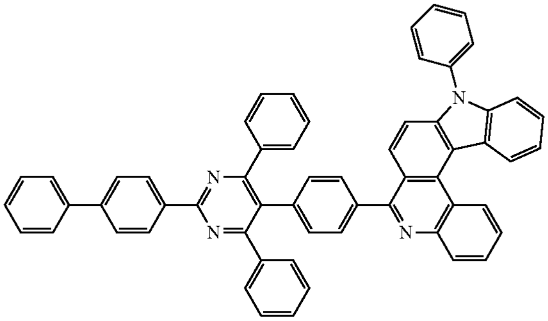
1-324
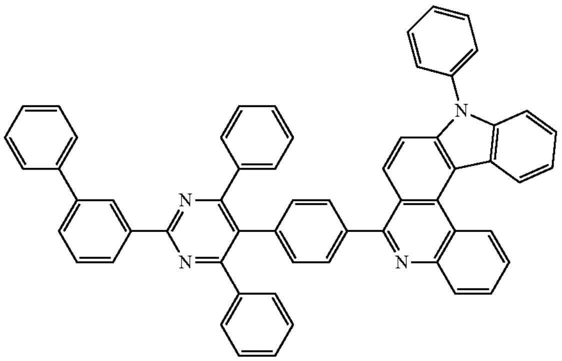
1-325
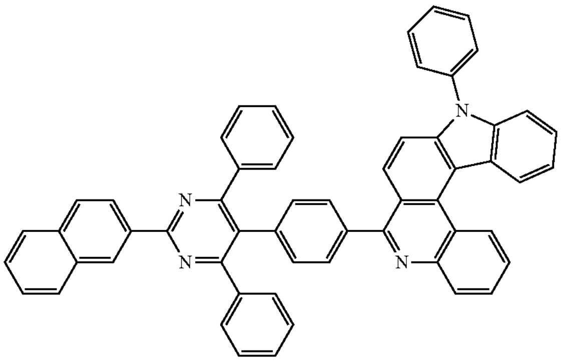
1-326
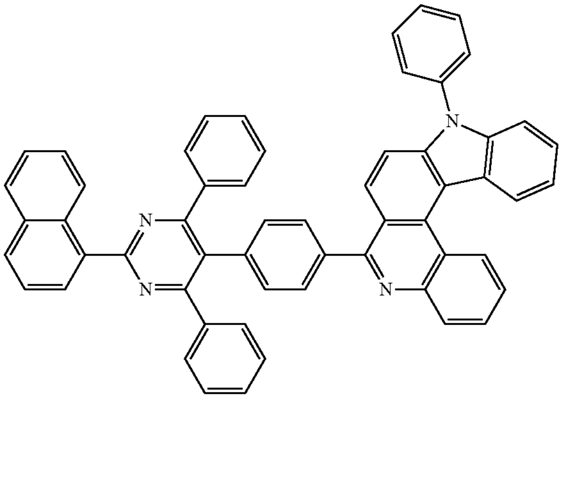
1-327
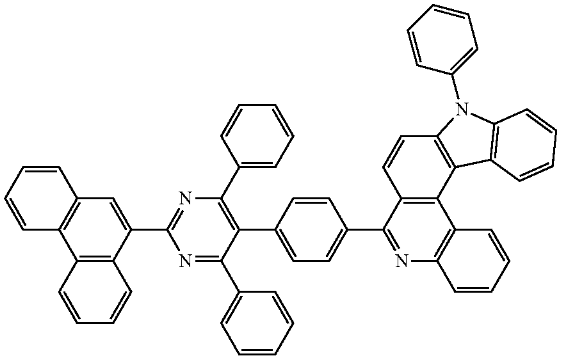

-continued
1-328
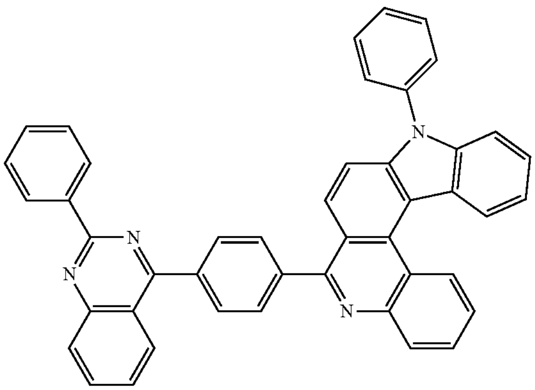
1-329
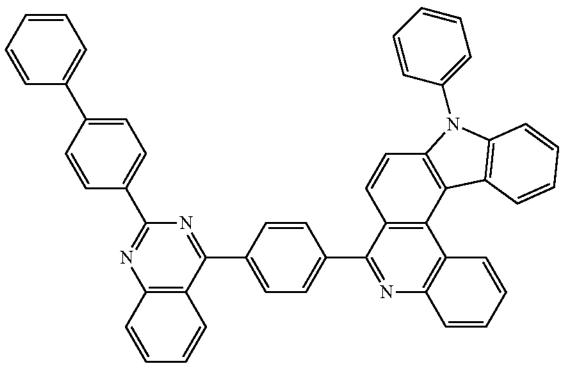
1-330
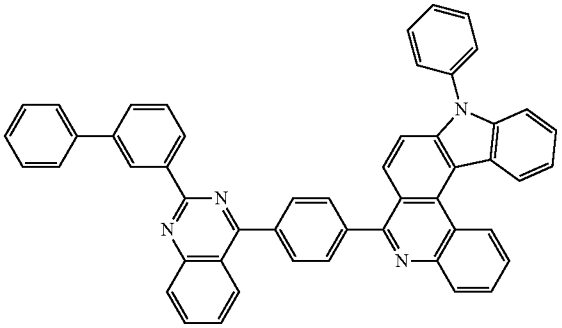
1-331
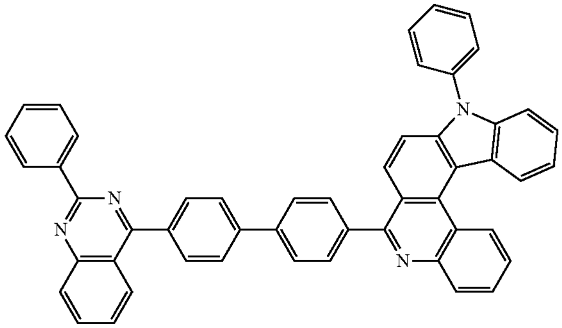
1-332
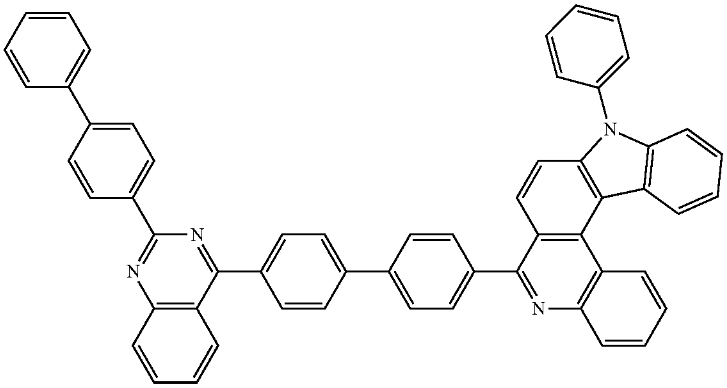
1-333
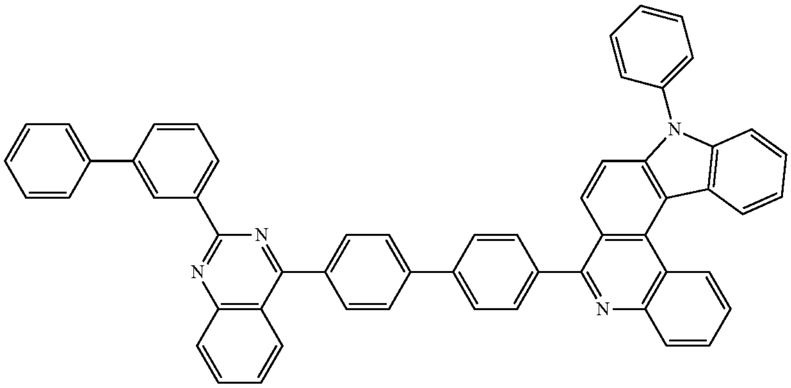

-continued
1-334
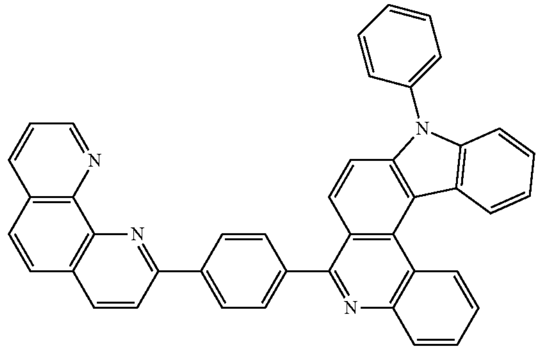
1-335
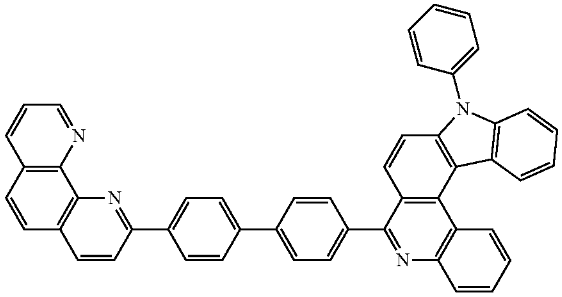
1-336
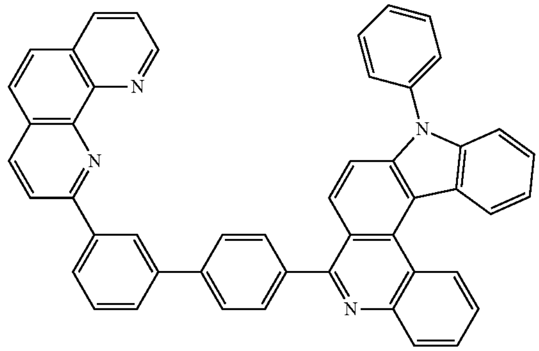
1-337
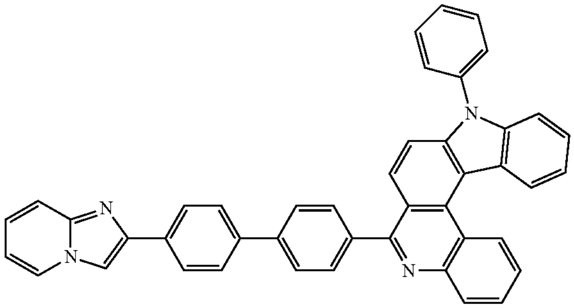
1-338
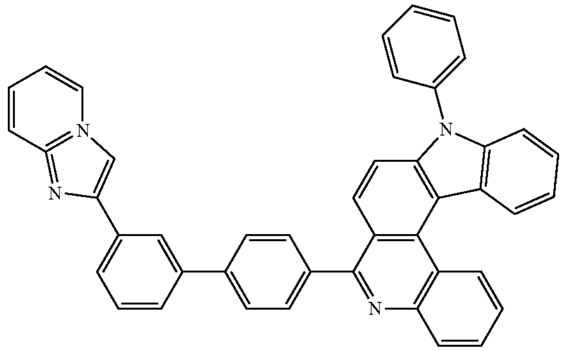
1-339
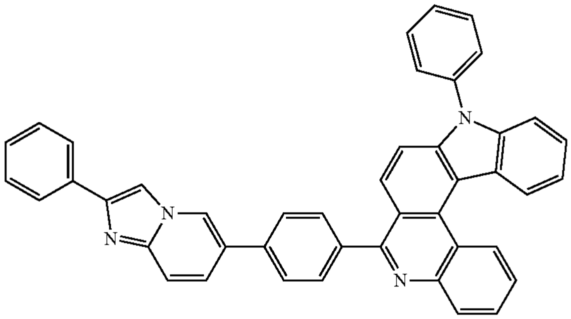
1-340
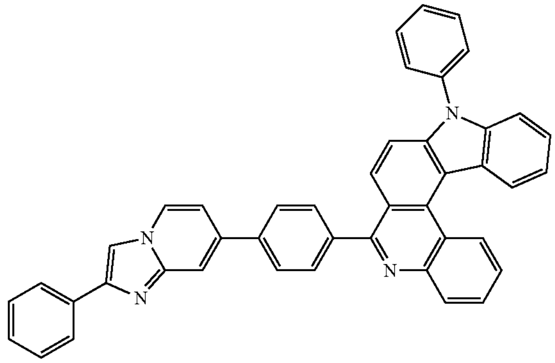
1-341
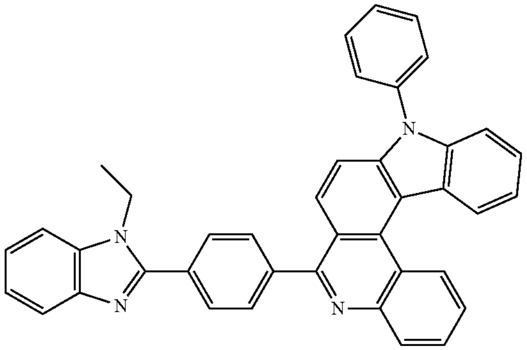

-continued
1-342
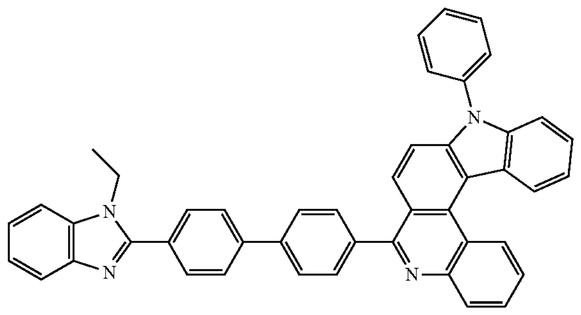
1-343
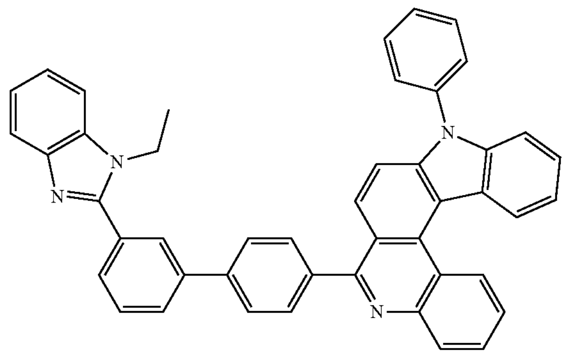
1-344
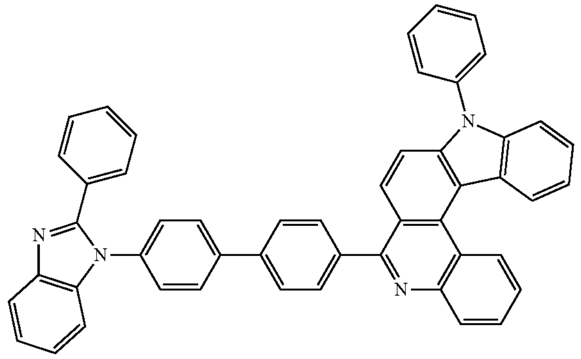
1-345
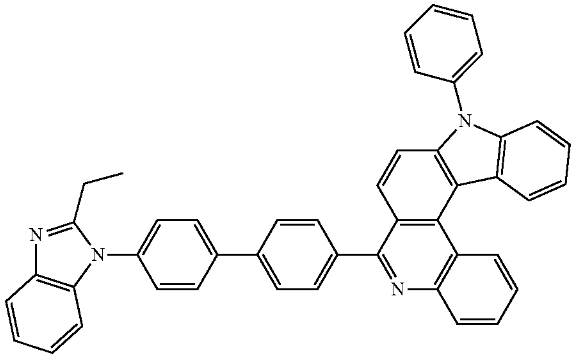
1-346
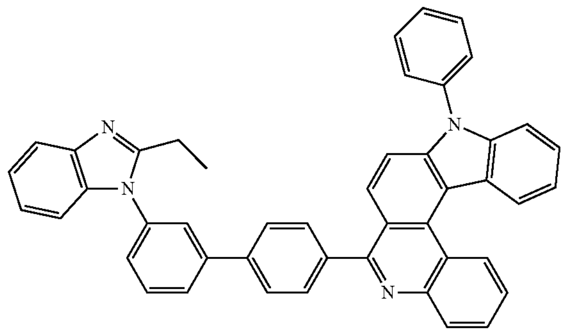
1-347
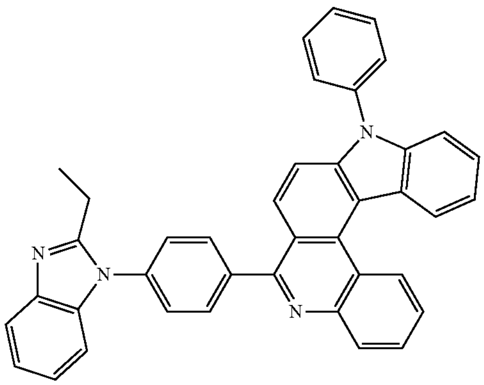
1-348
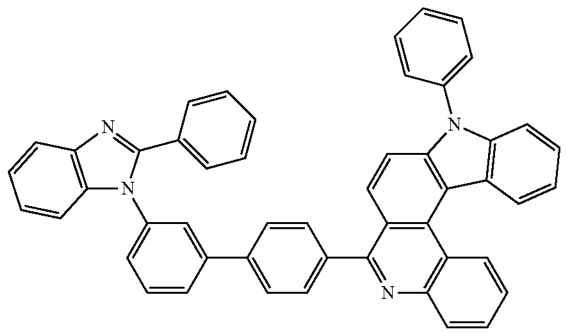
1-349
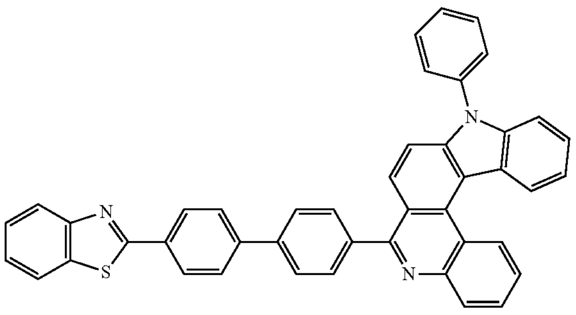

-continued
1-350
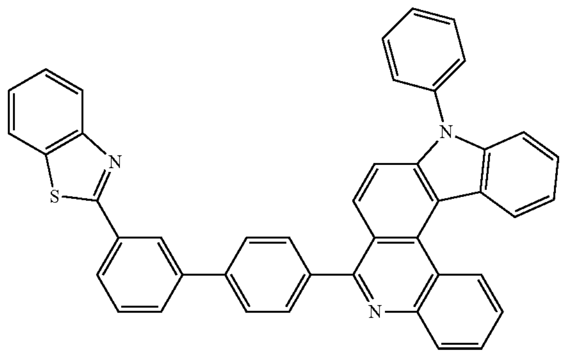
1-351
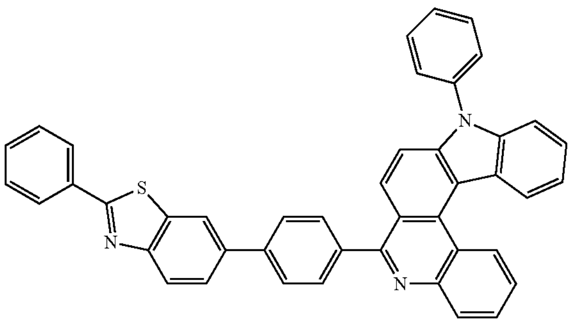
1-352
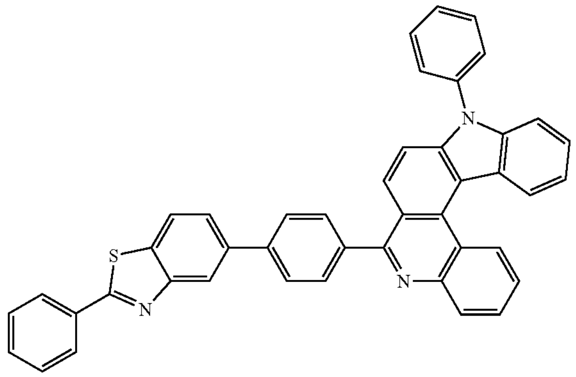
1-353
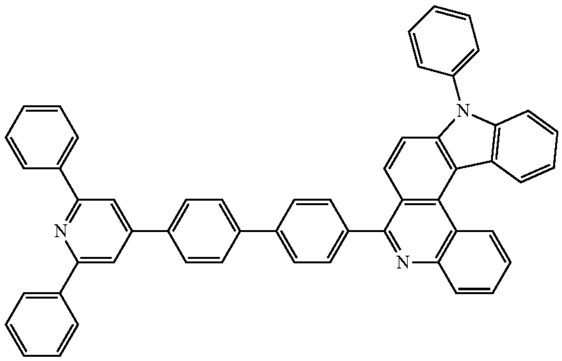
1-354
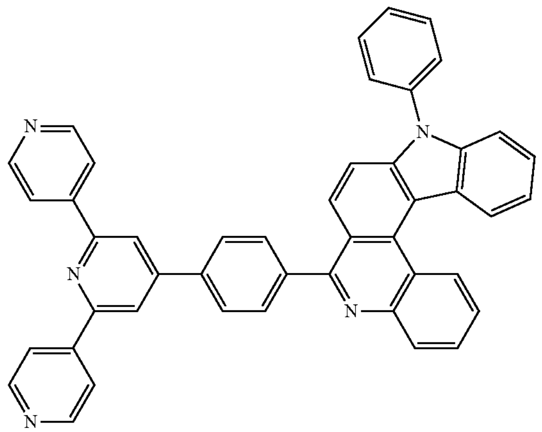
1-355
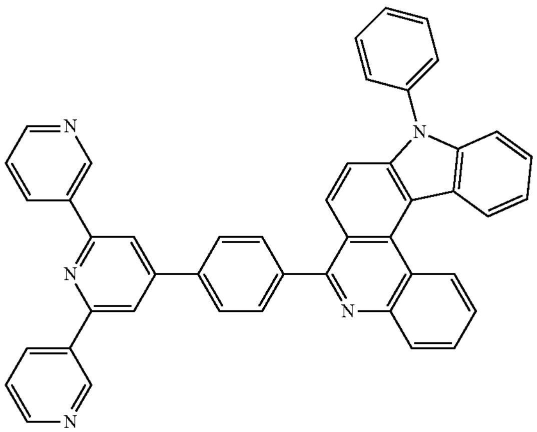

-continued
1-356
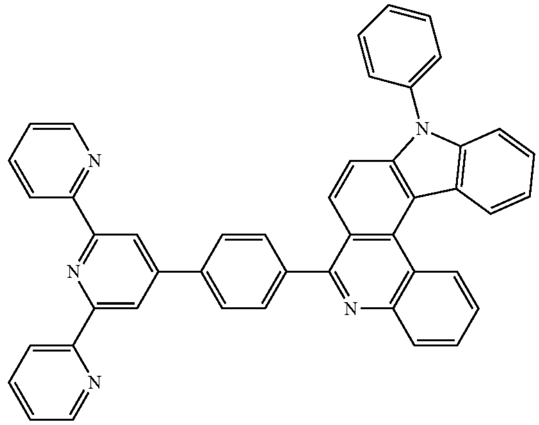
1-357
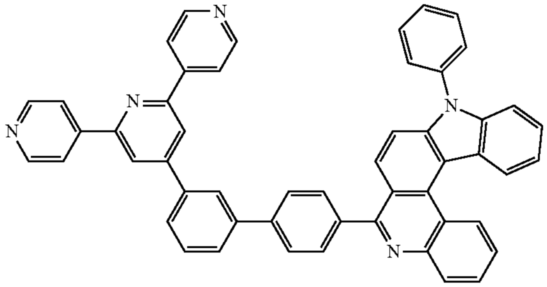
1-358
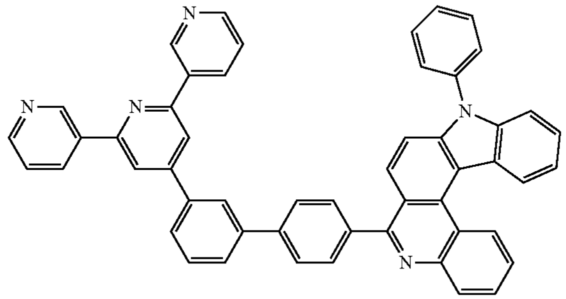
1-359
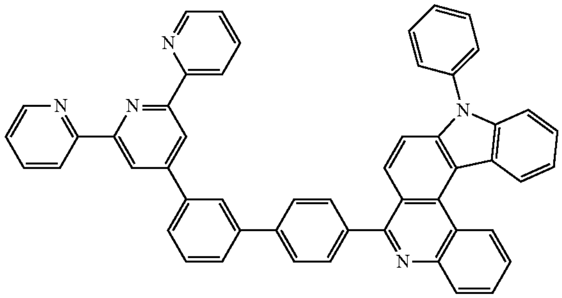
1-360
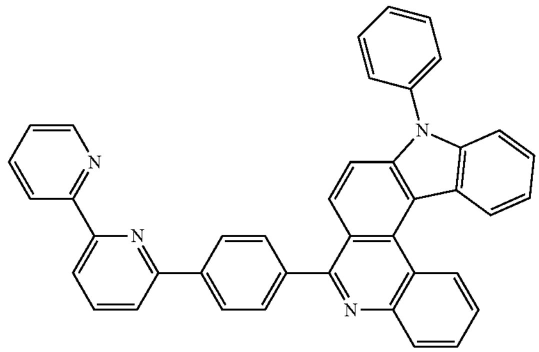
1-361
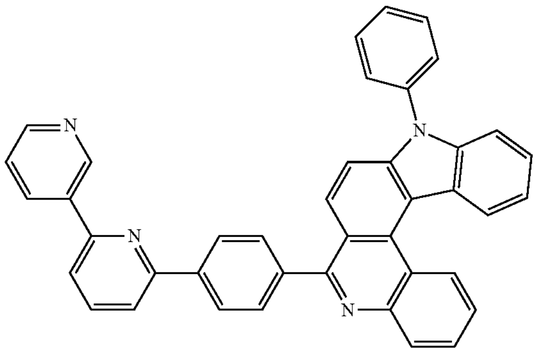
1-362
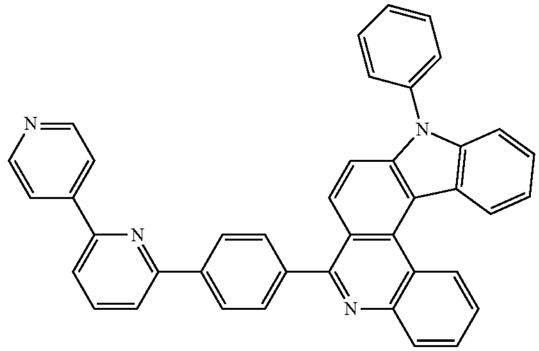
1-363
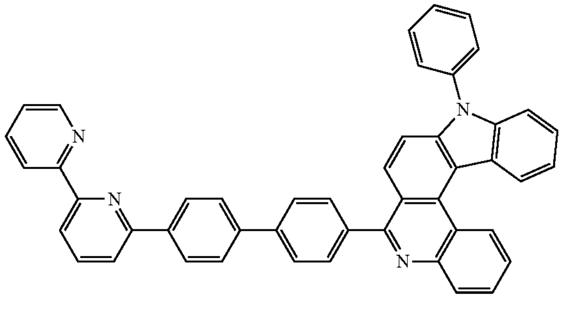

-continued
1-364
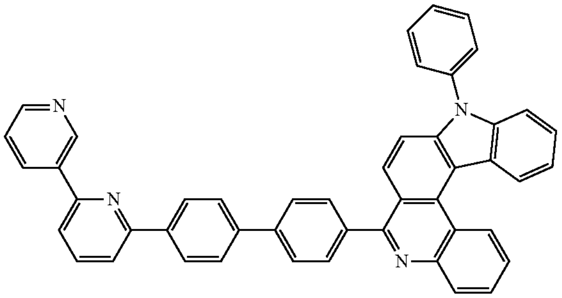
1-365
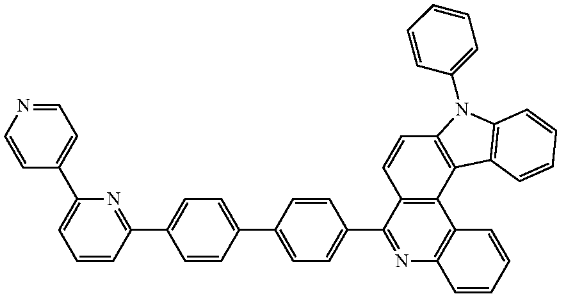
1-495
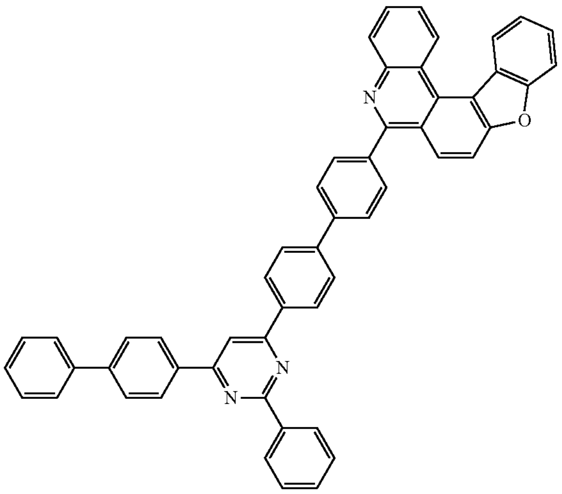
1-496
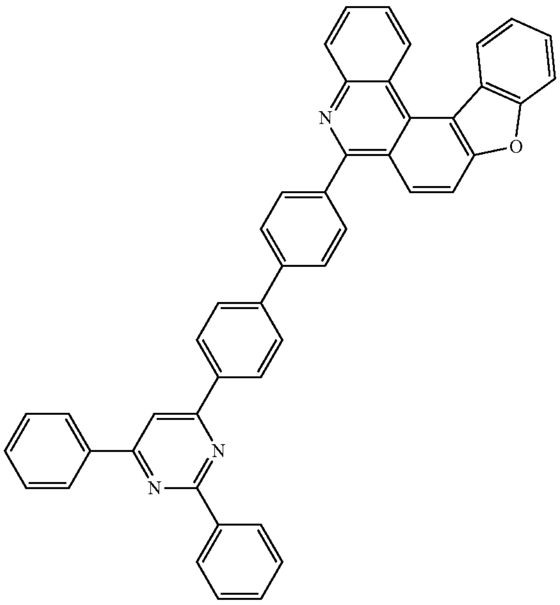
1-497
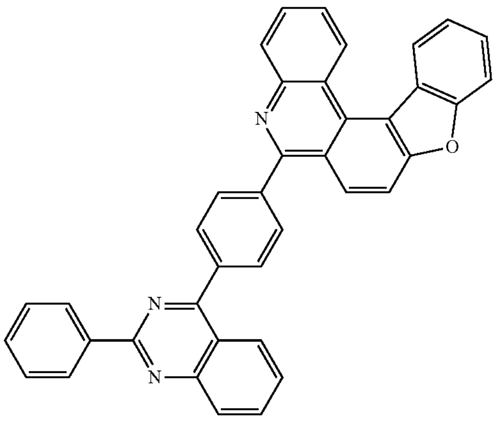
1-498
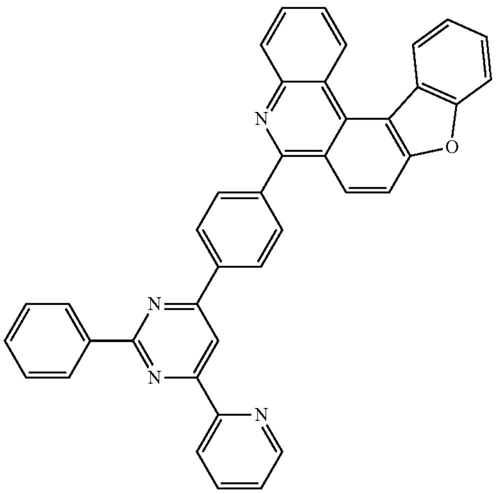

-continued
1-499
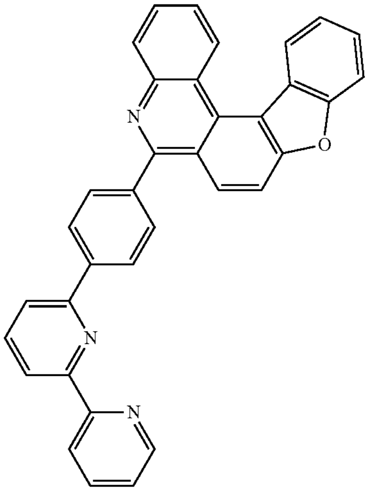
1-500
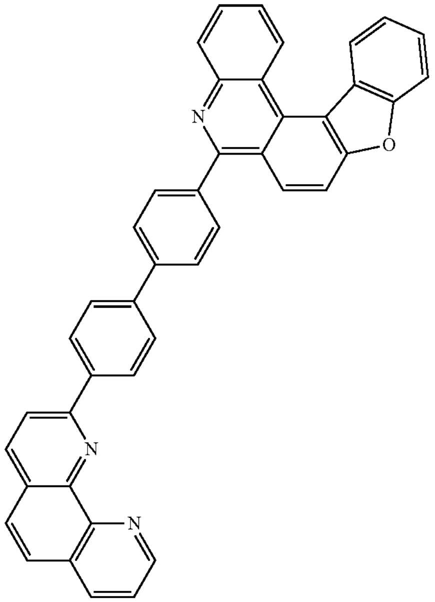
1-501
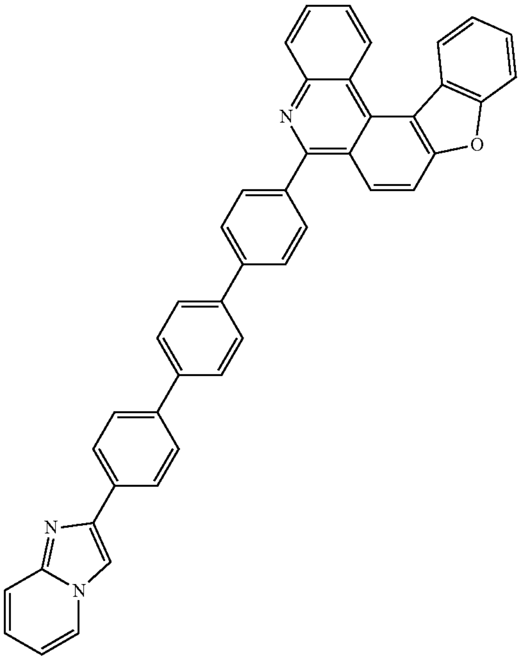
1-502
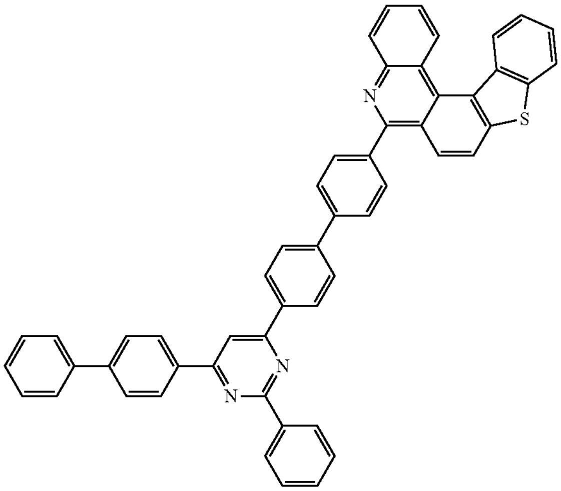

-continued
1-503
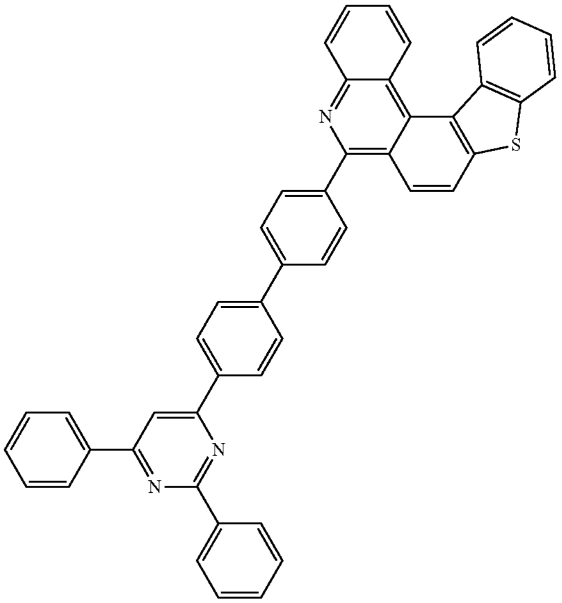
1-504
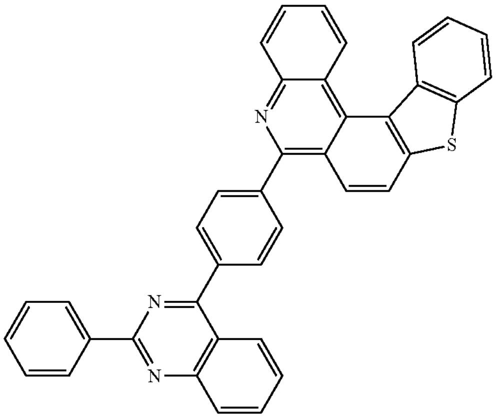
1-505
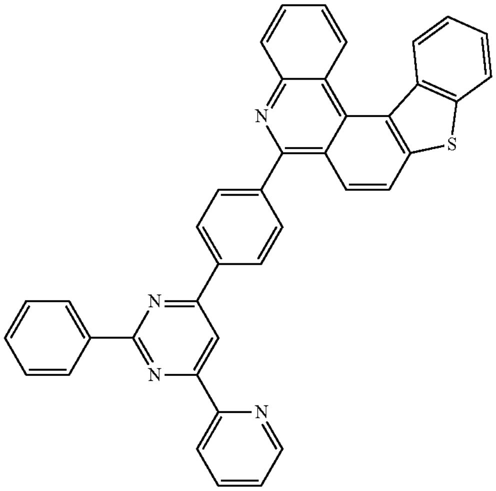
1-506
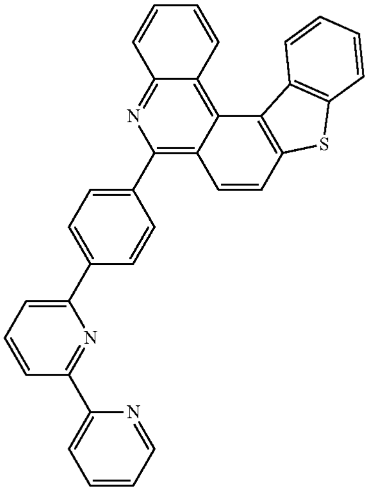

-continued
1-507
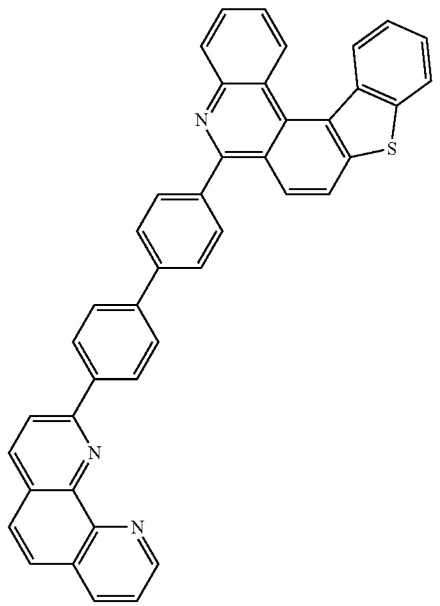
1-508
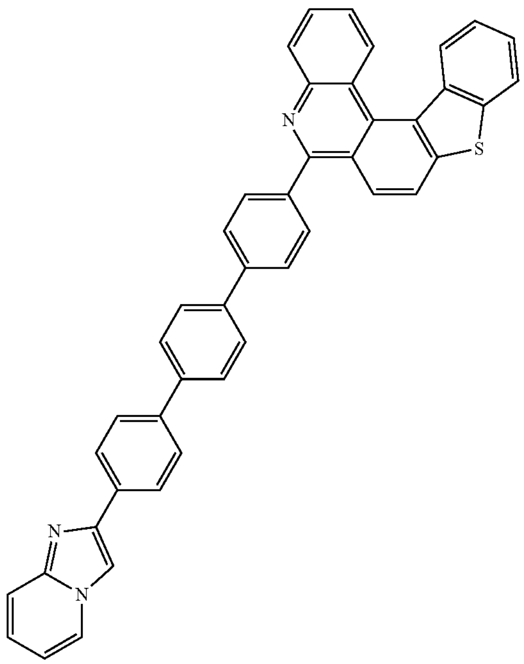
1-509
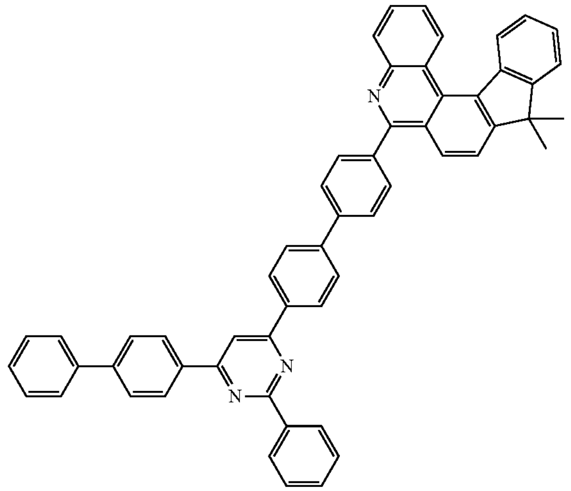
1-510
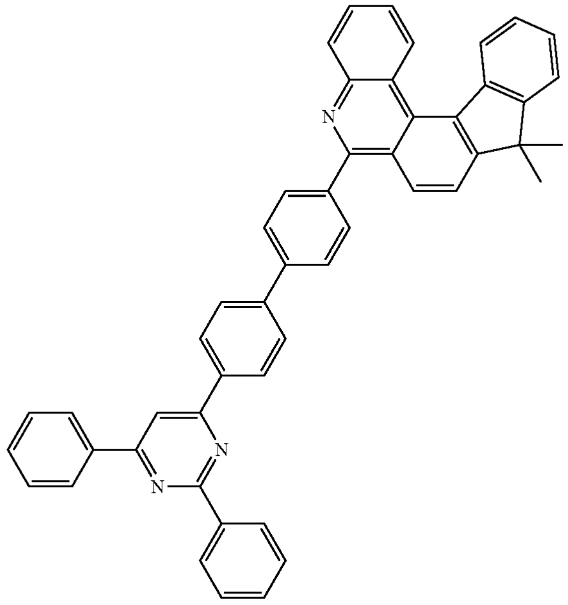

-continued
1-511
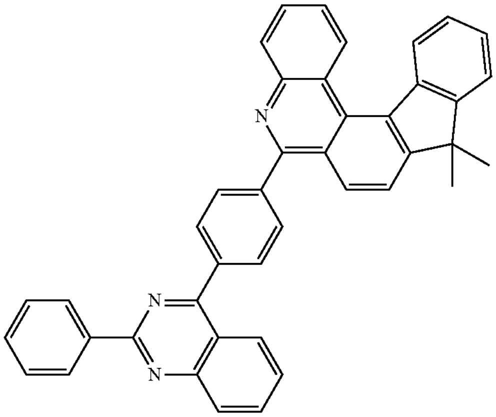
1-512
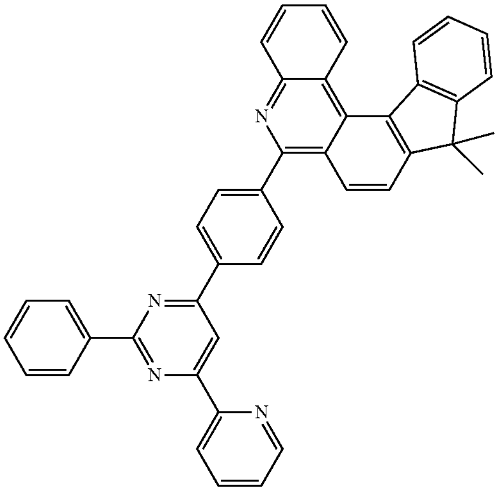
1-513
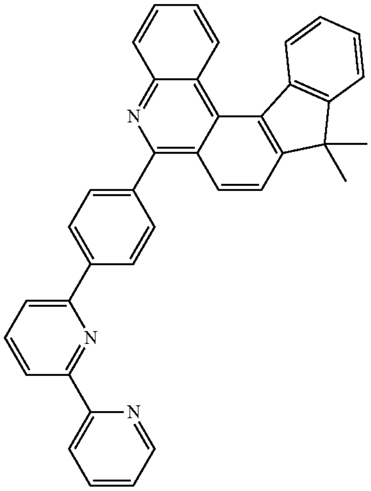
1-514
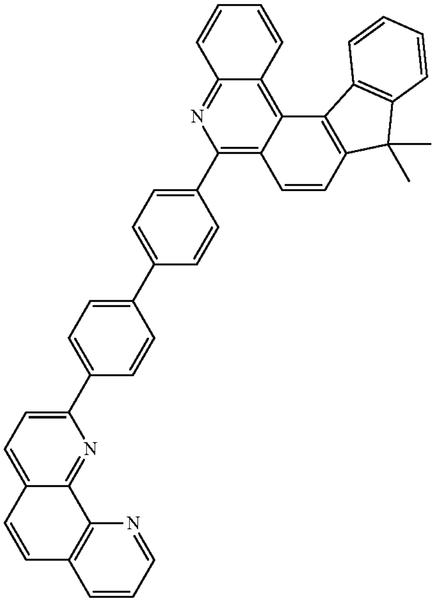

-continued
1-515
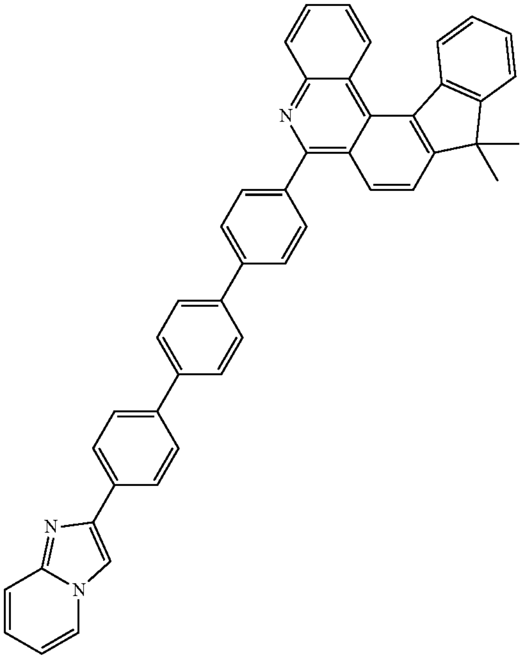
1-91
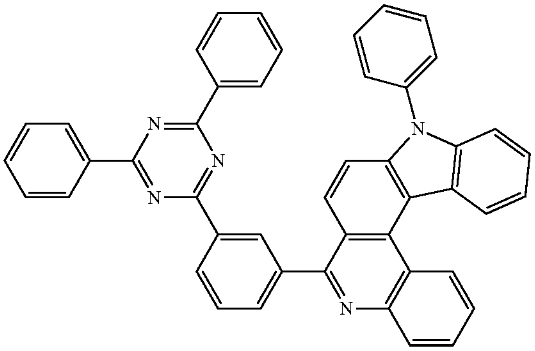
1-92
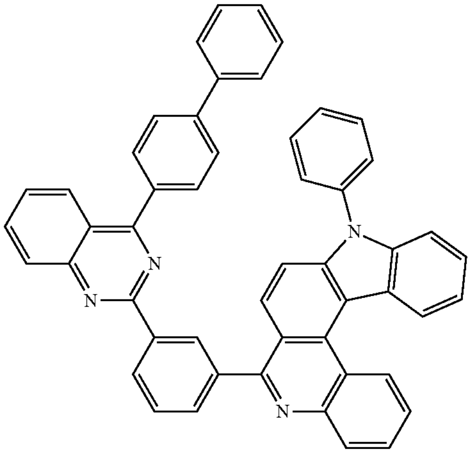
1-93
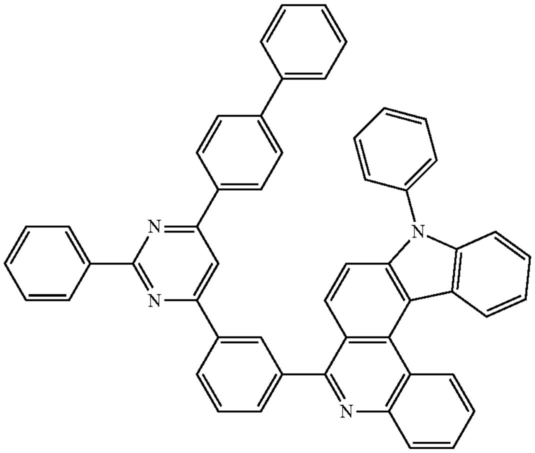
1-94
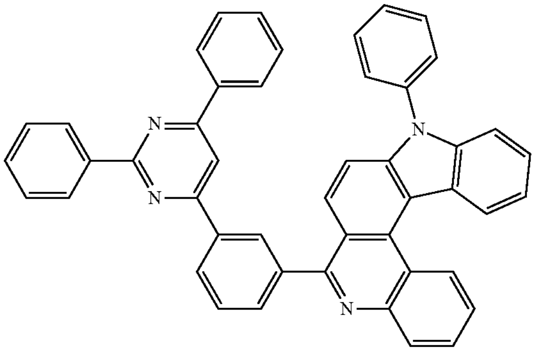
1-95
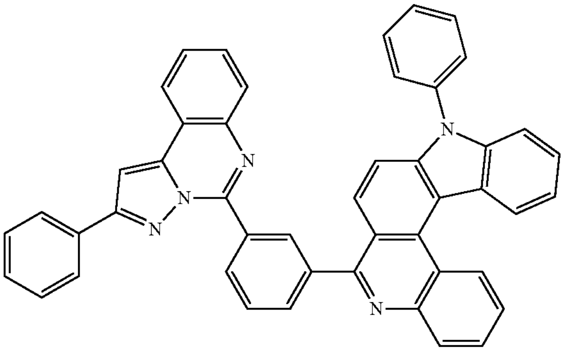

-continued
1-96
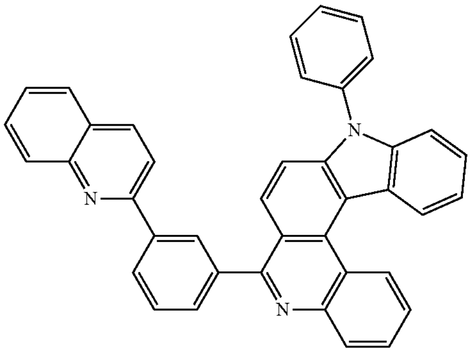
1-97
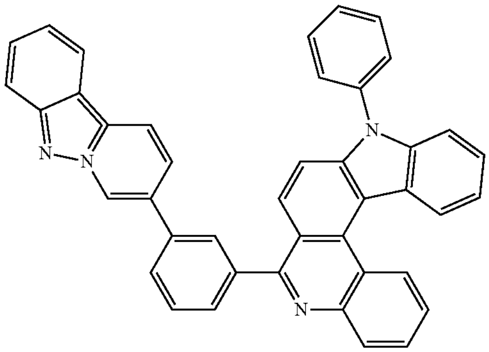
1-98
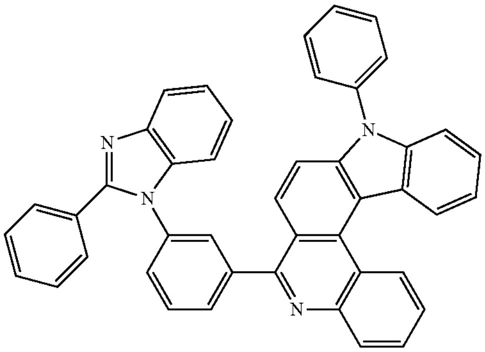
1-99
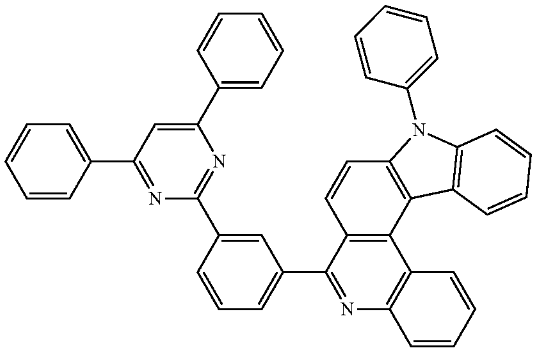
1-100
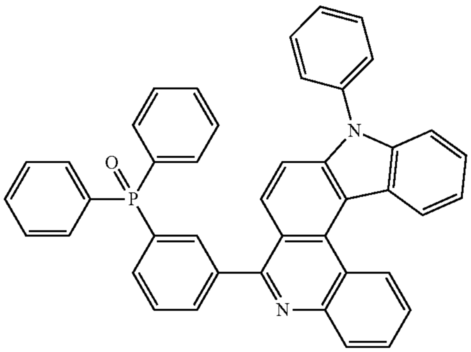
1-101
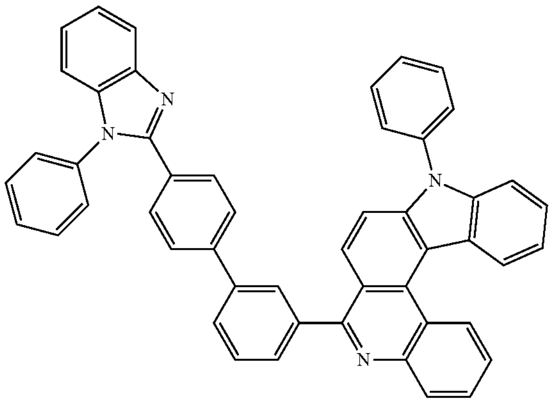
1-102
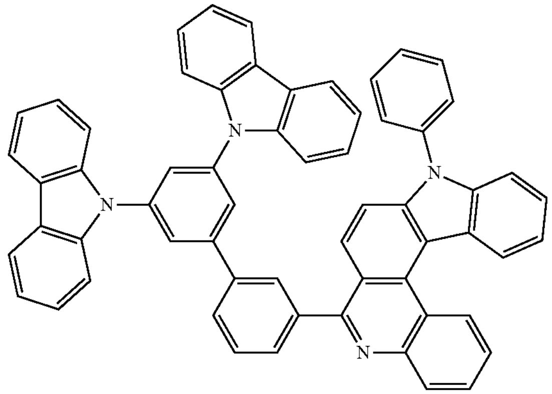
1-103
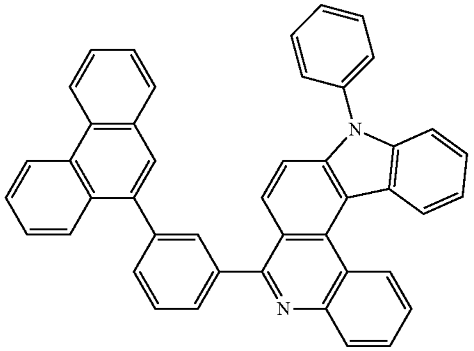

-continued
1-104
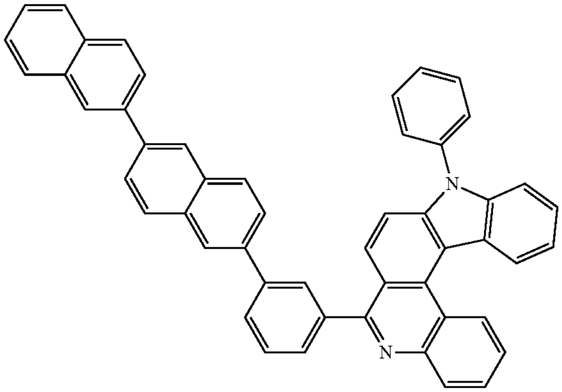
1-105
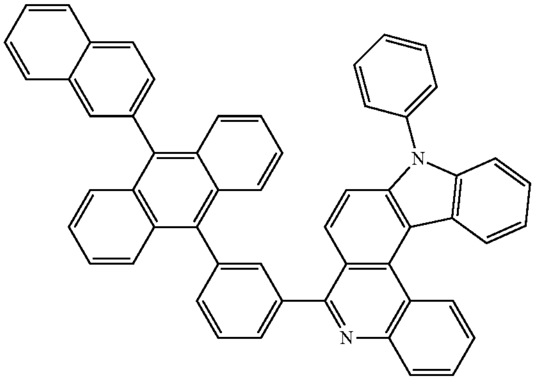
1-106
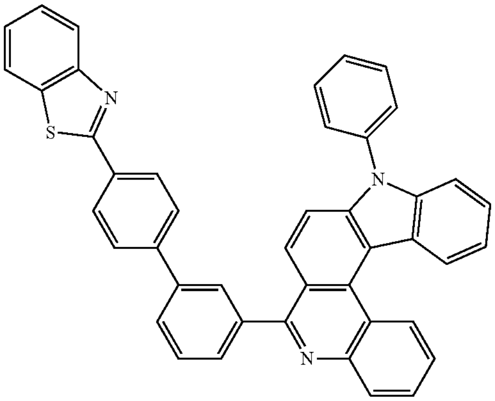
1-107
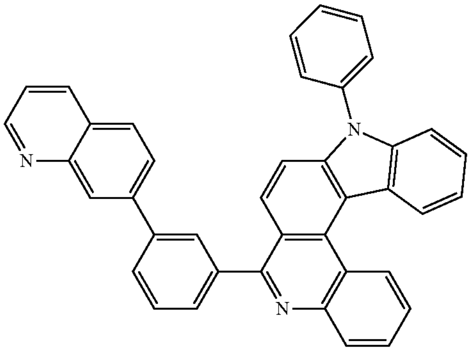
1-108
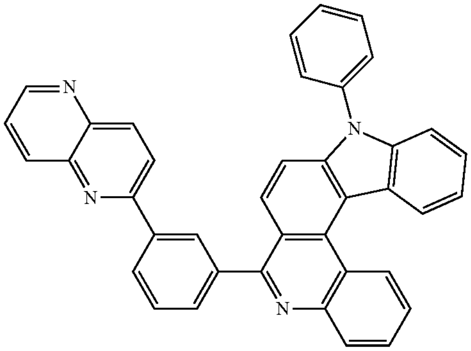
1-109
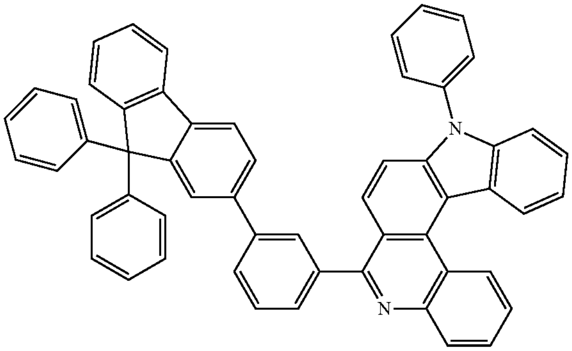
1-110
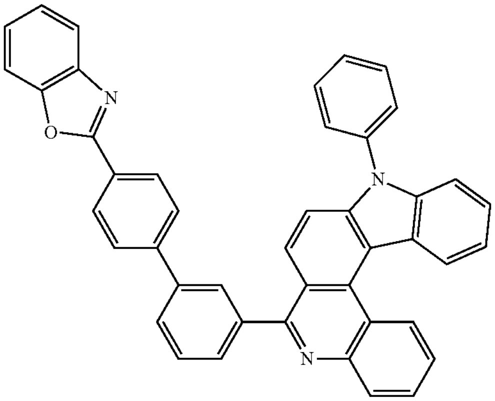
1-111
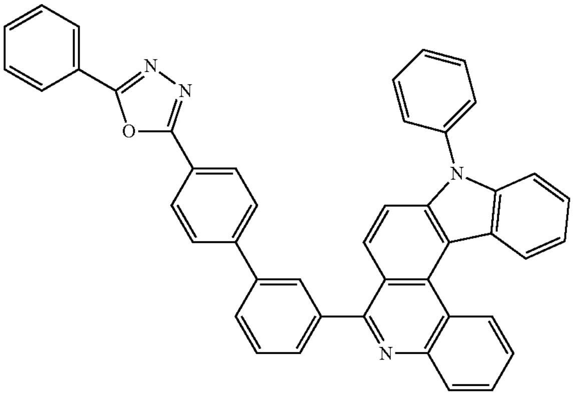

-continued
1-112
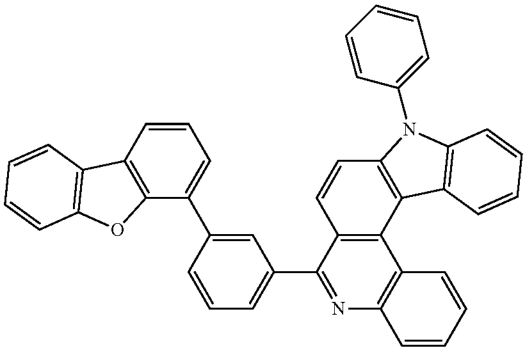
1-113
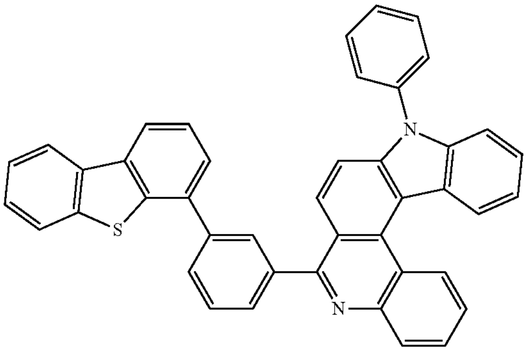
1-114
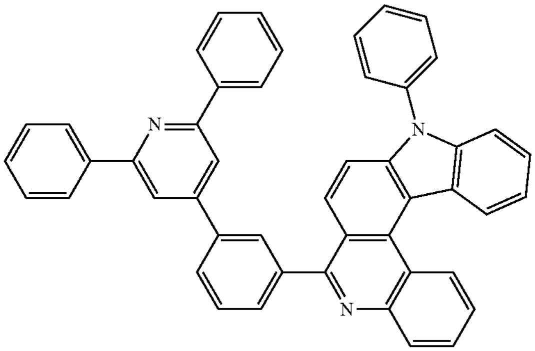
1-115
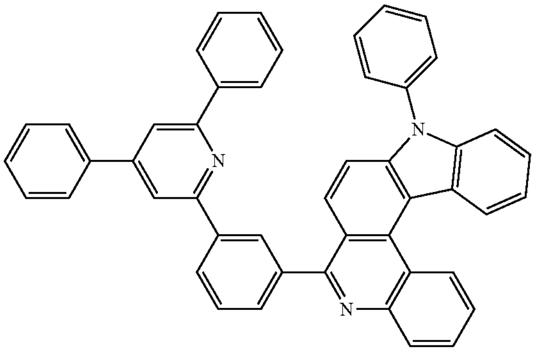
1-116
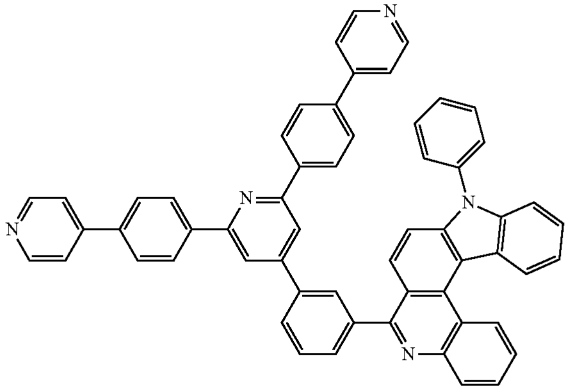
1-117
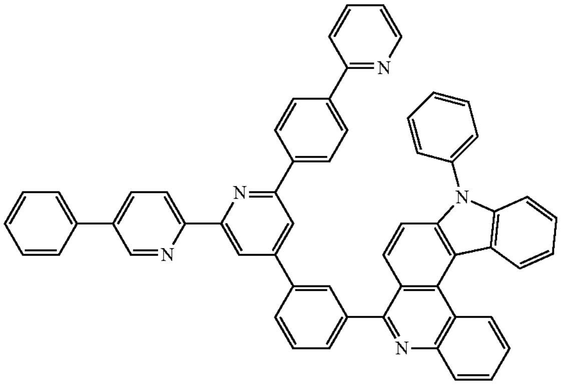
1-118
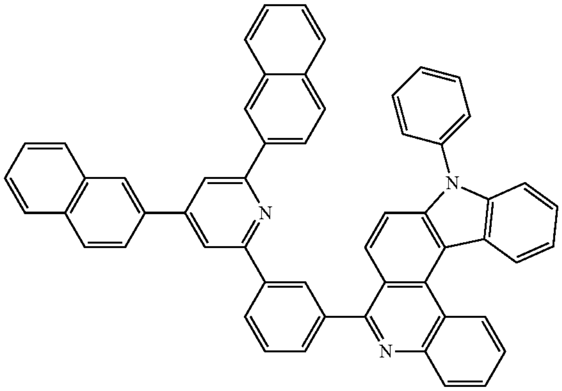
1-119
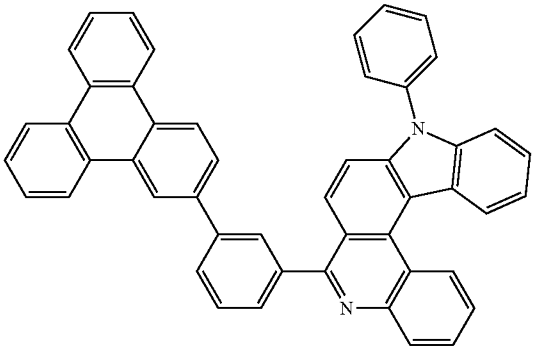

-continued
1-120
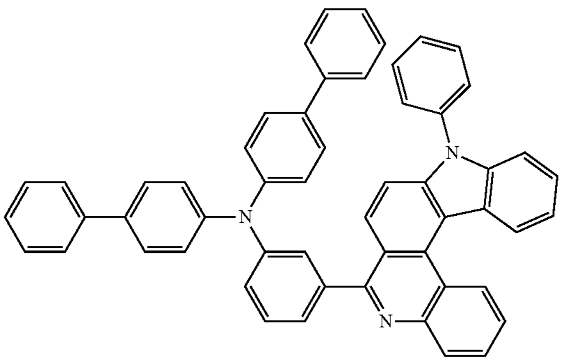
1-121
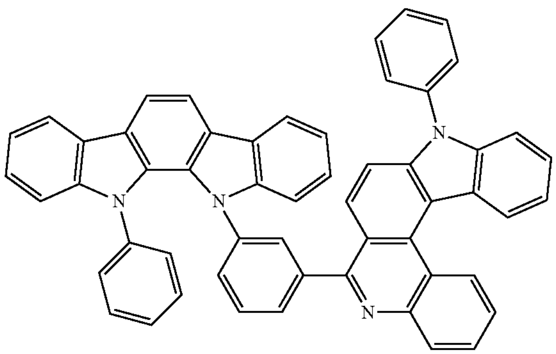
1-122
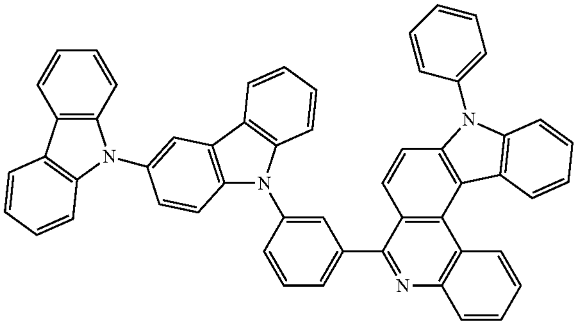
1-123
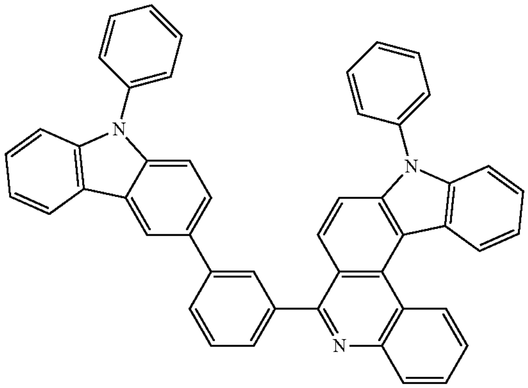
1-124
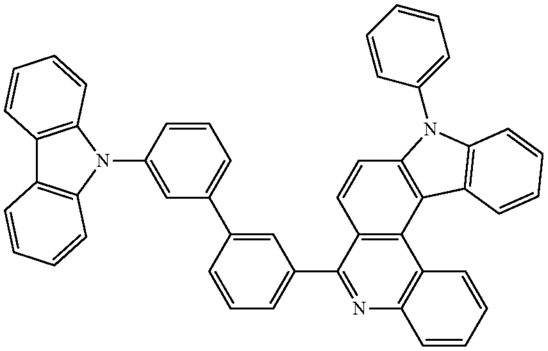
1-125
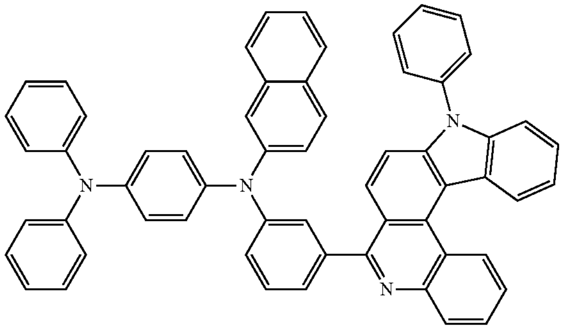
1-126
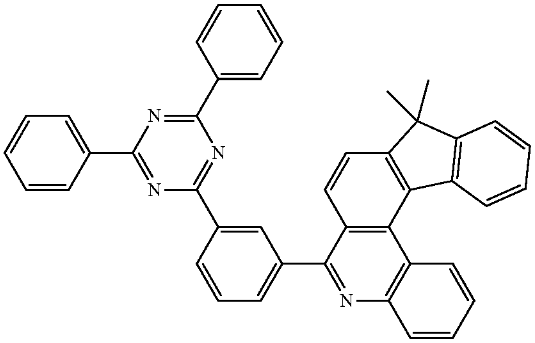
1-127
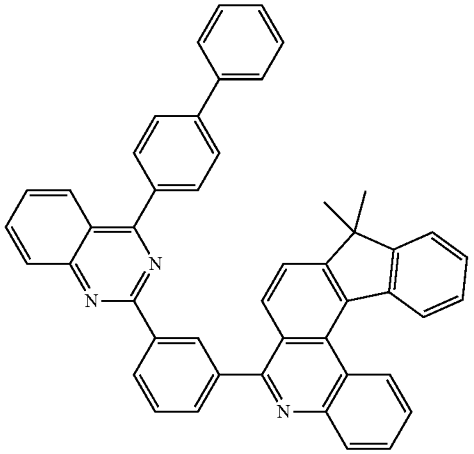

-continued
1-128
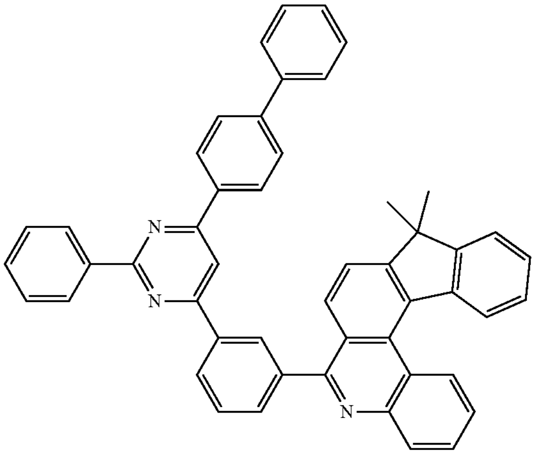
1-129
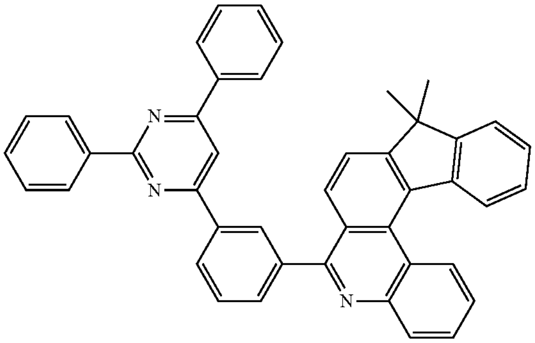
1-130
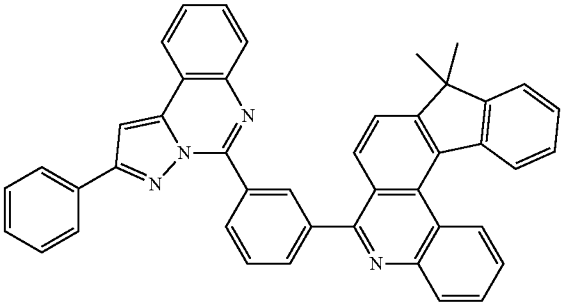
1-131
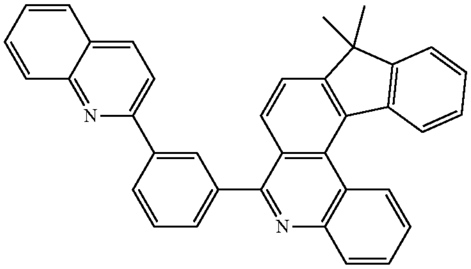
1-132
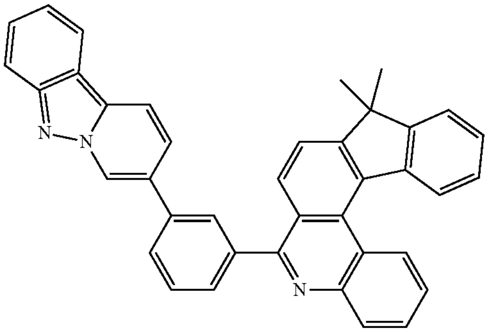
1-133
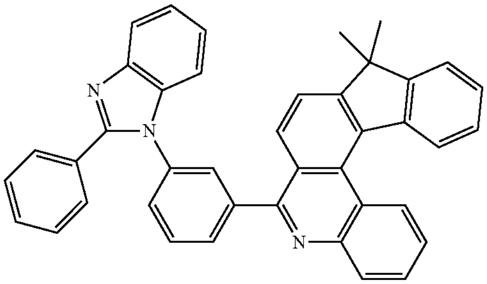
1-134
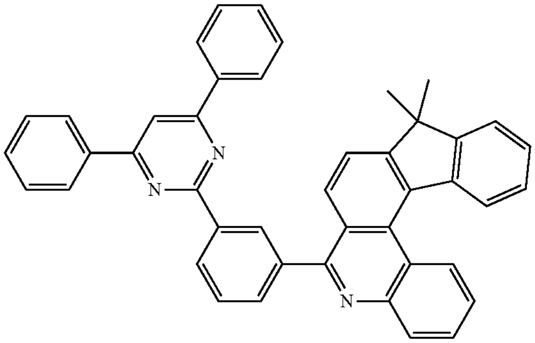
1-135
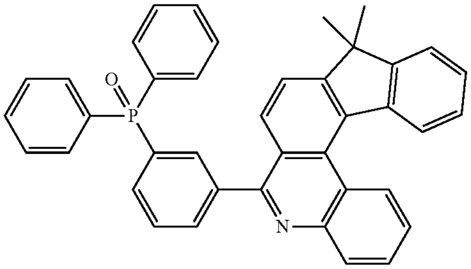

-continued
1-136
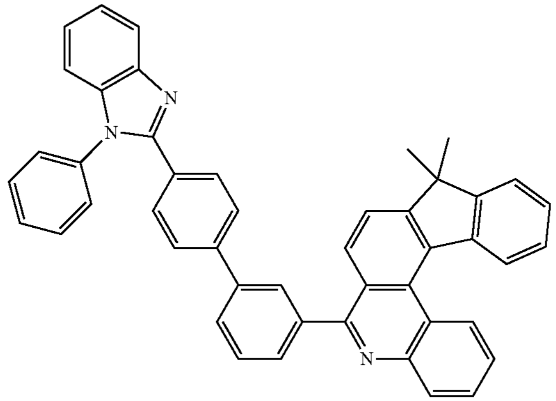
1-137
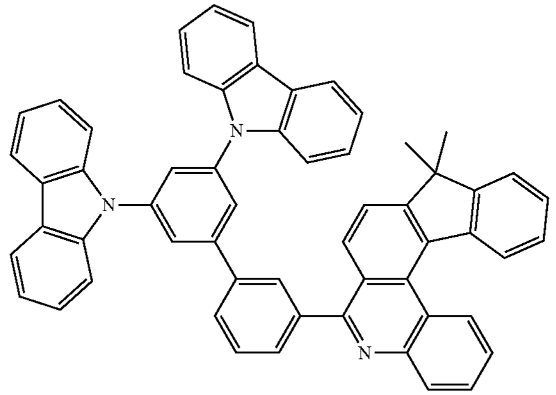
1-138
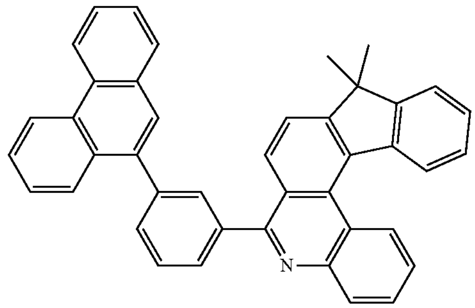
1-139
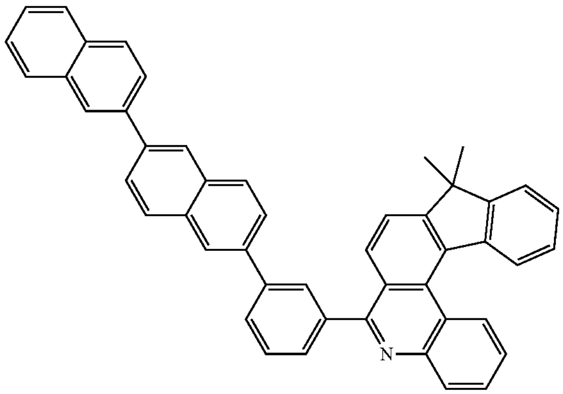
1-140
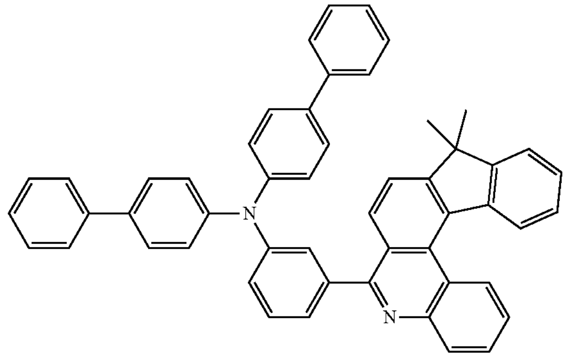
1-141
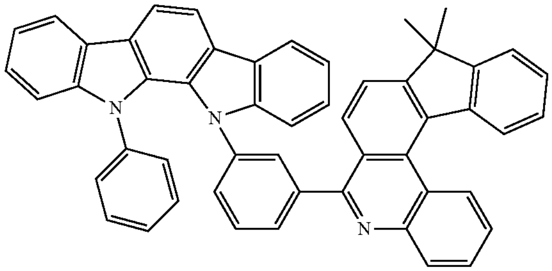
1-142
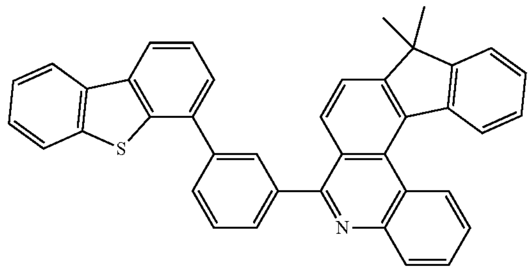
1-143
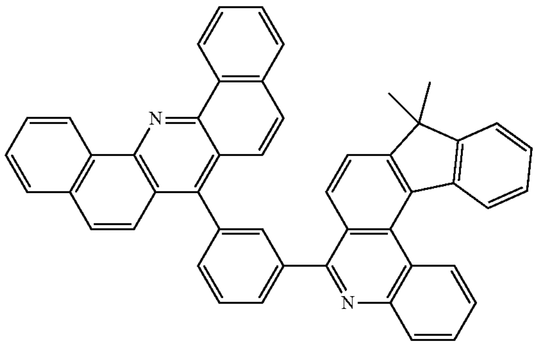

-continued
1-144
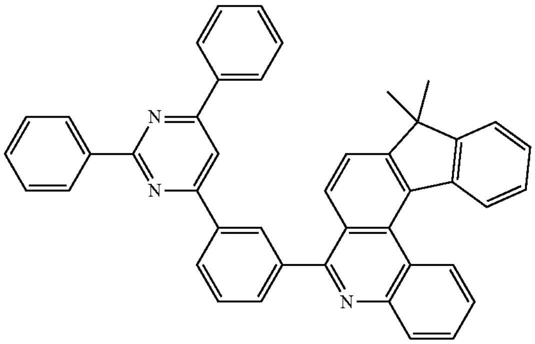
1-145
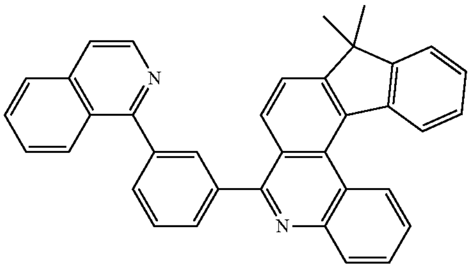
1-146
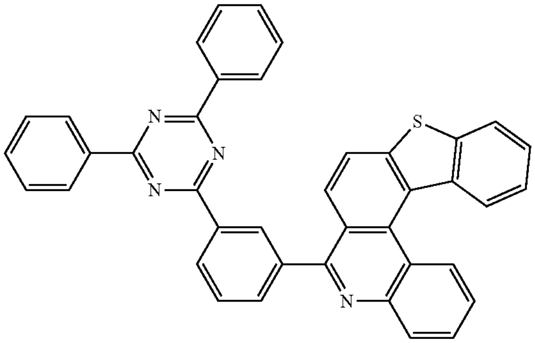
1-147
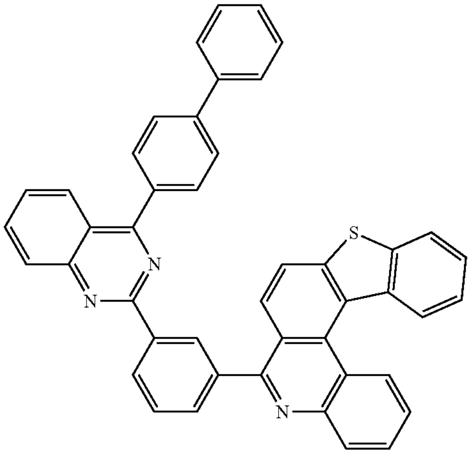
1-148
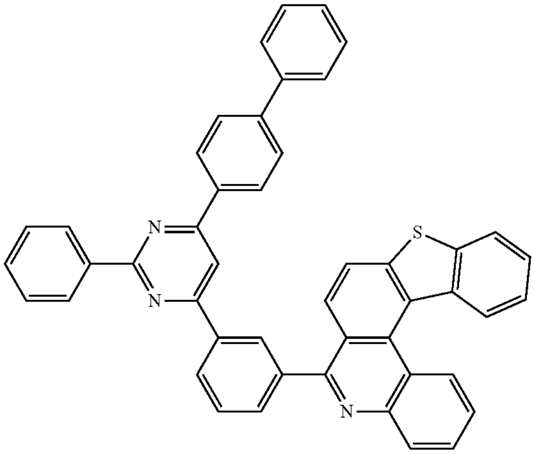
1-149
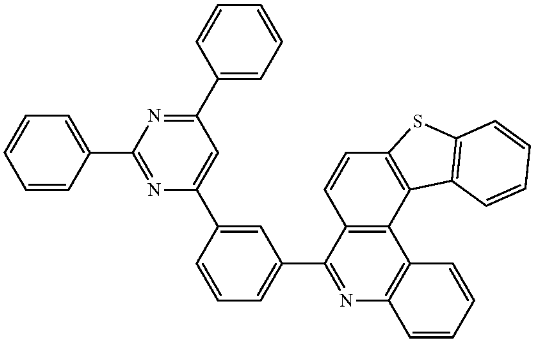
1-150
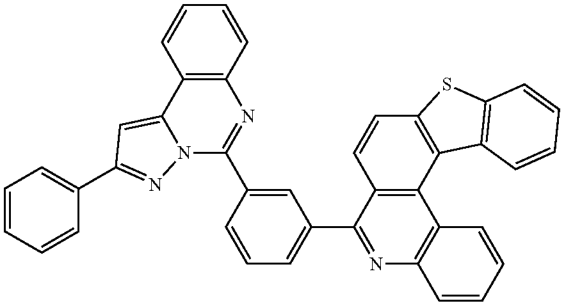
1-151
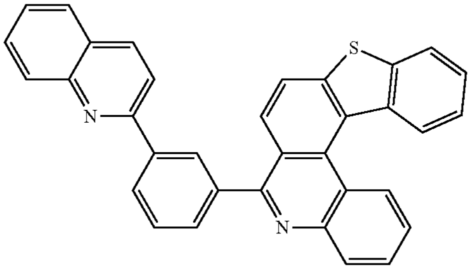

-continued
1-152
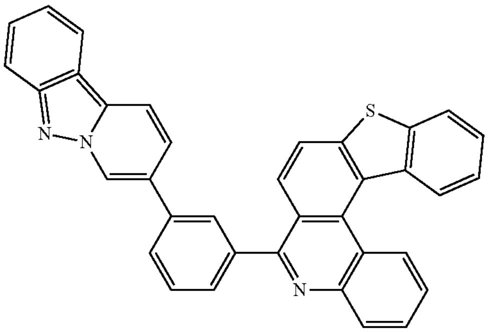
1-153
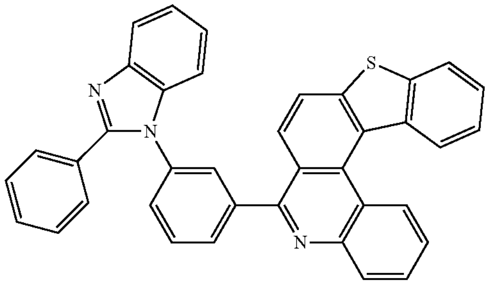
1-154
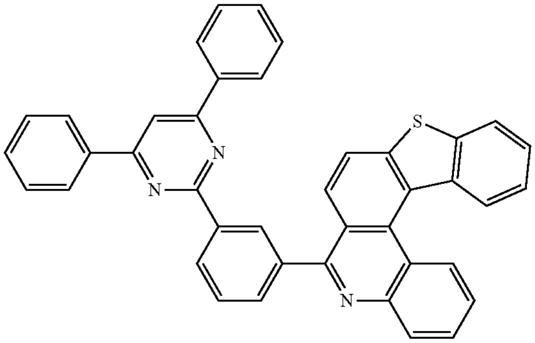
1-155
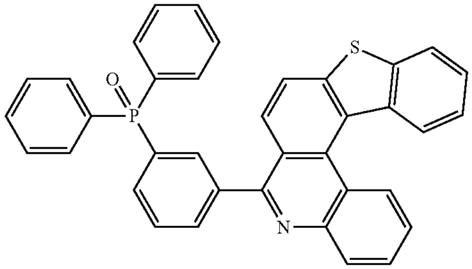
1-156
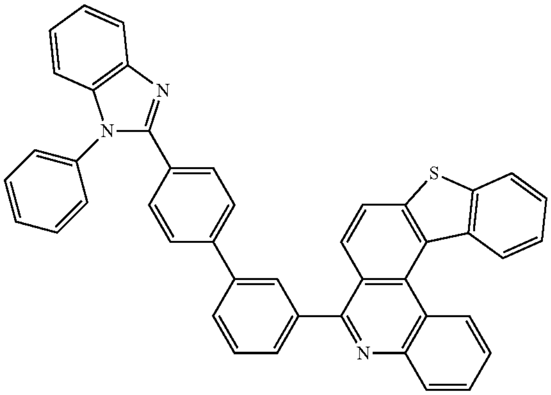
1-157
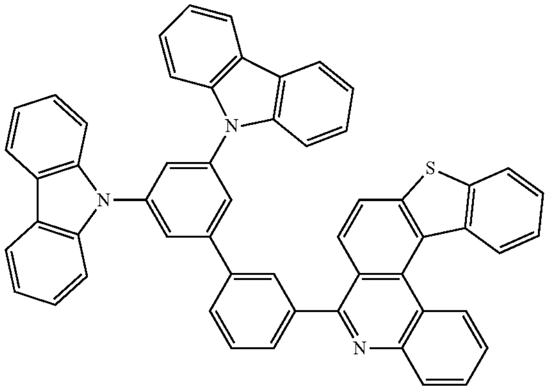
1-158
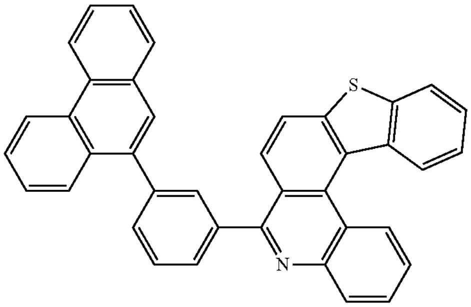
1-159
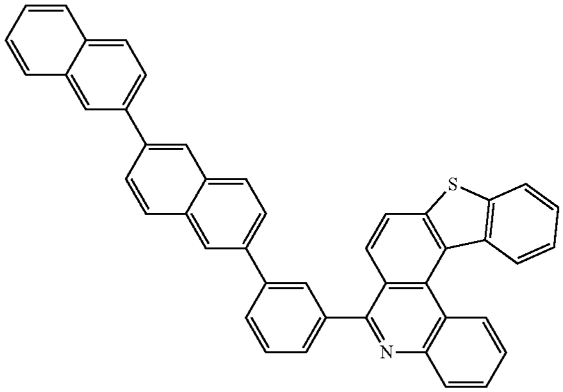

-continued
1-160
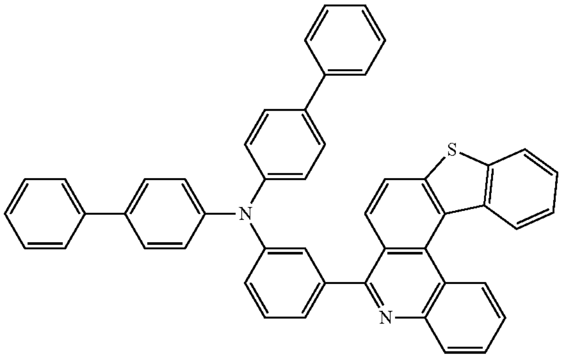
1-161
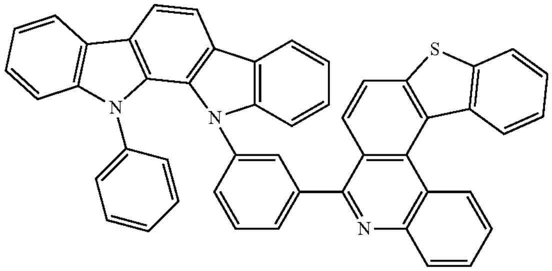
1-162
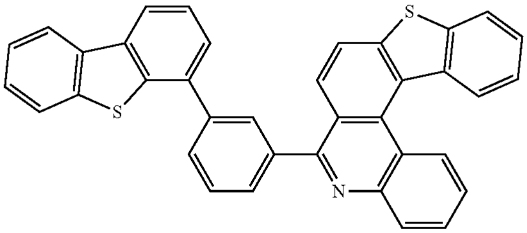
1-163
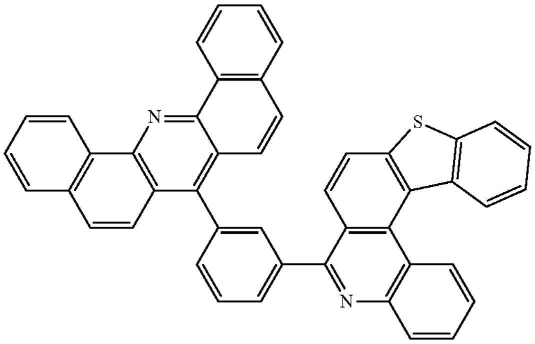
1-164
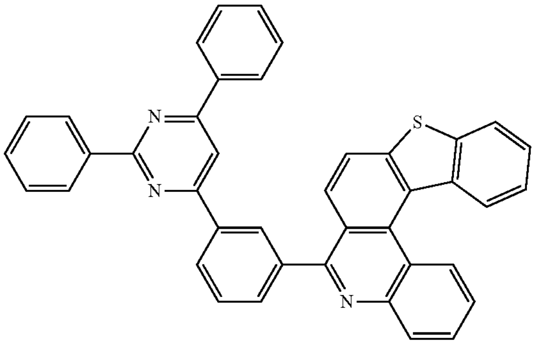
1-165
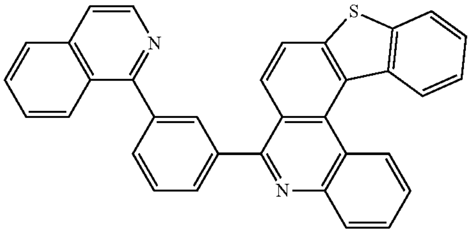
1-166
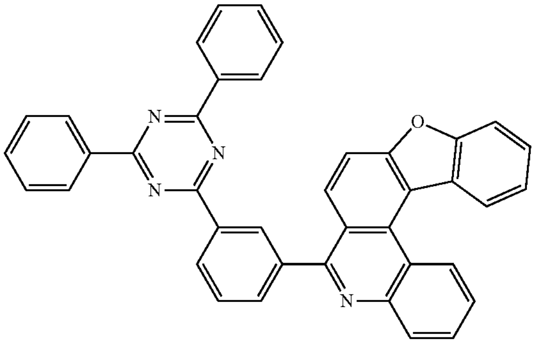
1-167
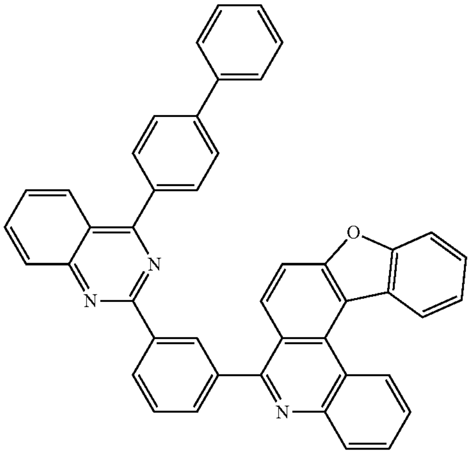

-continued
1-168
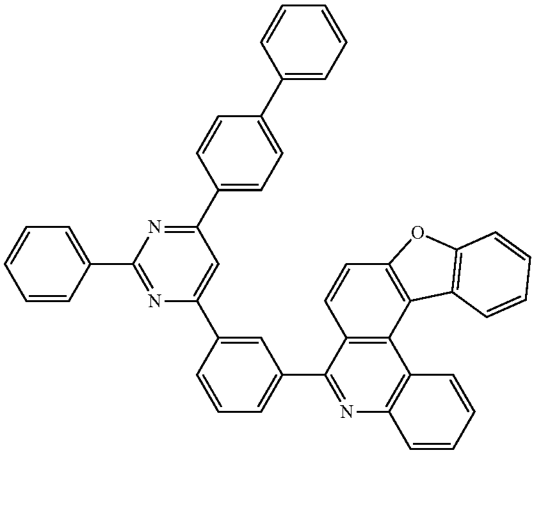
1-169
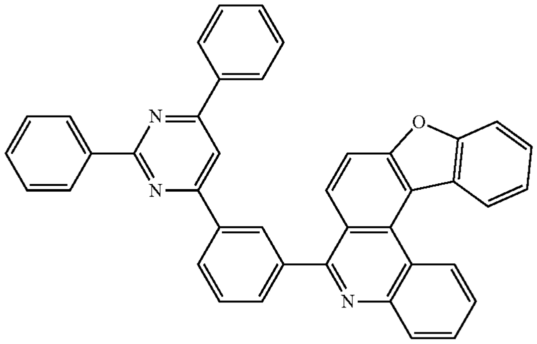
1-170
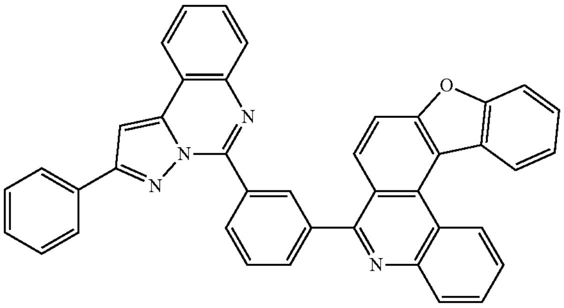
1-171
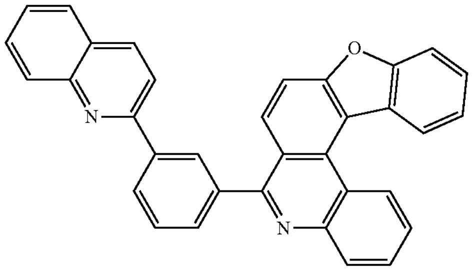
1-172
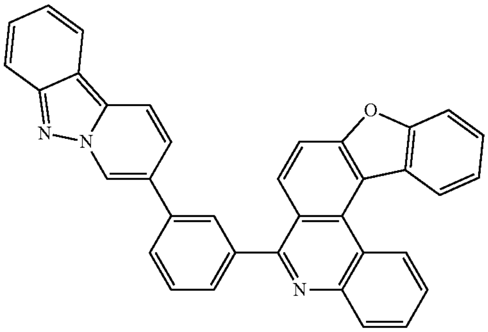
1-173
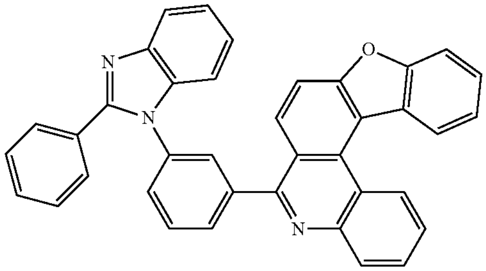
1-174
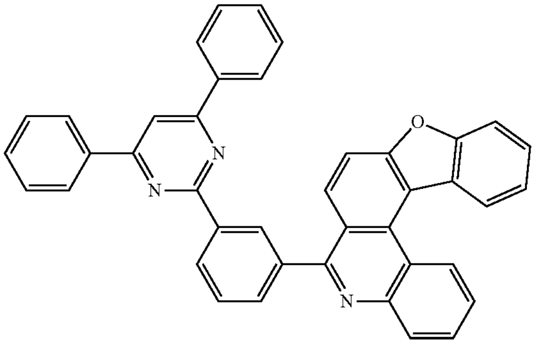
1-175
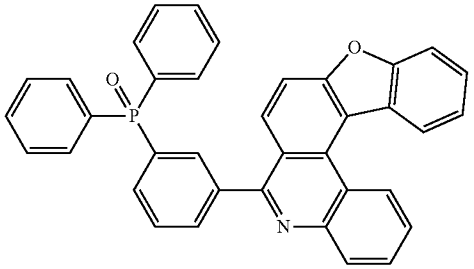

-continued
1-176
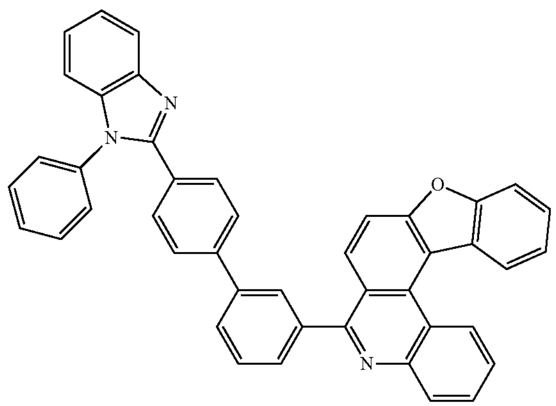
1-177
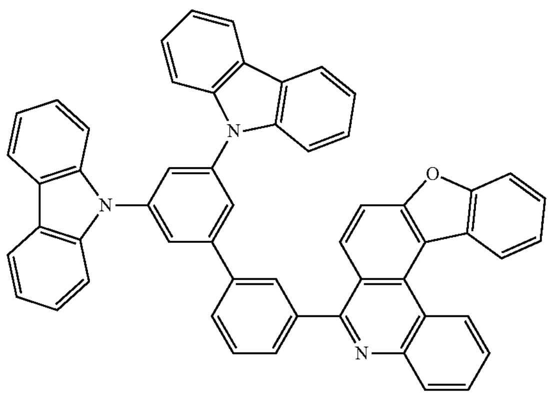
1-178
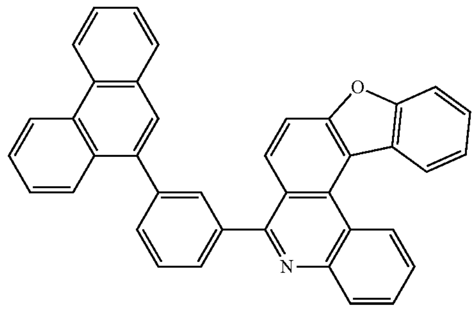
1-179
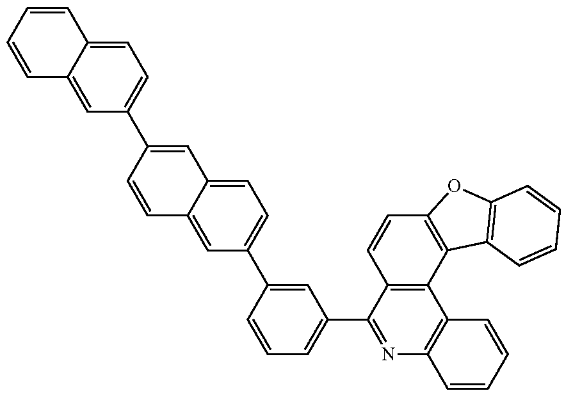
1-180
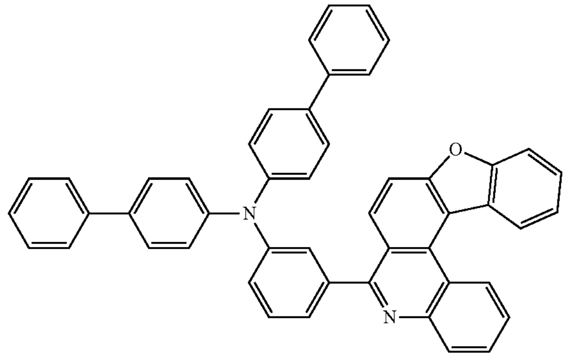
1-366
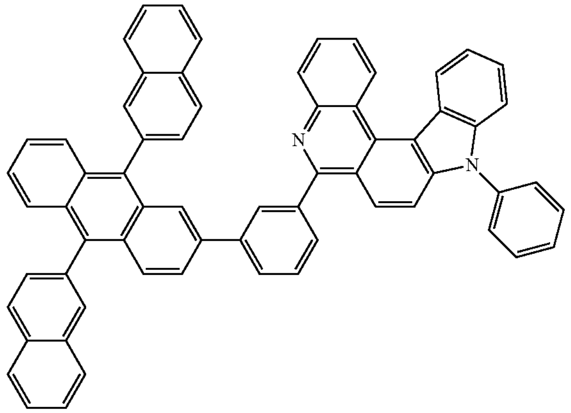
1-367
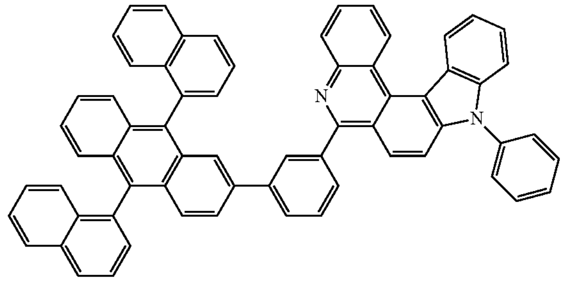
1-368
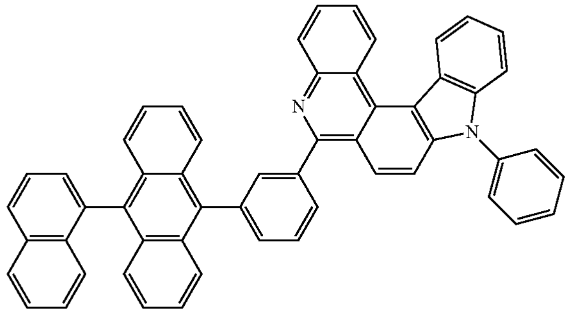

-continued
1-369
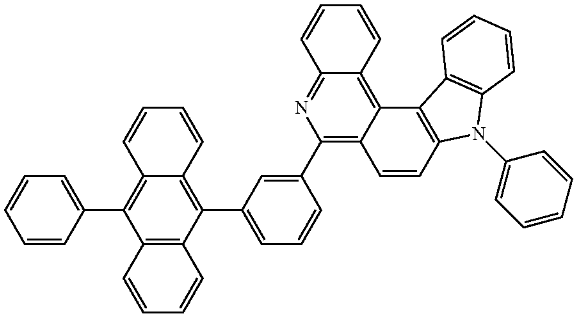
1-370
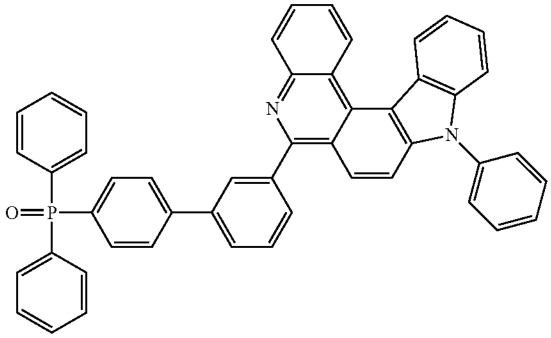
1-371
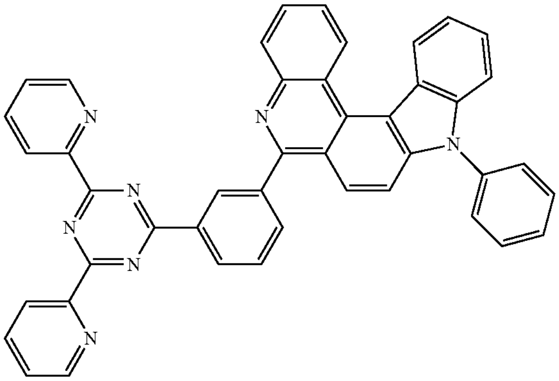
1-372
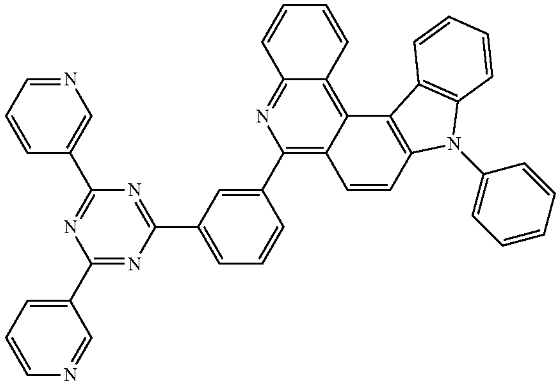
1-373
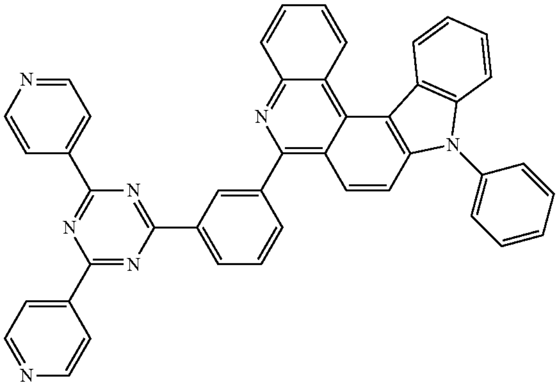
1-374
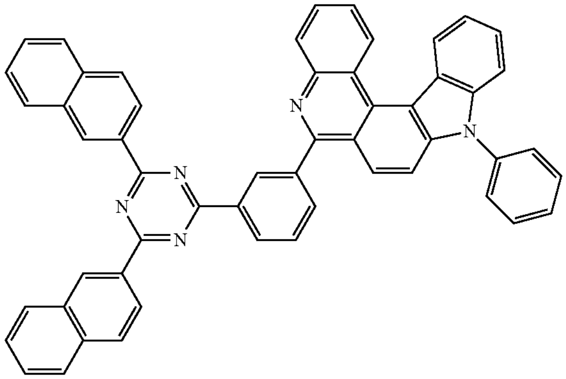
1-375
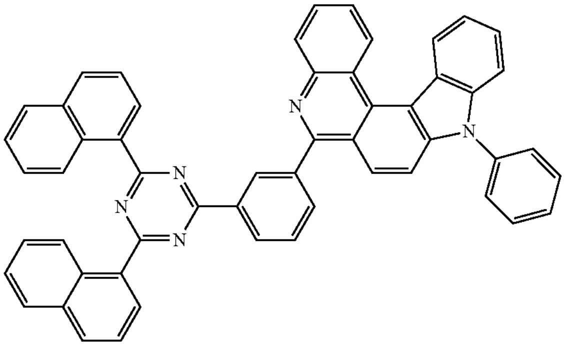
1-376
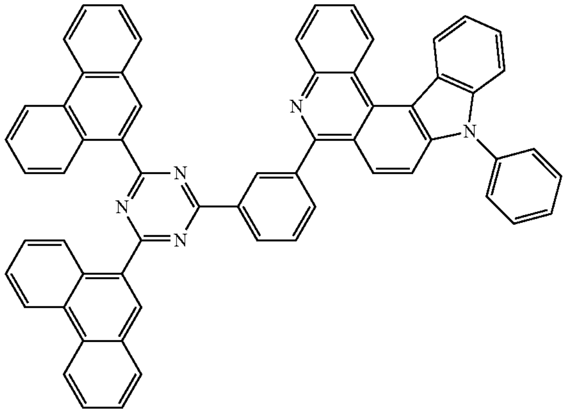

-continued
1-377
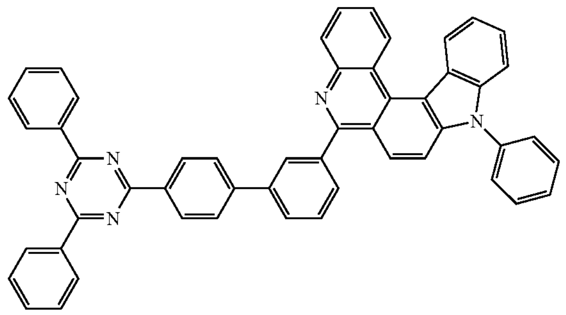
1-378
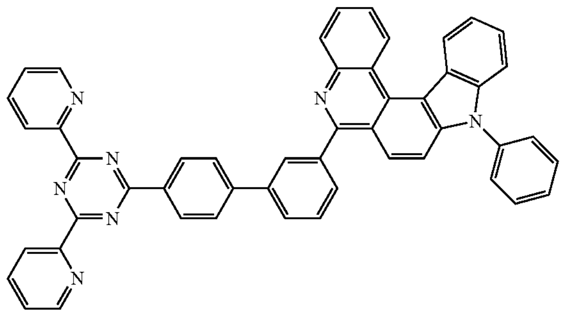
1-379
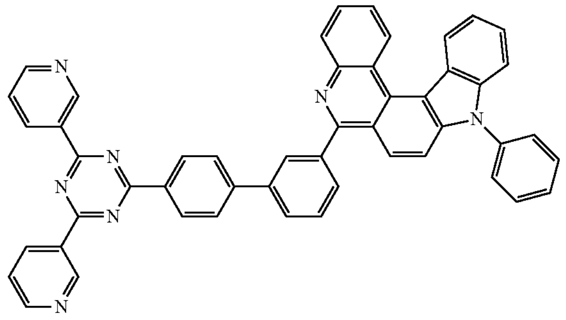
1-380
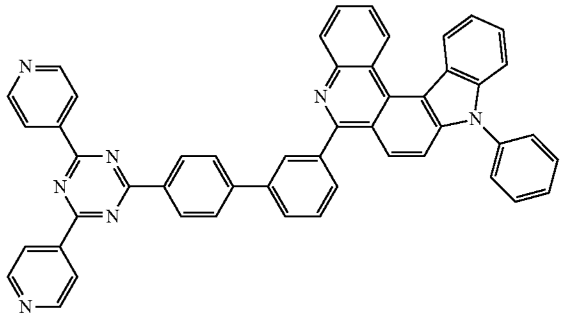
1-381
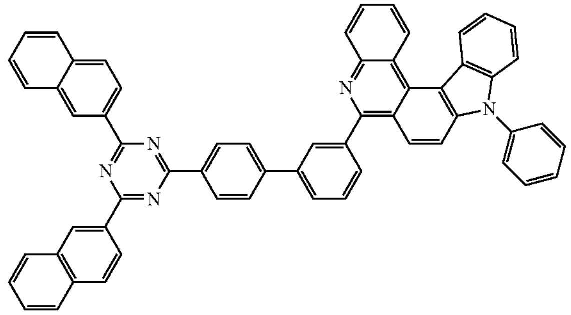
1-382
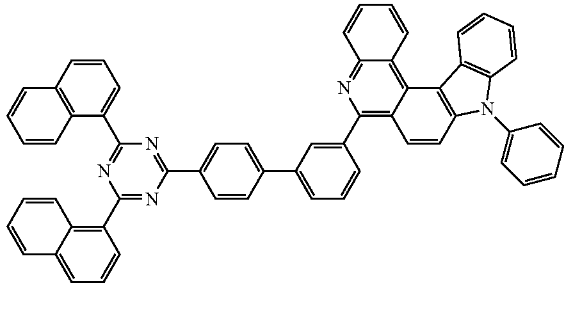
1-383
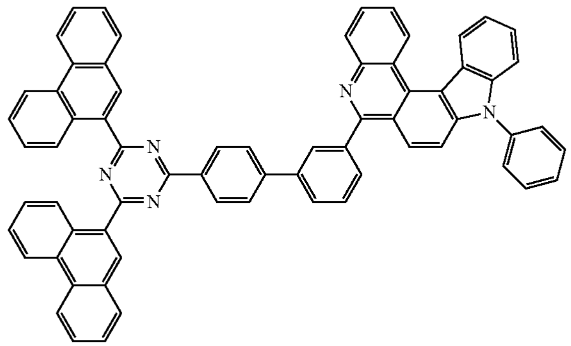
1-384
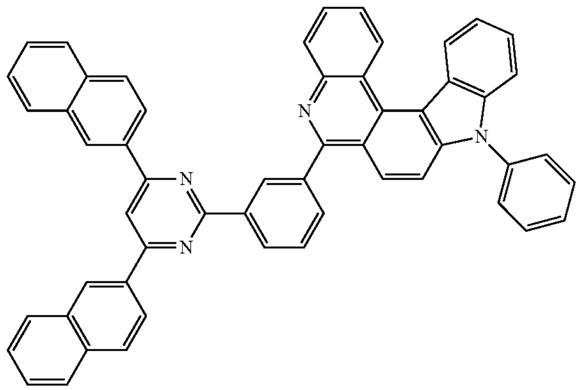

-continued
1-385
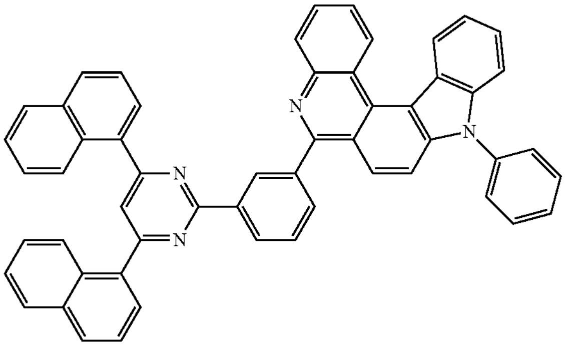
1-386
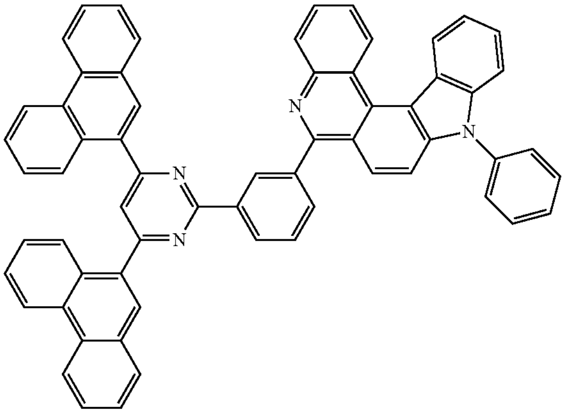
1-387
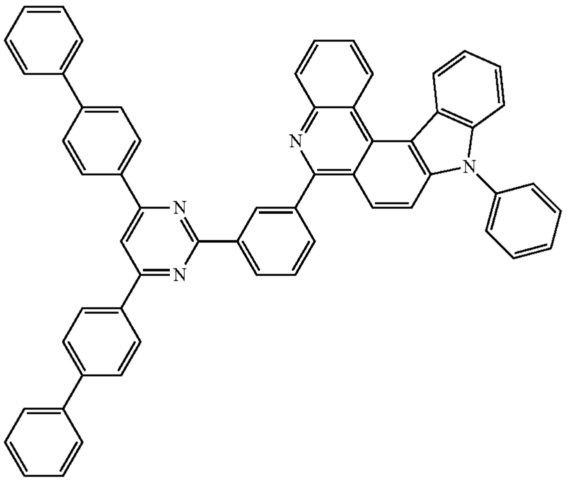
1-388
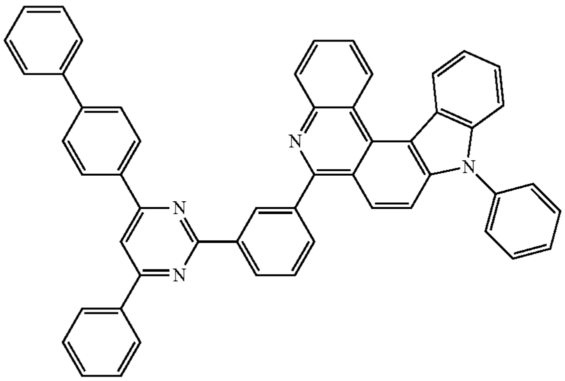
1-389
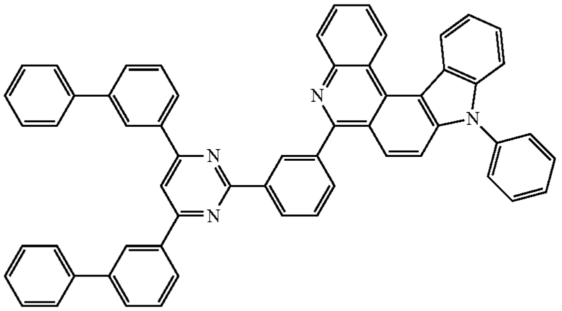
1-390
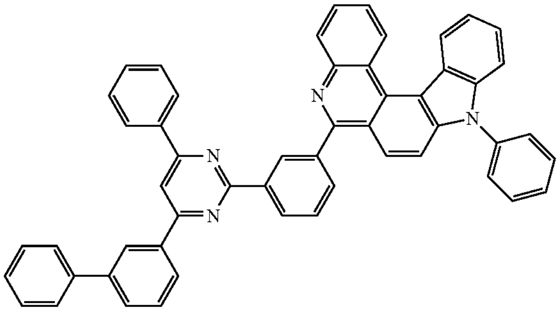
1-391
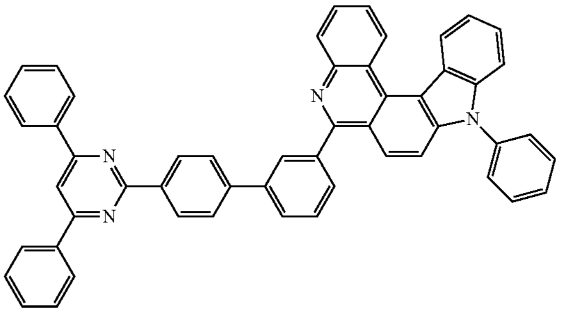
1-392
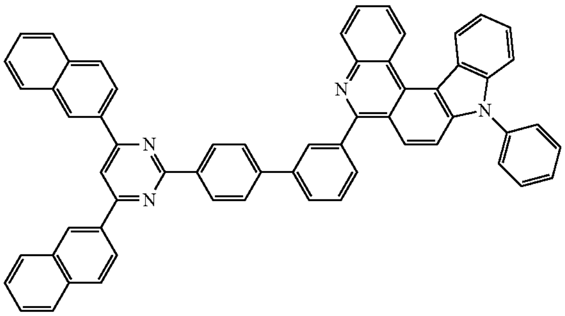

-continued
1-393
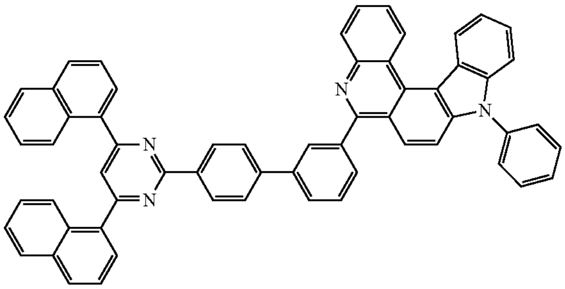
1-394
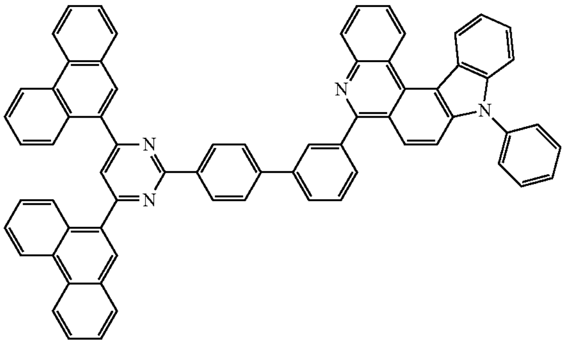
1-395
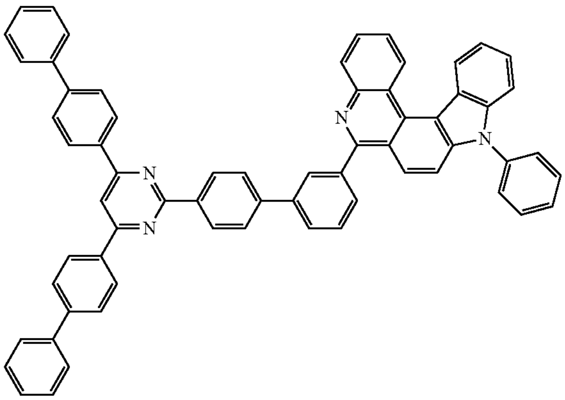
1-396
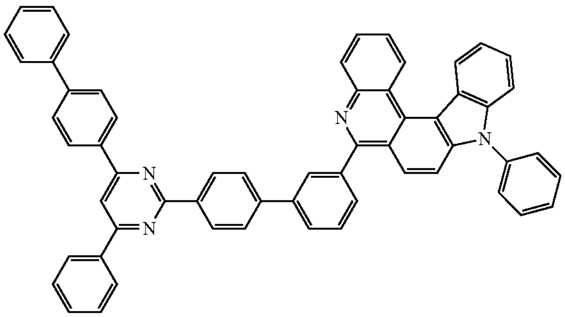
1-397
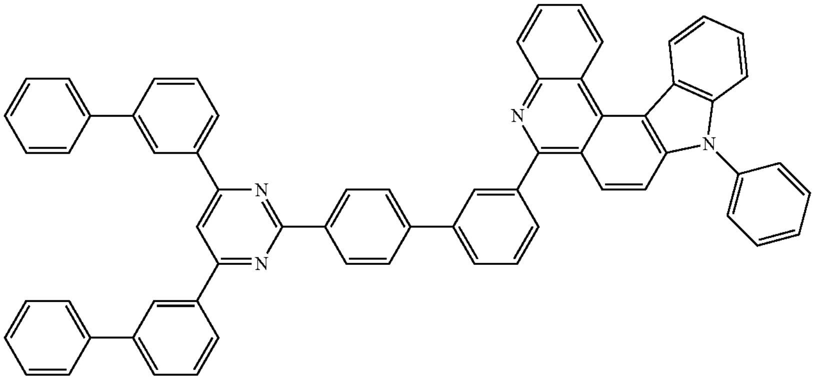
1-398
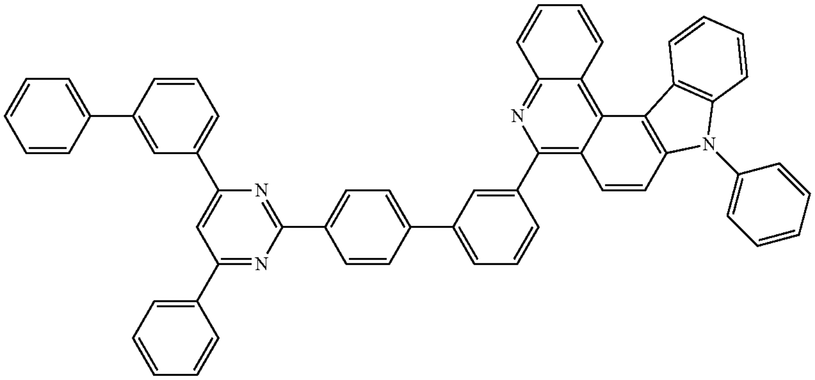

-continued
1-399
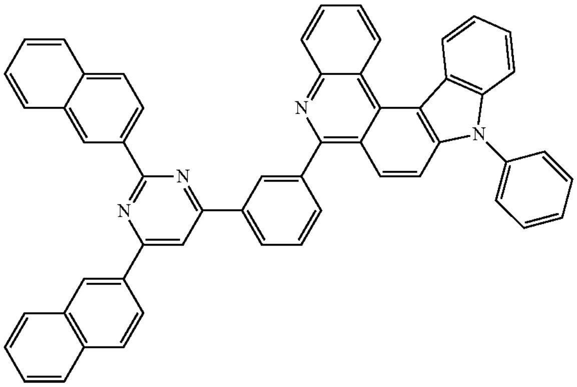
1-400
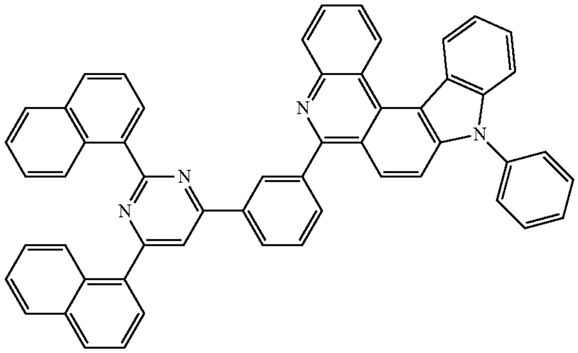
1-401
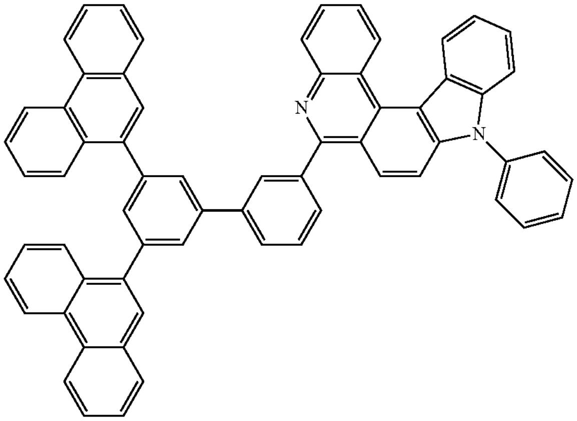
1-402
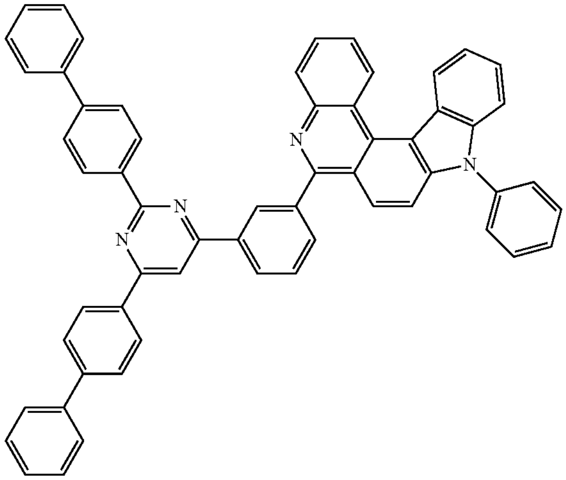
1-403
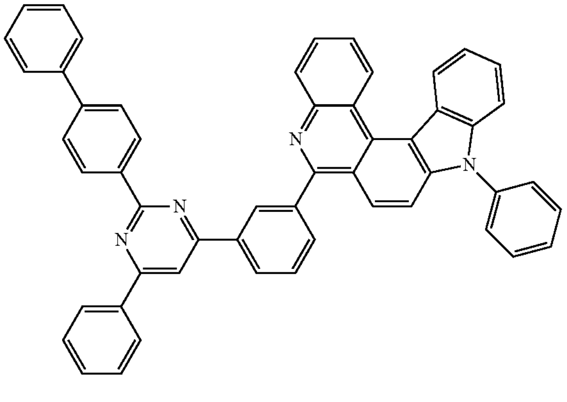
1-404
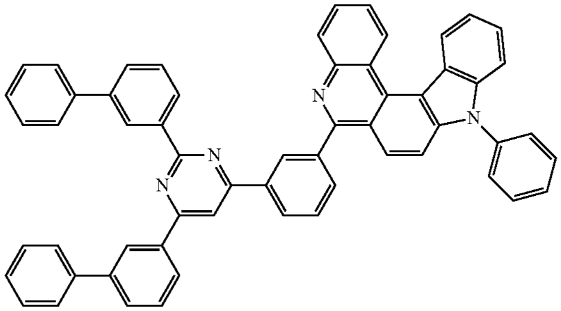

-continued
1-405
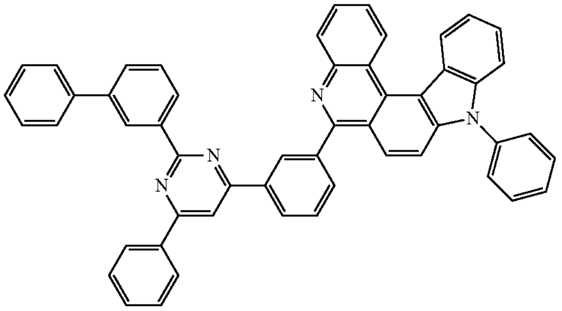
1-406
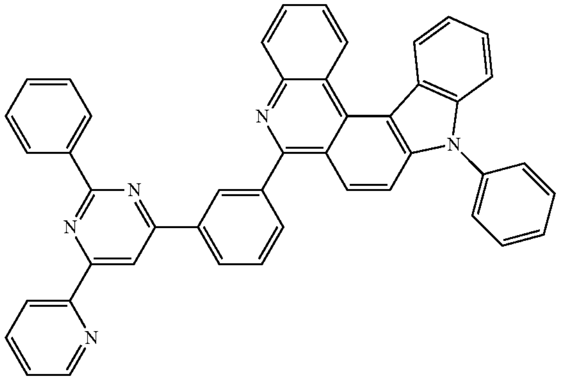
1-407
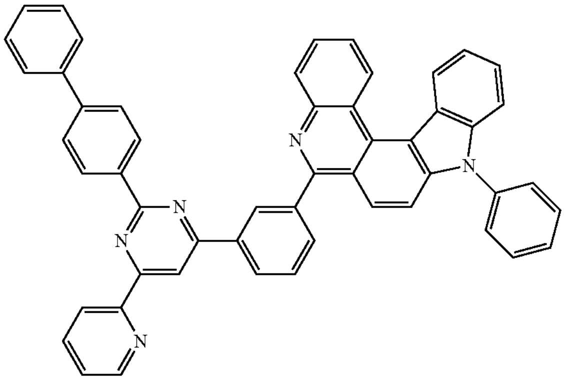
1-408
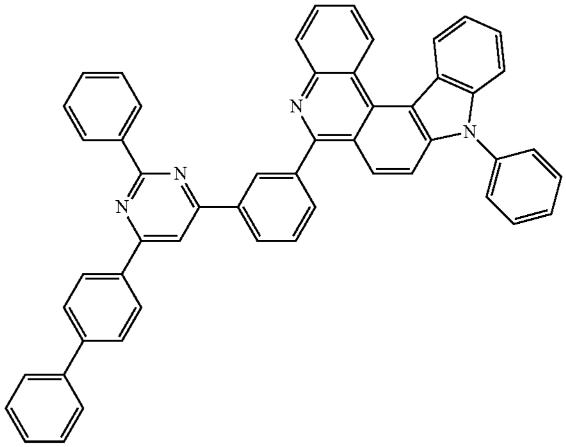
1-409
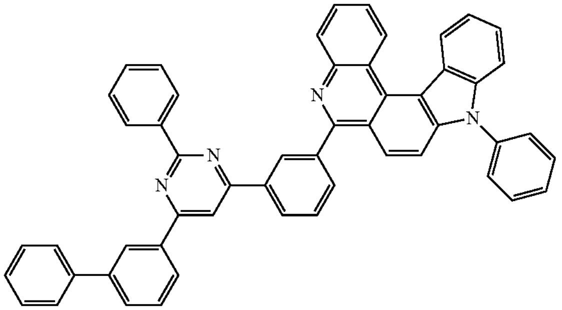
1-410
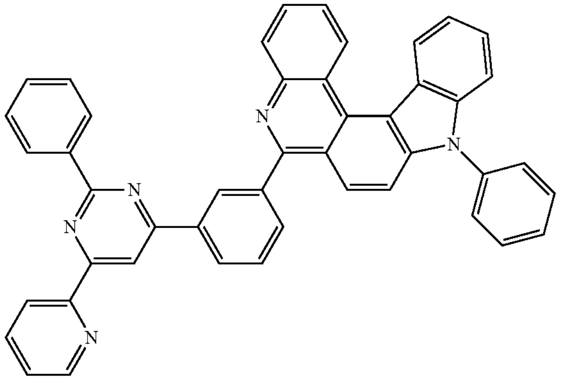
1-411
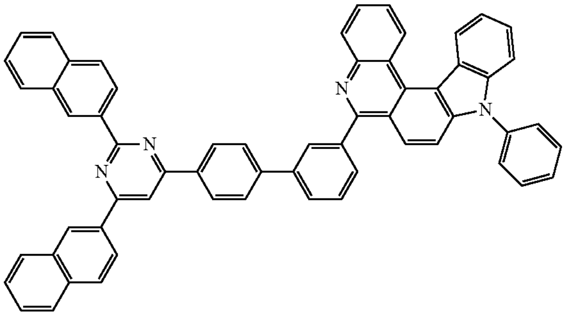
1-412
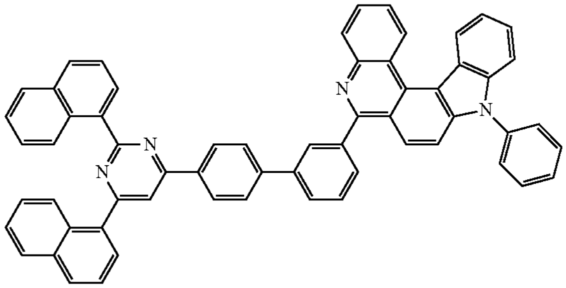

-continued
1-413
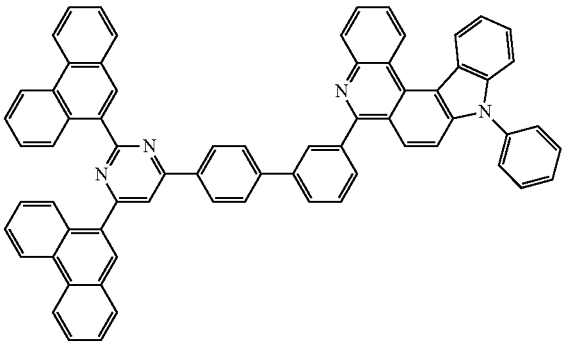
1-414
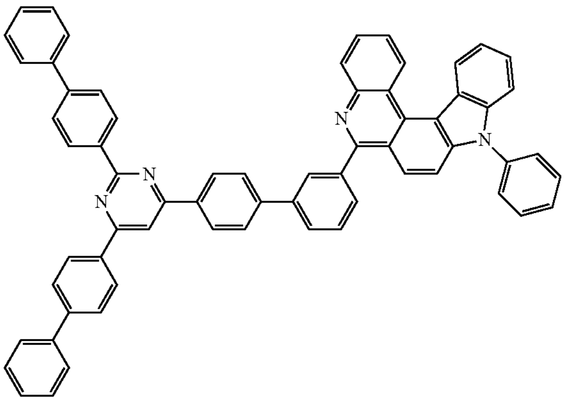
1-415
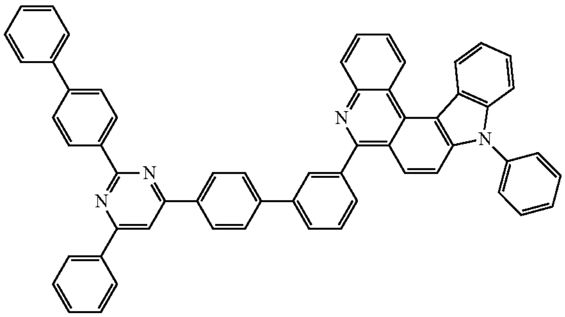
1-416
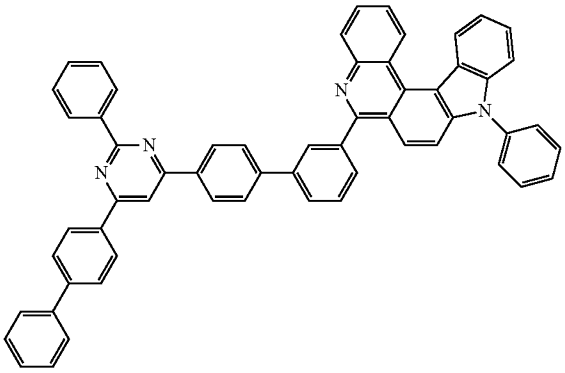
1-417
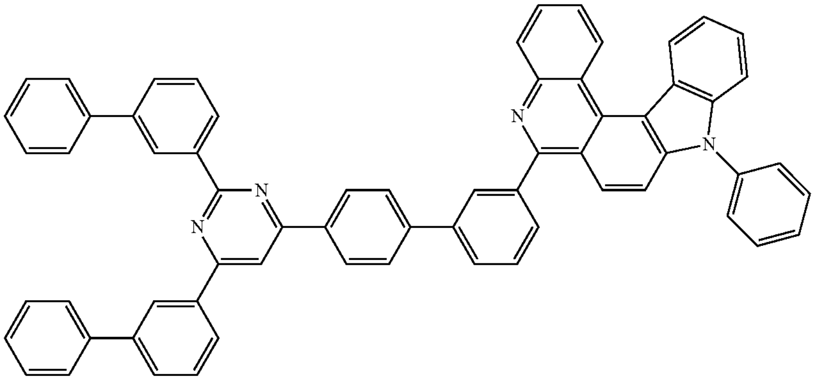
1-418
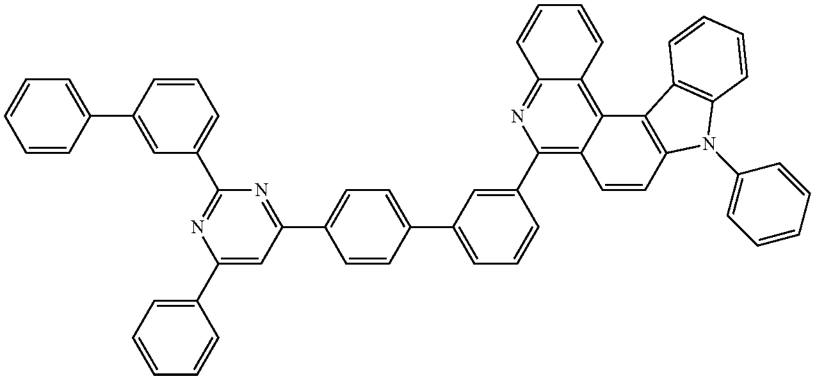

-continued
1-419
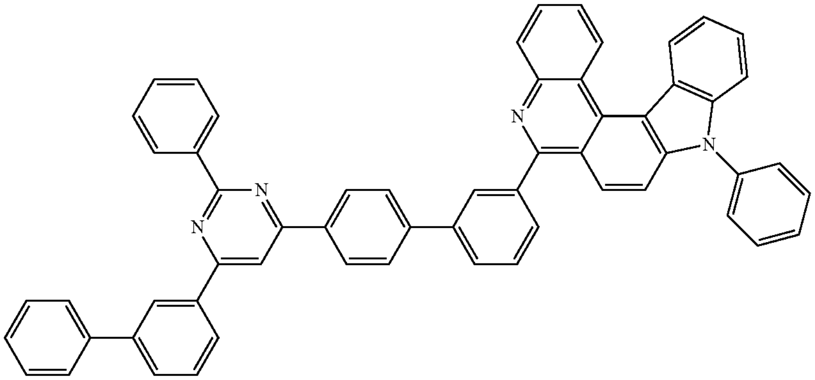
1-420
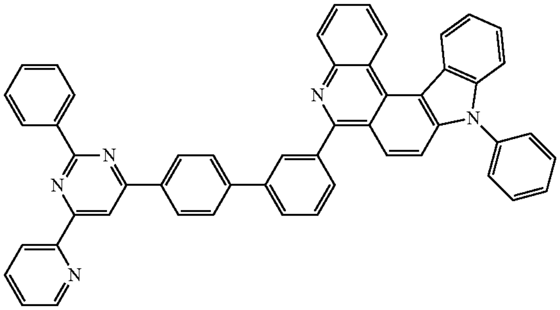
1-421
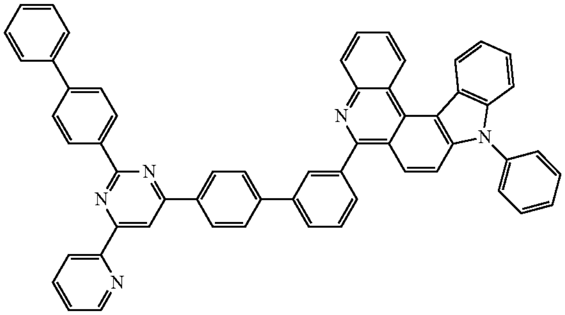
1-422
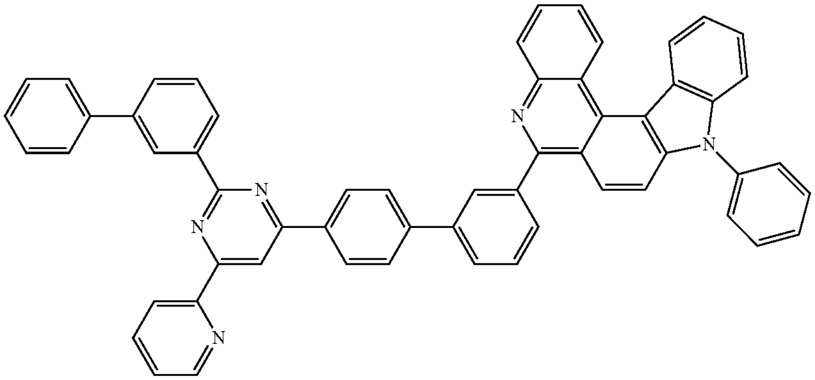
1-423
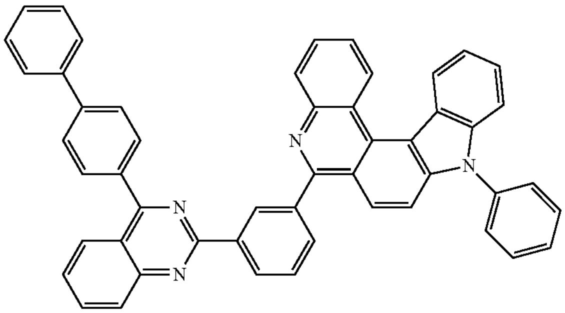
1-424
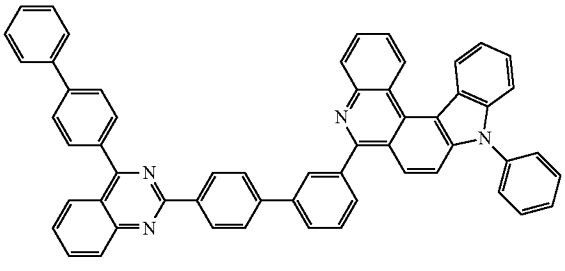

-continued
1-425
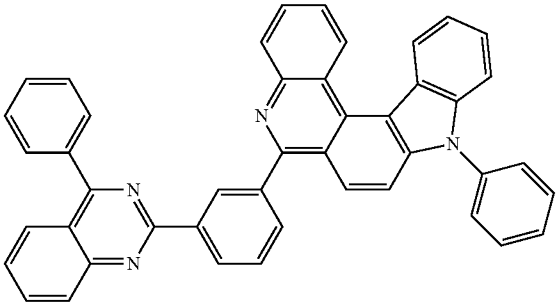
1-426
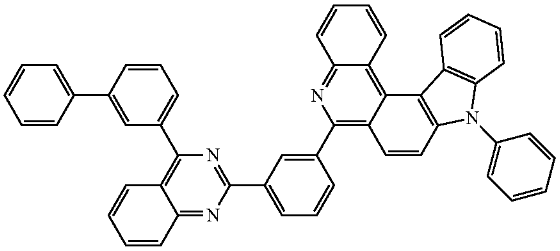
1-427
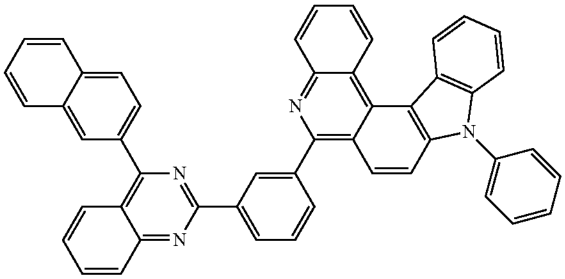
1-428
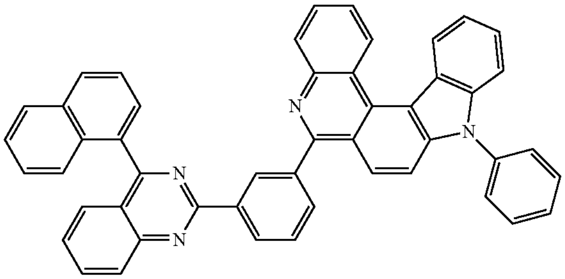
1-429
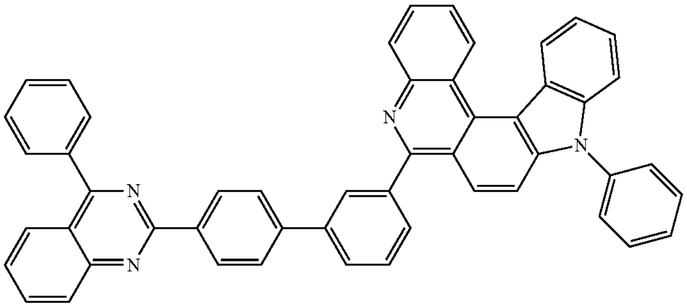
1-430
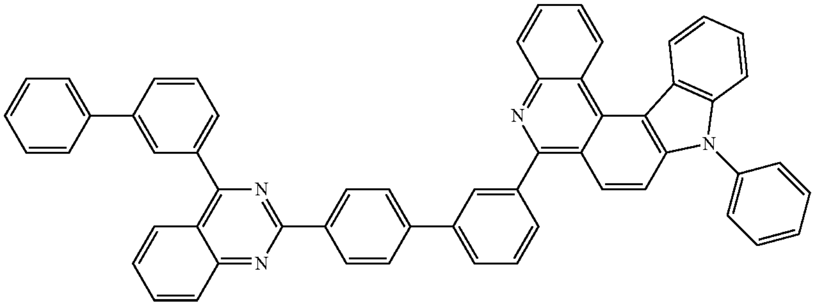
1-431
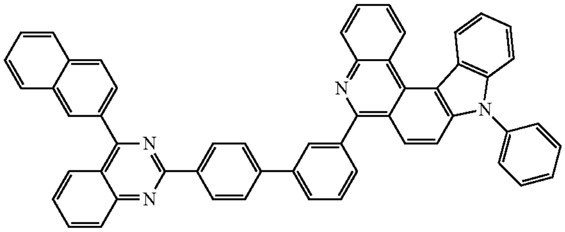
1-432
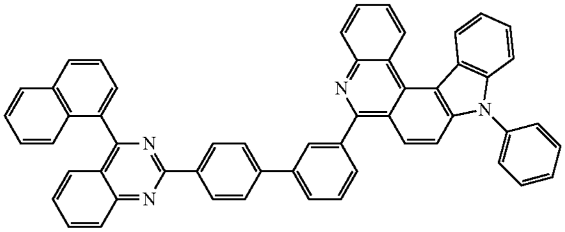

-continued
1-433
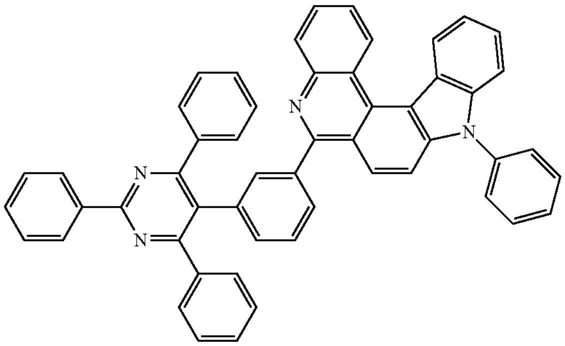
1-434
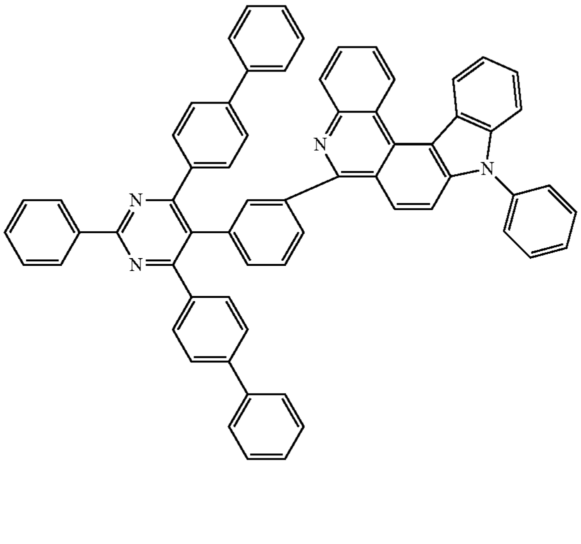
1-435
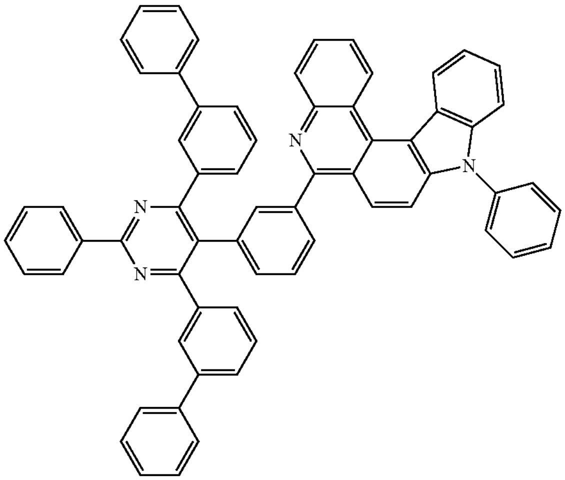
1-436
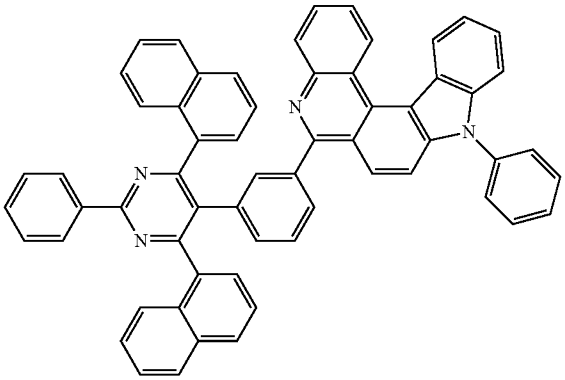
1-437
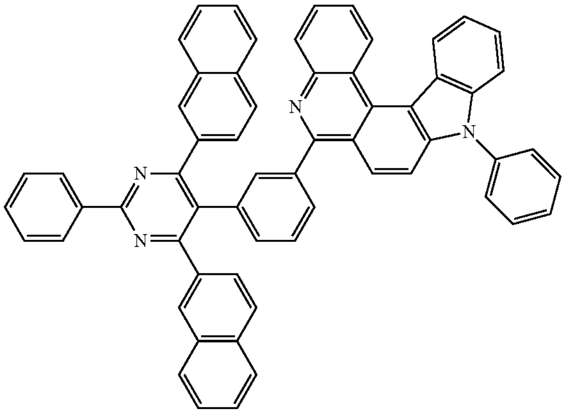
1-438
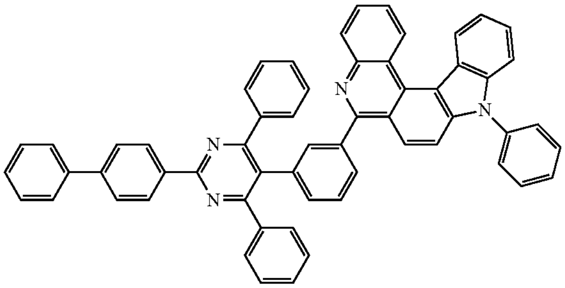

-continued
1-439
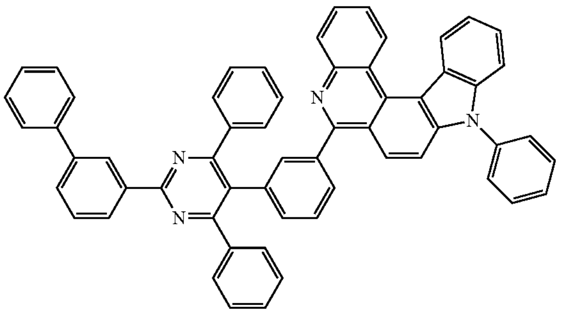
1-440
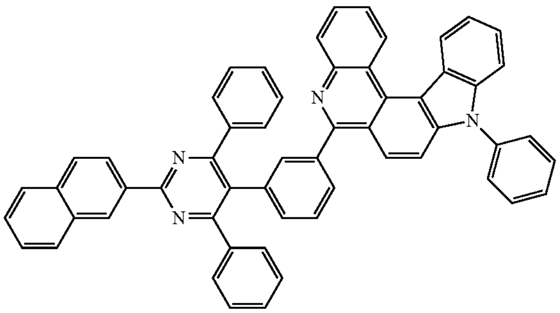
1-441
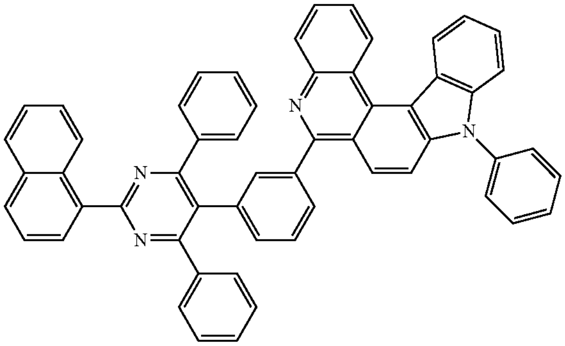
1-442
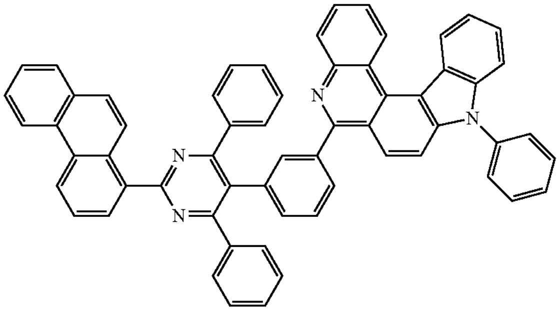
1-443
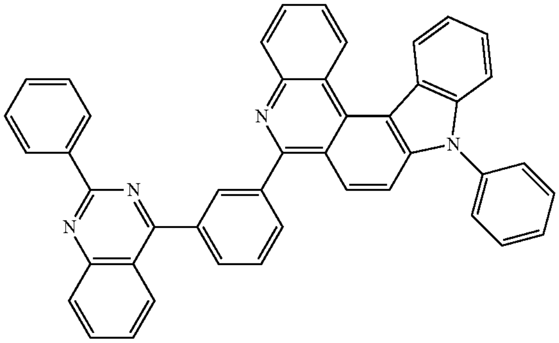
1-444
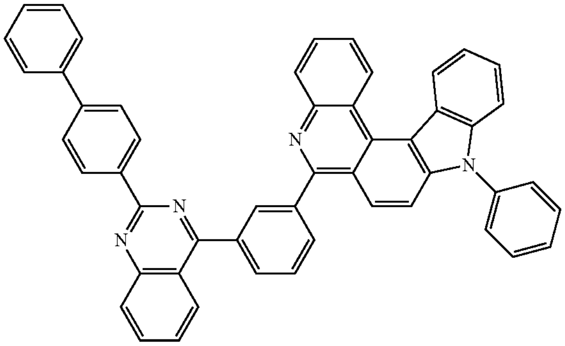
1-445
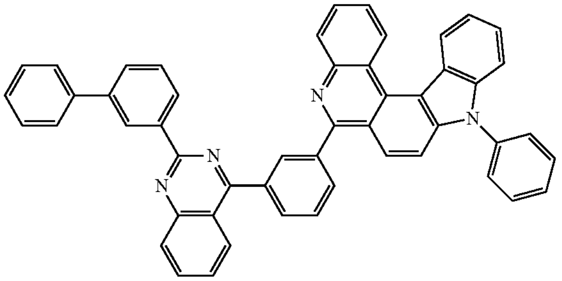
1-446
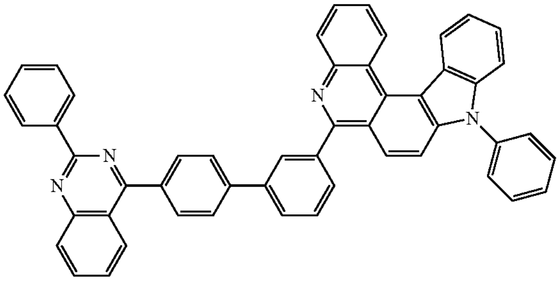

-continued
1-447
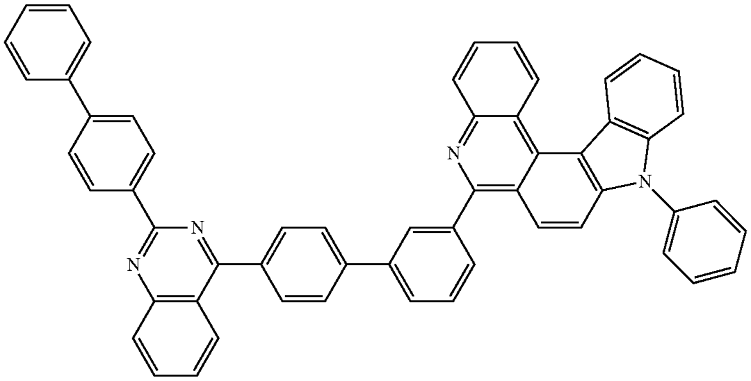
1-448
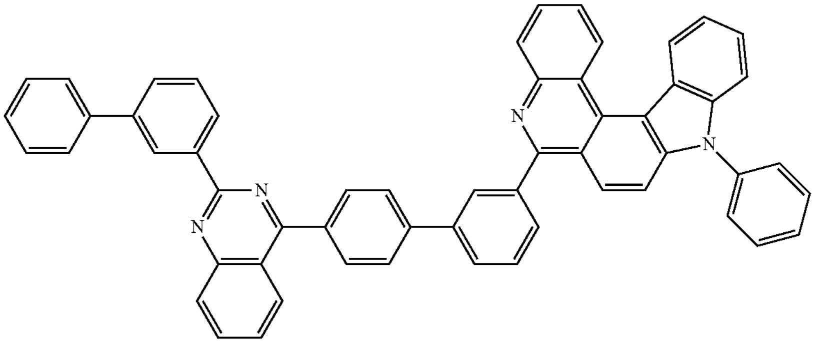
1-449
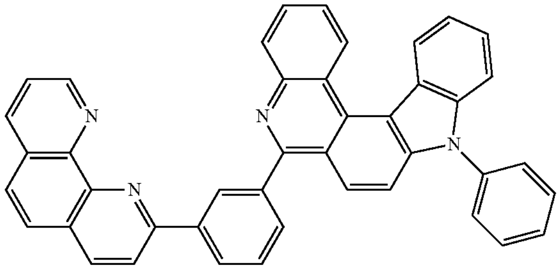
1-450
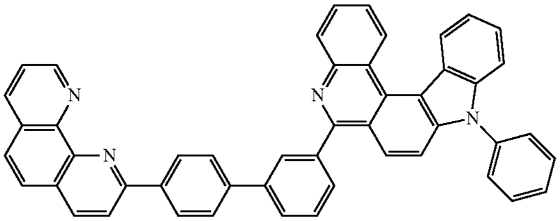
1-451
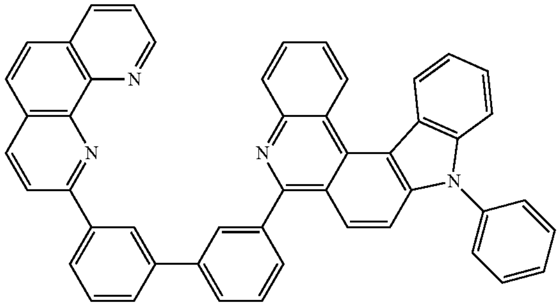
1-452
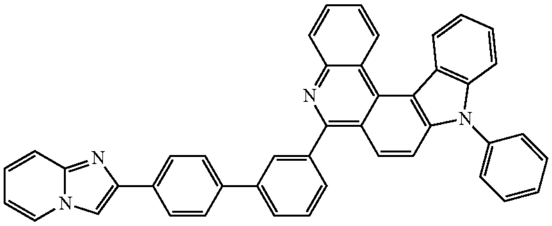
1-453
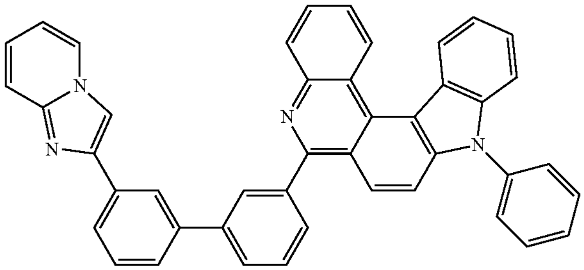
1-454
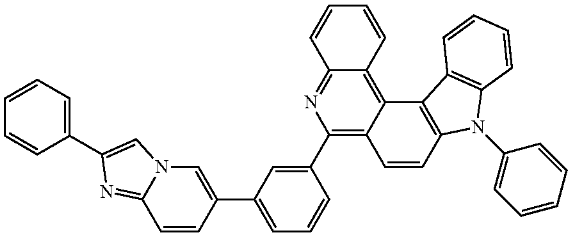

-continued
1-455
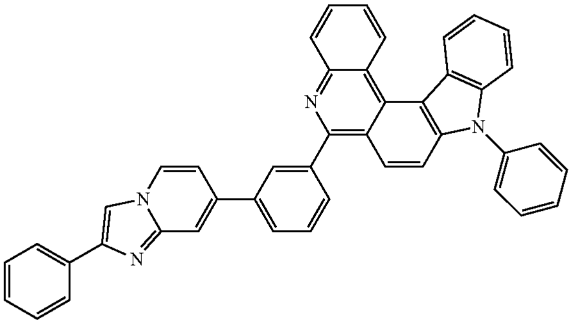
1-456
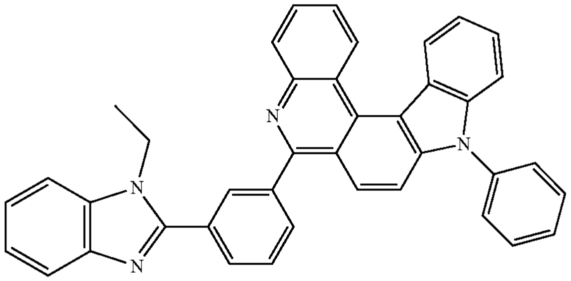
1-457
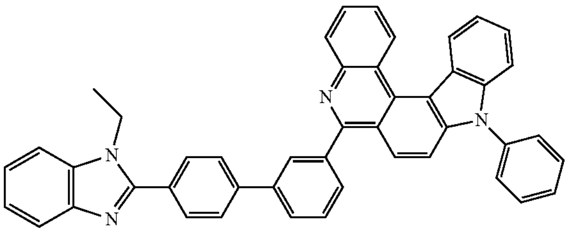
1-458
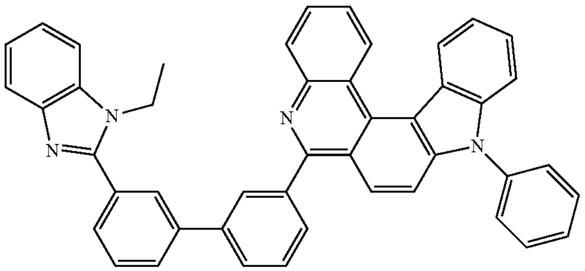
1-459
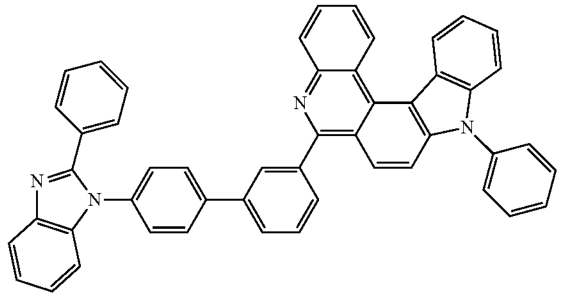
1-460
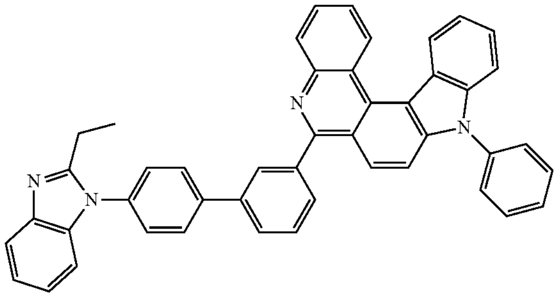
1-461
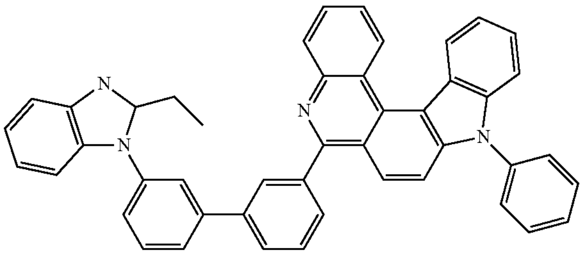
1-462
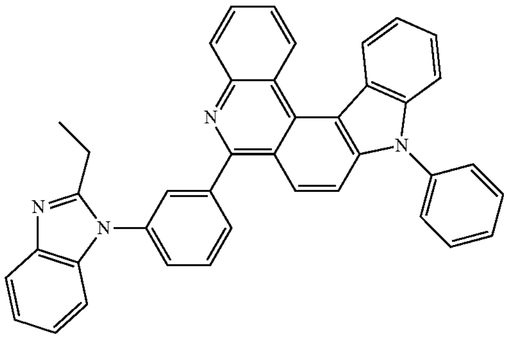
1-463
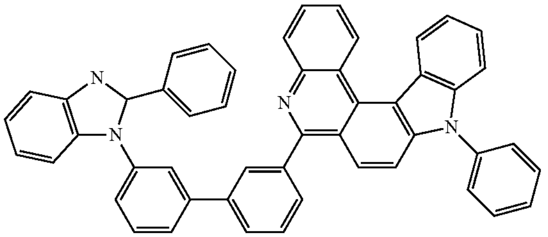
1-464
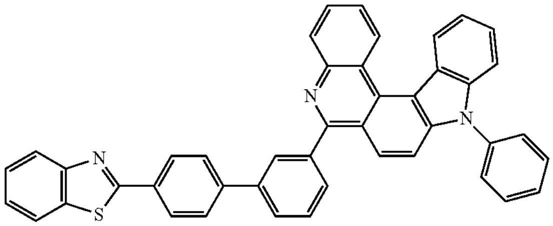

-continued
1-465
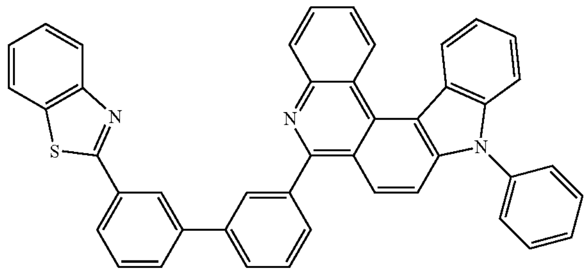
1-466
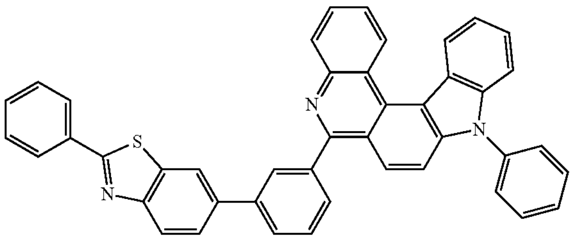
1-467
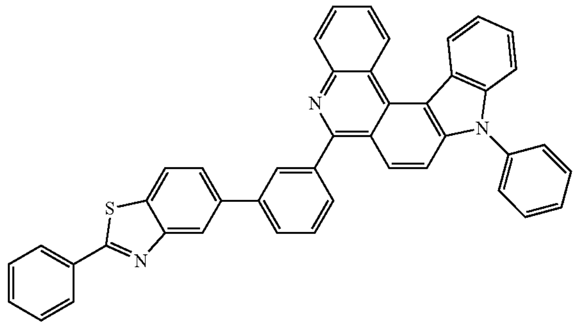
1-468
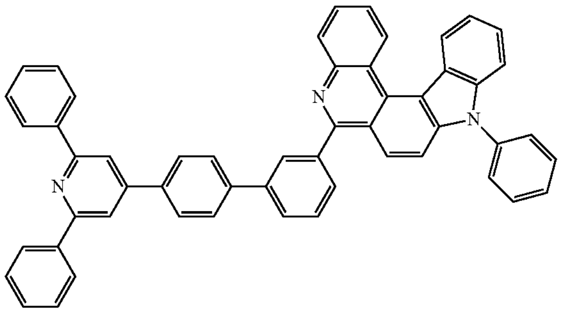
1-469
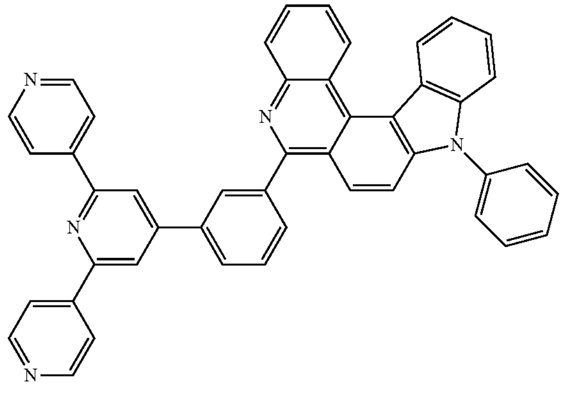
1-470
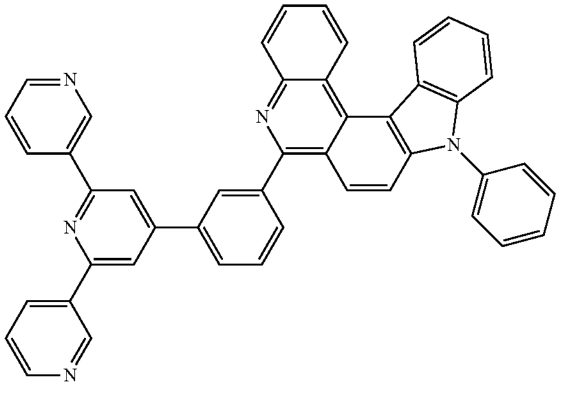
1-471
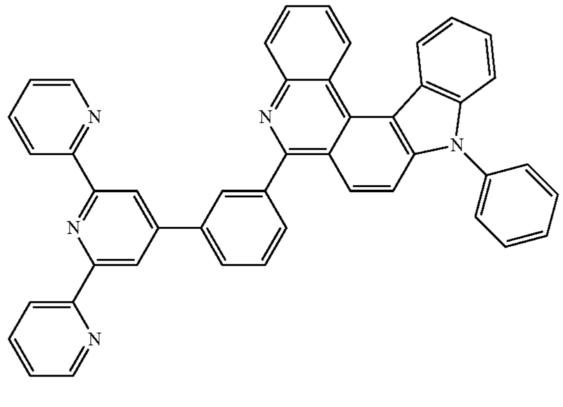
1-472
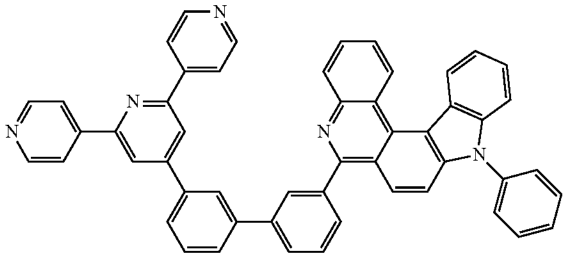

-continued
1-473
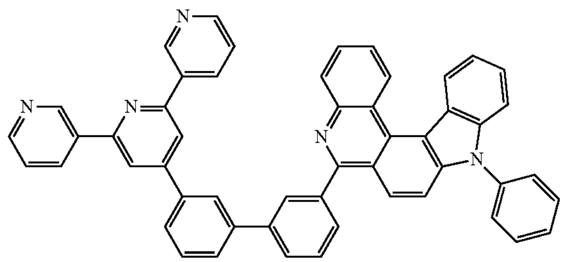
1-474
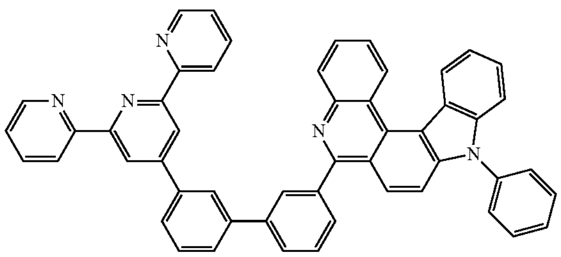
1-475
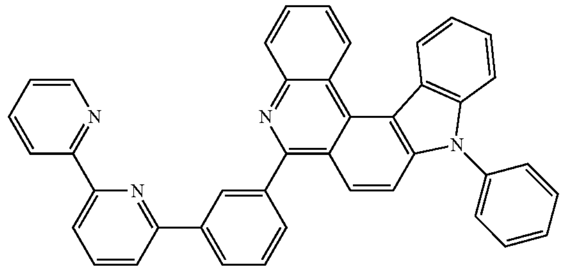
1-476
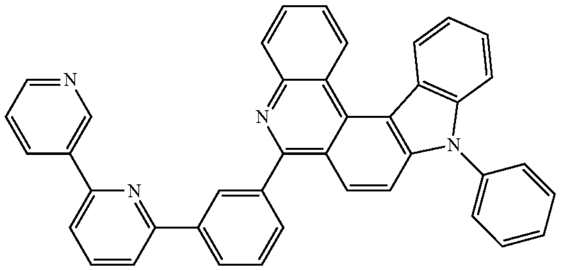
1-477
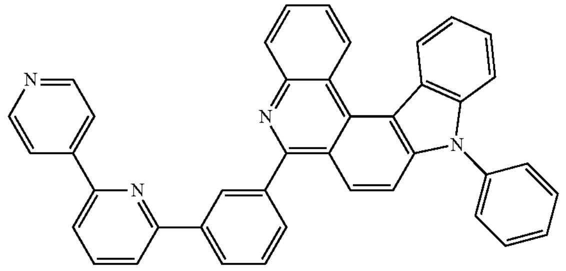
1-478
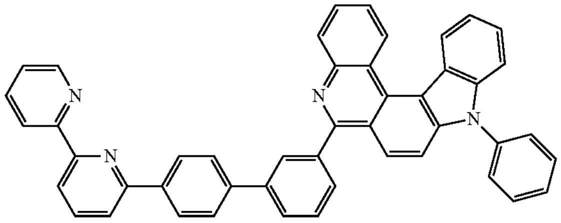
1-479
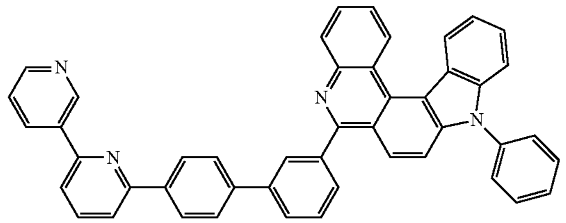
1-480
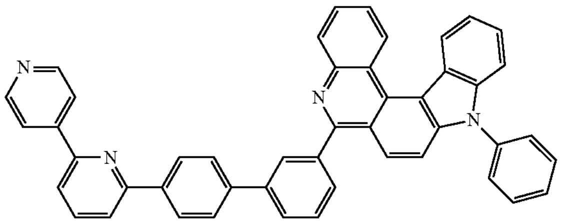
1-181
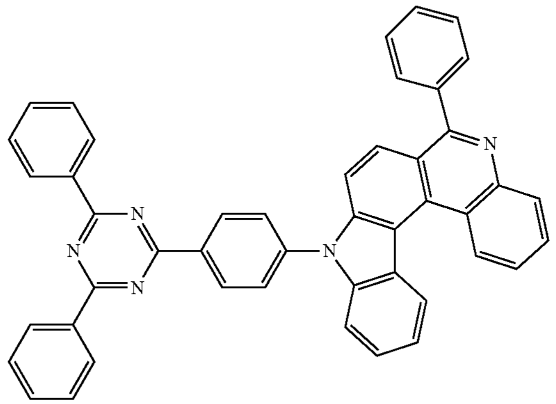
1-182
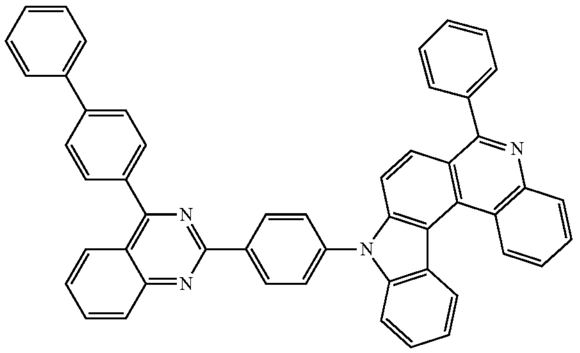

-continued
1-183
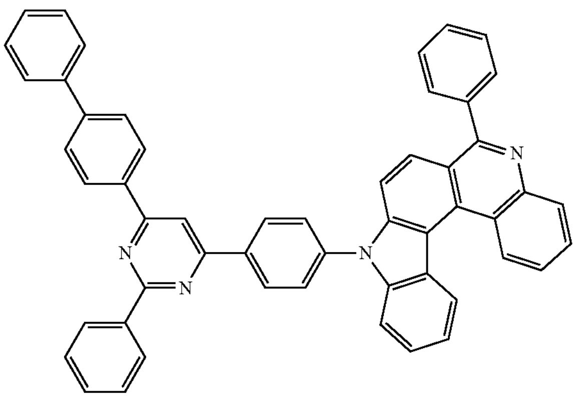
1-184
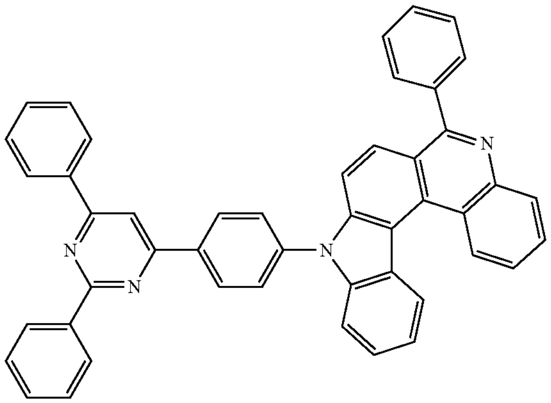
1-185
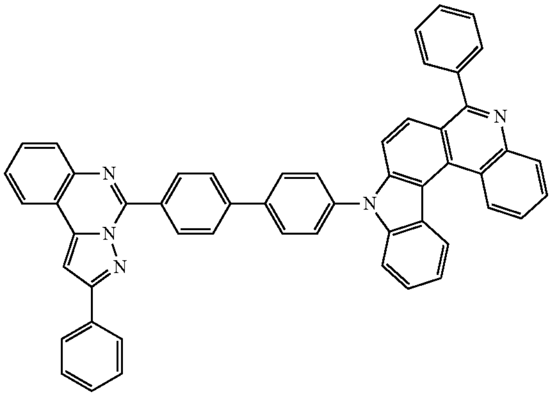
1-186
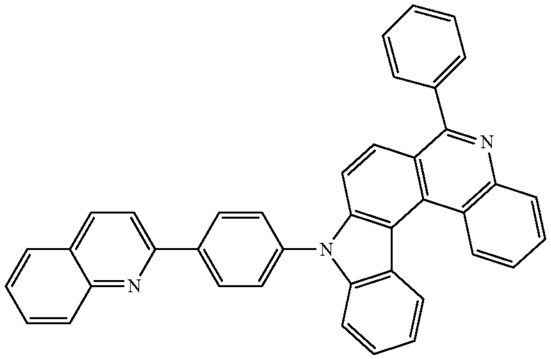
1-187
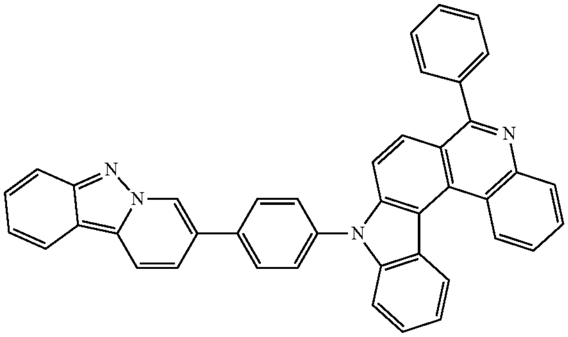
1-188
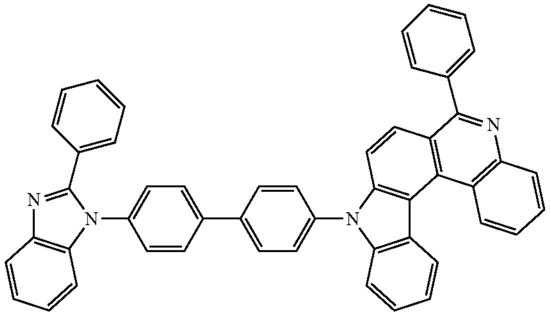
1-189
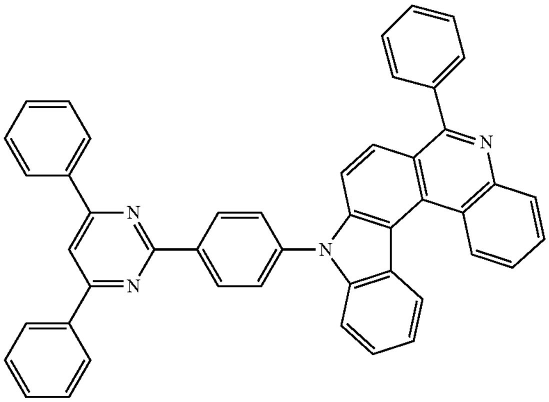
1-190
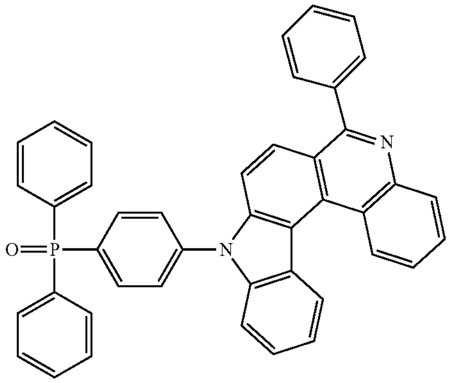

-continued
1-191
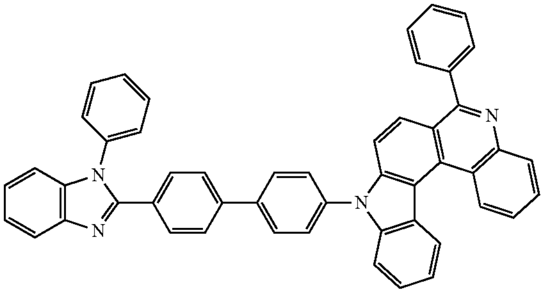
1-192
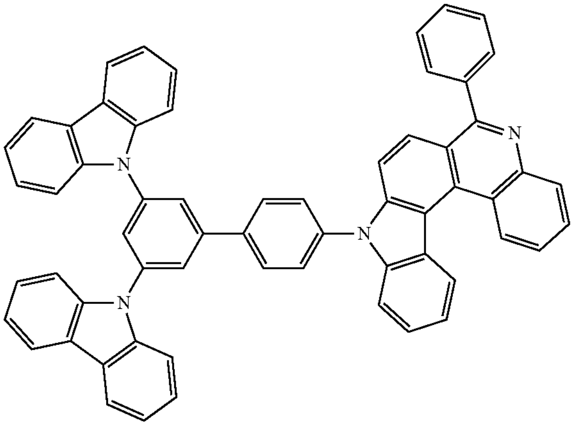
1-193
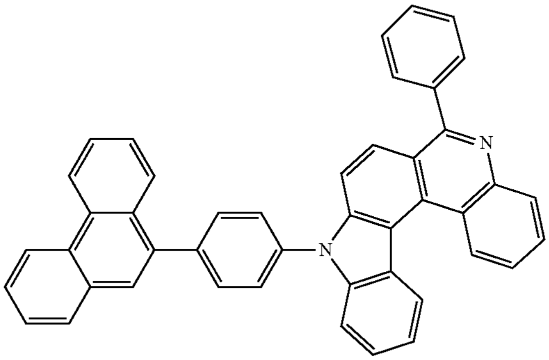
1-194
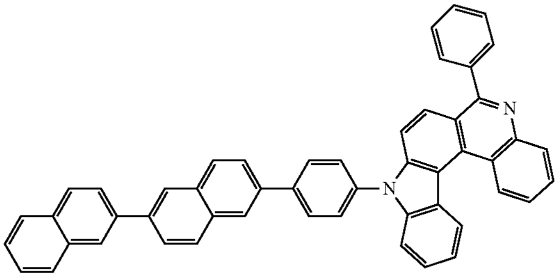
1-195
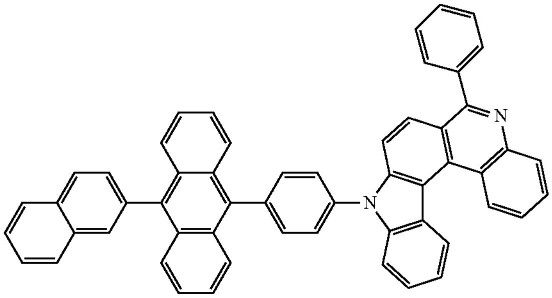
1-196
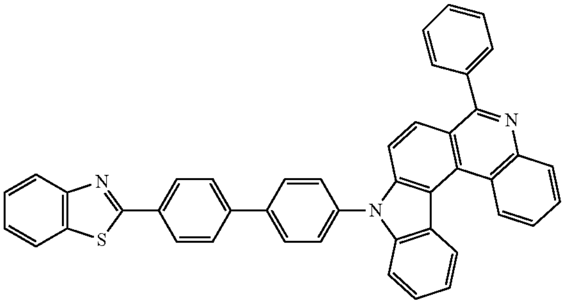
1-197
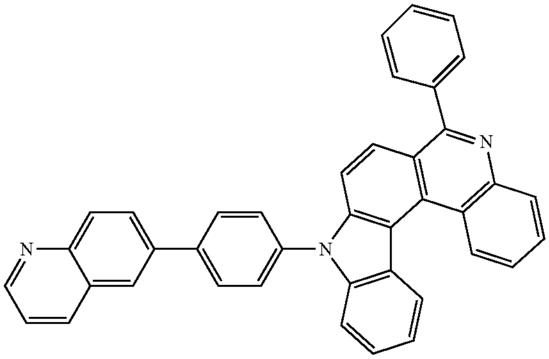
1-198
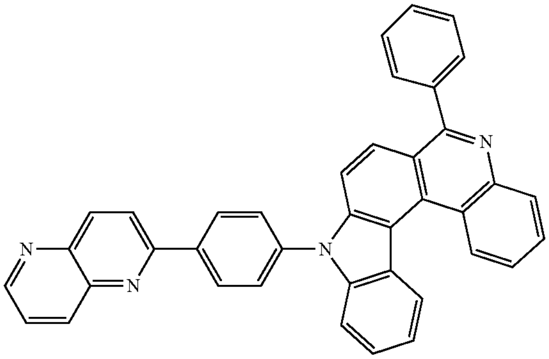

-continued
1-199
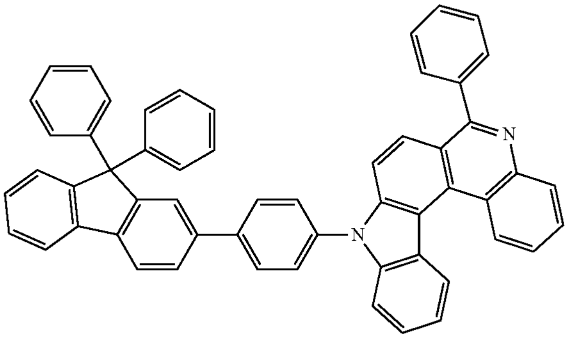
1-200
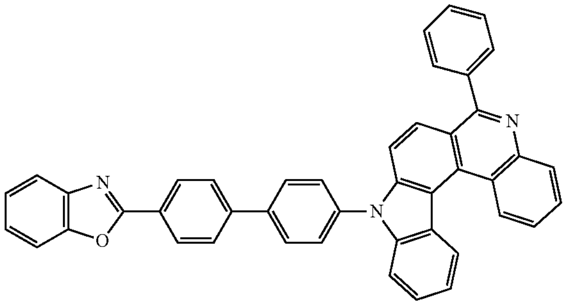
1-201
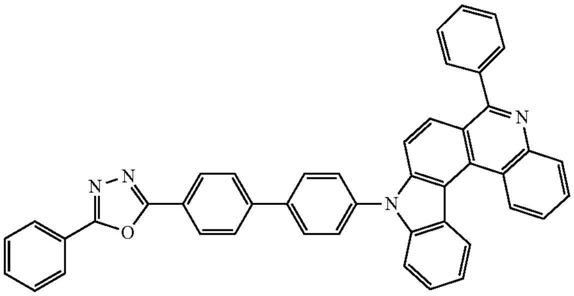
1-202
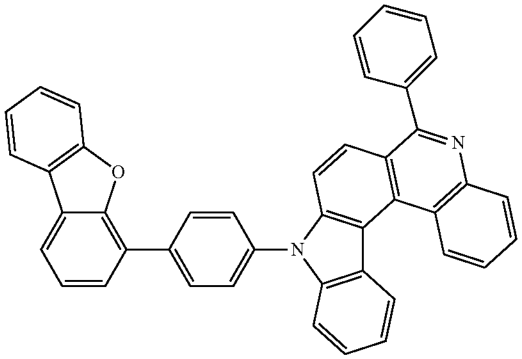
1-203
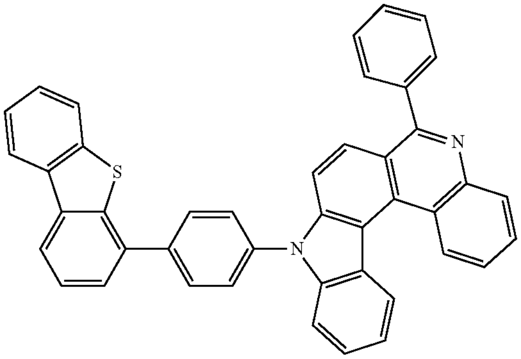
1-204
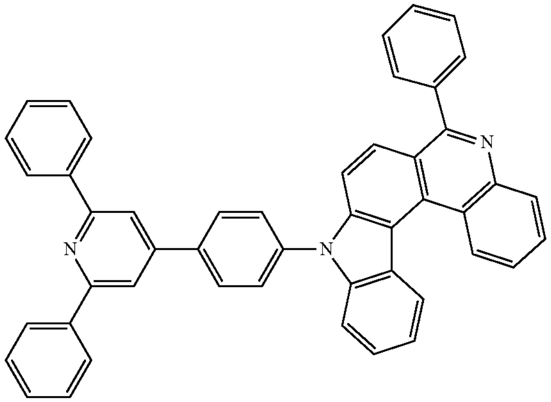

-continued
1-205
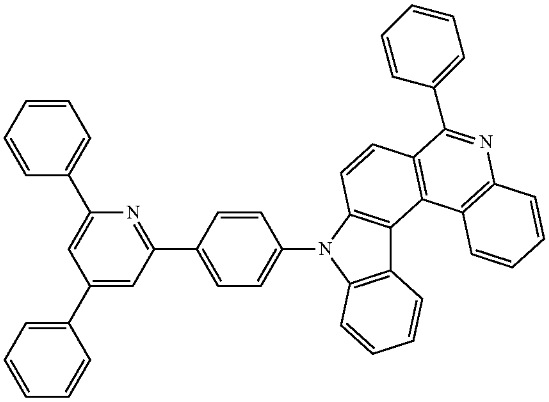
1-206
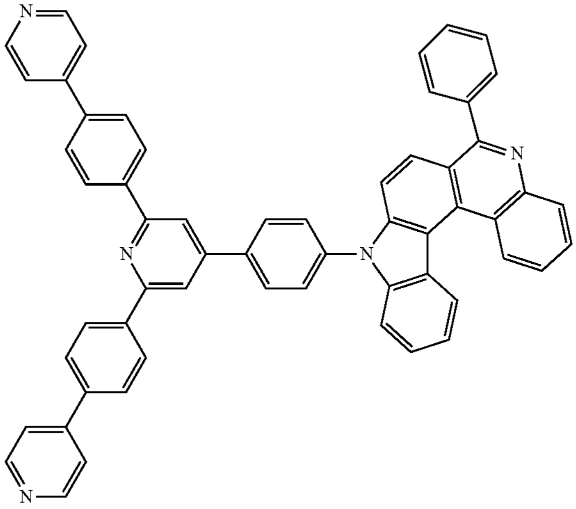
1-207
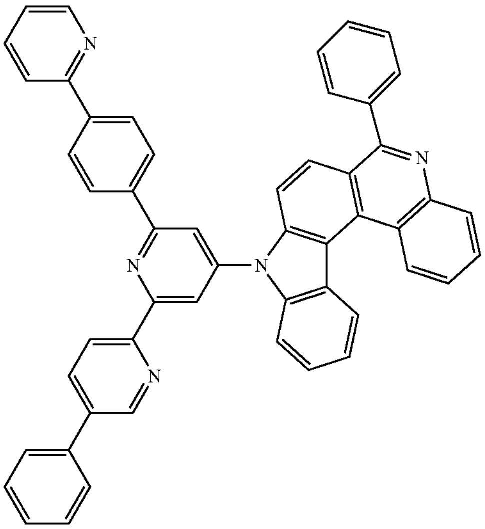
1-208
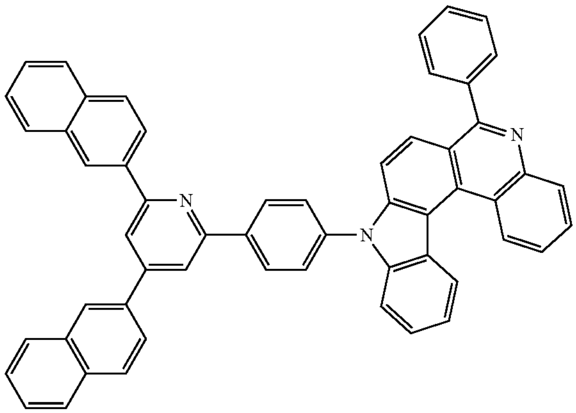
1-209
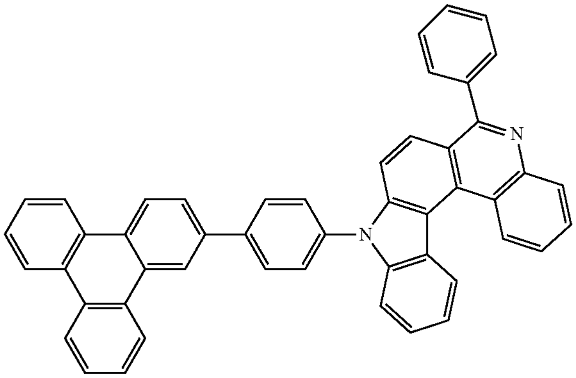
1-210
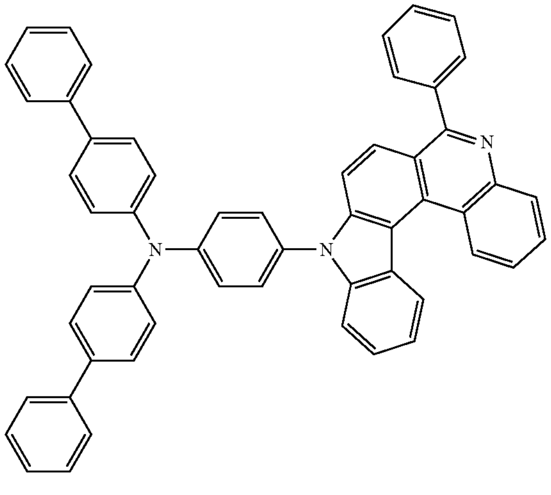

-continued
1-211
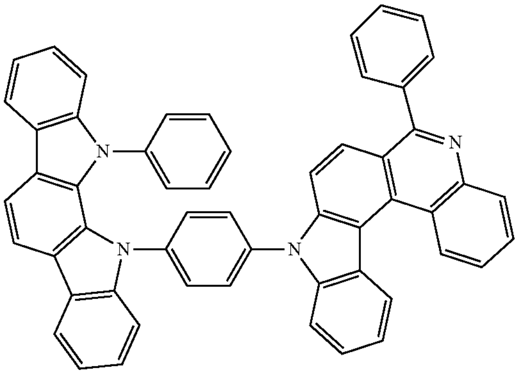
1-212
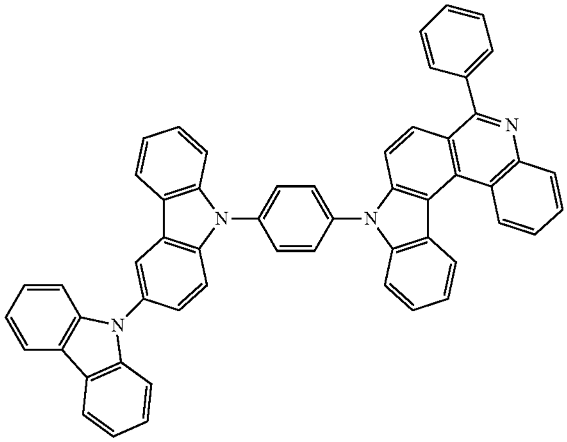
1-213
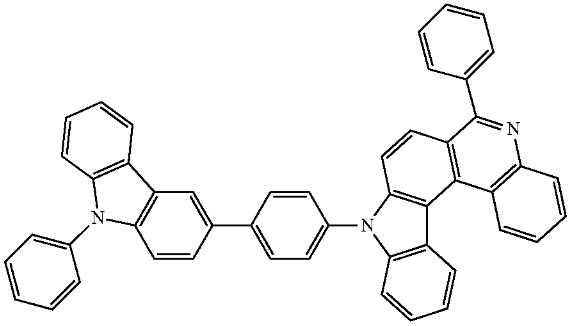
1-214
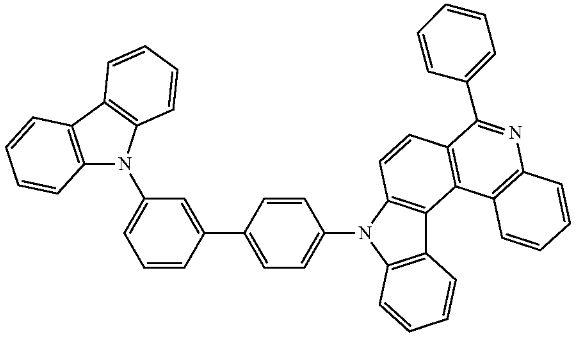
1-215
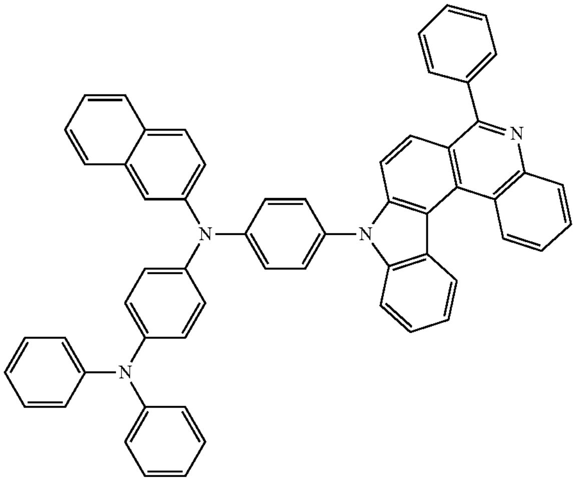
1-481
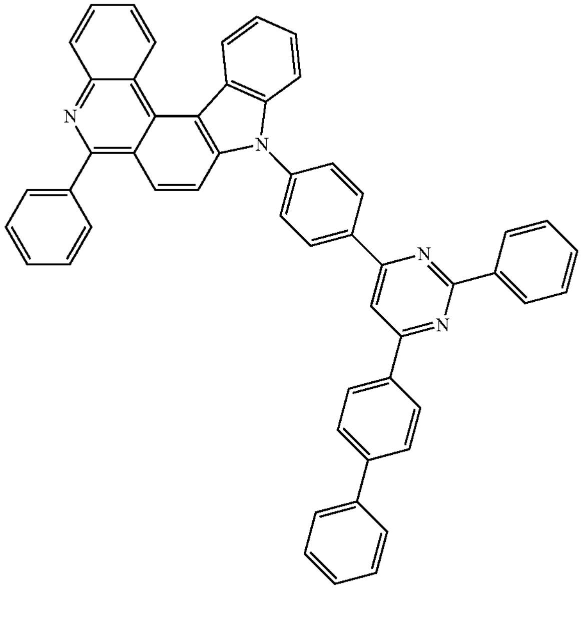

-continued
1-482
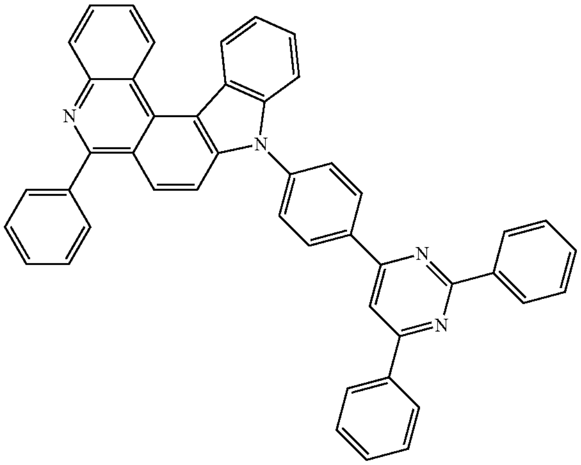
1-483
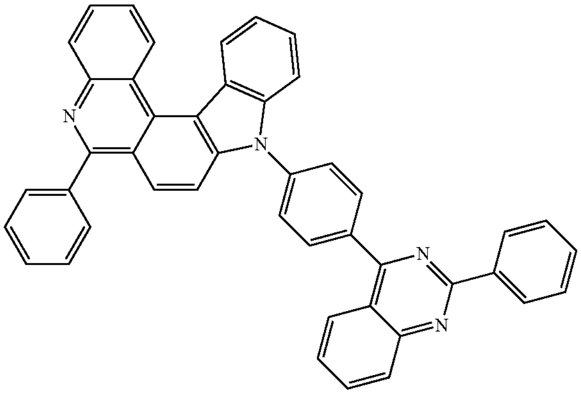
1-484
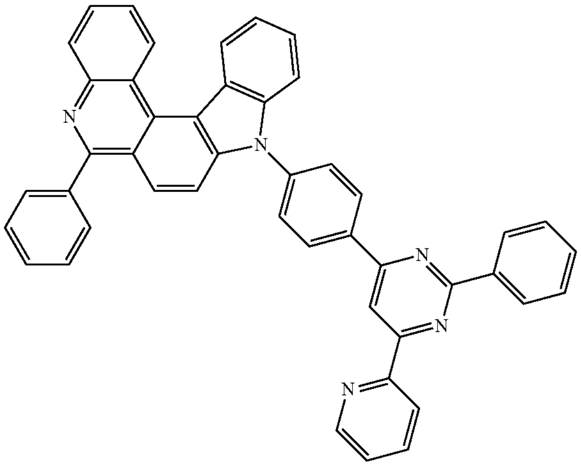
1-485
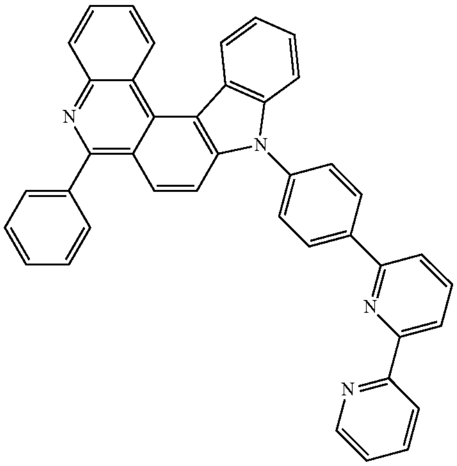
1-486
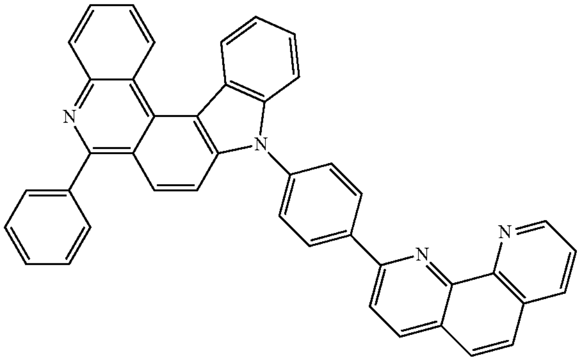
1-487
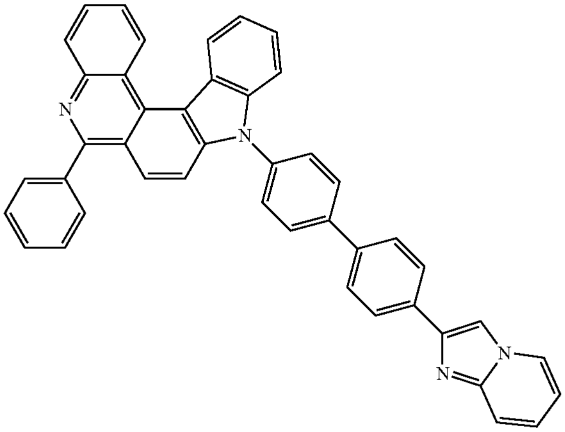

-continued
1-216
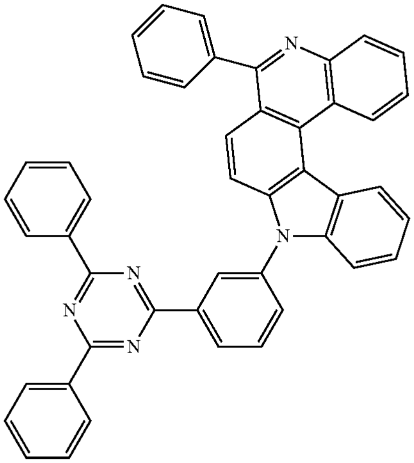
1-217
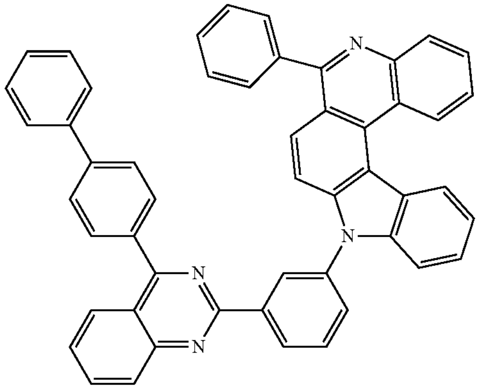
1-218
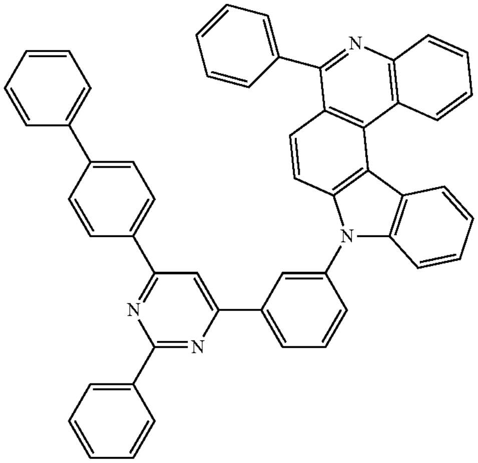
1-219
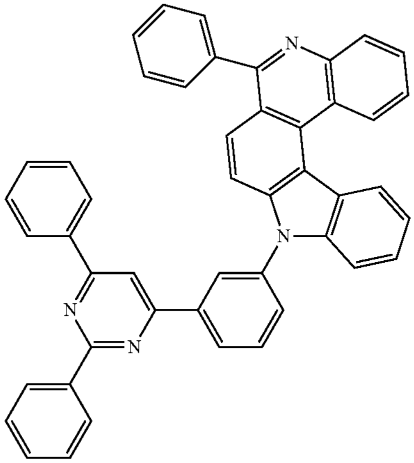
1-220
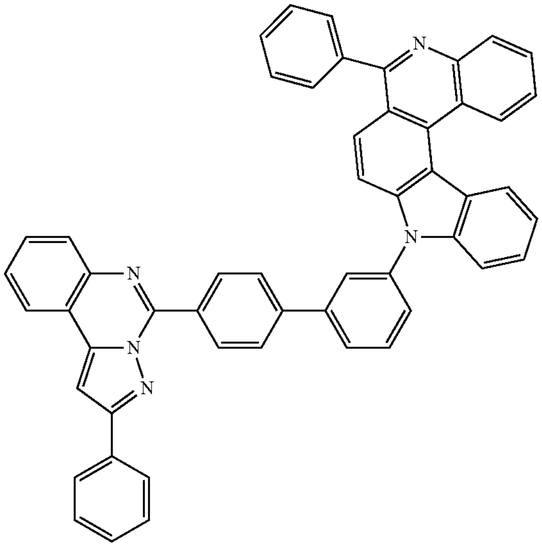
1-221
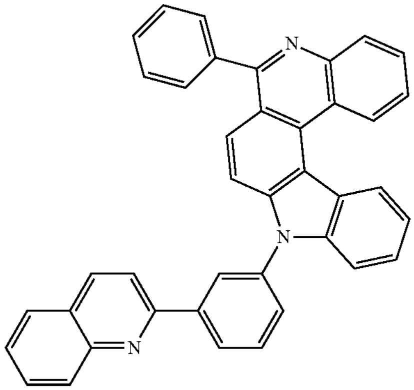

-continued
1-222
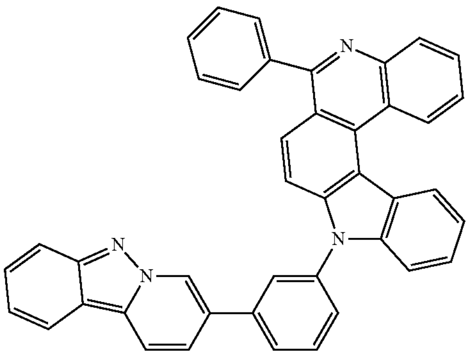
1-223
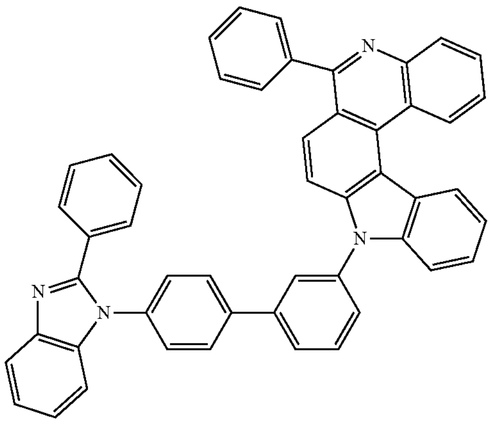
1-224
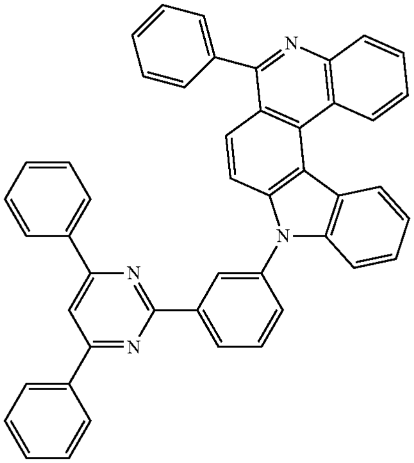
1-225
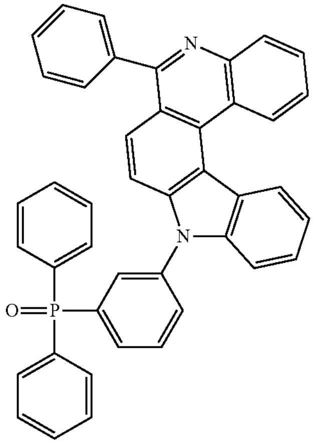
1-226
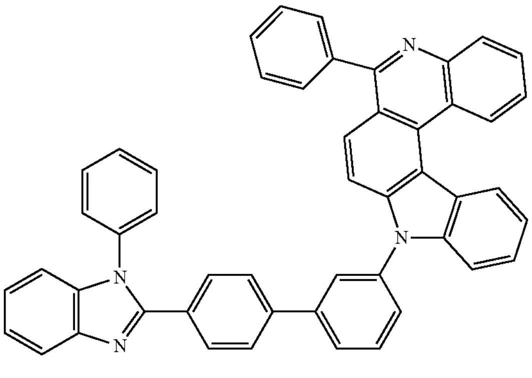
1-227
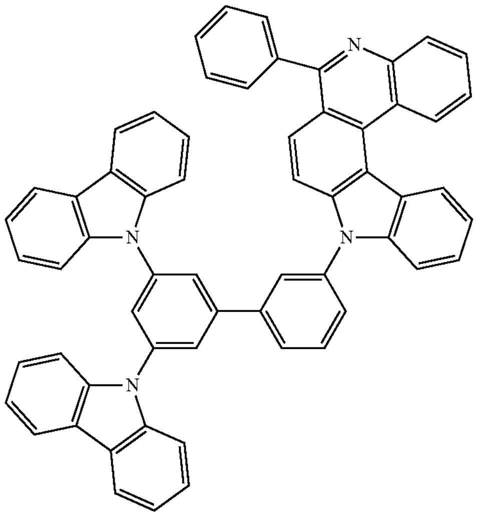

-continued
1-228
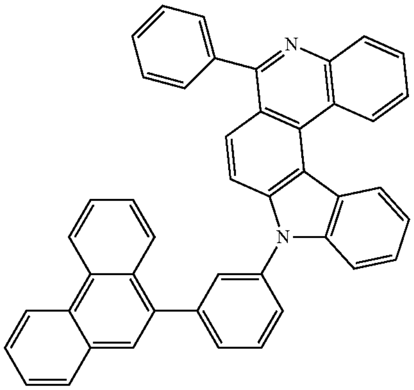
1-229
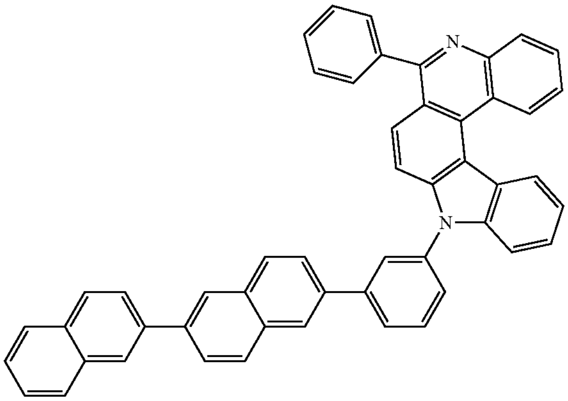
1-230
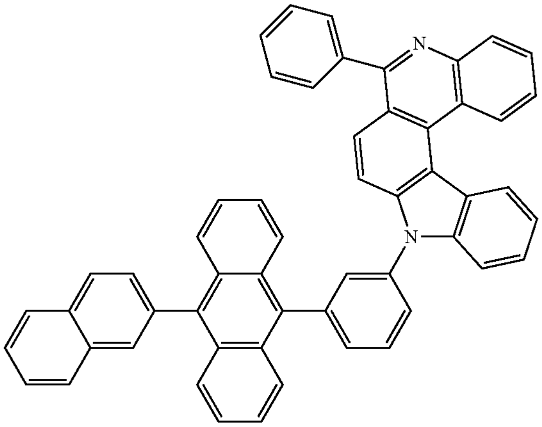
1-231
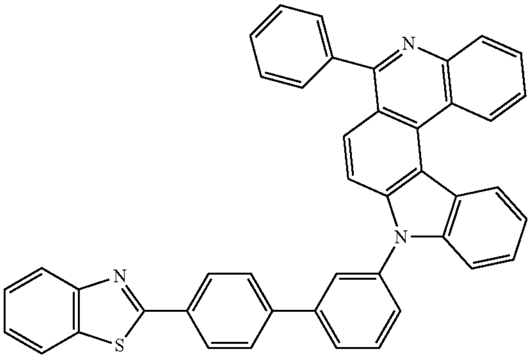
1-232
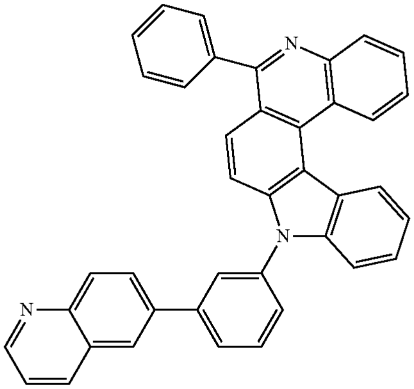
1-233
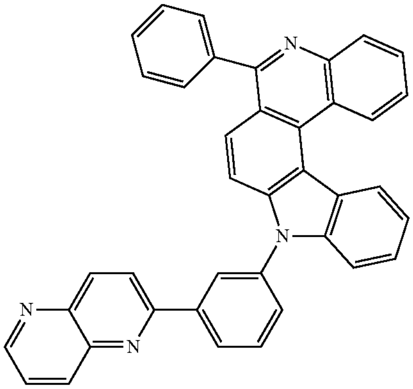
1-234
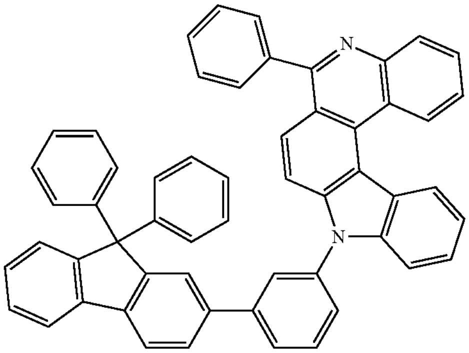
1-235
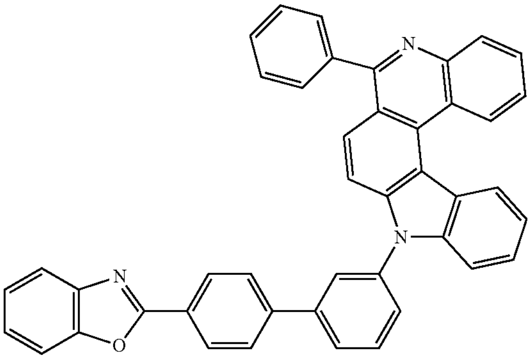

-continued
1-236
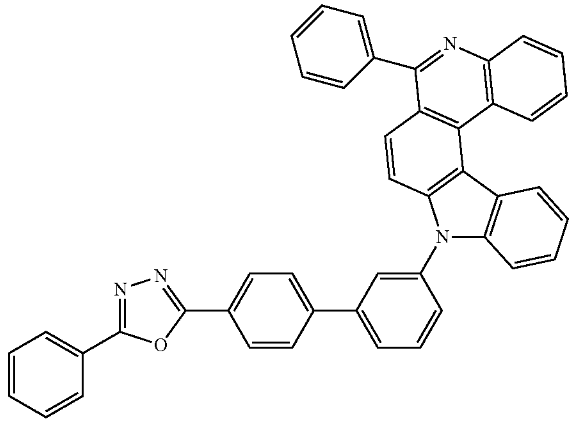
1-237
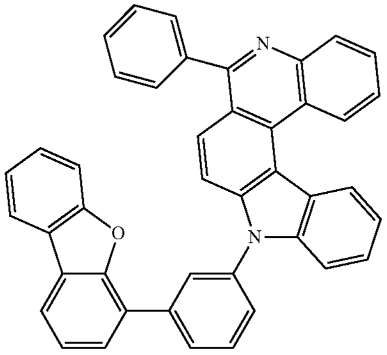
1-238
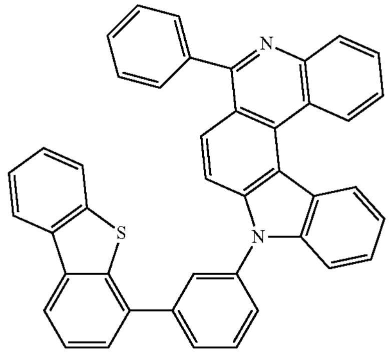
1-239
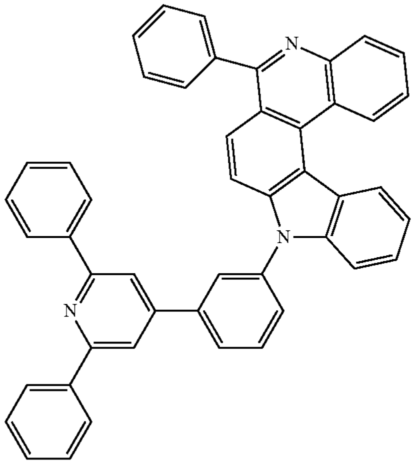
1-240
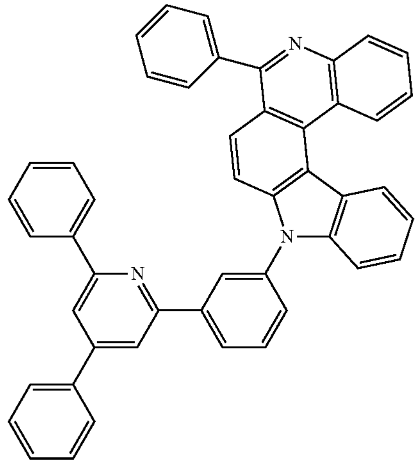
1-241
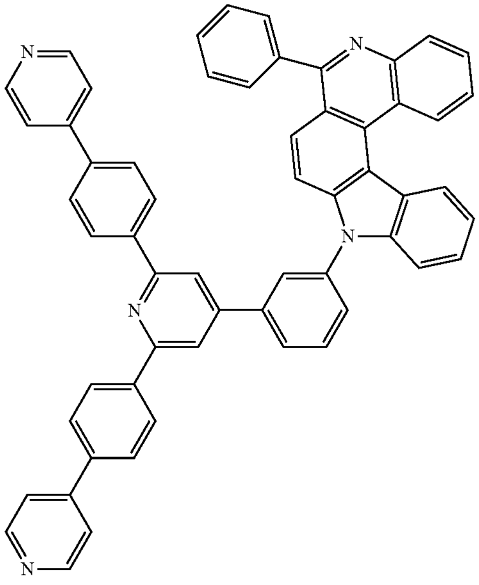

-continued
1-242
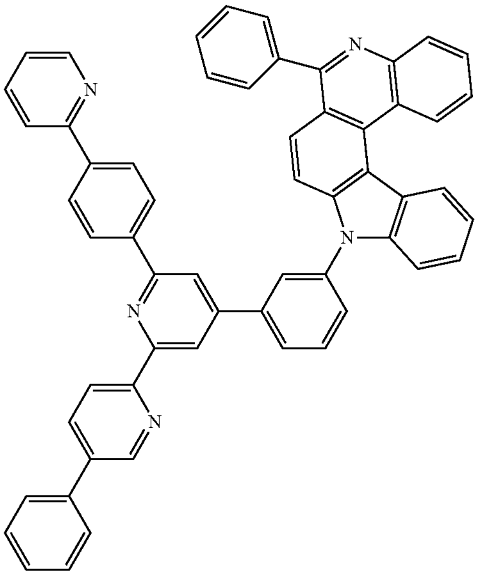
1-243
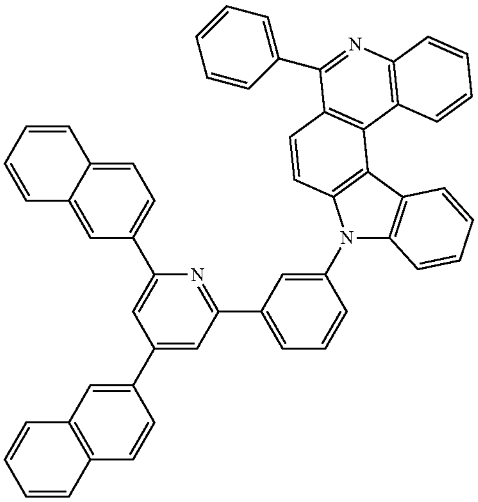
1-244
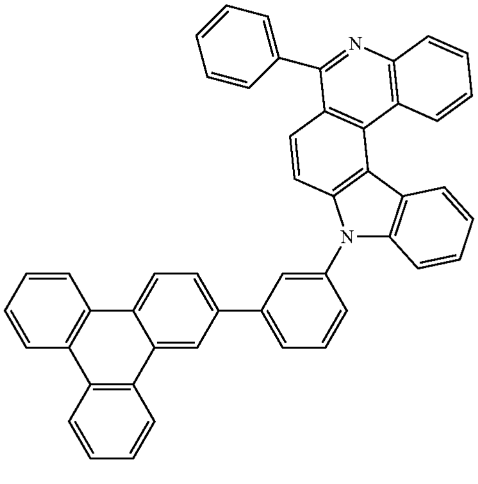
1-245
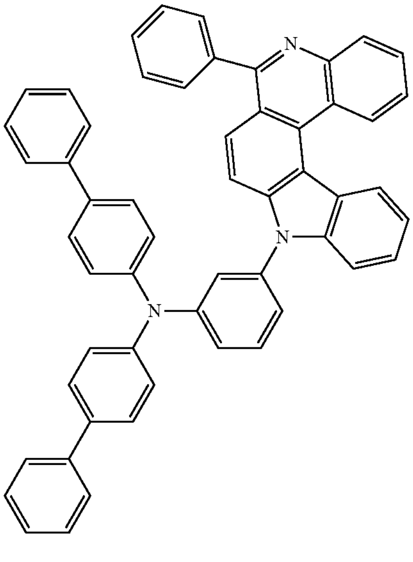

-continued
1-246
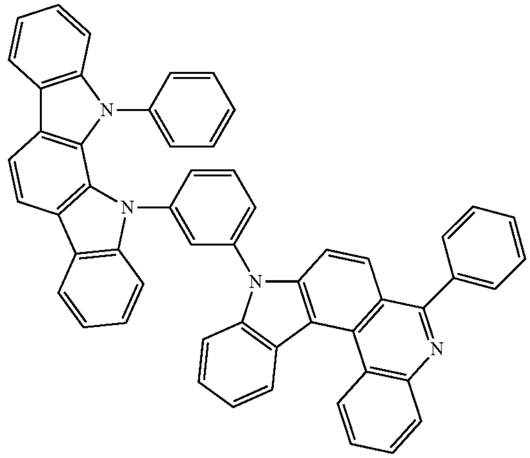
1-247
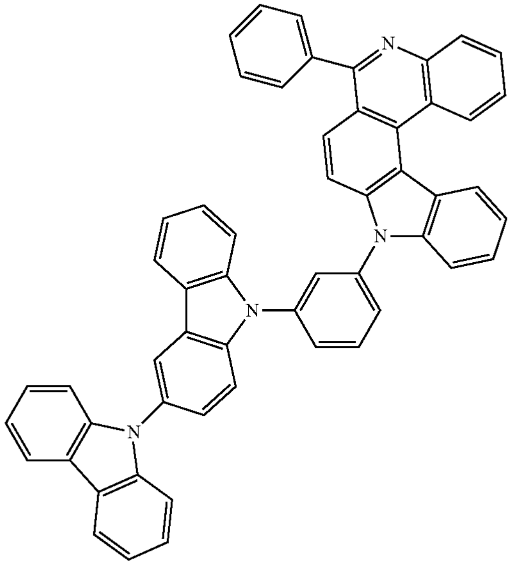
1-248
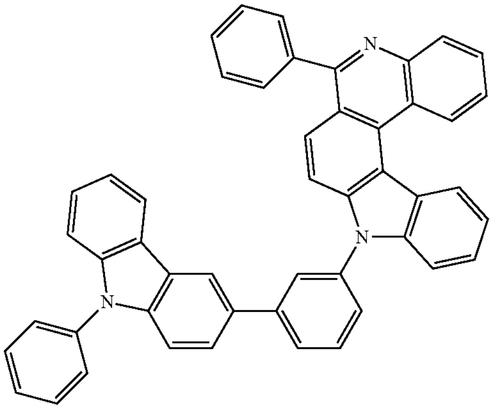
1-249
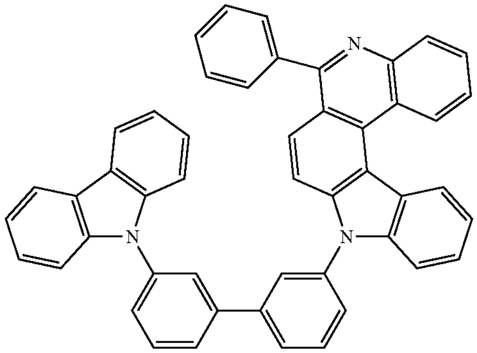
1-250
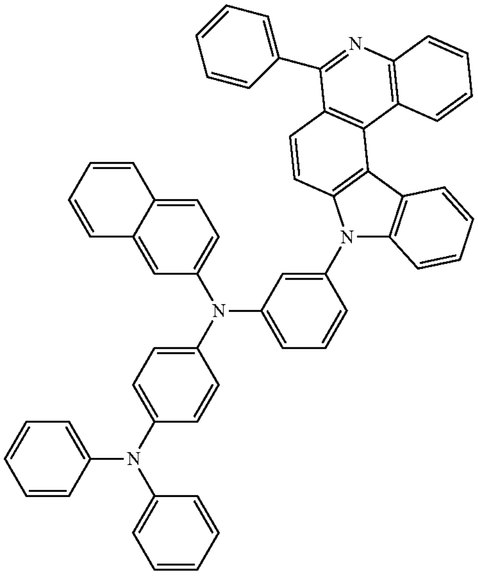
1-488
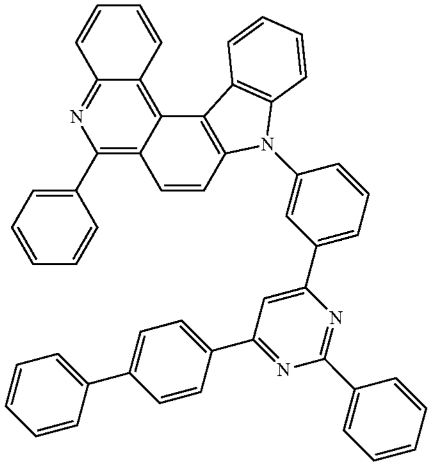

-continued
1-489
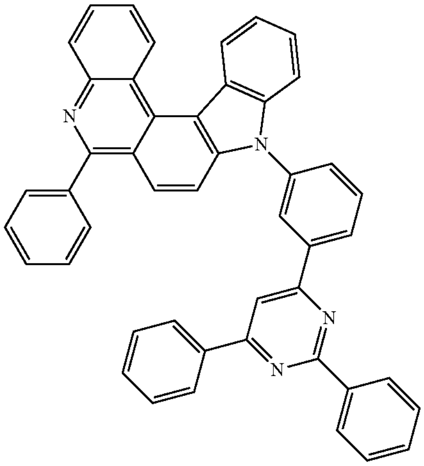
1-490
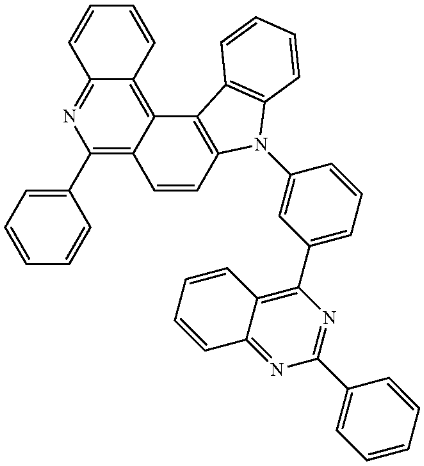
1-491
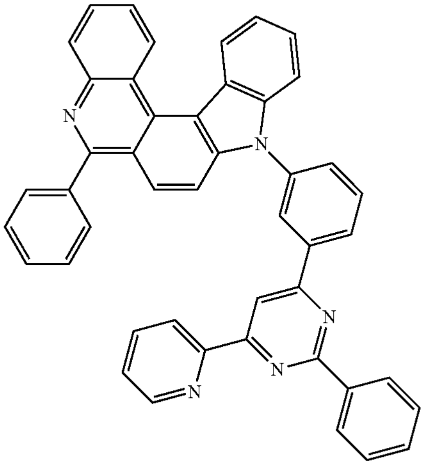
1-492
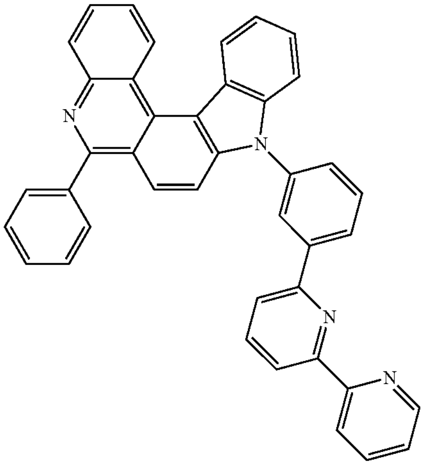
1-493
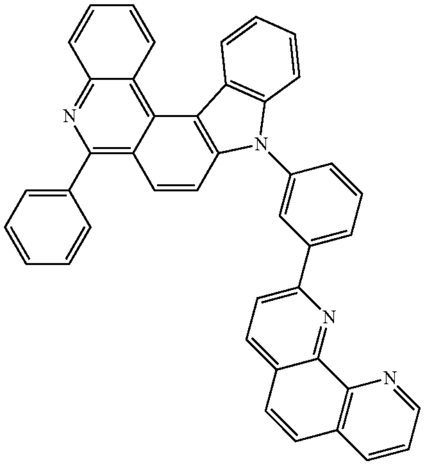
1-494
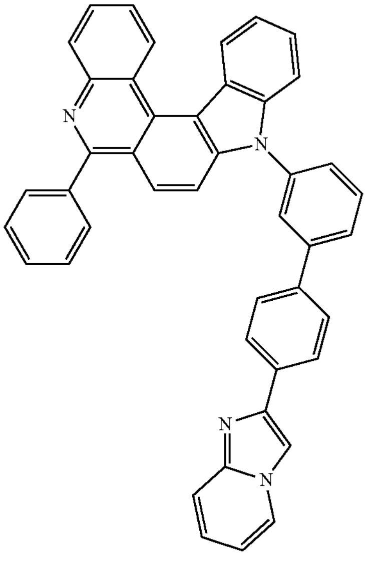

-continued
2-1
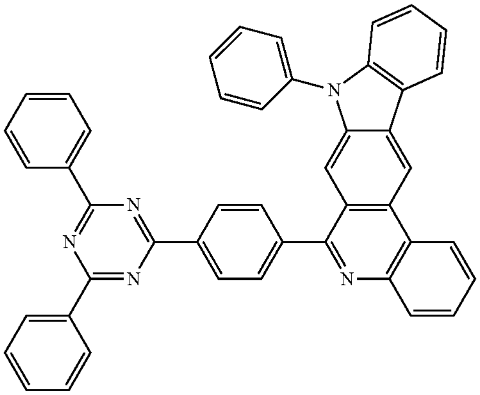
2-2
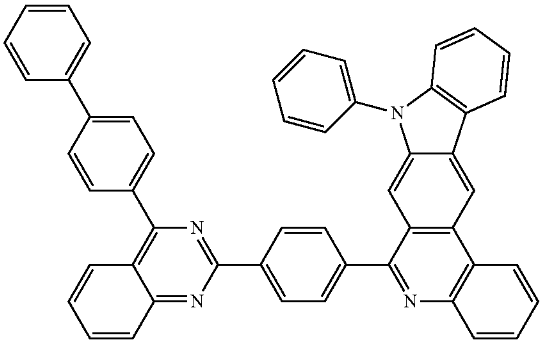
2-3
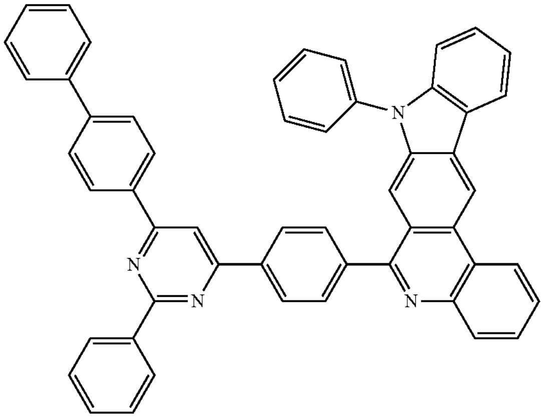
2-4
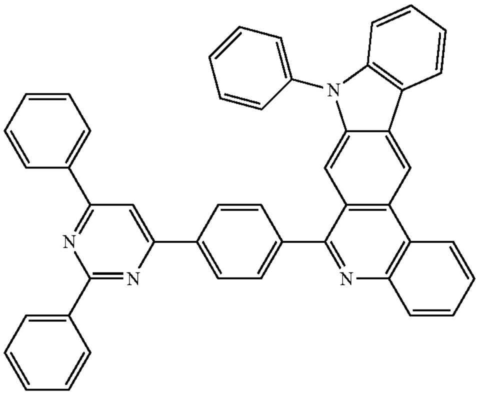
2-5
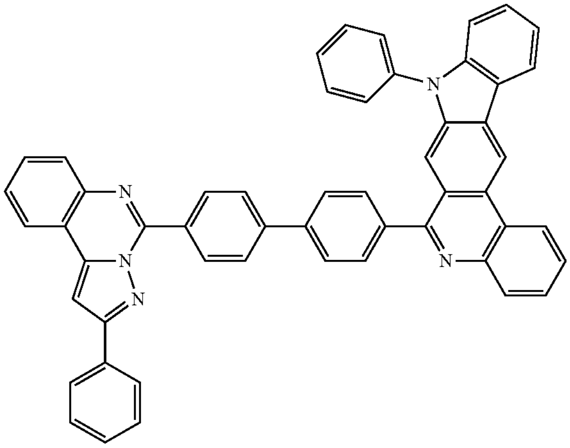
2-6
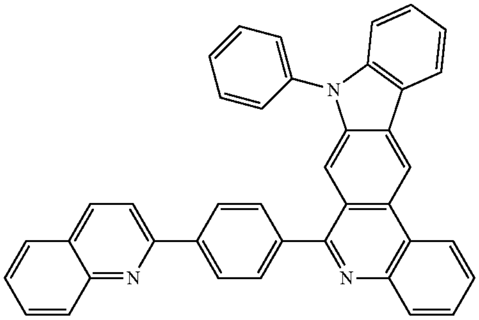

-continued
2-7
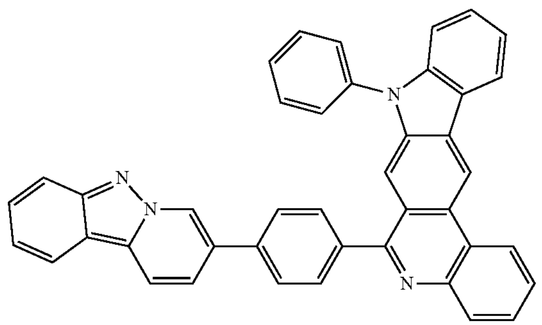
2-8
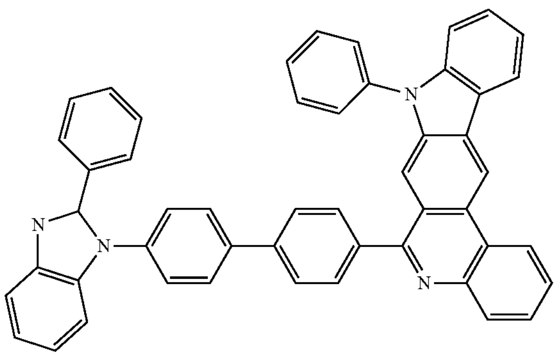
2-9
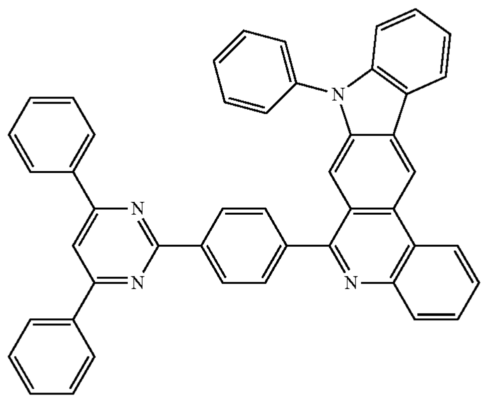
2-10
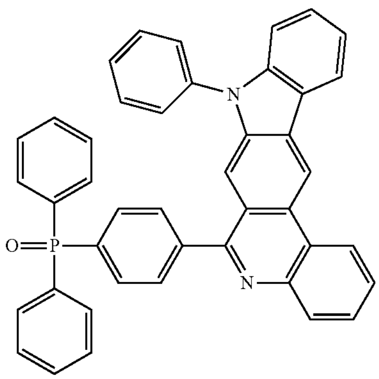
2-11
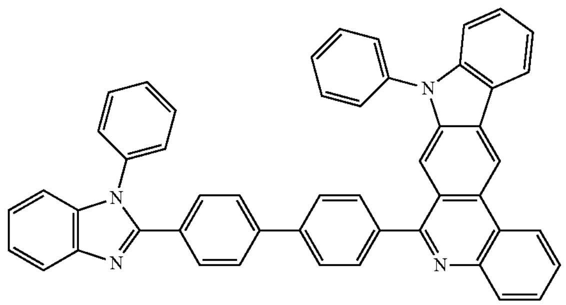
2-12
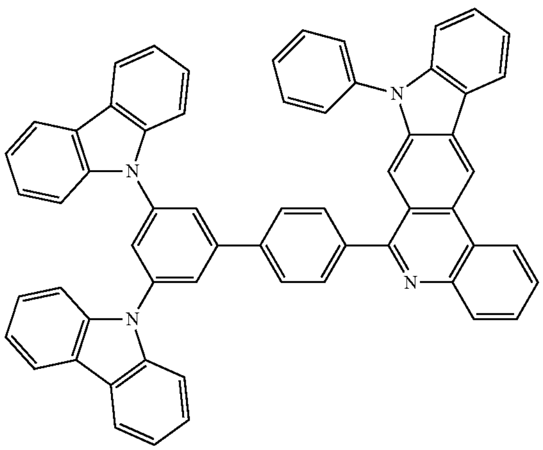
2-13
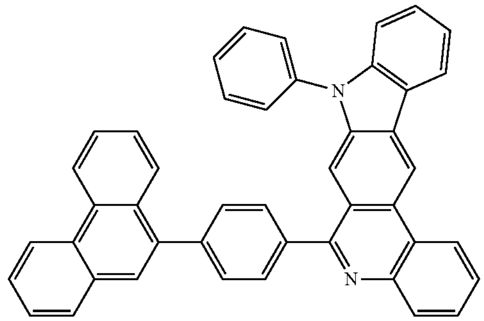
2-14
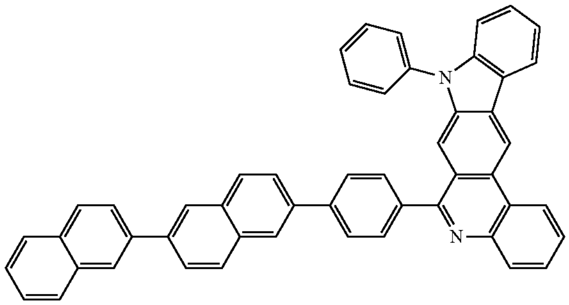

-continued
2-15
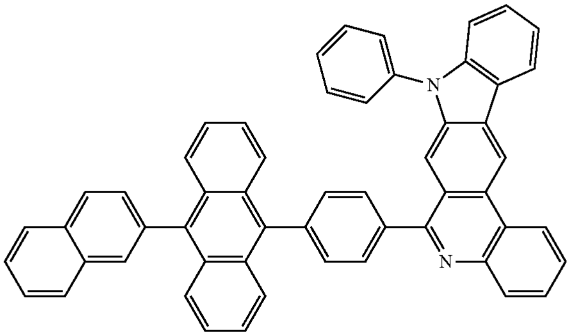
2-16
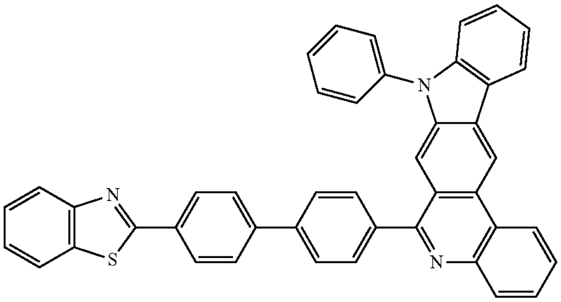
2-17
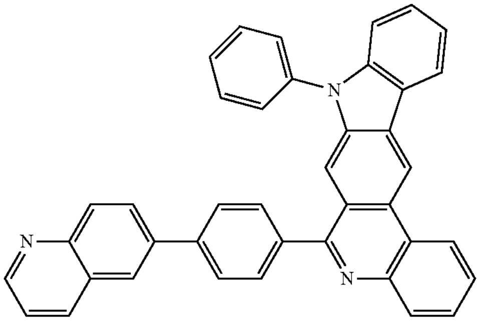
2-18
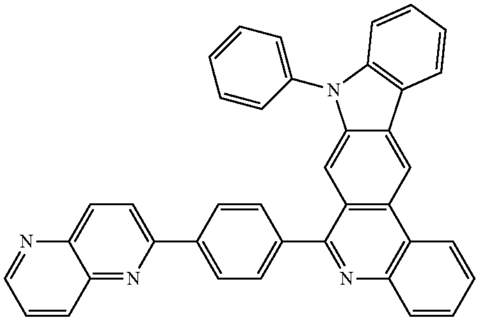
2-19
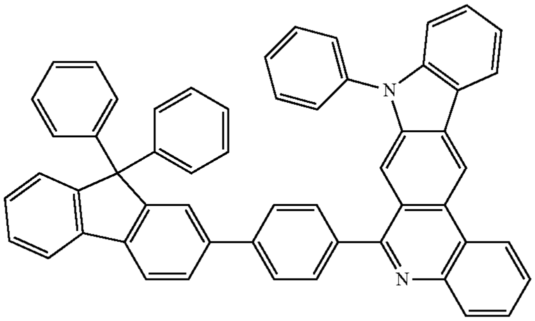
2-20
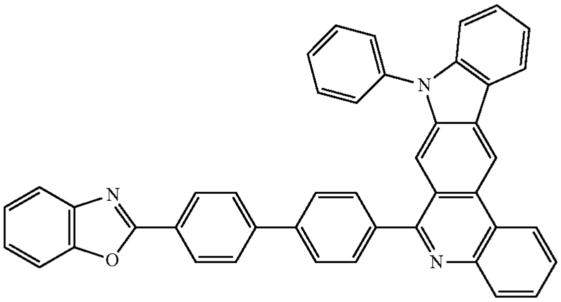
2-21
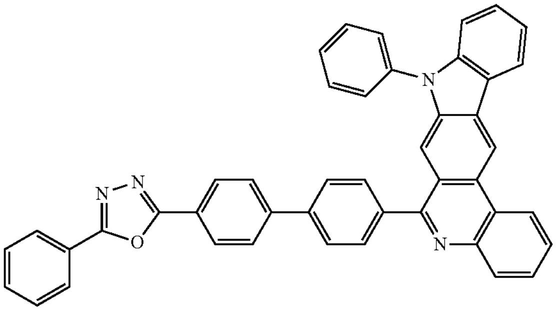
2-22
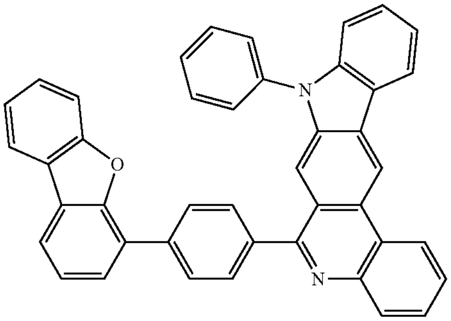

-continued
2-23
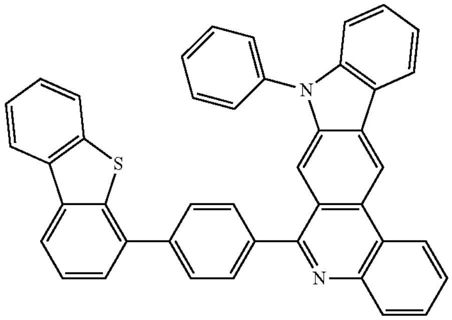
2-24
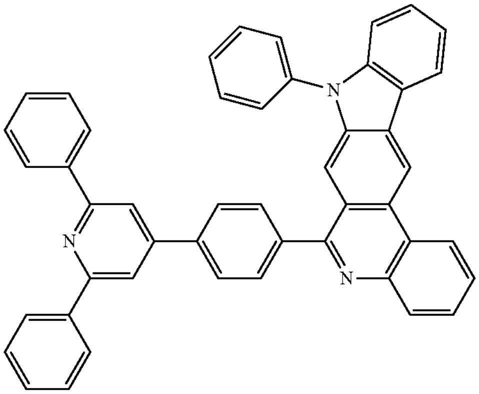
2-25
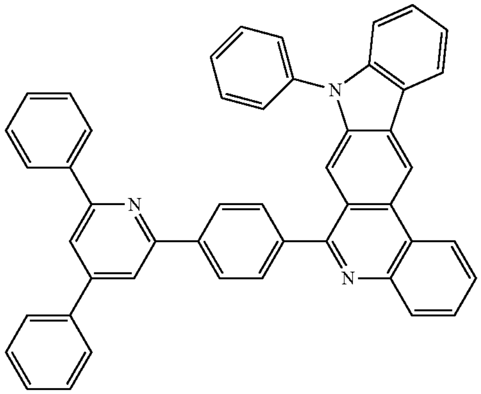
2-26
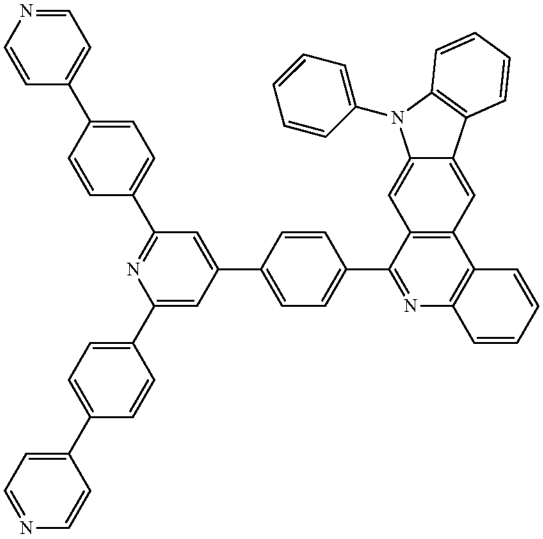
2-27
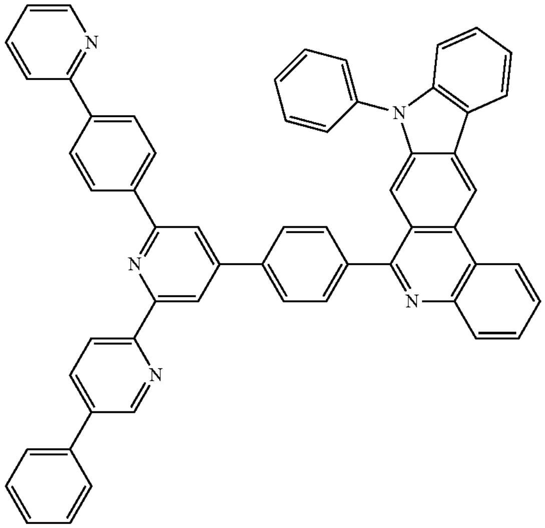
2-28
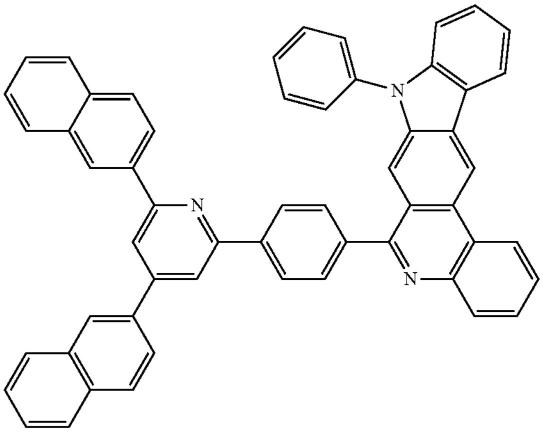

-continued
2-29
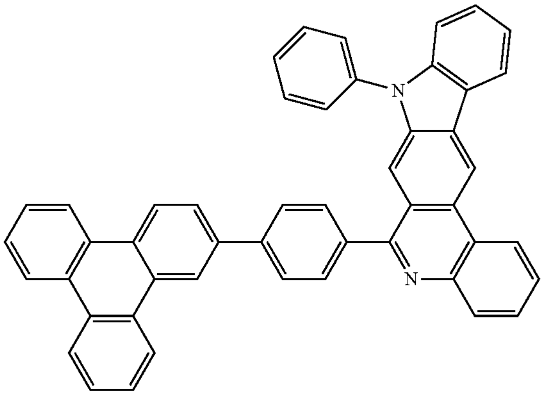
2-30
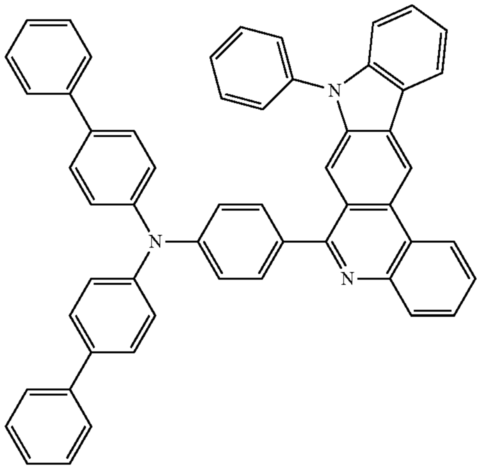
2-31
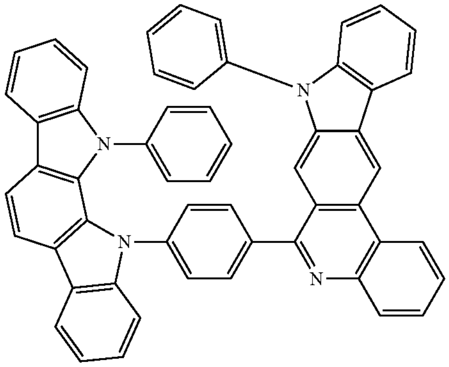
2-32
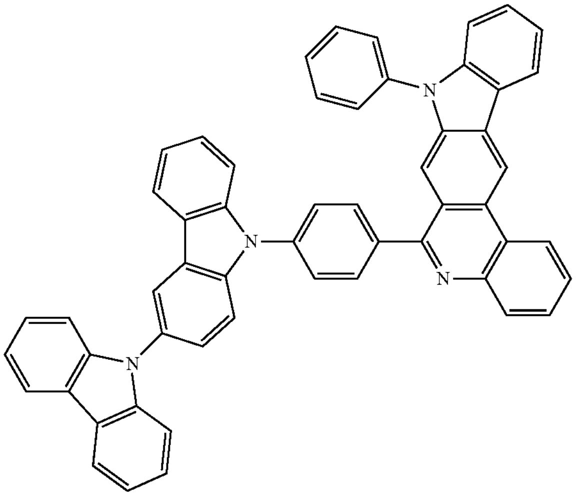
2-33
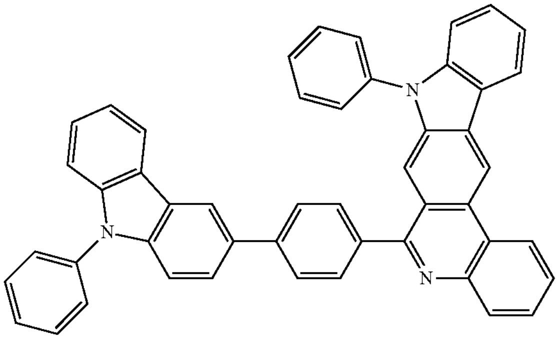
2-34
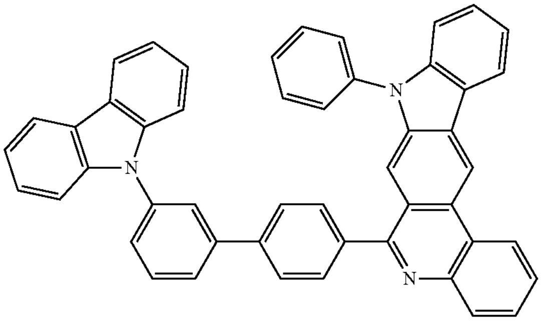

-continued
2-35
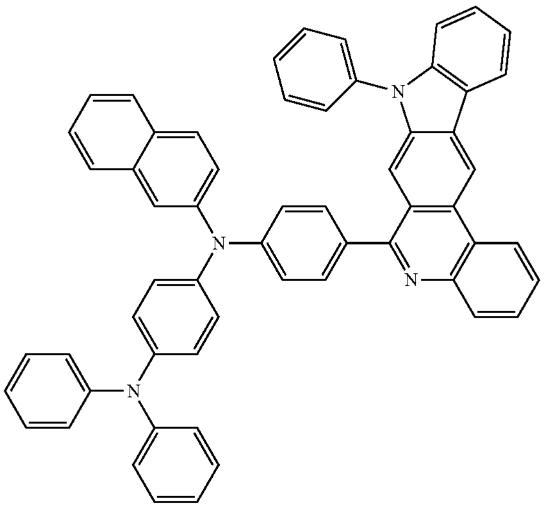
2-36
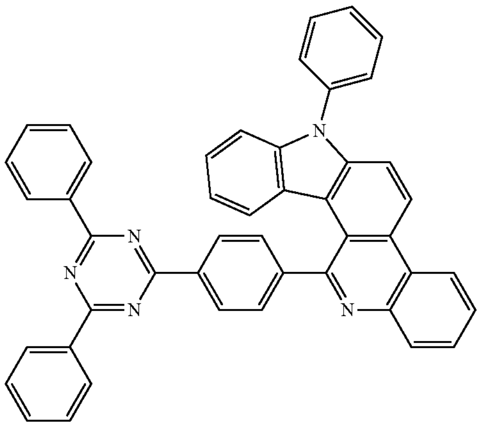
2-37
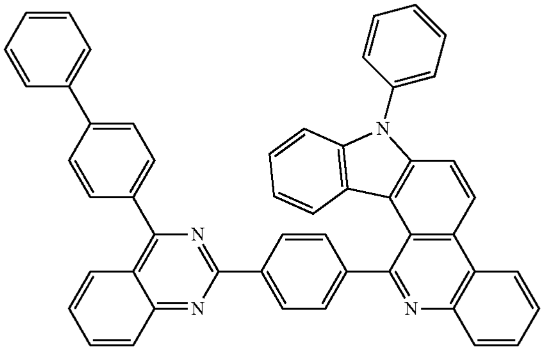
2-38
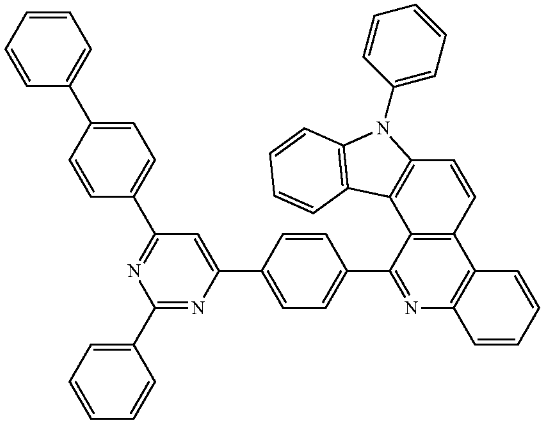
2-39
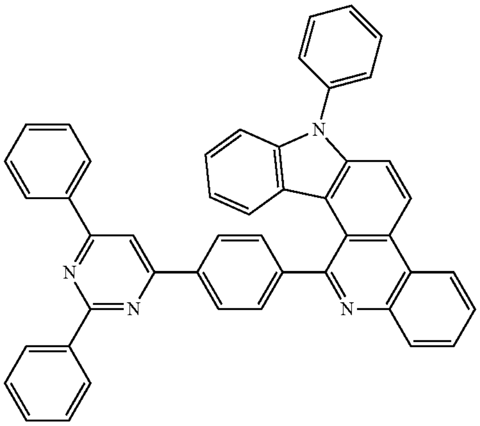
2-40
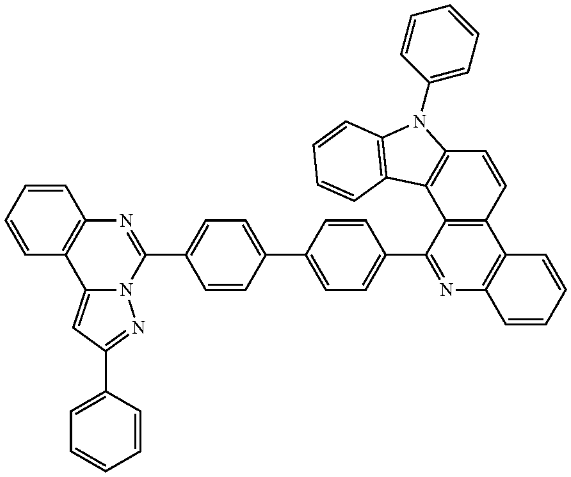

-continued
2-41
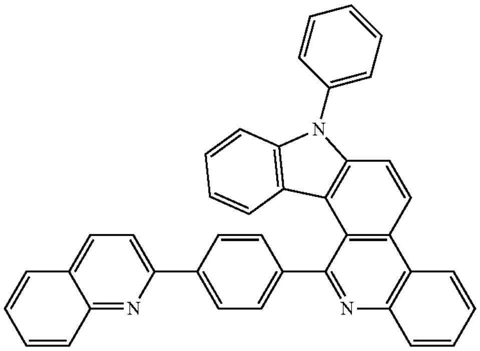
2-42
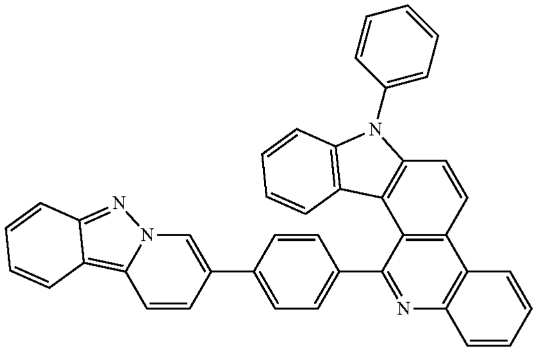
-243
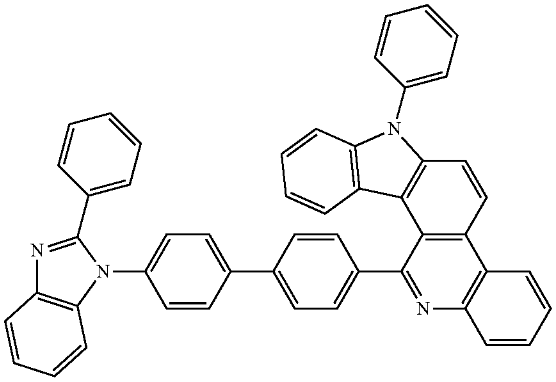
2-44
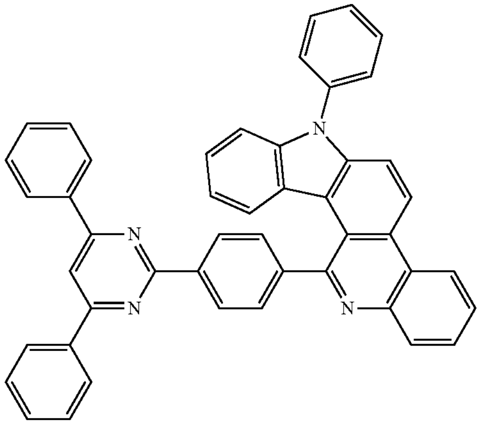
2-45
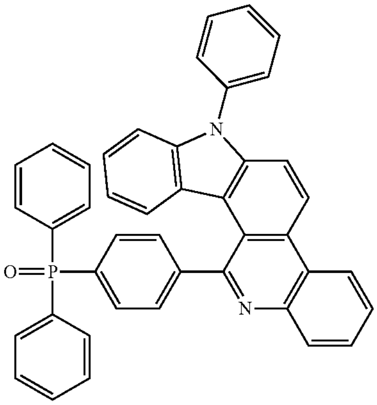
2-46
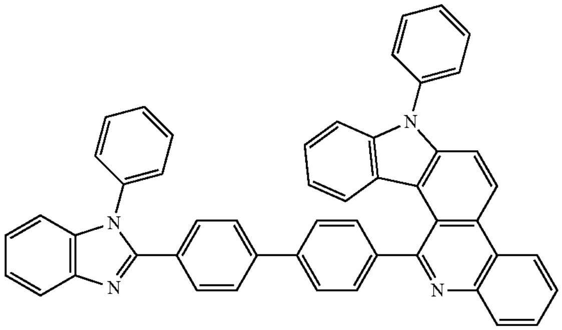

-continued
2-47
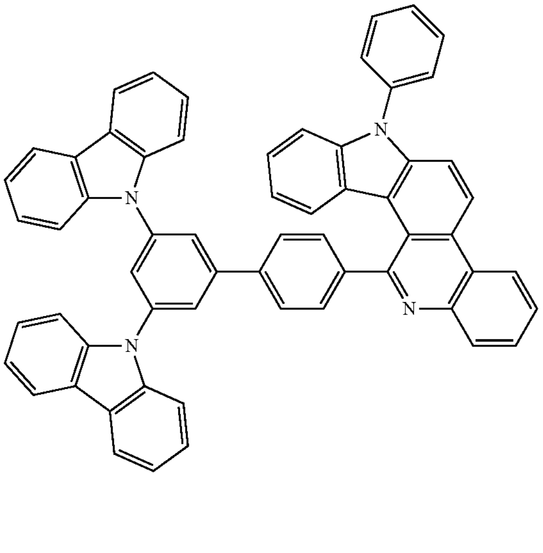
2-48
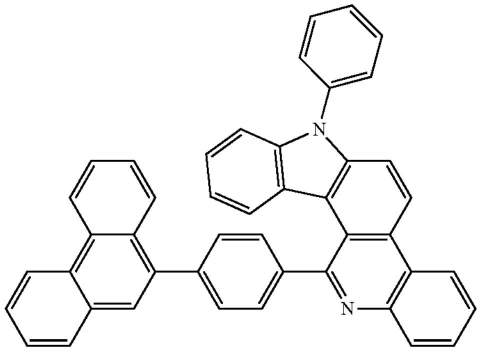
2-49
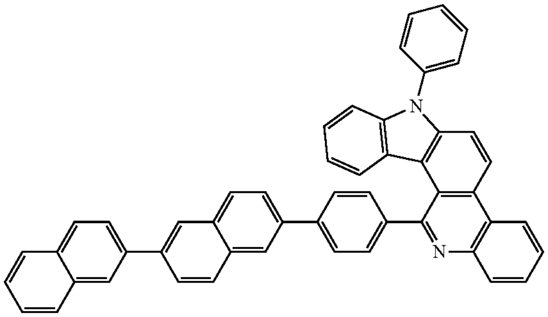
2-50
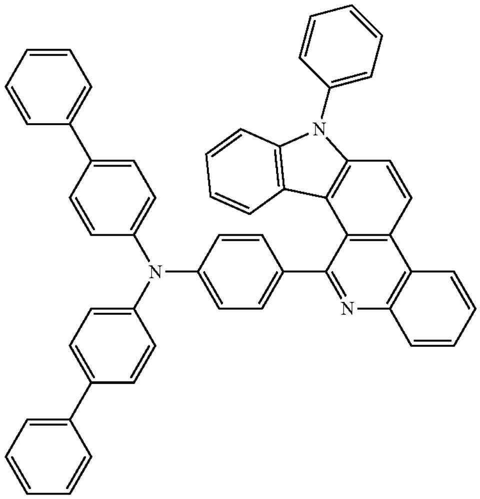
2-51
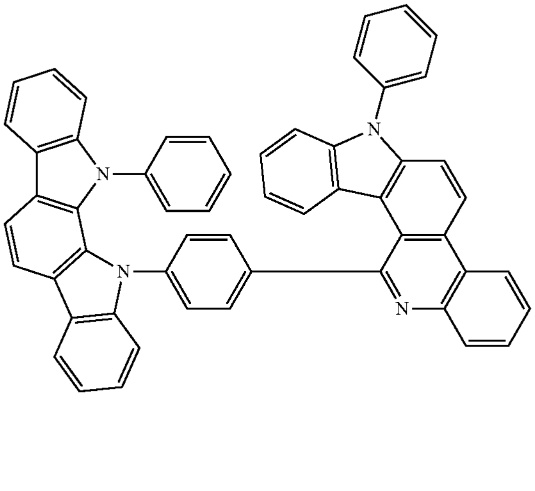
2-52
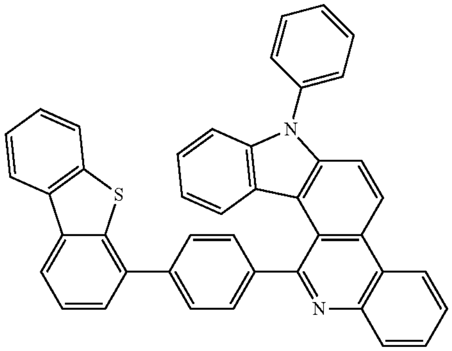

-continued
2-53
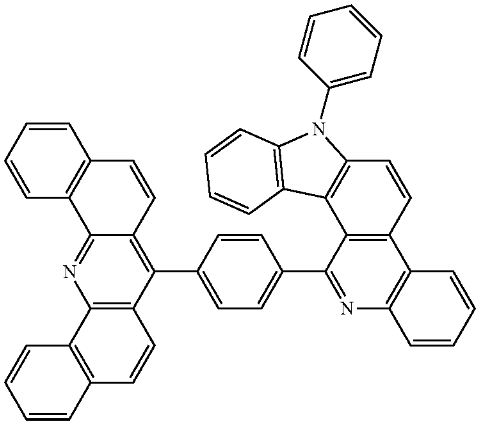
2-54
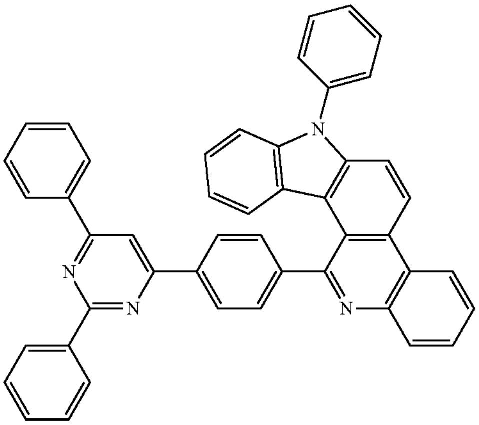
2-55
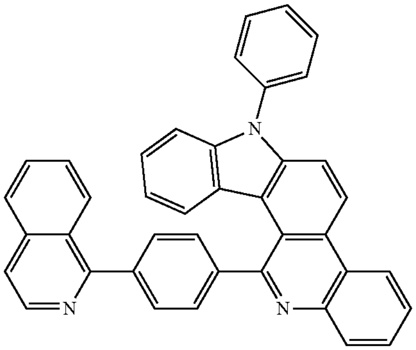
2-56
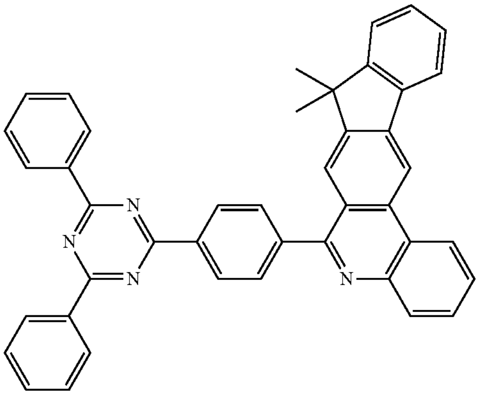
2-57
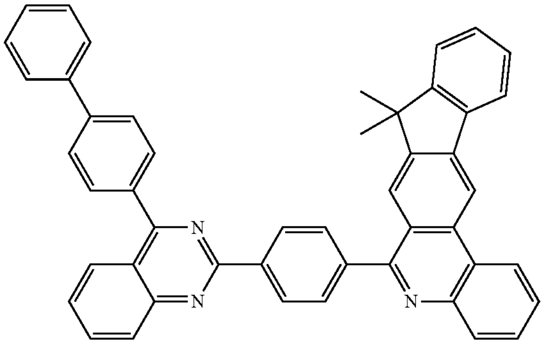
2-58
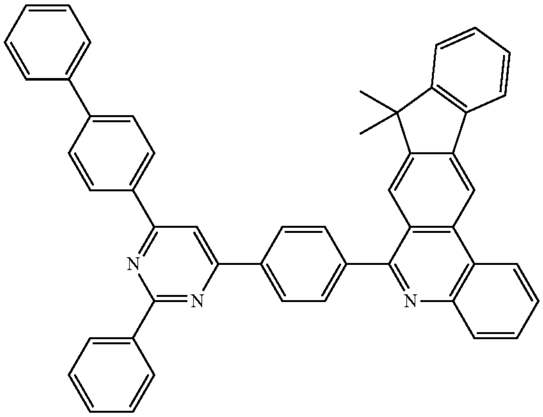

-continued
2-59
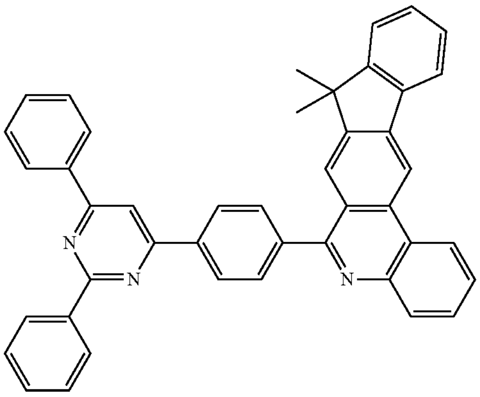
2-60
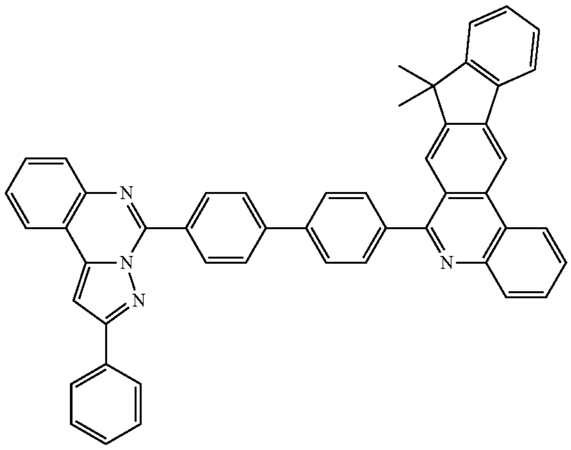
2-61
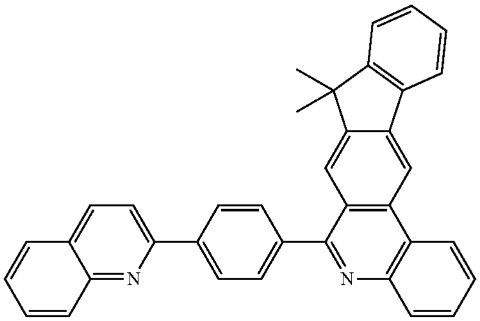
2-62
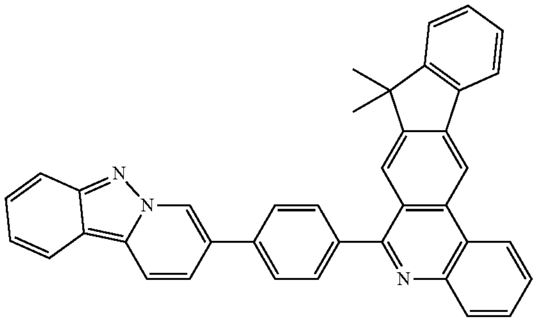
2-63
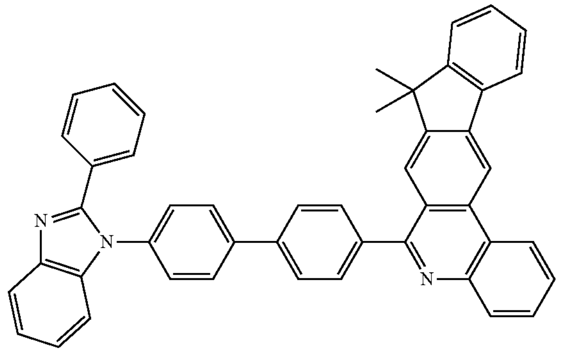
2-64
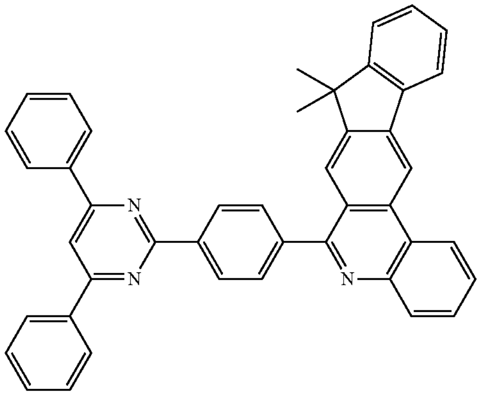
2-65
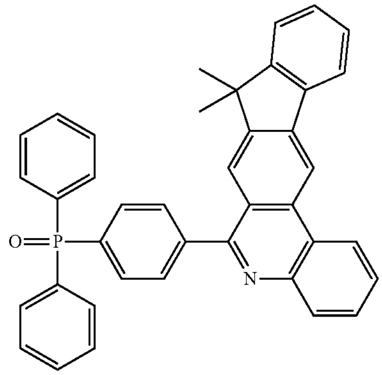
2-66
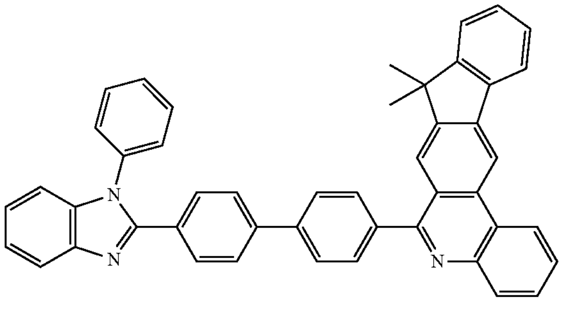

-continued
2-67
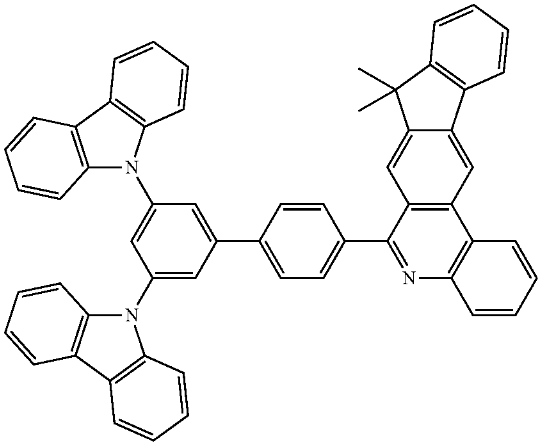
2-68
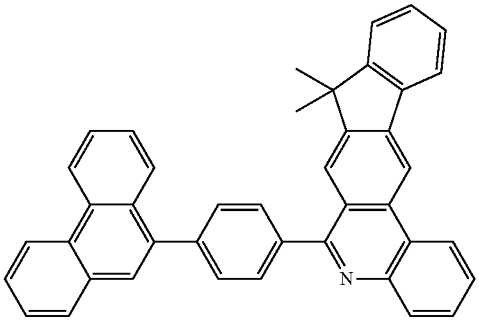
2-69
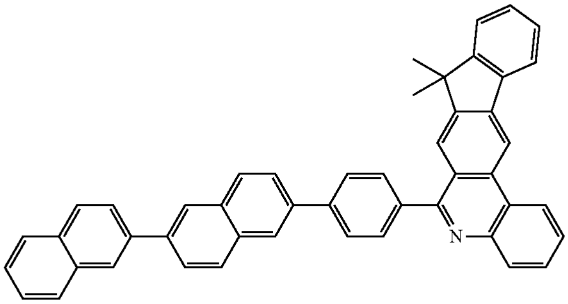
2-70
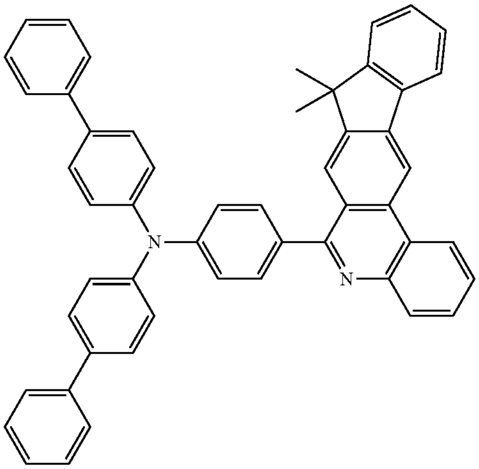
2-71
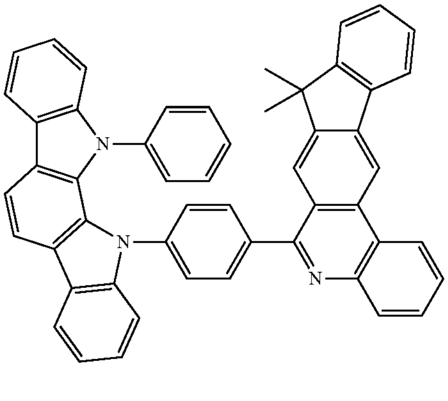
2-72
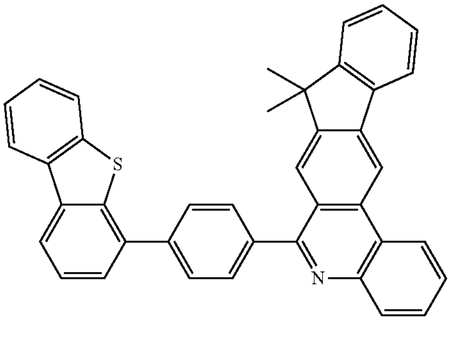

-continued
2-73
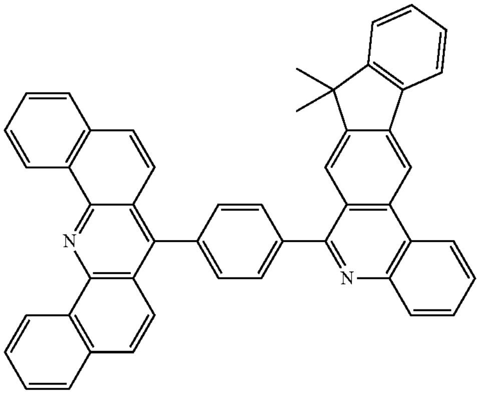
2-74
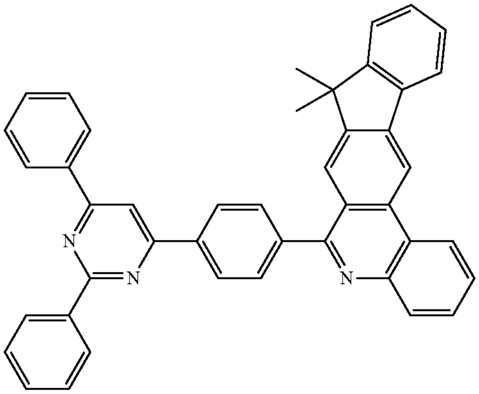
2-75
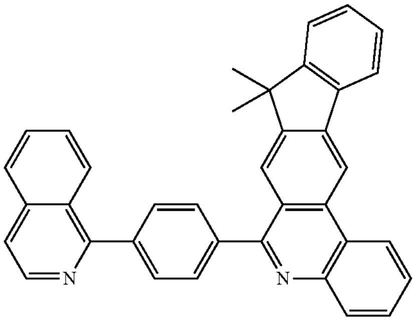
2-76
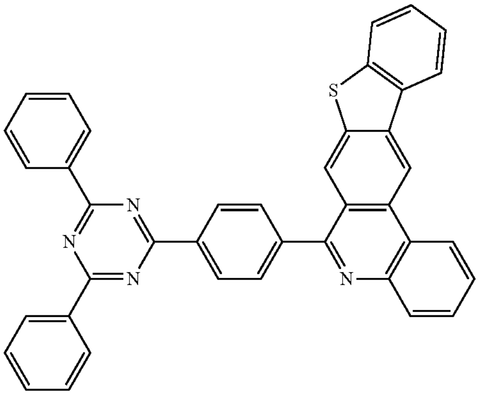
2-77
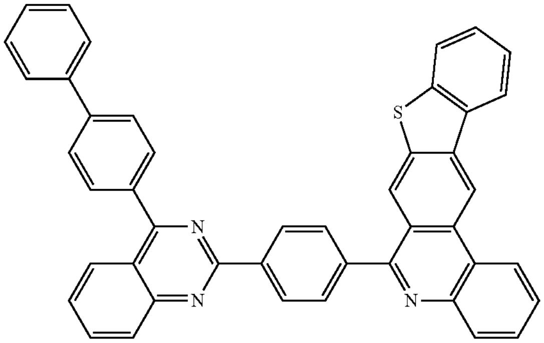
2-78
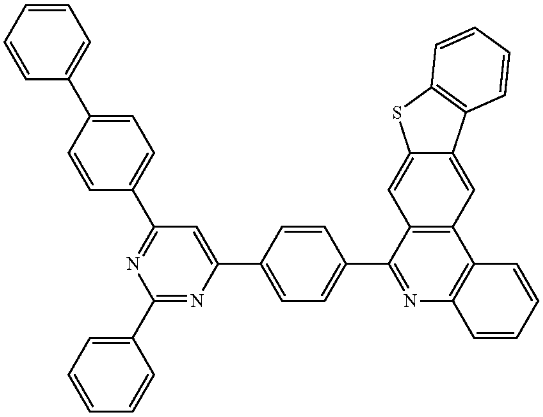
2-79
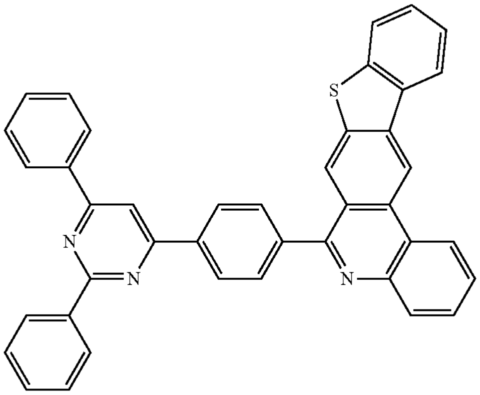

-continued
2-80
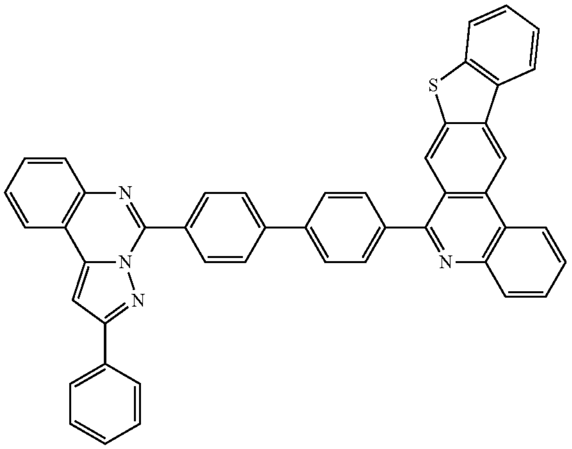
2-81
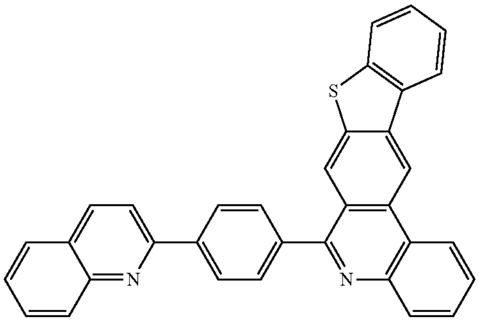
2-82
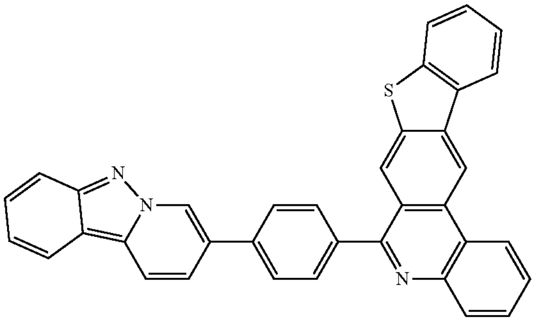
2-83
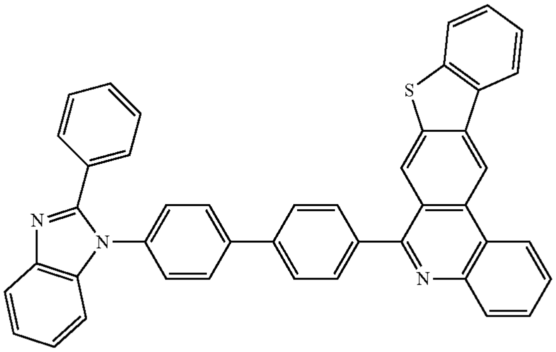
2-84
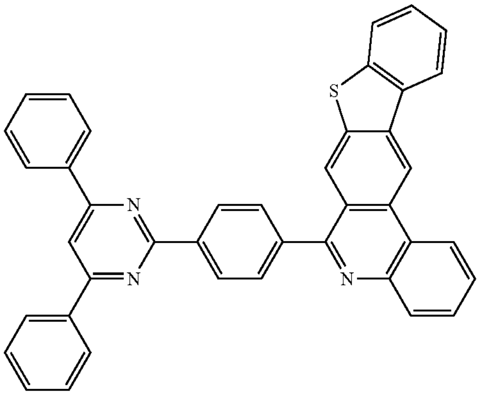
2-85
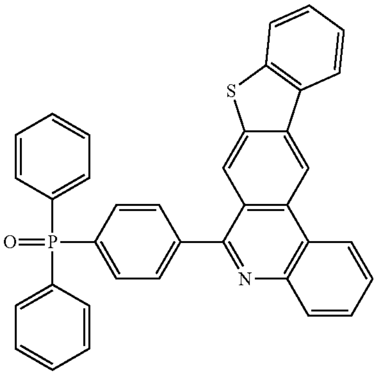

-continued
2-86
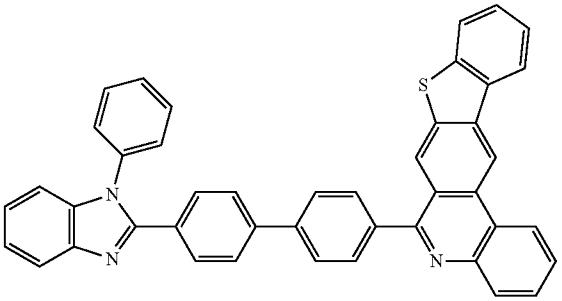
2-87
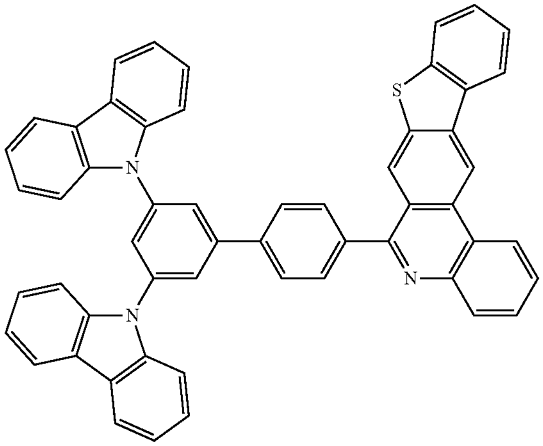
2-88
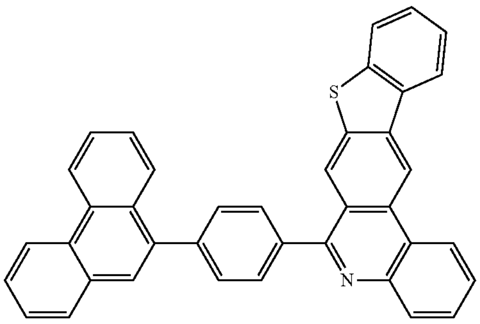
2-89
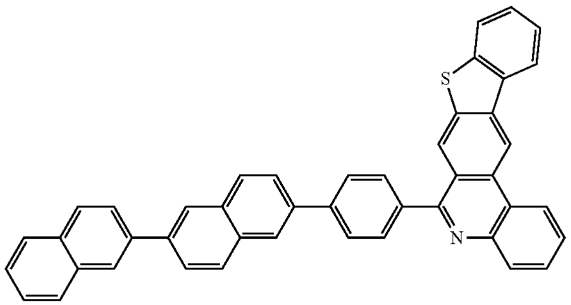
2-90
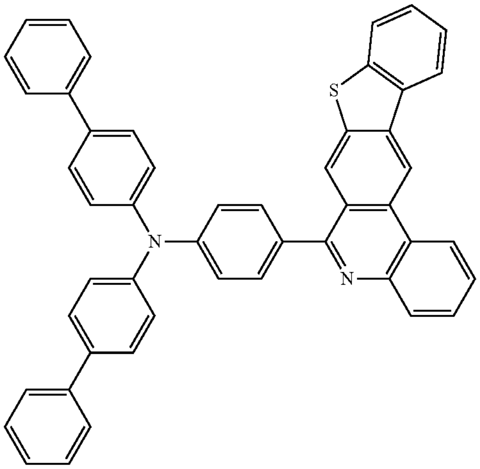
2-91
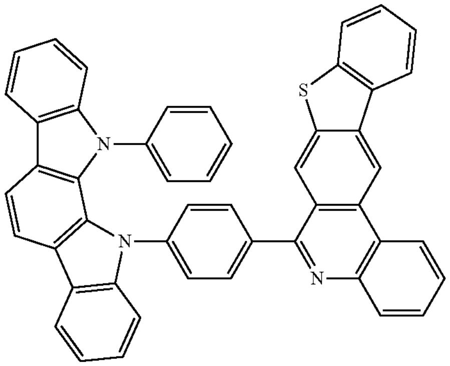

-continued
2-92
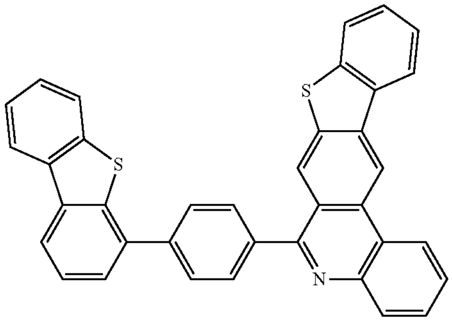
2-93
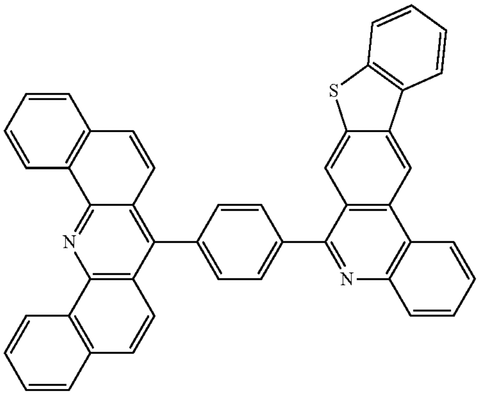
2-94
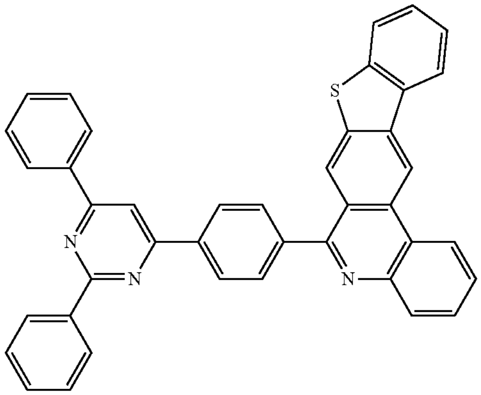
2-95
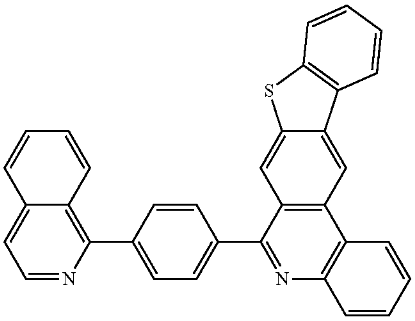
2-96
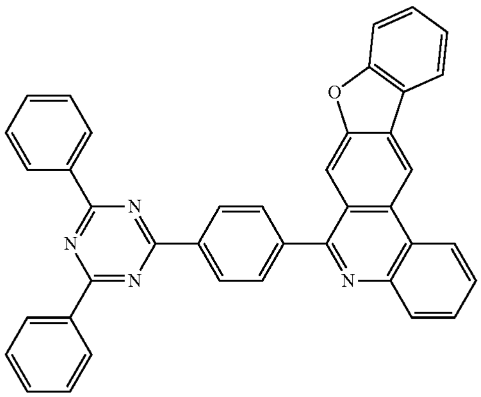
2-97
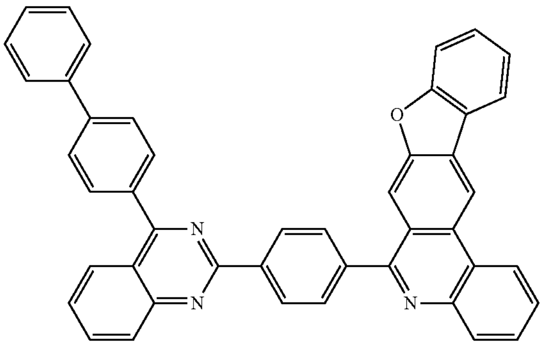
2-98
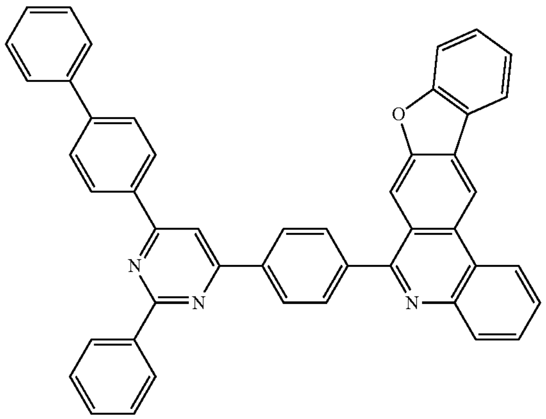
2-99
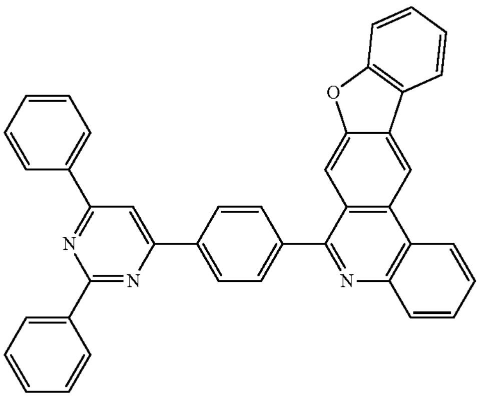

-continued
2-100
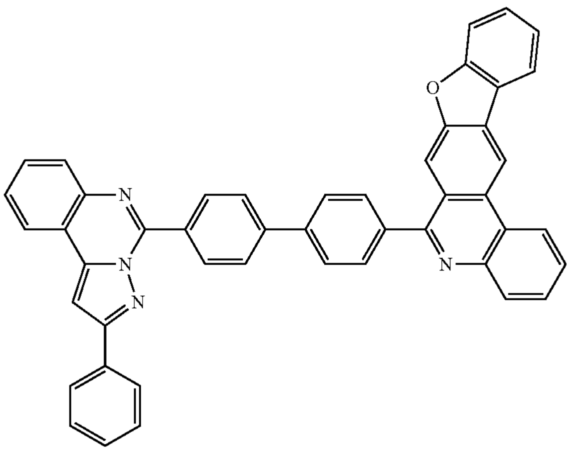
2-101
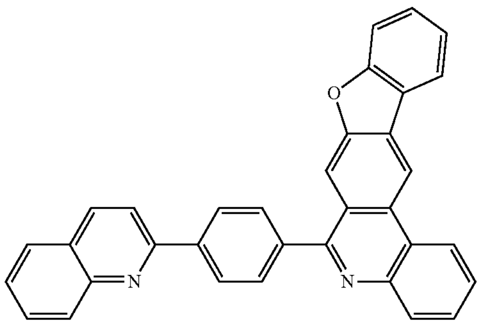
2-102
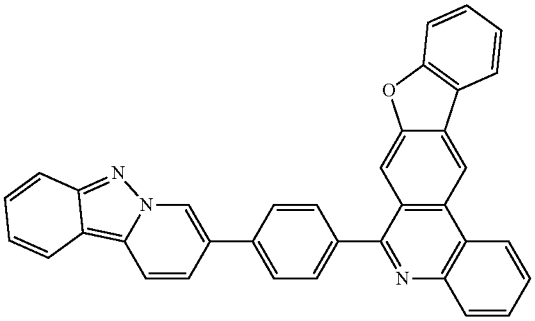
1-103
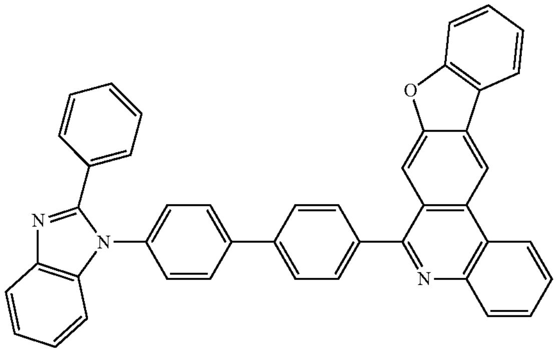
2-104
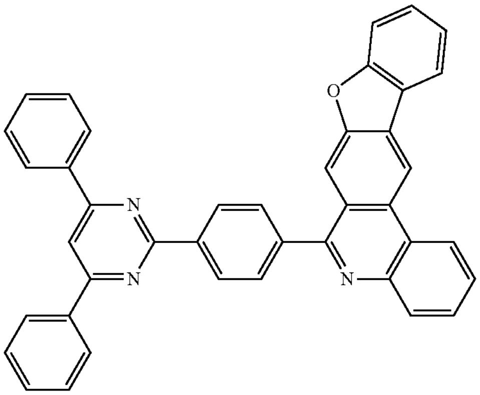
2-105
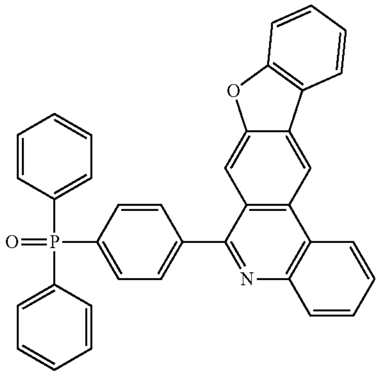

-continued
2-106
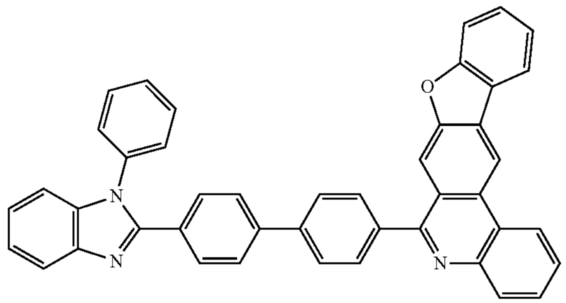
2-107
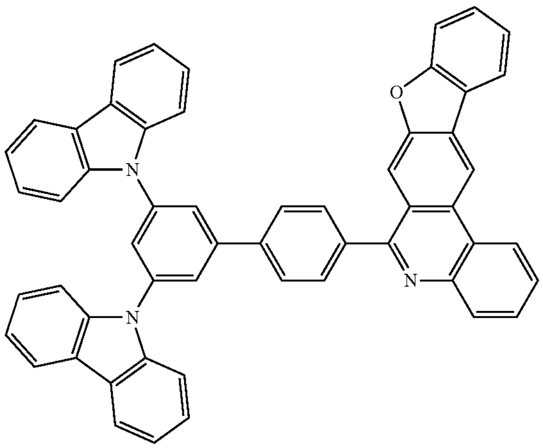
2-108
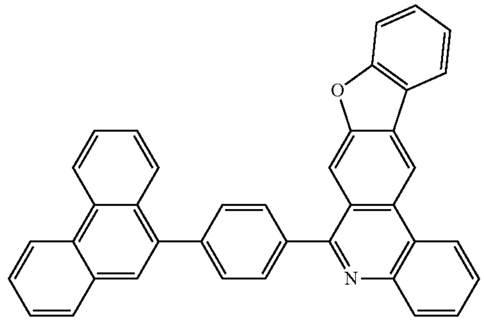
2-109
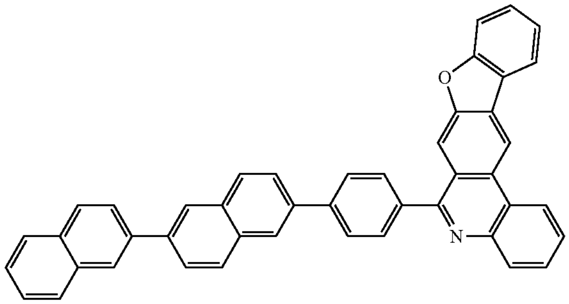
2-110
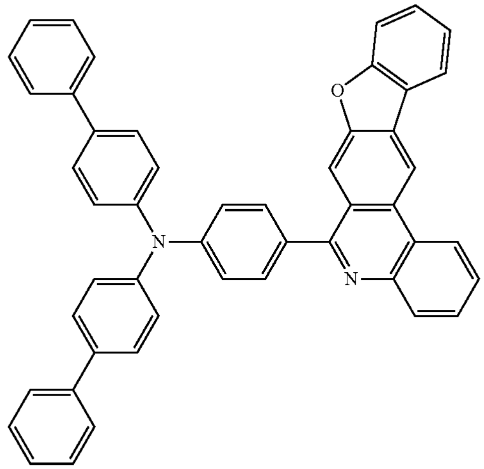
2-111
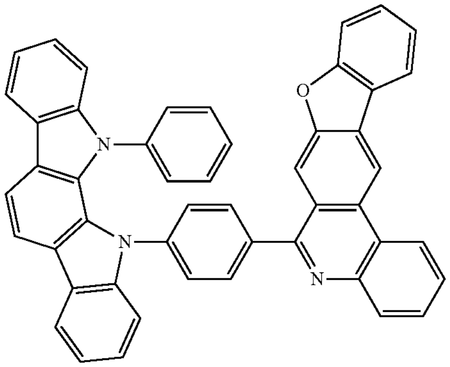

-continued
2-112
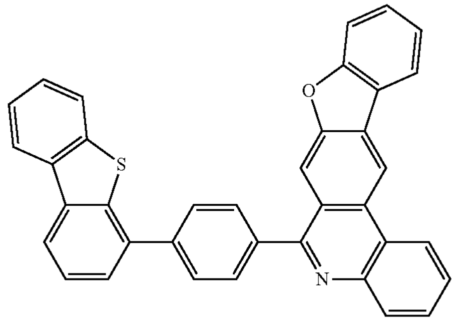
2-113
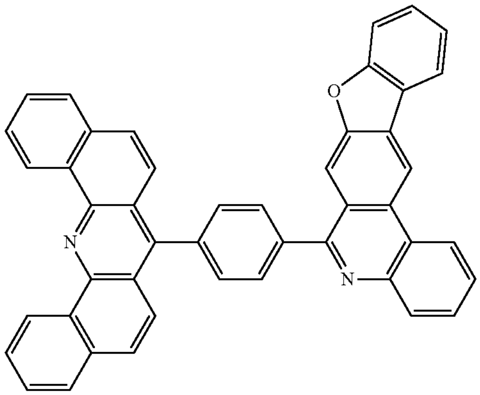
2-114
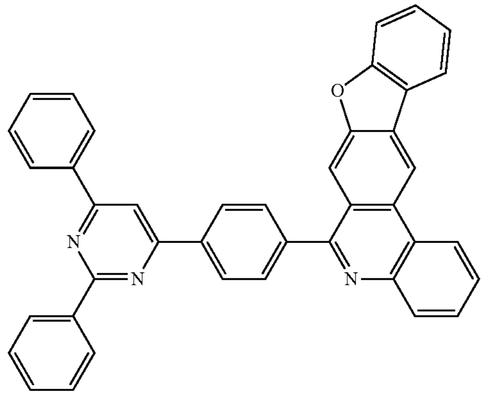
2-115
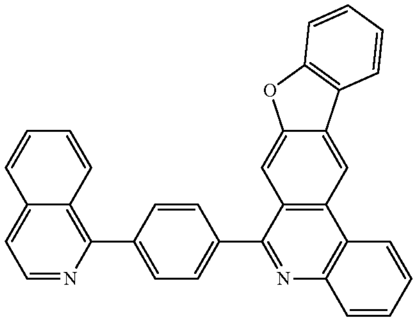
2-116
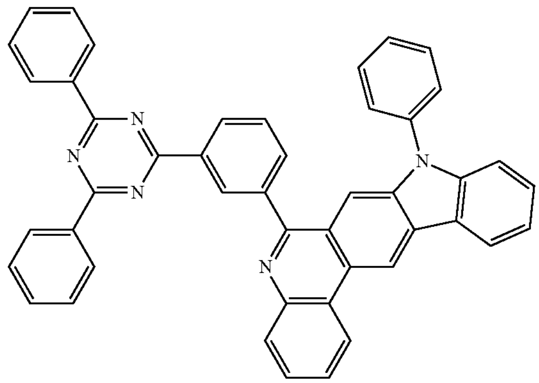
2-117
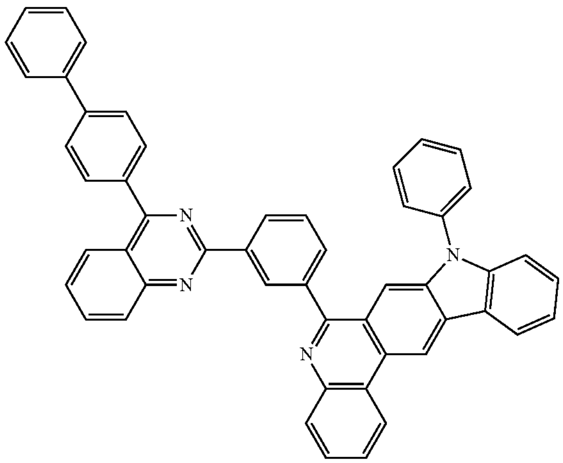

-continued
2-118
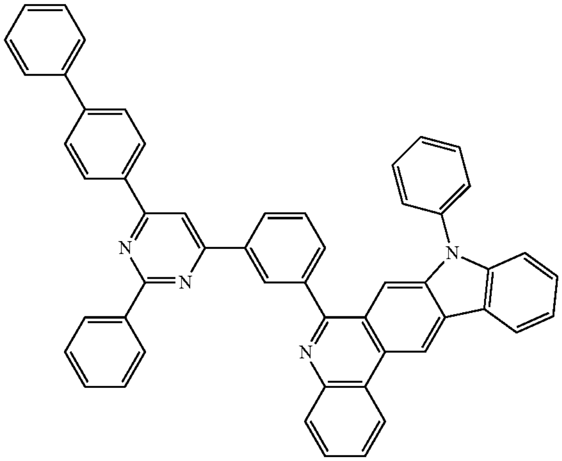
2-119
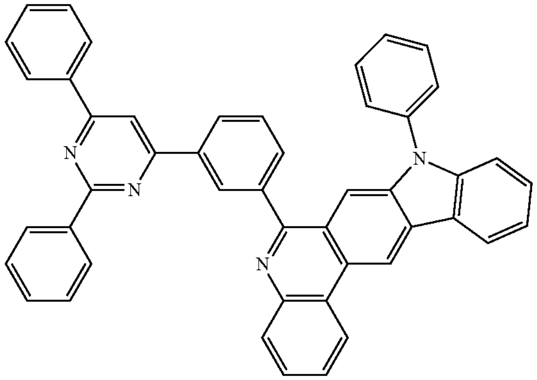
2-120
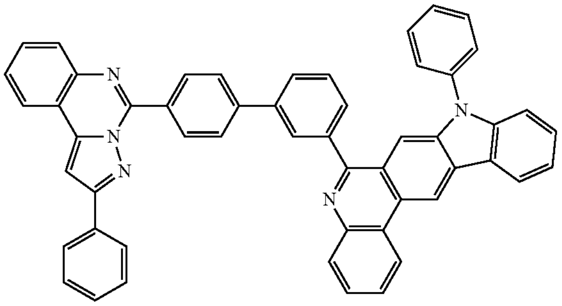
2-121
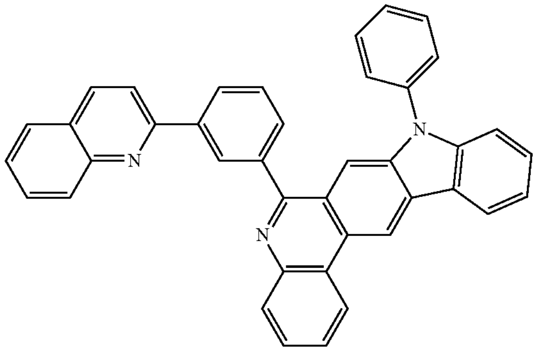
2-122
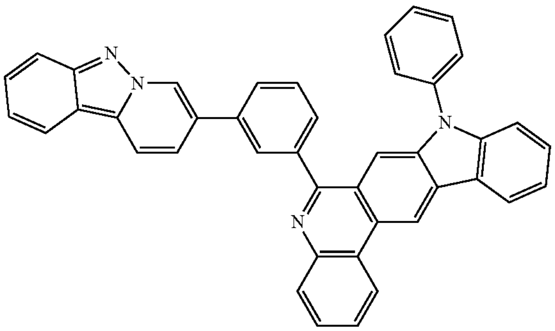
2-123
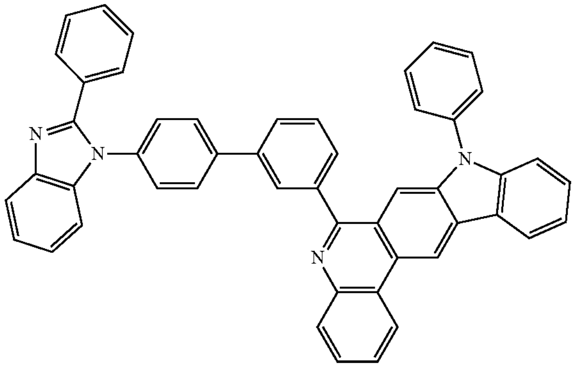
2-124
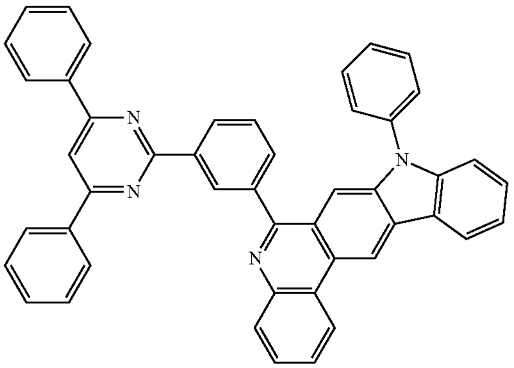
2-125
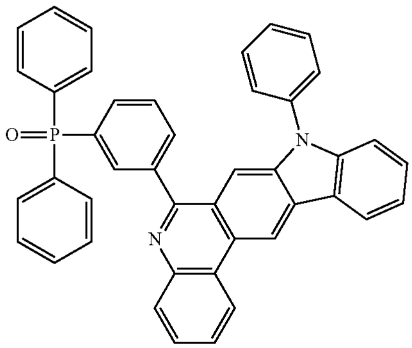

-continued
2-126
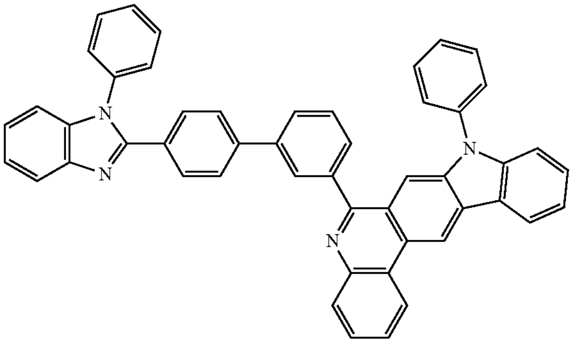
2-127
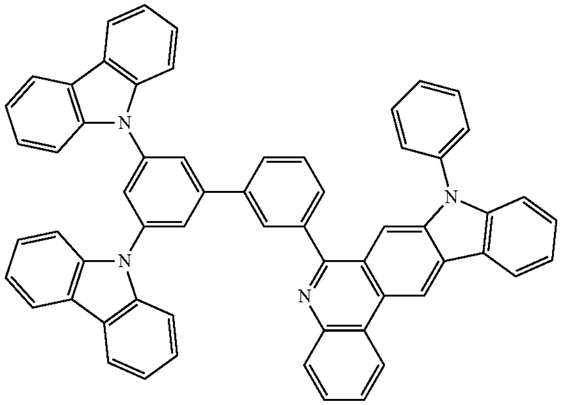
2-128
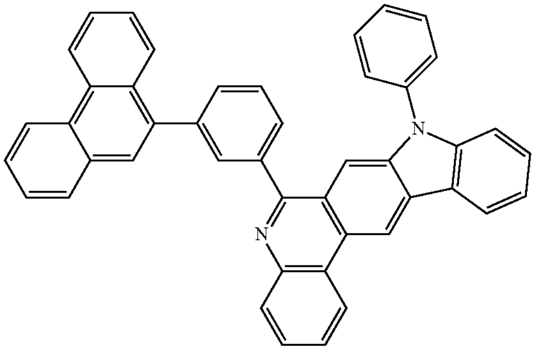
2-129
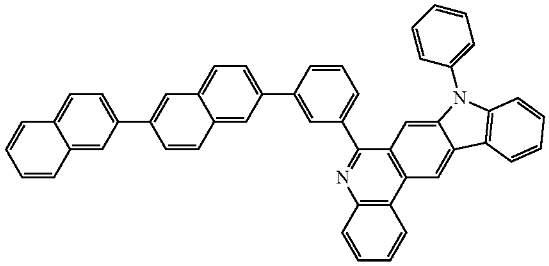
2-130
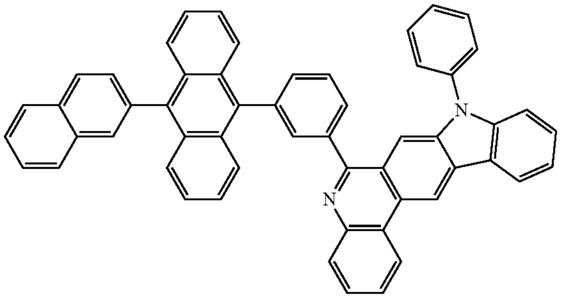
2-131
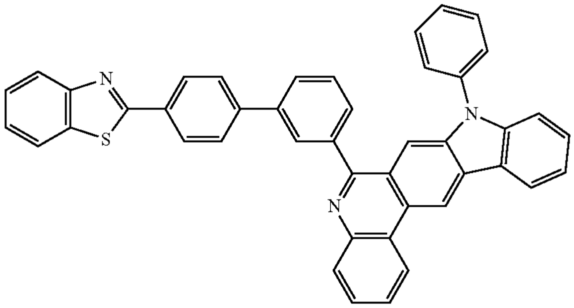
2-132
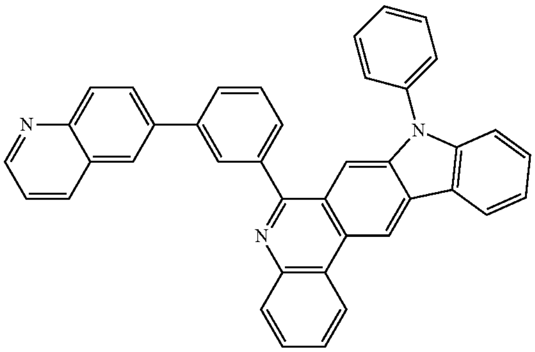
2-133
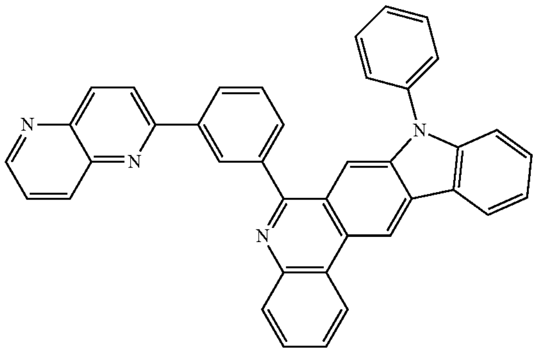

-continued
2-134
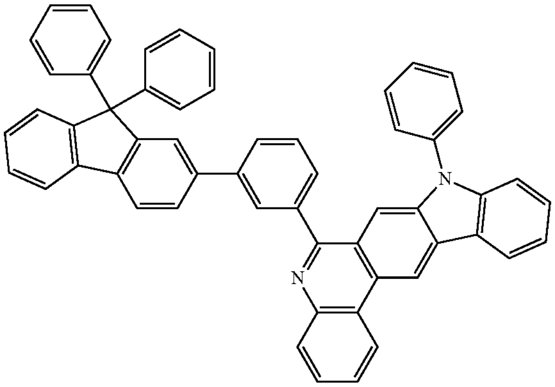
2-135
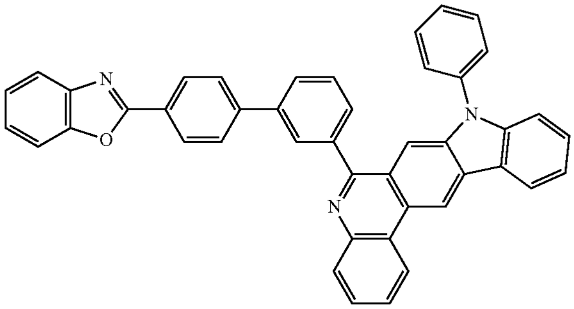
2-136
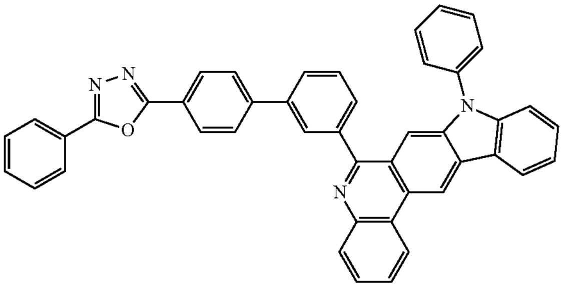
2-137
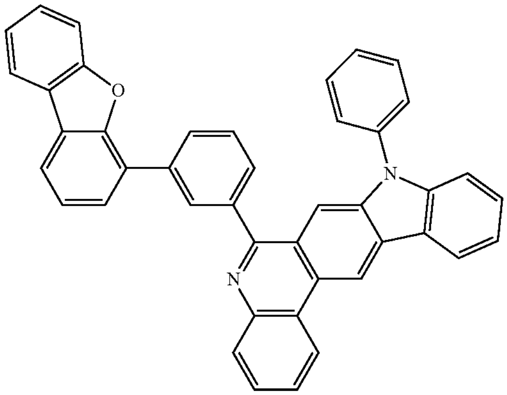
2-138
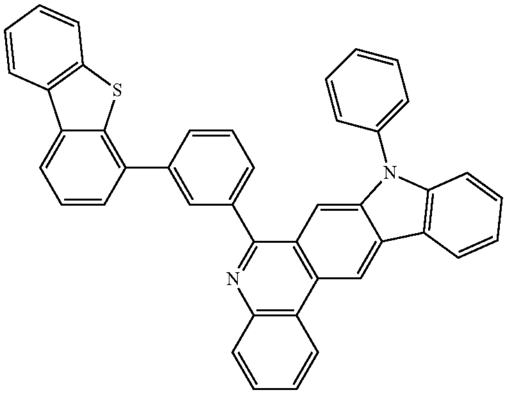
2-139
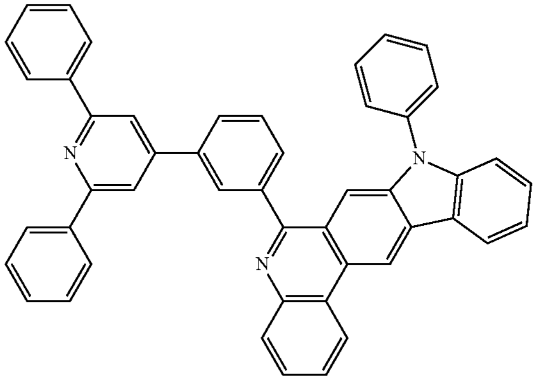

-continued
2-140
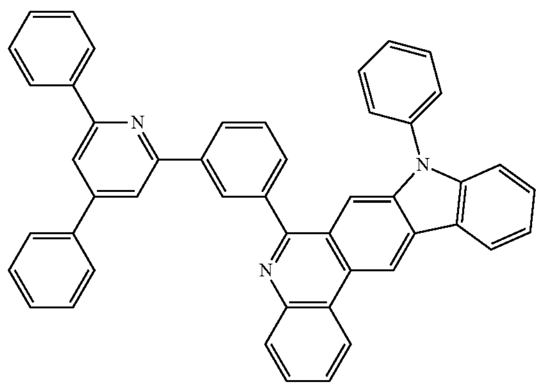
2-141
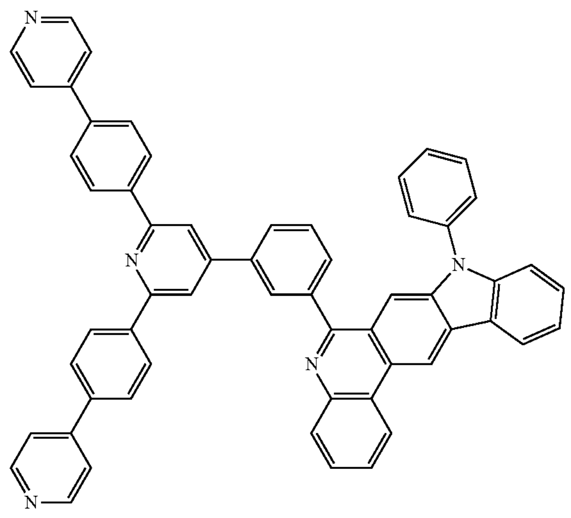
2-142
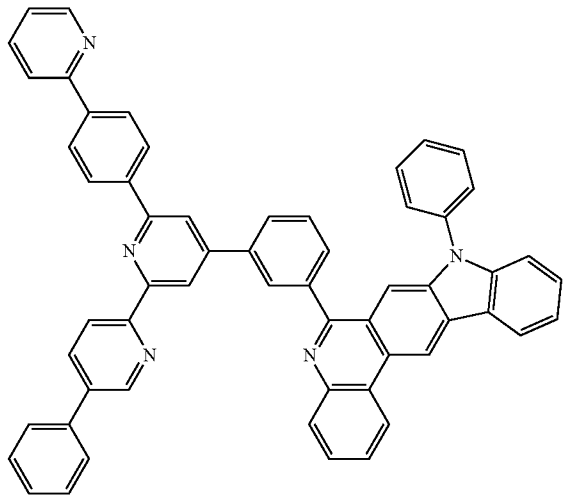
2-143
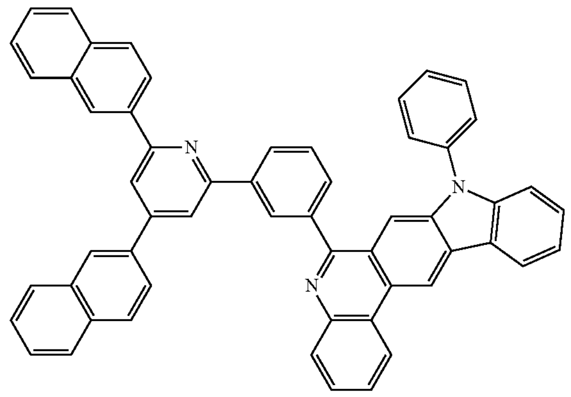
2-144
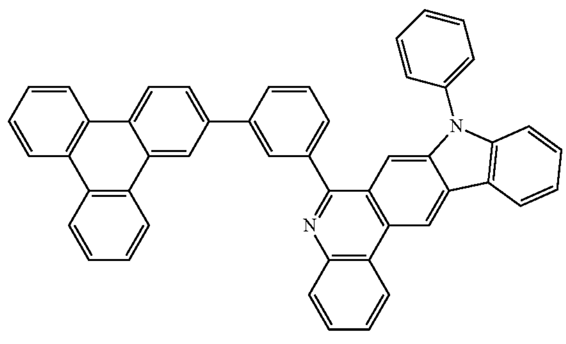
2-145
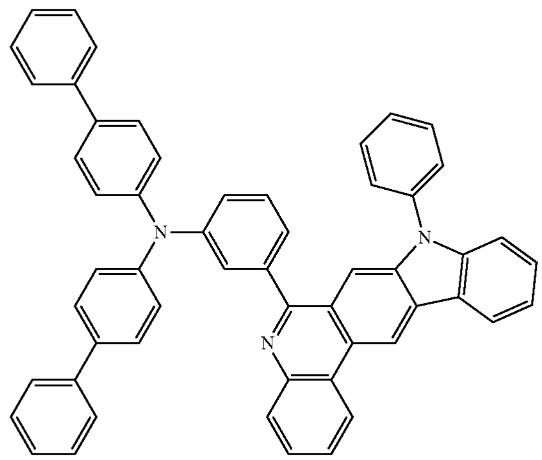

-continued
2-146
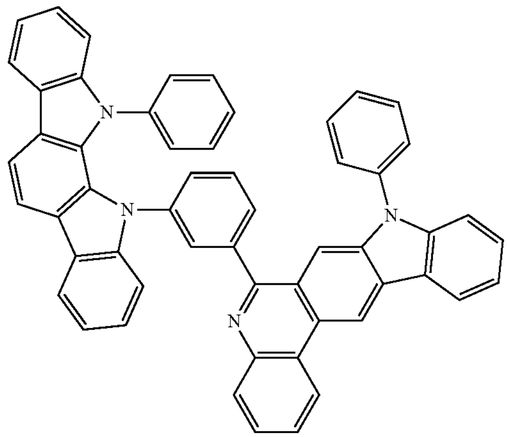
2-147
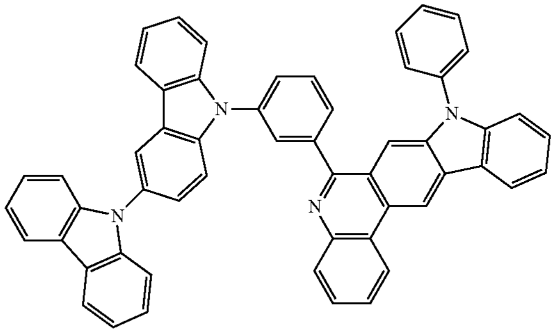
2-148
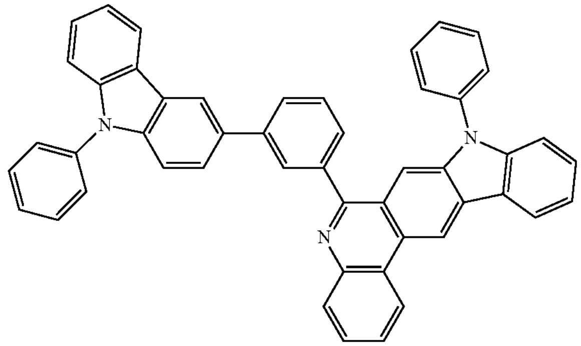
2-149
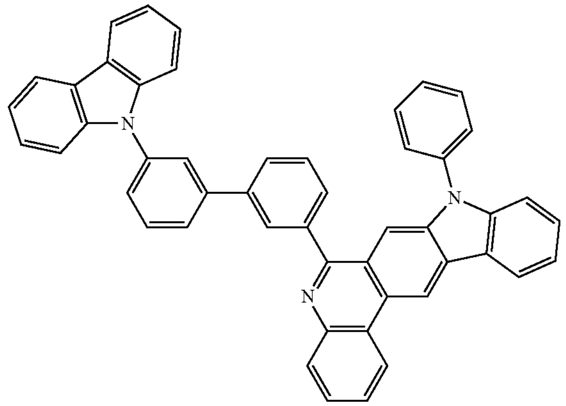
2-150
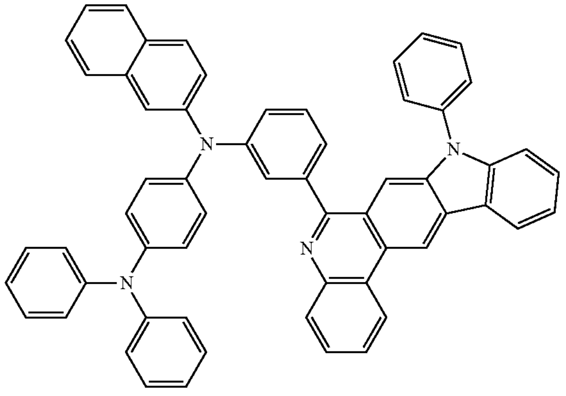

-continued
2-151
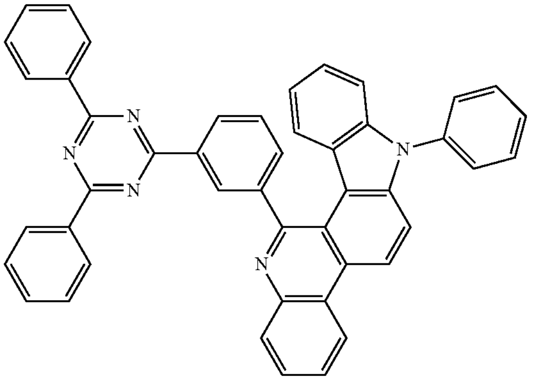
2-152
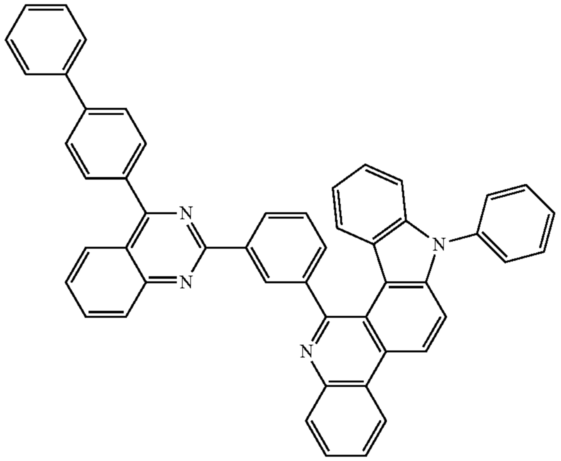
2-153
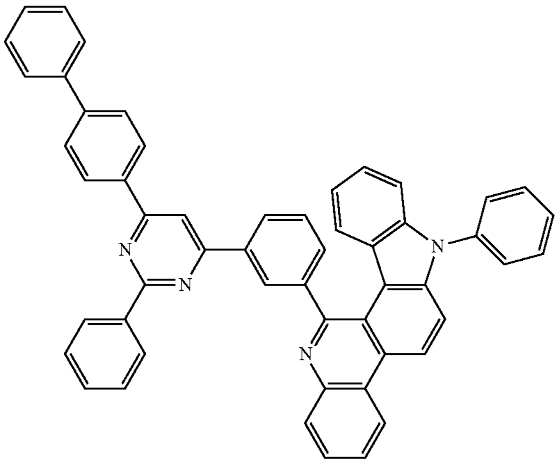
2-154
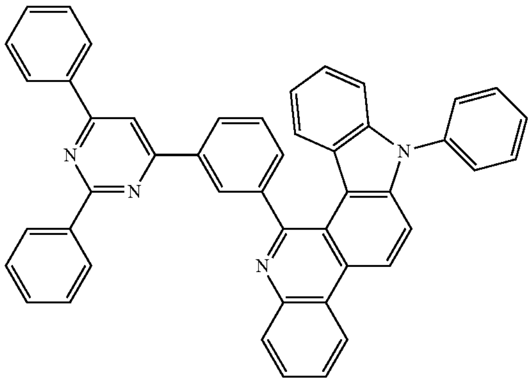
2-155
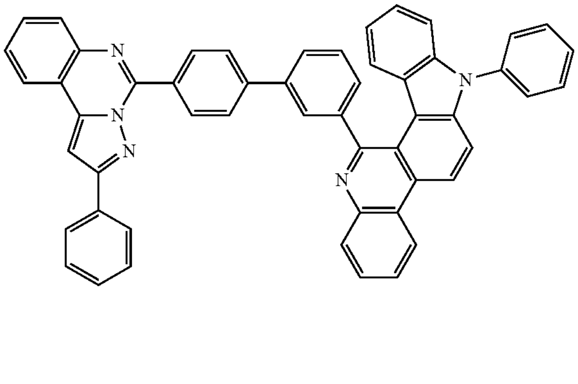
2-156
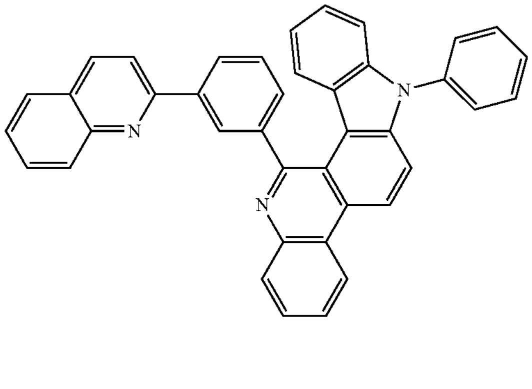

-continued
2-157
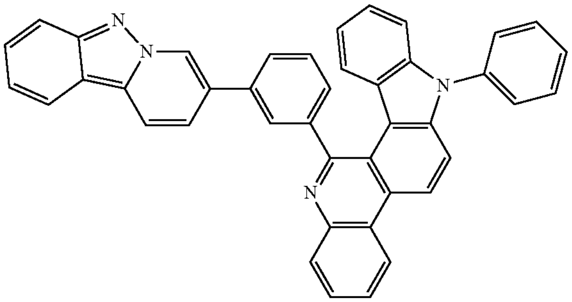
2-158
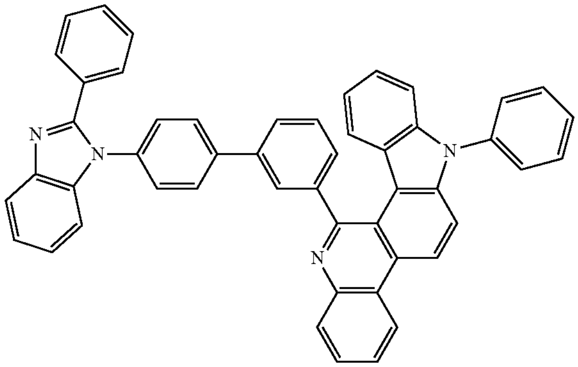
2-159
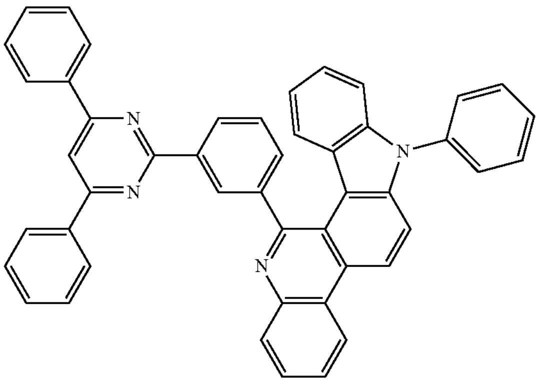
2-160
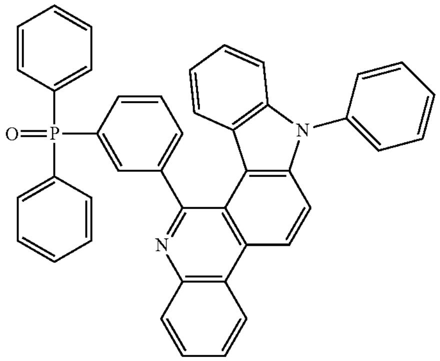
2-161
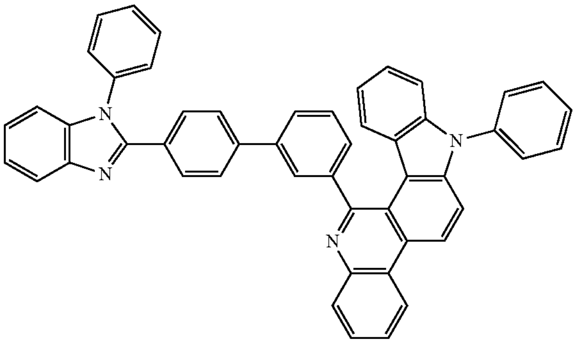
2-162
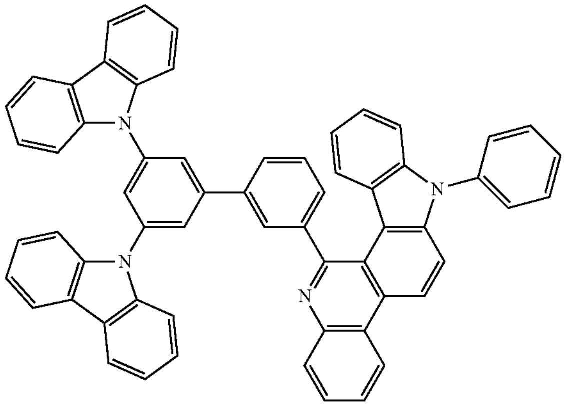
2-163
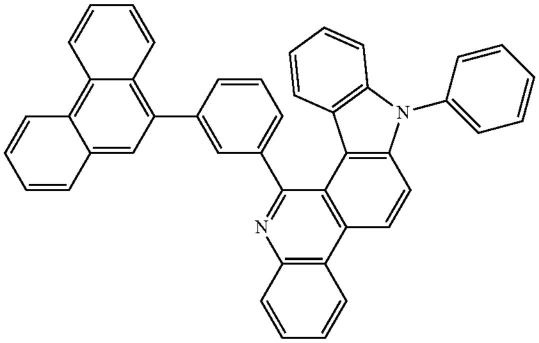
2-164
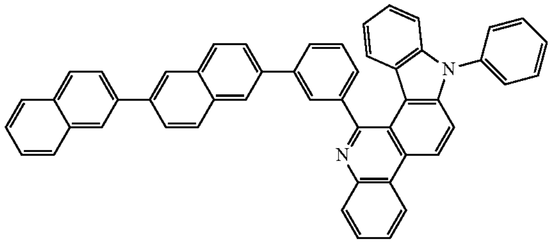

-continued
2-165
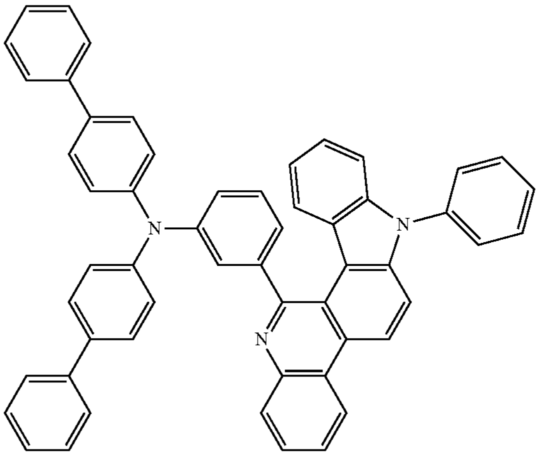
2-166
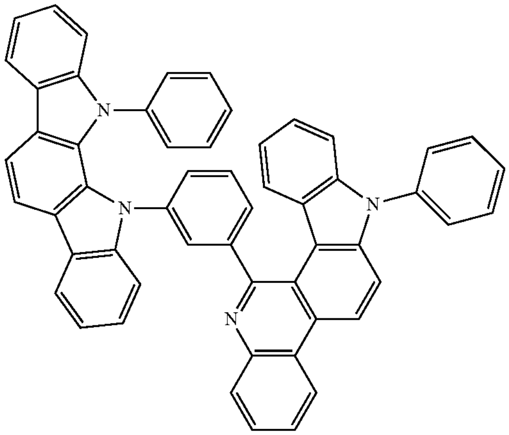
2-167
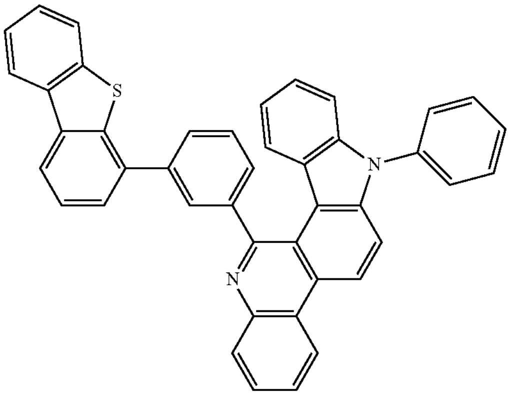
2-168
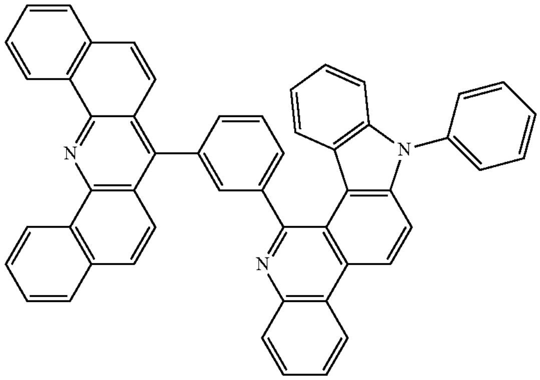
2-169
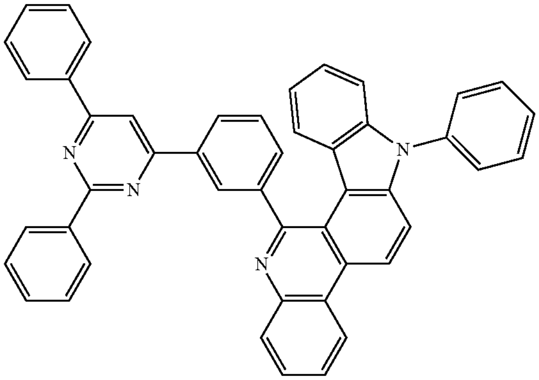
2-170
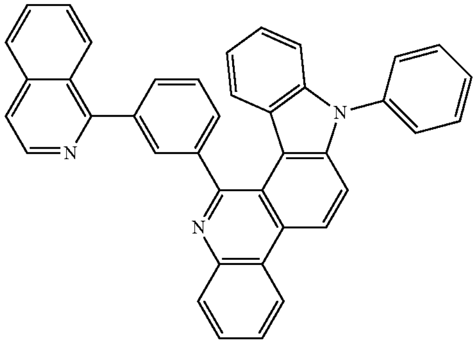

-continued
2-171
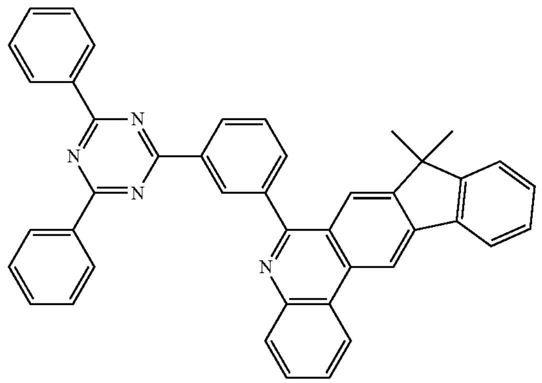
2-172
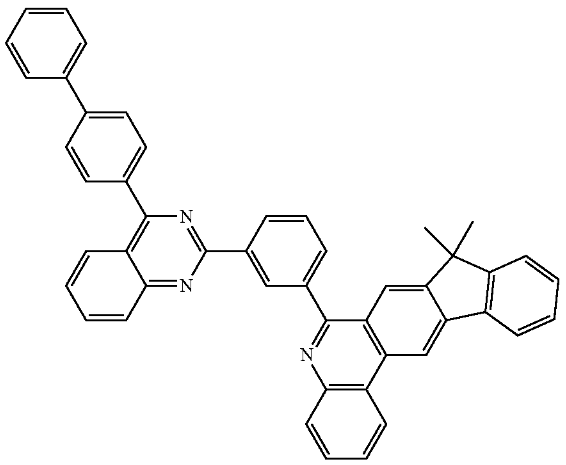
2-173
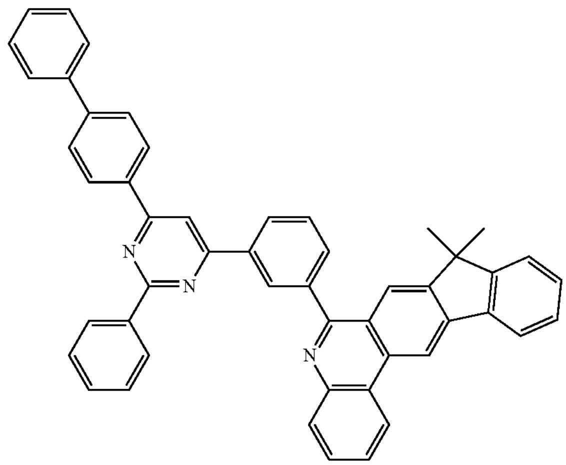
2-174
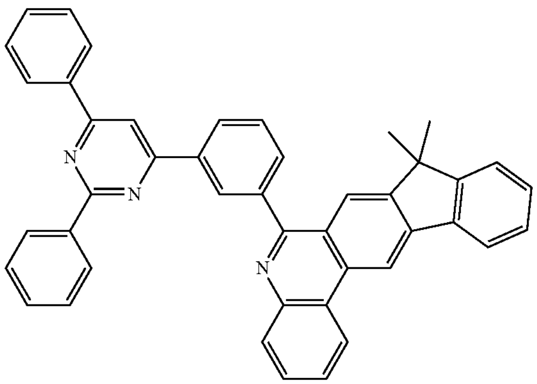
2-175
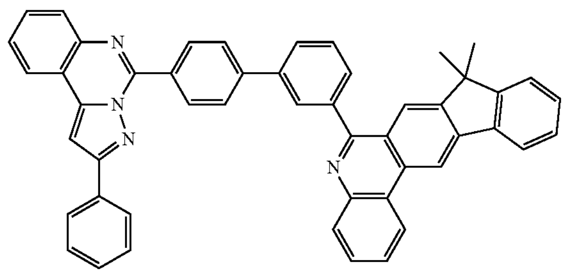
2-176
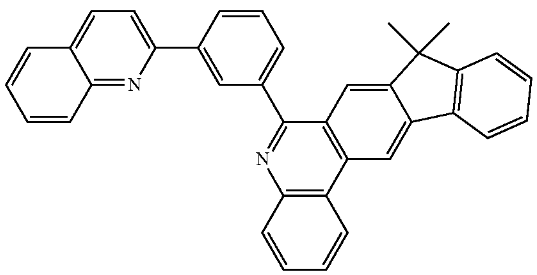
2-177
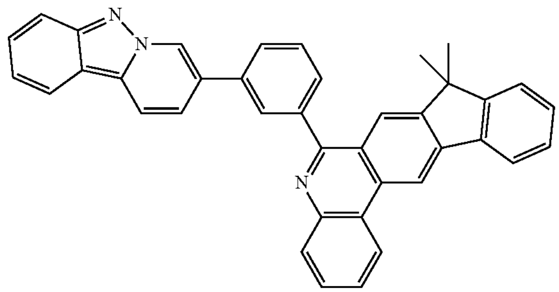
2-178
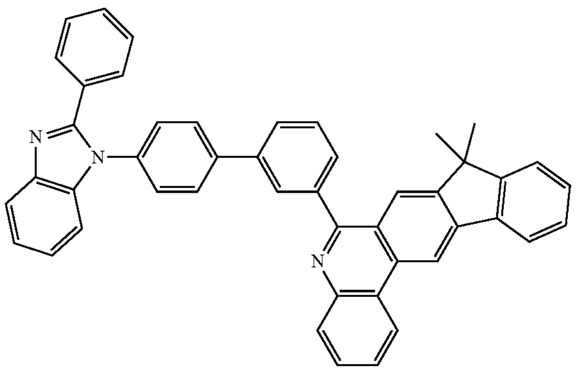

-continued
2-179
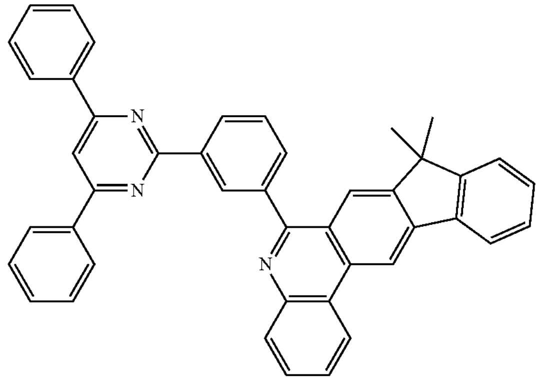
2-180
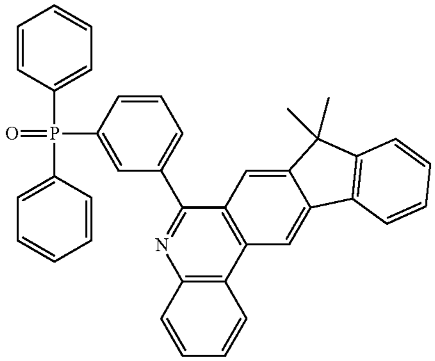
2-181
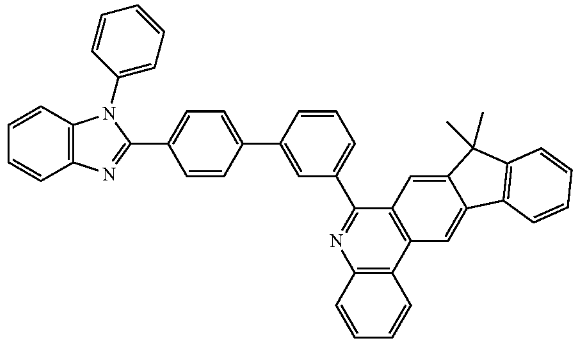
2-182
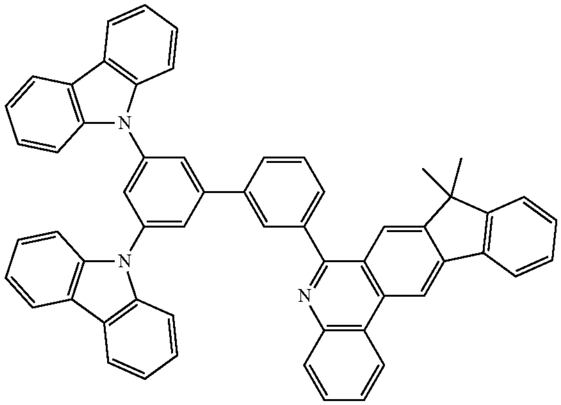
2-183
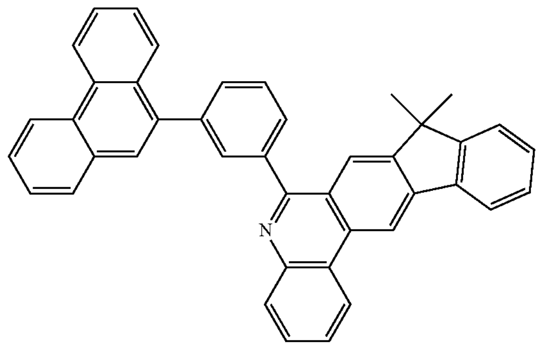
2-184
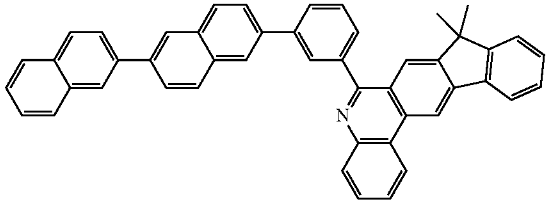

-continued
2-185
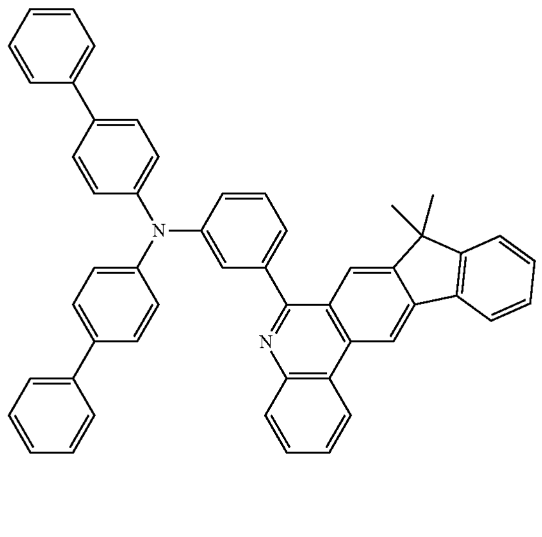
2-186
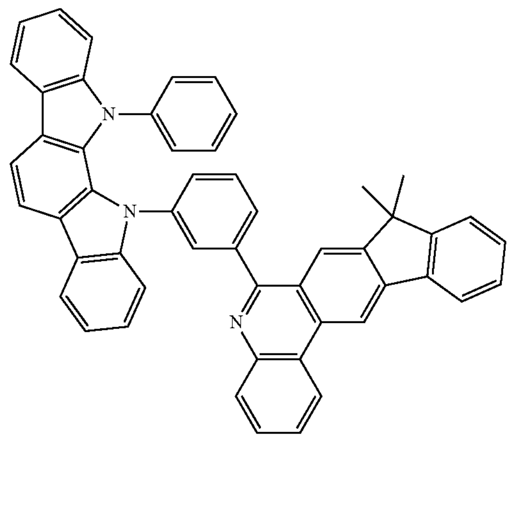
2-187
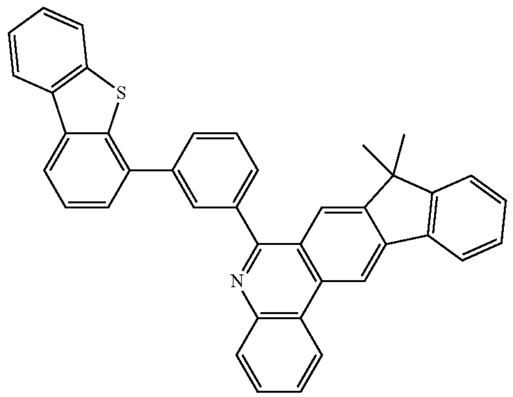
2-188
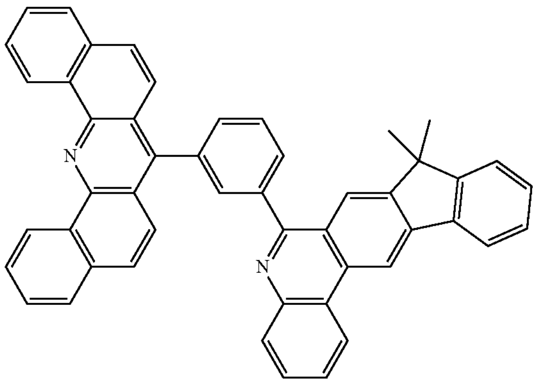
2-189
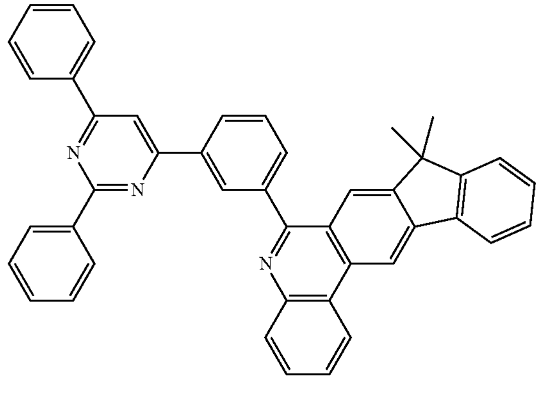
2-190
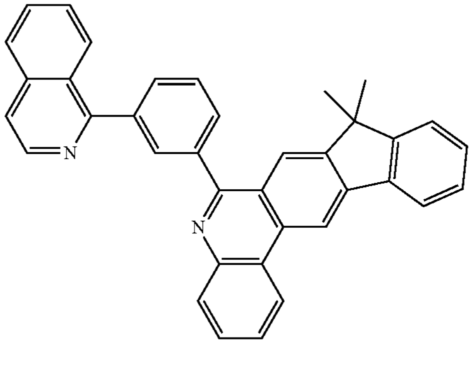

-continued
2-191
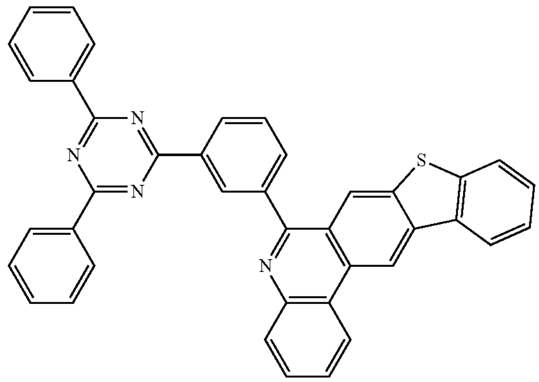
2-192
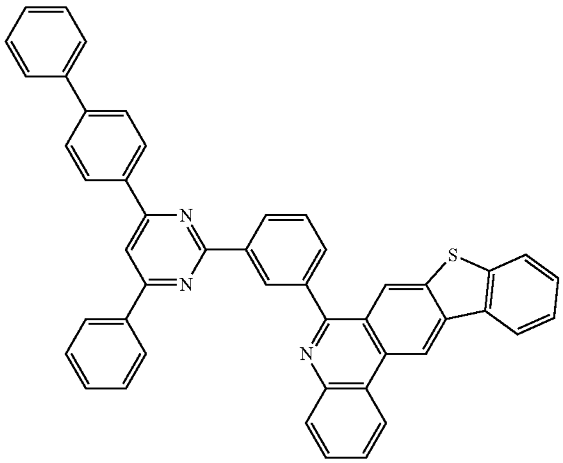
2-193
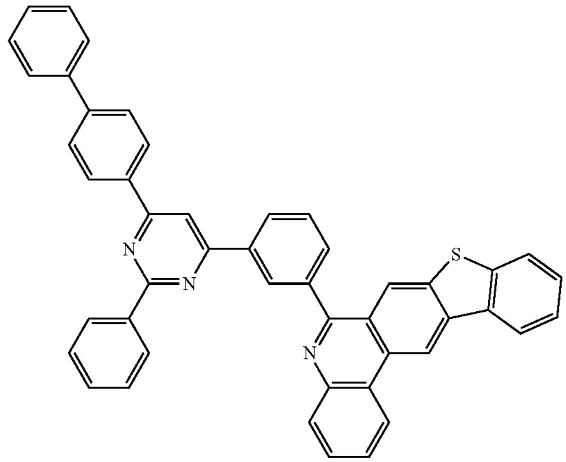
2-194
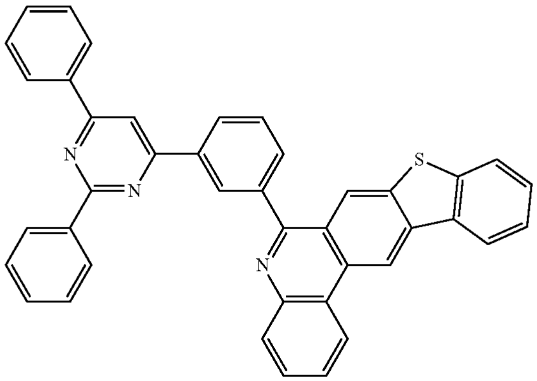
2-195
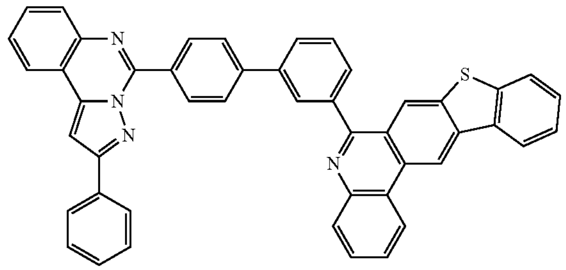
2-196
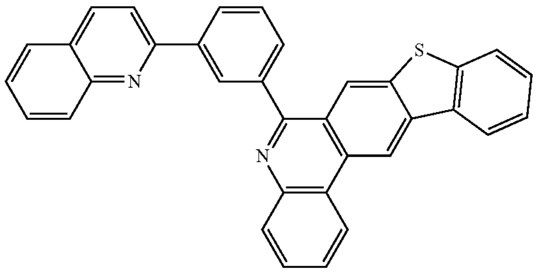
2-197
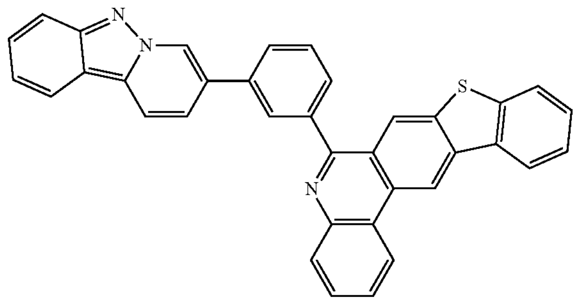
2-198
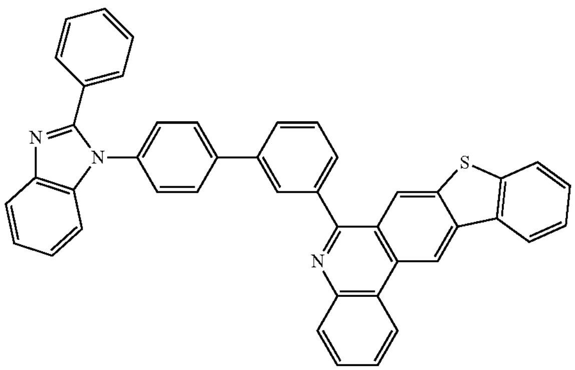

-continued
2-199
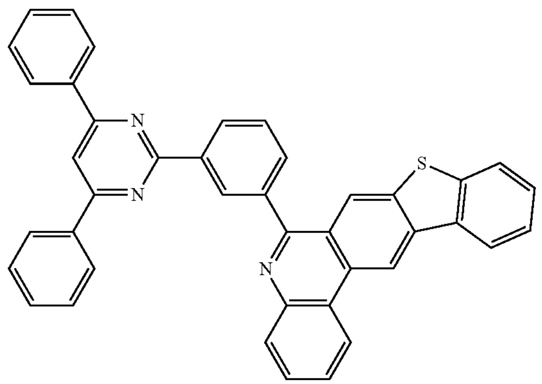
2-200
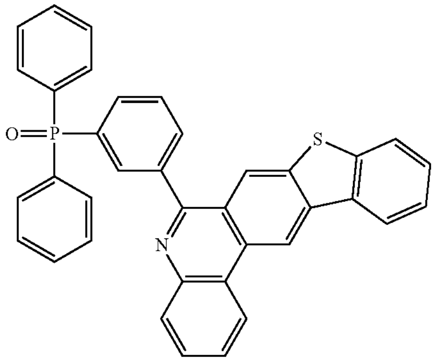
2-201
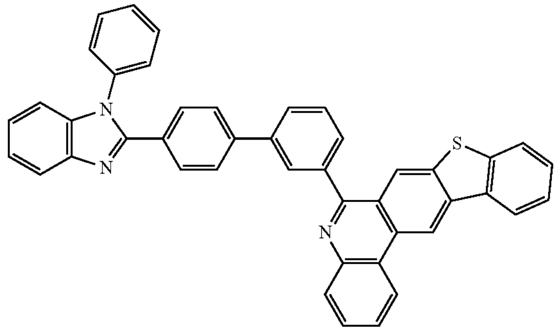
2-202
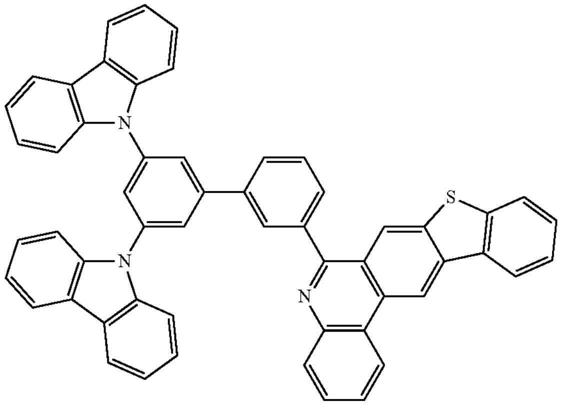
2-203
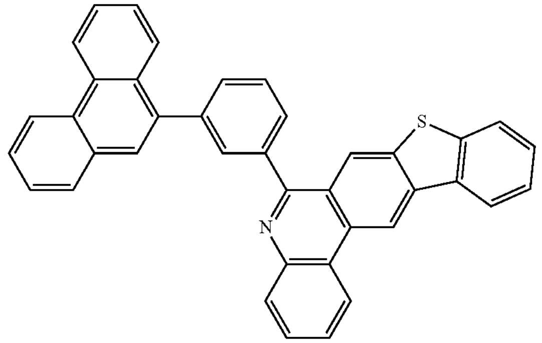
2-204
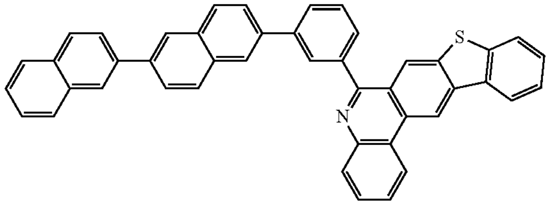

-continued
2-205
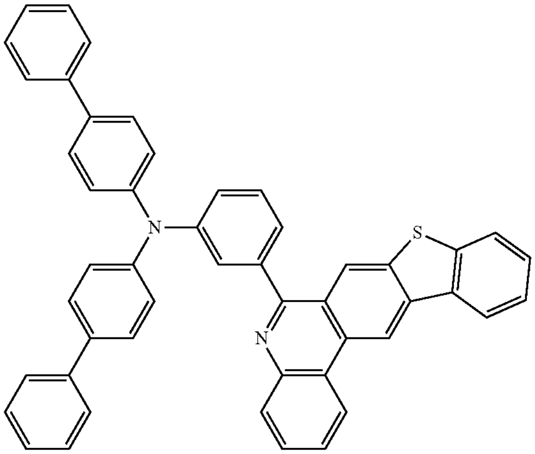
2-206
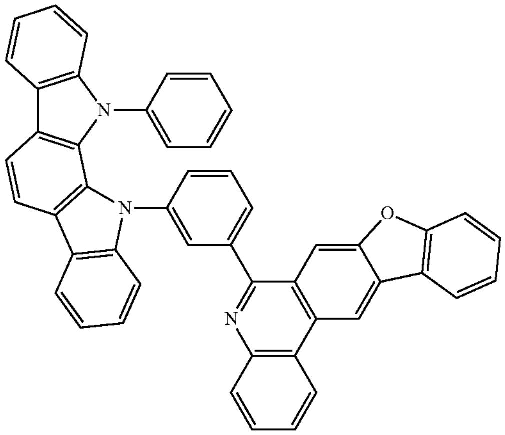
2-207
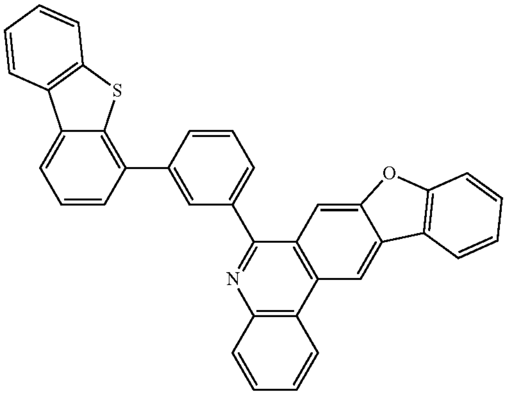
2-208
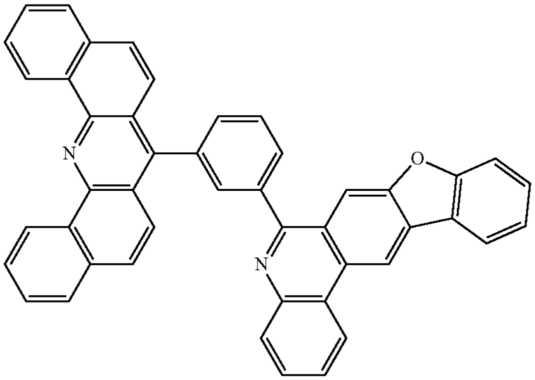
2-209
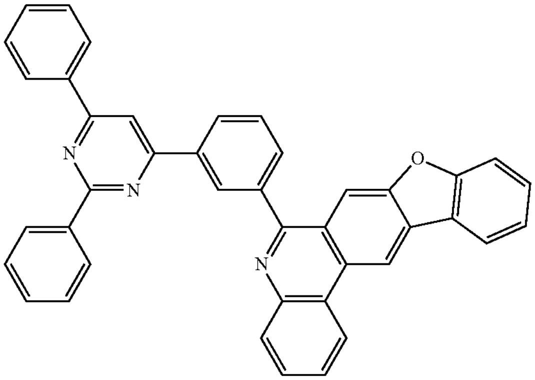
2-210
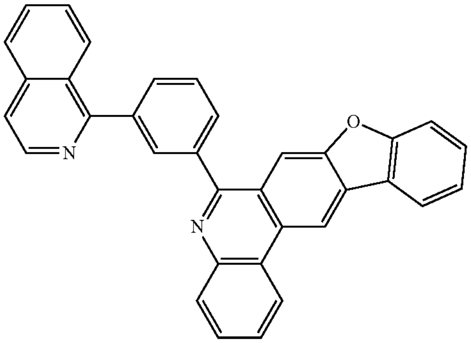

-continued
2-211
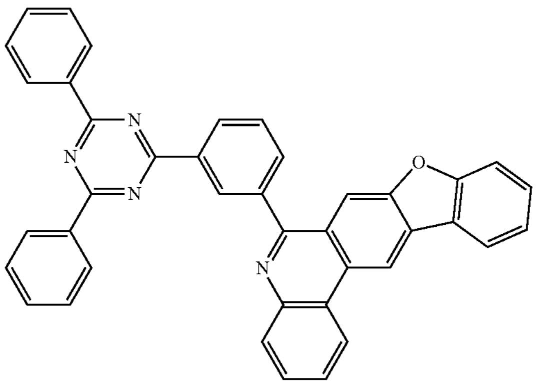
2-212
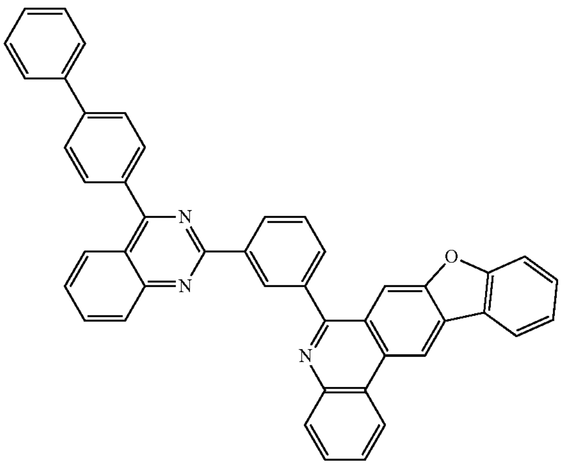
2-213
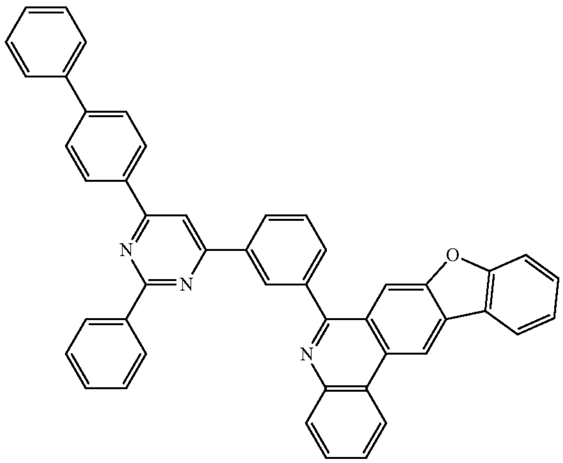
2-214
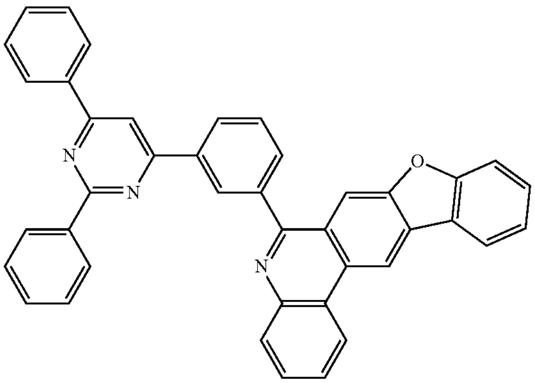
2-215
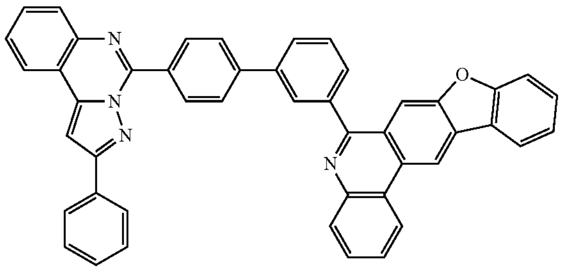
2-216
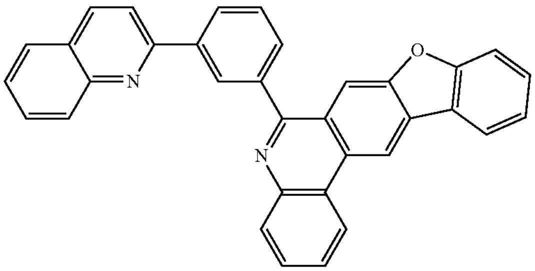
2-217
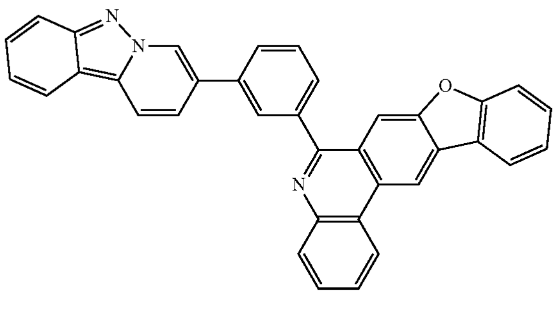
2-218
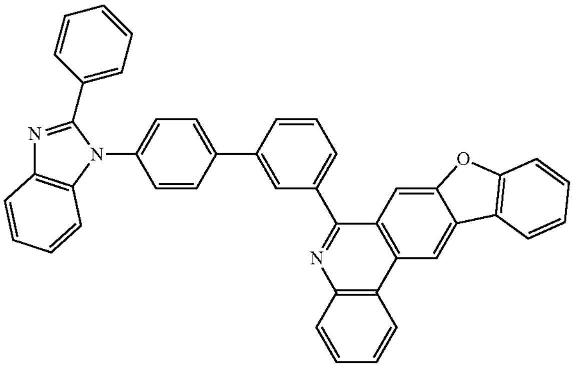

-continued
2-219
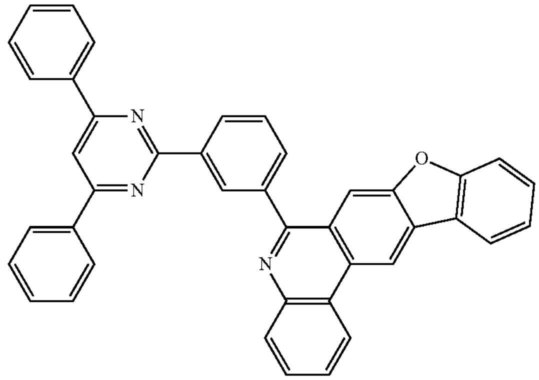
2-220
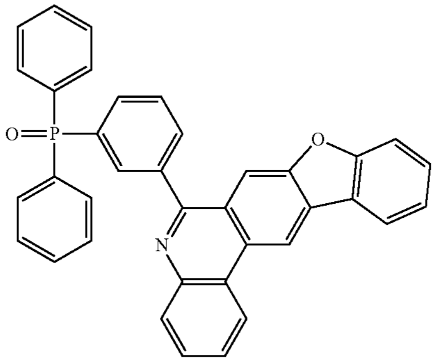
2-221
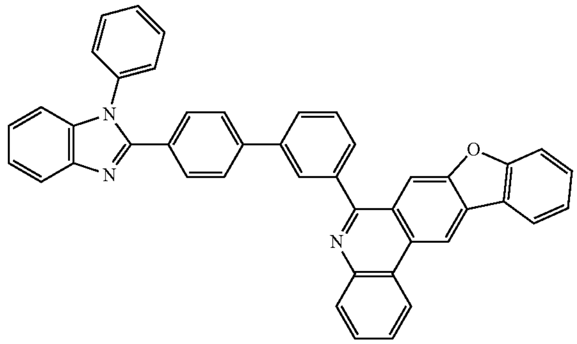
2-222
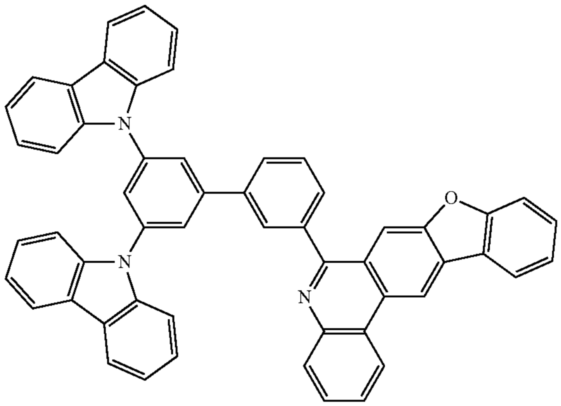
2-223
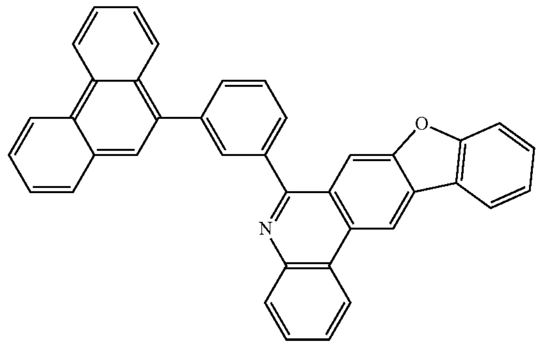
2-224
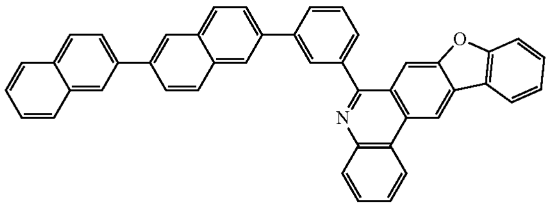

-continued
2-225
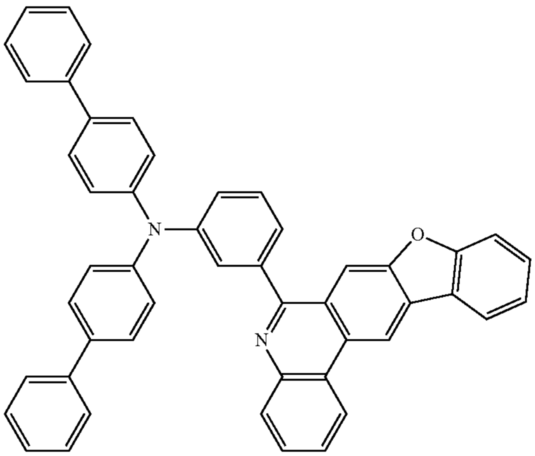
2-226
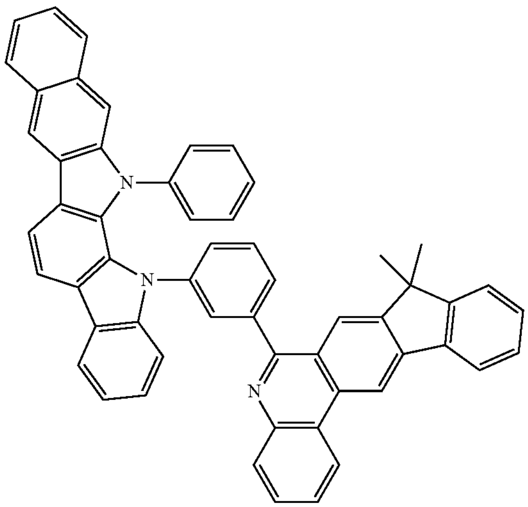
2-227
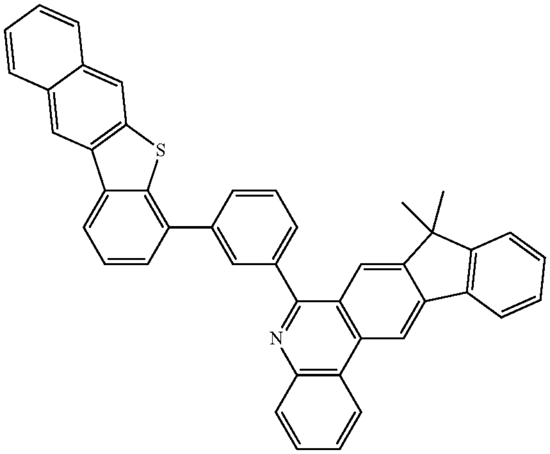
2-228
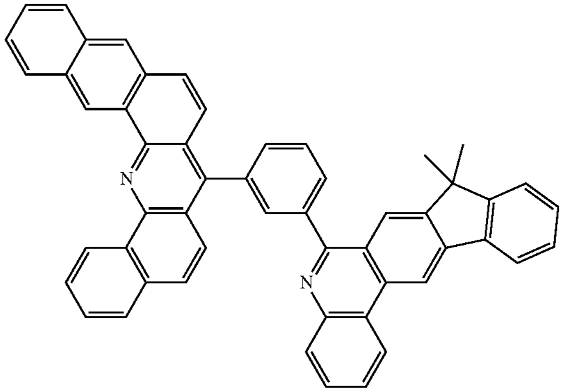
2-229
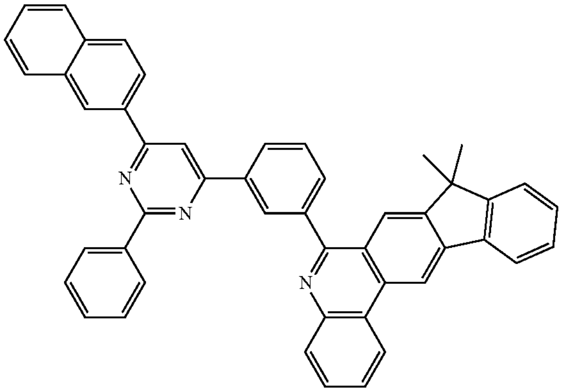
2-230
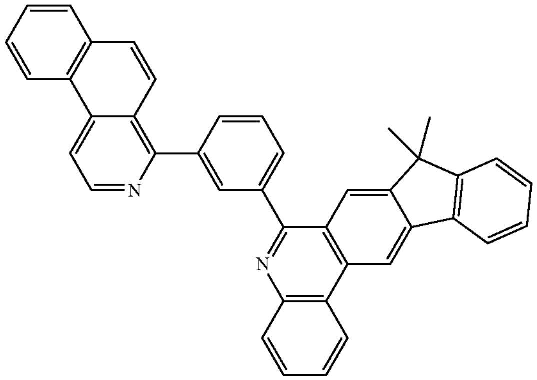

-continued
2-231
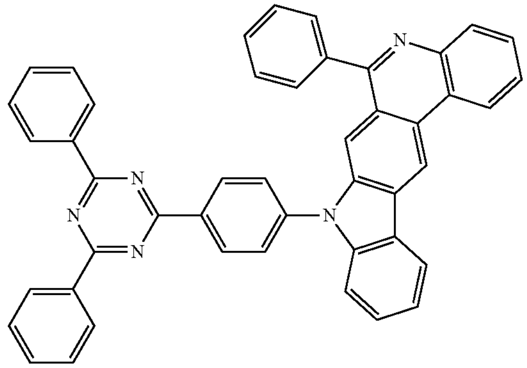
2-232
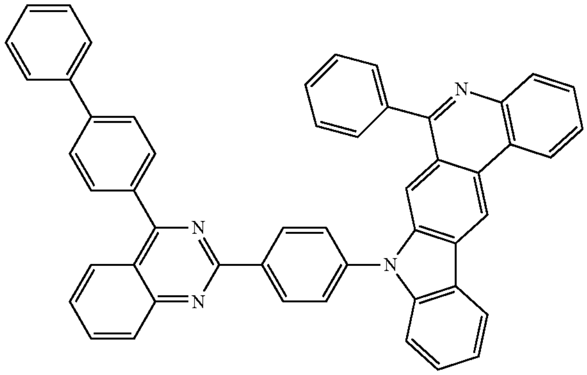
2-233
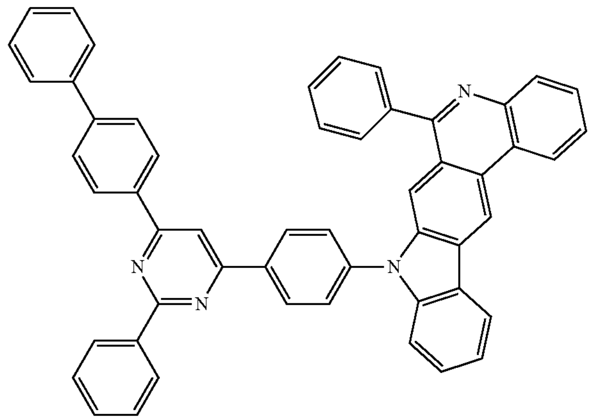
2-234
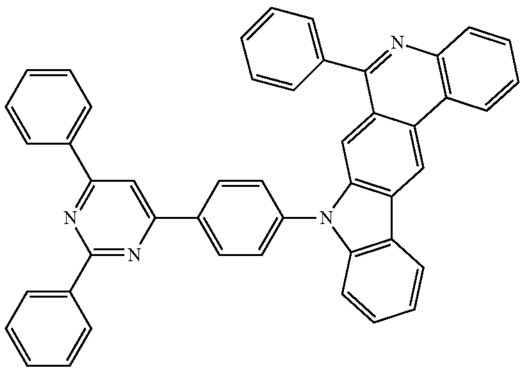
2-235
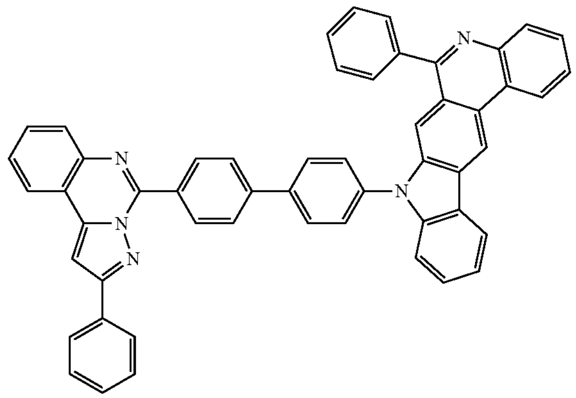
2-236
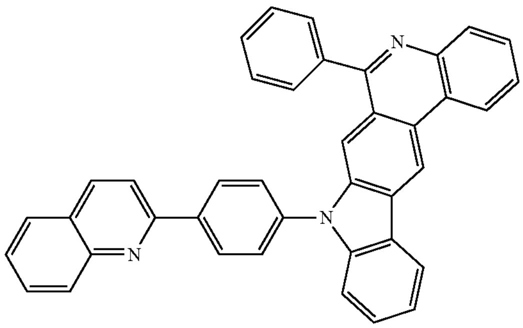
2-237
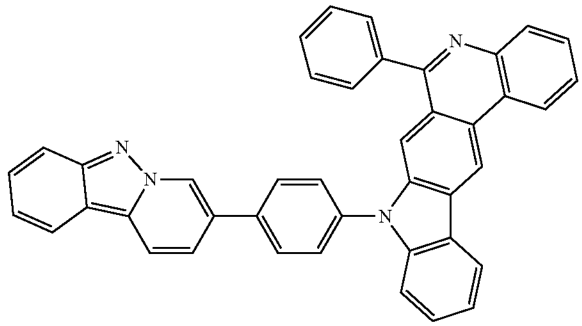
2-238
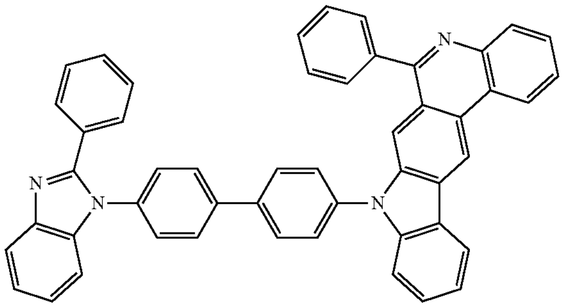

-continued
2-239
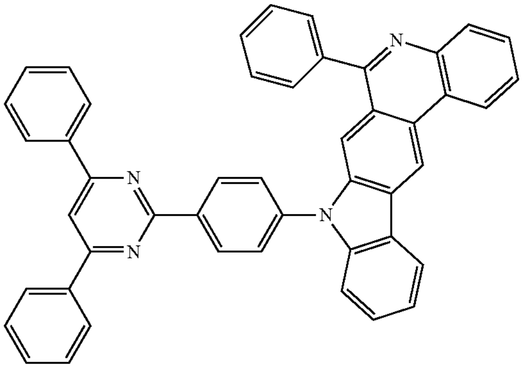
2-240
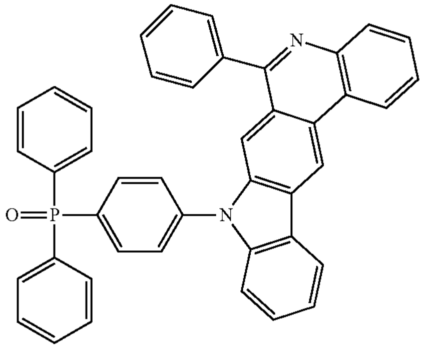
2-241
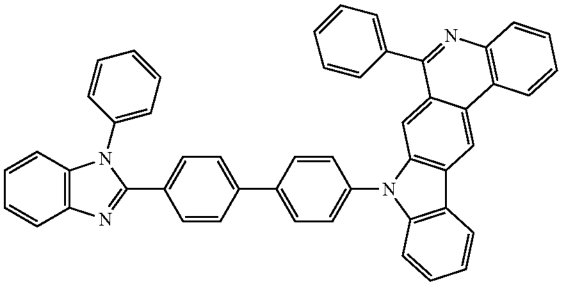
2-242
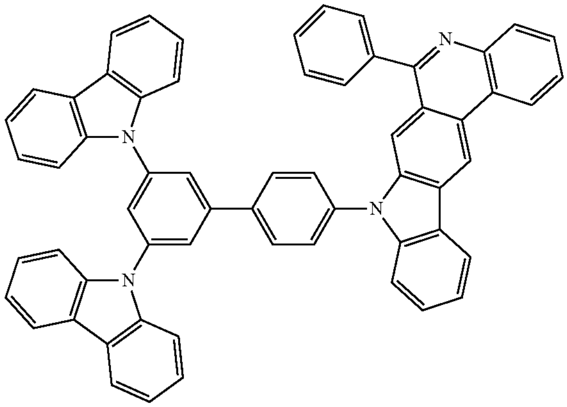
2-243
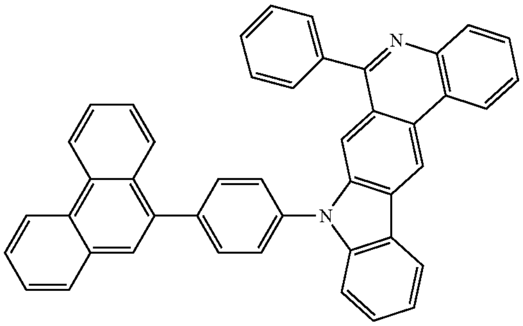
2-244
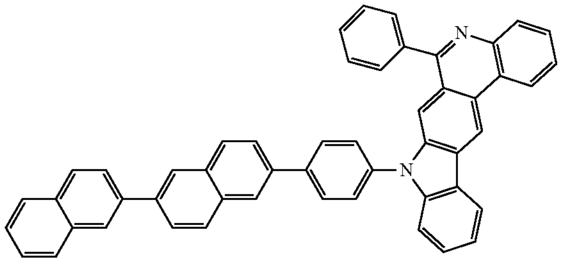
2-245
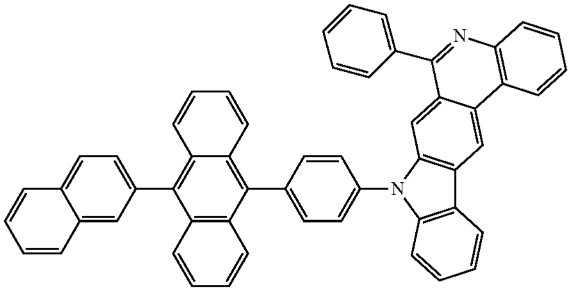
2-246
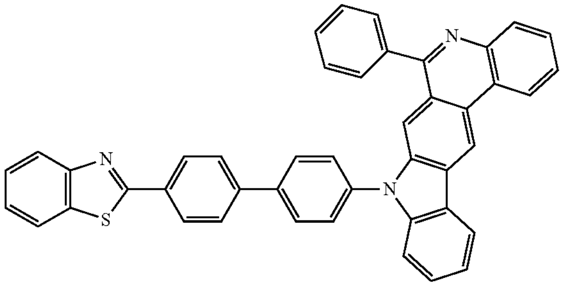

-continued
2-247
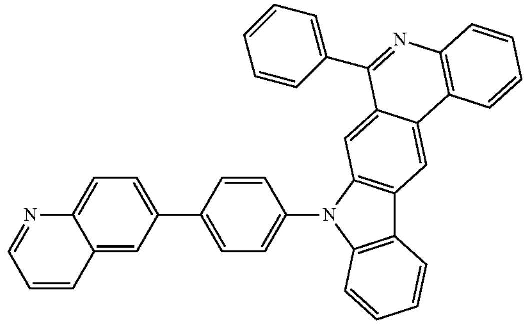
2-248
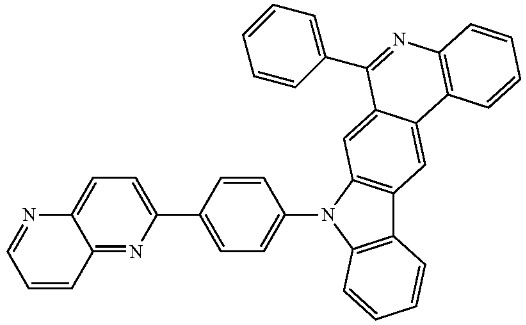
2-249
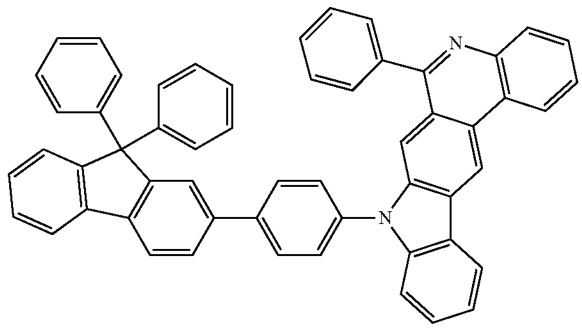
2-250
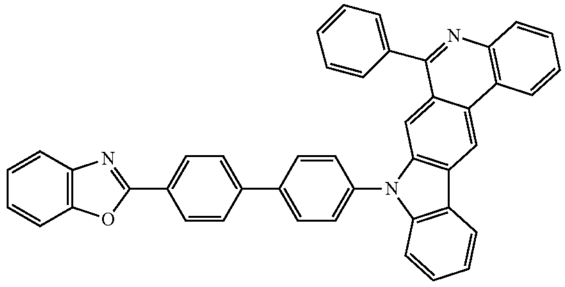
2-251
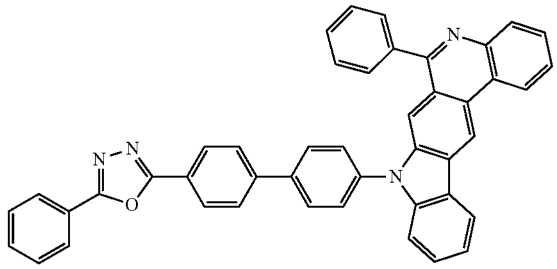
2-252
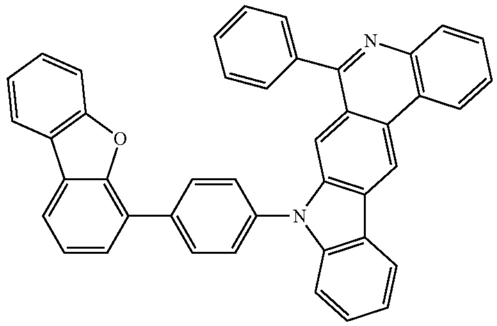
2-253
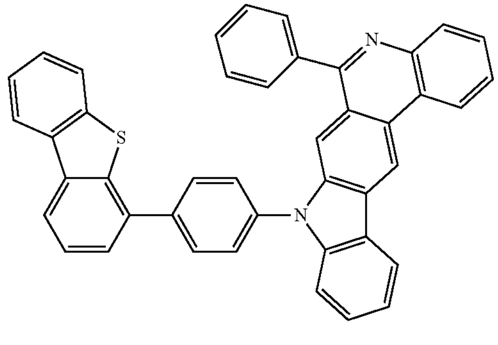
2-254
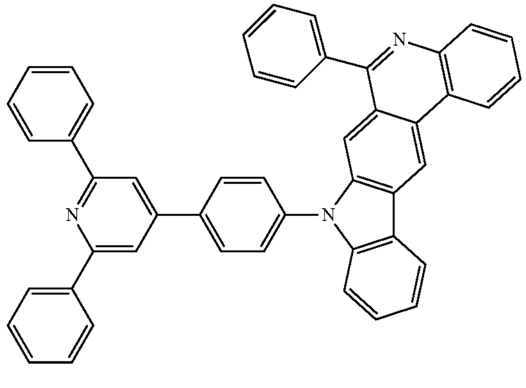

-continued
2-255
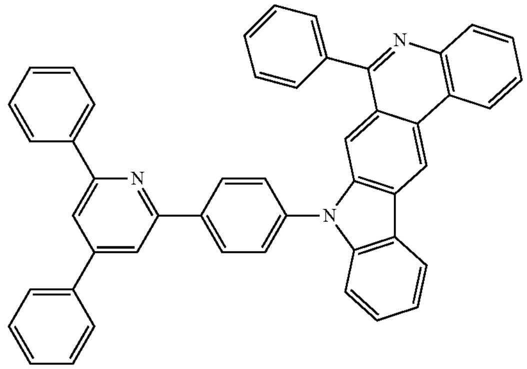
2-256
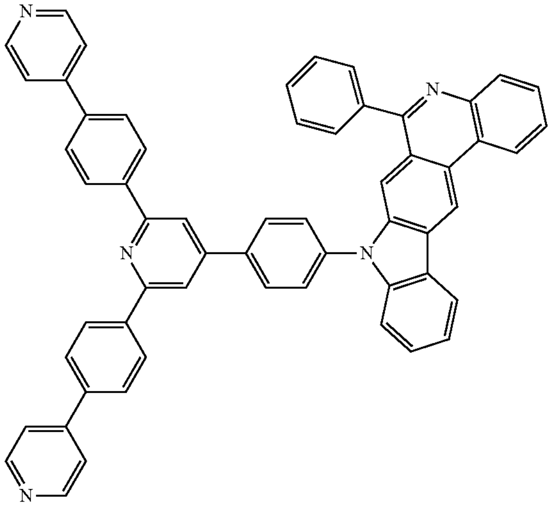
2-257
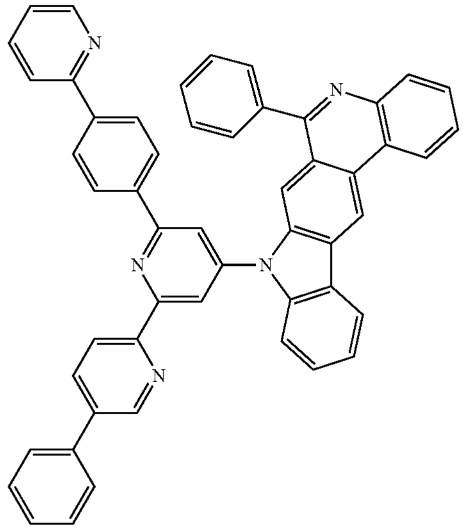
2-258
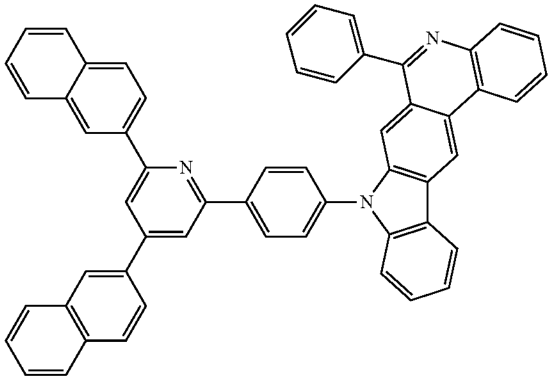
2-259
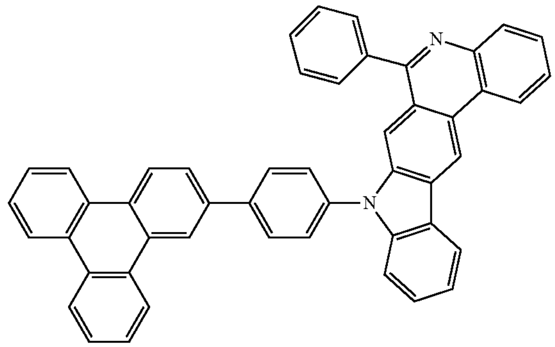
2-260
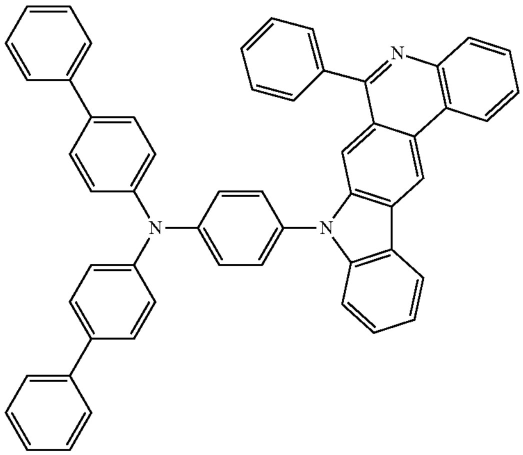

-continued
2-261
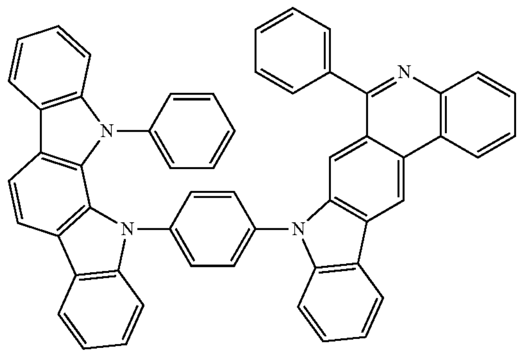
2-262
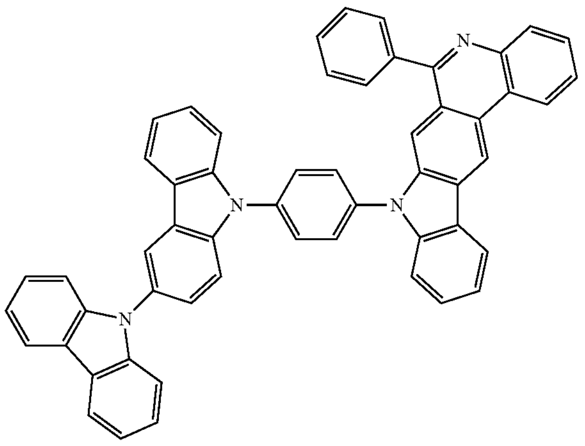
2-263
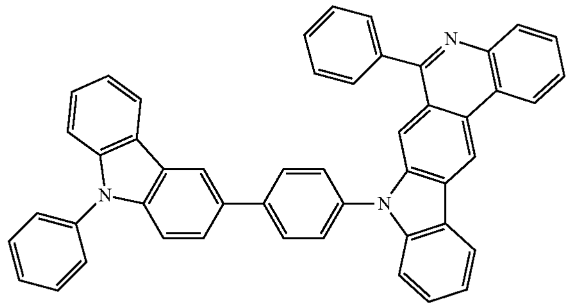
2-264
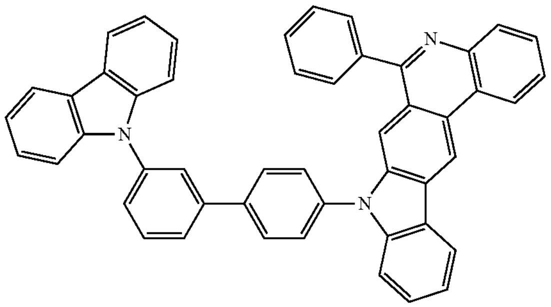
2-265
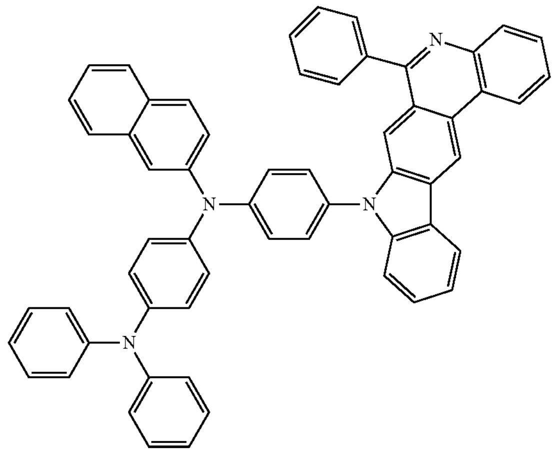
2-266
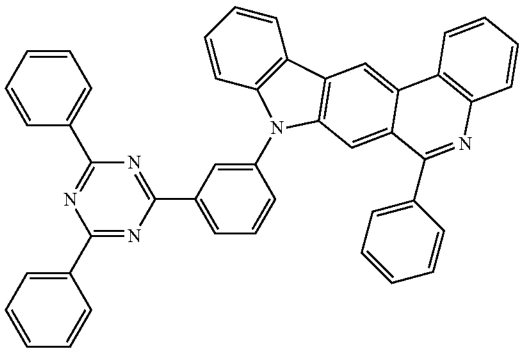

-continued
2-267
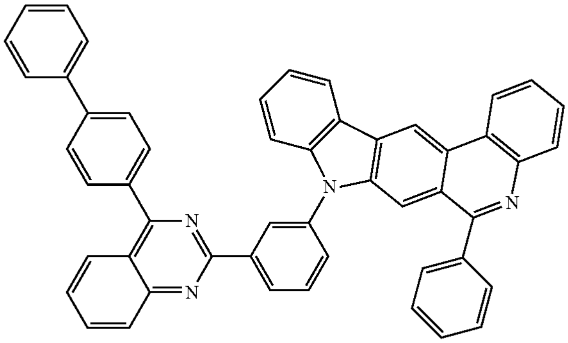
2-268
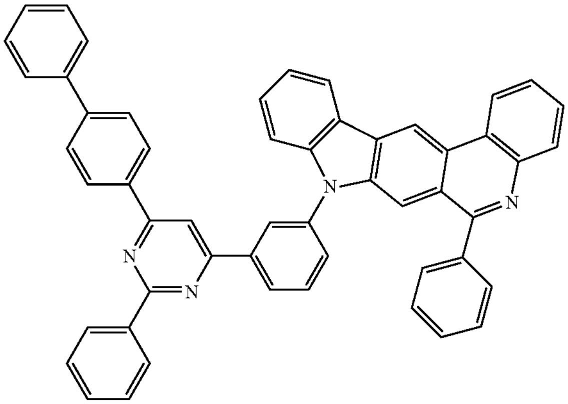
2-269
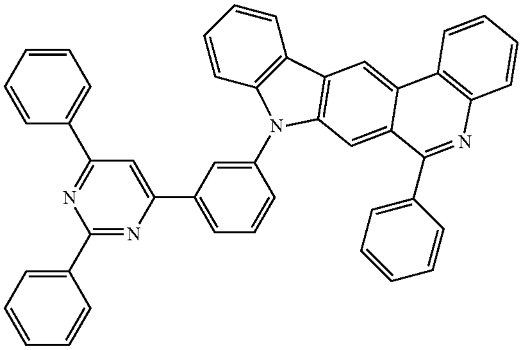
2-270
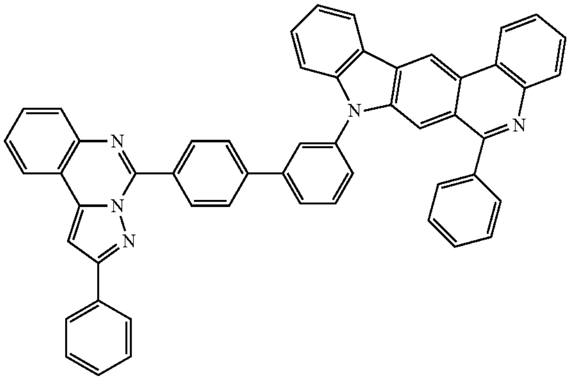
2-271
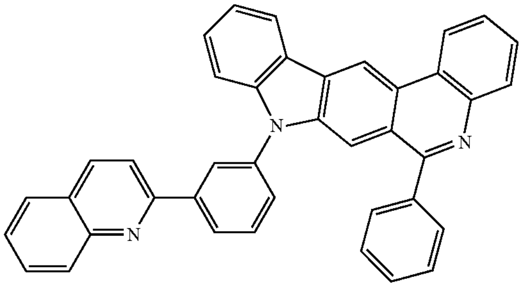
2-272
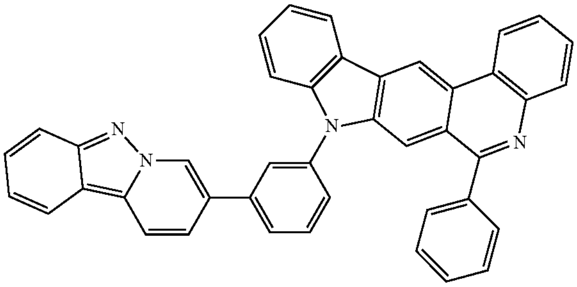
2-273
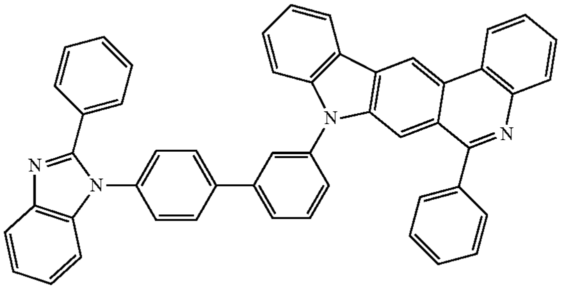
2-274
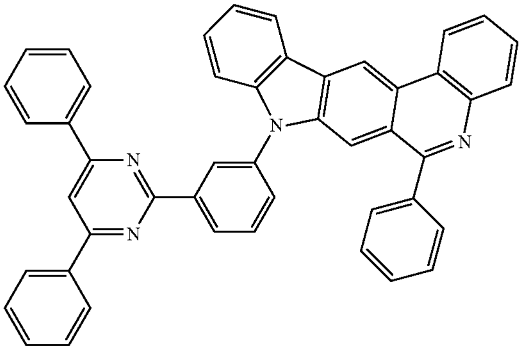

-continued
2-275
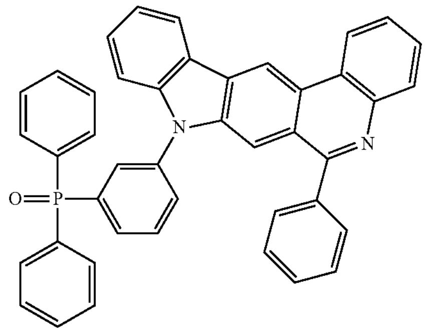
2-276
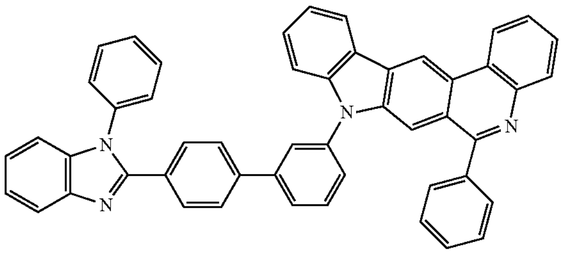
2-277
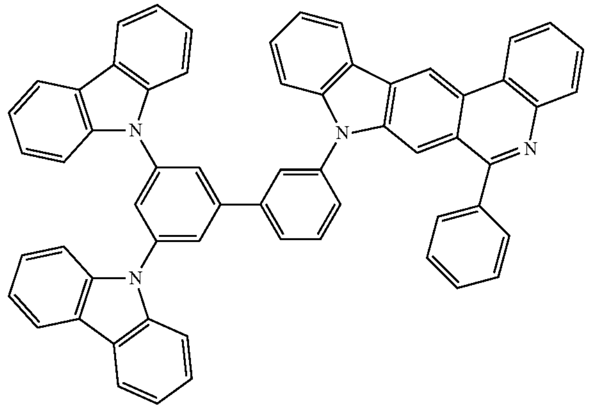
2-278
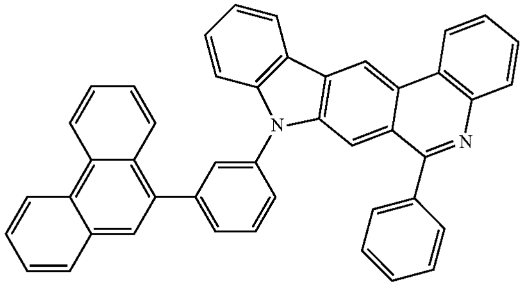
2-279
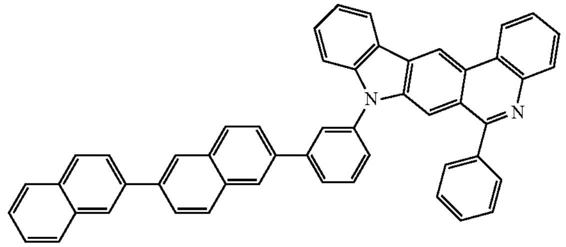
2-280
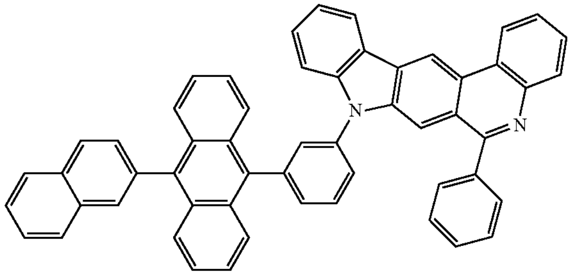
2-281
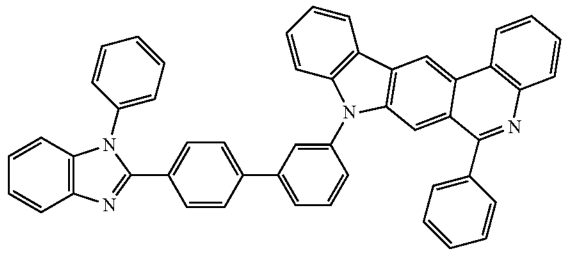
2-282
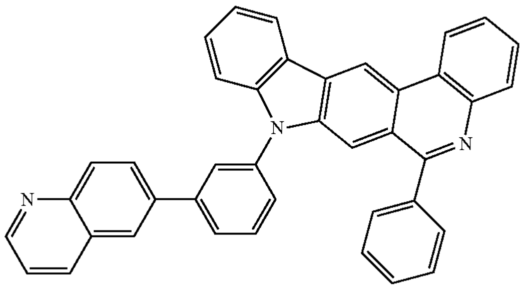

-continued
2-283
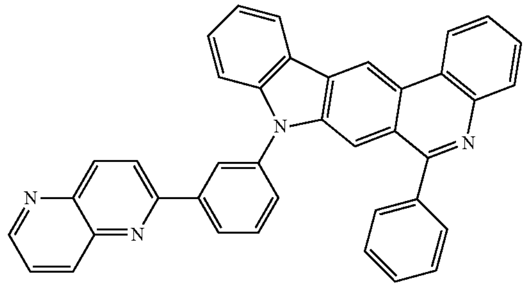
2-284
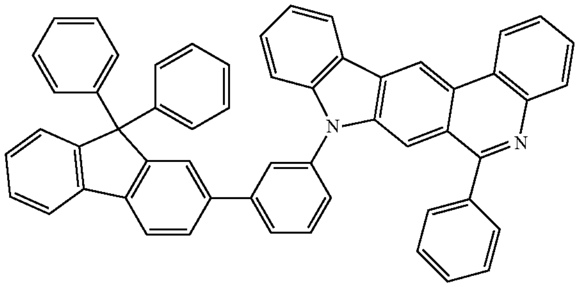
2-285
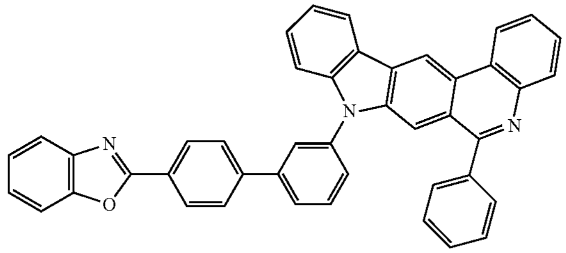
2-286
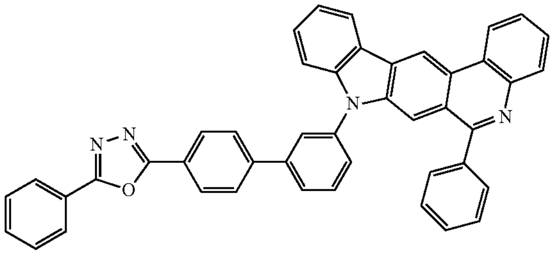
2-287
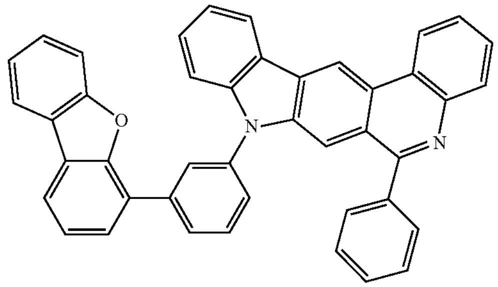
2-288
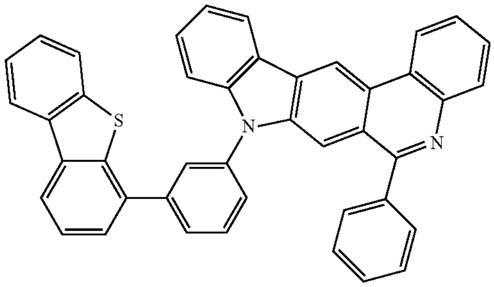
2-289
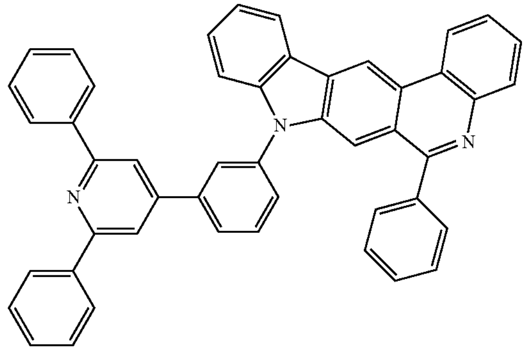
2-290
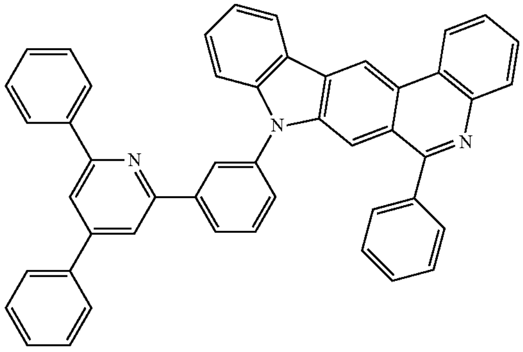

-continued
2-291
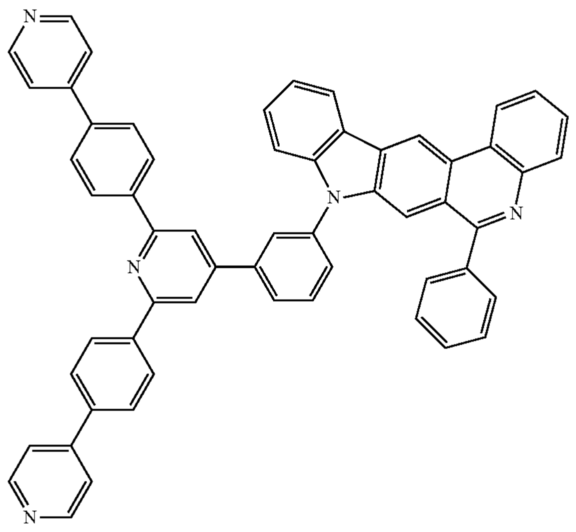
2-292
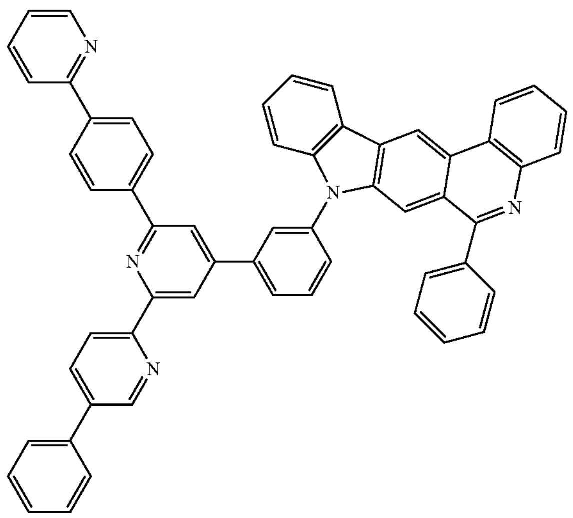
2-293
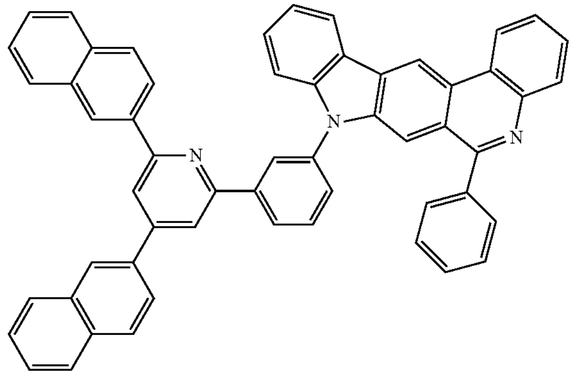
2-294
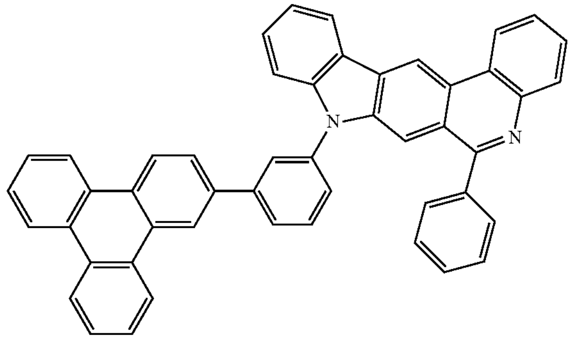
2-295
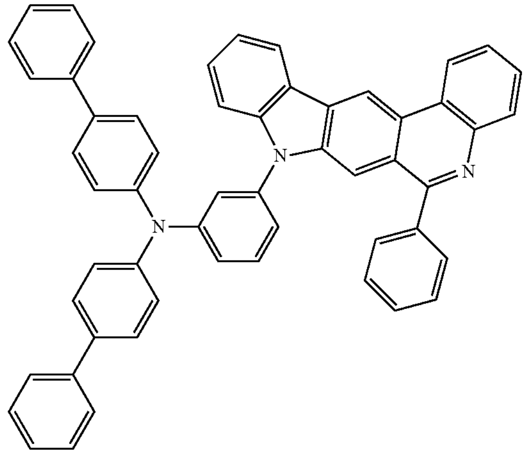
2-296
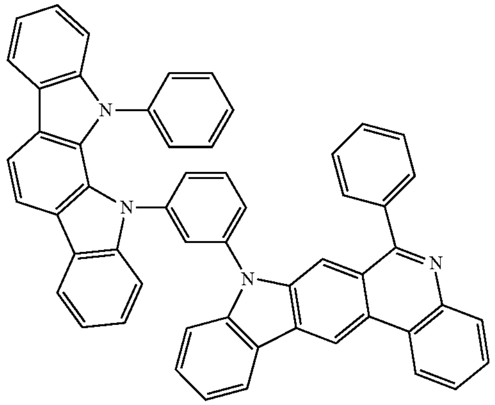

-continued
2-297
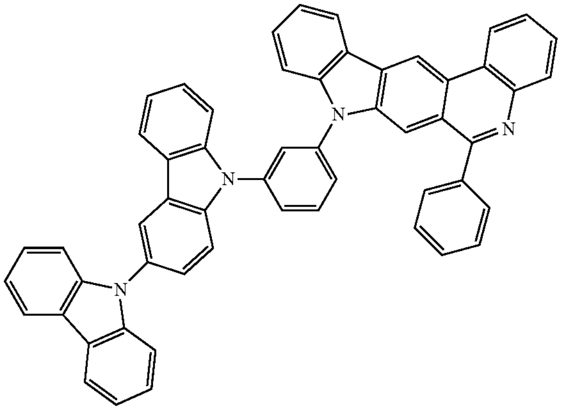
2-298
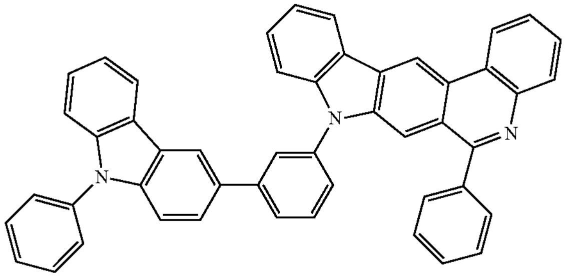
2-299
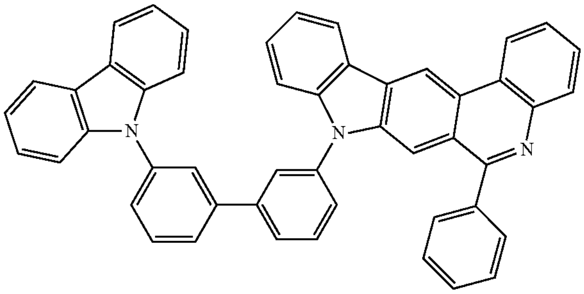
2-300
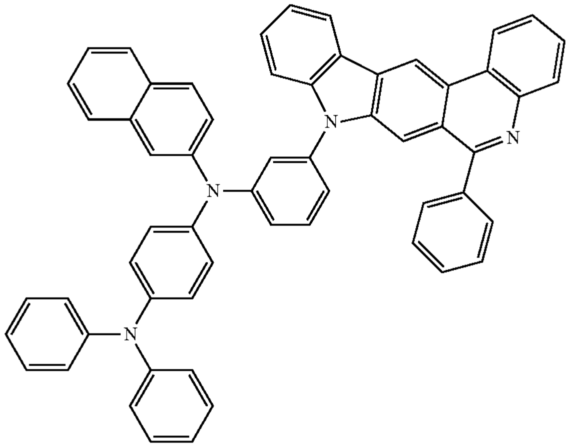
3-1
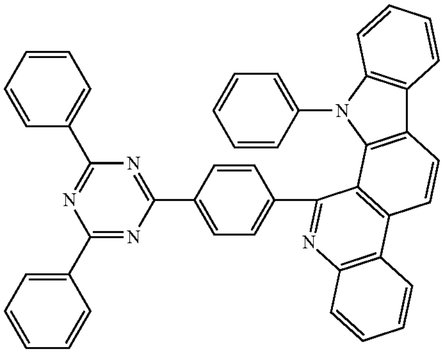
3-2
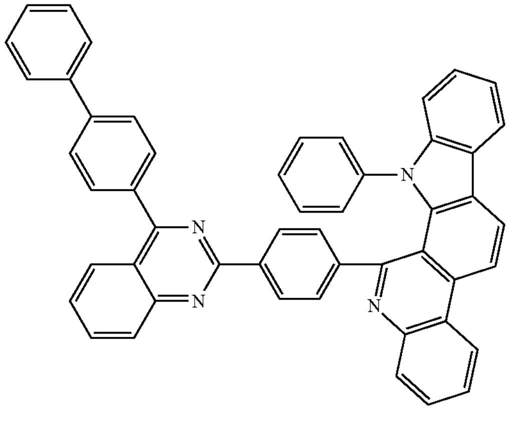

-continued
3-3
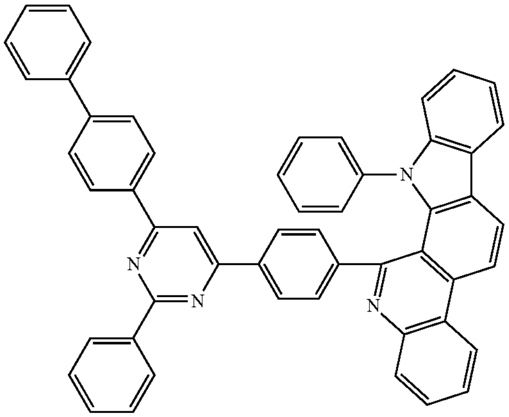
3-4
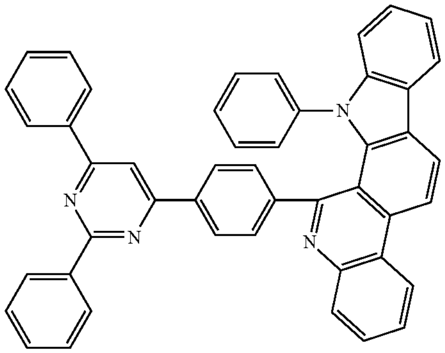
3-5
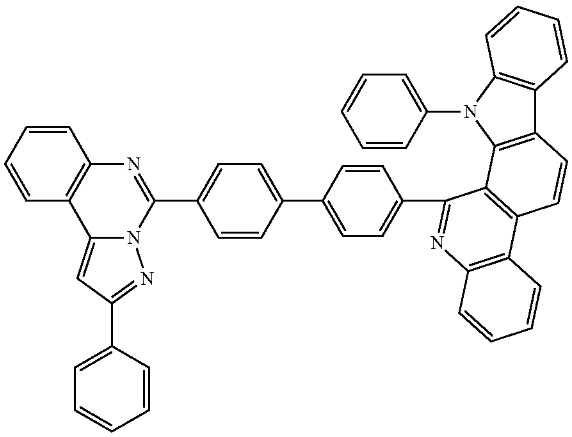
3-6
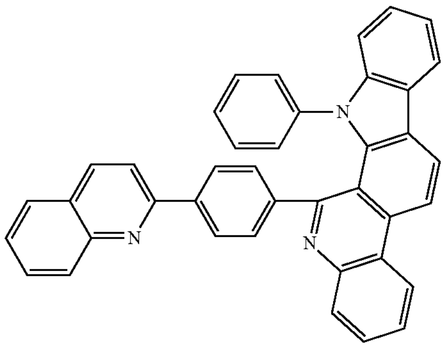
3-7
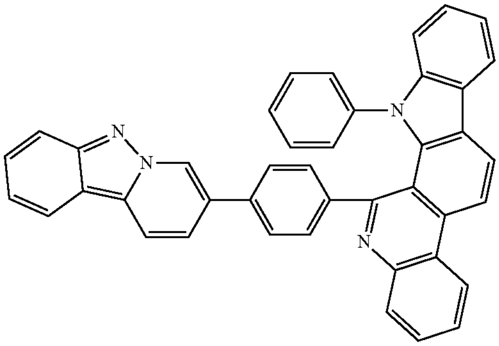
3-8
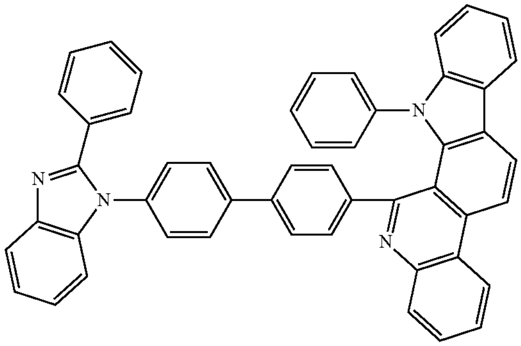
3-9
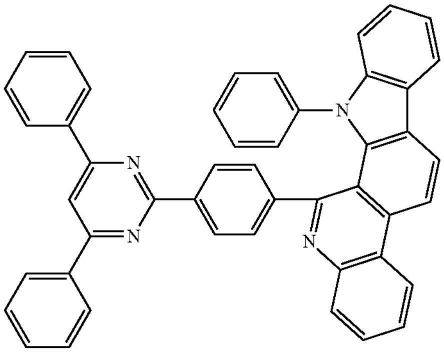
3-10
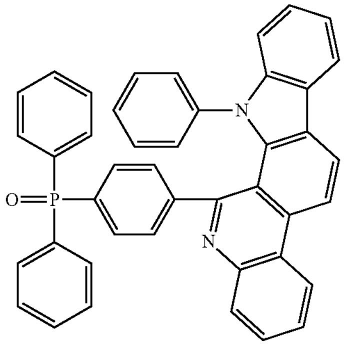

-continued
3-11
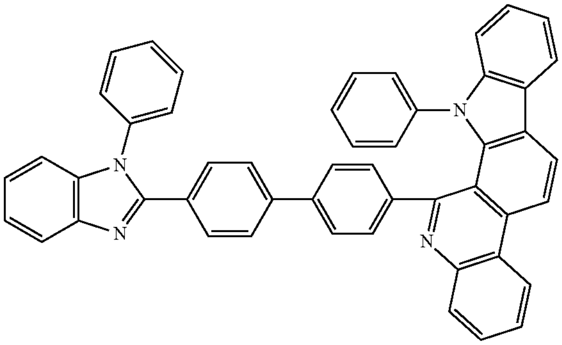
3-12
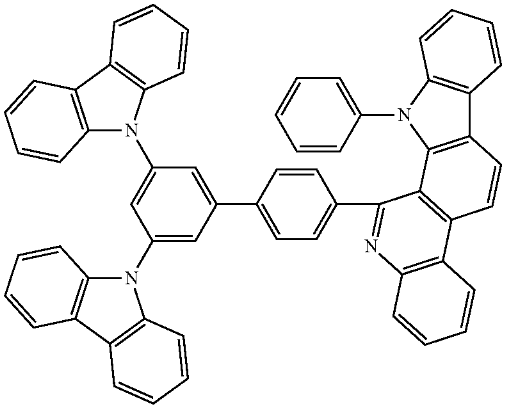
3-13
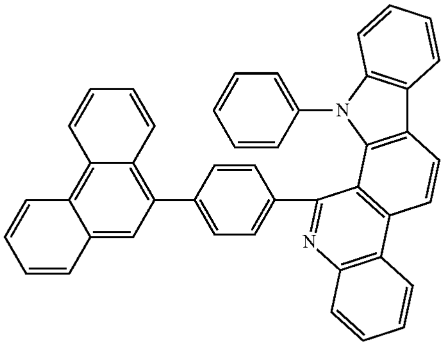
3-14
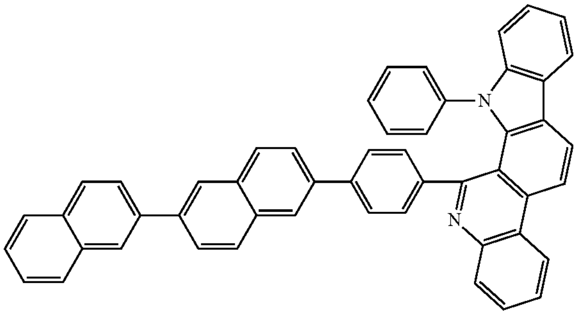
3-15
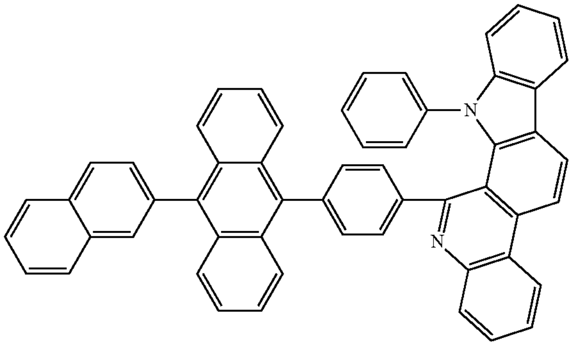
3-16
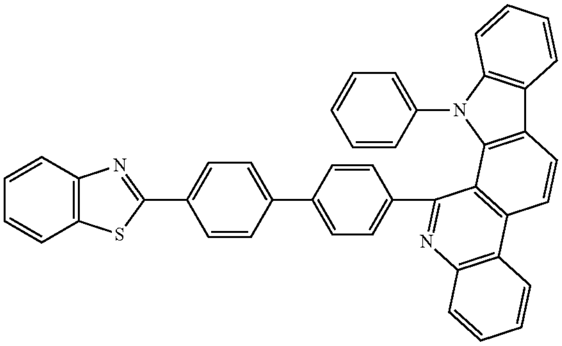
3-17
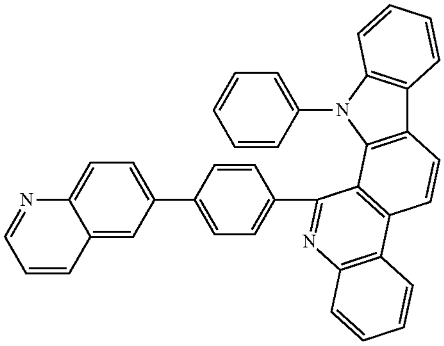
3-18
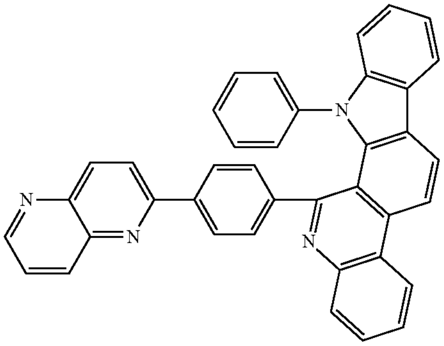

-continued
3-19
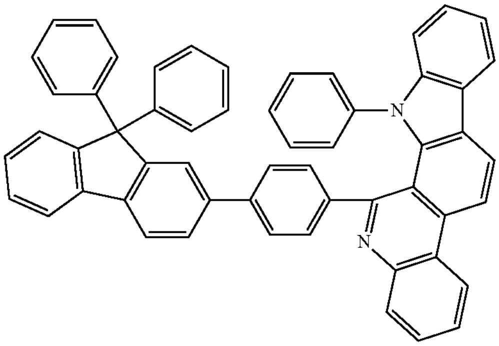
3-20
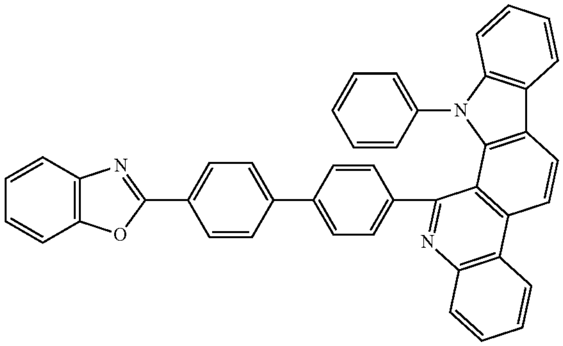
3-21
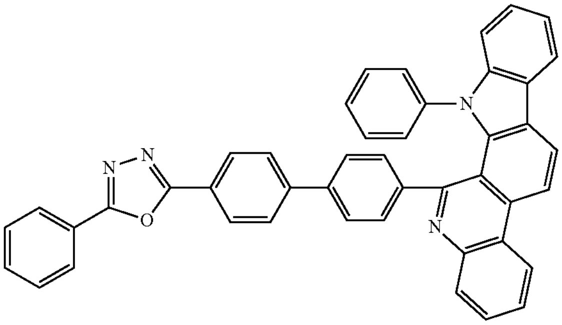
3-22
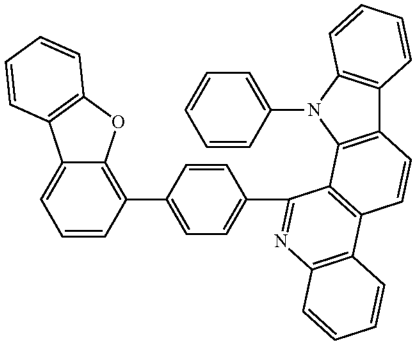
3-23
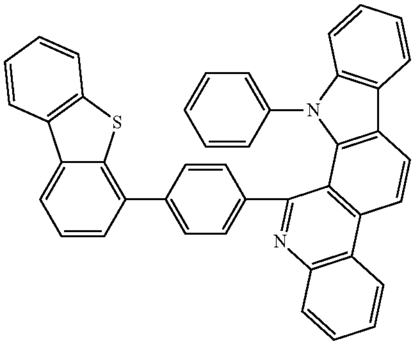
3-24
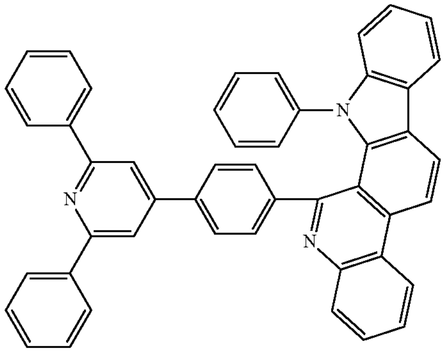
3-25
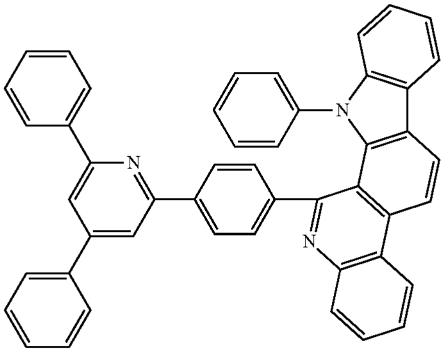
3-26
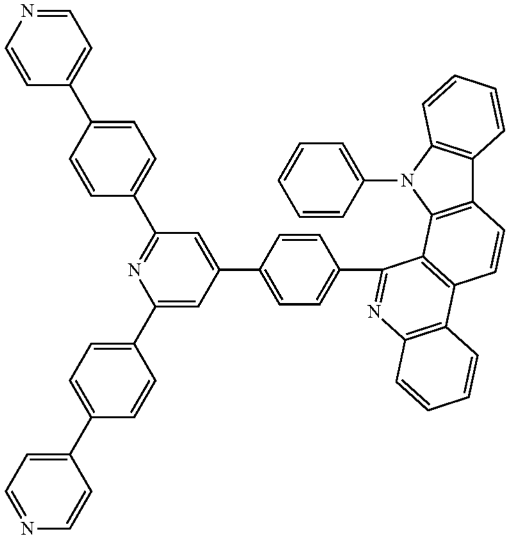

-continued
3-27
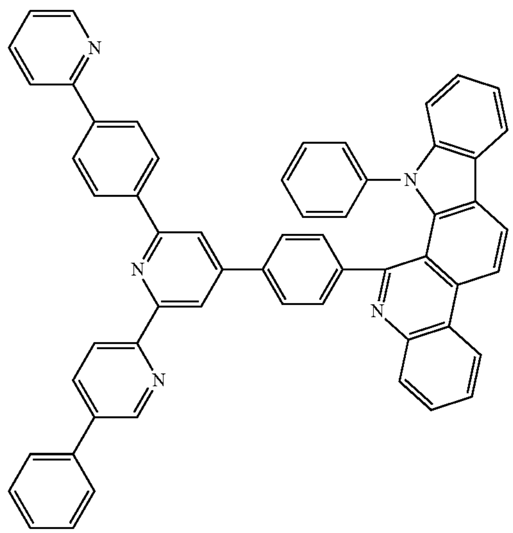
3-28
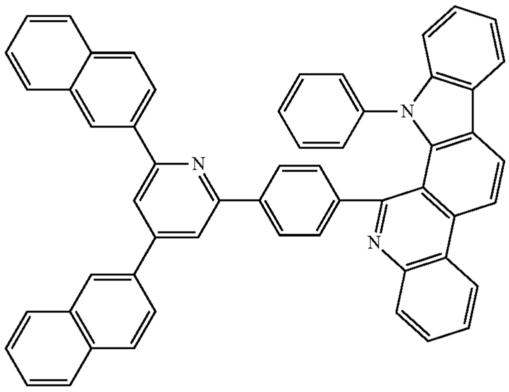
3-29
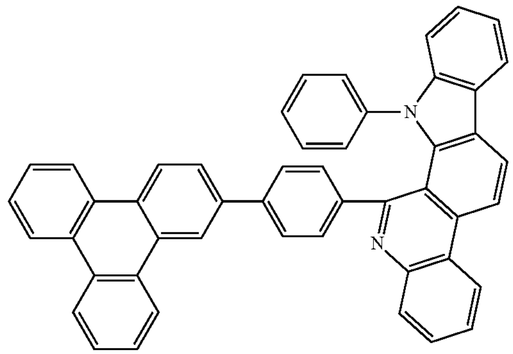
3-30
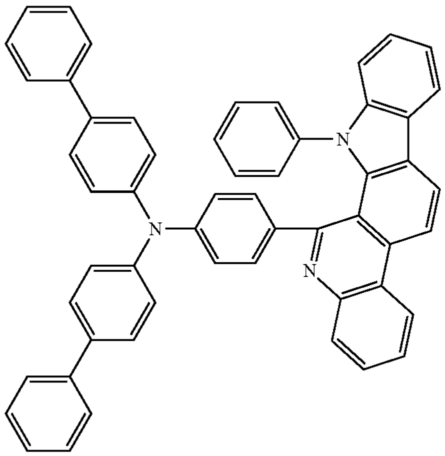
3-31
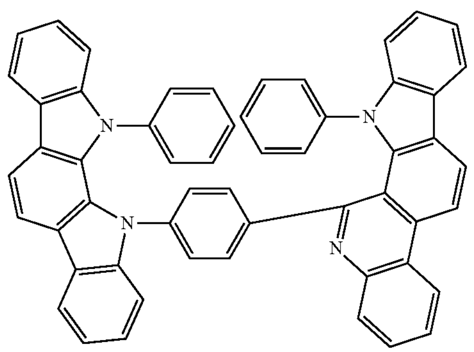
3-32
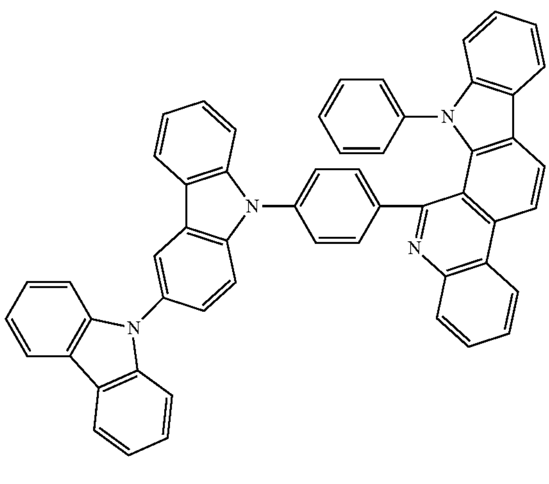

-continued
3-33
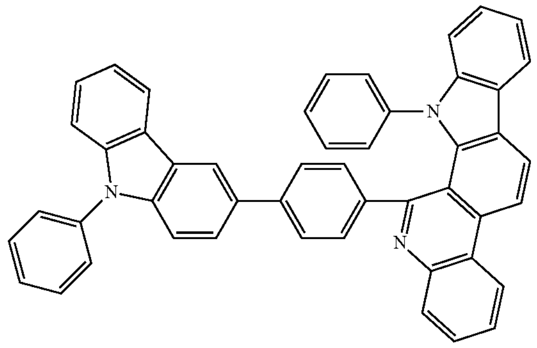
3-34
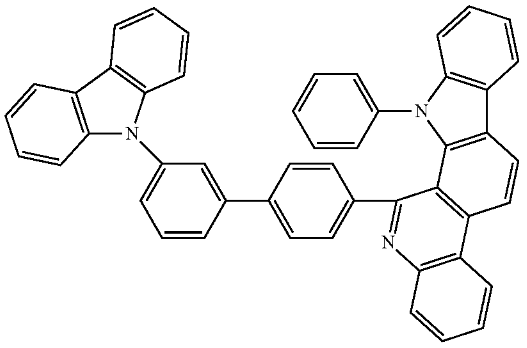
3-35
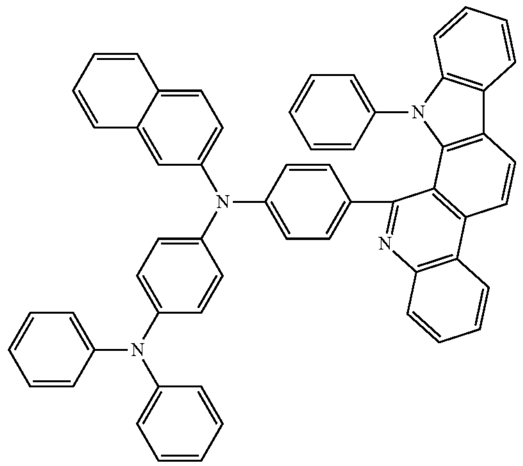
3-36
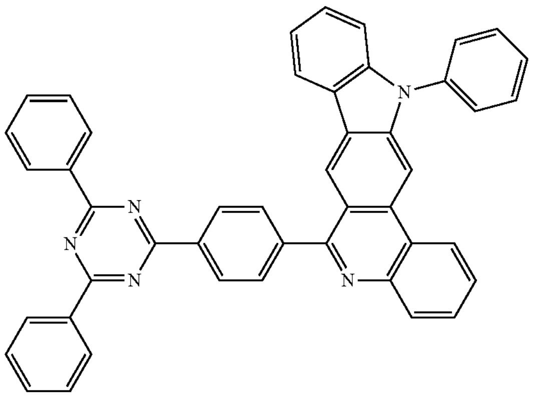
3-37
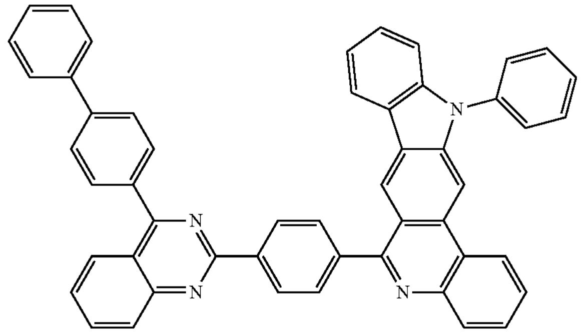
3-38
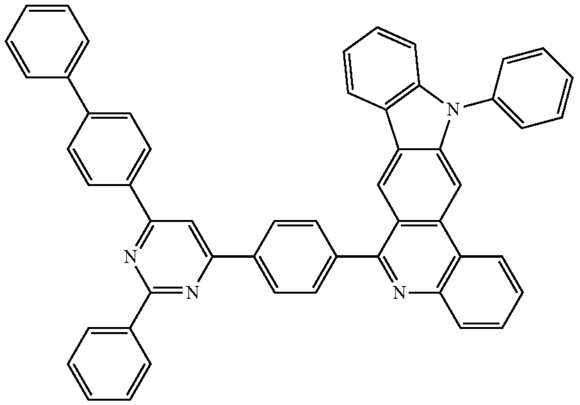

-continued
3-39
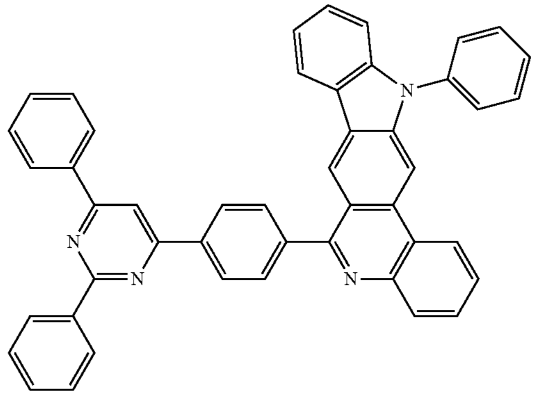
3-40
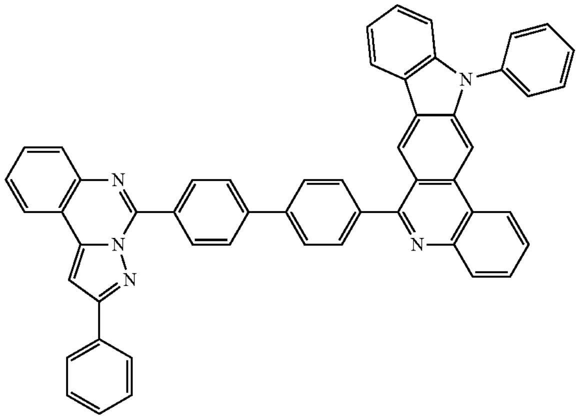
3-41
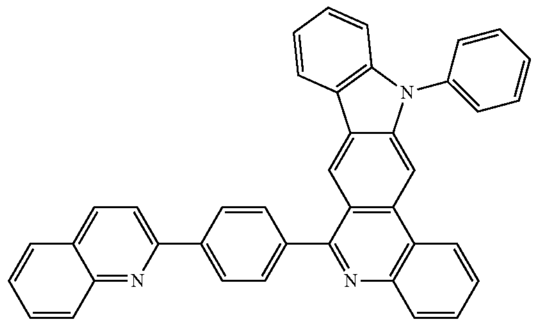
3-42
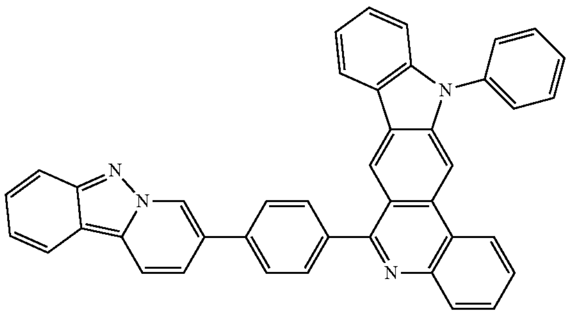
3-43
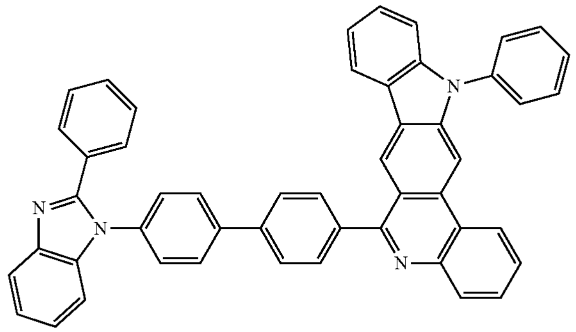
3-44
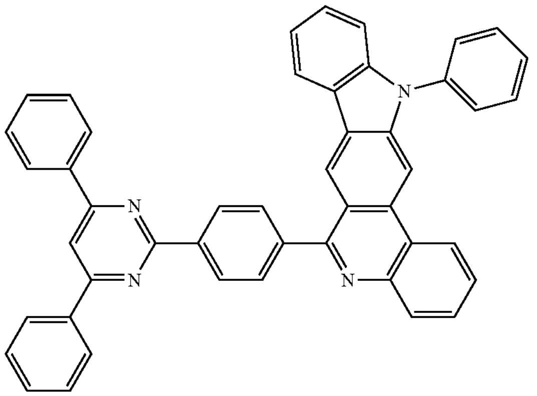
3-45
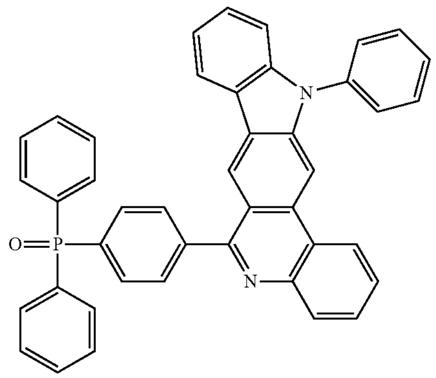
3-46
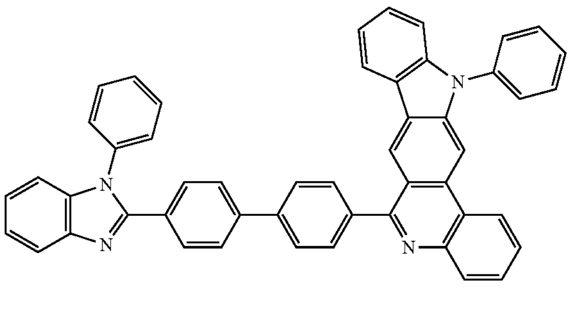

-continued
3-47
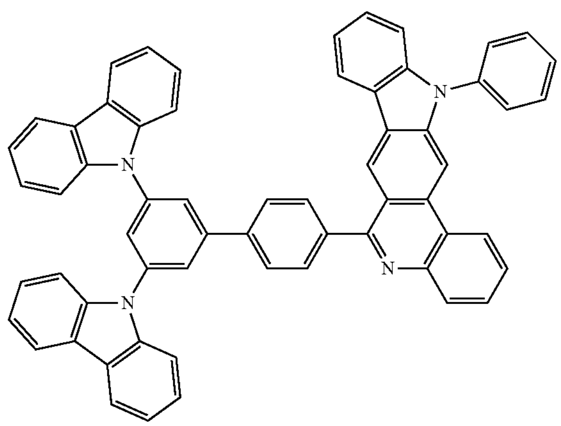
3-48
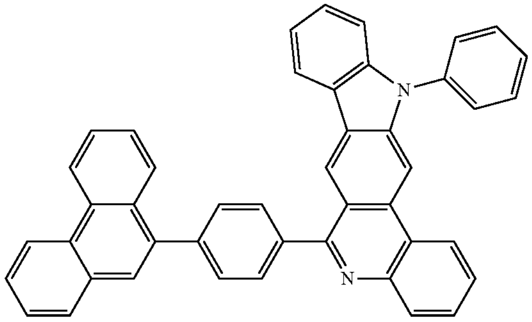
3-49
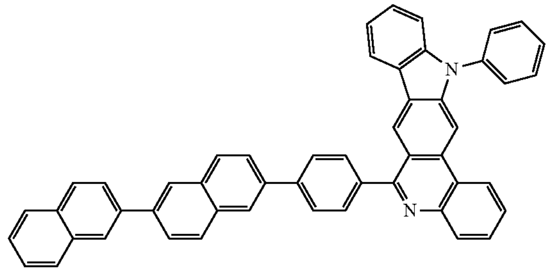
3-50
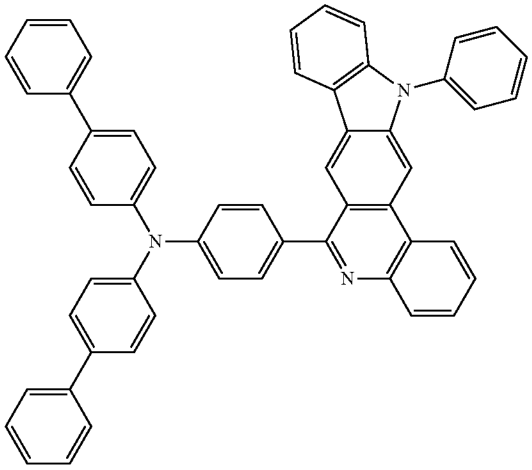
3-51
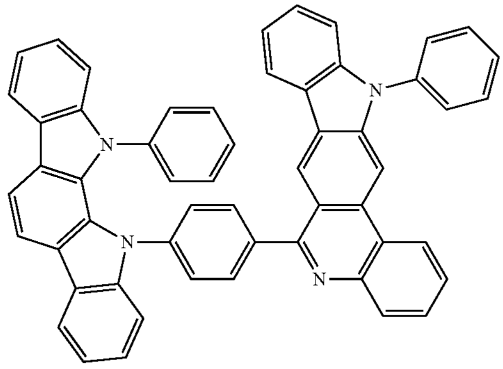
3-52
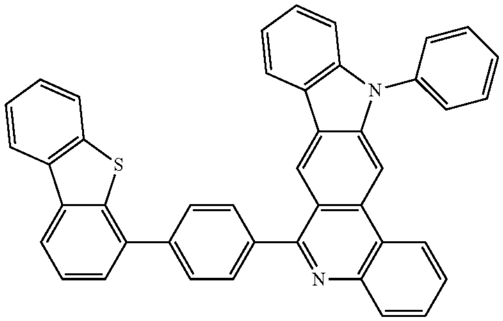

-continued
3-53
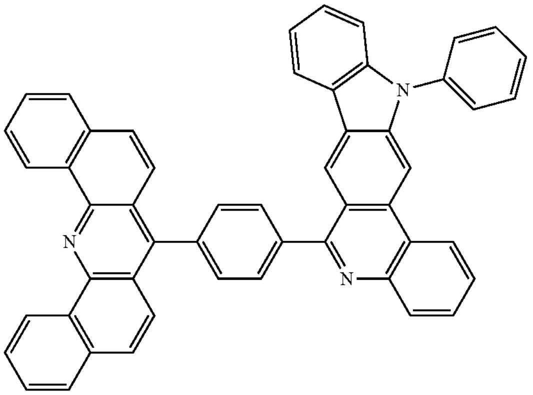
3-54
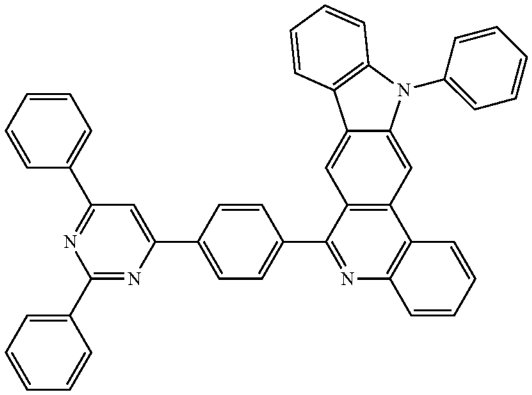
3-55
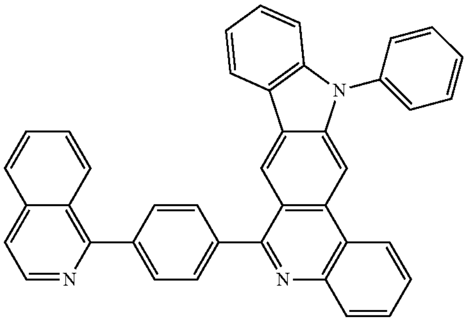
3-56
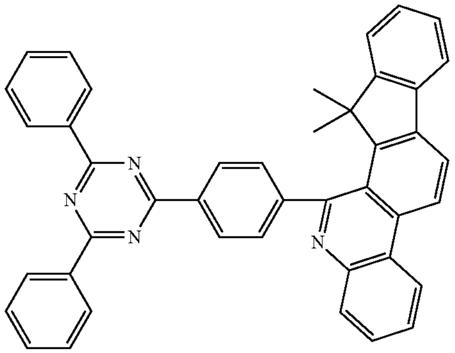
3-57
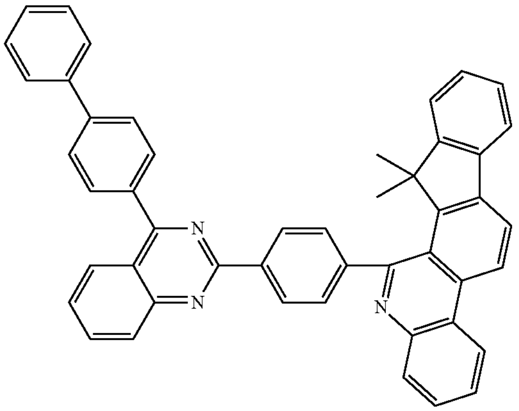
3-58
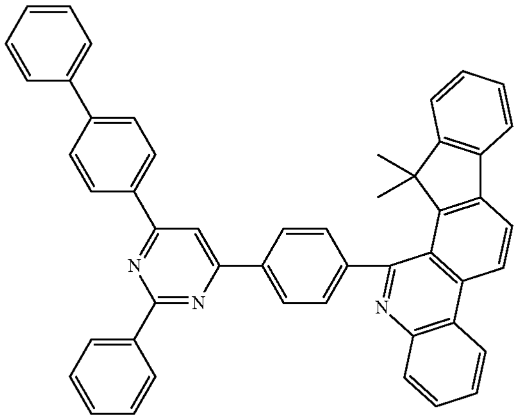
3-59
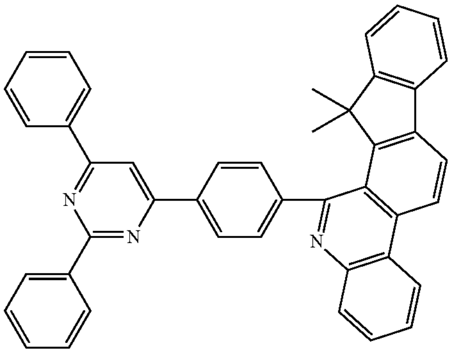
3-60
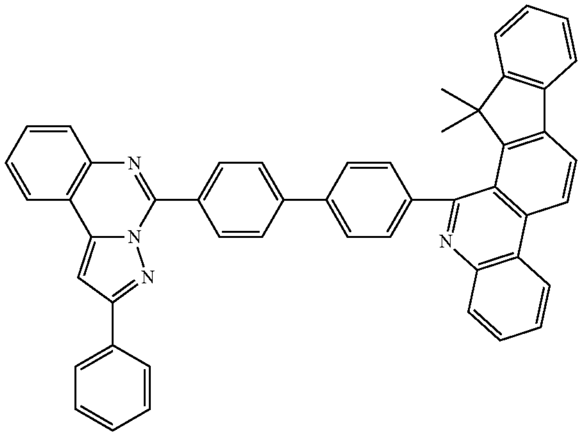

-continued
3-61
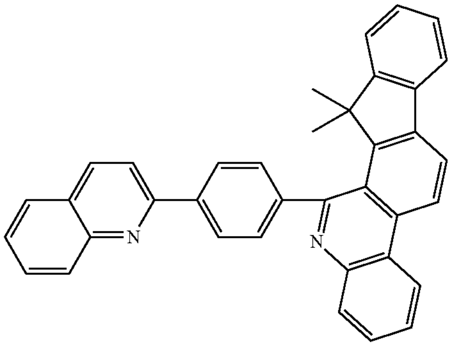
3-62
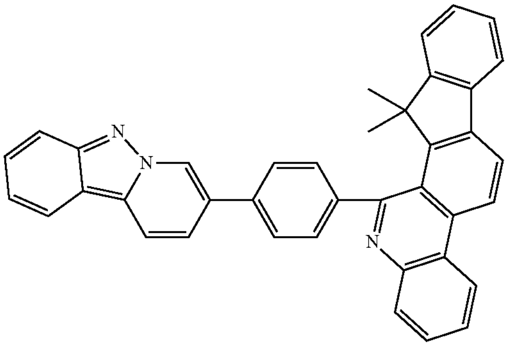
3-63
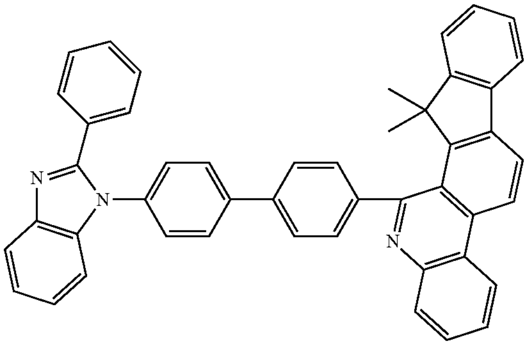
3-64
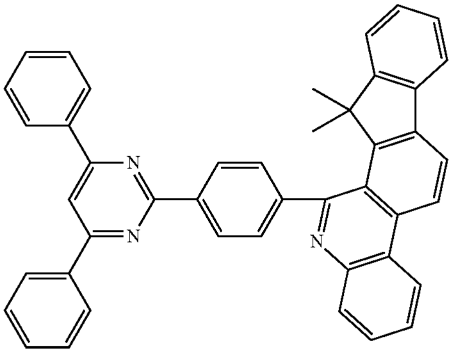
3-65
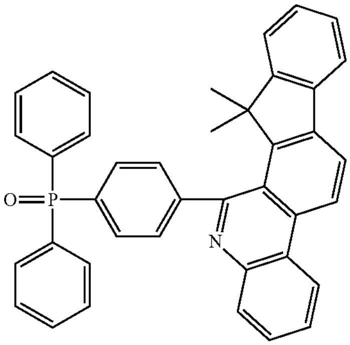
3-66
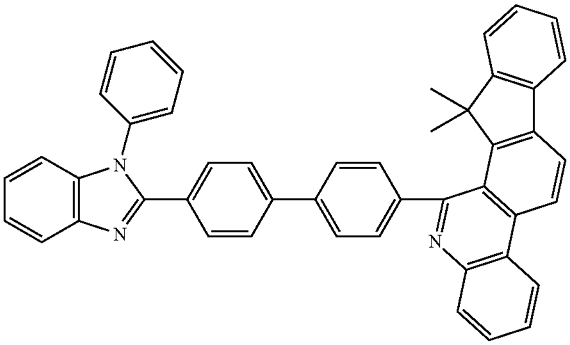
3-67
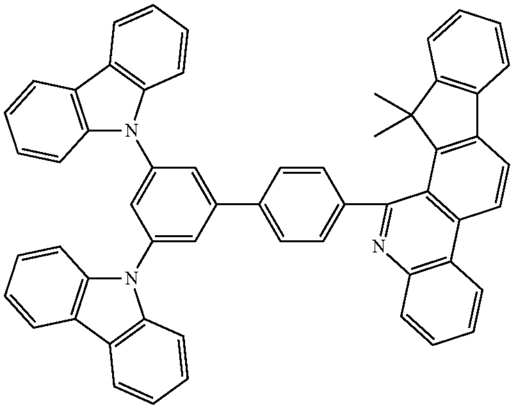
3-68
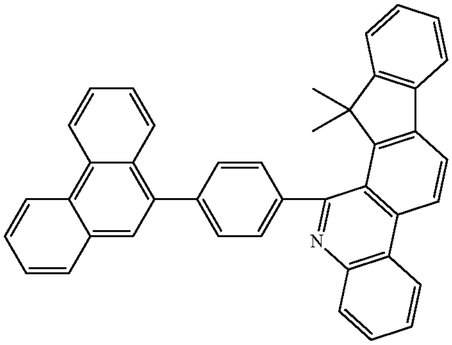

-continued
3-69
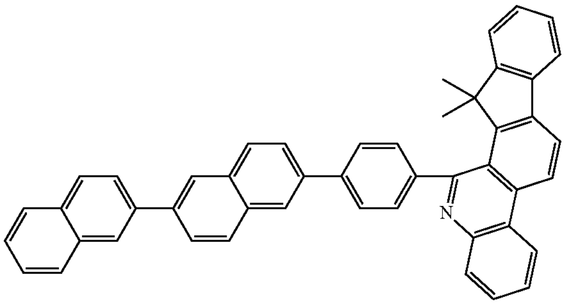
3-70
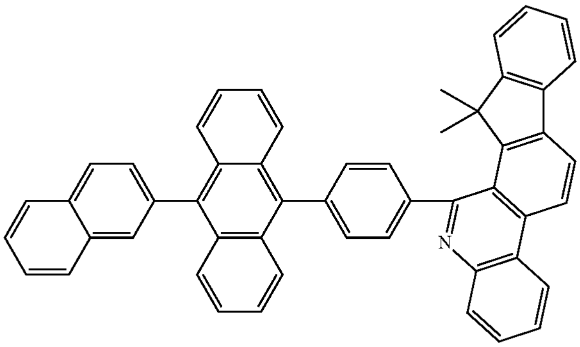
3-71
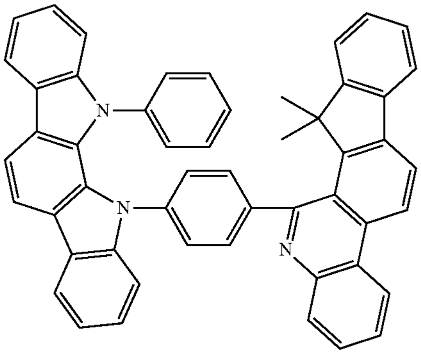
3-72
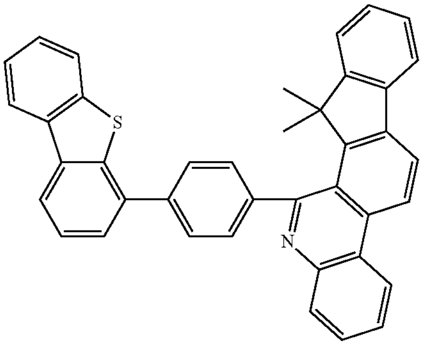
3-73
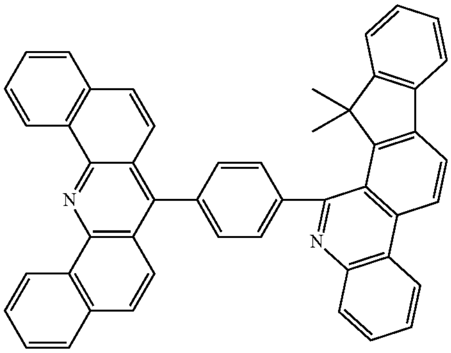
3-74
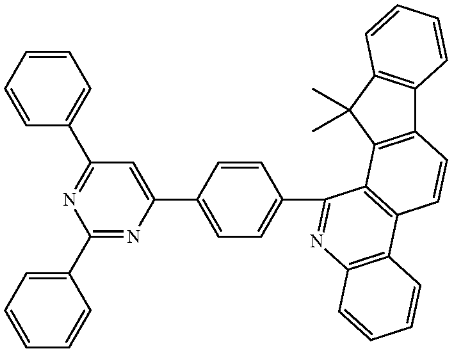
3-75
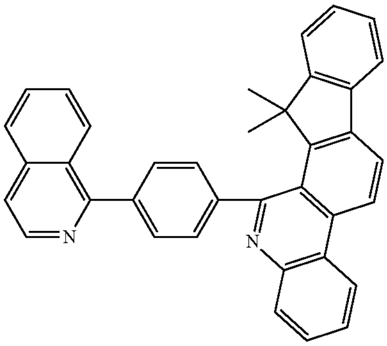
3-76
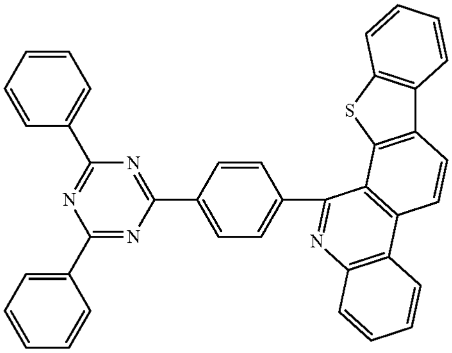

-continued
3-77
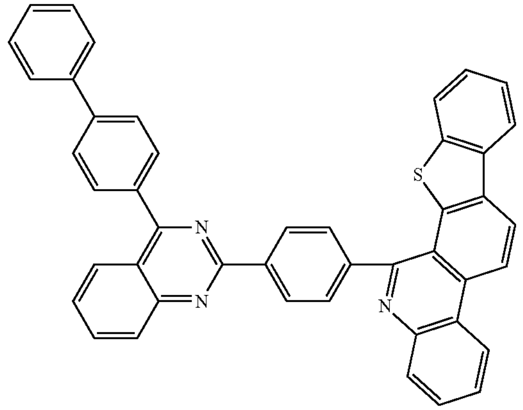
3-78
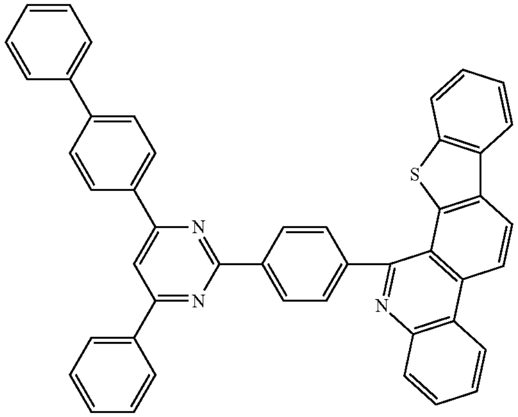
3-79
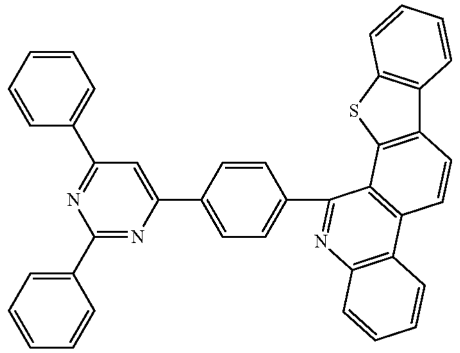
3-80
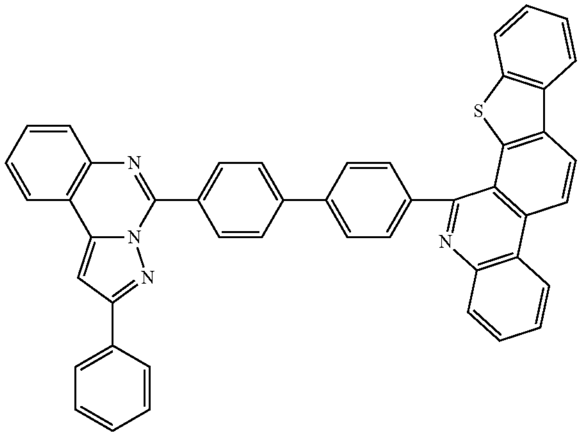
3-81
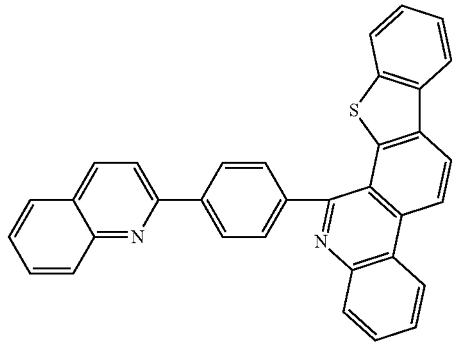
3-82
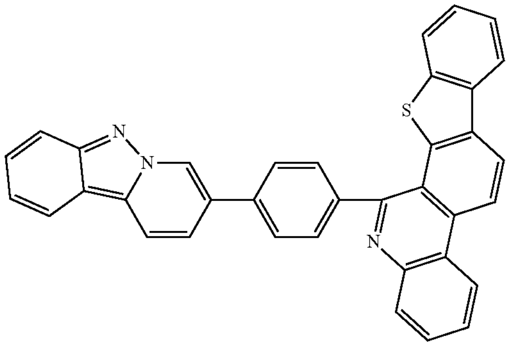
3-83
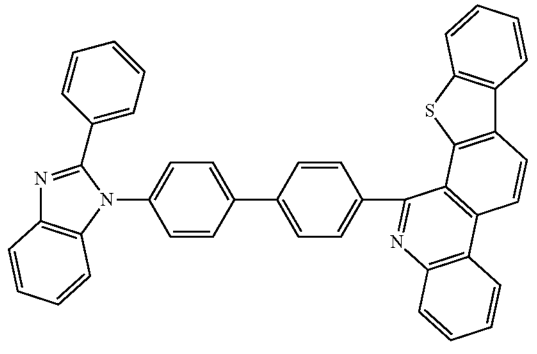
3-84
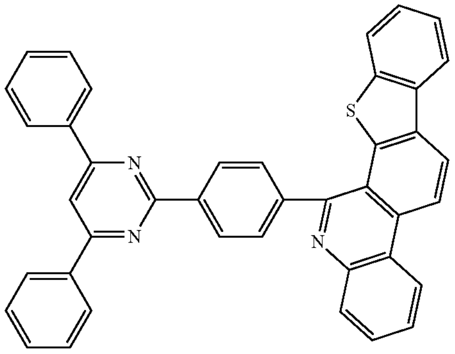

-continued
3-85
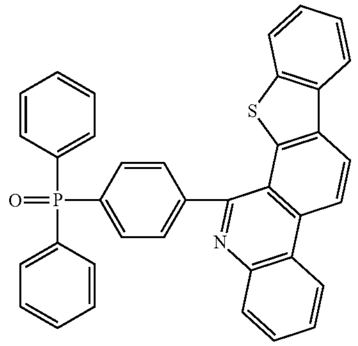
3-86
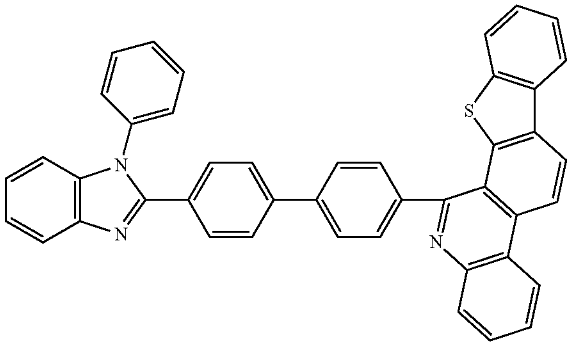
3-87
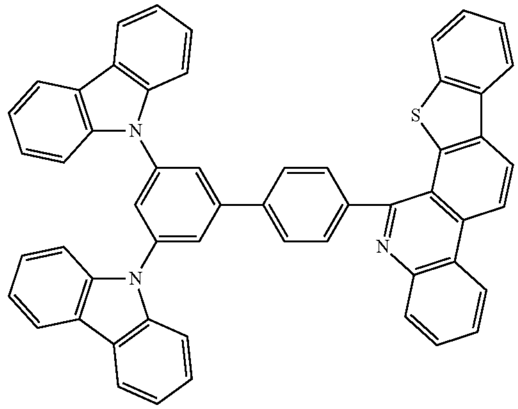
3-88
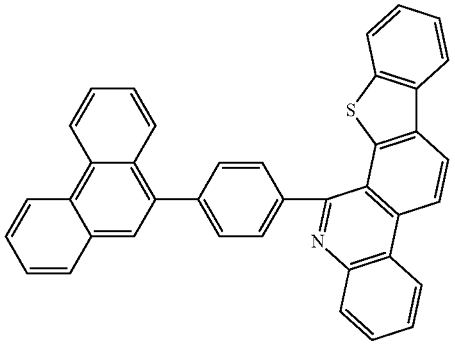
3-89
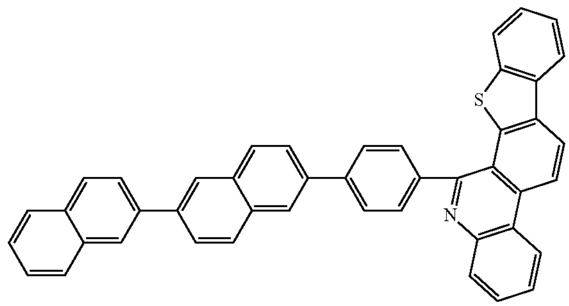
3-90
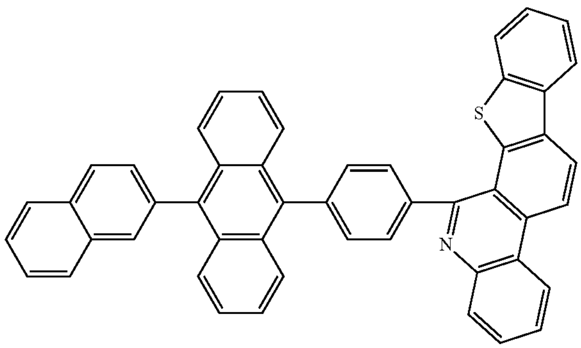
3-91
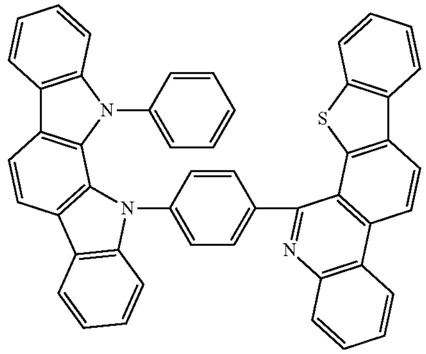
3-92
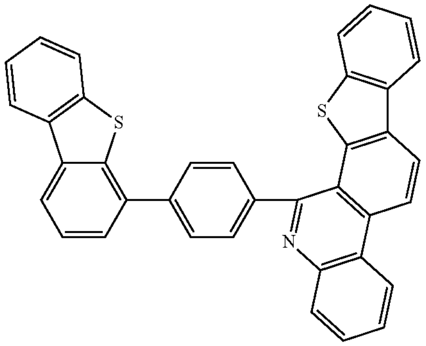

-continued
3-93
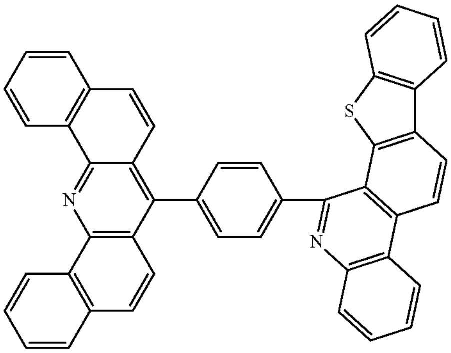
3-94
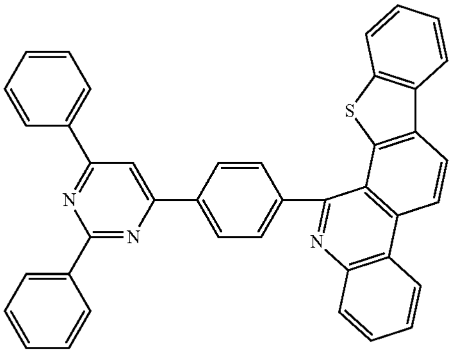
3-95
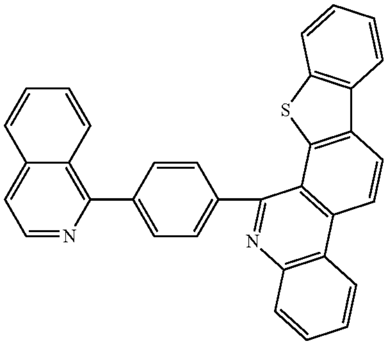
3-96
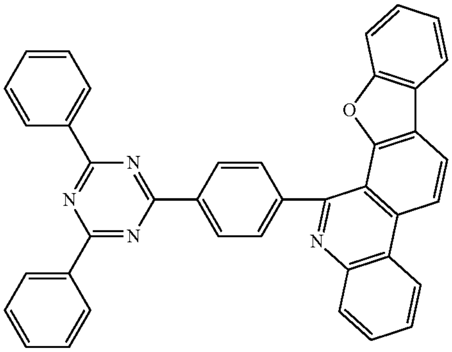
3-97
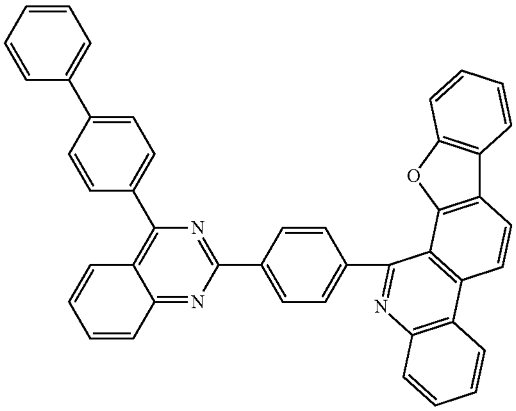
3-98
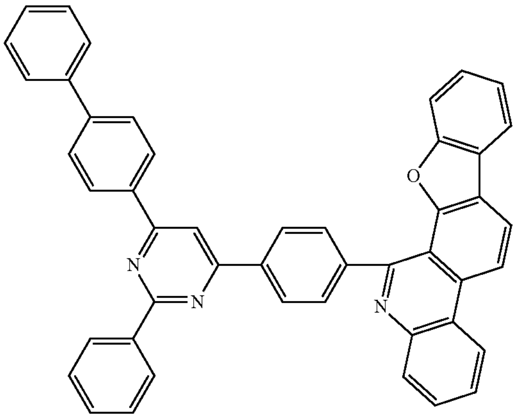
3-99
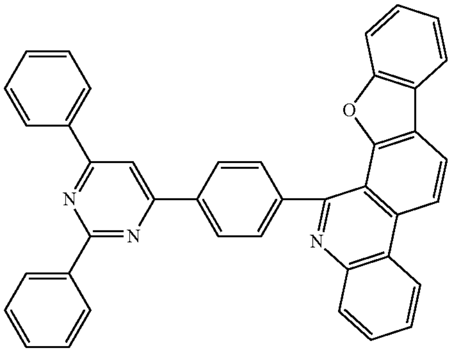
3-100
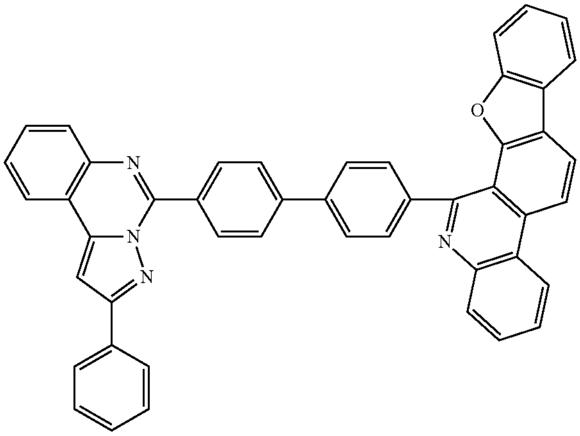

-continued
3-101
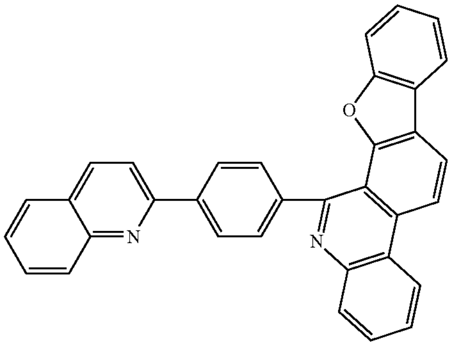
3-102
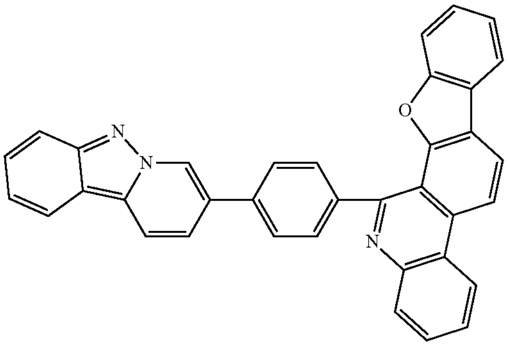
3-103
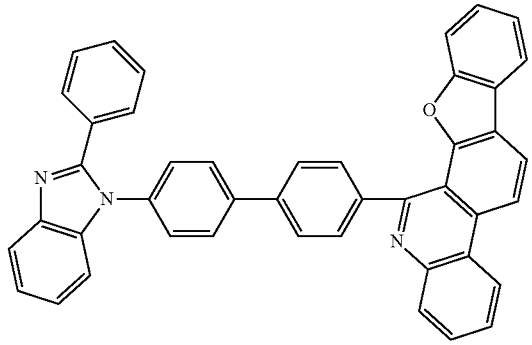
3-104
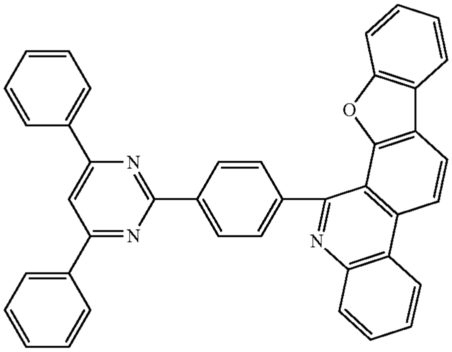
3-105
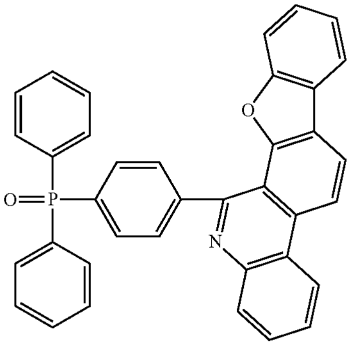
3-106
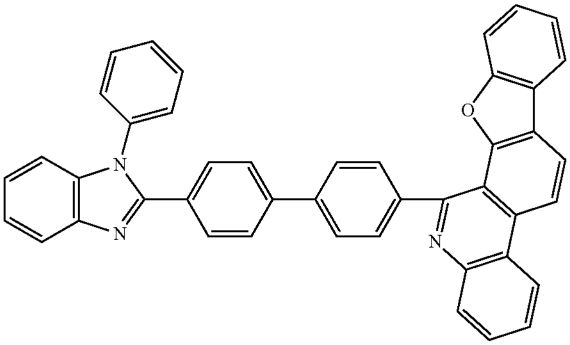
3-107
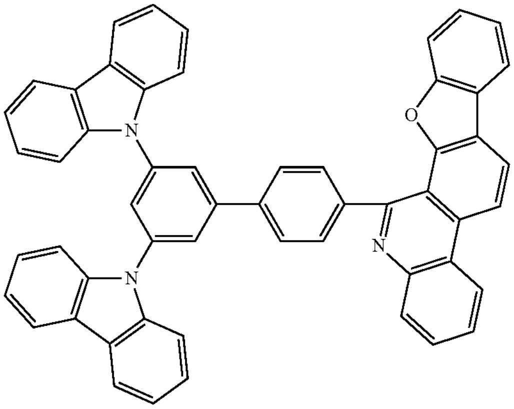
3-108
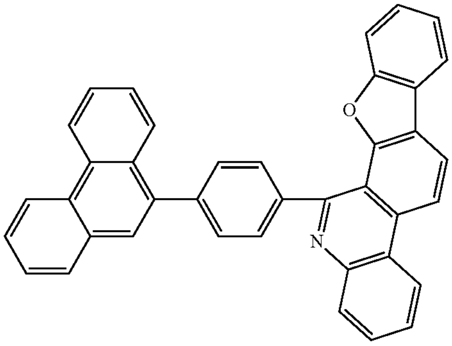

-continued
3-109
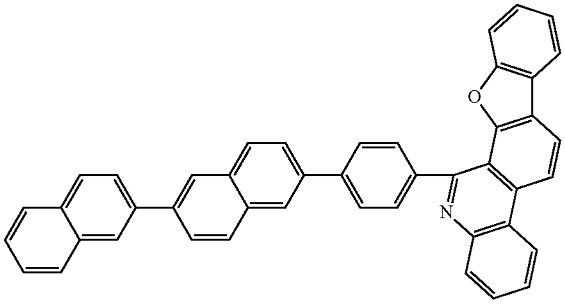
3-110
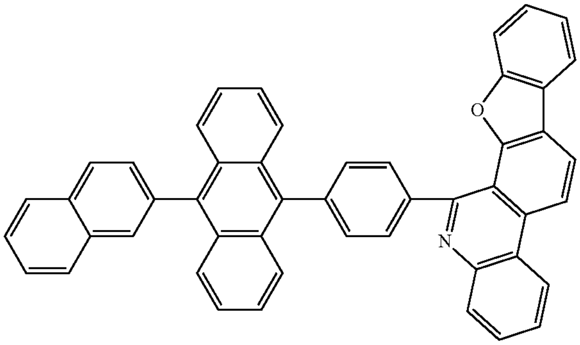
3-111
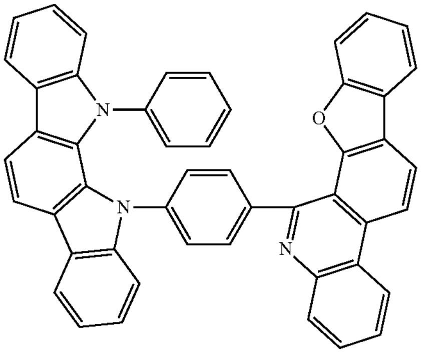
3-112
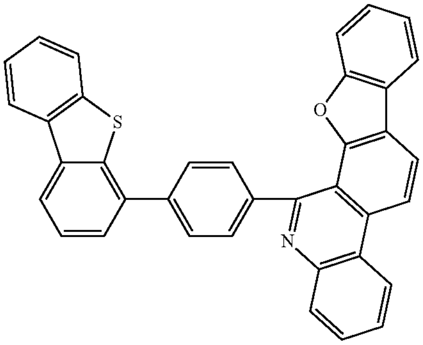
3-113
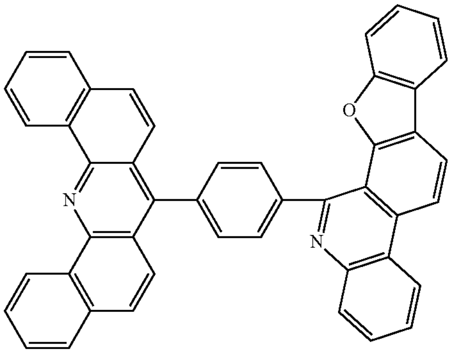
3-114
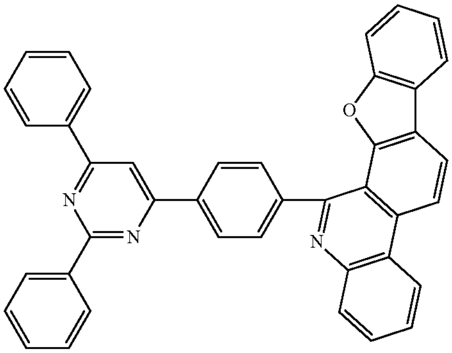
3-115
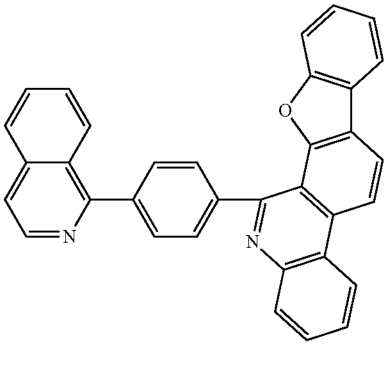
3-116
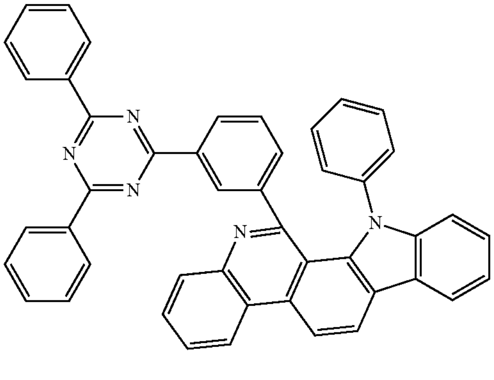

-continued
3-117
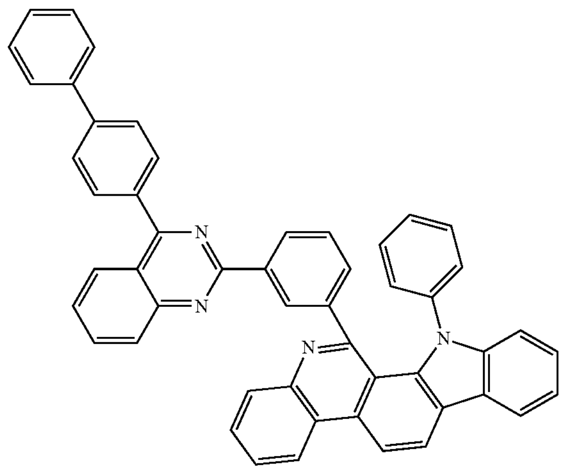
3-118
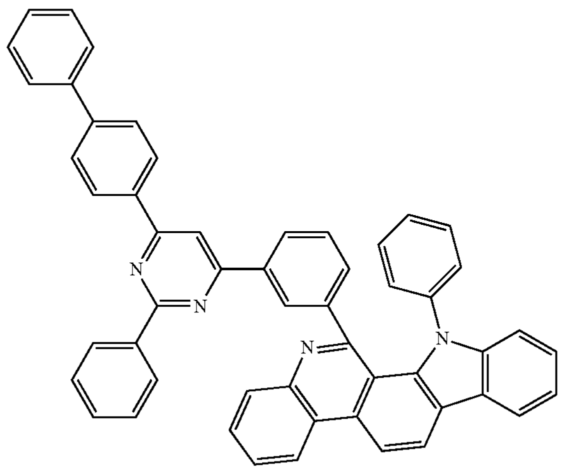
3-119
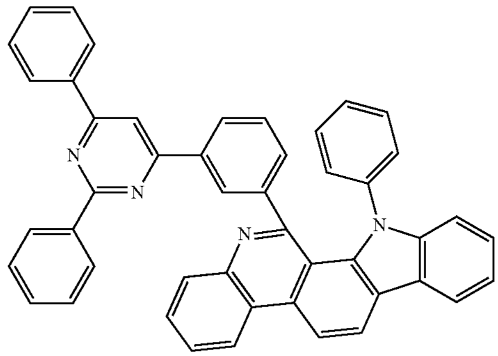
3-120
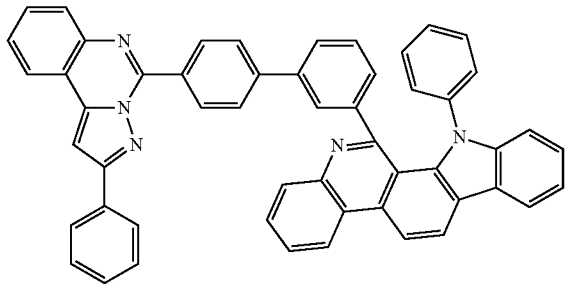
3-121
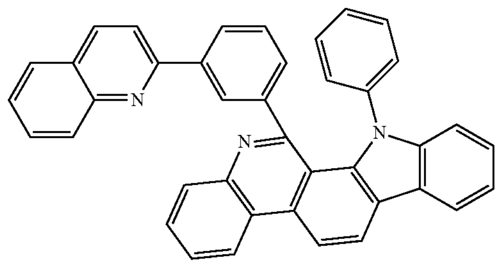
3-122
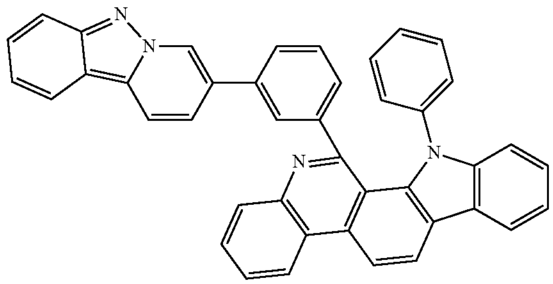
3-123
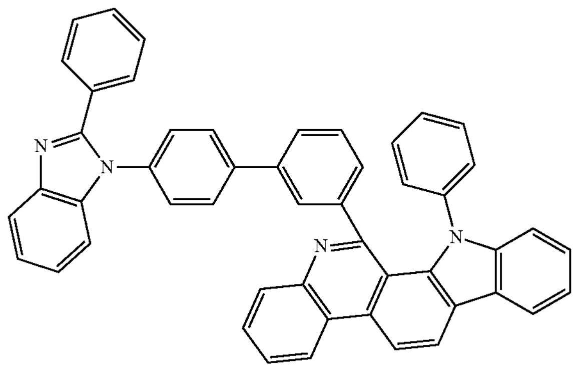
3-124
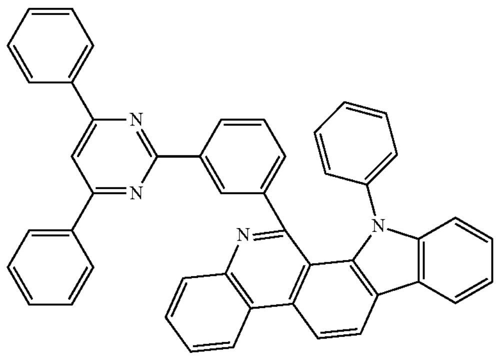

-continued
3-125
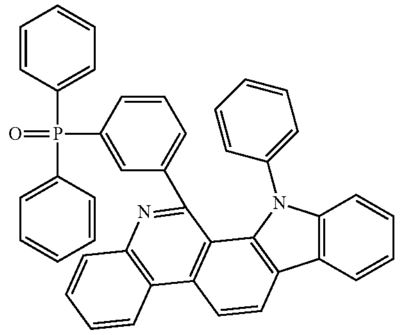
3-126
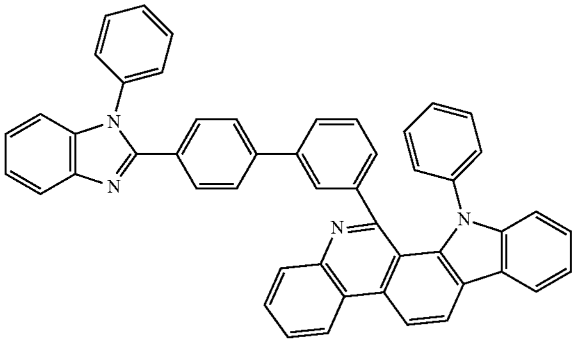
3-127
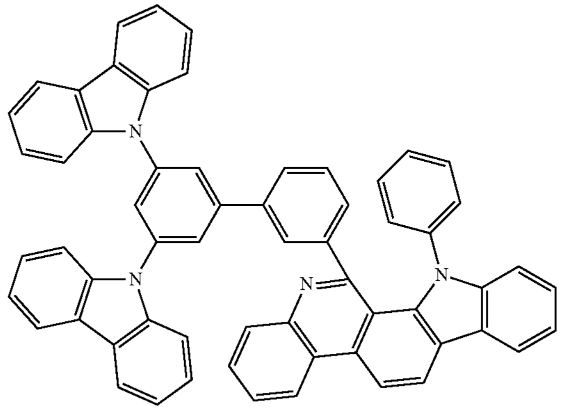
3-128
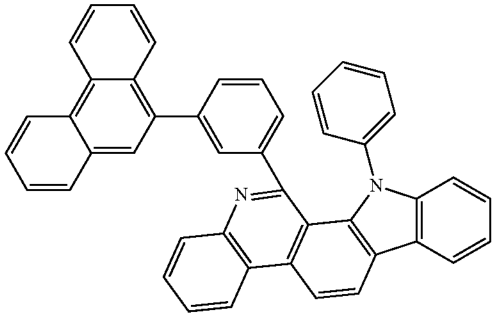
3-129
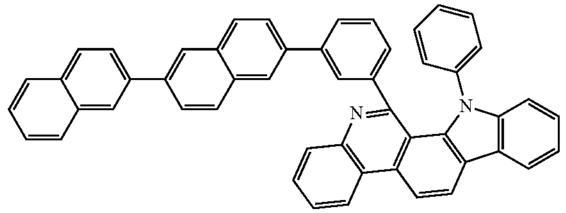
3-130
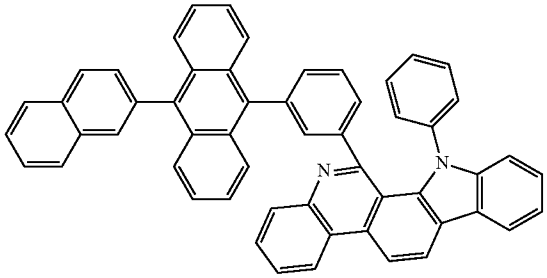
3-131
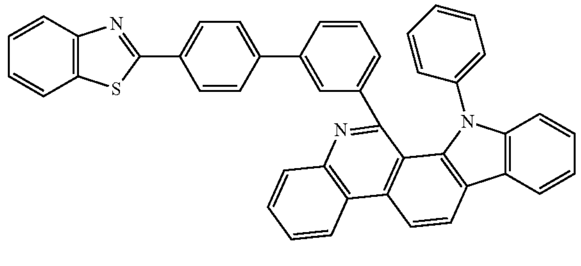
3-132
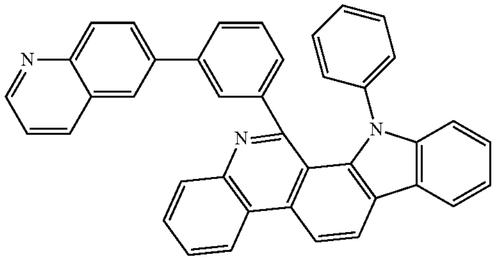

-continued
3-133
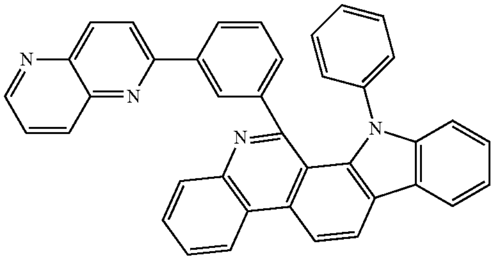
3-134
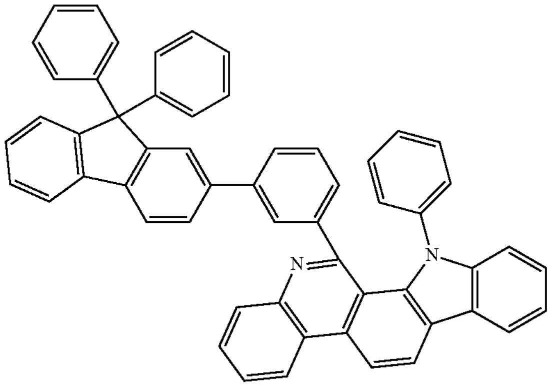
3-135
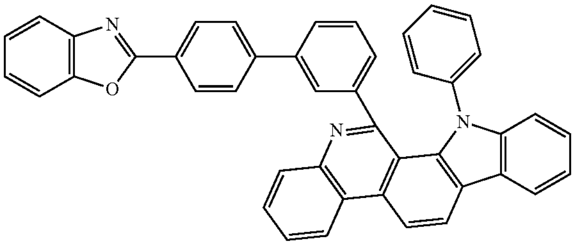
3-136
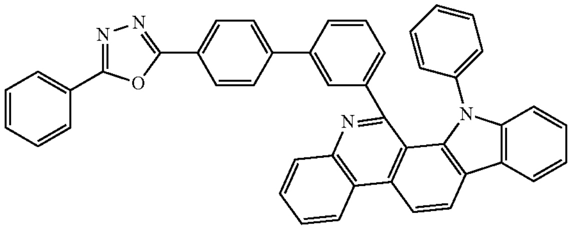
3-137
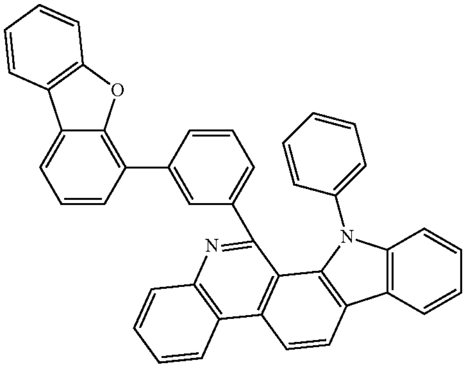
3-138
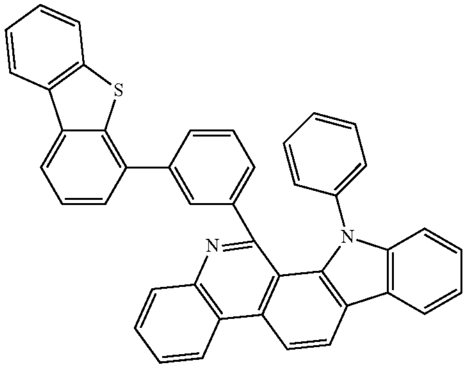
3-139
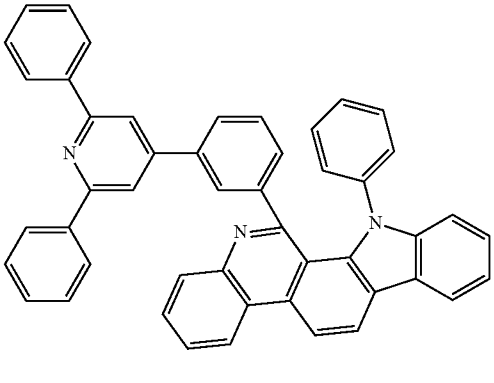
3-140
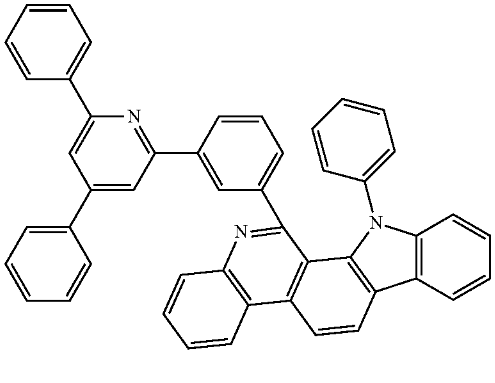

-continued
3-141
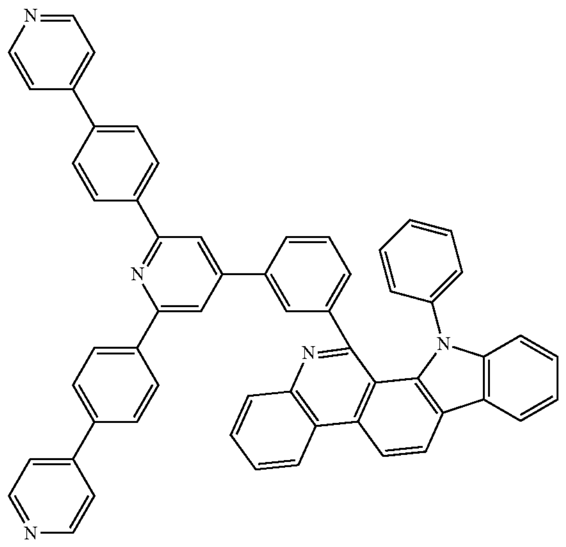
3-142
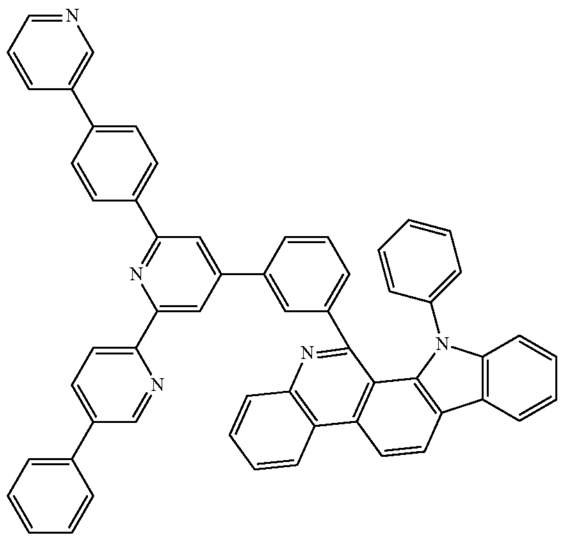
3-143
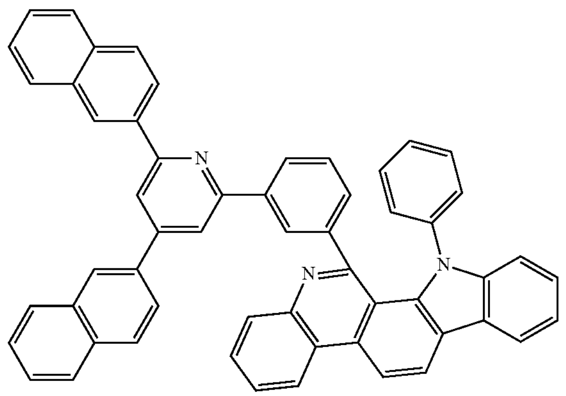
3-144
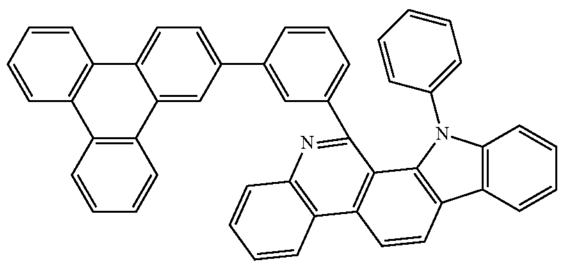
3-145
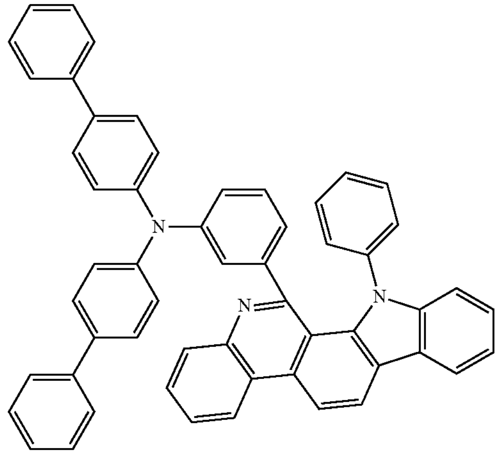
3-146
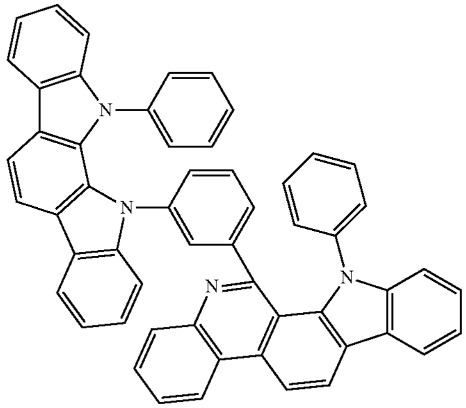

-continued
3-147
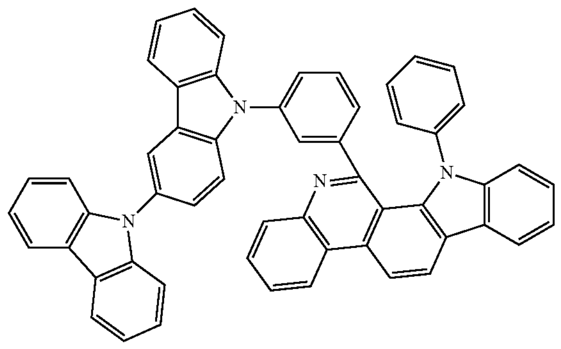
3-148
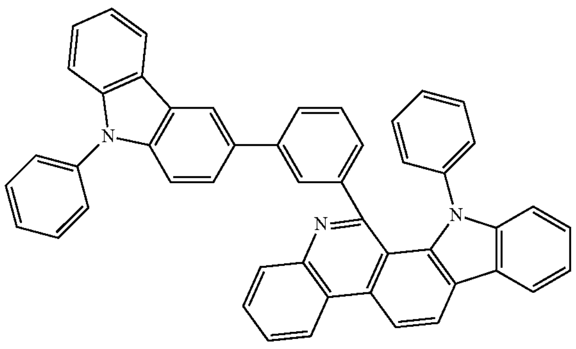
3-149
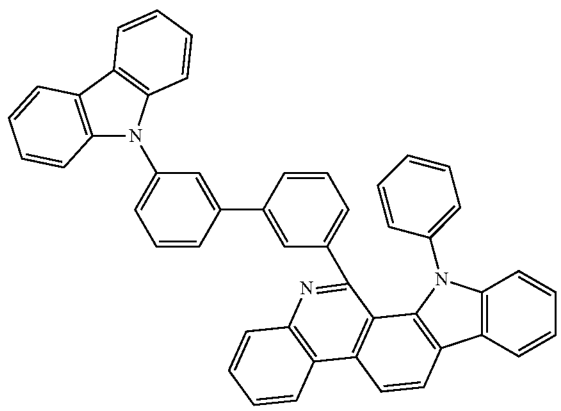
3-150
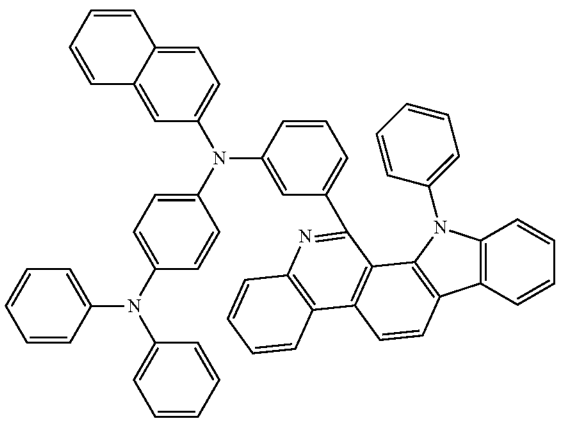
3-151
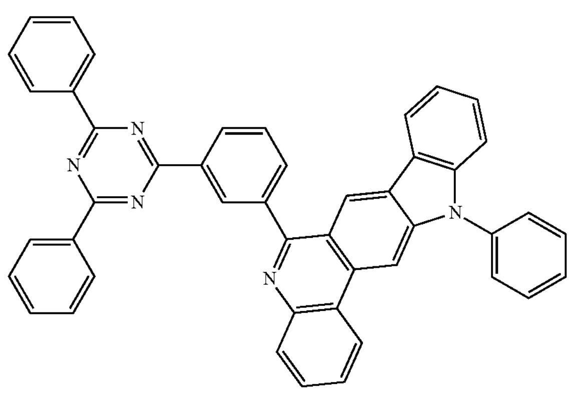
3-152
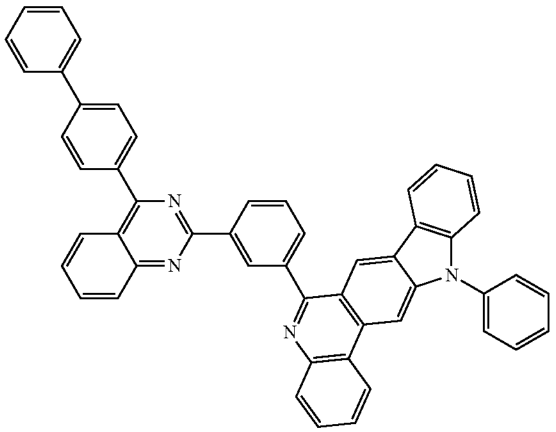

-continued
3-153
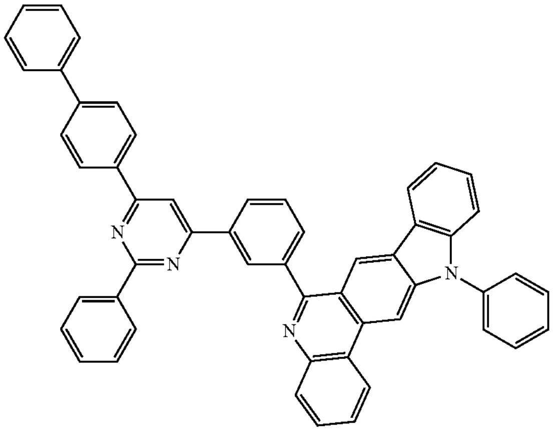
3-154
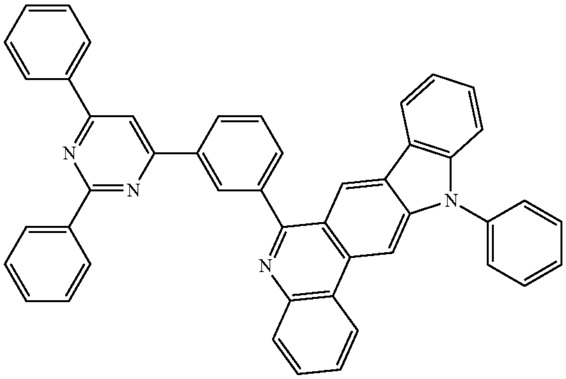
3-155
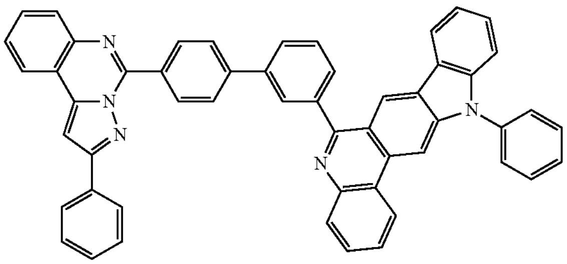
3-156
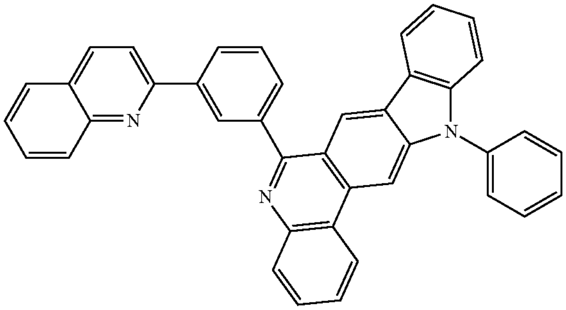
3-157
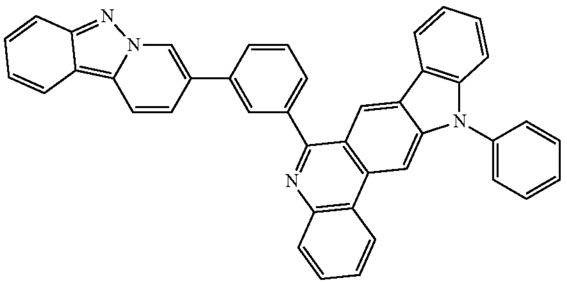
3-158
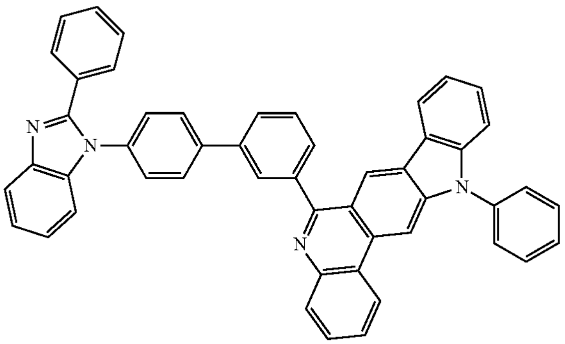
3-159
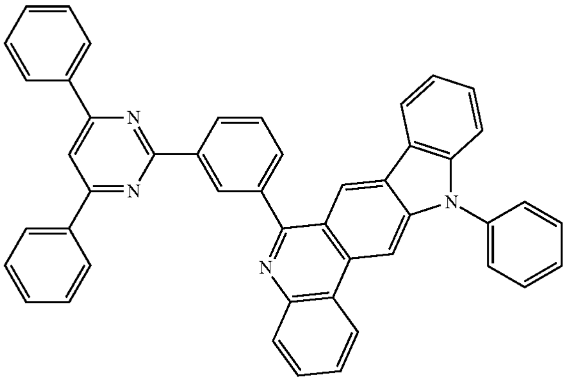
3-160
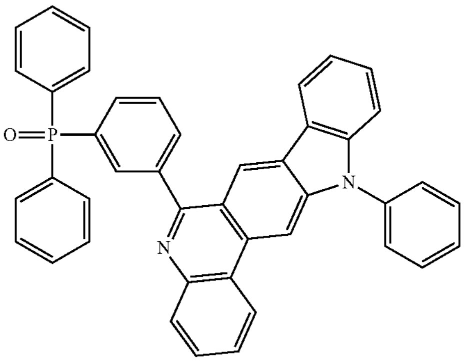

-continued
3-161
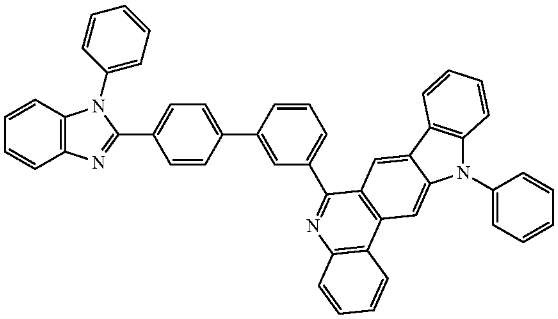
3-162
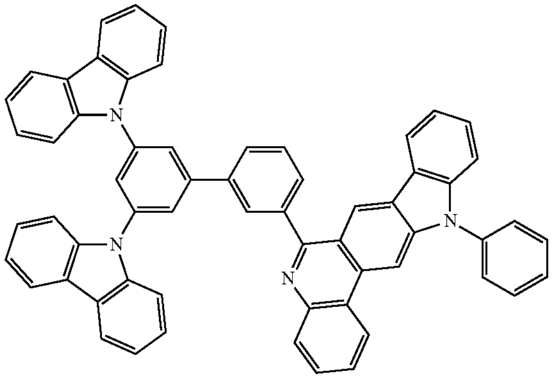
3-163
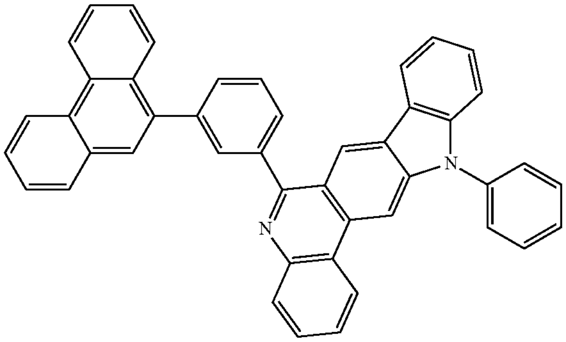
3-164
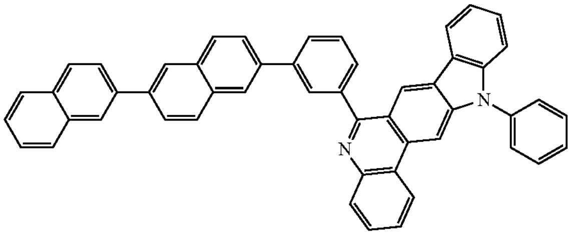
3-165
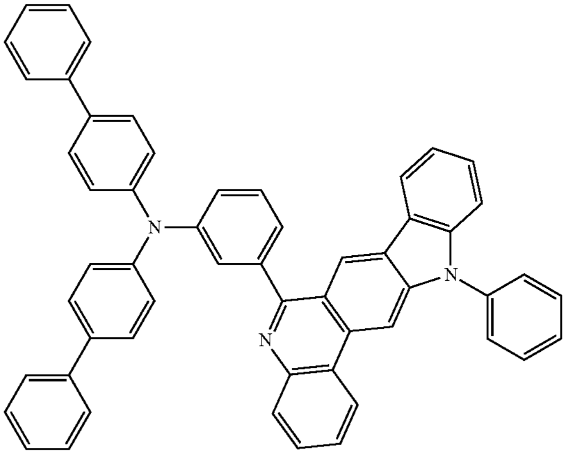
3-166
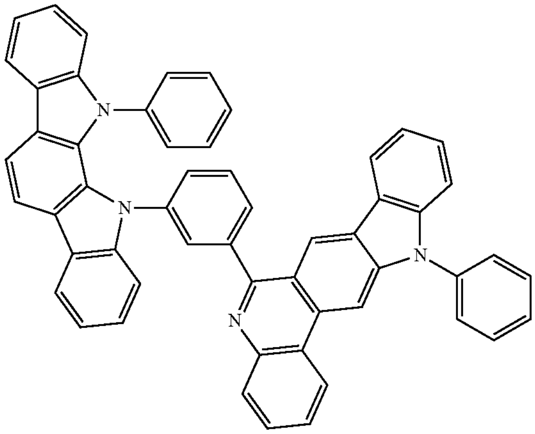
3-167
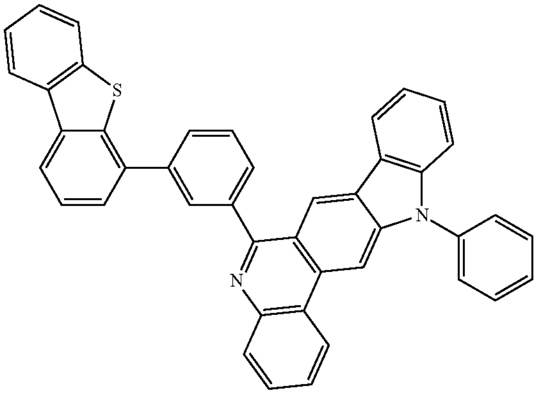
3-168
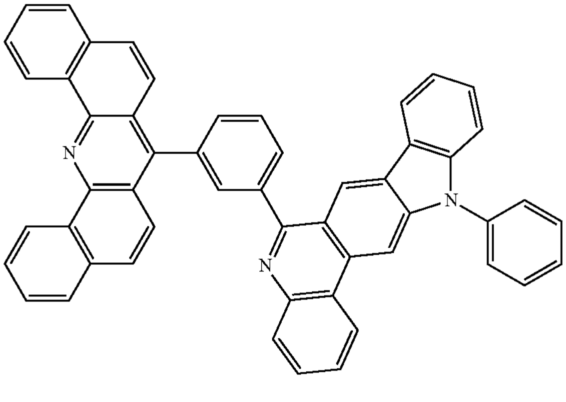

-continued
3-169
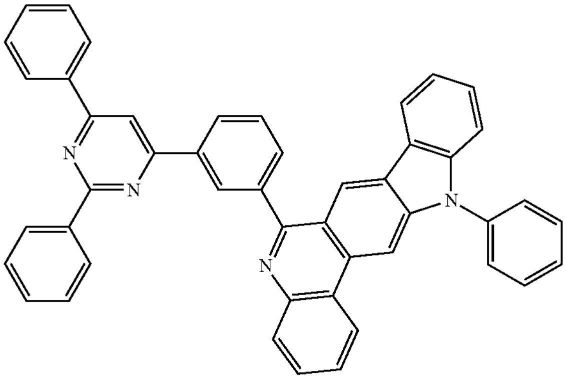
3-170
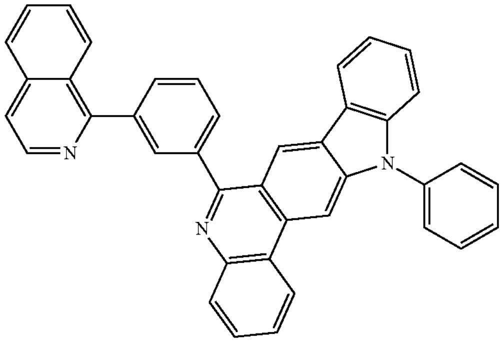
3-171
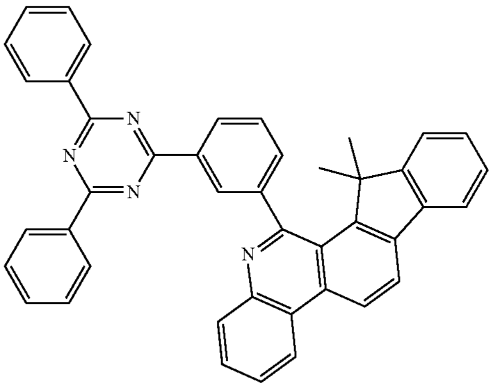
3-172
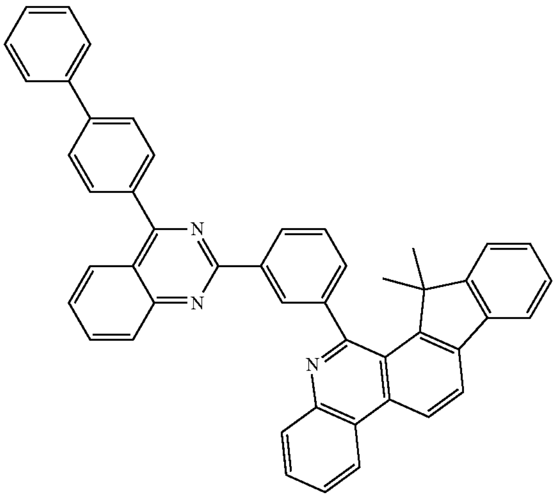
3-173
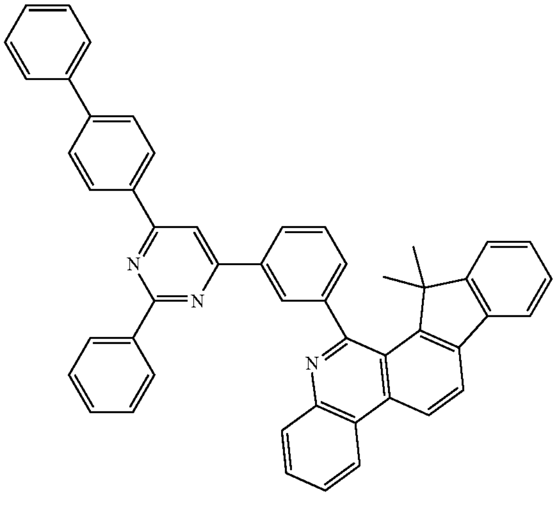
3-174
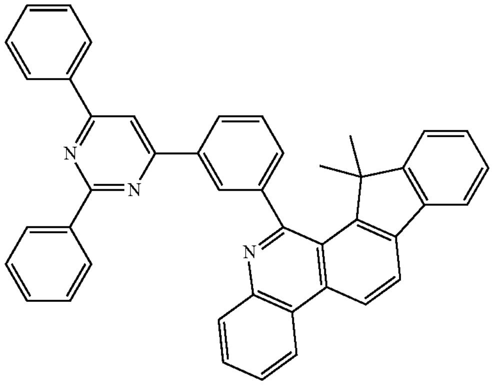

-continued
3-175
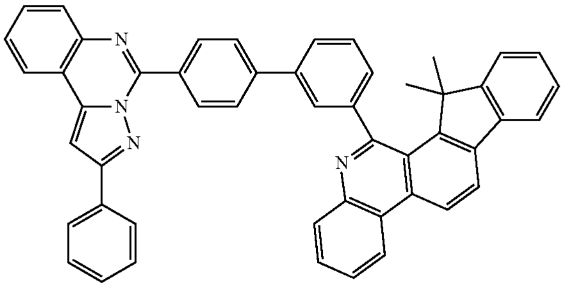
3-176
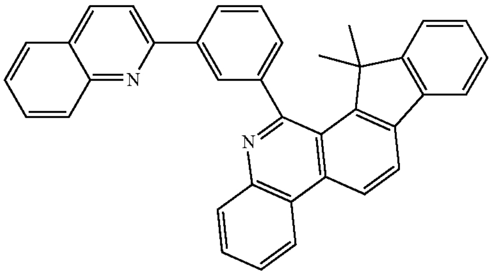
3-177
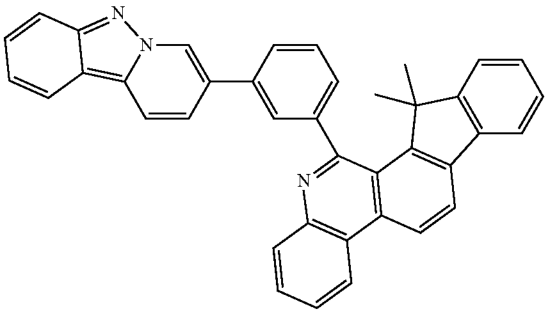
3-178
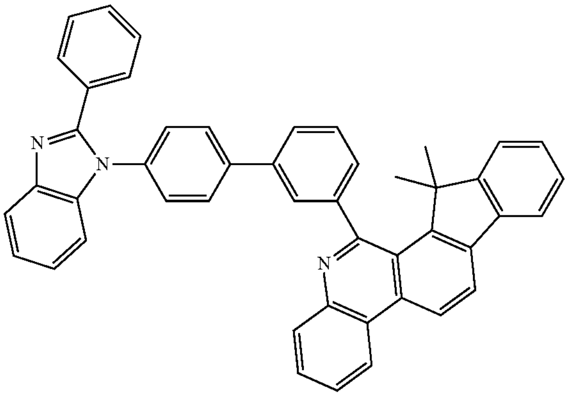
3-179
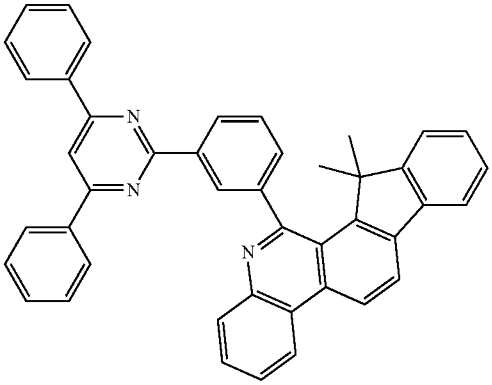
3-180
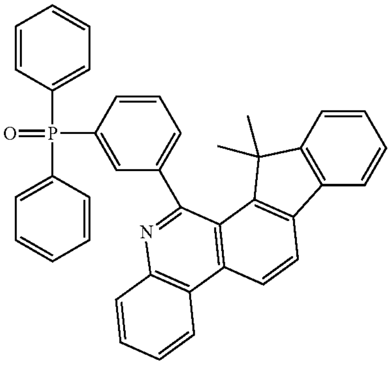
3-181
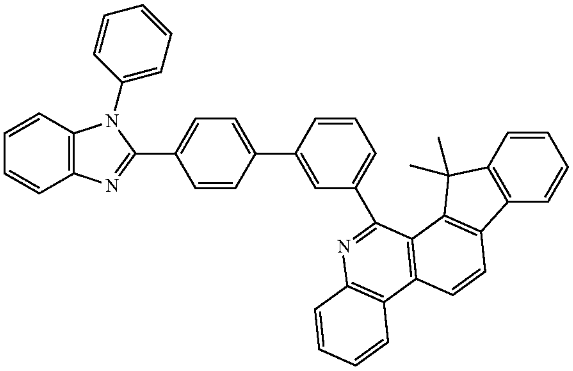
3-182
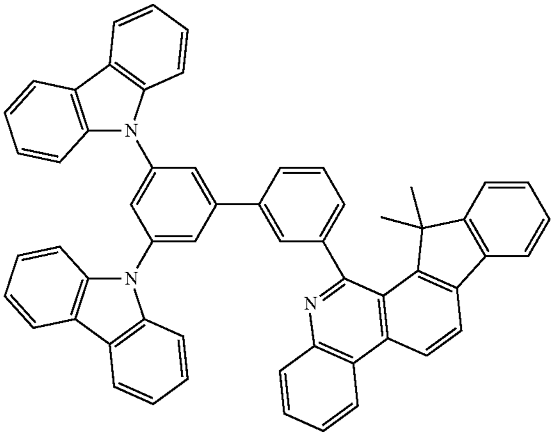

-continued
3-183
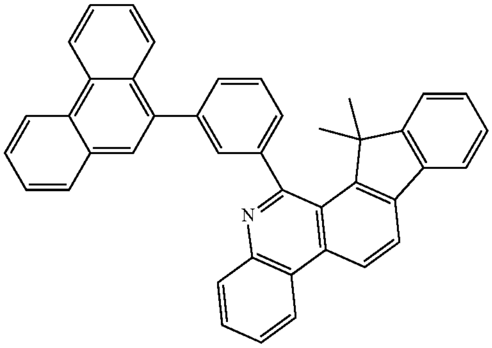
3-184
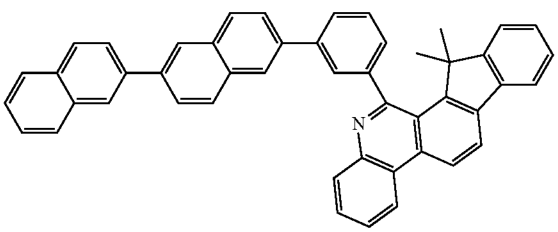
3-185
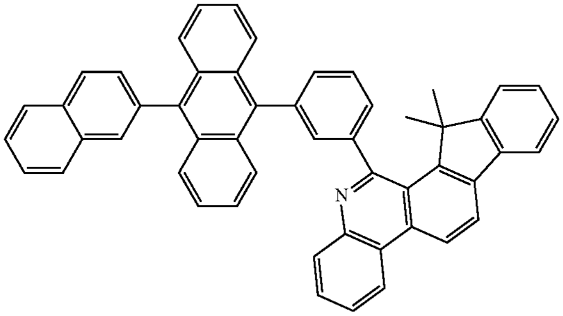
3-186
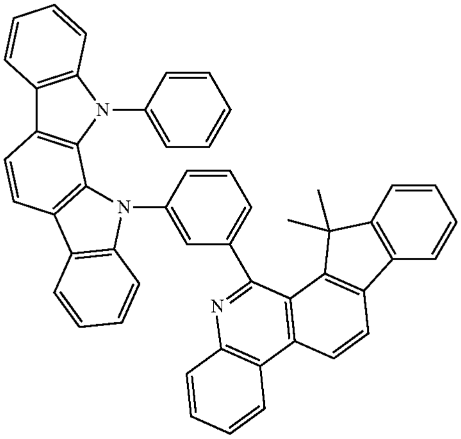
3-187
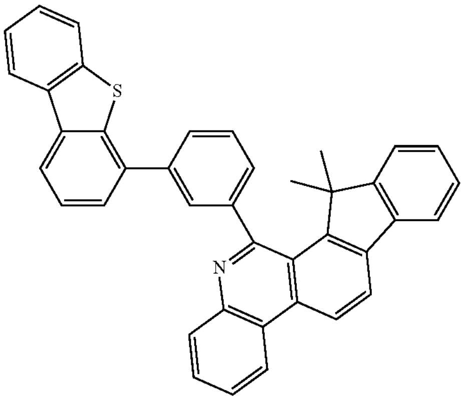
3-188
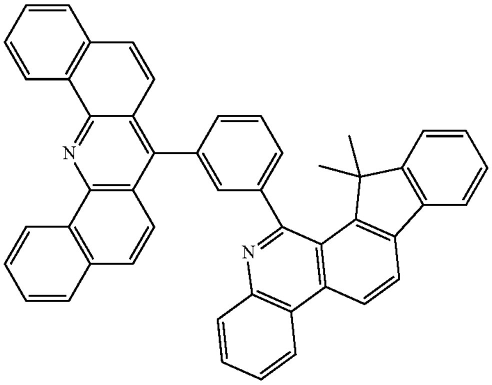
3-189
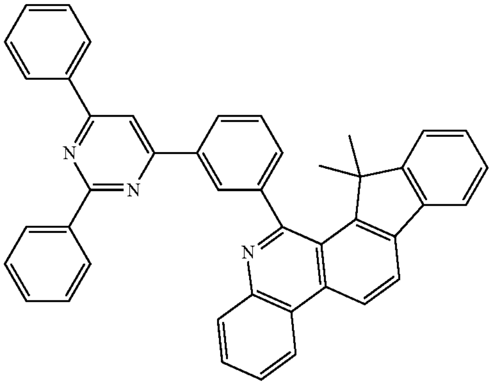
3-190
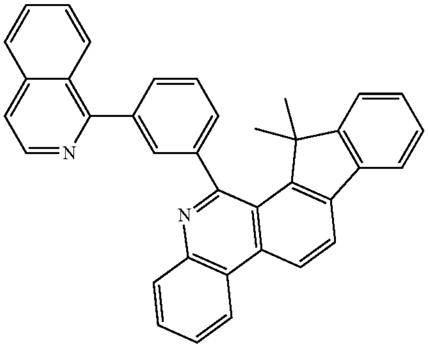

-continued
3-191
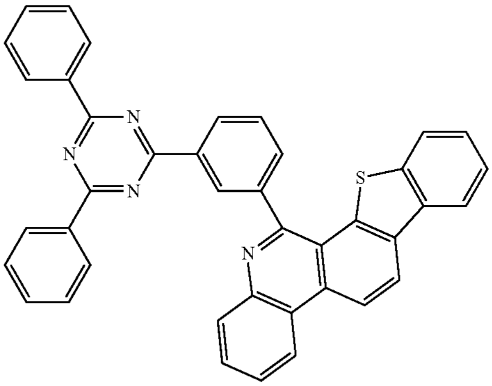
3-192
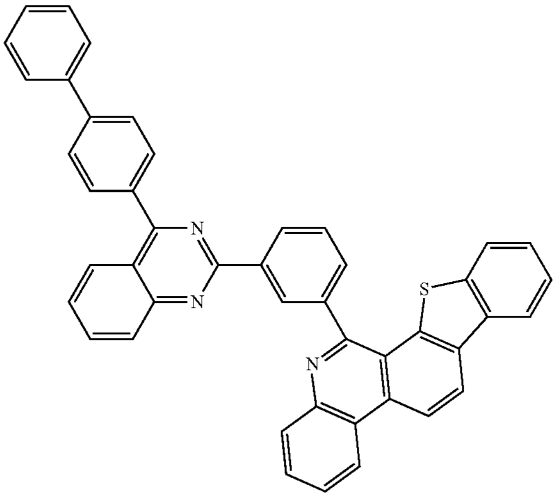
3-193
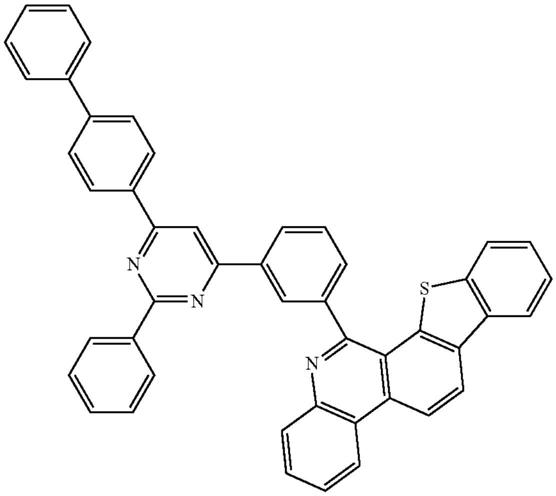
3-194
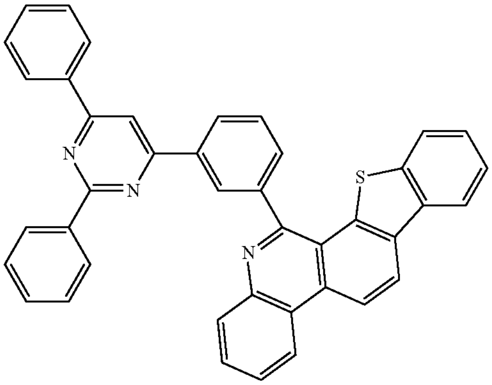
3-195
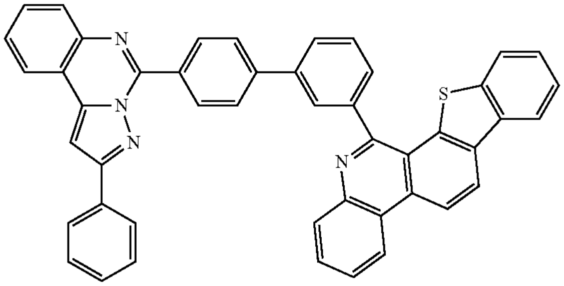
3-196
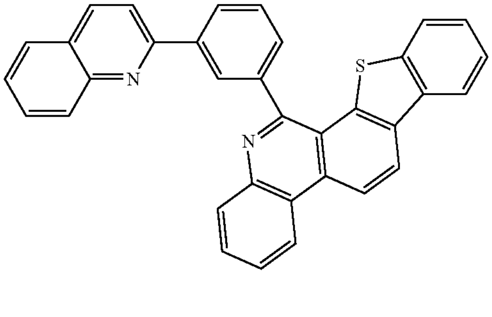

-continued
3-197
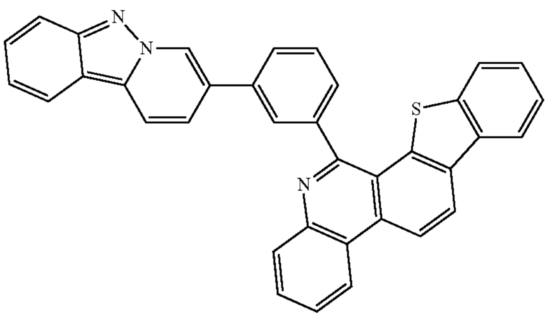
3-198
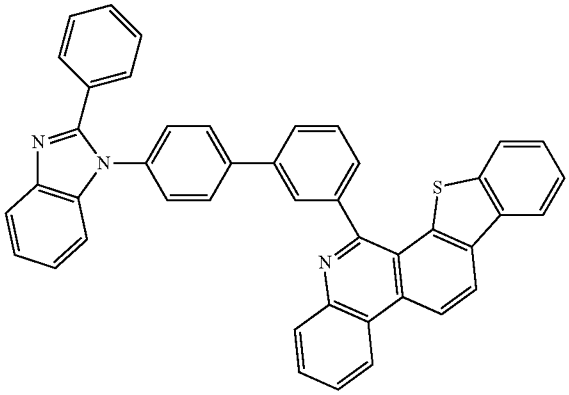
3-199
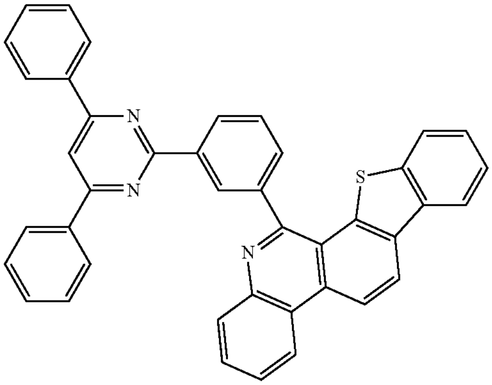
3-200
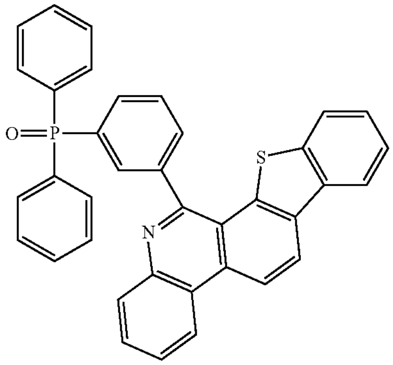
3-201
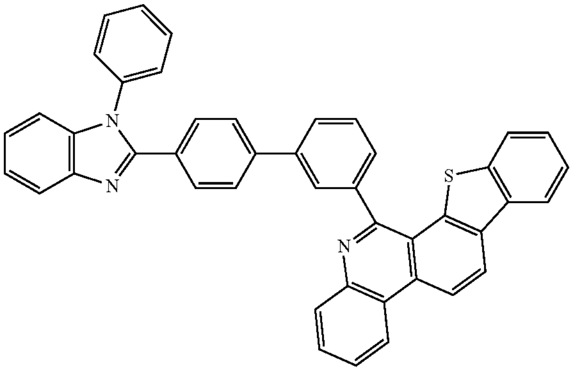
3-202
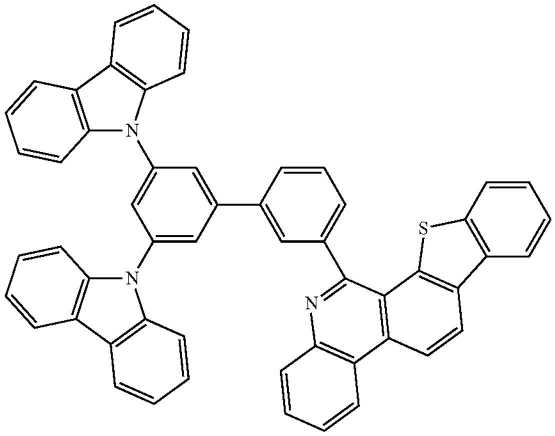
3-203
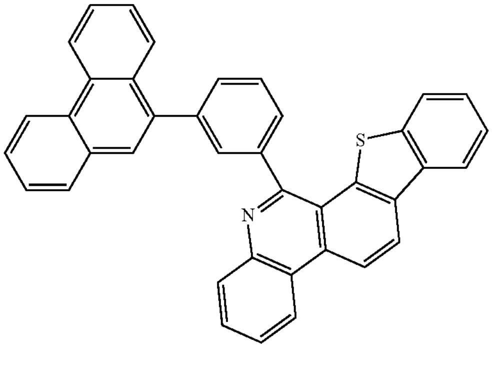
3-204
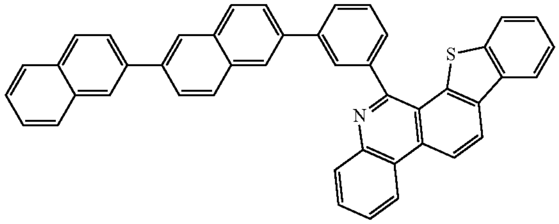

-continued
3-205
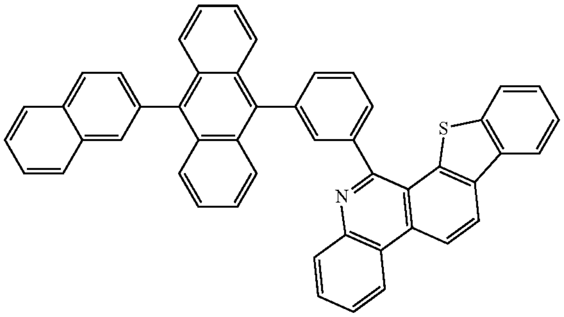
3-206
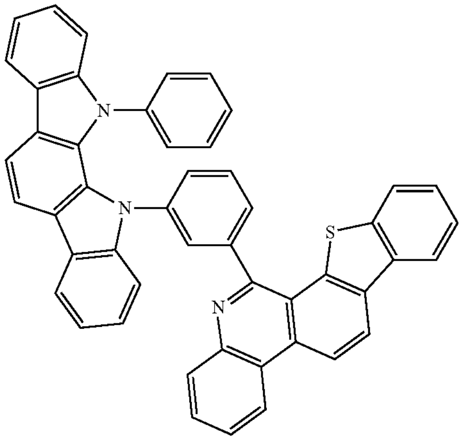
3-207
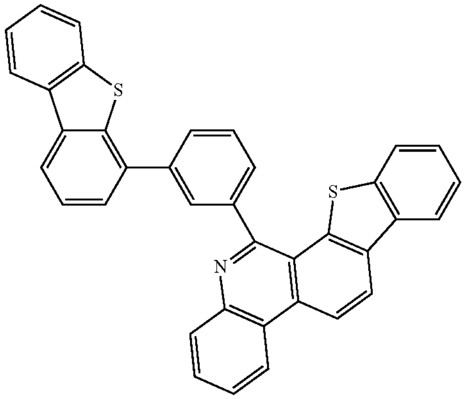
3-208
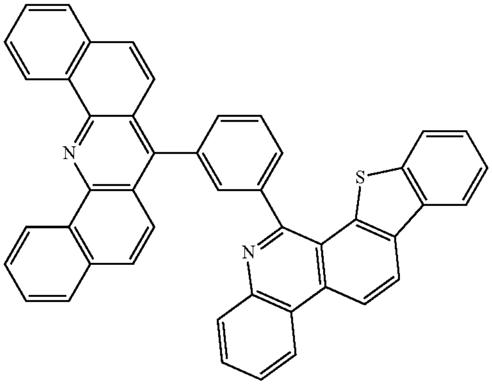
3-209
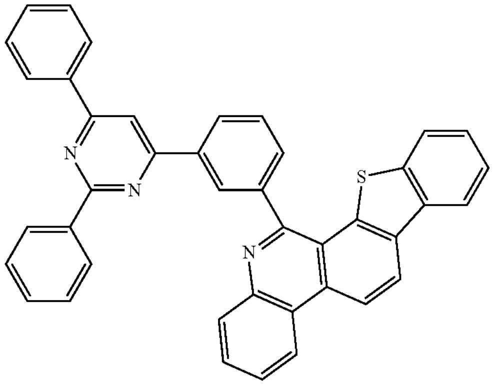
3-210
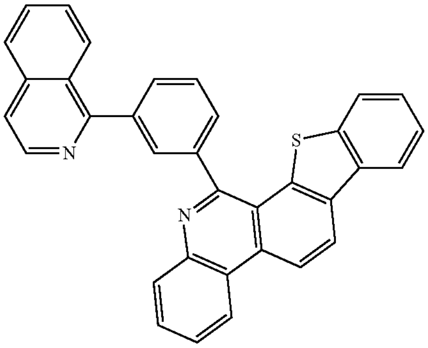

-continued
3-211
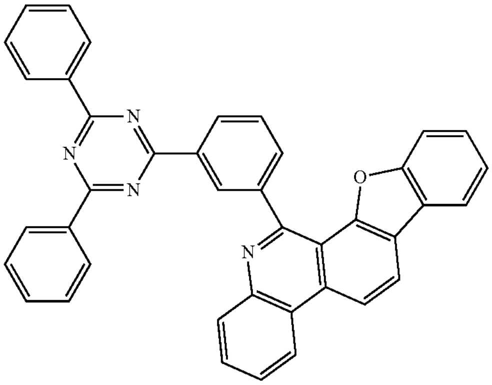
3-212
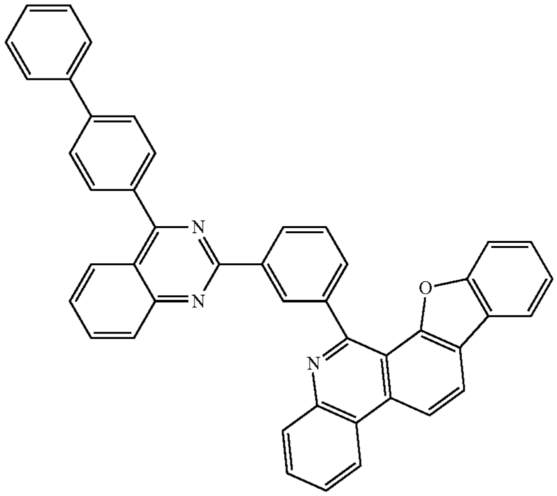
3-213
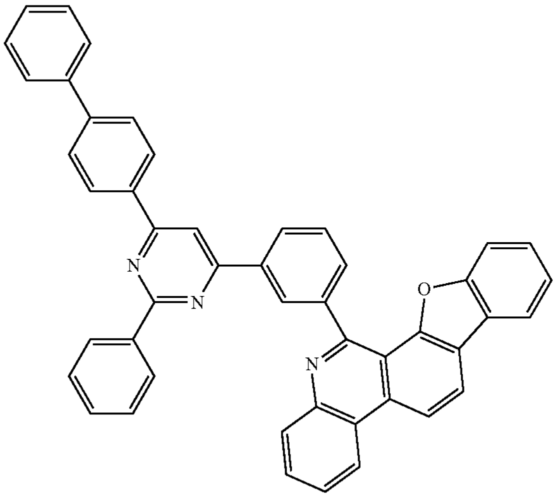
3-214
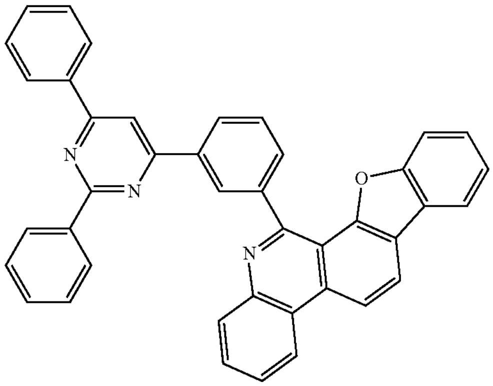
3-215
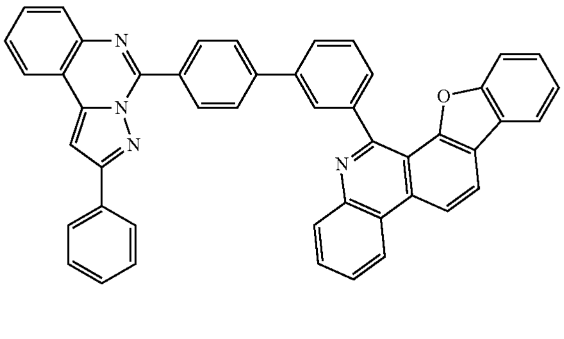
3-216
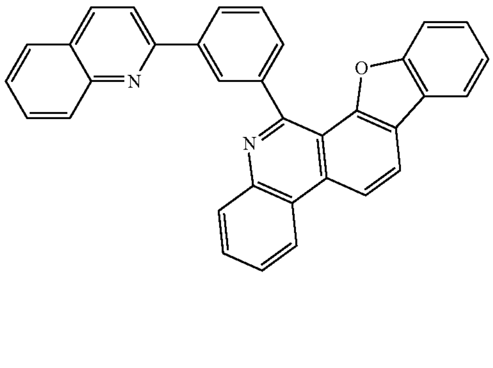

-continued
3-217
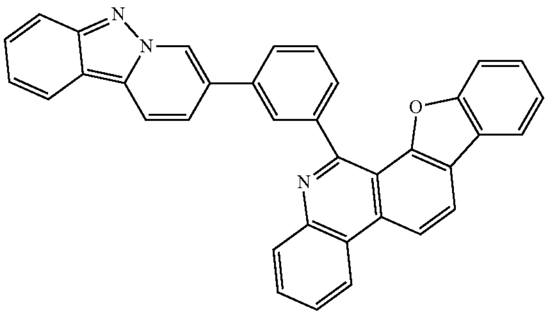
3-218
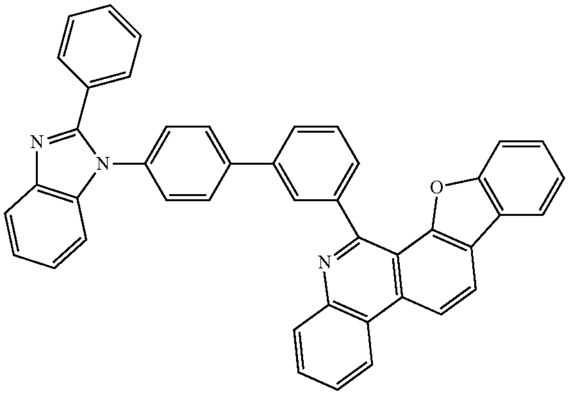
3-219
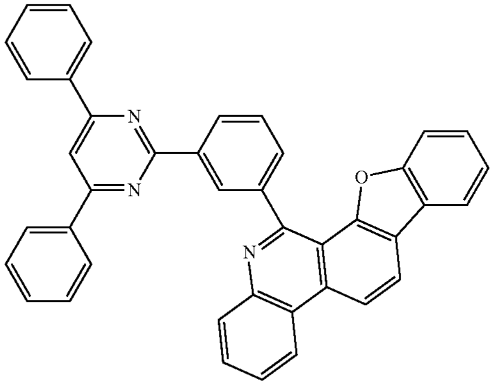
3-220
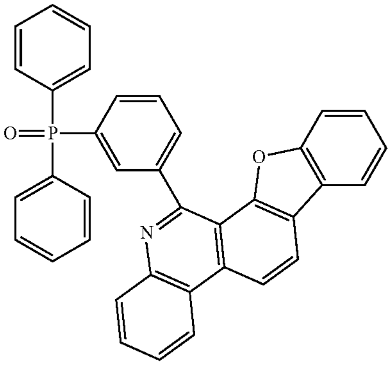
3-221
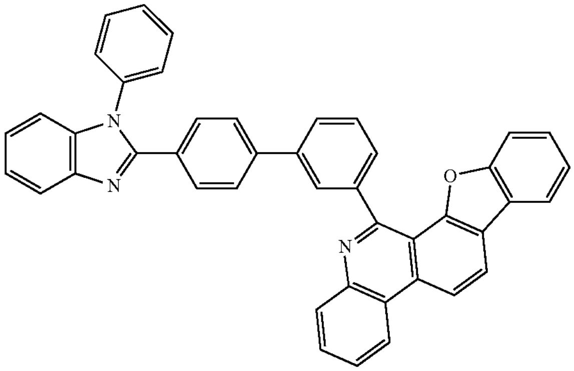
3-222
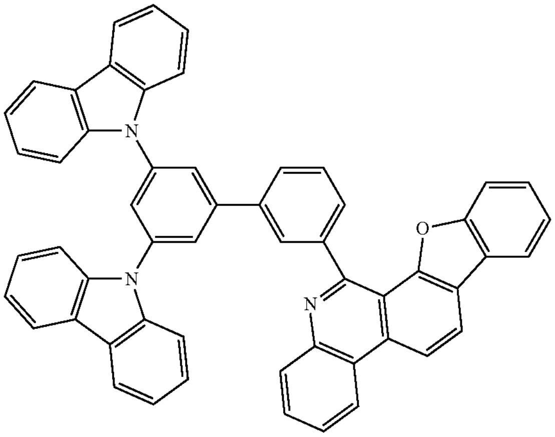
3-223
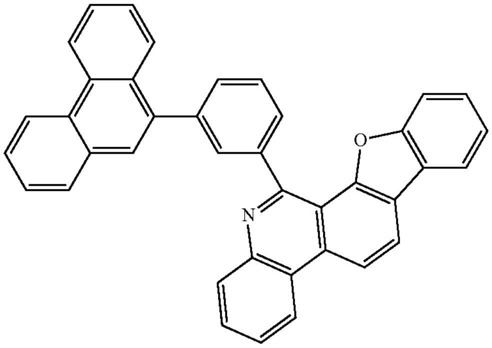

-continued
3-224
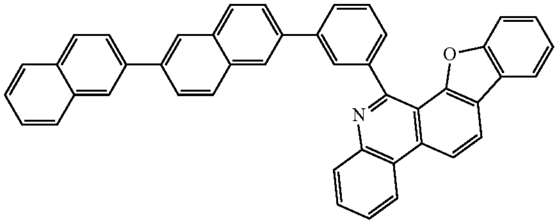
3-225
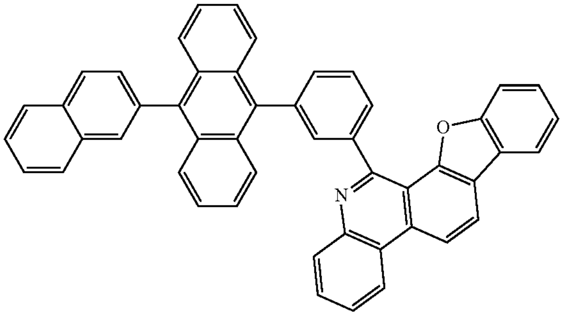
3-226
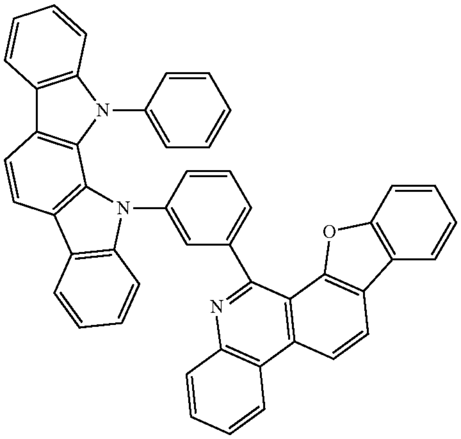
3-227
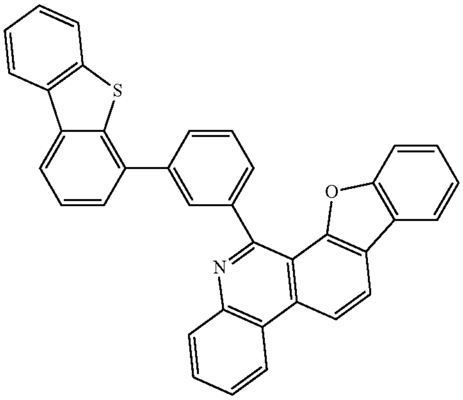
3-228
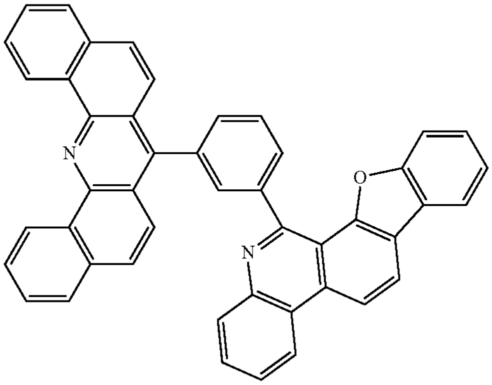
3-229
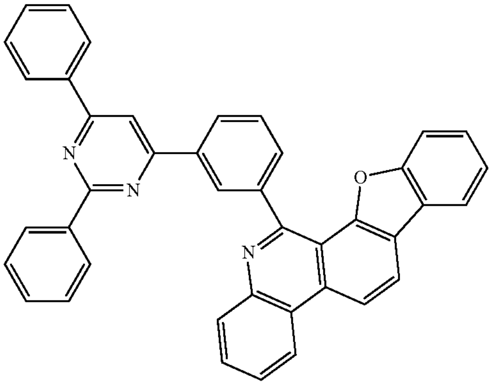
3-230
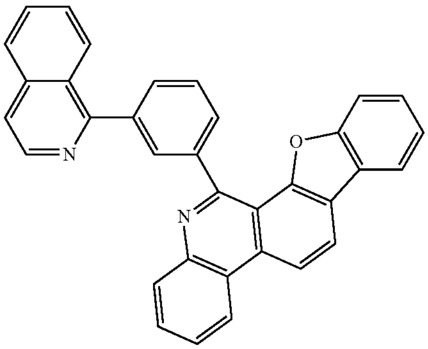
2-231
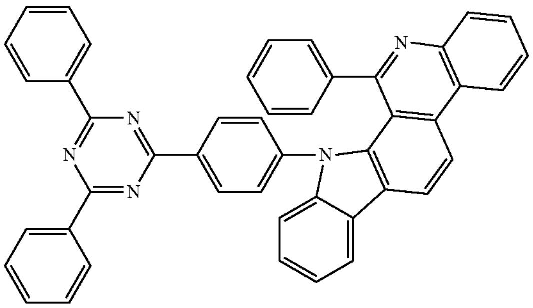

-continued
3-232
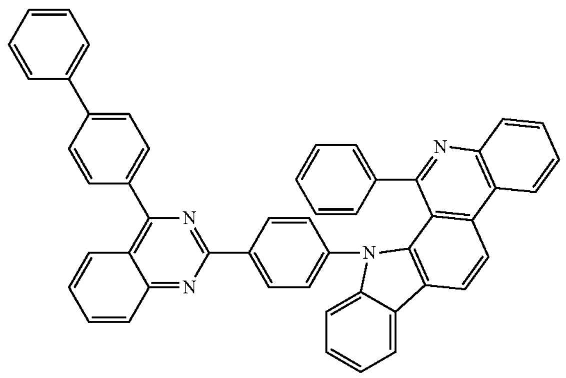
2-233
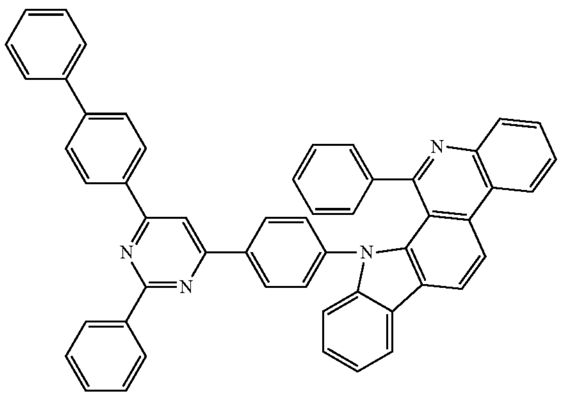
3-234
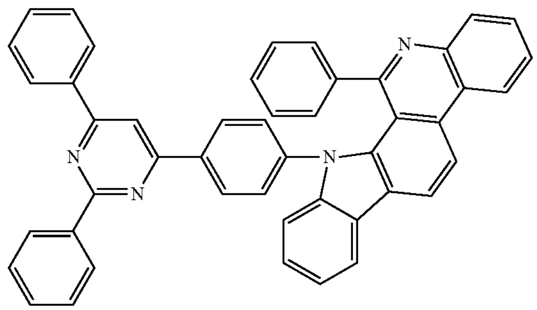
3-235
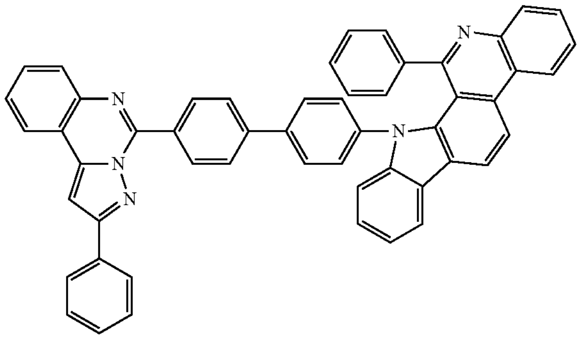
3-236
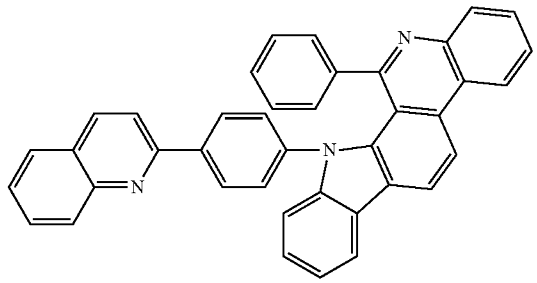
3-237
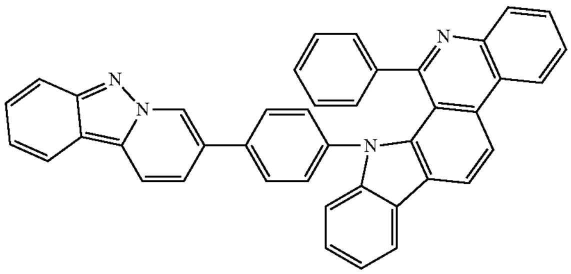
3-238
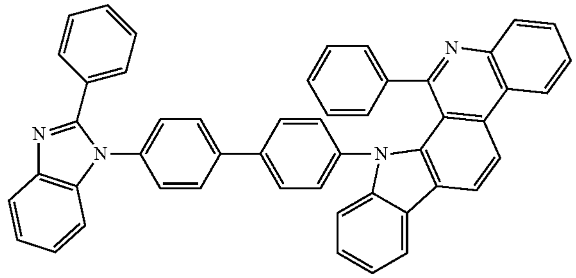
3-239
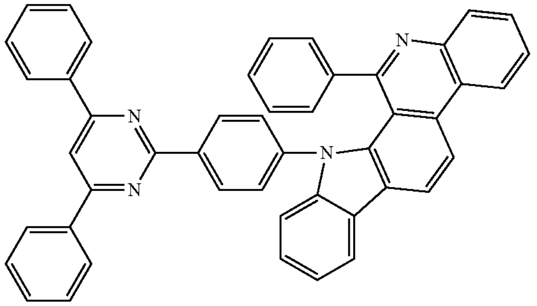

-continued
3-240
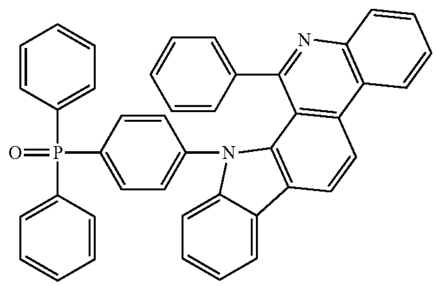
3-341
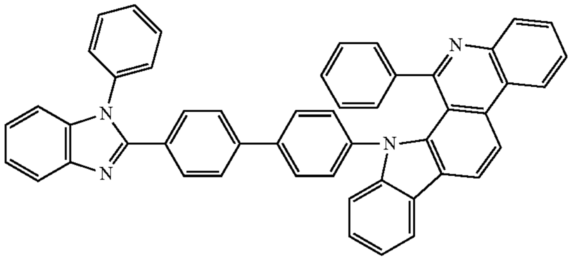
3-242
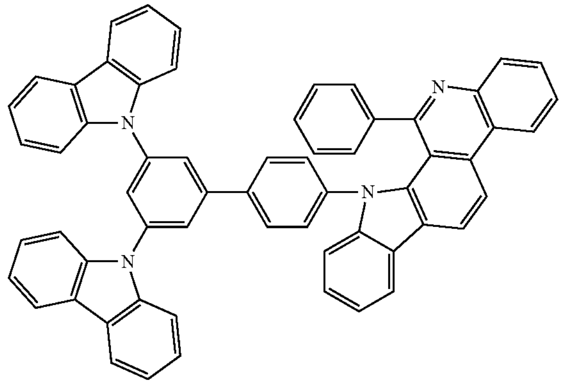
3-243
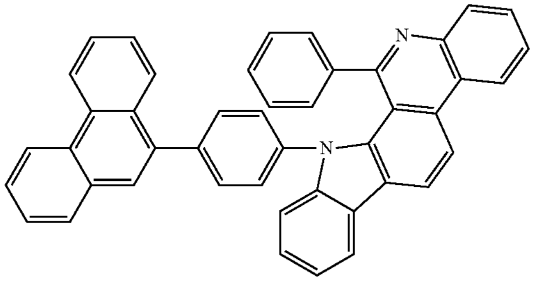
3-244
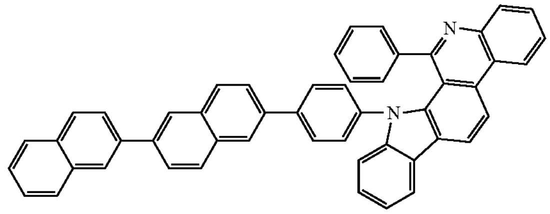
3-245
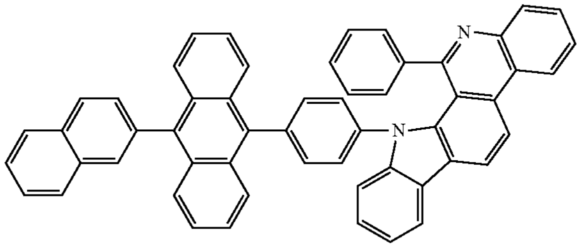
3-246
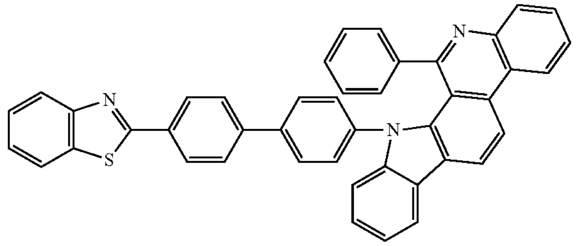
3-247
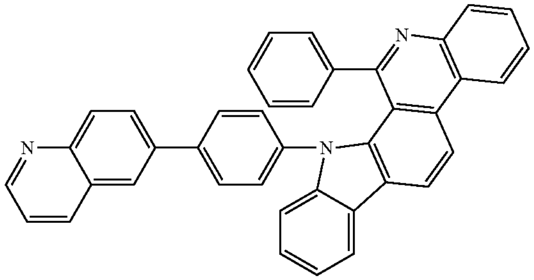
3-248
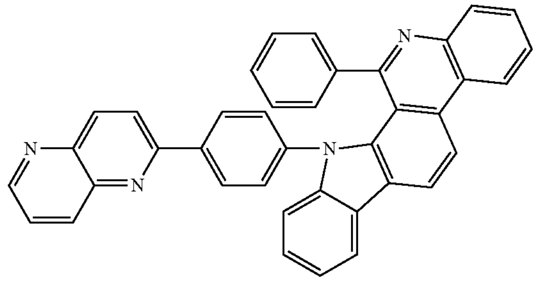
3-249
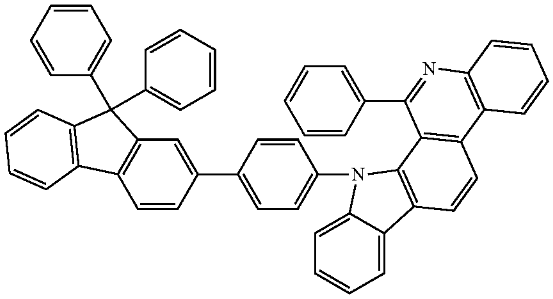

-continued
3-250
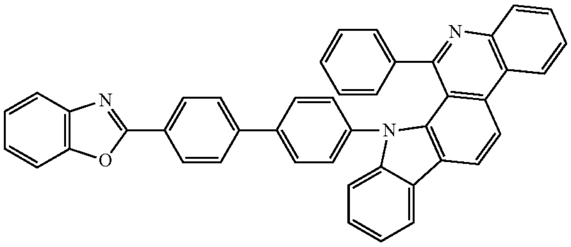
3-251
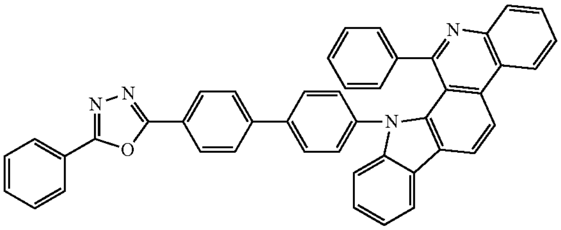
3-252
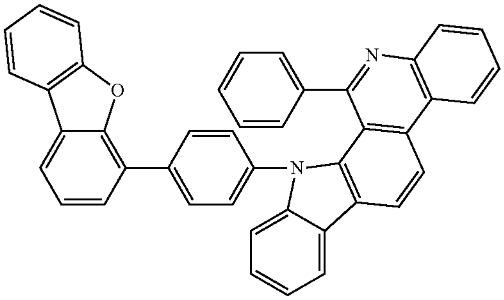
3-253
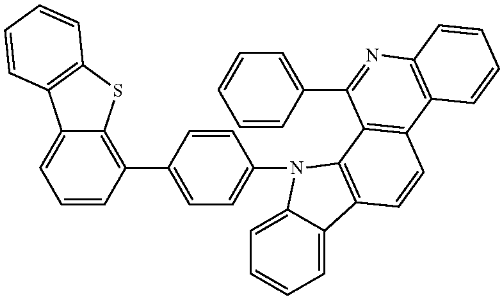
3-254
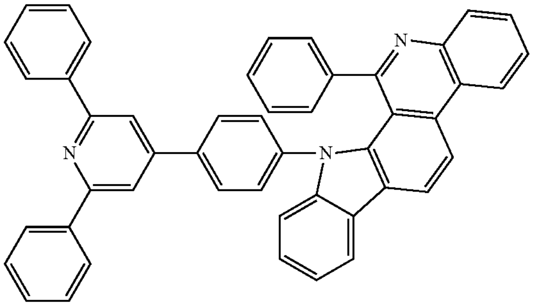
3-255
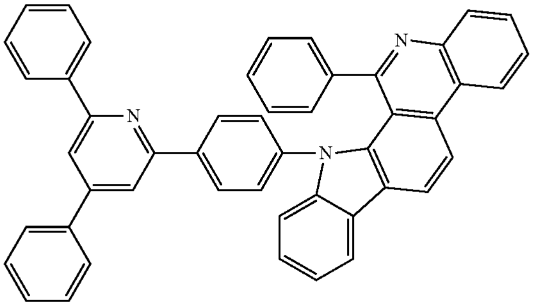
3-256
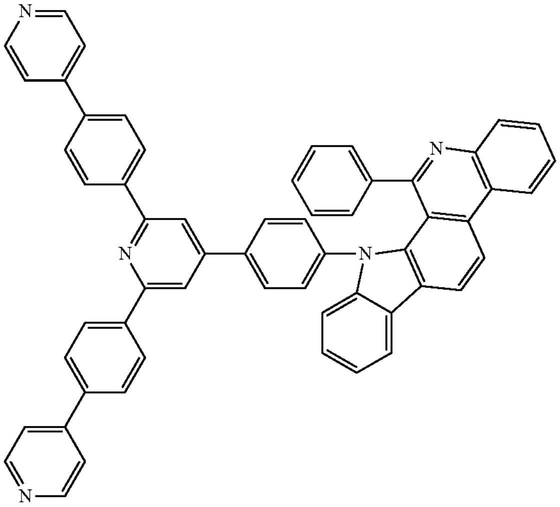
3-257
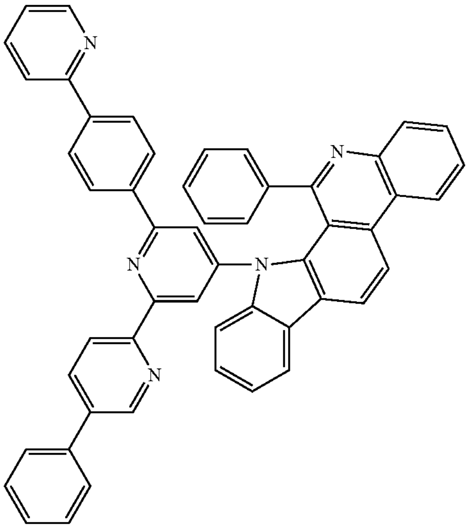

-continued
3-258
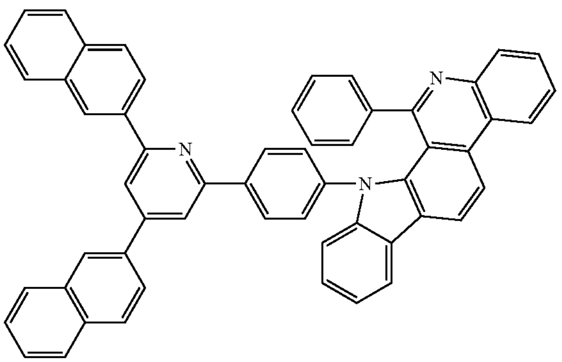
3-259
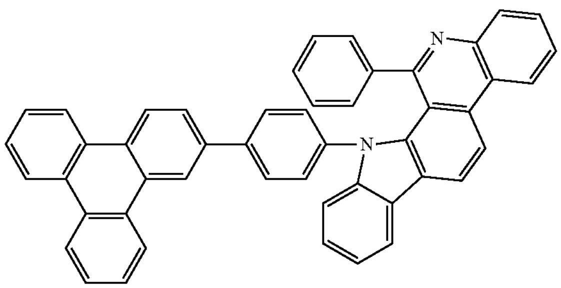
3-260
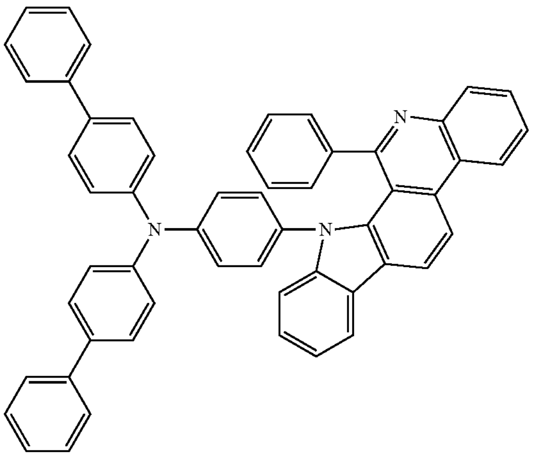
3-261
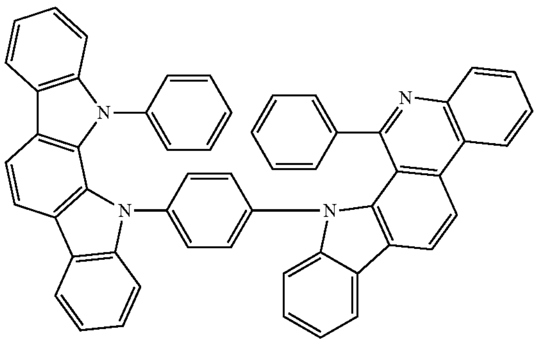
3-262
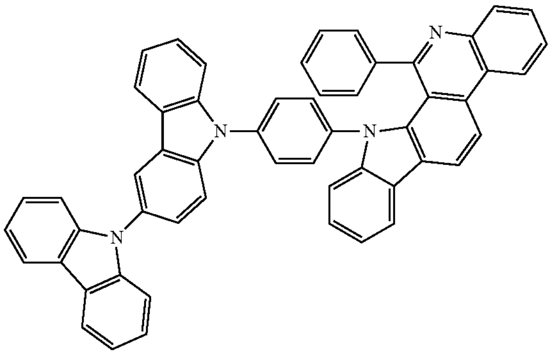
3-263
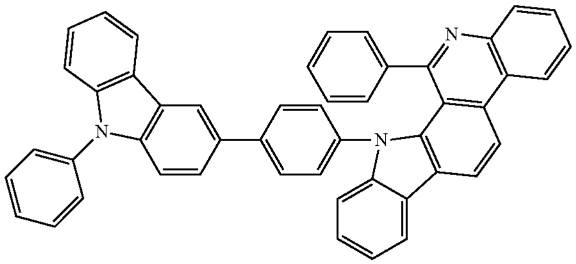
3-264
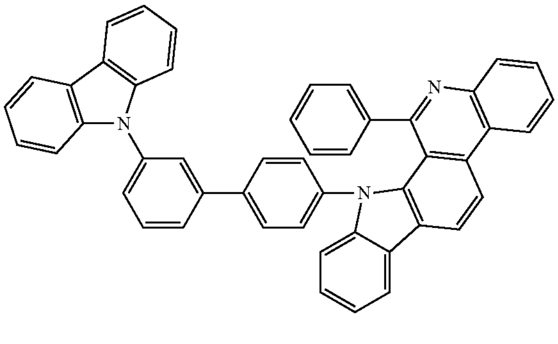
3-265
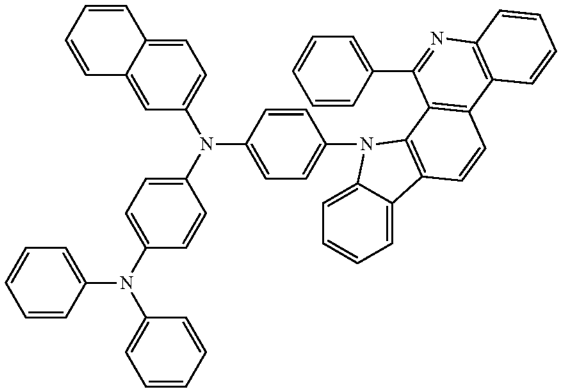

-continued
3-266
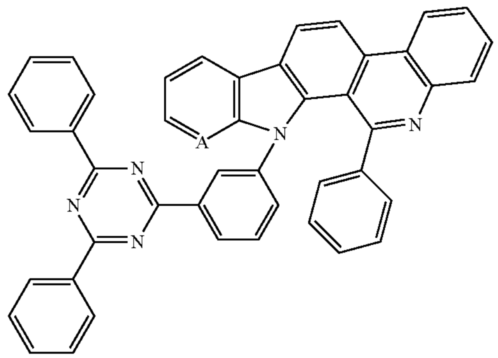
3-267
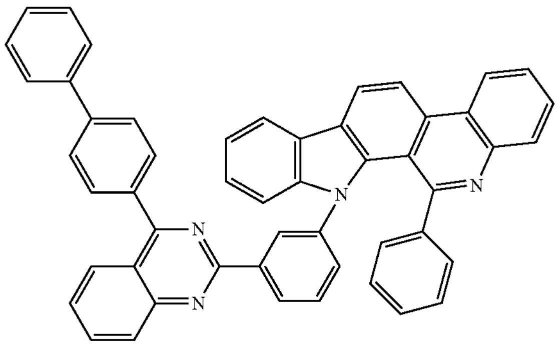
3-268
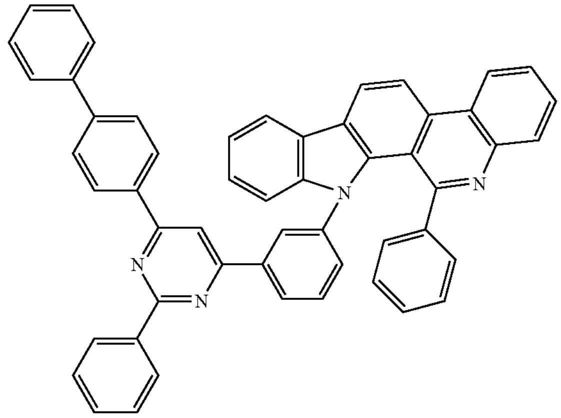
3-269
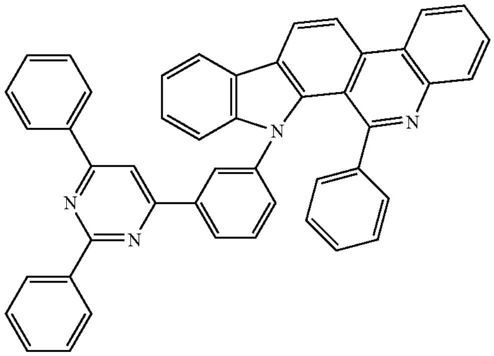
3-270
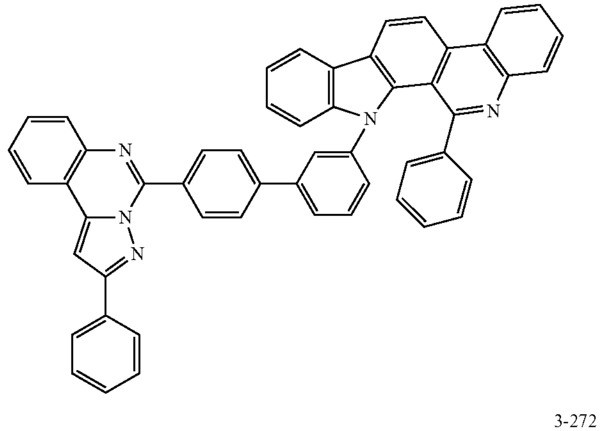
3-271
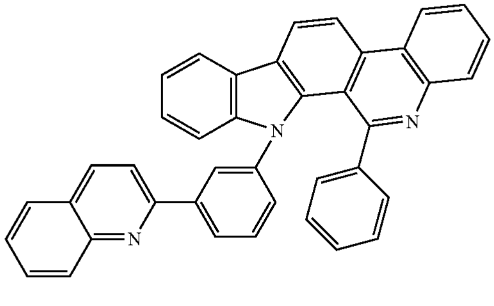
3-272
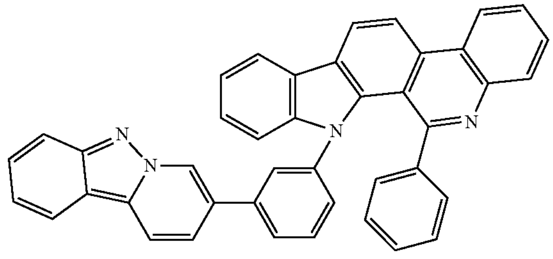
3-273
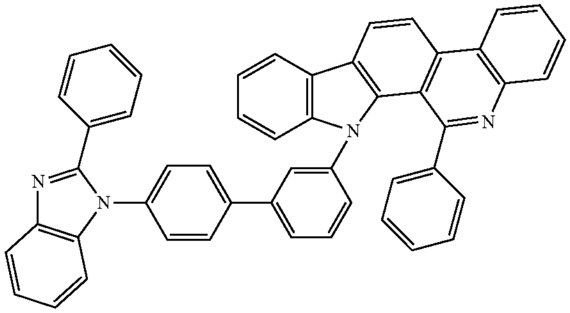

-continued
3-274
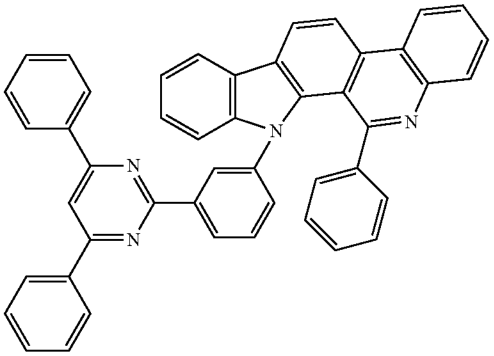
3-275
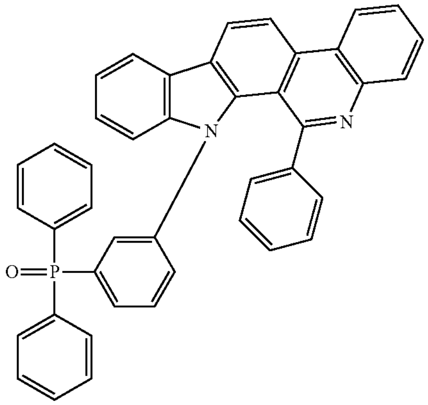
3-276
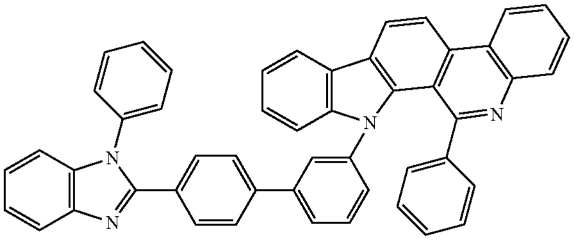
3-277
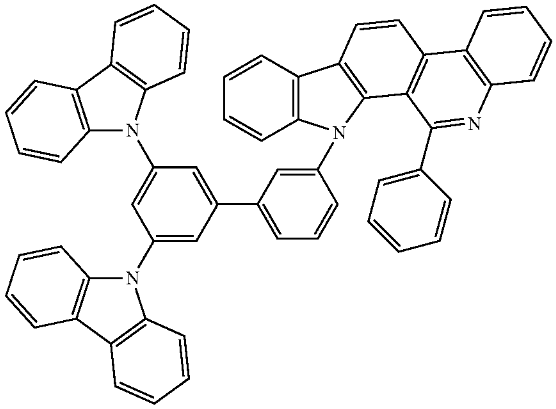
3-278
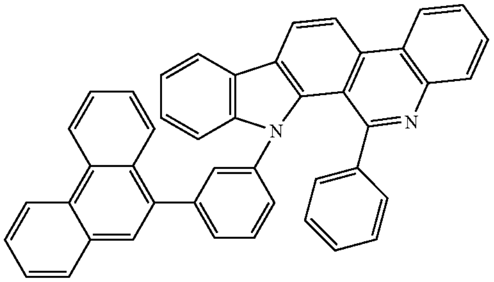
3-279
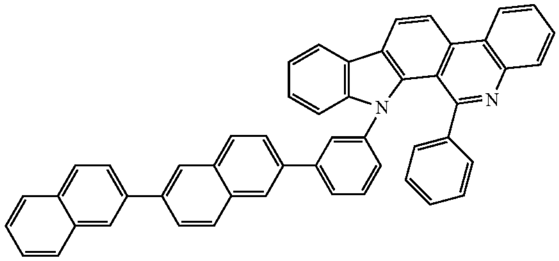
3-280
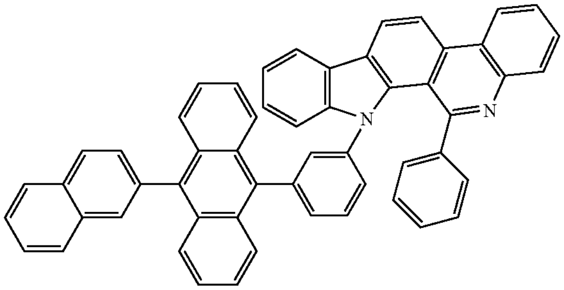
3-281
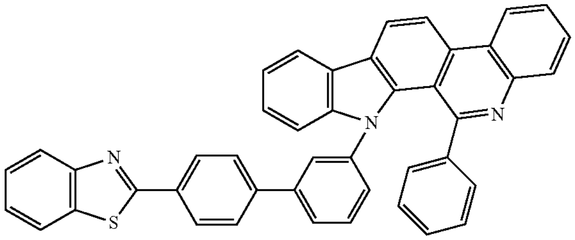

-continued
3-282
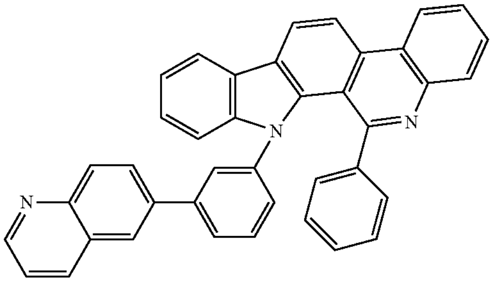
3-283
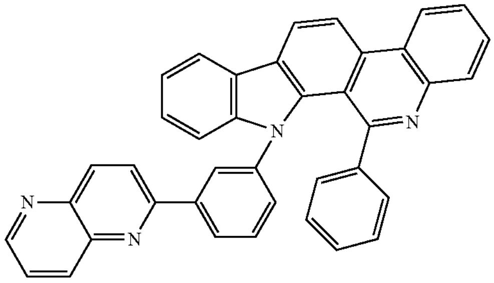
3-284
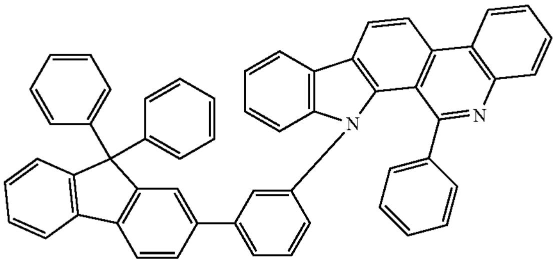
3-285
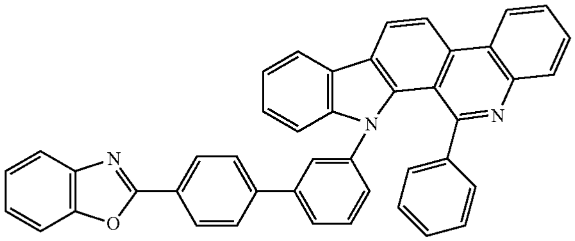
3-286
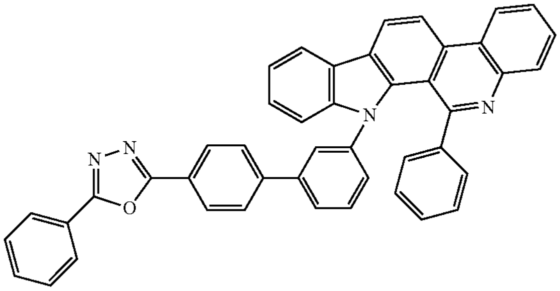
3-287
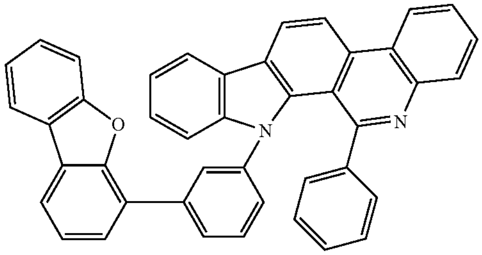
3-288
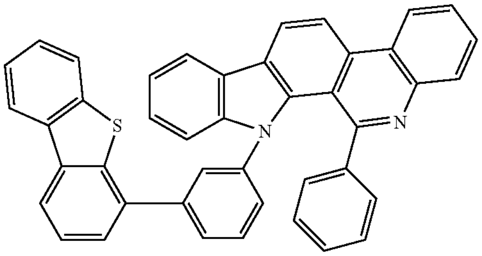
3-289
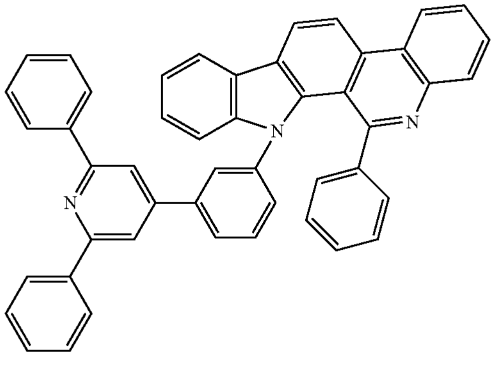

-continued
3-290
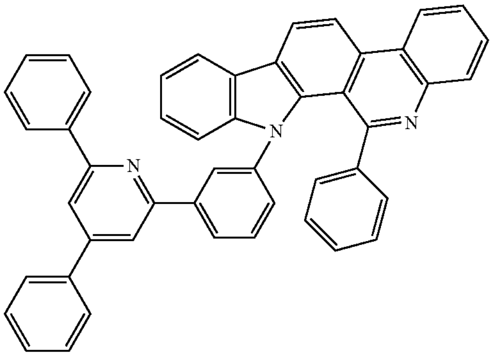
3-291
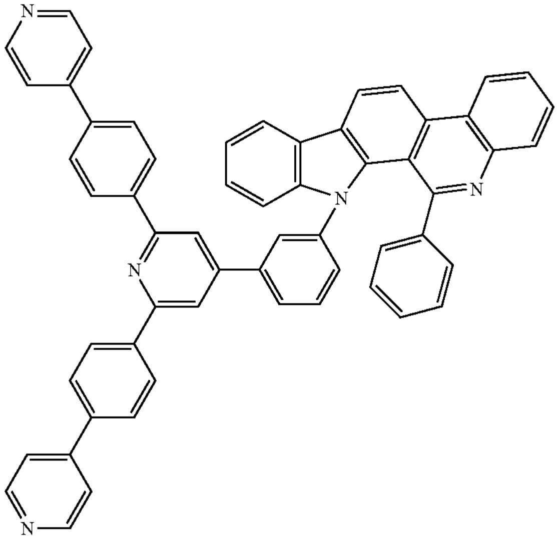
3-292
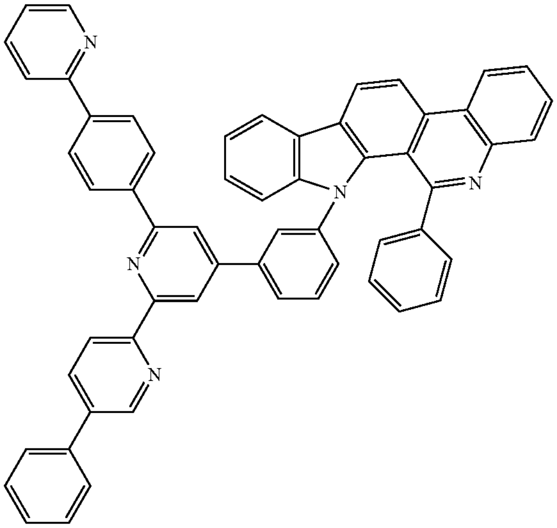
3-293
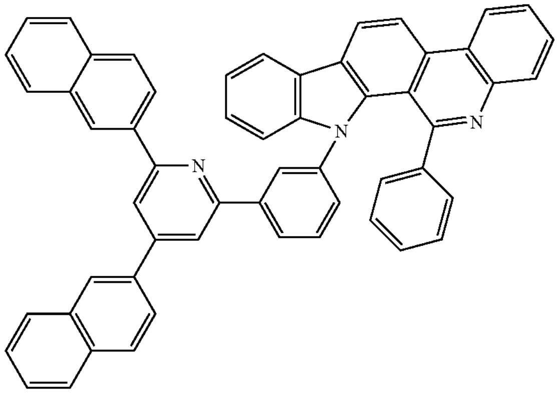
3-294
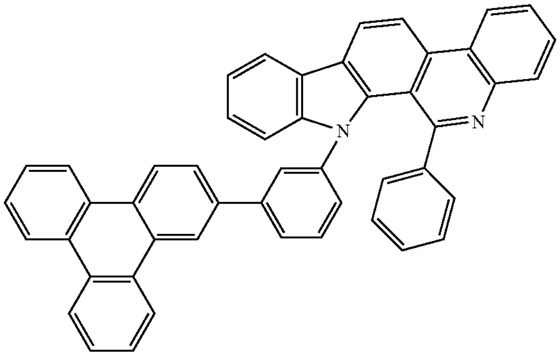
3-295
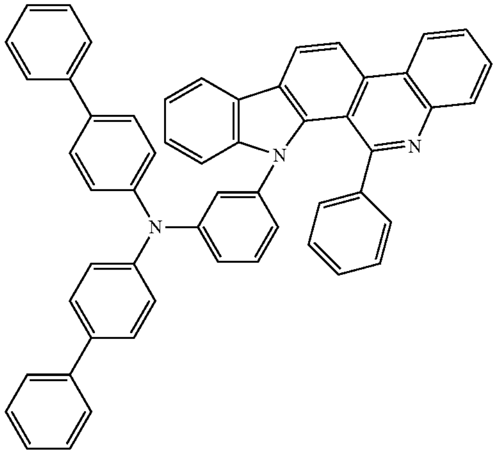

-continued
3-296
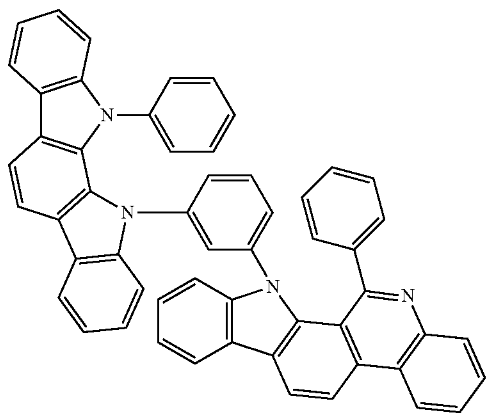
3-297
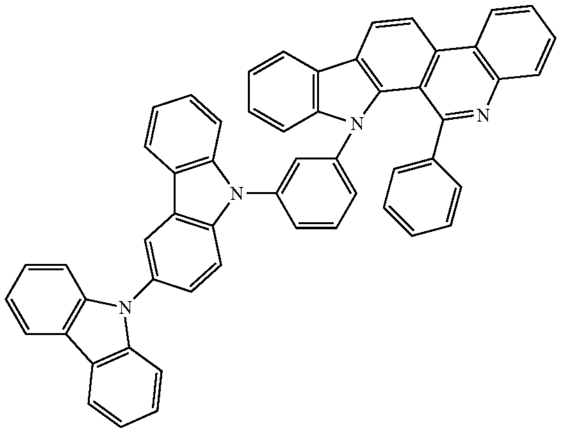
3-298
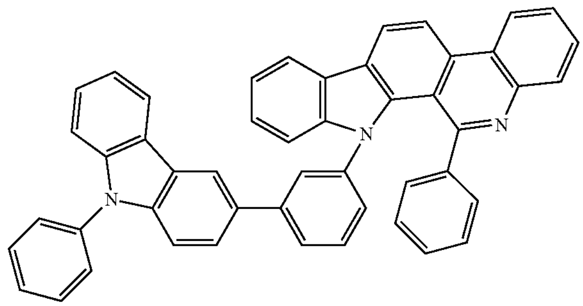
3-299
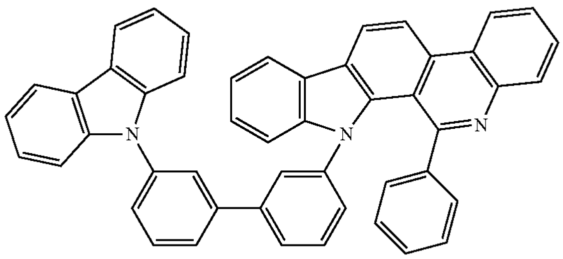
3-300
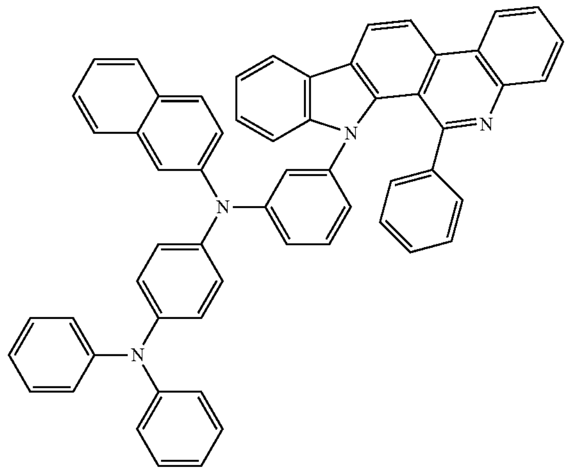
4-1
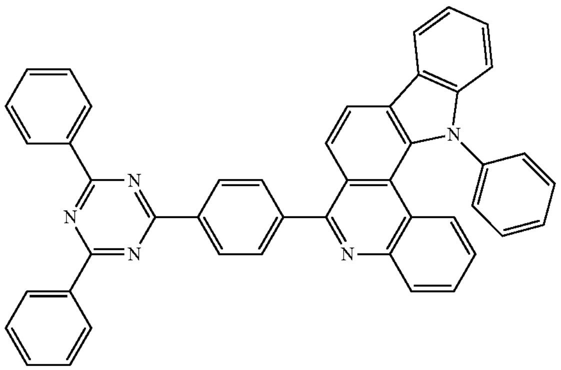

-continued
4-2
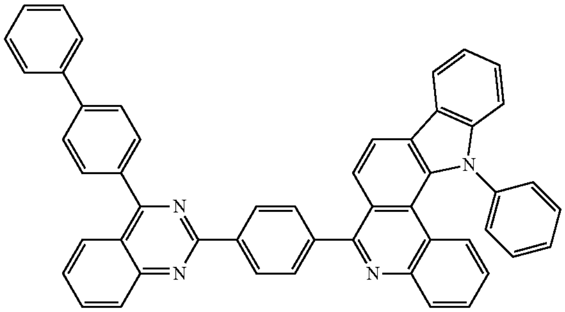
4-3
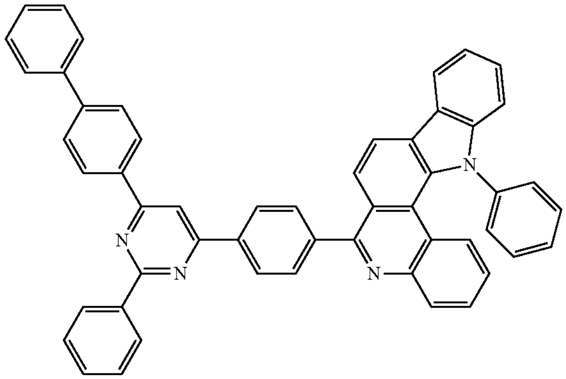
4-4
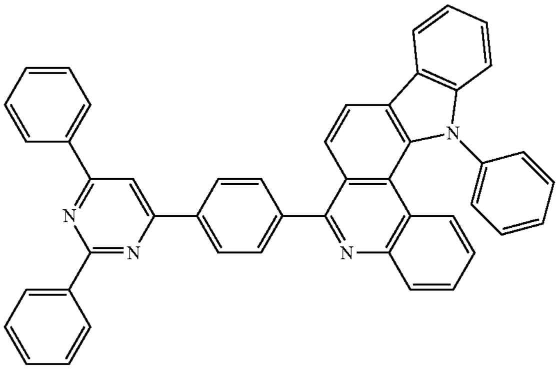
4-5
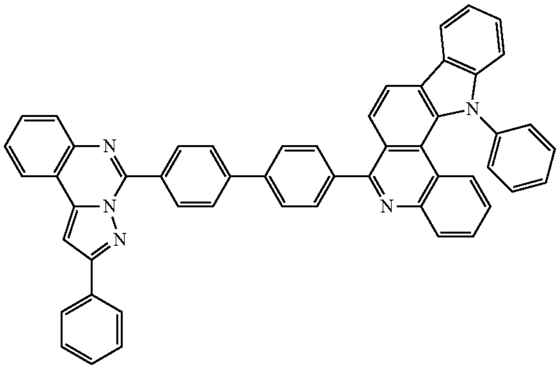
4-6
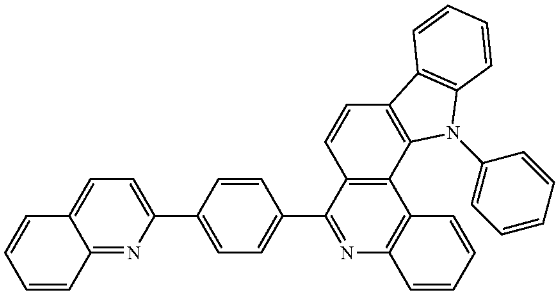
4-7
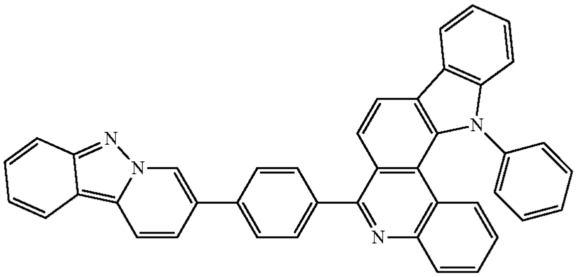
4-8
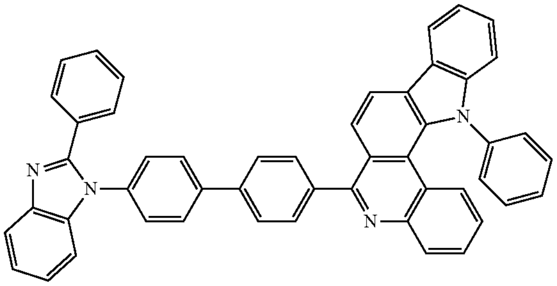
4-9
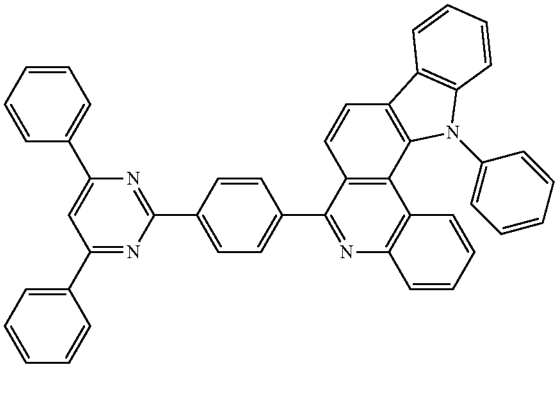

-continued
4-10
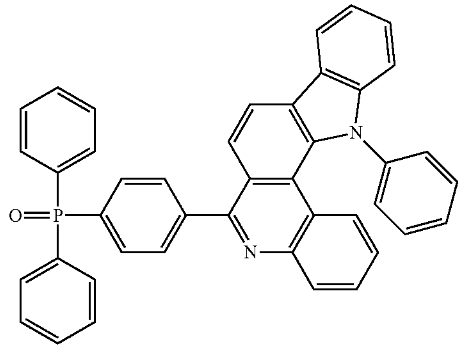
4-11
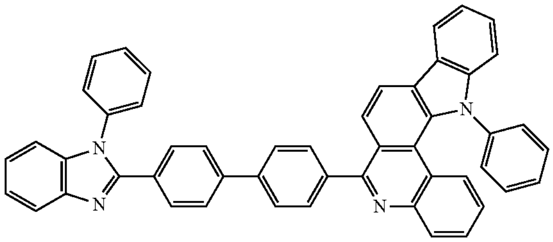
4-12
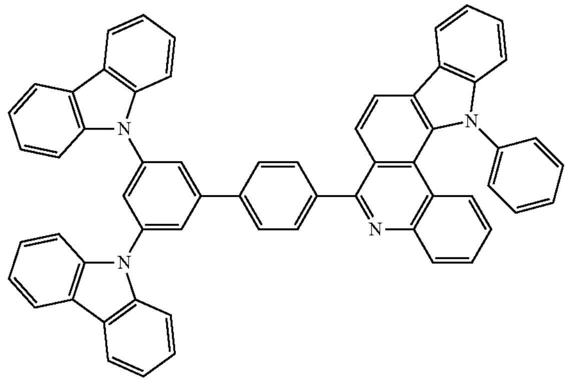
4-13
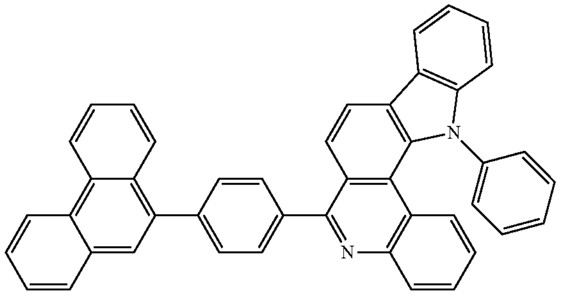
4-14
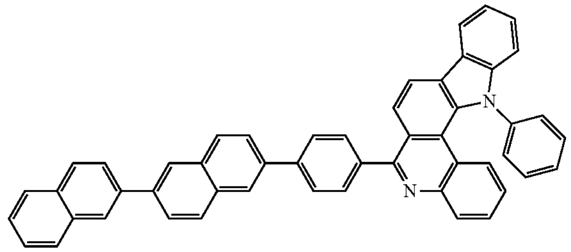
4-15
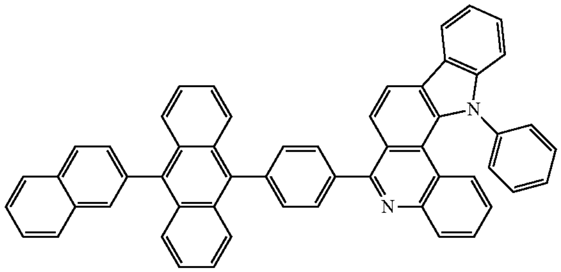
4-16
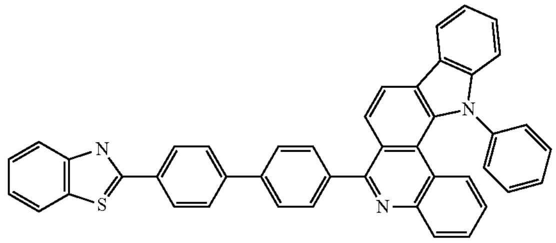
4-17
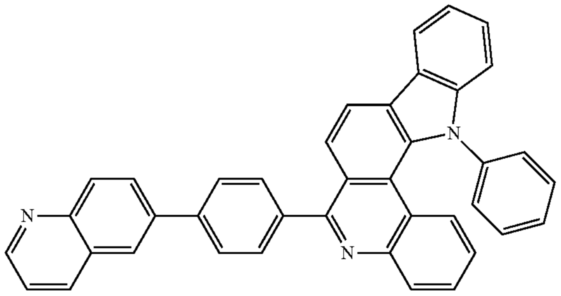

-continued
4-18
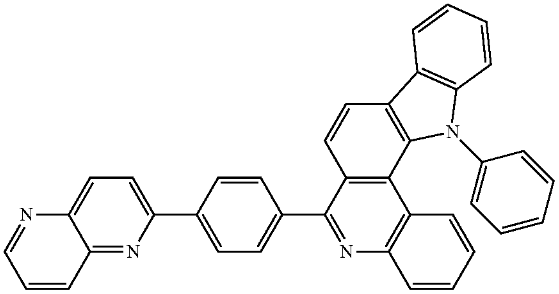
4-19
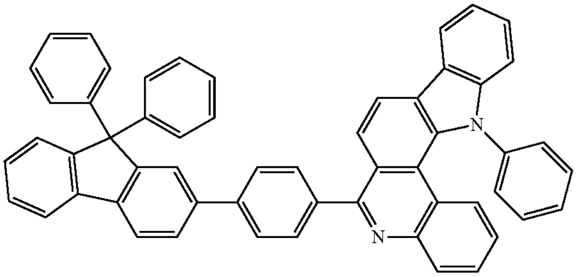
4-20
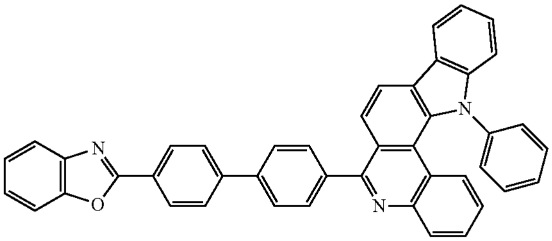
4-21
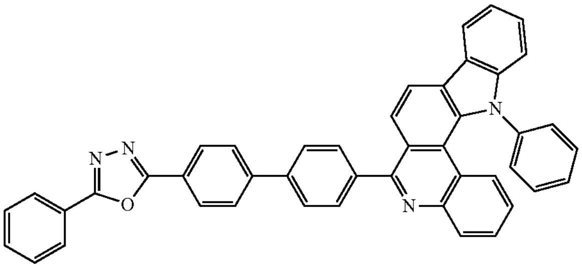
4-22
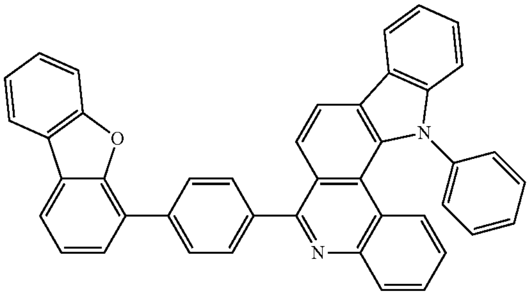
4-23
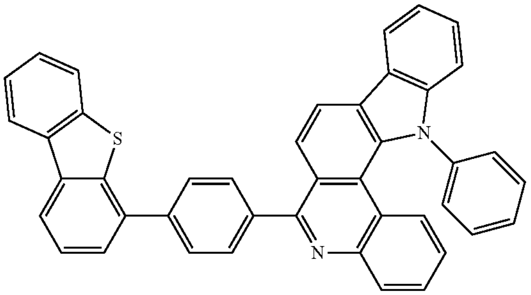
4-24
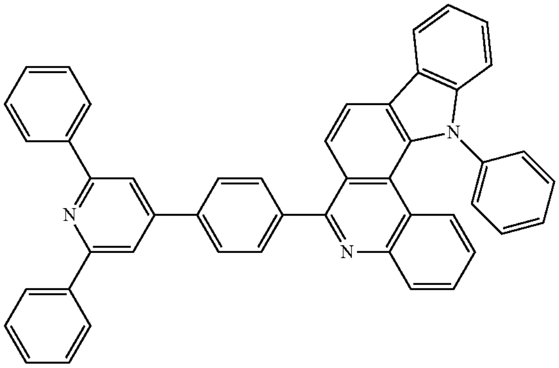
4-25
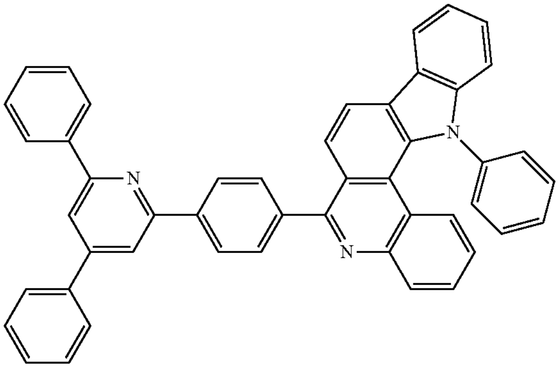

-continued
4-26
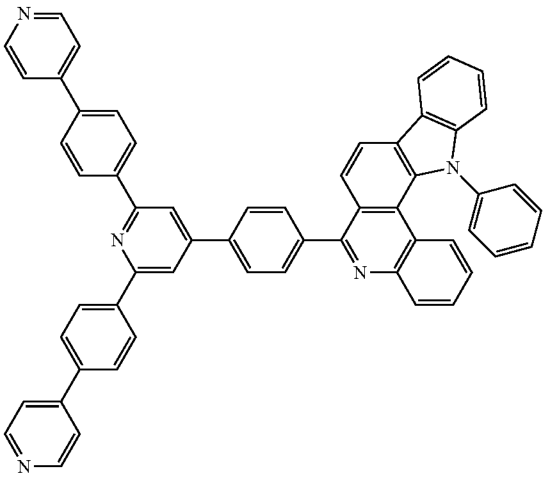
4-27
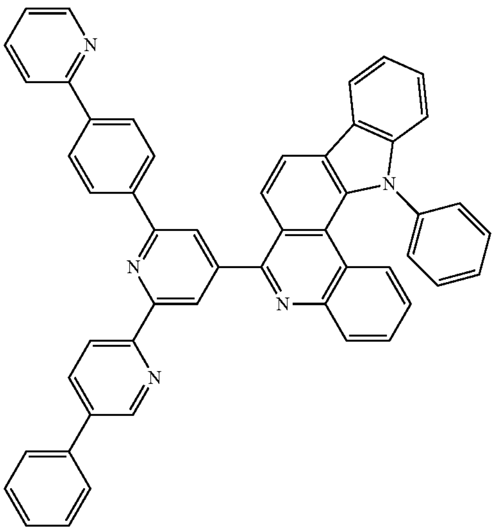
4-28
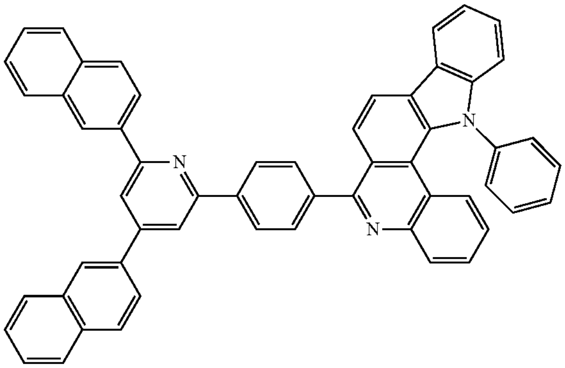
4-29
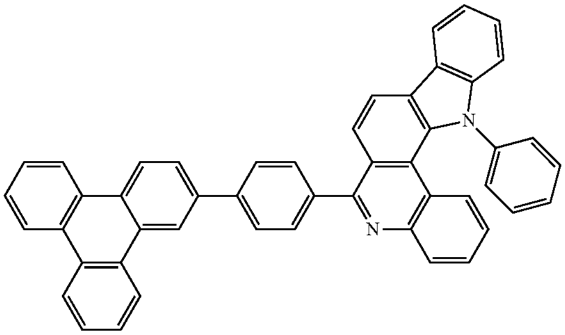
4-30
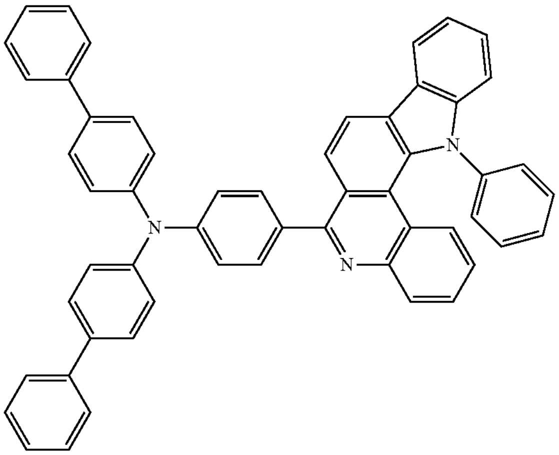
4-31
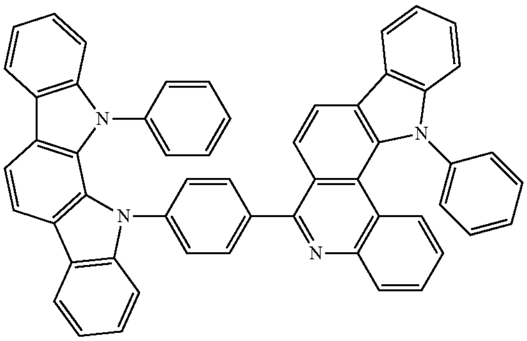

-continued
4-32
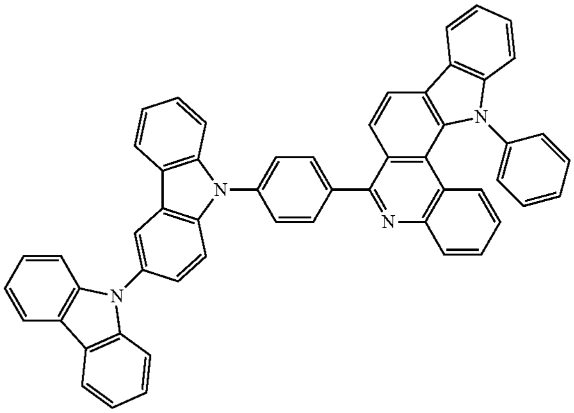
4-33
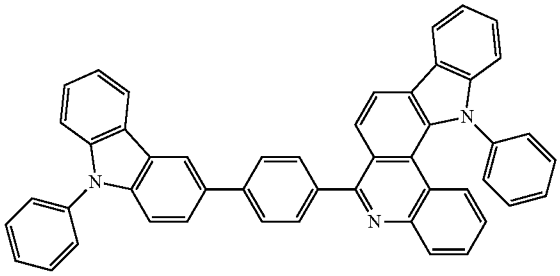
4-34
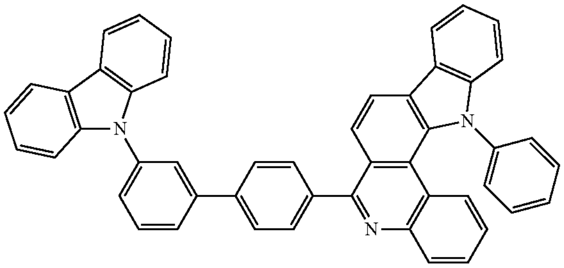
4-35
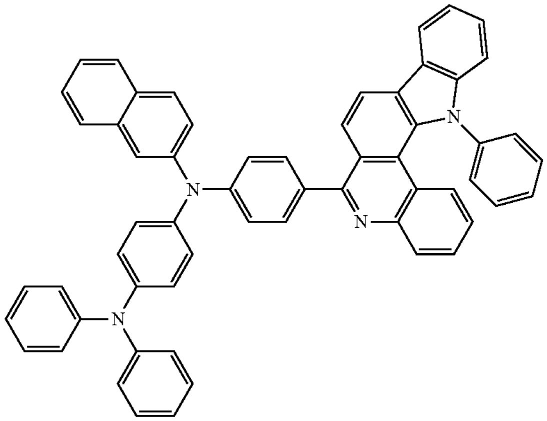
4-36
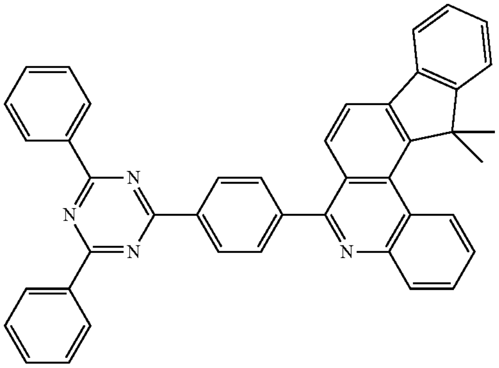
4-37
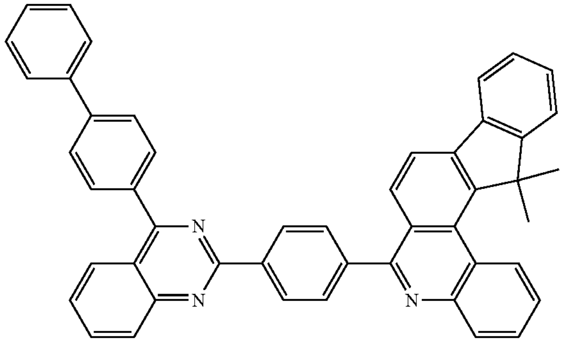

-continued
4-38
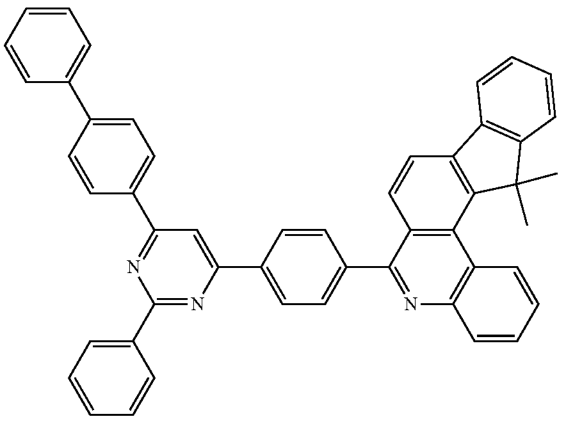
4-39
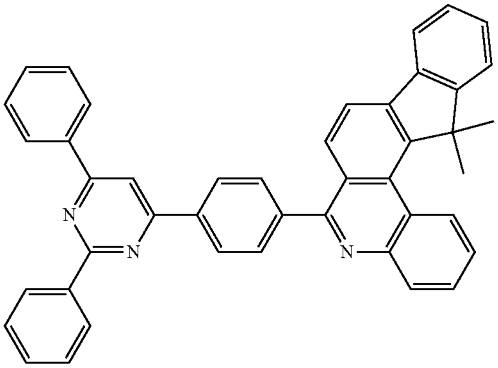
4-40
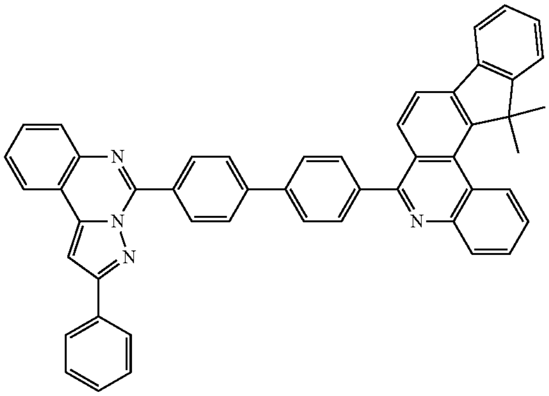
4-41
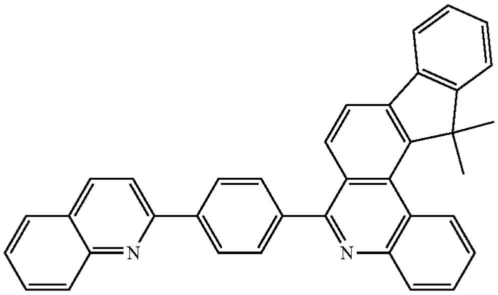
4-42
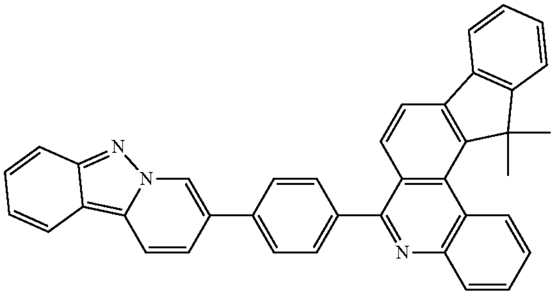
4-43
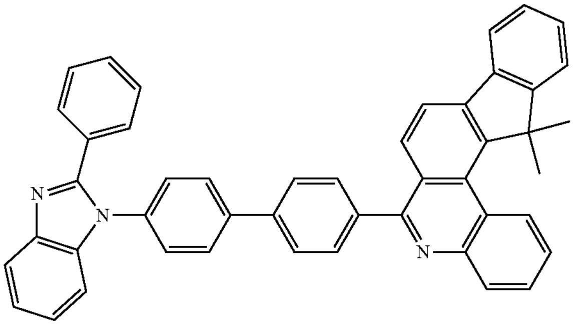
4-44
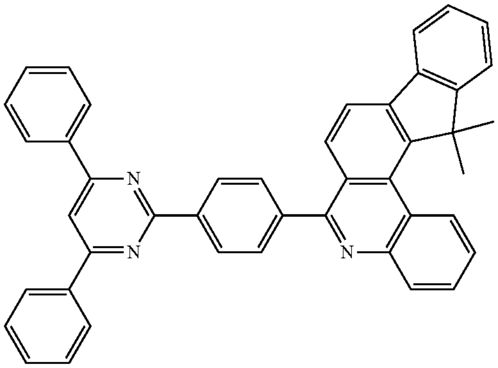
4-45
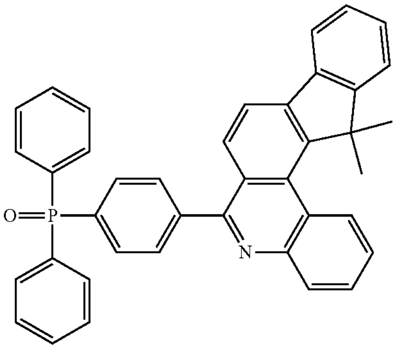

-continued
4-46
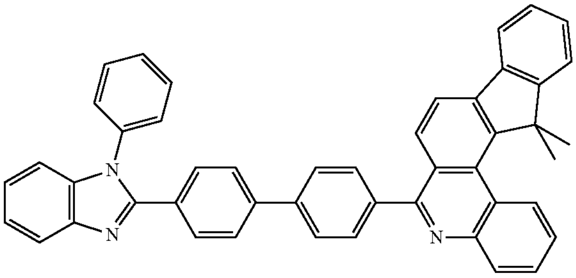
4-47
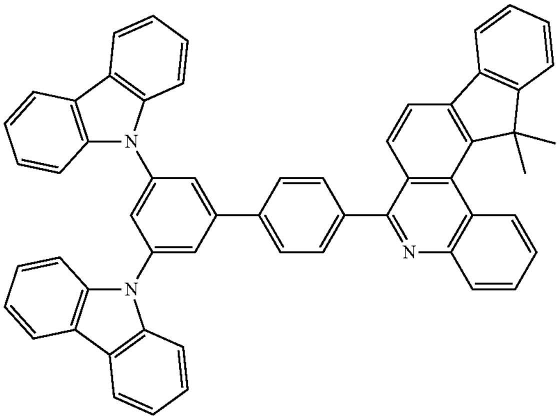
4-48
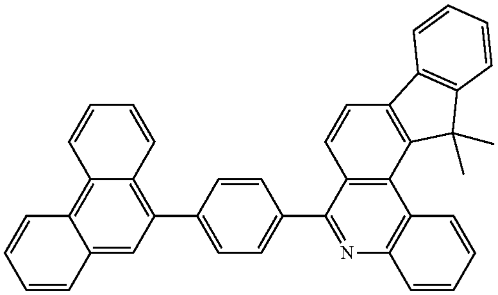
4-49
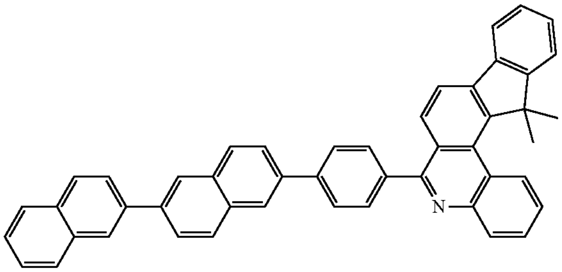
4-50
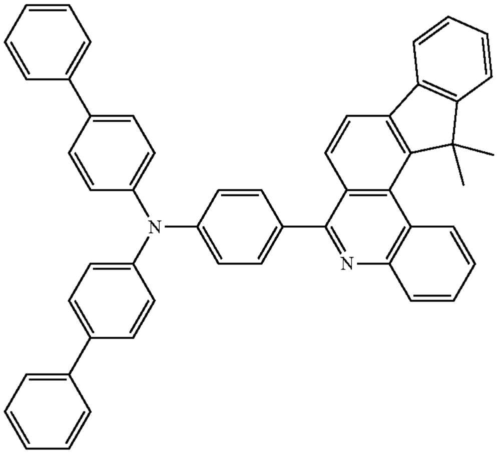
4-51
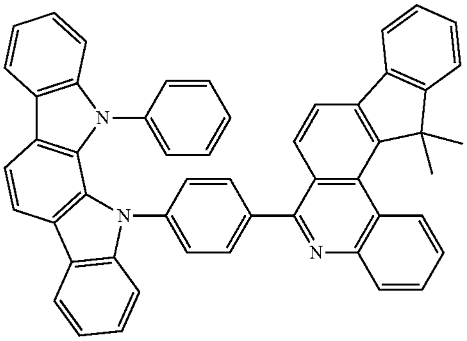
4-52
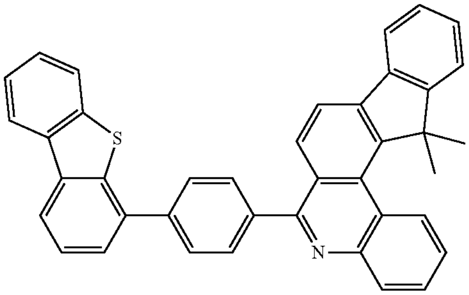
4-53
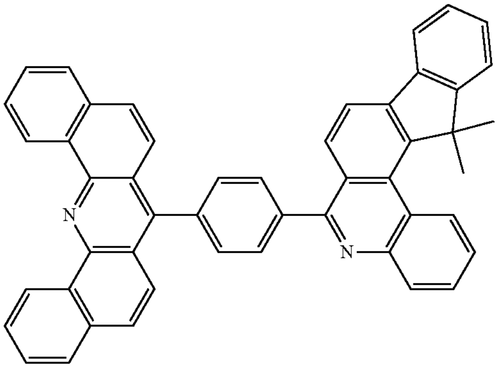

-continued
4-54
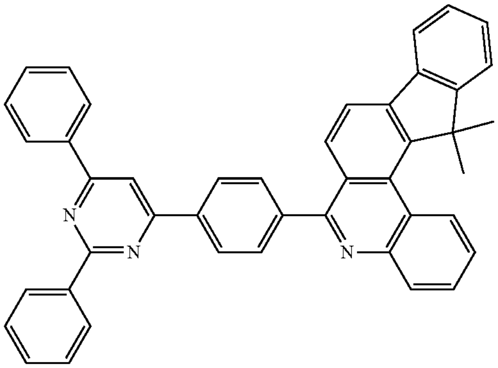
4-55
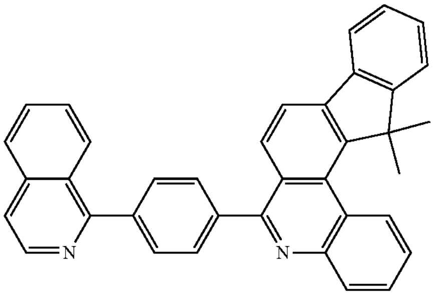
4-56
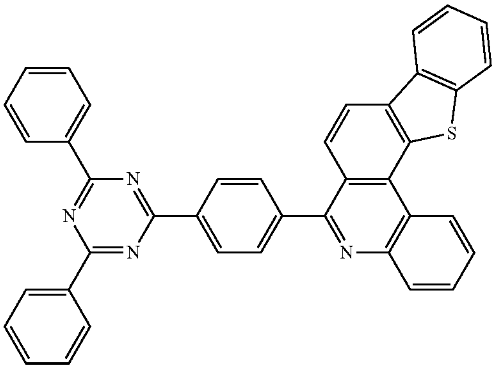
4-57
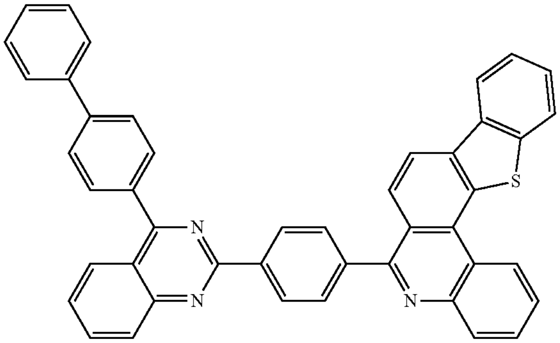
4-58
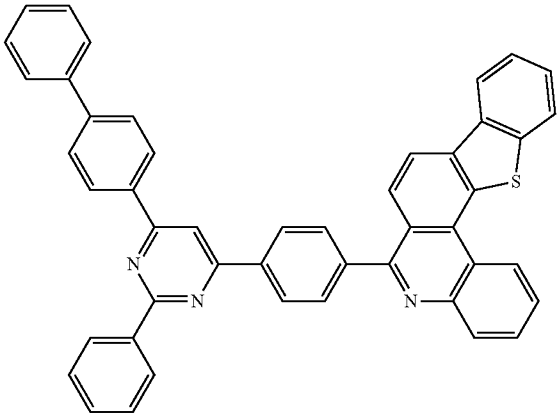
4-59
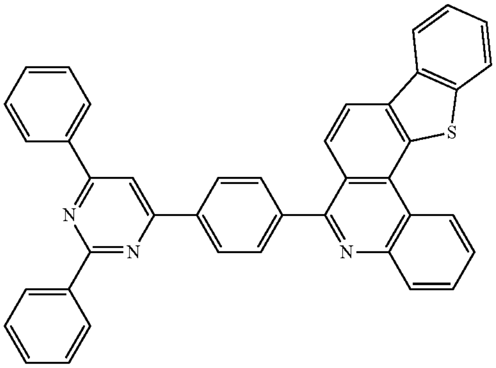
4-60
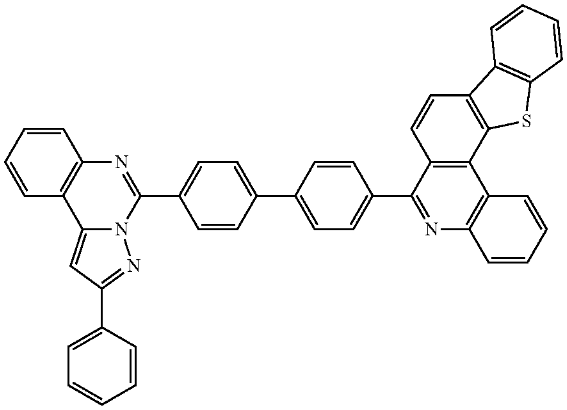
4-61
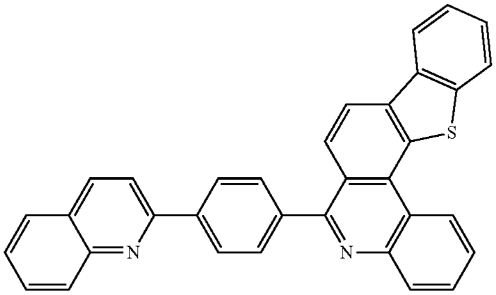

-continued
4-62
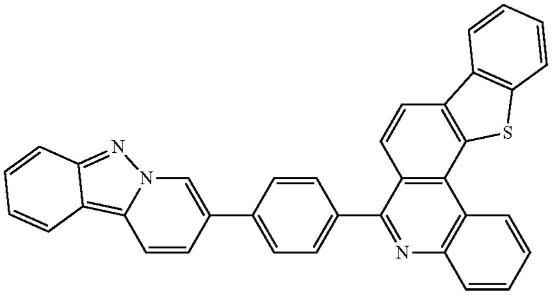
4-63
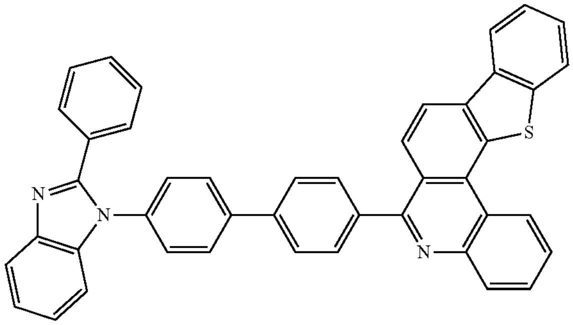
4-64
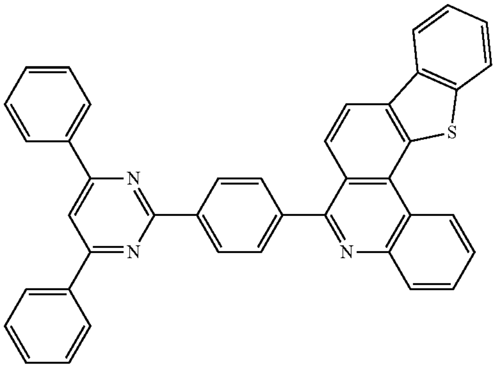
4-65
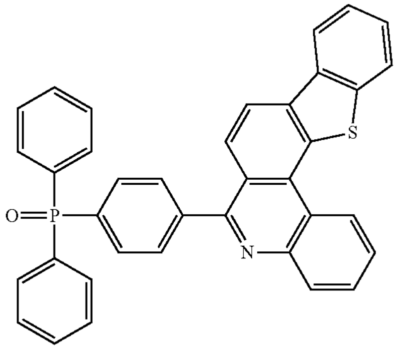
4-66
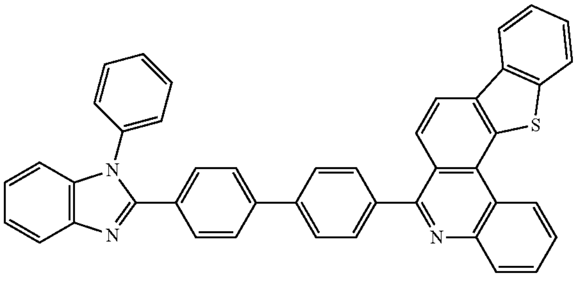
4-67
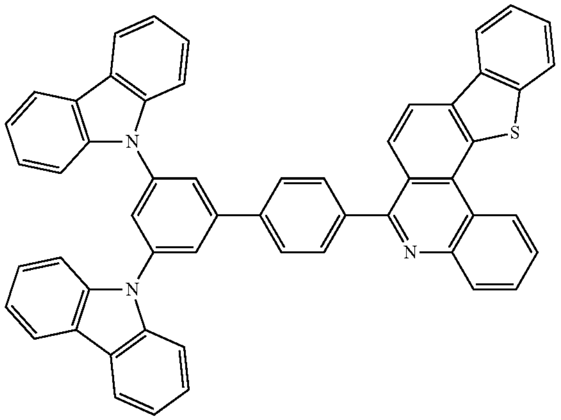
4-68
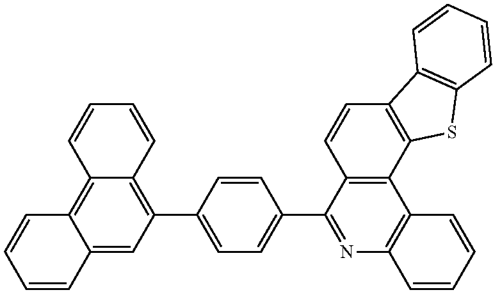
4-69
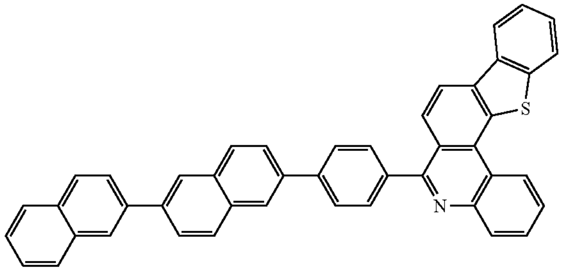

-continued
4-70
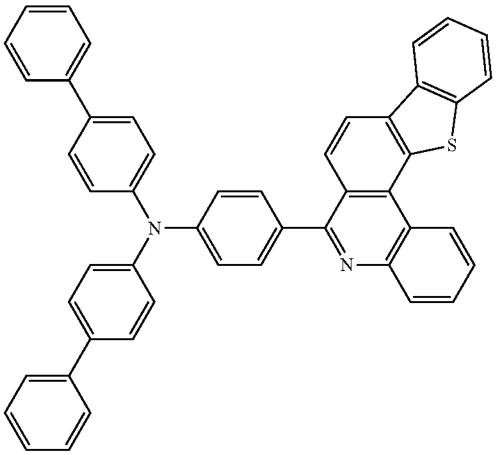
4-71
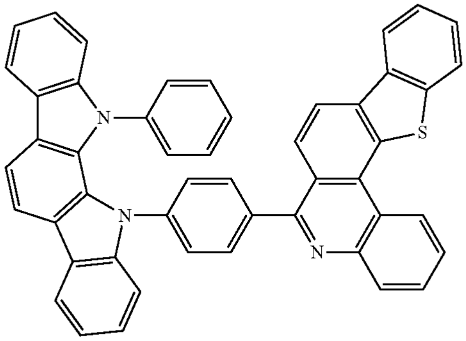
4-72
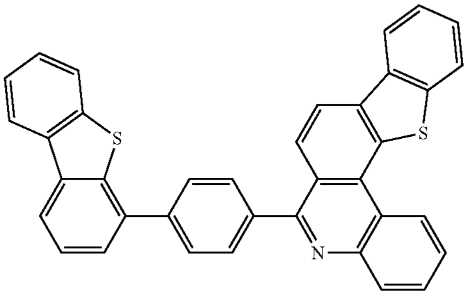
4-73
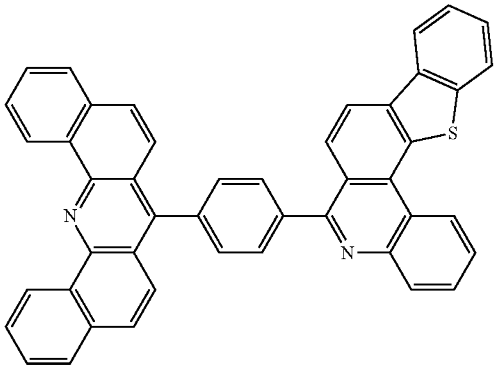
4-74
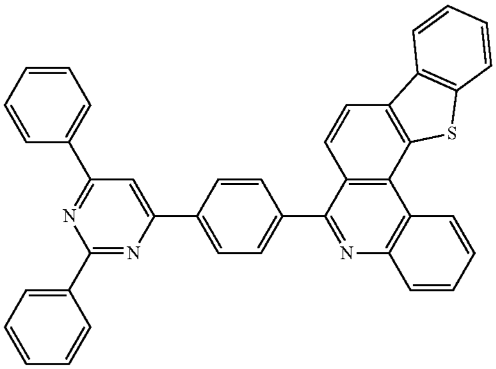
4-75
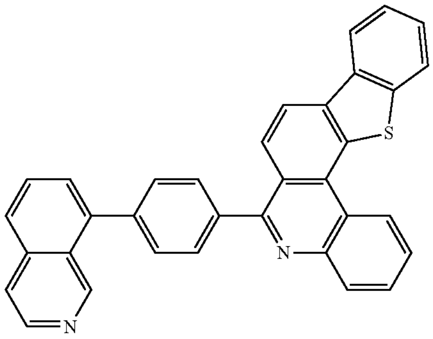
4-76
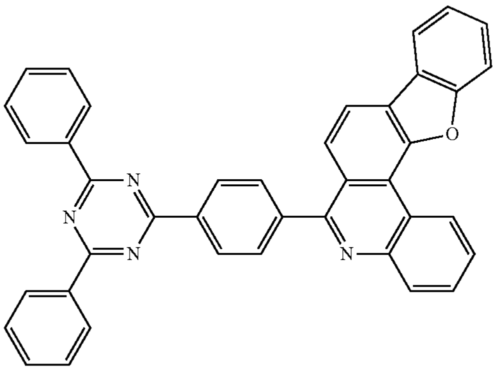
4-77
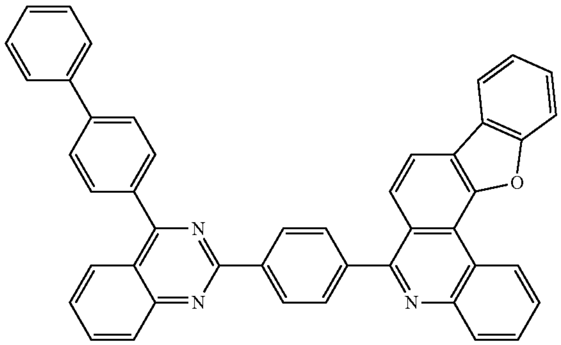

-continued
4-78
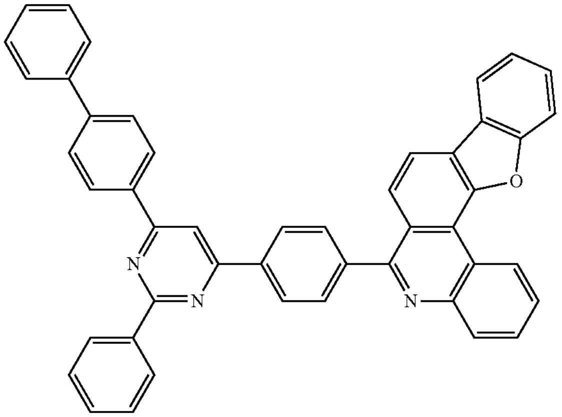
4-79
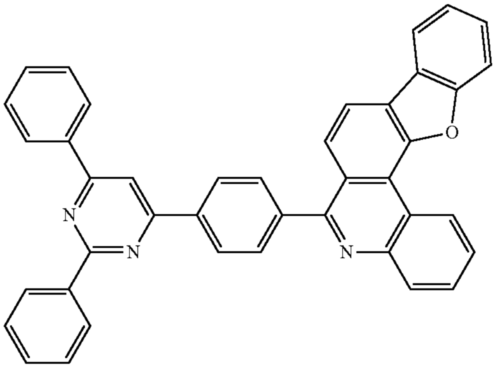
4-80
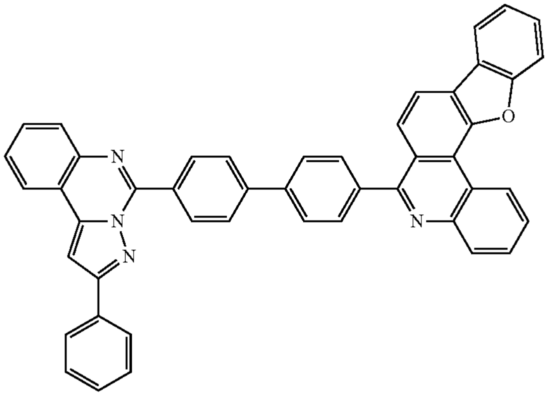
4-81
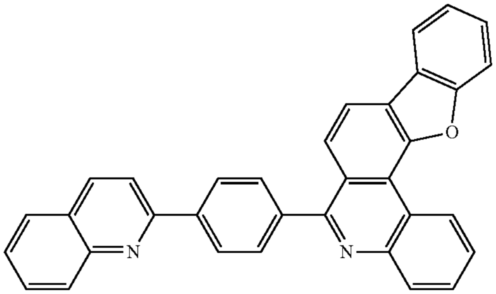
4-82
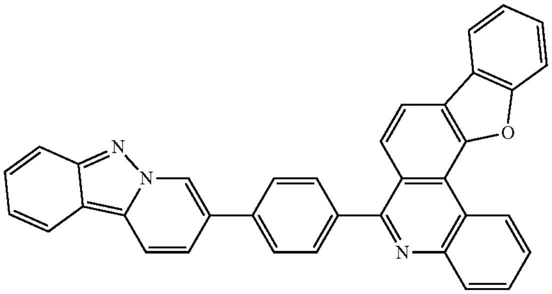
4-83
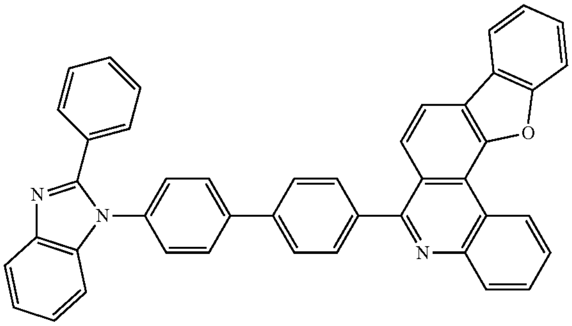
4-84
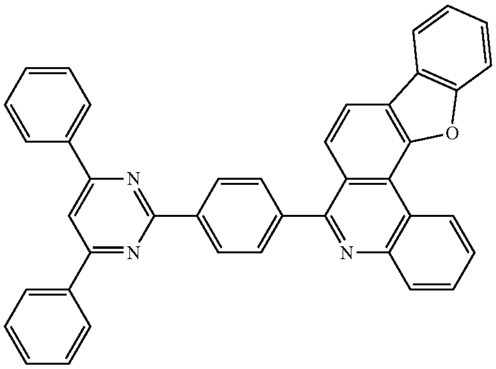
4-85
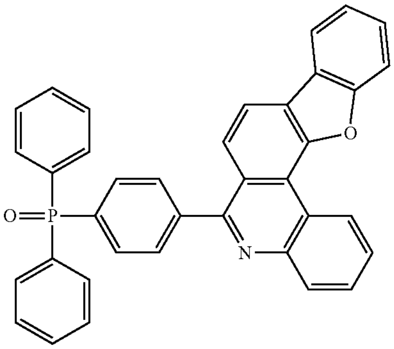

-continued
4-86
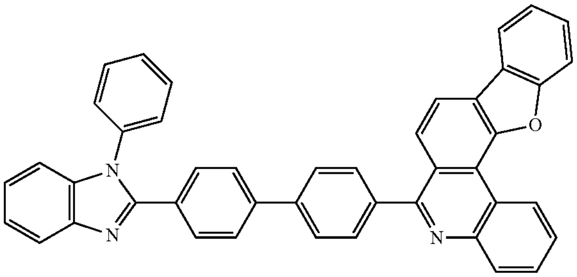
4-87
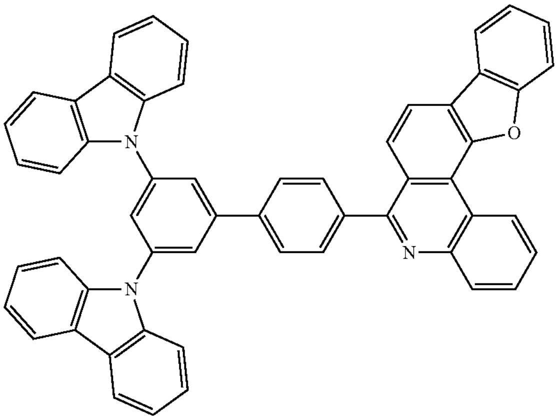
4-88
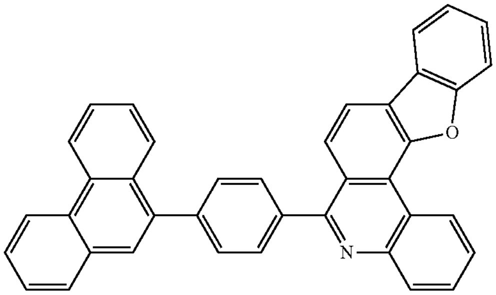
4-89
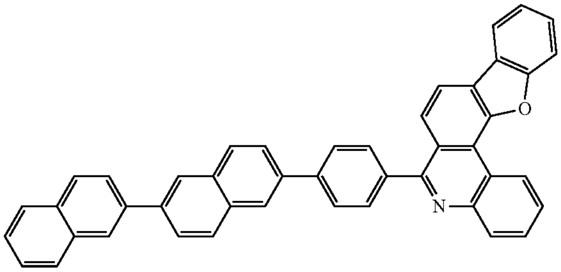
4-90
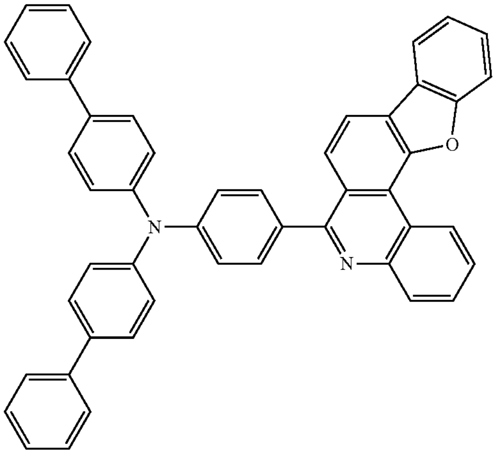
4-251
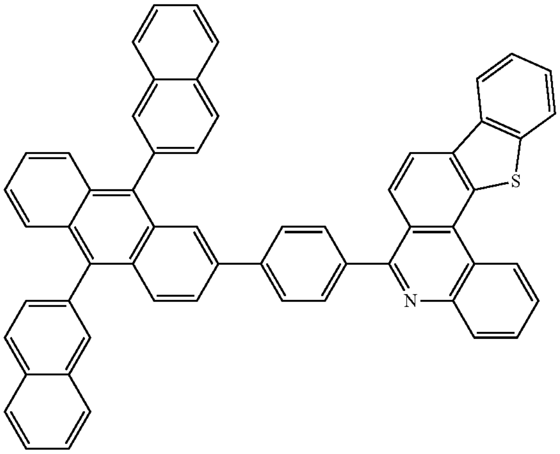
4-252
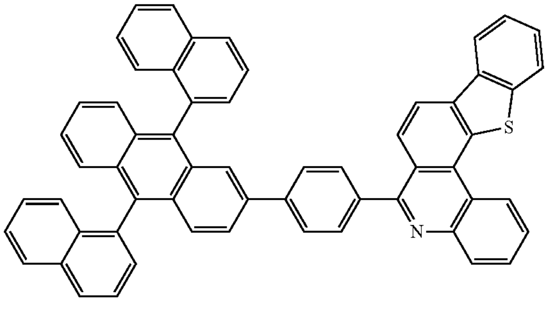
4-253
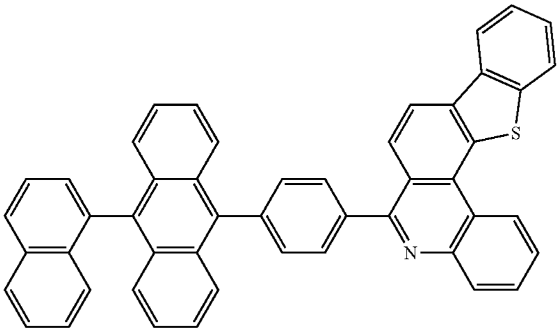

-continued
4-254
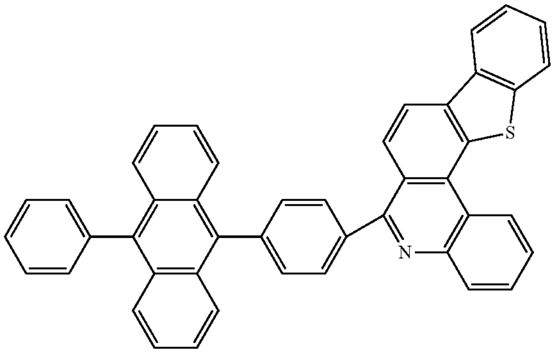
4-255
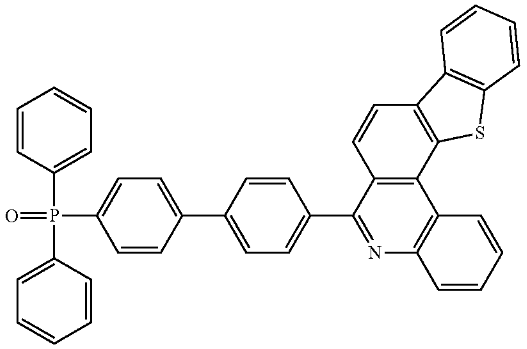
4-256
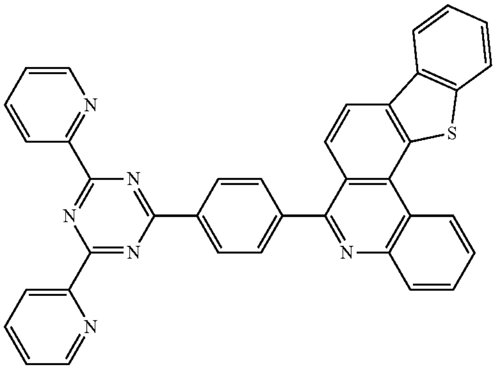
4-257
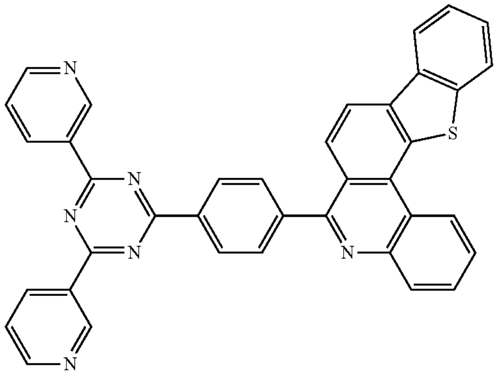
4-258
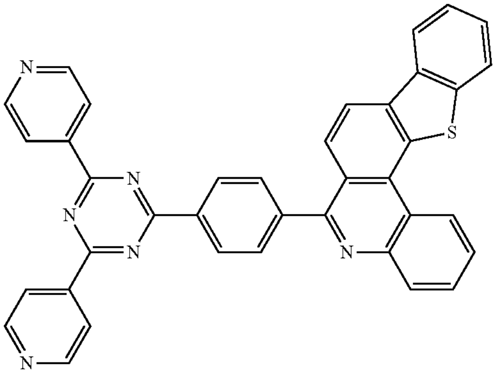
4-259
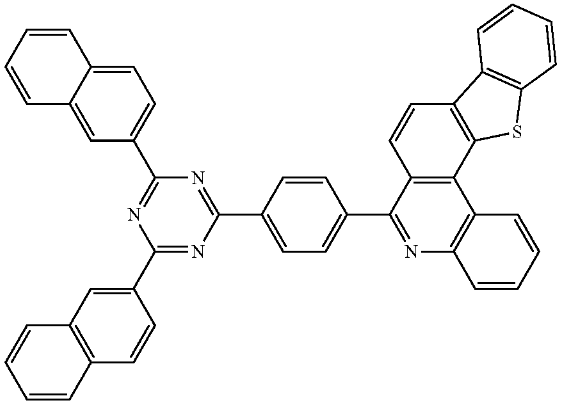
4-260
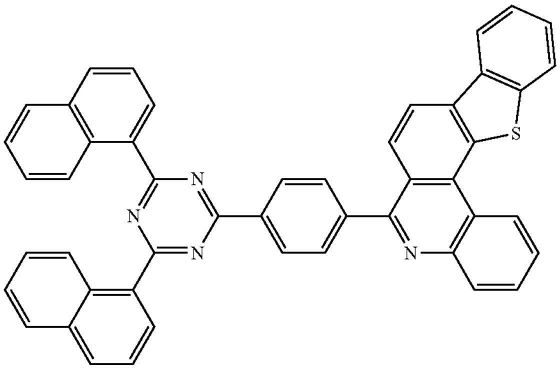
4-261
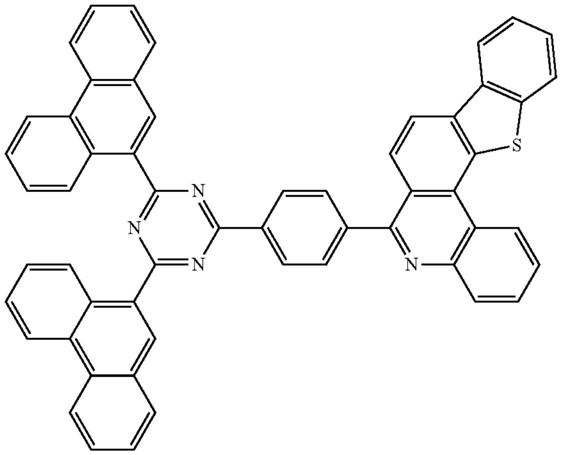

-continued
4-262
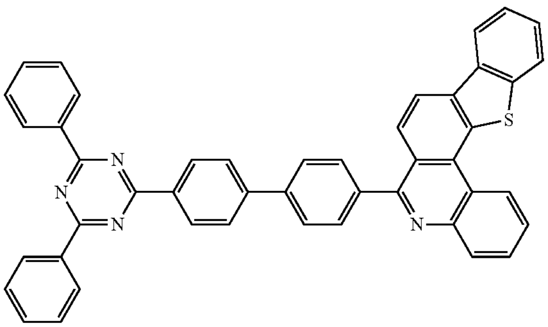
4-263
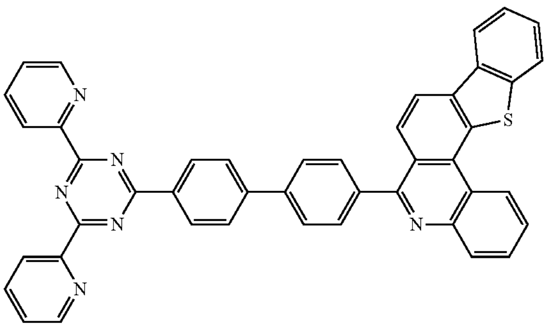
4-264
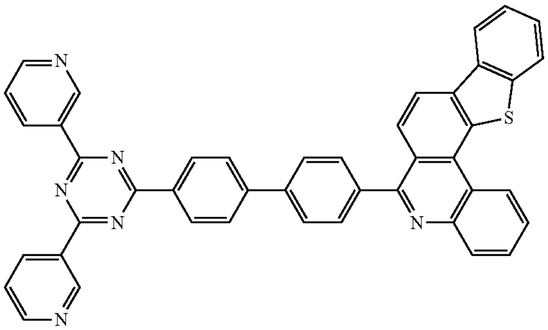
4-265
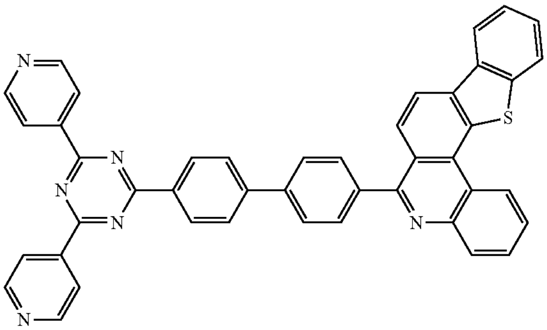
4-266
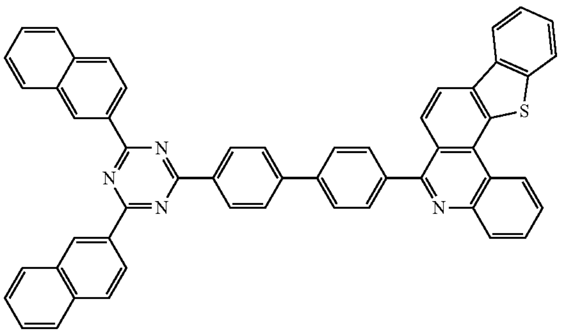
4-267
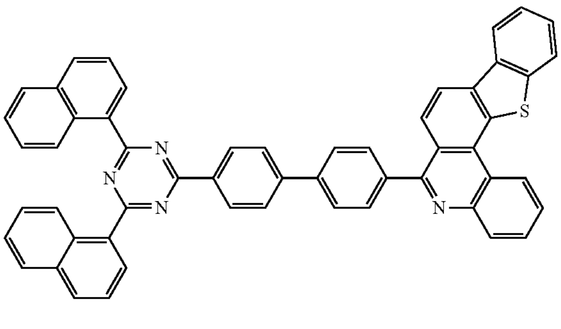
4-268
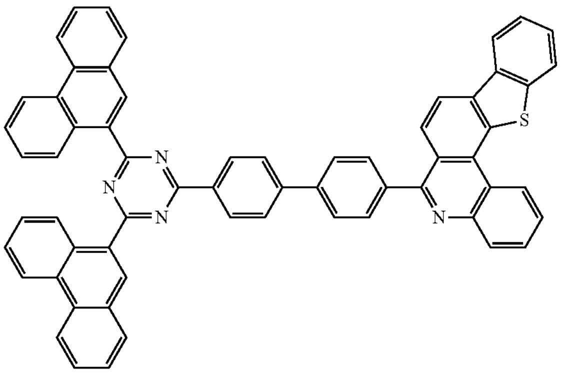
4-269
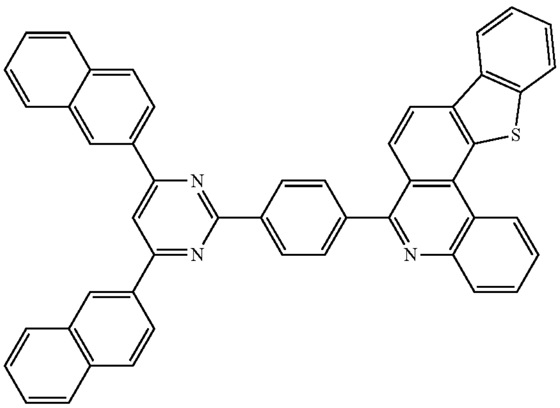

-continued
4-270
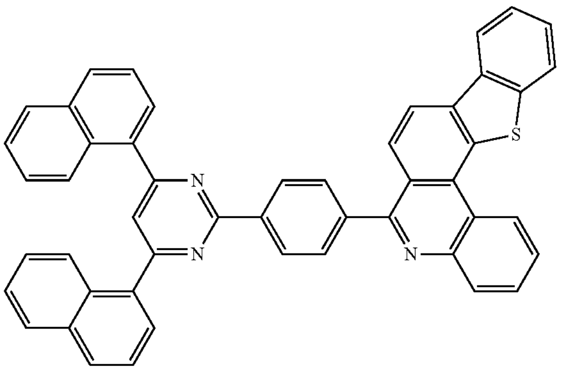
4-271
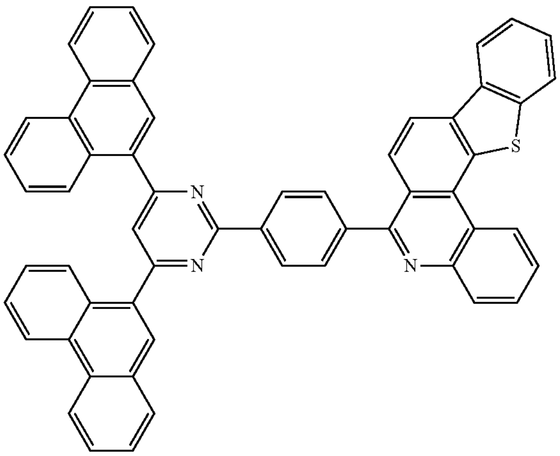
4-272
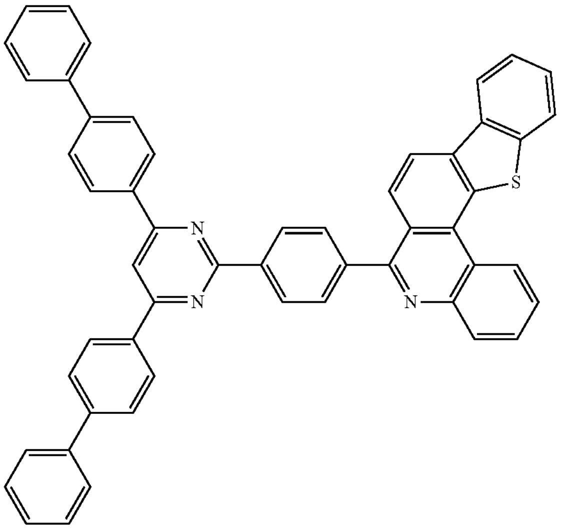
4-273
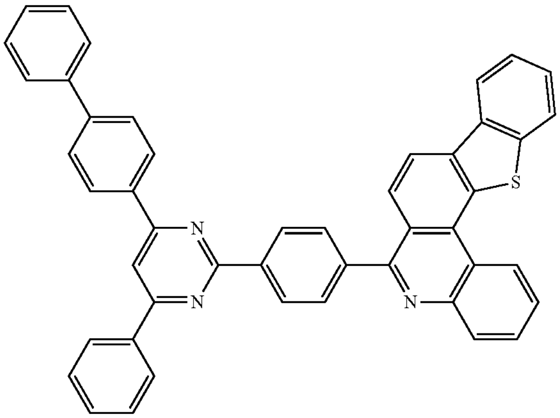
4-274
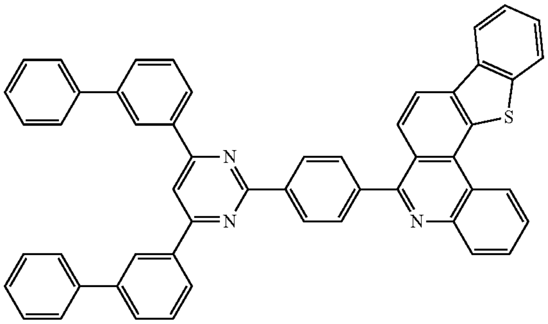
4-275
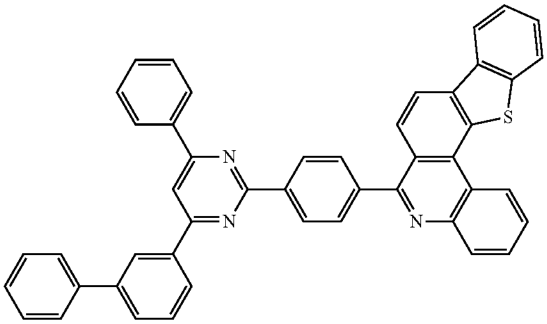

-continued
4-276
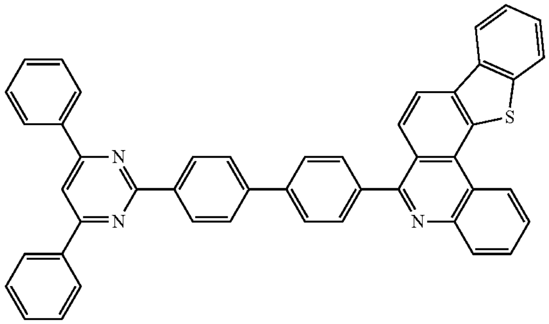
4-277
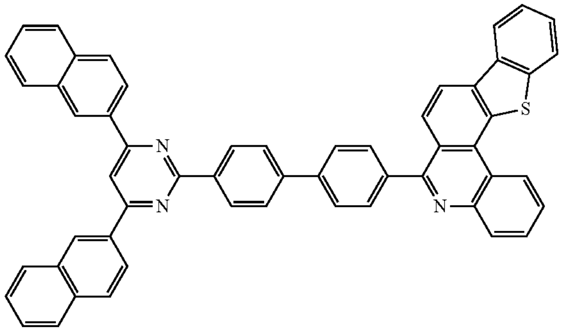
4-278
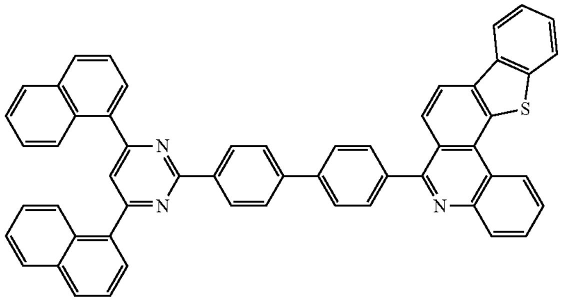
4-279
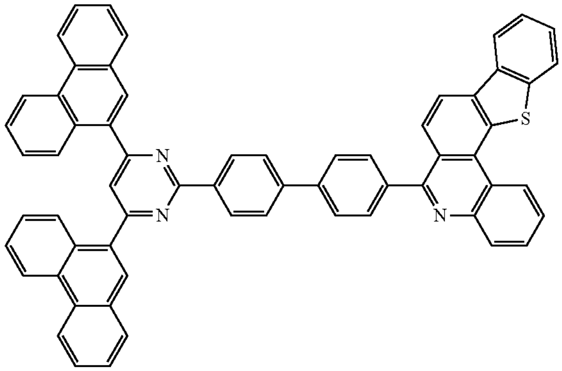
4-280
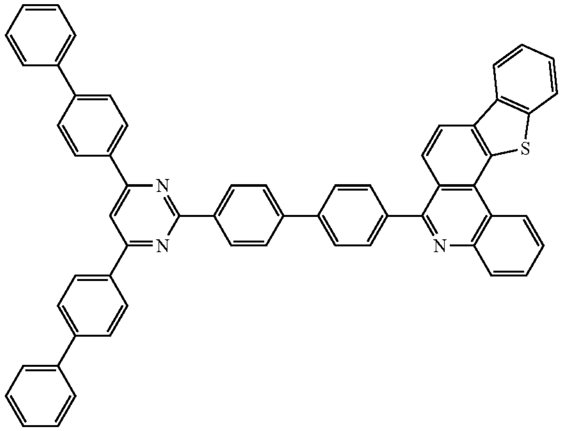
4-281
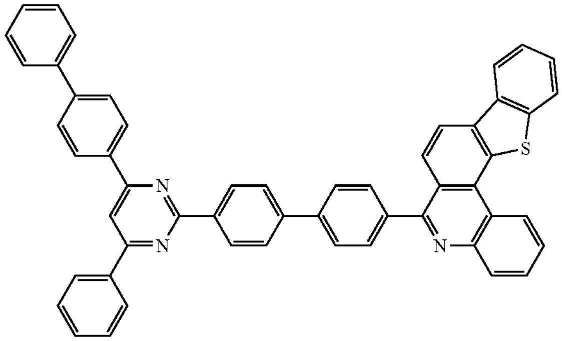
4-282
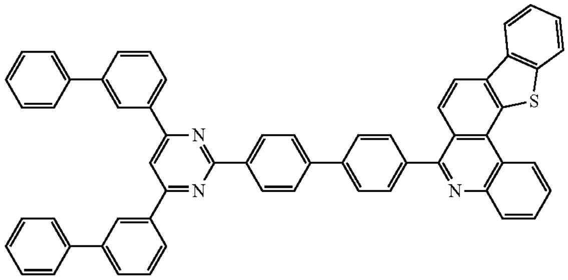
4-283
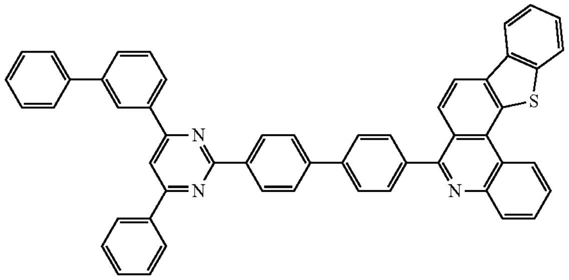

-continued
4-284
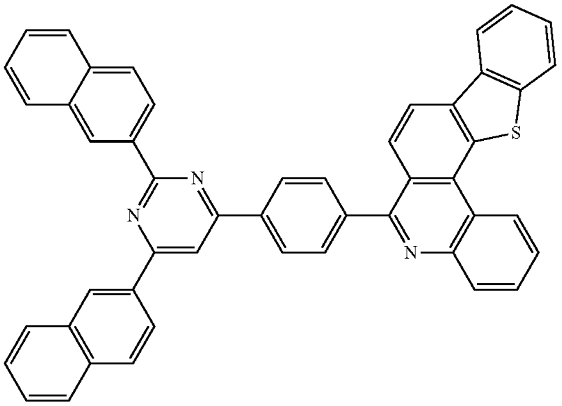
4-285
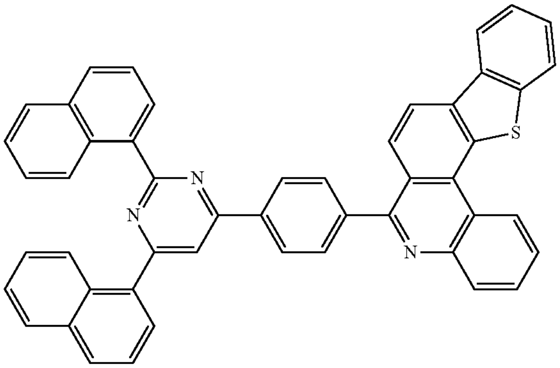
4-286
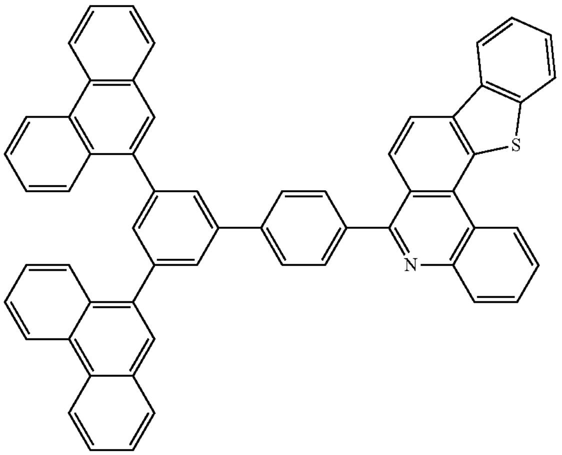
4-287
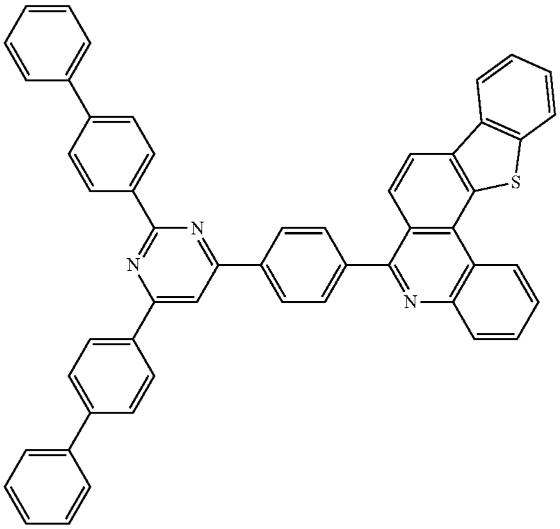
4-288
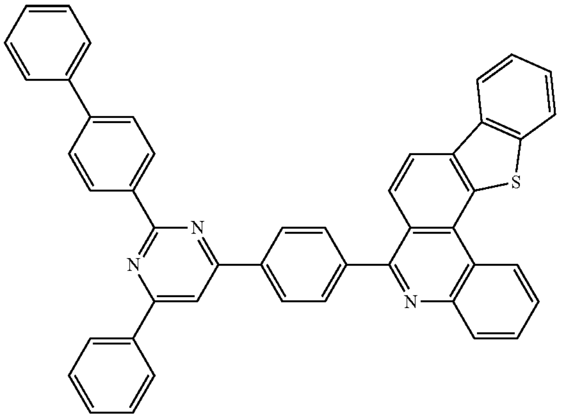
4-289
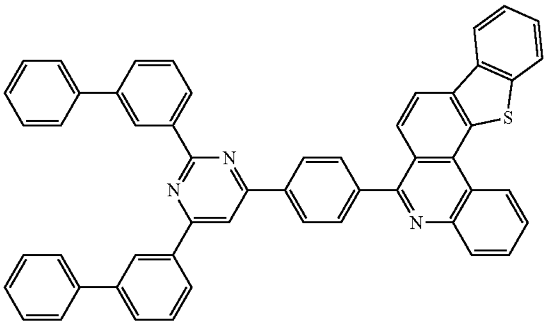

-continued
4-290
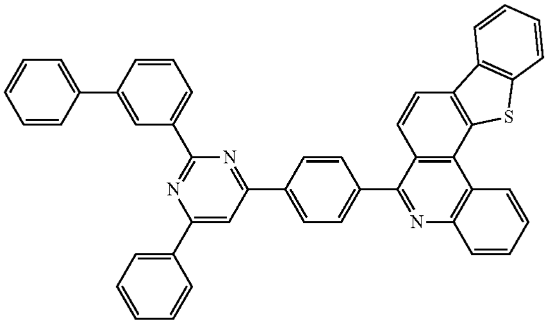
4-291
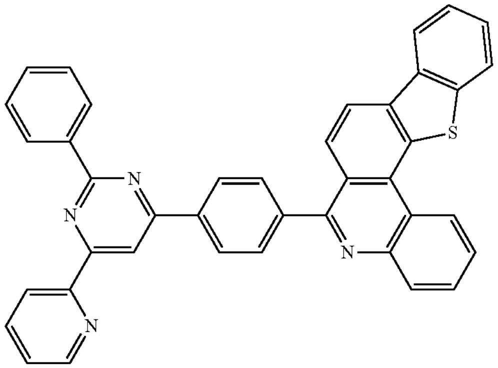
4-292
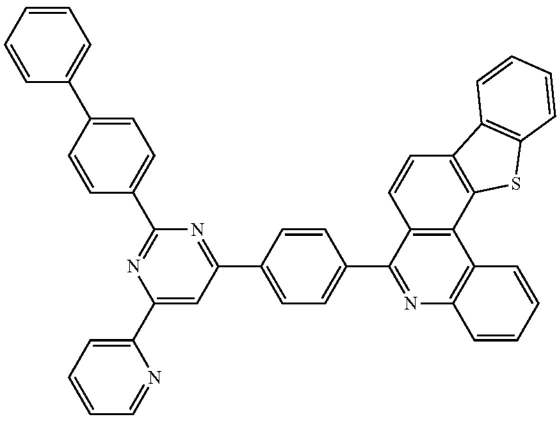
4-293
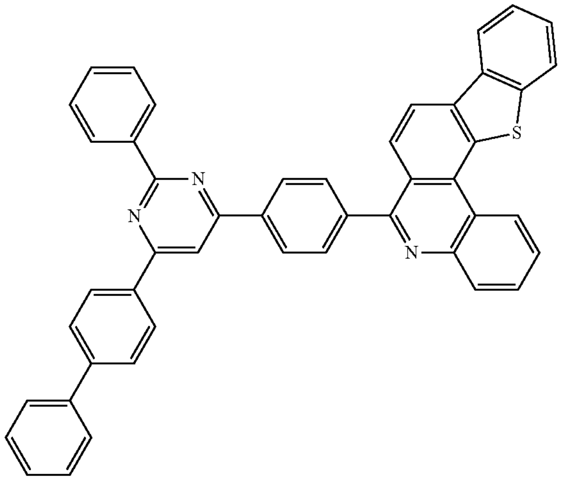
4-294
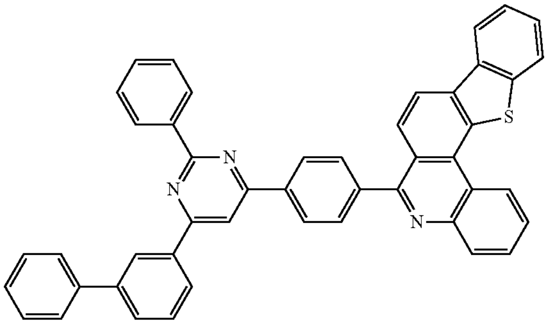
4-295
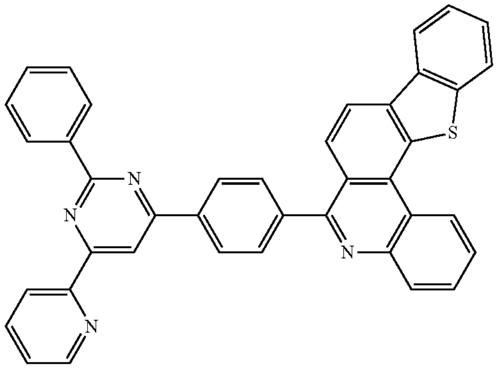
4-296
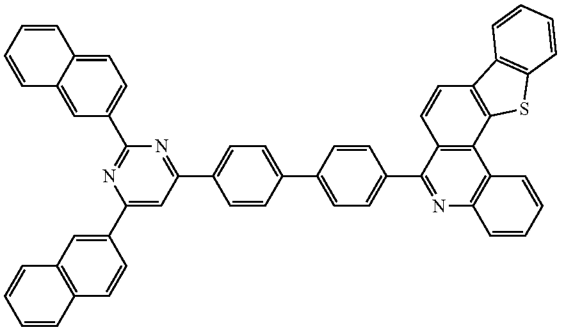
4-297
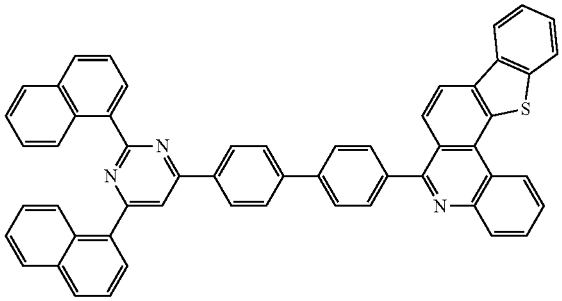

-continued
4-298
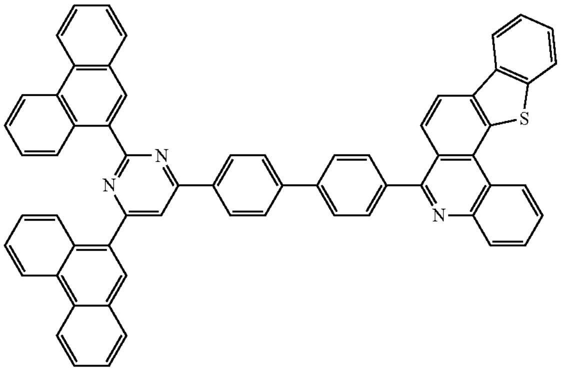
4-299
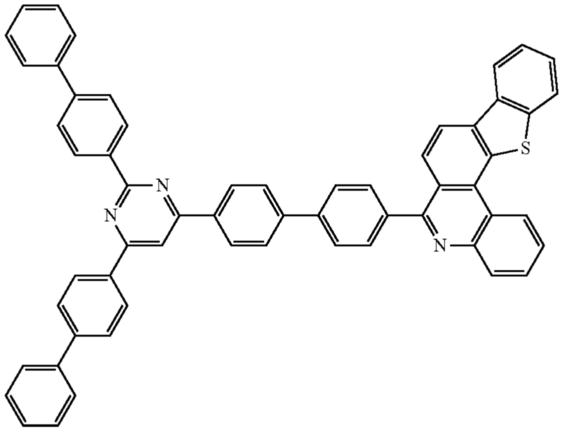
4-300
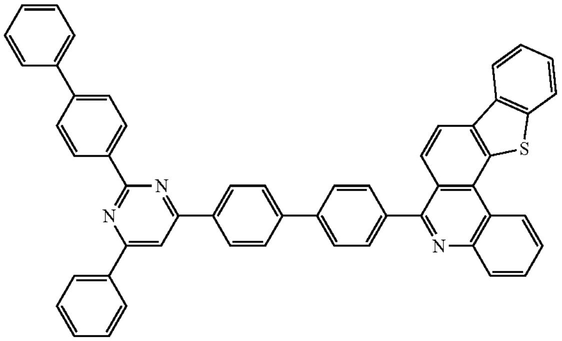
4-301
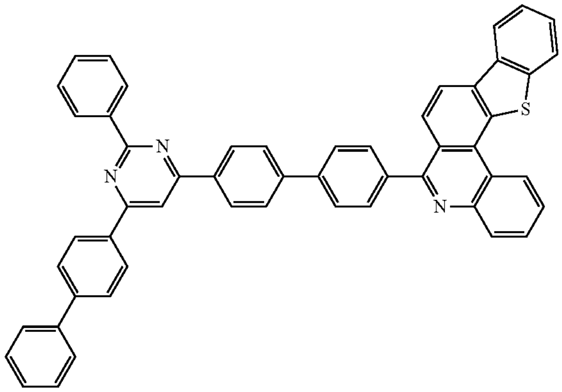
4-302
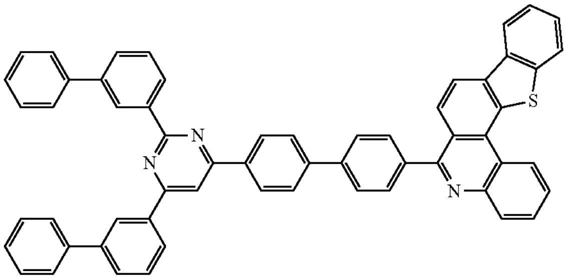
4-303
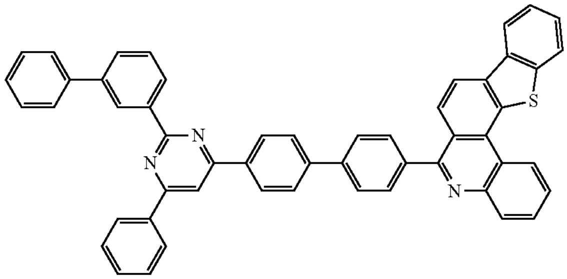
4-304
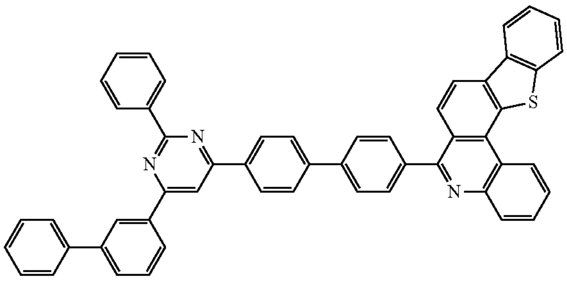
4-305
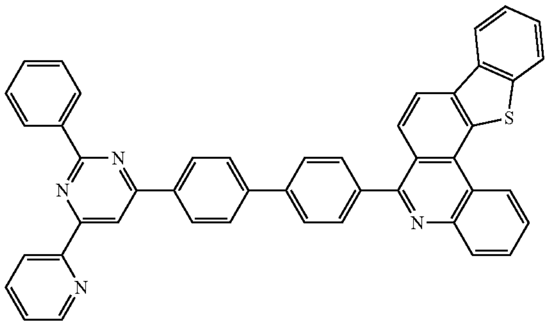

-continued
4-306
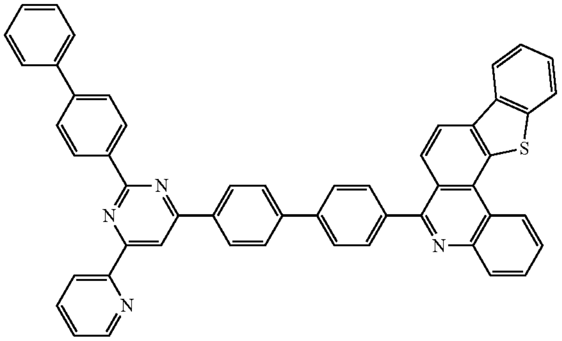
4-307
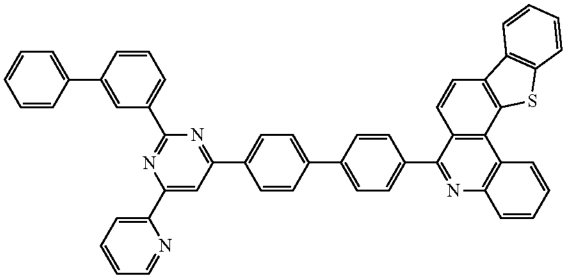
4-308
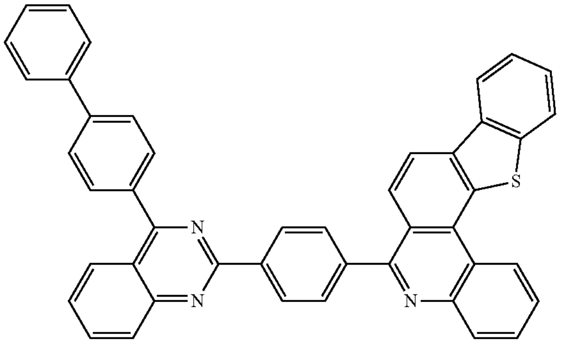
4-309
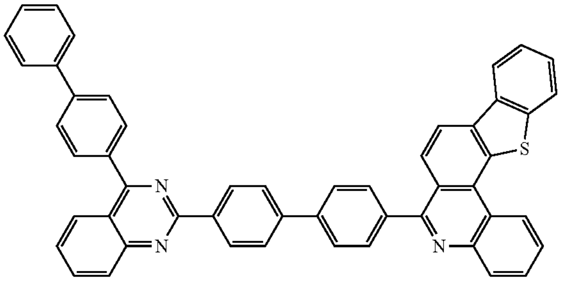
4-310
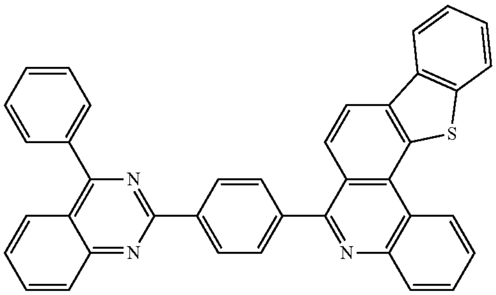
4-311
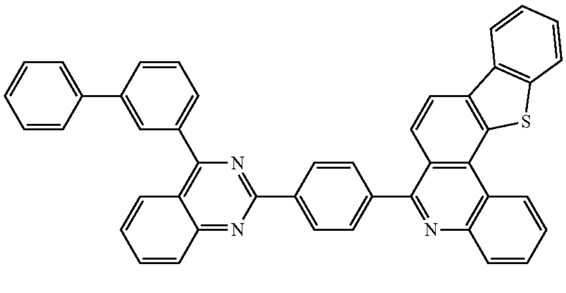
4-312
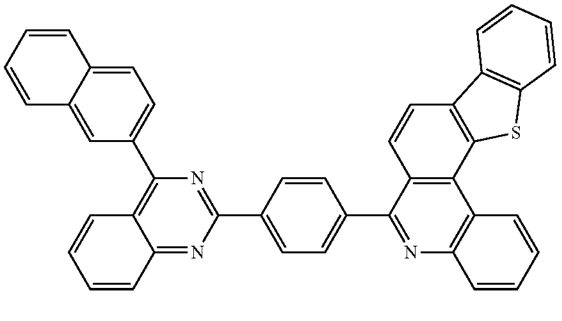
4-313
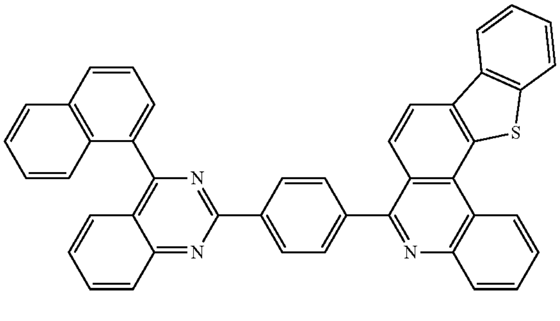

-continued
4-314
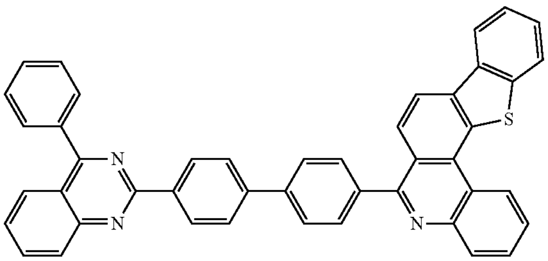
4-315
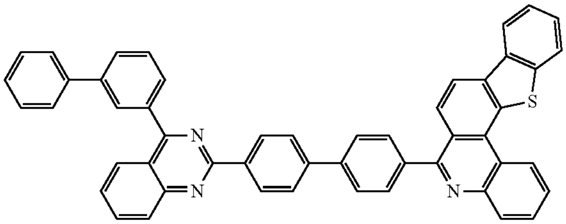
4-316
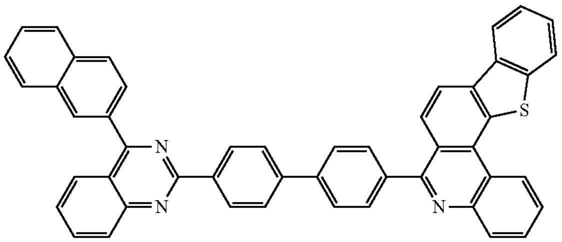
4-317
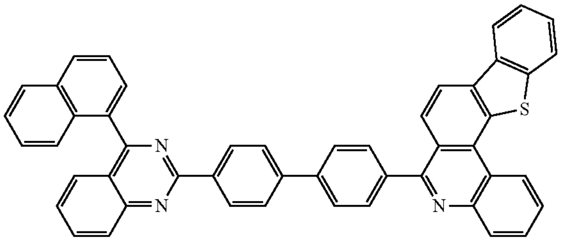
4-318
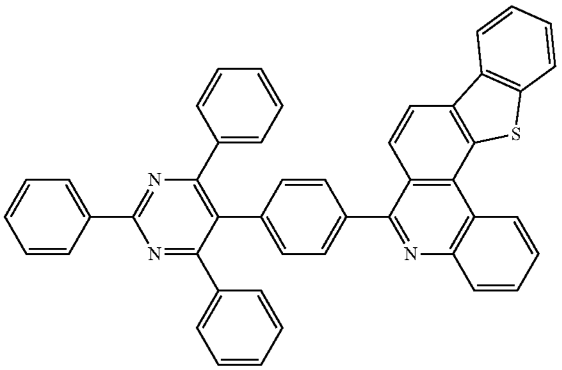
4-319
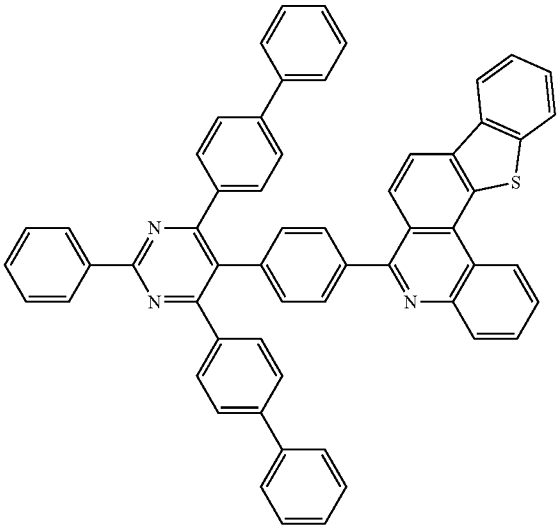
4-320
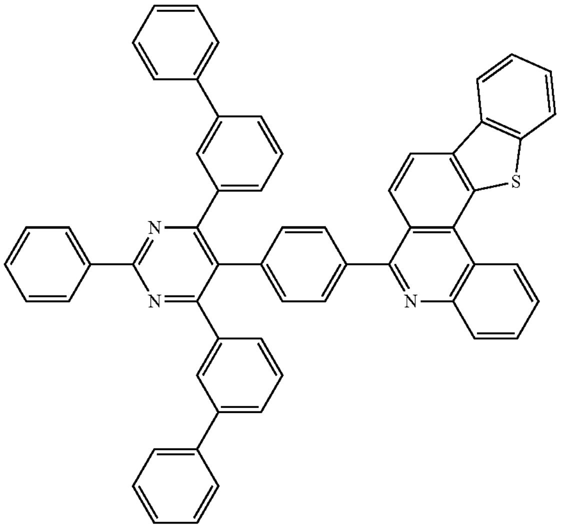
4-321
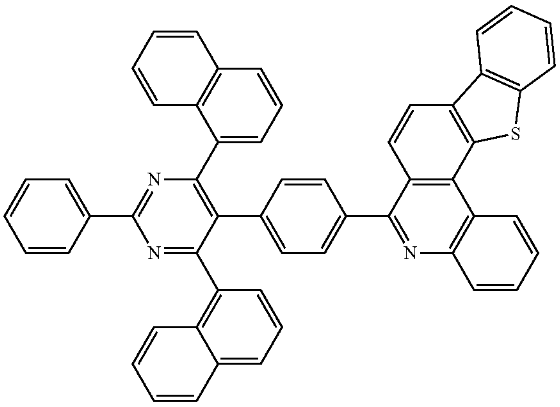

-continued
4-322
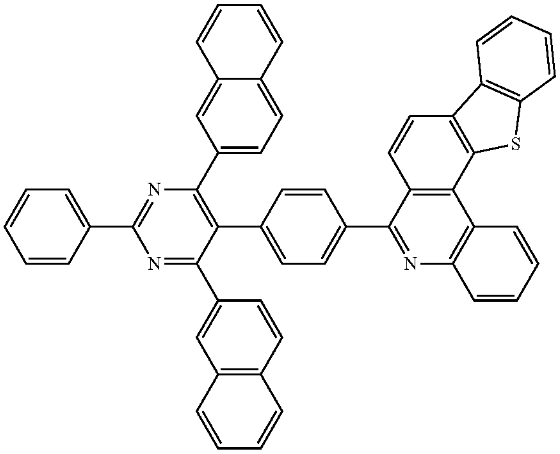
4-323
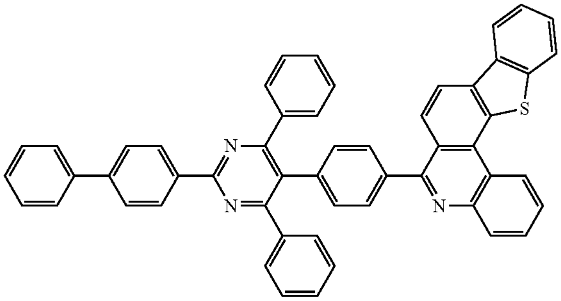
4-324
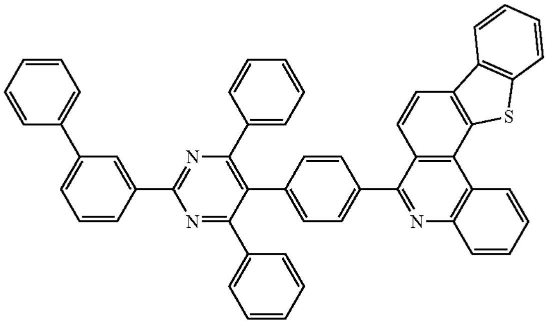
4-325
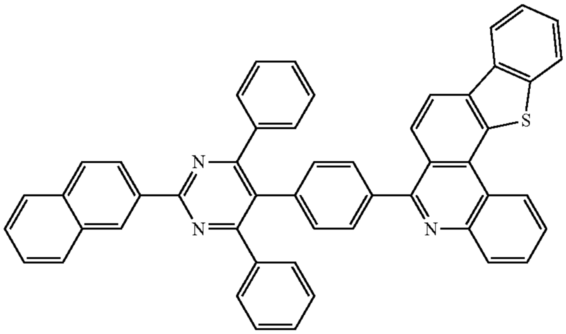
4-326
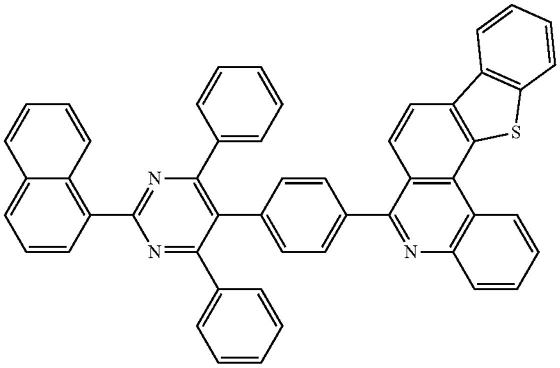
4-327
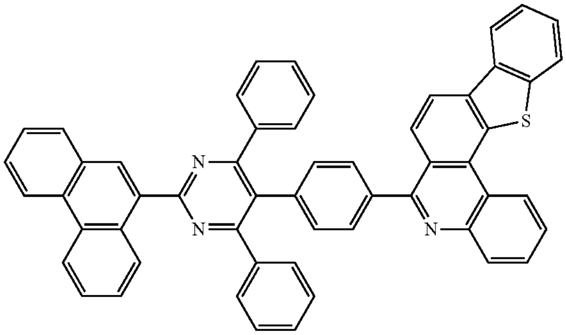
4-328
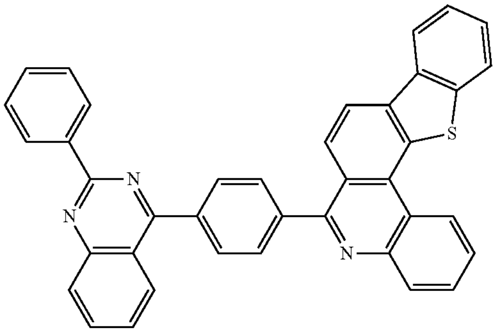
4-329
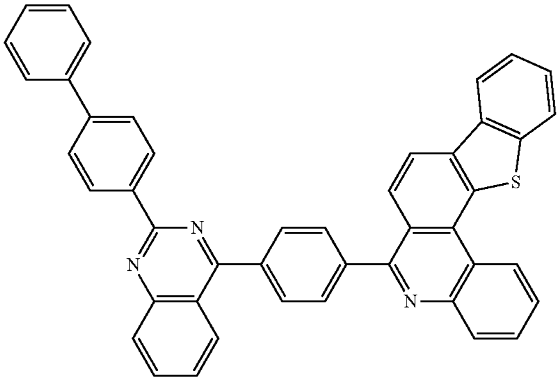

-continued
4-330
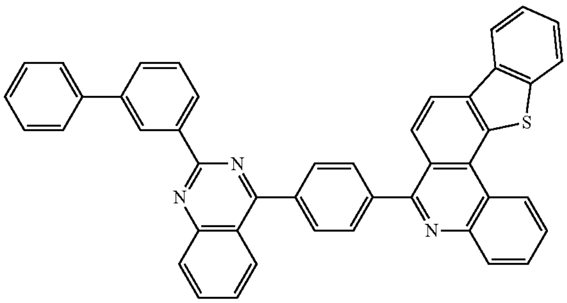
4-331
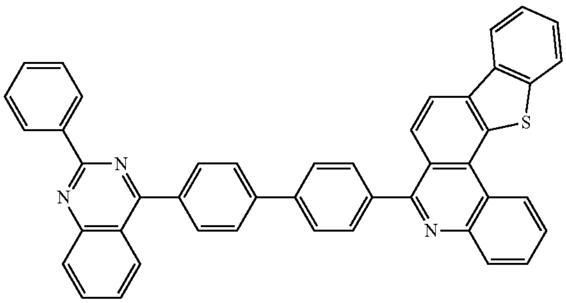
4-332
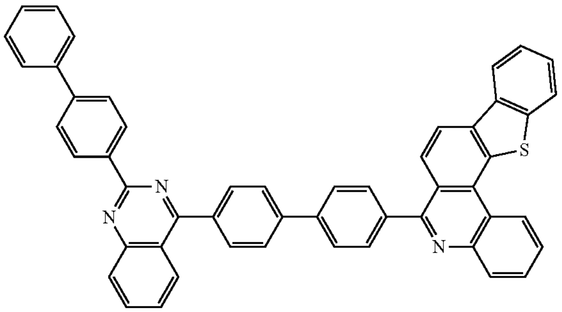
4-333
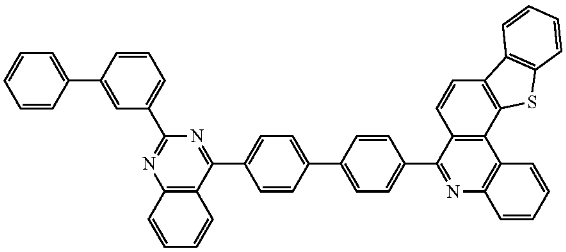
4-334
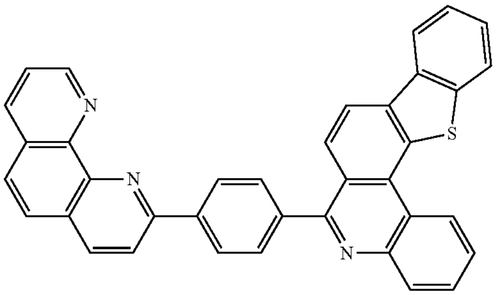
4-335
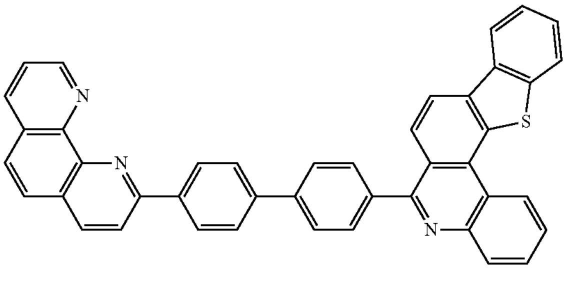
4-336
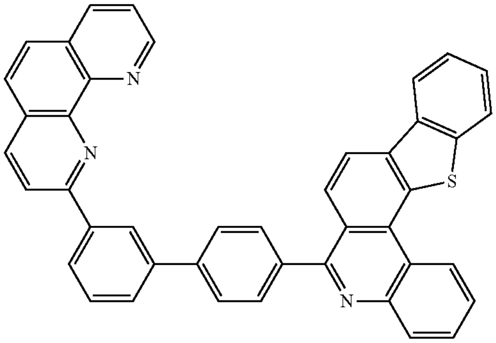
4-337
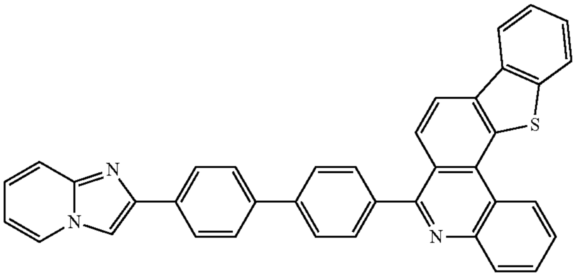

-continued
4-338
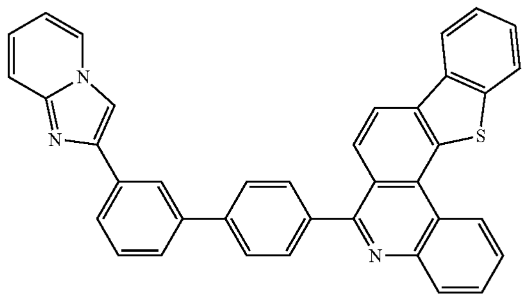
4-339
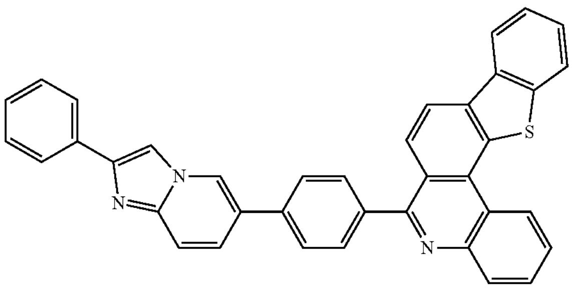
4-340
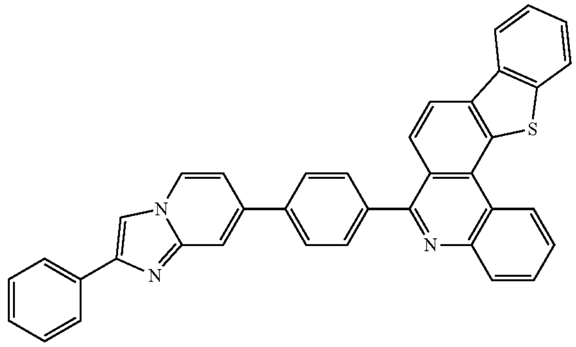
4-341
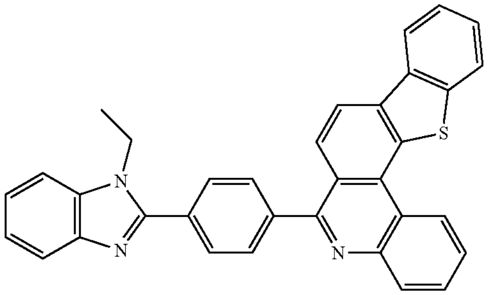
4-342
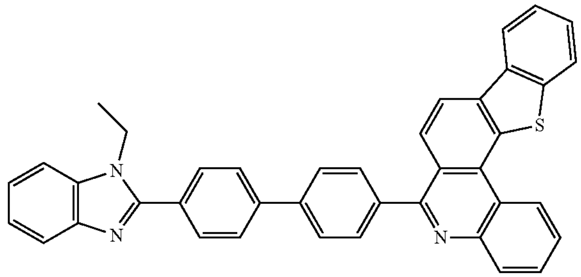
4-343
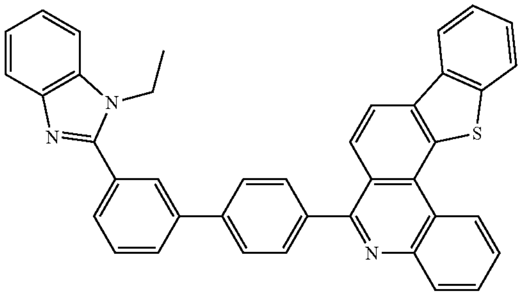
4-344
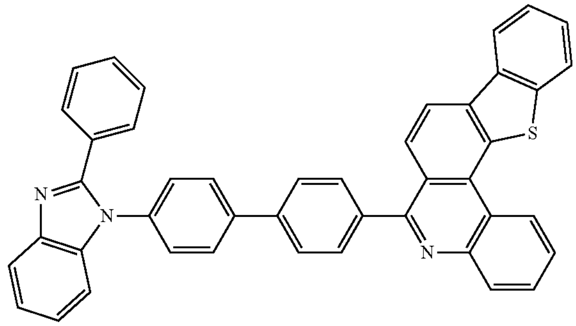
4-345
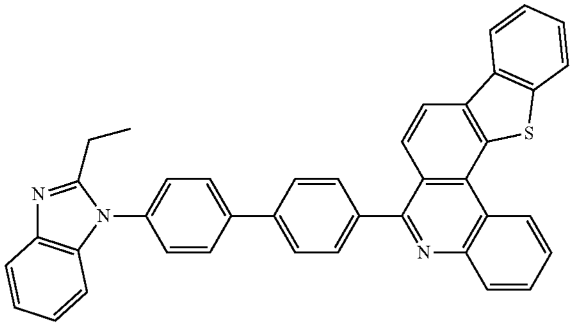

-continued
4-346
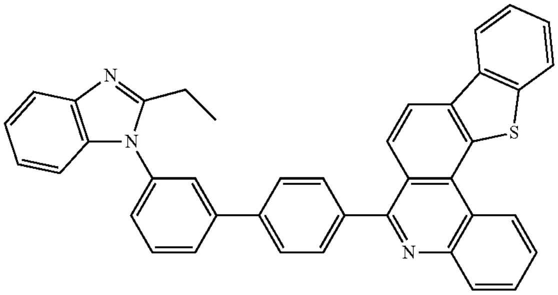
4-347
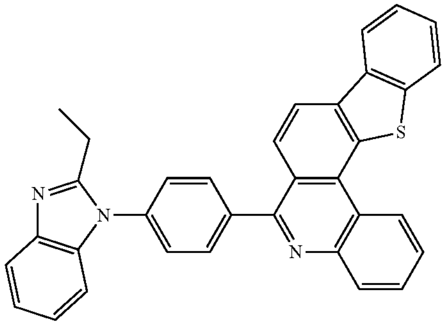
4-348
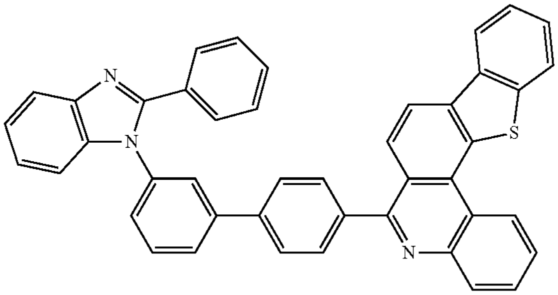
4-349
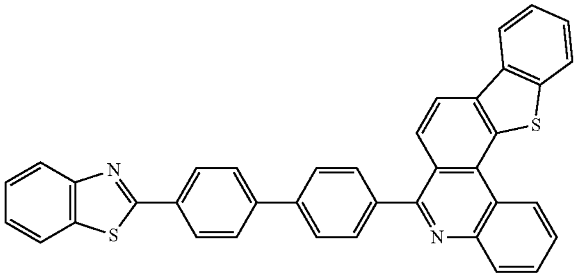
4-350
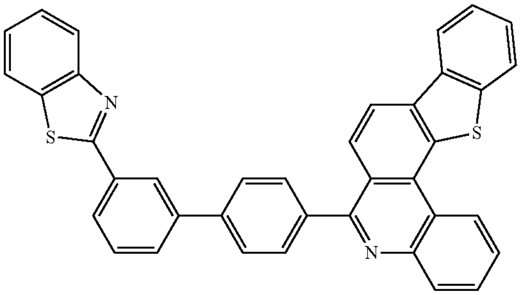
4-351
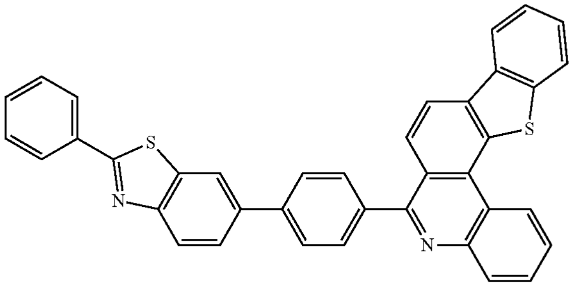
4-352
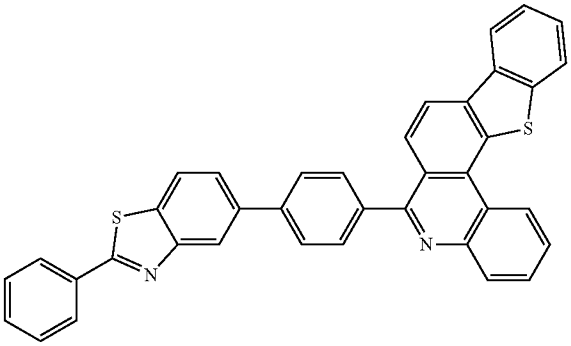
4-353
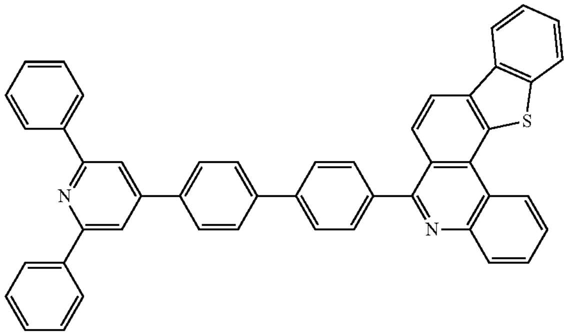

-continued
4-354
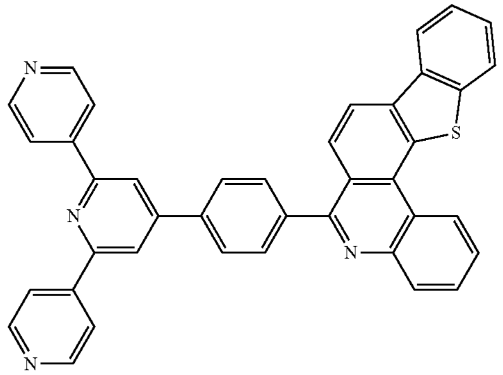
4-355
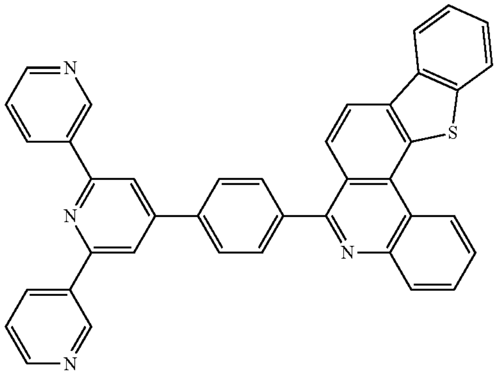
4-356
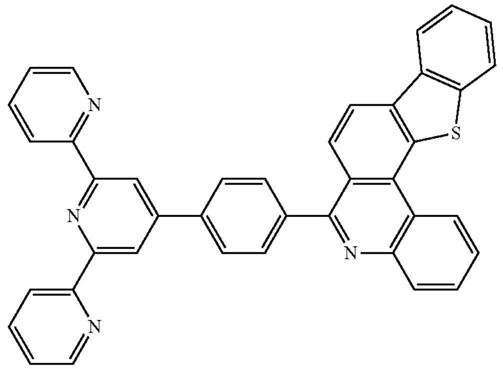
4-357
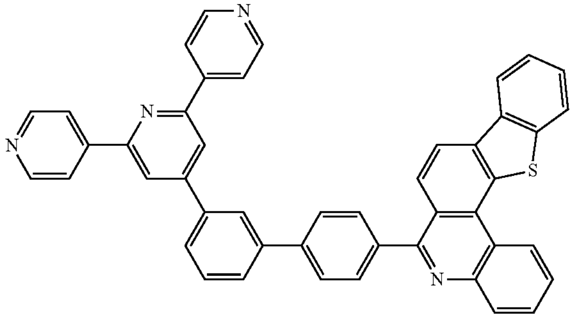
4-358
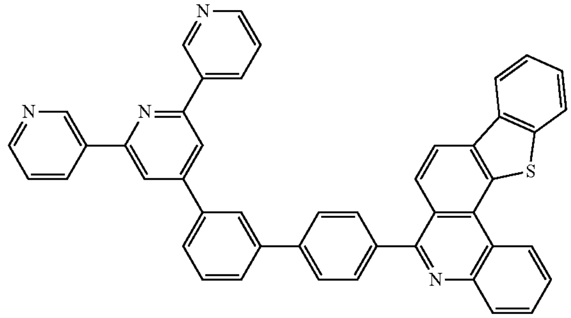
4-359
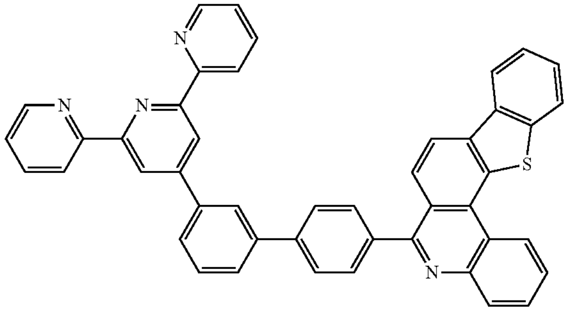
4-360
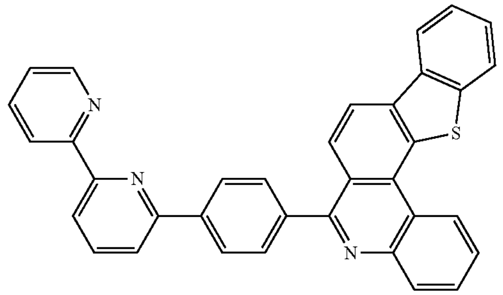
4-361
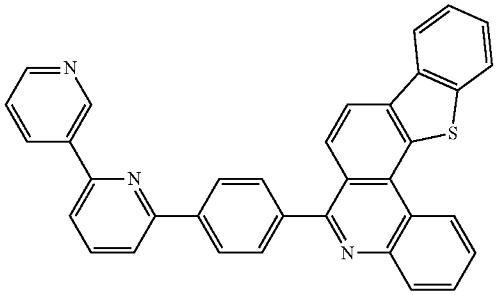

-continued
4-362
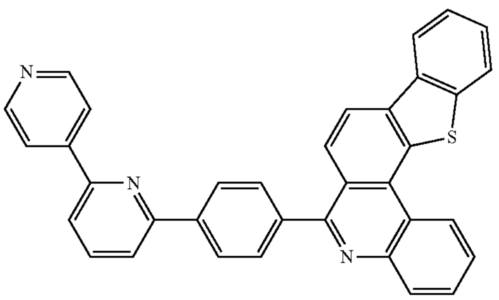
4-363
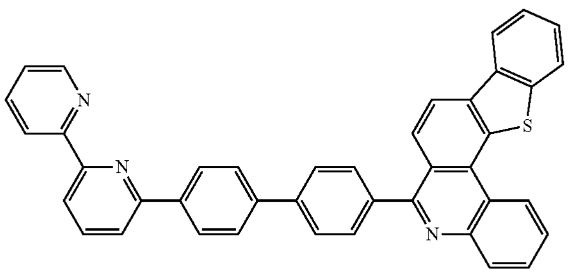
4-364
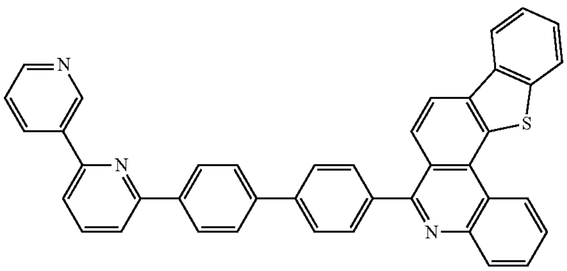
4-365
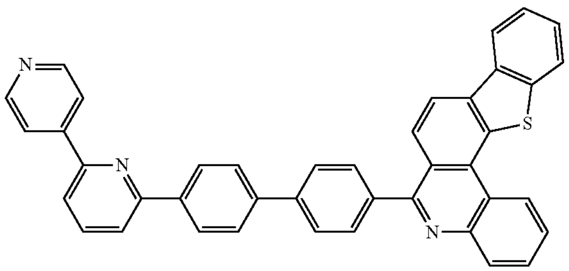
4-481
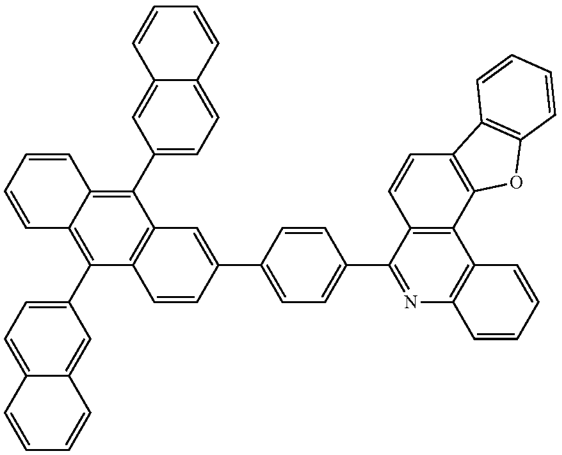
4-482
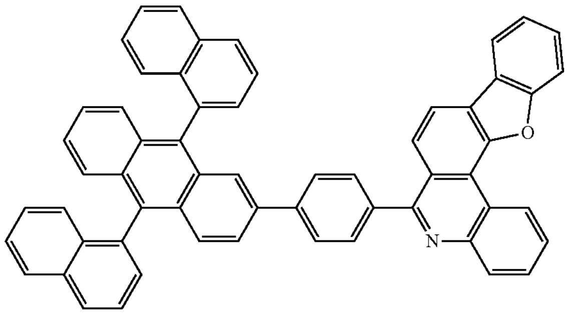
4-483
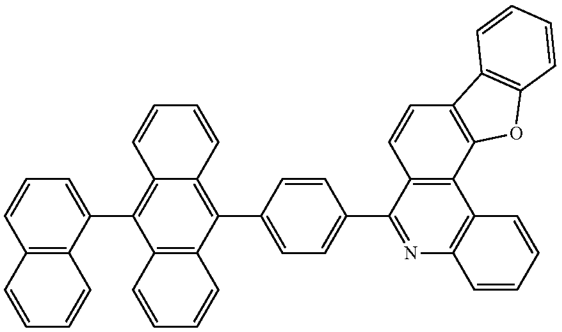
4-484
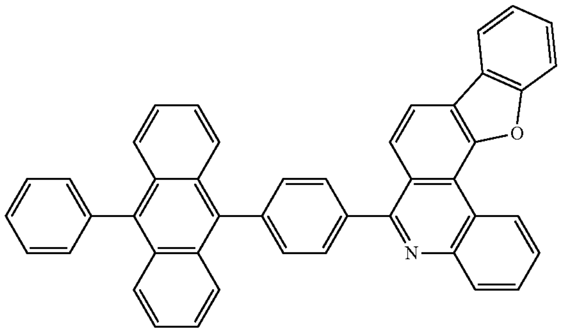

-continued
4-485
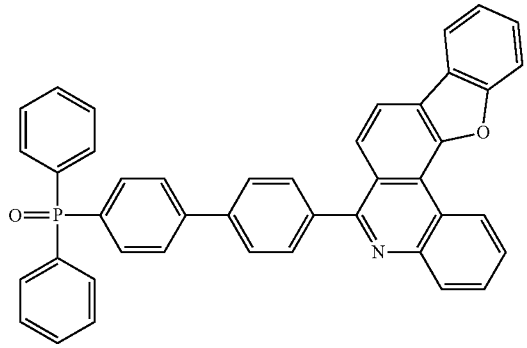
4-486
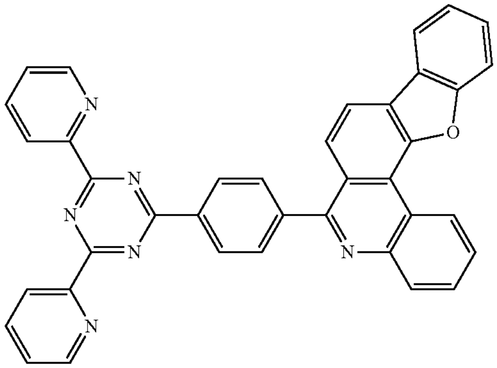
4-487
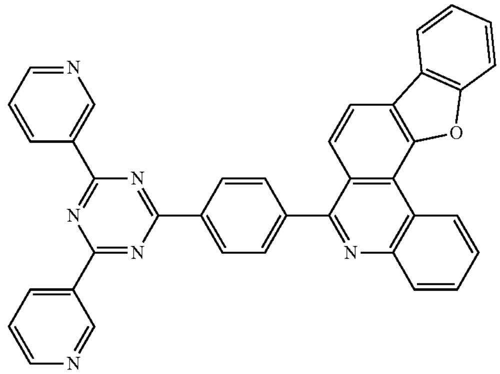
4-488
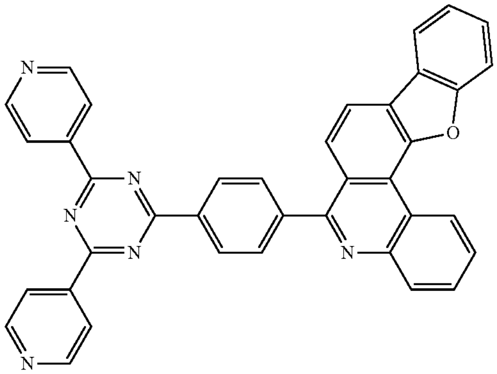
4-489
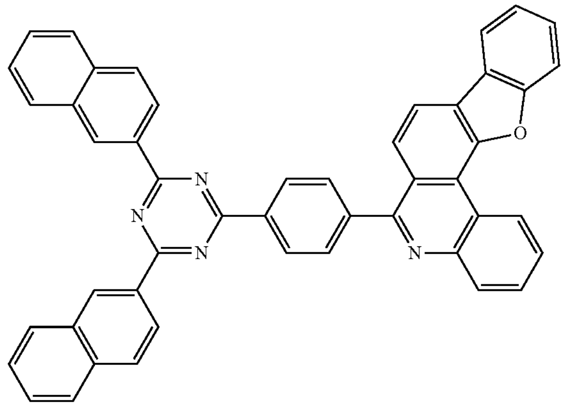
4-490
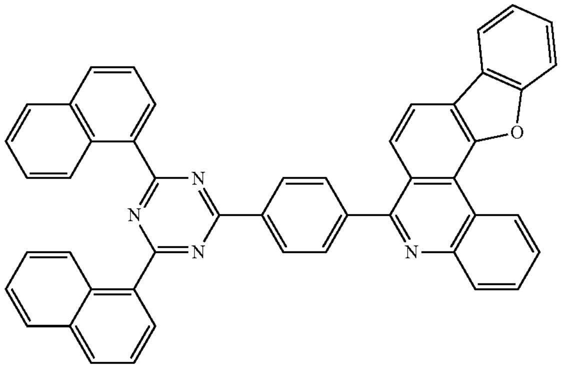
4-491
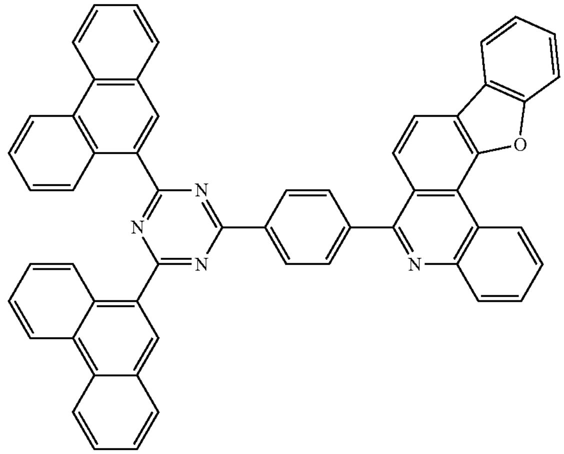
4-492
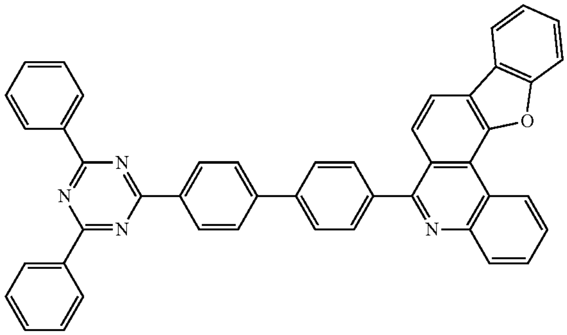

-continued
4-493
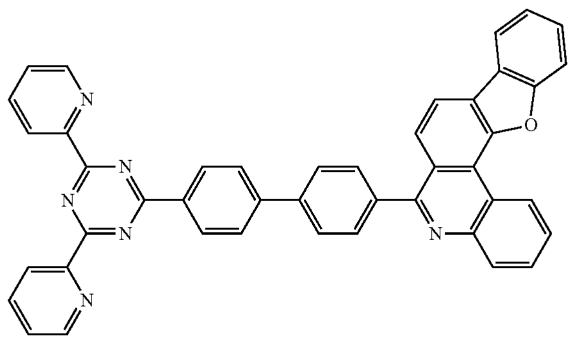
4-494
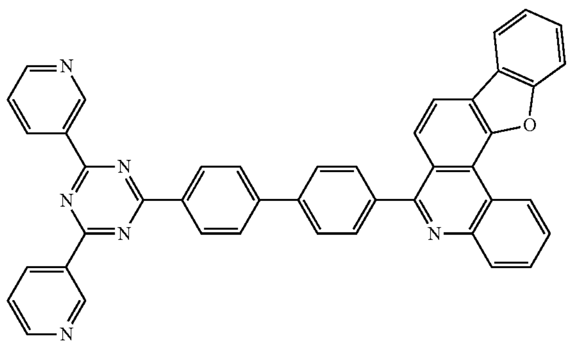
4-495
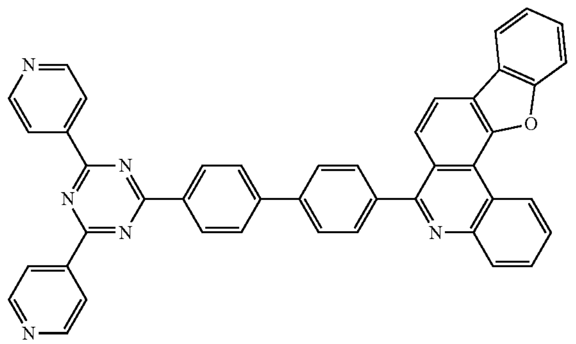
4-496
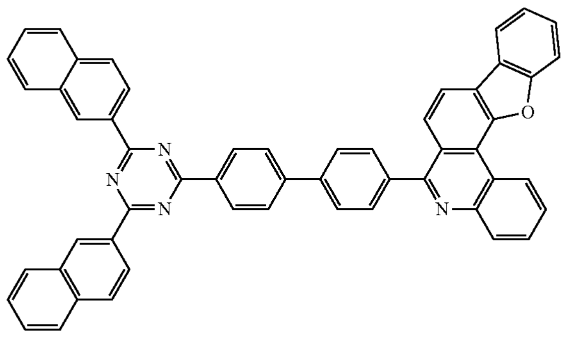
4-497
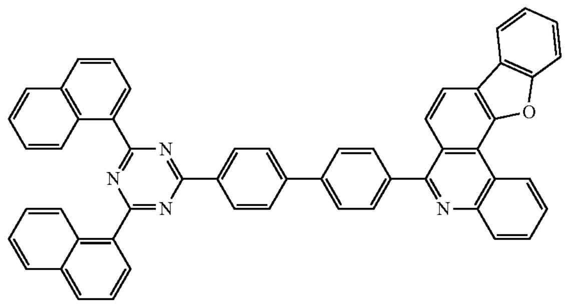
4-498
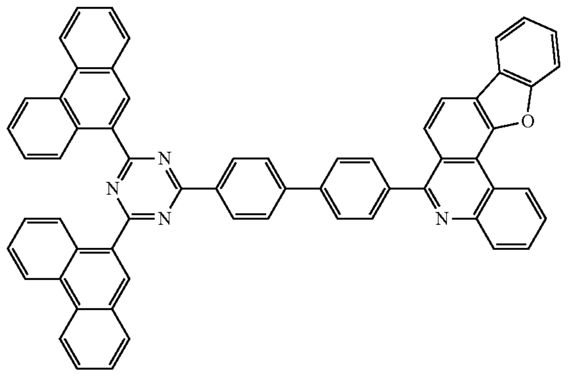
4-499
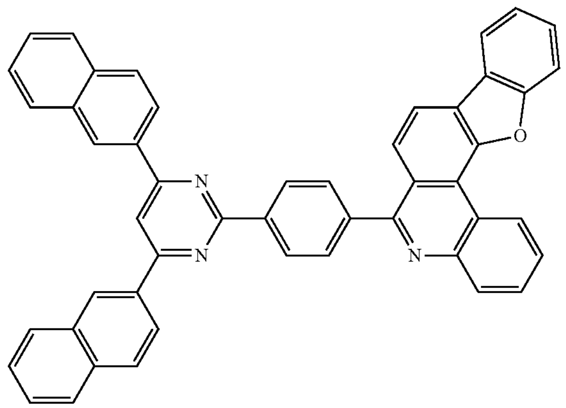
4-500
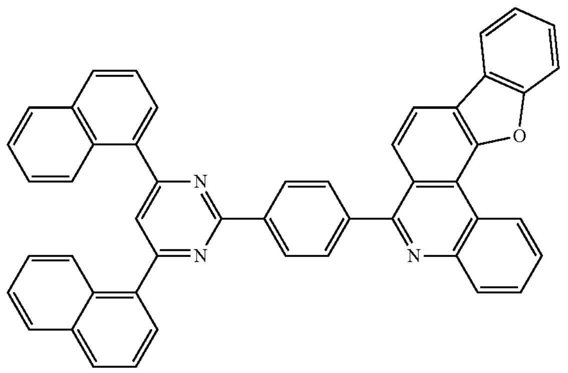

4-501
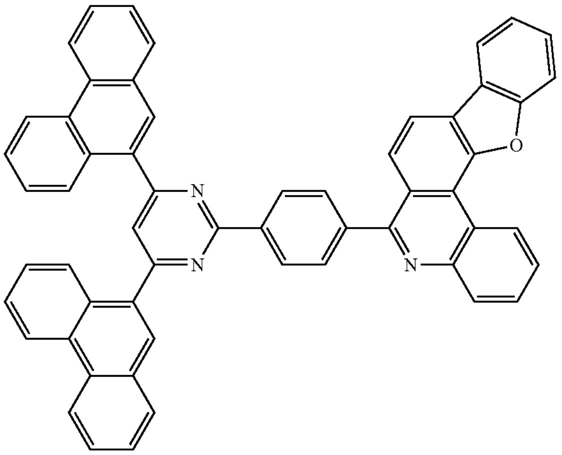
4-502
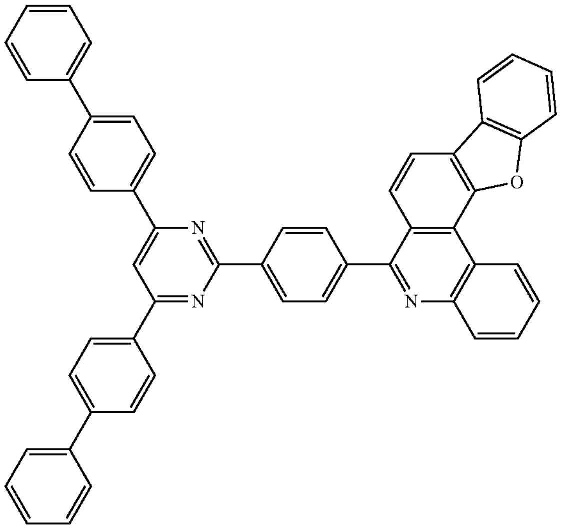
4-503
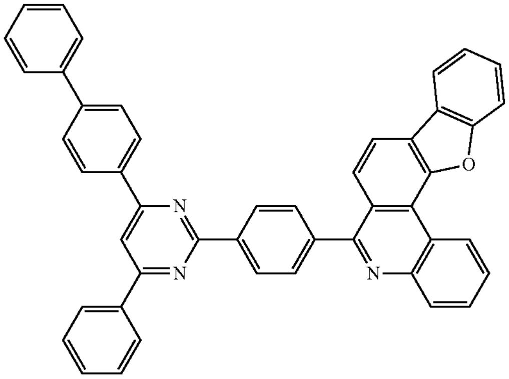
4-504
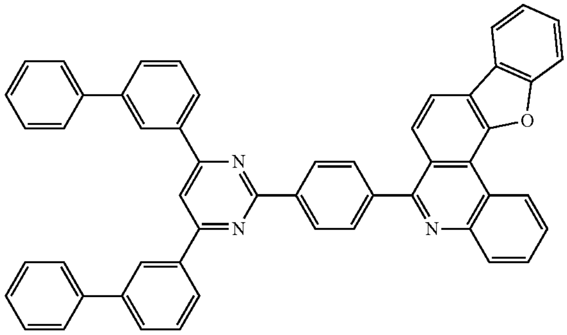
4-505
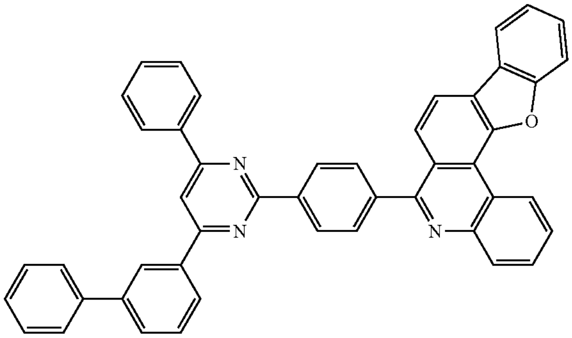
4-506
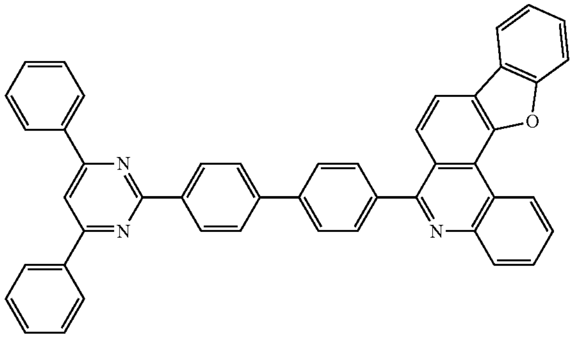
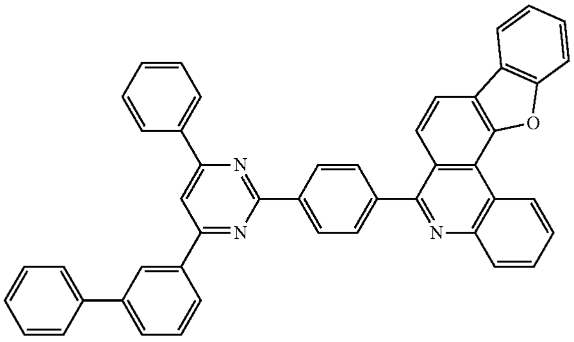

-continued
4-507
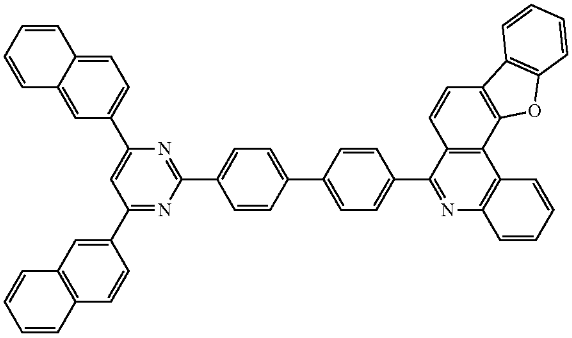
4-508
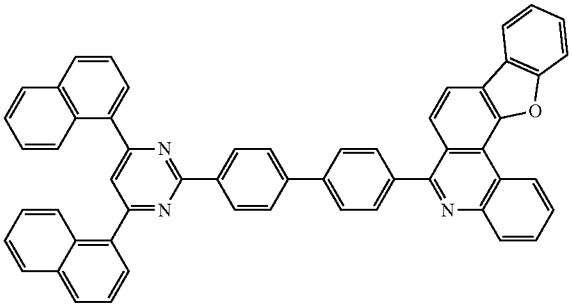
4-509
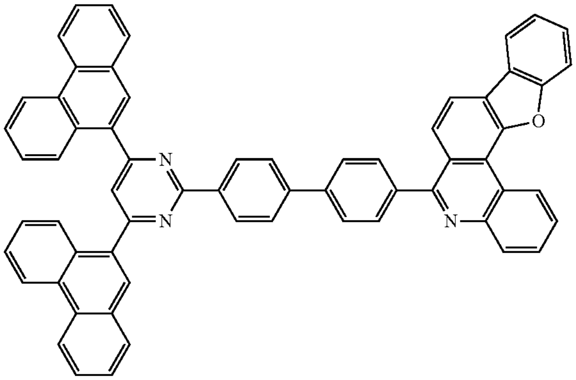
4-510
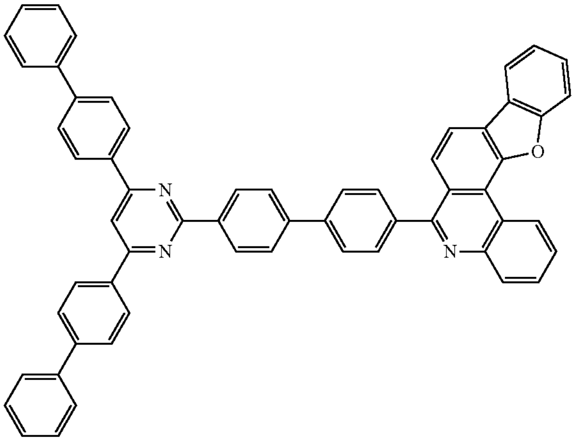
4-511
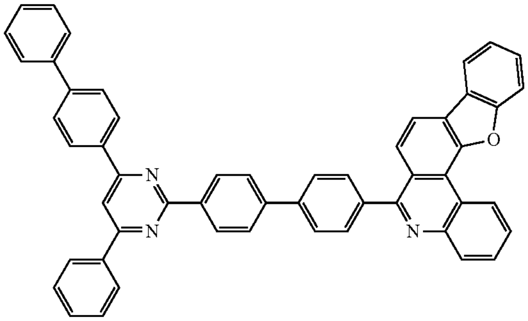
4-512
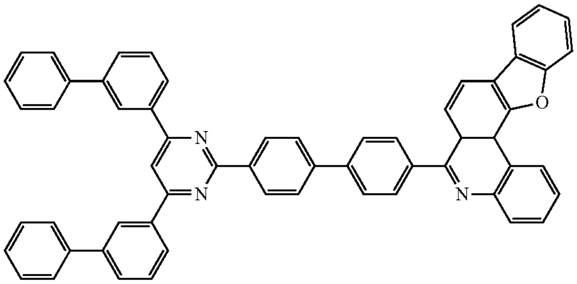
4-513
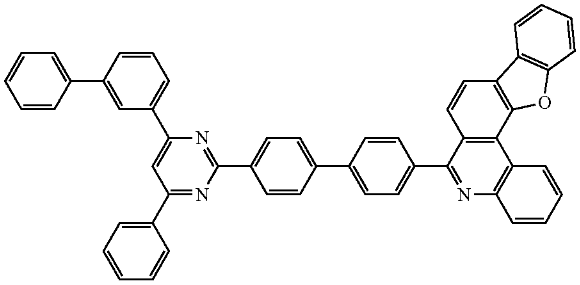
4-514
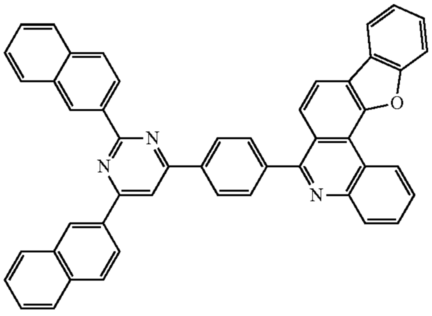

-continued
4-515
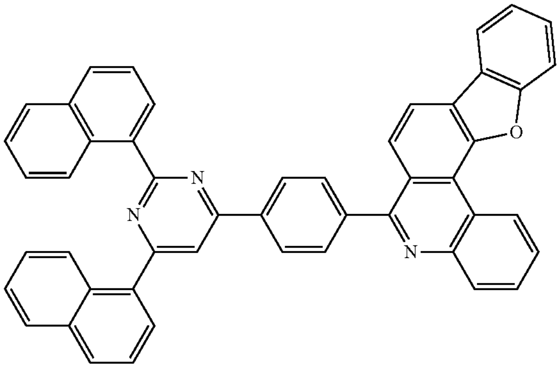
4-516
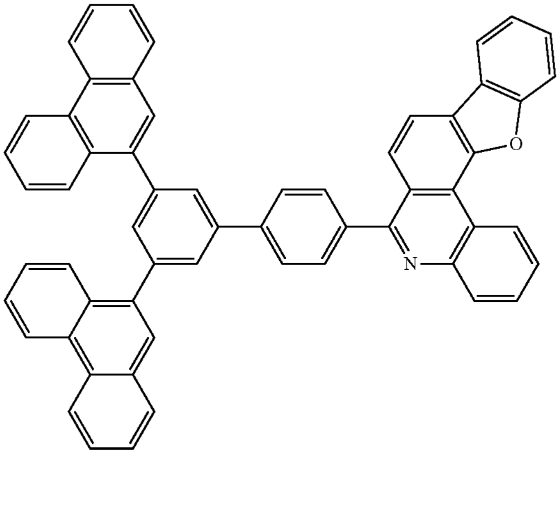
4-517
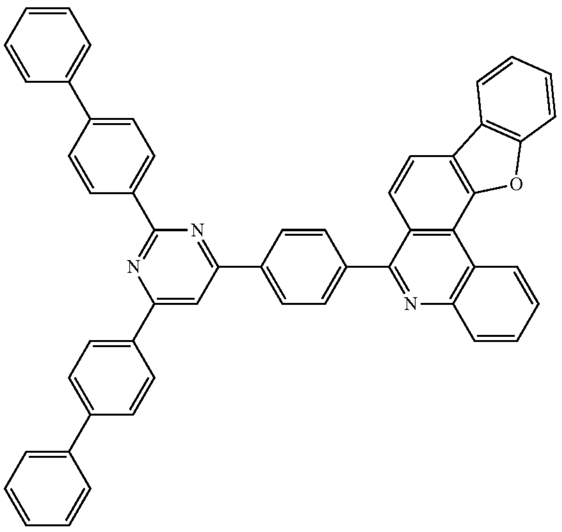
4-518
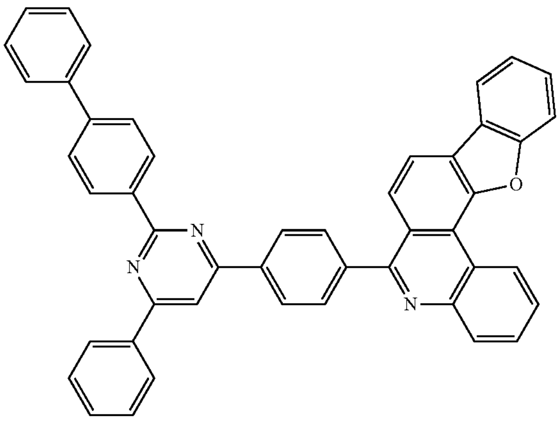
4-519
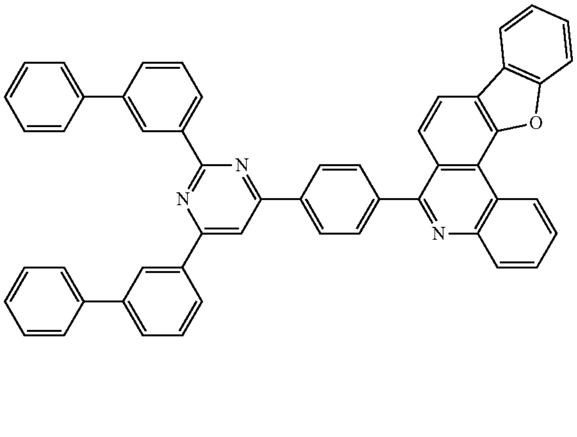
4-520
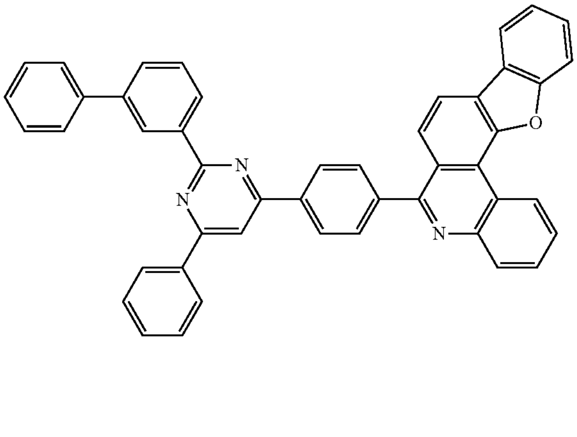

-continued
4-521
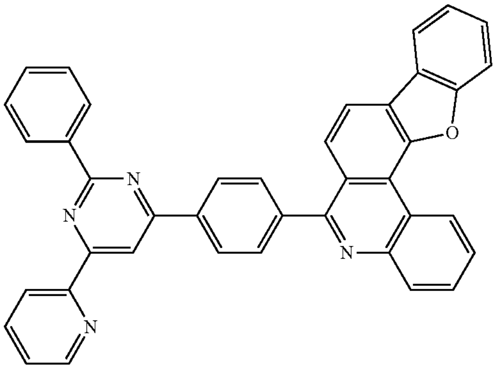
4-522
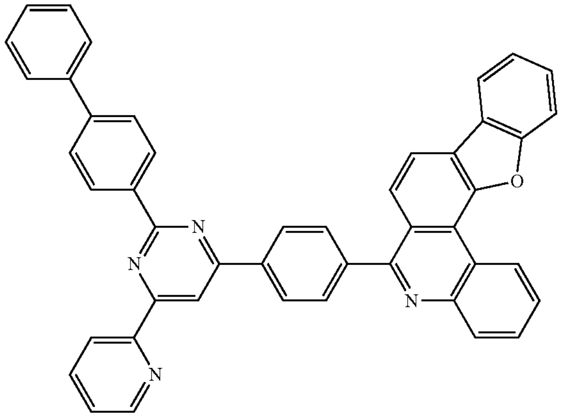
4-523
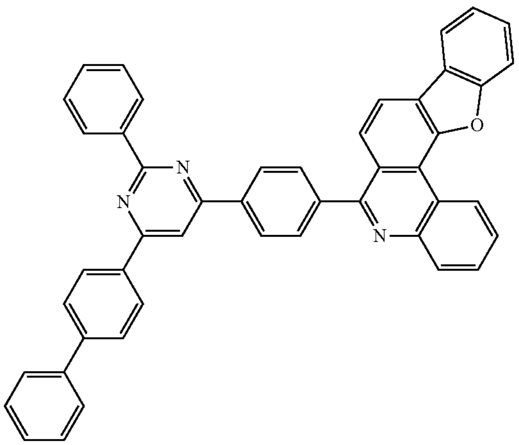
4-524
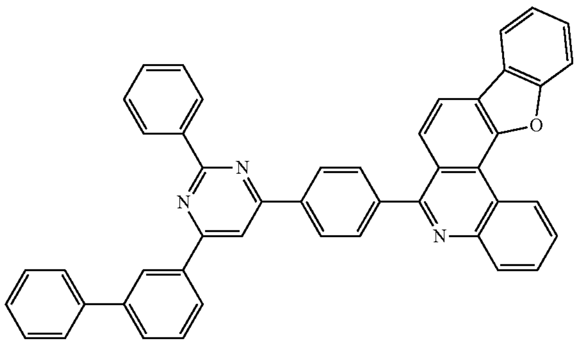
4-525
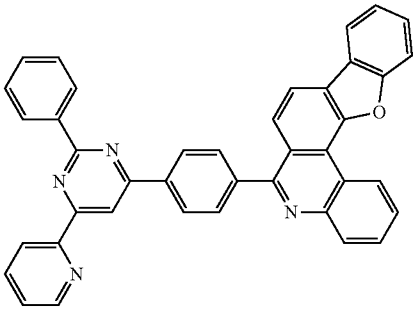
4-526
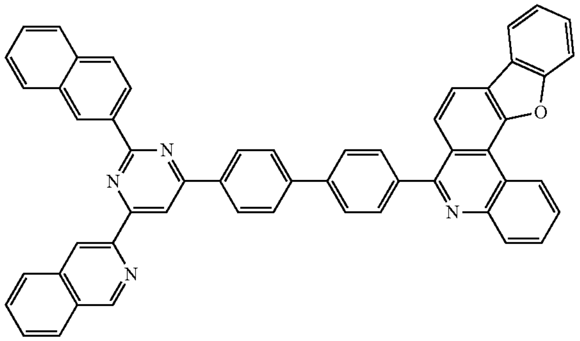

-continued
4-527
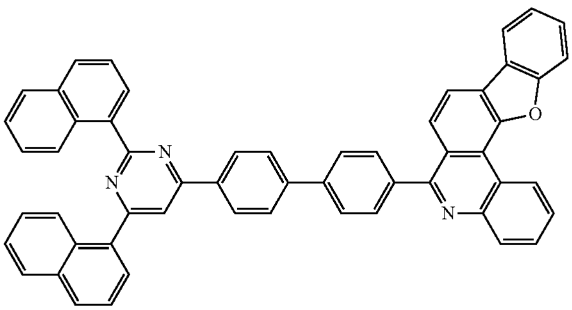
4-528
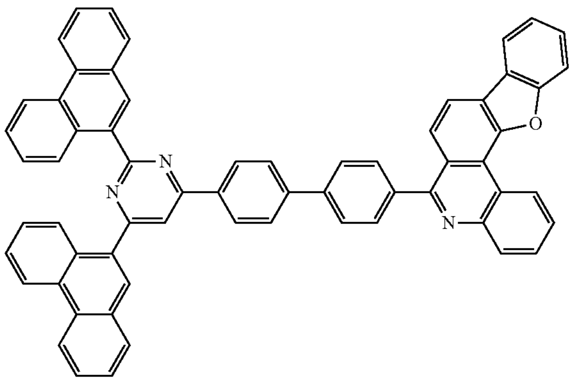
4-529
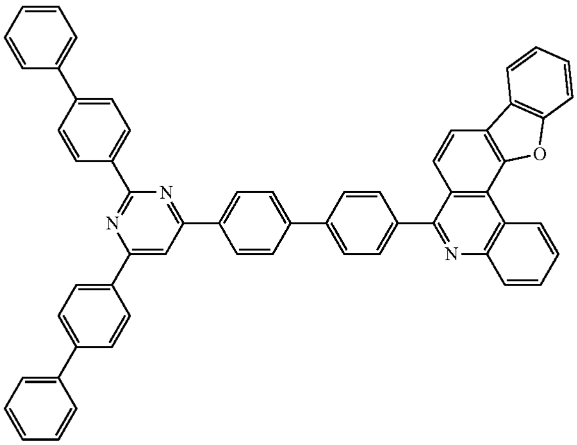
4-530
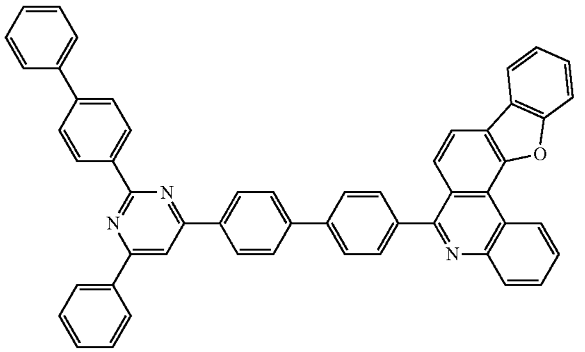
4-531
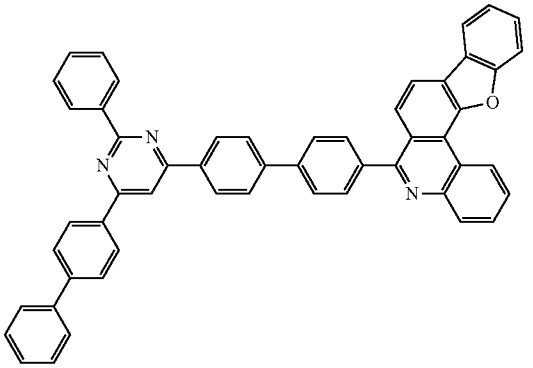
4-532
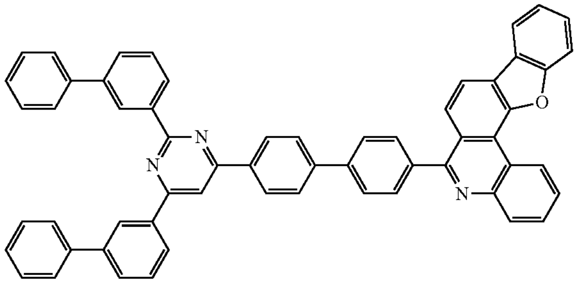
4-533
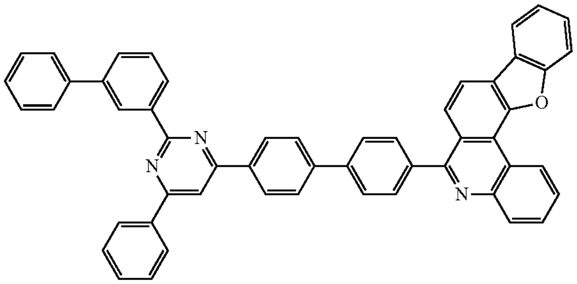
4-534
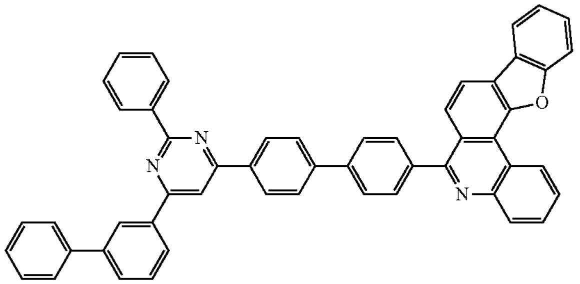

-continued
4-535
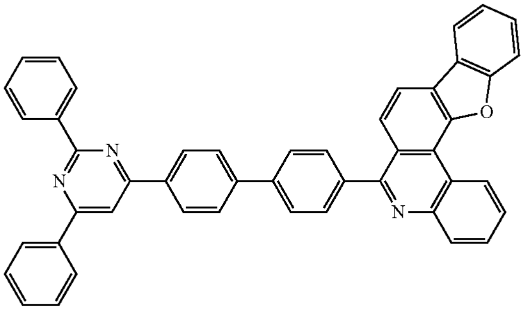
4-536
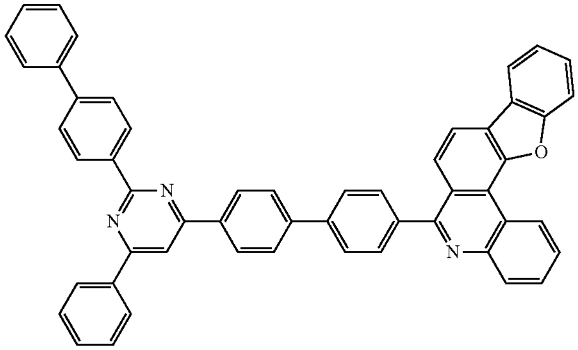
4-537
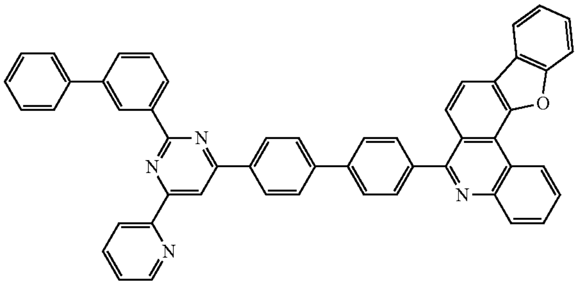
4-538
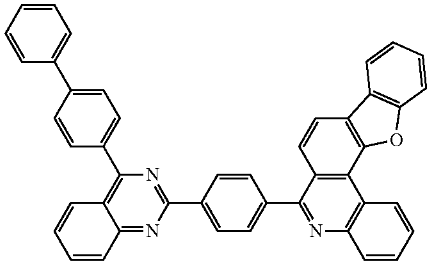
4-539
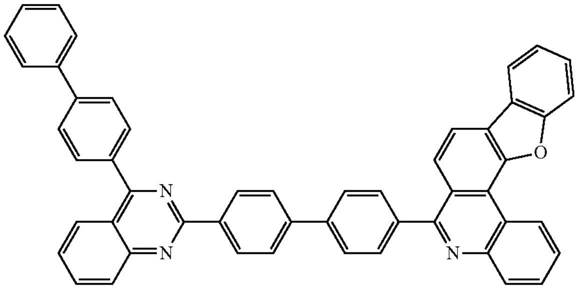
4-540
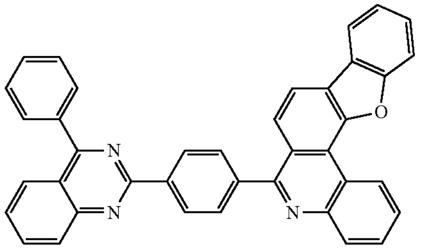
4-541
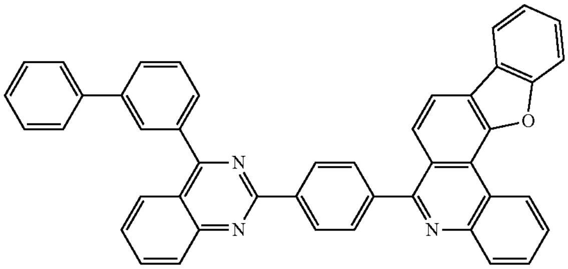
4-542
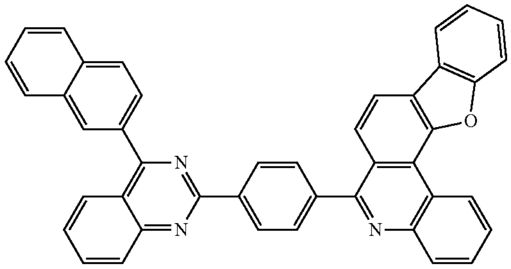
4-543
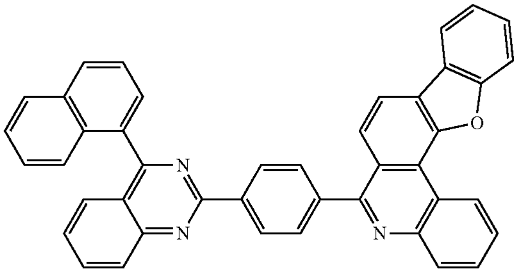
4-544
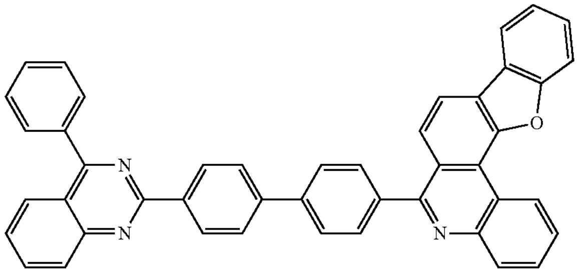

-continued
4-545
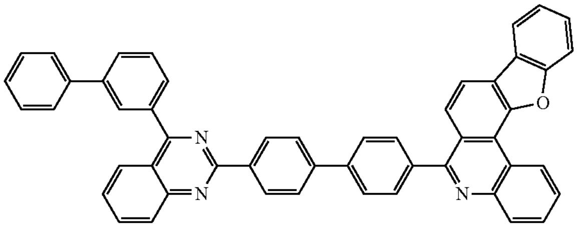
4-546
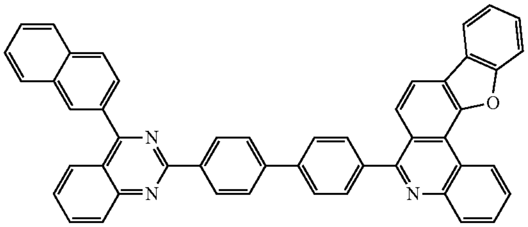
4-547
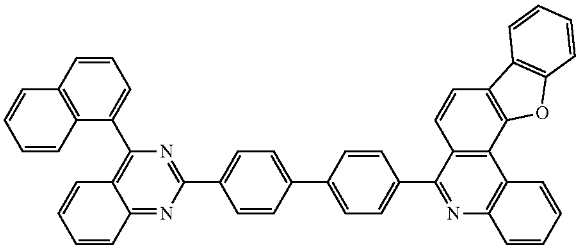
4-548
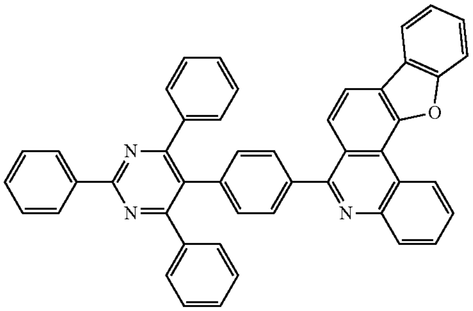
4-549
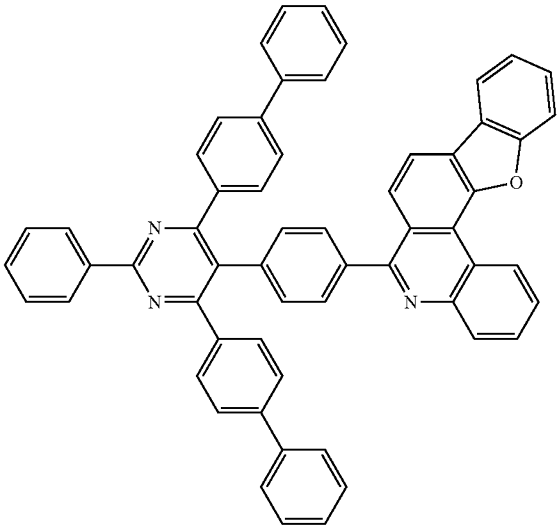
4-550
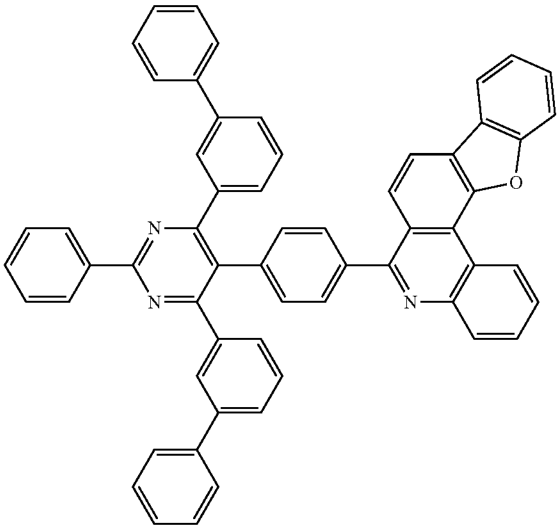
4-551
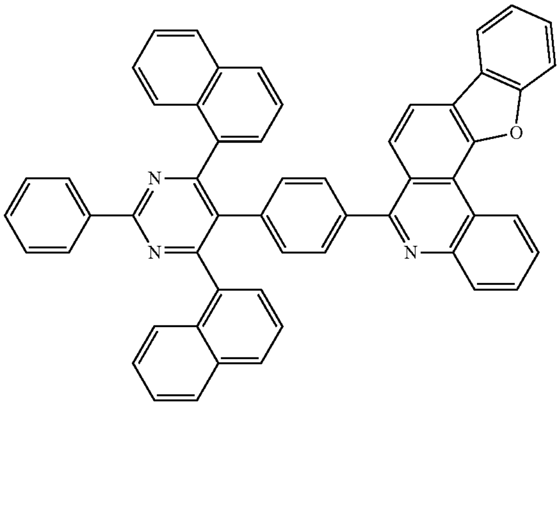
4-552
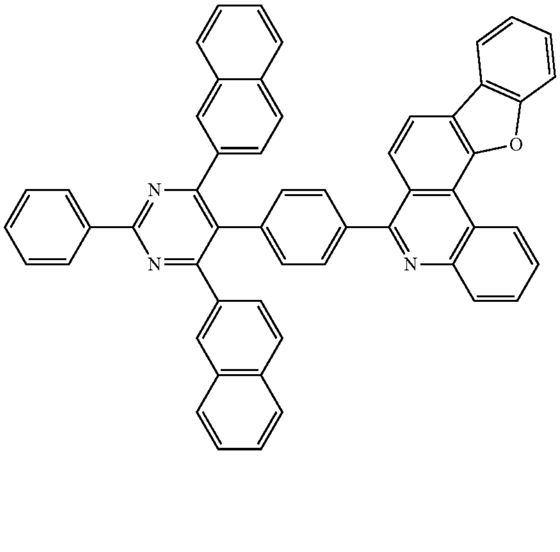

-continued
4-553
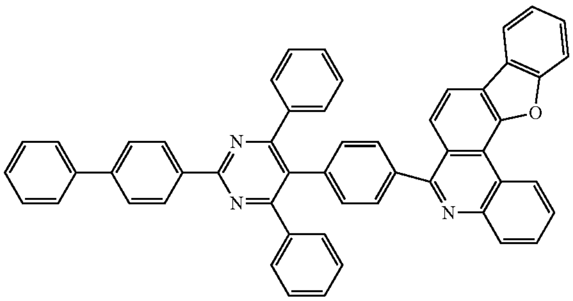
4-554
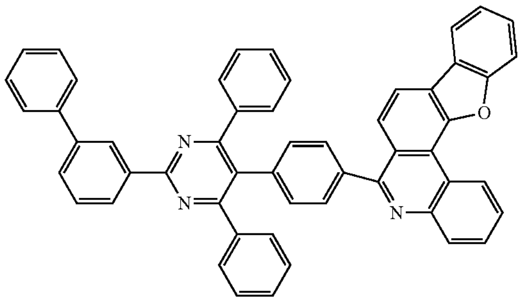
4-555
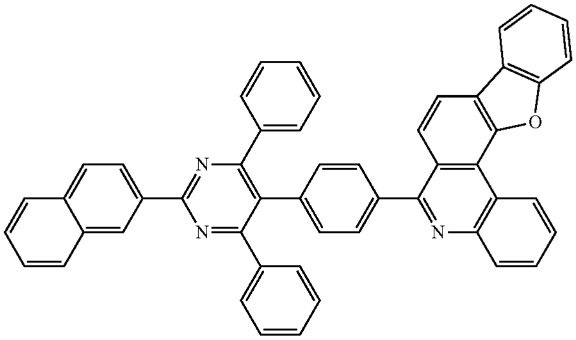
4-556
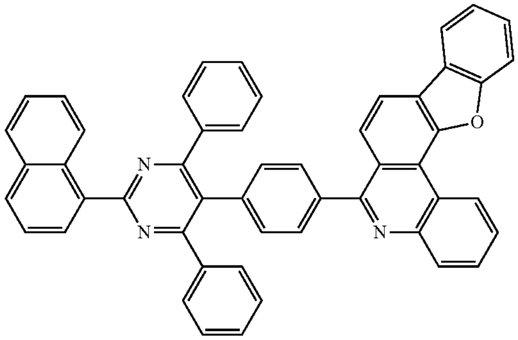
4-557
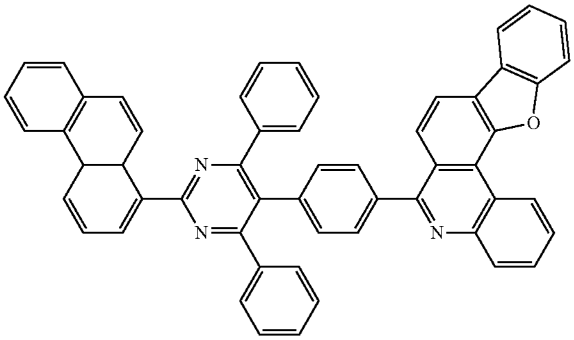
4-558
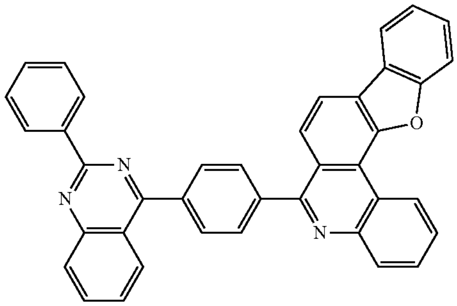
4-559
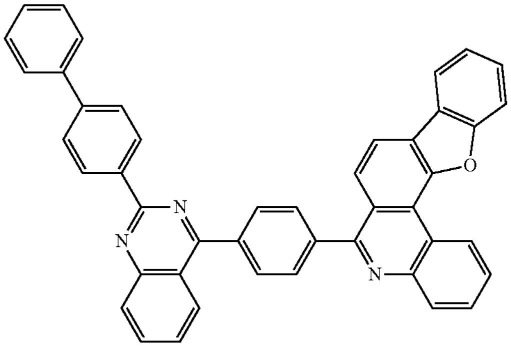
4-560
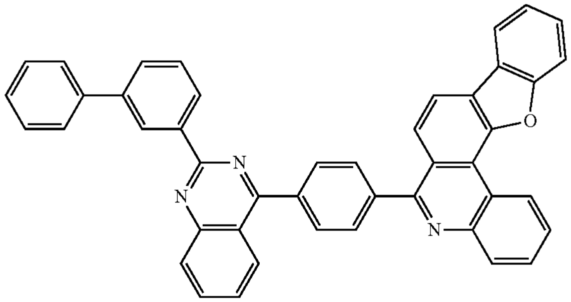

-continued
4-561
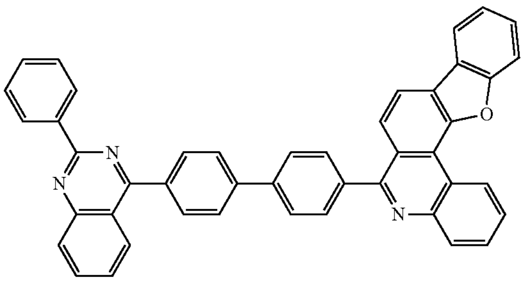
4-562
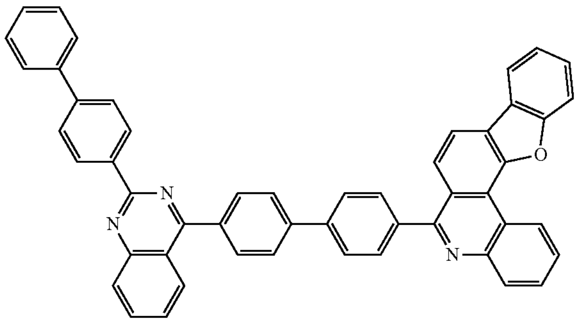
4-563
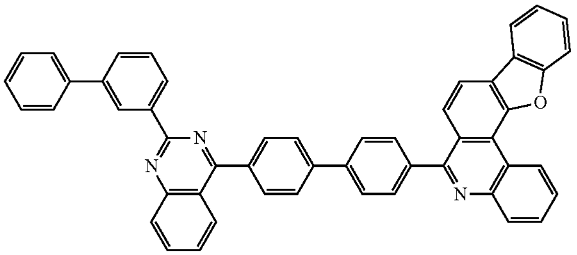
4-564
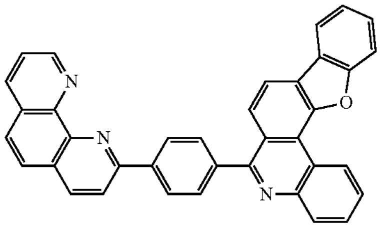
4-565
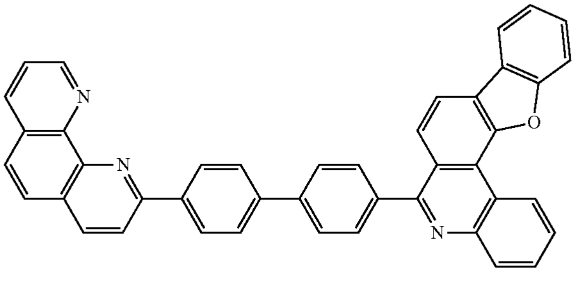
4-566
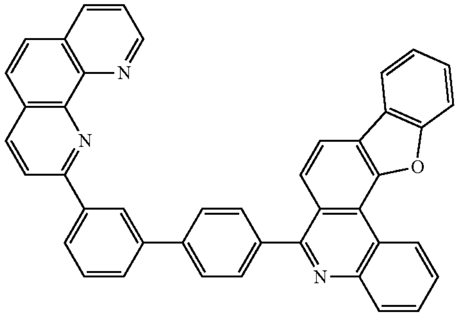
4-567
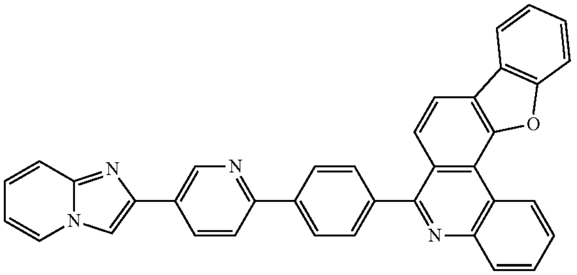
4-568
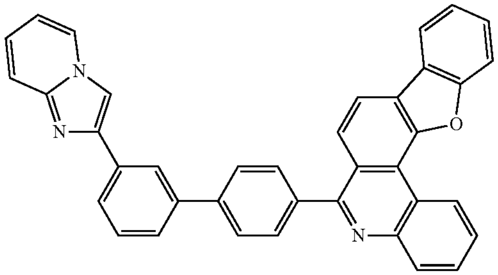
4-569
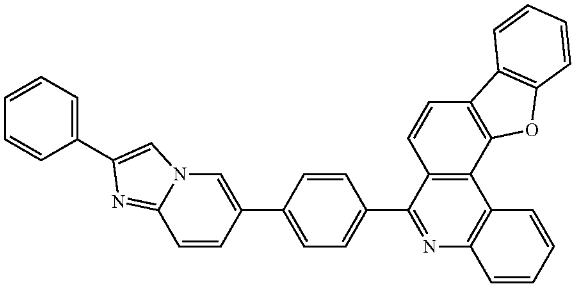
4-570
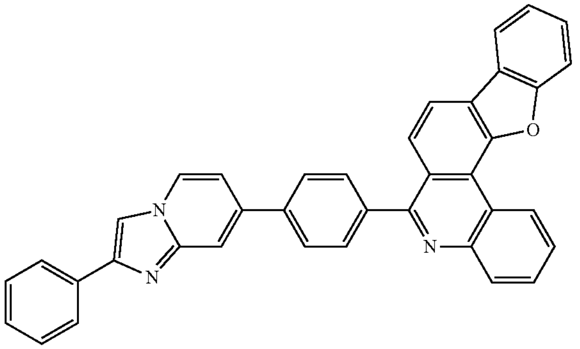

-continued
4-571
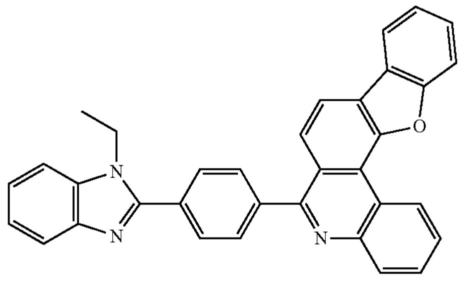
4-572
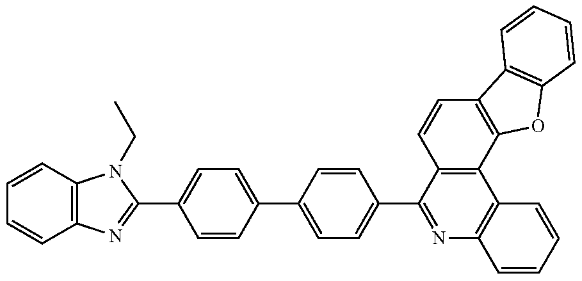
4-573
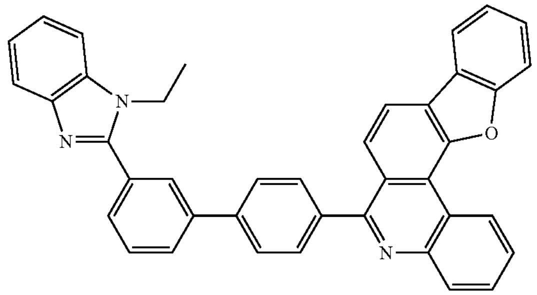
4-574
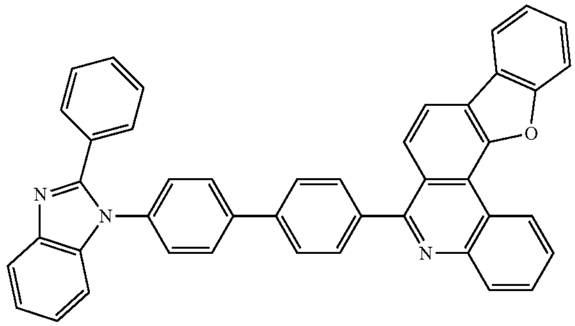
4-575
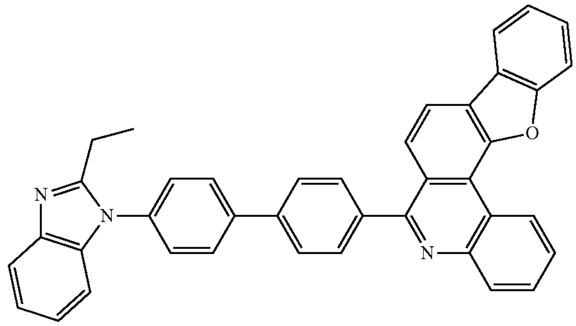
4-576
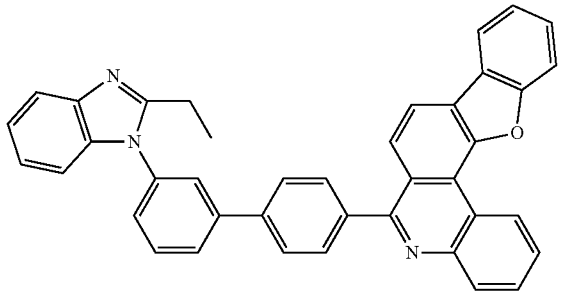
4-577
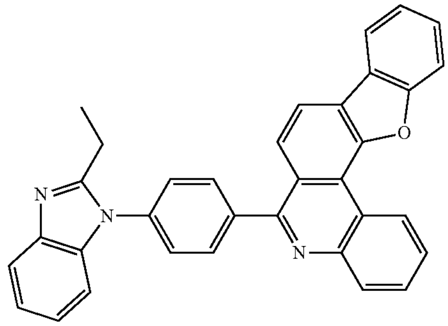
4-578
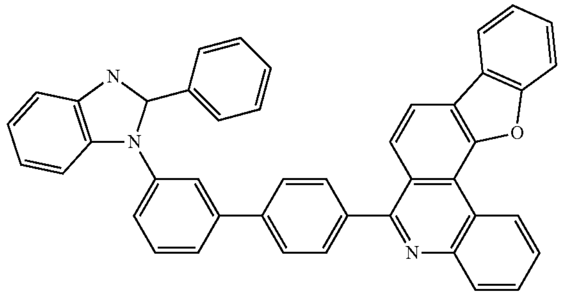

-continued
4-579
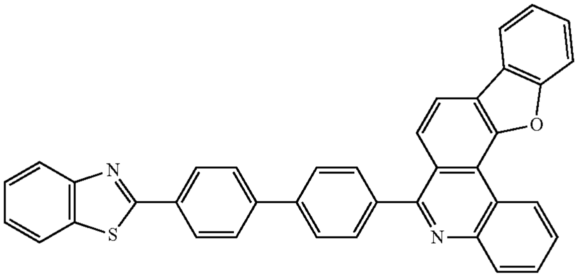
4-580
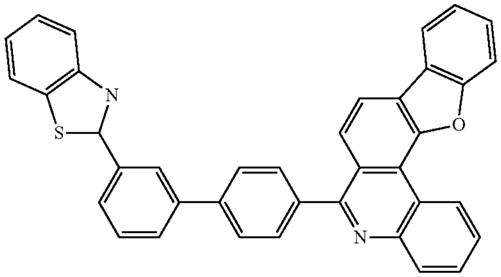
4-581
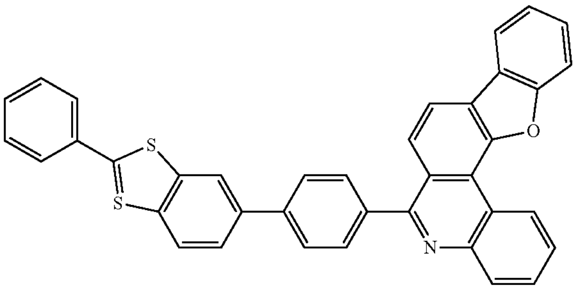
4-582
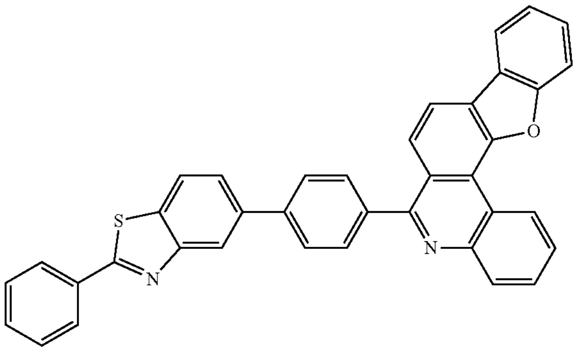
4-583
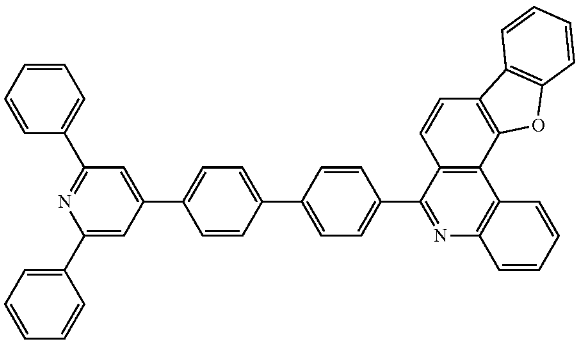
4-584
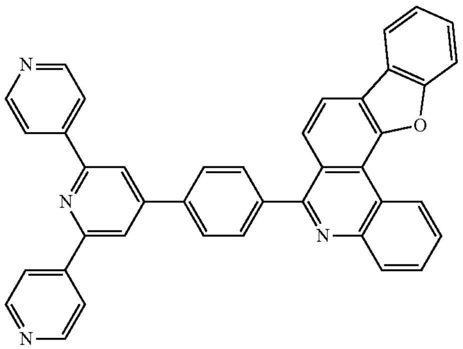
4-585
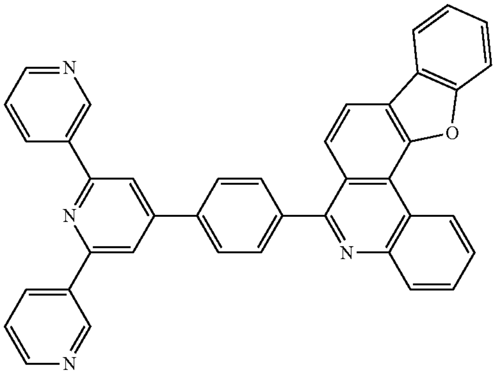
4-586
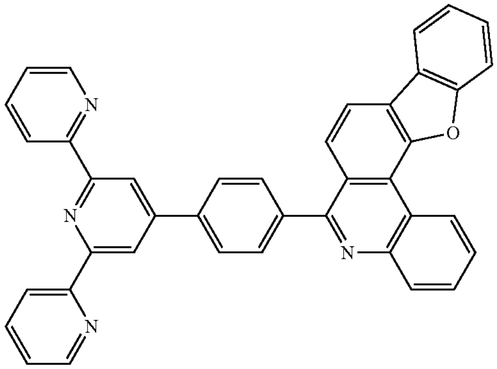

-continued
4-587
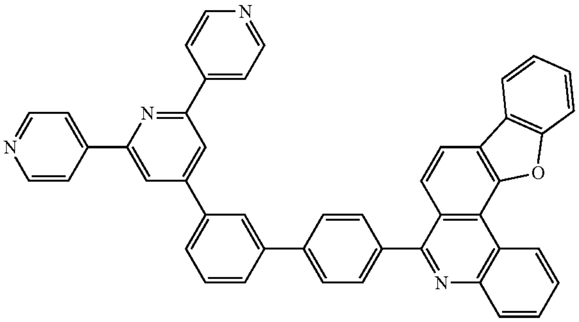
4-588
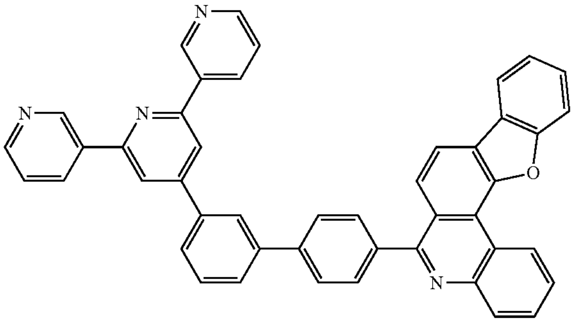
4-589
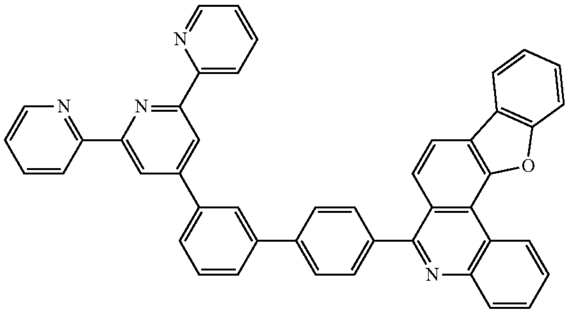
4-590
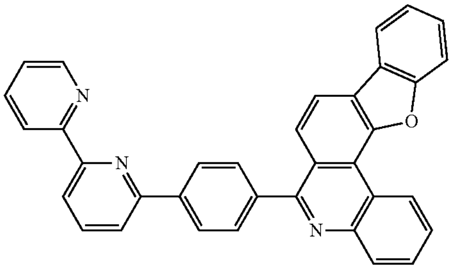
4-591
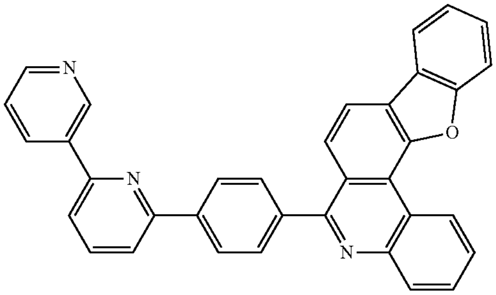
4-592
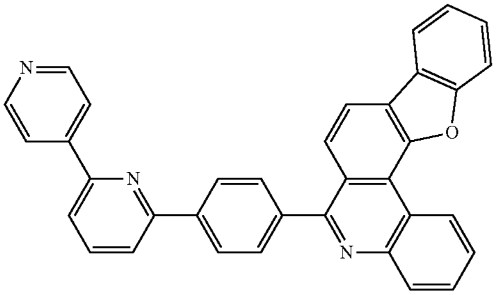
4-593
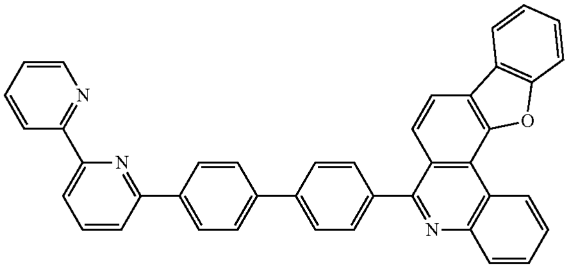
4-594
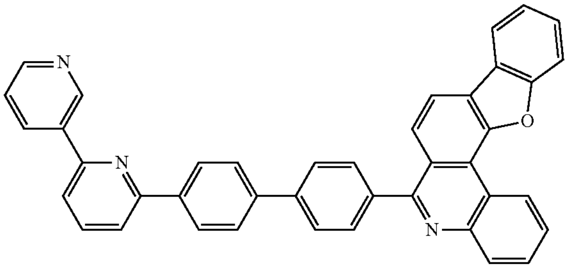
4-595
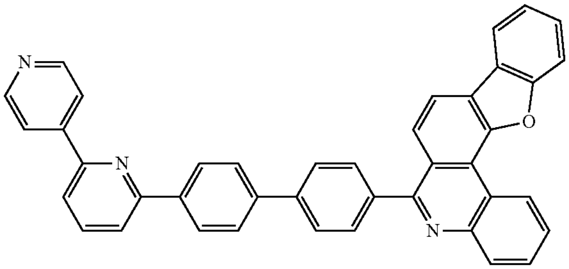
4-91
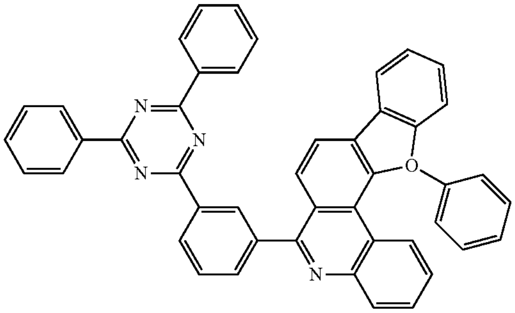

-continued
4-92
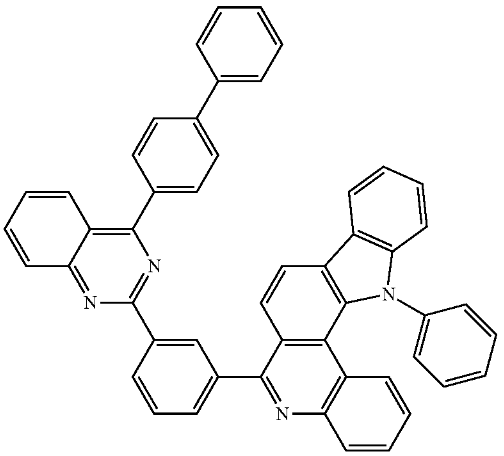
4-83
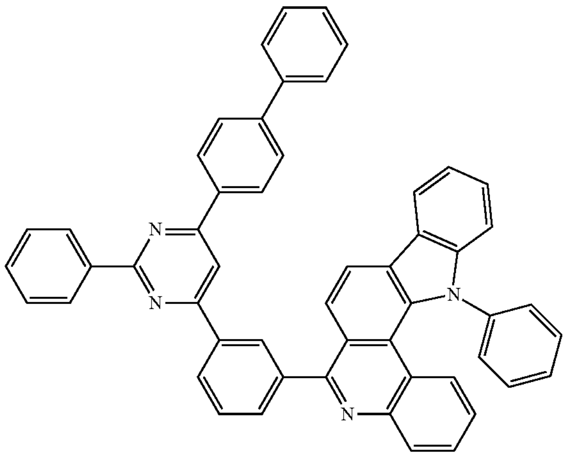
4-46
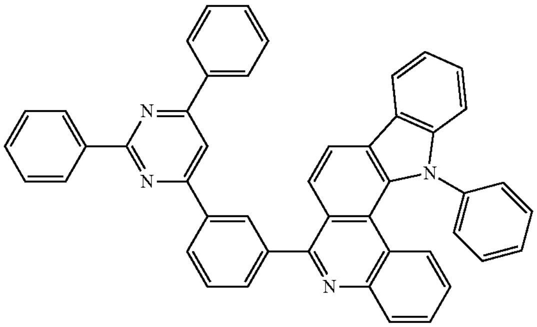
4-86
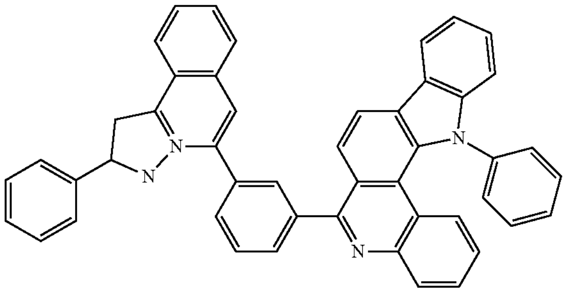
4-446
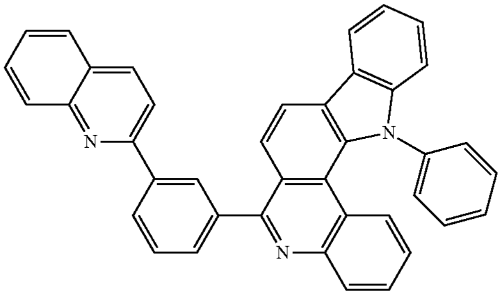
4-87
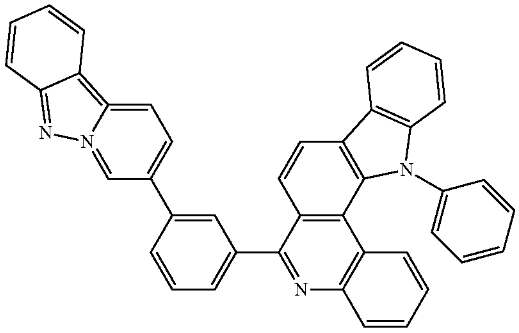
4-88
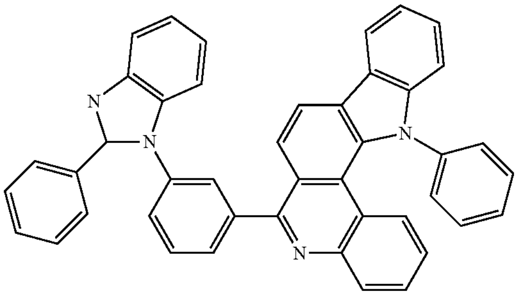
4-89
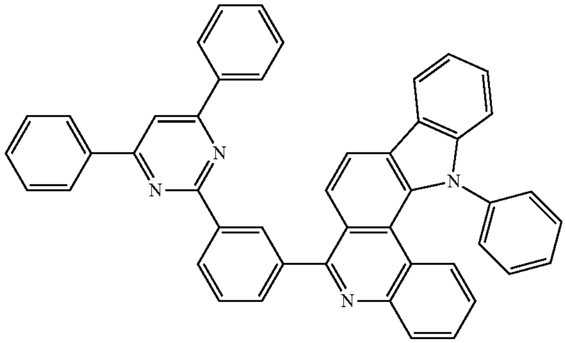

-continued
4-100
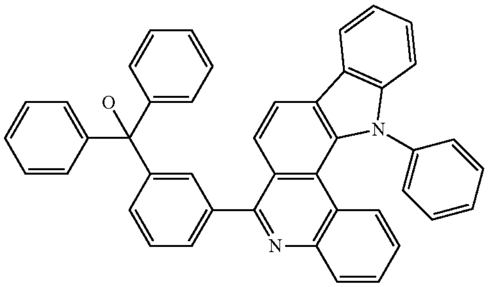
4-101
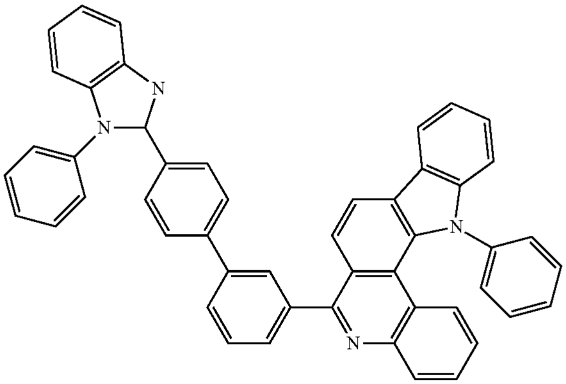
4-102
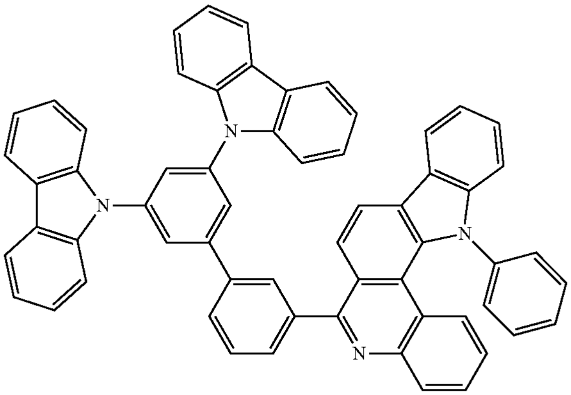
4-103
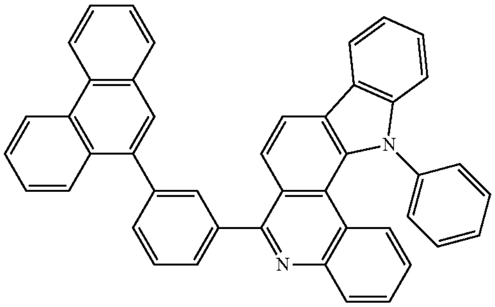
4-104
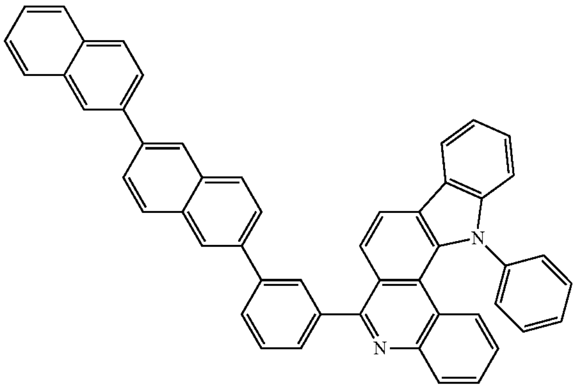
4-105
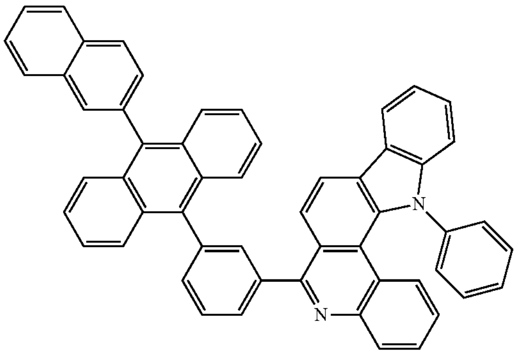
4-106
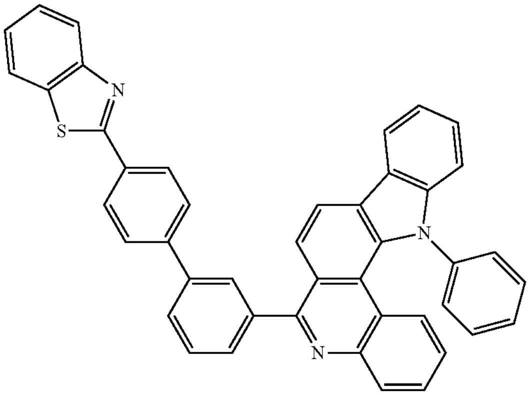
4-107
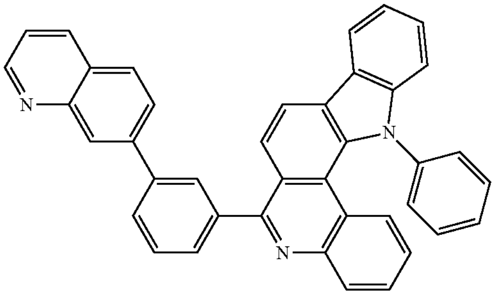

-continued
4-108
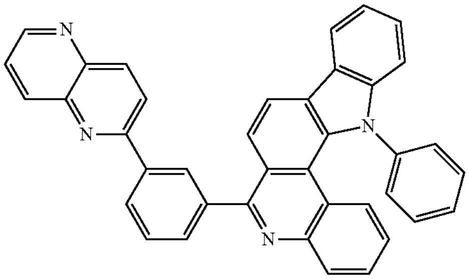
4-109
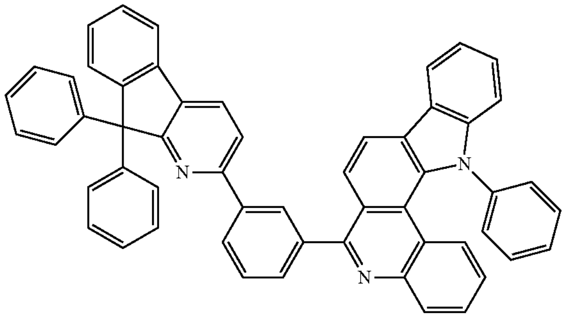
4-110
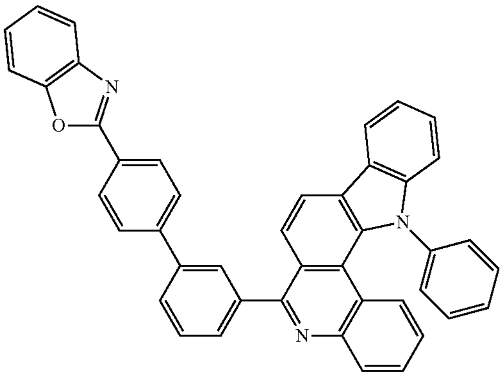
4-111
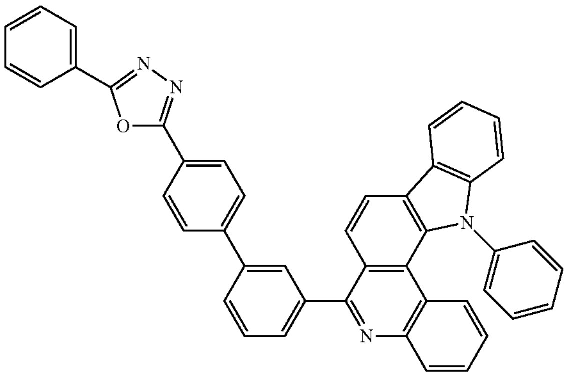
4-112
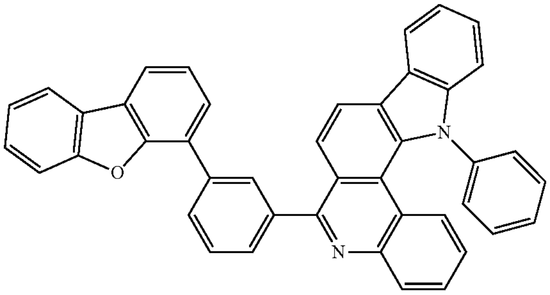
4-113
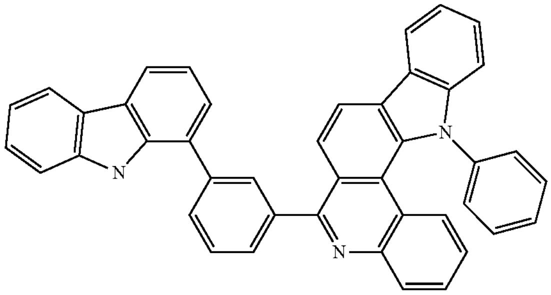
4-114
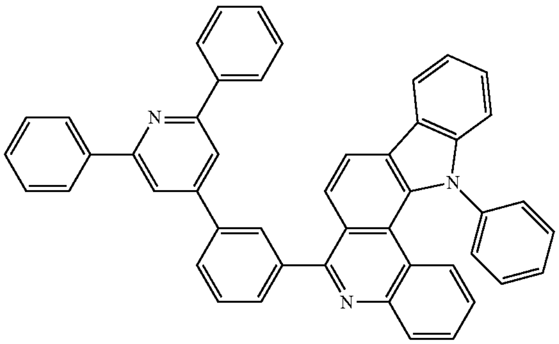
4-115
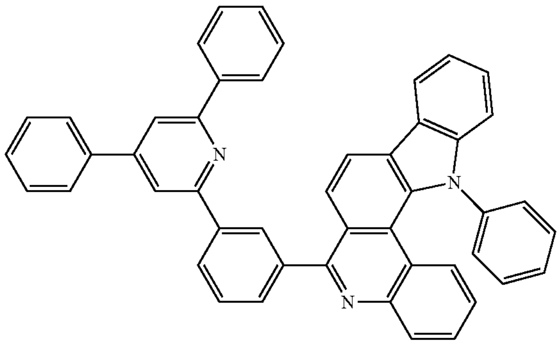

-continued
4-116
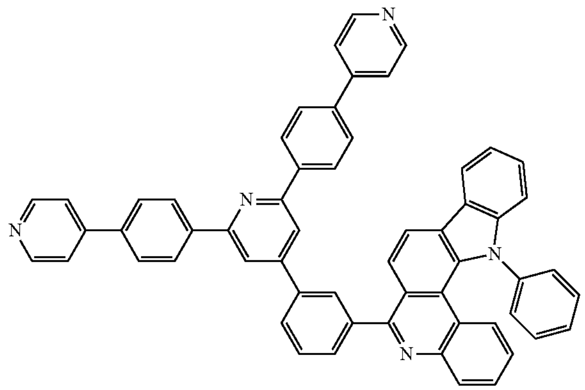
4-117
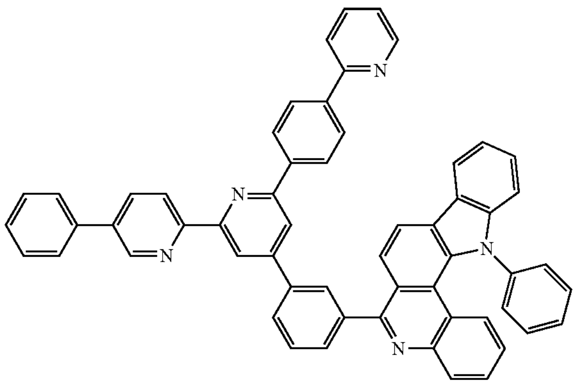
4-118
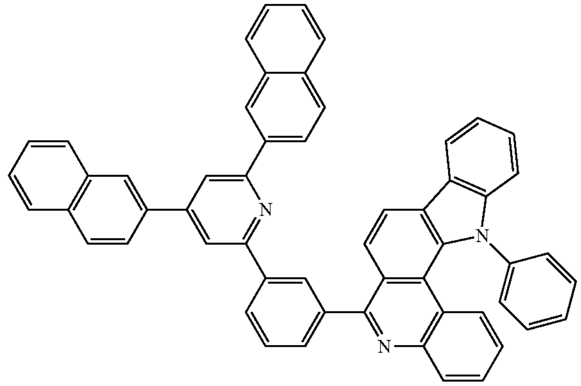
4-119
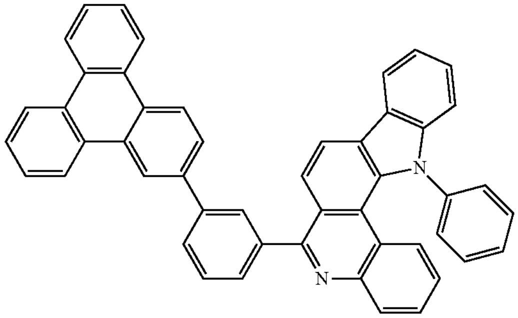
4-120
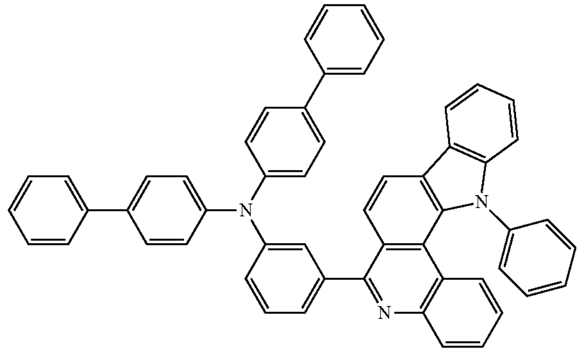
4-121
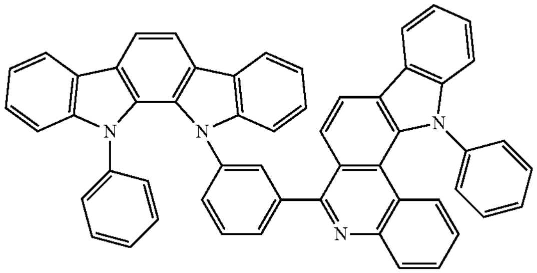
4-122
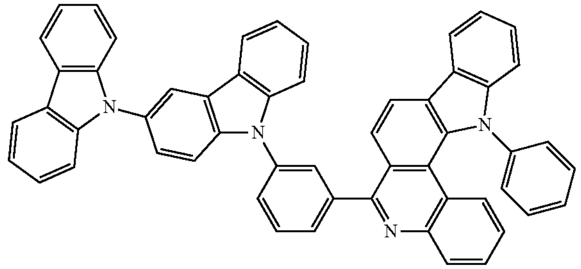
4-123
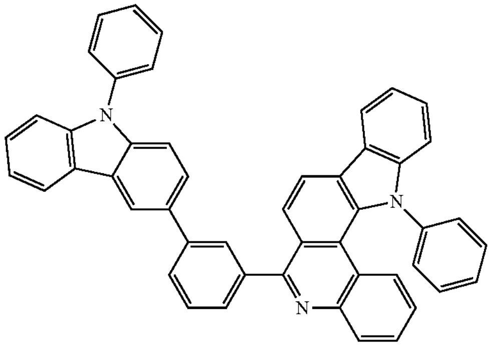

-continued
4-124
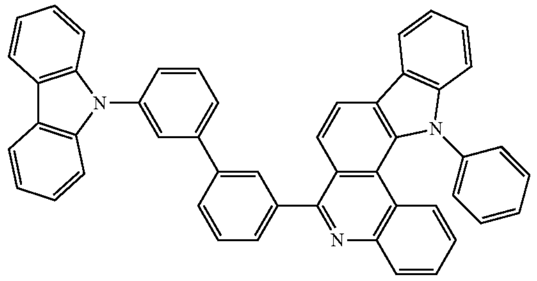
4-125
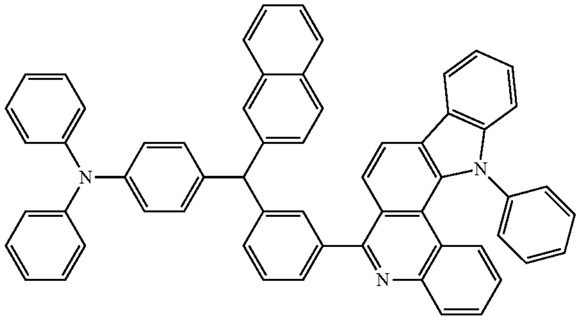
4-126
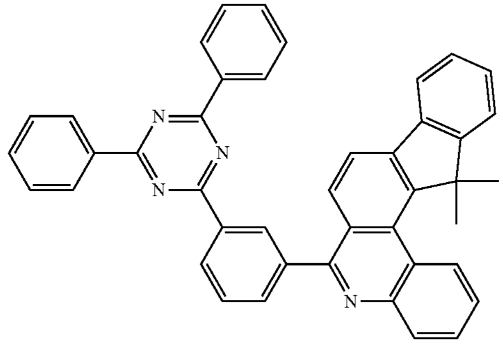
4-127
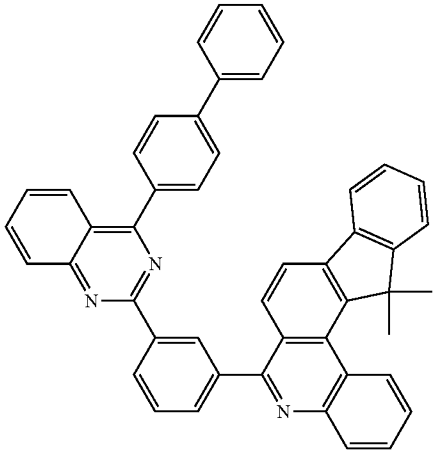
4-128
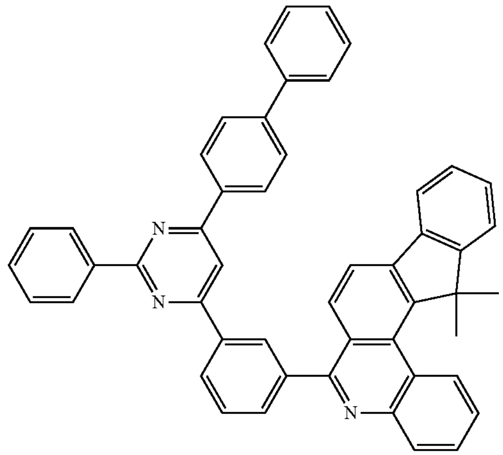
4-129
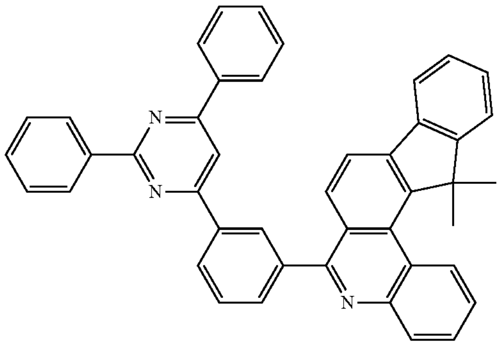
4-130
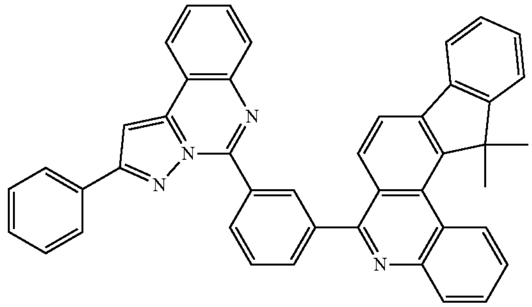
4-131
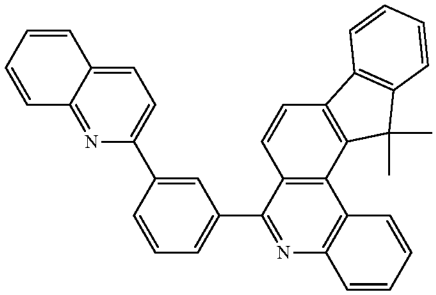

-continued
4-132
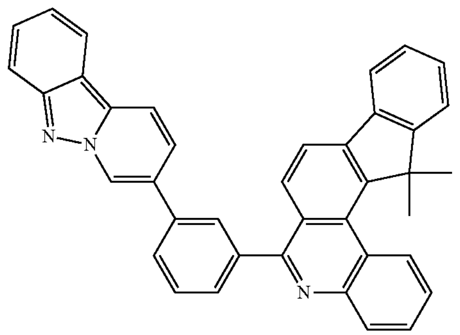
4-133
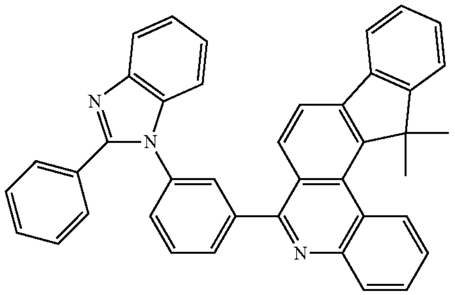
4-134
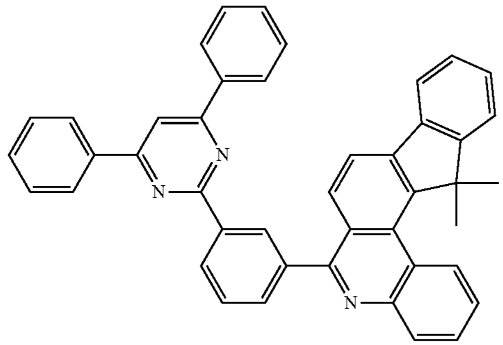
4-135
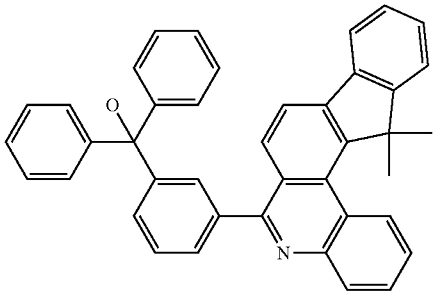
4-136
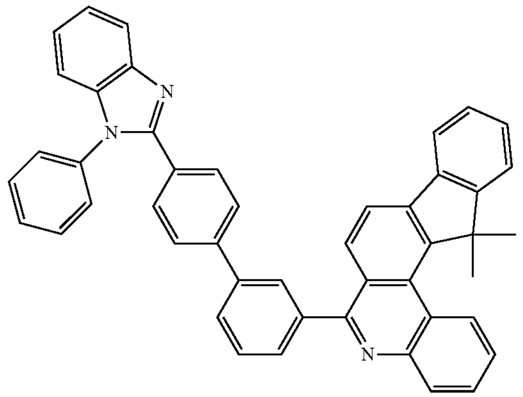
4-137
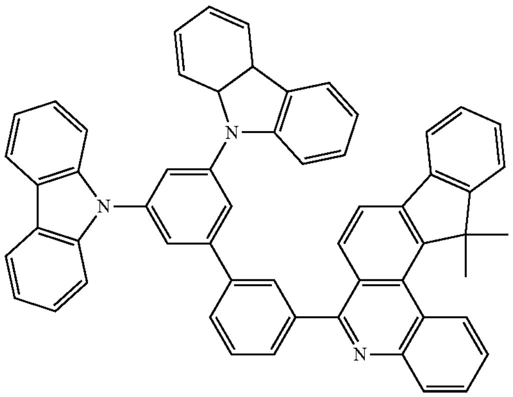
4-138
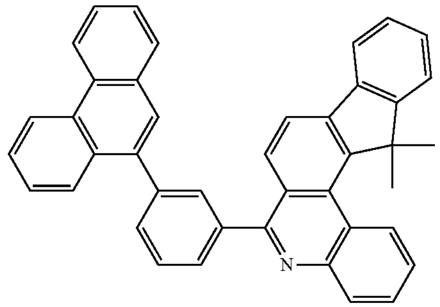
4-139
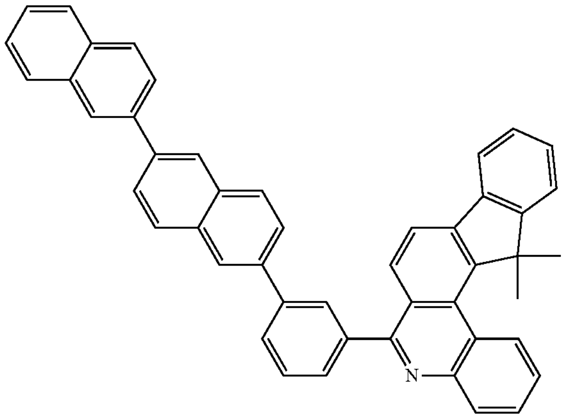

-continued
4-140
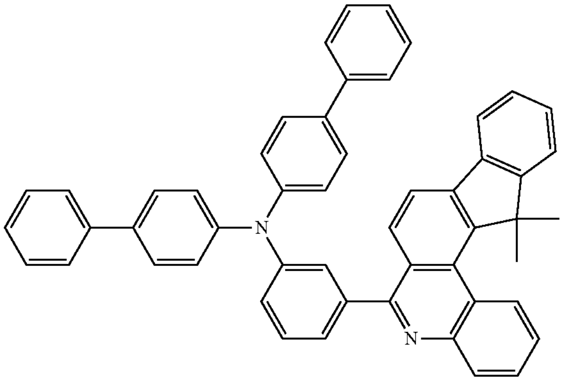
4-141
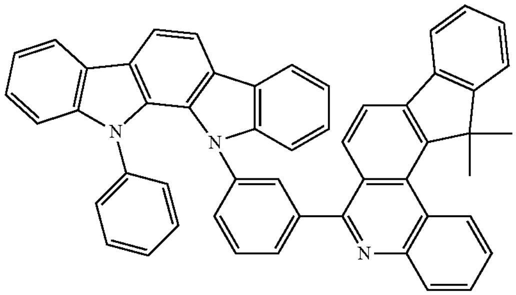
4-142
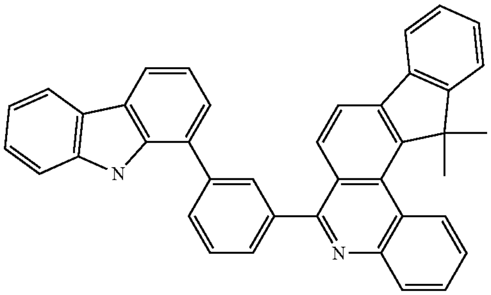
4-143
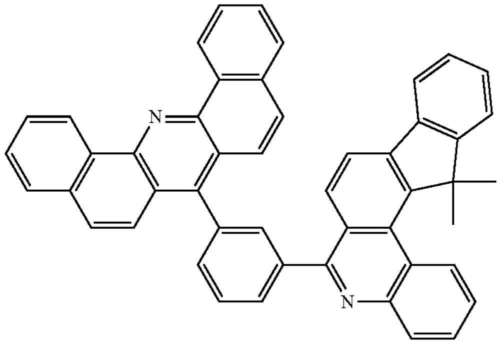
4-144
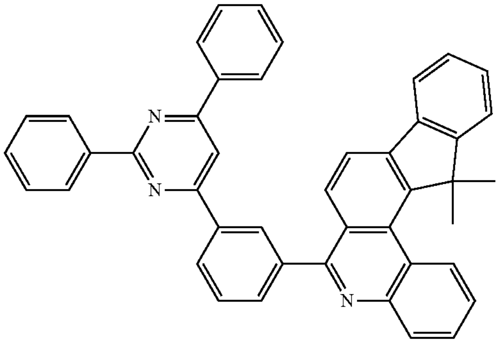
4-145
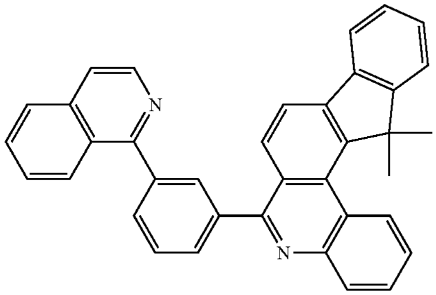
4-146
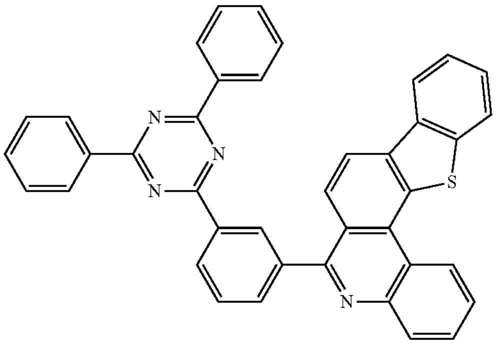
4-147
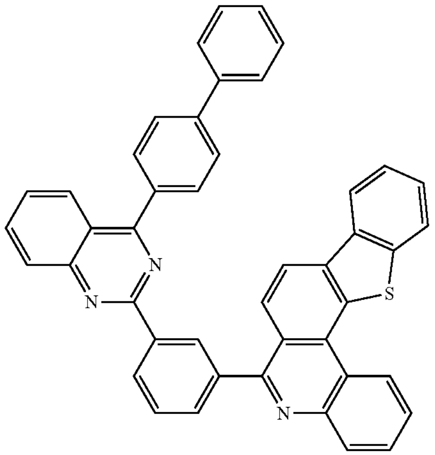

-continued
4-148
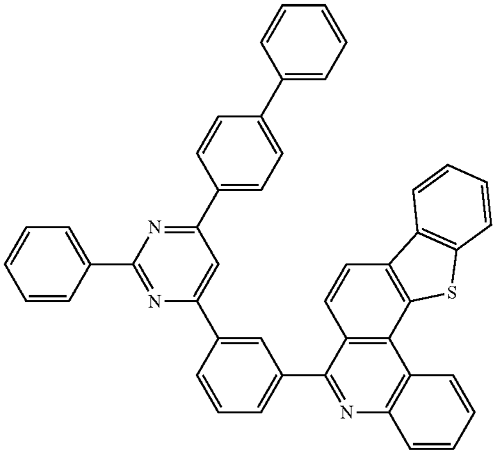
4-149
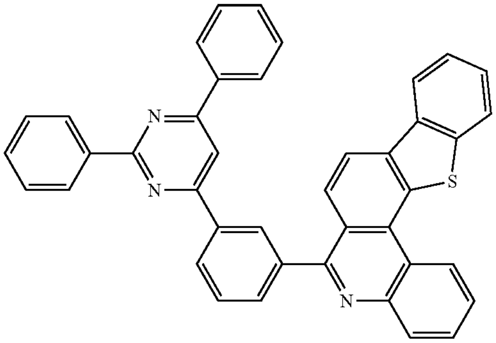
4-150
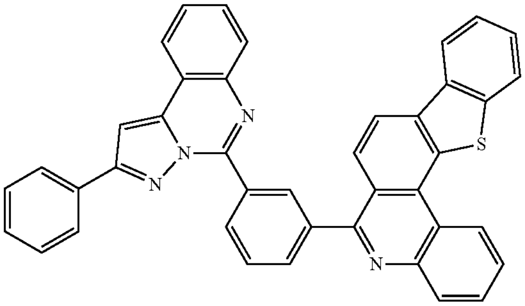
4-135
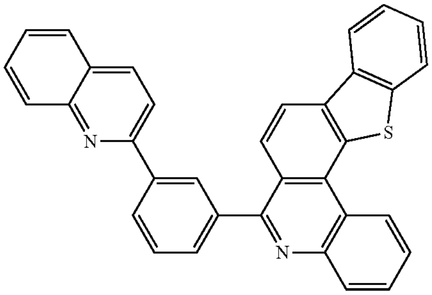
4-152
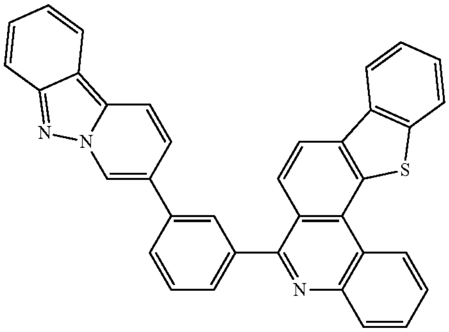
4-153
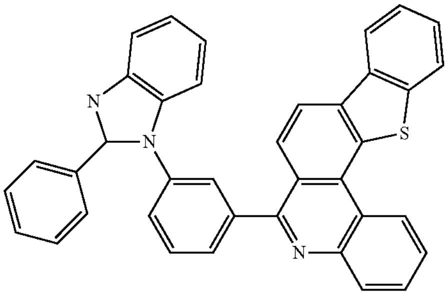
4-154
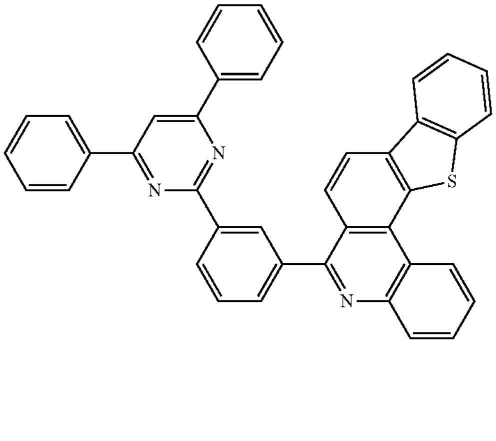
4-155
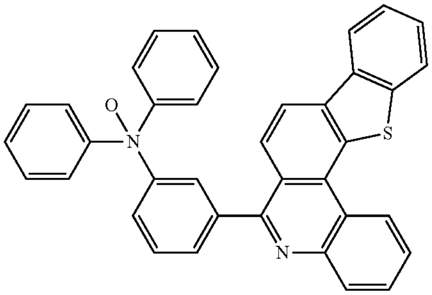

-continued
4-156
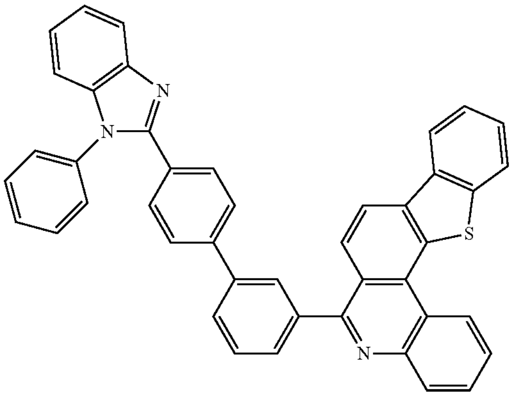
4-157
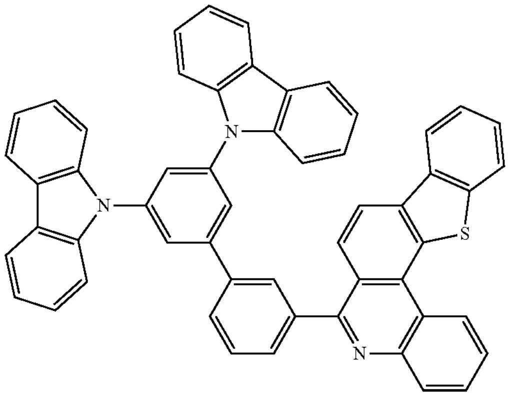
4-158
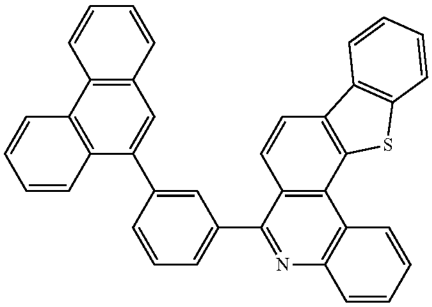
4-159
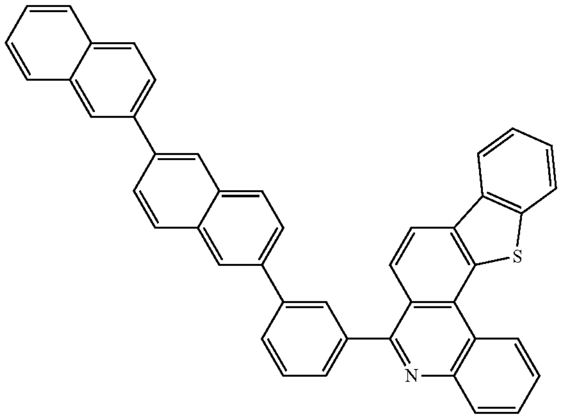
4-100
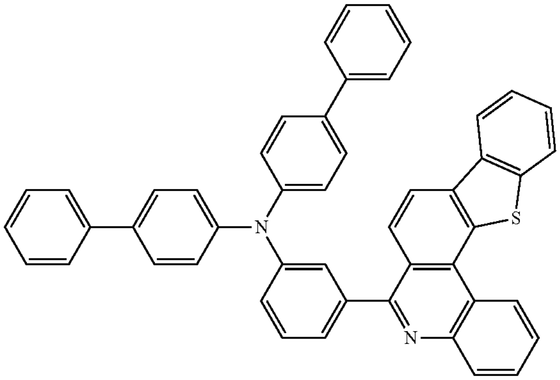
4-161
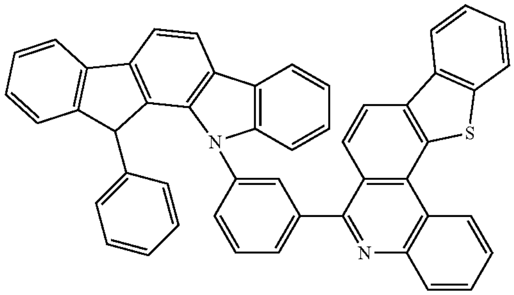
4-162
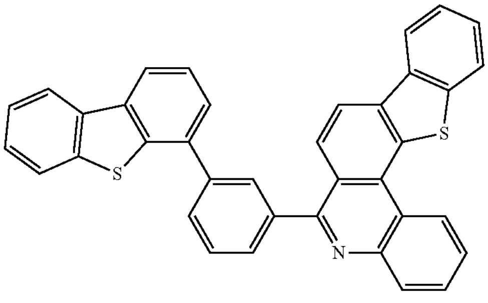
4-163
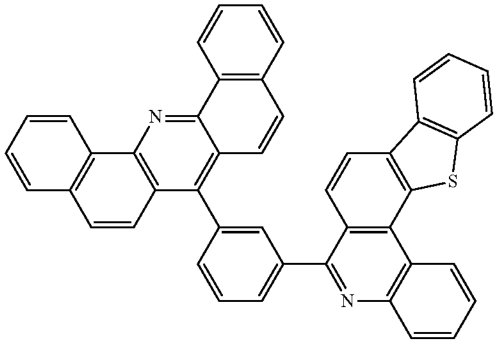

-continued
4-164
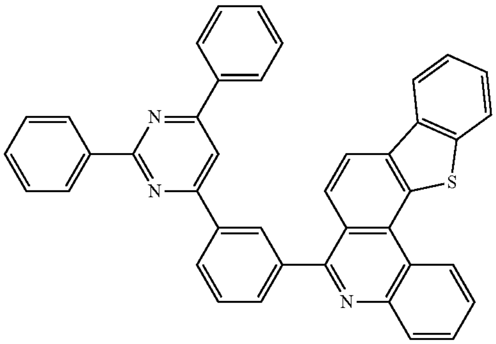
4-165
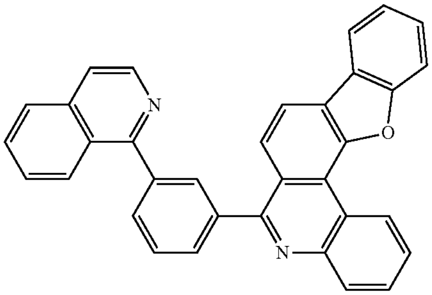
4-166
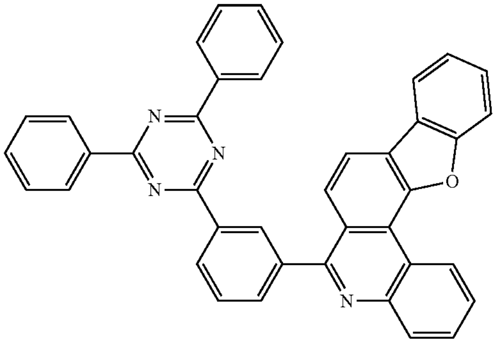
4-167
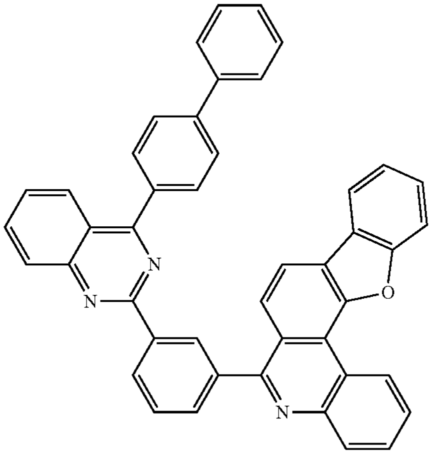
4-168
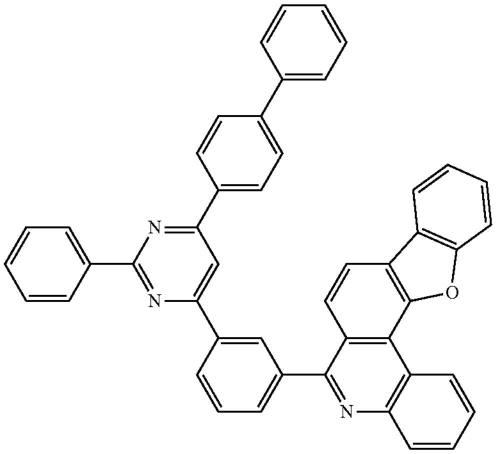
4-169
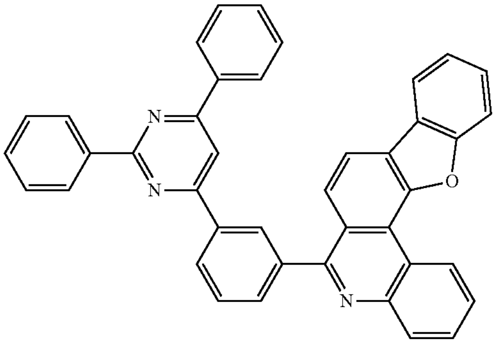
4-170
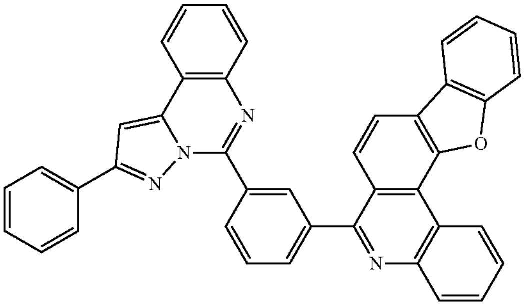
4-171
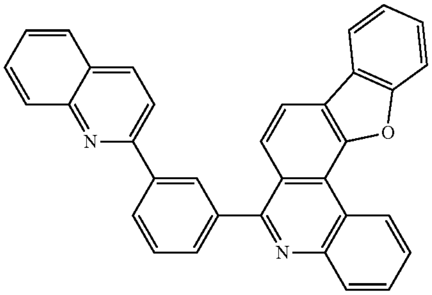

-continued
4-172
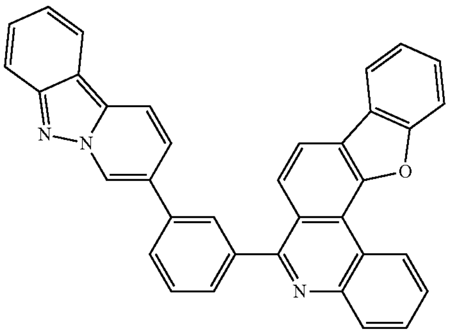
4-173
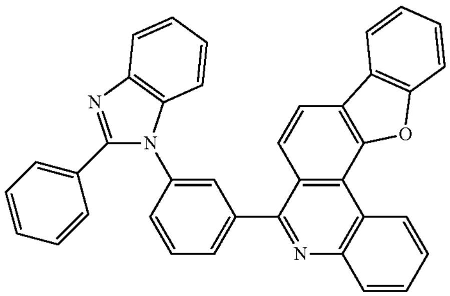
4-174
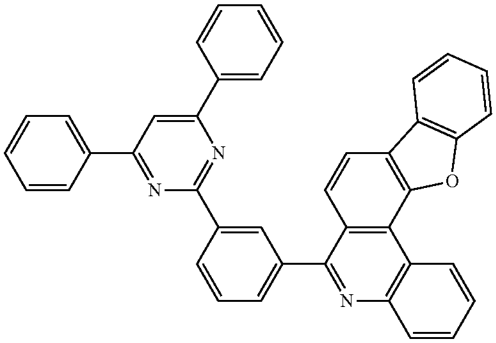
4-175
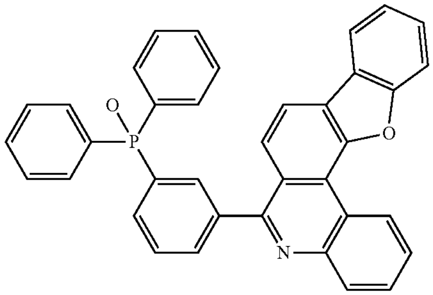
4-176
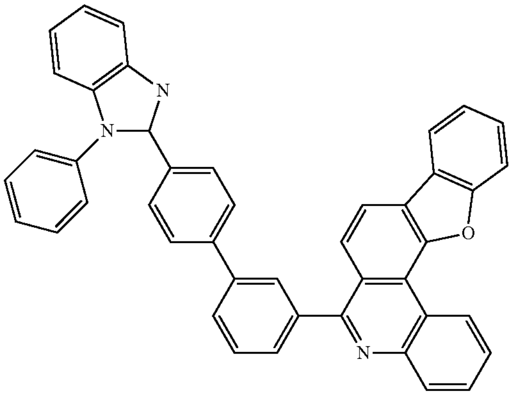
4-177
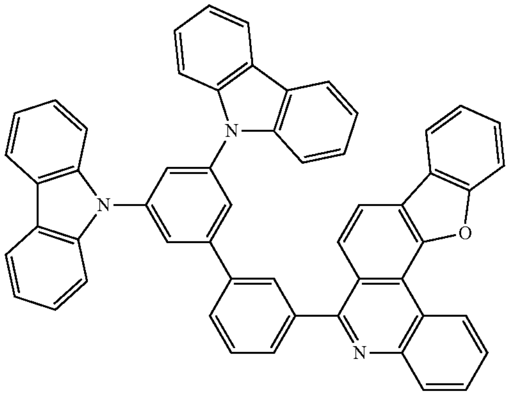
4-178
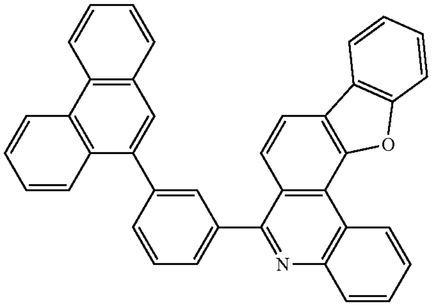
4-179
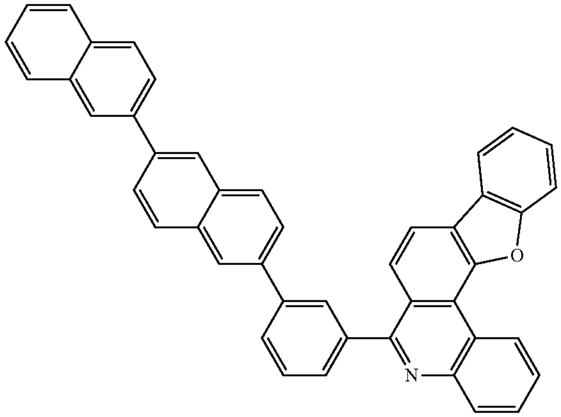

-continued
4-180
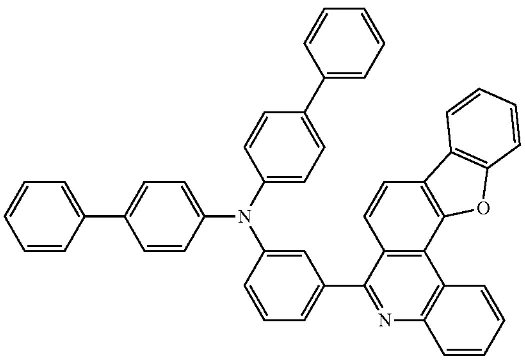
4-366
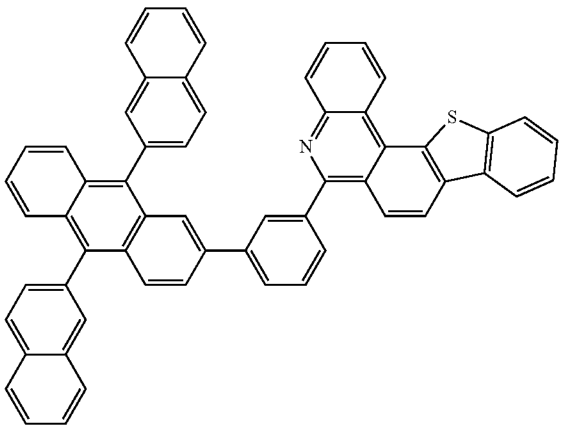
4-367
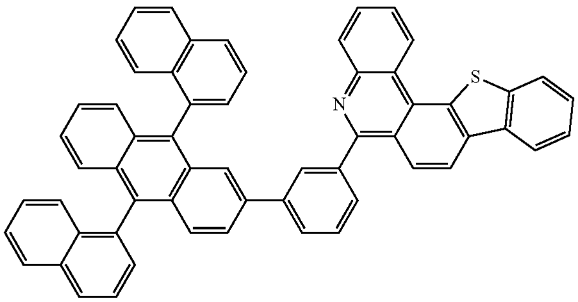
4-368
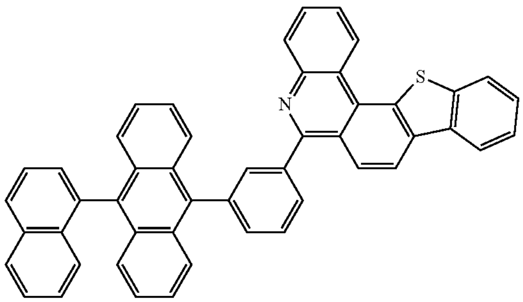
4-369
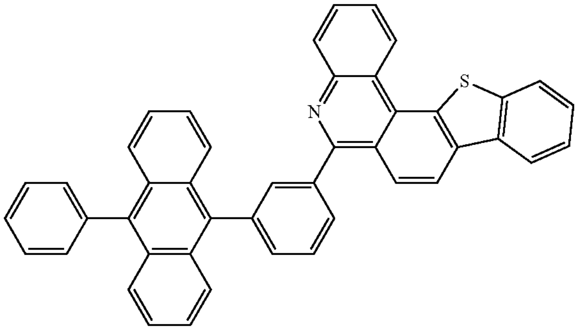
4-370
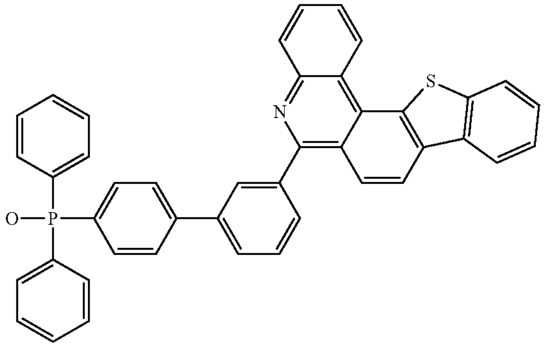
4-371
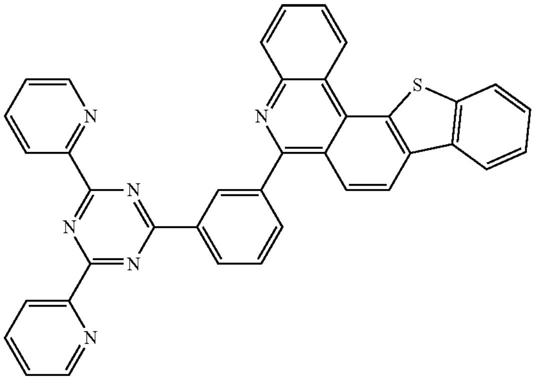
4-372
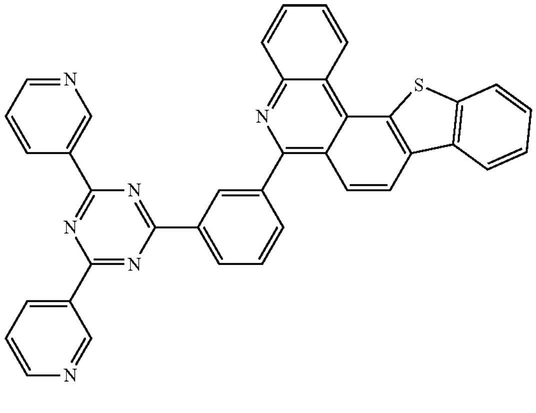

-continued
4-373
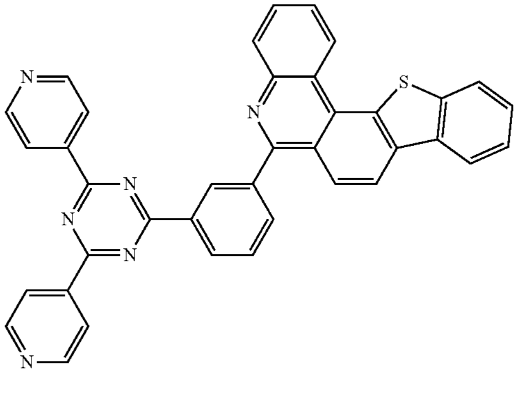
4-374
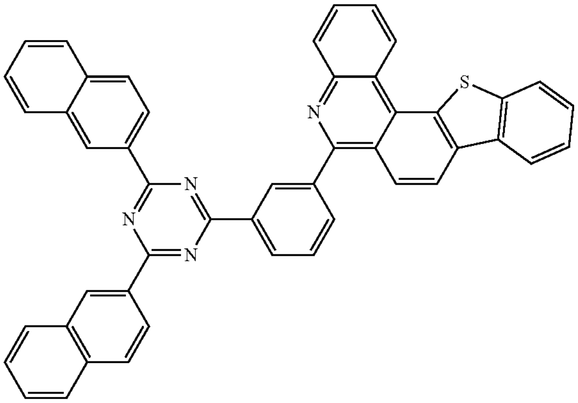
4-375
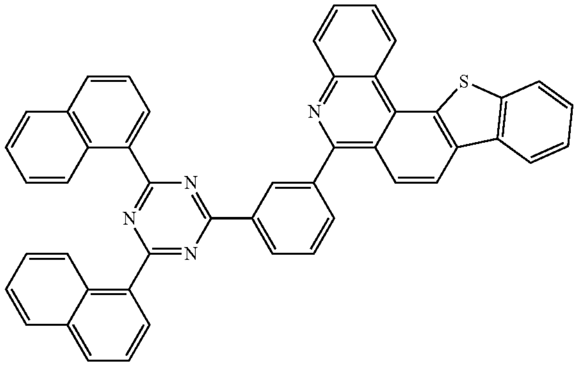
4-376
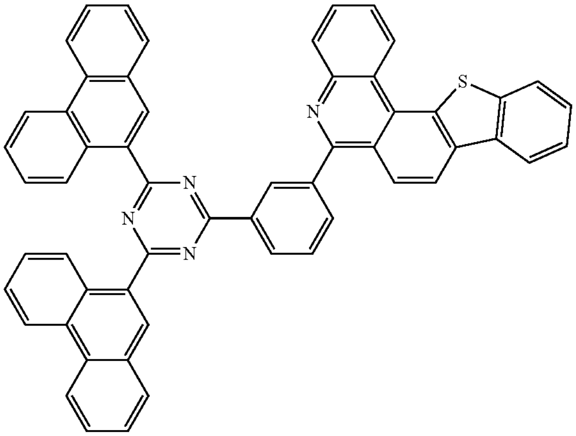
4-377
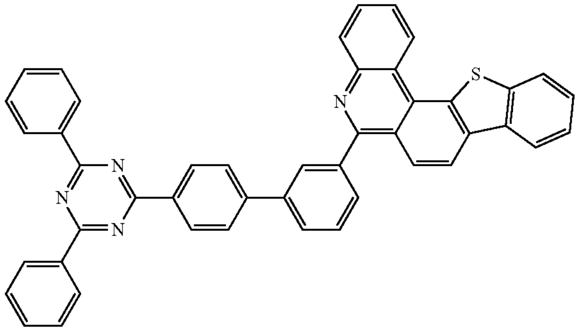
4-378
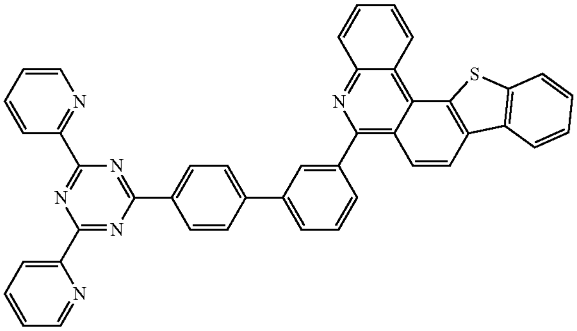
4-379
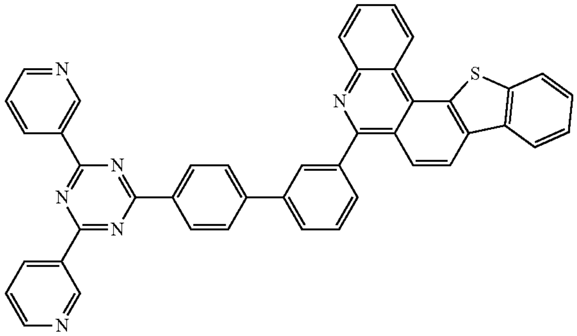
4-380
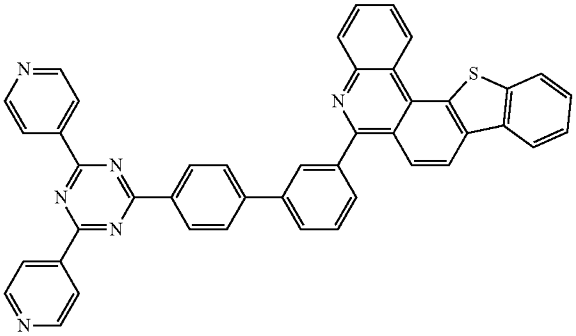

-continued
4-381
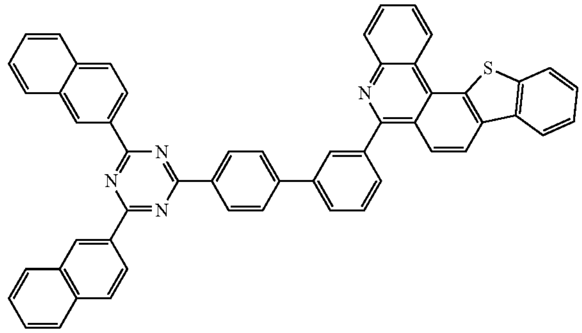
4-382
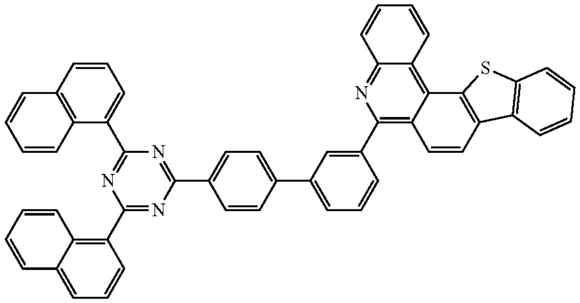
4-383
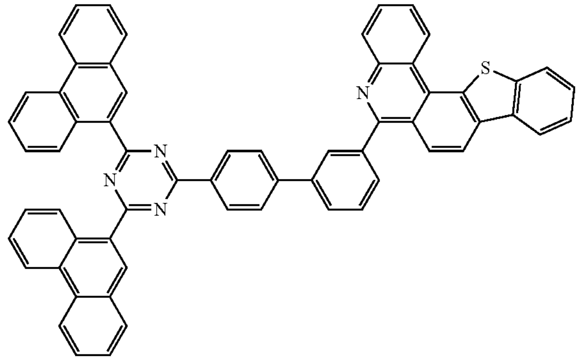
4-384
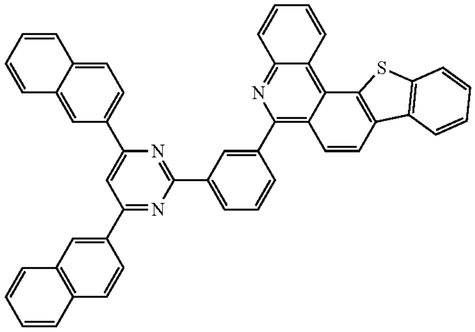
4-385
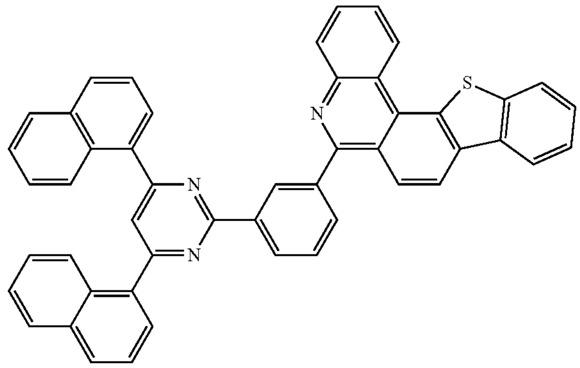
4-386
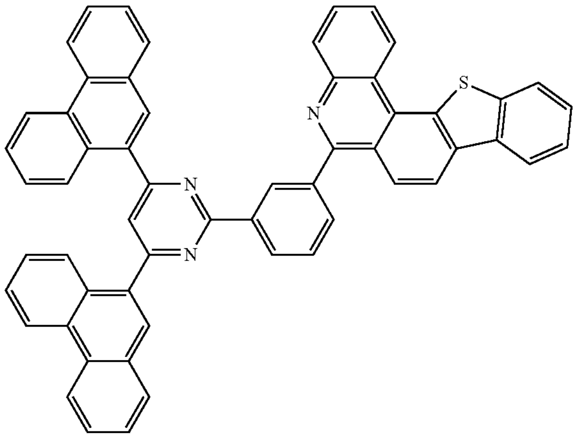

-continued
4-387
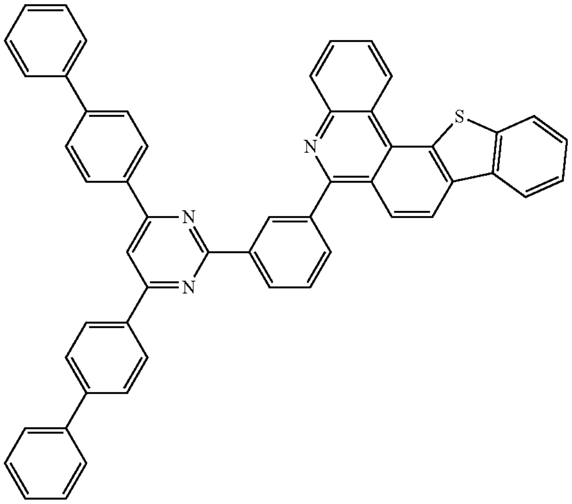
4-388
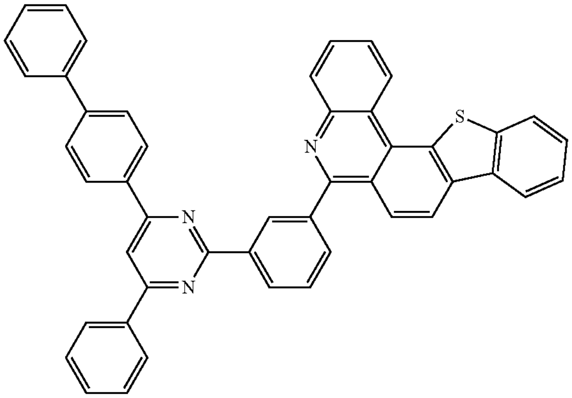
4-389
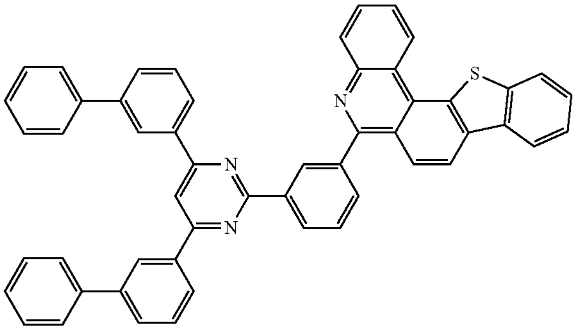
4-390
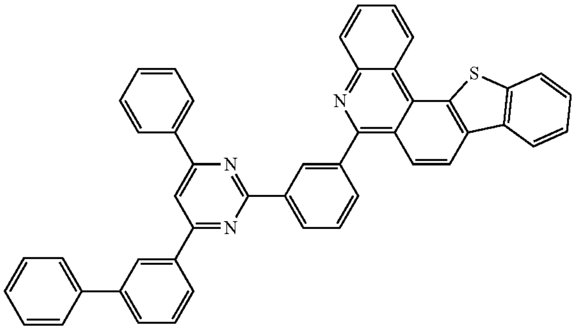
4-391
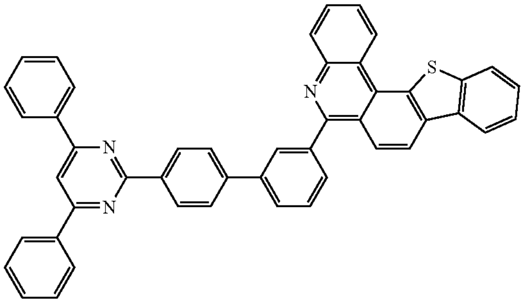
4-392
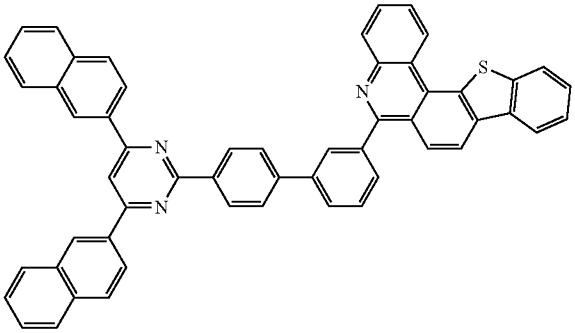
4-393
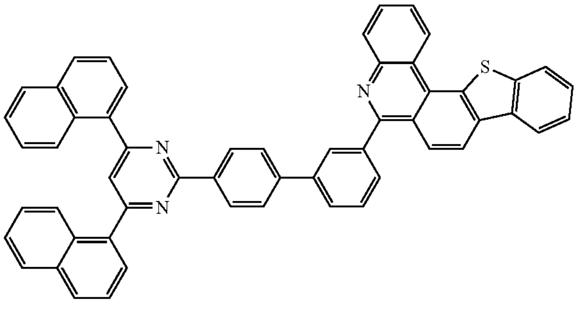
4-394
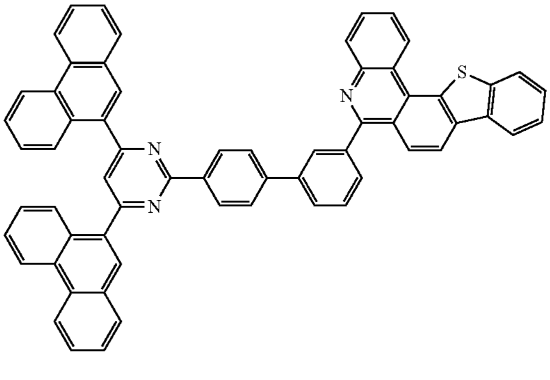

-continued
4-395
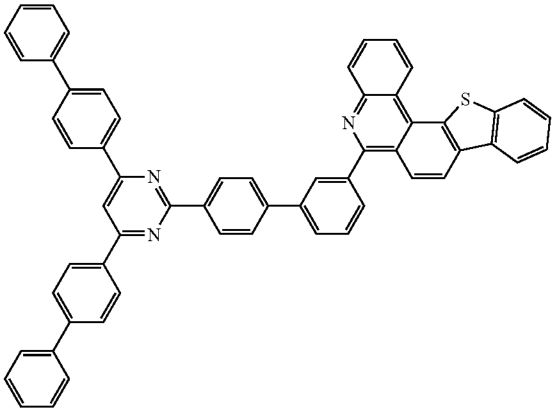
4-396
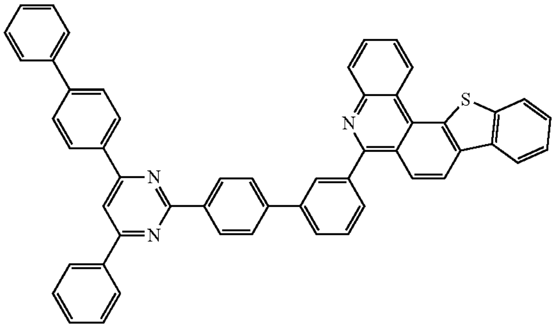
4-397
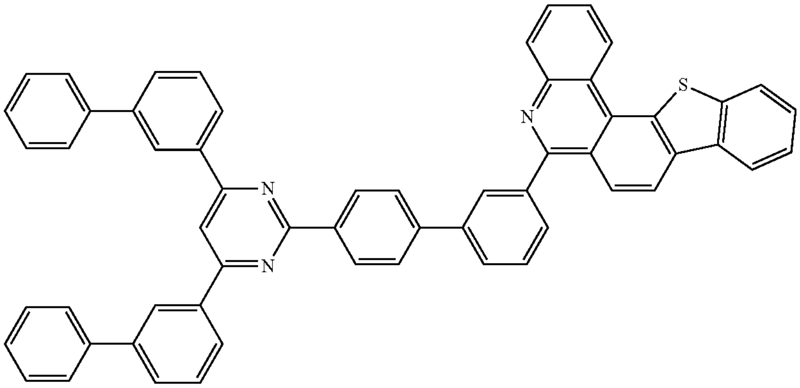
4-398
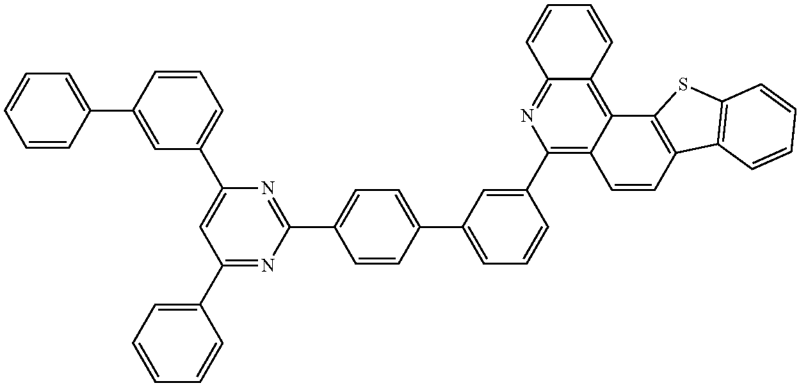
4-399
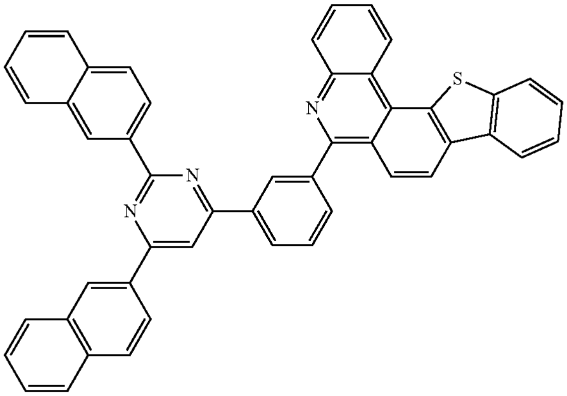
4-400
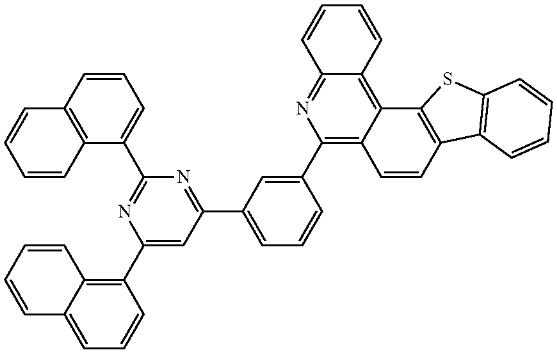

-continued
4-401
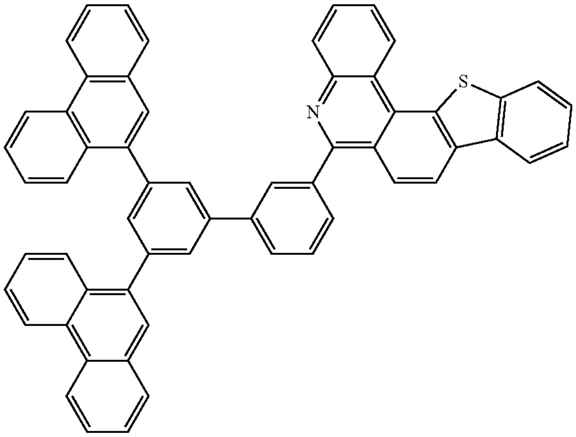
4-402
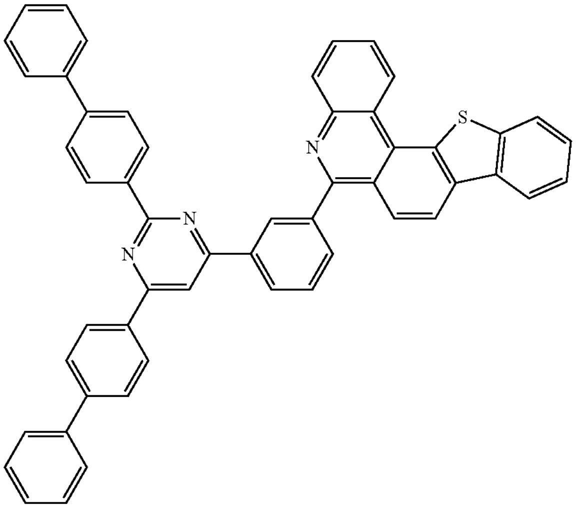
4-403
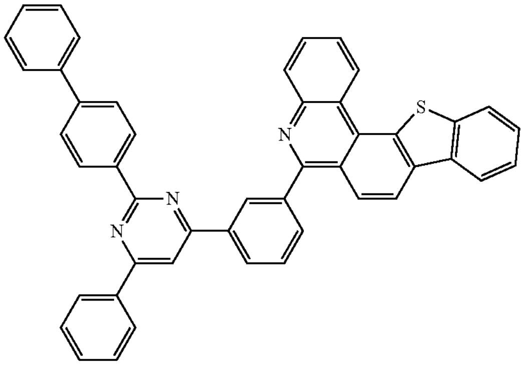
4-404
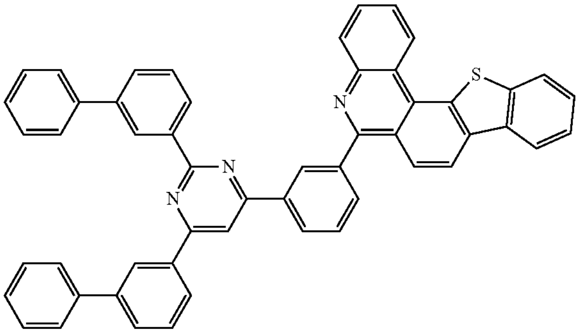
4-405
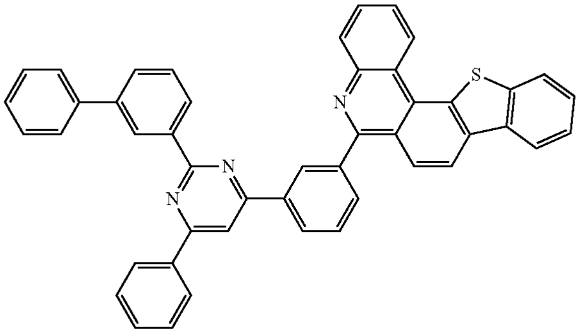
4-406
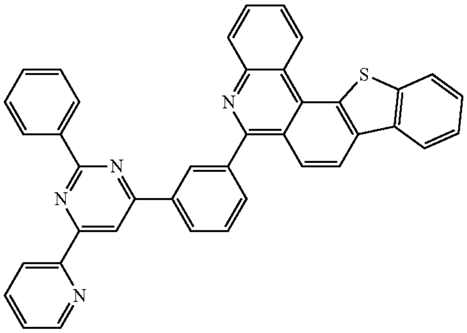

-continued
4-407
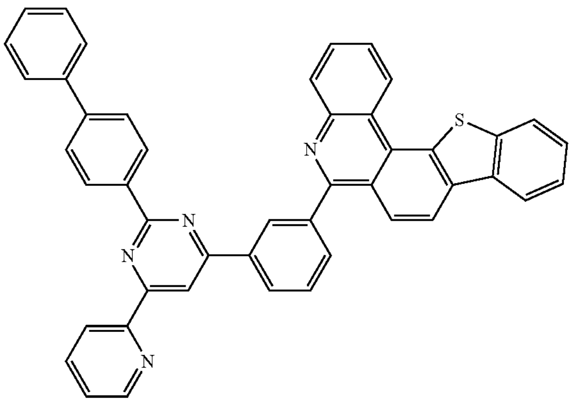
4-408
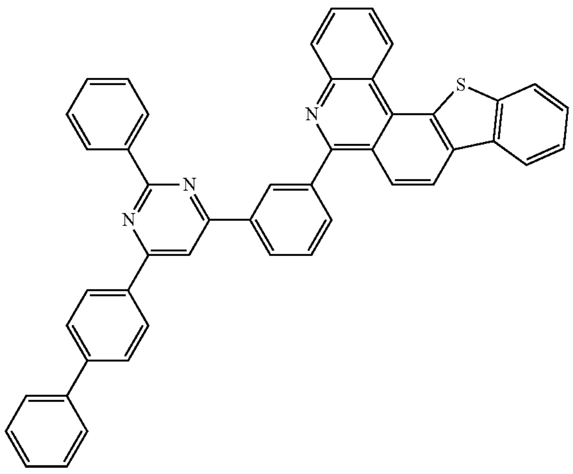
4-409
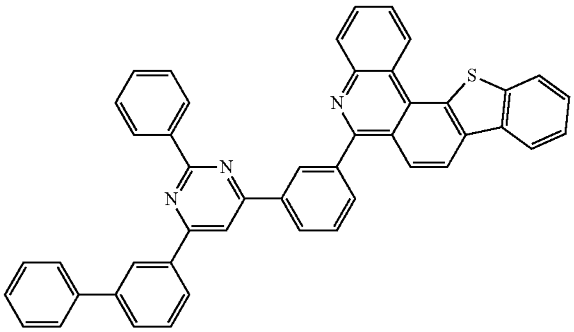
4-410
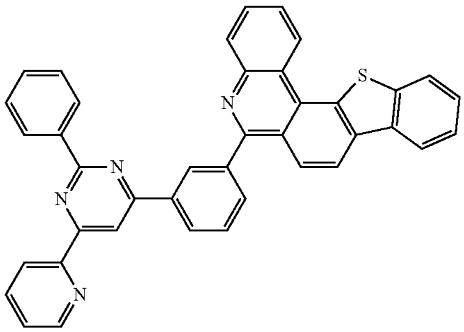
4-411
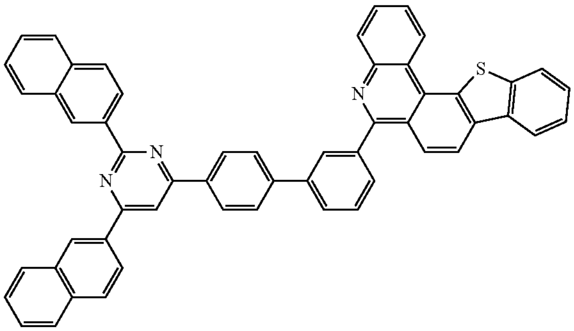
4-412
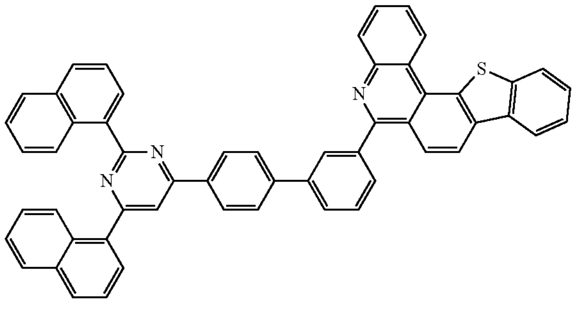
4-413
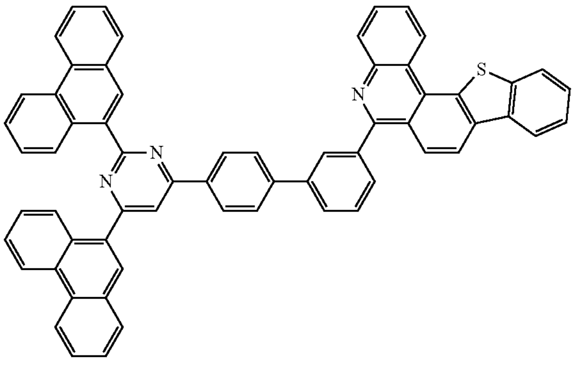
4-414
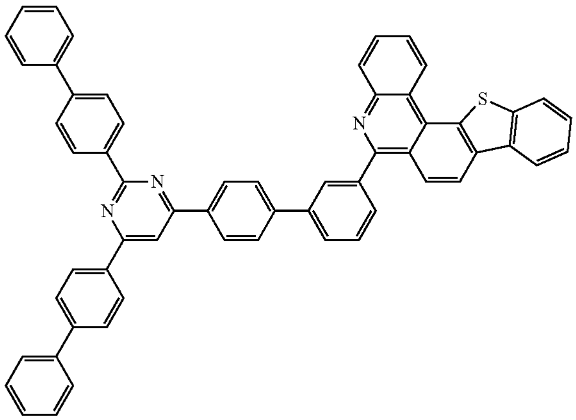

-continued
4-415
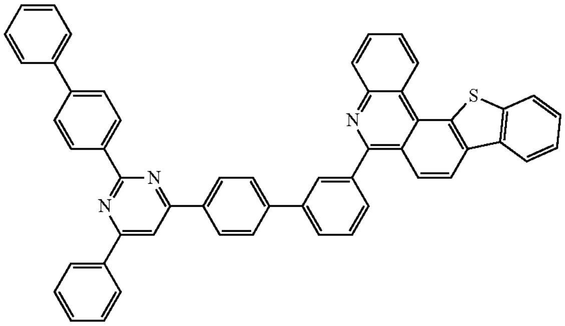
4-416
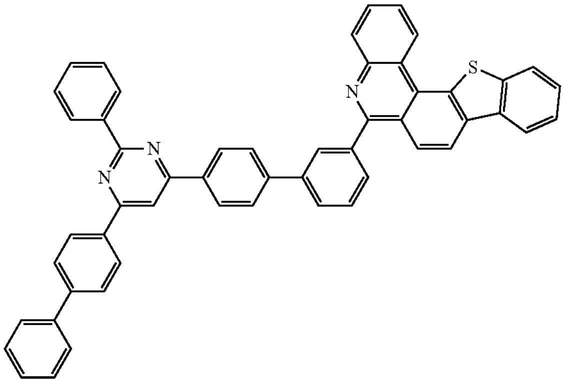
4-417
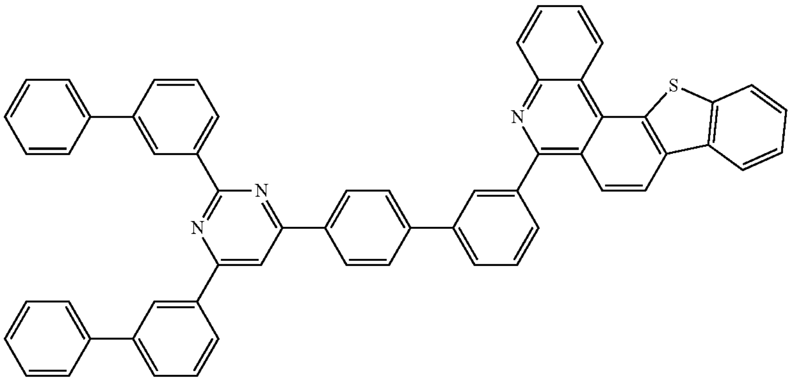
4-418
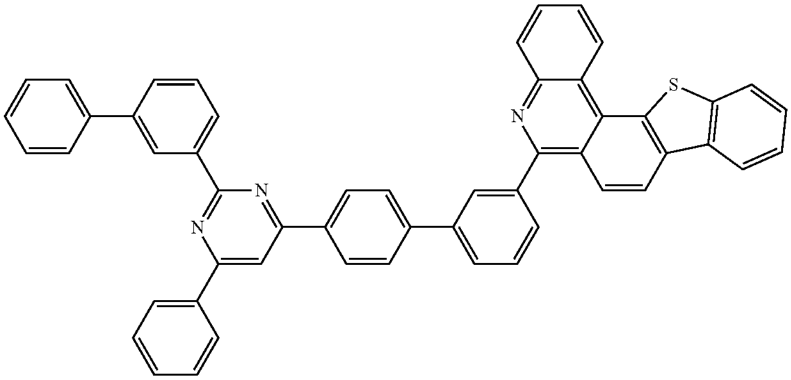
4-419
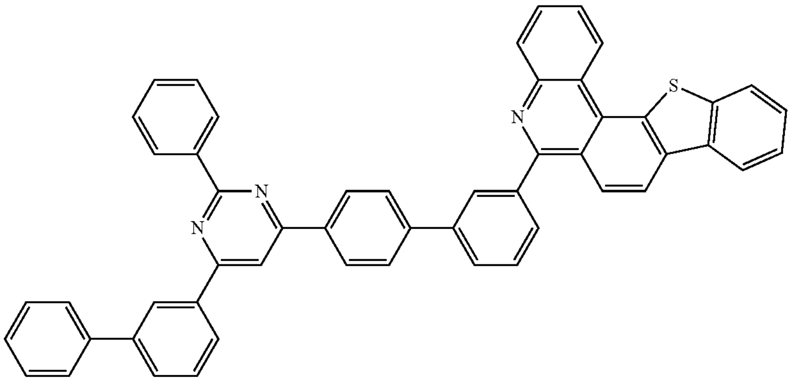

-continued
4-420
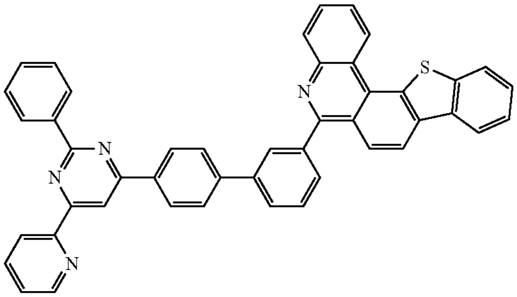
4-421
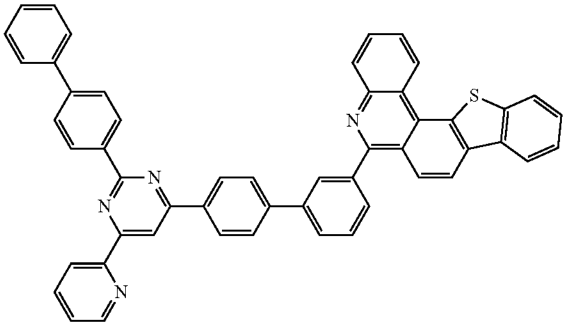
4-422
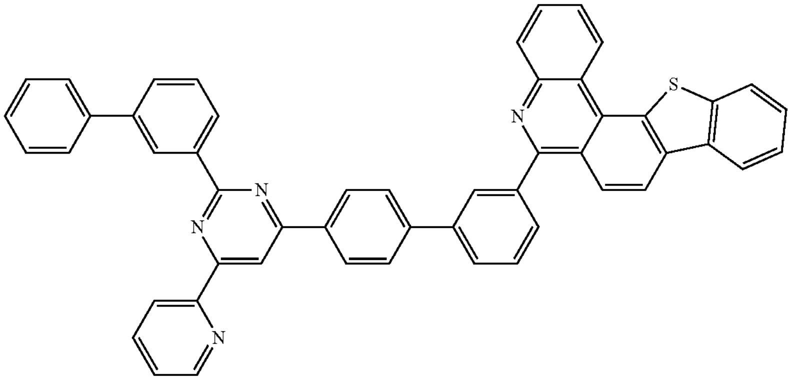
4-423
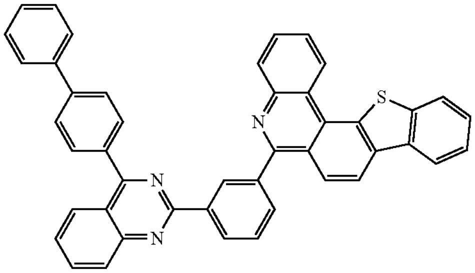
4-424
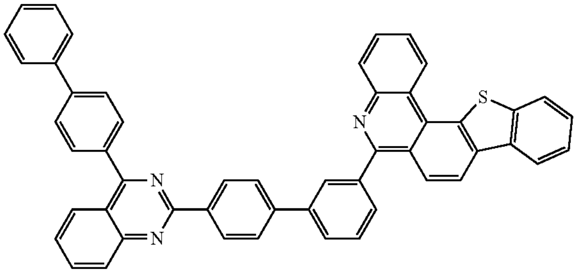
4-425
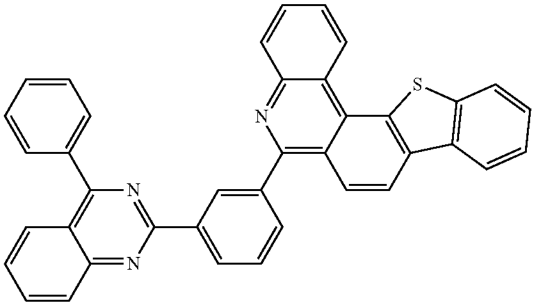
4-426
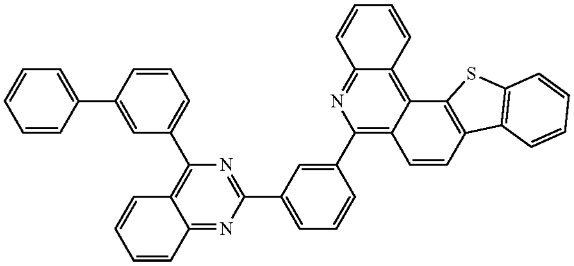

-continued
4-427
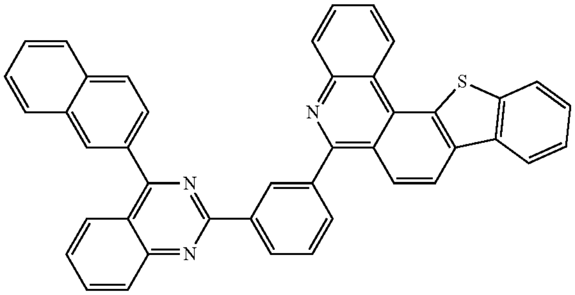
4-428
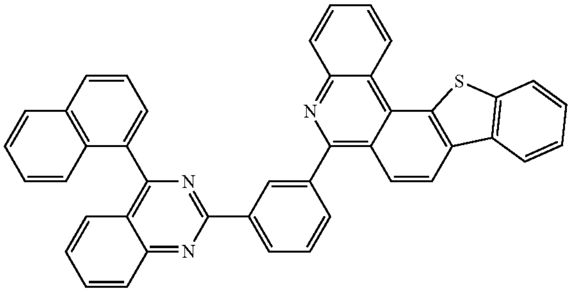
4-429
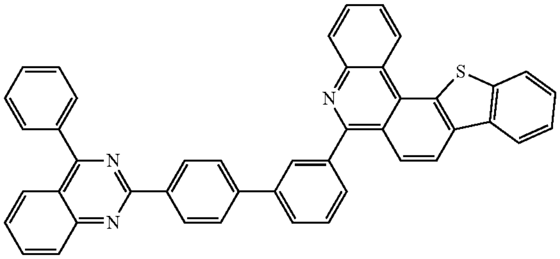
4-430
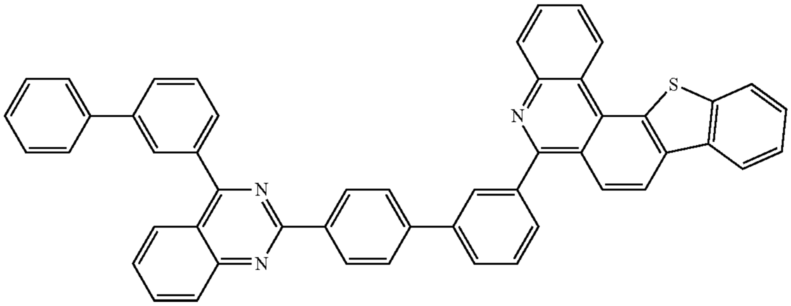
4-431
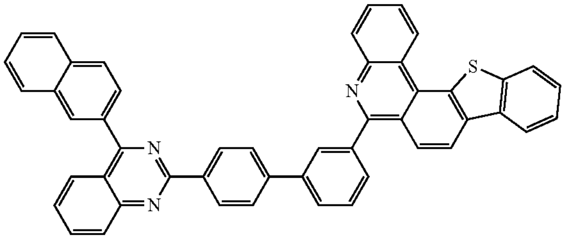
4-432
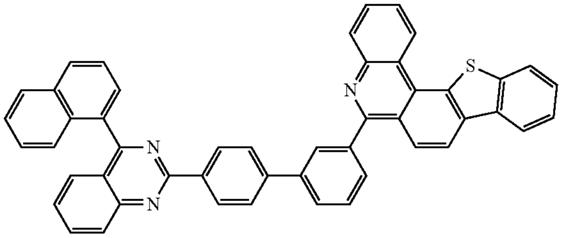
4-433
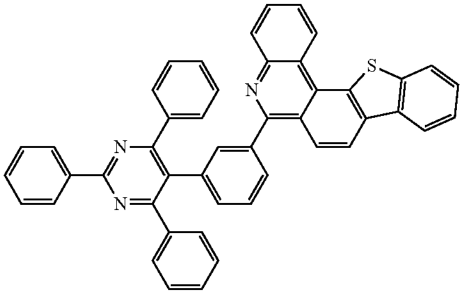

-continued
4-434
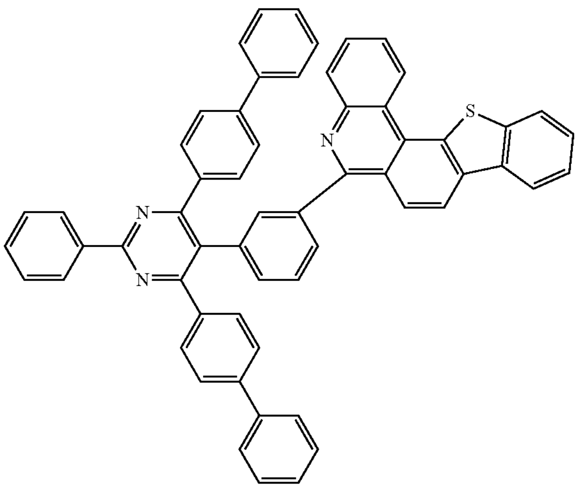
4-435
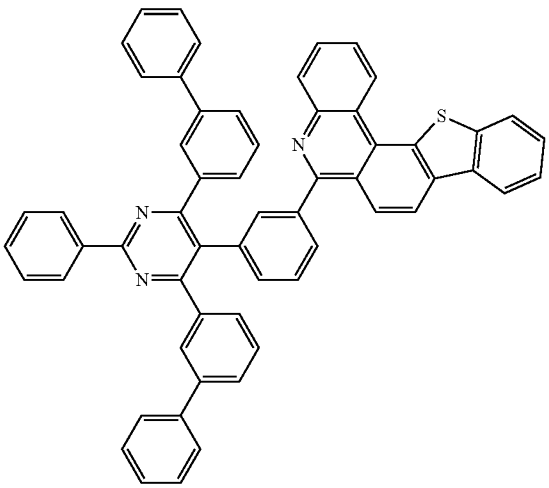
4-436
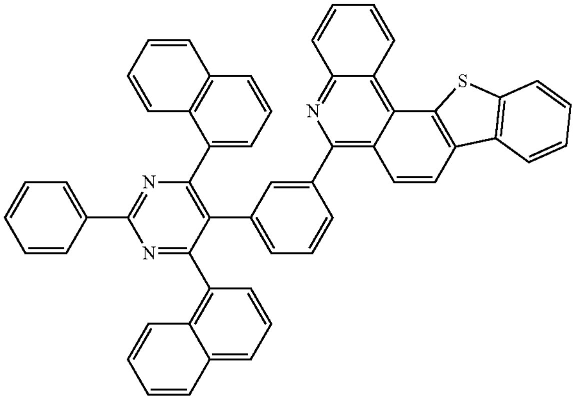
4-437
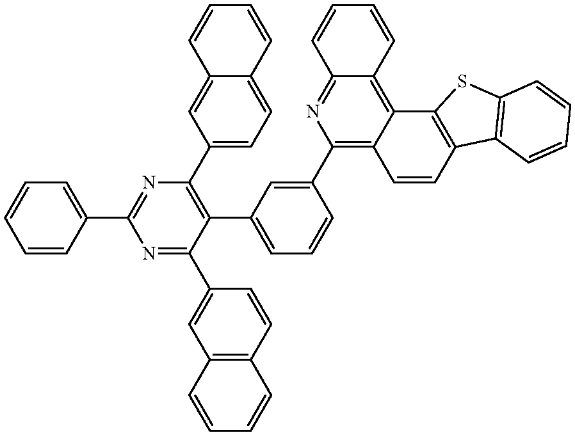
4-438
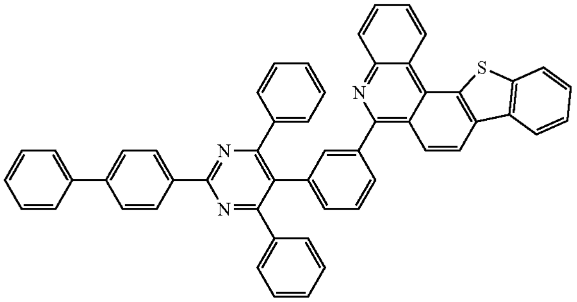
4-439
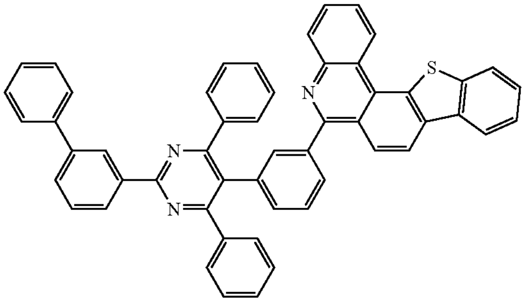
4-440
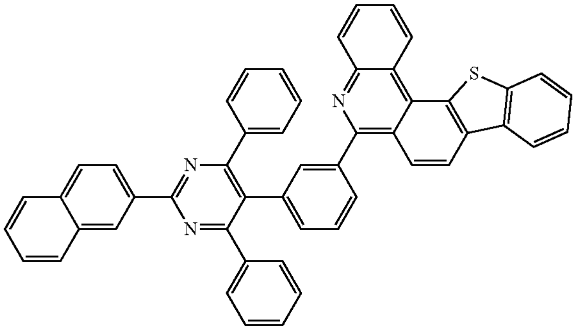
4-441
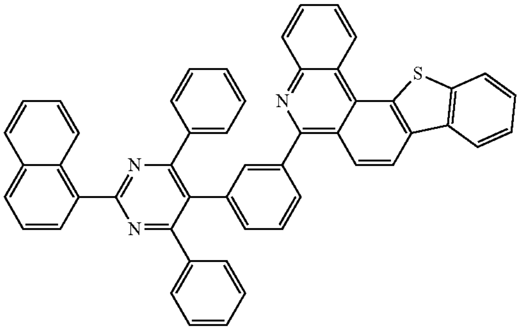

-continued
4-442
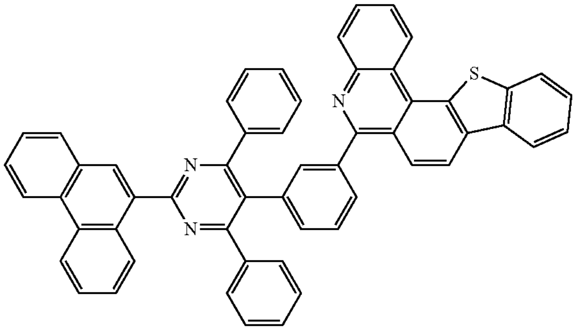
4-443
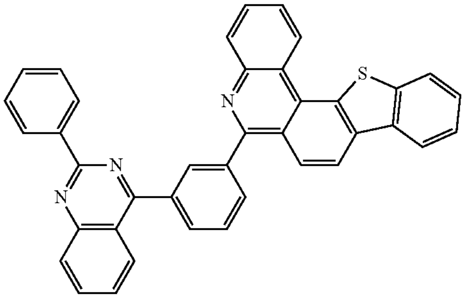
4-444
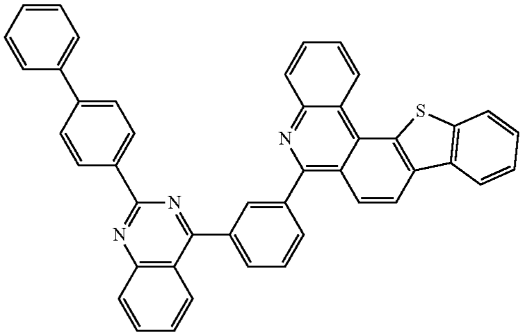
4-445
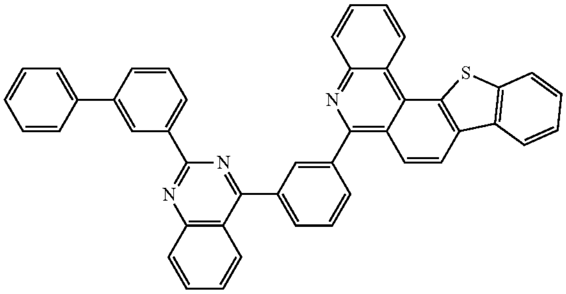
4-446
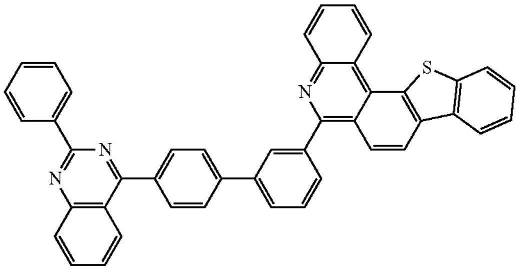
4-447
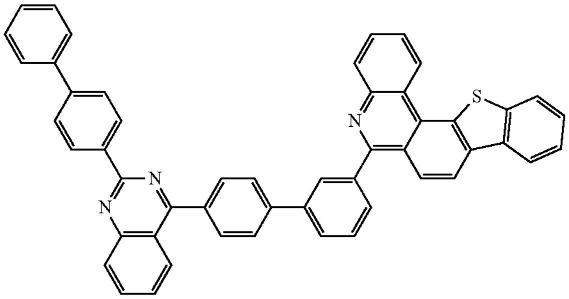
4-448
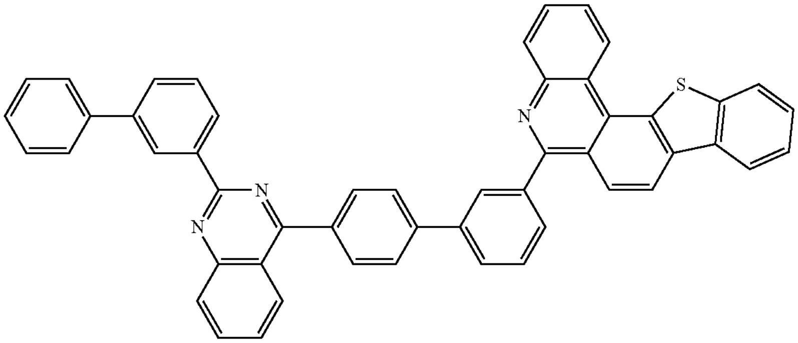
4-449
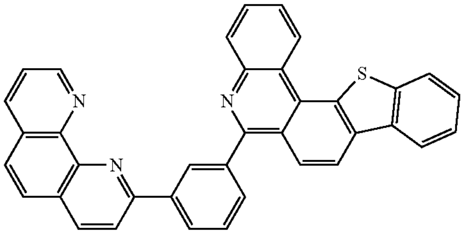
4-450
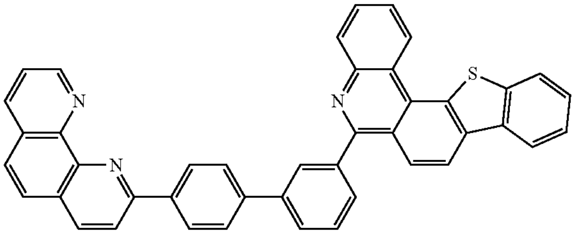

-continued
4-451
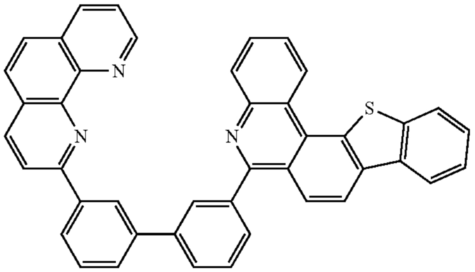
4-452
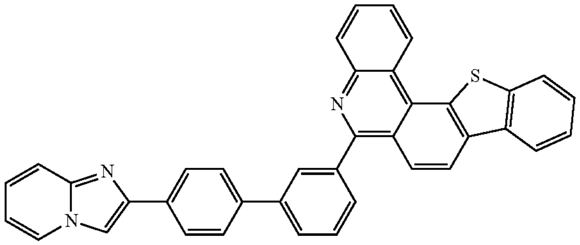
4-453
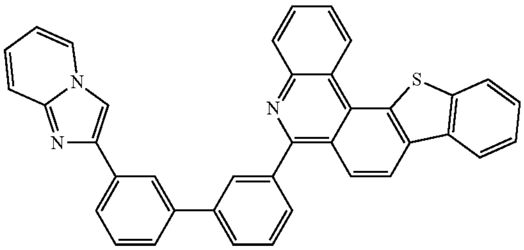
4-454
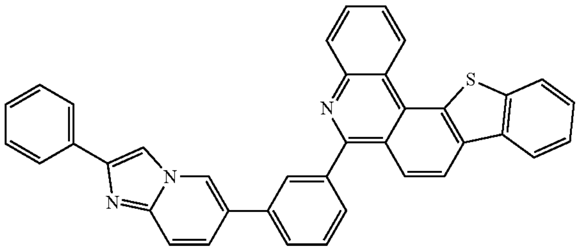
4-455
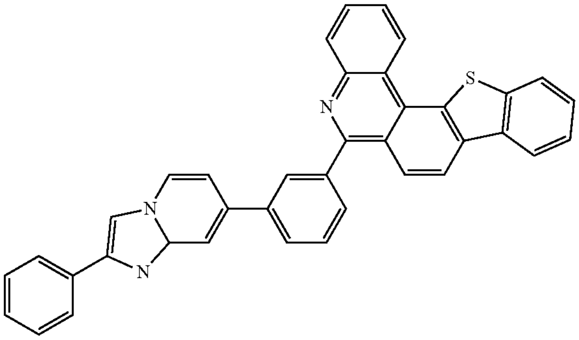
4-456
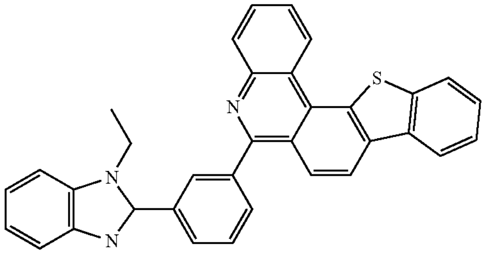
4-457
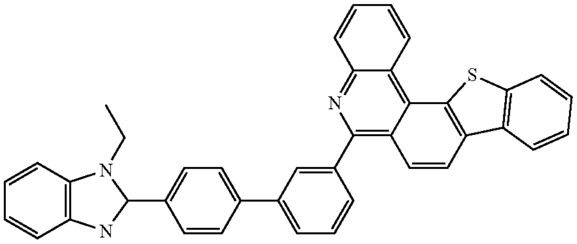
4-458
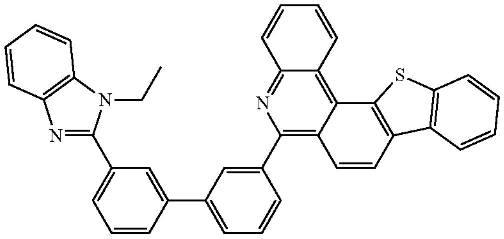
4-459
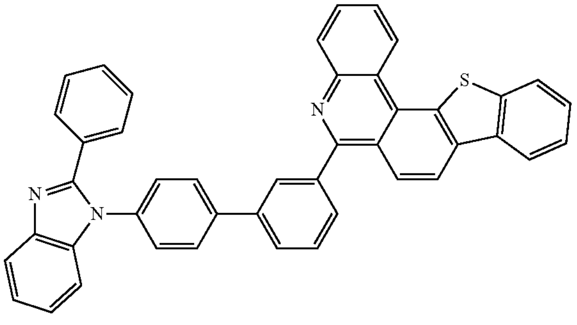
4-460
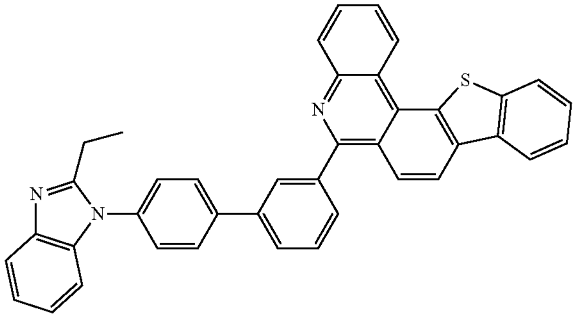

-continued
4-461
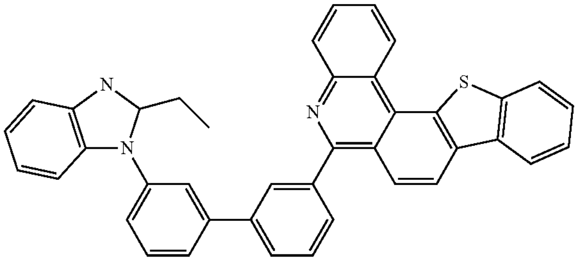
4-462
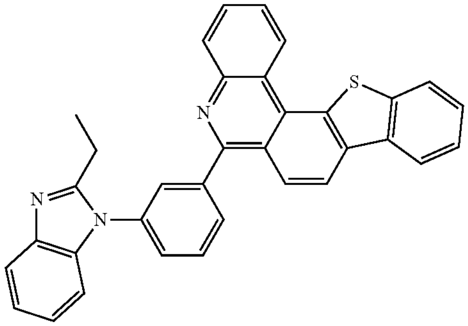
4-463
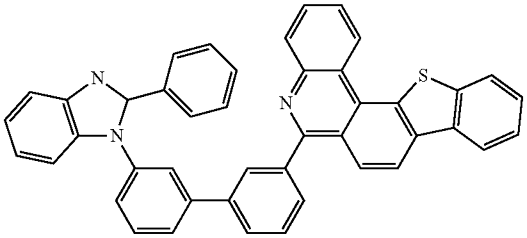
4-464
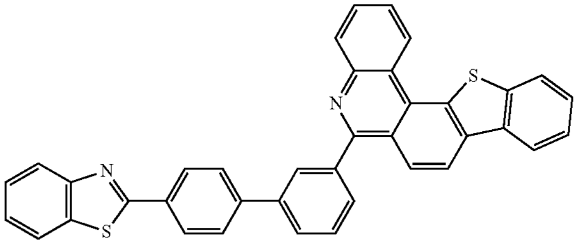
4-465
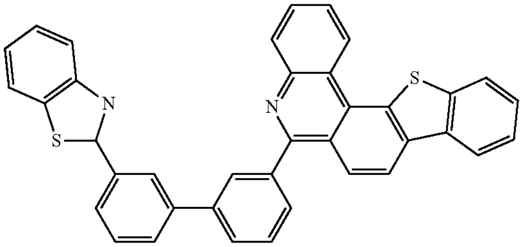
4-466
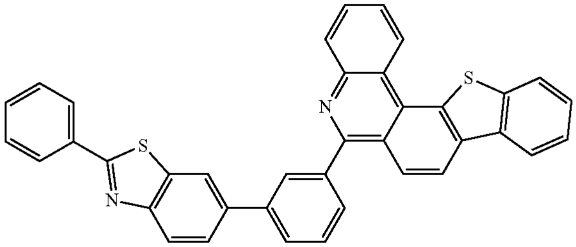
4-467
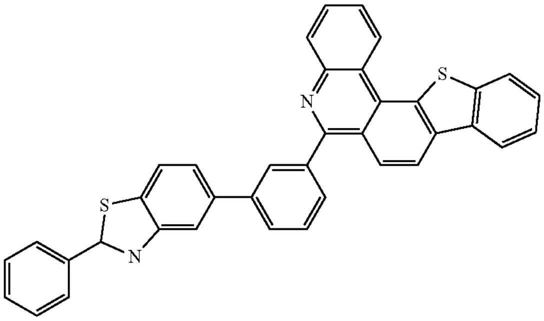
4-468
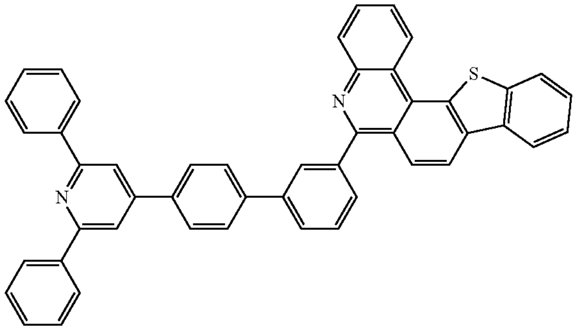

-continued
4-469
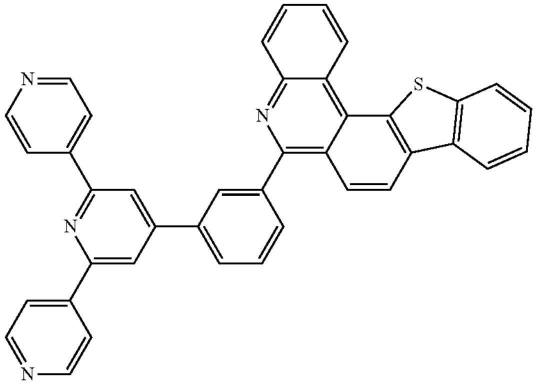
4-470
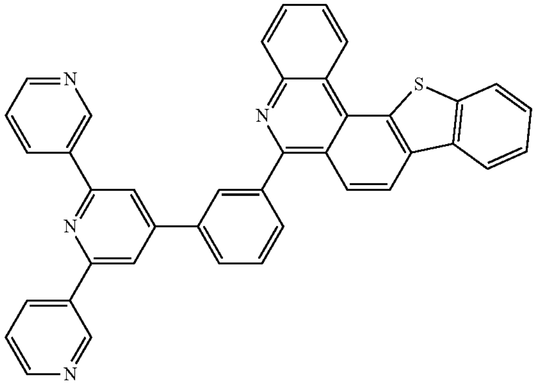
4-471
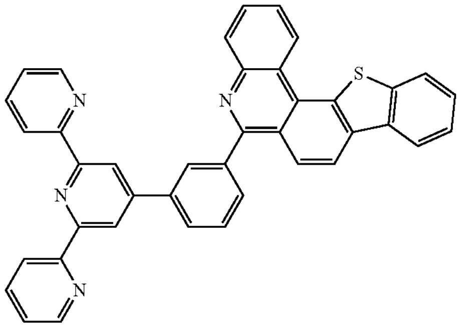
4-472
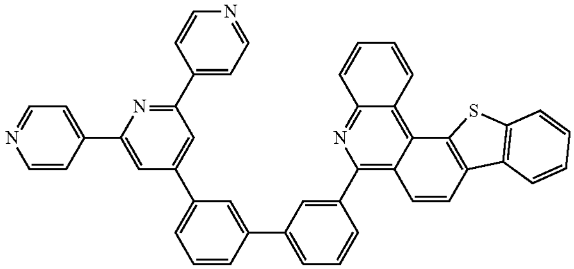
4-473
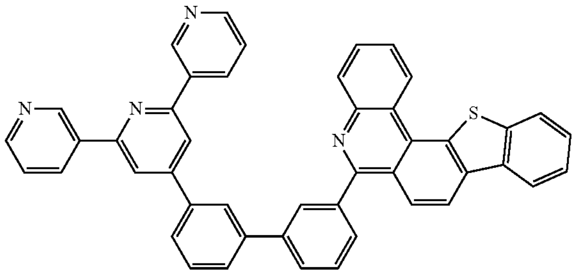
4-474
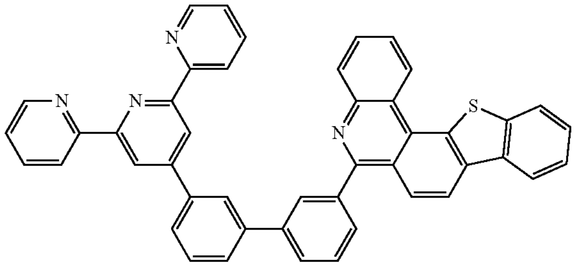
4-475
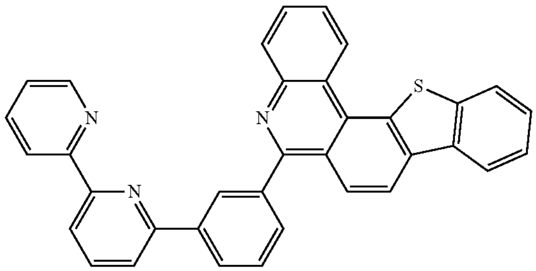
4-476
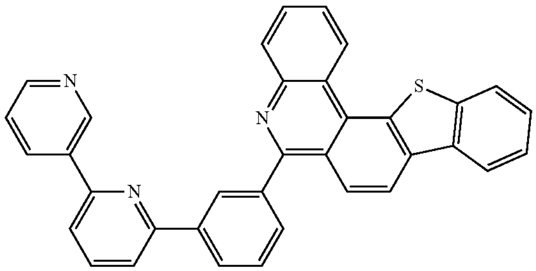
4-477
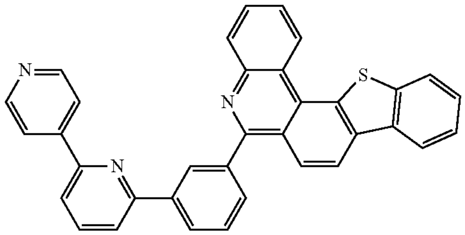
4-478
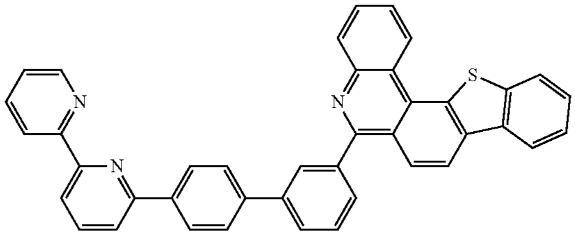

-continued
4-479
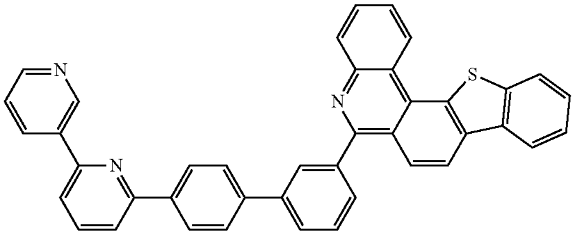
4-480
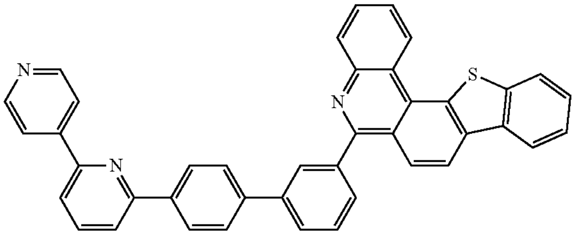
4-596
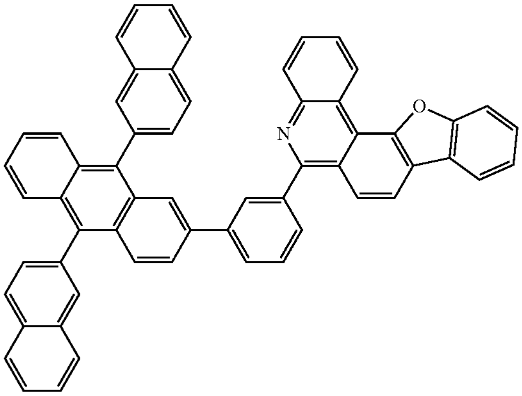
4-597
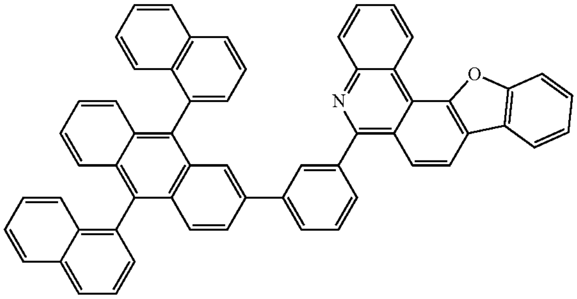
4-598
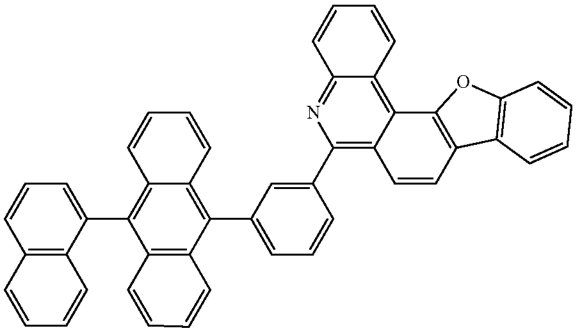
4-599
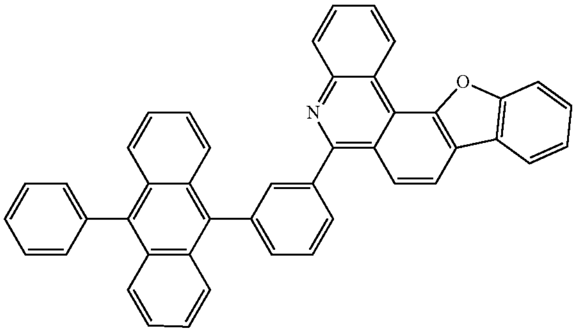
4-600
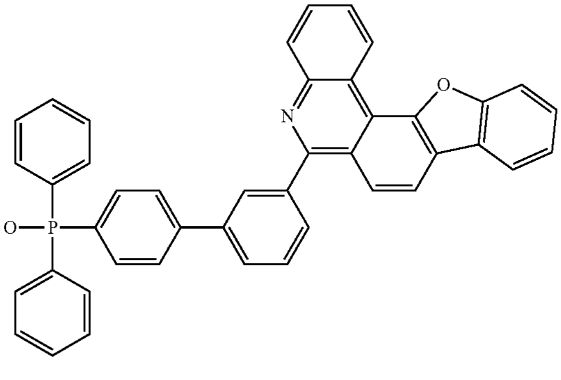
4-601
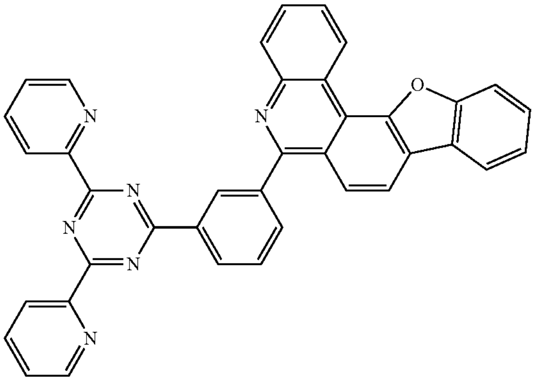

-continued
4-602
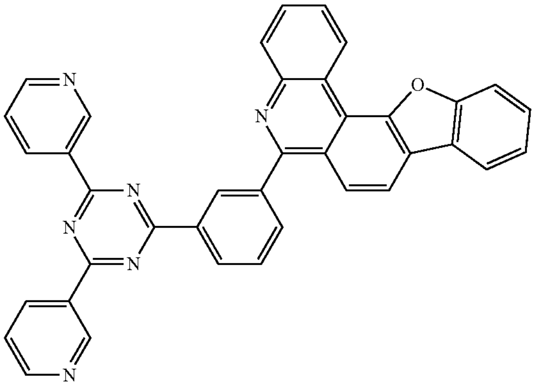
4-603
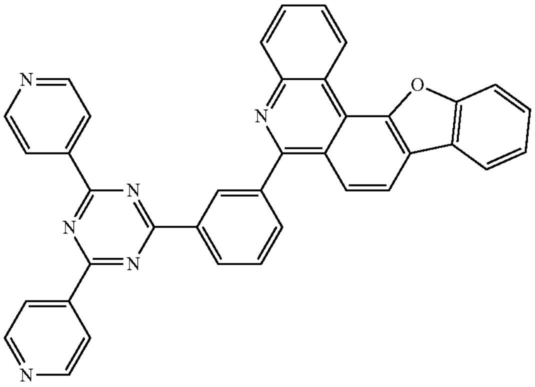
4-604
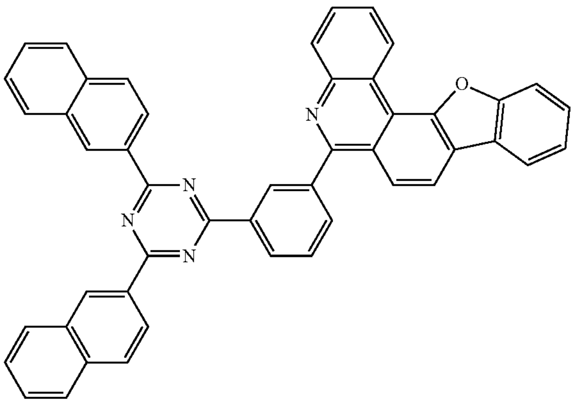
4-605
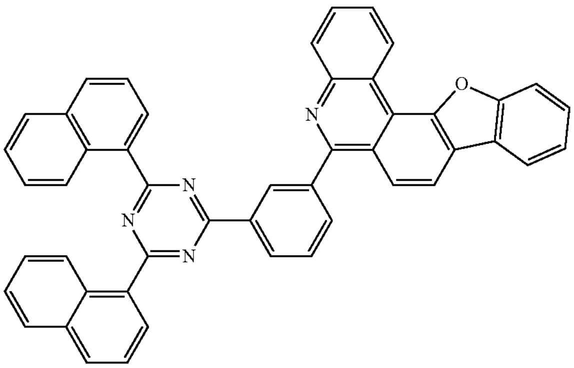
4-606
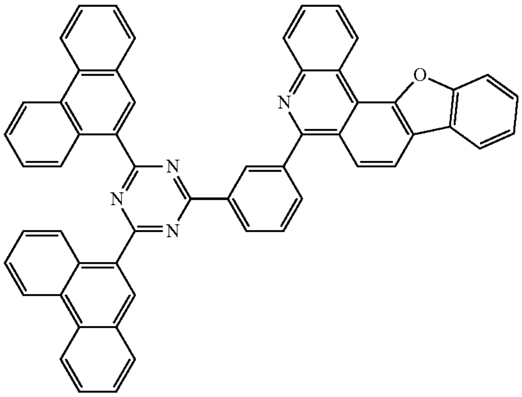
4-607
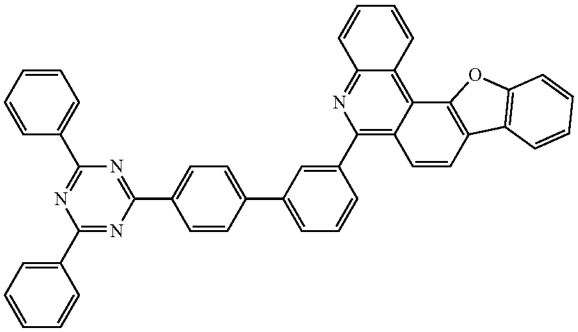
4-608
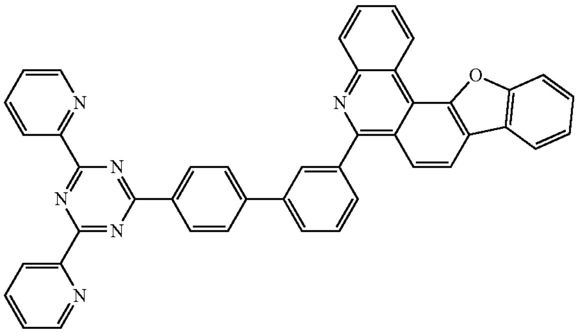
4-609
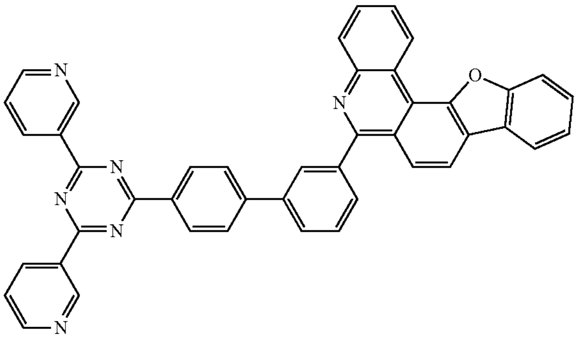

-continued
4-610
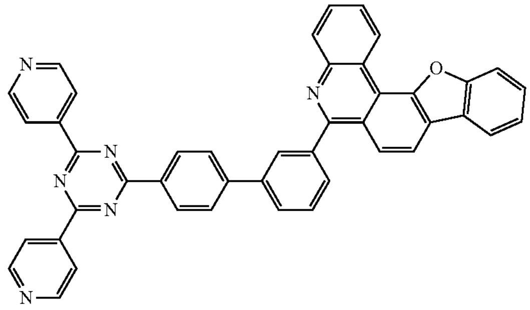
4-611
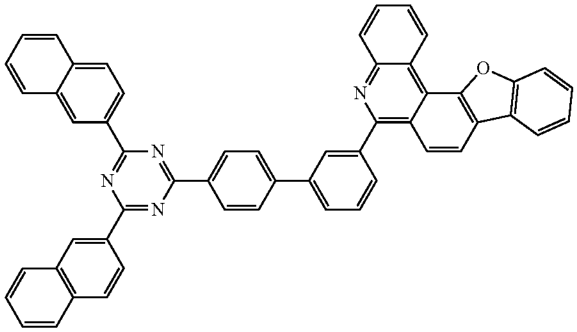
4-612
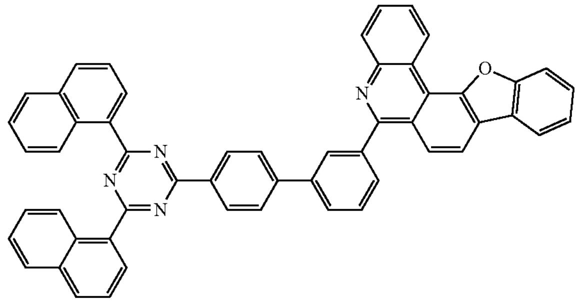
4-613
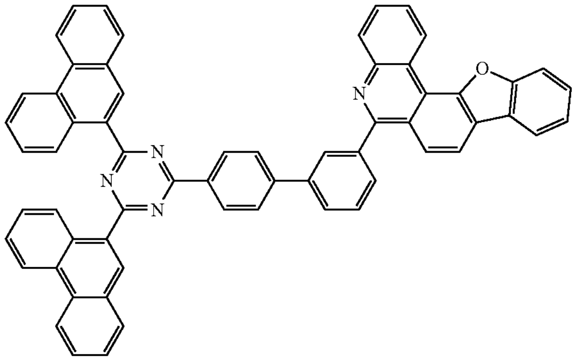
4-614
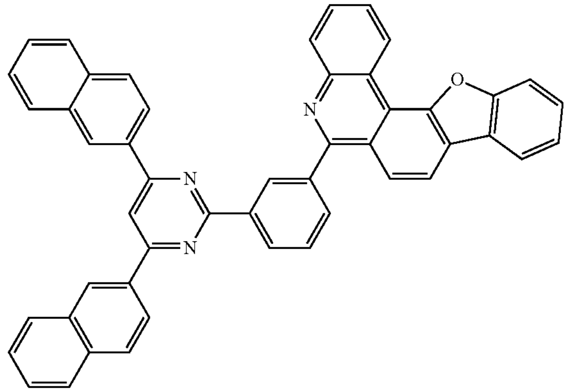
4-615
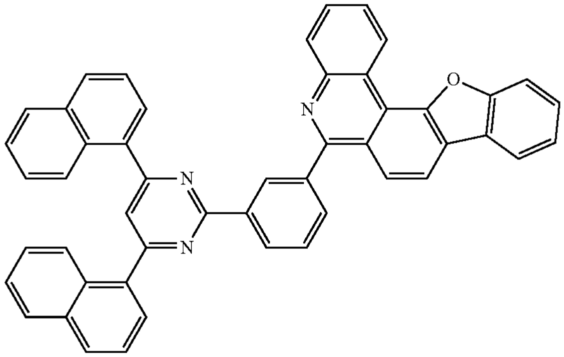

-continued
4-616
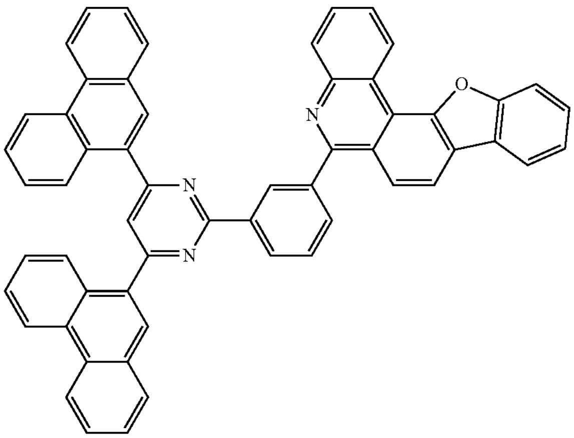
4-617
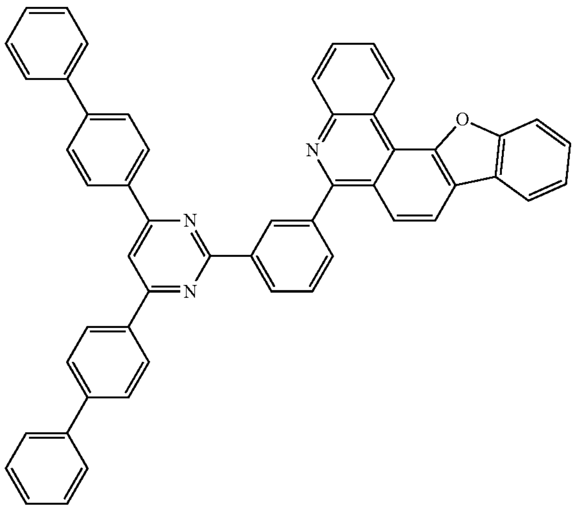
4-618
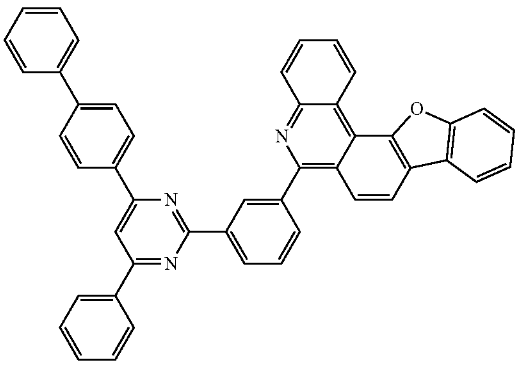
4-619
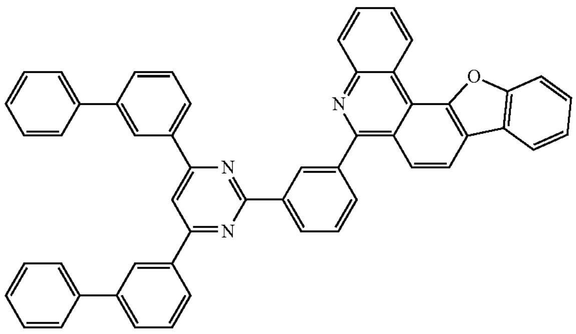
4-620
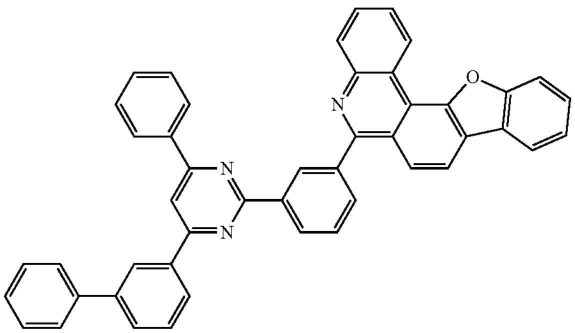
4-621
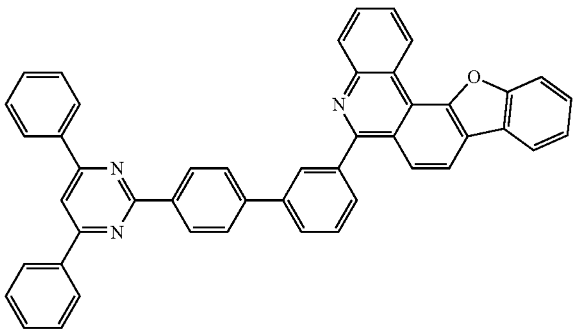
4-622
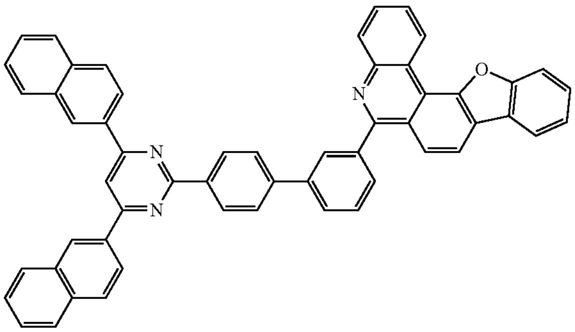
4-623
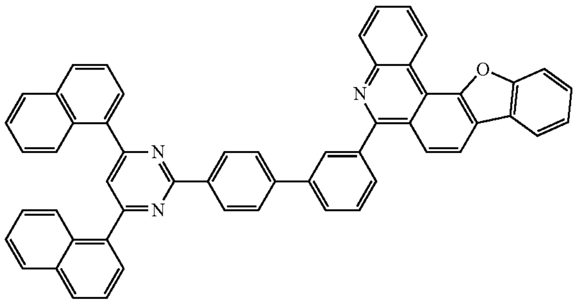

-continued
4-624
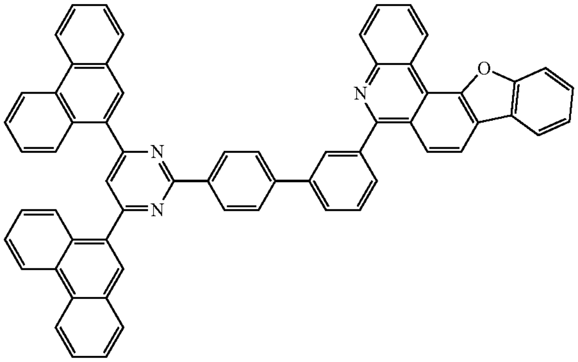
4-625
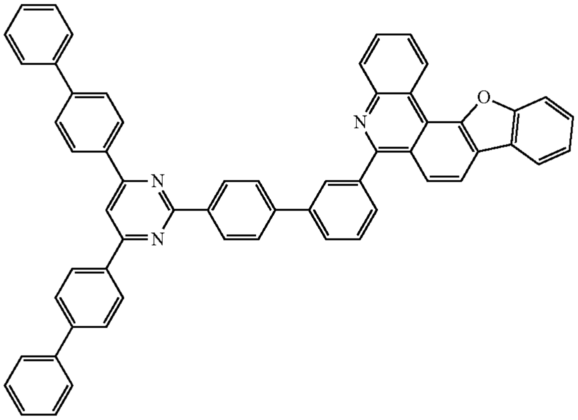
4-626
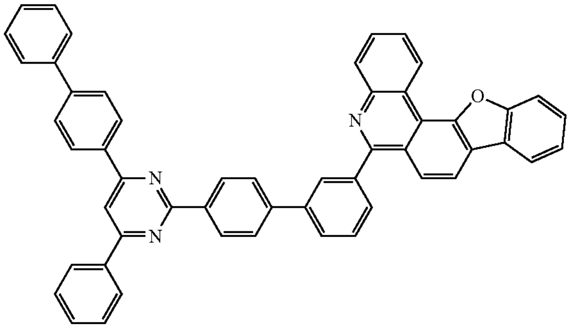
4-627
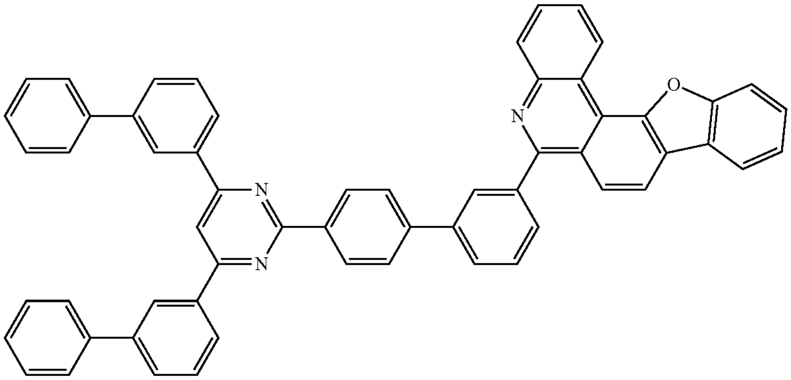
4-628
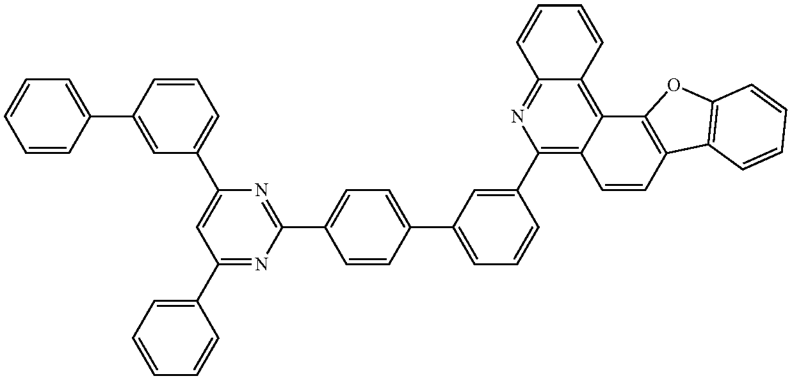

-continued
4-629
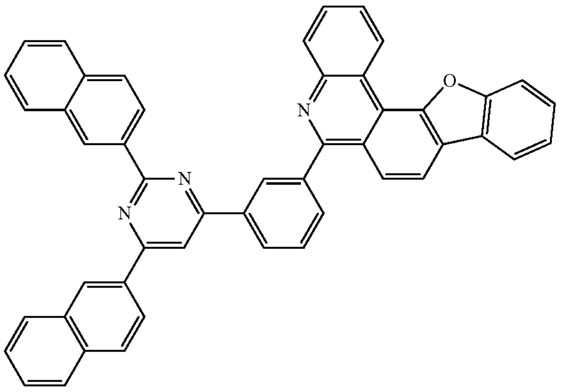
4-630
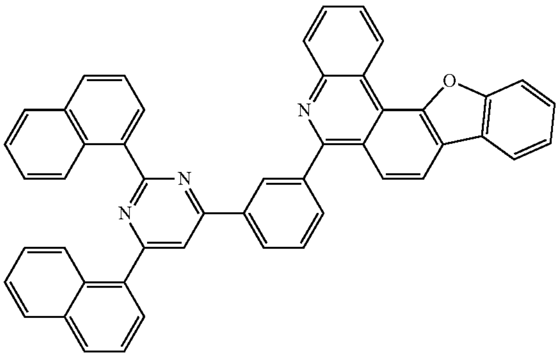
4-631
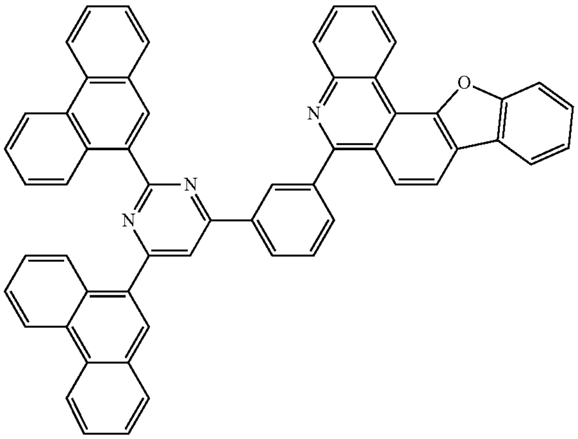
4-632
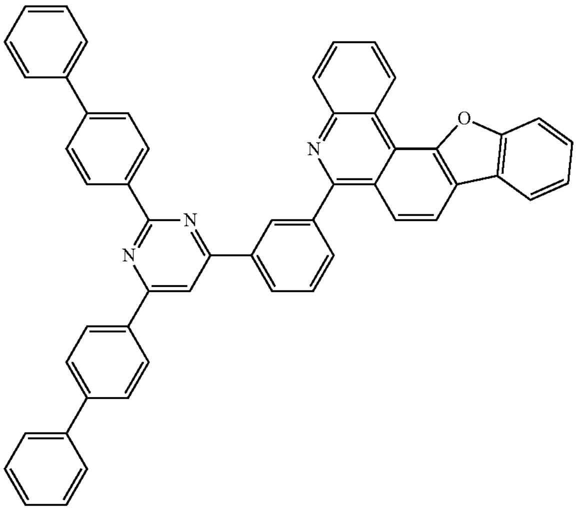
4-633
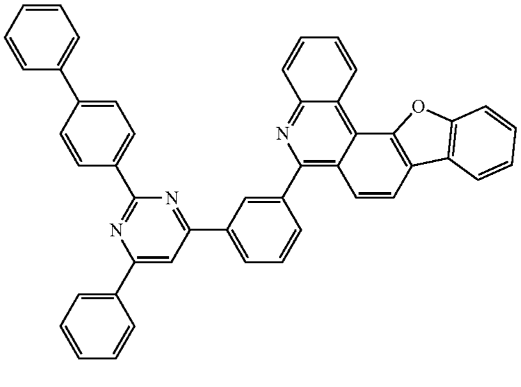
4-634
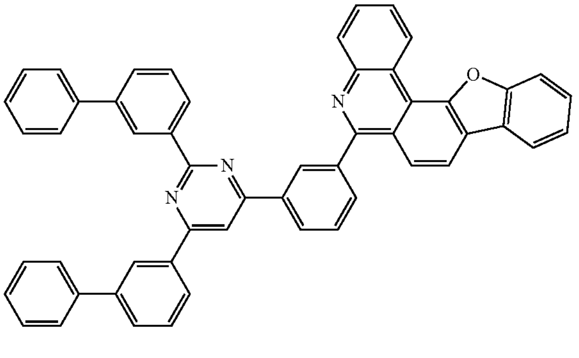

-continued
4-635
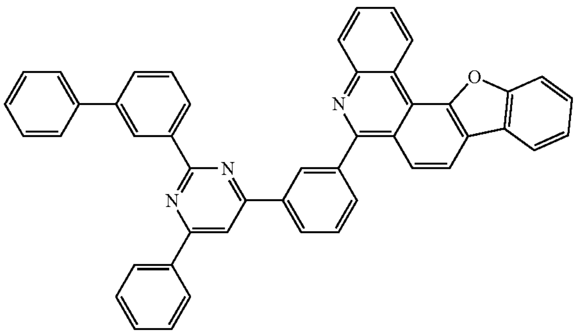
4-636
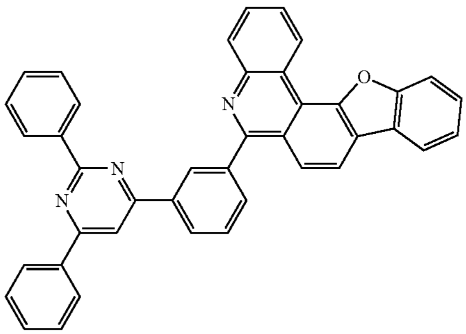
4-637
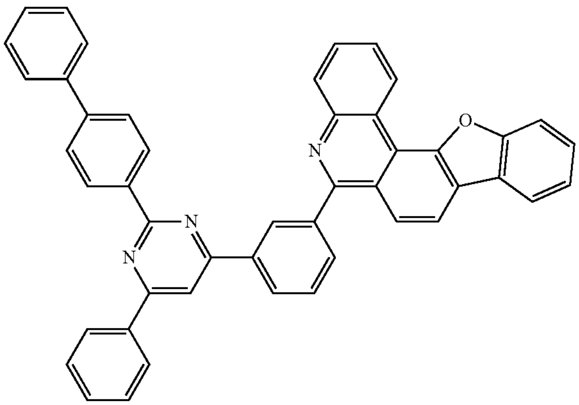
4-638
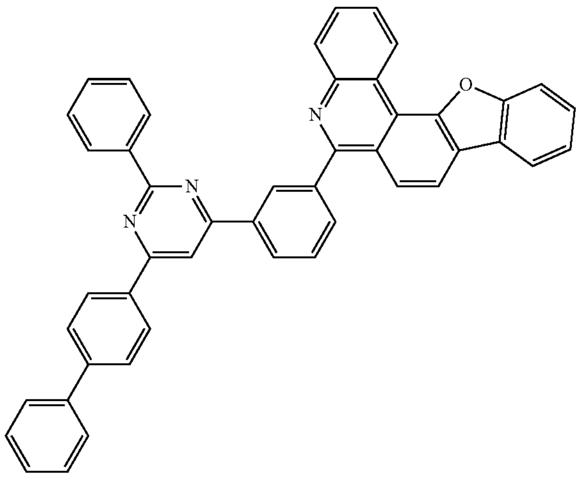
4-639
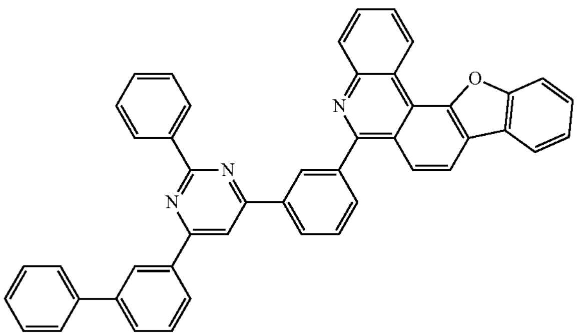
4-640
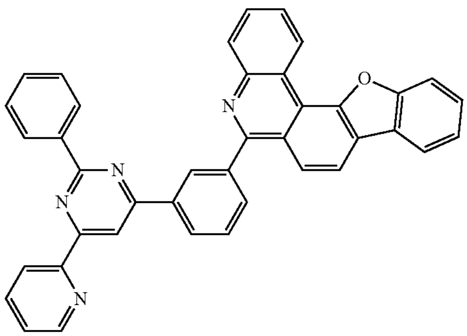
4-641
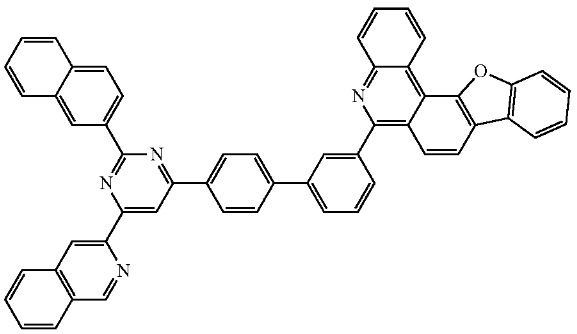
4-642
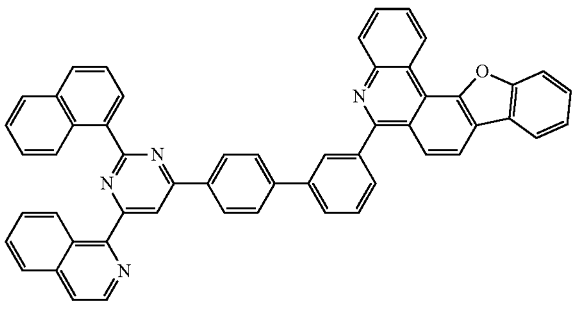

-continued
4-643
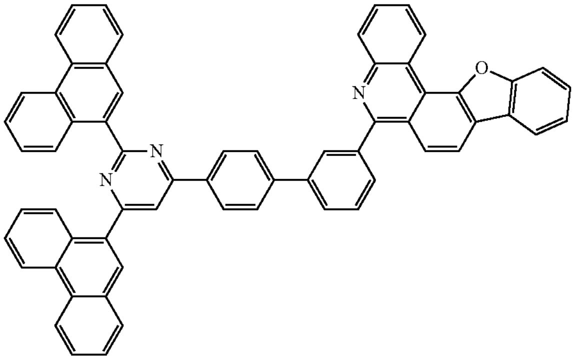
4-644
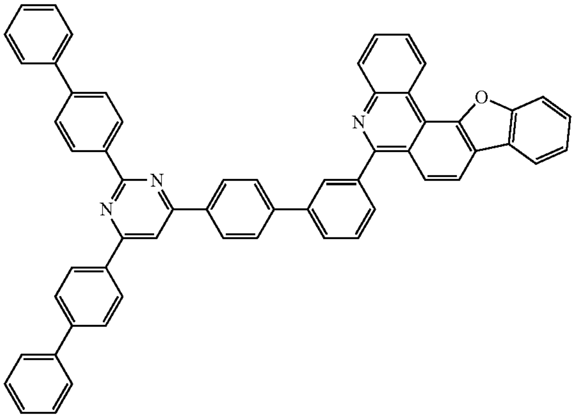
4-645
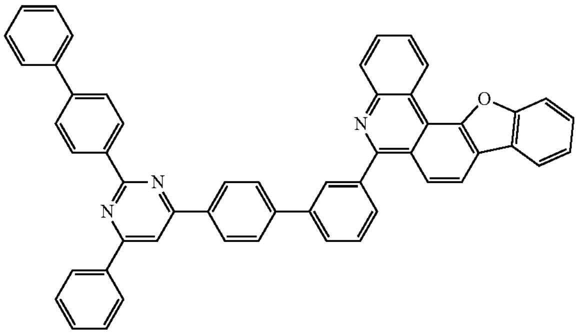
4-646
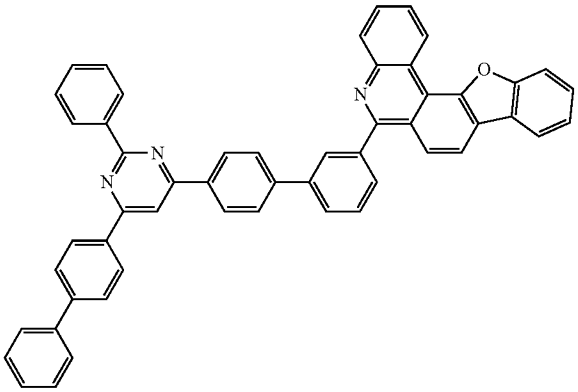
4-647
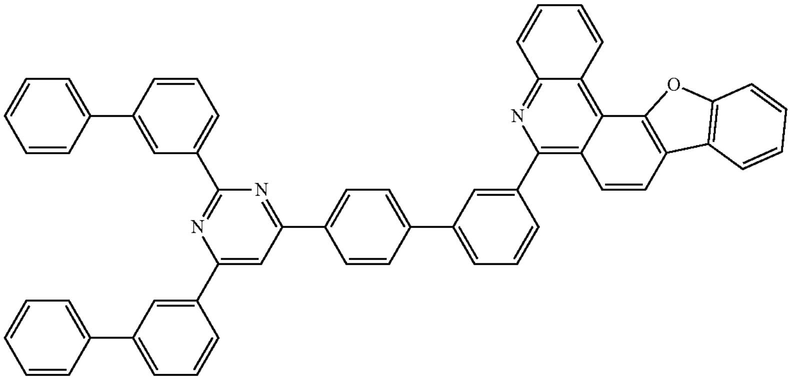
4-648
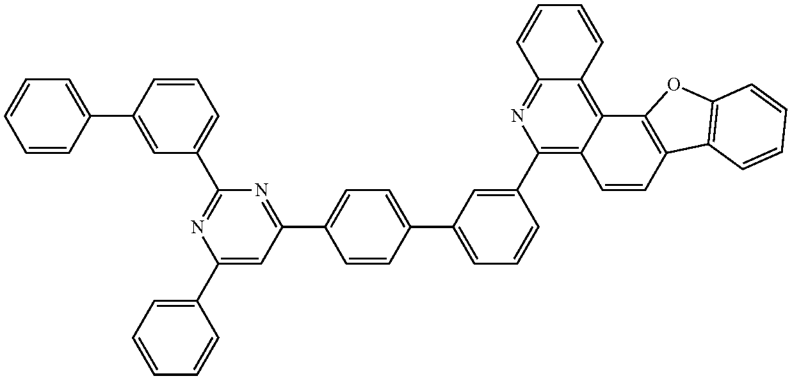

-continued
4-649
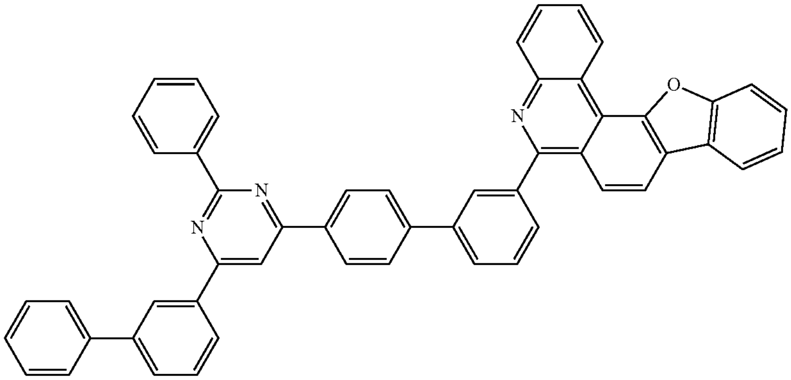
4-650
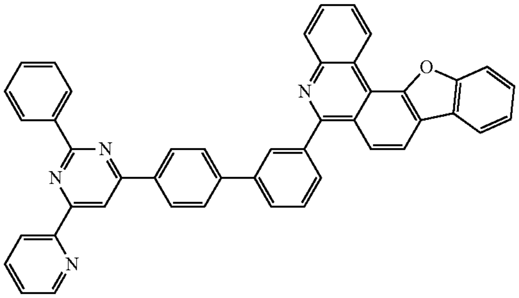
4-651
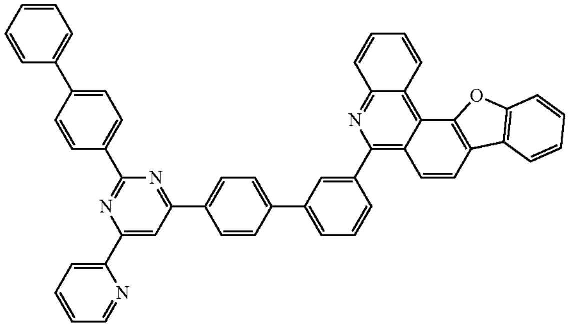
4-652
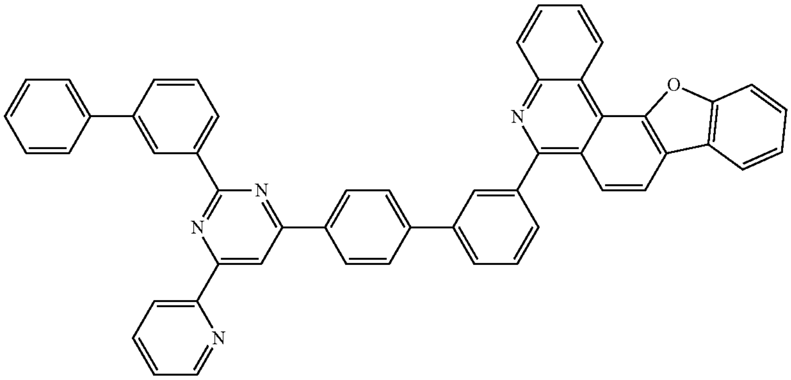
4-653
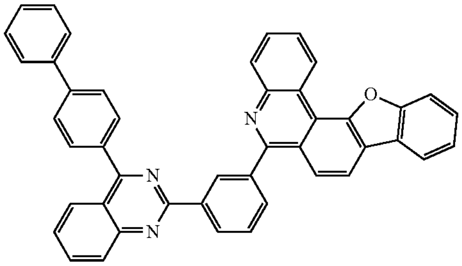
4-654
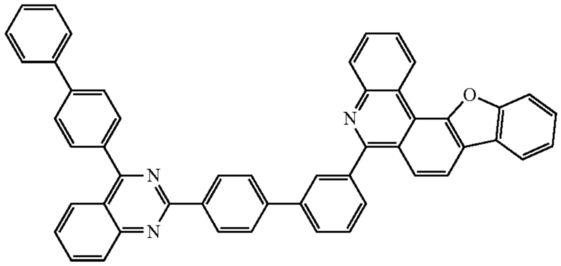

-continued
4-655
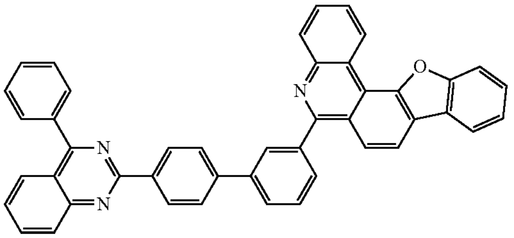
4-656
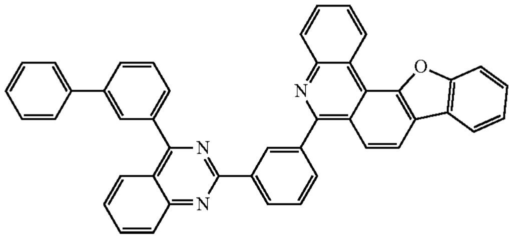
4-657
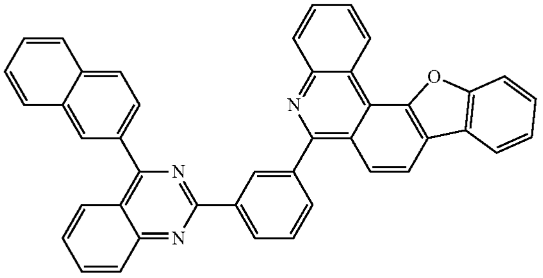
4-658
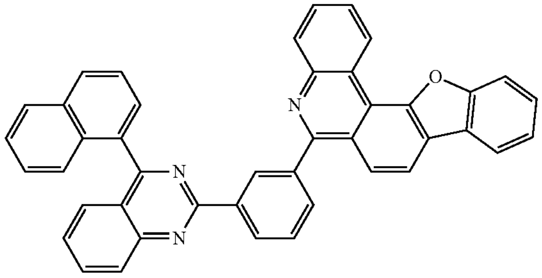
4-659
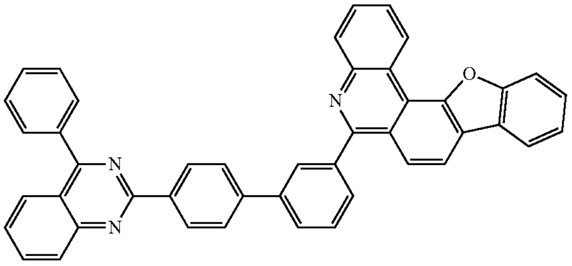
4-660
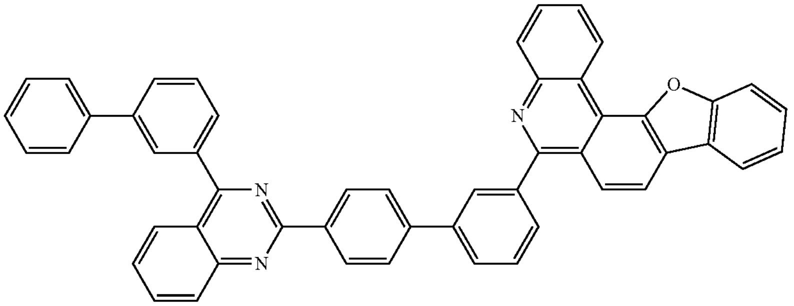
4-661
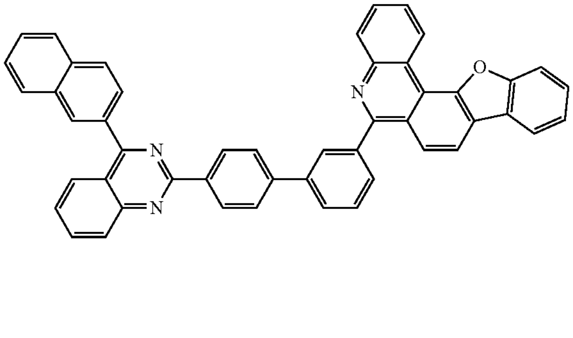
4-662
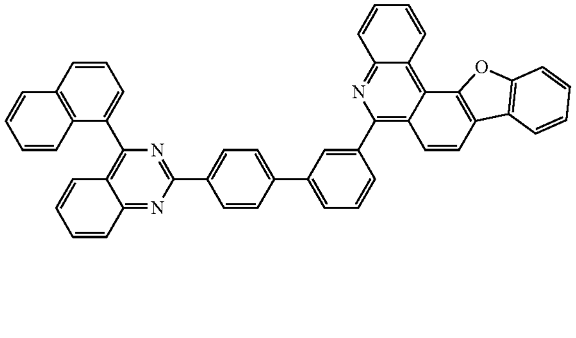

-continued
4-663
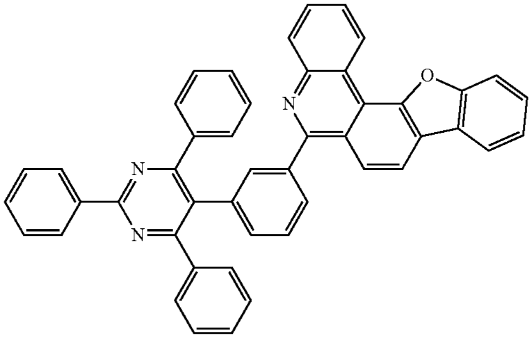
4-664
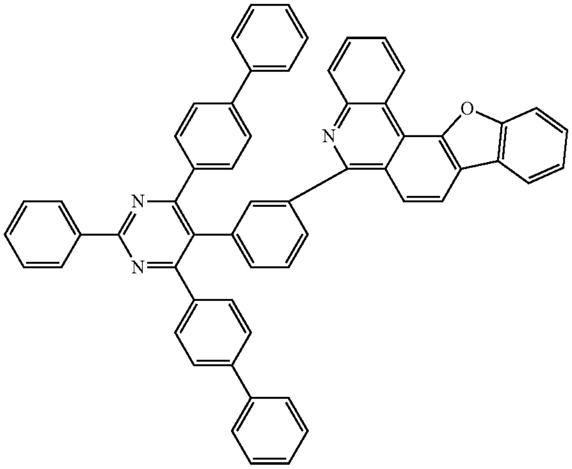
4-665
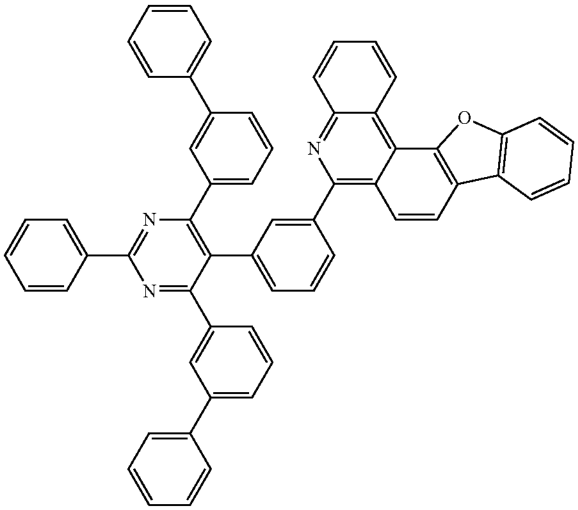
4-666
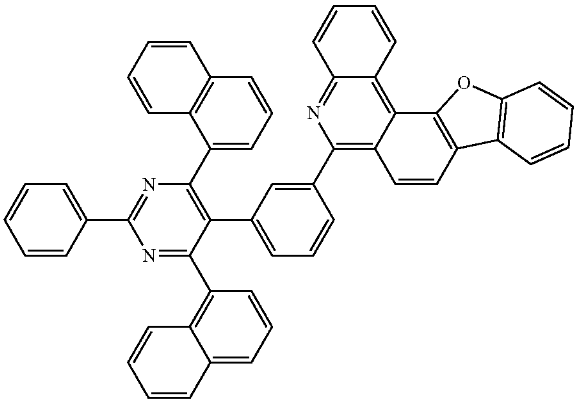
4-667
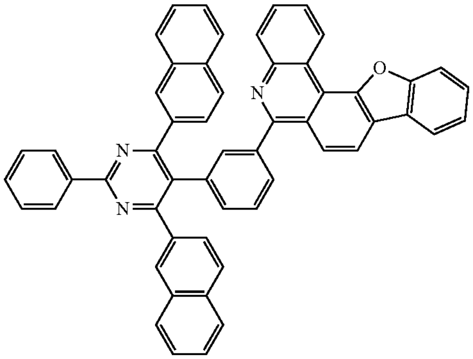
4-668
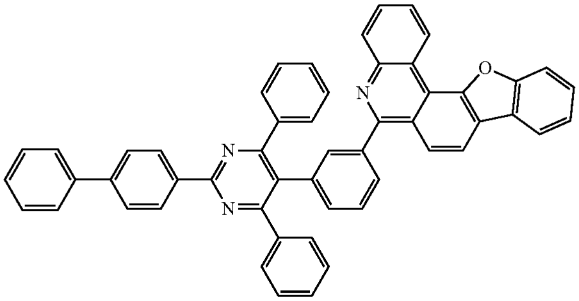

-continued
4-669
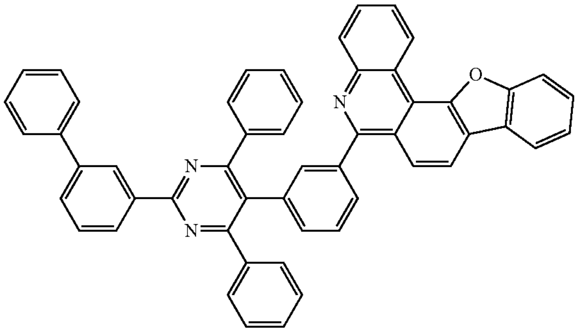
4-670
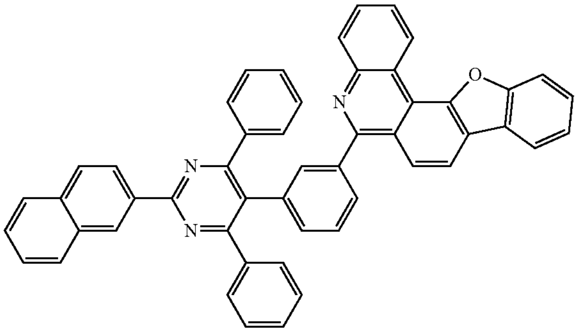
4-671
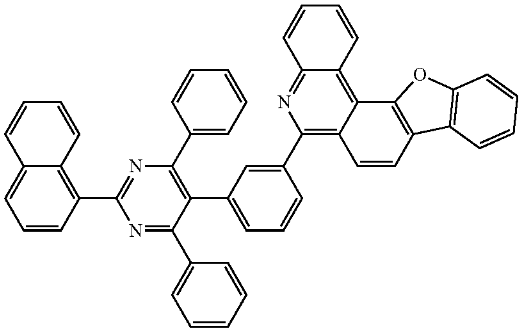
4-672
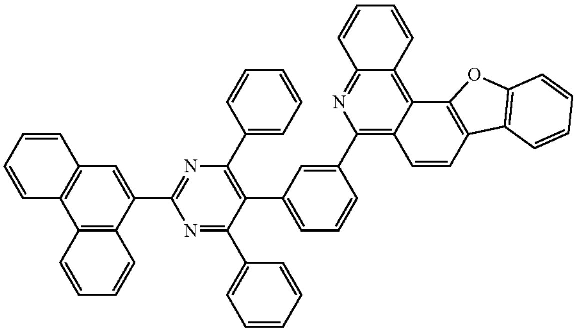
4-673
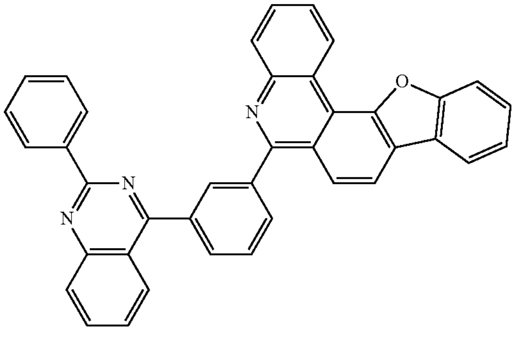
4-674
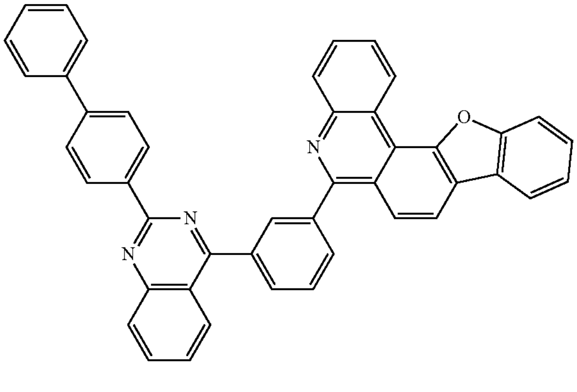
4-675
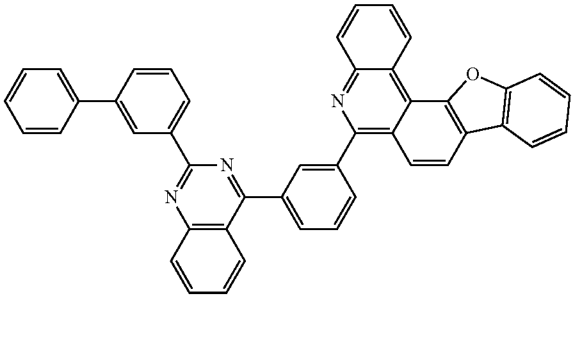
4-676
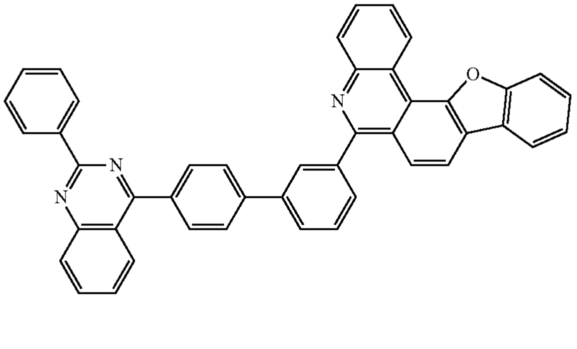

-continued
4-677
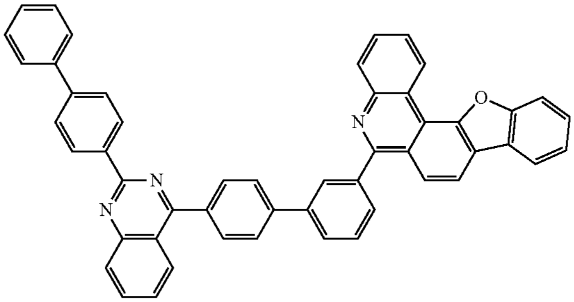
4-678
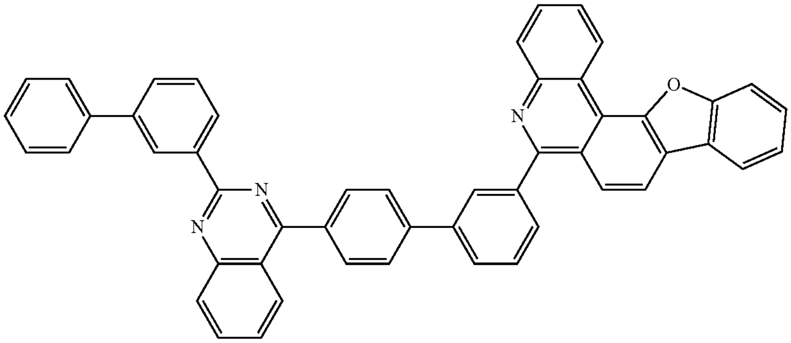
4-679
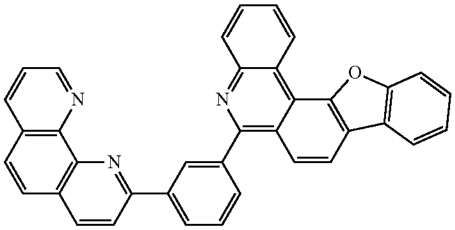
4-680
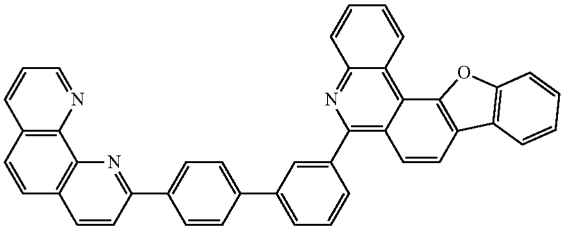
4-681
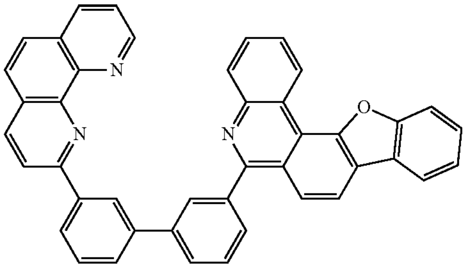
4-682
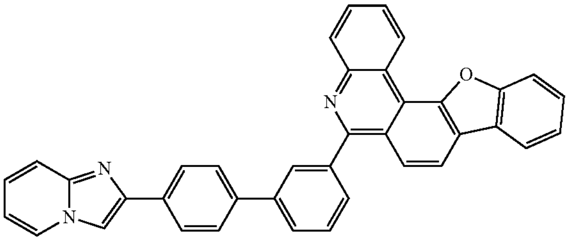
4-683
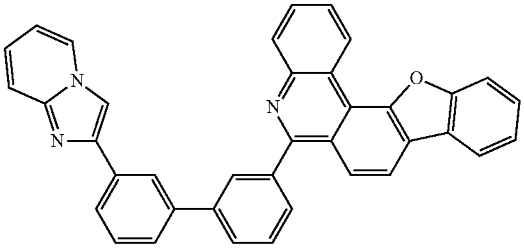
4-684
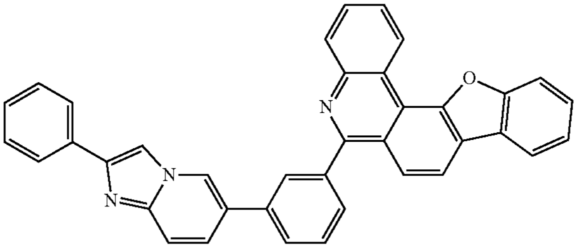

-continued
4-685
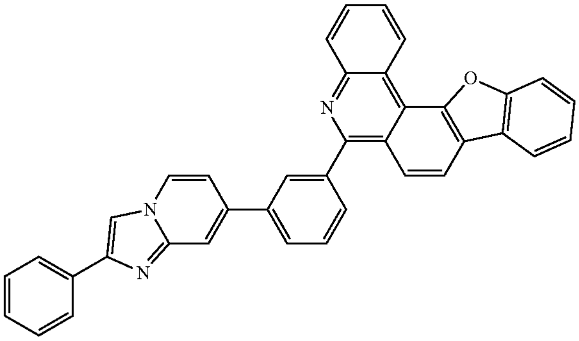
4-686
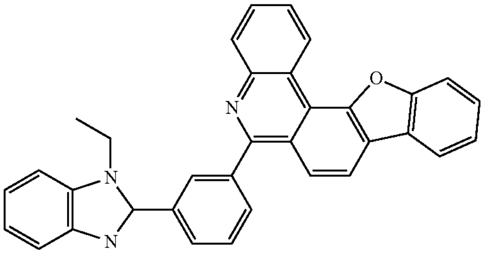
4-687
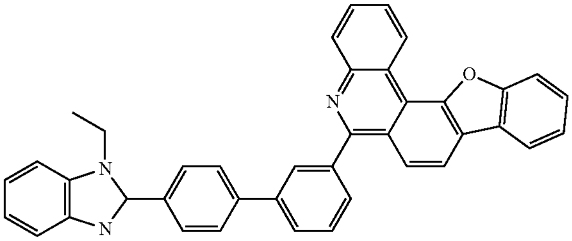
4-688
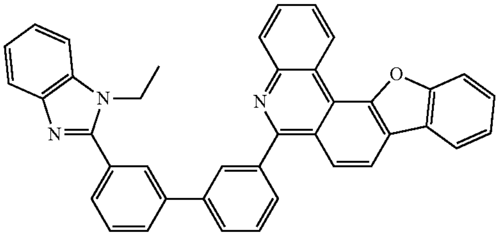
4-689
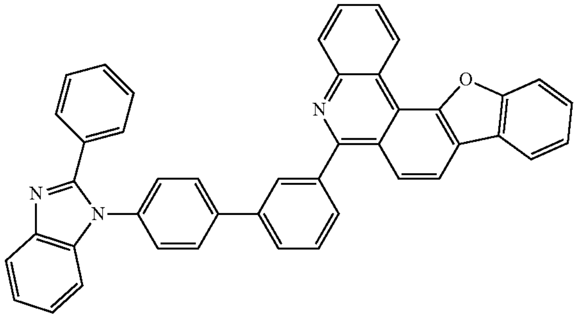
4-690
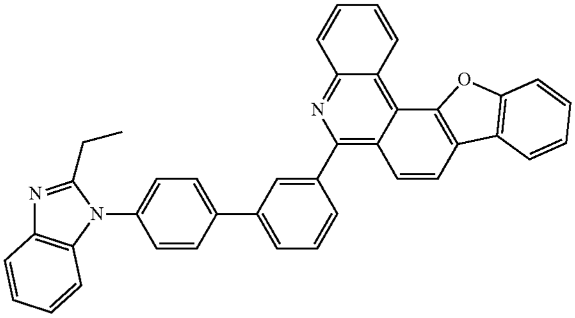
4-691
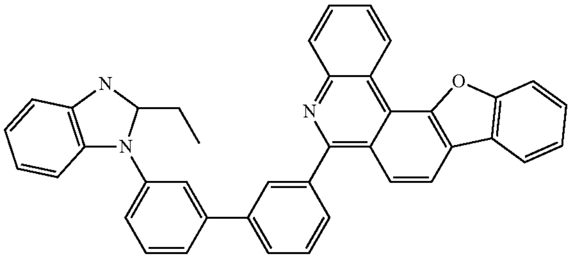
4-692
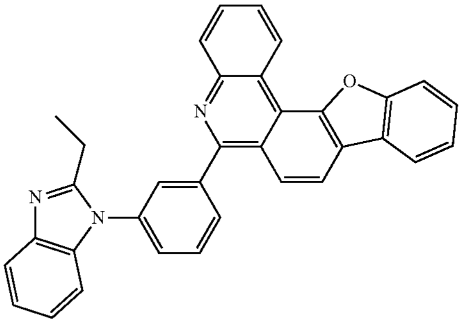
4-693
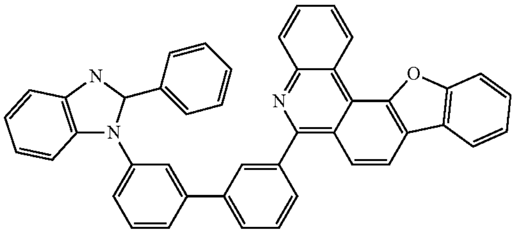
4-694
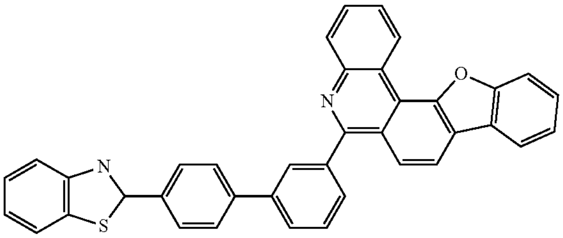

-continued
4-695
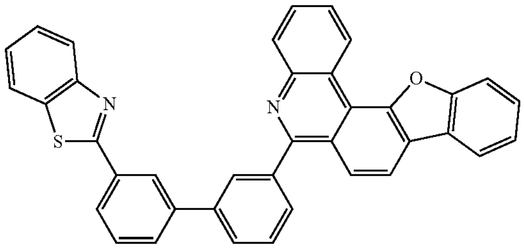
4-696
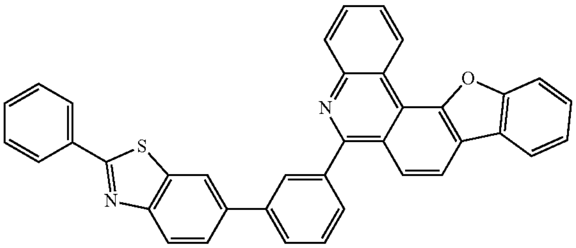
4-697
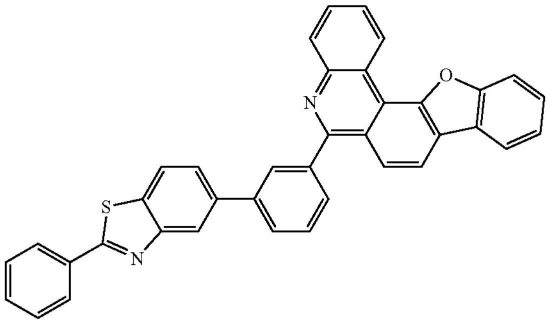
4-698
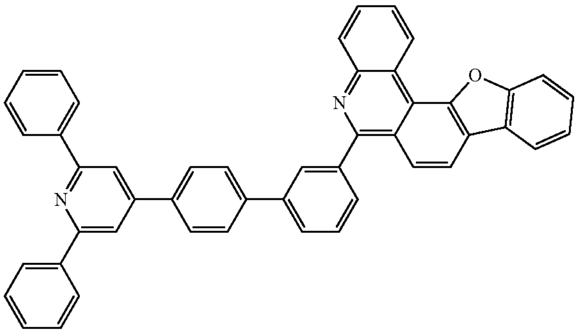
4-699
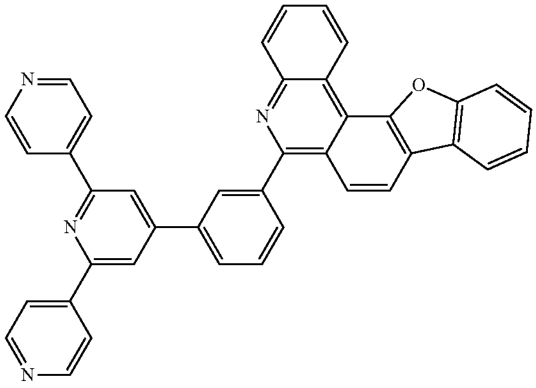
4-700
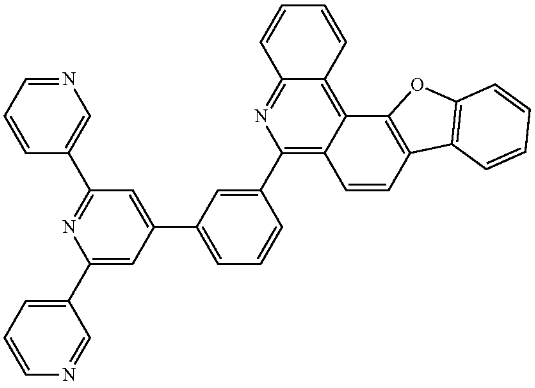
4-701
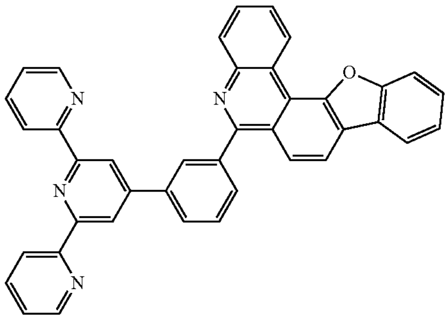
4-702
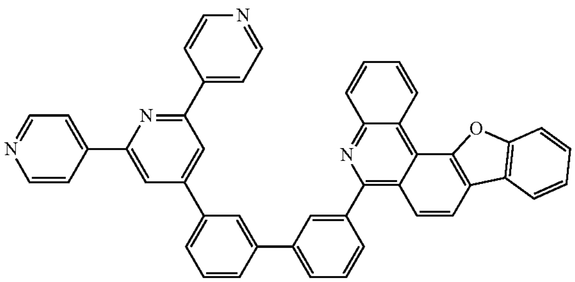

-continued
4-703
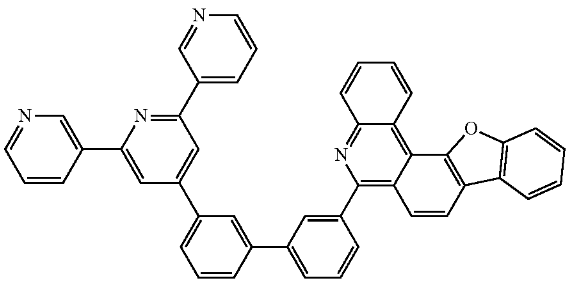
4-704
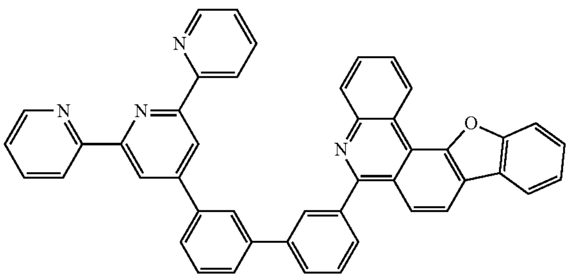
4-705
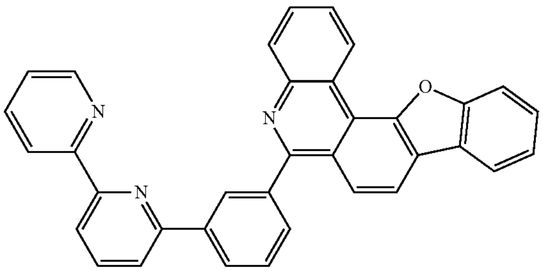
4-706
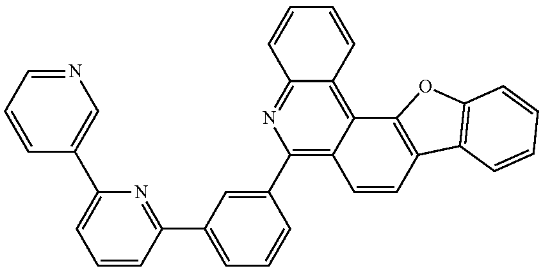
4-707
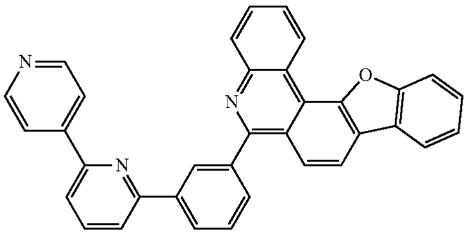
4-708
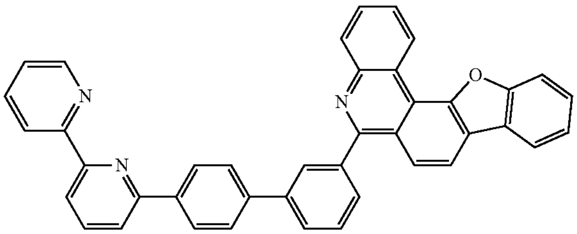
4-709
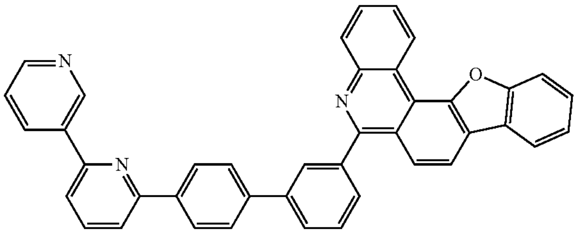
4-710
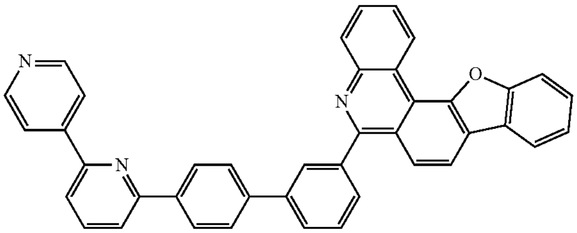
4-141
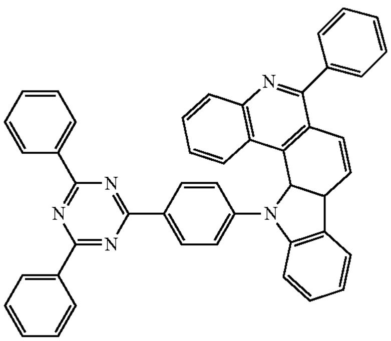

-continued
4-142
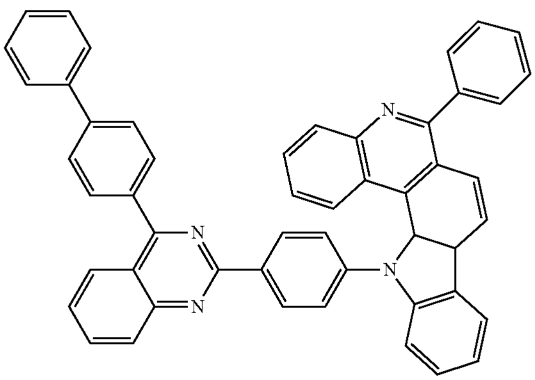
4-143
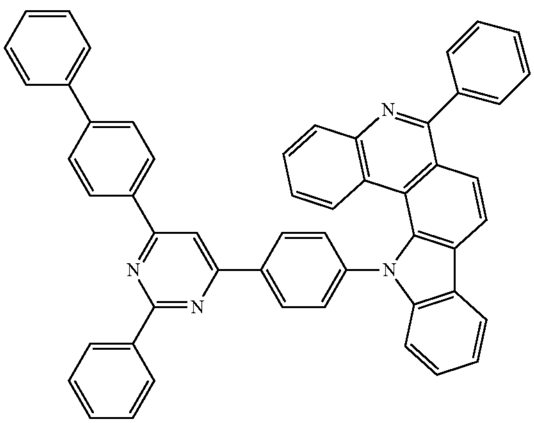
4-184
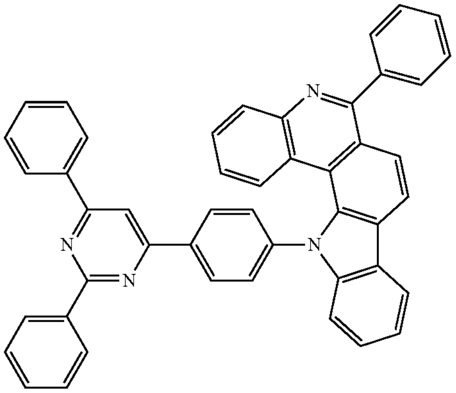
4-185
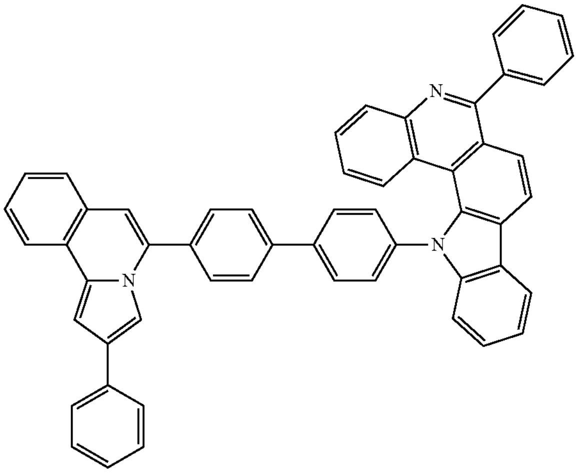
4-186
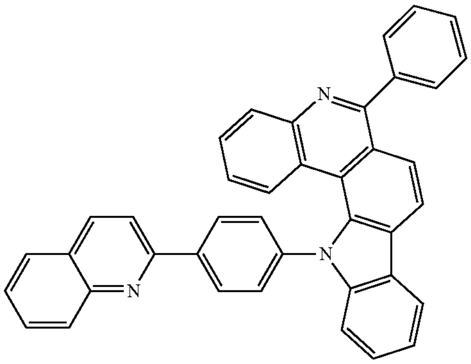
4-187
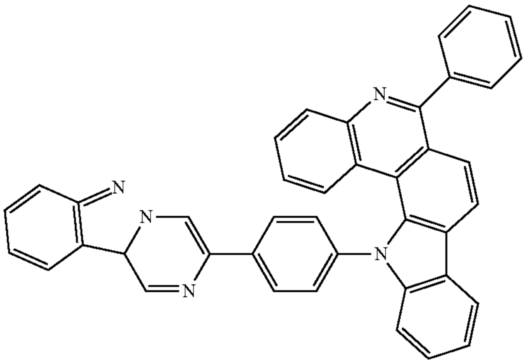

-continued
4-188
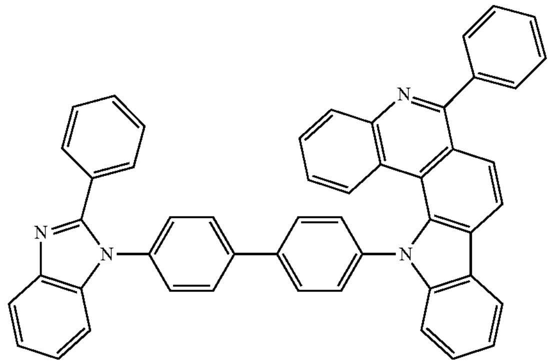
4-189
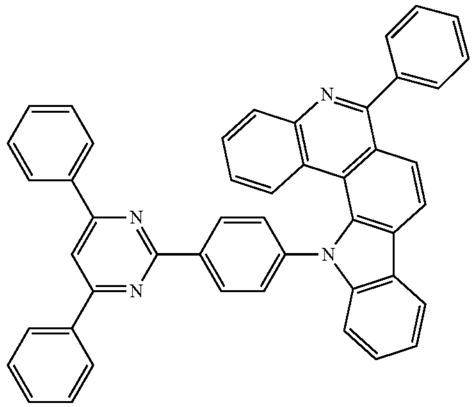
4-190
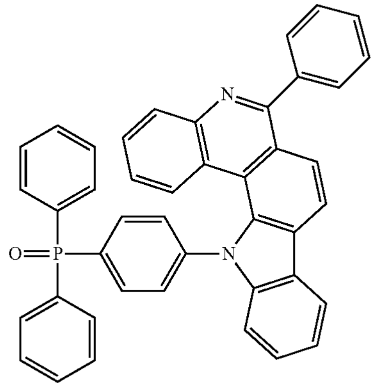
4-191
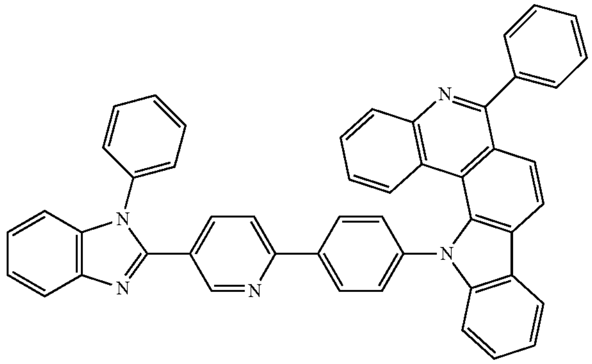
4-192
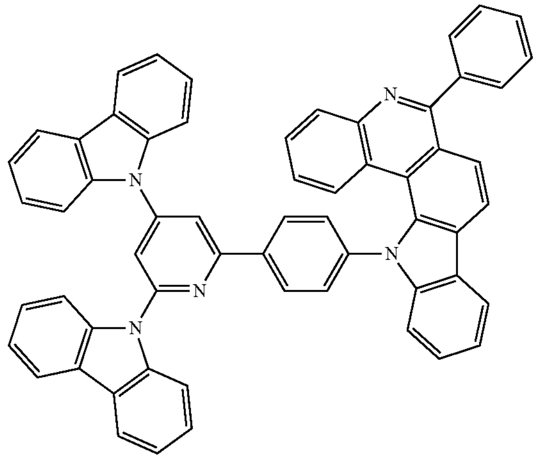
4-193
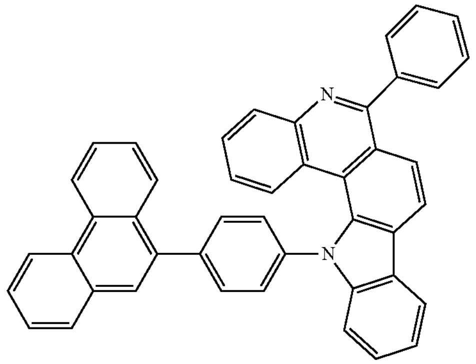
4-194
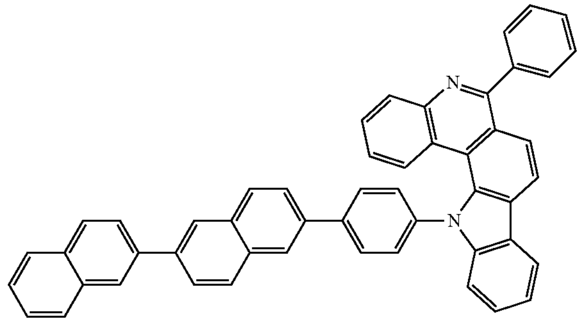
4-195
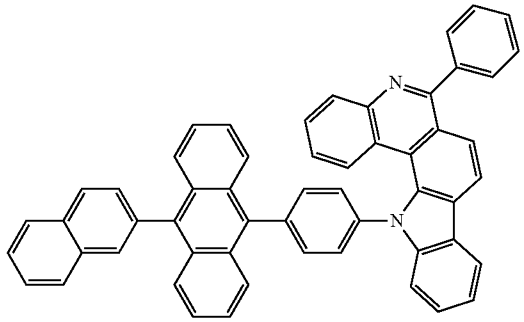

-continued
4-196
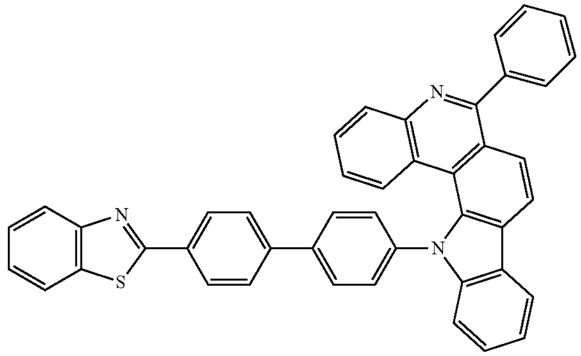
4-197
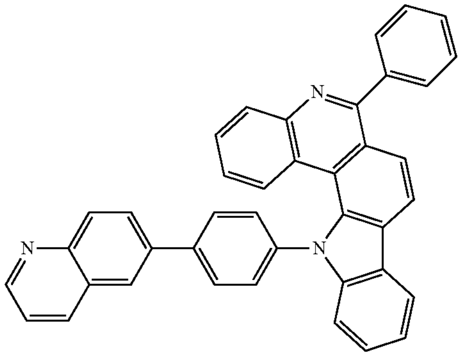
4-198
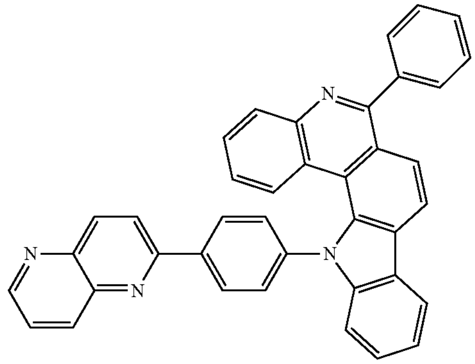
4-199
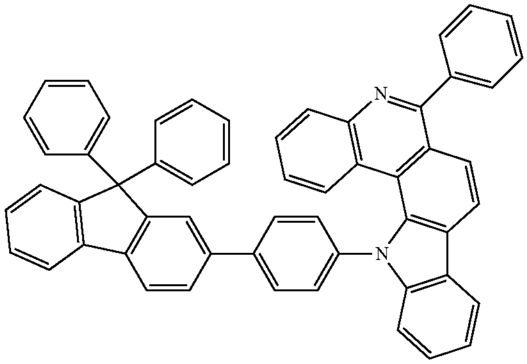
4-200
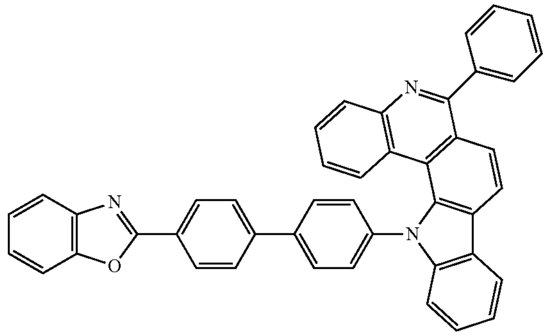
4-201
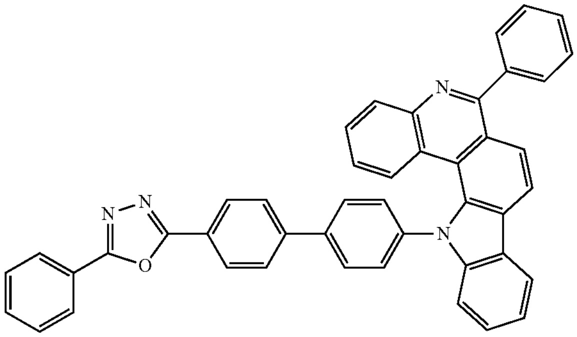
4-202
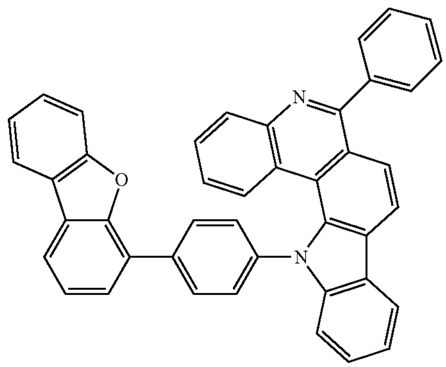
4-203
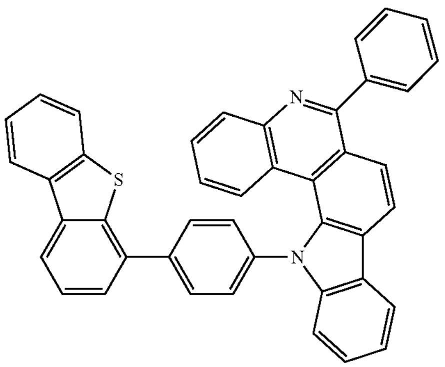

-continued
4-204
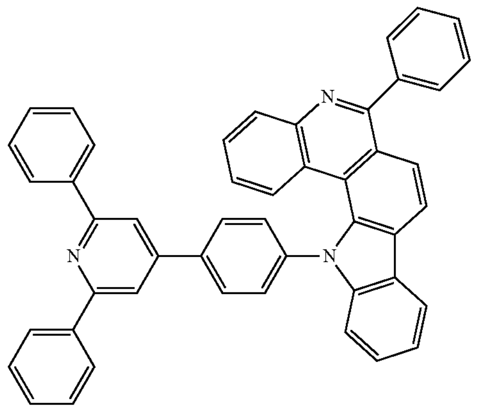
4-205
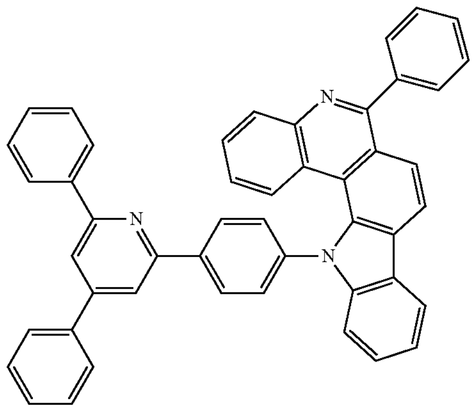
4-206
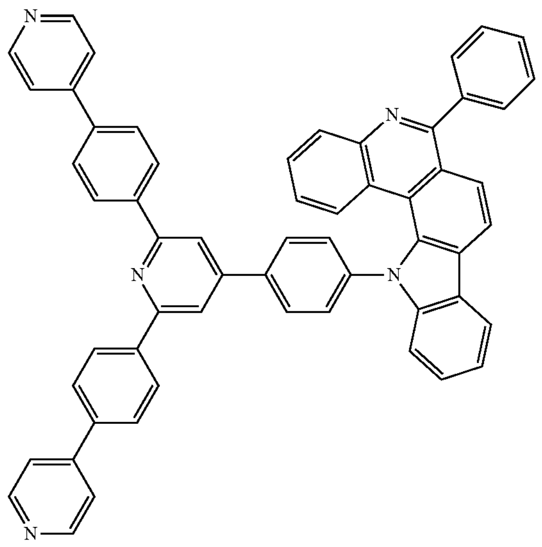
4-207
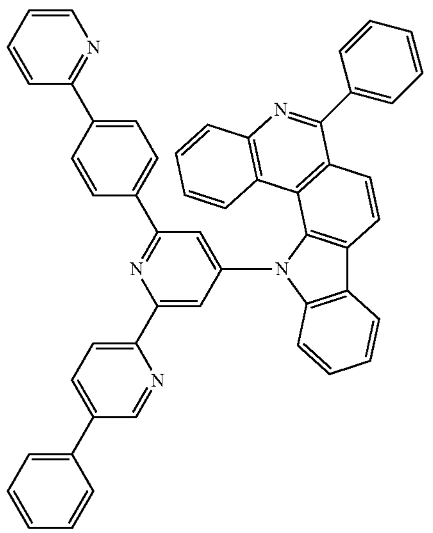
4-208
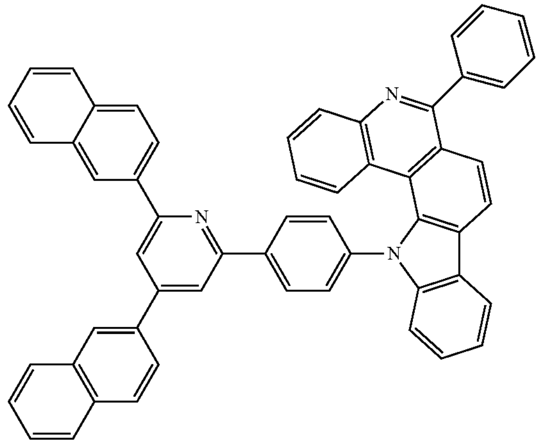
4-209
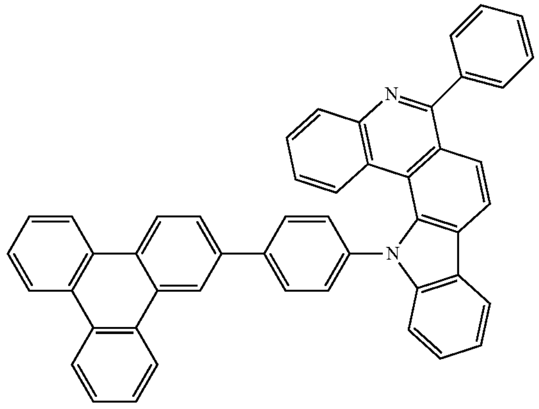

-continued
4-210
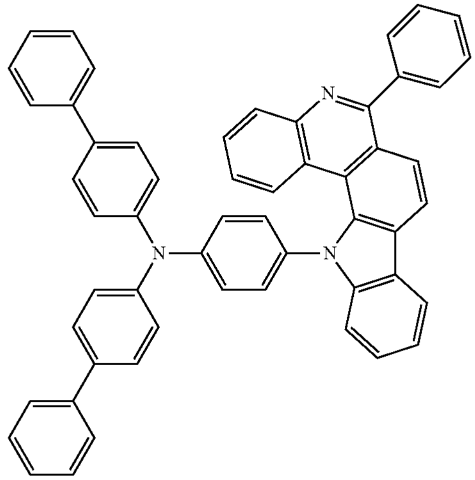
4-211
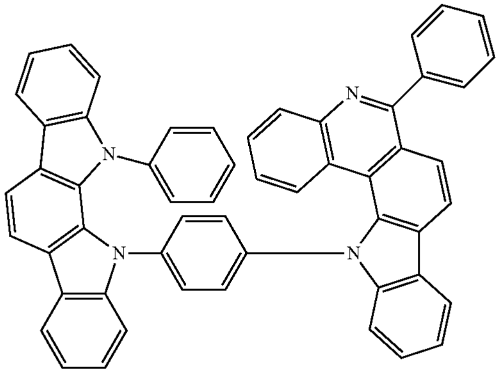
4-212
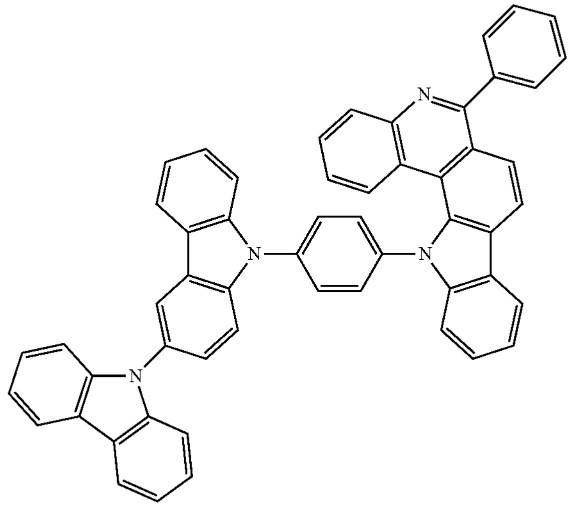
4-213
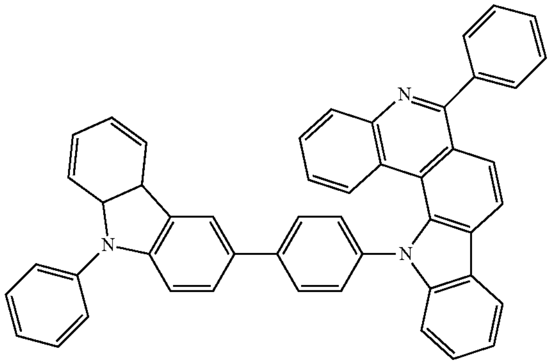
4-214
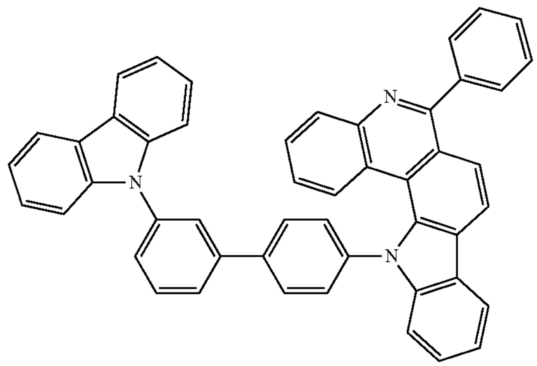
4-215
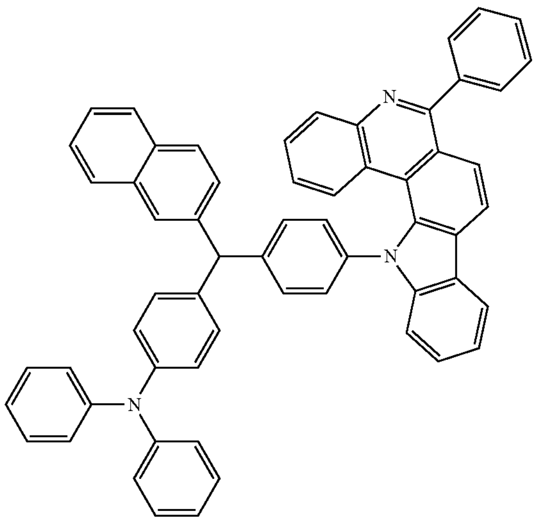

-continued
4-216
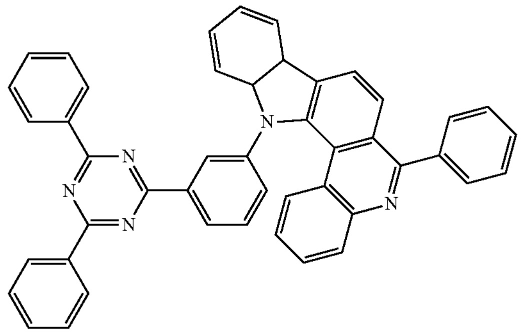
4-217
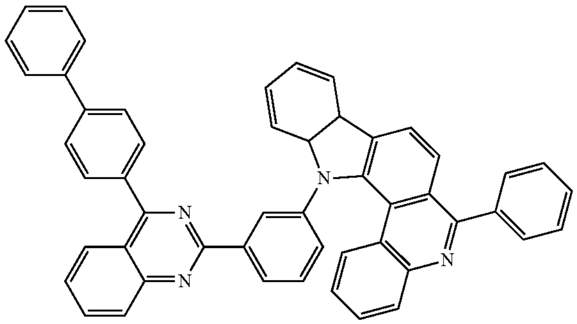
4-218
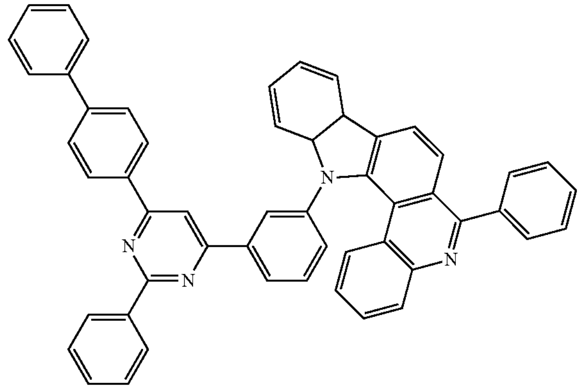
4-219
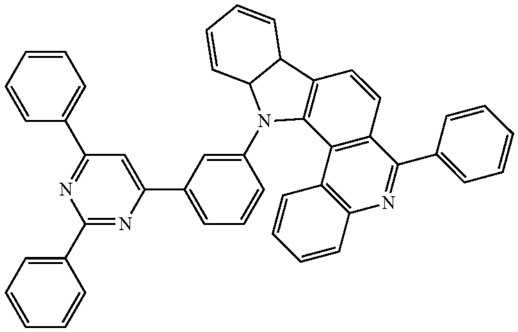
4-220
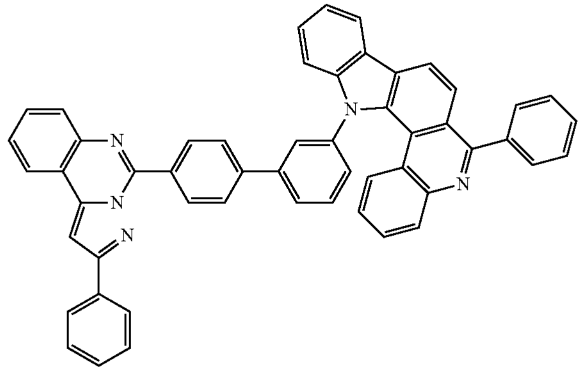
4-221
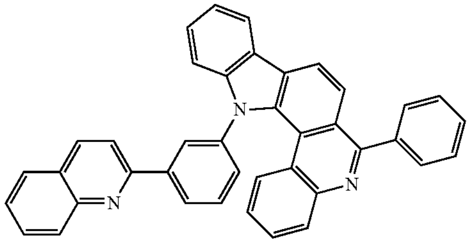
4-222
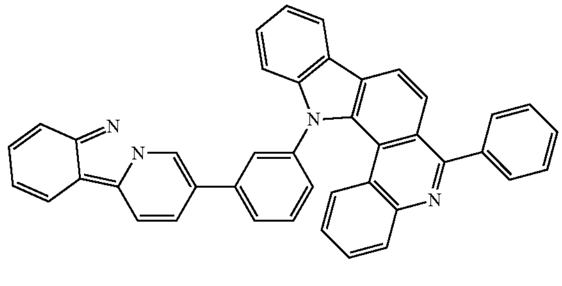
4-223
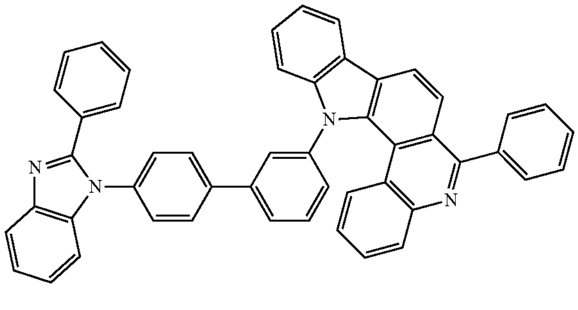

-continued
4-224
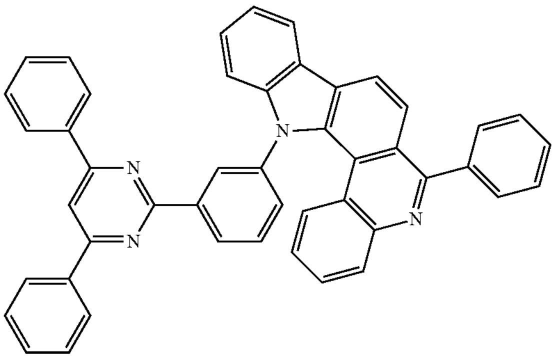
4-225
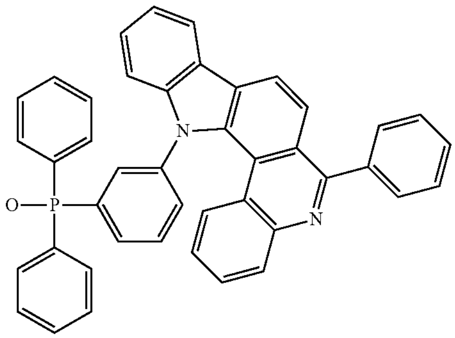
4-226
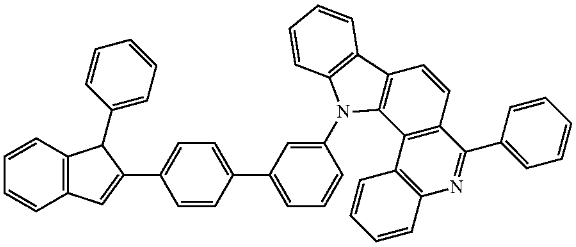
4-227
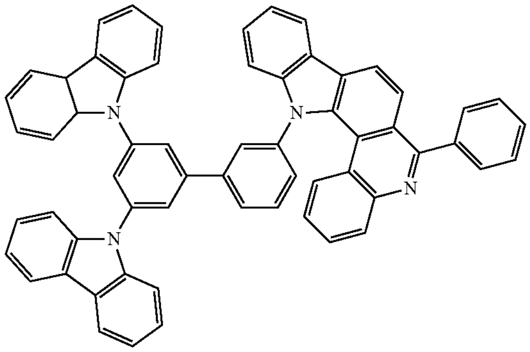
4-228
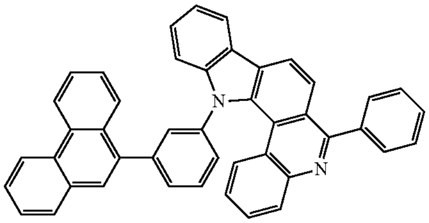
4-229
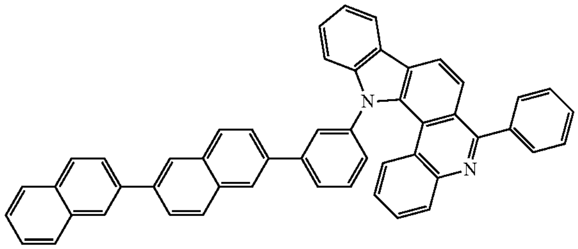
4-230
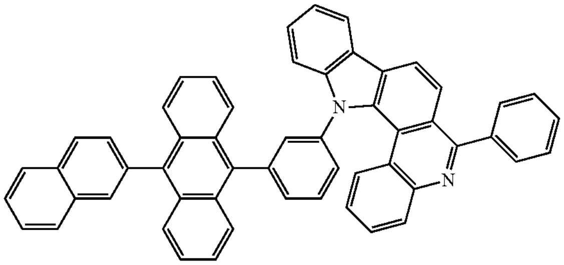
4-231
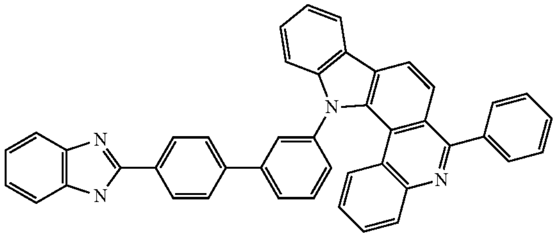
4-232
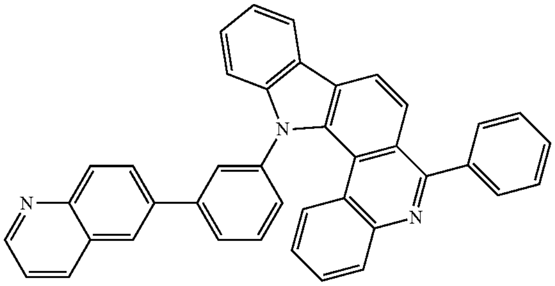
4-233
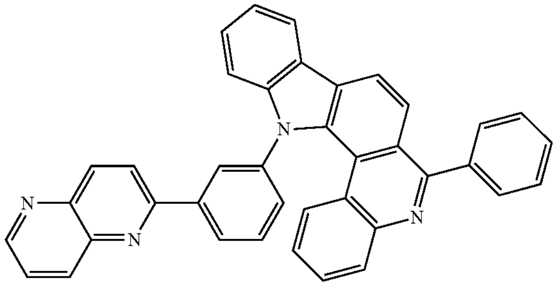

-continued
4-234
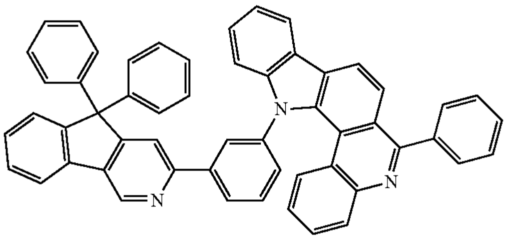
4-235
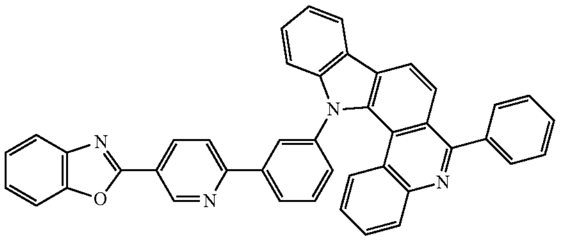
4-236
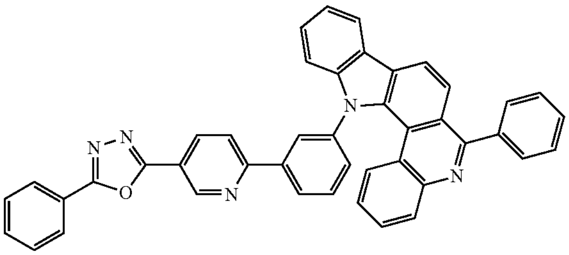
4-237
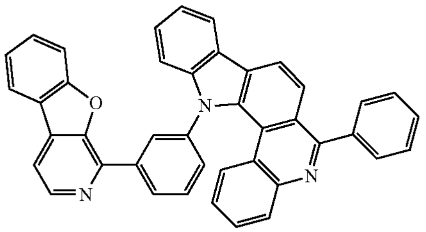
4-238
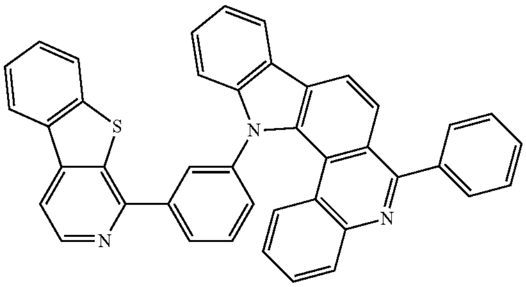
4-239
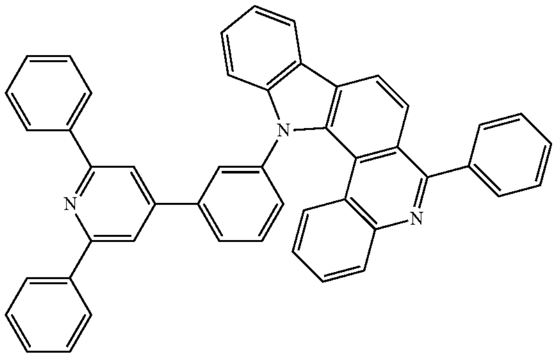
4-240
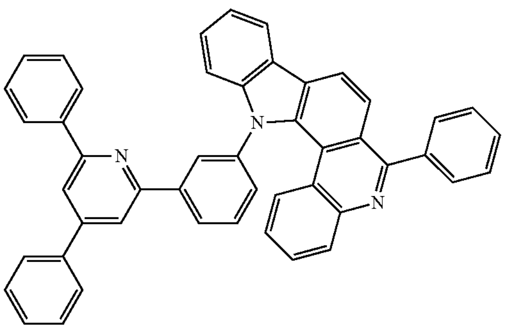
4-241
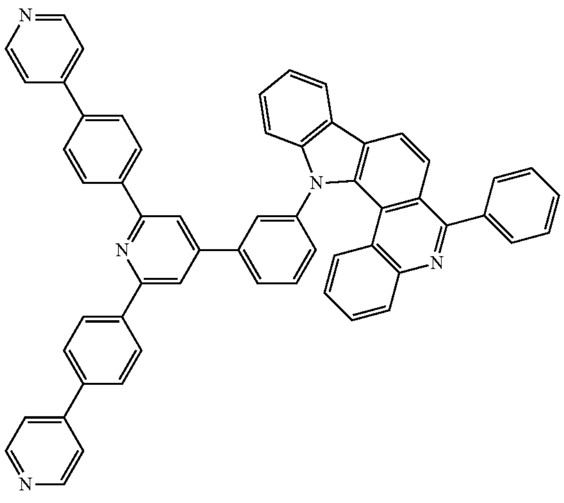

-continued
4-242
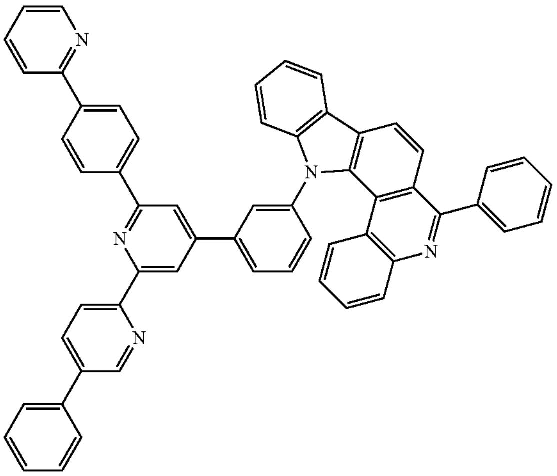
4-243
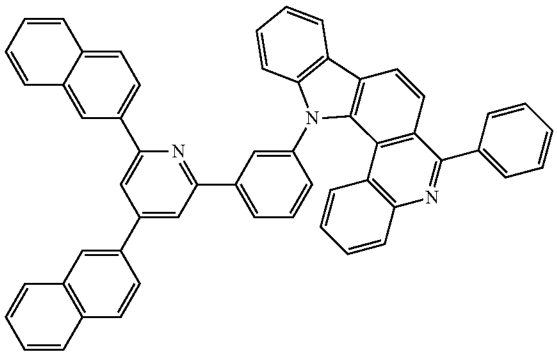
4-244
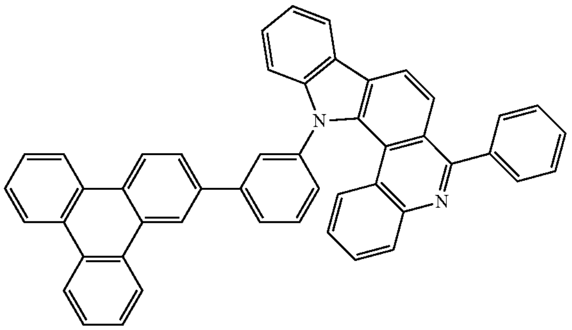
4-245
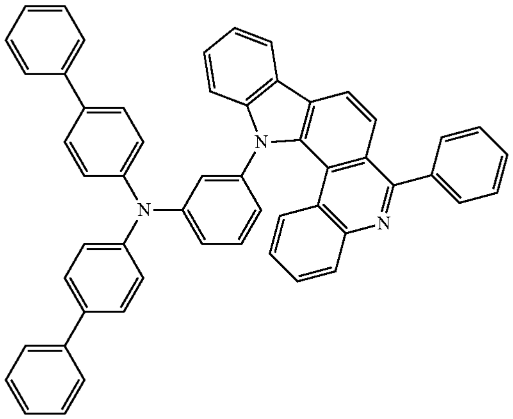
4-246
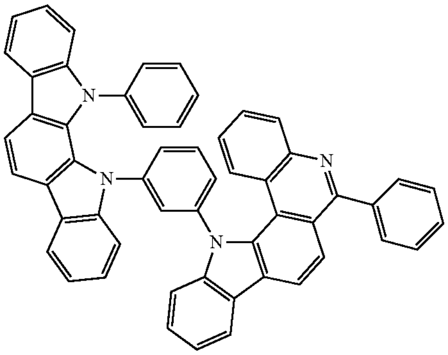
4-247
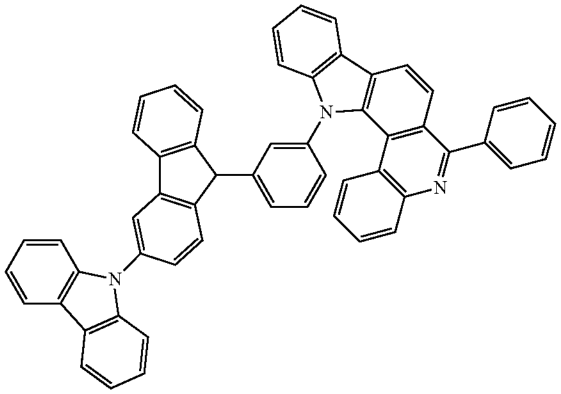
4-248
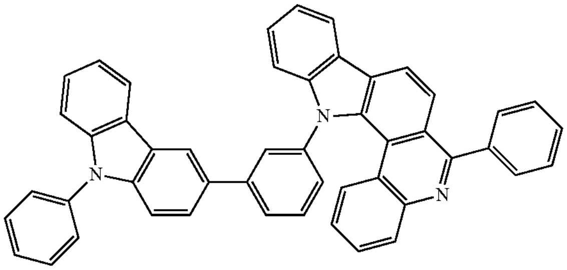
4-249
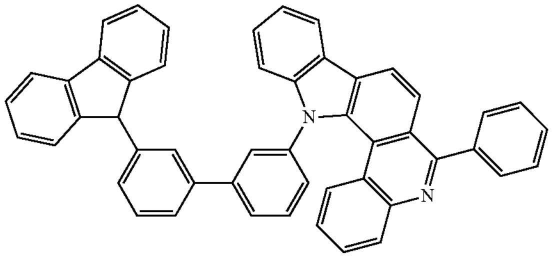

-continued
4-250
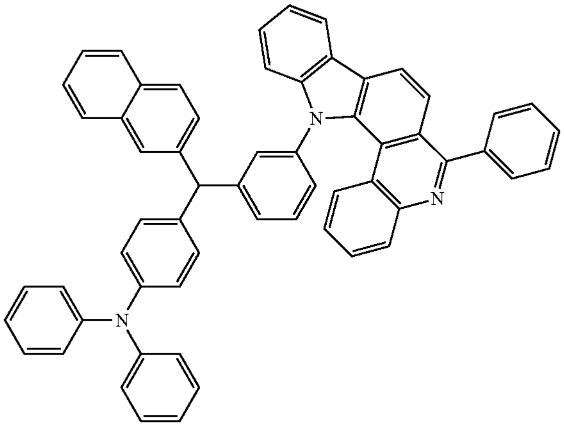
5-1
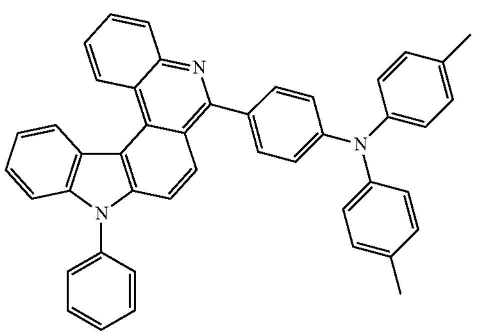
5-2
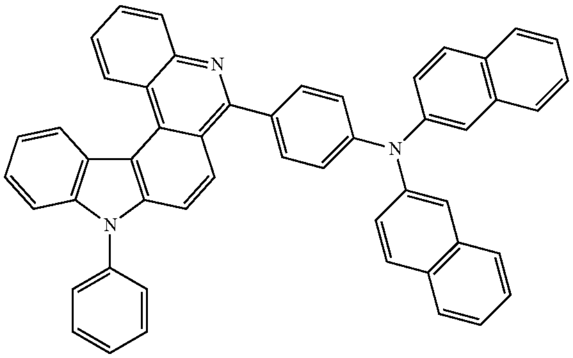
5-3
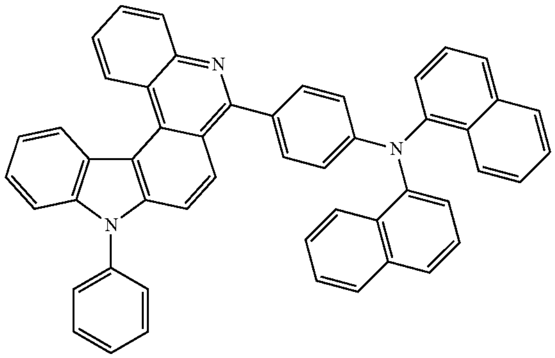
5-4
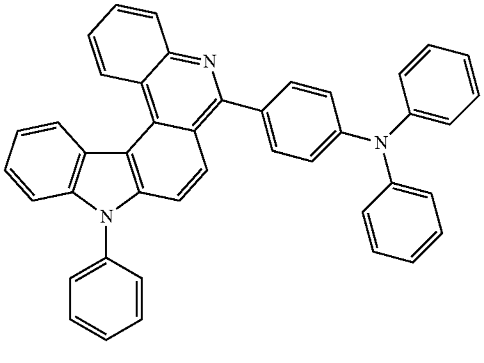
5-5
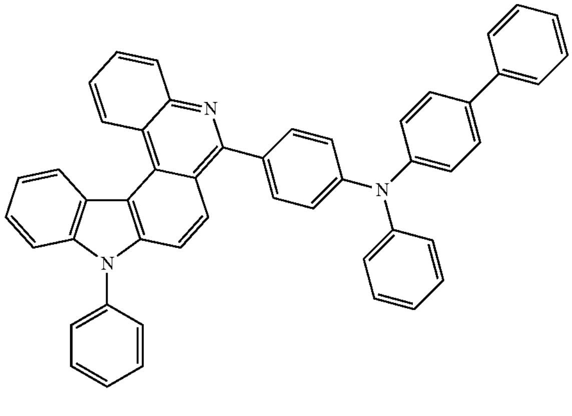

-continued
5-6
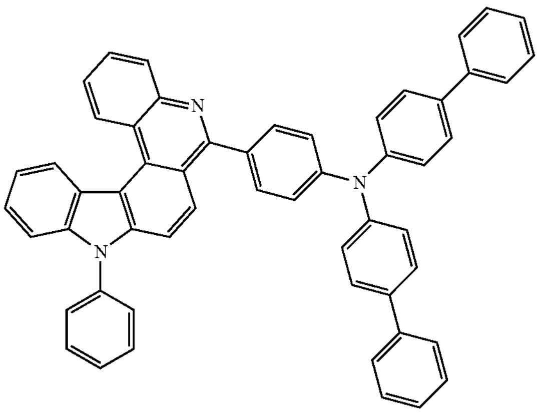
5-7
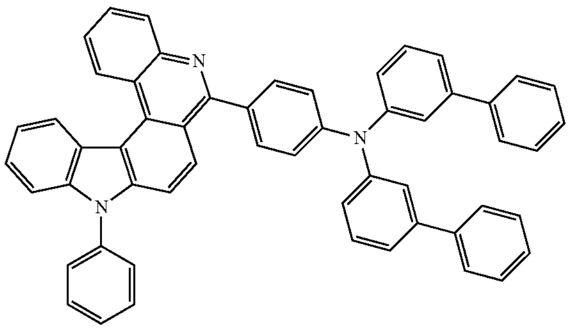
5-8
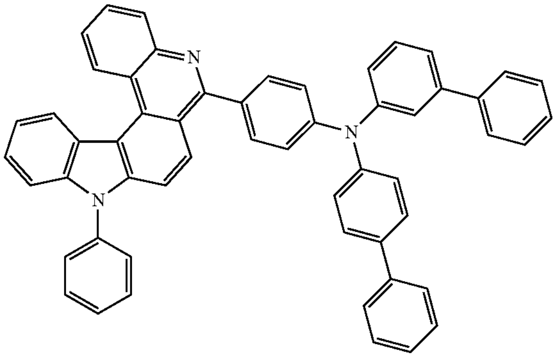
5-9
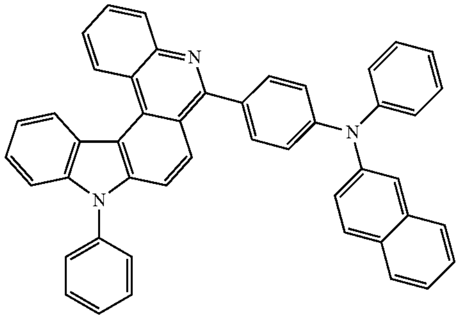
5-10
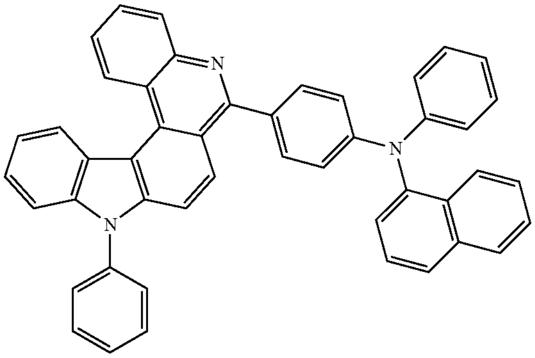
5-11
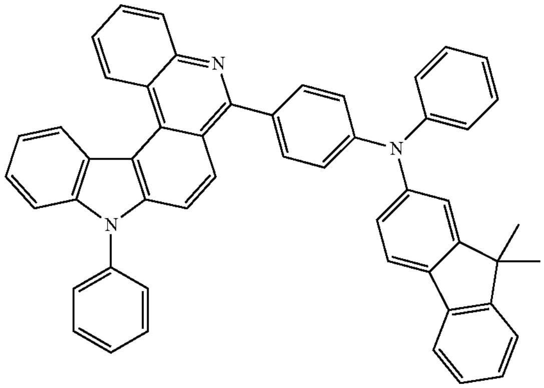
5-12
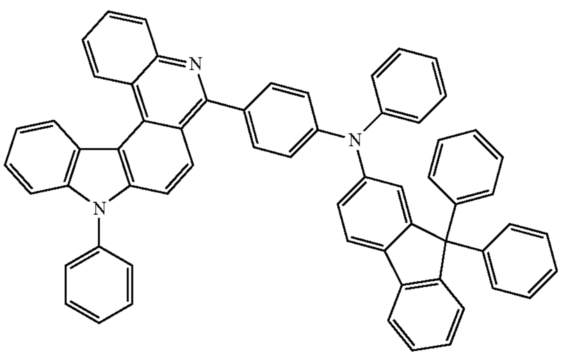
5-13
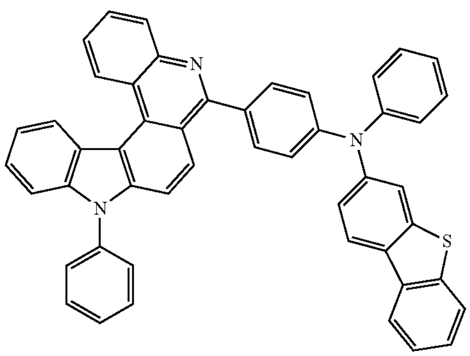

-continued
5-14
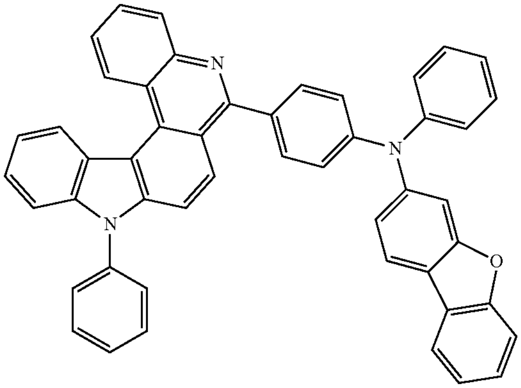
5-15
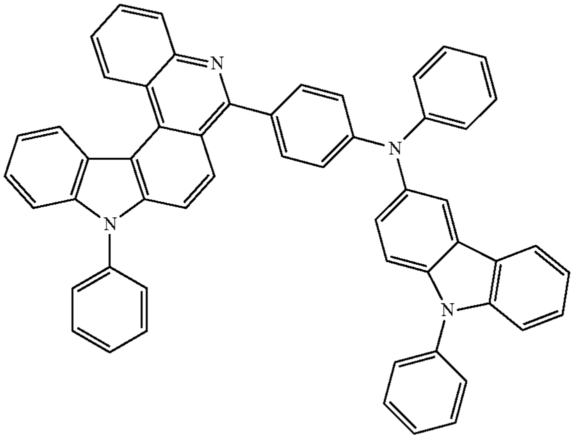
5-16
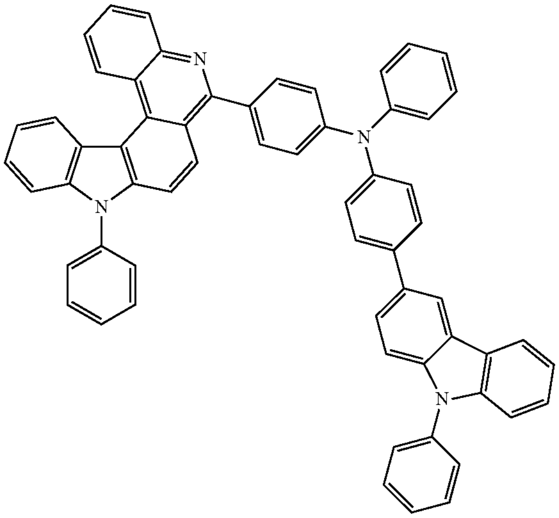
5-17
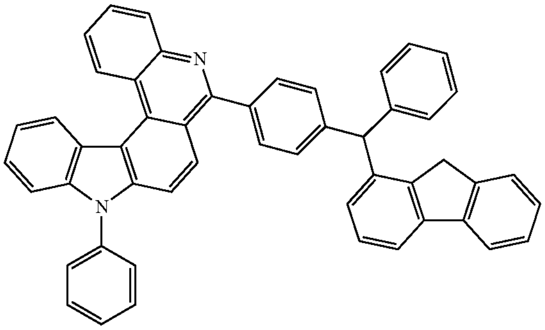
5-18
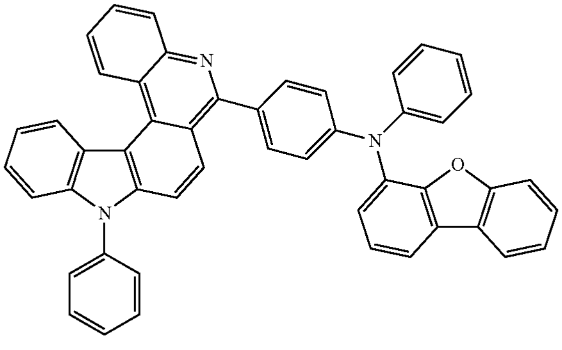
5-19
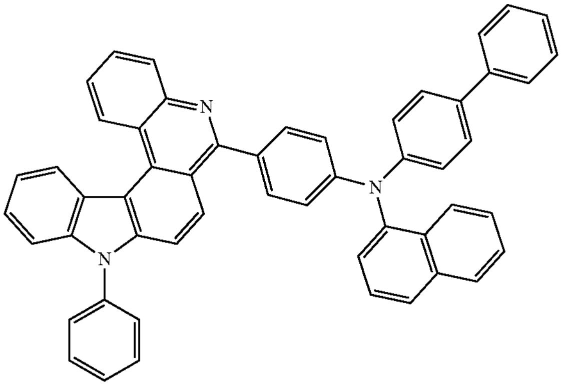

-continued
5-20
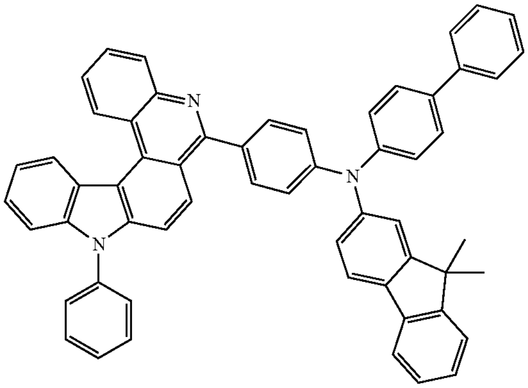
5-21
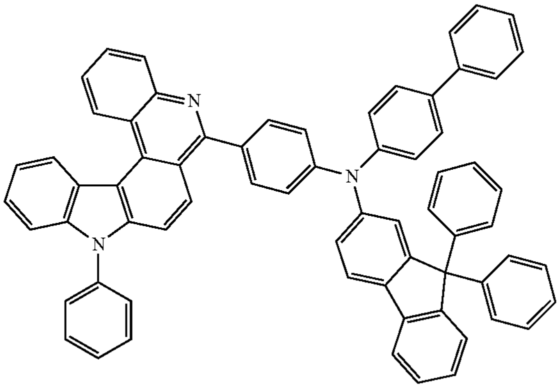
5-22
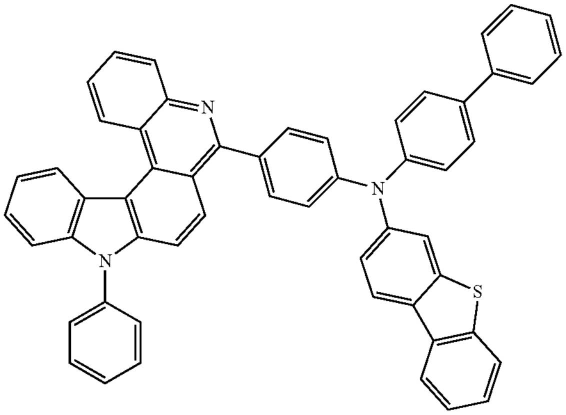
5-23
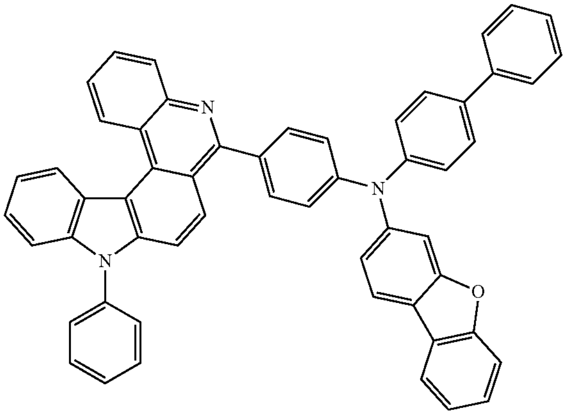
5-24
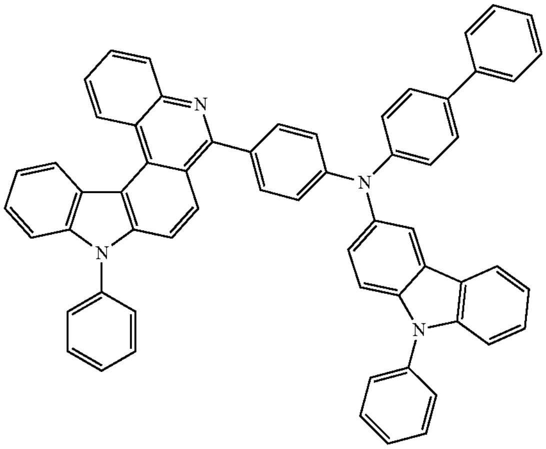
5-25
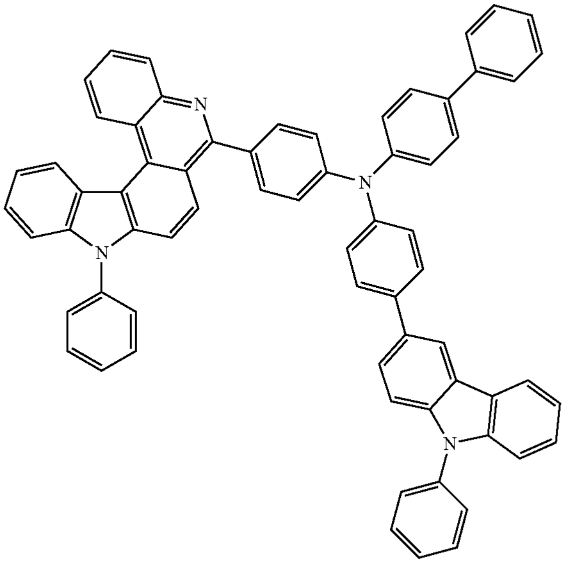

-continued
5-26
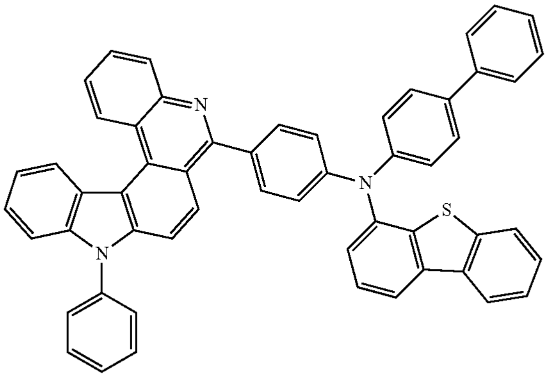
5-27
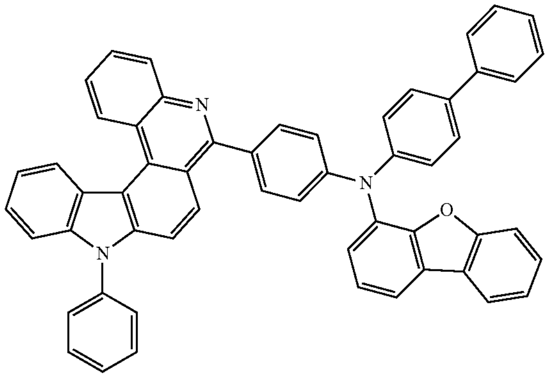
5-28
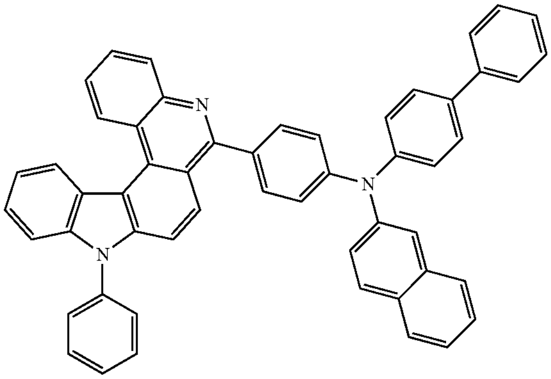
5-29
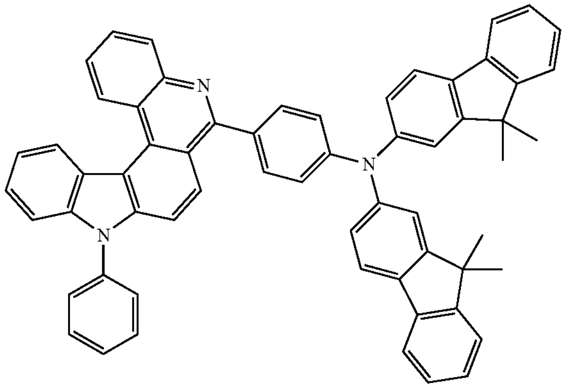
5-30
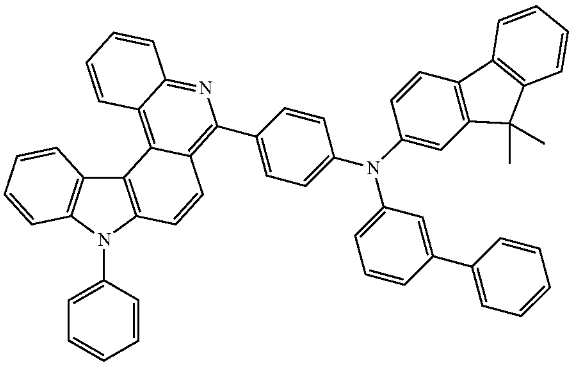
5-31
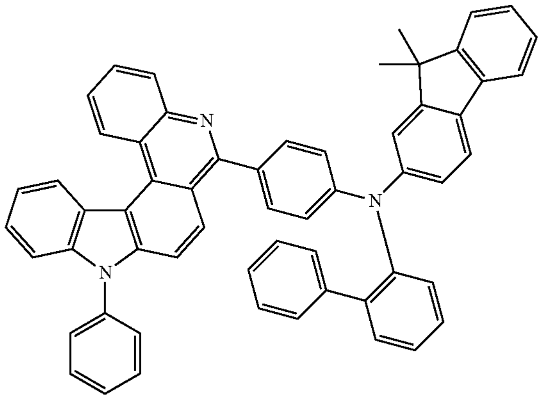

-continued
5-32
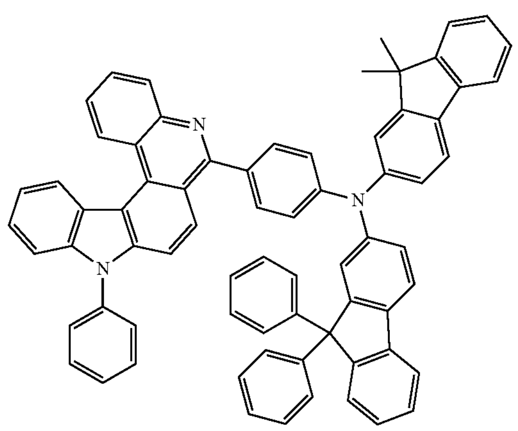
5-33
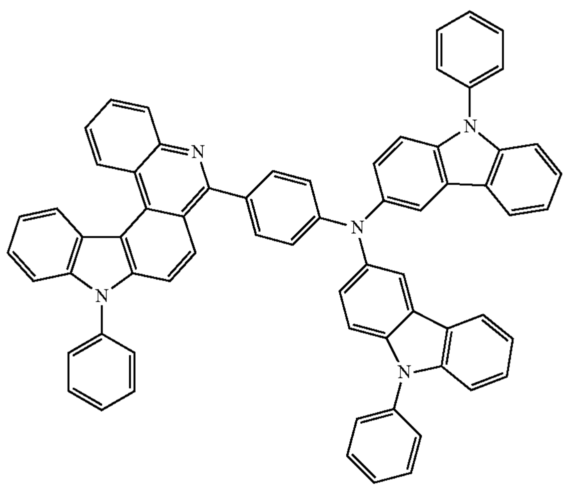
5-34
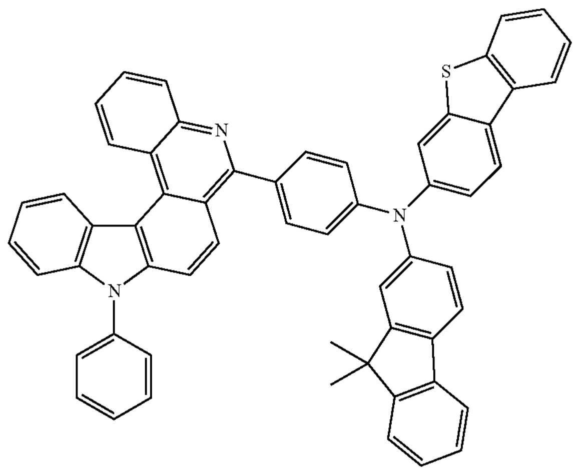
5-35
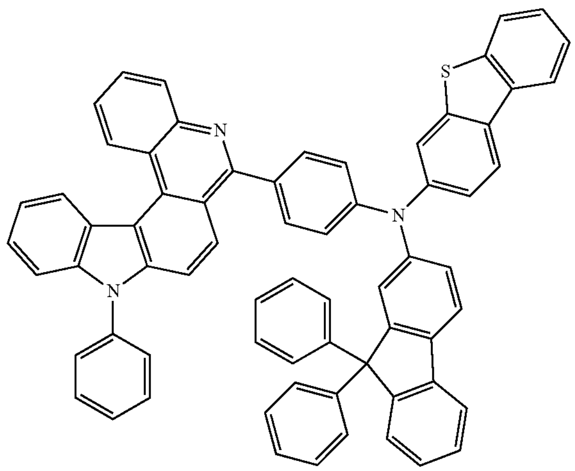
5-36
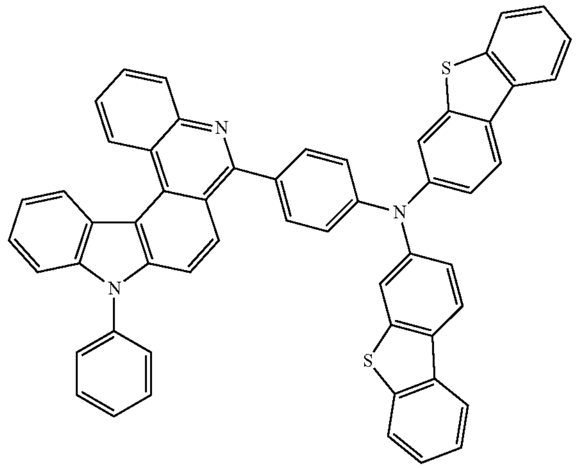
5-37
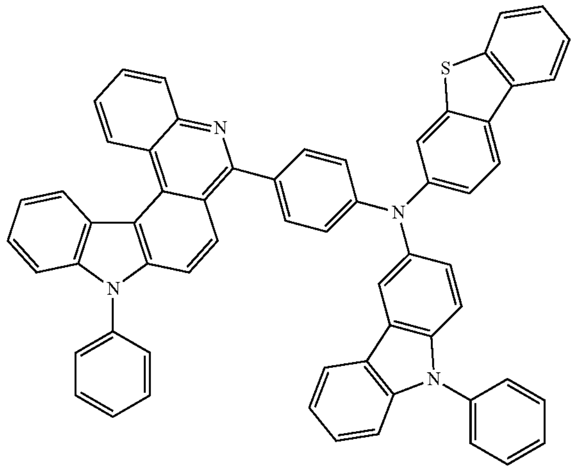

-continued
5-38
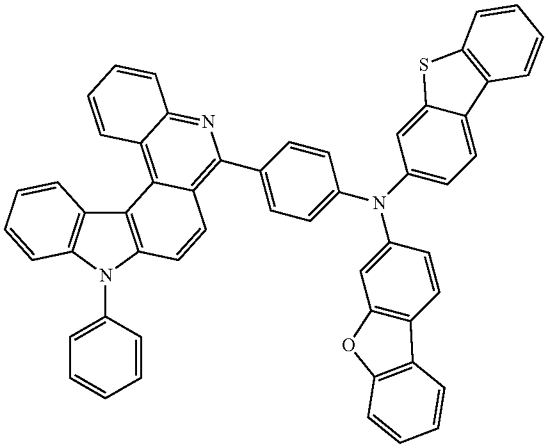
5-39
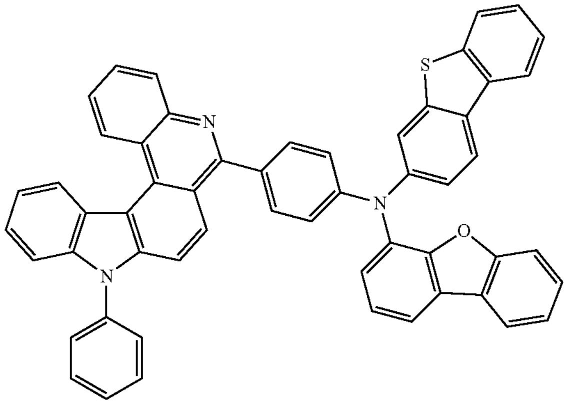
5-40
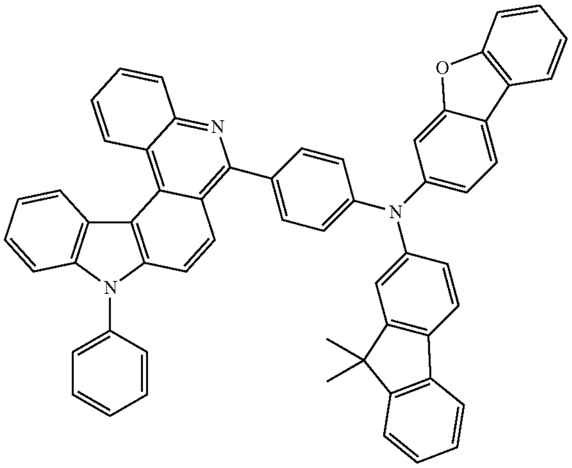
5-41
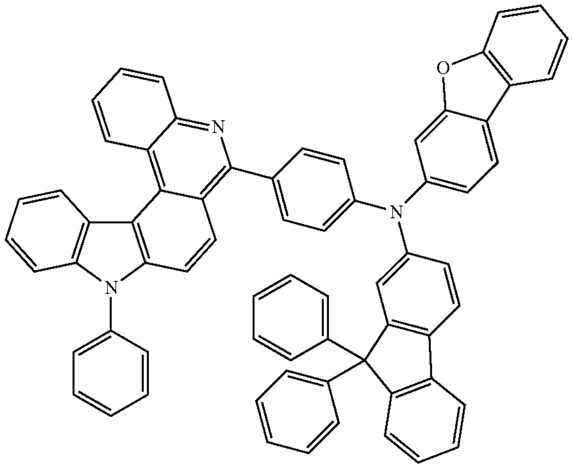
5-42
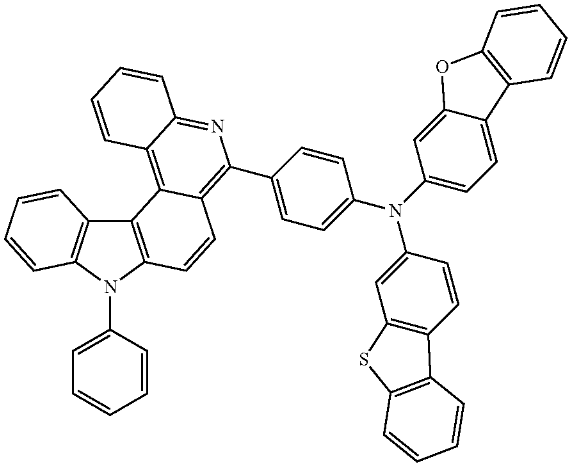
5-43
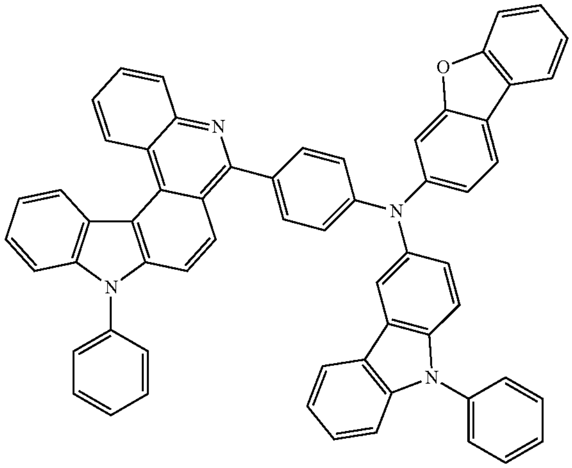

-continued
5-44
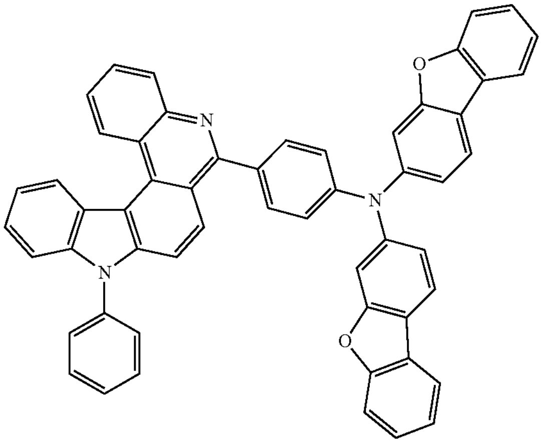
5-45
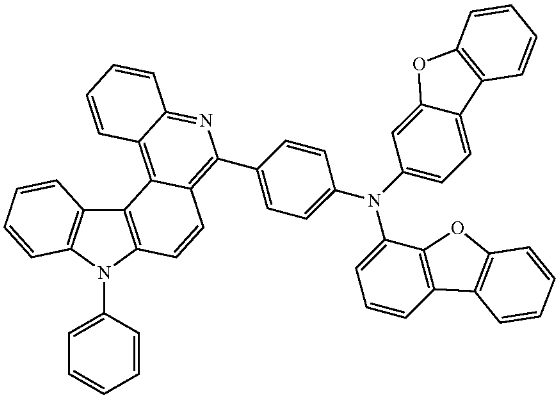
5-46
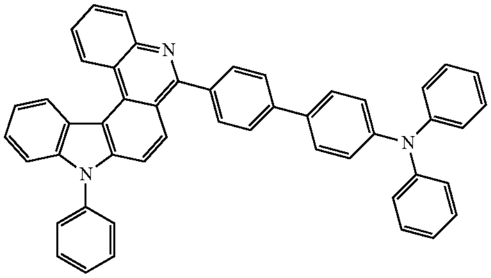
5-47
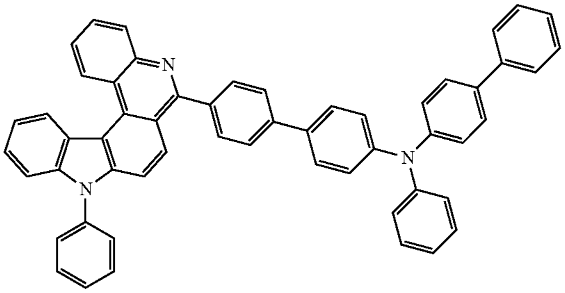
5-48
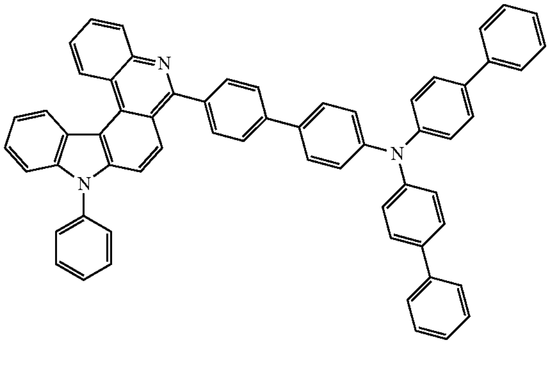
5-49
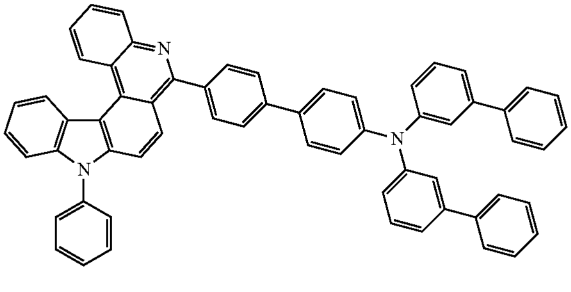
5-50
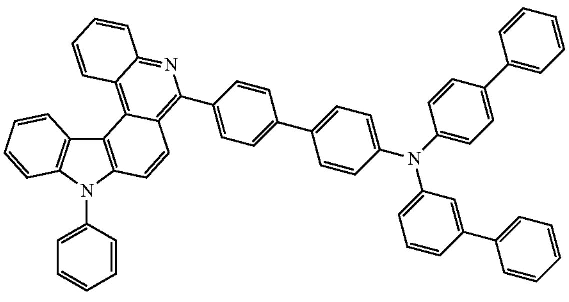
5-51
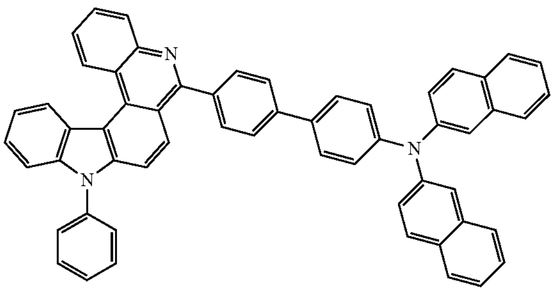

-continued
5-52
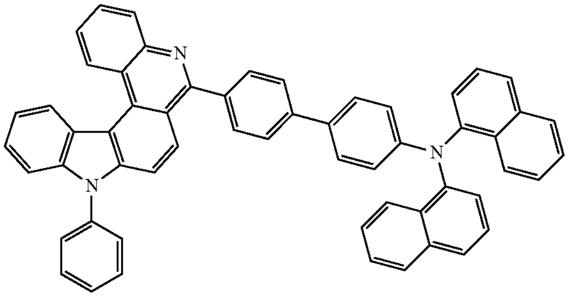
5-53
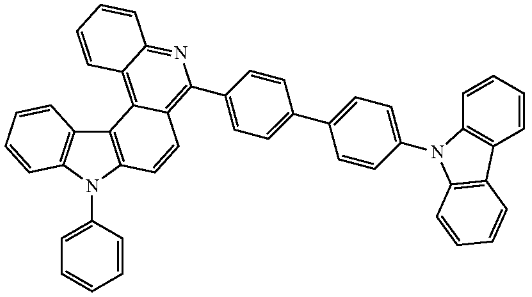
5-54
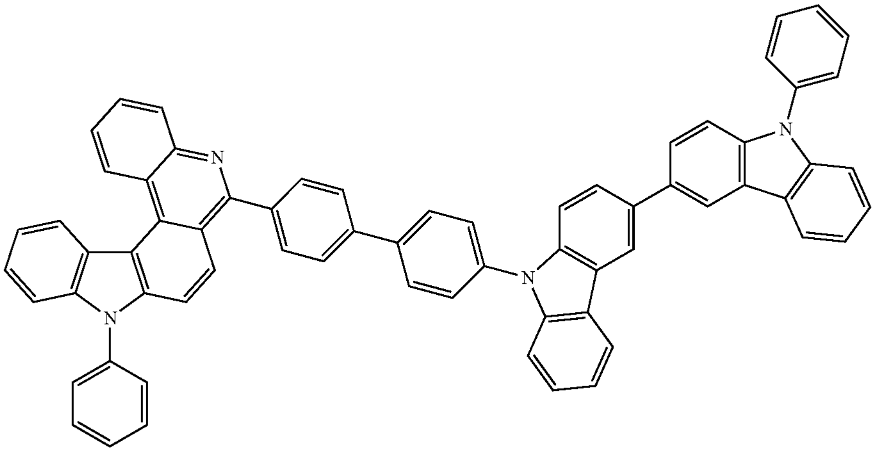
5-55
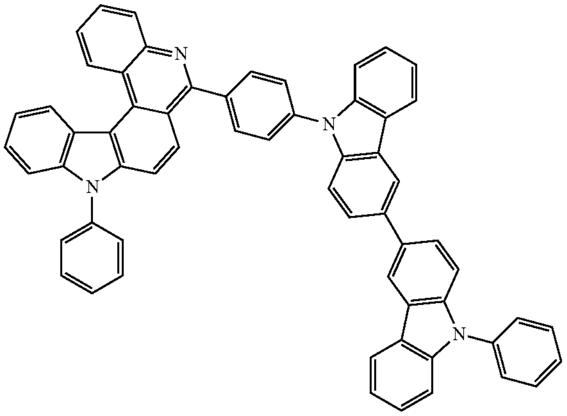
5-56
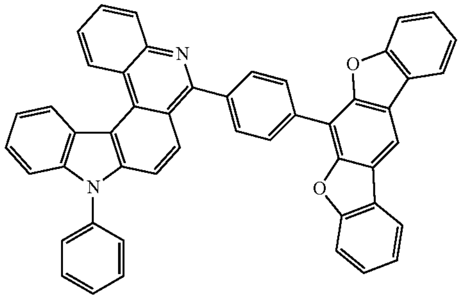

-continued
5-57
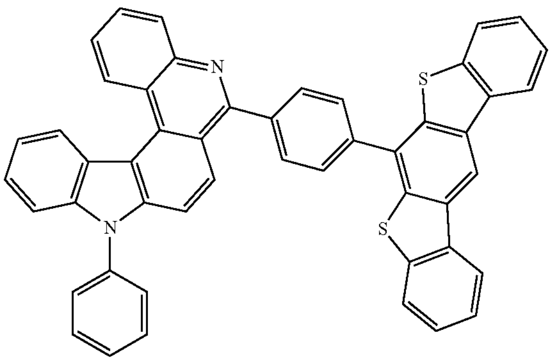
5-58
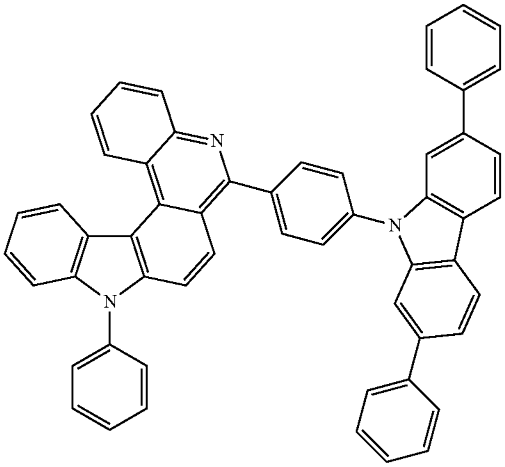
5-59
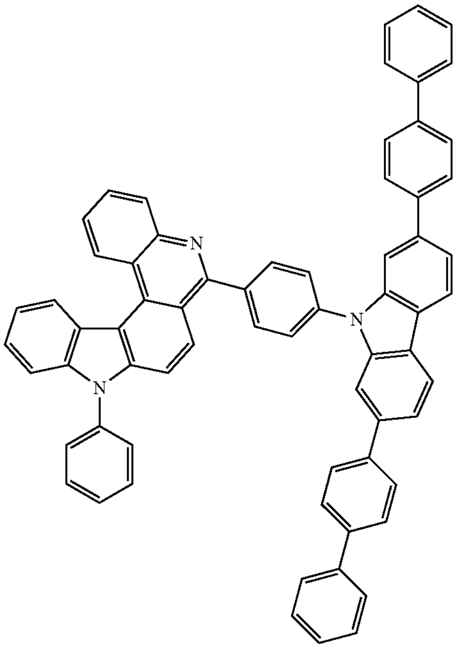
5-60
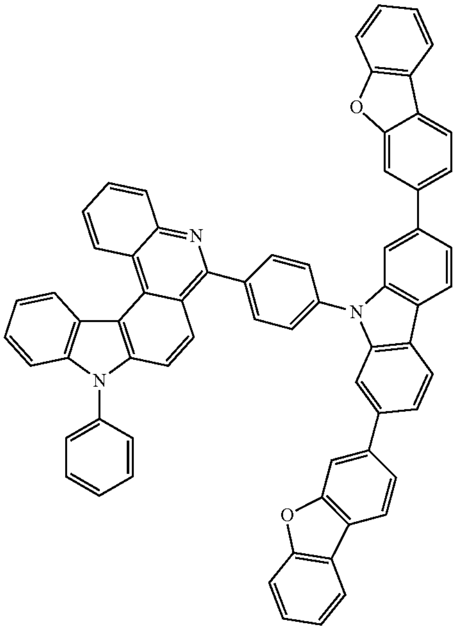
5-61
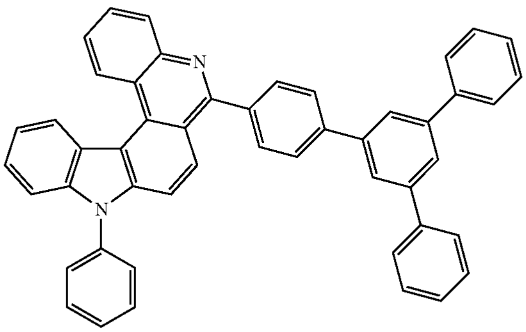
5-62
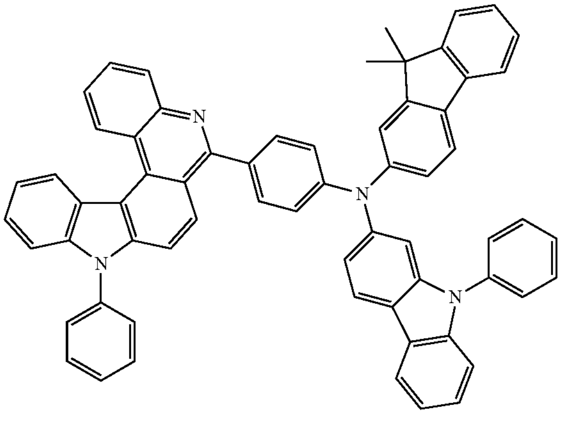

-continued
5-63
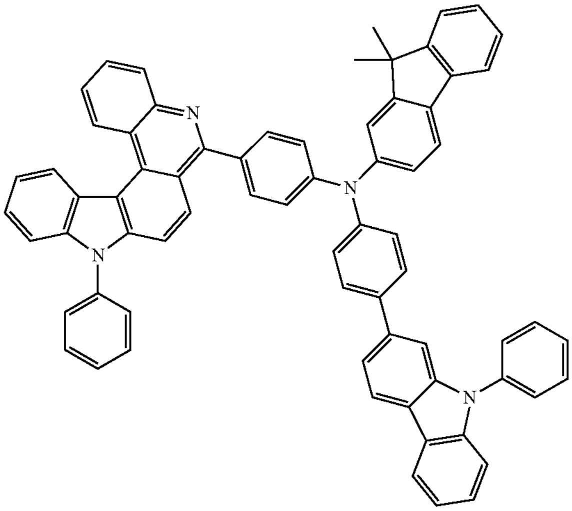
5-64
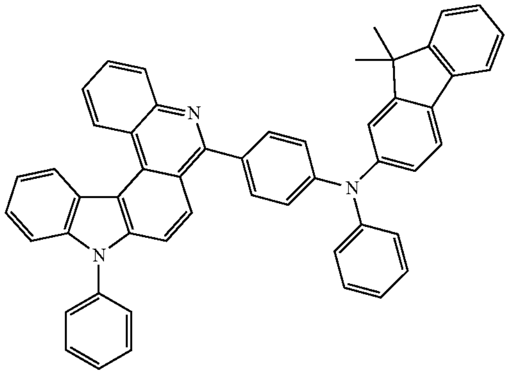
5-65
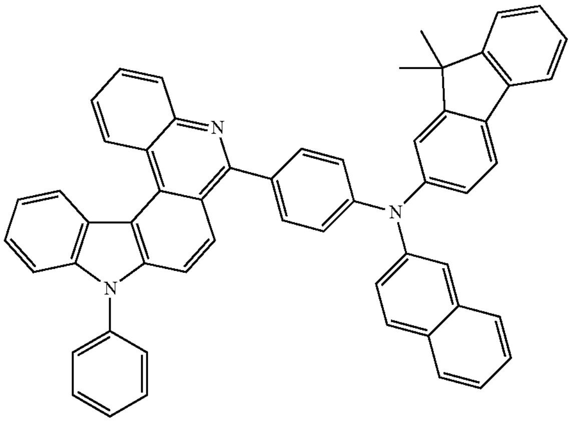
5-66
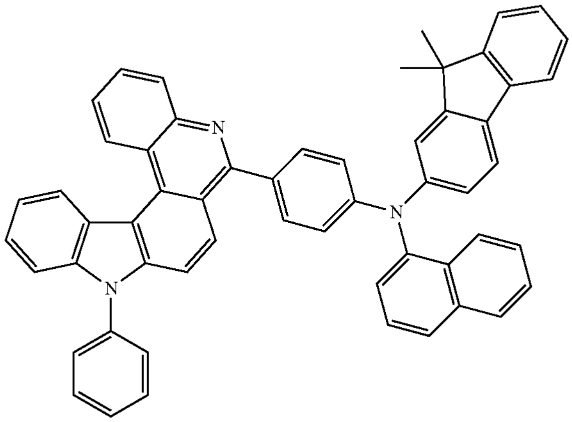
5-67
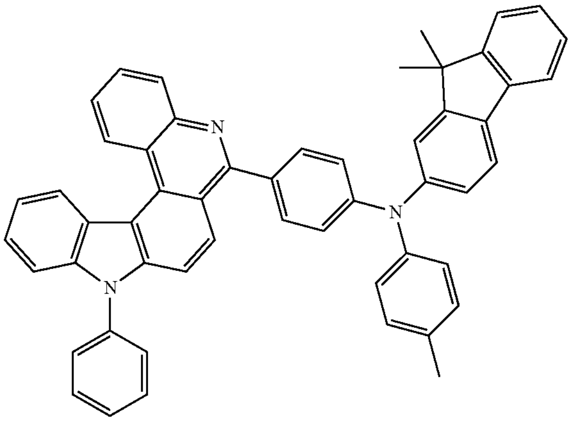
5-68
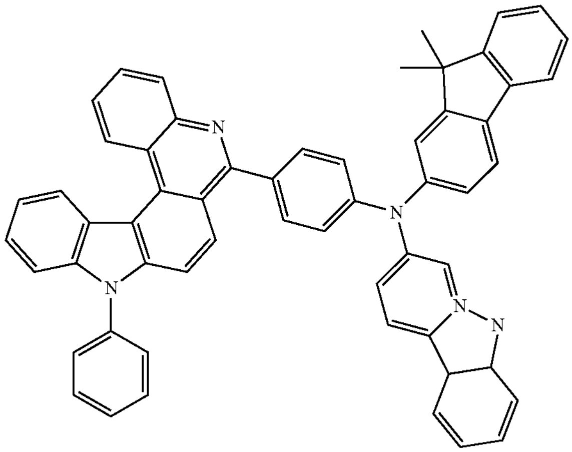

-continued
5-69
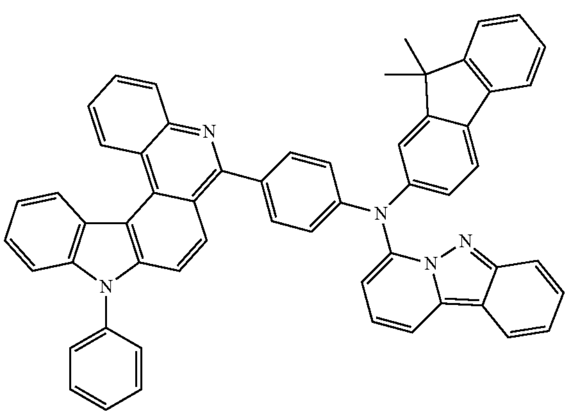
5-70
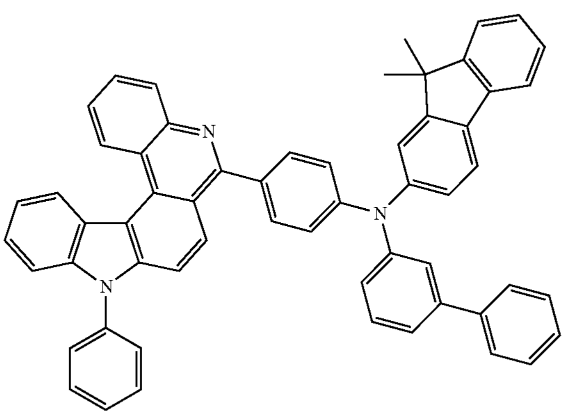
5-71
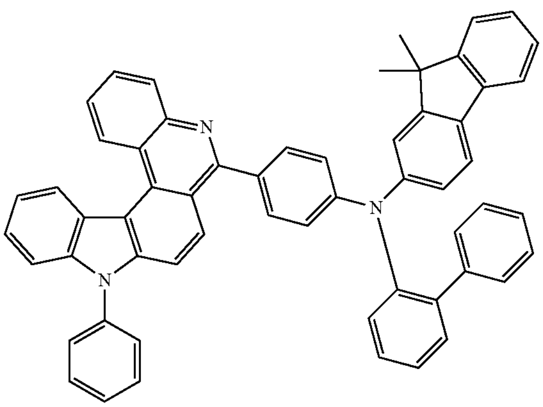
5-72
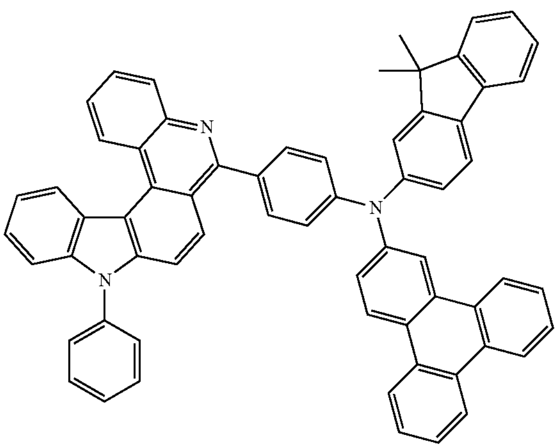
5-73
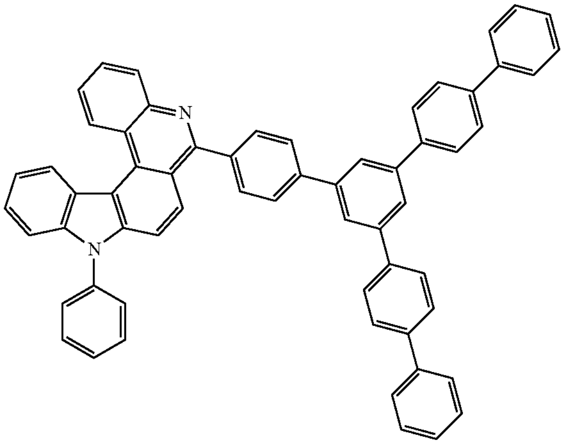
5-74
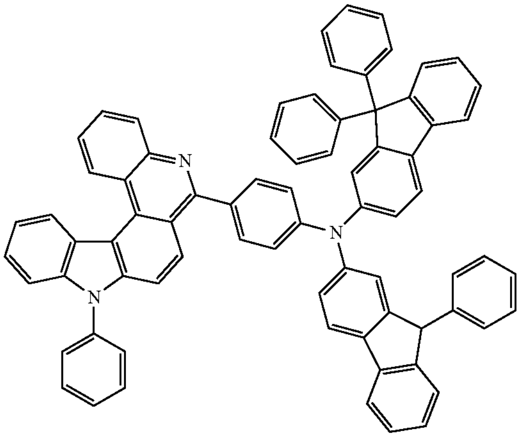

-continued
5-75
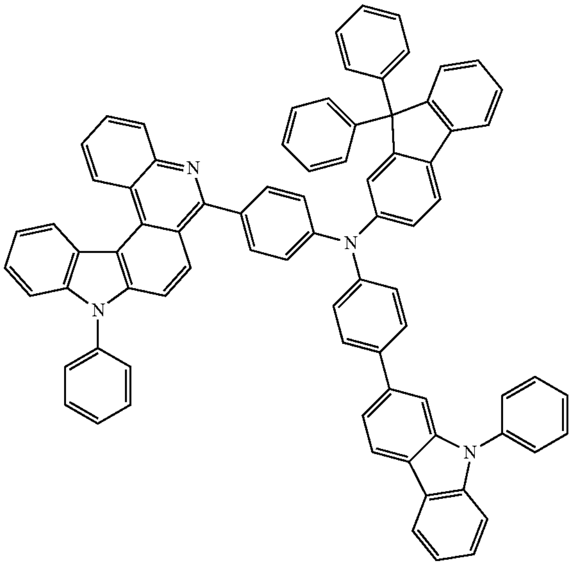
7-76
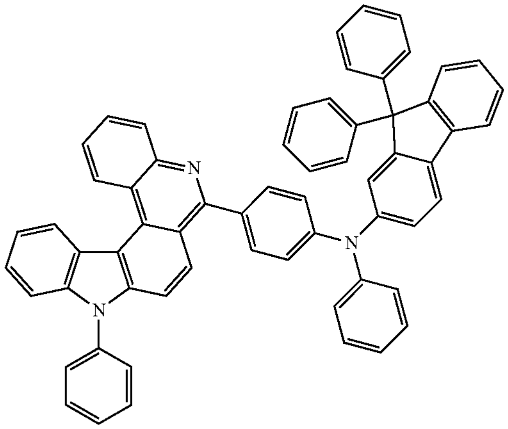
5-77
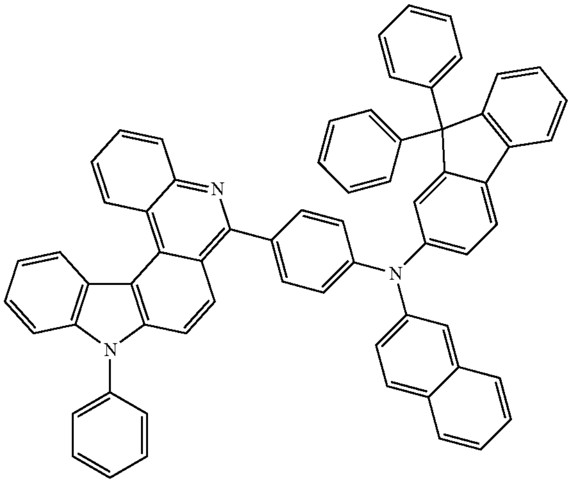
5-78
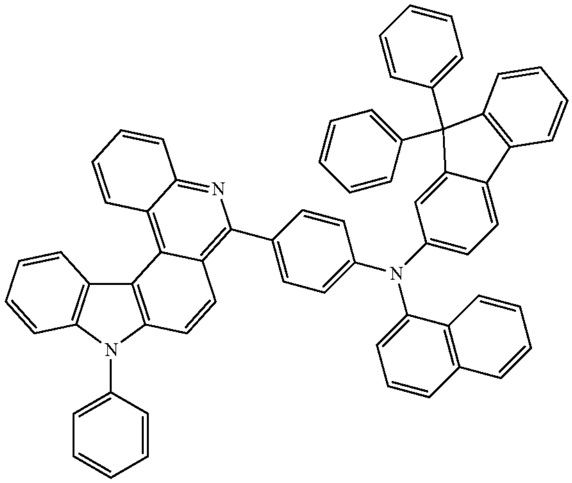
5-79
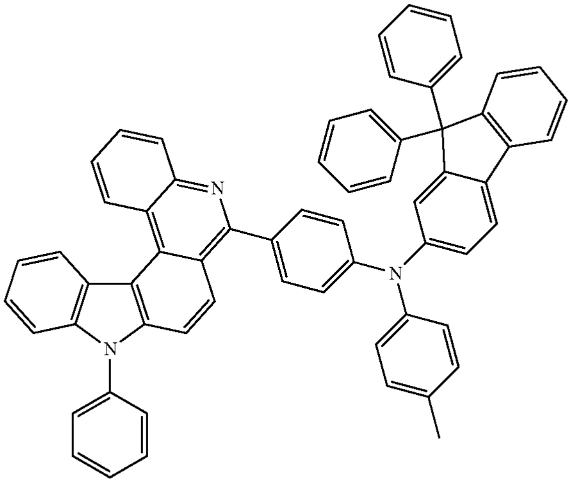
5-80
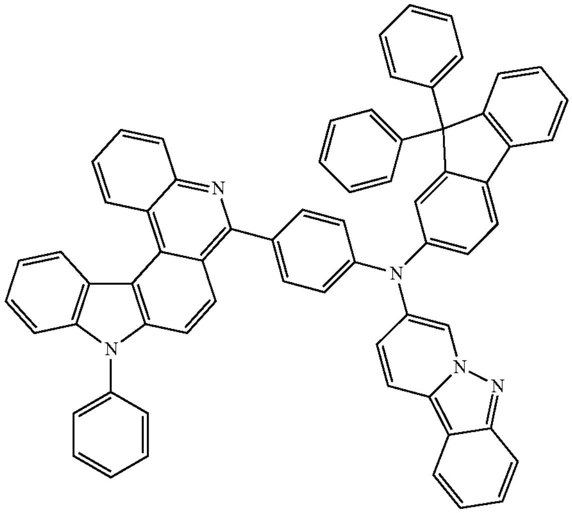

-continued
5-81
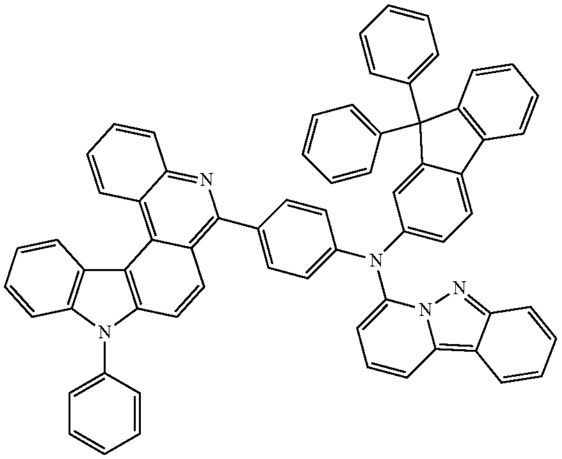
5-82
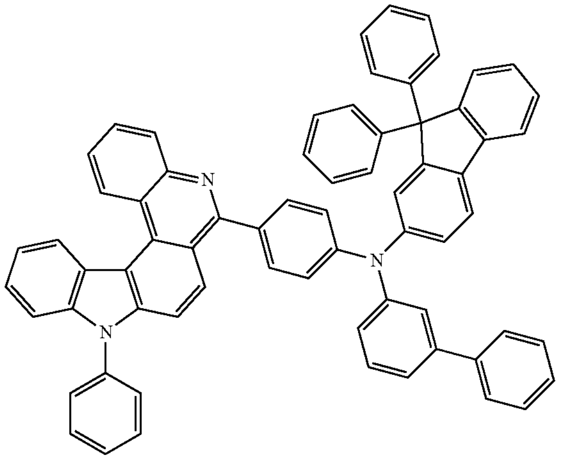
5-83
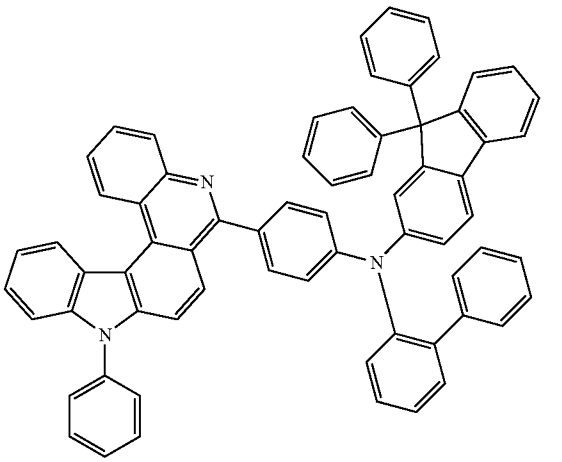
5-84
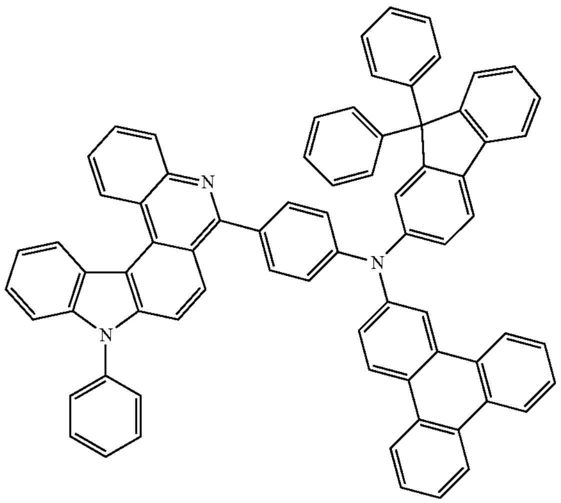
5-85
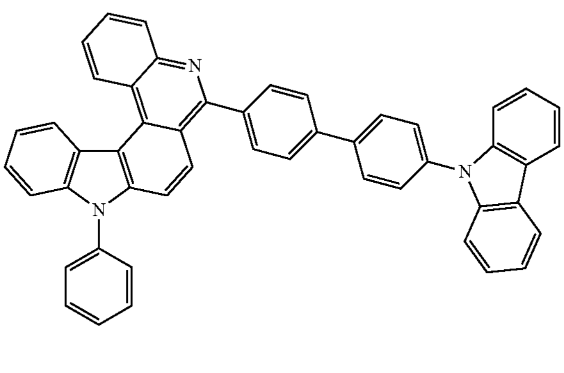
5-86
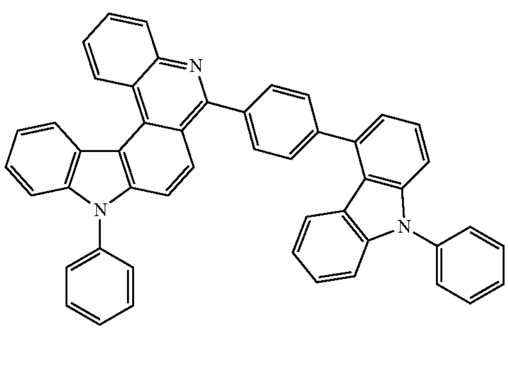

-continued
5-87
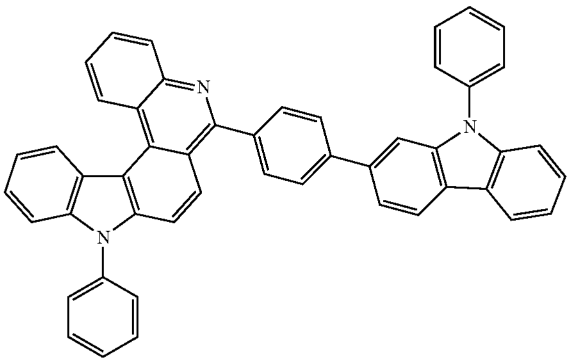
5-88
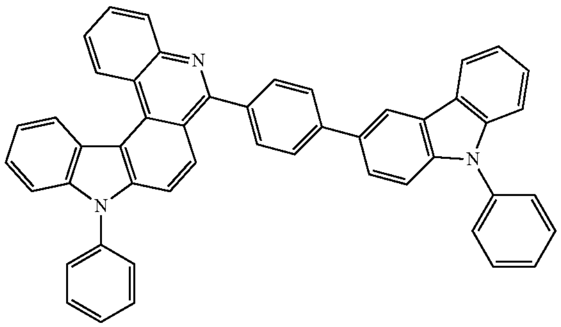
6-1
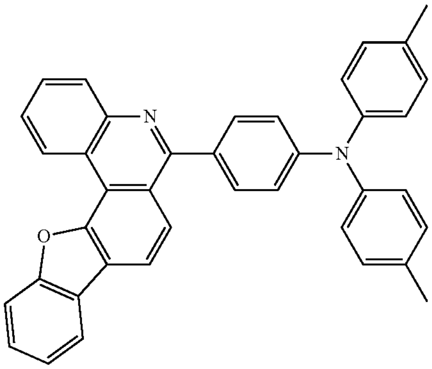
6-2
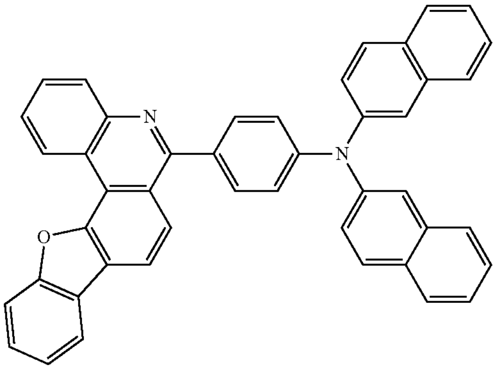
6-3
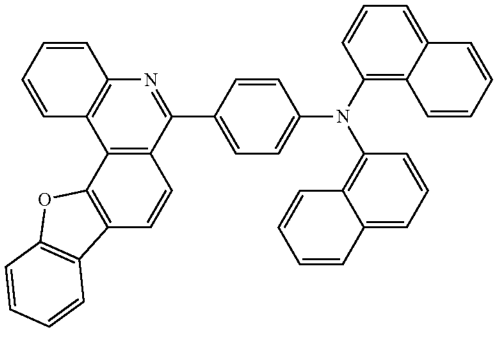
6-4
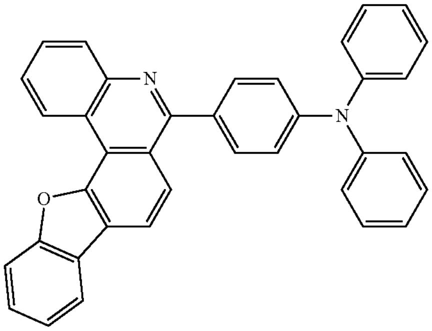
6-5
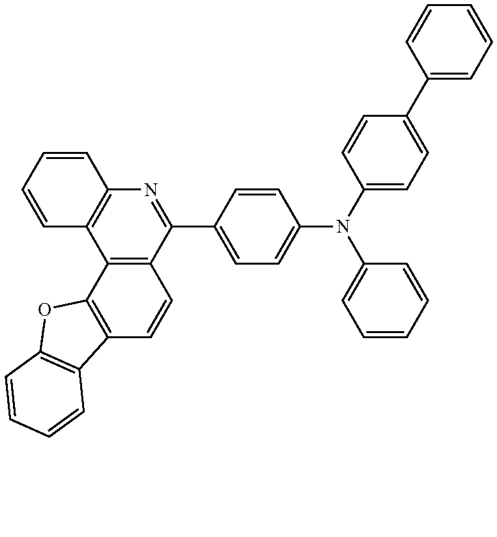

-continued
6-6
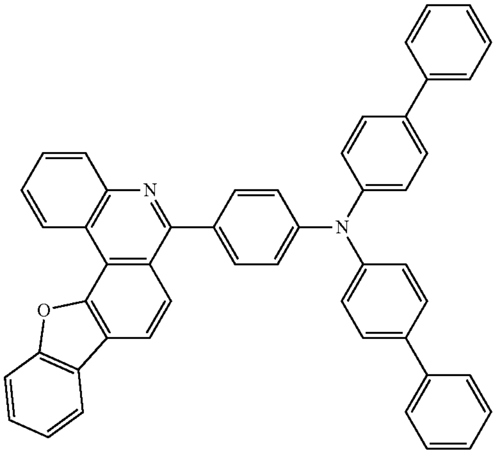
6-7
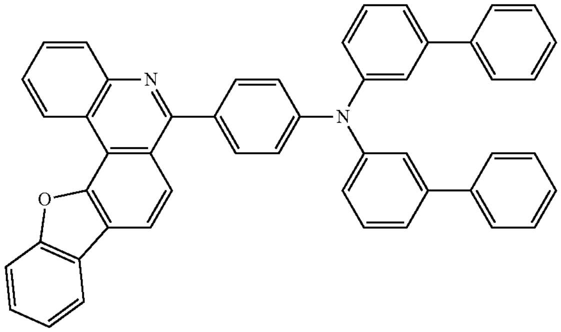
6-8
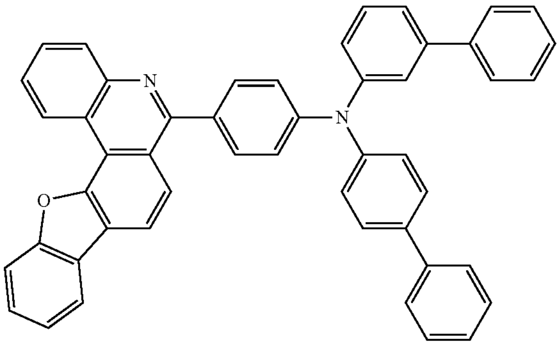
6-9
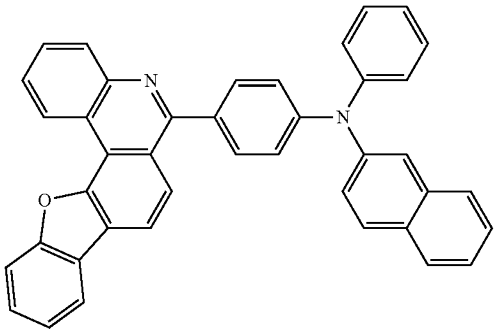
6-10
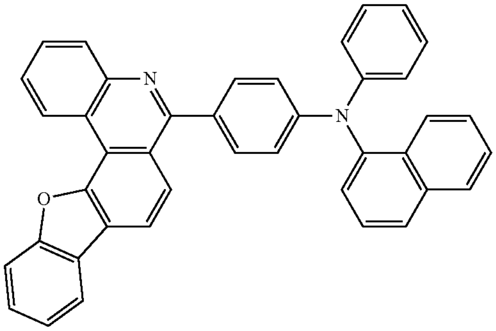
6-11
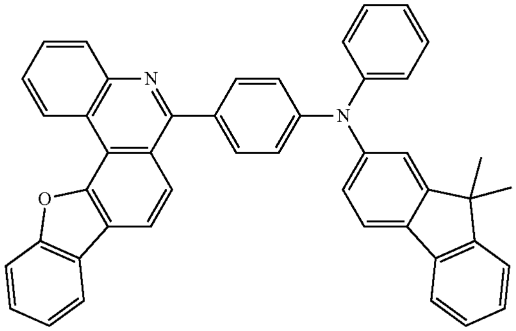
6-12
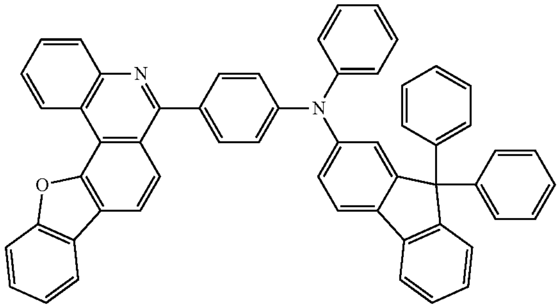
6-13
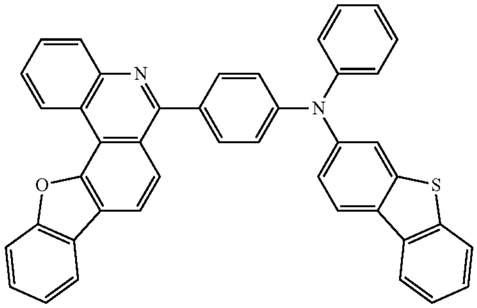

-continued
6-14
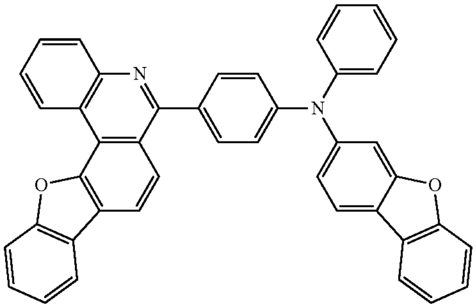
6-15
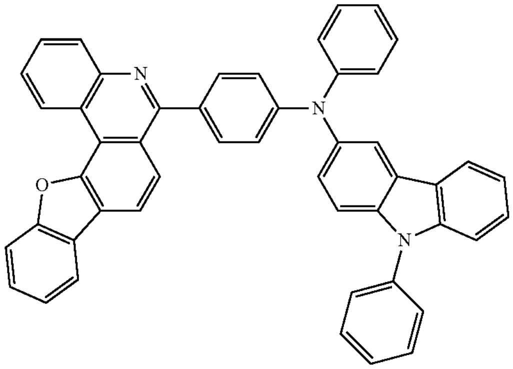
6-16
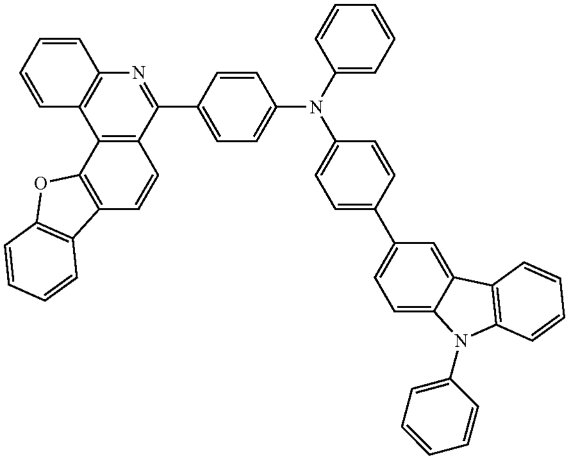
6-17
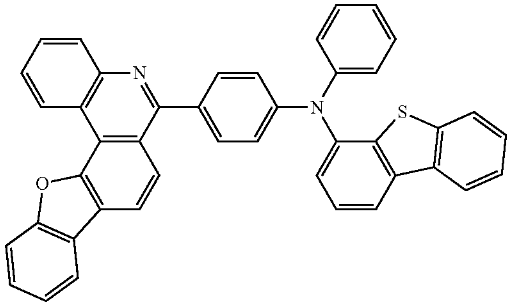
6-18
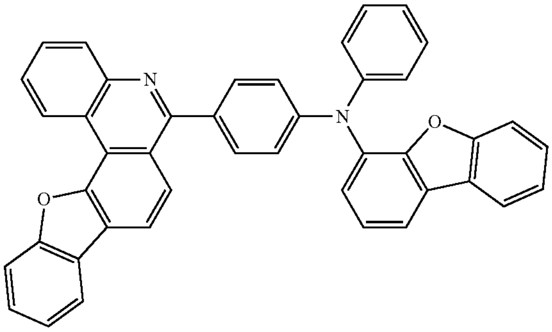
6-19
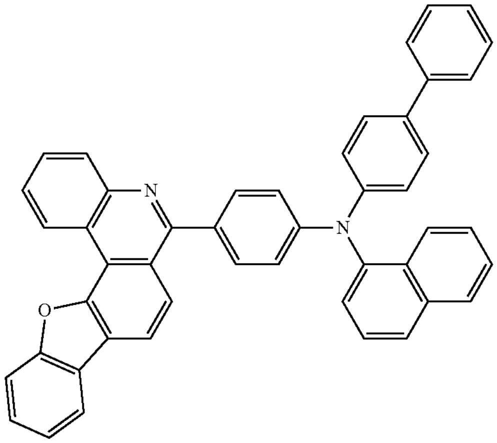

-continued
6-20
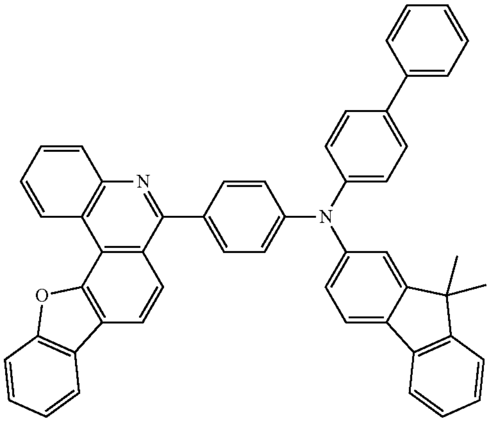
6-21
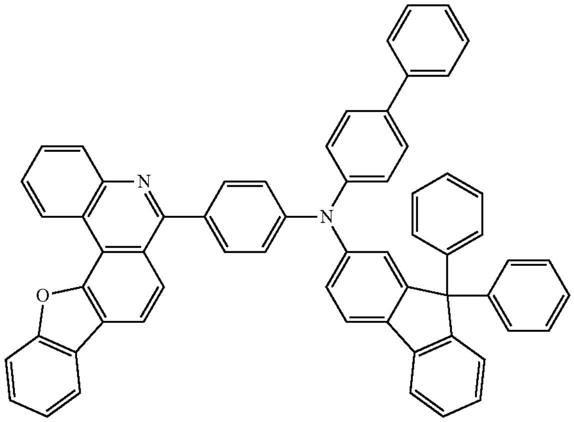
6-22
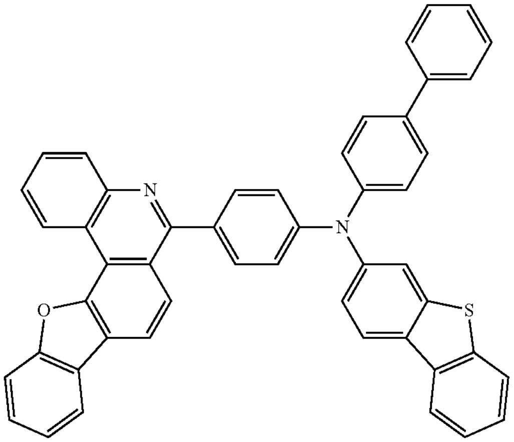
6-23
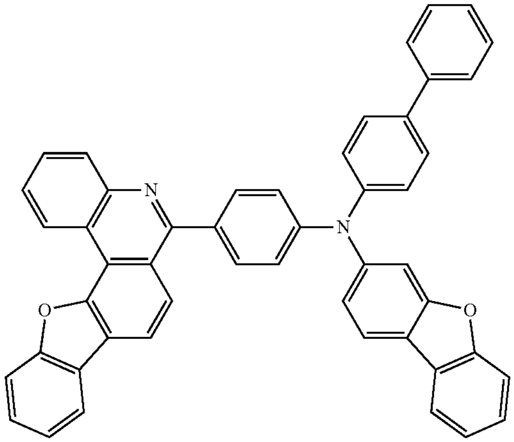
6-24
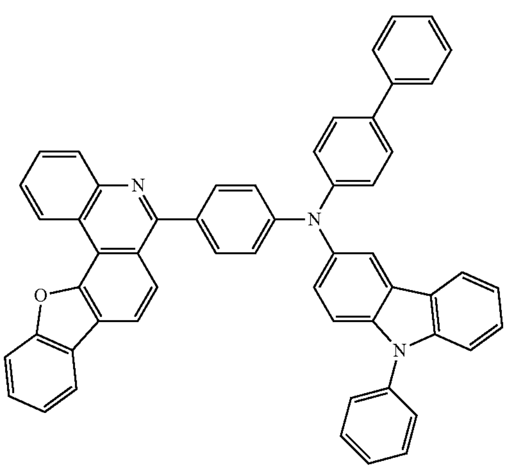
6-25
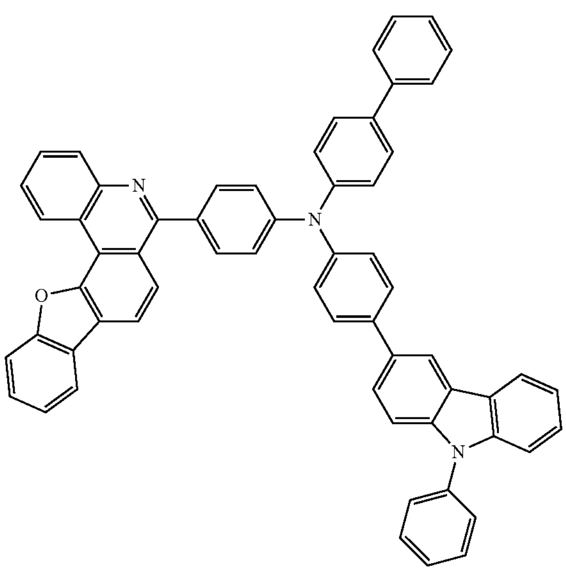

-continued
6-26
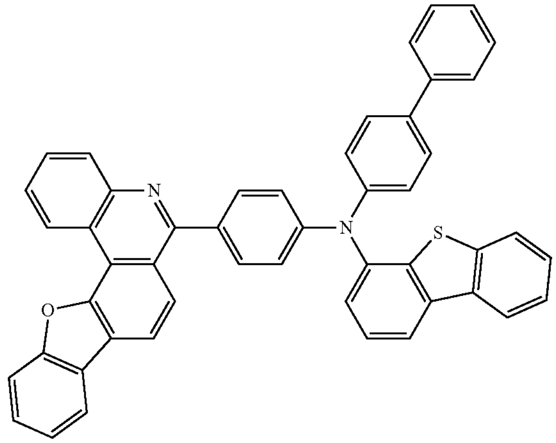
6-27
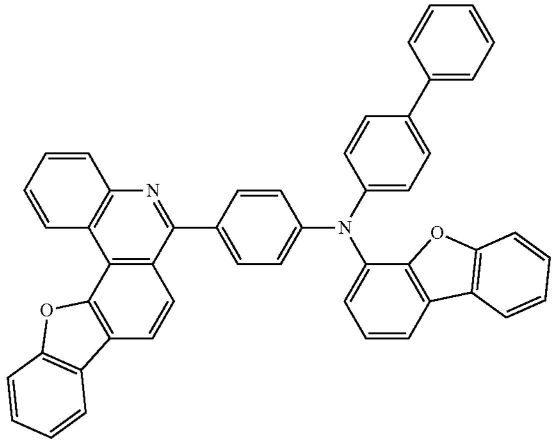
6-28
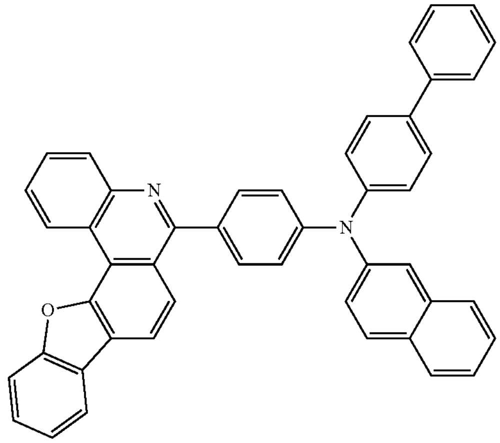
6-29
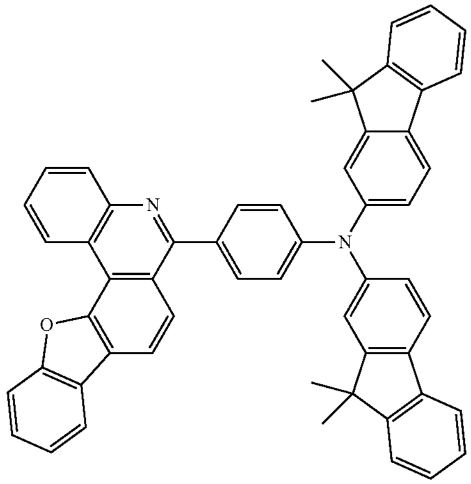
6-30
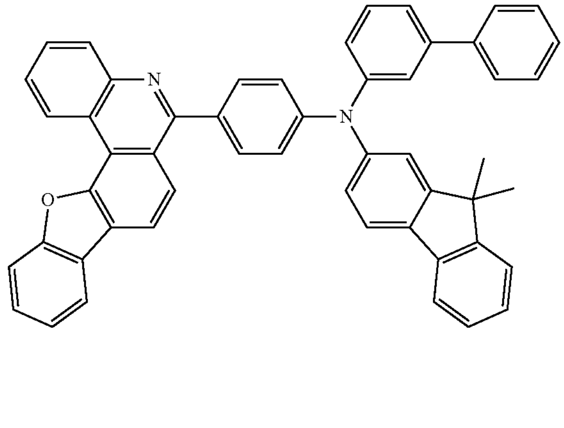
6-31
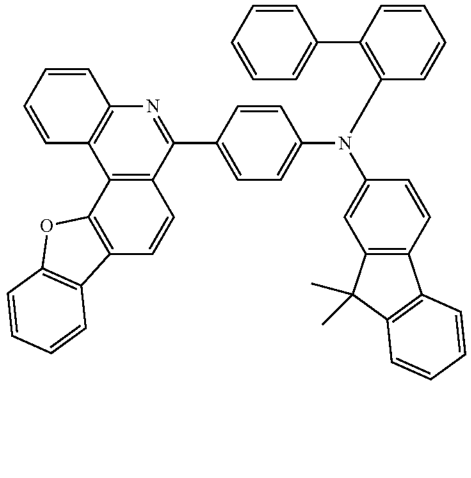

-continued
6-32
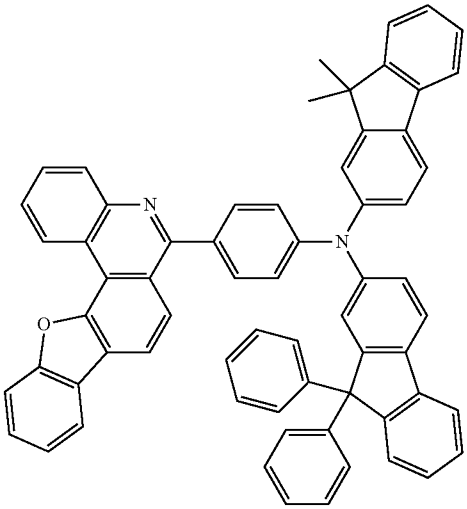
6-33
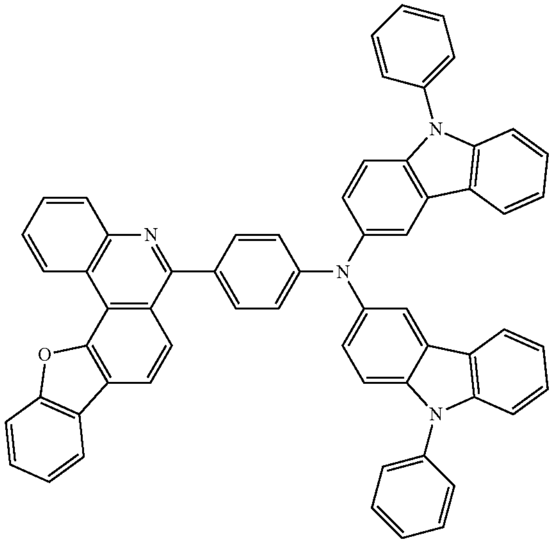
6-34
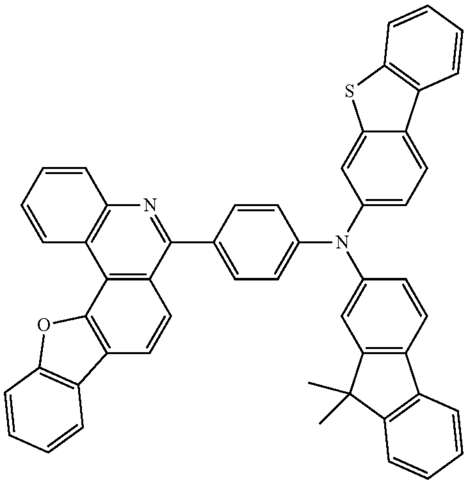
6-35
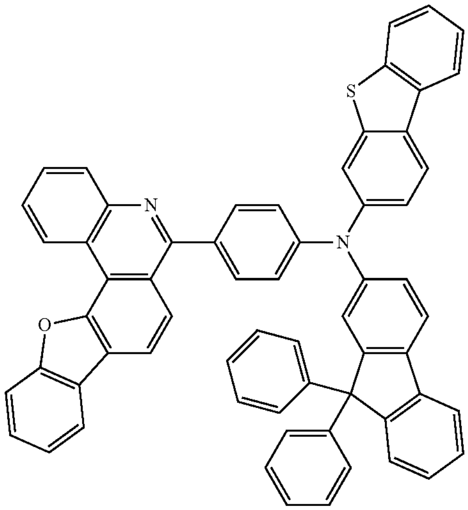
6-36
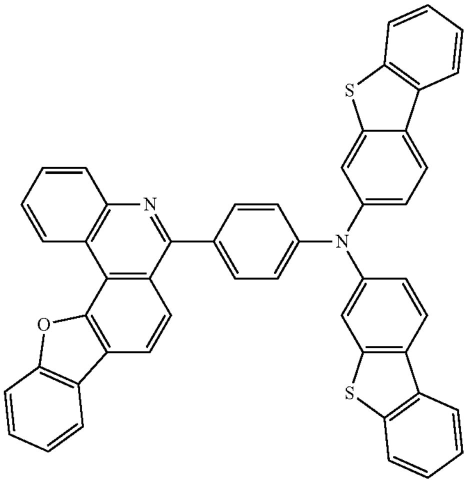
6-37
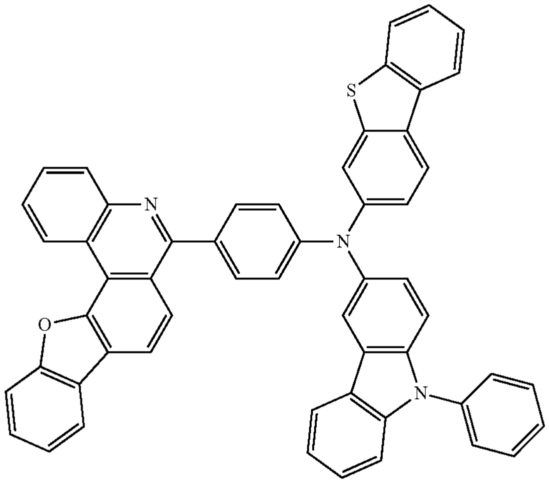

-continued
6-38
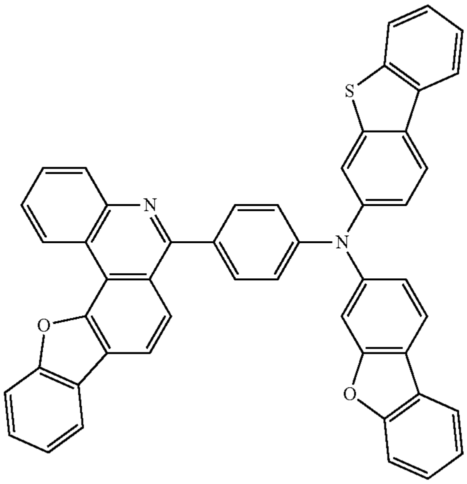
6-39
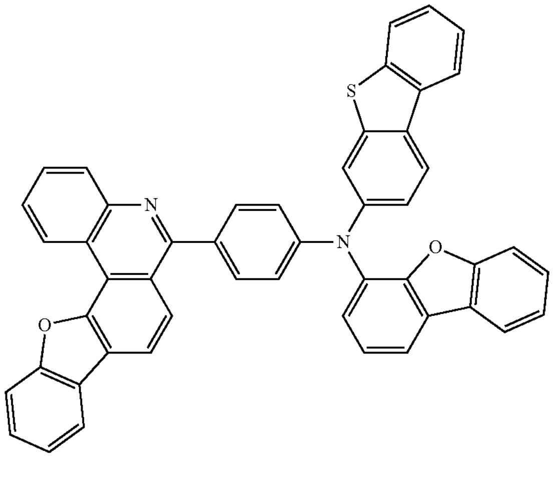
6-40
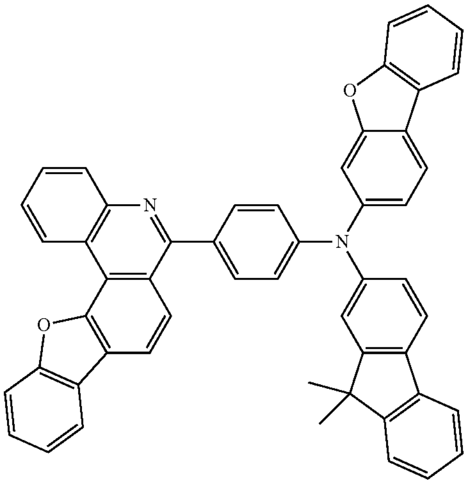
6-41
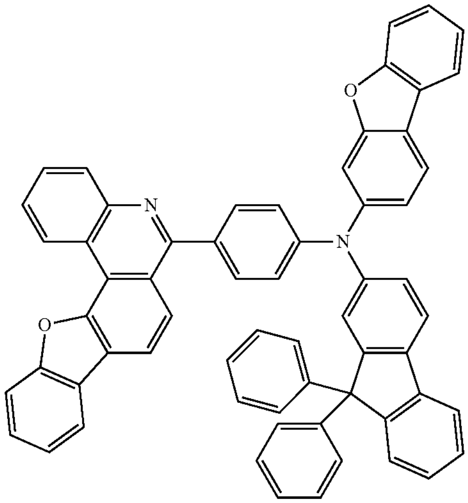
6-42
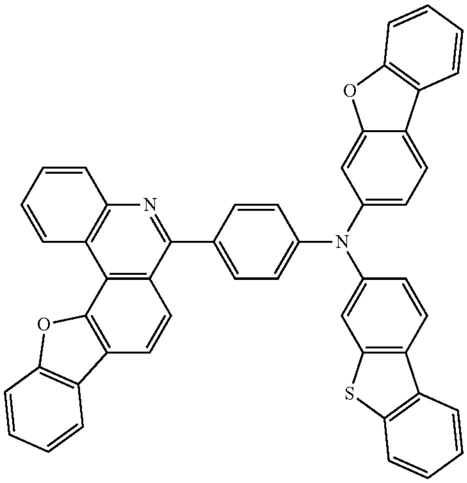
6-43
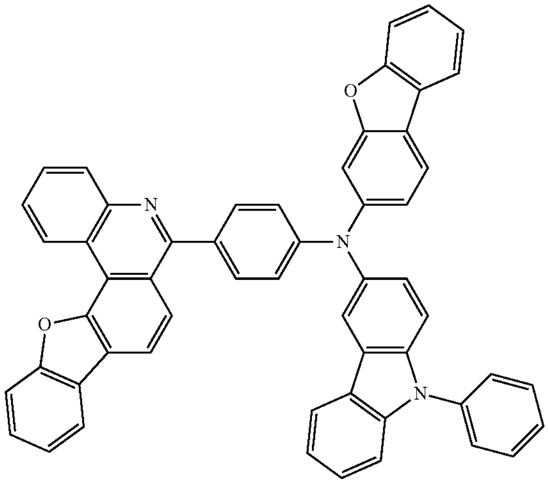

-continued
6-44
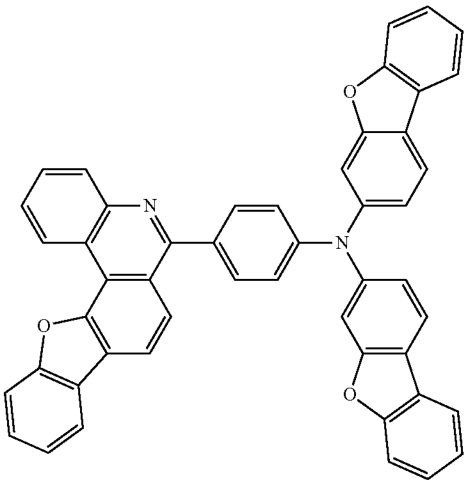
6-45
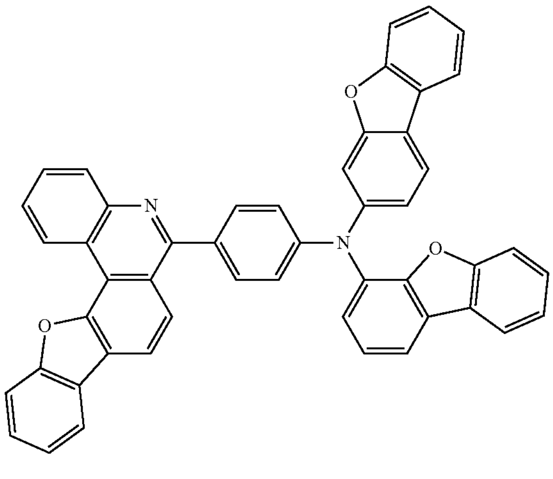
6-46
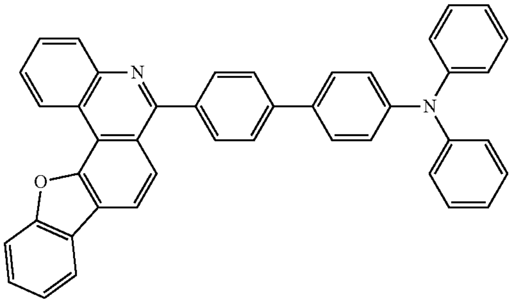
6-47
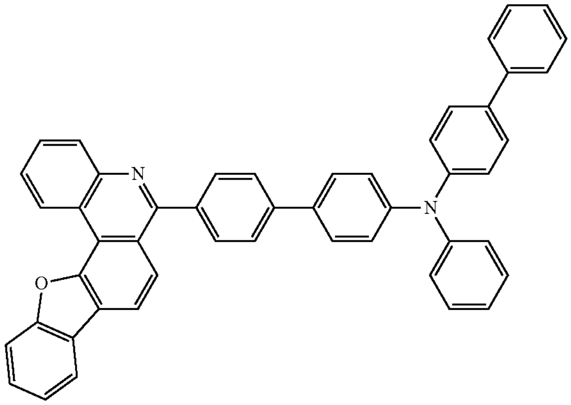
6-48
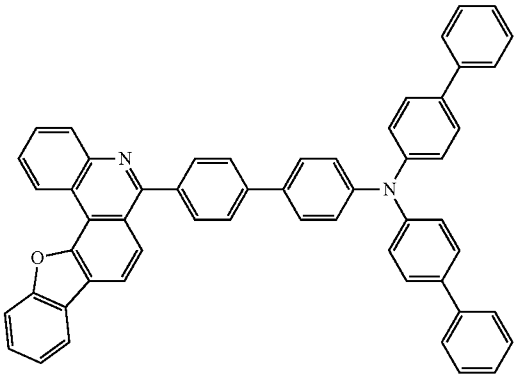
6-49
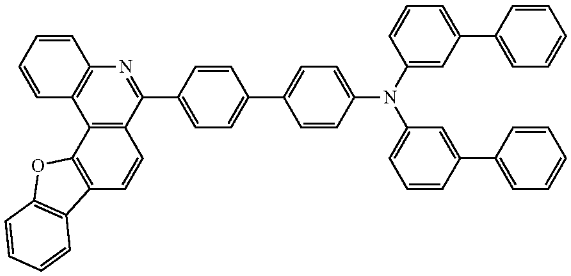

-continued
6-50
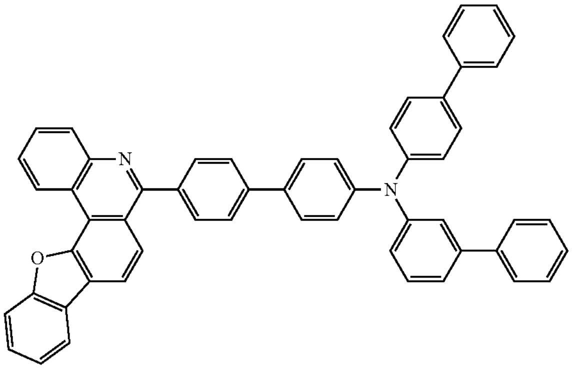
6-51
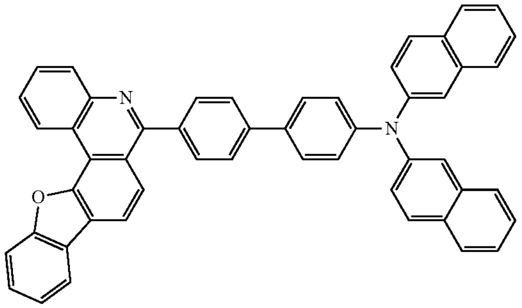
6-52
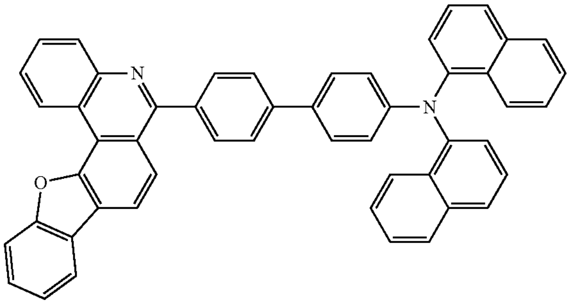
6-53
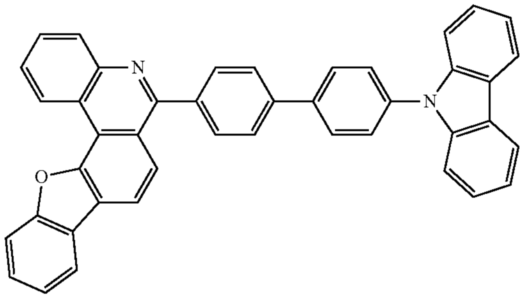
6-54
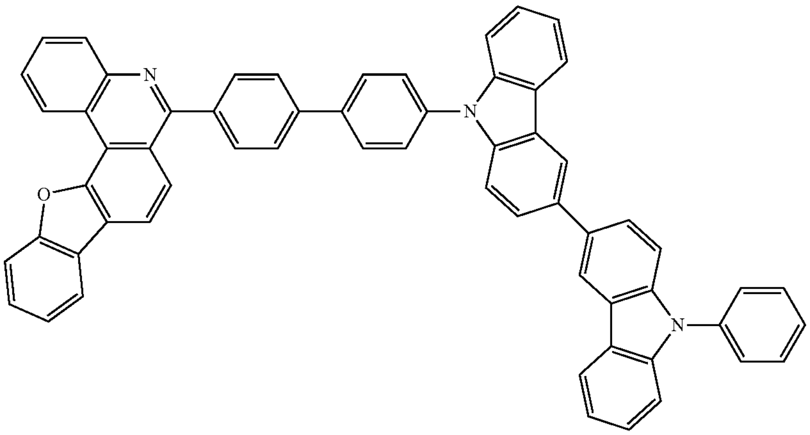
6-55
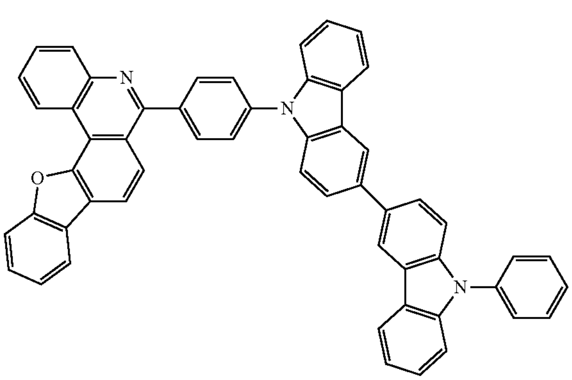
6-56
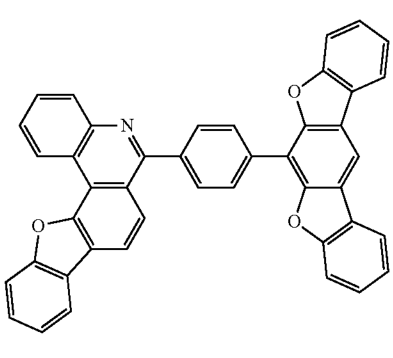

-continued
6-57
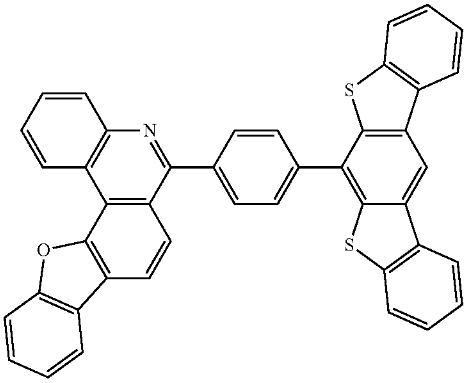
6-58
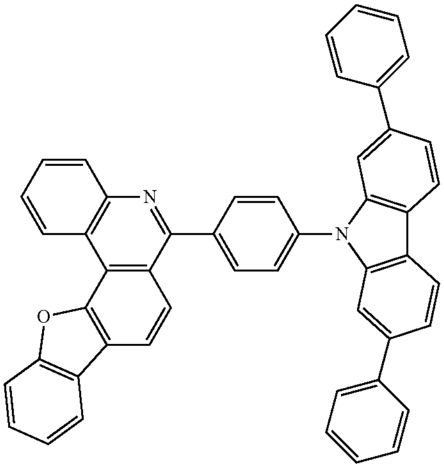
6-59
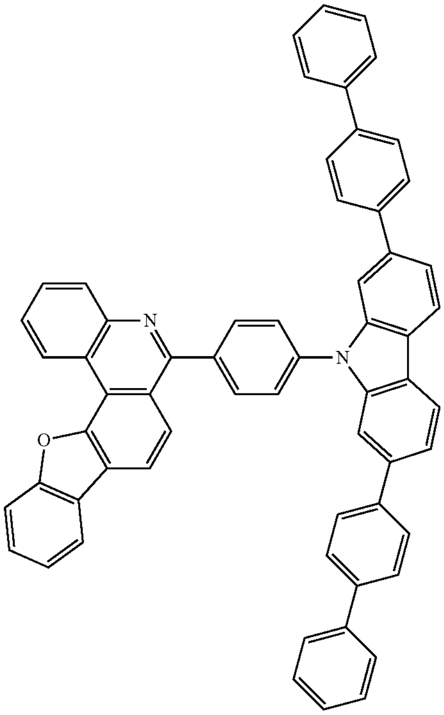
6-60
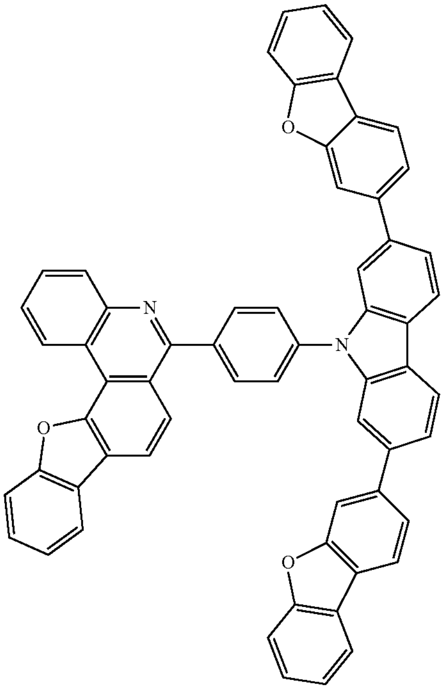
6-61
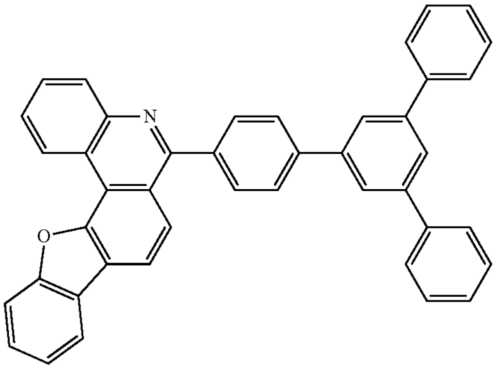
6-62
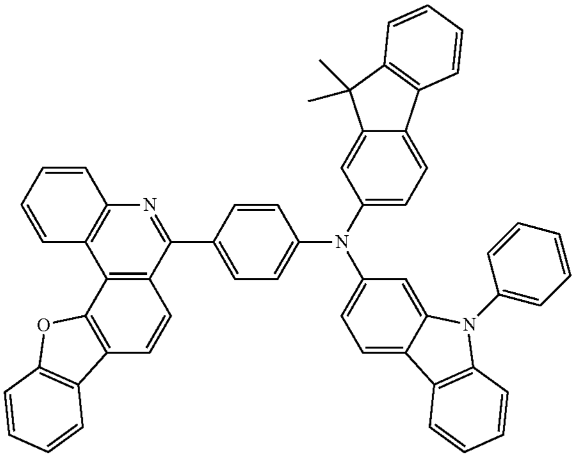

-continued
6-63
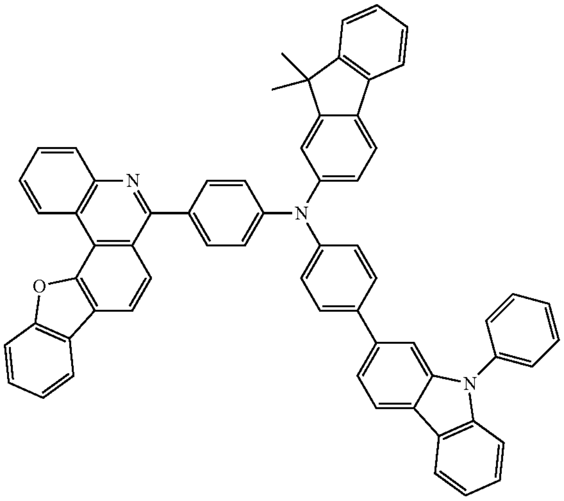
6-64
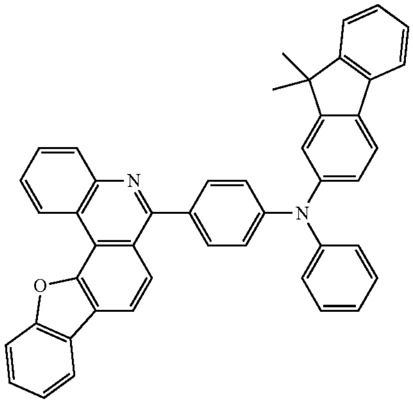
6-65
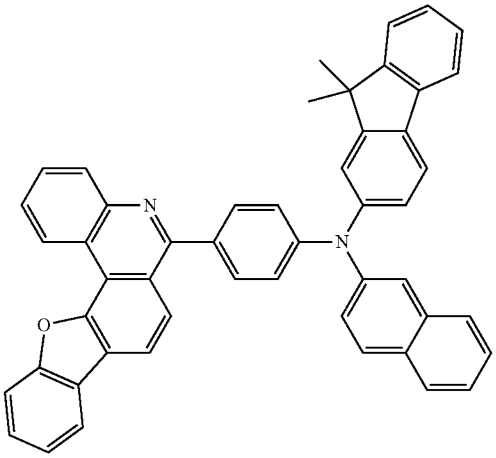
6-66
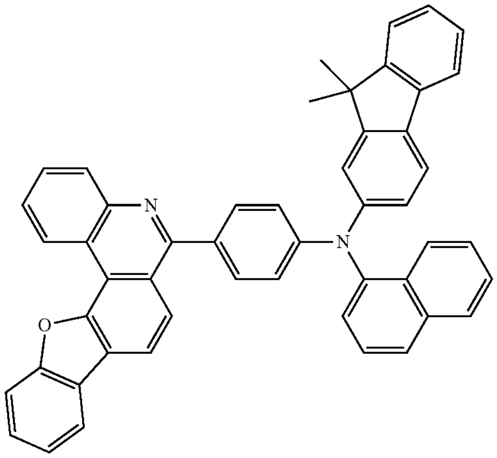
6-67
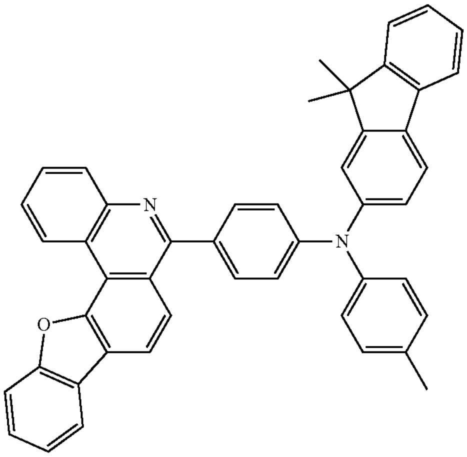
6-68
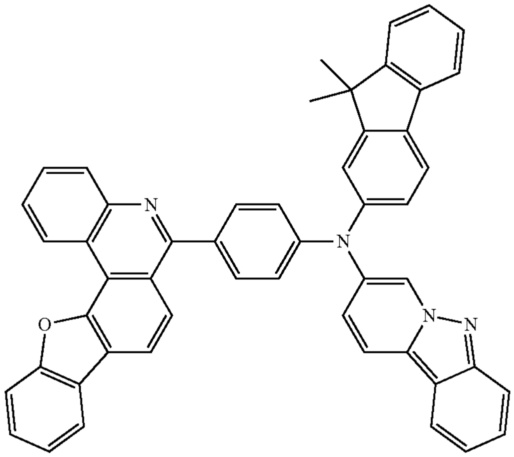

-continued
6-69
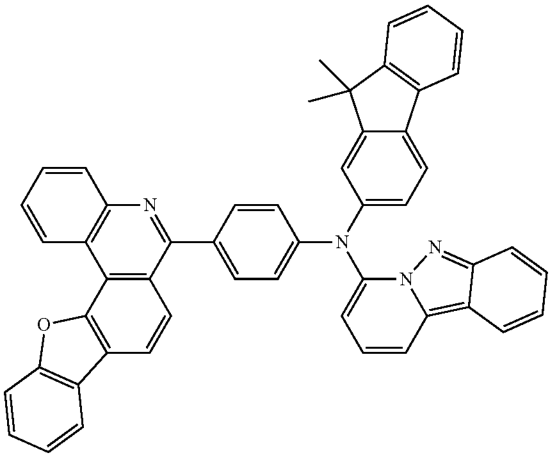
6-70
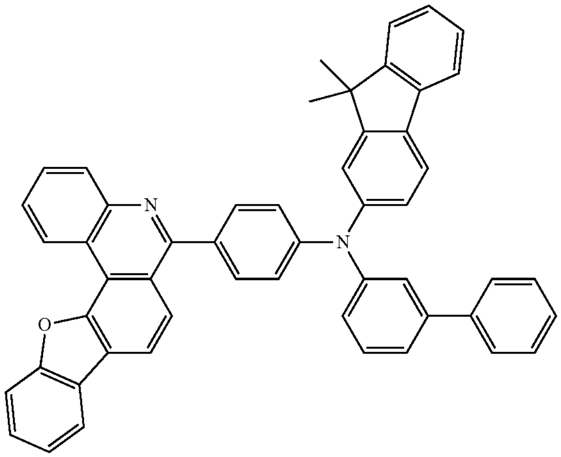
6-71
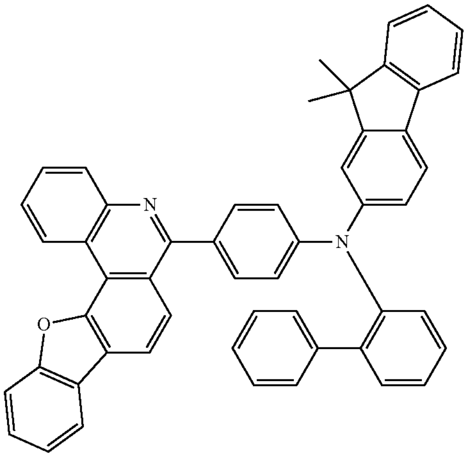
6-72
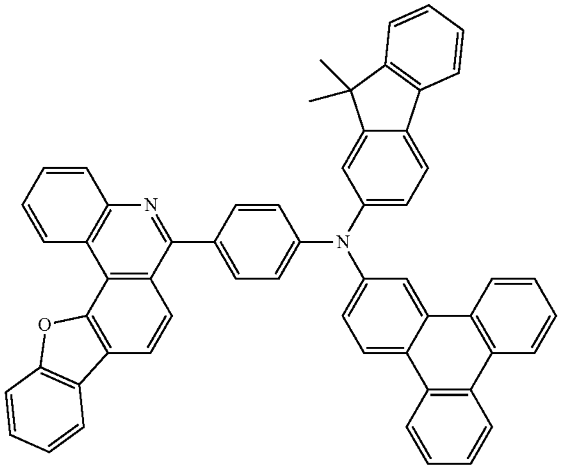
6-73
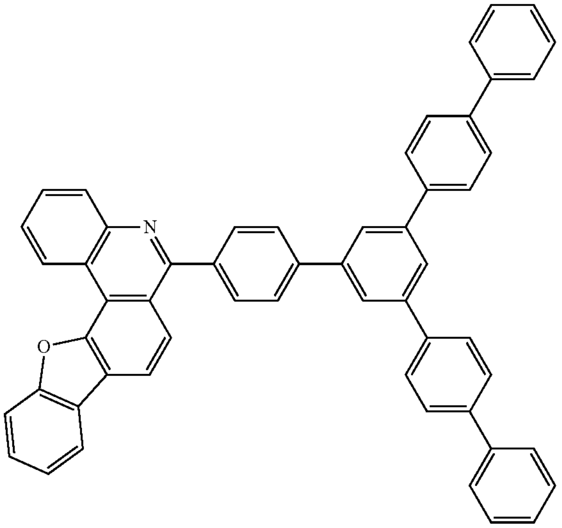
6-74
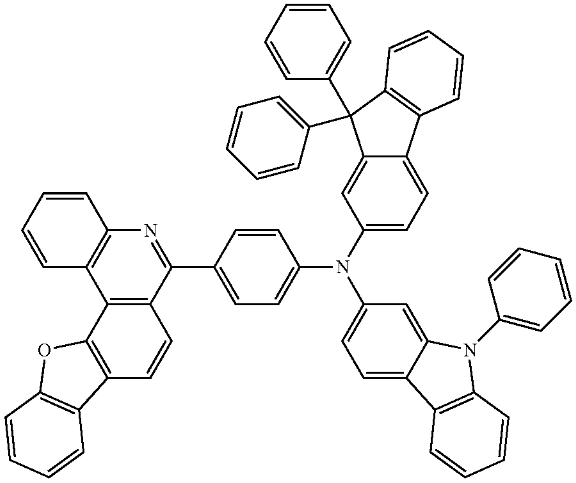

-continued
6-75
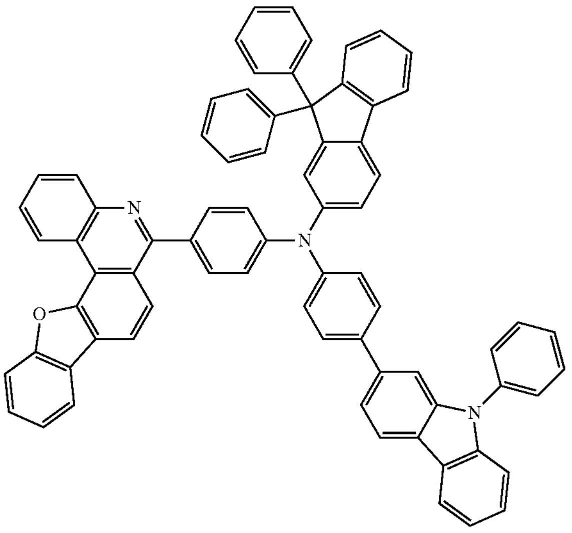
6-76
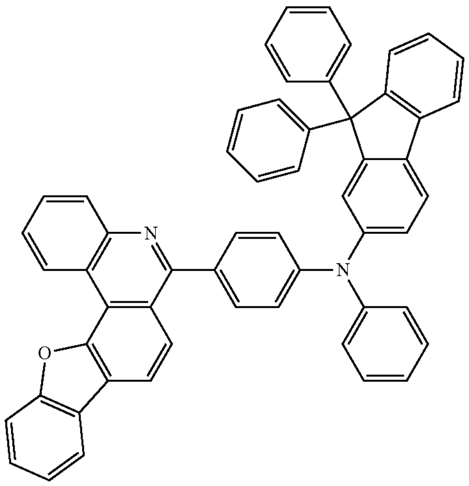
6-77
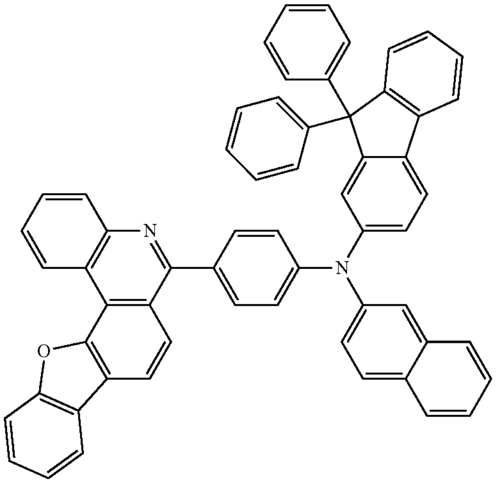
6-78
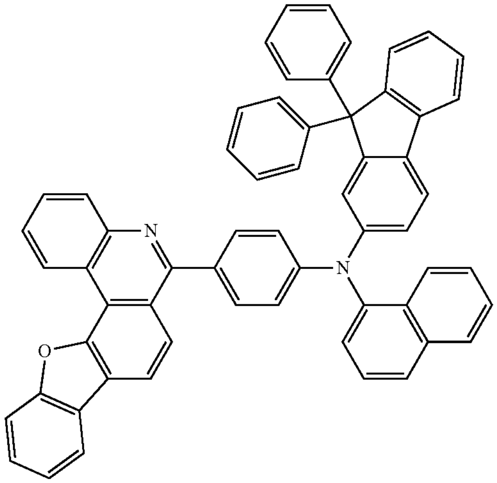
6-79
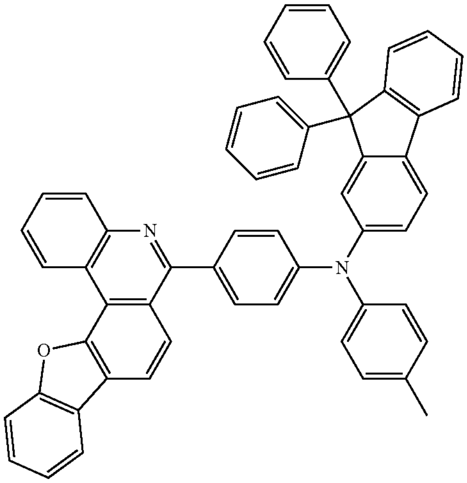
6-80
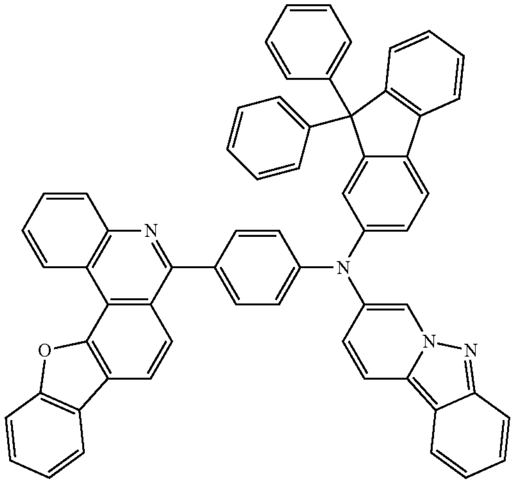

-continued
6-81
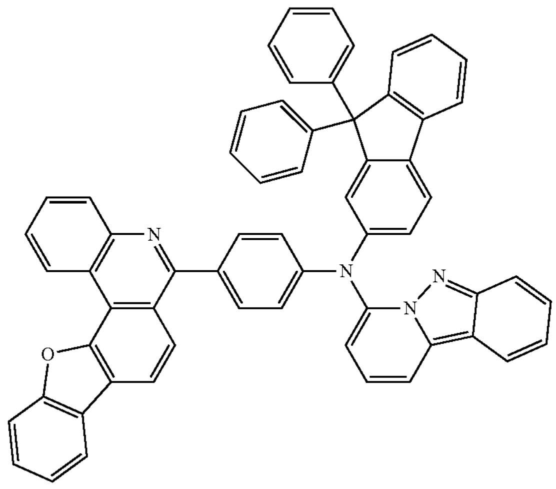
6-82
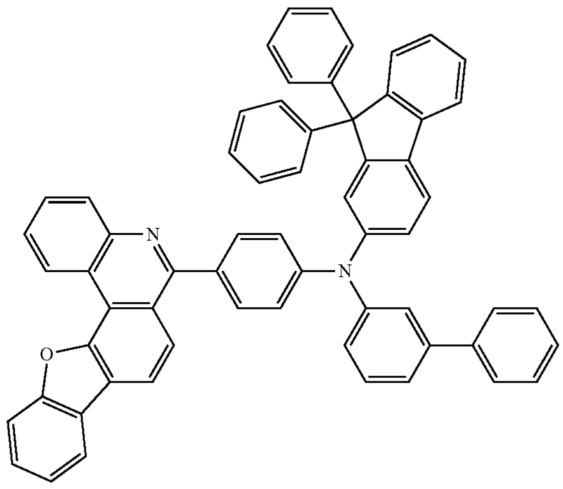
6-83
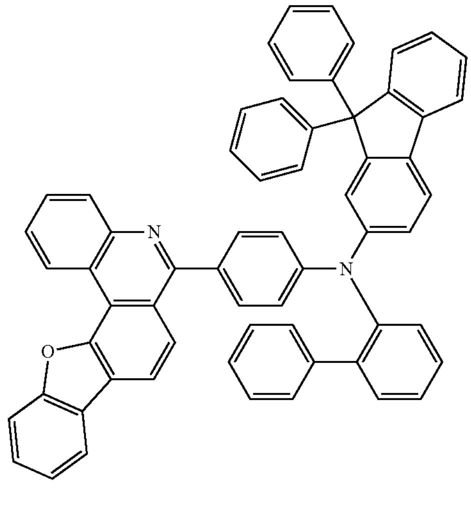
6-84
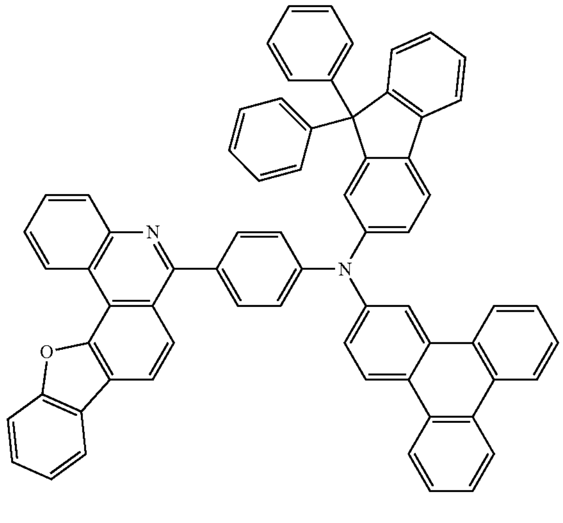
6-85
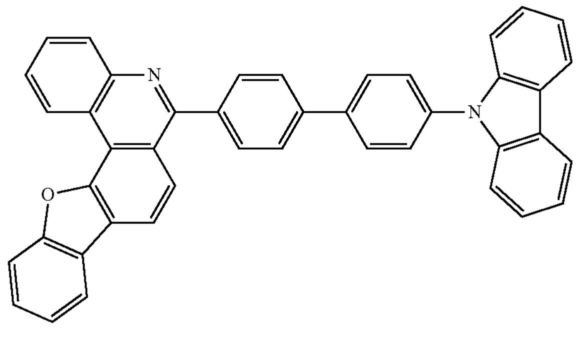
6-86
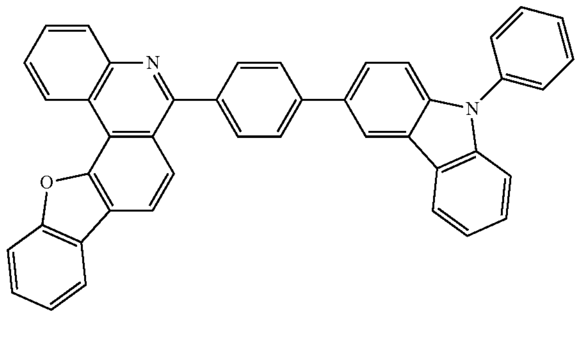

-continued
6-87
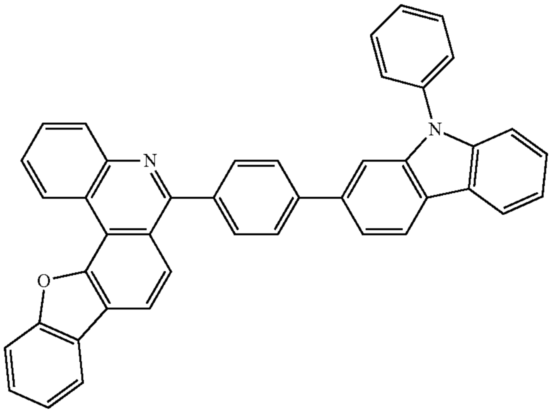
6-88
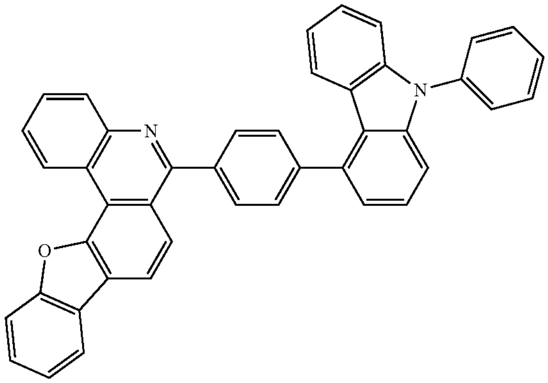
7-1
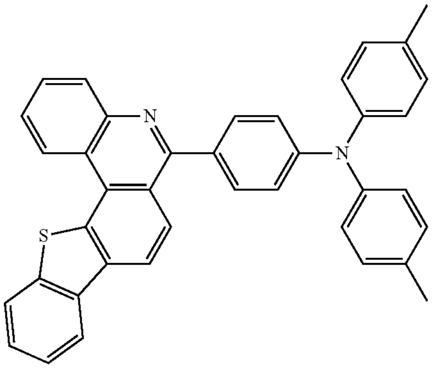
7-2
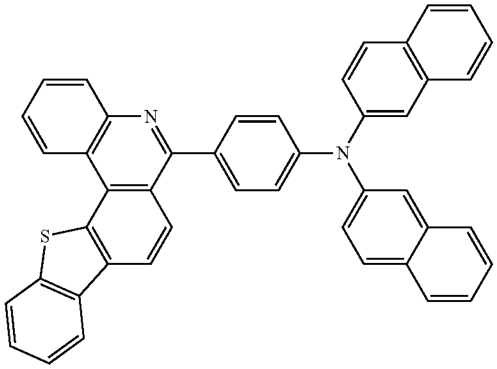
7-3
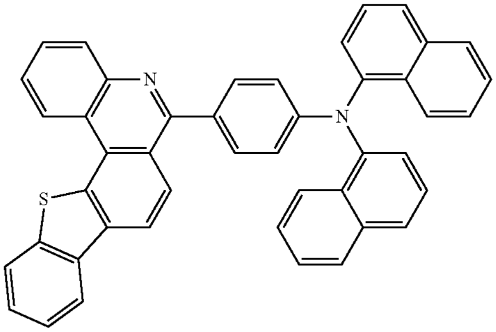
7-4
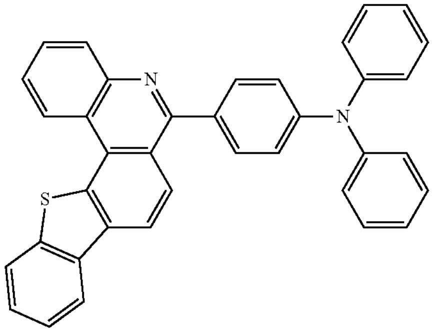
7-5
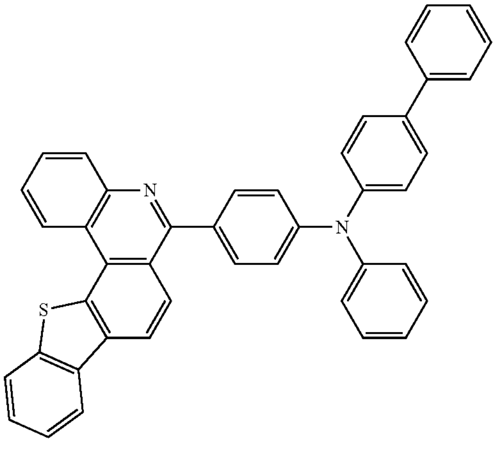
7-6
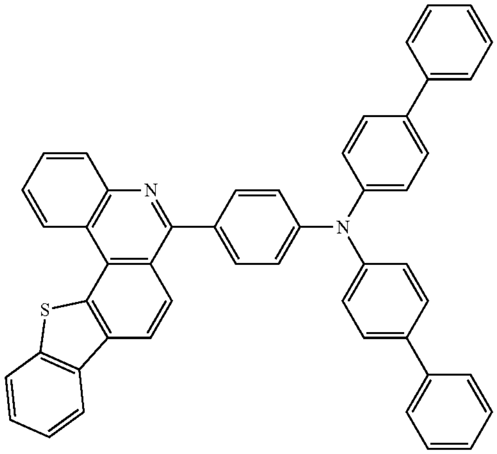

-continued
7-7
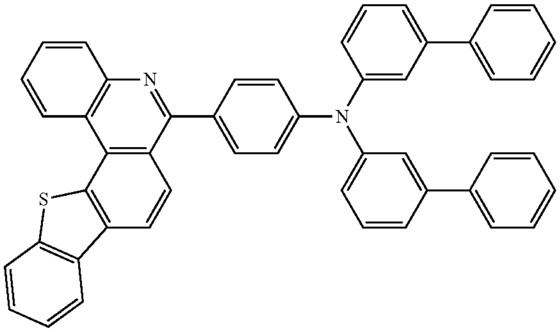
7-8
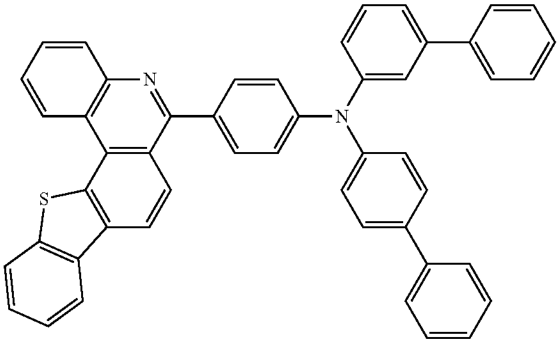
7-9
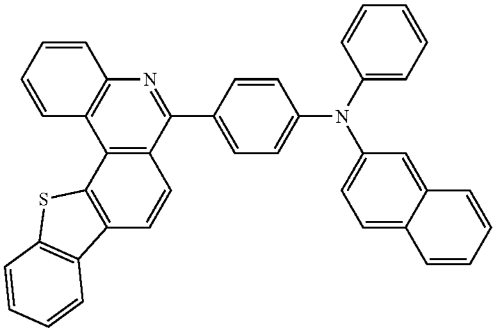
7-10
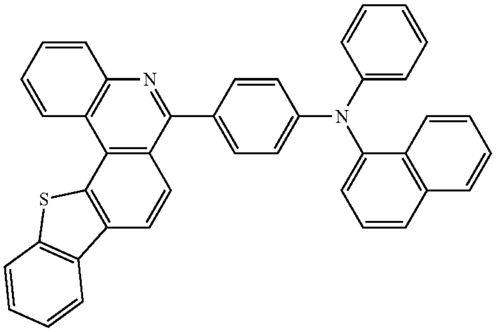
7-11
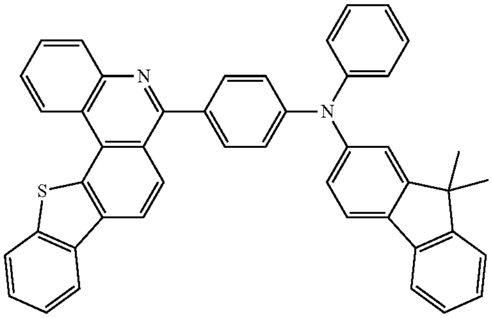
7-12
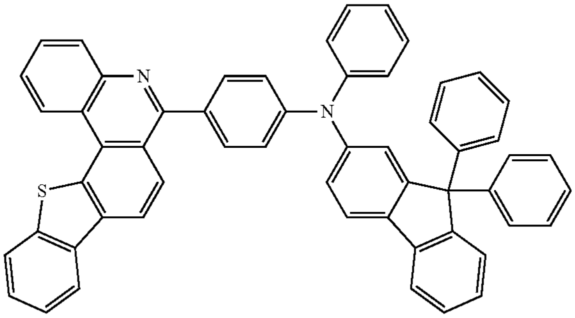
7-13
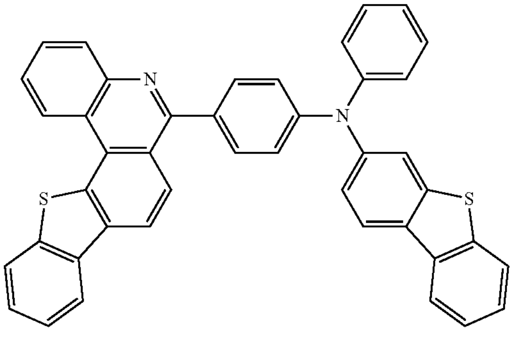
7-14
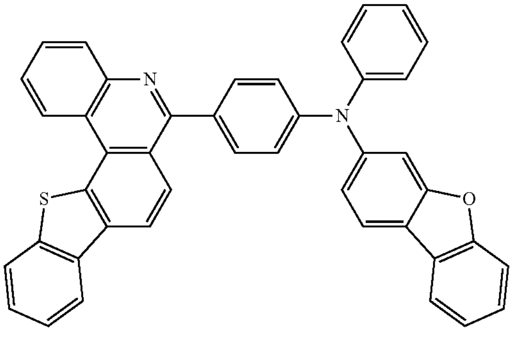

-continued
7-15
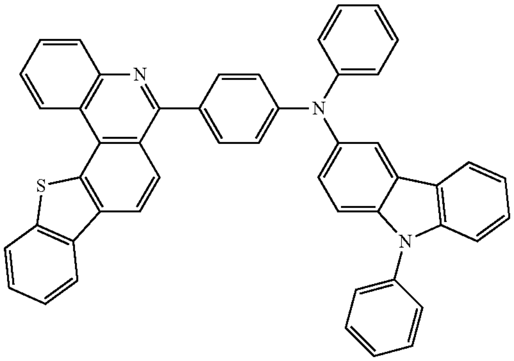
7-16
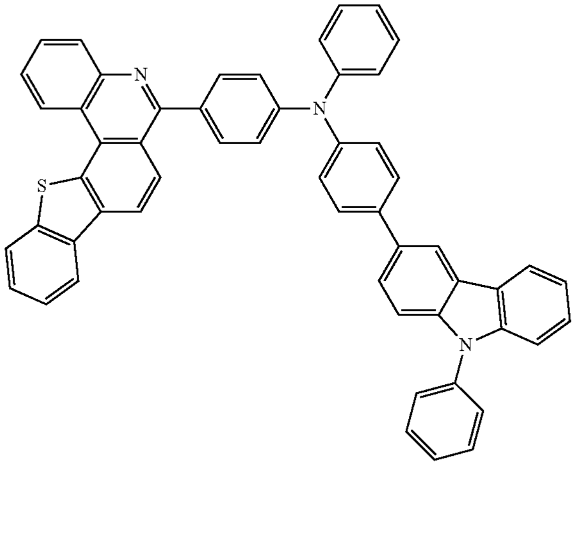
7-17
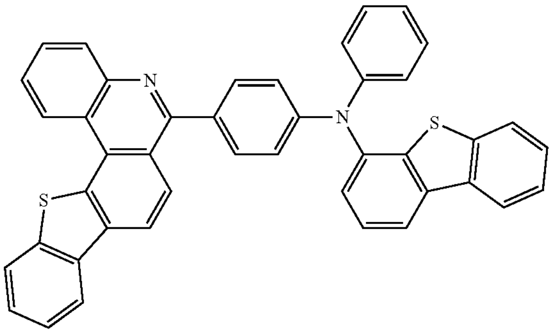
7-18
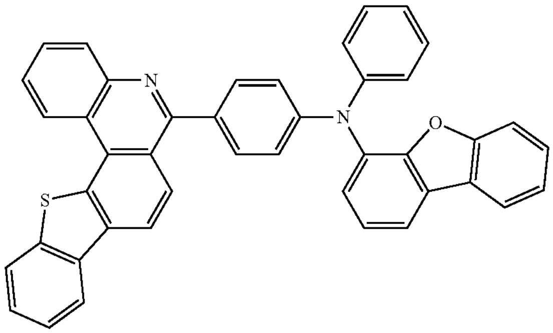
7-19
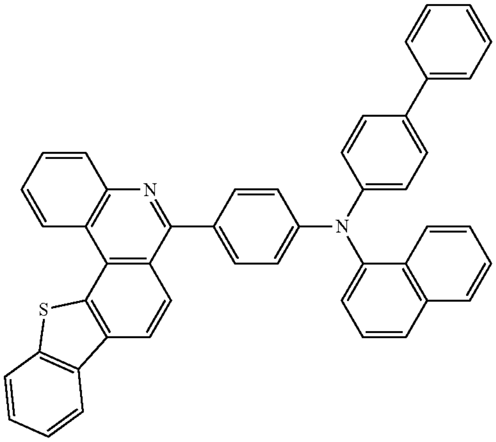
7-20
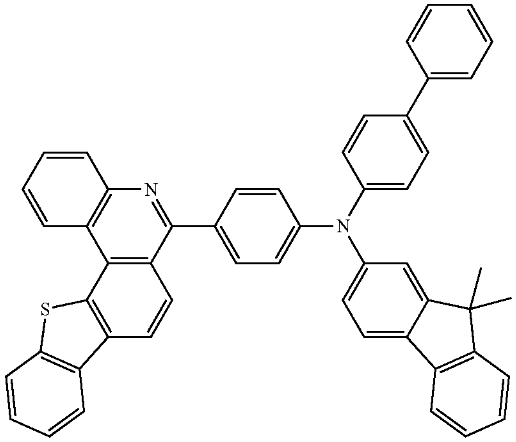

-continued
7-21
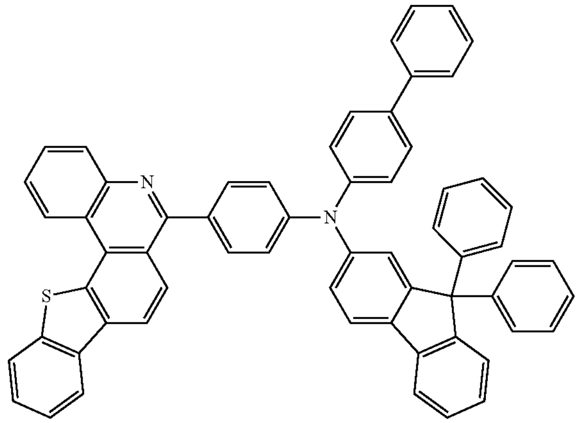
7-22
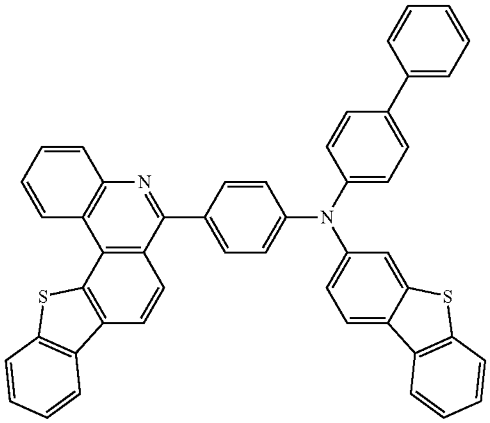
7-23
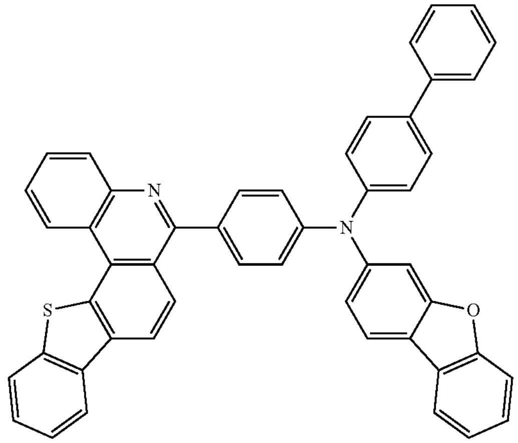
7-24
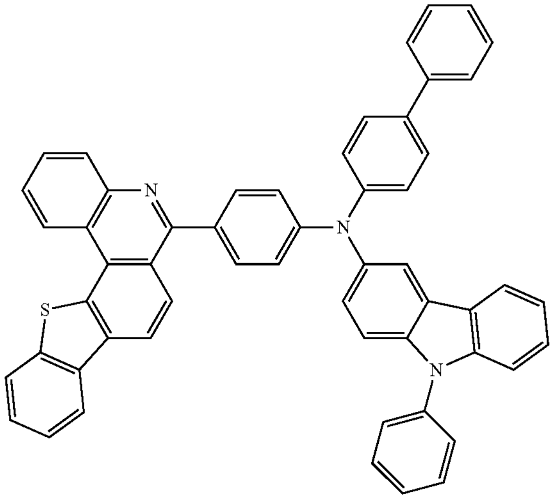
7-25
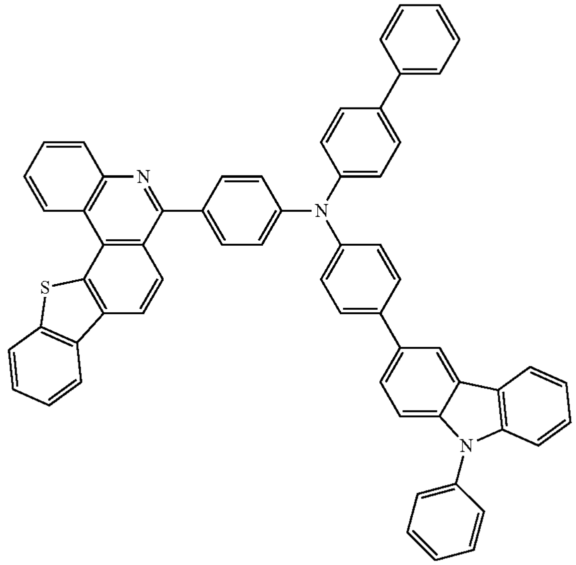
7-26
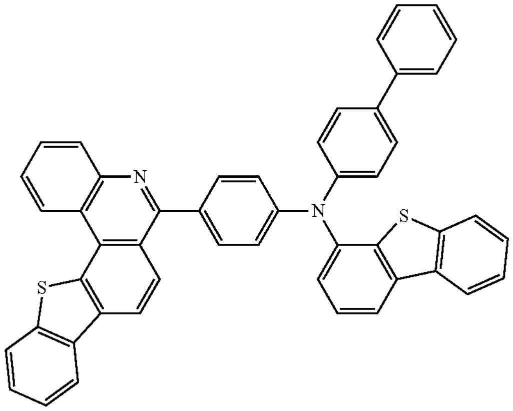

-continued
7-27
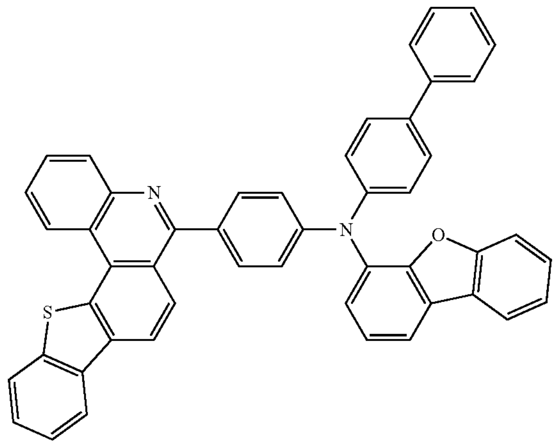
7-28
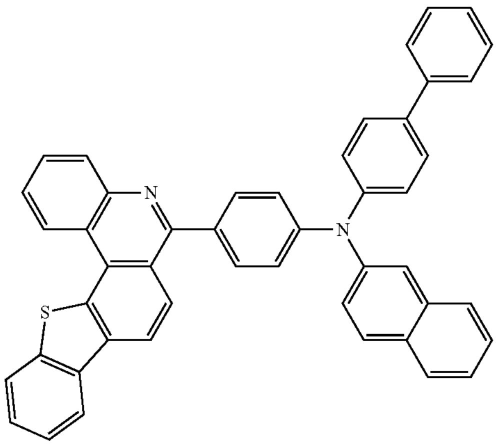
7-29
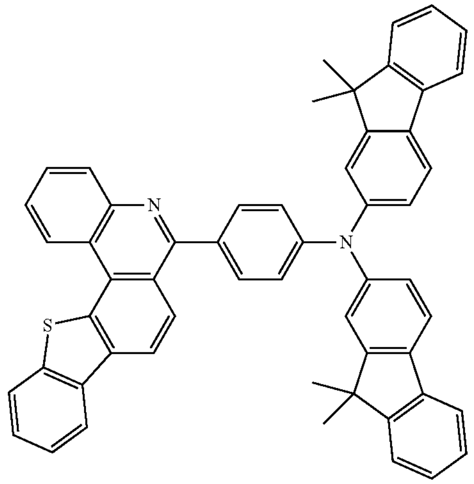
7-30
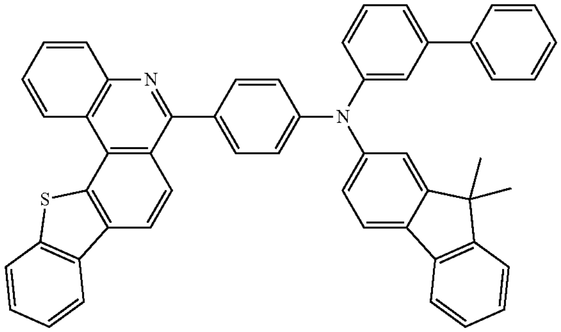
7-31
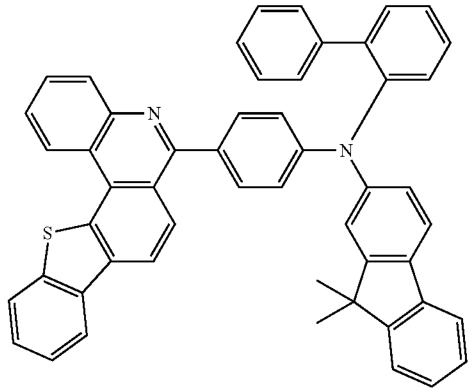
7-32
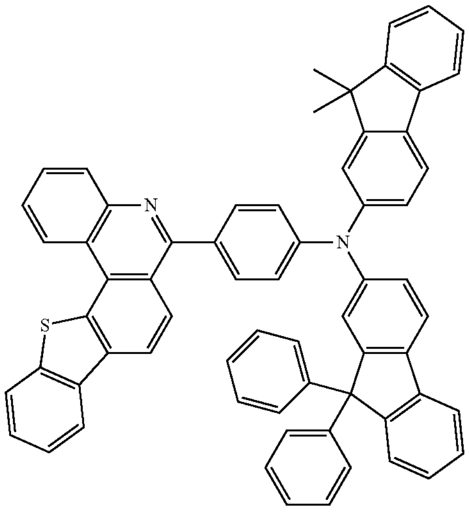

-continued
7-33
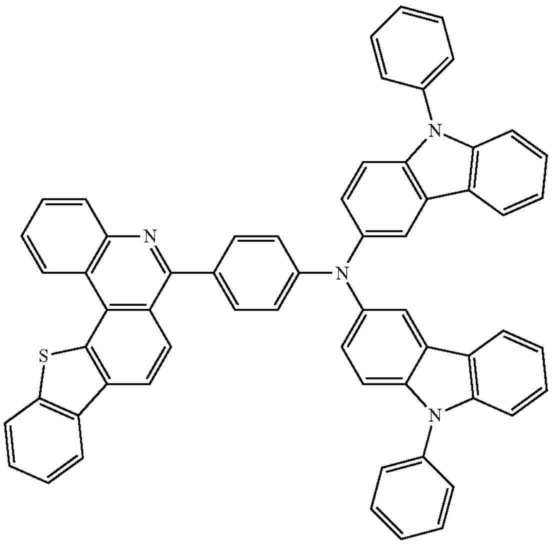
7-34
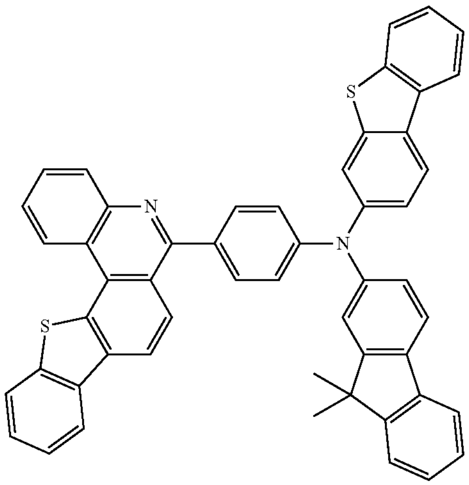
7-35
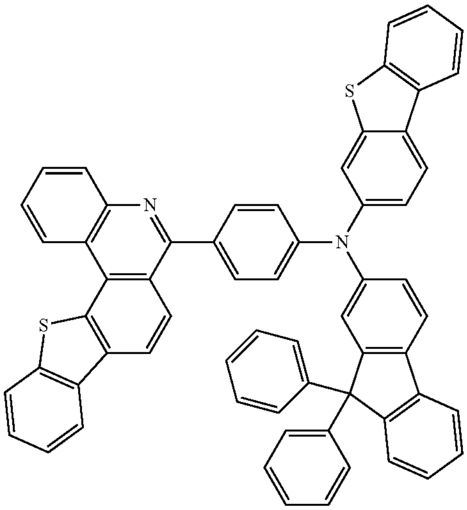
7-36
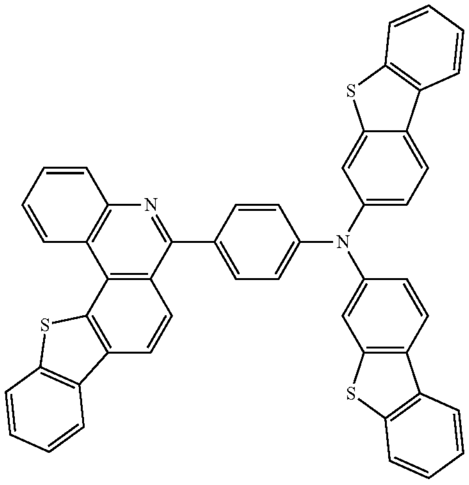
7-37
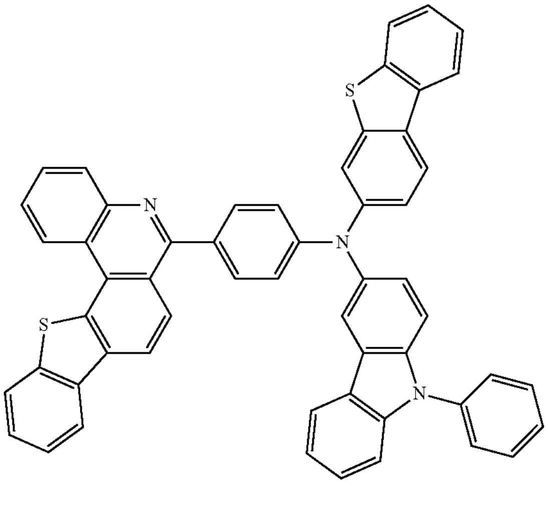
7-38
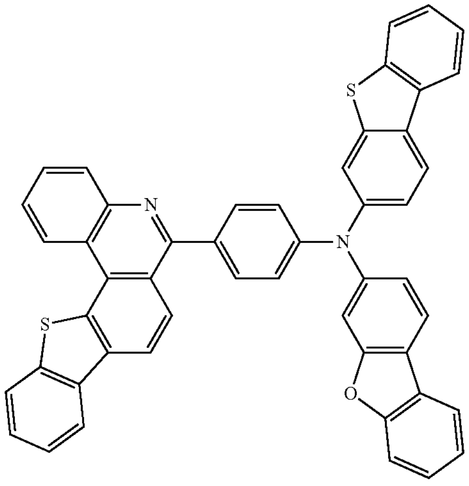

-continued
7-39
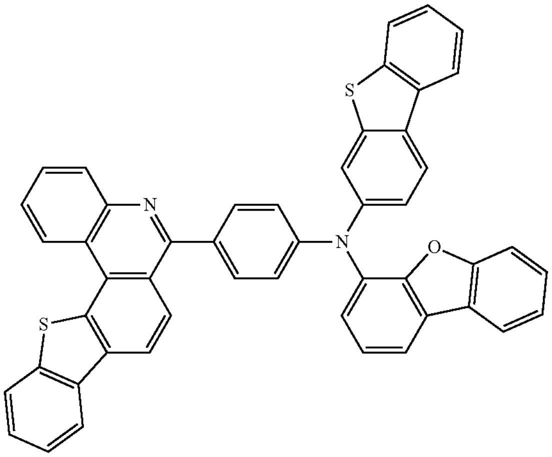
7-40
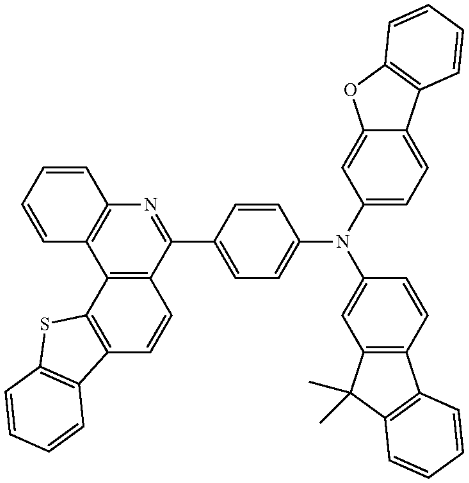
7-41
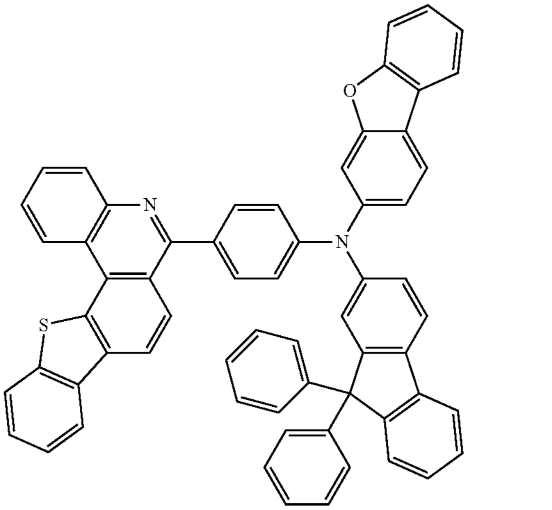
7-42
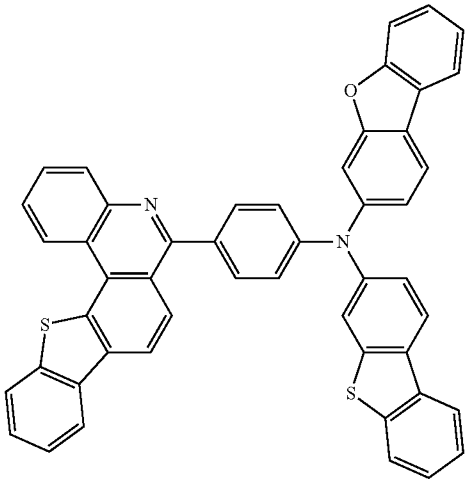
7-43
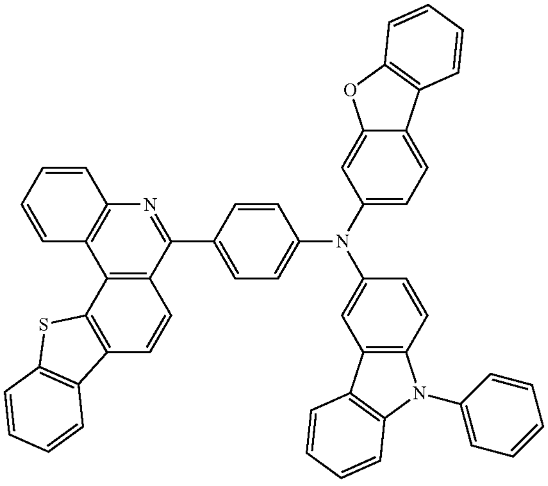
7-44
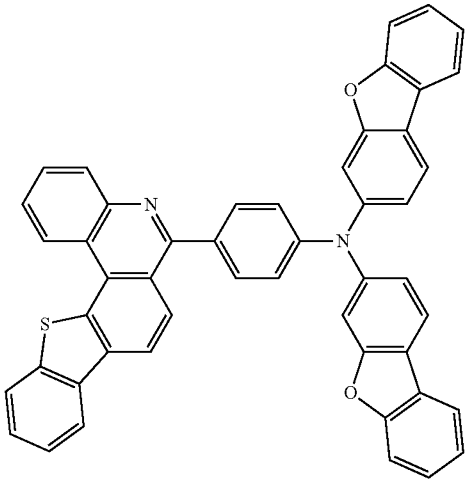

-continued
7-45
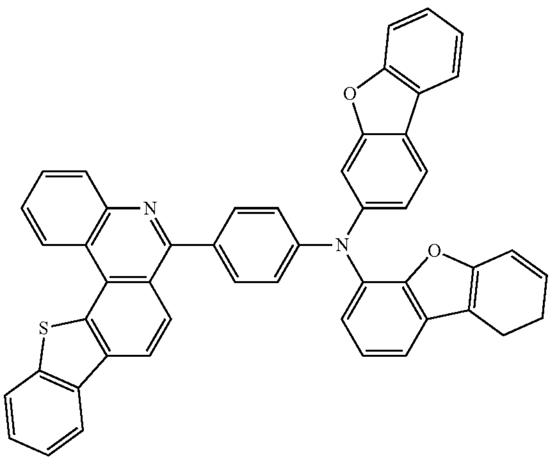
7-46
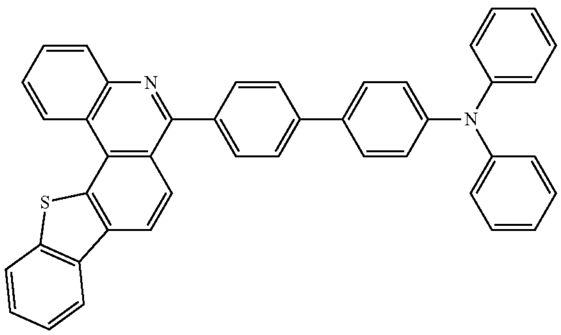
7-47
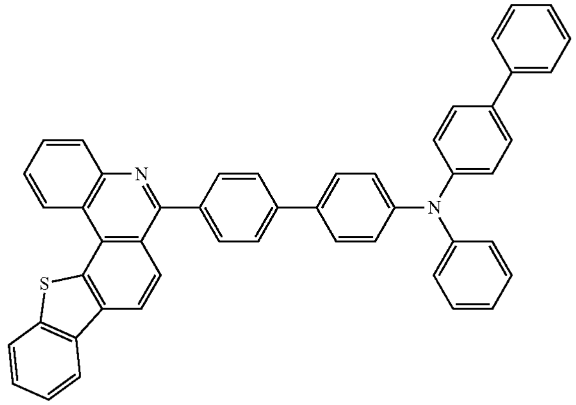
7-48
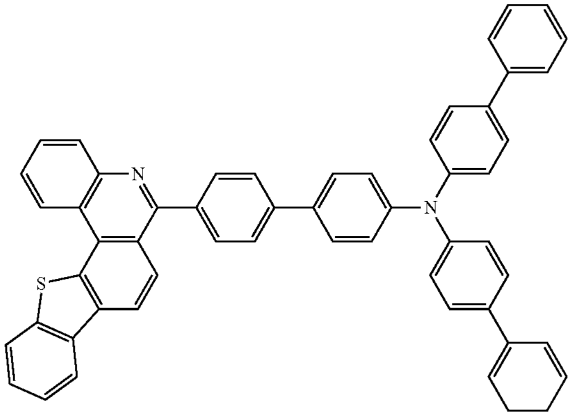
7-49
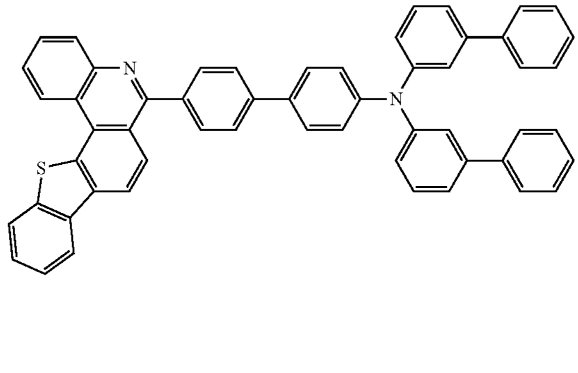
7-50
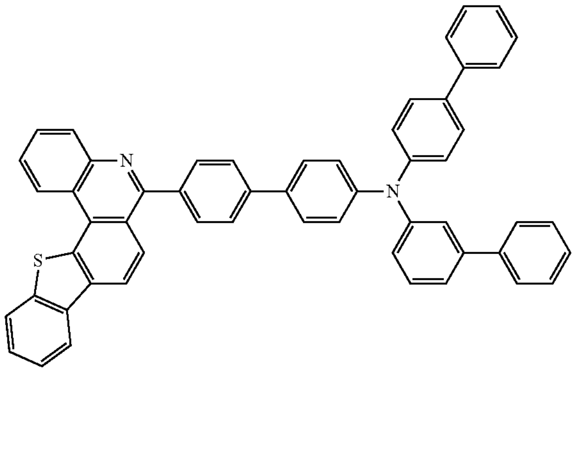

-continued
7-51
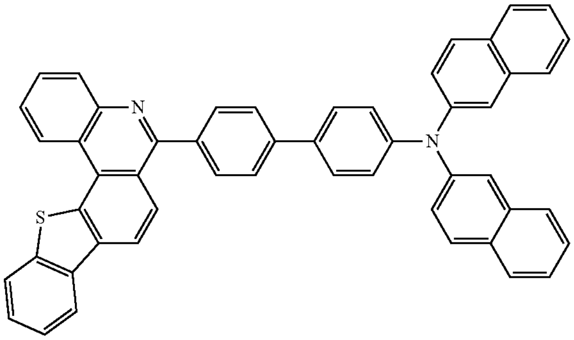
7-52
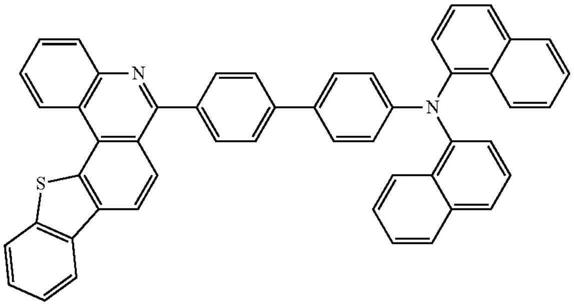
7-53
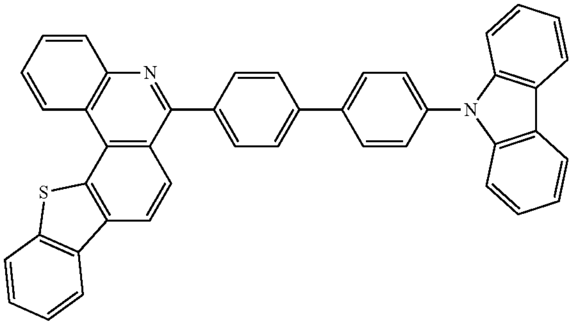
7-54
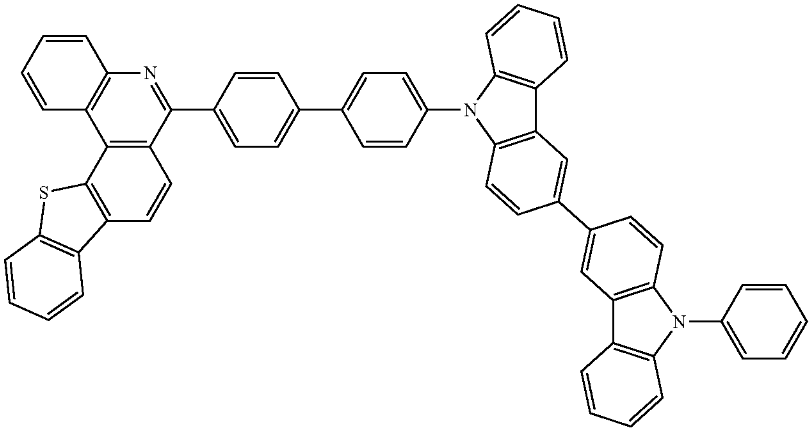
7-55
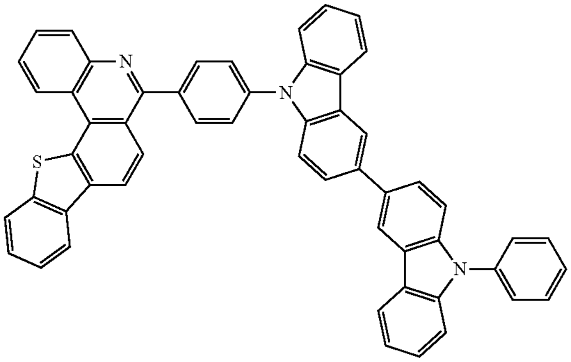
7-56
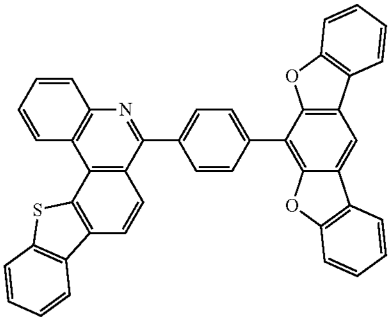

-continued
7-57
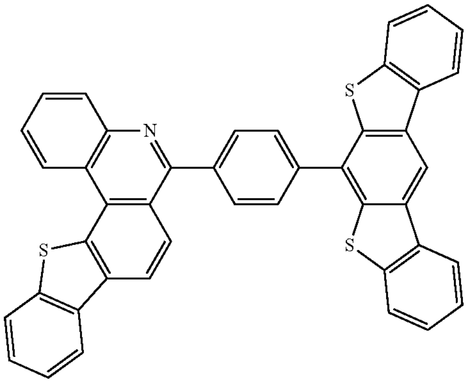
7-58
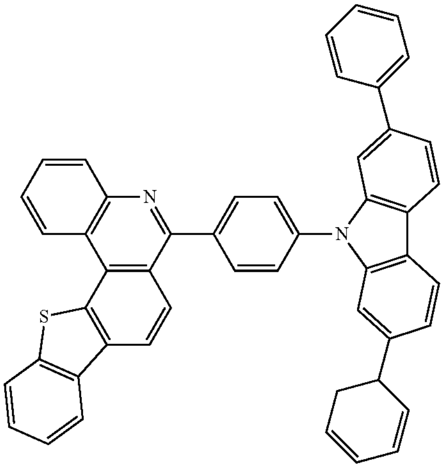
7-59
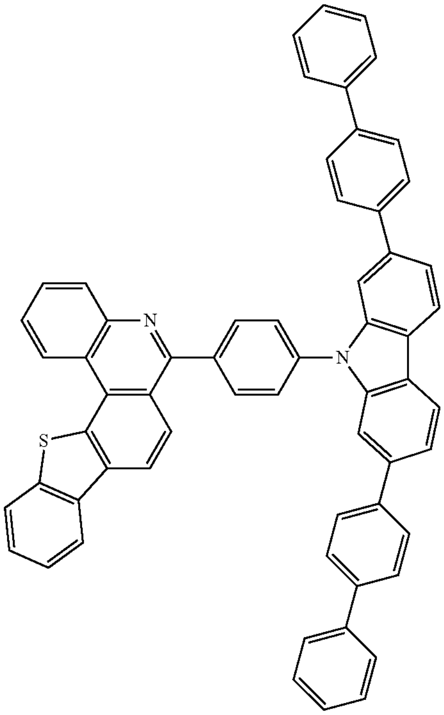
7-60
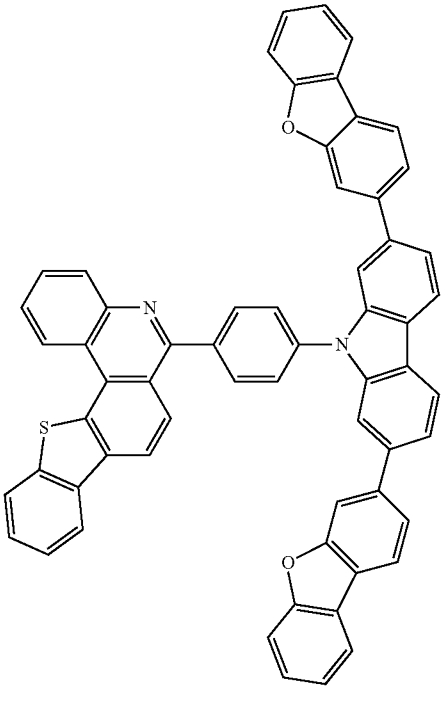
7-61
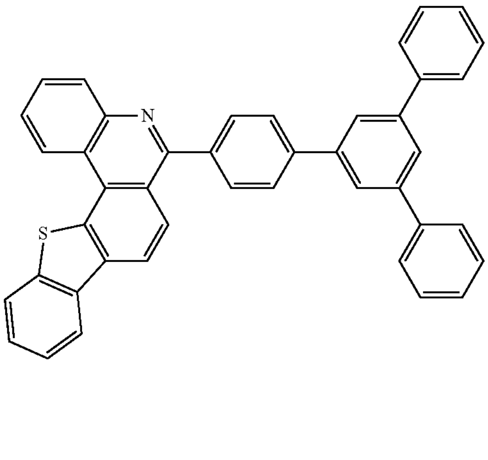
7-62
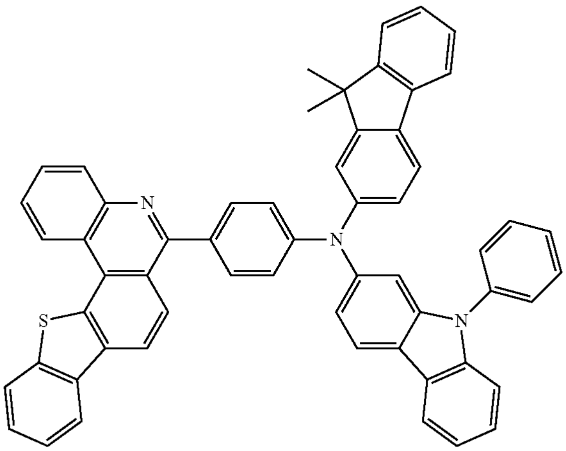

-continued
7-63
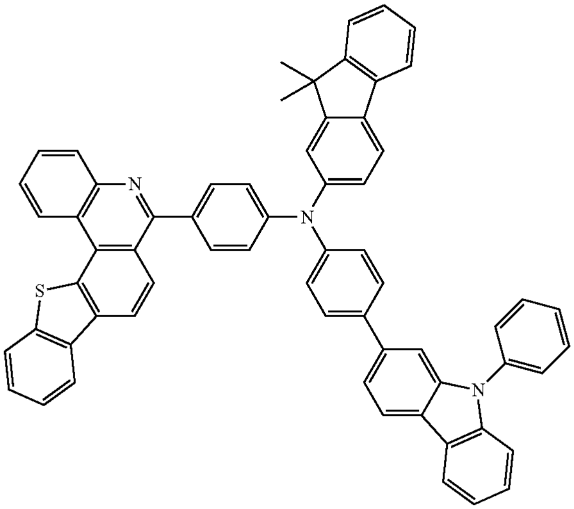
7-64
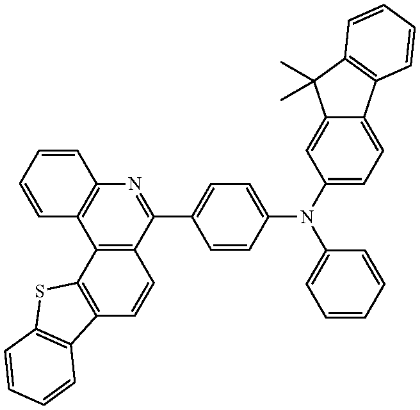
7-65
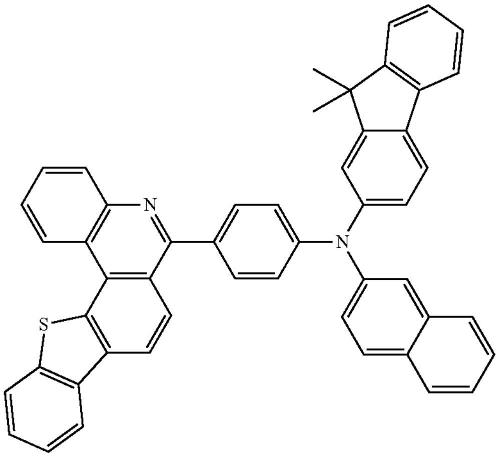
7-66
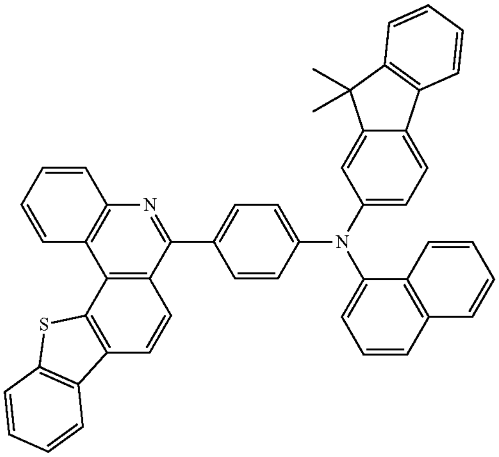
7-67
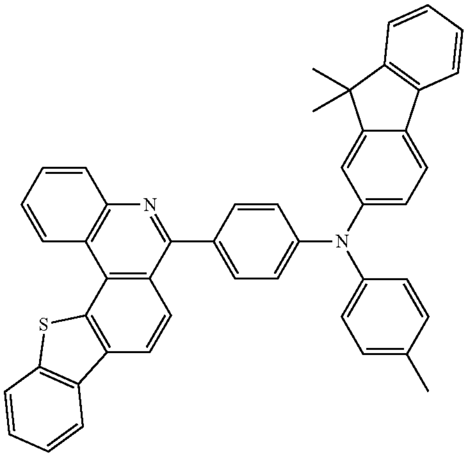
7-68
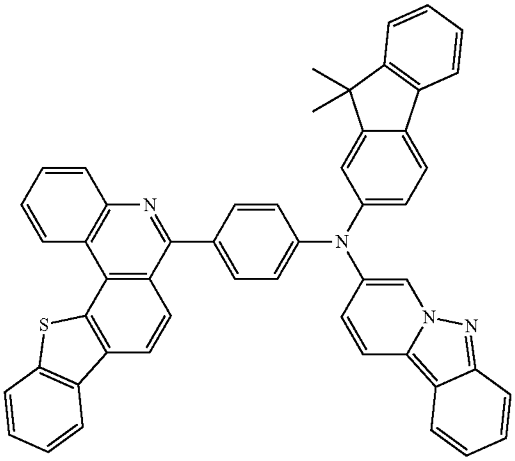

-continued
7-69
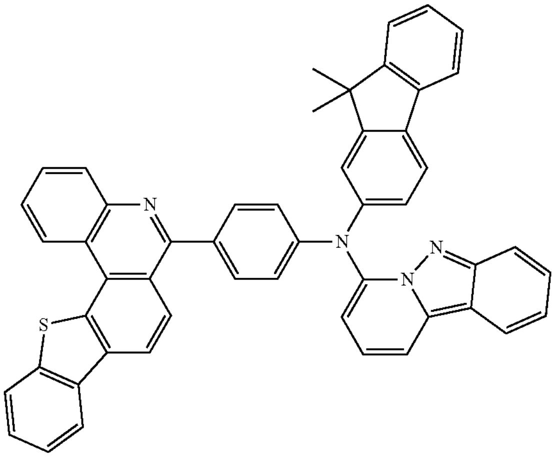
7-70
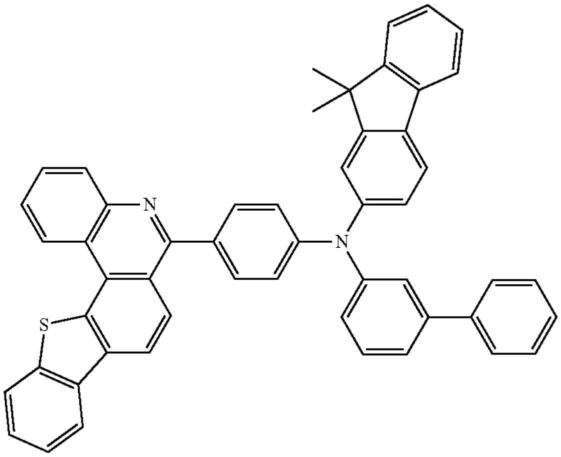
7-71
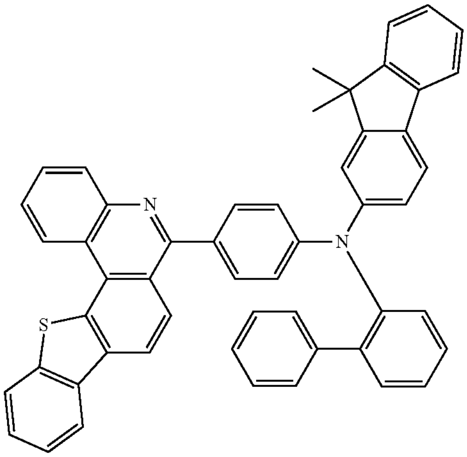
7-72
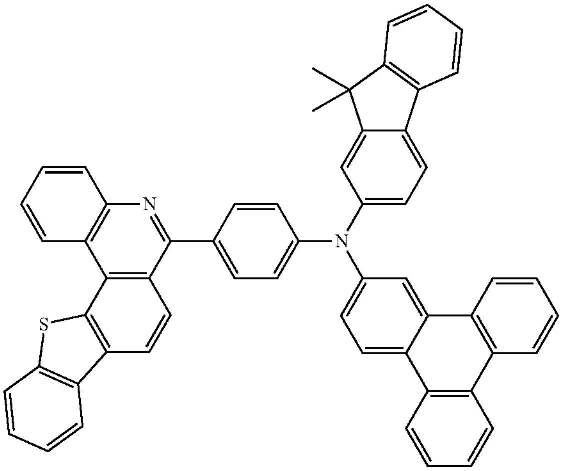
7-73
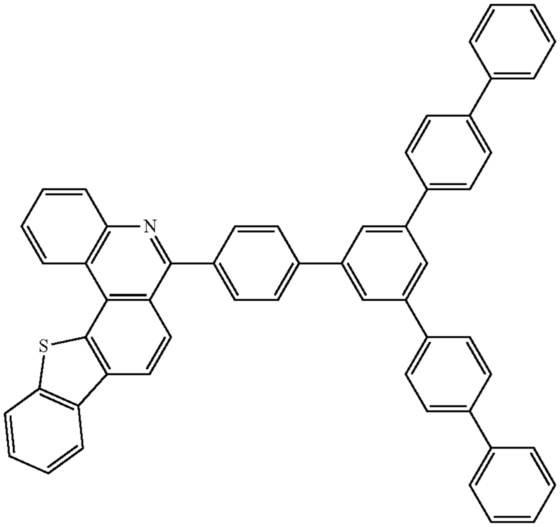
6-74
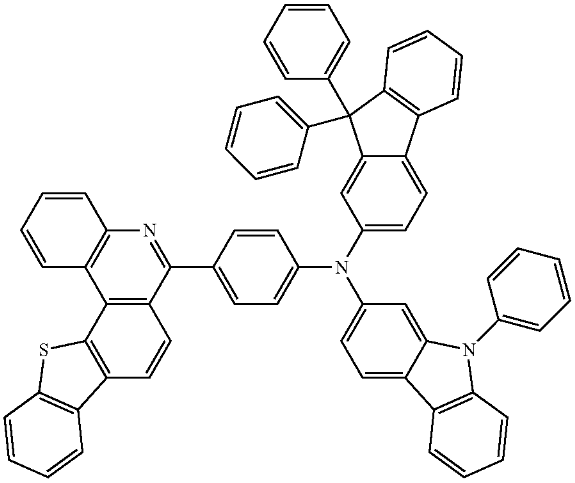

-continued
7-75
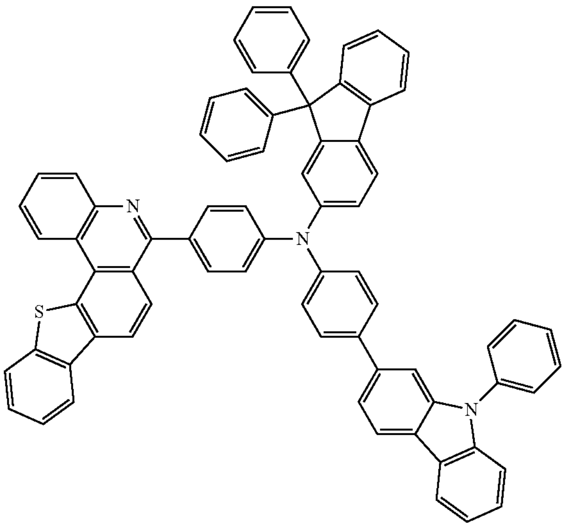
7-76
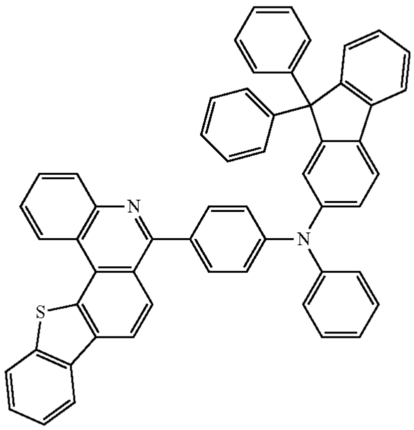
7-77
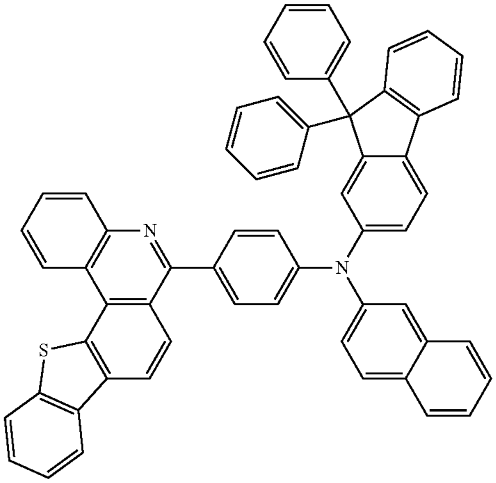
7-78
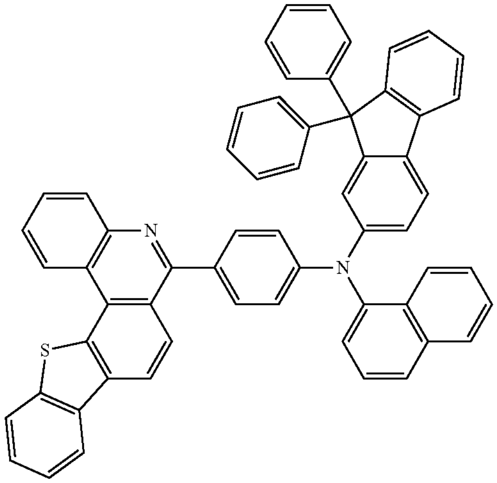
7-79
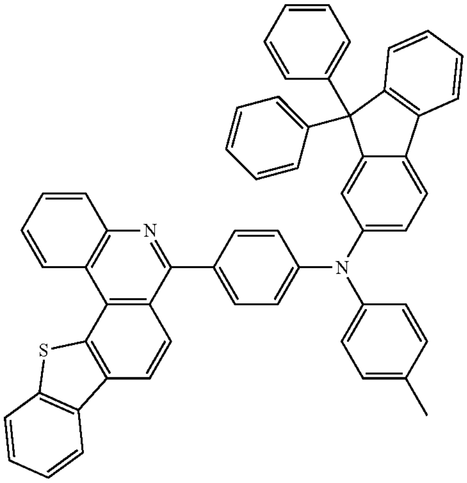
7-80
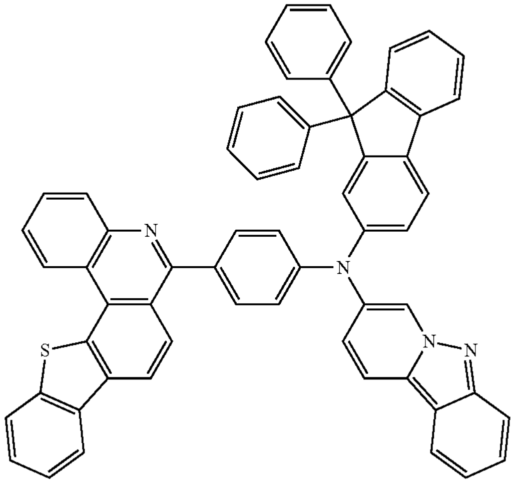

-continued
7-81
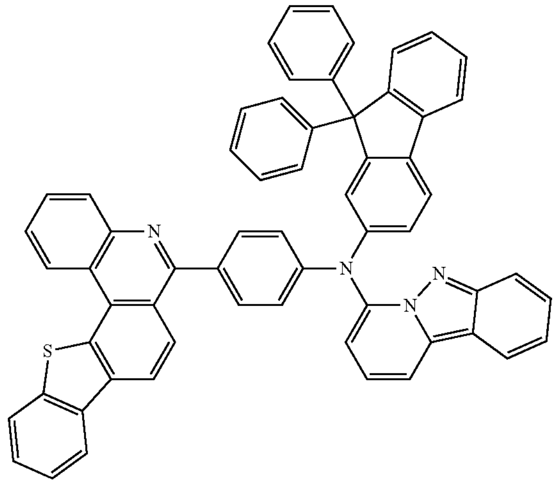
7-82
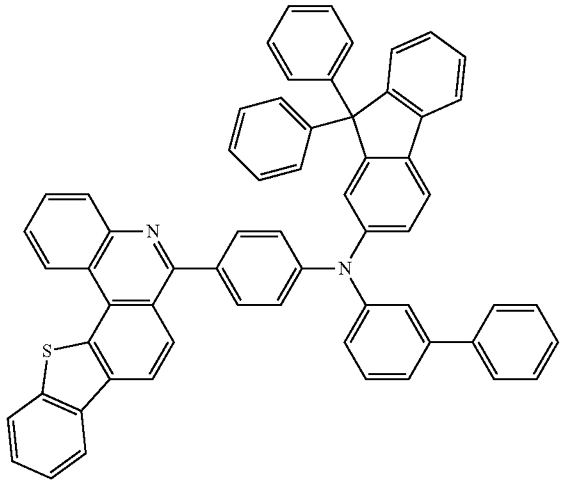
7-83
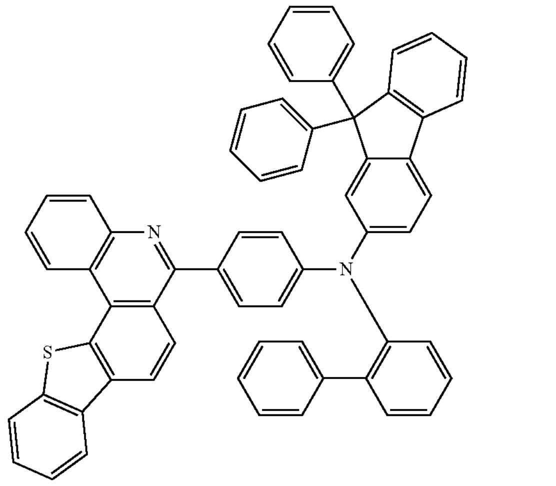
7-84
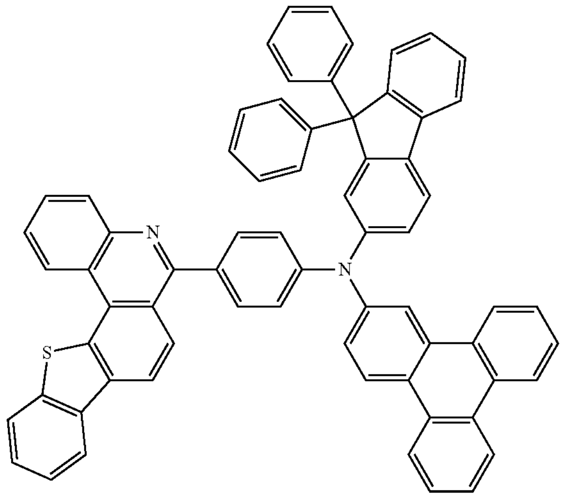
7-85
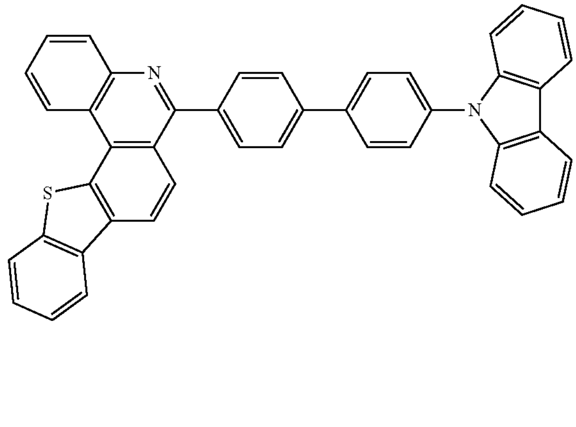
7-86
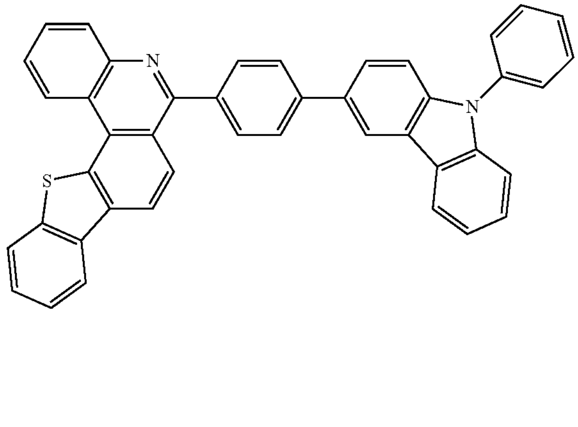

-continued
7-87
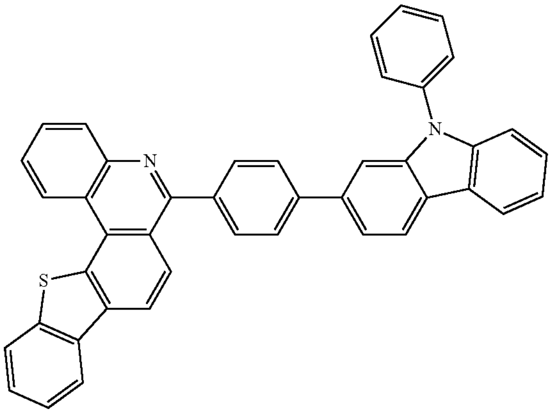
7-88
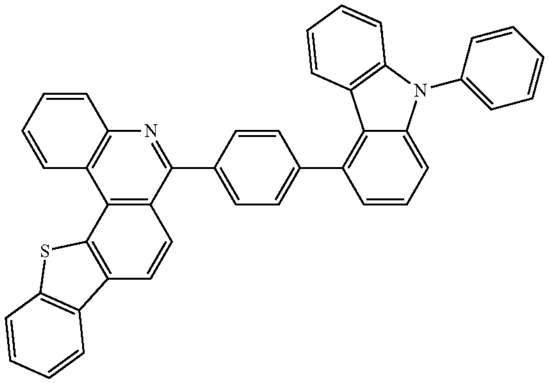
10-1
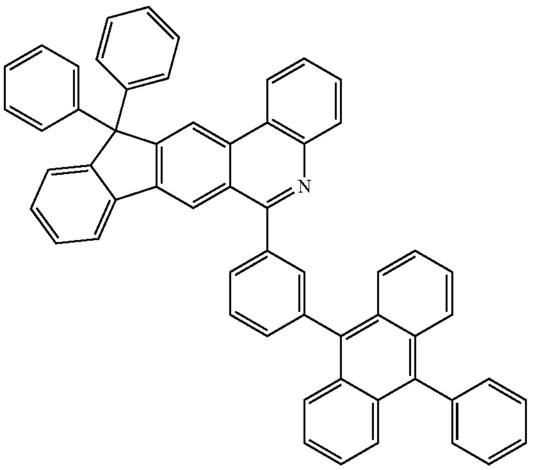
10-2
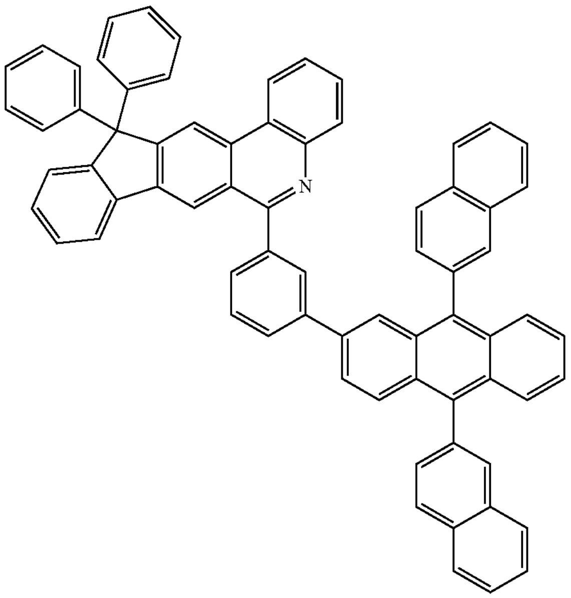
10-3
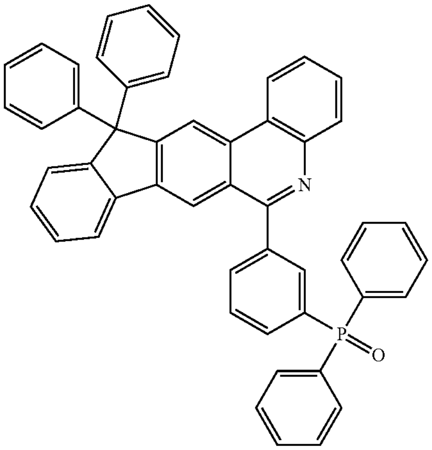
10-4
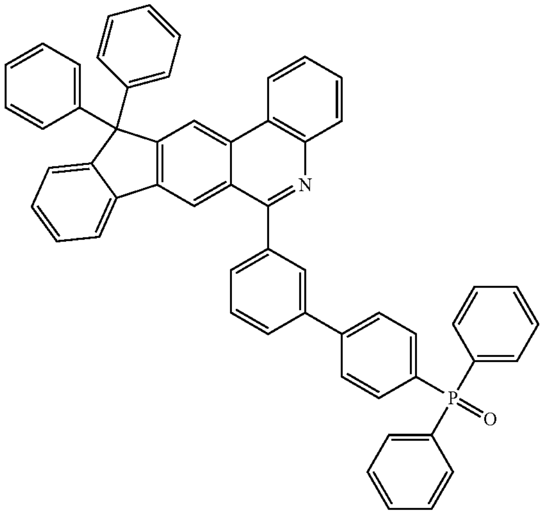

-continued
10-5
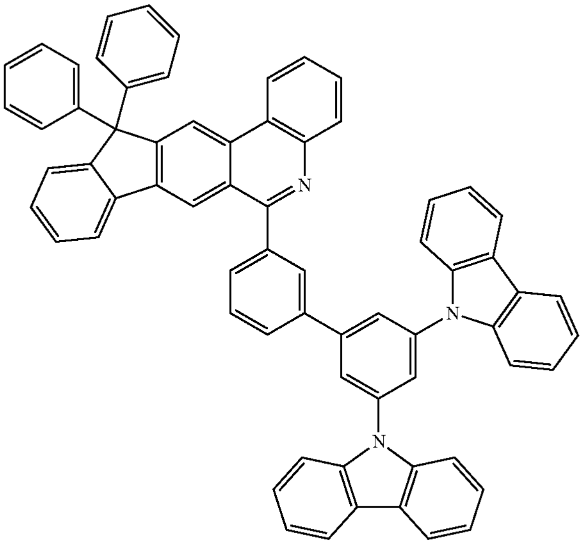
10-6
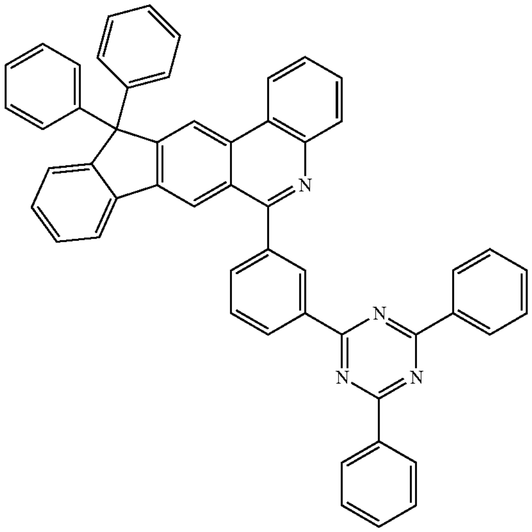
10-7
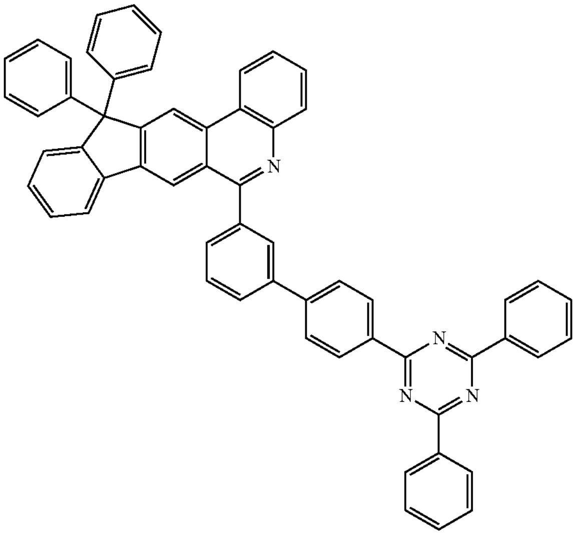
10-8
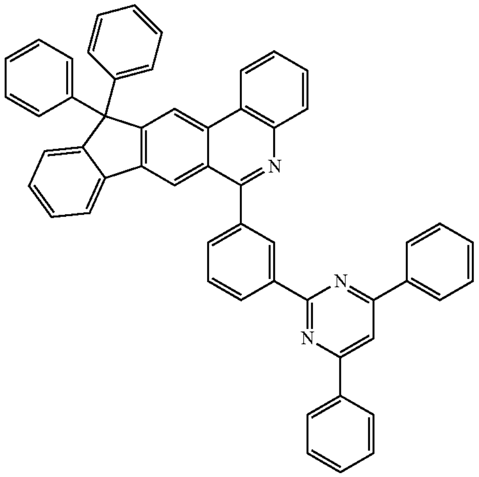
10-9
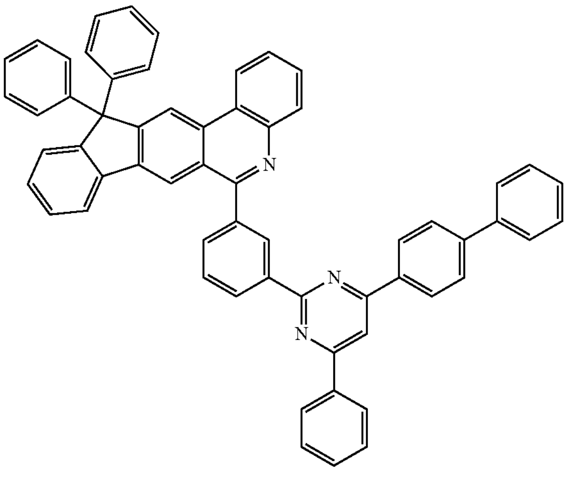
10-10
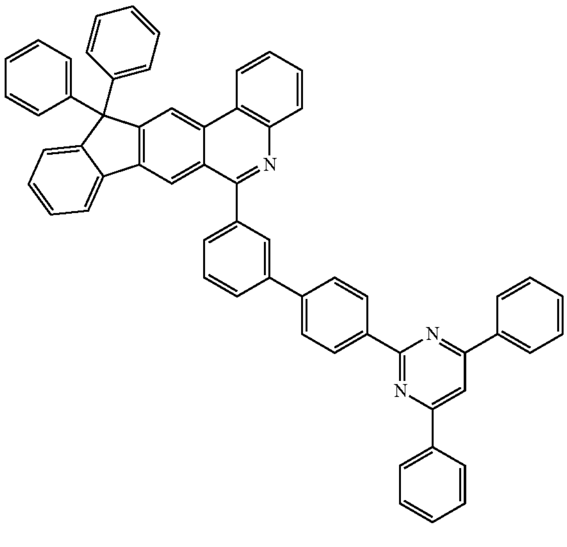

-continued
10-11
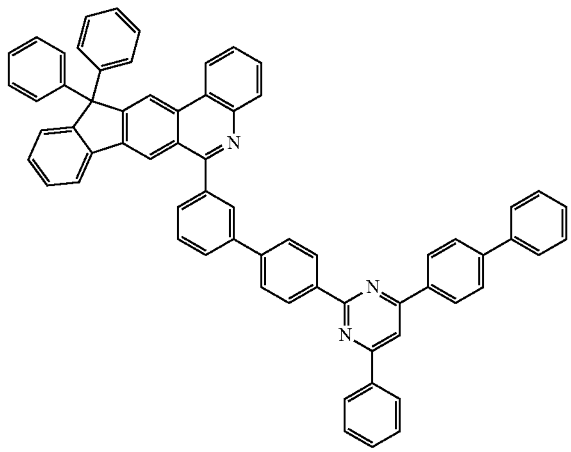
10-12
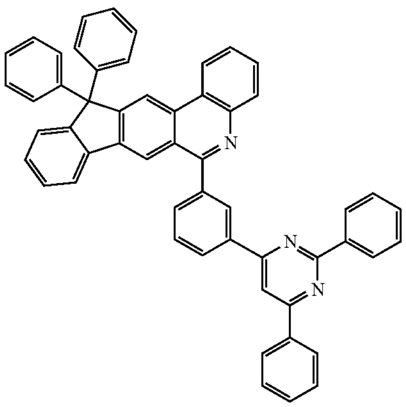
10-13
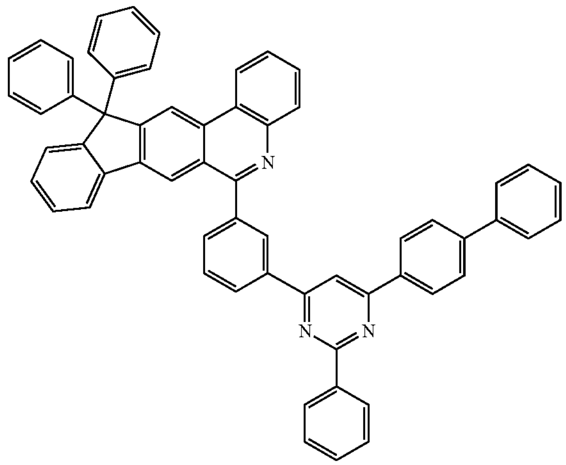
10-14
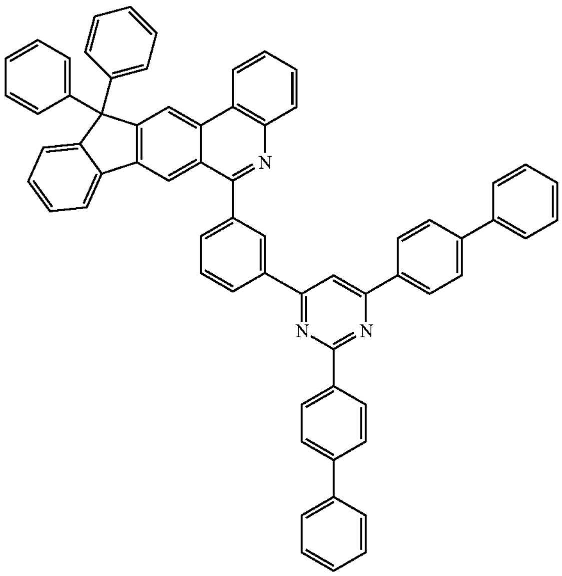
10-15
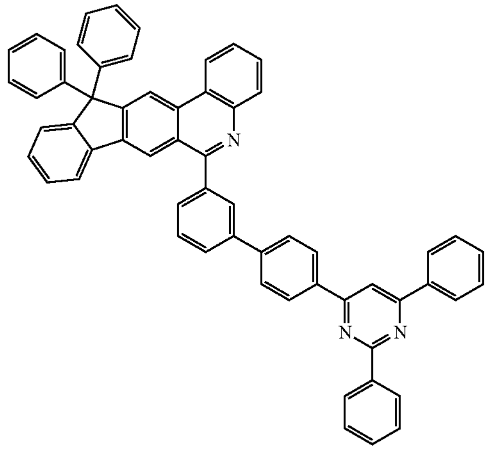
10-16
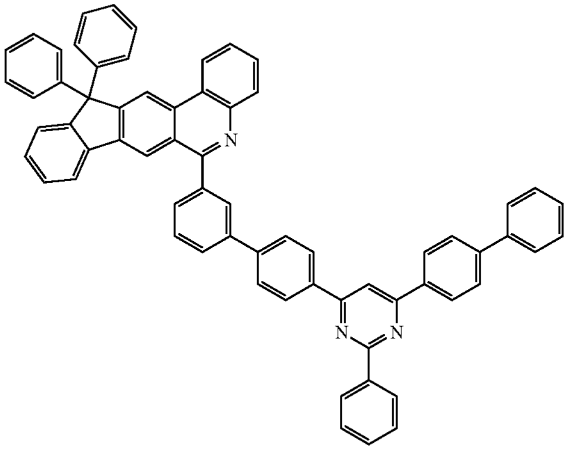

-continued
10-17
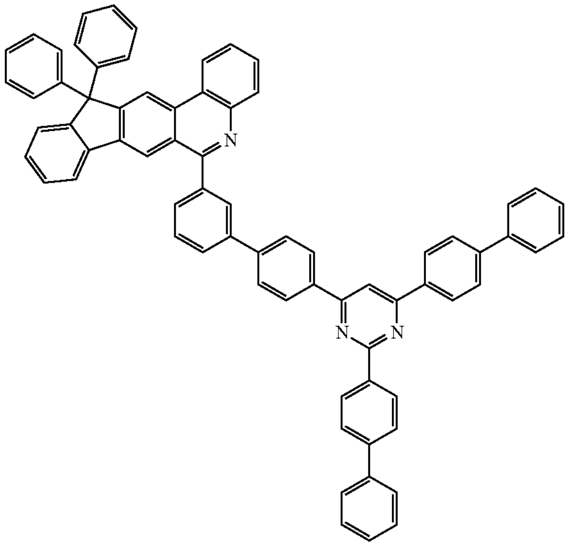
10-18
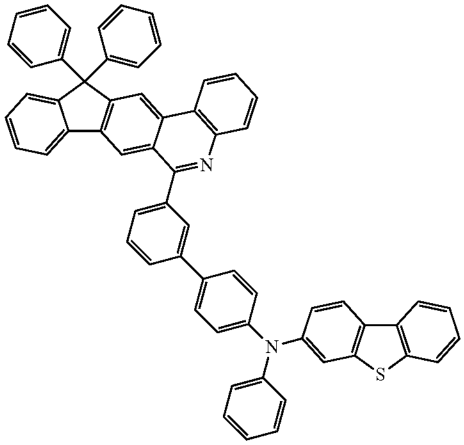
10-19
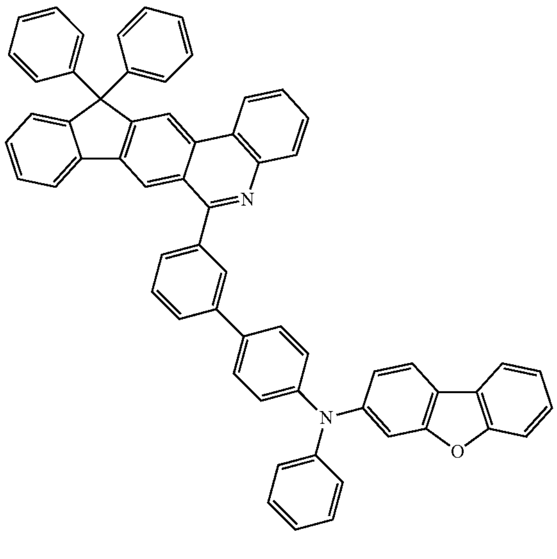
10-20
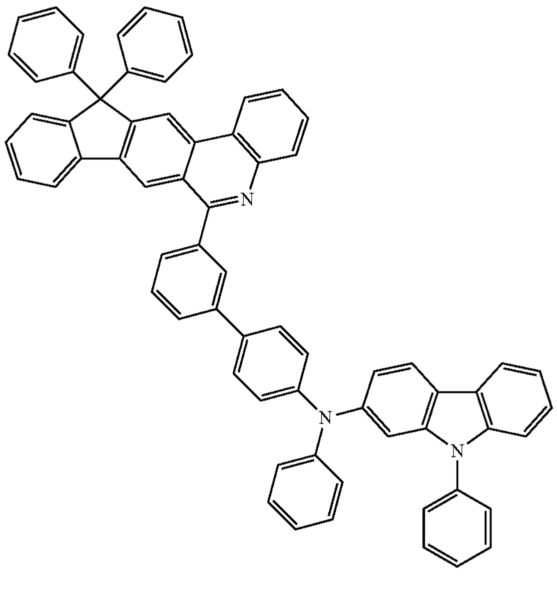

-continued
10-21
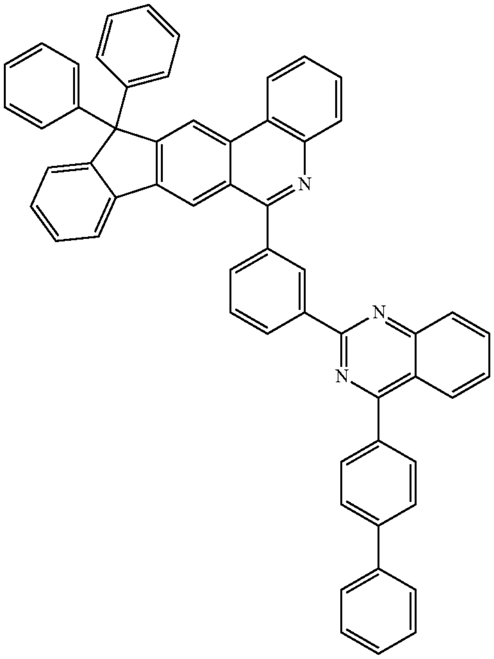
10-22
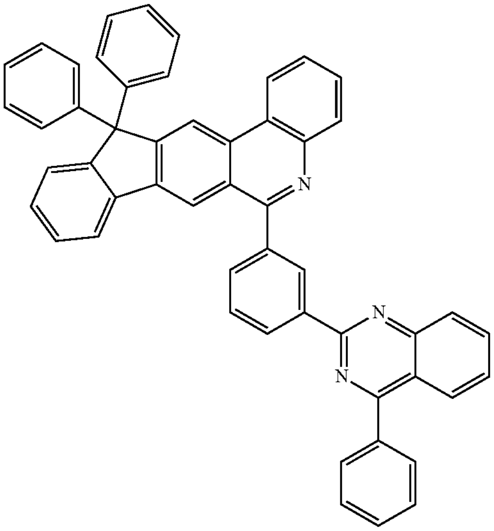
10-23
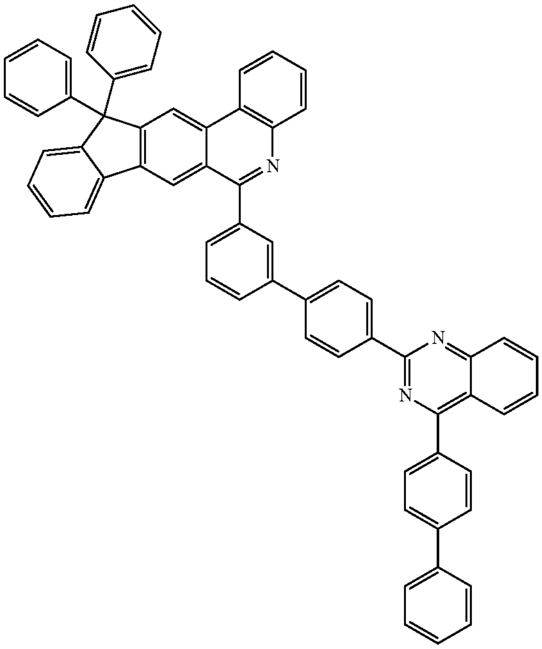
10-24
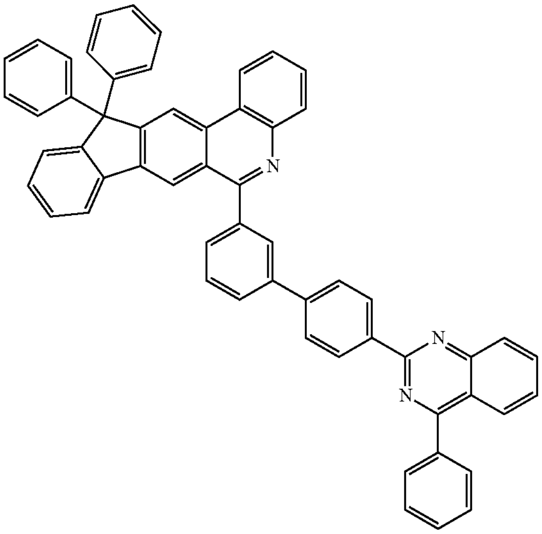

-continued
10-25
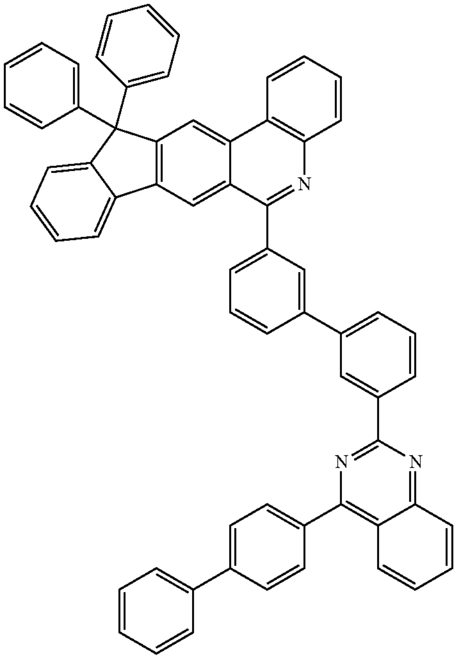
10-26
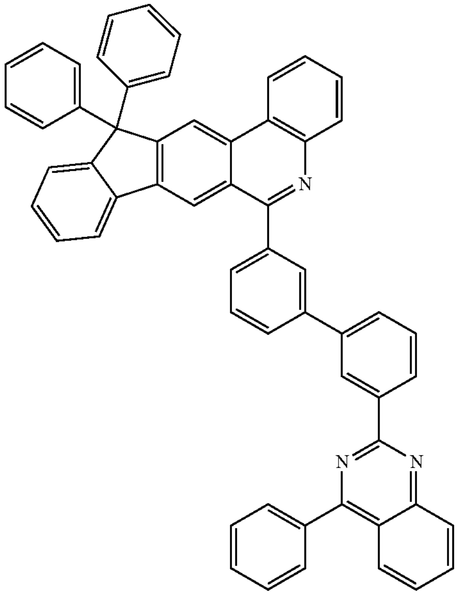
10-27
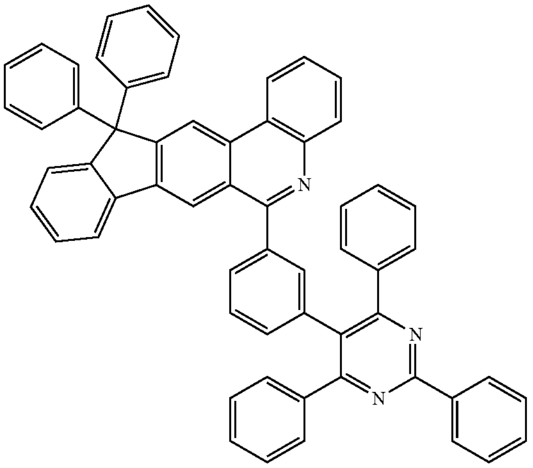
10-28
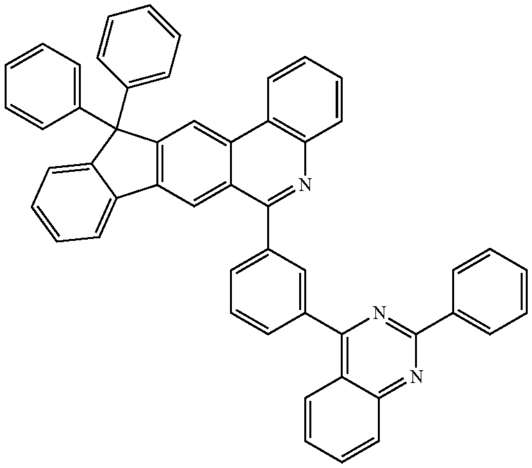
10-29
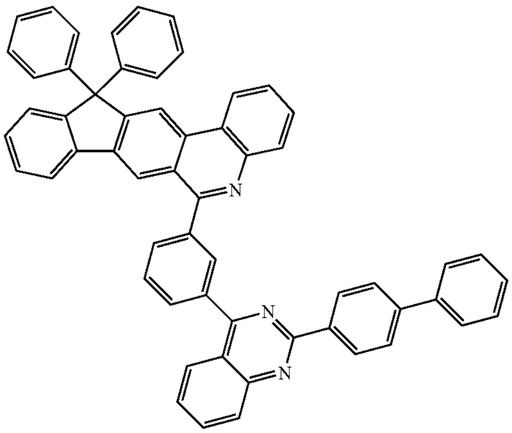
10-30
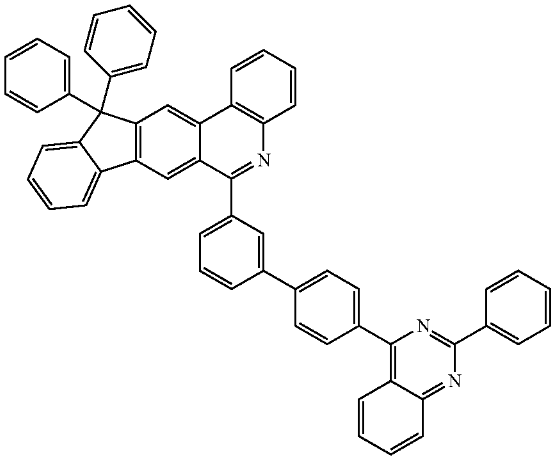

-continued
10-31
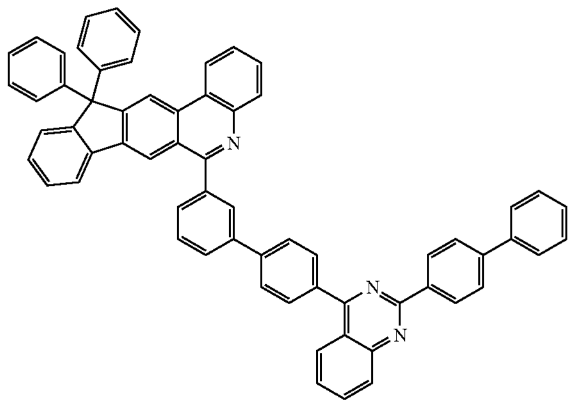
10-32
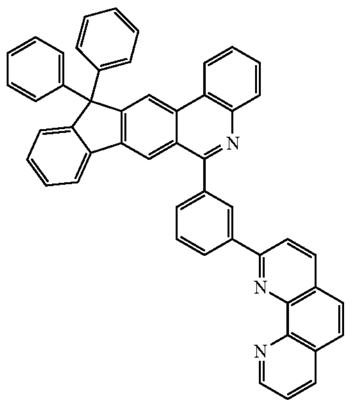
10-33
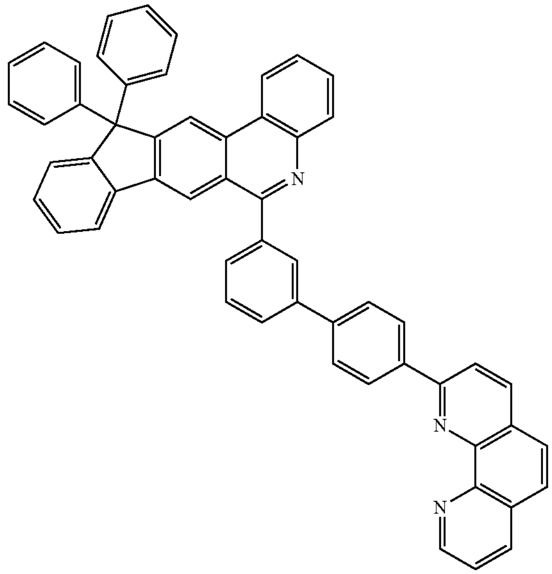
10-34
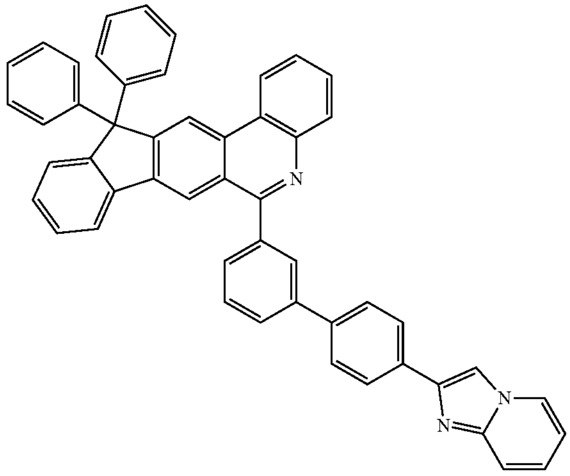
10-35
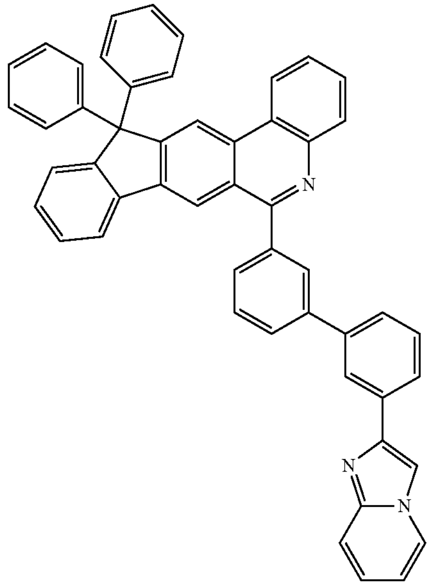
10-36
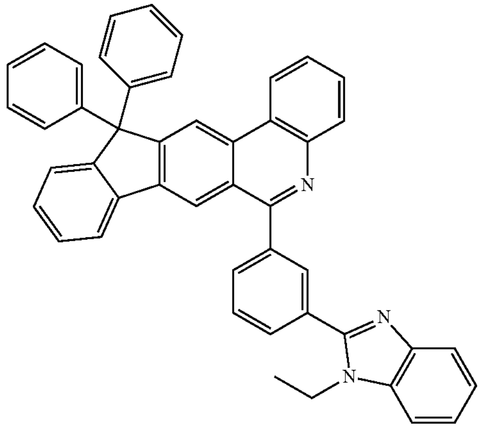

-continued
10-37
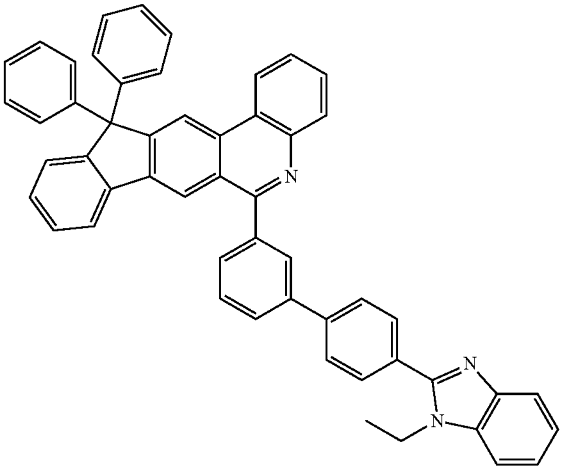
10-38
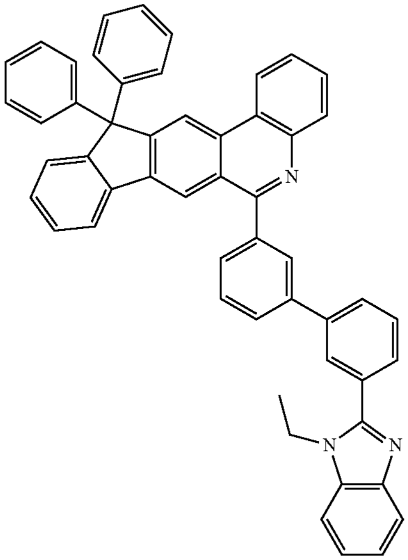
10-39
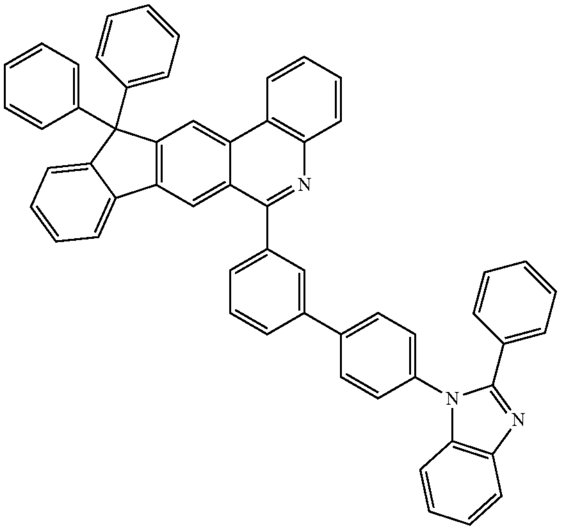
10-40
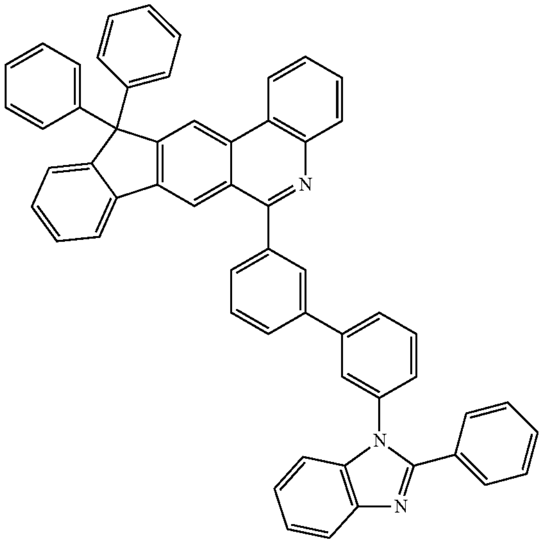
10-41
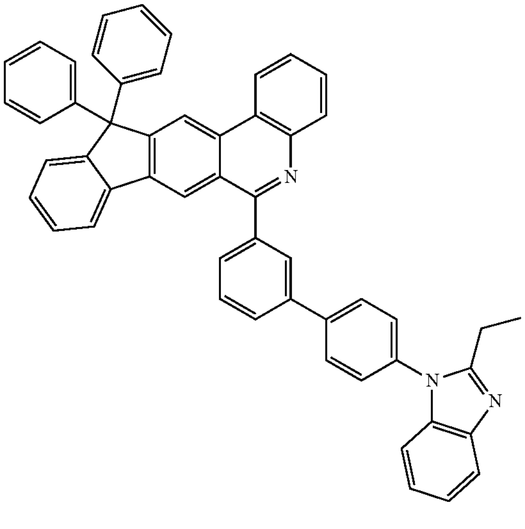
10-42
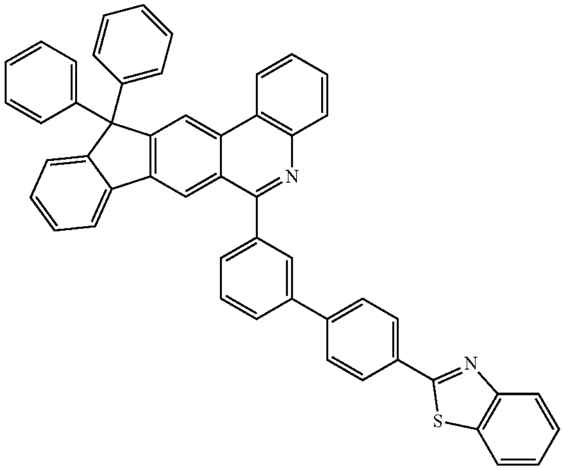

-continued
10-43
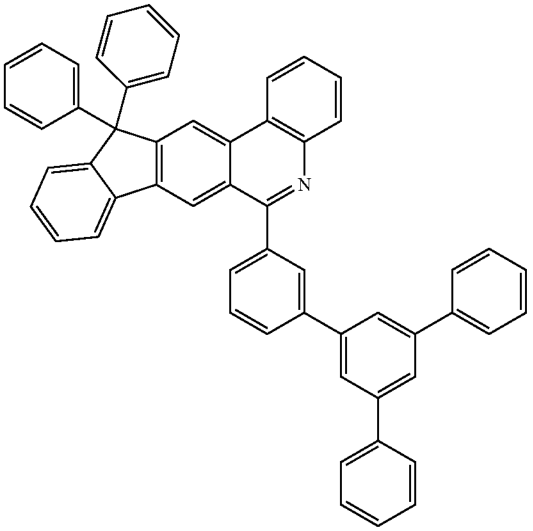
10-44
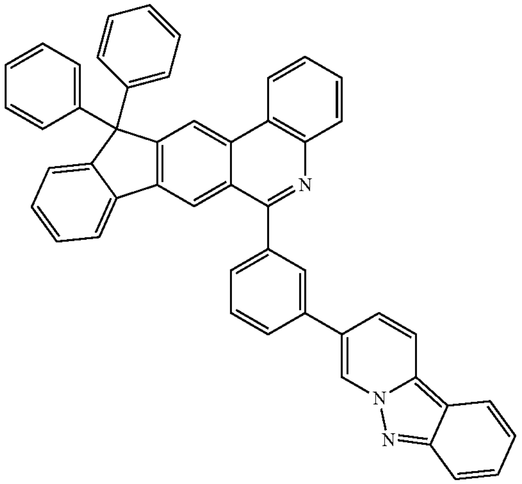
10-45
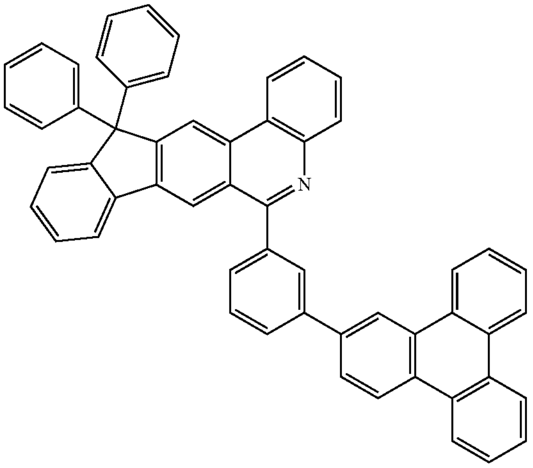
10-46
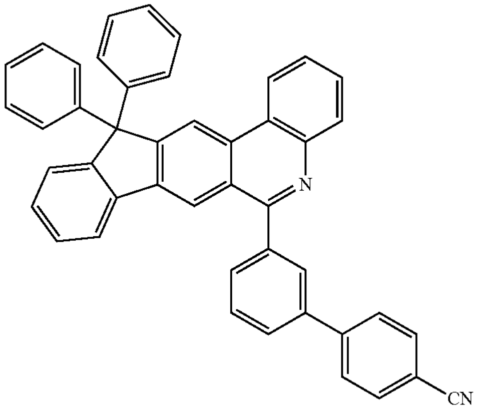
10-47
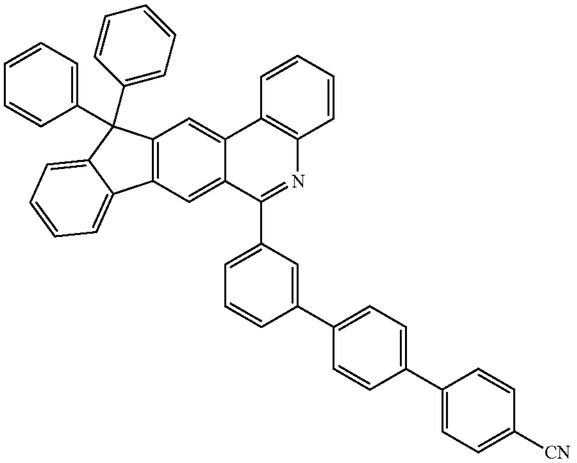
10-48
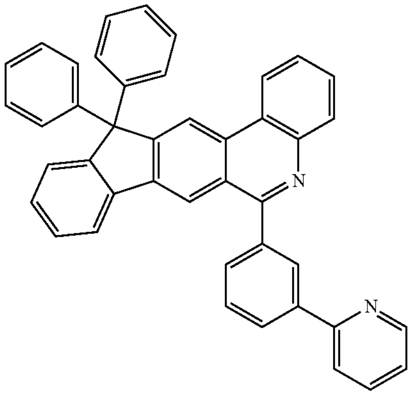

-continued
10-49
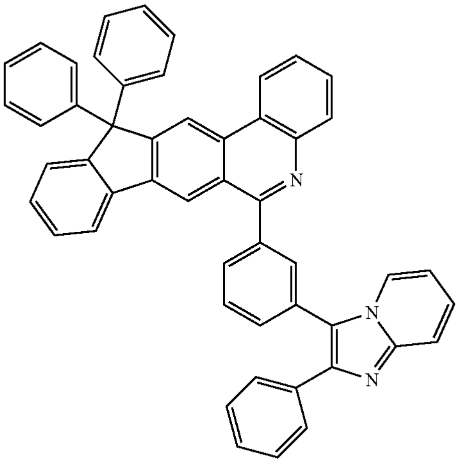
10-50
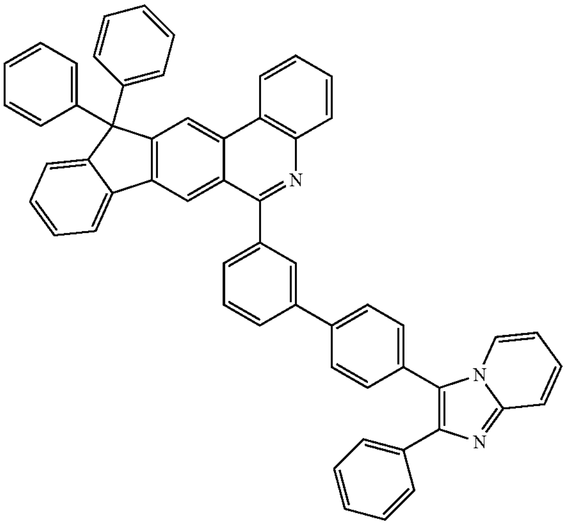
10-51
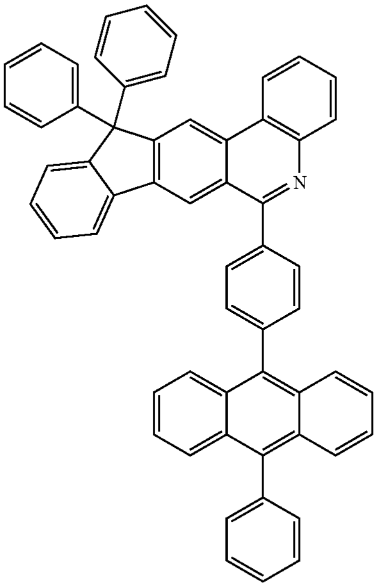
10-52
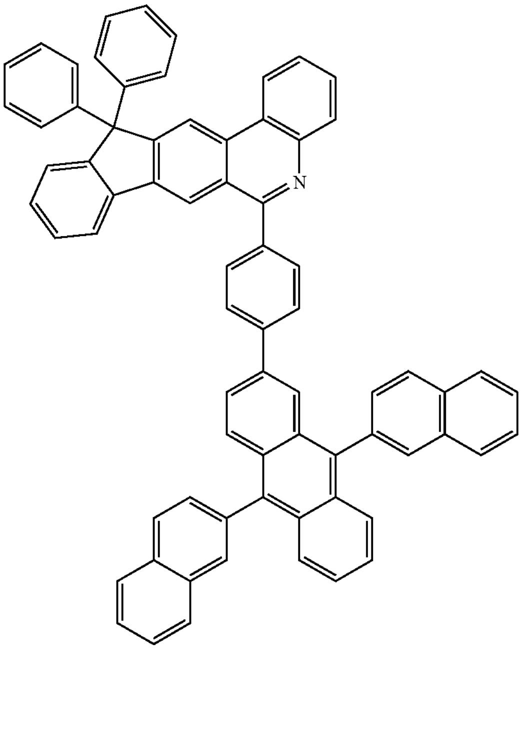

-continued
10-53
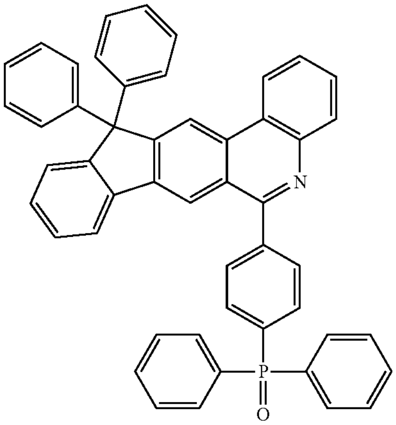
10-54
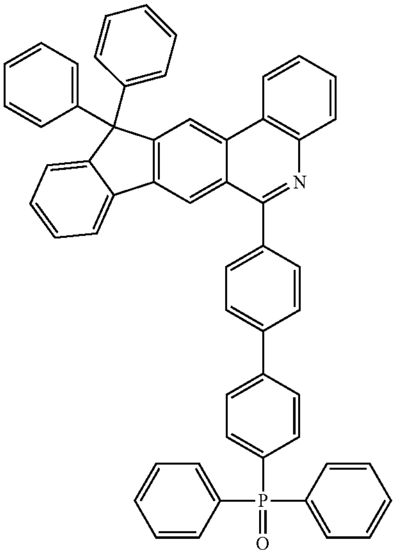
-continued
10-55
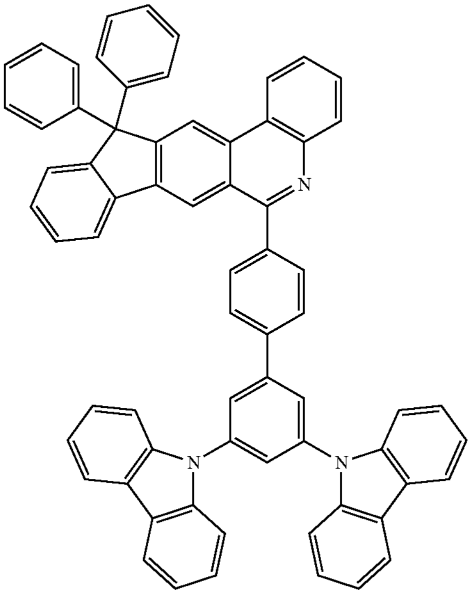
10-56
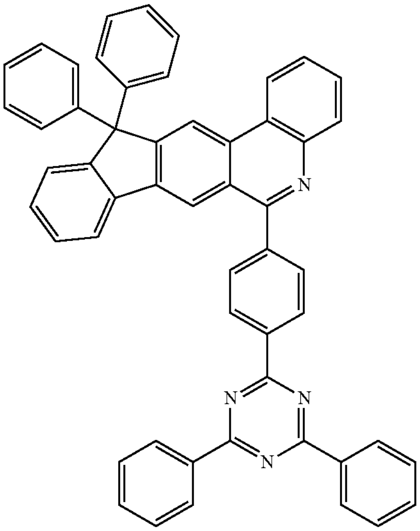

-continued
10-57
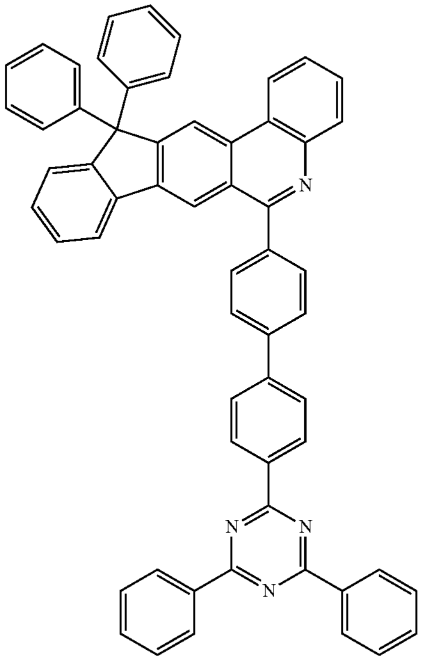
10-58
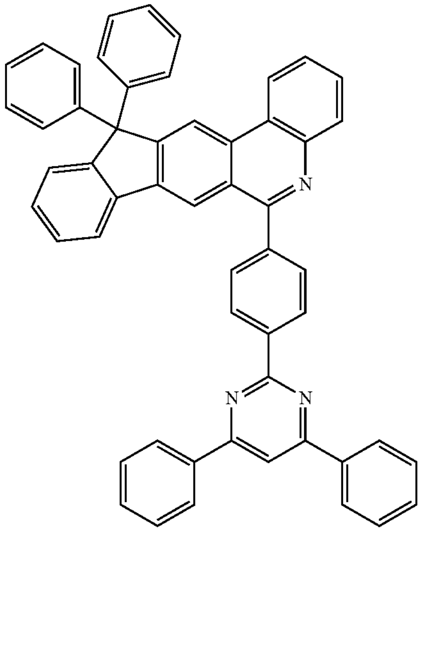
-continued
10-59
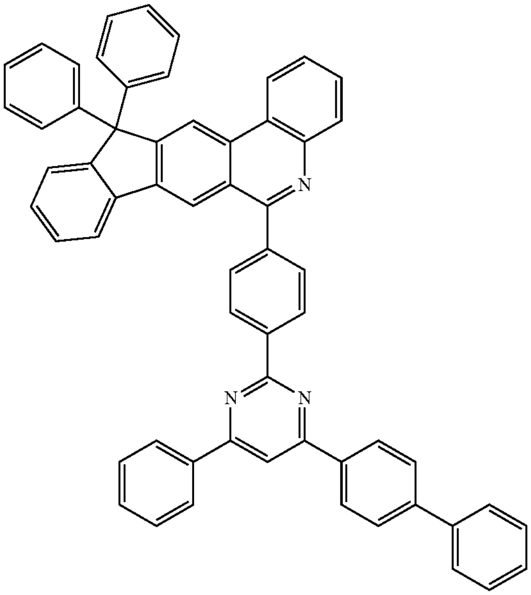
10-60
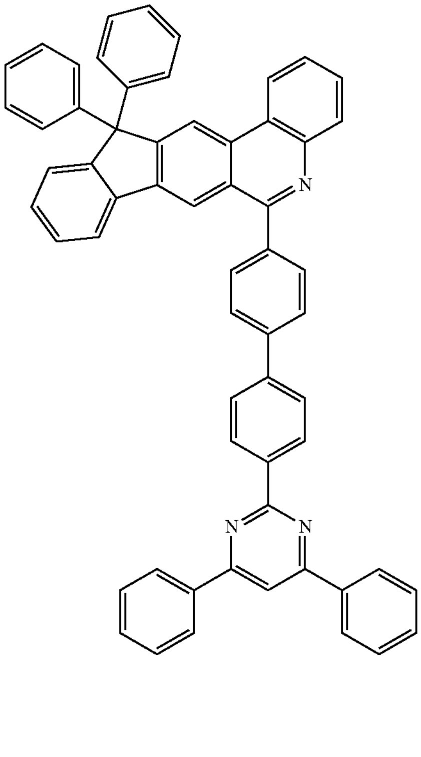

-continued
10-61
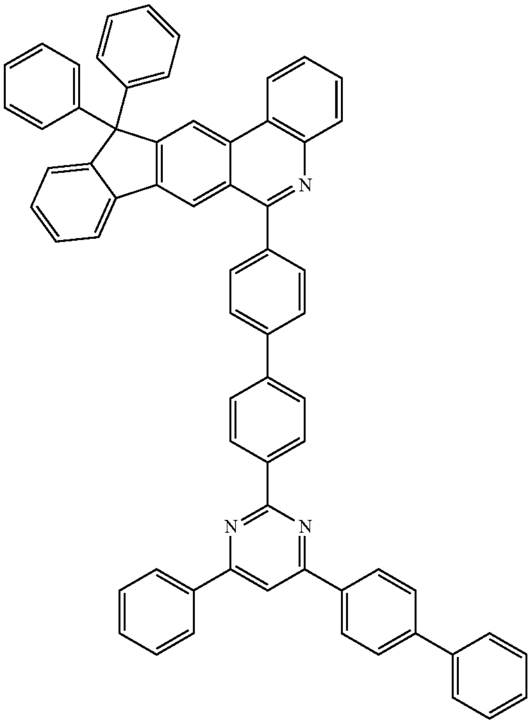
10-62
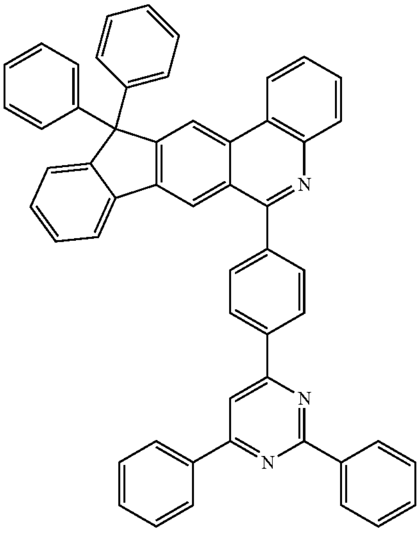
-continued
10-63
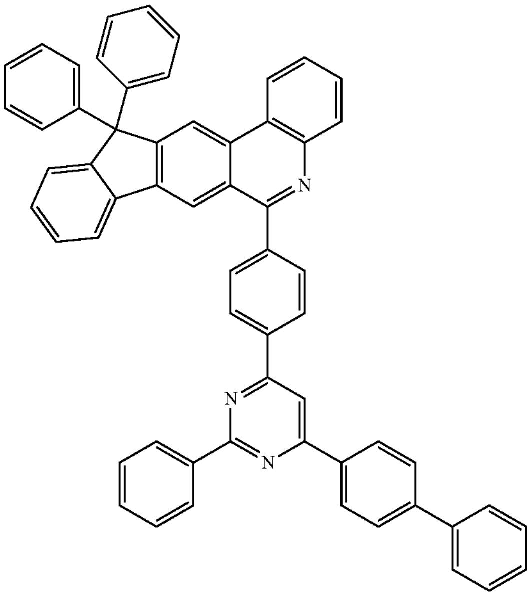
10-64
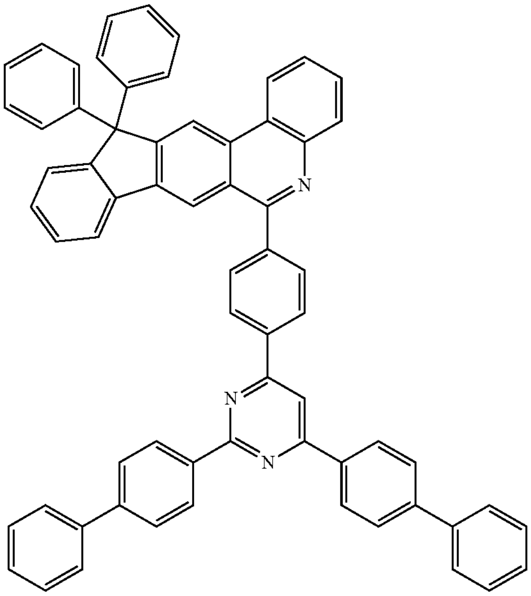

10-65
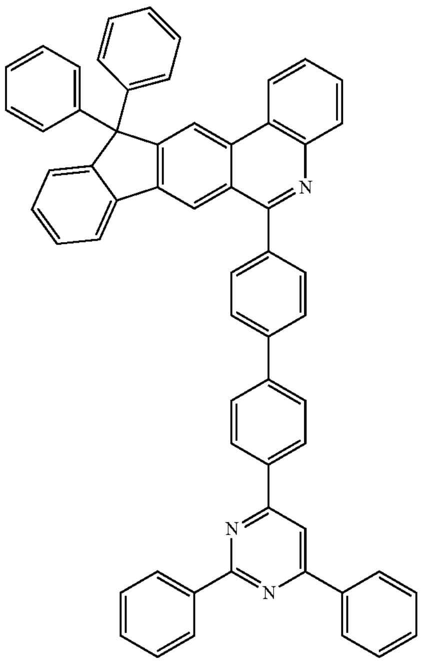
10-66
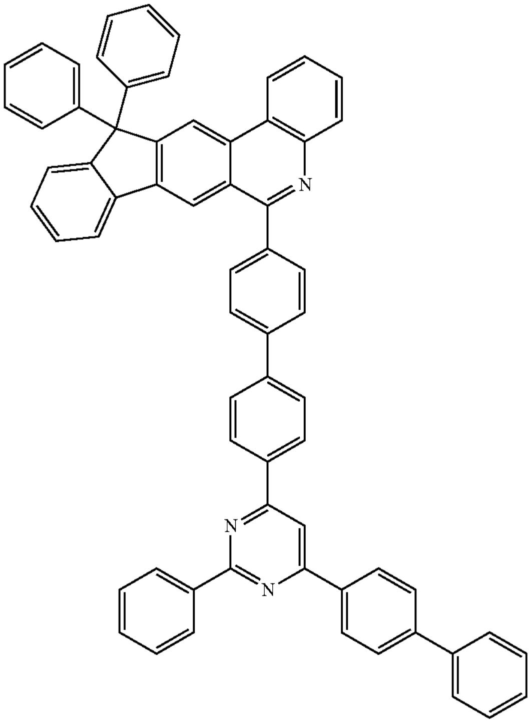
10-67
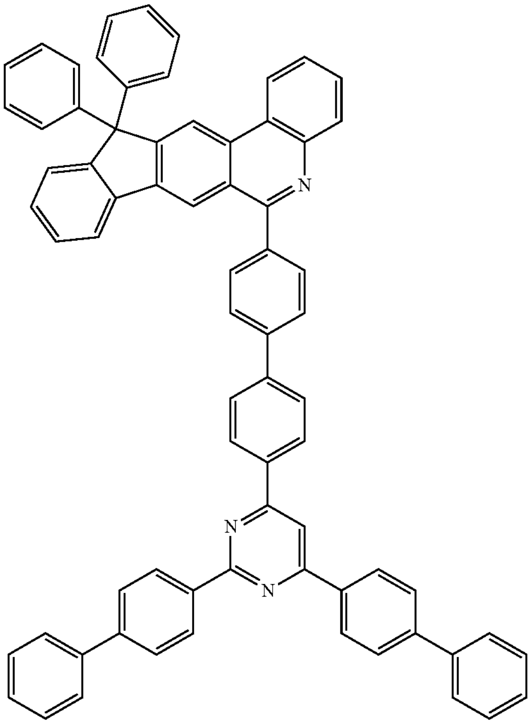
10-68
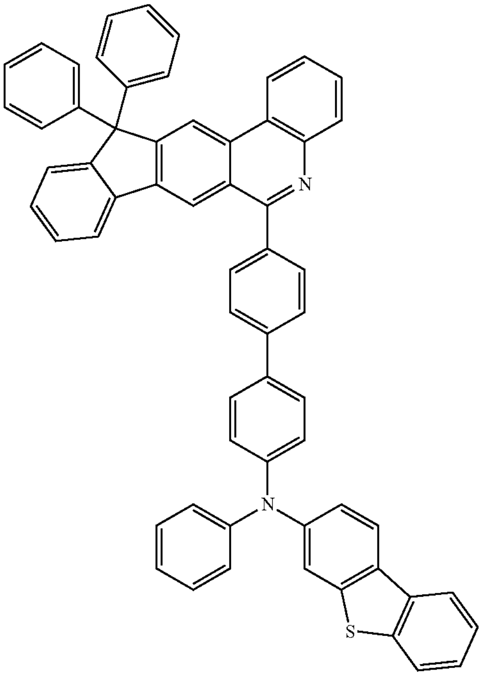

10-69
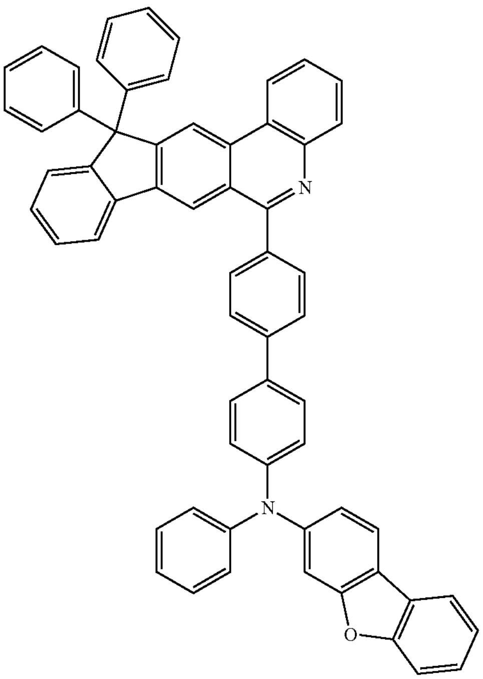
10-70
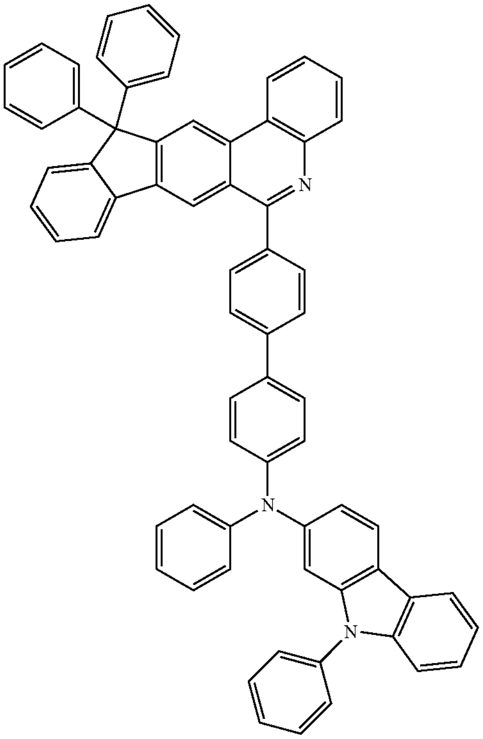
10-71
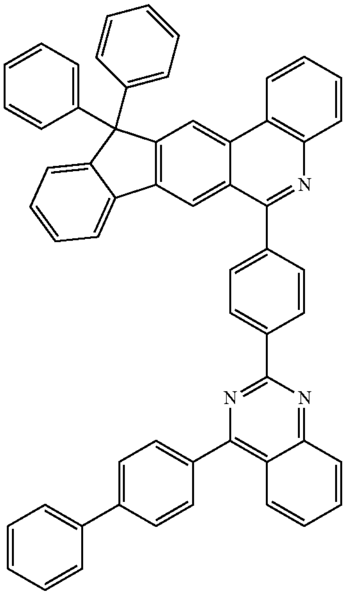
10-72
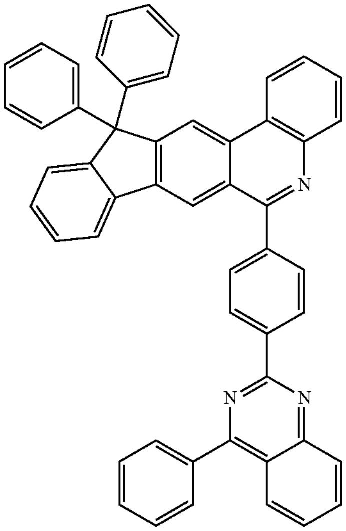

-continued
10-73
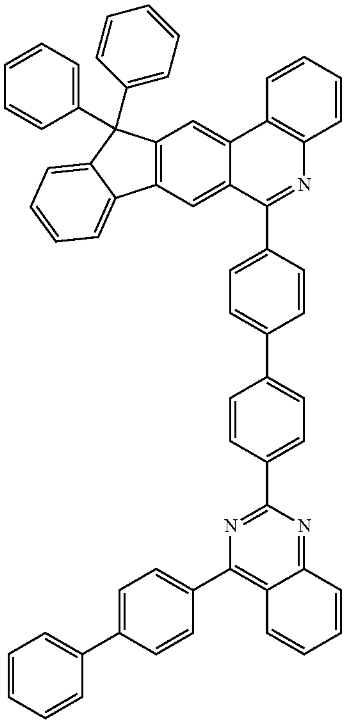
10-74
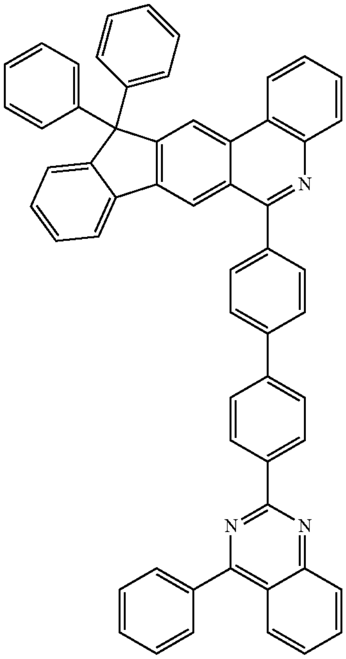
-continued
10-75
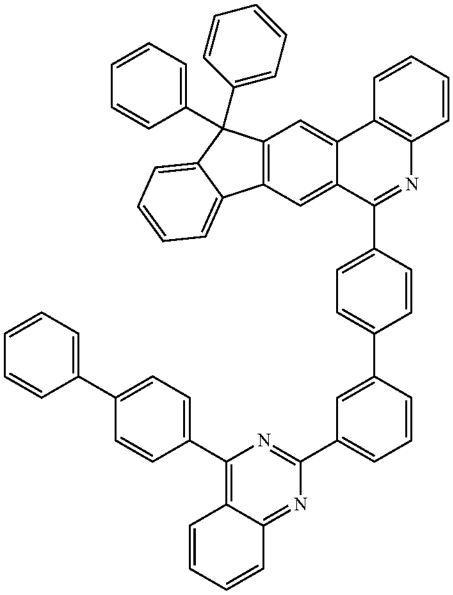
10-76
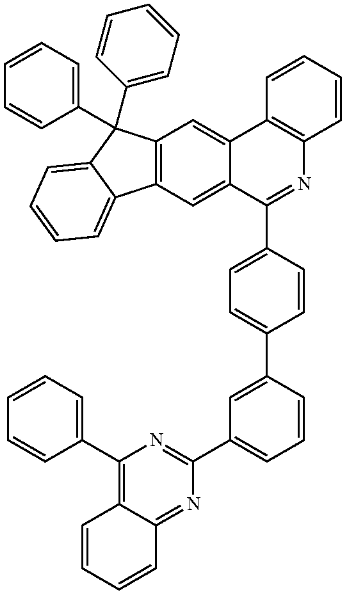

-continued
1-77
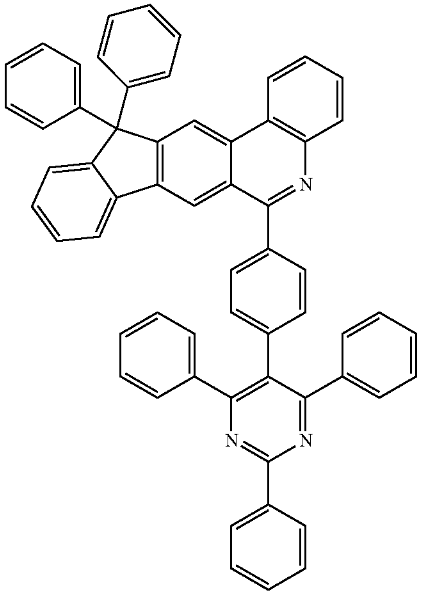
10-77
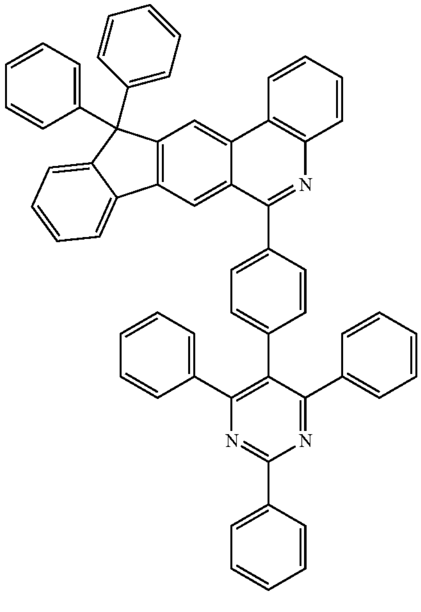
-continued
10-78
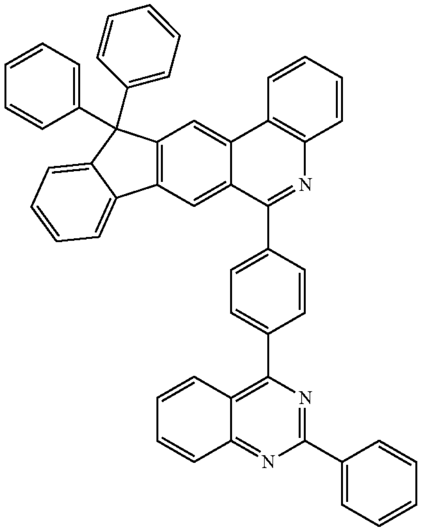
10-79
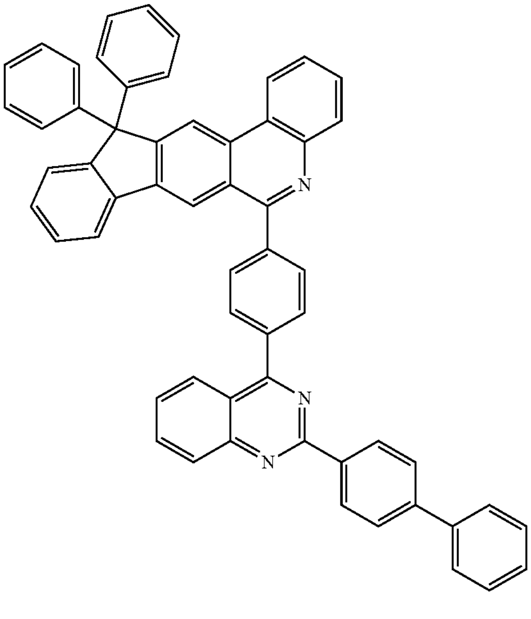

10-79
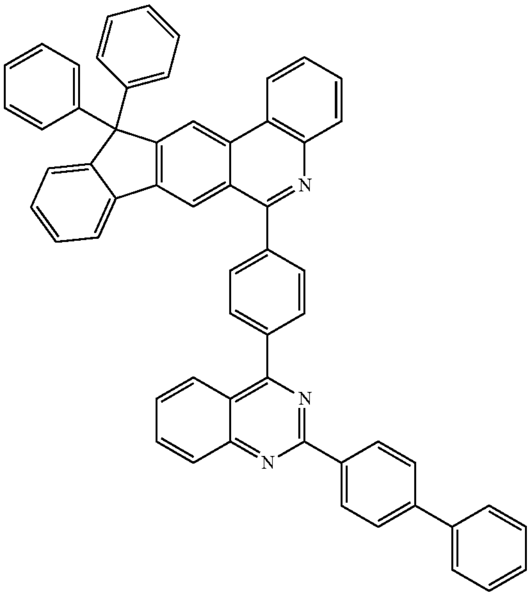
10-80
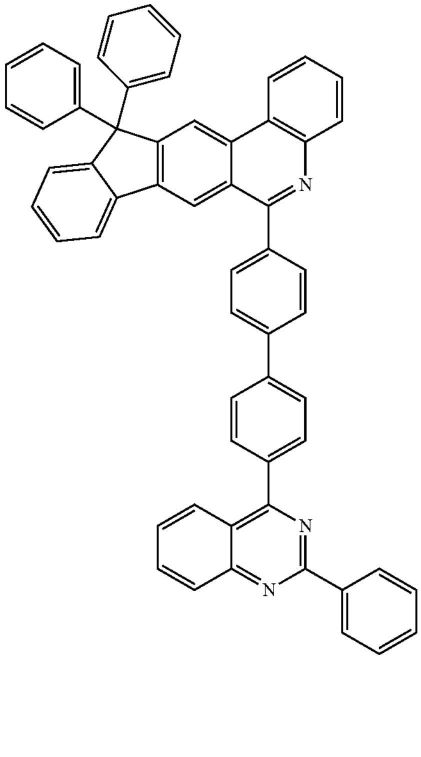
10-81
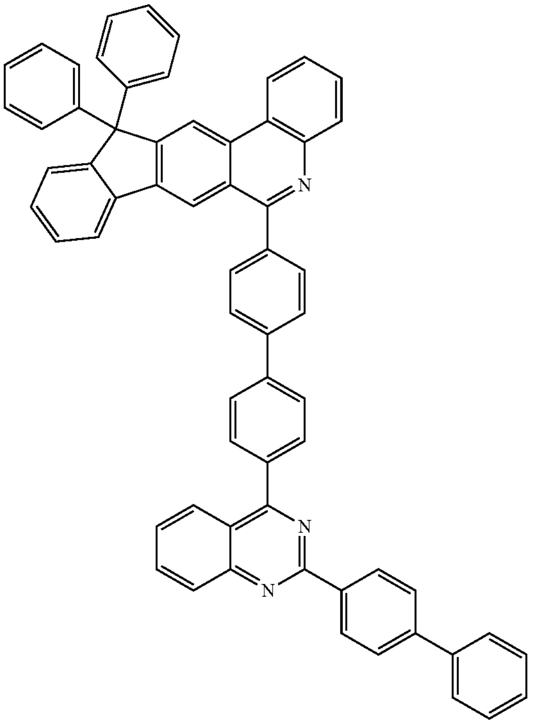
10-82
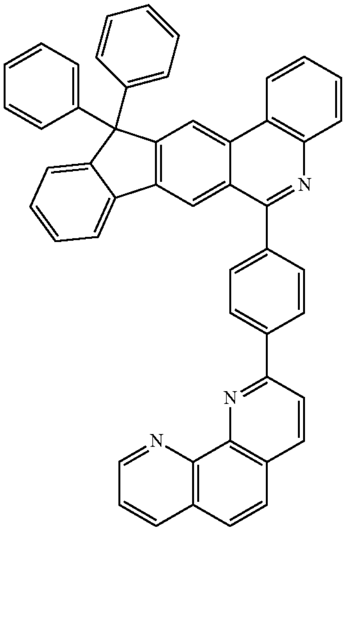

-continued
10-83
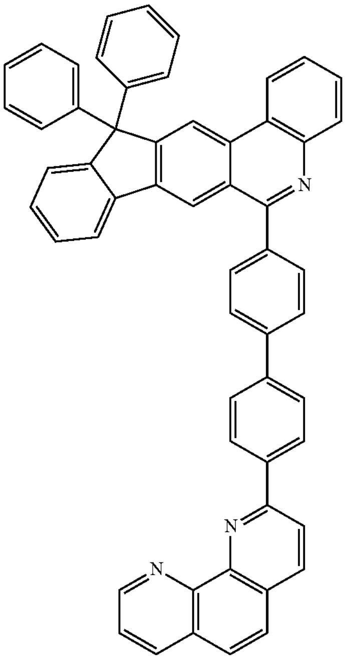
10-84
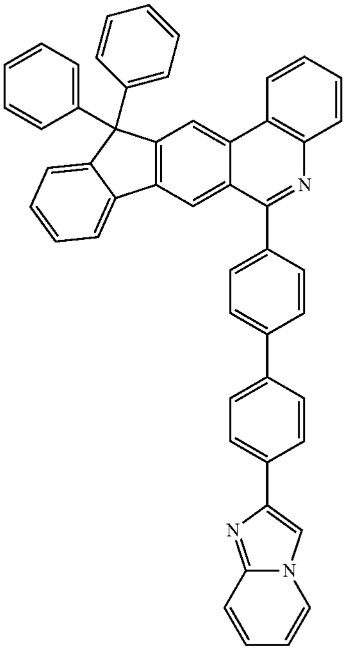
-continued
10-85
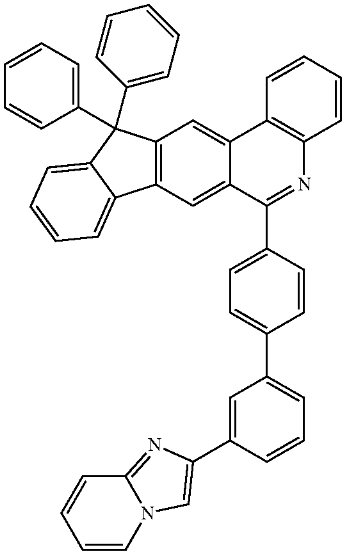
10-86
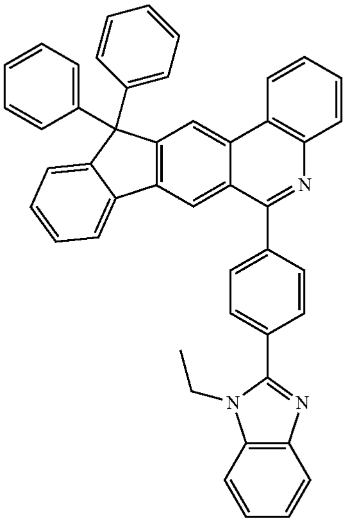

-continued
10-87
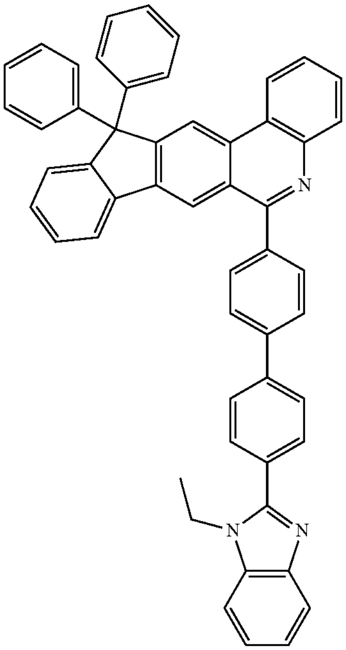
10-88
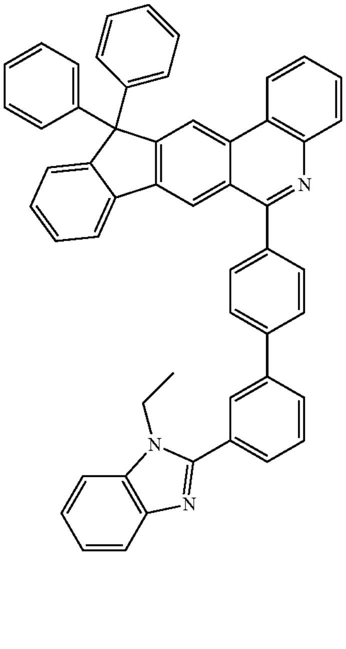
-continued
10-89
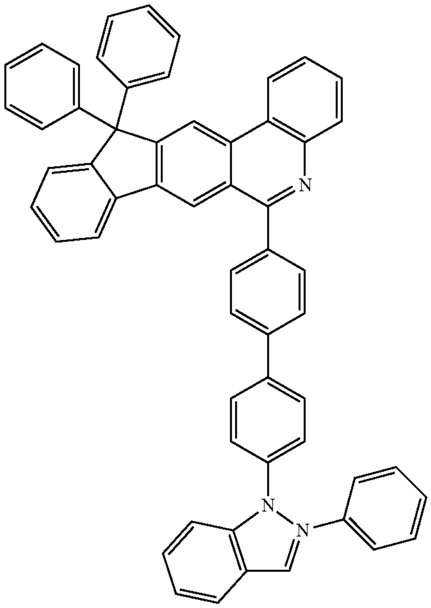
10-90
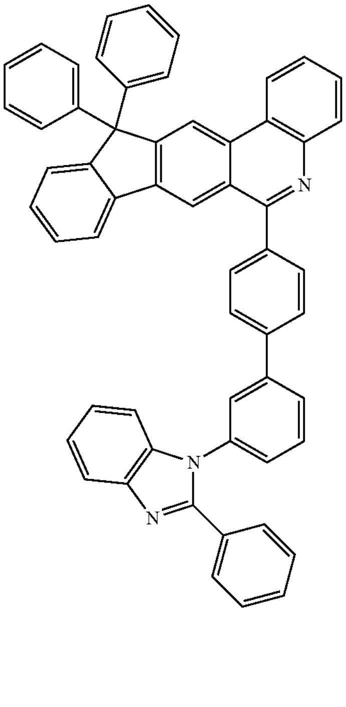

-continued
10-91
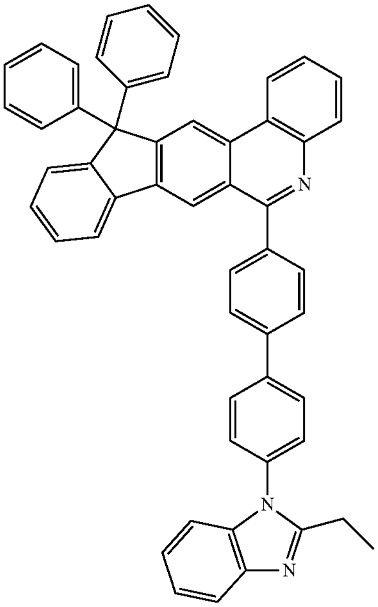
10-92
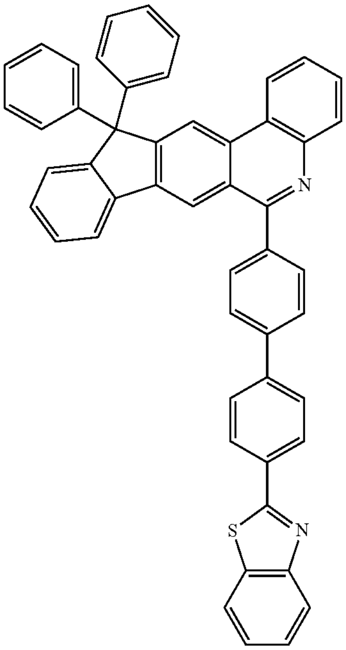
-continued
10-93
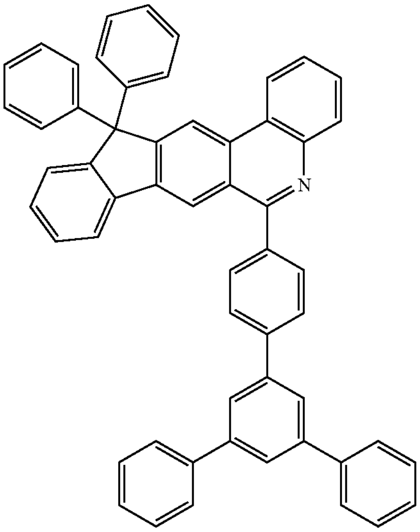
10-94
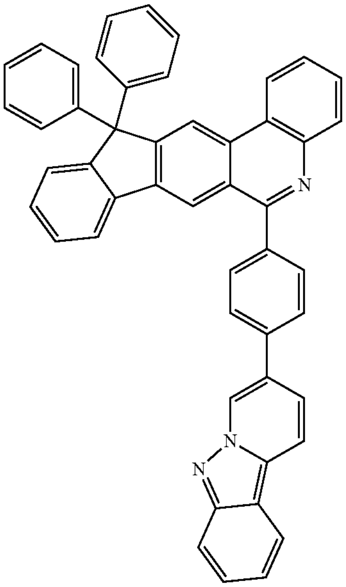

-continued
10-95
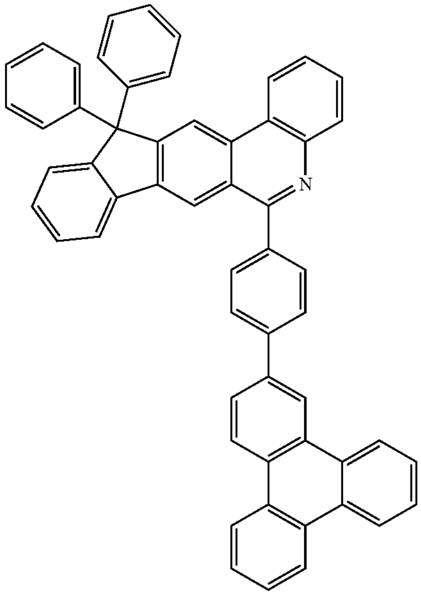
10-96
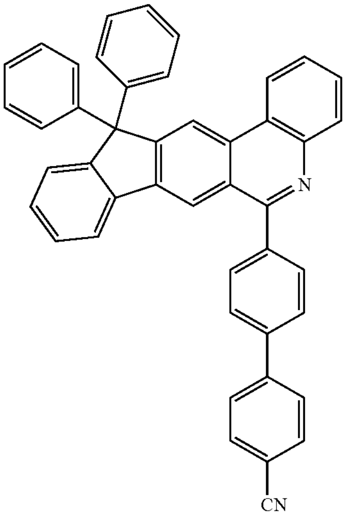
-continued
10-97
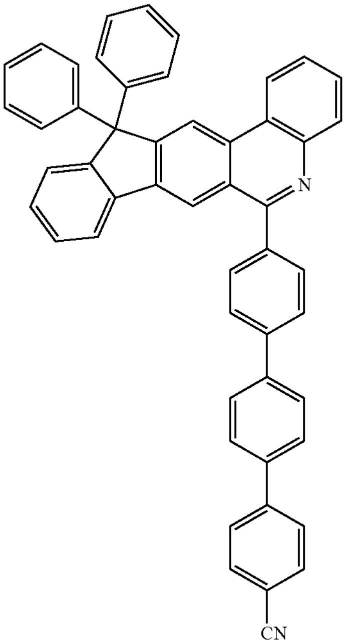
10-98
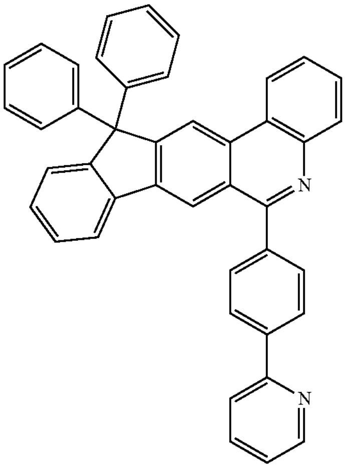
10-99
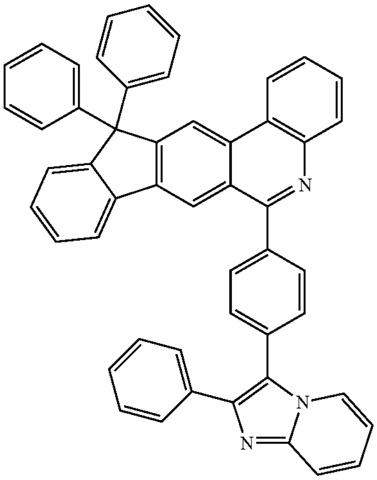

10-100
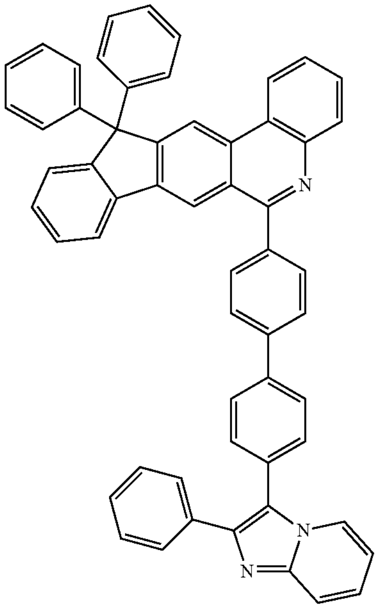
11-1
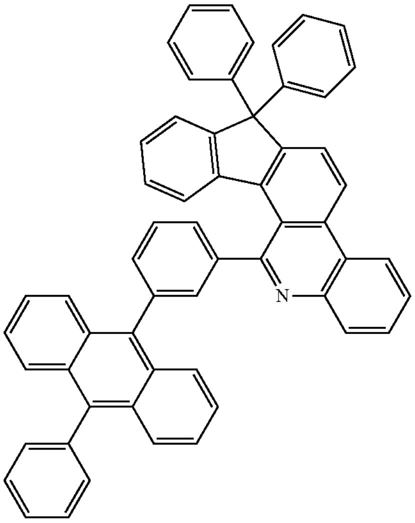
11-2
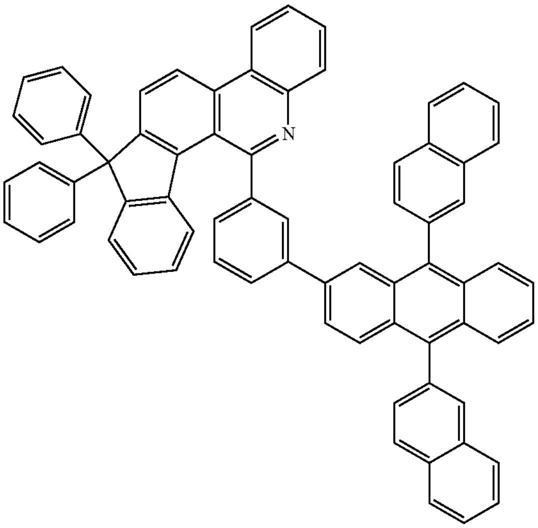
11-3
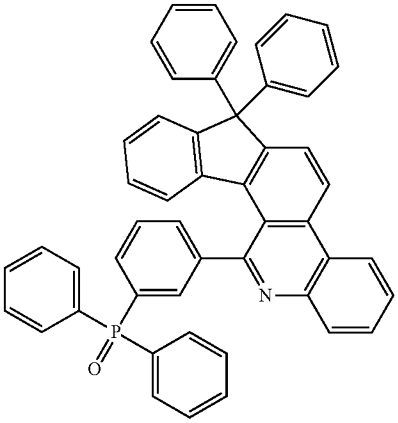
11-4
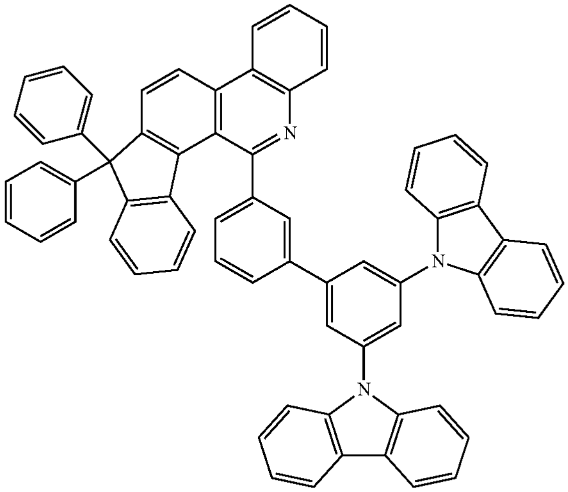

-continued
11-5
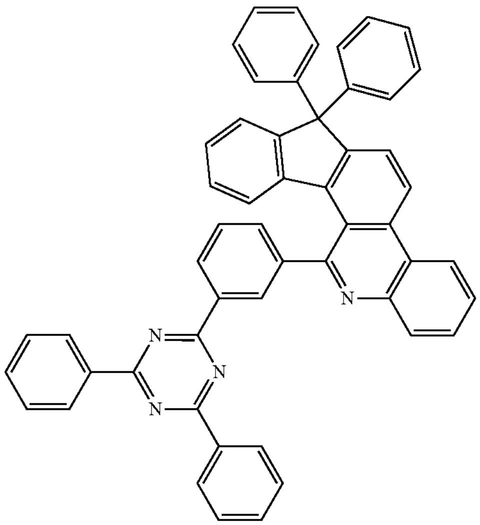
11-6
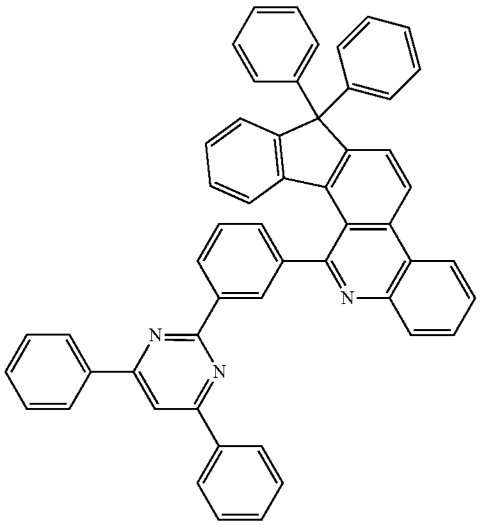
-continued
11-7
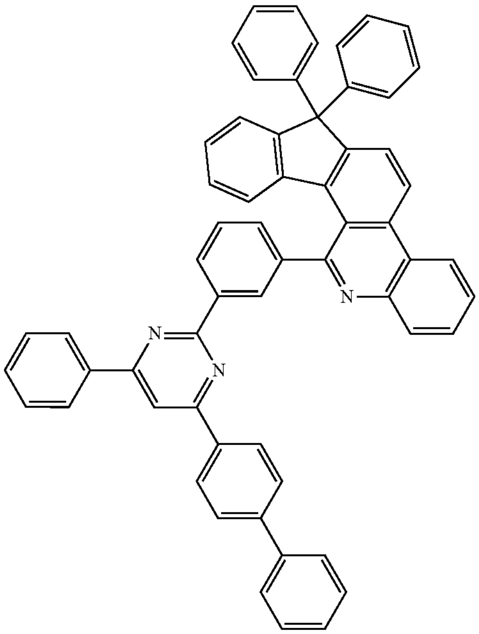
11-8
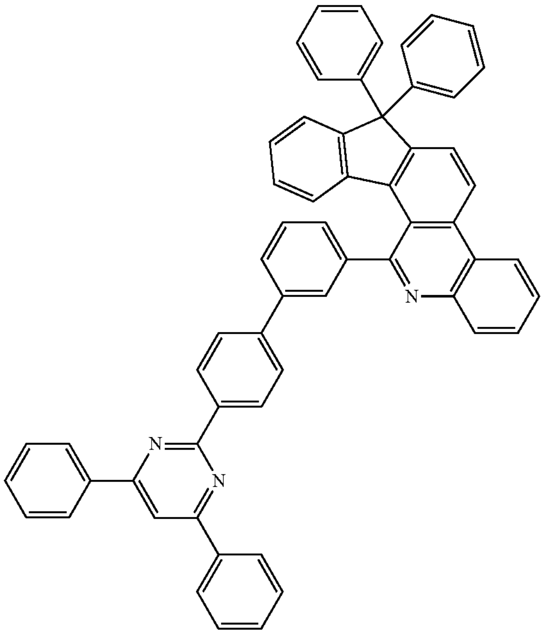

-continued
11-9
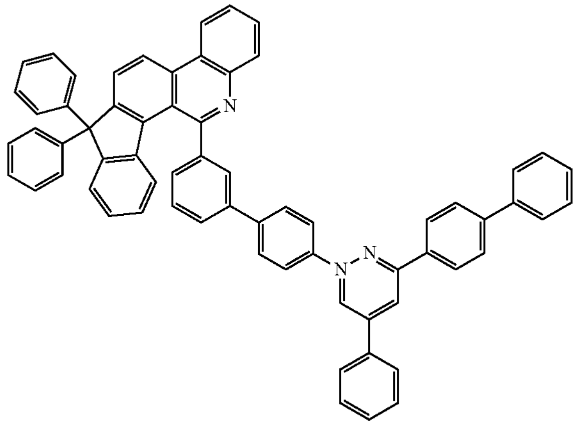
11-10
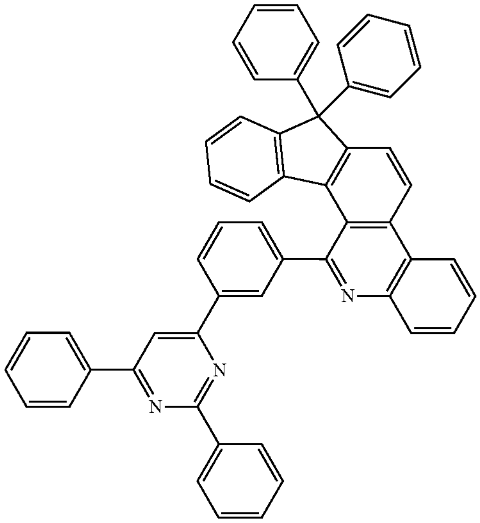
11-11
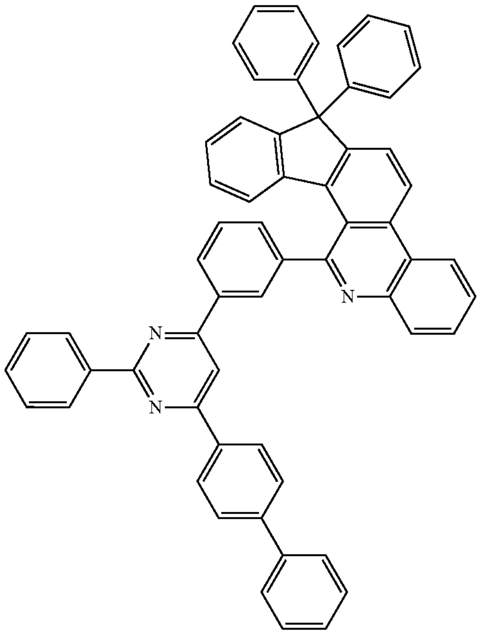
-continued
11-12
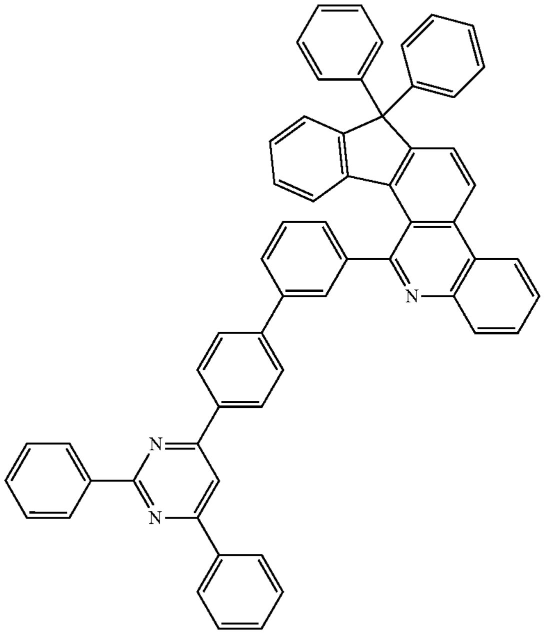
11-13
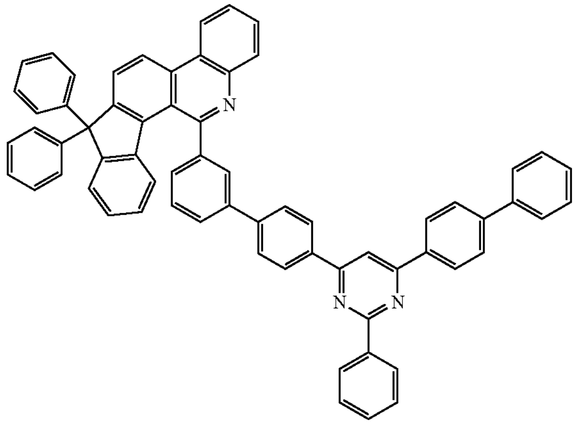
11-14
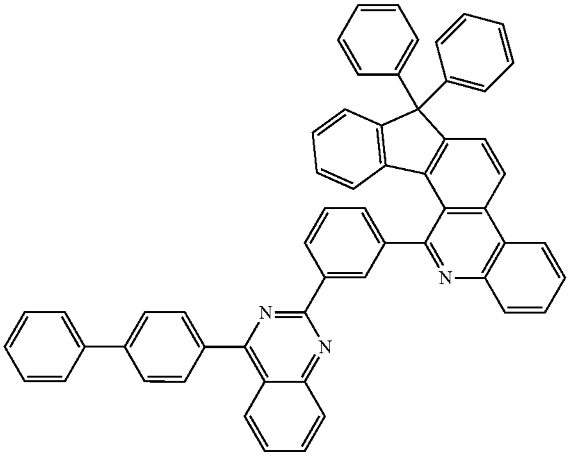

-continued
11-15
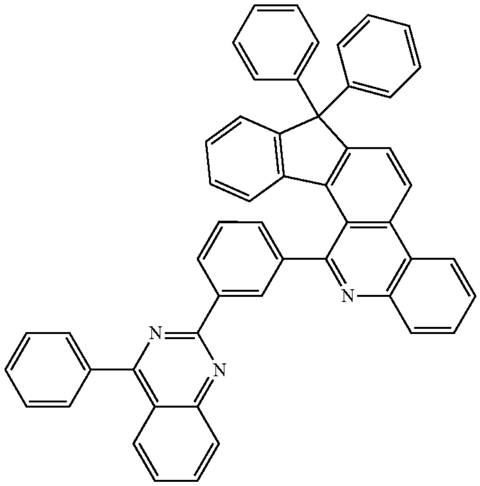
11-16
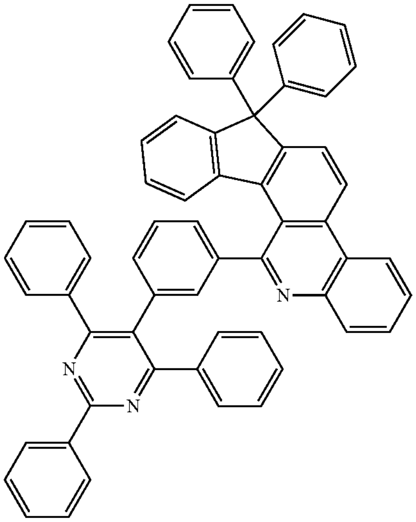
11-17
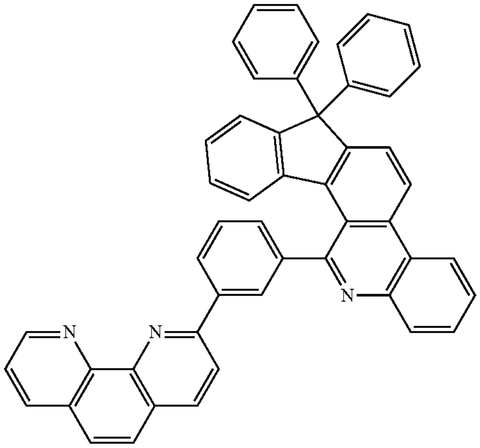
-continued
11-18
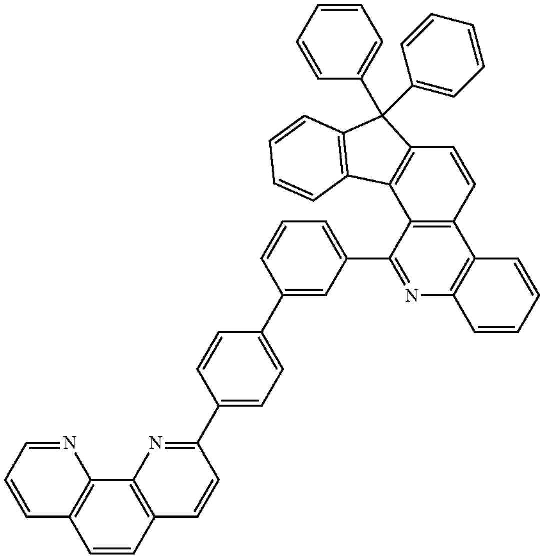
11-19
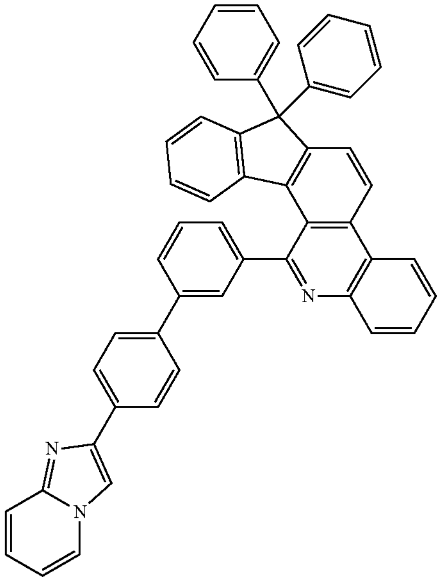

-continued
11-20
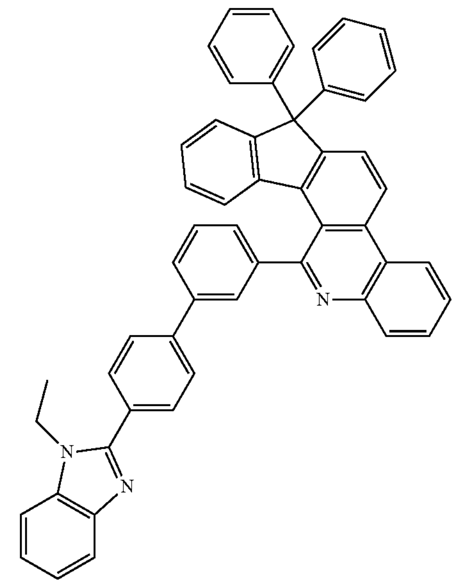
11-21
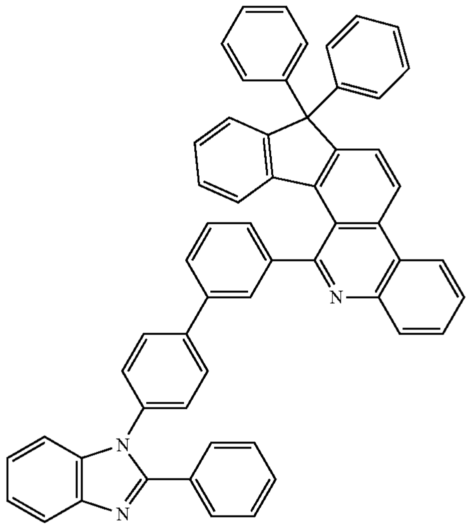
11-22
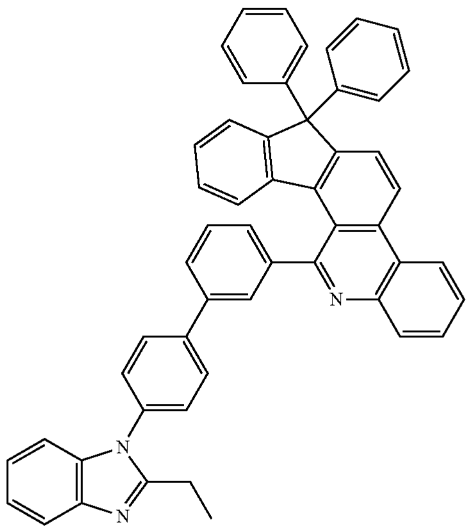
-continued
11-23
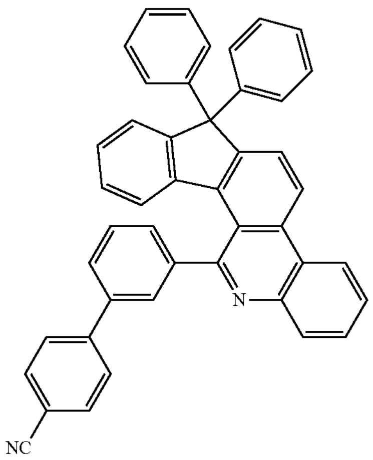
11-24
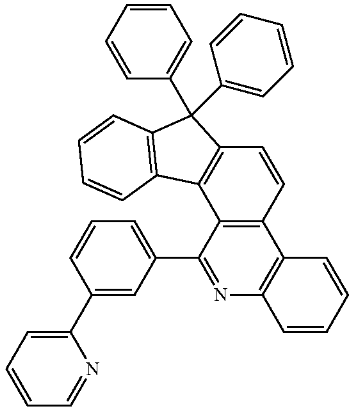
11-25
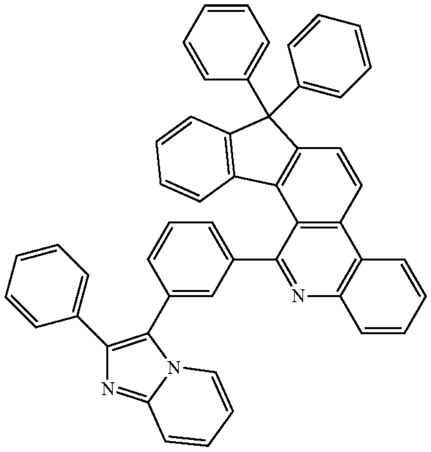

-continued
11-26
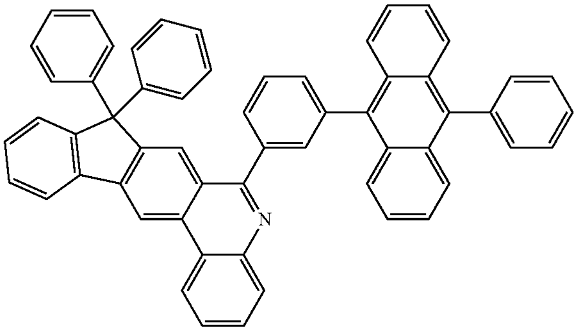
11-27
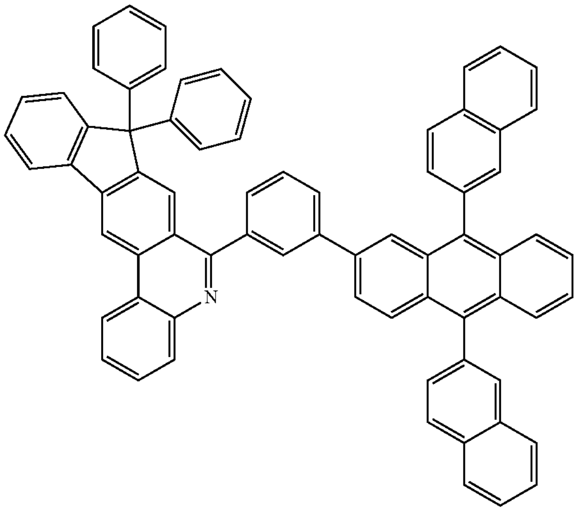
11-28
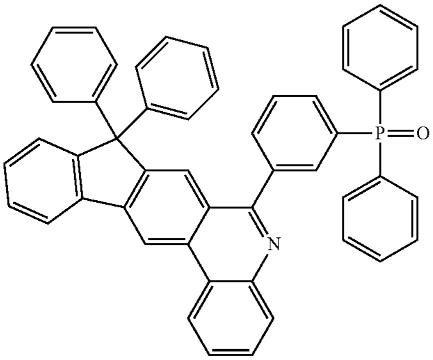
-continued
11-29
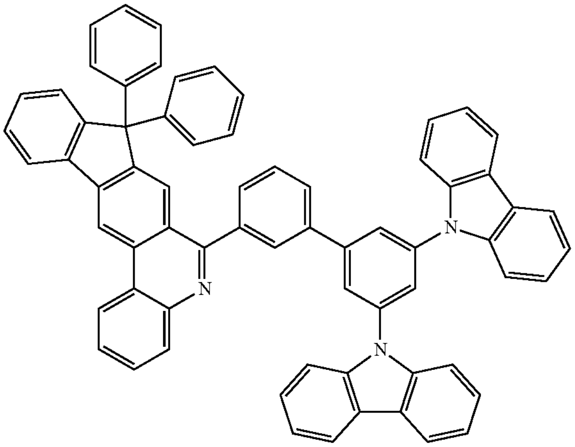
11-30
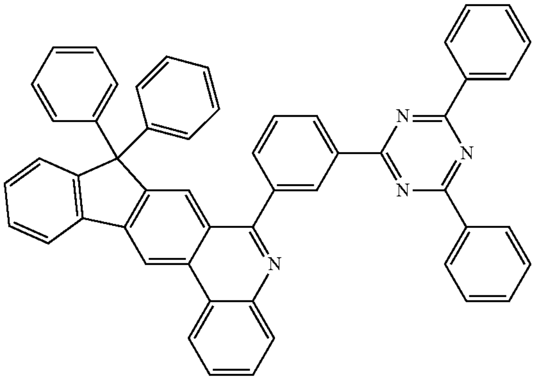
11-31
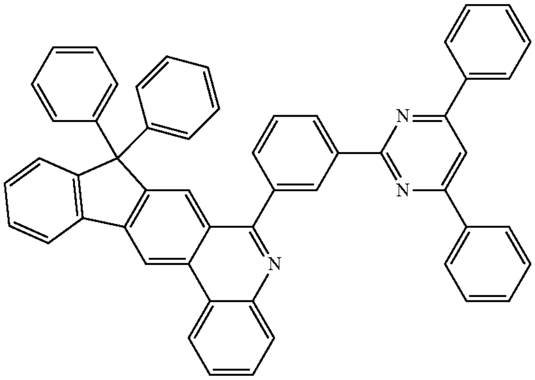

-continued
11-32
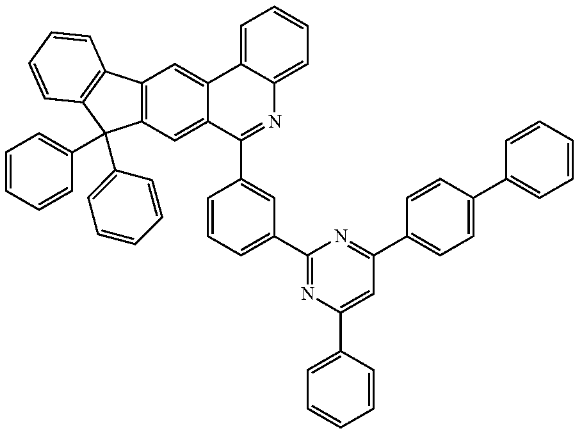
11-33
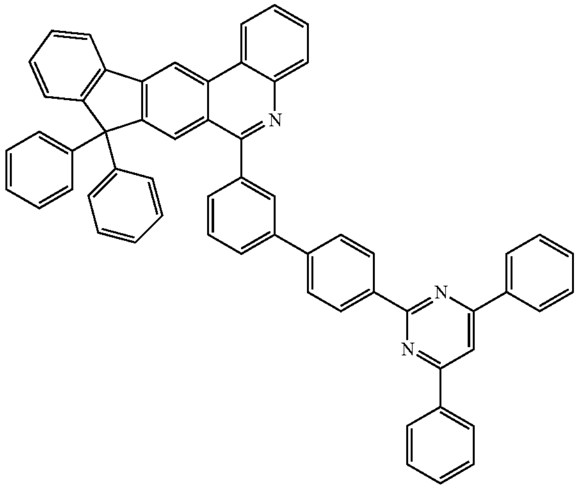
11-34
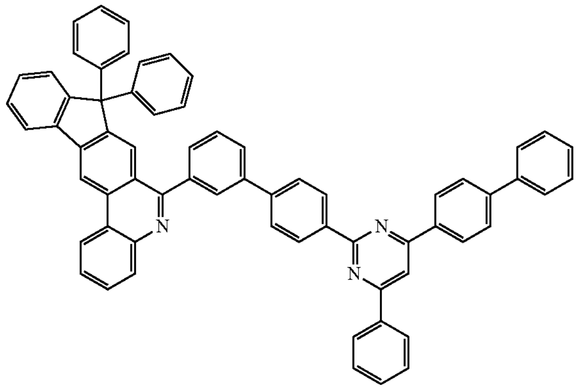
-continued
11-35
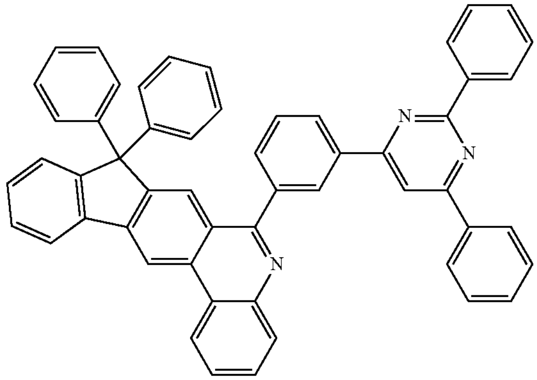
11-36
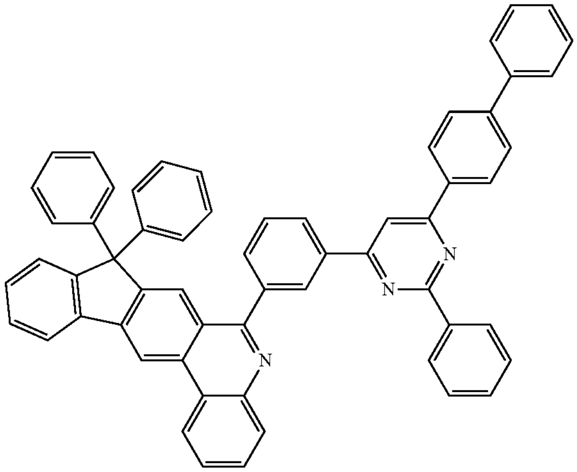
11-37
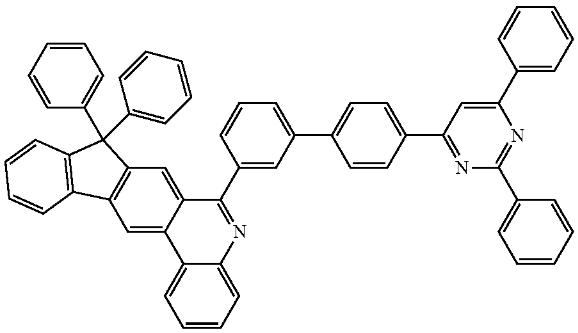

-continued
11-38
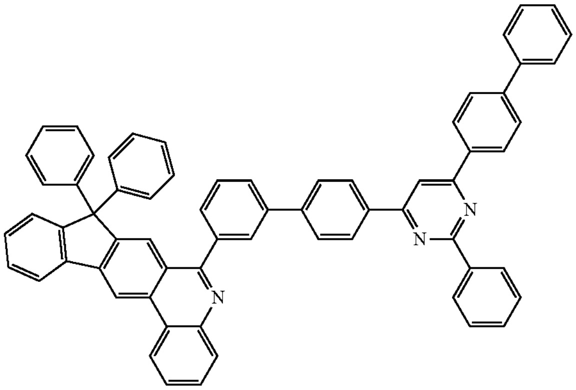
11-39
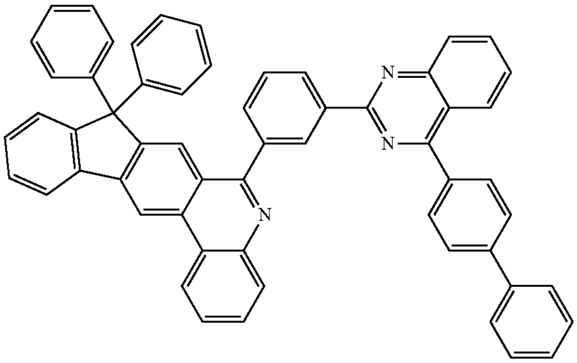
11-40
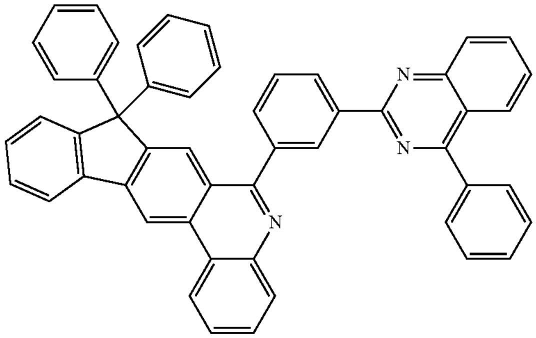
11-41
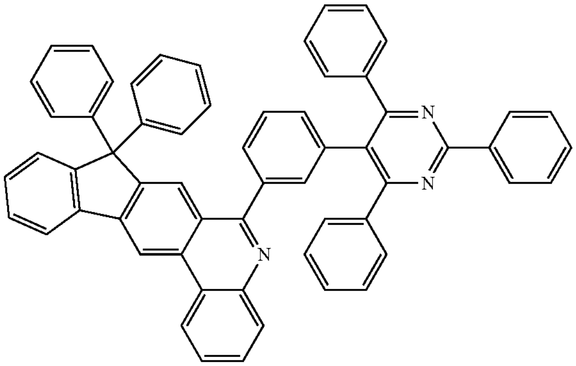
-continued
11-42
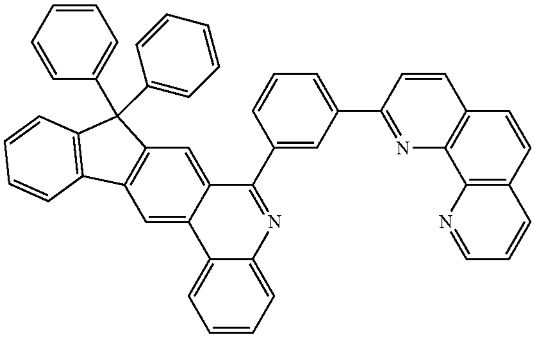
11-43
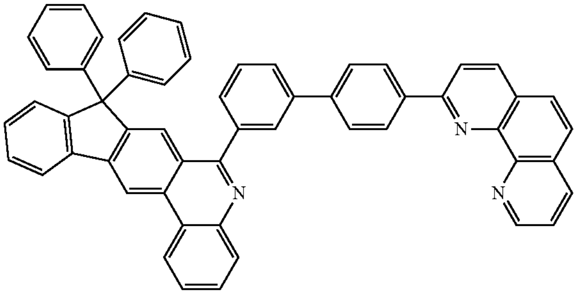
11-44
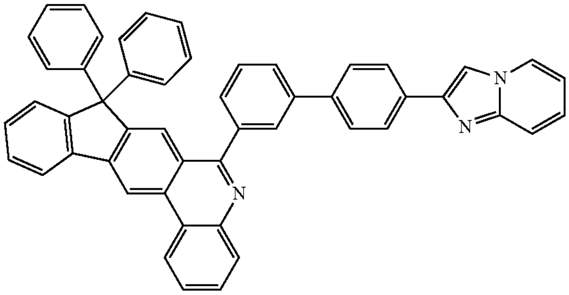
11-45
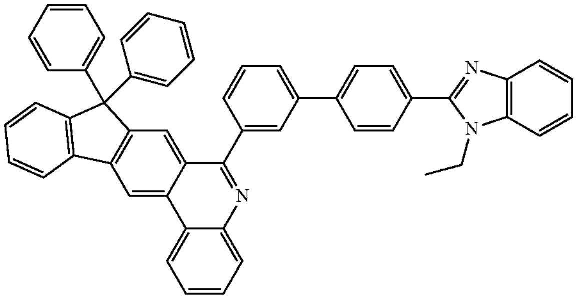

-continued
11-46
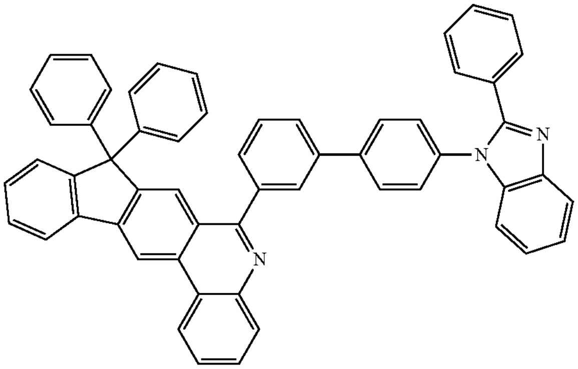
11-47
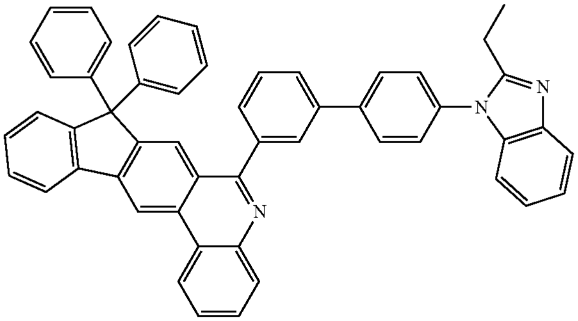
11-48
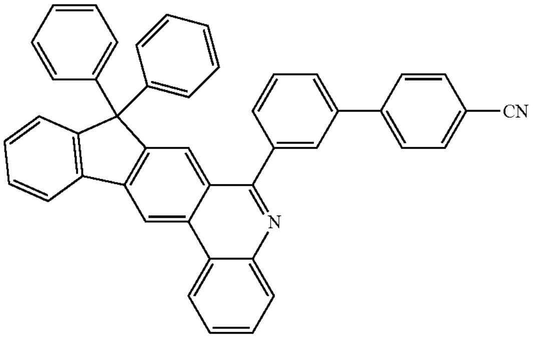
11-49
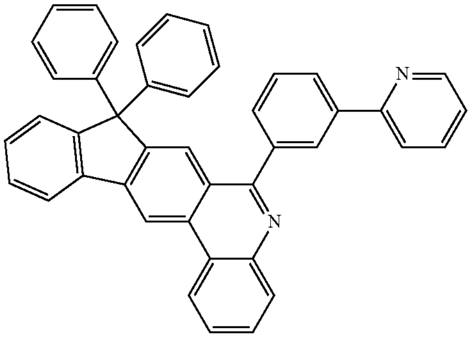
-continued
11-50
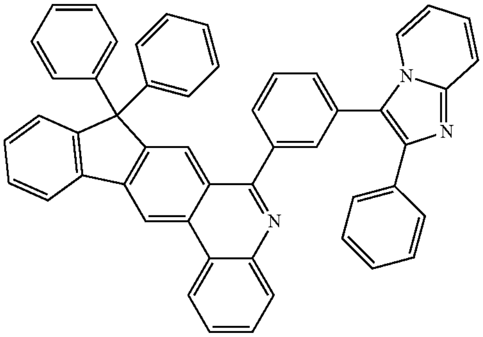
11-51
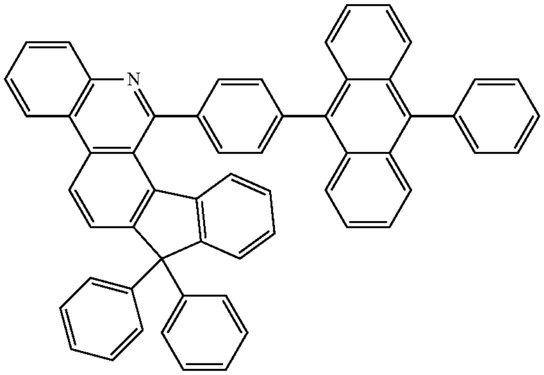
11-52
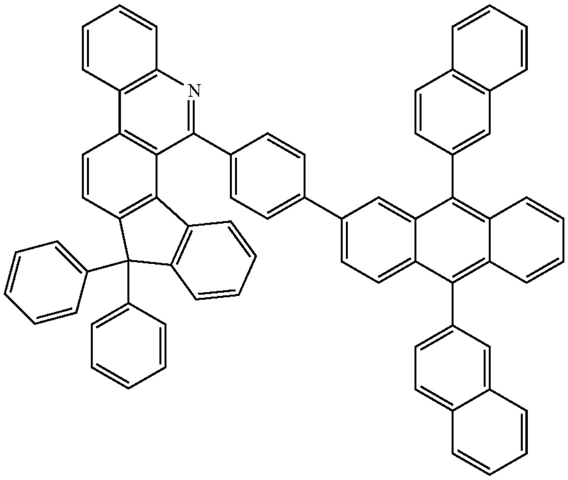
11-53
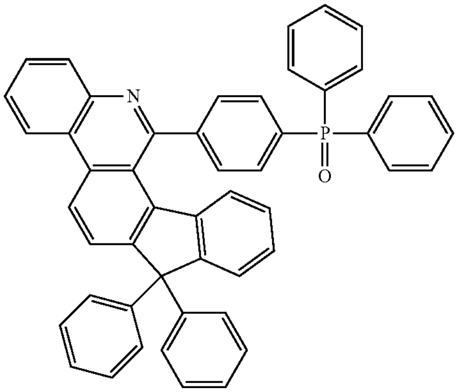

-continued
11-54
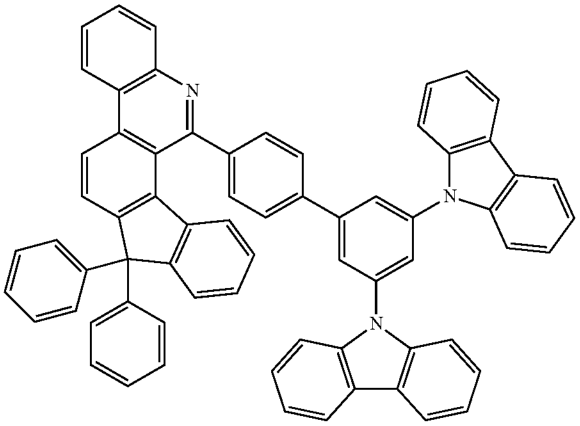
11-55
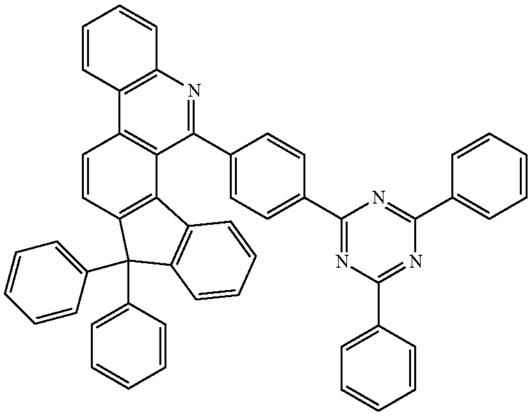
11-56
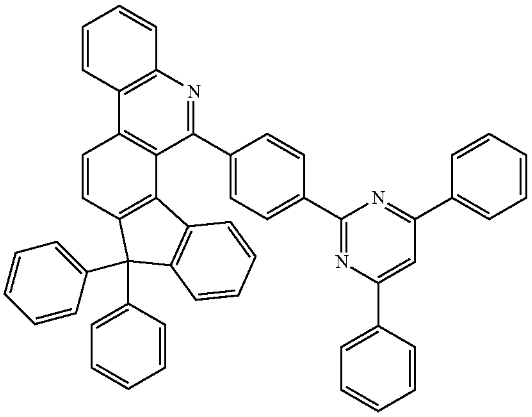
-continued
11-57
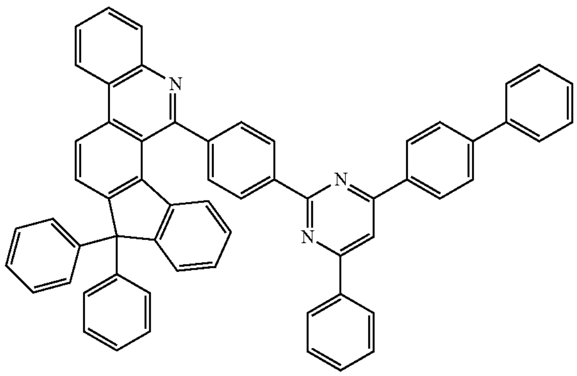
11-58
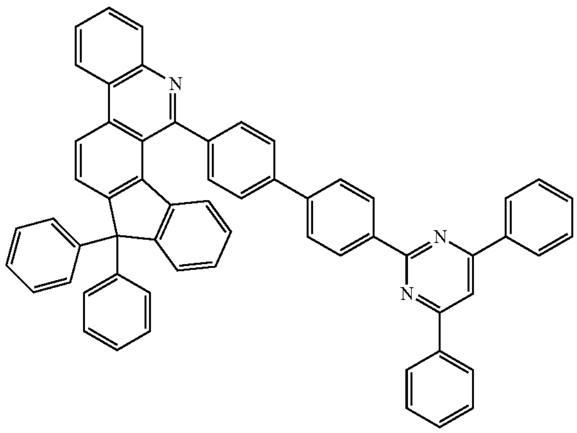
11-59
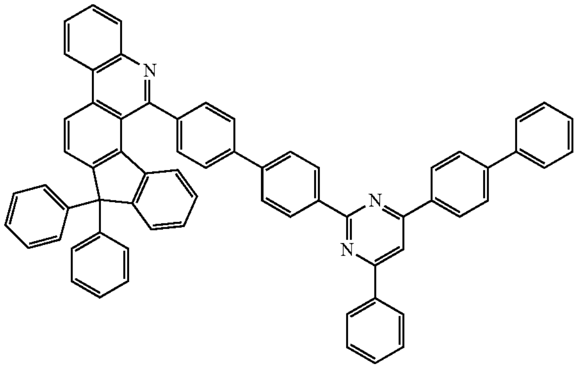

-continued
11-60
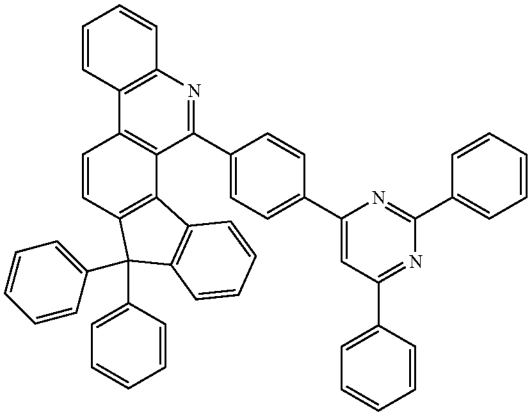
11-61
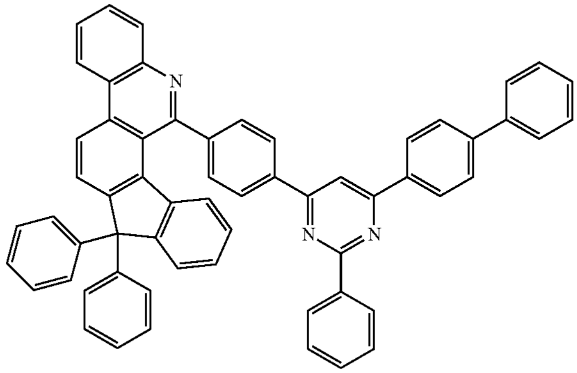
11-62
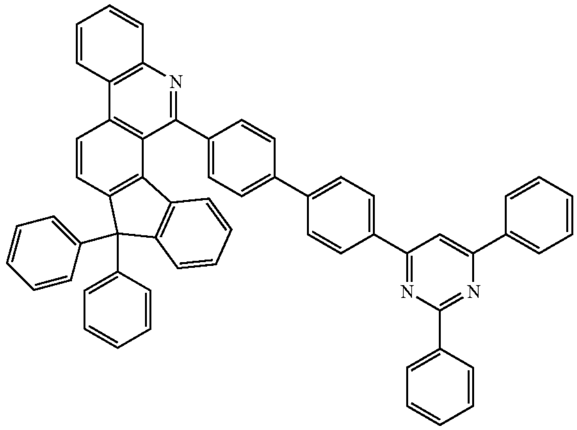
-continued
11-63
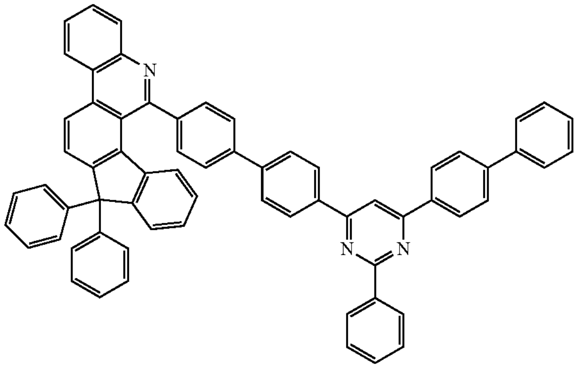
11-64
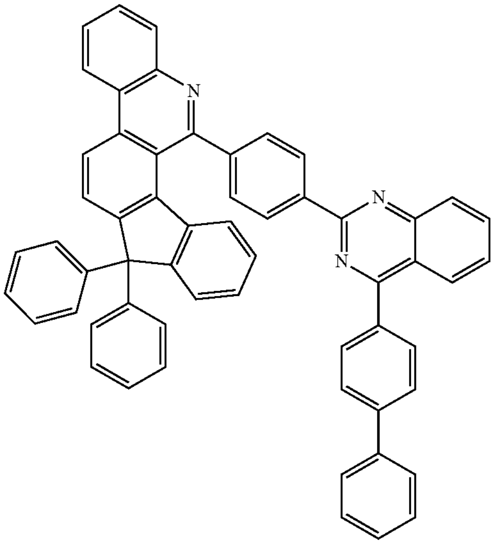
11-65
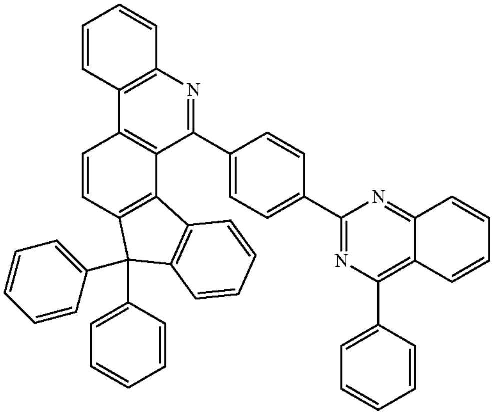

11-66
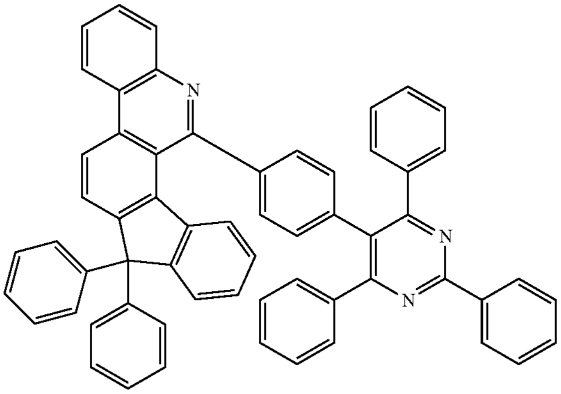
11-67
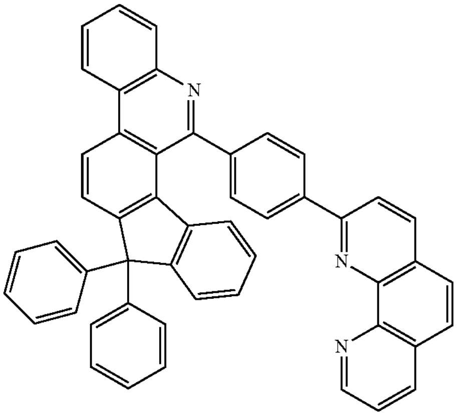
11-68
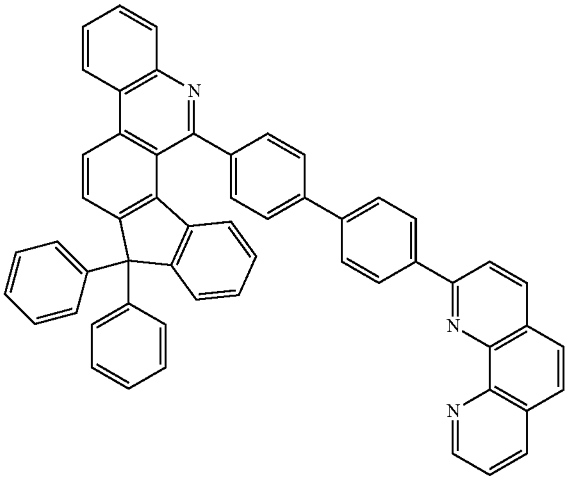
11-69
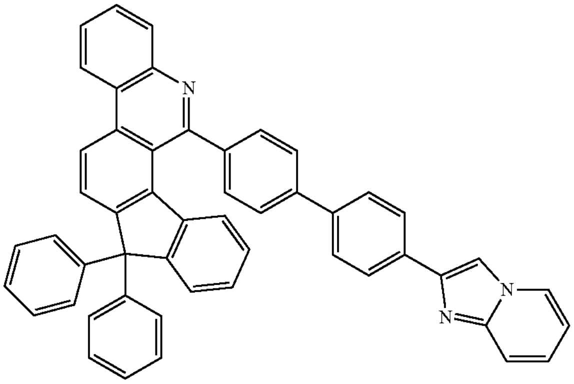
11-70
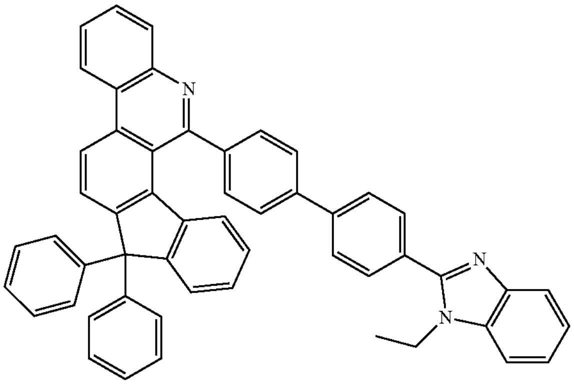
11-71
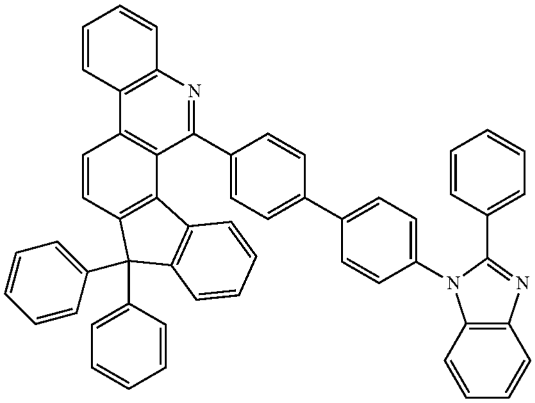

-continued
11-72
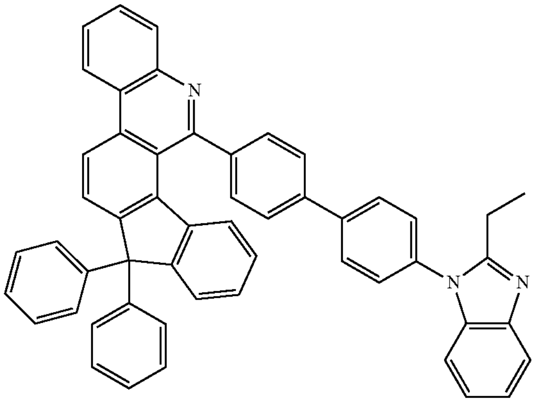
11-73
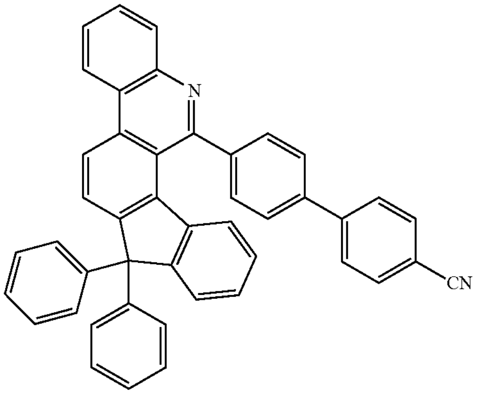
11-74
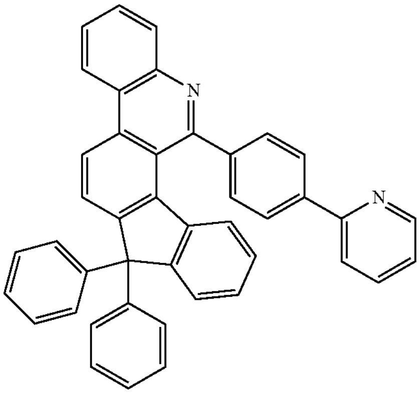
11-75
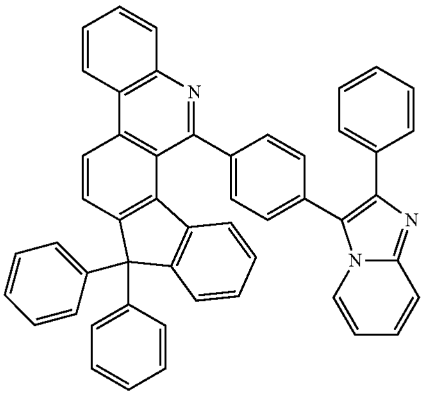
-continued
11-76
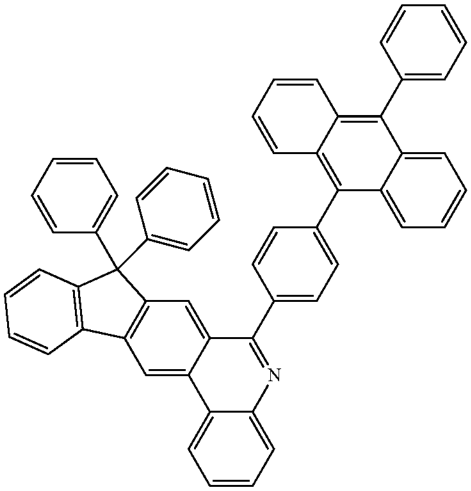
11-77
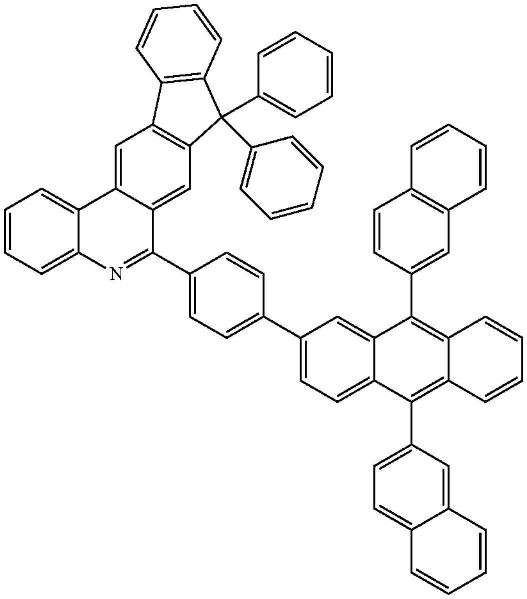
11-78
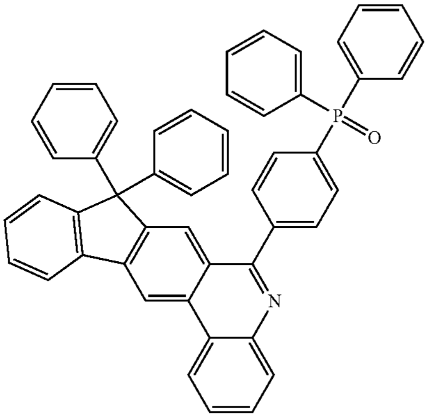

-continued
11-79
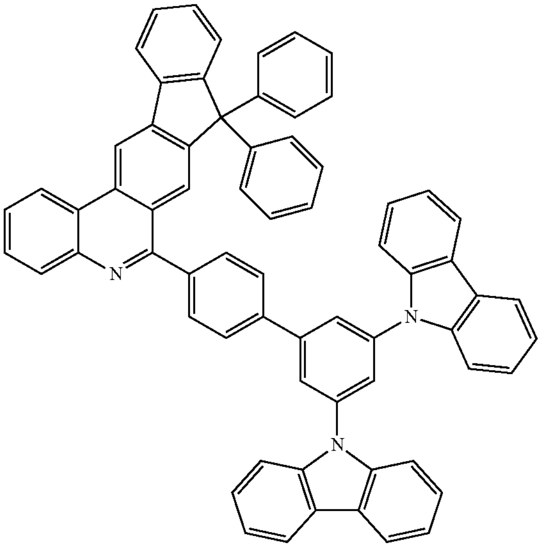
11-80
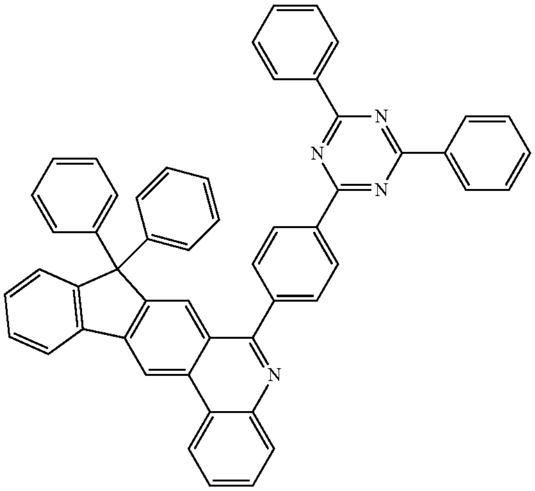
11-81
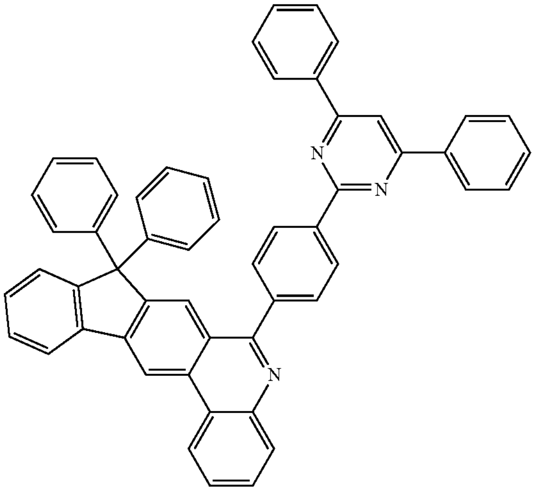
-continued
11-82
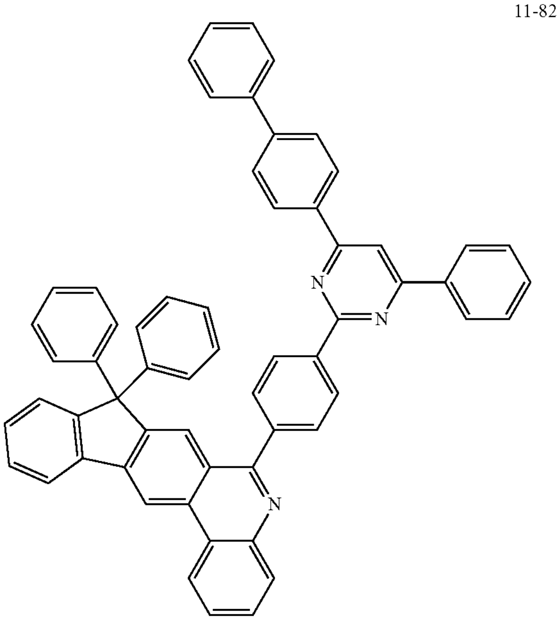
11-83
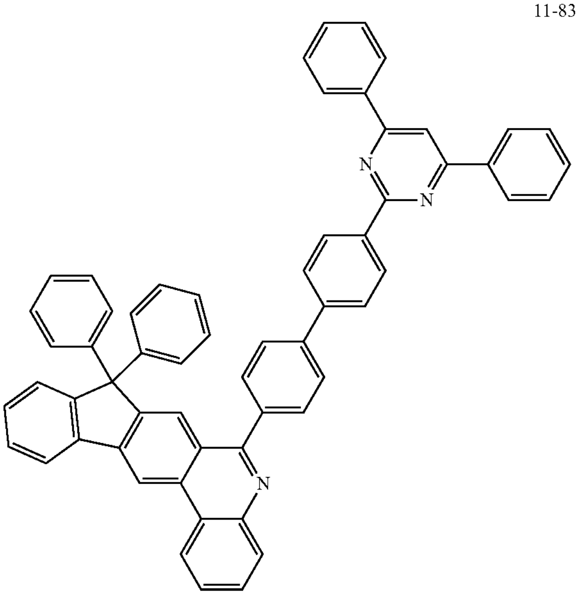
11-84
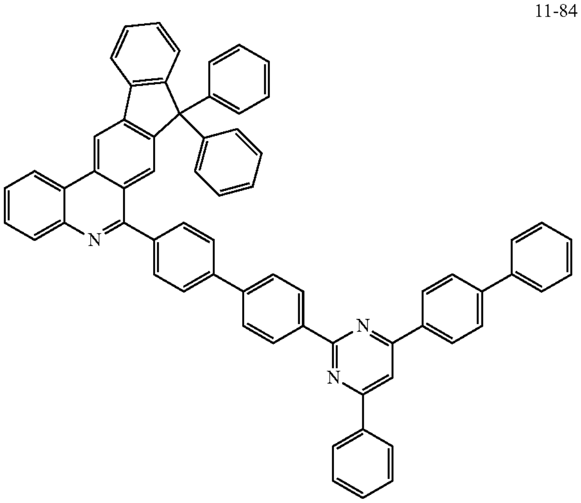

-continued
11-85
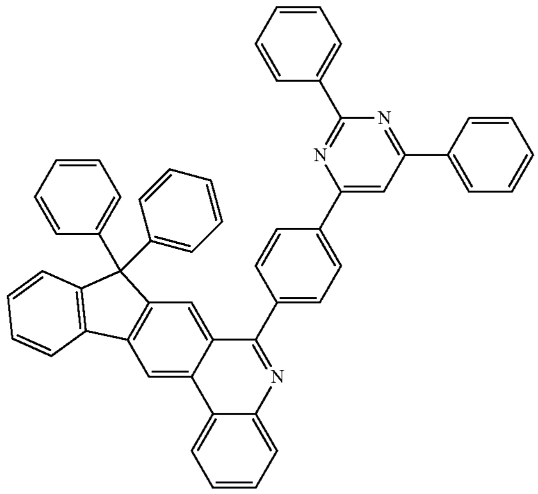
11-86
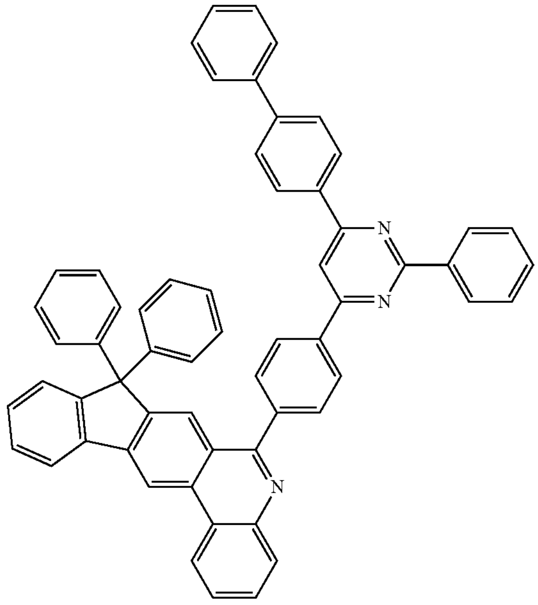
-continued
11-87
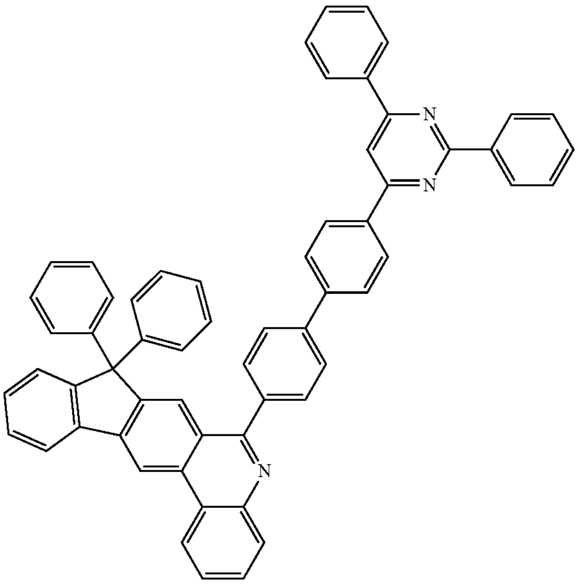
11-88
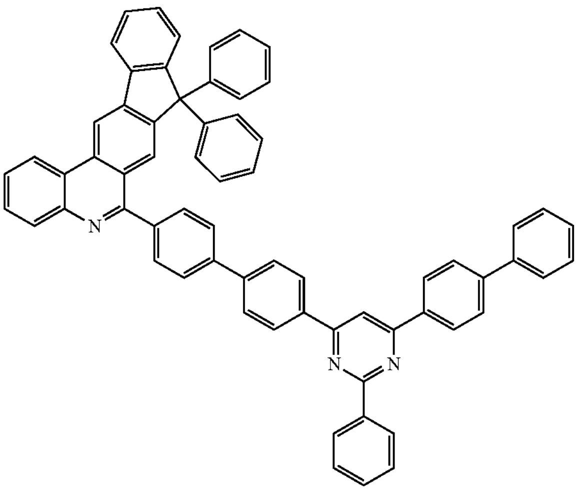
11-89
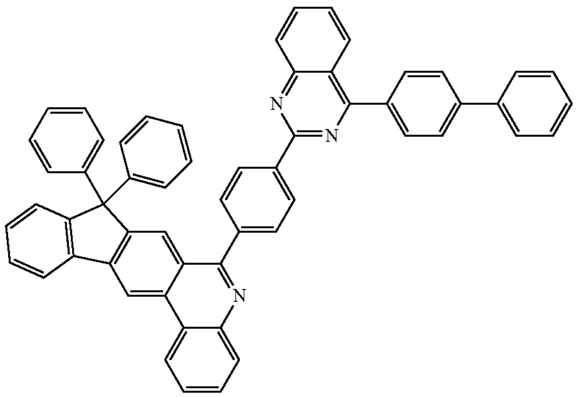

-continued
11-90
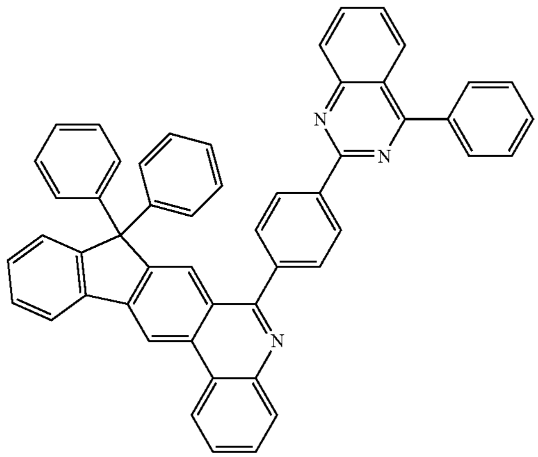
11-91
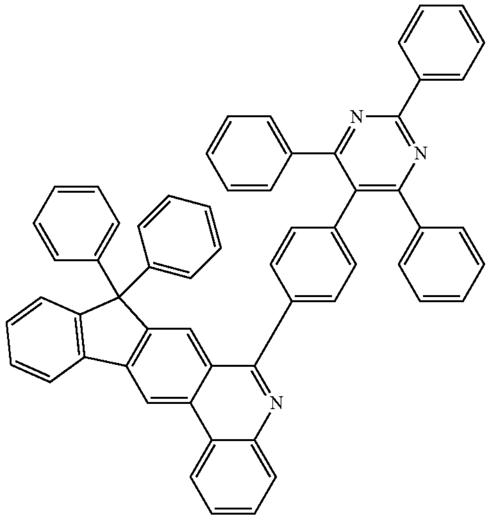
11-92
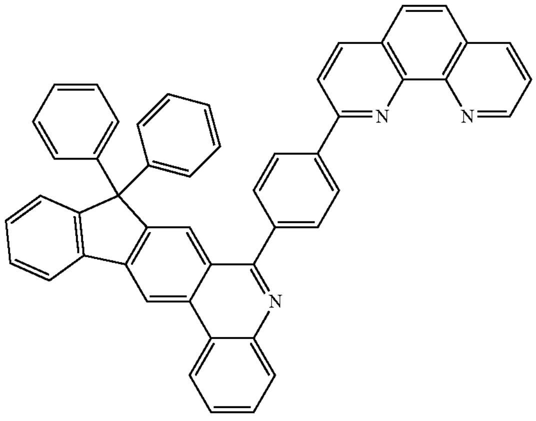
-continued
11-93
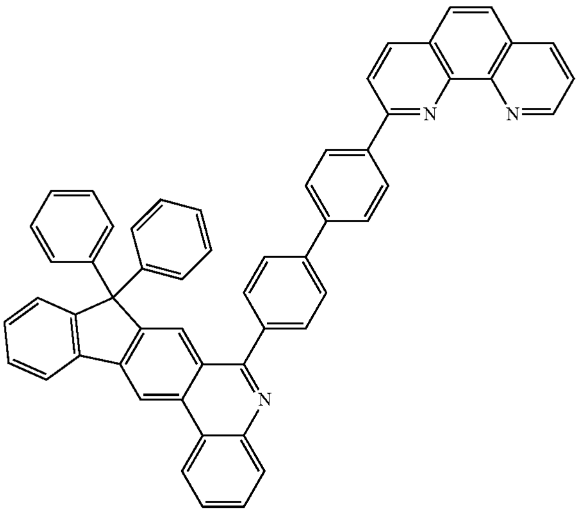
11-94
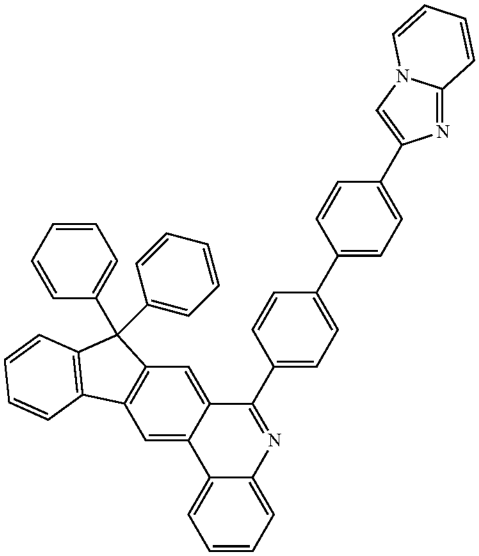
11-95
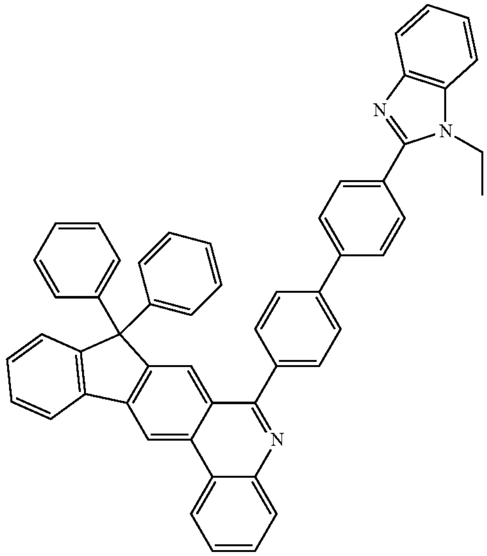

-continued
11-96
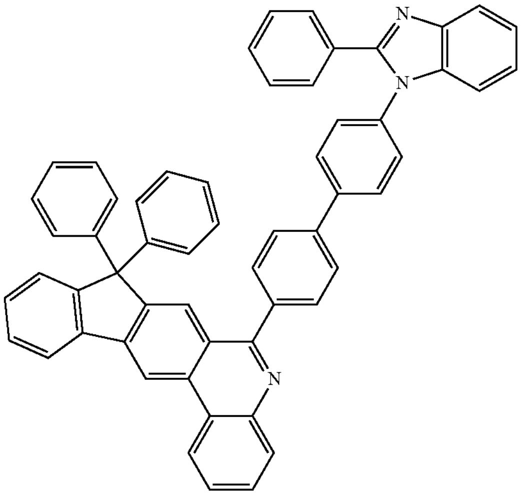
11-97
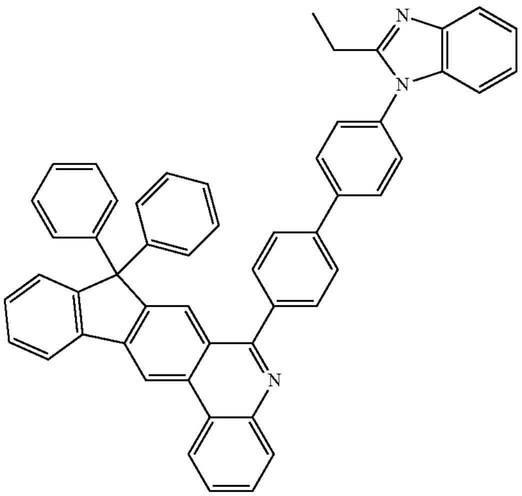
11-98
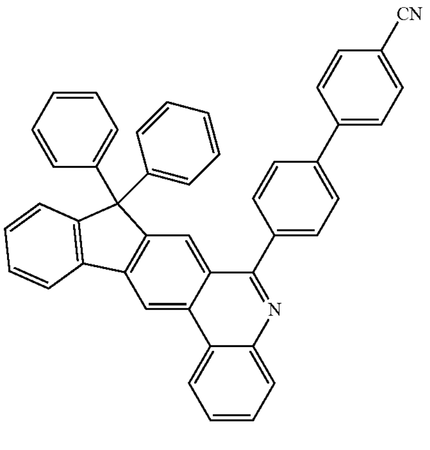
-continued
11-99
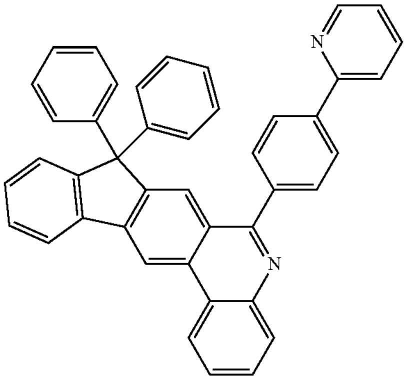
11-100
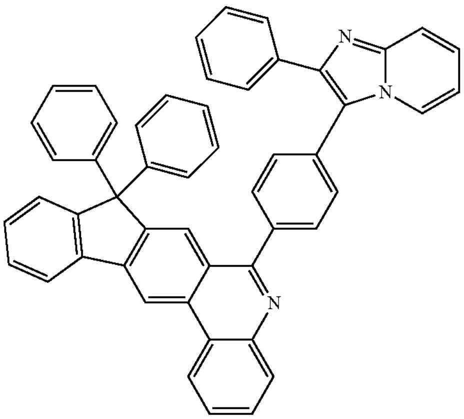
12-1
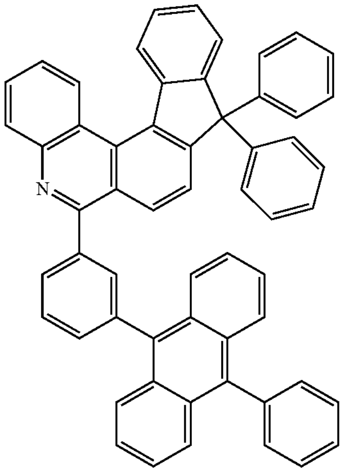

-continued
12-2
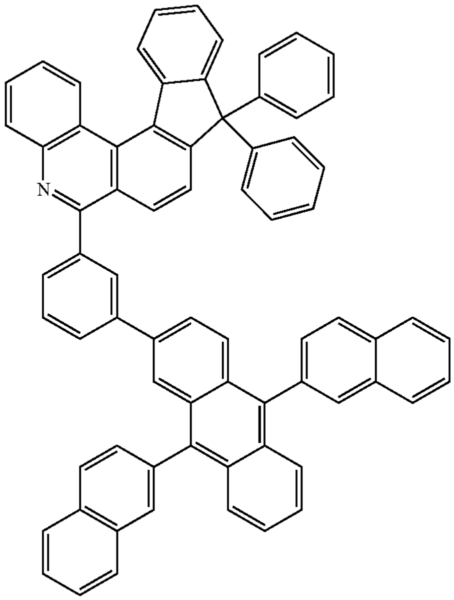
12-3
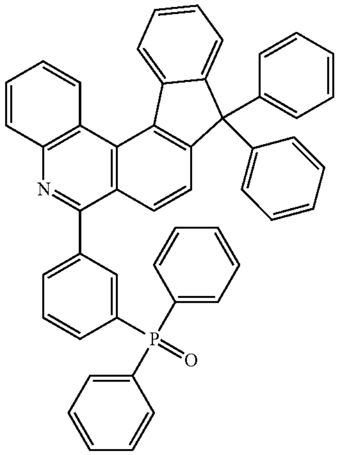
12-4
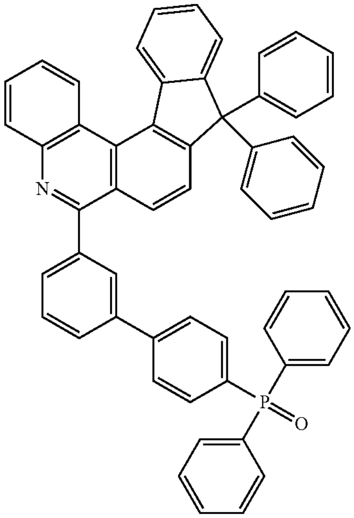
-continued
12-5
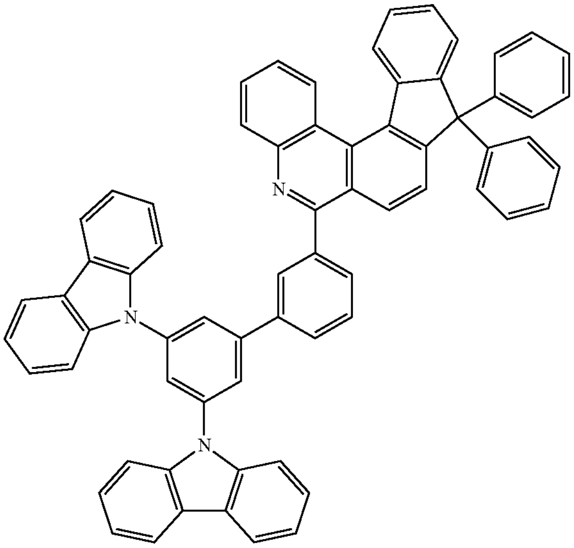
12-6
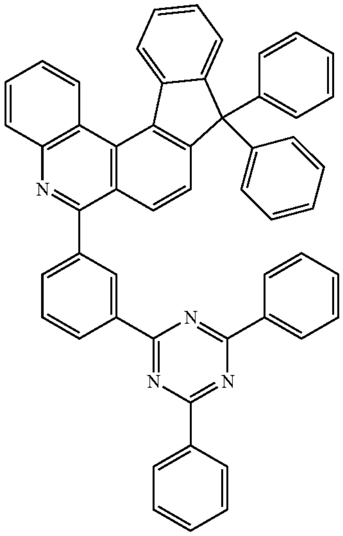

-continued
12-7
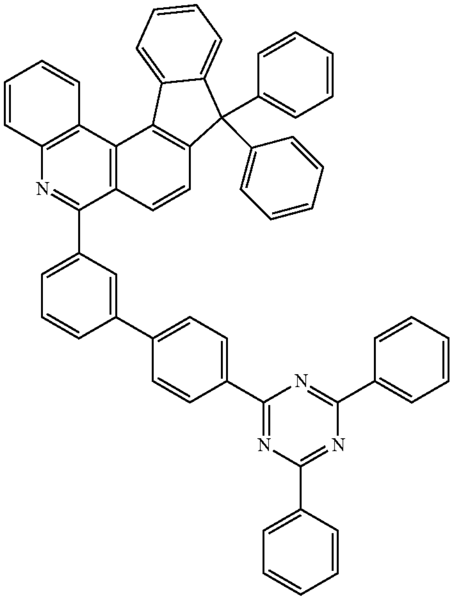
12-8
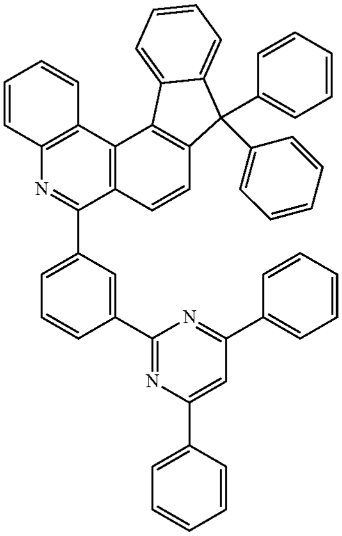
-continued
12-9
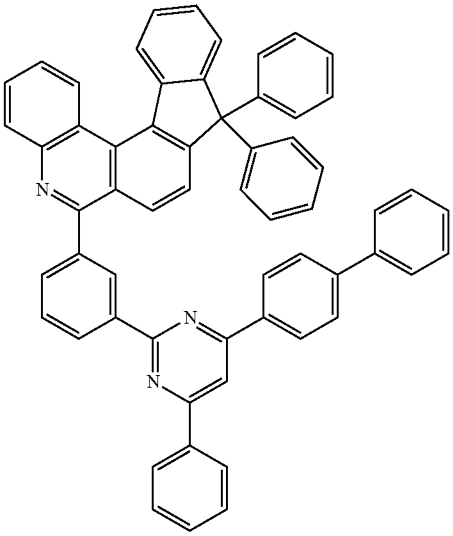
12-10
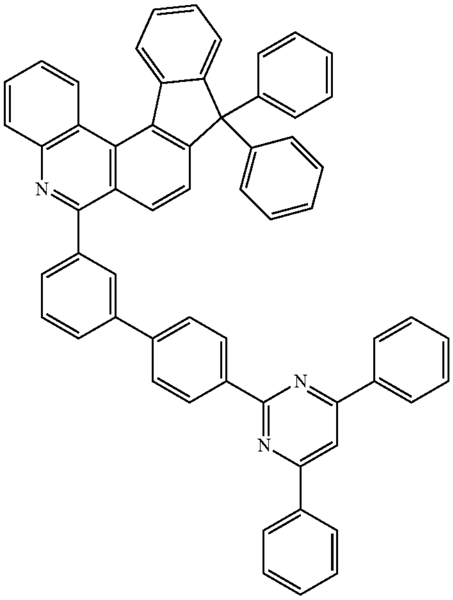

-continued
12-11
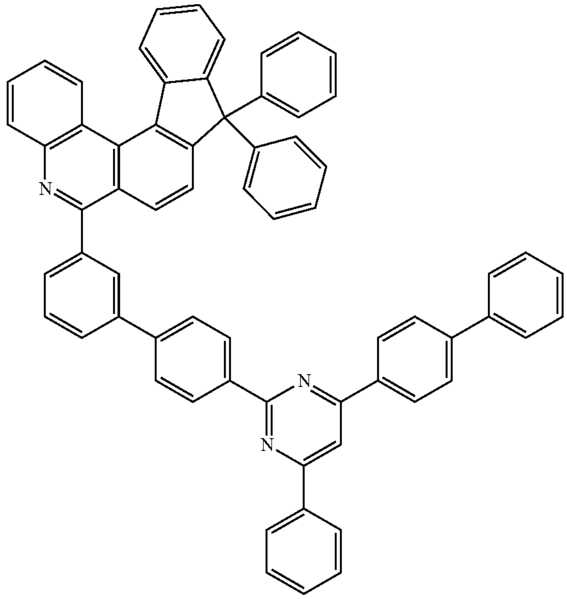
12-12
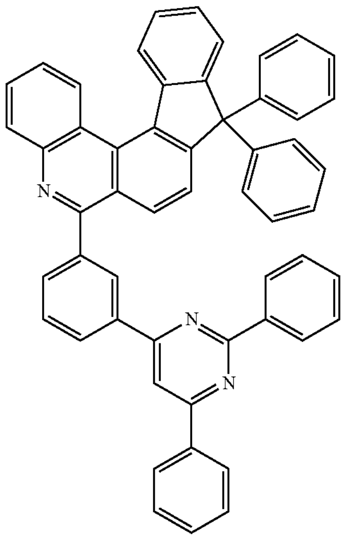
-continued
12-13
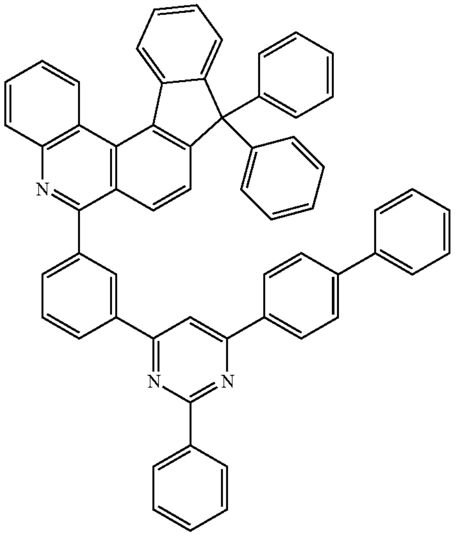
12-14
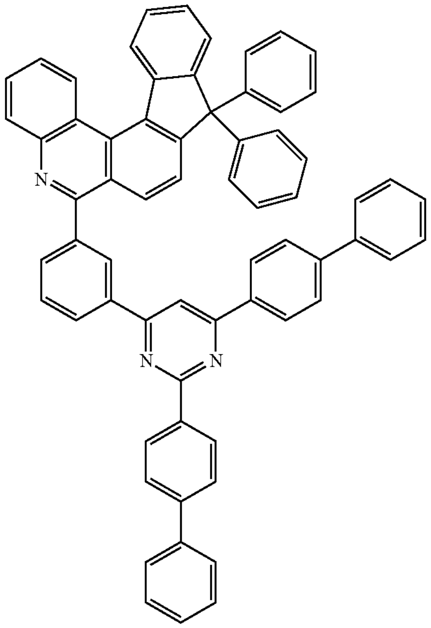

-continued
12-15
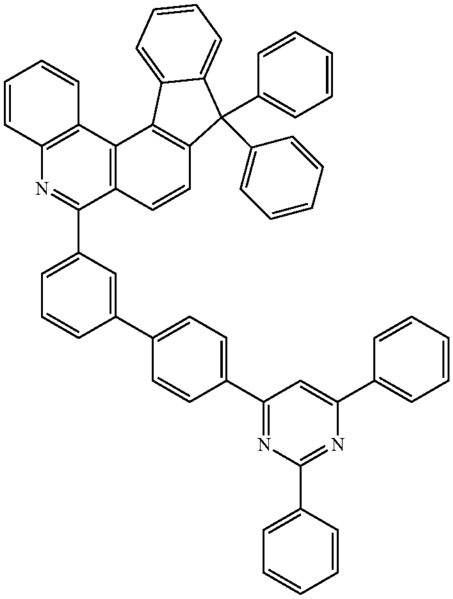
12-16
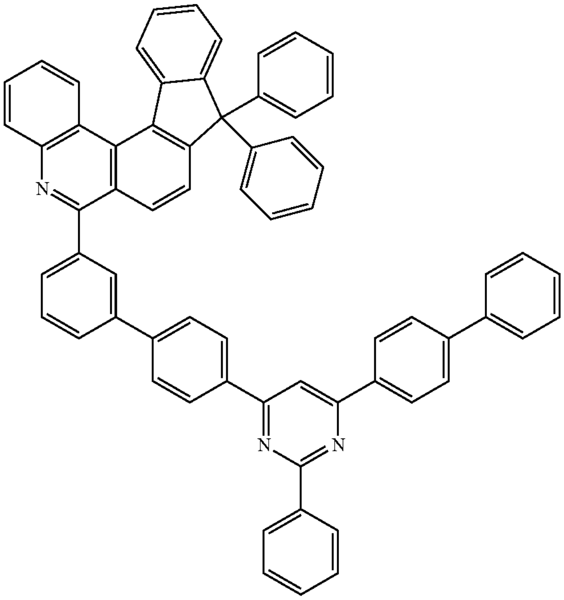
12-17
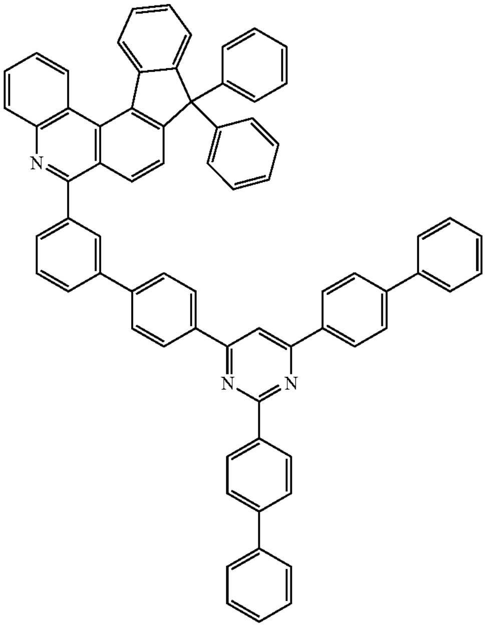
12-18
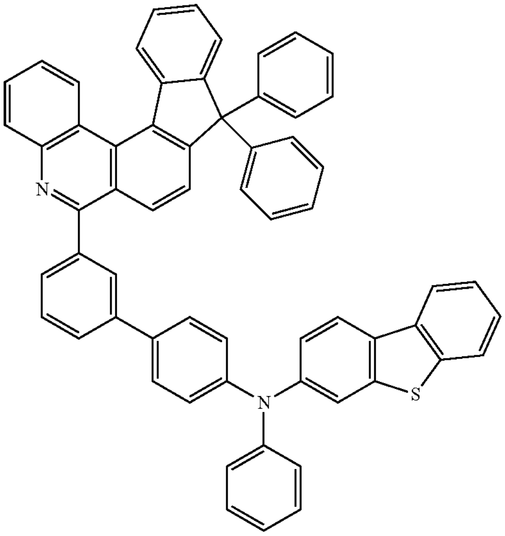

-continued
12-19
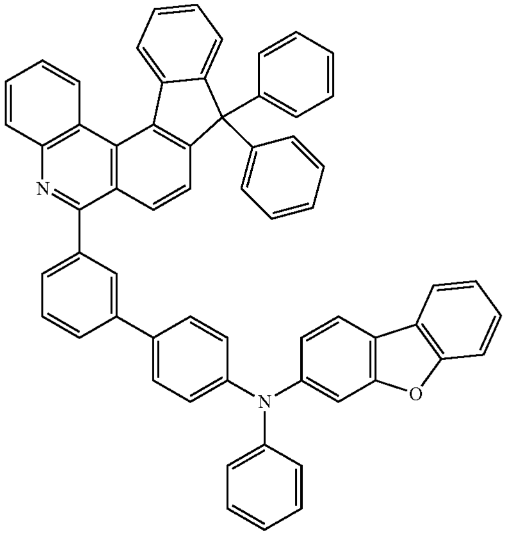
12-20
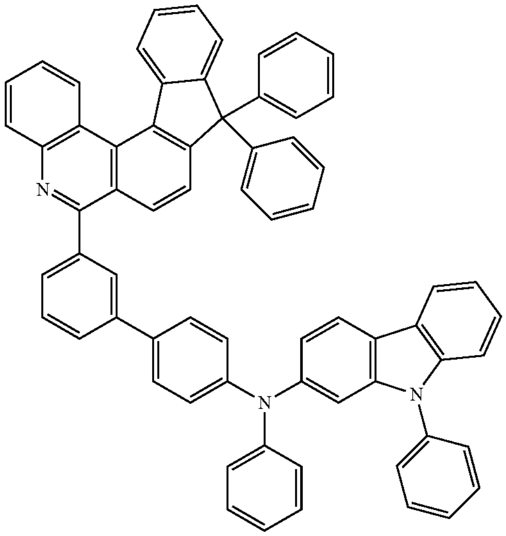
-continued
12-21
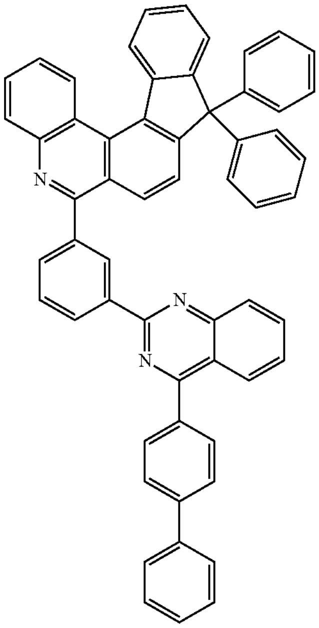
12-22
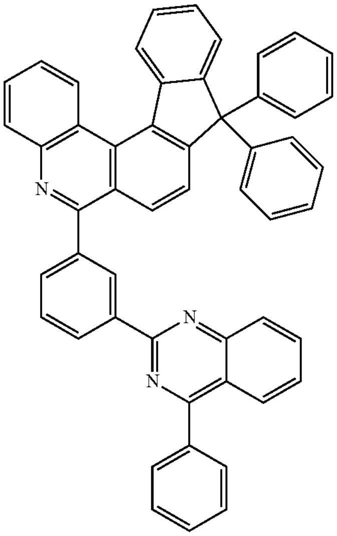

-continued
12-23
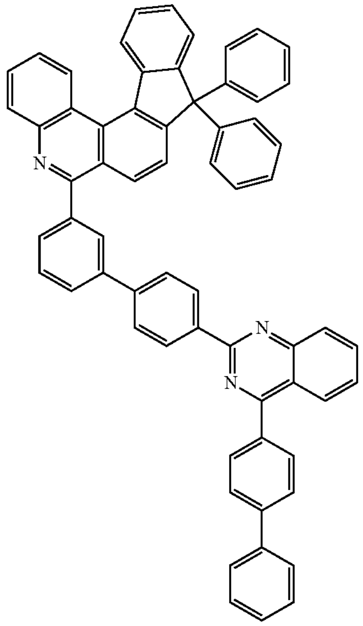
-continued
12-25
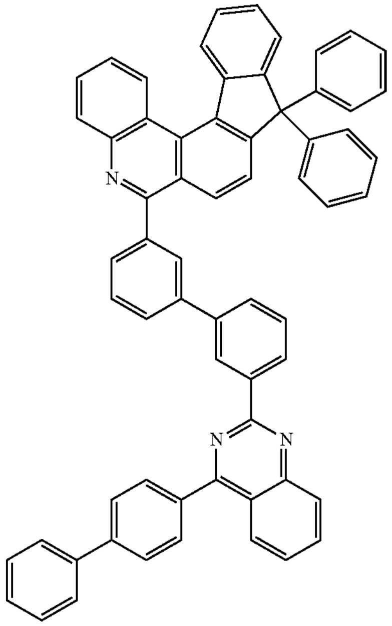
12-24
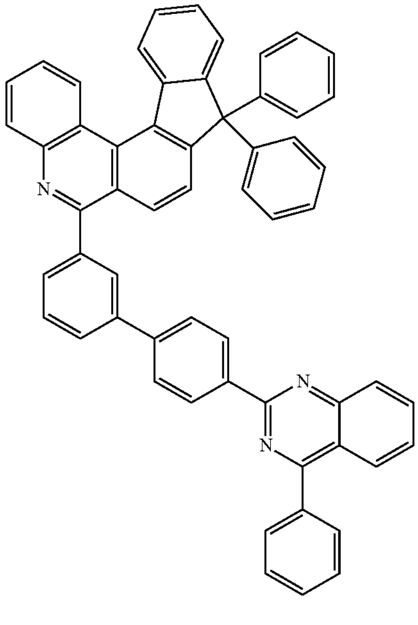
12-26
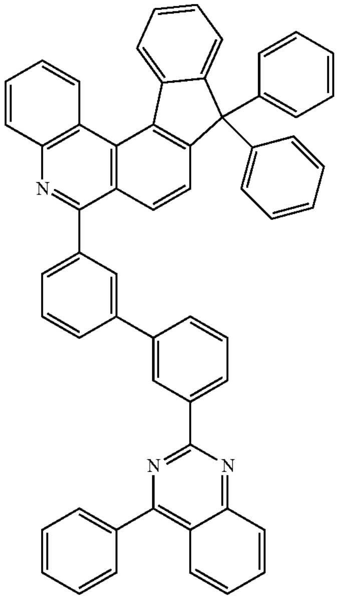

-continued
12-27
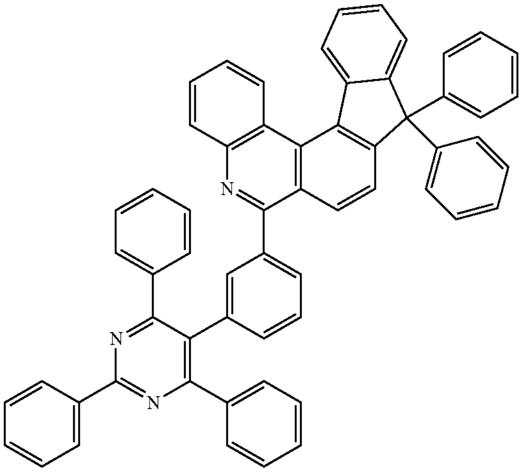
12-28
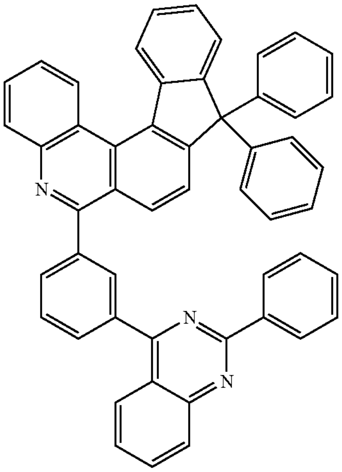
12-29
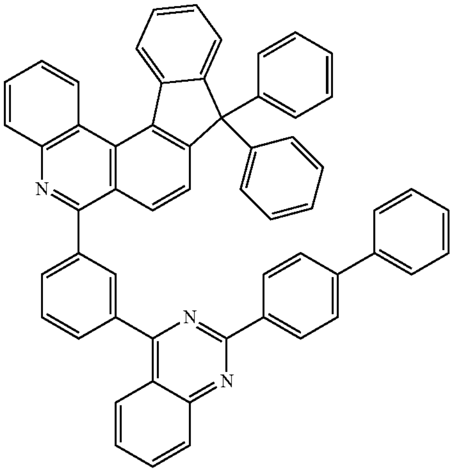
-continued
12-30
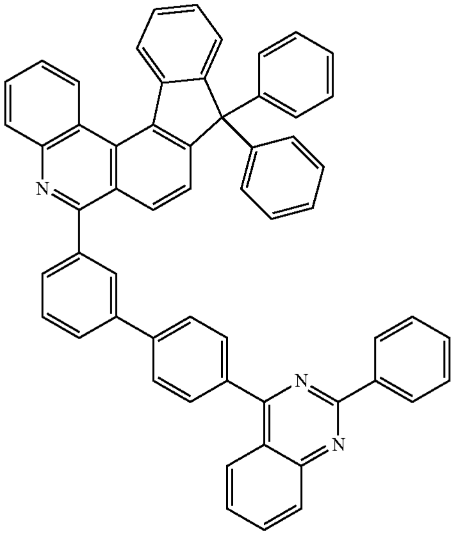
12-31
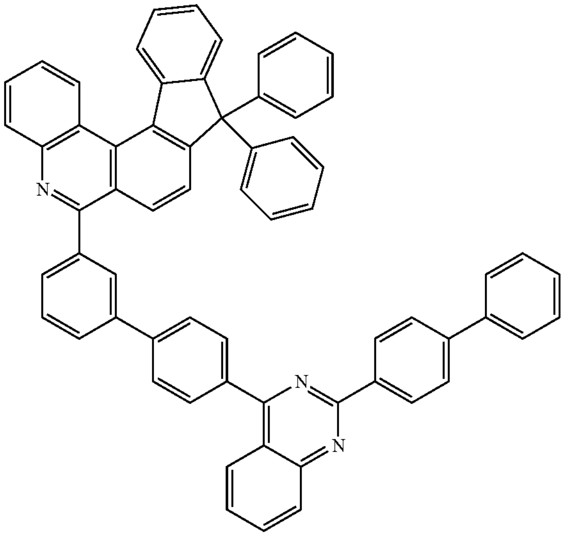
12-32
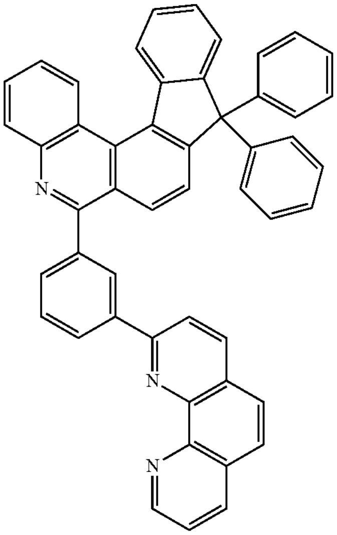

-continued
12-33
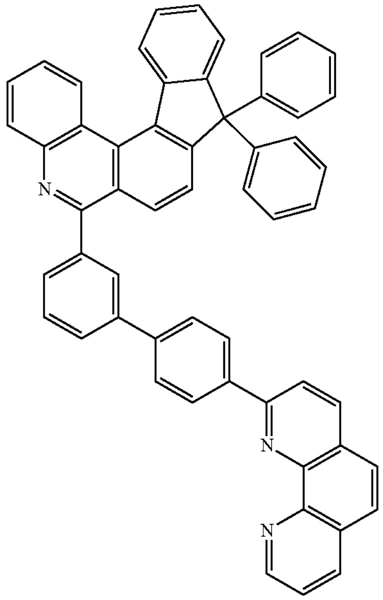
12-34
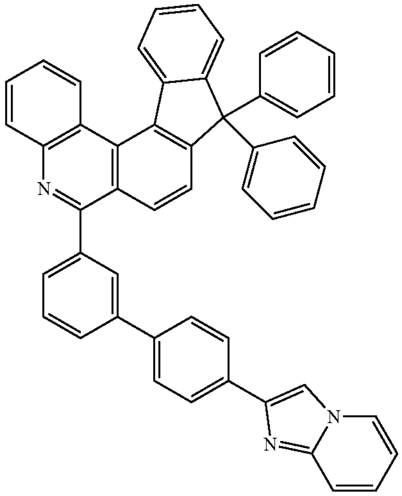
-continued
12-35
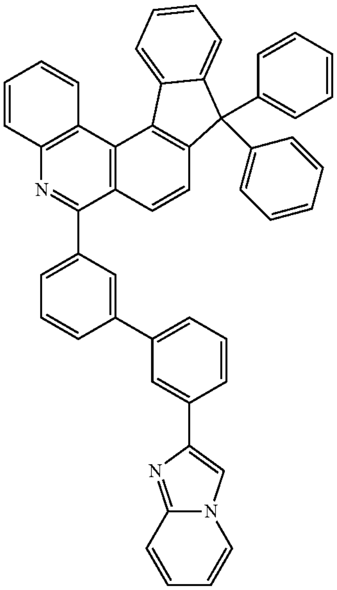
12-36
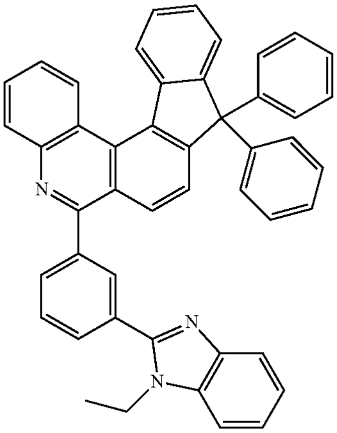
12-37
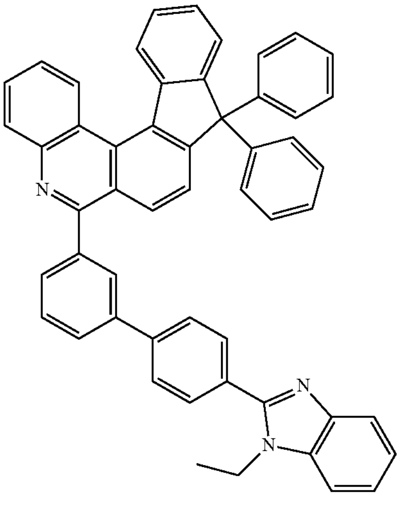

12-38
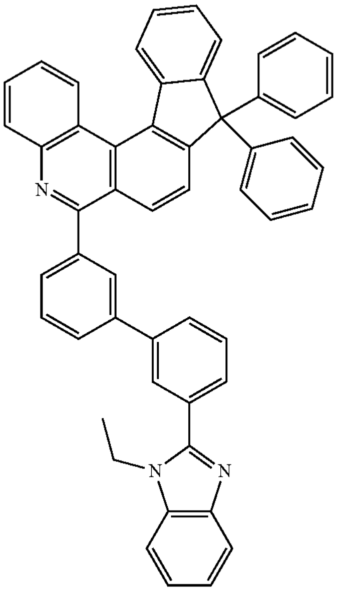
12-39
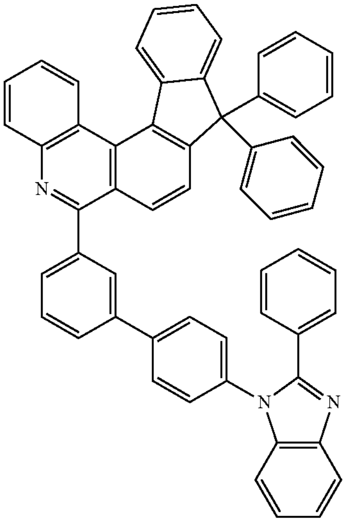
12-40
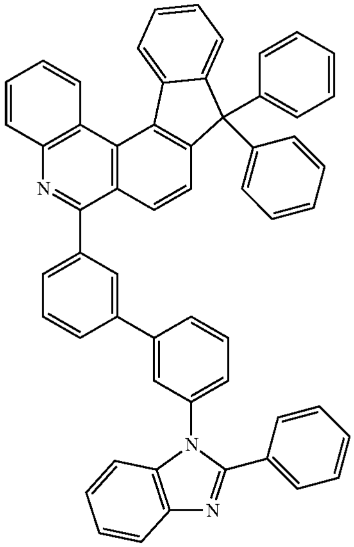
12-41
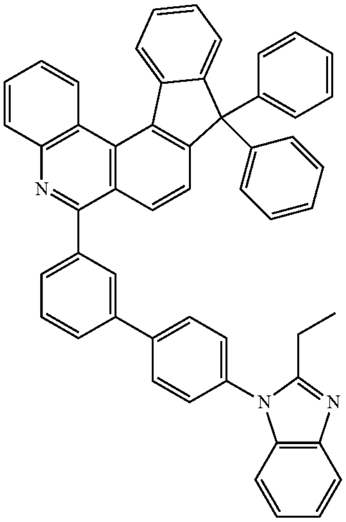
12-42
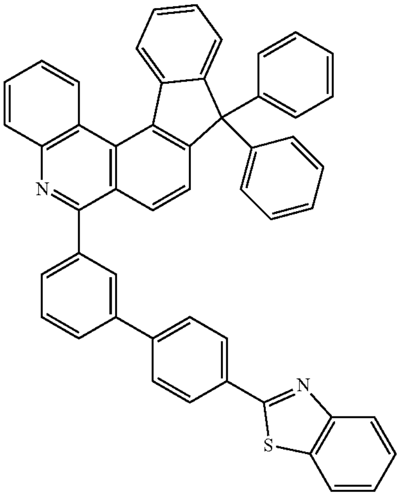
12-43
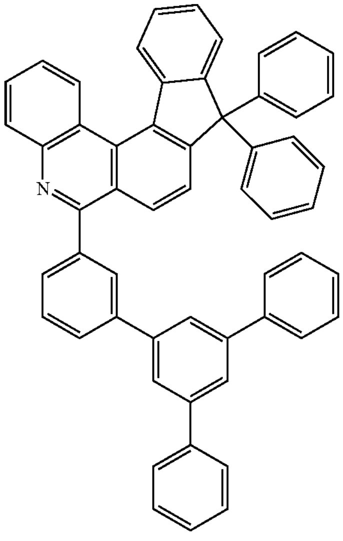

-continued
12-44
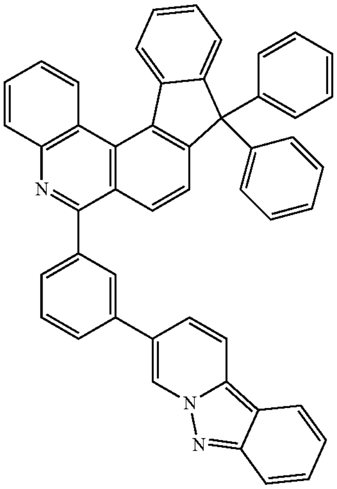
12-45
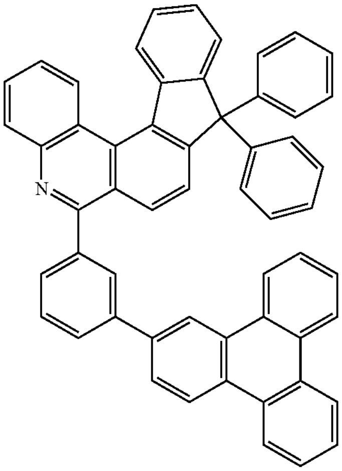
12-46
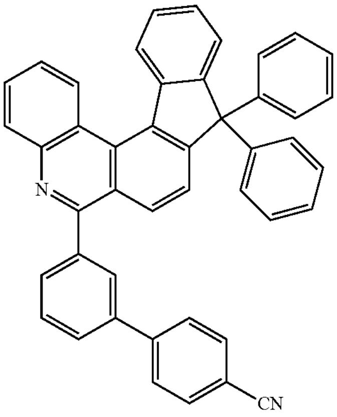
-continued
12-47
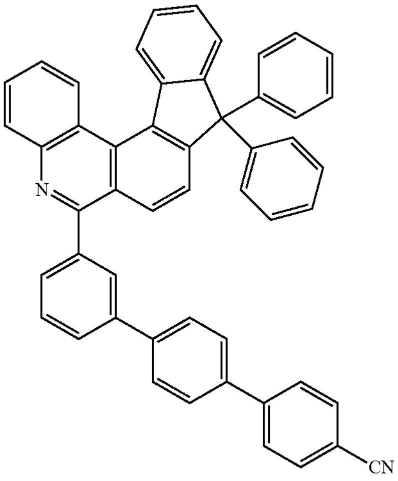
12-48
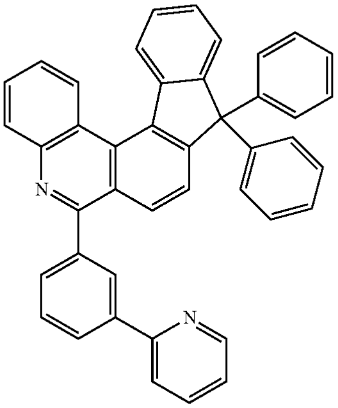
12-49
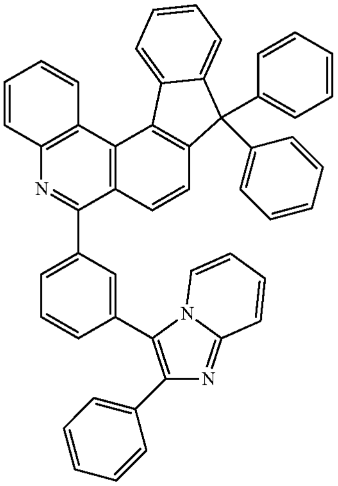

-continued
12-50
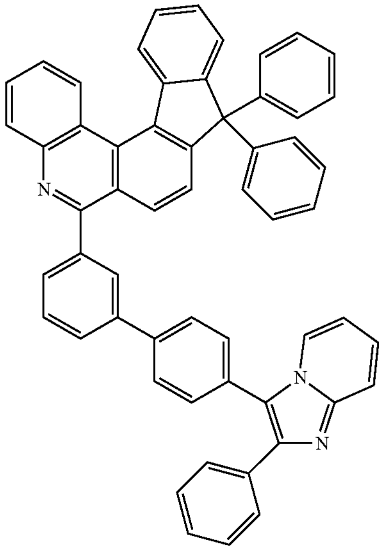
12-51
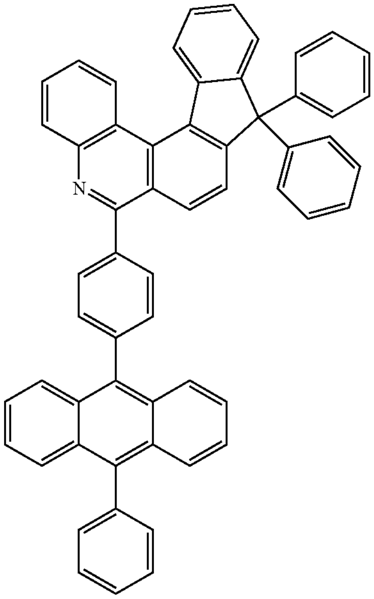
-continued
12-52
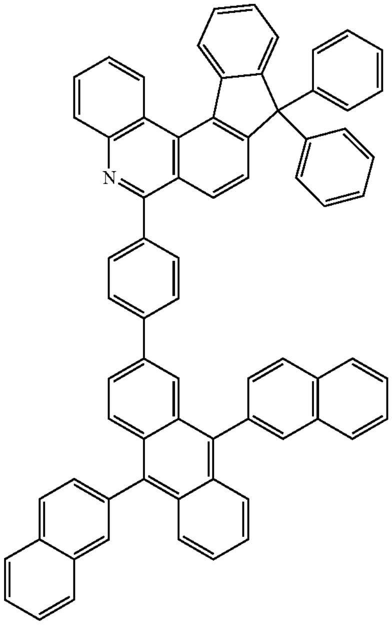
12-53
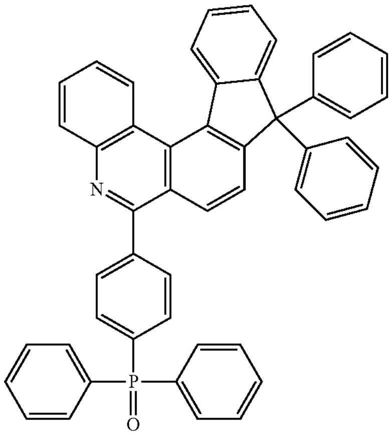
12-54
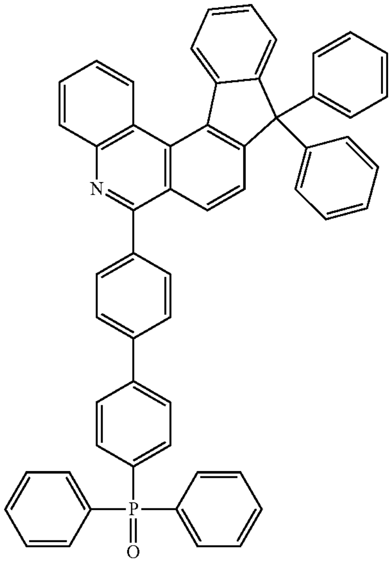

-continued
12-55
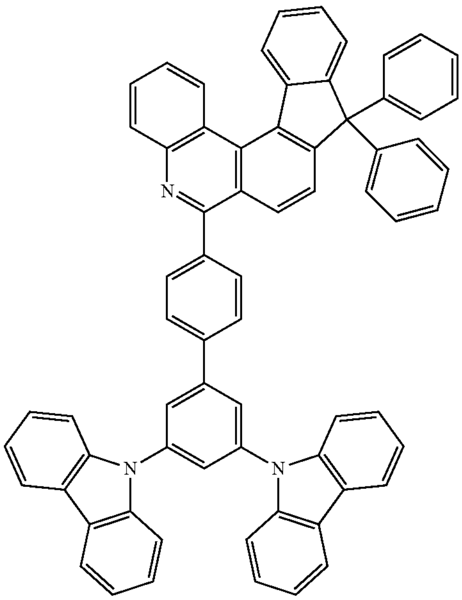
12-56
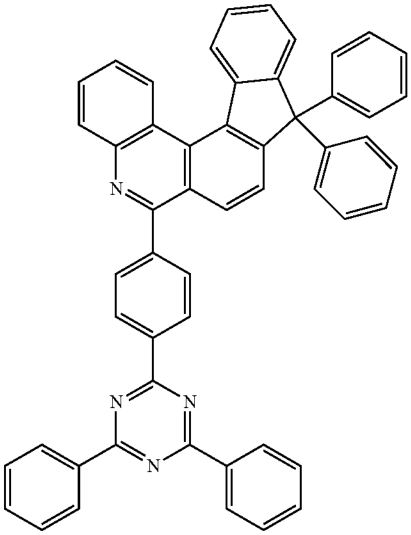
-continued
12-57
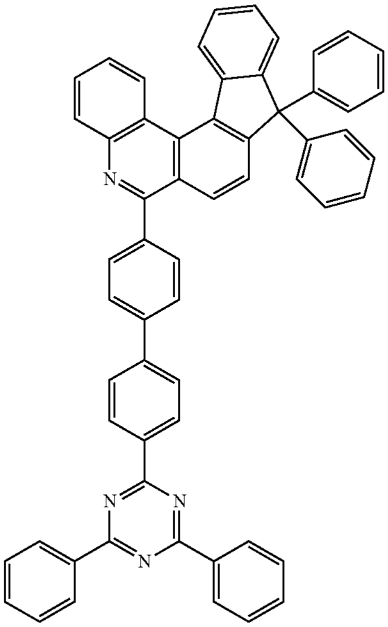
12-58
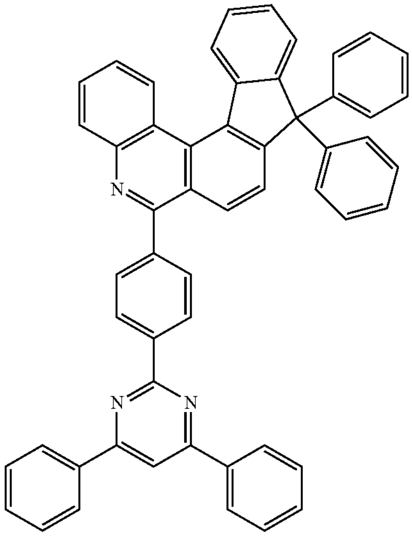

-continued
12-59
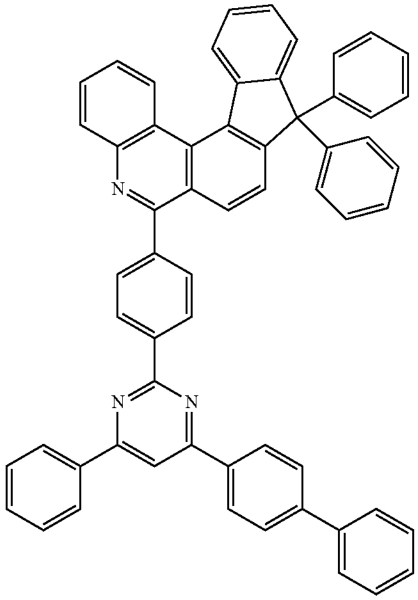
12-60
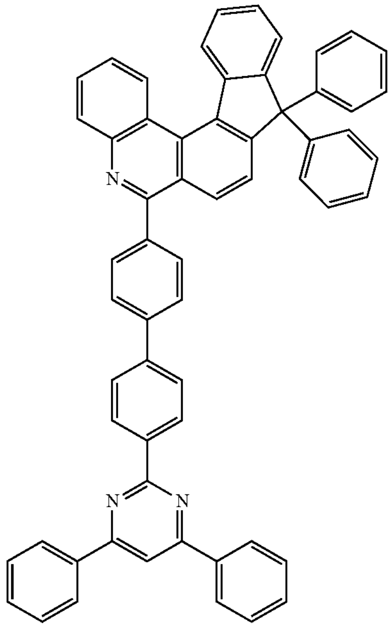
-continued
12-61
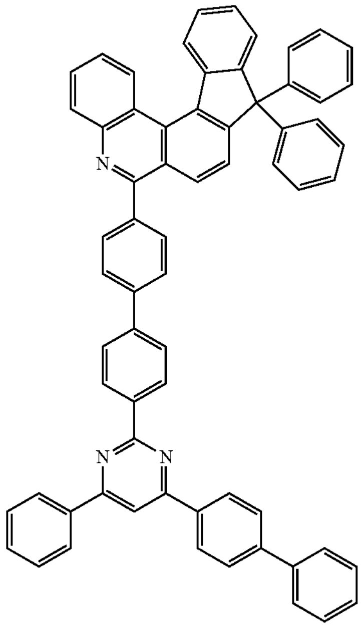
12-62
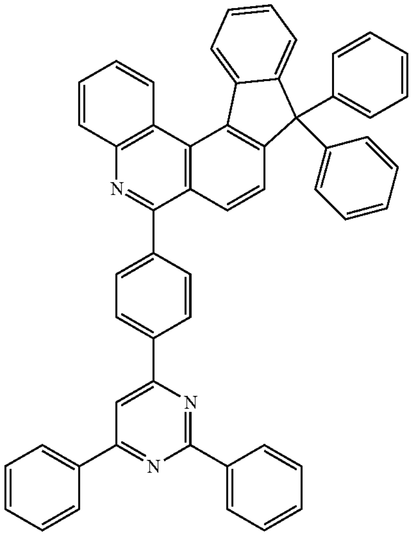

-continued
12-63
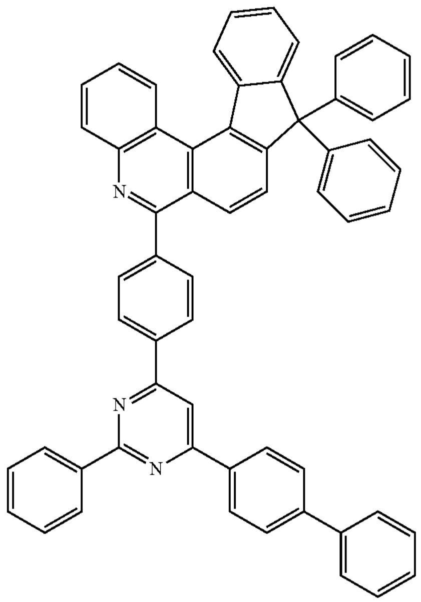
12-64
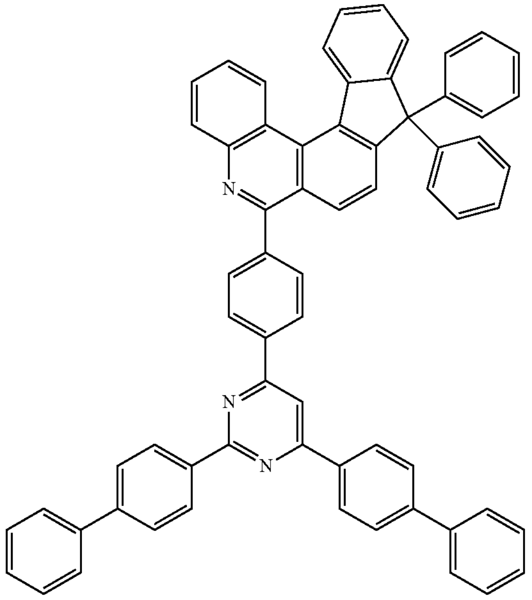
-continued
12-65
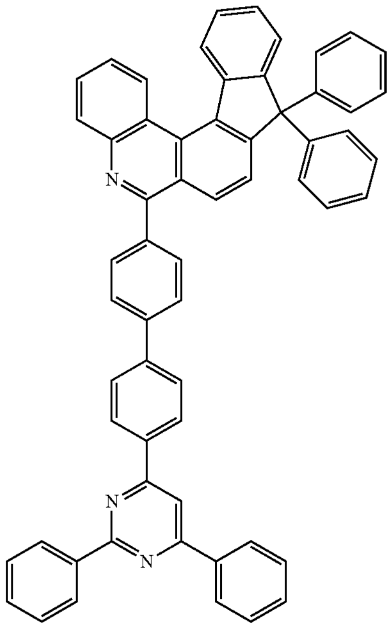
12-66
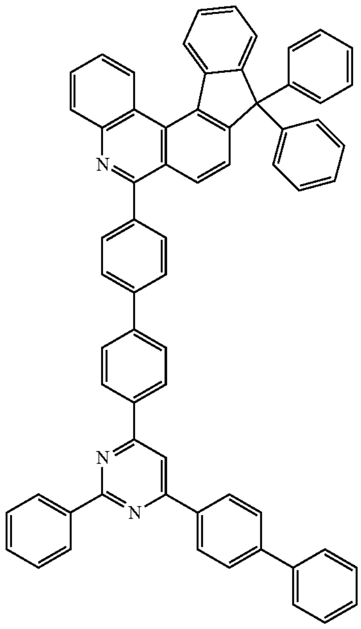

-continued
12-67
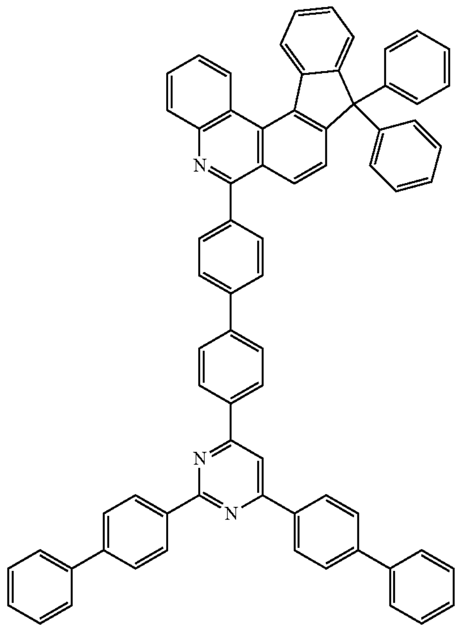
12-68
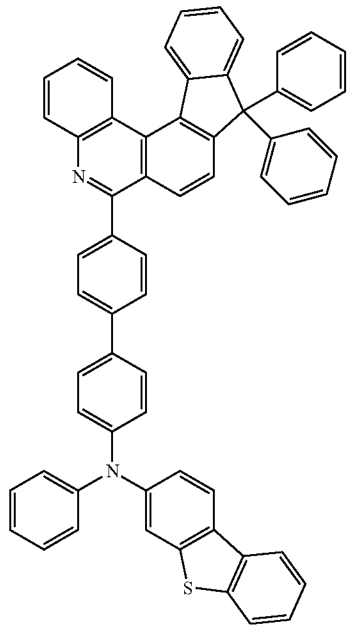
-continued
12-69
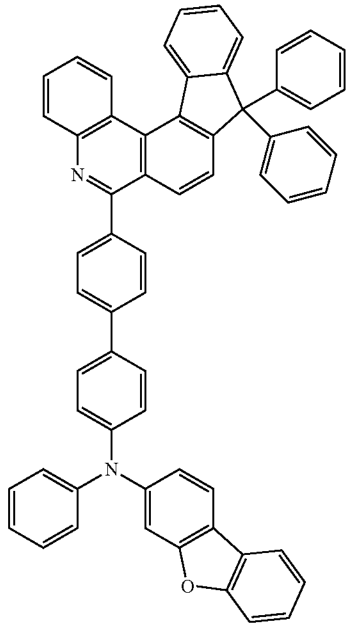
12-70
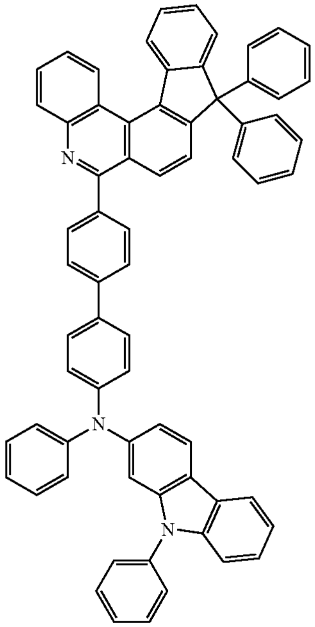

-continued
12-71
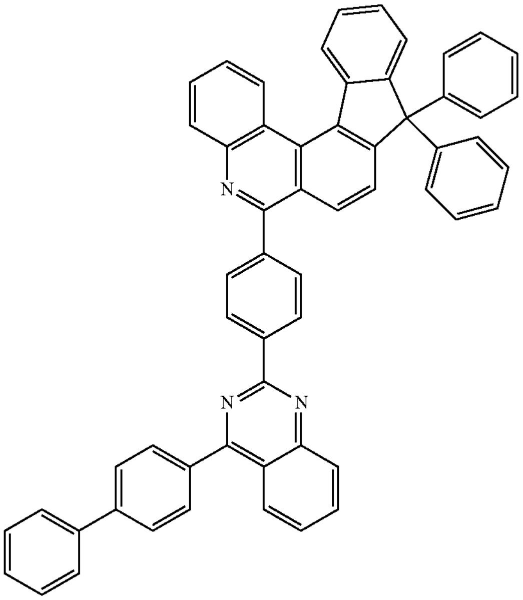
12-72
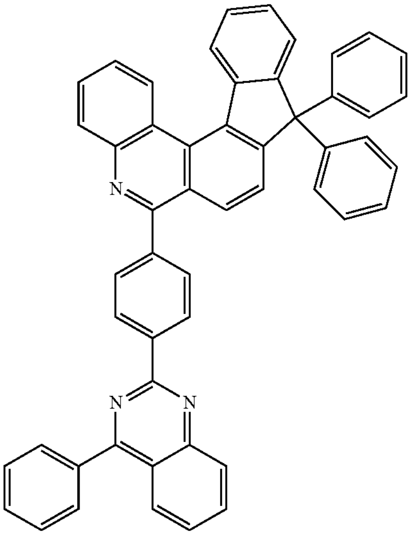
-continued
12-73
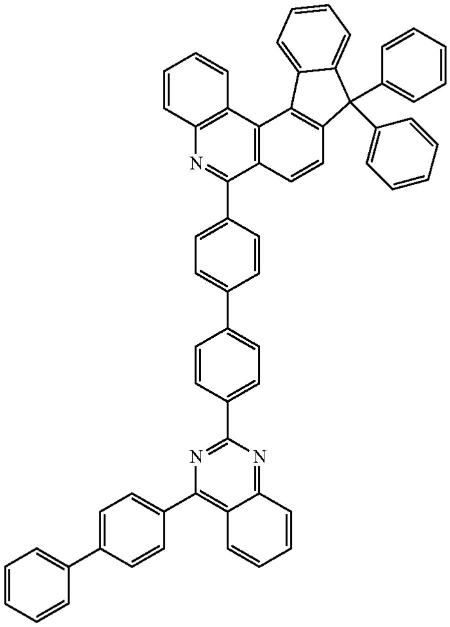
12-74
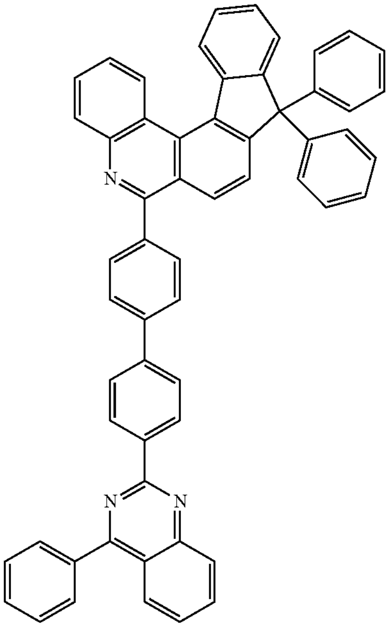

-continued
12-75
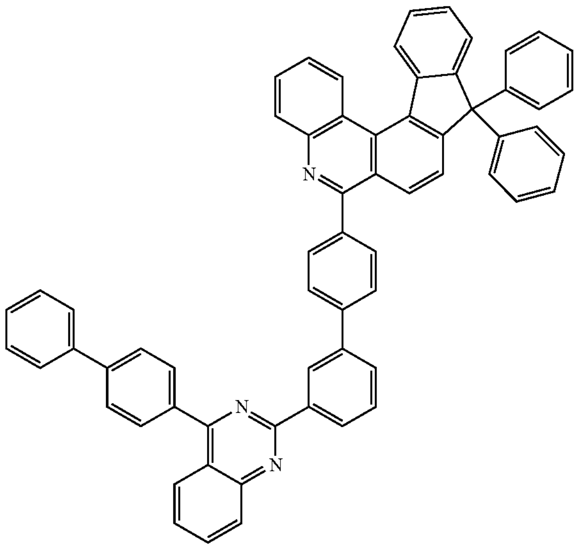
12-76
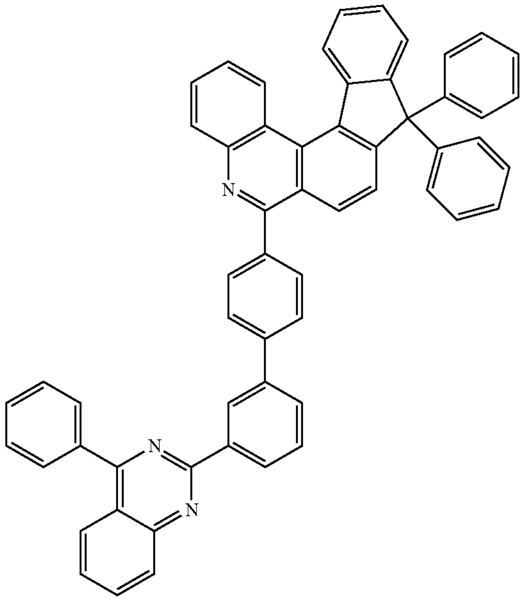
-continued
12-77
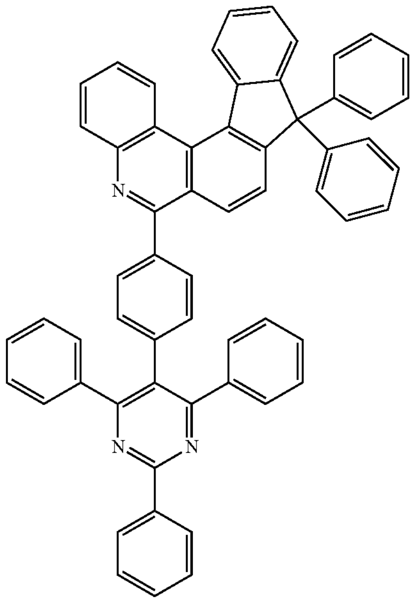
12-78
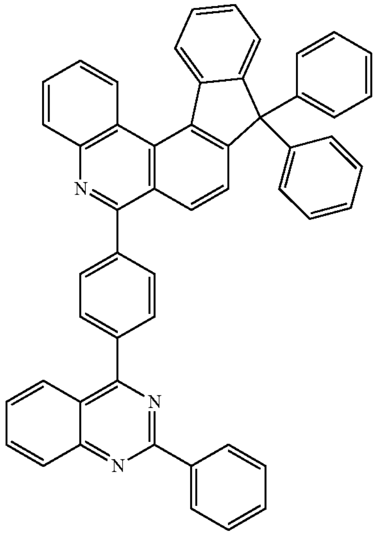

-continued
12-79
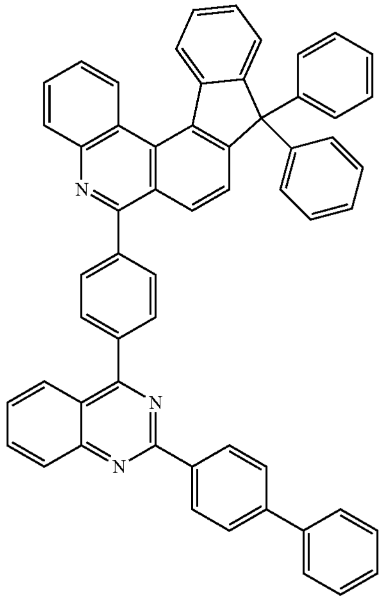
12-80
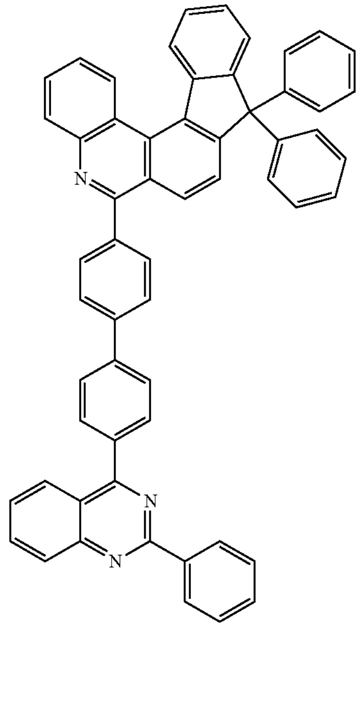
-continued
12-81
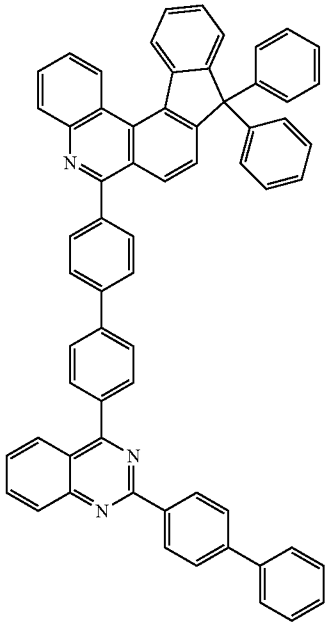
12-82
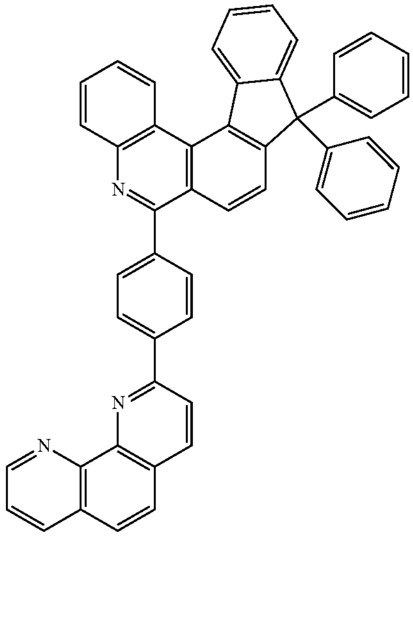

12-83
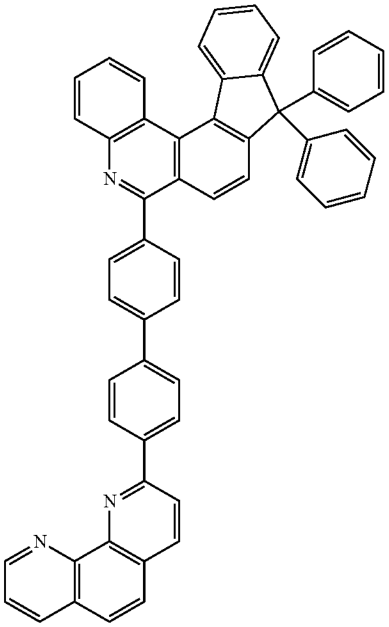
12-84
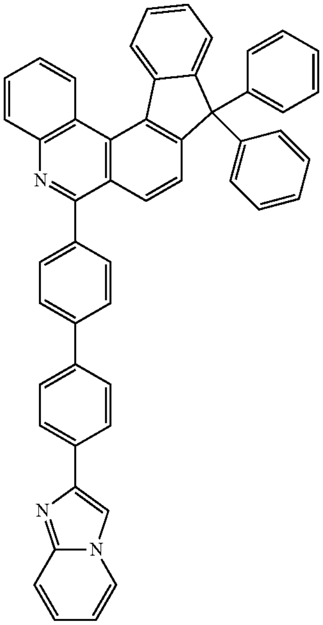
12-85
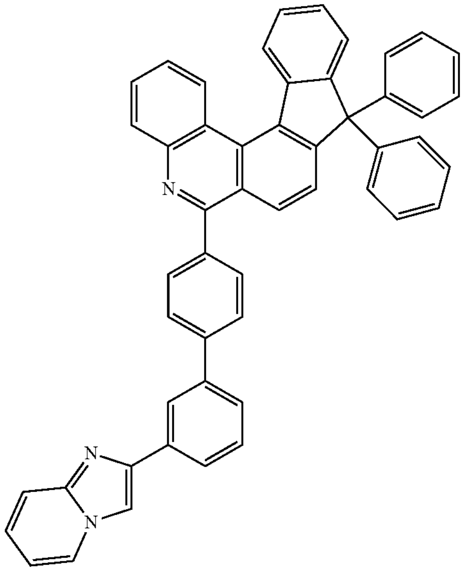
12-86
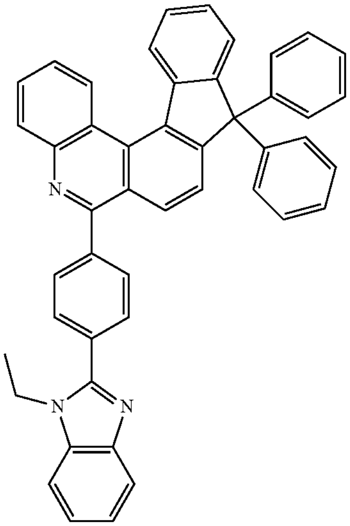

-continued
12-87
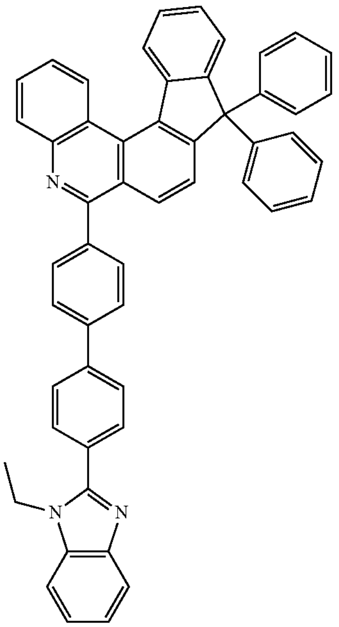
12-88
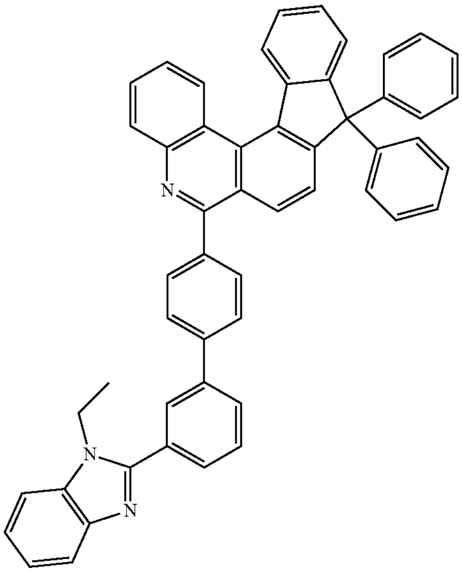
-continued
12-89
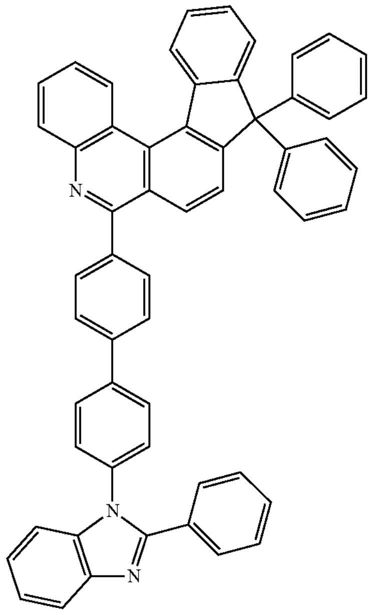
12-90
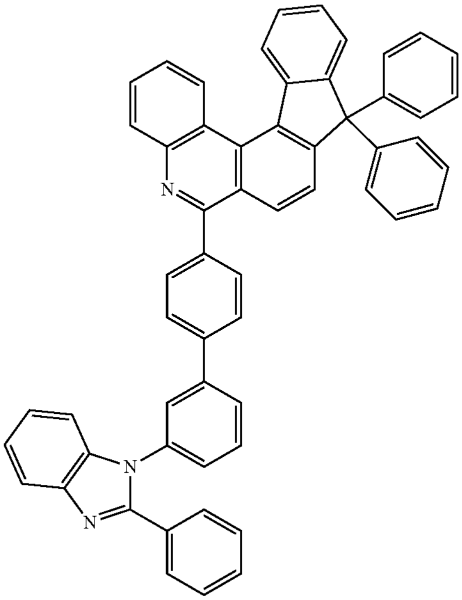

-continued
12-91
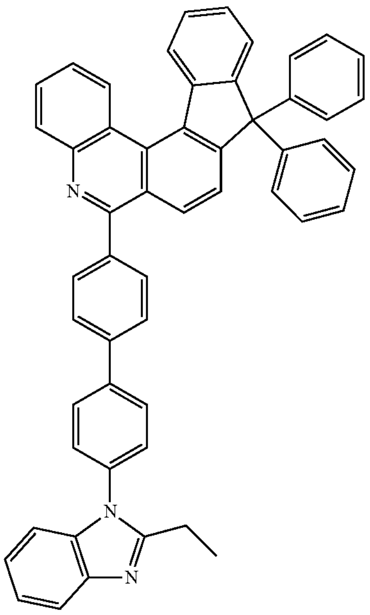
12-92
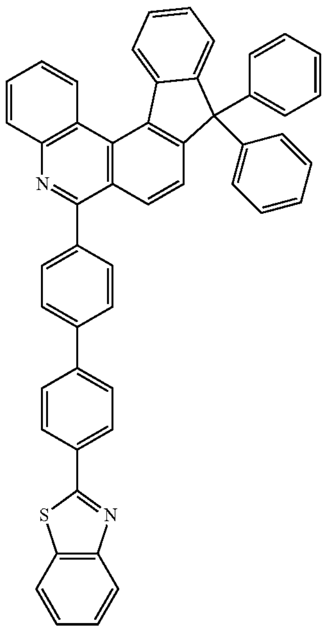
-continued
12-93
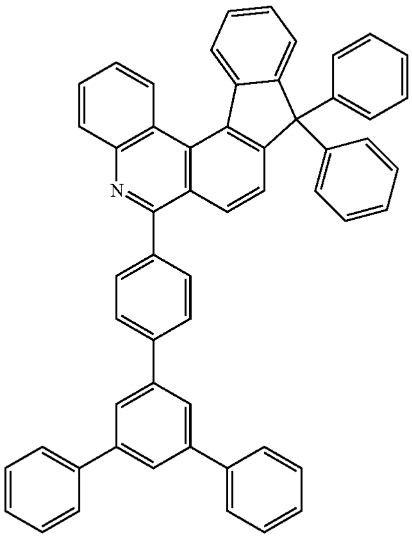
12-94
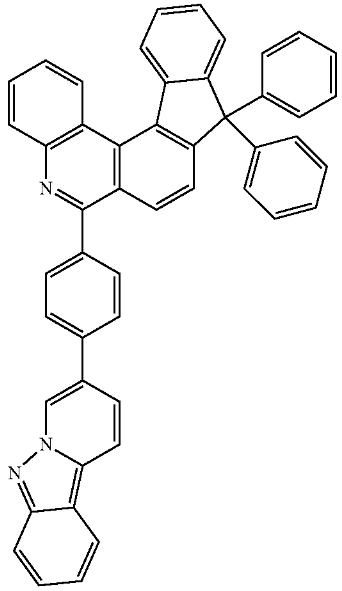

-continued
12-95
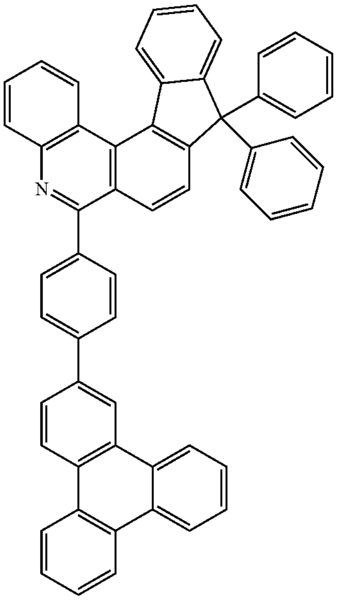
12-96
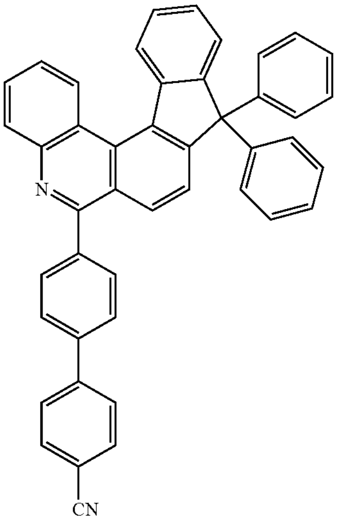
CN
-continued
12-97
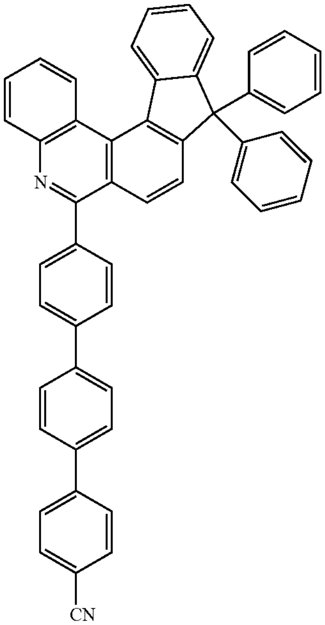
CN
12-98
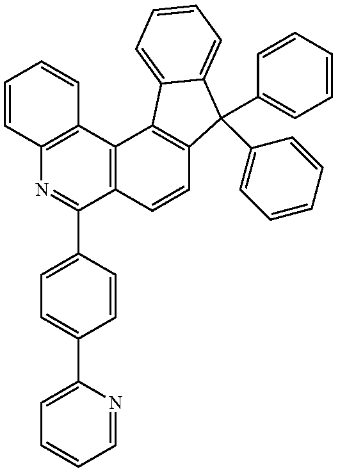
12-99
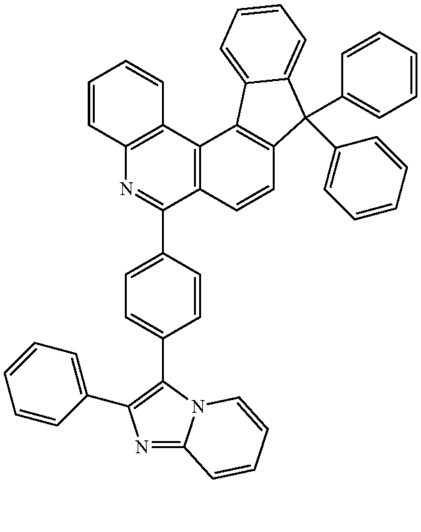

-continued 12-100

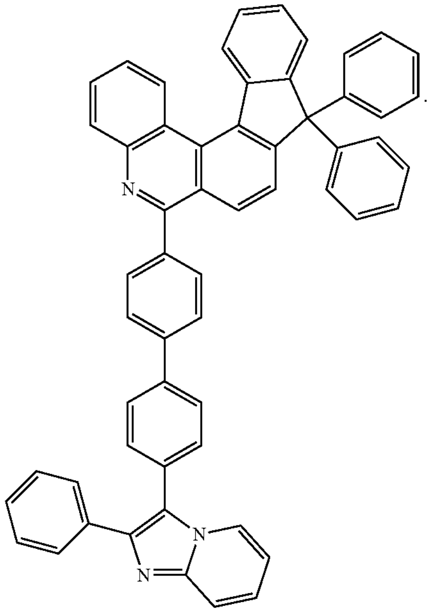

12. An organic light emitting device comprising:

an anode, a cathode, and one or more layers of organic material layers provided between the anode and the cathode, wherein one or more layers of the organic material layers include the compound of Chemical Formula 1 according to claim 1.

13. The organic light emitting device of claim 12, wherein the organic material layer including the compound of Chemical Formula 1 is at least one layer selected from a hole injection layer, a hole transport layer, a light emitting layer, an electron transport layer, and an electron injection layer.

14. The organic light emitting device of claim 12, wherein the organic material layer including the compound of Chemical Formula 1 is an electron transport layer or a light emitting layer.

* * * * *